US012807599B2

(12) United States Patent
Du et al.

(10) Patent No.: US 12,807,599 B2
(45) **Date of Patent: *Nov. 24, 2026**

(54) BIFUNCTIONAL CHIMERIC HETEROCYCLIC COMPOUNDS FOR TARGETED DEGRADATION OF ANDROGEN RECEPTORS AND USE THEREOF

(71) Applicant: HINOVA PHARMACEUTICALS INC., Chendu (CN)

(72) Inventors: Wu Du, Chendu (CN); Kun Wen, Chendu (CN); Yiwei Fu, Chendu (CN); Haibin Lv, Chendu (CN); Jinyun He, Chendu (CN); Dekun Qin, Chendu (CN); Yu Li, Chendu (CN); Jingyi Duan, Chendu (CN); Yong Li, Chendu (CN); Chaowu Ai, Chendu (CN); Zhilin Tu, Chendu (CN); Yuanwei Chen, Chendu (CN); Xinghai Li, Chendu (CN); Haibo Li, Chendu (CN)

(73) Assignee: HINOVA PHARMACEUTICALS INC., Chengdu (CN)

( * ) Notice: Subject to any disclaimer, the term of this patent is extended or adjusted under 35 U.S.C. 154(b) by 921 days.

This patent is subject to a terminal disclaimer.

(21) Appl. No.: 17/594,474

(22) PCT Filed: Apr. 16, 2020

(86) PCT No.: PCT/CN2020/085201

§ 371 (c)(1),
(2) Date: Oct. 18, 2021

(87) PCT Pub. No.: WO2020/211822

PCT Pub. Date: Oct. 22, 2020

(65) Prior Publication Data

US 2023/0091225 A1 Mar. 23, 2023

(30) Foreign Application Priority Data

Apr. 18, 2019 (CN) ......................... 201910314555.6
Sep. 20, 2019 (CN) ......................... 201910895235.4
Nov. 20, 2019 (CN) ......................... 201911144251.6

(51) Int. Cl.
*C07D 401/04* (2006.01)
*A61K 31/427* (2006.01)
(Continued)

(52) U.S. Cl.
CPC ......... *C07D 417/12* (2013.01); *C07D 401/04* (2013.01); *C07D 403/06* (2013.01); *C07D 403/12* (2013.01); *C07D 413/12* (2013.01); *C07D 413/14* (2013.01); *C07D 417/14* (2013.01); *C07D 471/04* (2013.01); *C07D 471/10* (2013.01); *C07D 487/04* (2013.01);
(Continued)

(58) Field of Classification Search
CPC ................ C07D 401/04; C07D 401/14; C07D 403/06; C07D 403/12; C07D 413/12; C07D 413/14; C07D 417/12; C07D 417/14; C07D 471/04; C07D 471/10; C07D 487/04; C07D 487/08; C07D 487/10; C07D 491/08; C07D 491/18; C07D 498/22; C07D 519/00; C07B 2200/05; C07K 5/06; C07K 5/06034; C07K 5/08; C07K 5/0806; C07K 5/0808; A61K 31/427; A61K 31/506; A61K 31/53; A61K 38/05; A61K 38/06; A61K 47/545; A61K 47/55; A61P 21/00; A61P 35/00
See application file for complete search history.

(56) References Cited

U.S. PATENT DOCUMENTS

2016/0214972 A1 † 7/2016 Jin
2017/0008904 A1 † 1/2017 Crew
2017/0327469 A1 11/2017 Crew et al.
2018/0099940 A1 † 4/2018 Crew
2025/0082763 A1 * 3/2025 Li .......................... A61K 45/06
2025/0082764 A1 * 3/2025 Li .......................... A61K 31/52

FOREIGN PATENT DOCUMENTS

CN 107428734 A 12/2017
CN 108137507 A 6/2018
WO 2012145361 A1 10/2012
WO 2018071606 A1 4/2018
WO 2019023553 A1 1/2019

* cited by examiner
† cited by third party

*Primary Examiner* — Brenda L Coleman
(74) *Attorney, Agent, or Firm* — NKL Law; Allen Xue

(57) ABSTRACT

Bifunctional chimeric heterocyclic compounds of formula (I) is effective for targeted degradation of androgen receptors and use thereof. The compound of formula (I) also has an isotopic compound, an optical isomer, a tautomer, pharmacologically acceptable salt, a prodrug thereof, or a solvate. In formula (I), ARB is an androgen receptor recognition/binding part, L is a link part, and U is a ubiquitin protease recognition/binding part; and the three parts are connected by means of chemical bonds. The compound can perform targeted degradation on androgen receptors in prostate cancer cells, and suppress proliferation of the prostate cancer cells, and also show good metabolic stability and pharmacokinetic properties. The compound has good application prospect in preparation of targeted chimeras for protein degradation of androgen receptors and in the preparation of drugs for treating related diseases regulated by the androgen receptors.

(I)

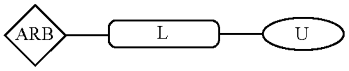

7 Claims, 1 Drawing Sheet

(51) Int. Cl.

| | |
|---|---|
| ***A61K 31/506*** | (2006.01) |
| ***A61K 31/53*** | (2006.01) |
| ***A61K 38/06*** | (2006.01) |
| ***A61K 38/08*** | (2019.01) |
| ***A61K 47/55*** | (2017.01) |
| ***A61P 21/00*** | (2006.01) |
| ***A61P 35/00*** | (2006.01) |
| ***C07D 401/14*** | (2006.01) |
| ***C07D 403/06*** | (2006.01) |
| ***C07D 403/12*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 487/08*** | (2006.01) |
| ***C07D 487/10*** | (2006.01) |
| ***C07D 491/08*** | (2006.01) |
| ***C07D 491/18*** | (2006.01) |
| ***C07D 498/22*** | (2006.01) |
| ***C07D 519/00*** | (2006.01) |
| ***C07K 5/06*** | (2006.01) |
| ***C07K 5/08*** | (2006.01) |

(52) U.S. Cl.

CPC ......... *C07D 487/08* (2013.01); *C07D 487/10* (2013.01); *C07D 491/08* (2013.01); *C07D 491/18* (2013.01); *C07D 498/22* (2013.01); *C07D 519/00* (2013.01); *C07B 2200/05* (2013.01)

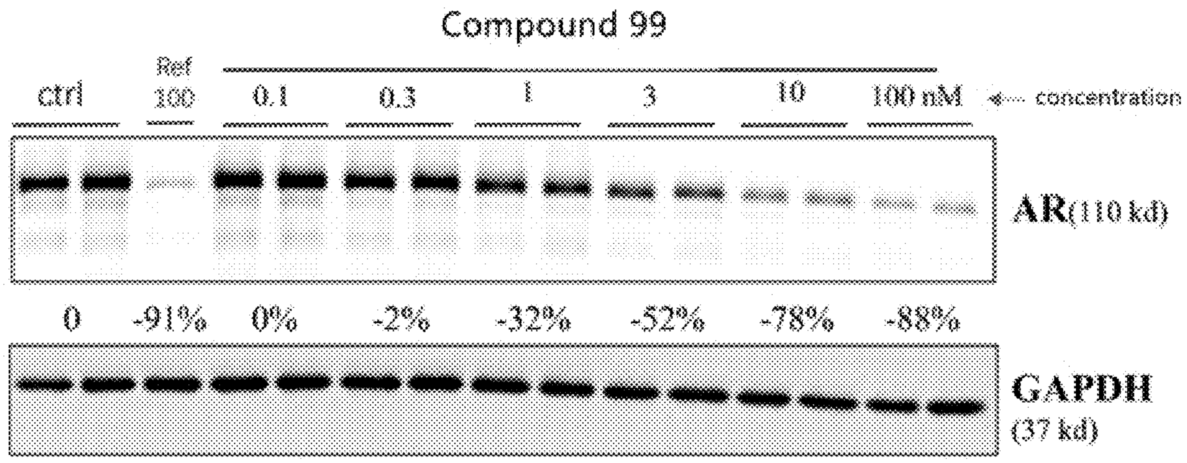
Compound 99
ctrl
Ref 100
0.1
0.3
1
3
10
100 nM
concentration
AR(110 kd)
0
-91%
0%
-2%
-32%
-52%
-78%
-88%
GAPDH
(37 kd)

BIFUNCTIONAL CHIMERIC HETEROCYCLIC COMPOUNDS FOR TARGETED DEGRADATION OF ANDROGEN RECEPTORS AND USE THEREOF

TECHNICAL FIELD

The present invention belongs to the field of medicine, and in particular, the present invention relates to a class of bifunctional chimeric heterocyclic compounds for targeted degradation of androgen receptors and the use thereof.

BACKGROUND TECHNOLOGY

As the growing and aging of global population, the incidence of prostate cancer continues to increase. At present, the main treatment is androgen-deprivation therapy. Androgen receptor (AR) belongs to the nuclear receptor family and is a type of ligand-dependent transcription factor. The abnormal regulation of AR signaling pathway plays an important role in the occurrence and development of prostate cancer. Studies have shown that castration-resistant prostate cancer (CRPC) still depends on the role of AR. The androgen receptor contains 918 amino acids, and has a similar structure and function to other nuclear receptors. It consists of three important domains, namely the DNA binding domain (DBD), the ligand binding domain (LBD), and N-terminal domain (NTD), in which DBD and LBD are connected by a hinge region. The LBD present at C-terminal of AR is the site where AR binds to the ligand, which determines the specificity of the binding of the ligand to AR, and the ligand binds to the LBD to activate AR. Two transcriptional activation domains have been identified in AR, namely activation function 1 (AF1) in the NTD domain and the highly conserved hydrophobic pocket activation function 2 (AF2) in the LBD domain. Before 2010, docetaxel-based chemotherapy was the only treatment that could prolong the survival of patients with metastatic CRPC.

Proteolytic targeting chimeras (PROTACs) have attracted widespread attention as small molecules that can induce degradation of target proteins. PROTACs, as bifunctional molecules, include a small molecule compound that can bind to the protein of interest (POI), a linking group introduced at its suitable position, and a small molecule compound which can bind to a ubiquitin protease. The small molecule probe obtained can simultaneously bind to the target protein and the ubiquitin protease, thereby promoting the ubiquitination of the target protein, and by multiple ubiquitination, the protein can be recognized and degraded by the proteasome Using the strategy of PROTACs, a proteolytic targeting chimera, capable of special recognition/binding to the androgen receptor, has been prepared, which can regulate the level of the androgen receptor by intracellular ubiquitin-proteasome degradation system and induce the degradation of the androgen receptor, so as to achieve the effect of treating prostate cancer and other related diseases regulated by androgen receptors.

Therefore, a bifunctional chimeric molecule, that can specifically bind to the androgen receptor and effectively degrade the androgen receptor, has been developed, which has good application prospects in the treatment of related diseases regulated by the androgen receptor.

Content of the Invention

The object of the present invention is to provide a proteolytic targeting chimera, which has a stronger ability of specially binding to the androgen receptor, as well as a higher activity of degrading the androgen receptor. The present invention provides compound of formula (I), or an isotopic compound thereof, or an optical isomer thereof, or a tautomer thereof, or a pharmaceutically acceptable salt thereof, or a prodrug thereof, or a solvate thereof:

(I)

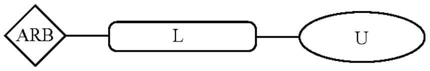

wherein, ARB is an androgen receptor recognition/binding part, L is the linking part, and U is a ubiquitin protease recognition/binding part; and the three parts are connected by chemical bonds;

wherein, said ARB is selected from the structure of formula (I-A):

(I-A)

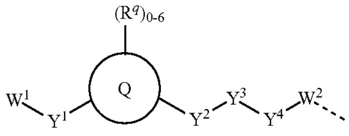

wherein, $W^1$ is selected from substituted or unsubstituted aryl or heteroaryl, and the substituent of $W^1$ is each independently selected from the group consisting of halogen, hydroxyl, amino, mercapto, sulfone, sulfoxide, nitro, cyano. $CF_3$, heterocyclic group, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof. $C_{1-6}$ alkylamino group, $C_{2-6}$ alkenyl or $C_{2-6}$ alkynyl;

each of $Y^1$, $Y^2$, $Y^3$, and $Y^4$ is independently selected from the group consisting of a bond, O, S, $NR^1$, $CR^2R^3$, C=O, C=S, SO or $SO_2$; each of said $R^1$, $R^2$, and $R^3$ is independently selected from the group consisting of H, $C_{1-6}$ alkyl or a halogenated compound thereof or a deuterated compound thereof, 3-8 membered cycloalkyl or heterocyclic group containing 0-2 heteroatoms, or $R^2$ and $R^3$ are linked to form a 3-8 membered ring containing 0-2 heteroatoms;

Q is selected from a saturated cycloalkyl, a saturated heterocyclic group, or an aryl or a heteroaryl containing 0-4 heteroatoms substituted with 0-6 $R^q$, and said $R^q$ is each independently selected from the group consisting of H, D, OH, halogen, $C_{1-6}$ alkyl or a halogenated compound thereof. $C_{1-6}$ alkoxy or a halogenated compound thereof, or two substituents are linked together to form a 3-8 membered ring containing 0-2 heteroatoms;

$W^2$ is selected from a bond, or the following groups substituted with 0-4 $R^4$: alkenyl, alkynyl, $C_{1-6}$ alkyl, $C_{1-6}$ alkoxy, monocyclic alkyl, monocyclic heterocyclic group, aryl, heteroaryl, bridged cycloalkyl, bridged heterocyclic group, spirocycloalkyl, heterospirocyclic group, fused cycloalkyl, fused heterocyclic group; said $R^4$ is each independently selected from the group consisting of H, halogen, hydroxy, amino, mercapto, sulfone, sulfoxide, nitro, cyano, $CF_3$, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino, $C_{2-6}$ alkynyl, $C_{2-6}$ alkenyl, or $R^4$ is selected from

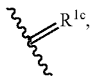

and $R^{1c}$ is selected from O or S; or,

ARB is selected from the structure of formula (I-B):

(I-B)

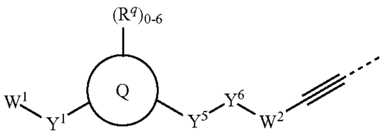

wherein, $W^1$ is selected from substituted or unsubstituted aryl or heteroaryl, and the substituent of $W^1$ is each independently selected from the group consisting of halogen, hydroxyl, amino, mercapto, sulfone, sulfoxide, nitro, cyano. $CF_3$, heterocyclic group, $C_{1-6}$ alkyl or a halogenated compound thereof or a deuterated compound thereof. $C_{3-6}$ cycloalkyl, $C_{1-4}$ alkoxy or a halogenated compound thereof or a deuterated compound thereof. $C_{1-6}$ alkylamino group, $C_{2-6}$ alkenyl or $C_{2-6}$ alkynyl;

each of $Y^1$, $Y^5$, and $Y^6$ is independently selected from the group consisting of a bond, O, S, $NR^1$, $CR^2R^3$, C═O, C═S, SO, $SO_2$ each of said $R^1$, $R^2$, and $R^3$ is independently selected from the group consisting of H, $C_{1-6}$ alkyl or a halogenated compound thereof or a deuterated compound thereof, 3-8 membered cycloalkyl or heterocyclic group containing 0-2 heteroatoms, or $R^2$ and $R^3$ are linked to form a 3-8 membered ring containing 0-2 heteroatoms;

Q is selected from a saturated cycloalkyl, a saturated heterocyclic group, or an aryl or a heteroaryl containing 0-4 heteroatoms substituted with 0-6 $R^q$, and said $R^q$ is each independently selected from the group consisting of H, D, OH, halogen, $C_{1-6}$ alkyl or a halogenated compound thereof. $C_{1-6}$ alkoxy or a halogenated compound thereof, or two substituents are linked together to form a 3-8 membered ring containing 0-2 heteroatoms; $W^2$ is selected from a bond, or 0-3 $R^4$-substituted alkenyl, alkynyl, $C_{1-6}$ alkyl, $C_{1-4}$ alkoxy, monocyclic alkyl, monocyclic heterocyclic group, aryl, heteroaryl, bridged cycloalkyl, bridged heterocyclic group, spirocycloalkyl, heterospirocyclic group, fused cycloalkyl, fused heterocyclic group;

wherein, $R^4$ is each independently selected from the group consisting of H, halogen, hydroxy, amino, mercapto, sulfone, sulfoxide, nitro, cyano, $CF_3$, $C_{1-4}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino, $C_{2-6}$ alkynyl, $C_{2-6}$ alkenyl;

or,

ARB is selected from the structure of formula (I-C):

(I-C)

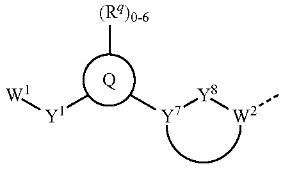

wherein, $W^1$ is selected from substituted or unsubstituted aryl or heteroaryl, and the substituent of $W^1$ is each independently selected from the group consisting of halogen, hydroxyl, amino, mercapto, sulfone, sulfoxide, nitro, cyano, $CF_3$, heterocyclic group, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino group, $C_{2-6}$ alkenyl or $C_{2-6}$ alkynyl;

$Y^1$ is selected from the group consisting of a bond, O, S, $NR^1$, $CR^2R^3$, C═O, C═S, SO, $SO_2$;

$Y^7$ is selected from N and $CR^2$; $Y^8$ is selected from the group consisting of a bond, O, S, $NR^1$, $CR^2R^3$, C═O, C═S, SO, $SO_2$;

$Y^7$ and $W^2$ are connected, and together with $Y^8$, form a 4-7 membered ring, and the ring is substituted with 0-4 deuteriums and halogens;

each of said $R^1$, $R^2$, and $R^3$ is independently selected from the group consisting of H, $C_{1-6}$alkyl or a halogenated compound thereof or a deuterated compound thereof, 3-8 membered cycloalkyl or heterocyclic group containing 0-2 heteroatoms, or $R^2$ and $R^3$ are linked to form a 3-8 membered ring containing 0-2 heteroatoms; Q is selected from a saturated cycloalkyl, a saturated heterocyclic group, or an aryl or a heteroaryl containing 0-4 heteroatoms substituted with 0-6 $R^q$, and said $R^q$ is each independently selected from the group consisting of H, D, OH, halogen, $C_{1-6}$ alkyl or a halogenated compound thereof, $C_{1-4}$ alkoxy or a halogenated compound thereof, or two substituents are linked together to form a 3-8 membered ring containing 0-2 heteroatoms;

$W^2$ is selected from a bond, or 0-3 $R^4$-substituted alkenyl, alkynyl, $C_{1-6}$ alkyl, $C_{1-6}$ alkoxy, monocyclic alkyl, monocyclic heterocyclic group, aryl, heteroaryl, bridged cycloalkyl, bridged heterocyclic group, spirocycloalkyl, heterospirocyclic group, fused cycloalkyl, fused heterocyclic group;

wherein, $R^4$ is each independently selected from the group consisting of H, halogen, hydroxy, amino, mercapto, sulfone, sulfoxide, nitro, cyano, $CF_3$, $C_{1-6}$ alkyl or a halogenated compound thereof or a deuterated compound thereof. $C_{3-6}$ cycloalkyl, $C_{1-6}$ alkoxy or a halogenated compound thereof or a deuterated compound thereof, $C_{1-6}$ alkylamino, $C_{2-4}$ alkynyl, $C_{2-6}$ alkenyl;

or,

ARB is selected from the structure of formula (I-D):

I-D

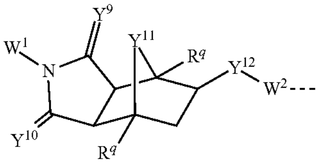

wherein, $W^1$ is selected from substituted or unsubstituted aryl or heteroaryl, and the substituent of $W^1$ is each independently selected from the group consisting of halogen, hydroxyl, amino, mercapto, sulfone, sulfoxide, nitro, cyano, $CF_3$, heterocyclic group, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino group, $C_{2-6}$ alkenyl or $C_{2-6}$ alkynyl;

each of $Y^9$, $Y^{10}$, and $Y^{11}$ is independently selected from the group consisting of CH, O, and S;

$Y^{12}$ is selected from a bond or CO, $CO_2$, O, S, $NR^{1e}$, $NR^{1c}O$, $NR^{1e}SO_2$; and said $R^{1e}$ is selected from H, $C_{1-4}$ alkyl or a halogenated compound thereof or a deuterated compound thereof, and 3-8 membered cycloalkyl or heterocyclic group containing 0-2 heteroatoms;

$R^q$ is each independently selected from the group consisting of H, D, OH, halogen, $C_{1-6}$ alkyl or a halogenated compound thereof, $C_{1-6}$ alkoxy or a halogenated compound thereof, or two $R^4$ are linked together to form a 3-8 membered ring containing 0-2 heteroatoms;

$W^1$ is selected from a bond, or 0-3 $R^4$-substituted alkenyl, alkynyl. $C_{1-6}$ alkyl, $C_{1-6}$ alkoxy, monocyclic alkyl, monocyclic heterocyclic group, aryl, heteroaryl, bridged cycloalkyl, bridged heterocyclic group, spirocycloalkyl, heterospirocyclic group, fused cycloalkyl, fused heterocyclic group;

$R^4$ is each independently selected from the group consisting of H, halogen, hydroxy, amino, mercapto, sulfone, sulfoxide, nitro, cyano, $CF_3$, $C_{1-6}$ alkyl or a halogenated compound thereof or a deuterated compound thereof. $C_{3-6}$ cycloalkyl, $C_{1-6}$ alkoxy or a halogenated compound thereof or a deuterated compound thereof, $C_{1-6}$ alkylamino, $C_{2-6}$ alkynyl, $C_2$. 6 alkenyl.

Further, the structure

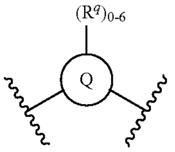

in said formula (I-A), formula (I-B) or formula (I-C) is as shown in the following formula (II-A), formula (IV-B), formula (IV-C), formula (IV-D), formula (IV-E), formula (IV-F), formula (IV-G) or formula (IV-H):

II-A

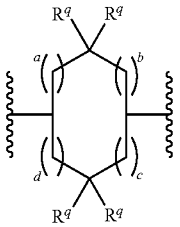

IV-B

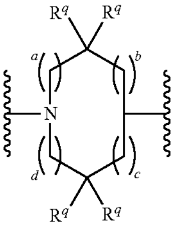

IV-C

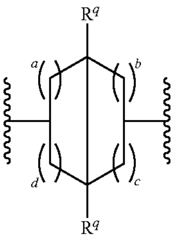

-continued

IV-D

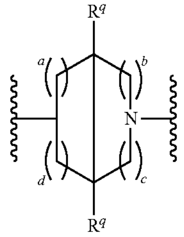

IV-E

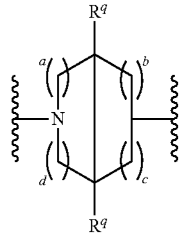

IV-F

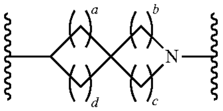

IV-G

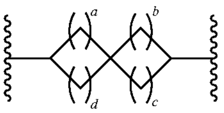

IV-H

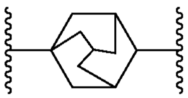

wherein, $R^q$ is each independently selected from the group consisting of H, OH, halogen. $C_{1-6}$ alkyl or a halogenated compound thereof, $C_{1-6}$ alkoxy or a halogenated compound thereof, or two $R^q$ are linked together to form a 3-8 membered ring containing 0-2 heteroatoms;

each of a, b, c, and d is independently selected from an integer of 0 to 3.

Further, the structure

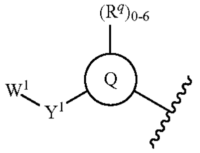

in said formulas (I-A), (I-B) or (I-C) is as shown in the following formula (III-A) or formula (III-B) or formula (Ill-C) or formula (III-D):

III-A

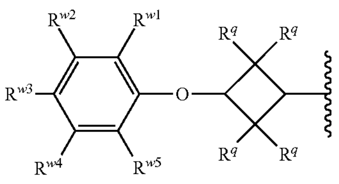

-continued

III-B

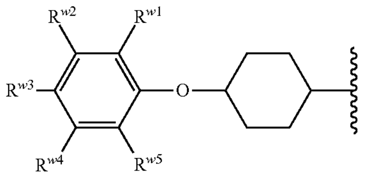

III-C

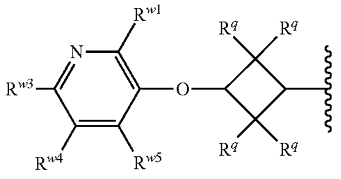

III-D

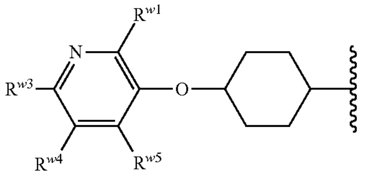

or, the structure

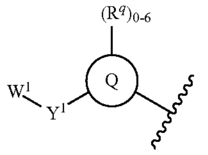

in said formula (I-A), formula (I-B) or formula (I-C) is as shown in the following formula (III-E), formula (III-F), formula (III-G), formula (III-H), formula (III-I), formula (III-J), formula (III-K), formula (III-L), formula (III-M) or formula (III-N):

III-E

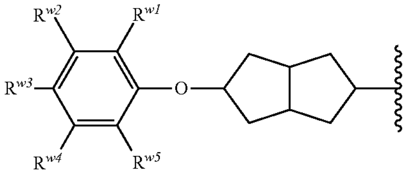

III-F

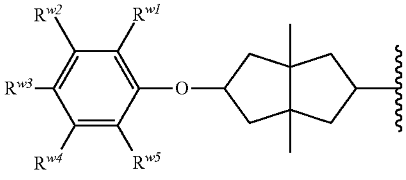

III-G

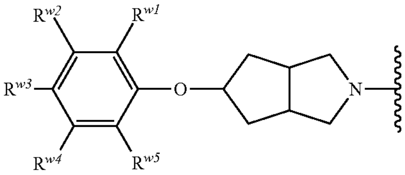

-continued

III-H

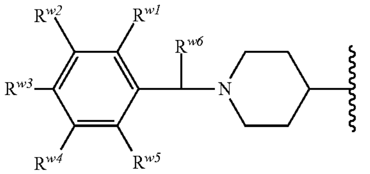

III-I

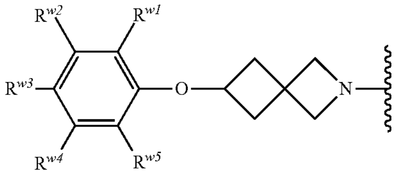

III-J

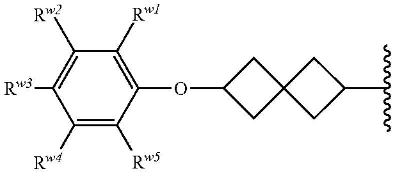

III-K

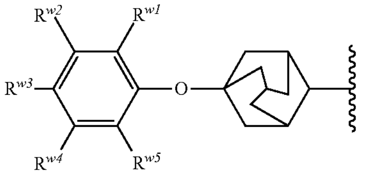

III-L

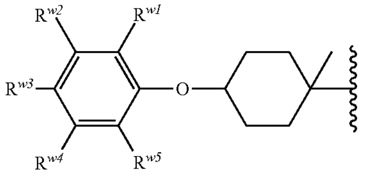

III-M

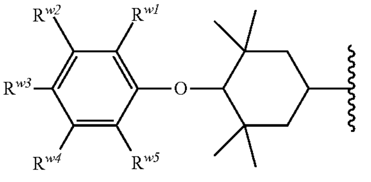

III-N

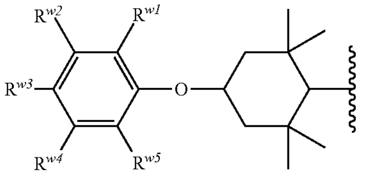

wherein, each of $R^{w1}$, $R^{w2}$, $R^{w3}$, $R^{w4}$, and $R^{w5}$ is independently selected from the group consisting of halogen, hydroxyl, amino, mercapto, sulfone, sulfoxide, nitro, cyano, $CF_3$, heterocyclic group, $C_{1-6}$ alkyl or a halogenated compound thereof or a deuterated compound thereof. $C_{3-6}$ cycloalkyl, $C_{1-6}$ alkoxy or a halogenated compound thereof or a deuterated compound thereof, $C_{1-6}$ alkylamino, $C_{2-6}$ alkenyl or $C_{2-6}$ alkynyl, said halogen is preferably chlorine or bromine, said $C_{1-6}$ alkyl is preferably methyl, and said $C_{1-6}$ alkoxy is preferably methoxy or ethoxy;

$R^q$ is each independently selected from the group consisting of H, OH, halogen, $C_{1-6}$ alkyl or a halogenated compound thereof, $C_{1-6}$ alkoxy or a halogenated compound thereof, or two $R^q$ are linked together to form a 3-8 membered ring containing 0-2 heteroatoms.
Further, the structure
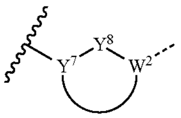
in said formula (I-C) is selected from the following structures:
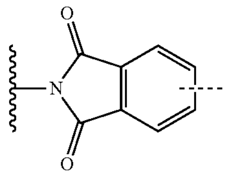
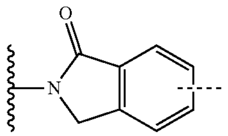
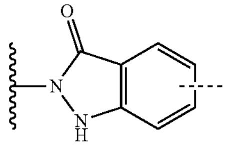
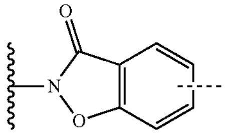
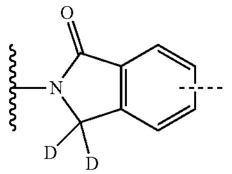
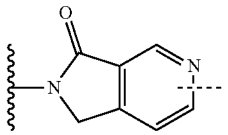
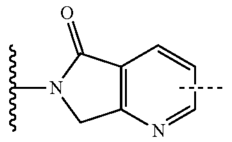
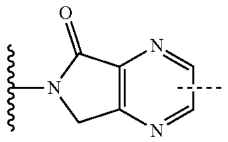
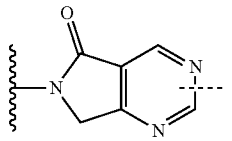
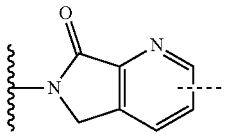
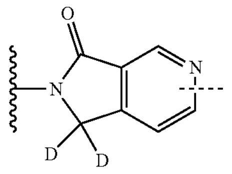
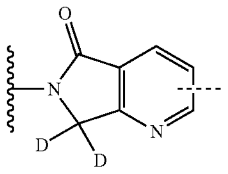
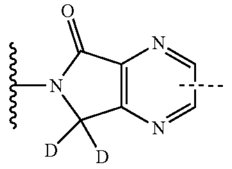
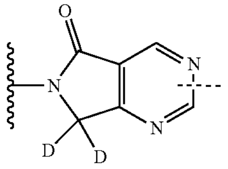
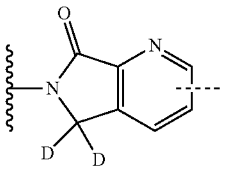
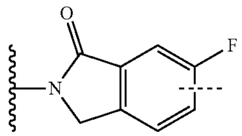
-continued
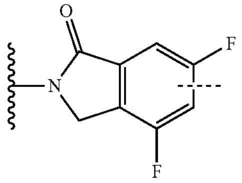
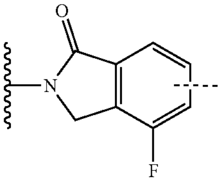
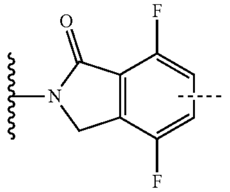
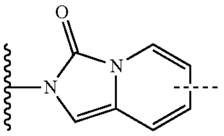
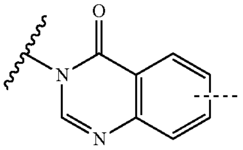
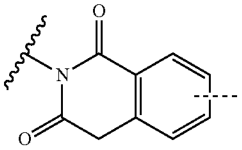
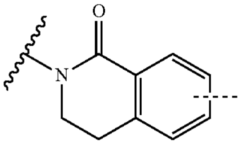
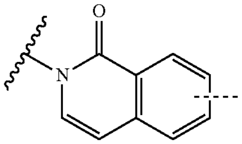
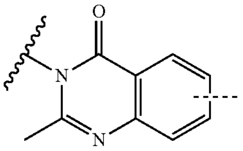
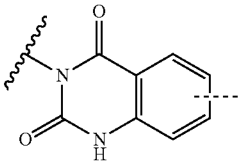
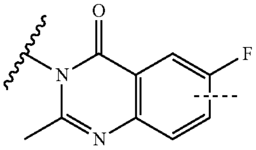
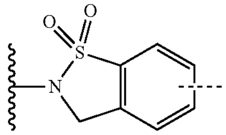
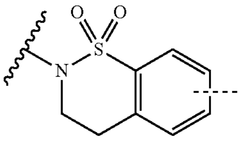
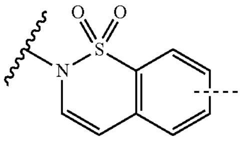
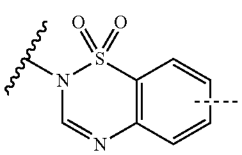
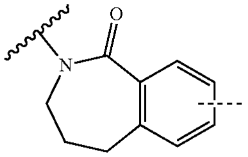
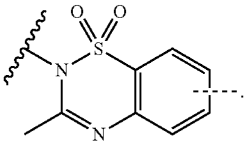

Further, the structure of said formula (I-D) is as shown in the following formula (V-D):
V-D
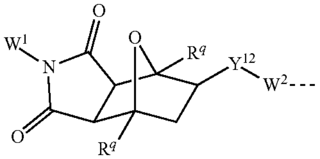
wherein, $W^1$, $W^2$, $Y^{12}$, and $R^q$ are as described in formula (I-D) mentioned above.
Further, said ARB is selected from the following structures:
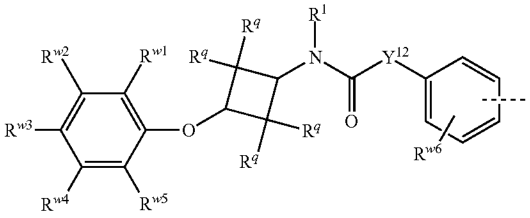
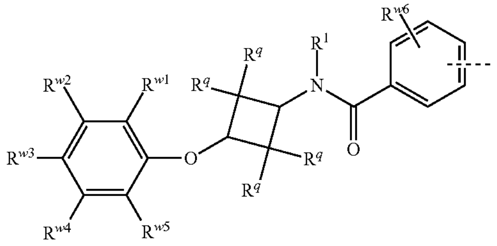
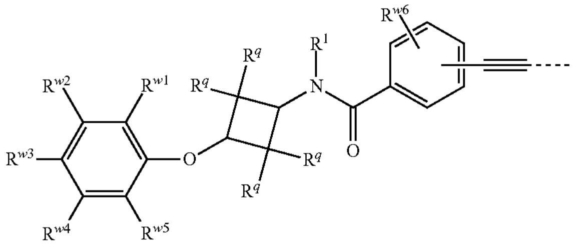
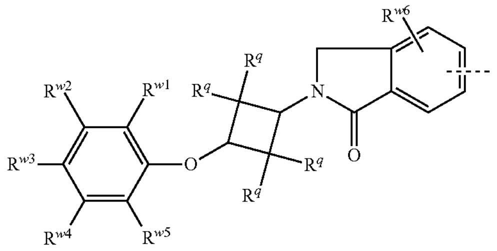
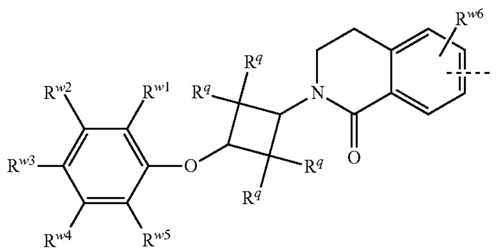
-continued
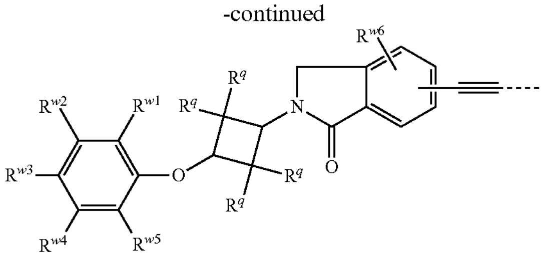
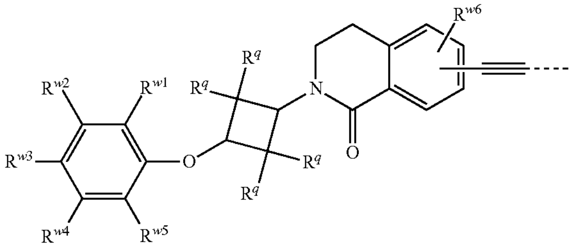
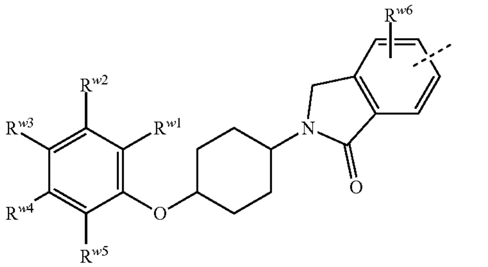
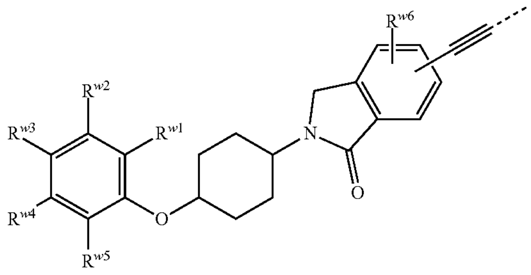
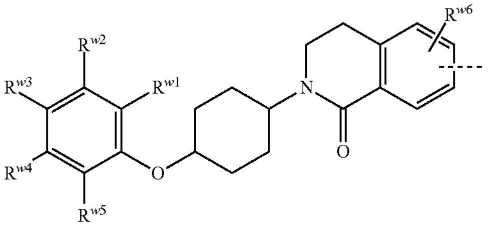
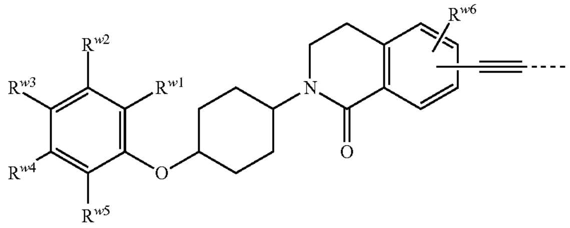
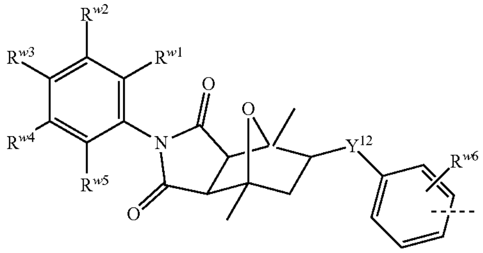

-continued
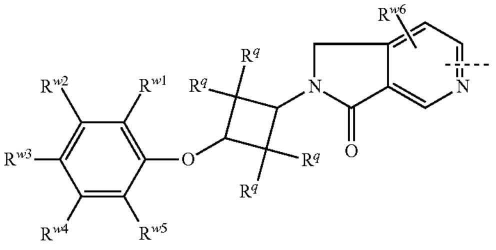
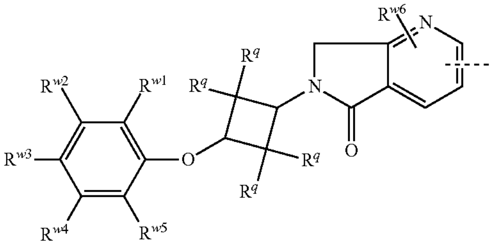
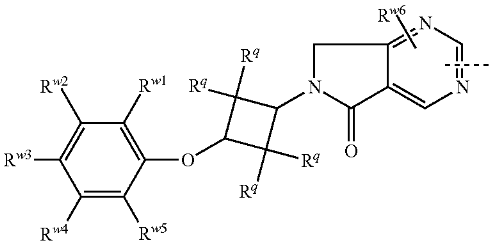
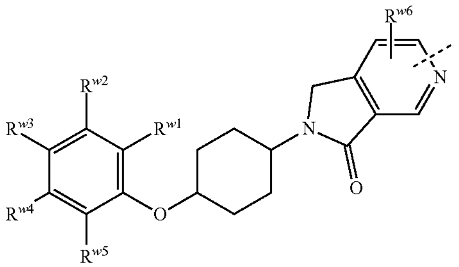
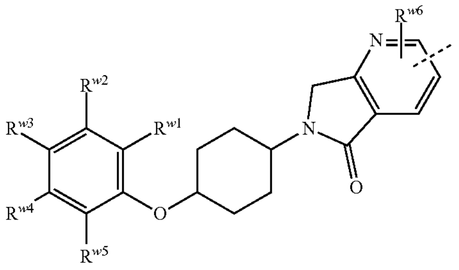
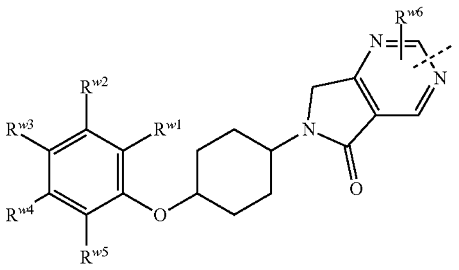
-continued
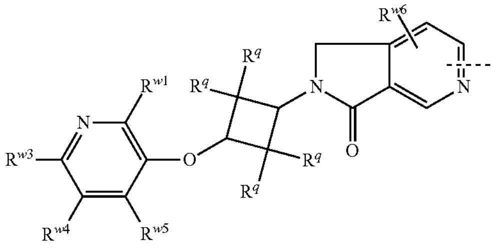
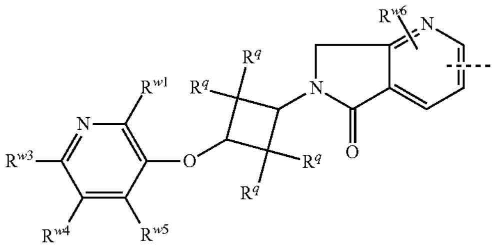
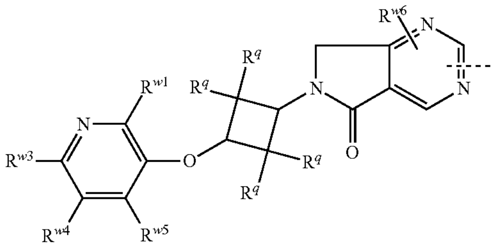
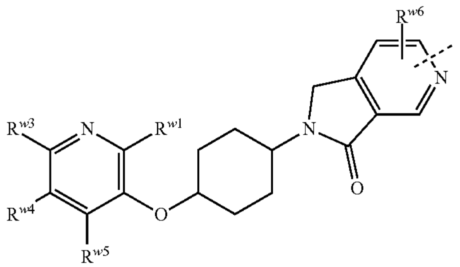
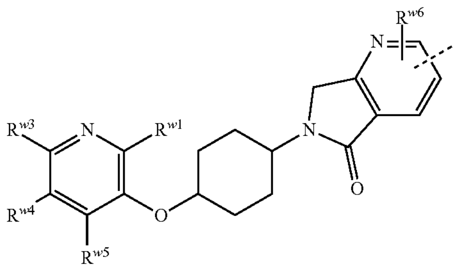
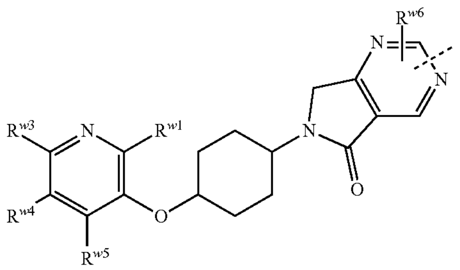

-continued
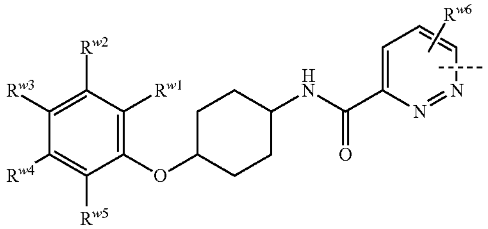
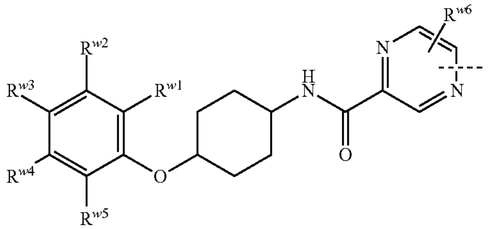
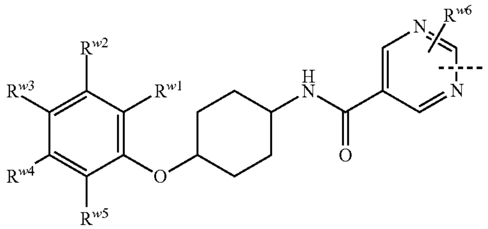
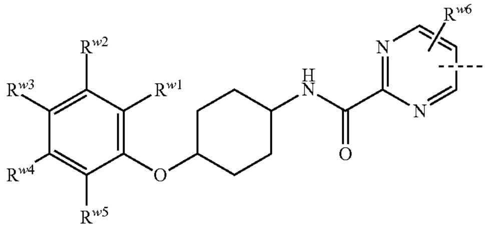
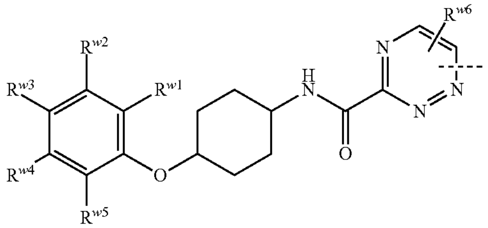
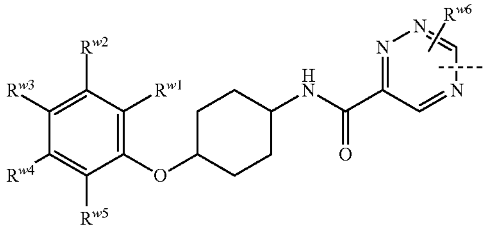
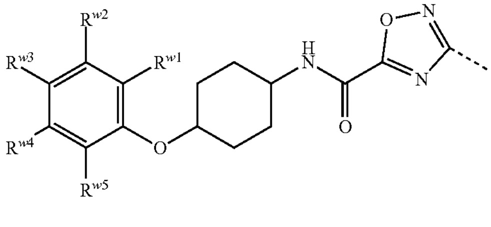
-continued
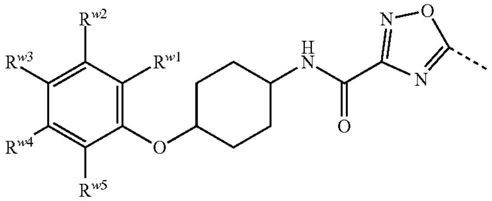
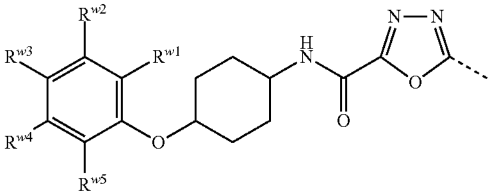
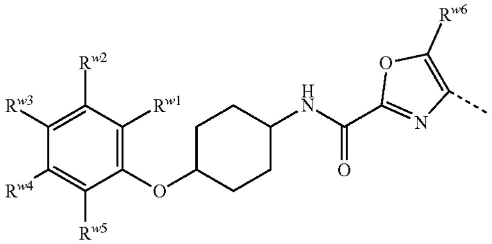
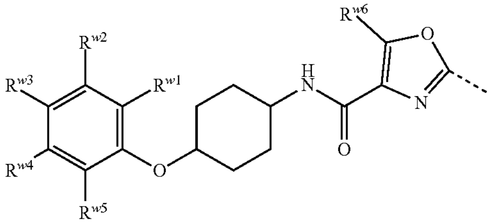
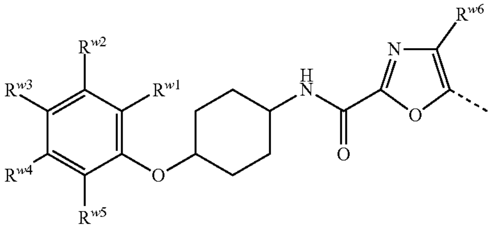
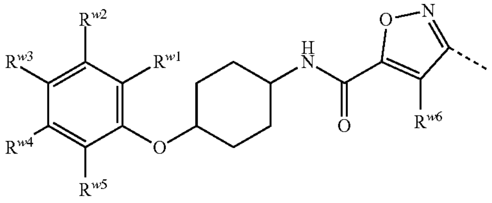
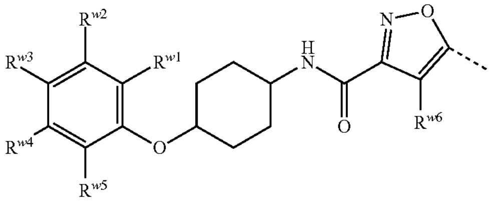
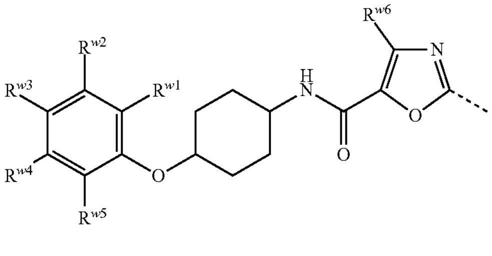

-continued
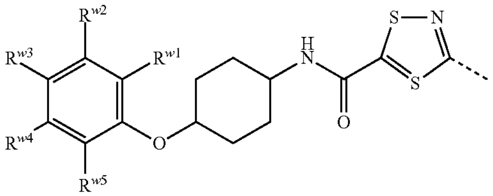
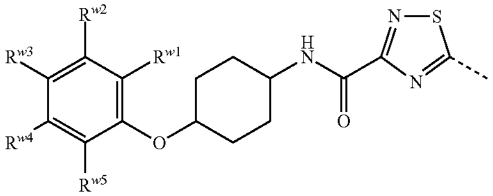
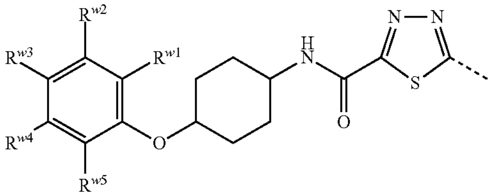
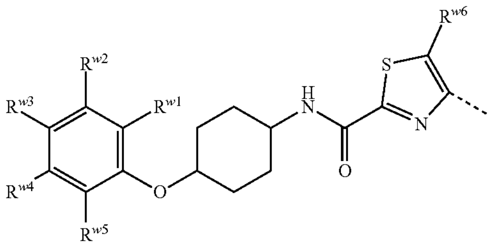
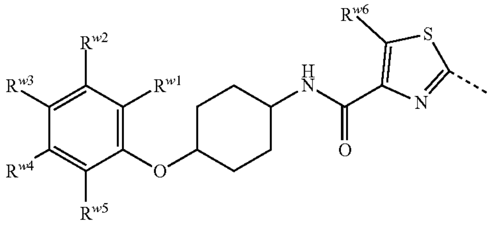
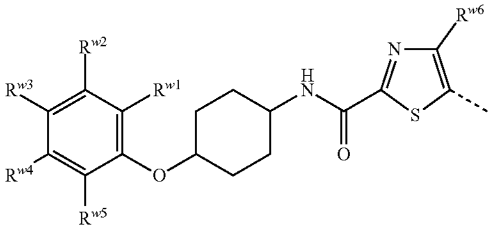
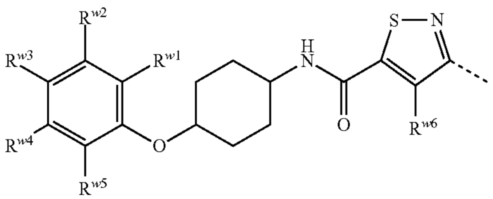
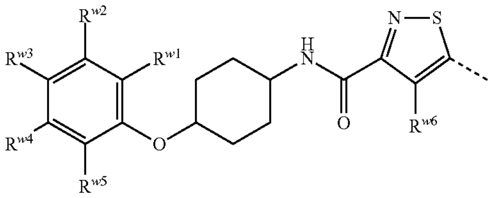
-continued
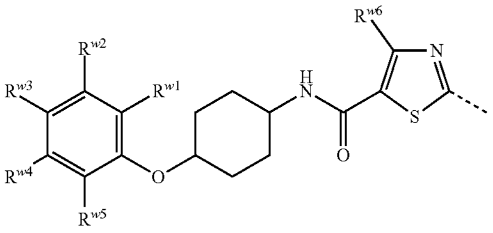
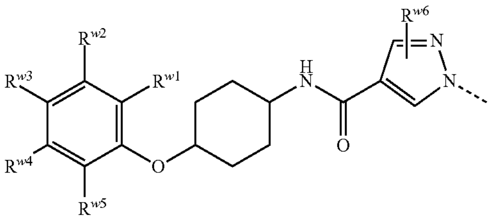
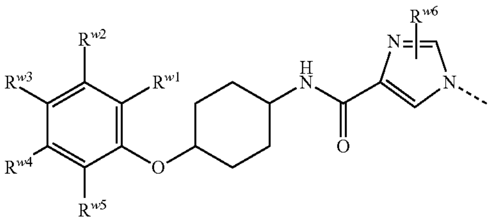
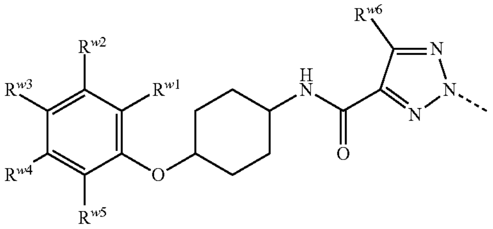
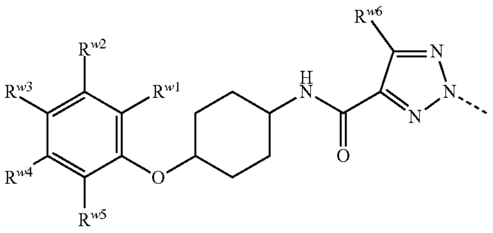
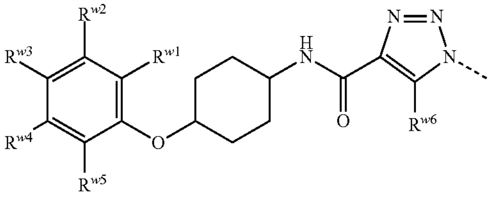
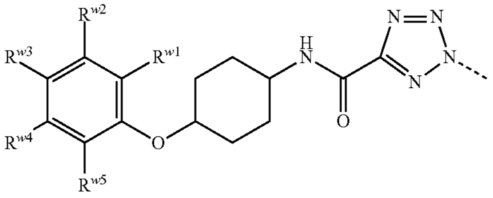

-continued
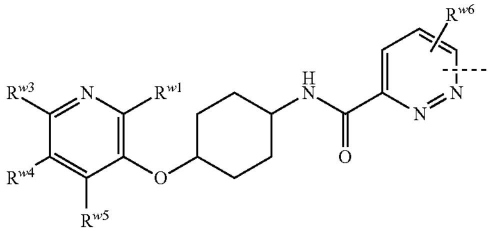
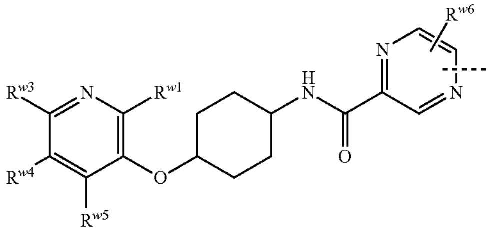
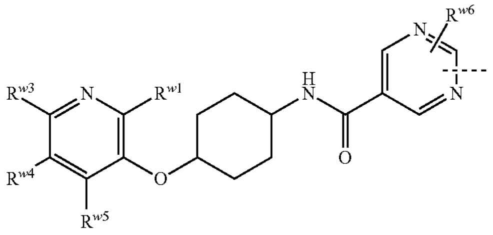
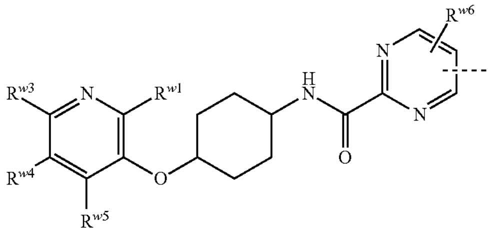
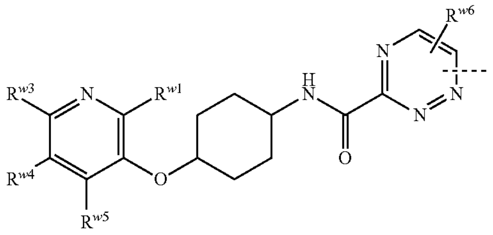
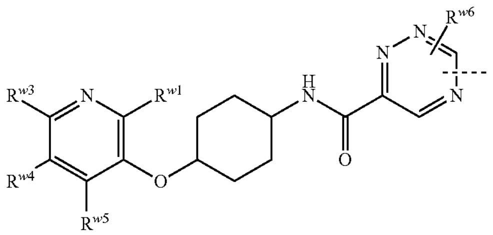
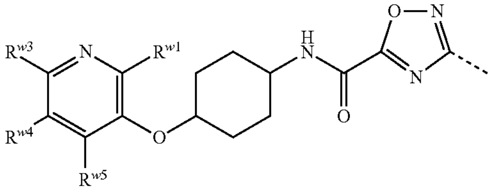
-continued
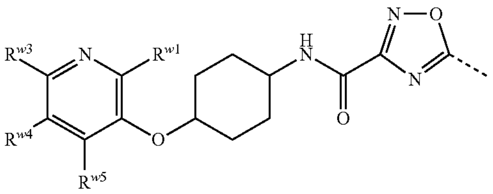
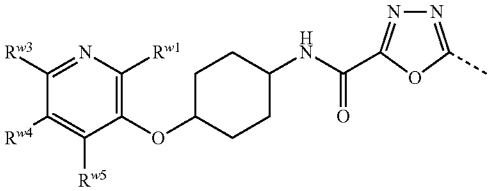
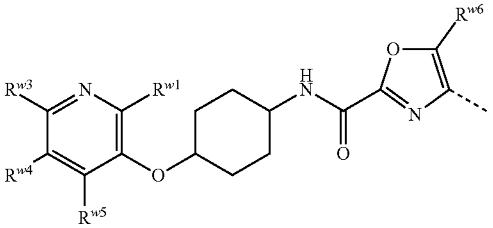
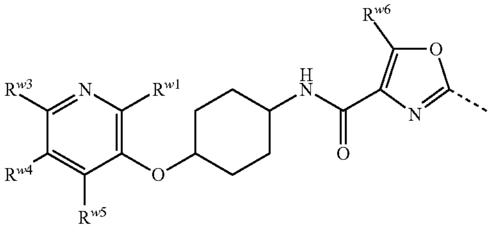
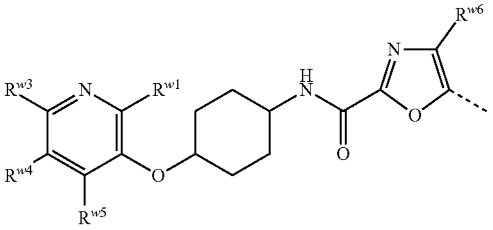
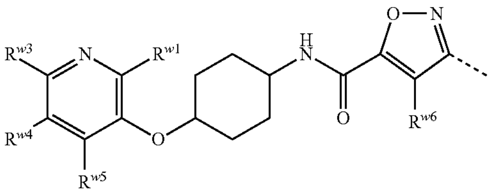
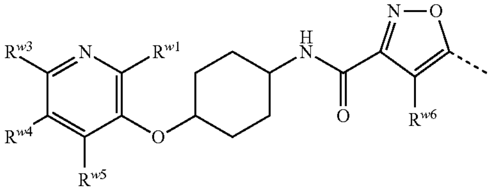
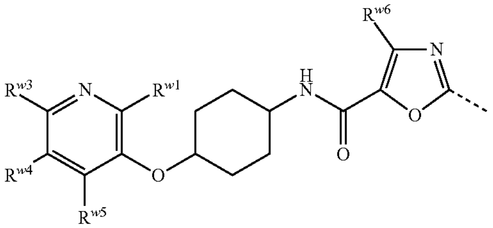

-continued

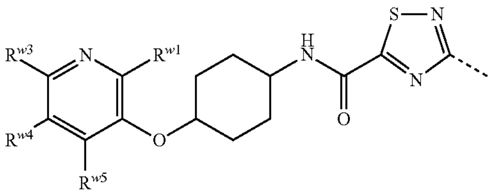

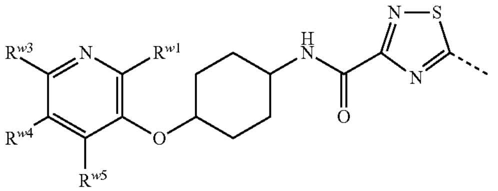

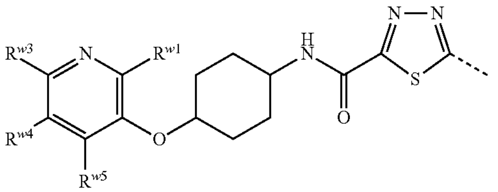

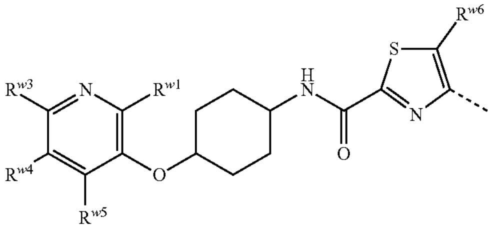

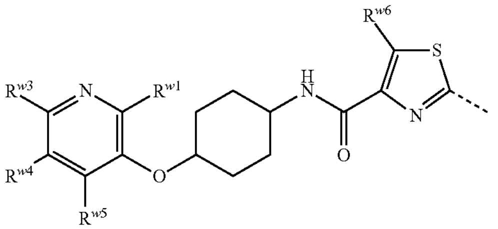

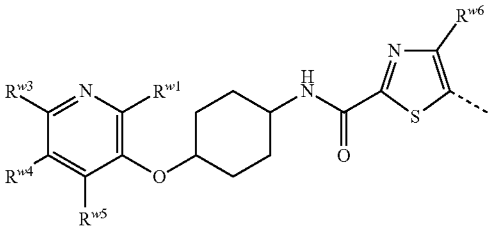

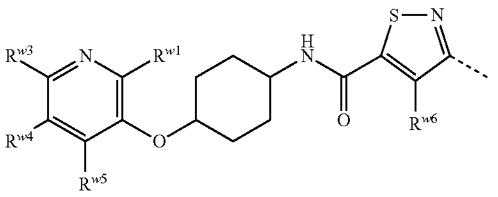

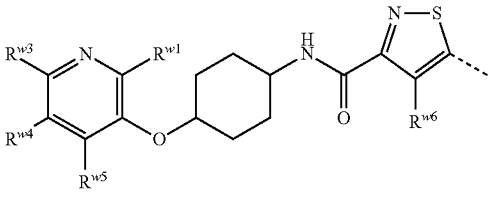

-continued

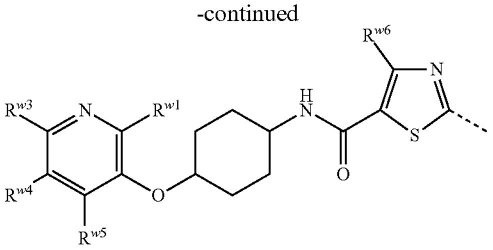

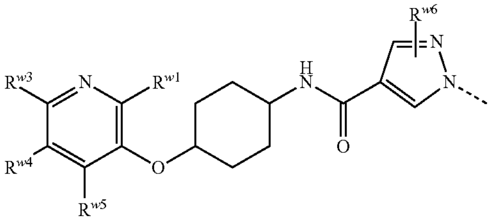

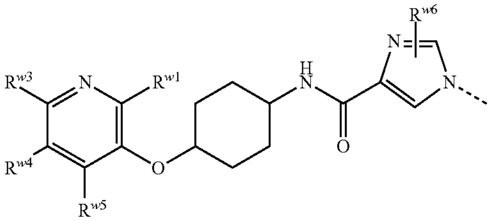

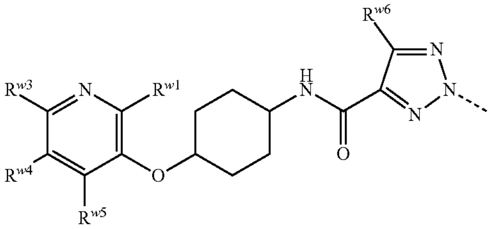

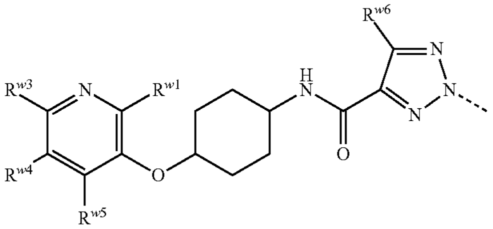

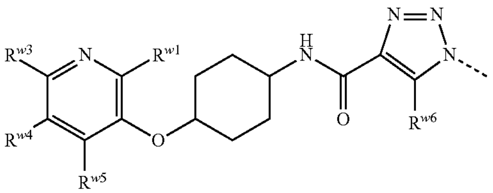

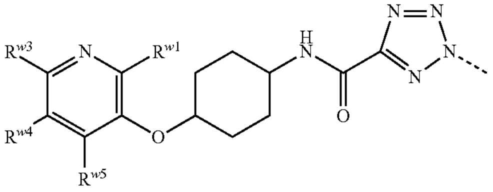

wherein, each of $R^{w1}$, $R^{w2}$, $R^{w3}$, $R^{w4}$, and $R^{w5}$ is independently selected from the group consisting of halogen, hydroxyl, amino, mercapto, sulfone, sulfoxide, nitro, cyano, heterocyclic group, $CF_3$, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino, $C_{2-6}$ alkenyl or $C_{2-6}$ alkynyl; said halogen is preferably chlorine or bromine, said $C_{1-6}$ alkyl is preferably methyl, and said $C_{1-6}$ alkoxy is preferably methoxy or ethoxy;

$R^{w6}$ is selected from the group consisting of H, halogen, hydroxyl, amino, mercapto, sulfone, sulfoxide, nitro, cyano, $CF_3$, $C_{1-6}$ alkyl or a halogenated compound thereof or a deuterated compound thereof, $C_{3-6}$ cycloalkyl, $C_{1-6}$ alkoxy or a halogenated compound thereof or a deuterated compound thereof, $C_{1-6}$ alkylamino, $C_{2-6}$ alkenyl or $C_{2-6}$ alkynyl;

$R^q$ is each independently selected from the group consisting of H, OH, halogen, $C_{1-6}$ alkyl or a halogenated compound thereof, $C_{1-6}$ alkoxy or a halogenated compound thereof, or two $R^q$ are linked together to form a 3-8 membered ring containing 0-2 heteroatoms.

$Y^{12}$ is selected from a bond or CO, $CO_2$, O, S, $NR^{1e}$, $NR^{1e}CO$, $NR^{1e}SO_2$; said $R^{1e}$ is selected from H, $C_{1-6}$ alkyl or a halogenated compound thereof or a deuterated compound thereof.

Further, said ARB is selected from the structures of the following formulas:

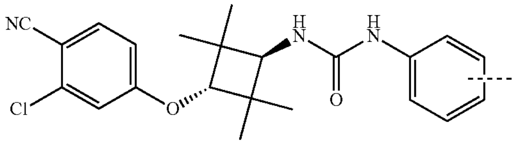

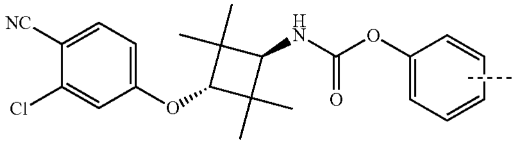

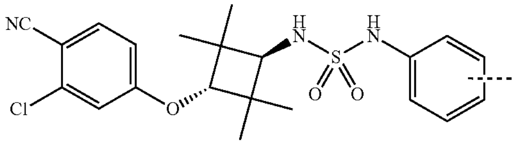

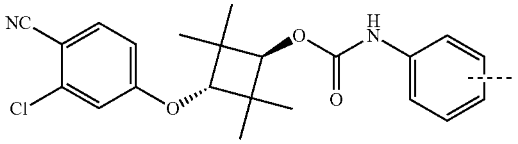

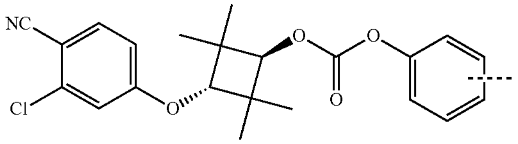

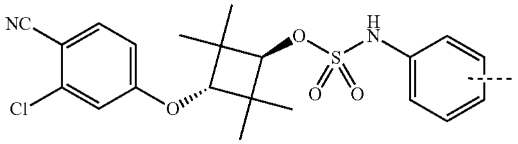

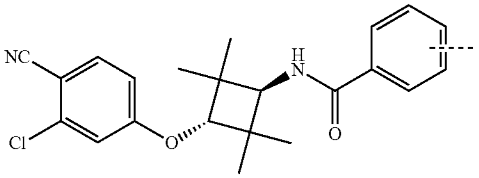

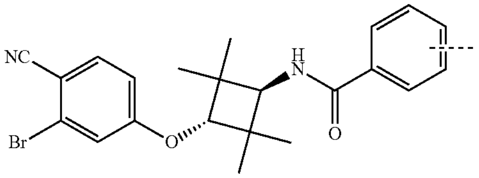

-continued

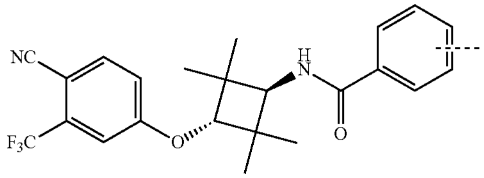

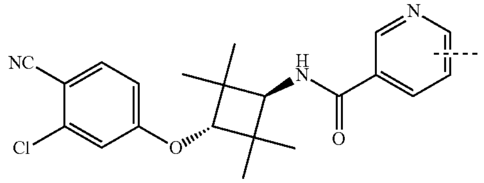

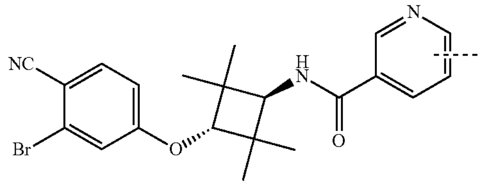

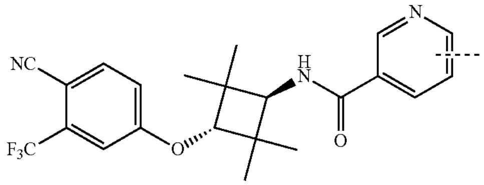

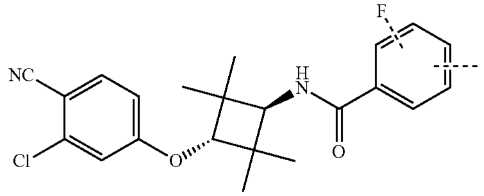

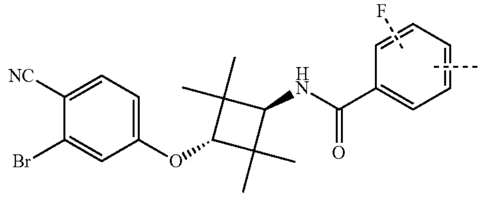

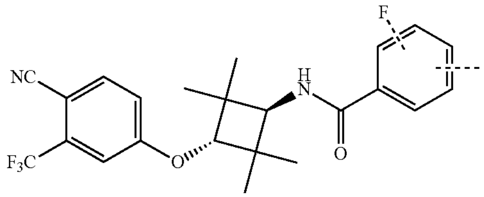

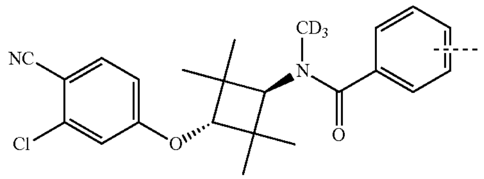

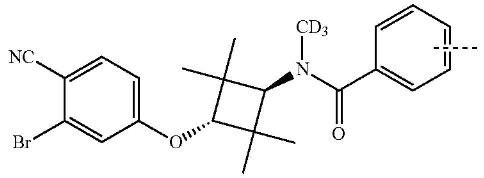

-continued
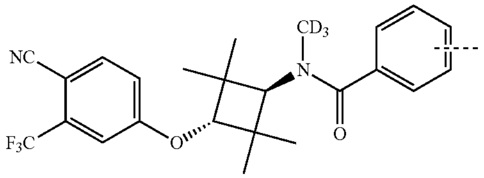
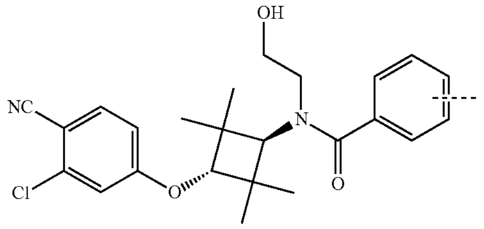
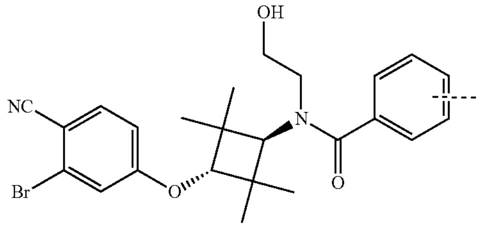
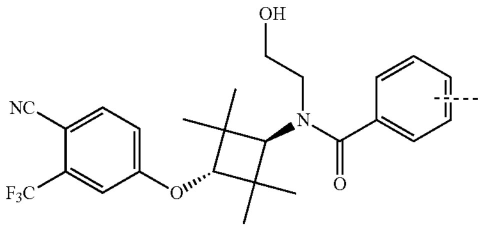
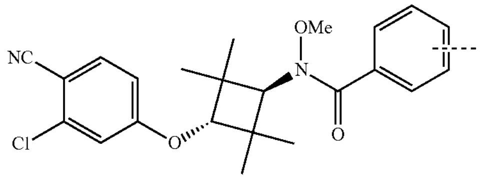
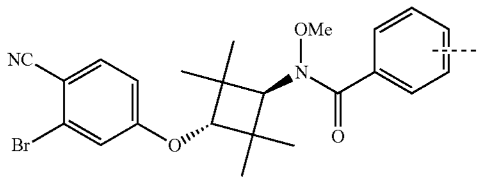
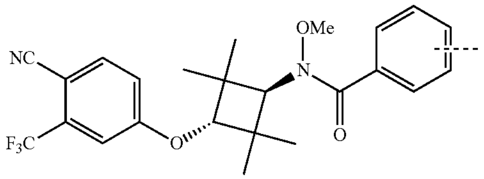
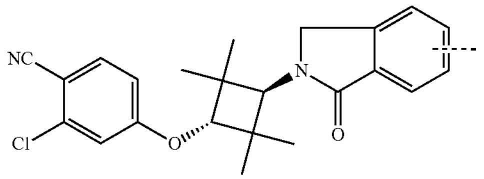
-continued
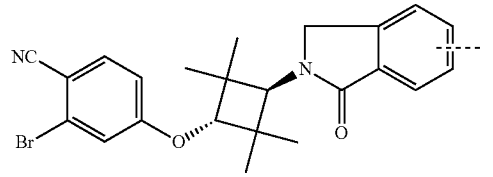
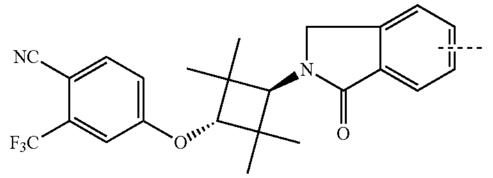
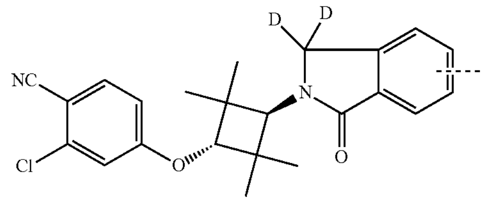
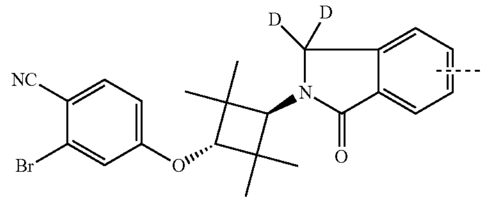
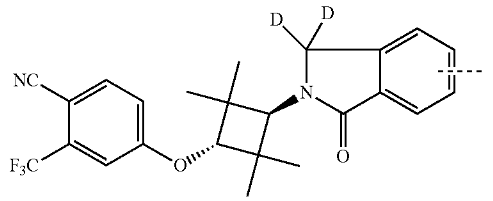
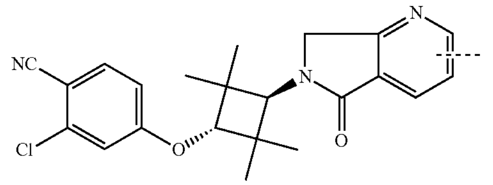
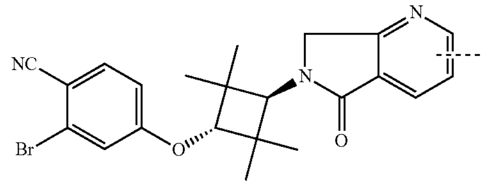
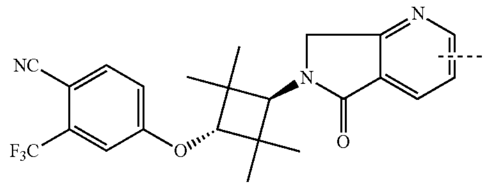
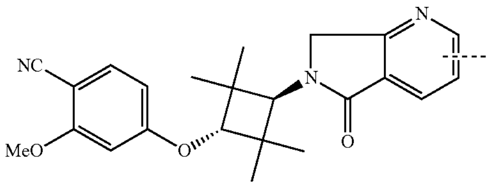

-continued
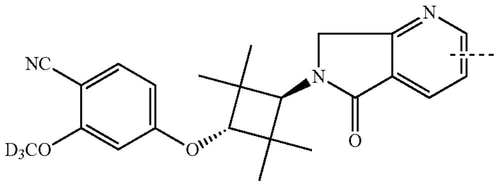
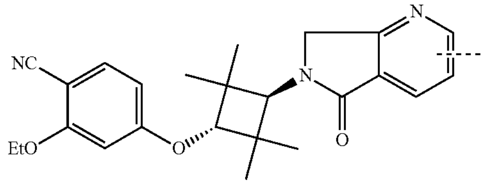
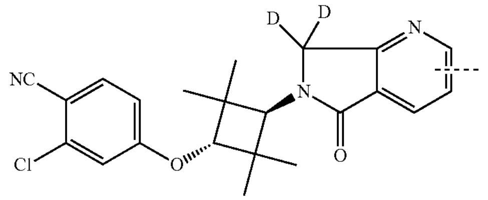
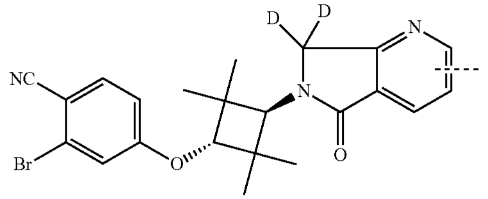
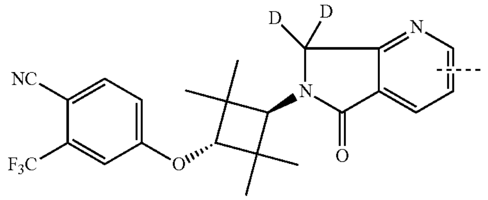
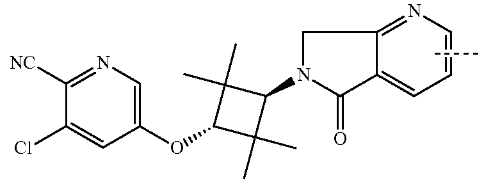
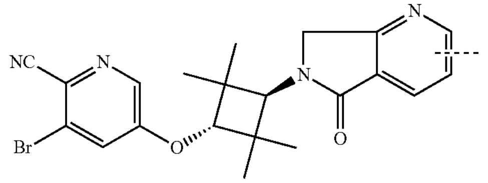
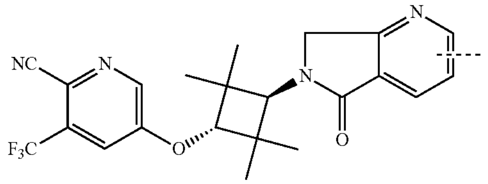
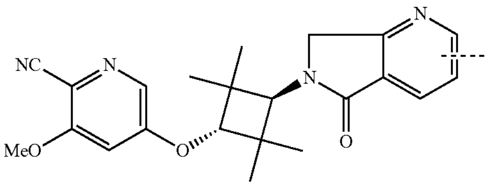
-continued
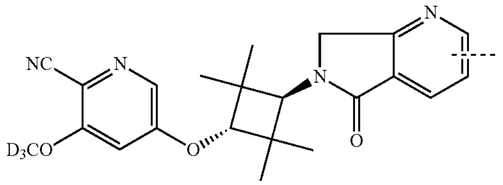
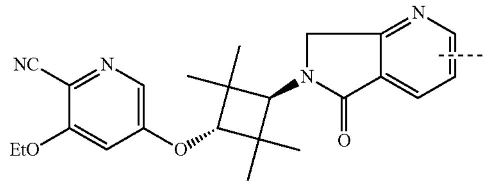
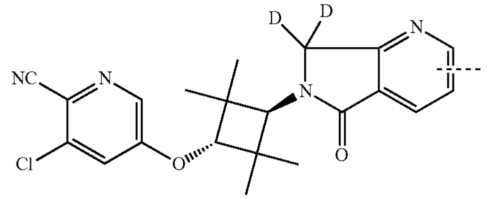
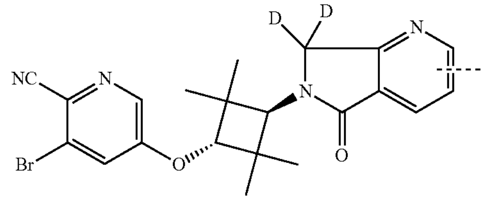
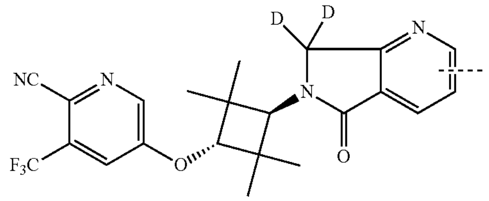
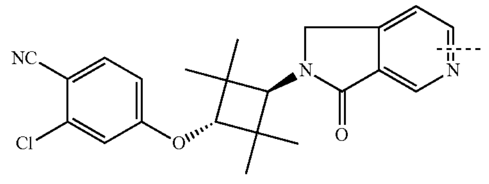
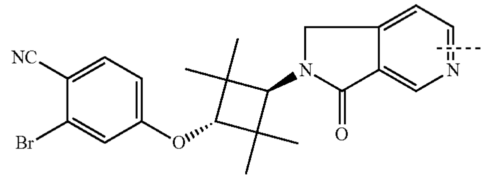
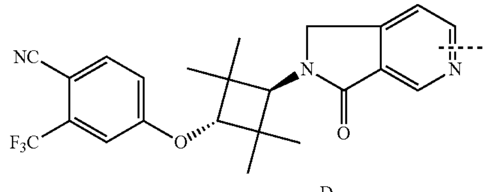
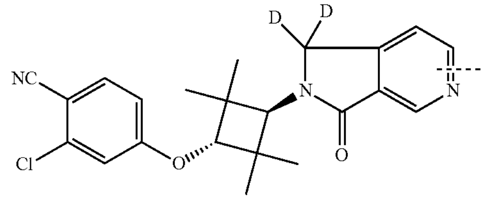

-continued
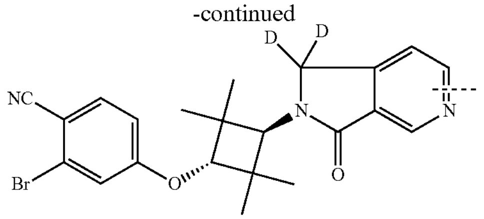
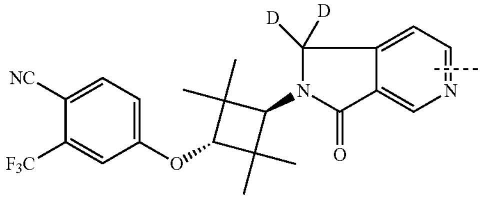
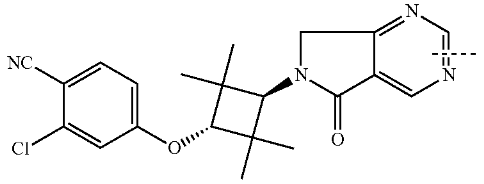
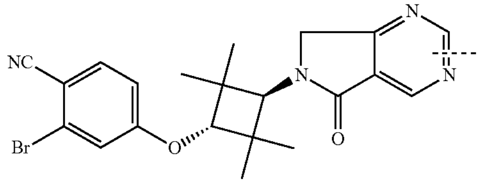
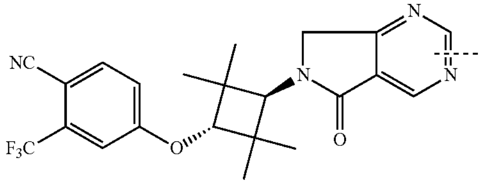
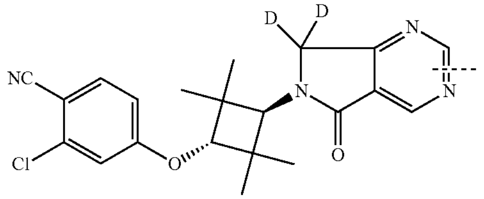
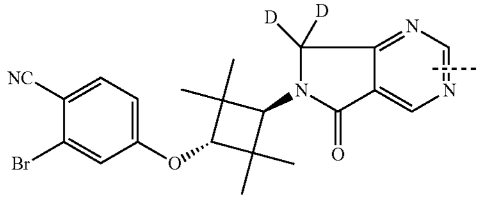
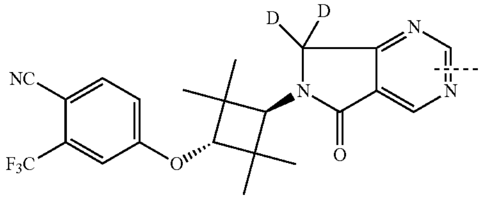
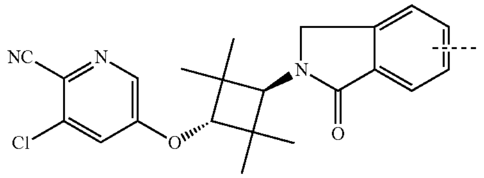
-continued
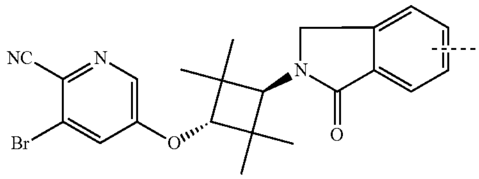
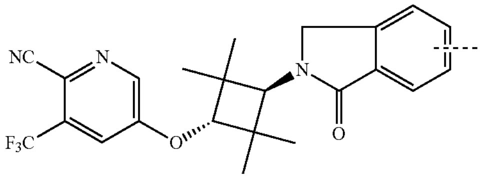
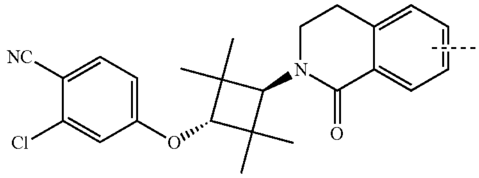
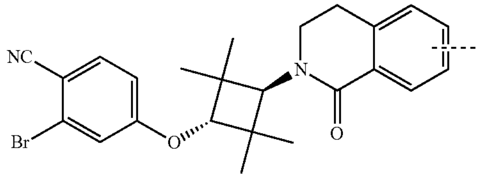
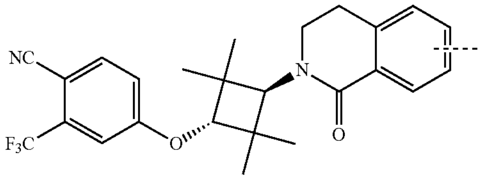
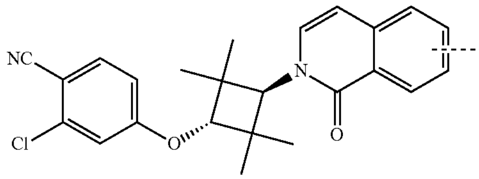
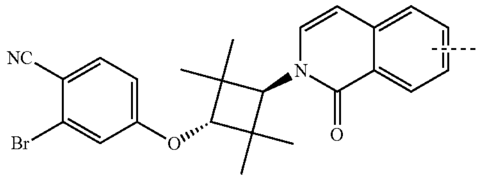
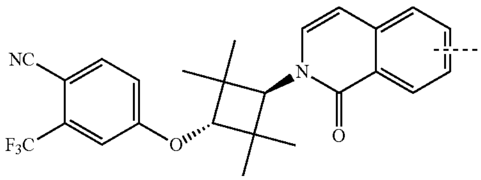
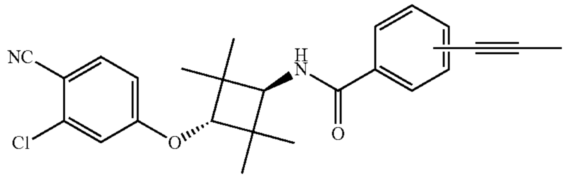

-continued
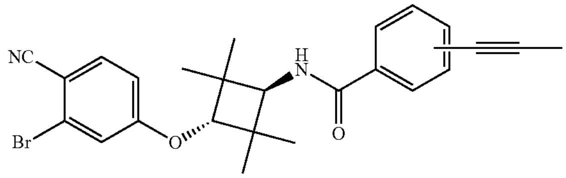
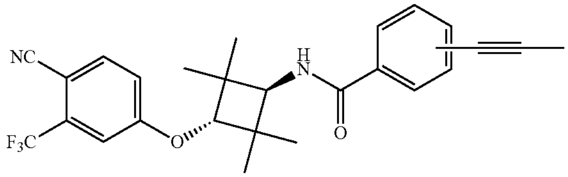
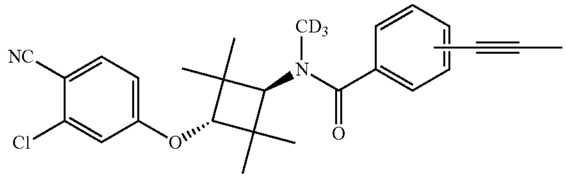
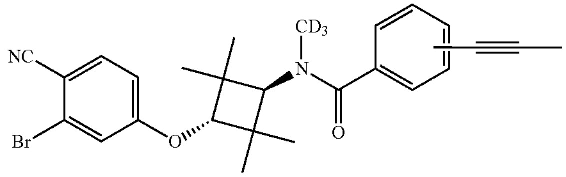
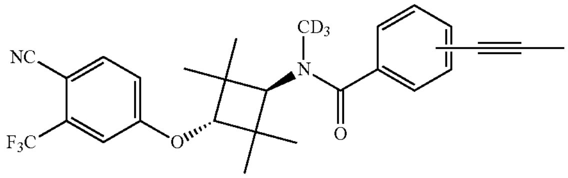
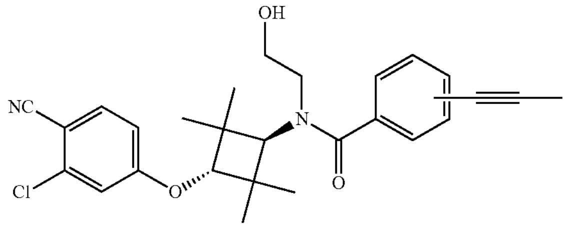
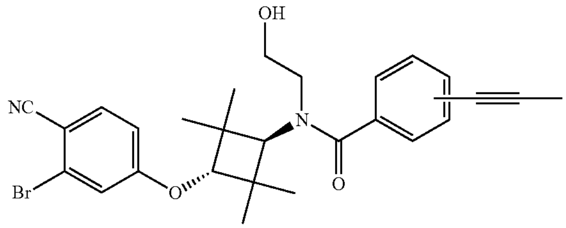
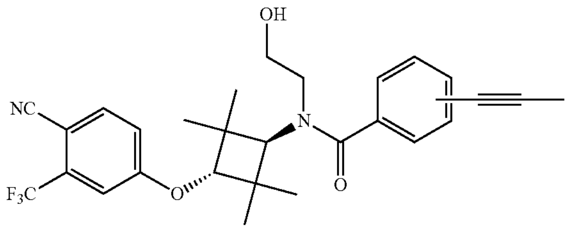
-continued
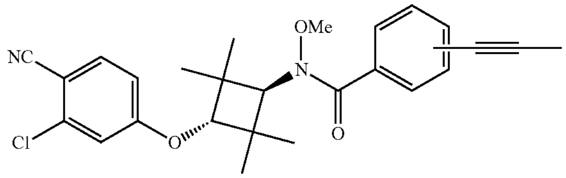
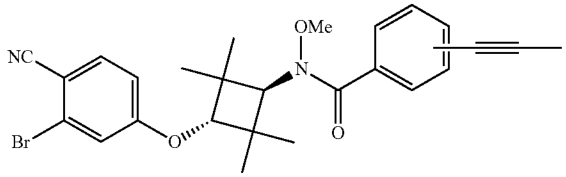
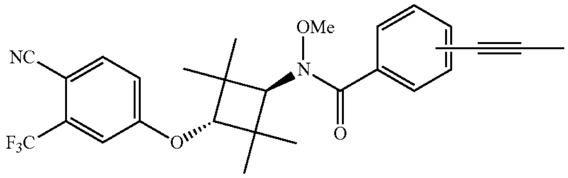
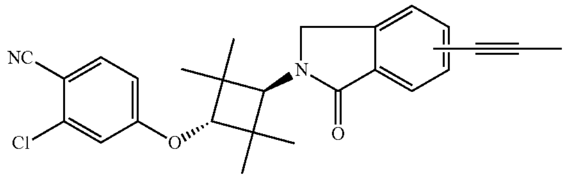
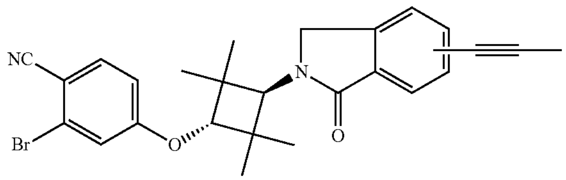
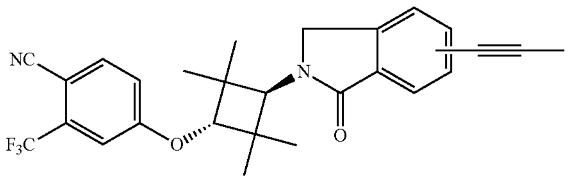
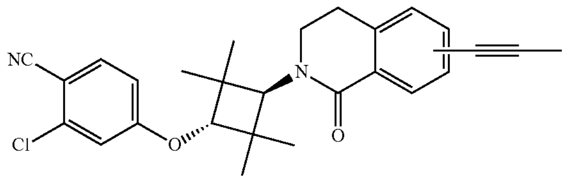
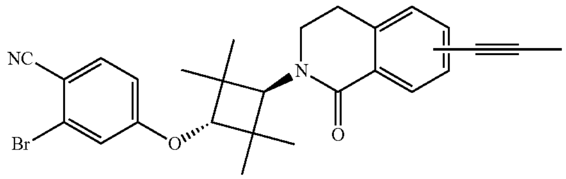
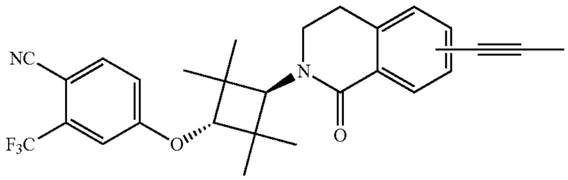

-continued
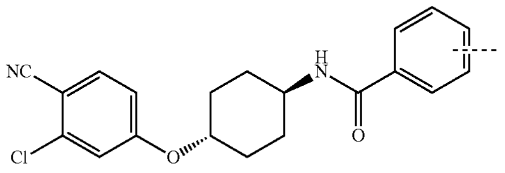
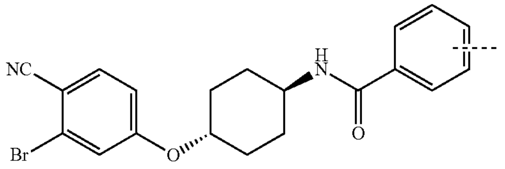
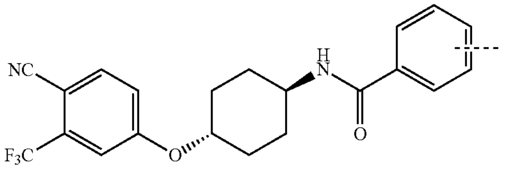
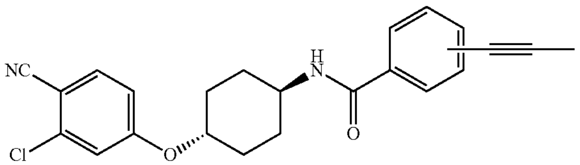
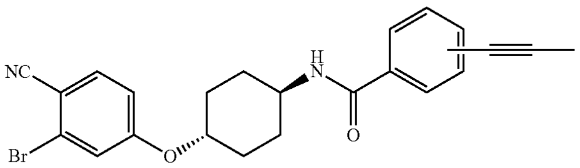
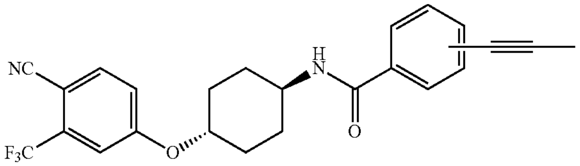
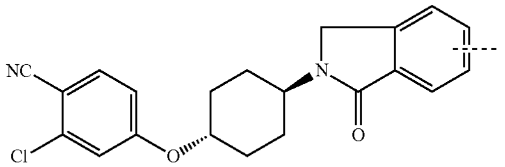
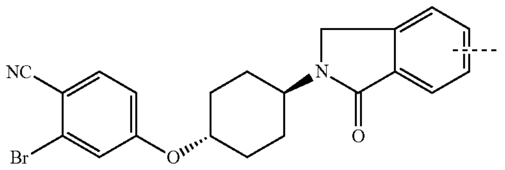
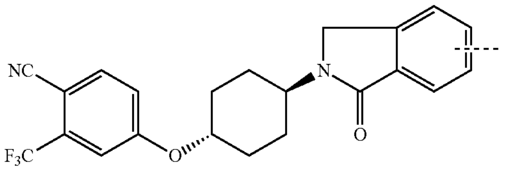
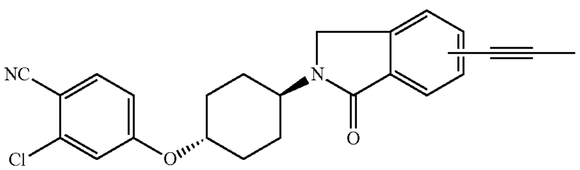
-continued
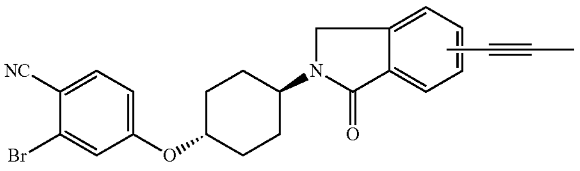
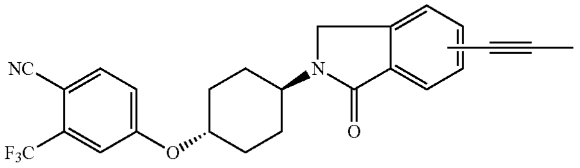
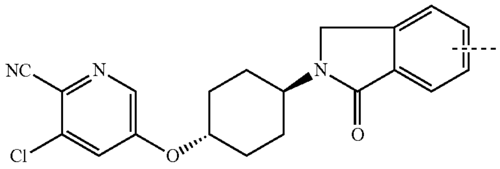
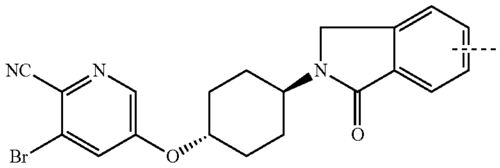
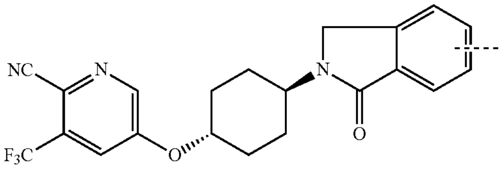
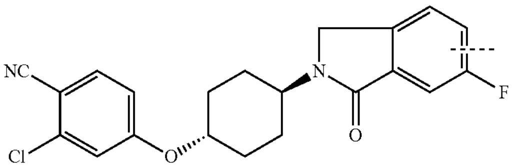
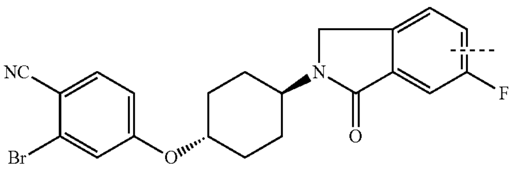
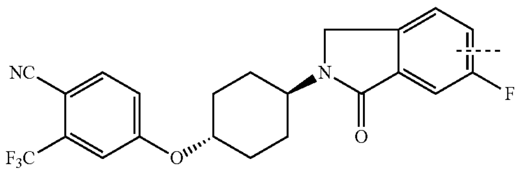
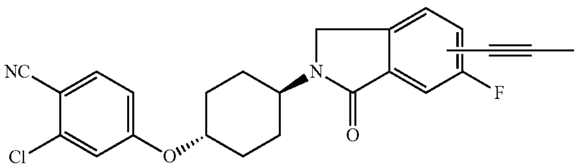
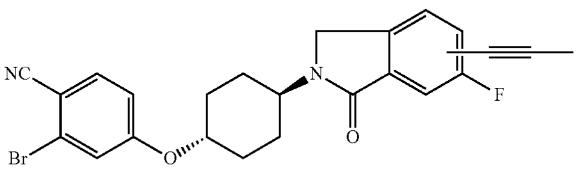

-continued
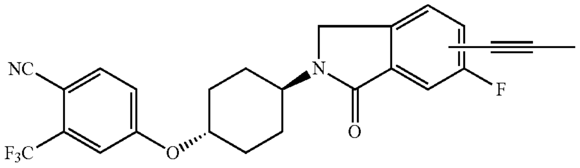
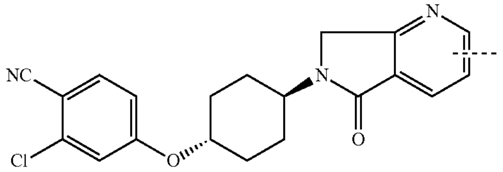
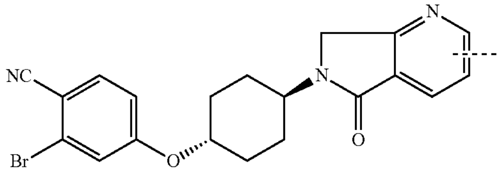
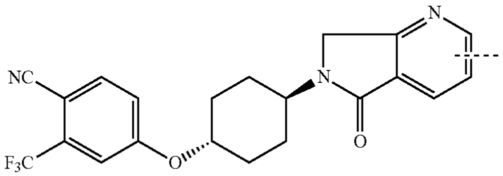
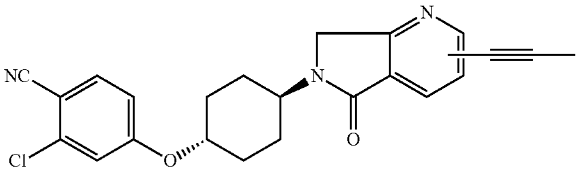
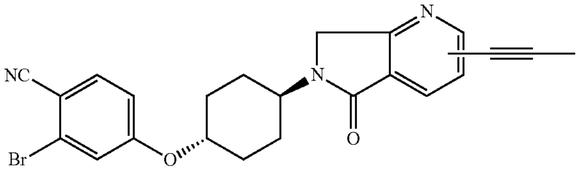
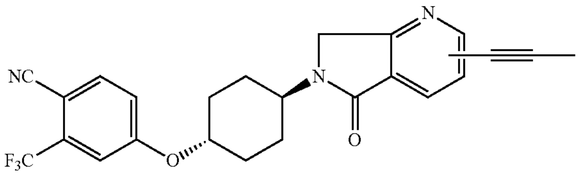
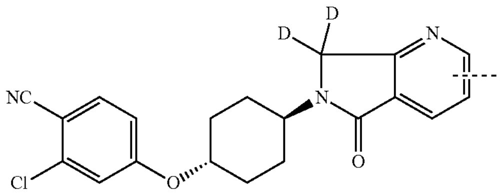
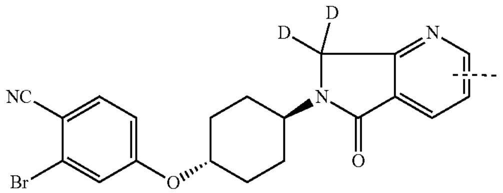
-continued
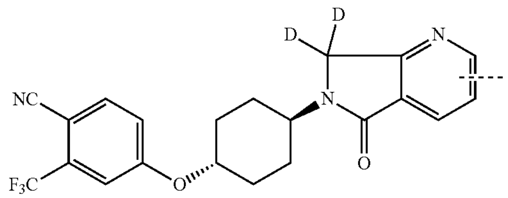
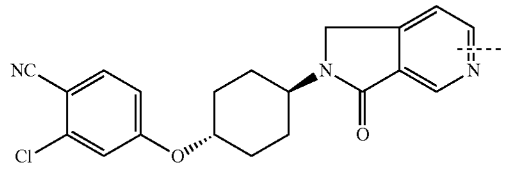
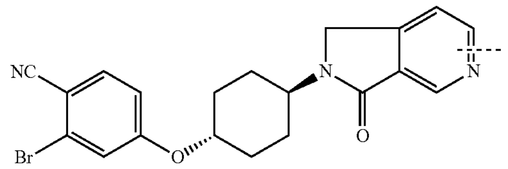
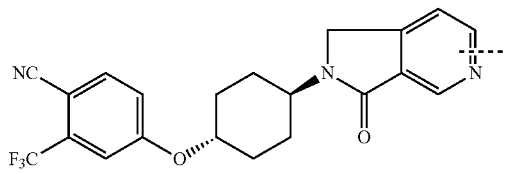
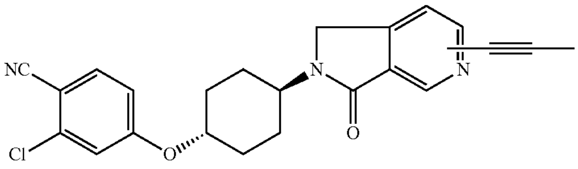
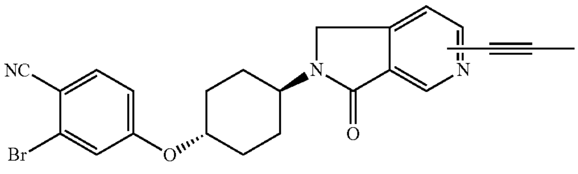
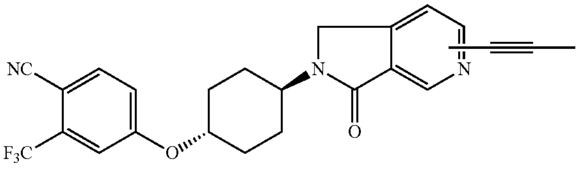
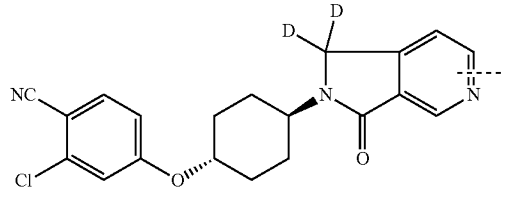
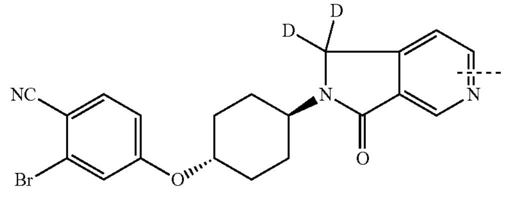

-continued
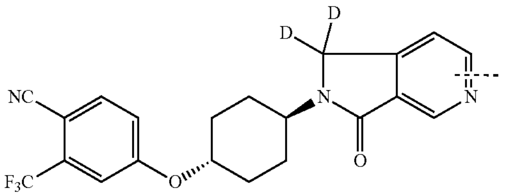
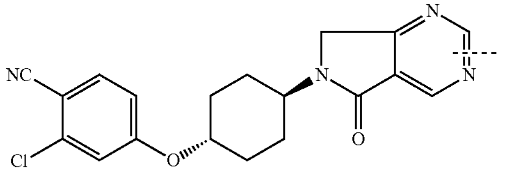
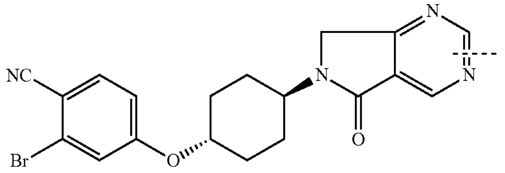
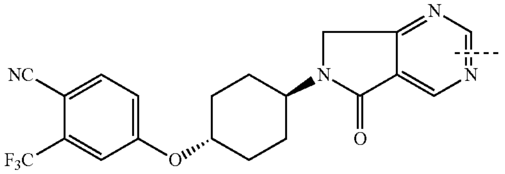
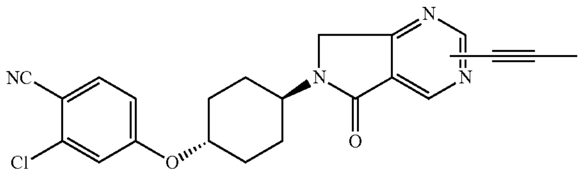
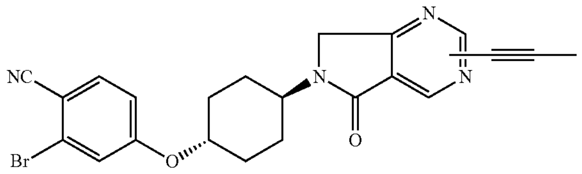
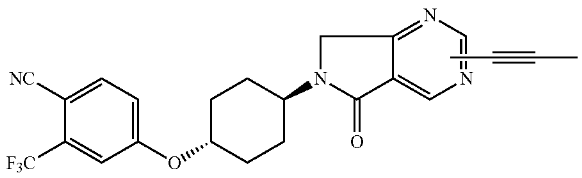
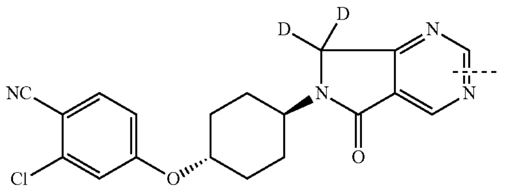
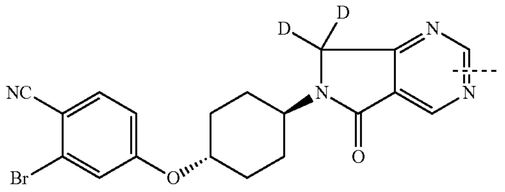
-continued
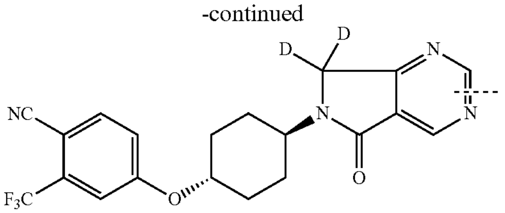
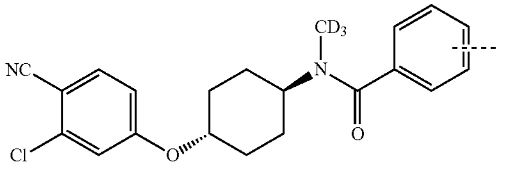
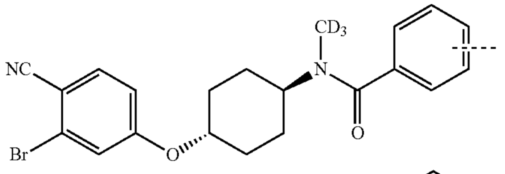
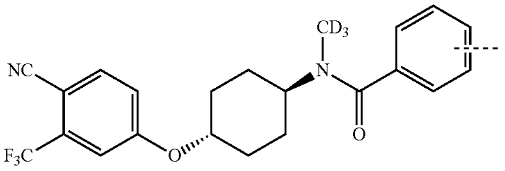
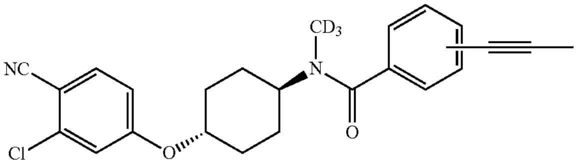
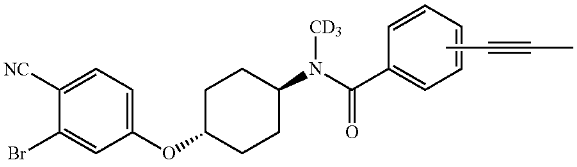
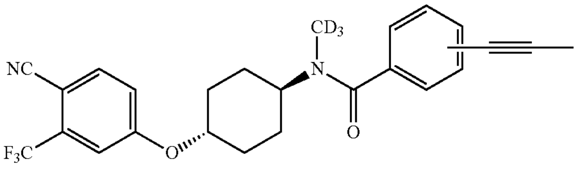
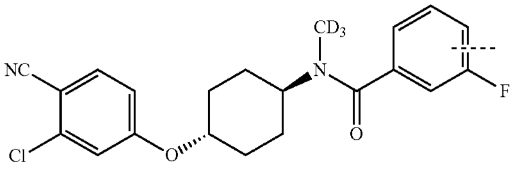
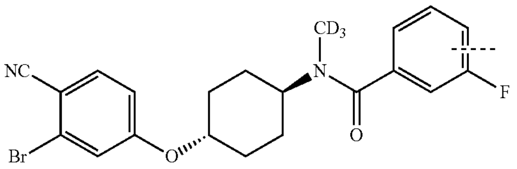
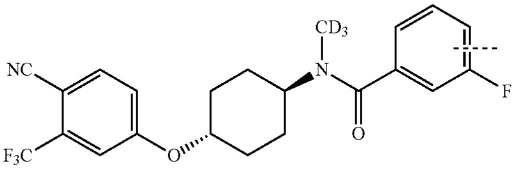

-continued
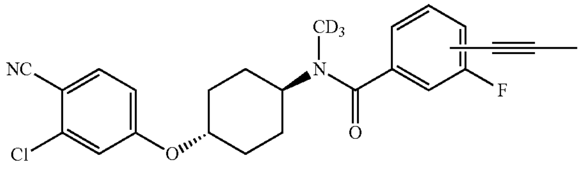
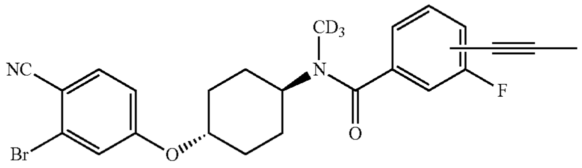
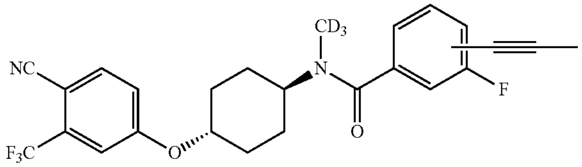
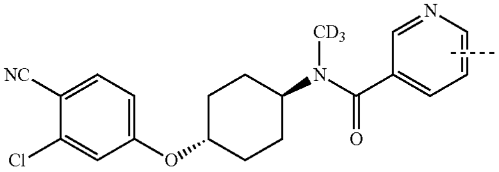
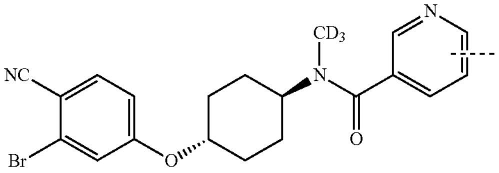
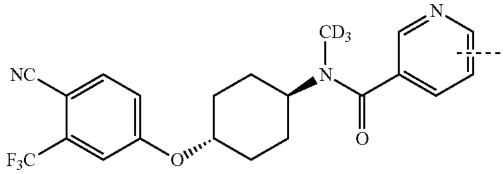
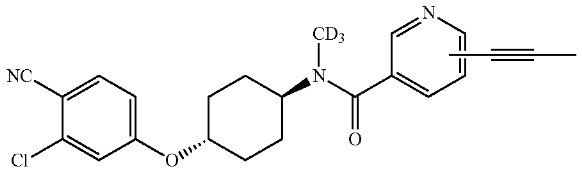
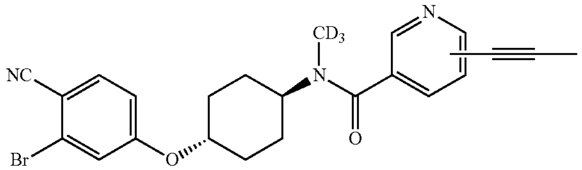
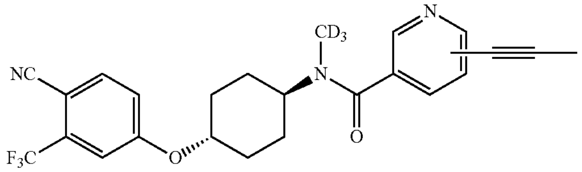
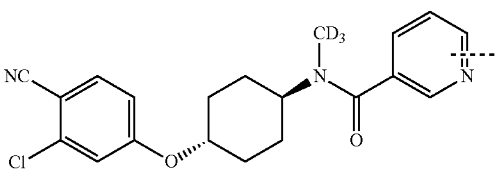
-continued
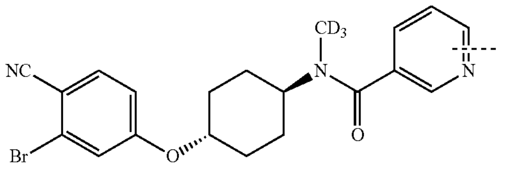
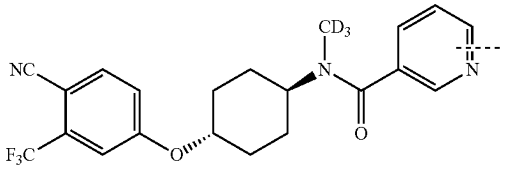
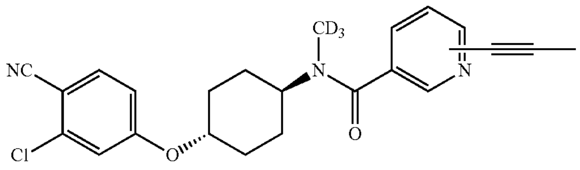
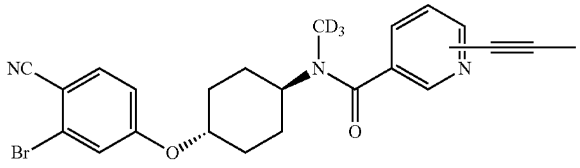
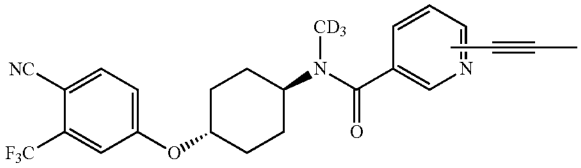
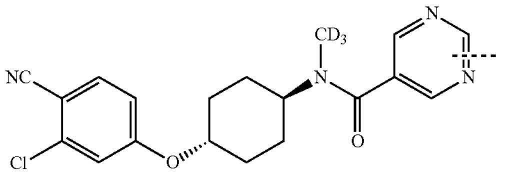
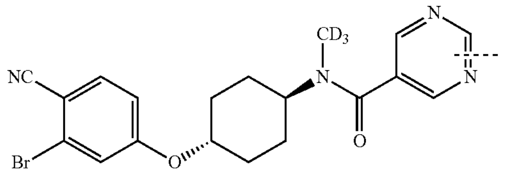
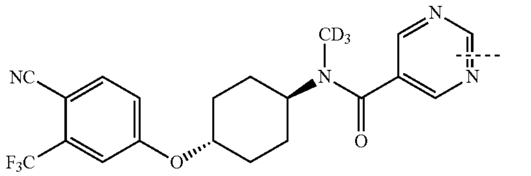
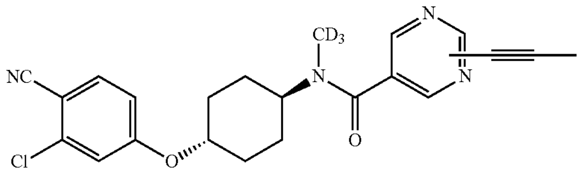
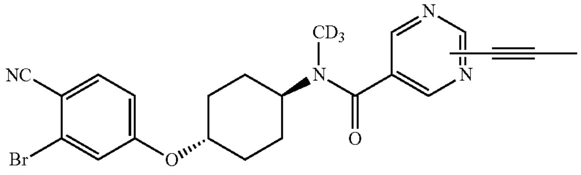

-continued
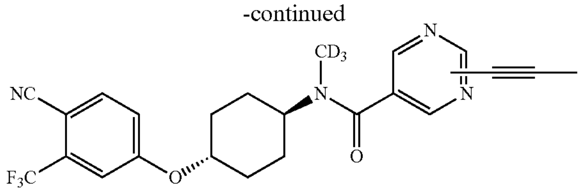
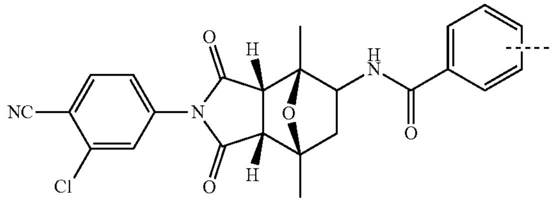
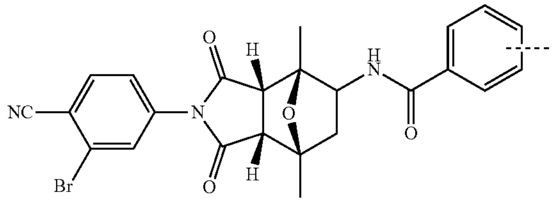
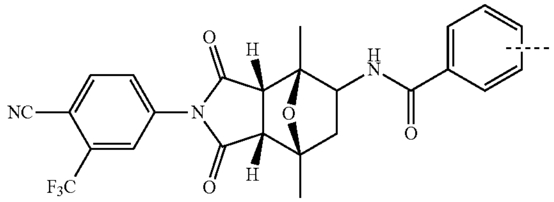
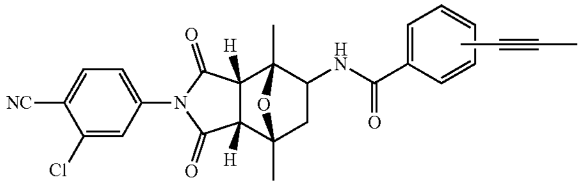
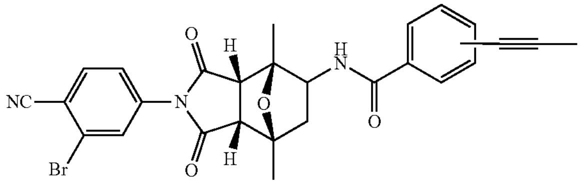
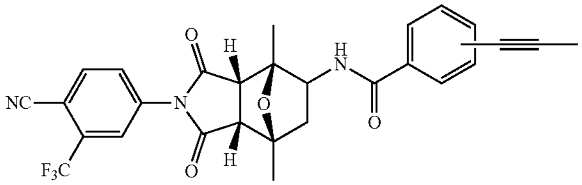
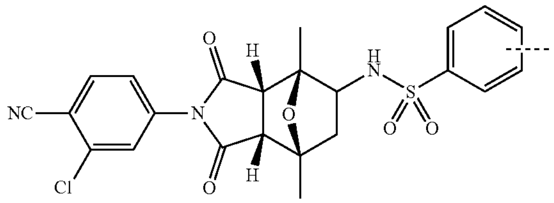
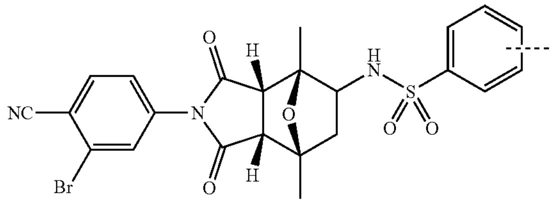
-continued
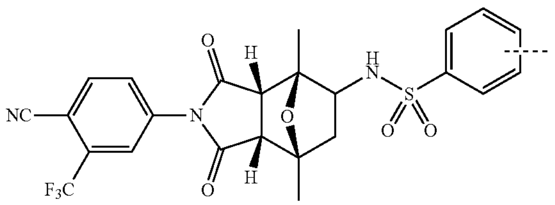
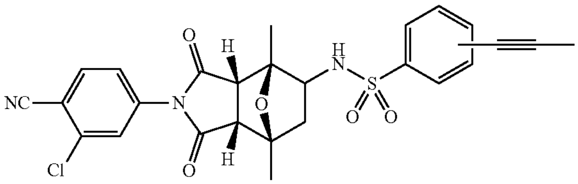
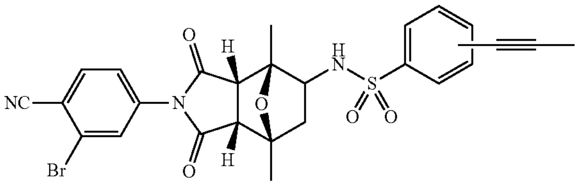
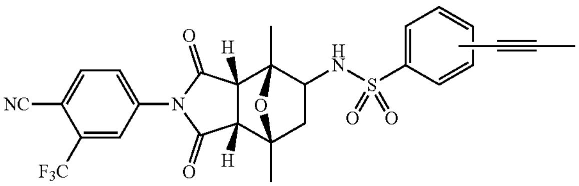
or, said ARB is selected from the structures of the following formulas:
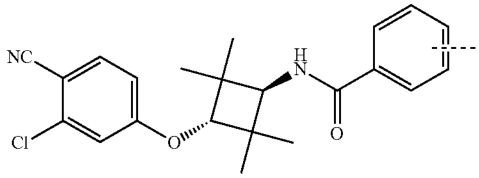
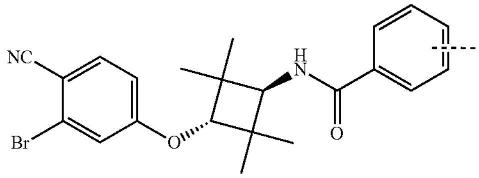
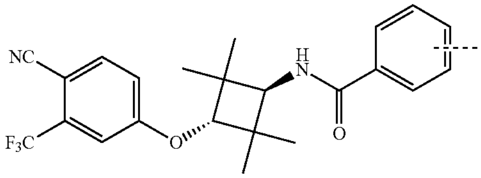
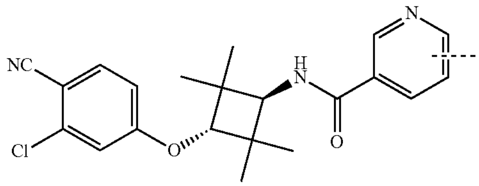

-continued
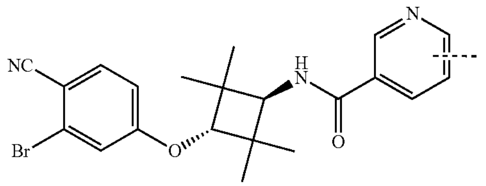
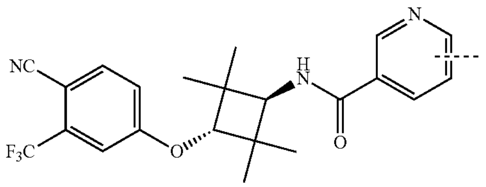
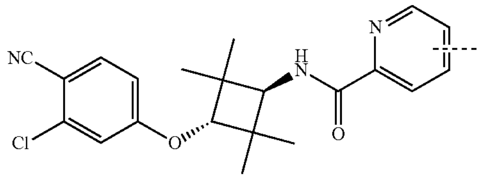
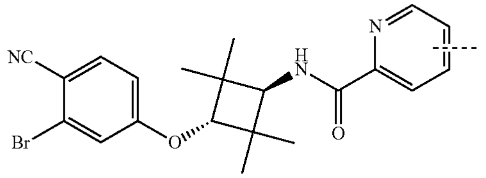
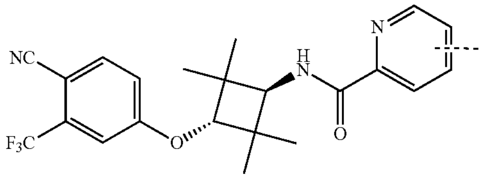
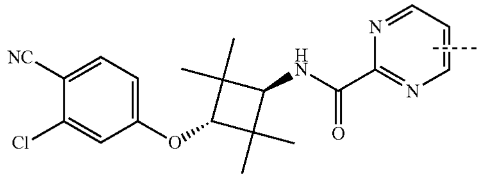
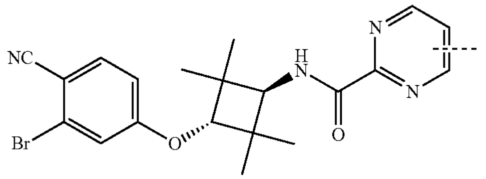
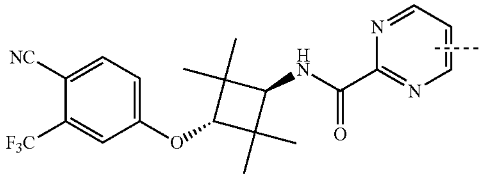
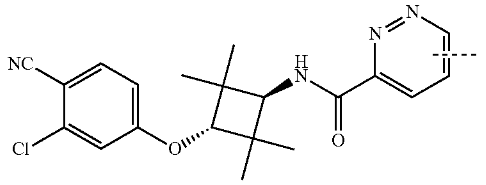
-continued
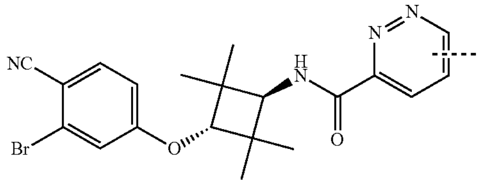
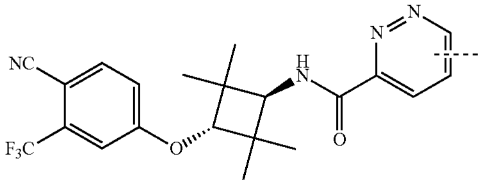
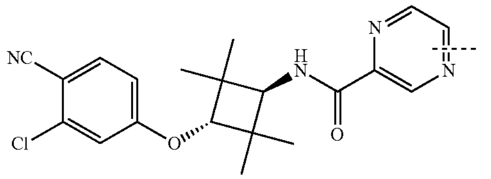
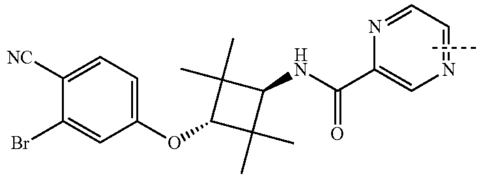
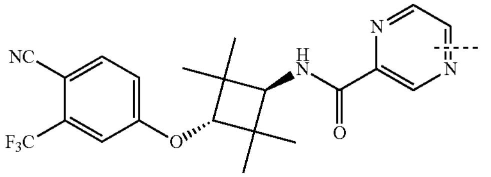
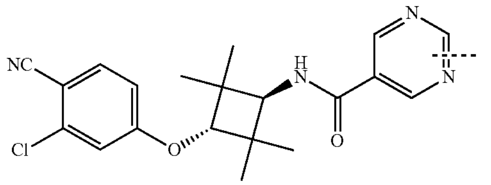
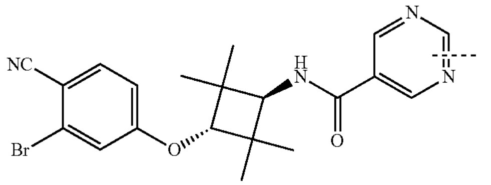
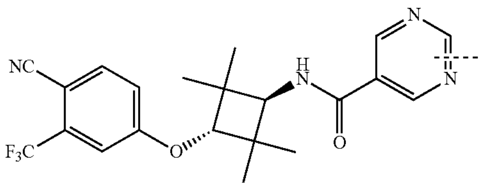
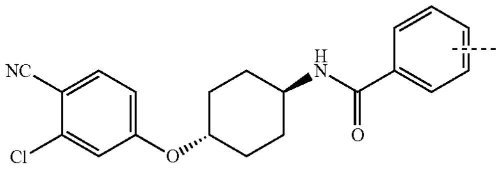

-continued
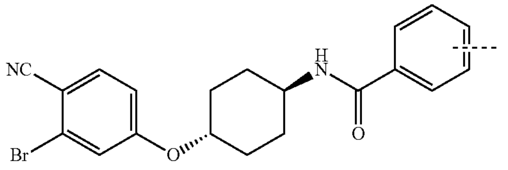
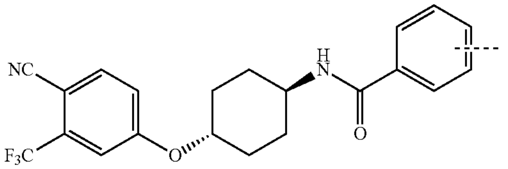
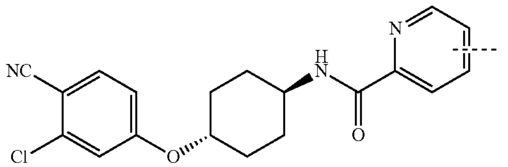
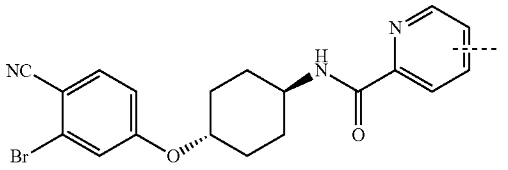
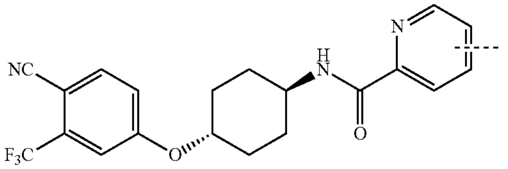
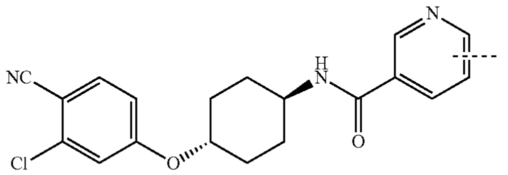
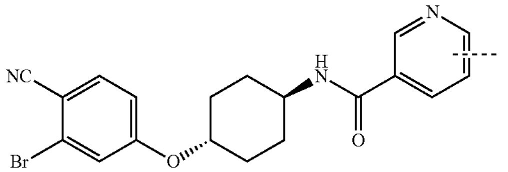
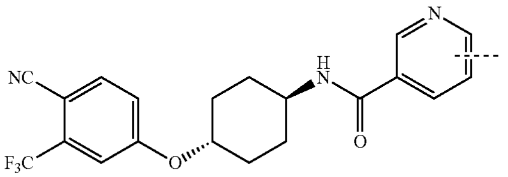
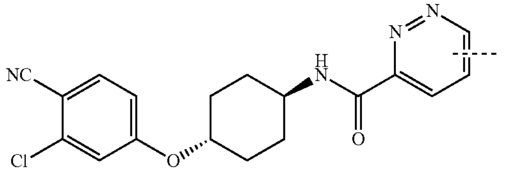
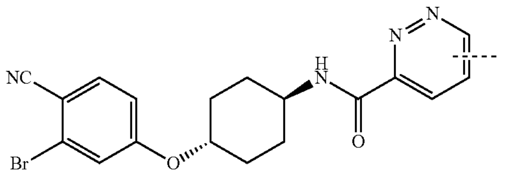
-continued
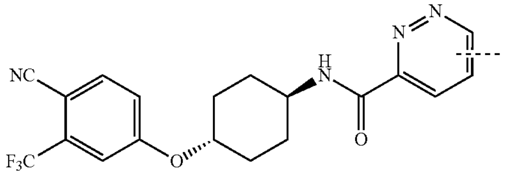
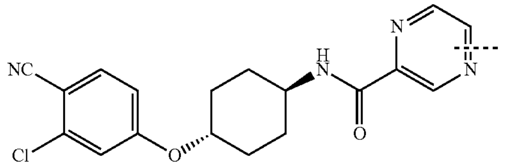
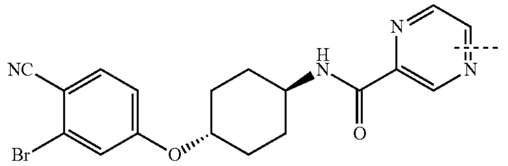
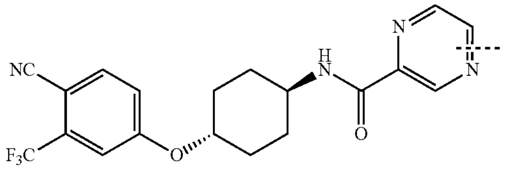
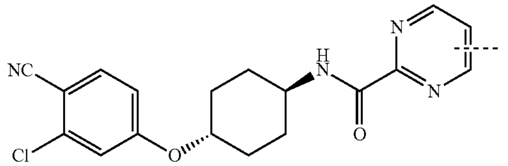
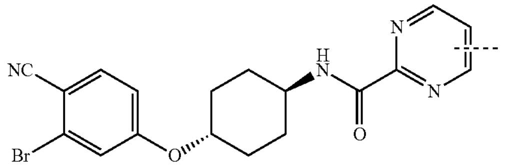
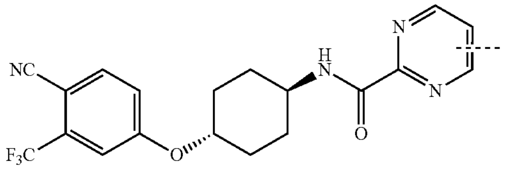
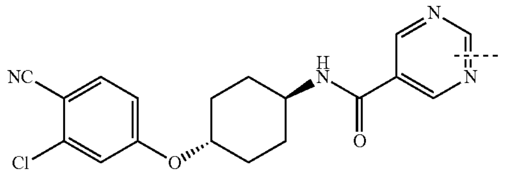
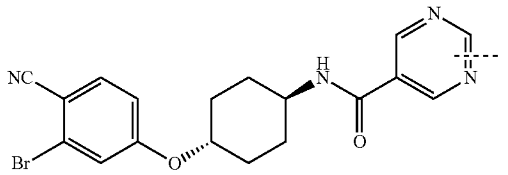
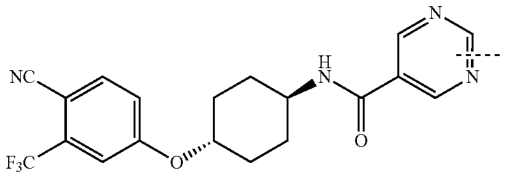

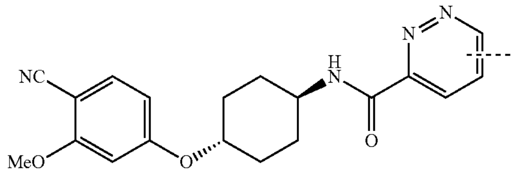
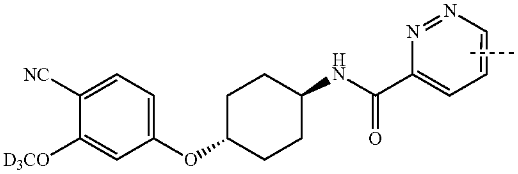
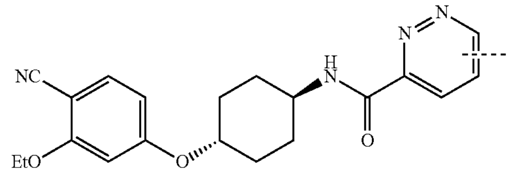
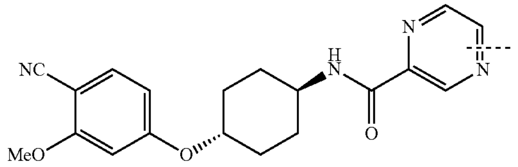
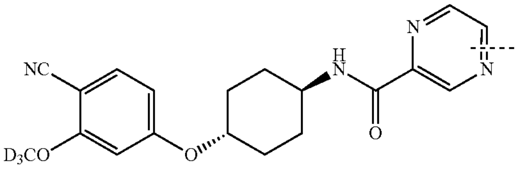
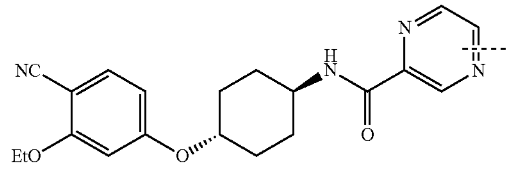
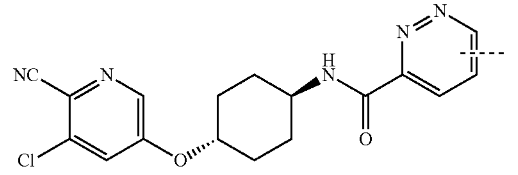
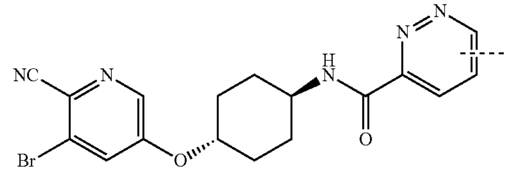
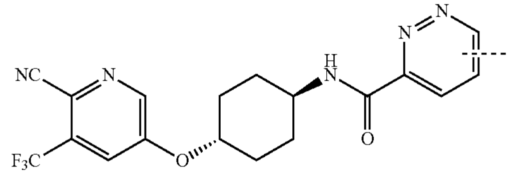
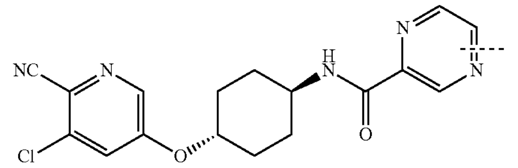
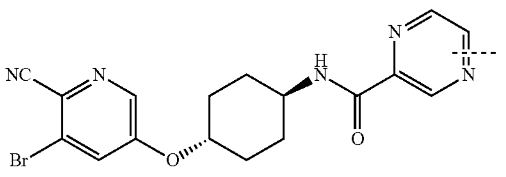
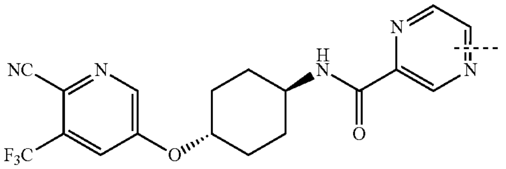
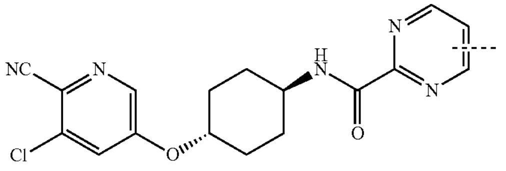
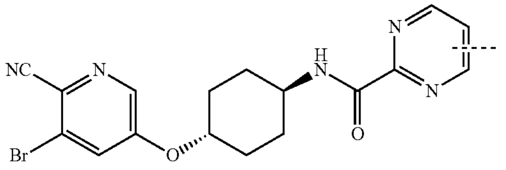
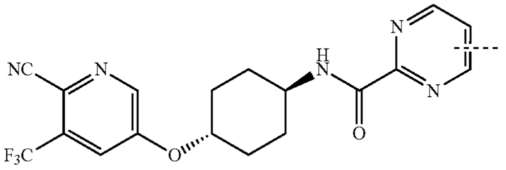
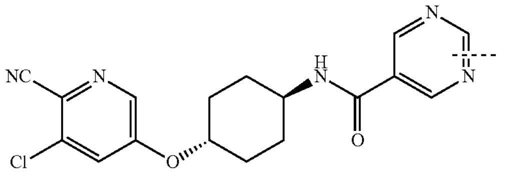
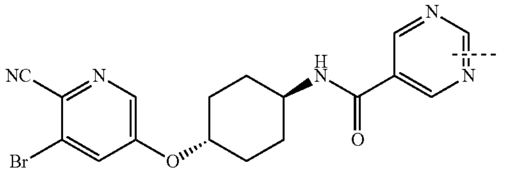
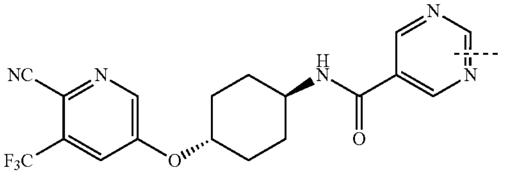
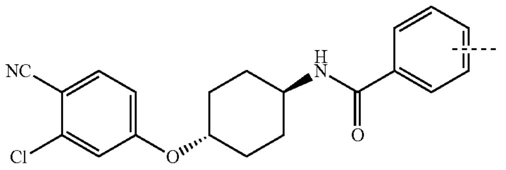
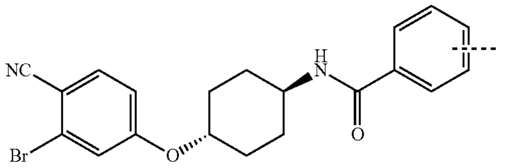

-continued
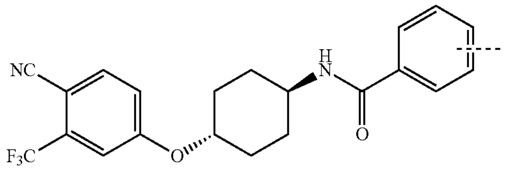
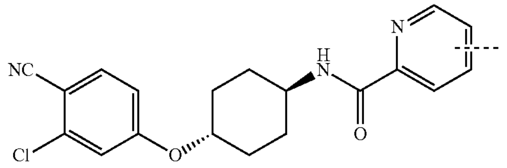
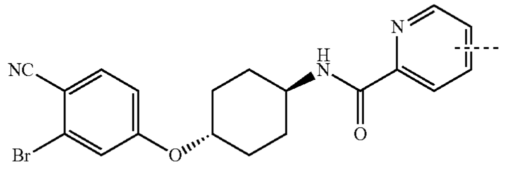
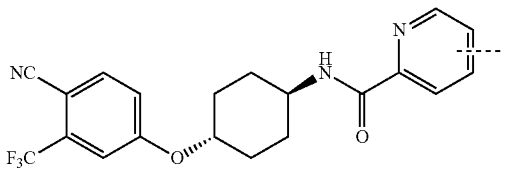
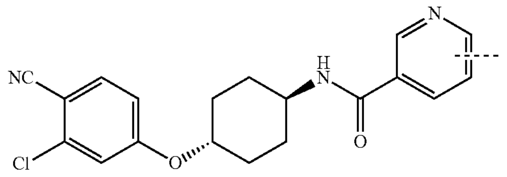
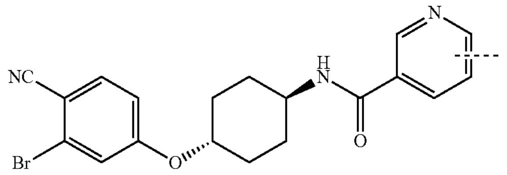
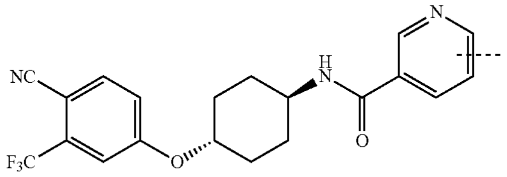
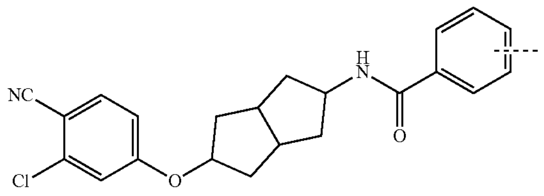
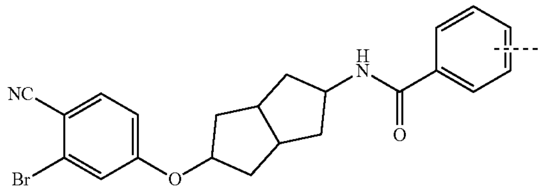
-continued
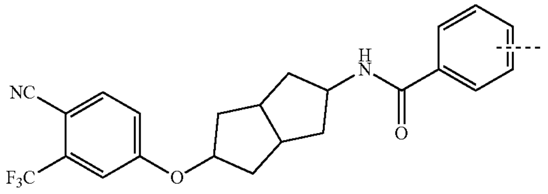
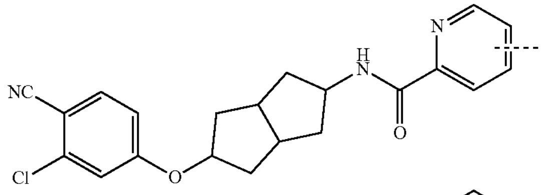
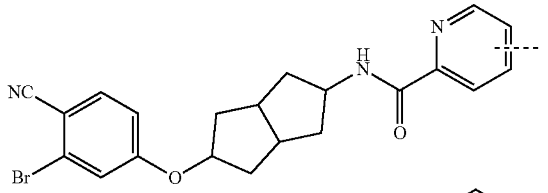
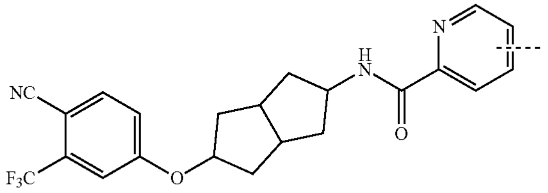
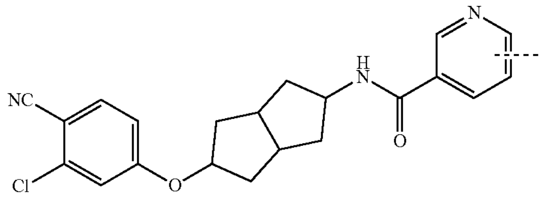
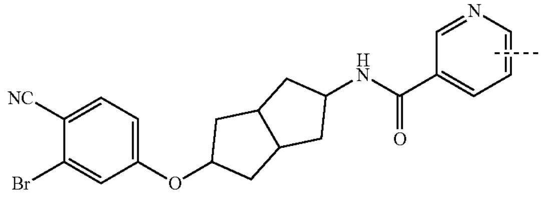
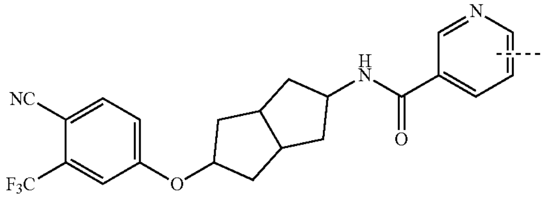
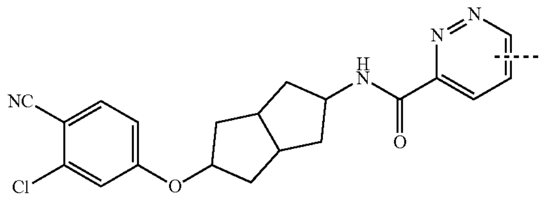
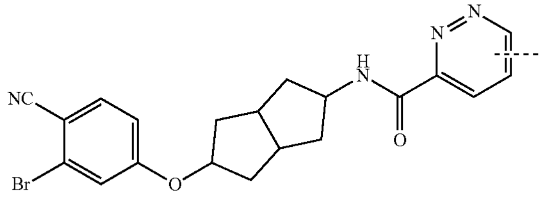

-continued
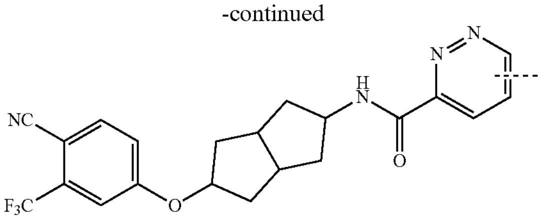
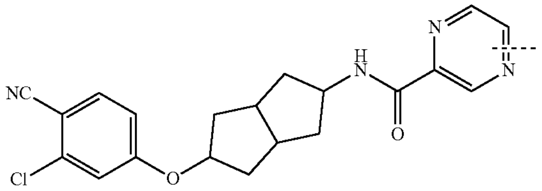
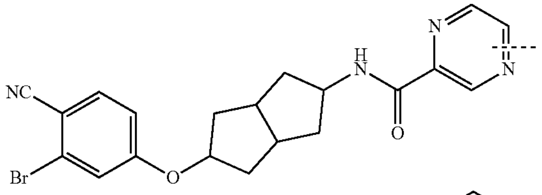
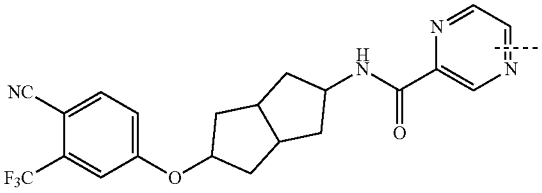
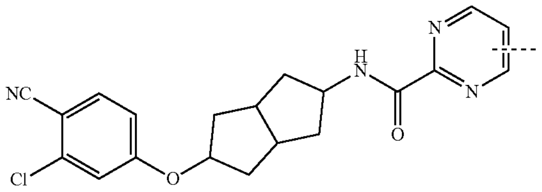
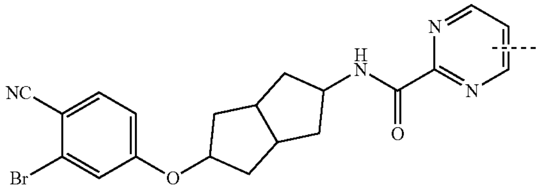
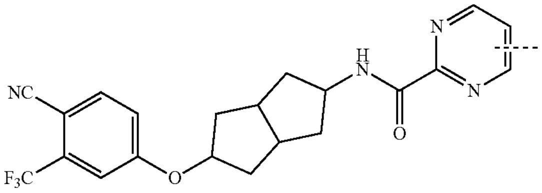
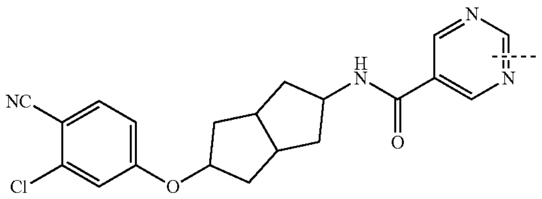
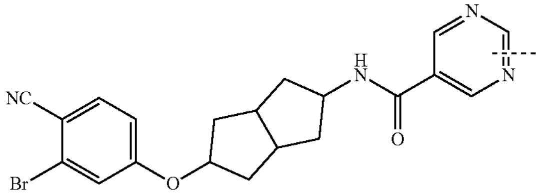
-continued
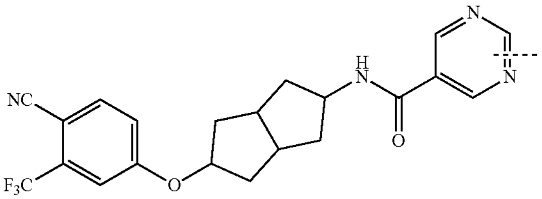
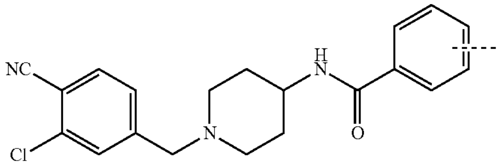
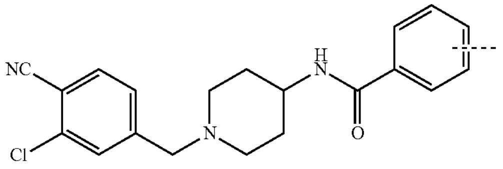
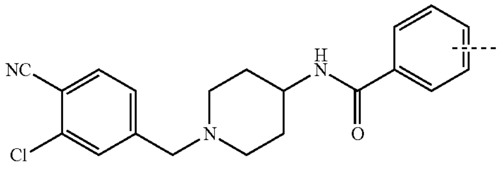
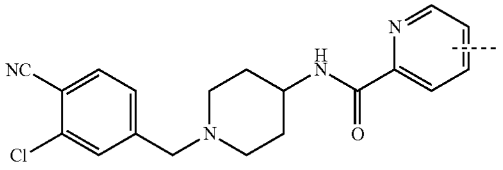
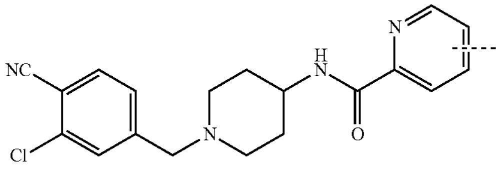
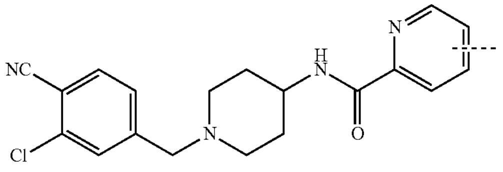
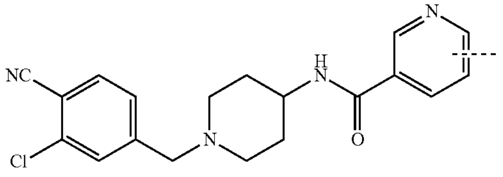
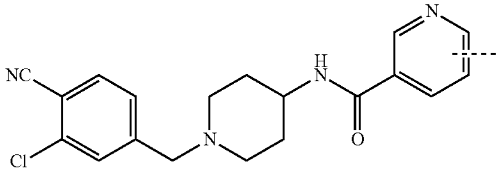
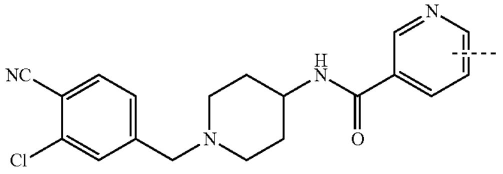

-continued
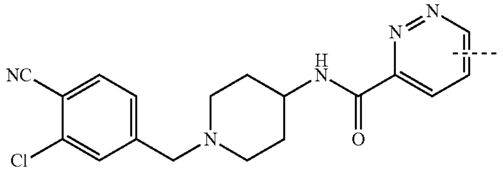
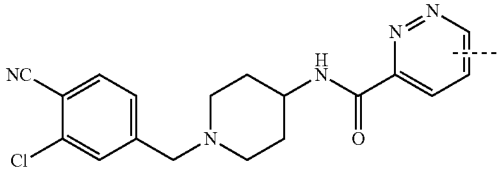
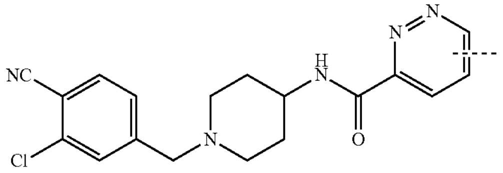
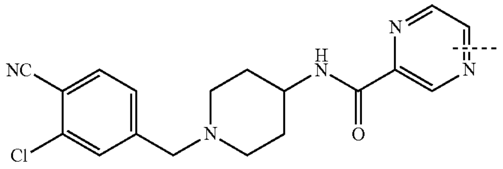
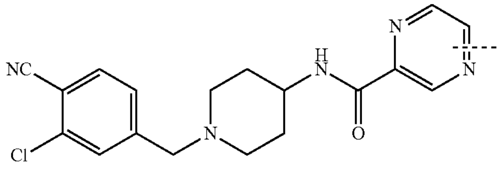
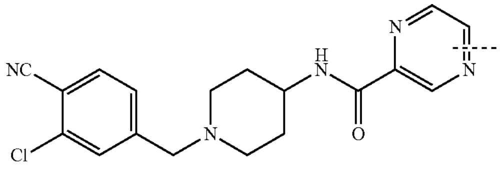
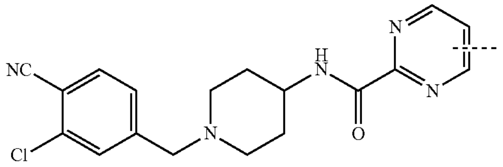
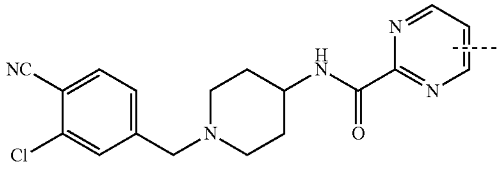
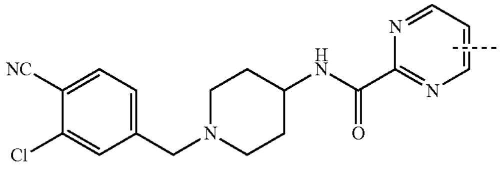
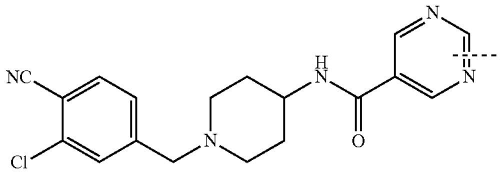
-continued
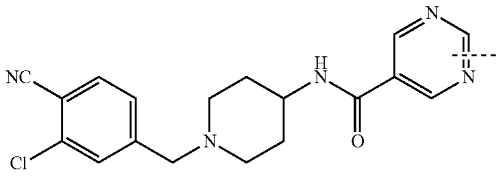
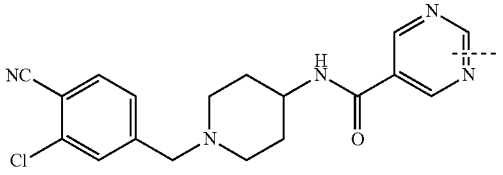
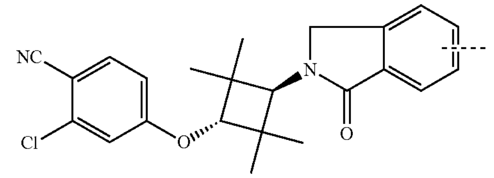
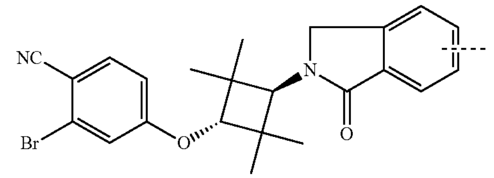
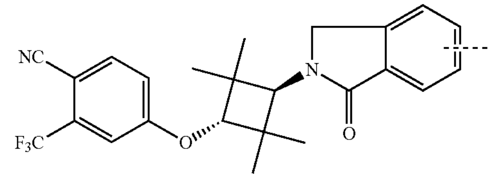
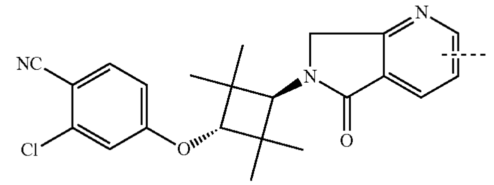
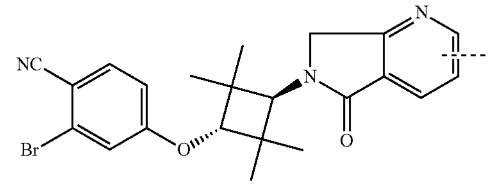
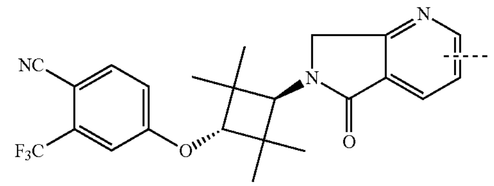
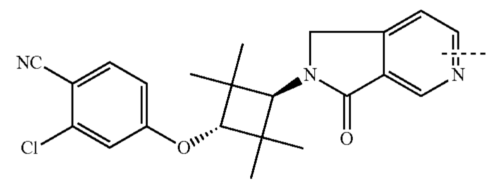

-continued
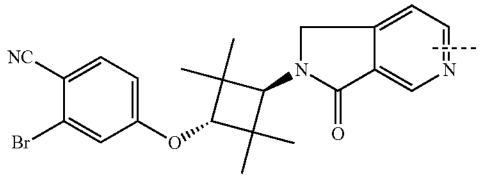
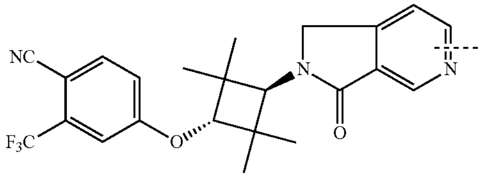
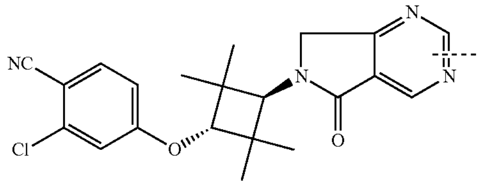
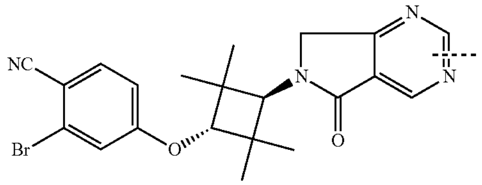
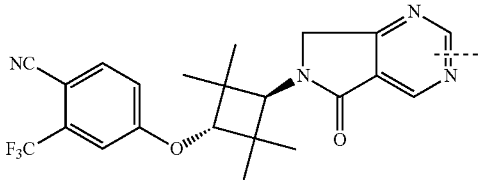
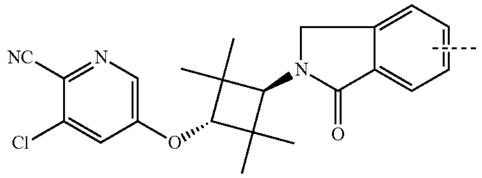
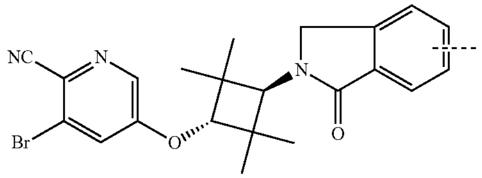
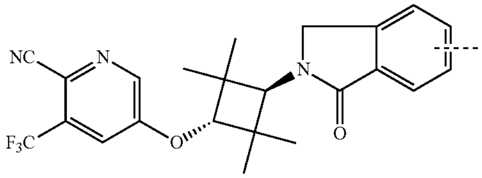
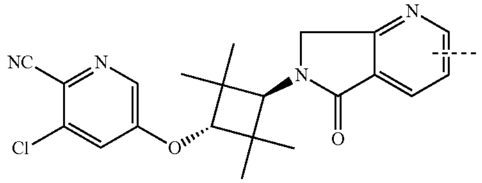
-continued
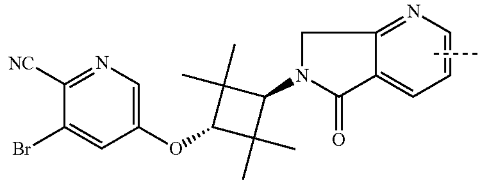
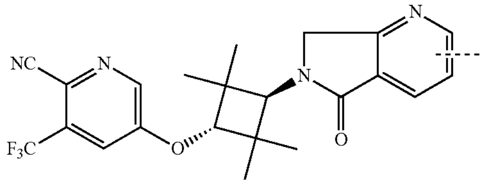
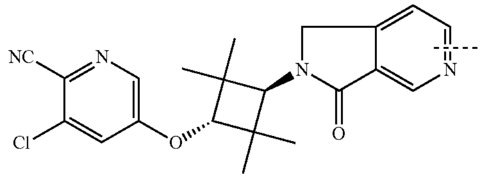
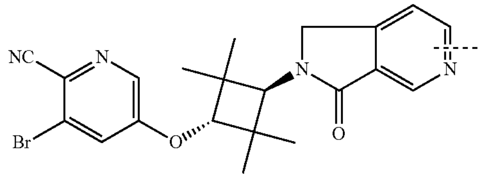
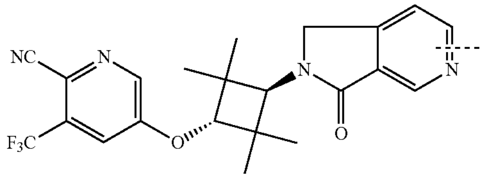
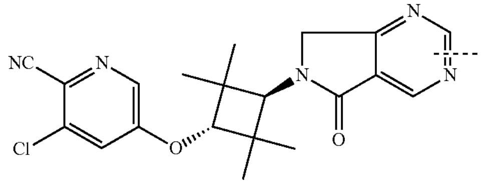
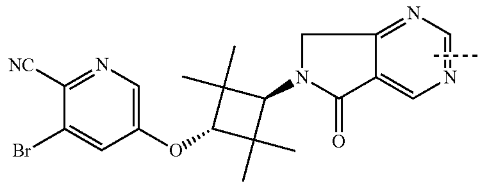
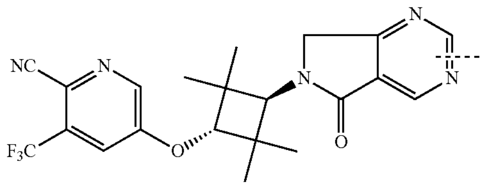
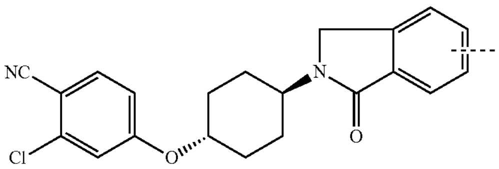

-continued
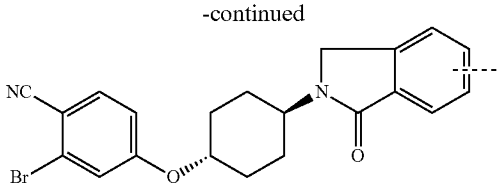
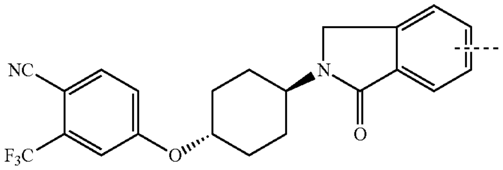
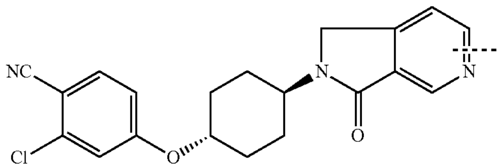
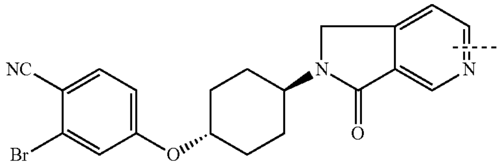
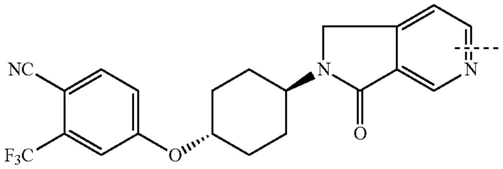
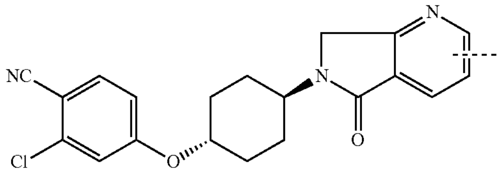
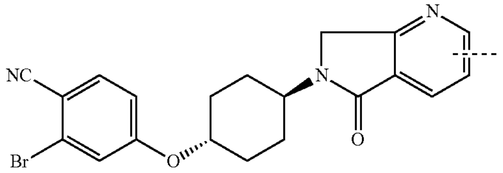
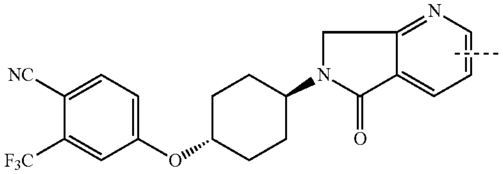
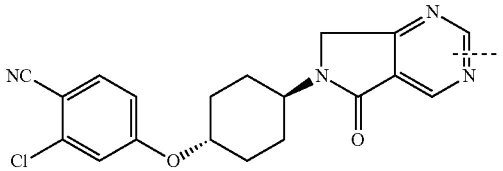
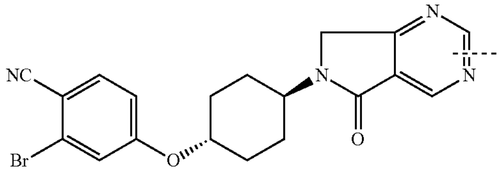
-continued
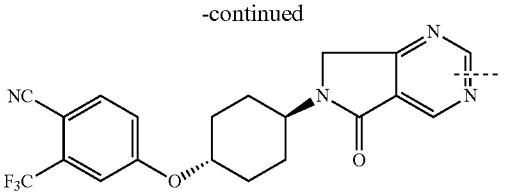
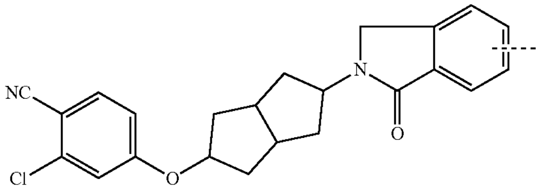
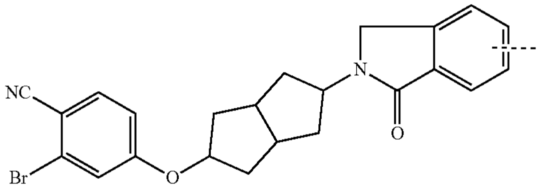
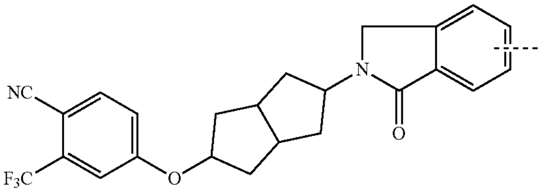
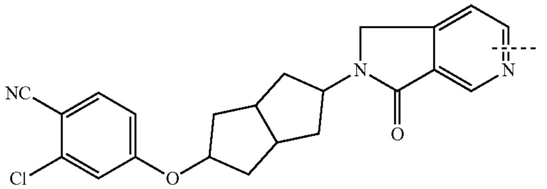
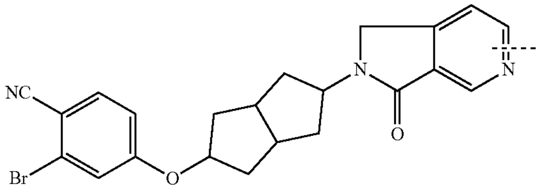
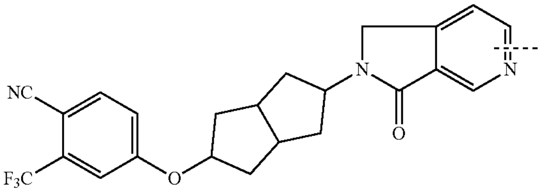
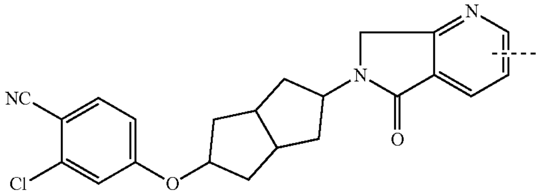
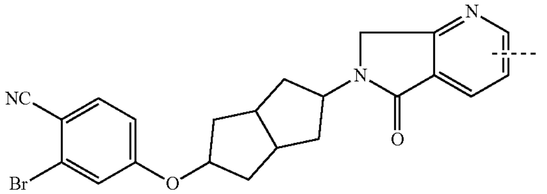

-continued
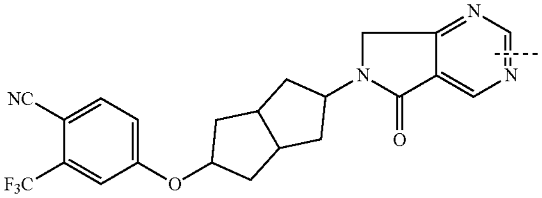
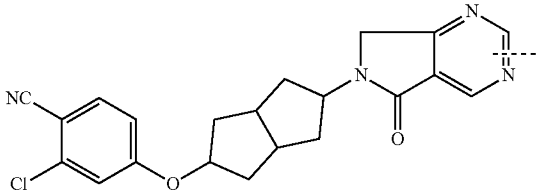
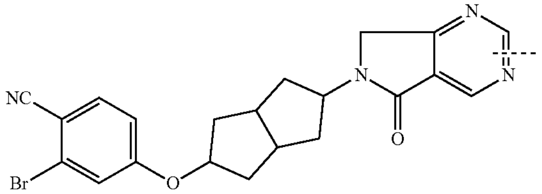
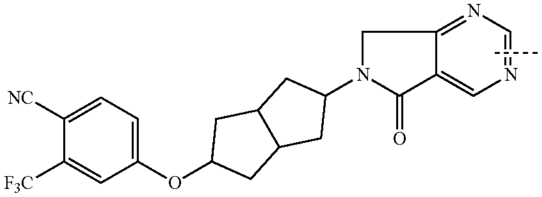
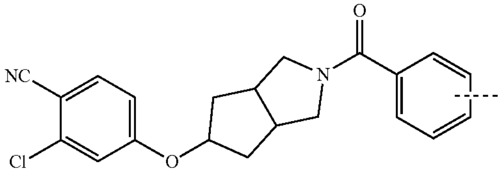
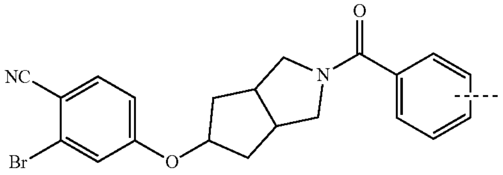
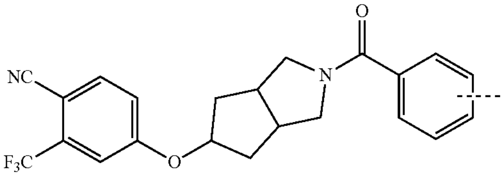
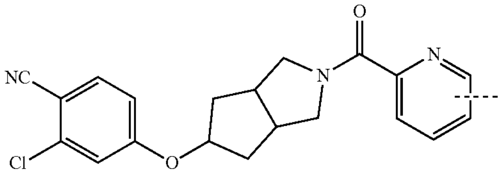
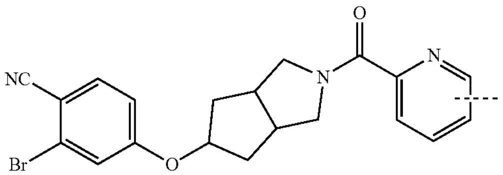
-continued
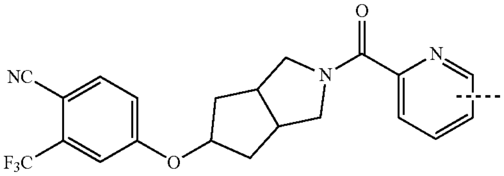
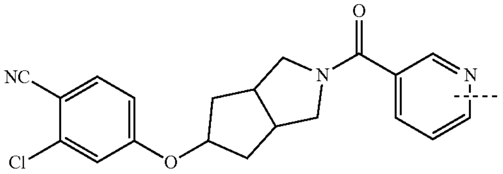
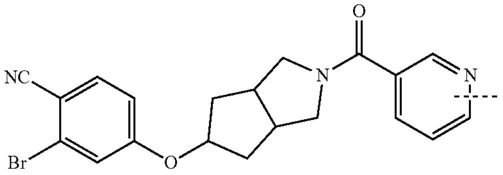
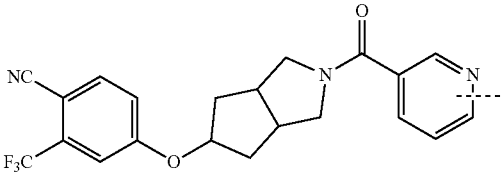
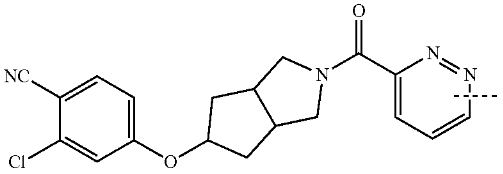
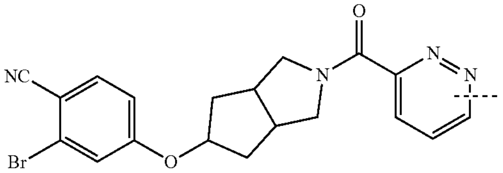
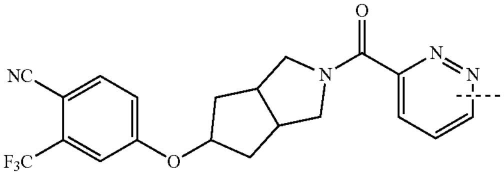
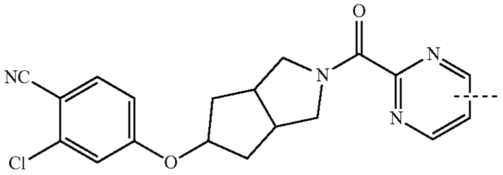
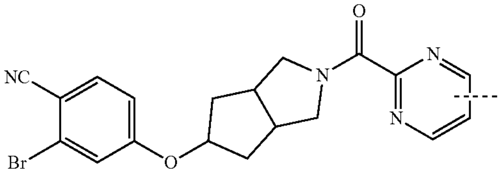

-continued
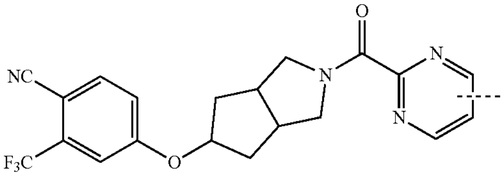
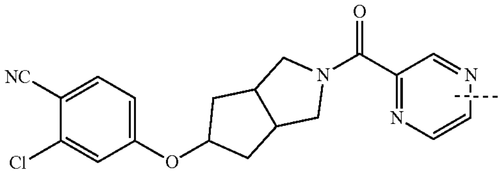
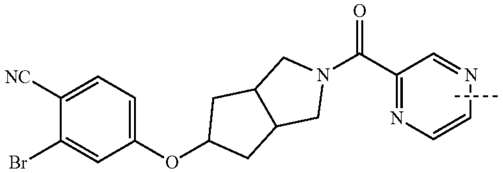
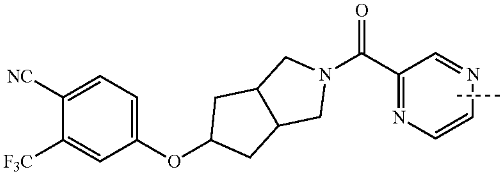
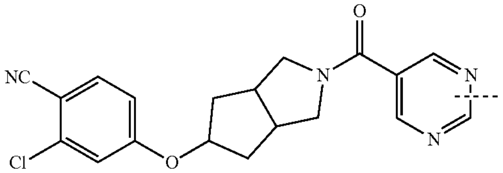
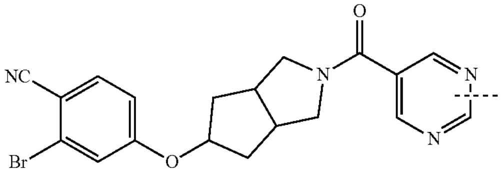
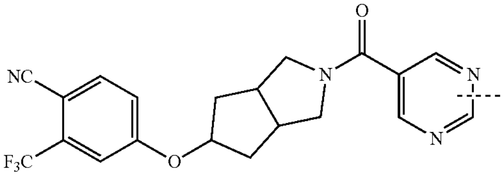
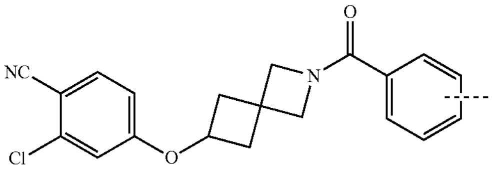
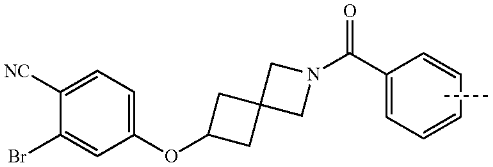
-continued
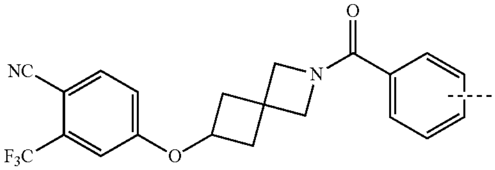
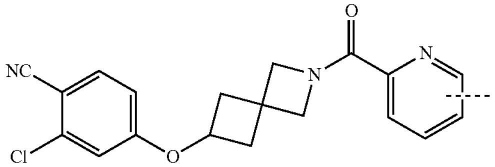
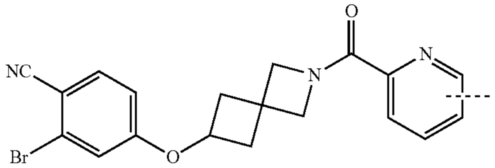
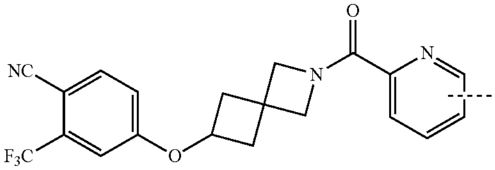
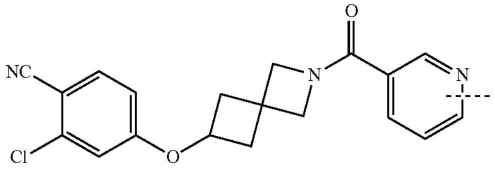
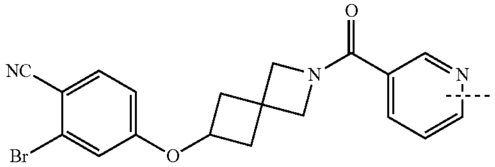
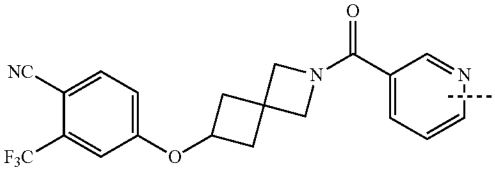
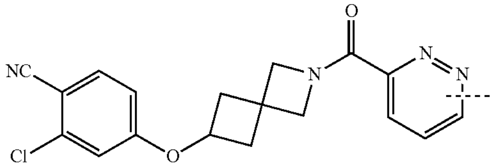
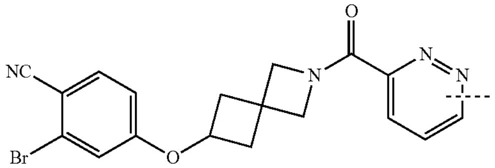
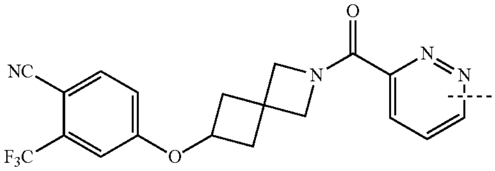

-continued
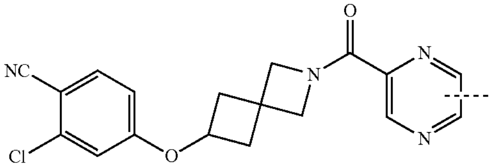
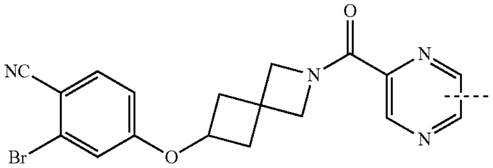
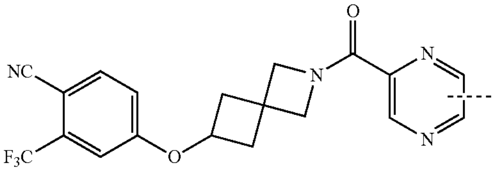
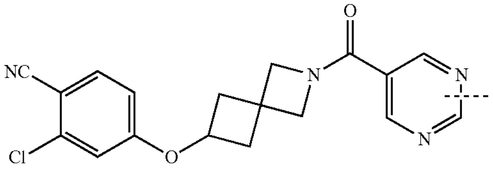
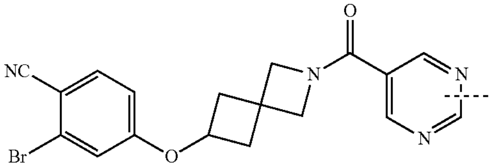
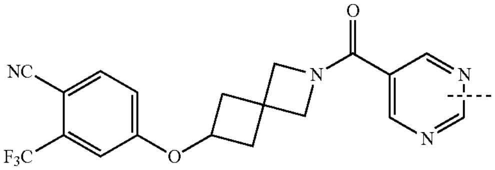
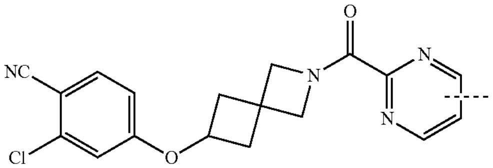
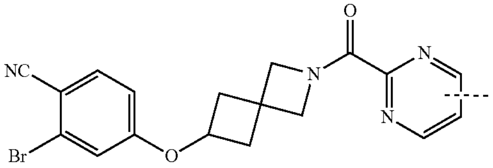
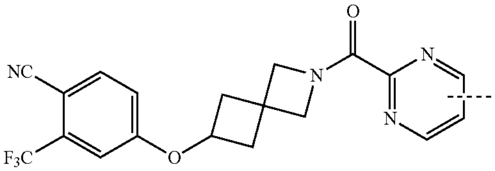
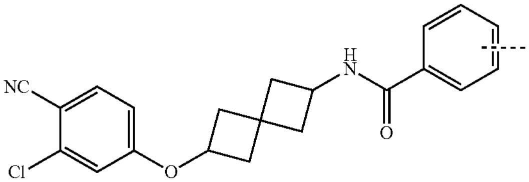
-continued
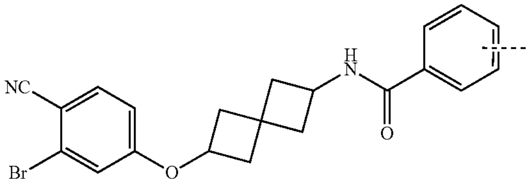
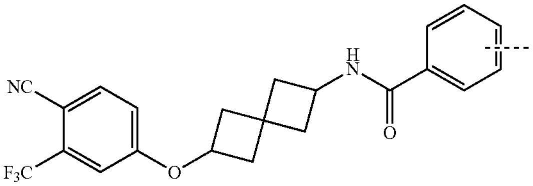
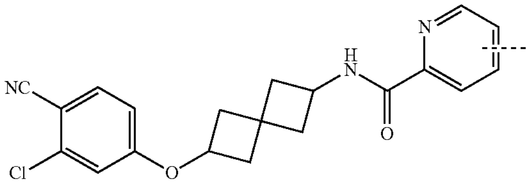
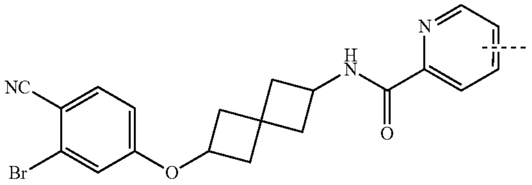
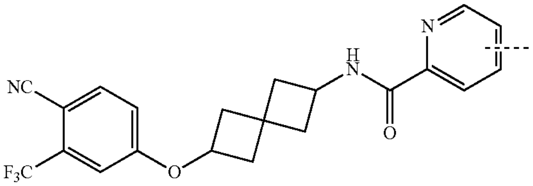
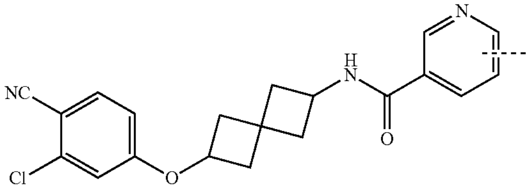
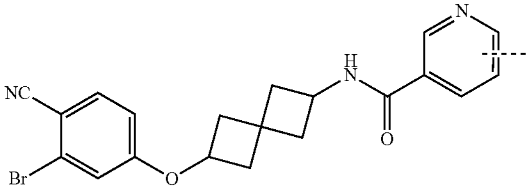
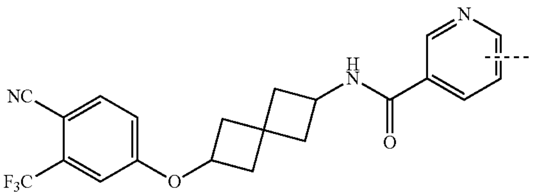
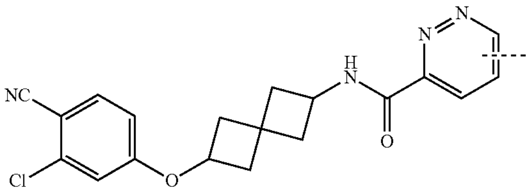

-continued
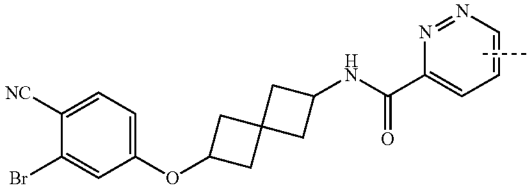
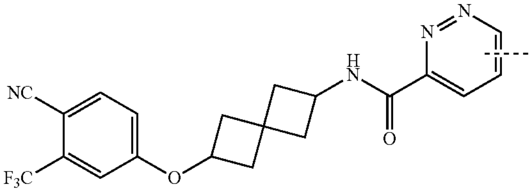
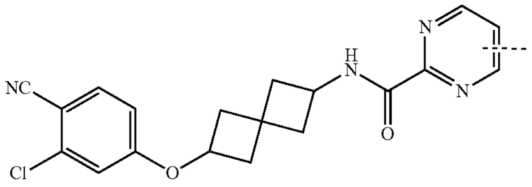
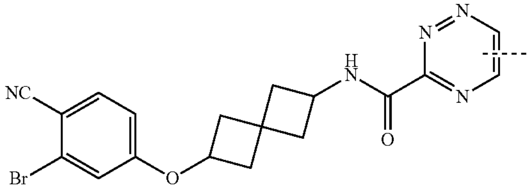
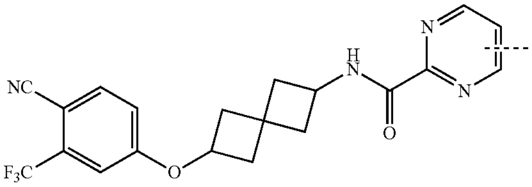
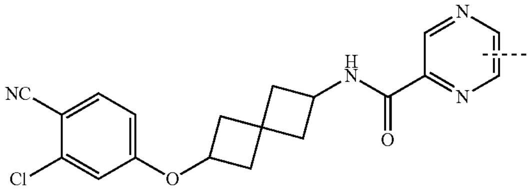
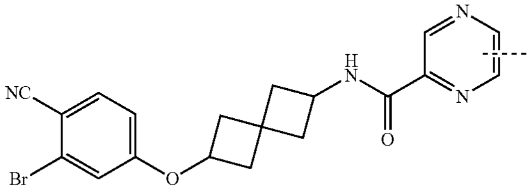
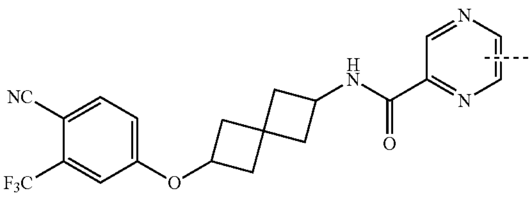
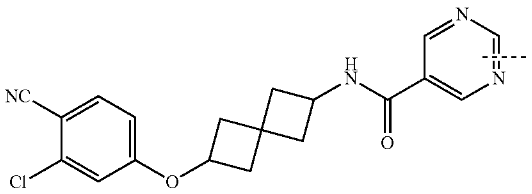
-continued
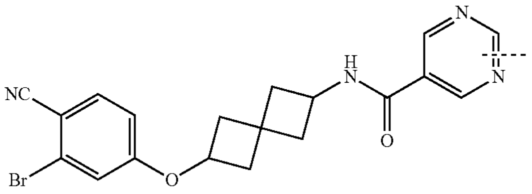
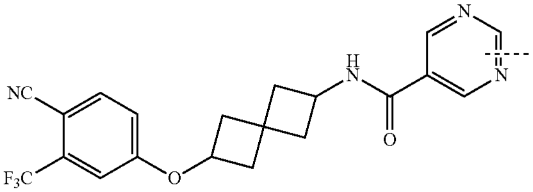
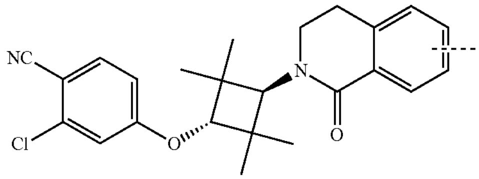
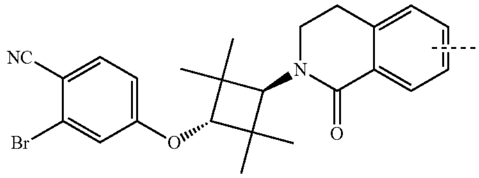
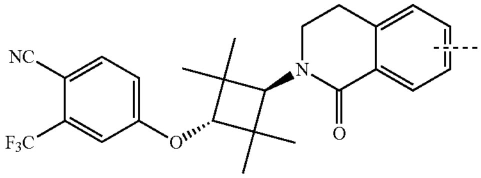
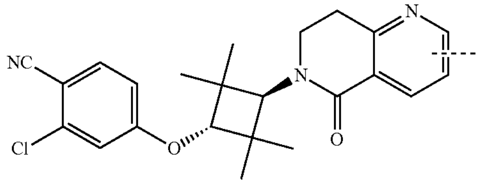
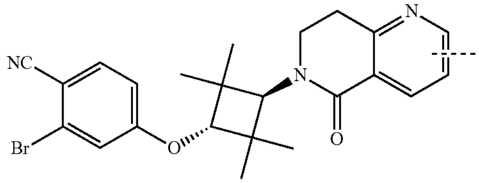
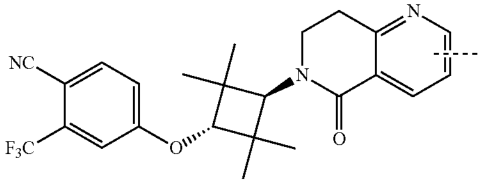
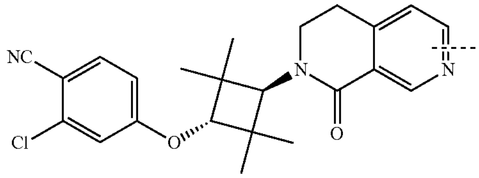

-continued
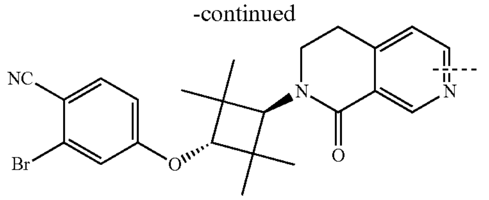
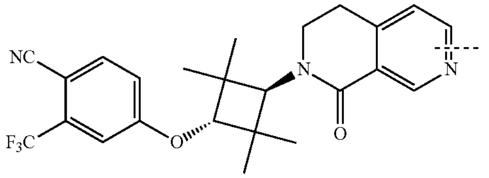
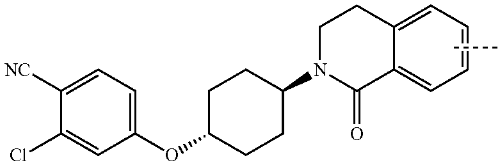
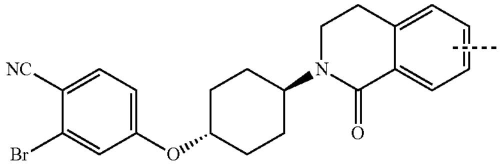
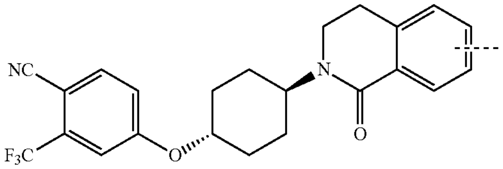
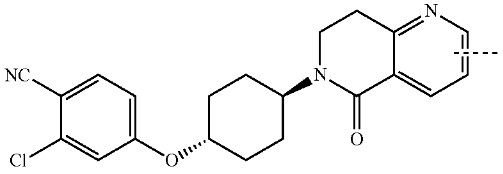
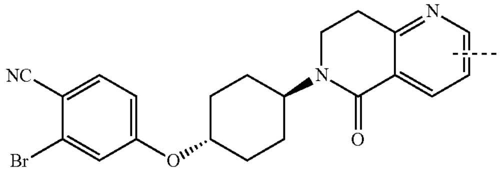
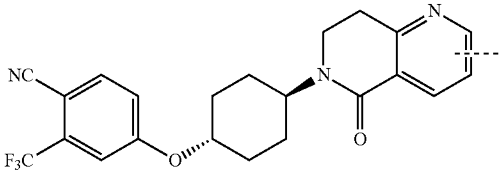
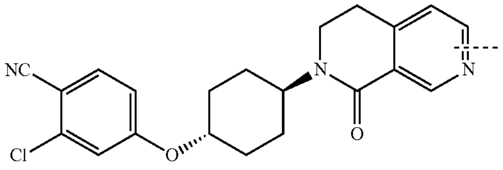
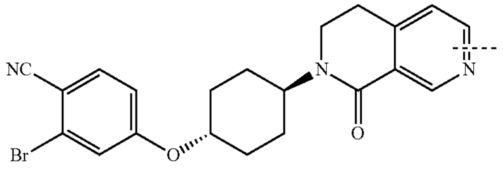
-continued
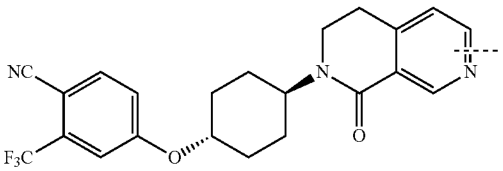
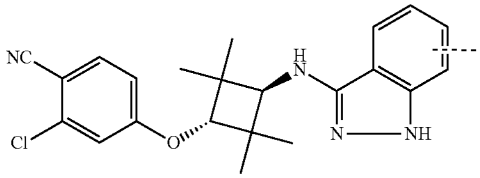
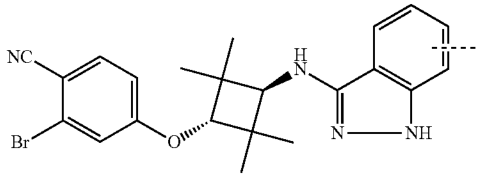
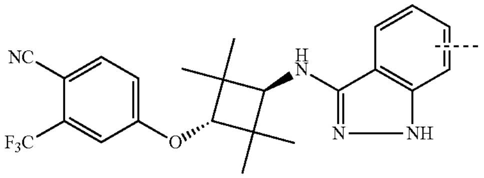
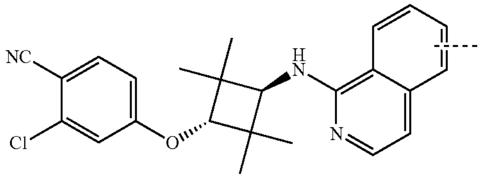
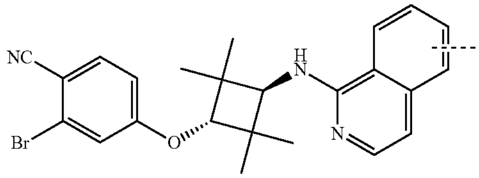
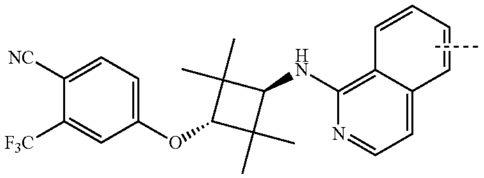
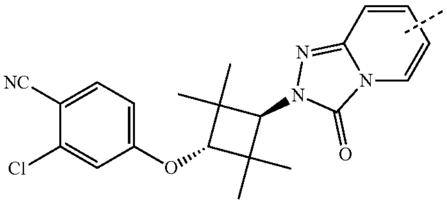
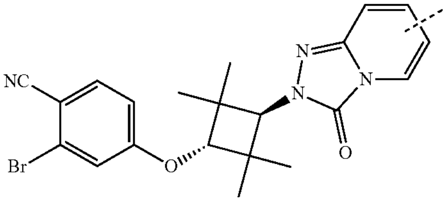

-continued
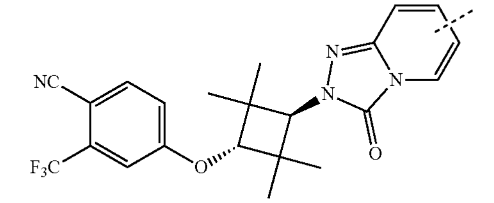
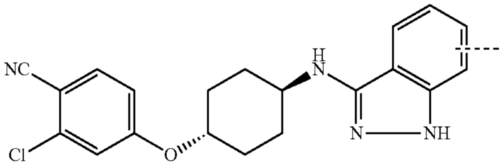
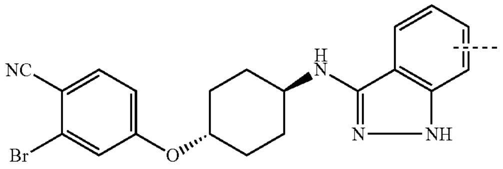
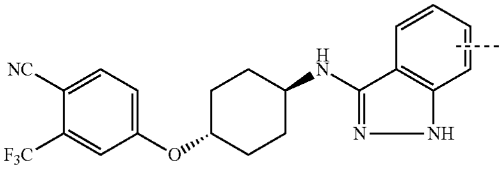
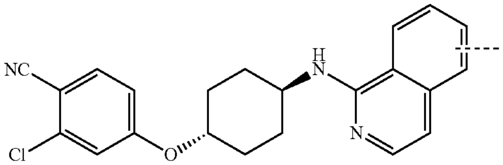
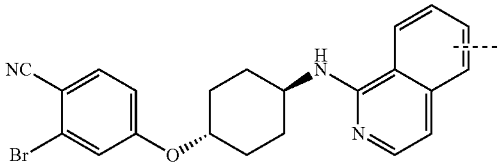
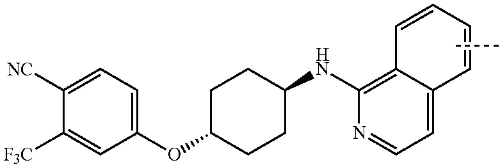
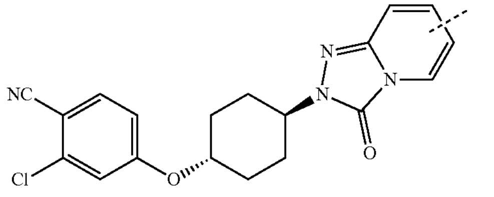
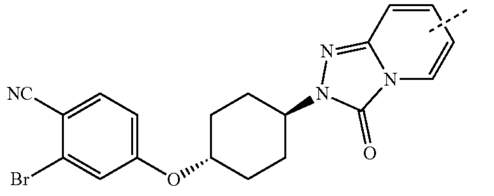
-continued
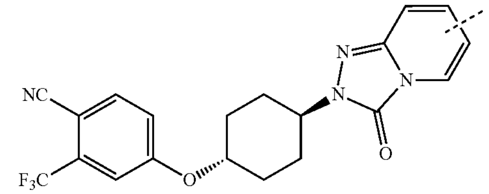
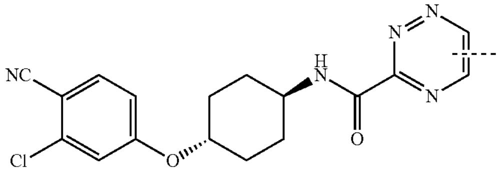
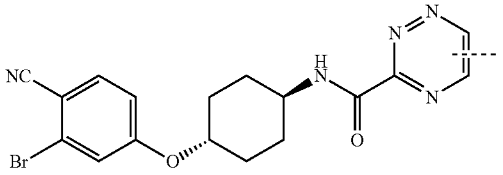
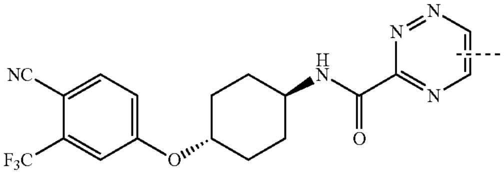
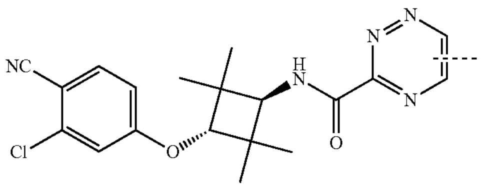
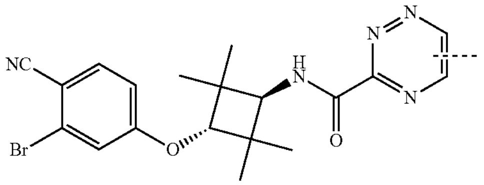
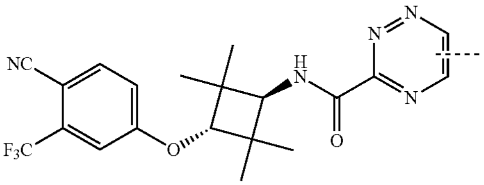
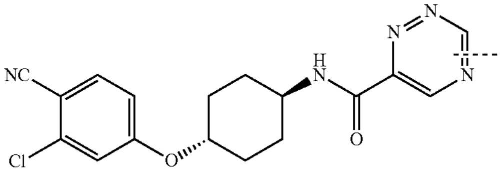
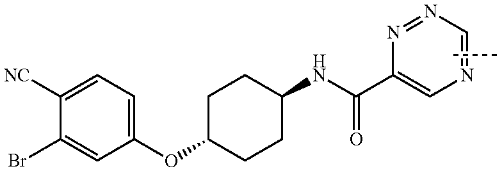

-continued
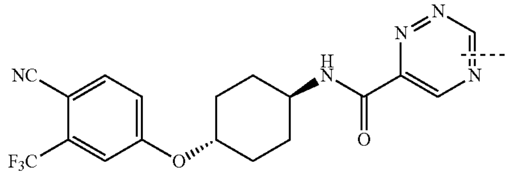
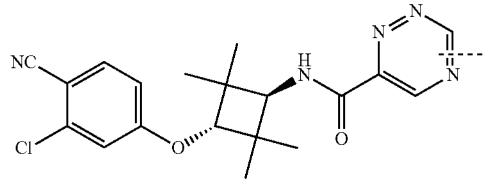
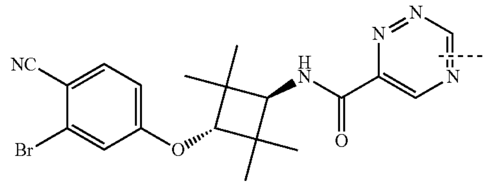
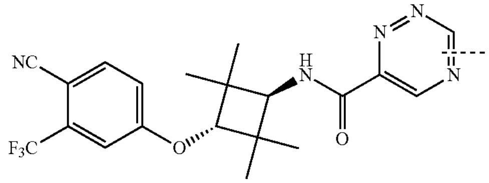
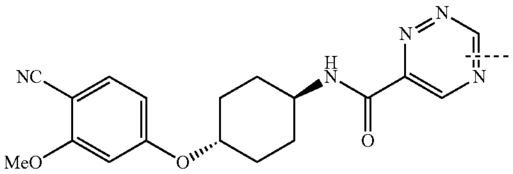
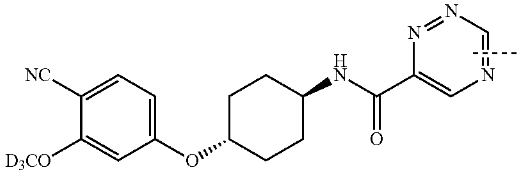
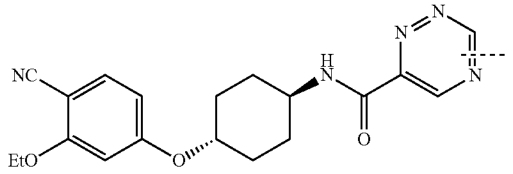
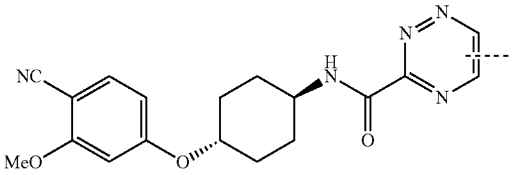
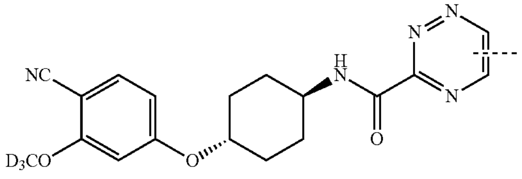
-continued
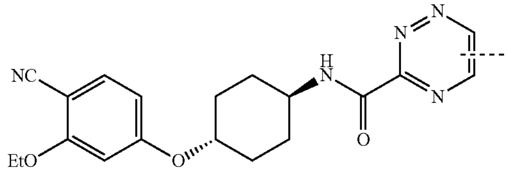
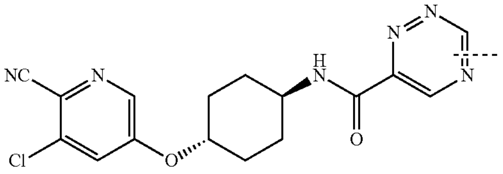
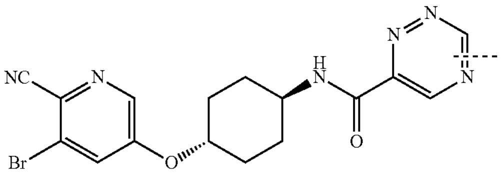
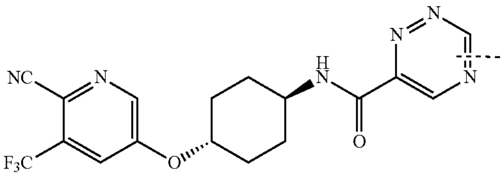
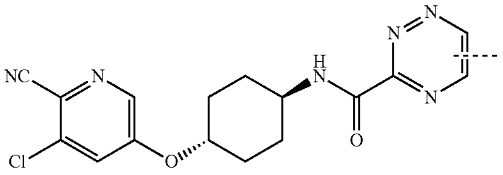
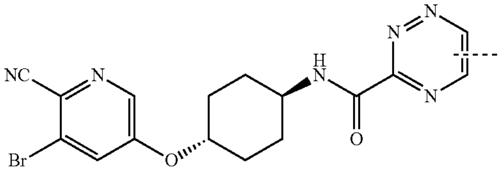
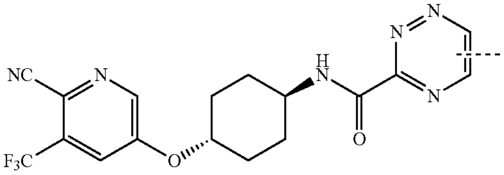
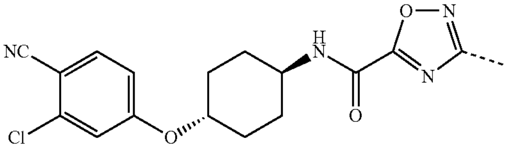
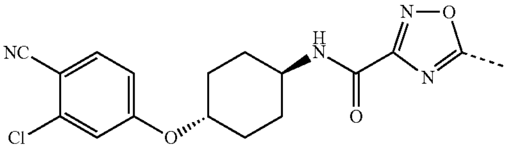
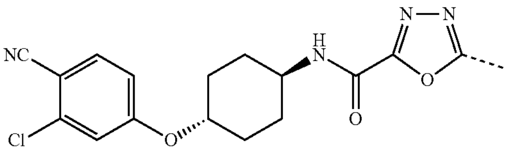

-continued
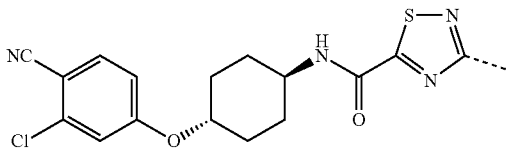
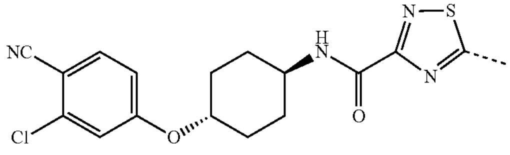
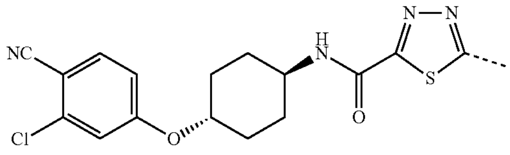
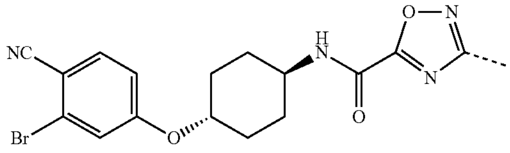
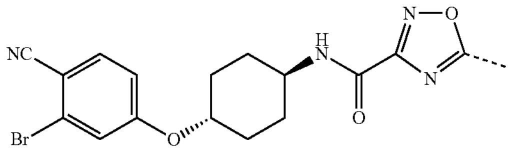
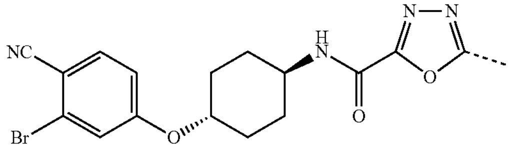
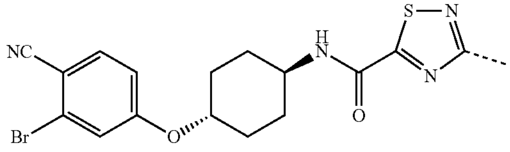
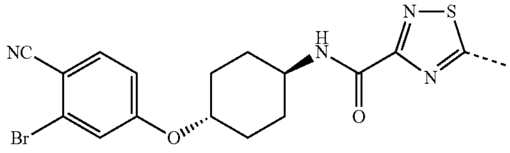
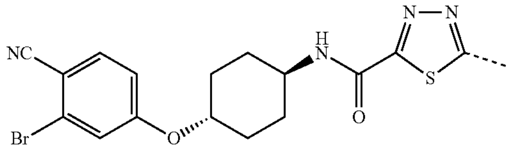
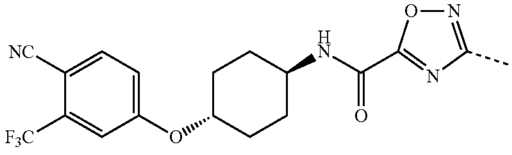
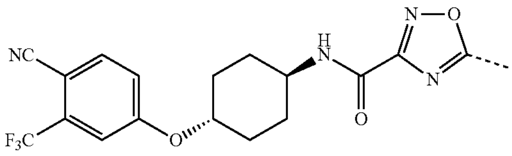
-continued
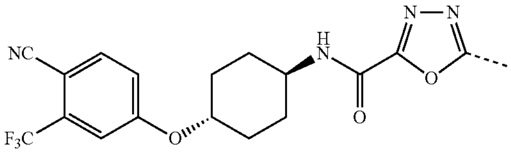
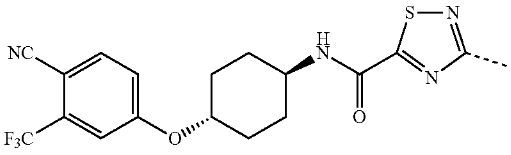
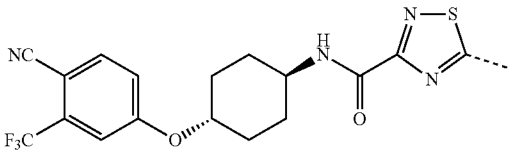
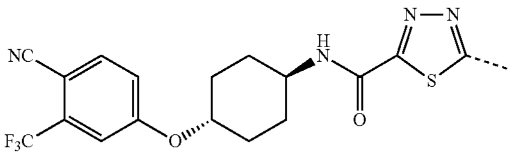
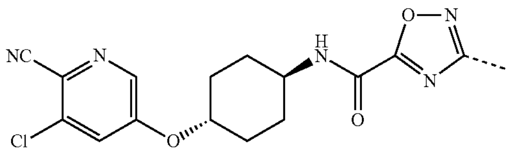
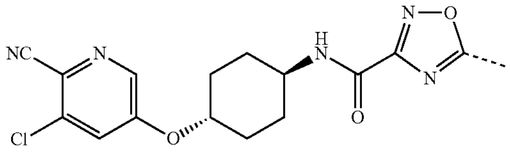
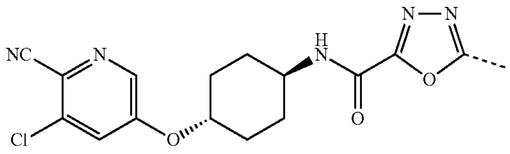
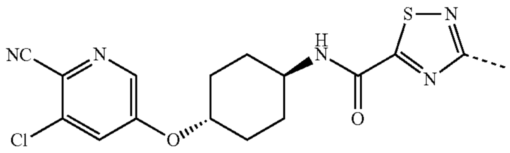
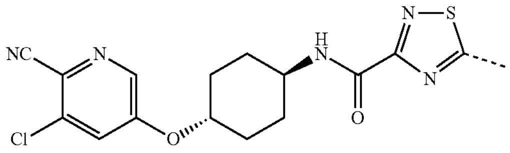
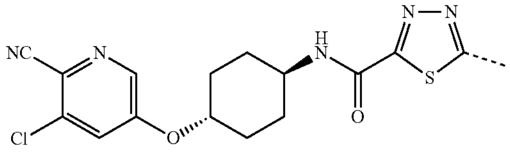
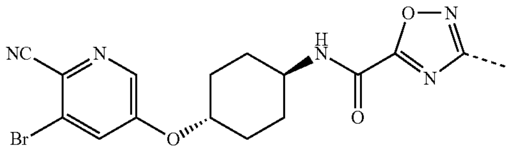

-continued
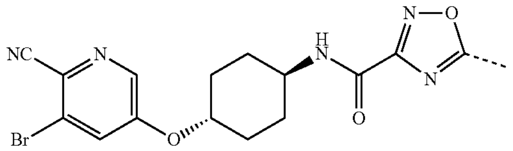
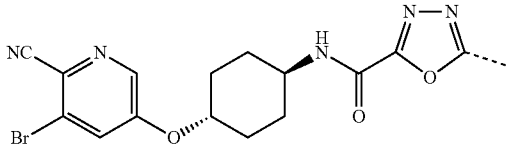
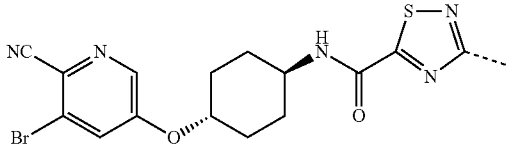
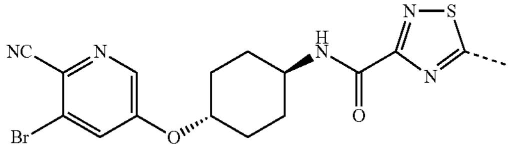
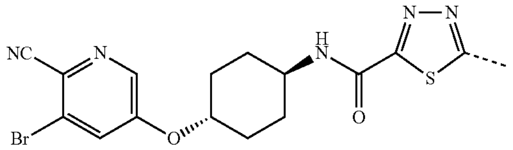
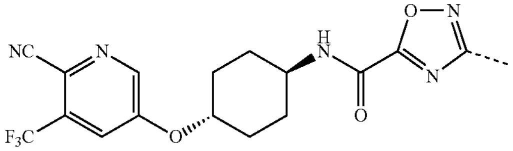
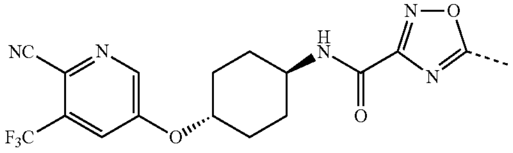
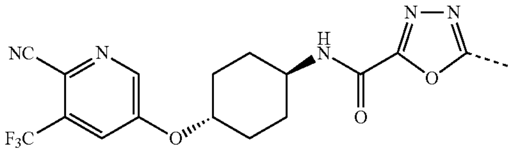
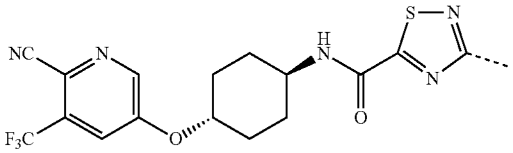
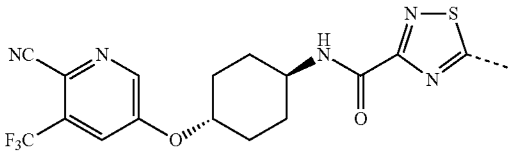
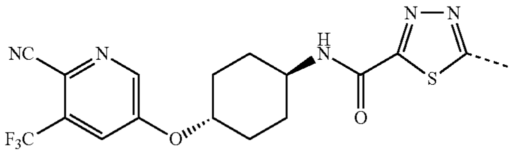
-continued
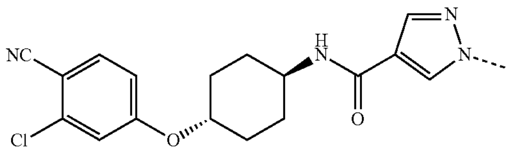
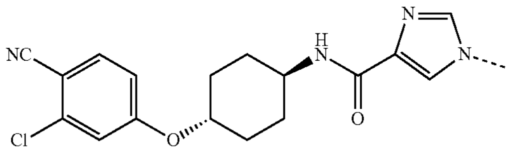
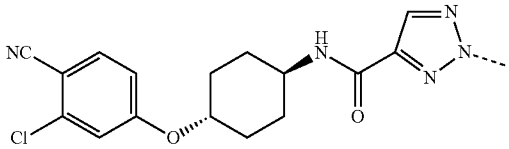
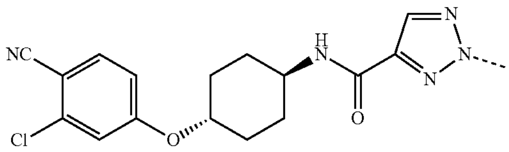
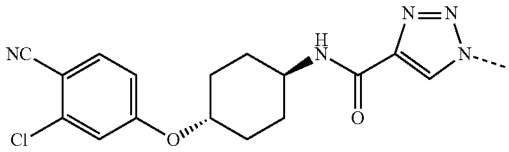
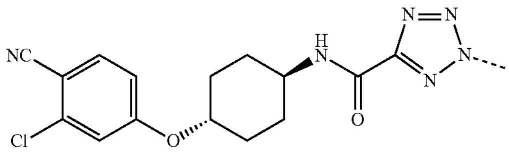
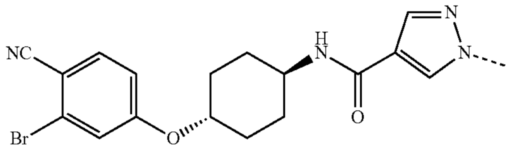
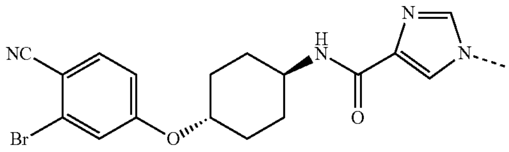
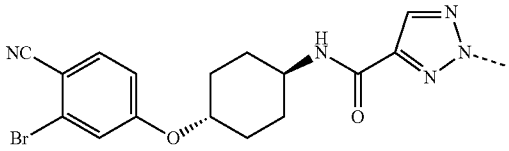
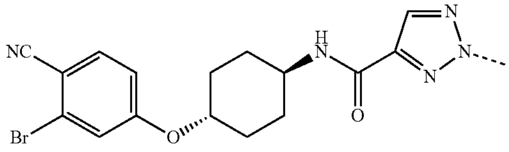
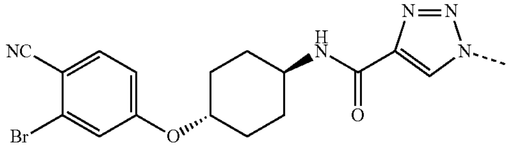

-continued

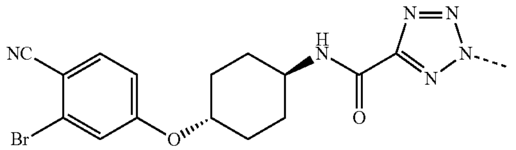

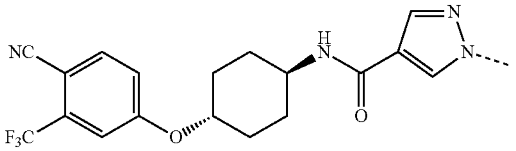

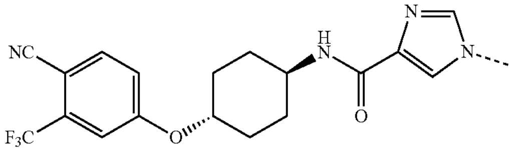

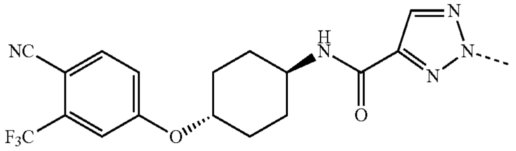

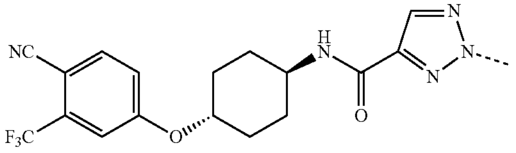

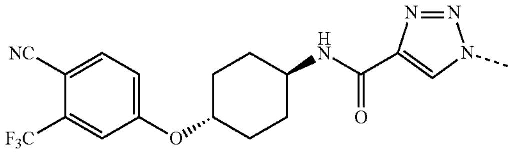

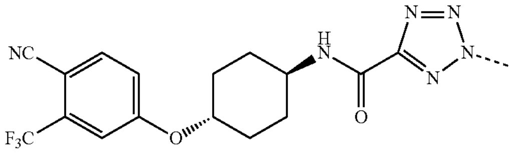

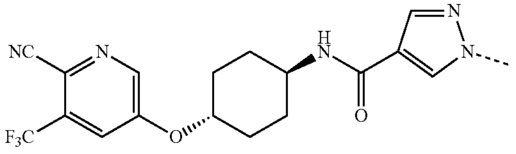

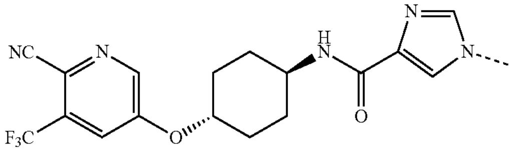

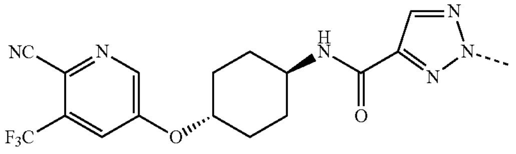

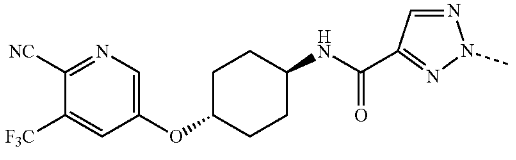

-continued

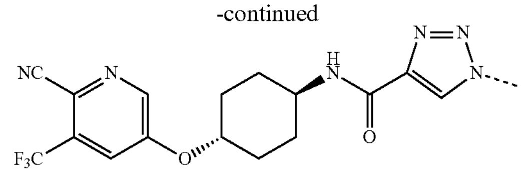

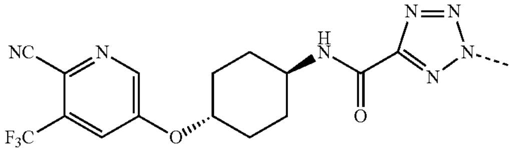

.

Further, said L is selected from the structure of following formula (VIII-A):

VIII-A

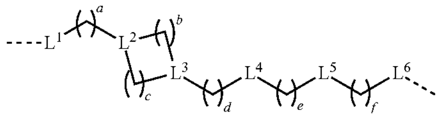

wherein, each of $L^1$, $L^2$, $L^3$, $L^4$, $L^5$, and $L^6$ is independently selected from none, a bond, O, S, $NR^{L1}$, $CR^{L2}R^{L3}$, C═O, C═S, SO, SO2, substituted or unsubstituted alkenyl, substituted or unsubstituted alkynyl, substituted or unsubstituted monocyclic alkyl, substituted or unsubstituted monocyclic heterocyclic group, substituted or unsubstituted aryl, substituted or unsubstituted heteroaryl, substituted or unsubstituted bridged cycloalkyl, substituted or unsubstituted bridged heterocyclic group, substituted or unsubstituted spirocycloalkyl, substituted or unsubstituted heterospirocyclic group, substituted or unsubstituted fused cycloalkyl, and substituted or unsubstituted fused heterocyclic group;

the above-mentioned substituents are selected from $C_{1-6}$ alkyl, $-L^7$-OH, halogen, and L7 is selected from 0-6 methylenes;

each of $R^{L1}$, $R^{L2}$, and $R^{L3}$ is independently selected from the group consisting of H, $C_{1-6}$ alkyl or a halogenated compound thereof or a deuterated compound thereof, 3-8 membered cycloalkyl or heterocyclic group containing 0-2 heteroatoms, or $R^{L2}$ and $R^{L3}$ are linked to form a 3-8 membered ring containing 0-2 heteroatoms; each of a, b, c, d, e, and f is independently selected from an integer of 0 to 5;

$L^1$ and $L^6$ can freely link to ARB or U respectively;

or, said L is selected from the structure of formula (VIII-B):

(VIII-B)

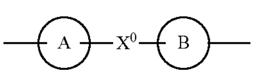

wherein ring A and ring B are each independently selected from the following structures which are halogenated or non-halogenated:

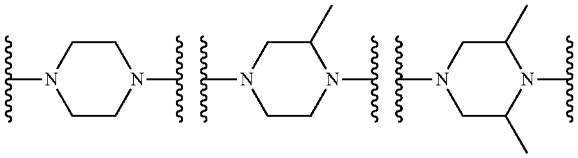

-continued
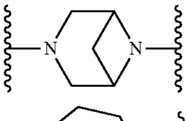
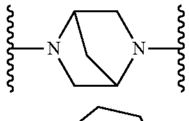
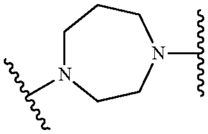
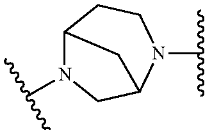
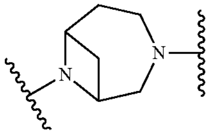
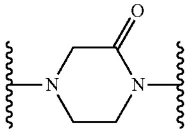
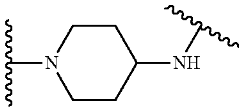
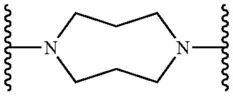
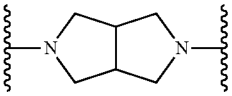
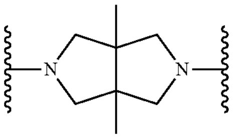
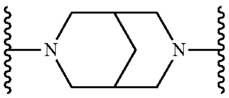
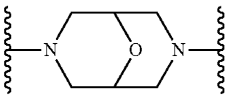
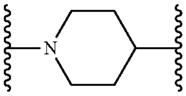
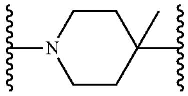
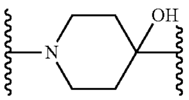
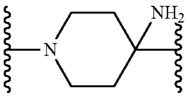
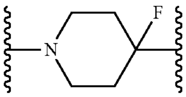
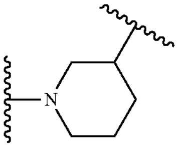
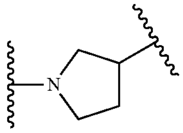
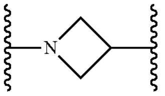
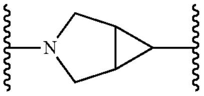
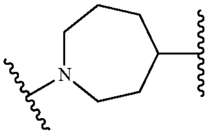
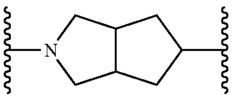
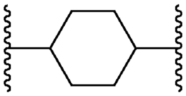
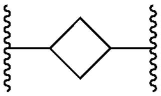
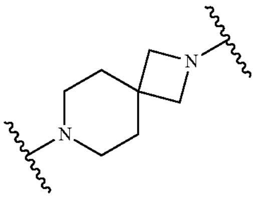
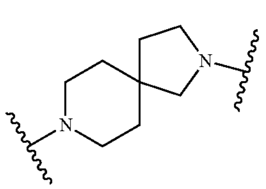
-continued
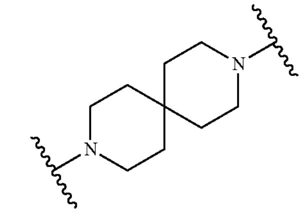
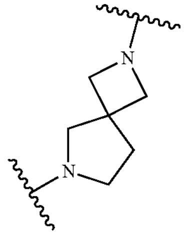
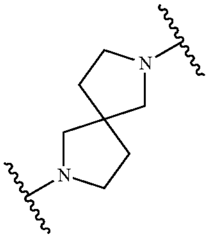
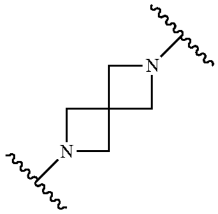
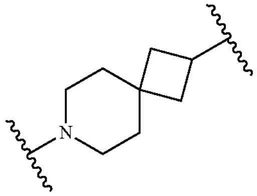
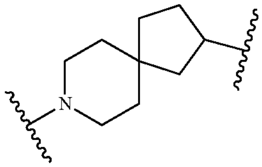
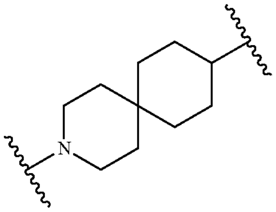
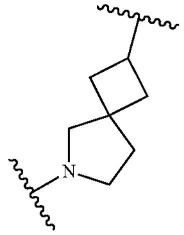
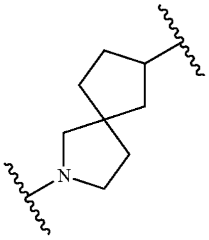
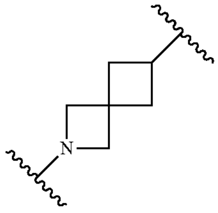
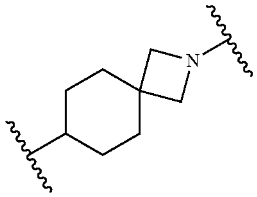
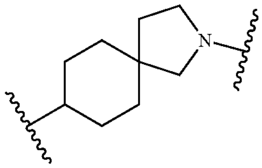
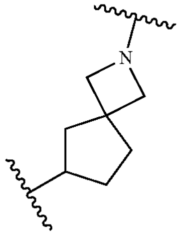
$X^0$ is selected from the group consisting of none, O, S, SO, $SO_2$, $NR^{X1}$, $CR^{X1}R^{X2}$, $R^{X1}$ and $R^{X2}$ are each independently selected from H, halogen, $C_1$-$C_6$ alkyl, $C_3$-$C_6$ cycloalkyl, halogen- or hydroxyl- or amino-substituted $C_1$-$C_6$ alkyl, the group obtained by substituting the carbon in the main chain of $C_1$-$C_6$ alkyl with oxygen or nitrogen, heterocyclic group, aryl, hydroxyl, amino, or $R^{X1}$ and $R^{X2}$ are linked to form 3-7 membered ring;
ring A and ring B can freely link to ARB or U respectively.
Further, said formula (VIII-A) is selected from the following structures:
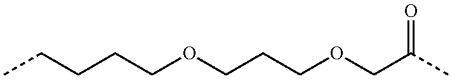
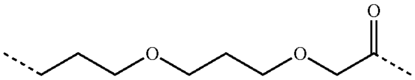
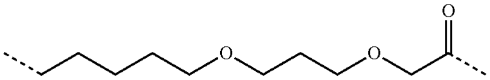
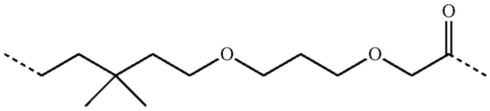
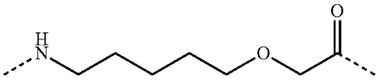
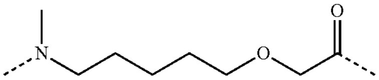
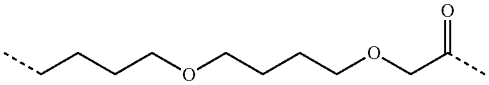
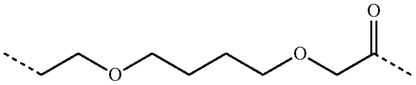
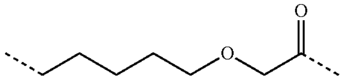
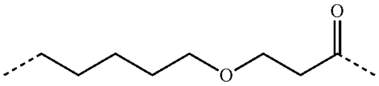
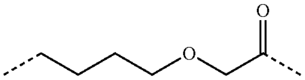
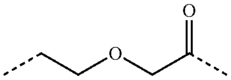
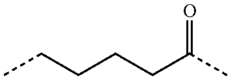
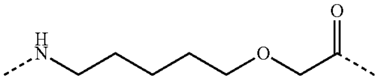
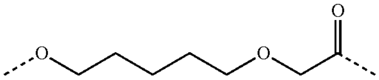
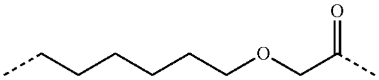
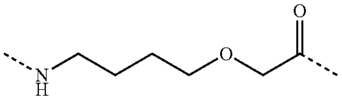
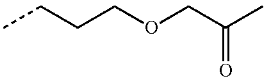
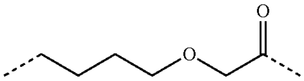
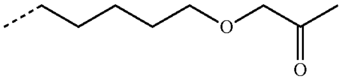
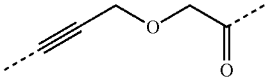
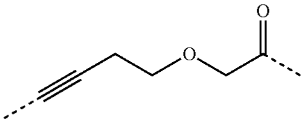
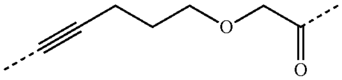
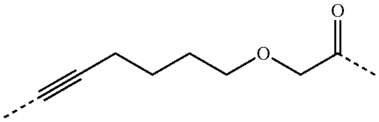
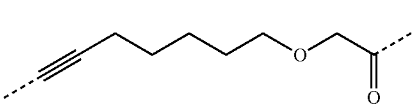
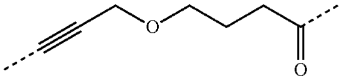
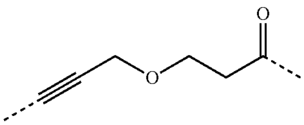
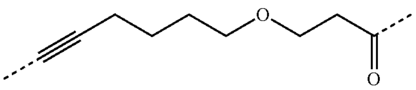
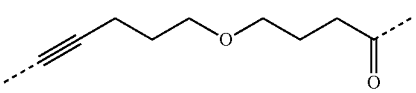
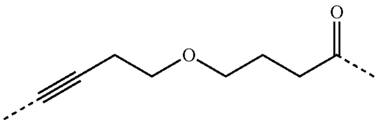
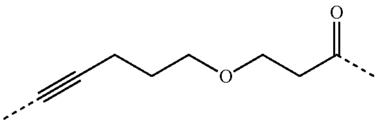
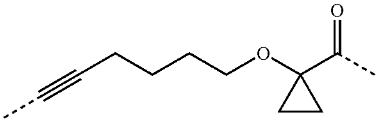
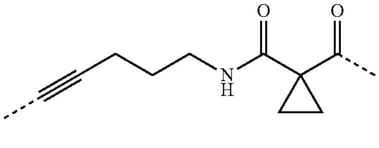
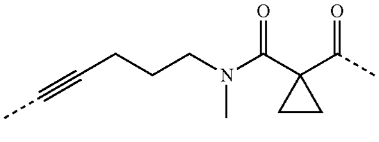

-continued
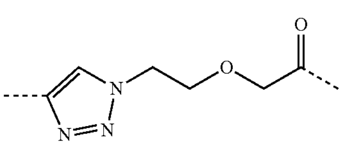 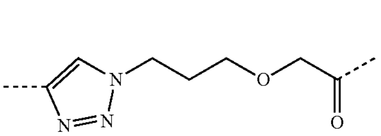 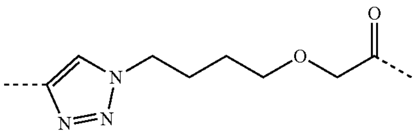
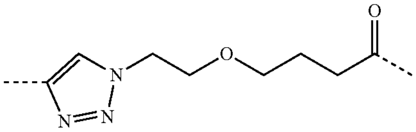 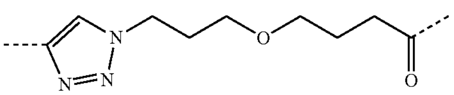
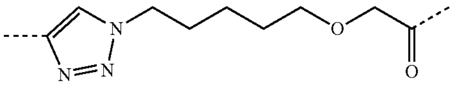 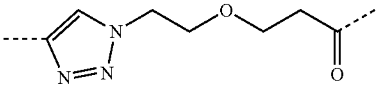
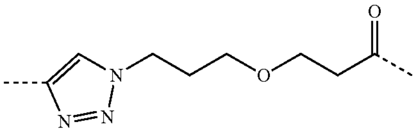 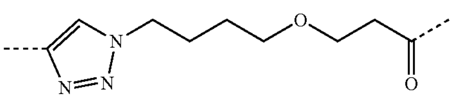
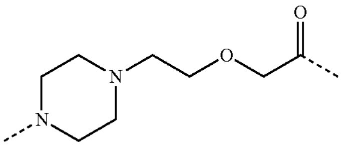 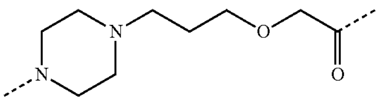
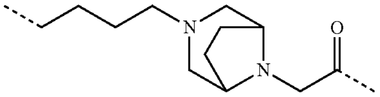 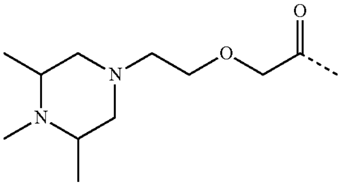
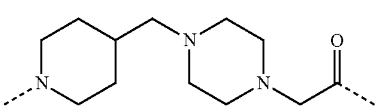 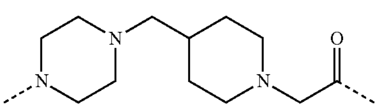 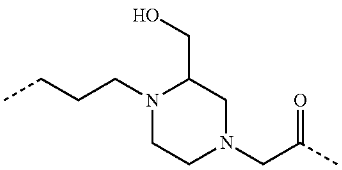
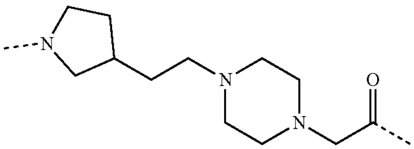 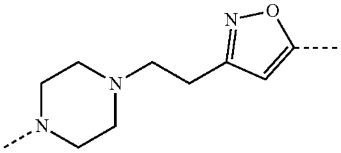 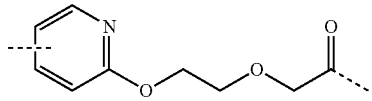
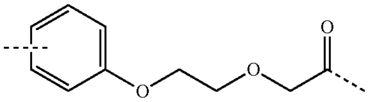 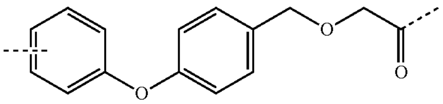
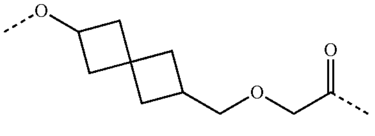 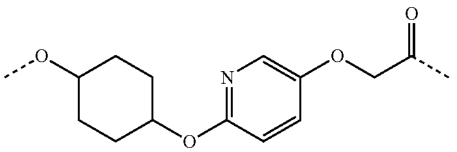 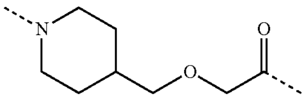
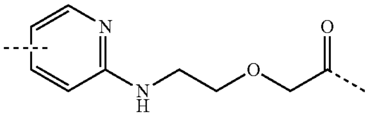 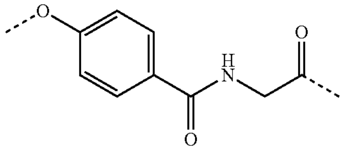 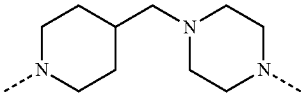

-continued
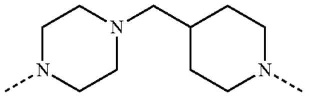
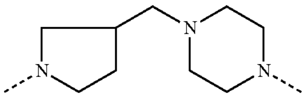
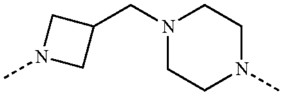
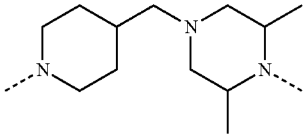
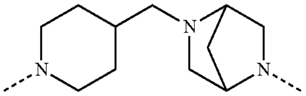
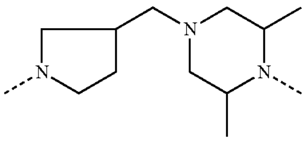
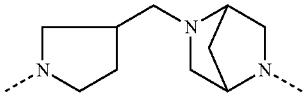
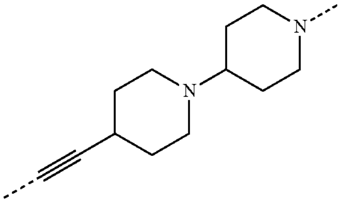
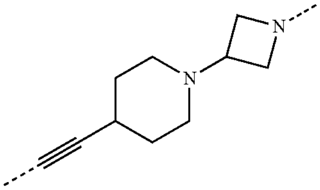
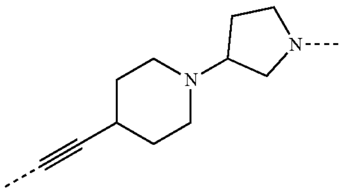
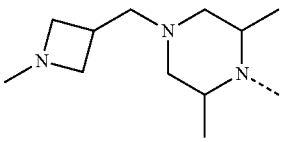
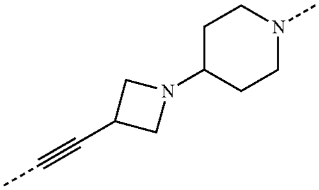
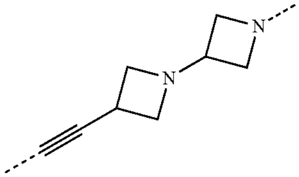
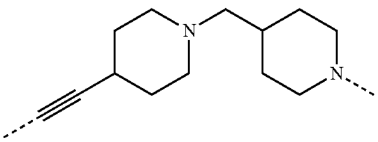
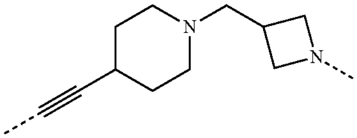
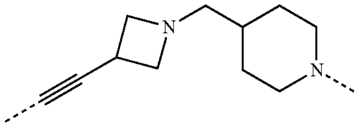
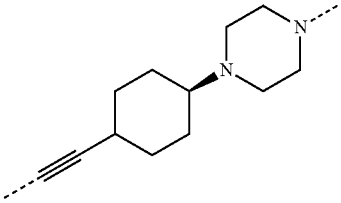
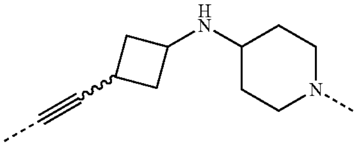
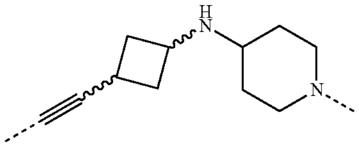
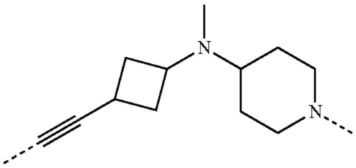
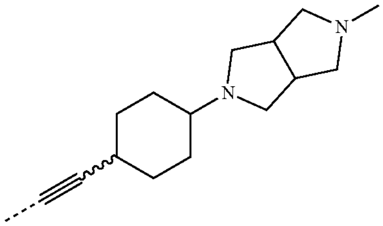
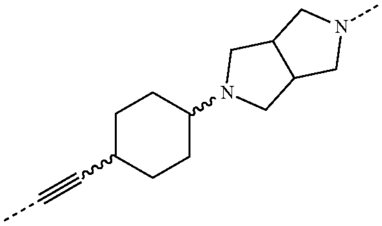
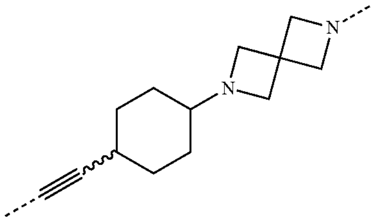
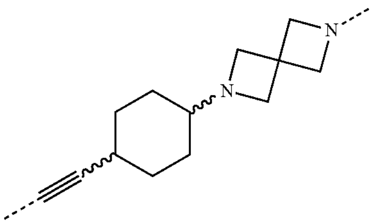
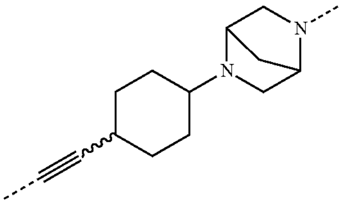

-continued
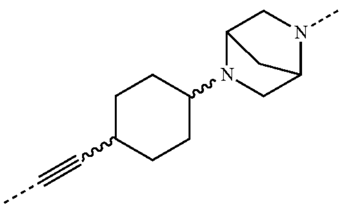
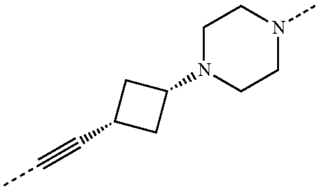
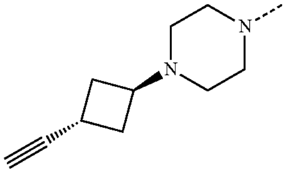
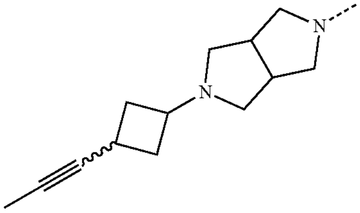
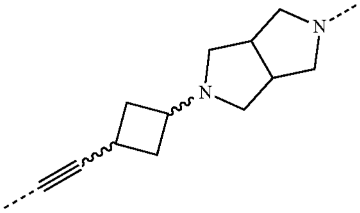
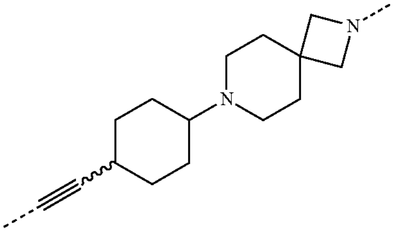
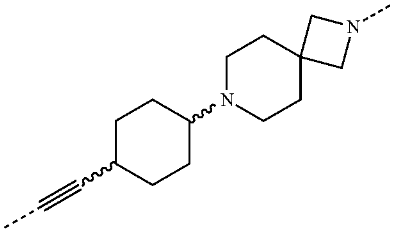
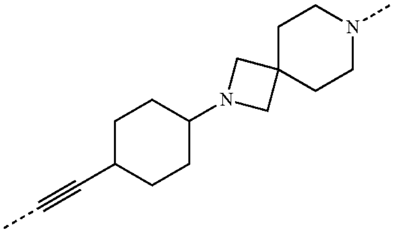
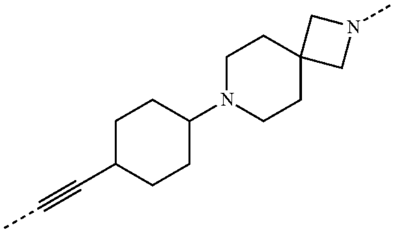
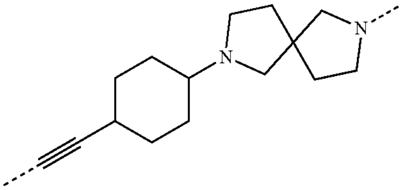
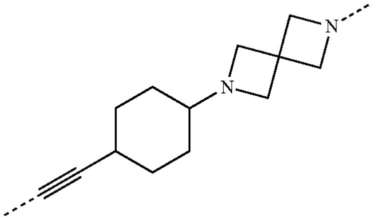
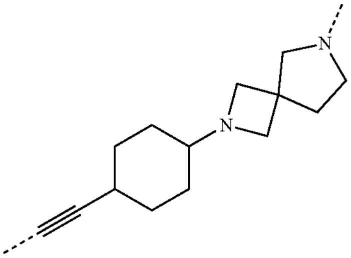
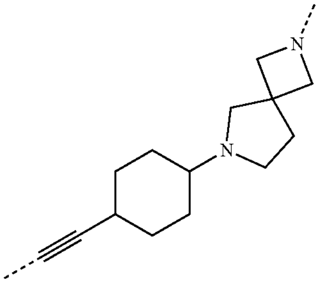
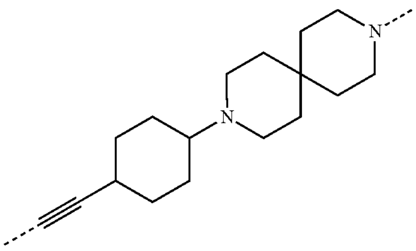
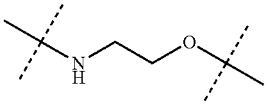,
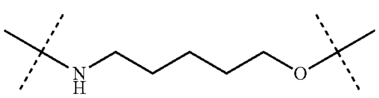,
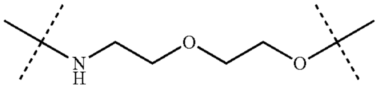,
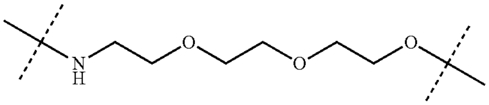,
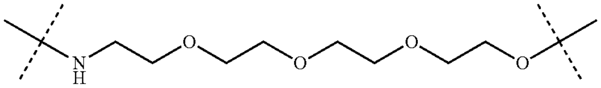, -continued
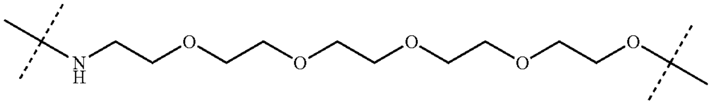,
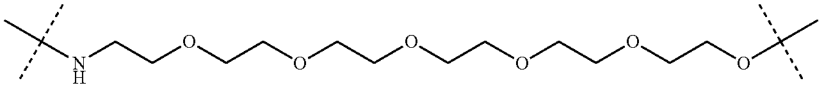,
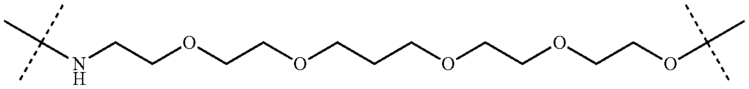,
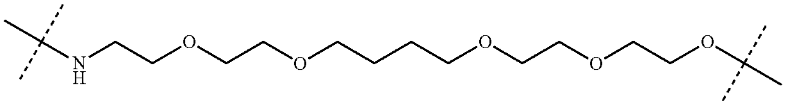,
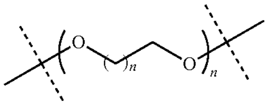, 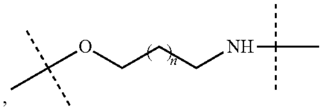, 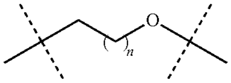, 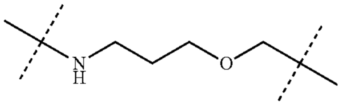,
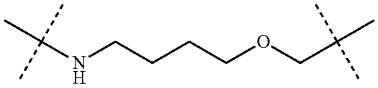, 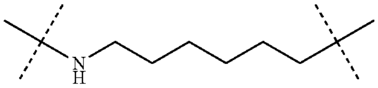,
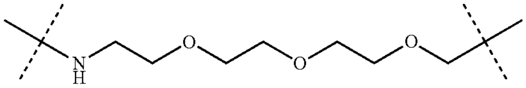,
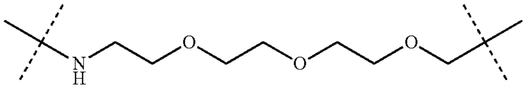, 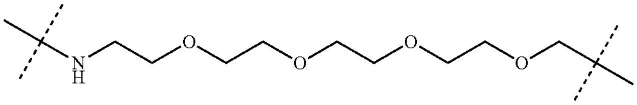,
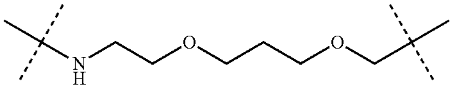, 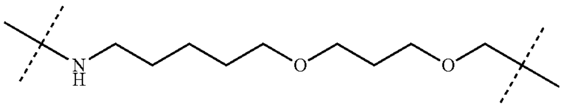,
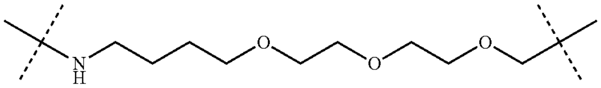, 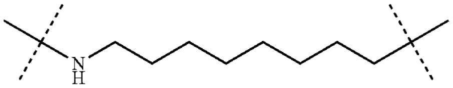,
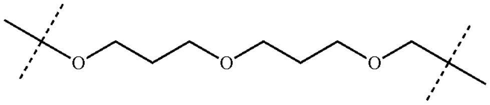, 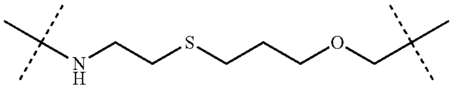,
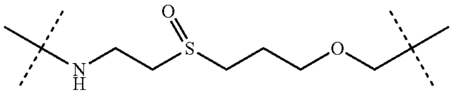, 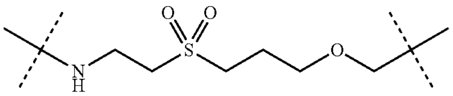,
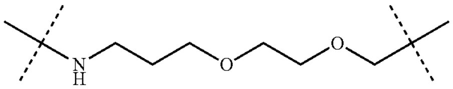, 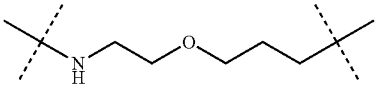,
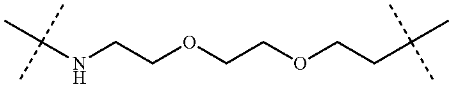, 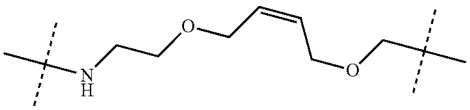,
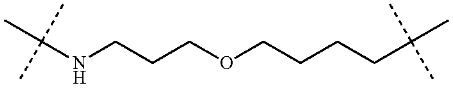, 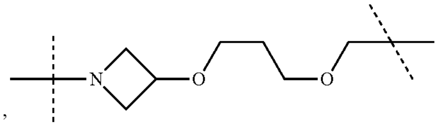,
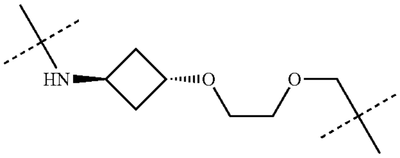, 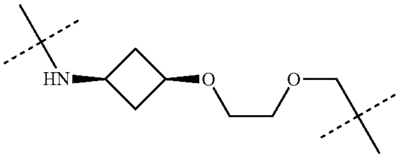, -continued
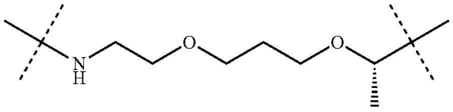,
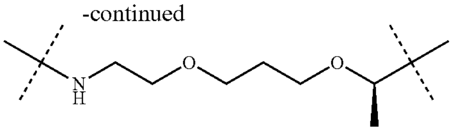,
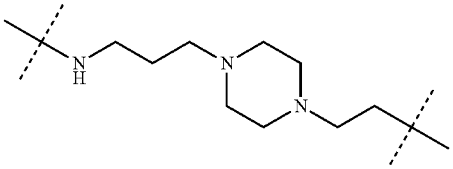,
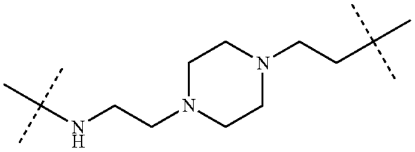,
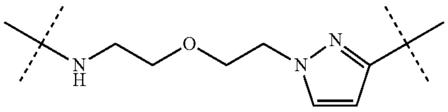,
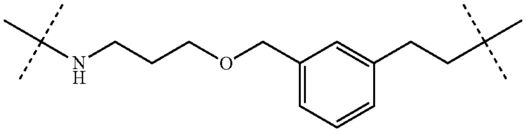,
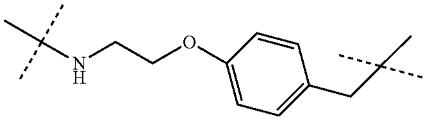,
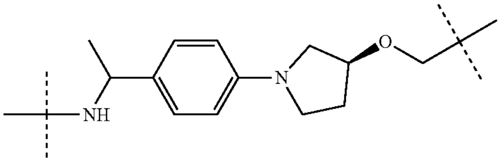,
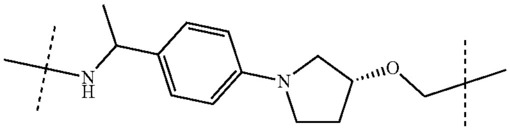,
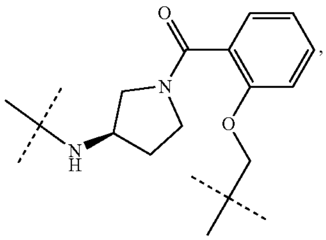,
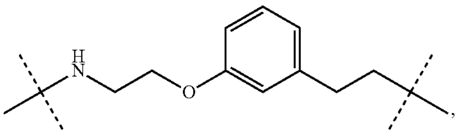,
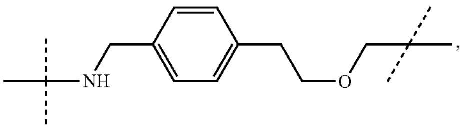,
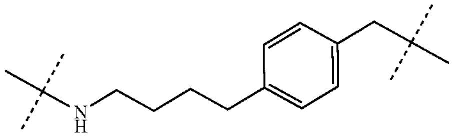,
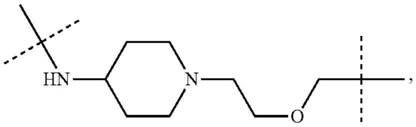,
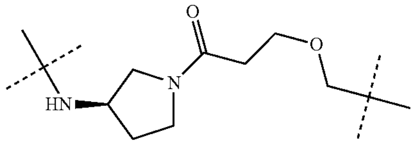,
-continued
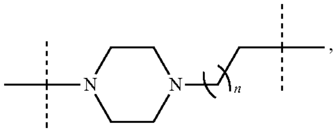,
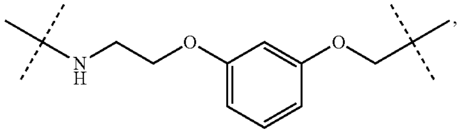,
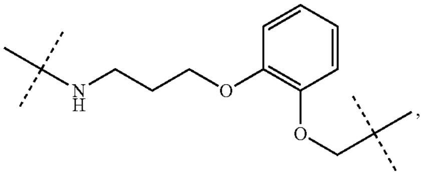,
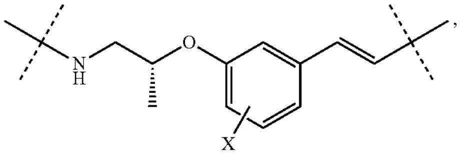,
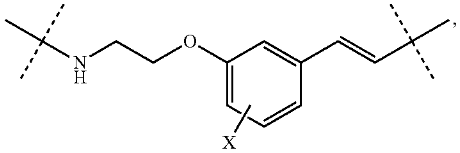,
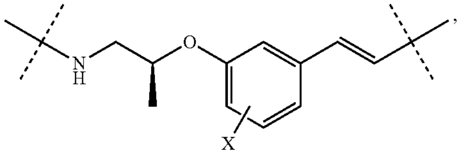, -continued
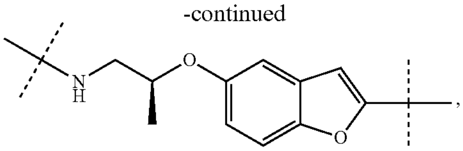,
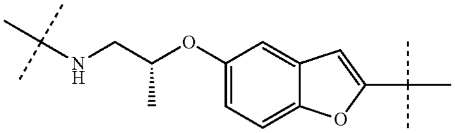,
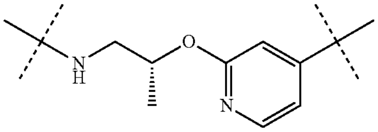,
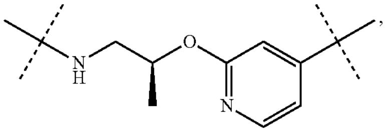,
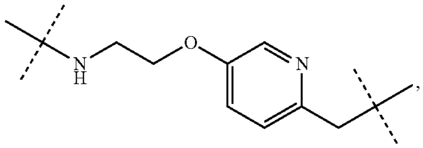,
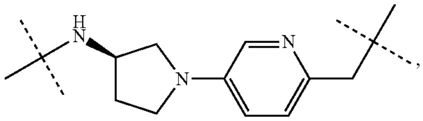,
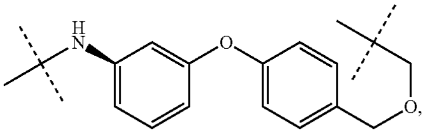,
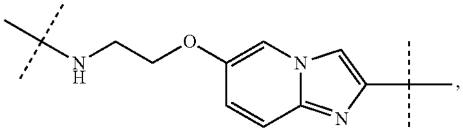,
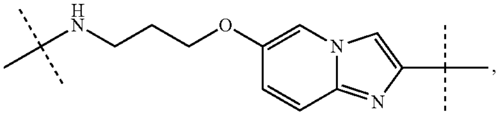,
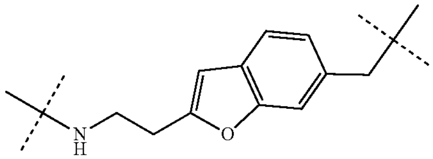
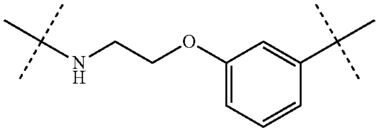,
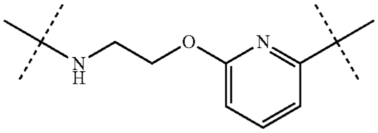,
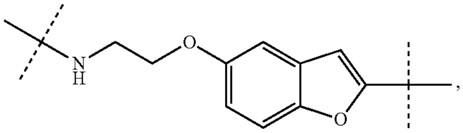,
-continued
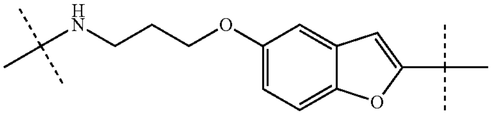,
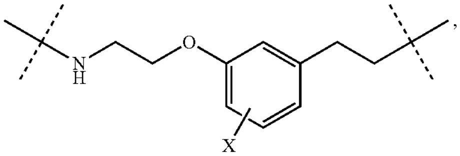,
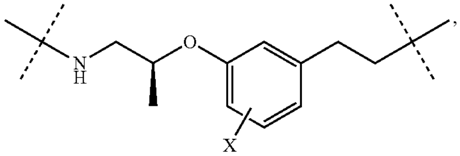,
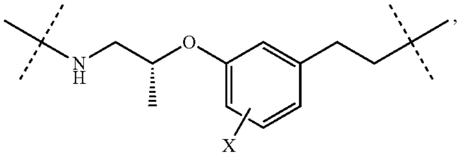,
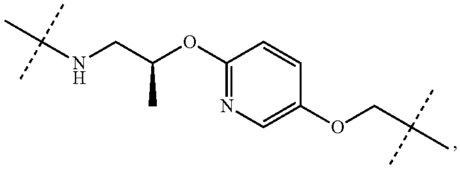,
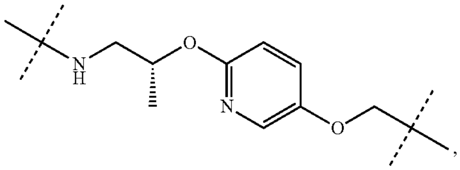,
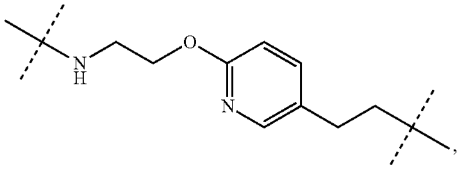,
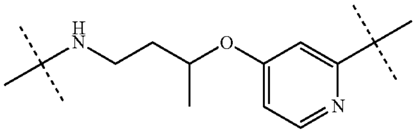,
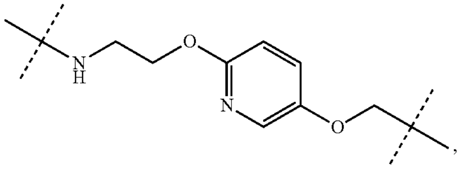,
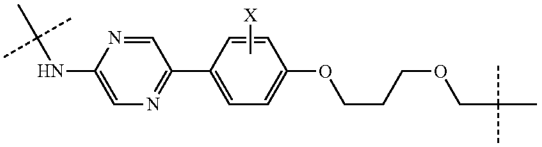,
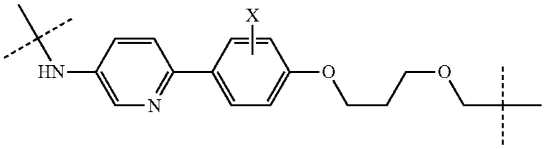, -continued
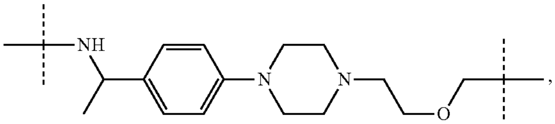
,
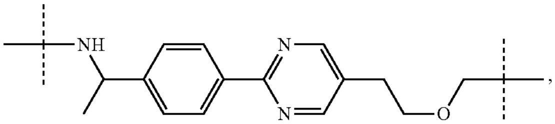
,
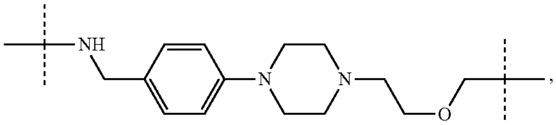
,
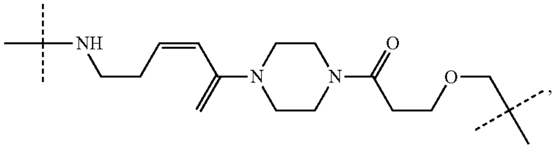
,
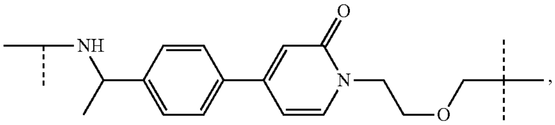
,
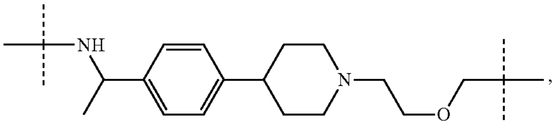
,
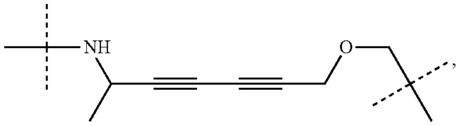
,
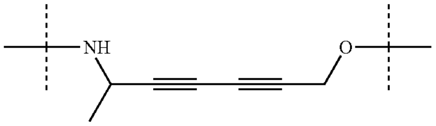
,
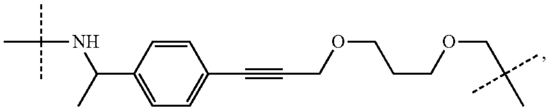
,
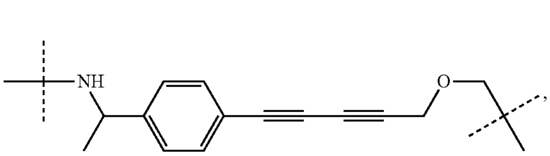
,
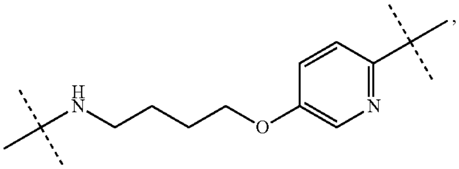
,
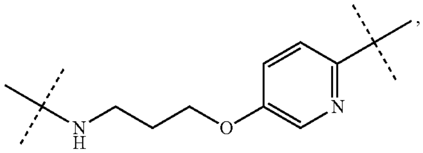
,
-continued
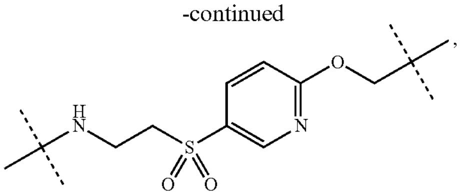
,
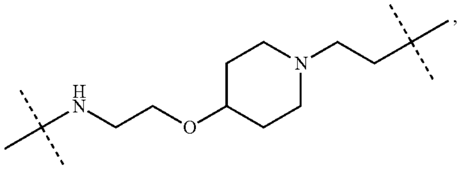
,
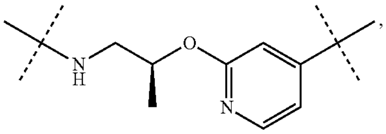
,
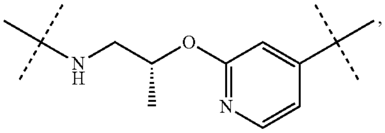
,
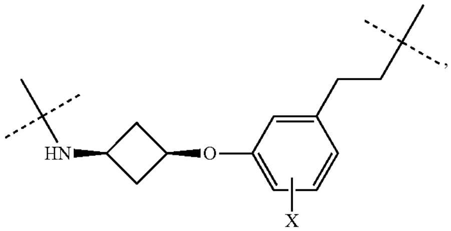
,
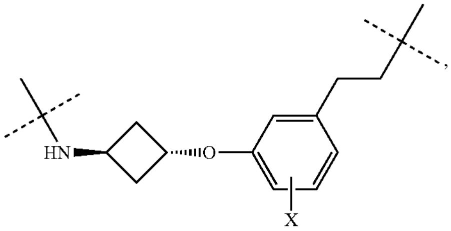
,
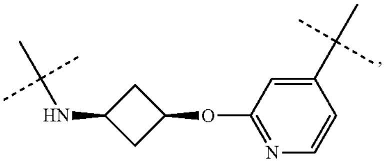
,
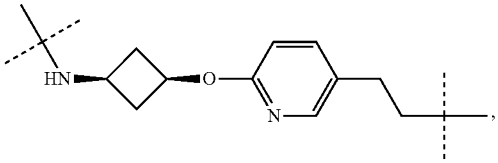
,
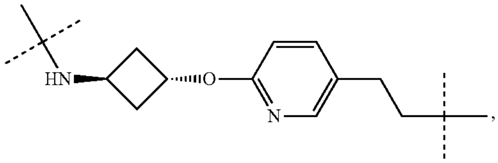
,
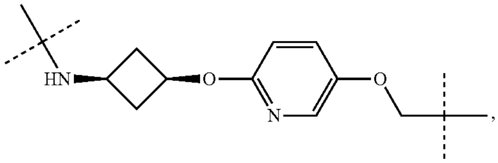
, -continued
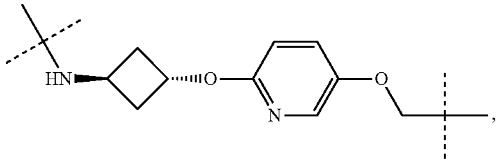
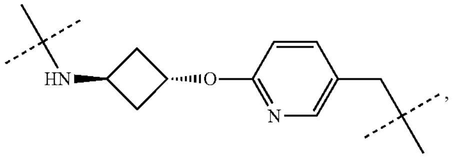
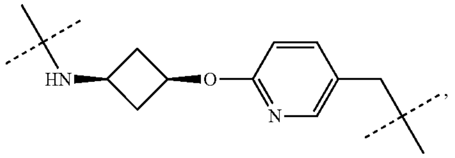
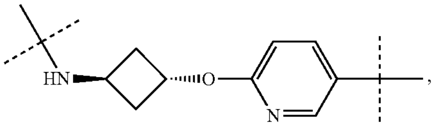
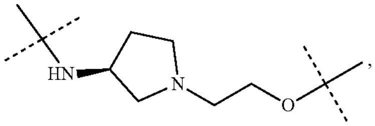
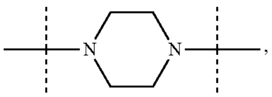
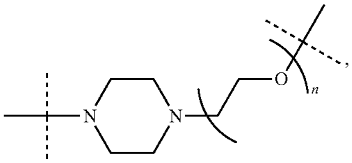
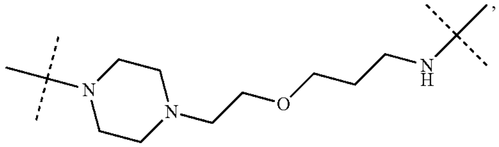
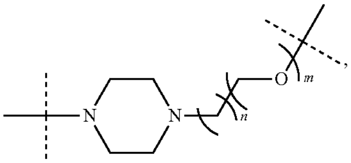
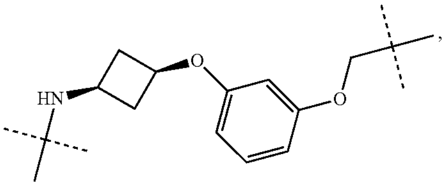
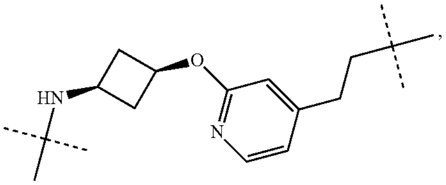
-continued
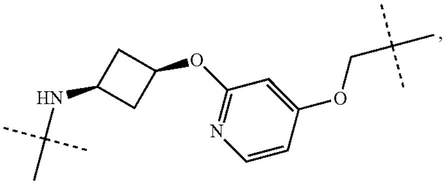
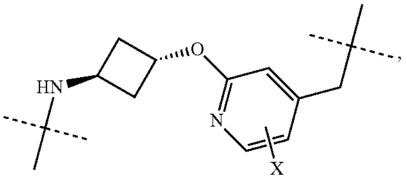
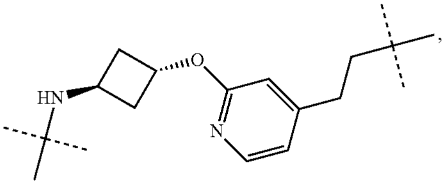
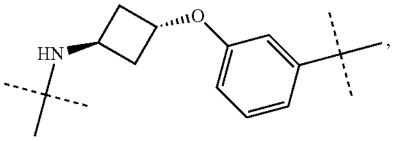
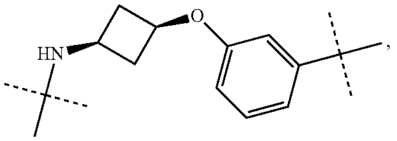
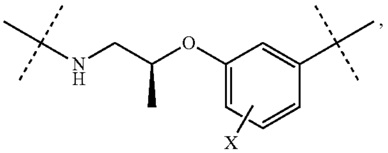
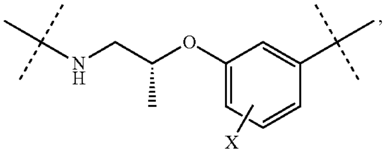
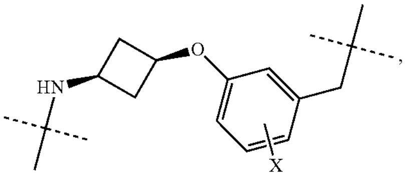
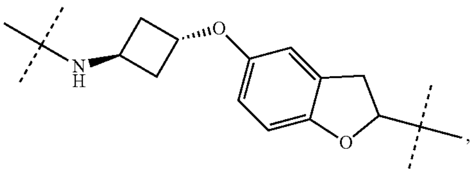
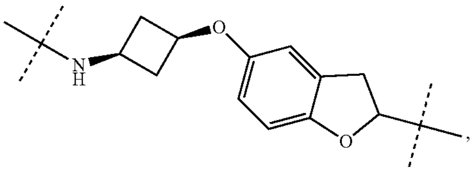

-continued
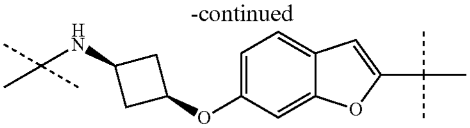
,
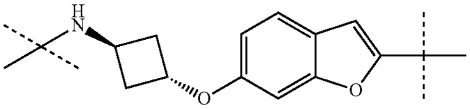
,
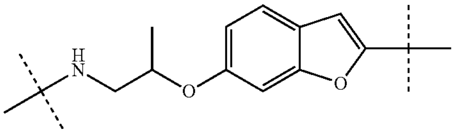
,
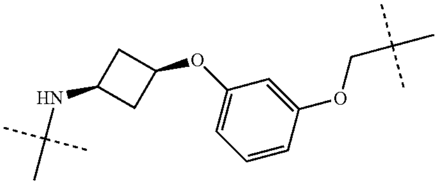
,
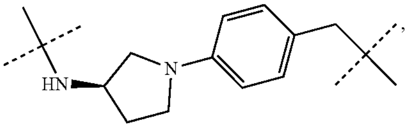
,
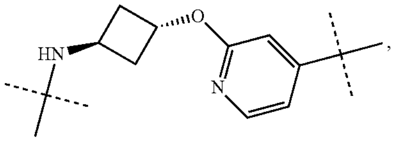
,
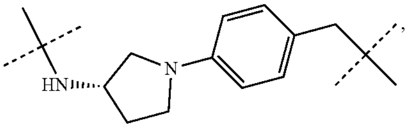
,
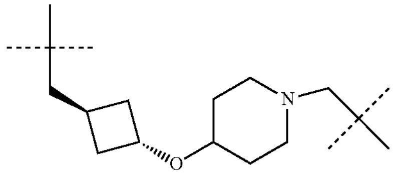
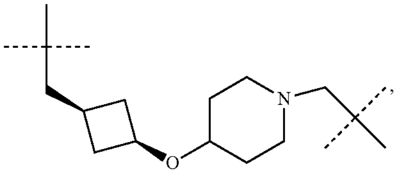
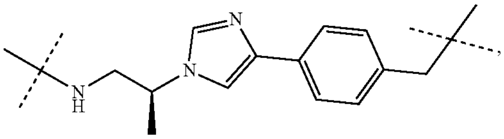
,
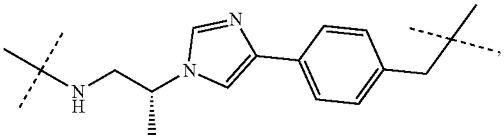
,
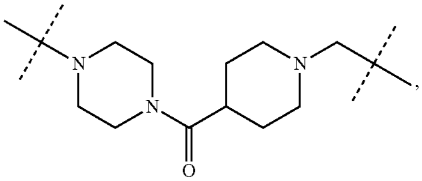
,
-continued
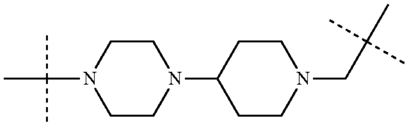
,
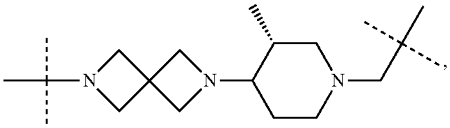
,
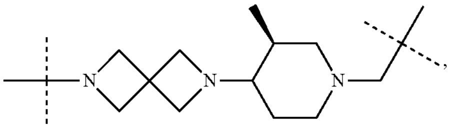
,
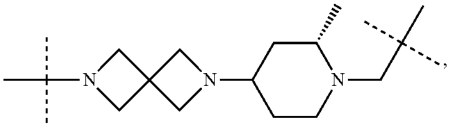
,
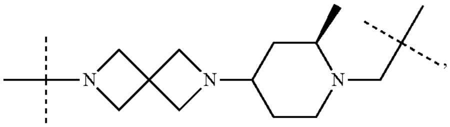
,
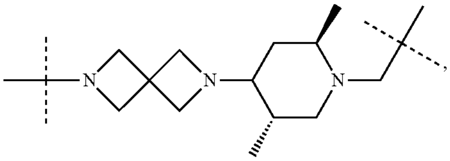
,
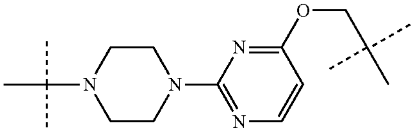
,
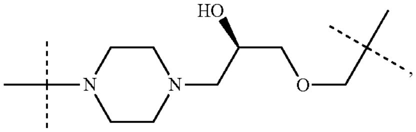
,
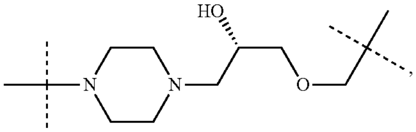
,
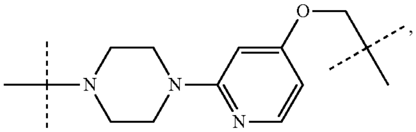
,
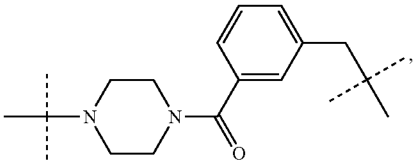
,
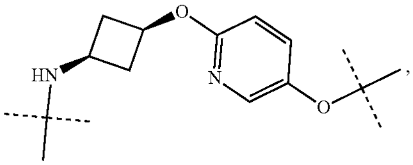
,

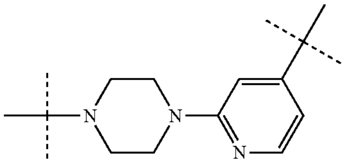
,
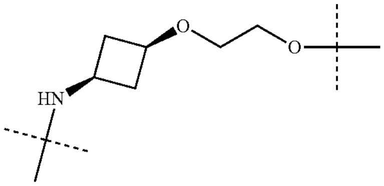
,
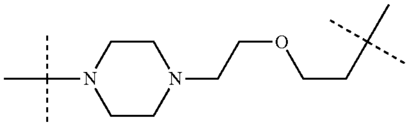
,
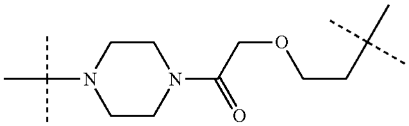
,
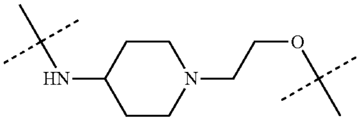
,
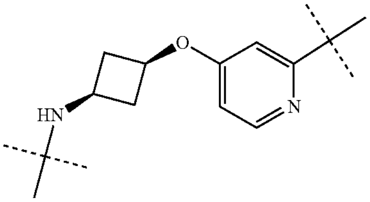
,
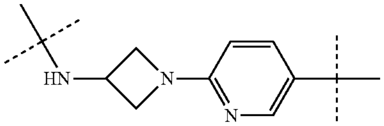
,
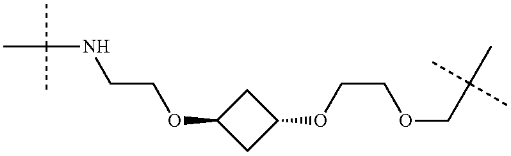
,
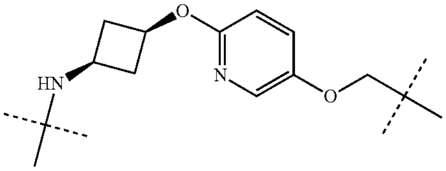
,
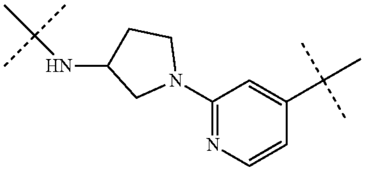
,
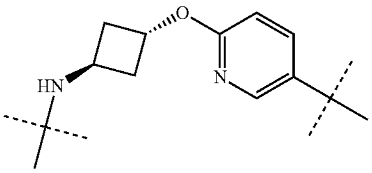
,
-continued
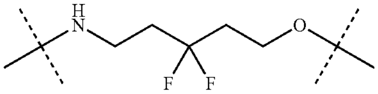
,
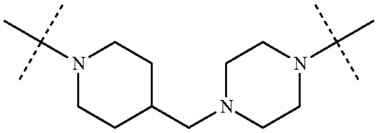
,
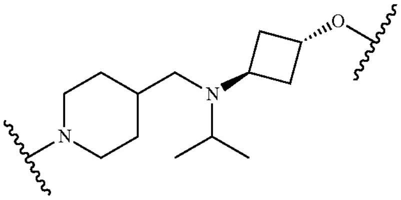
,
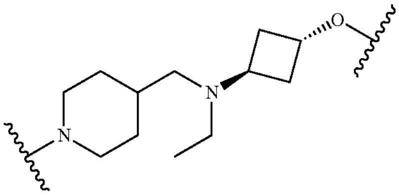
,
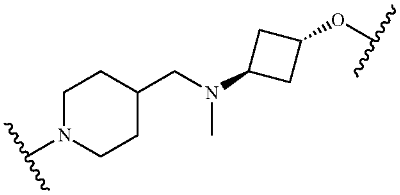
,
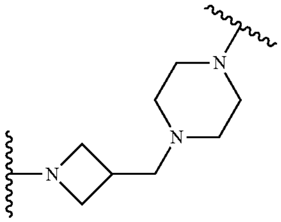
,
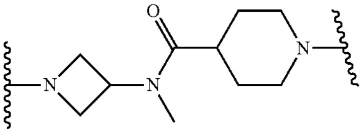
,
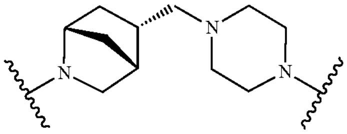
,
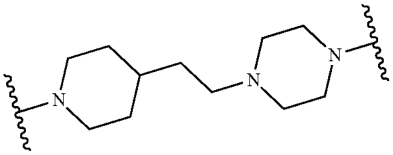
,
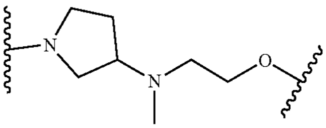
, -continued
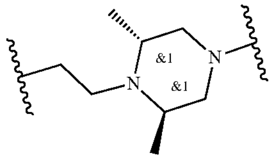
,
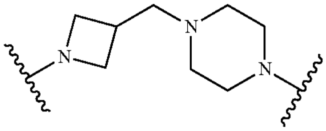
,
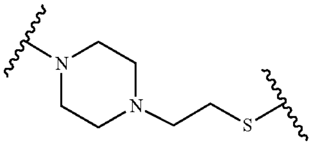
,
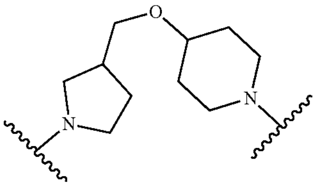
,
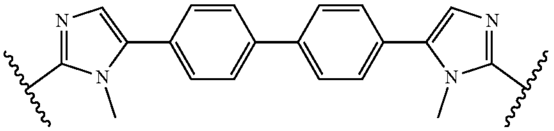
,
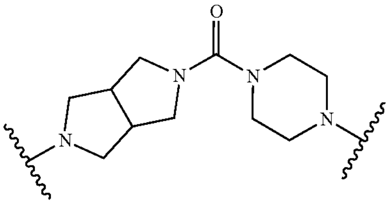
,
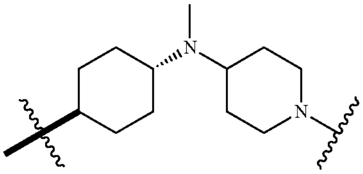
,
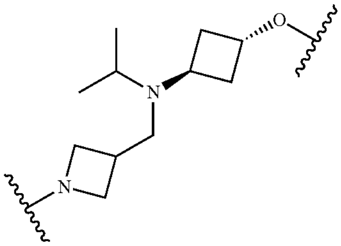
,
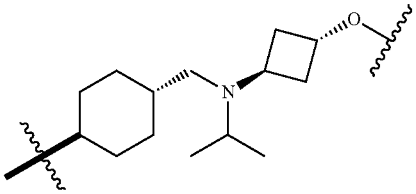
,
-continued
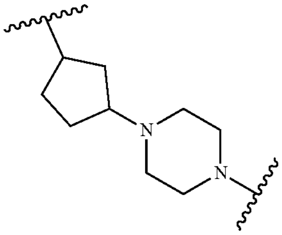
,
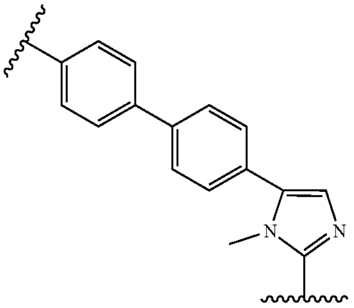
,
wherein, X is selected from H or halogen, and m and n are each independently selected from an integer of 0 to 5.
Further, said L is selected from the following structures:
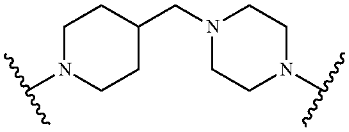
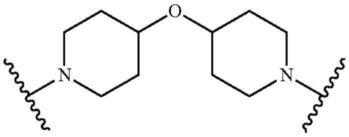
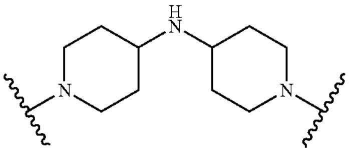
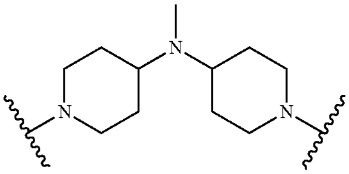
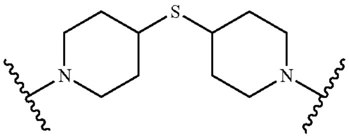
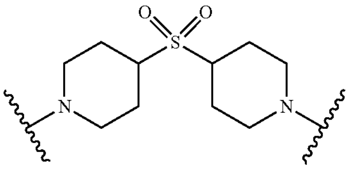

-continued
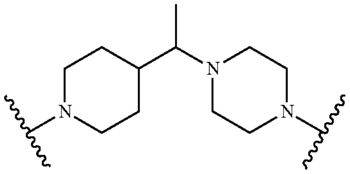
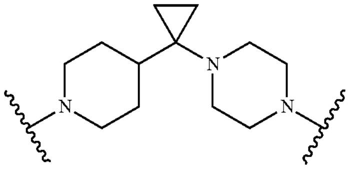
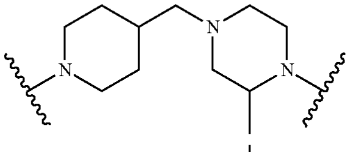
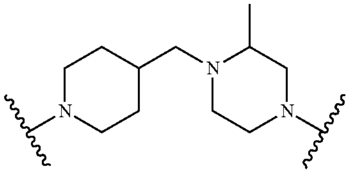
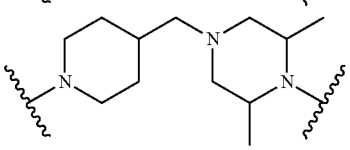
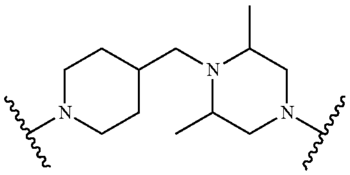
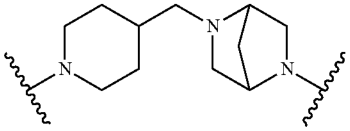
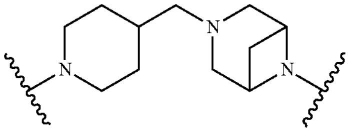
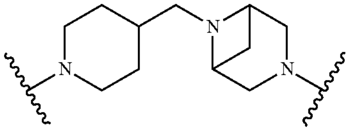
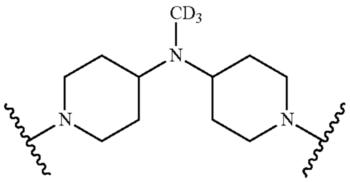
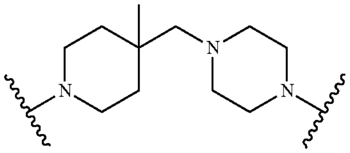
-continued
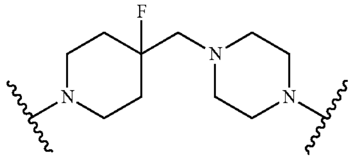
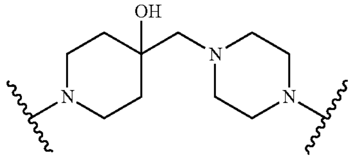
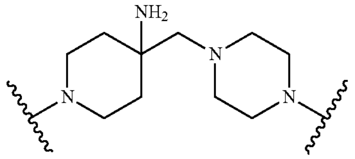
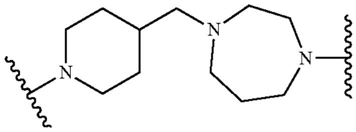
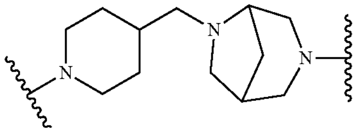
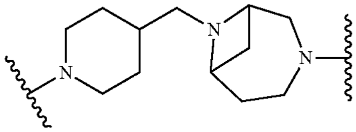
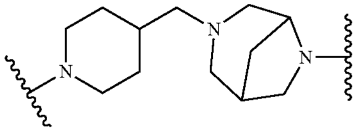
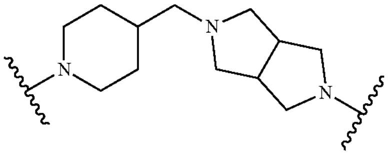
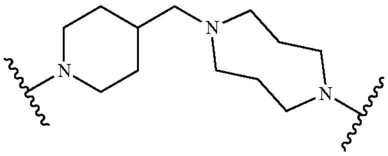
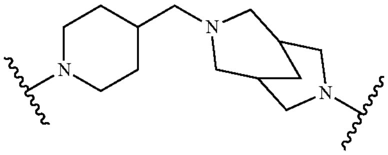
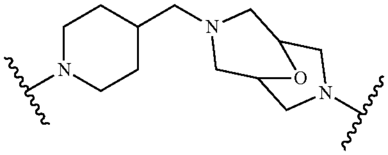

-continued
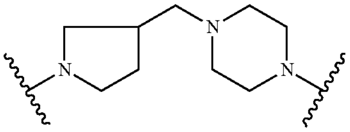
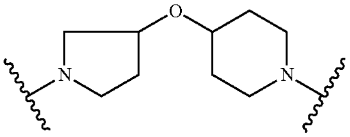
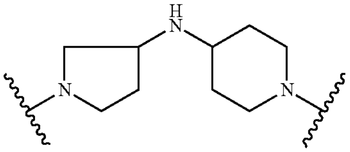
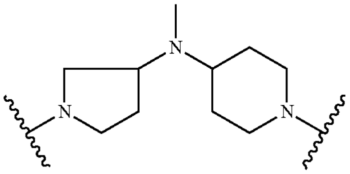
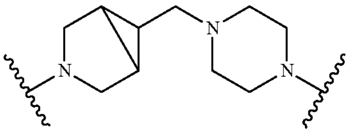
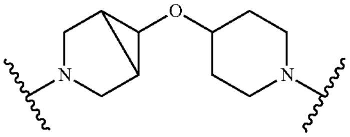
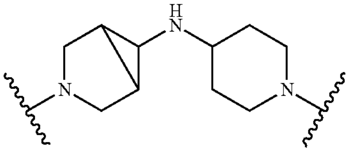
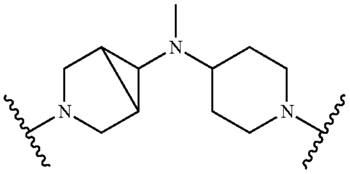
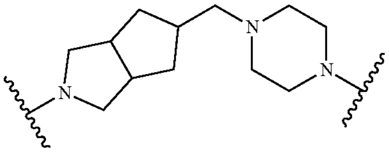
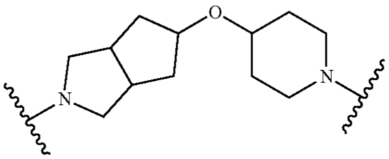
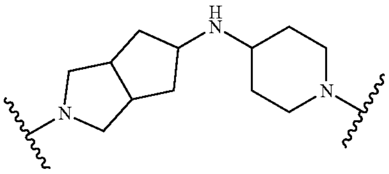
-continued
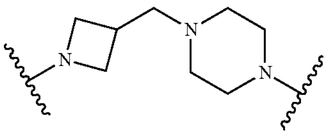
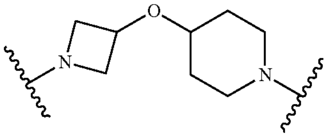
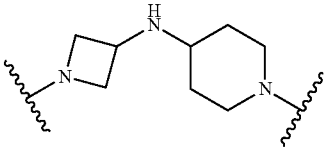
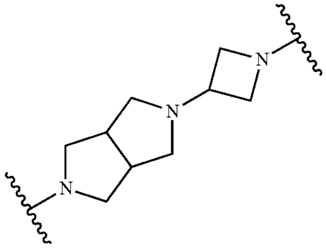
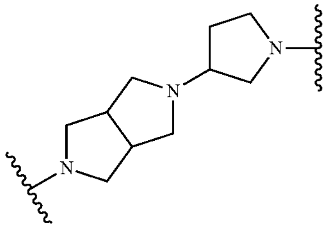
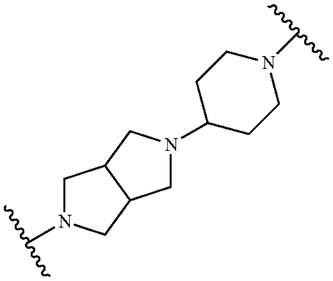
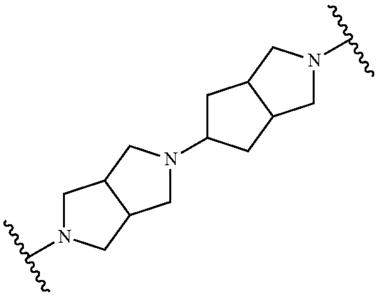

-continued
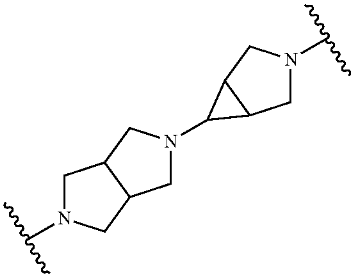
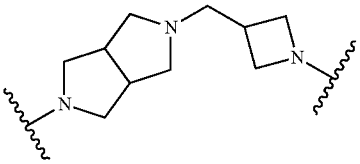
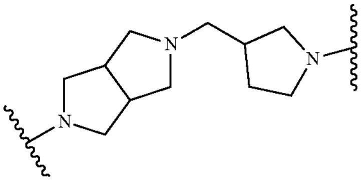
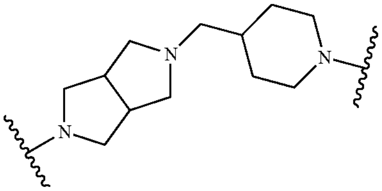
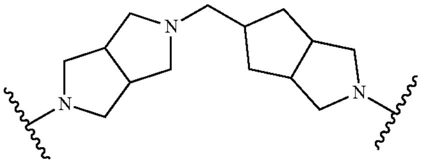
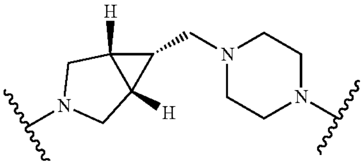
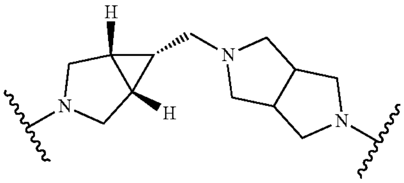
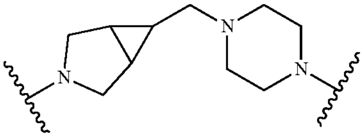
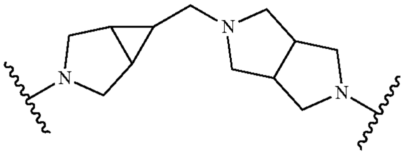
-continued
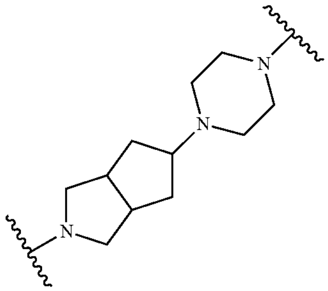
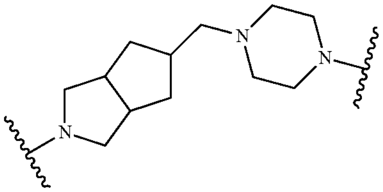
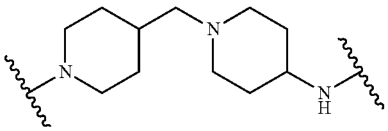
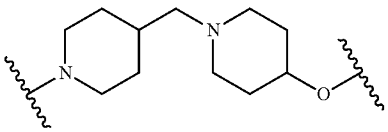
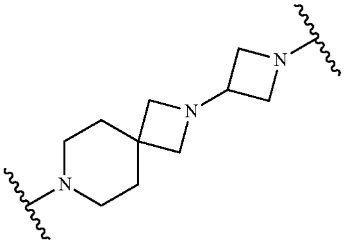
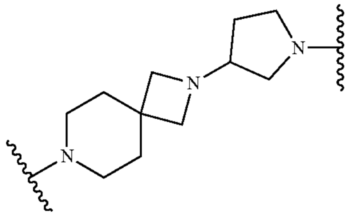
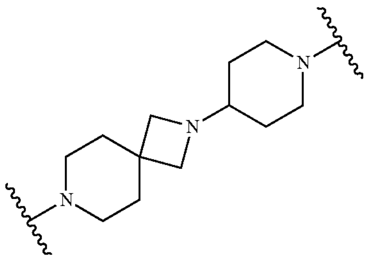

-continued
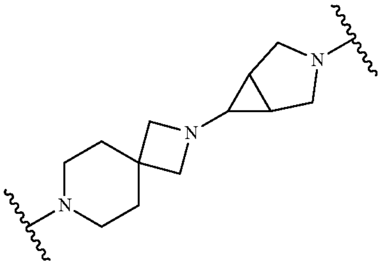
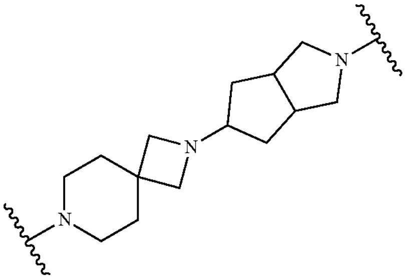
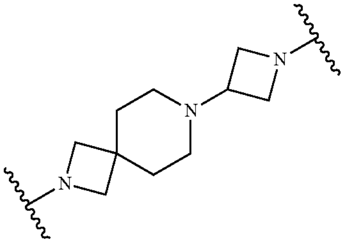
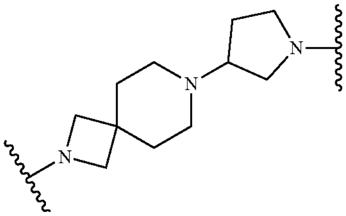
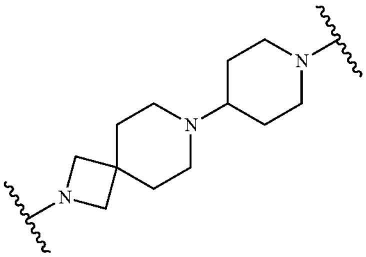
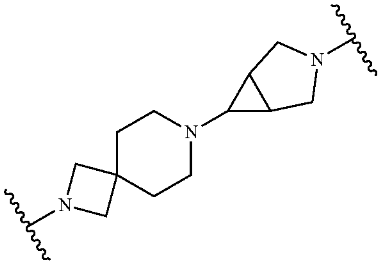
-continued
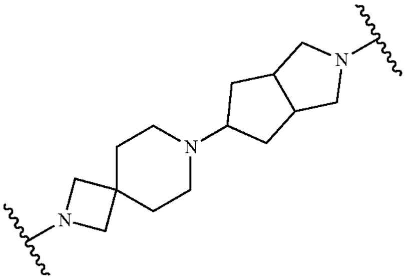
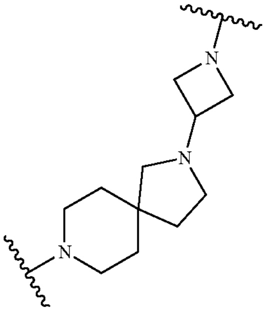
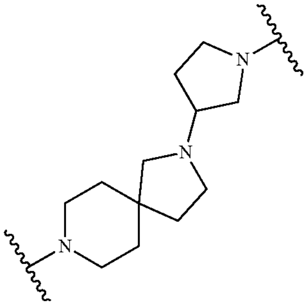
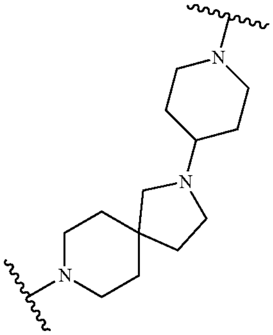
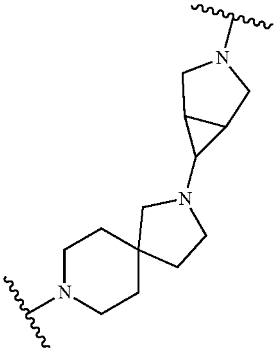
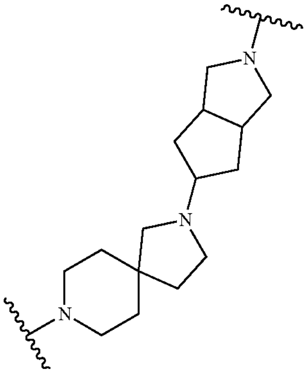
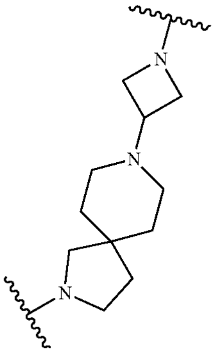

-continued
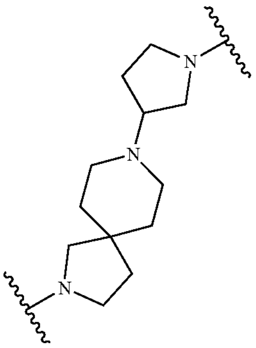
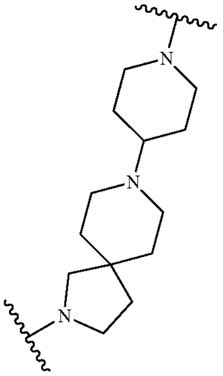
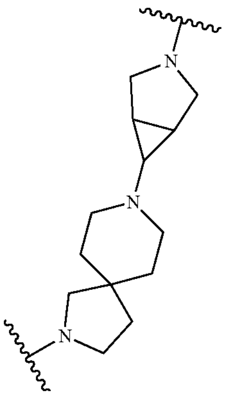
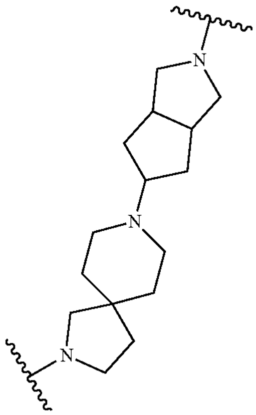
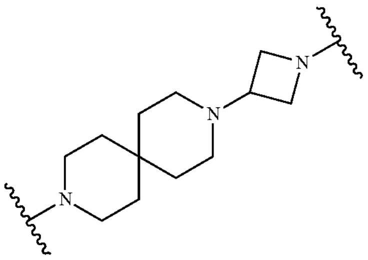
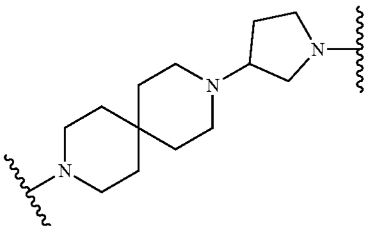
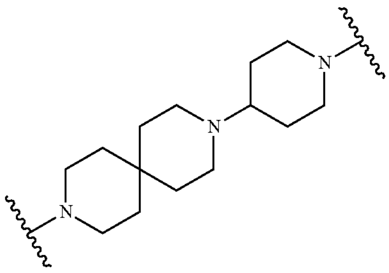
-continued
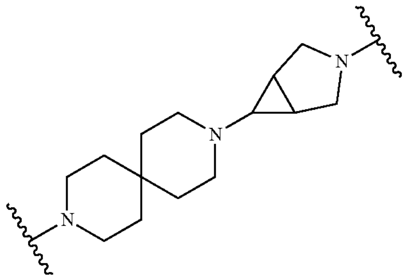
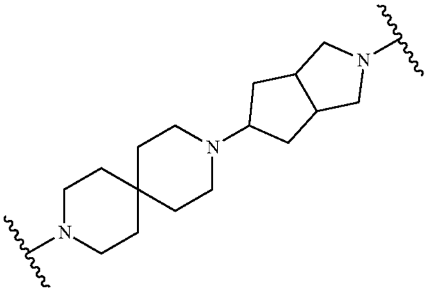
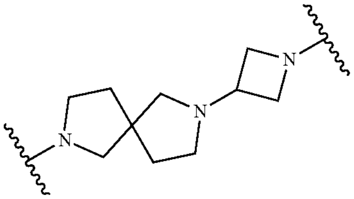
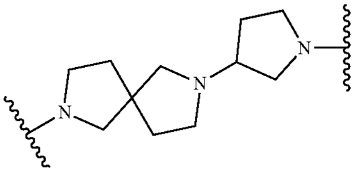
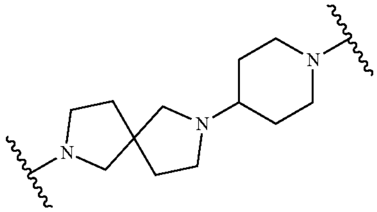
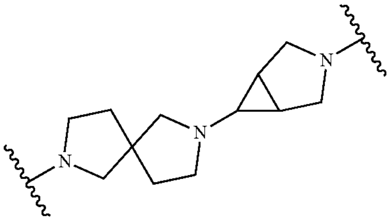
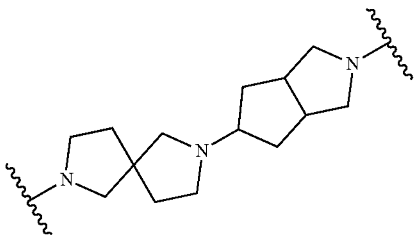

-continued
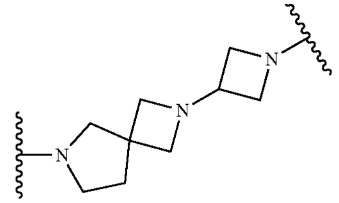
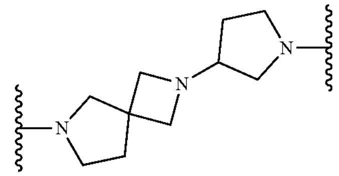
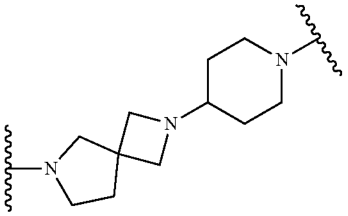
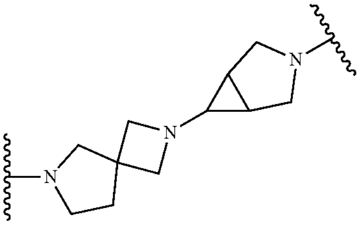
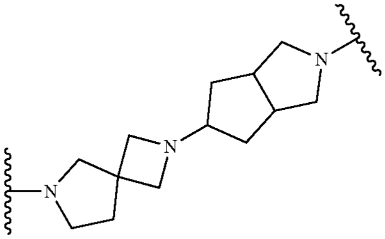
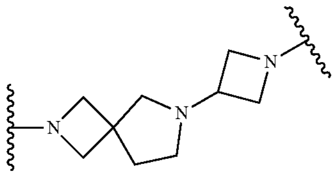
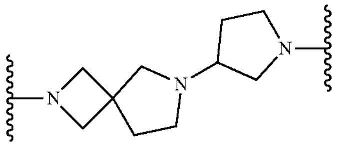
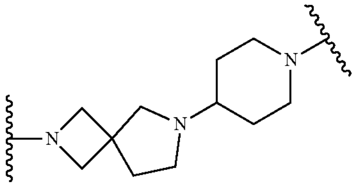
-continued
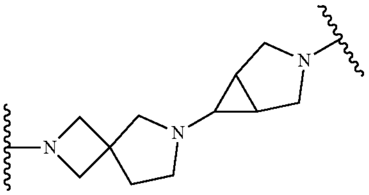
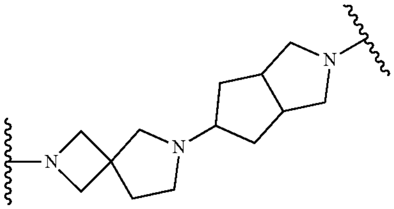
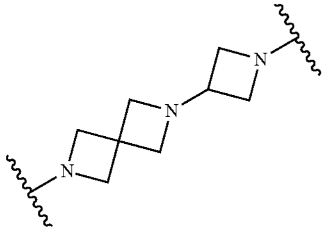
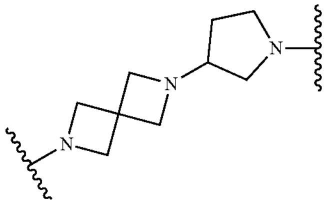
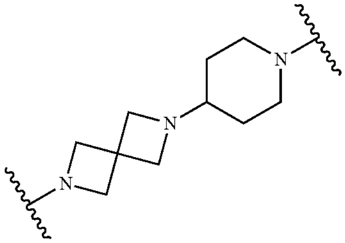
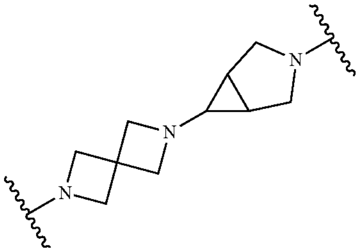
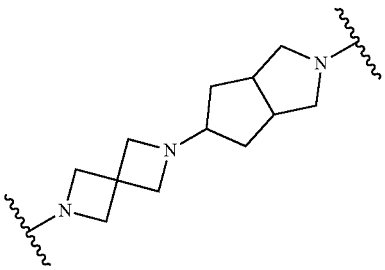

-continued
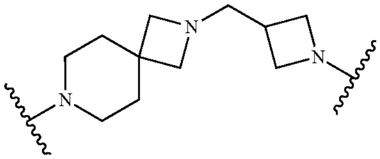
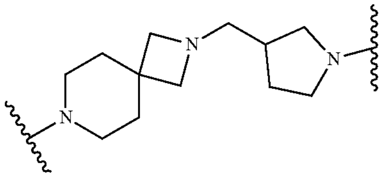
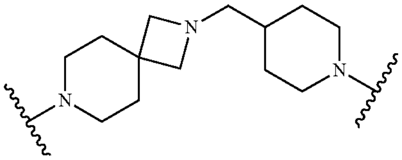
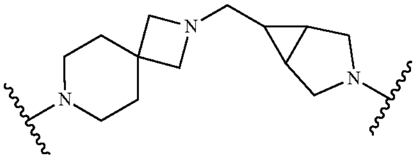
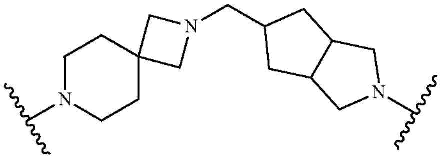
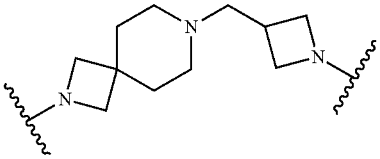
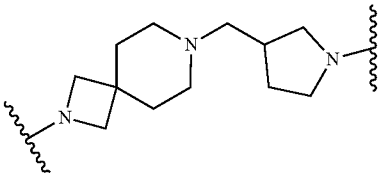
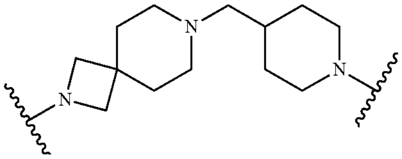
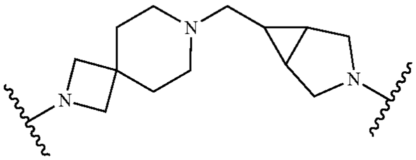
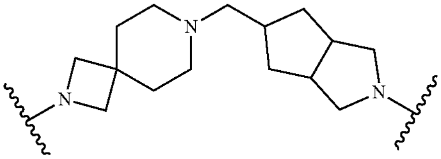
-continued
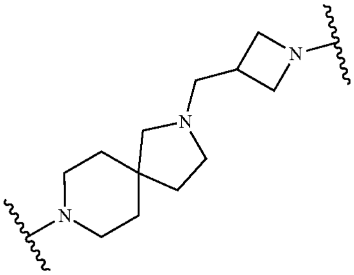
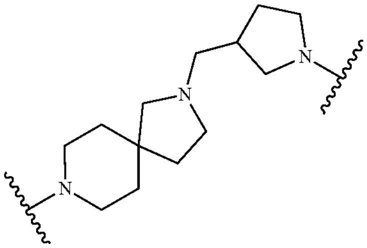
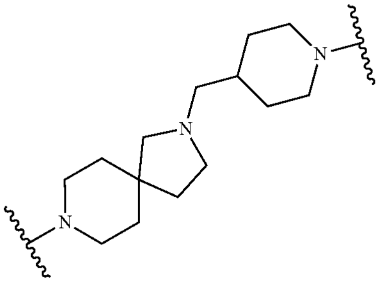
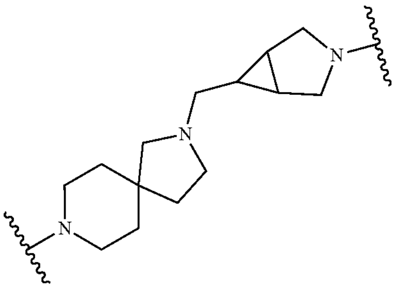
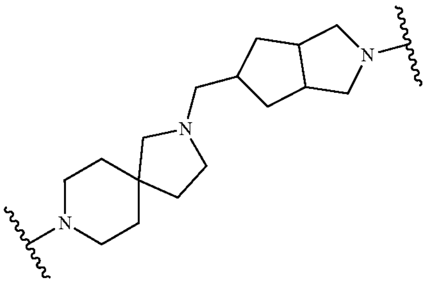
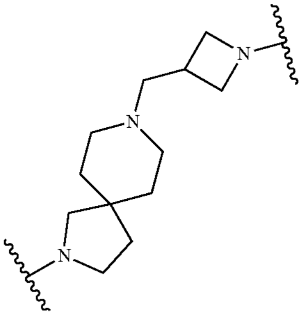

-continued
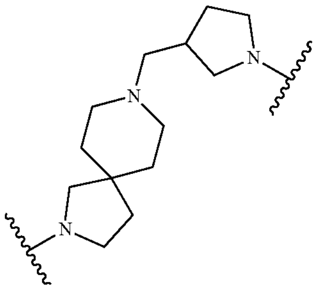
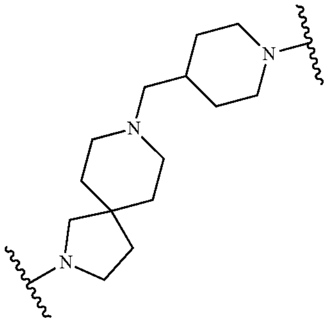
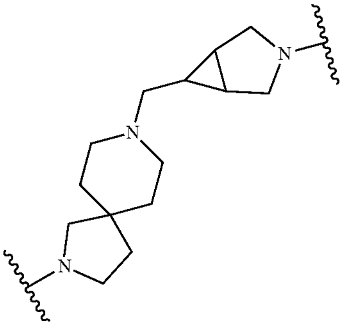
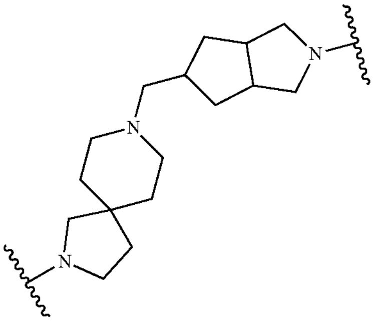
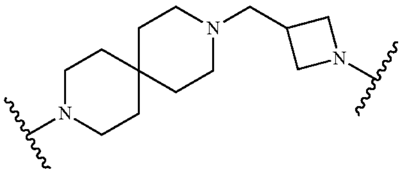
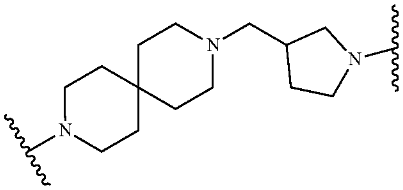
-continued
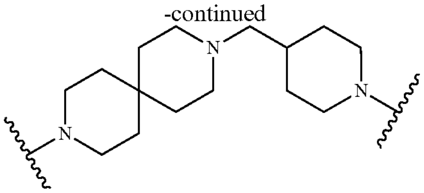
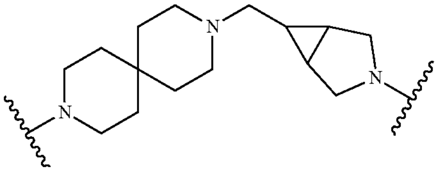
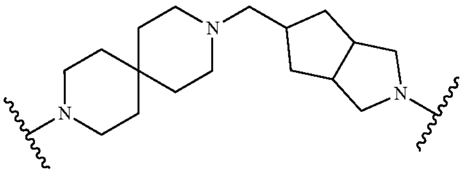
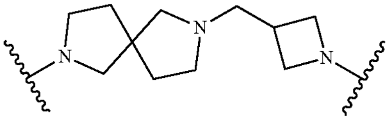
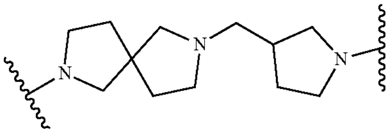
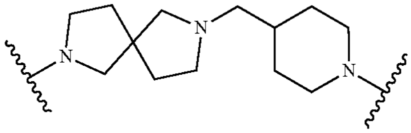
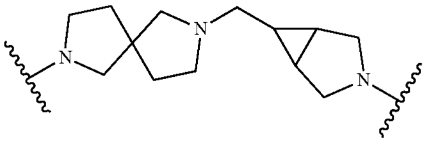
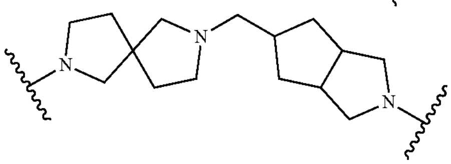
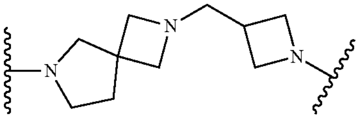
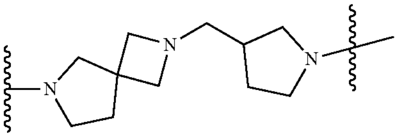
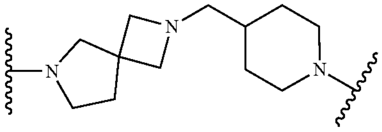
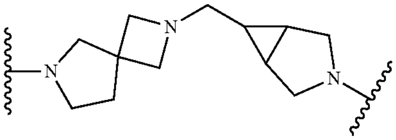

-continued
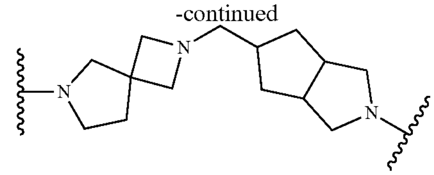
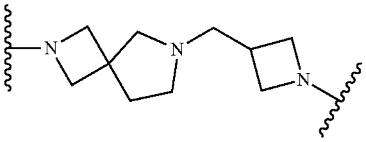
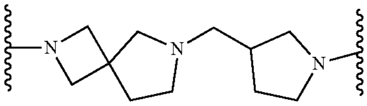
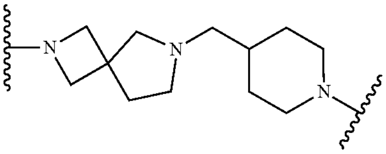
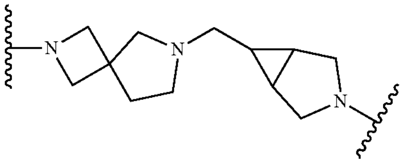
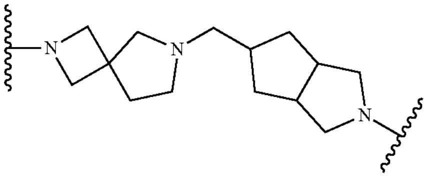
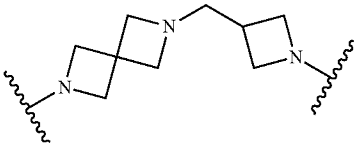
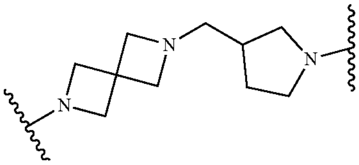
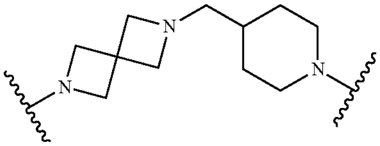
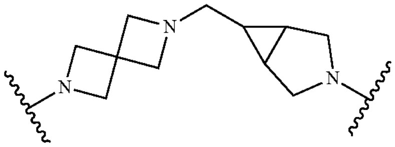
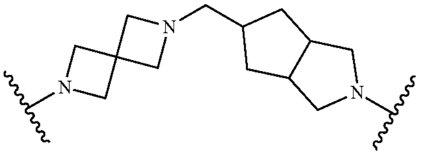
;
Preferably, said L is selected from the following structures:
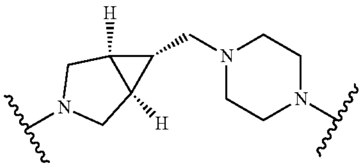
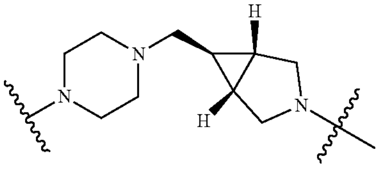
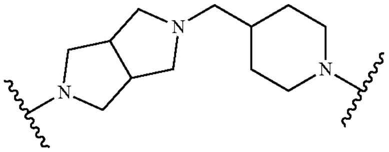
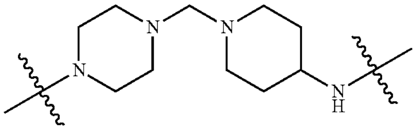
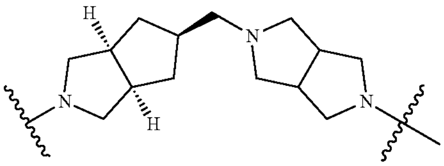
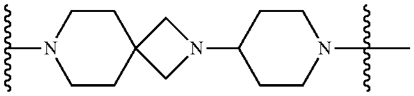
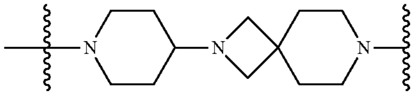
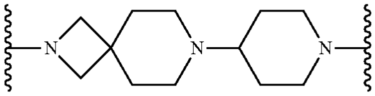
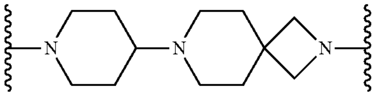
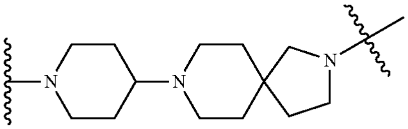
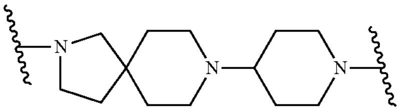
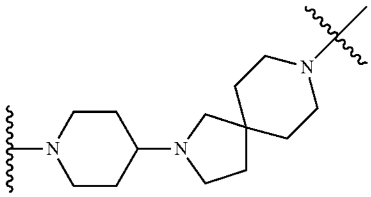

-continued
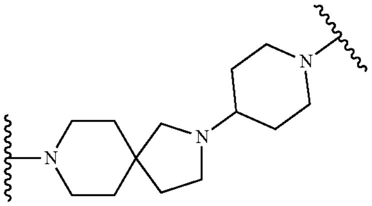
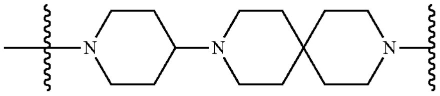
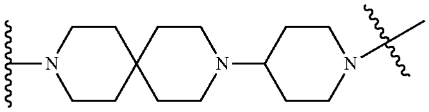
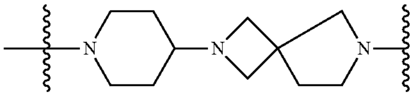
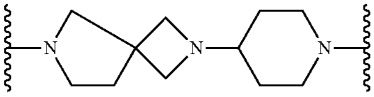
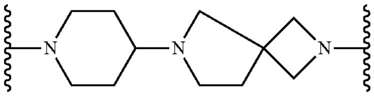
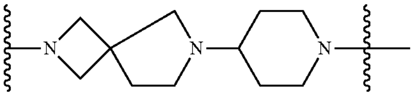
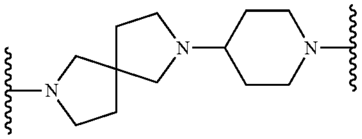
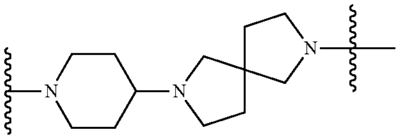
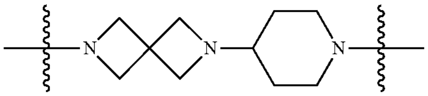
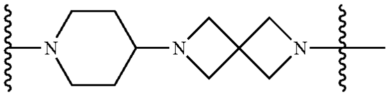
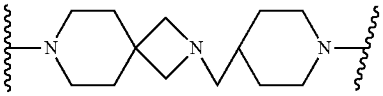
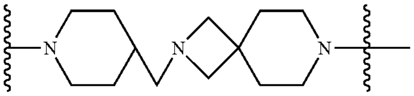
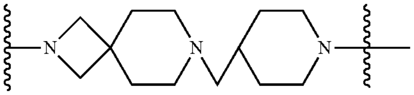
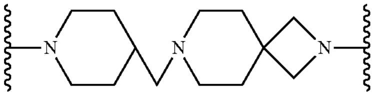
-continued
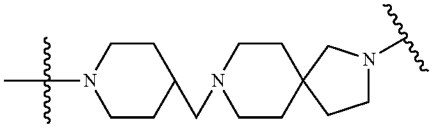
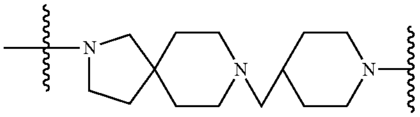
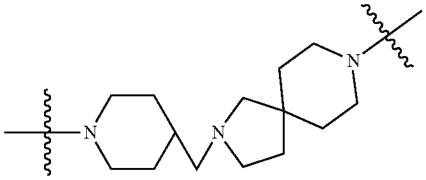
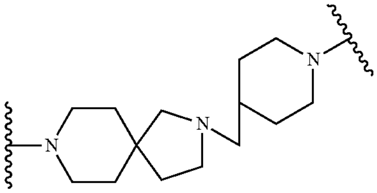
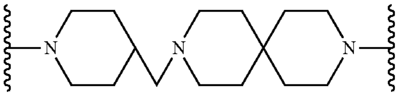
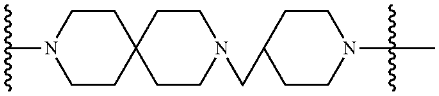
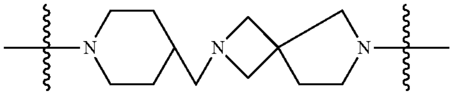
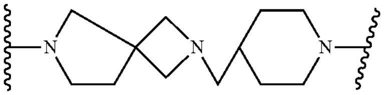
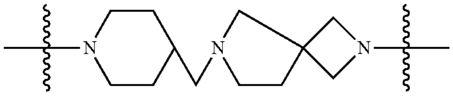
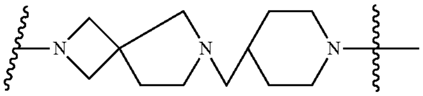
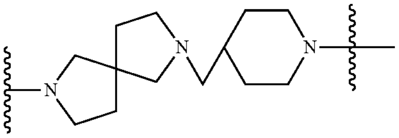
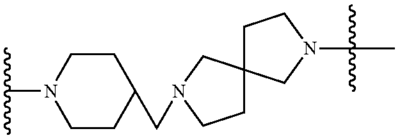
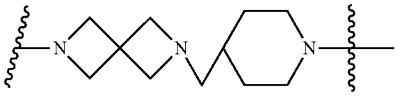
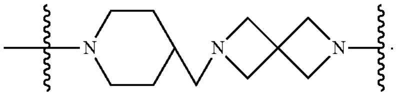

Further, said U is selected from the structure of formula (X-A):

X-A

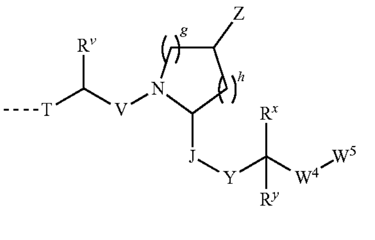

wherein, T and Y are each independently selected from a bond, O, S, $NR^{T1}$ or $CR^{T2}R^{T3}$;

V and J are each independently selected from a bond, C═O, —SO—, —$SO_2$— or $CR^2R^3$;

$R^{T1}$, $R^{T2}$, and $R^{T3}$ are each independently selected from the group consisting of H, $C_{1-6}$ alkyl or a halogenated compound thereof or a deuterated compound thereof, 3-8 membered cycloalkyl or heterocyclic group containing 0-2 heteroatoms, or $R^{T2}$ and $R^{T3}$ are linked together to form a 3-8 membered ring containing 0-2 heteroatoms;

$R^v$ is selected from the group consisting of H, $C_{1-6}$ alkyl or a halogenated compound thereof or a deuterated compound thereof, a cycloalkyl or a heterocyclic group containing 0-3 heteroatoms or a halogenated compound thereof, or $R^{T2}$ and $R^{T3}$ are linked together to form a 3-8 membered ring containing 0-2 heteroatoms;

each of g and h is independently selected from an integer of 0 to 3, and g and h are not 0 at the same time;

Z is selected from the group consisting of H, hydroxy, amino, $C_{1-6}$ alkyl, $C_{3-6}$ cycloalkyl, $C_{1-6}$ alkyl substituted with oxygen or halogen, —$OR^{Z1}$, —$NR^{Z1}R^{Z2}$, —$COR^{Z3}$, —$CO_2R^{Z3}$, —$OCOR^{Z3}$, —$NHCOR^{Z3}$, —$CONHR^{Z3}$, —$SO_2R^{Z3}$; $R^{Z1}$ and $R^{Z2}$ are each independently selected from the group consisting of H, $C_{1-6}$ alkyl or a halogenated compound thereof or a deuterated compound thereof, 3-8 membered cycloalkyl or heterocyclic group containing 0-2 heteroatoms;

said $R^{Z3}$ is selected from the group consisting of substituted or unsubstituted $C_{1-4}$ alkyl, substituted or unsubstituted $C_{3-6}$ cycloalkyl, substituted or unsubstituted $C_{3-6}$ heterocyclic group, substituted or unsubstituted aryl, substituted or unsubstituted heteroaryl; the substituent on said $R^{Z3}$ is selected from halogen and $C_{1-3}$ alkyl; each of $R^x$ and $R_y$ is independently selected from the group consisting of H, $C_{1-6}$ alkyl, halogenated $C_{1-6}$ alkyl, $C_{1-6}$ alkyl substituted with a heteroatom-containing group, -$L_y$-OH, a cycloalkyl or a heterocyclic group containing 0-3 heteroatoms or a halogenated compound thereof, or $R^x$ and $R^y$ are linked together to form a 3-8 membered ring containing 0-2 heteroatoms; wherein, $L_y$ is selected from 0-5 methylenes;

$W^4$ and $W^5$ are each independently selected from aryl and heteroaryl substituted with 0-3 substituents, and said substituents are each independently selected from H, halogen, hydroxyl, amino, mercapto, sulfone, sulfoxide, nitro, cyano, $CF_3$, heterocyclyl, $C_{1-6}$ alkyl, $C_{3-6}$ cycloalkyl, $C_{1-6}$ alkoxy, $C_{1-6}$ alkylamino, $C_{2-6}$ alkenyl, and $C_{2-6}$ alkynyl;

or, said U is selected from the structure of the following formula (X-B):

X-B

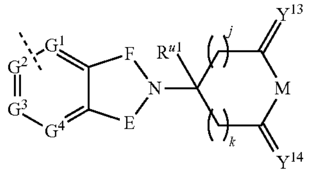

wherein, M is selected from the group consisting of O, S, and $NR^m$; wherein $R^m$ is selected from the group consisting of H, $C_{1-6}$ alkyl, $C_{3-6}$ cycloalkyl, $C_{3-6}$ heterocyclyl,

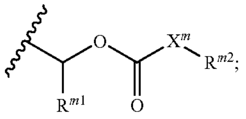

said $R^{m1}$ is selected from the group consisting of H, $C_{1-6}$ alkyl, and $C_{3-6}$ cycloalkyl; $X^m$ is selected from the group consisting of none, O, S, $NR^{m3}$;

each of $R^{m2}$ and $R^{m3}$ is independently selected from the group consisting of H, $C_{1-6}$ alkyl, $C_{3-6}$ cycloalkyl, $C_{3-6}$ heterocyclyl,

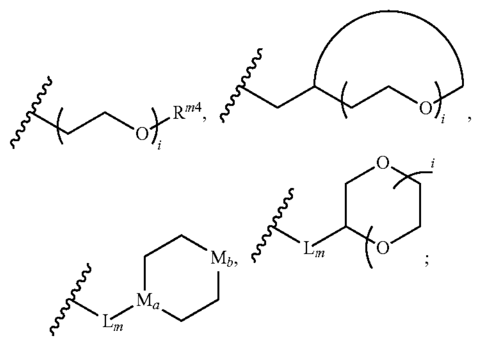

said i is selected from an integer of 0 to 12; $R^{m4}$ is selected from H and $C_{1-6}$ alkyl; $L_m$ is selected from 0-5 alkylenes; $M_a$ is selected from N and CH; $M_b$ is selected from the group consisting of O, S, $CH_2$, NH;

each of E and F is independently selected from the group consisting of CO, CS, $NR^{e1}$, O, S, $SO_2$, $CH_2$, $CD_2$, $CR^{e2}R^{e3}$,

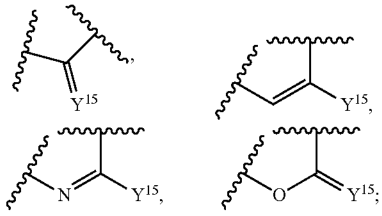

each of $R^{e1}$, $R^{e2}$, and $R^{e3}$ is independently selected from the group consisting of $C_{1-6}$ alkyl, H, halogen, hydroxy, amino; each of $Y^{15}$, $Y^{13}$, and $Y^{14}$ is independently selected from the group consisting of H, O, S, $C_{1-3}$ alkyl;

each of j and k is independently selected from an integer of 0 to 3, and j and k are not 0 at the same time; each of $G^1$, $G^2$, $G^3$, and $G^4$ is independently selected from the group consisting of O, S, N, $CR^{g1}$, $CR^{g2}$, $CR^{g3}$, $CR^{g4}$; wherein, each of $R^{g1}$, $R^{g2}$, $R^{g3}$, and $R^{g4}$ is independently selected from the group consisting of H, halogen, hydroxyl, amino, mercapto, sulfone, sulfoxide, nitro, cyano, $CF_3$, heterocyclyl, $C_{1-6}$ alkyl, $C_{3-6}$, cycloalkyl, $C_{1-6}$ alkoxy, $C_{1-6}$ alkylamino. $C_{2-6}$, alkenyl, and $C_{2-6}$, alkynyl:

$R^{u1}$ is selected from H and C1-C6 alkyl;

or, said U is selected from the structure of the following formula (X-C):

X-C

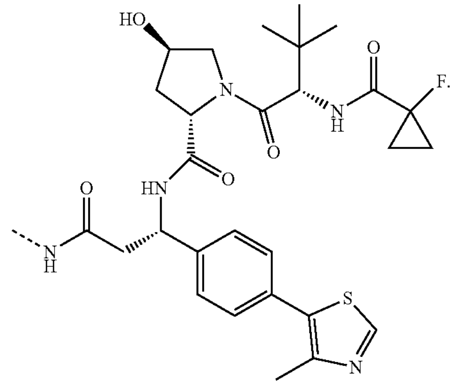

Further, said formula (X-A) is selected from the structure of formula (XI-A):

XI-A

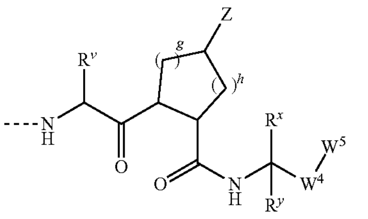

wherein, the optional scope of $R^v$, Z, g, h, $R^x$, $R^y$, $W^4$, $W^5$ is the same as that of formula (II-A) mentioned above;

or,

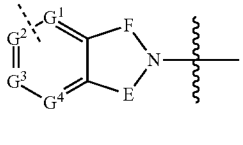

in said formula (X-B) is selected from the structures of formulas (XI-B), (XI-C), (XI-D), (XI-E) or (XI-F):

XI-B

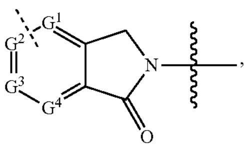

-continued

XI-C

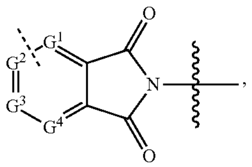

XI-D

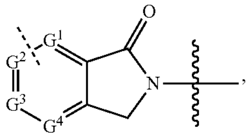

XI-E

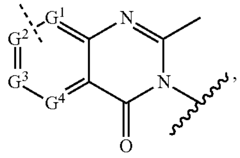

XI-F

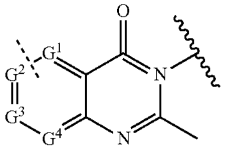

wherein, the optional scope of $G^1$, $G^2$, $G^3$, and $G^4$ is the same as that of formula (X-B) mentioned above.

Further, said formula (XI-A) is selected from the structure of formula (XII-A):

XII-A

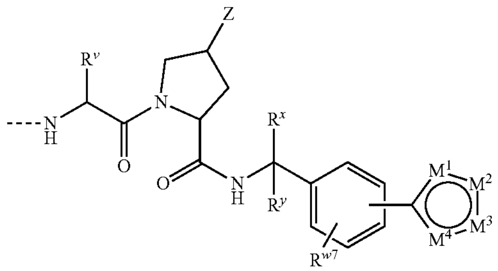

wherein, $R^{w7}$ is selected from the group consisting of H, halogen, hydroxyl, amino, mercapto, sulfone, sulfoxide, nitro, cyano, $CF_3$, heterocyclyl, $C_{1-6}$ alkyl, $C_{3-6}$ cycloalkyl, $C_{1-6}$ alkoxy, $C_{1-6}$ alkylamino, $C_{2-6}$, alkenyl, and $C_{2-6}$ alkynyl;

each of $M^1$, $M^2$, $M^3$, $M^4$ is independently selected from the group consisting of O, S, N $R^{12}$, $C(R^{12})_2$; wherein $R^{12}$ is selected from the group consisting of H, halogen, hydroxyl, amino, mercapto, sulfone, sulfoxide, nitro, cyano, $CF_3$, heterocyclyl, $C_{1-6}$ alkyl, $C_{3-6}$ cycloalkyl, $C_{1-6}$ alkoxy, $C_{1-6}$ alkylamino, $C_{2-6}$ alkenyl, and $C_{2-6}$ alkynyl; the optional scope of $R^v$, Z, $R^x$, and $R^y$ is the same as that of formula (XI-A) mentioned above.

Further, $W^5$ in said formula XI-A is selected from the following structures:
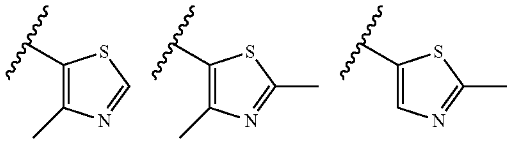
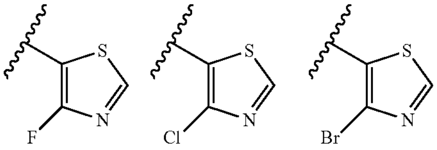
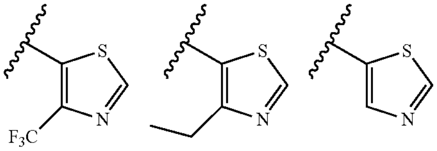
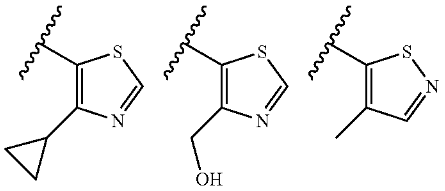
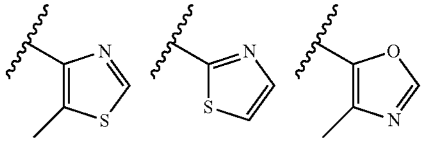
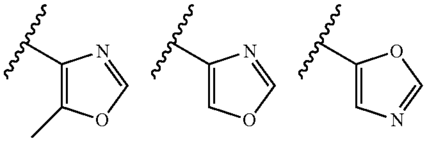
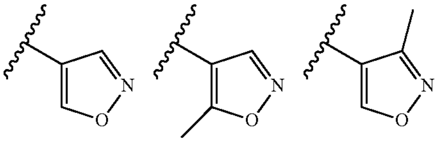
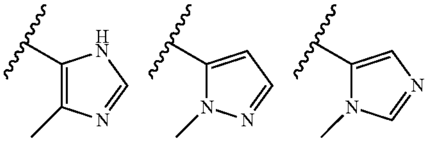
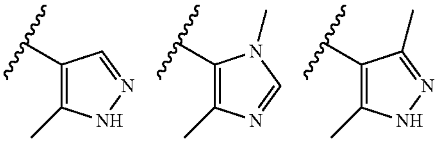
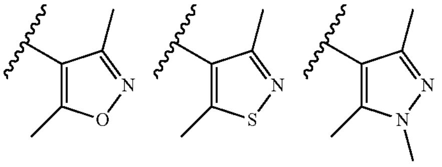
-continued
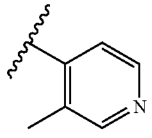
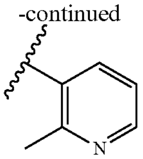
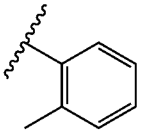
Further, said U is selected from the following structures:
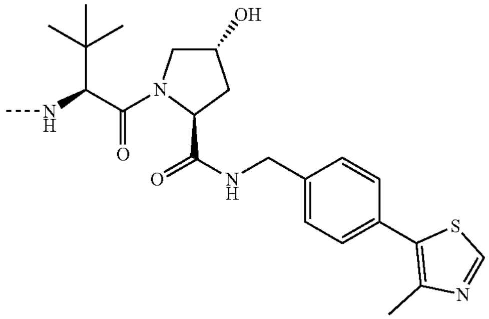
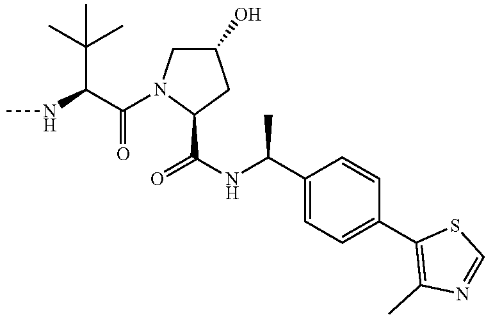
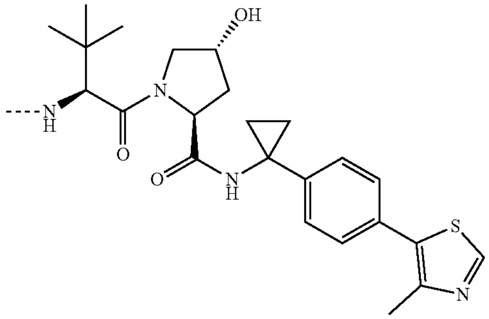
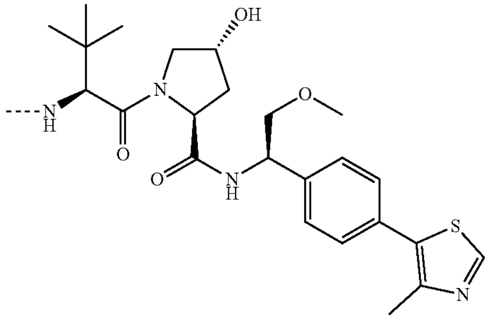
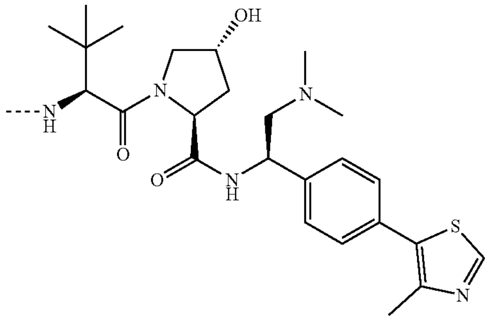

-continued
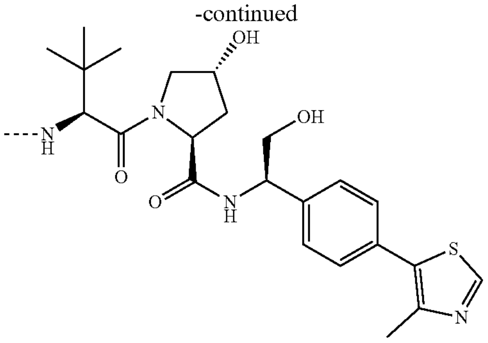
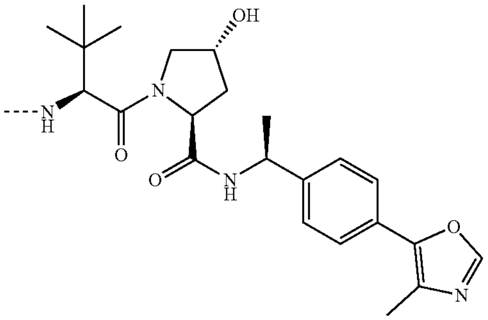
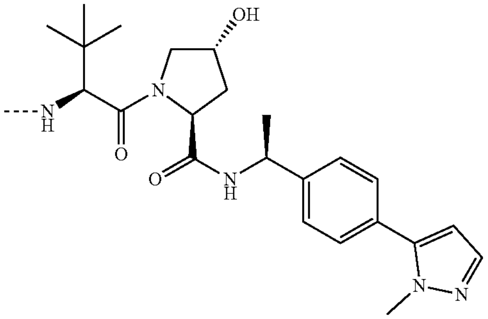
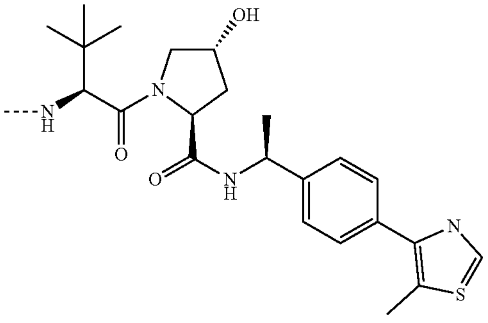
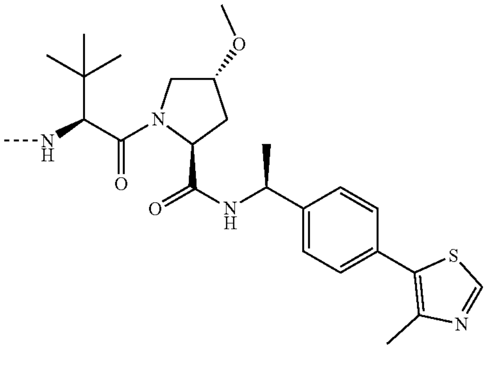
-continued
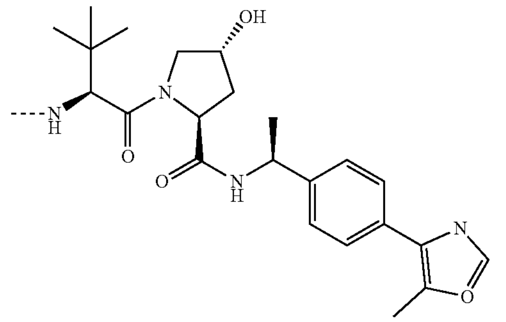
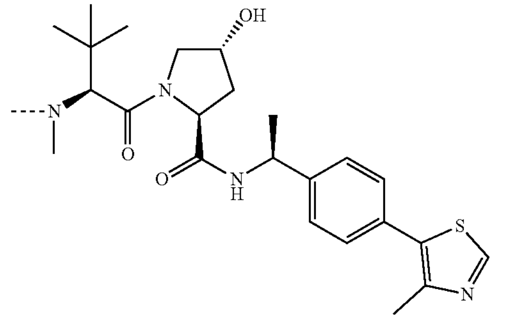
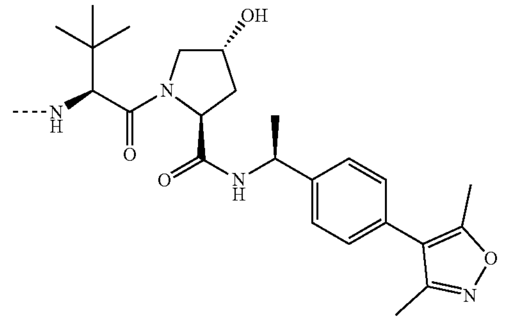
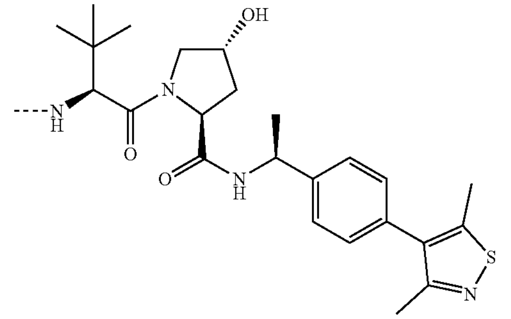
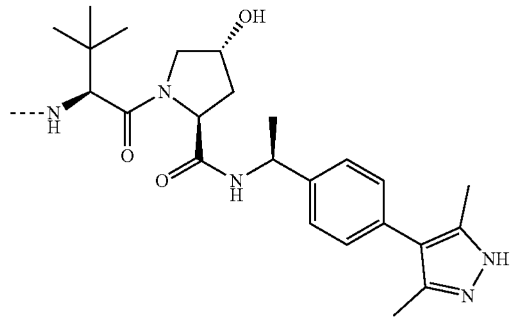

-continued
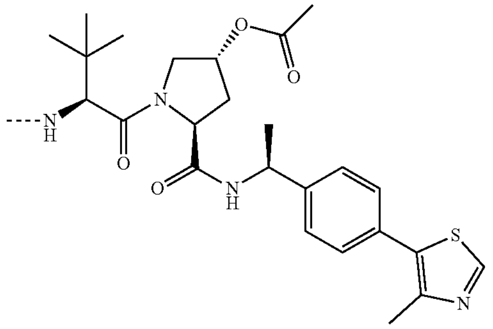
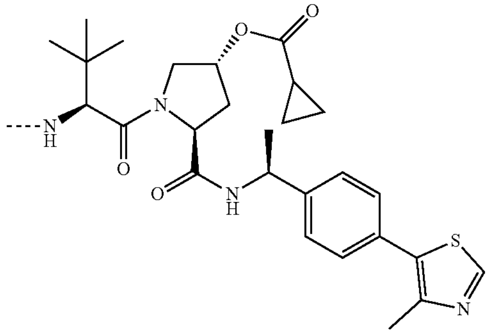
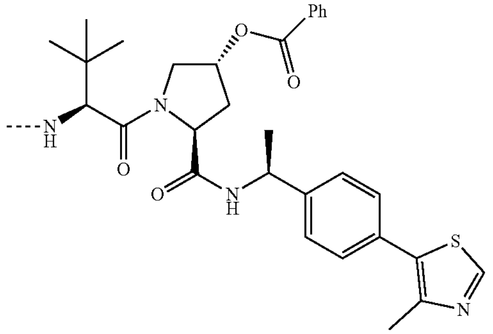
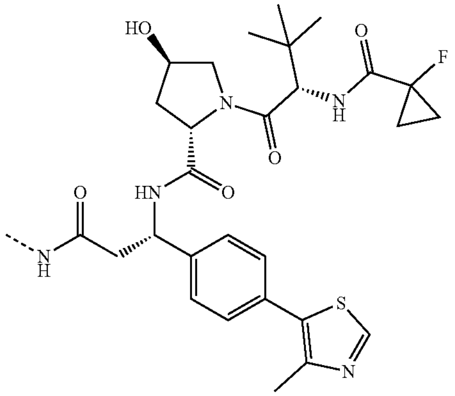
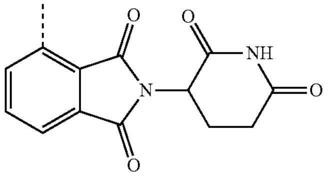
-continued
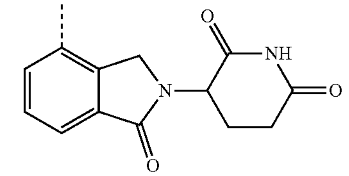
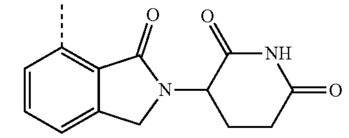
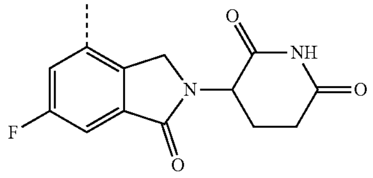
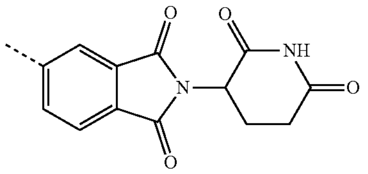
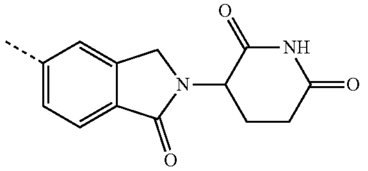
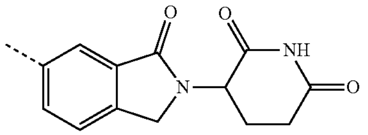
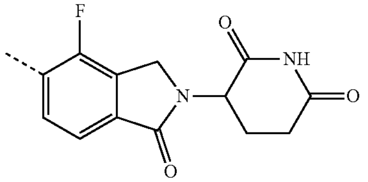
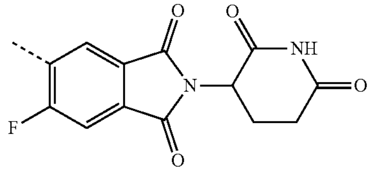
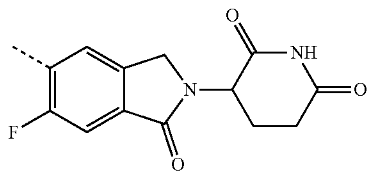
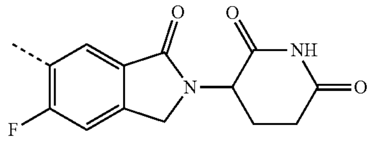

-continued
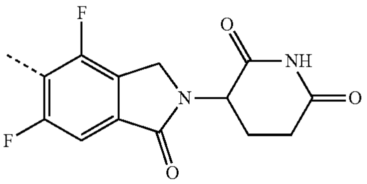
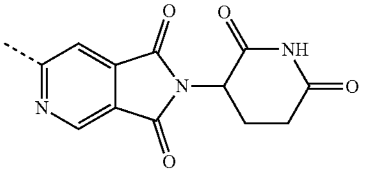
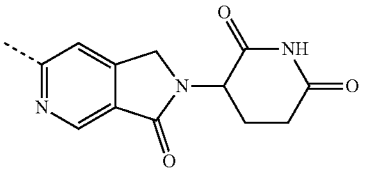
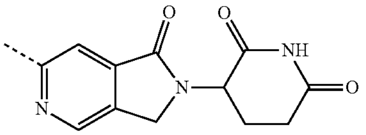
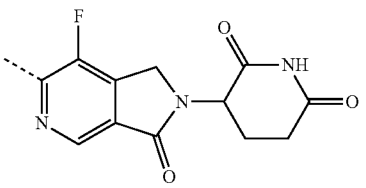
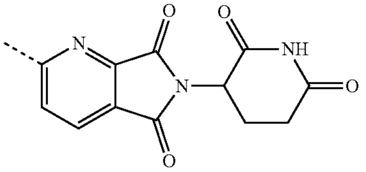
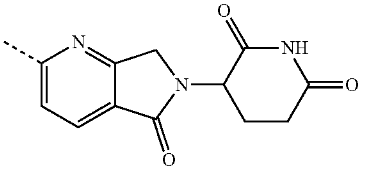
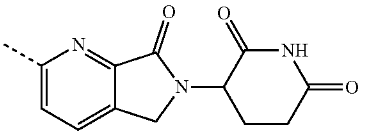
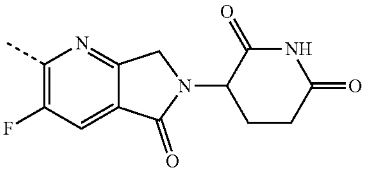
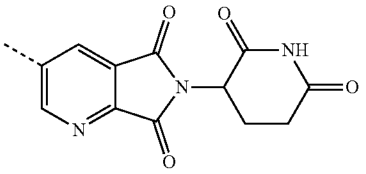
-continued
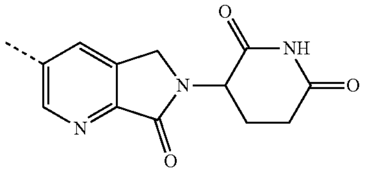
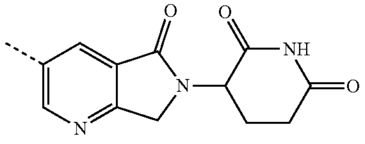
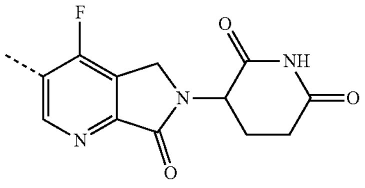
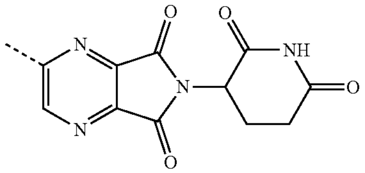
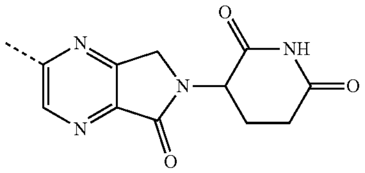
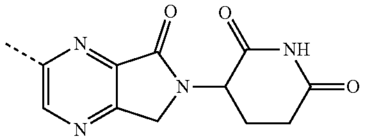
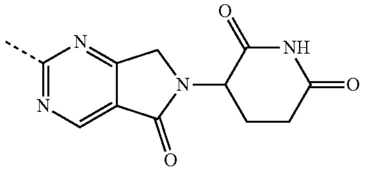
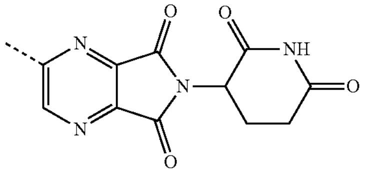
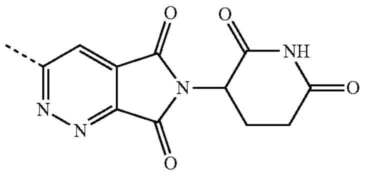
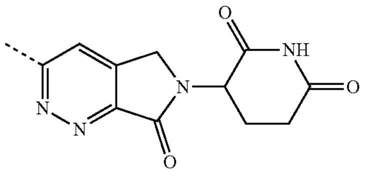

-continued
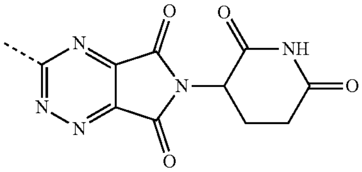
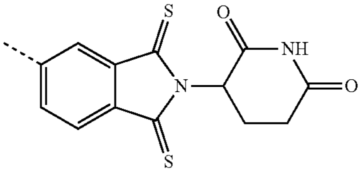
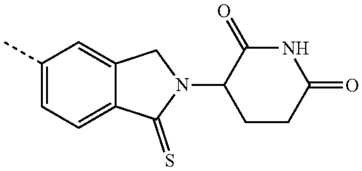
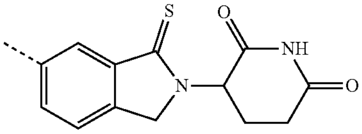
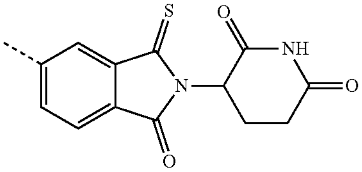
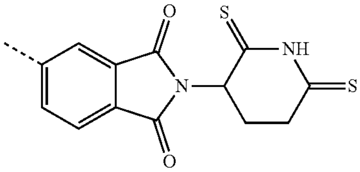
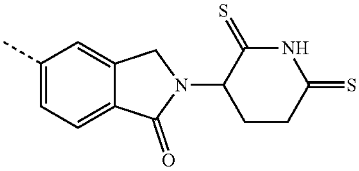
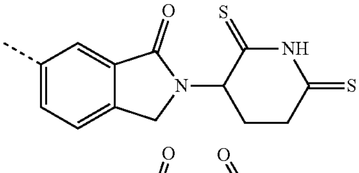
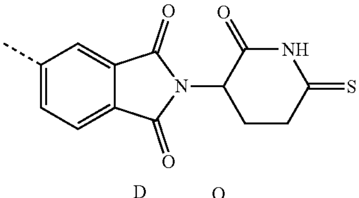
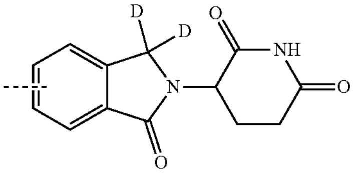
-continued
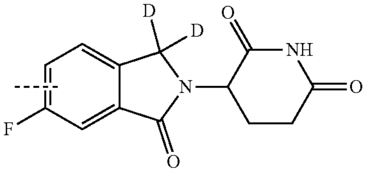
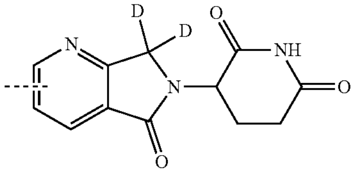
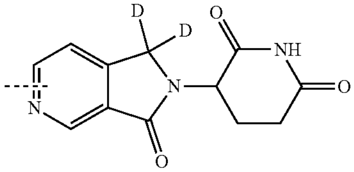
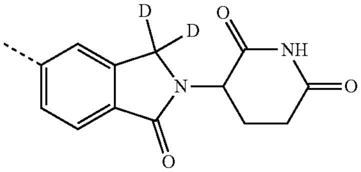
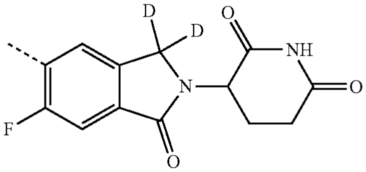
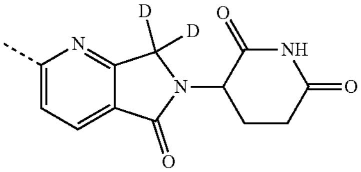
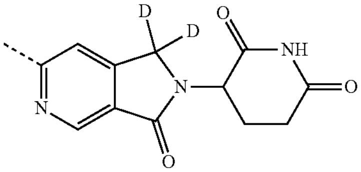
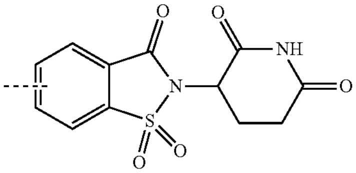
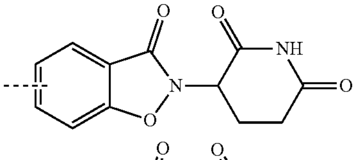
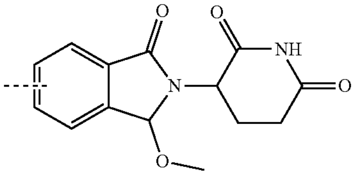

-continued
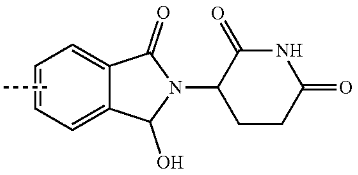
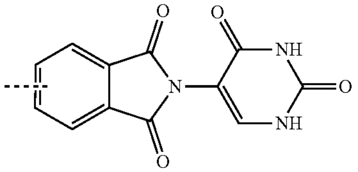
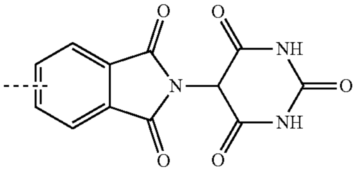
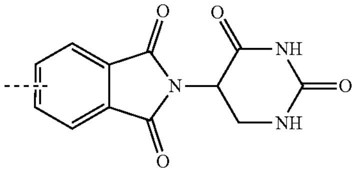
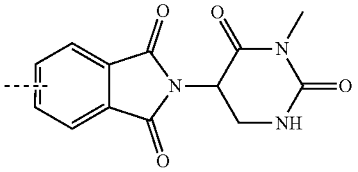
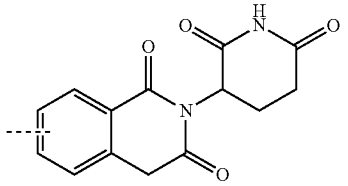
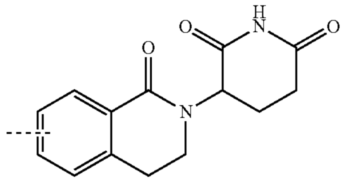
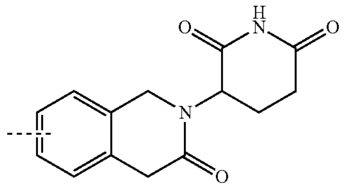
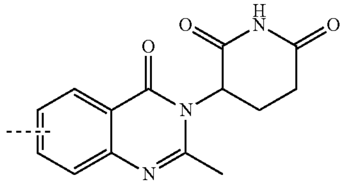
-continued
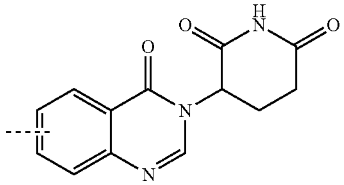
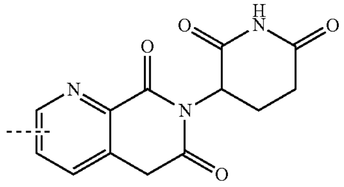
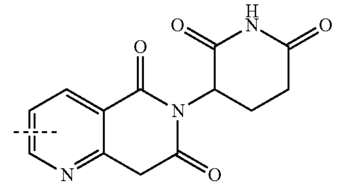
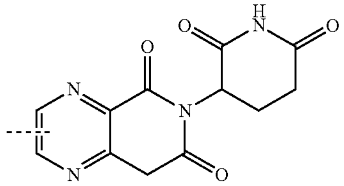
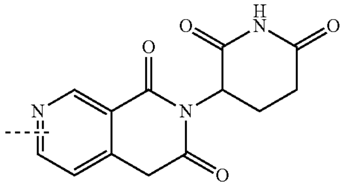
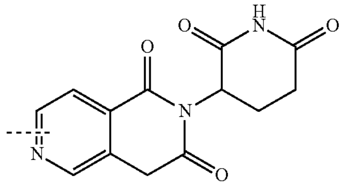
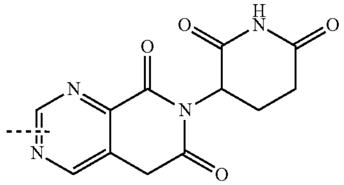
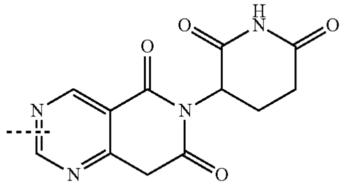
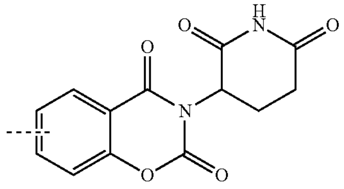

-continued
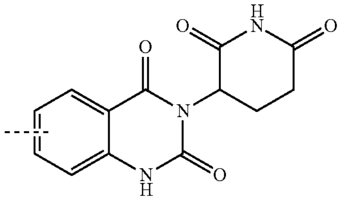
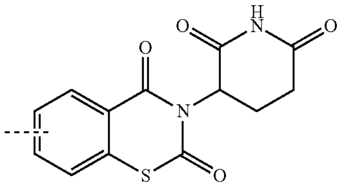
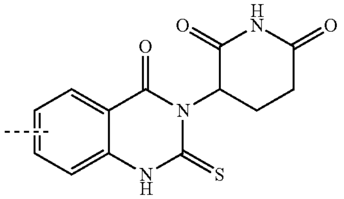
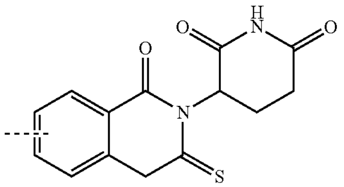
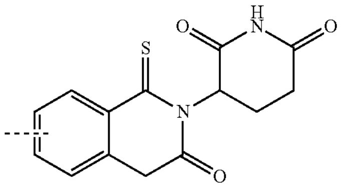
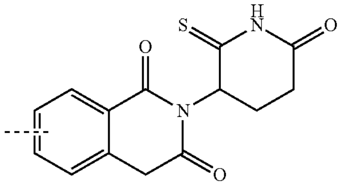
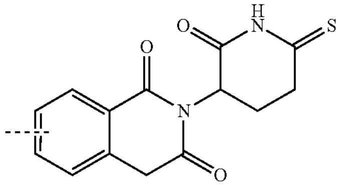
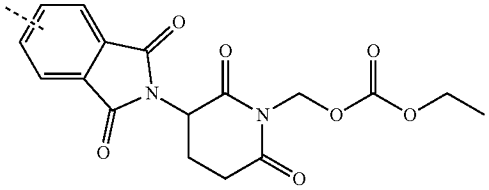
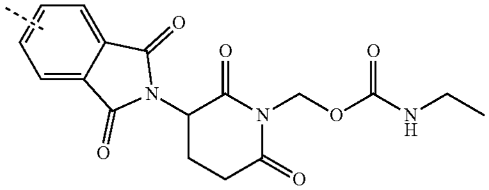
-continued
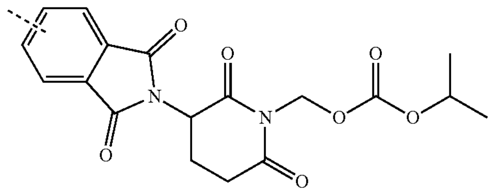
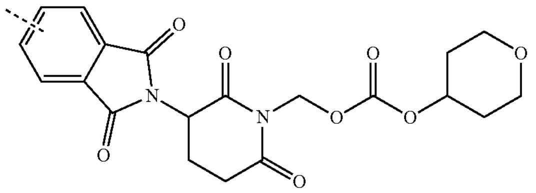
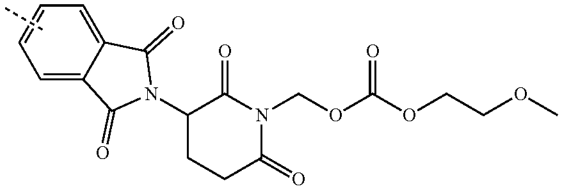
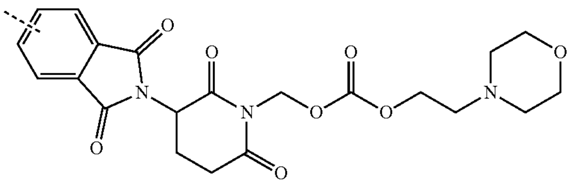
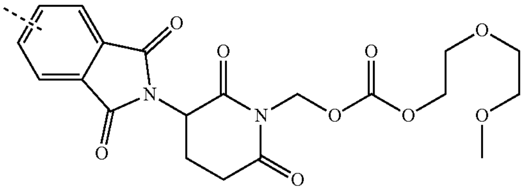
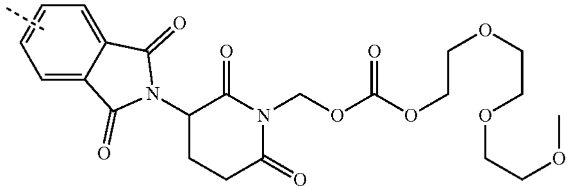
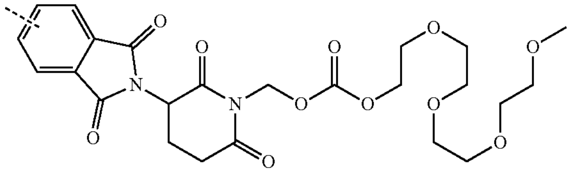
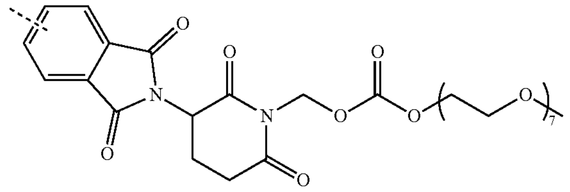
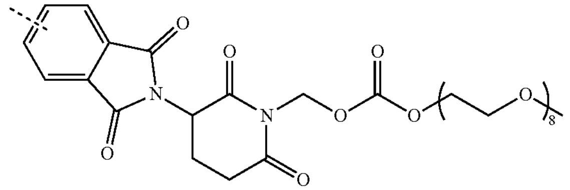

-continued
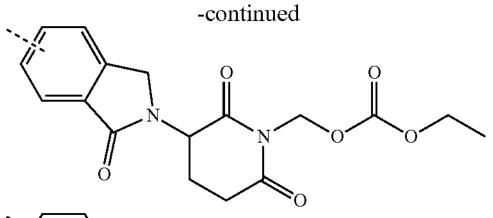
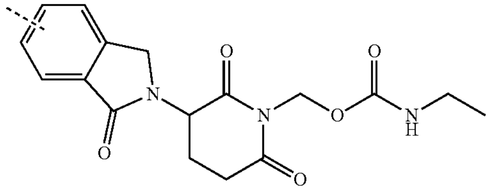
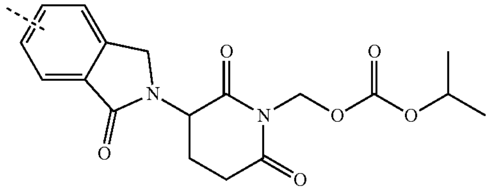
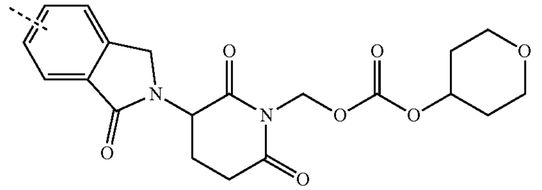
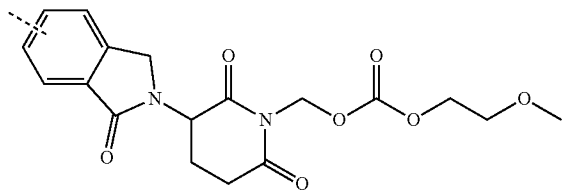
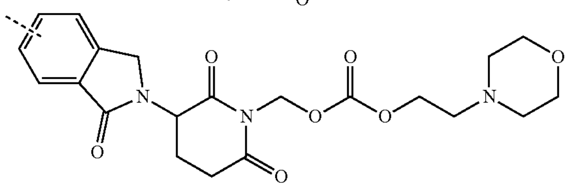
-continued
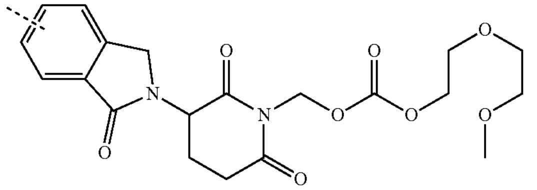
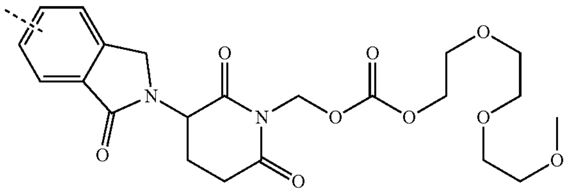
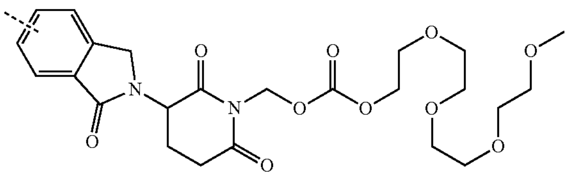
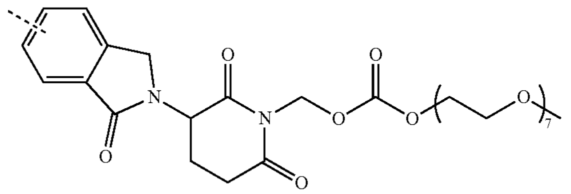
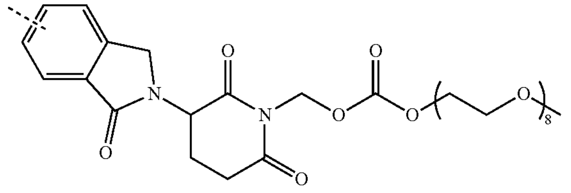
Further, said compound is selected from one of the following compounds:
1
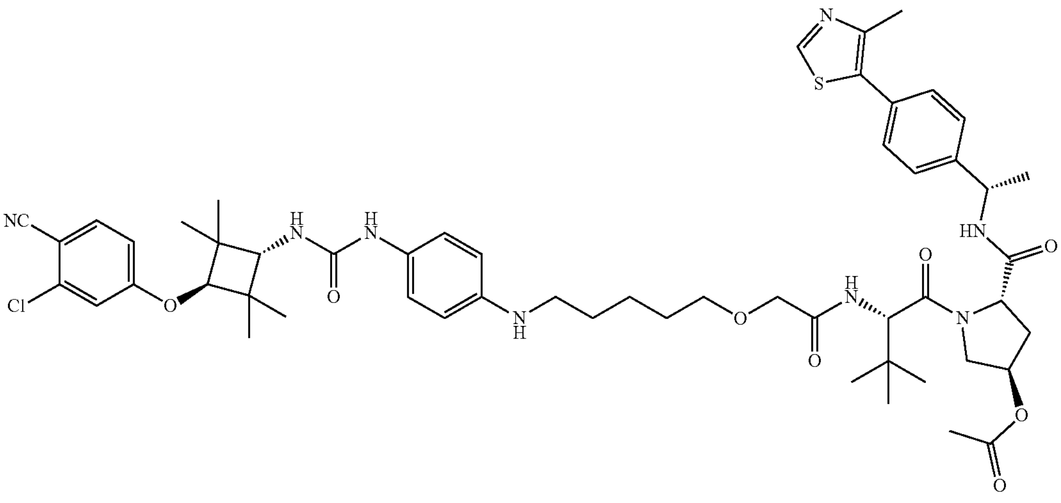

-continued
2
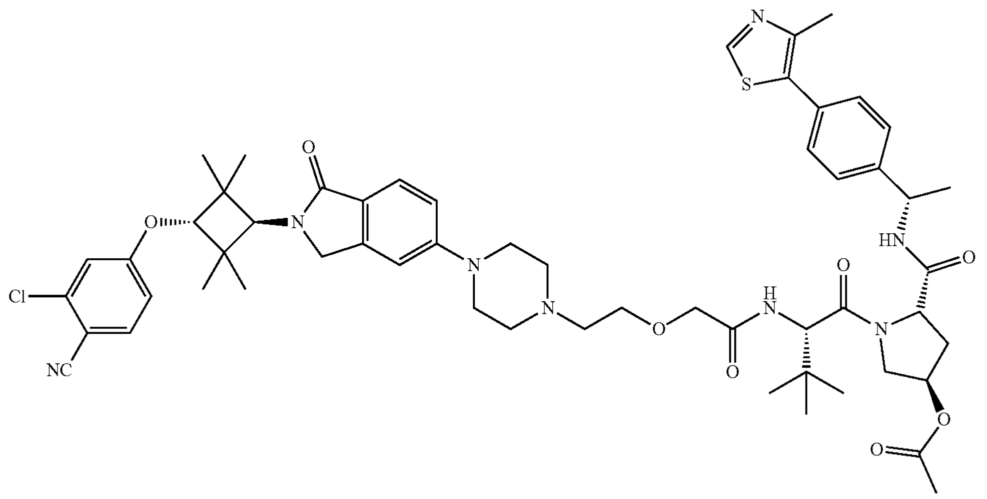
3
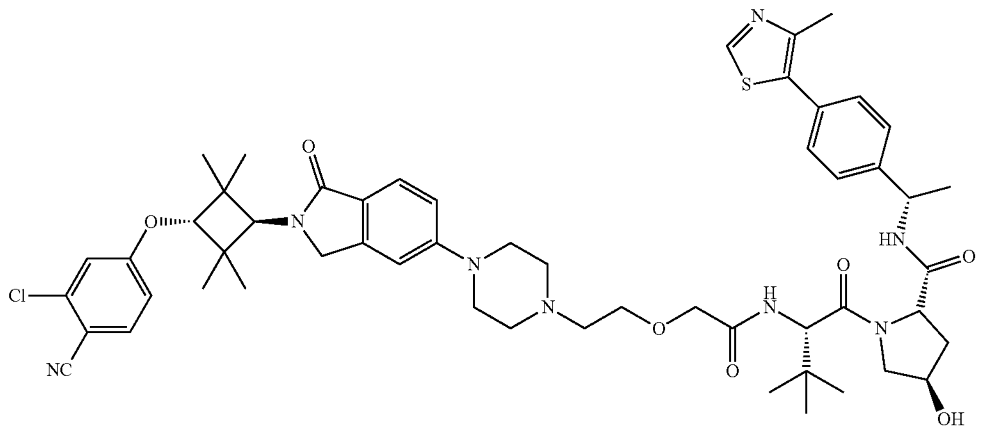
4
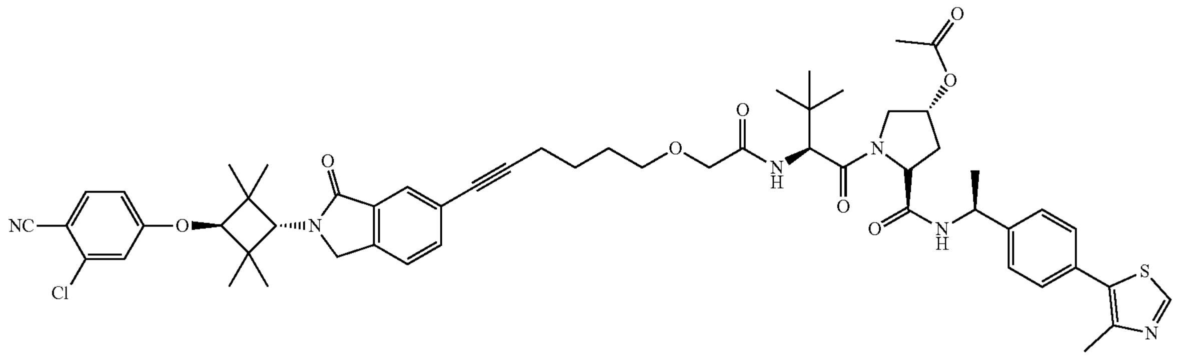
5
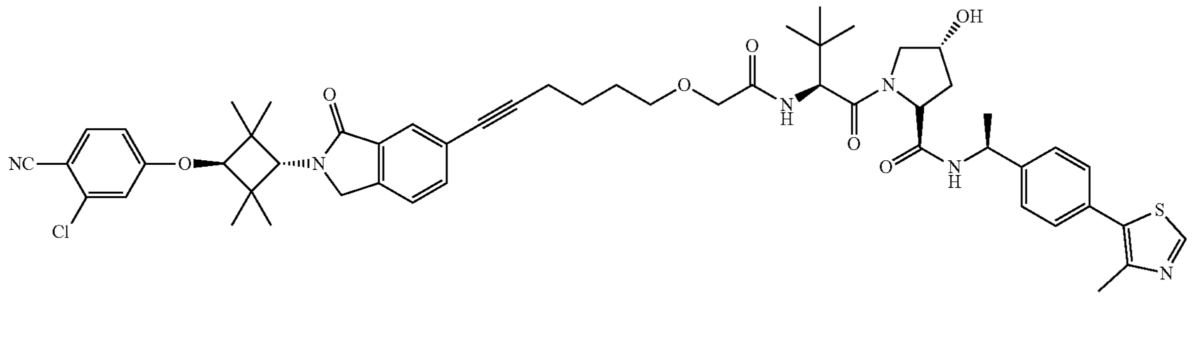

-continued
6
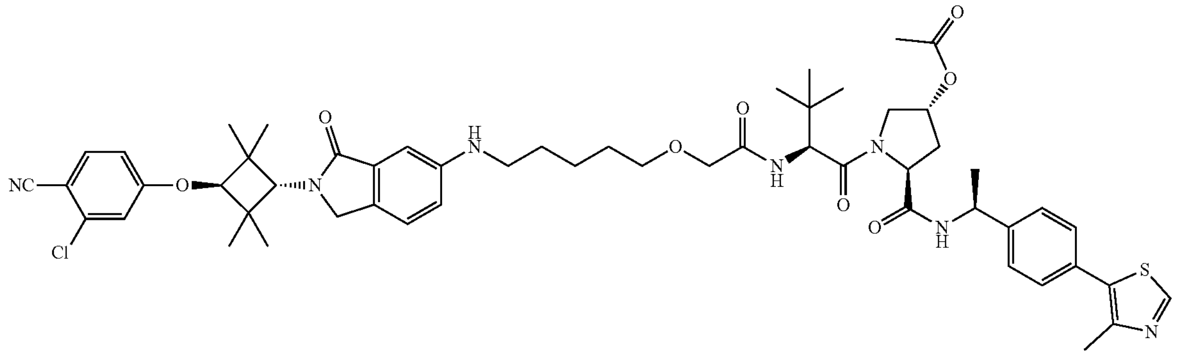
7
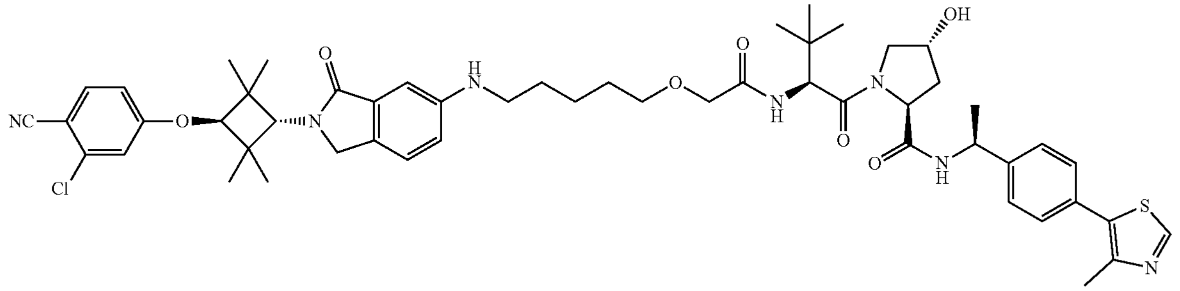
8
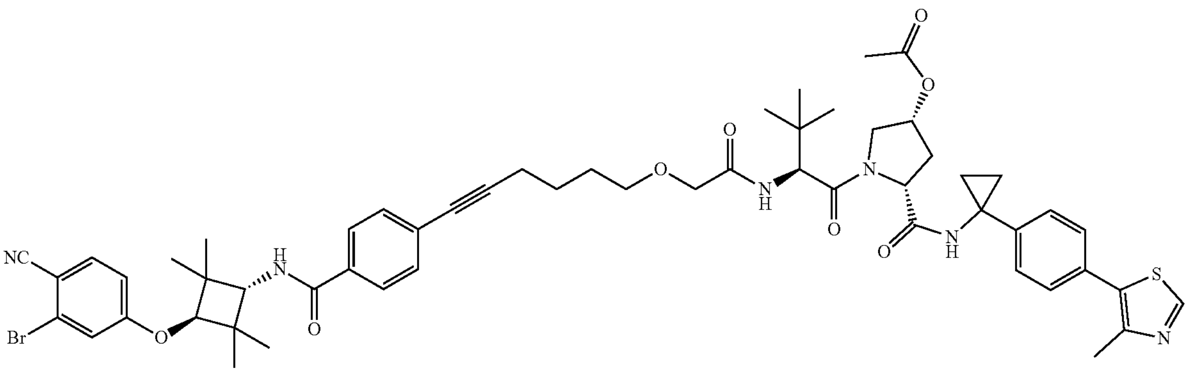
9
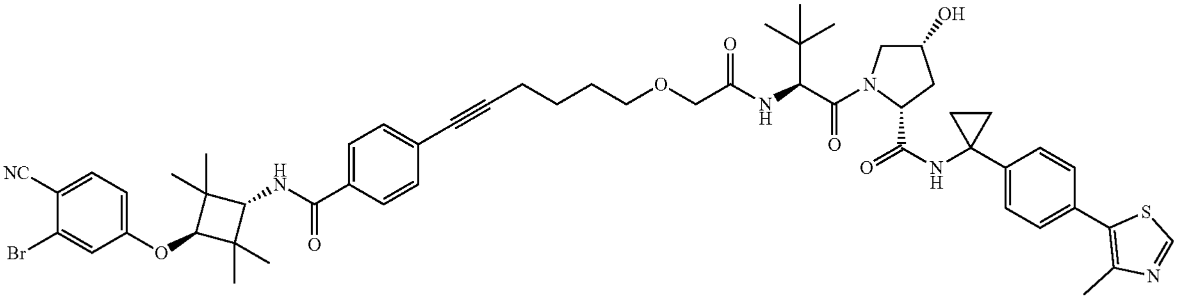

-continued
10
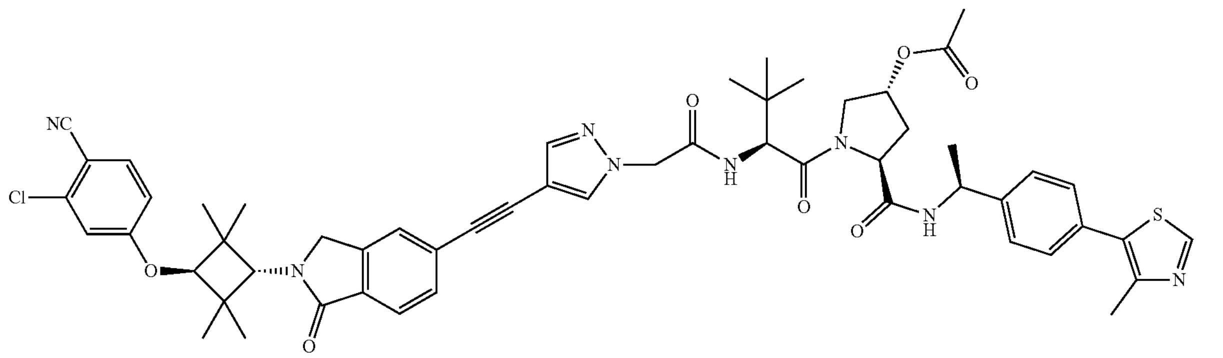
11
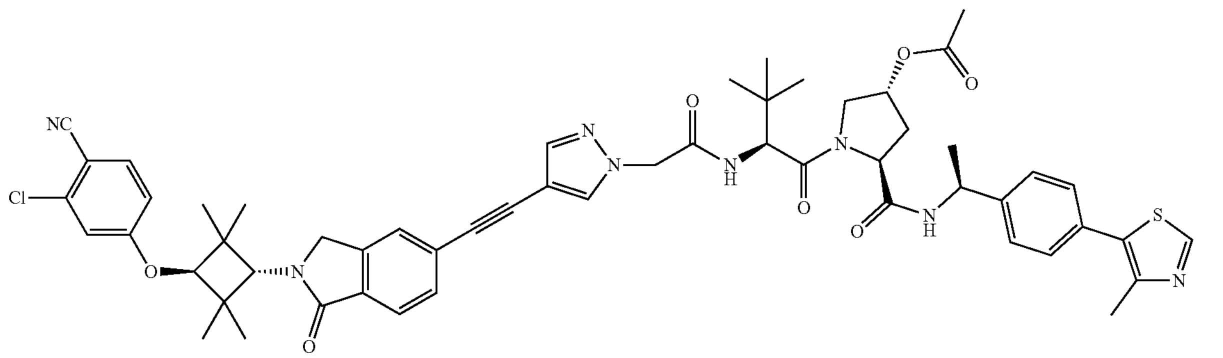
12
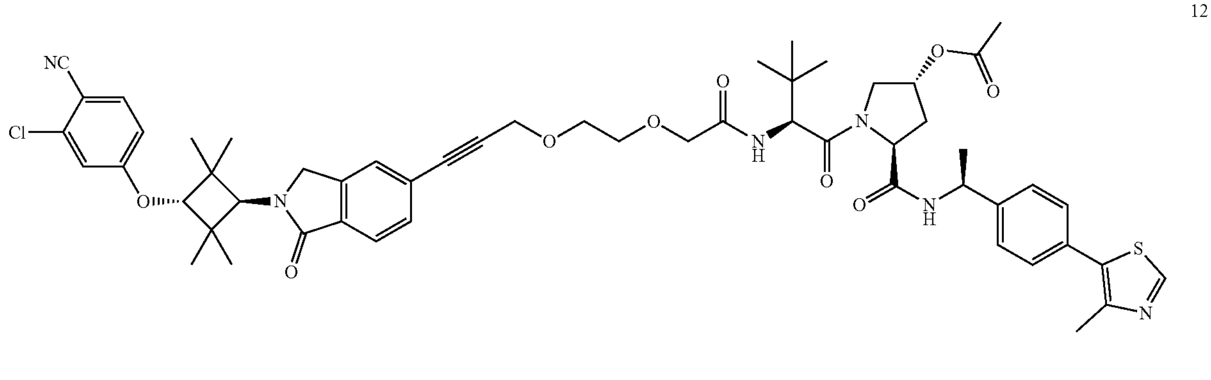
13
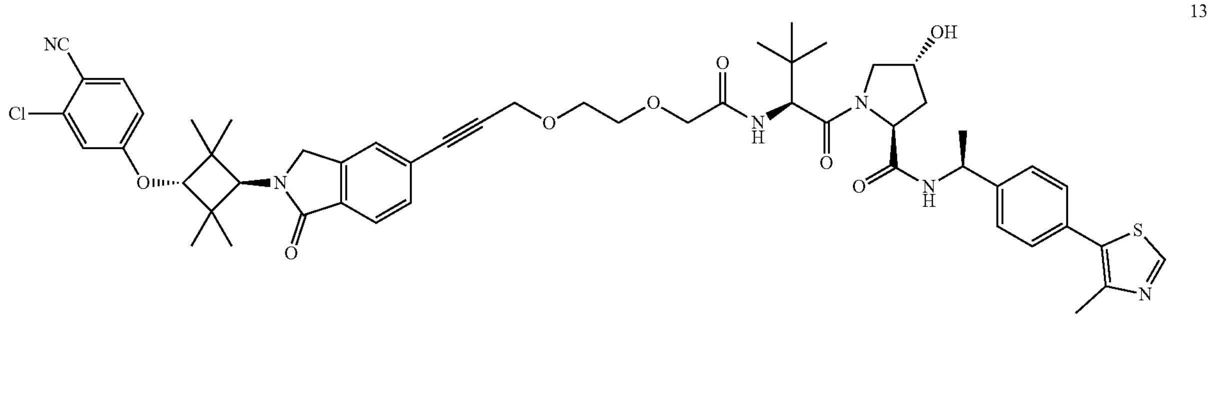

-continued
14
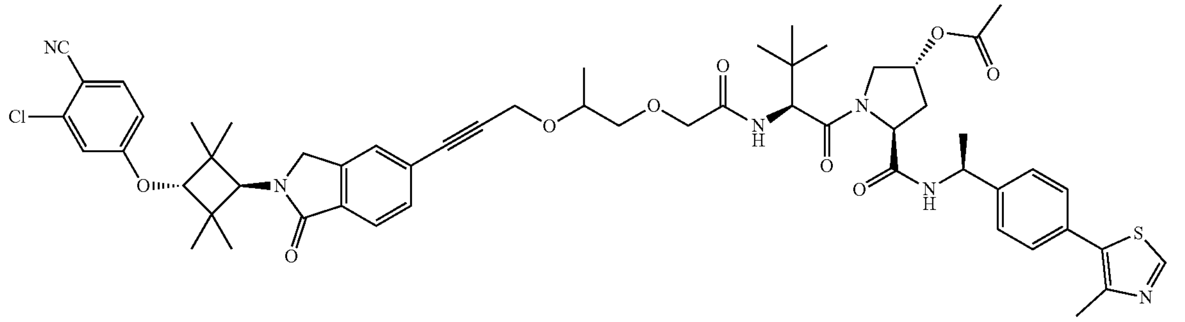
15
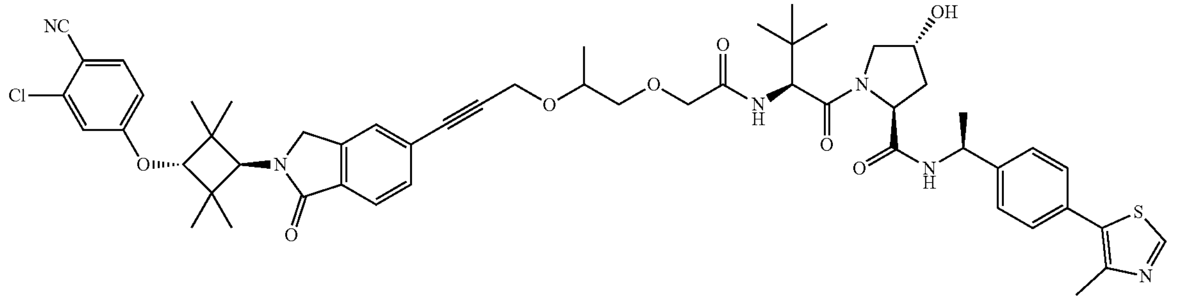
16
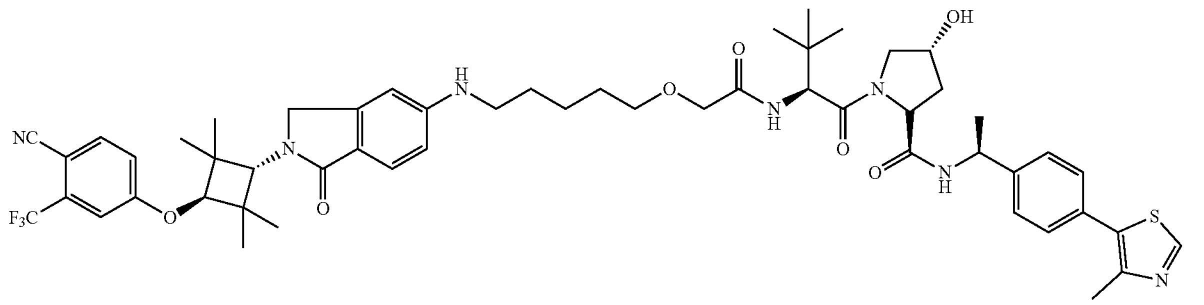
17
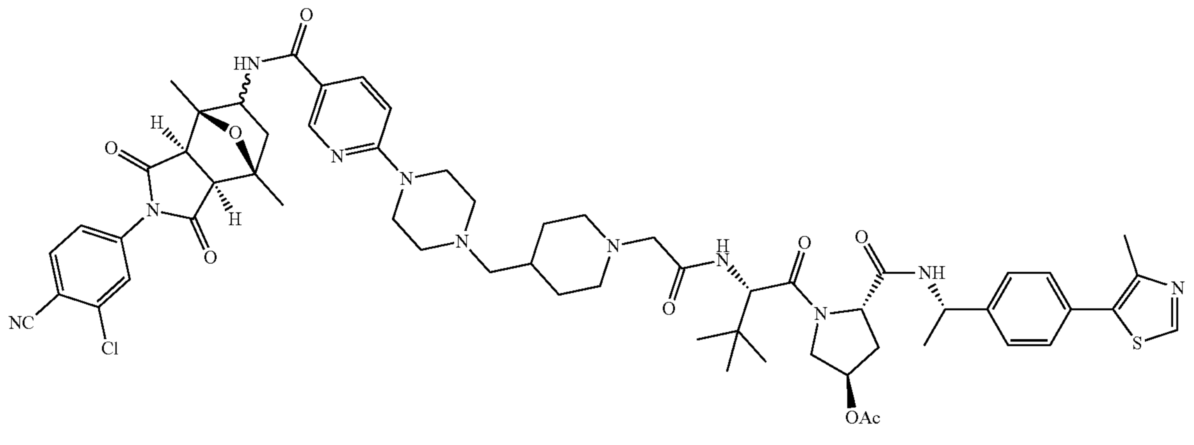

-continued
18
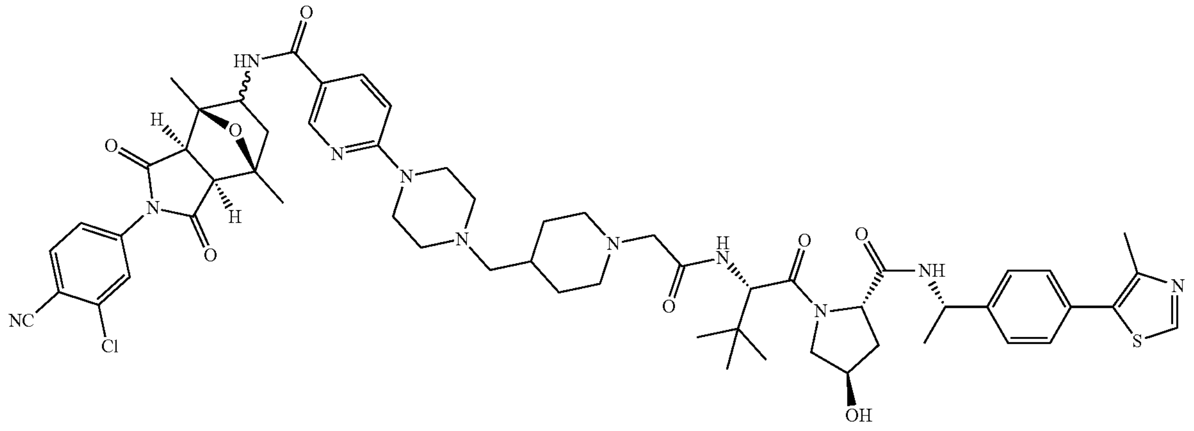
19
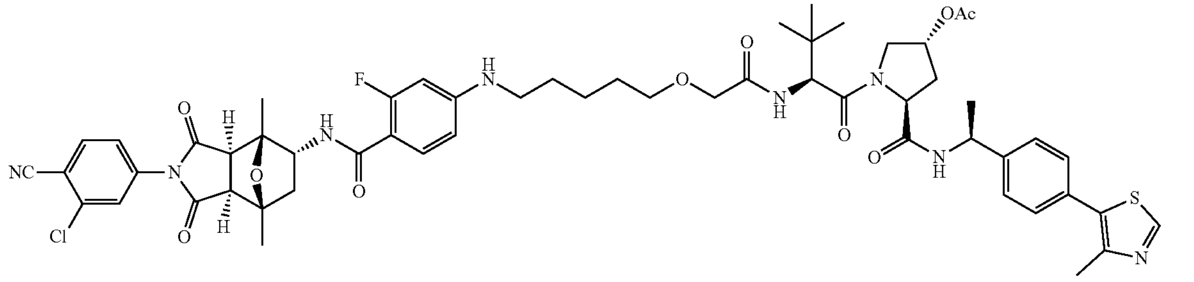
20
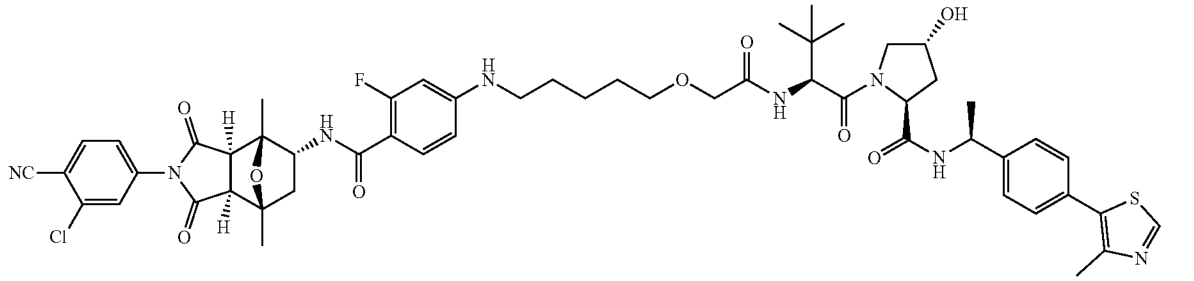
21
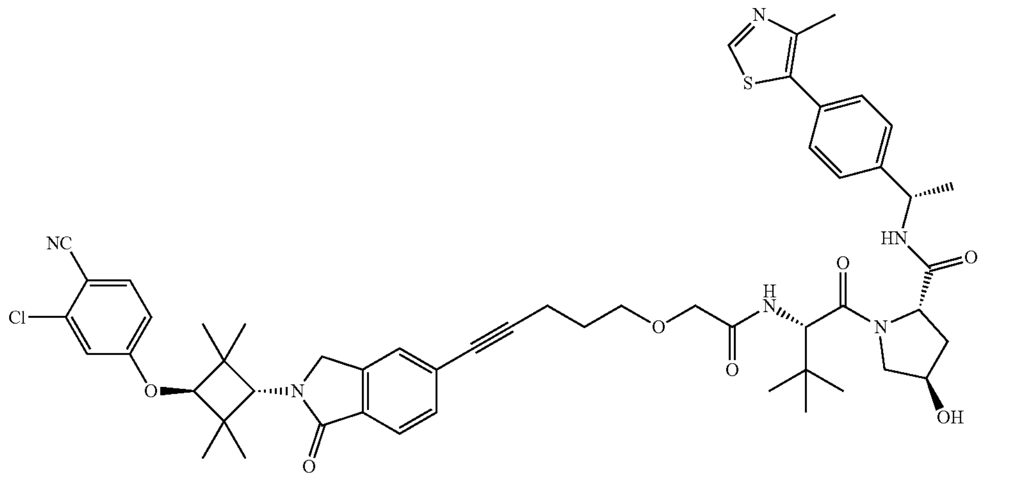

-continued
22
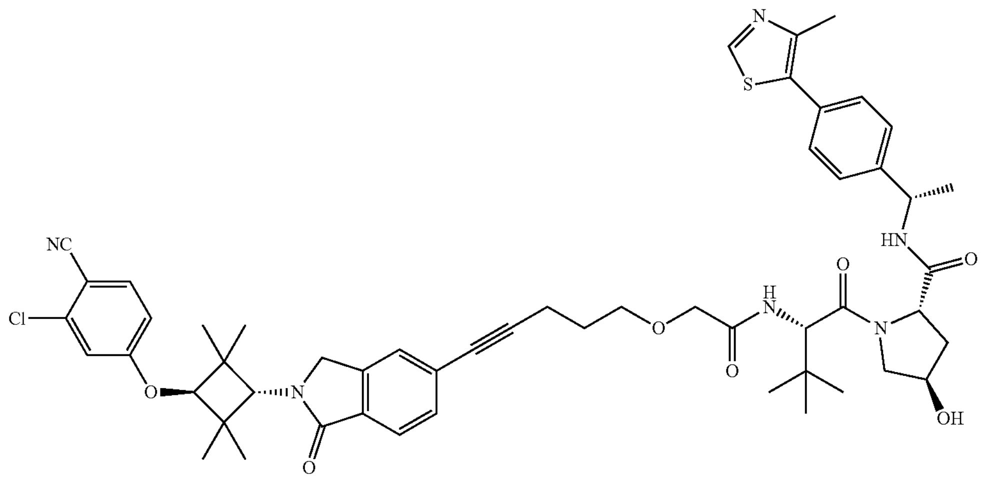
23
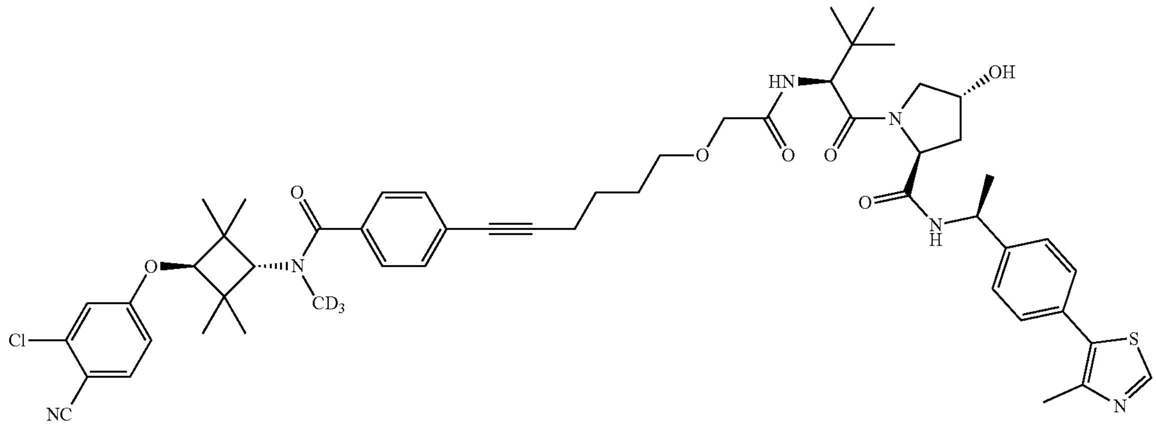
24
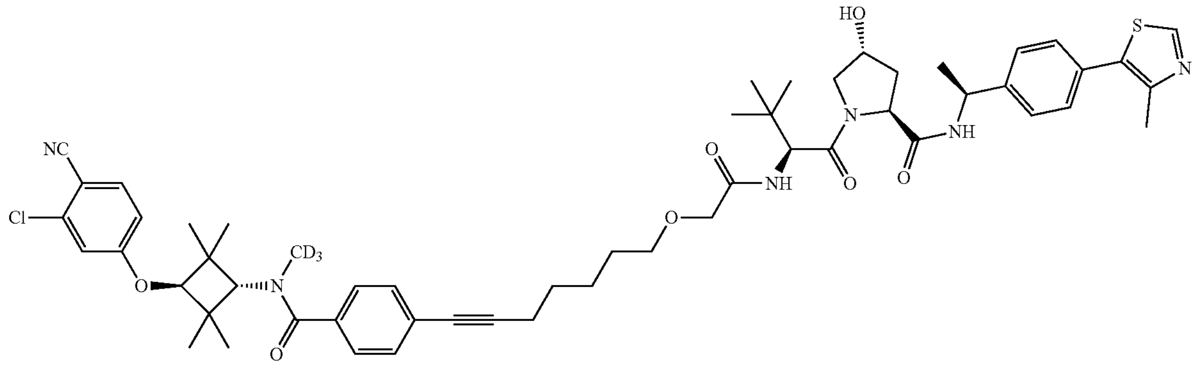
25
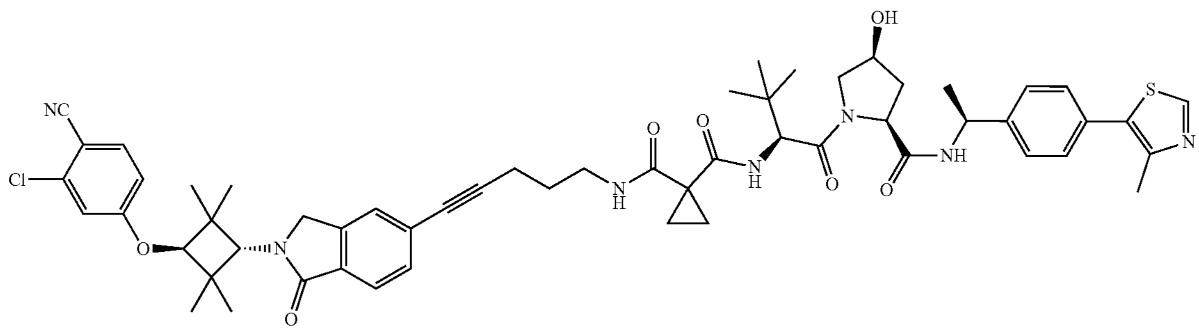

-continued
26
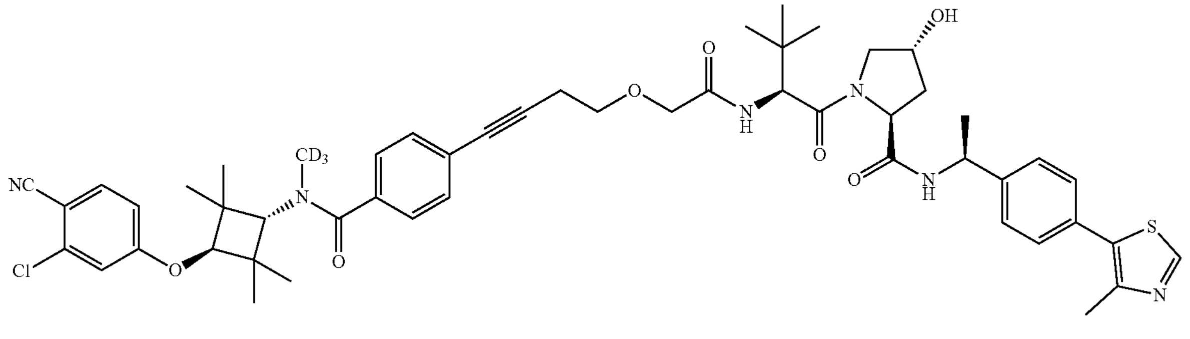
27
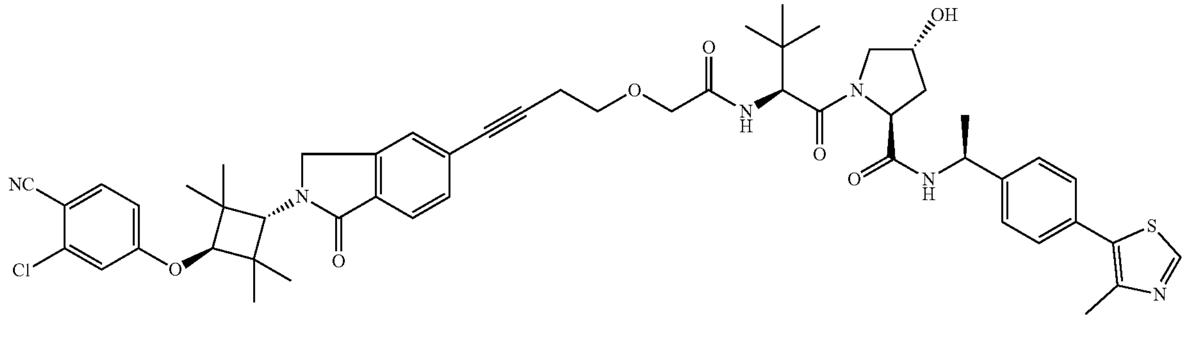
28
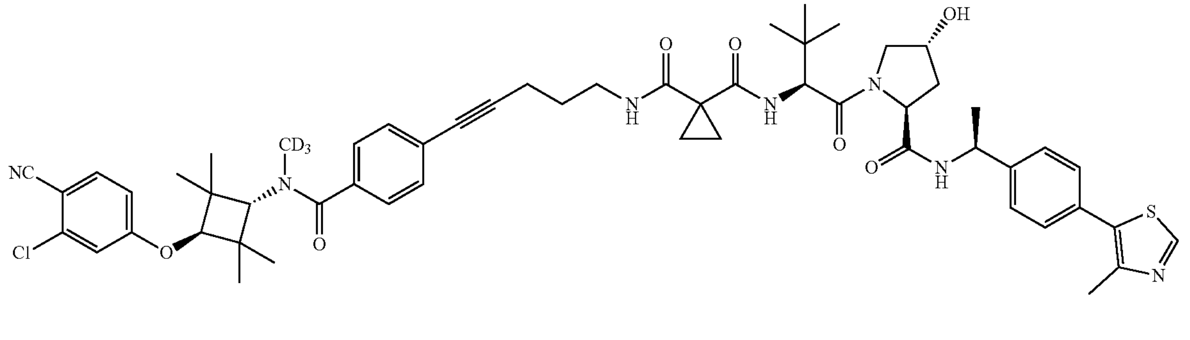
29
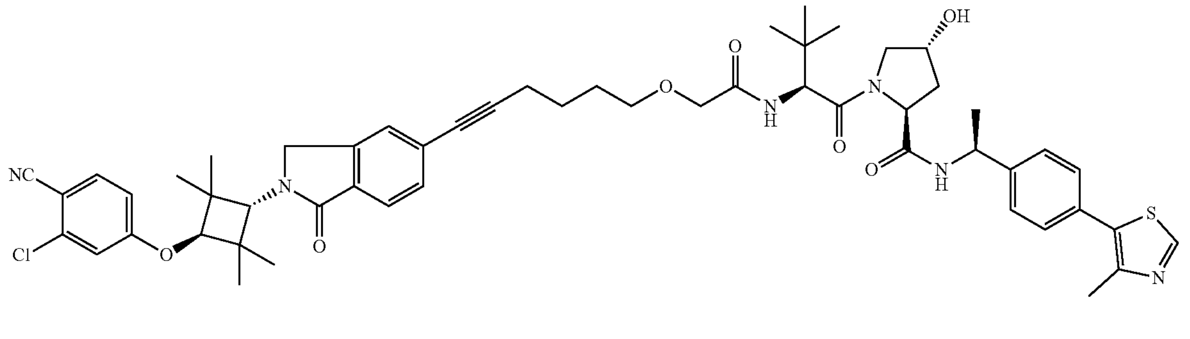

-continued
30
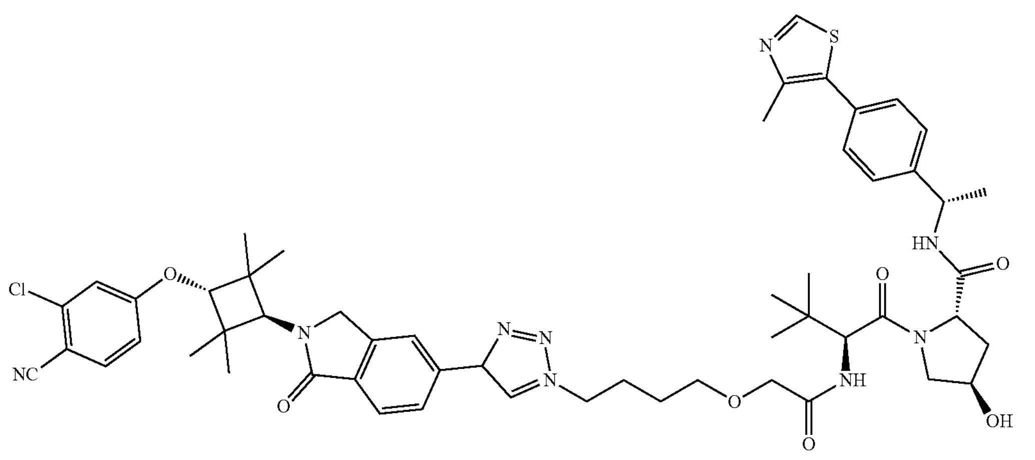
31
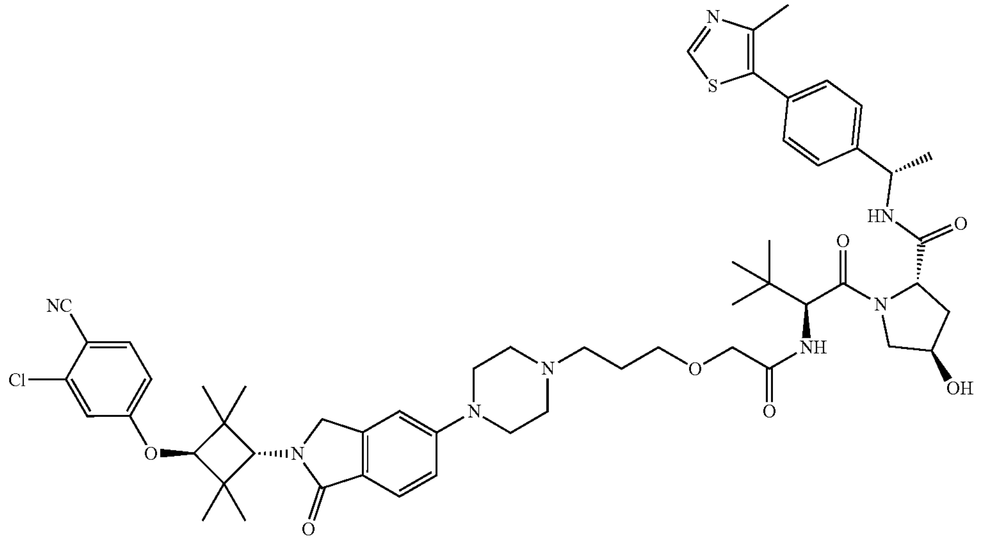
32
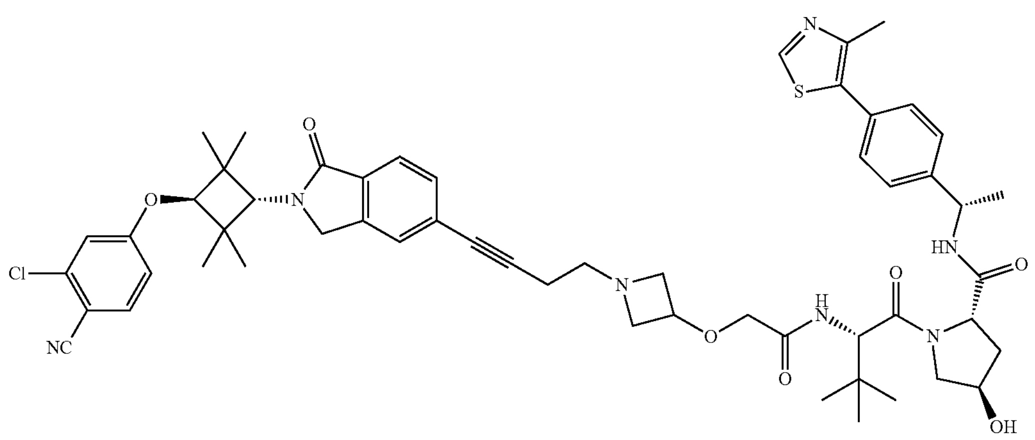

-continued
33
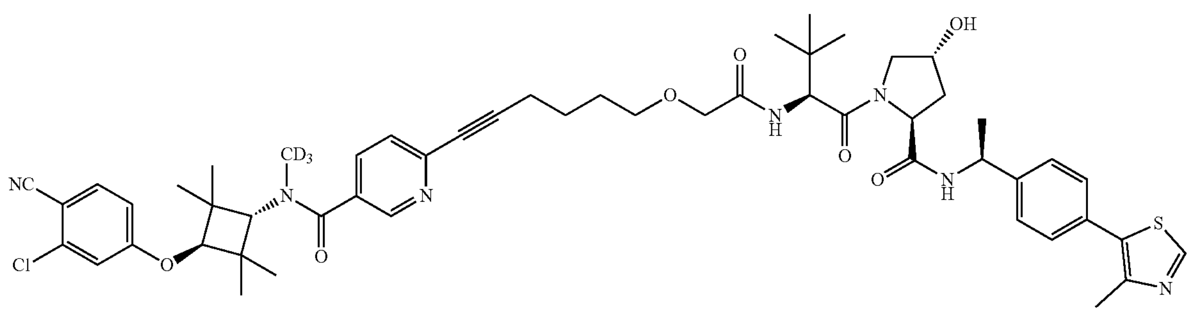
34
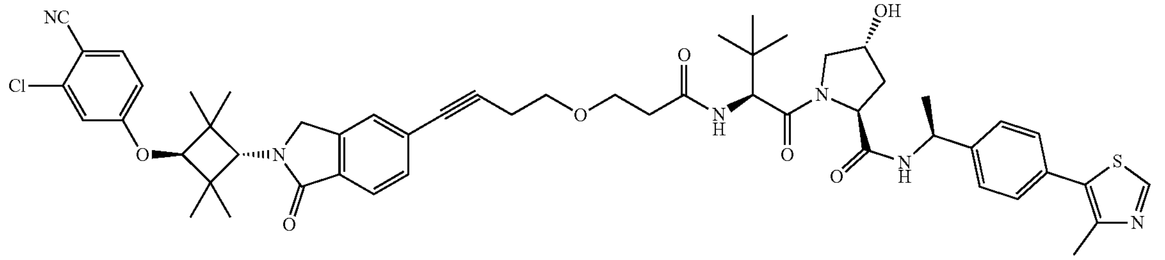
35
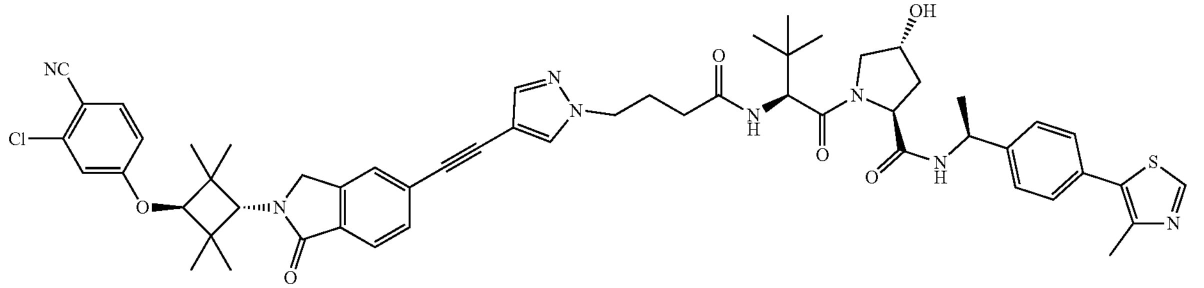
36
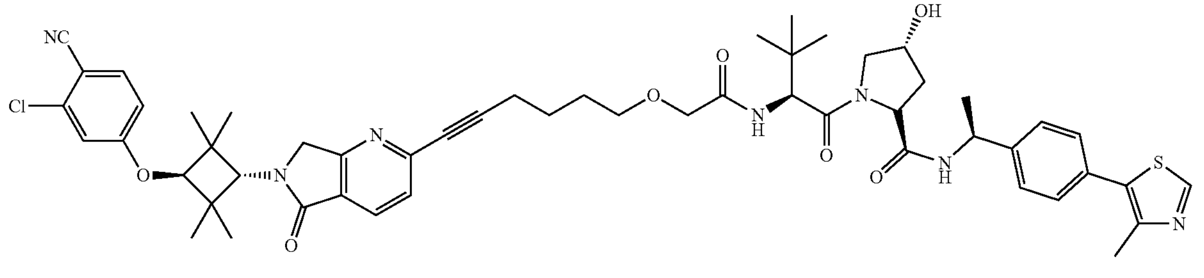
37
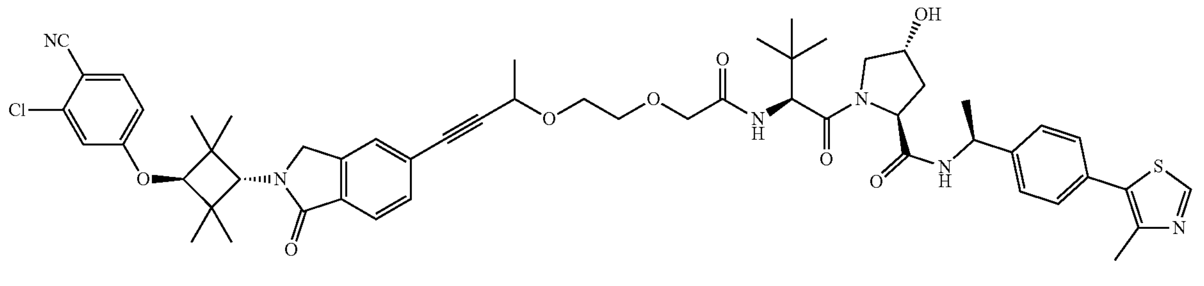

-continued
38
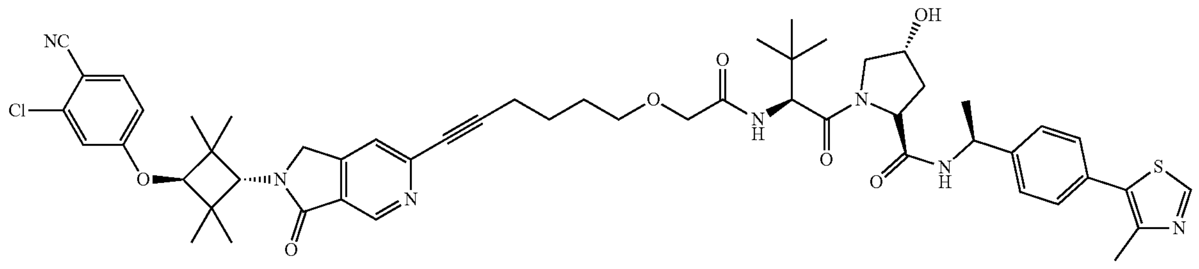
39
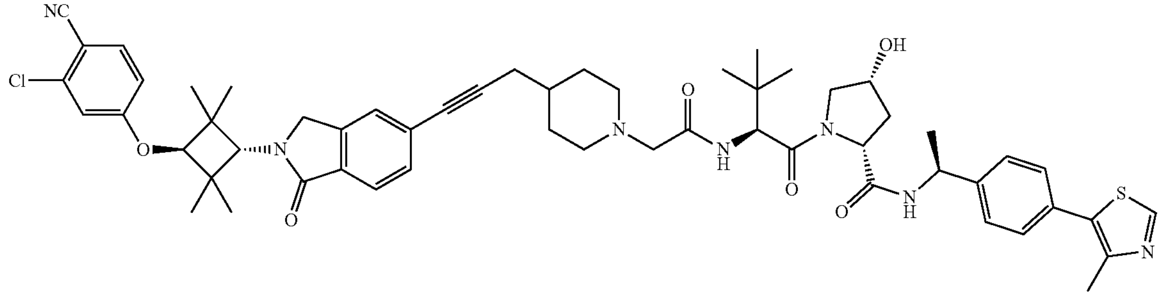
40
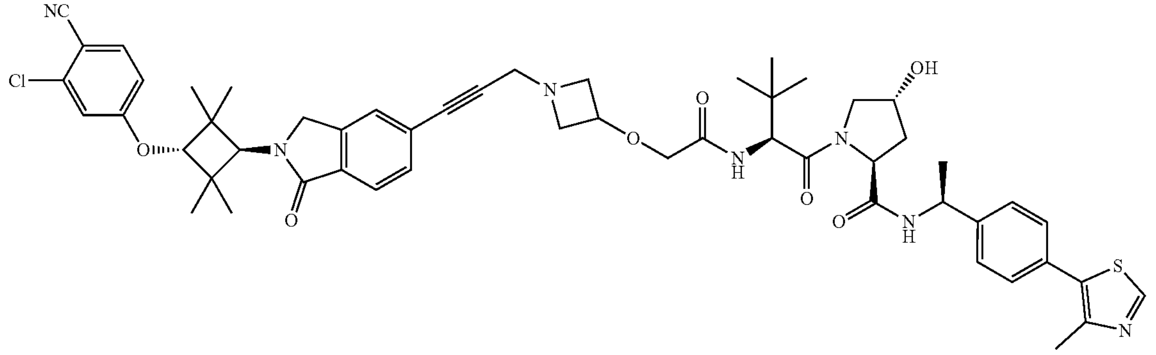
41
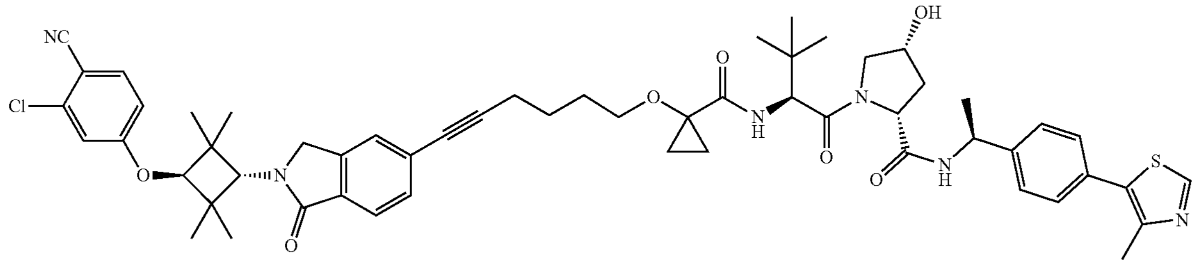
42
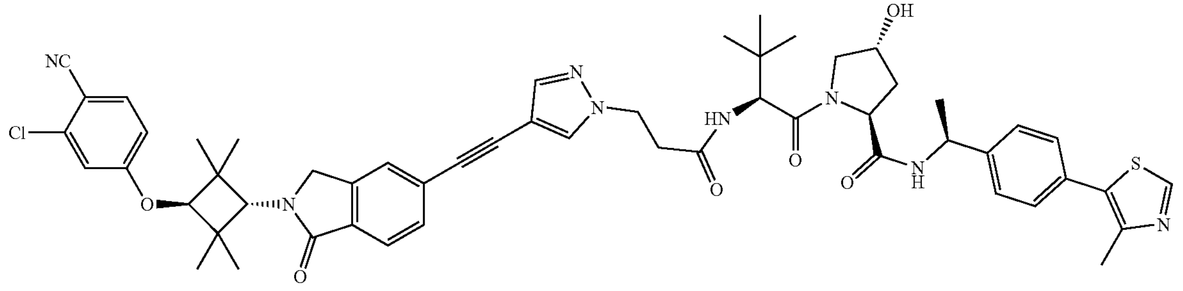

-continued
43
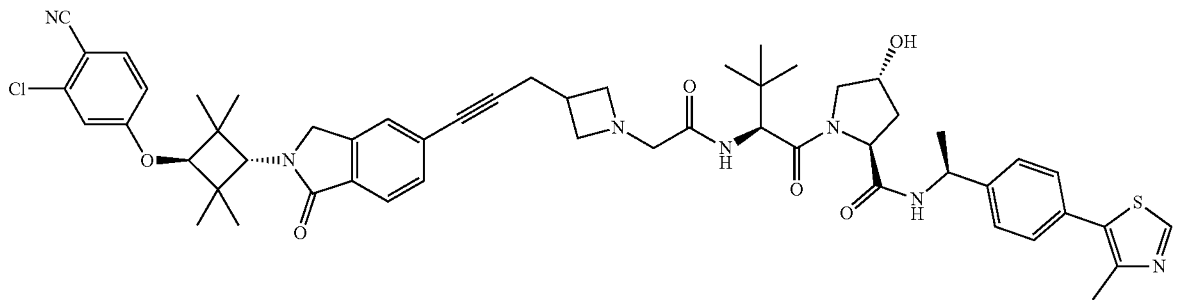
44
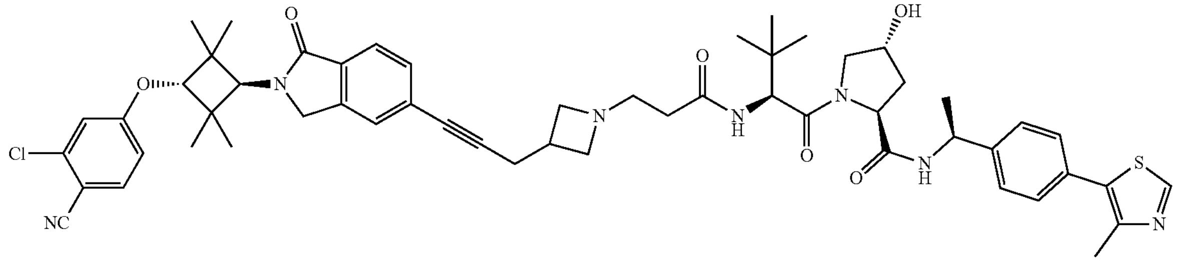
45
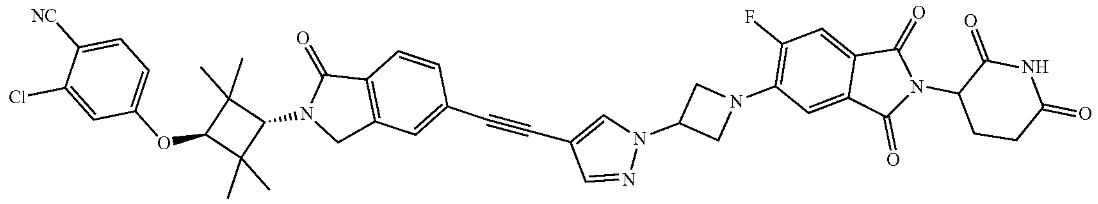
46
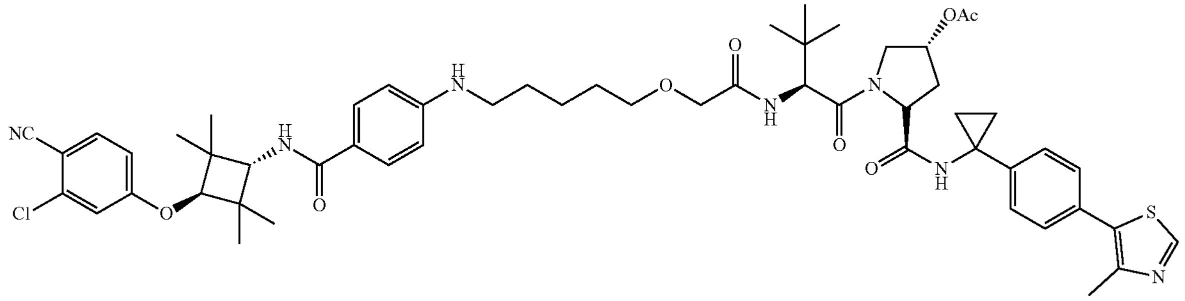
47
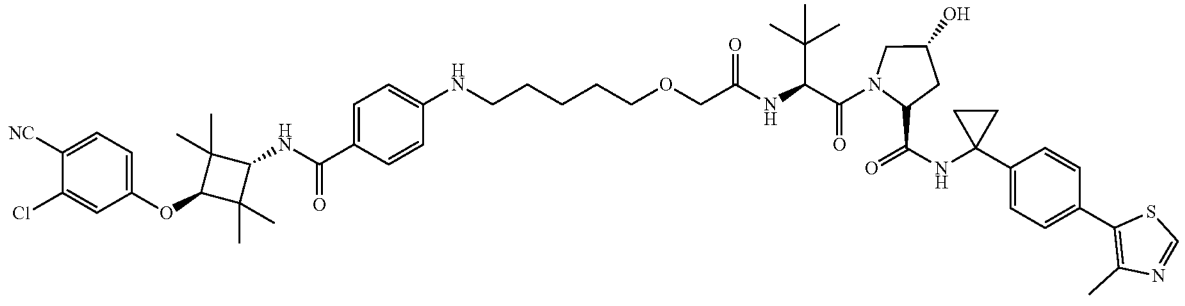

-continued
48
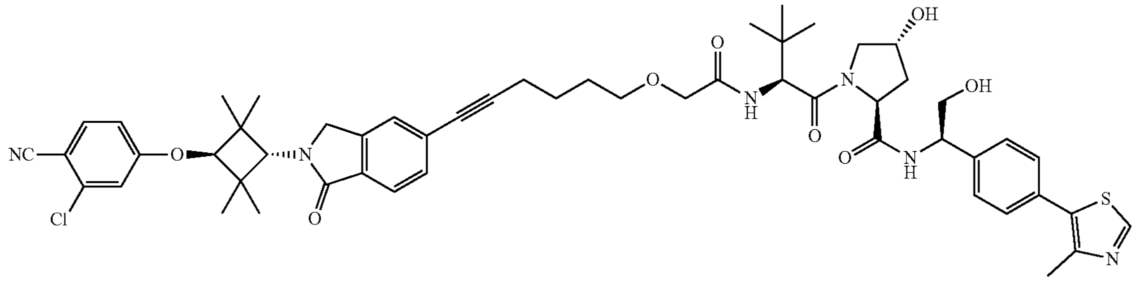
49
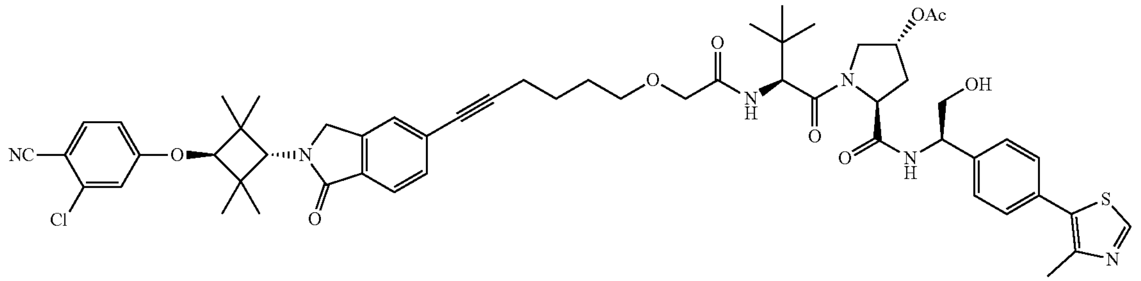
51
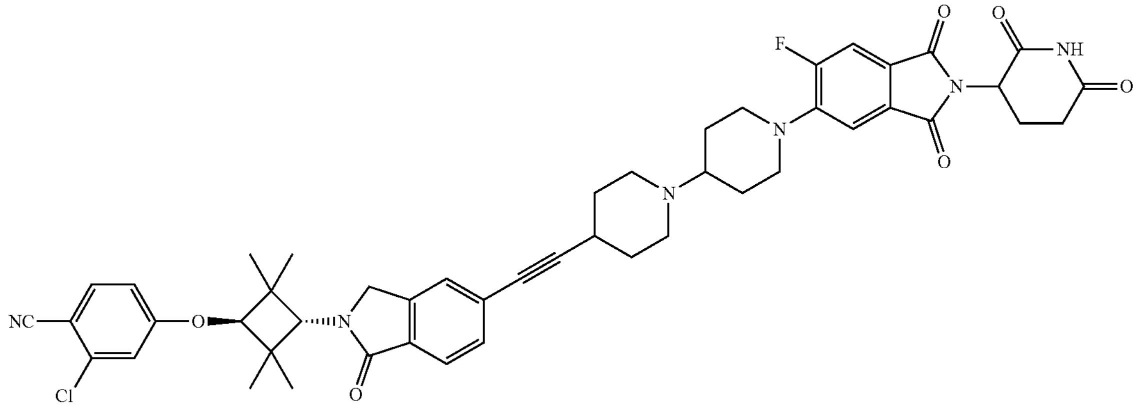
52
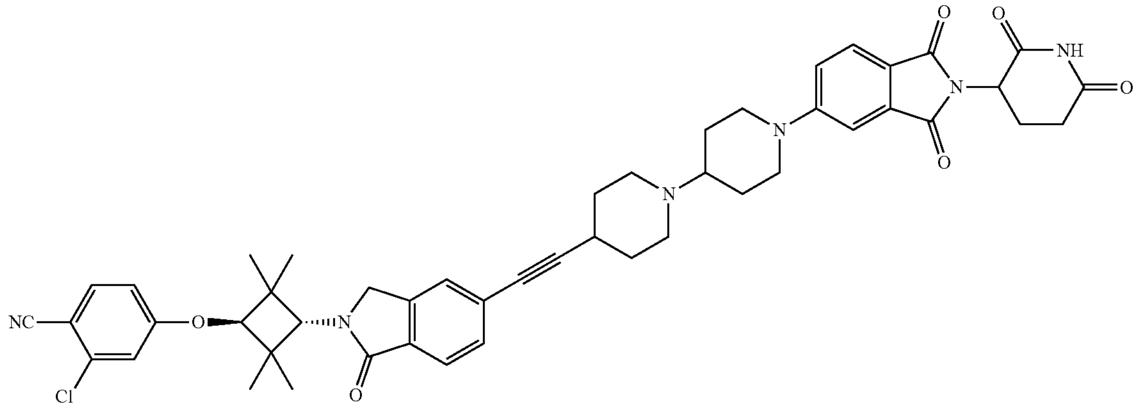

-continued
53
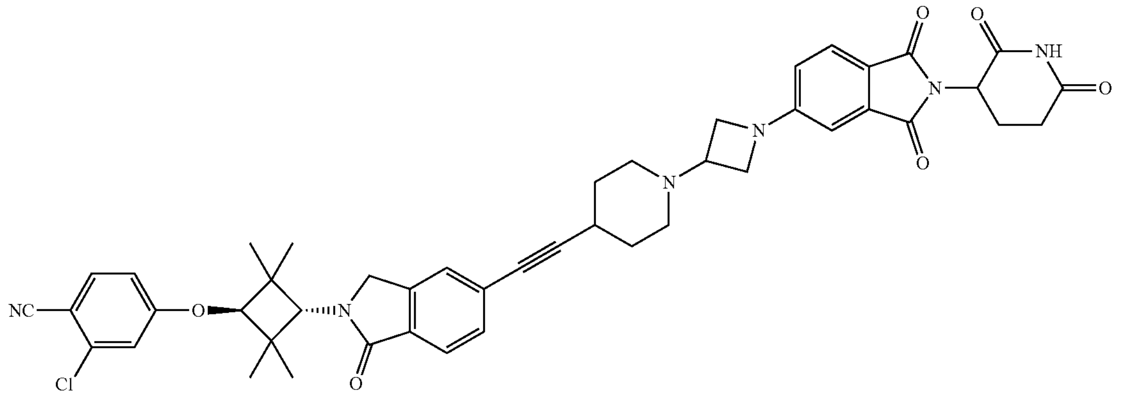
54
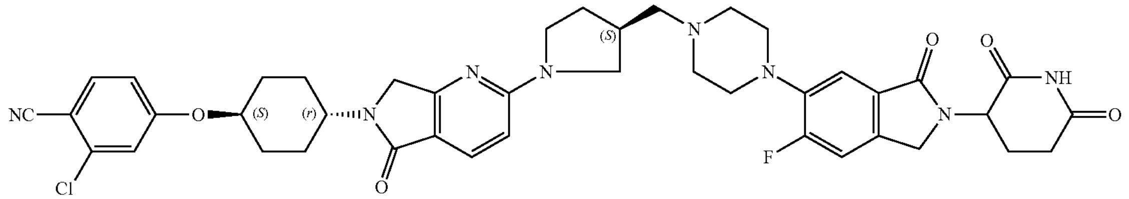
55
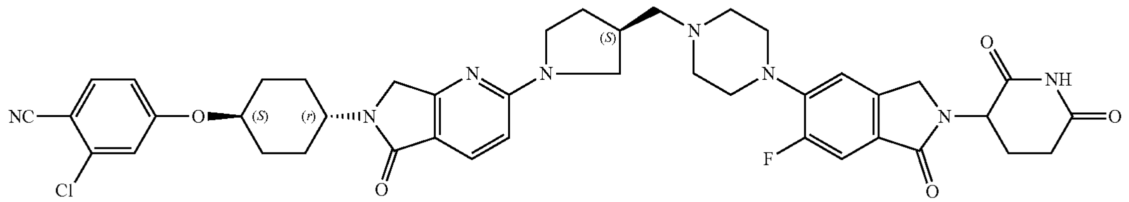
56
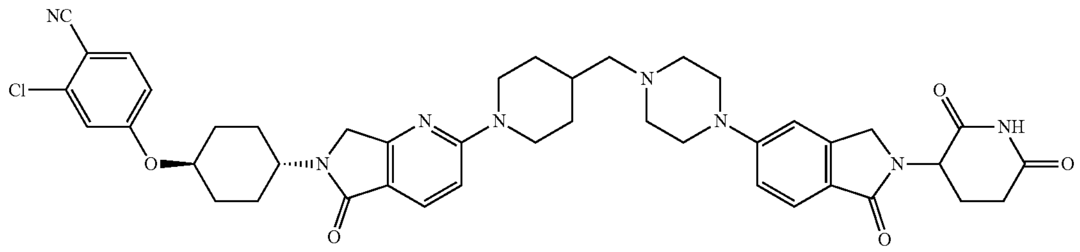
57
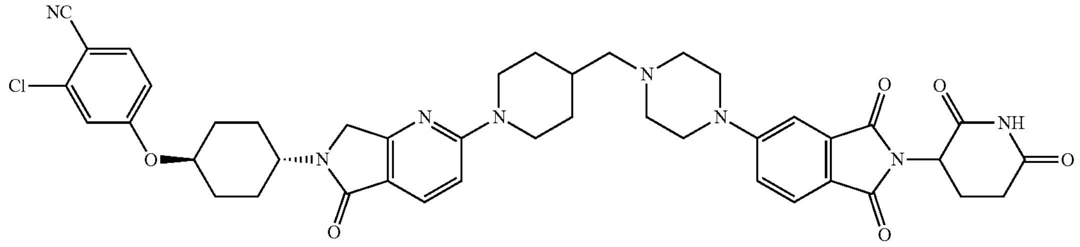
58
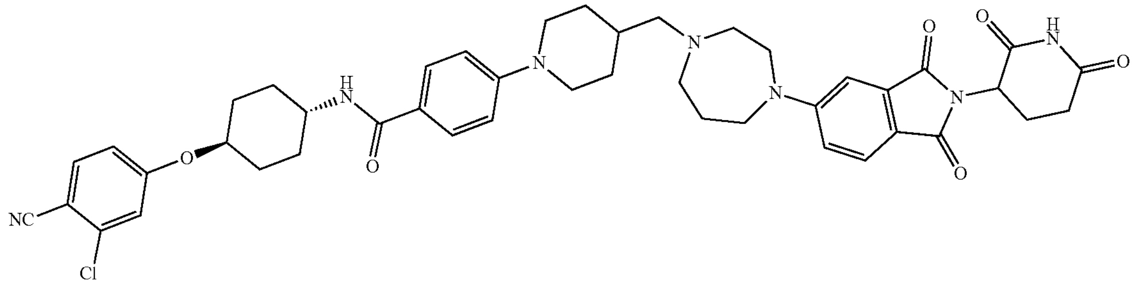

-continued
59
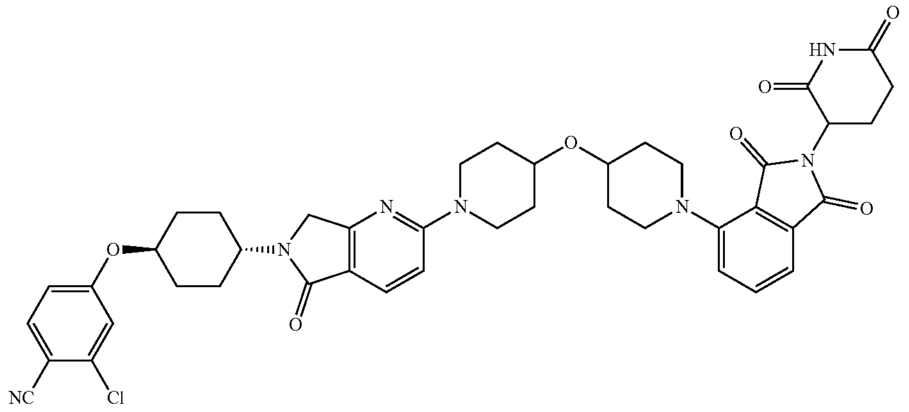
60
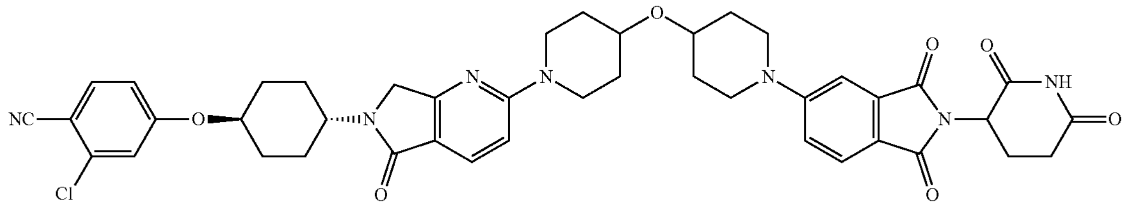
61
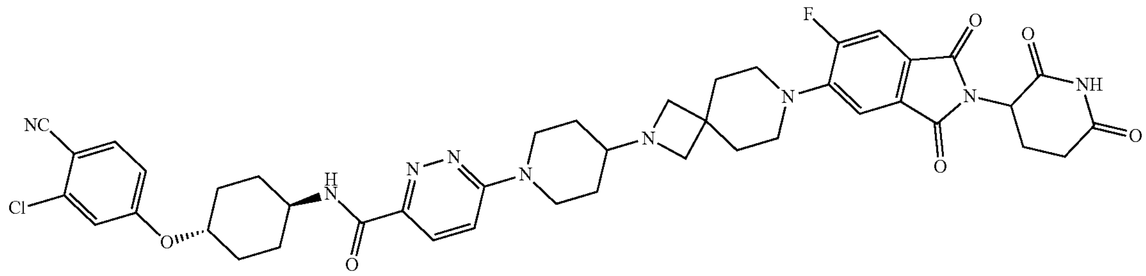
62
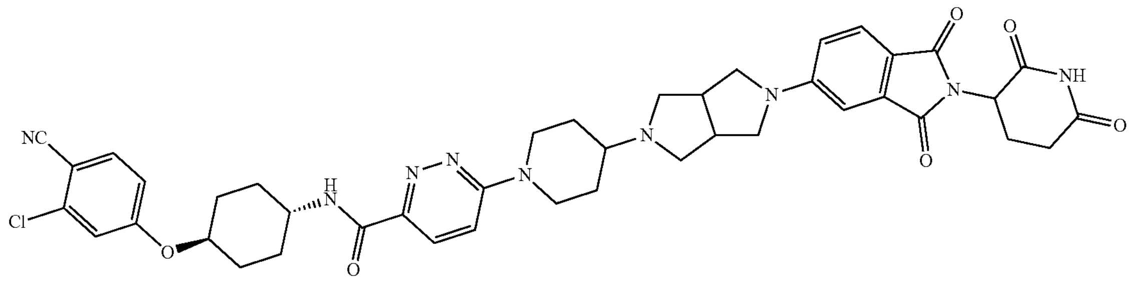
63
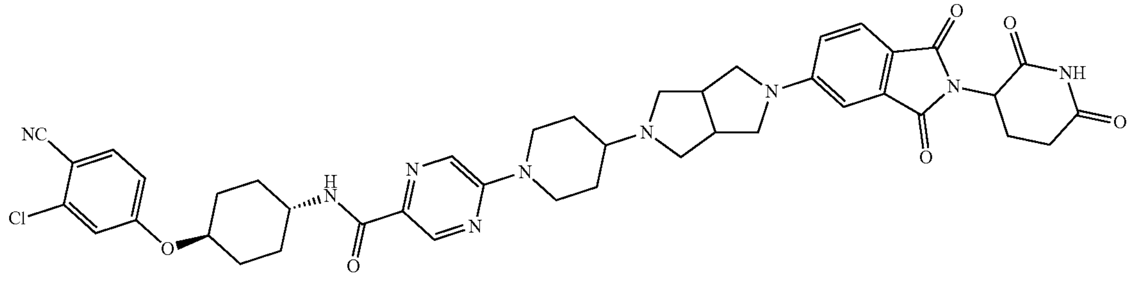

-continued
64
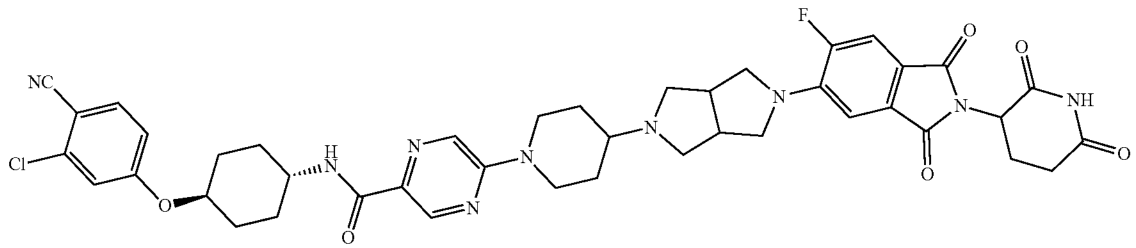
65
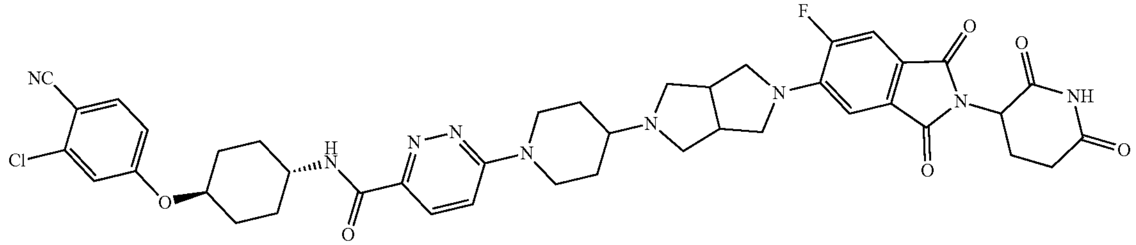
66
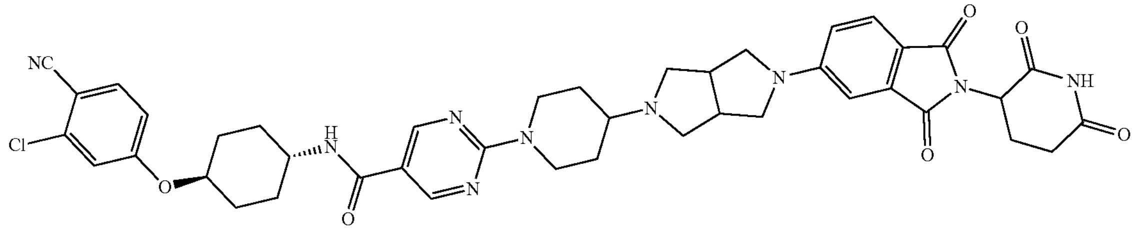
67
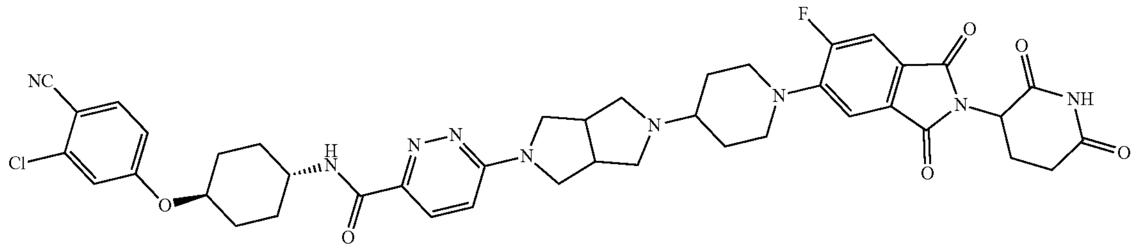
68
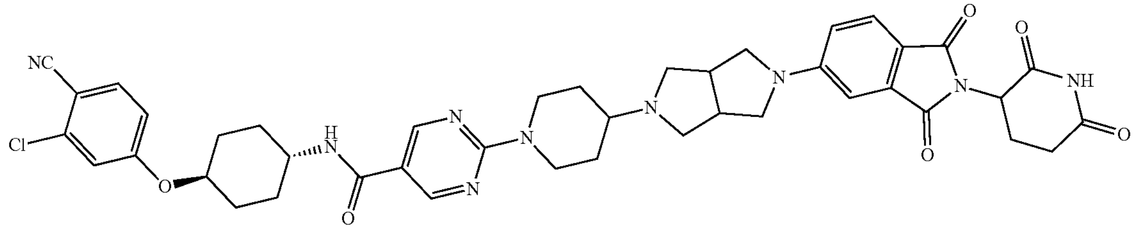
69
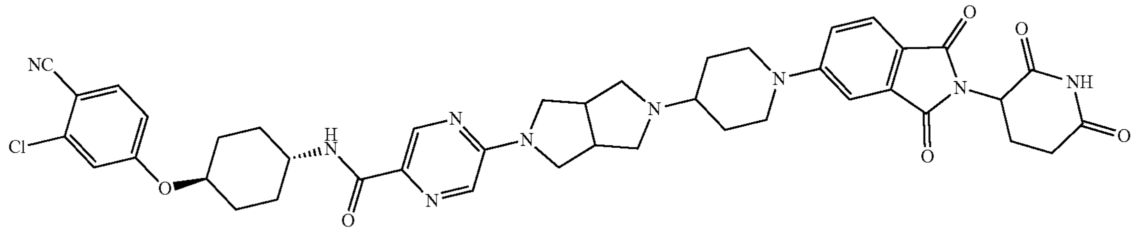

-continued
70
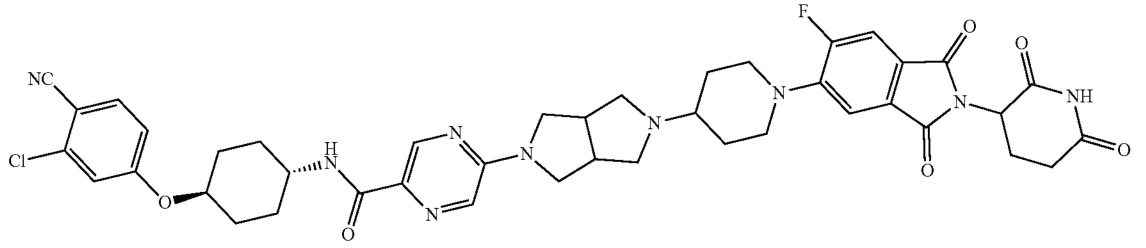
71
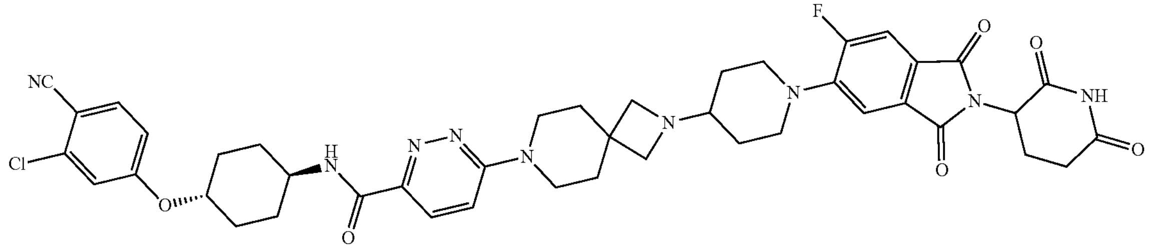
72
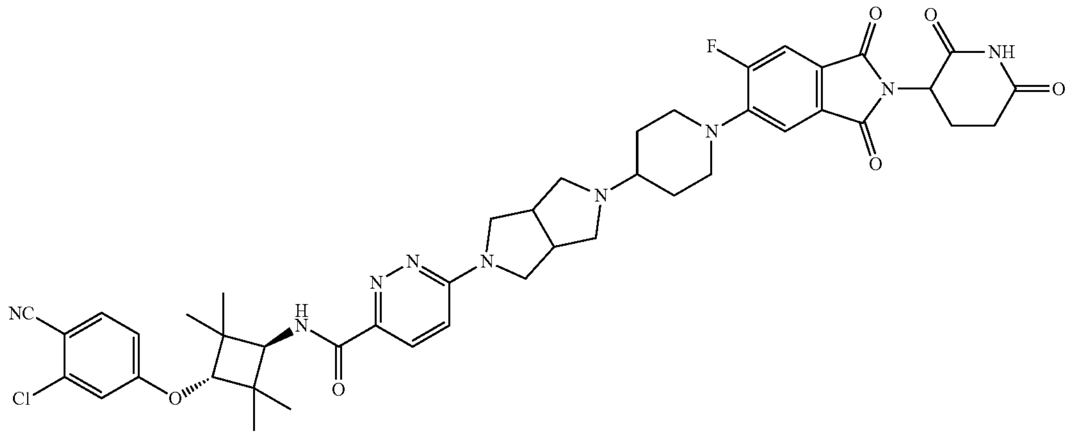
73
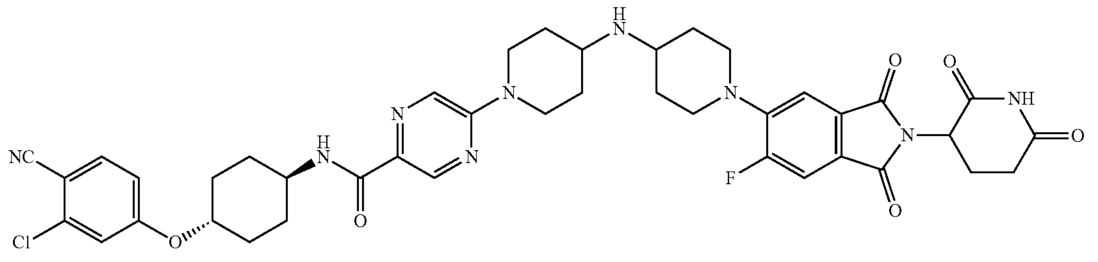
74
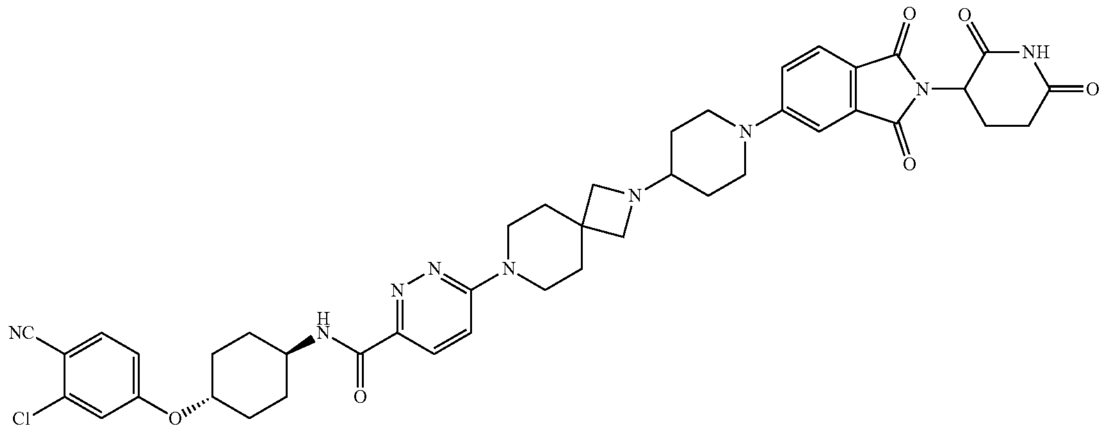

-continued
75
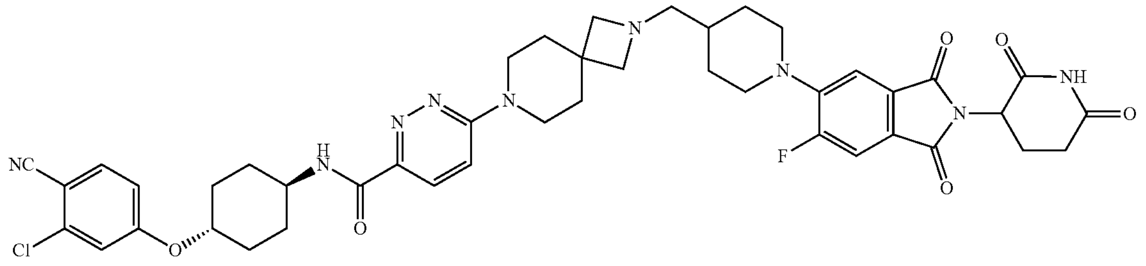
76
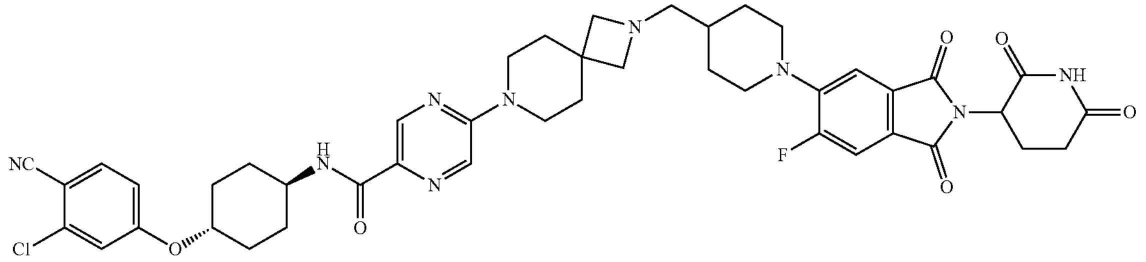
77
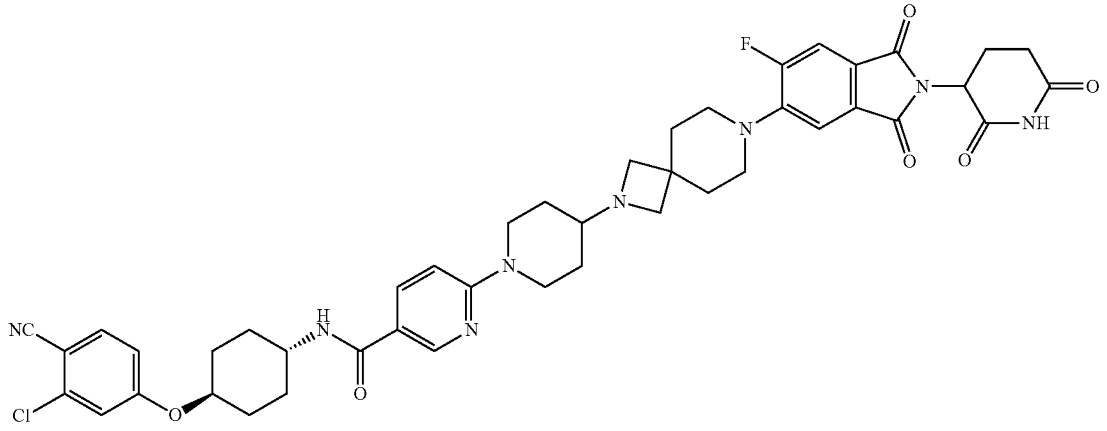
78
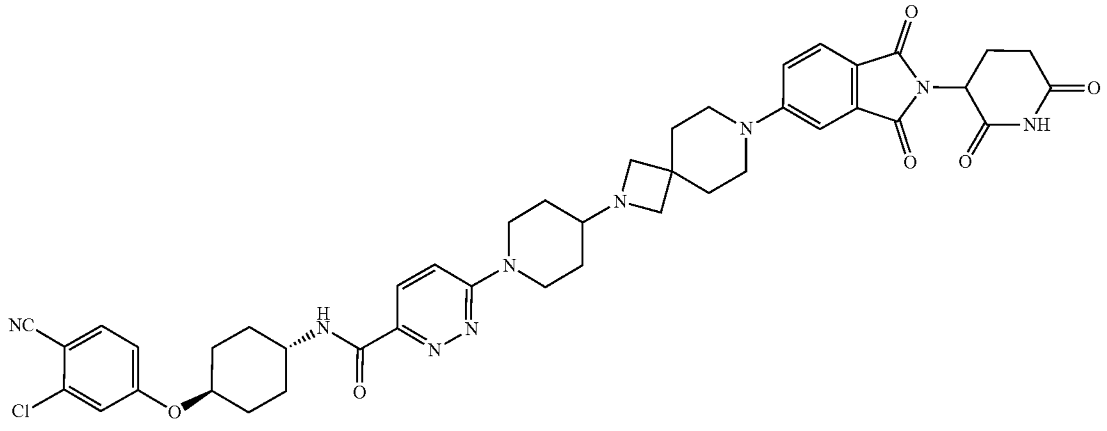

-continued
79
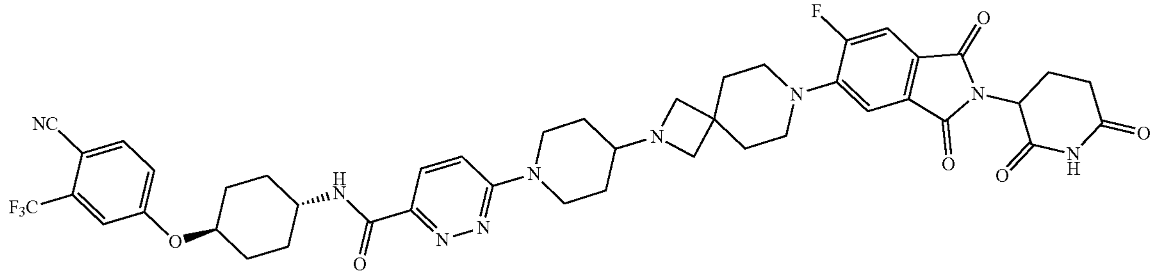
80
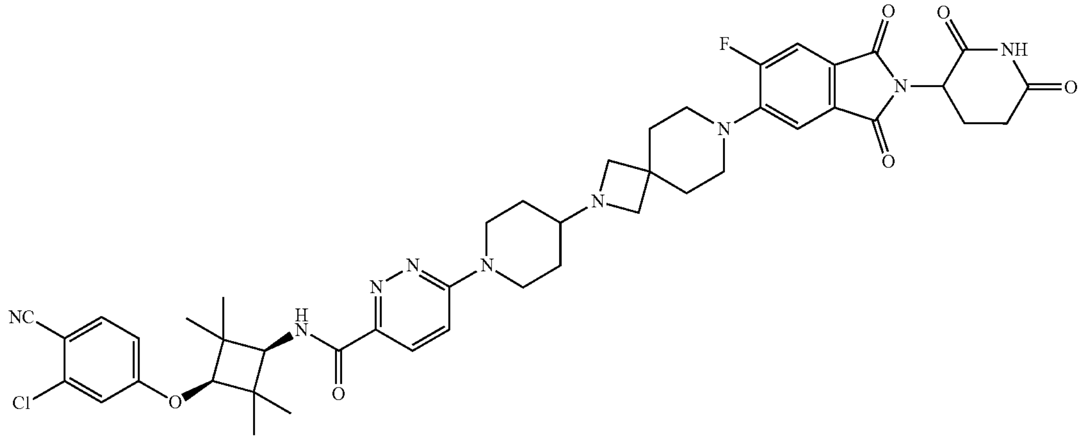
81
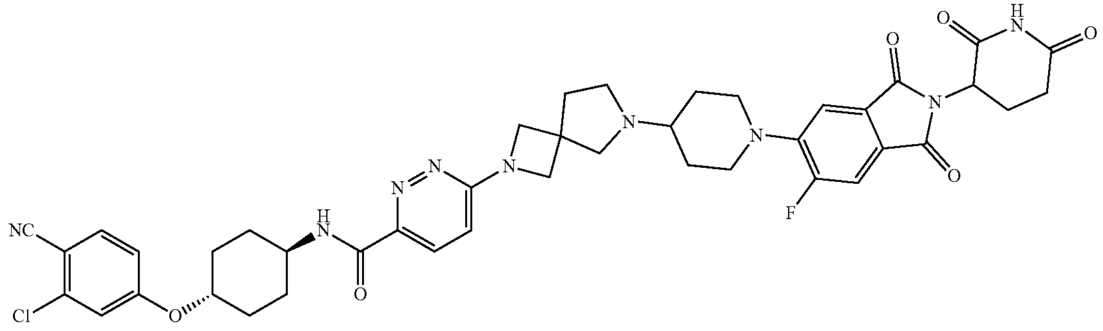
82
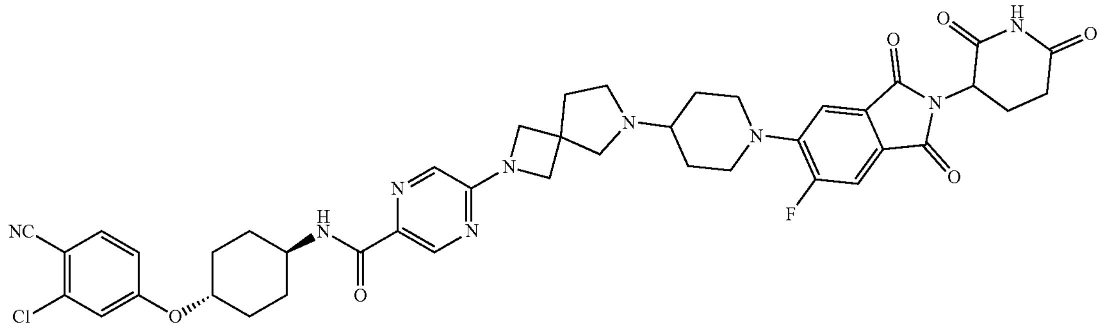

-continued
83
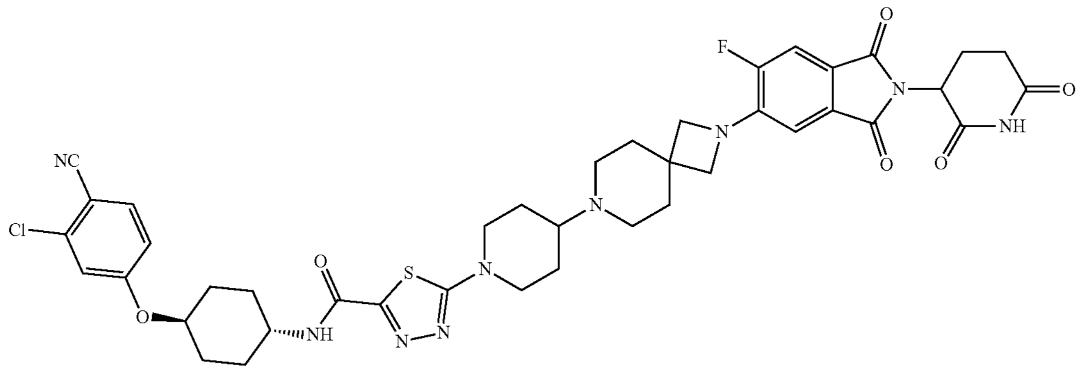
84
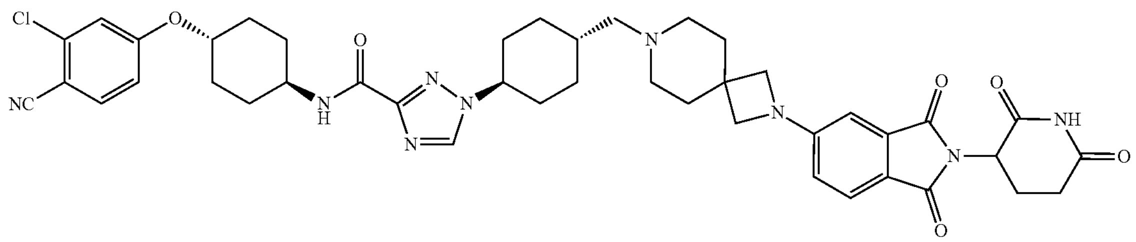
85
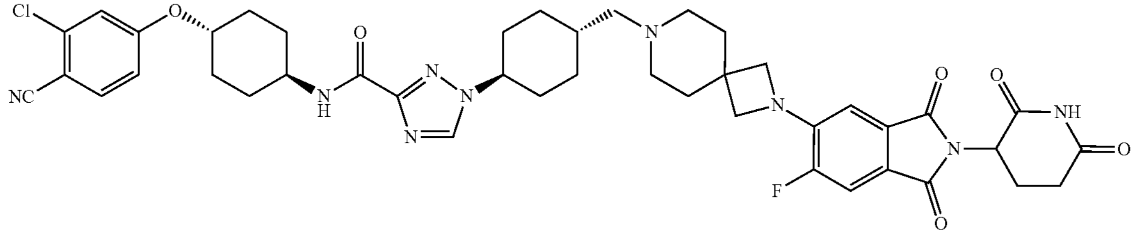
86
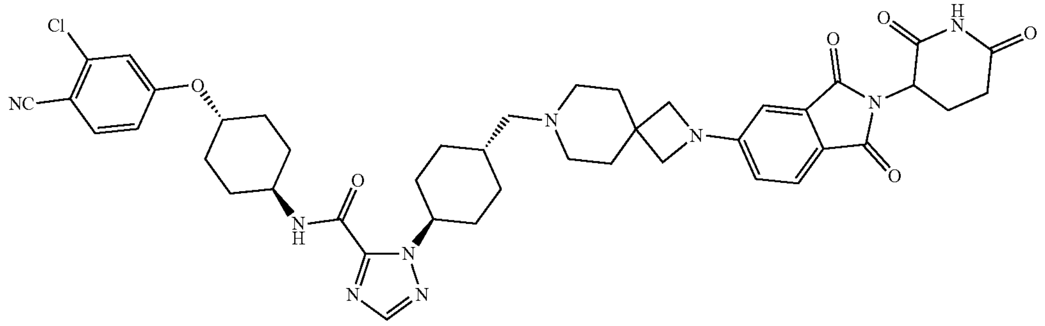
87
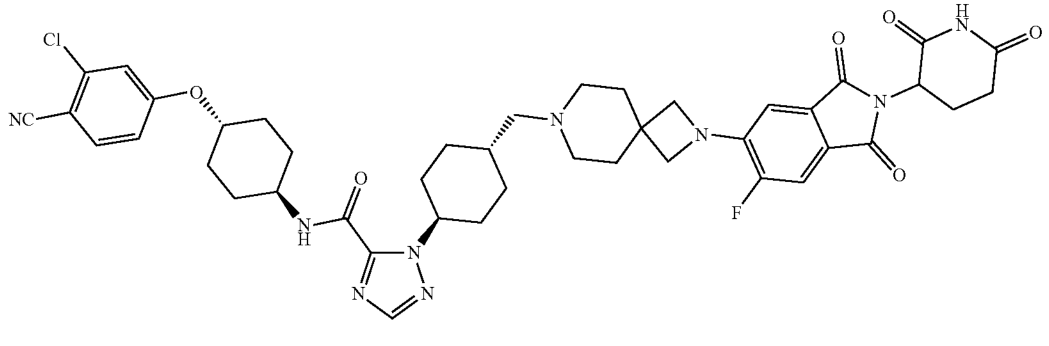

-continued
88
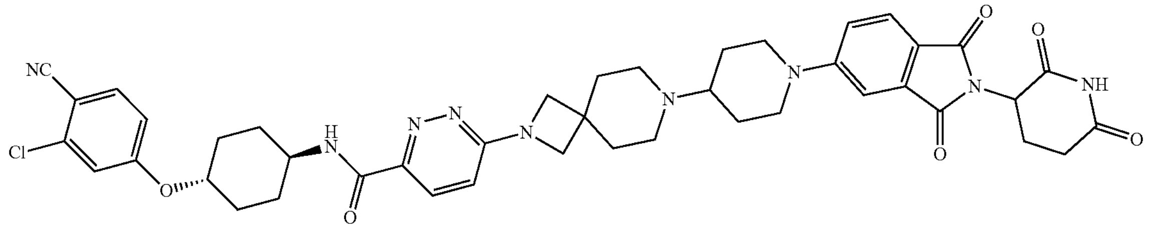
89
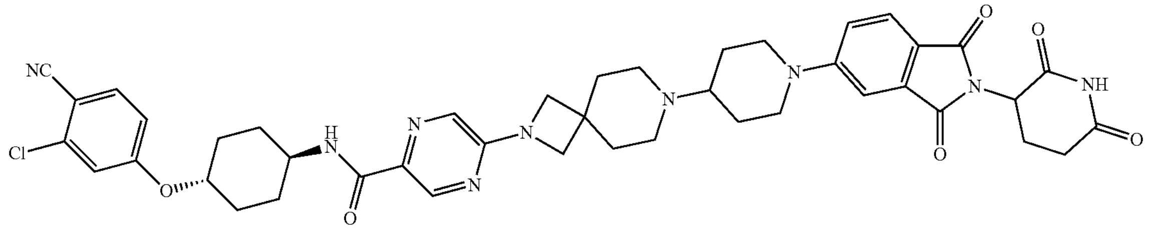
90
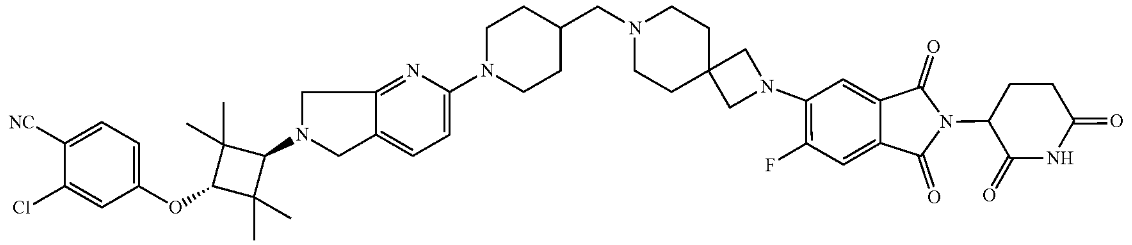
91
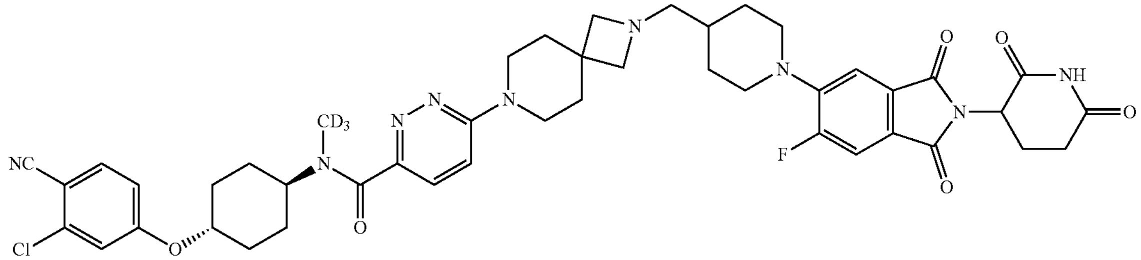
92
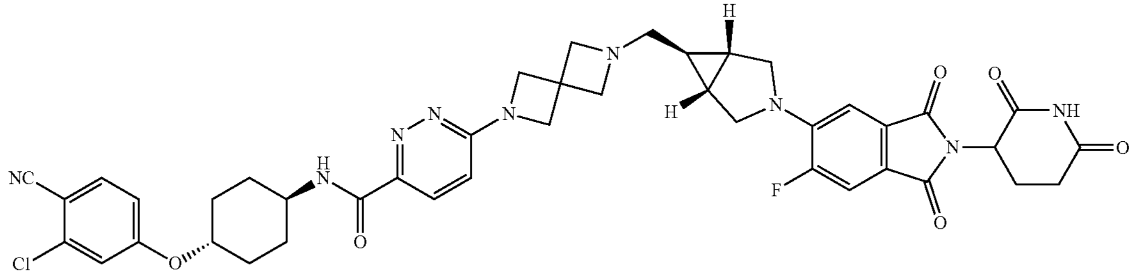
93
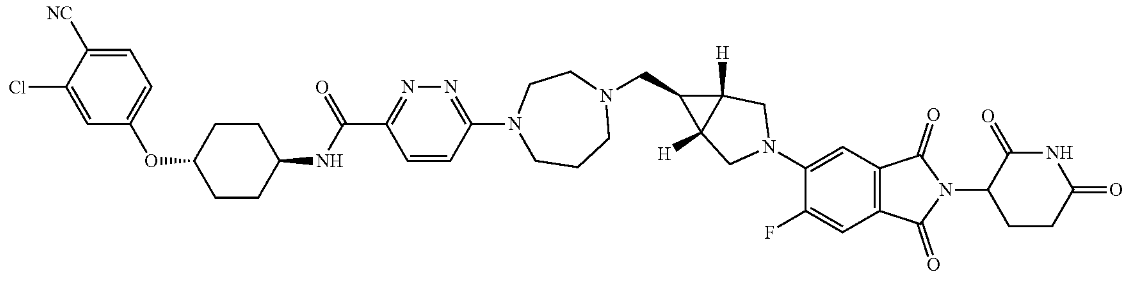

-continued
94
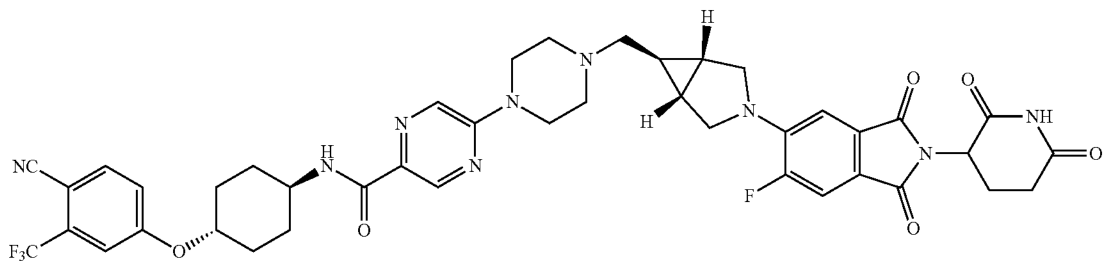
95
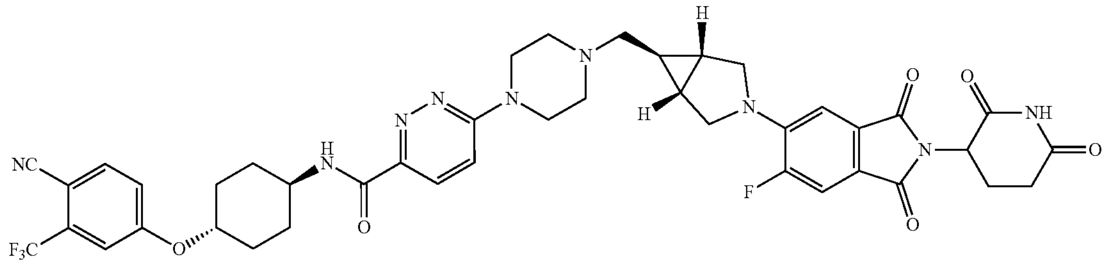
96
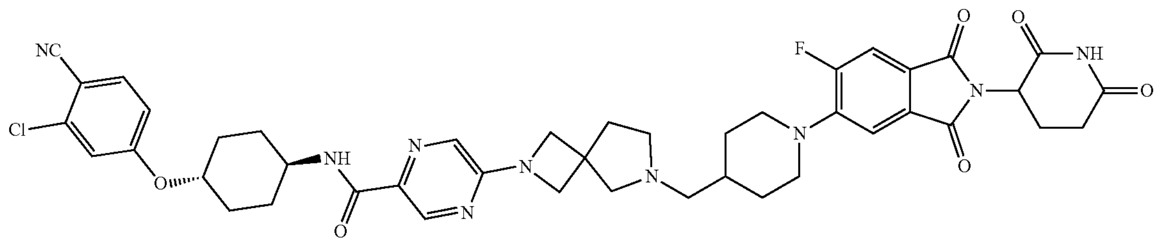
97
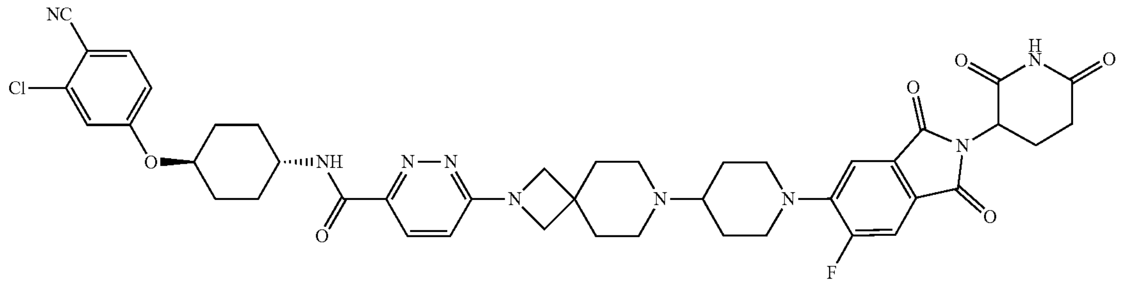
98
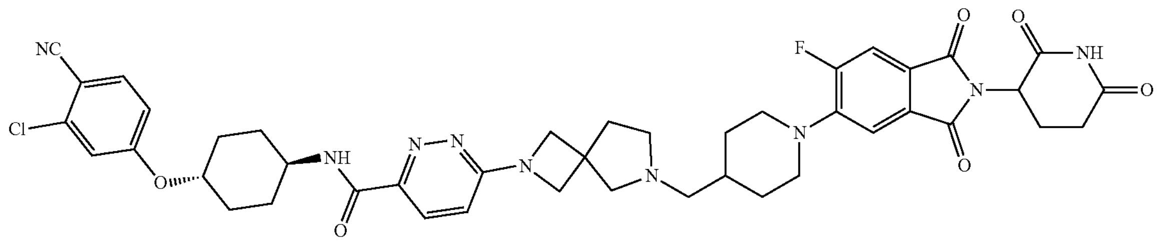
99
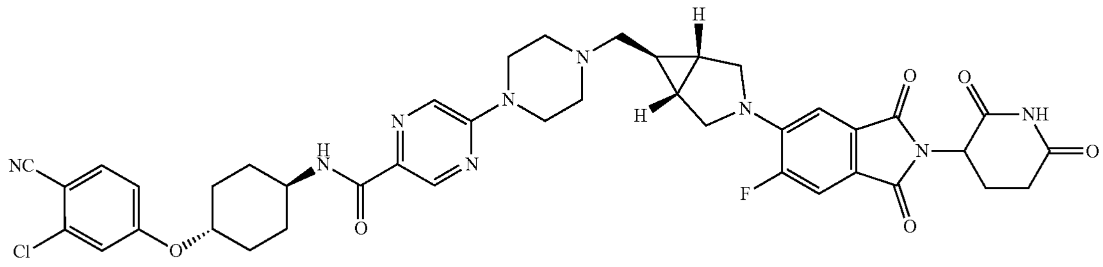

-continued
100
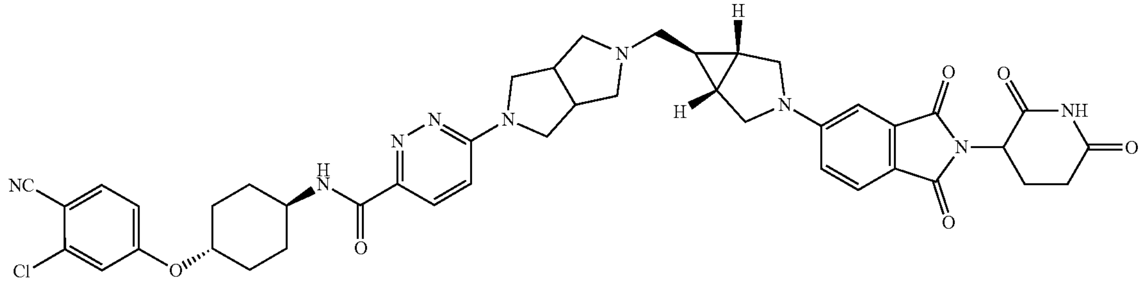
101
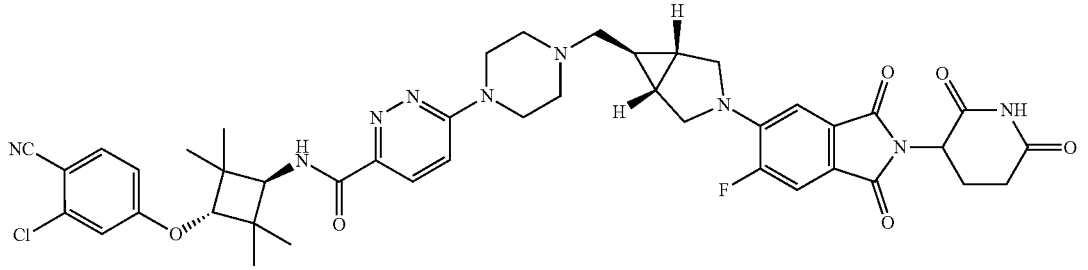
102
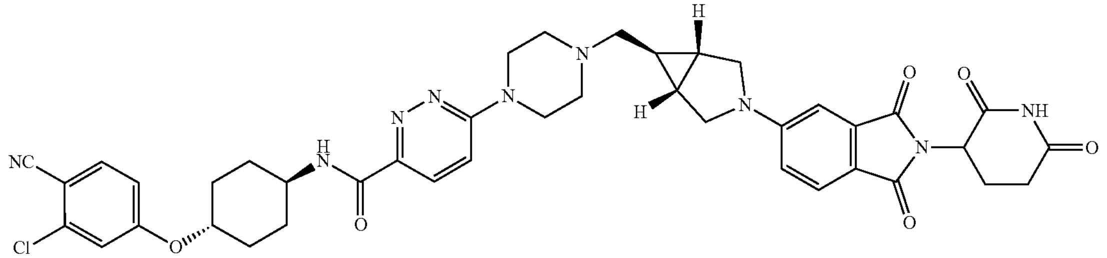
103
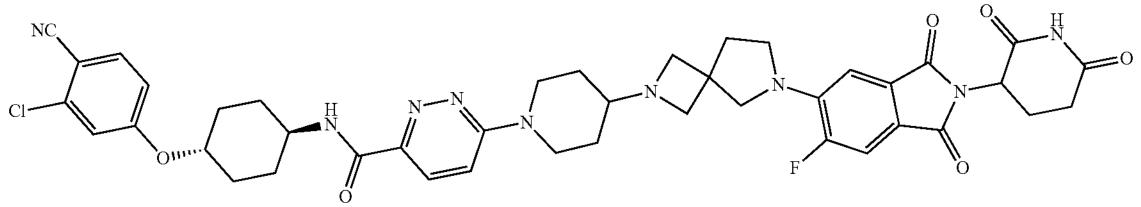
104
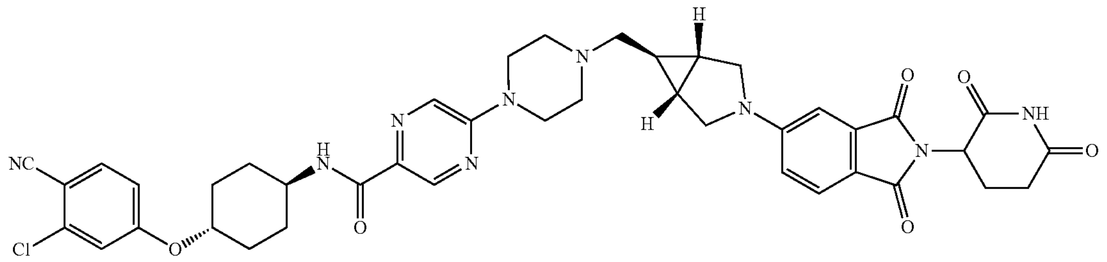
105
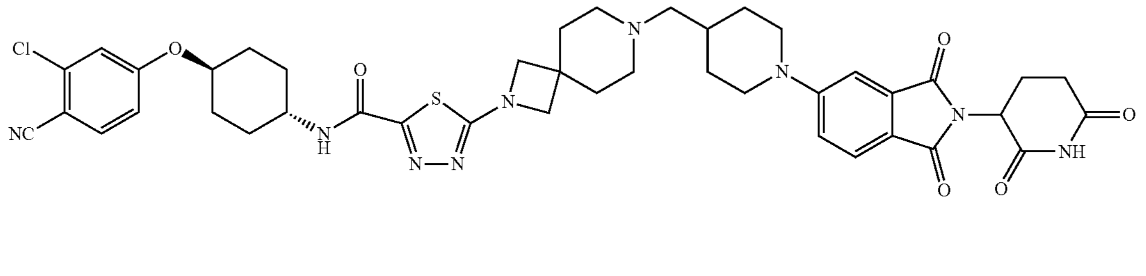

-continued
106
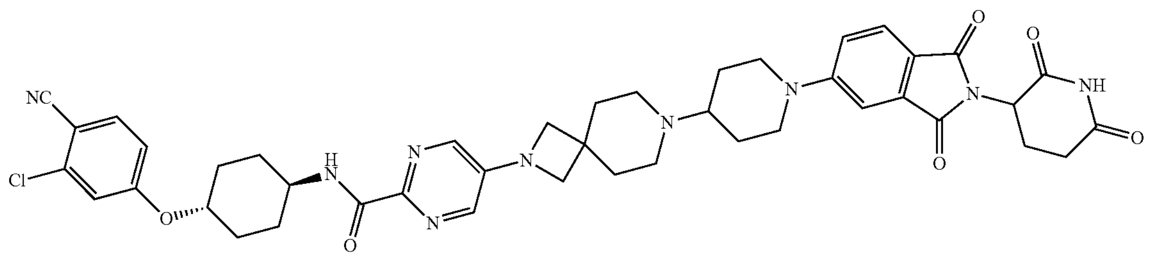
107
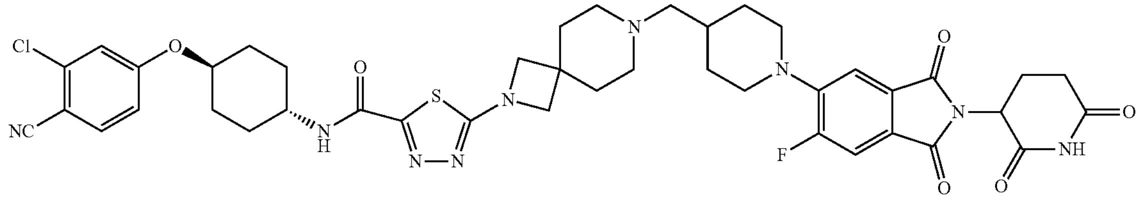
108
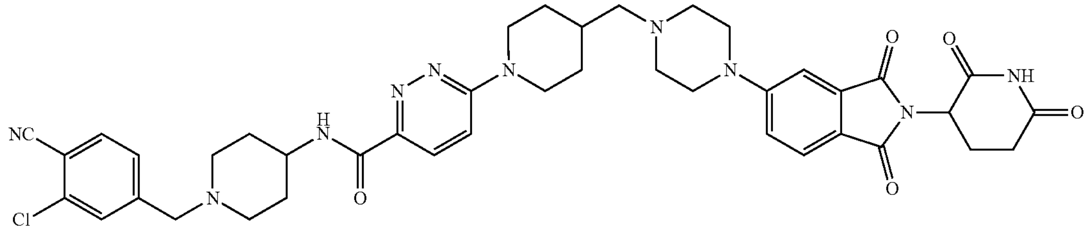
109
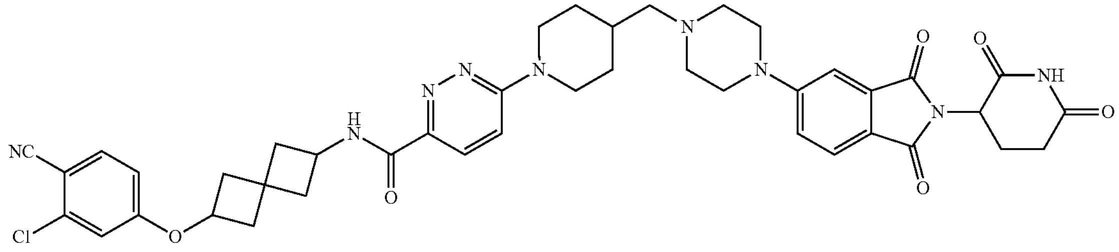
110
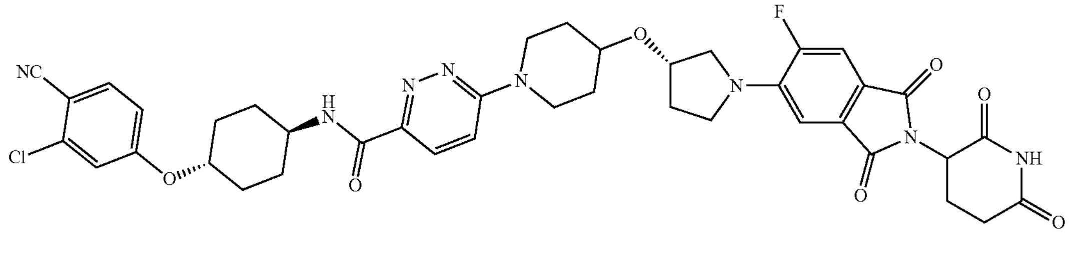
111
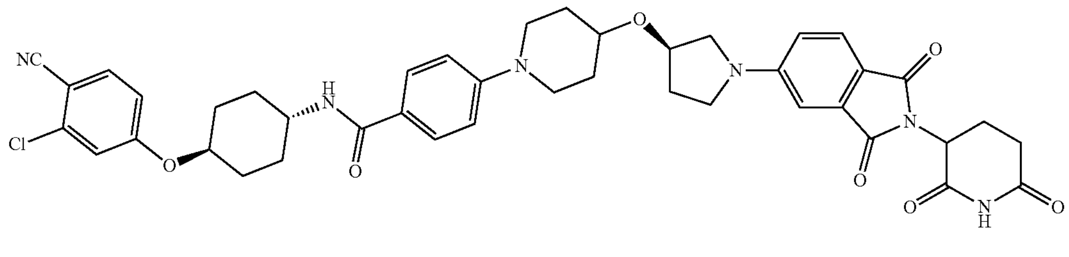

-continued
112
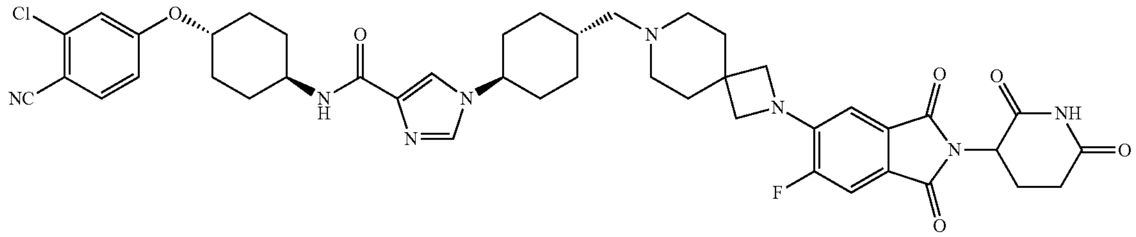
113
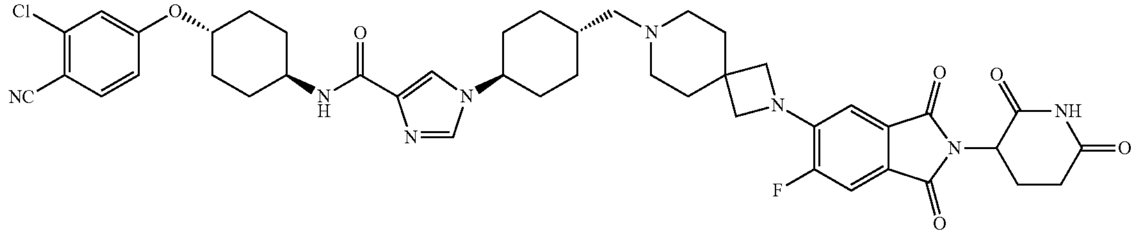
114
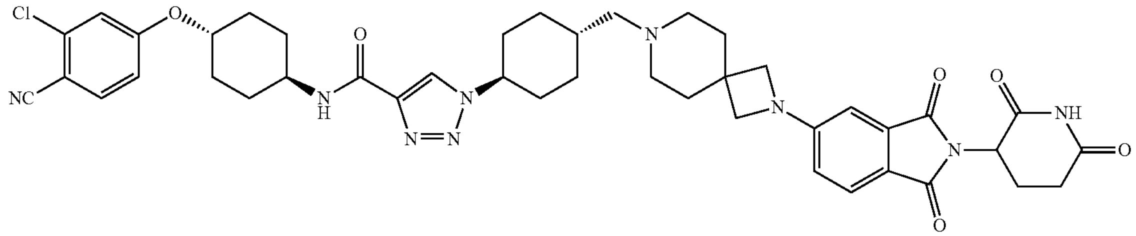
115
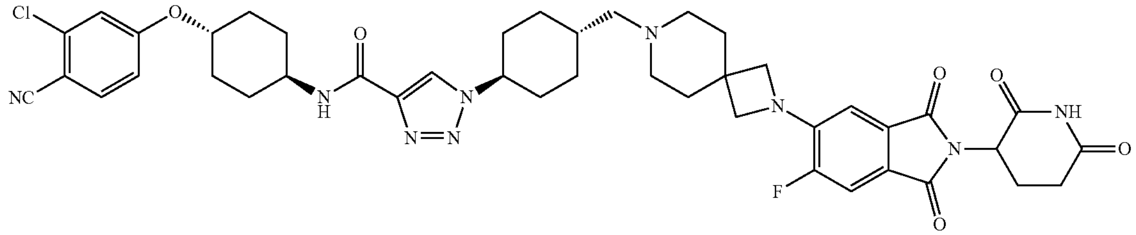
116
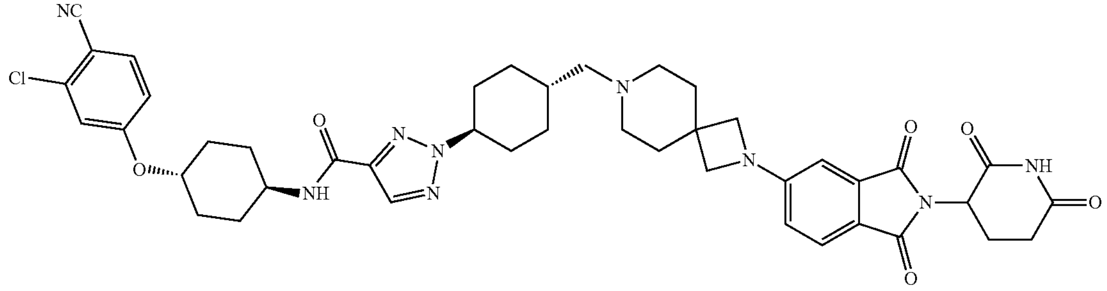
117
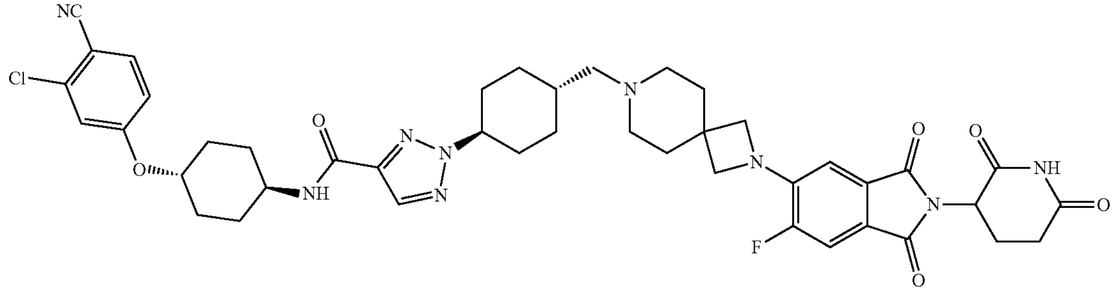

-continued
118
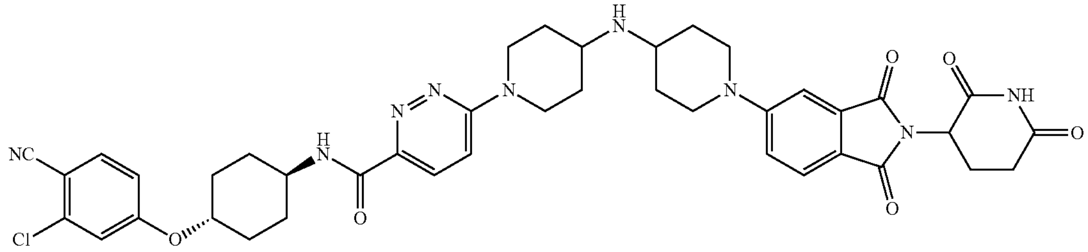
119
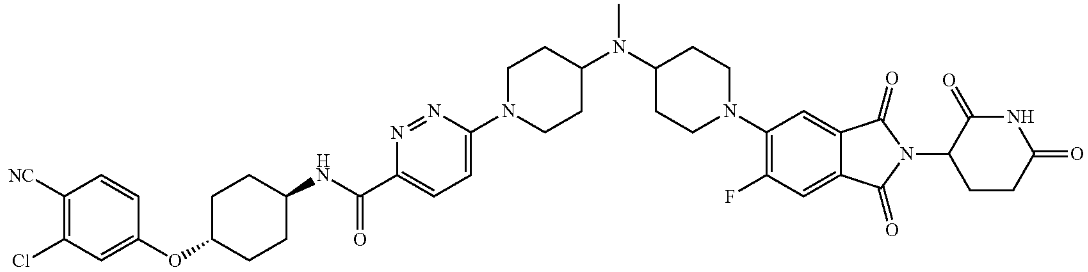
120
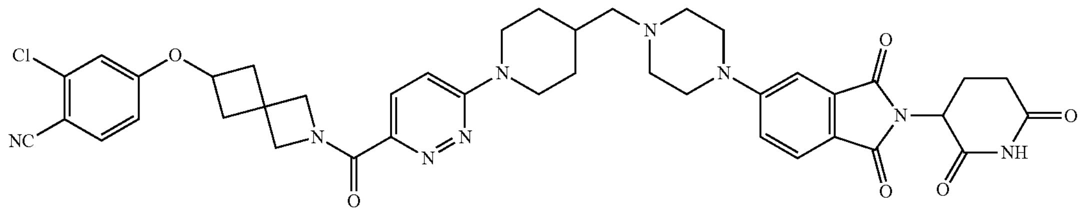
121
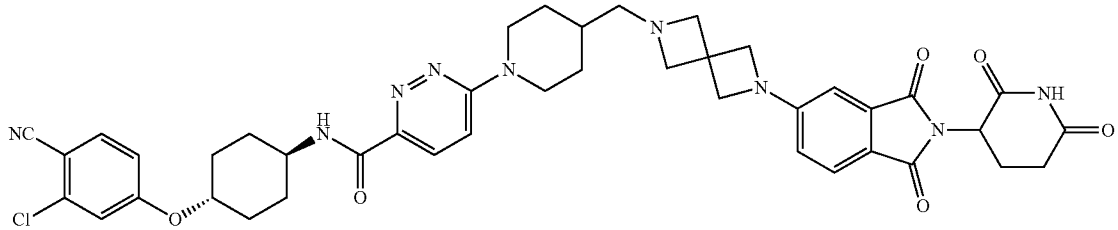
122
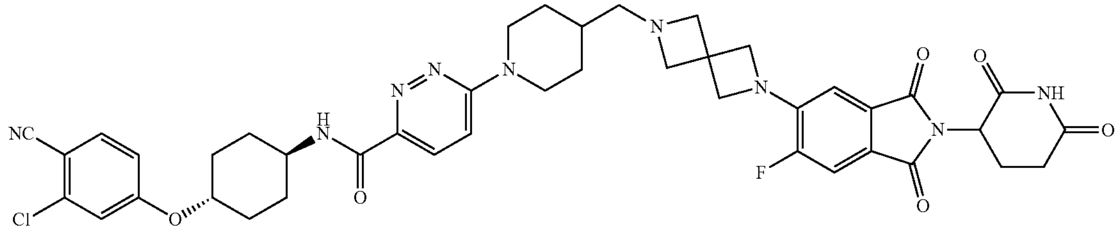
123
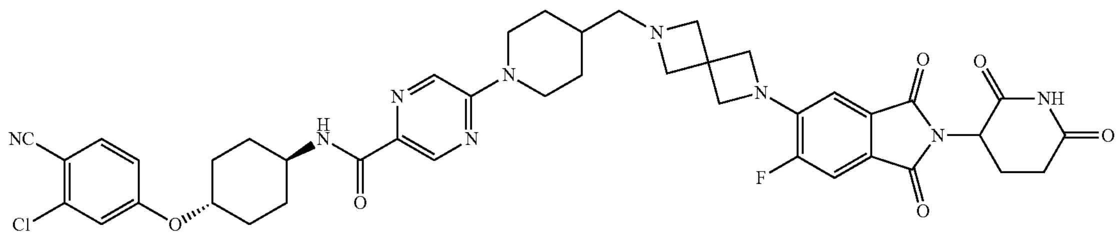

-continued
124
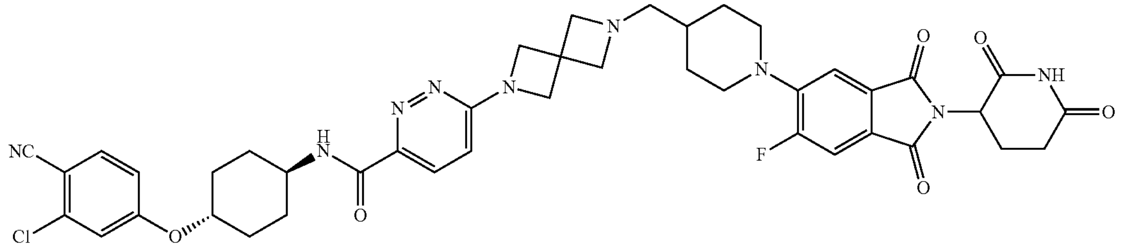
125
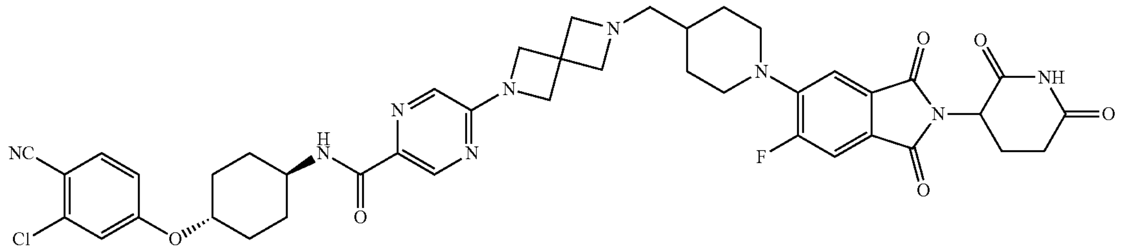
126
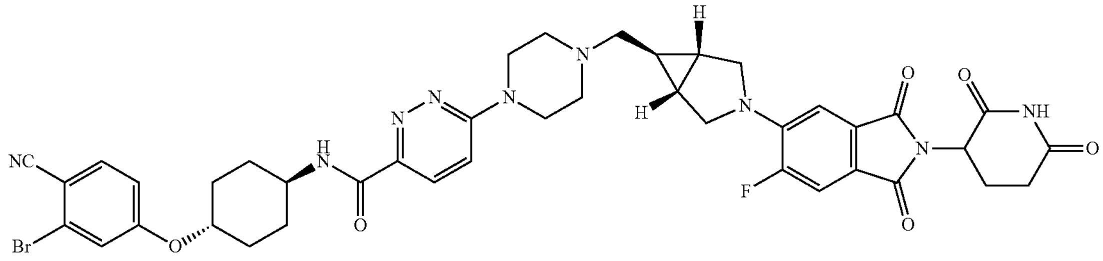
127
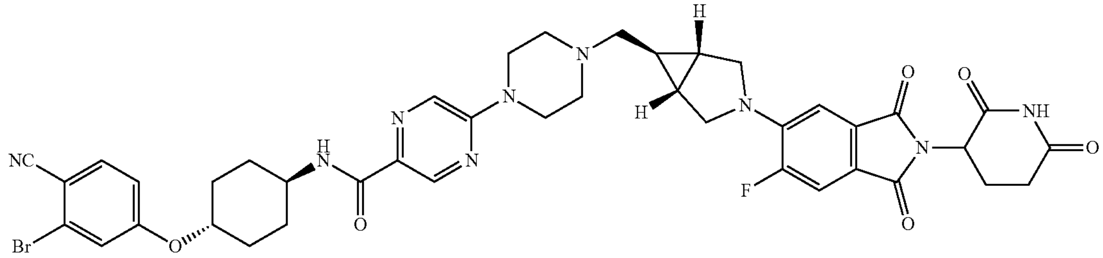
128
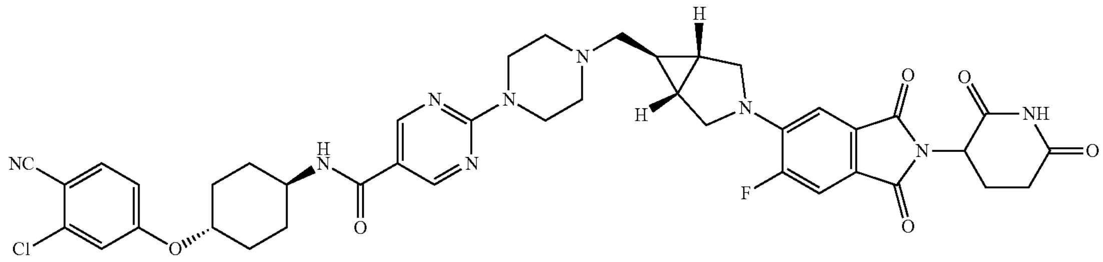

-continued
129
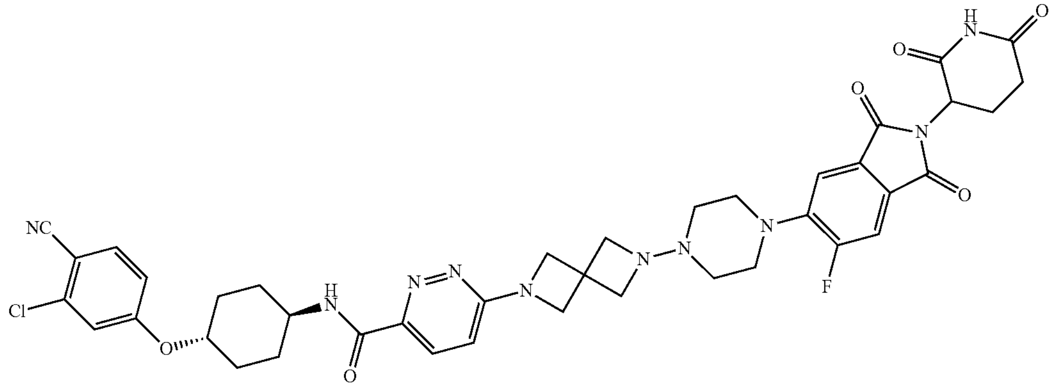
130
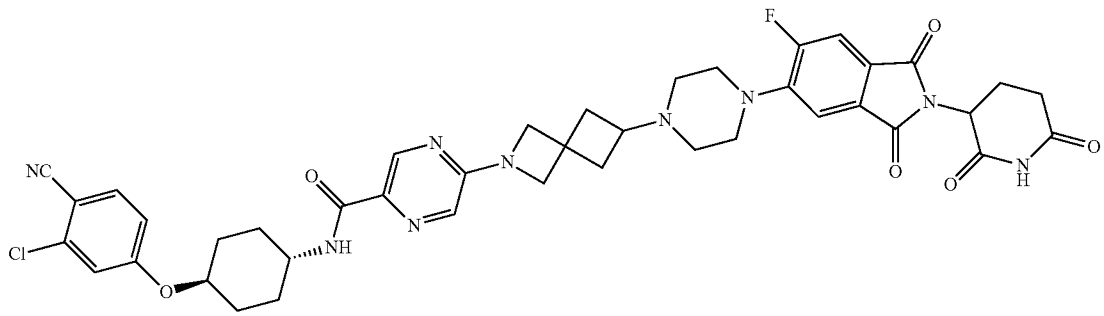
131
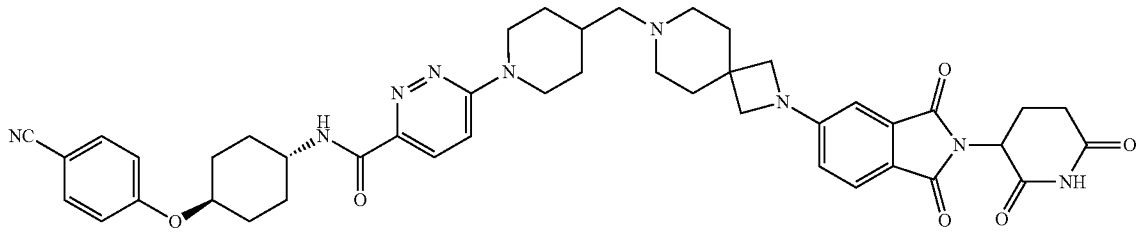
132
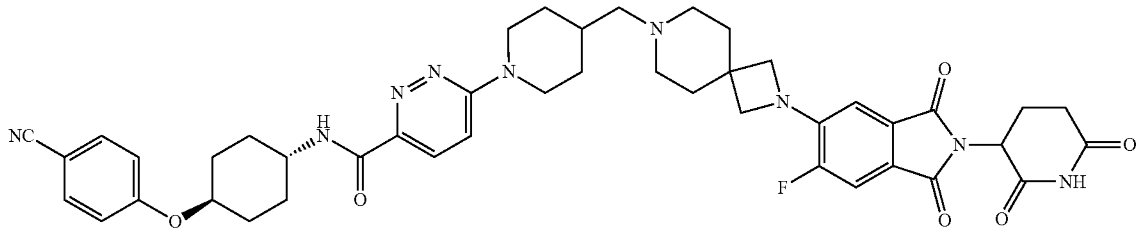
133
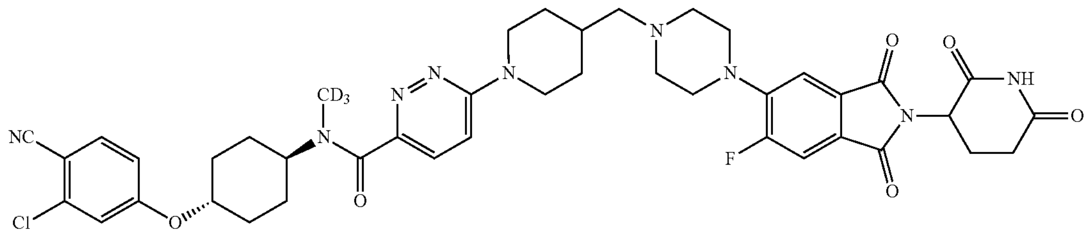

-continued
134
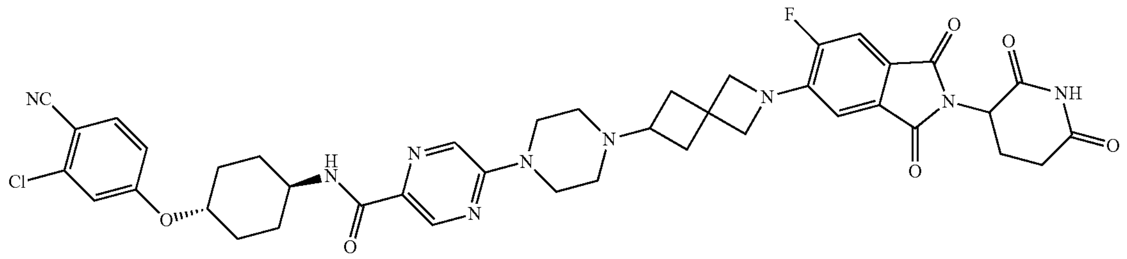
135
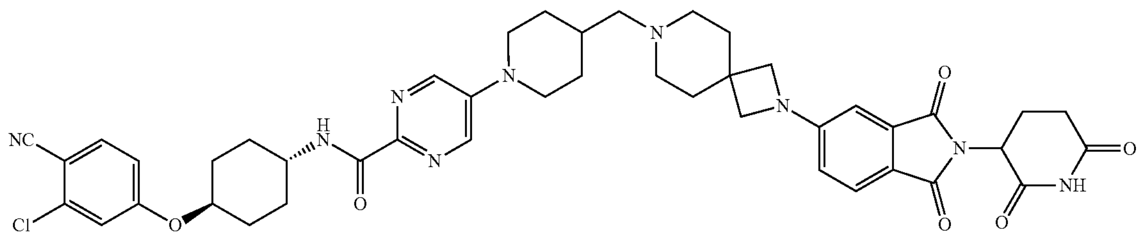
136
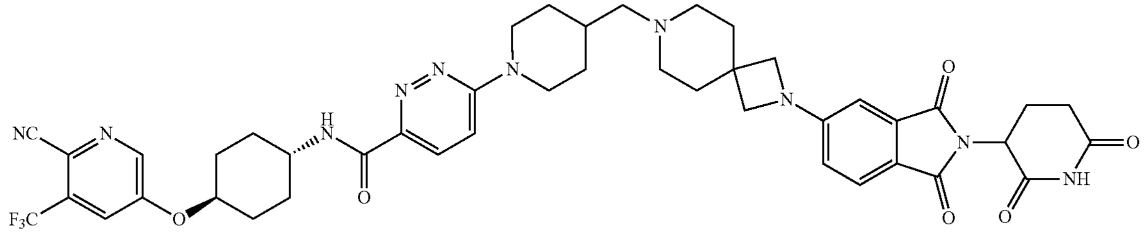
137
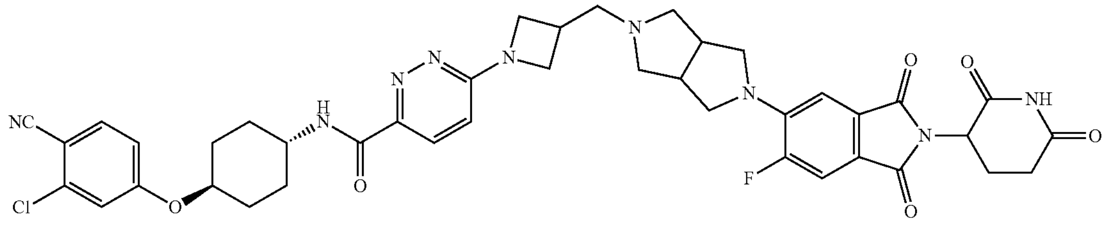
138
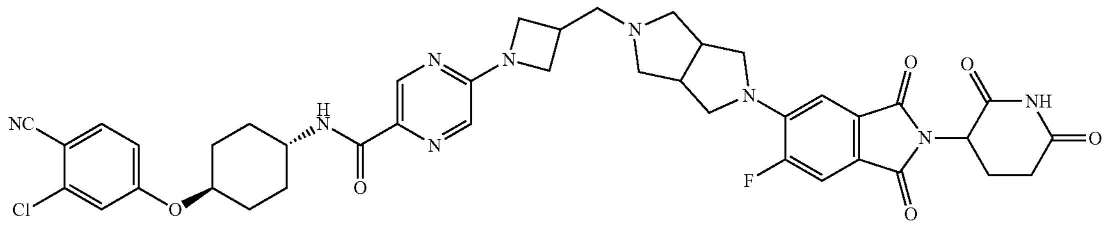
139
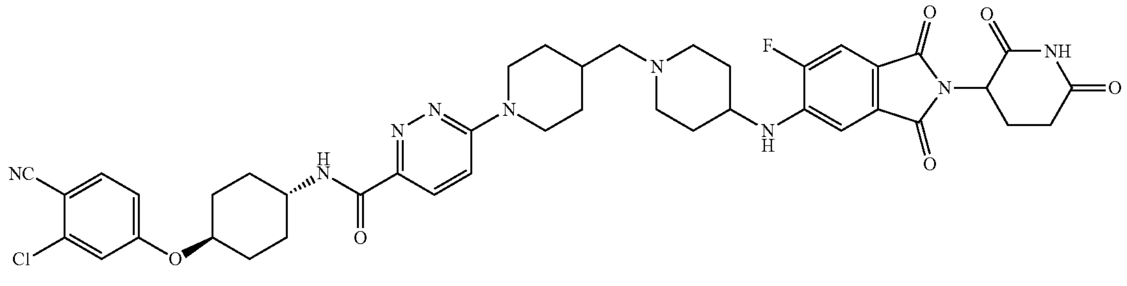

-continued
140
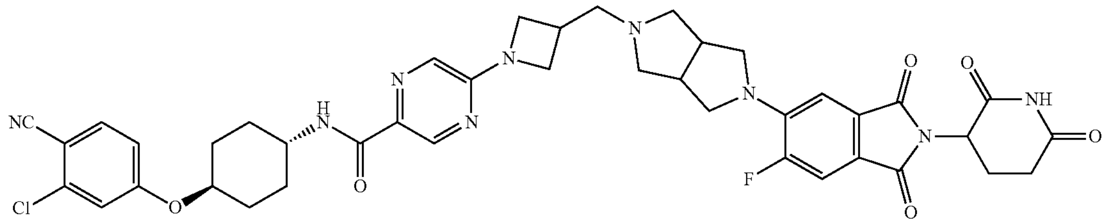
141
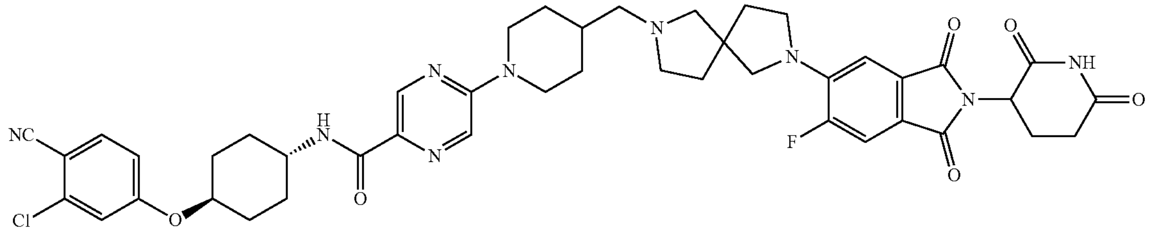
142
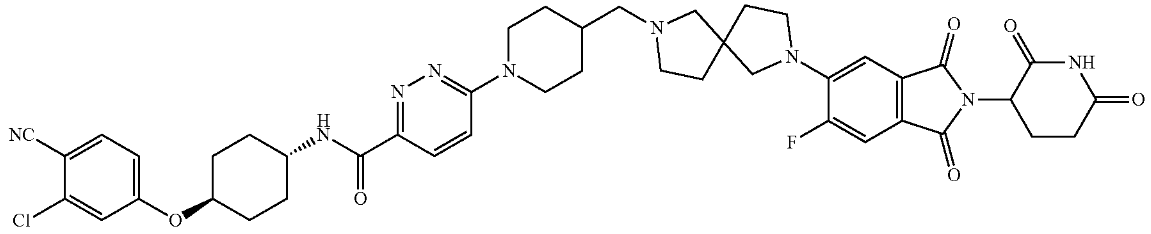
143
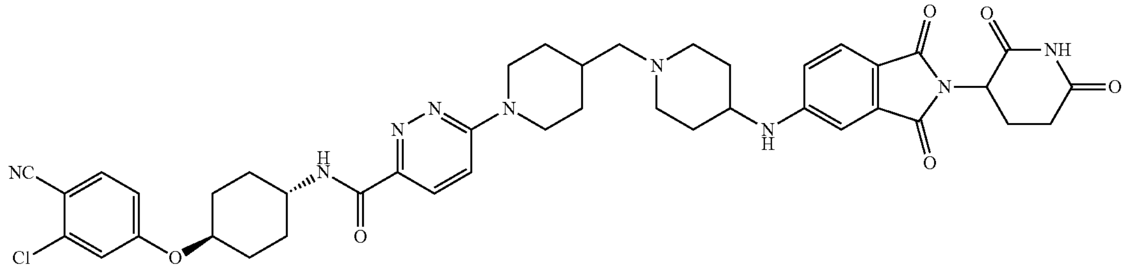
145
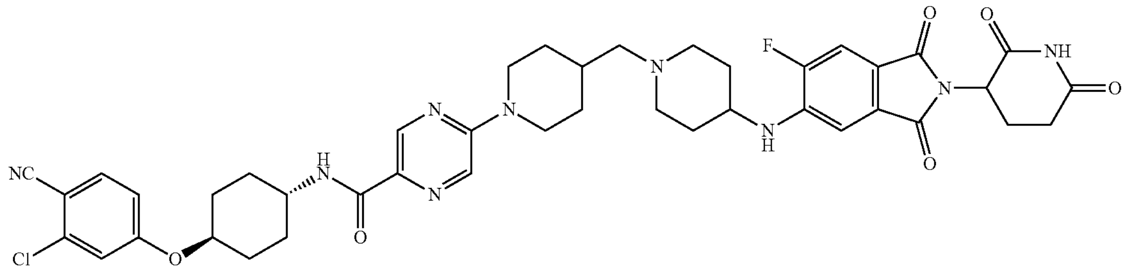
146
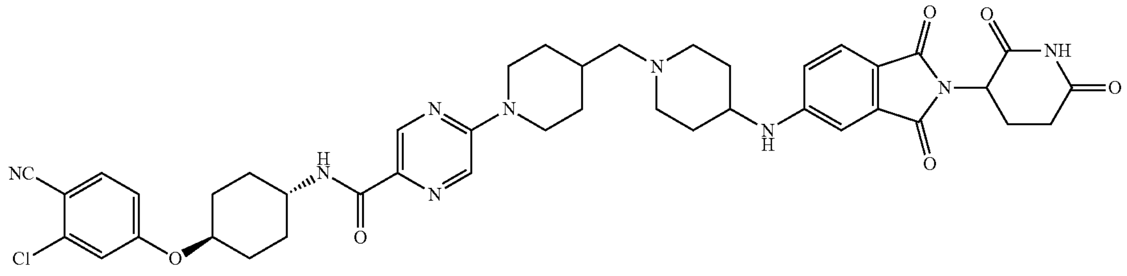

-continued
147
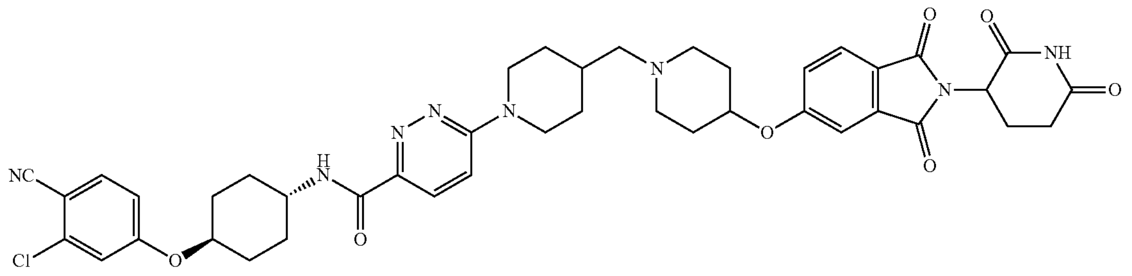
148
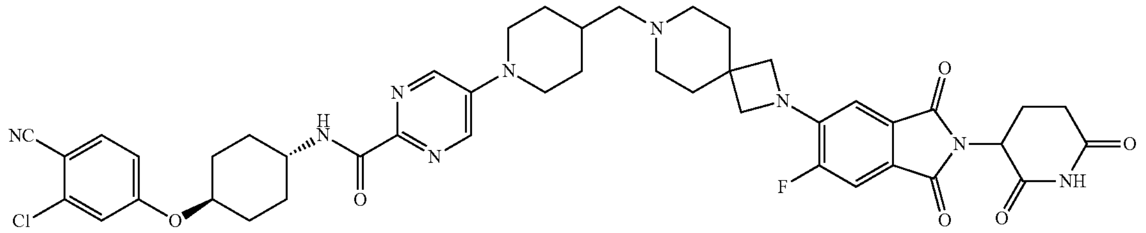
149
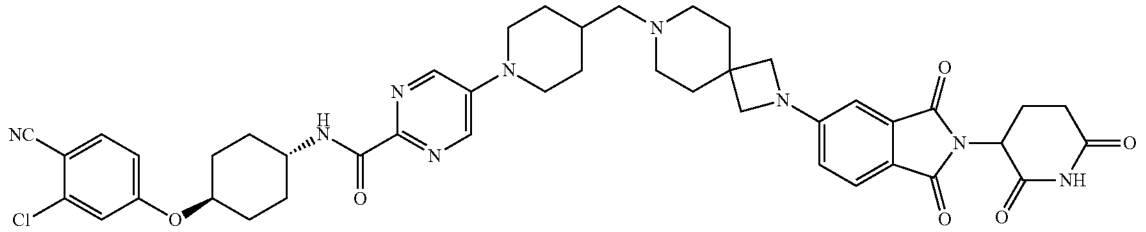
150
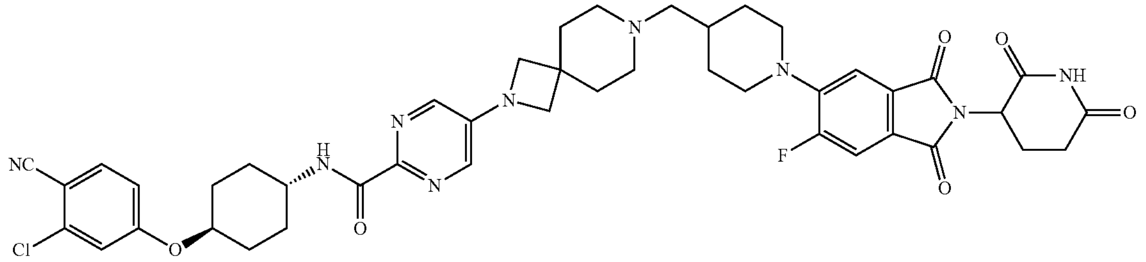
151
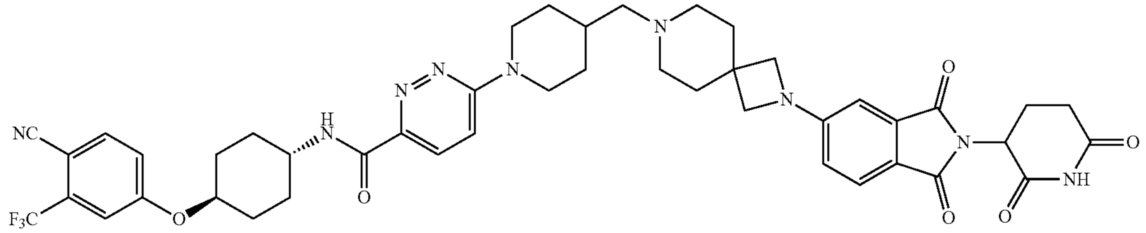
152
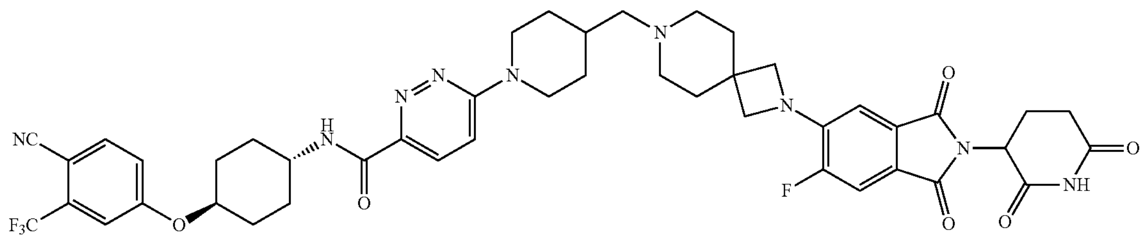

-continued
153
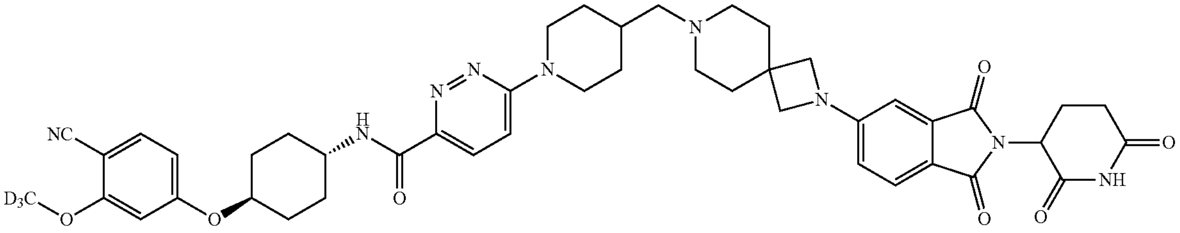
154
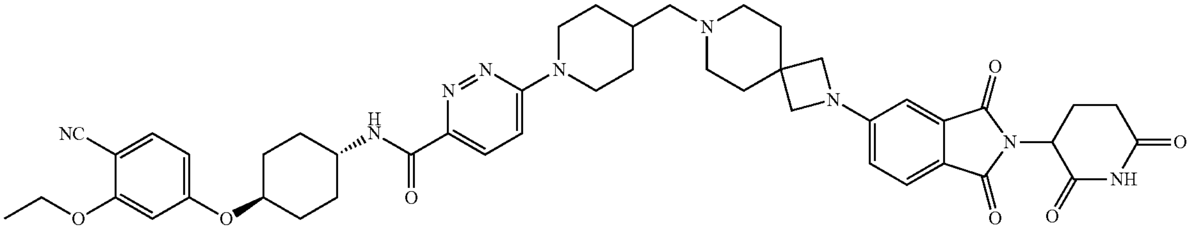
155
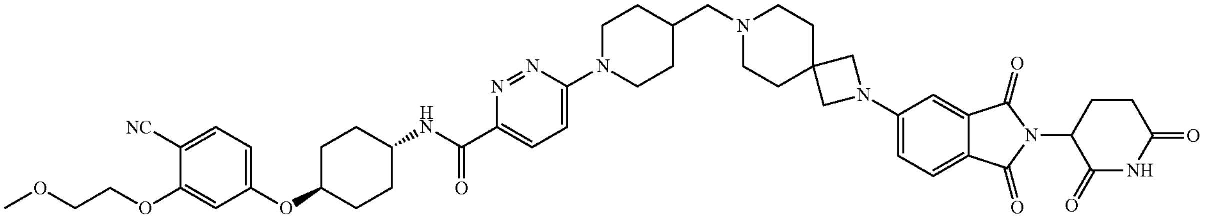
156
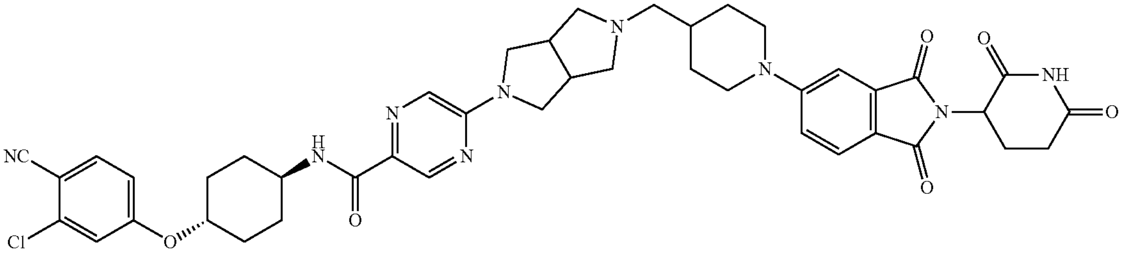
157
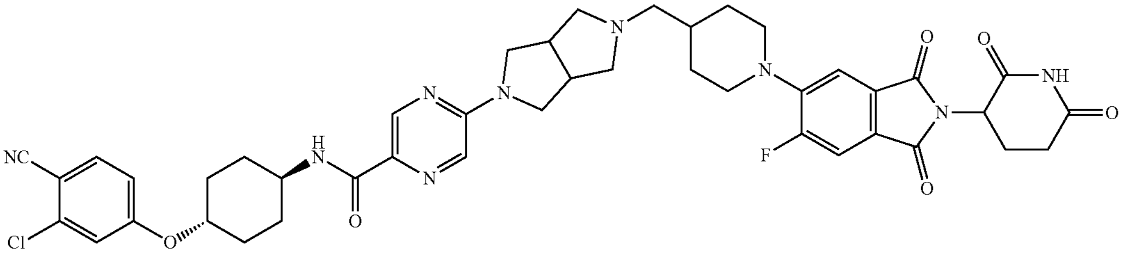
158
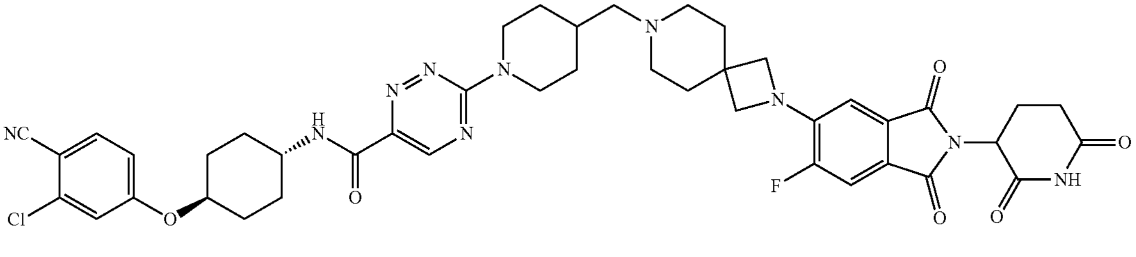

-continued
159
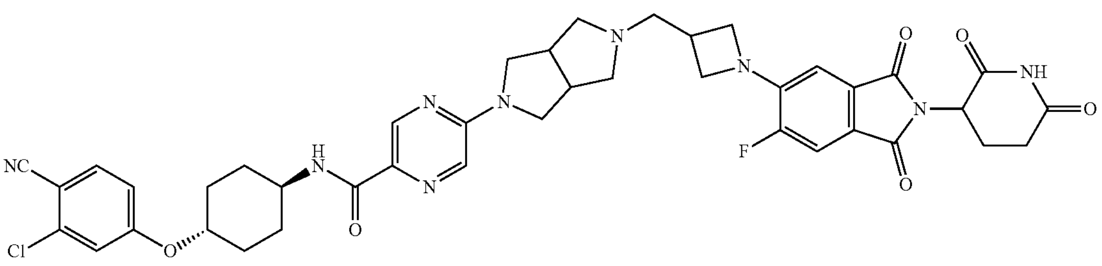
160
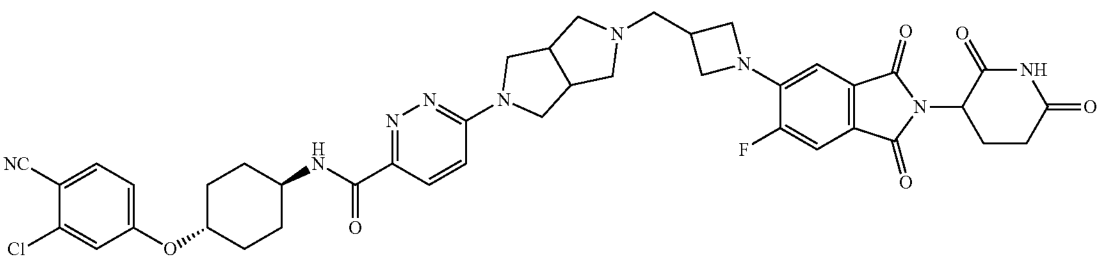
161
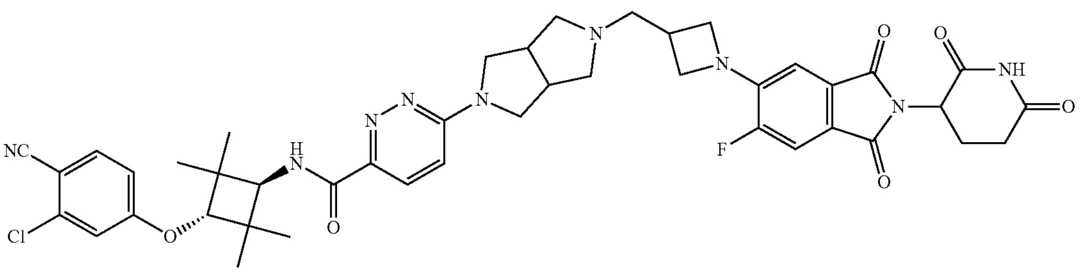
162
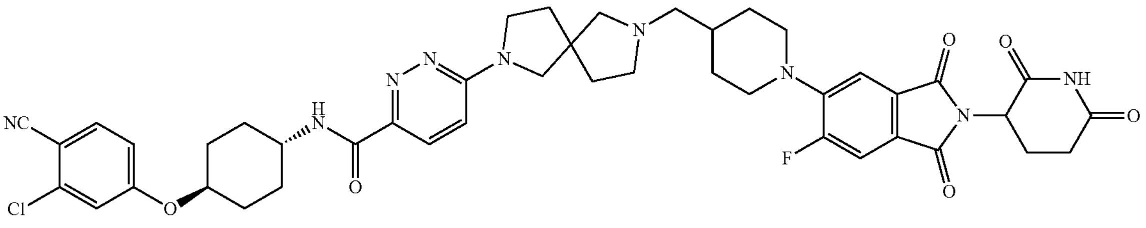
163
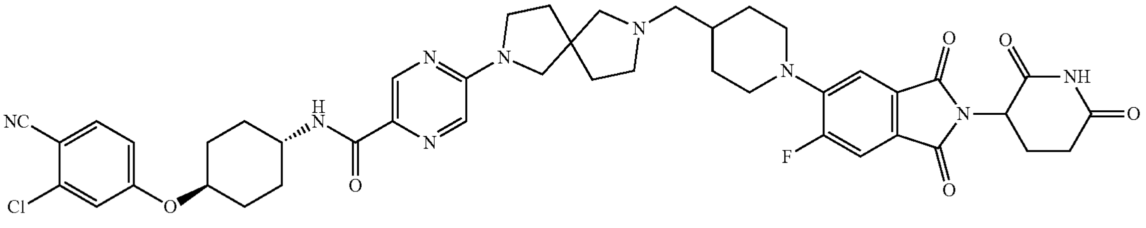
164
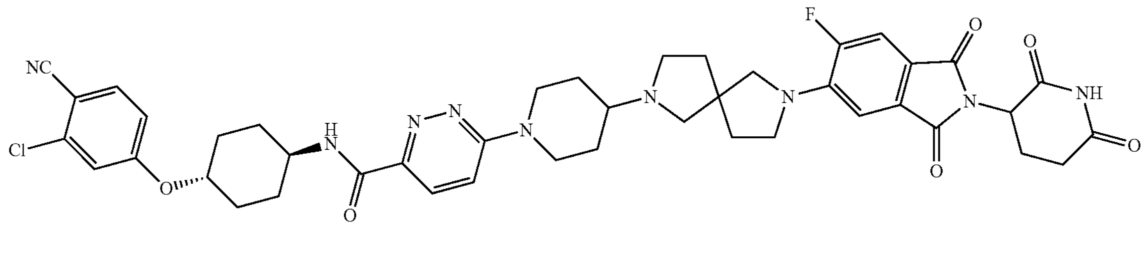

-continued
165
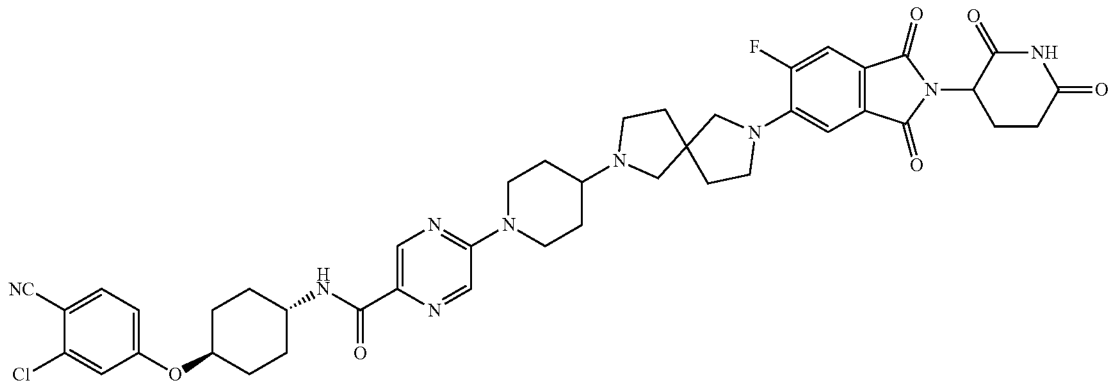
166
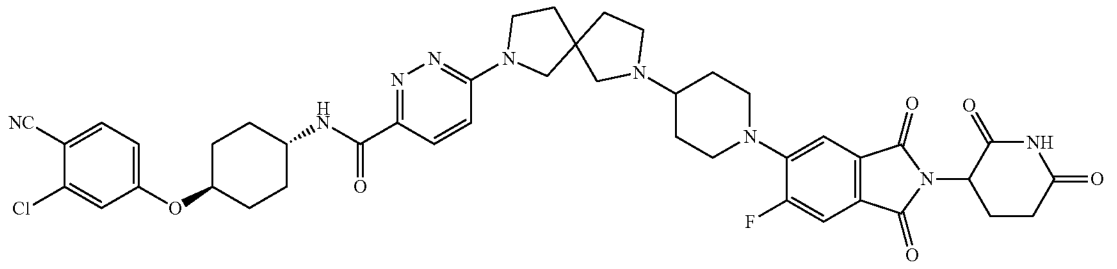
167
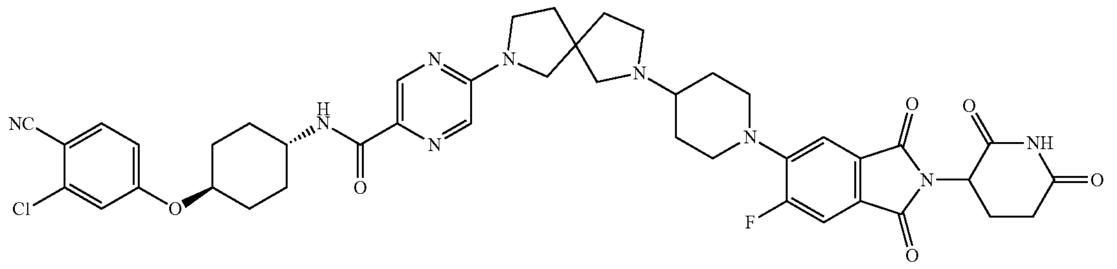
168
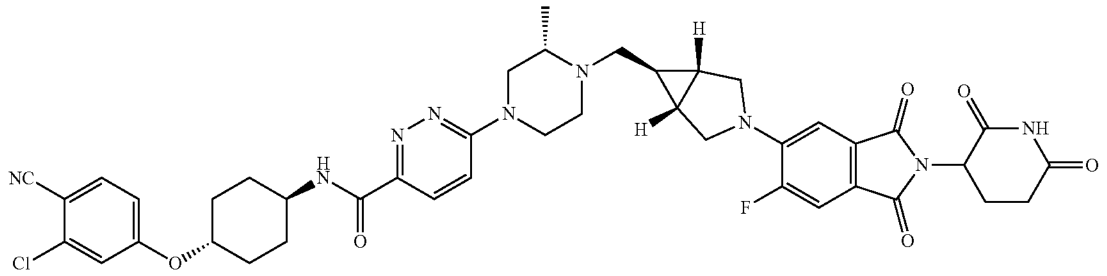
169
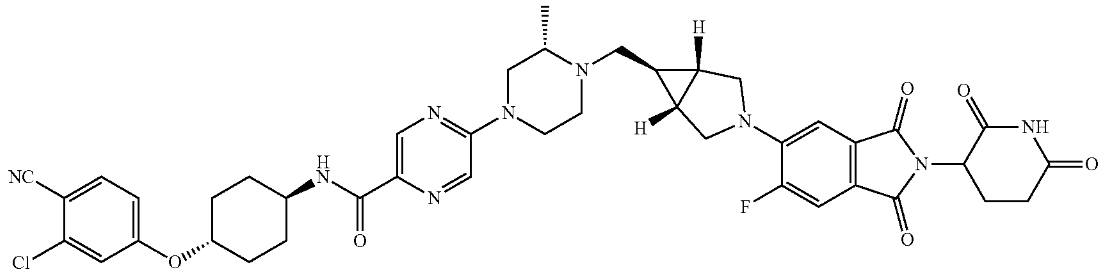

-continued
170
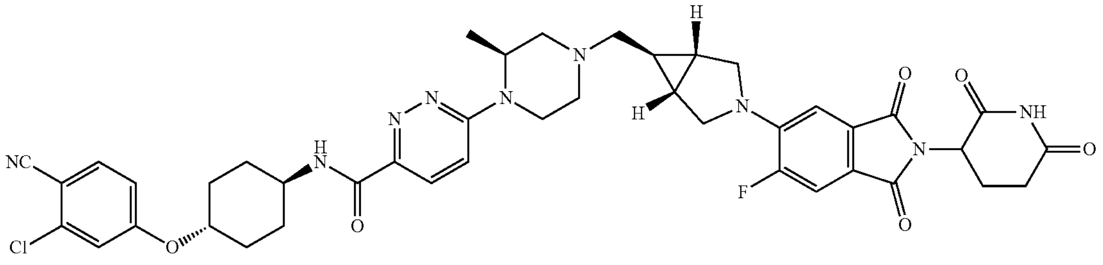
171
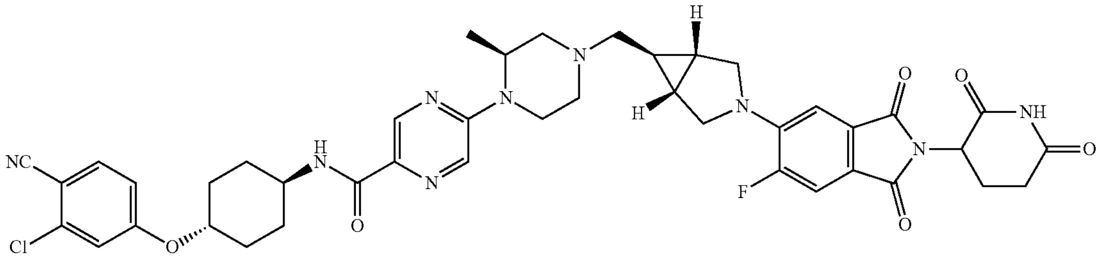
172
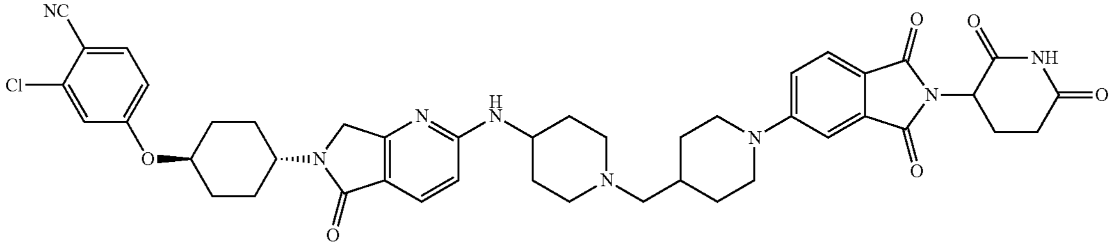
173
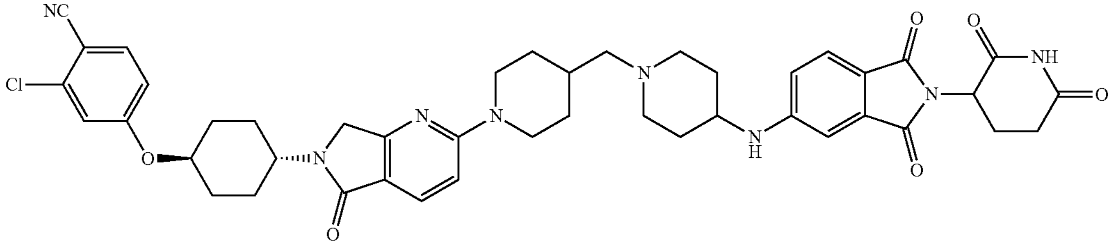
174
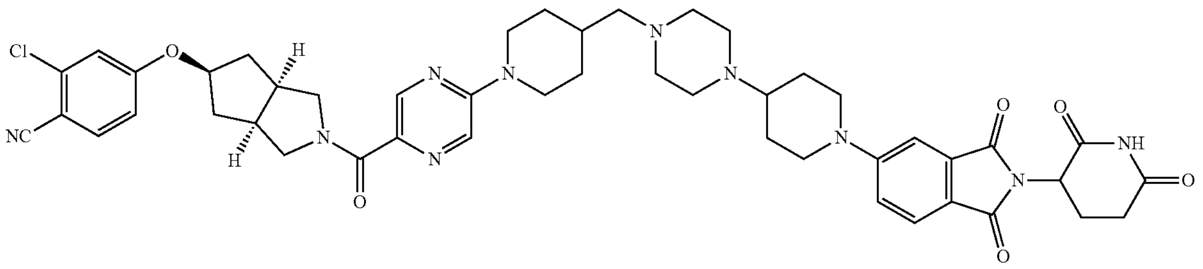
175
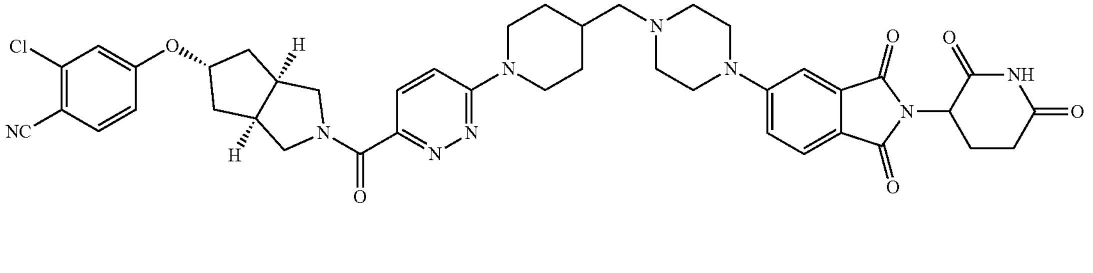

-continued
176
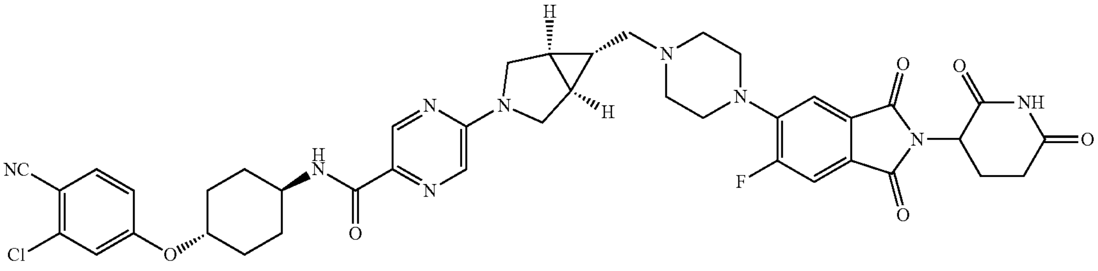
177
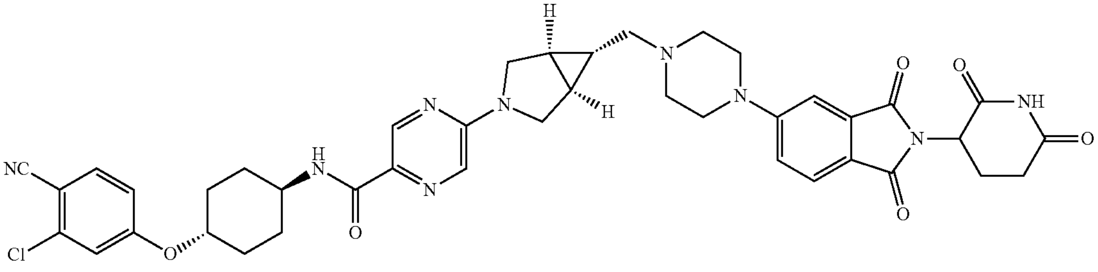
178
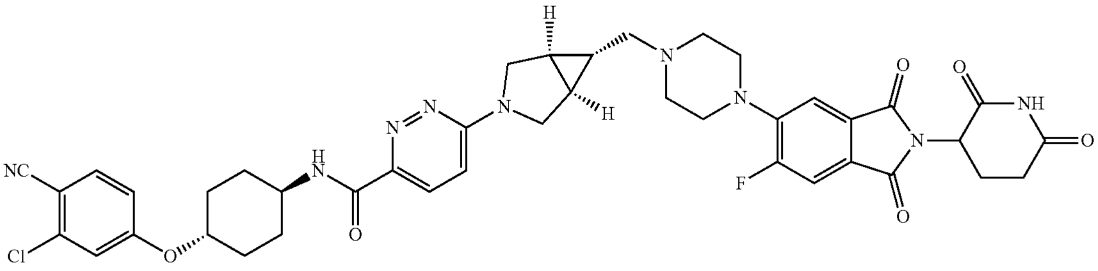
179
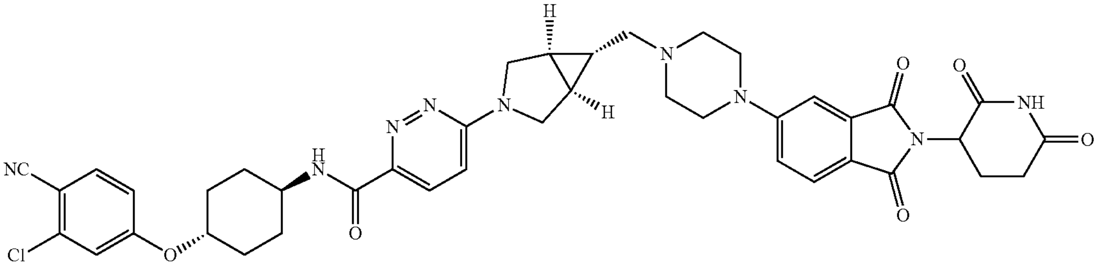
180
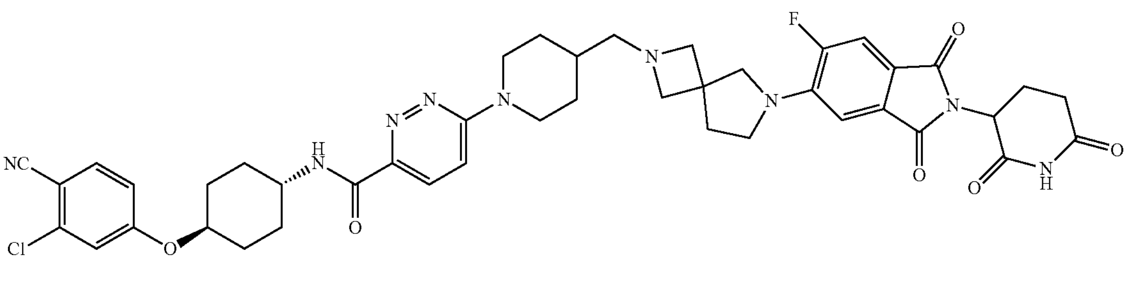

-continued
181
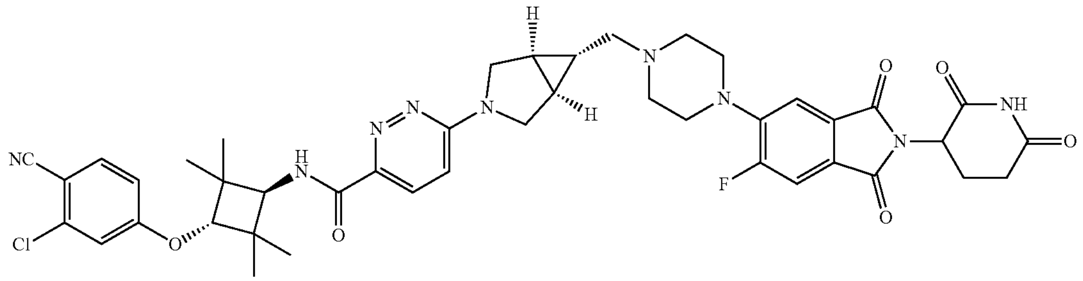
182
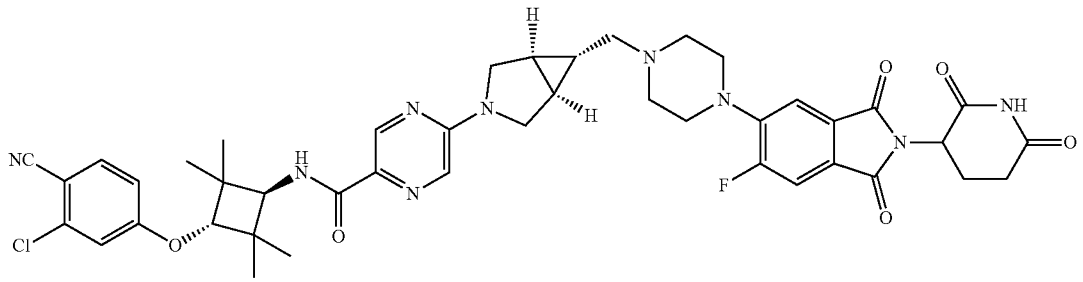
183
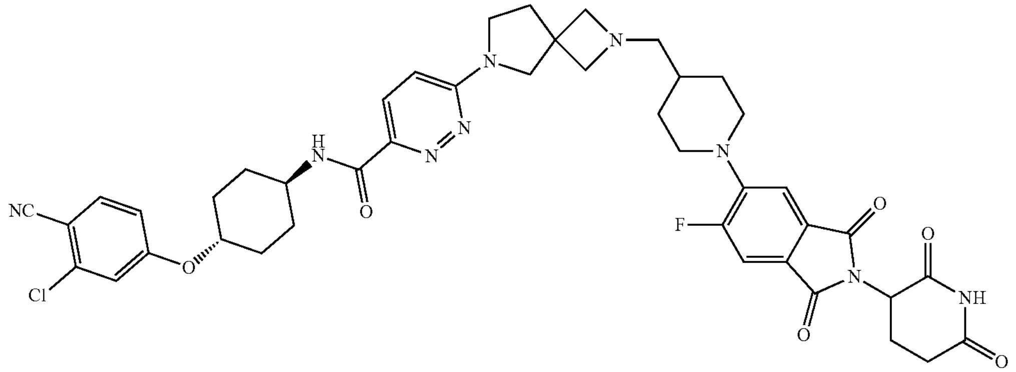
184
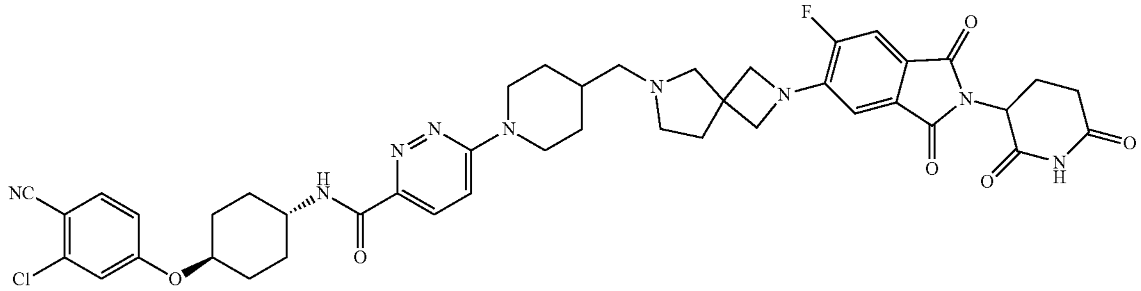
185
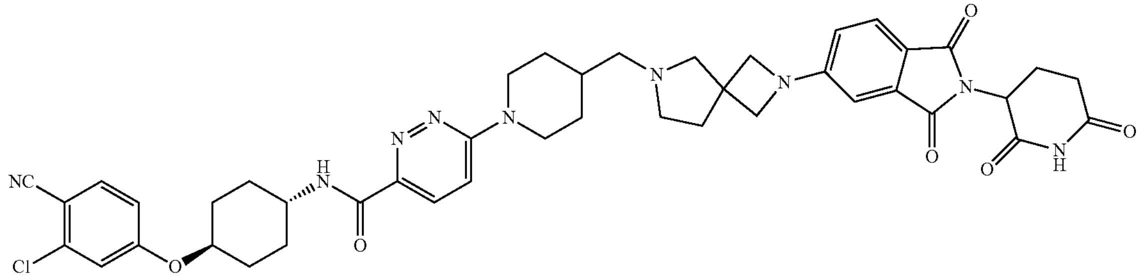

-continued
186
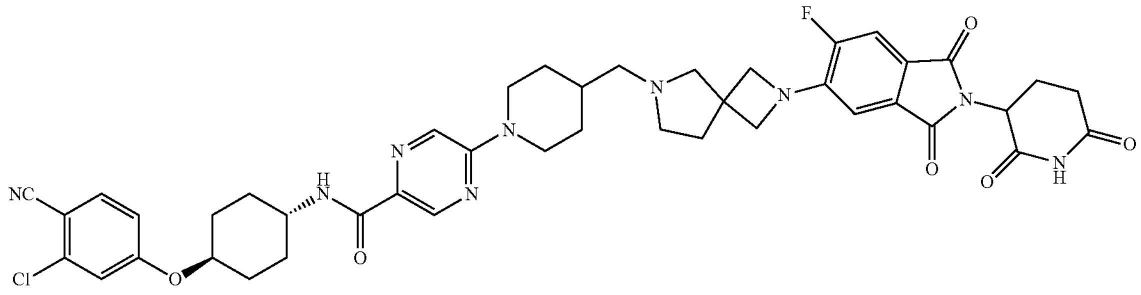
187
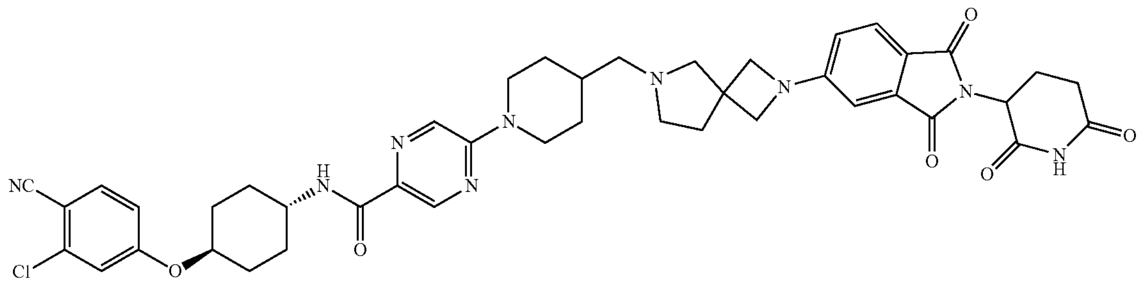
188
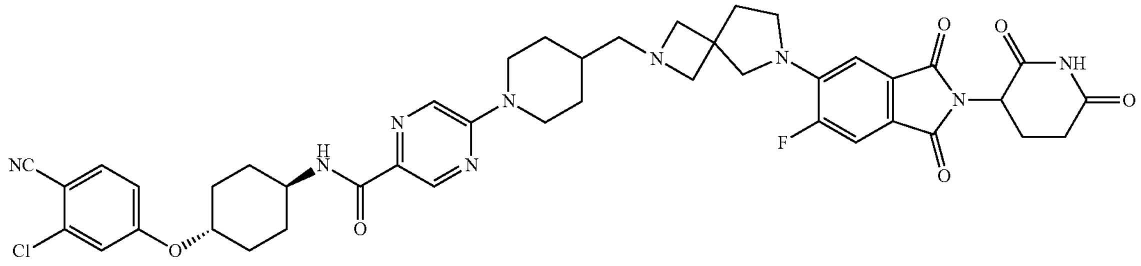
189
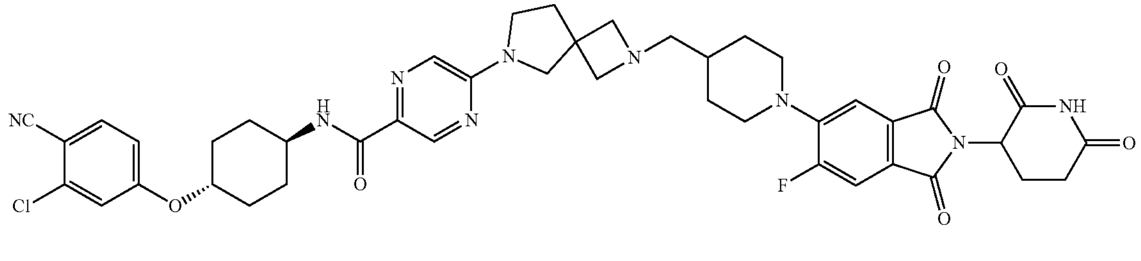
190
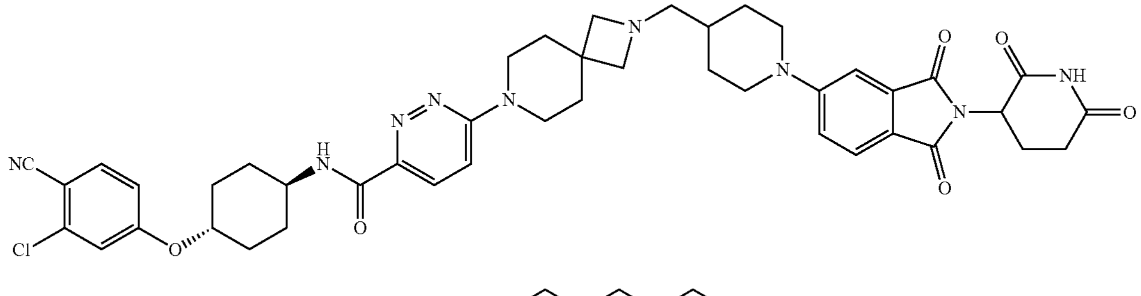
191
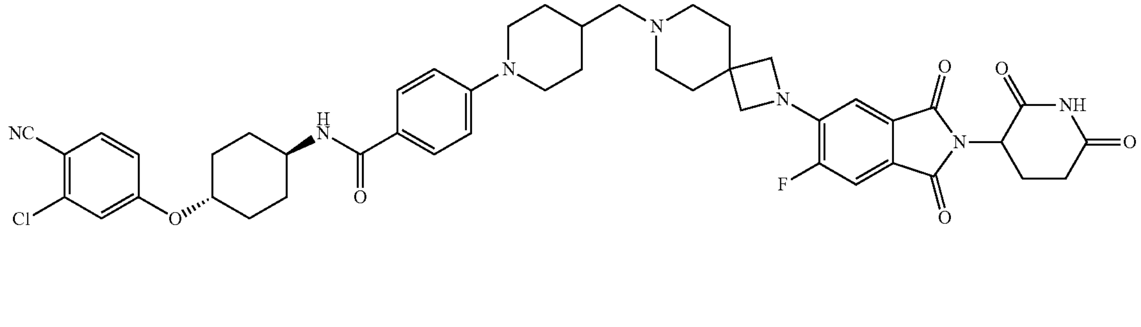

-continued
192
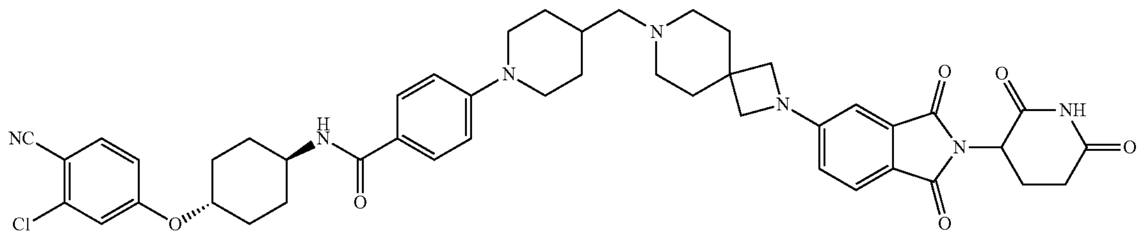
193
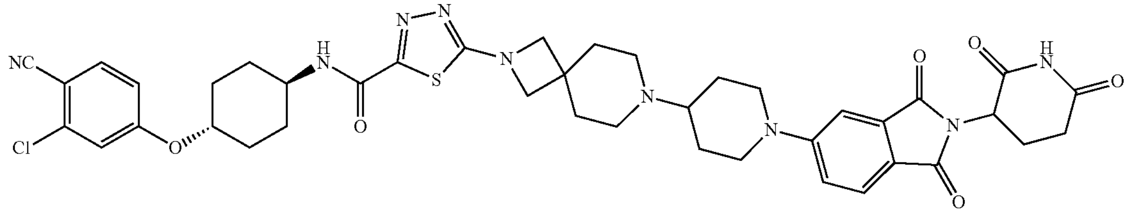
194
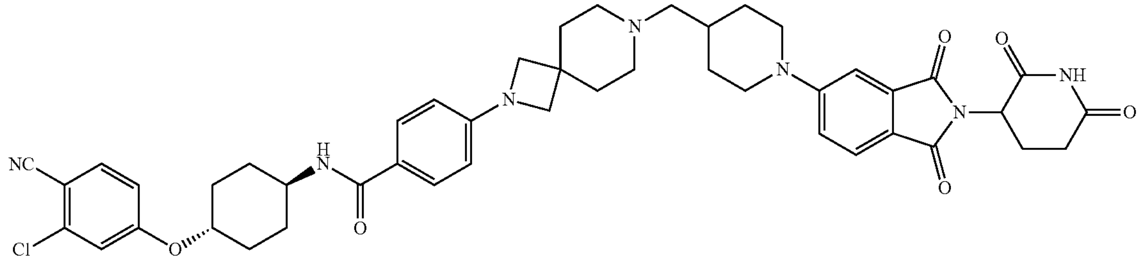
195
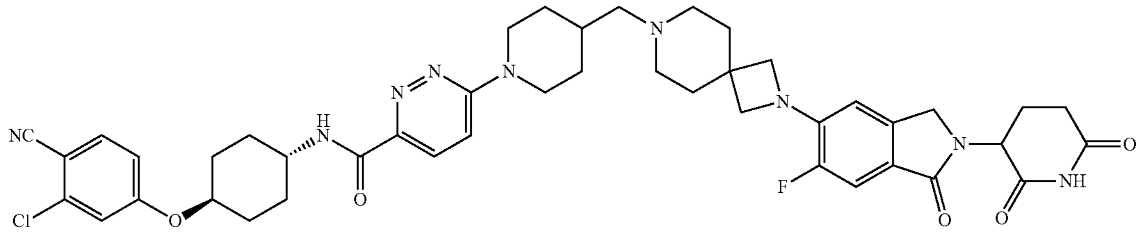
196
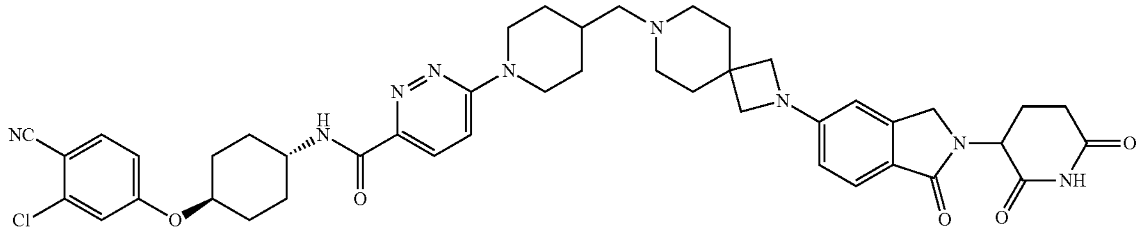
197
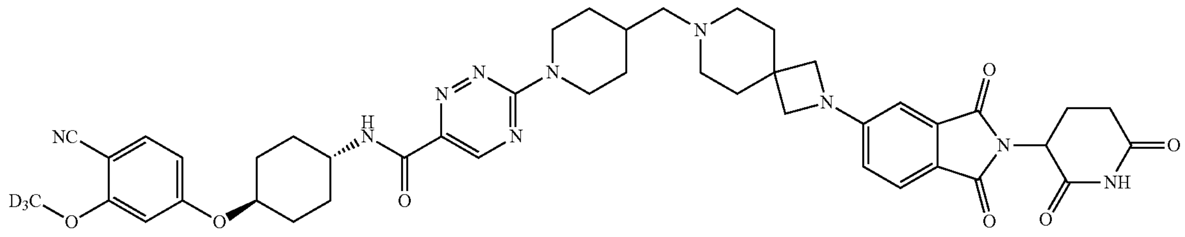

-continued
198
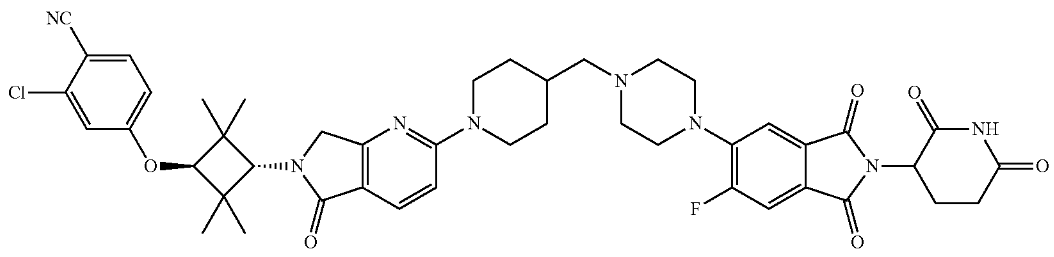
199
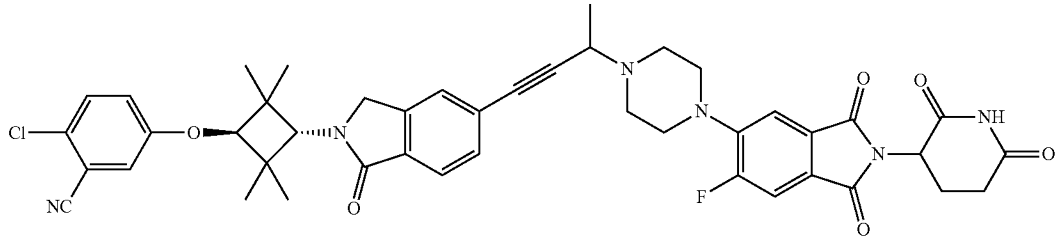
200
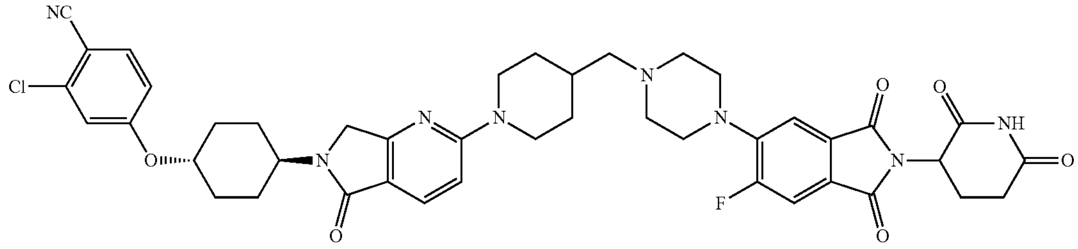
201
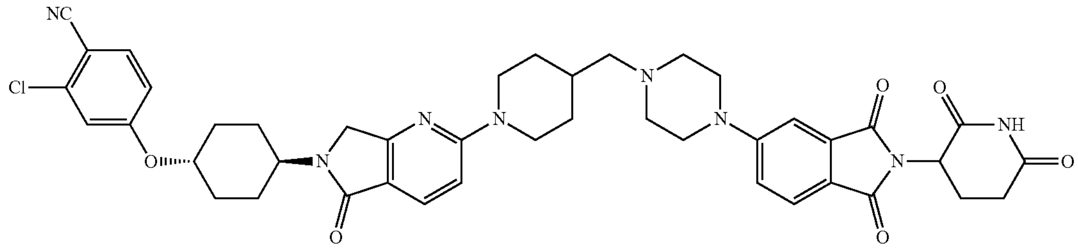
202
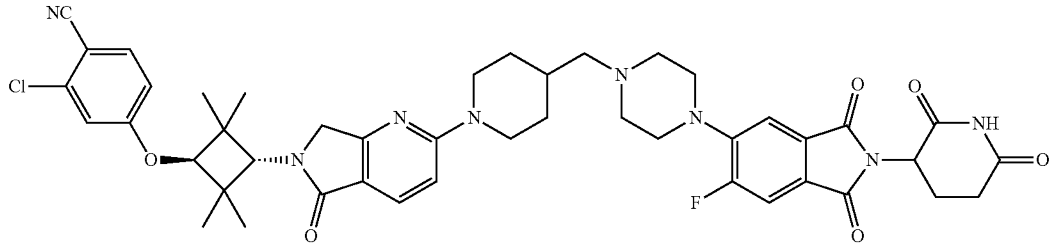
203
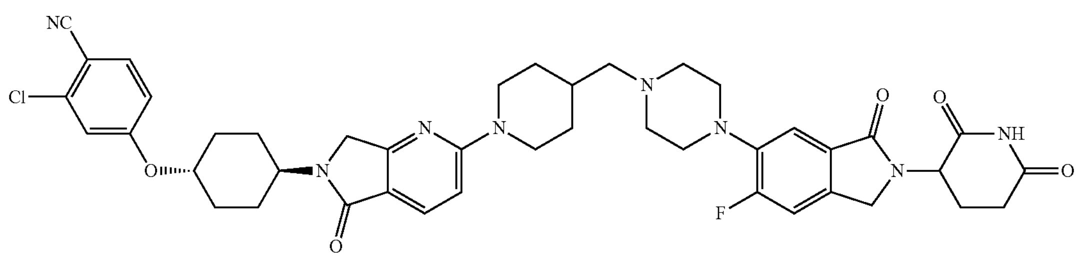

-continued
204
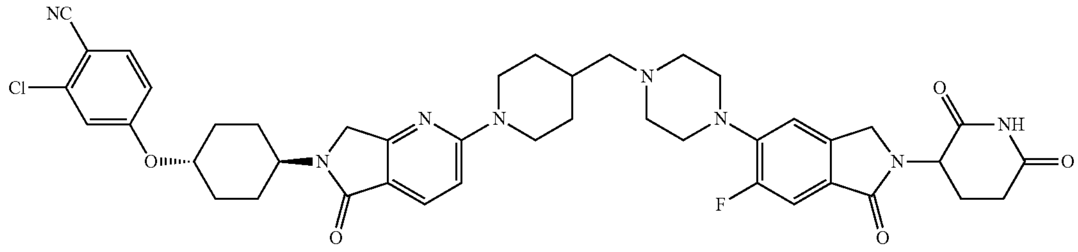
205
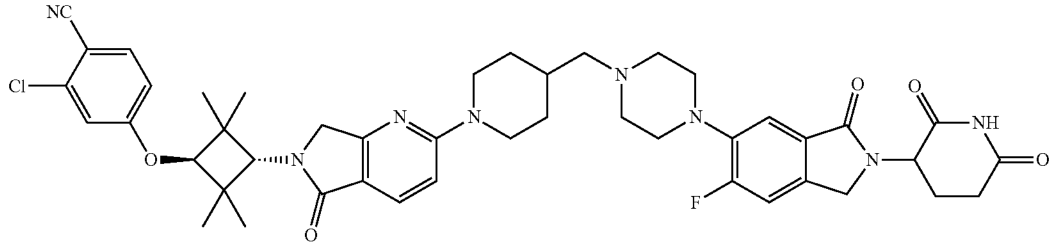
206
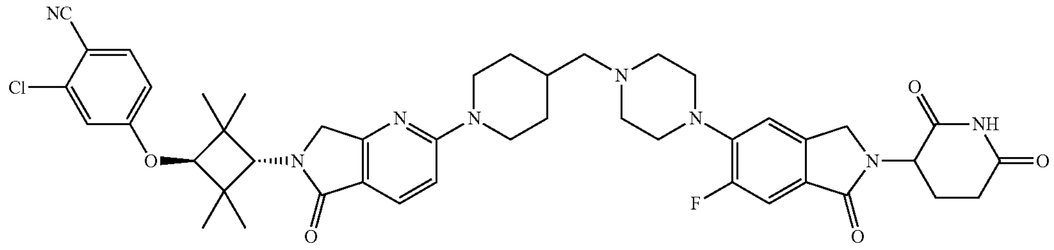
207
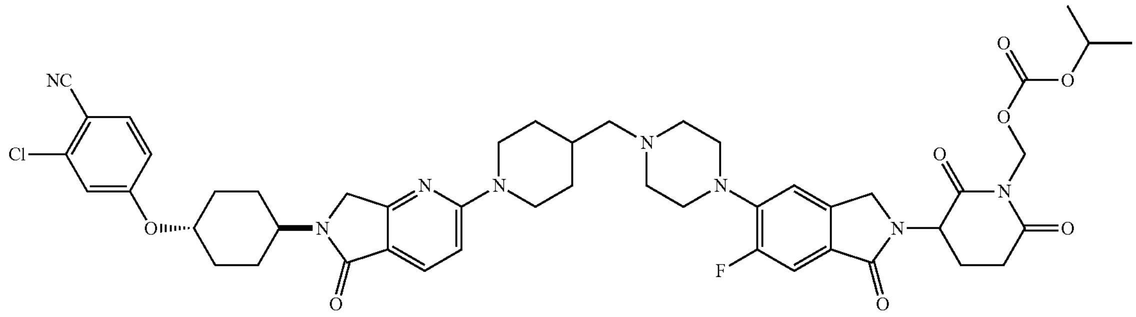
208
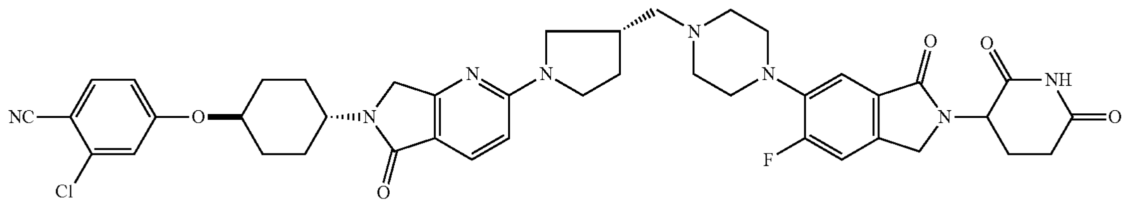
209
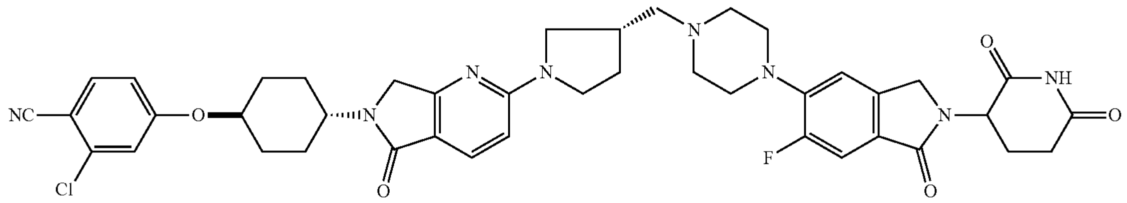

-continued
210
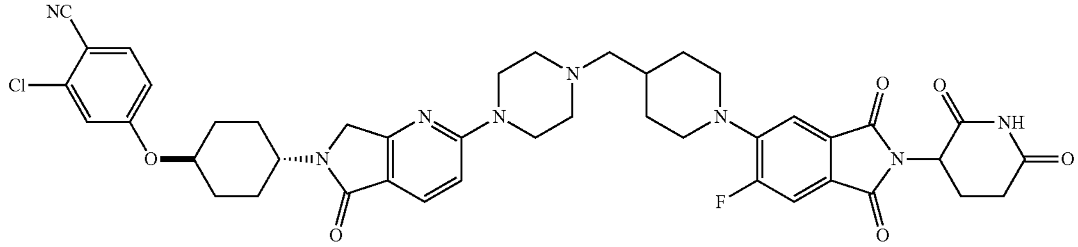
211
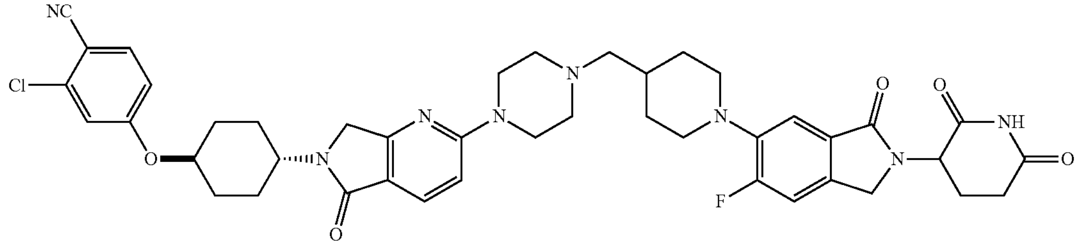
212
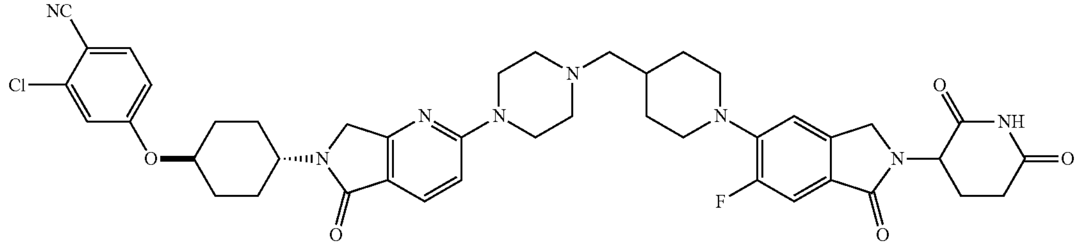
213
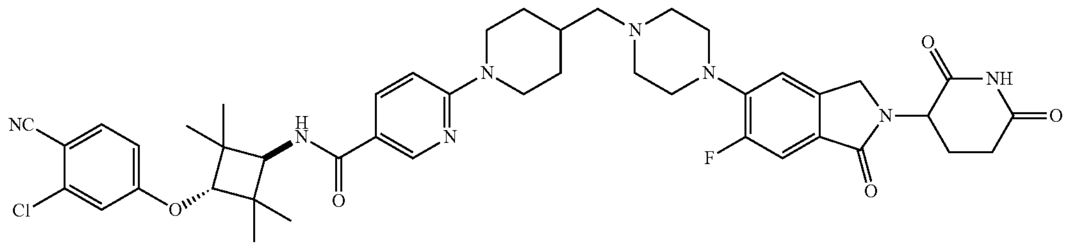
214
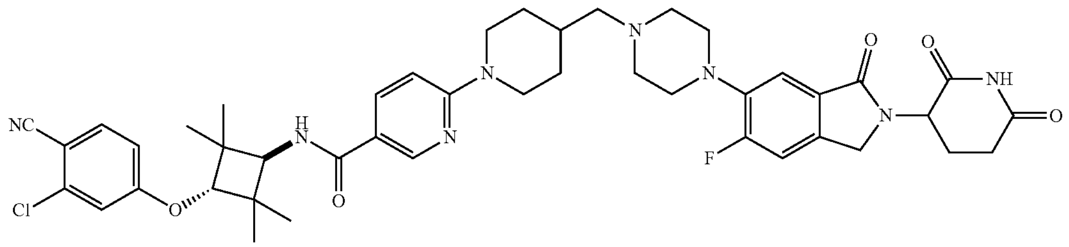
215
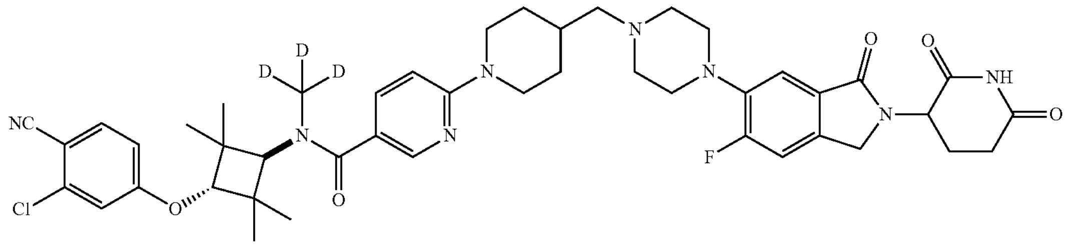

-continued
216
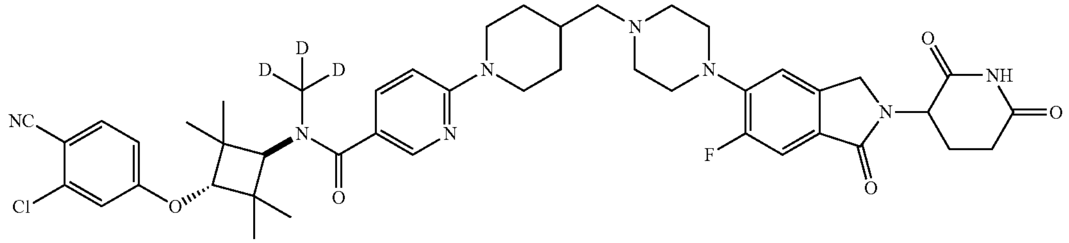
217
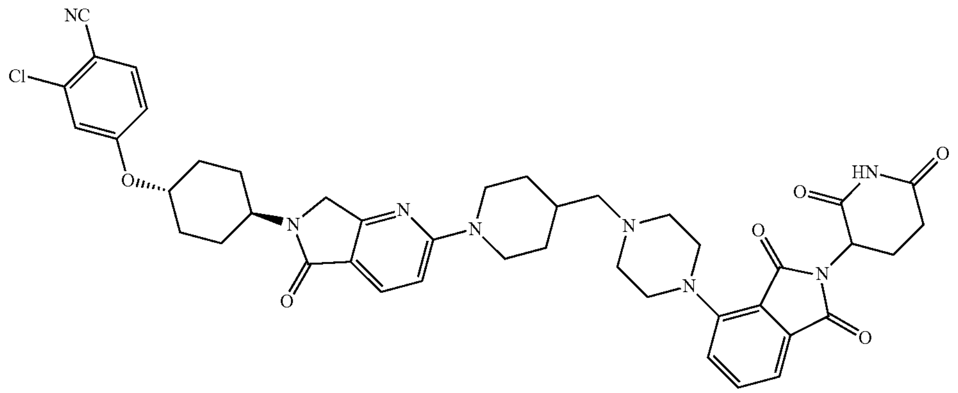
218
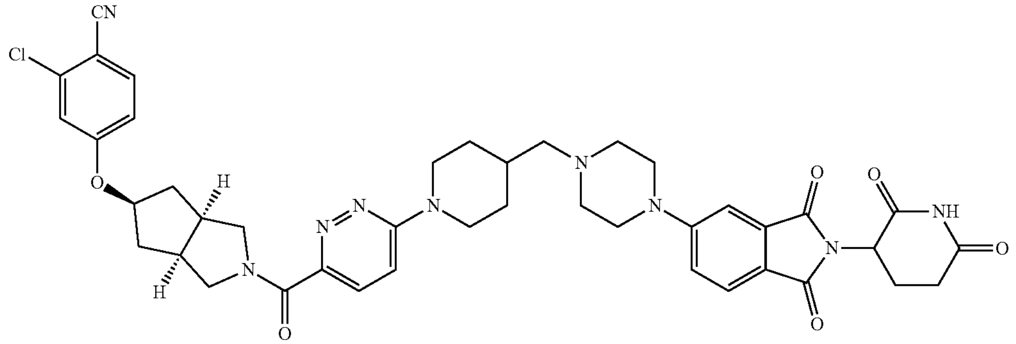
219
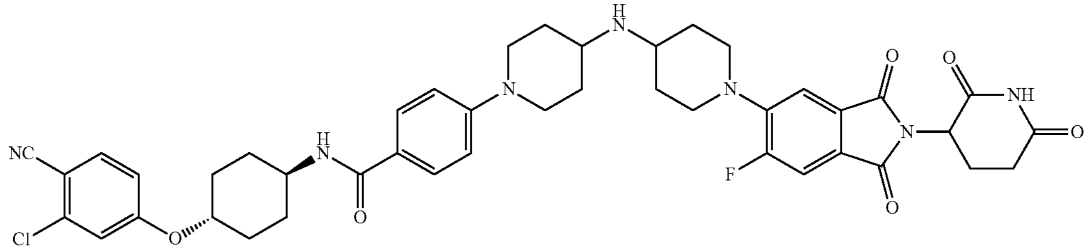
220
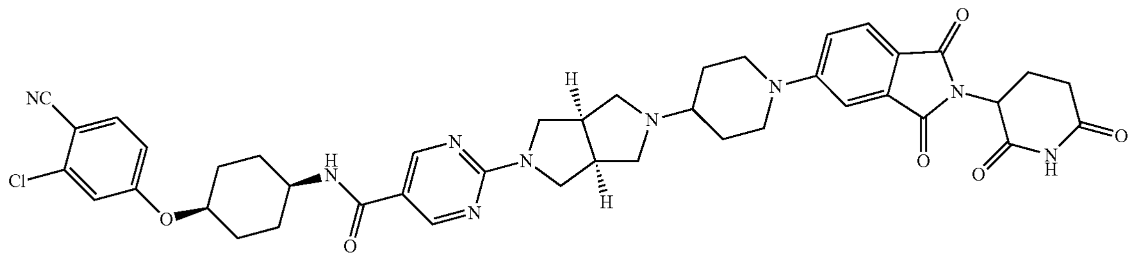

-continued
221
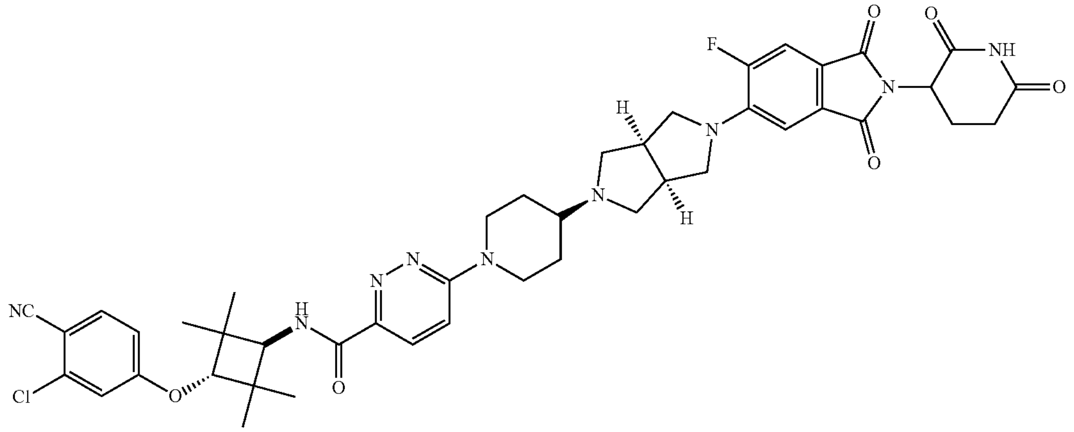
222
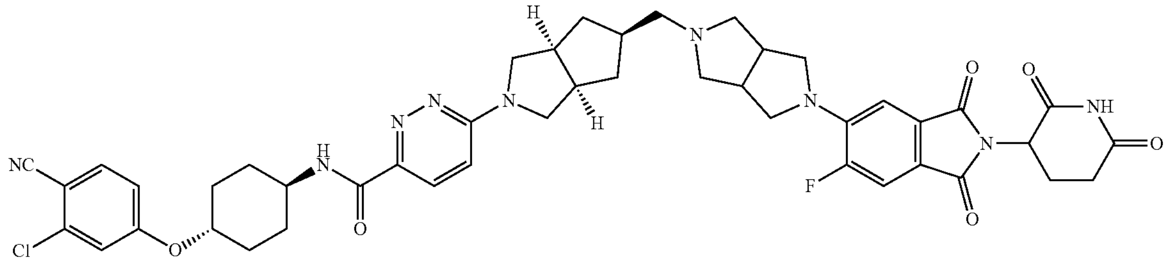
223
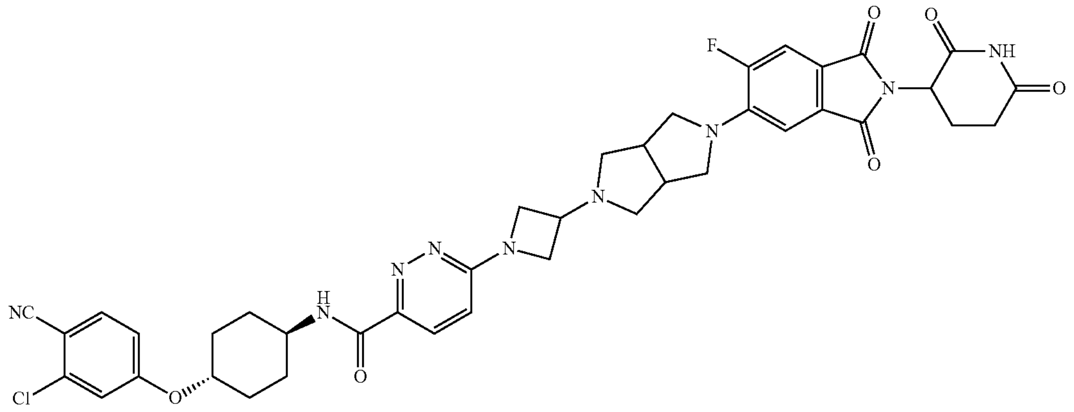
224
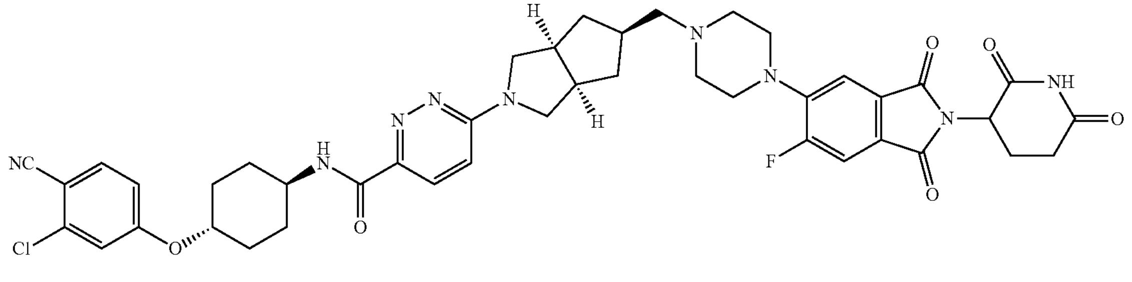

225
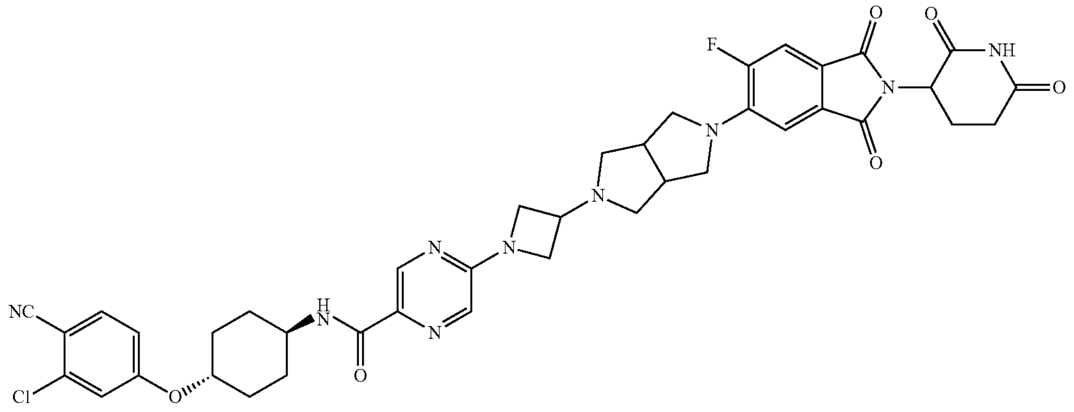
226
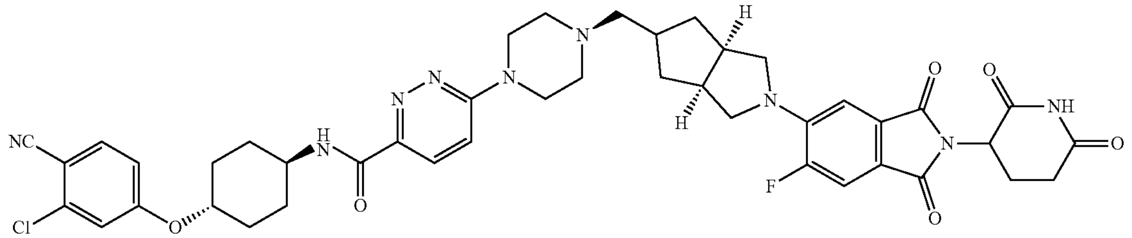
227
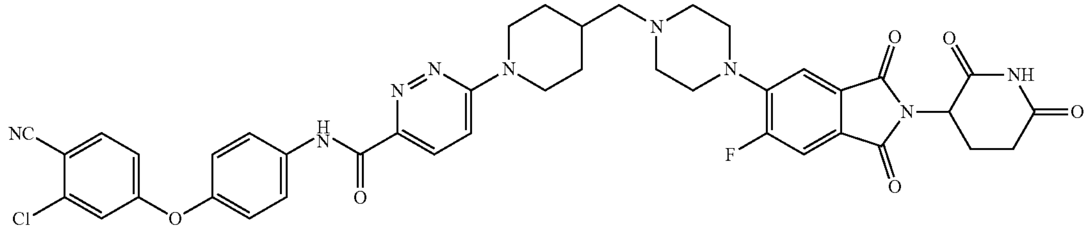
228
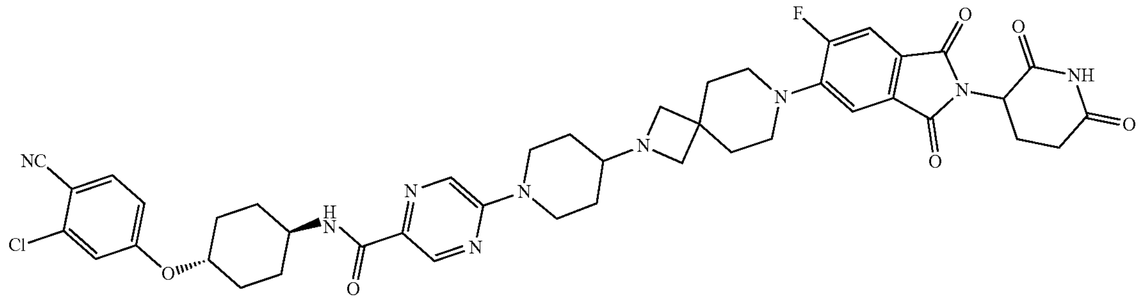
229
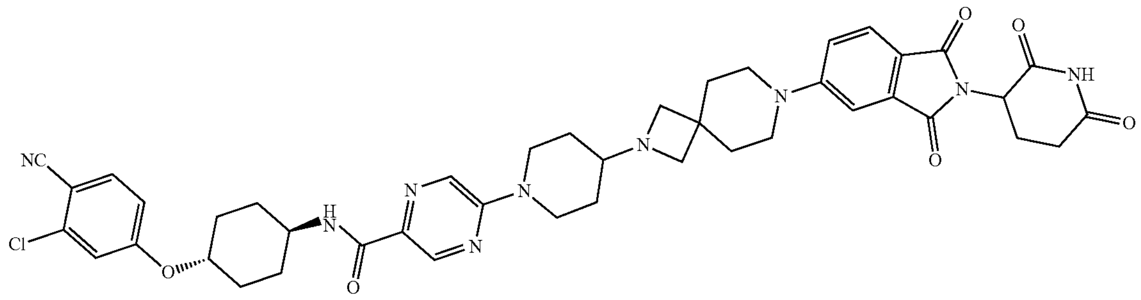

-continued
230
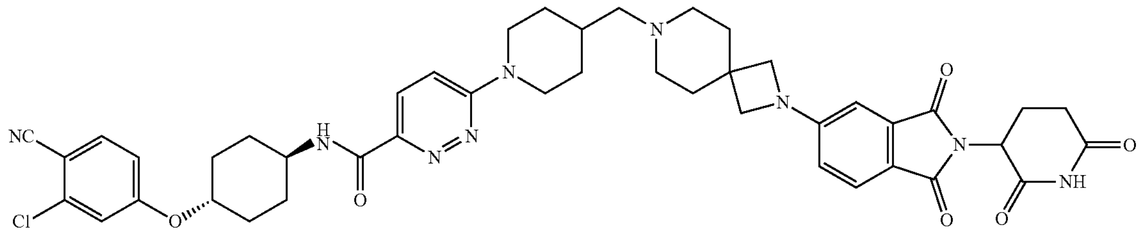
231
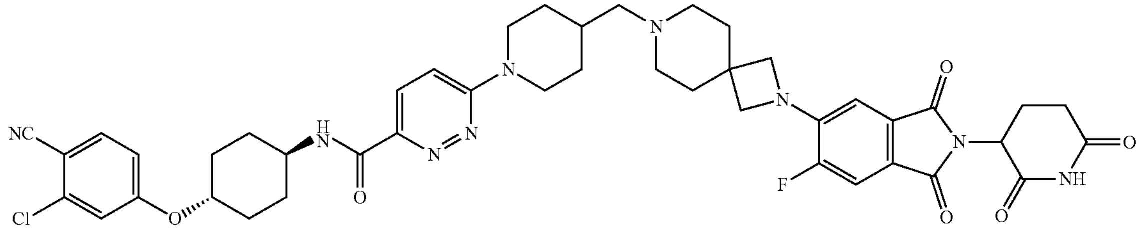
232
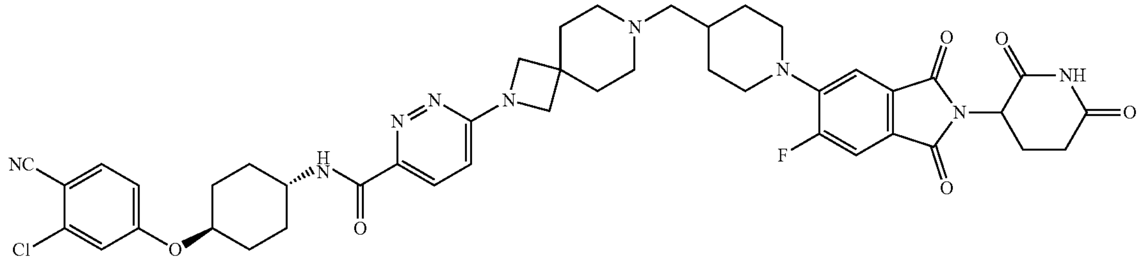
233
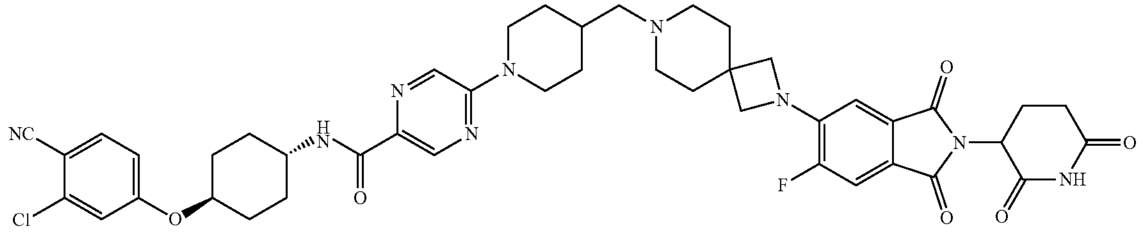
234
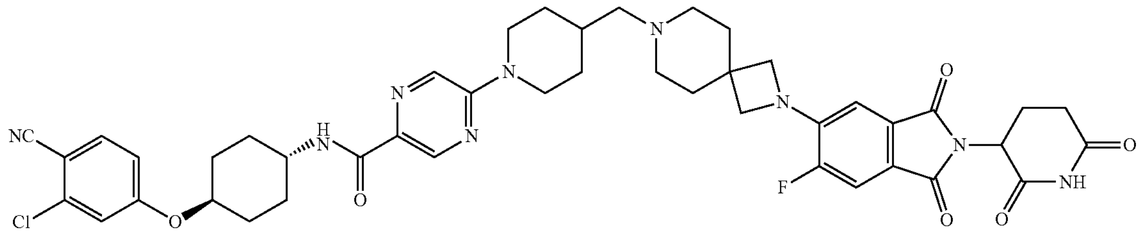
235
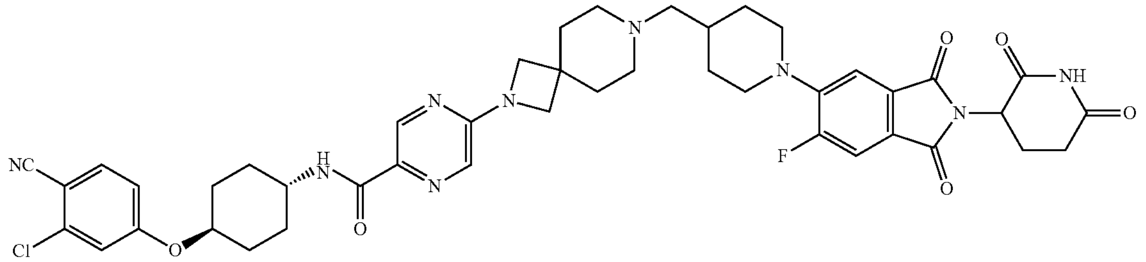

-continued
236
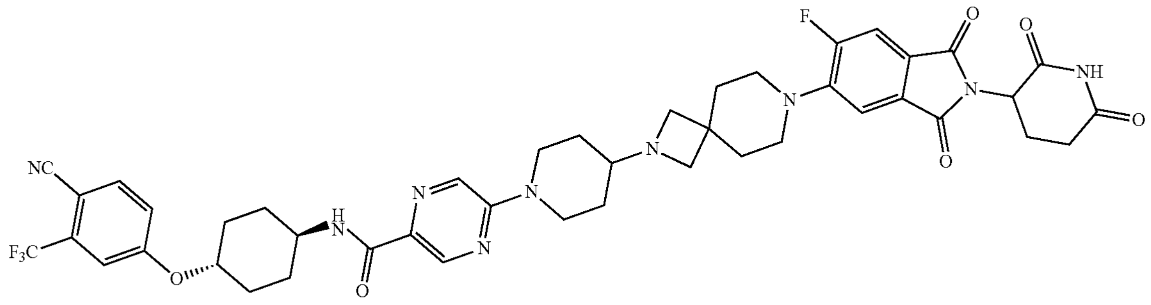
237
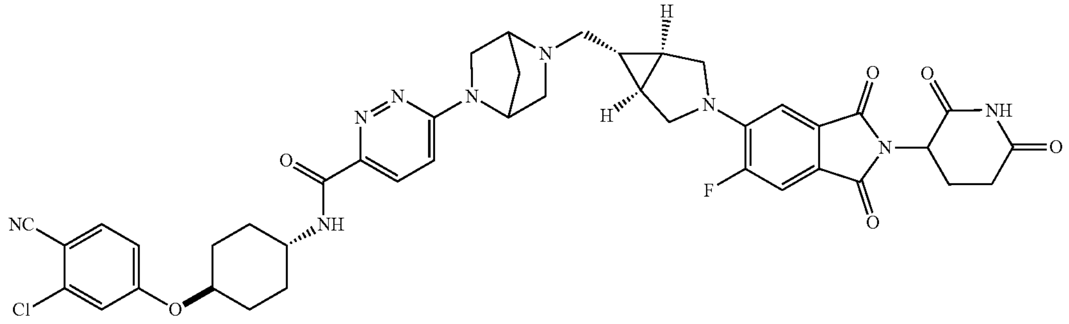
238
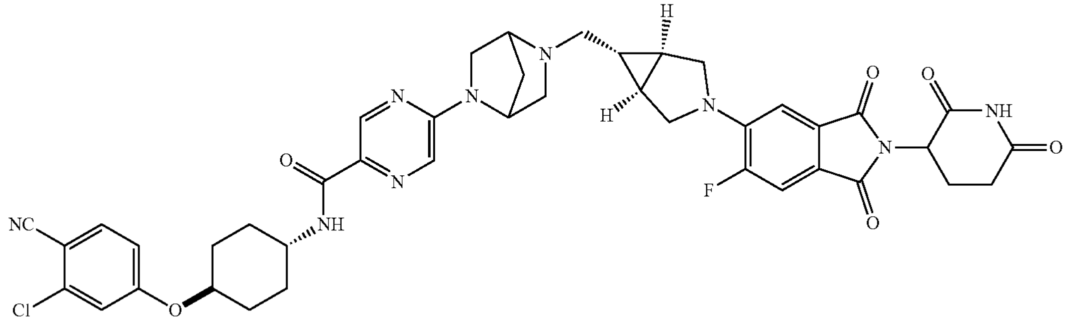
239
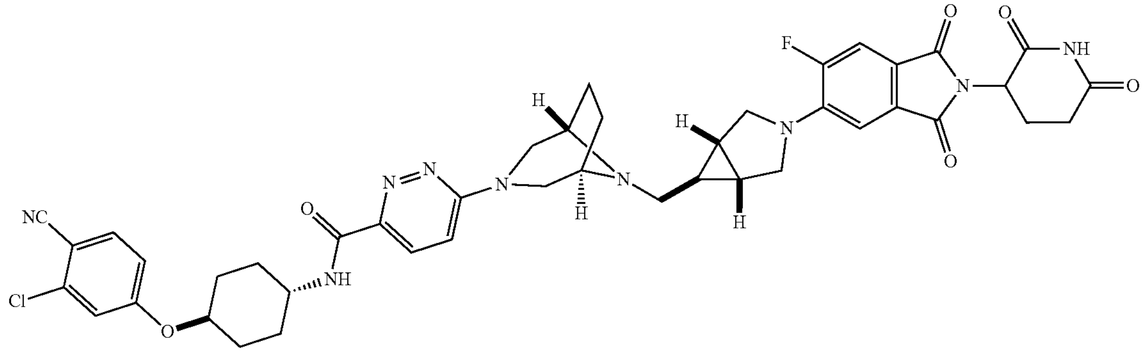

-continued
240
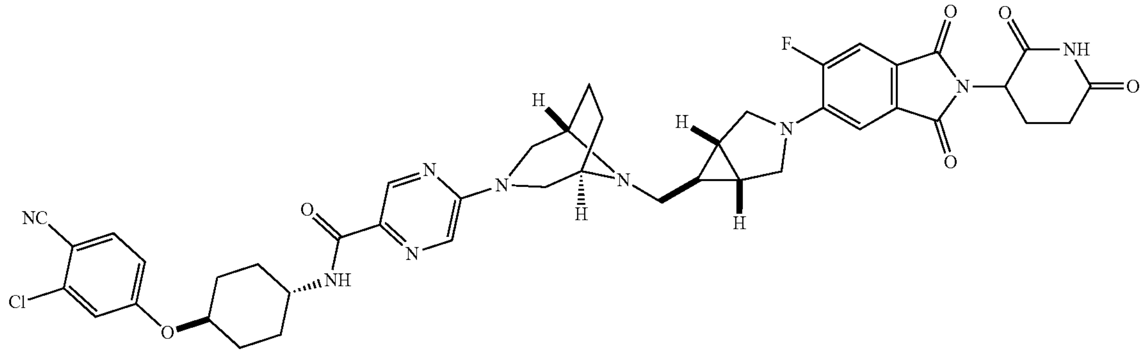
241
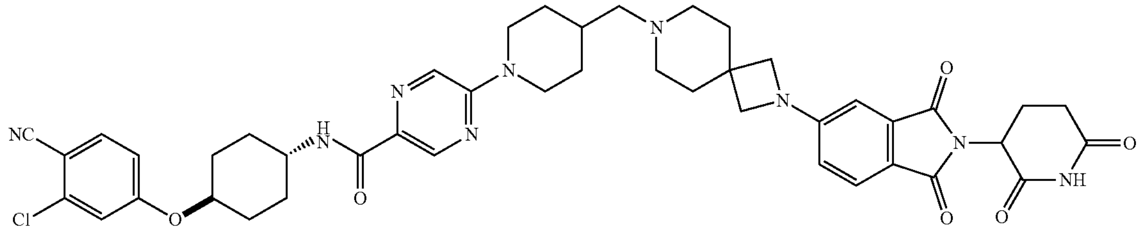
242
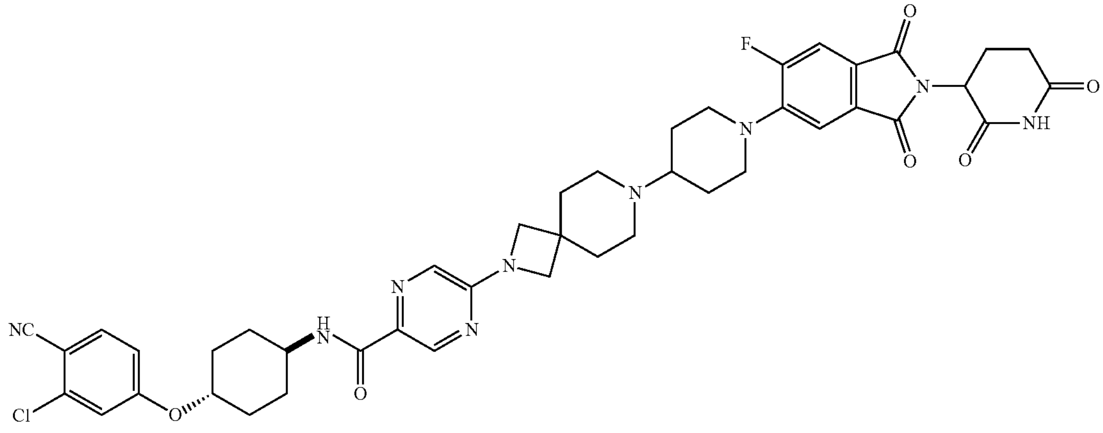
243
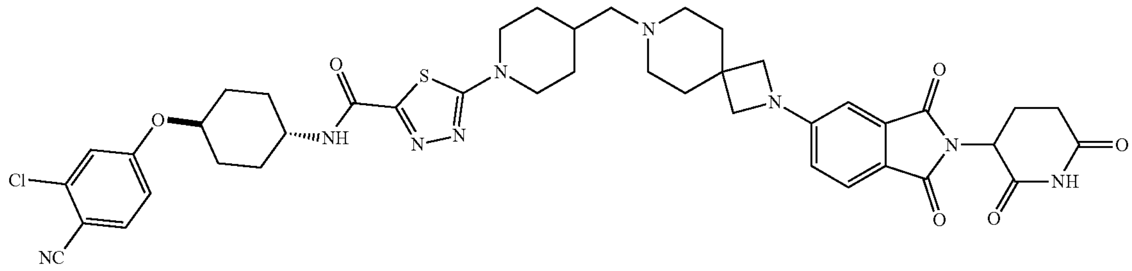
244
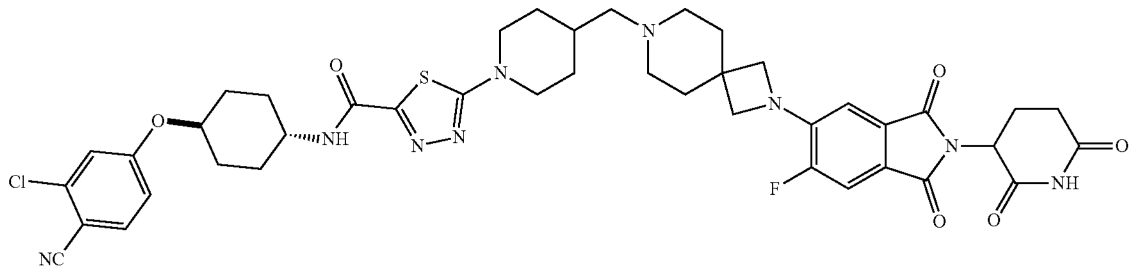

-continued
245
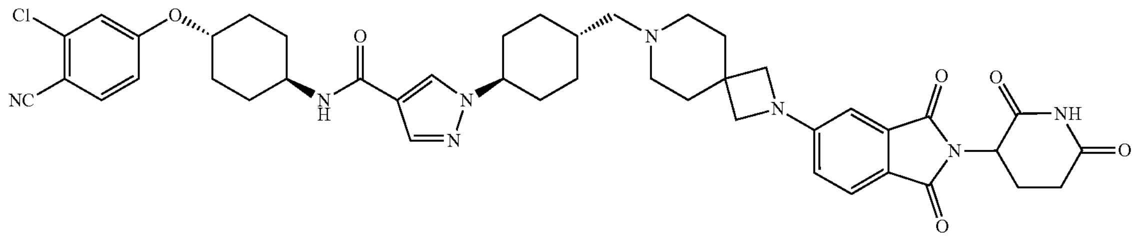
246
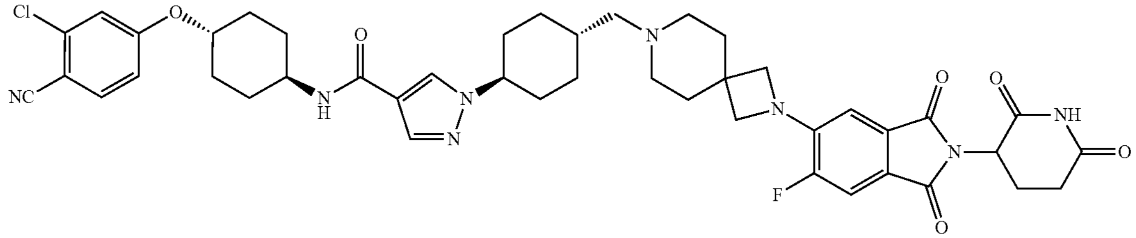
247
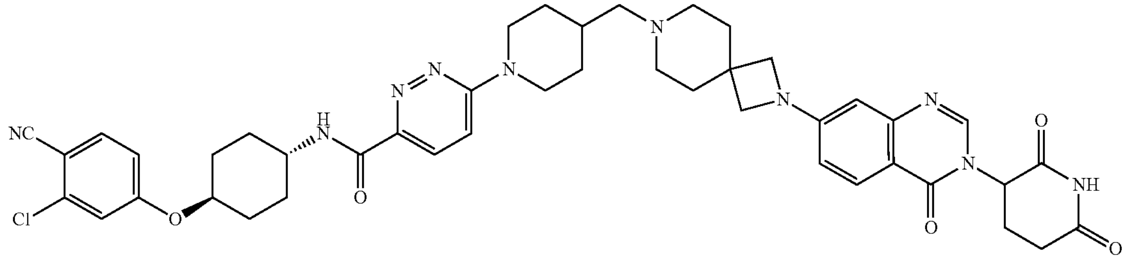
248
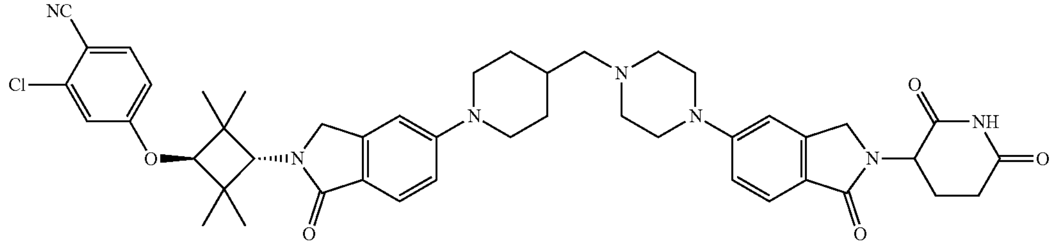
249
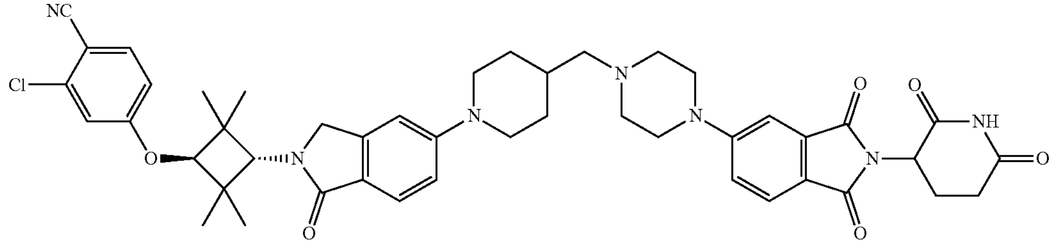
250
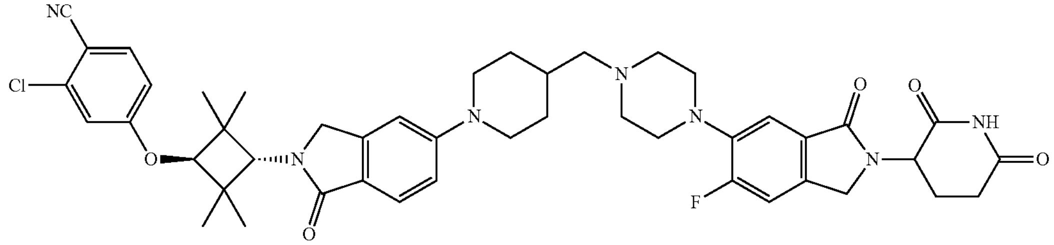

-continued
251
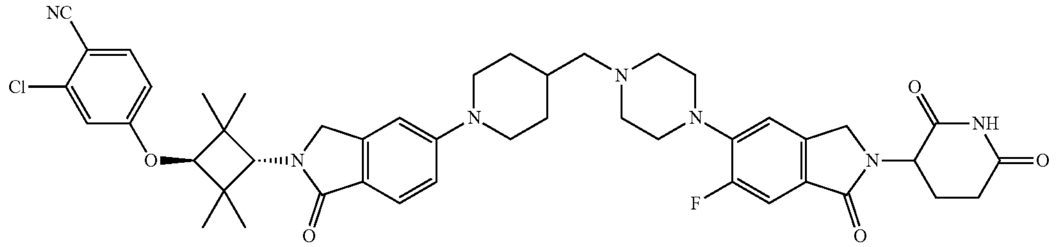
252
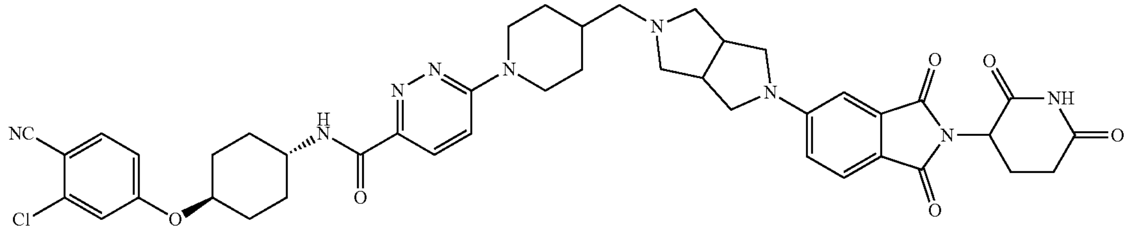
253
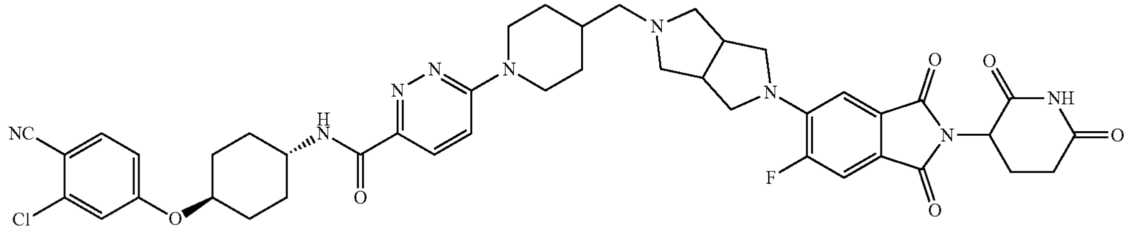
254
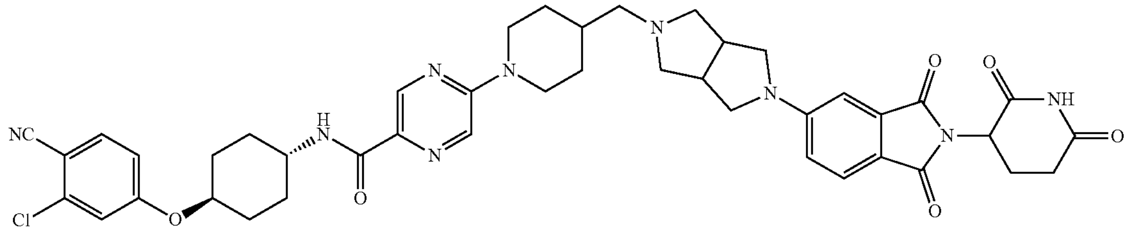
255
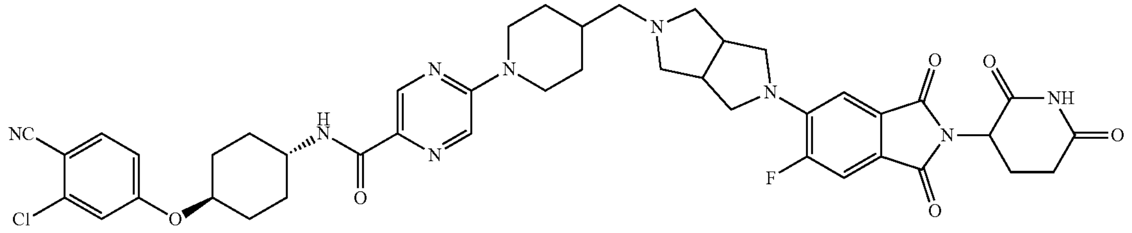
256
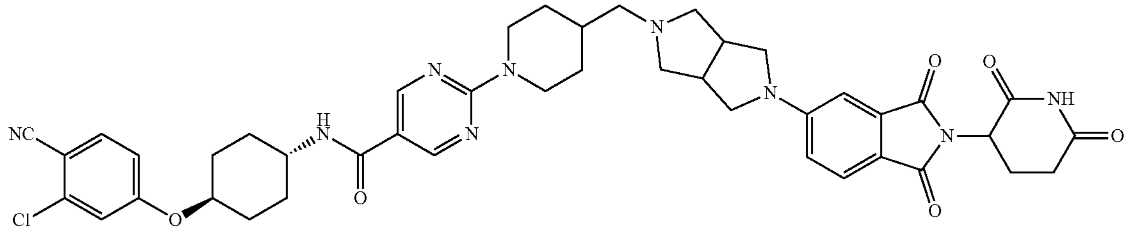

-continued
257
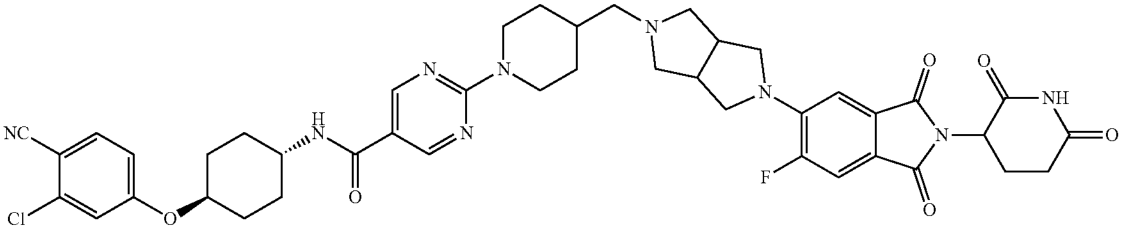
258
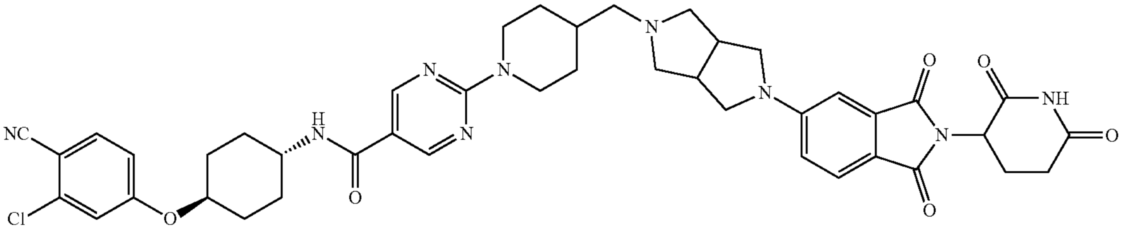
259
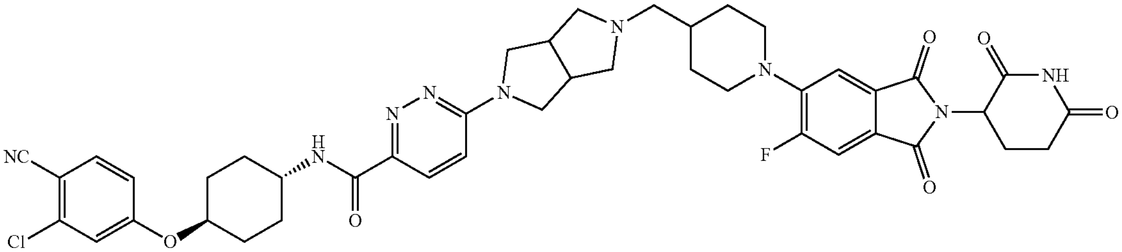
260
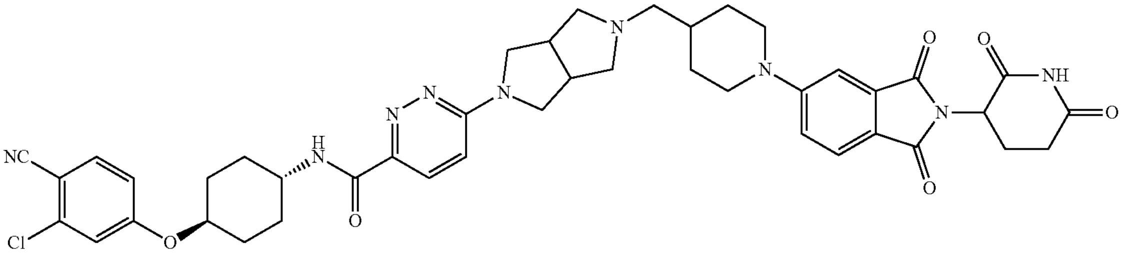
261
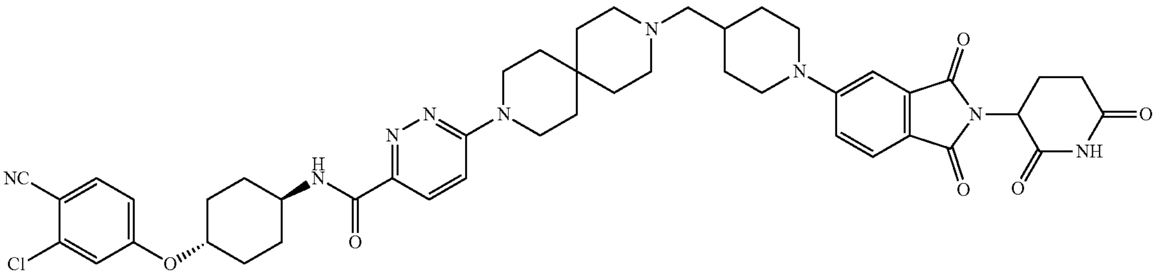
262
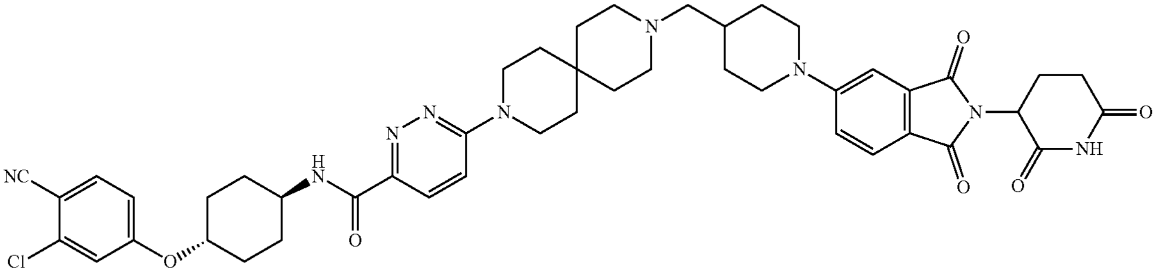

-continued
263
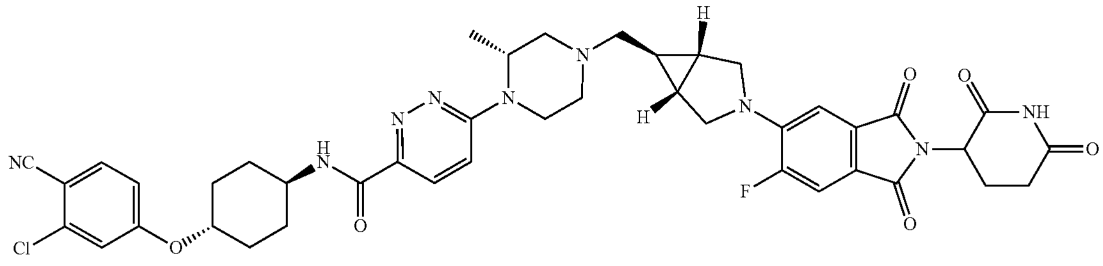
264
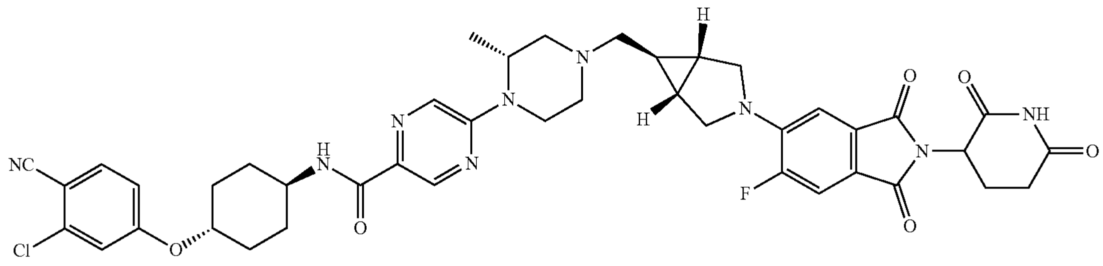
265
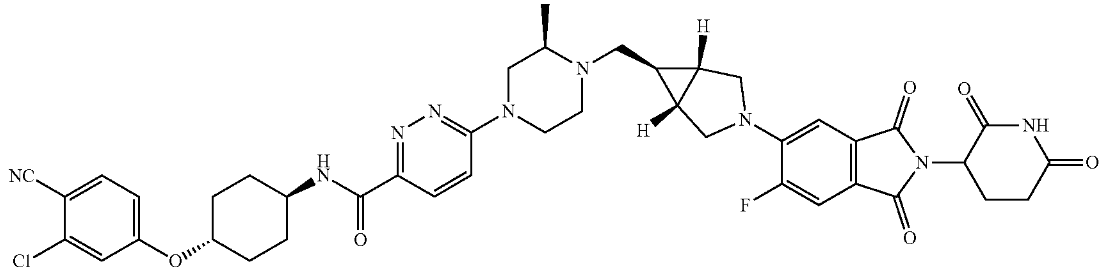
266
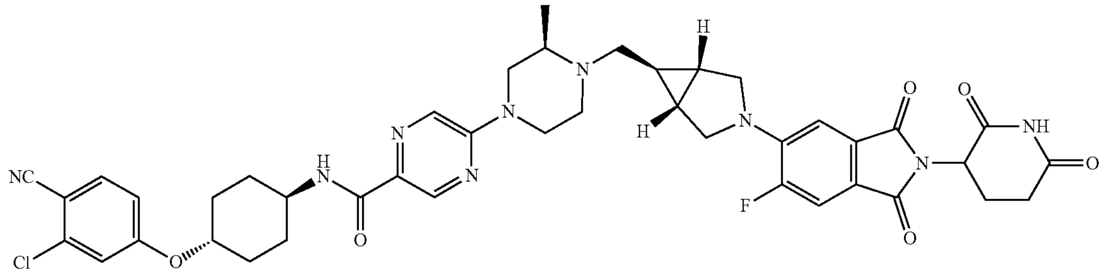
267
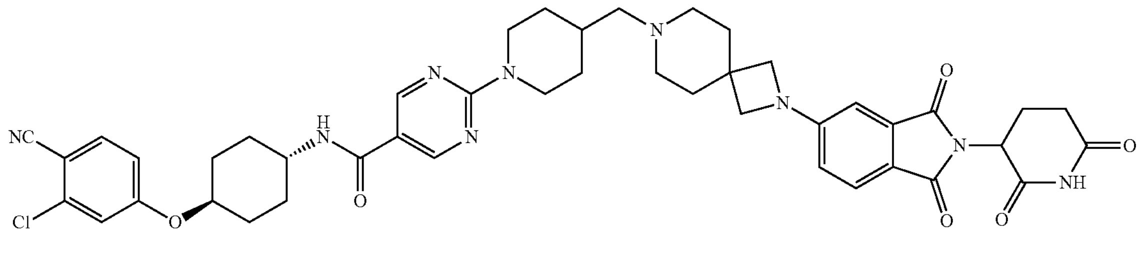
268
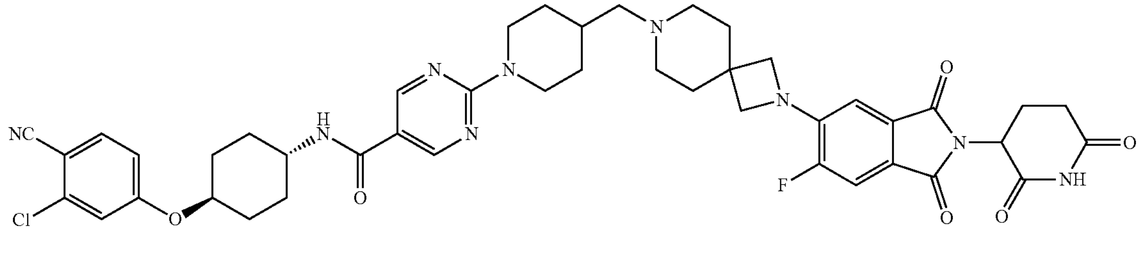

-continued
269
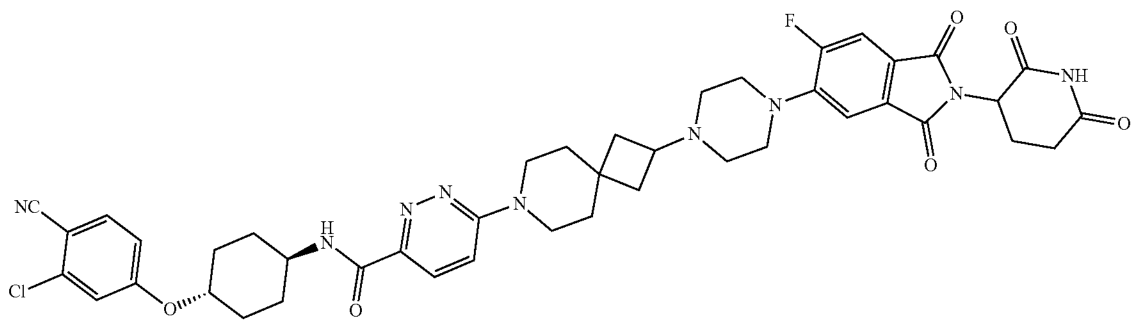
270
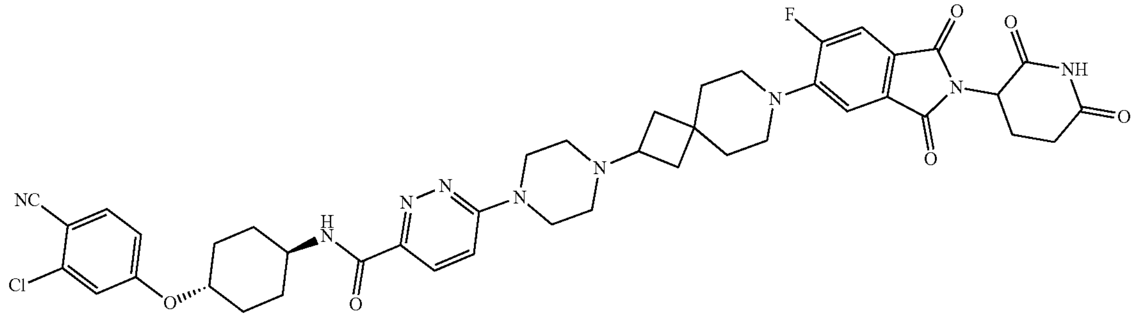
271
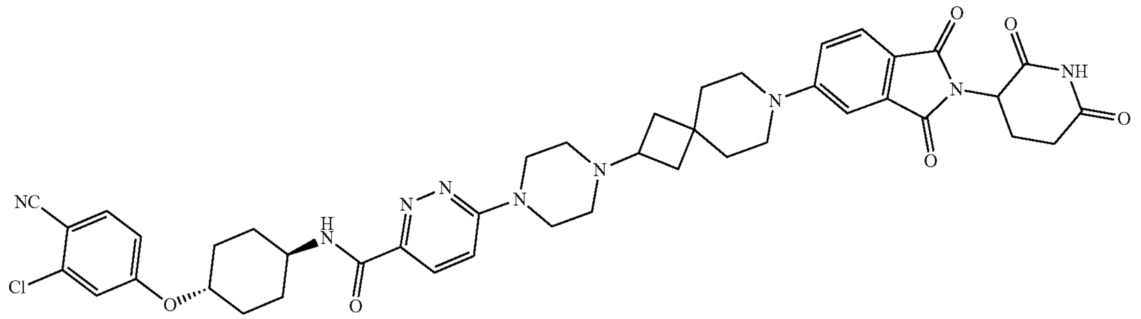
272
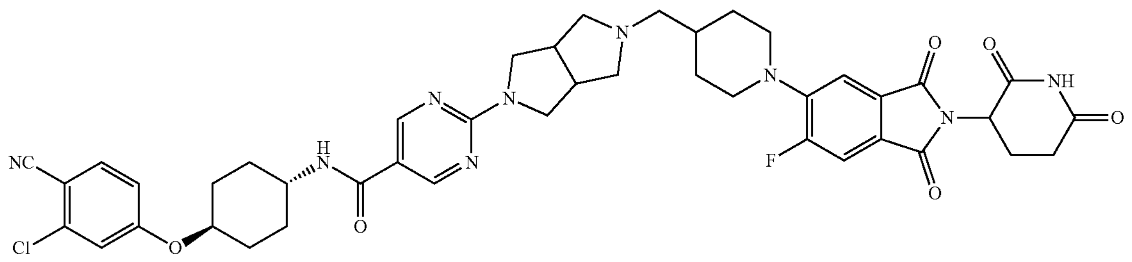
273
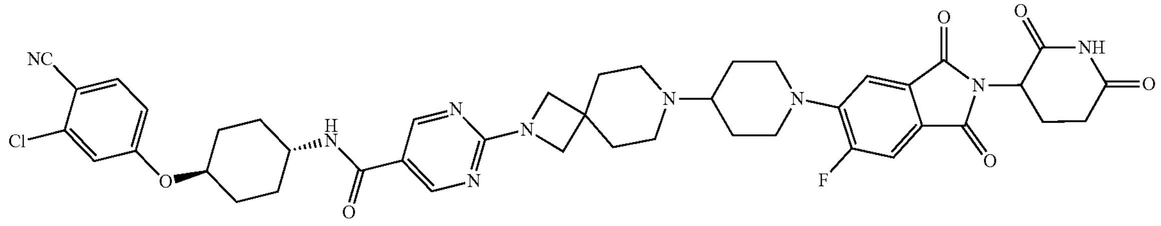

-continued
274
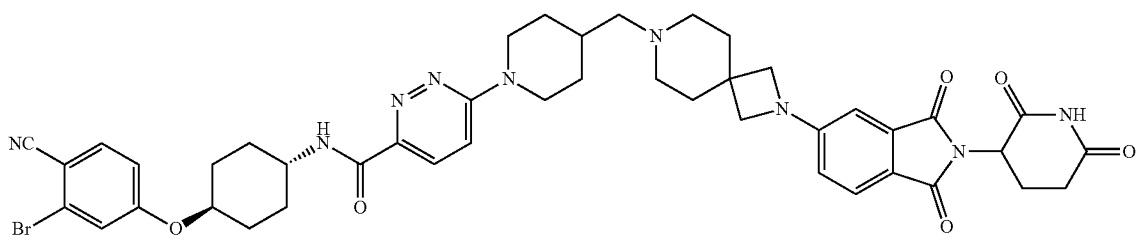
275
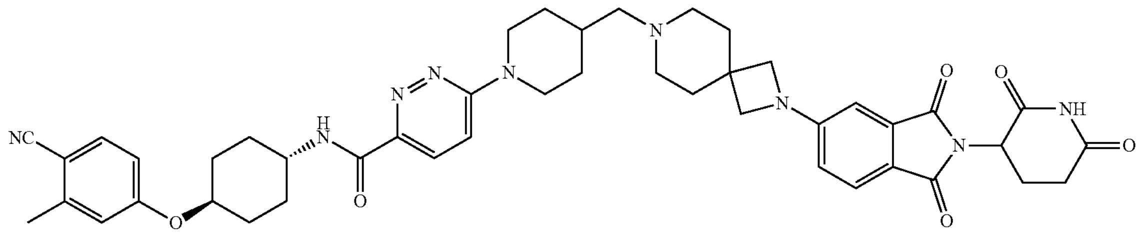
276
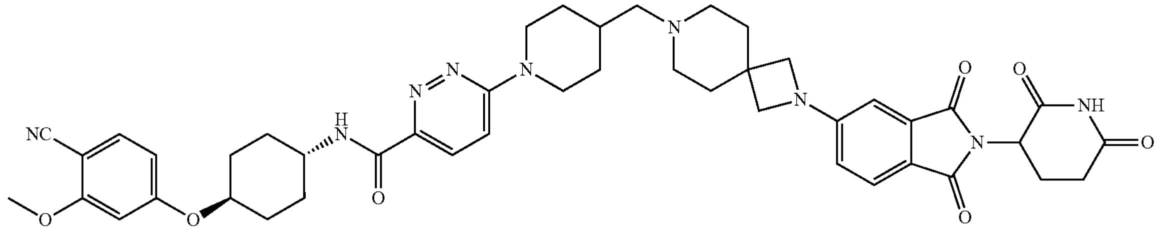
277
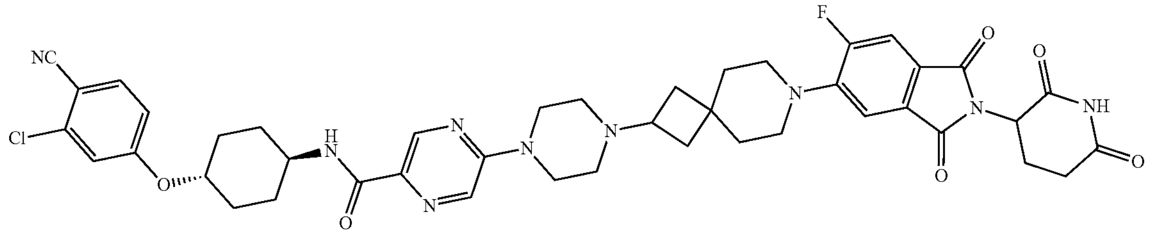
278
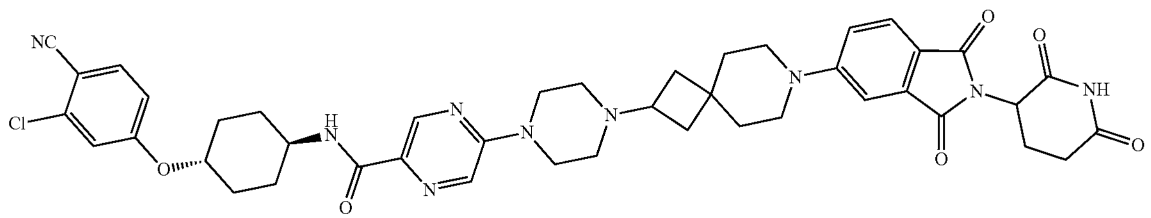
279
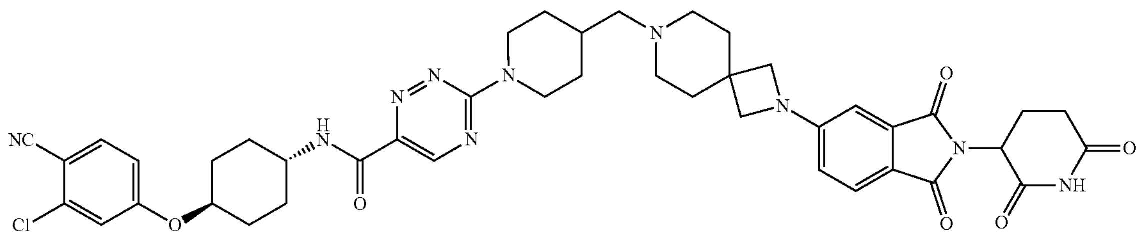

-continued
280
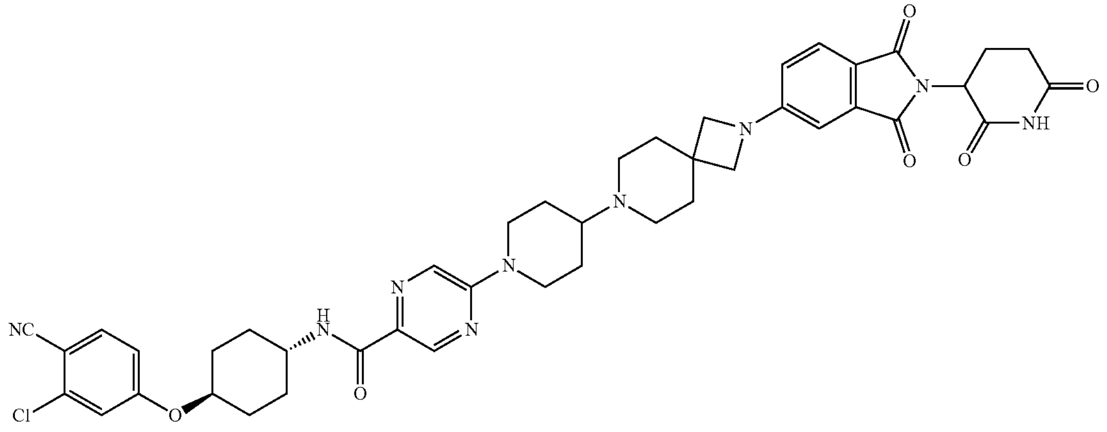
281
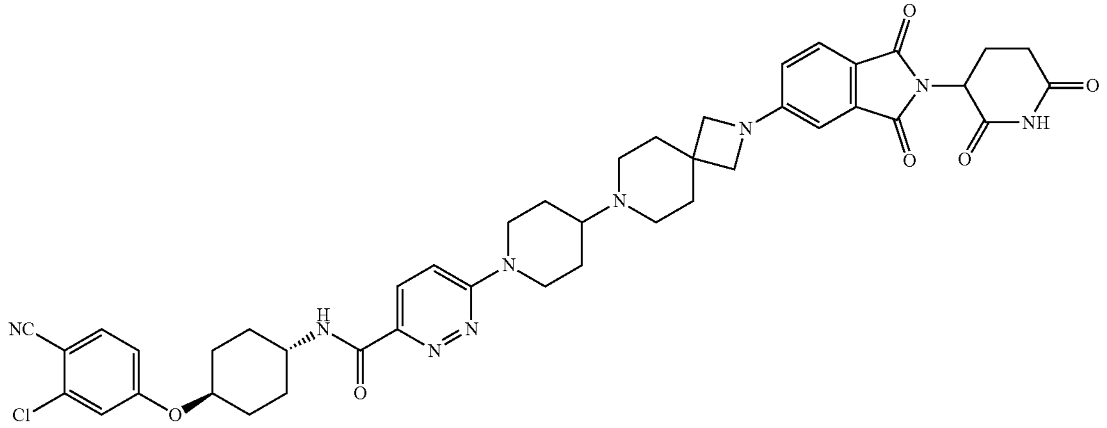
282
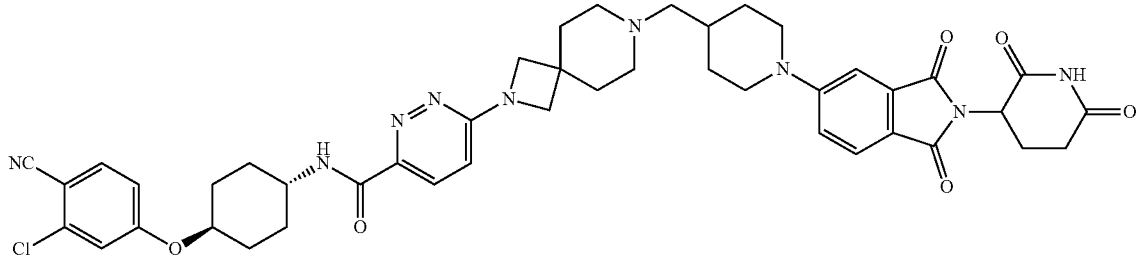
283
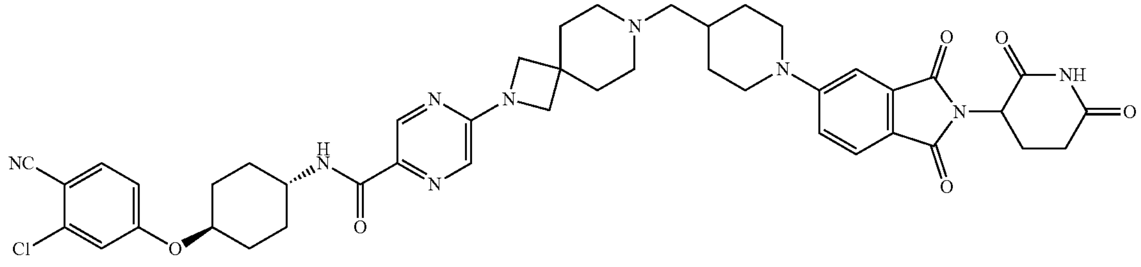

-continued
284
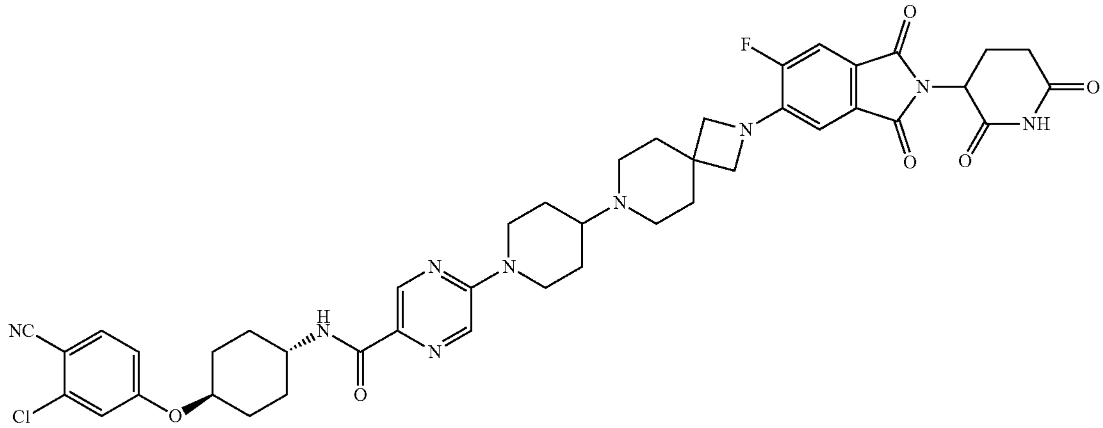
285
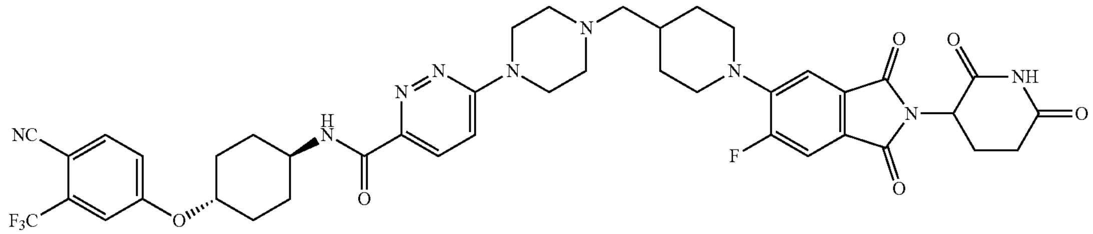
286
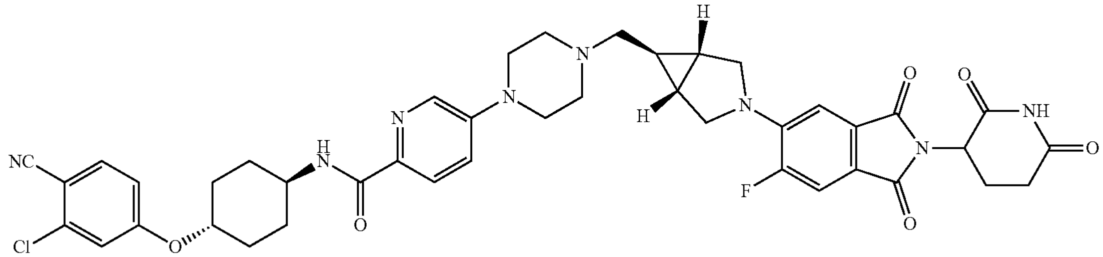
287
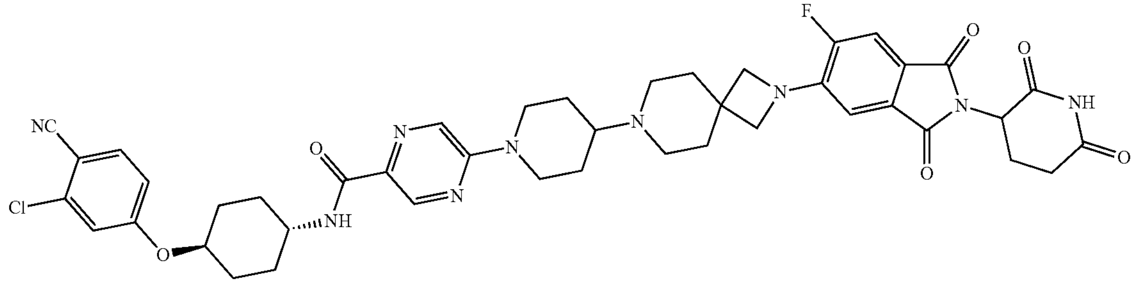
288
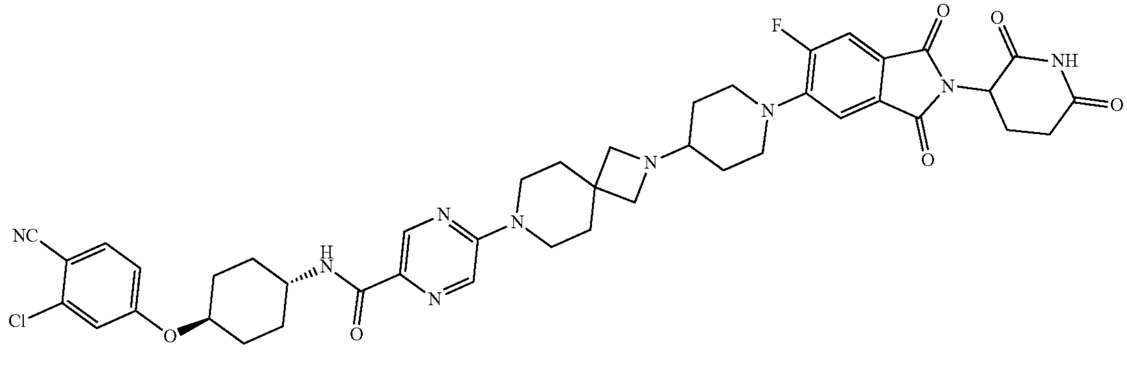

-continued
289
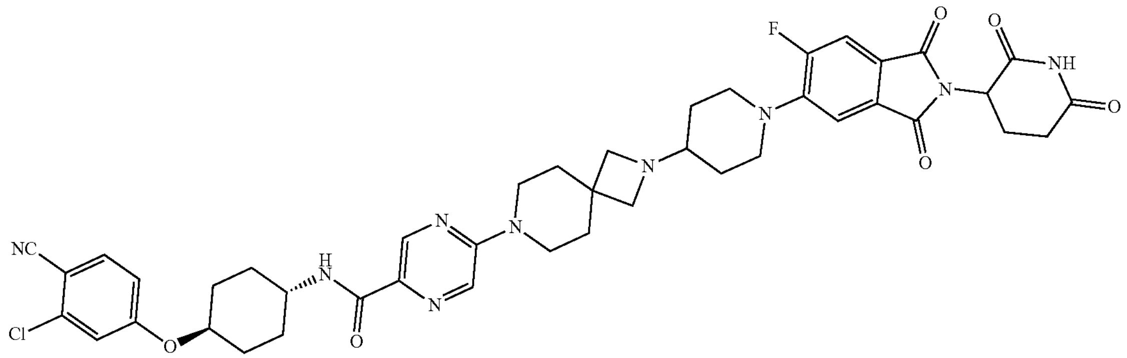
290
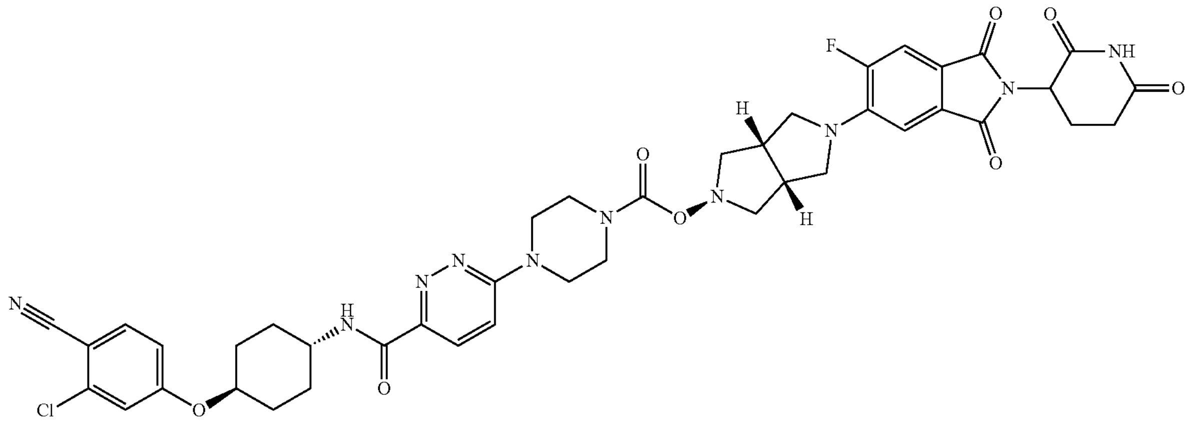
291
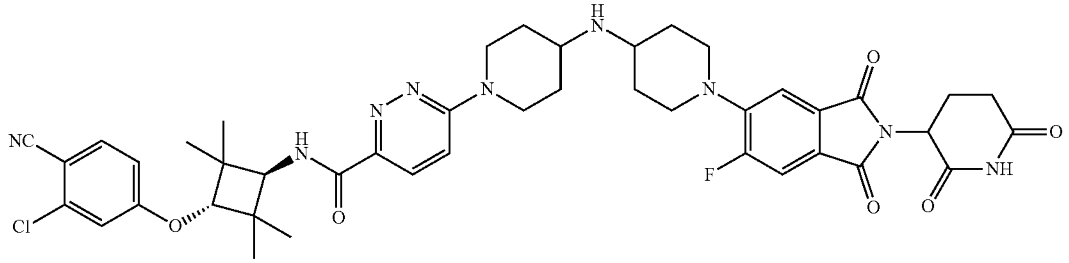
292
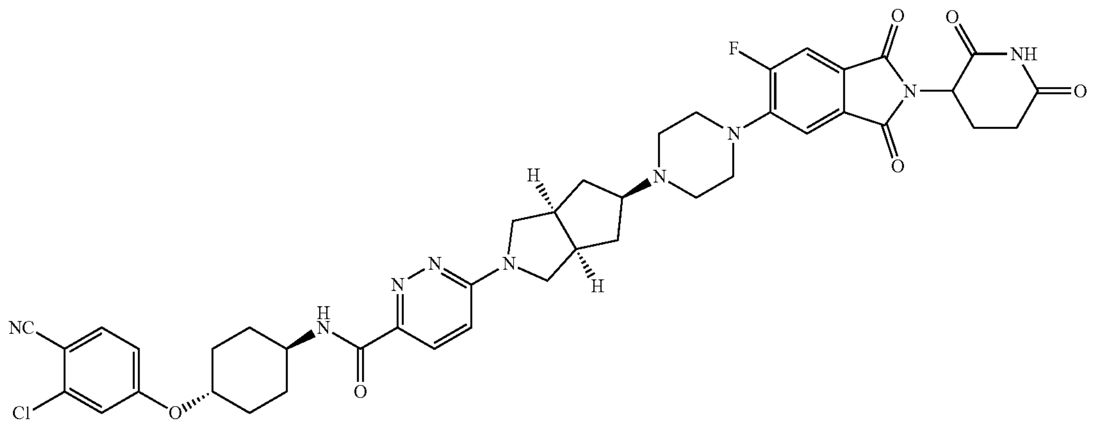

-continued
293
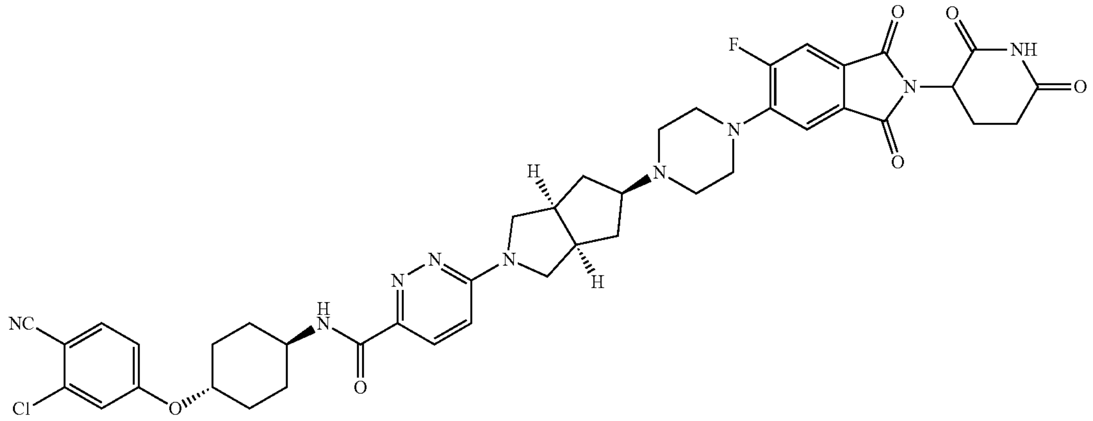
294
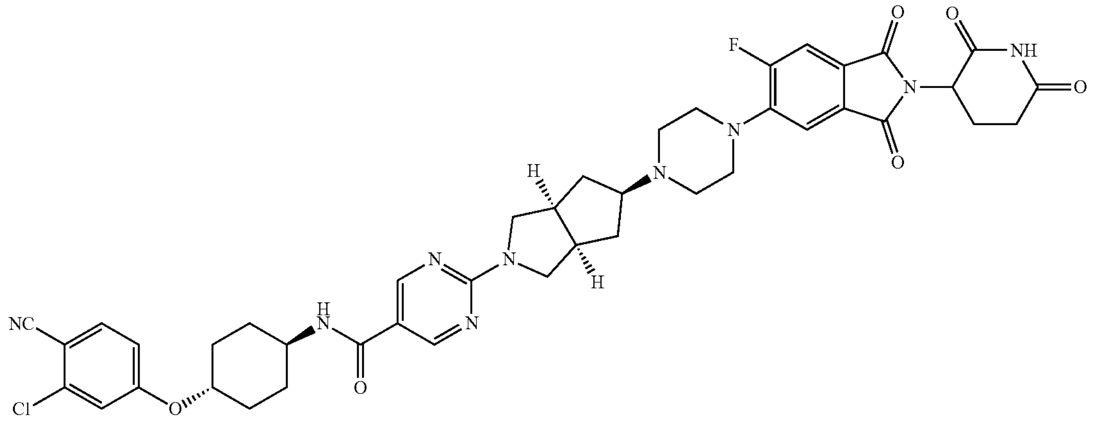
295
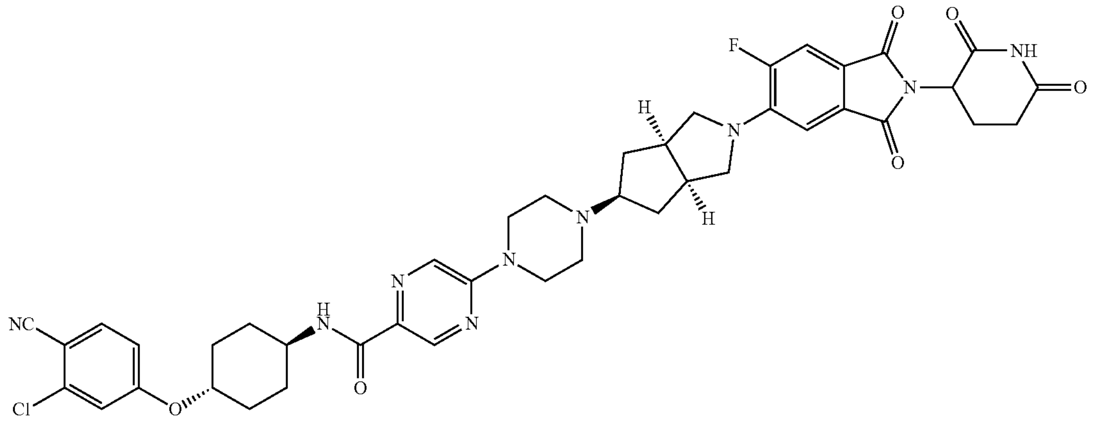

-continued
296
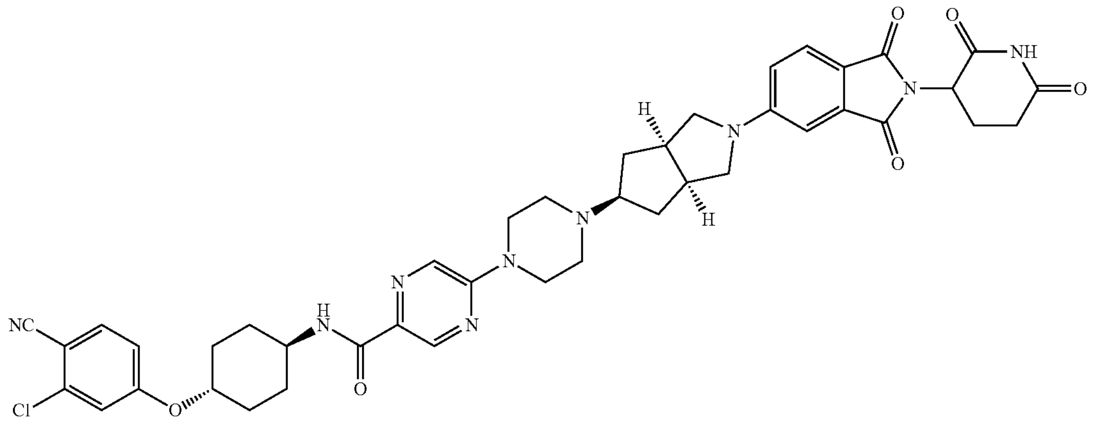
297
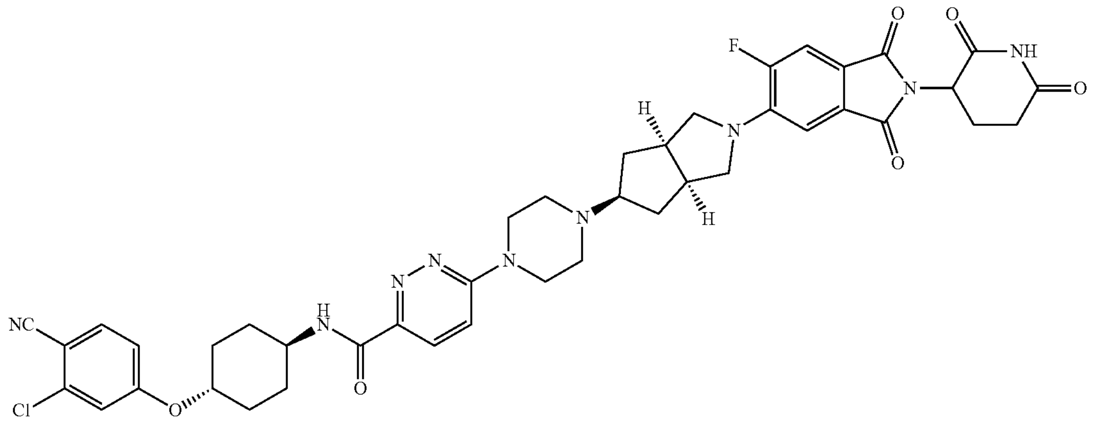
298
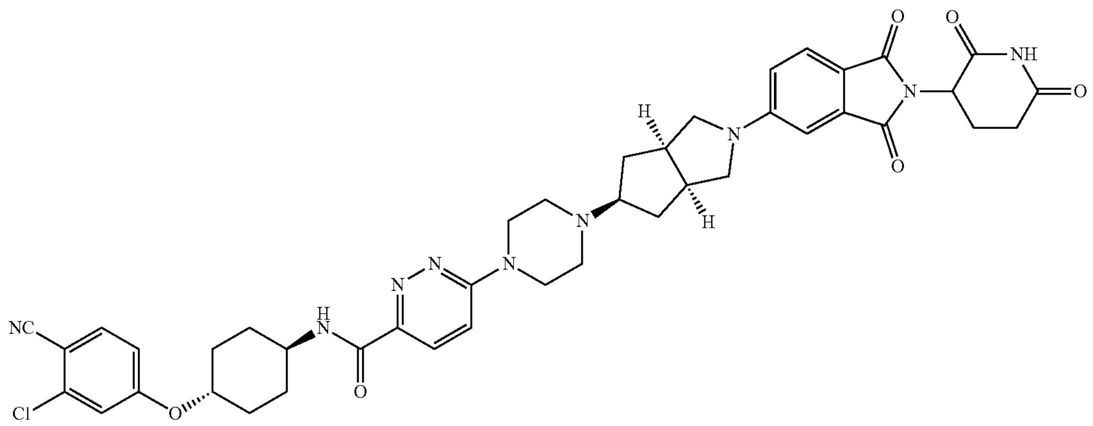

-continued
299
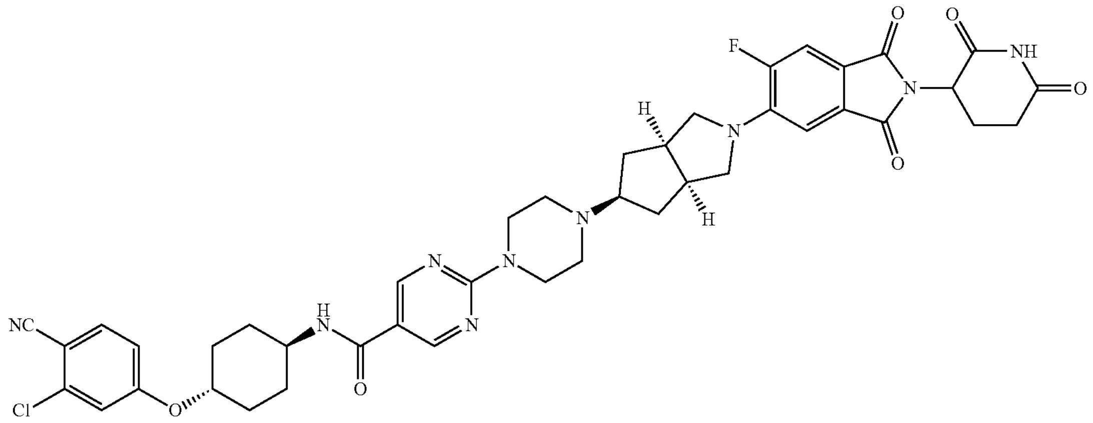
300
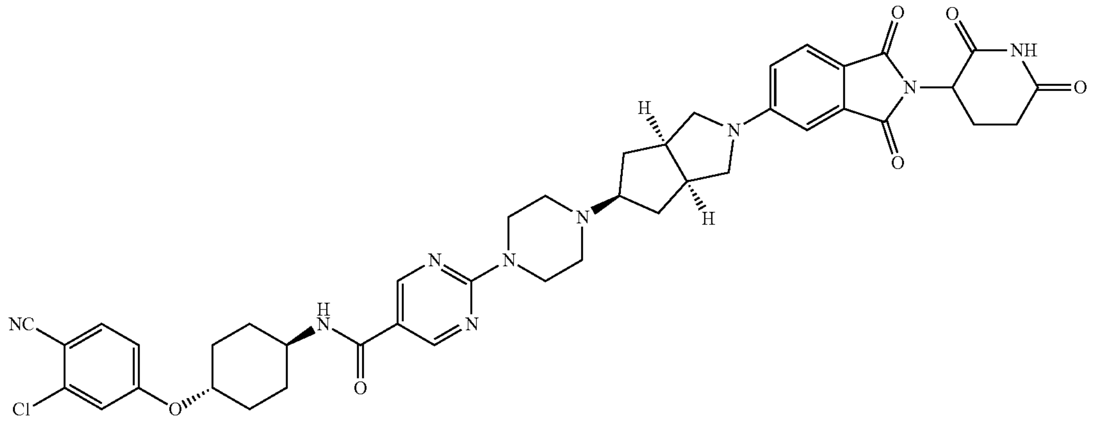
301
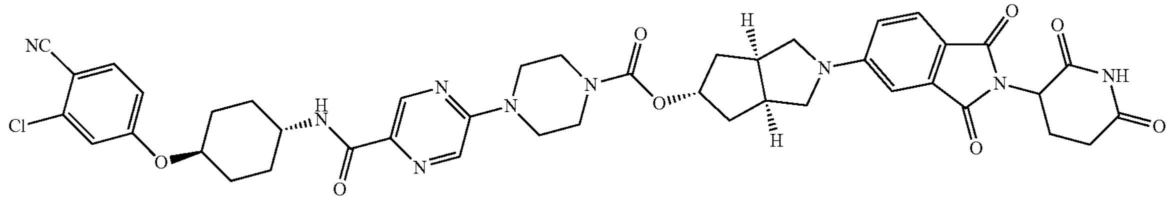
302
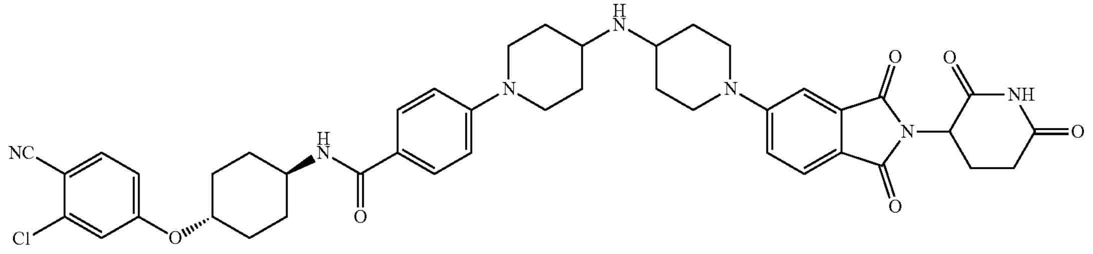
303
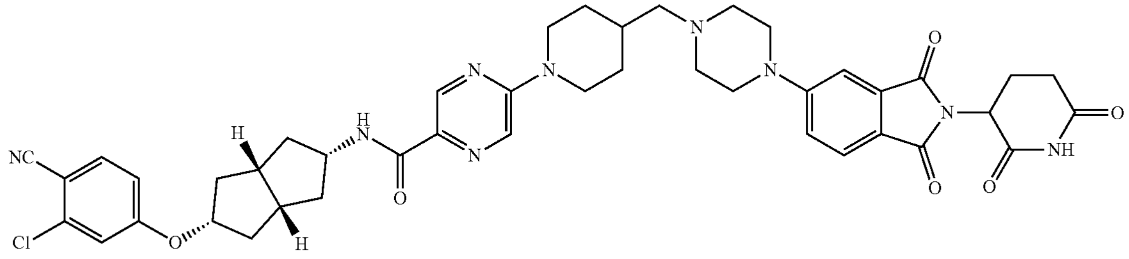

-continued
304
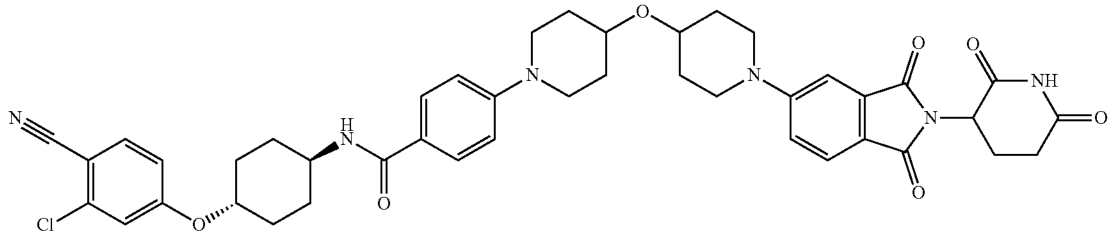
305
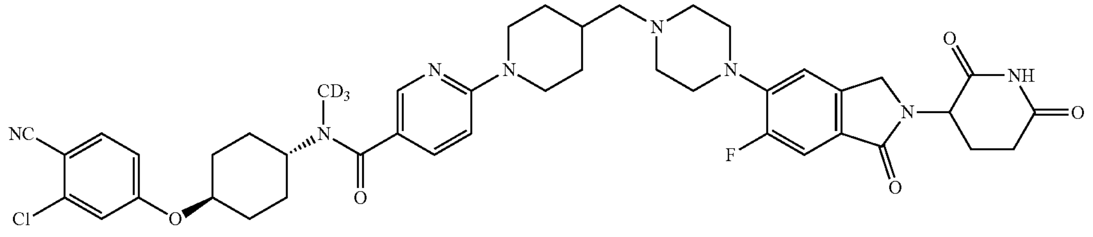
306
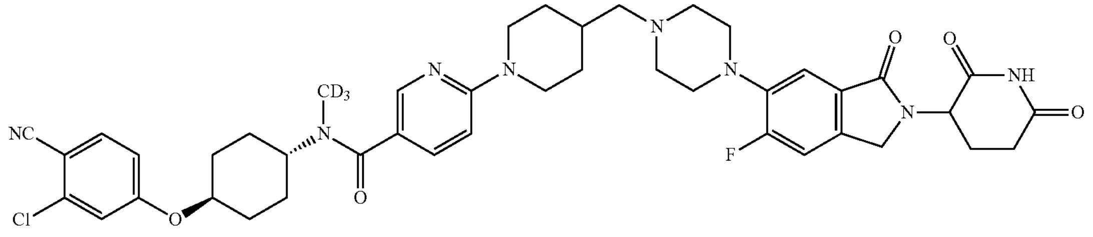
307
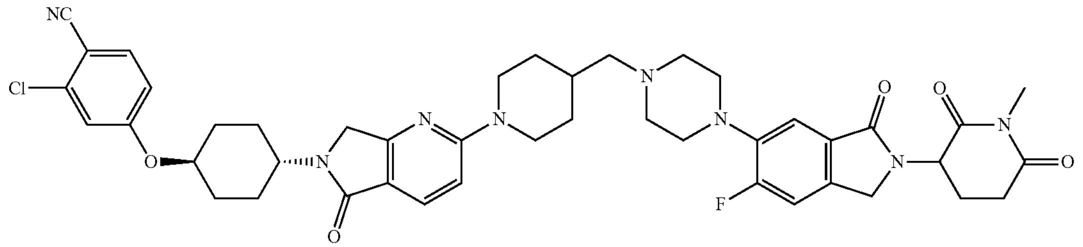
308
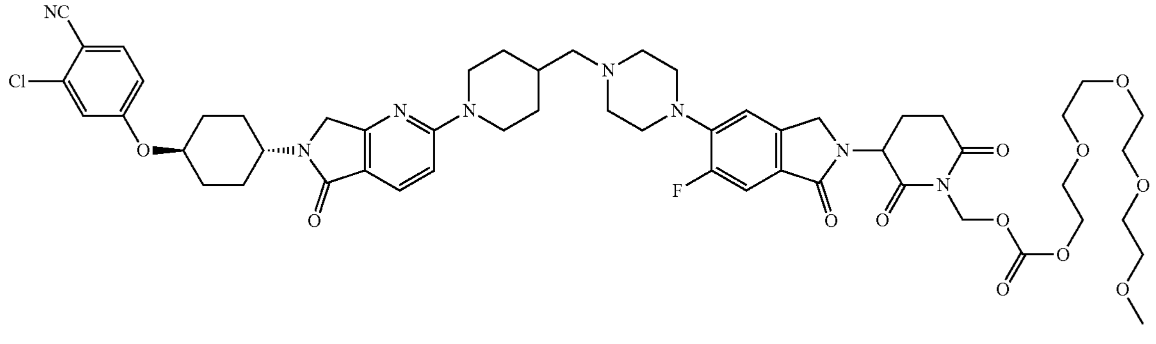
309
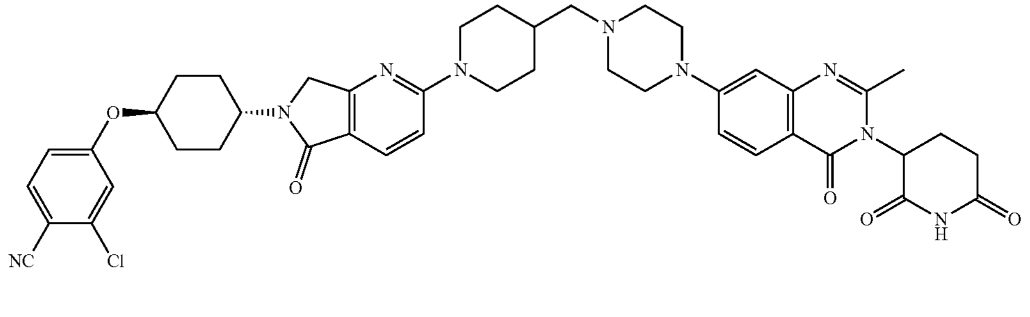

-continued
310
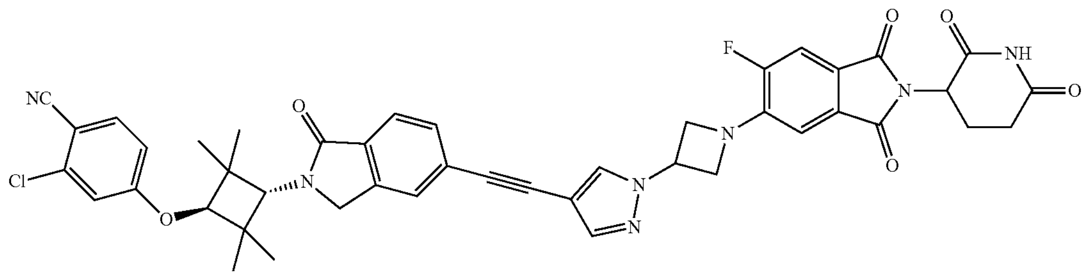
311
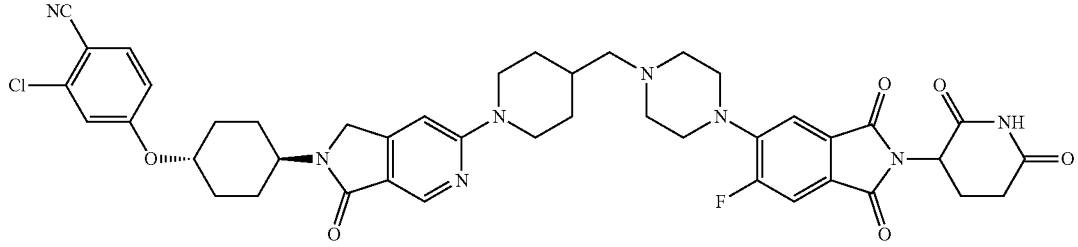
312
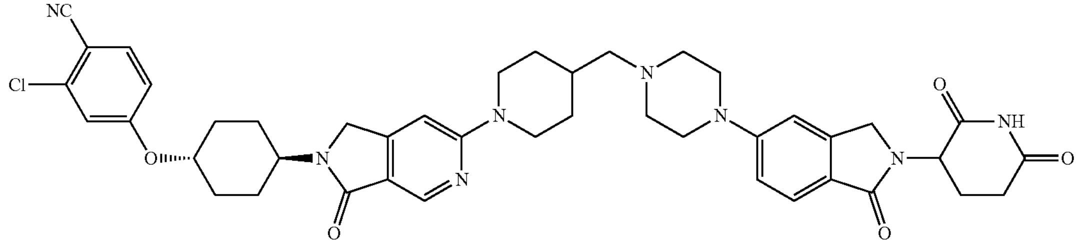
313
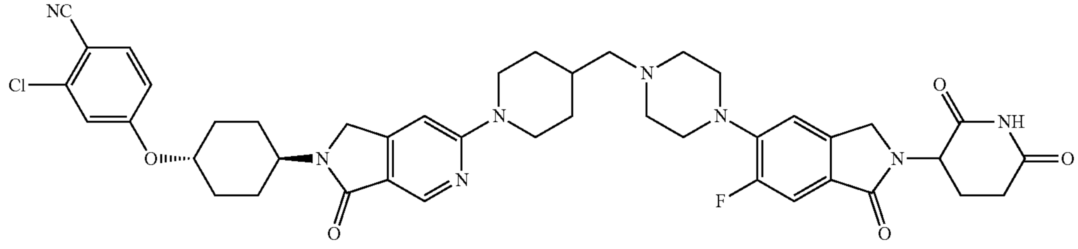
314
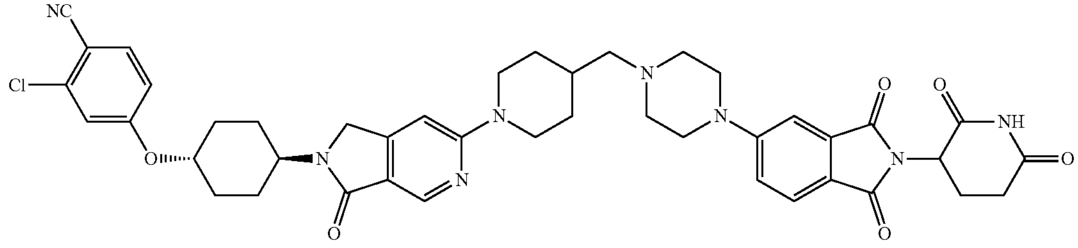

-continued
315
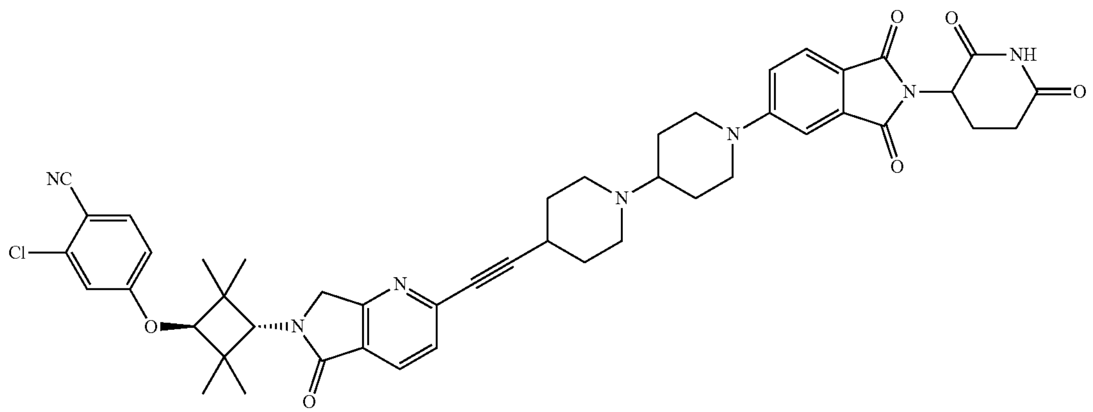
316
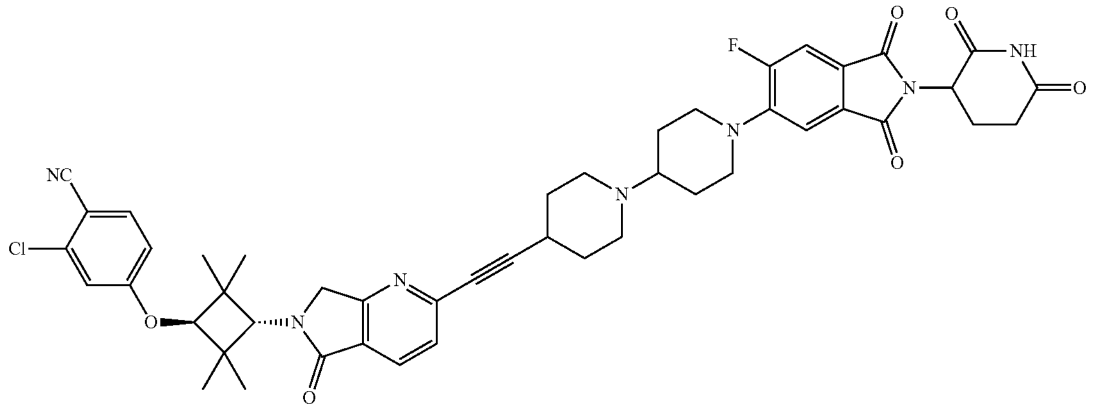
317
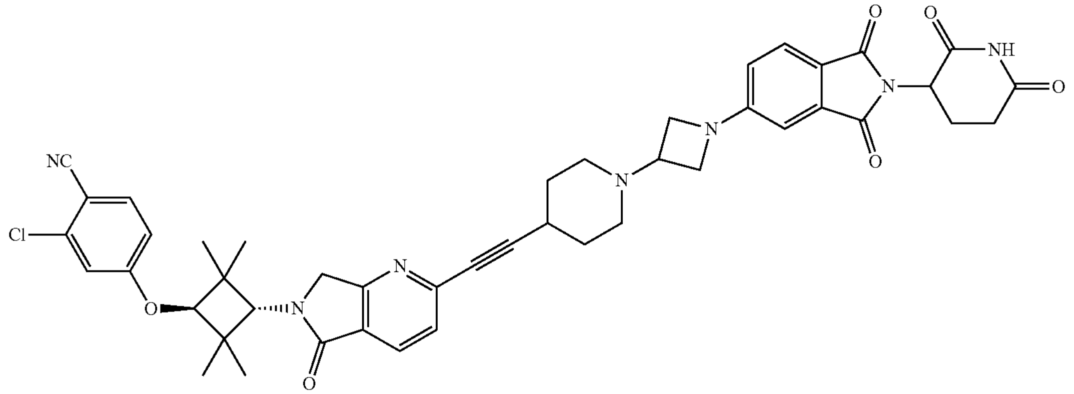
318
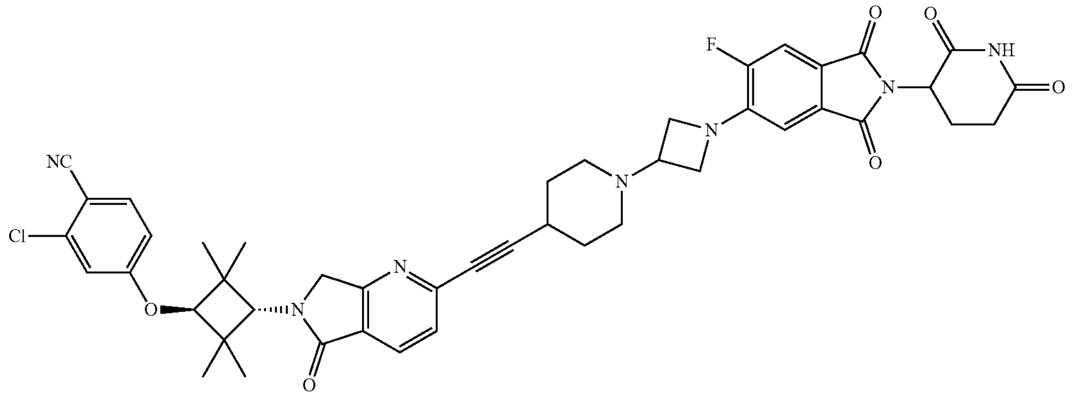

-continued
319
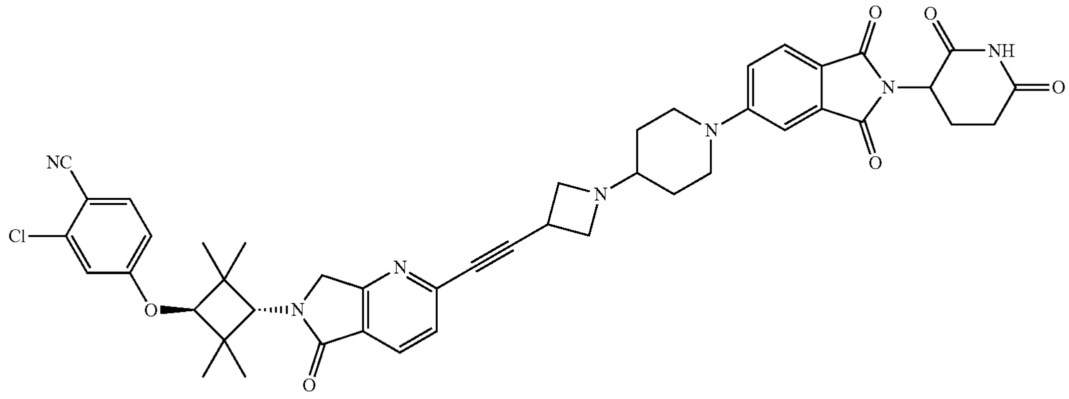
320
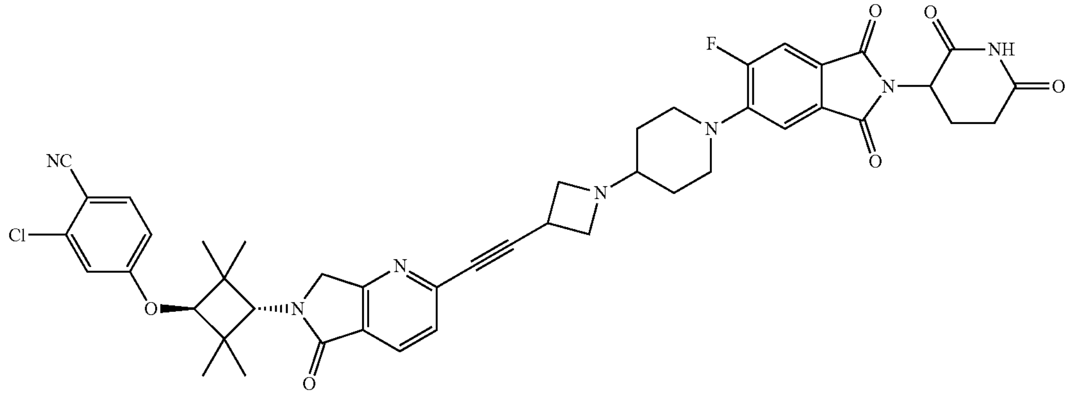
320
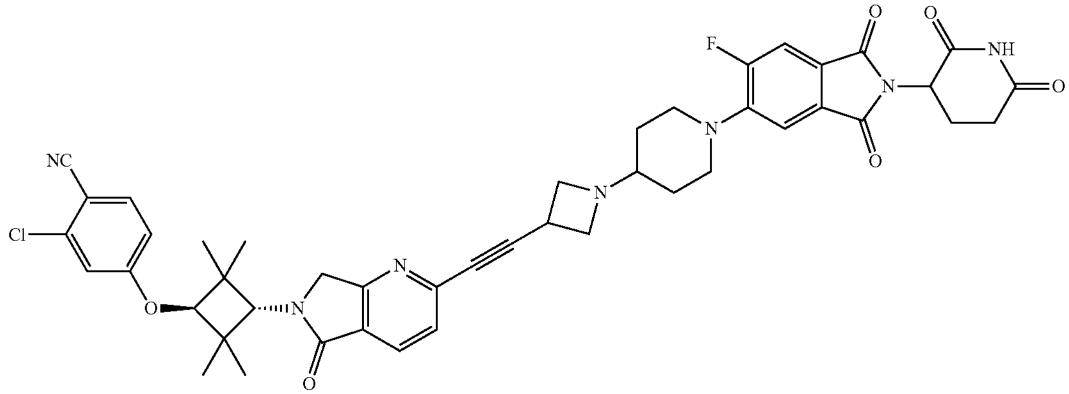
321
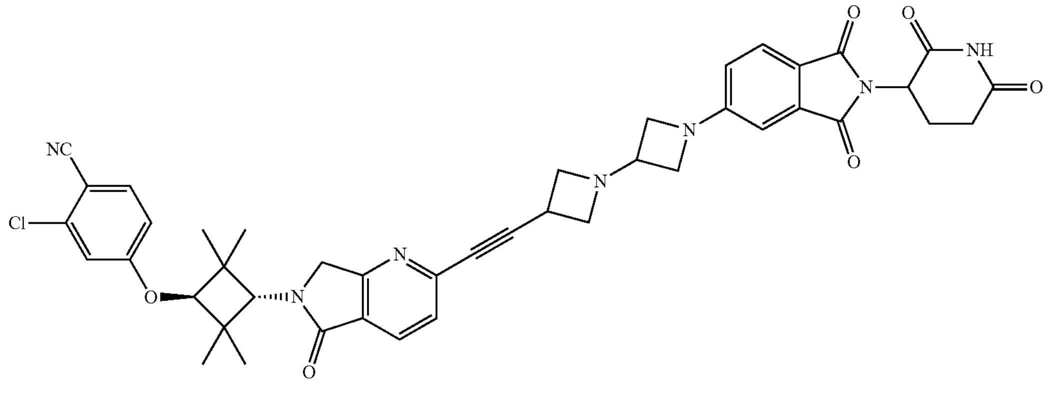

-continued
322
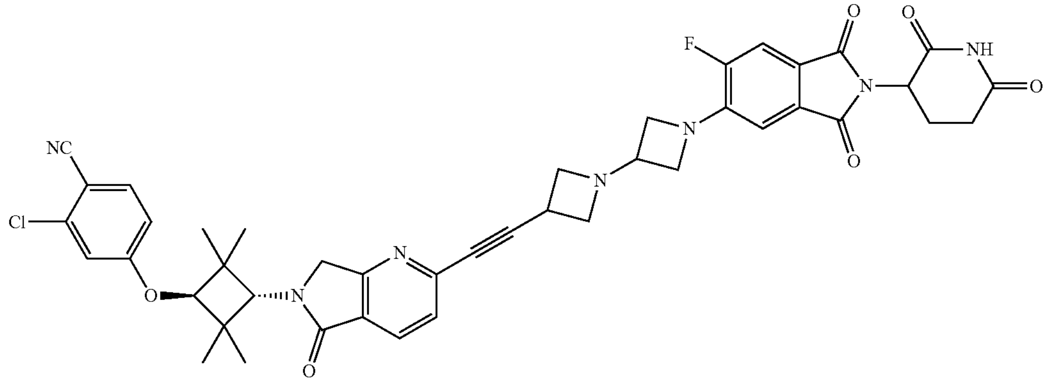
323
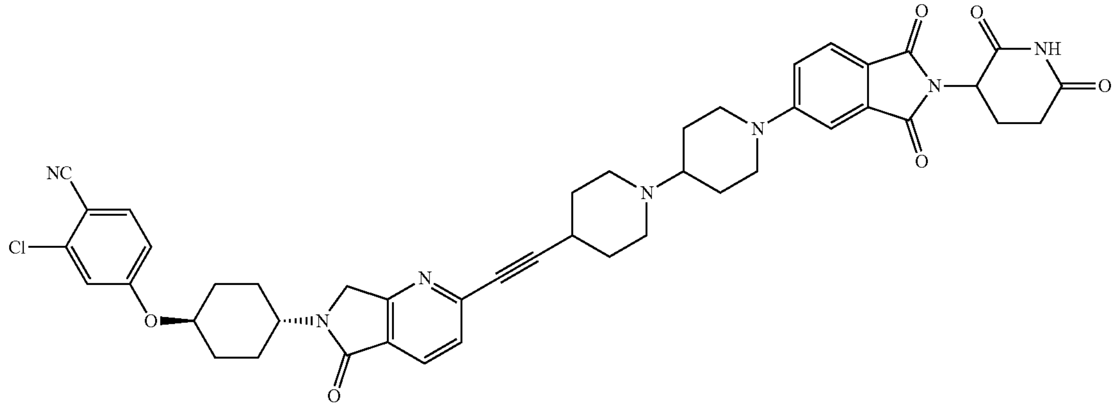
324
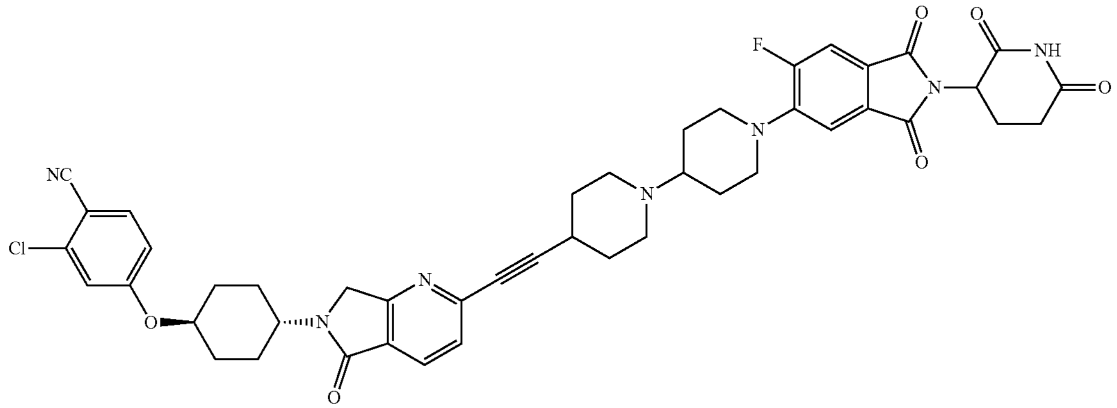
325
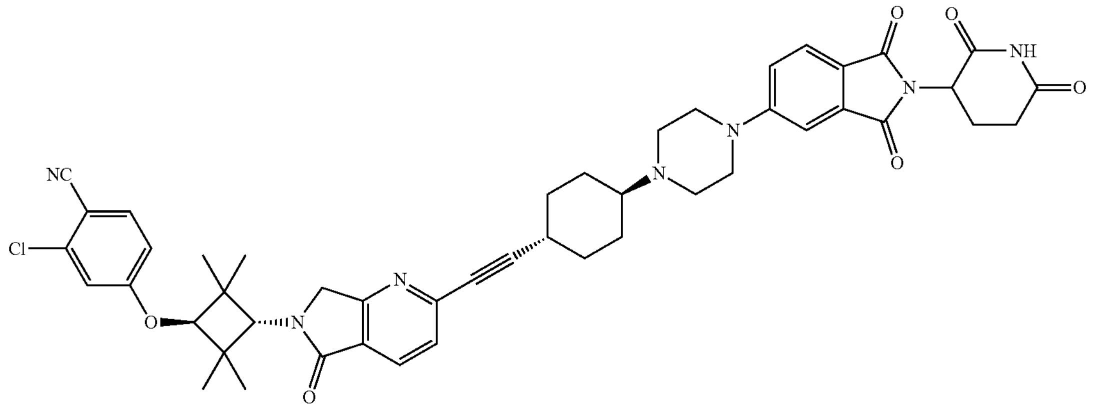

-continued
326
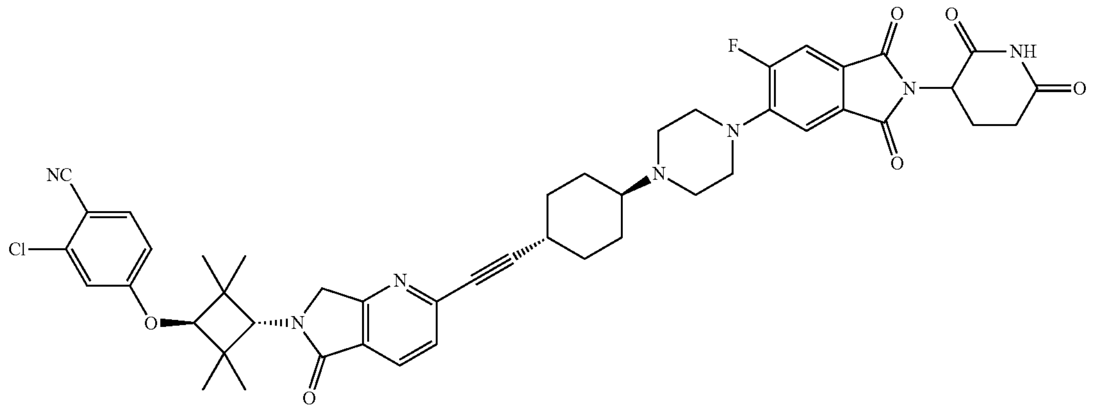
327
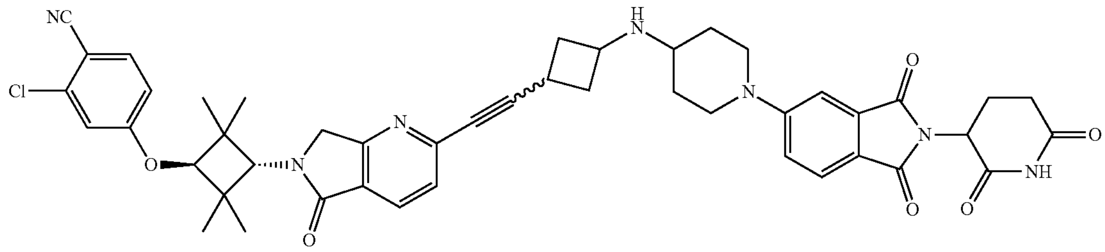
328
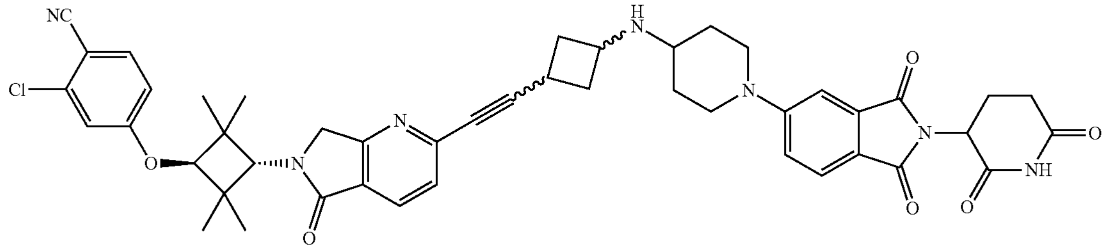
329
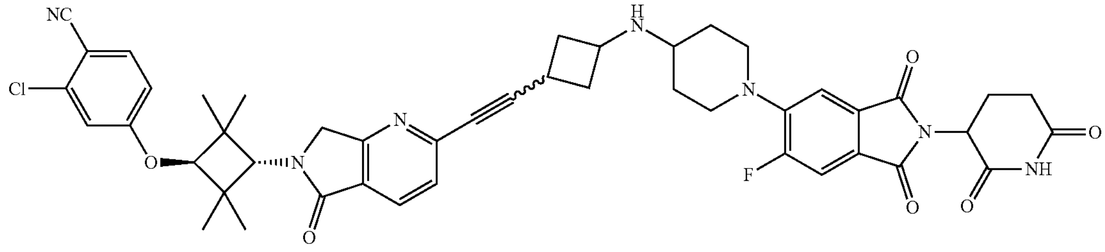
330
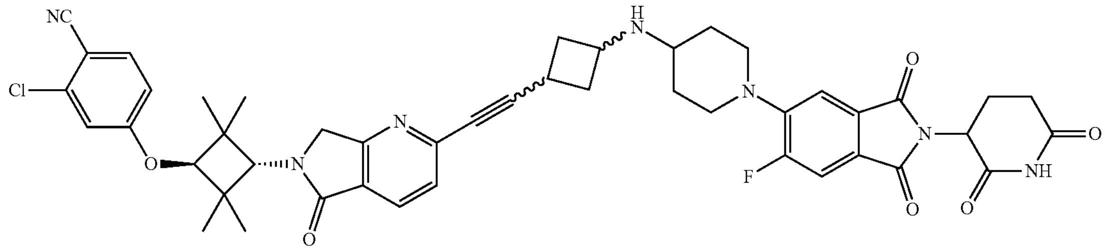

-continued
331
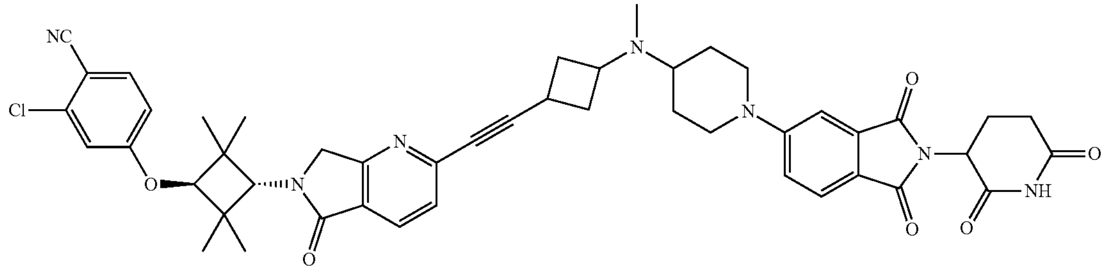
332
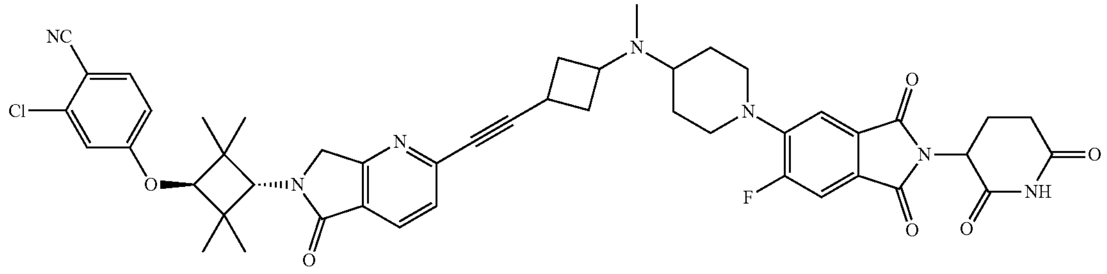
333
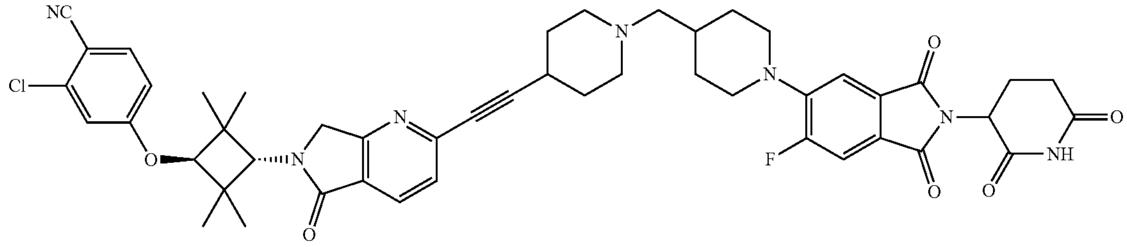
334
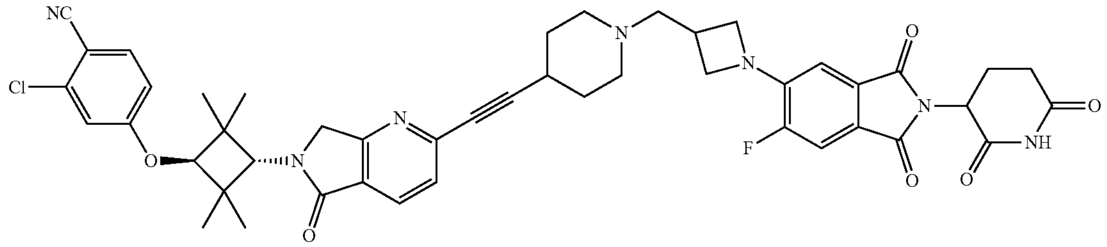
335
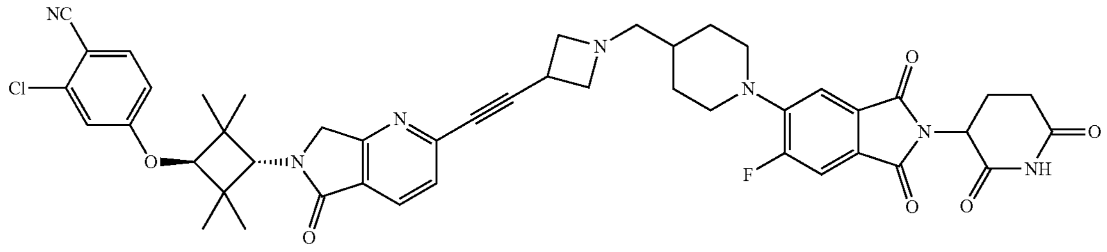
336
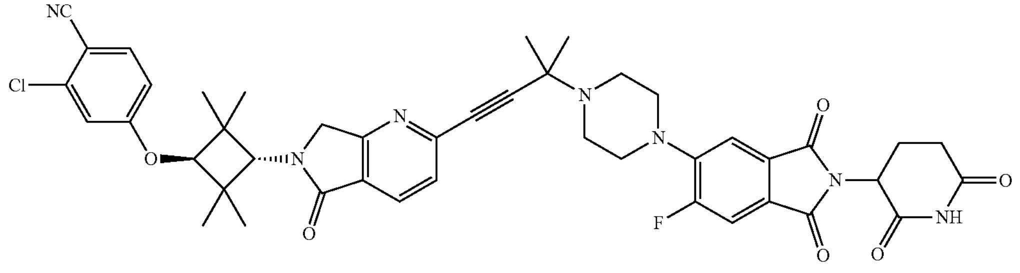

-continued
337
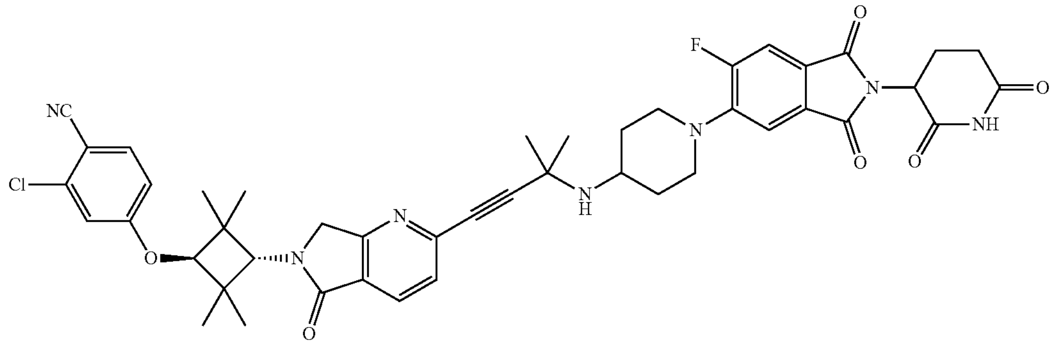
338
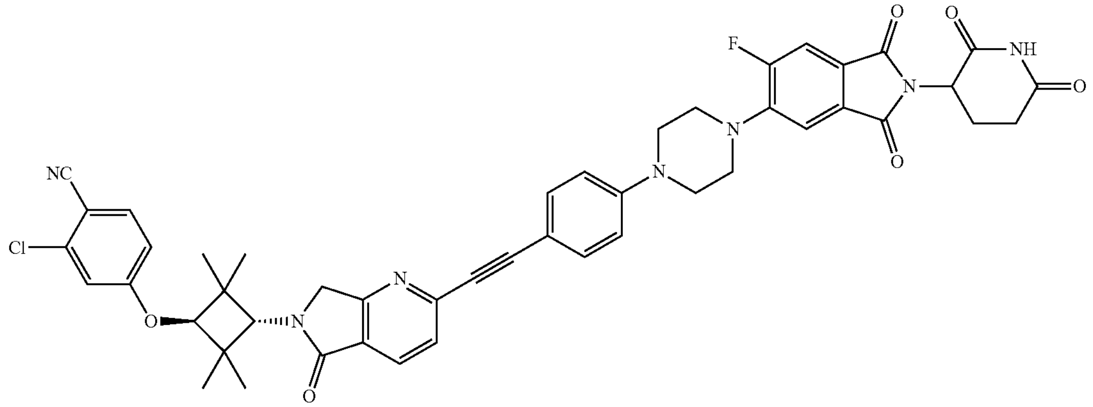
339
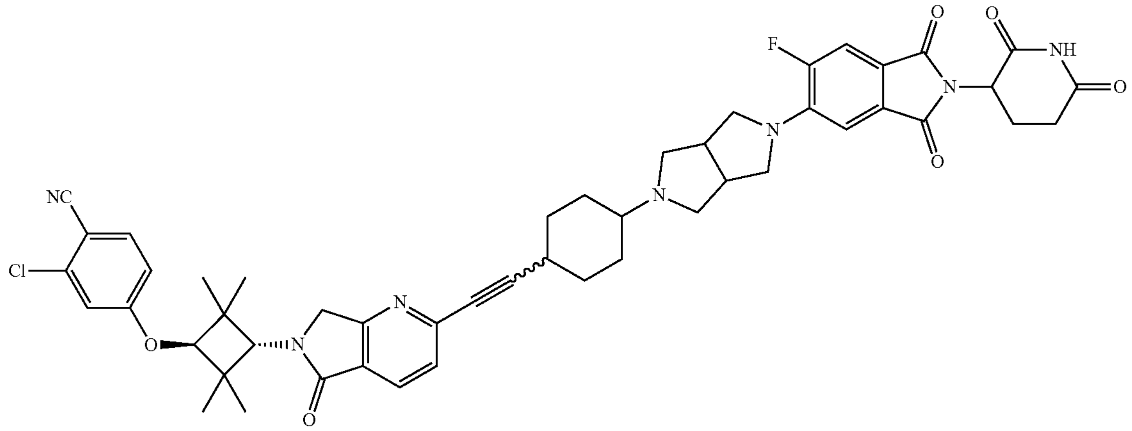
340
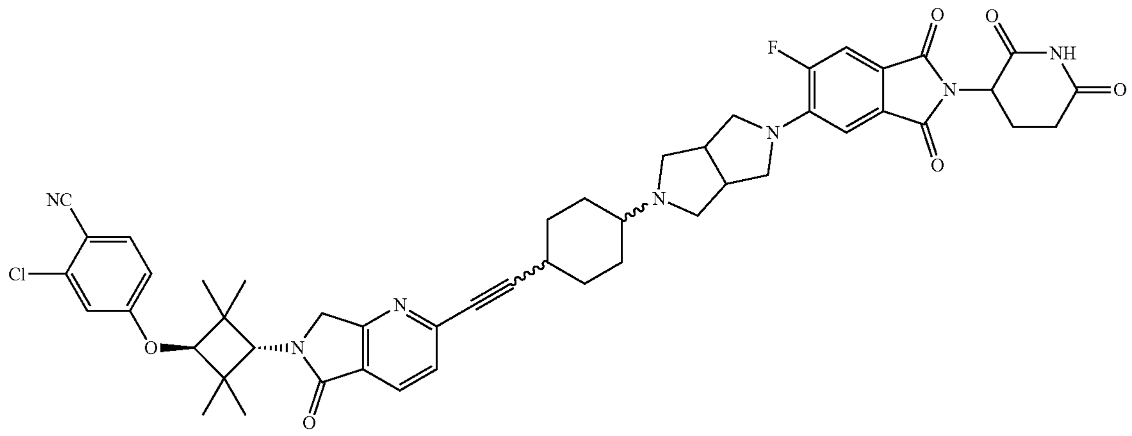

-continued
341
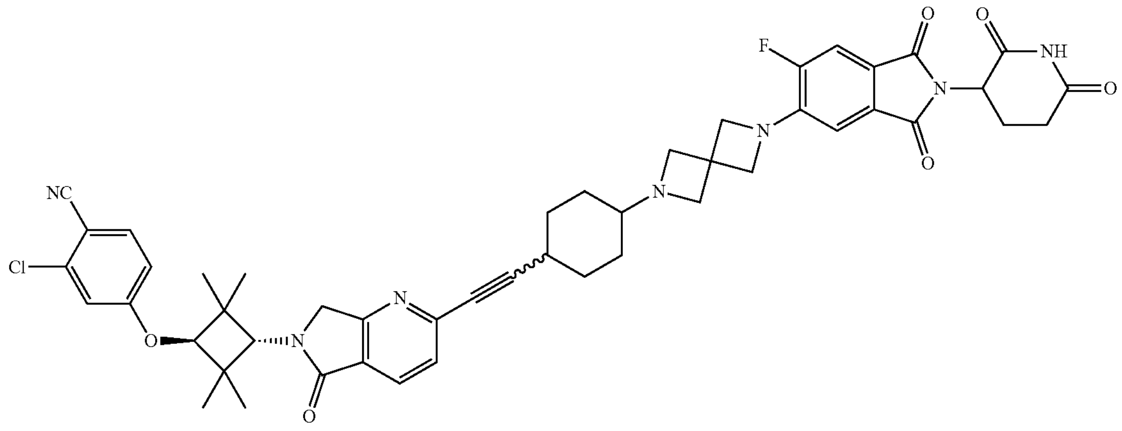
342
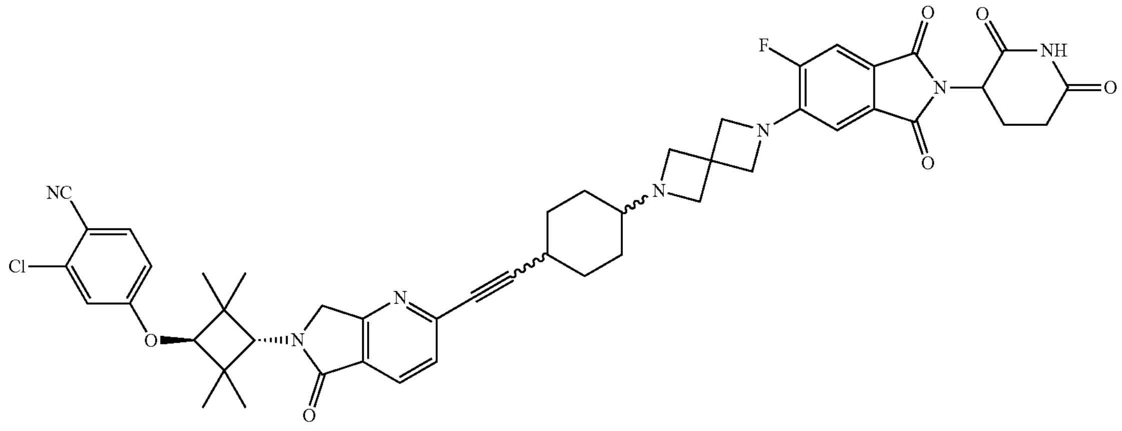
343
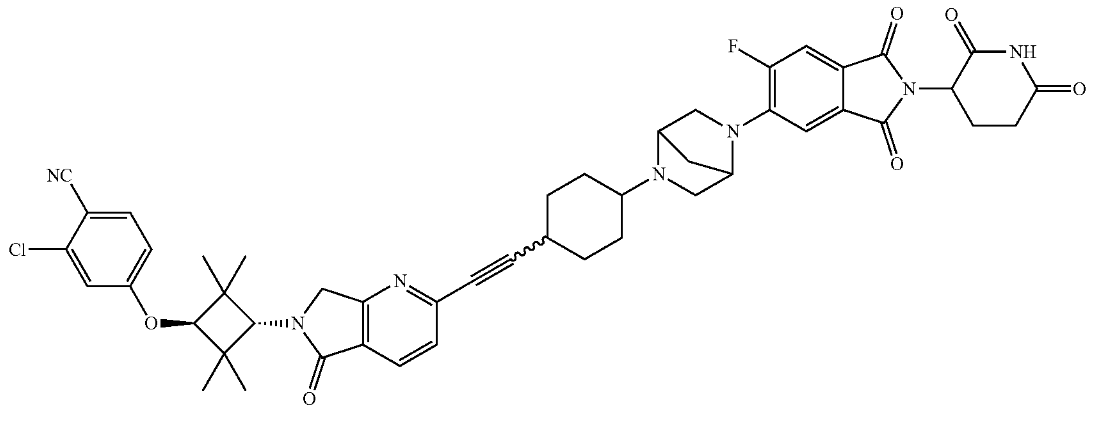

-continued
344
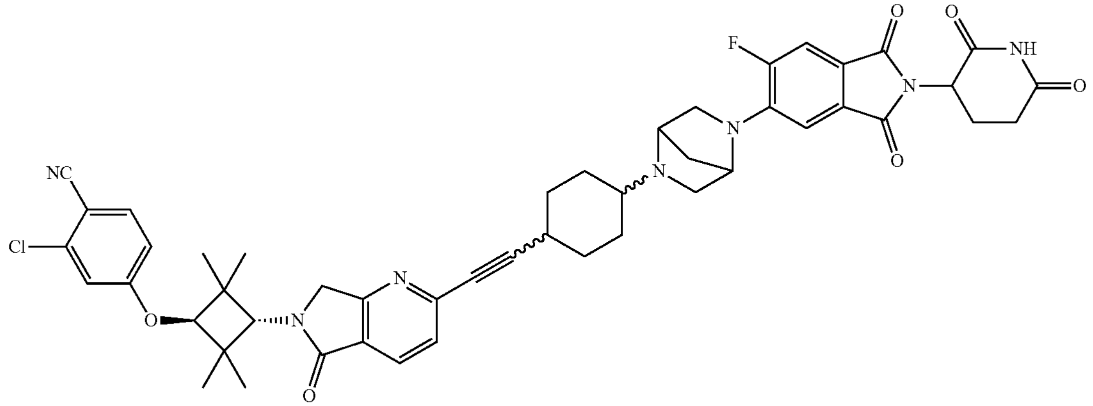
345
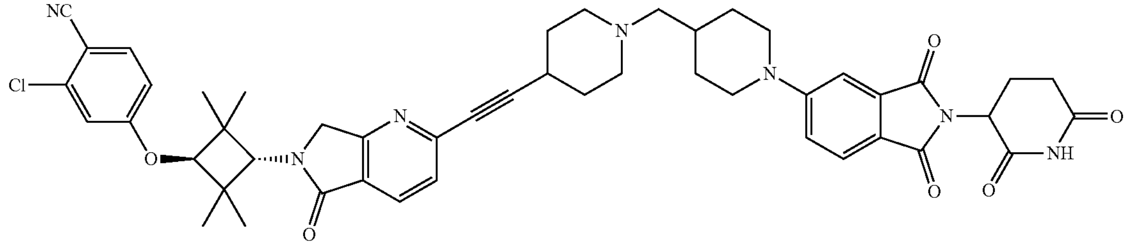
346
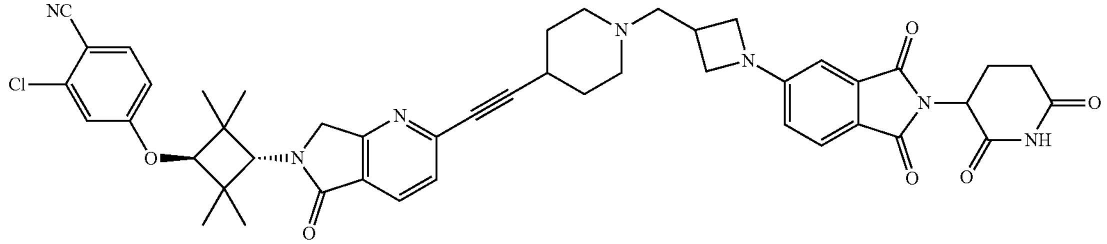
347
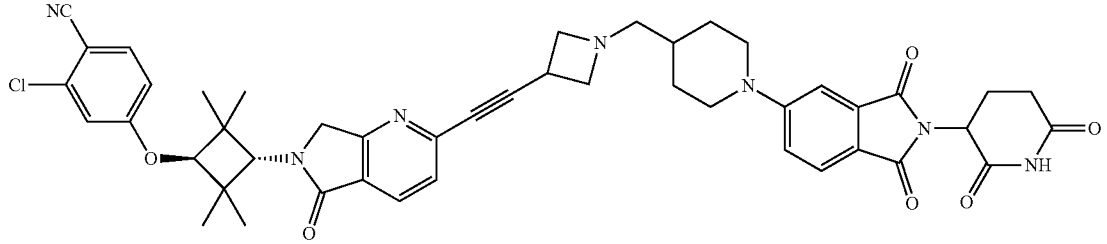
348
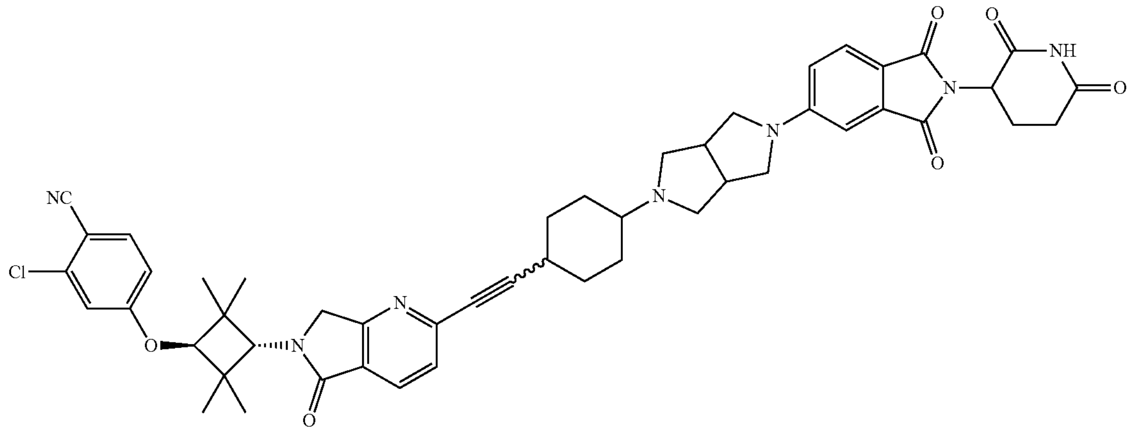

-continued
349
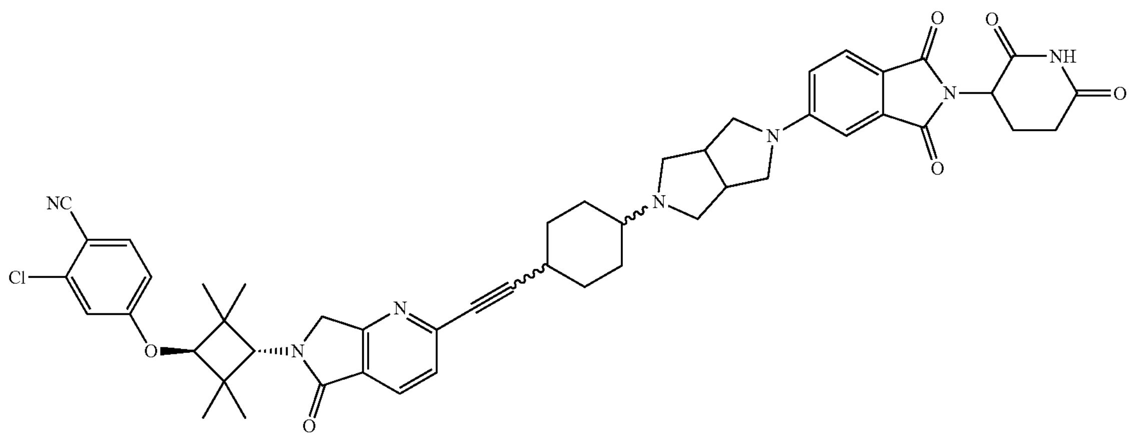
350
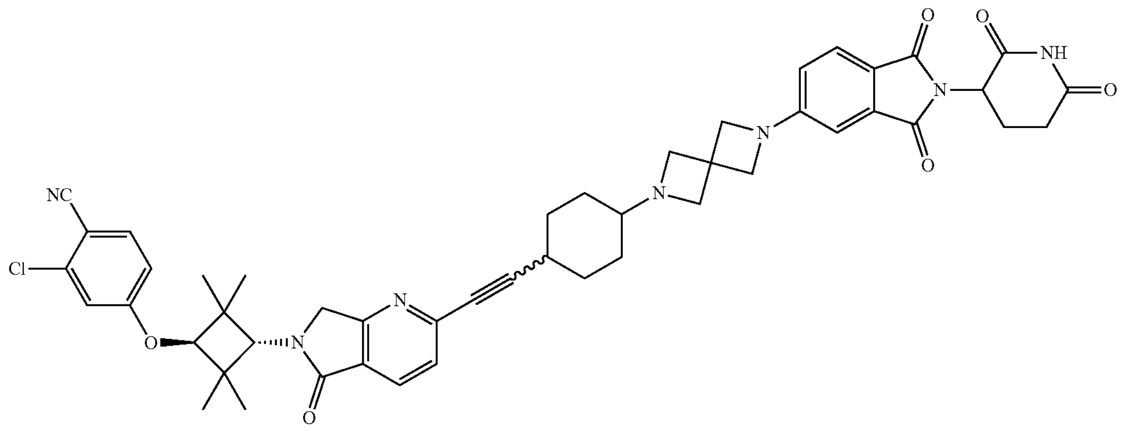
351
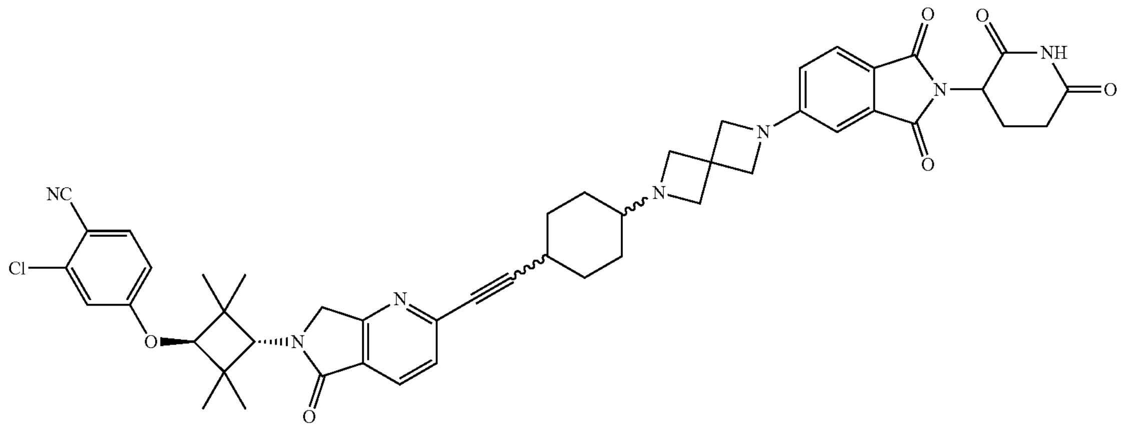

-continued
352
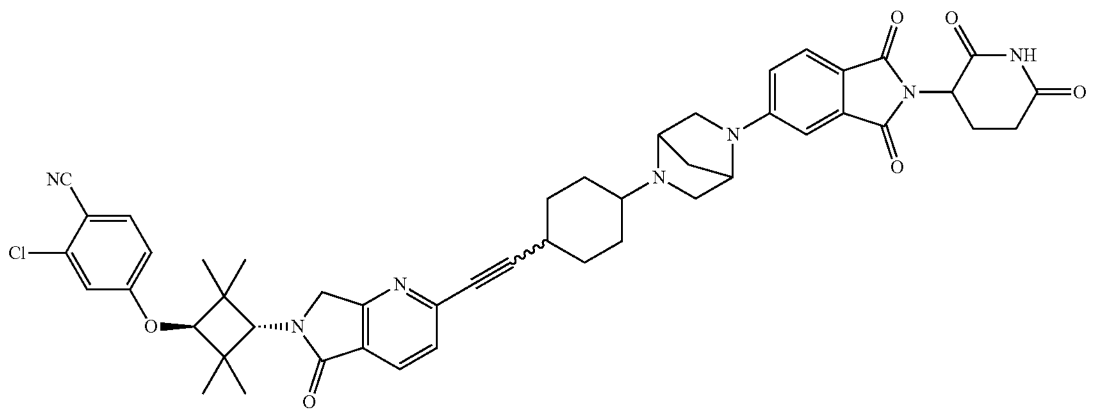
353
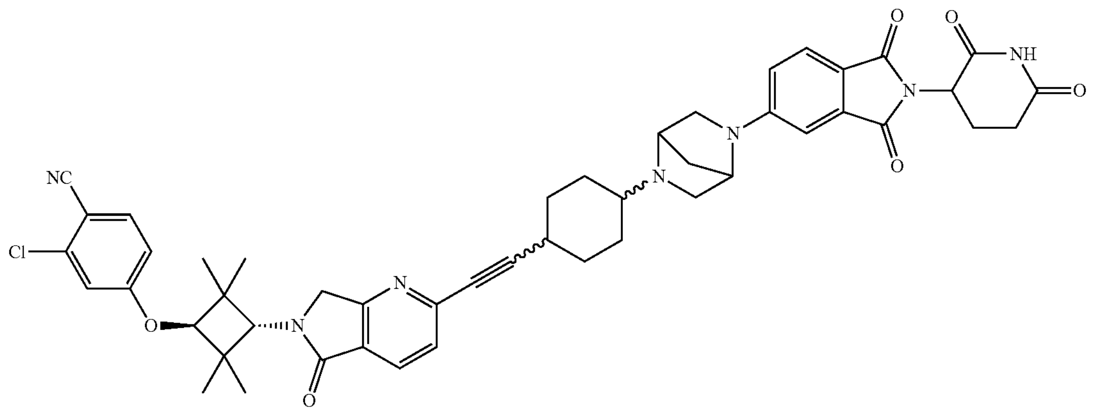
354
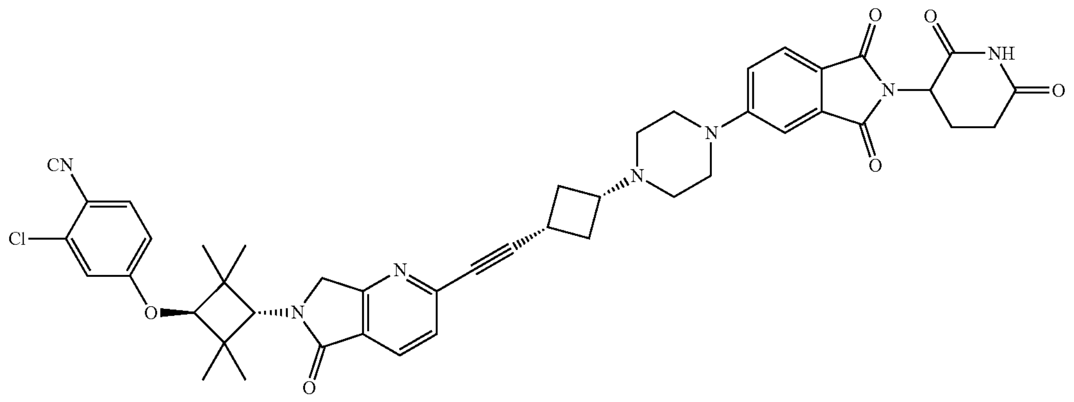
355
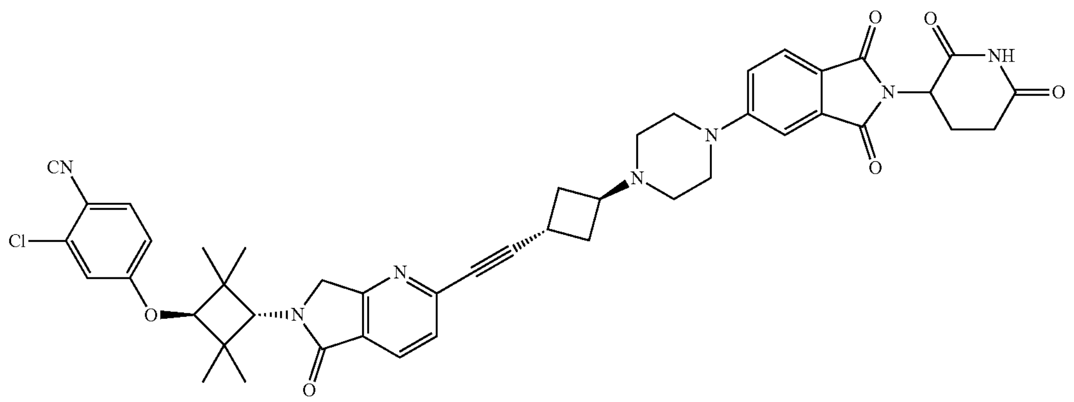

-continued
356
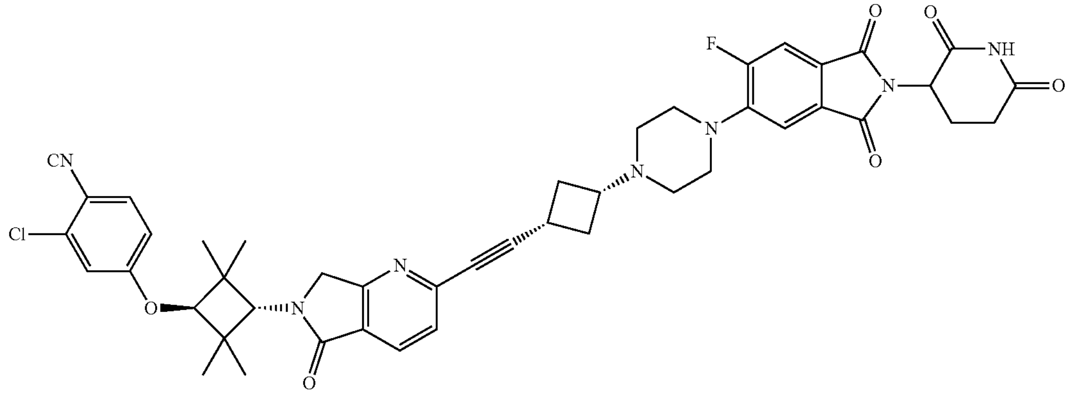
357
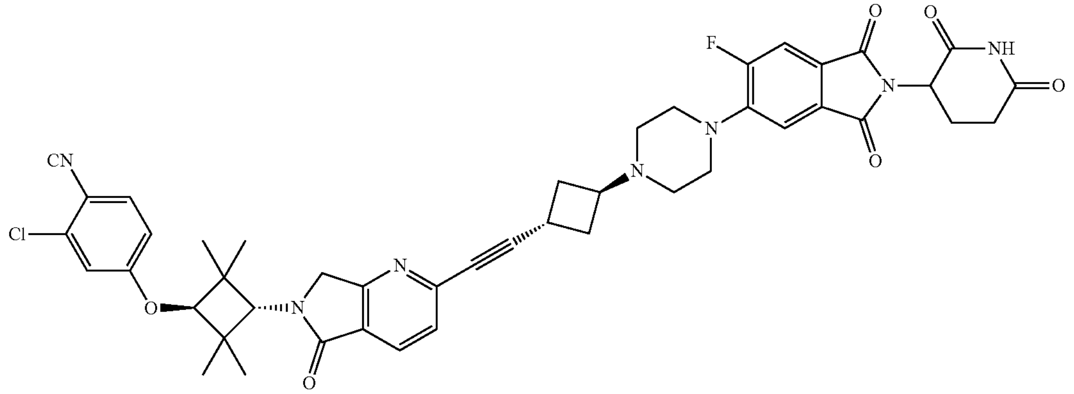
358
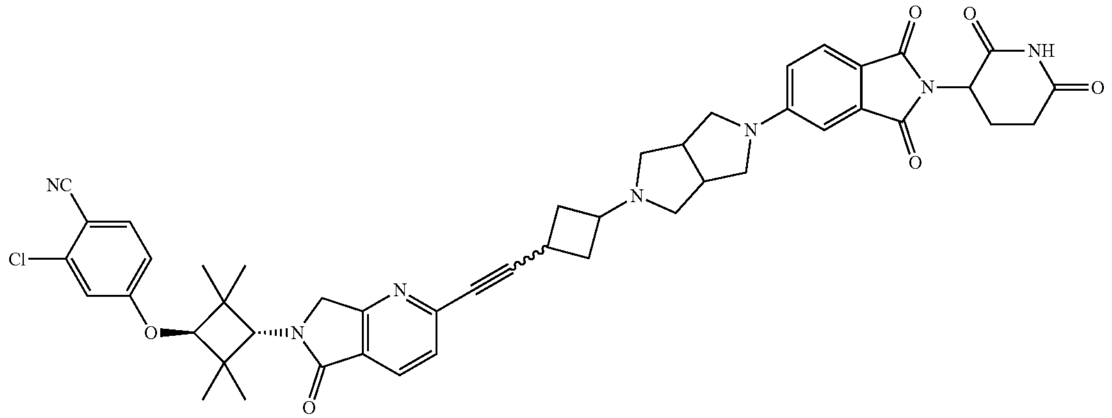
359
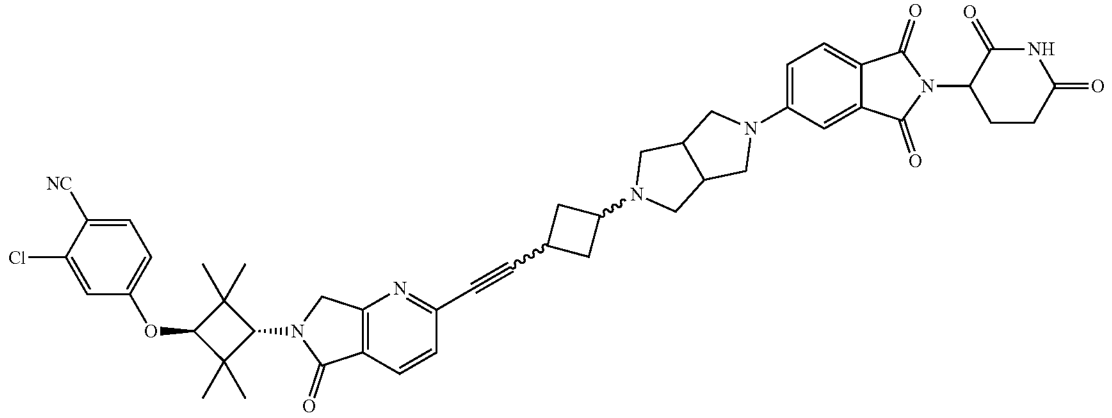

-continued
360
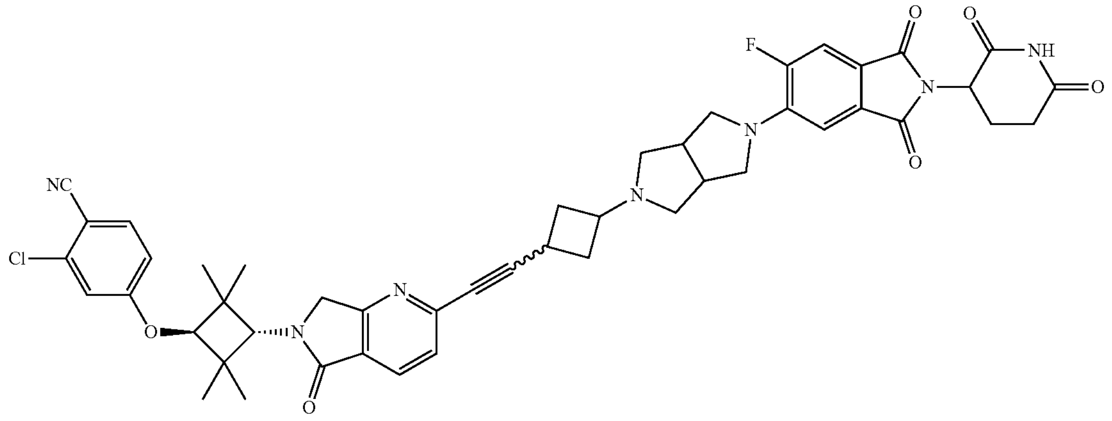
361
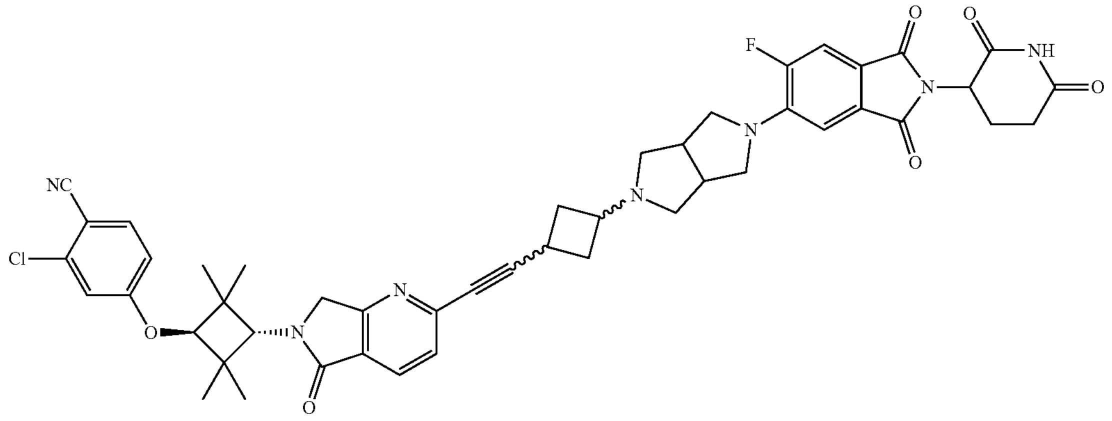
362
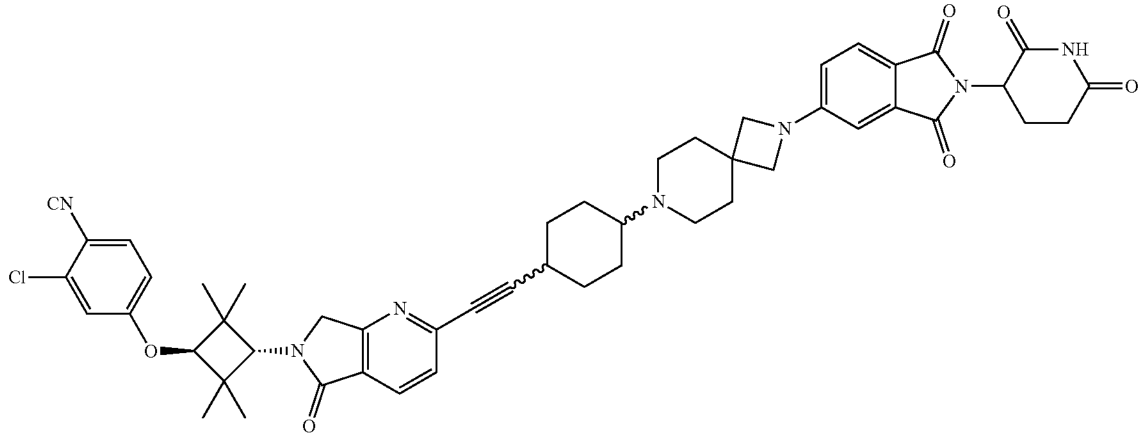

-continued
363
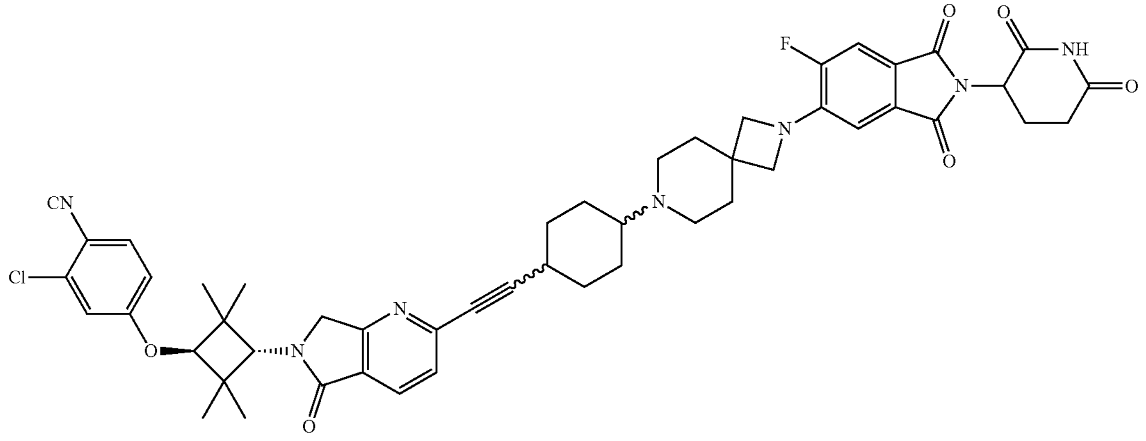
364
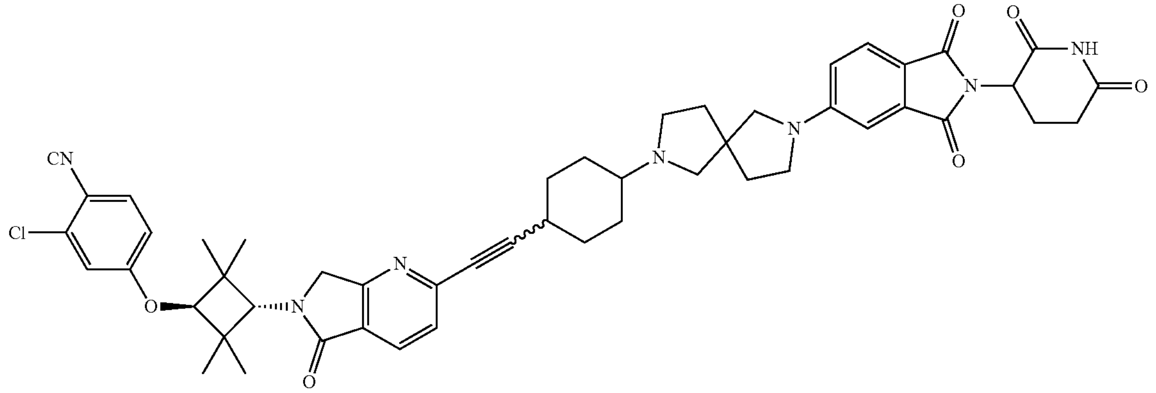
365
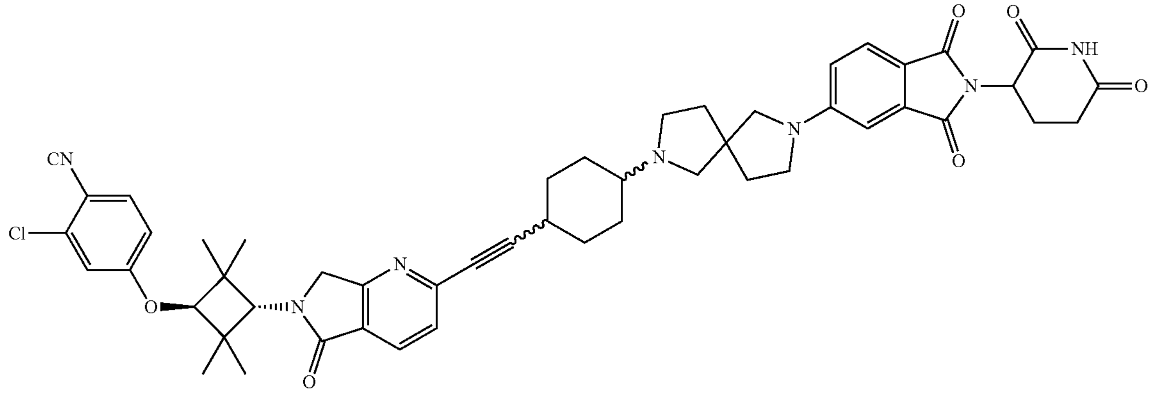
366
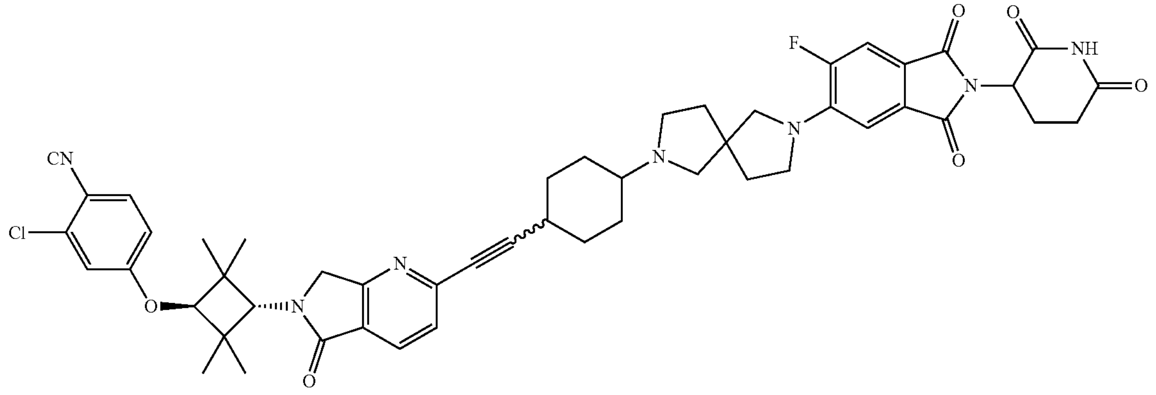

-continued
367
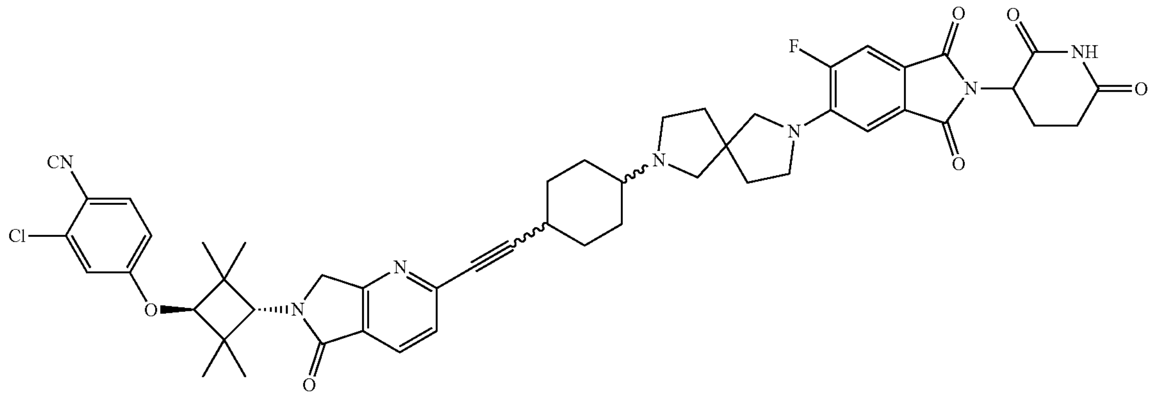
368
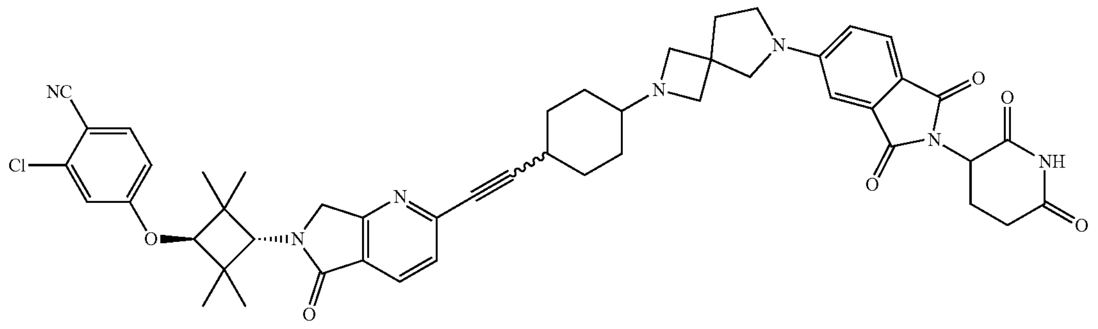
369
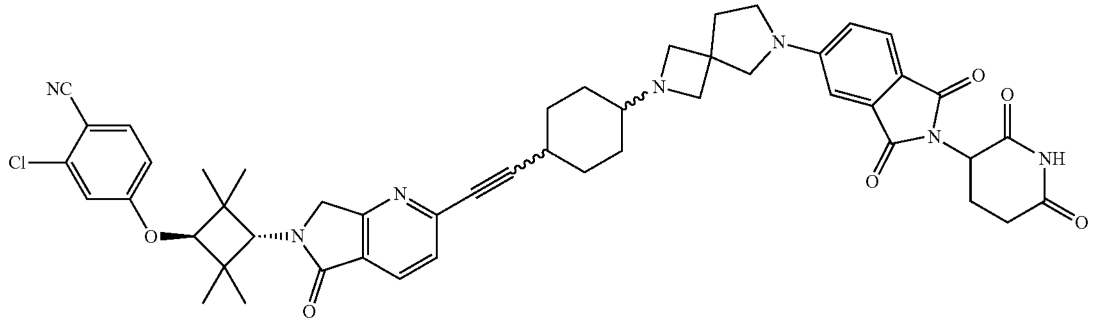
370
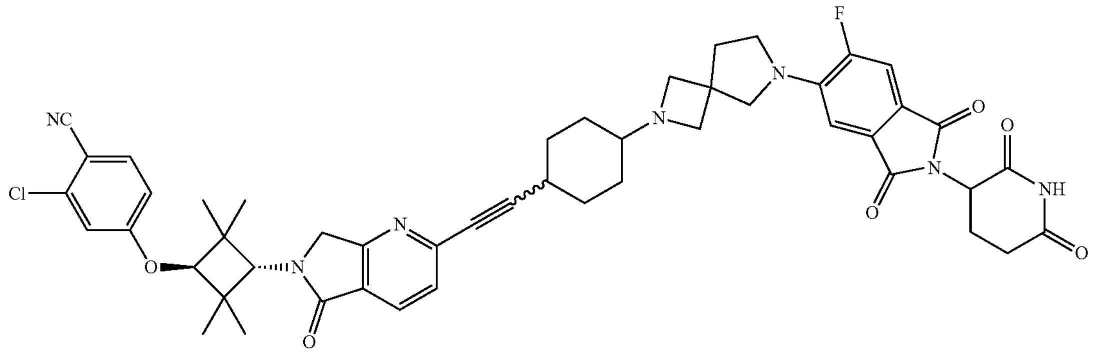

-continued
371
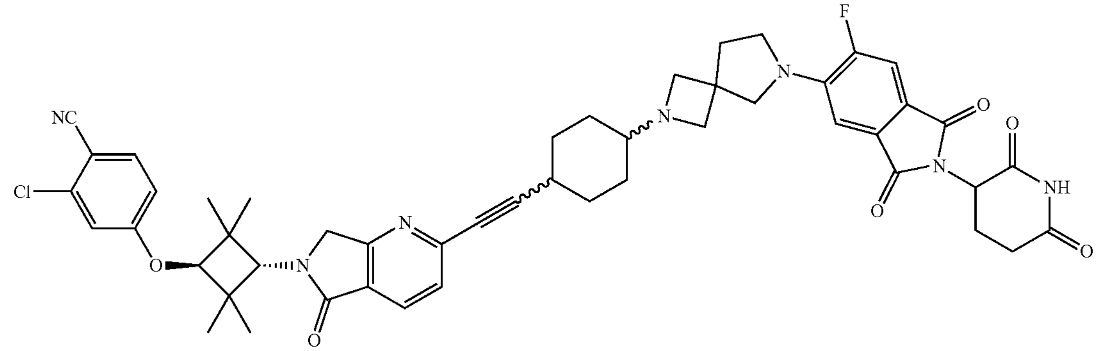
372
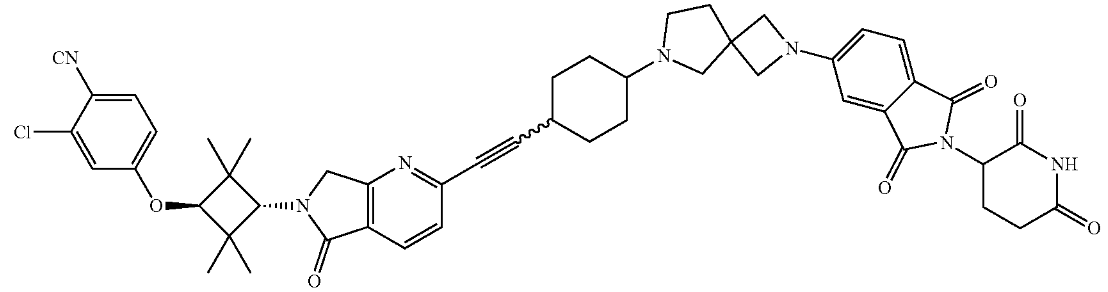
373
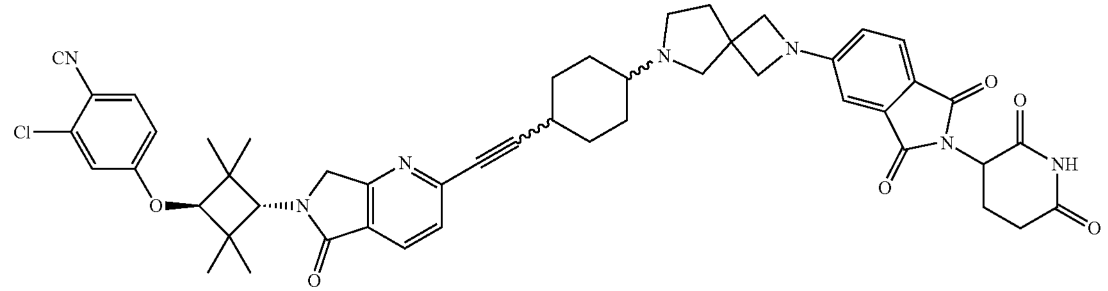
374
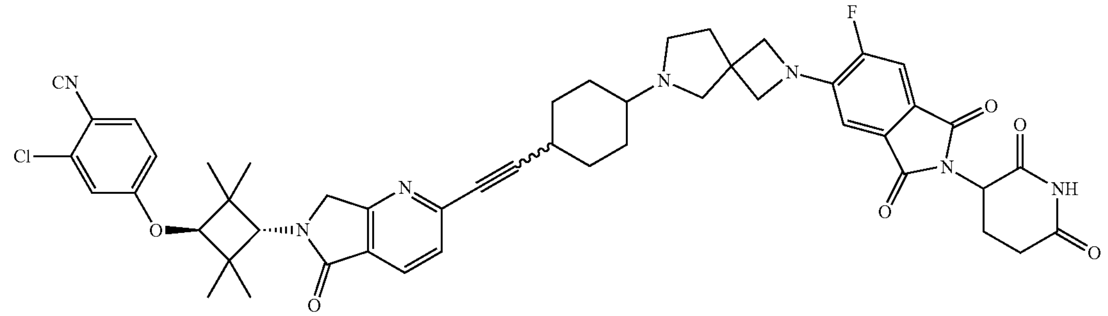
375
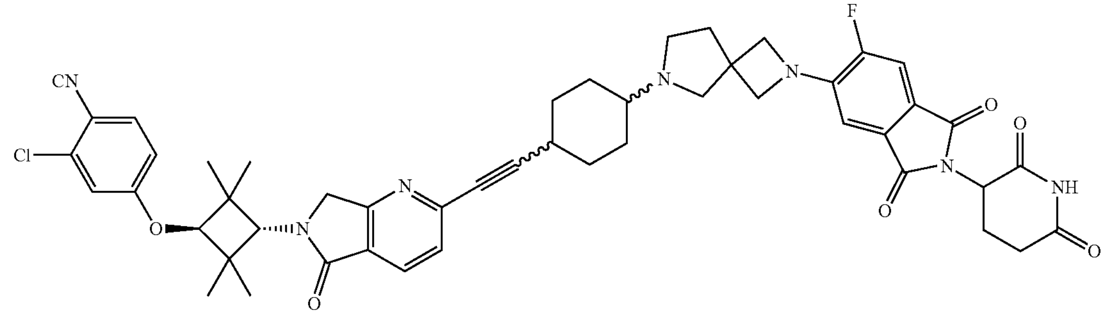

-continued
376
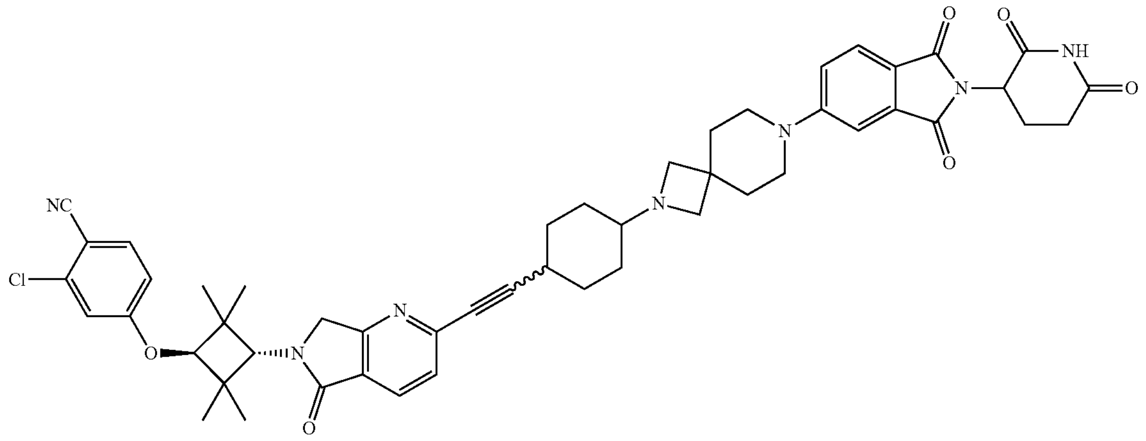
377
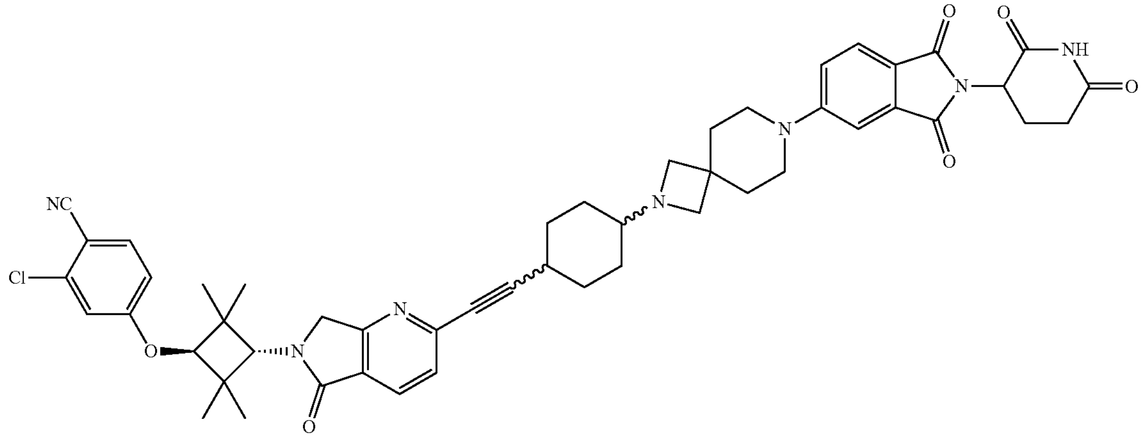
378
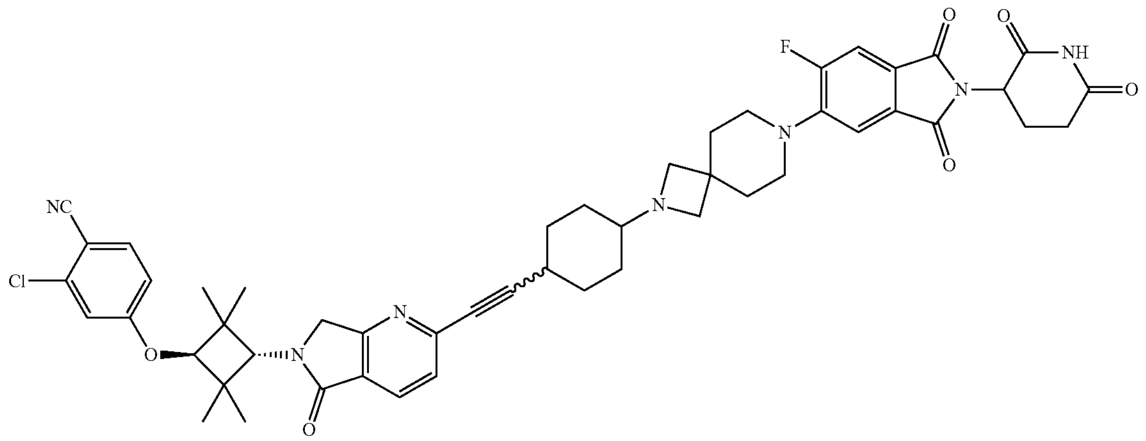

-continued
379
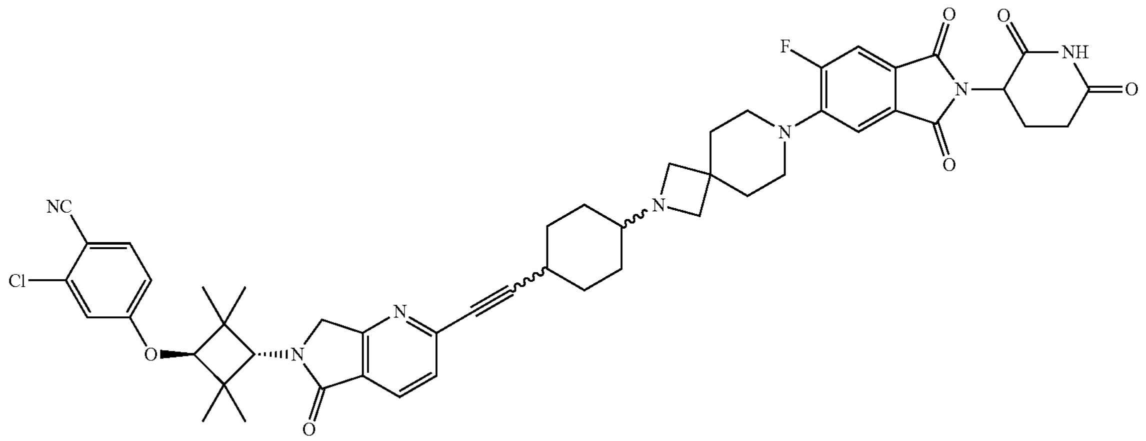
380
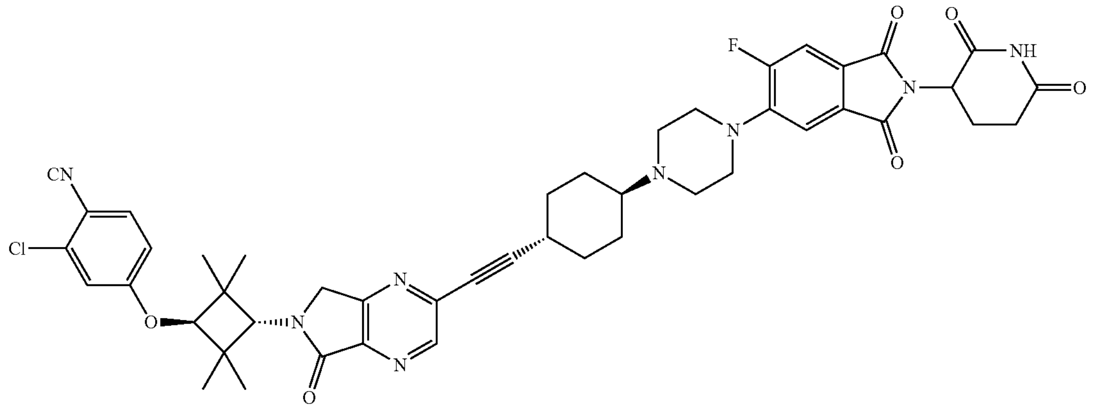
381
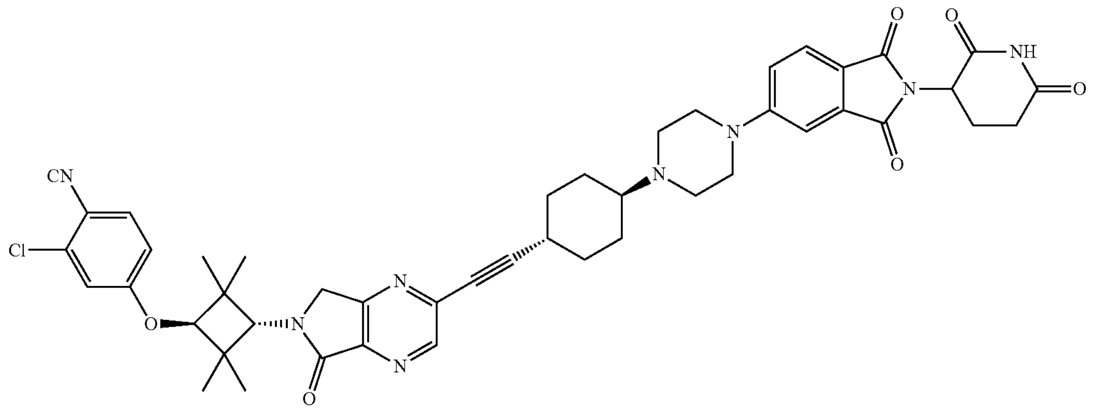
382
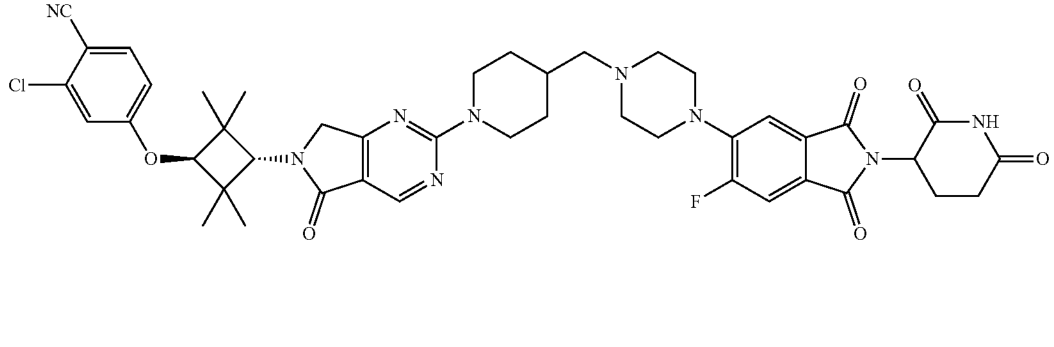

-continued
383
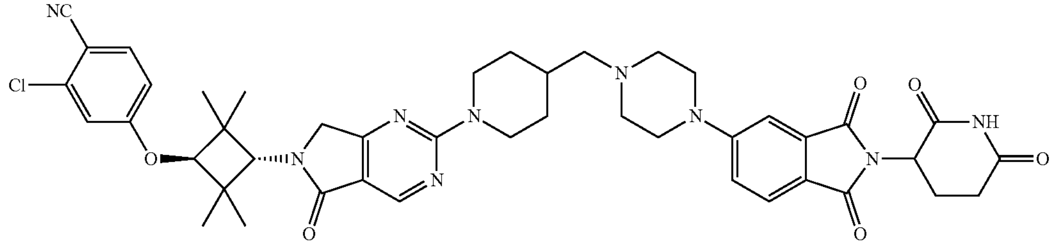
384
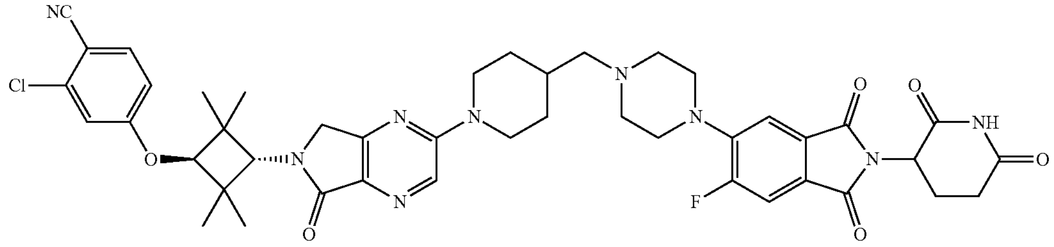
385
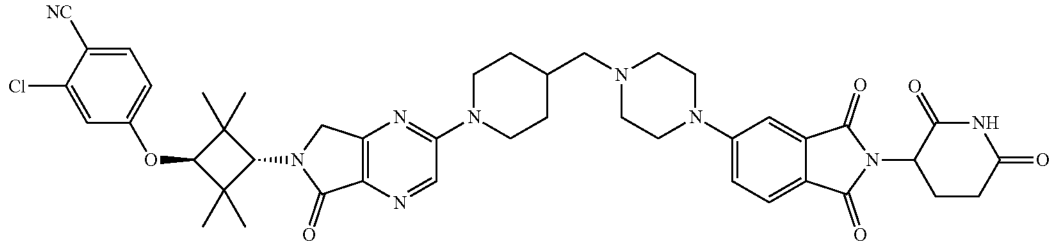
386
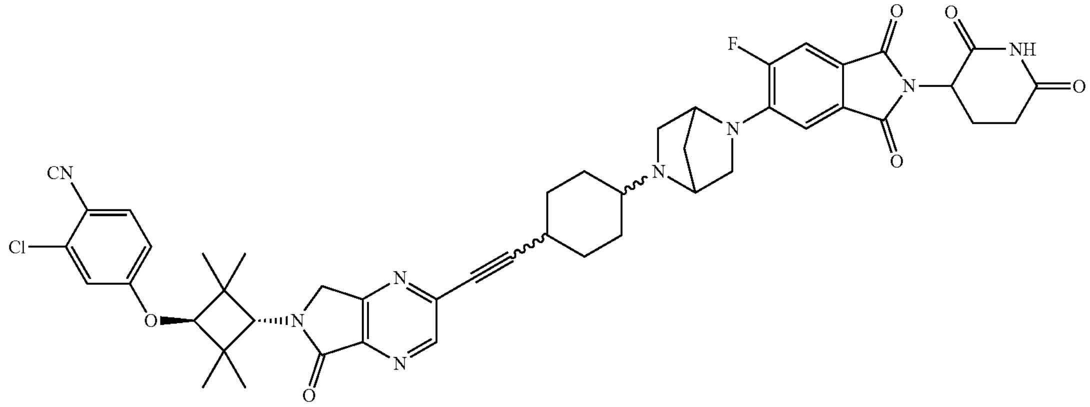
387
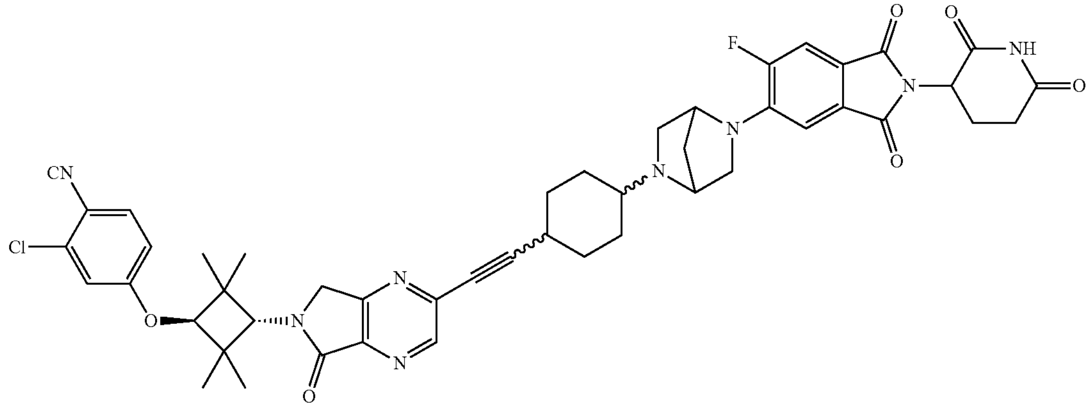

-continued
388
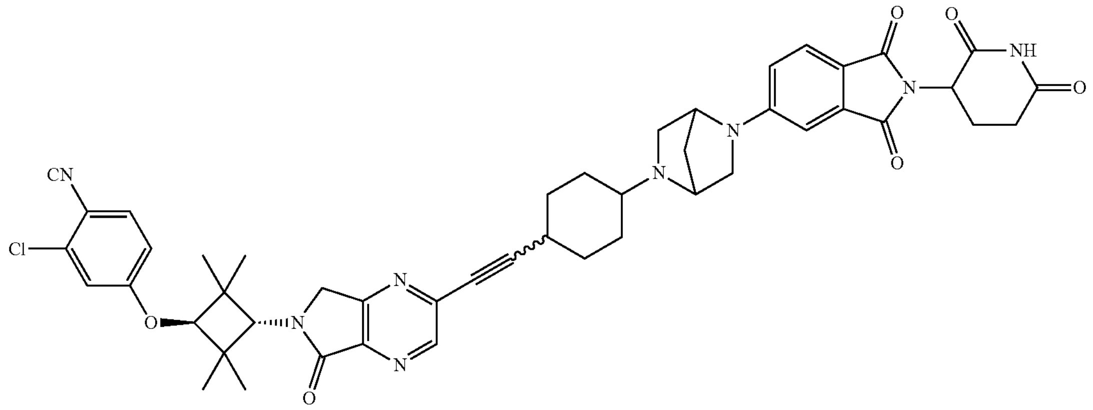
389
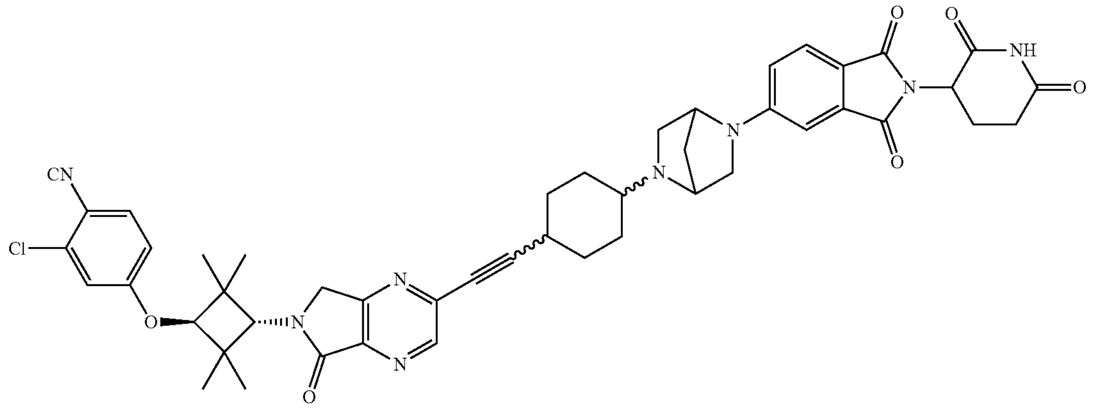
390
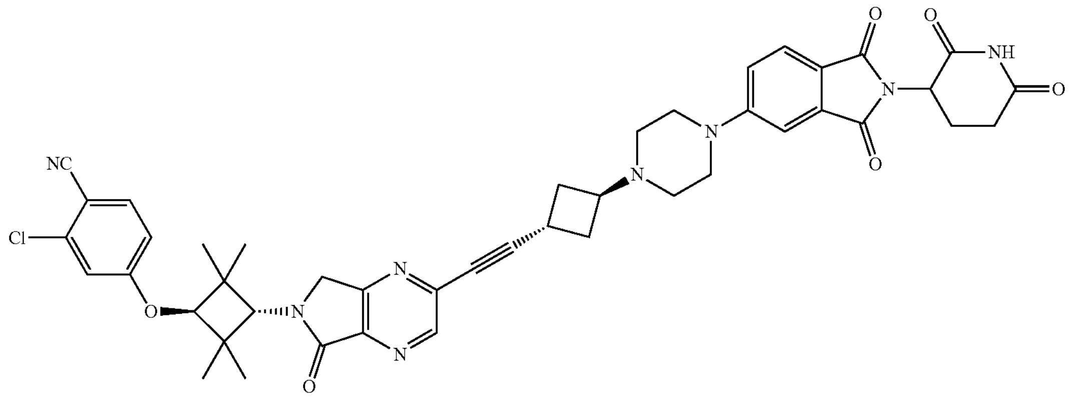
391
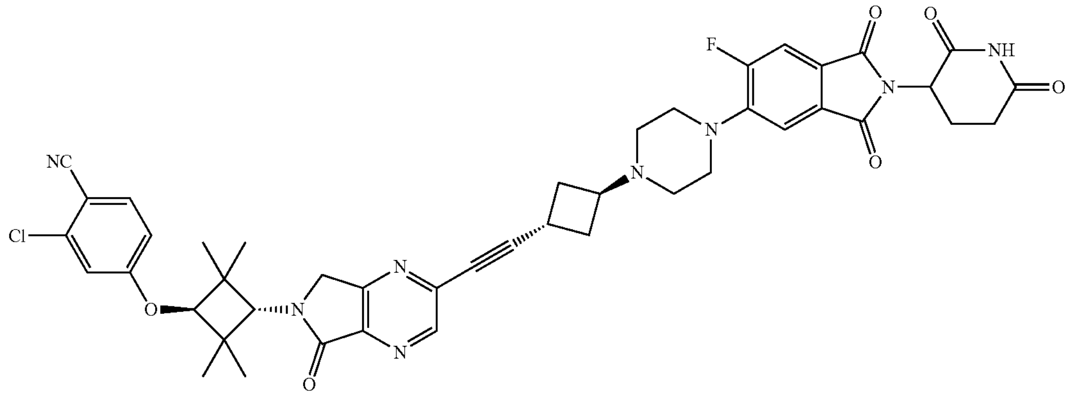

-continued
392
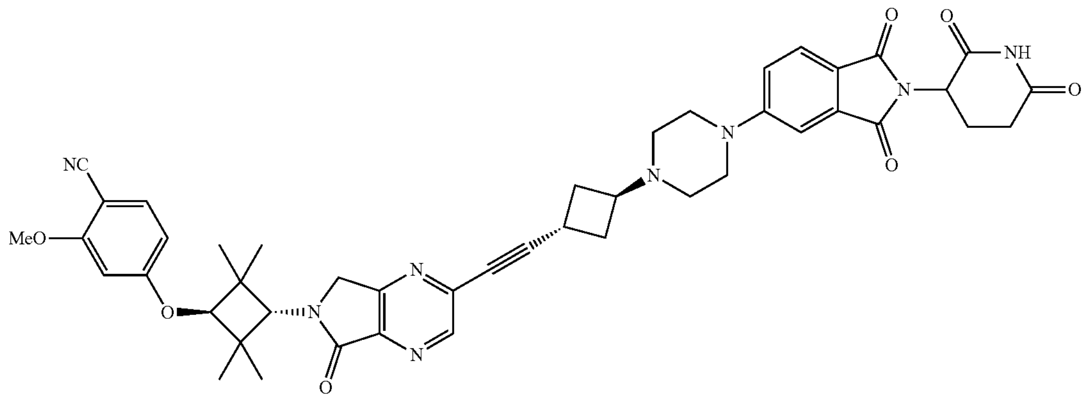
393
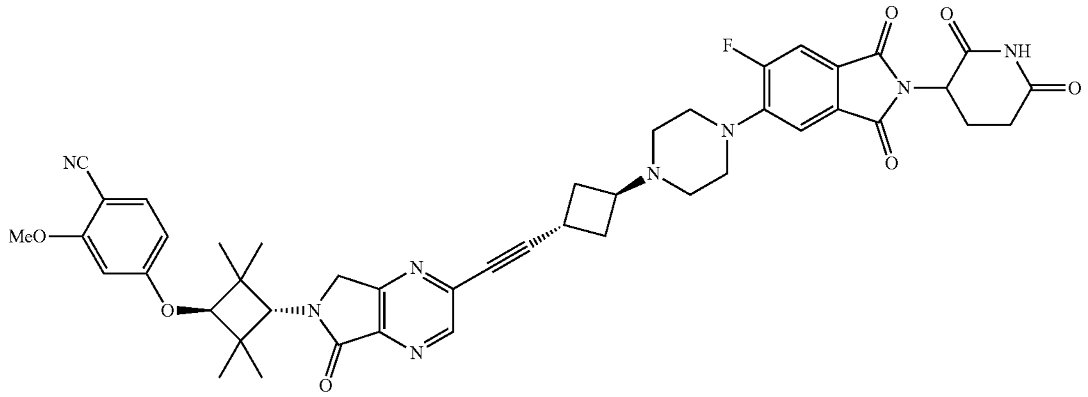
394
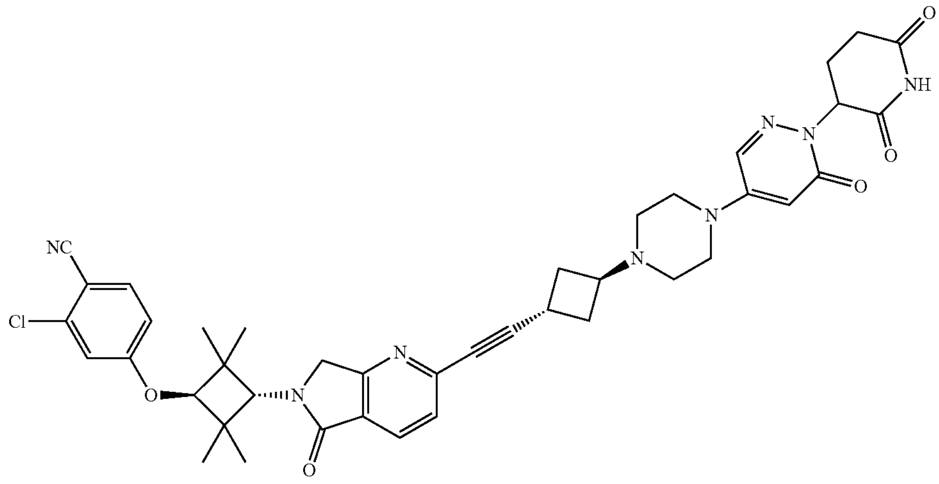

-continued
395
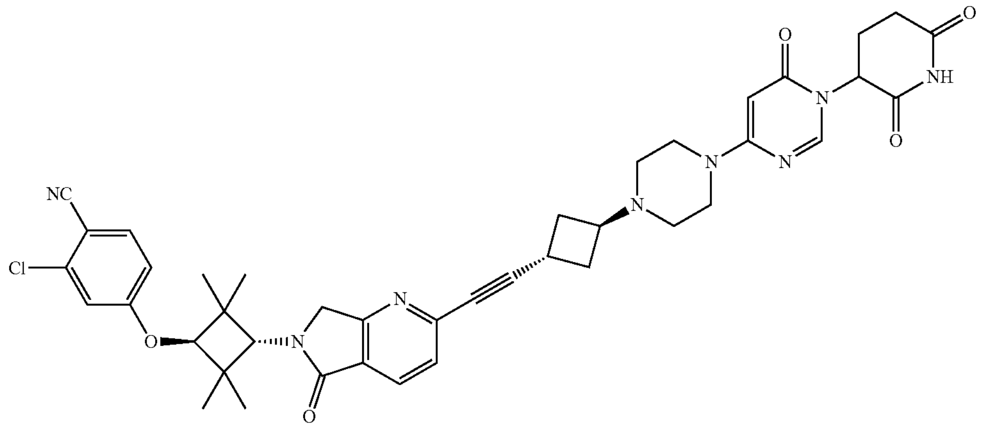
396
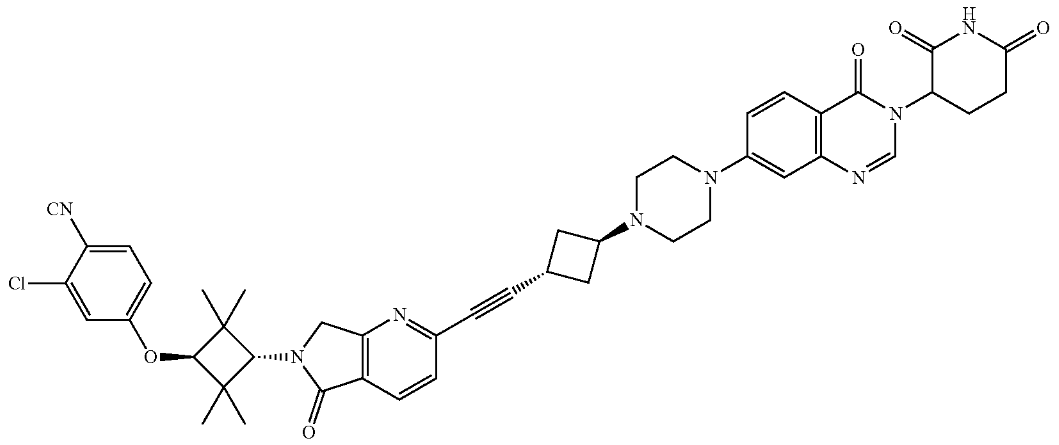
397
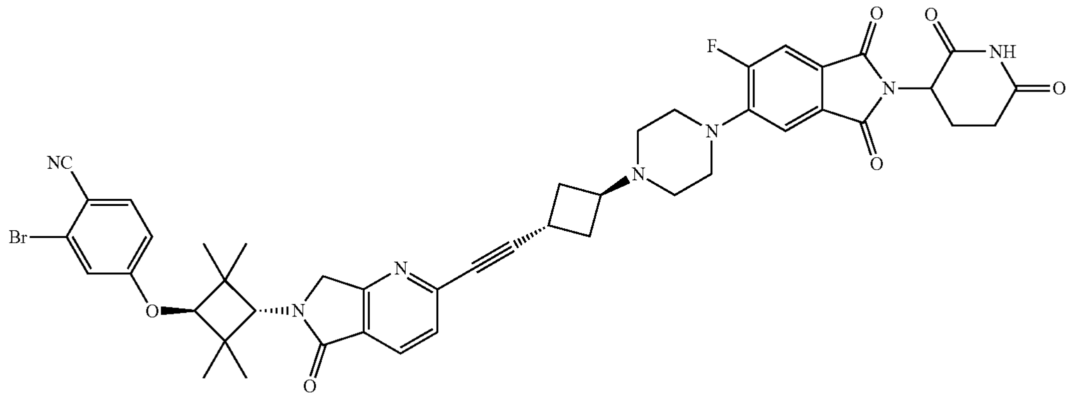

-continued
398
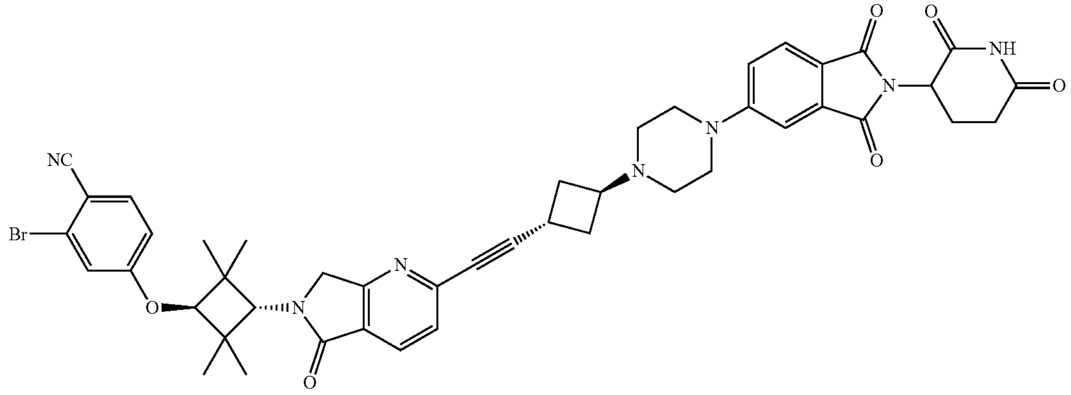
399
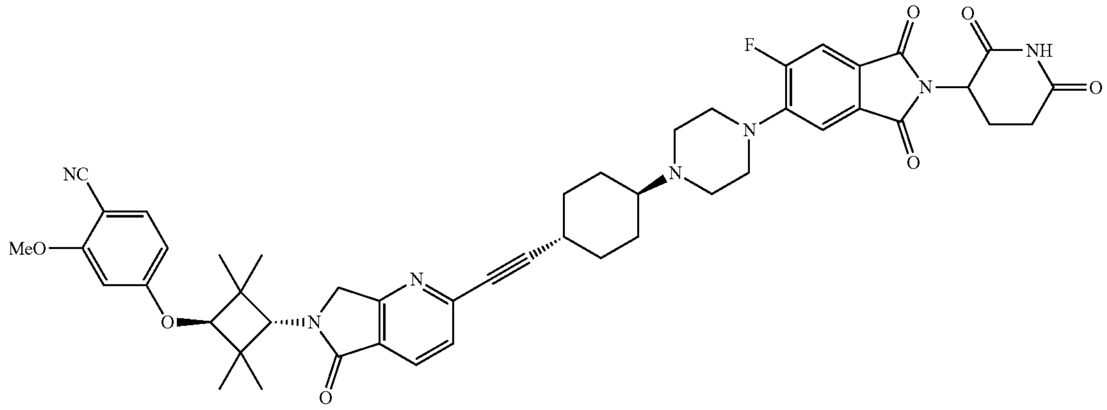
400
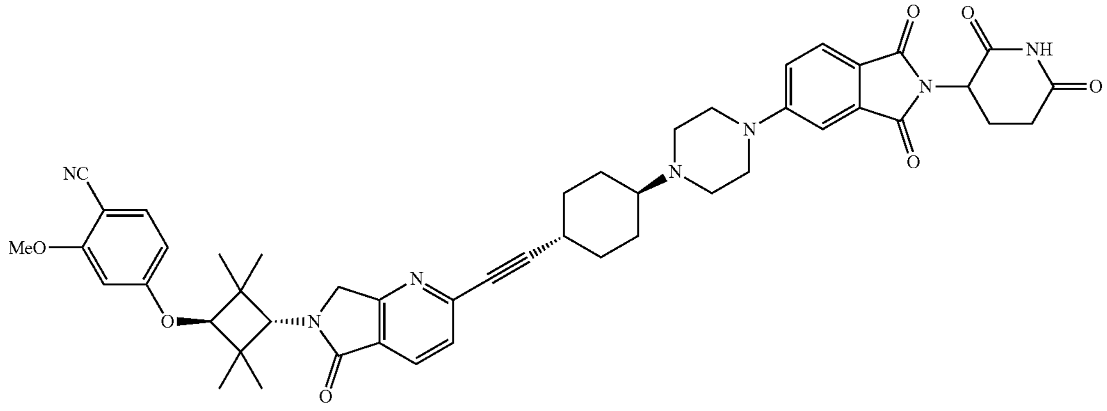
401
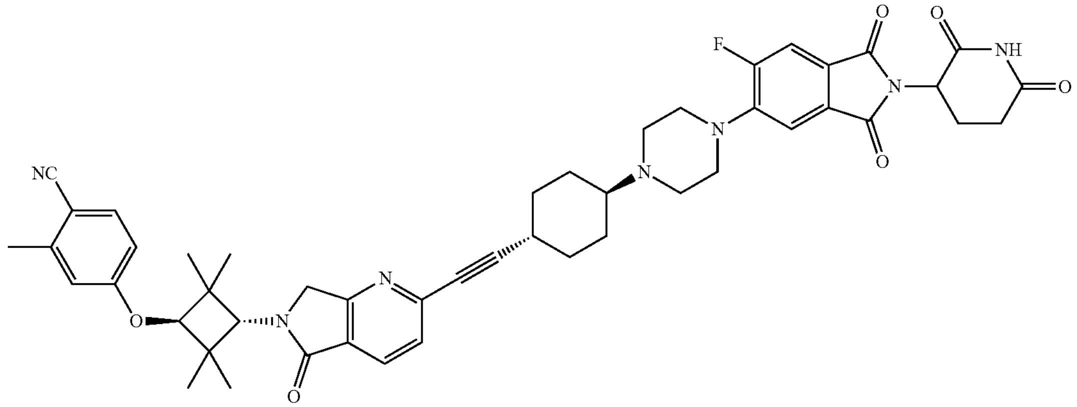

-continued
402
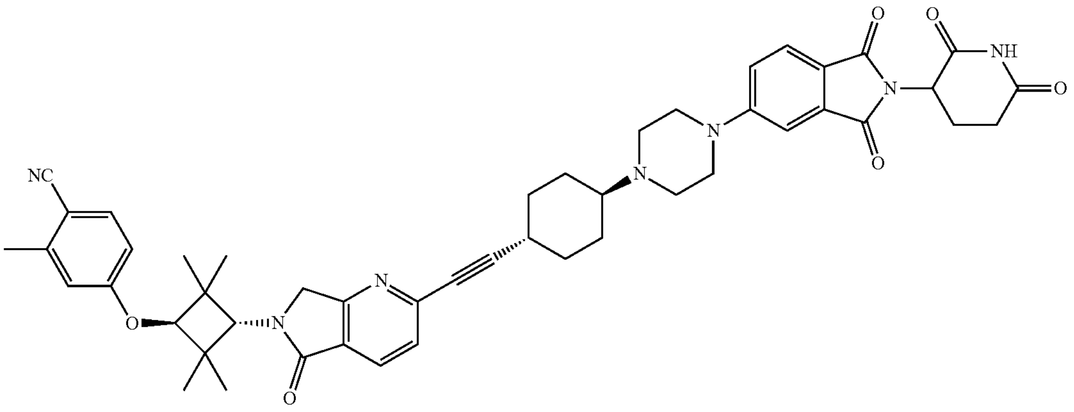
403
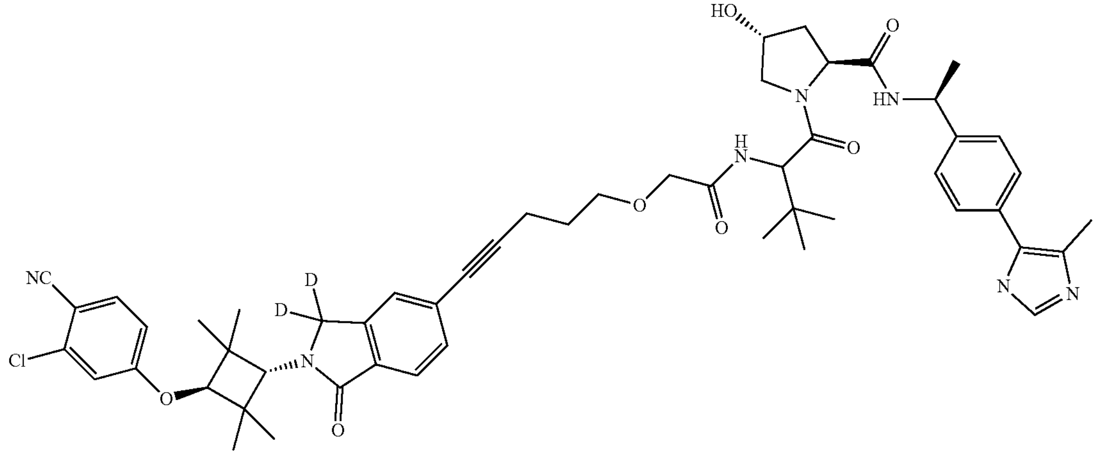
404
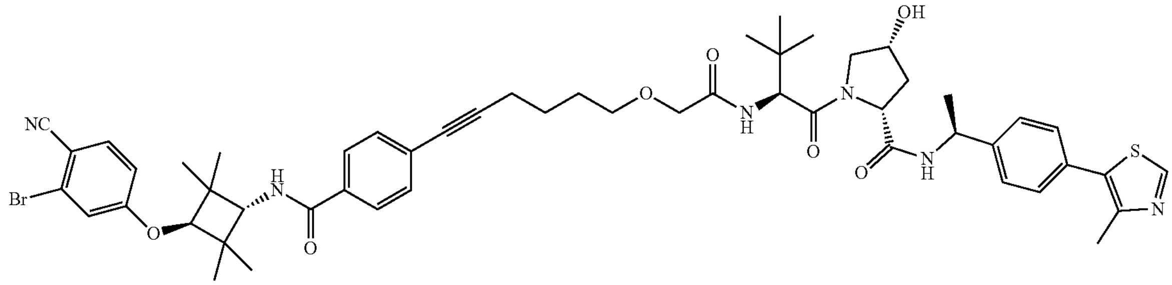
405
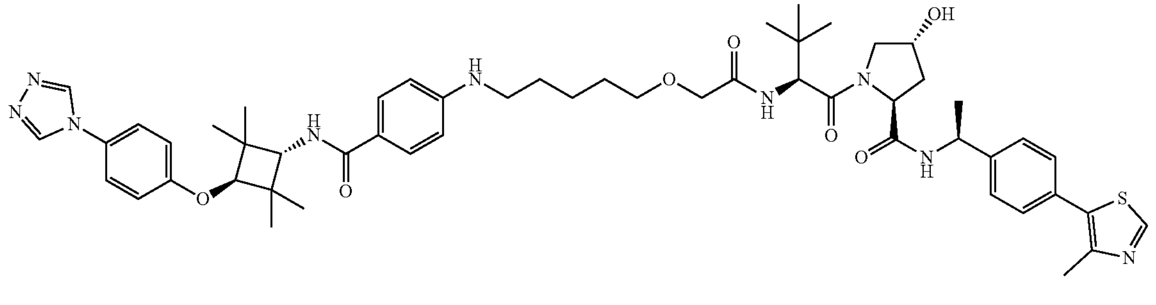

-continued
406
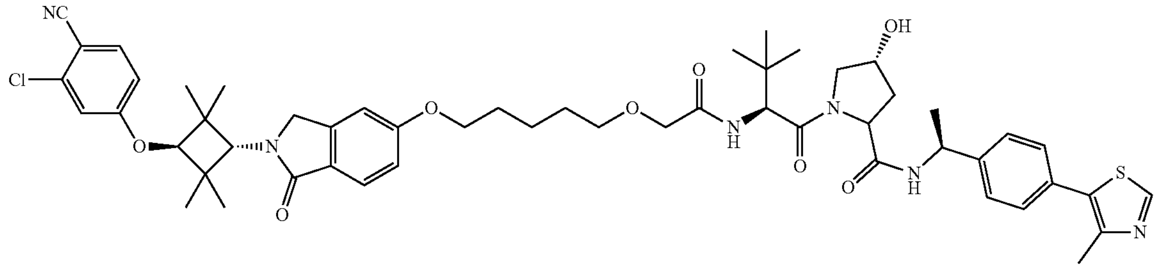
407
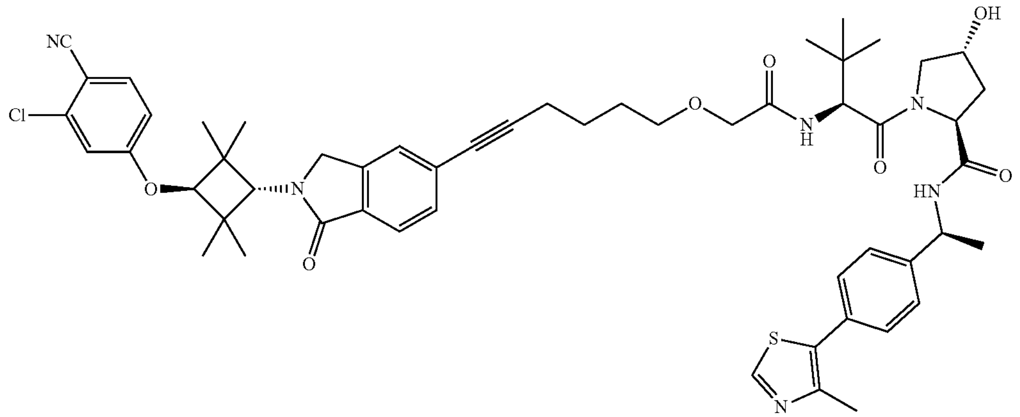
408
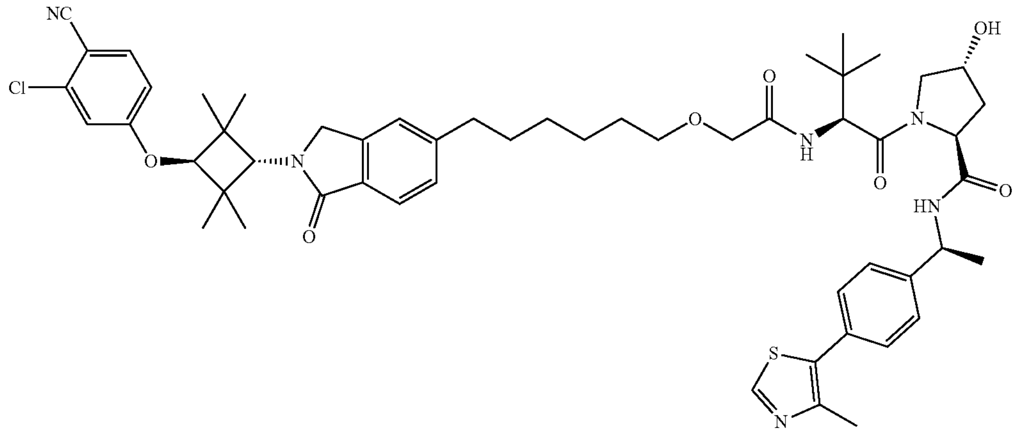
409
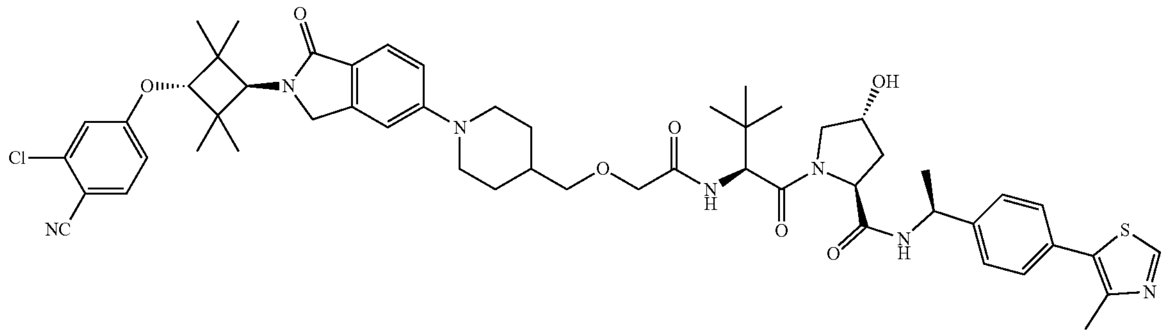

-continued
410
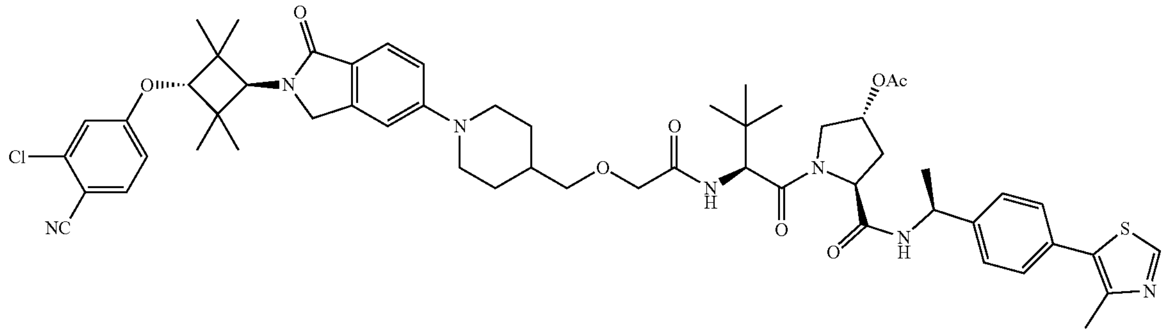
411
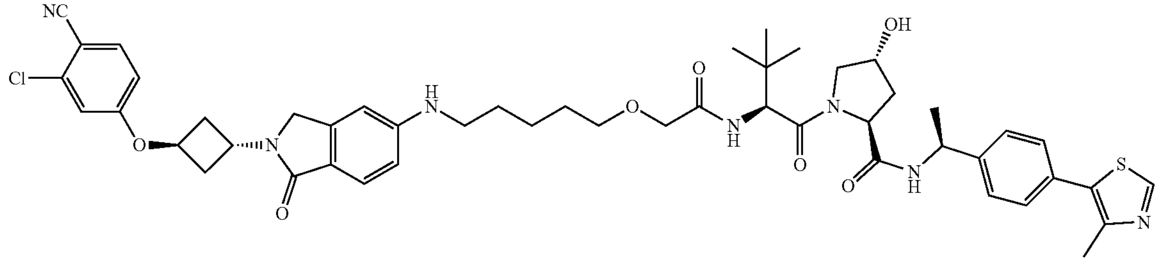
412
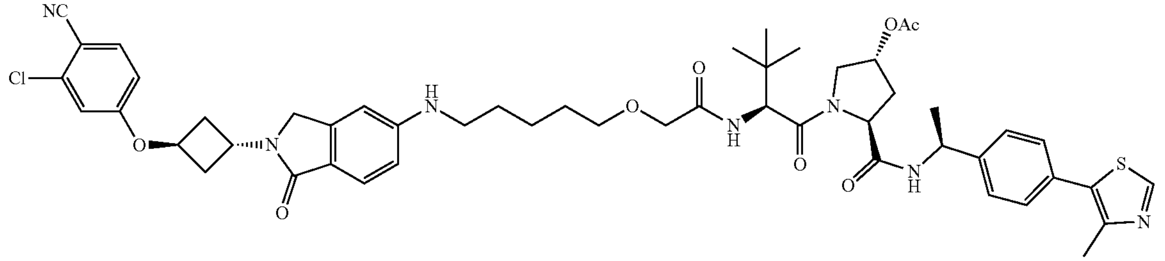
413
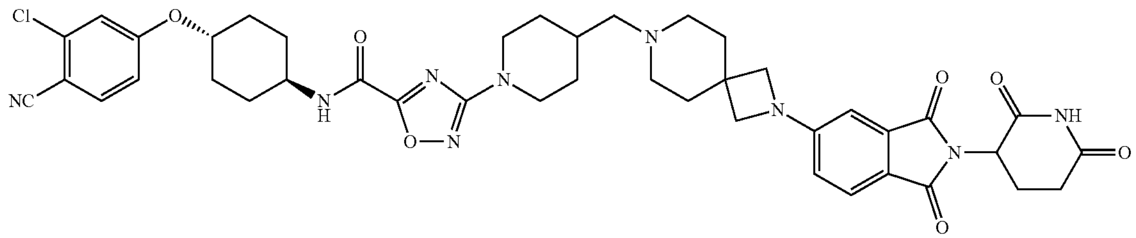
414
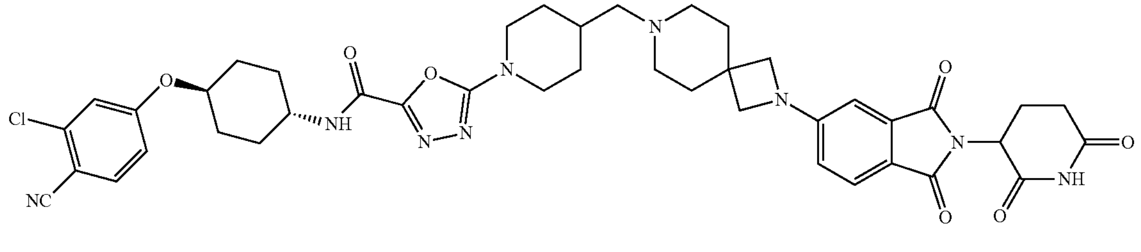
415
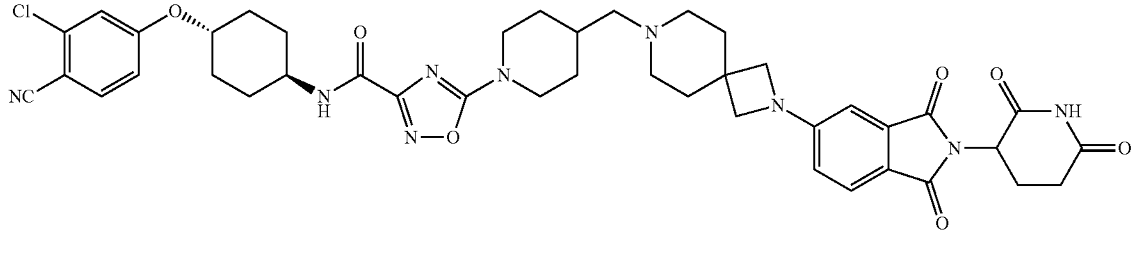

-continued
416
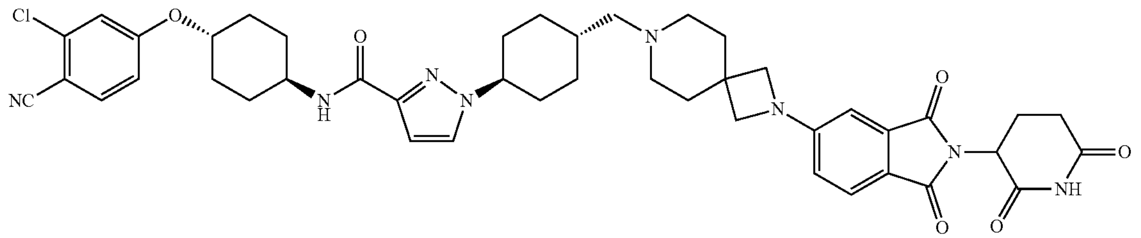
417
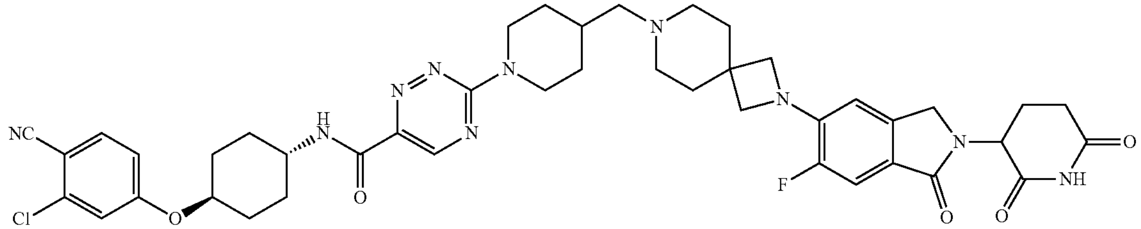
418
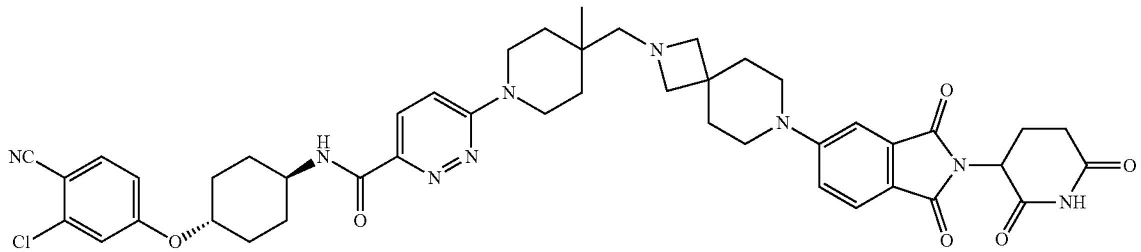
419
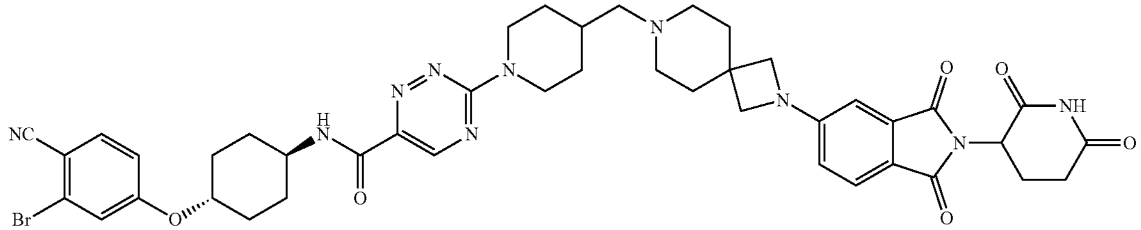
420
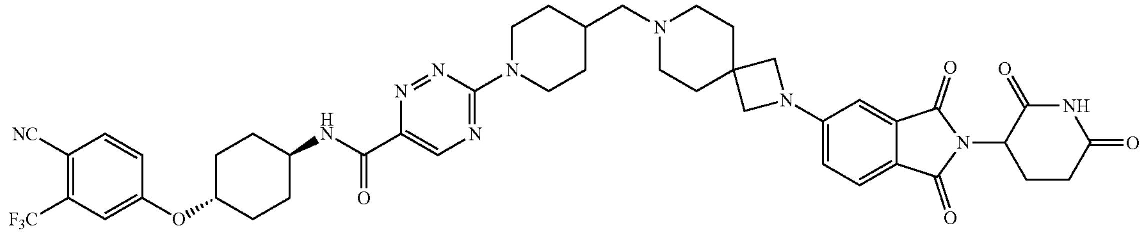
421
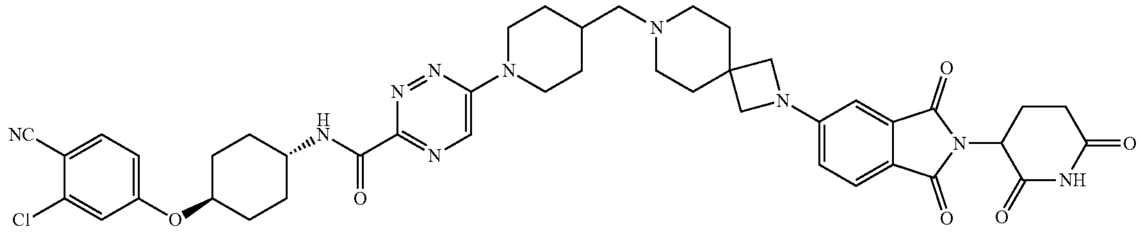

-continued
422
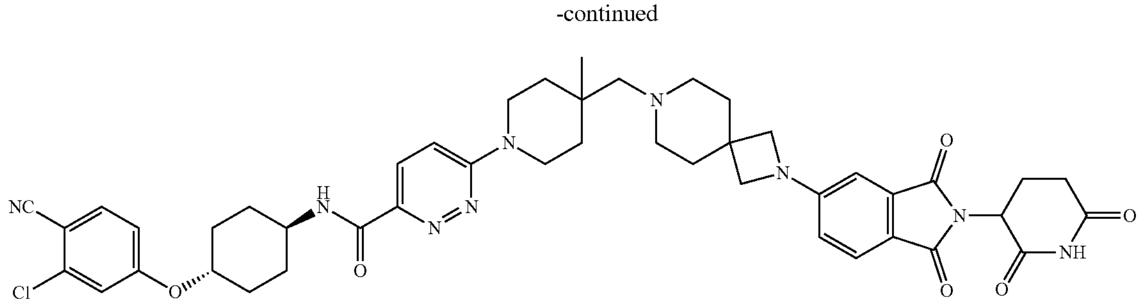
423
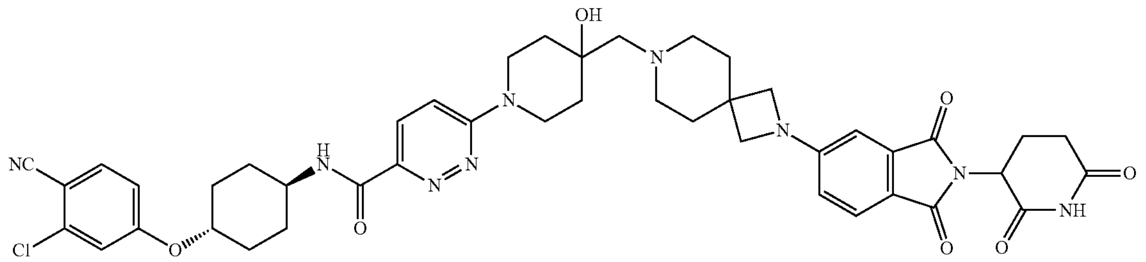
424
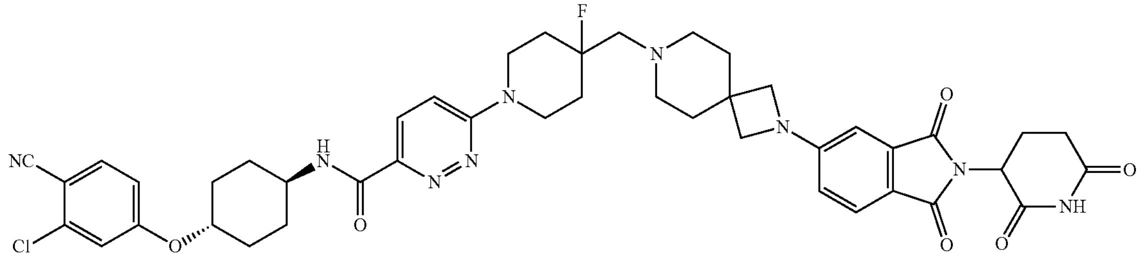
425
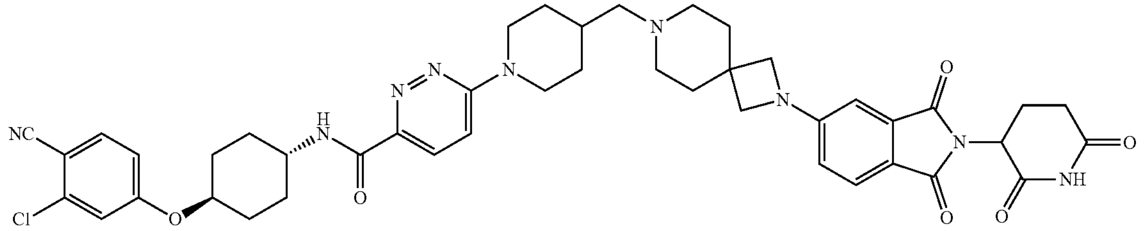
426
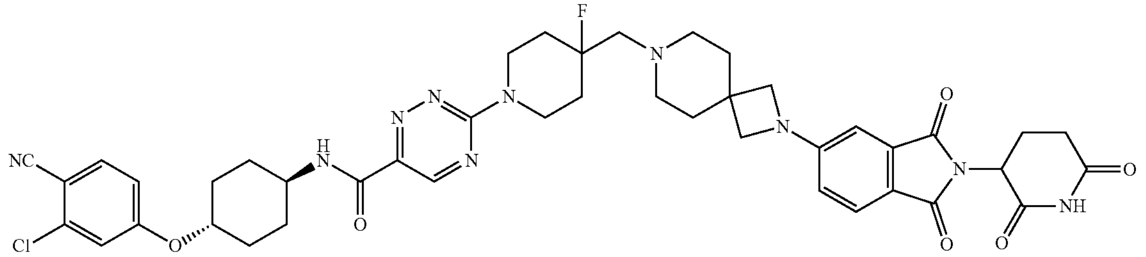
427
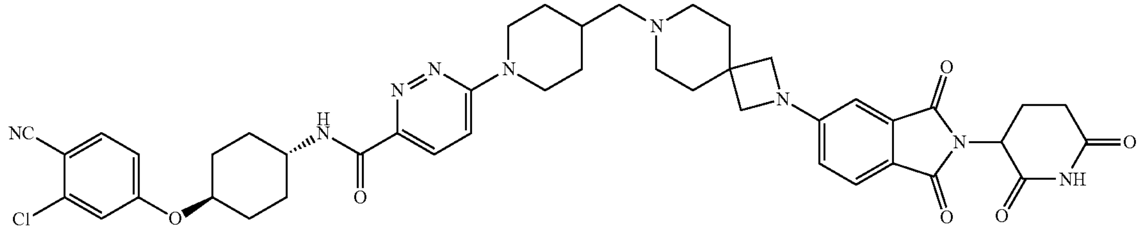

-continued
428
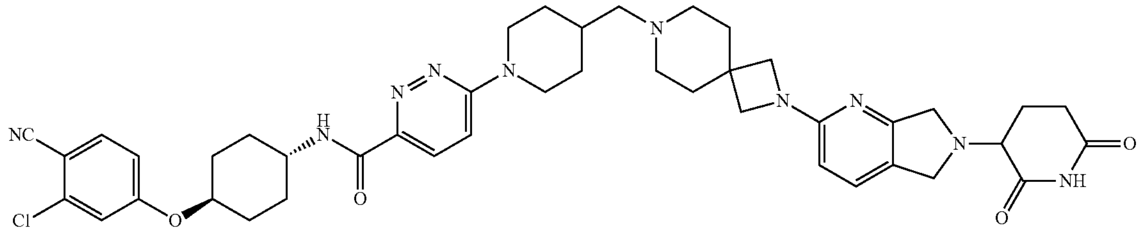
429
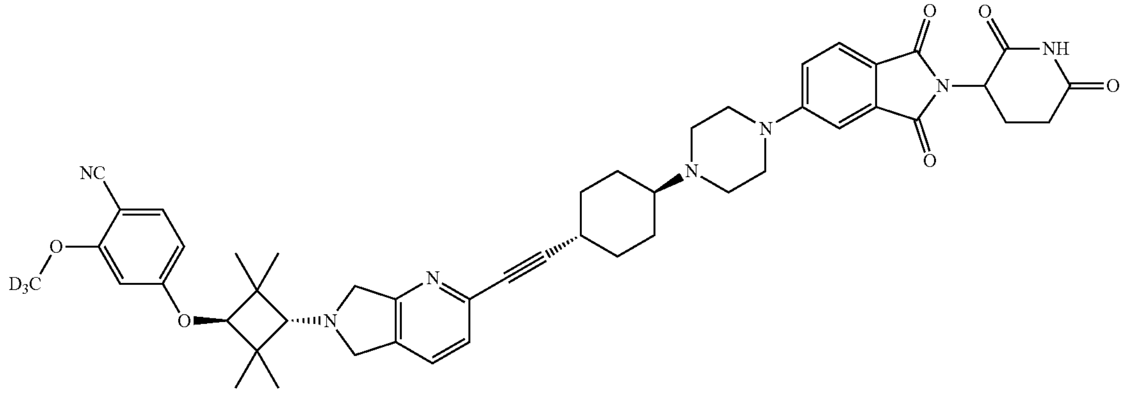
430
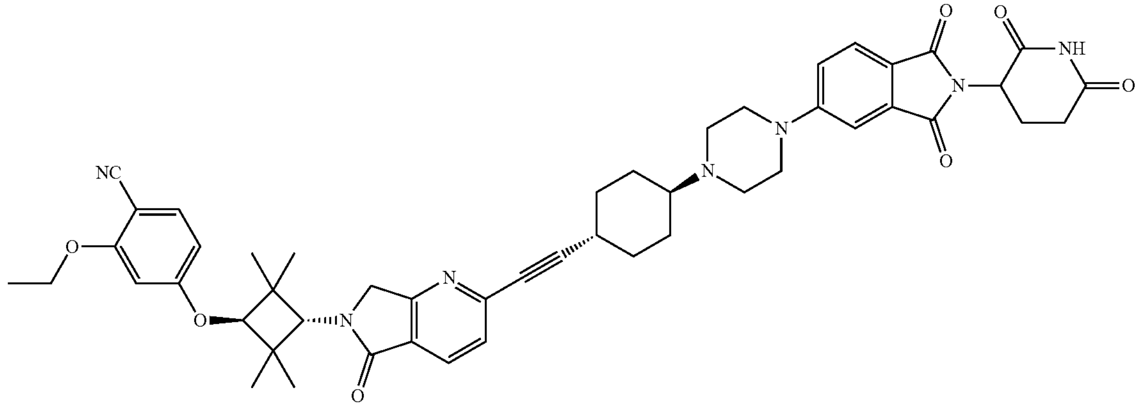
431
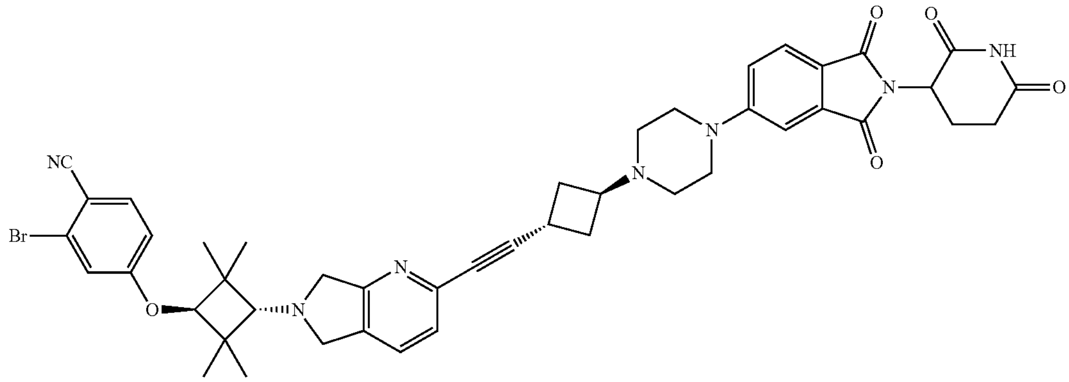

-continued

432

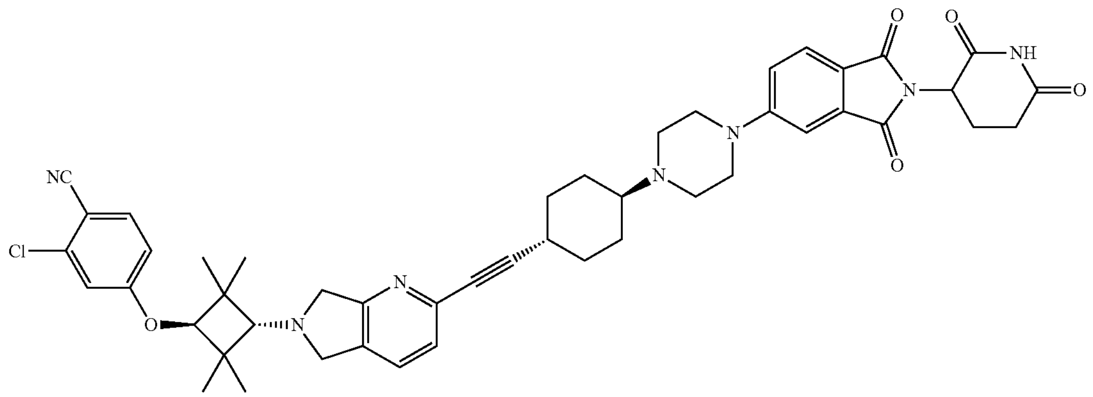

433

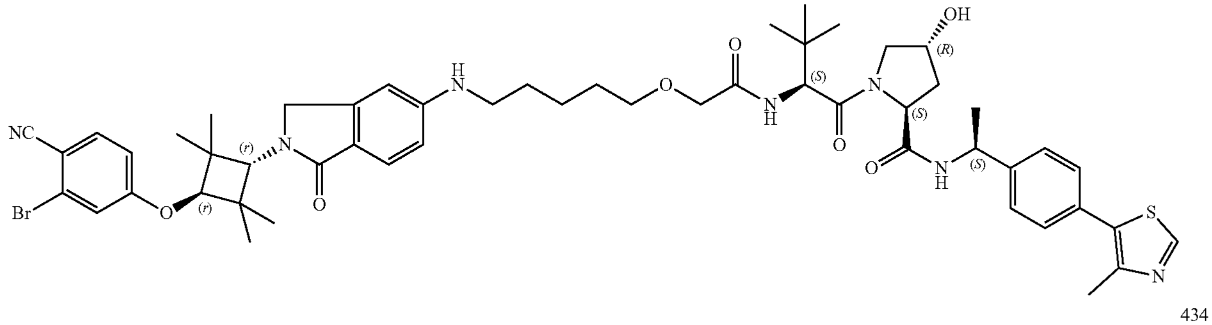

434

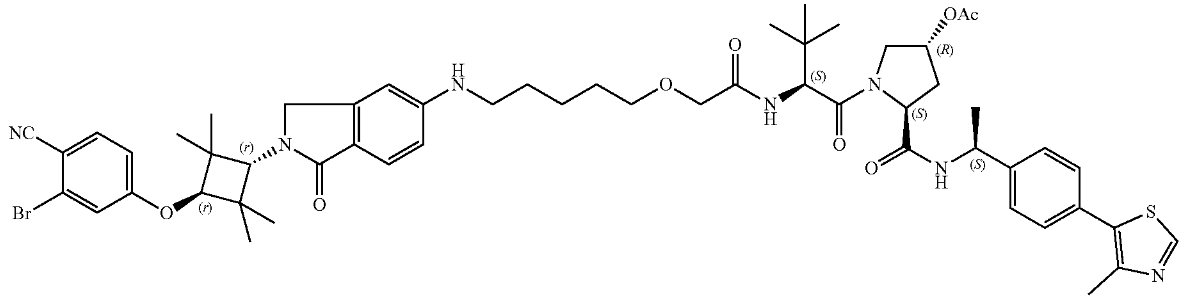

435

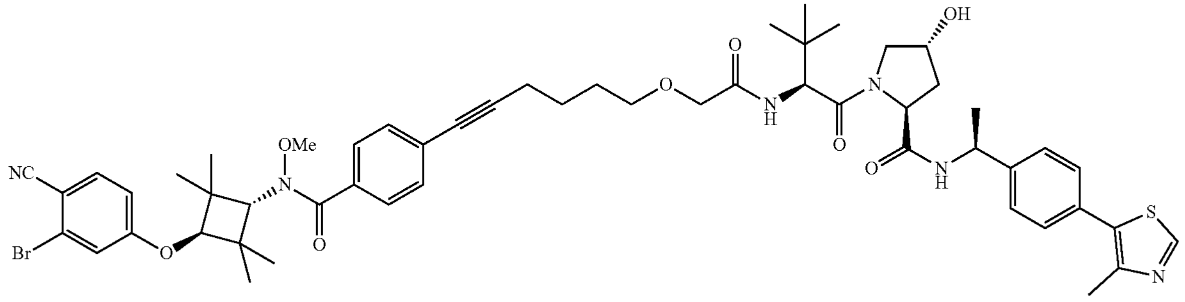

The present invention also provides the use of the compound mentioned above, or an isotopic compound thereof, or an optical isomer thereof, or a tautomer thereof, or a pharmaceutically acceptable salt thereof, or a prodrug thereof, or a solvate thereof, in preparation of targeting chimeras for protein degradation of androgen receptors. Further, said proteolytic targeting chimeras can specifically recognize and/or bind to androgen receptors. Further, said proteolytic targeting chimeras can degrade and/or down-regulate androgen receptors.

Further, said proteolytic targeting chimeras is an active ingredient of drugs for the treatment of related diseases regulated by androgen receptors.

Further, said disease is selected from prostate cancer, breast cancer, Kennedy's disease.

The present invention also provides a drug for the treatment of related diseases regulated by androgen receptors, which is a preparation prepared by using the compound mentioned above, or an isotopic compound thereof, or an optical isomer thereof, or a tautomer thereof, or a pharmaceutically acceptable salt thereof, or a prodrug thereof, or a solvate thereof as an active ingredient, with the addition of pharmaceutically acceptable excipients As demonstrated by the experiments, the compound of formula (I) provided in the present invention can perform targeted degradation on androgen receptors in prostate cancer cells, and suppress the proliferation of prostate cancer cells, as well as also show good metabolic stability and pharmacokinetic properties. The compound of the present invention has good application prospect in preparation of targeting chimeras for protein degradation of androgen receptors and in the preparation of drugs for treating related diseases regulated by androgen receptors.

For the definition of the term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

The minimum and the maximum for the content of carbon atoms in hydrocarbon groups are represented by prefixes, for example, the prefix $C_{a-b}$ alkyls indicate any alkyls containing "a" to "b" carbon atoms. For example, $C_{1-6}$ alkyls denote straight or branched alkyls containing 1-6 carbon atoms.

Herein, "substitution" means that one, two or more hydrogens in a molecule are substituted by other different atoms or molecules, including one, two or more substitutions on the same or different atoms in the molecule. Herein, the minimum and the maximum for the content of carbon atoms in hydrocarbon groups are represented by prefixes, for example, $C_{1-6}$ alkyls denote any straight or branched alkyl containing 1-6 carbon atoms; $C_{1-6}$ alkoxys denote any straight or branched alkoxy containing 1-6 carbon atoms.

In the present invention, "aryls" denote all-carbon monocyclic or fused polycyclic (i.e. rings sharing adjacent carbon atom pairs) groups with conjugated π electron system, such as phenyl and naphthyl. Said aryl ring can be fused to other cyclic groups (including saturated and unsaturated rings), but can not contain hetero atoms such as nitrogen, oxygen, or sulfur. At the same time, the point connecting with the parent must be on the carbon in the ring having the conjugated π electron system. Aryls can be substituted or unsubstituted.

"Heteroaryls" denote the heteroaromatic group containing one or more heteroatoms, and herein, said heteroatom includes O, S, or N. For example, furanyl, thienyl, pyridyl, pyrazolyl, pyrrolyl. N-alkylpyrrolyl, pyrimidinyl, pyrazinyl, imidazolyl, tetrazolyl, etc. The heteroaromatic ring can be fused to aryls, heterocyclic group or cycloalkyl ring, in which the ring connected with the parent structure is heteroaromatic ring. Heteroaryls can be substituted or unsubstituted.

"Alkyls" is a hydrocarbon group formed by losing one hydrogen in an alkane molecule, such as methyl $-CH_3$, ethyl $-CH_3CH_2$, etc.

"Alkylamino" is a group obtained by substituting one or more hydrogens in an alkyl with an amino.

"Alkynyls" denote aliphatic hydrocarbon groups with at least one C≡C triple bond. Said alkynyls can be straight or branched chain. When alkynyls have a limit on carbon numbers before them, for example, "$C_{2-6}$ alkynyls" denote a straight or branched alkynyl having 2-6 carbons.

"Alkenyls" denote aliphatic hydrocarbon groups with at least one C═C double bond. Said alkenyls can be straight or branched chain. When alkenyls have a limit on carbon numbers before them, for example, "$C_{2-6}$ alkenyls" denote a straight or branched alkenyl with 2-6 carbons.

"Substituted or unsubstituted alkenyl" means that the alkenyl group may be substituted or unsubstituted.

"Cycloalkyls" denote saturated or unsaturated cyclic hydrocarbon substituents; cyclic hydrocarbon can have one or more rings. For example, "$C_{3-8}$ cycloalkyls" denote cycloalkyls having 3-8 carbons.

"Saturated cycloalkyl" denotes a saturated cycloalkyl.

"Monocyclic cycloalkyl" means that the cycloalkyl is monocyclic.

"Bridged cycloalkyl" denotes a polycyclic cycloalkyl group in which two rings share two non-adjacent carbon atoms.

"Spirocycloalkyl" refers to a polycyclic cycloalkyl group in which two rings share one carbon atom.

"Fused cycloalkyl" refers to a polycyclic cycloalkyl group in which two rings share two adjacent carbon atoms.

"Heterocyclic group" denotes a saturated or unsaturated cyclic hydrocarbon substituent; the cyclic hydrocarbon may be monocyclic or polycyclic, and carry at least one ring heteroatom (including but not limited to O, S or N). For example, "$C_{3-8}$ heterocyclic group" denotes a heterocyclic group having 3-8 carbons.

"Saturated heterocyclic group" denotes a saturated heterocyclic group.

"Monocyclic heterocyclic group" means that the heterocyclic group is monocyclic.

"Bridged heterocyclic group" means a polycyclic heterocyclic group in which two rings share two non-adjacent carbon atoms or heteroatoms.

"Heterospirocyclyl" means a polycyclic heterocyclic group in which two rings share one carbon atom or heteroatom.

"Fused heterocyclic group" means a polycyclic heterocyclic group in which two rings share two adjacent carbon atoms or heteroatoms.

Halogen is fluorine, chlorine, bromine, or iodine.

"Isotopic compound" denotes a compound obtained by substituting one or more atoms in a compound with the corresponding isotope. For example, the compound obtained by substituting one or more hydrogens (H) in a compound with deuterium (D) or tritium (T); for example, the compound obtained by substituting one or more $C^{12}$ in a compound with $C^{11}$ or $C^{13}$.

"Pharmaceutically acceptable" means a certain carrier, vehicle, diluent, excipient, and/or formed salt is usually chemically or physically compatible with other ingredients constituting a certain pharmaceutical dosage form, as well as physiologically compatible with the recipient.

"Salt" means acid and/or basic salt that is formed by reaction of compound or its stereoisomer with inorganic and/or organic acid and/or base, and also includes zwitterionic salts (inner salts), and further includes quaternary ammonium salts, such as alkylammonium salt. These salts can be directly obtained during the final isolation and purification of a compound. The salts can also be obtained by mixing the compound or its stereoisomers with a certain amount of acid or base appropriately (for example, in equivalent). These salts may form a precipitate in the solution, and be collected by filtration, or recovered after evaporation of the solvent, or obtained by freeze-drying after reaction in an aqueous medium. The salt in the present invention may be compounds' hydrochloride, sulfate, citrate, benzenesulfonate, hydrobromide, hydrofluoride, phosphate, acetate, propionate, succinate, oxalate, malate, succinate, fumarate, maleate, tartrate or trifluoroacetate.

"Solvate thereof" means a solvate formed by the compound of the present invention and a solvent, wherein the solvent includes (but is not limited to) water, ethanol, methanol, isopropanol, propanediol, tetrahydrofuran, and dichloromethane.

In the compound of the present invention, ARB is the recognition/binding part of androgen receptor, and plays the role of the ligand of androgen receptor in the compound.

In the present invention, "selected from a bond" means that the group or atom is absent, and the connection sites at both ends are directly linked, such as in formula (I-A)

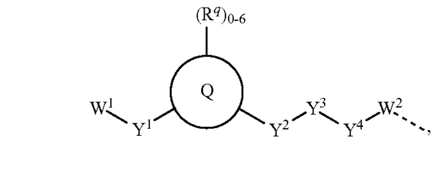

when $Y^3$ is selected from a bond, said structure is

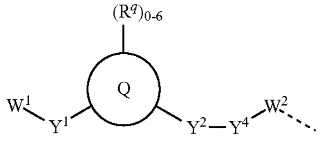

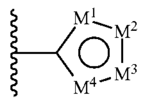

in formula (XII-A) of the present invention represents a five-membered ring with a conjugated structure, which is composed of CH, $M^1$, $M^2$, $M^3$, and $M^4$.

In formula (VIII-A) of the present invention, "$L^1$ and $L^6$ can be freely connected to ARB or U, respectively" means that $L^1$ is connected to ARB, and $L^6$ is connected to U at the same time, or $L^1$ is connected to U, and $L^6$ is connected to ARB at the same time.

Similarly, in formula (VIII-B) of the present invention, "ring A and ring B can be freely connected to ARB or U, respectively" means that ring A is connected to ARB, and ring B is connected to U at the same time, or ring A is connected to U, and ring B is connected to ARB at the same time.

In the present invention, "D" represents deuterium.

There are many ways of naming specific compounds of the present invention: (1) numerical numbers, such as compounds "315" and "3"; (2) compound naming, such as (3R,5S)-1-((S)-2-(2-((5-((4-(3-((1R,3R)-3-(3-chloro-4-cyanophenoxy)-2,2,4,4-tetramethylcyclobutyl)ureido)phenyl)amino)pentyl)oxy)acetylamino)-3,3-dimethylbutyryl)-5-(((S)-1-(4-(4-methylthiazol-5-yl))phenyl)ethyl)carbamoyl)pyrrolidin-3-yl acetate. Although the naming way is different, each specific compound of the present invention can be uniquely determined according to its structure.

Obviously, based on the above content of the present invention, according to the common technical knowledge and the conventional means in the field, without department from the above basic technical spirits, other various modifications, alternations, or changes can further be made.

By following specific examples of said embodiments, the above content of the present invention is further illustrated. But it should not be construed that the scope of the above subject matter of the present invention is limited to the following examples. The techniques realized based on the above content of the present invention are all within the scope of the present invention.

DESCRIPTION OF FIGURE

FIG. 1. Western blot experimental results of compound 99 according to the present invention at different concentrations.

EXAMPLES

The starting materials and equipments used in the examples of the present invention are all known products and can be obtained by purchasing commercially available products.

First, Synthesis of Intermediates:

SM-A-1

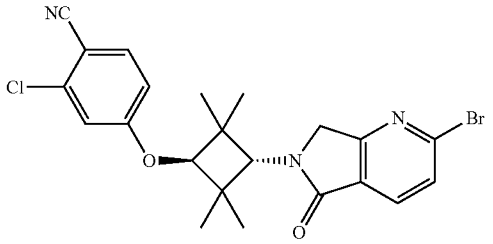

SM-A-2

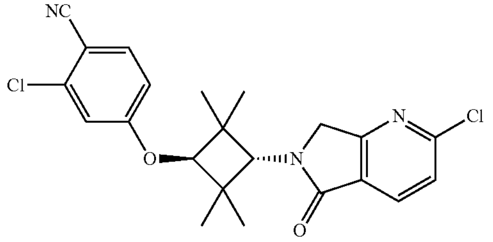

SM-A-3

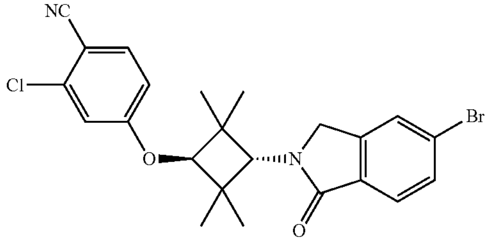

SM-A-4

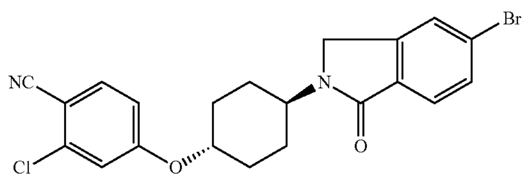

SM-A-5

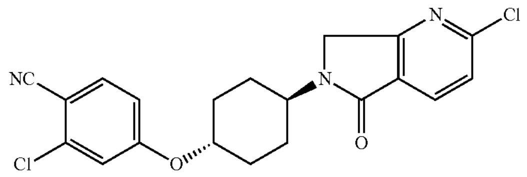

SM-A-1:4-(1r,3r)-3-(2-bromo-5-oxo-5,7-dihydro-6H-pyrrolo[3,4-b]pyridin-6-yl)-2,2,4,4-tetramethyl-cyclobotoxy)-2-chlorobenzonitrile

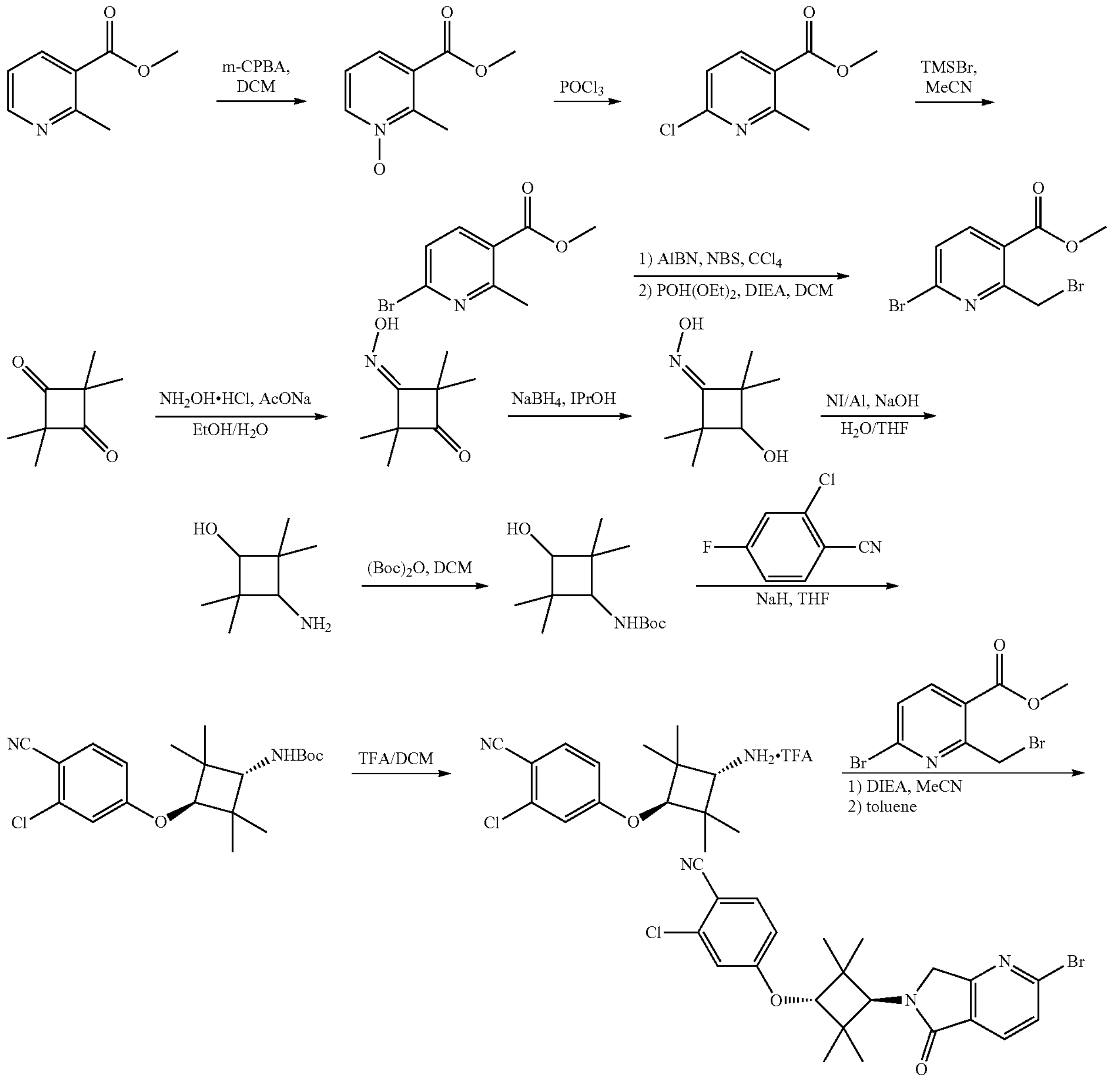

SM-A-1

1. Compound 3-(methoxycarbonyl)-2-methylpyridin-1-oxide

Compound methyl 2-methylnicotinate (30.0 g, 199.0 mmol) was dissolved in dichloromethane (500 mL), to which was then added m-chloroperoxybenzoic acid (68.7 g, 398.0 mmol) in portions. The reaction was stirred overnight at room temperature, and then filtered. The filter cake was washed with dichloromethane. The filtrate was added with 5% sodium sulfite solution (200 mL) and stirred for 30 minutes, and the solution was separated. The aqueous layer was extracted with dichloromethane (100 mL×3), and the filtrates were combined, dried over anhydrous sodium sulfate, rotatory evaporated to dry, and purified by silica gel column chromatography ($CH_2Cl_2$:MeOH=100:1 to 20:1), to provide compound 3-(methoxycarbonyl)-2-methylpyridin-1-oxide as a white solid (18 g, 107.8 mmol), yield: 54%. MS: calcd. for $C_8H_9NO_3$ $[M+H]^+$: 168.0; found: 168.1.

2. Compound methyl 6-chloro-2-methylnicotinate

Compound 3-(methoxycarbonyl)-2-methylpyridin-1-oxide (36.5 g, 218.6 mmol) was added to $POCl_3$ (300 mL) in batches in an ice bath. Then, the mixture was slowly warmed, and allowed to react under reflux for 3 h. The reaction solution was evaporated under reduced pressure to remove most of the solvent, diluted with ethyl acetate (500 mL), and then washed with 10% $Na_2CO_3$ aqueous solution (100 mL×3), and further washed with saturated brine (100 mL×3). The organic layer was dried over anhydrous sodium sulfate, rotatory evaporated to dry, and purified by silica gel column chromatography (petroleum ether:ethyl acetate=10:1 to 5:1), to provide methyl 6-chloro-2-methylnicotinate as a white solid (8 g, 43.2 mmol), yield: 20%. MS: calcd. for $C_8H_8ClNO_2$ $[M+H]^+$: 186.0; found: 186.1.

3. Compound methyl 6-bromo-2-methylnicotinate

Compound methyl 6-chloro-2-methylnicotinate (8.0 g, 43.2 mmol) was dissolved in acetonitrile (80 mL), to which was then added trimethylsilyl bromide (19.8 g, 129.7 mmol), and the reaction solution was heated overnight under reflux. The reaction solution was evaporated to remove the solvent under reduced pressure, and the residue was purified by silica gel column chromatography (petroleum ether:ethyl acetate=30:1 to 10:1), to provide methyl 6-bromo-2-methylnicotinate (7.0 g, 30.6 mmol) as a yellow solid, with a yield of 71%. MS: calcd. for $C_8H_8BrNO_2$ $[M+H]^+$: 230.0; found: 230.1.

4. Compound methyl 2-(bromomethyl)-6-bromonicotinate

Compound methyl 6-bromo-2-methylnicotinate (7.0 g, 30.6 mmol) and N-bromosuccinimide (8.16 g, 45.9 mmol) were added to $CCl_4$ (100 mL), to which was then added azobisisobutyronitrile (566 mg, 3.06 mmol), and the reaction solution was refluxed overnight. The reaction solution was evaporated under reduced pressure to remove the solvent, and the residue was subjected to silica gel column chromatography (petroleum ether:ethyl acetate=30:1 to 10:1) to obtain crude methyl 2-(bromomethyl)-6-bromonicotinate (A-1-5).

The crude product was dissolved in dichloromethane (60 mL), to which was added N,N-diisopropylethylamine (2.36 g, 18.3 mmol), and then diethyl phosphite (1.21 g, 8.76 mmol) was added dropwise in an ice bath. The reaction solution was stirred overnight at room temperature, and then diluted with water (100 mL), extracted with dichloromethane (40 mL×3), washed with saturated brine (50 mL×3). The organic phase was combined, dried over anhydrous sodium sulfate, and rotatory evaporated to dry. The residue was purified by silica gel column chromatography (petroleum ether:ethyl acetate=30:1 to 10:1), to provide methyl 2-(bromomethyl)-6-bromonicotinate as white solid (6.0 g, 19.5 mmol), with a yield of 64%. MS: calcd. for $C_8H_7Br_2NO_2$ $[M+H]^+$: 307.9; found: 308.1.

5. Compound 3-carbonyl-2,2,4,4-tetramethylcyclobutanone oxime

Hydroxyamine hydrochloride (26.0 g, 374.5 mmol) was dissolved in water (40 mL) and ethanol (250 mL), to which were then added 1,3-tetramethylcyclobutanedione (50 g, 356.7 mmol) and sodium acetate (29.3 g, 356.7 mmol). The reaction solution was heated under reflux for 2 h, and then rotatory evaporated to remove ethanol and water. The residue was added with toluene (300 mL) and refluxed for 3 h, and then filtered while hot. The filter cake was washed with toluene (100 mL), and the filtrate was rotatory evaporated to dry, to provide 3-carbonyl-2,2,4,4-tetramethylcyclobutanone oxime as white solid (32.0 g, 206.5 mmol), with a yield of 59%. MS: calcd. for $C_8H_{13}NO_2$ $[M+H]^+$: 156.1; found: 156.1.

6. Compound 3-hydroxy-2,2,4,4-tetramethylcyclobutanone oxime

3-Carbonyl-2,2,4,4-tetramethylcyclobutanone oxime (110.9 g, 714.6 mmol) was dissolved in isopropanol (715 mL), to which was then added sodium borohydride (18.9 g, 500.2 mmol) in portions. The reaction solution was stirred overnight at room temperature, quenched with sodium hydroxide (2000 mL) at 5° C., and then extracted with ethyl acetate (700 mL×3). The organic phases were combined, dried over sodium sulfate, and rotatory evaporated to dry, to provide 3-hydroxy-2,2,4,4-tetramethylcyclobutanone oxime (100.8 g, 642.0 mmol) as white solid, with a yield of 90%.

MS: calcd. for $C_8H_{15}NO_2$ $[M+H]^+$: 158.1; found: 158.1.

7. Compound 3-aminotetramethylcyclobutanone

3-Hydroxy-2,2,4,4-tetramethylcyclobutanone oxime (A-1-7) (35.1 g, 223.3 mmol) was dissolved in tetrahydrofuran (300 mL), to which was then added nickel aluminum alloy (76.5 g, 893.3 mmol) under the protection of nitrogen. After the reaction solution was refluxed for 30 min, 15% sodium hydroxide (300 mL) was added under refluxing. After the addition, reflux was continued for 2 h. After the reaction was completed, the reaction solution was filtered, and the filter cake was washed with tetrahydrofuran (100 mL×3). The filtrate was extracted with ethyl acetate (200 mL×3). The organic phases were combined, washed with saturated brine (200 mL×3), dried over anhydrous sodium sulfate, and rotatory evaporated to dry, to provide 3-aminotetramethylcyclobutanone (24.5 g, 171.3 mmol) as pale yellow solid, with a yield of 77%.

MS: calcd. for $C_8H_{17}NO$ $[M+H]^+$: 144.1; found: 144.1.

8. Compound t-butyl 3-hydroxy-2,2,4,4-tetramethylcyclobutylcarbamate

3-Aminotetramethylcyclobutanone (26.9 g, 188.1 mmol) was dissolved in dichloromethane (500 mL), to which were then added di-t-butyl dicarbonate (41.4 g, 190.0 mmol) and triethylamine (38.0 g, 376.2 mmol). The reaction solution was stirred overnight at room temperature, diluted with water (300 mL), and extracted with dichloromethane (100 mL×3). The organic phases were combined and washed with saturated brine (200 mL×3), dried over anhydrous sodium sulfate, and purified by silica gel column chromatography (petroleum ether:ethyl acetate=10:1 to 1:1), to provide a pale yellow solid t-butyl 3-hydroxy-2, 2,4,4-tetramethylcyclobutylcarbamate (30.1 g, 123.9 mmol), with a yield of 66%.

MS: calcd. for $C_8H_{17}NO$ $[M+H]^+$: 244.2; found: 244.2.

9. Compound t-butyl (1r,3r)-3-(3-chloro-4-cyanophenoxy)-2,2,4,4-tetramethylcyclobutylcarbamate T-butyl 3-hydroxy-2,2,4,4-tetramethylcyclobutylcarbamate (25.0 g, 102.9 mmol) was dissolved in tetrahydrofuran (250 mL), to which was added sodium hydride (60% in mineral oil) (8.23 g, 205.8 mmol) in portions in an ice bath, and then the reaction was stirred in an ice bath for 30 min. Then, 2-chloro-4-fluorobenzonitrile (17.6 g, 113.2 mmol) was dissolved in tetrahydrofuran (50 mL) and slowly added dropwise to the reaction solution. The reaction solution was heated to 60° C. and reacted for 3 h. The reaction solution was quenched with water (300 mL) and extracted with ethyl acetate (100 mL×3). The organic phases were combined, washed with saturated brine (200 mL×3), dried over anhydrous sodium sulfate, and purified by silica gel column chromatography (petroleum ether:ethyl acetate=50:1 to 30:1), to provide t-butyl (1r,3r)-3-(3-chloro-4-cyanophenoxy)-2,2,4,4-tetramethylcyclobutylcarbamate (15.0 g, 39.7 mmol) as white solid, with a yield of 39%. MS: calcd. for $C_{20}H_{27}ClN_2O_3[M+H]^+$: 379.2; found: 279.2.

10. Compound 4-((1r,3r)-3-amino-2,2,4,4-tetramethylcyclobutoxy)-2-chlorobenzonitrile trifluoroacetate t-Butyl (1r,3r)-3-(3-chloro-4-cyanophenoxy)-2,2,4,4-tetramethylcyclobutylcarbamate (5.0 g, 13.2 mmol) was dissolved in dichloromethane (50 mL), to which was added trifluoroacetic acid (50 mL) in an ice bath. The reaction solution was stirred 1 h at room temperature, and rotatory evaporated to dry, to provide crude 4-((1r,3r)-3-amino-2,2,4,4-tetramethylcyclobutoxy)-2-chlorobenzonitrile trifluoroacetate, which was directly used in next reaction. MS: calcd. for $C_{17}H_{19}ClF_3N_2O_2$ $[M+H]^+$: 376.1; found: 279.1.

11. Compound 4-((1r,3r)-3-(2-bromo-5-oxo-5,7-dihydro-6H-pyrrolo[3,4-b]pyridin-6-yl)-2,2,4,4-tetramethylcyclobutoxy)-2-chlorobenzonitrile 4-((1r,3r)-3-Amino-2,2,4,4-tetramethylcyclobutoxy)-2-chlorobenzonitrile trifluoroacetate (13.2 mmol, the crude product from the previous step) was dissolved in acetonitrile (240 mL), to which were then added N,N-diisopropylethylamine (8.51 g, 66.0 mmol) and compound methyl 2-(bromomethyl)-6-bromonicotinate (4.0 g, 13.2 mmol). The reaction solution was heated overnight under reflux. After the reaction solution was rotatory evaporated to dry, toluene (50 mL) was added, and the resultant reaction solution was refluxed overnight. The reaction solution was cooled and filtered. The filter cake was washed with toluene, and dried to obtain the target compound as a white solid (3.95 g, 8.3 mmol), with a two-step yield of 63%. MS: calcd. for $C_{22}H_{21}BrClN_3O_2$ $[M+H]^+$: 474.0; found: 474.0.

SM-A-2, SM-A-3, SM-A-4, and SM-A-S were Prepared by Using a Method Similar to SM-A-1.

SM-A-2: 2-chloro-4-((1r,3r)-3-(2-chloro-5-oxo-5,7-dihydro-6H-pyrrolo[3,4-b]pyridin-6-yl)-2,2,4,4-tetramethylcyclobutoxy)benzonitrile

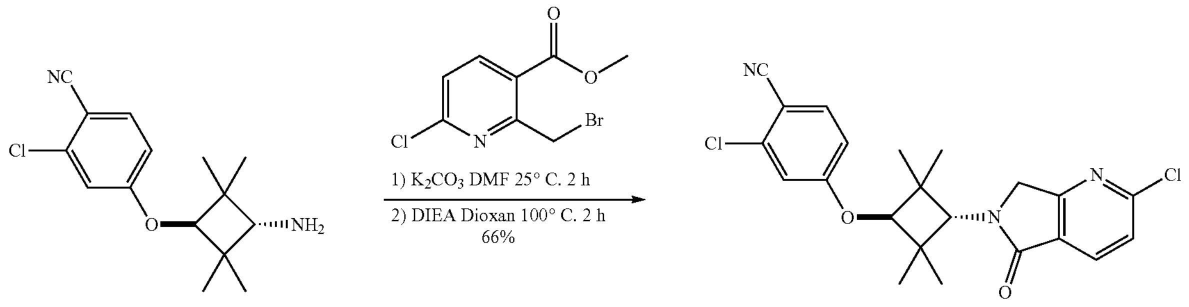

Compound 4-((1r,3r)-3-amino-2,2,4,4-tetramethylcyclobutoxy)-2-chlorobenzonitrile (527 mg, 1.89 mmol), potassium carbonate (392 mg, 2.84 mmol), and 10 mL DMF were successively added, and then under nitrogen protection, after stirring evenly, the solution of methyl 2-(bromomethyl)-6-chloronicotinate (500 mg, 1.89 mmol) in DMF was added dropwise. The mixture was stirred at room temperature for 2 h. The end point of the reaction was determined by TLC. The reaction solution was added with water, extracted three times with ethyl acetate, and dried over anhydrous sodium sulfate. The reaction solution was extracted and washed with saturated brine three times, dried over anhydrous sodium sulfate, and rotatory evaporated to dry, to provide a crude product, which was separated by silica gel column chromatography, to provide the intermediate. To the intermediate, were added DIEA (734 mg, 1.48 mmol) and 5 mL of 1,4-dioxane, and the mixture was allowed to react at 100° C. for two days. The end point of the reaction was confirmed by TLC ANALYSIS, followed by separation by silica gel column chromatography, to provide the intermediate 2-chloro-4-((1r,3r)-3-(2-chloro-5-oxo-5,7-dihydro-6H-pyrrolo[3,4-b]pyridin-6-yl)-2,2,4,4-tetramethylcyclobutoxy) benzonitrile (536 mg, 1.25 mmol), with a yield of 66%. LC/MS (ESI+) calcd for $C_{22}H_{21}C_{12}N_3O_2[M+H]+$ m/z, 430.1; found, 430.1.

SM-A-3: Synthesis of 4-((1r,3r)-3-(5-bromo-1-isoindolin-2-yl)-2,2,4,4-tetramethylcyclobutyl ether)-2-chlorobenzonitrile

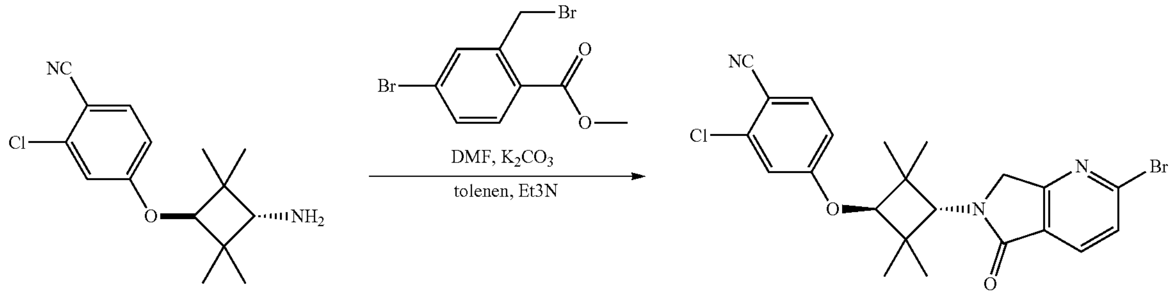

Compound 4-((1r,3r)-3-amino-2,2,4,4-tetramethylcyclobutyl ether)-2-chlorobenzonitrile (1.0 g, 3.59 mmol) and $K_2CO_3$ (743.0 mg, 5.38 mmol) were added to 20 mL DMF, and methyl 4-bromo-2-(bromomethyl)benzoate (1.10 g, 3.59 mmol) was added to the reaction solution in portions. The reaction solution was stirred at room temperature for 1 h. The reaction was completed by TLC detection, and a new spot was formed, to which were added ethyl acetate and saturated brine for extraction. The organic layer was washed twice with saturated brine, dried with anhydrous sodium sulfate, rotatory evaporated to dry, and purify by silica gel column chromatography, to provide 1.2 g of oily liquid, to which were added 10 mL of toluene and 1 mL of triethylamine. The resultant solution was heated and stirred for 16 h under reflux. The solvent was rotatory evaporated, and then a small amount of petroleum ether and ethyl acetate (4:1) were added. The solid was filtered and dried, to provide 4-((1r,3r)-3-(5-bromo-1-isoindolin-2-yl))-2,2,4,4-tetramethylcyclobutyl ether)-2-chlorobenzonitrile as a white solid (900.0 mg, 1.9 mmol), with a yield of 52.9%.

SM-A-4: 4-(((1r,4r)-4-(5-bromo-1-oxoisoindolin-2-yl)cyclohexyl)oxy)-2-chlorobenzonitrile

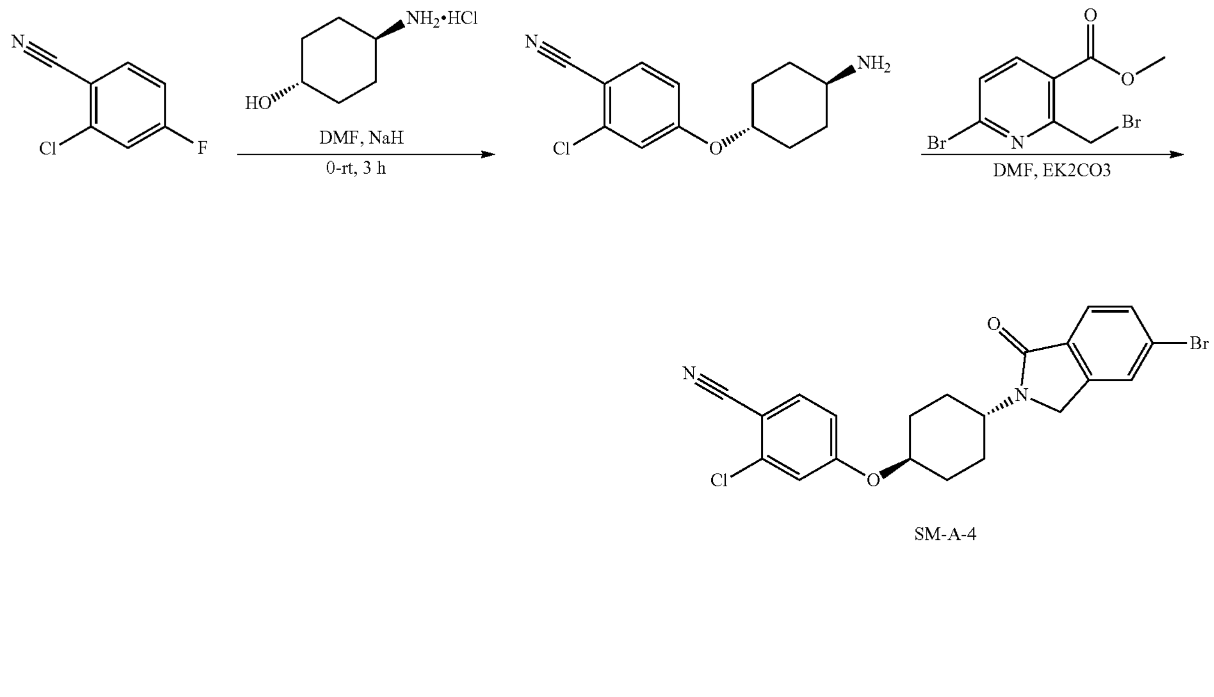

SM-A-4

Step 1: Synthesis of 4-(((1r,4r)-4-aminocyclohexyl)oxy)-2-chlorobenzonitrile

The compound trans-p-aminocyclohexanol hydrochloride (26.8 g, 177 mmol) was dissolved in 0.8 L of DMF, to which was added NaH (22.3 g, 531 mmol) in portions in an ice bath under $N_2$ protection, and the mixture was allowed to react at 0° C. for 1 h. The compound 2-chloro-4-fluoro-benzonitrile was dissolved in 200 ml DMF, which was slowly added dropwise to the reaction solution, and then the mixture was incubated at 0° C. for 0.5 h, warmed to the room temperature, stirred for 3 h. The reaction was completed by TLC detection, to which were added ethyl acetate (EA) and water for extraction. EA layer was further washed twice with saturated brine, and then dried over anhydrous sodium sulfate, rotatory evaporated to dry, and purified by silica gel column chromatography to obtain the product 4-(((1r,4r)-4-aminocyclohexyl)oxy)-2-chlorobenzonitrile as a white solid (27.7 g).

Step 2

The compound 4-(((1r,4r)-4-aminocyclohexyl)oxy)-2-chlorobenzonitrile (1 g, 4 mmol) was dissolved in 20 mL DMF, to which was added $K_2CO_3$ (0.82 g, 6 mmol), and then the compound methyl 4-bromo-2-(bromomethyl)benzoate (1.2 g, 4 mmol) was added in portions. The mixture was stirred overnight at room temperature. Water was added to precipitate a white solid, and the resultant solid was filtered and dried to obtain the compound SM-A-3 (1.3 g, 2.9 mmol).

SM-A-5:2-chloro-4-((1r,4r)-4-(2-chloro-5-oxo-5,7-dihydro-6H-pyrrolo[3,4-b]pyridin-6-yl) cyclohexyl) oxy)benzonitrile

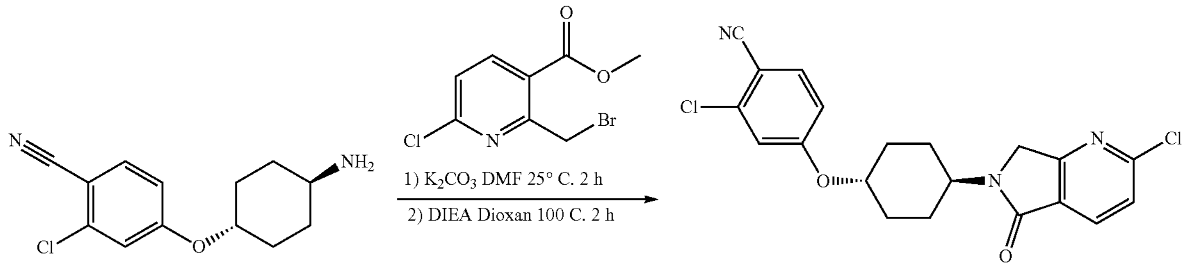

SM-A-5

The compound 4-((1r,4r)-4-aminocyclohexyl)oxy)-2-chlorobenzonitrile (2.37 g, 9.45 mmol), potassium carbonate (1.96 g, 14.18 mmol), and 40 ml DMF were successively added, and then under nitrogen protection, after stirring evenly, the solution of methyl 2-(bromomethyl)-6-chloronicotinate (2.5 g, 9.45 mmol) in DMF was added dropwise. The mixture was stirred at room temperature for 2 h. The end point of the reaction was determined by TLC ANALYSIS. The reaction solution was added with water, extracted three times with ethyl acetate, washed three times with saturated brine, dried over anhydrous sodium sulfate, and rotatory evaporated to dry, to provide a crude product, which was separated by silica gel column chromatography, to provide the intermediate. To the intermediate, were added DIEA (4.73 mg, 36.61 mmol) and 20 mL of 1,4-dioxane, and the mixture was allowed to react at 100° C. for two days. The end point of the reaction was confirmed by TLC ANALYSIS, followed by separation by silica gel column chromatography, to provide the intermediate 2-chloro-4-((1r,4r)-4-(2-chloro-5-oxo-5,7-dihydro-6H-pyrrolo[3,4-b]pyridin-6-yl)cyclohexyl)oxy)benzonitrile (1.85 g, 4.60 mmol), with a yield of 49%.

LC/MS (ESI$^+$) calcd for $C_{20}H_{17}Cl_2N_3O_2$ [M+H]+m/z, 402.1; found, 402.1.

SM-A-6: 2-chloro-4-((1r,3r)-2,2,4,4-tetramethyl-3-(2-(methylthio)-5-oxo-5,7-dihydro-6H-pyrrolo[3,4-d]pyrimidin-6-yl)cyclobutyloxy)benzonitrile

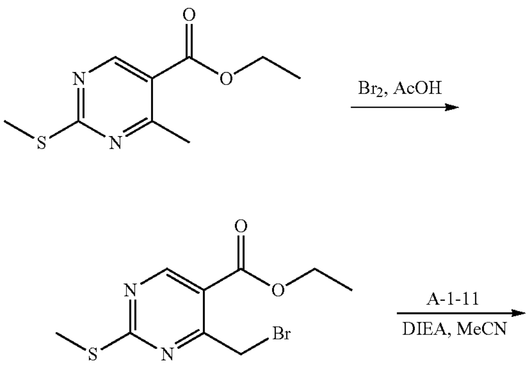

-continued

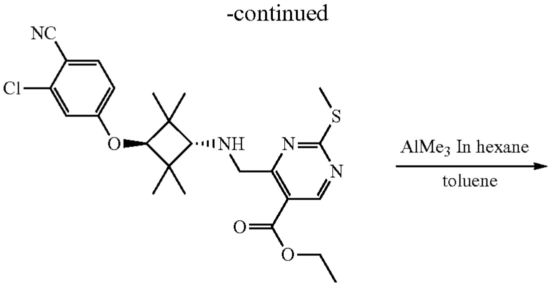

-continued

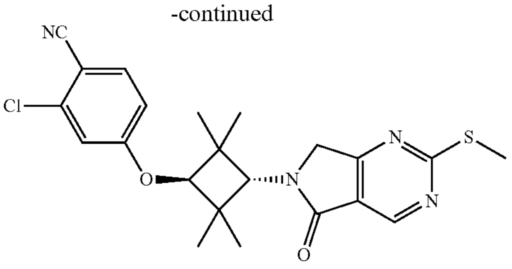

SM-A-6

1. Eethyl 4-(bromomethyl)-2-(methylthio)pyrimidin-5-carboxylate

Ethyl 4-methyl-2-(methylthio)pyrimidin-5-carboxylate (10.6 g, 50.0 mmol) was dissolved in acetic acid (30 mL), to which was added bromine (9.6 g, 60.0 mmol) dropwise in an ice bath. The reaction solution was heated to 60° C. and allowed to react for 3 h. The reaction solution was poured into ice water (100 mL), and then extracted with ethyl acetate (50 mL×3). The organic phase was combined, washed with saturated brine (50 mL×3), dried over anhydrous sodium sulfate, and purified by silica gel column chromatography (petroleum ether:ethyl acetate=50:1 to 30:1) to obtain a yellow oily ethyl 4-(bromomethyl)-2-(methylthio)pyrimidin-5-carboxylate (8.3 g, 28.6 mmol), with a yield of 57%. MS: calcd. for $C_9H_{11}BrN_2O_2S$ $[M+H]^+$: 291.0; found: 291.0.

2. Ethyl 4-((1r,3r)-3-(3-chloro-4-cyanophenoxy)-2,2,4,4-tetramethylcyclobutyl amino)methyl)-2-(methylthio)pyrimidin-5-carboxylate 4-((1r,3r)-3-amino-2,2,4,4-tetramethylcyclobutoxy)-2-chlorobenzonitrile trifluoroacetate (11.4 mmol, the crude product from the previous route) was dissolved in acetonitrile (120 mL), to which were then added N,N-diisopropylethylamine (7.35 g, 11.4 mmol) and 4-(bromomethyl)-2-(methylthio)pyrimidin-5-carboxylate ethyl (4.3 g, 11.4 mmol). The reaction solution was stirred overnight at room temperature. The reaction solution was diluted with water (100 mL) and extracted with ethyl acetate (50 mL×3). The organic phase was combined, washed with saturated brine (50 mL×3), dried over anhydrous sodium sulfate, and purified by silica gel column chromatography (petroleum ether: ethyl acetate=50:1 to 10:1), to provide ethyl 4-((1r,3r)-3-(3-chloro-4-cyanophenoxy)-2,2,4,4-tetramethylcyclobutylamino)methyl)-2-(methylthio) pyrimidin-5-carboxylate as off-white solid (3.4 g, 7.0 mmol), with a yield of 61%. MS: calcd. for $C_{24}H_{29}ClN_4O_3S$ $[M+H]^+$: 489.2; found: 489.2.

3. 2-Chloro-4-((1r,3r)-2,2,4,4-tetramethyl-3-(2-(methylthio)-5-oxo-5H-pyrrolo[3,4-d]pyrimidin-6(7H)-yl)cyclobutyloxy)benzonitrile (SM-A-6)

Ethyl 4-((1r,3r)-3-(3-chloro-4-cyanophenoxy)-2,2,4,4-tetramethylcyclobutylamino) methyl)-2-(methylthio)pyrimidin-5-carboxylate (2.0 g, 4.1 mmol) was dissolved in toluene (100 mL), and then nitrogen was purged, to which was added the solution of trimethylaluminum in n-hexane (2.0 M) (4.1 mL, 8.2 mmol) dropwise in an ice bath. The reaction solution was heated to 110° C. and allowed to react for 20 h. The reaction solution was diluted with water (100 mL) and extracted with ethyl acetate (50 mL×3). The organic phases were combined, washed with saturated brine (50 mL×3), dried over anhydrous sodium sulfate, and purified by silica gel column chromatography (petroleum ether:ethyl acetate=50:1 to 30:1), to provide 2-chloro-4-((1r,3r)-2,2,4,4-tetramethyl-3-(2-(methylthio)-5-oxo-5H-pyrrolo[3,4-d] pyrimidin-6(7H)-yl) cyclobutyloxy)benzonitrile as a yellow solid (0.8 g, 1.8 mmol), with a yield of 49%. MS: calcd. for $C_{22}H_{23}ClN_4O_2S$ $[M+H]^+$: 443.1; found: 443.1.

Other lactam intermediates were synthesized by a method similar to the above-mentioned route.

The following amide intermediate compounds were synthesized by methods described in literature (US20180099940, US20170327469) or similar methods.

SM-A-7

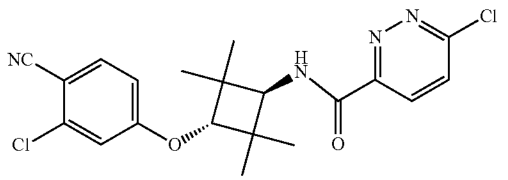

SM-A8

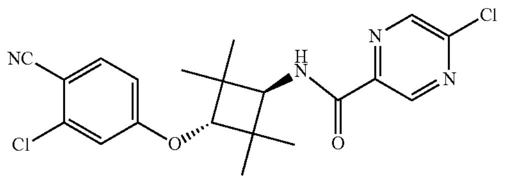

SM-A-9

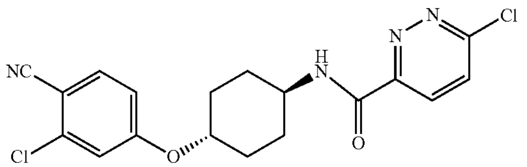

SM-A-10

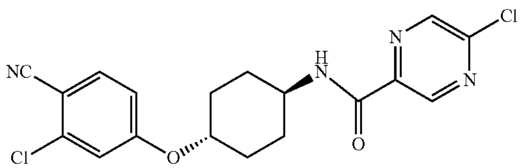

SM-A-11

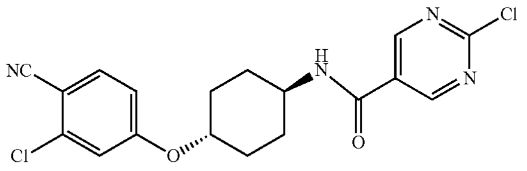

SM-A-12

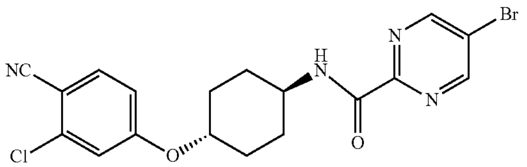

-continued

SM-A-13

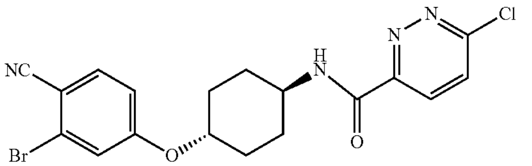

SM-A-14

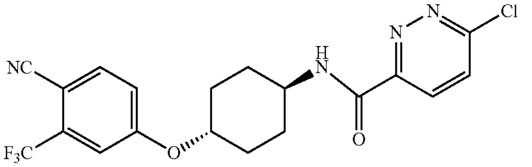

The following SM-E intermediate compounds were synthesized by methods described in literature (US20180099940, US20170327469) or similar methods.

SM-E-1

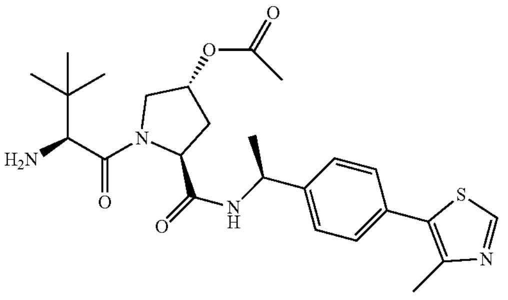

SM-E-2

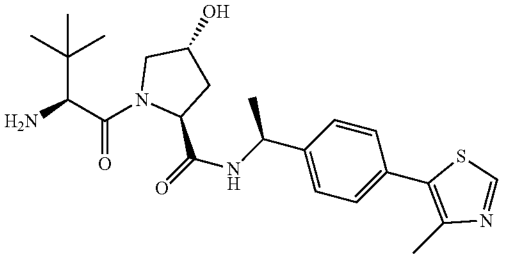

SM-E-3

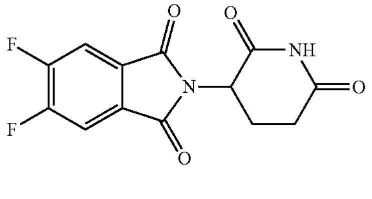

SM-E-4

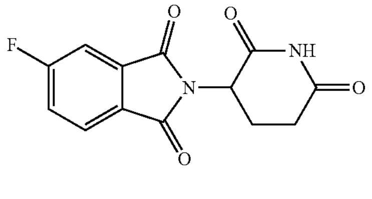

Intermediate SM-L-1: t-butyl 4-ethynyl-1,4'-dipiperidine-1'-carboxylate

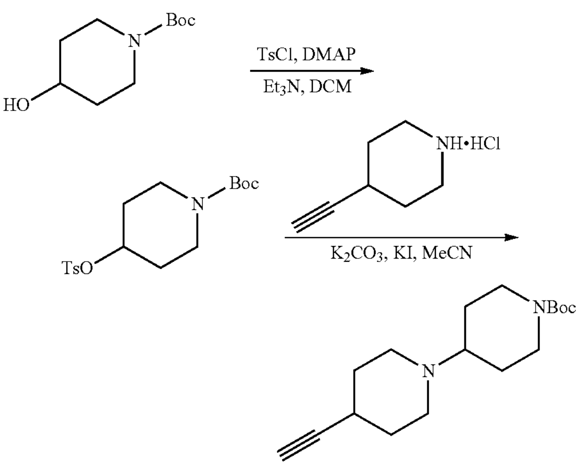

SM-L-1

1. Compound t-butyl 4-(p-toluenesulfonyloxy)piperidine-1-carboxylate t-Butyl 4-hydroxypiperidine-1-carboxylate (10.0 g, 49.7 mmol) was dissolved in dichloromethane, to which was then added p-toluenesulfonyl chloride (10.8 g, 56.6 mmol), triethylamine (7.5 g, 74.5 mmol) and 4-dimethylaminopyridine (183 mg, 1.5 mmol). The reaction solution was stirred overnight at room temperature. The reaction solution was diluted with water (100 mL) and extracted with dichloromethane (50 mL×3). The organic phase was combined, washed with saturated brine (50 mL×3), dried over anhydrous sodium sulfate, and purified by silica gel column chromatography (petroleum ether:ethyl acetate=10:1 to 30:1), to provide t-butyl 4-(p-toluenesulfonyloxy)piperidine-1-carboxylate as a white solid (13.2 g, 37.2 mmol), with a yield of 83%. MS: calcd. for $C_{17}H_{25}NO_5S$ $[M+H]^+$: 356.1; found: 356.1.

2. Synthesis of Compound t-butyl 4-ethynyl-1,4‘-dipiperidine-1’-carboxylate (SM-L-1)

t-Butyl 4-(p-toluenesulfonyloxy)piperidine-1-carboxylate (1.2 g, 3.4 mmol) was dissolved in acetonitrile, to which were then added 4-ethynylpiperidine hydrochloride (490 mg, 3.4 mmol), potassium carbonate (1.0 g, 7.5 mmol) and potassium iodide (113 mg, 0.68 mmol). The reaction solution was heated under reflux for 36 h. The reaction solution was diluted with water (50 mL) and extracted with ethyl acetate (20 mL×3). The organic phases were combined, washed with saturated brine (20 mL×3), dried over anhydrous sodium sulfate, and purified by silica gel column chromatography (petroleum ether:ethyl acetate=10:1 to 0:100), to provide t-butyl 4-ethynyl-1,4‘-dipiperidine-1’-carboxylate (0.6 g, 2.1 mmol) as a white solid, with a yield of 60%. MS: calcd. for $C_{17}H_{2}N_{2}O_{2}[M+H]^+$: 293.1; found: 293.1.

SM-L-3 was prepared by a method similar to the synthetic method of SM-L-1

SM-L-3

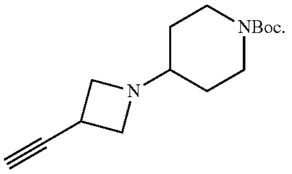

Intermediate SM-L-2: t-butyl 3-(4-ethynylpiperidin-1-yl)azetidine-1-carboxylate

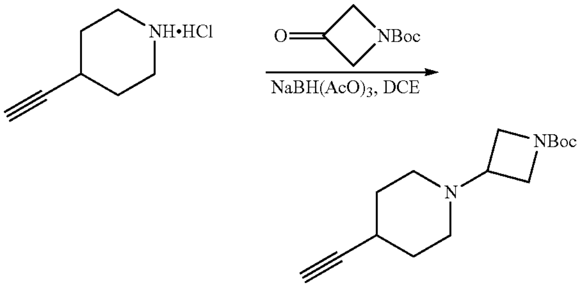

SM-L-2

4-ethynylpiperidine hydrochloride (2.0 g, 13.8 mmol) and 3-t-butoxycarbonyl-3-azetidinone (2.35 g, 13.8 mmol) were dissolved in 1,2-dichloroethane (40 mL), to which was added acetic acid (1 mL), and finally sodium triacetoxyborohydride (5.85 g, 27.6 mmol) was added. The reaction solution was stirred overnight at room temperature. The reaction solution was diluted with water (50 mL) and extracted with dichloromethane (30 mL×3). The organic phase was combined, washed with saturated brine (30 mL×3), dried over anhydrous sodium sulfate, and purified by silica gel column chromatography (petroleum ether:ethyl acetate=10:1 to 0:100), to provide t-butyl 3-(4-ethynylpiperidin-1-yl)azetidine-1-carboxylate as a colorless oil (1.0 g, 3.8 mmol), with a yield of 27%. MS: calcd. for $C_{15}H_{24}N_2O_2$ $[M+H]^+$: 265.2; found: 265.2.

The synthesis of intermediates SM-L-4, SM-L-8, SM-L-9 and SM-L-10 was similar to that of SM-L-2.

SM-L-4

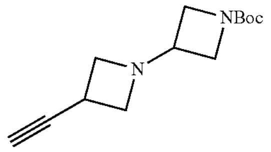

SM-L-8

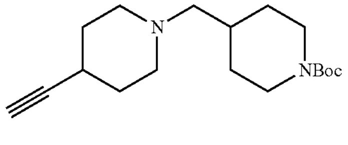

SM-L-9

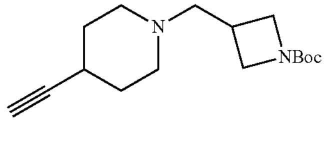

-continued

SM-L-10

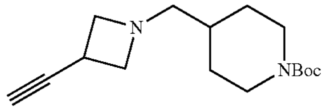

Intermediate SM-L-11: t-butyl 4-(2-methyl-3-butyn-2-yl)piperazine-1-carboxylate

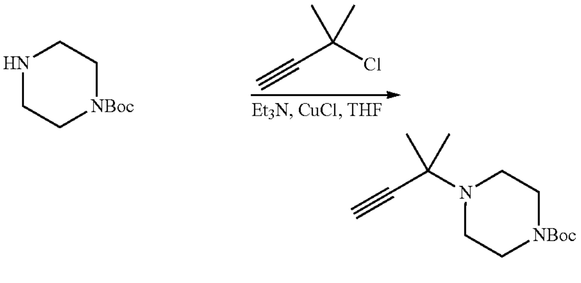

SM-L-11 t-Butyl piperazine-1-carboxylate (3.3 g, 17.7 mmol), triethylamine (3.57 g, 35.4 mmol) and 3-chloro-3-methylbutyne (1.8 g, 17.7 mmol) were dissolved in tetrahydrofuran (30 mL), to which was then added CuCl (179 mg, 1.8 mmol). The reaction solution was stirred for 10 min at room temperature. The reaction solution was diluted with water (100 mL) and extracted with ethyl acetate (50 mL×3). The organic phase was combined, washed with saturated brine (50 mL×3), dried over anhydrous sodium sulfate, and purified by silica gel column chromatography (petroleum ether: ethyl acetate=10:1 to 2:1), to provide t-butyl 4-(2-methyl-3-butyn-2-yl)piperazine-1-carboxylate as colorless oil (3.0 g, 11.9 mmol), with a yield of 67%. MS: calcd. for $C_{14}H_{24}N_2O_2$ $[M+H]^+$: 253.2; found: 253.2.

Intermediate SM-L-13: t-butyl 4-(2-methyl-3-butyn-2-ylamino)piperidine-1-carboxylate

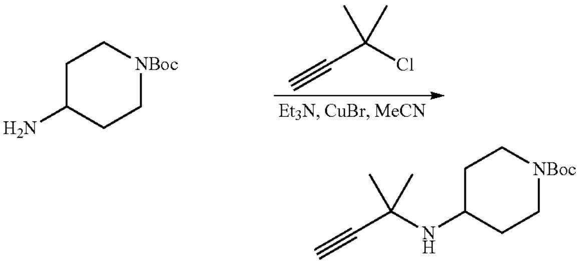

SM-L-13 t-Butyl 4-aminopiperdine-1-carboxylate (2.6 g, 13.0 mmol), triethylamine (1.51 g, 15.0 mmol) and CuBr (144 mg, 1.0 mmol) were added to acetonitrile (30 mL), to which was then added the solution of 3-chloro-3-methylbutyne (1.0 g, 10.0 mmol) in acetonitrile (10 mL) dropwise. The reaction solution was stirred 1 h at room temperature. The reaction solution was diluted with water (100 mL) and extracted with ethyl acetate (50 mL×3). The organic phase was combined, washed with saturated brine (50 mL×3), dried over anhydrous sodium sulfate, and purified by silica gel column chromatography (petroleum ether:ethyl acetate=10:1 to 2:1), to provide t-butyl 4-(2-methyl-3-butyn-2-ylamino)piperidine-1-carboxylate as colorless oil (0.6 g, 2.3 mmol), with a yield of 22%. MS: calcd. for $C_{15}H_{26}N_2O_2[M+H]^+$: 267.2; found: 267.2.

Intermediate SM-L-14: t-butyl 4-(4-ethynylphenyl)piperazine-1-carboxylate

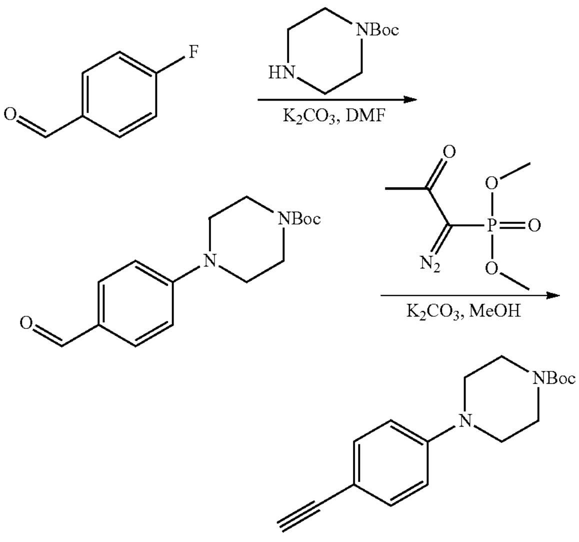

SM-L-14

1. Compound t-butyl 4-(4-formylphenyl)piperazine-1-carboxylate

4-Fluorobenzaldehyde (5.0 g, 40.3 mmol) and t-butyl piperazine-1-carboxylate (7.5 g, 40.3 mmol) were dissolved in N,N-dimethylformamide (100 mL), to which was then added potassium carbonate (11.2 g, 80.6 mmol). The reaction solution was stirred for two days at 110° C. The reaction solution was diluted with water (150 mL) and extracted with ethyl acetate (100 mL×3). The organic phase was combined, washed with saturated brine (100 mL×3), dried over anhydrous sodium sulfate, and purified by silica gel column chromatography (petroleum ether:ethyl acetate=20:1 to 5:1), to provide t-butyl 4-(4-formylphenyl)piperazine-1-carboxylate as a white solid (7.1 g, 24.5 mmol), with a yield of 61%. MS: calcd. for $C_{16}H_{23}O_2N_3$ $[M+H]^+$: 290.2; found: 290.0.

2. Compound t-butyl 4-(4-ethynylphenyl)piperazine-1-carboxylate t-Butyl 4-(4-formylphenyl)piperazine-1-carboxylate (B-14-1) (2.9 g, 10.0 mmol) and dimethyl 1-diazo-2-oxopropylphosphonate (3.8 g, 20.0 mmol) were dissolved in methanol (50 mL), to which was added potassium carbonate (5.5 g, 40 mmol) in an ice bath. The reaction solution was slowly warmed to room temperature and allowed to stand overnight. The reaction solution was rotatory evaporated to dry and purified by silica gel column chromatography (petroleum ether:ethyl acetate=50:1 to 15:1), to provide t-butyl 4-(4-ethynylphenyl)piperazine-1-carboxylate as a white solid (1.5 g, 5.2 mmol), with a yield of 54%. MS: calcd. for $C_{17}H_{23}O_2N_2$ $[M+H]^+$: 287.2; found: 287.2.

Intermediate SM-L-18: t-butyl 4-((1s,3s)-3-ethynylcyclobutyl)piperazine-1-carboxylate (SM-L-18Q) and t-butyl 4-((1r,3r)-3-ethynylcyclobutyl)piperazine-1-carboxylate (SM-L-18H)

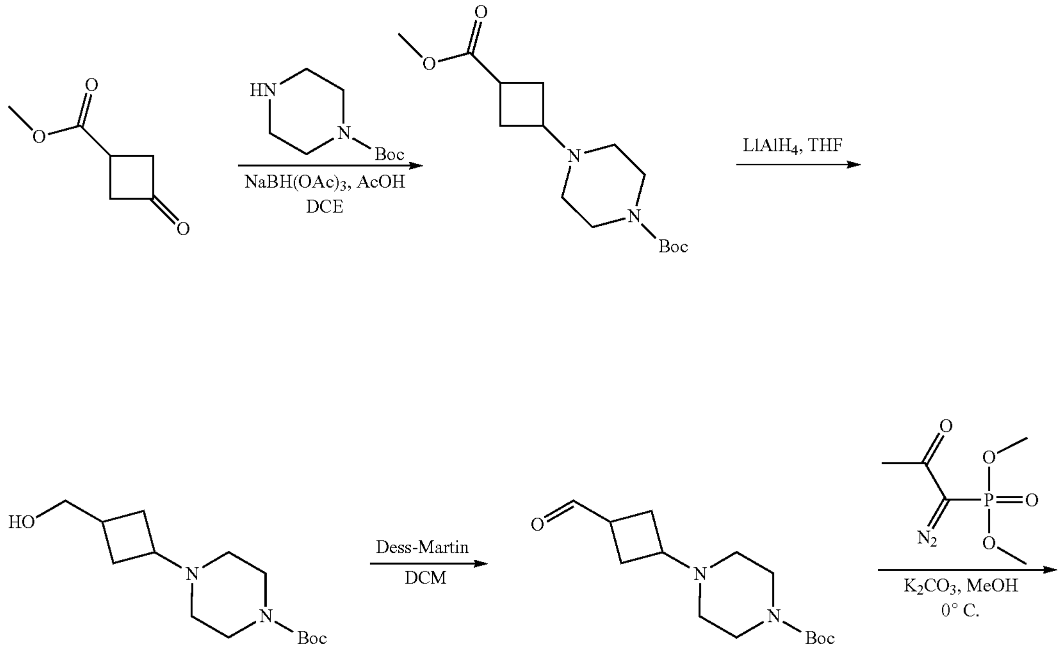

-continued

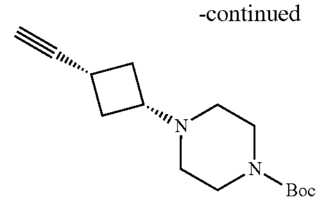

SM-L-18Q

+

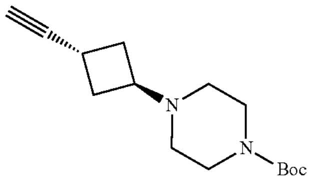

SM-L-18H

1. Compound t-butyl 4-(3-(methoxycarbonyl)cyclobutyl)piperazine-1-carboxylate

Methyl 3-oxocyclobutanecarboxylate (5.12 g, 40.0 mmol) and t-butyl piperazine-1-carboxylate (8.9 g, 48.0 mmol) were dissolved in 1,2-dichloroethane (100 mL), to which was then added acetic acid (4.8 g, 80.0 mmol), and finally sodium triacetoxyborohydride (21.2 g, 100 mmol) was added. The reaction solution was stirred overnight at room temperature. The reaction solution was diluted with water (100 mL) and extracted with dichloromethane (50 mL×3). The organic phase was combined, washed with saturated brine (50 mL×3), dried over anhydrous sodium sulfate, and purified by silica gel column chromatography (petroleum ether:ethyl acetate=10:1 to 0:100), to provide t-butyl 4-(3-(methoxycarbonyl)cyclobutyl)piperazine-1-carboxylate (6.0 g, 20.8 mmol), with a yield of 52%. MS: calcd. for $C_{15}H_{26}N_2O_4$ $[M+H]^+$: 299.2; found: 299.4.

2. Compound t-butyl 4-(3-(hydroxymethyl)cyclobutyl)piperazine-1-carboxylate t-Butyl 4-(3-(methoxycarbonyl)cyclobutyl)piperazine-1-carboxylate (6.0 g, 20.8 mmol) was dissolved in tetrahydrofuran (120 mL), to which was added lithium aluminum hydride (4.8 g, 80.0 mmol) in an ice bath. The reaction solution was continuously stirred in an ice bath for 1 h. The reaction solution was diluted with tetrahydrofuran (100 mL), kept in an ice bath, and then water (4.8 mL) was added dropwise. The mixture was further stirred for 10 min, and then 15% sodium hydroxide solution (4.8 mL) was added. The reaction solution was stirred for additional 10 min, to which was further added water (14.4 mL), and the resultant solution was continually stirred for 20 min. Finally, anhydrous magnesium sulfate was added, and the mixture was stirred for 20 min. The reaction mixture was filtered, and the filtrate was rotatory evaporated to dry, to obtain t-butyl 4-(3-(hydroxymethyl)cyclobutyl)piperazine-1-carboxylate (4.4 g, 14.8 mmol) as colorless oil, with a yield of 78%. MS: calcd. for $C_{14}H_{26}N_2O_3$ $[M+H]^+$: 271.2. found: 271.4.

3. Compound t-butyl 4-(3-formylcyclobutyl)piperazine-1-carboxylate t-Butyl 4-(3-(hydroxymethyl)cyclobutyl)piperazine-1-carboxylate (4.0 g, 14.8 mmol) was dissolved in dichloromethane (80 mL), to which was then added 1,1,1'-(3-oxo-1λ5-1,2-phenyliodo-1(3H)-yelidone)acetoacetate (9.4 g, 22.2 mmol). The reaction solution was stirred at room temperature for 24 h, and then filtered. The filtrate was rotatory evaporated to dry, to provide crude t-butyl 4-(3-formylcyclobutyl)piperazine-1-carboxylate (5.3 g), which was directly used in next reaction. MS: calcd. for $C_{14}H_{24}N_2O_3$ $[M+H]^+$: 269.2; found: 269.4.

4. Synthesis of Compound t-butyl 4-((1s,3s)-3-ethynylcyclobutyl)piperazine-1-carboxylate (SM-L-18Q) and t-butyl 4-((1r,3r)-3-ethynylcyclobutyl) piperazine-1-carboxylate (SM-L-18H)

t-Butyl 4-(3-formylcyclobutyl)piperazine-1-carboxylate (14.8 mmol, the crude product from the previous step) and dimethyl 1-diazo-2-oxopropylphosphonate (5.68 g, 29.6 mmol) were dissolved in methanol (100 mL), to which was added potassium carbonate (10.2 g, 74.0 mmol) in an ice bath. The reaction solution was slowly warmed to room temperature and allowed to stand overnight. The reaction solution was diluted with water (200 mL) and extracted with ethyl acetate (80 mL×3). The organic phase was combined, washed with saturated brine (80 mL×3), dried over anhydrous sodium sulfate, and purified by silica gel column chromatography (petroleum ether:ethyl acetate=20:1 to 12:1), to provide t-butyl 4-((1s, 3s)-3-ethynylcyclobutyl) piperazine-1-carboxylate (SM-L-18Q) as off-white solid (0.84 g, 3.2 mmol), with a two-step yield of 16%. MS: calcd. for $C_{15}H_{24}N_2O_2$ $[M+H]^+$: 265.2; found: 265.4. At the same time, t-butyl 4-((1r,3r)-3-ethynylcyclobutyl)piperazine-1-carboxylate (SM-L-18H)(0.36 g, 1.4 mmol) was obtained as off-white solid, with a two-step yield of 7%. MS: calcd. for $C_{15}H_{24}N_2O_2$ $[M+H]^+$: 265.2; found: 265.4.

Synthesis of Intermediate SM-L-5

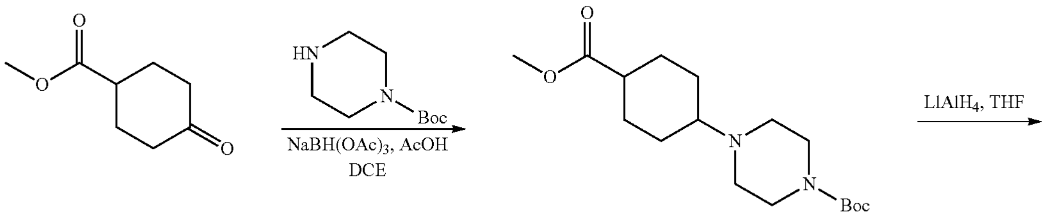

-continued

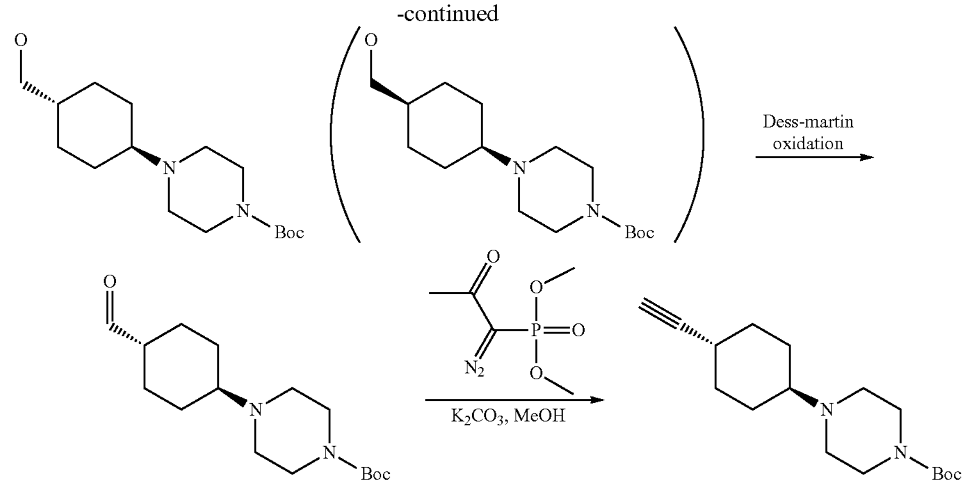

SM-L-5

1. Synthesis of Compound t-butyl 4-(4-(methoxycarbonyl)cyclohexyl)piperazine-1-carboxylate Methyl 4-oxocyclohexylcarboxylate (10.0 g, 64.0 mmol) and t-butyl piperazine-1-carboxylate (13.0 g, 70.0 mmol) were dissolved in 1,2-dichloroethane (200 mL), to which was then added acetic acid (7.6 g, 128.0 mmol), and finally sodium triacetoxyborohydride (34.0 g, 160 mmol) was added. The reaction solution was stirred overnight at room temperature. The reaction solution was diluted with water (200 mL) and extracted with dichloromethane (100 mL×3). The organic phase was combined, washed with saturated brine (50 mL×3), dried over anhydrous sodium sulfate, and purified by silica gel column chromatography (petroleum ether:ethyl acetate=1:1), to provide t-butyl 4-(4-(methoxycarbonyl)cyclohexyl)piperazine-1-carboxylate as a white solid (9.6 g, 29.4 mmol), with a yield of 46%. MS: calcd. for $C_{17}H_{30}N_2O_4[M+H]^+$: 327.2; found: 327.4.

2. Synthesis of Compound t-butyl 4-((1r,4r)-4-(hydroxymethyl)cyclohexyl) piperazine-1-carboxylate t-Butyl 4-(4-(methoxycarbonyl)cyclohexyl)piperazine-1-carboxylate (9.6 g, 29.4 mmol) was dissolved in tetrahydrofuran (200 mL), to which was added lithium aluminum hydride (2.23 g, 58.8 mmol) in portions in an ice bath. The reaction solution was continuously stirred in an ice bath for 1 h. The reaction solution was diluted with tetrahydrofuran (100 mL), kept in an ice bath, and then water (2.3 mL) was added dropwise. The mixture was further stirred for 10 min, and then 15% sodium hydroxide solution (2.3 mL) was added. The reaction solution was stirred for additional 10 min, to which was further added water (6.9 mL), and the resultant solution was continually stirred for 20 min. Finally, anhydrous magnesium sulfate was added, and the mixture was stirred for 20 min. The reaction mixture was filtered, and the filtrate was rotatory evaporated to dry. The residue was purified by silica gel column chromatography (petroleum ether:ethyl acetate=1:1 to 0:100), to provide t-butyl 4-((1r,4r)-4-(hydroxymethyl)cyclohexyl)piperazine-1-carboxylate (1.2 g, 4.0 mmol) as light yellow oil, with a yield of 14%. The configuration was determined by referring patent WO2012145361. MS: calcd. for $C_{14}H_{26}N_2O_3[M+H]^+$: 299.2; found: 299.4. $^1H$ NMR (400 MHz, $CDCl_3$): δ 3.46-3.33 (m, 6H), 2.51-2.38 (m, 4H), 2.28-2.17 (m, 1H), 1.91-1.84 (m, 4H), 1.62-1.48 (m, 1H), 1.42 (s, 9H), 1.27-1.13 (m, 3H), 1.02-0.88 (m, 2H).

At the same time, t-butyl 4-((1s,4s)-4-(hydroxymethyl) cyclohexyl)piperazine-1-carboxylate (3.0 g, 10.0 mmol) was obtained as light yellow oil, with a yield of 34%. MS: calcd. for $C_{14}H_{26}N_2O_3[M+H]^+$: 299.2; found: 299.4.

3. Synthesis of Compound t-butyl 4-((1r,4r)-4-(formyl)cyclohexyl)piperazine-1-carboxylate t-Butyl 4-((1r,4r)-4-(hydroxymethyl)cyclohexyl)piperazine-1-carboxylate (1.2 g, 4.0 mmol) was dissolved in dichloromethane (50 mL), to which was then added 1,1',1'-(3-oxo-1λ5-1,2-phenyliodo-1(3H)-yelidone)acetoacetate (2.0 g, 4.8 mmol). The reaction solution was stirred at room temperature for 24 h, and then filtered. The filtrate was rotatory evaporated to dry, to provide crude t-butyl 4-((1r,4r)-4-(formyl)cyclohexyl) piperazine-1-carboxylate (1.4 g), which was directly used in next reaction. MS: calcd. for $C_{16}H_{28}N_2O_3[M+H]^+$: 297.2; found: 297.4.

4. Synthesis of Compound t-butyl 4-((1r,3r)-4-ethynylcyclohexyl)piperazine-1-carboxylate t-Butyl 4-((1r,4r)-4-(formyl)cyclohexyl) piperazine-1-carboxylate (4.0 mmol, the crude product from step 1 of the previous method) and dimethyl 1-diazo-2-oxopropylphosphonate (7.2 g, 6.0 mmol) were dissolved in methanol (50 mL), to which was added potassium carbonate (1.1 g, 8.0 mmol) in an ice bath. The reaction solution was slowly warmed to room temperature and allowed to stand overnight. The reaction solution was diluted with water (50 mL) and extracted with ethyl acetate (50 mL×3). The organic phase was combined, washed with saturated brine (50 mL×3), dried over anhydrous sodium sulfate, and purified by silica gel column chromatography (petroleum ether:ethyl acetate=3:1 to 2:1), to provide t-butyl 4-((1r,3r)-3-ethynylcyclohexyl) piperazine-1-carboxylate as pale yellow solid (0.67 g, 2.3 mmol), with a two-step yield of 57%. MS: calcd. for $C_{17}H_{28}N_2O_2[M+H]^+$: 293.2; found: 293.2. $^1H$ NMR (400 MHz, $CDCl_3$): δ 3.46-3.36 (m, 4H), 2.53-2.44 (m, 4H), 2.35-2.23 (m, 1H), 2.22-2.11 (m, 1H), 2.09-2.00 (m, 3H), 1.93-1.83 (m, 2H), 1.45 (s, 9H), 1.43-1.34 (m, 2H), 1.28-1.20 (m, 2H).

The synthesis of intermediates SM-L-6, SM-L-7, SM-L-15. SM-L-16, SM-L-17, SM-L-18, SM-L-19, SM-L-20, SM-L-21, SM-L-22, SM-L-23 and SM-L-24 was similar to that of SM-L-18.
SM-L-5
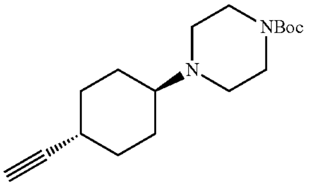
SM-L-6Q
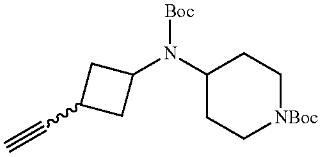
SM-L-6H
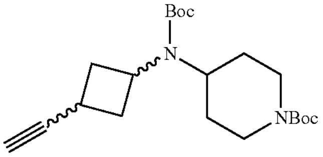
SM-L-7
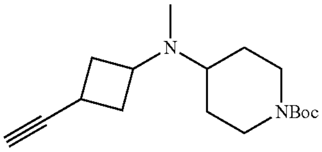
SM-L-15Q
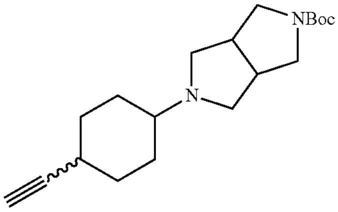
SM-L-15H
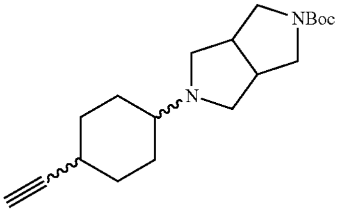
SM-L-16Q
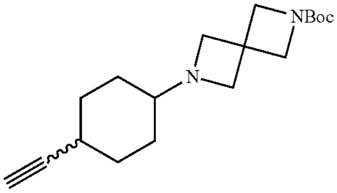
-continued
SM-L-16H
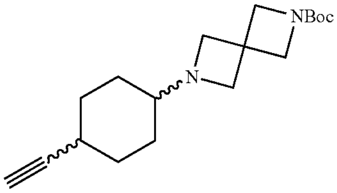
SM-L-17Q
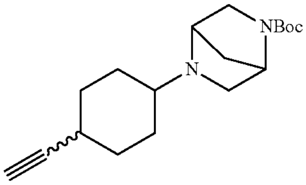
SM-L-17H
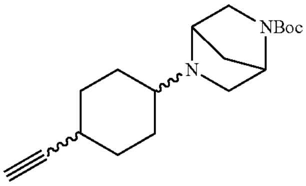
SM-L-18Q
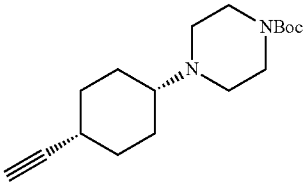
SM-L-18H
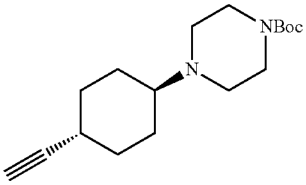
SM-L-19Q
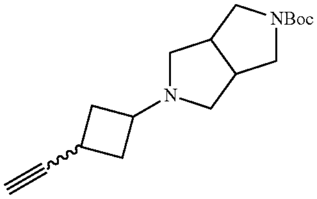
SM-L-19H
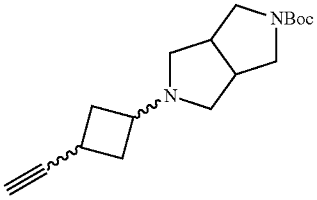
SM-L-20Q
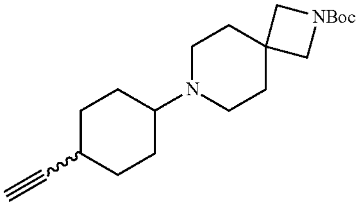

-continued
SM-L-20H
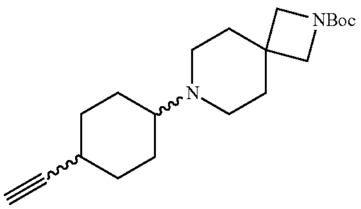
SM-L-21Q
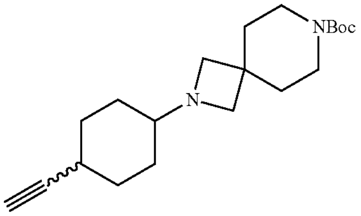
SM-L-21H
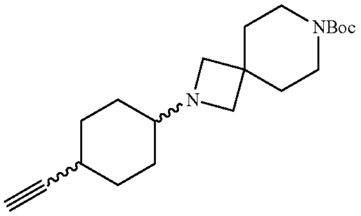
SM-L-22Q
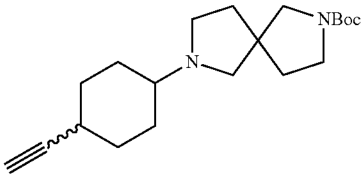
SM-L-22H
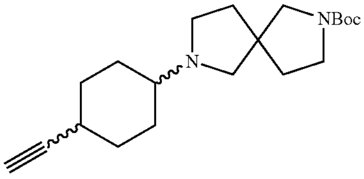
-continued
SM-L-23Q
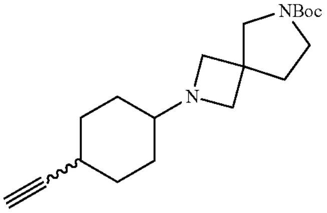
SM-L-23H
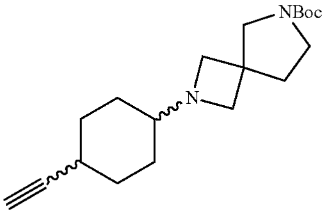
SM-L-24Q
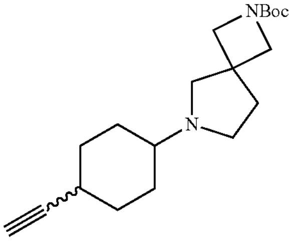
SM-L-24H
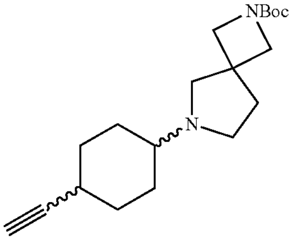
The following is the preparative examples of specific compounds provided in the present invention: 1: (3R,5S)-1-((S)-2-(2-((5-((4-(3-((1R,3R)-3-(3-chloro-4-cyanophenoxy)-2,2,4,4-tetramethylcyclobutyl)ureido)phenyl)amino)pentyl)oxy)acetylamino)-3,3-dimethylbutyryl)-5-(((S)-1-(4-(4-methylthiazol-5-yl))phenyl)ethyl)carbamoyl) pyrrolidin-3-yl acetate
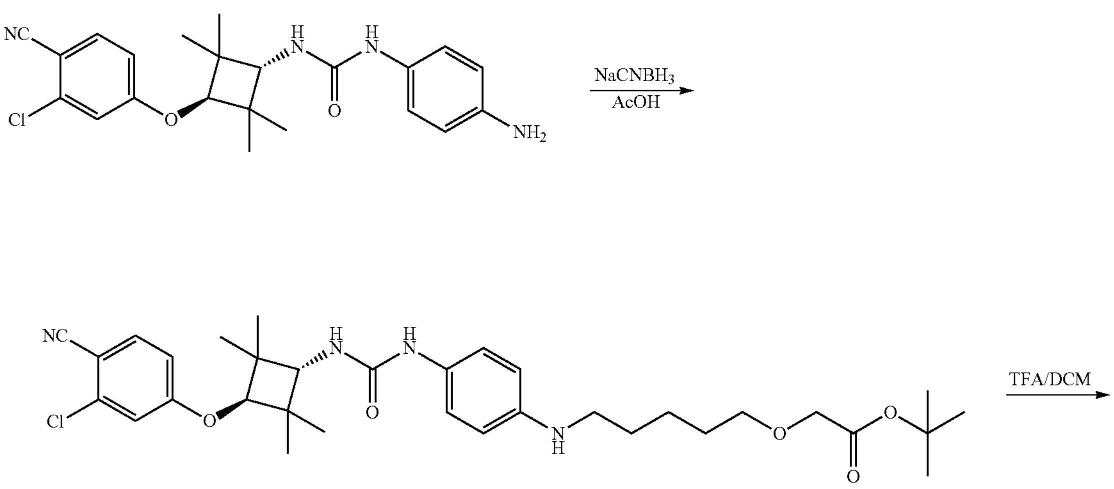

-continued

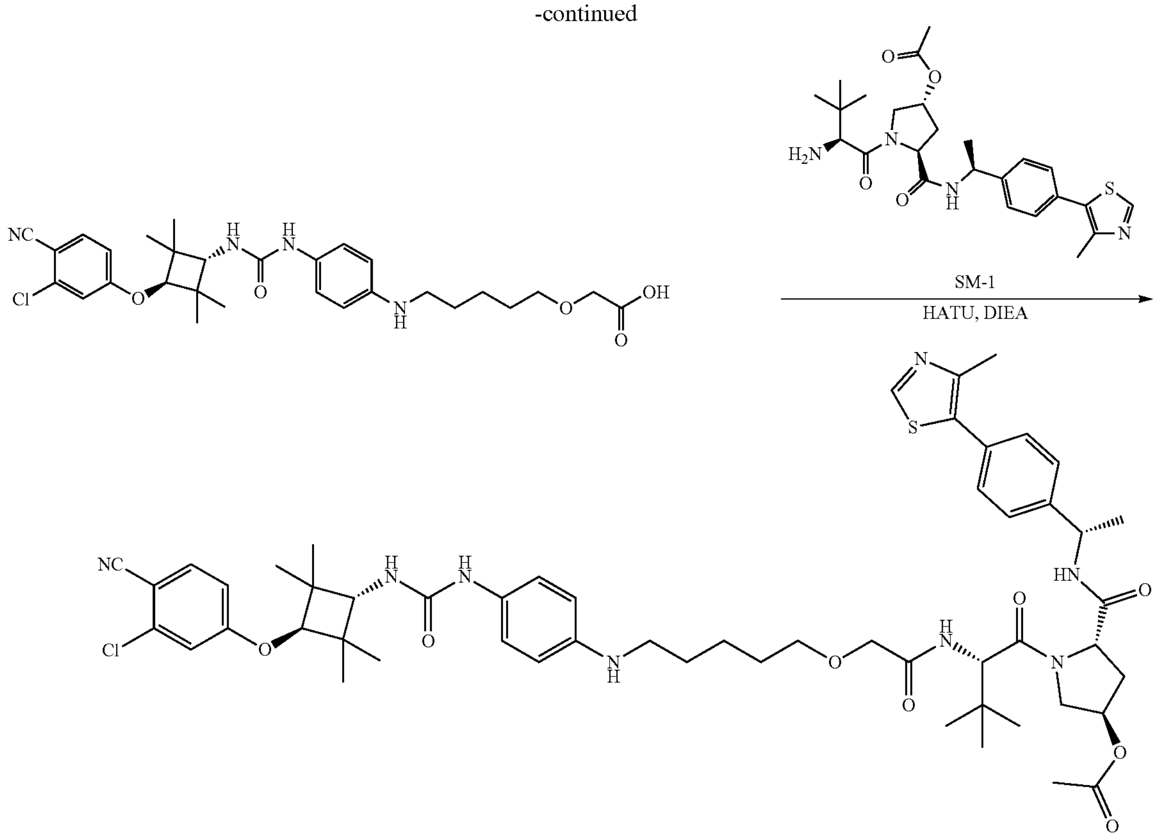

1

1. Synthesis of 2-((5-((4-(3-((1r,3r)-3-(3-chloro-4-cyanophenoxy)-2,2,4,4-tetramethylcyclobutyl) ureido)phenyl)ethyl)pentyl)oxy)amino t-butyl ester 1-(4-aminophenyl)-3-((1r,3r)-3-(3-chloro-4-cyanophenoxy)-2,2,4,4-tetramethylcyclobutyl)urea (100.0 mg, 0.24 mmol) and t-butyl 2-((5-oxopentyl)oxy)acetate (52.4 mg, 0.24 mmol) were dissolved in 5 ml DCM, and then the mixture was cooled to 0° C., to which was added one drop of acetic acid, followed by addition of sodium cyanoborohydride (45.6 mg, 0.73 mmol) in batches. The reaction mixture was warmed to room temperature and stirred overnight, to which was added water. The reaction solution was extracted with DCM, rotatory evaporated to dry, and purified by Pre-TLC, to provide compound 2-((5-((4-(3-((1r,3r)-3-(3-chloro-4-cyanophenoxy)-2,2,4,4-tetramethylcyclobutyl) ureido)phenyl)ethyl)pentyl)oxy)amino t-butyl ester (73.4 mg), with a yield of 54.6%. LC/MS (ESI+) Calcd for $C_{33}H_{45}ClN_4O_5(M-56+H^+)$ m/z, 612.3; Found, 557.3.

2. 2-((5-((4-(3-((1r,3r)-3-(3-chloro-4-cyanophenoxy)-2,2,4,4-tetramethylcyclobutyl)ureido)phenyl) amino)pentyl)oxy)acetic acid 2-((5-((4-(3-((1r,3r)-3-(3-chloro-4-cyanophenoxy)-2,2,4, 4-tetramethylcyclobutyl) ureido)phenyl)ethyl)pentyl)oxy) amino t-butyl ester (70.0 mg, 0.09 mmol) was dissolved in 2 ml DCM, to which was added 5 ml TFA, and the mixture was stirred for 1 h at room temperature. The raw material was completely reacted by TLC detection, and then the system was rotatory evaporated to dry, to which was added DCM to dissolve the residue. The resultant solution was washed with saturated $NaHCO_3$ aqueous solution until the pH was about 6. The organic phase was dried, filtered, and concentrated, to provide 2-((5-((4-(3-((1r,3r)-3-(3-chloro-4-cyanophenoxy)-2,2,4,4-tetramethylcyclobutyl)ureido)phenyl)amino)pentyl)oxy)acetic acid (21.3 mg), with a yield of 32.6%.

3. Synthesis of (3R,5S)-1-((S)-2-(2-((5-((4-(3-((1R, 3R)-3-(3-chloro-4-cyanophenoxy)-2,2,4,4-tetramethylcyclobutyl)ureido)phenyl)amino)pentyl) oxy) acetylamino)-3,3-dimethylbutyryl)-5-(((S)-1-(4-(4-methylthiazol-5-yl)) phenyl)ethyl)carbamoyl) pyrrolidin-3-yl acetate 2-((5-((4-(3-((1r,3r)-3-(3-chloro-4-cyanophenoxy)-2,2,4, 4-tetramethylcyclobutyl) ureido)phenyl)amino)pentyl)oxy) acetic acid (20.0 mg, 0.09 mmol) was dissolved in 2 ml DMF, and then cooled to about 0° C. to which were added 0.5 ml DIEA and HATU (29.1 mg, 0.13 mmol). The mixture was stirred 5 min, to which was then added (3R,5S)-1-((S)-2-amino-3,3-dimethylbutyryl)-5-(((S)-1-(4-(4-methylthiazol-5-yl)phenyl)ethyl) amido)pyrrolidine-3-acetate (26.0 mg, 0.10 mmol). The resultant mixture was warmed to room temperature and stirred 1 h, and then ethyl acetate and 1N hydrochloric acid solution were added for extraction. The organic layer was washed twice with brine, dried, rotatory evaporated to dry, and purified by silica gel column chromatography, to provide compound (3R,5S)-1-((S)-2-(2-((5-((4-(3-((1R,3R)-3-(3-chloro-4-cyanophenoxy)-2,2,4,4-tetramethylcyclobutyl)ureido)phenyl)amino)pentyl)oxy)

acetylamino)-3,3-dimethylbutyryl)-5-(((S)-1-(4-(4-methylthiazol-5-yl))phenyl)ethyl) carbamoyl)pyrrolidin-3-yl acetate (8.2 mg), with a yield of 37.2%. LC/MS ($ESI^+$) Calcd for $C_{54}H_{69}ClN_8O_8S$ ($M+H^+$) m/z, 1024.5; Found, 1024.4. $^1H$ NMR (400 MHz, DMSO-$d_6$) δ 9.21 (m, 1H), 9.11 (m, 1H), 8.87-8.82 (d, J=7.6 Hz, 1H), 8.13 (m, 1H), 7.90 (d, J=8.8 Hz, 1H), 7.38 (dt, J=8.7, 7.5 Hz, 6H), 7.28 (d, J=2.4 Hz, 1H), 7.06 (dd, J=8.8, 2.4 Hz, 1H), 6.85 (d, J=8.3 Hz, 1H), 6.77 (s, 1H), 5.87 (s, 1H), 5.20 (s, 1H), 4.93-4.88 (m, 1H), 4.60 (s, 2H), 4.53 (s, 1H), 4.45 (dd, J=14.4, 8.7 Hz, 2H), 4.29 (s, 1H), 3.90 (dd, J=16.2, 6.4 Hz, 31), 3.77 (dd, J=11.8, 3.9 Hz, 1H), 3.49 (t, J=6.4 Hz, 2H), 3.05 (s, 2H), 2.45 (s, 3H), 2.29-2.23 (m, 1H), 2.09 (s, 1H), 1.99 (s, 3H), 1.98 (d, J=3.1 Hz, 1H), 1.62-1.56 (m, 4H), 1.45 (d, J=4.9 Hz, 3H), 1.39 (s, 6H), 1.31 (s, 1H), 1.21 (s, 6H), 0.93 (s, 9H).

2: (3R,5S)-1-((S)-2-(2-(2-(4-(2-((1R,3R)-3-(3-chloro-4-cyanophenoxy)-2,2,4,4-tetramethylcyclobutyl)-1-oxoisoindolin-5-yl)piperazin-1-yl)ethoxy)acetylamino)-3,3-dimethylbutyryl)-5-(((S)-1-(4-(4-methylthiazol-5-yl)phenyl)ethyl)carbamoyl)pyrrolidin-3-yl acetate

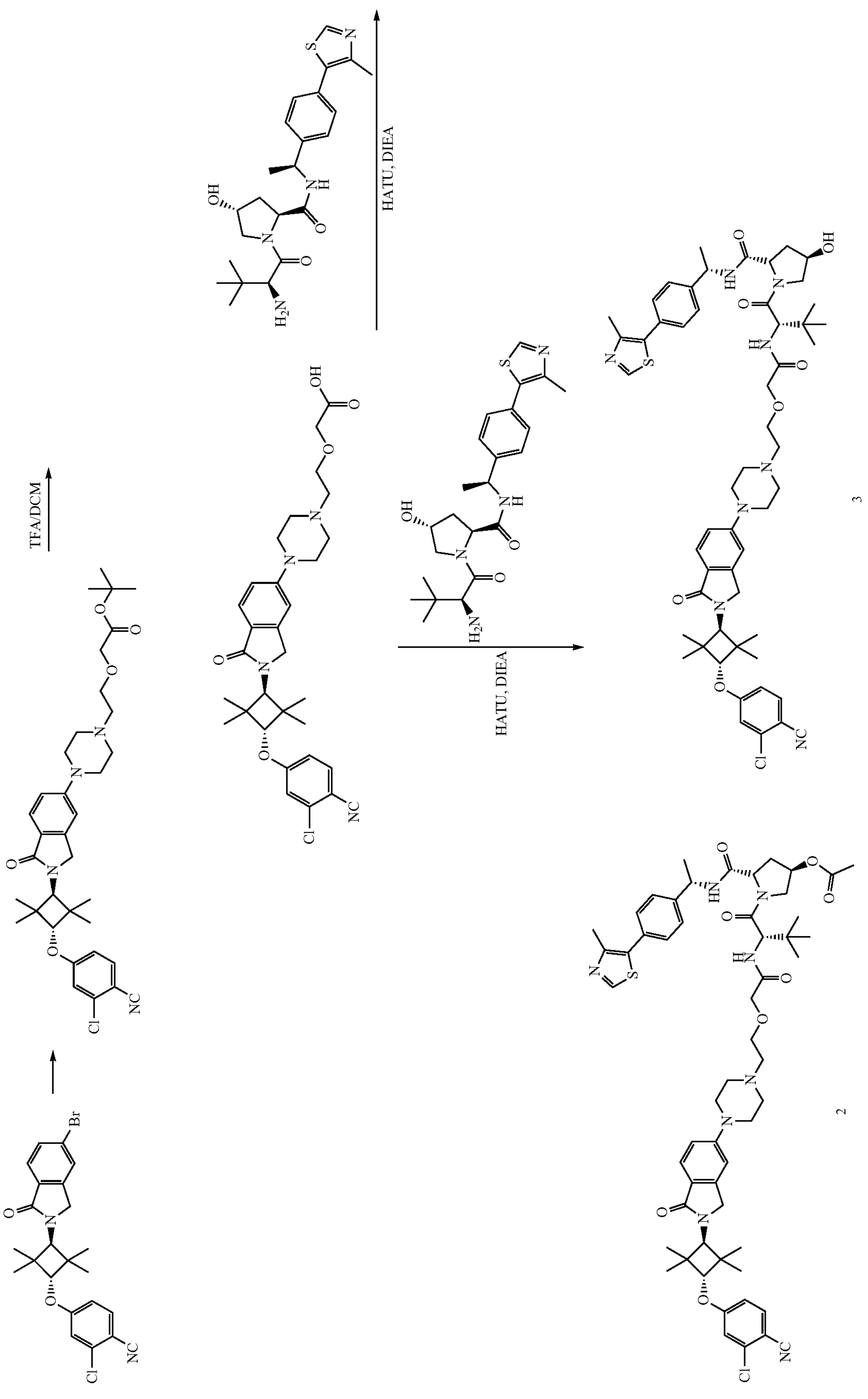
3
2

1. Synthesis of t-butyl 2-(2-(4-(2-((1r,3r)-3-(3-chloro-4-cyanophenoxy)-2,2,4,4-tetramethylcyclobutyl)-1-oxoisoindoline)piperazin-1-yl) ethoxy)-5-acetate t-Butyl 4-((1r,3r)-3-(5-bromo-1-oxoisoindolin-2-yl))-2,2,4,4-tetramethylcyclobutoxy)-2-chlorobenzonitrile (100.0 mg, 0.21 mmol), t-butyl 2-(2-(piperazin-1-yl)ethoxy)acetate (154.5 mg, 0.63 mmol), BINAP (39.0 mg, 0.633 mmol), $Pb_2(dba)_3$ (19.1 mg, 0.02 mmol), and $Cs_2CO_3$ (137.5 mg, 0.42 mmol) were dissolved in 10 ml of toluene, and the mixture was heated to 100° C. after purging nitrogen, then allowed to react overnight. The reaction solution was filtered through a pad of celite, and the filtrate was concentrated. To the residue, was added water, and then extracted with dichloromethane. The organic phase was dried, filtered, concentrated, and purified by Pre-TLC, to provide the compound t-butyl 2-(2-(4-(2-((1r,3r)-3-(3-chloro-4-cyanophenoxy)-2,2,4,4-tetramethylcyclobutyl)-1-oxoisoindoline)piperazin-1-yl) ethoxy)-5-acetate (94.7 mg), with a yield of 49.3%. LC/MS ($ESI^+$) Calcd for $C_{33}H_{45}ClN_4O$ ($M-56+H^+$) m/z, 636.3; Found, 581.2.

2. Synthesis of Compound 2-(2-(4-(2-((1r,3r)-3-(3-chloro-4-cyanophenoxy)-2,2,4,4-tetramethylcyclobutane)-1-dioxoisoindolin-5-yl)piperazin-1-yl) ethoxy) acetic acid t-Butyl 2-(2-(4-(2-((1r,3r)-3-(3-chloro-4-cyanophenoxy)-2,2,4,4-tetramethyl cyclobutyl)-1-oxoisoindoline)piperazin-1-yl)ethoxy)-5-acetate (90.0 mg, 0.19 mmol) was dissolved in 1 ml dichloromethane, to which was then added 5 ml trifluoroacetic acid, and the mixture was stirred 30 min at room temperature. Once the reaction was completed by TLC detection, the reaction solution was directly rotatory evaporated to dry, and then dichloromethane was added to dissolve the residue. The resultant solution was adjusted to pH=6 with saturated aqueous solution of sodium bicarbonate, and the solution was separated. The organic phase was dried with anhydrous sodium sulfate, filtered, and rotatory evaporated to dry, to provide the compound 2-(2-(4-(2-((1r,3r)-3-(3-chloro-4-cyanophenoxy)-2,2,4,4-tetramethylcyclobutane)-1-dioxoisoindolin-5-yl) piperazin-1-yl)ethoxy)acetic acid (63.3 mg), with a yield of 89.3%.

3. Synthesis of (3R,5S)-1-((S)-2-(2-(2-(4-(2-((1R,3R)-3-(3-chloro-4-cyanophenoxy)-2,2,4,4-tetramethylcyclobutyl)-1-oxoisoindolin-5-yl)piperazin-1-yl) ethoxy) acetylamino)-3,3-dimethylbutyryl)-5-(((S)-1-(4-(4-methylthiazol-5-yl)phenyl) ethyl)carbamoyl) pyrrolidin-3-yl acetate 2-(2-(4-(2-((1r,3r)-3-(3-chloro-4-cyanophenoxy)-2,2,4,4-tetramethylcyclobutane)-1-dioxoisoindolin-5-yl)piperazin-1-yl)ethoxy)acetic acid (30.0 mg, 0.09 mmol) was dissolved in 2 ml DMF, and then cooled to about 0° C., to which were added 0.5 ml DIEA and HATU (29.1 mg, 0.13 mmol). The mixture was stirred 5 min, to which was then added (3R,5S)-1-((S)-2-amino-3,3-dimethylbutyryl)-5-(((S)-1-(4-(4-methylthiazol-5-yl)phenyl)ethyl)amido)pyrrolidine-3-acetate (26.0 mg, 0.10 mmol). The resultant mixture was warmed to room temperature and stirred 1 h, and then ethyl acetate and 1N hydrochloric acid solution were added for extraction. The organic layer was washed twice with brine, dried, rotatory evaporated to dry, and purified by silica gel column chromatography, to provide compound (3R,5S)-1-((S)-2-(2-(2-(4-(2-((1R,3R)-3-(3-chloro-4-cyanophenoxy)-2,2,4,4-tetramethylcyclobutyl)-1-oxoisoindolin-5-yl) piperazin-1-yl)ethoxy)acetylamino)-3,3-dimethylbutyryl)-5-(((S)-1-(4-(4-methylthiazol-5-yl)phenyl)ethyl)carbamoyl) pyrrolidin-3-yl acetate (11.6 mg), with a yield of 33.5%. LC/MS ($ESI^+$) Calcd for $C_{56}H_{69}ClN_8O_8S$ ($M+H^+$) m/z, 1048.5; Found, 1048.5. $^1H$ NMR (400 MHz, DMSO-$d_6$) δ 9.02 (m, 1H), 8.98-8.93 (m, 1H), 8.47 (d, J=7.6 Hz, 1H), 7.97 (d, J=8.8 Hz, 1H), 7.38 (dt, J=8.7, 7.5 Hz, 6H), 7.28 (d, J=2.4 Hz, 1H), 7.06 (dd, J=8.8, 2.4 Hz, 1H), 6.85 (d, J=8.3 Hz, 1H), 6.77 (s, 1H), 5.87 (s, 1H), 5.20 (s, 1H), 4.93-4.88 (m, 1H), 4.60 (s, 2H), 4.53 (s, 1H), 4.45 (dd, J=14.4, 8.7 Hz, 2H), 4.29 (s, 1H), 4.22-4.05 (m, 4H), 3.90 (dd, J=16.2, 6.4 Hz, 3H), 3.77 (dd, J=11.8, 3.9 Hz, 1H), 3.49 (t, J=6.4 Hz, 2H), 3.05 (s, 2H), 2.29-2.23 (m, 1H), 2.09 (s, 1H), 1.99 (s, 3H), 1.98 (d, J=3.1 Hz, 1H), 1.45 (d, J=4.9 Hz, 3H), 1.37 (s, 6H), 1.35 (s, 1H), 1.14 (s, 6H), 0.95 (s, 9H).

3: Compound (2S,4R)-1-((S)-2-(2-(2-(4-(2-((1R,3R)-3-(3-chloro-4-cyanophenoxy)-2,2,4,4-tetramethylcyclobutyl)-1-oxoisoindolin-5-yl)piperazin-1-yl) ethoxy) acetylamino)-3,3-dimethylbutyryl)-4-hydroxy-N-((S)-1-(4-(4-methylthiazol-5-yl)phenyl) ethyl)pyrrolidine-2-carboxamide

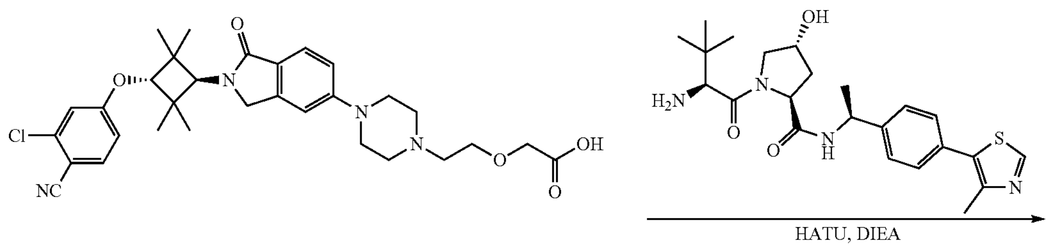

-continued

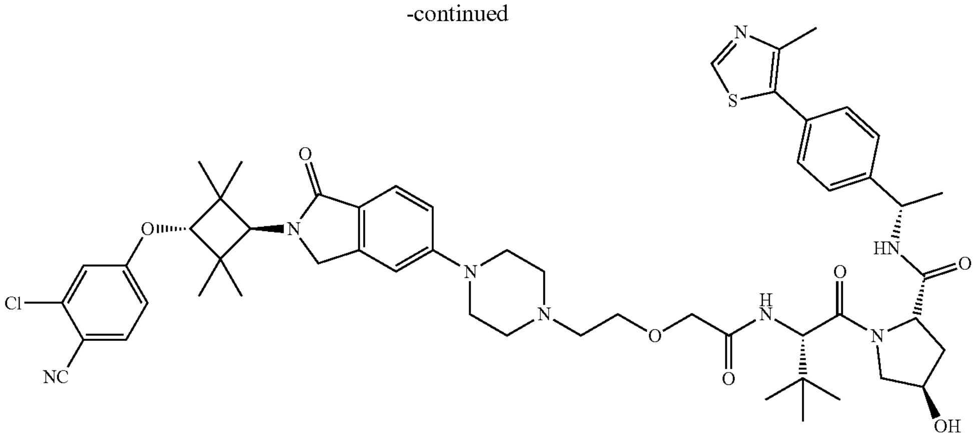

3

2-(2-(4-(2-((1r,3r)-3-(3-chloro-4-cyanophenoxy)-2,2,4,4-tetramethylcyclobutane)-1-dioxoisoindolin-5-yl)piperazin-1-yl)ethoxy)acetic acid (30.0 mg, 0.09 mmol) was dissolved in 2 ml DMF, and then cooled to about 0° C., to which were added 0.5 ml DIEA and HATU (29.1 mg, 0.13 mmol). The mixture was stirred 5 min, to which was then added (2S, 4R)-1-((S)-2-amino-3,3-dimethylbutyryl)-4-hydroxy-N-((S)-1-(4-(4-methylthiazol-5-yl)phenyl)ethyl)amido)pyrrolidine-2-carboxamide (24.0 mg, 0.10 mmol). The resultant mixture was warmed to room temperature and stirred 1 h, and then ethyl acetate and 1N hydrochloric acid solution were added for extraction. The organic layer was washed twice with brine, dried, rotatory evaporated to dry, and purified by silica gel column chromatography, to provide compound (3R,5S)-1-((S)-2-(2-(2-(4-(2-((1R,3R)-3-(3-chloro-4-cyanophenoxy)-2,2,4,4-tetramethylcyclobutyl)-1-oxoisoindolin-5-yl)piperazin-1-yl) ethoxy)acetylamino)-3,3-dimethylbutyryl)-5-(((S)-1-(4-(4-methylthiazol-5-yl) phenyl)ethyl)carbamoyl)pyrrolidin-3-yl acetate (8.2 mg), with a yield of 31.7%. LC/MS ($ESI^+$) Calcd for $C_{54}H_{67}ClN_8O_7S$ ($M+H^+$) m/z, 1007.5; Found, 1007.5. $^1H$ NMR (400 MHz, DMSO-$d_6$) δ 9.14 (m, 1H), 9.02 (m, 1H), 8.47 (d, J=7.6 Hz, 1H), 7.97 (d, J=8.8 Hz, 1H), 7.38 (dt, J=8.7, 7.5 Hz, 6H), 7.28 (d, J=2.4 Hz, 1H), 7.06 (dd, J=8.8, 2.4 Hz, 1H), 6.85 (d, J=8.3 Hz, 1H), 6.77 (s, 1H), 5.87 (s, 1H), 5.20 (s, 1H), 4.93-4.88 (m, 1H), 4.60 (s, 2H), 4.53 (s, 1H), 4.45 (dd, J=14.4, 8.7 Hz, 2H), 4.29 (s, 1H), 4.22-4.05 (m, 4H), 3.90 (dd, J=16.2, 6.4 Hz, 3H), 3.77 (dd, J=11.8, 3.9 Hz, 1H), 3.49 (t, J=6.4 Hz, 2H), 3.05 (s, 2H), 2.45 (s, 3H), 2.29-2.23 (m, 1H), 2.09 (s, 1H), 1.99 (s, 3H), 1.98 (d, J=3.1 Hz, 1H), 1.45 (d, J=4.9 Hz, 3H), 1.37 (s, 6H), 1.35 (s, 1H), 1.14 (s, 6H), 0.95 (s, 9H).

4: (3R,5R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-5-(((S)-1-(4-(4-methylthiazol-5-yl)phenyl)ethyl)carbamoyl) pyrrolidin-3-yl acetate

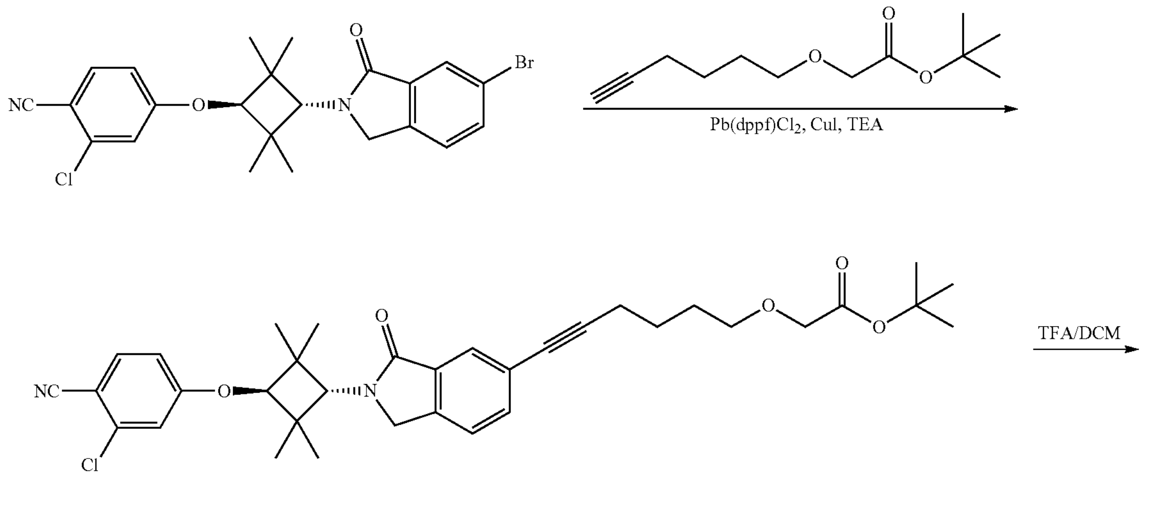

-continued

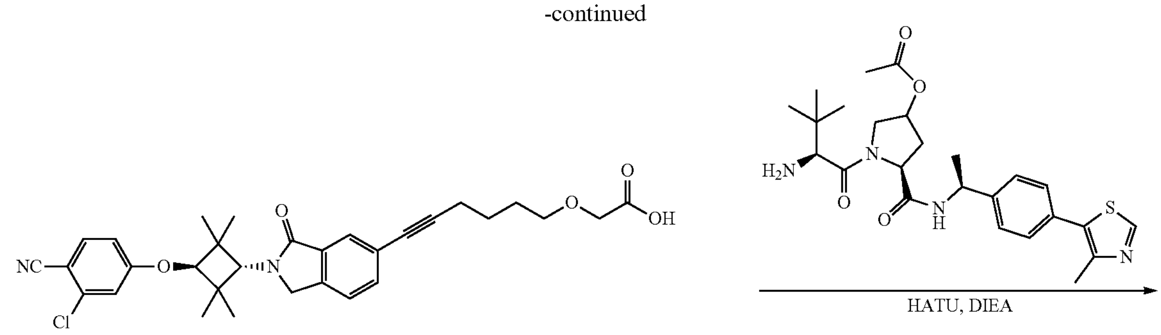

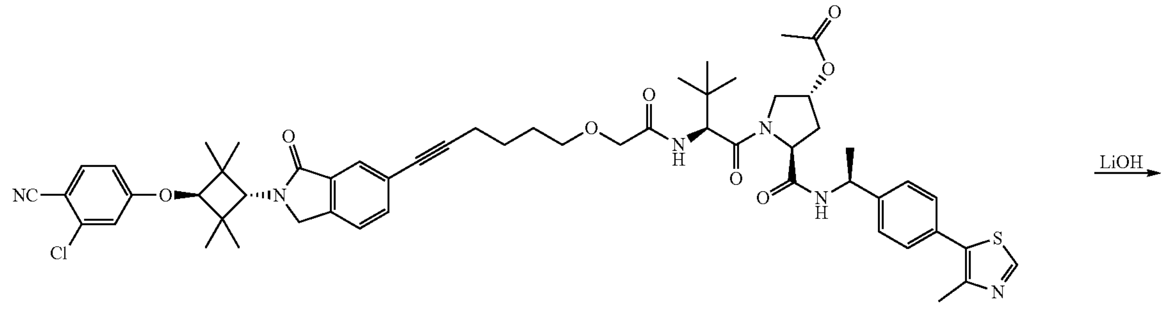

4

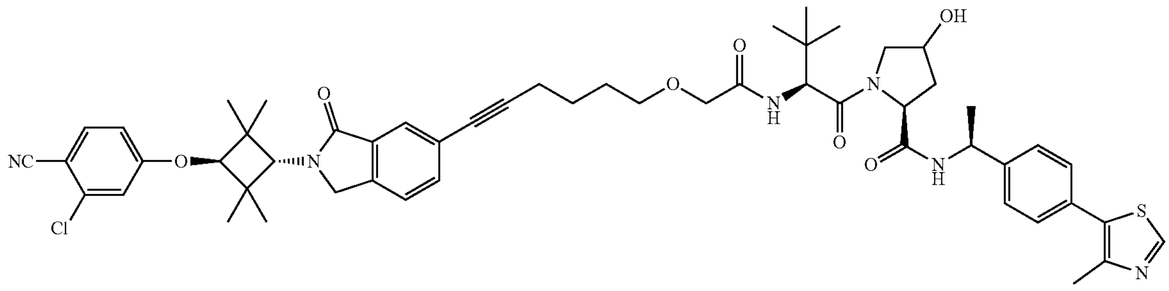

5

1. Synthesis of Compound t-butyl 2-((6-(2-((1r,3r)-3-(3-chloro-4-cyanophenoxy)-2,2,4,4-tetramethylcyclobutyl)-3-oxoisoindol-5-yl)hex-5-yn-1-yl)oxy) acetate 4-((1r,3r)-3-)-6-Bromo-1-oxoisoindolin-2-yl))-2,2,4,4-tetramethylcyclobutoxy)-2-chlorobenzonitrile (85.0 mg, 0.18 mmol), $PbdppfCl_2$ (26.5 mg, 0.04 mmol), CuI (17.5 mg, 0.09 mmol), and t-butyl 2-(hex-5-yn-1-yloxy)acetate (38.5 mg, 0.18 mmol) were sequentially added to the reaction flask, and then nitrogen was purged, to which were added 1.2 ml of toluene and 0.4 ml of triethylamine by syringe. After that, the system was purged with nitrogen again. The mixture was allowed to react overnight at 110° C., and the reaction was completed by TLC detection. The system was cooled to room temperature and filtered through a pad of celite. The filtrate was concentrated, to which was added dichloromethane, and then the organic phase was successively washed with 0.5 M HCl and saturated brine. The organic phase was dried, filtered, concentrated in vacuo, and purified by Pre-TLC, to provide t-butyl 2-((6-(2-((1 r,3r)-3-(3-chloro-4-cyanophenoxy)-2,2,4,4-tetramethylcyclobutyl)-3-oxoisoindol-5-yl)hex-5-yn-1-yl)oxy) acetate (97.3 mg), with a yield of 78.8%. LC/MS (ESI+) Calcd for $C_{35}H_{41}ClN_2O_5$($M-56+H^+$) m/z, 604.3; Found, 549.2.

2. Synthesis of 2-((6-(2-((1r,3r)-3-(3-chloro-4-cyanophenoxy)-2,2,4,4-tetramethylcyclobutyl)-3-oxoisoindol-5-yl)hex-5-yn-1-yl)oxy)acetic acid t-Butyl 2-((6-(2-((1r,3r)-3-(3-chloro-4-cyanophenoxy)-2,2,4,4-tetramethylcyclobutyl)-3-oxoisoindol-5-yl)hex-5-yn-1-yl)oxy)acetic acid (95.0 mg, 0.15 mmol) was dissolved in 1 ml DCM, to which was added 5 ml TFA, and the mixture was allowed to react 1 h at room temperature. The raw material was completely reacted by TLC detection, and then the system was rotatory evaporated to dry, to which was added DCM to dissolve the residue. The resultant solution was washed with saturated $NaHCO_3$ aqueous solution until the pH was about 6. The organic phase was dried, filtered, and concentrated, to provide 2-((6-(2-((1r,3r)-3-(3-chloro-4-cyanophenoxy)-2,2,4,4-tetramethylcyclobutyl)-3-oxoisoindol-5-yl)hex-5-yn-1-yl)oxy)acetic acid (81.2 mg), with a yield of 92.6%.

3. (3R,5R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-5-(((S)-1-(4-(4-methylthiazol-5-yl)phenyl)ethyl)carbamoyl) pyrrolidin-3-yl acetate (4)

2-((6-(2-((1r,3r)-3-(3-Chloro-4-cyanophenoxy)-2,2,4,4-tetramethylcyclobutyl)-3-oxoisoindol-5-yl)hex-5-yn-1-yl)oxy)acetic acid (80.0 mg, 0.12 mmol) was dissolved in 2 ml DMF, to which was added DIEA (98.5 mg, 0.76 mmol), and the mixture was cooled to about 0° C., to which was added HATU (96.0 mg, 0.18 mmol). The mixture was stirred 10 min, to which was then added (2S,4R)-1-((S)-2-amino-3,3-dimethylbutyryl)-4-hydroxy-N-((S)-1-(4-(4-methylthiazol-5-yl)phenyl)ethyl)amido) pyrrolidine-2-carboxamide (130.1 mg, 0.22 mmol). The resultant mixture was warmed to room temperature and allowed to react 2 h. The reaction was completed by TLC detection, and then 5 ml $H_2O$ was slowly added to the system. The resultant solution was extracted with ethyl acetate, and the organic phase was washed with water for 5 times, followed by washing with 0.5 M HCl and saturated brine, respectively. The organic phase was dried, filtered, concentrated n vacuo, and purified by Pre-TLC, to provide (3R,5R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-5-(((S)-1-(4-(4-methylthiazol-5-yl)phenyl)ethyl) carbamoyl) pyrrolidin-3-yl acetate (38.0 mg), with a yield of 53.8%. $^1H$ NMR (400 MHz, $CDCl_3$) δ 8.69 (s, 1H), 7.88 (s, 1H), 7.59-7.54 (m, 2H), 7.38 (dd, J=16.0, 8.3 Hz, 6H), 7.19 (d, J=9.2 Hz, 1H), 6.99 (d, J=2.4 Hz, 1H), 6.83 (dd, J=8.7, 2.4 Hz, 1H), 5.35 (s, 1H), 5.10-5.05 (m, 1H), 4.75 (dd, J=8.3, 6.5 Hz, 1H), 4.65 (s, 2H), 4.59 (d, J=9.3 Hz, 1H), 4.39 (s, 1H), 4.31 (s, 1H), 4.05 (d, J=13.0 Hz, 1H), 3.96 (d, J=6.2 Hz, 2H), 3.83 (dd, J=11.6, 4.9 Hz, 1H), 3.59 (t, J=6.2 Hz, 2H), 2.74-2.68 (m, 1H), 2.53 (s, 3H), 2.50 (s, 1H), 2.16-2.10 (m, 1H), 2.03 (d, J=8.6 Hz, 4H), 1.86-1.80 (m, 2H), 1.73 (dd, J=11.5, 4.6 Hz, 2H), 1.47 (d, J=6.9 Hz, 3H), 1.44 (t, J=3.1 Hz, 6H), 1.25 (s, 6H), 1.05 (s, 9H). LC/MS ($ESI^+$) Calcd for $C_{56}H_{65}ClN_6O_8S$ ($M/2+H^+$) m/z, 1016.5; Found, 509.3.

5: (2R,4R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-4-hydroxy-N-((S)-1-(4-(4-methylthiazol-5-yl)phenyl)ethyl) pyrrolidine-2-carboxamide (5)

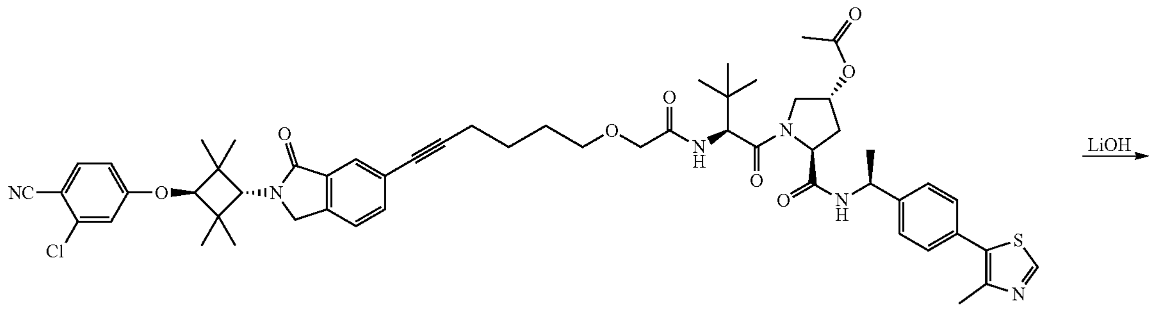

4

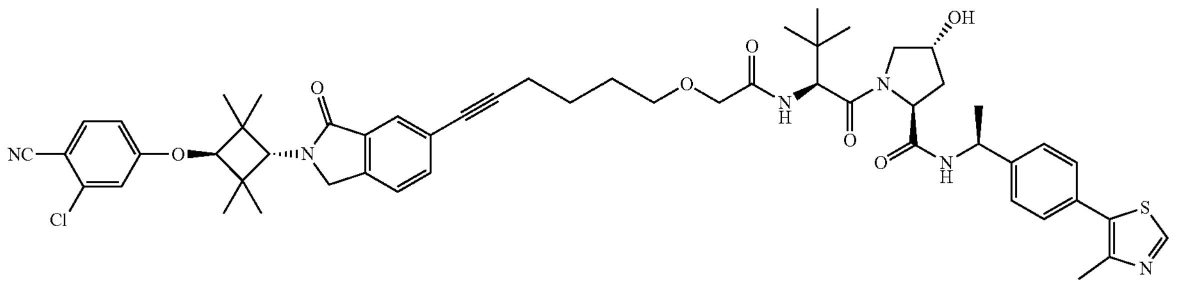

5

(3R,5R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-5-(((S)-1-(4-(4-methylthiazol-5-yl)phenyl)ethyl) carbamoyl) pyrrolidin-3-yl acetate (5.0 mg, 4.54 μmol) was dissolved in 1 ml methanol, to which was slowly added the mixed system of $LiOH.H_2O$ (0.9 mg, 0.02 mmol) and 0.5 ml $H_2O$. After about 30 min, TLC ANALYSIS indicated that the reaction was completed. The system was added with water, extracted with DCM, and purified by Pre-TLC, to provide the compound (2R,4R)-1-((S)-2-(2-((6-(2-((1R,3R)-3-(3-chloro-4-cyanophenoxy)-2,2,4,4-tetramethylcyclobutyl)-3-oxoisoindolin-5-yl)hex-5-yn-1-yl)oxy)acetylamino)-3,3-dimethylbutyryl)-4-hydroxy-N-((S)-1-(4-(4-methylthiazol-5-yl)phenyl)ethyl) pyrrolidine-2-carboxamide (3.0 mg), with a yield of 84.3%. $^1$H NMR (400 MHz, $CDCl_3$) δ 8.71 (s, 1H), 7.86 (s, 1H), 7.57 (dd, J=7.6, 4.6 Hz, 2H), 7.53-7.46 (m, 1H), 7.38 (q, J=8.5 Hz, 5H), 7.23 (d, J=9.0 Hz, 1H), 6.99 (d, J=2.3 Hz, 1H), 6.83 (dd, J=8.7, 2.3 Hz, 1H), 5.11-5.03 (m, 1H), 4.78 (t, J=7.9 Hz, 1H), 4.65 (s, 2H), 4.54 (d, J=8.4 Hz, 2H), 4.40 (s, 1H), 4.31 (s, 1H), 4.15 (d, J=11.3 Hz, 1H), 3.95 (t, J=11.5 Hz, 2H), 3.60 (t, J=6.1 Hz, 3H), 2.54 (s, 4H), 2.50 (t, J=6.7 Hz, 2H), 2.13-1.98 (m, 2H), 1.82 (d, J=6.6 Hz, 2H), 1.78-1.73 (m, 2H), 1.47 (d, J=6.9 Hz, 3H), 1.44 (s, 6H), 1.25 (s, 6H), 1.07 (s, 9H). LC/MS ($ESI^+$) Calcd for $C_{54}H_{63}ClN_6O_7S$ ($M+H^+$) m/z, 975.4; Found, 975.5.

6: (3R,5S)-1-((S)-2-(2-((5-((2-((1R,3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-5-(((S)-1-(4-(4-methylthiazol-5-yl)phenyl)ethyl)carbamoyl) pyrrolidin-3-yl acetate (6)

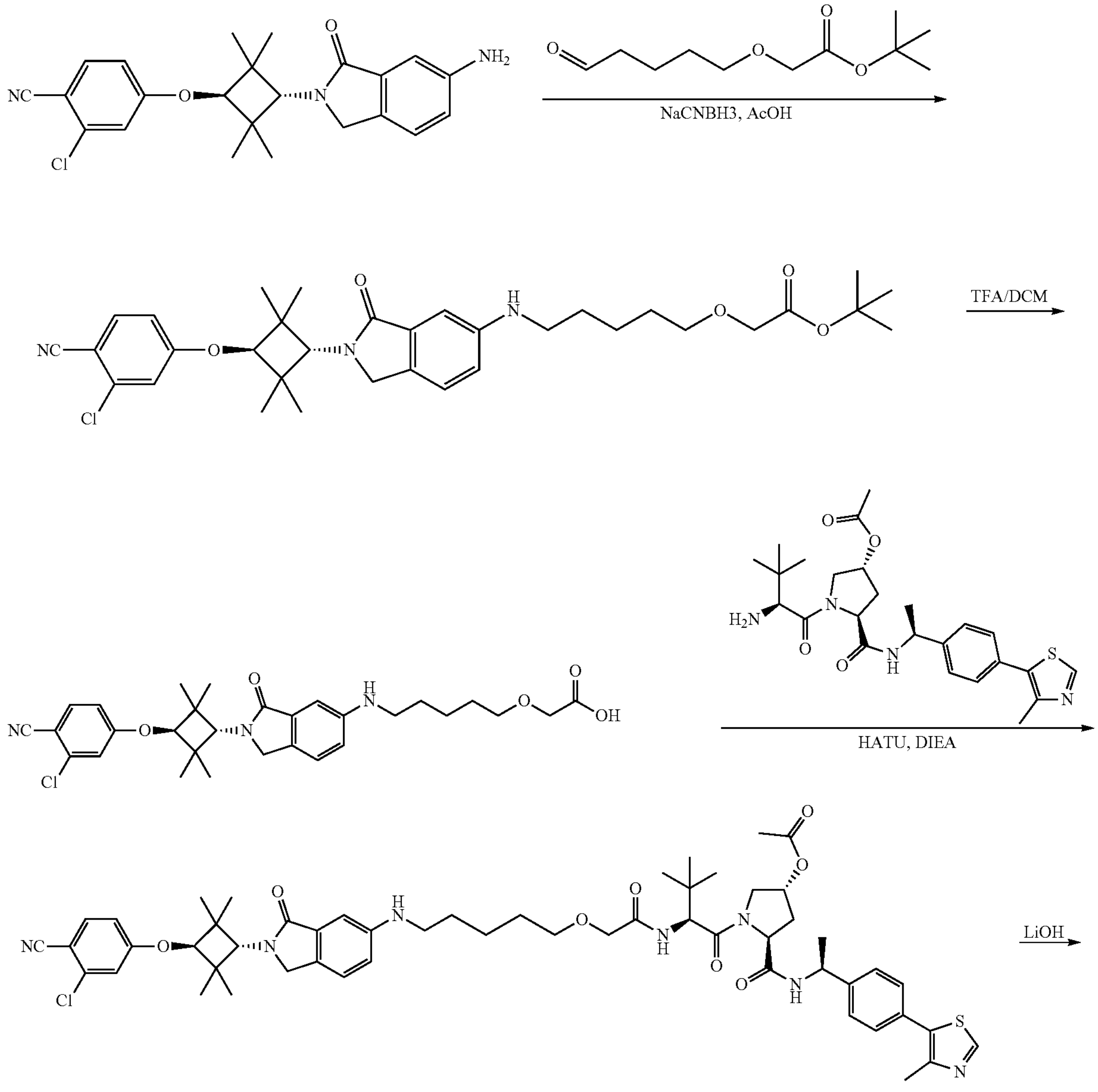

6

-continued

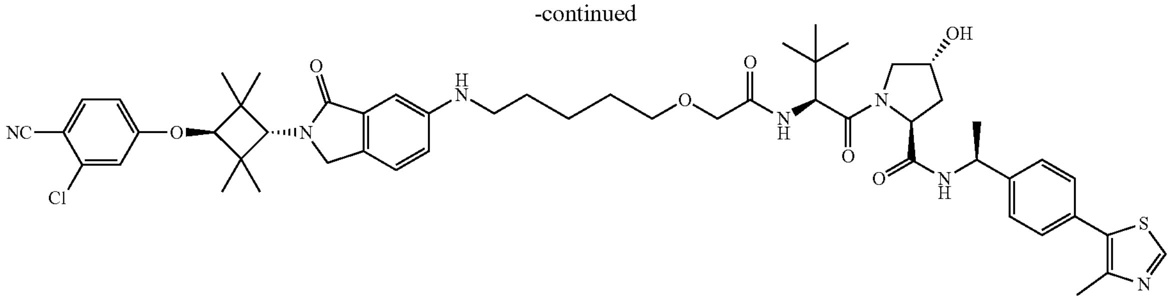

7

1. Synthesis of t-butyl 2-((2-((2-((1r,3r)-3-(3-chloro-4-cyanophenoxy)-2,2,4,4-tetramethylcyclobutyl)-3-oxoisoindol-5-yl)amino)pentyl)oxy)acetate 4-((1r,3r)-3-(6-amino-1-oxoisoindolin-2-yl))-2,2,4,4-tetramethylcyclobutoxy)-2-chlorobenzonitrile (150.0 mg, 0.37 mmol) and t-butyl 2-((5-oxopentyl)oxy)acetate (79.1 mg, 0.35 mmol) were dissolved in 5 ml DCM, and then the mixture was cooled to 0° C., to which was added one drop of acetic acid, followed by addition of sodium cyanoborohydride (58.6 mg, 0.92 mmol) in batches. The reaction mixture was warmed to room temperature and stirred overnight, to which was added water. The reaction solution was extracted with DCM, rotatory evaporated to dry, and purified by Pre-TLC, to provide the compound t-butyl 2-((2-((2-((1r, 3r)-3-(3-chloro-4-cyanophenoxy)-2,2,4,4-tetramethylcyclobutyl)-3-oxoisoindol-5-yl)amino)pentyl)oxy)acetate (74.4 mg), with a yield of 67.5%. LC/MS (ESI$^+$) Calcd for $C_{34}H_{44}ClN_3O_5$ (M-56+H$^+$) m/z, 609.3; Found, 554.2.

2. Synthesis of 2-((2-((2-((1r,3r)-3-(3-chloro-4-cyanophenoxy)-2,2,4,4-tetramethylcyclobutyl)-3-oxoisoindol-5-yl)amino)pentyl)oxy)acetic acid t-Butyl 2-((2-((2-((1r,3r)-3-(3-chloro-4-cyanophenoxy)-2,2,4,4-tetramethylcyclobutyl)-3-oxoisoindol-5-yl)amino)pentyl)oxy)acetate (74.0 mg, 0.12 mmol) was dissolved 1 ml DCM, to which was added 5 ml TFA, and the mixture was allowed to react 1 h at room temperature. The raw material was completely reacted by TLC detection, and then the system was rotatory evaporated to dry, to which was added DCM to dissolve the residue. The resultant solution was washed with saturated $NaHCO_3$ aqueous solution until the pH was about 6. The organic phase was dried, filtered, and concentrated, to provide 2-((2-((2-((1r,3r)-3-(3-chloro-4-cyanophenoxy)-2,2,4,4-tetramethylcyclobutyl)-3-oxoisoindol-5-yl)amino)pentyl)oxy)acetic acid (70.3 mg), with a yield of 96.3%.

3. Synthesis of (3R,5S)-1-((S)-2-(2-((5-((2-((1R, 3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-5-((S)-1-(4-(4-methylthiazol-5)-yl)phenyl)ethyl)carbamoyl) pyrrolidin-3-yl acetate 2-((2-((2-((1r,3r)-3-(3-chloro-4-cyanophenoxy)-2,2,4,4-tetramethylcyclobutyl)-3-oxoisoindol-5-yl)amino)pentyl)oxy)acetic acid (70.0 mg, 0.13 mmol) was dissolved in 4 ml DMF, to which was added DIEA (81.5 mg, 0.63 mmol), and the mixture was cooled to about 0° C., to which was added HATU (72.0 mg, 0.19 mmol). The mixture was stirred 10 min, to which was then added (2S,4R)-1-((S)-2-amino-3,3-dimethylbutyryl)-4-hydroxy-N-((S)-1-(4-(4-methylthiazol-5-yl)phenyl)ethyl)amido)pyrrolidine-2-carboxamide (92.1 mg, 0.19 mmol). The resultant mixture was warmed to room temperature and allowed to react 2 h. The reaction was completed by TLC detection, and then 5 ml $H_2O$ was slowly added to the system. The resultant solution was extracted with ethyl acetate, and the organic phase was washed with water for 5 times, followed by washing with 0.5 M HCl and saturated brine, respectively. The organic phase was dried, filtered, concentrated in vacuo, and purified by Pre-TLC, to provide (3R,5S)-1-((S)-2-(2-((5-((2-((1R,3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-5-(((S)-1-(4-(4-methylthiazol-5)-yl)phenyl) ethyl)carbamoyl) pyrrolidin-3-yl acetate (31.3 mg), with a yield of 38.8%. $^1H$ NMR (400 MHz, DMSO-$d_6$) δ 8.98 (m, 1H), 8.47 (d, J=7.61 Hz, 1H), 7.90 (d, J=8.8 Hz, 1H), 7.38 (dt, J=8.7, 7.5 Hz, 6H), 7.28 (d, J=2.4 Hz, 1H), 7.06 (dd, J=8.8, 2.4 Hz, 1H), 6.85 (d, J=8.3 Hz, 1H), 6.77 (s, 1H), 5.87 (s, 1H), 5.20 (s, 1H), 4.93-4.88 (m, 1H), 4.60 (s, 2H), 4.53 (s, 1H), 4.45 (dd, J=14.4, 8.7 Hz, 2H), 4.29 (s, 1H), 3.90 (dd, J=16.2, 6.4 Hz, 3H), 3.77 (dd, J=11.8, 3.9 Hz, 1H), 3.49 (t, J=6.4 Hz, 2H), 3.05 (s, 2H), 2.45 (s, 3H), 2.29-2.23 (m, 1H), 2.09 (s, 1H), 1.99 (s, 3H), 1.98 (d, J=3.1 Hz, 1H), 1.62-1.56 (m, 4H), 1.45 (d, J=4.9 Hz, 3H), 1.37 (s, 6H), 1.35 (s, 1H), 1.14 (s, 6H), 0.95 (s, 9H). LC/MS (ESI$^+$) Calcd for $C_{55}H_{68}ClN_7O_8S$ (M+H$^+$) m/z, 1021.5; Found, 1022.5.

7: (2S,4R)-1-((S)-2-(2-((5-((2-((1R,3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-4-hydroxy-N-((S)-1-(4-(4-methylthiazol-5-yl)phenyl)ethyl) pyrrolidine-2-carboxamide (7)

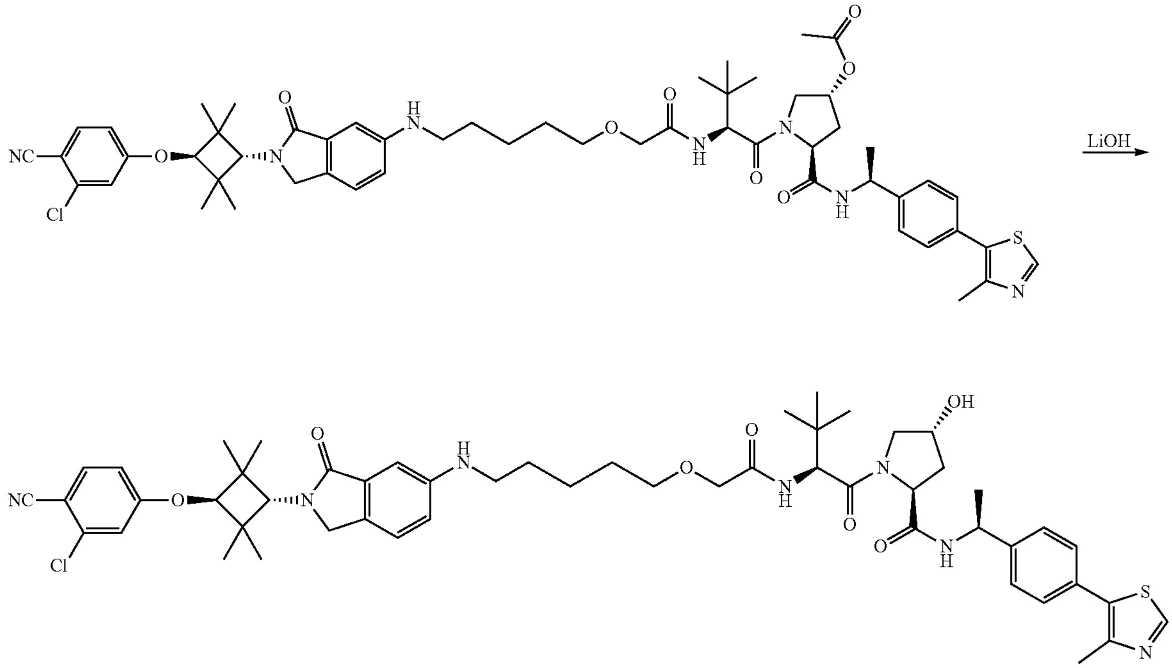

(3R,5S)-1-((S)-2-(2-((5-((2-((1R,3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-5-(((S)-1-(4-(4-methylthiazol-5)-yl)phenyl)ethyl) carbamoyl) pyrrolidin-3-yl acetate (5.0 mg, 4.30 μmol) was dissolved in 1 ml methanol, to which was slowly added the mixed system of LiOH.$H_2O$ (0.9 mg, 0.02 mmol) and 0.5 ml $H_2O$. After about 30 min, TLC analysis indicated that the reaction was completed. The system was added with water, extracted with DCM, and purified by Pre-TLC, to provide the compound (2S,4R)-1-((S)-2-(2-((5-((2-((1R,3R)-3-(3-chloro-4-cyanophenoxy)-2,2,4,4-tetramethylcyclobutyl)-3-oxoisoindolin-5-yl)amino)pentyl)oxy)acetylamino)-3,3-dimethylbutyryl)-4-hydroxy-N-((S)-1-(4-(4-methylthiazol-5-yl)phenyl)ethyl) pyrrolidine-2-carboxamide (3.3 mg), with a yield of 87.4%. $^1H$ NMR (400 MHz, DMSO-$d_6$) δ 8.97 (m, 1H), 8.46 (d, J=7.6 Hz, 1H), 7.89 (d, J=8.8 Hz, 1H), 7.38 (dt, J=8.7, 7.5 Hz, 6H), 7.28 (d, J=2.4 Hz, 1H), 7.06 (dd, J=8.8, 2.4 Hz, 1H), 6.85 (d, J=8.3 Hz, 1H), 6.77 (s, 1H), 5.87 (s, 1H), 5.20 (s, 1H), 4.93-4.88 (m, 1H), 4.60 (s, 2H), 4.53 (s, 1H), 4.45 (dd, J=14.4, 8.7 Hz, 2H), 4.29 (s, 1H), 3.90 (dd, J=16.2, 6.4 Hz, 3H), 3.77 (dd, J=11.8, 3.9 Hz, 1H), 3.49 (t, J=6.4 Hz, 2H), 3.05 (s, 2H), 2.45 (s, 3H), 2.28-2.22 (m, 1H), 2.08 (s, 1H), 1.98 (d, J=3.1 Hz, 1H), 1.62-1.54 (m, 4H), 1.43 (d, J=4.9 Hz, 3H), 1.36 (s, 6H), 1.35 (s, 1H), 1.13 (s, 6H), 0.95 (s, 9H). LC/MS ($ESI^+$) Calcd for $C_{53}H_{66}ClN_7O_7S$ ($M+H^+$) m/z, 979.4; Found, 980.3.

8: (3R,5R)-1-((S)-2-(2-((6-(4-(((1R,3R)-3-(3-bromo-4-cyanophenoxy)-2,2,4,4-tetramethylcyclobutyl) carbamoyl)phenyl)hex-5-yn-1-yl)oxy)acetylamino)-3,3-dimethylbutyryl)-5-((1-(4-(4-methylthiazol-5-yl) phenyl)cyclopropyl)carbamoyl) pyrrolidin-3-yl acetate (8)

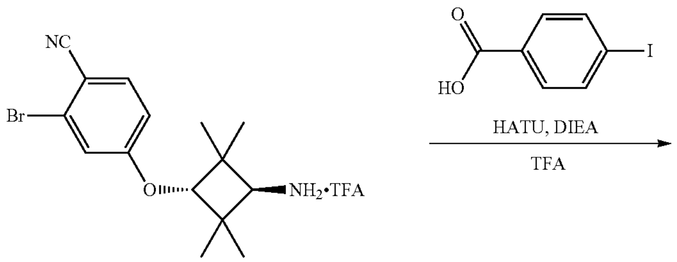

-continued
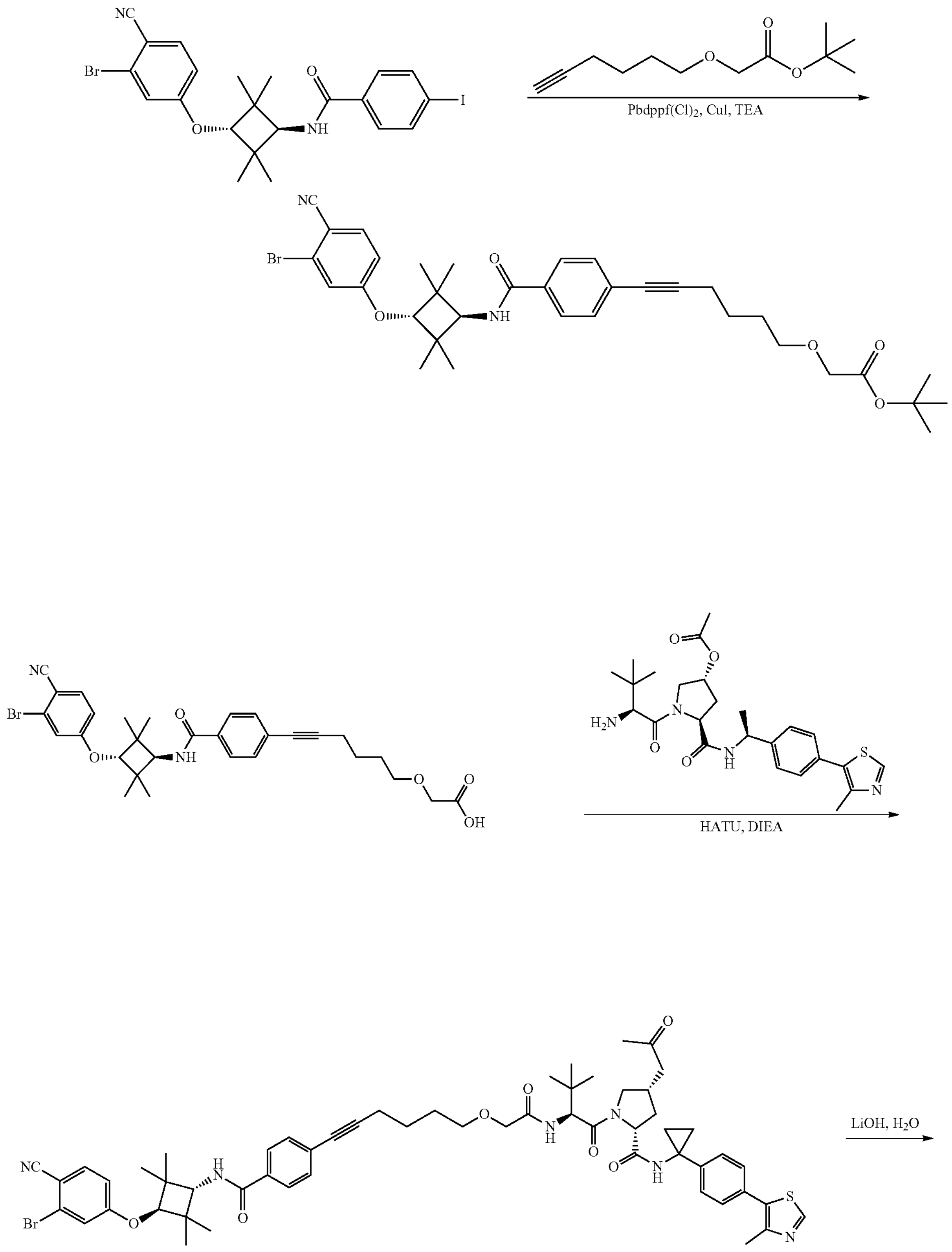

-continued

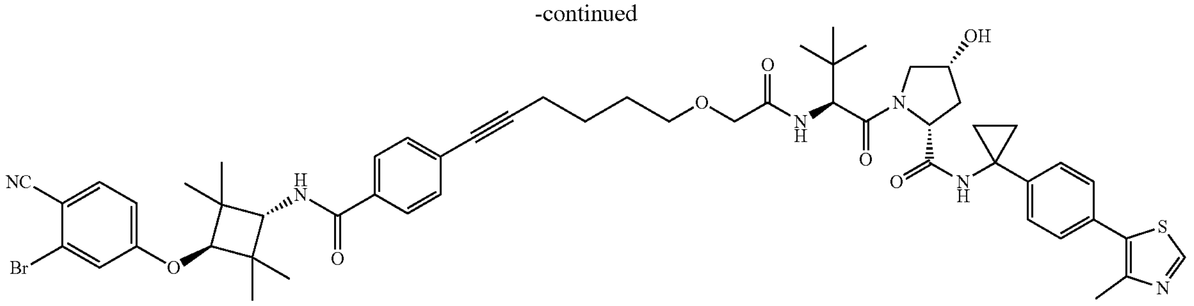

9

1. Synthesis of N-((1R,3R)-3-(3-bromo-4-cyanophenoxy)-2,2,4,4-tetramethylcyclobutyl)-4-iodobenzamide p-iodobenzoic acid (103.0 mg, 0.42 mmol) was dissolved in 2 ml DCM, and the mixture was cooled to about 0° C., to which were sequentially added DIEA (266.6 mg, 2.08 mmol) and HATU (237.2 mg, 0.62 mmol). The mixture was stirred 10 min at low temperature, to which was added 4-((1R,3R)-3-amino-2,2,4,4-tetramethylcyclobutyl)-2-chlorobenzonitrile trifluoroacetate (200.0 mg, 0.46 mmol), and the ice bath was removed. The resultant solution was allowed to react for 2 h at room temperature, and TLC ANALYSIS indicated that the reaction was completed. The reaction system was successively washed with 0.5 M HCl aqueous solution and saturated brine, dried, concentrated in vacuo, and purified by column chromatography, to provide N-((1R,3R)-3-(3-bromo-4-cyanophenoxy)-2,2,4,4-tetramethylcyclobutyl)-4-iodobenzamide (221.0 mg), with a yield of 73.7%. LC/MS (ESI) Calcd for $C_{22}H_{22}BrIN_2O_2(M+H^+)$ m/z, 554.0; Found, 555.1.

2. Synthesis of t-Butyl 2-(6-(4-((1r,3r)-3-(3-bromo-4-cyanophenoxy)-2,2,4,4-tetramethylcyclobutyl) carbamoyl-phenyl)hex-5-yn-1-yloxy)acetate N-((1R,3R)-3-(3-bromo-4-cyanophenoxy)-2,2,4,4-tetramethylcyclobutyl)-4-iodobenzamide (100.0 mg, 0.18 mmol), $PbdppfCl_2$ (26.5 mg, 0.04 mmol), CuI (17.5 mg, 0.09 mmol), and t-Butyl 2-(hex-5-yn-1-yloxy)acetate (38.5 mg, 0.18 mmol) were sequentially added to the reaction flask, and then nitrogen was purged, to which were added 1.2 ml of toluene and 0.4 ml of triethylamine by syringe. After that, the system was purged with nitrogen again. The mixture was allowed to react 3 h at 90° C., and the reaction was completed by TLC detection. The system was cooled to room temperature and filtered through a pad of celite. The filtrate was concentrated, to which was added dichloromethane to dissolve the residue, and then the organic phase was successively washed with 0.5 M HCl and saturated brine. The organic phase was dried, filtered, concentrated in vacuo, and purified by Pre-TLC, to provide t-butyl 2-(6-(4-((1r,3r)-3-(3-bromo-4-cyanophenoxy)-2,2,4,4-tetramethylcyclobutyl)carbamoyl-phenyl)hex-5-yn-1-yloxy)acetate (121.3 mg), with a yield of 91.6%. LC/MS (ESI+) Calcd for $C_{34}H_{41}BrN_2O_5(M-56^+)$ m/z, 638.2; Found, 583.2.

3. Synthesis of 2-(6-(4-((1r,3r)-3-(3-bromo-4-cyanophenoxy)-2,2,4,4-tetramethylcyclobutyl)carbamoyl-phenyl)hex-5-yn-1-yloxy)acetic acid t-Butyl 2-(6-(4-((1r,3r)-3-(3-bromo-4-cyanophenoxy)-2,2,4,4-tetramethylcyclobutyl) carbamoyl-phenyl)hex-5-yn-1-yloxy)acetate (120.0 mg, 0.19 mmol) was dissolved in 1 ml DCM, to which was added 5 ml TFA, and the mixture was allowed to react 1 h at room temperature. The raw material was completely reacted by TLC detection, and then the system was rotatory evaporated to dry, to which was added DCM to dissolve the residue. The resultant solution was washed with saturated $NaHCO_3$ aqueous solution until the pH was about 6. The organic phase was dried, filtered, and concentrated, to provide 2-(6-(4-((1r,3r)-3-(3-bromo-4-cyanophenoxy)-2,2,4,4-tetramethylcyclobutyl) carbamoylphenyl)hex-5-yn-1-yloxy)acetic acid (95.2 mg), with a yield of 92.4%.

4. Synthesis of (3R,5R)-1-((S)-2-(2-((6-(4-(((1R,3R)-3-(3-bromo-4-cyanophenoxy)-2,2,4,4-tetramethylcyclobutyl)carbamoyl)phenyl)hex-5-yn-1-yl)oxy) acetylamino)-3,3-dimethylbutyryl)-5-((1-(4-(4-methylthiazol-5-yl)phenyl)cyclopropyl)carbamoyl) pyrrolidin-3-yl acetate 2-(6-(4-((1r,3r)-3-(3-bromo-4-cyanophenoxy)-2,2,4,4-tetramethylcyclobutyl) carbamoylphenyl)hex-5-yn-1-yloxy) acetic acid (95.0 mg, 0.16 mmol) was dissolved in 2 ml DMF, to which was added DIEA (113.5 mg, 0.89 mmol), and the mixture was cooled to about 0° C., to which was added HATU (101.0 mg, 0.24 mmol). The mixture was stirred 10 min, to which was then added (2S,4R)-1-((S)-2-amino-3,3-dimethylbutyryl)-4-hydroxy-N-((S)-1-(4-(4-methylthiazol-5-yl)phenyl)ethyl)amido) pyrrolidine-2-cyclopropylamide (130.1 mg, 0.22 mmol). The resultant mixture was warmed to room temperature and allowed to react 2 h. The reaction was completed by TLC detection, and then 5 ml $H_2O$ was slowly added to the system. The resultant solution was extracted with ethyl acetate, and the organic phase was washed with water for 5 times, followed by washing with 0.5 M HCl and saturated brine, respectively. The organic phase was dried, filtered, concentrated in vacuo, and purified by Pre-TLC, to provide (3R,5R)-1-((S)-2-(2-((6-(4-(((1R,3R)-3-(3-bromo-4-cyanophenoxy)-2,2,4,4-tetramethylcyclobutyl)carbamoyl)phenyl)hex-5-yn-1-yl)oxy) acetylamino)-3,3-dimethylbutyryl)-5-((1-(4-(4-methylthiazol-5-yl)phenyl)cyclopropyl)carbamoyl) pyrrolidin-3-yl acetate (40.0 mg), with a yield of 46.7%. $^1H$ NMR (400 MHz, $CDCl_3$) δ 8.81 (s, 1H), 7.70 (d, J=8.1 Hz, 2H), 7.56 (d, J=8.7 Hz, 1H), 7.45 (d, J=8.4 Hz, 3H), 7.33 (d, J=3.6 Hz, 4H), 7.15 (d, J=2.3 Hz, 2H), 6.85 (dd, J=8.7, 2.3 Hz, 1H), 6.27 (d, J=8.3 Hz, 1H), 5.37 (s, 1H), 4.64 (t, J=7.4 Hz, 1H), 4.54 (d, J=9.3 Hz, 1H), 4.15 (d, J=8.2 Hz, 1H), 4.06 (s, 1H), 4.01-3.92 (m, 2H), 3.80 (dd, J=11.6, 4.5 Hz, 1H), 3.60 (t, J=6.1 Hz, 3H), 2.68-2.61 (m, 1H), 2.52 (d, J=3.4 Hz, 3H), 2.50 (s, 1H), 2.18 (d, J=11.2 Hz, 1H), 2.05 (s, 3H), 1.83 (d, J=7.3 Hz, 2H), 1.75 (dd, J=13.6, 6.7 Hz, 4H), 1.27 (s, 6H), 1.25 (s, 4H), 1.23 (s, 6H), 0.97 (s, 9H). LC/MS (ESI+) Calcd for $C_{56}H_{65}BrN_6O_8S$ $(M+H^+)$ m/z, 1062.4; Found, 1063.4.

9: Compound (2R,4R)-1-((S)-2-(2-((6-(4-(((1R,3R)-3-(3-bromo-4-cyanophenoxy)-2,2,4,4-tetramethylcyclobutyl)carbamoyl)phenyl)hex-5-yn-1-yl)oxy) acetylamino)-3,3-dimethylbutyryl)-4-hydroxy-N-(1-(4-(4-methyl-5-yl)phenyl)cyclopropyl) pyrrolidine-2-carboxamide (9)

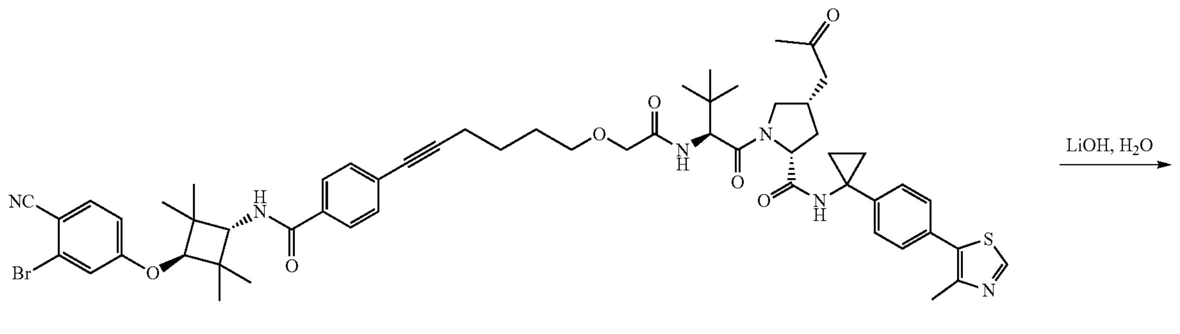

8

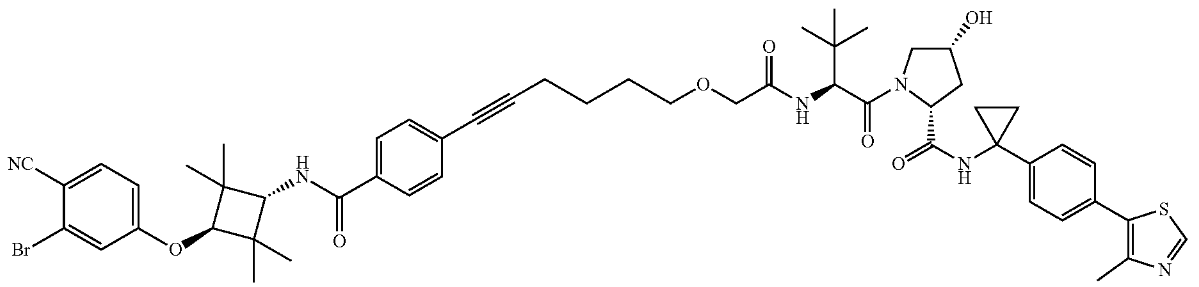

9

(3R,5R)-1-((S)-2-(2-((6-(4-(((1R,3R)-3-(3-bromo-4-cyanophenoxy)-2,2,4,4-tetramethylcyclobutyl)carbamoyl)phenyl)hex-5-yn-1-yl)oxy)acetylamino)-3,3-dimethylbutyryl)-5-((1-(4-(4-methylthiazol-5-yl)phenyl)cyclopropyl) carbamoyl) pyrrolidin-3-yl acetate (5.0 mg, 4.70 μmol) was dissolved in 1 ml methanol, to which was slowly added the mixed system of $LiOH.H_2O$ (0.9 mg, 0.02 mmol) and 0.5 ml $H_2O$. After about 30 min, TLC ANALYSIS indicated that the reaction was completed. The system was added with water, extracted with DCM, and purified by Pre-TLC, to provide the compound (2R,4R)-1-((S)-2-(2-((6-(4-(((1R, 3R)-3-(3-bromo-4-cyanophenoxy)-2,2,4,4-tetramethylcyclobutyl)carbamoyl)phenyl)hex-5-yn-1-yl)oxy)acetylamino)-3,3-dimethylbutyryl)-4-hydroxy-N-(1-(4-(4-methyl-5-yl)phenyl)cyclopropyl) pyrrolidine-2-carboxamide (3.0 mg), with a yield of 84.3%. LC/MS ($ESI^+$) Calcd for $C_{56}H_{65}BrN_6O_8S$ ($M+H^+$) m/z, 1020.4; Found, 1021.4. $^1H$ NMR (400 MHz, $CDCl_3$) δ 8.96 (s, 1H), 7.70 (s, 1H), 7.59-7.49 (m, 2H), 7.43 (s, 1H), 7.35 (s, 2H), 7.31 (s, 1H), 7.21 (d, J=8.5 Hz, 1H), 7.15 (s, 1H), 6.85 (d, J=8.0 Hz, 1H), 6.44-6.34 (m, 1H), 4.66 (s, 1H), 4.58-4.43 (m, 2H), 4.23-4.06 (m, 3H), 4.03-3.89 (m, 2H), 3.62 (d, J=16.3 Hz, 3H), 2.53 (d, J=13.9 Hz, 3H), 2.47-2.39 (m, 1H), 2.38-2.29 (m, 1H), 2.14 (s, 2H), 2.04 (s, 1H), 1.82 (s, 4H), 1.75 (s, 10H), 1.29 (s, 6H), 1.25 (s, 9H), 1.23 (s, 6H), 1.01 (s, 7H), 0.93-0.78 (m, 5H).

10: (3R,5S)-1-((S)-2-(2-(4-((2-((1r,3r)-3-(3-chloro-4-cyanophenoxy)-2,2,4,4-tetramethylcyclobutyl)-1-oxoisoindolin-5-ylethynyl)-1H-pyrazol-1-yl) acetylamino)-3,3-dimethylbutyryl)-5-((((S)-1-(4-(4-methylthiazol-5-yl)phenyl) ethyl carbamoyl) pyrrolidin-3-yl acetate (10)

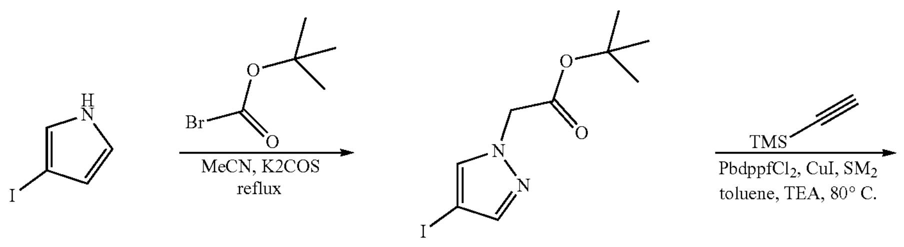

-continued
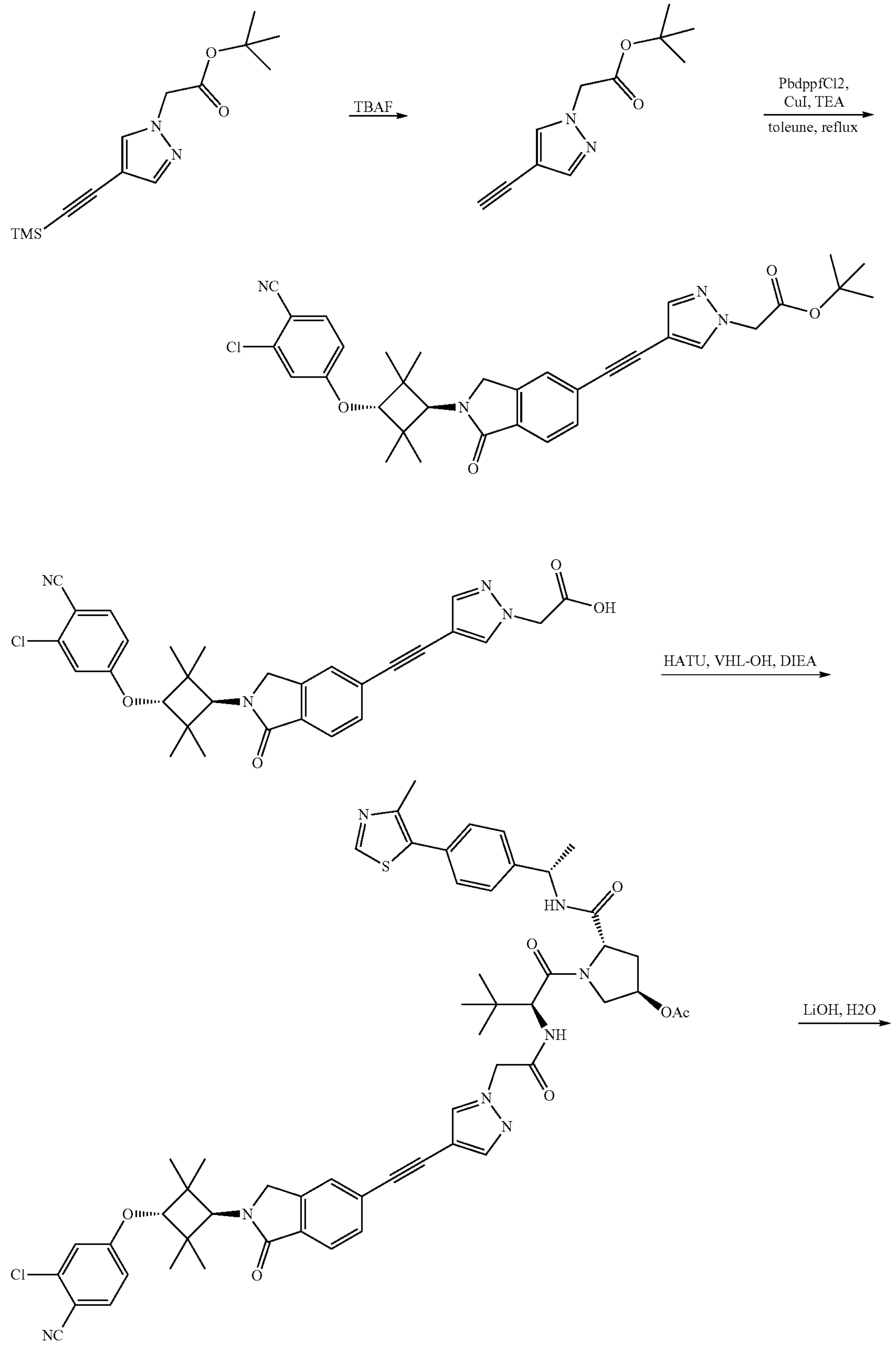

-continued

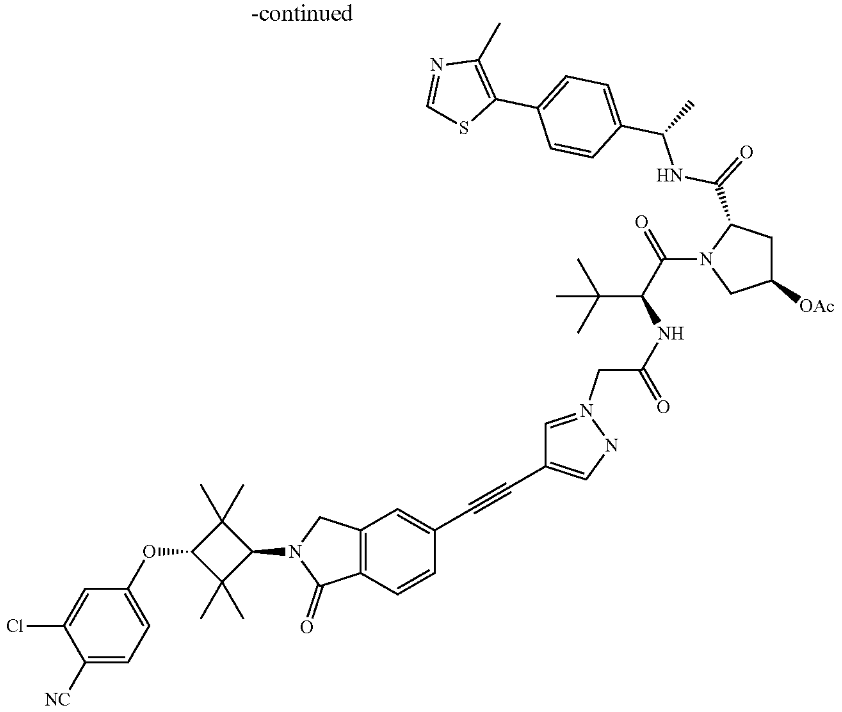

11

LC/MS ($ESI^+$) Calcd for $C_{55}H_{59}ClN_8O7S$ ($M+H^+$) m/z, 1011.4; found 1011.4. $^1H$ NMR (400 MHz, DMSO-$d_6$) δ 8.99 (s, 1H), 8.47 (d, J=7.6 Hz, 1H), 8.32 (d, J=8.5 Hz, 1H), 8.13 (d, J=6.3 Hz, 1H), 7.91 (d, J=8.8 Hz, 1H), 7.76 (s, 1H), 7.70 (d, J=7.1 Hz, 2H), 7.59 (d, J=8.1 Hz, 1H), 7.41 (dd, J=25.1, 8.2 Hz, 4H), 7.30 (d, J=2.4 Hz, 1H), 7.08 (dd, J=8.8, 2.4 Hz, 1H), 5.76 (s, 1H), 5.17 (s, 1H), 5.02-4.90 (m, 3H), 4.79 (d, J=15.3 Hz, 2H), 4.55 (s, 1H), 4.48 (t, J=8.3 Hz, 1H), 4.41-4.31 (m, 2H), 3.90 (d, J=11.8 Hz, 1H), 3.74 (dd, J=11.6, 3.9 Hz, 1H), 3.32 (s, 1H), 2.46 (s, 3H), 1.93 (s, 3H), 1.43-1.34 (m, 9H), 1.16 (s, 6H), 0.98 (s, 9H).

11: (2S,4R)-1-((S)-2-(2-(4-((2-((1R,3R)-3-(3-chloro-4-cyanophenoxy)-2,2,4,4-tetramethylcyclobutyl)-1-oxoisoindolin-5-ylethynyl)-1H-pyrazol-1-yl) acetylamino)-3,3-dimethylbutyryl)-4-hydroxy-N-((S)-1-(4-(4-methylthiazol-5-yl) phenyl)ethyl)pyrrolidine-2-carboxamide (11)

LC/MS (ESI+) Calcd for $C_{53}H_{57}ClN_8O_6S$ ($M+H^+$) m/z, 969.4; found 969.4. $^1H$ NMR (400 MHz, DMSO-$d_6$) δ 8.99 (d, J=3.0 Hz, 1H), 8.45 (d, J=7.6 Hz, 1H), 8.27 (d, J=8.8 Hz, 1H), 8.14 (d, J=2.8 Hz, 1H), 7.91 (dd, J=8.7, 3.1 Hz, 1H), 7.77 (d, J=2.9 Hz, 1H), 7.73-7.67 (m, 2H), 7.59 (d, J=7.9 Hz, 1H), 7.46-7.35 (m, 4H), 7.30 (d, J=2.5 Hz, 1H), 7.08 (dd, J=8.8, 2.5 Hz, 1H), 5.76 (d, J=3.1 Hz, OH), 5.14 (d, J=3.3 Hz, 1H), 4.96 (dd, J=21.1, 4.4 Hz, 3H), 4.81 (s, 2H), 4.58-4.49 (m, 2H), 4.44 (d, J=7.9 Hz, 1H), 4.33 (s, 1H), 4.28 (s, 1H), 3.66-3.51 (m, 2H), 2.45 (d, J=3.1 Hz, 3H), 2.03 (s, 1H), 1.77 (d, J=8.8 Hz, 1H), 1.44-1.36 (m, 9H), 1.16 (d, J=2.7 Hz, 6H), 0.96 (s, 9H).

12: (3R,5S)-1-((S)-2-(2-(2-((3-(2-((1r,3r)-3-(3-chloro-4-cyanophenoxy)-2,2,4,4-tetramethylcyclobutyl)-1-oxoisoindolin-5-yl)prop-2-yn-1-yl)oxy) propoxy) acetylamino)-3,3-dimethylbutyryl)-5-((((S)-1-acetic acid (4-(4-methylthiazol-5-yl)phenyl) ethyl)carbamoyl)pyrrolidin-3-yl acetate (12)

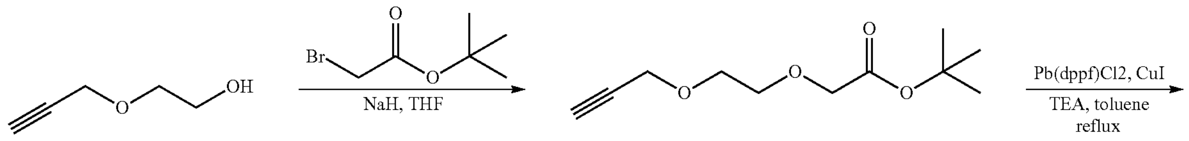

-continued

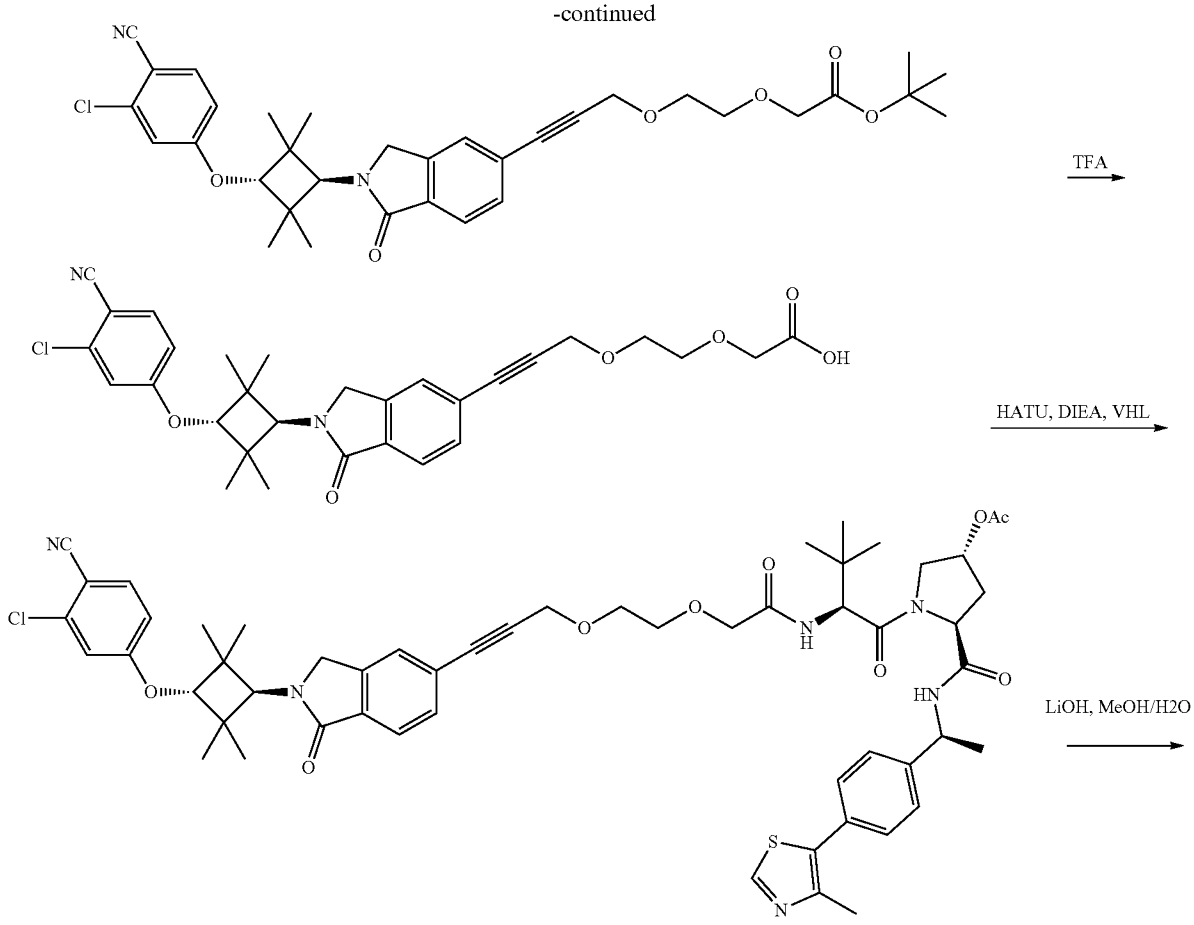

12

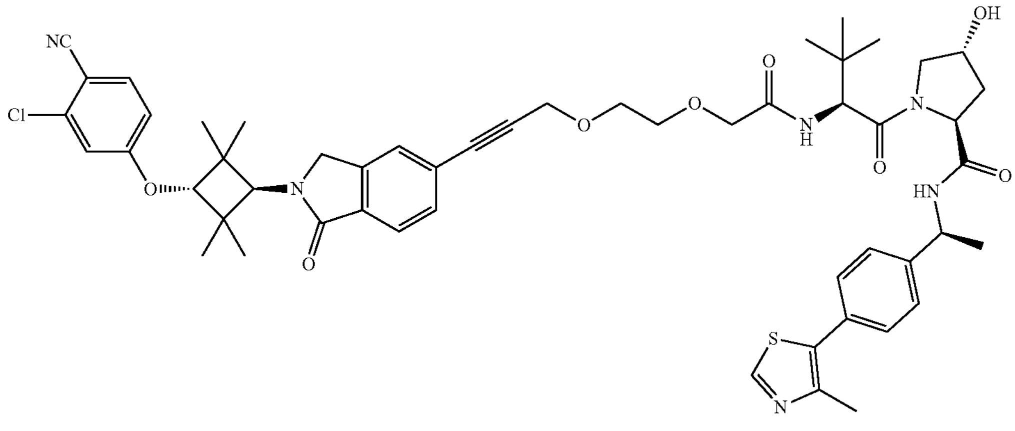

13

LC/MS ($ESI^+$) Calcd for $C_{55}H_{63}ClN_6O_9S$ ($M+H^+$) m/z, 1019.4; found 1019.4. $^1H$ NMR (400 MHz, DMSO-$d_6$) δ 8.99 (s, 1H), 8.47 (d, J=7.6 Hz, 1H), 7.91 (d, J=8.8 Hz, 1H), 7.69 (d, J=2.9 Hz, 2H), 7.57 (d, J=7.9 Hz, 1H), 7.43 (d, J=8.3 Hz, 3H), 7.37 (s, 2H), 7.29 (d, J=2.3 Hz, 1H), 7.07 (dd, J=8.7, 2.4 Hz, 1H), 5.20 (s, 1H), 4.90 (s, 1H), 4.79 (s, 2H), 4.54 (s, 1H), 4.49 (s, 5H), 4.32 (s, 1H), 3.99 (s, 3H), 3.75-3.67 (m, 4H), 3.38 (s, 1H), 3.32 (s, 2H), 2.45 (s, 3H), 2.00 (s, 5H), 1.37 (dd, J=19.0, 4.4 Hz, 9H), 1.23 (s, 1H), 1.15 (s, 6H), 0.95 (d, J=7.4 Hz, 9H).

13: (2S,4R)-1-((S)-2-(2-(2-((3-(2-((1r,3r)-3-(3-chloro-4-cyanophenoxy)-2,2,4,4-tetramethylcyclobutyl)-1-oxoisoindolin-5-yl)prop-2-yn-1-yl)oxy)propoxy) acetylamino)-3,3-dimethylbutyryl)-4-hydroxy-N-((S)-1-(4-(4-(4-methylthiazol-5-yl)phenyl)ethyl)pyrrolidine-2-carboxamide (13)

LC/MS ($ESI^+$) Calcd for $C_{53}H_{61}ClN_6O_8S$ ($M+H^+$) m/z, 977.4; found 977.4. $^1H$ NMR (400 MHz, DMSO-$d_6$) δ 8.99 (s, 1H), 8.47 (d, J=7.6 Hz, 1H), 8.32 (d, J=8.5 Hz, 1H), 8.13 (d, J=6.3 Hz, 1H), 7.91 (d, J=8.8 Hz, 1H), 7.76 (s, 1H), 7.70

(d, J=7.1 Hz, 2H), 7.59 (d, J=8.1 Hz, 1H), 7.41 (dd, J=25.1, 8.2 Hz, 4H), 7.30 (d, J=2.4 Hz, 1H), 7.08 (dd, J=8.8, 2.4 Hz, 1H), 5.76 (s, 1H), 5.17 (s, 1H), 5.02-4.90 (m, 3H), 4.79 (d, J=15.3 Hz, 2H), 4.55 (s, 1H), 4.48 (t, J=8.3 Hz, 1H), 4.41-4.31 (m, 2H), 3.90 (d, J=11.8 Hz, 1H), 3.74 (dd, J=11.6, 3.9 Hz, 1H), 3.32 (s, 1H), 2.46 (s, 3H), 1.93 (s, 3H), 1.43-1.34 (m, 9H), 1.16 (s, 6H), 0.98 (s, 9H).
14: (3R,5S)-1-((2S)-2-(2-(2-((3-(2-((1r,3r)-3-(3-chloro-4-cyanophenoxy)-2,2,4,4-tetramethylcyclobutyl)-1-oxoisoindol-5-yl)prop-2-yn-1-yl)oxy)propoxy) acetylamino)-3,3-dimethylbutyryl)-5-((((S)-1-acetic acid (4-(4-methylthiazol-5-yl)phenyl) ethyl)carbamoyl)pyrrolidin-3-yl acetate (14)
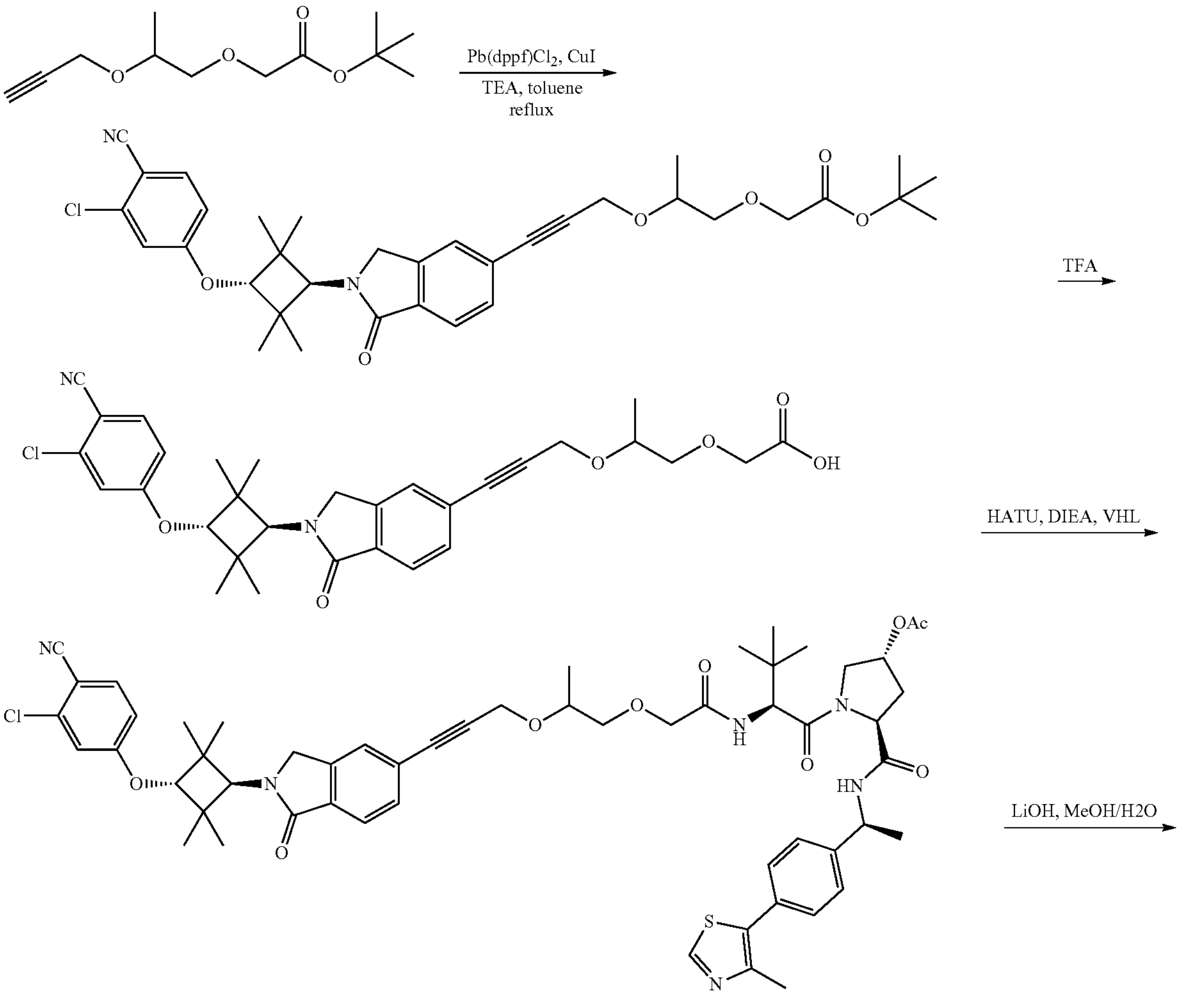
14
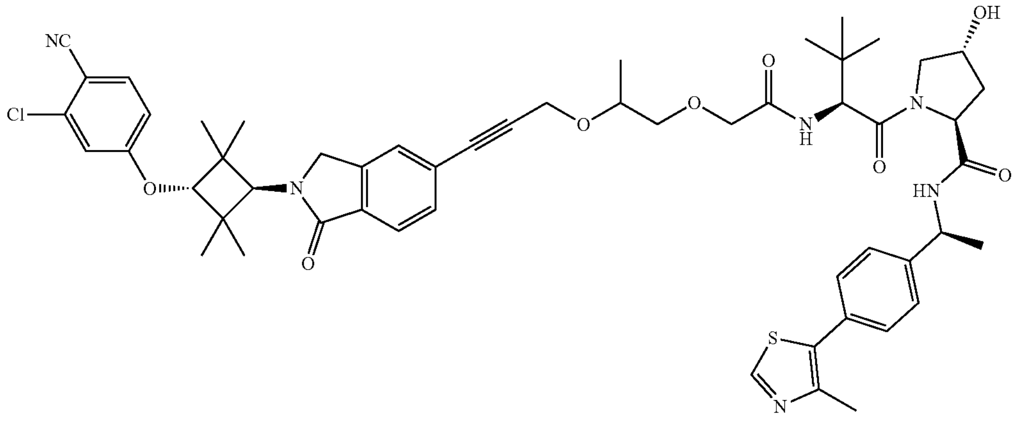
15

LC/MS (ESI+) Calcd for $C_{56}H_{65}ClN_6O_9S$ (M+H$^+$) m/z, 1033.4; found 1033.4. $^1$H NMR (400 MHz, DMSO-d$_6$) δ 8.98 (s, 1H), 8.48 (d, J=6.7 Hz, 1H), 7.91 (d, J=8.8 Hz, 1H), 7.70 (d, J=7.6 Hz, 2H), 7.58 (t, J=6.0 Hz, 1H), 7.40 (dd, J=27.2, 7.6 Hz, 4H), 7.29 (d, J=2.3 Hz, 1H), 7.07 (dd, J=8.8, 2.3 Hz, 1H), 5.20 (s, 1H), 4.89 (s, 1H), 4.79 (s, 2H), 4.56-4.42 (m, 5H), 4.32 (s, 1H), 4.00 (d, J=6.7 Hz, 2H), 3.93-3.85 (m, 1H), 3.81-3.70 (m, 2H), 3.57 (s, 3H), 3.41-3.37 (m, 1H), 3.20-3.10 (m, 1H), 2.69 (s, 9H), 2.45 (s, 3H), 2.31-2.21 (m, 1H), 2.00 (s, 3H), 1.98 (s, 1H), 1.39 (s, 5H), 1.36 (dd, J=6.9, 3.2 Hz, 3H), 1.26 (t, J=6.4 Hz, 6H), 1.14 (d, J=6.0 Hz, 7H), 0.97 (s, 9H).

15: (2S,4R)-1-((2S)-2-(2-(2-((3-(2-((1r,3r)-3-(3-chloro-4-cyanophenoxy)-2,2,4,4-tetramethylcyclobutyl)-1-oxoisoindol-5-yl)prop-2-yn-1-yl)oxy) propoxy) acetylamino)-3,3-dimethylbutyryl)-4-hydroxy-N-((S)-1-(4-(4-(4-methylthiazol-5-yl) phenyl)ethyl)pyrrolidine-2-carboxamide (15)

LC/MS (ESI$^+$) Calcd for $C_{54}H_{63}ClN_6O_8S$ (M+H$^+$) m/z, 991.4; found 991.4. $^1$H NMR (400 MHz, DMSO-d$_6$) δ 8.98 (s, 1H), 8.46 (d, J=6.7 Hz, 1H), 7.90 (d, J=8.8 Hz, 1H), 7.71 (d, J=7.6 Hz, 2H), 7.58 (t, J=6.0 Hz, 1H), 7.42 (dd, J=27.2, 7.6 Hz, 4H), 7.31 (d, J=2.3 Hz, 1H), 7.07 (dd, J=8.8, 2.3 Hz, 1H), 5.21 (s, 1H), 4.89 (s, 1H), 4.79 (s, 2H), 4.57-4.43 (m, 5H), 4.32 (s, 1H), 4.00 (d, J=6.7 Hz, 2H), 3.92-3.84 (m, 1H), 3.81-3.70 (m, 2H), 3.41-3.37 (m, 1H), 3.20-3.10 (m, 1H), 2.69 (s, 9H), 2.45 (s, 3H), 2.31-2.21 (m, 1H), 2.00 (s, 3H), 1.98 (s, 1H), 1.39 (s, 5H), 1.38 (dd, J=6.9, 3.2 Hz, 3H), 1.26 (t, J=6.4 Hz, 6H), 1.11 (d, J=6.0 Hz, 7H), 0.97 (s, 9H).

16: Synthesis of (2R,4R)-1-((S)-2-(2-((5-((2-((1r, 3r)-3-(4-cyano-3-(trifluoromethyl) phenoxy)-2,2,4,4-tetramethylcyclobutyl)-1-oxoisoindolin-5-yl)amino) phenyl)oxy) acetylamino)-3,3-dimethylbutyryl)-4-hydroxy-N-((R)-1-(4-(4-methylthiazol-5-yl)phenyl) ethyl)pyrrole-2-formamide (16)

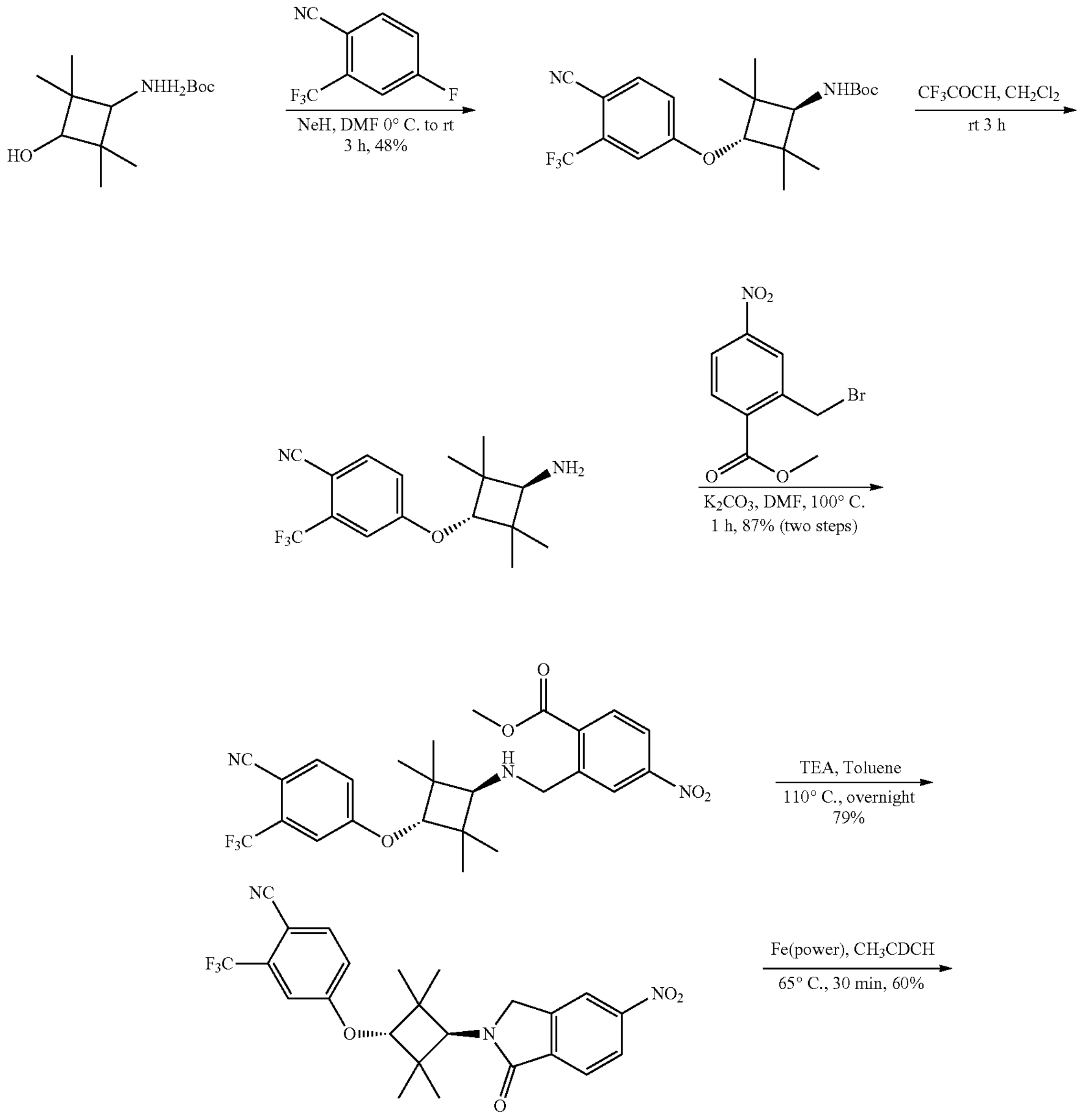

-continued

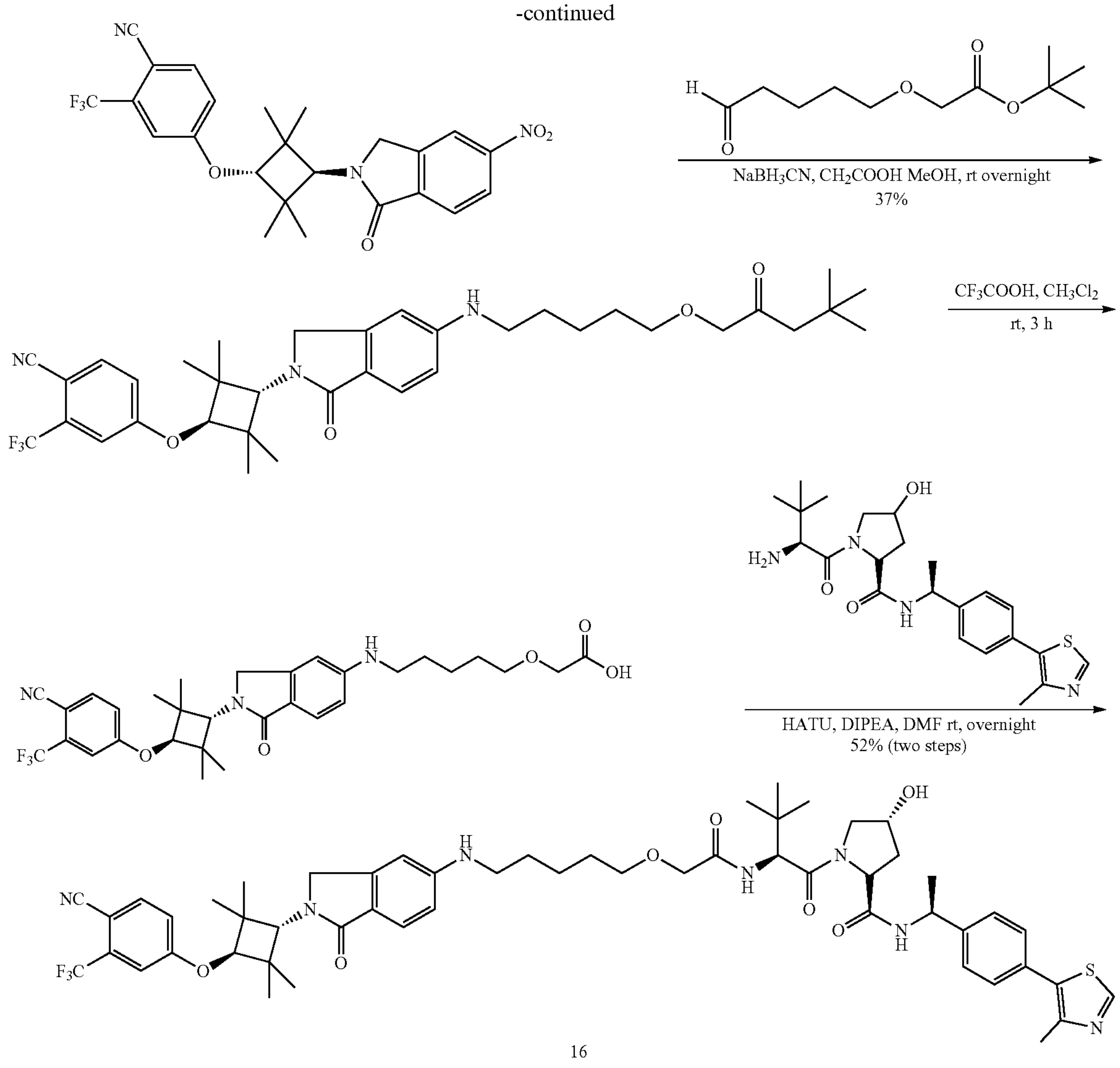

16

1. Synthesis of t-butyl ((1r,3r)-3-(4-cyano-3-(trifluoromethyl)phenoxy)-2,2,4,4-tetramethylcyclobutyl)carbamate t-Butyl (3-hydroxy-2,2,4,4-tetramethylcyclobutyl)carbamate (4700 mg, 19.31 mmol) was dissolved in 100 mL DMF, and then, the system was subjected to purging argon, which was repeated 8 times to ensure an inert gas atmosphere in the system. Then, the system was transferred to an ice-water bath to cool down under stirring. When the internal temperature of the system was lowered to about 0° C., NaH (60%) (1600 mg, 40.55 mmol) was slowly added to the system. After addition, the system was kept at 0° C. and stirred for 1 h. Then, the solution of 2-trifluoromethyl-4-fluorobenzonitrile (1700 mg, 11.00 mmol) in DMF (50 mL) was added dropwise to the system, and the dropping rate was controlled, so that the internal temperature of the system did not exceed 5° C. After that, the system was allowed to further react at 0° C. After 2 h, the sample of reaction solution was taken out and subjected to TLC, and the result indicated the completion of the reaction. The system was slowly poured into ice water with stirring, and a large amount of solid (sticky) precipitated. The filter cake was dissolved in ethyl acetate, dried over anhydrous sodium sulfate, filtered, and concentrated, to provide a crude product, which was separated and purified by column chromatography, to obtain an off-white solid (t-butyl (1r,3r)-3-(4-cyano-3-(trifluoromethyl)phenoxy)-2,2,4,4-tetramethylcyclobutyl)carbamate (3700 mg), with a yield of 46%.

LC/MS (ESI$^+$) Calcd for $C_{21}H_{27}F_3N_2O_3$ $[M+H]^+$ m/z, 412.2; Found:357.1

2. Synthesis of 4-((1r,3r)-3-amino-2,2,4,4-tetramethylcyclobutoxy)-2-(trifluoromethyl) benzonitrile t-Butyl ((1r,3r)-3-(4-cyano-3-(trifluoromethyl)phenoxy)-2,2,4,4-tetramethylcyclobutyl) carbamate (650 mg, 1.58 mmol) was weighed and placed in a 25 mL single-neck round bottom flask, to which was added dichloromethane (15 mL), and the solution was stirred at room temperature. Subsequently, trifluoroacetic acid (3 mL) was added to the system. After that, the system was stirred and reacted at room temperature. After 3 h. the sample was taken out and subjected to TLC, and the result showed that the raw materials had disappeared. The solvent and excess trifluoroacetic acid were removed by rotatory evaporation, and the residual trifluoroacetic acid was removed by repeated evaporation with dichloromethane, to provide 4-((1r,3r)-3-amino-2,2,4,4-tetramethylcyclobutoxy)-2-(trifluoromethyl)benzonitrile trifluoroacetate, which was directly used in the next reaction, without further purification as a off-white solid.

3. Synthesis of methyl 2-((((1r,3r)-3-(4-cyano-3-(trifluoromethyl)phenoxy)-2,2,4,4-tetramethylcyclobutyl)amino)methyl)-4-nitrobenzoate To a 25 mL single-neck round bottom flask containing 4-((1r,3r)-3-amino-2,2,4,4-tetramethylcyclobutoxy)-2-(trifluoromethyl)benzonitrile trifluoroacetate, was added DMF (10 mL), and the mixture was stirred at room temperature to dissolve and make the solution become clear. Subsequently, potassium carbonate (437 mg, 3.16 mmol) and methyl 2-(bromomethyl)-4-nitrobenzoate (433 mg, 1.58 mmol) were sequentially added to the system. After that, the system was stirred and reacted in an oil bath at 100° C. After 1 h, the sample was taken out and subjected to TLC, and the result showed that the raw materials had disappeared. Ethyl acetate (15 mL) and water (10 mL) were added to the system, and the resultant mixture was stirred vigorously, stood still for 3 min for separation of the layers. The aqueous layer was extracted with ethyl acetate (10 mL*3). The organic phases were combined, and successively washed with water (10 mL*3) and saturated brine (15 mL), dried over anhydrous sodium sulfate, and concentrated in vacuo, to provide a crude product, which was separated and purified by column chromatography to obtain methyl 2-((((1r,3r)-3-(4-cyano-3-(trifluoromethyl) phenoxy)-2,2,4,4-tetramethylcyclobutyl)amino)methyl)-4-nitrobenzoate (532 mg), with a two-step yield of 67%.

LC/MS (ESI$^+$) Calcd for $C_{25}H_{26}F_3N_3O_5$[M+H]$^+$ m/z, 505.1; Found:506.3.

4. 4-((1r,3r)-2,2,4,4-Tetramethyl-3-(5-nitro-1-oxoisoindolin-2-yl)cyclobutyloxy)-2-(trifluoromethyl) benzonitrile Methyl 2-((((1r,3r)-3-(4-cyano-3-(trifluoromethyl)phenoxy)-2,2,4,4-tetramethyl cyclobutyl)amino)methyl)-4-nitrobenzoate (532 mg, 1.05 mmol) was weighed and placed in a 25 mL single-neck round bottom flask, to which was added toluene (10 mL), and the mixture was stirred at room temperature. Subsequently, triethylamine (319 mg, 3.15 mmol) was added to the system. After that, the system was moved to an oil bath at 110° C. for further heating under reflux and reacting overnight with stirring. The next day, the sample was taken out and subjected to TLC, and the result indicated the completion of the reaction. After the system was cooled to room temperature, the solvent was removed by rotary evaporation to obtain a crude product, which was beated in n-hexane (20 mL) and ethyl acetate (1 mL) at room temperature. After 30 min, the system was subjected to the suction filtration, and the filter cake was rinsed with n-hexane (30 mL) and dried, to provide 4-((1r,3r)-2,2,4,4-tetramethyl-3-(5-nitro-1-oxoisoindolin-2-yl)cyclobutyloxy)-2-(trifluoromethyl)benzonitrile as a white solid (395 mg), with a yield of 79%.

LC/MS (ESI$^+$) Calcd for $C_{24}H_{22}F_3N_3O_4$[M+H]$^+$ m/z, 473.1; Found: 474.3.

5. 4-((1r,3r)-3-(5-Amino-1-oxoisoindolin-2-yl)-2,2,4,4-tetramethylcyclobutyloxy)-2-(trifluoromethyl) benzonitrile 4-((1r,3r)-2,2,4,4-Tetramethyl-3-(5-nitro-1-oxoisoindolin-2-yl)cyclobutyloxy)-2-(trifluoromethyl)benzonitrile (395 mg, 0.83 mmol) was weighed and placed in a 25 mL single-neck round bottom flask, to which was added glacial acetic acid (12 mL), and the mixture was stirred at room temperature. Then, the reduced iron powder (1400 mg, 24.90 mmol) was added to the system. After that, the system was moved to an oil bath at 65° C. for further heating and reacting with stirring. After 30 min, the sample was taken out and subjected to TLC, and the result indicated the starting material had disappeared. The heating was stopped. The system was filtered while hot, and the filter cake was rinsed with glacial acetic acid (36 mL). The filtrate was collected, and acetic acid was removed by rotary evaporation to obtain a crude product, which was beated in n-hexane (5 mL) and ethyl acetate (2 mL) at room temperature. After 20 min, the system was subjected to the suction filtration, and the filter cake was rinsed with n-hexane (5 mL) and dried, to provide 4-((1r,3r)-3-(5-amino-1-oxoisoindolin-2-yl)-2,2,4,4-tetramethylcyclobutyloxy)-2-(trifluoromethyl) benzonitrile (324 mg) as off-white solid, with a yield of 88%.

LC/MS (ESI$^+$) Calcd for $C_{24}H_{24}F_3N_3O_2$[M+H]$^+$ m/z, 443.1; Found: 444.2.

6. Synthesis of t-butyl 2-((5-((2-((1r,3r)-3-(4-cyano-3-(trifluoromethyl)phenoxy)-2,2,4,4-tetramethylepoxybutyl)-1-oxoisoindolin-5-yl)amino)pentyl)oxy) acetate 4-((1r,3r)-3-(5-Amino-1-oxoisoindolin-2-yl)-2,2,4,4-tetramethylcyclobutyloxy)-2-(trifluoromethyl)benzonitrile (150 mg, 0.34 mmol) was weighed and placed in 50 mL single-neck round bottom flask, to which were sequentially added t-butyl 2-((5-oxopentyl)oxy)acetate (73 mg, 0.34 mmol), methanol (15 mL) and acetic acid (61 mg, 1.02 mmol), and the mixture was stirred to dissolve and make the solution become clear at room temperature. After 15 min, $NaBH_3CN$ (86 mg, 1.36 mmol) was added to the system. After that, the system was stirred and reacted overnight at room temperature. The next day, the sample was taken out and subjected to TLC, and the result indicated that the starting material had disappeared. After the solvent was removed by rotatory evaporation, ethyl acetate (20 mL) and water (10 mL) were added to the system and stirred vigorously. After 3 min, the layers were separated and the aqueous layer was extracted with ethyl acetate (10 mL*3). The organic phases were combined, successively washed with water (10 mL*3) and saturated brine (15 mL), dried over anhydrous sodium sulfate, and concentrated in vacuo to obtain a crude product, which was separated and purified by Pre-TLC to provide t-butyl 2-((5-((2-((1r,3r)-3-(4-cyano-3-(trifluoromethyl)phenoxy)-2,2,4,4-tetramethylepoxybutyl)-1-oxoisoindolin-5-yl)amino)pentyl)oxy)acetate as an off-white solid (80 mg), with a yield of 37%.

LC/MS (ESI$^+$) Calcd for $C_{35}H_{44}F_3N_3O_5$ [M+H]$^+$ m/z, 643.3; Found: 644.3.

7. Synthesis of 2-((5-((2-((1r,3r)-3-(4-cyano-3-(trifluoromethyl)phenoxy)-2,2,4,4-tetramethylcyclobutyl)-1-oxoisoindolin-5-yl)amino)pentyl)oxy) acetic acid t-Butyl 2-((5-((2-((1r,3r)-3-(4-cyano-3-(trifluoromethyl) phenoxy)-2,2,4,4-tetramethyl epoxybutyl)-1-oxoisoindolin-5-yl)amino)pentyl)oxy)acetate (38 mg, 0.06 mmol) was weighed and placed in a 25 mL single-neck round bottom flask, to which was added dichloromethane (10 mL), and the solution was stirred at room temperature. Subsequently, trifluoroacetic acid (1 mL) was added to the system. After that, the system was stirred and reacted at room temperature. After 3 h, the sample was taken out and subjected to TLC, and the result showed that the raw materials had disappeared. The solvent and excess trifluoroacetic acid were removed by rotatory evaporation, and the residual trifluoroacetic acid was removed by repeated evaporation with dichloromethane, to provide 2-((5-((2-((1r,3r)-3-(4-cyano-3-(trifluoromethyl) phenoxy)-2,2,4,4-tetramethylcyclobutyl)-1-oxoisoindolin-5-yl)amino)pentyl) oxy)acetic acid as an off-white solid, which was directly used in the next reaction, without further purification.

8. Synthesis of (2R,4R)-1-((S)-2-(2-((5-((2-((1r,3r)-3-(4-cyano-3-(trifluoromethyl)phenoxy)-2,2,4,4-tetramethylcyclobutyl)-1-oxoisoindolin-5-yl)amino) phenyl)oxy)acetylamino)-3,3-dimethylbutyryl)-4-hydroxy-N-((R)-1-(4-(4-methylthiazol-5-yl)phenyl) ethyl)pyrrole-2-formamide To a 25 mL single-neck round bottom flask containing 2-((5-((2-((1r,3r)-3-(4-cyano-3-(trifluoromethyl)phenoxy)-2,2,4,4-tetramethylcyclobutyl)-1-oxoisoindolin-5-yl)amino) pentyl)oxy)acetic acid, were successively added HATU (34 mg, 0.09 mmol). DMF (5 mL), VHL(OAc) (39 mg, 0.07 mmol), and diisopropylethylamine (23 mg, 0.18 mmol), and then the system was stirred and reacted overnight at room temperature. The next day, the sample was taken out and subjected to TLC, and the result indicated that the starting material had disappeared. Ethyl acetate (15 mL) and water (10 mL) were added to the system and stirred vigorously. After 3 min, the layers were separated and the aqueous layer was extracted with ethyl acetate (10 mL*3). The organic phases were combined, successively washed with water (10 mL*3) and saturated brine (15 mL), and dried over anhydrous sodium sulfate. The solvent was removed by rotatory evaporation to obtain a crude product, which was separated and purified by Pre-TLC, to provide (2R,4R)-1-((S)-2-(2-((5-((2-((1r,3r)-3-(4-cyano-3-(trifluoromethyl)phenoxy)-2,2,4,4-tetramethylcyclobutyl)-1-oxoisoindolin-5-yl)amino) phenyl)oxy)acetylamino)-3,3-dimethylbutyryl)-4-hydroxy-N-((R)-1-(4-(4-methylthiazol-5-yl)phenyl)ethyl)pyrrole-2-formamide as an off-white solid (31 mg), with a two-step yield of 52%.

LC/MS (ESI$^+$) Calcd for $C_{54}H_{66}F_3N_7O_7S$ $[M+H]^+$ m/z, 1013.4; Found: 1014.2.

$^1$H NMR (400 MHz, DMSO-$d_6$) δ 8.98 (s, 1H), 8.44 (d, J=7.8 Hz, 1H), 8.10 (d, J=8.7 Hz, 1H), 7.46-7.31 (m, 10H), 6.69-6.57 (m, 2H), 6.39-6.27 (m, 1H), 5.14 (s, 1H), 4.92-4.84 (m, 1H), 4.62 (s, 2H), 4.58 (s, 1H), 4.55 (d, J=9.8 Hz, 1H), 4.45 (t, J=8.3 Hz, 1H), 3.92 (d, J=2.2 Hz, 2H), 3.60-3.56 (dd, J=4.8, 1.8 Hz, 2H), 3.50 (t, J=6.3 Hz, 3H), 3.13-3.05 (m, 2H), 2.45 (s, 3H), 2.11-2.01 (m, 1H), 1.80-1.73 (m, 1H), 1.66-1.54 (m, 4H), 1.50-1.41 (m, 2H), 1.38 (s, 6H), 1.34 (d, J=6.9 Hz, 2H), 1.13 (s, 6H), 0.94 (s, 9H).

17. (3R,5S)-1-((2S)-2-(2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl)carbamoyl) (pyridin-2-yl)piperazin-1-yl)methyl) piperidin-1-yl)acetylamino)-3,3-dimethylbutyryl)-5-(((S)-1-(4-(4-methylthiazol-5-yl)phenyl)ethyl) carbamoyl) pyrrolidin-3-yl acetate

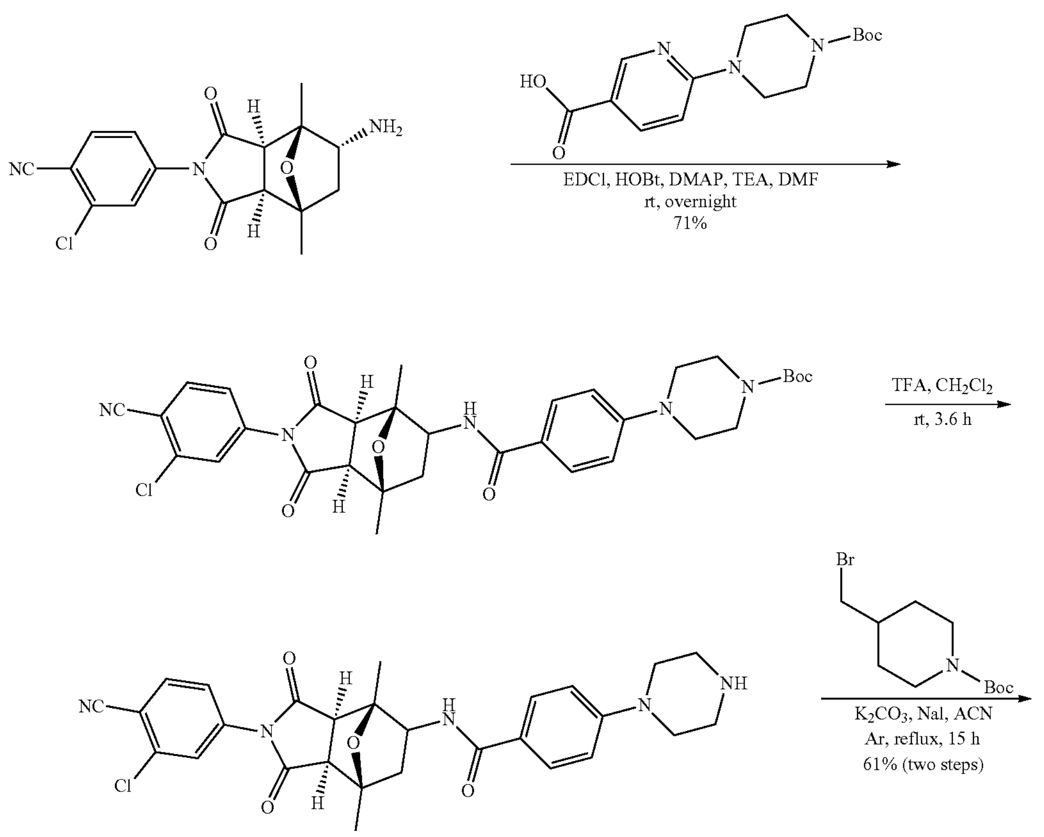

-continued

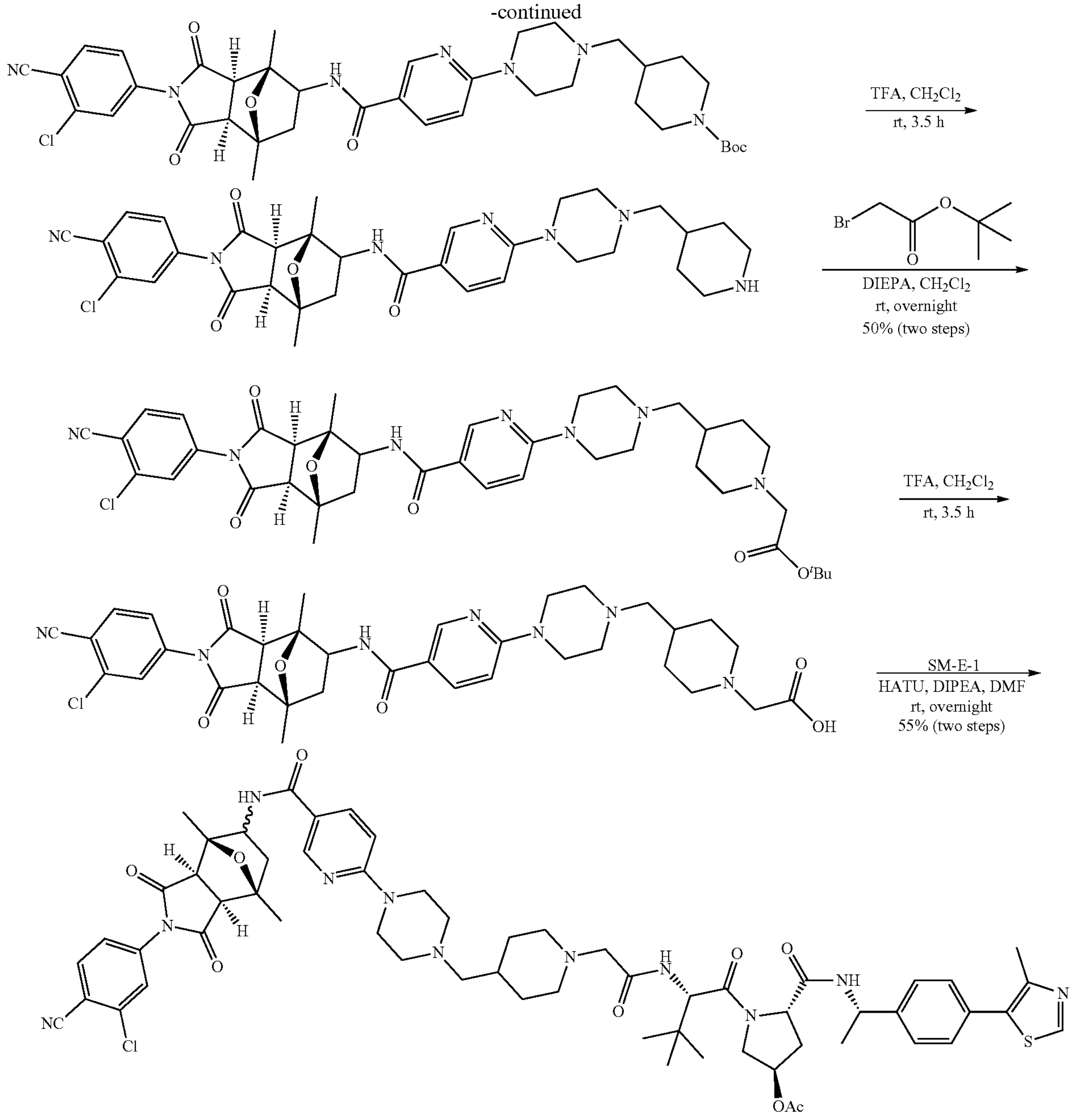

1. Synthesis of Intermediate t-butyl 4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl) (pyridin-2-yl)piperazine-1-carboxylate 6-[4-(t-Butoxycarbonyl)piperazin-1-yl]nicotinic acid (130 mg, 0.42 mmol) was weighed and placed in a 25 mL single-neck round bottom flask, to which was added. DMF (8 mL), and the mixture was stirred at room temperature to dissolve and make the solution become clear. Subsequently, EDCI (200 mg, 1.05 mmol), HOBt (85 mg, 0.63 mmol), DMAP (5 mg, 0.04 mmol) and triethylamine (106 mg, 1.05 mmol) were successively added to the system. After that, the system was stirred and reacted for 5 min at room temperature. Then, 4-((3aR,4R,7R,7aS)-5-amino-4,7-dimethyl-1,3-dioxohexahydro-1H-4,7-epoxyisoindol-2(3H)-yl)-2-chlorobenzonitrile (145 mg, 0.42 mmol), prepared according to the literatural method, was added to the system, and the system was allowed to stir and react overnight at room temperature. The next day, TLC detection indicated the completion of the reaction. Ethyl acetate (20 mL) and water (15 mL) were added to the system, and then the system was stirred vigorously, stood still 5 min for separation of the layers. The aqueous layer was extracted with ethyl acetate (10 mL*3). The organic phase was combined, and successively washed with water (10 mL*3) and saturated brine (15 mL), dried with anhydrous sodium sulfate, and concentrated in vacuo to obtain a crude product, which was separated and purified by Pre-TLC, to provide t-butyl 4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl) piperazine-1-carboxylate (191 mg), with a yield of 71%. LCMS ($ESI^+$) Calcd for $C_{32}H_{35}ClN_6O_6$ $[M+H]^+$ m/z, 635.1; Found: 634.7.

2. Synthesis of N-((3aR,4R,7R,7aS)-2-(3-chloro-4-benzonitrile)-4,7-dimethyl-1,3-dioxooctahydro-1H-4,7-epoxyisoindol-5-yl)-6-(piperazin-1-yl)nicotinamide trifluoroacetate t-Butyl 4-(5-(((3aR,4R,7R,7aS)-2-(3-chloro-4-benzonitrile)-4,7-dim ethyl-1,3-dioxooctahydro-1H-4,7-epoxyisoindol-5-yl)carbamoyl)(pyridin-2-yl)piperazine-1-carboxylate (175 mg, 0.28 mmol) was weighed and placed in a 25 mL single-neck round bottom flask, to which was added dichloromethane (10 mL), and the solution was stirred at room temperature. Subsequently, trifluoroacetic acid (1 mL) was added to the system. After that, the system was stirred and reacted at room temperature. After 3.5 h, the sample was taken out and subjected to TLC, and the result showed that the raw materials had disappeared. The solvent and excess trifluoroacetic acid were removed by rotatory evaporation, and the residual trifluoroacetic acid was removed by repeated evaporation with dichloromethane, to provide N-((3aR,4R,7R,7aS)-2-(3-chloro-4-benzonitrile)-4,7-dimethyl-1,3-dioxooctahydro-1H-4,7-epoxyisoindol-5-yl)-6-(piperazin-1-yl)nicotinamide trifluoroacetate as an off-white solid, which was directly used in the next reaction, without further purification.

3. Synthesis of t-butyl 4-((4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl)piperazin-1-yl)methyl)piperidine-1-carboxylate To a 25 mL single-neck round bottom flask containing N-((3aR,4R,7R,7aS)-2-(3-chloro-4-benzonitrile)-4,7-dimethyl-1,3-dioxooctahydro-1H-4,7-epoxyisoindol-5-yl)-6-(piperazin-1-yl)nicotinamide trifluoroacetate, were added 1-Boc-4-bromomethylpiperidine (86 mg, 0.31 mmol), potassium carbonate (155 mg, 1.12 mmol), sodium iodide (42 mg, 0.28 mmol) and acetonitrile (10 mL), and the mixture were stirred at room temperature to dissolve. After that, the system was evacuated and purged with argon gas, that was repeated 5 times, to ensure the inert gas atmosphere in the system. After that, the system was moved to an oil bath for heating under reflux and reacting overnight. After 15 h, the sample was taken out and subjected to TLC, and the result indicated the completion of the reaction. The solvent was removed by rotatory evaporation, and then ethyl acetate (15 mL) and water (10 mL) were added to the system. The system was stirred vigorously, and stood still 3 min for separation of the layers. The aqueous layer was extracted with ethyl acetate (10 mL*3). The organic phase was combined, and successively washed with water (10 mL*3) and saturated brine (15 mL), dried with anhydrous sodium sulfate, and concentrated in vacuo to obtain a crude product, which was separated and purified by Pre-TLC, to provide t-butyl 4-((4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl)piperazin-1-yl)methyl)piperidine-1-carboxylate (124 mg), with a two-step yield of 61%. LC/MS (ESI$^+$) Calcd for $C_{38}H_{46}ClN_7O_6$ [M+H]+m/z, 732.3; Found: 732.2.

4. Synthesis of N-((3aR,4R,7R,7aS)-2-(3-chloro-4-benzonitrile)-4,7-dimethyl-1,3-dioxooctahydro-1H-4,7-epoxyisoindol-5-yl)-6-(4-(piperidin-4-ylmethyl)piperazin-1-yl)nicotinamide trifluoroacetate t-Butyl 4-((4-(5-(((3aR,4R,7R,7aS)-2-(3-chloro-4-benzonitrile)4,7-dimethyl-1,3-dioxooctahydro-1H-4,7-epoxyisoindol-5-yl)carbamoyl)(pyridin-2-yl)piperazin-1-yl)methyl)piperidine-1-carboxylate (124 mg, 0.16 mmol) was weighed and placed in a 25 mL single-neck round bottom flask, to which was added dichloromethane (8 mL), and the solution was stirred at room temperature. Subsequently, trifluoroacetic acid (1 mL) was added to the system. After that, the system was stirred and reacted at room temperature. After 3 h, the sample was taken out and subjected to TLC, and the result indicated that the completion of the reaction. The solvent and excess trifluoroacetic acid were removed by rotatory evaporation, and the residual trifluoroacetic acid was removed by repeated evaporation with dichloromethane, to provide N-((3aR,4R,7R,7aS)-2-(3-chloro-4-benzonitrile)-4,7-dimethyl-1,3-dioxooctahydro-1H-4,7-epoxyisoindol-5-yl)-6-(4-(piperidin-4-ylmethyl)piperazin-1-yl) nicotinamide trifluoroacetate as an off-white solid, which was directly used in the next reaction, without further purification.

5. Synthesis of t-butyl 2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl)carbamoyl)(pyridin-2-yl)piperazin-1-yl)methyl) piperidin-1-yl)acetate To a 25 mL single-neck round bottom flask containing N-((3aR,4R,7R,7aS)-2-(3-chloro-4-benzonitrile)-4,7-dimethyl-1,3-dioxooctahydro-1H-4,7-epoxyisoindolin-5-yl)-6-(4-(piperidin-4-ylmethyl)piperazin-1-yl)nicotinamide trifluoroacetate, were successively added t-butyl bromoacetate (62 mg, 0.32 mmol), dichloromethane (10 mL) and diisopropylethylamine (83 mg, 0.64 mmol), and then the system was stirred and reacted overnight at room temperature. The next day, the sample was taken out and subjected to TLC, and the result indicated the completion of the reaction. Dichloromethane (10 mL) and water (10 mL) were added to the system and stirred vigorously. After 3 min, the layers were separated and the aqueous layer was extracted with dichloromethane (5 mL*3). The organic phases were combined, successively washed with water (5 mL*3) and saturated brine (10 mL), dried over anhydrous sodium sulfate, and concentrated in vacuo to obtain a crude product, which was separated and purified by Pre-TLC to provide t-butyl 2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl) carbamoyl)(pyridin-2-yl)piperazin-1-yl)methyl)piperidin-1-yl)acetate (74 mg), with a two-step yield of 59%.

LC/MS (ESI$^+$) Calcd for $C_{39}H_{48}ClN_7O_6[M+H]^+$ m/z, 746.3; Found: 745.2.

6. Synthesis of 2-(4-((4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl)piperazin-1-yl)methyl)piperidin-1-yl)acetic acid t-Butyl 2-(4-((4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl)piperazin-1-yl) methyl)piperidin-1-yl)acetic acid (40 mg, 0.05 mmol) was weighed and placed in a 25 mL single-neck round bottom flask, to which was added dichloromethane (5 mL), and the solution was stirred at room temperature. Subsequently, trifluoroacetic acid (1 mL) was added to the system. After that, the system was stirred and reacted at room temperature. After 3 h, the sample was taken out and subjected to TLC, and the result indicated that the completion of the reaction.

The solvent and excess trifluoroacetic acid were removed by rotatory evaporation, and the residual trifluoroacetic acid was removed by repeated evaporation with dichloromethane, to provide 2-(4-((4-(5-(((3aR,4R,7R,7aS)-2-(3-chloro-4-benzonitrile)-4,7-dimethyl-1,3-dioxooctahydro-1H-4,7-epoxyisoindol-5-yl)carbamoyl)(pyridin-2-yl)piperazin-1-yl)methyl)piperidin-1-yl)acetic acid as an off-white solid, which was directly used in the next reaction, without further purification.

7. (3R,5S)-1-((2S)-2-(2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl)carbamoyl)(pyridin-2-yl)piperazin-1-yl)methyl)piperidin-1-yl)acetylamino)-3,3-dimethylbutyryl)-5-(((S)-1-(4-(4-methylthiazol-5-yl)phenyl)ethyl)carbamoyl)pyrrolidin-3-yl acetate To a 25 mL single-neck round bottom flask containing 2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl)carbamoyl)(pyridin-2-yl)piperazin-1-yl)methyl)piperidin-1-yl)acetic acid, were successively added HATU (29 mg, 0.08 mmol), DMF (5 mL), VHL(OAc) (36 mg, 0.06 mmol), and diisopropylethylamine (19 mg, 0.15 mmol), and then the system was stirred and reacted overnight at room temperature. The next day, the sample was taken out and subjected to TLC, and the result indicated the starting material had disappeared. Ethyl acetate (15 mL) and water (10 mL) were added to the system, and the system was stirred vigorously, and then allowed to stand still for separation of the layers. The aqueous layer was extracted with ethyl acetate (10 mL*3). The organic phase was combined, and successively washed with water (10 mL*3) and saturated brine (15 mL), dried with anhydrous sodium sulfate, and concentrated in vacuo to obtain a crude product, which was separated and purified by Pre-TLC, to provide (3R,5S)-1-((2S)-2-(2-(4-((4-(5-(((3aR,4R,7R,7aS)-2-(3-chloro-4-benzonitrile)-4,7-dimethyl-1,3-dioxooctahydro-1H-4,7-epoxyisoindolin-5-yl)carbamoyl)(pyridin-2-yl)piperazin-1-yl)methyl)piperidin-1-yl)acetylamino)-3,3-dimethylbutyryl)-5-(((S)-1-(4-(4-methylthiazol-5-yl)phenyl)ethyl)carbamoyl)pyrrolidin-3-yl acetate (34 mg), with a two-step yield of 55%. LC/MS (ESI$^+$) Calcd for $C_{60}H_{72}ClN_{11}O_9S$ $[M+H]^+$ m/z, 1158.8; Found: 1157.6.

$^1$H NMR (400 MHz, DMSO-$d_6$) δ 8.98 (s, 1H), 8.46 (d, J=7.7 Hz, 1H), 8.30 (d, J=7.7 Hz, 1H), 8.13 (d, J=8.4 Hz, 1H), 7.77 (dd, J=8.4, 5.3 Hz, 3H), 7.70 (d, J=9.4 Hz, 1H), 7.53 (dd, J=8.4, 1.8 Hz, 1H), 7.40 (dd, J=28.8, 8.2 Hz, 4H), 6.98 (d, J=8.5 Hz, 2H), 5.20 (s, 1H), 4.94-4.86 (m, 1H), 4.49-4.43 (m, 1H), 4.41-4.30 (m, 2H), 3.88 (d, J=12.2 Hz, 1H), 3.76 (dd, J=11.1, 4.0 Hz, 1H), 3.47 (d, J=7.2 Hz, 1H), 3.29-3.25 (m, 7H), 2.86-2.76 (m, 2H), 2.46 (s, 3H), 2.35-2.05 (m, 7H), 2.00 (s, 3H), 1.94-1.85 (m, 2H), 1.79-1.70 (m, 2H), 1.49 (s, 3H), 1.42 (s, 3H), 1.38 (d, J=7.0 Hz, 3H), 1.24 (s, 2H), 1.17-1.10 (m, 3H), 0.95 (s, 9H).

18. Synthesis of N-((3aR,4R,7R,7aS)-2-(3-chloro-4-benzonitrile)-4,7-dimethyl-1,3dioxooctahydro-1H-4,7-epoxyisoindolin-5-yl)-6-(4-((1-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidine-4-yl)methyl) piperazin-1-yl)nicotinamide

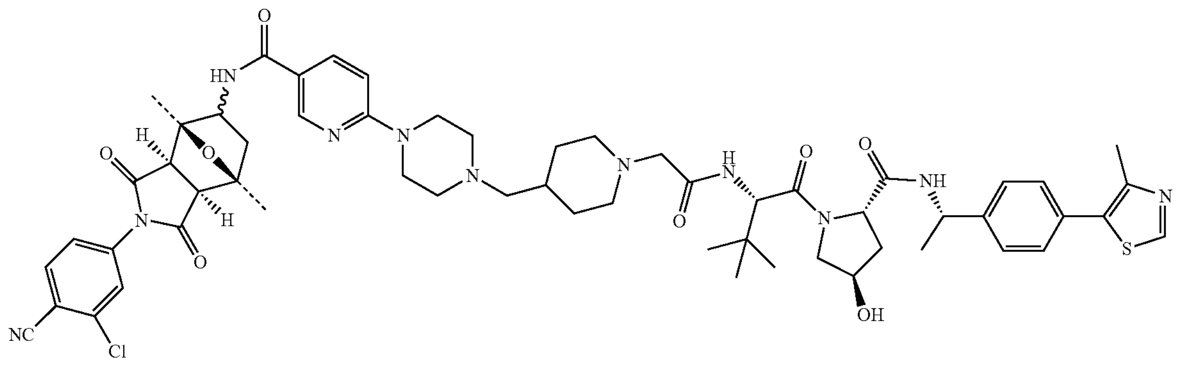

LC/MS (ESI$^+$) Calcd for $C_{58}H_{70}ClN_{11}O_8S$ $[M+H]^+$ m/z, 1116.8; Found: 1116.6.

$^1$H NMR (400 MHz, DMSO-$d_6$) δ 8.99 (s, 1H), 8.66 (d, J=2.2 Hz, 1H), 8.45 (d, J=7.7 Hz, 1H), 8.37 (d, J=7.2 Hz, 1H), 8.13 (d, J=8.4 Hz, 1H), 7.99 (dd, J=9.2, 2.2 Hz, 1H), 7.76 (d, J=1.8 Hz, 1H), 7.53 (dd, J=8.4, 1.9 Hz, 1H), 7.40 (dd, J=28.7, 8.2 Hz, 4H), 6.88 (d, J=9.0 Hz, 1H), 5.13 (d, J=3.1 Hz, 1H), 4.92-4.86 (m, 1H), 4.50 (d, J=9.8 Hz, 1H), 4.44 (t, J=8.1 Hz, 1H), 4.38-4.31 (m, 1H), 4.28 (dt, J=9.2, 5.6 Hz, 1H), 3.61-3.52 (m, 7H), 3.48 (d, J=7.2 Hz, 1H), 2.84-2.75 (m, 3H), 2.46 (s, 3H), 2.11-1.94 (m, 9H), 1.89 (dd, J=12.8, 5.2 Hz, 2H), 1.79-1.69 (m, 3H), 1.49 (s, 3H), 1.43 (s, 3H), 1.38 (d, J=7.0 Hz, 3H), 1.18-0.97 (m, 5H), 0.94 (s, 9H).

19: (3S,5R)-1-((2R)-2-(2-((5-((4-(((3aS,4S,7S,7aR)-2-(3-chloro-4-benzonitrile)4,7-dimethyl-1,3-dioxooctahydro-1H-4,7-epoxyisoindolin-5-yl)carbamoyl)-3-fluorophenyl)amino)pentyl)oxy)acetylamino)-3,3-dimethylbutyryl)-5-(((R)-1-(4-(4-methylthiazol-5-yl)phenyl)ethyl)carbamoyl)pyrrolidin-3-yl acetate

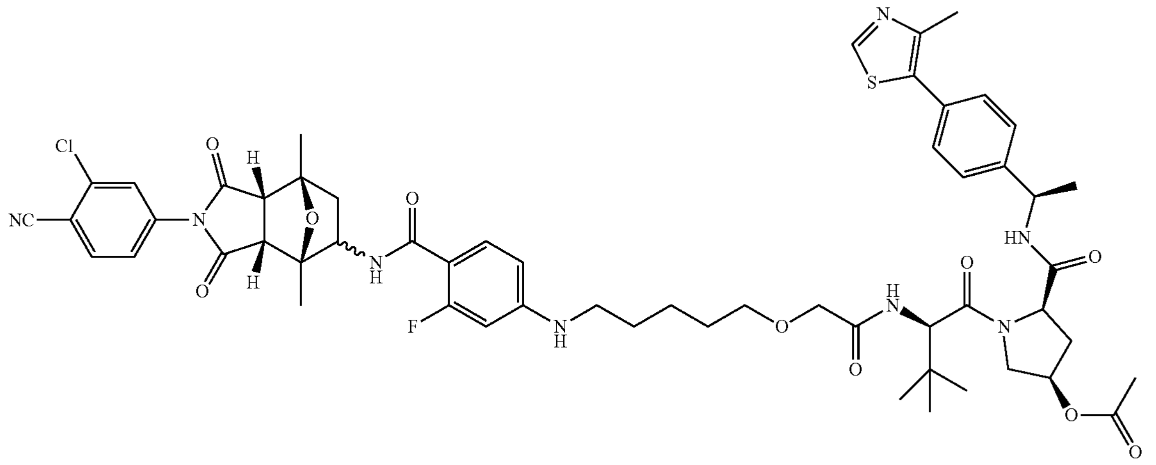 [SMILES: CC(=O)O[C@@H]1C[C@H](C(=O)N[C@H](C)c2ccc(-c3scnc3C)cc2)N(C(=O)[C@H](NC(=O)COCCCCCNc2ccc(C(=O)NC3C[C@]4(C)O[C@@]3(C)[C@@H]3C(=O)N(c5ccc(C#N)c(Cl)c5)C(=O)[C@@H]34)c(F)c2)C(C)(C)C)C1]

LC/MS (ESI+) Calcd for $C_{56}H_{64}ClFN_8O_{10}S$ $[M+H]^+$ m/z, 1095.7; Found: 1095.2.

$^1H$ NMR (400 MHz, DMSO-$d_6$) δ 8.98 (s, 1H), 8.44 (dd, J=11.8, 7.4 Hz, 2H), 8.13 (d, J=8.5 Hz, 1H), 7.92 (s, 1H), 7.76 (d, J=1.7 Hz, 1H), 7.69 (dd, J=8.7, 6.6 Hz, 1H), 7.53 (dd, J=8.4, 1.5 Hz, 1H), 7.39 (dt, J=14.0, 7.0 Hz, 5H), 6.47 (dd, J=12.9, 2.3 Hz, 1H), 6.40 (td, J=8.2, 2.4 Hz, 1H), 5.20 (dd, J=4.0, 3.1 Hz, 1H), 4.94-4.85 (m, 1H), 4.44 (dd, J=16.0, 8.7 Hz, 2H), 4.31 (td, J=12.6, 5.8 Hz, 1H), 3.95-3.84 (m, 3H), 3.76 (dd, J=11.5, 3.5 Hz, 1H), 3.48 (m, 3H), 3.11 (dd, J=11.6, 6.0 Hz, 2H), 2.69 (s, 3H), 2.45 (s, 3H), 2.30-2.21 (m, 1H), 2.11 (t, J=12.0 Hz, 1H), 1.90 (dd, J=13.4, 4.6 Hz, 1H), 1.65-1.55 (m, 4H), 1.49 (s, 3H), 1.46-1.39 (m, 5H), 1.36 (d, J=7.1 Hz, 3H), 1.23 (s, 2H), 0.94 (s, 9H).

20: (2R,4S)-1-((2R)-2-(2-((5-((4-(((3aS,4S,7S,7aR)-2-(3-chloro-4-benzonitrile)-4,7-dimethyl-1,3-dioxooctahydro-1H-4,7-epoxyisoindolin-5-yl)carbamoyl)-3-fluorophenyl)amino)pentyl)oxy)acetylamino)-3,3-dimethylbutyryl)-4-hydroxy-N-((R)-1-(4-(4-methylthiazol-5-yl)phenyl)ethyl)pyrrolidine-2-carboxamide

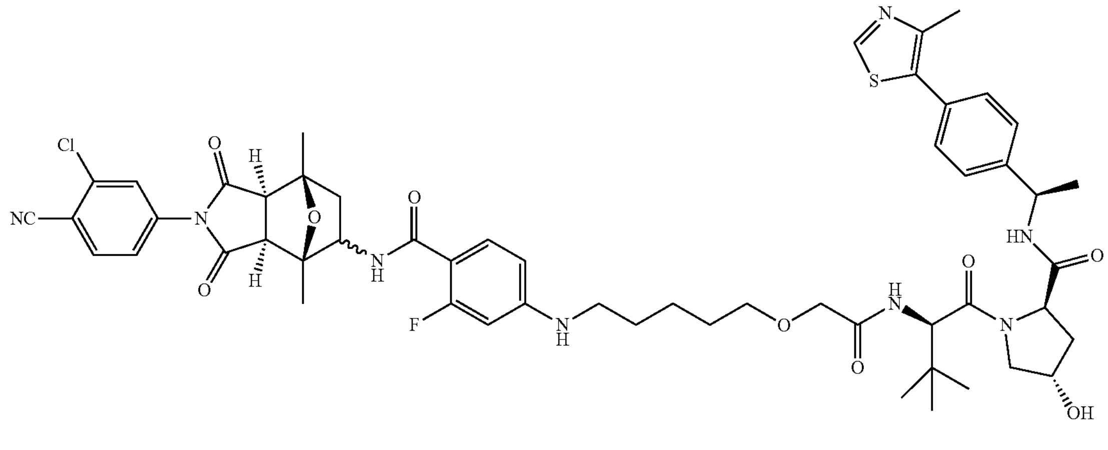 [SMILES: Cc1ncsc1-c1ccc([C@@H](C)NC(=O)[C@H]2C[C@H](O)CN2C(=O)[C@H](NC(=O)COCCCCCNc2ccc(C(=O)NC3C[C@]4(C)O[C@@]3(C)[C@H]3C(=O)N(c5ccc(C#N)c(Cl)c5)C(=O)[C@H]34)c(F)c2)C(C)(C)C)cc1]

LC/MS (ESI+) Calcd for $C_{54}H_{62}ClFN_8O_9S$ $[M+H]^+$ m/z, 1053.6; Found: 1053.5.

$^1H$ NMR (400 MHz, DMSO-$d_6$) δ 8.98 (s, 1H), 8.43 (t, = 6.6 Hz, 2H), 8.13 (d, J=8.4 Hz, 1H), 7.92 (s, 1H), 7.76 (d, J=1.7 Hz, 1H), 7.69 (dd, J=8.2, 6.9 Hz, 1H), 7.53 (dd, J=8.5, 1.7 Hz, 1H), 7.48-7.25 (m, 6H), 6.52-6.36 (m, 2H), 5.13 (d, J=3.5 Hz, 1H), 4.89 (m, 1H), 4.54 (d, J=9.6 Hz, 1H), 4.45 (t, J=7.9 Hz, 1H), 4.28 (m, 1H), 3.92 (s, 2H), 3.60-3.55 (m,

2H), 3.49 (dd, J=12.5, 7.0 Hz, 3H), 3.30 (s, 3H), 3.11 (qd, J=7.3, 1.4 Hz, 2H), 2.45 (s, 3H), 2.16-2.01 (m, 2H), 1.93-1.86 (m, 1H), 1.81-1.72 (m, 1H), 1.67-1.54 (m, 4H), 1.49 (s, 3H), 1.43 (s, 3H), 1.36 (d, J=6.8 Hz, 3H), 0.93 (s, 9H).
21: (2S, 4R)-1-((S)-2-(2-((6-(4-(((1r,3r)-3-(3-chloro-4-cyanophenoxy)-2,2,4,4-tetramethylcyclobutyl)-1-oxoisoindolin-5-yl)pent-4-yn-1-yl)oxy)acetamido)-3,3-dimethylbutyryl)-4H-N-((S)-1-(4-(4-methylthiazol-5-yl)phenyl)ethyl)pyrrolidine-2-carboxamide (21)
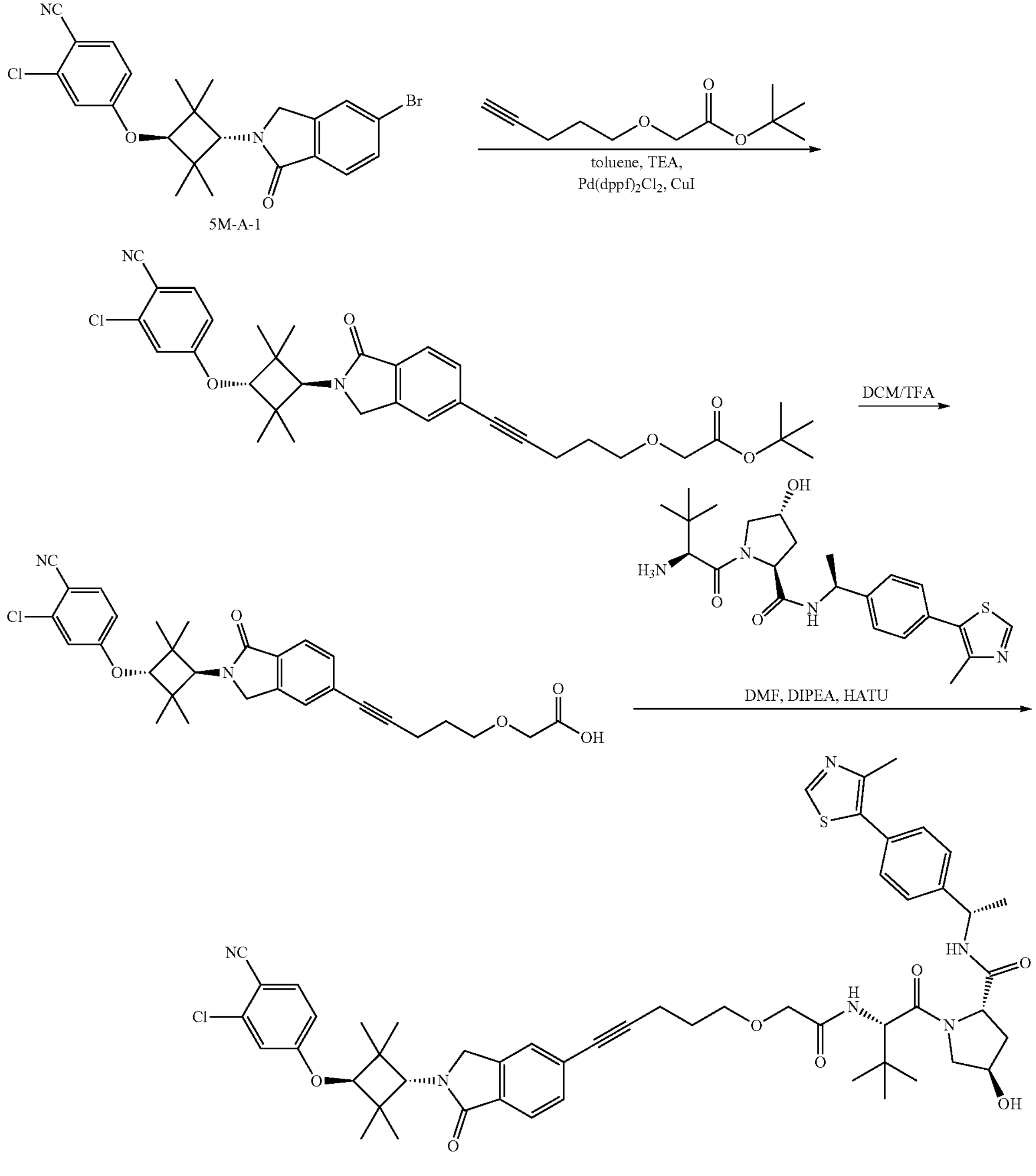
21

1. Synthesis of t-butyl 2-((5-(2-((1R,3R)-3-(3-chloro-4-cyanophenoxy)-2,2,4,4-tetramethylcyclobutyl)-1-oxoisoindolin-5-yl)pent-4-yn-1-yl)oxy) acetate Compounds 4-((1R,3R)-3-(5-bromo-1-oxoisoindolin-2-yl))-2,2,4,4-tetramethylcyclobutoxy)-2-chlorobenzonitrile (1-1) (189 mg, 0.4 mmol) and t-butyl 2-(pent-4-yn-1-oxy) acetate (119 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 hours under stirring. After the reaction was completed, the solvent was removed by evaporation under reduced pressure. The crude product was purified by TLC (PE:EA=3:1), to obtain 177 mg of intermediate 1-2, with a yield of 75%. MS (ES): m/z 591 $[M+H]^+$.

2. Synthesis of Intermediate 2-((5-(2-((1R,3R)-3-(3-chloro-4-cyanophenoxy)-2,2,4,4-tetramethylcyclobutyl)-1-oxoisoindolin-5-yl)pent-4-yn-1-yl)oxy) acetic acid Compound t-butyl 2-((5-(2-((1R,3R)-3-(3-chloro-4-cyanophenoxy)-2,2,4,4-tetramethylcyclobutyl)-1-oxoisoindolin-5-yl)pent-4-yn-1-yl)oxy)acetic acid (intermediate 1-2) (118 mg, 0.2 mmol) was dissolved in 2 mL of dichloromethane, to which was added 1 mL of trifluoroacetic acid, and the mixture was stirred 2 h at room temperature. The reaction was completed. The solvent was removed by evaporation under reduced pressure. The residue was directly used in next reaction, without further purification.

3. Synthesis of Final Product (2S,4R)-1-((S)-2-(2-((6-(4-(((1r,3r)-3-(3-chloro-4-cyanophenoxy)-2,2,4,4-tetramethylcyclobutyl)-1-oxoisoindolin-5-yl)pent-4-yn-1-yl) oxy)acetamido)-3,3-dimethylbutyryl)-4H-N-((S)-1-(4-(4-methylthiazol-5-yl)phenyl) ethyl) pyrrolidine-2-carboxamide Compounds 2-((5-(2-((1R,3R)-3-(3-chloro-4-cyanophenoxy)-2,2,4,4-tetramethylcyclobutyl)-1-oxoisoindolin-5-yl) pent-4-yn-1-yl)oxy)acetic acid (intermediate 1-3) (53.5 mg, 0.1 mmol) and ((2s,4r)-1-((s)-2-amino-3,3-dimethylbutyryl)-4-hydroxy-N-((s)-1-(4-(4-methylthiazol-5-yl)phenyl) ethyl) pyrrolidine-2-carboxamide (44.5 mg, 0.1 mmol) were dissolved in 2 mL of dichloromethane, to which were added DIPEA (38.7 mg, 0.3 mmol) and HATU (76.05 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 52 mg of the final product, with a yield of 54%. MS (ES): m/z 961 $[M+H]^+$. $^1H$ NMR (400 MHz, DMSO-$d_6$) δ 8.98 (s, 1H), 8.51-8.44 (m, 1H), 7.91 (s, 1H), 7.63 (d, J=9.9 Hz, 2H), 7.54-7.33 (m, 6H), 7.29 (s, 1H), 7.11-7.03 (m, 1H), 5.25-5.17 (m, 2H), 4.95-4.86 (m, 1H), 4.77 (s, 2H), 4.54 (s, 3H), 4.31 (s, 1H), 3.98 (s, 3H), 3.82-3.73 (m, 1H), 3.63 (s, 2H), 2.46 (s, 3H), 2.32-2.21 (m, 2H), 1.86 (s, 2H), 1.39 (s, 8H), 1.24 (s, 3H), 1.15 (s, 6H), 0.96 (s, 9H).

22: (2S,4R)-1-((S)-2-(2-((5-(4-(((1r,3r)-3-(3-chloro-4-cyanophenoxy)-2,2,4,4-tetramethylcyclobutyl) (trideuteromethyl)benzamide)-pent-4-yn-1-yl-oxyacetamido-3,3-dimethylbutane)-4-hydroxy-N-((s)-1-(4-methylthiazol-5-yl)phenyl)ethyl) pyrrolidine-2-carboxamide

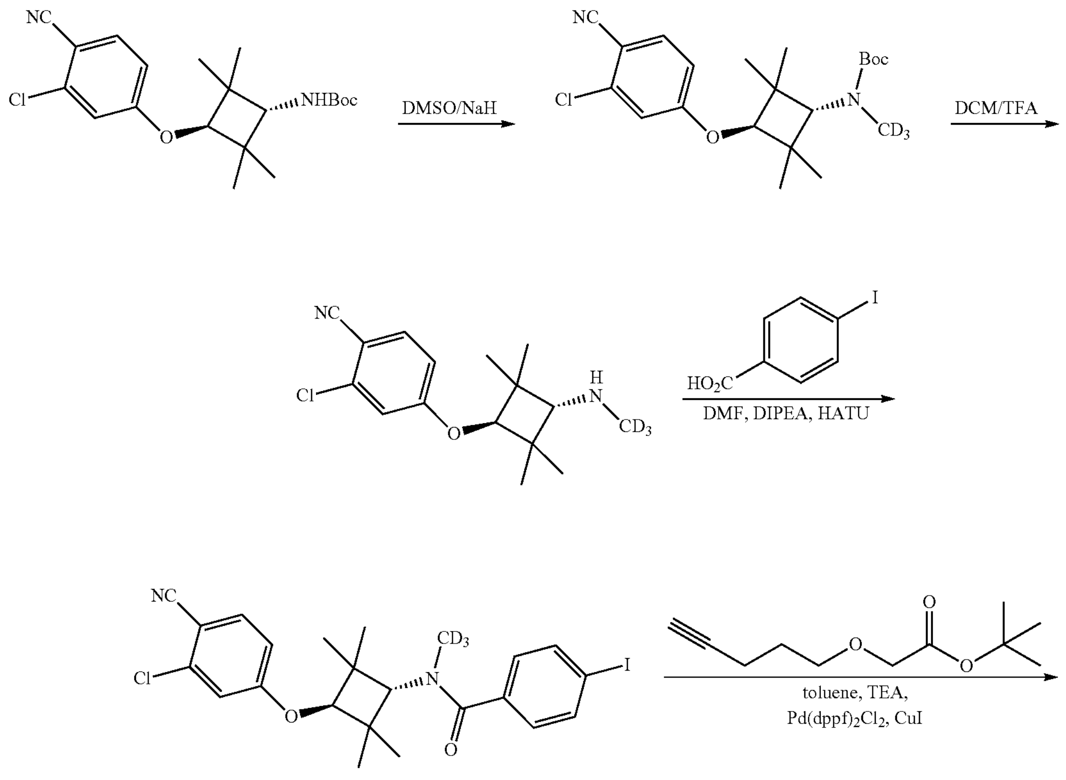

-continued

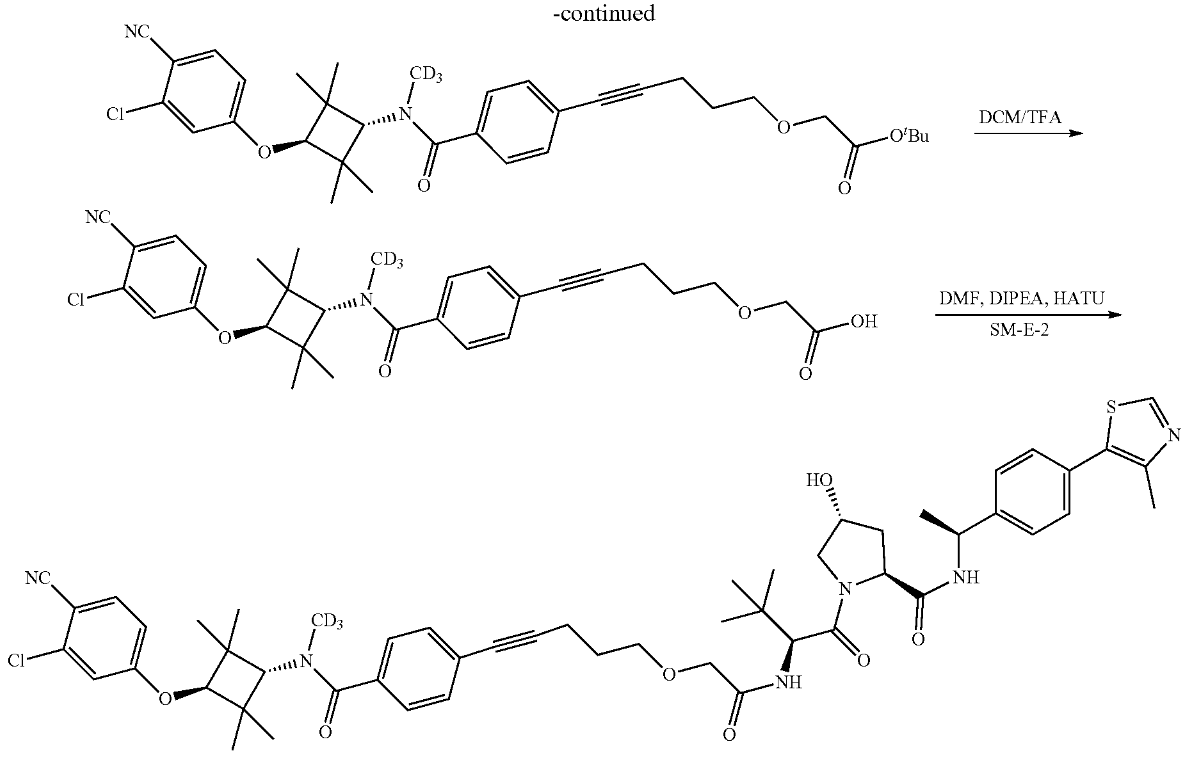

22

Synthesis of intermediate t-butyl ((1R,3R)-3-(3-chloro-4-cyanophenoxy)-2,2,4,4-tetramethylcyclobutyl)(deuteromethyl)carbamate Compound t-butyl ((1R,3R)-3-(3-chloro-4-cyanophenoxy)-2,2,4,4-tetramethylcyclobutyl)carbamate (1.89 g, 5 mmol) was dissolved in 5 mL of DMF, to which was added NaH (0.4 g, 10 mmol) in an ice bath, and the mixture was stirred for 0.5 h at room temperature. Deuteromethyl iodide (1.09 g, 7.5 mmol) was added, and the resultant mixture was further stirred and reacted for 3 h. After completion of the reaction, water was added, and then the reaction solution was extracted with ethyl acetate. The organic phase was evaporated under reduced pressure to remove the solvent, and the crude product was purified by column chromatography to obtain 1.74 g of intermediate 2-2, with a yield of 88%. MS (ES): m/z 397 $[M+H]^+$.

Synthesis of Intermediate ((1R,3R)-3-(3-chloro-4-cyanophenoxy)-2,2,4,4-tetramethylcyclobutyl)(deuteromethyl)carbamic acid Compound t-butyl ((1R,3R)-3-(3-chloro-4-cyanophenoxy)-2,2,4,4-tetramethylcyclobutyl)(deuteromethyl)carbamate (intermediate 2-2) (396 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

Synthesis of Intermediate N-((1R,3R)-3-(3-chloro-4-cyanophenoxy)-2,2,4,4-tetramethylcyclobutyl)-4-iodo-N-deuteromethylbenzamide Compound ((1R,3R)-3-(3-chloro-4-cyanophenoxy)-2,2,4,4-tetramethylcyclobutyl) (deuteromethyl)carbamic acid (intermediate 2-3) (296 mg, 1 mmol) and p-iodobenzoic acid (248 mg, 1 mmol) were dissolved in 2 mL of DMF, to which were added DIPEA (258 mg, 2 mmol) and HATU (570 mg, 1.5 mmol), and the mixture was stirred for 3 h at room temperature. After completion of the reaction, water was added, and then the reaction solution was extracted with ethyl acetate. The resultant organic phase was evaporated under reduced pressure to remove the solvent. The crude product was purified by TLC (PE:EA=3:1), to obtain 395 mg of intermediate 2-4, with a yield of 75%. MS (ES): m/z 526 $[M+H]^+$.

Synthesis of Intermediate t-butyl 2-((5-(4-(((1r,3r)-3-(3-chloro-4-cyanophenoxy)-2,2,4,4-tetramethylcyclobutyl)(deuteromethyl)carbamoyl)phenyl)pent-5-yn-1-yl)oxy) acetate Compound N-((1R,3R)-3-(3-chloro-4-cyanophenoxy)-2,2,4,4-tetramethylcyclobutyl)-4-iodo-N-deuteromethylbenzamide (intermediate 2-4) (210 mg, 0.4 mmol) and t-butyl 2-(pent-4-yne-1-oxy)acetate (119 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 hours under stirring. After the reaction was completed, the solvent was removed by evaporation under reduced pressure. The crude product was purified by TLC (PE:EA=3:1), to obtain 203 mg of intermediate 2-5, with a yield of 85%. MS (ES): m/z 596 $[M+H]^+$.

Synthesis of Intermediate 2-((5-(4-(((1r,3r)-3-(3-chloro-4-cyanophenoxy)-2,2,4,4-tetramethylcyclobutyl)(deuteromethyl)carbamoyl)phenyl)pent-5-yn-1-yl)oxy)acetic acid Compound t-butyl 2-((5-(4-(((1r,3r)-3-(3-chloro-4-cyanophenoxy)-2,2,4,4-tetramethylcyclobutyl)(deuteromethyl)carbamoyl)phenyl)pent-5-yn-1-yl)oxy)acetate (intermediate 2-5) (59.6 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

Compound 2-((5-(4-(((1r,3r)-3-(3-chloro-4-cyanophenoxy)-2,2,4,4-tetramethylcyclobutyl)(deuteromethyl)carbamoyl)phenyl)pent-5-yn-1-yl)oxy)acetic acid (intermediate 2-6) (54 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.05 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 49 mg of the final product HC-2797-01, with a yield of 51%. MS (ES): m/z 966[M+H]$^+$. $^1$H NMR (400 MHz, DMSO-$d_6$) δ 8.98 (s, 1H), 8.46 (d, J=7.6 Hz, 1H), 7.87 (d, J=8.7 Hz, 1H), 7.45 (dd, J=12.0, 8.1 Hz, 5H), 7.41-7.34 (m, 4H), 7.25 (s, 1H), 7.03 (d, J=8.4 Hz, 1H), 5.16 (d, J=3.3 Hz, 1H), 4.96-4.87 (m, 1H), 4.67 (d, J=7.9 Hz, 1H), 4.56 (d, J=9.5 Hz, 1H), 4.46 (t, J=8.1 Hz, 1H), 4.29 (s, 1H), 3.98 (s, 2H), 3.62 (dd, J=13.7, 7.8 Hz, 4H), 2.58-2.49 (m, 8H), 2.12-2.02 (m, 1H), 1.90-1.74 (m, 3H), 1.48 (d, J=6.9 Hz, 1H), 1.40-1.32 (m, 9H), 1.23 (s, 3H), 0.94 (s, 9H).

23 (2S,4R)-1-((S)-2-(2-((6-(4-(((1r,3r)-3-(3-chloro-4-cyanophenoxy)-2,2,4,4-tetramethylcyclobutyl)(deuteromethyl)benzamide)-hex-5-yn-1-yl-oxyacetamido-3,3-dimethylbutane)-4-hydroxy-N-((S)-1-(4-methylthiazol-5-yl)phenyl)ethyl) pyrrolidine-2-carboxamide

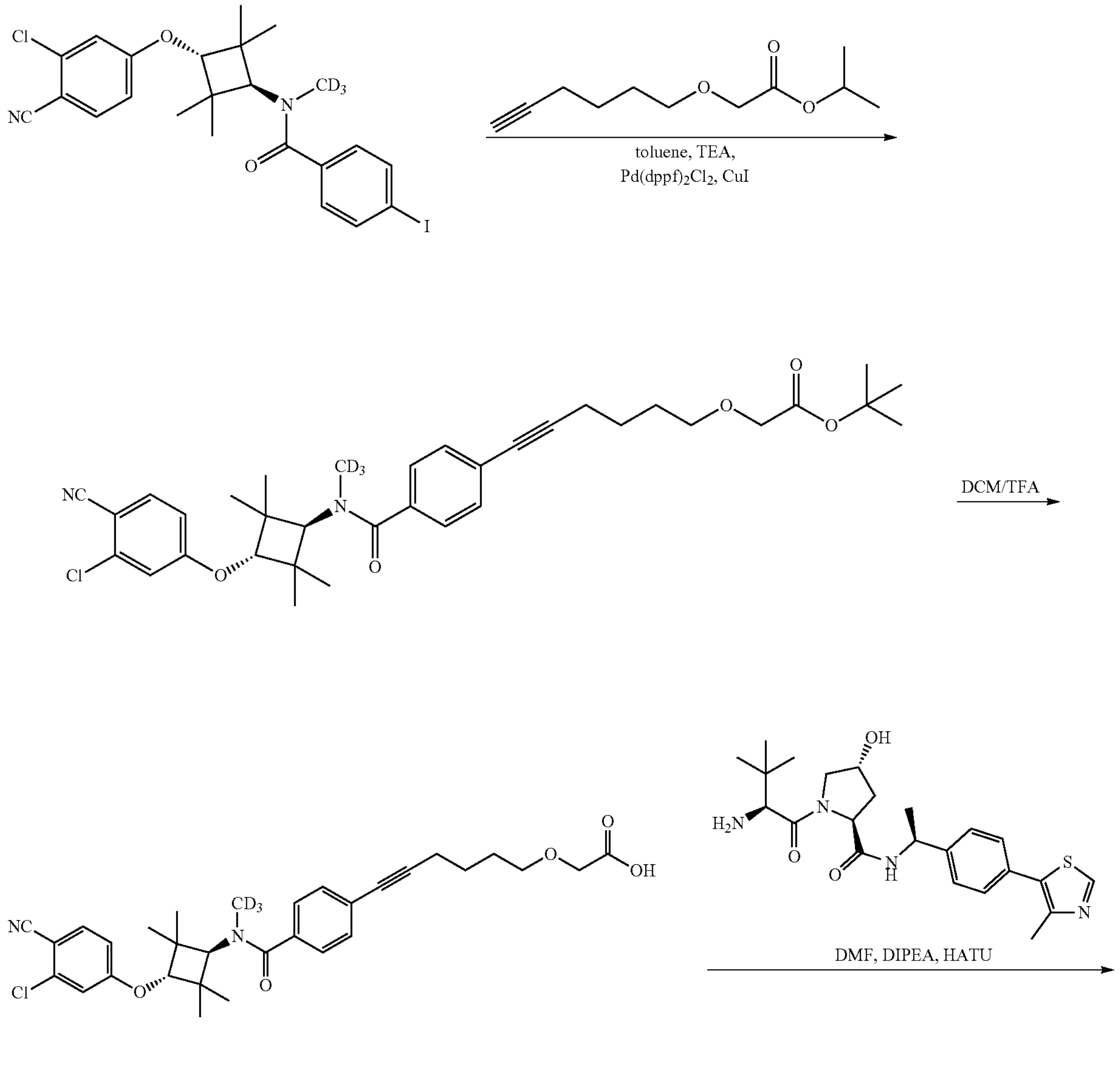

-continued

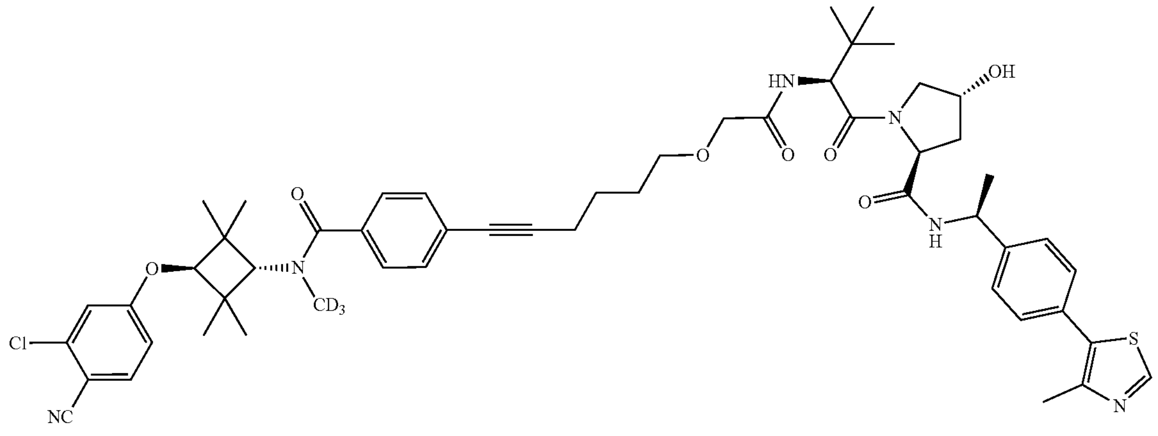

23

1. Synthesis of Intermediate t-butyl 2-((6-(4-(((1 r,3r)-3-(3-chloro-4-cyanophenoxy)-2,2,4,4-tetramethylcyclobutyl)(deuteromethyl)carbamoyl)phenyl) hex-5-yn-1-yl)oxy)acetate Compound N-((1R,3R)-3-(3-chloro-4-cyanophenoxy)-2,2,4,4-tetramethylcyclobutyl)-4-iodo-N-deuteromethylbenzamide (intermediate 2-4) (210 mg, 0.4 mmol) and t-butyl 2-(hex-5-yn-1-oxy)acetate (127 mg, 0.6 mmol) were dissolved in 3 mL of toluene, to which were added triethylamine (1 mL), $Pd(dppf)_2Cl_3$ (30 mg), and CuI (150 mg). Under $N_2$ protection, the reaction solution was heated to 90-100° C., and reacted for additional 12 hours under stirring. After the reaction was completed, the solvent was removed by evaporation under reduced pressure. The crude product was purified by TLC (PE:EA=3:1), to obtain 205 mg of intermediate 4-1, with a yield of 84%. MS(ES): m/z 610 $[M+H]^+$.

2. Synthesis of Intermediate 2-((6-(4-(((1 r,3r)-3-(3-chloro-4-cyanophenoxy)-2,2,4,4-tetramethylcyclobutyl)(deuteromethyl)carbamoyl)phenyl)hex-5-yn-1-yl)oxy)acetic acid Compound t-butyl 2-((6-(4-(((1r,3r)-3-(3-chloro-4-cyanophenoxy)-2,2,4,4-tetramethylcyclobutyl)(deuteromethyl) carbamoyl)phenyl)hex-5-yn-1-yl)oxy)acetic acid (intermediate 4-1) (61 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

3. Synthesis of final product HC-2799-01: (2S,4R)-1-((S)-2-(2-((6-(4-(((1r,3r)-3-(3-chloro-4-cyanophenoxy)-2,2,4,4-tetramethylcyclobutyl)(deuteromethyl) benzamide)-hex-5-yn-1l-yl-oxyacetamido-3,3-dimethylbutane)-4-hydroxy-N-((S)-1-(4-methylthiazol-5-yl)phenyl) ethyl)pyrrolidine-2-carboxamide Compounds 2-((6-(4-(((1r,3r)-3-(3-chloro-4-cyanophenoxy)-2,2,4,4-tetramethylcyclobutyl)(deuteromethyl)carbamoyl)phenyl)hex-5-yn-1-yl)oxy)acetic acid (intermediate 4-2) (55 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 53 mg of the final product HC-2799-01, with a yield of 54%. MS(ES): m/z 980 $[M+H]^+$. $^1H$ NMR (400 MHz, DMSO-$d_6$) δ 8.98 (s, 1H), 8.45 (d, J=7.7 Hz, 1H), 7.87 (d, J=8.6 Hz, 1H), 7.38 (ddd, J=48.2, 28.5, 19.8 Hz, 9H), 7.25 (s, 1H), 7.03 (d, J=9.0 Hz, 1H), 5.15 (d, J=3.4 Hz, 1H), 4.95-4.85 (m, 1H), 4.77-4.61 (m, 1H), 4.55 (d, J=9.6 Hz, 1H), 4.46 (t, J=8.2 Hz, 1H), 4.29 (s, 1H), 3.92 (d, J=16.9 Hz, 2H), 3.56 (dd, J=14.7, 9.1 Hz, 4H), 2.48 (d, J=21.7 Hz, 11H), 2.05 (d, J=8.4 Hz, 1H), 1.82-1.59 (m, 4H), 1.42-1.17 (m, 11H), 0.94 (s, 9H).

24: (2S,4R)-1-((S)-2-(2-((7-(4-(((1r,3r)-3-(3-chloro-4-cyanophenoxy)-2,2,4,4-tetramethylcyclobutyl)(deuteromethyl)benzamide)-hept-6-yn-1-yl-oxyacetamido-3,3-dimethylbutane)-4-hydroxy-N-((S)-1-(4-methylthiazol-5-yl)phenyl)ethyl) pyrrolidine-2-carboxamide

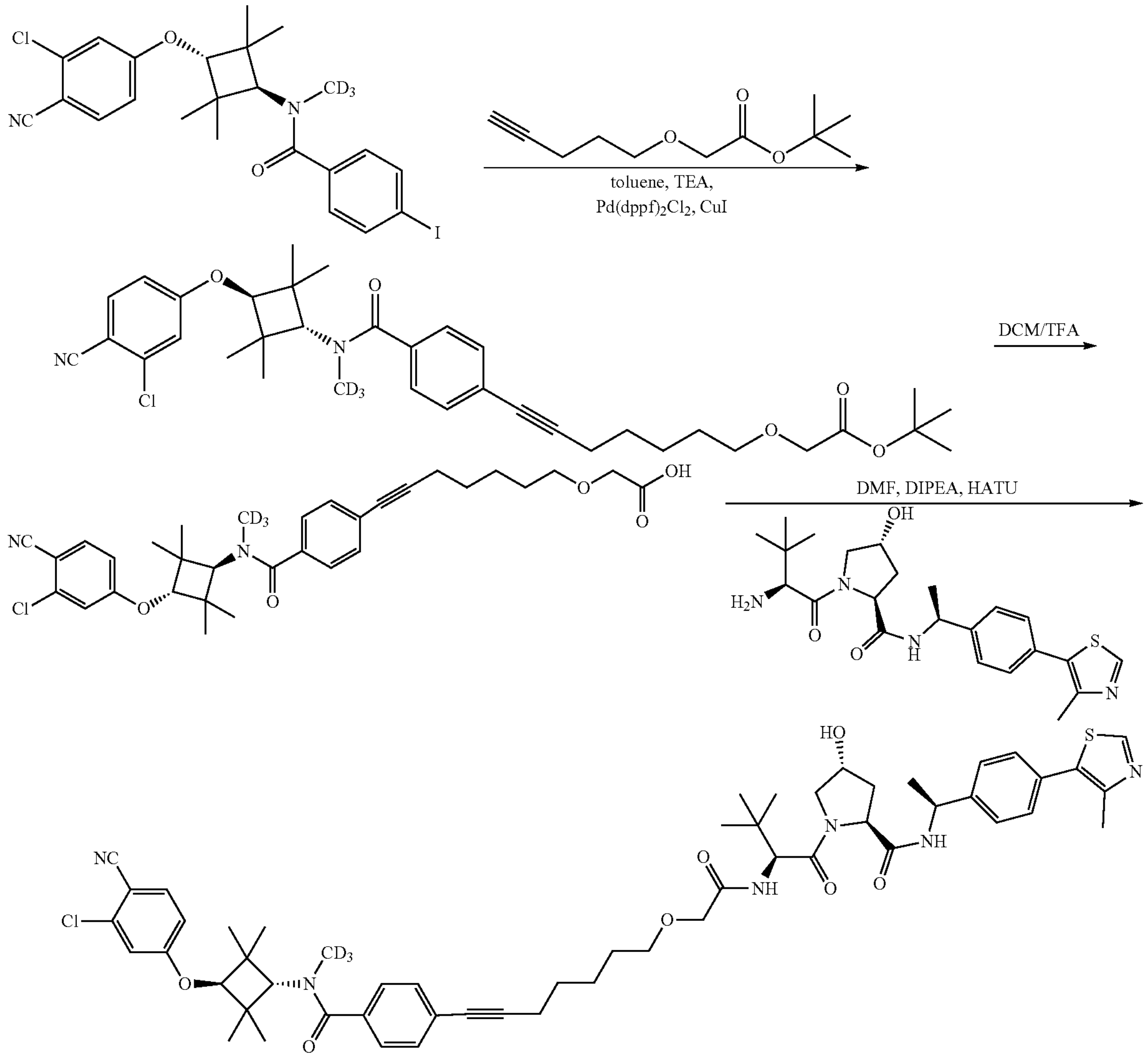

24

1. Synthesis of Intermediate t-butyl 2-((7-(4-(((1r,3r)-3-(3-chloro-4-cyanophenoxy)-2,2,4,4-tetramethylcyclobutyl)(deuteromethyl)carbamoyl)phenyl) hept-6-yn-1-yl)oxy)acetate Compounds N-((1R,3R)-3-(3-chloro-4-cyanophenoxy)-2,2,4,4-tetramethylcyclobutyl)-4-iodo-N-deuteromethylbenzamide (intermediate 2-4) (210 mg, 0.4 mmol) and t-butyl 2-(hept-6-yn-1-oxy)acetate (136 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 h under stirring. After the reaction was completed, the solvent was removed by evaporation under reduced pressure. The crude product was purified by TLC (PE:EA=3:1), to obtain 212 mg of intermediate 6-1, with a yield of 85%. MS(ES): m/z 624 $[M+H]^+$.

2. Synthesis of Intermediate 2-((7-(4-(((1r,3r)-3-(3-chloro-4-cyanophenoxy)-2,2,4,4-tetramethylcyclobutyl)(deuteromethyl)carbamoyl)phenyl)hept-6-yn-1-yl)oxy)acetic acid Compound t-butyl 2-((7-(4-(((1r,3r)-3-(3-chloro-4-cyanophenoxy)-2,2,4,4-tetramethylcyclobutyl)(deuteromethyl) carbamoyl)phenyl)hept-6-yn-1-yl)oxy)acetate (intermediate 6-1) (62 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

3. Synthesis of Final Product 24: (2S,4S)-1-((S)-2-(2-((7-(4-(((1r,3r)-3-(3-chloro-4-cyanophenoxy)-2,2,4,4-tetramethylcyclobutyl)(deuteromethyl)benzamide)hept-6-yn-1-yl-oxyacetamido-3,3-dimethylbutane)-4-hydroxy-N-((s)-1-(4-methylthiazol-5-yl)phenyl)ethyl)pyrrolidine-2-carboxamide Compounds 2-((7-(4-(((1r,3r)-3-(3-chloro-4-cyanophenoxy)-2,2,4,4-tetramethylcyclobutyl)(deuteromethyl)carbamoyl)phenyl)hept-6-yn-1-yl)oxy)acetic acid (intermediate 6-2) (57 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 50 mg of the final product HC-2801-01, with a yield of 50%. MS(ES): m/z 994[M+H]. $^1$H NMR (400 MHz, DMSO-$d_6$) δ 8.98 (s, 1H), 8.45 (d, J=7.7 Hz, 1H), 7.87 (d, J=8.6 Hz, 1H), 7.38 (ddd, J=48.2, 28.5, 19.8 Hz, 9H), 7.25 (s, 1H), 7.03 (d, J=9.0 Hz, 1H), 5.15 (d, J=3.4 Hz, 1H), 4.95-4.85 (m, 1H), 4.77-4.61 (m, 1H), 4.55 (d, J=9.6 Hz, 1H), 4.46 (t, J=8.2 Hz, 1H), 4.29 (s, 1H), 3.92 (d, J=16.9 Hz, 2H), 3.56 (dd, J=14.7, 9.1 Hz, 4H), 2.48 (d, J=21.7 Hz, 11H), 2.05 (d, J=8.4 Hz, 1H), 1.82-1.59 (m, 4H), 1.42-1.17 (m, 13H), 0.94 (s, 9H).

25: N-(5-(2-((1r,3r)-3-(3-chloro-4-cyanophenoxy)-2,2,4,4-tetramethylcyclobutyl)-1-oxoisoindolin-5-yl)pent-4-yn-1-yl)-N-((S)-1-((2S,4R)-4-hydroxy-2-((S)-1-(4-(4-methylthiazol-5-yl)phenyl)ethyl)carbamoyl)pyrrolidin-1-yl)-3,3-dimethyl-1-oxobutan-2-yl)cyclopropane-1,1-dimethylamide

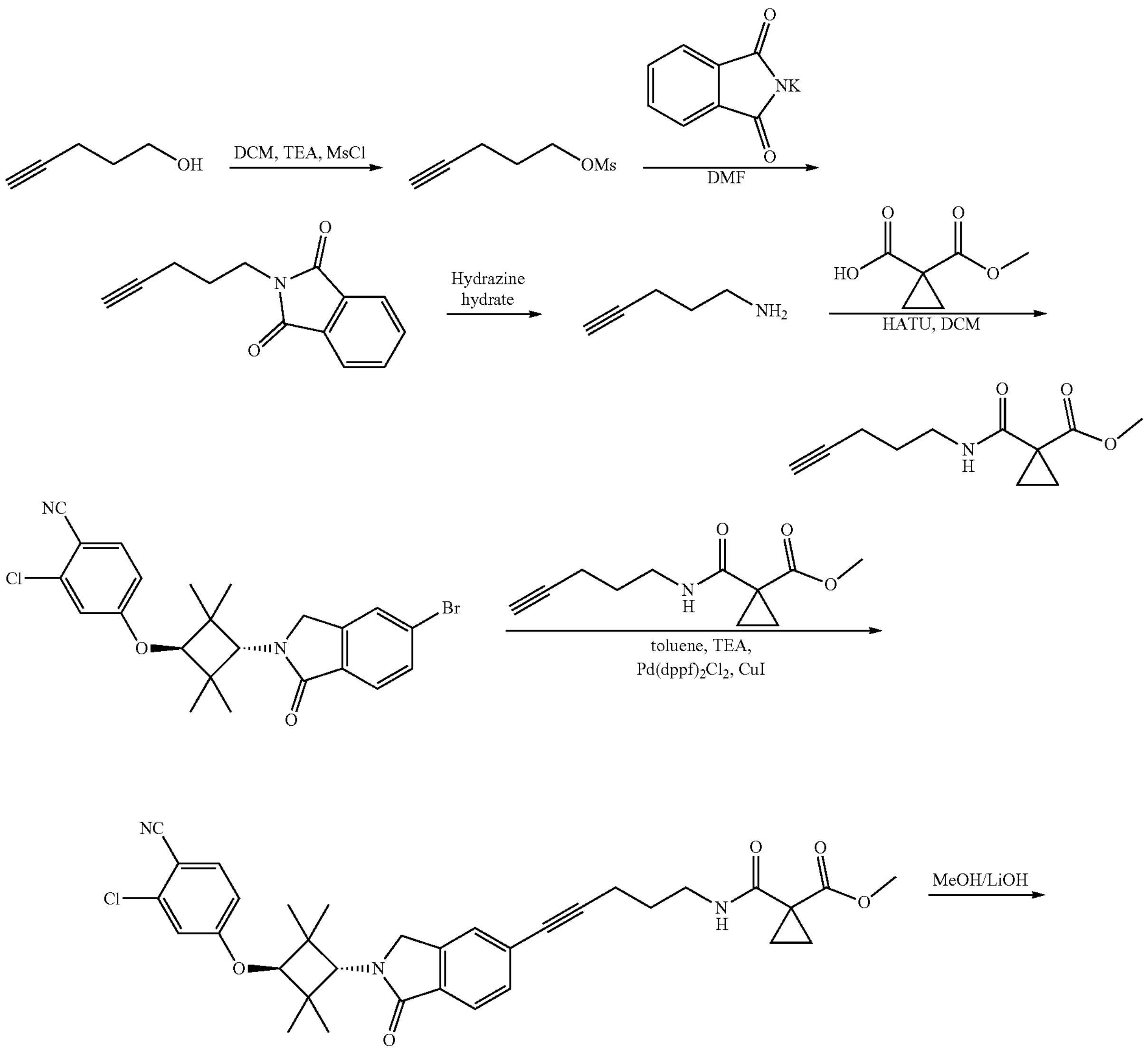

-continued

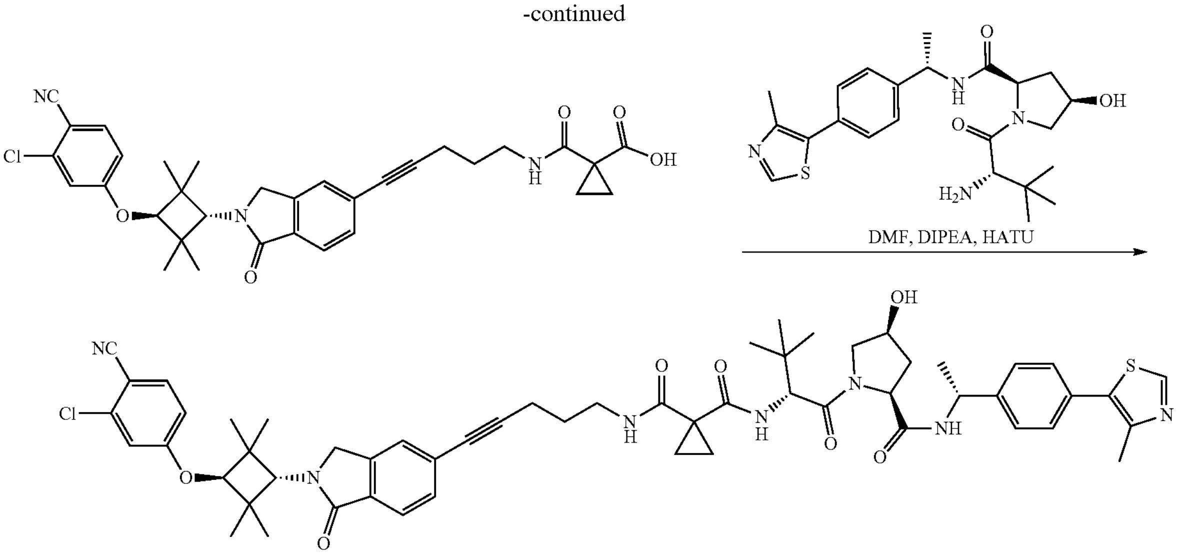

25

1. Synthesis of Intermediate 2-(pent-4-en-1-yl)isoindoline-1,3-dione

Pent-4-yn-1-ol (4.2 g, 0.05 mol) was dissolved in 30 mL DCM, to which was added TEA (7.6 g, 0.075 mol), and then methylsulfonyl chloride (6.9 g, 0.06 mol) was added drop-wise in an ice bath. The reaction was stirred for 5 h. After the reaction was completed, 25 mL of water and 30 mL of dichloromethane were added for extraction, and the organic phase obtained was evaporated under reduced pressure, to remove the solvent. The crude product was directly used in next reaction, without further purification.

The above product (3.2 g, 0.02 mol) was dissolved in 20 mL DMF, to which was added phthalimide potassium salt (5.6 g, 0.03 mol), and then the reaction solution was heated to 80° C., and allowed to react for 6 h under stirring. After completion of the reaction, 30 mL of water and 90 mL of ethyl acetate were added for extraction, and the organic phase obtained was evaporated under reduced pressure, to remove the solvent. The crude product was purified by column chromatography (PE:EA=3:1), to obtain intermediate 8-3 (3.9 g), with a yield of 91%. MS(ES): m-z 214 $[M+H]^+$.

2. Synthesis of Intermediate pent-4-yn-1-amine

The above product (2.1 g, 0.01 mol) was dissolved in 30 mL of absolute ethanol, to which was added hydrazine hydrate (0.75 g, 0.015 mol), and then the reaction solution was heated to 80° C., and allowed to react for 5 h under stirring. After completion of the reaction, the reaction solution was cooled, and then filtered to remove insoluble matter. To the filtrate, were added 30 mL of water and 90 mL of ethyl acetate for extraction, and the organic phase obtained was evaporated under reduced pressure, to remove the solvent. The crude product was directly used in next reaction, without further purification.

3. Synthesis of Intermediate: methyl 1-(4-pentyne-1-carbamoyl)cyclopropane-1-carboxylate The above product pentynamine (830 mg, 10 mmol) and 1-methoxycarbonylcyclopropane-1-carboxylic acid (1.44 g, 10 mmol) were dissolved in 2 mL of dichloromethane, to which were added DIPEA (3.9 g, 30 mmol) and HATU (7.6 g, 20 mmol), and then the mixture was stirred 4 h at room temperature. After completion of the reaction, the reaction solution was added with water and then extracted with dichloromethane. The resultant organic phase was evaporated under reduced pressure to remove the solvent. The crude product was purified by TLC (PE:EA=3:1) to obtain 1.79 g of intermediate 8-5, with a yield of 85%. MS(ES): m/z 210 $[M+H]^+$.

4. Synthesis of Intermediate methyl 1-((5-(2-((1r,3r)-3-(3-chloro-4-cyanophenoxy)-2,2,4,4-tetramethylcyclobutyl)-1-oxoisoindolin-5-yl)pent-4-yn-1-yl)carbamoyl) cyclopropane-1-carboxylate Compounds 4-((1R,3R)-3-(5-bromo-1-oxoisobutanol-2-yl)-2,2,4,4-tetramethylcyclobutoxy)-2-chlorobenzonitrile (1-1) (189 mg, 0.4 mmol) and methyl 1-(4-pentyne-1-carbamoyl)cyclopropane-1-carboxylate (126 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 h under stirring. After the reaction was completed, the solvent was removed by evaporation under reduced pressure. The crude product was purified by TLC (PE:EA=2:1), to obtain 188 mg of intermediate 8-6, with a yield of 78%. MS(ES): m/z 602 $[M+H]^+$.

5. Synthesis of Intermediate 1-((5-(2-((1r,3r)-3-(3-chloro-4-cyanophenoxy)-2,2,4,4-tetramethylcyclobutyl)-1-oxoisoindolin-5-yl)pent-4-yn-1-yl)carbamoyl)cyclopropane-1-carboxylic acid Compound 1-((5-(2-((1r,3r)-3-(3-chloro-4-cyanophenoxy)-2,2,4,4-tetramethylcyclobutyl)-1-oxoisoindolin-5-yl)pent-4-yn-1-yl)carbamoyl)cyclopropane-1-carboxylate methyl (intermediate 8-6) (60 mg, 0.1 mmol) was dissolved in 2 mL of anhydrous methanol, to which was added lithium hydroxide (9.6 mg, 0.4 mmol), and then the reaction solution was stirred for 5 h at room temperature. After completion of the reaction, to the filtrate, were added 10 mL of water and 20 mL of ethyl acetate for extraction. The organic phase obtained were evaporated under reduced pressure to remove the solvent. The crude product was directly used in next reaction, without further purification.

6. Synthesis of Final Product 25: N-(5-(2-((1r,3r)-3-(3-chloro-4-cyanophenoxy)-2,2,4,4-tetramethylcyclobutyl)-1-oxoisoindolin-5-yl)pent-4-yn-1-yl)-N-((S)-1-((2S,4R)-4-hydroxy-2-((S)-1-(4-(4-methylthiazol-5-yl)phenyl)ethyl)carbamoyl) pyrrolidin-1-yl)-3,3-dimethyl-1-oxobutan-2-yl) cyclopropane-1,1-diformamide Compounds 1-((5-(2-((1r,3r)-3-(3-chloro-4-cyanophenoxy)-2,2,4,4-tetramethylcyclobutyl)-1-oxoisoindolin-5-yl) pent-4-yn-1-yl)carbamoyl)cyclopropane-1-carboxylic acid (intermediate 8-7) (59 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 55 mg of final product HC-2803-01, with a yield of 54%. MS (ES): m/z 1014 $[M+H]^+$. $^1$H NMR (400 MHz, DMSO-$d_6$) δ 9.40 (d, J=8.7 Hz, 1H), 8.98 (s, 1H), 8.42 (d, J=7.7 Hz, 1H), 7.90 (d, J=8.8 Hz, 1H), 7.82 (s, 1H), 7.66 (d, J=7.9 Hz, 1H), 7.61 (s, 1H), 7.51 (d, J=7.8 Hz, 1H), 7.43 (d, J=8.3 Hz, 2H), 7.37 (d, J=8.2 Hz, 2H), 7.28 (d, J=2.3 Hz, 1H), 7.07 (dd, J=8.8, 2.4 Hz, 1H), 5.13 (d, J=3.5 Hz, 1H), 4.90 (s, 1H), 4.77 (s, 2H), 4.59-4.38 (m, 3H), 4.30 (d, J=10.6 Hz, 2H), 3.59 (s, 2H), 3.23 (d, J=6.2 Hz, 2H), 2.49-2.43 (m, 4H), 2.08-1.97 (m, 1H), 1.83-1.68 (m, 3H), 1.42-1.34 (m, 8H), 1.32-1.21 (m, 8H), 1.15 (s, 4H), 0.94 (d, J=11.9 Hz, 9H).

26: (2S,4R)-1-((S)-2-(2-((4-(4-(((1r,3r)-3-(3-chloro-4-cyanophenoxy)-2,2,4,4-tetramethylcyclobutyl) (deuteromethyl)benzamide)-but-3-yn-1-yl-oxyacetamido-3, 3-dimethylbutane)-4-hydroxy-N-((S)-1-(4-methylthiazol-5-yl)phenyl)ethyl) pyrrolidine-2-carboxamide

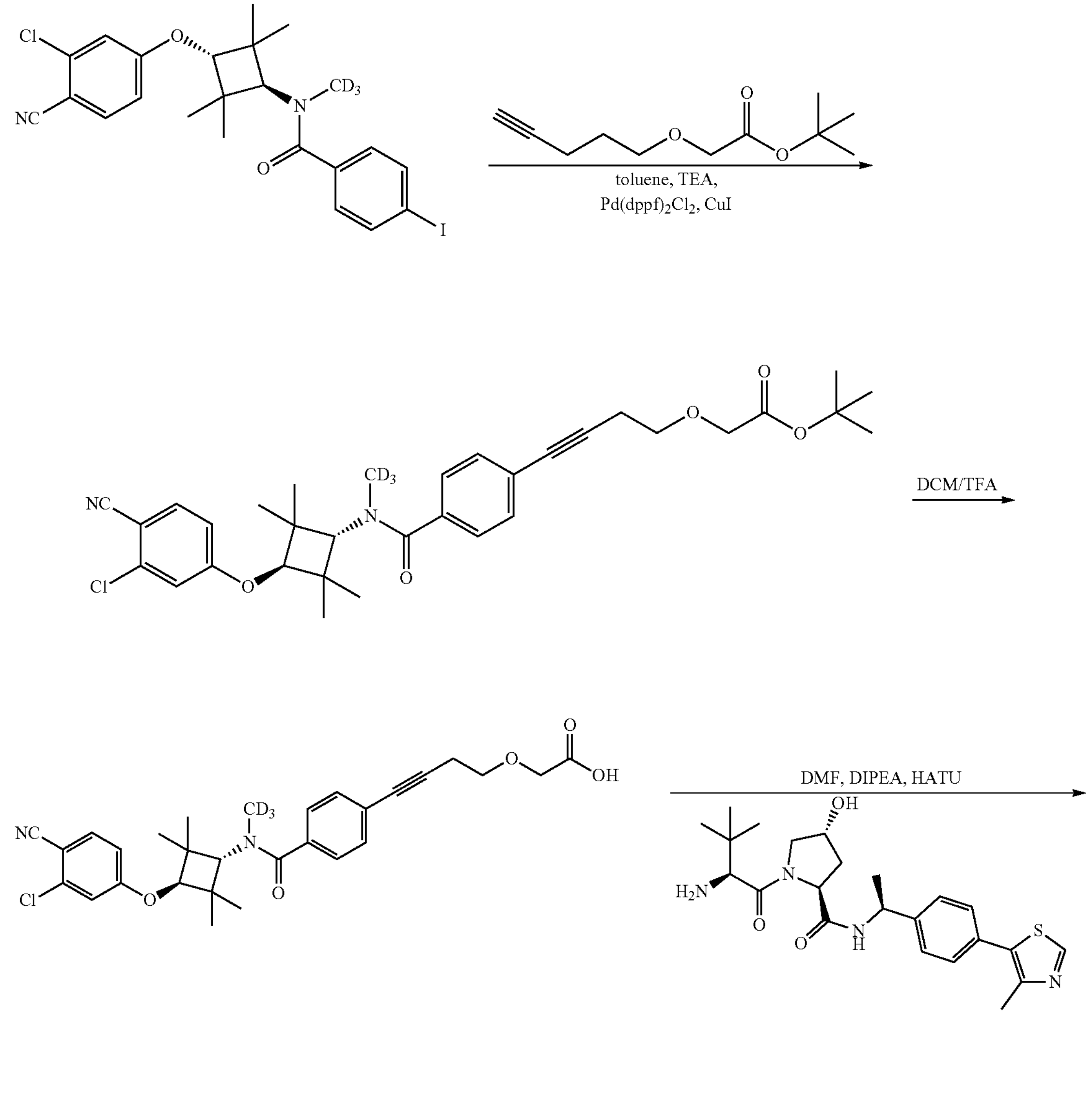

-continued

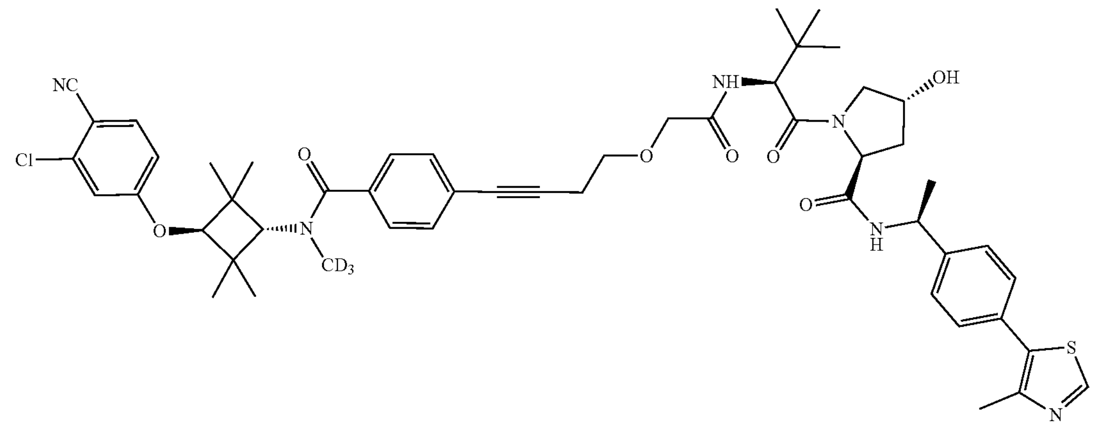

26

1. Synthesis of Intermediate t-butyl 2-((4-(4-((1r, 3r)-3-(3-chloro-4-cyanophenoxy)-2,2,4,4-tetramethylcyclobutyl)(methyl-$d_3$)carbamoyl)phenyl)-but-3-yn-1-yl)oxy) acetate Compounds N-((1r,3r)-3-(3-chloro-4-cyanophenoxy)-2, 2,4,4-tetramethylcyclobutyl)-4-iodo-N-deuteromethylbenzamide (210 mg, 0.4 mmol) and t-butyl 2-(but-3-yne-1-oxy) acetate (111 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 h under stirring. After the reaction was completed, the solvent was removed by evaporation under reduced pressure. The crude product was purified by TLC (PE:EA=3:1), to obtain 203 mg of product, with a yield of 87%. MS (ES): m/z 582 $[M+H]^+$.

2. Synthesis of Intermediate 2-((4-(4-((1r,3r)-3-(3-chloro-4-cyanophenoxy)-2,2,4,4-tetramethylcyclobutyl)(methyl-d3)carbamoyl)phenyl)-but-3-yn-1-yl-)oxy)acetic acid Compound t-butyl 2-((4-(4-((1r,3r)-3-(3-chloro-4-cyanophenoxy)-2,2,4,4-tetramethylcyclobutyl)(methyl-d3)carbamoyl)phenyl)-but-3-yn-1-yl-)oxy)acetate (58 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

3. Synthesis of Final Product 26: (2S, 4R)-1-((S)-2-(2-((4-(4-(((1r,3r)-3-(3-chloro-4-cyanophenoxy)-2,2,4,4-tetramethylcyclobutyl)(deuteromethyl)benzamide)-but-3-yn-1-yl-oxyacetamido-3,3-dimethylbutane)-4-hydroxy-N-((S)-1-(4-methylthiazol-5-yl)phenyl)ethyl)pyrrolidine-2-carboxamide Compounds 2-((4-(4-((1r,3r)-3-(3-chloro-4-cyanophenoxy)-2,2,4,4-tetramethylcyclobutyl)(methyl-d3)carbamoyl)phenyl)-but-3-yn-1-yl-)oxy)acetic acid (53 mg, 0.1 mmol) and ((2s, 4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 50 mg of final product 26, with a yield of 52%. MS (ES): m/z 952 $[M+H]^+$. $^1H$ NMR (400 MHz, DMSO-$d_6$) δ 8.99 (s, 1H), 8.46 (d, J=7.8 Hz, 1H), 7.88 (d, J=8.5 Hz, 1H), 7.55-7.35 (m, 9H), 7.26 (s, 1H), 7.08-7.00 (m, 1H), 5.38 (s, 1H), 5.15 (s, 1H), 4.92 (s, 1H), 4.56 (d, J=9.3 Hz, 2H), 4.46 (s, 2H), 4.29 (s, 1H), 4.04 (s, 3H), 3.65 (d, J=40.9 Hz, 6H), 2.77 (s, 2H), 2.12-1.93 (m, 2H), 1.83-1.67 (m, 2H), 1.36 (d, J=12.4 Hz, 9H), 0.92 (s, 12H).

27: (2R,4R)-1-((R)-2-(2-((4-(2-((1r,3r)-3-(3-chloro-4-cyanophenoxy)-2,2,4,4-tetramethylcyclobutyl)-1-oxoisobutanol-5-yl)-3-butyne-1-yl)oxy)acetamido)-3, 3-dimethylbutyryl)-4-hydroxy-N-((S)-1-(4-methylthiazol-5-yl)phenyl)ethyl) pyrrolidine-2-carboxamide

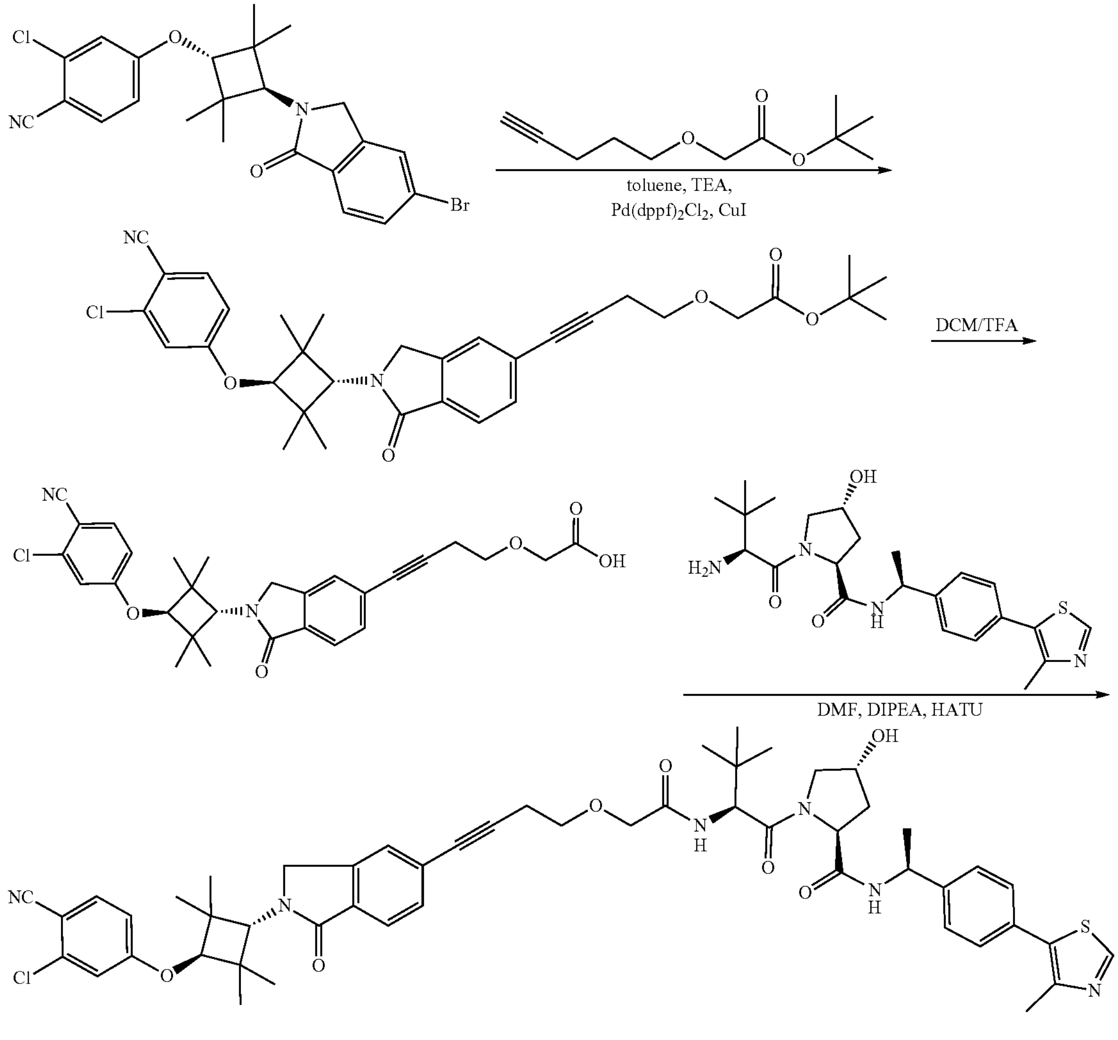

27

1. Synthesis of Intermediate t-butyl 2-((4-(2-((1r, 3r)-3-(3-chloro-4-cyanophenoxy)-2,2,4,4-tetramethylcyclobutyl)-1-oxoisoindolin-5-yl)-3-butyne-1-yl) oxy)acetate Compounds 4-((1R,3R)-3-(5-bromo-1-oxoisobutanol-2-yl)-2,2,4,4-tetramethylcyclobutoxy)-2-chlorobenzonitrile (1-1) (189 mg, 0.4 mmol) and t-butyl 2-(but-3-yne-1-oxy) acetate (119 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 h under stirring. After the reaction was completed, the solvent was removed by evaporation under reduced pressure. The crude product was purified by TLC (PE:EA=3:1), to obtain 180 mg of intermediate 12-1, with a yield of 78%. MS (ES): m/z 577 $[M+H]^+$.

2. Synthesis of Intermediate 2-((4-(2-((1r,3r)-3-(3-chloro-4-cyanophenoxy)-2,2,4,4-tetramethylcyclobutyl)-1-oxoisoindolin-5-yl)-3-butyne-1-yl)oxy) acetic acid Compound t-butyl 2-((4-(2-((1r,3r)-3-(3-chloro-4-cyanophenoxy)-2,2,4,4-tetramethylcyclobutyl)-1-oxoisoindolin-5-yl)-3-butyne-1-yl)oxy)acetate (intermediate 12-1) (58 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

3. Synthesis of Final Product 27: (2R,4R)-1-((R)-2-(2-((4-(2-((1r,3r)-3-(3-chloro-4-cyanophenoxy)-2,2,4,4-tetramethylcyclobutyl)-1-oxoisobutanol-5-yl)-3-butyne-1-yl)oxy)acetamido)-3,3-dimethylbutyryl)-4-hydroxy-N-((S)-1-(4-methylthiazol-5-yl)phenyl) ethyl)pyrrolidine-2-carboxamide Compounds 2-((4-(4-((1r,3r)-3-(3-chloro-4-cyanophenoxy)-2,2,4,4-tetramethylcyclobutyl)(methyl-d3)carbamoyl)phenyl)-but-3-yn-1-yl-)oxy)acetic acid (intermediate 10-2) (52 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 53 mg of final product 27, with a yield of 56%. MS (ES): m/z 947 $[M+H]^+$. $^1H$ NMR (400 MHz, DMSO-$d_6$) δ 8.98 (s, 1H), 8.51-8.44 (m, 1H), 7.91 (s, 1H), 7.63 (d, J=9.9 Hz, 2H), 7.54-7.33 (m, 6H), 7.29 (s, 1H), 7.11-7.03 (m, 1H), 5.25-5.17 (m, 2H), 4.95-4.86 (m, 1H), 4.77 (s, 2H), 4.54 (s, 3H), 4.31 (s, 1H), 3.98 (s, 3H), 3.82-3.73 (m, 1H), 3.63 (s, 2H), 2.46 (s, 3H), 2.32-2.21 (m, 2H), 1.86 (s, 2H), 1.39 (s, 8H), 1.24 (s, 3H), 1.15 (s, 6H), 0.96 (s, 9H).

28: N-(5-(4-((1r,3r)-3-(3-chloro-4-cyanophenoxy)-2,2,4,4-tetramethylcyclobutyl)(methyl-d3)carbamoyl) phenyl)-4-pentyne-1-yl)-N-((S)-1-((2S,4R)-4-hydroxy-2-((S)-1-(4-(4-methylthiazol-5-yl)phenyl) ethyl)carbamoyl) pyrrolidin-1-yl)-3,3-dimethyl-1-oxobutan-2-yl)cyclopropane-1,1-diformamide

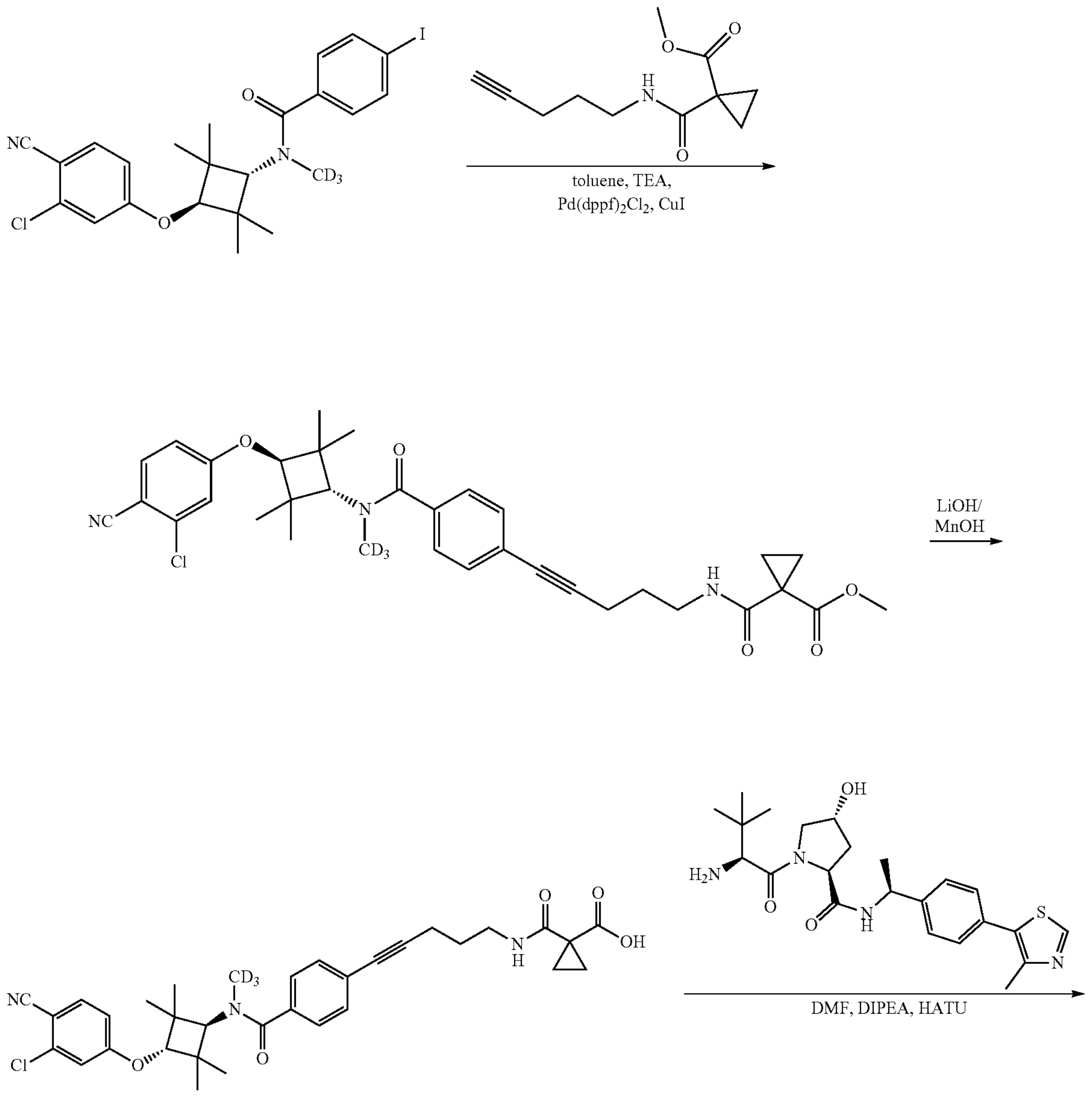

-continued

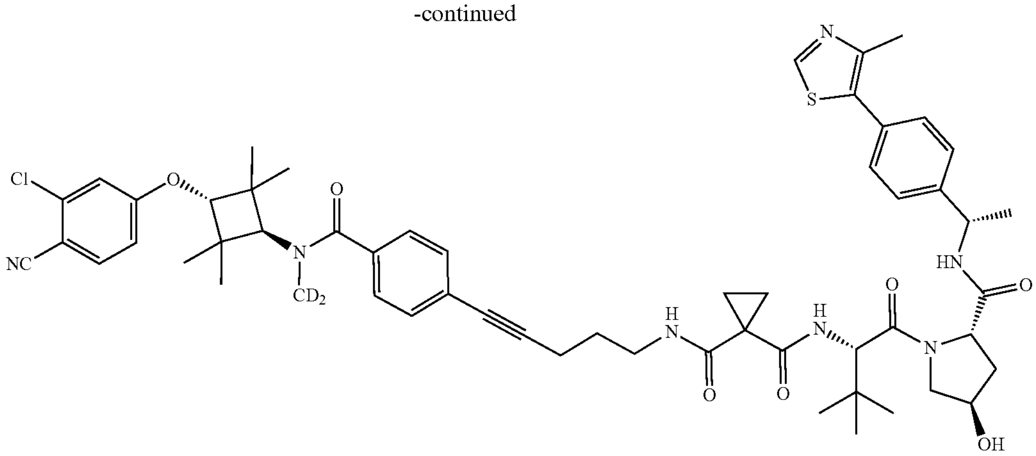

28

51 mg of final product 28 was obtained, with a yield of 50%. MS (ES): m/z 1019 $[M+H]^+$. $^1H$ NMR (400 MHz, DMSO-$d_6$) δ 9.39 (d, J=8.8 Hz, 1H), 8.99 (s, 1H), 8.42 (d, J=7.7 Hz, 1H), 7.89-7.80 (m, 2H), 7.49-7.41 (m, 4H), 7.37 (d, J=8.0 Hz, 2H), 7.26 (s, 1H), 7.04 (s, 1H), 5.12 (s, 1H), 4.92 (d, J=7.0 Hz, 1H), 4.78-4.60 (m, 2H), 4.46 (dd, J=21.3, 8.4 Hz, 3H), 4.29 (s, 1H), 3.55 (d, J=29.2 Hz, 5H), 3.22 (s, 2H), 3.00-2.83 (m, 1H), 2.46 (s, 5H), 2.07-1.95 (m, 1H), 1.84-1.64 (m, 3H), 1.41-1.31 (m, 9H), 1.28 (d, J=9.5 Hz, 4H), 0.94 (d, J=

29: (2S,4R)-1-((S)-2-(2-((6-(2-(((1r,3r)-3-(3-chloro-4-cyanophenoxy)-2,2,4,4-tetramethylcyclobutyl)-1-oxoisobutanol-5-yl)hept-5-yn-1-yl)oxy)acetamido)-3,3-dimethylbutyryl)-N-((S)-1-(4-(3,5-dimethylthiazol-4-yl)phenyl)ethyl)-4-hydroxypyrrolidine-2-carboxamide

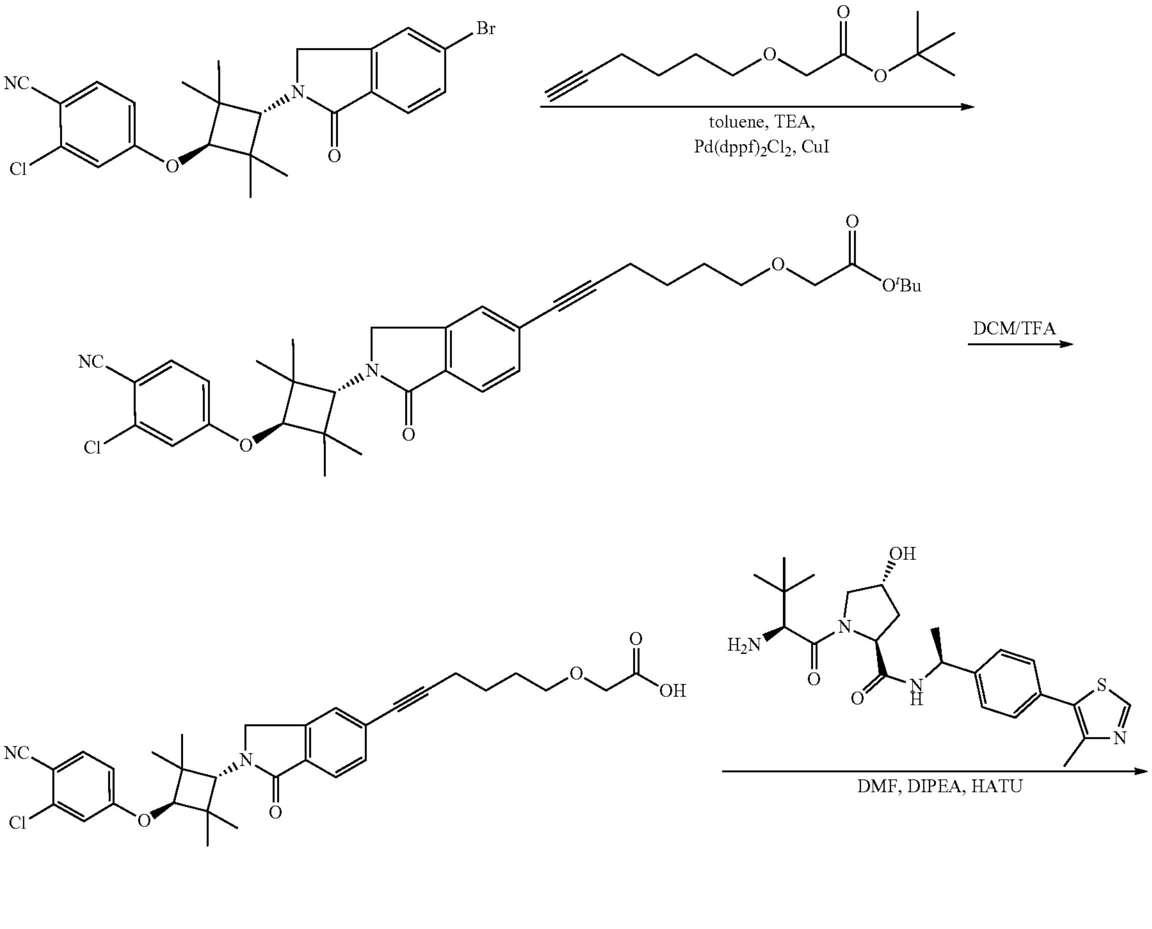

-continued
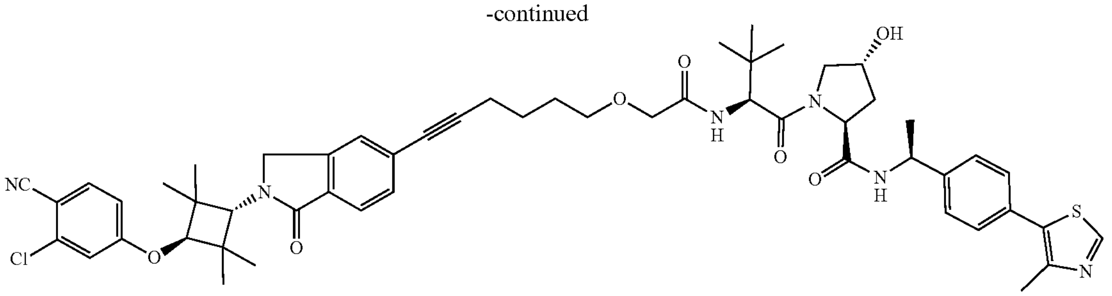
29
51 mg of final product HC-2820-01 was obtained, with a yield of 52%. MS (ES): m/z 975 [M+H]$^+$. $^1$H NMR (400 MHz, DMSO-$d_6$) δ 8.98 (s, 1H), 8.51-8.44 (m, 8H), 7.91 (s, 1H), 7.63 (d, J=9.9 Hz, 2H), 7.54-7.33 (m, 6H), 7.29 (s, 1H), 7.11-7.03 (m, 1H), 5.25-5.17 (m, 2H), 4.95-486 (m, 1H), 4.77 (s, 2H), 4.54 (s 3H), 4.31 (s, 1H), 3.98 (s, 3H), 3.82-3.73 (m, 1H), 3.63 (s, 2H), 2.46 (s, 3H), 2.32-2.21 (m, 2H), 1.76 (m 2H), 1.52 (m, 2H), 1.39 (s, 8H), 1.24 (s, 3H) 1.15 (s, 6H), 0.96 (s, 9H).
30: (2s,4r)-1-((s)-2-(2-(4-(4-(2-((1r,3r)-3-(3-chloro-4-cyanophenoxy)-2,2,4,4-tetramethylcyclobutyl)-1-oxoisobutanol-5-yl)-1H-1,2,3-triazol-1-yl)butoxy) acetamido)-3,3-dimethylbutyryl)-4-hydroxy-N-((S)-1-(4-(4-methylthiazol-5-yl) phenyl)ethyl)pyrrolidine-2-carboxamide
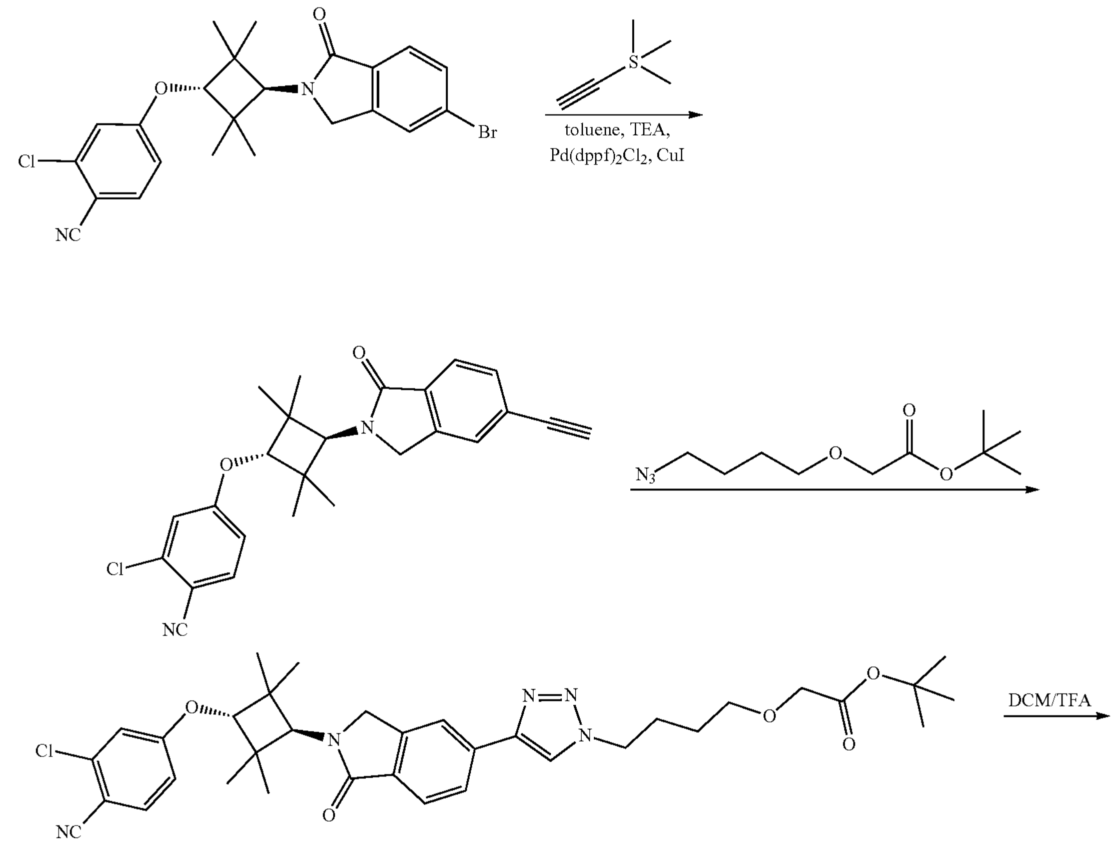

-continued

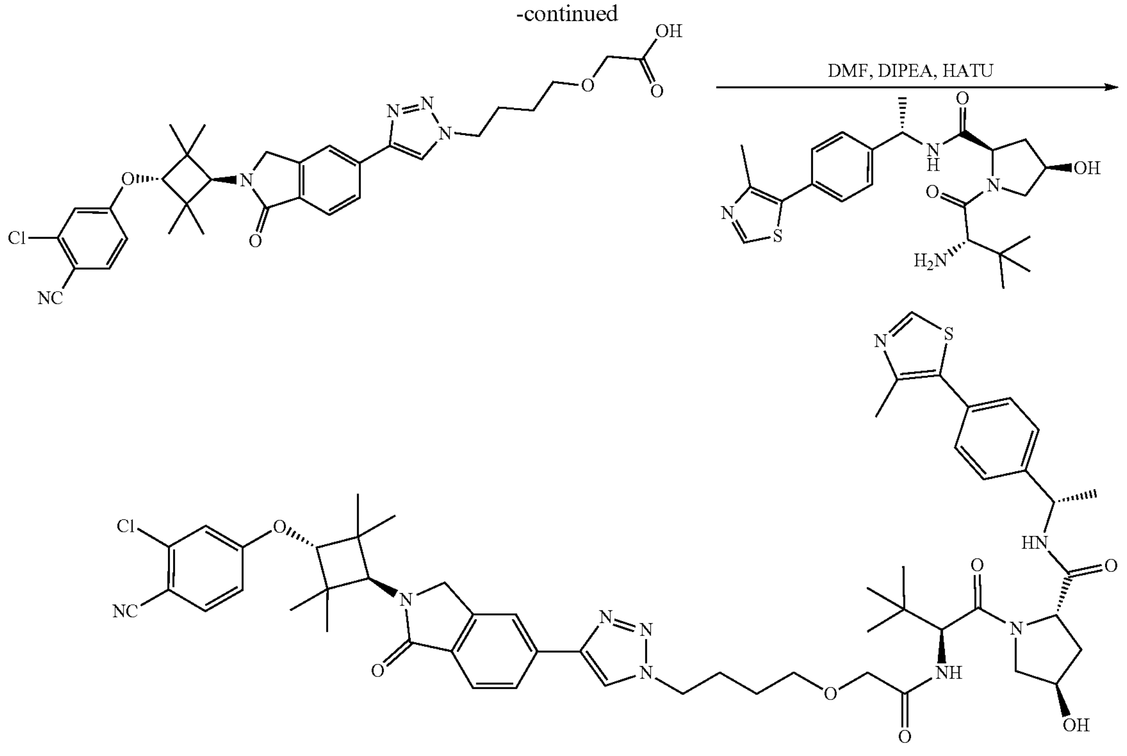

30

1. Synthesis of Intermediate 2-chloro-4-((1r,3r)-3-(5-ethynyl-1-oxoisobutanol-2-yl)-2,2,4,4-tetramethylcyclobutoxy)benzonitrile Compound 4-((1R,3R)-3-(5-bromo-1-oxoisobutanol-2-yl)-2,2,4,4-tetramethylcyclobutoxy)-2-chlorobenzonitrile (189 mg, 0.4 mmol) and trimethylsilylacetylene (59 mg, 0.6 mmol) were dissolved in 3 mL of toluene, to which were added triethylamine (1 mL), $Pd(dppf)_2Cl_2$ (30 mg), and CuI (150 mg). Under $N_2$ protection, the reaction solution was heated to 90-100° C., and reacted for additional 12 h under stirring. After the reaction was completed, the solvent was removed by evaporation under reduced pressure. The crude product was purified by TLC (PE:EA=3:1), to obtain 147 mg of intermediate 17-1, with a yield of 88%. MS (ES): m/z 419 $[M+H]^+$.

2. Synthesis of Intermediate t-butyl 2-(4-(4-(2-((1r,3r)-3-(3-chloro-4-cyanophenoxy)-2,2,4,4-tetramethylcyclobutyl)-1-oxoisoindolin-5-yl)-1H-1,2,3-triazol-1-yl)butoxy) acetate Compounds 2-chloro-4-((1r,3r)-3-(5-ethynyl-1-oxoisobutanol-2-yl)-2,2,4,4-tetramethylcyclobutoxy)benzonitrile (17-1) (419 mg, 1 mmol) and t-butyl 2-(4-azidobutoxy) acetate (229 mg, 1 mmol) were dissolved in 5 mL DMF, to which were added CuI (38 mg, 0.2 mmol) and triethylamine (0.1 mL), and then the mixture was stirred and reacted 4 h at room temperature. After completion of the reaction, the reaction solution was added with water and then extracted with ethyl acetate. The resultant organic phase was evaporated under reduced pressure to remove the solvent. The crude product was purified by TLC (PE:EA=3:1) to obtain 558 mg of intermediate 17-2, with a yield of 86%. MS (ES): m/z 648 $[M+H]^+$ 3. Synthesis of Intermediate 2-(4-(4-(2-((1r,3r)-3-(3-chloro-4-cyanophenoxy)-2,2,4,4-tetramethylcyclobutyl)-1-oxoisoindolin-5-yl)-1H-1, 2, 3-triazol-1-yl)butoxy)acetic acid Compound t-butyl 2-(4-(4-(2-((1r,3r)-3-(3-chloro-4-cyanophenoxy)-2,2,4,4-tetramethylcyclobutyl)-1-oxoisoindolin-5-yl)-1H-1, 2, 3-triazol-1-yl)butoxy)acetate (intermediate 17-2) (65 mg, 0.1 mmol) was dissolved in 2 mL of dichloromethane, to which was added 1 mL of trifluoroacetic acid, and the mixture was stirred 2 h at room temperature, and the reaction was completed. The solvent was removed by evaporation under reduced pressure, and the residue was directly used in next reaction, without further purification.

4. Synthesis of Final Product 30: (2s,4r)-1-((s)-2-(2-(4-(4-(2-((1r,3r)-3-(3-chloro-4-cyanophenoxy)-2,2,4,4-tetramethylcyclobutyl)-1-oxoisobutanol-5-yl)-1H-1,2,3-triazol-1-yl)butoxy)acetamido)-3,3-dimethylbutyryl)-4-hydroxy-N-((S)-1-(4-(4-methylthiazol-5-yl)phenyl)ethyl)pyrrolidine-2-carboxamide Compounds 2-(4-(4-(2-((1r,3r)-3-(3-chloro-4-cyanophenoxy)-2,2,4,4-tetramethylcyclobutyl)-1-oxoisoindolin-5-yl)-1H-1,2,3-triazol-1-yl)butoxy)acetic acid (59 mg, 0.1 mmol) and ((2s,4r)-1-((s)-2-amino-3,3-dimethylbutyryl)-4-hydroxy-N-((s)-1-(4-(4-methylthiazol-5-yl)phenyl)ethyl) pyrrolidine-2-carboxamide (44.5 mg, 0.1 mmol) were dissolved in 2 mL of dichloromethane, to which were added DIPEA (38.7 mg, 0.3 mmol) and HATU (76.1 mg, 0.2 mmol), and then the mixture was stirred 2 h at room temperature. After completion of the reaction, the reaction solution was added with water and then extracted with dichloromethane. The resultant organic phase was evaporated under reduced pressure to remove the solvent. The crude product was purified by TLC (MeOH:DCM=10:1) to obtain 56 mg of target product, with a yield of 55%. MS (ES): m/z 1018 $[M+H]^+$. $^1H$ NMR (400 MHz, DMSO-$d_6$) δ 8.98 (s, 1H), 8.75 (s, 1H), 8.45 (d, J=7.7 Hz, 1H), 8.09 (s, 1H), 7.97 (d, J=7.8 Hz, 1H), 7.91 (d, J=8.7 Hz, 1H), 7.77 (d, J=8.0 Hz, 1H), 7.47-7.28 (m, 6H), 7.08 (d, J=8.7 Hz, 1H), 5.35 (s, 1H), 5.21 (s, 1H), 4.81 (d, J=36.8 Hz, 3H), 4.44 (ddd, J=61.5, 38.1, 19.5 Hz, 6H), 3.98-3.72 (m, 4H), 3.52 (t, J=6.1 Hz, 2H), 2.30-2.22 (m, 1H), 1.99 (d, J=5.2 Hz, 5H), 1.59 (d, J=7.3 Hz, 2H), 1.39 (d, J=20.9 Hz, 6H), 1.34-1.21 (m, 4H), 1.15 (d, J=12.8 Hz, 6H), 0.95 (s, 9H).

31: (2s,4r)-1-((s)-2-(2-(3-(2-((1r,3r)-3-(3-chloro-4-cyanophenoxy)-2,2,4,4-tetramethylcyclobutyl)-1-oxoisoindolin-5-yl)piperazin-1-yl)propoxy)acetamido)-3,3-dimethylbutyryl)-4-hydroxy-N-((s)-1-(4-methylthiazol-5-yl)phenyl)ethyl) pyrrolidine-2-carboxamide

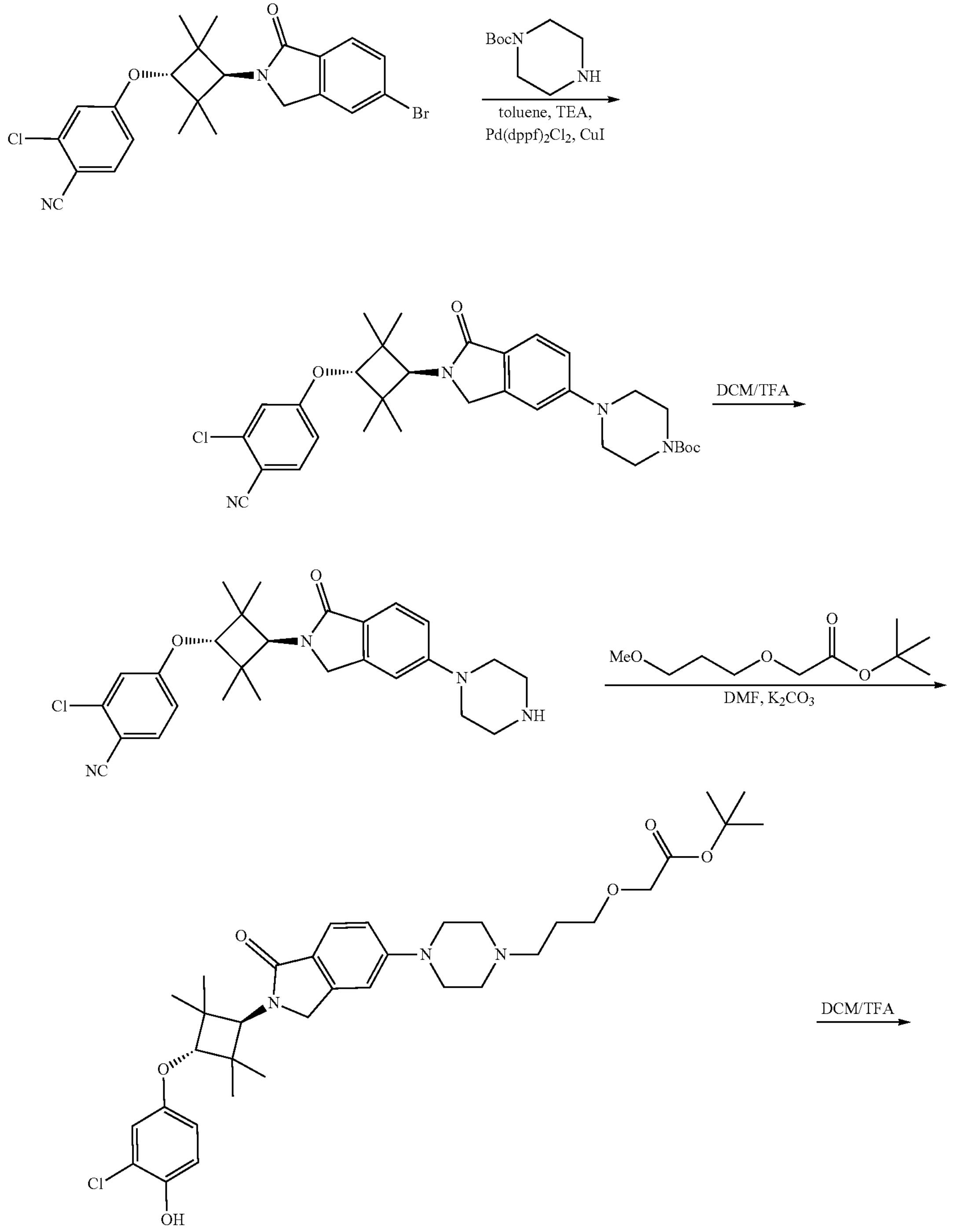

-continued

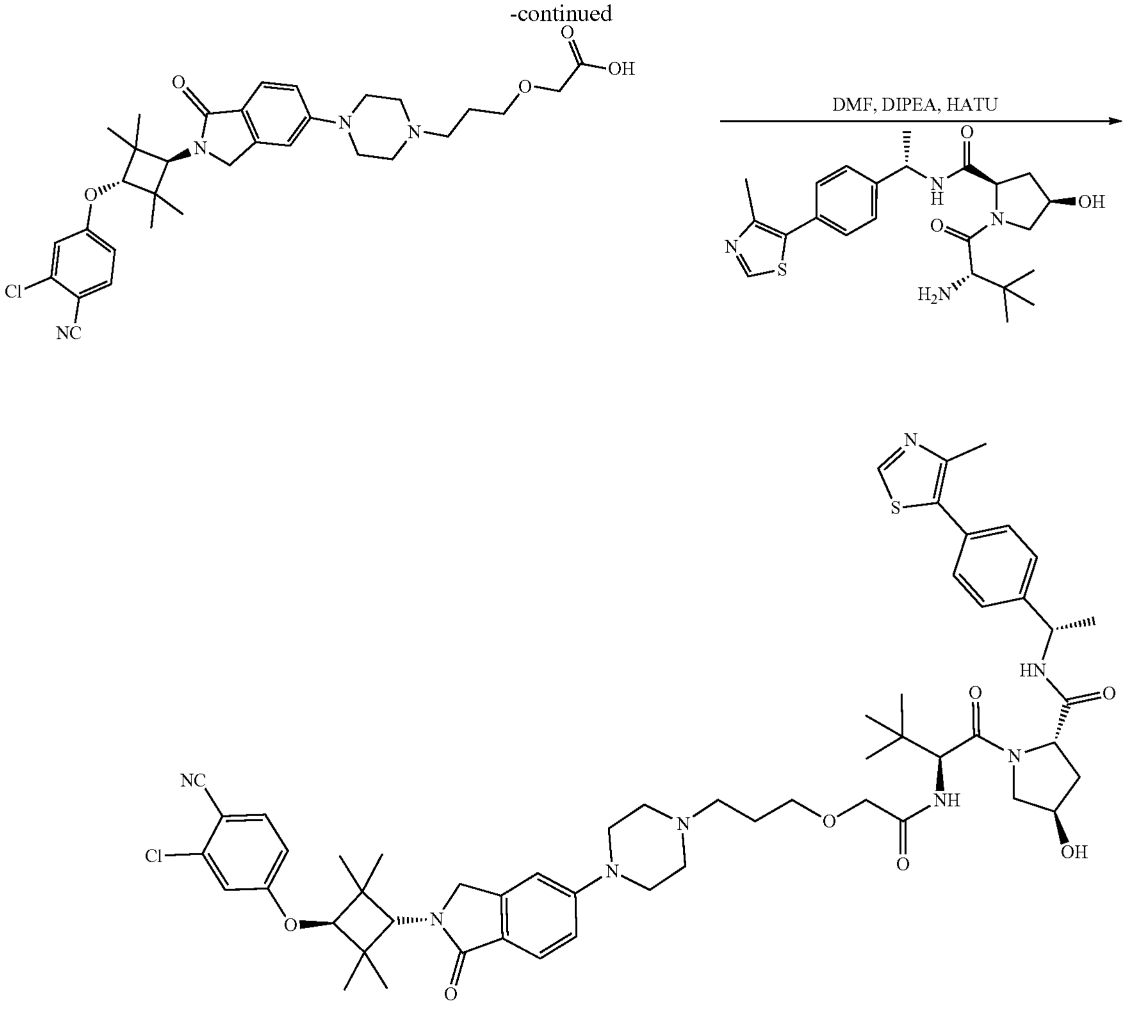

31

59 mg of final product 31 was obtained, with a yield of 58%. MS (ES): m/z 1021 $[M+H]^+$. H NMR (400 MHz, DMSO-$d_6$) δ 8.98 (s, 1H), 8.75 (s, 1H), 8.45 (d, J=7.7 Hz, 1H), 8.09 (s, 1H), 7.97 (d, J=7.8 Hz, 1H), 7.91 (d, J=8.7 Hz, 1H), 7.77 (d, J=8.0 Hz, 1H), 7.47-7.28 (m, 5H), 7.08 (d, J=8.7 Hz, 1H), 5.35 (s, 1H), 5.21 (s, 1H), 4.81 (d, J=36.8 Hz, 3H), 4.44 (ddd, J=61.5, 38.1, 19.5 Hz, 4H), 3.98-3.72 (m, 4H), 3.52 (t, J=6.1 Hz, 2H), 3.48 (m, 8H), 2.30-2.22 (m, 1H), 1.99 (d, J=5.2 Hz, 5H), 1.59 (d, J=7.3 Hz, 2H), 1.39 (d, J=20.9 Hz, 6H), 1.34-1.21 (m, 4H), 1.15 (d, J=12.8 Hz, 6H), 0.95 (s, 9H).

32: (2s,4r)-1-((s)-2-(2-((1-(4-(2-((1r,3r)-3-(3-chloro-4-cyanophenoxy)-2,2,4,4-tetramethylcyclobutyl)-1-oxoheteroin-5-yl)-3-butyne-1-yl)azetidine-3-yl)oxy)acetamido)-3,3-dimethylbutyryl)-4-hydroxy-N-((S)-1-(4-(4-methylthiazol-5-yl)phenyl)ethyl)pyrrolidine-2-carboxamide

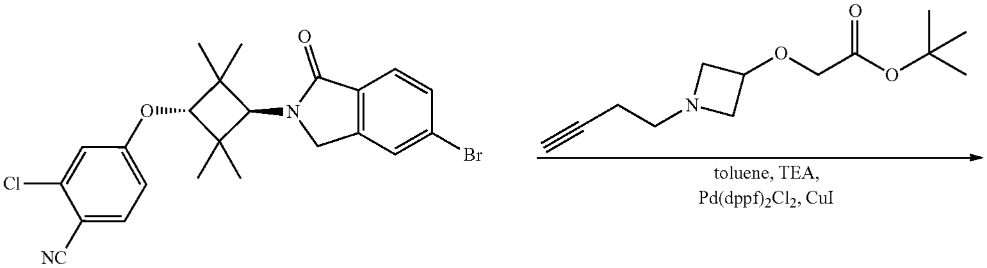

-continued
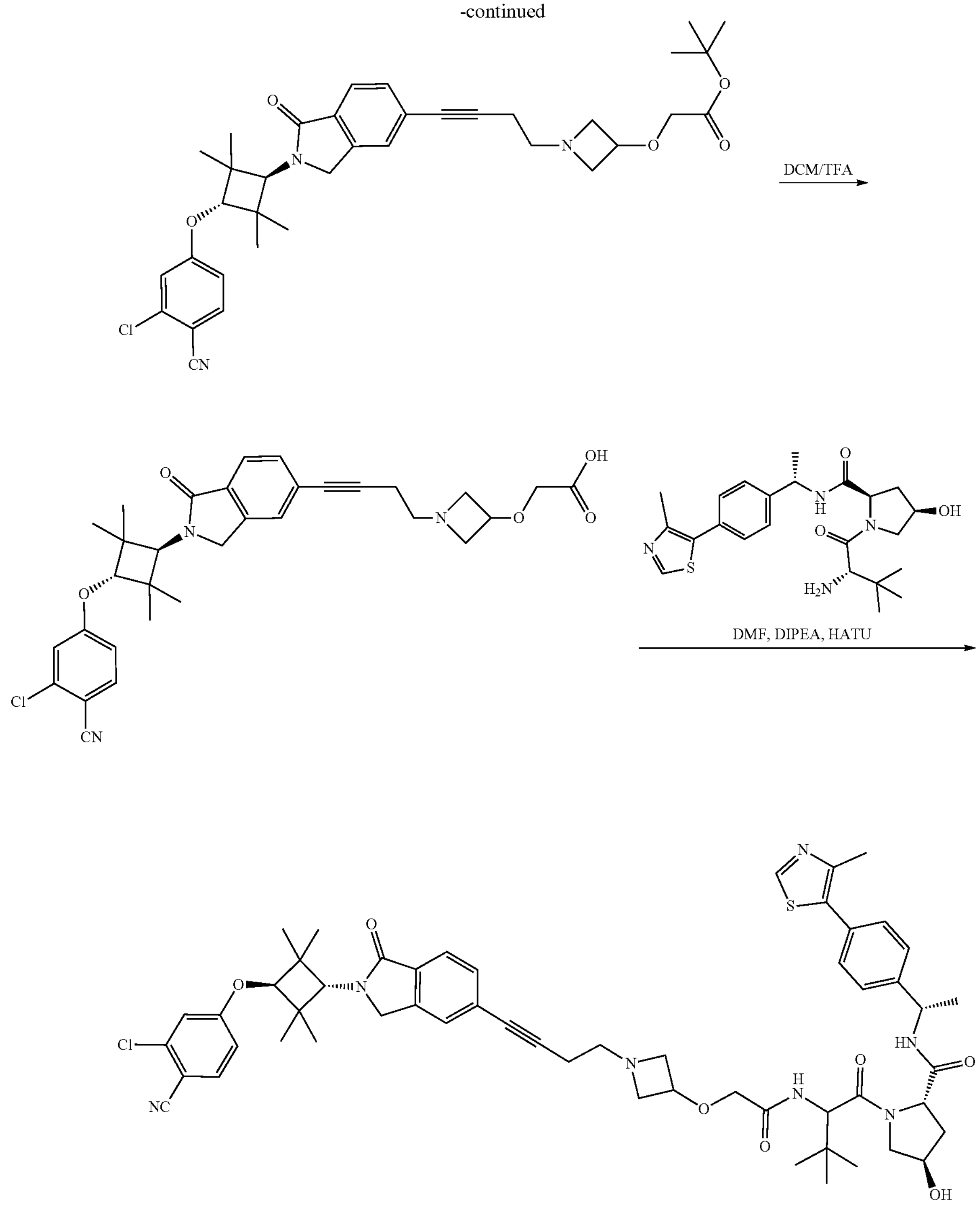
32
51 mg of final product 32 was obtained, with a yield of 50%. MS (ES): m/z 1002 $[M+H]^+$. $^1H$ NMR (400 MHz, DMSO-$d_6$) δ 8.98 (s, 1H), 8.51-8.44 (m, 1H), 7.91 (s, 1H), 7.63 (d, J=9.9 Hz, 2H), 7.54-7.33 (m, 6H), 7.29 (s, 1H), 7.11-7.03 (m, 1H), 5.25-5.17 (m, 2H), 4.95-4.86 (m, 1H), 4.77 (s, 2H), 4.54 (s, 3H), 4.31 (s, 1H), 3.98 (s, 3H), 3.82-3.73 (m, 1H), 3.65 (m, 2H), 3.45 (m, 2H), 2.58 (m, 2H), 2.46 (m, 4H), 2.32-2.21 (m, 2H), 1.39 (s, 8H), 1.24 (s, 3H), 1.15 (s, 6H), 0.96 (s, 9H).

33: N-((1r,3r)-3-(3-chloro-4-cyanophenoxy)-2,2,4,4-tetramethylcyclobutyl)-6-(6-(2-((S)-1-((2R,4R)-4-hydroxy-2-((S)-1-(4-(4-methylthiazol-5-yl)phenyl) ethyl) carbamoyl)pyrrolidin-1-yl)-3,3-dimethyl-1-oxobutan-2-yl)amino)-2-oxoethoxy)-1-hexyn-1-yl)-N-(methyl-d3)nicotinamide

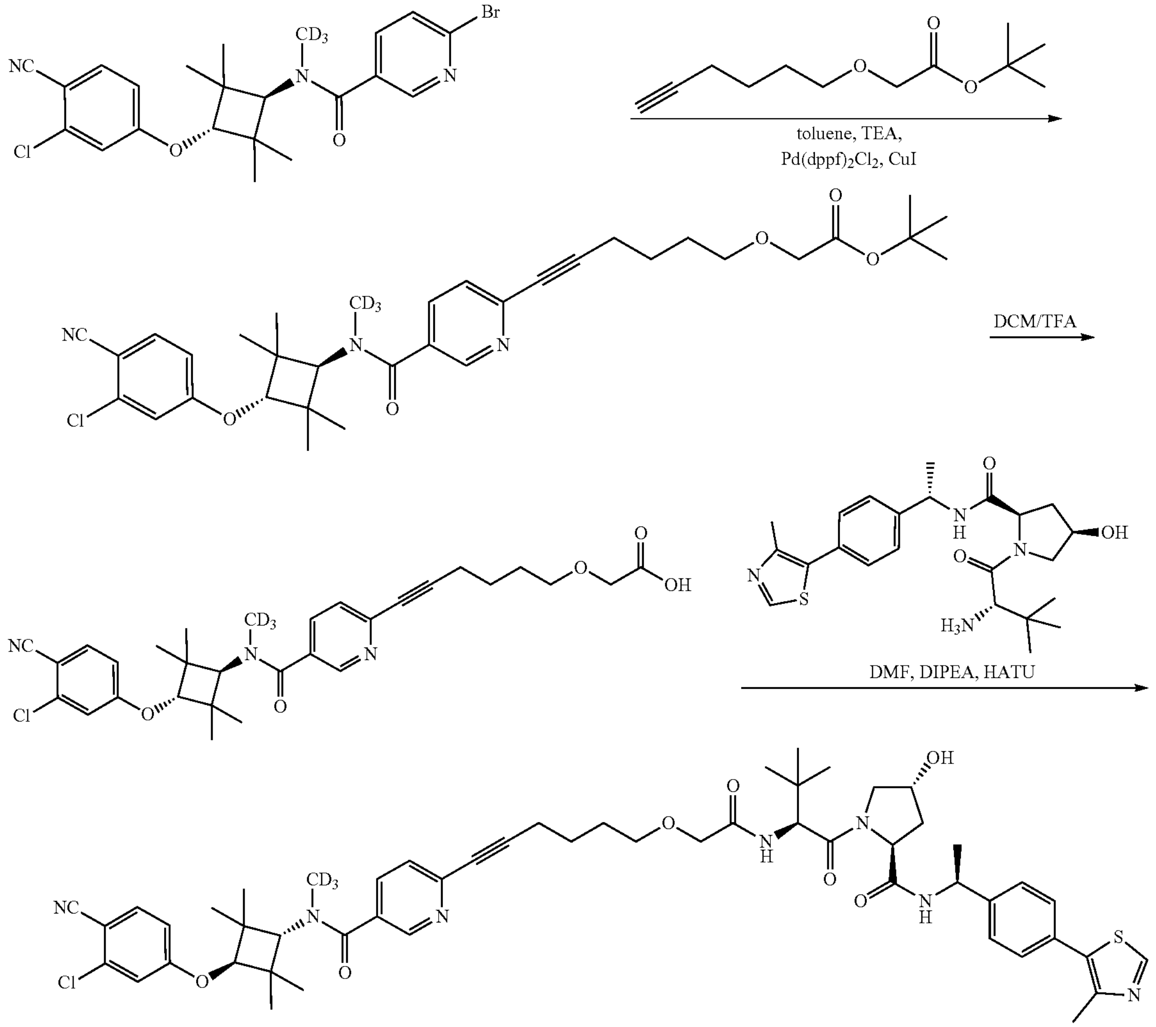

33

59 mg of final product 33 was obtained, with a yield of 60%. MS (ES): m/z 981 $[M+H]^+$. $^1$H NMR (400 MHz, DMSO-$d_6$) δ 8.99 (s, 1H), 8.47 (d, J=7.3 Hz, 2H), 7.82 (dd, J=50.3, 8.4 Hz, 2H), 7.56-6.89 (m, 12H), 5.29 (s, 1H), 5.20 (s, 1H), 4.90 (d, J=7.3 Hz, 1H), 4.45 (dd, J=15.1, 8.9 Hz, 2H), 3.98-3.71 (m, 5H), 3.57 (t, J=26.1 Hz, 4H), 2.46 (m, 1H), 2.35-2.22 (m, 2H), 1.68 (dd, J=12.9, 6.1 Hz, 6H), 1.36 (s, 9H), 0.95 (s, 12H).

34: (2S,4R)-1-((S)-2-(3-((4-(2-((1r,3r)-3-(3-chloro-4-cyanophenoxy)-2,2,4,4-tetramethylcyclobutyl)-1-oxoisoindolin-5-yl)3-butynoxy)propylamino)-3,3-dimethylbutanol)-4-hydroxy-N-(S)-1-(4-(4-methylthiazole)phenyl)ethyl) formamide

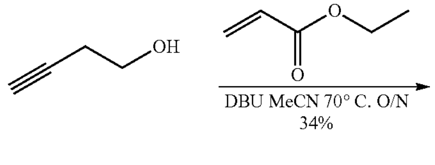

-continued

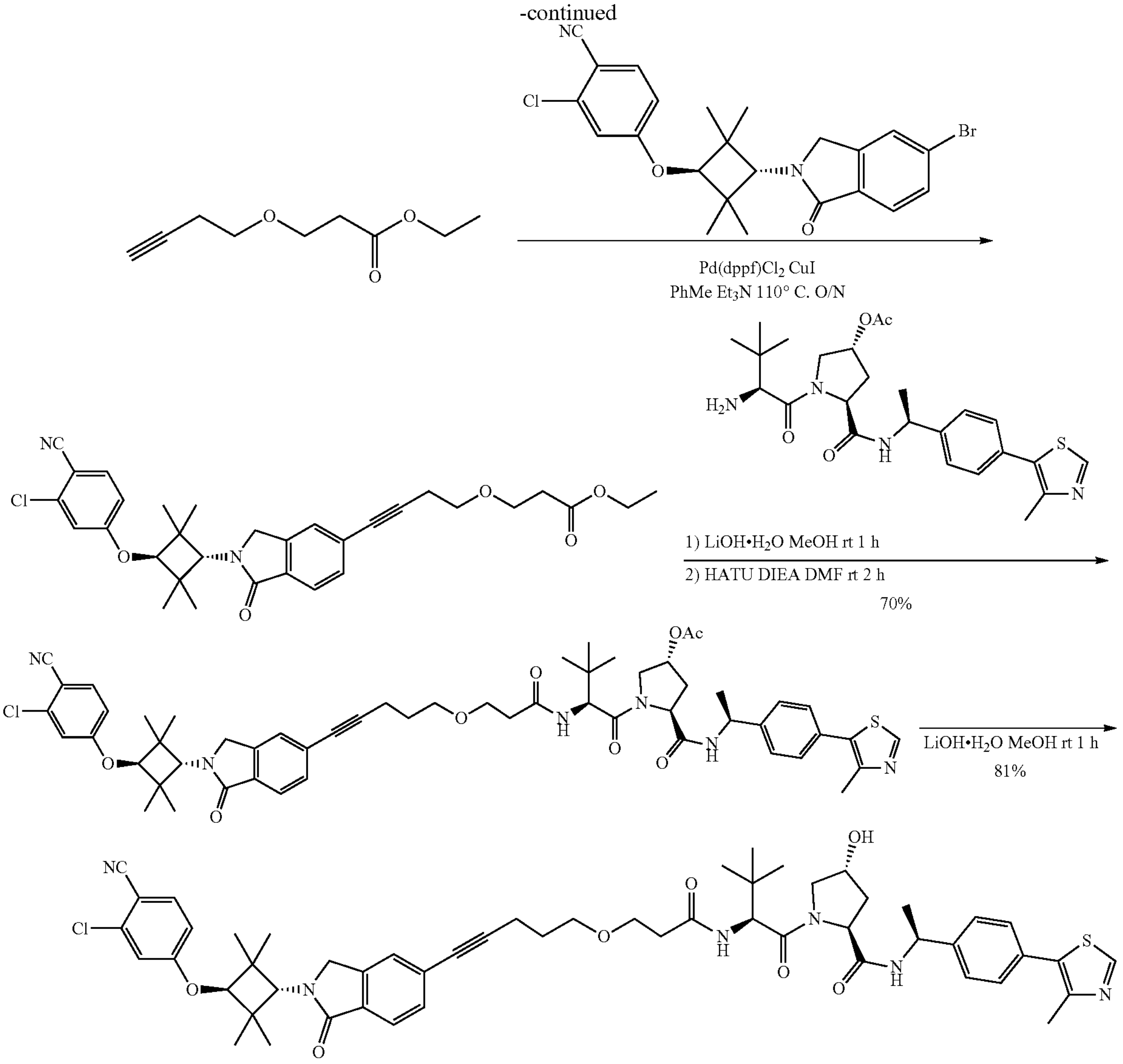

34

1. Synthesis of Compound ethyl 3-(3-butynoxy)propionate

Compound 3-butyn-1-ol (1.00 g, 14.27 mmol), ethyl acrylate (1.71 g, 17.12 mmol), 10 mL of acetonitrile and DBU (1.09 g, 7.13 mmol) were successively added to the reaction flask, and under nitrogen protection, the mixture was allowed to react overnight at 70° C. TLC indicated the completion of the reaction, and to the reaction solution, were added water and ethyl acetate for extracting 3 times. The organic layers were combined, sequentially washed with 10% citric acid aqueous solution once and saturated brine thrice, dried over anhydrous sodium sulfate, rotatory evaporated to dry, and purified by silica gel column chromatography, to obtain the colorless oily compound ethyl 3-(3-butynoxy)propionate (826 mg, 4.85 mmol), with a yield of 34%. LC/MS ($ESI^+$) calcd for $C_9H_{14}O_3[M+H]^+$ m/z, 171.1. found, 171.2.

2. Synthesis of Compound ethyl 3-((4-(2-((1r,3r)-3-(3-chloro-4-cyanophenoxy)-2,2,4,4-tetramethylcyclobutyl)-1-oxoisoindol-5-yl)-3-butynoxy)oxy)propionate Compound ethyl 3-(3-butynoxy)propionate (150 mg, 0.32 mmol), 4-((1r,3r)-3-(5-bromo-1-oxoisoindol-2-yl)-2,2,4,4-tetramethylcyclobutoxy)-2-chlorobenzonitrile (108 mg, 0.64 mmol), [1,1'-bis(diphenylphosphino)ferrocene]dichloropalladium (46 mg, 0.06 mmol), CuI (30 mg, 0.16 mmol), 0.5 mL of triethylamine and 1.5 mL of toluene were sequentially added to the reactor, and under nitrogen protection, the mixture was allowed to react overnight at 110° C. TLC indicated the completion of the reaction, and the reaction solution was filtered. The filter cake was rinsed with dichloromethane, rotatory evaporated to dry, and purified by silica gel column chromatography, to obtain ethyl 3-((4-(2-((1r, 3r)-3-(3-chloro-4-cyanophenoxy)-2,2,4,4-tetramethylcyclobutyl)-1-oxoisoindol-5-yl)-3-butynoxy)oxy)propionate as an off-white solid (56 mg, 0.10 mmol), with a yield of 31%.

LC/MS ($ESI^+$) calcd for $C_{32}H_{35}ClN_2O_5$ $[M+H]^+$ m/z, 563.2; found, 563.2.

3. Synthesis of Compound (3R,5S)-1-((S)-2-(3-((4-(2-((1r,3r)-3-(3-chloro-4-cyanophenoxy)-2,2,4,4-tetramethylcyclobutyl)-1-oxoisoindol-5-yl)-3-butynoxy)oxy) propylamino)-3,3-dimethylbutanol)-5-((S)-1-(4-methylthiazol-5-yl)phenyl)ethyl) carbamoyl)pyrrolidin-3-ylacetic acid Compound ethyl 3-((4-(2-((1r,3r)-3-(3-chloro-4-cyanophenoxy)-2,2,4,4-tetramethylcyclobutyl)-1-oxoisoindol-5-yl)-3-butynoxy)oxy)propionate (50 mg, 0.09 mmol) was dissolved in 2 mL of methanol, and then the solution of lithium hydroxide monohydrate (15 mg, 0.36 mmol) in 0.5 mL water was added to the reactor. The mixture was stirred 3 h at room temperature. TLC indicated the completion of the reaction. To the reaction solution, was added water, and then the solution was adjusted to pH 2-3 with 1N hydrochloric acid solution, followed by extraction three times with ethyl acetate. The organic phase was dried with anhydrous sodium sulfate, and then rotatory evaporated to dry to obtain the crude product, to which were added 2 mL of DMF and DIPEA (54 mg, 0.42 mmol). HATU (64 mg, 0.17 mmol) was added in an ice bath, and the mixture was stirred 0.5 h, to which was added (3R,5S)-1-((S)-2-amino-3,3-dimethylbutyryl)-5-((((S)-1-(4-(4-methylthiazol-5-yl)phenyl)ethyl)) carbamoyl)pyrrolidine-3-acetate (45 mg, 0.09 mmol). The mixture was stirred 2 h at room temperature, and TLC indicated the completion of the reaction, to which were added water and ethyl acetate for extraction three times. The organic phase was washed with saturated brine three times, dried over anhydrous sodium sulfate, rotatory evaporated to dry, and purified by pre-TLC, to obtain (3R,5S)-1-((S)-2-(3-((4-(2-((1r,3r)-3-(3-chloro-4-cyanophenoxy)-2,2,4,4-tetramethylcyclobutyl)-1-oxoisoindolin-5-yl)-3-butynoxy) oxy)propylamino)-3,3-dimethylbutanol)-5-((S)-1-(4-methylthiazol-5-yl)phenyl)ethyl)carbamoyl) pyrrolidin-3-ylacetic acid as an off-white solid (59 mg, 0.06 mmol), with a yield of 70%.

LC/MS ($ESI^+$) calcd for $C_{55}H_{63}ClN_6O_8S$ $[M+H]^+$ m/z, 1003.4; found, 1003.5.

$^1H$ NMR (400 MHz, $CDCl_3$) δ 8.78 (s, 1H), 7.76 (d, J=7.8 Hz, 1H), 7.57 (d, J=8.7 Hz, 1H), 7.48 (d, J=8.0 Hz, 1H), 7.45 (s, 1H), 7.43-7.31 (m, 5H), 7.00 (d, J=2.4 Hz, 1H), 6.87-6.78 (m, 2H), 5.35 (s, 1H), 5.08 (p, J=7.1 Hz, 1H), 4.73 (dd, J=8.2, 6.3 Hz, 1H), 4.63 (s, 2H), 4.56 (d, J=8.9 Hz, 1H), 4.39 (s, 1H), 4.32 (s, 1H), 4.07 (d, J=11.4 Hz, 1H), 3.82-3.77 (m, 2H), 3.72 (t, J=7.1 Hz, 2H), 2.79-2.70 (m, 3H), 2.56 (s, 3H), 2.53 (t, J=6.1 Hz, 2H), 2.16-2.07 (m, 2H), 2.06 (s, 3H), 1.48 (d, J=6.9 Hz, 3H), 1.43 (d, J=12.3 Hz, 6H), 1.26 (s, 6H), 1.05 (d, J=8.6 Hz, 9H).

4. Synthesis of Compound (2S,4R)-1-((S)-2-(3-((4-(2-((1r,3r)-3-(3-chloro-4-cyanophenoxy)-2,2,4,4-tetramethylcyclobutyl)-1-oxoisoindolin-5-yl)-3-butynoxy) propylamino)-3,3-dimethylbutanol)-4-hydroxy-N-(S)-1-(4-(4-methylthiazole)phenyl) ethyl) formamide Compound (3R,5S)-1-((S)-2-(3-((4-(2-((1r,3r)-3-(3-chloro-4-cyanophenoxy)-2,2,4,4-tetramethylcyclobutyl)-1-oxoisoindolin-5-yl)-3-butynoxy)oxy)propylamino)-3,3-dimethylbutanol)-5-((S)-1-(4-methylthiazol-5-yl)phenyl) ethyl)carbamoyl)pyrrolidin-3-yl-acetic acid (24 mg, 0.02 mmol) was dissolved in 2 mL of methanol, and then the solution of lithium hydroxide monohydrate (4 mg, 0.10 mmol) in 0.5 mL water was added to the reactor. The mixture was stirred 3 h at room temperature. TLC indicated the completion of the reaction. To the reaction solution, was added water, and then the resultant solution was extracted three times with ethyl acetate. The organic phase was dried with anhydrous sodium sulfate, and then rotatory evaporated to dry to obtain the crude product, which was separated by pre-TLC to provide compound (2S,4R)-1-((S)-2-(3-((4-(2-((1r,3r)-3-(3-chloro-4-cyanophenoxy)-2,2,4,4-tetramethylcyclobutyl)-1-oxoisoindol-5-yl)-3-butynoxy)propylamino)-3,3-dimethylbutanol)-4-hydroxy-N-(S)-1-(4-(4-methylthiazole)phenyl)ethyl)formamide as a light yellow solid (21 mg, 0.02 mmol), with a yield of 91%. LC/MS ($ESI^+$) calcd for $C_{53}H_{61}ClN_6O_7S$ $[M+H]^+$ m/z, 961.4; found, 961.4. $^1H$ NMR (400 MHz, $CDCl_3$) δ 8.69 (s, 1H), 7.76 (d, J=7.9 Hz, 1H), 7.58 (d, J=8.7 Hz, 1H), 7.52-7.43 (m, 3H), 7.39 (q, J=8.4 Hz, 4H), 6.99 (t, J=6.3 Hz, 2H), 6.84 (dd, J=8.7, 2.4 Hz, 1H), 5.12-5.02 (m, 1H), 4.75 (t, J=7.9 Hz, 1H), 4.63 (s, 2H), 4.51 (d, J=8.1 Hz, 2H), 4.40 (s, 1H), 4.32 (s, 1H), 4.15 (d, J=11.6 Hz, 1H), 3.78 (d, J=2.6 Hz, 2H), 3.72 (t, J=7.0 Hz, 2H), 3.57 (dd, J=11.4, 3.3 Hz, 1H), 2.76 (t, J=7.0 Hz, 2H), 2.53 (d, J=7.3 Hz, 5H), 2.12-2.02 (m, 1H), 1.46 (dd, J=10.7, 3.9 Hz, 9H), 1.25 (s, 9H), 1.02 (d, J=30.5 Hz, 9H).

35: Synthesis of (2S,4R)-1-((S)-2-(4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butylamino)-3,3-dimethylbutanol)-4-hydroxy-N-((S)-1-(4-methylthiazol-5-yl)phenyl)ethyl) pyrrolidine-2-carboxamide

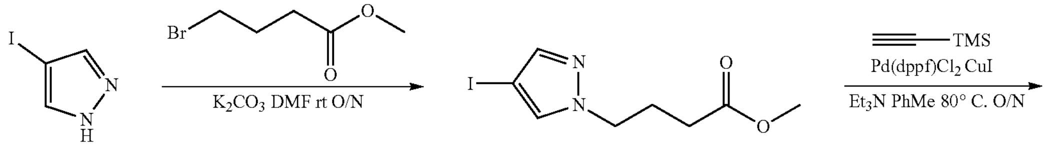

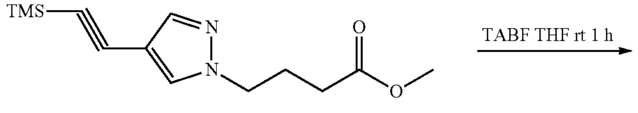

-continued

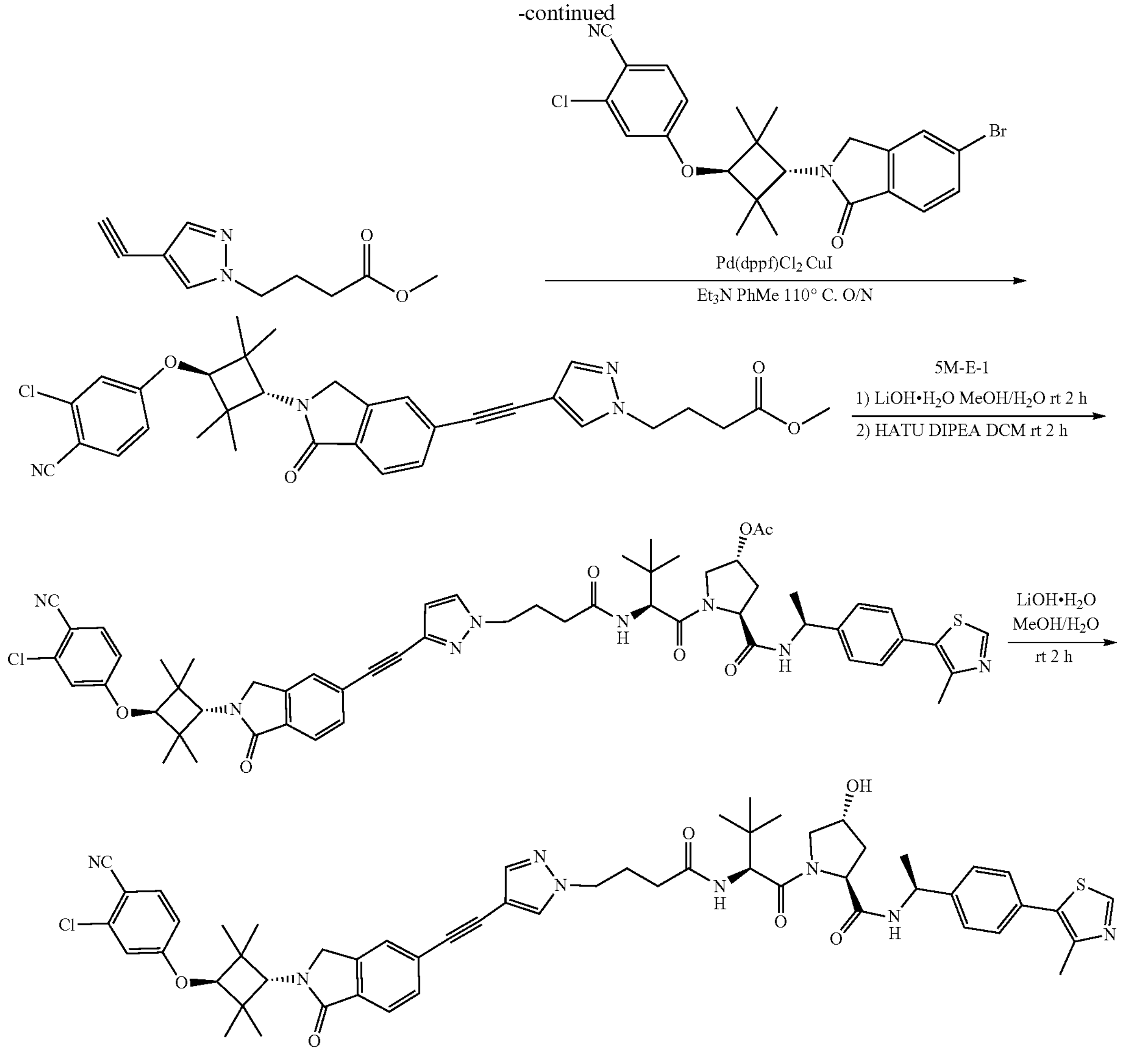

1. Synthesis of Compound methyl 4-(4-iodo-1H-pyrazol-1-yl)butyrate

Compound 4-iodopyrazole (1.00 g, 5.16 mmol), methyl 4-bromobutyrate (1.03 g, 5.68 mmol), 50 mL of acetonitrile and potassium carbonate (1.07 g, 7.73 mmol) were successively added to the reaction flask, and under the nitrogen protection, the reaction solution was stirred and reacted overnight at room temperature. TLC indicated the completion of the reaction. To the reaction solution, was added water, and then the resultant solution was extracted three times with ethyl acetate. The organic layers were combined, successively washed once with 10% citric acid aqueous solution and thrice with saturated brine, dried over anhydrous sodium sulfate, and then rotatory evaporated to dry, purified by silica gel column chromatography, to provide compound methyl 4-(4-iodo-1H-pyrazol-1-yl)butyrate as colorless oil (1.23 mg, 4.18 mmol), with a yield of 81%.

LC/MS (ESI$^+$) calcd for $C_8H_{11}IN_2O_2$[M+H]$^+$ m/z, 295.0; found, 295.0.

2. Synthesis of Compound methyl 4-(4-((trimethylsilyl)ethynyl)-1H-pyrazol-1-yl)butyrate Compound methyl 4-(4-iodo-1H-pyrazol-1-yl)butyrate (1.00 g, 3.40 mmol), trimethylsilyne (510 mg, 5.10 mmol), [1,1'-bis(diphenylphosphino)ferrocene] dichloropalladium (249 mg, 0.34 mmol), CuI (259 mg, 1.36 mmol), 6 mL of triethylamine and 17 mL of toluene were sequentially added to the reactor, and under nitrogen protection, the mixture was allowed to react overnight at 80° C. TLC indicated the completion of the reaction, and the reaction solution was filtered. The filter cake was rinsed with dichloromethane, rotatory evaporated to dry, and purified by silica gel column chromatography, to obtain methyl 4-(4-((trimethylsilyl)ethynyl)-1H-pyrazol-1-yl)butyrate as pale brown oil (806 mg, 3.05 mmol), with a yield of 90%.

LC/MS (ESI$^+$) calcd for $C_{13}H_{20}N_2O_2Si$ [M+H]$^+$ m/z, 265.1; found, 265.1.

3. Synthesis of Compound methyl 4-(4-ethynyl-1H-pyrazol-1-yl)butyrate

Compound methyl 4-(4-((trimethylsilyl)ethynyl)-1H-pyrazol-1-yl)butyrate (800 mg, 3.03 mmol), TBAF (1.91 g, 7.30 mmol), and 20 mL THF were successively introduced into the reactor, and under nitrogen protection, the mixture was stirred and reacted 1 h at room temperature. TLC indicated the completion of the reaction. To the reaction solution, was added water, and then the resultant solution was extracted three times with ethyl acetate. The organic phase was washed twice with saturated brine, combined, dried over anhydrous sodium sulfate, and then rotatory evaporated to dry, to provide crude methyl 4-(4-ethynyl-1H-pyrazol-1-yl)butyrate as pale brown oil (580 mg, 3.02 mmol), with a yield of 100%. LC/MS ($ESI^+$) calcd for $C_{10}H_{12}N_2O_2$ $[M+H]^+$ m/z, 193.1; found, 193.1.

4. Synthesis of Compound methyl 4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl) butyrate Compound crude methyl 4-(4-ethynyl-1H-pyrazol-1-yl) butyrate (151 mg, 0.78 mmol), 4-((1r,3r)-3-(5-bromo-1-oxoisoindolin-2-yl))-2,2,4,4-tetramethylcyclobutoxy)-2-chlorobenzonitrile (200 mg, 0.42 mmol), [1,1'-bis (diphenylphosphino)ferrocene] dichloropalladium (59 mg, 0.081 mmol), CuI (55 mg, 0.29 mmol), 1 mL of triethylamine and 3 mL of toluene were sequentially added to the reactor, and under nitrogen protection, the mixture was allowed to react overnight at 110° C. TLC indicated the completion of the reaction, and the reaction solution was filtered. The filter cake was rinsed with dichloromethane, rotatory evaporated to dry, and purified by silica gel column chromatography, to obtain methyl 4-(4-((2-((1r,3r)-3-(3-chloro-4-cyanophenoxy)-2,2,4,4-tetramethylcyclobutyl)-1-oxoisoindol-5-yl)ethynyl)-1H-pyrazol-1-yl)butyrate as a pale yellow solid (228 mg, 0.10 mmol), with a yield of 92%. LC/MS ($ESI^+$) calcd for $C_{33}H_{33}ClN_4O_4$ $[M+H]^+$ m/z, 545.2; found, 545.2.

5. Synthesis of Compound (3R,5S)-1-((S)-2-(4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butyramido)-3,3-dimethylbutanol)-5-((S)-1-(4-methylthiazol-5-yl) phenyl) ethyl)carbamoyl)-3-pyrrolidinyl acetate Compound methyl 4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butyrate (130 mg, 0.22 mmol) was dissolved in 2 mL of methanol, and then the solution of lithium hydroxide monohydrate (37 mg, 0.89 mmol) in 0.5 mL water was added to the reactor. The mixture was stirred 3 h at room temperature. TLC indicated the completion of the reaction. To the reaction solution, was added water, and then the resultant solution was adjusted to pH 2-3 and extracted three times with ethyl acetate. The organic phase was dried with anhydrous sodium sulfate, and then rotatory evaporated to dry, to obtain the crude product, to which was added 3 mL DCM and DIPEA (135 mg, 1.04 mmol). HATU (127 mg, 0.33 mmol) was added in an ice bath, and the mixture was stirred 0.5 h, to which was added (3R,5S)-1-((S)-2-amino-3,3-dimethylbutyryl)-5-((((S)-1-(4-(4-methylthiazol-5-yl)phenyl)ethyl))carbamoyl)pyrrolidine-3-acetate (151 mg, 0.29 mmol). The mixture was stirred and reacted 2 h at room temperature, and TLC indicated the completion of the reaction, to which were added water, and the resultant solution was extracted three times with ethyl acetate. The organic phase was dried over anhydrous sodium sulfate, rotatory evaporated to dry, and separated by pre-TLC, to obtain (3R,5S)-1-((S)-2-(4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butyramido)-3,3-dimethylbutanol)-5-((S)-1-(4-methylthiazol-5-yl) phenyl)ethyl)carbamoyl)-3-pyrrolidinyl acetate as an off-white solid (123 mg, 0.12 mmol), with a yield of 53%. LC/MS (ESI) calcd for $C_{57}H_{63}ClN_8O_7S$ $[M+H]^+$ m/z, 1039.4; found, 1039.5. $^1H$ NMR (400 MHz, $CDCl_3$) δ 8.77 (s, 1H), 7.80 (d, J=7.8 Hz, 1H), 7.67 (t, J=8.6 Hz, 2H), 7.56 (t, J=7.7 Hz, 2H), 7.52 (s, 1H), 7.42-7.35 (m, 4H), 7.33 (d, J=7.8 Hz, 1H), 6.99 (d, J=2.4 Hz, 1H), 6.84 (dd, J=8.7, 2.4 Hz, 1H), 6.56 (d, J=8.6 Hz, 1H), 5.07 (p, J=7.0 Hz, 1H), 4.74 (dd, J=8.2, 6.5 Hz, 1H), 4.66 (s, 2H), 4.54-4.49 (m, 1H), 4.40 (s, 1H), 4.33 (s, 111), 4.21 (dt, J=14.3, 7.1 Hz, 2H), 4.10 (d, J=11.6 Hz, 1H), 3.81 (dd, J=11.6, 4.7 Hz, 1H), 2.74 (dt, J=13.7, 6.0 Hz, 1H), 2.55 (s, 3H), 2.25-2.10 (m, 6H), 2.06 (s, 3H), 1.47 (d, J=9.3 Hz, 9H), 1.26 (s, 6H), 1.06 (d, J=6.0 Hz, 9H).

6. Synthesis of Compound (2S,4R)-1-((S)-2-(4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butylamino)-3,3-dimethylbutanol)-4-hydroxy-N-((S)-1-(4-methylthiazol-5-yl)phenyl)ethyl)pyrrolidine-2-carboxamide Compound (3R,5S)-1-((S)-2-(4-(4-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl)butyramido)-3,3-dimethylbutanol)-5-((S)-1-(4-methylthiazol-5-yl) phenyl)ethyl)carbamoyl)-3-pyrrolidinyl acetate (60 mg, 0.058 mmol) was dissolved in 2 mL of methanol, and then the solution of lithium hydroxide monohydrate (24 mg, 0.58 mmol) in 0.5 mL water was added to the reactor. The mixture was stirred 3 h at room temperature. TLC indicated the completion of the reaction. To the reaction solution, was added water, and then the resultant solution was extracted three times with ethyl acetate. The organic phase was dried with anhydrous sodium sulfate, and then rotatory evaporated to dry, to obtain the crude product, which was separated by prep-TLC to provide compound (2S,4R)-1-((S)-2-(4-(4-((2-((1r,3r)-3-(3-chloro-4-cyanophenoxy)-2,2,4,4-tetramethylcyclobutyl)-1-oxoisoindol-5-yl)ethynyl)-1H-pyrazol-1-yl) butylamino)-3,3-dimethylbutanol)-4-hydroxy-N-((S)-1-(4-methylthiazol-5-yl)phenyl)ethyl)pyrrolidine-2-carboxamide as an off-white solid (50 mg, 0.050 mmol), with a yield of 87%. LC/MS ($ESI^+$) calcd for $C_{55}H_{61}ClN_8O_6S$ $[M+H]^+$ m/z, 997.4; found, 997.5. $^1H$ NMR (400 MHz, $CDCl_3$) δ 8.73 (s, 1H), 7.73 (d, J=7.9 Hz, 1H), 7.61 (d, J=3.2 Hz, 2H), 7.50 (t, J=8.4 Hz, 2H), 7.45 (s, 1H), 7.41 (d, J=7.7 Hz, 1H), 7.36-7.28 (m, 4H), 6.92 (dd, J=8.2, 5.2 Hz, 2H), 6.77 (dd, J=8.7, 2.4 Hz, 1H), 5.01 (p, J=6.8 Hz, 1H), 4.72 (t, J=7.9 Hz, 1H), 4.59 (s, 2H), 4.44 (dd, J=11.8, 6.1 Hz, 2H), 4.34 (s, 1H), 4.26 (s, 1H), 4.21-4.08 (m, 3H), 3.52 (dd, J=11.4, 3.2 Hz, 1H), 2.49 (s, 4H), 2.11 (ddd, J=24.9, 14.0, 5.4 Hz, 6H), 1.40 (d, J=7.9 Hz, 9H), 1.18 (d, J=7.8 Hz, 6H), 0.99 (d, J=20.9 Hz, 9H).

36: Synthesis of (2S,4R)-1-((S)-2-(2-((6-(6-((1r,3r)-3-(3-chloro-4-cyanophenoxy)-2,2,4,4-tetramethylcyclobutyl)-5-oxo-6,7-dihydro-5H-pyrrolo[3,4-b]pyridin-2-yl)hex-5-yn-1-yl)oxy)acetylamino)-3,3-dimethylbutyryl)-4-hydroxy-N-((S)-1-(4-(4-methylthiazol-5-yl)phenyl)ethyl)pyrrolidine-2-carboxamide

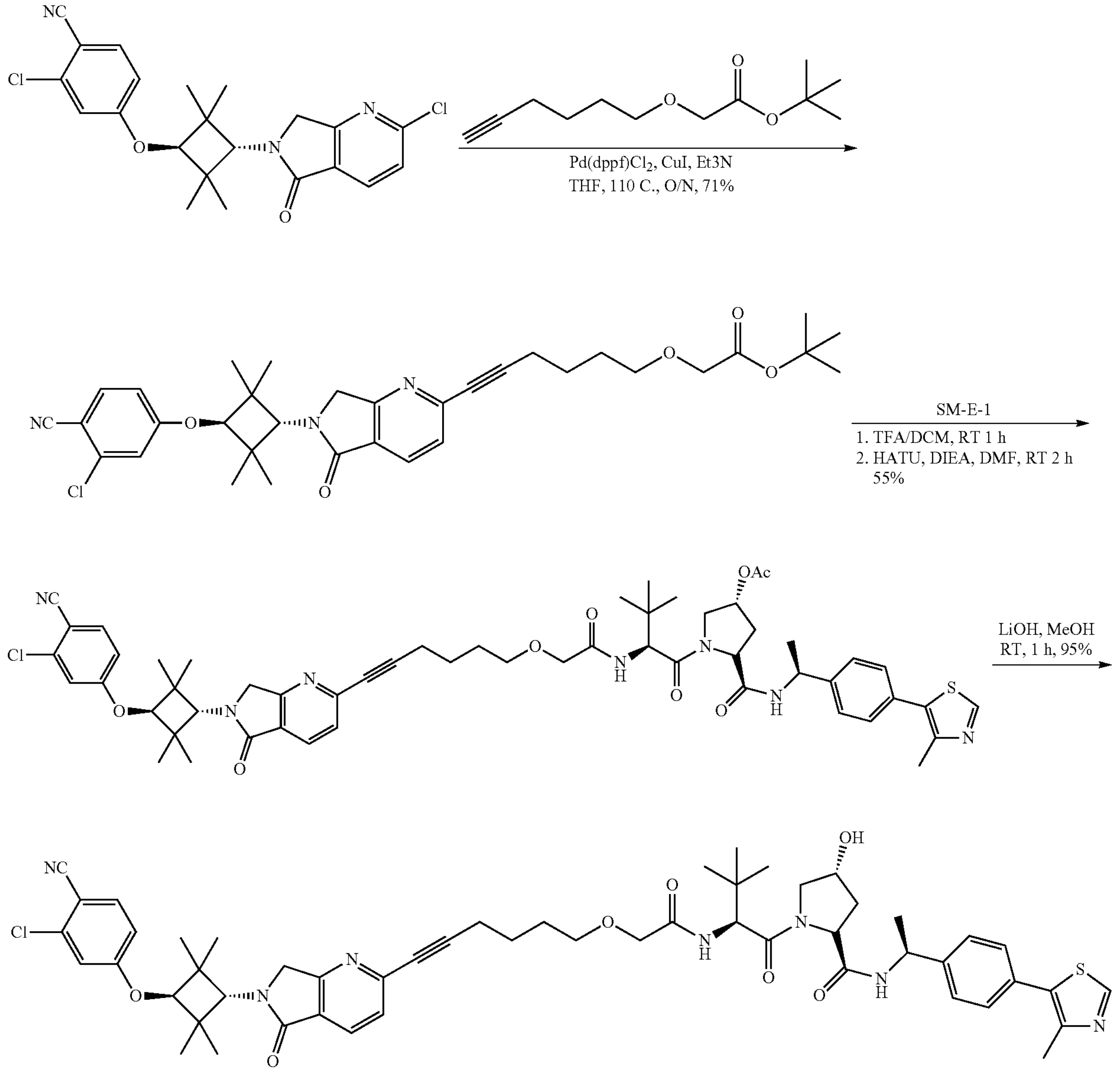

36

LC/MS (ESI+) calcd for $C_{53}H_{62}ClN_7O_7S$ $[M+H]^+$ m/z, 108.4. found, 996.4.

$^1H$ NMR (400 MHz, $CDCl_3$) δ8.77 (s, 1H), 7.98 (d, J=7.9 Hz, 1H), 7.51 (d, J=8.7 Hz, 1H), 7.40 (t, J=7.6 Hz, 2H), 7.36-7.29 (m, 4H), 7.13 (d, J=8.6 Hz, 1H), 6.93 (t, J=2.7 Hz, 1H), 6.76 (dd, J=8.7, 2.4 Hz, 1H), 5.01 (p, J=6.9 Hz, 1H), 4.69 (t, J=7.7 Hz, 1H), 4.62 (s, 2H), 4.47 (d, J=8.7 Hz, 2H), 4.38 (s, 1H), 4.23 (s, 1H), 3.89 (q, J=15.4 Hz, 2H), 3.57-3.48 (m, 3H), 2.51 (s, 6H), 1.98 (s, 3H), 1.73 (ddd, J=19.9, 13.9, 7.2 Hz, 4H), 1.41 (d, J=6.9 Hz, 3H), 1.38 (s, 6H), 1.19 (d, J=1.3 Hz, 6H), 1.00 (s, 9H).

37: Synthesis of (2S,4R)-1-((2S)-2-(2-((4-(2-((1r, 3r)-3-(3-chloro-4-cyanophenoxy)-2,2,4,4-tetramethylcyclobutyl)-1-oxoisoindolin-5-yl)but-3-yn-2-yl) oxy)ethoxy) acetamide)-3,3-dimethylbutyryl)-4-hydroxy-N-((S)-1-(4-methylthiazol-5-yl)phenyl) ethyl)pyrrolidine-2-carboxamide
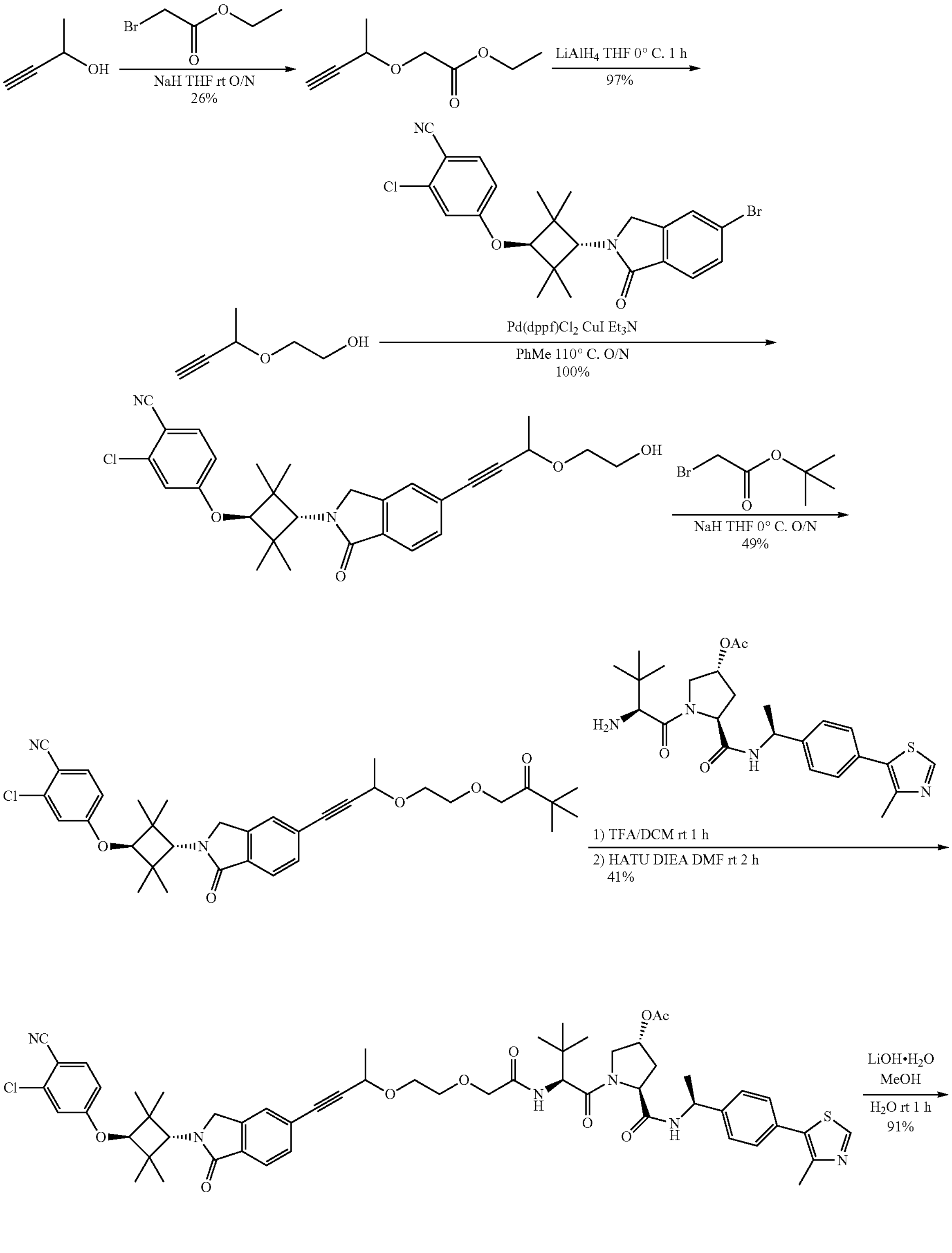

-continued

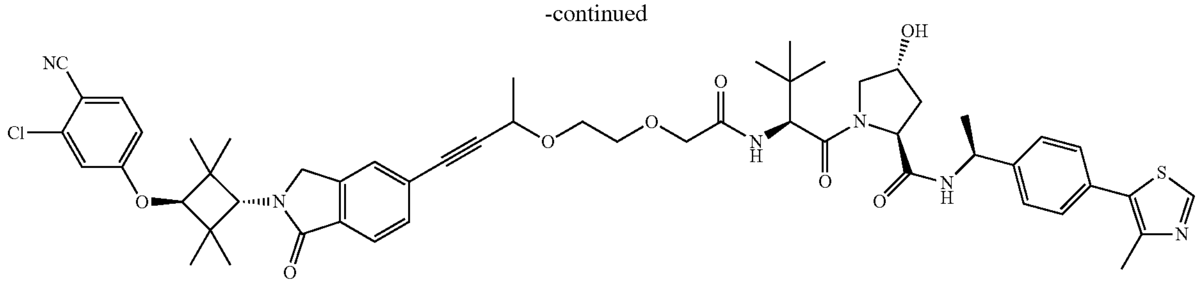

37

Compound 37 was obtained as a off-white solid (14 mg, 0.014 mmol). LCMS (ESI+) calcd for $C_{54}H_{63}ClN_6O_8S$ $[M+H]^+$ m/z, 991.4; found, 991.5. $^1H$ NMR (400 MHz, $CDCl_3$) δ 8.78 (s, 1H), 7.83-7.74 (m, 1H), 7.57 (d, J=8.61 Hz, 1H), 7.52 (d, J=8.1 Hz, 3H), 7.38 (s, 5H), 6.99 (s, 1H), 6.83 (d, J=7.4 Hz, 1H), 5.07 (s, 1H), 4.75 (s, 1H), 4.64 (s, 2H), 4.58-4.44 (m, 3H), 4.40 (s, 1H), 4.31 (s, 1H), 4.10 (s, 1H), 4.05 (s, 2H), 3.99 (s, 1H), 3.72 (t, J=14.8 Hz, 5H), 3.60 (d, J=9.5 Hz, 1H), 2.08 (s, 1H), 1.56 (d, J=3.7 Hz, 3H), 1.46 (d, J=12.9 Hz, 9H), 1.25 (s, 9H), 1.07 (s, 9H).

38: Synthesis of (2R,4R)-1-((S)-2-(2-((6-(2-((1r,3r)-3-)3-chloro-4-cyanophenoxy)-2,2,4,4-tetramethylcyclobutyl)-3-oxo-2,3-dihydro-1H-pyrrolo[3,4-c]pyridin-6-yl)hex-5-yn-1-yl)oxy)acetylamino)-3,3-dimethylbutyryl)-4-hydroxy-N-((S)-1-(4-(4-methylthiazol-5-yl)phenyl)ethyl)pyrrolidine-2-carboxamide

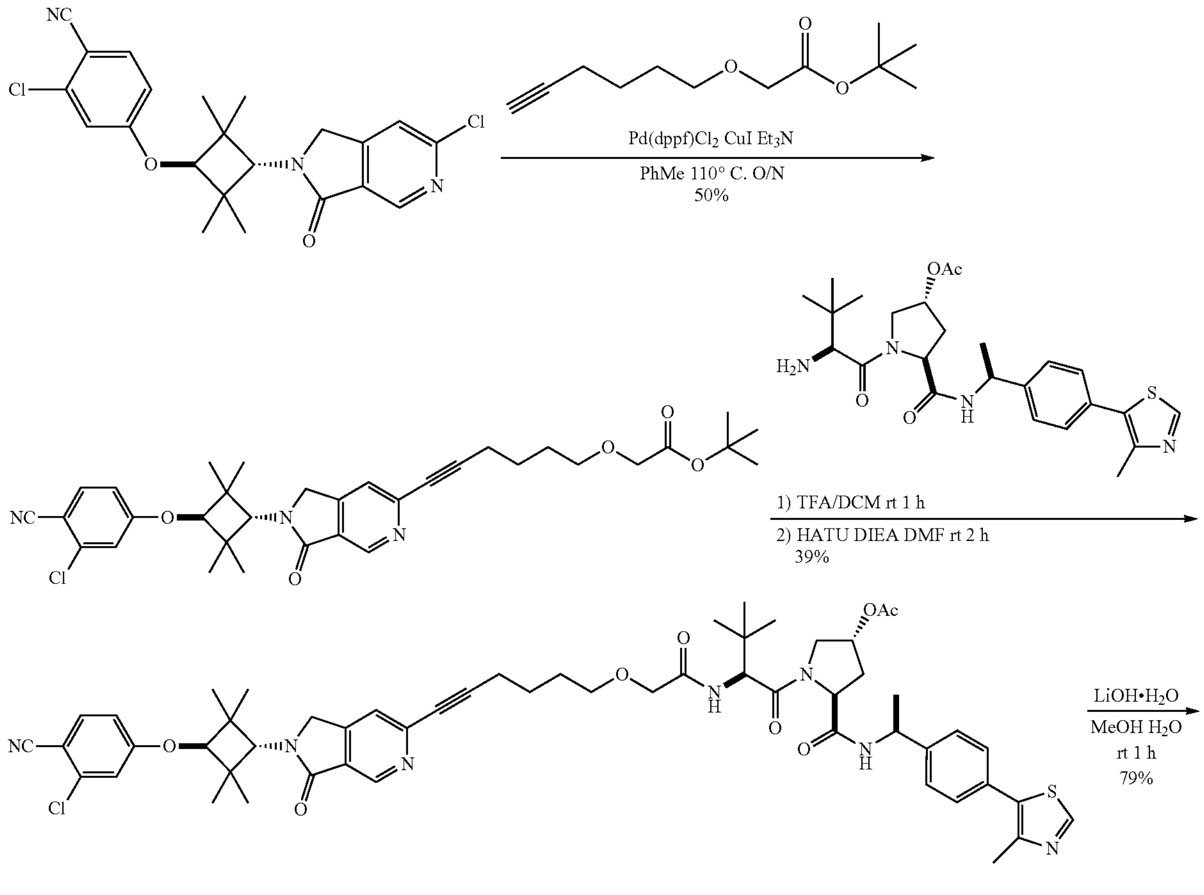

-continued

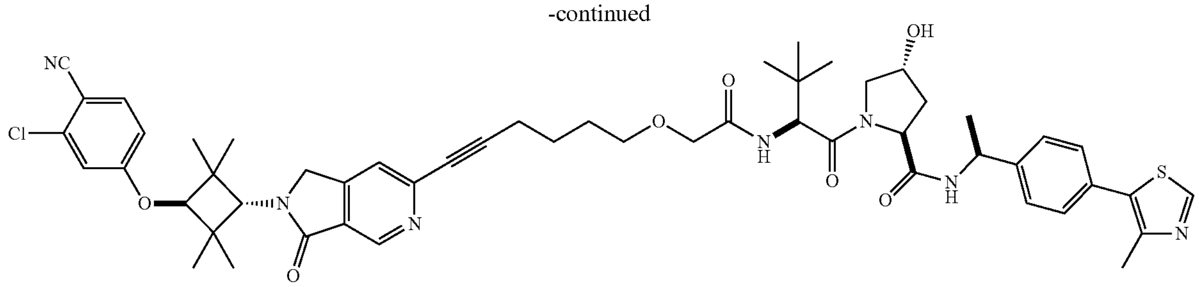

38

LC/MS ($ESI^+$) calcd for $C_{53}H_{62}ClN_7O_7S$ $[M+H]^+$ m/z, 996.4. found, 996.7.

$^1H$ NMR (400 MHz, $CDCl_3$) δ 9.01 (s, 1H), 8.70 (s, 1H), 8.02 (s, 1H), 7.58 (d, J=8.7 Hz, 1H), 7.48 (s, 2H), 7.44-7.31 (m, 4H), 7.23 (s, 2H), 6.99 (d, J=2.0 Hz, 1H), 6.90-6.77 (m, 1H), 5.16-5.00 (m, 1H), 4.75 (s, 1H), 4.68 (s, 2H), 4.62-4.47 (m, 2H), 4.41 (s, 1H), 4.30 (s, 1H), 4.10 (d, J=11.2 Hz, 1H), 3.96 (q, J=15.2 Hz, 2H), 3.61 (d, J=14.3 Hz, 3H), 2.54 (d, J=8.4 Hz, 5H), 1.79 (dd, J=23.9, 6.3 Hz, 4H), 1.53-1.38 (m, 8H), 1.25 (s, 6H), 1.06 (s, 9H).

39: (2S,4R)-1-((S)-2-(2-(4-(3-(2((1s,3s)-3-(3-chloro-4-cyanophenoxy)-2,2,4,4-tetramethylcyclobutyl)-1-oxoisoindolin-5-yl)prop-2-yn-1-yl)piperidin-1-yl) acetylamino)-3,3-dimethylbutyryl)-4-hydroxy-N-((S)-1-(4-(4-methylthiazol-5-yl)phenyl)ethyl) pyrrolidine-2-carboxamide

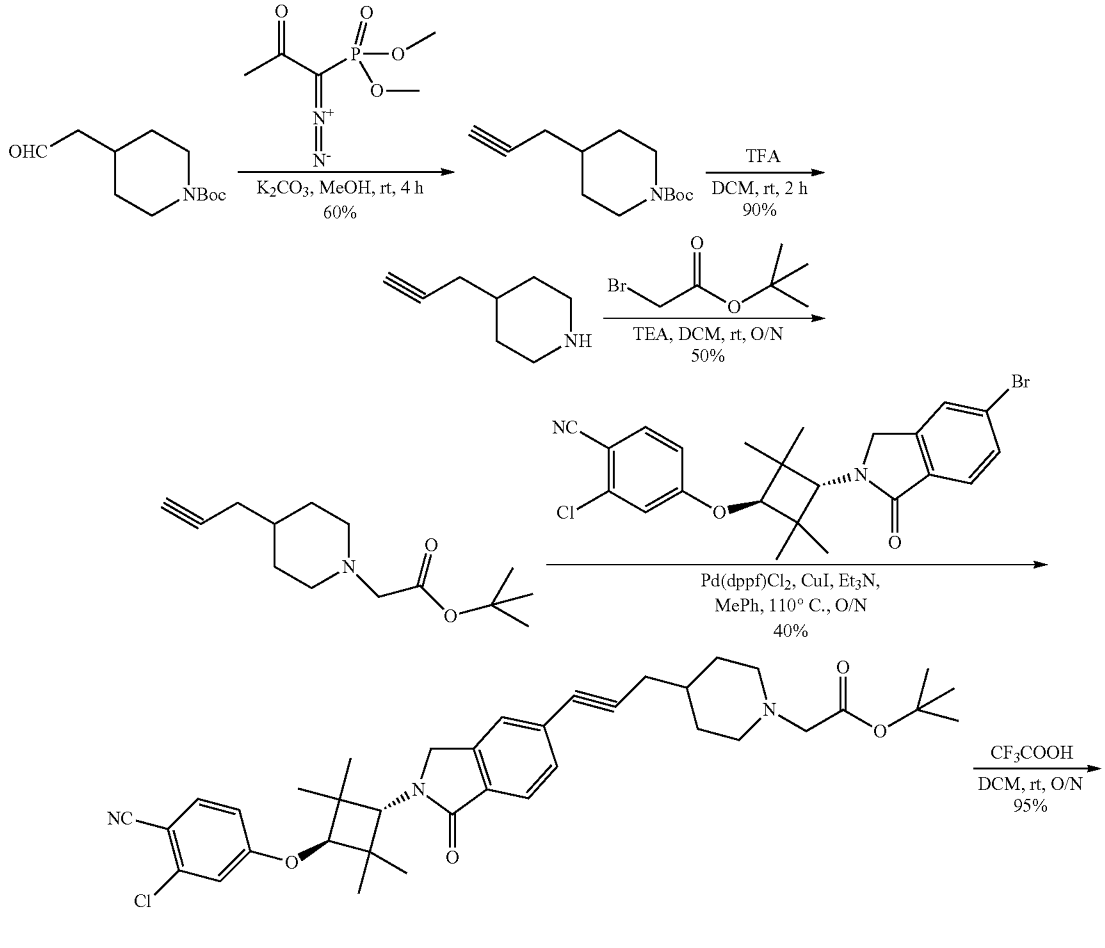

-continued

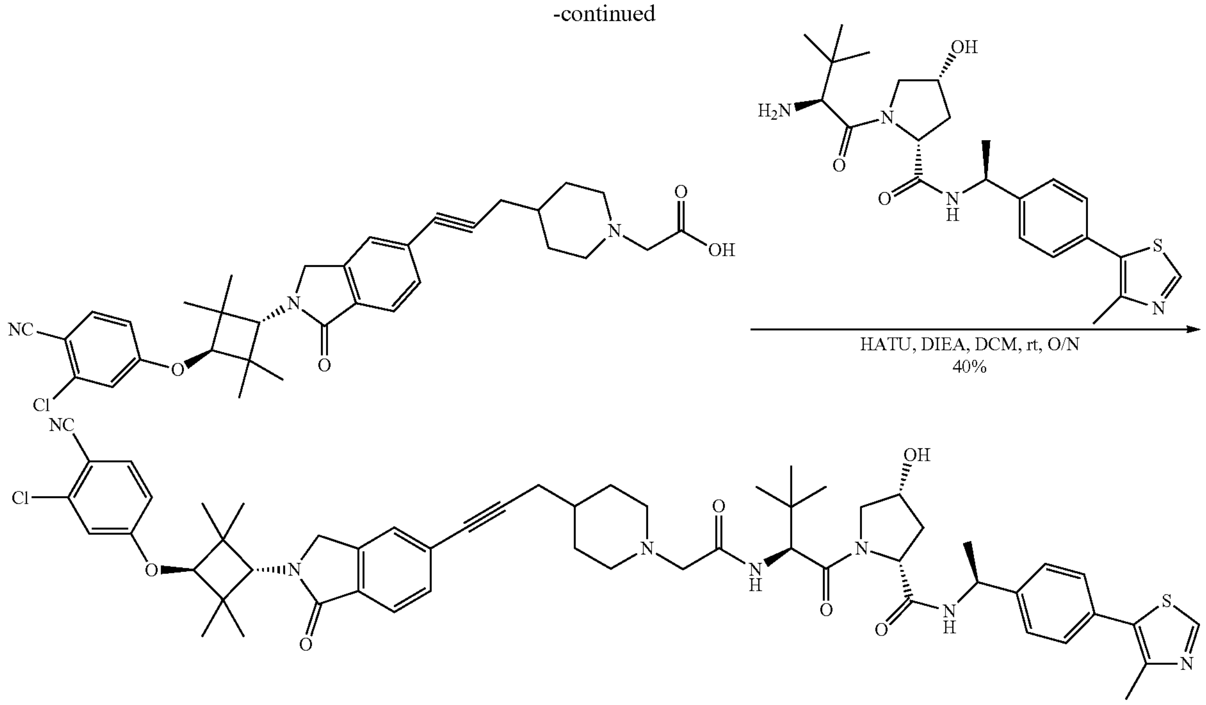

39

LC/MS (ESI$^+$) calcd for $C_{56}H_{66}ClN_7O_6S$ [M+H]$^+$ m/z, 1000.5, found, 1000.5.

$^1$H NMR (400 MHz, DMSO-d$_6$) δ 8.98 (s, 1H), 8.44 (d, J=7.6 Hz, 1H), 7.90 (d, J=8.8 Hz, 1H), 7.85 (d, J=9.7 Hz, 1H), 7.65 (d, J=8.3 Hz, 3H), 7.54 (dd, J=7.9, 1.4 Hz, 1H), 7.43 (d, J=8.2 Hz, 3H), 7.29 (d, J=2.4 Hz, 1H), 7.06 (dd, J=8.8, 2.4 Hz, 1H), 5.32 (t, J=4.8 Hz, 1H), 5.14 (d, J=3.4 Hz, 1H), 4.77 (s, 3H), 4.53 (d, J=5.0 Hz, 2H), 4.47-4.43 (m, 2H), 3.59 (d, J=14.9 Hz, 4H), 3.41-3.36 (m, 2H), 3.02 (d, J=16.4 Hz, 2H), 2.89 (t, J=17.4 Hz, 6H), 2.70-2.62 (m, 1H), 2.04 (d, J=11.3 Hz, 2H), 2.02-1.96 (m, 1H), 1.76 (d, J=12.7 Hz, 5H), 1.15 (s, 9H), 0.94 (d, J=6. Hz, 12H).

40: (2R,4R)-1-((S)-2-(2-((1-(3-(2-((1r,3r)-3-(3-chloro-4-cyanophenoxy)-2,2,4,4-tetramethylcyclobutyl)-1-oxoisoindolin-5-yl)prop-2-yn-1-yl)azetidine-3-yl)oxy) acetylamino)-3,3-dimethylbutyryl)-4-hydroxy-N-((S)-1-(4-(4-(4-methylthiazol-5-yl) phenyl)ethyl)pyrrolidine-2-carboxamide

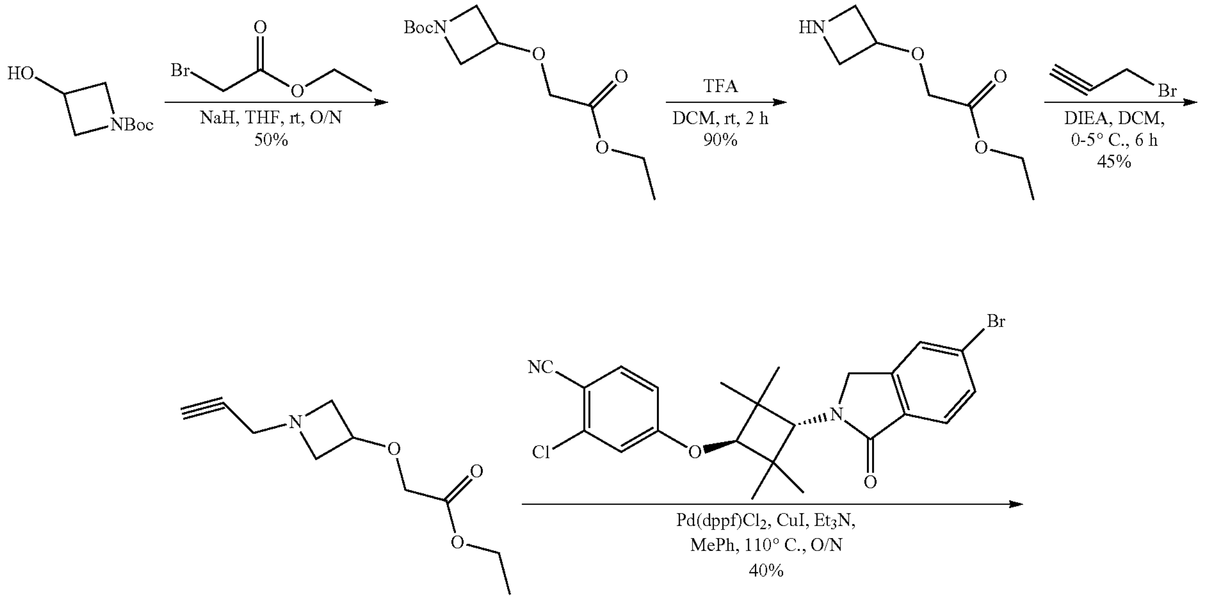

-continued
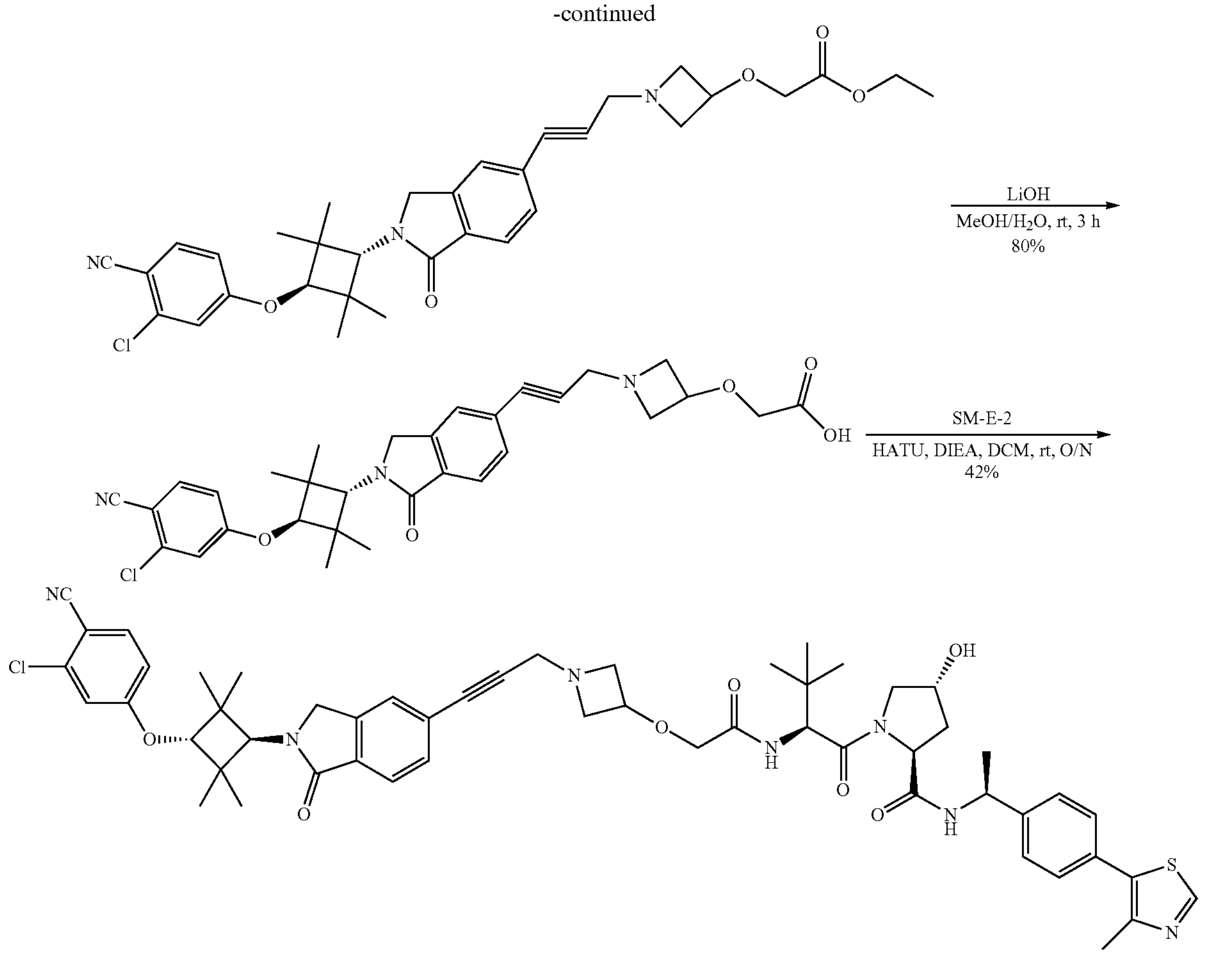
41: (2S, 4R)-1-((S)-2-(1-((6-(2-((1 r,3r)-3-(3-chloro-4-cyanophenoxy)-2,2,4,4-tetramethylcyclobutyl)-1-oxoisoindolin-5-yl)hexy-5-yn-1-yl)oxy) cyclopropaneformamide)-3,3-dimethylbutyryl)-4-hydroxy-N-((S)-1-(4-methylthiazol-5-yl)phenyl)ethyl) pyrrolidine-2-carboxamide
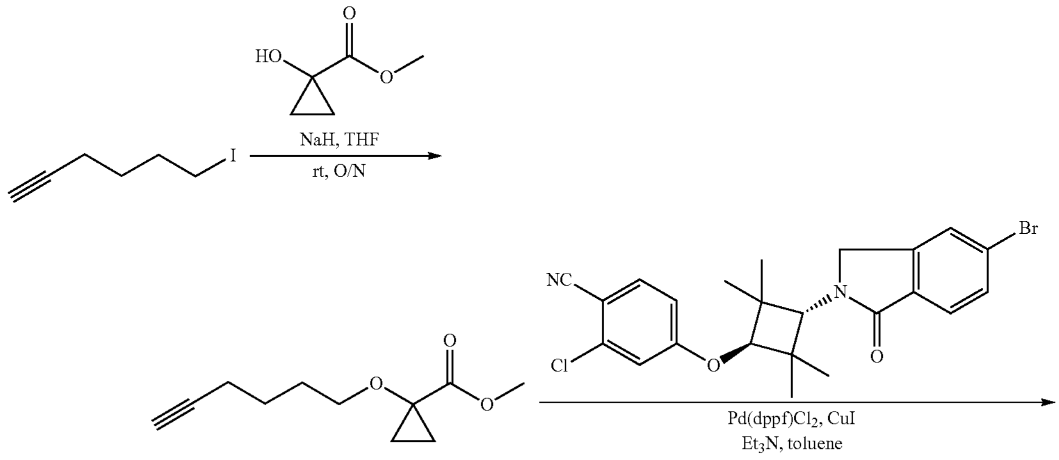

-continued

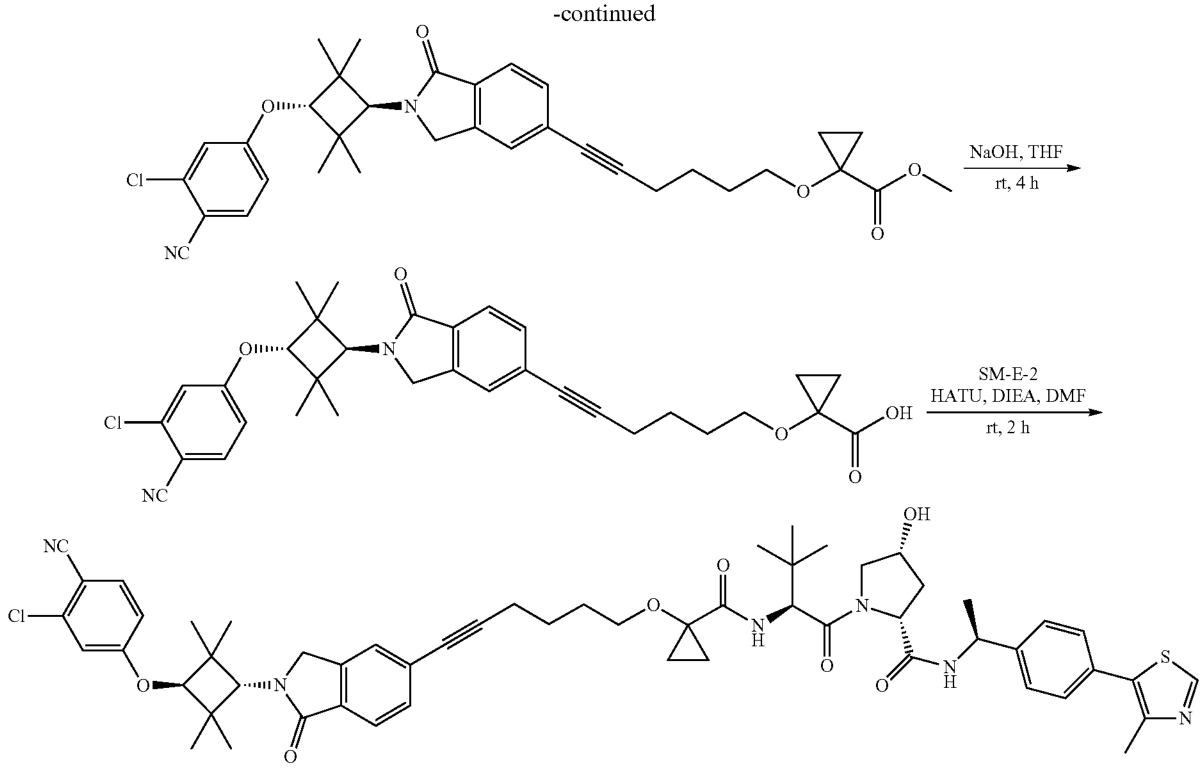

41

1. Synthesis of Compound ethyl 1-(5-pentynyl-1-oxy)cyclopropanecarboxylate

Under the protection of nitrogen, methyl 1-hydroxycyclopropanecarboxylate (100.0 mg, 0.86 mmol) was dissolved in 2 mL of THF in an ice bath, to which was added NaH (41.0 mg, 1.03 mmol), and the mixture was stirred for 30 min. Then, 6-iodo-hexy-1-yne was also added (179.0 mg, 0.86 mmol). The resultant mixture was stirred overnight at room temperature, to which were added ethyl acetate and water for extraction. The organic laver was washed with saturated brine, dried, rotatory evaporated to dry, and purified by silica gel column chromatography, to provide compound ethyl 1-(5-pentynyl-1-oxy)cyclopropanecarboxylate (110.0 mg, 0.56 mmol), with a yield of 65.1%.

LC/MS ($ESI^+$) calcd for $C_{11}H_{17}O_3^+$ ($[M+H]^+$) m/z: 197.1; found 197.1.

2. Synthesis of methyl 1-((6-(2-((1r,3r)-3-(3-chloro-4-cyanophenoxy)-2,2,4,4-tetramethylcyclobutyl)-1-oxoisoindol-5-yl)hex-5-yn-1-yl)oxy) cyclopropanecarboxylate Under the nitrogen protection, ethyl 1-(5-pentynyl-1-oxy) cyclopropanecarboxylate (110.0 mg, 0.56 mmol), 4-((1r,3r)-3-(5-bromo-1-oxoisoindol-2-yl)-2,2,4,4-tetramethylcyclobutoxy)-2-chlorobenzonitrile (100.0 mg, 0.21 mmol), $Pd(PPh_3)_2Cl_2$ (50.0 mg, 0.05 mmol), CuI (4.0 mg, 0.1 mmol), and 0.5 mL triethylamine were dissolved in 2 mL of toluene, and the mixture was heated to 110° C. and stirred overnight. The reaction solution was cooled to room temperature and filtered. The filter cake was washed with ethyl acetate, dried, rotatory evaporated to dry, and purified by silica gel column chromatography, to provide compound methyl 1-((6-(2-((1r,3r)-3-(3-chloro-4-cyanophenoxy)-2,2,4,4-tetramethylcyclobutyl)-1-oxoisoindol-5-yl)hex-5-yn-1-yl)oxy)cyclopropanecarboxylate (65.0 mg, 0.13 mmol), with a yield of 52.3%.

LC/MS ($ESI^+$) calcd for $C_{34}H_{38}ClN_2O_5^+$ ($[M+H]^+$) m/z: 589.2; found 589.1.

3. Synthesis of Compound 1-((6-(2-((1r,3r)-3-(3-chloro-4-cyanophenoxy)-2,2,4,4-tetramethylcyclobutyl)-1-oxoisoindolin-5-yl)hex-5-yn-1-yl)oxy) cyclopropanecarboxylic acid Methyl 1-((6-(2-((1r,3r)-3-(3-chloro-4-cyanophenoxy)-2,2,4,4-tetramethylcyclobutyl)-1-oxoisoindol-5-yl)hex-5-yn-1-yl)oxy)cyclopropanecarboxylate (65.0 mg, 0.13 mmol) was dissolved in methanol (2 mL), to which was added 2 N NaOH (2 mL), and the mixture was stirred 2 h at room temperature. The reaction solution was adjusted to pH 4-5 with 1N HCl, and then extracted with dichloromethane. The organic layer was washed with saturated brine, dried, and rotatory evaporated, to provide compound 1-((6-(2-((1r,3r)-3-(3-chloro-4-cyanophenoxy)-2,2,4,4-tetramethylcyclobutyl)-1-oxoisoindol-5-yl)hex-5-yn-1-yl)oxy)cyclopropanecarboxylic acid (65.0 mg, 0.13 mmol), with a yield of 100.0%.

4. Synthesis of Compound (2S,4R)-1-((S)-2-(1-((6-(2-((1r,3r)-3-(3-chloro-4-cyanophenoxy)-2,2,4,4-tetramethylcyclobutyl)-1-oxoisoindolin-5-yl)hexy-5-yn-1-yl)oxy)cyclopropaneformamide)-3,3-dimethylbutyryl)-4-hydroxy-N-((S)-1-(4-methylthiazol-5-yl)phenyl)ethyl)pyrrolidine-2-carboxamide 1-((6-(2-((1r,3r)-3-(3-chloro-4-cyanophenoxy)-2,2,4,4-tetramethylcyclobutyl)-1-oxoisoindol-5-yl)hex-5-yn-1-yl)

oxy)cyclopropanecarboxylic acid (50.0 mg, 0.08 mmol), HATU (37.0 mg, 0.08 mmol), and DIEA (35.0 mg, 0.24 mmol) were dissolved in 2 mL DMF, to which was added (2R,4R)-1-((S)-2-amino-3,3-dimethylbutanol)-4-hydroxy-N-((S)-1-(4-(4-methylthiazol-5-yl)phenyl)ethyl)pyrrolidine-2-carboxamide (46.0 mg, 0.08 mmol). The mixture was stirred 2 h at room temperature, to which were added water and ethyl acetate for extraction. The organic layer was washed with saturated brine, dried, rotatory evaporated to dry, and purified by silica gel column chromatography, to provide (2S,4R)-1-((S)-2-(1-((6-(2-((1r,3r)-3-(3-chloro-4-cyanophenoxy)-2,2,4,4-tetramethylcyclobutyl)-1-oxoisoindolin-5-yl)hexy-5-yn-1-yl)oxy)cyclopropaneformamide)-3,3-dimethylbutyryl)-4-hydroxy-N-((S)-1-(4-methylthiazol-5-yl)phenyl)ethyl)pyrrolidine-2-carboxamide (40.0 mg, 0.04 mmol), with a yield of 44.9%. LC/MS (ESI$^+$) calcd for $C_{56}H_{66}ClN_6O_7S^+$ ([M+H]$^+$) m/z: 1001.4; found 1001.5. $^1$H NMR (400 MHz, $CDCl_3$) δ 8.75 (s, 1H), 7.76 (d, J=7.8 Hz, 1H), 7.57 (d, J=8.7 Hz, 1H), 7.47 (d, J=7.9 Hz, 2H), 7.44 (s, 1H), 7.39 (q, J=8.3 Hz, 4H), 7.31 (d, J=8.4 Hz, 1H), 6.99 (d, J=2.3 Hz, 1H), 6.84 (dd, J=8.7, 2.4 Hz, 1H), 5.14-5.02 (m, 1H), 4.81-4.73 (m, 1H), 4.66-4.57 (m, 2H), 4.54-4.45 (m, 2H), 4.42-4.36 (m, 1H), 4.35-4.28 (m, 1H), 4.21-4.12 (m, 1H), 3.63-3.52 (m, 3H), 2.65 (d, J=9.4 Hz, 1H), 2.59-2.46 (m, 6H), 2.14-2.04 (m, 2H), 1.82-1.71 (m, 4H), 1.47 (d, J=6.9 Hz, 3H), 1.43 (d, J=5.8 Hz, 6H), 1.25 (s, 6H), 1.07 (d, J=17.6 Hz, 11H), 0.88 (t, J=6.7 Hz, 2H).

42: ((2S,4R)-1-((S)-2-(3-((2-((1r,3r)-3-(3-chloro-4-cyanophenoxy)-2,2,4,4-tetramethylcyclobutyl)-1-oxoisoindolin-5-yl)ethynyl)-1H-pyrazol-1-yl) propionamido)-3,3-dimethylbutanol)-4-hydroxy-N-((S)-1-(4-methylthiazol-5-yl)phenyl)ethyl)pyrrolidine-2-carboxamide

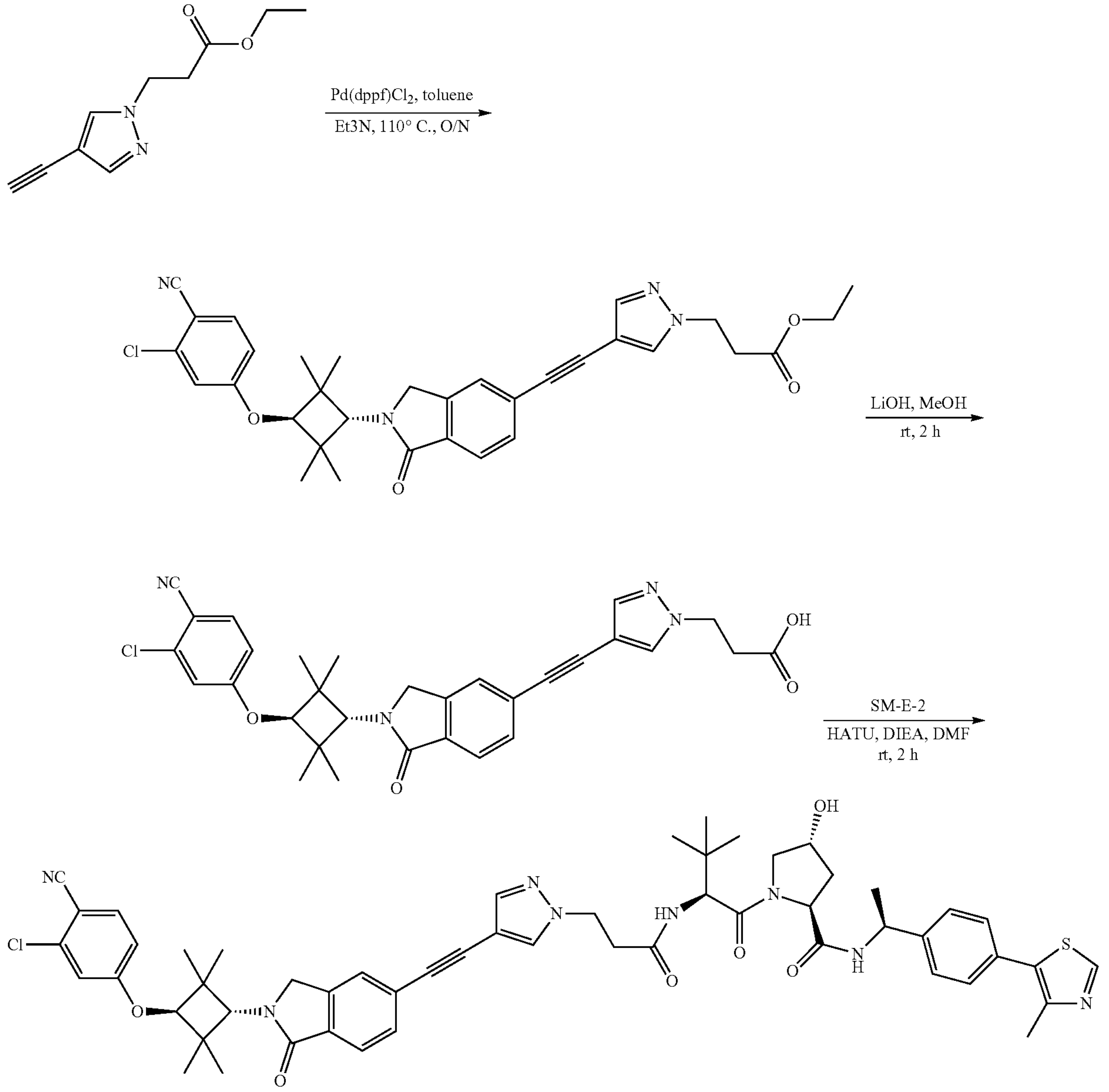

42

Compound 42 (45.0 mg, 0.04 mmol) was obtained. LC/MS (ESI$^+$) calcd for $C_{54}H_{60}ClN_8O_6S^+$ ([M+H]$^+$) m/z: 983.4; found 983.4. $^1$H NMR (400 MHz, $CDCl_3$) δ 9.02 (s, 1H), 7.79 (d, J=7.8 Hz, 1H), 7.67 (d, J=15.9 Hz, 2H), 7.58 (d, J=8.7 Hz, 1H), 7.53 (d, J=8.6 Hz, 1H), 7.50 (s, 1H), 7.45 (s, 1H), 7.37 (d, J=10.7 Hz, 4H), 7.00 (d, J=2.2 Hz, 1H), 6.88-6.81 (m, 1H), 6.62 (s, 1H), 5.06 (d, J=6.1 Hz, 1H), 4.78 (s, 1H), 4.64 (s, 2H), 4.39 (s, 1H), 4.33 (s, 1H), 4.10 (d, J=12.7 Hz, 1H), 3.75-3.57 (m, 4H), 2.84 (d, J=25.6 Hz, 2H), 2.62 (s, 4H), 2.03 (d, J=7.1 Hz, 2H), 1.47-1.40 (m, 9H), 1.28 (d, J=3.0 Hz, 6H), 1.00 (s, 9H).

43: (2S,4R)-1-((S)-2-(3-(3-(2-((1r,3r)-3-(3-chloro-4-cyanophenoxy)-2,2,4,4-tetramethylcyclobutyl)-1-oxoisoindolin-5-yl)prop-2-yn-1-yl)azetidin-1-yl) acetamide)-3,3-dimethylbutyryl)-4-hydroxy-N-((S)-1-(4-(4-methylthiazol-5-yl)phenyl)ethyl)pyrrolidine-2-carboxamide

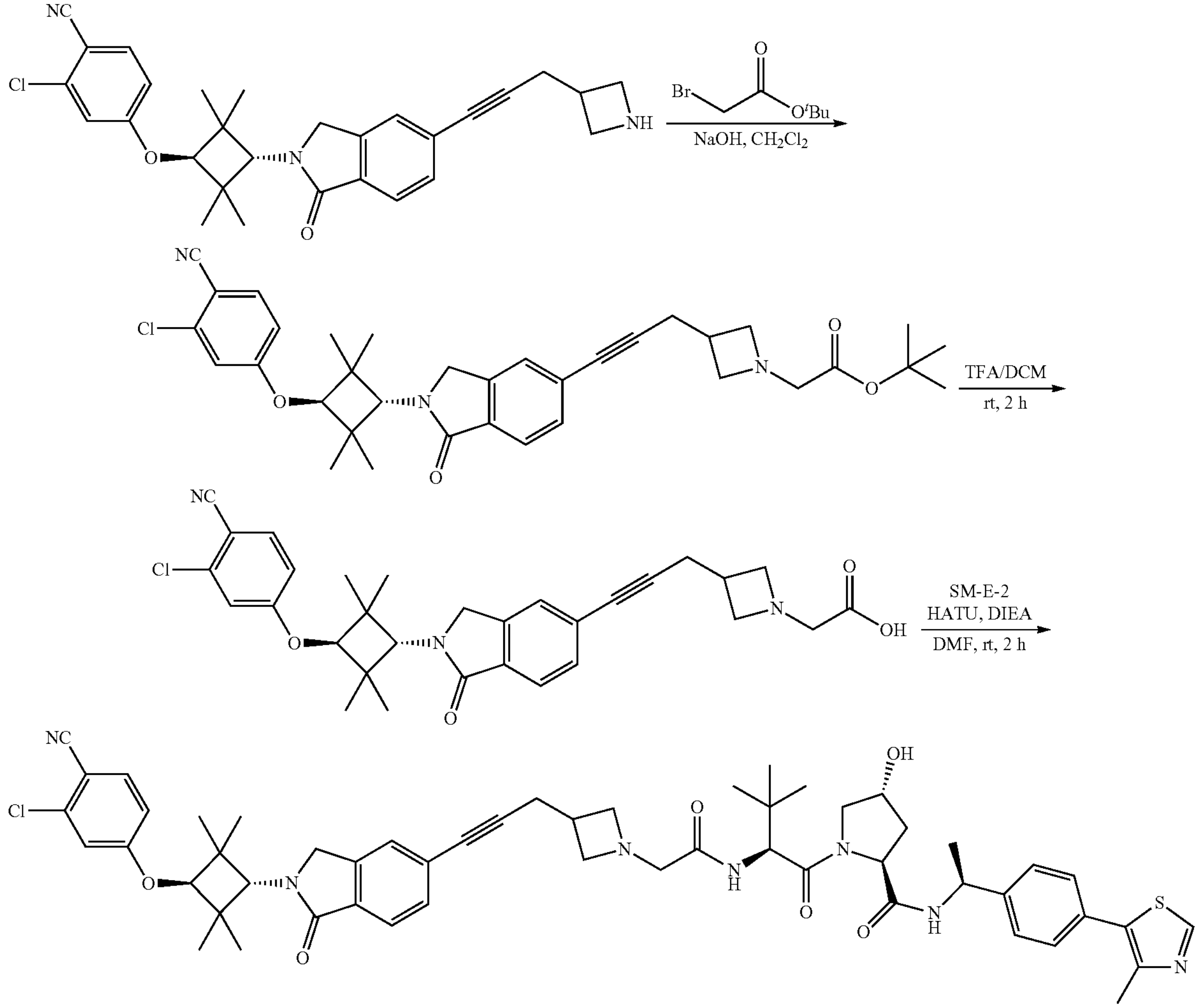

43

Compound 43 (18.0 mg, 0.02 mmol) was obtained. LC/MS (ESI$^+$) calcd for $C_{54}H_{63}ClN_7O_6S^+$ ([M+H]$^+$) m/z: 972.4; found 972.5. $^1$H NMR (400 MHz, $CDCl_3$) δ 8.67 (s, 1H), 7.90 (s, 1H), 7.78 (d, J=8.2 Hz, 1H), 7.57 (d, J=8.7 Hz, 1H), 7.50 (d, J=7.0 Hz, 2H), 7.43-7.31 (m, 4H), 6.99 (d, J=2.3 Hz, 1H), 6.84 (dd, J=8.7, 2.3 Hz, 1H), 5.11-5.02 (m, 1H), 4.77 (t, J=7.9 Hz, 1H), 4.65 (s, 2H), 4.51 (d, J=8.8 Hz, 2H), 4.40 (s, 1H), 4.32 (s, 1H), 4.12 (d, J=11.9 Hz, 1H), 3.85 (s, 21H), 3.59 (d, J=8.5 Hz, 1H), 3.47 (s, 2H), 2.95 (s, 1H), 2.73 (s, 2H), 2.53 (d, J=3.7 Hz, 4H), 2.13 (s, 1H), 1.74 (s, 3H), 1.47 (d, J=8.3 Hz, 3H), 1.45 (s, 6H), 1.26 (s, 6H), 1.07 (s, 9H).

44: ((2S,4R)-1-((S)-2-(3-(3-(3-(2-((1r,3r)-3-(3-chloro-4-cyanophenoxy)-2,2,4,4-tetramethylcyclobutyl)-1-oxoisoindolin-5-yl)prop-2-yn-1-yl)azetidin-1-yl)propylamino)-3,3-dimethylbutanol)-4-hydroxy-N-((S)-1-(4-(4-methylthiazol-5-yl)phenyl)ethyl)pyrrolidine-2-carboxamide
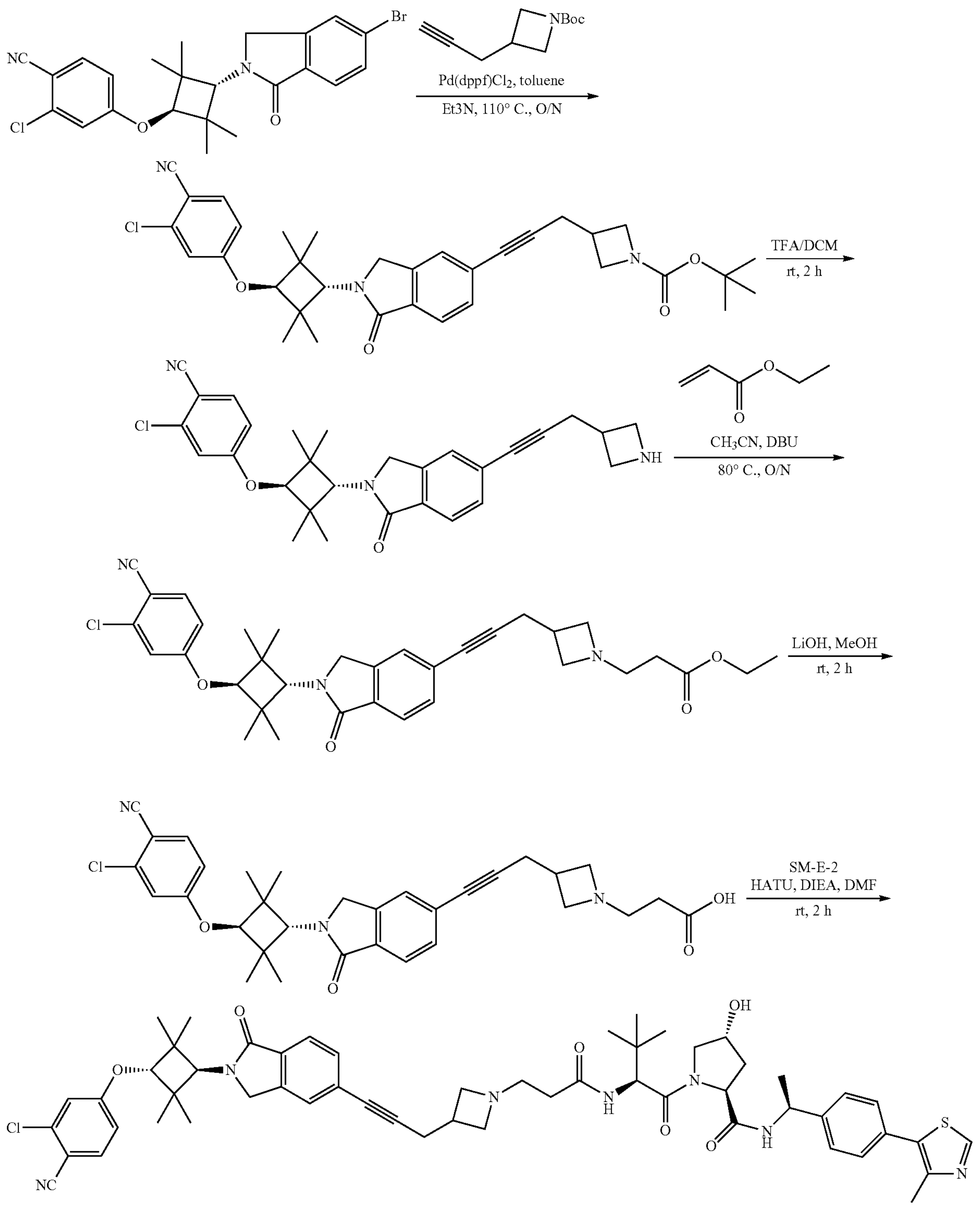

Compound 44 (20 mg, 0.02 mmol) was obtained. LC/MS ($ESI^+$) calcd for $C_{55}H_{65}ClN_7O_6S^+$ ($[M+H]^+$) m/z: 986.4; found 986.5. $^1H$ NMR (400 MHz, $CDCl_3$) δ 8.67 (s, 1H), 8.20 (s, 1H), 7.80 (d, J=7.8 Hz, 1H), 7.74 (d, J=7.8 Hz, 1H), 7.58 (d, J=8.7 Hz, 1H), 7.54-7.46 (m, 2H), 7.38 (s, 4H), 6.99 (d, J=2.3 Hz, 1H), 6.84 (dd, J=8.7, 2.3 Hz, 1H), 5.12-5.05 (m, 1H), 4.81 (d, J=8.2 Hz, 1H), 4.65 (s, 2H), 4.58 (d, J=8.3 Hz, 1H), 4.47 (s, 1H), 4.40 (s, 1H), 4.31 (s, 1H), 4.19 (s, 2H), 4.10 (d, J=11.5 Hz, 1H), 3.78 (d, J=31.2 Hz, 2H), 3.61 (d, J=8.9 Hz, 1H), 3.38 (s, 1H), 3.21 (d, J=42.9 Hz, 2H), 2.76 (s, 21-), 2.64 (s, 2H), 2.52 (s, 31H), 2.34 (s, 2H), 1.48 (d, J=6.9 Hz, 3H), 1.45 (s, 6H), 1.25 (s, 6H), 1.08 (s, 9H).

45: 2-chloro-4-((1 r,3r)-3-(5-((1-(1-(2-(2,6-dioxopiperidin-3-yl)-6-fluoro-1,3-dioxoisoindol-5-yl)azelaic acid-3-yl)-1H-pyrazol-4-yl)ethynyl)-1-oxoisoindolin-2-yl-2,2,4,4-tetramethylcyclobutoxy)benzonitrile

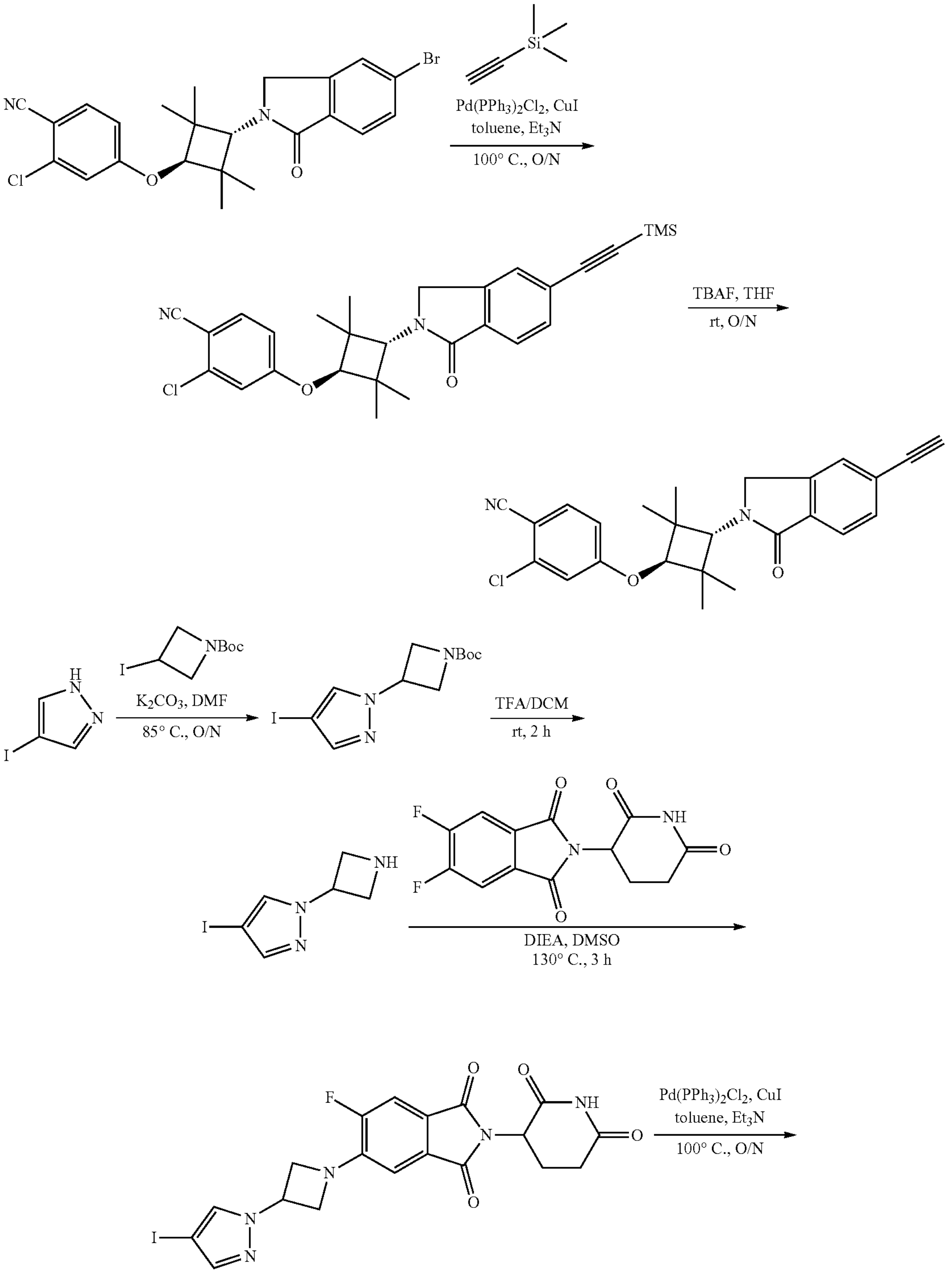

-continued

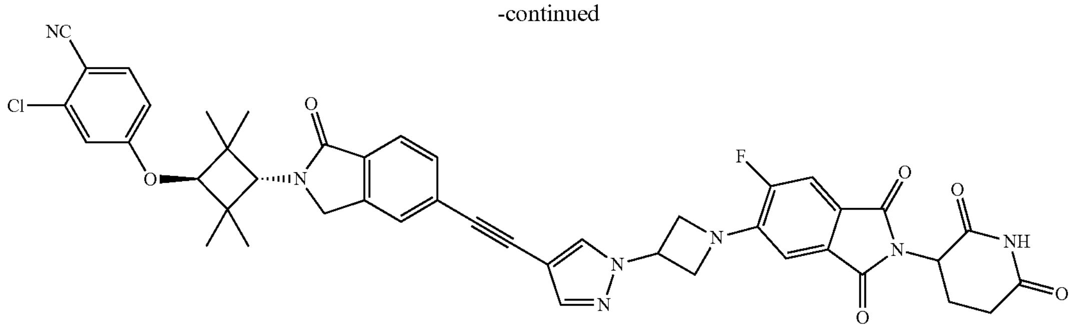

45

1. Synthesis of Compound (2-chloro-4-((1r,3r)-2,2,4,4-tetramethyl-3-(1-oxo-5-((trimethylsilyl)ethynyl)isoindolin-2-yl)cyclobutyloxy)benzonitrile Under the nitrogen protenction, 4-((1r,3r)-3-(5-bromo-1-oxoisoindolin-2-yl)-2,2,4,4-tetramethylcyclobutoxy)-2-chlorobenzonitrile (500.0 mg, 1.06 mmol), ethynyltrimethylsilane (518.0 mg, 5.28 mmol), $Pd(PPh_3)_2Cl_2$ (100.0 mg, 0.1 mmol), CuI (60.0 mg, 0.2 mmol), and 2 mL triethylamine were dissolved in 6 mL of toluene, and the mixture was heated to 110° C. and stirred overnight. The reaction solution was cooled to room temperature and filtered. The filter cake was washed with ethyl acetate, dried, rotatory evaporated to dry, and purified by silica gel column chromatography, to provide compound (2-chloro-4-((1r,3r)-2,2,4,4-tetramethyl-3-(1-oxo-5-((trimethylsilyl)ethynyl)isoindol-2-yl)cyclobutyloxy)benzonitrile (400 mg, 0.80 mmol), with a yield of 77.2%. LC/MS ($ESI^+$) calcd for $C_{28}H_{32}ClN_2O_2Si^+$ ($[M+H]^+$) m/z: 491.2; found 491.1.

2. Synthesis of Compound 2-chloro-4-((1r,3r)-3-(5-ethynyl-1-oxoisoindolin-2-yl)-2,2,4,4-tetramethylcyclobutoxy)benzonitrile 2-Chloro-4-((1r,3r)-2,2,4,4-tetramethyl-3-(1-oxo-5-((trimethylsilyl)ethynyl)isoindol-2-yl)cyclobutyloxy)benzonitrile (400.0 mg, 0.80 mmol) and TBAF (1.0 g, 1.60 mmol) were dissolved in 10 mL of THF, and the mixture was stirred overnight at room temperature, to which were added ethyl acetate and water for extraction. The organic layer was washed with saturated brine, dried, rotatory evaporated to dry, and purified by silica gel column chromatography, to provide compound 2-chloro-4-((1r,3r)-3-(5-ethynyl-1-oxoisoindol-2-yl)-2,2,4,4-tetramethylcyclobutoxy)benzonitrile (150 mg, 0.35 mmol), with a yield of 43.9%.

LC/MS ($ESI^+$) calcd for $C_{25}H_{24}ClN_2O_2^+$ ($[M+H]^+$) m/z: 419.2; found 419.1.

3. Synthesis of t-butyl 3-(4-iodo-1H-pyrazol-1-yl)azelate

4-Iodo-1H-pyrazole (400.0 mg, 1.40 mmol), t-butyl 3-iodoazetidin-1-carboxylate (274.0 mg, 1.41 mmol), and $K_2CO_3$ (292.0 mg, 2.12 mmol) were dissolved in 5 mL of DMF, and the mixture was heated to 85° C. and stirred overnight. The reaction solution was cooled to room temperature, to which were added water and ethyl acetate for extraction. The organic layer was washed with saturated brine, dried, rotatory evaporated to dry, and purified by silicagel column chromatography, to provide compound t-butyl 3-(4-iodo-1H-pyrazol-1-yl)azelate (380 mg, 1.08 mmol), with a yield of 77.0%.

4. Synthesis of Compound 1-(azelaic acid-3-yl)-4-iodo-1H-pyrazole t-Butyl 3-(4-iodo-1H-pyrazol-1-yl)azelate (380 mg, 1.08 mmol) was dissolved in 2 mL of dichloromethane and 2 mL of trifluoroacetic acid, and the solution was stirred 2 h at room temperature. The reaction solution was concentrated, and rotatory evaporated to dry, to provide compound 1-(azelaic acid-3-yl)-4-iodo-1H-pyrazole (180 mg, 1.08 mmol), with a yield of 100.0%.

5. Synthesis of Compound 2-(2,6-dioxopiperidin-3-yl)-5-fluoro-6-(3-(4-iodo-1H-pyrazol-1-yl)azelaic acid-1-yl)isoindoline-1,3-dione 1-(Azelaic acid-3-yl)-4-iodo-1H-pyrazole (180.0 mg, 1.08 mmol), 2-(2,6-dioxopiperidin-3-yl)-5,6-difluoroisoindol-1,3-dione (100.0 mg, 0.339 mmol), and DIEA (219.0 mg, 1.70 mmol) were dissolved in 3 mL DMSO, and the resultant solution was heated to 130° C. and stirred for 3 h. The reaction solution was cooled to room temperature, to which were added water and ethyl acetate for extraction. The organic layer was washed with saturated brine, dried, rotatory evaporated to dry, and purified by silica gel column chromatography, to provide compound 2-(2,6-dioxopiperidin-3-yl)-5-fluoro-6-(3-(4-iodo-1H-pyrazol-1-yl)azelaic acid-1-yl)isoindoline-1,3-dione (150 mg, 0.26 mmol), with a yield of 84.0%.

LC/MS (ESI+) calcd for $C_{19}H_{16}FIN_5O_4^+$ ($[M+H]^+$) m/z: 524.0; found 524.0.

6. Synthesis of Compound 2-chloro-4-((1r,3r)-3-(5-((1-(I-(2-(2,6-dioxopiperidin-3-yl)-6-fluoro-1,3-dioxoisoindolin-5-yl)azelaic acid-3-yl)-1H-pyrazol-4-yl)ethynyl)-1-oxoisoindol-2-yl)-2,2,4,4-tetramethylcyclobutoxy)benzonitrile Under the nitrogen protection, 2-(2,6-dioxopiperidin-3-yl)-5-fluoro-6-(3-(4-iodo-1H-pyrazol-1-yl)azelaic acid-1-yl)isoindoline-1,3-dione (50.0 mg, 0.10 mmol), 2-chloro-4-((1r,3r)-3-(5-ethynyl-1-oxoisoindolin-2-yl)-2,2,4,4-tetramethylcyclobutoxy) benzonitrile (40.0 mg, 0.10 mmol), $Pd(PPh_3)_2Cl_2$ (8.0 mg, 0.01 mmol), CuI (10.0 mg, 0.02 mmol), and 0.3 mL of triethylamine were added in 1 mL of toluene, and the resultant solution was heated to 100° C. and stirred overnight. The reaction solution was cooled to room temperature and filtered. The filter cake was washed with ethyl acetate, dried, rotatory evaporated to dry, and purified by silica gel column chromatography, to provide compound (2-chloro-4-((1r,3r)-3-(5-((1-(1-(2-(2,6-dioxopiperidin-3-yl)-6-fluoro-1,3-dioxoisoindol-5-yl)azelaic acid-3-yl)-1H-pyrazol-4-yl)ethynyl)-1-oxoisoindolin-2-yl)-2,2,4,4-tetramethylcyclobutoxy)benzonitrile (15 mg, 0.80 mmol), with a yield of 19.2%.

LC/MS (ESI$^+$) calcd for $C_{44}H_{38}ClFN_7O_6^+$ ([M+H]$^+$) m/z: 814.3; found 814.2.

$^1$H NMR (400 MHz, $CDCl_3$) δ8.05-7.98 (m, 1H), 7.81 (d, J=7.9 Hz, 1H), 7.74 (s, 1H), 7.64 (s, 1H), 7.60-7.49 (m, 3H), 7.41 (d, J=12.2 Hz, 1H), 7.09 (d, J=7.2 Hz, 1H), 7.00 (d, J=2.4 Hz, 1H), 6.85 (dd, J=8.7, 2.4 Hz, 1H), 5.11-4.98 (m, 1H), 4.97-4.88 (m, 1H), 4.66 (s, 2H), 3.81-3.69 (m, 3H), 3.23 (td, J=9.8, 5.1 Hz, 1H), 2.99-2.85 (m, 5H), 2.85-2.70 (m, 2H), 2.16-2.08 (m, 1H), 1.46 (s, 6H), 1.27 (s, 6H).

46: (3R,5S)-1-((S)-2-(2-((5-((4-(((1r,3r)-3-(3-chloro-4-cyanophenoxy)-2,2,4,4-tetramethylcyclobutyl)carbamoyl)phenyl)amino)pentyl)oxy)acetamido)-3,3-dimethylbutanol)-5-((1-(4-methylthiazol-5-yl)phenyl)cyclopropyl)carbamoyl) pyrrolidin-3-yl acetate

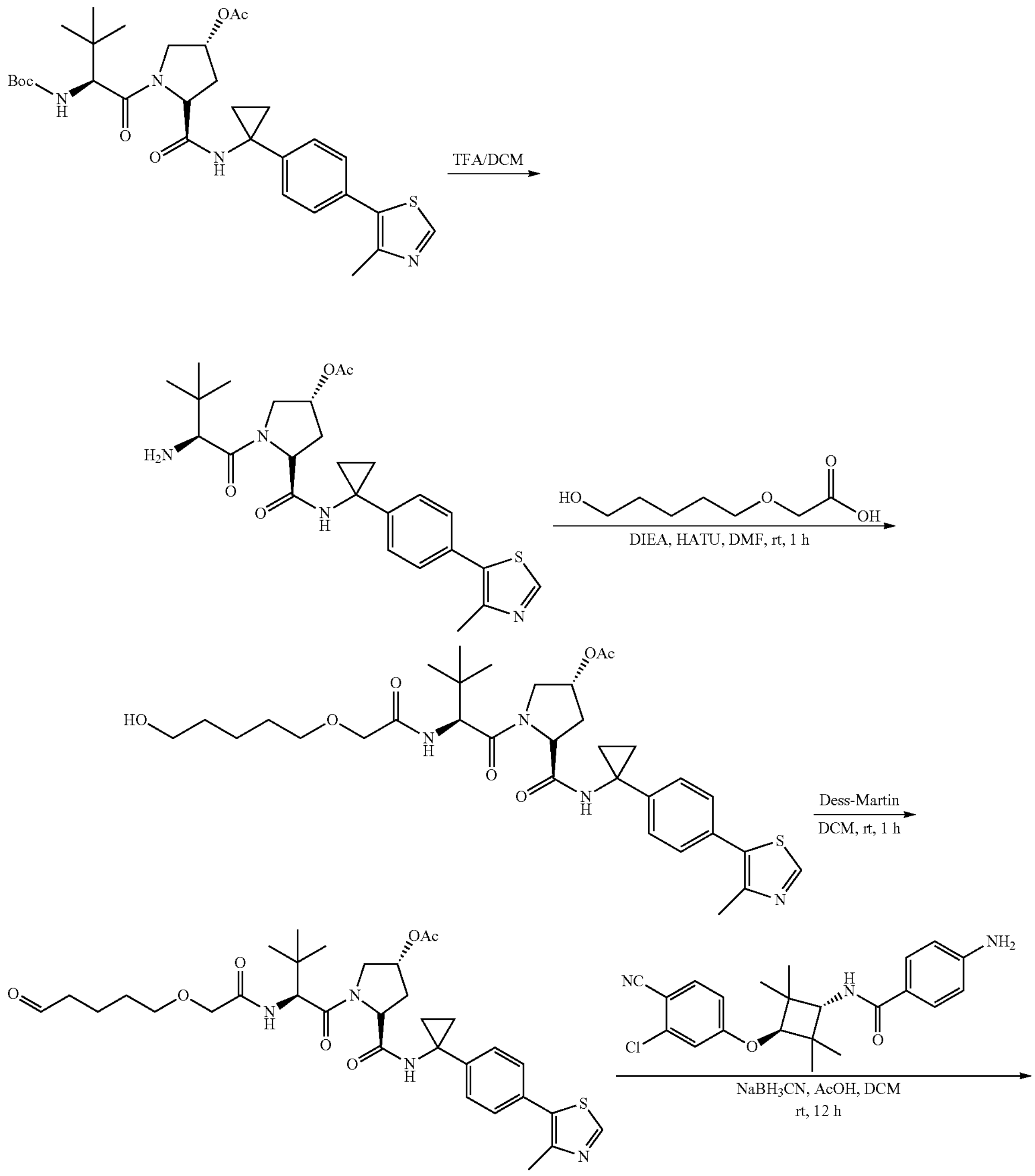

-continued

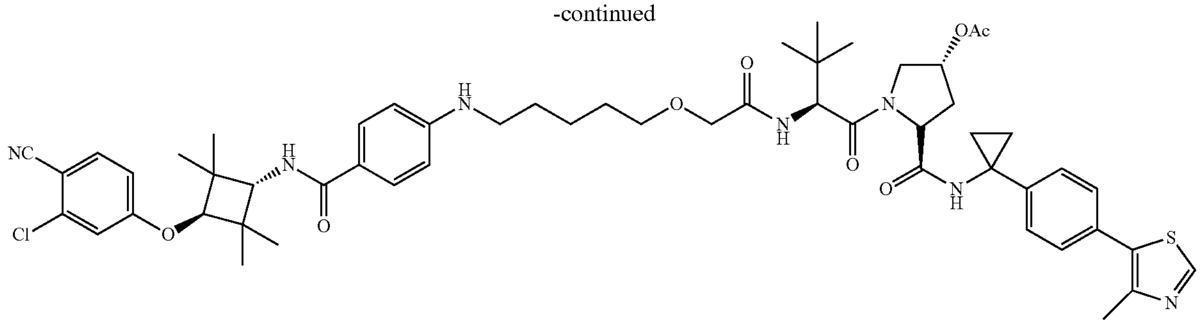

46

$^{1}$H NMR (400 MHz, DMSO-$d_6$) δ 8.95 (s, 1H), 8.87 (s, 1H), 7.90 (d, J=8.8 Hz, 1H), 7.63 (d, J=8.7 Hz, 2H), 7.47 (d, J=9.1 Hz, 1H), 7.32 (d, J=9.4 Hz, 1H), 7.21 (d, J=2.3 Hz, 1H), 7.00 (dd, J=8.8, 2.3 Hz, 1H), 6.59-6.51 (m, 2H), 6.17 (s, 1H), 5.28 (s, 1H), 4.31 (s, 1H), 4.06-4.03 (m, 1H), 3.94 (s, 2H), 3.49 (t, J=6.3 Hz, 2H), 3.05 (d, J=5.5 Hz, 2H), 2.69 (s, 6H), 2.43 (s, 2H), 2.04-1.96 (m, 4H), 1.65-1.50 (m, 4H), 1.44 (d, J=6.4 Hz, 2H), 1.20 (d, J=4.6 Hz, 6H), 1.17 (d, J=7.1 Hz, 2H), 1.11 (s, 9H), 1.02-0.80 (m, 12H). LC/MS (ESI$^+$) calcd for $C_{55}H_{68}ClN_7O_8S$ ([M+H]$^+$) m/z: 1022.70; found 511.8.

47: (2S,4R)-1-((S)-2-(2-((5-((4-(((1r,3r)-3-(3-chloro-4-cyanophenoxy)-2,2,4,4-tetramethylcyclobutyl)carbamoyl)phenyl)amino)pentyl)oxy)acetamide)-3,3-dimethylbutyryl)-4-hydroxy-N-(1-(4-methylthiazol-5-yl)phenyl)cyclopropyl) pyrrolidine-2-carboxamide

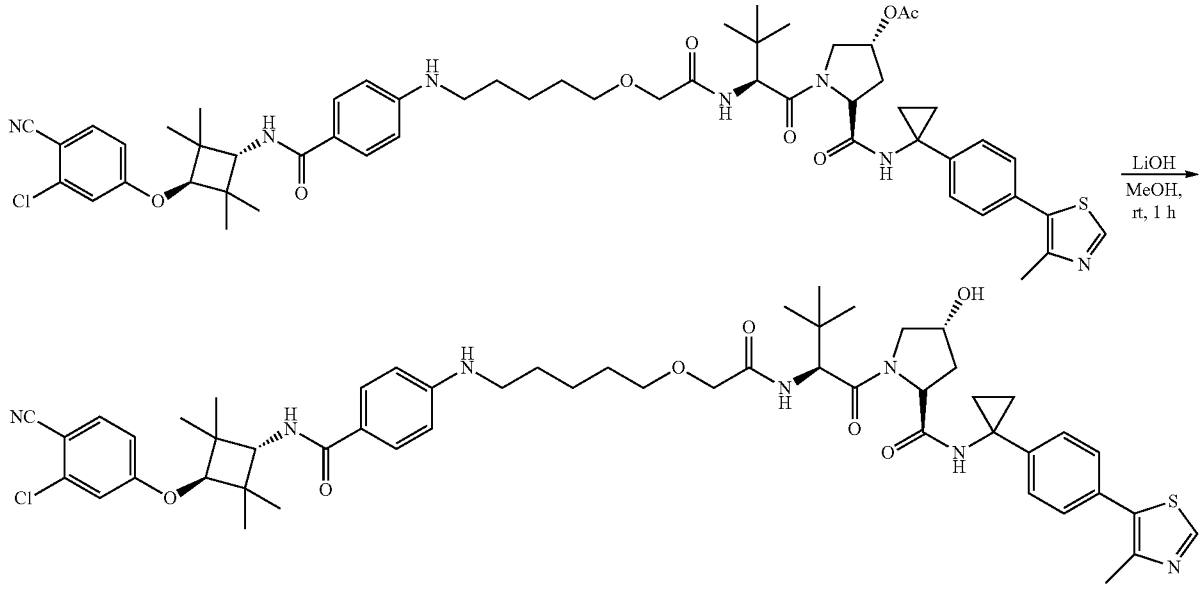

47

$^{1}$H NMR (400 MHz, DMSO-$d_6$) δ 8.94 (s, 1H), 8.84 (s, 1H), 7.90 (d, J=8.8 Hz, 1H), 7.66-7.60 (m, 2H), 7.45 (d, J=9.5 Hz, 1H), 7.33 (s, 2H), 7.20 (d, J=2.3 Hz, 1H), 7.00 (dd, J=8.8, 2.4 Hz, 1H), 6.54 (d, J=8.7 Hz, 2H), 6.16 (s, 1H), 5.17 (s, 1H), 4.56 (d, J=9.7 Hz, 1H), 4.42 (t, J=8.3 Hz, 1H), 4.35 (s, 1H), 4.31 (s, 1H), 4.03 (d, J=7.1 Hz, 2H), 3.94 (s, 1H), 3.63 (d, J=11.2 Hz, 1H), 3.50 (t, J=6.6 Hz, 3H), 3.17 (s, 2H), 3.05 (d, J=5.9 Hz, 2H), 2.43 (d, J=6.4 Hz, 3H), 1.99 (s, 3H), 1.59 (d, J=6.1 Hz, 4H), 1.44 (s, 2H), 1.11 (s, 9H), 0.94 (s, 12H). LC/MS (ESI+) calcd for $C_{53}H_{66}ClN_7O_7S$ ([M+H]$^+$) m/z: 980.66; found 980.3.

48: (2S,4R)-1-((S)-2-(2-((6-(2-(((1r,3r)-3-(3-chloro-4-cyanophenoxy))-2,2,4,4-tetramethylcyclobutyl)-1-oxoisoindolin-5-yl)hex-5-yn-1-yl)oxy)acetamido)-3,3-dimethylbutyryl)-4-hydroxy-N-((R)-2-hydroxy-1-(4-(4-methylthiazol-5-yl)phenyl) ethyl)pyrrolidine-2-carboxamide 49: (3R,5S)-1-((S)-2-(2-((6-(2-(((1r,3r)-3-(3-chloro-4-cyanophenoxy))-2,2,4,4-tetramethylcyclobutyl)-1-oxoisoindolin-5-yl)hex-5-yn-1-yl)oxy)acetamido)-3,3-dimethylbutyryl)-5-(((R)-2-hydroxy-1-(4-(4-methylthiazol-5-yl)phenyl)ethyl) carbamoyl) pyrrolidin-3-yl acetate

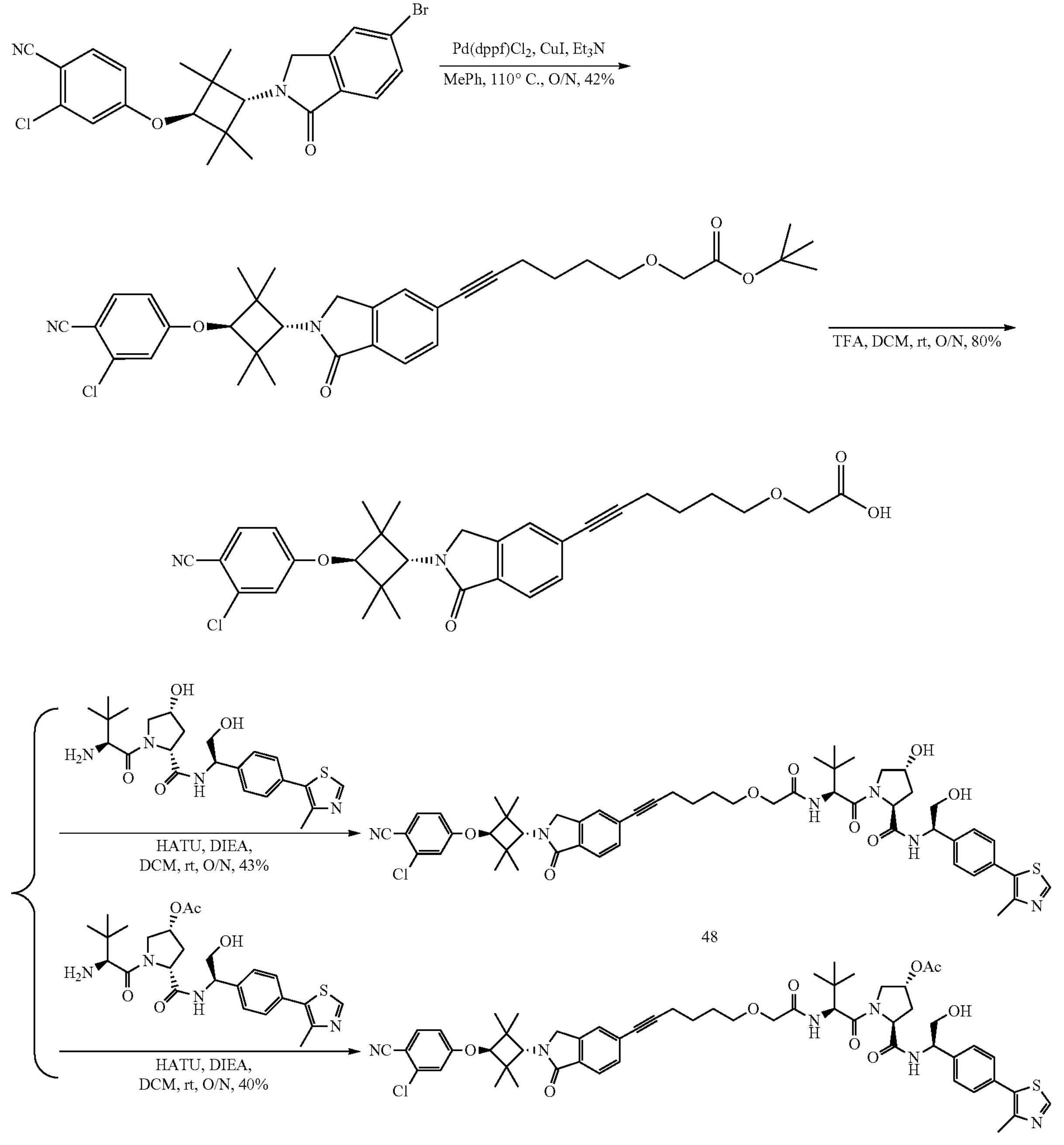

48

49

1. Synthesis of t-Butyl 2-((6-(2-(((1r,3r)-3-(3-chloro-4-cyanophenoxy)-2,2,4,4-tetramethylcyclobutyl)-1-oxoisoindol-5-yl)hex-5-yn-1-yl)oxy) acetate Synthesized according to the previous example, with a yield of 42%. LC/MS ($ESI^+$) calcd for: $C_{35}H_{41}ClN_2O_5$ $[M+H]^+$ m/z, 605.2; found, 605.2.

2. Synthesis of 2-((6-(2-(((1r,3r-3-(3-chloro-4-cyanophenoxy)-2,2,4,4-tetramethylcyclobutyl)-1-oxoisoindol-5-yl)hex-5-yn-1-yl))oxy)acetic acid Synthesized according to the previous example, with a yield of 80%. LC/MS ($ESI^+$) calcd for: $C_{31}H_{33}ClN_2O_5$ $[M+H]^+$ m/z, 549.2; found, 549.2.

3. Synthesis of (2S,4R)-1-((S)-2-(2-((6-(2-(((1r,3r)-3-(3-chloro-4-cyanophenoxy))-2,2,4,4-tetramethylcyclobutyl)-1-oxoisoindol-5-yl)hex-5-yn-1-yl)oxy) acetamido)-3,3-dimethylbutyryl)-4-hydroxy-N-((R)-2-hydroxy-1-(4-(4-methylthiazol-5-yl)phenyl)ethyl) pyrrolidine-2-carboxamide Synthesized according to the previous example, with a yield of 43%. LC/MS ($ESI^+$) calcd for: $C_{54}H_{63}ClN_6O_8S$ $[M+H]^+$ m/z, 991.4; found, 991.4. $^1H$ NMR (400 MHz, $CDCl_3$) δ 7.77 (d, J=7.6 Hz, 1H), 7.57 (d, J=8.7 Hz, 1H), 7.54-7.37 (m, 6H), 7.20 (m, 2H), 6.99 (d, J=2.9 Hz, 1H), 6.84 (d, J=8.8 Hz, 1H), 5.17 (s, 1H), 4.64 (s, 2H), 4.54 (s, 3H), 4.39 (s, 1H), 4.31 (s, 1H), 3.97 (s, 3H), 3.83 (m, 1H), 3.73 (m, 2H), 3.59 (s, 2H), 2.65 (s, 2H), 2.51 (m, 2H), 2.25-2.15 (m, 2H), 1.25 (s, 19H), 1.07 (s, 9H).

4. Synthesis of (3R,5S)-1-((S)-2-(2-((6-(2-(((1r,3r)-3-(3-chloro-4-cyanophenoxy))-2,2,4,4-tetramethylcyclobutyl)-1-oxoisoindol-5-yl)hex-5-yn-1-yl)oxy) acetamido)-3,3-dimethylbutyryl)-5-(((R)-2-hydroxy-1-(4-(4-methylthiazol-5-yl)phenyl)ethyl)carbamoyl) pyrrolidin-3-yl acetate Synthesized according to the previous example, with a yield of 40%. LC/MS ($ESI^+$) calcd for: $C_{56}H_{65}ClN_6O_9S$ $[M+H]^+$ m/z, 1033.4; found, 1033.4. $^1H$ NMR (400 MHz, $CDCl_3$) δ 9.23 (s, 1H), 7.78 (d, J=7.9 Hz, 1H), 7.57 (d, J=8.6 Hz, 1H), 7.54-7.38 (m, 6H), 7.16 (d, J=9.1 Hz, 1H), 6.99 (d, J=2.5 Hz, 1H), 6.84 (d, J=8.6 Hz, 1H), 5.15 (s, 1H), 4.68-4.51 (m, 4H), 4.40 (s, 1H), 4.31 (s, 1H), 4.13 (d, J=11.9 Hz, 1H), 4.07-3.94 (m, 3H), 3.89 (dd, J=11.7.4.4 Hz, 1H), 3.60 (s, 2H), 2.69 (s, 3H), 2.52 (t, J=6.7 Hz, 3H), 2.31-2.18 (m, 2H), 2.05 (d, J=2.3 Hz, 2H), 1.25 (d, J=2.4 Hz, 19H), 1.05 (s, 9H).

51: 2-chloro-4-((1R,3R)-3-(5-((1'-(2-(2,6-dioxopiperidin-3-yl)-6-fluoro-1,3-dioxoisoindolin-5-yl)-[1,4'-bispiperidin]-4-yl)ethynyl)-1-oxoisoindolin-2-yl))-2,2,4,4-tetramethylcyclobutoxy)benzonitrile

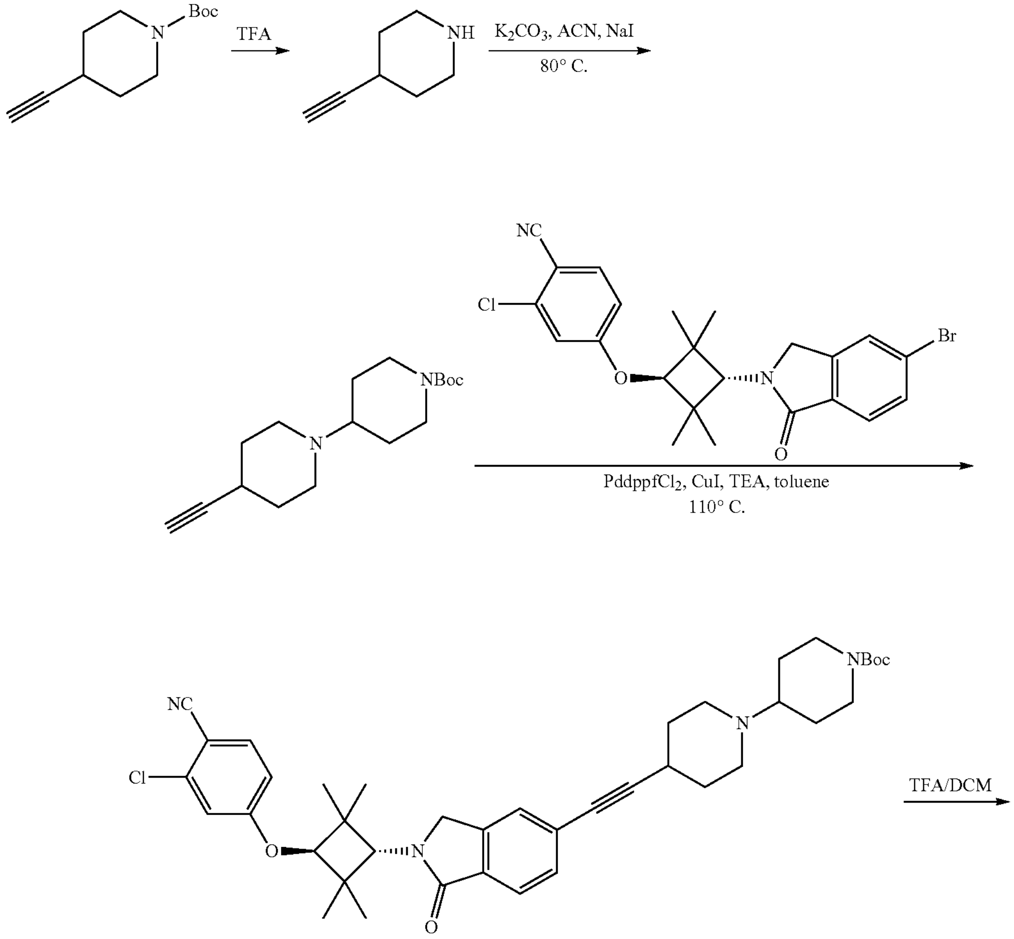

-continued
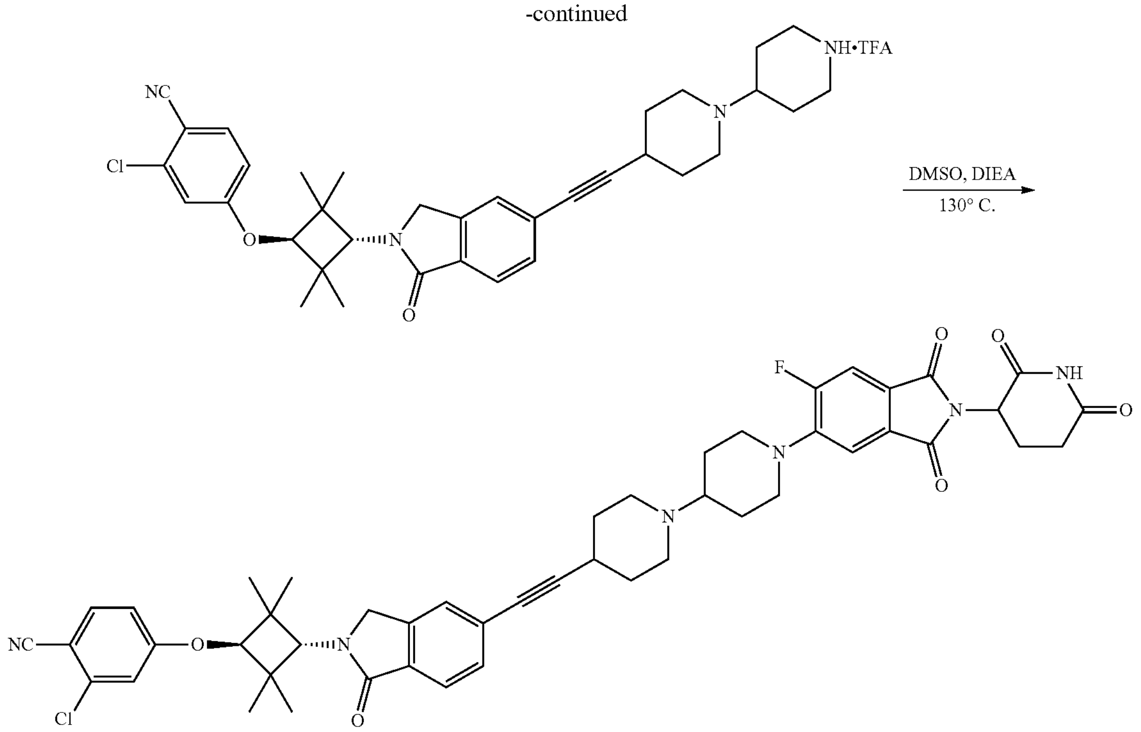
51
LC/MS (ESI+) Calcd for $C_{48}H_{48}ClFN_6O_6$ (M+$H^+$) m/z, 859.3; found 859.3. $^1$H NMR (400 MHz, $CDCl_3$) δ 7.78 (d, J=7.9 Hz, 1H), 7.58 (d, J=8.7 Hz, 1H), 7.48 (dd, J=12.8, 6.1 Hz, 3H), 7.39 (d, J=7.3 Hz, 1H), 7.00 (d, J=2.4 Hz, 1H), 6.84 (dd, J=8.7, 2.4 Hz, 1H), 4.93 (dd, J=12.3, 5.3 Hz, 1H), 4.64 (s, 2H), 4.40 (s, 1H), 4.32 (s, 1H), 3.74 (d, J=11.6 Hz, 2H), 3.01 (s, 2H), 2.88 (dd, J=23.1, 12.0 Hz, 4H), 2.81-2.69 (m, 4H), 2.62 (s, 1H), 2.13 (d, J=5.0 Hz, 3H), 2.05 (d, J=8.0 Hz, 4H), 1.45 (s, 6H), 1.26 (s, 6H).
52: 2-chloro-4-((1R,3R)-3-(5-((1'-(2-(2,6-dioxopiperidin-3-yl)-1,3-dioxoisoindolin-5-yl)-[1,4'-bispiperidin]-4-yl)ethynyl)-1-oxoisoindolin-2-yl))-2,2,4,4-tetramethylcyclobutoxy)benzonitrile
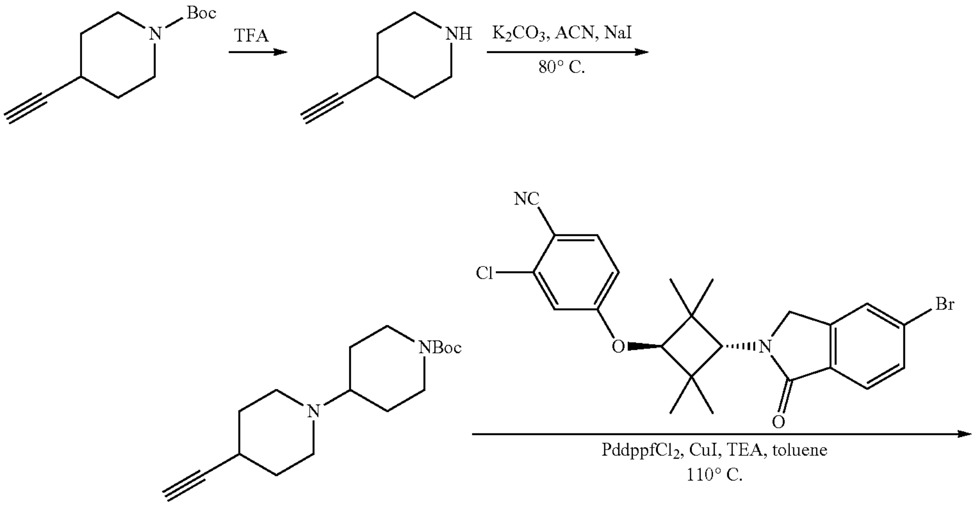

-continued
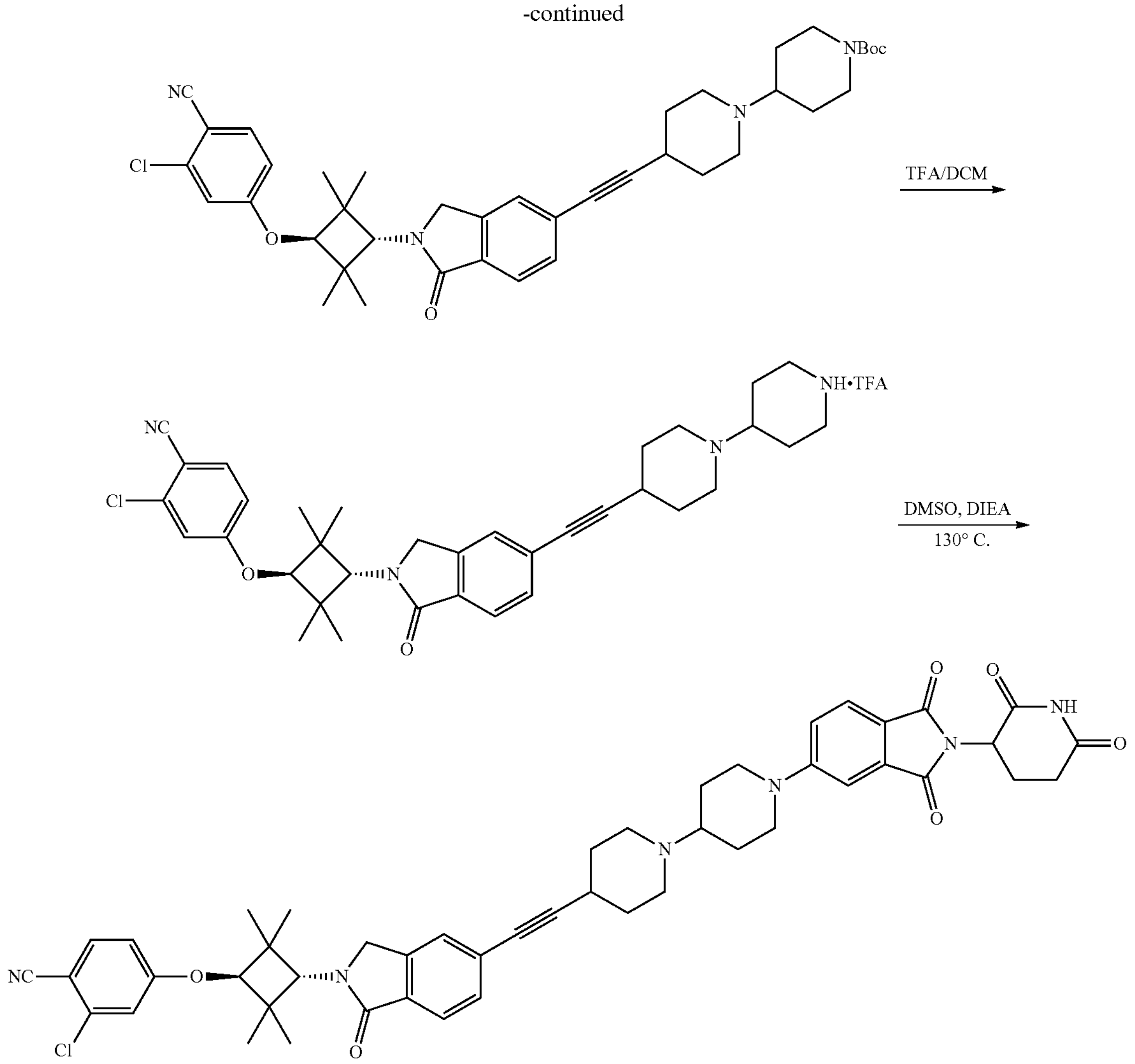
52
LC/MS (ESI+) Calcd for $C_{48}H_{49}ClN_6O_6(M+H^+)$ m/z, 841.3; found 841.3. $^1H$ NMR (400 MHz, $CDCl_3$) δ 8.20-7.96 (m, 1H), 7.78 (d, J=7.8 Hz, 1H), 7.70 (d, J=8.4 Hz, 1H), 7.58 (d, J=8.7 Hz, 1H), 7.53-7.44 (m, 2H), 7.28 (s, 1H), 7.07 (d, J=6.7 Hz, 1H), 7.00 (d, J=2.3 Hz, 1H), 6.84 (dd, J=8.7, 2.2 Hz, 1H), 4.94 (dd, J=12.0, 5.3 Hz, 1H), 4.64 (s, 2H), 4.40 (s, 1H), 4.33 (s, 1H), 4.05 (d, J=12.1 Hz, 2H), 3.75 (s, 1H), 3.10-2.98 (m, 5H), 2.95-2.69 (m, 6H), 2.26 (s, 2H), 2.16 (s, 2H), 1.98 (s, 3H), 1.45 (s, 6H), 1.26 (s, 6H).
53: Synthesis of 2-chloro-4-((1r,3r)-3-(5-((1-(I-(2-(2,6-dioxopiperidin-3-yl)-1,3-dioxoisoindolin-5-yl) azelaic acid-3-yl)piperidin-4-yl)ethynyl)-1-oxoisoindolin-2-yl)-2,2,4,4-tetramethylcyclobutoxy) benzonitrile
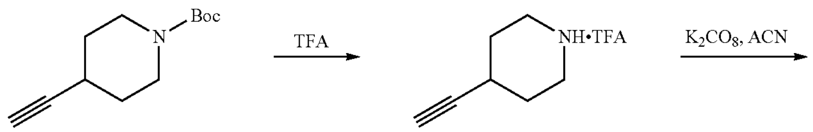

-continued
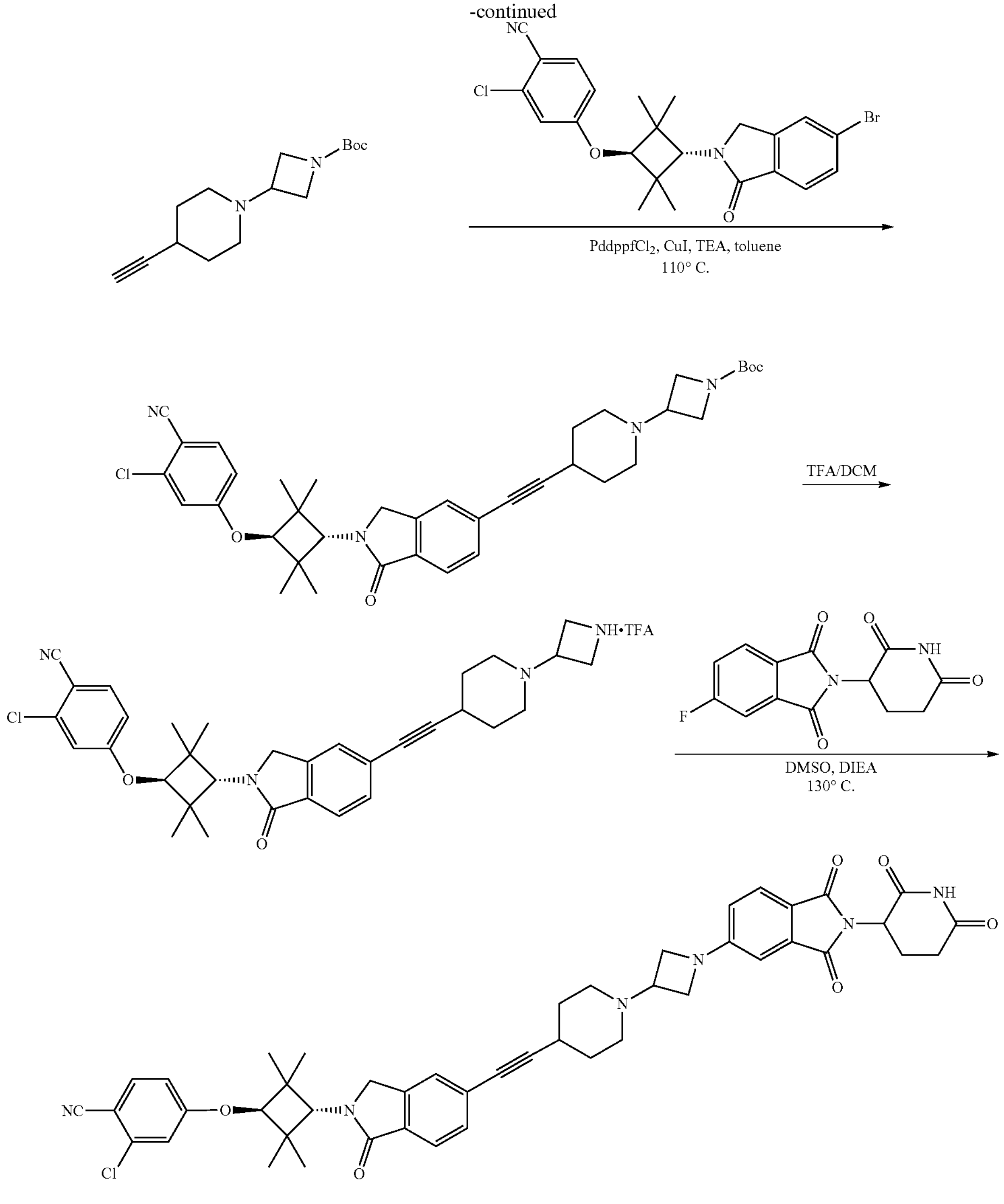
53
LC/MS ($ESI^+$) Calcd for $C_{46}H_{45}ClFN_6O_6$ ($M+H^+$) m/z, 813.3; found 813.3. $^1H$ NMR (400 MHz, $CDCl_3$) δ 8.18 (s, 1H), 7.78 (d, J=7.9 Hz, 1H), 7.65 (d, J=8.3 Hz, 1H), 7.57 (d, J=8.7 Hz, 1H), 7.54-7.45 (m, 2H), 7.00 (d, J=2.4 Hz, 1H), 6.89-6.76 (m, 2H), 6.54 (dd, J=8.3, 2.0 Hz, 1H), 4.93 (dd, J=12.3, 5.3 Hz, 1H), 4.64 (s, 2H), 4.40 (s, 1H), 4.32 (s, 1H), 4.12 (t, J=7.5 Hz, 2H), 3.94 (s, 2H), 3.42 (s, 1H), 3.01 (d, J=16.1 Hz, 1H), 2.92-2.81 (m, 2H), 2.80-2.71 (m, 4H), 2.29 (s, 2H), 2.02 (s, 2H), 1.84 (d, J=9.1 Hz, 2H), 1.45 (s, 6H), 1.26 (s, 7H).

54: 2-Chloro-4-((1S,4r)-4-(2-((3S)-3-((4-(2-(2,6-dioxopiperidin-3-yl)-6-fluoro-3-oxoisoindolin-5-yl)piperazin-1-yl)methyl)pyrrolidin-1-yl)-5-oxo-5H-pyrrolo[3,4-b]pyridin-6(7H)-yl)cyclohexyl)oxy)benzonitrile
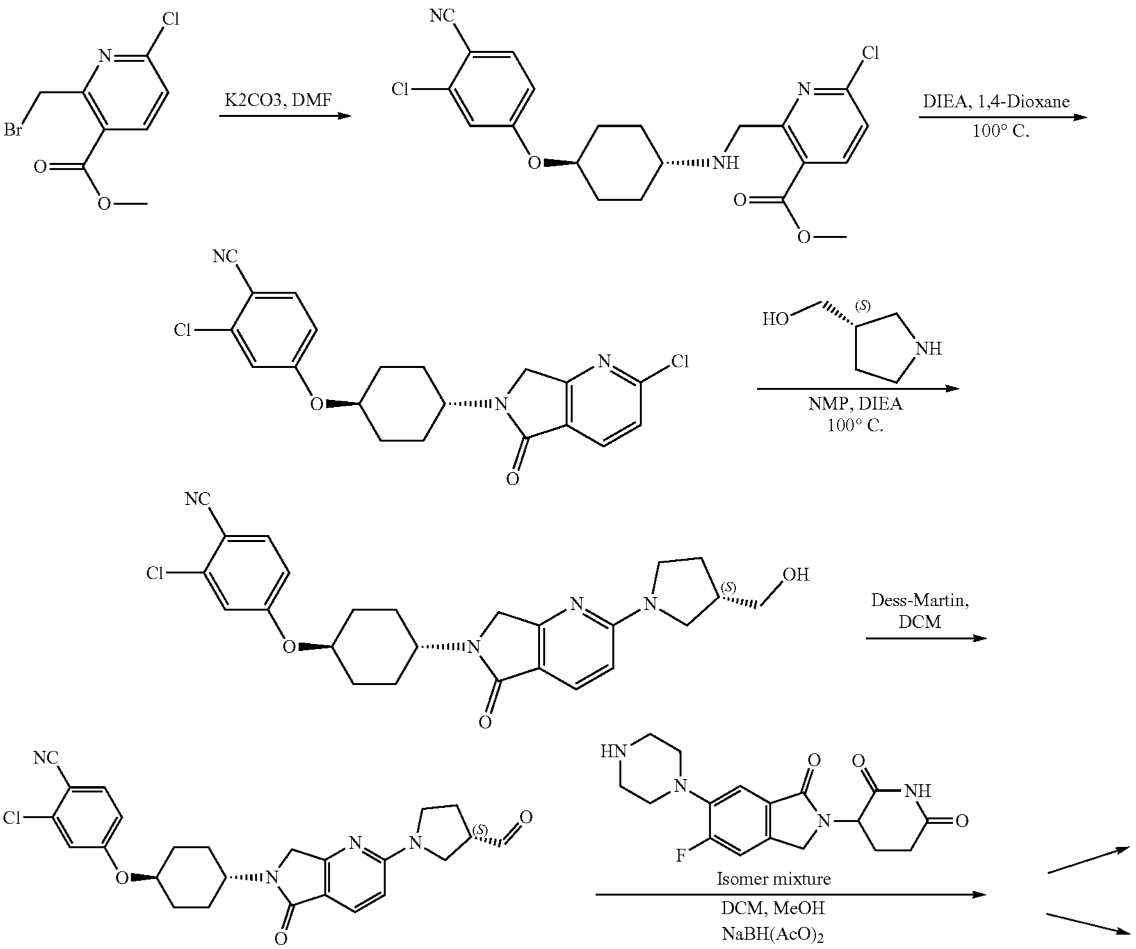
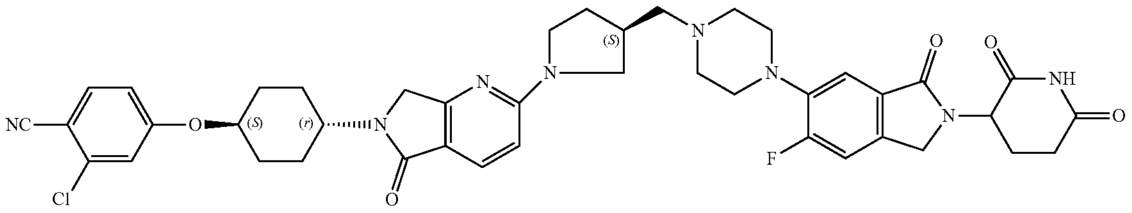
84
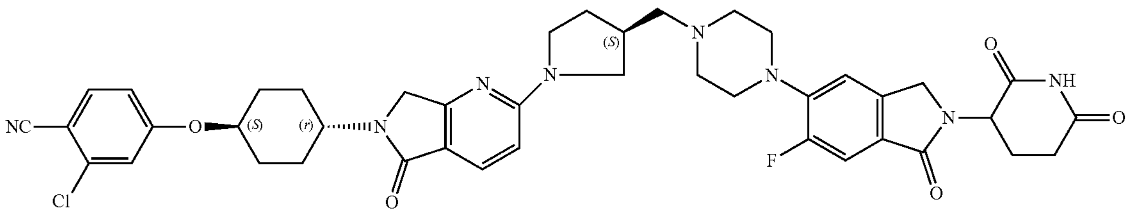
85
LC/MS (ESI$^+$) Calcd for $C_{42}H_{44}ClFN_8O_5$ (M+H$^+$) m/z, 795.3; found 795.3. $^1$H NMR (400 MHz, DMSO-$d_6$) δ 7.88 (d, J=8.7 Hz, 1H), 7.69 (d, J=8.7 Hz, 1H), 7.45 (d, J=11.5 Hz, 1H), 7.40 (d, J=2.4 Hz, 1H), 7.31 (d, J=7.8 Hz, 1H), 7.18-7.11 (m, 1H), 6.49 (d, J=8.7 Hz, 1H), 5.33 (s, 1H), 5.09 (d, J=12.9 Hz, 1H), 4.57 (s, 2H), 4.45 (s, 1H), 4.38 (d, J=17.6

Hz, 1H), 4.26 (d, J=8.8 Hz, 2H), 4.07 (s, 2H), 3.68 (s, 1H), 3.58 (s, 1H), 3.49-3.37 (m, 3H), 3.21 (s, 1H), 3.09 (s, 3H), 2.91 (s, 2H), 2.68 (s, 4H), 2.60 (d, J=17.0 Hz, 3H), 2.46-2.38 (m, 2H), 2.34 (s, 1H), 2.14 (s, 2H), 2.00 (d, J=7.5 Hz, 2H), 1.80 (s, 3H), 1.57 (s, 2H), 1.24 (s, 2H).

55: 2-Chloro-4-((1S,4r)-4-(2-((3S)-3-((4-(2-(2,6-dioxopiperidin-3-yl)-6-fluoro-1-oxoisoindolin-5-yl)piperazin-1-yl)methyl)pyrrolidin-1-yl)-5-oxo-5H-pyrrolo[3,4-b]pyridin-6(7H)-yl)cyclohexyl)oxy)benzonitrile LC/MS (ESI+) Calcd for $C_{42}H_{44}ClFN_8O_5$ (M+H+) m/z, 795.3; found 795.3. $^1$H NMR (400 MHz, DMSO-$d_6$) δ 10.99 (s, 1H), 7.88 (d, J=8.7 Hz, 1H), 7.69 (d, J=8.7 Hz, 1H), 7.45 (d, J=11.5 Hz, 1H), 7.40 (d, J=2.4 Hz, 1H), 7.31 (d, J=7.8 Hz, 1H), 7.18-7.11 (m, 1H), 6.49 (d, J=8.7 Hz, 1H), 5.33 (s, 1H), 5.09 (d, J=12.9 Hz, 1H), 4.57 (s, 2H), 4.45 (s, 1H), 4.38 (d, J=17.6 Hz, 1H), 4.26 (d, J=8.8 Hz, 2H), 4.07 (s, 2H), 3.60 (s, 1H), 3.49-3.37 (m, 3H), 3.21 (s, 1H), 3.15 (s, 2H), 2.91 (s, 2H), 2.68 (s, 4H), 2.60 (d, J=17.0 Hz, 31-1), 2.46-2.38 (m, 2H), 2.34 (s, 1H), 2.14 (s, 2H), 2.00 (d, J=7.5 Hz, 2H), 1.80 (s, 3H), 1.57 (s, 2H), 1.24 (s, 2H).

56: Synthesis of 2-chloro-4-((1r,4r)-4-(2-(4-((4-(2,6-dioxopiperidin-3-yl)-1-oxoisoindolin-5-yl)piperazin-1-yl)methyl)piperidin-1-yl)-5-oxo-5H-pyrrolo[3,4-b]pyridin-6(7H)-yl)cyclohexyl)oxy)benzonitrile

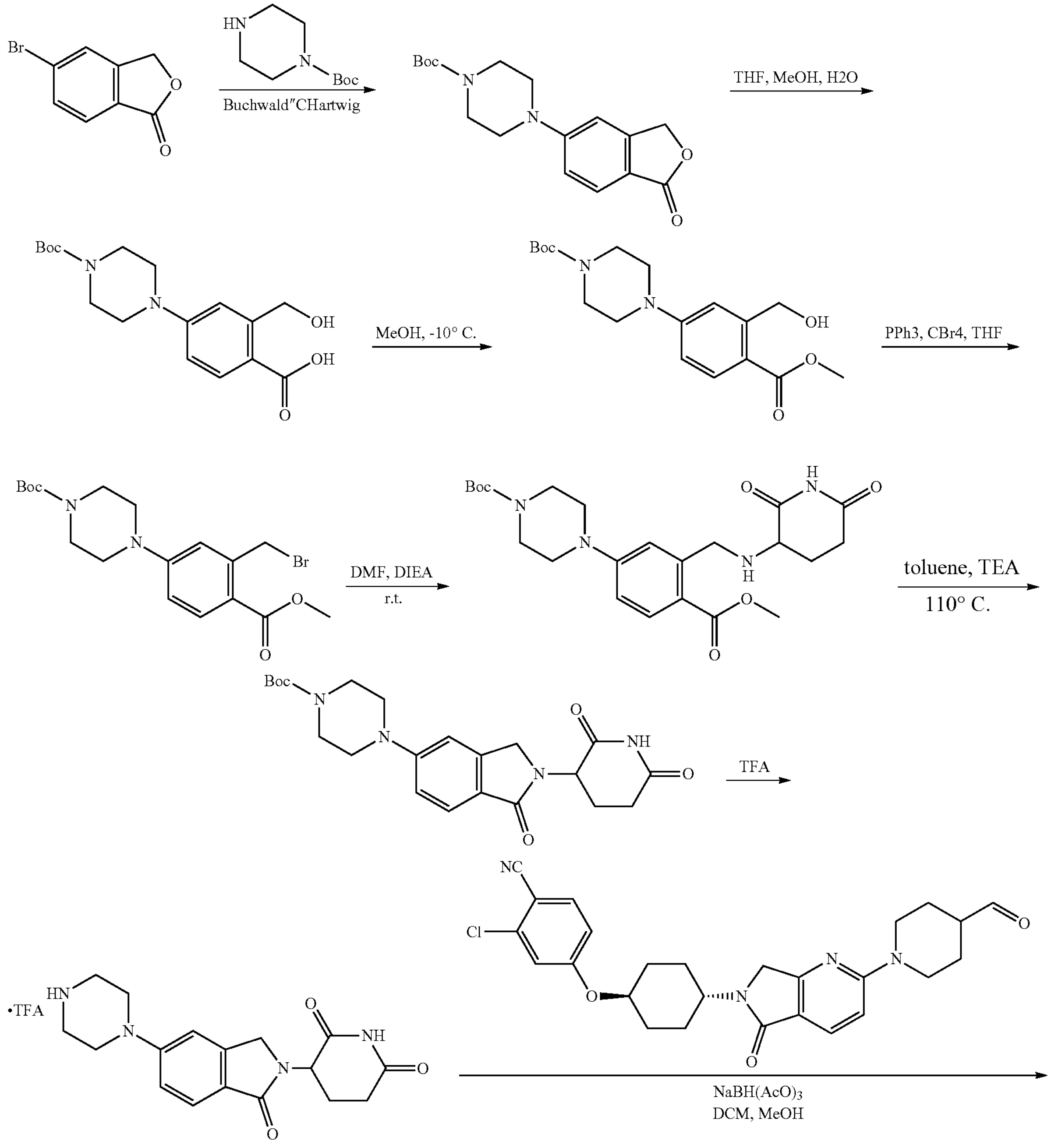

-continued
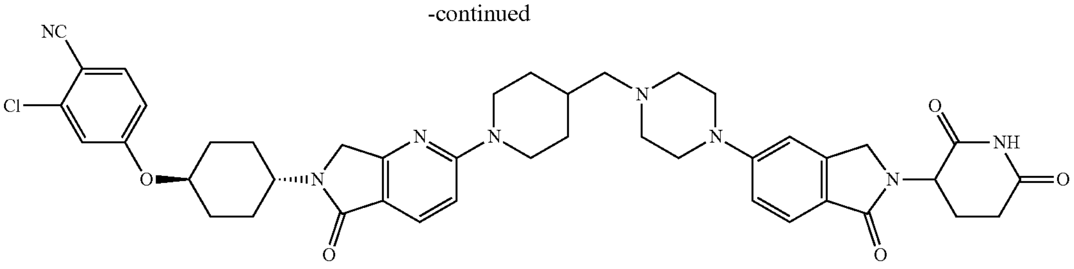
56
LC/MS (ESI$^+$) Calcd for $C_{43}H_{47}ClN_8O_5$ (M+H$^+$) m/z, 791.3, found 791.3.
57: Synthesis of 2-chloro-4-(1r,4r)-4-(2-(4-((4-(2,6-dioxopiperidin-3-yl)-1,3-dioxoisoindolin-5-yl)piperidin-1-yl)methyl)piperidin-1-yl)-5-oxo-5H-pyrrolo[3,4-b]pyridin-6(7H)-yl)cyclohexyl)oxy)benzonitrile
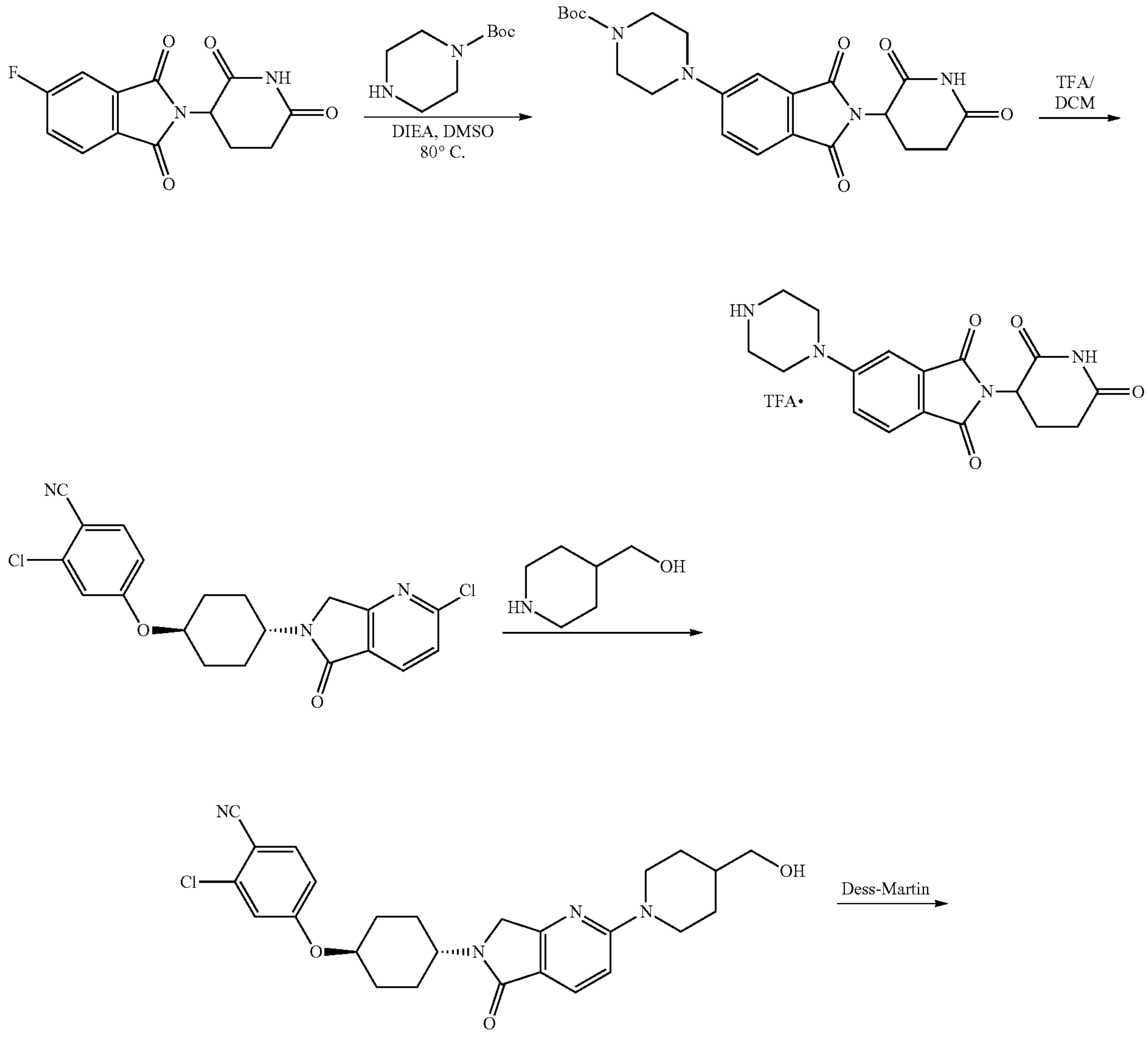

-continued
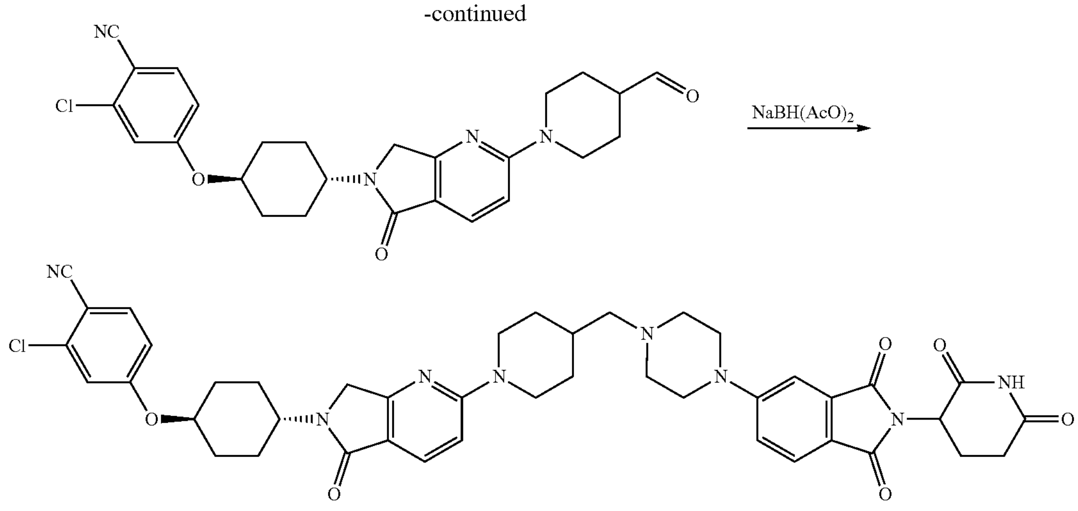
57
LC/MS (ESI+) Calcd for $C_{43}H_{45}ClN_8O_6$ (M+$H^+$) m/z, 805.3; found 805.3.
$^1$H NMR (400 MHz, $CDCl_3$) δ 8.07 (s, 1H), 7.84 (d, J=8.7 Hz, 1H), 7.74 (s, 1H), 7.58 (d, J=8.7 Hz, 1H), 7.33 (s, 1H), 7.11 (s, 1H), 7.03 (d, J=2.3 Hz, 1H), 6.88 (dd, J=8.7, 2.4 Hz, 1H), 6.68 (d, J=8.9 Hz, 1H), 4.97 (dd, J=12.0, 5.1 Hz, 1H), 4.51 (s, 2H), 4.32 (d, J=7.4 Hz, 2H), 4.22 (s, 2H), 3.91 (s, 1H), 3.75 (s, 1H), 3.56 (s, 1H), 3.46 (s, 2H), 2.97 (d, J=17.2 Hz, 4H), 2.91 (s, 1H), 2.88-2.82 (m, 1H), 2.78 (d, J=16.0 Hz, 1H), 2.61 (s, 3H), 2.26 (s, 4H), 2.16 (d, J=7.2 Hz, 2H), 1.98 (d, J=43.1 Hz, 5H), 1.72 (dd, J=16.4, 8.0 Hz, 4H).
58: Synthesis of N-((1R,4R)-4-(3-chloro-4-cyano-phenoxy)cyclohexyl)-4-(4-((4-(2-(2,6-dioxopiperidin-3-yl)-1,3-dioxoisoindolin-5-yl)-1,4-diazepan-1-yl)methyl) piperidin-1-yl)benzamide
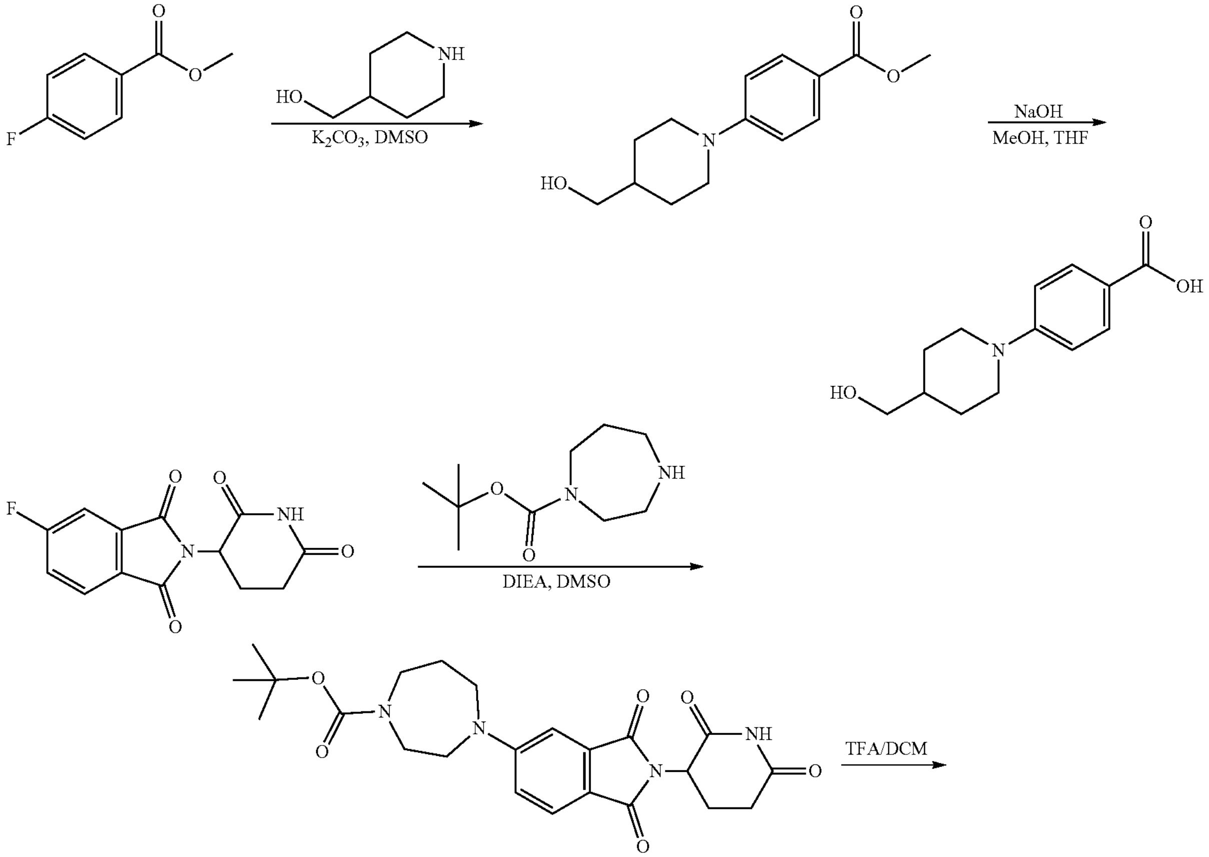

-continued

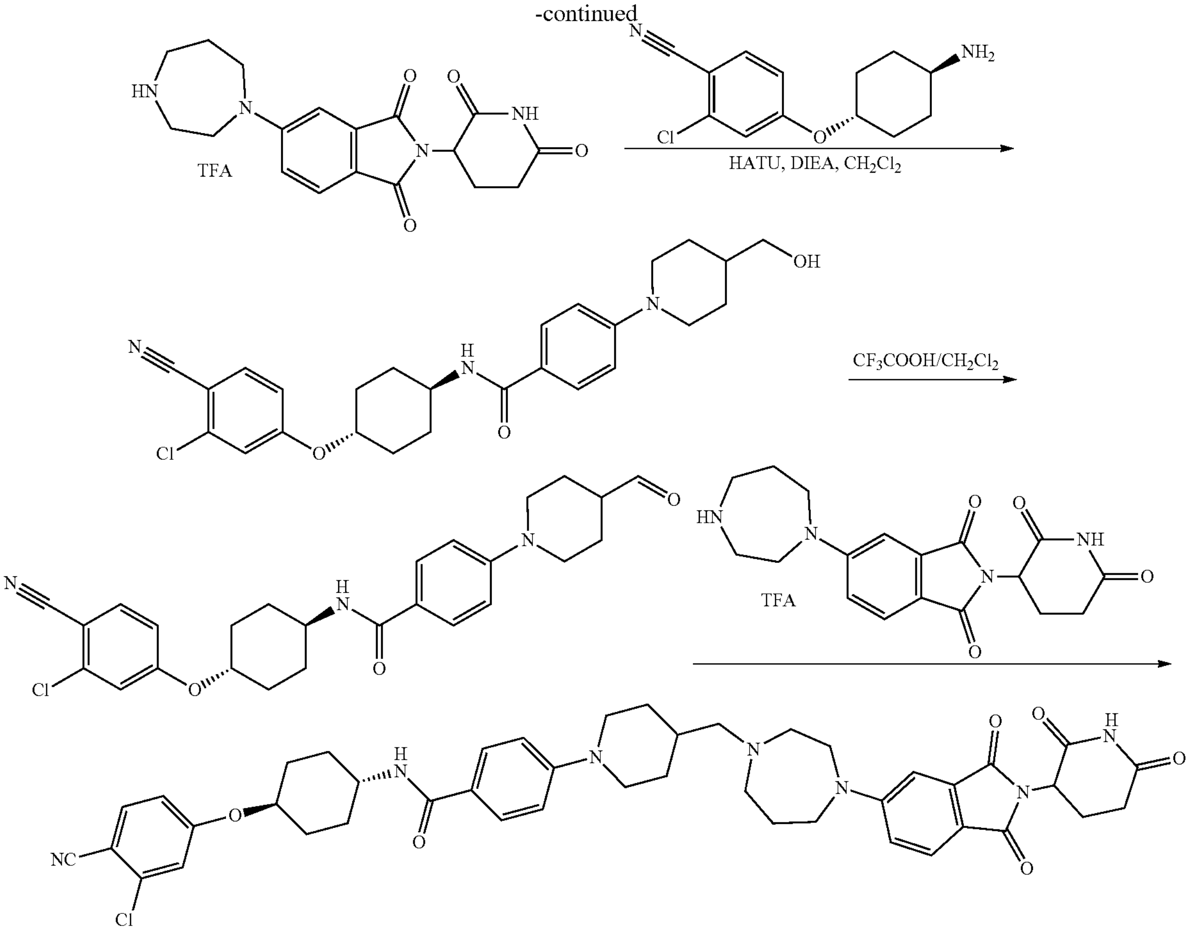

58

1. Synthesis of Compound methyl 4-(hydroxymethyl)piperidin-1-yl)benzoate

Methyl p-fluorobenzoate (1.0 g, 6.5 mmol) was dissolved in 30 mL of DMSO, to which were added 4-hydroxymethylpiperidine (2.2 g, 19.5 mmol) and potassium carbonate (2.7 g, 19.5 mmol), and the reaction solution was heated to 100° C. and reacted overnight. The next day, once TLC indicated that methyl p-fluorobenzoate had disappeared, the reaction solution was cooled to room temperature, to which were added water and ethyl acetate for extraction. The organic phase was successively washed with 0.05 M HCl solution and saturated brine, dried over anhydrous sodium sulfate, and concentrated to obtain methyl 4-(4-(hydroxymethyl)piperidin-1-yl)benzoate (1.1 g), with a yield of 68.1%. MS (ESI) m/z 249.1 $[M+H]^+$.

2. Synthesis of Compound 4-(4-(hydroxymethyl)piperidin-1-yl)benzoic acid

Methyl 4-(4-(hydroxymethyl)piperidin-1-yl)benzoate (1.0 g, 4.0 mmol) was dissolved in 8 mL MeOH/THF (1:1), to which was added 3 mL of 5 N NaOH, and the reaction solution was stirred at room temperature for 16 h. To the reaction solution, were added water and DCM to extract organic impurities, and the aqueous phase was slowly adjusted to pH4-5 with 1 N HCl. Lots of white solid was precipitated, and the solution was filtered. The filter cake was dried to obtain 4-(4-(hydroxymethyl)piperidin-1-yl) benzoic acid (510.0 mg), with a yield of 54.1%. MS (ESI) m/z 235.1 $[M+H]^+$.

3. Compound N-((1R,4R)-4-(3-chloro-4-cyanophenoxy)cyclohexyl)-4-(4-(hydroxymethyl)piperidin-1-yl)benzamide 4-((1R,4R)-4-Aminocyclohexyl)oxy)-2-chlorobenzonitrile (328.0 mg, 1.3 mmol) was dissolved in DCM, and the mixture was cooled to 0° C., to which were added HATU (475.1 mg, 1.3 mmol) and DIEA (461.4 mg, 3.6 mmol). Then, 4-(4-(hydroxymethyl)piperidin-1-yl)benzoic acid (280.0 mg, 1.2 mmol) was added, and the mixture was warmed to room temperature and reacted for 2 h. $CH_2Cl_2$ and water were added for extraction, and the organic layer was washed with brine, dried over anhydrous sodium sulfate, rotatory evaporated to dry, and purified by silica gel column chromatography, to provide compound N-((1R,4R)-4-(3-chloro-4-cyanophenoxy)cyclohexyl)-4-(4-(hydroxymethyl)piperidin-1-yl)benzamide (370.0 mg), with a yield of 66.4%.

MS (ESI) m/z 467.2 $[M+H]^+$.

4. Compound N-((1R,4R)-4-(3-chloro-4-cyanophenoxy)cyclohexyl)-4-formylpiperidin-1-yl)benzamide N-((1R,4R)-4-(3-chloro-4-cyanophenoxy)cyclohexyl)-4-(4-(hydroxymethyl) piperidin-1-yl)benzamide (370 mg, 0.8 mmol) was dissolved in the mixed solvent of 10 mL DCM and 1 mL tetrahydrofuran, to which was added Dess-Martin (373.2 mg, 0.9 mmol), and the mixture was allowed to react at room temperature for 1 h. The reaction solution was filtered through a pad of celite, and the filtrate was successively washed with the aqueous solution of sodium bisulfite and saturated brine. DCM phase was dried over anhydrous sodium sulfate, filtered, and concentrated, to provide N-((1R,4R)-4-(3-chloro-4-cyanophenoxy)cyclohexyl)-4-formylpiperidin-1-yl)benzamide (310.2 mg), with a yield of 81.4%. MS (ESI) m/z 465.2 [M+H]$^+$.

5. t-Butyl 4-(2-(2,6-dioxopiperidin-3-yl)-1,3-dioxoisoindol-5-yl)-1,4-diazacycloheptane-1-carboxylate 2-(2,6-Dioxopiperidin-3-yl)-5-fluoroisoindoline-1,3-dione (200.0 mg, 0.7 mmol) and t-butyl 1,4-diazepan-1-carboxylate (174.1 mg, 0.9 mmol) were dissolved in 6 mL of DMSO, to which was added 0.5 mL DIEA, and the mixture was allowed to react at 100° C. for 1.5 h. The reaction solution was cooled to room temperature, to which were added water and ethyl acetate for extraction. The organic phase was washed with saturated brine, dried, concentrated, and subjected to column chromatography, to obtain t-butyl 4-(2-(2,6-dioxopiperidin-3-yl)-1,3-dioxoisoindol-5-yl)-1,4-diazacycloheptane-1-carboxylate (185.3 mg), with a yield of 56.2%. MS (ESI) m/z 401.2 (M-56+H)$^+$.

6. 5-(1,4-diazepan-1-yl)-2-(2,6-dioxopiperidin-3-yl) isodihydroindole-1,3-dione trifluoroacetate t-Butyl 4-(2-(2,6-dioxopiperidin-3-yl)-1,3-dioxoisoindol-5-yl)-1,4-diazacycloheptane-1-carboxylate (185.0 mg, 0.4 mmol) was dissolved in 2 mL DCM, to which was added 6 mL TFA, and the solution was reacted 1 h. The solution was directly concentrated to dry for later use, and the product (191 mg) was 5-(1,4-diazepan-1-yl)-2-(2,6-dioxopiperidin-3-yl)isodihydroindole-1,3-dione trifluoroacetate, with a yield of 99.0%. MS (ESI) m/z 356.2 [M+H]$^+$.

7. Preparation of Compound N-((1R,4R)-4-(3-chloro-4-cyanophenoxy)cyclohexyl)-4-(4-((4-(2-(2,6-dioxopiperidin-3-yl)-1,3-dioxoisoindolin-5-yl)-1,4-diazepan-1-yl)methyl)piperidin-1-yl)benzamide 5-(1,4-Diazepan-1-yl)-2-(2,6-dioxopiperidin-3-yl)Isodihydroindole-1,3-dione trifluoroacetate (121.2 mg, 0.3 mmol) and N-((1R,4R)-4-(3-chloro-4-cyanophenoxy) cyclohexyl)-4-formylpiperidin-1-yl)benzamide (100.0 mg, 0.2 mmol) were dissolved in 8 mL of mixed solvent (DCM/MeOH=5/1), to which was added sodium triacetoxyborohydride (170.0 mg, 0.8 mmol). The mixture was allowed to react 4 h at room temperature, and the reaction was quenched by adding water. The reaction solution was extracted with DCM, and the organic phase was dried, concentrated, and subjected to column chromatography, to provide N-((1R,4R)-4-(3-chloro-4-cyanophenoxy)cyclohexyl)-4-(4-((4-(2-(2,6-dioxopiperidin-3-yl)-1,3-dioxoisoindolin-5-yl)-1,4-diazepan-1-yl)methyl)piperidin-1-yl) benzamide (101.5 mg), with a yield of 58.8%. MS (ESI) m/z 805.3 [M+H]$^+$. $^1$H NMR (400 MHz, CDCl3) δ 8.20 (s, 1H), 7.67 (dd, J=8.6, 3.4 Hz, 3H), 7.57 (d, J=8.7 Hz, 1H), 7.12 (d, J=2.1 Hz, 1H), 7.01 (d, J=2.3 Hz, 1H), 6.94-6.83 (m, 4H), 5.91 (d, J=7.8 Hz, 1H), 4.96 (dd, J=12.2, 5.3 Hz, 1H), 4.29 (dd, J=12.2, 8.4 Hz, 1H), 4.05 (dd, J=11.0, 7.3 Hz, 1H), 3.82 (d, J=12.7 Hz, 2H), 3.64 (t, J=6.0 Hz, 4H), 2.97-2.73 (m, 7H), 2.65 (s, 2H), 2.38 (s, 2H), 2.18 (dd, J=28.4, 13.7 Hz, 6H), 1.99 (s, 2H), 1.83 (s, 2H), 1.69 (s, 4H), 1.46-1.37 (m, 2H).

59: Synthesis of 2-chloro-4-(((1r,4r)-4-(2-(4-((1-(2-(2,6-dioxopiperidin-3-yl)-1,3-dioxoisoindolin-4-yl) piperidine-4-yl)oxy)piperidin-1-yl)-5-oxo-5H-pyrrolo[3,4-b]pyridin-6(7H)-yl)cyclohexyl)oxy) benzonitrile

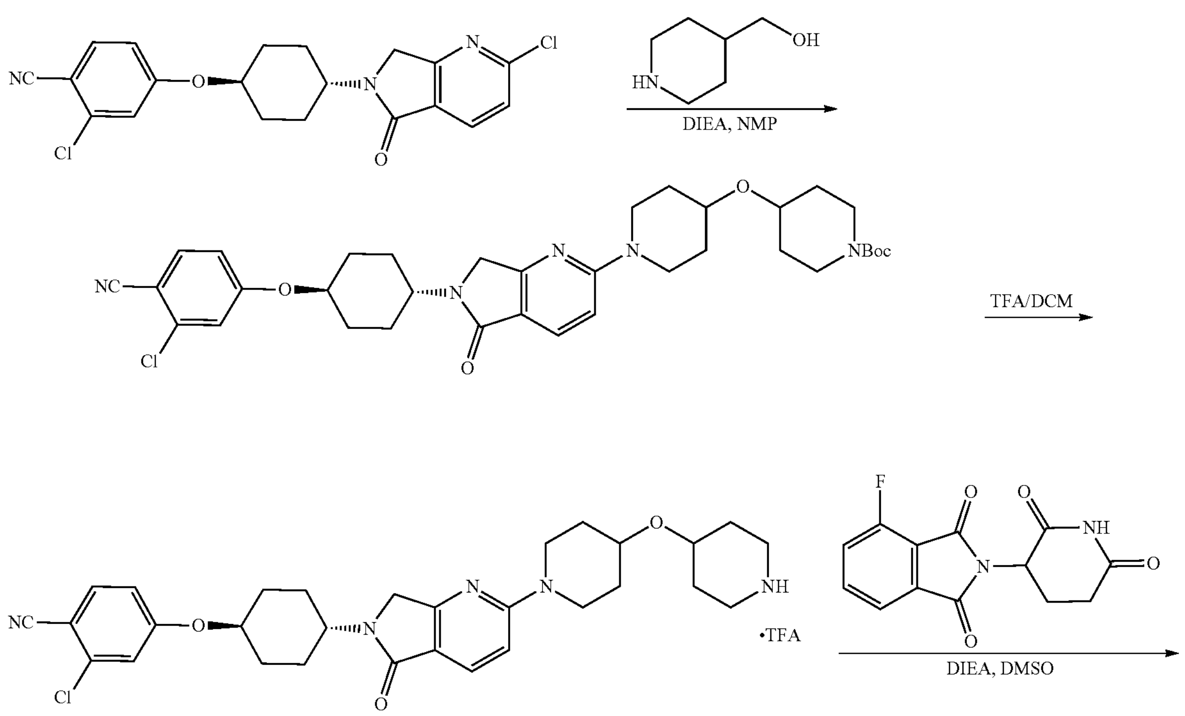

-continued
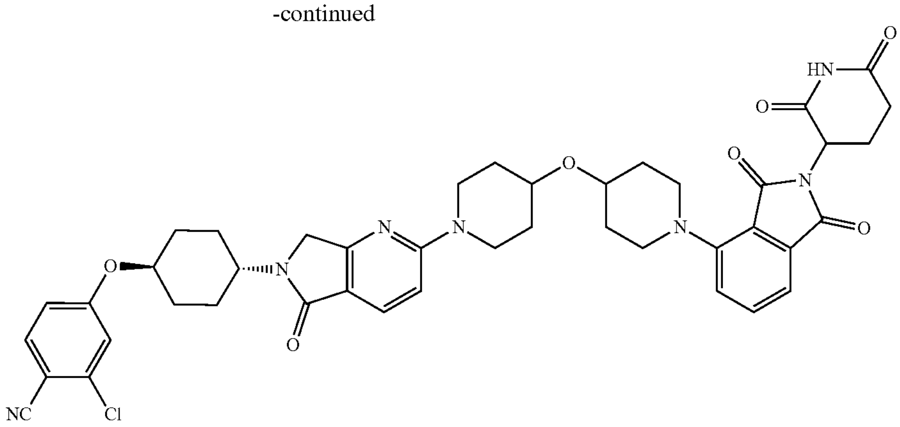
59
LC/MS (ESI+) Calcd for $C_{43}H_{44}ClN_7O_7$ (M+H) m, 806.3; found 806.3.
$^{1}$H NMR (400 MHz, $CDCl_3$) δ 8.08 (s, 1H), 7.84 (d, J=8.8 Hz, 1H), 7.59 (t, J=8.1 Hz, 2H), 7.40 (d, J=7.0 Hz, 1H), 7.20 (d, J=8.4 Hz, 1H), 7.03 (d, J=2.3 Hz, 1H), 6.88 (dd, J=8.8, 2.3 Hz, 1H), 6.70 (d, J=8.8 Hz, 1H), 4.99 (dd, J=12.1, 5.3 Hz, 1H), 4.31 (s, 2H), 4.22 (s, 2H), 4.07 (d, J=15.7 Hz, 2H), 3.76 (s, 2H), 3.66-3.56 (m, 2H), 3.52-3.42 (m, 2H), 3.20 (d, J=8.3 Hz, 2H), 2.94-2.71 (m, 3H), 2.26 (s, 2H), 2.14 (d, J=7.8 Hz, 1H), 2.04 (s, 4H), 1.94 (s, 2H), 1.88 (s, 2H), 1.71 (d, J=8.4 Hz, 5H).
60: Synthesis of 2-chloro-4-(((1r,4r)-4-(2-(4-((1-(2-(2,6-dioxopiperidin-3-yl)-1,3-dioxoisoindolin-5-yl)piperidine-4-yl)oxy)piperidin-1-yl)-5-oxo-5H-pyrrolo[3,4-b]pyridin-6(7H)-yl)cyclohexyl)oxy)benzonitrile
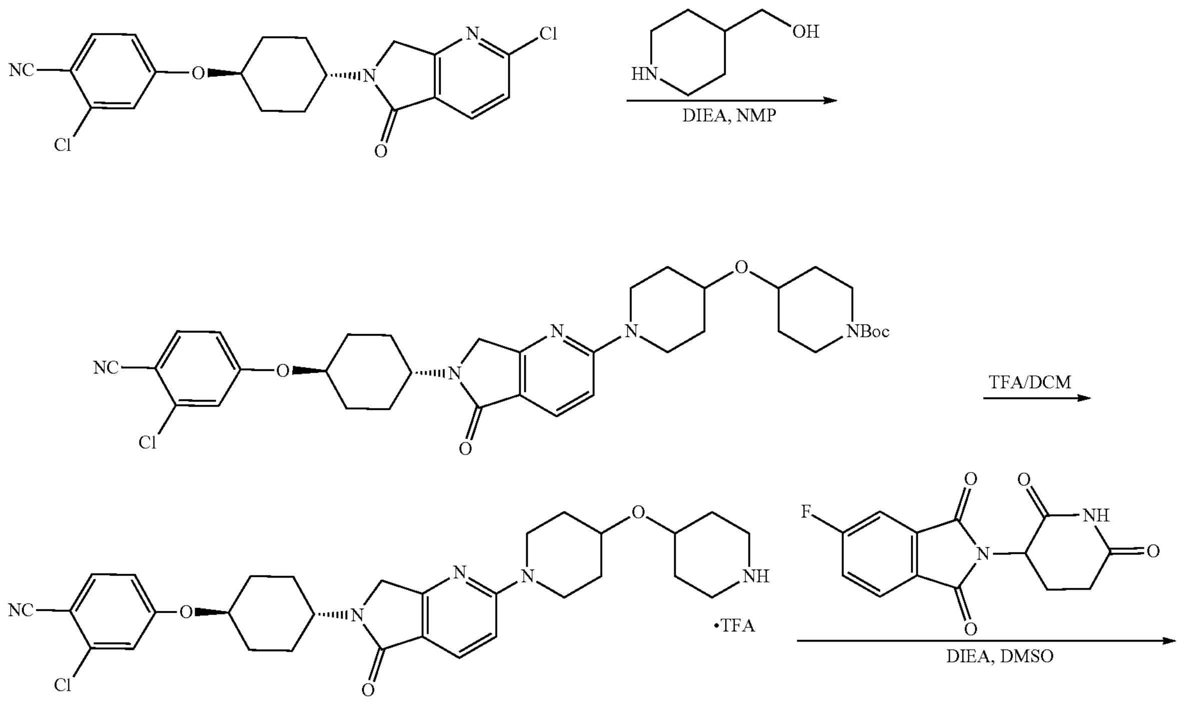

-continued

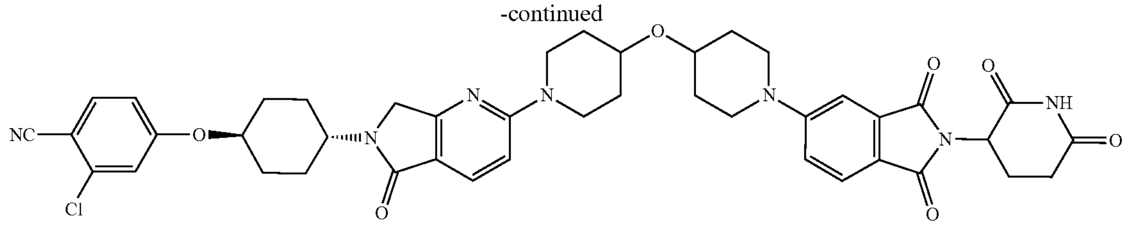

60

1. t-Butyl 4-((1-(6-((1r,4r)-4-(3-Chloro-4-cyanophenoxy)cyclohexyl)-5-oxo-6,7-dihydro-5H-pyrrolo[3,41-b](pyridin-2-yl)piperidine-4-yl)oxy)piperidine-1-formate 2-Chloro-4-(((1R,4R)-4-(2-chloro-5-oxo-5H-pyrrolo[3,4-b]pyridin-6(7H)-yl) cyclohexyl)oxy)benzonitrile (100.0 mg, 0.3 mmol) and t-butyl 4-(piperidin-4-yloxy)piperidine-1-carboxylate (212.1 mg, 0.8 mmol) were dissolved in 3 mL NMP, to which was added 0.5 mL DIEA, and then the reaction solution was heated to 100° C. and reacted overnight. The solution was cooled to room temperature, to which were added water and EA for extraction. The organic phase was further washed with water, 0.5 M HCl aqueous solution, and saturated brine, followed by drying with anhydrous sodium sulfate and concentrating, to provide t-butyl 4-((1-(6-((1r,4r)-4-(3-chloro-4-cyanophenoxy)cyclohexyl)-5-oxo-6,7-dihydro-5H-pyrrolo[3,4-b](pyridin-2-yl) piperidine-4-yl)oxy)piperidine-1-formate (142.1 mg), with a yield of 88.2%. MS (ESI) m-z 594.3 $(M-56+H)^+$.

2. 2-chloro-4-(((1R,4R)-4-(5-oxo-2-(4-(piperidin-4-yloxy)piperidin-1-yl)-5,7-dihydro-6H-pyrrolo[3,4-b]pyridin-6-yl)cyclohexyl)oxy)benzonitrile trifluoroacetate Compound t-butyl 4-((1-(6-((1r,4r)-4-(3-chloro-4-cyanophenoxy)cyclohexyl)-5-oxo-6,7-dihydro-5H-pyrrolo[3,4-b](pyridin-2-yl)piperidine-4-yl)oxy)piperidine-1-formate (140.0 mg, 0.2 mmol) was dissolved in 1 mL DCM, to which was added 3 mL TFA, and the reaction was stirred 1 h. TLC detection indicated the completion of the reaction. The reaction solution was directly concentrated under reduced pressure until viscous, and then repeatedly evaporated with DCM to form a solid, to provide 2-chloro-4-(((1R,4R)-4-(5-oxo-2-(4-(piperidin-4-yloxy)piperidin-1-yl)-5,7-dihydro-6H-pyrrolo[3,4-b]pyridin-6-yl) cyclohexyl)oxy)benzonitrile trifluoroacetate (142.1 mg), with a yield of 99.2%. MS (ESI) m/z 549.1 $[M+H]^+$.

3. 2-Chloro-4-(((1r,4r)-4-(2-(4-((1-(2-(2,6-dioxopiperidin-3-yl)-1,3-dioxoisoindolin-5-yl)piperidine-4-yl)oxy)piperidin-1-yl)-5-oxo-5,7-dihydro-6H-pyrrolo[3,4-b]pyridin-6-yl)cyclohexyl)oxy)benzonitrile Intermediate 2-chloro-4-(((1R,4R)-4-(5-oxo-2-(4-(piperidin-4-yloxy)piperidin-1-yl)-5,7-dihydro-6H-pyrrolo[3,4-b]pyridin-6-yl)cyclohexyl)oxy)benzonitrile trifluoroacetate (100.0 mg, 0.2 mmol) was dissolved in 2 mL DMSO, to which was added DIEA (97.3 mg, 0.8 mmol), and after stirred well, 2-(2,6-dioxopiperidin-3-yl)-5-fluoroisoindoline-1,3-dione (49.9 mg, 0.2 mmol) was added. The reaction solution was heated to 120° C. and reacted 2 h. TLC detection indicated the completion of the reaction. After the reaction solution was cooled to room temperature, water and ethyl acetate were added for extraction. The organic phase was washed with 0.5 M HCl aqueous solution and saturated brine, dried over anhydrous sodium sulfate, concentrated, and subjected to column chromatography, to provide 2-chloro-4-(((1r,4r)-4-(2-(4-((1-(2-(2,6-dioxopiperidin-3-yl)-1,3-dioxoisoindolin-5-yl)piperidine-4-yl)oxy)piperidin-1-yl)-5-oxo-5,7-dihydro-6H-pyrrolo[3,4-b]pyridin-6-yl)cyclohexyl)oxy)benzonitrile (61.2 mg), with a yield of 41.6%. MS (ESI) m/z 805.3 $[M+H]^+$. $^1H$ NMR (400 MHz, $CDCl_3$) δ 8.11 (s, 1H), 7.84 (d, J=8.8 Hz, 1H), 7.70 (d, J=8.5 Hz, 1H), 7.58 (d, J=8.7 Hz, 1H), 7.31 (d, J=2.1 Hz, 1H), 7.08 (dd, J=8.6, 2.1 Hz, 1H), 7.03 (d, J=2.3 Hz, 1H), 6.88 (dd, J=8.7, 2.2 Hz, 1H), 6.70 (d, J=8.9 Hz, 1H), 4.96 (dd, J=12.1, 5.2 Hz, 1H), 4.32 (d, J=8.0 Hz, 2H), 4.22 (s, 2H), 4.12-4.02 (m, 2H), 3.86-3.68 (m, 4H), 3.52-3.40 (m, 2H), 3.37-3.28 (m, 2H), 2.96-2.71 (m, 3H), 2.26 (s, 2H), 2.20-2.10 (m, 1H), 2.06-1.89 (m, 6H), 1.72 (d, J=8.3 Hz, 8H).

61: Synthesis of N-((1R,4R)-4-(3-chloro-4-cyanophenoxy)cyclohexyl)-6-(4-(7-(2-(2,6-dioxopiperidin-3-yl)-6-fluoro-1,3-dioxoisoindolin-5-yl)-2,7-diazaspiro[3.5]nonyl-2-yl)piperidin-1-yl)pyridazine-3-carboxamide

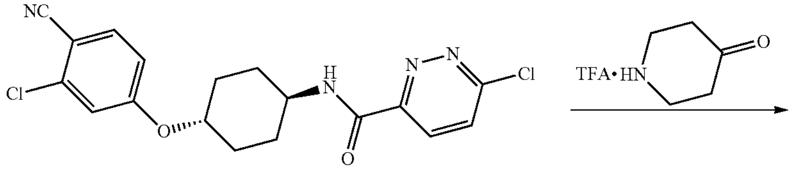

-continued

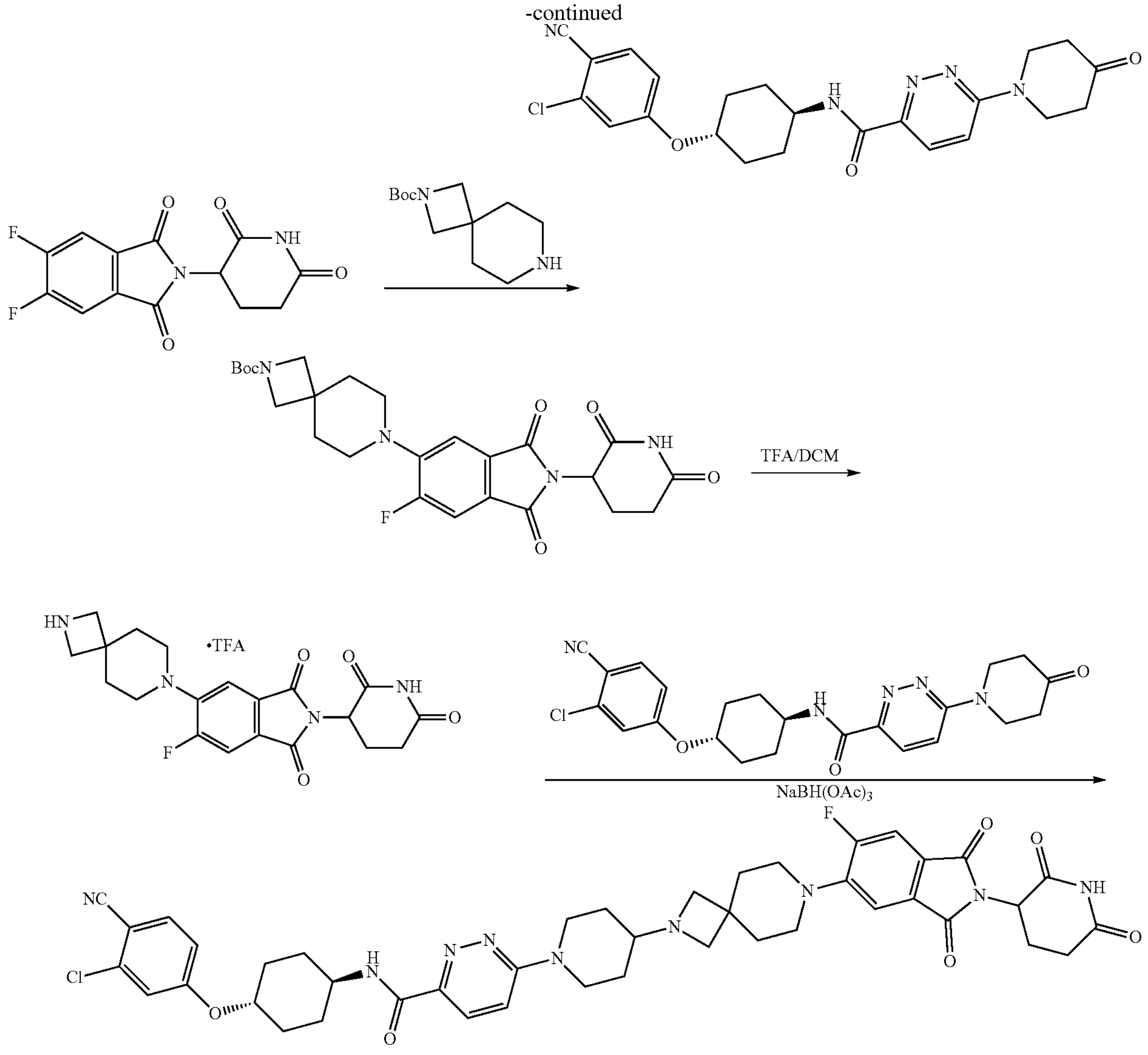

61

1. Synthesis of Compound N-((1R,4R)-4-(3-chloro-4-cyanophenoxy)cyclohexyl)-6-(4-oxopiperidin-1-yl)pyridazine-3-formamide 6-Chloro-N-((1R,4R)-4-(3-chloro-4-cyanophenoxy)cyclohexyl)pyridazine-3-formamide (200.0 mg, 0.51 mmol) and 4-piperidone trifluoroacetate (217.9 mg, 1.02 mmol) were dissolved in 5 mL NMP, to which was added 0.5 mL DIEA, and then the reaction solution was heated to 100° C. and reacted overnight. The reaction solution was cooled to room temperature, to which were added water and EA for extraction, and then the organic phase was further washed with water, saturated citric acid aqueous solution, and saturated brine. Then, the organic phase was dried with anhydrous sodium sulfate, concentrated, and purified by column chromatography, to provide N-((1R,4R)-4-(3-chloro-4-cyanophenoxy)cyclohexyl)-6-(4-oxopiperidin-1-yl)pyridazine-3-formamide (120.1 mg), with a yield of 51.7%. MS (ESI) m-z 453.9 [M+H]$^+$.

2. t-Butyl 7-(2-(2-(2,6-dioxopiperidin-3-yl)-6-fluoro-1,3-dioxoisoindolin-5-yl)-2,7-diazaspiro[3.5]nonane-2-carboxylate 2-(2,6-Dioxapiperidin-3-yl)-5,6-difluoroisoindoline-1,3-dione (500 mg, 1.7 mmol) and 2-t-butoxycarbonyl-2,7-diazaspiro[3.5]nonane (461.54 mg, 2.04 mmol) were dissolved in 8 mL DMSO, to which was added 0.5 mL DIEA, and the reaction solution was heated to 130° C. and reacted 2 h. TLC detection indicated the completion of the reaction. The reaction solution was cooled to room temperature, to which were added 10 mL water and 10 mL ethyl acetate for extraction. The organic phase was washed with saturated citric acid aqueous solution and saturated brine. Then, the organic phase was dried with anhydrous sodium sulfate, concentrated, and purified by column chromatography, to provide t-butyl 7-(2-(2-(2,6-dioxopiperidin-3-yl)-6-fluoro-1,3-dioxoisoindolin-5-yl)-2,7-diazaspiro[3.5]nonane-2-carboxylate (750.6 mg), with a yield of 88.2%. MS (ESI) m/z 445.2 (M-56+H)$^+$.

3. 2-(2,6-Dioxapiperidin-3-yl)-5-fluoro-6-(2,7-diazaspiro[3.5]nonan-7-yl)isoindoline-1,3-dione trifluoroacetate t-Butyl 7-(2-(2-(2,6-dioxopiperidin-3-yl)-6-fluoro-1,3-dioxoisoindolin-5-yl)-2,7-diazaspiro[3.5]nonane-2-carboxylate (750 mg, 1.51 mmol) was dissolved in the mixed solvent of 4 mL DCM and 8 mL trifluoroacetic acid, and the reaction solution was stirred 1 h at room temperature. The reaction solution was directly concentrated in vacuo, and then repeatedly evaporated with DCM until the system became yellow solid, followed by weighing, to provide 2-(2,6-dioxapiperidin-3-yl)-5-fluoro-6-(2,7-diazaspiro[3.5]nonan-7-yl)isoindoline-1,3-dione trifluoroacetate (822.6 mg), with a yield of 99.5%. MS (ESI) m/z 400.1 $[M+H]^+$.

4. Compound N-((1R,4R)-4-(3-chloro-4-cyanophenoxy)cyclohexyl)-6-(4-(7-(2-(2,6-dioxopiperidin-3-yl)-6-fluoro-1,3-dioxoisoindolin-5-yl)-2,7-diazaspiro[3.5]nonyl-2-yl)piperidin-1-yl)pyridazine-3-carboxamide Compounds N-((1R,4R)-4-(3-chloro-4-cyanophenoxy)cyclohexyl)-6-(4-oxopiperidin-1-yl)pyridazine-3-formamide (50.0 mg, 0.11 mmol) and 2-(2,6-dioxapiperidin-3-yl)-5-fluoro-6-(2,7-diazaspiro[3.5]nonan-7-yl)isoindoline-1,3-dione trifluoroacetate (62.3 mg, 0.12 mmol) in the mixed solvent of 2 mL dichloromethane and 1 mL methanol, to which was added sodium triacetoxyborohydride (93.4 mg, 0.44 mmol). The mixture was allowed to react overnight at room temperature, and the reaction was quenched by adding water. The reaction solution was extracted with DCM, and the organic phase was washed with saturated brine, dried, filtered, concentrated, and purified, to provide N-((1R,4R)-4-(3-chloro-4-cyanophenoxy)cyclohexyl)-6-(4-(7-(2-(2,6-dioxopiperidin-3-yl)-6-fluoro-1,3-dioxoisoindolin-5-yl)-2,7-diazaspiro[3.5]nonyl-2-yl)piperidin-1-yl) pyridazine-3-carboxamide (23.3 mg). MS (ESI) m-z 837.3 $[M+H]^+$. $^1$H NMR (400 MHz, DMSO-$d_6$) δ 11.11 (s, 1H), 8.60 (d, J=8.1 Hz, 1H), 7.85 (d, J=8.8 Hz, 1H), 7.80 (d, J=9.5 Hz, 1H), 7.71 (d, J=11.4 Hz, 1H), 7.44 (d, J=7.4 Hz, 1H), 7.39 (d, J=2.3 Hz, 1H), 7.34 (d, J=9.6 Hz, 1H), 7.13 (dd, J=8.8, 2.4 Hz, 1H), 5.10 (dd, J=12.8, 5.4 Hz, 1H), 4.53 (s, 1H), 4.21 (d, J=13.0 Hz, 2H), 3.85 (d, J=8.3 Hz, 1H), 3.24 (s, 1H), 3.17 (s, 4H), 2.99 (s, 4H), 2.91-2.80 (m, 1H), 2.59 (d, J=18.4 Hz, 1H), 2.35 (d, J=18.7 Hz, 2H), 2.10 (d, J=10.0 Hz, 2H), 2.03 (s, 1H), 1.89 (d, J=10.2 Hz, 2H), 1.81 (s, 4H), 1.73 (d, J=11.0 Hz, 2H), 1.64 (d, J=12.8 Hz, 2H), 1.51 (d, J=12.3 Hz, 2H), 1.28-1.11 (m, 3H).

62: Synthesis of N-((1r,4r)-4-(3-chloro-4-cyanophenoxy)cyclohexyl)-6-(4-(5-(2-(2,6-dioxopiperidin-3-yl)-1,3-dioxoisoindolin-5-yl)hexahydropyrrolo[3,4-c]pyrrol-2(1H)-yl)piperidin-1-yl)pyridazine-3-carboxamide

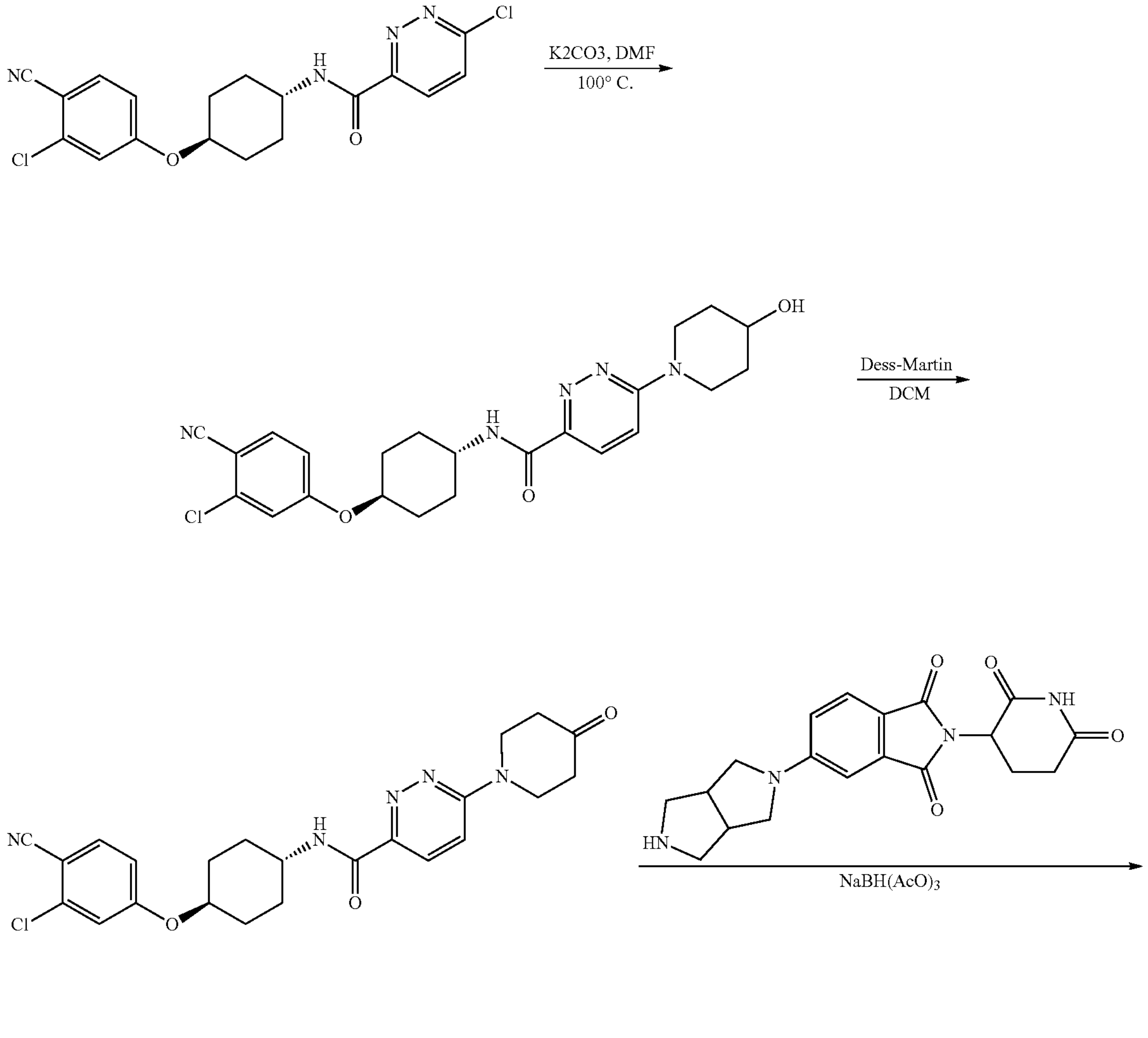

-continued
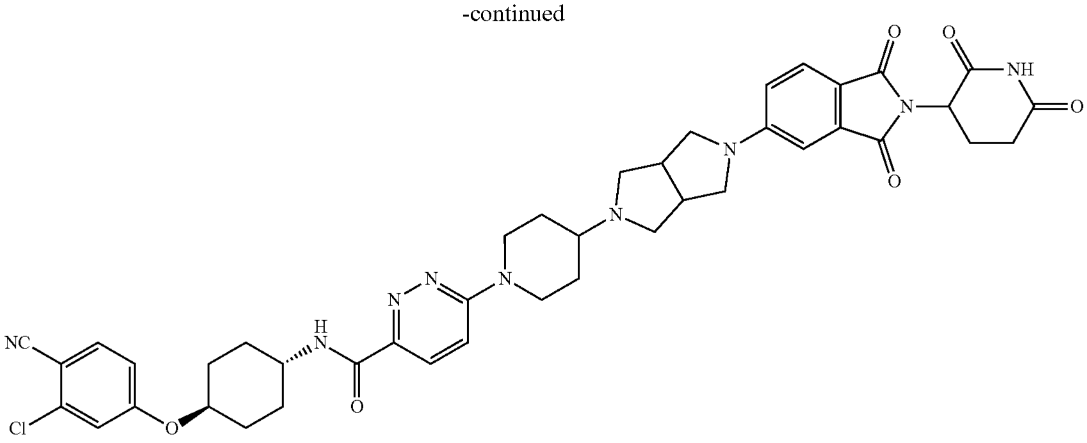
62
LC/MS (ESI$^+$) Calcd for $C_{42}H_{44}ClN_9O_6(M+H^+)$ m/z, 806.3; found 806.3.
$^1$H NMR (400 MHz, $CDCl_3$) δ 8.16 (s, 1H), 8.00 (d, J=9.5 Hz, 1H), 7.86 (d, J=8.1 Hz, 1H), 7.68 (d, J=8.3 Hz, 1H), 7.56 (d, J=8.7 Hz, 1H), 7.00 (d, J=2.2 Hz, 3H), 6.85 (dd, J=8.8, 2.2 Hz, 1H), 6.76 (d, J=7.1 Hz, 1H), 4.94 (dd, J=12.1, 5.3 Hz, 1H), 4.52 (s, 2H), 4.31 (s, 2H), 4.02 (s, 2H), 3.59 (s, 2H), 3.51 (s, 2H), 3.40 (s, 2H), 3.02 (s, 3H), 2.93-2.66 (m, 6H), 2.17 (d, J=4.1 Hz, 6H), 2.02 (d, J=14.6 Hz, 2H), 1.54-1.42 (m, 4H).
63: Synthesis of N-((1r,4r)-4-(3-chloro-4-cyanophenoxy)cyclohexyl)-5-(4-(5-(2-(2,6-dioxopiperidin-3-yl)-1,3-dioxoisoindolin-5-yl)hexahydropyrrolo[3,4-c]pyrrol-2(1H)-yl)piperidin-1-yl)pyrazine-2-carboxamide
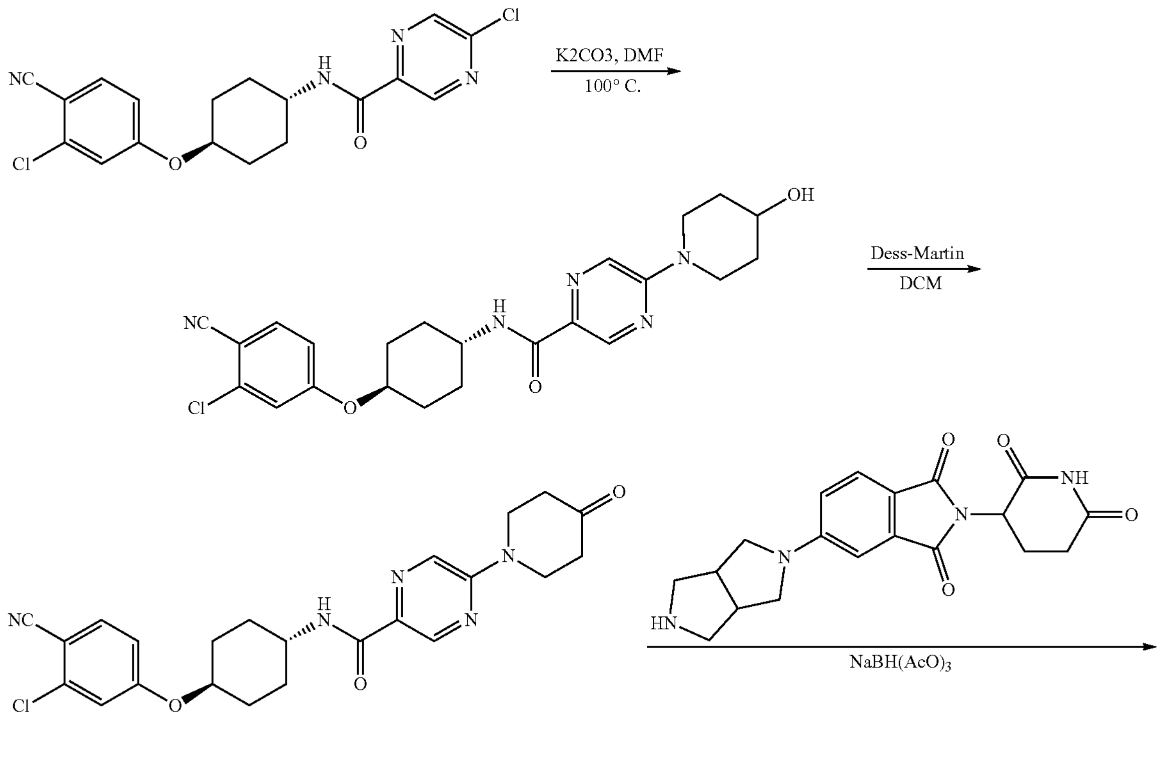

-continued
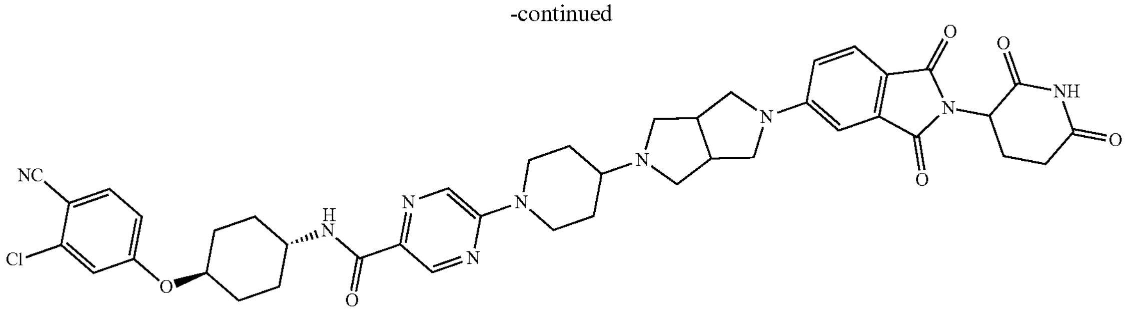
63
LC/MS (ESI$^+$) Calcd for $C_{42}H_{44}ClN_9O_6$(M+H$^+$) m/z, 806.3; found 806.3.
$^1$H NMR (400 MHz, $CDCl_3$) δ 8.83 (s, 1H), 8.19 (s, 1H), 7.98 (s, 1H), 7.70 (d, J=8.3 Hz, 1H), 7.56 (d, J=8.7 Hz, 1H), 7.40 (d, J=8.1 Hz, 1H), 7.05-6.97 (m, 2H), 6.85 (dd, J=8.8, 2.3 Hz, 1H), 6.78 (d, J=7.4 Hz, 1H), 4.94 (dd, J=12.1, 5.3 Hz, 1H), 4.52 (s, 2H), 4.31 (s, 2H), 4.02 (s, 2H), 3.59 (s, 2H), 3.51 (s, 2H), 3.40 (s, 2H), 3.02 (s, 3H), 2.93-2.66 (m, 6H), 2.17 (d, J=4.1 Hz, 6H), 2.02 (d, J=14.6 Hz, 2H), 1.53-1.41 (m, 4H).
64: Synthesis of N-((1r,4r)-4-(3-chloro-4-cyanophenoxy)cyclohexyl)-5-(4-(5-(2-(2,6-dioxopiperidin-3-yl)-6-fluoro-1,3-dioxoisoindolin-5-yl)hexahydropyrrolo[3,4-c]pyrrol-2(1H)-yl)piperidin-1-yl)pyrazine-2-carboxamide
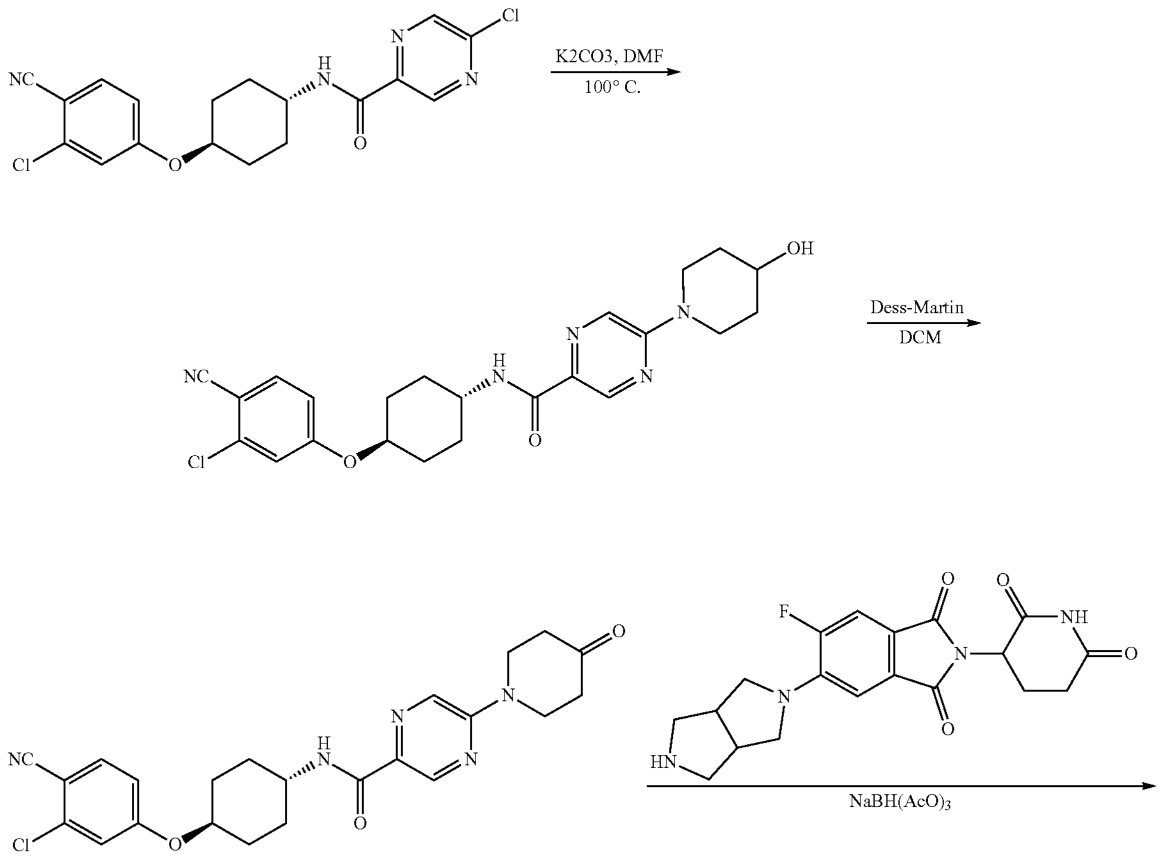

-continued
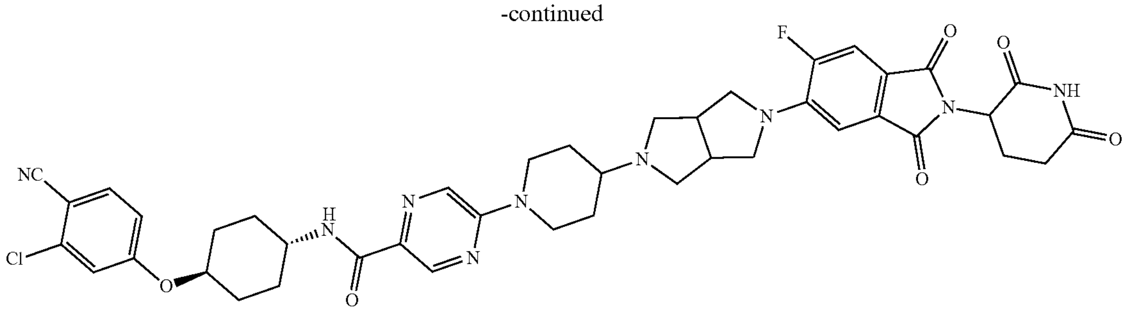
64
LC/MS (ESI+) Calcd for $C_{42}H_{43}ClFN_9O_6(M+H^+)$ m/z, 826.3; found 826.3.
$^1H$ NMR (400 MHz, $CDCl_3$) δ 8.80 (s, 1H), 8.21 (d, J=9.5 Hz, 1H), 7.86 (d, J=8.2 Hz, 1H), 7.56 (d, J=8.7 Hz, 1H), 7.17 (d, J=6.7 Hz, 1H), 7.00 (dd, J=5.9, 3.6 Hz, 2H), 6.85 (dd, J=8.7, 2.4 Hz, 1H), 4.92 (dd, J=12.3, 5.3 Hz, 1H), 4.49 (s, 2H), 4.32 (t, J=10.1 Hz, 2H), 4.05 (d, J=8.2 Hz, 2H), 3.53 (s, 4H), 3.12 (s, 4H), 2.91-2.66 (m, 6H), 2.20-2.10 (m, 7H), 1.51-1.35 (m, 4H).
65: Synthesis of N-((1r,4r)-4-(3-chloro-4-cyanophenoxy)cyclohexyl)-6-(4-(5-(2-(2,6-dioxopiperidin-3-yl)-6-fluoro-1,3-dioxoisoindolin-5-yl)hexahydropyrrolo[3,4-c]pyrrol-2(1H)-yl)piperidin-1-yl) pyridazine-3-carboxamide
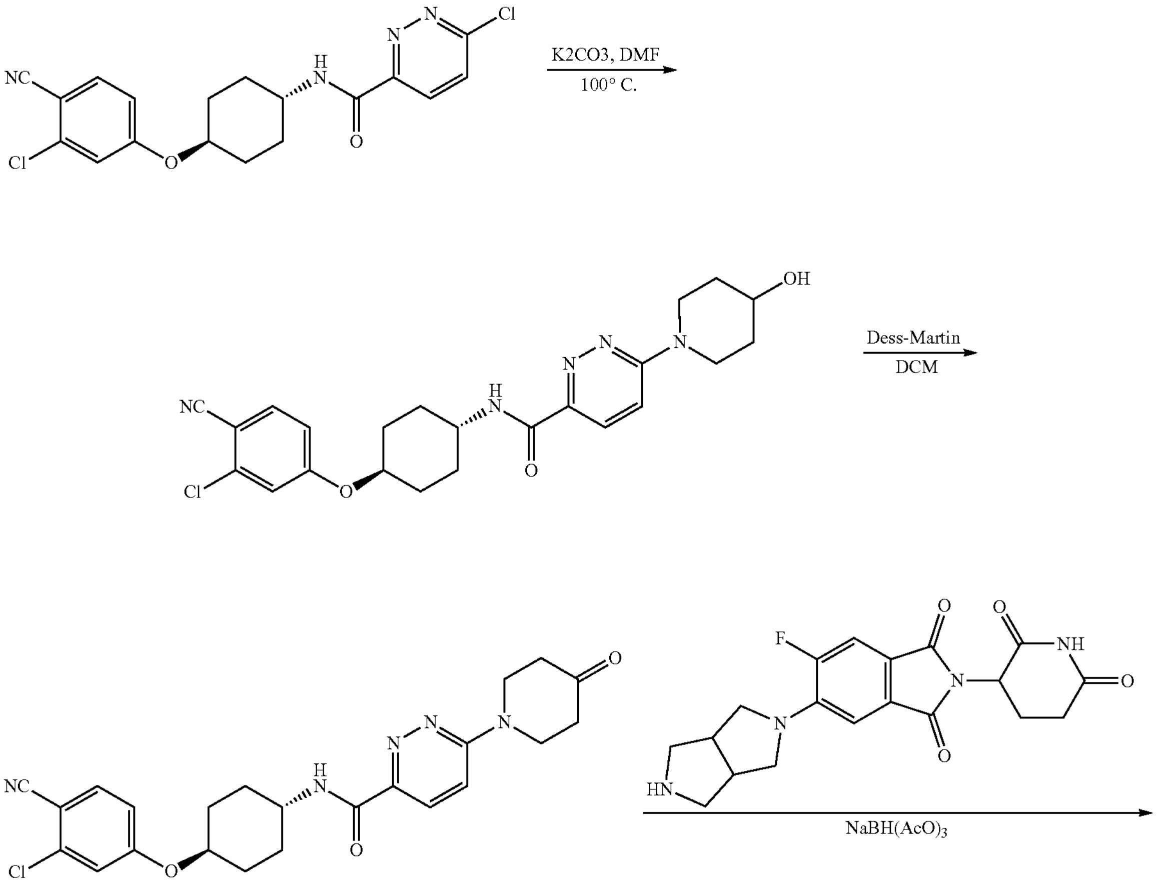

-continued
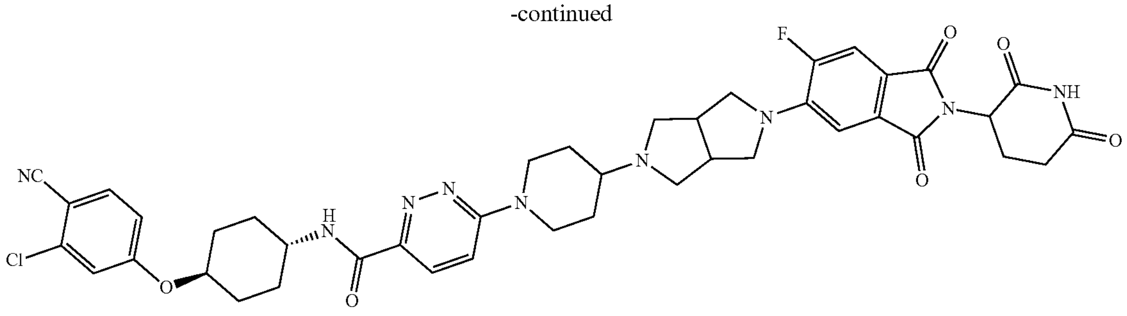
LC/MS ($ESI^+$) Calcd for $C_{42}H_{43}ClFN_9O_6(M+H^+)$ m/z, 826.3; found 826.3.
$^1H$ NMR (400 MHz, $CDCl_3$) δ 8.10 (s, 1H), 8.00 (d, J=9.5 Hz, 1H), 7.86 (d, J=8.2 Hz, 1H), 7.56 (d, J=8.7 Hz, 1H), 7.45 (d, J=11.8 Hz, 1H), 7.17 (d, J=6.7 Hz, 1H), 7.00 (dd, J=5.9, 3.6 Hz, 2H), 6.85 (dd, J=8.7, 2.4 Hz, 1H), 4.92 (dd, J=12.3, 5.3 Hz, 1H), 4.49 (s, 2H), 4.32 (t, J=10.1 Hz, 2H), 4.05 (d, J=8.2 Hz, 2H), 3.53 (s, 4H), 3.14 (s, 4H), 2.91-2.66 (m, 6H), 2.20-2.10 (m, 7H), 1.54-1.38 (m, 4H).
66: Synthesis of N-((1r,4r)-4-(3-chloro-4-cyanophenoxy)cyclohexyl)-2-(4-(5-(2-(2,6-dioxopiperidin-3-yl)-6-fluoro-1,3-dioxoisopentanol-5-yl)hexahydropyrrolo [3,4-c]pyrrol-2(1H)-yl)piperidin-1-yl) pyrimidine-5-formamide
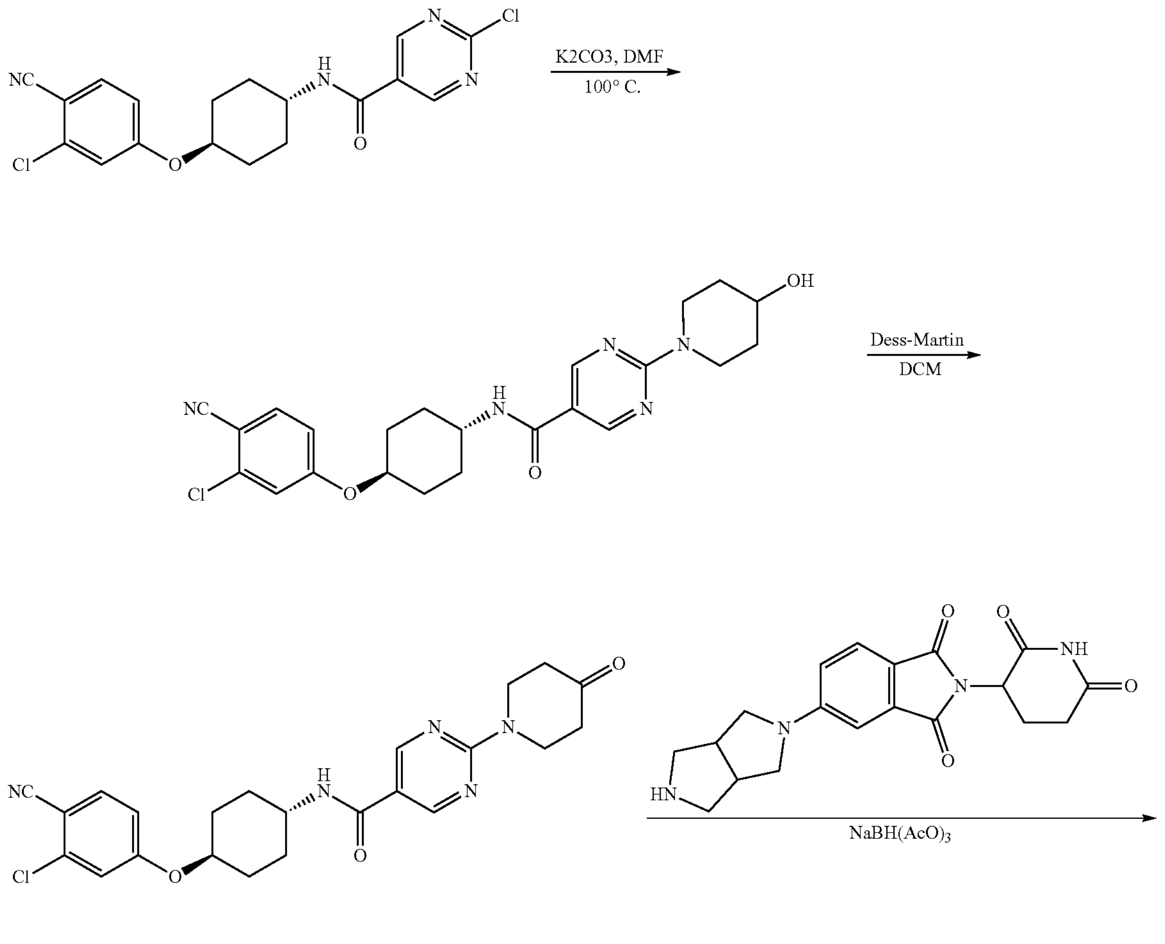

-continued
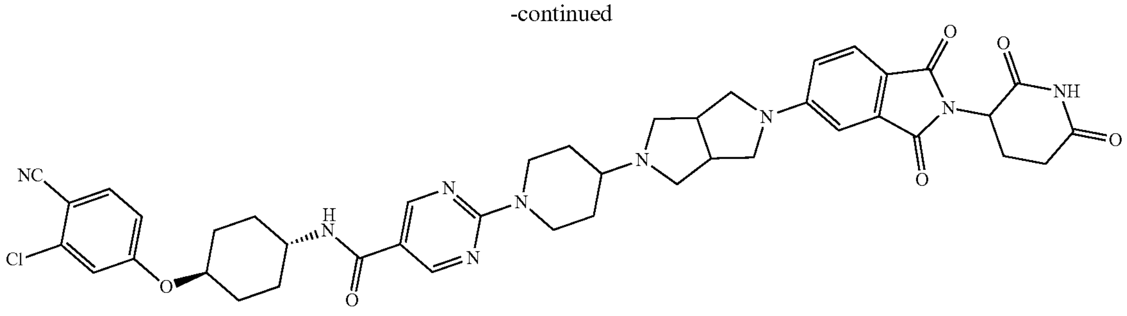
66
LC/MS ($ESI^+$) Calcd for $C_{42}H_{44}ClN_9O_6(M+H^+)$ m/z, 806.3; found 806.3.
$^1$H NMR (400 MHz, $CDCl_3$) δ 8.81 (s, 1H), 8.18 (d, J=9.5 Hz, 1H), 7.86 (d, J=8.2 Hz, 1H), 7.56 (d, J=8.7 Hz, 1H), 7.17 (d, J=6.7 Hz, 1H), 7.00 (dd, J=5.9, 3.6 Hz, 2H), 6.85 (dd, J=8.7, 2.4 Hz, 1H), 4.82 (dd, J=12.3, 5.3 Hz, 1H), 4.56 (s, 2H), 4.32 (t, J=10.1 Hz, 2H), 4.05 (d, J=8.2 Hz, 2H), 3.51 (s, 4H), 3.12 (s, 4H), 2.91-2.66 (m, 6H), 2.20-2.10 (m, 7H), 1.55-1.38 (m, 4H).
67: Synthesis of N-((1r,4r)-4-(3-chloro-4-cyanophenoxy)cyclohexyl)-6-(5-(1-(2-(2,6-dioxopiperidin-3-yl)-6-fluoro-1,3-dioxoisoindolin-5-yl)hexahydropyrrolo[3,4-c]pyrrol-2(1H)-yl)pyridazine-3-carboxamide
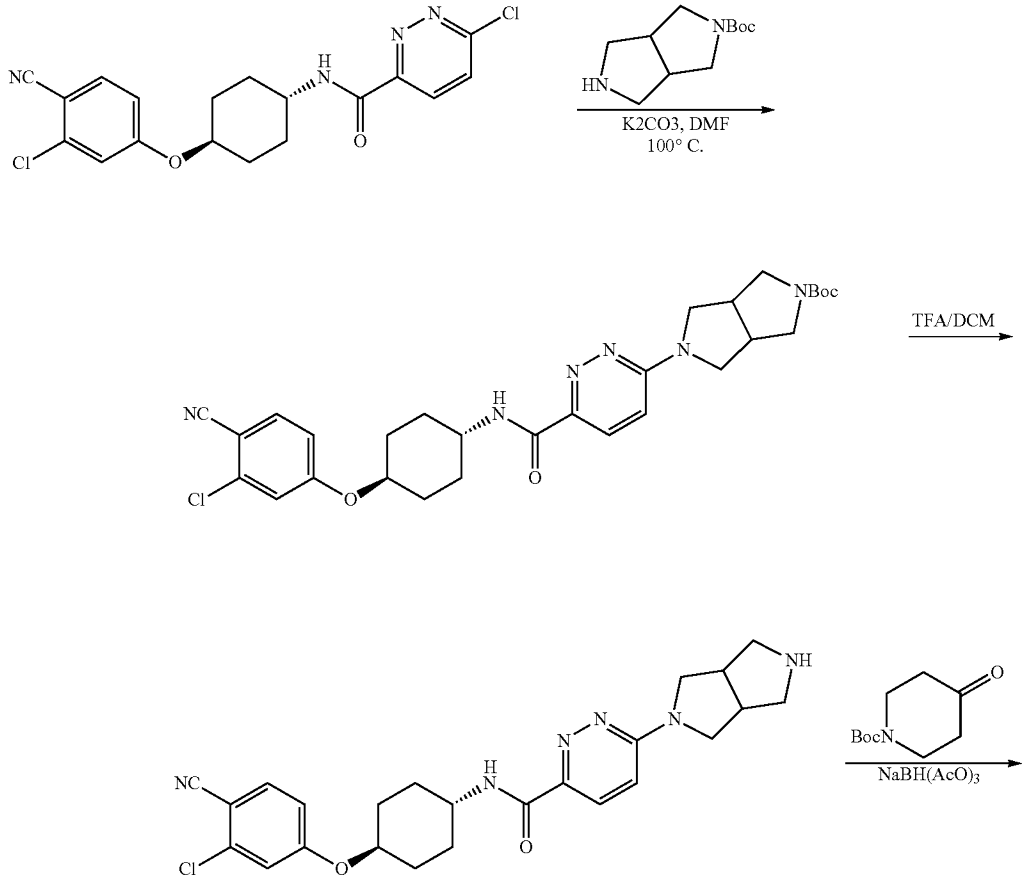

-continued

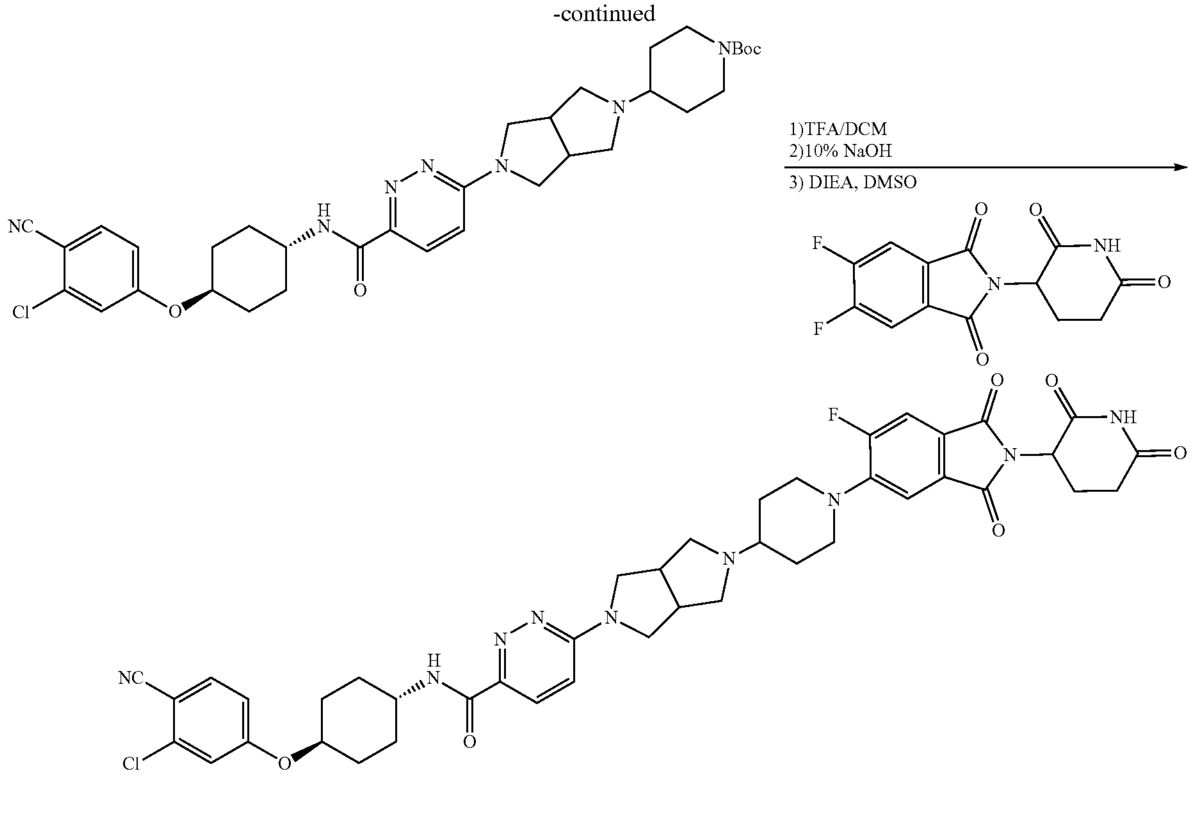

67

LC/MS (ESI+) Calcd for $C_{42}H_{43}ClFN_9O_6$ (M+H+) m/z, 824.3; found 824.3.

$^1$H NMR (400 MHz, $CDCl_3$) δ 7.99 (d, J=9.4 Hz, 1H), 7.91 (d, J=8.2 Hz, 1H), 7.56 (d, J=8.7 Hz, 1H), 7.45 (d, J=11.0 Hz, 1H), 7.37 (d, J=7.3 Hz, 1H), 7.00 (d, J=2.4 Hz, 1H), 6.86 (dd, J=8.8, 2.4 Hz, 1H), 6.74 (d, J=9.4 Hz, 1H), 4.92 (dd, J=12.3, 5.3 Hz, 3H), 4.32 (t, J=9.9 Hz, 1H), 4.11-3.99 (m, 2H), 3.84 (s, 2H), 3.59 (dd, J=24.3, 11.8 Hz, 5H), 3.08 (s, 2H), 2.95-2.86 (m, 5H), 2.83-2.62 (m, 6H), 2.32 (d, J=10.1 Hz, 4H), 2.16 (dd, J=22.5, 11.8 Hz, 7H), 2.05-1.95 (m, 4H), 1.89 (s, 2H), 1.71 (dt, J=22.4, 10.2 Hz, 5H), 1.54-1.40 (m, 3H).

68: Synthesis of N-((1r,4r)-4-(3-chloro-4-cyanophenoxy)cyclohexyl)-2-(4-(5-(2-(2,6-dioxopiperidin-3-yl)-1,3-dioxoisoindolin-5-yl)hexahydropyrrolo[3,4-c]pyrrol-2(1H)-yl)piperidin-1-yl)pyrimidine-5-formamide

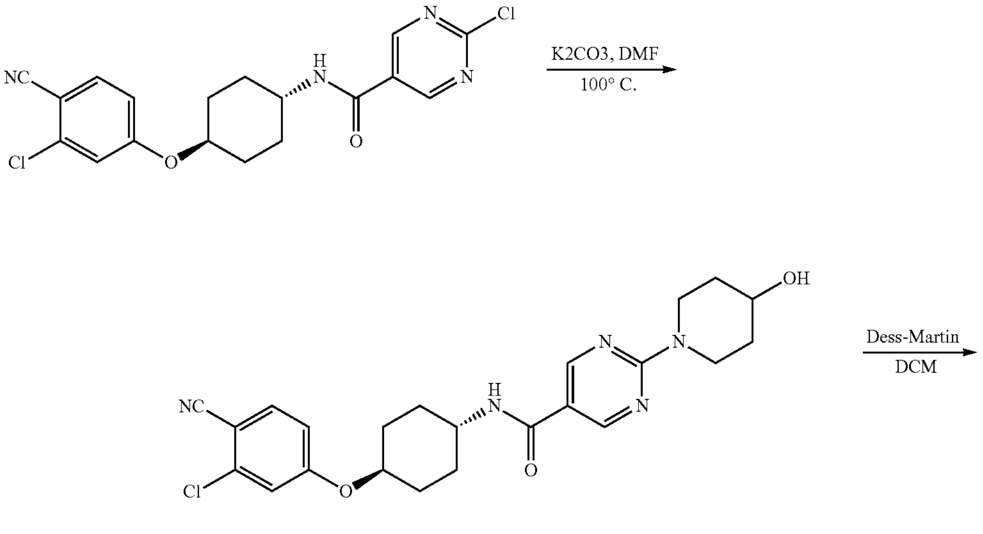

-continued
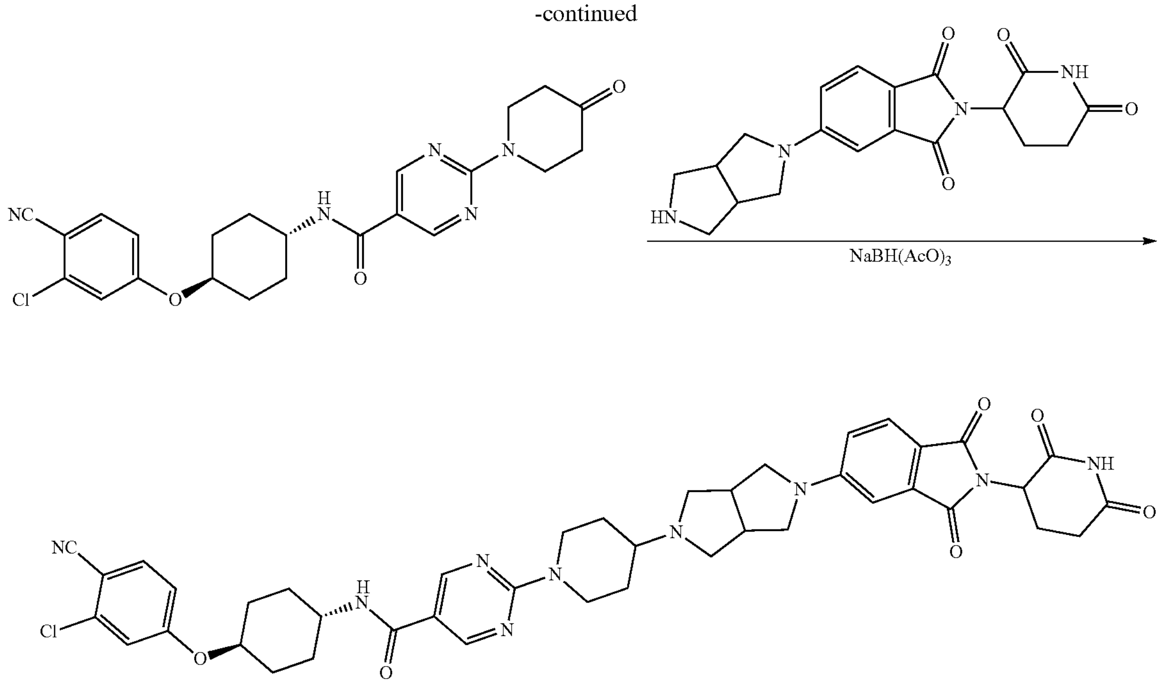
68
LC/MS ($ESI^+$) Calcd for $C_{42}H_{44}ClN_9O_6$ ($M+H^+$) m/z, 806.3; found 806.3. $^1H$ NMR (400 MHz, $CDCl_3$) δ 8.67 (s, 2H), 8.45 (s, 1H), 7.66 (d, J=8.4 Hz, 1H), 7.55 (d, J=8.7 Hz, 1H), 7.02-6.95 (m, 2H), 6.84 (dd, J=8.8, 2.4 Hz, 1H), 6.75 (s, 1H), 5.91 (s, 1H), 4.94 (s, 1H), 4.66 (d, J=9.8 Hz, 2H), 4.26 (d, J=10.3 Hz, 1H), 4.00 (s, 1H), 3.64 (d, J=7.5 Hz, 2H), 3.37 (d, J=7.2 Hz, 2H), 3.08 (s, 3H), 2.92-2.62 (m, 6H), 2.14 (s, 5H), 1.87 (s, 2H), 1.46 (s, 5H), 1.25 (s, 2H).
69: Synthesis of N-((1r,4r)-4-(3-chloro-4-cyanophenoxy)cyclohexyl)-5-(5-(1-(2-(2,6-dioxopiperidin-3-yl)-1,3-dioxoisoindolin-5-yl)piperidine-4-yl) hexahydropyrrolo[3,4-c]pyrrol-2(1H)-yl)pyrazine-2-carboxamide
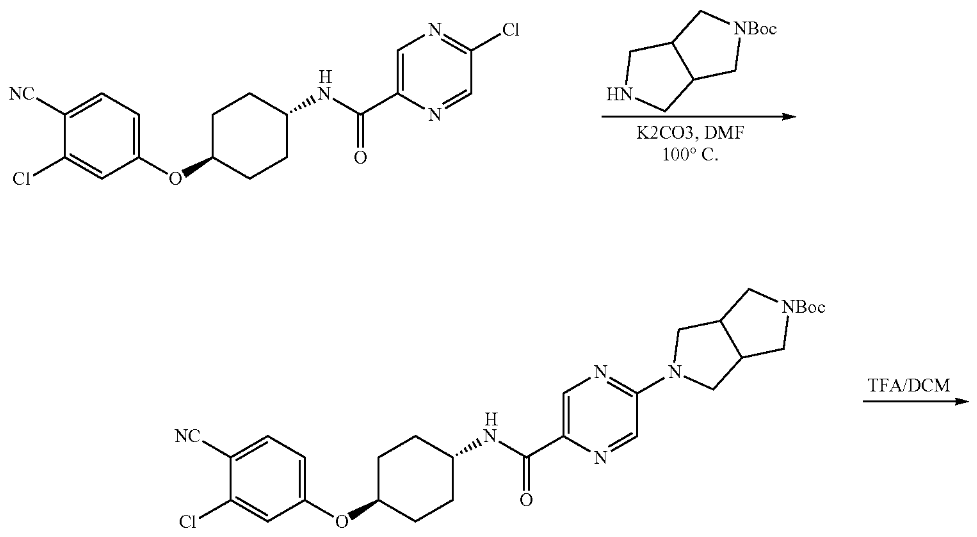

-continued

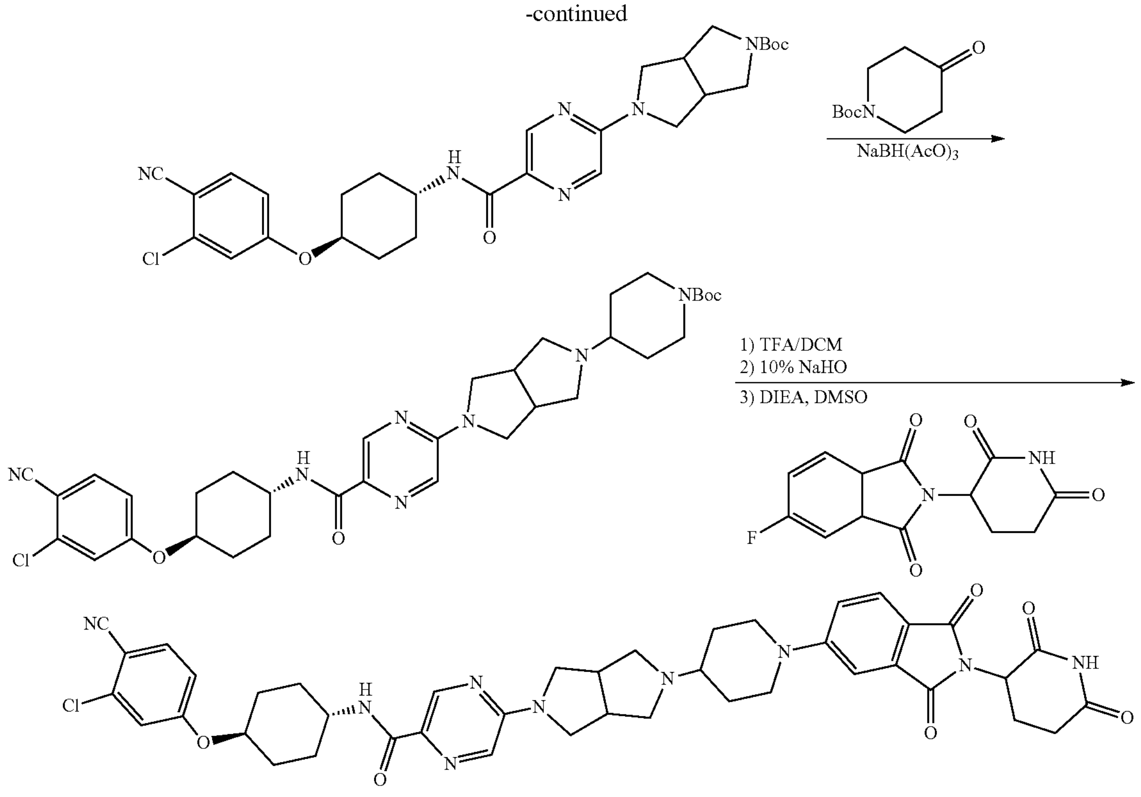

69

LC/MS ($ESI^+$) Calcd for $C_{42}H_{44}ClN_9O_6(M+H^+)$ m/z, 806.3; found 806.3.

$^1H$ NMR (400 MHz, $CDCl_3$) δ 8.81 (d, J=1.3 Hz, 1H), 7.72 (d, J=1.3 Hz, 1H), 7.56 (d, J=8.7 Hz, 1H), 7.45 (d, J=11.1 Hz, 1H), 7.38 (dd, J=10.5, 7.8 Hz, 2H), 7.16 (d, J=5.6 Hz, 1H), 6.99 (d, J=2.4 Hz, 1H), 6.85 (dd, J=8.8, 2.4 Hz, 1H), 4.92 (dd, J=12.3, 5.3 Hz, 1H), 4.35-4.26 (m, 1H), 4.08-3.98 (m, 1H), 3.82 (dd, J=11.0, 8.1 Hz, 2H), 3.62 (d, J=12.3 Hz, 2H), 3.50 (d, J=11.0 Hz, 2H), 3.05 (s, 2H), 2.98-2.83 (m, 6H), 2.80-2.71 (m, 2H), 2.71-2.65 (m, 2H), 2.33 (d, J=10.3 Hz, 2H), 2.21-2.11 (m, 6H), 2.05 (s, 3H), 1.77-1.61 (m, 5H), 1.42 (d, J=12.0 Hz, 3H).

70: Synthesis of N-((1r,4r)-4-(3-chloro-4-cyanophenoxy)cyclohexyl)-5-(5-(1-(2-(2,6-dioxopiperidin-3-yl)-6-fluoro-1,3-dioxoisoindolin-5-yl)piperidine-4-yl)hexahydropyrrolo[3,4-c]pyrrol-2(1H)-yl) pyrazine-2-carboxamide

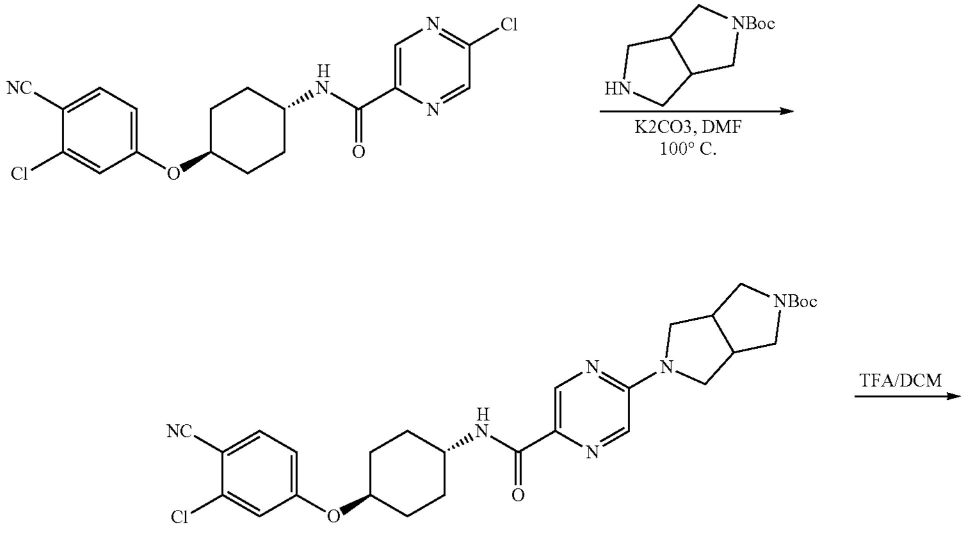

-continued
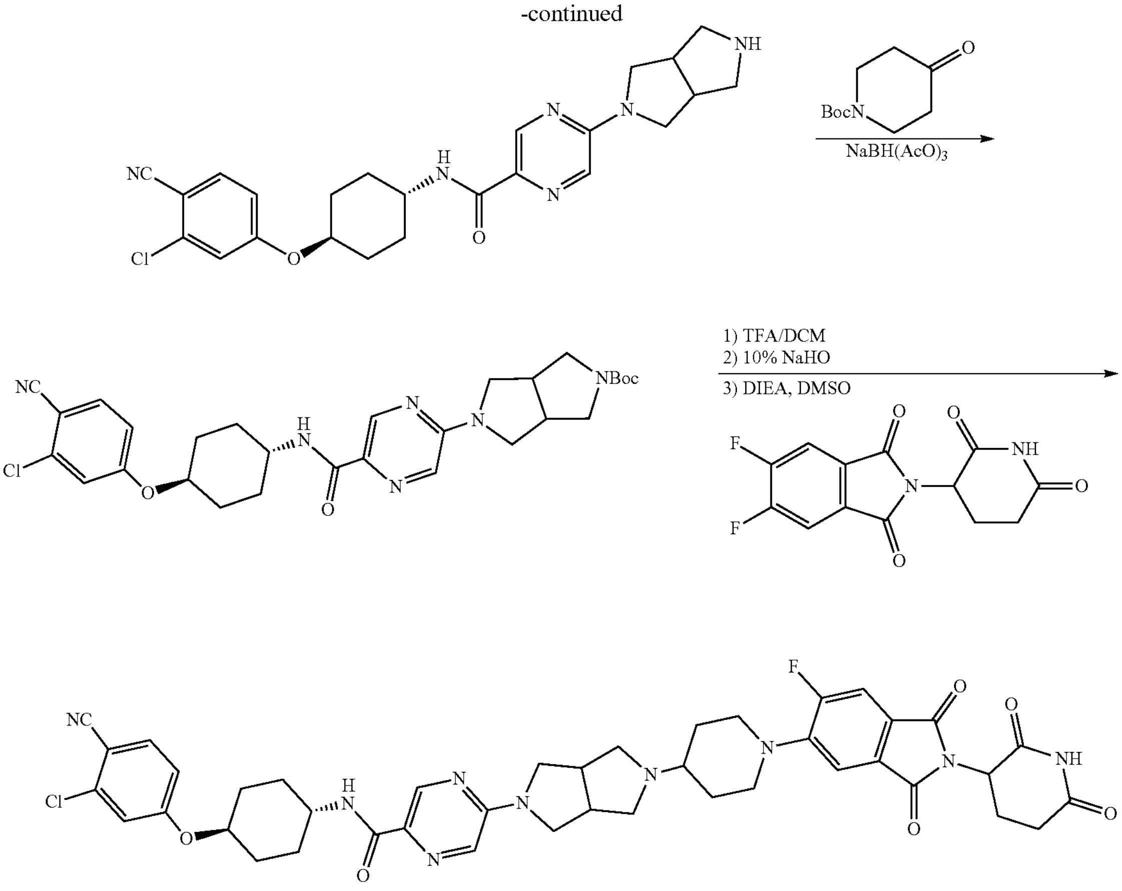
70
LC/MS (ESI+) Calcd for $C_{42}H_{43}ClFN_9O_6(M+H^+)$ m/z, 824.3; found 824.3.
$^1H$ NMR (400 MHz, $CDCl_3$) δ 8.85 (d, J=1.3 Hz, 1H), 7.72 (d, J=1.3 Hz, 1H), 7.56 (d, J=8.7 Hz, 1H), 7.45 (d, J=11.1 Hz, 1H), 7.38 (dd, J=10.5, 7.8 Hz, 2H), 6.99 (d, J=2.4 Hz, 1H), 6.85 (dd, J=8.8, 2.4 Hz, 1H), 4.92 (dd, J=12.3, 5.3 Hz, 1H), 4.35-4.26 (m, 1H), 4.08-3.98 (m, 1H), 3.82 (dd, J=11.0, 8.1 Hz, 2H), 3.62 (d, J=12.3 Hz, 2H), 3.50 (d, J=11.0 Hz, 2H), 3.05 (s, 2H), 2.98-2.83 (m, 6H), 2.80-2.71 (m, 2H), 2.71-2.65 (m, 2H), 2.31 (d, J=10.3 Hz, 2H), 2.21-2.11 (m, 6H), 2.05 (s, 3H), 1.78-1.62 (m, 5H), 1.46 (d, J=12.0 Hz, 3H).
71: Synthesis of N-((1r,4r)-4-(3-chloro-4-cyanophenoxy)cyclohexyl)-6-(2-(2,6-dioxopiperidin-3-yl)-6-fluoro-1,3-dioxoisoindolin-5-yl)piperidine-4-yl)-2,7-diazaspiro[3.5]nonan-7-yl)pyridazine-3-formamide
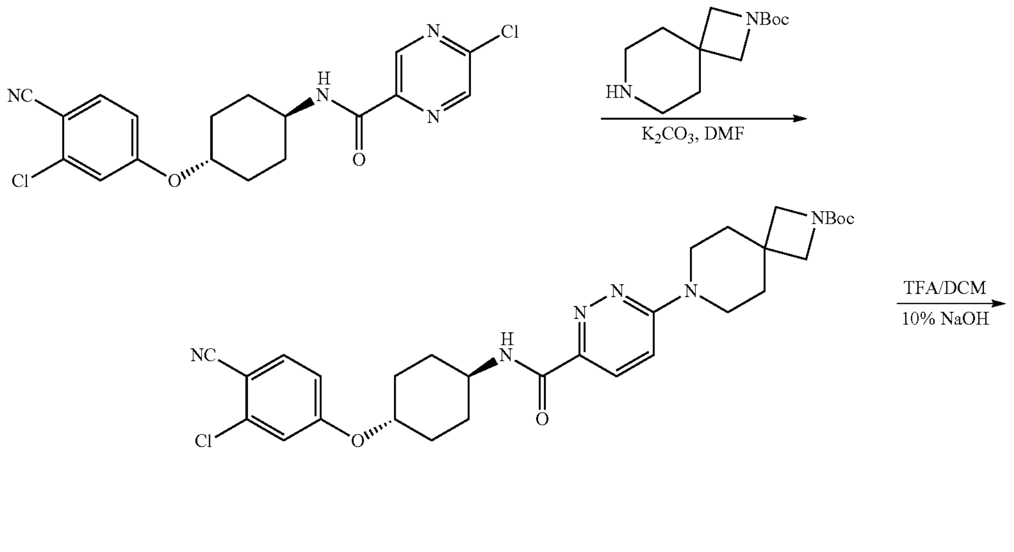

-continued

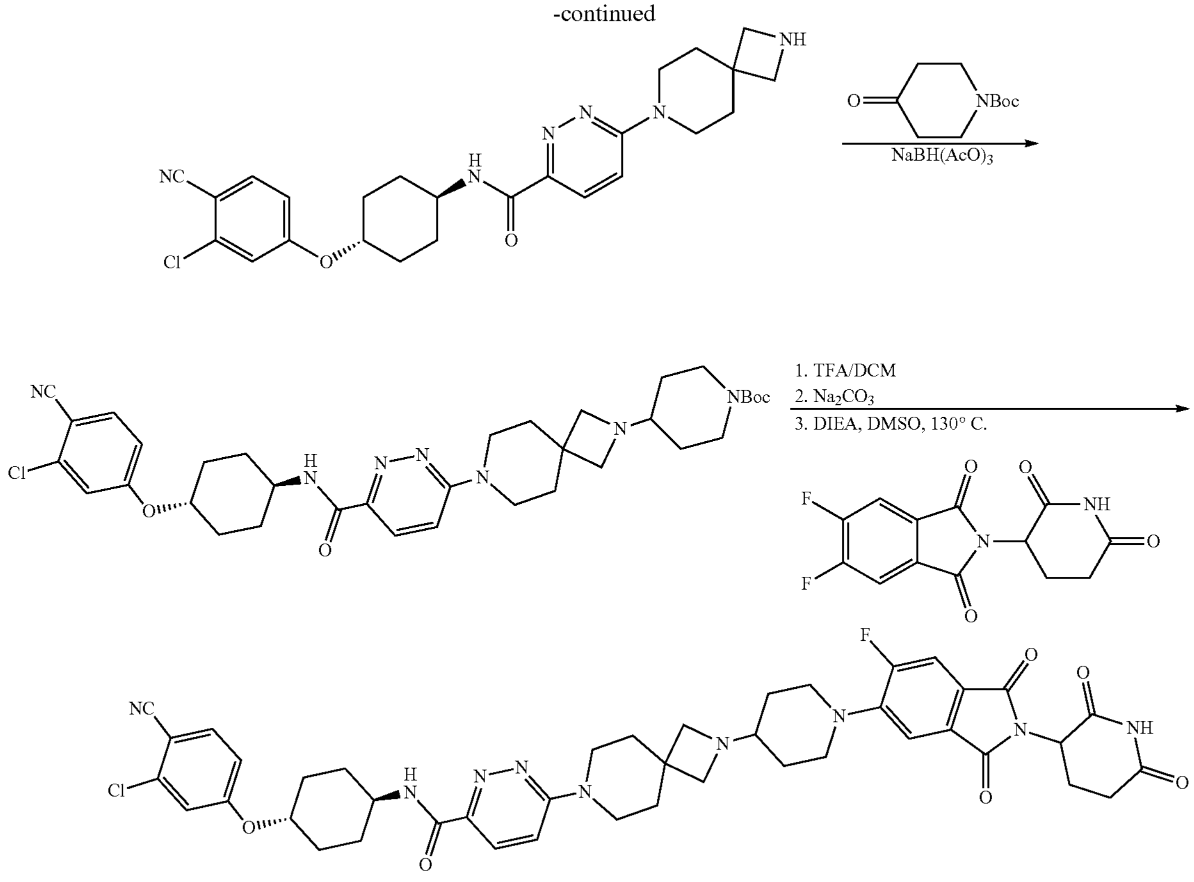

71

LC/MS (ESI+) Calcd for $C_{43}H_{45}ClFN_9O_6$ (M+H+) m/z, 838.3; found 838.3.

$^1$H NMR (400 MHz, DMSO-$d_6$) δ 11.01 (s, 1H), 8.60 (d, J=8.1 Hz, 1H), 7.87 (d, J=8.8 Hz, 1H), 7.82 (d, J=9.5 Hz, 1H), 7.70 (d, J=11.4 Hz, 1H), 7.41 (d, J=7.4 Hz, 1H), 7.36 (d, J=2.3 Hz, 1H), 7.32 (d, J=9.6 Hz, 1H), 7.13 (dd, J=8.8, 2.4 Hz, 1H), 5.09 (dd, J=12.8, 5.4 Hz, 1H), 4.53 (s, 1H), 4.21 (d, J=13.0 Hz, 2H), 3.85 (d, J=8.3 Hz, 1H), 3.24 (s, 1H), 3.17 (s, 4H), 2.99 (s, 4H), 2.91-2.80 (m, 1H), 2.59 (d, J=18.4 Hz, 1H), 2.35 (d, J=18.7 Hz, 2H), 2.10 (d, J=10.0 Hz, 2H), 2.03 (s, 1H), 1.89 (d, J=10.2 Hz, 2H), 1.81 (s, 4H), 1.73 (d, J=11.0 Hz, 2H), 1.64 (d, J=12.8 Hz, 2H), 1.51 (d, J=12.3 Hz, 2H), 1.2-1.10 (m, 3H).

72: N-((1r,3r)-3-(3-chloro-4-cyanophenoxy)-2,2,4,4-tetramethylcyclobutyl)-6-(5-(1-(2-(2,6-dioxopiperidin-3-yl)-6-fluoro-1,3-dioxoisoindolin-5-yl)piperidine-4-yl)hexahydropyrrolo[3,4-c]pyrrol-2(1H)-yl) pyridazine-3-formamide

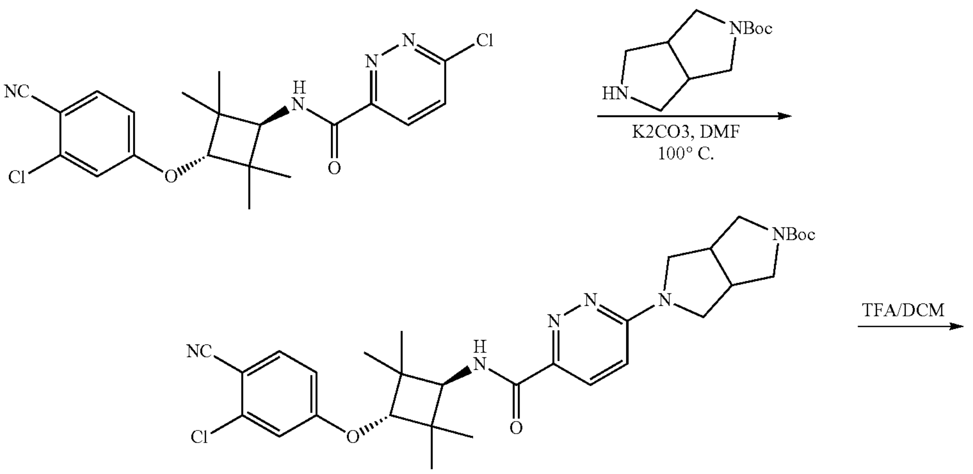

-continued
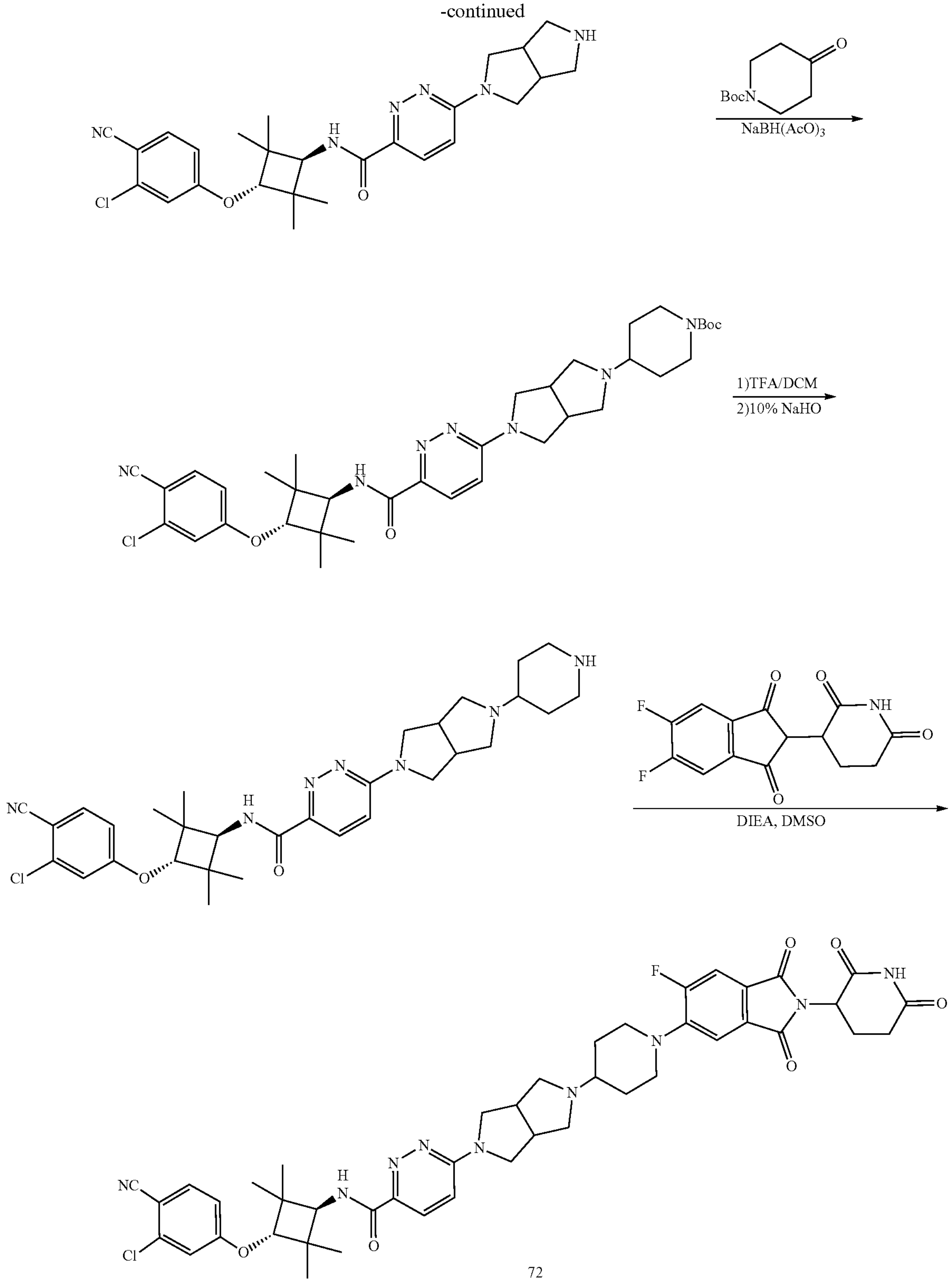
72
LC/MS (ESI+) Calcd for $C_{44}H_{47}ClFN_9O_6$ (M+H+) m/z, 852.3; found 852.3.
$^1$H NMR (400 MHz, $CDCl_3$) δ 8.19 (d, J=9.1 Hz, 1H), 7.99 (d, J=9.4 Hz, 1H), 7.57 (d, J=8.7 Hz, 1H), 7.45 (d, J=11.0 Hz, 1H), 7.37 (d, J=7.3 Hz, 1H), 6.97 (d, J=2.4 Hz, 1H), 6.81 (dd, J=8.7, 2.4 Hz, 1H), 6.76 (d, J=9.4 Hz, 1H), 4.92 (dd, J=12.3, 5.3 Hz, 1H), 4.55 (s, 1H), 4.19 (d, J=9.1 Hz, 1H), 4.07 (s, 1H), 3.85 (s, 2H), 3.61 (t, J=13.4 Hz, 4H), 3.10 (s, 2H), 2.91 (dd, J=22.3, 8.6 Hz, 5H), 2.85-2.65 (m, 4H), 2.13 (dd, J=11.3, 6.2 Hz, 2H), 2.07-1.95 (m, 4H), 1.74 (dd, J=20.5, 9.9 Hz, 2H), 1.28 (s, 5H), 1.21 (s, 6H).

73: Synthesis of N-((1r,4r)-4-(3-chloro-4-cyanophenoxy)cyclohexyl)-5-(4-((1-(2,6-dioxopiperidin-3-yl-6-fluoro-1,3-dioxoisoindolin-5-yl)piperidine-4-yl) amino) piperidin-1-yl)pyrazine-2-carboxamide

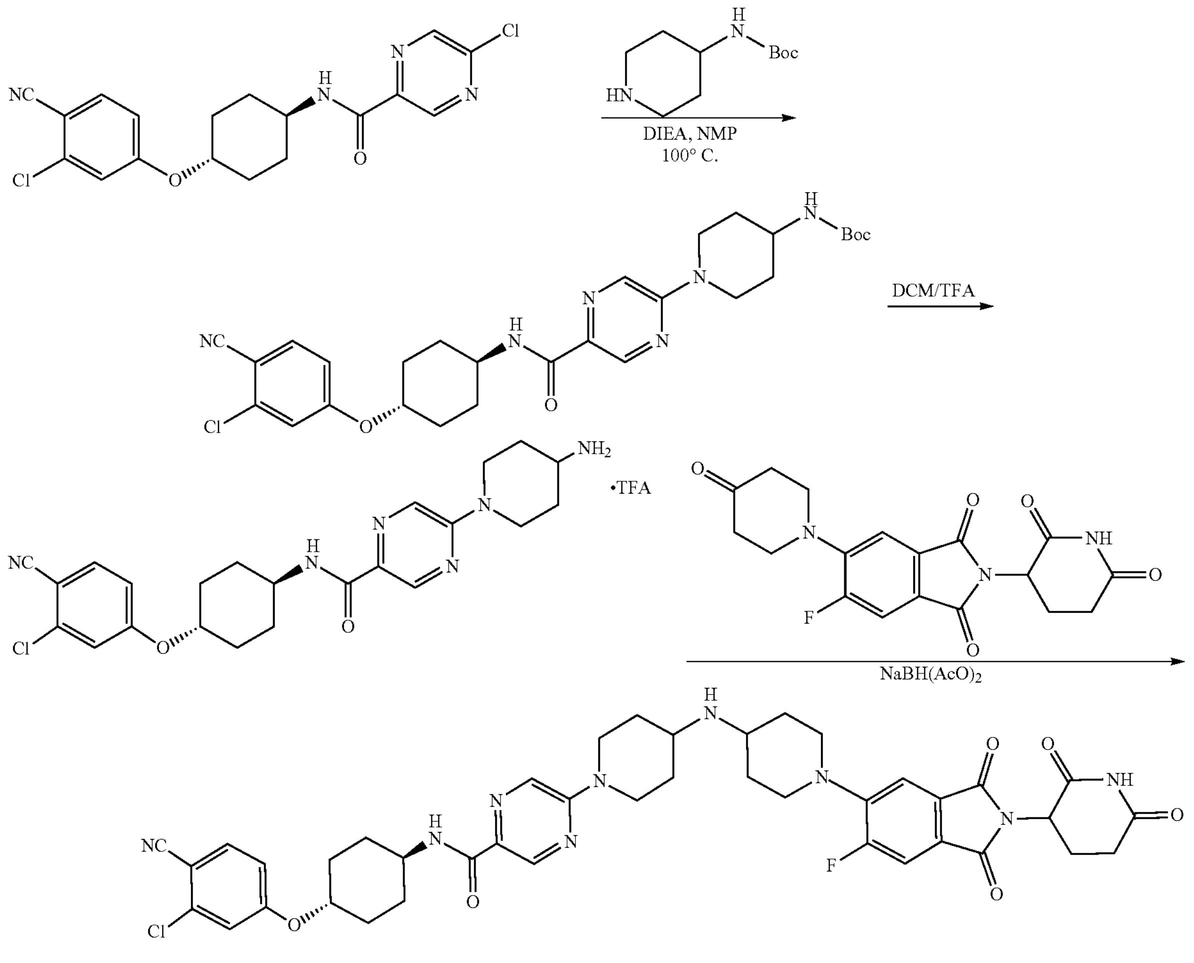

73

1. Synthesis of t-butyl (1-(5-((1r,4r)-4-(3-chloro-4-cyanophenoxy)cyclohexyl) carbamoyl)pyrazine-2-yl)piperidine-4-yl)carbamate 5-Chloro-N-((1r,4r)-4-(3-chloro-4-cyanophenoxy)cyclohexyl)pyrazine-2-carboxamide (400 mg, 1.02 mmol) was dissolved in 10 mL of NMP, to which were added t-butyl piperidin-4-ylcarbamate (246 mg, 1.23 mmol) and DIEA (661 mg, 5.11 mmol), and then the reaction solution was heated to 100° C. and reacted. The reaction was quenched by adding water, and then extracted with EA. The organic phase was washed with saturated citric acid aqueous solution, and then purified to provide t-butyl (1-(5-((1r,4r)-4-(3-chloro-4-cyanophenoxy)cyclohexyl)carbamoyl)pyrazine-2-yl)piperidine-4-yl) carbamate (450 mg), with a yield of 79.3%. LC/MS ($ESI^+$) Calcd for $C_{28}H_{33}ClN_6O_4(M-56+H^+)$ m/z, 500.2; found 500.2.

2. 5-(4-Aminopiperdine-1-yl)-N-((1r,4r)-4-(3-chloro-4-cyanophenoxy)hexyl)pyrazine-2-carboxamide trifluoroacetate t-Butyl (1-(5-((1r,4r)-4-(3-chloro-4-cyanophenoxy)cyclohexyl)carbamoyl)pyrazine-2-yl)piperidine-4-yl)carbamate (300 mg, 0.54 mmol) was dissolved in 2 mL of DCM, to which was added 4 mL of trifluoroacetic acid, and the mixture was stirred 2 h. The reaction solution was directly concentrated to dry, and most of TFA was removed by evaporation with DCM, to provide 5-(4-aminopiperdine-1-yl)-N-((1r,4r)-4-(3-chloro-4-cyanophenoxy)hexyl)pyrazine-2-carboxamide trifluoroacetate (325 mg).

3. Synthesis of N-((1r,4r)-4-(3-chloro-4-cyanophenoxy)cyclohexyl)-5-(4-((1-(2,6-dioxopiperidin-3-yl-6-fluoro-1,3-dioxoisoindolin-5-yl)piperidine-4-yl) amino) piperidin-1-yl)pyrazine-2-carboxamide 5-(4-Aminopiperdine-1-yl)-N-((1r,4r)-4-(3-chloro-4-cyanophenoxy)hexyl)pyrazine-2-carboxamide trifluoroacetate (100 mg, 0.22 mmol) and 2-(2,6-dioxopiperidin-3-yl)-5-fluoro-6-(4-oxopiperidin-1-yl)isoindoline-1,3-dione (83 mg, 0.22 mmol) were dissolved in the mixed solvent of 2 mL dichloromethane and 1 mL methanol, to which was slowly added sodium triacetoxyborohydride (186 mg, 0.88 mmol). The mixture was allowed to react 5 h, and then purified by TLC, to provide N-((1r,4r)-4-(3-chloro-4-cyanophenoxy)cyclohexyl)-5-(4-((1-(2,6-dioxopiperidin-3-yl-6-fluoro-1,3-dioxoisoindolin-5-yl)piperidine-4-yl)amino)piperidin-1-yl) pyrazine-2-carboxamide (12 mg), with a yield of 7.3%. LC/MS (ESI) Calcd for $C_{28}H_{35}ClN_6O_4(M+H^+)$ m/z, 812.3; found 812.3. $^1H$ NMR (400 MHz, $CDCl_3$) δ 8.84 (s, 1H), 7.99 (s, 1H), 7.56 (d, J=8.7 Hz, 1H), 7.47 (dd, J=11.0, 2.7 Hz, 1H), 7.40 (dd, J=13.9, 7.5 Hz, 2H), 7.00 (d, J=2.3 Hz, 1H), 6.85 (dd, J=8.8, 2.4 Hz, 1H), 4.99-4.88 (m, 2H), 4.48 (s, 2H), 4.31 (s, 2H), 4.05 (s, 2H), 3.71 (d, J=7.5 Hz, 2H), 3.61-3.51 (m, 1H), 3.16 (s, 1H), 3.08 (d, J=10.3 Hz, 3H), 2.93 (t, J=12.9 Hz, 4H), 2.79 (dd, J=25.3, 13.3 Hz, 3H), 2.18 (d, J=4.6 Hz, 8H), 2.07 (s, 1H), 1.25 (s, 3H).

74: Synthesis of N-((1r,4r)-4-(3-chloro-4-cyanophenoxy)cyclohexyl)-6-(2-(2,6-dioxopiperidin-3-yl)-1,3-dioxoisoindolin-5-yl)piperidine-4-yl)-2,7-diazaspiro [3.5]nonan-7-yl)pyridazine-3-formamide

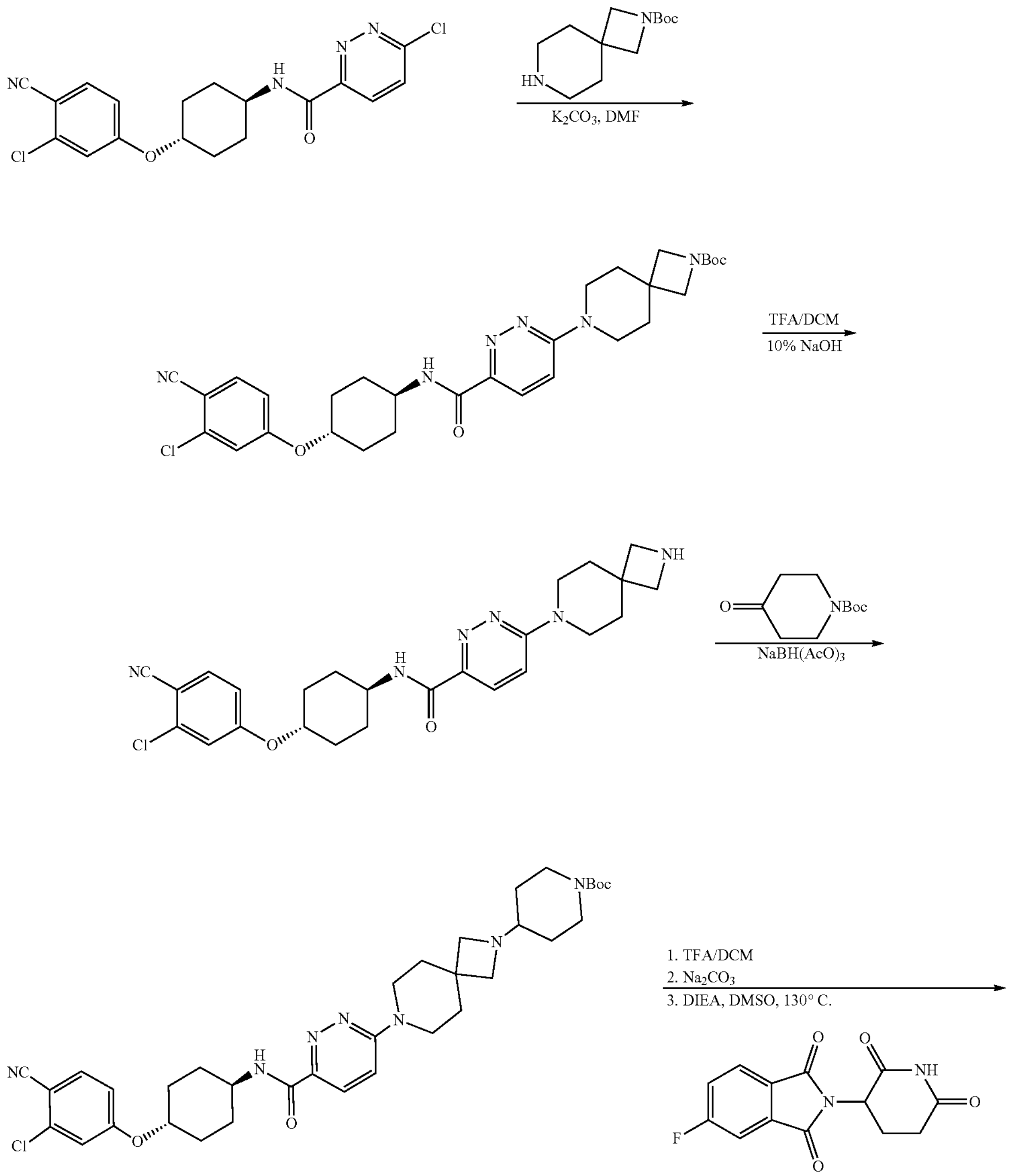

-continued

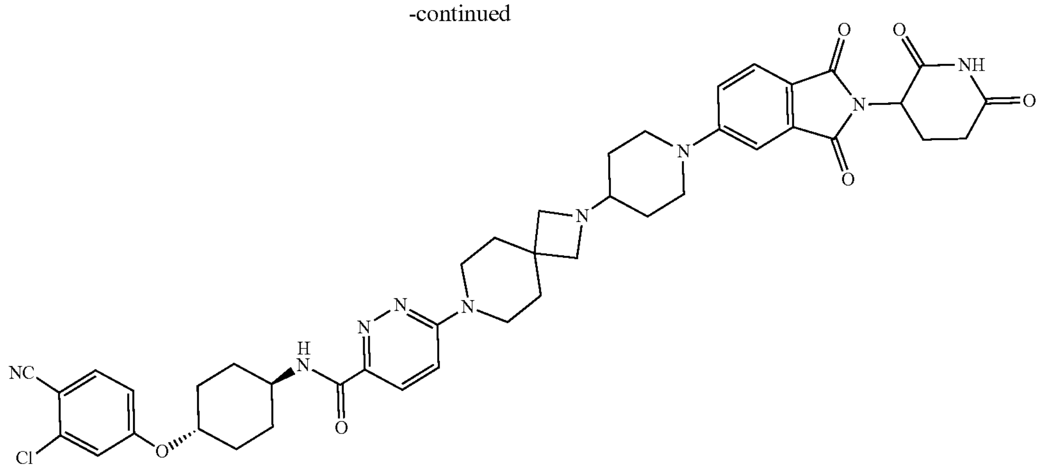

74

LCMS ($ESI^+$) Calcd for $C_{43}H_{46}ClN_9O_6$ ($M+H^+$) m/z, 80.3; found 820.3.

$^1$H NMR (400 MHz, $CDCl_3$) δ 8.21 (s, 1H), 7.94 (d, J=9.5 Hz, 1H); 7.87 (d, J=8.2 Hz, 1H), 7.66 (d, J=8.5 Hz, 1H), 7.56 (d, J=8.7 Hz, 1H), 7.28 (d, J=2.2 Hz, 1H), 7.06 (dd, J=8.6, 2.2 Hz, 1H), 7.00 (t, J=10.0 Hz, 2H), 6.86 (dd, J=8.8, 2.4 Hz, 1H), 4.97 (dd, J=12.3, 5.3 Hz, 1H), 4.55 (s, 2H), 4.32 (t, J=10.0 Hz, 1H), 4.05 (dd, J=11.4, 7.2 Hz, 3.43-3.37 (m, 4H), 3.22 (d, J=10.9 Hz, 3H), 2.94-2.67 (m, 4H), 2.24-2.10 (m, 6H), 1.94 (s, 6H), 1.78-1.63 (m, 8H), 1.52-1.40 (m, 3H).

75: Synthetic Route for N-((1r,4r)-4-(3-chloro-4-cyanophenoxy)cyclohexyl)-6-(2-((1-(2,6-dioxopiperidin-3-yl)-6-fluoro-1,3-dioxoisoindolin-5-yl)piperidine-4-yl)methyl)-2,7-diazaspiro[3.5]nonan-7-yl) pyridazine-3-formamide

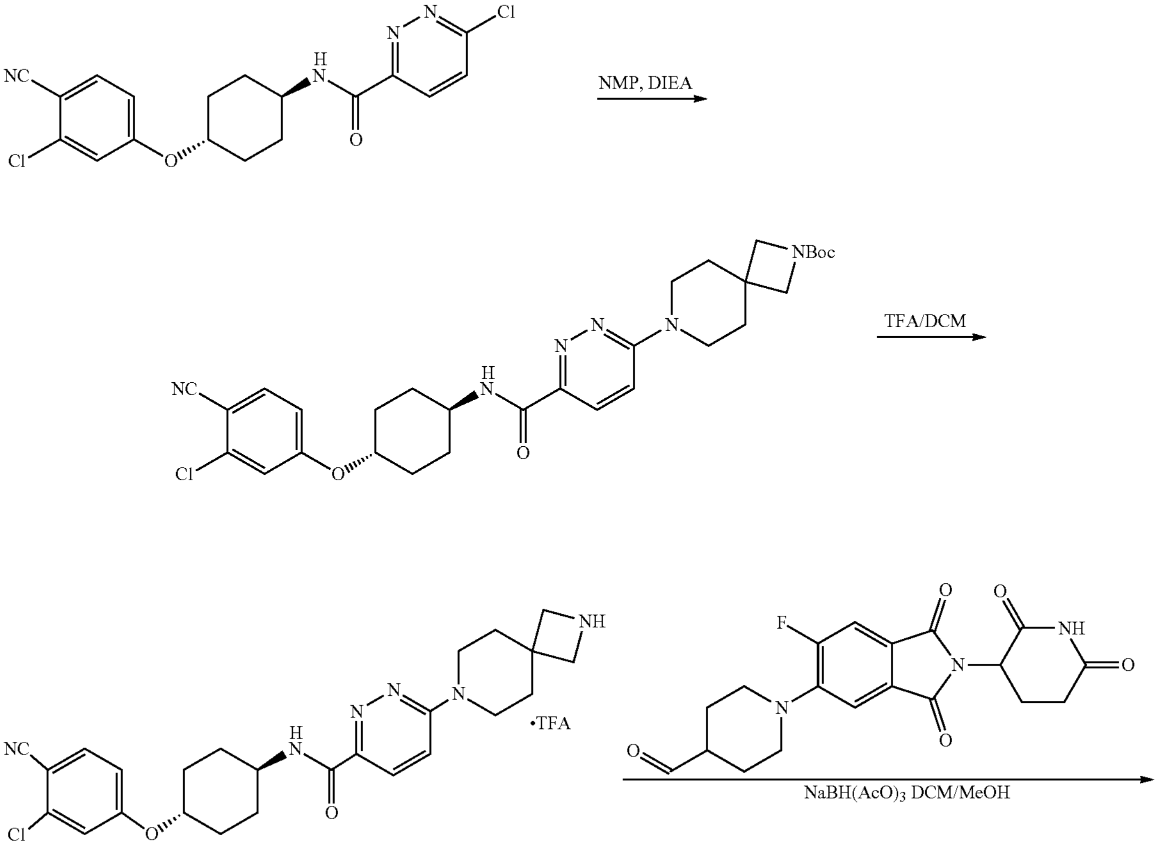

-continued
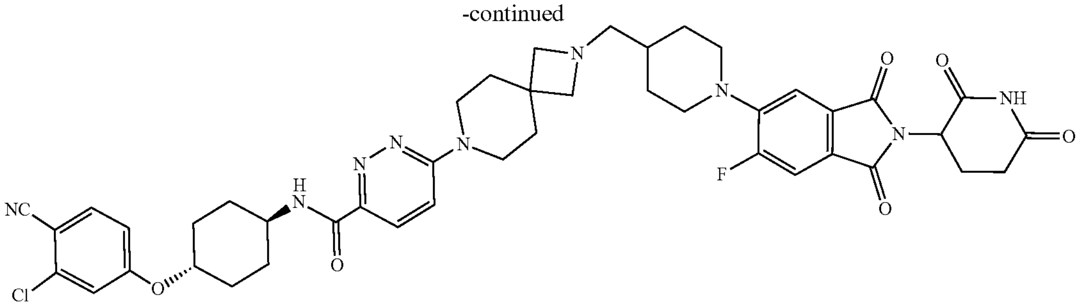
75
LC/MS (ESI+) Calcd for $C_{44}H_{47}ClFN_9O_6$(M+H+) m/z, 852.3, found 852.3. $^1$H NMR (400 MHz, $CDCl_3$) δ 8.46 (d, J=2.3 Hz, 1H), 7.58 (dd, J=9.0, 2.4 Hz, 1H), 7.55 (d, J=8.7 Hz, 1H), 7.47 (d, J=10.9 Hz, 11H), 7.38 (d, J=7.3 Hz, 1H), 6.99 (d, J=2.4 Hz, 1H), 6.85 (dd, J=8.7, 2.4 Hz, 1H), 6.64 (d, J=9.0 Hz, 1H), 5.90 (d, J=7.7 Hz, 1H), 4.93 (dd, J=12.3, 5.3 Hz, 1H), 4.52-4.25 (m, 4H), 4.04 (d, J=7.7 Hz, 1H), 3.33 (s, 3H), 3.18 (s, 3H), 3.04-2.65 (m, 6H), 2.57 (s, 1H), 2.27 (s, 4H), 2.17 (dd, J=25.9, 12.6 Hz, 9H), 2.05 (s, 3H), 1.98 (s, 4H), 1.86 (d, J=11.4 Hz, 2H), 1.76 (d, J=12.9 Hz, 2H), 1.48-1.36 (m, 4H).
76: N-((1r,4r)-4-(3-chloro-4-cyanophenoxy)cyclohexyl)-5-(2-((1-(2,6-dioxopiperidin-3-yl)-6-fluoro-1,3-dioxoisoindolin-5-yl)piperidine-4-yl)methyl)-2,7-diazaspiro[3.5]nonan-7-yl)pyridazine-2-carboxamide
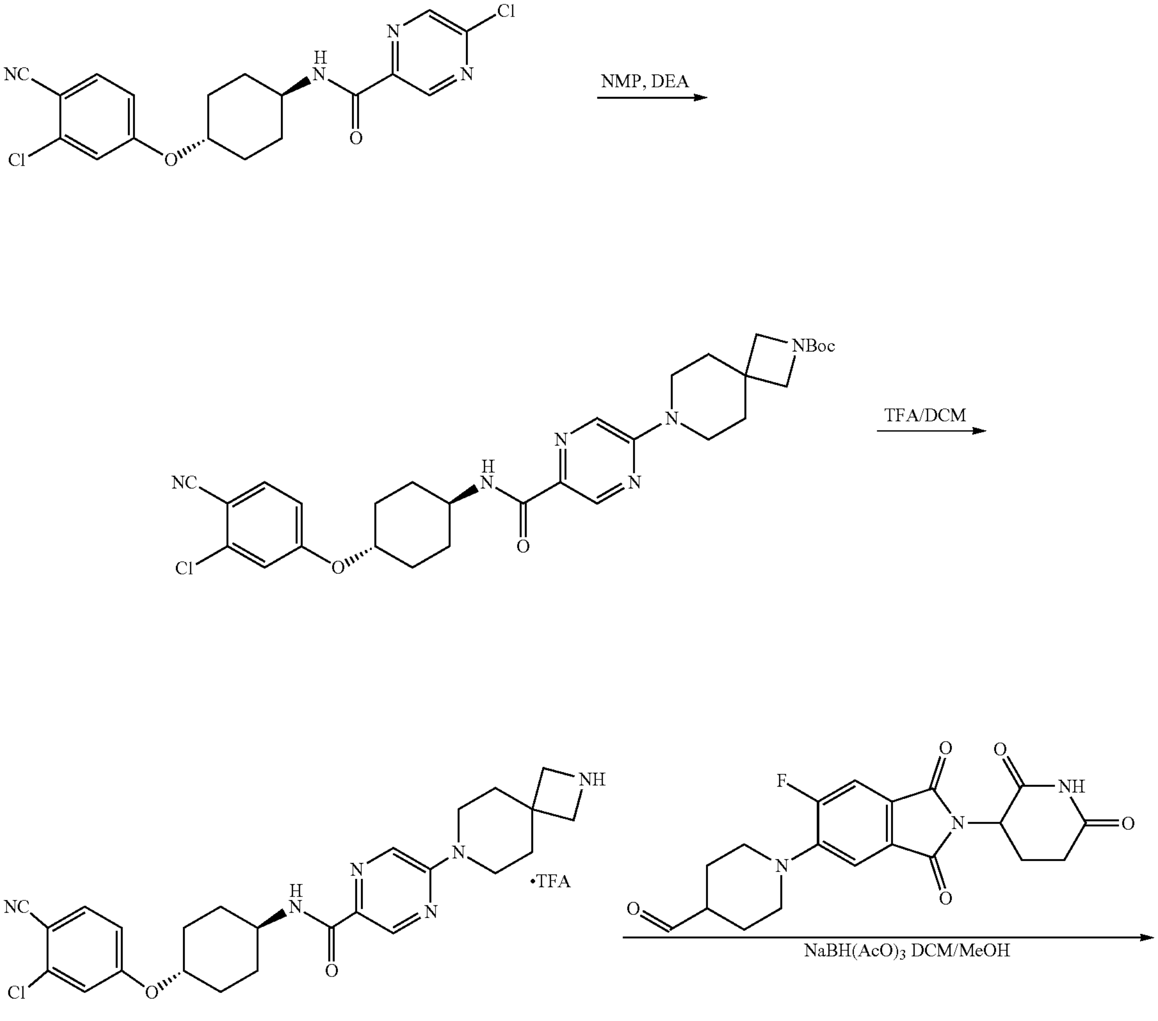

-continued
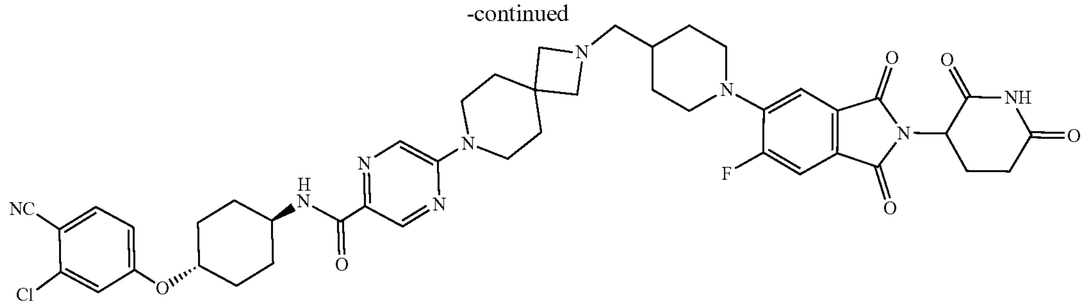
76
LC/MS (ESI+) Calcd for $C_{44}H_{47}ClFN_9O_6$ (M+H+) m/z, 852.3; found 852.3. $^1$H NMR (400 MHz, $CDCl_3$) δ 8.84 (d, J=2.3 Hz, 1H), 8.25 (dd, J=9.0, 2.4 Hz, 1H), 7.56 (d, J=8.7 Hz, 1H), 7.47 (d, J=10.9 Hz, 1H), 7.38 (d, J=7.3 Hz, 1H), 6.99 (d, J=2.4 Hz, 1H), 6.85 (dd, J=8.7, 2.4 Hz, 1H), 6.77 (d, J=9.0 Hz, 1H), 5.93 (d, J=7.7 Hz, 1H), 4.93 (dd, J=12.3, 5.3 Hz, 1H), 4.52-4.25 (m, 4H), 4.04 (d, J=7.7 Hz, 1H), 3.33 (s, 3H), 3.18 (s, 3H), 3.04-2.65 (m, 6H), 2.57 (s, 1H), 2.27 (s, 4H), 2.17 (dd, J=25.9, 12.6 Hz, 9H), 2.05 (s, 3H), 1.97 (s, 4H), 1.85 (d, J=11.4 Hz, 2H), 1.67 (d, J=12.9 Hz, 2H), 1.45-1.33 (m, 4H).
77: N-((1r,4r)-4-(3-chloro-4-cyanophenoxy)cyclohexyl)-6-(4-(7-(2-(2,6-dioxopiperidin-3-yl)-6-fluoro-1,3-dioxoisoindolin-5-yl)-2,7-diazaspiro[3.5]nonan-2-yl)piperidin-1-yl)nicotinamide
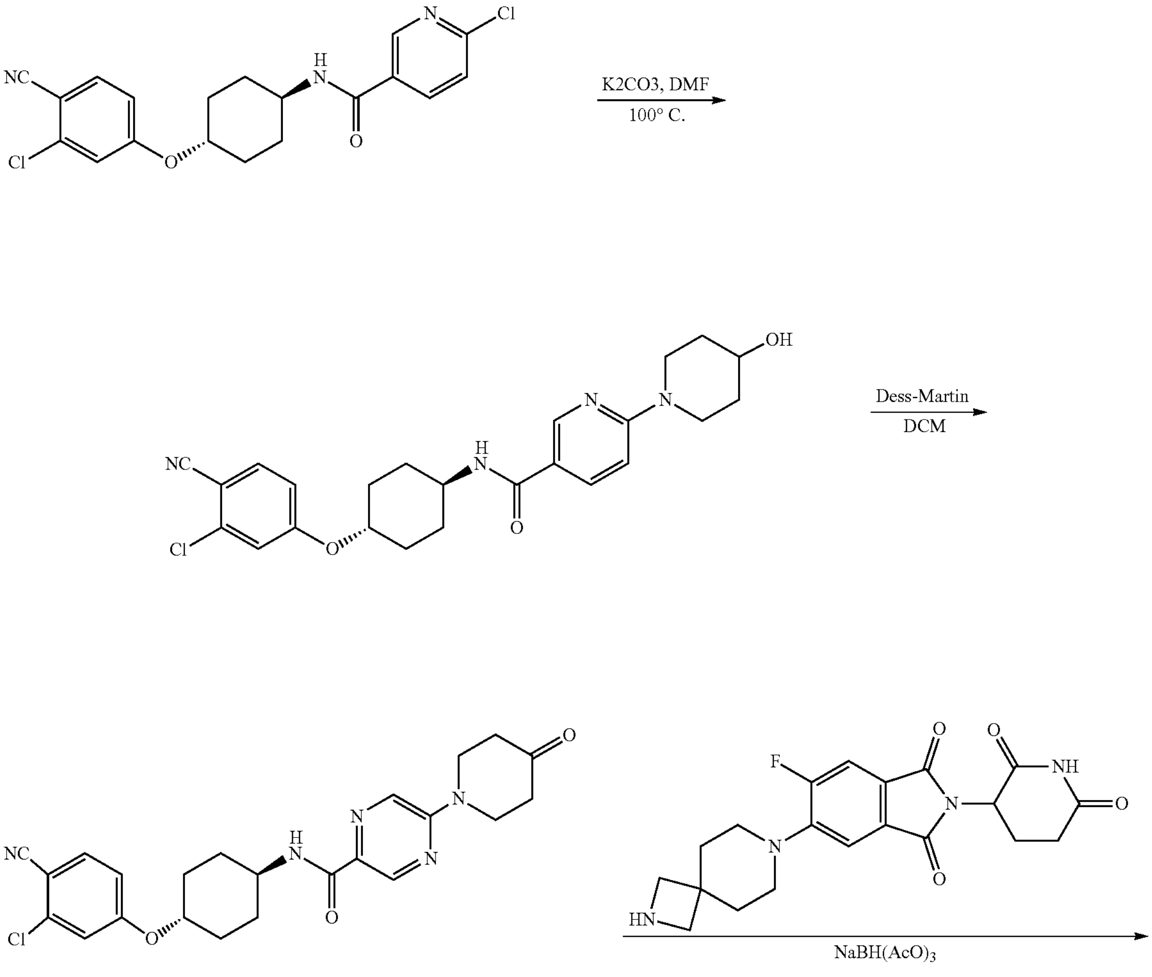

-continued
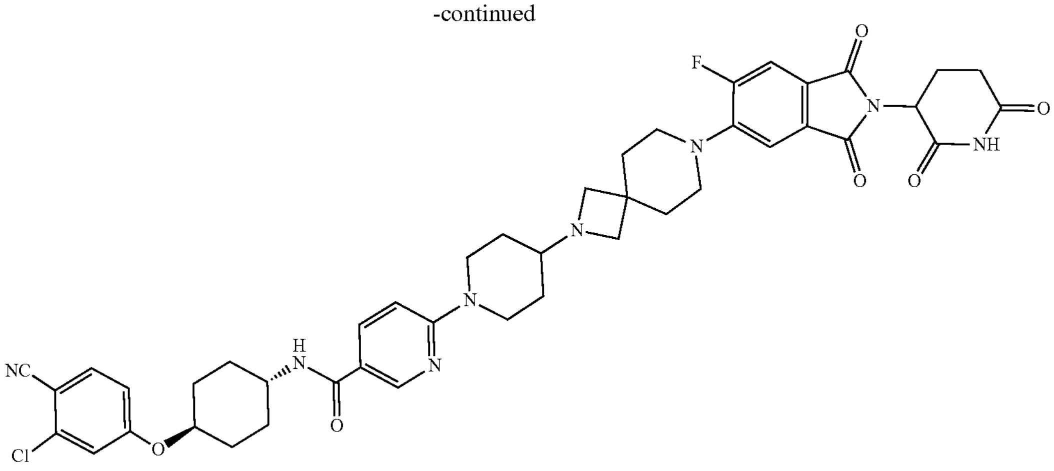
77
LC/MS (ESI+) Calcd for $C_{44}H_{46}ClFN_8O_6$ (M+H+) m/z, 837.3; found 837.3. $^1H$ NMR (400 MHz, $CDCl_3$) δ 8.84 (d, J=2.3 Hz, 1H), 8.25 (dd, J=9.0, 2.4 Hz, 1H), 7.56 (d, J=8.7 Hz, 1H), 7.47 (d, J=10.9 Hz, 1H), 7.38 (d, J=7.3 Hz, 1H), 6.99 (d, J=2.4 Hz, 1H), 6.85 (dd, J=8.7, 2.4 Hz, 1H), 6.77 (d, J=9.0 Hz, 1H), 5.93 (d, J=7.7 Hz, 1H), 4.93 (dd, J=12.3, 5.3 Hz, 1H), 4.52-4.25 (m, 4H), 4.04 (d, J=7.7 Hz, 1H), 3.33 (s, 3H), 3.18 (s, 3H), 3.04-2.65 (m, 6H), 2.57 (s, 1H), 2.27 (s, 4H), 2.17 (dd, J=25.9, 12.6 Hz, 9H), 2.05 (s, 3H), 1.97 (s, 4H), 1.85 (d, J=11.4 Hz, 2H), 1.67 (d, J=12.9 Hz, 2H), 1.45-1.33 (m, 4H).
78: HC-4304-01: N-((1r,4r)-4-(3-chloro-4-cyano-phenoxy)cyclohexyl)-6-(4-(7-(2-(2,6-dioxopiperidin-3-yl)-1,3-dioxoisoindolin-5-yl)-2,7-diazaspiro[3.5] nonan-2-yl)piperidin-1-yl) piperazine-3-formamide
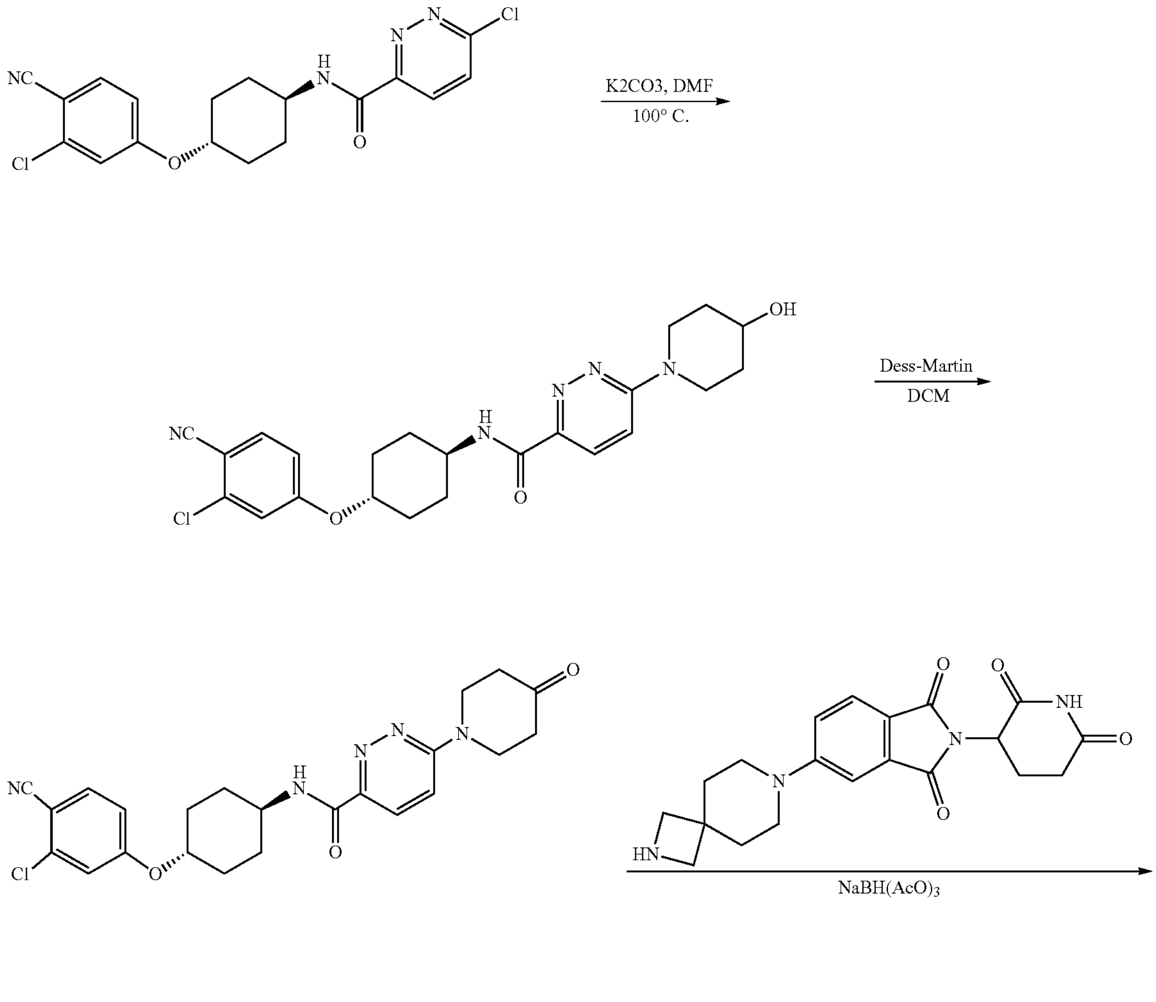

-continued
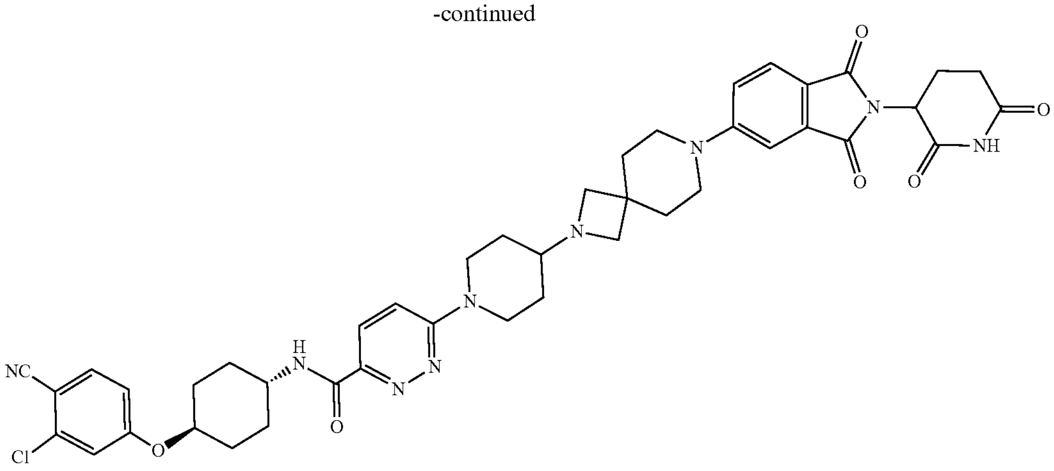
78
LC/MS (ESI+) Calcd for $C_{43}H_{46}ClNO_6$ (M+H+) m/z, 820.3. found 820.3. $^1H$ NMR (400 MHz, $CDCl_3$) δ 8.21 (s, 1H), 7.99 (d, J=9.5 Hz, 1H), 7.87 (d, J=8.2 Hz, 1H), 7.69 (d, J=8.5 Hz, 1H), 7.56 (d, J=8.7 Hz, 1H), 7.28 (d, J=2.2 Hz, 1H), 7.06 (dd, J=8.6, 2.2 Hz, 1H), 7.00 (t, J=5.7 Hz, 2H), 6.86 (dd, J=8.8, 2.4 Hz, 1H), 4.94 (dd, J=12.3, 5.3 Hz, 1H), 4.39 (s, 2H), 4.32 (t, J=10.0 Hz, 1H), 4.05 (dd, J=11.4, 7.2 Hz, 1H), 3.43-3.37 (m, 4H), 3.22 (d, J=10.9 Hz, 3H), 2.94-2.67 (m, 4H), 2.24-2.10 (m, 6H), 1.94 (s, 6H), 1.78-1.63 (m, 8H), 1.52-1.40 (m, 3H).
79: N-((1r,4r)-4-(4-cyano-3-(trifluoromethyl)phenoxy)cyclohexyl)-6-(4-(7-(2-(2,6-dioxopiperidin-3-yl)-6-fluoro-1,3-dioxoisoindolin-5-yl)-2,7-diazaspiro[3.5]nonan-2-yl)piperidin-1-yl)pyridazine-3-formamide
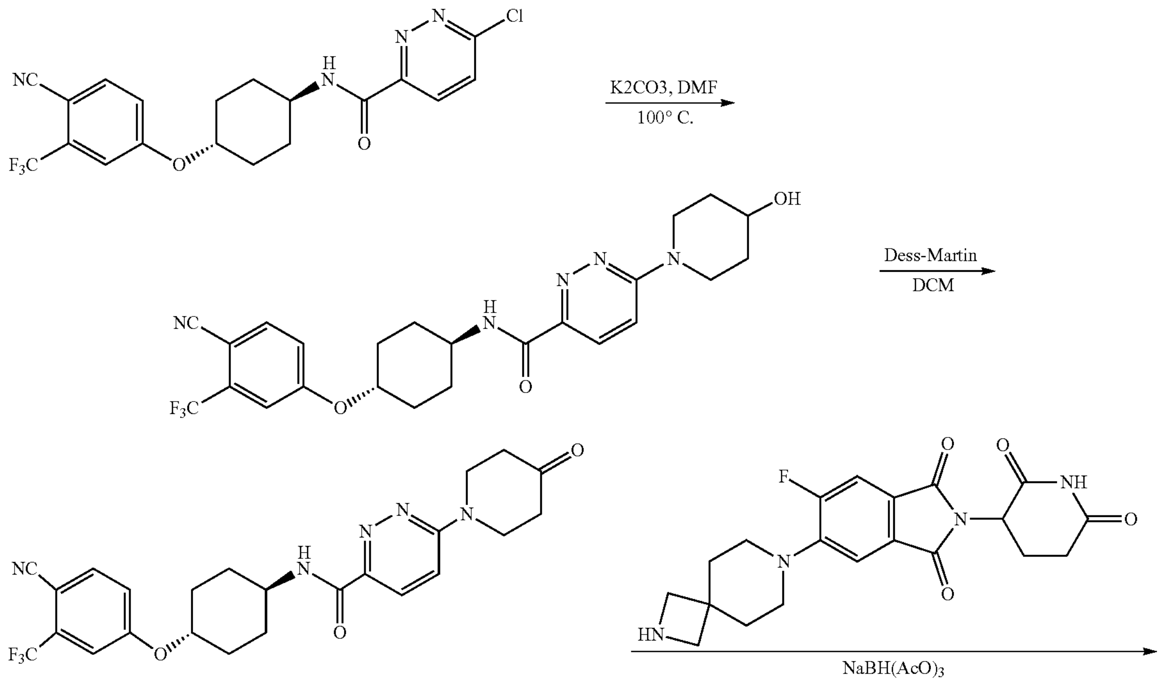

-continued
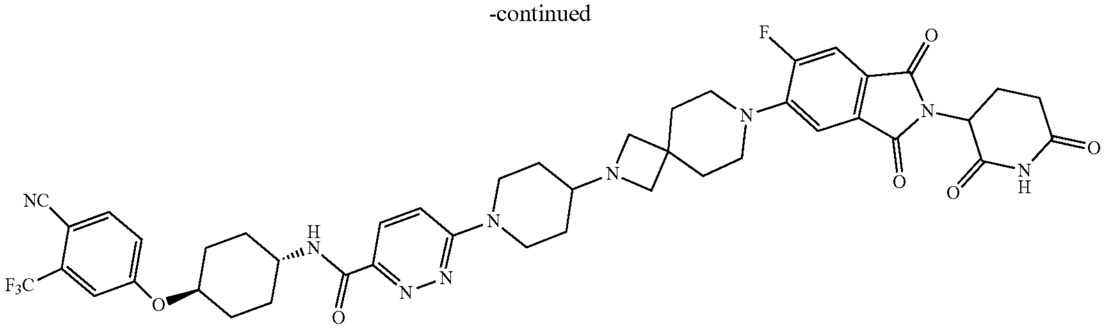
78
LC/MS (ESI) Calcd for $C_{44}H_{45}F4N_9O_6(M+H^+)$ m/z, 872.3. found 872.3. $^1$H NMR (400 MHz, $CDCl_3$) δ 8.45 (s, 1H), 8.00 (d, J=9.5 Hz, 1H), 7.89 (d, J=8.2 Hz, 1H), 7.75 (d, J=8.6 Hz, 1H), 7.47 (d, J=10.8 Hz, 1H), 7.38 (d, J=7.2 Hz, 1H), 7.26 (s, 1H), 7.11 (dd, J=8.7, 2.4 Hz, 1H), 7.00 (d, J=9.6 Hz, 1H), 4.93 (dd, J=12.3, 5.3 Hz, 1H), 4.48 (d, J=13.3 Hz, 2H), 4.40 (dd, J=11.8, 8.1 Hz, 2H), 4.13-4.01 (m, 2H), 3.49 (s, 4H), 3.16 (d, J=14.6 Hz, 7H), 2.96-2.68 (m, 6H), 2.24-2.16 (m, 7H), 2.05 (s, 2H), 2.02 (s, 6H), 1.95 (s, 2H), 1.77-1.67 (m, 3H), 1.49 (d, J=12.2 Hz, 3H).
80: N-((1s,3s)-3-(3-chloro-4-cyanophenoxy)-2,2,4,4-tetramethylcyclobutyl)-6-(4-(7-(2-(2,6-dioxopiperidin-3-yl)-6-fluoro-1,3-dioxoisoindolin-5-yl)-2,7-diazaspiro [3.5]nonan-2-yl)piperidin-1-yl) pyridazine-3-formamide
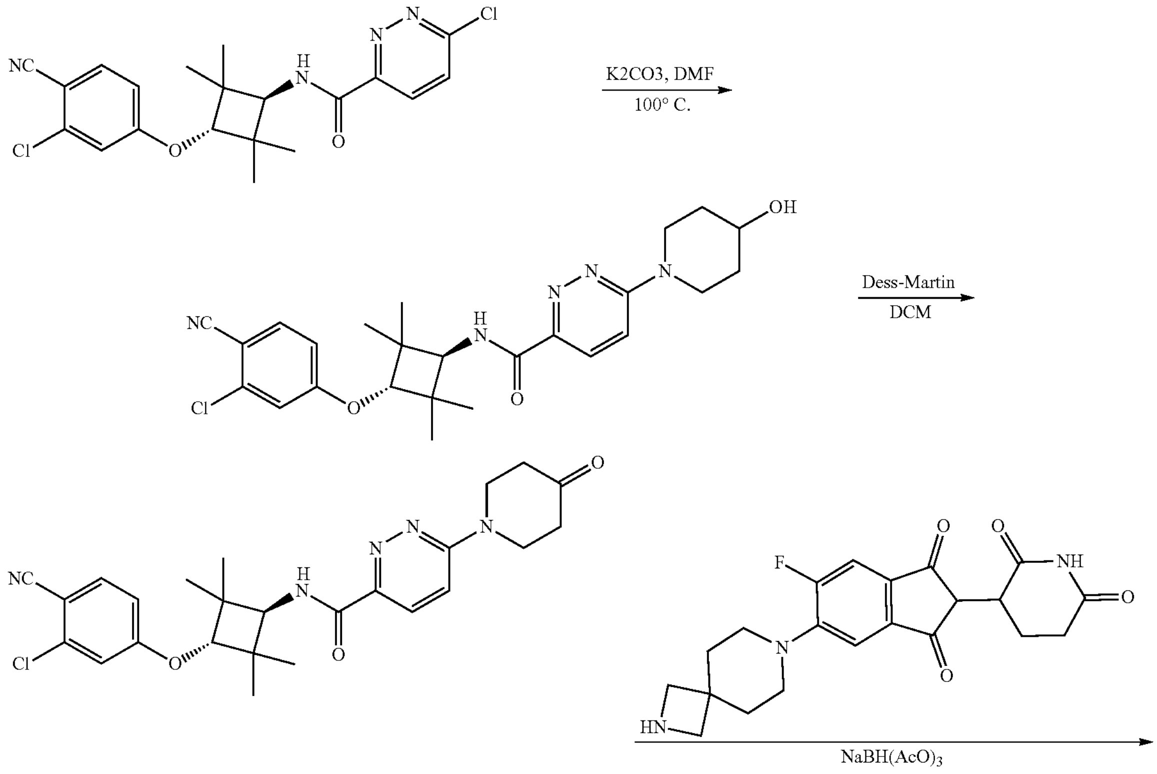

-continued
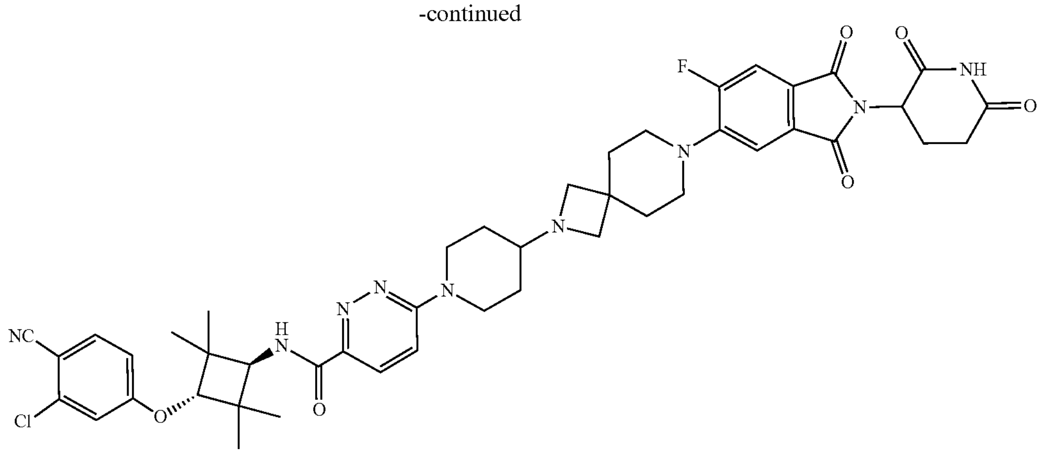
80
LC/MS (ESI+) Calcd for $C_{45}H_{49}ClF_4N_9O_6$ (M+H+) m/z, 866.3; found 866.3. $^1$H NMR (400 MHz, $CDCl_3$) δ 8.55-8.41 (m, 1H), 8.16 (d, J=9.1 Hz, 1H), 7.99 (d, J=9.5 Hz, 1H), 7.57 (d, J=8.7 Hz, 1H), 7.47 (d, J=10.9 Hz, 1H), 7.38 (d, J=7.2 Hz, 1H), 6.99 (dd, J=12.0, 6.0 Hz, 2H), 6.81 (dd, J=8.7, 2.4 Hz, 1H), 4.93 (dd, J=12.3, 5.3 Hz, 2H), 4.44 (d, J=13.4 Hz, 3H), 4.19 (d, J=9.0 Hz, 1H), 4.07 (s, 1H), 3.30 (s, 4H), 3.18 (d, J=6.2 Hz, 6H), 2.96-2.72 (m, 6H), 2.17-2.10 (m, 2H), 2.05 (s, 4H), 2.00-1.85 (m, 9H), 1.51 (d, J=10.6 Hz, 3H), 1.28 (s, 6H), 1.25 (s, 1H), 1.21 (s, 6H).
81: N-((1r,4r)-4-(3-chloro-4-cyanophenoxy)cyclohexyl)-6-(6-(1-(2-(2,6-dioxopiperidin-3-yl)-6-fluoro-1,3-dioxoisoindolin-5-yl)piperidine-4-yl)-2,6-diazaspiro[3.4]octan-2-yl)pyridazine-3-formamide
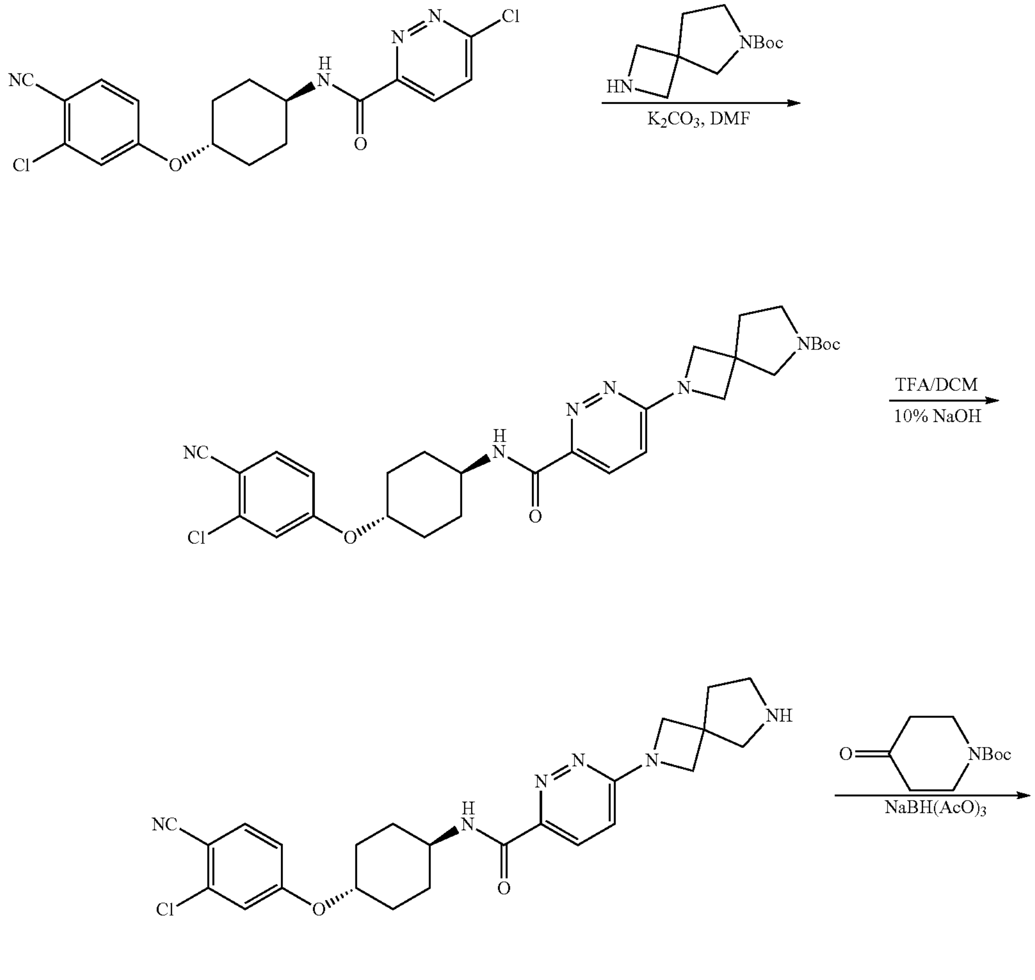

-continued
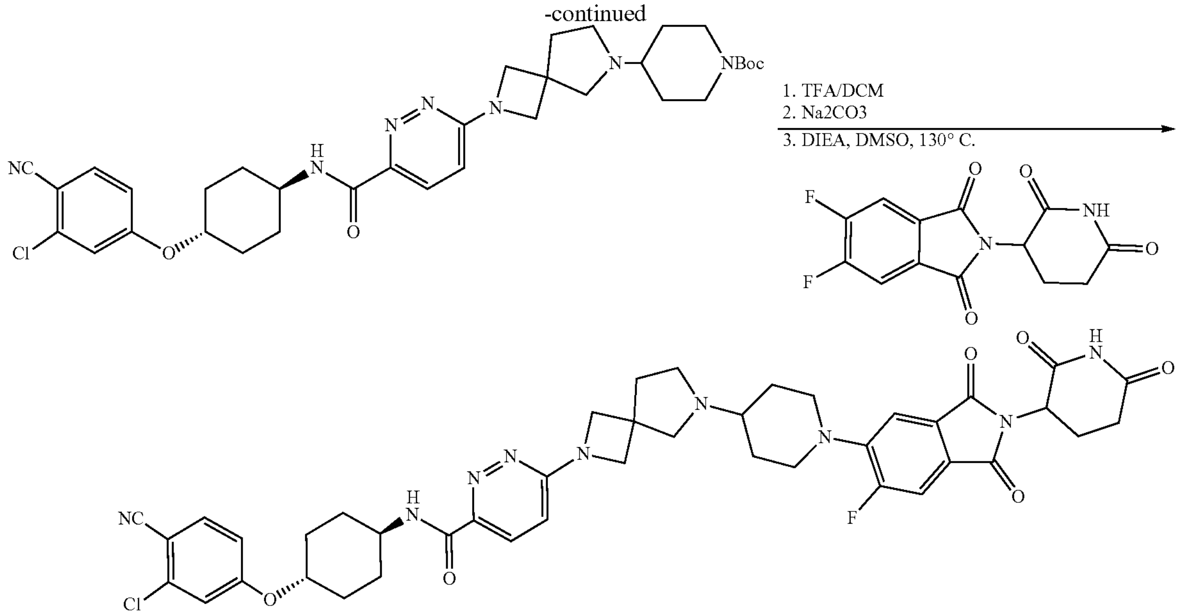
81
LC/MS (ESI+) Calcd for $C_{41}H_{43}ClFN_9O_6s$ (M+H+) m/z, 824.3; found 824.3. $^1$H NMR (400 MHz, $CDCl_3$) δ 8.20 (s, 1H), 7.99 (d, J=9.2 Hz, 1H), 7.88 (d, J=8.2 Hz, 1H), 7.56 (d, J=8.7 Hz, 1H), 7.47 (d, J=10.9 Hz, 1H), 7.39 (d, J=7.3 Hz, 1H), 7.00 (d, J=2.3 Hz, 1H), 6.86 (dd, J=8.7, 2.3 Hz, 1H), 6.61 (d, J=9.2 Hz, 1H), 4.94 (dd, J=12.3, 5.3 Hz, 1H), 4.32 (t, J=9.8 Hz, 1H), 4.19 (dd, J=24.2, 8.6 Hz, 4H), 4.05 (d, J=7.9 Hz, 1H), 3.67 (d, J=11.9 Hz, 2H), 3.06 (s, 2H), 2.98-2.70 (m, 8H), 2.54-2.36 (m, 1H), 2.27 (s, 2H), 2.16 (d, J=10.3 Hz, 6H), 2.05 (d, J=11.8 Hz, 3H), 1.83 (s, 3H), 1.69 (d, J=11.8 Hz, 9H), 1.47 (dd, J=22.4, 10.4 Hz, 3H).
82: N-((1r,4r)-4-(3-chloro-4-cyanophenoxy)cyclohexyl)-5-(6-(1-(2-(2,6-dioxopiperidin-3-yl)-6-fluoro-1,3-dioxoisoindolin-5-yl)piperidine-4-yl)-2,6-diazaspiro [3.4] octane-2-yl)pyrazine-2-carboxamide
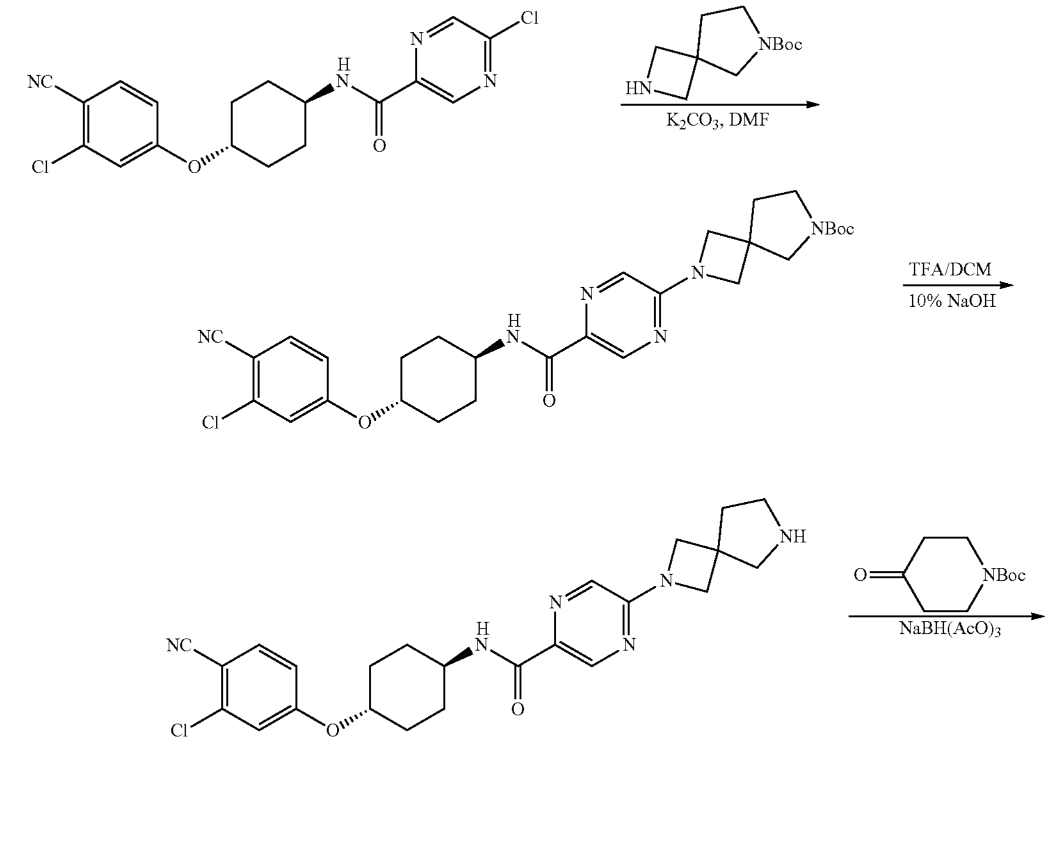

-continued
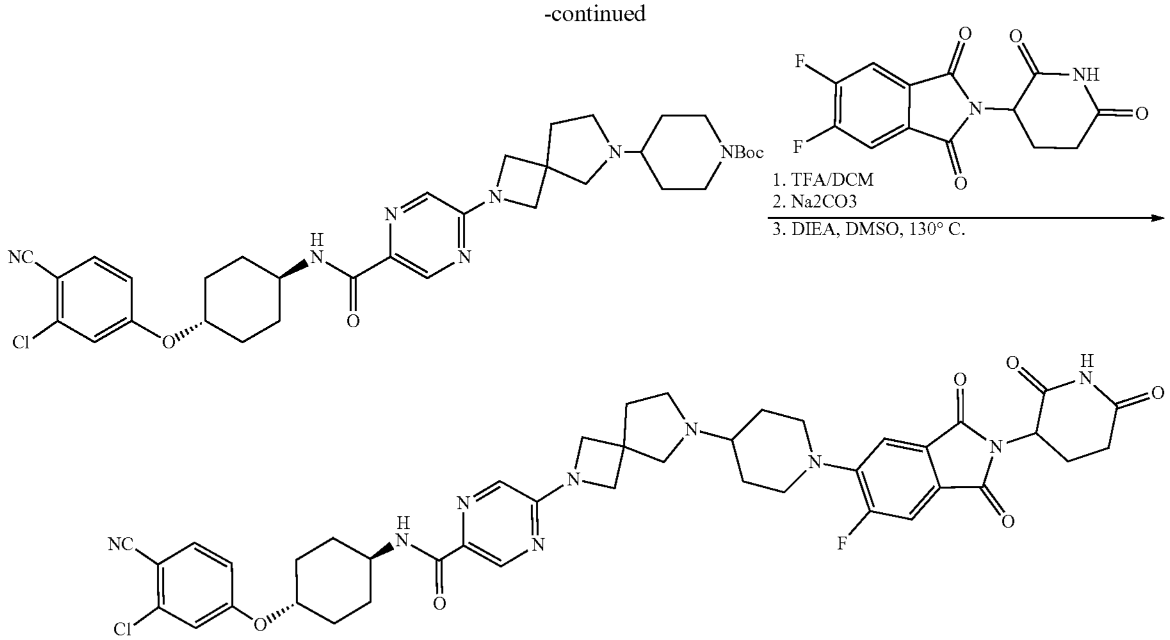
82
LC/MS ($ESI^+$) Calcd for $C_{44}H_{43}ClFN_9O_6s$ (M+H) m/z, 824.3; found 824.3. $^1H$ NMR (400 MHz, $CDCl_3$) δ 8.83 (d, J=1.3 Hz, 1H), 8.16 (s, 1H), 7.62-7.53 (m, 2H), 7.47 (d, J=10.9 Hz, 1H), 7.40 (dd, J=12.6, 7.8 Hz, 2H), 6.99 (d, J=2.4 Hz, 1H), 6.85 (dd, J=8.8, 2.4 Hz, 1H), 4.94 (dd, J=12.3, 5.3 Hz, 1H), 4.31 (s, 1H), 4.20 (s, 2H), 4.14 (d, J=8.6 Hz, 2H), 4.03 (d, J=7.8 Hz, 1H), 3.68 (d, J=12.7 Hz, 2H), 3.07 (s, 2H), 2.91 (dd, J=21.2, 10.1 Hz, 4H), 2.86-2.71 (m, 3H), 2.62 (s, 2H), 2.29 (s, 2H), 2.24-2.11 (m, 6H), 2.05 (s, 2H), 1.88 (s, 2H), 1.69 (dd, J=22.2, 9.9 Hz, 8H), 1.53-1.39 (m, 3H).
83: N-((1r,4r)-4-(3-chloro-4-cyanophenoxy)cyclohexyl)-5-(4-(2-(2,6-dioxopiperidin-3-yl)-6-fluoro-1,3-dioxoisoindolin-5-yl)-2,7-diazaspiro[3.5]nonan-7-yl)piperidin-1-yl)-1,3,4-thiadiazole-2-carboxamide
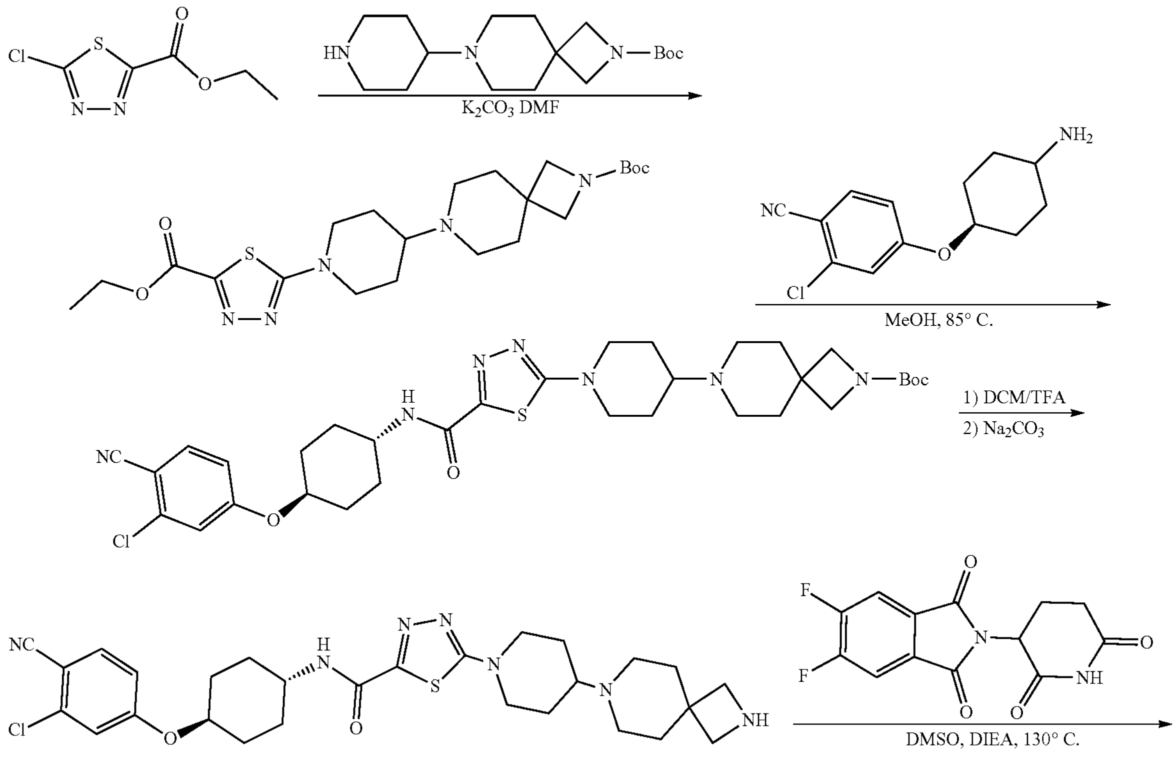

-continued
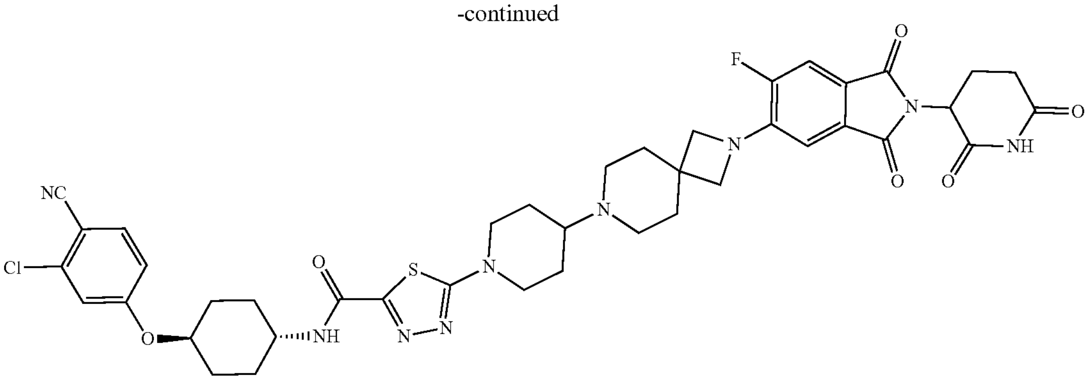
83
LC/MS (ESI+) Calcd for $C_{41}H_{43}ClFN_9O_6S$ (M+H+) m/z, 844.3; found 844.3. $^1$H NMR (400 MHz, $CDCl_3$) δ 8.00 (s, 1H), 7.56 (d, J=8.7 Hz, 1H), 7.38 (dd, J=11.6, 5.3 Hz, 1H), 7.05-6.97 (m, 2H), 6.88-6.78 (m, 2H), 4.91 (dd, J=12.0, 5.4 Hz, 1H), 4.31 (s, 1H), 4.13 (s, 2H), 3.98 (s, 1H), 3.95-3.85 (m, 4H), 3.59 (d, J=7.0 Hz, 2H), 3.23 (t, J=12.3 Hz, 2H), 2.80 (ddd, J=30.6, 27.4, 9.4 Hz, 6H), 2.16 (d, J=10.4 Hz, 6H), 1.68 (s, 2H), 1.62 (s, 4H), 1.53-1.46 (m, 2H), 1.25 (s, 6H).
84: Synthesis of N-((1r,4R)-4-(3-chloro-4-cyano-phenoxy)cyclohexyl)-1-(1r,4R)-4-((2-(2-(2,6-di-oxopiperidin-3-yl)-1,3-dioxoisoindolin-5-yl)-2,7-diazaspiro[3.5]nonan-7-yl)methyl)cyclohexyl)-1H-1,2,4-triazole-3-carboxamide

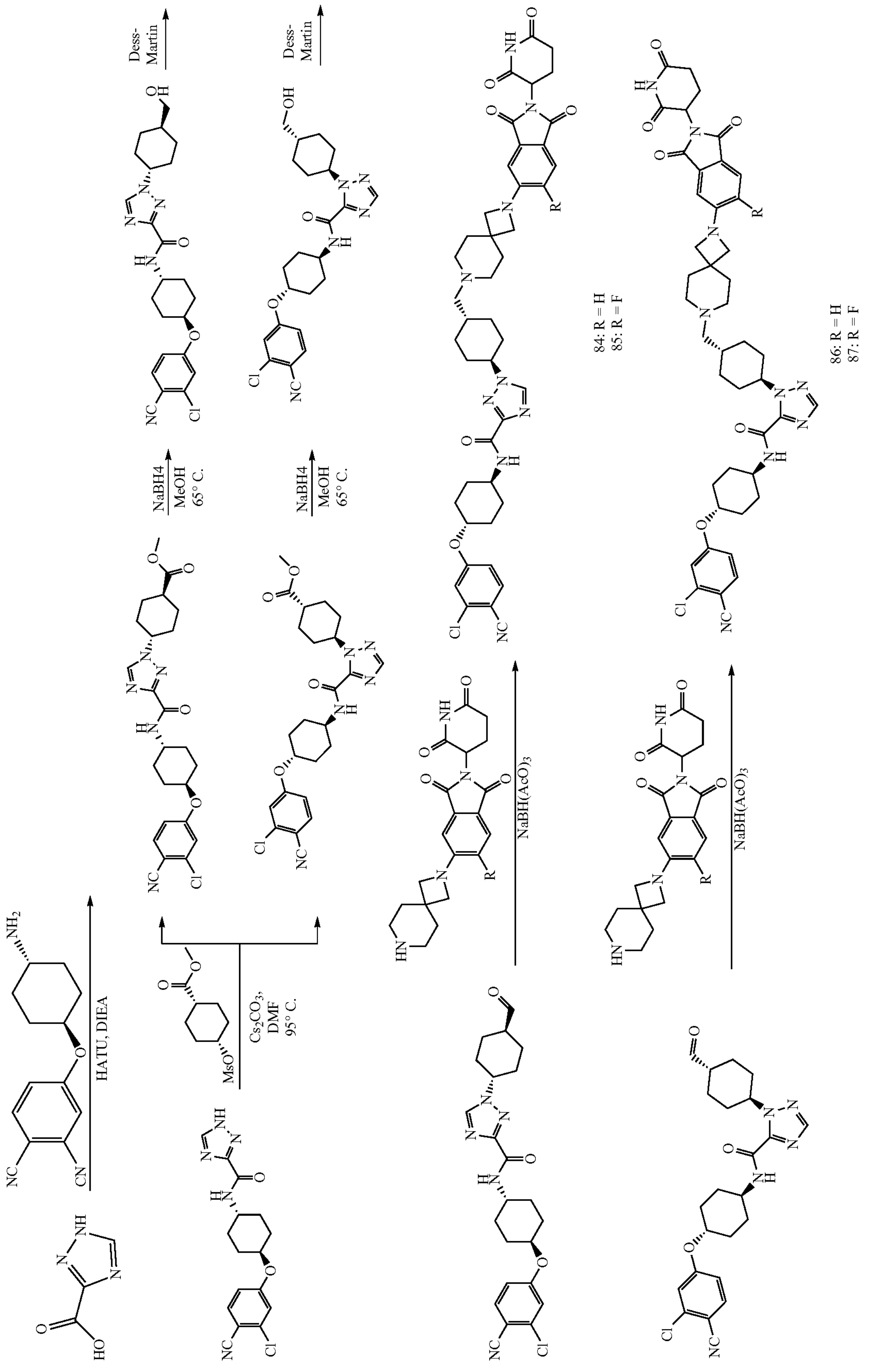
84: R = H
85: R = F
86: R = H
87: R = F

1. Synthesis of N-((1r,4r)-4-(3-chloro-4-cyanophenoxy)cyclohexyl)-1H-1,2,4-triazole-3-formamide 1H-1,2,4-triazole-3-carboxylic acid (500 mg, 1.99 mmol) was mixed with 10 mL of DMF, that is insoluble. To the mixture, was added DIEA (309 mg, 2.39 mmol). The reaction solution became clear, and then was cooled to −5° C., to which was added HATU (796 mg, 2.09 mmol). The resultant solution was stirred for more than 1 h, to which was then added 4-(((1r,4r)-4-aminocyclohexyl)oxy)-2-chlorobenzonitrile (237 mg, 2.09 mmol), and the mixture was stirred at low temperature for 30 min. The ice-salt bath was removed, and the reaction solution was naturally warmed to room temperature, and allowed to reacted for 2 h. Water was added to the reaction system under stirring, and lots of solid was precipitated. The solution was filtered, and the filter cake was dried to provide N-((1r,4r)-4-(3-chloro-4-cyanophenoxy)cyclohexyl)-1H-1,2,4-triazole-3-formamide (660 mg), with a yield of 95.7%. LC/MS (ESI$^+$) Calcd for $C_{16}H_{16}ClN_5O_2$ (M+H$^+$) m/z, 346.1; found 346.1.

2. Synthesis of (1R,4r)-methyl 4-(3-((1R,4r)-4-(3-chloro-4-cyanophenoxy)cyclohexyl) carbamoyl)-1H-1,2,4-triazol-1-yl)cyclohexanoate N-((1r,4r)-4-(3-chloro-4-cyanophenoxy)cyclohexyl)-1H-1,2,4-triazole-3-formamide (500 mg, 1.45 mmol) was dissolved in DMF, to which were then added (1s,4s)-methyl 4-((methylsulfonyl)oxy)cyclohexanecarboxylate (1.02 g, 4.34 mmol) and cesium carbonate (1.41 g, 4.34 mmol). The mixture was heated to 95° C. and reacted overnight. The reaction was quenched by adding water to the system. The resultant solution was extracted with EA, dried, concentrated, and purified, to provide (1R,4r)-methyl 4-(3-((1R,4r)-4-(3-chloro-4-cyanophenoxy)cyclohexyl)carbamoyl)-1H-1,2,4-triazol-1-yl)cyclohexanecarboxylate (210 mg), with a yield of 31.65%. LC/MS (ESI$^+$) Calcd for $C_{24}H_{28}ClN_5O4$ (M+H$^+$) m/z, 486.2; found 486.2.

3. N-((1r,4R)-4-(3-chloro-4-cyanophenoxy)cyclohexyl)-1-((1r,4R)-4-(hydroxymethyl) cyclohexyl)-1H-1,2,4-triazole-3-formamide (1R,4r)-methyl 4-(3-((1R,4r)-4-(3-chloro-4-cyanophenoxy)cyclohexyl)carbamoyl)-1H-1,2,4-triazol-1-yl)cyclohexanecarboxylate (200 mg, 0.41 mmol) was dissolved in a 1:1 mixed solvent of THF and methanol, to which was slowly added sodium borohydride (62 mg, 1.65 mmol). The reaction solution was allowed to react for 2 h under reflux at 65° C., and then the reaction was completed. The reaction solution was cooled to room temperature, to which was added water to quench the reaction. The resultant solution was extracted with EA, dried, and purified by TLC, to provide N-((1r,4R)-4-(3-chloro-4-cyanophenoxy)cyclohexyl)-1-((1r,4R)-4-(hydroxymethyl) cyclohexyl)-1H-1,2,4-triazole-3-formamide (140 mg), with a yield of 61.87%. LC/MS (ESI$^+$) Calcd for $C_{23}H_{28}ClN_5O_3$ (M+H$^+$) m/z, 458.2; found 458.2.

4. Synthesis of Compound N-((1r,4R)-4-(3-chloro-4-cyanophenoxy)cyclohexyl)-1-((1r,4R)-4-formylcyclohexyl)-1H-1,2,4-triazole-3-formamide N-((1r,4R)-4-(3-chloro-4-cyanophenoxy)cyclohexyl)-1-((1r,4R)-4-(hydroxymethyl) cyclohexyl)-1H-1,2,4-triazole-3-formamide (130 mg, 0.28 mmol) was dissolved in 3 mL DCM, to which was added Dess-Martin periodinane (181 mg, 0.43 mmol) at room temperature, and the mixture was allowed to react 1 h. The reaction solution was filtered, and the filtrate was successively washed with the solution of sodium bisulfite and the saturated solution of sodium bicarbonate, dried, filtered, concentrated, and purified, to provide N-((1r,4R)-4-(3-chloro-4-cyanophenoxy)cyclohexyl)-1-((1r,4R)-4-formylcyclohexyl)-1H-1,2,4-triazole-3-formamide (80 mg), with a yield of 61.84%.

5. N-((1r,4R)-4-(3-chloro-4-cyanophenoxy)cyclohexyl)-1-(1r,4R)-4-((2-(2-(2,6-dioxopiperidin-3-yl)-1,3-dioxoisoindolin-5-yl)-2,7-diazaspiro[3.5]nonan-7-yl)methyl) cyclohexyl)-1H-1,2,4-triazole-3-carboxamide N-((1r,4R)-4-(3-chloro-4-cyanophenoxy)cyclohexyl)-1-((1r,4R)-4-formylcyclohexyl)-1H-1,2,4-triazole-3-formamide (40 mg, 0.09 mmol) and 2-(2,6-dioxopiperidin-3-yl)-5-(2,7-diazaspiro[3.5]nonan-2-yl)isoindoline-1,3-dione (37 mg, 0.10 mmol) were dissolved in a mixed solvent of DCM and MeOH (1:1, 2 mL), to which was slowly added sodium triacetoxyborohydride (75 mg, 0.35 mmol). After 2 h, TLC indicated the completion of the reaction. The reaction was quenched by adding water, and the resultant solution was extracted with DCM, dried, and purified to provide N-((1r,4R)-4-(3-chloro-4-cyanophenoxy)cyclohexyl)-1-(1r,4R)-4-((2-(2-(2,6-dioxopiperidin-3-yl)-1,3-dioxoisoindolin-5-yl)-2,7-diazaspiro[3.5]nonan-7-yl)methyl)cyclohexyl)-1H-1,2,4-triazole-3-carboxamide (35 mg), with a yield of 48.57%. LC/MS (ESI$^+$) Calcd for $C_{43}H_{48}ClN_9O_6$(M+H$^+$) m/z, 822.3; found 822.3. $^1$H NMR (400 MHz, $CDCl_3$) δ 8.11 (s, 1H), 7.64 (d, J=8.3 Hz, 1H), 7.55 (d, J=8.7 Hz, 1H), 7.15 (d, J=8.2 Hz, 1H), 6.98 (d, J=2.3 Hz, 1H), 6.84 (dd, J=8.7, 2.3 Hz, 1H), 6.77 (d, J=1.7 Hz, 1H), 6.50 (dd, J=8.3, 1.9 Hz, 1H), 4.94 (dd, J=12.3, 5.3 Hz, 2H), 4.72 (d, J=25.2 Hz, 6H), 4.25 (dt, J=15.4, 11.1 Hz, 3H), 4.09 (d, J=8.1 Hz, 1H), 3.73 (s, 4H), 2.81 (ddd, J=33.0, 24.0, 10.4 Hz, 3H), 2.40 (s, 3H), 2.23-2.16 (m, 6H), 1.87 (s, 6H), 1.67 (dd, J=23.0, 10.0 Hz, 4H), 1.47 (dd, J=23.1, 10.5 Hz, 2H), 1.25 (s, 1H).

85: N-((1r,4R)-4-(3-chloro-4-cyanophenoxy)cyclohexyl)-1-((1r,4R)-4-((2-(2-(2,6-dioxopiperidin-3-yl)-6-fluoro-1,3-dioxoisoindolin-5-yl)-2,7-diazaspiro[3.5]nonan-7-yl)methyl)cyclohexyl)-1H-1,2,4-triazole-3-formamide LC/MS (ESI$^+$) Calcd for $C_{41}H_{43}ClFN_9O_6s$ (M+H$^+$) m/z, 844.3; found 844.3. $^1$H NMR (400 MHz, $CDCl_3$) δ 8.63 (s, 1H), 8.12 (s, 1H), 7.56 (d, J=8.7 Hz, 1H), 7.36 (d, J=10.8 Hz, 1H), 7.18 (d, J=8.3 Hz, 1H), 6.99 (d, J=2.4 Hz, 1H), 6.87-6.77 (m, 2H), 4.92 (dd, J=12.2, 5.3 Hz, 1H), 4.63 (s, 2H), 4.32-4.18 (m, 2H), 4.15-4.05 (m, 1H), 3.89 (s, 4H), 2.97-2.65 (m, 4H), 2.41 (s, 5H), 2.27 (d, J=6.9 Hz, 4H), 2.15 (dd, J=8.9, 6.4 Hz, 5H), 2.08 (s, 4H), 1.92 (s, 4H), 1.67 (dd, J=22.6, 9.8 Hz, 4H), 1.47 (d, J=12.7 Hz, 2H).

86: N-((1r,4R)-4-(3-chloro-4-cyanophenoxy)cyclohexyl)-1-((1r,4R)-4-((2-(2-(2,6-dioxopiperidin-3-yl)-1,3-dioxoisoindolin-5-yl)-2,7-diazaspiro[3.5]nonan-7-yl)methyl)cyclohexyl)-1H-1,2,4-triazole-5-formamide LC/MS (ESI$^+$) Calcd for $C_{43}H_{48}ClN_9O_6$(M+H$^+$) m/z, 822.3; found 822.3. $^1$H NMR (400 MHz, $CDCl_3$) δ 8.35 (s, 1H), 7.86 (s, 1H), 7.64 (d, J=8.3 Hz, 1H), 7.56 (d, J=8.7 Hz, 1H), 7.48 (d, J=8.2 Hz, 1H), 6.99 (d, J=2.4 Hz, 1H), 6.84 (dd, J=8.7, 2.4 Hz, 1H), 6.77 (d, J=2.0 Hz, 1H), 6.50 (dd, J=8.4, 2.0 Hz, 1H), 5.39 (s, 1H), 4.93 (dd, J=12.3, 5.3 Hz, 2H), 4.79 (s, 4H), 4.30 (t, J=10.2 Hz, 1H), 3.99 (d, J=8.3 Hz, 1H), 3.73 (s, 4H), 2.93-2.69 (m, 3H), 2.28 (s, 4H), 2.07 (d, J=13.4 Hz, 4H), 1.98 (d, J=11.0 Hz, 4H), 1.91-1.82 (m, 6H), 1.70-1.60 (m, 3H), 1.57-1.47 (m, 2H).

87: N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5]nonan-7-yl)methyl)cyclohexyl)-1H-1,2,4-triazole-5-formamide LC/MS (ESI+) Calcd for $C_{41}H_{43}ClFN_9O_6s$ (M+H+) m/z, 844.3; found 844.3. $^1H$ NMR (400 MHz, $CDCl_3$) δ 8.36 (s, 1H), 7.86 (s, 1H), 7.56 (d, J=8.7 Hz, 1H), 7.48 (d, J=8.2 Hz, 1H), 7.36 (d, J=10.9 Hz, 1H), 6.99 (d, J=2.4 Hz, 1H), 6.84 (dd, J=8.8, 2.4 Hz, 1H), 6.80 (d, J=7.5 Hz, 1H), 5.39 (t, J=11.5 Hz, 1H), 4.91 (dd, J=12.2, 5.3 Hz, 1H), 4.58 (s, 4H), 4.30 (t, J=10.1 Hz, 1H), 3.99 (dd, J=11.6, 7.4 Hz, 1H), 3.89 (d, J=1.7 Hz, 4H), 2.95-2.65 (m, 4H), 2.20 (d, J=5.1 Hz, 4H), 2.08 (s, 3H), 2.04 (d, J=4.3 Hz, 1H), 1.97 (t, J=11.2 Hz, 4H), 1.89 (s, 4H), 1.72-1.59 (m, 4H), 1.51 (dd, J=21.8, 11.3 Hz, 3H).

88: Synthesis of N-((1r,4r)-4-(3-chloro-4-cyanophenoxy)cyclohexyl)-6-(7-(1-(2-(2,6-dioxopiperidin-3-yl)-1,3-dioxoisoindolin-5-yl)piperidine-4-yl)-2,7-diazaspiro[3.5]nonan-2-yl)pyridazine-3-formamide

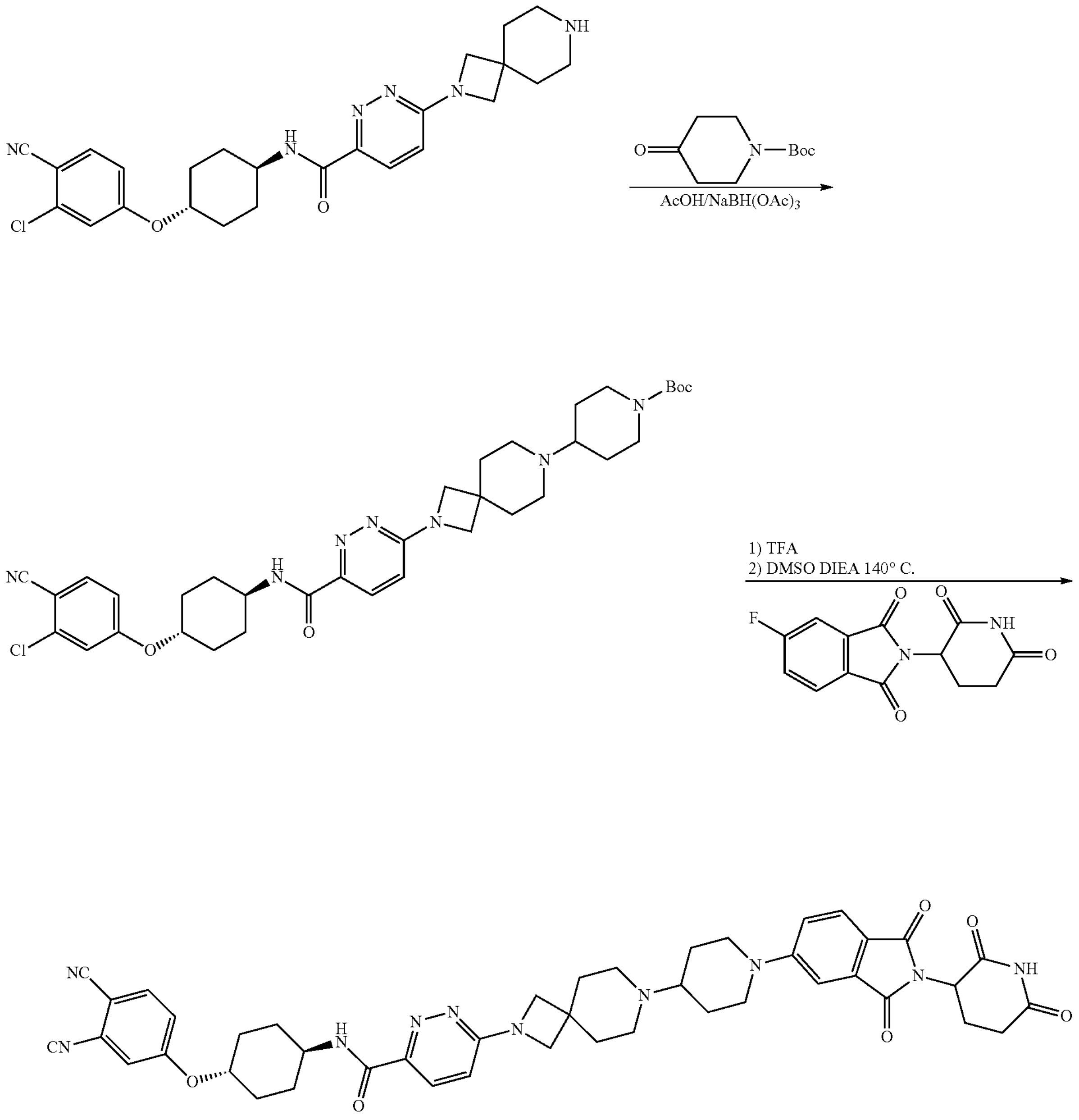

1. Synthesis of t-butyl 4-(2-{6-[4-(3-chloro-4-cyano-phenoxy)-cyclohexylcarbamoyl]-pyridazin-3-yl}-2,7-diaza-spirocyclo[3.5]nonan-7-yl)-piperidine-1-carboxylate N-((1r,4r)-4-(3-Chloro-4-cyanophenoxy)cyclohexyl)-6-(2,7-diazaspiro[3.5]nonan-2-yl)pyridazine-3-formamide (100 mg, 0.208 mmol) was dissolved in 5 mL of dichloromethane, to which was added 4-Bocpiperidone (414 mg, 2.1 mmol), and then 0.5 drops of acetic acid was added. The mixture was refluxed at 40° C. for 1 h, and cooled to room temperature, to which was added sodium triacetylborohydride (441 mg, 2.08 mmol). The reaction solution was refluxed at 40° C. overnight, and cooled to room temperature. The solution was washed with water, concentrated to dry under reduced pressure, and separated by TLC, to provide the product t-butyl 4-(2-{6-[4-(3-chloro-4-cyano-phenoxy)-cyclohexylcarbamoyl]-pyridazin-3-yl}-2,7-diaza-spirocyclo[3.5]nonan-7-yl)-piperidine-1-carboxylate (120 mg), with a yield of 86.8%, LC/MS (ESI$^+$) calcd for $C_{35}H_{46}ClN_7O_4$ ([M+H]$^+$) m/z 663.8.

2. Synthesis of N-((1r,4r)-4-(3-chloro-4-cyanophenoxy)cyclohexyl)-6-(7-(1-(2-(2,6-dioxopiperidin-3-yl)-1,3-dioxoisopentanol-5-yl)piperidine-4-yl)-2,7-diazaspiro[3.5]nonan-2-yl)pyridazine-3-formamide t-Butyl 4-(2-{6-[4-(3-chloro-4-cyano-phenoxy)-cyclohexylcarbamoyl]-pyridazin-3-yl}-2,7-diaza-spirocyclo[3.5]nonan-7-yl)-piperidine-1-carboxylate (45 mg, 0.068 mmol) was dissolved in 3 mL of dichloromethane, to which was added 3 mL of trifluoroacetic acid. The solution was stirred 2 h at room temperature, and concentrated to dry under reduced pressure. To the residue, was added dichloromethane, and the solution was concentrated under reduced pressure, that was repeated once. To the resultant solution, were successively added 3 mL of DMSO, 0.5 mL of DIEA, and 2-(2,6-dioxopiperidin-3-yl)-5-fluoroisoindole-1,3-dione. The reaction solution was refluxed at 135° C. for 1.5 h, and cooled to room temperature, to which was added 10 mL of dichloromethane. The reaction solution was washed twice with 10 mL of water, and then washed once with saturated brine, dried over anhydrous sodium sulfate, concentrated to dry under reduced pressure, and separated by thin-layer chromatography to obtain N-((1r,4r)-4-(3-chloro-4-cyano-phenoxy)cyclohexyl)-6-(7-(1-(2-(2,6-dioxopiperidin-3-yl)-1,3-dioxoisoindolin-5-yl)piperidine-4-yl)-2,7-diazaspiro[3.5]nonan-2-yl)pyridazine-3-formamide as a yellow solid product (35 mg), with a yield of 62.7%, LC/MS (ESI$^+$) calcd for $C_{43}H_{46}ClN_9O_6$ ([M+H]$^+$) m/z 820.3, $^1$H NMR (400 MHz, $CDCl_3$) 8.20 (s, 1H), 7.98 (d, J=9.2 Hz, 1H), 7.88 (d, J=8.3 Hz, 1H), 7.69 (d, J=8.5 Hz, 1H), 7.56 (d, J=8.7 Hz, 1H), 7.29 (d, J=2.2 Hz, 1H), 7.06 (dd, J=8.6, 2.2 Hz, 1H), 7.00 (d, J=2.3 Hz, 1H), 6.85 (dd, J=8.8, 2.4 Hz, 1H), 6.58 (d, J=9.3 Hz, 1H), 4.95 (dd, J=12.3, 5.3 Hz, 1H), 4.32 (dd, J=11.7, 8.1 Hz, 1H), 4.03 (t, J=11.6 Hz, 3H), 3.91 (s, 4H), 3.00 (t, J=11.8 Hz, 2H), 2.94-2.70 (m, 4H), 2.62 (s, 4H), 2.15 (dt, J=10.4, 7.8 Hz, 6H), 1.97 (s, 4H), 1.72-1.65 (m, 5H), 1.53-1.43 (m, 2H).

89: Synthesis of N-((1r,4r)-4-(3-chloro-4-cyanophenoxy)cyclohexyl)-5-(7-(1-(2-(2,6-dioxopiperidin-3-yl)-1,3-dioxoisoindolin-5-yl)piperidine-4-yl)-2,7-diazaspiro[3.5]nonan-2-yl)pyrazine-2-carboxamide

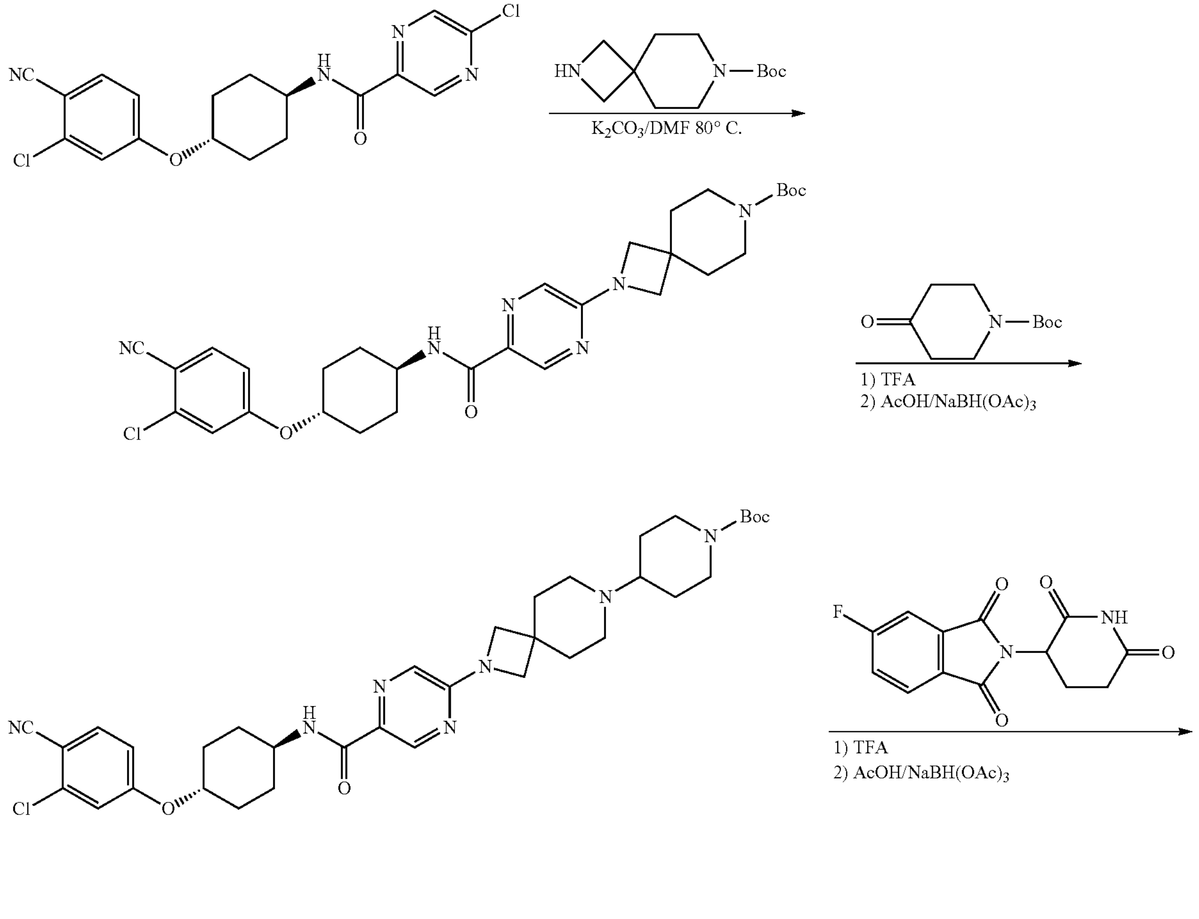

-continued

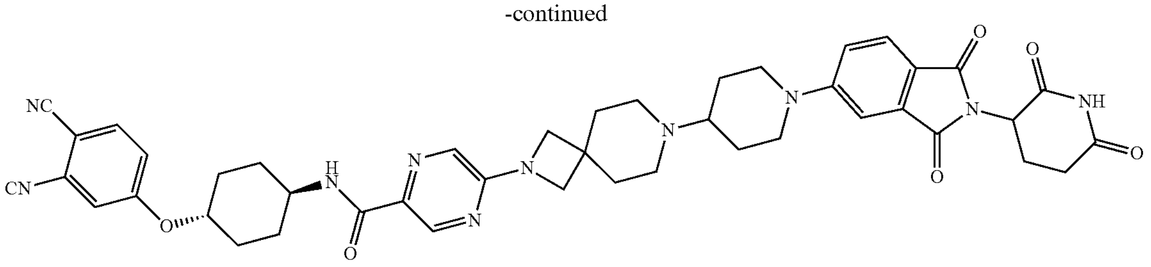

89

Synthetic procedures referred to 88.

LC/MS (ESI$^+$) calcd for $C_{43}H_{46}ClN_9O_6$ ([M+H]$^+$) m/z 820.3, $^1$H NMR (400 MHz, $CDCl_3$) δ 8.83 (d, J=1.2 Hz, 1H), 8.09 (s, 1H), 7.70 (d, J=8.5 Hz, 1H), 7.63-7.51 (m, 2H), 7.39 (d, J=8.2 Hz, 1H), 7.29 (d, J=2.0 Hz, 1H), 7.07 (dd, J=8.5, 2.0 Hz, 1H), 6.99 (d, J=2.3 Hz, 1H), 6.84 (dd, J=8.7, 2.4 Hz, 1H), 4.99-4.90 (m, 1H), 4.30 (td, J=10.1, 5.2 Hz, 1H), 4.03 (d, J=9.1 Hz, 3H), 3.91 (s, 4H), 3.00 (t, J=12.1 Hz, 2H), 2.94-2.72 (m, 4H), 2.66 (d, J=33.9 Hz, 4H), 2.29-2.09 (m, 6H), 1.99 (s, 4H), 1.71 (dd, J=18.7, 8.9 Hz, 5H), 1.48 (dd, J=18.3, 6.9 Hz, 2H).

90: 2-chloro-4-((1r,3r)-3-(2-(4-((2-(2,6-dioxopiperidin-3-yl)-6-fluoro-1,3-dioxoisoindolin-5-yl)-2,7-diazaspiro[3.5]nonane-7-yl)methyl)piperidin-1-yl)-5-oxo-5,7-dihydro-6H-pyrrolo[3,4-b]pyridin-6-yl)-2,2,4,4-tetramethylcyclobutoxy) benzonitrile

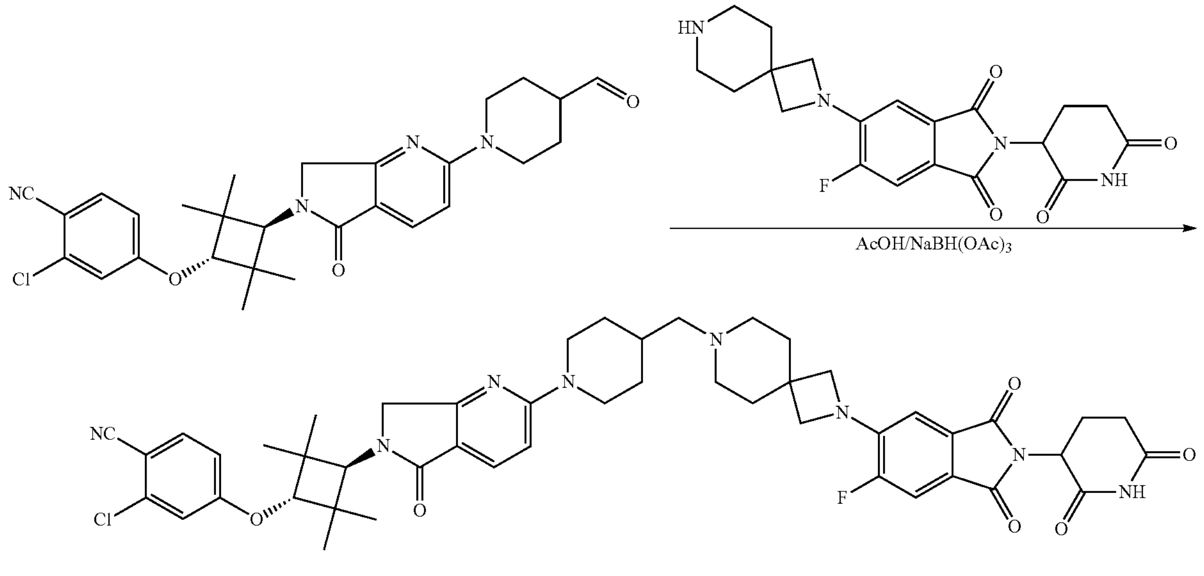

90

2-Chloro-4-(3-(2-(4-formylpiperidin-1-yl)-5-oxoisoindolin-5,7-dihydro-6H-pyrrolo[3,4-b]pyridin-6-yl)-2,2,4,4-tetramethylcyclobutoxy)benzonitrile (66 mg, 0.13 mmol) was dissolved in 5 mL of dichloromethane, to which were successively added 2-(2,6-dioxoisoindolin-3-yl)-5-fluoro-6-(2,7-diazaspiro[3.5]nonan-2-yl)isobenzyl-1,3-dione (45 mg, 0.11 mmol) and 0.3 drops of acetic acid. The mixture was allowed to react at room temperature for 15 min, to which was added sodium triacetylborohydride (200 mg, 0.94 mmol), followed by reacting at room temperature for 1 h. The resultant solution was washed with water, concentrated to dry under reduced pressure, and separated by TLC, to provide 2-chloro-4-(3-(2-(4-((2-(2,6-dioxopiperidin-3-yl)-6-fluoro-1,3-dioxoisoindolin-5-yl)-2,7-diazaspiro[3.5]nonan-7-yl)methyl)piperidin-1-yl)-5-oxo-5,7-dihydro-6H-pyrrolo[3,4-b]pyridin-6-yl)-2,2,4,4-tetramethylcyclobutoxy)benzonitrile as a yellow solid (55 mg), with a yield of 56.1%, LC/MS (ESI$^+$) calcd for $C_{48}H_{52}ClFN_8O_6$ ([M+H]$^+$) m/Z 891.3, $^1$H NMR (400 MHz, $CDCl_3$) δ 8.03 (s, 1H), 7.80 (d, J=8.8 Hz, 1H), 7.57 (d, J=8.7 Hz, 1H), 7.36 (d, J=10.5 Hz, 1H), 6.98 (d, J=2.4 Hz, 1H), 6.87-6.76 (m, 2H), 6.67 (d, J=8.9 Hz, 1H), 4.91 (dd, J=12.2, 5.3 Hz, 1H), 4.54 (s, 2H), 4.45 (d, J=10.1 Hz, 3H), 4.25 (s, 1H), 3.98 (s, 1H), 3.89 (s, 2H), 3.63 (t, J=34.0 Hz, 1H), 3.18-2.59 (m, 7H), 2.37 (s, 3H), 2.14 (dd, J=15.6, 7.6 Hz, 4H), 1.86 (s, 5H), 1.61 (s, 2H), 1.45 (s, 6H), 1.23 (s, 6H).

91: N-((1r,4r)-4-(3-chloro-4-cyanophenoxy)cyclohexyl)-6-(2-((1-(2,6-dioxopiperidin-3-yl)-6-fluoro-1,3-dioxoisoindolin-5-yl)piperidine-4-yl)methyl)-2,7-diazaspiro[(3.5]nonan-7-yl)-N-(methyl-$d_3$) pyridazine-3-formamide

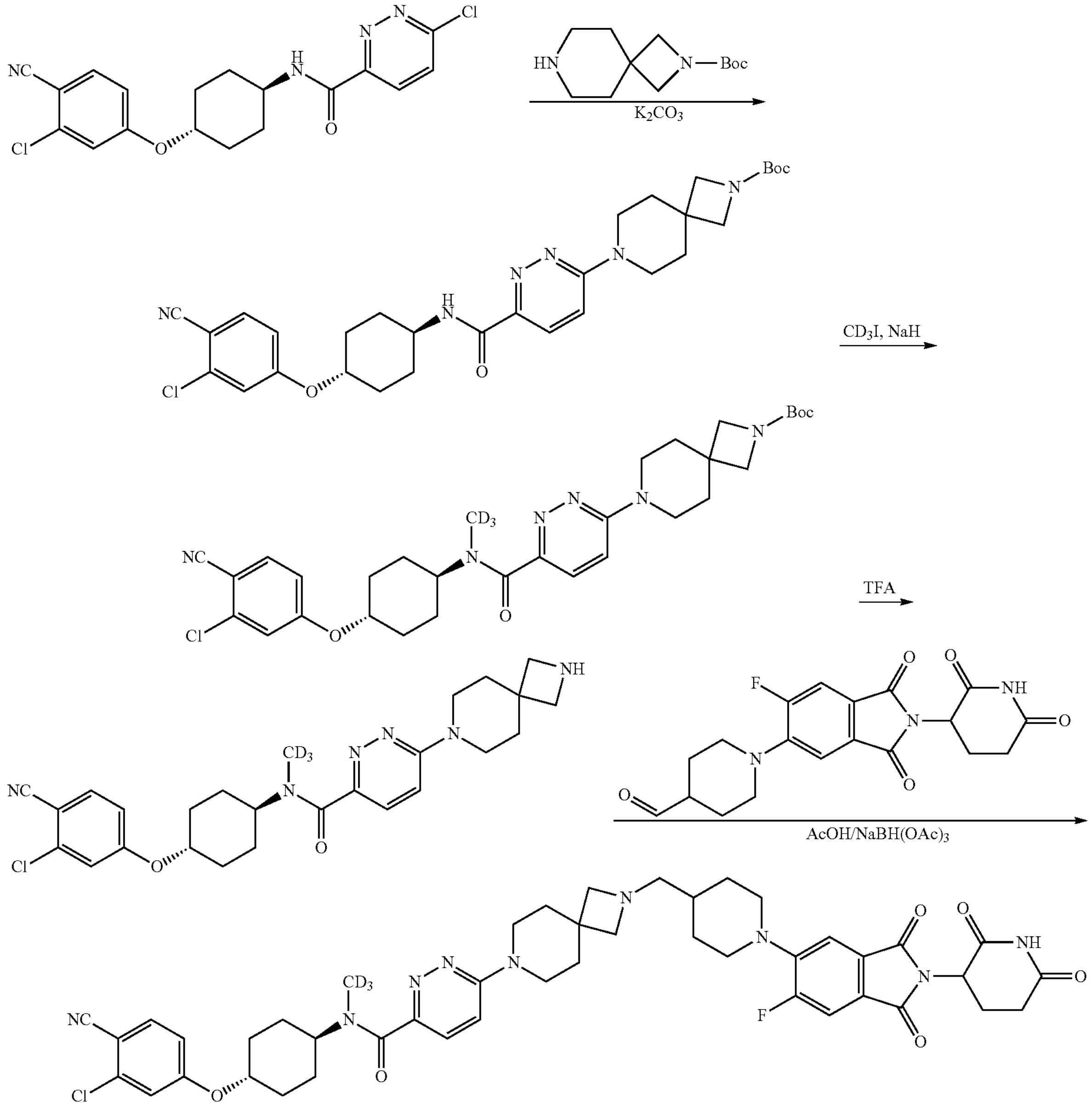

91

1. Synthesis of t-butyl 7-{6-[4-(3-chloro-4-cyano-phenoxy)-cyclohexylcarbamoyl]-pyridazin-3-yl}-2,7-diazaspiro[3.5]nonane-2-carboxylate t-Butyl 2,7-diazaspiro[3.5]nonane-2-carboxylate (113 mg, 0.5 mmol) was dissolved in 6 mL of DMF, to which were added anhydrous potassium carbonate (207 mg, 1.5 mmol) and 6-chloro-pyridazine-3-carboxylic acid [4-(3-chloro-4-cyano-phenoxy)-cyclohexyl]-amide (196 mg, 0.5 mmol). The mixture was allowed to react overnight at 80° C., and then cooled to room temperature, to which was added 15 mL of ethyl acetate. The resultant solution was washed three times with 10 mL water, and then wash once with saturated brine, dried over anhydrous sodium sulfate, filtered, concentrated under reduced pressure to dry, and separated by thin-layer chromatography, to provide the product t-butyl 7-{6-[4-(3-chloro-4-cyano-phenoxy)-cyclohexylcarbamoyl]-pyridazin-3-yl}-2,7-diazaspiro[3.5] nonane-2-carboxylate (190 mg), with a yield of 65.4%, LC/MS (ESI+) calcd for $C_{30}H_{37}ClN_6O_4$ ([M+H]+) m/z 581.2.

2. Synthesis of t-butyl 7-(6-((1r,4r)-4-(3-chloro-4-cyanophenoxy)cyclohexyl)(methyl-d3)carbamoyl) pyridazine-3-yl)-2,7-diazaspiro[3.5]nonan-2-carboxylate t-Butyl 7-{6-[4-(3-chloro-4-cyano-phenoxy)-cyclohexylcarbamoyl]-pyridazin-3-yl}-2,7-diazaspiro[3.5]nonane-2-carboxylate (58 mg, 0.1 mmol) was dissolved in 5 mL of DMF, to which was added sodium hydride (8 mg, 0.2 mmol). The mixture was stirred for 10 min at room temperature, to which was added deuteromethyl iodide (17 mg, 0.12 mmol), and the resultant solution was allowed to react at room temperature for 2 h. The reaction was quenched with water. The reaction solution was extracted with 15 mL ethyl acetate, and the organic layer was washed with water and saturated brine, dried over anhydrous sodium sulfate, filtered, concentrated to dry under reduced pressure, and separated by thin layer chromatography, to provide the product t-butyl 7-(6-((1r,4r)-4-(3-chloro-4-cyanophenoxy) cyclohexyl)(methyl-$d_3$)carbamoyl)pyridazin-3-yl)-2,7-diazaspiro[3.5]nonan-2-carboxylate (58 mg), with a yield of 97.15%, LC/MS (ESI) calcd for $C_{31}H_{36}D_3ClNO_4$ ([M+H]+) m/z 598.3.

3. Synthesis of N-((1r,4r)-4-(3-chloro-4-cyanophenoxy)cyclohexyl)-6-(2-((1-(2,6-dioxopiperidin-3-yl)-6-fluoro-1,3-dioxoisoindolin-5-yl)piperidine-4-yl) methyl)-2,7-diazaspiro[3.5]nonan-7-yl)-N-(methyl-d3)pyridazine-3-formamide t-Butyl 7-(6-((1r,4r)-4-(3-chloro-4-cyanophenoxy)cyclohexyl)(methyl-$d_3$)carbamoyl) pyridazine-3-yl)-2,7-diazaspiro[3.5]nonan-2-carboxylate (57 mg, 0.095 mmol) was dissolved in 3 mL of dichloromethane, to which was added 3 mL of trifluoroacetic acid. The reaction solution was stirred at room temperature for 2 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain 30 mg of white solid, which was dissolved in 5 mL of dichloromethane, to which were successively added 1-[2-(2,6-dioxopiperidin-3-yl)-6-fluoro-1,3-dioxo-2,3-dihydro-1H-isoindol-5-yl]-piperidine-4-caraldehyde (30 mg, 0.078 mmol) and 0.5 drops of acetic acid. The resultant solution was allowed to react 15 min, to which was added sodium triacetylborohydride (106 mg, 0.5 mmol), and then was reacted overnight at room temperature. The reaction solution was washed with water, concentrated to dryness under reduced pressure, and separated by thin layer chromatography, to obtain a yellow solid product N-((1r,4r)-4-(3-chloro-4-cyanophenoxy)cyclohexyl)-6-(2-((1-(2,6-dioxopiperidin-3-yl)-6-fluoro-1,3-dioxoisoindolin-5-yl)piperidine-4-yl) methyl)-2,7-diazaspiro[3.5]nonan-7-yl)-N-(methyl-$d_3$) pyridazine-3-formamide (40 mg), with a yield of 48.4%, LC/MS (ESI+) calcd for $C_{45}H_{46}D_3ClFN_9O_6$ ([M+H]+) m/z 869.3, $^1$H NMR (400 MHz, $CDCl_3$) δ 8.53 (s, 1H), 7.64 (t, J=10.8 Hz, 1H), 7.55 (dd, J=8.7, 5.2 Hz, 1H), 7.46 (d, J=11.0 Hz, 1H), 7.38 (d, J=7.3 Hz, 1H), 7.03-6.92 (m, 2H), 6.83 (ddd, J=18.8, 8.8, 2.1 Hz, 1H), 4.93 (dd, J=12.3, 5.3 Hz, 1H), 4.24 (s, 1H), 3.77-3.58 (m, 6H), 3.28 (s, 3H), 2.94-2.68 (m, 5H), 2.57 (d, J=5.2 Hz, 2H), 2.25 (d, J=8.6 Hz, 1H), 2.15 (dd, J=16.3, 8.4 Hz, 2H), 2.07 (d, J=7.6 Hz, 1H), 1.98 (d, J=10.1 Hz, 1H), 1.88 (d, J=13.0 Hz, 6H), 1.82-1.64 (m, 5H), 1.58-1.39 (m, 3H), 1.28-1.23 (m, 1H).

92: N-((1r,4r)-4-(3-chloro-4-cyanophenoxy)cyclohexyl)-6-(6-((1R,5S,6S)-3-(2-(2,6-dioxopiperidin-3-yl)-6-fluoro-1,3-dioxoisoindolin-5-yl)-3-azabicyclo [3.1.0]n-hexane-6-yl)methyl)-2,6-diazaspiro[3.3] heptane-2-yl)pyridazine-3-formamide

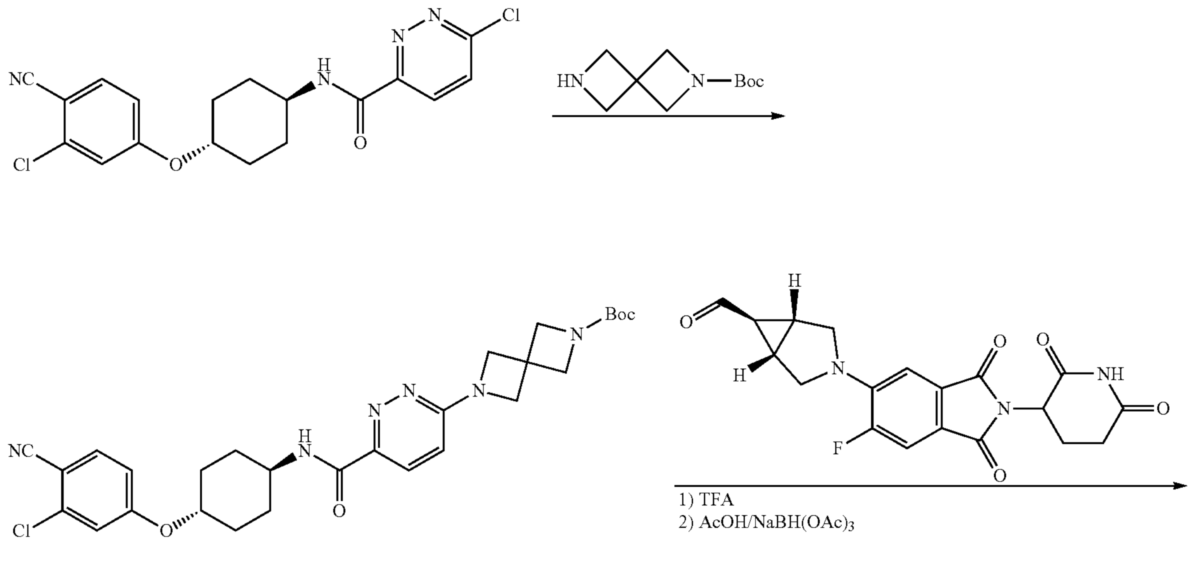

-continued

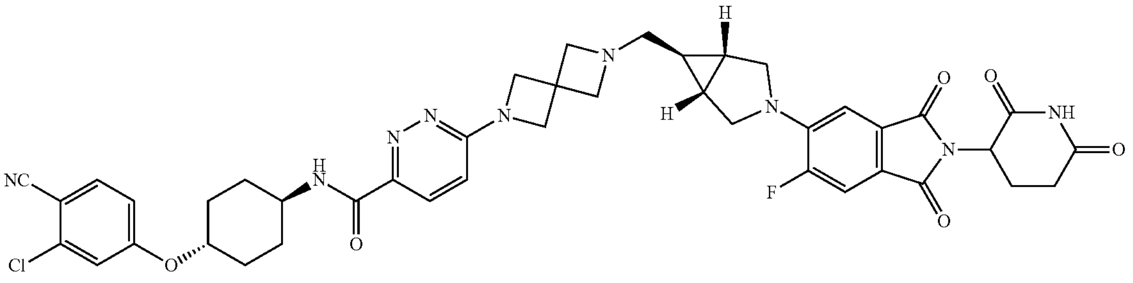

92

1. t-Butyl 6-(6-((1r,4r)-4-(3-chloro-4-cyanophenoxy)cyclohexyl)carbamoyl) pyridazine-3-yl)-2,6-diazaspiro[3.3]heptane-2-carboxylate t-Butyl 2,6-diazaspiro[3.3]heptane-2-carboxylate (182 mg, 0.75 mmol) was dissolved in 5 mL of DMF, to which was added 6-chloro-N-((1r,4r)-4-(3-chloro-4-cyanophenoxy)cyclohexyl)pyridazine-3-formamide (196 mg, 0.5 mmol), and the mixture was allowed to react at 80° C. for 3 h. The reaction solution was cooled to room temperature, to which was added 15 mL of ethyl acetate. The resultant solution was washed with water and saturated brine, dried over anhydrous sodium sulfate, filtered, concentrated to dryness under reduced pressure, and separated by thin-layer chromatography, to obtain the product t-butyl 6-(6-((1r,4r)-4-(3-chloro-4-cyanophenoxy)cyclohexyl)carbamoyl) pyridazine-3-yl)-2,6-diazaspiro[3.3]heptane-2-carboxylate (220 mg), with a yield of 79.6%, LC/MS ($ESI^+$) calcd for $C_{28}H_{33}ClN_6O_4$ ($[M+H]^+$) m/e 553.2.

2. Synthesis of N-((1r,4r)-4-(3-chloro-4-cyanophenoxy)cyclohexyl)-6-(6-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2,6-diazaspiro[3.3]heptane-2-yl)pyridazine-3-formamide t-Butyl 6-(6-((1r,4r)-4-(3-chloro-4-cyanophenoxy)cyclohexyl)carbamoyl)pyridazine-3-yl)-2,6-diazaspiro[3.3]heptane-2-carboxylate (220 mg, 0.4 mmol) was dissolved in 3 mL of dichloromethane, to which was added 3 mL of trifluoroacetic acid. The reaction solution was stirred at room temperature for 2 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain 210 mg of white solid. The obtained product (45 mg, 0.1 mmol) was dissolved in 5 mL of dichloromethane, to which were successively added 3-[2-(2,6-dioxopiperidin-3-yl)-6-fluoro-1,3-dioxo-2,3-dihydro-1H-isoindolin-5-yl]-3-aza-bicyclo[3.1.0]hexane-6-carbaldehyde (37 mg, 0.096 mmol) and 0.5 drops of acetic acid. The resultant solution was allowed to react 5 min at room temperature, to which was added sodium triacetylborohydride (212 mg, 1.0 mmol), and then was stirred overnight at room temperature. The reaction solution was washed with water, concentrated to dryness under reduced pressure, and separated by thin layer chromatography, to obtain a yellow solid product N-((1r,4r)-4-(3-chloro-4-cyanophenoxy)cyclohexyl)-6-(6-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2,6-diazaspiro[3.3]heptane-2-yl)pyridazine-3-formamide (50 mg), with a yield of 60.8%. LC/MS ($ESI^+$) calcd for $C_{42}H_{41}ClFN_9O_6$ ($[M+H]^+$) m/z 822.3. $^1H$ NMR (400 MHz, $CDCl_3$) δ 8.39 (s, 1H), 8.01 (d, J=9.2 Hz, 1H), 7.86 (d, J=8.1 Hz, 1H), 7.56 (d, J=8.7 Hz, 1H), 7.39 (d, J=12.5 Hz, 1H), 7.03 (d, J=7.4 Hz, 1H), 7.00 (d, J=2.3 Hz, 1H), 6.85 (dd, J=8.8, 2.4 Hz, 1H), 6.63 (d, J=9.2 Hz, 1H), 4.91 (dd, J=12.2, 5.3 Hz, 1H), 4.42-4.28 (m, 4H), 4.05 (d, J=8.0 Hz, 1H), 3.87 (d, J=7.9 Hz, 2H), 3.77 (s, 3H), 3.57 (d, J=9.9 Hz, 2H), 2.96-2.70 (m, 3H), 2.70-2.52 (m, 2H), 2.25-2.07 (m, 5H), 1.72-1.67 (m, 6H), 1.46 (dd, J=22.5, 10.3 Hz, 3H).

93: N-((1r,4r)-4-(3-Chloro-4-cyanophenoxy)cyclohexyl)-6-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-1,4-diaza-1-yl) pyridazine-3-carboxamide

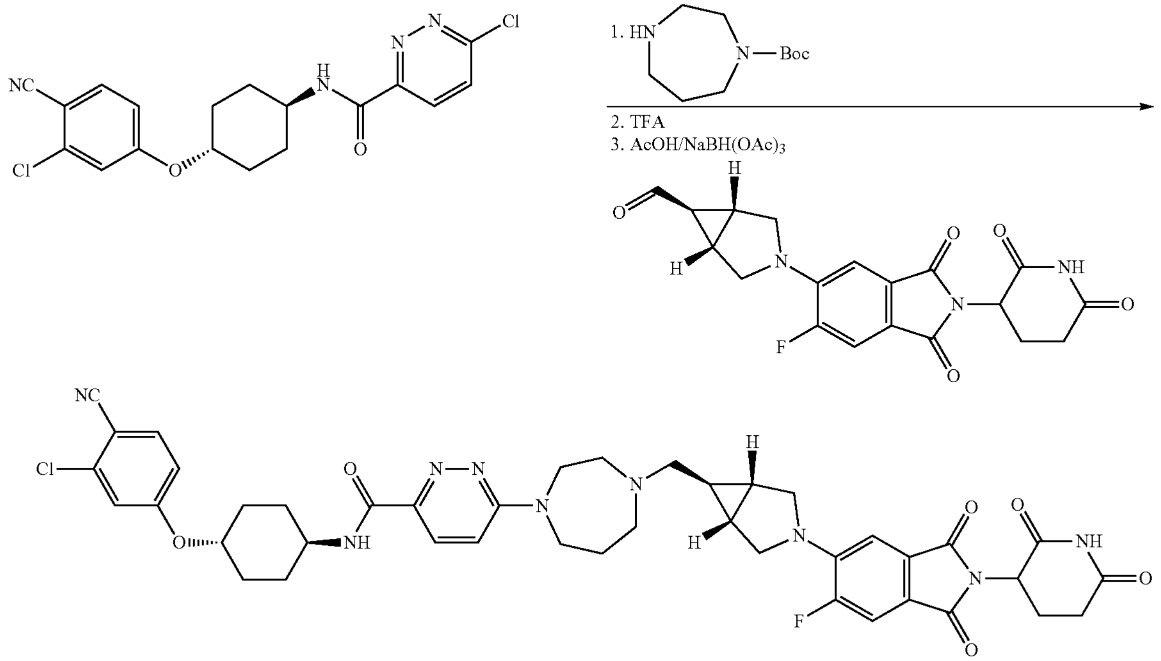

93

Synthetic procedures referred to 92.

LC/MS (ESI$^+$) calcd for $C_{42}H_{43}ClFN_9O_6$ ($[M+H]^+$) m/z 824.3, $^1$H NMR (400 MHz, $CDCl_3$) A 8.27 (s, 1H), 8.01 (d, J=9.5 Hz, 1H), 7.88 (d, J=8.2 Hz, 1H), 7.56 (d, J=8.7 Hz, 1H), 7.40 (s, 1H), 7.01 (dd, J=7.5, 4.9 Hz, 2H), 6.91-6.82 (m, 2H), 4.91 (dd, J=12.2, 5.3 Hz, 1H), 4.37-4.25 (m, 1H), 4.05 (dd, J=11.5, 7.4 Hz, 2H), 3.86 (dd, J=9.9, 2.3 Hz, 2H), 3.74 (d, J=5.0 Hz, 2H), 3.57 (d, J=9.2 Hz, 2H), 2.81 (qdd, J=17.5, 15.9, 10.0 Hz, 7H), 2.59 (s, 2H), 2.22-2.05 (m, 6H), 1.75-1.64 (m, 6H), 1.54-1.36 (m, 3H).

94: N-((1r,4r)-4-(4-cyano-3-(trifluoromethyl)phenoxy)cyclohexyl)-5-(4-((1R, 5S, 6s)-3-(2-(2,6-dioxopiperidin-3-yl)-6-fluoro-1,3-dioxoisoindolin-5-yl)-3-azabicyclo[3.1.0]n-hexane-6-yl)methyl) piperazin-1-yl)pyrazine-2-carboxamide

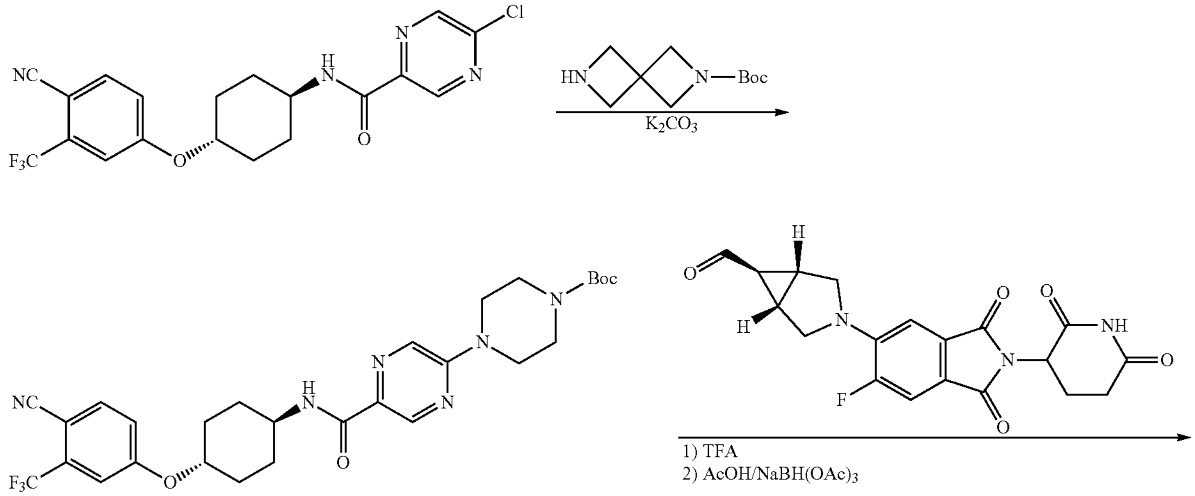

-continued

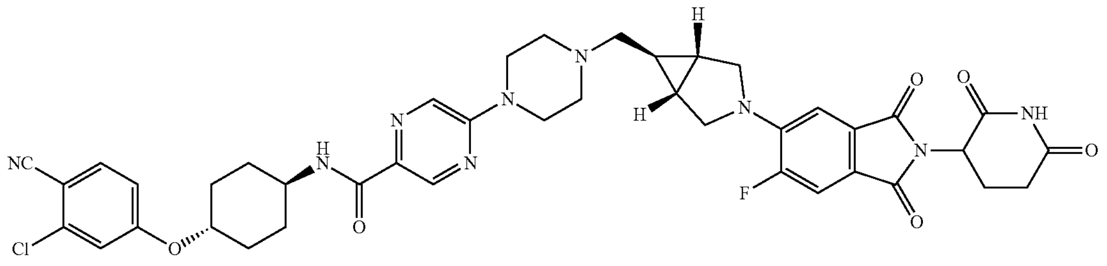

94

1. Synthesis of t-butyl 5'-[4-(4-cyano-3-trifluoromethylphenoxy)-cyclohexylcarbamoyl]-2,3,5,6-tetrahydro-[1,2']bipyrazinyl-4-carboxylate N-Bocpiperazine (93 mg, 0.5 mmol) was dissolved in 5 ml DMF, to which were added potassium carbonate (138 mg, 1.0 mmol) and 5-chloro-pyrazine-2-carboxylic acid [4-(4-cyano-3-trifluoromethyl-phenoxy)-cyclohexyl]-amide (142 mg, 0.33 mmol), and the mixture was allowed to react at 80° C. for 3 h, to which was added 15 ml ethyl acetate. The reaction solution was successively washed with water and saturated brine, dried over anhydrous sodium sulfate, filtered, concentrated to dryness under reduced pressure, and separated by thin layer chromatography, to provide t-butyl 5'-[4-(4-cyano-3-trifluoromethylphenoxy)-cyclohexylcarbamoyl]-2,3,5,6-tetrahydro-[1,2']bipyrazinyl-4-carboxylate (120 mg), with a yield of 63.3%, LC/MS ($ESI^+$) $C_{28}H_{33}F_3ClN_6O_4$ ($[M+H]^+$) m/z 574.9.

2. Synthesis of N-((1r,4r)-4-(4-cyano-3-(trifluoromethyl)phenoxy)cyclohexyl)-5-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyrazine-2-carboxamide 5'-[4-(4-Cyano-3-trifluoromethylphenoxy)-cyclohexylcarbamoyl]-2,3,5,6-tetrahydro-[1,2']bipyrazinyl-4-carboxylate t-butyl (120 mg, 0.21 mmol) was dissolved in 3 mL of dichloromethane, to which was added 3 mL of trifluoroacetic acid. The reaction solution was stirred at room temperature for 2 h, and concentrated to dryness under reduced pressure. The pH of the reaction solution was adjusted to be alkaline with saturated $Na_2CO$ aqueous solution, and then extracted twice with DCM. The organic layers were combined, washed once with saturated brine, dried over anhydrous magnesium sulfate, filtered, and concentrated to dryness under reduced pressure, to obtain 100 mg of white solid. The obtained product (49 mg, 0.103 mmol) was dissolved in 5 mL of dichloromethane, to which were added 3-[2-(2,6-dioxopiperidin-3-yl)-6-fluoro-1,3-dioxo-2,3-dihydro-1h-isoindol-5-yl]-3-aza-bicyclo[3.1.0]hexane-6-formaldehyde (39 mg, 0.1 mmol) and 0.5 drops of acetic acid. The resultant solution was stirred 15 min at room temperature, to which was added sodium triacetylborohydride (212 mg, 1.0 mmol), and then was allowed to react overnight at room temperature. The reaction solution was washed with water, concentrated to dryness under reduced pressure, and separated by thin layer chromatography, to obtain a yellow solid product N-((1r,4r)-4-(4-cyano-3-(trifluoromethyl)phenoxy)cyclohexyl)-5-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyrazine-2-carboxamide (45 mg), with a yield of 50%, LC/MS ($ESI^+$) calcd for $C_{42}H_{41}F_4ClN_9O_6$ ($[M+H]^+$) m/z 844.3, $^1H$ NMR (400 MHz, $CDCl_3$) δ 8.86 (s, 1H), 8.24 (s, 1H), 7.97 (s, 1H), 7.74 (d, J=8.6 Hz, 1H), 7.45-7.35 (m, 2H), 7.25 (d, J=2.1 Hz, 1H), 7.10 (dd, J=8.7, 2.2 Hz, 1H), 7.04 (d, J=7.3 Hz, 1H), 4.92 (dd, J=12.0, 5.3 Hz, 1H), 4.38 (t, J=10.0 Hz, 1H), 4.05 (dd, J=18.5, 11.1 Hz, 1H), 3.87 (dd, J=23.6, 6.9 Hz, 4H), 3.60 (d, J=9.5 Hz, 2H), 2.95-2.66 (m, 6H), 2.56 (d, J=14.1 Hz, 2H), 2.28-2.09 (m, 5H), 1.73-1.64 (m, 5H), 1.56-1.45 (m, 3H), 1.25 (dd, J=8.4, 5.6 Hz, 1H), 1.10-0.99 (m, 1H).

95: N-((1r,4r)-4-(4-cyano-3-(trifluoromethyl)phenoxy)cyclohexyl)-6-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyridazine-3-formamide

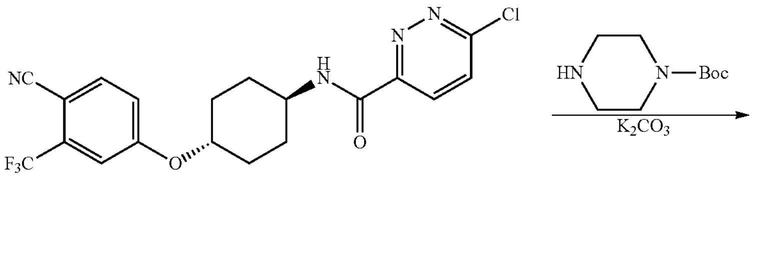

-continued

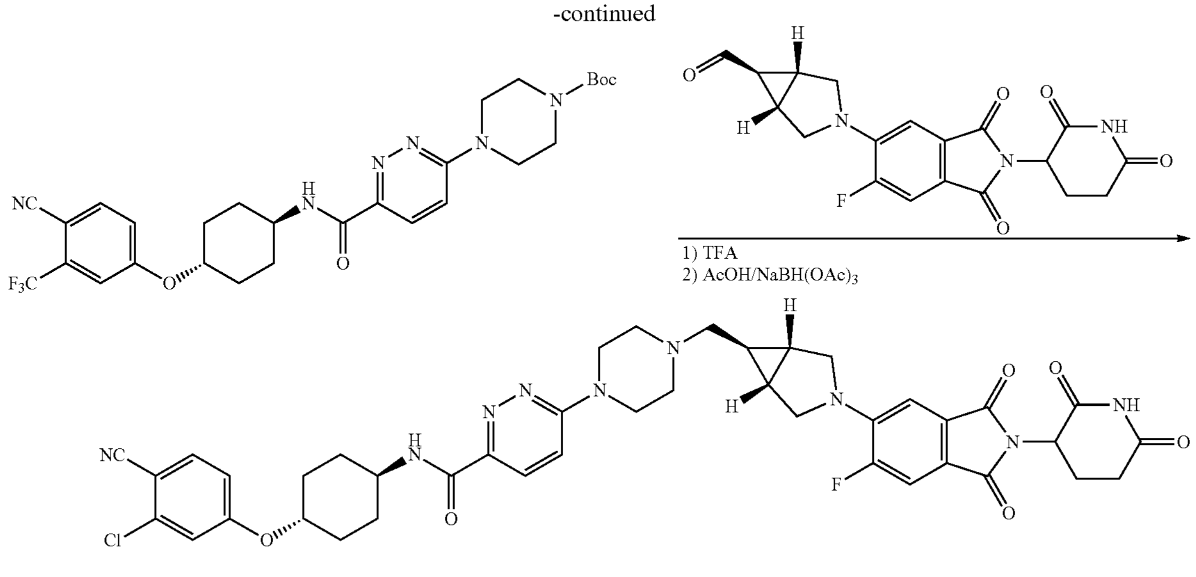

95

Synthetic procedures referred to 94.

LC/MS ($ESI^+$) calcd for $C_{42}H_{41}F_4ClFN_9O_6$ ($[M+H]^+$) m/z 844.3, $^1H$ NMR (400 MHz, $CDCl_3$) β 8.27 (s, 1H), 8.05 (d, J=9.4 Hz, 1H), 7.88 (d, J=8.2 Hz, 1H), 7.75 (d, J=8.6 Hz, 1H), 7.40 (d, J=12.4 Hz, 1H), 7.26 (d, J=2.5 Hz, 1H), 7.11 (dd, J=8.6, 2.4 Hz, 1H), 7.03 (dd, J=11.8, 8.6 Hz, 2H), 4.92 (dd, J=12.2, 5.3 Hz, 1H), 4.39 (dd, J=11.9, 8.3 Hz, 1H), 4.07 (dd, J=11.4, 7.5 Hz, 1H), 3.91 (d, J=7.7 Hz, 4H), 3.60 (d, J=9.0 Hz, 2H), 2.96-2.67 (m, 6H), 2.67-2.44 (m, 2H), 2.28-2.09 (m, 5H), 1.74 (dd, J=18.1, 8.7 Hz, 5H), 1.55-1.40 (m, 3H), 1.25 (dd, J=8.5, 5.5 Hz, 1H), 1.06 (d, J=1.1 Hz, 1H).

96: N-((1r,4r)-4-(3-chloro-4-cyanophenoxy)cyclohexyl)-5-(6-((1-(2,6-dioxopiperidin-3-yl)-6-fluoro-1,3-dioxoisoindolin-5-yl)piperidine-4-yl)methyl)-2,6-diazaspiro[3.4]octan-2-yl)pyrazine-2-carboxamide

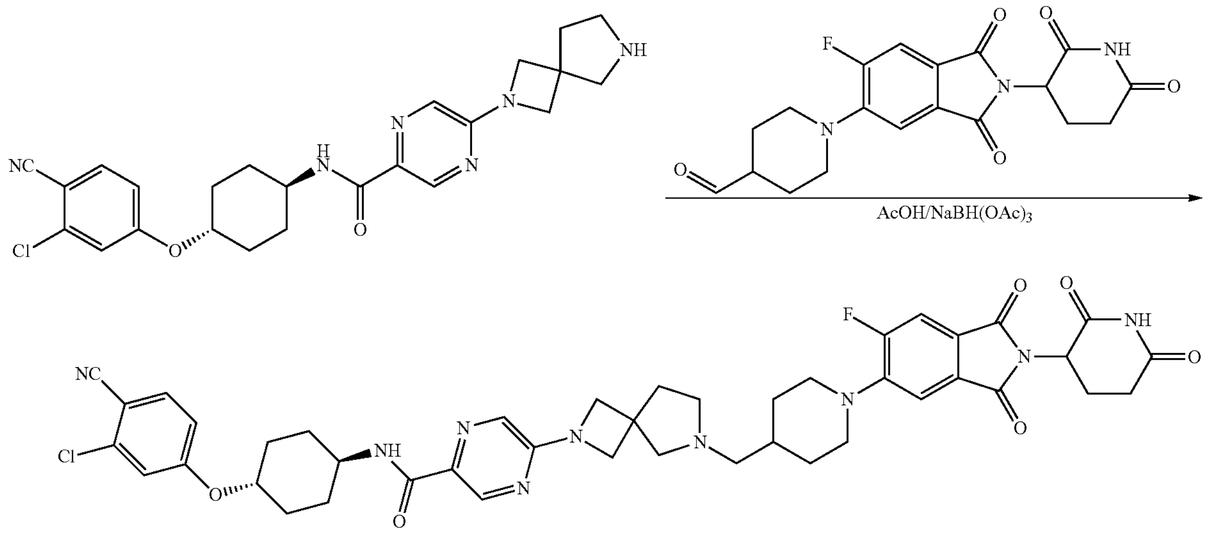

96

N-((1r,4r)-4-(3-Chloro-4-cyanophenoxy)cyclohexyl)-5-(2,6-diazaspiro[3.4]octane-2-yl)pyrazine-2-carboxamide (50 mg, 0.11 mmol) was dissolved in 5 mL of dichloromethane, to which were added 1-[2-(2,6-dioxopiperidin-3-yl)-6-fluoro-1,3-dioxo-2,3-dihydro-1h-isoindol-5-yl]-piperidine-4-carbaldehyde (45 mg, 0.12 mmol) and 0.5 drops of acetic acid. The resultant solution was allowed to react 15 min at room temperature, to which was added sodium triacetylborohydride ( ), and then was allowed to react overnight at room temperature. The reaction solution was cooled to room temperature and washed with water, concentrated to dryness under reduced pressure, and separated by thin layer chromatography, to obtain a yellow solid product N-((1r,4r)-4-(3-chloro-4-cyanophenoxy)cyclohexyl)-5-(6-((1-(2,6-dioxopiperidin-3-yl)-6-fluoro-1,3-dioxoisoindolin-5-yl)piperidine-4-yl)methyl)-2,6-diazaspiro[3.4]octan-2-yl)pyrazine-2-carboxamide (35 mg), with a yield of 39.0%. LC/MS (ESI+) calcd for $C_{43}H_{45}ClFN_9O_6$ ([M+H]+) m/z 837.7.

97: N-((1r,4r)-4-(3-chloro-4-cyanophenoxy)cyclohexyl)-6-(7-(1-(2-(2,6-dioxopiperidin-3-yl)-6-fluoro-1,3-dioxoisoindolin-5-yl)piperidine-4-yl)-2,7-diazaspiro[3.5]nonan-2-yl)pyridazine-3-carboxamide

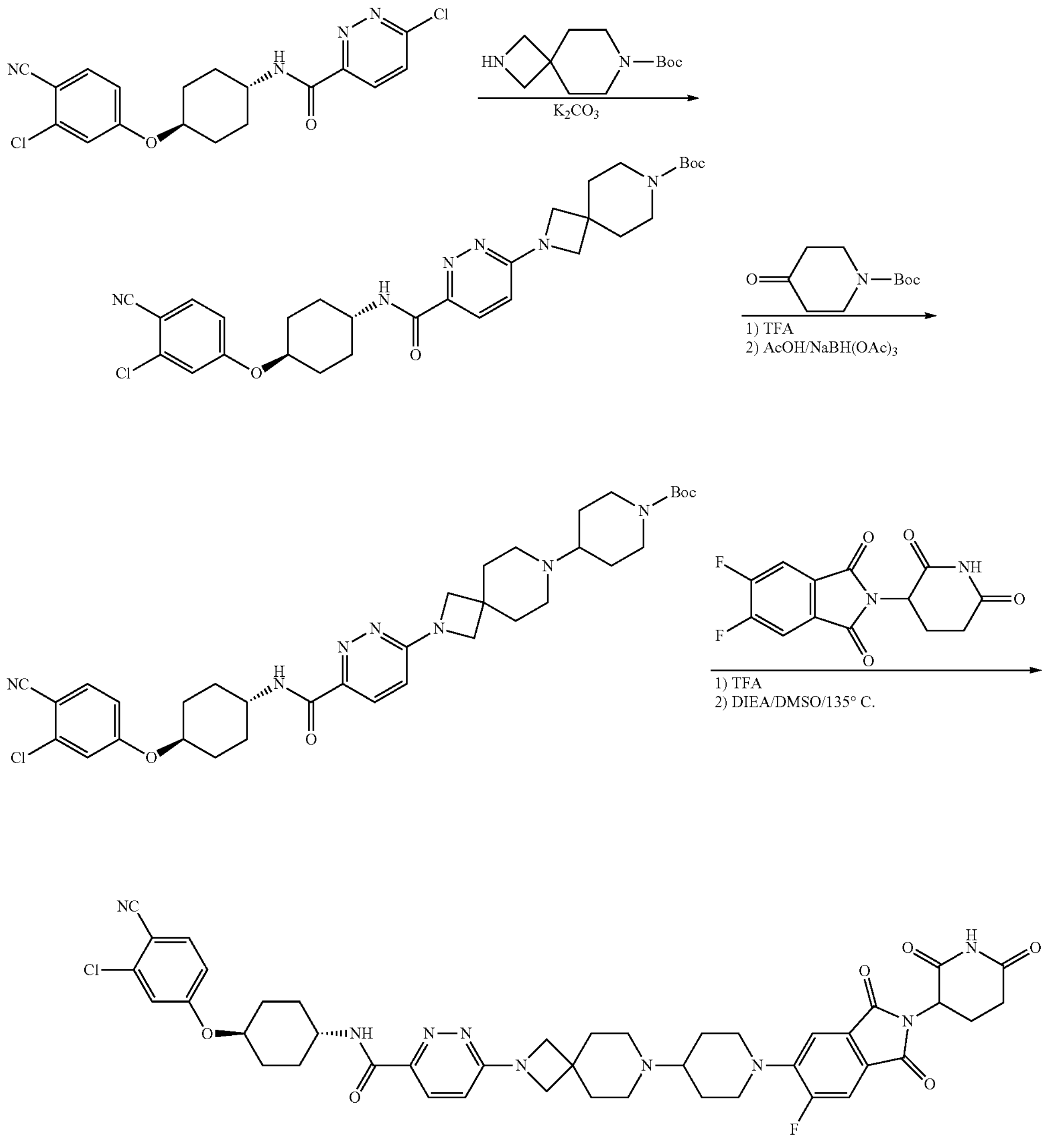

97

Synthetic procedures referred to 88.

Characteristic data: LC/MS (ESI$^+$) calcd for $C_{43}H_{45}ClFN_9O_6$ ([M+H]$^+$) m/z 837.7. $^1$H NMR (400 MHz, $CDCl_3$) δ 8.42-8.26 (m, 1H), 7.99 (d, J=9.2 Hz, 1H), 7.88 (d, J=8.1 Hz, 1H), 7.56 (d, J=8.7 Hz, 1H), 7.48 (d, J=10.9 Hz, 1H), 7.39 (d, J=7.3 Hz, 1H), 7.00 (d, J=2.3 Hz, 1H), 6.86 (dd, J=8.8, 2.4 Hz, 1H), 6.60 (d, J=9.3 Hz, 1H), 5.00-4.90 (m, 1H), 4.77-4.59 (m, 2H), 4.38-4.26 (m, 1H), 4.12-4.00 (m, 1H), 3.93 (s, 4H), 3.74 (d, J=12.0 Hz, 2H), 2.91 (d, J=12.2 Hz, 3H), 2.82-2.69 (m, 4H), 2.22-2.13 (m, 5H), 2.04 (s, 5H), 1.82 (s, 3H), 1.69 (d, J=12.2 Hz, 3H), 1.47 (d, J=12.1 Hz, 2H).

98: N-((1r,4r)-4-(3-chloro-4-cyanophenoxy)cyclohexyl)-6-(6-((1-(2,6-dioxopiperidin-3-yl)-6-fluoro-1,3-dioxoisoindol-5-yl)piperidine-4-yl)methyl)-2,6-diazaspiro [3.4] octane-2-yl)pyridazine-3-formamide

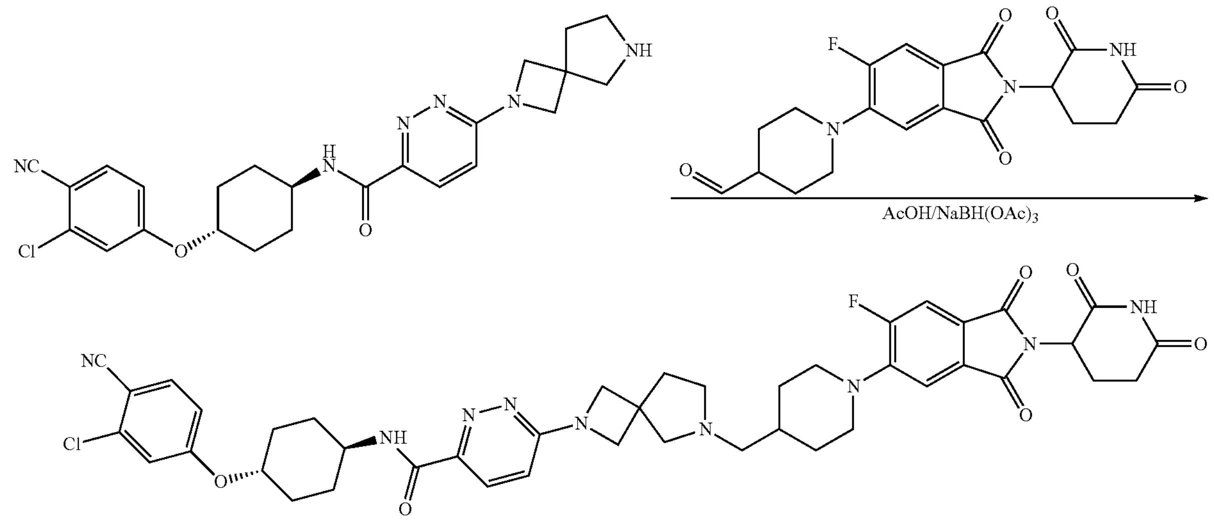

98

Synthetic procedures referred to 96.

Characteristic data: LC/MS (ESI$^+$) $C_{43}H_{45}ClFN_9O_6$ ([M+H]$^+$) m/z 838.

99: N-((1r,4r)-4-(3-chloro-4-cyanophenoxy)cyclohexyl)-5-(4-((1R,5S,6s)-3-(2-(2,6-dioxopiperidin-3-yl)-6-fluoro-1,3-dioxoisoindolin-5-yl)-3-azabicyclo [3.1.0]n-hexane-6-yl)methyl)piperazin-1-yl) pyrazine-2-carboxamide

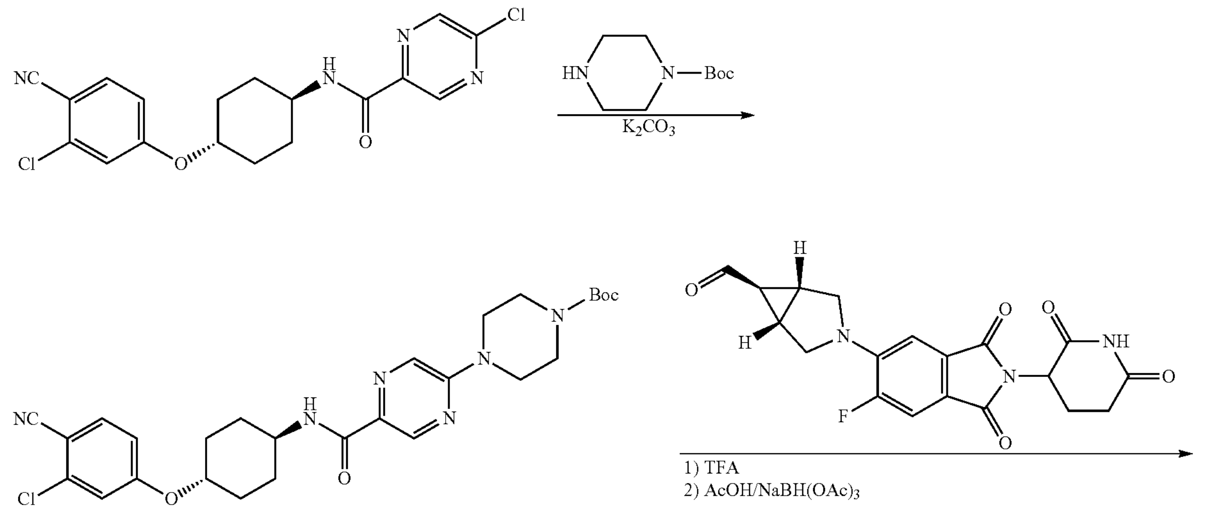

-continued

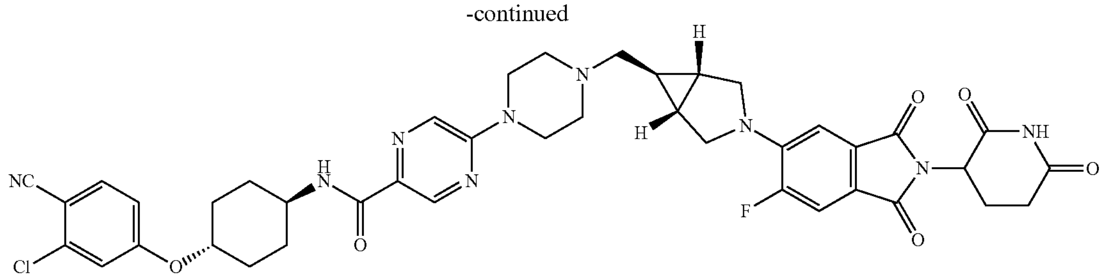

99

1. t-Butyl 5'-[4-(3-chloro-4-cyano-phenoxy)-cyclohexylcarbamoyl]-2,3,5,6-tetrahydro-[1,2']bipyrazinyl-4-carboxylate N-Bocpiperazine (140 mg, 0.75 mmol) was dissolved in 5 ml DMF, to which were successively added anhydrous potassium carbonate (207 mg, 1.5 mmol) and 5-chloro-pyrazine-2-carboxylic acid [4-(4-cyano-3-chloro-phenoxy)-cyclohexyl]-amide (196 mg, 0.5 mmol), and the mixture was allowed to react at 80° C. for 3 h, to which was added 15 ml ethyl acetate. The reaction solution was successively washed with water and saturated brine, dried over anhydrous sodium sulfate, filtered, concentrated to dryness under reduced pressure, and separated by thin layer chromatography, to provide the product t-butyl 5'-[4-(3-chloro-4-cyano-phenoxy)-cyclohexylcarbamoyl]-2,3,5,6-tetrahydro-[1,2']bipyrazinyl-4-carboxylate (130 mg), with a yield of 46%, LC/MS ($ESI^+$) calcd for $C_{27}H_{33}ClN_6O_4$ ($[M+H]^+$) m/z 540.8.

2. Synthesis of N-((1r,4r)-4-(3-chloro-4-cyanophenoxy)cyclohexyl)-5-(4-((1R, 5S, 6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyrazine-2-carboxamide t-Butyl 5'-[4-(3-chloro-4-cyano-phenoxy)-cyclohexylcarbamoyl]-2,3,5,6-tetrahydro-[1,2']bipyrazinyl-4-carboxylate (130 mg, 0.23 mmol) was dissolved in 3 mL of dichloromethane, to which was added 3 mL of trifluoroacetic acid. The reaction solution was stirred at room temperature for 2 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain 100 mg of white solid. The obtained product (45 mg, 0.1 mmol) was dissolved in 5 mL of dichloromethane, to which were added 3-[2-(2,6-dioxopiperidin-3-yl)-6-fluoro-1,3-dioxo-2,3-dihydro-1H-isoindol-5-yl]-3-aza-bicyclo[3.1.0]hexane-6-formaldehyde (37 mg, 0.1 mmol) and 0.5 drops of acetic acid. The resultant solution was allowed to react 15 min at room temperature, to which was added sodium cyanobohydride (80 mg, 1.3 mmol), and then was allowed to react overnight at room temperature. The reaction solution was cooled to room temperature and washed with water, concentrated to dryness under reduced pressure, and separated by thin layer chromatography, to obtain a yellow solid product N-((1r,4r)-4-(3-chloro-4-cyanophenoxy)cyclohexyl)-5-(4-((1R,5S,6s)-3-(2-(2,6-dioxopiperidin-3-yl)-6-fluoro-1,3-dioxoisoindol-5-yl)-3-azabicyclo[3.1.0]n-hexane-6-yl)methyl)piperazin-1-yl)pyrazine-2-carboxamide (20 mg), with a yield of 24.7%, LC/MS ($ESI^+$) for $C_{41}H_{41}ClFN_9O_6$ ($[M+H]^+$) m/z 809.8, $^1H$ NMR (400 MHz, $CDCl_3$) δ 8.86 (d, J=1.0 Hz, 1H), 8.26 (s, 1H) 7.97 (s, 1H) 7.56 (d, J=8.7 Hz, 1H), 7.44-7.36 (m, 2H), 7.04 (d, J=7.4 Hz, 1H), 6.99 (d, J=2.3 Hz, 1H), 6.85 (dd, J=8.8, 2.4 Hz, 1H), 4.96-4.86 (m, 1H), 4.34-4.26 (m, 1H), 4.08-3.97 (m, 1H), 3.88 (s, 2H), 3.82 (s, 3H), 3.65-3.53 (m, 2H), 2.73 (s, 6H), 2.58-2.42 (m, 2H), 2.17 (d, J=11.9 Hz, 4H), 1.74-1.68 (m, 6H), 1.56-1.38 (m, 3H).

100: N-((1r,4r)-4-(3-chloro-4-cyanophenoxy)cyclohexyl)-6-(5-((1R,5S,6s)-3-(2-(2,6-dioxopiperidin-3-yl)-1,3-dioxoisoindolin-5-yl)-3-azabicyclo[3.1.0]n-hexane-6-yl)methyl)hexahydropyrrolo[3,4-c]pyrrol-2(1H)-yl)pyridazine-3-formamide

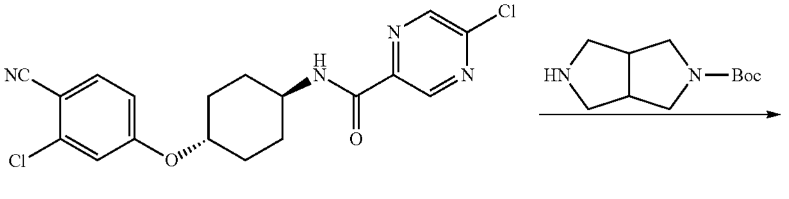

-continued

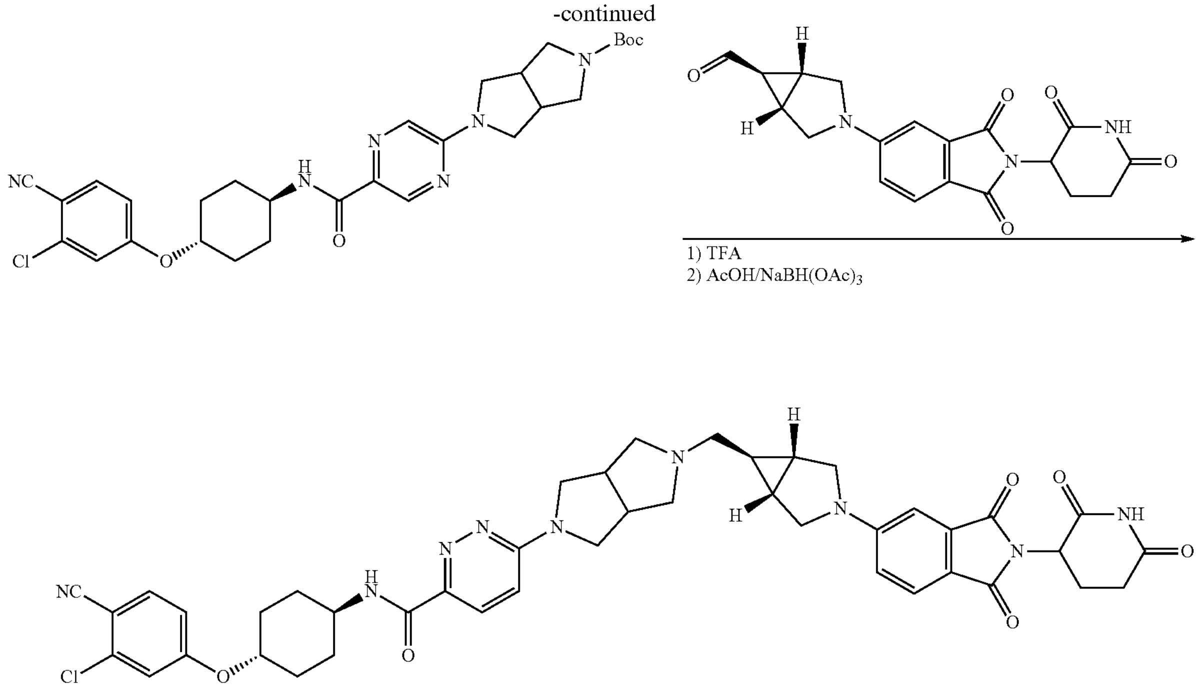

100

LC/MS ($ESI^+$) calcd for $C_{43}H_{44}ClN_9O_6$ ($[M+H]^+$) m/z 817.8. $^1H$ NMR (400 MHz, $CDCl_3$) δ 8.34 (s, 1H), 8.05 (d, J=9.5 Hz, 1H), 7.93 (d, J=8.2 Hz, 1H), 7.67 (d, J=8.4 Hz, 1H), 7.58 (d, J=8.7 Hz, 1H), 7.02 (d, J=2.3 Hz, 1H), 6.94 (d, J=1.8 Hz, 1H), 6.87 (dd, J=8.8, 2.4 Hz, 1H), 6.81 (d, J=9.0 Hz, 1H), 6.68 (d, J=6.9 Hz, 1H), 4.94 (dd, J=12.2, 5.4 Hz, 1H), 4.35 (d, J=4.1 Hz, 1H), 4.09 (s, 1H), 3.78 (s, 2H), 3.68 (d, J=10.0 Hz, 2H), 3.48 (d, J=8.6 Hz, 2H), 3.36-3.25 (m, 1H), 2.95-2.65 (m, 6H), 2.44 (d, J=5.0 Hz, 1H), 2.30 (d, J=5.4 Hz, 1H), 2.23-2.10 (m, 5H), 1.87 (s, 2H), 1.71 (d, J=12.7 Hz, 4H), 1.55-1.43 (m, 3H), 1.28 (d, J=7.8 Hz, 2H).

101: N-((1r,3R)-3-(3-chloro-4-cyanophenoxy)-2,2,4,4-tetramethylcyclobutyl)-6-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl) piperazin-1-yl)pyridazine-3-formamide

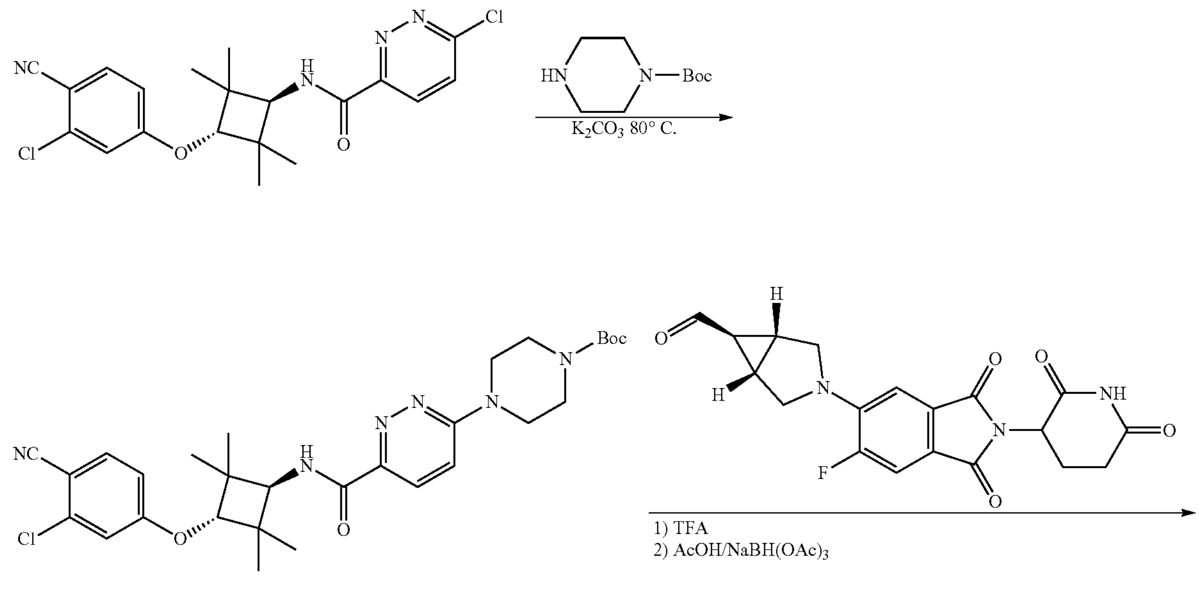

-continued

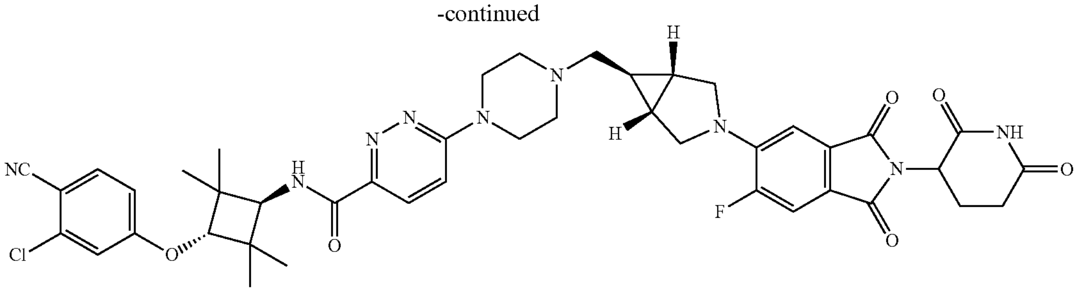

101

1. Synthesis of t-butyl 4-(6-((1r,3r)-3-(3-chloro-4-cyanophenoxy)-2,2,4,4-tetramethylcyclobutyl)carbamoyl)pyridazine-3-yl)piperazine-1-carboxylate N-Bocpiperazine (60 mg, 0.38 mmol) was dissolved in 5 ml DMF, to which were successively added anhydrous potassium carbonate (100 mg, 0.75 mmol) and 6-chloro-pyridazine-3-carboxylic acid [3-(3-chloro-4-cyano-phenoxy)-2,2,4,4-tetramethyl-cyclohexyl]-amide (105 mg, 0.25 mmol), and the mixture was allowed to react at 80° C. for 3 h, to which was added 15 ml ethyl acetate. The reaction solution was successively washed with water and saturated brine, dried over anhydrous sodium sulfate, filtered, concentrated to dryness under reduced pressure, and separated by thin layer chromatography, to provide the product t-butyl 4-(6-((1r,3r)-3-(3-chloro-4-cyanophenoxy)-2,2,4,4-tetramethylcyclobutyl)carbamoyl)pyridazine-3-yl)piperazine-1-carboxylate (85 mg), with a yield of 59.7%, LC/MS ($ESI^+$) calcd for $C_{29}H_{37}ClN_6O_4$ ($[M+H]^+$) m/z 568.9.

2. N-((1r,3R)-3-(3-chloro-4-cyanophenoxy)-2,2,4,4-tetramethylcyclobutyl)-6-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyridazine-3-formamide t-Butyl 4-(6-((1r,3r)-3-(3-chloro-4-cyanophenoxy)-2,2,4,4-tetramethylcyclobutyl) carbamoyl)pyridazine-3-yl)piperazine-1-carboxylate (85 mg, 0.15 mmol) was dissolved in 3 mL of dichloromethane, to which was added 3 mL of trifluoroacetic acid. The reaction solution was stirred at room temperature for 2 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain 70 mg of white solid. The obtained product (35 mg, 0.07 mmol) was dissolved in 5 mL of dichloromethane, to which were added 3-[2-(2,6-dioxopiperidin-3-yl)-6-fluoro-1,3-dioxo-2,3-dihydro-1H-isoindol-5-yl]-3-aza-bicyclo[3.1.0]hexane-6-formaldehyde (30 mg, 0.077 mmol) and 0.5 drops of acetic acid. The resultant solution was allowed to react 15 min at room temperature, to which was added sodium triacetylbohydride (224 mg, 1.0 mmol), and then was allowed to react overnight at room temperature. The reaction solution was cooled to room temperature and washed with water, concentrated to dryness under reduced pressure, and separated by thin layer chromatography, to obtain a yellow solid product N-((1r,3R)-3-(3-chloro-4-cyanophenoxy)-2,2,4,4-tetramethylcyclobutyl)-6-(4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl)pyridazine-3-formamide (20 mg), with a yield of 34%, LC/MS ($ESI^+$) for $C_{43}H_{45}ClFN_9O_6$ ($[M+H]^+$) m/z 837.7, $^1H$ NMR (400 MHz, $CDCl_3$) δ 8.25-8.12 (m, 2H), 8.06 (d, J=9.5 Hz, 1H), 7.59 (d, J=8.7 Hz, 1H), 7.42 (d, J=12.5 Hz, 1H), 7.06 (t, J=8.8 Hz, 2H), 6.99 (d, J=2.3 Hz, 1H), 6.83 (dd, J=8.7, 2.4 Hz, 1H), 4.97-4.88 (m, 1H), 4.21 (d, J=9.0 Hz, 1H), 4.09 (s, 1H), 3.93 (d, J=7.4 Hz, 2H), 3.62 (d, J=9.1 Hz, 2H), 3.08-2.70 (m, 6H), 2.70-2.52 (m, 2H), 2.20-2.11 (m, 1H), 1.76 (s, 6H), 1.29 (d, J=12.5 Hz, 6H), 1.23 (s, 6H), 1.07 (s, 1H), 0.88 (d, J=20.0 Hz, 1H).

102: N-((1r,4r)-4-(3-chloro-4-cyanophenoxy)cyclohexyl)-6-(4-((1R,5S,6s)-3-(2-(2,6-dioxopiperidin-3-yl)-1,3-dioxoisoindolin-5-yl)-3-azabicyclo[3.1.0]n-hexane-6-yl)methyl)piperazin-1-yl)pyridazine-3-formamide

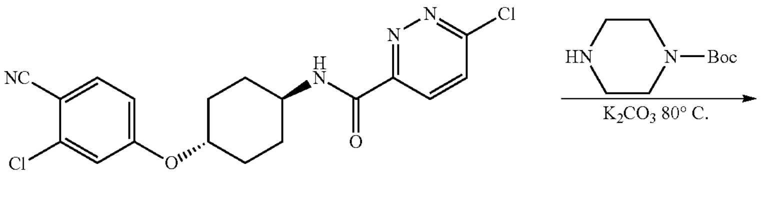

-continued
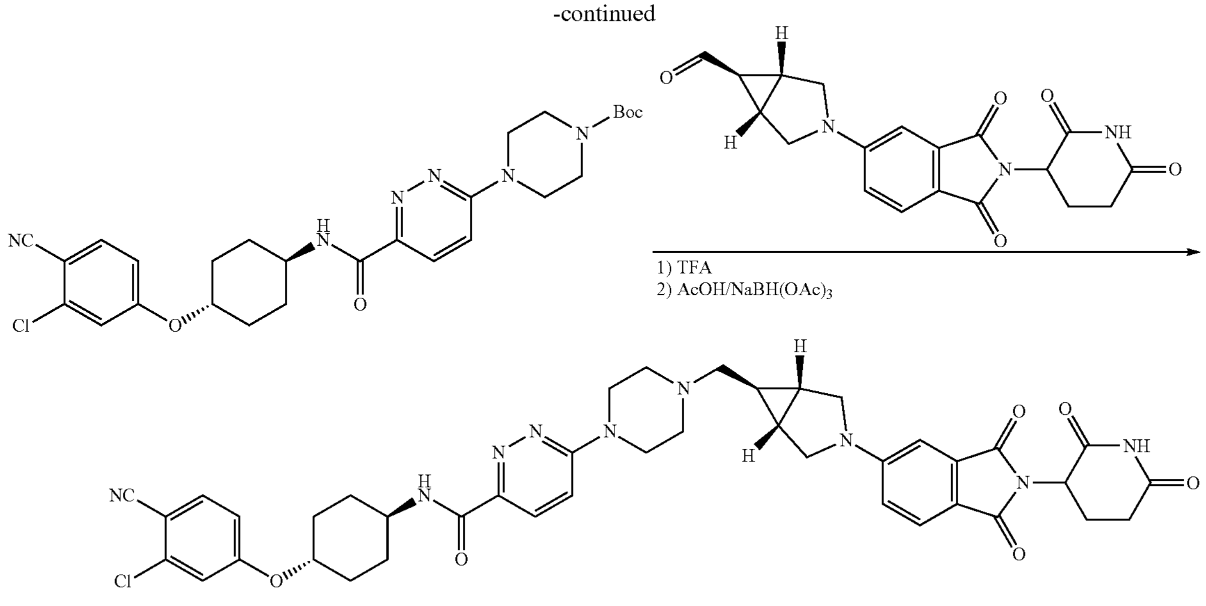
102
LC/MS ($ESI^+$) for $C_{41}H_{42}ClN_9O_6$ ($[M+H]^+$) m/z 791.7, $^1H$ NMR (400 MHz, $CDCl_3$) δ 8.26 (s, 1H), 8.07 (d, J=9.1 Hz, 1H), 7.90 (d, J=8.1 Hz, 1H), 7.67 (d, J=8.4 Hz, 1H), 7.58 (d, J=8.7 Hz, 1H), 7.06-7.00 (m, 2H), 6.96 (d, J=2.0 Hz, 1H), 6.87 (dd, J=8.7, 2.4 Hz, 1H), 6.70 (dd, J=8.4, 2.1 Hz, 1H), 4.96 (dd, J=12.2, 5.3 Hz, 1H), 4.34 (t, J=10.0 Hz, 1H), 4.08 (d, J=8.0 Hz, 1H), 3.93 (s, 2H), 3.71 (d, J=9.9 Hz, 2H), 3.52 (d, J=9.7 Hz, 2H), 2.83 (ddd, J=33.3, 23.9, 10.4 Hz, 5H), 2.20 (s, 4H), 1.73-1.59 (m, 111H), 1.55-1.42 (m, 3H).
103: N-((1r,4r)-4-(3-chloro-4-cyanophenoxy)cyclohexyl)-6-(4-(6-(2-(2,6-dioxopiperidin-3-yl)-6-fluoro-1,3-dioxoisoindolin-5-yl)-2,6-diazaspiro[3.4]octane-2-yl)piperidin-1-yl)pyridazine-3-formamide
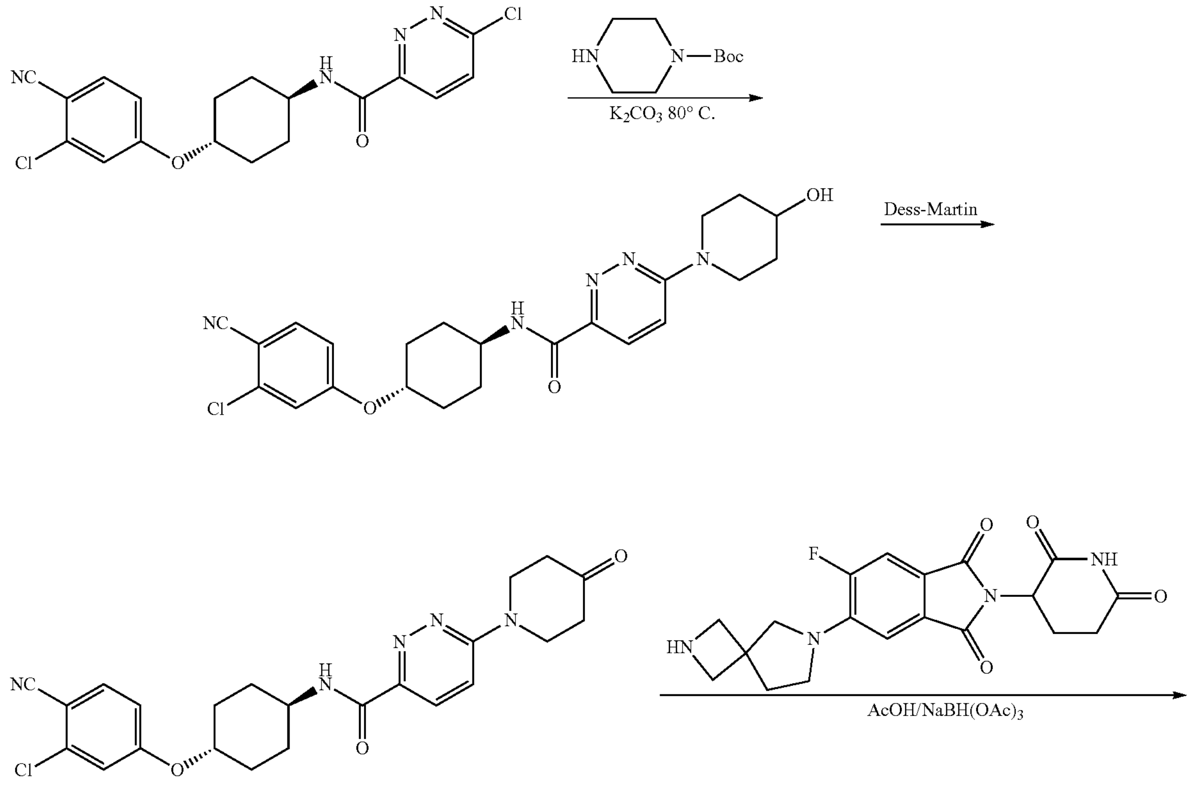

-continued

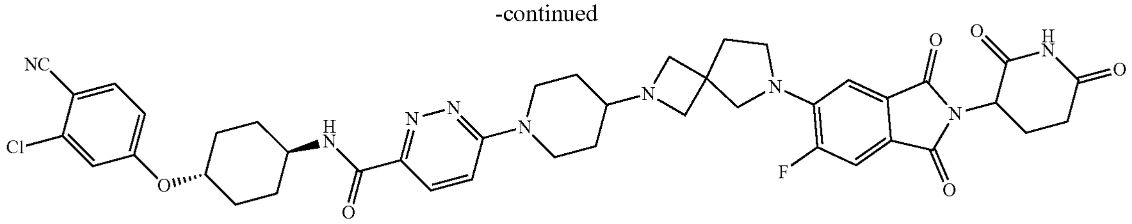

103

1. Synthesis of 6-(4-hydroxypiperidin-1-yl)-pyridazine-3-carboxylic acid [4-(3-chloro-4-cyano-phenoxy)-cyclohexyl]-amide Piperidine-4-ol (100 mg, 1.0 mmol) was dissolved in 5 ml DMF, to which were successively added anhydrous potassium carbonate (415 mg, 3.0 mmol) and 5-chloro-pyridazine-2-carboxylic acid [4-(4-cyano-3-chloro-phenoxy)-cyclohexyl]-amide (390 mg, 1.0 mmol), and the mixture was allowed to react at 80° C. for 3 h, to which was added 15 ml ethyl acetate. The reaction solution was successively washed with water and saturated brine, dried over anhydrous sodium sulfate, filtered, concentrated to dryness under reduced pressure, and separated by thin layer chromatography, to provide the product 6-(4-hydroxypiperidin-1-yl)-pyridazine-3-carboxylic acid [4-(3-chloro-4-cyano-phenoxy)-cyclohexyl]-amide (310 mg), with a yield of 68.3%, LC/MS ($ESI^+$) calcd for $C_{23}H_{26}ClN_5O_3$ ($[M+H]^+$) m/z 455.9.

2. 6-(4-Oxopiperidin-1-yl)-pyridazine-3-carboxylic acid [4-(3-chloro-4-cyano-phenoxy)-cyclohexyl]-amide 6-(4-Hydroxypiperidin-1-yl)-pyridazine-3-carboxylic acid [4-(3-chloro-4-cyano-phenoxy)-cyclohexyl]-amide (250 mg, 0.55 mmol) was dissolved in 10 mL of dichloromethane, to which was added Dess-Martin periodinane (280 mg, 0.66 mmol). The solution was stirred and reacted at room temperature for 3 h, filtered, concentrated to dryness under reduced pressure, and separated by thin layer chromatography, to obtain the product 6-(4-oxopiperidin-1-yl)-pyridazine-3-carboxylic acid [4-(3-chloro-4-cyano-phenoxy)-cyclohexyl]-amide (180 mg), with a yield of 72%, LC/MS ($ESI^+$) calcd for $C_{23}H_{24}ClN_5O_3$ ($[M+H]^+$) m/z 453.9.

3. N-((1r,4r)-4-(3-chloro-4-cyanophenoxy)cyclohexyl)-6-(4-(6-(2-(2,6-dioxopiperidin-3-yl)-6-fluoro-1,3-dioxoisoindolin-5-yl)-2,6-diazaspiro[3.4]octane-2-yl)piperidin-1-yl)pyridazine-3-formamide 6-(4-Oxopiperidin-1-yl)-pyridazine-3-carboxylic acid [4-(3-chloro-4-cyano-phenoxy)-cyclohexyl]-amide (46 mg, 0.1 mmol) and 5-(2,6-diazaspiro[3.4]octane-6-yl)-2-(2,6-dioxopiperidin-3-yl)-6-fluoroisoindoline-1,3-dione) were dissolved in 5 ml of dichloromethane, to which was added one drop of acetic acid. The resultant solution was allowed to react at room temperature for 15 min, to which was added sodium cyanoborohydride (80 mg, 1.3 mmol). The reaction solution was allowed to react overnight at room temperature, cooled to room temperature, washed with water, concentrated to dryness under reduced pressure, and separated by thin layer chromatography, to obtain the yellow solid product N-((1r,4r)-4-(3-chloro-4-cyanophenoxy)cyclohexyl)-6-(4-(6-(2-(2,6-dioxopiperidin-3-yl)-6-fluoro-1,3-dioxoisoindolin-5-yl)-2,6-diazaspiro[3.4]octane-2-yl)piperidin-1-yl) pyridazine-3-formamide (16 mg), with a yield of 19.5%, LC/MS ($ESI^+$) for $C_{42}H_{43}ClFN_9O_6$ ($[M+H]^+$) m/z 823.8. $^1H$ NMR (400 MHz, $CDCl_3$) δ 8.14-8.06 (m, 1H), 8.06-8.01 (m, 1H), 7.91-7.85 (m, 1H), 7.61-7.56 (m, 1H), 7.47-7.41 (m, 1H), 7.03 (s, 3H), 6.90-6.85 (m, 1H), 4.94 (dd, J=12.2, 5.3 Hz, 1H), 4.53 (s, 1H), 4.34 (s, 1H), 4.07 (s, 1H), 3.81 (d, J=4.5 Hz, 2H), 3.65 (s, 2H), 3.20 (s, 2H), 2.93-2.75 (m, 3H), 2.19 (d, J=11.1 Hz, 5H), 1.99 (d, J=6.6 Hz, 2H), 1.71 (d, J=12.4 Hz, 2H), 1.61 (s, 9H), 1.52 (dd, J=18.4, 7.6 Hz, 3H).

104: N-((1r,4r)-4-(3-chloro-4-cyanophenoxy)cyclohexyl)-5-(4-((1R, 5S, 6s)-3-(2-(2,6-dioxopiperidin-3-yl)-1,3-dioxoisoindolin-5-yl)-3-azabicyclo[3.1.0]n-hexane-6-yl)methyl)piperazin-1-yl)pyrazine-2-carboxamide

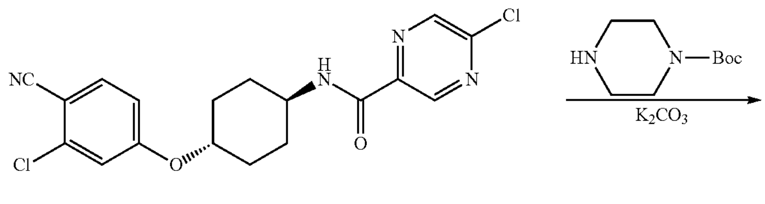

-continued
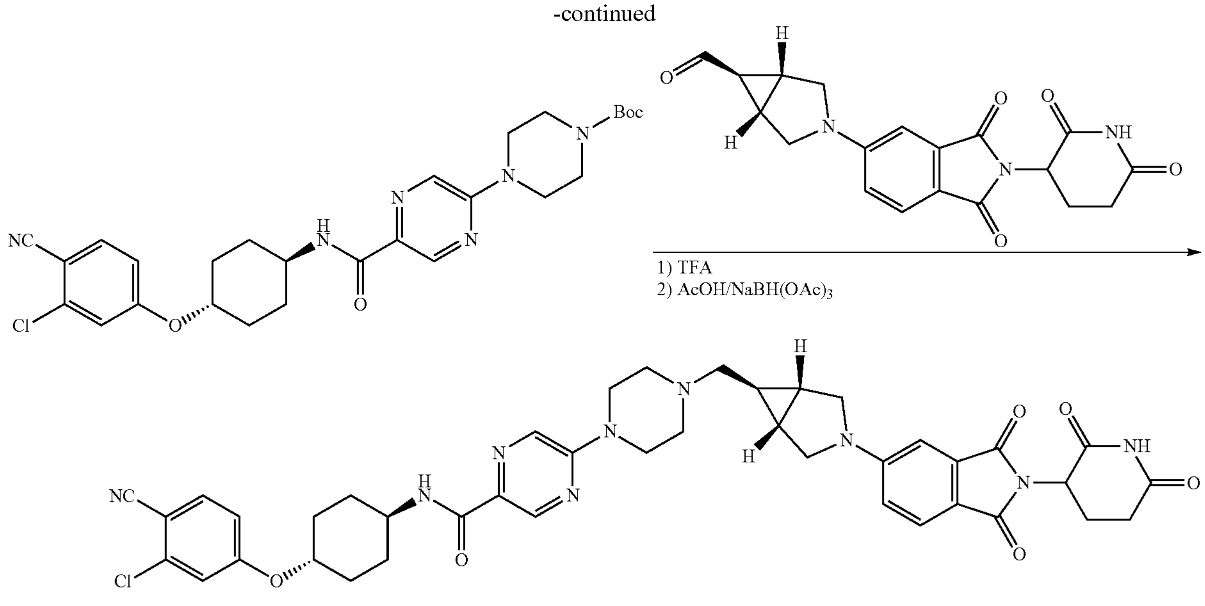
104
LC/MS (ESI+) m/z 791.8 for $C_{42}H_{43}ClN_9O_6$ ([M+H]+). $^1$H NMR (400 MHz, $CDCl_3$) δ 8.88 (s, 1H), 8.34-8.24 (m, 1H), 8.04-7.96 (m, 1H), 7.72-7.64 (m, 1H), 7.62-7.55 (m, 1H), 7.47-7.38 (m, 1H), 7.02 (s, 1H), 6.99-6.93 (m, 1H), 6.90-6.83 (m, 1H), 6.74-6.66 (m, 1H), 4.95 (dd, J=12.1, 5.2 Hz, 1H), 4.32 (dd, J=12.9, 6.8 Hz, 1H), 4.06 (d, J=10.0 Hz, 2H), 3.88 (s, 3H), 3.70 (d, J=9.9 Hz, 2H), 3.53 (d, J=8.5 Hz, 2H), 2.98-2.69 (m, 6H), 2.58 (s, 2H), 2.29-2.09 (m, 5H), 1.73 (dd, J=19.2, 9.9 Hz, 5H), 1.55-1.45 (m, 3H).
105: N-((1r,4r)-4-(3-chloro-4-cyanophenoxy)cyclohexyl)-5-(7-((1-(2-(2,6-dioxopiperidin-3-yl)-1,3-dioxoisoindolin-5-yl)piperidine-4-yl)methyl)-2,7-diazaspiro[3.5]nonan-2-yl)-1,3,4-thiadiazole-2-carboxamide
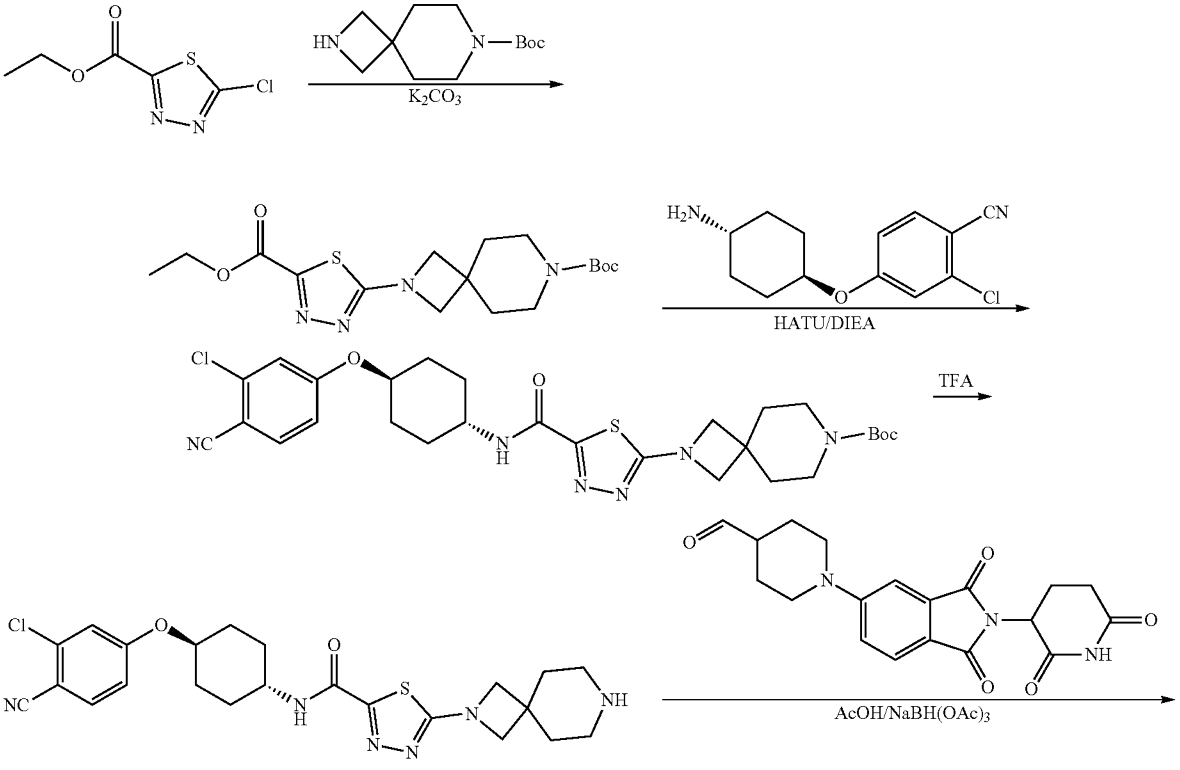

-continued

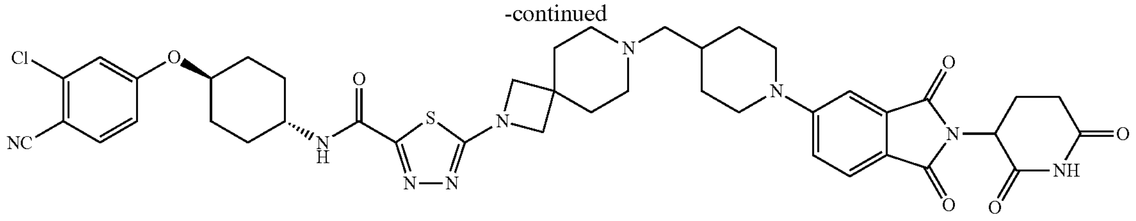

105

1. Synthesis of ethyl 5-(7-(t-butoxycarbonyl)-2,7-diazaspiro[3.5]nonan-2-yl)-1,3,4-thiadiazole-2-carboxylate t-Butyl 2,7-diazaspiro[3.5]nonane-7-carboxylate (249 mg, 1.1 mmol) was dissolved in 6 ml of DMF, to which were successively added anhydrous potassium carbonate (416 mg, 3.0 mmol) and ethyl 5-chloro-1,3,4-thiadiazole-2-carboxylate (193 mg, 1.0 mmol), and the mixture was allowed to react at 80° C. for 1.5 h. The reaction solution was cooled to room temperature, to which was added 20 ml ethyl acetate. The reaction solution was successively washed with water and saturated brine, dried over anhydrous sodium sulfate, filtered, concentrated to dryness under reduced pressure, and separated by thin layer chromatography, to provide the product ethyl 5-(7-(t-butoxycarbonyl)-2,7-diazaspiro[3.5]nonan-2-yl)-1,3,4-thiadiazole-2-carboxylate (295 mg), with a yield of 79.9%, LC/MS (ESI$^+$) calcd for $C_{17}H_{26}N_2O_2S$ ([M+H]$^+$) m/z 369.1.

2. Synthesis of 5-(2,7-diazaspiro[3.5]nonan-2-yl)-[1,3,4]thiadiazole-2-carboxylic acid [4-(3-chloro-4-cyano-phenoxy)-cyclohexyl]-amide 4-(4-Aminocyclohexyloxy)-2-chloro-benzonitrile (210 mg, 0.84 mmol) was dissolved in 5 mL of methanol, to which was added t-butyl 2-(5-ethoxycarbonyl-[1,3,4]thiadiazol-2-yl)-2,7-diazaspiro[3.5]nonan-7-carboxylate (268 mg, 0.7 mmol), and then the resultant solution was refluxed overnight at 85° C. and separated by thin layer chromatography, to obtain 360 mg of white solid product. The product was dissolved in 5 ml of dichloromethane, to which was added 3 mL of trifluoroacetic acid. The reaction solution was stirred at room temperature for 2.5 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain the white solid product 5-(2,7-diazaspiro[3.5]nonan-2-yl)-[1,3,4]thiadiazole-2-carboxylic acid [4-(3-chloro-4-cyano-phenoxy)-cyclohexyl]-amide (290 mg), with a yield of 85/a, LC/MS (ESI$^+$) calcd for $C_{23}H_{27}ClN_6O_2S$ ([M+H]$^+$) m/z 487.1.

3. Synthesis of N-((1r,4r)-4-(3-chloro-4-cyanophenoxy)cyclohexyl)-5-(7-((1-(2-(2,6-dioxopiperidin-3-yl)-1,3-dioxoisoindolin-5-yl)piperidine-4-yl)methyl)-2,7-diazaspiro[3.5]nonan-2-yl)-1,3,4-thiadiazole-2-carboxamide 5-(2,7-Diazaspiro[3.5]nonan-2-yl)-[1,3,4]thiadiazole-2-carboxylic acid [4-(3-chloro-4-cyano-phenoxy)-cyclohexyl]-amide (49 mg, 0.1 mmol) and 1-[2-(2,6-dioxopiperidin-3-yl)-1,3-dioxo-2,3-dihydro-1H-isoindol-5-yl]-piperidine-4-acetaldehyde (37 mg, 0.1 mmol) were added into a round bottom flask, to which was added 5 ml of dichloromethane, and then one drop of acetic acid was added to catalyze the reaction. Under the protection of argon, the reaction was stirred at room temperature for 10 min, to which was added sodium triacetylborohydride (212 mg, 1.0 mmol), and reacted at room temperature for 3 h. The organic layer was successively washed twice with water and then washed once with saturated brine, dried over anhydrous sodium sulfate, concentrated to dryness under reduced pressure, and separated by TLC, to provide the yellow solid product N-((1r,4r)-4-(3-chloro-4-cyanophenoxy)cyclohexyl)-5-(7-((1-(2-(2,6-dioxopiperidin-3-yl)-1,3-dioxoisoindolin-5-yl)piperidine-4-yl)methyl)-2,7-diazaspiro[3.5]nonan-2-yl)-1,3,4-thiadiazole-2-carboxamide (45 mg), with a yield of 53.6%, LC/MS (ESI$^+$) $C_{42}H_{46}ClN_9O_6S$ ([M+H]$^+$ m/z, 840.3. $^1$H NMR (400 MHz, $CDCl_3$) δ 8.14 (s, 1H), 7.67 (d, J=8.5 Hz, 1H), 7.56 (d, J=8.7 Hz, 1H), 7.27 (s, 1H), 7.08-6.95 (m, 3H), 6.84 (dd, J=8.8, 2.4 Hz, 1H), 4.94 (dd, J=12.3, 5.3 Hz, 1H), 4.30 (t, J=10.0 Hz, 1H), 3.96 (dd, J=26.6, 12.1 Hz, 6H), 3.07-2.66 (m, 6H), 2.35 (s, 2H), 2.18 (s, 6H), 1.88 (s, 4H), 1.65 (d, J=17.7 Hz, 7H), 1.53-1.44 (m, 2H), 1.25 (dd, J=8.5, 5.5 Hz, 3H).

106: N-((1r,4r)-4-(3-chloro-4-cyanophenoxy)cyclohexyl)-5-(7-(1-(2-(2,6-dioxopiperidin-3-yl)-1,3-dioxoisoindolin-5-yl)piperidine-4-yl)-2,7-diazaspiro[3.5]nonan-2-yl)pyrimidine-2-carboxamide

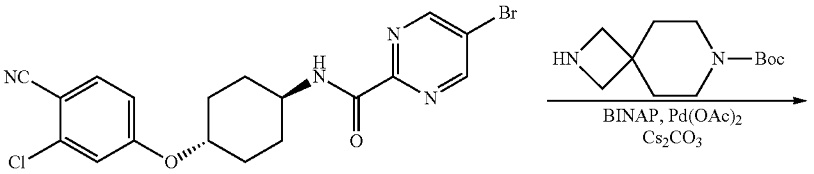

-continued

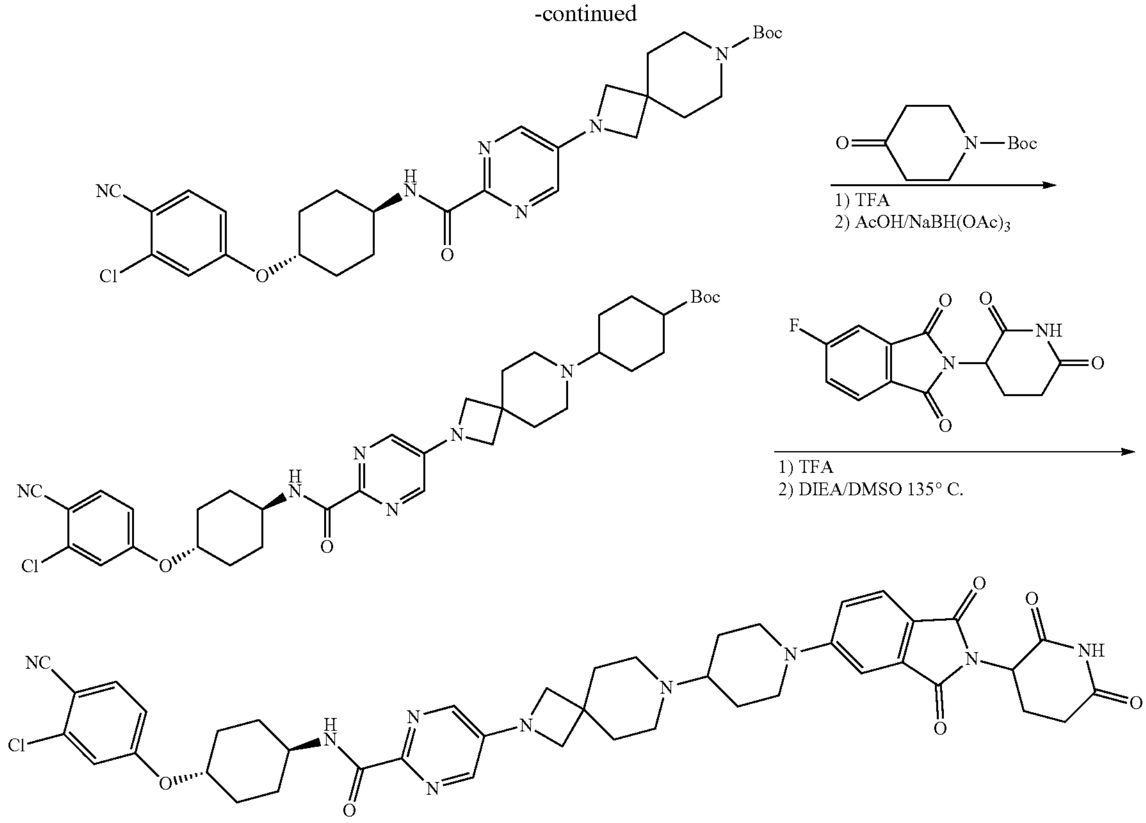

106

1. Synthesis of t-butyl 2-{2-[4-(3-chloro-4-cyano-phenoxy)-cyclohexylcarbamoyl]-pyrimidin-5-yl}-2,7-diazaspiro[3.5]nonane-7-carboxylate 5-Bromo-pyrimidine-2-carboxylic acid [4-(3-chloro-4-cyano-phenoxy)-cyclohexyl]-amide (109 mg, 0.25 mmol) was dissolved in 5 mL of 1,4-dioxane, to which were added t-butyl 2,7-diazaspiro[3.5]nonane-7-carboxylate (57 mg, 0.25 mmol). BINAP (8 mg, 12.5 μmol), $Cs_2CO_3$ (163 mg, 0.5 mmol), and $Pd(OAc)_2$ (3 mg, 12.5 μmol). Under argon protection, the reaction solution was refluxed overnight at 110° C., to which was added 15 ml of ethyl acetate. The organic phase was successively washed three times with 10 ml of water and washed once with saturated brine, dried over anhydrous sodium sulfate, concentrated to dryness under reduced pressure, and separated by TLC, to provide the product t-butyl 2-{2-[4-(3-chloro-4-cyano-phenoxy)-cyclohexylcarbamoyl]-pyrimidin-5-yl}-2,7-diazaspiro[3.5]nonane-7-carboxylate (100 mg), with a yield of 68.9%, LC/MS ($ESI^+$) calcd for $C_{30}H_{37}ClN_6O_4$ ($[M+H]^+$) m/z 580.9.

2. Synthesis of t-butyl 4-(2-{2-[4-(3-chloro-4-cyano-phenoxy)-cyclohexylcarbamoyl]-pyrimidin-5-yl}-2,7-diaza-spirocyclo[3.5]nonan-7-yl)-piperidine-1-carboxylate t-Butyl 2-{2-[4-(3-chloro-4-cyano-phenoxy)-cyclohexylcarbamoyl]-pyrimidin-5-yl}-2,7-diazaspiro[3.5]nonane-7-carboxylate (100 mg, 0.17 mmol) was dissolved in 5 mL of dichloromethane, to which was added 3 mL of trifluoroacetic acid. The reaction solution was stirred at room temperature for 3 h, and concentrated to dryness under reduced pressure. The pH of the reaction solution was adjusted to be alkaline with saturated $Na_2CO_3$ aqueous solution, and then extracted twice with DCM. The organic layers were combined, washed once with saturated brine, dried over anhydrous magnesium sulfate, filtered, and concentrated to dryness under reduced pressure, to obtain 80 mg of white solid. The obtained product (78 mg, 0.16 mmol) was dissolved in 5 mL of dichloromethane, to which were successively added 4-Bocpiperidone (199 mg, 0.98 mmol) and 0.5 drops of acetic acid. The resultant solution was allowed to ruflux 1 h at room temperature, and then cooled to room temperature, to which was added sodium triacetylbohydride (424 mg, 2.0 mmol). The resultant solution was allowed to react 5 h under reflux at 40° C. The reaction solution was cooled to room temperature and washed with water, concentrated to dryness under reduced pressure, and separated by thin layer chromatography, to obtain the product t-butyl 4-(2-{2-[4-(3-chloro-4-cyano-phenoxy)-cyclohexylcarbamoyl]-pyrimidin-5-yl}-2,7-diaza-spirocyclo[3.5]nonan-7-yl)-piperidine-1-carboxylate (50 mg), with a yield of 47.0%, LC/MS ($ESI^+$) calcd for $C_{35}H_{46}ClN_7O_4$ ($[M+H]^+$) m/z 664.3.

3. Synthesis of N-((1r,4r)-4-(3-chloro-4-cyanophenoxy)cyclohexyl)-5-(7-(1-(2-(2,6-dioxopiperidin-3-yl)-1,3-dioxoisopentanol-5-yl)piperidine-4-yl)-2,7-diazaspiro[3.5]nonan-2-yl)pyrimidine-2-carboxamide t-Butyl 4-(2-{2-[4-(3-chloro-4-cyano-phenoxy)-cyclohexylcarbamoyl]-pyrimidin-5-yl}-2,7-diaza-spirocyclo[3.5]nonan-7-yl)-piperidine-1-carboxylate (50 mg, 0.075 mmol) was dissolved in 3 mL of dichloromethane, to which was added 3 mL of trifluoroacetic acid. The reaction solution was stirred 2 h at room temperature, and concentrated to dryness under reduced pressure. To the residue, dichloromethane was added, followed by concentration under reduced pressure, that was repeated once. To the residue, were successively added 3 mL of DMSO, 0.5 mL of DIEA, and 2-(2,6-dioxopiperidin-3-yl)-5-fluoroisoindole-1,3-dione (30 mg, 0.11 mmol), and the resultant solution was refluxed 1.5 h at 135° C. The reaction solution was cooled to room temperature, to which was added 10 mL of dichloromethane. The organic phase was successively washed twice with 10 ml of water and washed once with saturated brine, dried over anhydrous sodium sulfate, concentrated to dryness under reduced pressure, and separated by thin layer chromatography, to provide the yellow solid product N-((1r,4r)-4-(3-chloro-4-cyanophenoxy)cyclohexyl)-5-(7-(1-(2-(2,6-dioxopiperidin-3-yl)-1,3-dioxoisoindolin-5-yl)piperidine-4-yl)-2,7-diazaspiro[3.5]nonan-2-yl)pyrimidine-2-carboxamide (26 mg), with a yield of 42.3%, LC/MS (ESI) m/z 820.3 for $C_{43}H_{46}ClN_9O_6$ ([M+H]$^+$). $^1$H NMR (400 MHz, $CDCl_3$) δ 8.16 (s, 11H), 7.95 (s, 2H), 7.69 (d, J=8.5 Hz, 2H), 7.56 (d, J=8.7 Hz, 1H), 7.28 (d, J=2.1 Hz, 1H), 7.06 (dd, J=8.6, 2.1 Hz, 1H), 6.99 (d, J=2.3 Hz, 1H), 6.85 (dd, J=8.8, 2.4 Hz, 1H), 4.99-4.90 (m, 1H), 4.34-4.25 (m, 1H), 4.15-4.07 (m, 1H), 4.02 (d, J=13.3 Hz, 2H), 3.80 (s, 4H), 3.00 (t, J=12.0 Hz, 2H), 2.95-2.71 (m, 4H), 2.25-2.13 (m, 7H), 2.01 (s, 4H), 1.69 (d, J=12.3 Hz, 8H), 1.46 (dd, J=24.4, 11.7 Hz, 2H).

107: N-((1r,4r)-4-(3-chloro-4-cyanophenoxy)cyclohexyl)-5-(7-((1-(2-(2,6-dioxopiperidin-3-yl)-6-fluoro-1,3-dioxoisoindolin-5-yl)piperidine-4-yl)methyl)-2,7-diazaspiro[3.5]nonan-2-yl)-1,3,4-thiadiazole-2-carboxamide

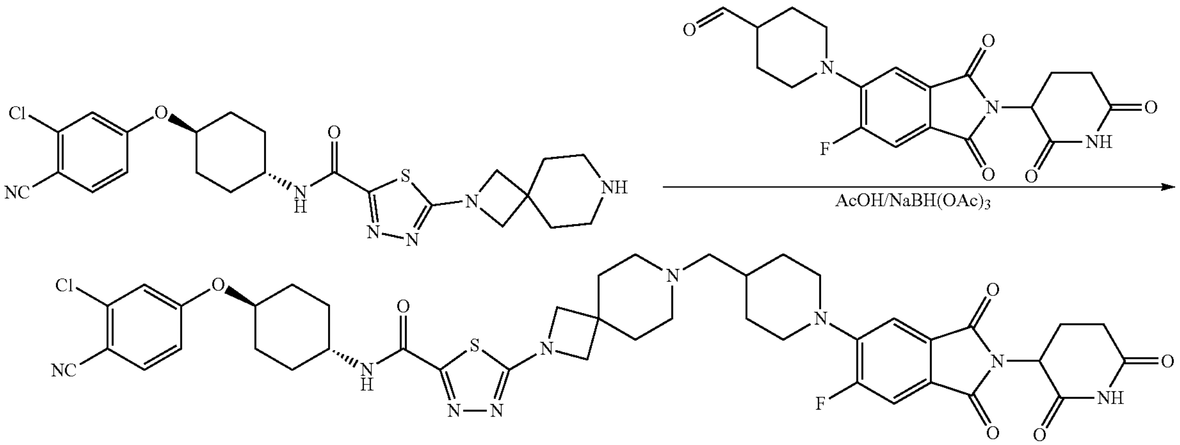

107

Synthetic procedures referred to 105.

Characteristic data: LC/MS (ESI$^+$) m-z 858.3 for $C_{42}H_{45}ClFN_9O_6S$ ([M+H]$^+$), $^1$H NMR (400 MHz, $CDCl_3$) δ 8.14-8.08 (m, 1H), 7.56 (d, J=8.7 Hz, 1H), 7.46 (d, J=11.0 Hz, 1H), 7.39 (d, J=7.3 Hz, 1H), 7.03 (d, J=8.2 Hz, 1H), 6.99 (d, J=2.3 Hz, 1H), 6.84 (dd, J=8.8, 2.4 Hz, 1H), 4.97-4.90 (m, 1H), 4.36-4.26 (m, 1H), 4.05-3.95 (m, 1H), 3.90 (s, 4H), 3.73 (q, J=7.0 Hz, 3H), 3.65 (d, J=12.1 Hz, 2H), 2.95-2.70 (m, 5H), 2.40-2.34 (m, 2H), 2.22 (d, J=7.6 Hz, 2H), 1.92-1.86 (m, 6H), 1.69-1.61 (m, 4H), 1.50 (dd, J=18.4, 7.7 Hz, 2H), 1.25 (t, J=7.0 Hz, 5H).

108: N-(1-(3-chloro-4-cyanobenzene)piperidine-4-yl)-6-(4-((4-(2-(2,6-dioxopiperidin-3-yl)-1,3-dioxoisoindolin-5-yl)piperazin-1-yl)methyl)piperidin-1-yl)pyridazine-3-formamide

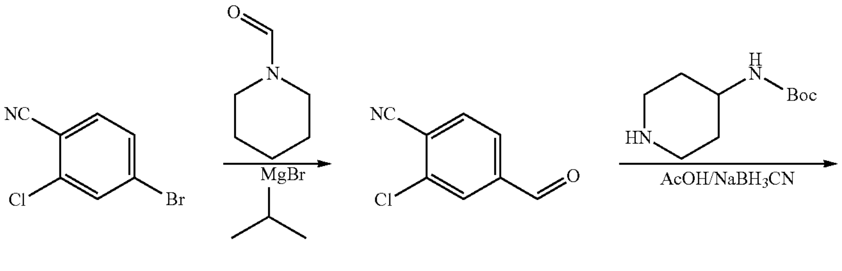

-continued

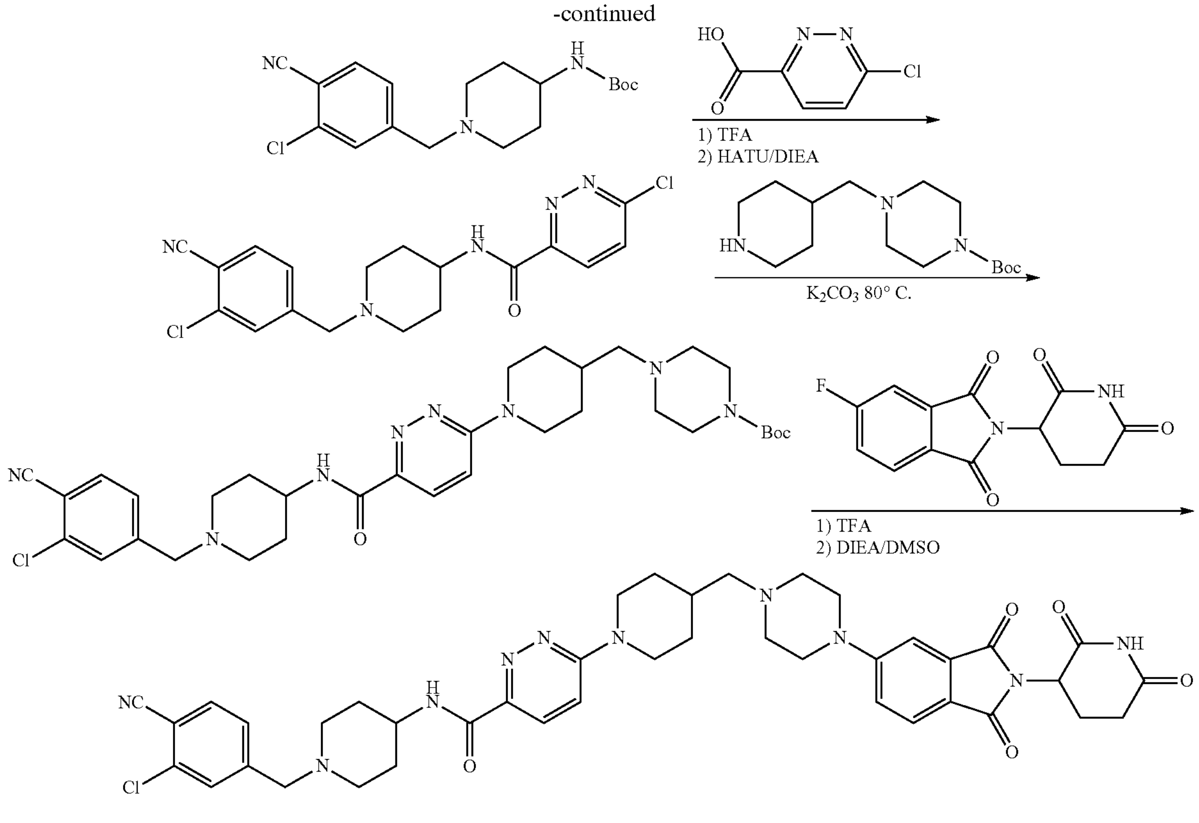

108

1) 2-chloro-4-formylbenzonitrile

4-Bromo-2-chloro-benzonitrile (5.0 g, 23.1 mmol) was dissolved in 10 ml of anhydrous tetrahydrofuran, and then under the protection of argon, 15 ml of 2N isopropylmagnesium bromide/THF solution was added dropwise in an ice water bath. After that, the reaction solution was stirred for 1 h in the ice water bath, to which was added piperidine-1-acetaldehyde (7.75 g, 68.5 mmol), and the solution was allowed to react for additional 2 h in the ice water bath, 15 ml of saturated ammonium chloride aqueous solution was added to quench the reaction, and extracted with 20 ml of ethyl acetate. The water layer is then extracted once with 20 ml of ethyl acetate, and the organic layer was combined. The organic layer was washed once with saturated brine, dried over anhydrous sodium sulfate, filtered, concentrated to dryness under reduced pressure, and separated and purified by column chromatography, to provide the product 2-chloro-4-formylbenzonitrile (2.22 g), with a yield of 58%.

2) t-Butyl (1-(3-chloro-4-cyanobenzene)piperidine-4-yl)carbamate

2-Chloro-4-formylbenzonitrile (820 mg, 5.0 mmol) and t-butyl piperidin-4-ylcarbamate (1.0 g, 5.0 mmol) were dissolved in 15 mL of anhydrous methanol, to which was added 2 drops of acetic acid. The reaction solution was allowed to react at 60° C. for 1 h, and then cooled to room temperature, to which was added sodium cyanoborohydride (942 mg, 15 mmol). The mixture was reacted overnight, to which was added 20 mL of acetone, and the resultant solution was stirred for 20 min, and concentrated to dryness under reduced pressure. To the residue, was added 20 mL of ethyl acetate, and then the solution was successively washed with water and saturated brine, dried over anhydrous sodium sulfate, and filtered. The filtrate was concentrated under reduced pressure to dryness, and then separated and purified by column chromatography, to provide the product t-butyl (1-(3-chloro-4-cyanobenzene)piperidin-4-yl)carbamate (680 mg), with a yield of 38.9%, LC/MS (ESI+) calcd for $C_{18}H_{24}ClN_3O_2$ ($[M+H]^+$) m/z 350.2.

3) 6-Chloro-N-(1-(3-chloro-4-cyanobenzene)piperidin-4-yl)pyridazine-3-formamide t-Butyl (1-(3-chloro-4-cyanobenzene)piperidin-4-yl)carbamate (370 mg, 0.95 mmol) was dissolved in 10 mL of dichloromethane, to which was added 8 mL of trifluoroacetic acid. The reaction solution was stirred at room temperature for 2 h, and concentrated to dryness under reduced pressure. The pH of the reaction solution was adjusted to be alkaline with saturated $Na_2CO_3$ aqueous solution, and then extracted twice with ethyl acetate. The organic layers were combined, dried over anhydrous sodium sulfate, and concentrated to dryness under reduced pressure, to obtain 230 mg of the product. 6-Chloropyridine-3-carboxylic acid (145 mg, 0.91 mmol) was dissolved in 5 mL of dichloromethane, to which was added N,N-diisopropylethylamine (235 mg, 1.82 mmol), and then HATU (533 mg, 1.38 mmol) was added to the solution in an ice-water bath. The compound obtained in the previous step was dissolved in 5 mL of dichloromethane, which was added dropwise to the reaction system. After that, the reaction solution was slowly warmed to room temperature and reacted for 2 h. The solution was successively washed with the saturated aqueous solution of ammonium chloride and saturated brine, dried over anhydrous magnesium sulfate, filtered, concentrated to dryness under reduced pressure, and separated and purified by thin layer chromatography, to provide the product 6-chloro-N-(1-(3-chloro-4-cyanobenzene)piperidine-4-yl)pyridazine-3-formamide (200 mg), with a yield of 53.7%. LC/MS ($ESI^+$) calcd for $C_{18}H_{17}Cl_2N_5O$ ($[M+H]^+$) m/z 390.

4) t-Butyl 4-((1-(6-((1-(3-Chloro-4-cyanobenzene) piperidine-4-yl)carbamoyl) pyridazin-3-yl)piperidin-4-yl)methyl)piperazine-1-carboxylate t-Butyl 4-(piperidin-4-ylmethyl)piperazine-1-carboxylate (71 mg, 0.25 mmol) was dissolved in 5 mL of DMF, to which were successively added potassium carbonate (102 mg, 0.75 mmol) and 6-chloro-N-(1-(3-chloro-4-cyanobenzene)piperidin-4-yl)pyridazine-3-formamide (100 mg, 0.25 mmol), and the mixture was allowed to react 3 h at 80° C. The reaction solution was cooled to room temperature, to which was added 20 mL ethyl acetate. The resultant solution was successively washed with water and saturated bine, dried over anhydrous sodium sulfate, filtered, concentrated to dryness under reduced pressure, and separated by thin layer chromatography, to provide the product t-butyl 4-((1-(6-((1-(3-chloro-4-cyanobenzene)piperidine-4-yl)carbamoyl) pyridazin-3-yl)piperidin-4-yl)methyl)piperazine-1-carboxylate (140 mg), with a yield of 87.9%, LC/MS ($ESI^+$) calcd for $C_{33}H_{45}ClN_8O_3$ ($[M+H]^+$) m/z 637.3.

5) N-(1-(3-Chloro-4-cyanobenzene)piperidin-4-yl)-6-(4-((4-(2-(2,6-dioxopiperidin-3-yl)-1,3-dioxoisoindolin-5-yl)piperazin-1-yl)methyl)piperidin-1-yl) pyridazine-3-formamide t-Butyl 4-((1-(6-((1-(3-chloro-4-cyanobenzene)piperidin-4-yl)carbamoyl)pyridazin-3-yl)piperidin-4-yl)methyl)piperazine-1-carboxylate (75 mg, 0.12 mmol) was dissolved in 3 mL of dichloromethane, to which was added 2 mL of trifluoroacetic acid. The reaction solution was stirred 2 h at room temperature, and concentrated to dryness under reduced pressure. To the residue, were successively added 5 mL of DMSO, 0.8 mL of DIEA, and 2-(2,6-dioxopiperidin-3-yl)-5-fluoroisoindole-1,3-dione (60 mg, 0.22 mmol), and the resultant solution was allowed to react 3 h at 140° C. The reaction solution was cooled to room temperature, to which was added 15 mL of dichloromethane. The organic phase was successively washed twice with the saturated aqueous solution of ammonium chloride and washed once with saturated brine, dried over anhydrous magnesium sulfate, concentrated to dryness under reduced pressure, and separated and purified by thin layer chromatography, to provide the product N-(1-(3-chloro-4-cyanobenzene)piperidine-4-yl)-6-(4-((4-(2-(2,6-dioxopiperidin-3-yl)-1,3-dioxoisoindolin-5-yl)piperazin-1-yl)methyl)piperidin-1-yl)pyridazine-3-formamide (42 mg), with a yield of 44.1%, LC/MS (ESI) for $C_{41}H_{45}ClN_{10}O_5$ ($[M+H]^+$) m/z 793.3. $^1H$ NMR (400 MHz, $CDCl_3$) δ 8.12 (s, 1H), 7.97 (d, J=9.5 Hz, 1H), 7.90 (d, J=8.0 Hz, 1H), 7.70 (d, J=8.5 Hz, 1H), 7.63 (d, J=7.9 Hz, 1H), 7.54 (s, 1H), 7.37 (d, J=8.5 Hz, 1H), 7.29 (d, J=2.0 Hz, 1H), 7.06 (dd, J=8.6, 2.0 Hz, 1H), 6.98 (d, J=9.6 Hz, 1H), 4.95 (dd, J=12.2, 5.2 Hz, 1H), 4.52 (d, J=13.0 Hz, 2H), 4.08-3.95 (m, 1H), 3.55 (s, 2H), 3.44 (s, 4H), 3.05 (t. J=12.0 Hz, 2H), 2.95-2.72 (m, 5H), 2.60 (s, 3H), 2.28 (d, J=11.0 Hz, 4H), 2.14 (dd, J=7.6, 5.3 Hz, 1H), 1.99 (dd, J=24.5, 13.5 Hz, 5H), 1.36-1.16 (m, 5H).

109: N-(6-(3-chloro-4-cyanophenoxy)spiro[3.3]heptan-2-yl)-6-(4-((4-(2,6-dioxopiperidin-3-yl)-1,3-dioxoisoindolin-5-yl)piperazin-1-yl)piperidin-1-yl) pyridazine-3-formamide

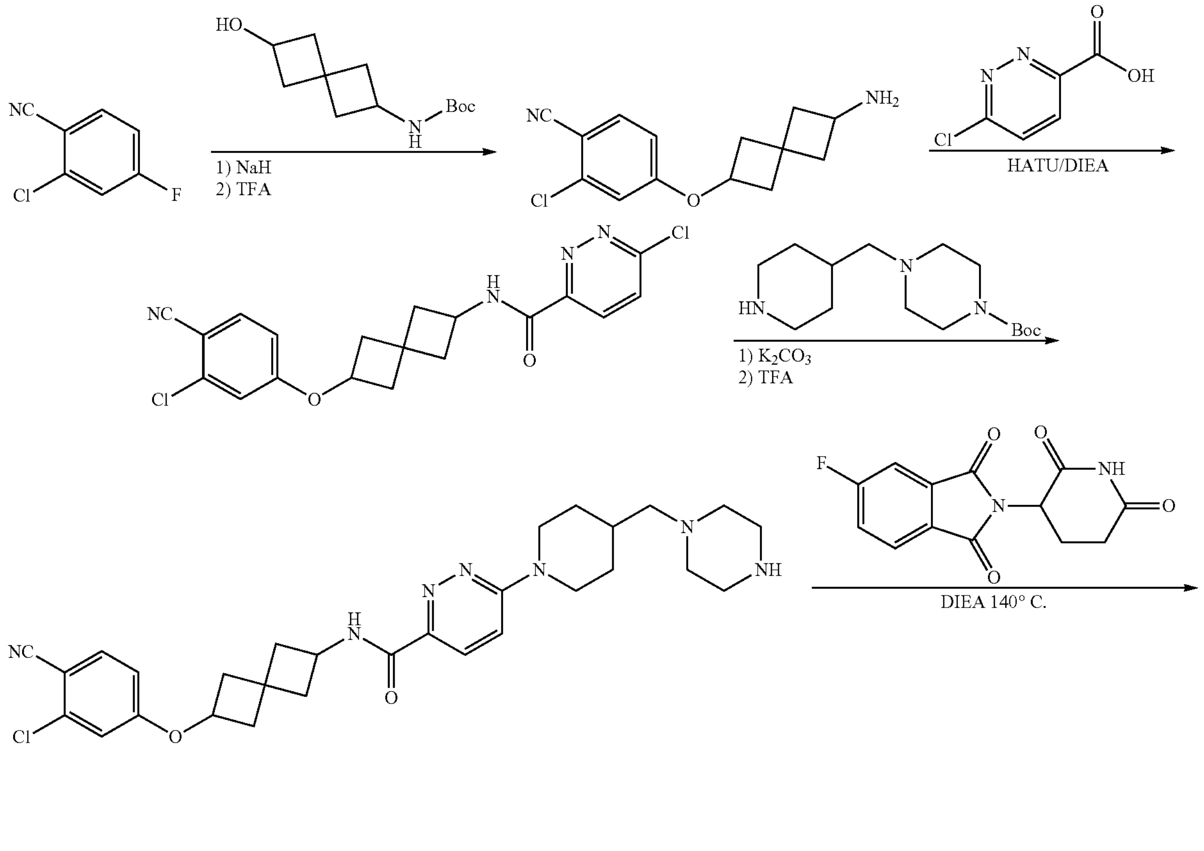

-continued

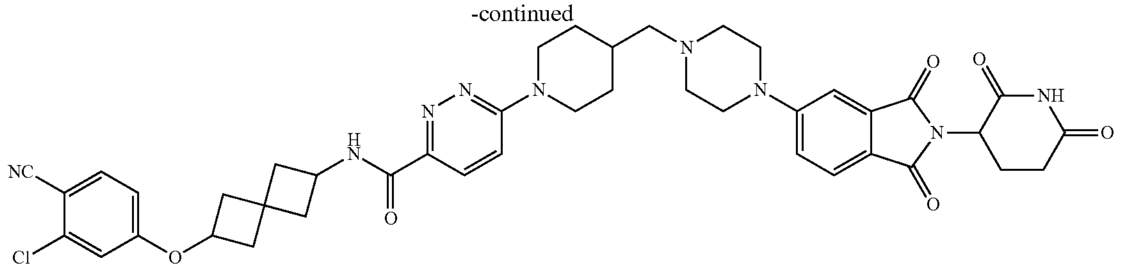

109

LC/MS (ESI+) for $C_{42}H_{44}ClN_9O_6$ ([M+H]+) m/z 806.2, $^1$H NMR (400 MHz, $CDCl_3$) δ 8.09 (s, 1H), 8.05 (d, J=8.1 Hz, 1H), 7.95 (d, J=9.6 Hz, 1H), 7.71 (d, J=8.5 Hz, 1H), 7.55 (d, J=8.7 Hz, 1H), 7.30 (d, J=2.1 Hz, 1H), 7.07 (dd, J=8.6, 2.1 Hz, 1H), 6.97 (d, J=9.7 Hz, 1H), 6.88 (d, J=2.3 Hz, 1H), 6.75 (dd, J=8.7, 2.4 Hz, 1H), 4.95 (dd, J=12.3, 5.3 Hz, 1H), 4.66-4.59 (m, 1H), 4.56-4.51 (m, 2H), 3.49 (s, 3H), 3.06 (t, J=12.1 Hz, 2H), 2.98-2.74 (m, 4H), 2.75-2.67 (m, 2H), 2.65-2.57 (m, 2H), 2.56-2.49 (m, 2H), 2.26 (ddd, J=24.1, 11.9, 6.9 Hz, 4H), 2.18-2.08 (m, 3H), 1.99 (d, J=12.8 Hz, 3H), 1.50-1.40 (m, 1H), 1.29 (dd, J=20.4, 11.2 Hz, 4H).

110: N-((1r,4S)-4-(3-chloro-4-cyanophenoxy)cyclohexyl)-6-(4-((3S)-1-(2-(2,6-dioxopiperidin-3-yl)-6-fluoro-1,3-dioxoisoindolin-5-yl)pyrrolidine-3-yl)oxy)piperidin-1-yl)pyridazine-3-formamide

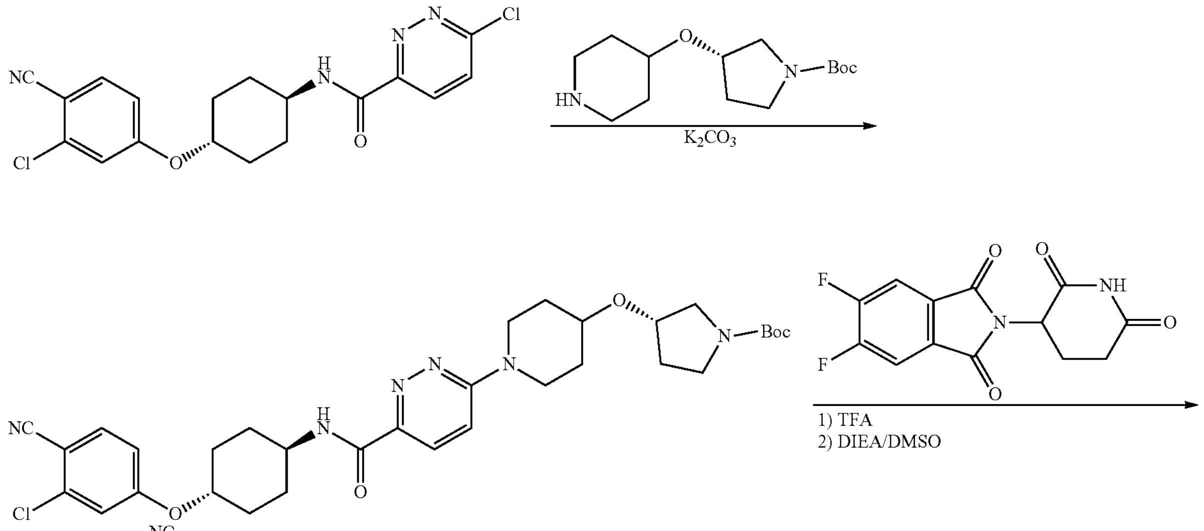

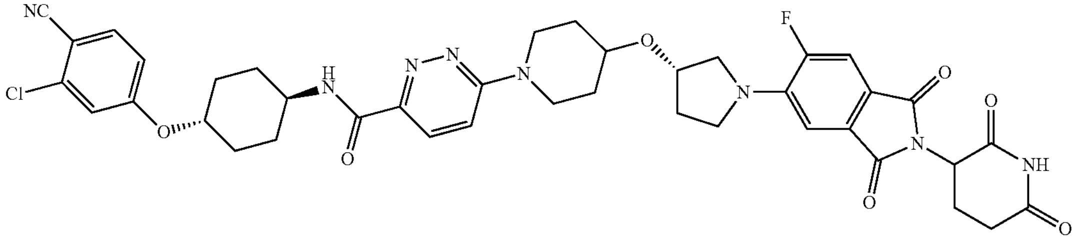

110

LC/MS (ESI+) calcd for $C_{40}H_{40}ClFN_8O_7$ ([M+H]+) m/z 799.2, $^1$H NMR (400 MHz, $CDCl_3$) δ 8.06 (d, J=6.8 Hz, 2H), 7.92 (d, J=7.8 Hz, 1H), 7.56 (d, J=8.7 Hz, 1H), 7.41 (d, J=12.3 Hz, 1H), 7.13 (d, J=9.7 Hz, 1H), 7.04 (d, J=7.5 Hz, 1H), 7.00 (d, J=2.3 Hz, 1H), 6.86 (dd, J=8.7, 2.3 Hz, 1H), 4.92 (dd, J=12.2, 5.3 Hz, 1H), 4.33 (dd, J=21.3, 12.3 Hz, 2H), 4.05 (d, J=3.7 Hz, 2H), 3.84-3.58 (m, 6H), 2.96-2.69 (m, 3H), 2.15 (t, J=13.5 Hz, 6H), 1.98 (s, 2H), 1.78 (s, 2H), 1.67 (dd, J=21.9, 10.8 Hz, 4H), 1.48 (dd, J=22.3, 11.5 Hz, 3H).

111: N-((1r,4R)-4-(3-chloro-4-cyanophenoxy)cyclohexyl)-4-(4-(((3R)-1-(2-(2,6-dioxopiperidin-3-yl)-1,3-dioxoisoindolin-5-yl)pyrrolidine-3-yl)oxy)piperidin-1-yl) benzamide

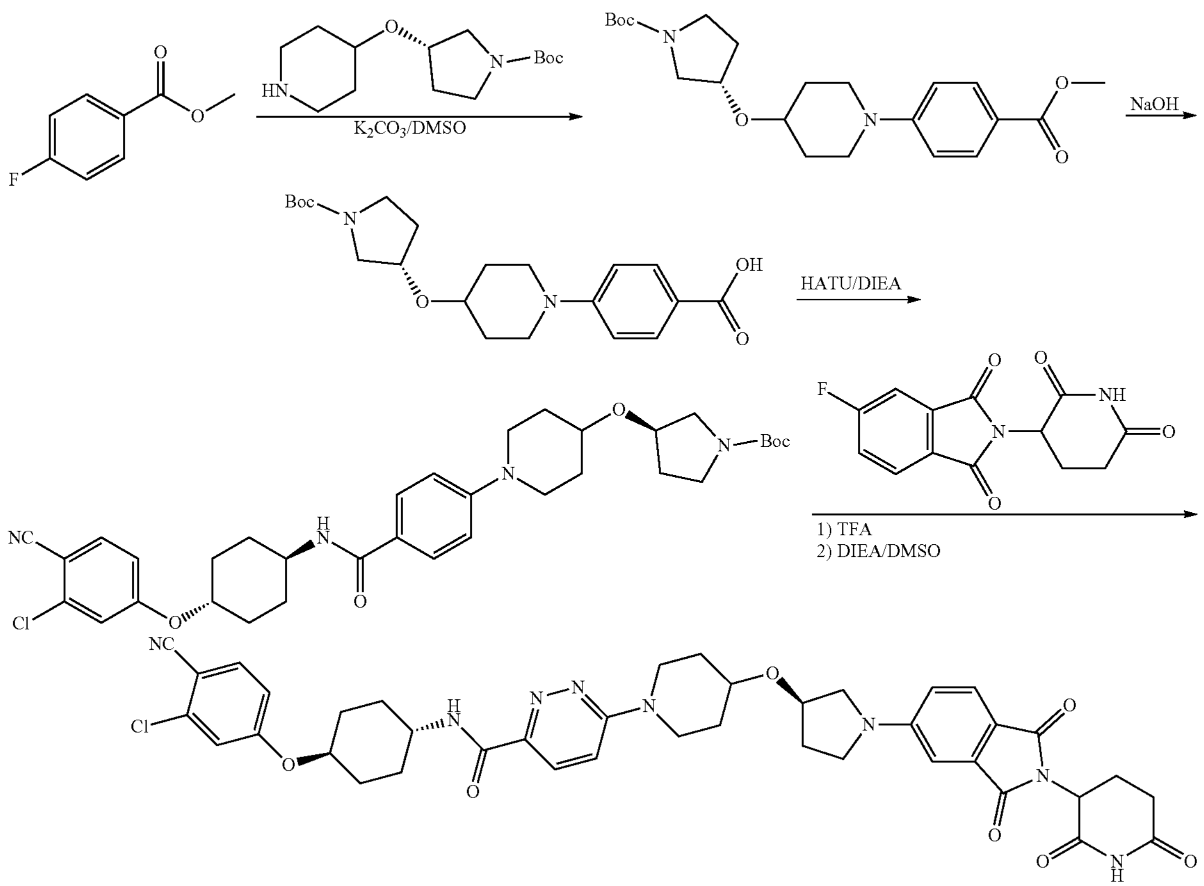

111

1) t-Butyl (S)-3-((1-(4-(methoxycarbonyl)phenyl) piperidine-4-yl)oxy)pyrrolidine-1-carboxylate t-Butyl (S)-3-(piperidine-4-oxy)pyrrolidine-1-carboxylate (260 mg, 0.96 mmol) was dissolved in 5 mL DMSO, to which were added potassium carbonate (420 mg, 3.0 mmol) and methyl p-fluorobenzoate (308 mg, 2.0 mmol), and the mixture was allowed to react at 100° C. for 3 h. The reaction solution was cooled to room temperature, to which was added 15 mL of ethyl acetate. The organic phase was successively washed with water and saturated brine, dried over anhydrous sodium sulfate, concentrated to dryness under reduced pressure, and separated and purified by thin layer chromatography, to provide the product t-butyl (S)-3-((1-(4-(methoxycarbonyl)phenyl)piperidine-4-yl)oxy)pyrrolidine-1-carboxylate (130 mg), with a yield of 33.5%, LC/MS (ESI+) calcd for $C_{22}H_{32}N_2O_5$ ([M+H]+) m/z 405.3.

2) t-Butyl (R)-3-((1-(4-((1r,4R)-4-(3-chloro-4-cyanophenoxy)cyclohexyl)carbamoyl) phenyl)piperidine-4-yl)oxy)pyrrolidine-1-carboxylate t-Butyl (S)-3-((1-(4-(methoxycarbonyl)phenyl)piperidine-4-yl)oxy)pyrrolidine-1-carboxylate (130 mg, 0.32 mmol) was dissolved in 5 mL of tetrahydrofuran, to which was added 5 mL of 2N NaOH aqueous solution, and the resultant solution was stirred overnight at room temperature. The solution was adjusted to pH=5 with 0.5 N HCl, to which was added 15 mL of ethyl acetate, and then successively washed with water and brine, dried over anhydrous sodium sulfate, and concentrated to dryness under reduced pressure, to provide the product. The product was dissolved in 5 mL of dichloromethane, to which were successively added DIEA (101 mg, 1.0 mmol) and HATU (141 mg, 0.37 mmol). The mixture was stirred at room temperature for 10 min. to which was added 4-(((1r,4r)-4-aminocyclohexyl)oxy)-2-chlorobenzonitrile (80 mg, 0.32 mmol). The solution was allowed to react overnight at room temperature, and then washed with the saturated aqueous solution of ammonium chloride, water, and saturated brine, respectively, followed by drying over anhydrous sodium sulfate, concentrating under reduced pressure to dryness, as well as separation and purification by thin-layer chromatography, to provide the product t-butyl (R)-3-((1-(4-((1r,4R)-4-(3-chloro-4-cyanophenoxy)cyclohexyl)carbamoyl)phenyl)piperidine-4-yl) oxy)pyrrolidine-1-carboxylate (160 mg), with a yield of 80.26%, LC/MS (ESI+) calcd for $C_{34}H_{43}ClN_4O_5$ ([M+H]+) m/z 623.2.

3) N-((1r,4R)-4-(3-chloro-4-cyanophenoxy)cyclohexyl)-4-(4-((3R)-1-(2-(2,6-dioxopiperidin-3-yl)-1,3-dioxoisoindolin-5-yl)pyrrolidine-3-yl)oxy)piperidin-1-yl) benzamide t-Butyl (R)-3-((1-(4-((1r,4R)-4-(3-chloro-4-cyanophenoxy)cyclohexyl)carbamoyl) phenyl)piperidine-4-yl)oxy) pyrrolidine-1-carboxylate (50 mg, 0.080 mmol) was dissolved in 3 mL of dichloromethane, to which was added 2 mL of trifluoroacetic acid. The reaction solution was stirred 2 h at room temperature, and concentrated to dryness under reduced pressure. To the residue, were successively added 5 mL of DMSO, 0.8 mL of DIEA, and 2-(2,6-dioxopiperidin-3-yl)-5-fluoroisoindole-1,3-dione (23 mg, 0.080 mmol), and the resultant solution was allowed to react 3 h at 140° C. The reaction solution was cooled to room temperature, to which was added 15 mL of dichloromethane. The organic phase was successively washed twice with the saturated aqueous solution of ammonium chloride and washed once with saturated brine, dried over anhydrous magnesium sulfate, concentrated to dryness under reduced pressure, and separated and purified by thin layer chromatography, to provide the product N-((1r,4R)-4-(3-chloro-4-cyanophenoxy)cyclohexyl)-4-(4-((3R)-1-(2-(2,6-dioxopiperidin-3-yl)-1,3-dioxoisoindolin-5-yl)pyrrolidine-3-yl)oxy)piperidin-1-yl) benzamide (36 mg), with a yield of 57.8%, LC/MS (ESI$^+$) for $C_{42}H_{43}ClN_6O_7$ ([M+H]$^+$) m/z 779.2, $^1$H NMR (400 MHz, $CDCl_3$) δ 8.13 (s, 1H), 7.67 (d, J=8.4 Hz, 3H), 7.56 (d, J=8.7 Hz, 1H), 6.99 (d, J=2.4 Hz, 1H), 6.95 (t, J=6.0 Hz, 2H), 6.84 (dd, J=8.8, 2.4 Hz, 1H), 6.69 (dd, J=8.5, 2.1 Hz, 1H), 5.90 (d, J=7.5 Hz, 1H), 4.94 (dd, J=12.3, 5.3 Hz, 1H), 4.62 (s, 1H), 4.42 (s, 1H), 4.33-4.23 (m, 1H), 4.08-4.00 (m, 1H), 3.60 (ddd, J=22.8, 13.9, 7.0 Hz, 5H), 3.53-3.46 (m, 1H), 3.43 (d, J=9.2 Hz, 1H), 3.17-3.03 (m, 2H), 2.81 (tdd, J=19.5, 17.2, 10.4 Hz, 3H), 2.26-2.10 (m, 7H), 2.01 (s, 2H), 1.64 (dd, J=13.1, 2.9 Hz, 3H), 1.51-1.30 (m, 3H).

112: N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5]nonan-7-yl)methyl)cyclohexyl)-1H-imidazole-4-carboxamide

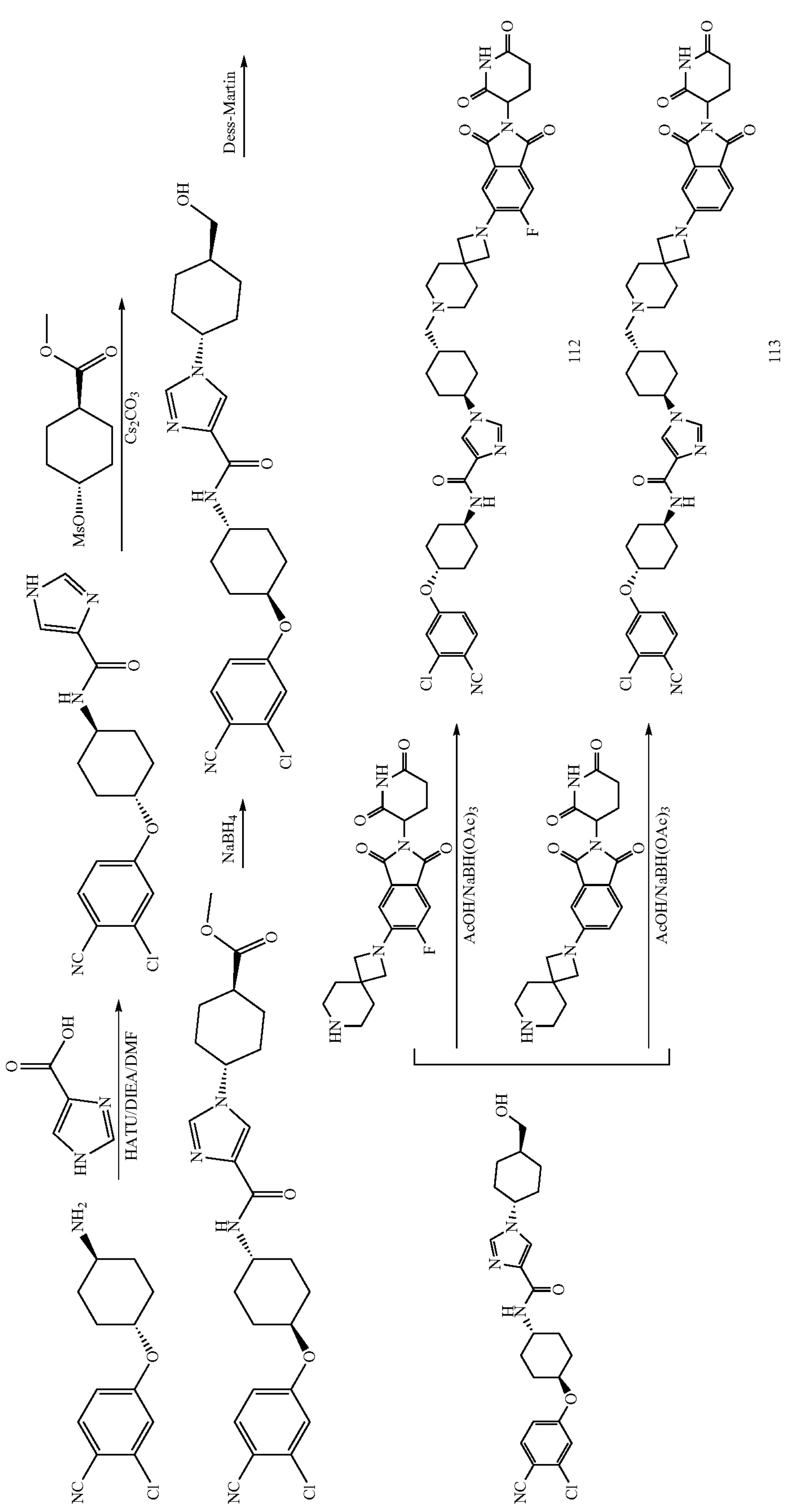
112
113

1) N-((1r,4r)-4-(3-chloro-4-cyanophenoxy)cyclohexyl)-1H-imidazole-4-formamide 1H-imidazole-4-carboxylic acid (448 mg, 4.0 mmol) was dissolved in 10 mL of DMF, to which were added DIEA (1.03 g, 8.0 mmol) and HATU (1.52 g, 4.0 mmol), and the mixture was stirred at room temperature for 30 min. 4-((1r,4r)-4-Aminocyclohexyl)oxy)-2-chlorobenzonitrile (1.0 g, 4.0 mmol) was added, and then the resultant solution was stirred overnight at room temperature, to which was added 25 mL of ethyl acetate. The solution was washed with 20 mL of water. The organic layers were further washed with water and saturated brine respectively, dried over anhydrous sodium sulfate, filtered, concentrated to dryness under reduced pressure, and separated and purified by column chromatography, to provide the product N-((1r,4r)-4-(3-chloro-4-cyanophenoxy)cyclohexyl)-1H-imidazole-4-formamide (610 mg), with a yield of 44.2%, LC/MS ($ESI^+$) calcd for $C_{17}H_{17}ClN_4O_2$ ($[M+H]^+$) m/z 345.1.

2) Methyl (1R,4r)-4-(4-((1R,4r)-4-(3-chloro-4-cyanophenoxy)cyclohexyl)carbamoyl)-1H-imidazol-1-yl)cyclohexane-1-carboxylate N-((1r,4r)-4-(3-Chloro-4-cyanophenoxy)cyclohexyl)-1H-imidazole-4-formamide (345 mg, 1.0 mmol) was dissolved in 6 mL of DMF, to which was added cesium carbonate (975 mg, 3.0 mmol), and the mixture was stirred at room temperature for 5 min. Methyl (1r,4r)-4-((methylsulfonyl)oxy) cyclohexane-1-carboxylate (354 mg, 4.5 mmol) was added, and the resultant solution was allowed to react at 95° C. overnight, to which was added 25 mL of ethyl acetate. The solution was washed with 20 mL of water, and then the organic layer was washed with water and saturated brine respectively, dried over anhydrous sodium sulfate, filtered, concentrated under reduced pressure, and separated and purified by thin layer chromatography, to provide the product methyl (1R,4r)-4-(4-((1R,4r)-4-(3-chloro-4-cyanophenoxy)cyclohexyl)carbamoyl)-1H-imidazole-1-yl)cyclohexane-1-carboxylate (130 mg), with a yield of 26.8%, LC/MS ($ESI^+$) calcd for $C_{25}H_{29}ClN_4O_4$ ($[M+H]^+$) m/z 485.3.

3) N-((1r,4R)-4-(3-chloro-4-cyanophenoxy)cyclohexyl)-1-((1r,4R)-4-(hydroxymethyl) cyclohexyl)-1H-imidazole-4-formamide Methyl (1R,4r)-4-(4-((1R,4r)-4-(3-chloro-4-cyanophenoxy)cyclohexyl)carbamoyl)-1H-imidazol-1-yl)cyclohexane-1-carboxylate (130 mg, 0.27 mmol) was dissolved in 5 mL of tetrahydrofuran, to which were successively added 4 mL of methanol and sodium borohydride (76 mg, 2.0 mmol). The mixture was allowed to react overnight at 70° C. and concentrated to dryness under reduced pressure. To the residue, was added 10 mL of ethyl acetate, and the solution was successively washed with water and saturated brine, dried over anhydrous sodium sulfate, concentrated to dryness under reduced pressure, and separated and purified by thin layer chromatography, to provide the product N-((1r,4R)-4-(3-chloro-4-cyanophenoxy)cyclohexyl)-1-((1r,4R)-4-(hydroxymethyl)cyclohexyl)-1H-imidazole-4-formamide (54 mg), with a yield of 43.8%, LC/MS ($ESI^+$) calcd for $C_{24}H_{29}ClN_4O_{43}$ ($[M+H]^+$) m/z 457.3.

4) N-((1r,4R)-4-(3-chloro-4-cyanophenoxy)cyclohexyl)-1-((1r,4R)-4-formylcyclohexyl)-1H-imidazole-4-formamide N-((1r,4R)-4-(3-Chloro-4-cyanophenoxy)cyclohexyl)-1-((1r,4R)-4-(hydroxymethyl) cyclohexyl)-1H-imidazole-4-formamide (54 mg, 0.12 mmol) was dissolved in 5 mL of dichloromethane, to which was added Dess-Martin periodinane (102 mg, 0.24 mmol). The reaction solution was stirred at room temperature for 1 h, filtered, and the filtrate was concentrated under reduced pressure to dryness, to provide the product N-((1r,4R)-4-(3-chloro-4-cyanophenoxy)cyclohexyl)-1-((1r,4R)-4-formylcyclohexyl)-1H-imidazole-4-formamide (45 mg), with a yield of 84.5%, LC/MS ($ESI^+$) calcd for $C_{24}H_{27}ClN_4O_3$ ($[M+H]^+$) m/z 455.2.

5) N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindol-5-yl)-2,7-diazaspiro[3.5] nonan-7-yl)methyl)cyclohexyl)-1H-imidazole-4-carboxamide N-((1r,4R)-4-(3-chloro-4-cyanophenoxy)cyclohexyl)-1-((1r,4R)-4-formylcyclohexyl)-1H-imidazole-4-formamide (30 mg, 0.066 mmol) and 2-(2,6-dioxopiperidin-3-yl)-5-fluoro-6-(2,7-diazaspiro[3.5]nonan-2-yl)isoindoline-1,3-dione (26 mg, 0.066 mmol) were dissolved in 5 mL of dichloromethane, to which was added 0.5 drops of acetic acid. The reaction solution was stirred at room temperature for 10 min, to which was added sodium triacetylborohydride (212 mg, 1.0 mmol). The resultant solution was stirred at room temperature for 3 h, successively washed with water and saturated brine, dried over anhydrous magnesium sulfate, concentrated to dryness under reduced pressure, separated and purified by thin layer chromatography, to provide the product N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5]nonan-7-yl) methyl)cyclohexyl)-1H-imidazole-4-carboxamide (16 mg), with a yield of 28.9%. LC/MS ($ESI^+$) for $C_{44}H_{48}ClFN_8O_6$ ($[M+H]^+$) m/z 839.2, $^1$H NMR (400 MHz, $CDCl_3$) δ 7.66 (s, 1H), 7.57 (d, J=8.8 Hz, 1H), 7.51 (s, 1H), 7.37 (d, J=10.9 Hz, 1H), 7.01 (d, J=2.3 Hz, 1H), 6.86 (dd, J=8.8, 2.3 Hz, 1H), 6.82 (d, J=7.5 Hz, 1H), 4.91 (dd, J=12.1, 5.3 Hz, 1H), 4.30 (d, J=10.3 Hz, 1H), 3.98 (d, J=11.1 Hz, 2H), 3.92 (s, 4H), 2.92-2.65 (m, 4H), 2.14 (dd, J=17.2, 7.5 Hz, 8H), 2.05 (s, 2H), 1.95 (s, 4H), 1.67 (dd, J=25.5, 12.2 Hz, 6H), 1.53-1.40 (m, 3H), 1.29 (s, 2H), 1.17 (s, 2H).

113: N-((1r,4R)-4-(3-chloro-4-cyanophenoxy)cyclohexyl)-1-((1r,4R)-4-((2-(2-(2,6-dioxopiperidin-3-yl)-1,3-dioxoisoindolin-5-yl)-2,7-diazaspiro[3.5]nonan-7-yl) methyl)cyclohexyl)-1H-imidazole-4-formamide N-((1r,4R)-4-(3-chloro-4-cyanophenoxy)cyclohexyl)-1-((1r,4R)-4-formylcyclohexyl)-1H-imidazole-4-formamide (15 mg, 0.033 mmol) and 2-(2,6-dioxopiperidin-3-yl)-5-fluoro-6-(2,7-diazaspiro[3.5]nonan-2-yl)isoindole-1,3-dione (13 mg, 0.033 mmol) were dissolved in 5 mL of dichloromethane, to which was added 0.3 drops of acetic acid. The reaction solution was stirred at room temperature for 10 min, to which was added sodium triacetylborohydride (106 mg, 0.5 mmol). The resultant solution was stirred at room temperature for 3 h, successively washed with water and saturated brine, dried over anhydrous magnesium sulfate, concentrated to dryness under reduced pressure, separated and purified by thin layer chromatography, to provide the product N-((1r,4R)-4-(3-chloro-4-cyanophenoxy)cyclohexyl)-1-((1r,4R)-4-((2-(2-(2,6-dioxopiperidin-3-yl)-1,3-dioxoisoindolin-5-yl)-2,7-diazaspiro[3.5]nonan-7-yl)methyl) cyclohexyl)-1H-imidazole-4-formamide (13 mg), with a yield of 47.0%. LC/MS ($ESI^+$) for $C_{44}H_{49}ClN_8O_6$ ($[M+H]^+$)

m/z 821.2, $^1$H NMR (400 MHz, $CDCl_3$) δ 8.58 (s, 1H), 7.64 (dd, J=13.2, 4.7 Hz, 2H), 7.55 (d, J=8.7 Hz, 1H), 7.50 (d, J=1.3 Hz, 1H), 7.06 (d, J=8.3 Hz, 1H), 6.98 (d, J=2.4 Hz, 1H), 6.84 (dd, J=8.8, 2.4 Hz, 1H), 6.78 (d, J=1.9 Hz, 1H), 6.51 (d, J=8.0 Hz, 1H), 4.94 (dd, J=12.3, 5.2 Hz, 1H), 4.27 (t, J=10.2 Hz, 1H), 4.08-3.89 (m, 2H), 3.76 (s, 4H), 2.96-2.64 (m, 4H), 2.38 (s, 2H), 2.15 (d, J=10.2 Hz, 8H), 1.95 (s, 2H), 1.77-1.59 (m, 13H), 1.45 (dd, J=23.1, 11.0 Hz, 3H).

114: N-((1r,4R)-4-(3-chloro-4-cyanophenoxy)cyclohexyl)-1-((1r,4R)-4-((2-(2-(2,6-dioxopiperidin-3-yl)-1,3-dioxoisoindolin-5-yl)-2,7-diazaspiro[3.5]nonan-7-yl) methyl)cyclohexyl)-1H-1,2,3-triazole-4-carboxamide

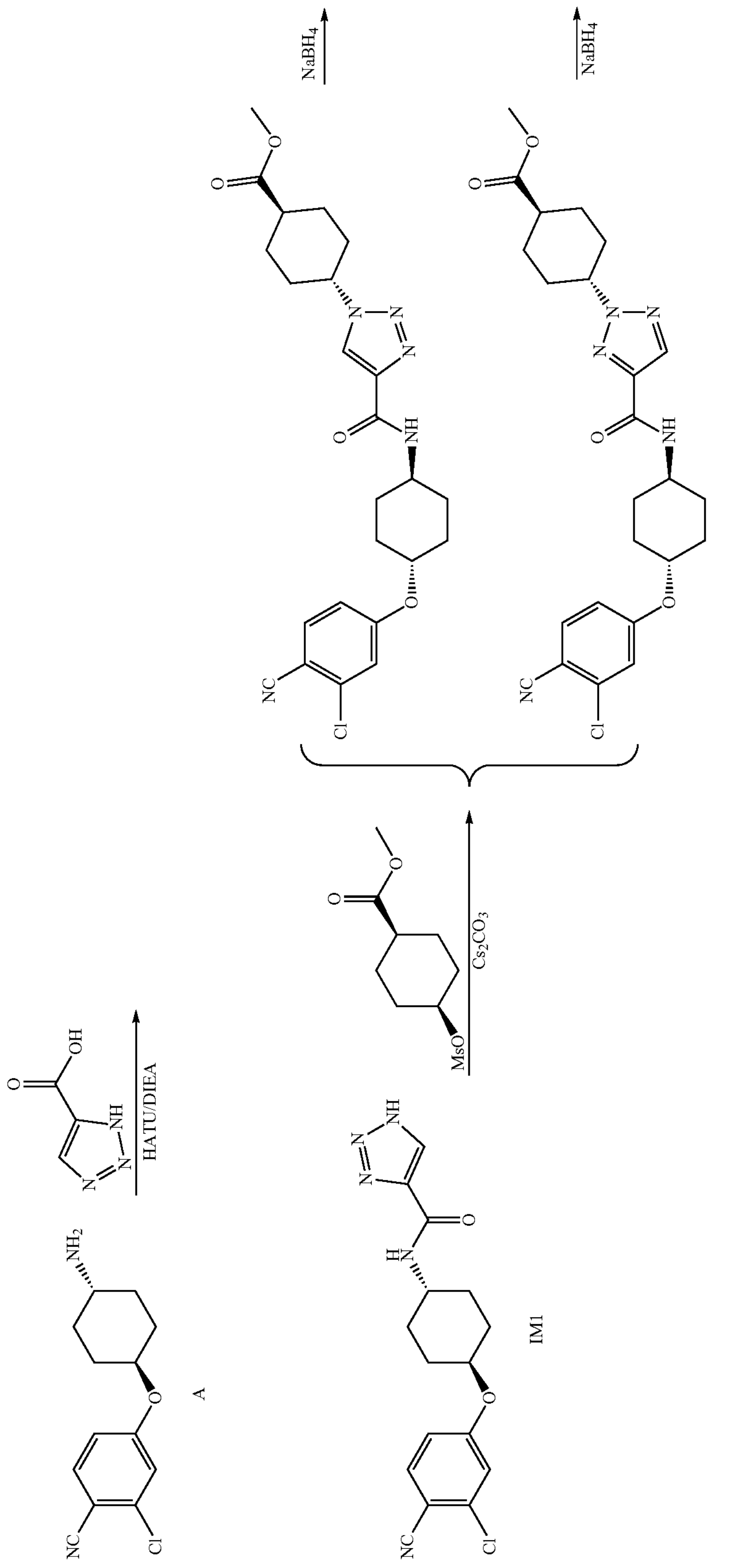
A
HATU/DIEA
IM1
Cs2CO3
NaBH4
NaBH4

-continued
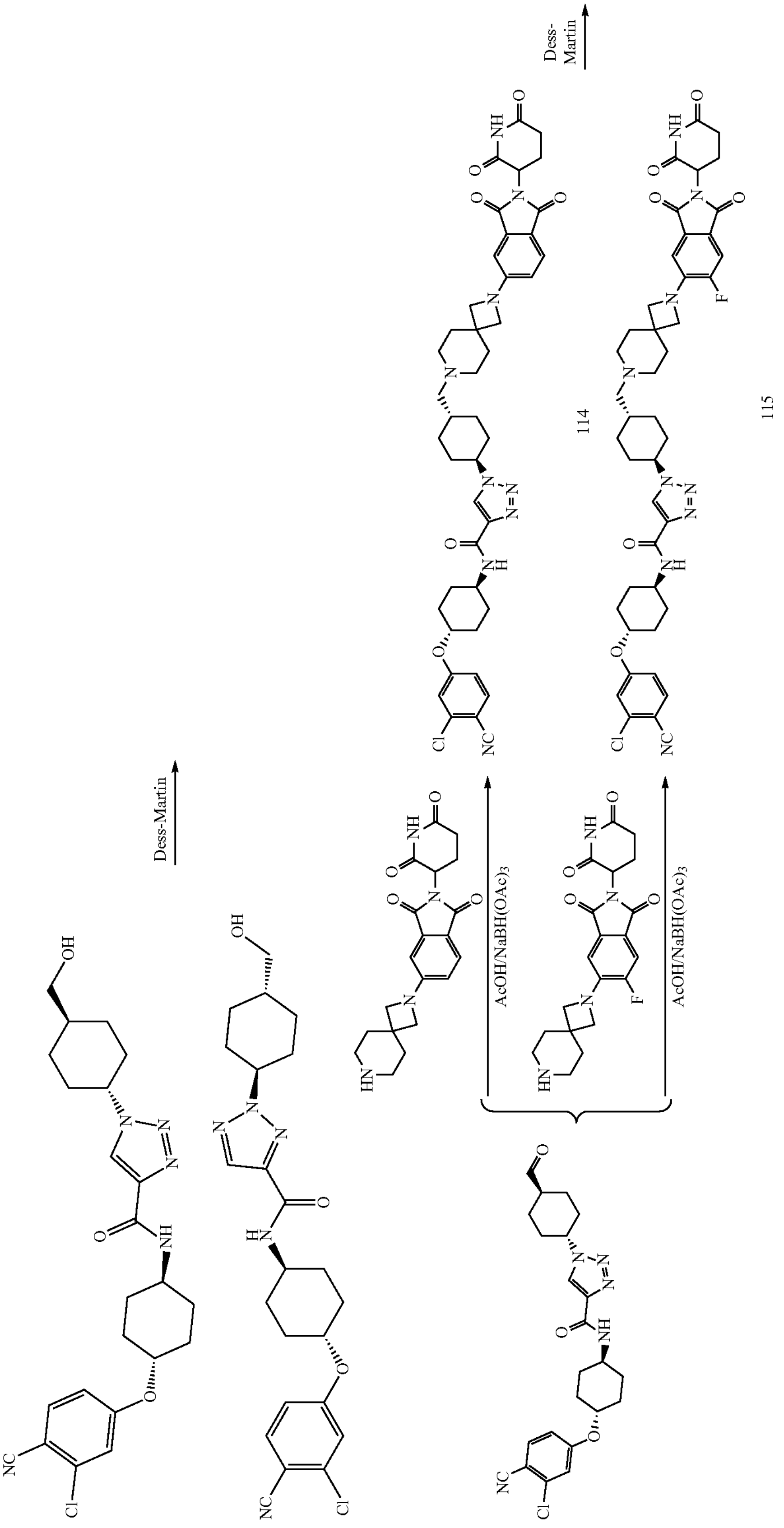
114
115

-continued
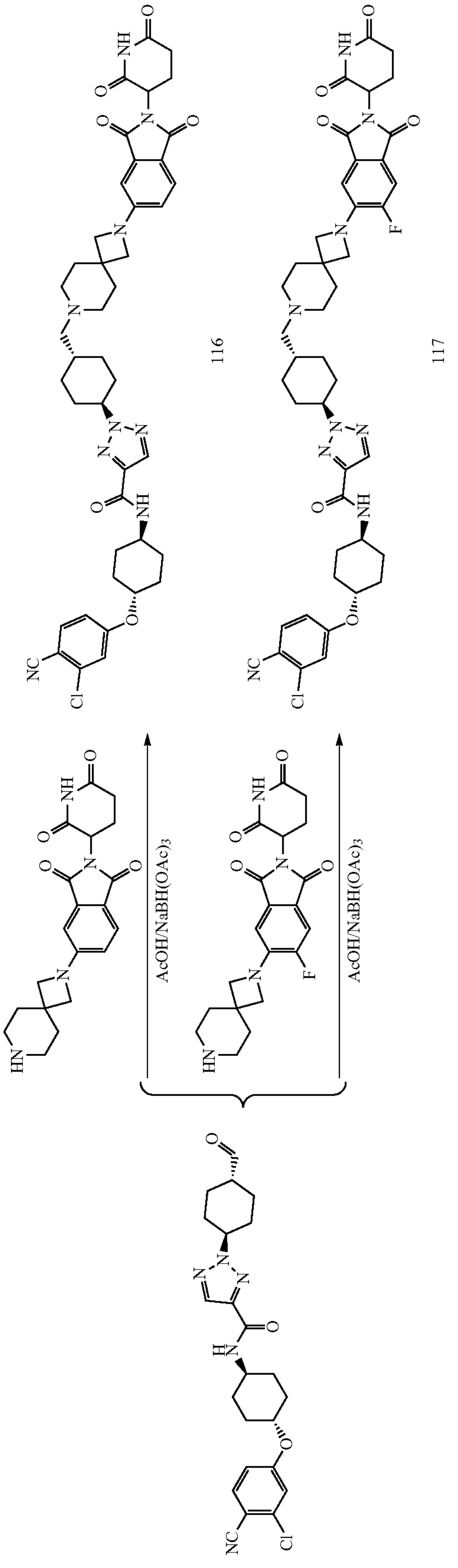
116
117

The synthetic procedures referred to 112.

Characteristic data: LC/MS ($ESI^+$) for $C_{43}H_{48}ClN_9O_6$ ($[M+H]^+$) m/z 822.3. $^1H$ NMR (400 MHz, $CDCl_3$) δ 8.09 (d, J=16.2 Hz, 2H), 7.68 (d, J=6.0 Hz, 1H), 7.56 (d, J=8.7 Hz, 1H), 7.08 (d, J=8.0 Hz, 1H), 7.00 (d, J=2.1 Hz, 1H), 6.85 (dd, J=8.8, 2.3 Hz, 1H), 6.80 (s, 1H), 6.56 (s, 1H), 4.94 (d, J=6.3 Hz, 1H), 4.48 (s, 1H), 4.31 (s, 1H), 4.05 (d, J=7.9 Hz, 1H), 3.85 (s, 4H), 2.96-2.69 (m, 7H), 2.33 (s, 4H), 2.24-2.02 (m, 8H), 1.89 (d, J=8.2 Hz, 2H), 1.67 (d, J=10.4 Hz, 8H), 1.53-1.46 (m, 2H).

115: N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5]nonan-7-yl)methyl)cyclohexyl)-1H-1,2,3-triazole-4-formamide LC/MS ($ESI^+$) for $C_{43}H_{47}ClFN_9O_6$ ($[M+H]^+$) m/z 840.3, $^1H$ NMR (400 MHz, $CDCl_3$) δ 8.10 (s, 1H), 8.08 (d, J=4.4 Hz, 1H), 7.56 (d, J=8.7 Hz, 1H), 7.39 (d, J=10.7 Hz, 1H), 7.07 (d, J=8.2 Hz, 1H), 7.00 (d, J=2.3 Hz, 1H), 6.89-6.80 (m, 2H), 4.96-4.88 (m, 1H), 4.53-4.42 (m, 1H), 4.31 (s, 1H), 4.05 (d, J=8.3 Hz, 1H), 4.01 (d, J=25.7 Hz, 4H), 3.63 (s, 2H), 3.01-2.60 (m, 7H), 2.34 (d, J=12.8 Hz, 3H), 2.17 (dd, J=17.1, 12.1 Hz, 7H), 1.97-1.82 (m, 2H), 1.67 (d, J=12.9 Hz, 2H), 1.62 (s, 6H), 1.48 (d, J=12.2 Hz, 2H).

116: N-((1r,4R)-4-(3-chloro-4-cyanophenoxy)cyclohexyl)-2-((1r,4R)-4-((2-(2-(2,6-dioxopiperidin-3-yl)-1,3-dioxoisoindolin-5-yl)-2,7-diazaspiro[3.5]nonan-7-yl) methyl)cyclohexyl)-2H-1,2,3-triazole-4-carboxamide LC/MS ($ESI^+$) for $C_{43}H_{48}ClN_9O_6$ ($[M+H]^+$) m/z 822.3, $^1H$ NMR (400 MHz, $CDCl_3$) δ 8.09-8.04 (m, 1H), 8.03 (s, 1H), 7.66 (d, J=8.3 Hz, 1H), 7.56 (d, J=8.7 Hz, 1H), 6.99 (d, J=2.4 Hz, 1H), 6.88-6.82 (m, 1H), 6.79 (d, J=2.0 Hz, 1H), 6.61-6.56 (m, 1H), 6.56-6.50 (m, 1H), 4.94 (dd, J=12.2, 5.3 Hz, 1H), 4.46 (dd, J=13.8, 10.0 Hz, 1H), 4.30 (s, 1H), 4.04 (d, J=7.9 Hz, 1H), 3.79 (s, 4H), 2.95-2.71 (m, 4H), 2.58 (s, 2H), 2.28 (d, J=11.1 Hz, 2H), 2.24-2.10 (m, 7H), 1.98 (d, J=13.5 Hz, 3H), 1.69 (d, J=10.0 Hz, 8H), 1.55-1.43 (m, 2H), 1.25 (s, 3H).

117: N-((1r,4R)-4-(3-chloro-4-cyanophenoxy)cyclohexyl)-2-((1r,4R)-4-((2-(2,6-dioxopiperidin-3-yl)-6-fluoro-1,3-dioxoisoindolin-5-yl)-2,7-diazaspiro[3.5]nonan-7-yl)methyl)cyclohexyl)-2H-1,2,3-triazole-4-formamide LC/MS ($ESI^+$) for $C_{43}H_{47}ClFN_9O_6$ ($[M+H]^+$) m/z 840.3, $^1H$ NMR (400 MHz, $CDCl_3$) δ 8.03 (s, 1H), 7.98 (s, 1H), 7.56 (d, J=8.7 Hz, 1H), 7.39 (d, J=10.8 Hz, 1H), 7.00 (d, J=2.4 Hz, 1H), 6.87-6.80 (m, 2H), 6.58 (d, J=8.2 Hz, 1H), 4.92 (dd, J=12.3, 5.2 Hz, 1H), 4.46 (t, J=11.9 Hz, 1H), 4.31 (t, J=9.9 Hz, 1H), 4.04 (d, J=7.8 Hz, 1H), 3.96 (s, 3H), 2.83 (ddd, J=28.3, 24.3, 14.8 Hz, 4H), 2.29 (d, J=10.8 Hz, 2H), 2.15 (dd, J=20.4, 8.2 Hz, 6H), 2.04-1.96 (m, 2H), 1.67 (d, J=22.9 Hz, 10H), 1.52-1.45 (m, 2H), 1.25 (s, 4H).

118: Synthesis of N-((1r,4r)-4-(3-chloro-4-cyanophenoxy)cyclohexyl)-6-(4-((1-(2-(2,6-dioxopiperidin-3-yl)-1,3-dioxoisoindolin-5-yl)piperidine-4-yl) amino) piperidin-1-yl)pyridazine-3-amide

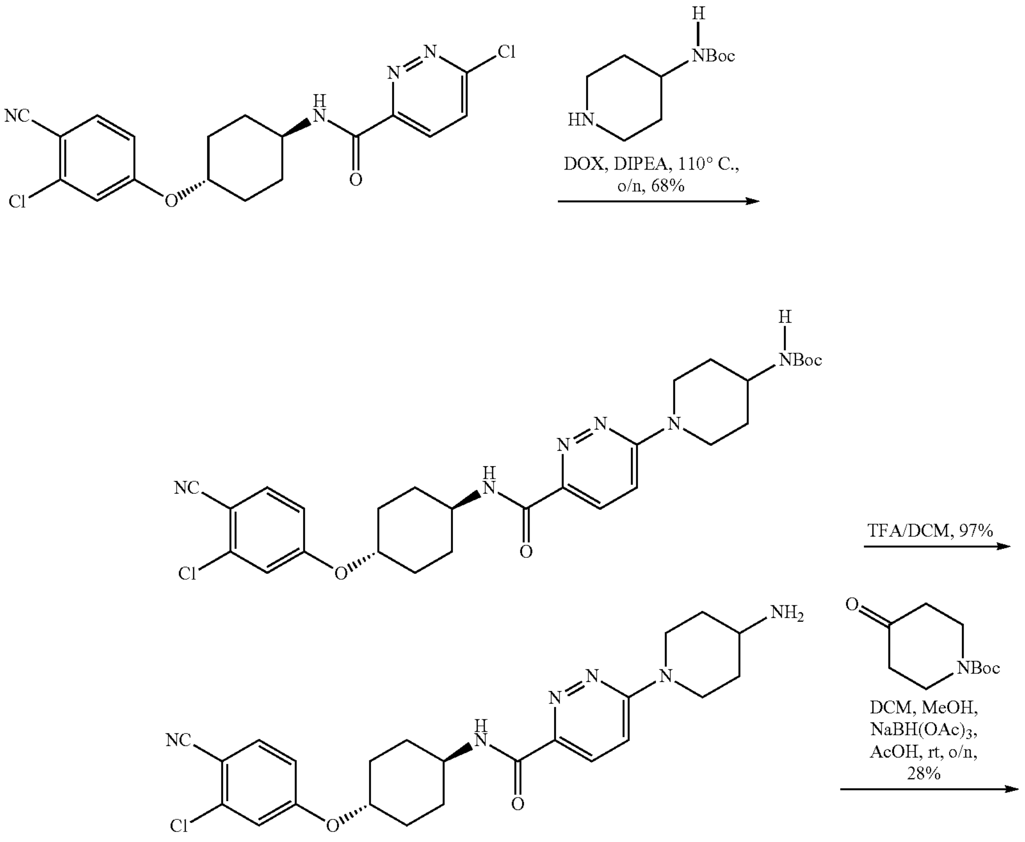

-continued

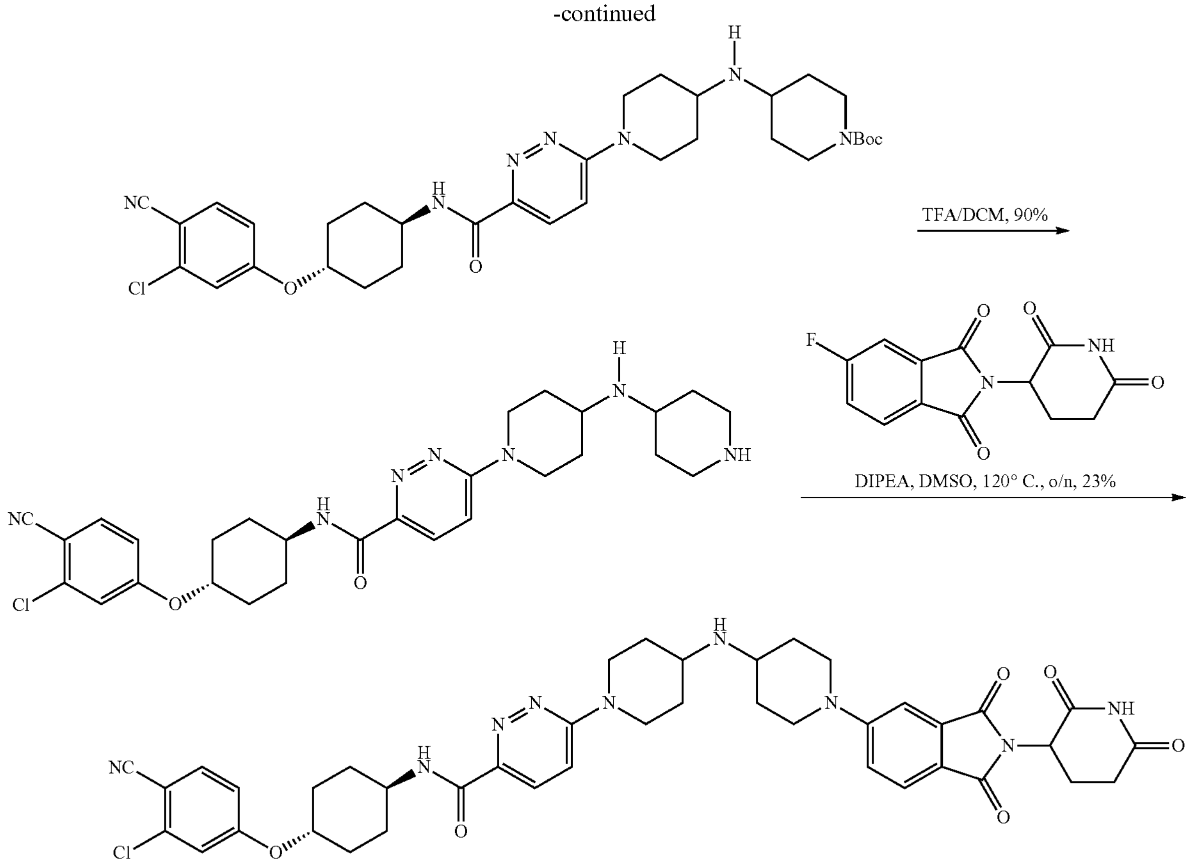

118

1. N-((1r,4r)-4-(3-chloro-4-cyanophenoxy)cyclohexyl)-6-(4-(t-butoxyamide-piperidin-1-yl) pyridazine-3-amide Compounds N-(1r,4r)-4-(3-chloro-4-cyanophenoxy)cyclohexyl)-6-chloropyridazine-3-carboxamide (500 g, 1.28 mmol), 4-t-butoxcarbonylaminopiperidine-(384 mg, 1.92 mmol) and N,N-diisopropylethylamine (496 mg, 3.84 mmol) were added to 10 mL DOX, and the solution was heated to 110° C. and stirred overnight. The solution was cooled to room temperature, to which were added water and ethyl acetate for extraction. The organic layer was respectively washed three times with saturated ammonium chloride solution and saturated brine, dried over anhydrous sodium sulfate, rotatory evaporated to dry and purified by silica gel column chromatography, to provide a white solid compound N-((1r,4r)-4-(3-chloro-4-cyanophenoxy)cyclohexyl)-6-(4-(t-butoxyamide)piperidine-4-yl)amino)piperidin-1-yl)pyridazine-3-amide (493 mg, 0.87 mmol), with a yield of 68%.

LC/MS ($ESI^+$) calcd for $C_{28}H_{35}ClN_6O_4^+$ $[M+H]^+$ m/z, 555.2; found 555.2.

2. N-((1r,4r)-4-(3-chloro-4-cyanophenoxy)cyclohexyl)-6-(4-aminopiperdine-4-yl) amino)piperidin-1-yl)pyridazine-3-amide Compound N-((1r,4r)-4-(3-chloro-4-cyanophenoxy)cyclohexyl)-6-(4-(t-butoxyamide) piperidine-4-yl)amino)piperidin-1-yl)pyridazine-3-carboxamide (200 mg, 0.36 mmol) was dissolved in 3 mL of dichloromethane, to which was added 6 mL of trifluoroacetic acid. The reaction solution was stirred at room temperature for 2 h, and concentrated under reduced pressure. After that, the reaction solution was adjusted to be pH 10 with saturated $Na_2CO_3$ aqueous solution, and then extracted with dichloromethane. The organic layer was washed with brine, dried over anhydrous sodium sulfate, and rotatory evaporated to dry, to provide light yellow oily compound N-((1r,4r)-4-(3-chloro-4-cyanophenoxy)cyclohexyl)-6-(4-aminopiperdine-4-yl)amino)piperidin-1-yl) pyridazine-3-amide (159 mg, 0.35 mmol), with a yield of 97%. LC/MS ($ESI^+$) calcd for $C_{23}H_{27}ClN_6O_2^+$ $[M+H]^+$ m/z, 455.2; found 455.2.

3. N-((1r,4r)-4-(3-chloro-4-cyanophenoxy)cyclohexyl)-6-(4-(4-t-butyloxycarbonylamino-piperidin-1-yl)-(4-aminopiperdine-1-yl)pyridazine-3-amide Compounds N-((1r,4r)-4-(3-chloro-4-cyanophenoxy)cyclohexyl)-6-(4-aminopiperdin-4-yl)amino)piperidin-1-yl) pyridazine-3-amide (150 mg, 0.33 mmol) and N-t-butoxycarbonyl-4-piperidone (131 mg, 0.66 mmol) were dissolved in a mixed solvent of 1 mL methanol and 2 mL dichloromethane. Under the catalysis of two drops of glacial acetic acid, the reaction solution was stirred at room temperature for half an hour, to which was then added sodium triacetoxyborohydride (91 mg, 0.43 mmol), and the solution was continually stirred at room temperature overnight. After the reaction solution was concentrated, water was added, and then the resultant solution was extracted with dichloromethane. The organic layer was washed with the saturated aqueous solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(4-(4-t-butyloxycarbonylamino-piperidin-1-yl)-(4-aminopiperdine-1-yl)pyridazine-3-amide as a white solid (60 mg, 0.094 mmol), with a yield of 28%. LC/MS ($ESI^+$) calcd for $C_{33}H_{44}ClNO_4^+$ $[M+H]^+$ m/z, 638.3; found 638.3.

4. N-((1r,4r)-4-(3-chloro-4-cyanophenoxy)cyclohexyl)-6-(4-(4-amino-piperidin-1-yl)-(4-aminopiperdine-1-yl)pyridazine-3-amide Compound N-((1r,4r)-4-(3-chloro-4-cyanophenoxy)cyclohexyl)-6-(4-(4-t-butyloxycarbonylamino-piperidin-1-yl)-(4-aminopiperdine-1-yl)pyridazine-3-amide (60 mg, 0.094 mmol) was dissolved in 3 mL of dichloromethane, to which was added 6 mL of trifluoroacetic acid, and the mixture was stirred at room temperature for 2 h. The resultant solution was concentrated under reduced pressure, to provide compound N-((1r,4r)-4-(3-chloro-4-cyanophenoxy)cyclohexyl)-6-(4-aminopiperdine-4-yl)amino) piperidin-1-yl) pyridazine-3-amide trifluoroacetate as a white solid (55 mg, 0.084 mmol), with a yield of 90%. LC/MS ($ESI^+$) calcd for $C_{28}H_{36}ClN_7O_2^+$ $[M+H]^+$ m/z, 538.3; found 538.3.

5. Synthesis of N-((1r,4r)-4-(3-chloro-4-cyanophenoxy)cyclohexyl)-6-(4-((1-(2-(2,6-dioxopiperidin-3-yl)-1,3-dioxoisoindolin-5-yl)piperidine-4-yl)amino) piperidin-1-yl) pyridazine-3-amide Compounds N-((1r,4r)-4-(3-chloro-4-cyanophenoxy)cyclohexyl)-6-(4-aminopiperdine-4-yl)amino)piperidin-1-yl) pyridazine-3-amide trifluoroacetate (55 mg, 0.084 mmol), 2-(2,6-dioxopiperidin-3-yl)-5-fluoro-1,3-dioxoisoindoline (23 mg, 0.084 mmol), and DIPEA (54 mg, 0.42 mmol) were added into 1 mL of DMSO. The mixture was heated to 130° C. and stirred for 3 h. After cooling to room temperature, water and ethyl acetate were added for extraction. The organic layer was washed with the saturated aqueous solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy) cyclohexyl)-6-(4-((1-(2-(2,6-dioxopiperidin-3-yl)-1,3-dioxoisoindolin-5-yl) piperidine-4-yl)amino)piperidin-1-yl)pyridazine-3-amide as a yellow solid (15 mg, 0.019 mmol), with a yield of 23%. LC/MS ($ESI^+$) calcd for $C_{41}H_{44}ClN_9O_6[M+H]^+$ m/z, 794.3; found 794.2. $^1H$ NMR (400 MHz, DMSO-$d_6$) δ 11.06 (s, 2H), 8.48 (d, J=2.0 Hz, 1H), 7.84 (d, J=4.4 Hz, 1H), 7.69 (d, J=4.4 Hz, 1H), 7.64 (d, J=4.4 Hz, 1H), 7.37 (d, J=1.2 Hz, 1H), 7.34-7.21 (m, 3H), 7.11 (dd, J=5.6, 3.2 Hz, 1H), 6.84 (d, J=4.8 Hz, 1H), 5.05 (dd, J=8.8, 3.6 Hz, 1H), 4.55-4.47 (m, 1H), 4.12-4.03 (m, 2H), 3.86-3.76 (m, 2H), 2.99-2.91 (m, 2H), 2.89-2.82 (m, 2H), 2.60-2.52 (m, 1H), 2.27-2.20 (m, 2H), 2.11-2.04 (m, 2H), 2.00-1.93 (m, 3H), 1.86-1.82 (m, 2H), 1.82-1.79 (m, 2H), 1.64-1.56 (m, 2H), 1.53-1.38 (m, 6H), 1.23-1.19 (m, 2H).

119: Synthesis of N-((1r,4r)-4-(3-chloro-4-cyanophenoxy)cyclohexyl)-6-(4-((1-(2-(2,6-dioxopiperidin-3-yl)-1,3-dioxoisoindolin-5-yl)piperidine-4-yl) methylamino) piperidin-1-yl)pyridazine-3-amide

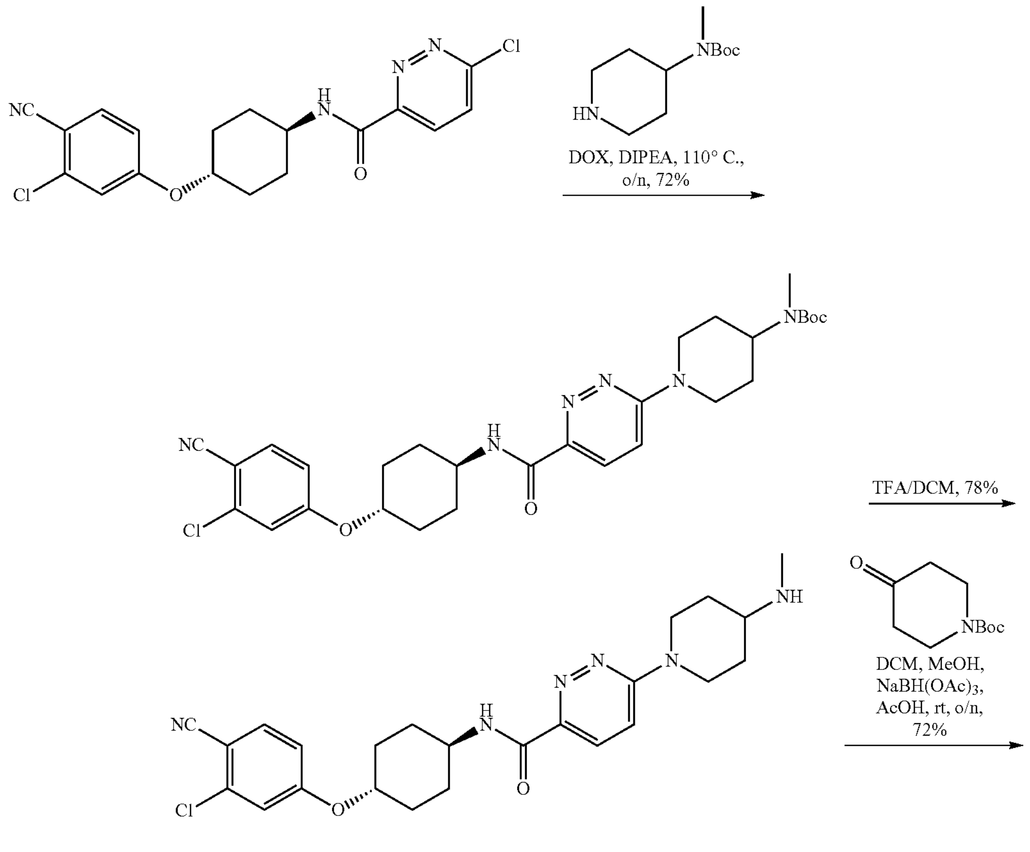

-continued
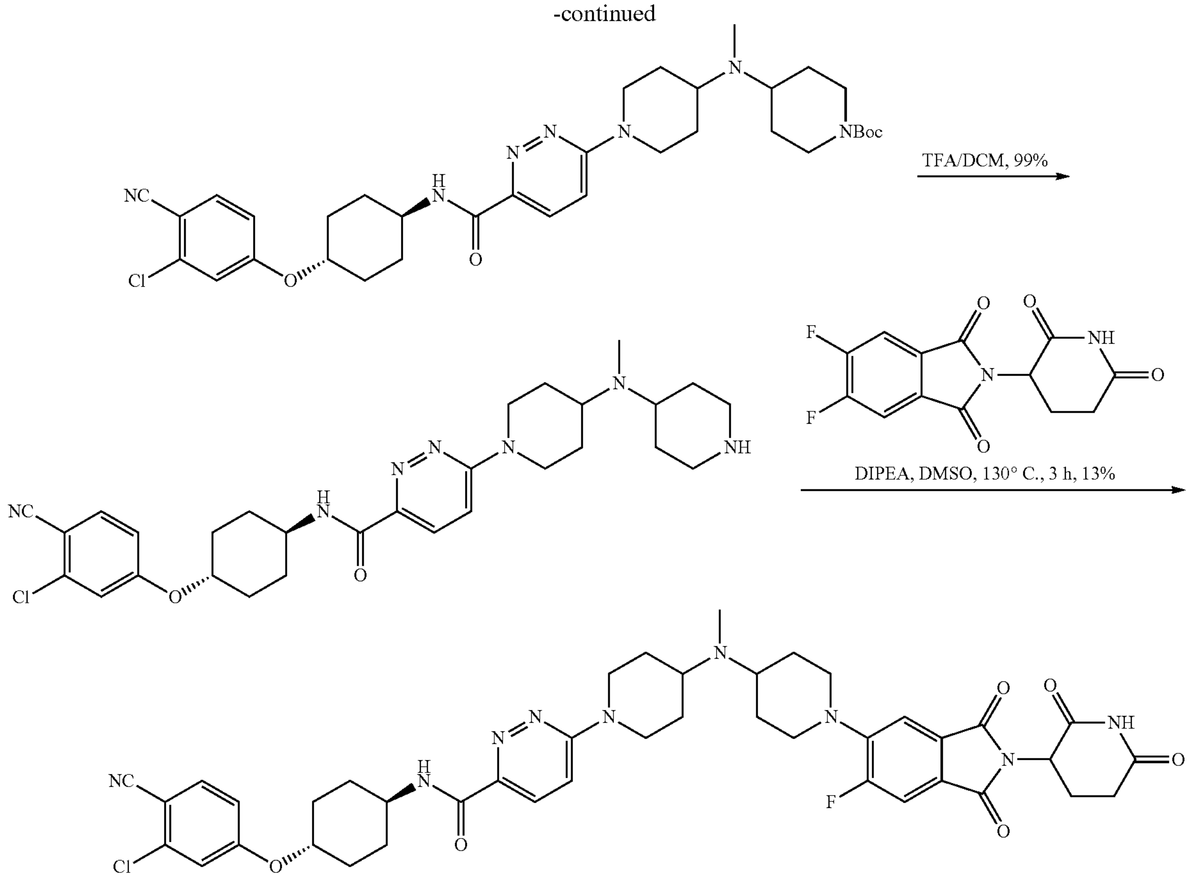
119
LC/MS ($ESI^+$) calcd for $C_{42}H_{45}ClFN_9O_6^+$ $[M+H]^+$ m/z, 826.3; found 826.3.
$^1H$ NMR (400 MHz, DMSO-$d_6$) δ 11.12 (s, 1H), 8.62 (d, J=4.0 Hz, 1H), 7.86 (d, J=4.4 Hz, 1H), 7.81 (d, J=4.8 Hz, 1H), 7.72 (d, J=5.6 Hz, 1H), 7.45 (d, J=4.0 Hz, 1H), 7.41-7.39 (m, 1H), 7.39-7.34 (m, 1H), 7.17-7.11 (m, 1H), 5.11 (dd, J=9.2, 3.6 Hz, 1H), 4.59-4.47 (m, 3H), 3.69-3.62 (m, 2H), 3.47-3.41 (m, 1H), 3.32-3.28 (m, 3H), 3.09-2.99 (m, 2H), 2.98-2.87 (m, 3H), 2.55 (s, 3H), 2.28-2.16 (m, 3H), 2.16-2.07 (m, 2H), 2.07-1.96 (m, 2H), 1.96-1.77 (m, 2H), 1.72-1.61 (m, 4H), 1.56-1.46 (m, 4H), 1.08-1.03 (m, 1H).
120: Synthesis of 2-chloro-4-((2-(6-(4-((4-(2-(2,6-dioxopiperidin-3-yl)-1,3-dioxoisoindolin-5-yl)piperazin-1-yl)methyl)piperidin-1-yl)pyridazine-3-carbonyl)-2-azaspiro[3.3]heptan-6-yl)oxy)benzonitrile
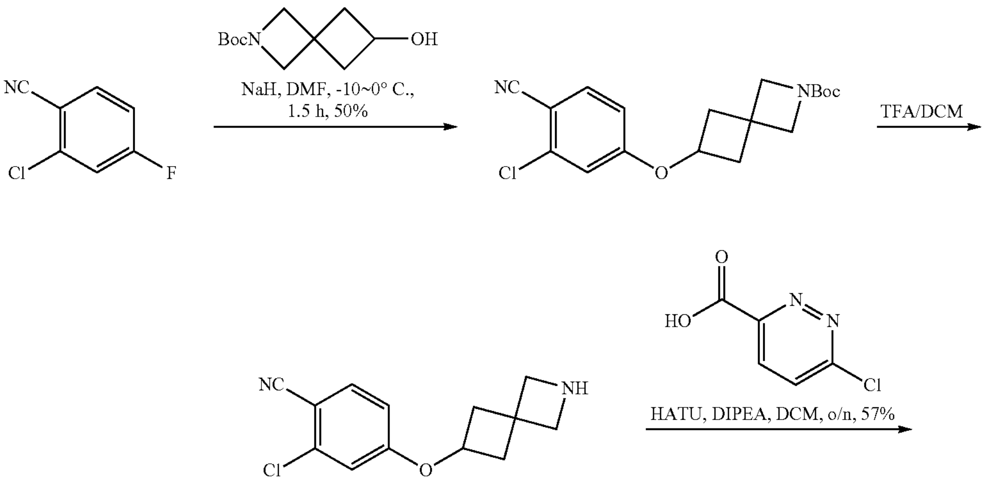

-continued

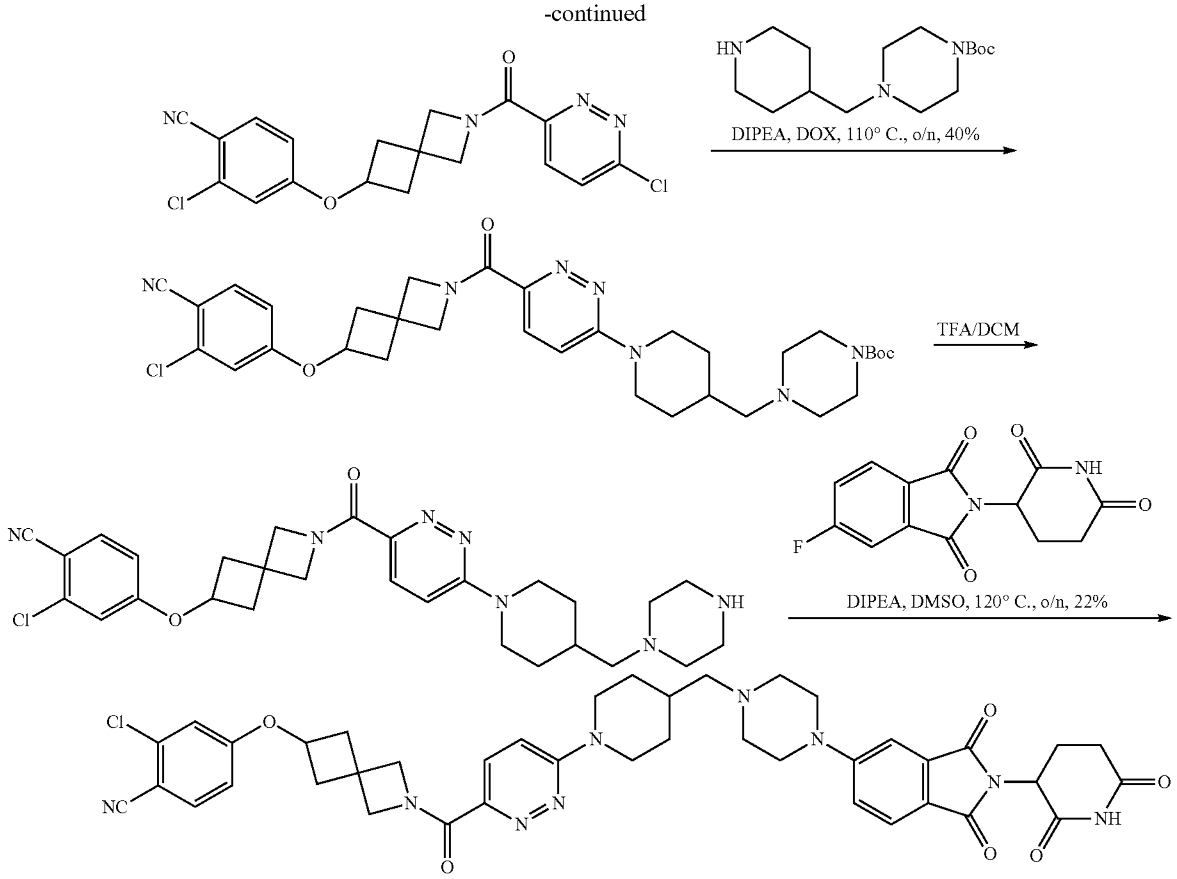

120

1. Synthesis of Compound t-butyl 6-(3-chloro-4-cyanophenoxy)-2-azaspiro[3.3]heptan-2-carboxylat Compound sodium hydride (60%) (514 mg, 12.86 mmol) was dissolved in 20 mL DMF, and the solution was stirred at −10° C. to 0° C. for 10 min, to which was then added t-butyl 6-hydroxy-2-azaspiro[3.3]heptan-2-carboxylate (2.05 g, 9.64 mmol). After the mixture was stirred for 30 min at −10° C. to 0° C., the solution of 2-chloro-4-fluorobenzonitrile (1.00 g, 6.43 mmol) in DMF was slowly added, and the reaction solution was stirred at −10° C. to 0° C. for 1 h. The solution was naturally warmed to room temperature and then stirred for 2 b. To the reaction solution, were added water and ethyl acetate for extraction. The organic layer was washed three times with the saturated solution of ammonium chloride and saturated brine, dried over anhydrous sodium sulfate, rotatory evaporated to dry, and purified by silica gel column chromatography, to provide a yellow oily compound t-butyl 6-(3-chloro-4-cyanophenoxy)-2-azaspiro[3.3]heptane-2-carboxylate (1.12 g, 3.21 mmol), with a yield of 50%.

LC/MS (ESI$^+$) calcd for $C_{18}H_{21}ClN_2O_3^+$[M+H]$^+$ m/z, 349.1; found 349.1.

2. Synthesis of Compound 4-(2-azaspiro[3.3]heptan-6-yloxy)-2-chlorobenzonitrile

Compound t-butyl 6-(3-chloro-4-cyanophenoxy)-2-azaspiro[3.3]heptan-2-carboxylate (348 mg, 1.00 mmol) and 2 mL of trifluoroacetic acid were dissolved in 1 mL of dichloromethane. After the reaction solution was stirred at room temperature for 1 h, TLC indicated that the reaction was completed, and the reaction solution was concentrated, to provide a white solid compound 4-(2-azaspiro[3.3]heptan-6-yloxy)-2-chlorobenzonitrile trifluoroacetate, which was directly used as the starting material for the next reaction, with a yield of 100%.

LC/MS (ESI$^+$) calcd for $C_{13}H_{13}ClN_2O^+$ [M+H]$^+$ m/z, 249.1; found 249.1.

3. Synthesis of Compound 2-chloro-4-((2-(6-chloropyridazine-3-carbonyl)-2-azaspiro[3.3]heptan-6-yl)oxy)benzonitrile Compounds 4-(2-azaspiro[3.3]heptan-6-yloxy)-2-chlorobenzonitrile trifluoroacetate (363 mg, 1.00 mmol), 6-chloropyridazine-3-carboxylic acid (316 mg, 2.00 mmol), and HATU (570 mg, 1.50 mmol) were added in 10 mL of dichloromethane, to which was added DIPEA (645 mg, 5.00 mmol) in an ice-water bath. The ice bath was removed, and the reaction solution was stirred overnight at room temperature, to which were added dichloromethane and water for extraction. The organic layer was washed with the saturated solution of ammonium chloride and saturated brine, dried over anhydrous sodium sulfate, rotatory evaporated to dry, and purified by silica gel column chromatography, to provide compound 2-chloro-4-((2-(6-chloropyridazine-3-carbonyl)-2-azaspiro[3.3]heptan-6-yl)oxy)benzonitrile (222 mg, 0.57 mmol), with a yield of 57%.

LC/MS (ESI+) calcd for $C_{18}H_{14}Cl_2N_4O_2^+$ [M+H]+ m/z, 389.0; found 389.0.

4. Synthesis of Compound t-butyl 4-((1-(6-(6-(3-chloro-4-cyanophenoxy)-2-azaspiro[3.3]heptan-2-carbonyl)pyridazine-3-yl)piperidine-4-yl)methylpiperazine-1-amide Compounds 2-chloro-4-((2-(6-chloropyridazine-3-carbonyl)-2-azaspiro[3.3]heptan-6-yl)oxy)benzonitrile (222 mg, 0.57 mmol), t-butyl 4-(piperidin-4-ylmethyl)piperazine-1-carboxylate (323 mg, 1.14 mmol), and DIPEA (221 mg, 1.71 mmol) were dissolved in 2 mL DOX, and the reaction solution was stirred overnight at 110° C. The reaction solution was added with water, and then extracted with ethyl acetate. The organic phase was washed three times with the saturated solution of ammonium chloride and saturated brine, dried over anhydrous sodium sulfate, filtered, concentrated, and purified by silica gel column chromatography, to provide compound t-butyl 4-((1-(6-(6-(3-chloro-4-cyanophenoxy)-2-azaspiro[3.3]heptan-2-carbonyl)pyridazine-3-yl)piperidine-4-yl)methylpiperazine-1-amide (150 mg, 0.23 mmol), with a yield of 40%.

LC/MS (ESI+) calcd for $C_{33}H_{42}ClN_7O_4^+$ [M+H]+ m/z, 636.3; found 636.3.

5. Synthesis of 2-chloro-4-((2-(6-(4-(4-piperazin-1-ylmethyl)piperidin-1-yl) pyridazine-3-carbonyl)-2-azaspiro[3.3]heptan-6-yl)oxy)benzonitrile Compound t-butyl 4-((1-(6-(6-(3-chloro-4-cyanophenoxy)-2-azaspiro[3.3]heptan-2-carbonyl)pyridazine-3-yl) piperidine-4-yl)methylpiperazine-1-amide (150 mg, 0.23 mmol) and 2 mL of trifluoroacetic acid were dissolved in 1 mL of dichloromethane. After the reaction solution was stirred at room temperature for 1 h, TLC indicated that the reaction was completed, and the reaction solution was concentrated, to provide a white solid compound 2-chloro-4-((2-(6-(4-(4-piperazin-1-ylmethyl)piperidin-1-yl) pyridazine-3-carbonyl)-2-azaspiro[3.3]heptan-6-yl)oxy) benzonitrile trifluoroacetate, which was directly used as the starting material for the next reaction, with a yield of 100%.

LC/MS (ESI+) calcd for $C_{28}H_{34}ClN_7O_2^+$ [M+H]+ m/z, 536.2; found 536.2.

6. Synthesis of 2-chloro-4-((2-(6-(4-((4-(2-(2,6-dioxopiperidin-3-yl))-1,3-dioxoisoindolin-5-yl)piperazin-1-yl)methyl)piperidin-1-yl)pyridazine-3-carbonyl)-2-azaspiro[3.3]heptan-6-yl)oxy)benzonitrile Compounds 2-chloro-4-((2-(6-(4-(4-piperazin-1-ylmethyl)piperidin-1-yl)pyridazine-3-carbonyl)-2-azaspiro[3.3]heptan-6-yl)oxy)benzonitrile trifluoroacetate (153 mg, 0.23 mmol), 2-(2,6-dioxopiperidin-3-yl)-5-fluoro-1,3-dioxoisoindoline (64 mg, 0.23 mmol), and DIPEA (149 mg, 1.15 mmol) were added in 2 mL of DMSO, and the reaction solution was heated to 130° C. and stirred for 3 h. The reaction solution was cooled to room temperature, to which were added water and ethyl acetate for extraction. The organic layer was washed with the saturated solution of ammonium chloride and brine, dried over anhydrous sodium sulfate, rotatory evaporated to dry, and purified by silica gel column chromatography, to provide compound 2-chloro-4-((2-(6-(4-((4-((2-(2,6-dioxopiperidin-3-yl))-1,3-dioxoisoindolin-5-yl)piperazin-1-yl)methyl)piperidin-1-yl)pyridazine-3-carbonyl)-2-azaspiro[3.3]heptan-6-yl)oxy)benzonitrile (40 mg, 0.50 mmol) as a yellow solid, with a yield of 22%. LC/MS (ESI+) calcd for $C_{41}H_{42}ClN_9O_6^+$ [M+H]+ m/z, 792.3; found 792.3. $^1$H NMR (400 MHz, DMSO-$d_6$) δ 11.93 (s, 2H), 11.09 (s, 1H), 7.89 (d, J=4.4 Hz, 1H), 7.73 (dd, J=6.0, 3.2 Hz, 1H), 7.68 (d, J=4.0 Hz, 1H), 7.35 (s, 1H), 7.32-7.23 (m, 3H), 7.05-7.00 (m, 1H), 5.07 (dd, J=8.8, 3.6 Hz, 1H), 4.86-4.79 (m, 1H), 4.68-4.55 (m, 2H), 4.67 (s, 1H), 4.56 (s, 1H), 4.15 (s, 1H), 4.07 (s, 1H), 3.48-3.43 (m, 3H), 3.05-2.95 (m, 2H), 2.84-2.78 (m, 2H), 2.71-2.66 (m, 1H), 2.32-2.26 (m, 2H), 2.25-2.18 (m, 2H), 2.06-1.95 (m, 2H), 1.91 (s, 2H), 1.87-1.79 (m, 2H), 1.26-1.21 (m, 2H), 1.18-1.08 (m, 3H).

121: Synthesis of N-((1r,4r)-4-(3-chloro-4-cyanophenoxy)cyclohexyl)-6-(4-((6-(2-(2,6-dioxopiperidin-3-yl)-1,3-dioxoisoindolin-5-yl)-2,6-diazaspiro[3.3]heptan-2-yl)methyl)piperidin-1-yl)pyridazine-3-amide

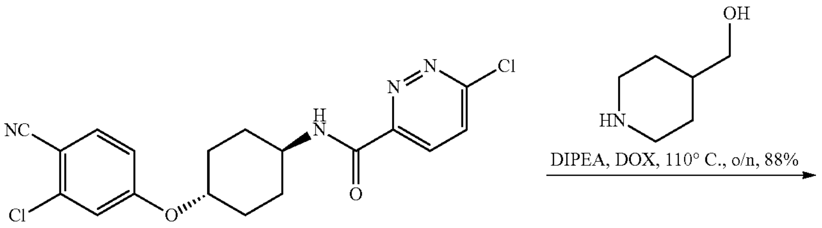

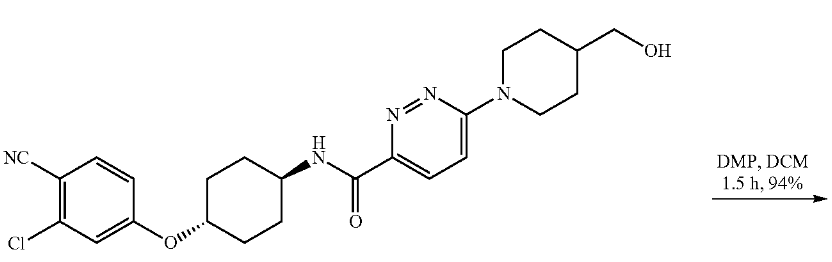

-continued

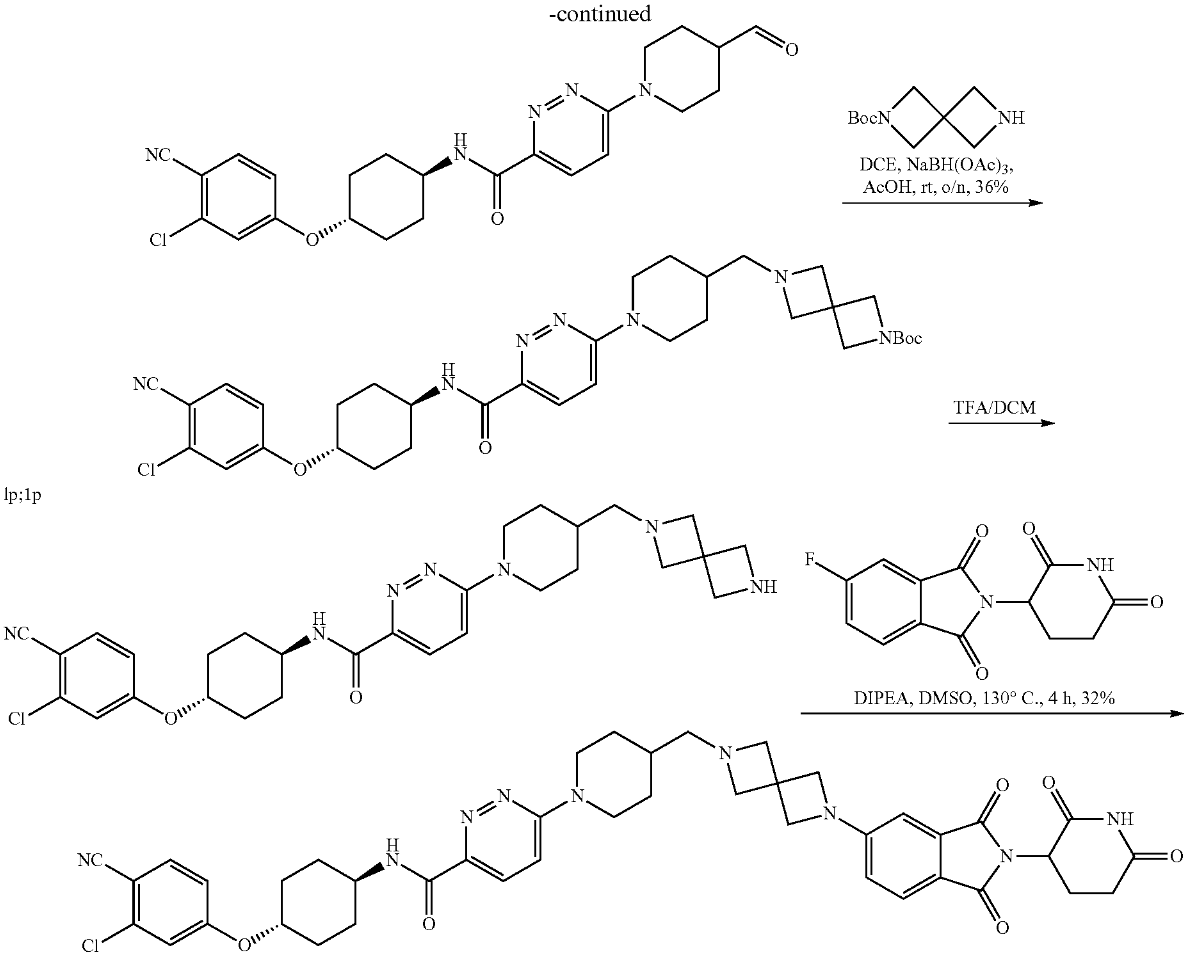

lp;1p

121

1. Synthesis of N-((1r,4r)-4-(3-chloro-4-cyanophenoxy)cyclohexyl)-6-(4-(hydroxymethyl)piperidin-1-yl)pyridazine-3-amide Compound 6-chloro-N-((1r,4r)-4-(3-chloro-4-cyanophenoxy)cyclohexyl)pyridazine-3-amide (300 mg, 0.77 mmol), 4-hydroxymethylpiperidine (177 mg, 1.54 mmol), and DIPEA (298 mg, 2.31 mmol) were dissolved in 5 mL DOX and stirred, and then the reaction solution was heated to 110° C. and stirred overnight. The reaction solution was added with water, and then extracted with ethyl acetate. The organic phase was washed three times with the saturated solution of ammonium chloride and saturated brine, dried over anhydrous sodium sulfate, concentrated, and purified by silica gel column chromatography, to provide compound N-((1r,4r)-4-(3-chloro-4-cyanophenoxy) cyclohexyl)-6-(4-(hydroxymethyl)piperidin-1-yl)pyridazine-3-amide (320 mg, 0.68 mmol), with a yield of 88%.

LC/MS (ESI$^+$) calcd for $C_{23}H_{24}ClN_5O_3^+$ [M+H]$^+$ m/z, 470.2; found 407.2.

2. Synthesis of N-((1r,4r)-4-(3-chloro-4-cyanophenoxy)cyclohexyl)-6-(4-formylpiperidin-1-yl) pyridazine-3-amide Compound N-((1r,4r)-4-(3-chloro-4-cyanophenoxy))cyclohexyl)-6-(4-(hydroxymethyl) piperidin-1-yl)pyridazine-3-amide (320 mg, 0.68 mmol) and Dess-Martin periodinane (377 mg, 0.89 mmol) were dissolved in 5 mL of dichloromethane. The solution was stirred at room temperature for 1.5 h, and TLC indicated the completion of the reaction. The reaction solution was filtered, and the filtrate was successively washed twice with the saturated solution of sodium bisulfite, once with the saturated solution of sodium carbonate, once with saturated brine, dried over anhydrous sodium sulfate, and concentrated, to provide N-((1r,4r)-4-(3-chloro-4-cyanophenoxy)cyclohexyl)-6-(4-formylpiperidin-1-yl) pyridazine-3-amide (300 mg, 0.64 mmol), with a yield of 94%.

LC/MS (ESI$^+$) calcd for $C_{24}H_{36}ClN_3O_3^+$ [M+H]$^+$ m/z, 468.2; found 468.2.

3. Synthesis of Compound t-butyl-6-((1-(6-(((1r,4r)-4-(3-chloro-4-cyanophenoxy) cyclohexyl)carbamoyl)pyridazine-3-yl)piperidine-4-yl)methyl)-2,6-diazaspiro[3.3]heptane-2-amide Compounds N-((1r,4r)-4-(3-chloro-4-cyanophenoxy)cyclohexyl)-6-(4-formylpiperidin-1-yl)pyridazine-3-amide (300 mg, 0.64 mmol) and t-butyl 2,6-diazaspiro[3.3]hep tane-2-carboxylate (255 mg, 1.28 mmol) were dissolved in 5 mL of 1,2-dichloroethane, and under the catalysis of two drops of glacial acetic acid, the mixture was stirred at room temperature for half an hour, to which was then added sodium triacetoxyborohydride (206 mg, 0.96 mmol). The mixture was continually stirred overnight at room temperature. After the reaction solution was concentrated, water was added, and the resultant solution was extracted with dichloromethane. The organic layer was washed with the saturated solution of ammonium chloride and brine, dried over anhydrous sodium sulfate, rotatory evaporated to dry, and purified by silica gel column chromatography, to provide compound t-butyl 6-((1-(6-(((1r,4r)-4-(3-chloro-4-cyanophenoxy)cyclohexyl)carbamoyl)pyridazine-3-yl) piperidine-4-yl) methyl)-2,6-diazaspiro[3.3]heptane-2-amide as a white solid (150 mg, 0.23 mmol), with a yield of 36%.

LC/MS ($ESI^+$) calcd for $C_{34}H_{44}ClN_4O_5^+$ $[M+H]^+$ m/z, 650.3; found 650.3.

4. Synthesis of Compound 6-((1-(6-(((1r,4r)-4-(3-chloro-4-cyanophenoxy)cyclohexyl) carbamoyl) pyridazine-3-yl)piperidine-4-yl)methyl)-2,6-diazaspiro[3.3]heptane-2-amide Compound t-butyl-6-((1-(6-(((1r,4r)-4-(3-chloro-4-cyanophenoxy)cyclohexyl) carbamoyl)pyridazine-3-yl)piperidine-4-yl)methyl)-2,6-diazaspiro[3.3]heptane-2-amide (50 mg, 0.77 mmol) and 2 mL of trifluoroacetic acid were dissolved in 1 mL of dichloromethane. After the reaction solution was stirred at room temperature for 1 h, TLC indicated that the reaction was completed, and the reaction solution was concentrated, to provide compound 6-((1-(6-(((1r,4r)-4-(3-chloro-4-cyanophenoxy) cyclohexyl)carbamoyl)pyridazine-3-yl)piperidine-4-yl)methyl)-2,6-diazaspiro [3.3]heptane-2-amide trifluoroacetate as a white solid, which was directly used as the starting material for the next reaction, with a yield of 100%.

LC/MS ($ESI^+$) calcd for $C_{29}H_{36}ClN_7O_2^+$ $[M+H]^+$ m/z, 550.3; found 550.3.

5. Synthesis of Compound N-((1r,4r)-4-(3-chloro-4-cyanophenoxy)cyclohexyl)-6-(4-((6-(2-(2,6-dioxopiperidin-3-yl)-1,3-dioxoisoindolin-5-yl)-2,6-diazaspiro[3.3]heptan-2-yl)methyl)piperidin-1-yl) pyridazine-3-amide Compound 6-((1-(6-(((1r,4r)-4-(3-chloro-4-cyanophenoxy)cyclohexyl)carbamoyl) pyridazine-3-yl)piperidine-4-yl)methyl)-2,6-diazaspiro[3.3]heptane-2-amide trifluoroacetate (51 mg, 0.077 mmol), 2-(2,6-dioxopiperidin-3-yl)-5-fluoro-1,3-dioxoisoindoline (22 mg, 0.077 mmol), and DIPEA (50 mg, 0.39 mmol) were added in 1 mL of DMSO, and the reaction solution was heated to 130° C. and stirred for 4 h. The reaction solution was cooled to room temperature, to which were added water and ethyl acetate for extraction. The organic layer was washed with the saturated solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(4-((6-(2-(2,6-dioxopiperidin-3-yl)-1,3-dioxoisoindolin-5-yl)-2,6-diazaspiro[3.3]heptan-2-yl)methyl) piperidin-1-yl)pyridazine-3-amide as a yellow solid (20 mg, 0.025 mmol), with a yield of 32%.

LC/MS ($ESI^+$) calcd for $C_{42}H_{44}ClN_4O_6^+$ $[M+H]^+$ m/z, 806.2; found 805.8.

$^1H$ NMR (400 MHz, DMSO-$d_6$) δ 11.09 (s, 1H), 8.61 (d, J=4.0 Hz, 1H), 7.86 (d, J=4.4 Hz, 1H), 7.80 (d, J=4.4 Hz, 1H), 7.65 (d, J=4.4 Hz, 1H), 7.39 (s, 1H), 7.34 (d, J=4.4 Hz, 1H), 7.14 (d, J=4.4 Hz, 1H), 6.80 (s, 1H), 6.66 (d, J=4.0 Hz, 1H), 5.10-5.03 (m, 1H), 4.59-4.41 (m, 3H), 4.16-4.09 (m, 3H), 3.93-3.74 (m, 2H), 3.20-3.14 (m, 1H), 3.05-2.93 (m, 2H), 2.91-2.81 (m, 1H), 2.63-2.58 (m, 1H), 2.54 (s, 3H), 2.14-2.05 (m, 2H), 2.03-1.99 (m, 1H), 1.94-1.84 (m, 2H), 1.84-1.72 (m, 2H), 1.71-1.58 (m, 3H), 1.57-1.45 (m, 2H), 1.30-1.20 (m, 2H), 1.20-1.03 (m, 3H).

122: Synthesis of N-((1r,4r)-4-(3-chloro-4-cyanophenoxy)cyclohexyl)-6-(4-((6-(2-(2,6-dioxopiperidin-3-yl)-6-fluoro-1,3-dioxoisoindolin-5-yl)-2,6-diazaspiro[3.3]heptan-2-yl)methyl)piperidin-1-yl) pyridazine-3-amide

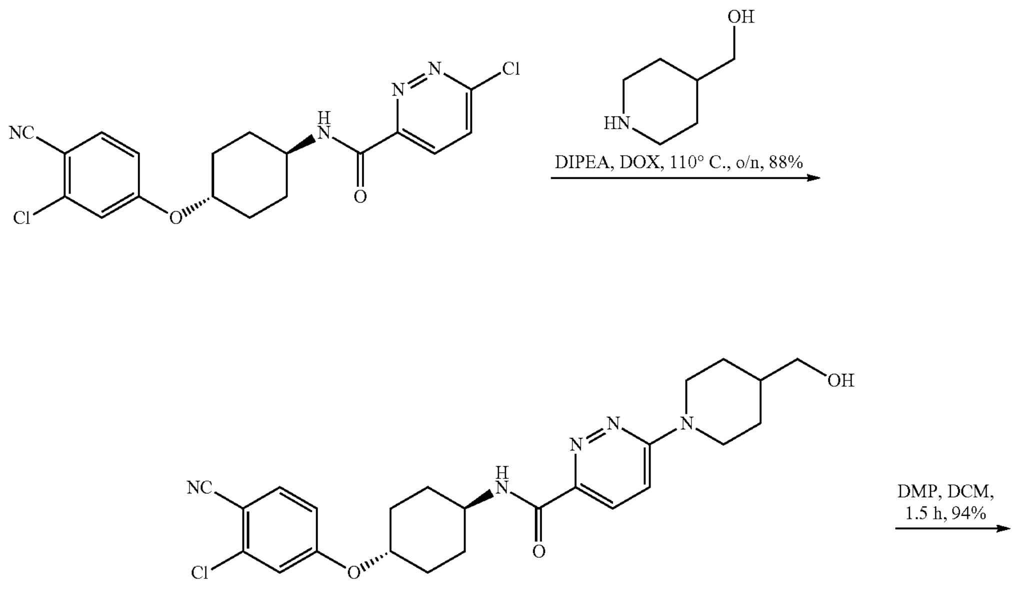

-continued
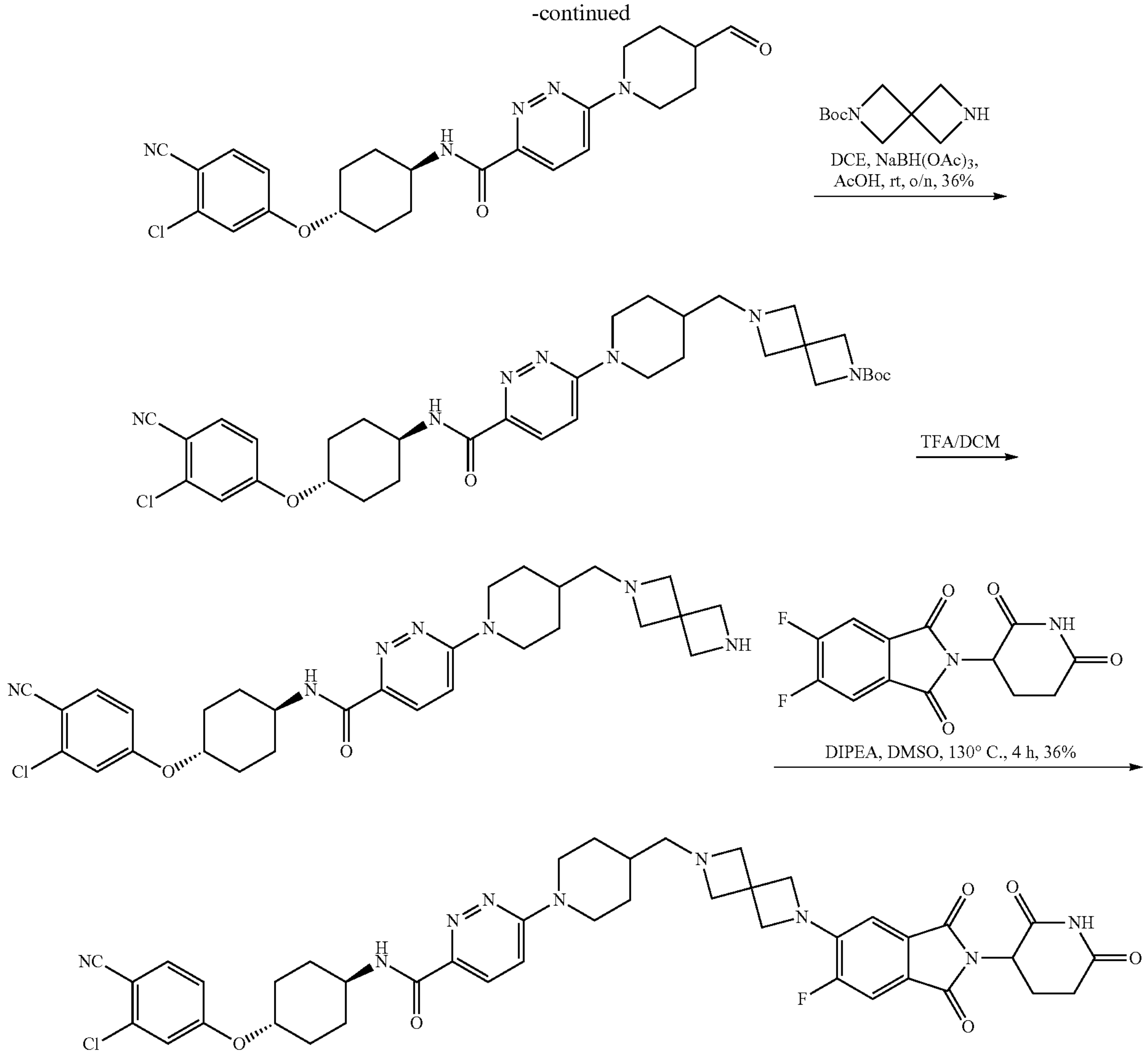
122
LC/MS (ESI+) calcd for $C_{42}H_{43}ClFN_9O_6^+$ $[M+H]^+$ m/z, 824.3; found 823.8.
$^1$H NMR (400 MHz, DMSO-$d_6$) δ 11.10 (s, 1H), 8.60 (d, J=4.0 Hz, 1H), 7.85 (d, J=4.4 Hz, 1H), 7.79 (d, J=4.4 Hz, 1H), 7.60 (d, J=4.4 Hz, 1H), 7.34 (s, 1H), 7.32 (d, J=4.0 Hz, 1H), 7.13 (d, J=4.4 Hz, 1H), 6.92 (s, 1H), 5.14-4.99 (m, 1H), 4.60-4.50 (m, 1H), 4.50-4.39 (m, 2H), 4.30-4.17 (m, 4H), 4.08-3.96 (m, 1H), 3.92-3.80 (m, 1H), 3.31-3.23 (m, 4H), 3.02-2.83 (m, 3H), 2.63-2.57 (m, 1H), 2.57-2.53 (m, 2H), 2.31-2.20 (m, 2H), 2.14-2.06 (m, 2H), 2.05-1.96 (m, 2H), 1.93-1.85 (m, 2H), 1.81-1.71 (m, 2H), 1.26-1.06 (m, 4H).
123: Synthesis of N-((1r,4r)-4-(3-chloro-4-cyanophenoxy)cyclohexyl)-6-(4-((6-(2-(2,6-dioxopiperidin-3-yl)-6-fluoro-1,3-dioxoisoindolin-5-yl)-2,6-diazaspiro[3.3]heptan-2-yl)methyl)piperidin-1-yl)pyrazine-2-amide
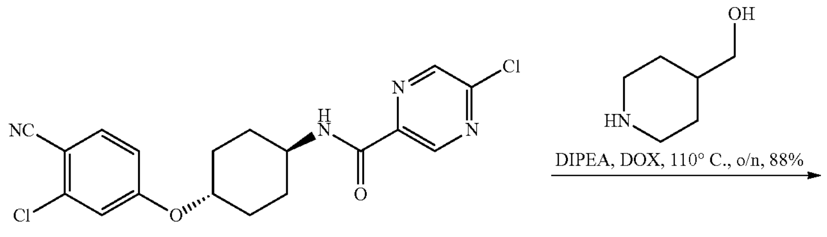

-continued
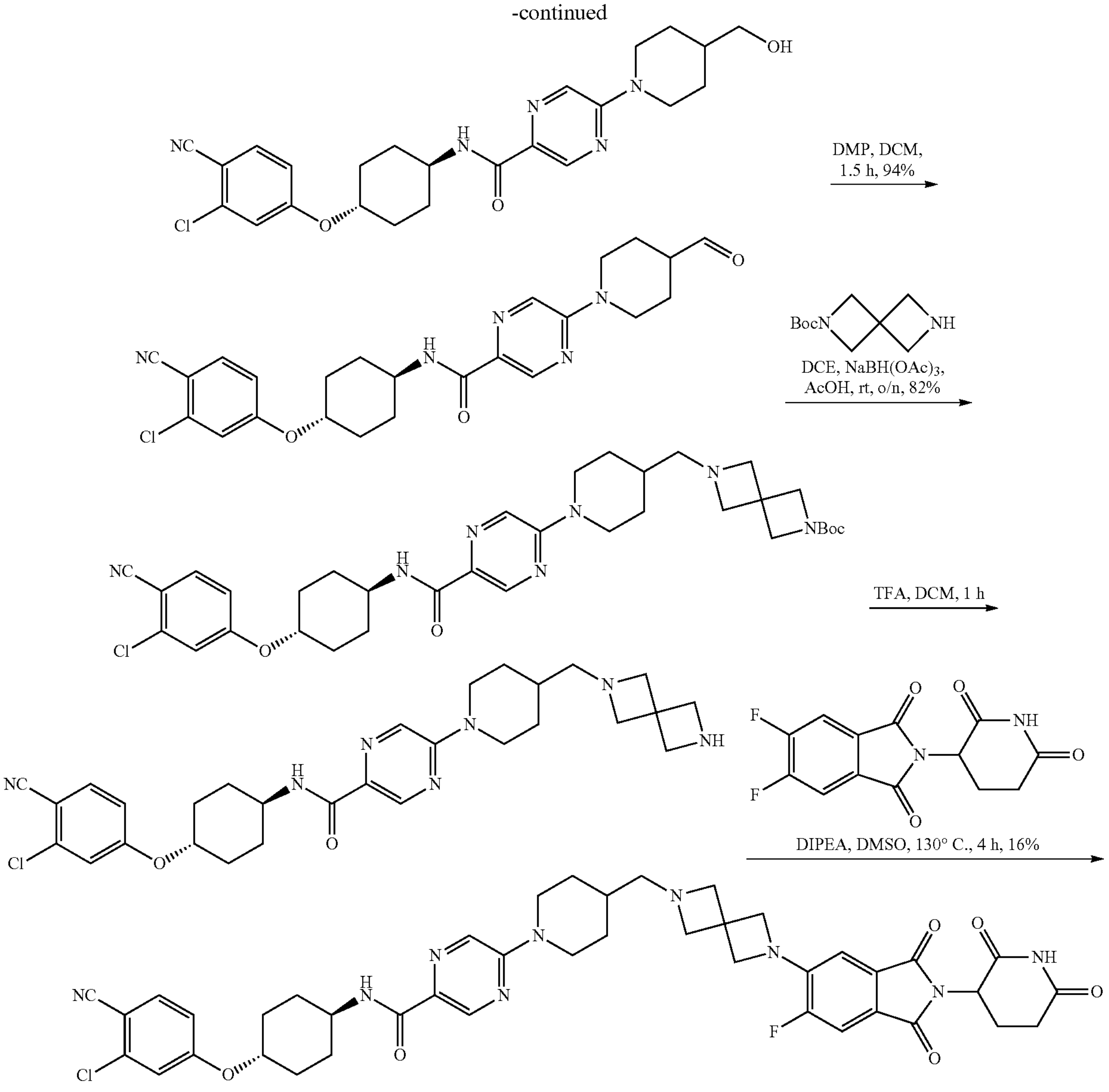
123
LC/MS (ESI$^+$) calcd for $C_{42}H_{43}ClFN_9O_6^+$ [M+H]$^+$ m/z, 824.3; found 824.2.
$^1$H NMR (400 MHz, DMSO-$d_6$) δ 11.09 (s, 1H), 8.58 (s, 11-1), 8.24 (s, 1H), 8.08 (d, J1=4.0 Hz, 1H), 7.86 (d, J=4.4 Hz, 1H), 7.61 (d, J=5.6 Hz, 1H), 7.38 (s, 1H), 7.13 (d, J=4.4 Hz, 1H), 6.92 (d, J=4.0 Hz, 1H), 5.10-5.03 (m, 1H), 4.56-4.48 (m, 1H), 4.48-4.39 (m, 2H), 4.28-4.21 (m, 3H), 3.85-3.79 (m, 1H), 3.31-3.29 (m, 2H), 3.00-2.81 (m, 4H), 2.71-2.67 (m, 1H), 2.63-2.58 (m, 1H), 2.21-2.14 (m, 1H), 2.13-2.05 (m, 2H), 2.05-1.97 (m, 2H), 1.90-1.85 (m, 21H), 1.80-1.71 (m, 2H), 1.63-1.57 (m, 2H), 1.53-1.48 (m, 2H), 1.13-1.07 (m, 2H), 0.89-0.80 (m, 3H).
124: Synthesis of N-((1r, 4r)-4-(3-chloro-4-cyano-phenoxy)cyclohexyl)-6-(6-yl)-6-fluoro-1,3-dioxoi-soindolin-5-yl)piperidine-4-yl)methyl)-2,6-diaz-aspiro[3.3]heptane-2-yl)pyridazine-3-amide
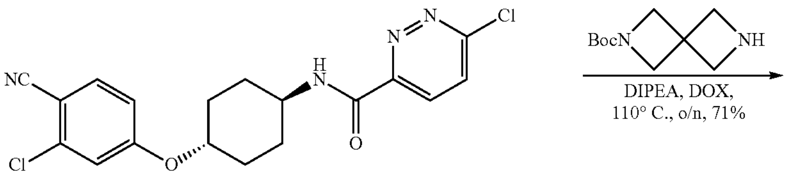

-continued

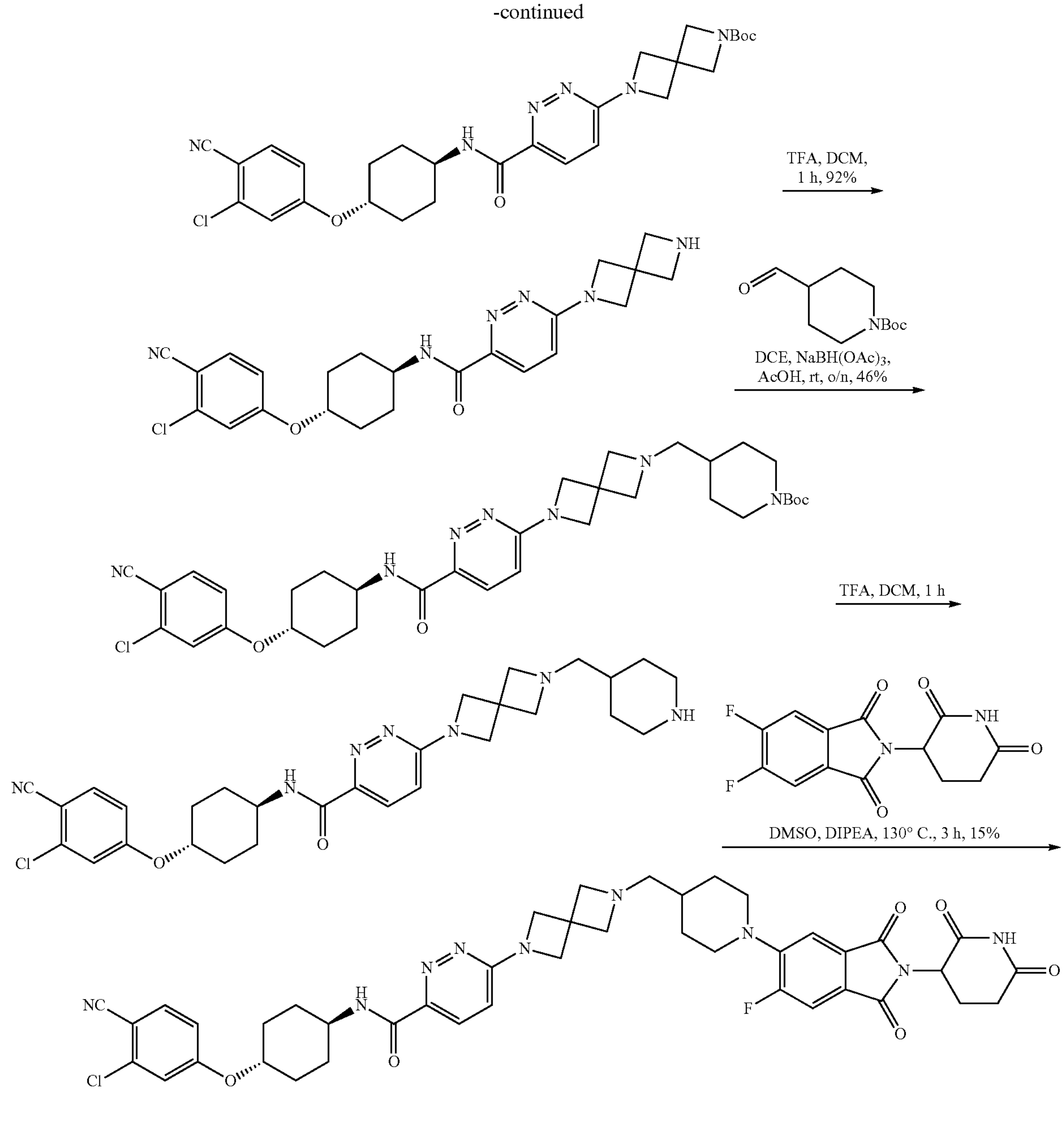

124

1. Synthesis of t-butyl 6-(6-(((1r,4r)-4-(3-chloro-4-cyanophenoxy)cyclohexyl) carbamoyl)pyridazine-3-yl)-2,6-diazaspiro[3.3]heptane-2-amide Compounds 6-chloro-N-((1r, 4r)-4-(3-chloro-4-cyanophenoxy)cyclohexyl)pyridazine-3-amide (200 mg, 0.51 mmol), t-butyl 2,6-diazaspiro[3.3]heptane-2-carboxylate (202 mg, 1.02 mmol), and DIPEA (198 mg, 1.53 mmol) were added in 5 mL DOX, and then the reaction solution was heated to 110° C. and stirred overnight. The reaction solution was cooled to room temperature, to which was added water, and then extracted with ethyl acetate. The organic layer was further washed three times with the saturated solution of ammonium chloride and brine, dried over anhydrous sodium sulfate, rotatory evaporated to dry, and purified by silica gel column chromatography, to provide compound t-butyl 6-(6-(((1r, 4r)-4-(3-chloro-4-cyanophenoxy) cyclohexyl) carbamoyl)pyridazine-3-yl)-2,6-diazaspiro[3.3] heptane-2-amide as a white solid (200 mg, 0.36 mmol), with a yield of 71%.

LC/MS (ESI$^+$) calcd for $C_{23}H_{35}N_2O_5^+$ [M+H]$^+$ m/z, 553.2; found 553.2.

2. N-((1r,4r)-4-(3-chloro-4-cyanophenoxy)cyclohexyl)-6-(2,6-diazaspiro[3.3]heptane-2-yl) pyridazine-3-amide Compound t-butyl 6-(6-(((1r,4r)-4-(3-chloro-4-cyanophenoxy)cyclohexyl)carbamoyl) pyridazine-3-yl)-2,6-diazaspiro[3.3]heptane-2-amide (200 mg, 0.36 mmol) and 2 mL of trifluoroacetic acid were dissolved in 1 mL of dichloromethane. After the reaction solution was stirred at room temperature for 1 h, TLC indicated that the reaction was completed, and then the reaction solution was concentrated. After that, the saturated solution of sodium carbonate was added to adjust the pH of the reaction solution to 10, and then the solution was extracted with dichloromethane. The organic phase was washed with saturated brine, dried over anhydrous sodium sulfate, and concentrated, to provide compound N-((1r,4r)-4-(3-chloro-4-cyanophenoxy)cyclohexyl)-6-(2,6-diazaspiro[3.3]heptane-2-yl)pyridazine-3-amide (150 mg, 0.33 mmol), with a yield of 92%. LC/MS (ESI$^+$) calcd for $C_{22}H_{33}N_2O_5^+$ [M+H]$^+$ m/z, 453.2; found 453.2.

3. Synthesis of t-butyl 4-((6-(6-(((1r,4r)-4-(3-chloro-4-cyanophenoxy)cyclohexyl) carbamoyl)pyridazine-3-yl)-2,6-diazaspiro[3.3]heptane-2-yl)piperidine-1-formate Compounds N-((1r,4r)-4-(3-chloro-4-cyanophenoxy)cyclohexyl)-6-(2,6-diazaspiro[3.3]heptane-2-yl)pyridazine-3-amide (150 mg, 0.33 mmol) and t-butyl 4-formylpiperidine-1-carboxylate (141 mg, 0.66 mmol) were dissolved in 3 mL of 1,2-dichloroethane, and under the catalysis of two drops of glacial acetic acid, the mixture was stirred at room temperature for half an hour, to which was then added sodium triacetoxyborohydride (186 mg, 0.49 mmol). The mixture was continually stirred overnight at room temperature. After the reaction solution was concentrated, water was added, and the resultant solution was extracted with dichloromethane. The organic layer was washed with the saturated solution of ammonium chloride and saturated brine, dried over anhydrous sodium sulfate, concentrated, and purified by silica gel column chromatography, to provide compound methyl 4-t-butyl 4-((6-(6-(((1r,4r)-4-(3-chloro-4-cyanophenoxy)cyclohexyl)carbamoyl)pyridazine-3-yl)-2,6-diazaspiro[3.3]heptane-2-yl)piperidine-1-formate (100 mg, 0.15 mmol), with a yield of 46%.

LC/MS (ESI$^+$) calcd for $C_{35}H_{46}ClN_4O_5^+$ [M+H]$^+$ m/z, 637.3; found 637.2.

4. Synthesis of Compound N-((1r, 4r)-4-(3-chloro-4-cyanophenoxy)cyclohexyl)-6-(6-(piperidin-4-yl-methyl)-2,6-diazaspiro[3.3]heptane-2-yl)pyridazine-3-amide Compound methyl 4-t-butyl 4-((6-(6-(((1r,4r)-4-(3-chloro-4-cyanophenoxy)cyclohexyl) carbamoyl)pyridazine-3-yl)-2,6-diazaspiro[3.3]heptane-2-yl)piperidine-1-formate (100 mg, 0.15 mmol) and 2 mL of trifluoroacetic acid were dissolved in 1 mL of dichloromethane. After the reaction solution was stirred at room temperature for 1 h, TLC indicated that the reaction was completed, and then the reaction solution was concentrated, to provide compound N-((1r,4r)-4-(3-chloro-4-cyanophenoxy) cyclohexyl)-6-(6-(piperidin-4-yl-methyl)-2,6-diazaspiro[3.3]heptane-2-yl) pyridazine-3-amide trifluoroacetate as a white solid, which was directly used as the starting material for the next reaction, with a yield of 100%.

LC/MS (ESI$^+$) calcd for $C_{30}H_{38}ClN_4O_3^+$ [M+H]$^+$ m/z, 537.3; found 537.3.

5. Synthesis of Compound N-((1r,4r)-4-(3-chloro-4-cyanophenoxy)cyclohexyl)-4-(4-((1-(2-(2,6-dioxopiperidin-3-yl)-1,3-dioxoisoindolin-5-yl)piperidine-4-yl)oxy) piperidin-1-yl)benzamide Compounds N-((1r,4r)-4-(3-chloro-4-cyanophenoxy)cyclohexyl)-6-(6-(piperidin-4-yl-methyl)-2,6-diazaspiro[3.3] heptane-2-yl)pyridazine-3-amide trifluoroacetate (97 mg, 0.15 mmol), 2-(2,6-dioxopiperidin-3-yl)-5-fluoroisoindole-1,3-dione (44 mg, 0.15 mmol), and DIPEA (97 mg, 0.75 mmol) were added in 3 mL of DMSO. The reaction solution was heated to 130° C. and stirred for 3 h. The reaction solution was cooled to room temperature, to which were added water and ethyl acetate for extraction. The organic layer was washed with the saturated solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-4-(4-((1-(2-(2,6-dioxopiperidin-3-yl)-1,3-dioxoisoindolin-5-yl)piperidine-4-yl)oxy)piperidin-1-yl)benzamide (18 mg, 0.022 mmol), with a yield of 15%. LC/MS (ESI$^+$) calcd for $C_{42}H_{43}ClN_9O_6^+$ [M+H]$^+$ m/z, 824.3; found 824.2. $^1$H NMR (400 MHz, DMSO-$d_6$) δ 11.09 (s, 1H), 8.64 (d, J=4.0 Hz, 1H), 7.83 (d, J=4.4 Hz, 2H), 7.61 (d, J=6.4 Hz, 1H), 7.50 (d, J=1.2 Hz, 1H), 7.36 (d, J=4.8 Hz, 1H), 7.17 (dd, J=5.2, 2.8 Hz, 1H), 7.09 (d, J=4.0 Hz, 1H), 5.86-5.70 (m, 1H), 5.10-5.03 (m, 1H), 4.57-4.49 (m, 1H), 3.90-3.83 (m, 3H), 3.78-3.68 (m, 4H), 3.62-3.58 (m, 2H), 3.31 (s, 3H), 2.98-2.80 (m, 2H), 2.64-2.54 (m, 4H), 2.41-2.31 (m, 3H), 2.13-2.07 (m, 2H), 2.05-1.97 (m, 2H), 1.94-1.90 (m, 1H), 1.89-1.87 (m, 1H), 1.65-1.62 (m, 2H), 1.25-1.23 (m, 2H).

125: Synthesis of N-((1r,4r)-4-(3-chloro-4-cyanophenoxy)cyclohexyl)-6-(6-yl)-6-fluoro-1,3-dioxoisoindolin-5-yl)piperidine-4-yl)methyl)-2,6-diazaspiro[3.3]heptane-2-yl)pyrazine-2-amide

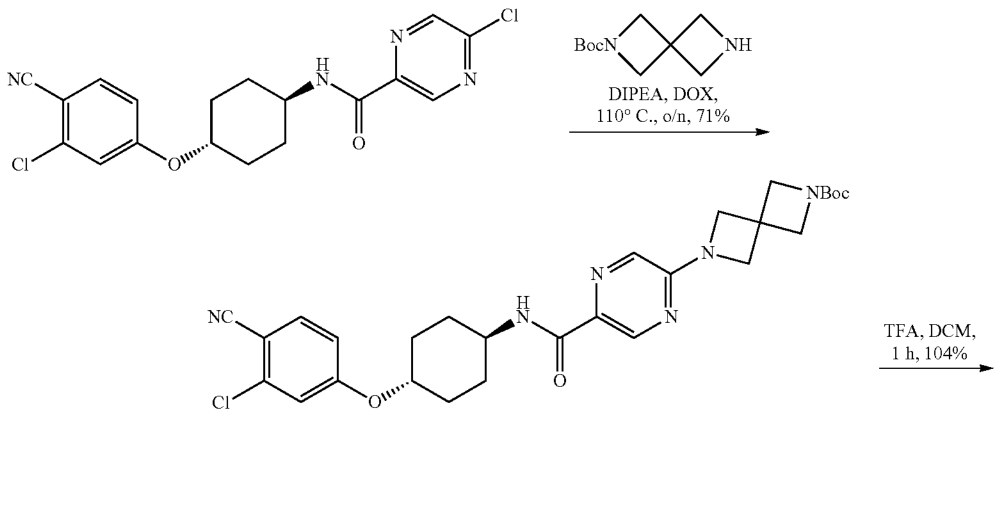

-continued
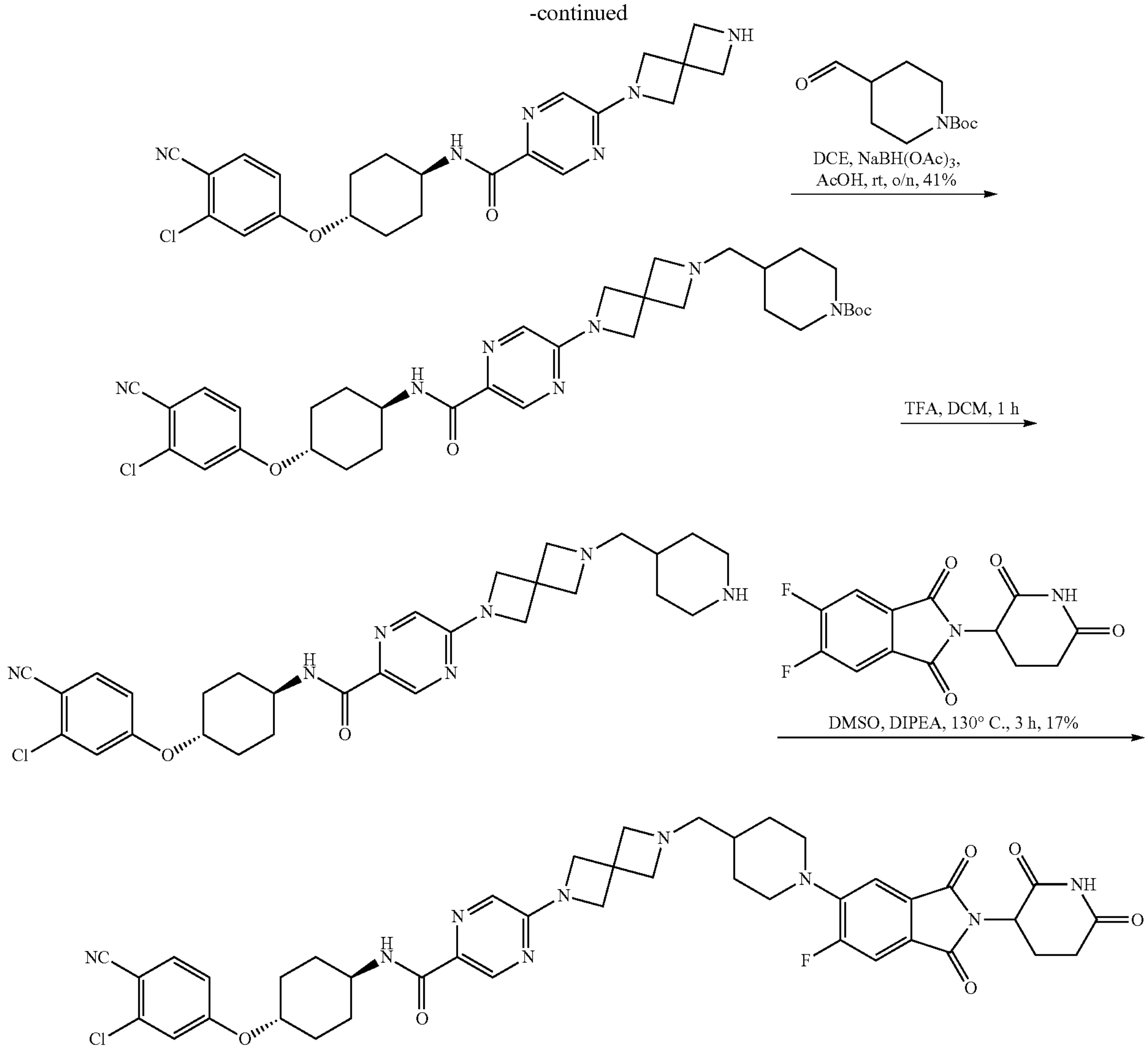
125
LC/MS (ESI+) calcd for $C_{42}H_{43}ClN_9O_6^+$ [M+H]+ m/z, 824.3; found 824.2.
$^1$H NMR (400 MHz, DMSO-$d_6$) δ 11.12 (s, 1H), 8.59 (s, 1H), 8.14 (d, J=4.0 Hz, 1H), 7.87-7.81 (m, 2H), 7.73 (d, J=5.6 Hz, 1H), 7.46 (m, J=4.0 Hz, 1H), 7.39-7.36 (m, 1H), 7.15-7.11 (m, 1H), 5.14-5.07 (m, 1H), 4.58-4.47 (m, 2H), 4.30-4.23 (m, 4H), 3.87-3.78 (m, 2H), 3.66-3.56 (m, 4H), 3.11-3.05 (m, 2H), 2.96-2.83 (m, 5H), 2.12-2.04 (m, 3H), 1.89-1.84 (m, 2H), 1.81-1.76 (m, 2H), 1.62-1.57 (m, 2H), 1.53-1.48 (m, 2H), 1.24-1.23 (m, 3H), 0.89-0.80 (m, 2H).
126: Synthesis of N-((1r,4r)-4-(3-bromo-4-cyanophenoxy)cyclohexyl)-6-(4-(((1R,5S,6s)-3-(2-(2,6-dioxopiperidin-3-yl)-6-fluoro-1,3-dioxoisoindolin-5-yl)-3-azabicyclo[3.1.0]hexan-6-yl)methyl)piperazin-1-yl)pyridazine-3-amide
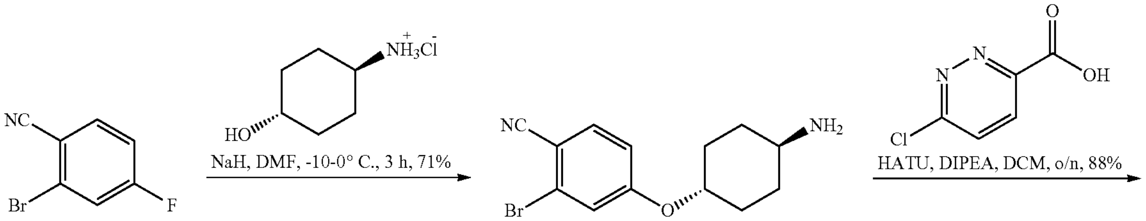

-continued

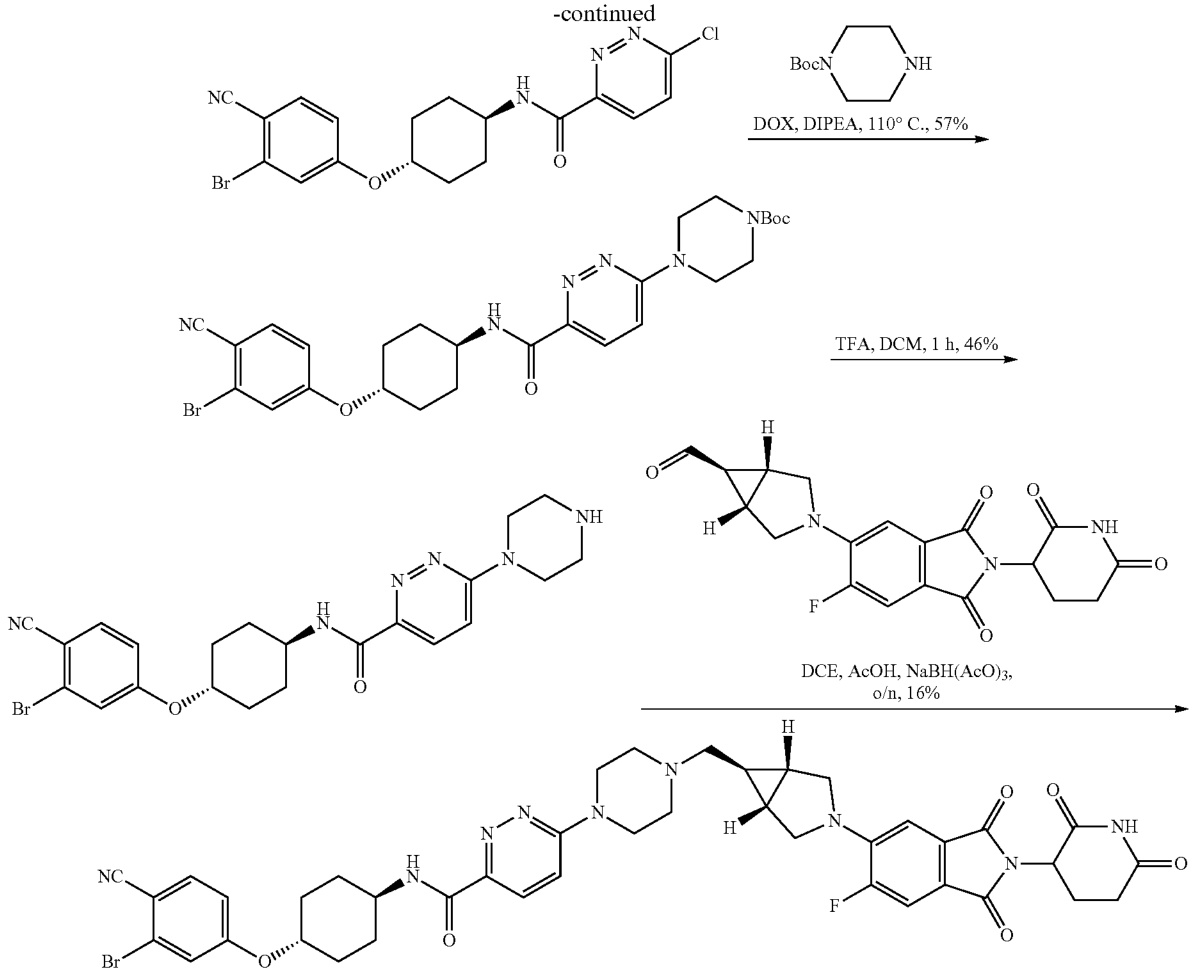

126

1. Synthesis of Compound 4-(((1r,4r)-4-aminocyclohexyl)oxy)-2-bromobenzonitrile

Compound sodium hydride (60%, 3.50 g, 87.50 mmol) was dissolved in 400 mL DMF, and then stirred at −10° C. to 0° C. for 10 min, to which was added (1r,4r)-4-hydroxycyclohexylamine hydrochloride (4.17 g, 27.5 mmol). After the reaction solution was stirred for 30 min at −10° C. to 0° C., the solution of 2-bromo-4-fluorobenzonitrile (5.00 g, 25.00 mmol) in DMF was slowly added, and the resultant solution was stirred at −10° C. to 0° C. for 1 h. The reaction solution was naturally warmed to room temperature, and then stirred for additional 4 h. The reaction solution was added with the mixture of ice-water, and then extracted with ethyl acetate. The organic layer was washed three times with saturated brine. The organic phase was adjusted to pH 1 with 1 mol/L dilute hydrochloric acid solution, and extracted three times with ethyl acetate, to which was then added the saturated solution of sodium hydroxide to adjust pH to 12. The resultant solution was extracted with ethyl acetate, and the organic phase was washed with saturated brine, dried over anhydrous sodium sulfate, and concentrated, to provide compound 4-(((1r, 4r)-4-aminocyclohexyl)oxy)-2-bromobenzonitrile (5.20 g, 17.63 mmol), with a yield of 71%.

LC/MS (ESI) calcd for $C_{13}H_{15}BrN_2O^+$ $[M+H]^+$ m/z, 295.0; found 295.0.

2. Synthesis of Compound N-((1r, 4r)-4-(3-bromo-4-ylphenoxy)cyclohexyl)-6-chloropyridazine-3-amide Compounds 4-(((1r, 4r)-4-aminocyclohexyl)oxy)-2-bromobenzonitrile (1.00 g, 3.39 mmol), 5-chloropyrazine-22-carboxylic acid (805 mg, 5.08 mmol), and HATU (1.67 g, 4.41 mmol) were added in 30 mL of dichloromethane, to which was added DIPEA (1.13 g, 10.17 mmol) in an ice-water bath. The ice bath was removed, and the reaction solution was stirred overnight at room temperature, to which were added water and ethyl acetate for extraction. The organic layer was washed with the saturated solution of ammonium chloride and saturated brine, dried over anhydrous sodium sulfate, rotatory evaporated to dry, and purified by silica gel column chromatography, to provide compound N-((1r,4r)-4-(3-bromo-4-ylphenoxy)cyclohexyl)-6-chloropyridazine-3-amide (1.30 g, 2.98 mmol), with a yield of 88%.

LC/MS ($ESI^+$) calcd for $C_{18}H_{16}BrClN_4O_2^+$ $[M+H]^+$ m/z, 435.0; found 435.0.

3. t-Butyl 4-(6-(((1r,4r)-4-(3-bromo-4-cyanophenoxy)cyclohexyl)carbamoyl) pyridazine-3-yl)piperazine-1-amide Compounds N-((1r,4r)-4-(3-bromo-4-ylphenoxy)cyclohexyl)-6-chloropyridazine-3-amide (200 mg, 0.46 mmol), t-butyl piperazine-1-carboxylate (172 mg, 0.92 mmol), and DIPEA (178 mg, 1.38 mmol) were dissolved in 3 mL of DOX and stirred. The reaction solution was stirred overnight at 110° C. The reaction solution was added with water, and then extracted with ethyl acetate. The organic phase was washed three times with the saturated solution of ammonium chloride and saturated brine, dried over anhydrous sodium sulfate, concentrated, and purified by silica gel column chromatography, to provide compound t-butyl 4-(6-(((1r,4r)-4-(3-bromo-4-cyanophenoxy)cyclohexyl)carbamoyl) pyridazine-3-yl)piperazine-1-amide (150 mg, 0.26 mmol), with a yield of 57%. LC/MS (ESI+) calcd for $C_{27}H_{33}BrN_6O_4^+$ $[M+H]^+$ m/z, 585.2; found 585.2.

4. Synthesis of Compound N-((1 r,4r)-4-(3-bromo-4-cyanophenoxy)cyclohexyl)-6-(piperazin-1-yl) pyridazine-3-amide Compound t-butyl 4-(6-(((1r,4r)-4-(3-bromo-4-cyanophenoxy)cyclohexyl)carbamoyl) pyridazine-3-yl)piperazine-1-amide (150 mg, 0.26 mmol) was dissolved in 1 mL of dichloromethane and 2 mL of trifluoroacetic acid. The reaction solution was stirred at room temperature for 2 h. The solvent was rotatory evaporated to dry, and to the residue, was added the saturated solution of sodium carbonate to adjust pH to 12. The resultant solution was extracted with dichloromethane. The organic phase was washed with saturated brine, dried over anhydrous sodium sulfate, and concentrated, to provide compound N-((1r,4r)-4-(3-chloro-4-cyanophenoxy)cyclohexyl)-4-(4-(piperidine-4-acyloxy) piperidin-1-yl)benzamide (60 mg, 0.12 mmol), with a yield of 46%.

LC/MS (ESI+) calcd for $C_{22}H_{25}BrN_6O_2^+$ $[M+H]^+$ m/z, 485.1; found 485.1.

5. N-((1r,4r)-4-(3-bromo-4-cyanophenoxy)cyclohexyl)-6-(4-(((1R,5S,6s)-3-(2-(2,6-dioxopiperidin-3-yl)-6-fluoro-1,3-dioxoisoindolin-5-yl)-3-azabicyclo [3.1.0]hexan-6-yl)methyl)piperazin-1-yl)pyridazine-3-amide Compounds N-((1r,4r)-4-(3-bromo-4-cyanophenoxy)cyclohexyl)-6-(piperazin-1-yl) pyridazine-3-amide (60 mg, 0.12 mmol) and (1R,5S,6r)-3-(2-(2,6-dioxopiperidin-3-yl)-6-fluoro-1,3-dioxoisoindol-5-yl)-3-azabicyclo[3.1.0]hexan-6-formaldehyde (48 mg, 0.12 mmol) were dissolved in 1 mL of 1,2-dichloroethane, and under the catalysis of two drops of glacial acetic acid, the mixture was stirred at room temperature for half an hour, to which was then added sodium triacetoxyborohydride (27 mg, 0.12 mmol). The mixture was continually stirred overnight at room temperature. After the reaction solution was concentrated, water was added, and the resultant solution was extracted with dichloromethane. The organic layer was washed with the saturated solution of ammonium chloride and saturated brine, dried over anhydrous sodium sulfate, concentrated, and purified by silica gel column chromatography, to provide compound N-((1r,4r)-4-(3-bromo-4-cyanophenoxy)cyclohexyl)6-(4-(((1R,5S,6s)-3-(2-(2,6-dioxopiperidin-3-yl)-6-fluoro-1,3-dioxoisoindolin-5-yl)-3-azabicyclo[3.1.0]hexan-6-yl)methyl) piperazin-1-yl)pyridazine-3-amide as a yellow solid (16 mg, 0.019 mmol), with a yield of 16%.

LC/MS (ESI+) calcd for $C_{41}H_{41}BrFN_9O_6^+$ $[M+H]^+$ m/z, 854.2; found 854.2.

$^1$H NMR (400 MHz, DMSO-$d_6$) δ 11.10 (s, 1H), 8.64 (d, J=4.0 Hz, 1H), 7.84 (d, J=4.0 Hz, 2H), 7.61 (d, J=6.4 Hz, 1H), 7.52-7.48 (m, 1H), 7.36 (d, J=3.6 Hz, 1H), 7.19-7.15 (m, 1H), 7.08 (d, J=3.6 Hz, 1H), 5.10-5.04 (m, 1H), 4.57-4.50 (m, 1H), 3.90-3.81 (m, 3H), 3.76-3.68 (m, 4H), 3.63-3.58 (m, 2H), 2.63-2.55 (m, 5H), 2.37-2.33 (m, 2H), 2.13-2.07 (m, 2H), 1.95-1.85 (m, 3H), 1.65-1.59 (m, 3H), 1.27-1.20 (m, 4H), 0.88-0.80 (m, 2H).

127: Synthesis of N-((1r,4r)-4-(3-bromo-4-cyanophenoxy)cyclohexyl)-6-(4-(((1R,5S,6s)-3-(2-(2,6-dioxopiperidin-3-yl)-6-fluoro-1,3-dioxoisoindolin-5-yl)-3-azabicyclo[3.1.0]hexan-6-yl)methyl)piperazin-1-yl)pyrazine-2-amide

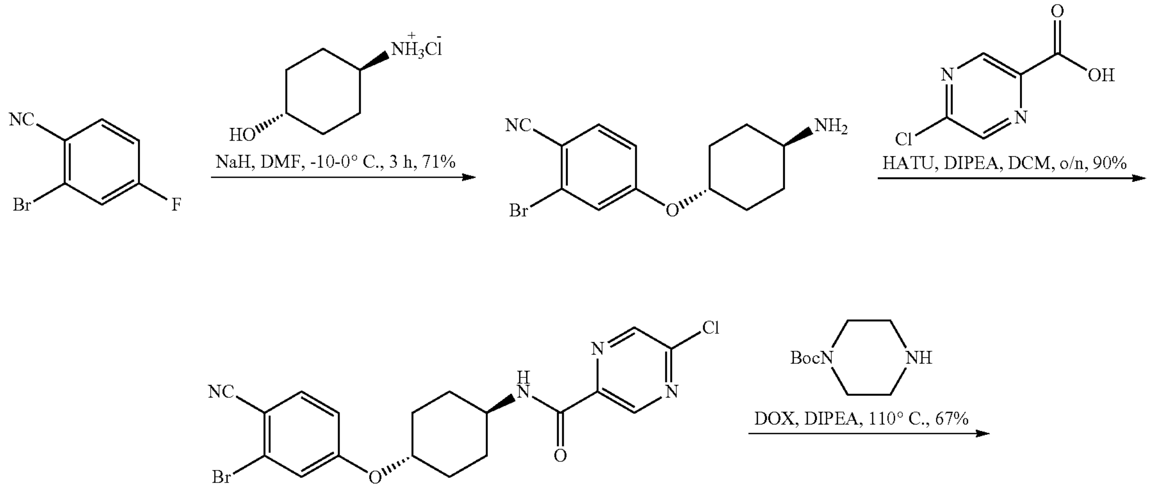

-continued
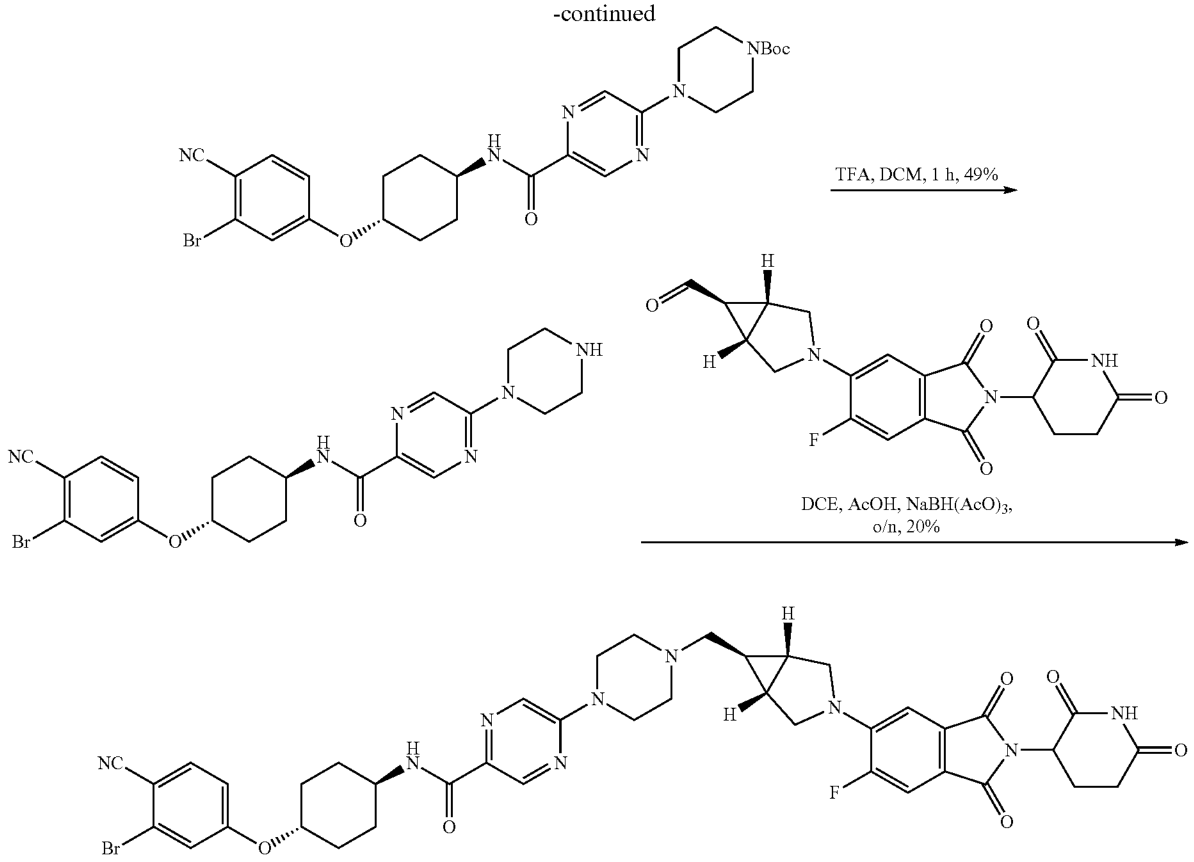
127
LC/MS (ESI+) calcd for $C_{41}H_{41}BrFN_9O_6^+$ [M+H]+ m/z, 854.2; found 854.3.
$^1$HNMR (400 MHz, DMSO-$d_6$) δ 11.10 (s, 1H), 8.61 (s, 1H), 8.27 (s, 1H), 8.13 (d, J=4.0 Hz, 1H), 7.84 (d, J=4.0 Hz, 1H), 7.60 (d, J=6.4 Hz, 1H), 7.48 (d, J=1.2 Hz, 1H), 7.19-7.13 (m, 1H), 7.08 (d, J=4.0 Hz, 1H), 4.56-4.46 (m, 5H), 3.89-3.80 (m, 3H), 3.76-3.65 (m, 4H), 3.63-3.55 (m, 2H), 2.94-2.81 (m, 1H), 2.61-2.55 (m, 4H), 2.41-2.31 (m, 2H), 2.13-2.05 (m, 2H), 1.99 (s, 2H), 1.91-1.83 (m, 1H), 1.68-1.58 (m, 3H), 1.58-1.43 (m, 3H), 1.27-1.21 (m, 1H), 0.90-0.74 (m, 2H).
128: N-((1r,4r)-4-(3-chloro-4-cyanophenoxy)cyclohexyl)-2-(4-(((((1R,5S,6s)-3-(2-(2,6-dioxapiperidin-3-yl)-6-fluoro-1,3-dioxoisoindolin-5-yl)-3-azabicyclo[3.1.0]hexan-6-yl)methyl)piperazin-1-yl) pyrimidine-5-amide
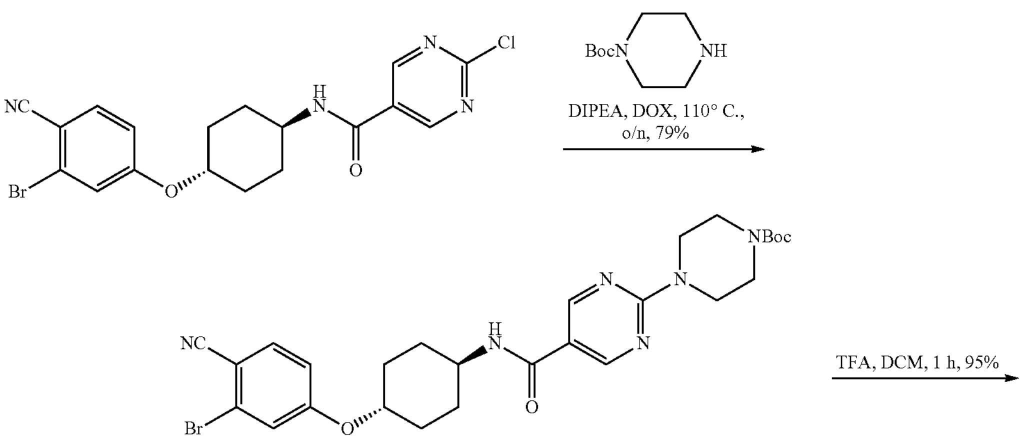

-continued
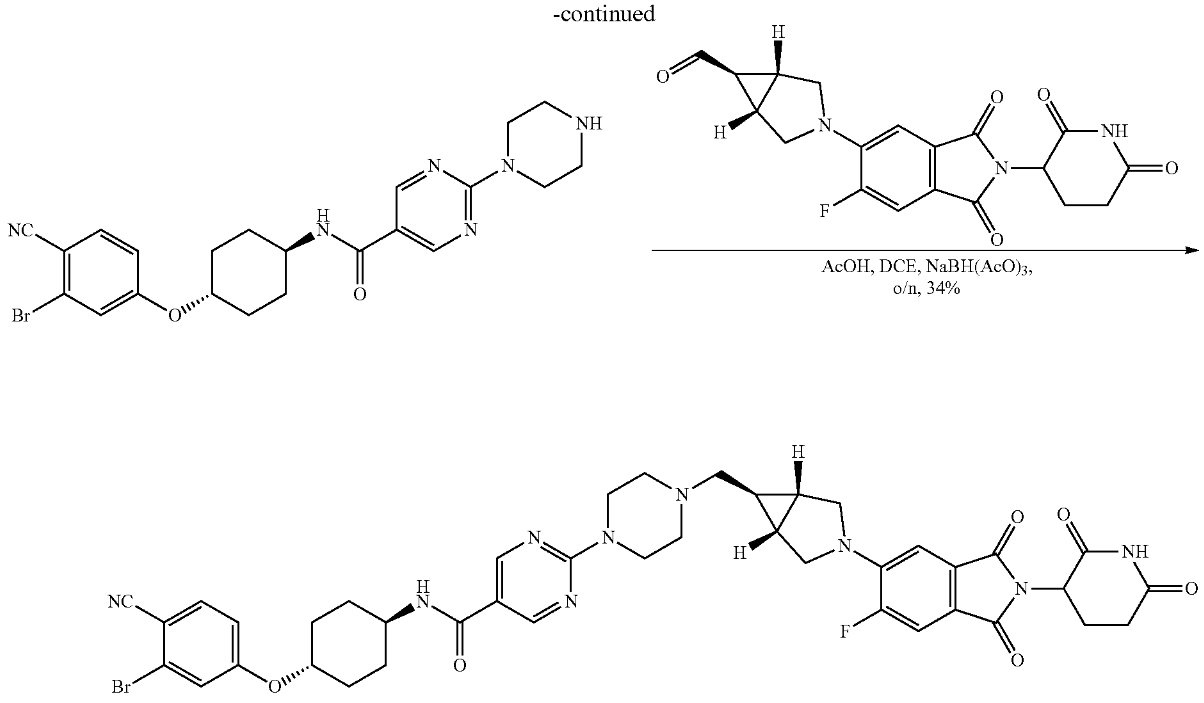
128
LC/MS (ESI+) calcd for $C_{41}H_{41}BrFN_9O_6^+$ $[M+H]^+$ m/z, 810 found, 810.3.
$^1$HNMR (400 MHz, DMSO-$d_6$) δ 11.11 (s, 1H), 8.76 (s, 2H), 8.15 (d, J=3.6 Hz, 1H), 7.86 (d, J=4.4 Hz, 1H), 7.60 (d, J=6.4 Hz, 1H), 7.39 (s, 1H), 7.14 (d, J=3.6 Hz, 1H), 7.07 (d, J=4.0 Hz, 1H), 5.78-5.74 (m, 1H), 5.10-5.02 (m, 1H), 4.58-4.50 (m, 1H), 3.86-3.80 (m, 5H), 3.61-3.56 (m, 2H), 2.92-2.81 (m, 1H), 2.63-2.57 (m, 1H), 2.35-2.29 (m, 2H), 2.13-2.07 (m, 2H), 2.03-1.98 (m, 1H), 1.95-1.87 (m, 4H), 1.62-1.58 (m, 2H), 1.54-1.45 (m, 4H), 1.27-1.19 (m, 3H), 0.86-0.79 (m, 2H).
129: Synthesis of N-((1r,4r)-4-(3-chloro-4-cyano-phenoxy)cyclohexyl)-6-(6-(4-(2-(2,6-dioxopiperidin-3-yl)-6-fluoro-1,3-dioxoisoindolin-5-yl)piperazin-1-yl)-2-azaspiro[3.3]heptan-2-yl)pyridazine-3-amide
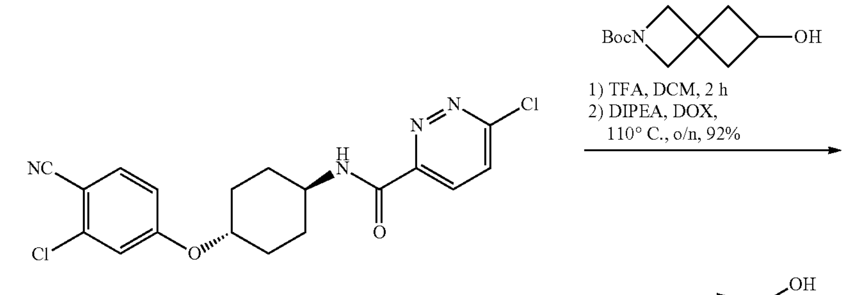
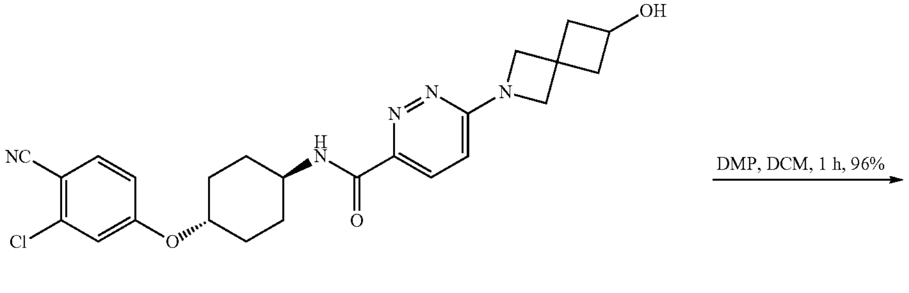

-continued

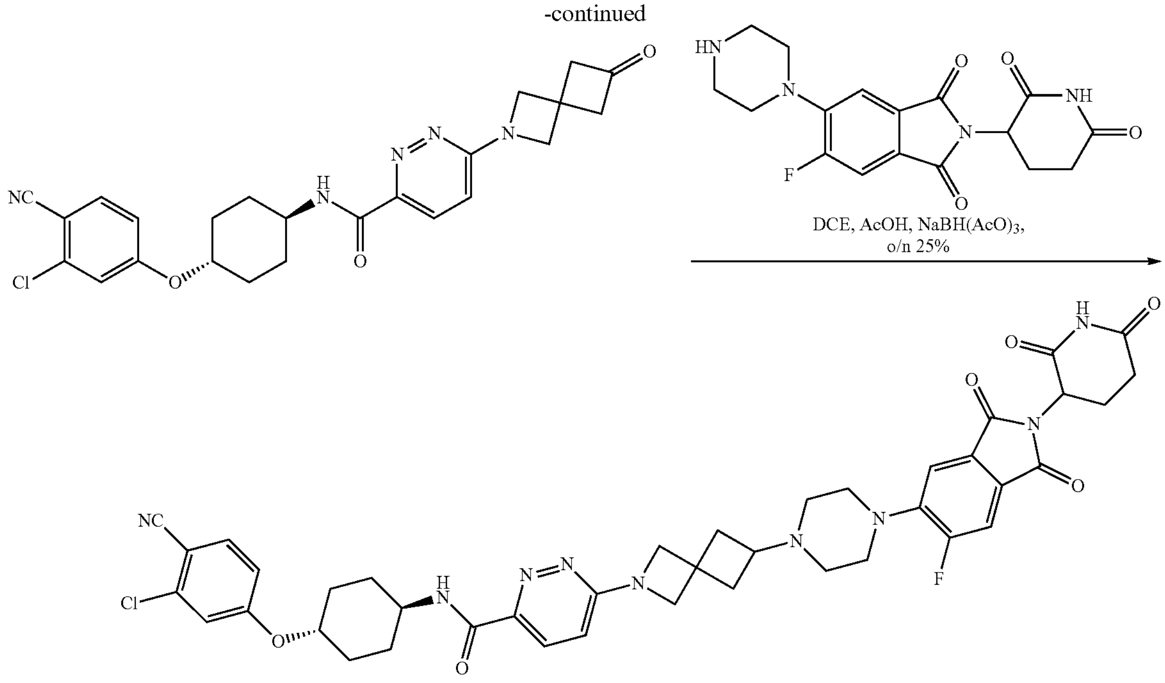

129

1. N-((1r,4r)-4-(3-chloro-4-cyanophenoxy)cyclohexyl)-6-(6-hydroxy-2-azaspiro[3.3]heptan-2-yl)pyridazine-3-amide Compound t-butyl 6-hydroxy-2-azaspiro[3.3]heptan-2-carboxylate (300 mg, 1.40 mmol) and 30 mL of trifluoroacetic acid were dissolved in 15 mL of dichloromethane. After the reaction solution was stirred at room temperature for 2 h, TLC indicated that the reaction was completed, and then the reaction solution was concentrated, to which were added 6-chloro-N-(((1r,4r)-4-(3-chloro-4-cyanophenoxy)cyclohexyl)pyridazine-3-carboxamide (200 mg, 0.51 mmol) and DIPEA (330 mg, 2.55 mmol). The mixture was dissolved in 5 mL DOX, and the solution was heated to 110° C. and stirred overnight. The reaction solution was cooled to room temperature, to which were added water and ethyl acetate for extraction. The organic layer was washed three times with the saturated solution of ammonium chloride and saturated brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(6-hydroxy-2-azaspiro[3.3]heptan-2-yl) pyridazine-3-amide as a white solid (220 mg, 0.47 mmol), with a yield of 92%. LC/MS ($ESI^+$) calcd for $C_{23}H_{35}N_2O_5^+$ $[M+H]^+$ m/z, 468.2; found 468.2.

2. N-(1r,4r)-4-(3-chloro-4-cyanophenoxy)cyclohexyl)-6-(6-oxo-2-azaspiro[3.3]heptan-2-yl)pyridazine-3-amide Compound N-((1r,4r)-4-(3-chloro-4-cyanophenoxy)cyclohexyl)-6-(6-hydroxy-2-azaspiro[3.3]heptan-2-yl) pyridazine-3-amide (220 mg, 0.41 mmol) and Dess-Martin periodinane (225 mg, 0.53 mmol) were dissolved in 4 mL of dichloromethane. The solution was stirred at room temperature for 1 h, and TLC indicated the completion of the reaction. The reaction solution was filtered, and the filtrate was successively washed twice with the saturated solution of sodium bisulfite, once with the saturated solution of sodium carbonate, once with saturated brine, dried over anhydrous sodium sulfate, filtered, and concentrated, to provide N-(1r,4r)-4-(3-chloro-4-cyanophenoxy)cyclohexyl)-6-(6-oxo-2-azaspiro[3.3]heptan-2-yl)pyridazine-3-amide (210 mg, 0.45 mmol), with a yield of 96%.

LC/MS ($ESI^+$) calcd for $C_{22}H_{33}N_2O_5^+$ $[M+H]^+$ m/z, 466.2; found 466.2.

3. Synthesis of Compound N-((1r,4r)-4-(3-chloro-4-cyanophenoxy)cyclohexyl)-6-(6-(4-(2-(2,6-dioxopiperidin-3-yl)-6-fluoro-1,3-dioxoisoindolin-5-yl)piperazin-1-yl)-2-azaspiro[3.3]heptan-2-yl)pyridazine-3-amide Compounds N-(1r,4r)-4-(3-chloro-4-cyanophenoxy)cyclohexyl)-6-(6-oxo-2-azaspiro[3.3]heptan-2-yl)pyridazine-3-amide (50 mg, 0.11 mmol) and 2-(2,6-dioxapiperidin-3-yl)-5-fluoro-6-(piperazin-1-yl)isoindoline-1,3-dione (40 mg, 0.11 mmol) were dissolved in 1 mL of 1,2-dichloroethane, to which was added two drops of glacial acetic acid. The mixture was stirred at room temperature for half an hour, to which was then added sodium triacetoxyborohydride (23 mg, 0.11 mmol). The mixture was continually stirred overnight at room temperature. After the reaction solution was concentrated, water was added, and the resultant solution was extracted with dichloromethane. The organic layer was washed with the saturated solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(6-(4-(2-(2,6-dioxopiperidin-3-yl)-6-fluoro-1,3-dioxoisoindolin-5-yl)piperazin-1-yl)-2-azaspiro[3.3]heptan-2-yl)pyridazine-3-amide as a yellow solid (22 mg, 0.027 mmol), with a yield of 25%. LC/MS (ESI+) calcd for $C_{41}H_{41}ClN_9O_6^+$ $[M+H]^+$ m/z, 810.3; found 810.3. $^1H$ NMR (400 MHz, DMSO-$d_6$) δ 11.13 (s, 1H), 8.56 (d, J=4.0 Hz, 1H), 7.86 (d, J=4.4 Hz, 1H), 7.82 (d, J=4.8 Hz, 1H), 7.74 (d, J=6.0 Hz, 1H), 7.46 (d, J=3.6 Hz, 1H), 7.39 (d, J=1.2 Hz, 1H), 7.16-7.10 (m, 1H), 6.83 (d, J=4.8 Hz, 1H), 5.76 (s, 1H), 5.12 (dd, J=9.2, 4.0 Hz, 1H), 4.58-4.49 (m, 1H), 4.18 (s, 1H), 4.06 (s, 1H), 3.89-3.81 (m, 1H), 3.29-3.21 (m, 4H), 2.93-2.84 (m, 1H), 2.47-2.37 (m, 5H), 2.14-2.06 (m, 4H), 1.93-1.86 (m, 2H), 1.67-1.60 (m, 2H), 1.56-1.47 (m, 3H), 1.28-1.20 (m, 3H), 0.89-0.78 (m, 1H).
130: Synthesis of N-((1r,4r)-4-(3-chloro-4-cyano-phenoxy)cyclohexyl)-6-(6-(4-(2-(2,6-dioxopiperidin-3-yl)-6-fluoro-1,3-dioxoisoindolin-5-yl)piperazin-1-yl)-2-azaspiro[3.3]heptan-2-yl)pyrazine-2-amide
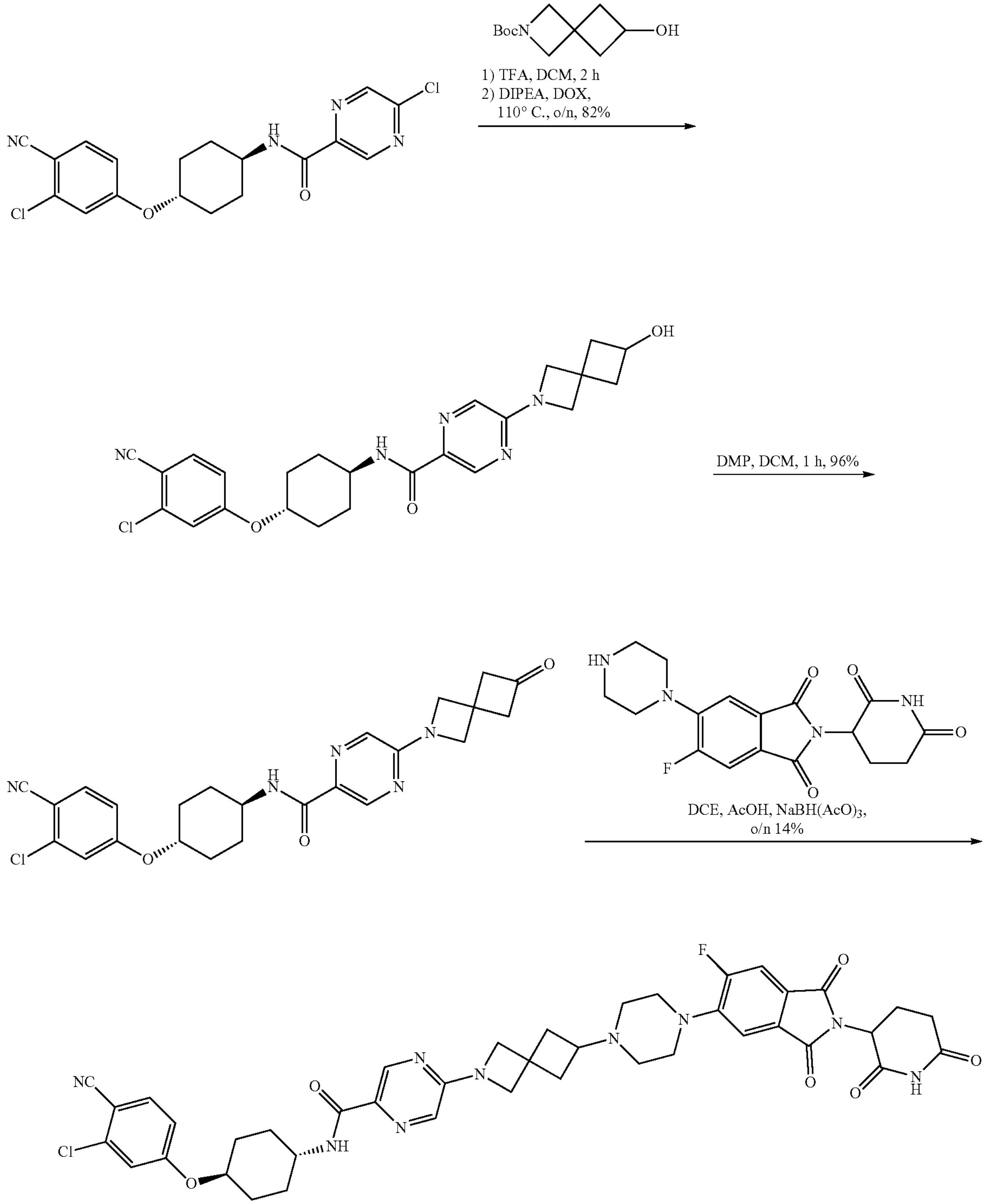

LC/MS (ESI+) calcd for $C_{41}H_{41}ClN_9O_6^+$ [M+H]+ m/z, 810.3; found 810.3.
$^1$H NMR (400 MHz, DMSO-$d_6$) δ 11.12 (s, 1H), 8.57 (s, 1H), 8.13 (d, J=4.0 Hz, 1H), 7.86 (d, J=4.0 Hz, 1H), 7.77-7.72 (m, 2H), 7.46 (d, J=4.4 Hz, 1H), 7.38 (d, J=1.2 Hz, 1H), 7.13 (dd, J=5.6, 3.2 Hz, 2H), 5.15-5.08 (m, 2H), 4.55-4.47 (m, 1H), 4.21-4.16 (m, 2H), 4.09-4.06 (m, 2H), 4.05-4.00 (m, 1H), 3.86-3.77 (m, 1H), 3.49-3.40 (m, 1H), 3.27-3.22 (m, 4H), 2.94-2.83 (m, 2H), 2.76-2.66 (m, 2H), 2.64-2.60 (m, 1H), 2.59-2.56 (m, 1H), 2.47-2.40 (m, 4H), 2.13-2.03 (m, 2H), 1.89-1.83 (m, 2H), 1.62-1.49 (m, 2H).
131: Synthesis of N-((1r,4r)-4-(4-cyanophenoxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide
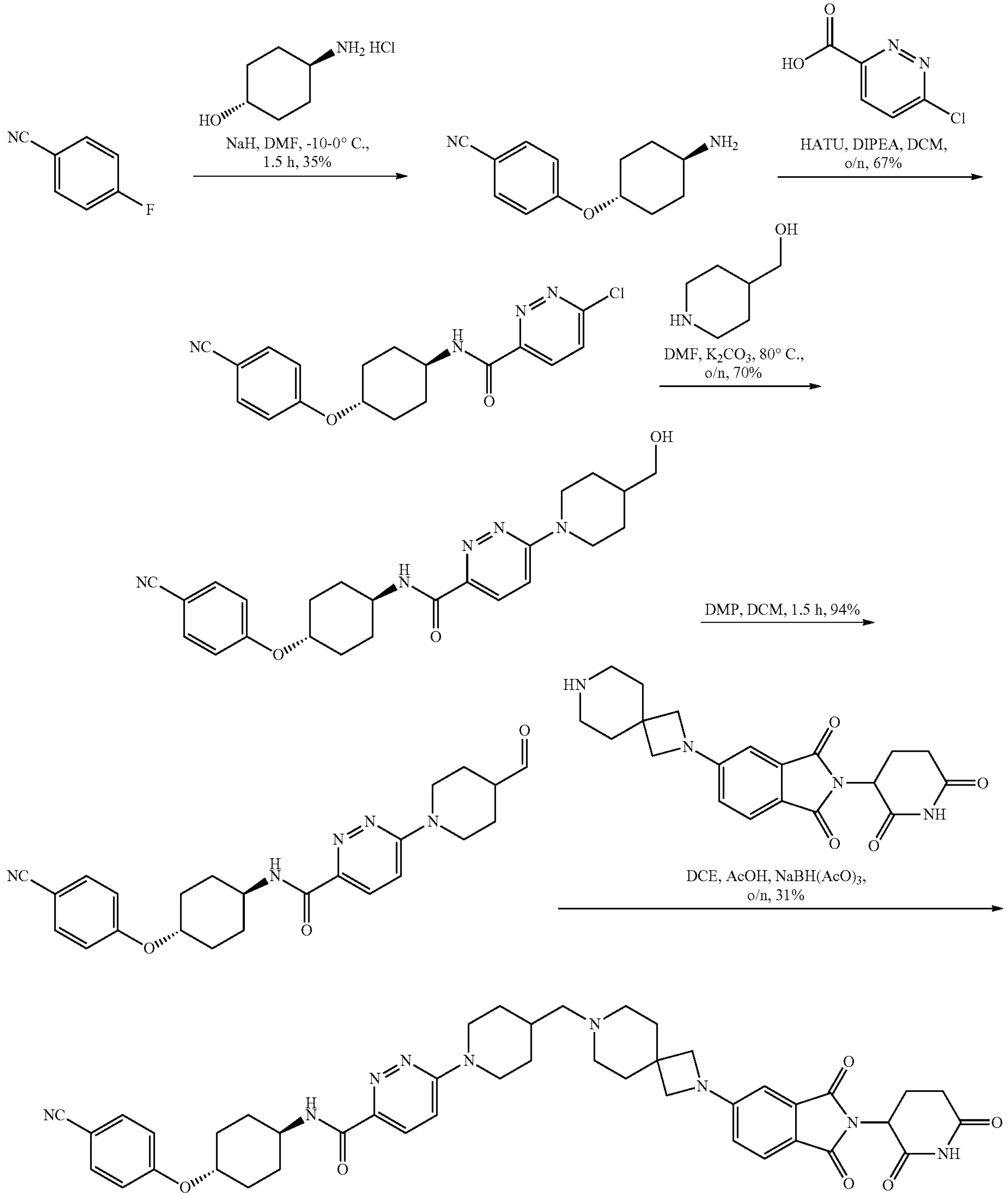

LC/MS (ESI$^+$) calcd for $C_{41}H_{41}ClN_9O_6^+$ [M+H]$^+$ m/z, 800.4; found 800.3.

$^1$H NMR (400 MHz, DMSO-$d_6$) δ 11.08 (s, 1H), 8.59 (d, J=4.4 Hz, 1H), 7.84 (d, J=4.8 Hz, 1H), 7.84 (d, J=4.4 Hz, 2H), 7.64 (d, J=4.4 Hz, 1H), 7.33 (d, J=4.8 Hz, 1H), 7.13 (d, J=4.4 Hz, 2H), 6.78 (s, 1H), 6.65 (d, J=4.0 Hz, 1H), 5.05 (dd, J=9.2, 3.6 Hz, 1H), 4.49-4.45 (m, 3H), 3.85 (m, 1H), 3.75 (s, 4H), 3.35 (s, 5H), 3.17 (s, 1H), 3.00 (t, J=8.0 Hz, 1H), 2.91-2.85 (m, 1H), 2.36-2.36 (m, 3H) 2.16-2.10 (m, 4H), 2.00-1.99 (m, 1H), 1.77-1.77 (m, 5H), 1.65-1.62 (N, 2H), 1.55-1.46 (m, 2H), 1.23-1.23 (m, 3H), 1.14-1.03 (m, 3H).

132: Synthesis of N-((1r,4r)-4-(4-cyanophenoxy)cyclohexyl)-6-(4-((2-(2-(2,6-dioxapiperidin-3-yl)-6-fluoro-1,3-dioxoisoindolin-5-yl)-2,7-diazaspiro[3.5]nonan-7-yl)methyl)piperidin-1-yl)pyridazine-3-carboxamide

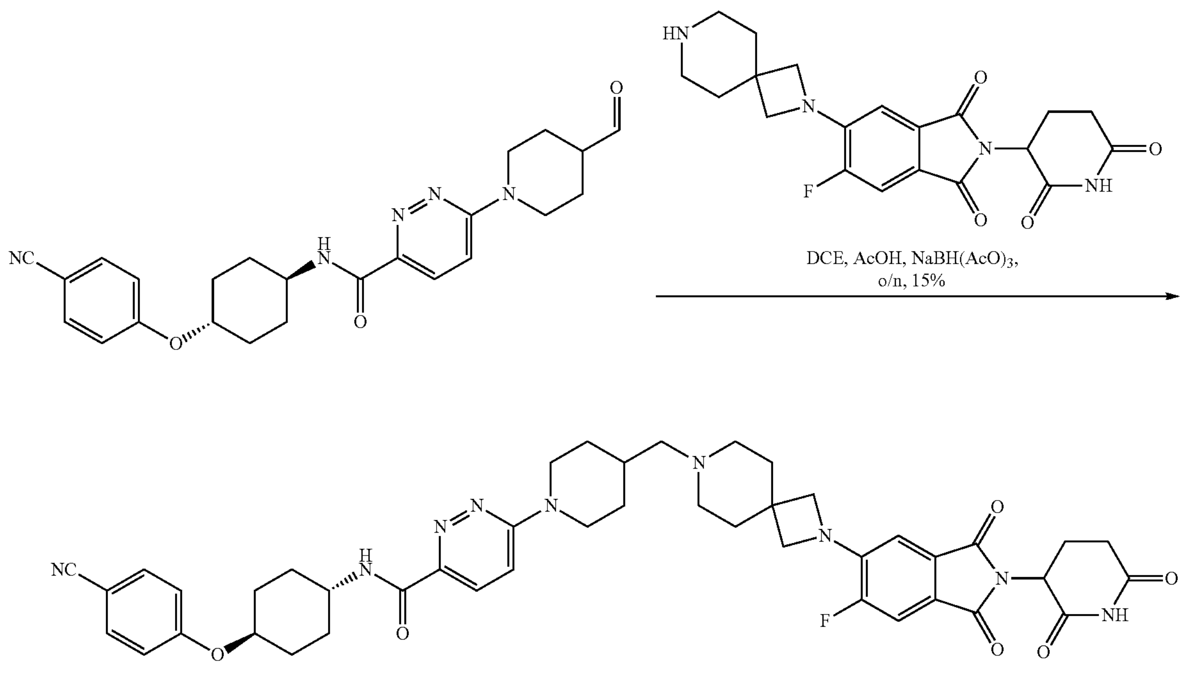

132

LC/MS (ESI$^+$) calcd for $C_{41}H_{41}ClNO_6^+$ [M+H]$^+$ m/z, 818.4; found 818.3.

$^1$H NMR (400 MHz, DMSO-$d_6$) δ 11.09 (s, 1H), 8.58 (d, J=4.4 Hz, 1H), 7.80 (d, J=4.8 Hz, 1H), 7.74 (d, J=4.4 Hz, 2H), 7.60 (d, J=6.0 Hz, 1H), 7.33 (d, J=4.8 Hz, 1H), 7.13 (d, J=4.4 Hz, 2H), 6.89 (d, J=2.4 Hz, 1H), 5.06 (dd, J=9.2, 4.0 Hz, 1H), 4.51-4.46 (m, 3H), 3.87 (m, 1H), 3.76 (s, 4H), 3.38 (s, 5H), 3.16 (s, 1H), 3.02 (t, J=8.0 Hz, 1H), 2.93-2.86 (m, 1H), 2.38-2.35 (m, 3H), 2.15-2.08 (m, 4H), 2.03-1.99 (m, 1H), 1.77-1.77 (m, 5H), 1.66-1.61 (m, 2H), 1.57-1.49 (m, 2H), 1.25-1.25 (m, 3H), 1.16-1.03 (m, 3H).

133: Synthesis of N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)-N-deuteromethylpyridazine-3-amide

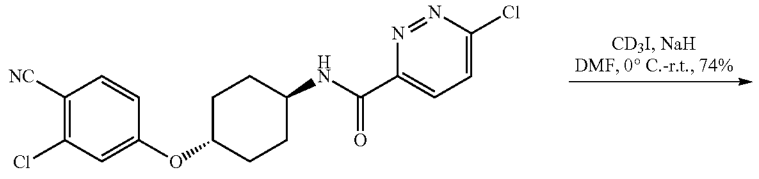

-continued

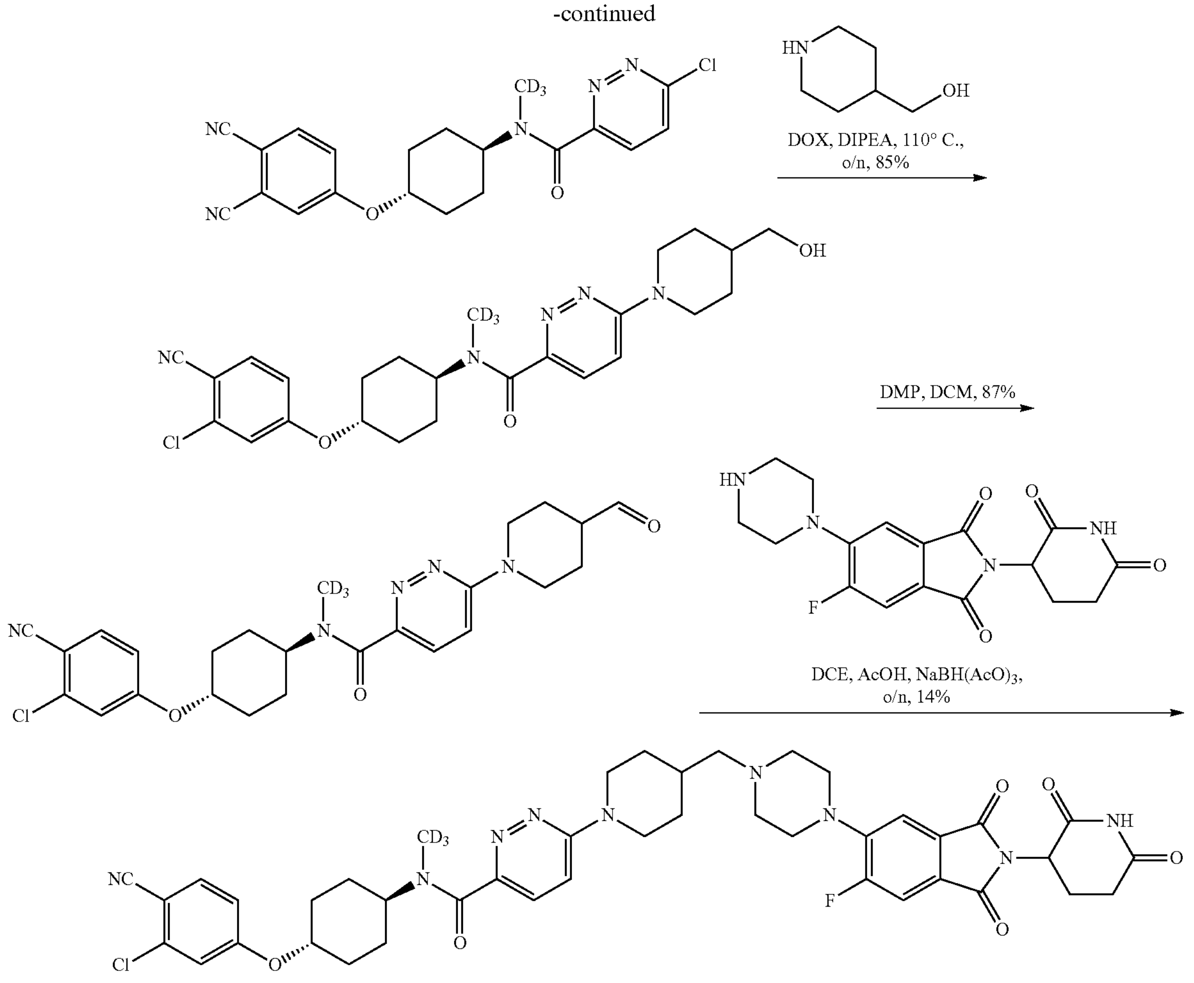

133

1. Synthesis of Compound 6-chloro-N-(((1r,4r)-4-(3,4-(dicyanophenoxy)cyclohexyl)-N-deuteromethylpyridazine-3-amide Compound sodium hydride (60%, 27 mg, 0.68 mmol) was dissolved in 2 mL DMF, and then stirred at −10° C. to 0° C. for 10 min, to which was added 6-chloro-N-(((1r,4r)-4-(3-chloro-4-cyanophenoxy)cyclohexyl)pyridazine-3-carboxamide (200 mg, 0.51 mmol). After the reaction solution was stirred for 30 min at −10° C. to 0° C., 2-chloro-4-fluorobenzonitrile (103 mg, 0.71 mmol) was slowly added, and the resultant solution was stirred at −10° C. to 0° C. for 1 h. The reaction solution was naturally warmed to room temperature, and then stirred for additional 2 h. The reaction solution was added with water and ethyl acetate for extraction. The organic layer was washed three times with the saturated solution of ammonium chloride and saturated brine, dried over anhydrous sodium sulfate, rotatory evaporated to dry, and purified by silica gel column chromatography, to provide yellow oily compound 6-chloro-N-(((1r,4r)-4-(3,4-(dicyanophenoxy)cyclohexyl)-N-deuteromethylpyridazine-3-amide (210 mg, 0.53 mmol), with a yield of 75%.

LC/MS (ESI$^+$) calcd for $C_{23}H_{35}N_2O_5^+$ [M+H]$^+$ m/z, 399.2; found 399.2.

2. Synthesis of Compound N-((1r,4r)-4-(3-chloro-4-cyanophenoxy)cyclohexyl)-6-(4-hydroxymethylpiperidin-1-yl)-N-deuteromethylpyridazine-3-carboxamide Compound 6-chloro-N-(((1r,4r)-4-(3,4-(dicyanophenoxy)cyclohexyl)-N-deuteromethylpyridazine-3-amide (210 mg, 0.53 mmol), piperidin-4-ylmethanol (92 mg, 0.80 mmol), and DIPEA (205 mg, 1.59 mmol) were dissolved in 5 mL of DOX. The reaction solution was heated to 110° C. and stirred overnight. The reaction solution was cooled to room temperature, to which was added water, and then extracted with ethyl acetate. The organic layer was washed three times with the saturated solution of ammonium chloride and saturated brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(4-hydroxymethylpiperidin-1-yl)-N-deuteromethylpyridazine-3-amide as a white solid (220 mg, 0.45 mmol), with a yield of 85%.

LC/MS (ESI$^+$) calcd for $C_{22}H_{33}N_2O_5^+$ [M+H]$^+$ m/z, 487.2; found 487.2.

3. Synthesis of Compound N-((1r,4r)-4-(3-chloro-4-cyanophenoxy)cyclohexyl)-6-(4-((4-(2-(2,6-dioxopiperidin-3-yl)-6-fluoro-1,3-dioxoisoindol-5-yl)piperazin-1-yl)methyl)piperidin-1-yl)-N-deuteromethyl-pyridazine-3-amide Compound N-((1r,4r)-4-(3-chloro-4-cyanophenoxy)cyclohexyl)-6-(4-hydroxymethylpiperidin-1-yl)-N-deuteromethylpyridazine-3-amide (220 mg, 0.45 mmol) and Dess-Martin periodinane (246 mg, 0.58 mmol) were dissolved in 4 mL of dichloromethane. The solution was stirred at room temperature for 1 h, and TLC indicated the completion of the reaction. The reaction solution was filtered, and the filtrate was successively washed twice with the saturated solution of sodium bisulfite, once with the saturated solution of sodium carbonate, once with saturated brine, dried over anhydrous sodium sulfate, filtered, and concentrated, to provide N-((1r,4r)-4-(3-chloro-4-cyanophenoxy)cyclohexyl)-6-(4-((4-(2-(2,6-dioxopiperidin-3-yl)-6-fluoro-1,3-dioxoisoindol-5-yl)piperazin-1-yl)methyl)piperidin-1-yl)-N-deuteromethyl-pyridazine-3-amide (200 mg, 0.45 mmol), with a yield of 87%.

LC/MS ($ESI^+$) calcd for $C_{35}H_{46}ClN_4O_5^+$ $[M+H]^+$ m/z, 485.2; found 485.2.

4. Synthesis of Compound N-((1r, 4 r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl) methyl)piperidin-1-yl)-N-deuteromethyl-pyridazine-3-amide Compounds N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl) piperidin-1-yl)-N-deuteromethyl-pyridazine-3-amide (50 mg, 0.10 mmol) and 2-(2,6-dioxapiperidin-3-yl)-5-fluoro-6-(piperazin-1-yl)isoindoline-1,3-dione (36 mg, 0.10 mmol) were dissolved in 1 mL of 1,2-dichloroethane, to which was added two drops of glacial acetic acid. The mixture was stirred at room temperature for half an hour, to which was then added sodium triacetoxyborohydride (21 mg, 0.10 mmol). The mixture was continually stirred overnight at room temperature. After the reaction solution was concentrated, water was added, and the resultant solution was extracted with dichloromethane. The organic layer was washed with the saturated solution of ammonium chloride and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl) piperidin-1-yl)-N-deuteromethyl-pyridazine-3-amide as a yellow solid (12 mg, 0.014 mmol), with a yield of 14%. LC/MS ($ESI^+$) calcd for $C_{42}H_{42}D_3ClN_9O_6^+$ $[M+H]^+$ m/z, 829.3; found 829.3.

$^1H$ NMR (400 MHz, DMSO-$d_6$) δ 11.13 (s, 1H), 7.87 (t. J=8.8 Hz, 1H), 7.74 (d, J=6.0 Hz, 1H), 7.51 (d, J=4.8 Hz, 1H), 7.46 (d, J=3.6 Hz, 1H), 7.41-7.30 (m, 2H), 7.16-7.04 (m, 1H), 5.76 (s, 1H), 5.11 (dd, J=9.2, 4.0 Hz, 1H), 4.61-4.32 (m, 4H), 3.34 (s, 5H), 3.33-3.30 (m, 1H), 3.26 (s, 3H), 3.02-2.84 (m, 3H), 2.57-2.52 (m, 3H), 2.27-2.19 (m, 2H), 2.19-2.11 (m, 1H), 2.10-2.01 (m, 2H), 1.88-1.81 (m, 4H), 1.77-1.69 (m, 1H), 1.62-1.51 (m, 1H), 1.38-1.20 (m, 3H), 1.17-1.10 (m, 2H), 0.92-0.71 (m, 2H).

134: Synthesis of N-((1r,4r)-4-(3-chloro-4-cyanophenoxy)cyclohexyl)-6-(4-(2-(2-(2,6-dioxopiperidin-3-yl)-6-fluoro-1,3-dioxoisoindolin-5-yl)-2-azaspiro[3.3]heptan-6-yl)piperazin-1-yl)pyridazine-3-amide

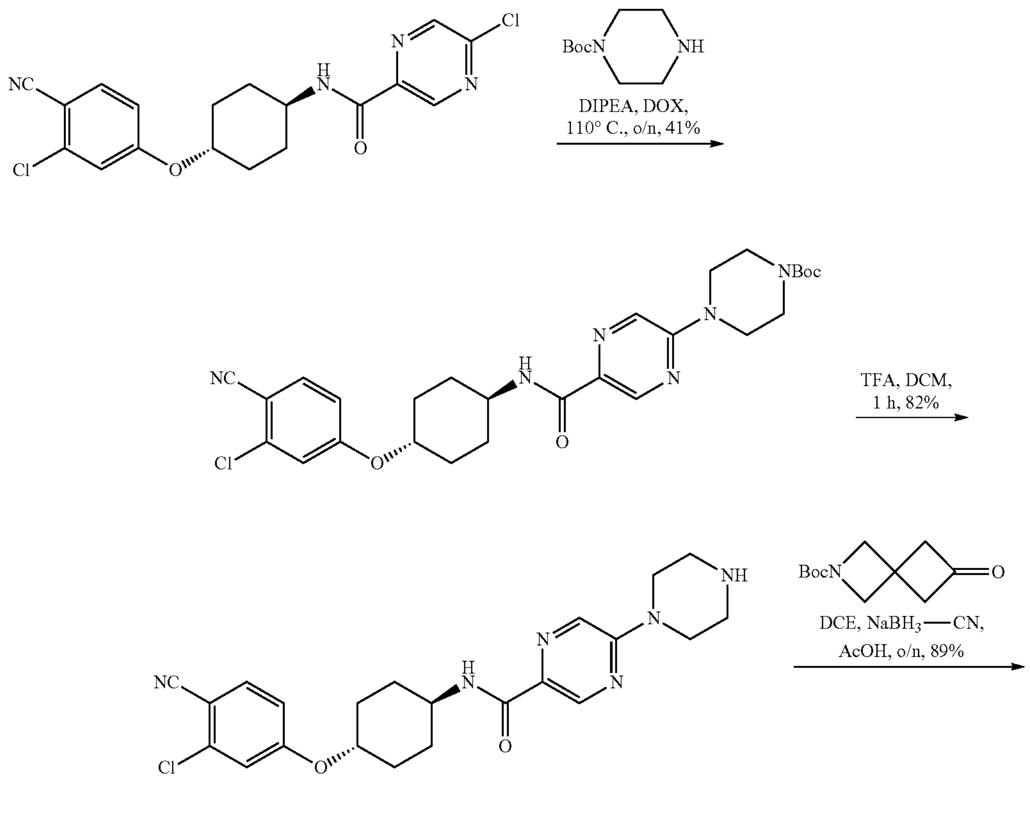

-continued

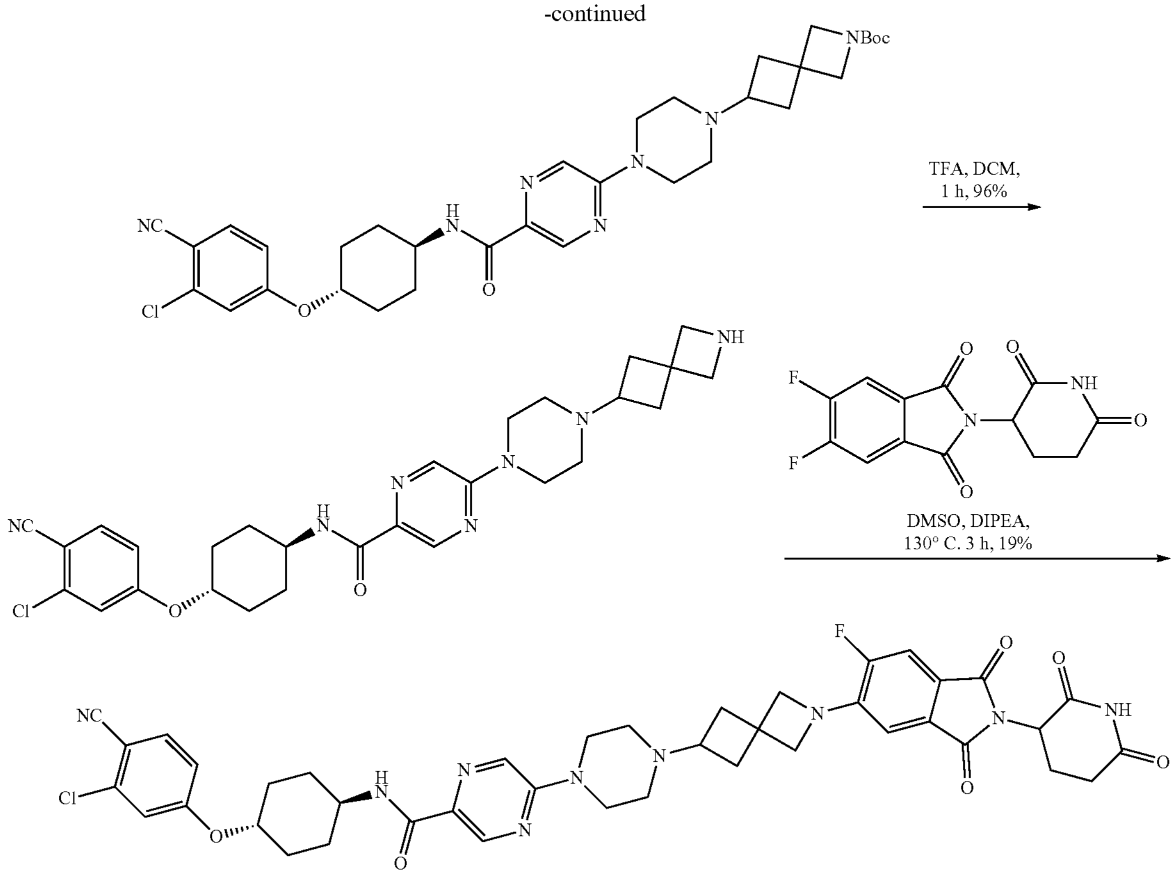

134

1. Synthesis of Compound t-butyl 4-(5-((((1r,4r)-4-(3-chloro-4-cyanophenoxy) cyclohexyl)carbamoyl) pyrazine-2-yl)piperazine-1-amide Compound t-butyl 5-chloro-N-(((1r,4r)-4-(3-chloro-4-cyanophenoxy)cyclohexyl) pyrazine-2-amide (200 mg, 0.51 mmol), piperazine-1-carboxylate (172 mg, 0.92 mmol) and DIPEA (178 mg, 1.38 mmol) were dissolved in 5 mL of DOX. The reaction solution was heated to 110° C. and stirred overnight. The reaction solution was added with water, and then extracted with ethyl acetate. The organic phase was washed three times with the saturated solution of ammonium chloride and saturated brine, dried over anhydrous sodium sulfate, rotatory evaporated to dry, and purified by silica gel column chromatography, to provide compound t-butyl 4-(5-((((1r,4r)-4-(3-chloro-4-cyanophenoxy) cyclohexyl)carbamoyl)pyrazine-2-yl)piperazine-1-amide (120 mg, 0.22 mmol), with a yield of 43%. LC/MS (ESI$^+$) calcd for $C_{23}H_{35}N_2O_5^+$ [M+H]$^+$ m/z, 419.2; found 419.2.

2. Synthesis of Compound N-((1r,4r)-4-(3-chloro-4-cyanophenoxy)cyclohexyl)-6-(piperazin-1-yl) pyridazine-3-amide Compound t-butyl 4-(5-((((1r,4r)-4-(3-chloro-4-cyanophenoxy)cyclohexyl)carbamoyl) pyrazine-2-yl)piperazine-1-amide (120 mg, 0.22 mmol) and 4 mL of trifluoroacetic acid were dissolved in 2 mL of dichloromethane. After the reaction solution was stirred at room temperature for 1 h, TLC indicated that the reaction was completed, and then the reaction solution was concentrated. After that, the saturated solution of sodium carbonate was added to adjust the pH of the reaction solution to 12, and then the solution was extracted with dichloromethane. The organic phase was washed twice with saturated brine, dried over anhydrous sodium sulfate, filtered, and concentrated, to provide N-((1r, 4r)-4-(3-chloro-4-cyanophenoxy)cyclohexyl)-6-(piperazin-1-yl) pyridazine-3-amide (80 mg, 0.18 mmol), with a yield of 82%.

LC/MS (ESI$^+$) calcd for $C_{23}H_{33}N_2O_5^+$ [M+H]$^+$ m/z, 441.2; found 441.2.

3. Synthesis of Compound t-butyl 6-(4-(5-((((1r,4r)-4-(3-chloro-4-cyanophenoxy)cyclohexyl)carbamoyl) pyrazine-2-yl)piperazin-1-yl)-2-azaspiro[3.3]heptan-2-carboxylate Compounds N-((1r,4r)-4-(3-chloro-4-cyanophenoxy)cyclohexyl)-6-(piperazin-1-yl)pyridazine-3-amide (80 mg, 0.18 mmol) and t-butyl 6-oxo-2-azaspiro[3.3]heptan-2-carboxylate (76 mg, 0.36 mmol) were dissolved in 1 mL of 1,2-dichloroethane, to which was added two drops of glacial acetic acid. The mixture was stirred at room temperature for half an hour, to which was then added sodium triacetoxyborohydride (57 mg, 0.27 mmol). The mixture was continually stirred overnight at room temperature. After the reaction solution was concentrated, water was added, and the resultant solution was extracted with dichloromethane. The organic layer was washed with the saturated solution of ammonium chloride and brine, dried over anhydrous sodium sulfate, rotatory evaporated to dry, and purified by silica gel column chromatography, to provide compound t-butyl 6-(4-(5-((((1r,4r)-4-(3-chloro-4-cyanophenoxy)cyclohexyl) carbamoyl)pyrazine-2-yl)piperazin-1-yl)-2-azaspiro[3.3]heptan-2-carboxylate (100 mg, 0.16 mmol), with a yield of 89%.

LC/MS (ESI$^+$) calcd for $C_{35}H_{46}ClN_4O_5^+$ [M+H]$^+$ m/z, 636.3; found 636.6.

4. Synthesis of Compound 6-(4-(6-((((1r,4r)-4-(3-chloro-4-cyanophenoxy)cyclohexyl)carbamoyl) pyridazine-3-ylpiperazin-1-yl)-2-azaspiro[3.3]heptan-2-carboxylate Compound t-butyl 6-(4-(5-((((1r,4r)-4-(3-chloro-4-cyanophenoxy)cyclohexyl) carbamoyl)pyrazine-2-yl)piperazin-1-yl)-2-azaspiro[3.3]heptan-2-carboxylate (50 mg, 0.080 mmol) and 2 mL of trifluoroacetic acid were dissolved in 1 mL of dichloromethane. After the reaction solution was stirred at room temperature for 1 h, TLC indicated that the reaction was completed, and then the reaction solution was concentrated, to provide 6-(4-(6-((((1r,4r)-4-(3-chloro-4-cyanophenoxy)cyclohexyl) carbamoyl)pyridazine-3-ylpiperazin-1-yl)-2-azaspiro[3.3]heptan-2-carboxylate trifluoroacetate (50 mg, 0.077 mmol), with a yield of 96%. LC/MS (ESI$^+$) calcd for $C_{30}H_{38}ClN_4O_3^+$ [M+H]$^+$ m/z, 536.2; found 536.2.

5. Synthesis of Compound N-((1r,4r)-4-(3-chloro-4-cyanophenoxy)cyclohexyl)-5-(4-(2-(2-(2,6-dioxopiperidin-3-yl)-6-fluoro-1,3-dioxoisoindolin-5-yl)-2-azaspiro[3.3]heptan-6-yl)piperazin-1-yl)pyrazine-2-amide Compounds 6-(4-(6-((((1r,4r)-4-(3-chloro-4-cyanophenoxy)cyclohexyl)carbamoyl) pyridazine-3-ylpiperazin-1-yl)-2-azaspiro[3.3]heptan-2-carboxylate trifluoroacetate (50 mg, 0.077 mmol), 2-(2,6-dioxapiperidin-3-yl)-5,6-difluoroisoindoline-1,3-dione (23 mg, 0.077 mmol) and DIPEA (50 mg, 0.39 mmol) were added in 1 mL of DMSO. The reaction solution was heated to 130° C. and stirred for 3 h. The reaction solution was cooled to room temperature, to which were added water and ethyl acetate for extraction. The organic layer was successively washed with 0.5 N HCl and brine, dried over anhydrous sodium sulfate, rotatory evaporated to dry, and purified by silica gel column chromatography, to provide compound N-((1r,4r)-4-(3-chloro-4-cyanophenoxy)cyclohexyl)-5-(4-(2-(2-(2,6-dioxopiperidin-3-yl)-6-fluoro-1,3-dioxoisoindolin-5-yl)-2-azaspiro[3.3] heptan-6-yl)piperazin-1-yl)pyrazine-2-amide (12 mg, 0.015 mmol), with a yield of 19%.

LC/MS (ESI$^+$) calcd for $C_{41}H_{41}ClFN_9O_6^+$ [M+H]$^+$ m/z, 810.3; found 809.7.

$^1$H NMR (400 MHz, DMSO-$d_6$) δ 11.09 (s, 1H), 8.76 (s, 2H), 8.14 (d, J=3.6 Hz, 1H), 7.86 (d, J=4.4 Hz, 1H), 7.59 (d, J=5.6 Hz, 1H), 7.39 (d, J=1.2 Hz, 1H), 7.14 (dd, J=5.6, 1.2 Hz, 1H), 6.88 (d, J=4.0 Hz, 1H), 5.06 (dd, J=9.2, 3.6 Hz, 1H), 4.60-4.50 (m, 1H), 4.20 (s, 2H), 4.09 (s, 2H), 3.87-3.73 (m, 5H), 2.94-2.81 (m, 1H), 2.69-2.58 (m, 2H), 2.58-2.53 (m, 1H), 2.38-2.25 (m, 6H), 2.13-1.96 (m, 6H), 1.94-1.88 (m, 2H), 1.54-1.45 (m, 4H).

135: N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl) methyl)piperidin-1-yl)pyrimidine-2-carboxamide

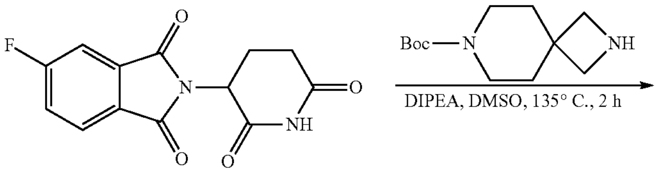

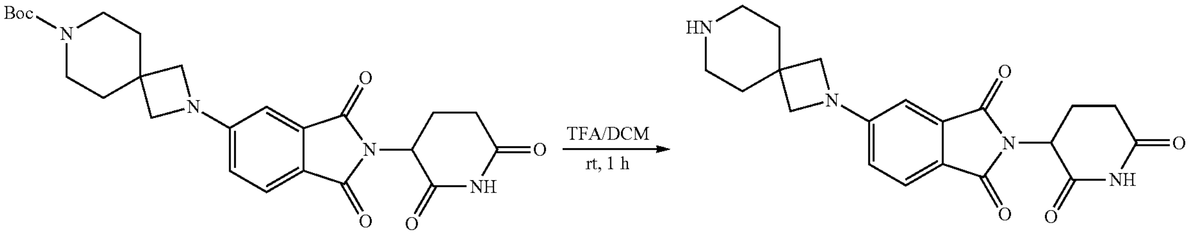

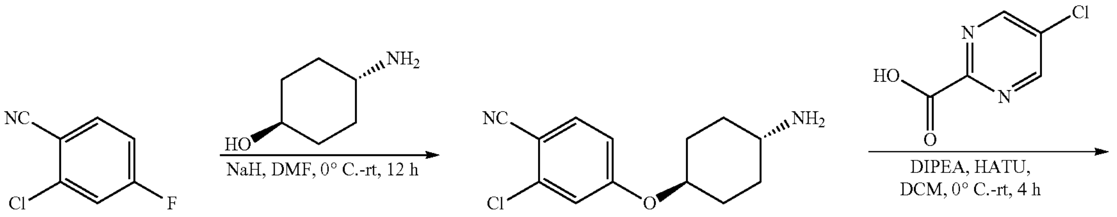

-continued

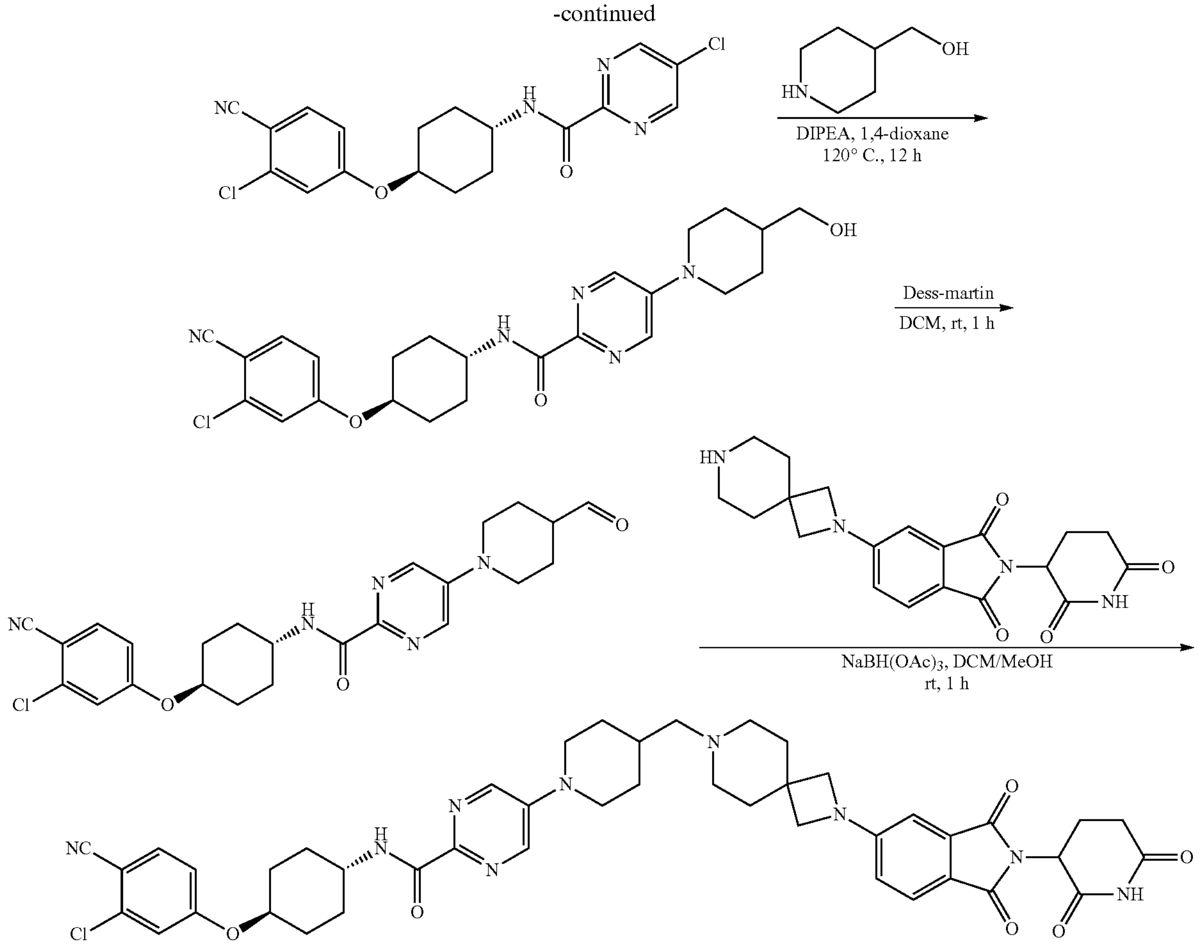

135

Step 1: 2-(2,6-dioxopiperidin-3-yl)-5-fluoroisoindoline-1,3-dione (553 mg, 2.0 mmol), t-butyl 2,7-diazaspiro[3.5]nonane-7-carboxylic acid (453 mg, 2.0 mmol) and diisopropylethylamine (1.3 g, 10.0 mmol) were added in 10 mL of DMSO. The reaction solution was heated to 135° C. and allowed to react overnight under stirring. The reaction solution was cooled to room temperature, to which were added ethyl acetate and water for extraction. The organic phase was washed with saturated brine and dried over anhydrous sodium sulfate. The solvent was removed by rotatory evaporation, to provide the crude product, which was purified by TLC, to obtain compound t-butyl 2-(2-(2,6-dioxopiperidin-3-yl)-1,3-dioxoisoindolin-5-yl)-2,7-diazaspiro[3.5]nonane-7-carboxylate (530 mg), with a yield of 55%. LC/MS (ESI+) calcd for $C_{25}H_{30}N_4O_6$ ([M+H]+) m/z 482.22; found 483.1.

Step 2: Compound t-butyl 2-(2-(2,6-dioxopiperidin-3-yl)-1,3-dioxoisoindolin-5-yl)-2,7-diazaspiro[3.5]nonane-7-carboxylate (530 mg, 1.09 mmol) was dissolved in 10 mL of dichloromethane, to which was added 4 mL of trifluoroacetic acid, and the mixture was allowed to stir at room temperature for 3 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound 2-(2,6-dioxopiperidin-3-yl)-5-(2,7-diazaspiro[3.5]nonan-2-yl)isoindole-1,3-dione (342 mg), with a yield of 82%. LC/MS (ESI+) calcd for $C_{20}H_{20}N_4O_4$ ([M+H]+) m/z 382.16; found 383.1.

Step 3: NaH (360 mg, 9.0 mmol) was added in 5 mL of DMF, and then the system was placed in an ice-water bath to cool down under stirring, to which was added (1r,4r)-4-aminocyclohexane-1-ol (455 mg, 3.0 mmol). The resultant solution was stirred for 10 min, to which was added 2-chloro-4-fluorobenzonitrile (460 mg, 3 mmol). The reaction was allowed to naturally warm and react overnight under stirring. TLC indicated the consumption of raw materials, to which were added ethyl acetate and water for extraction. The organic layer was washed with saturated brine, dried over anhydrous sodium sulfate, rotatory evaporated to dry, and separated and purified by Pre-TLC, to provide compound 4-((1r,4r)-4-aminocyclohexyl)oxy)-2-chlorobenzonitrile (279 mg), with a yield of 62%. LC/MS ($ESI^+$) calcd for $C_{13}H_{15}ClN_2O$ ($[M+H]^+$) m/z 250.73; found 251.1.

Step 4: compound 5-chloropyrimidine-2-carboxylic acid (79 mg, 0.50 mmol) and HATU (304 mg, 0.80 mmol) were added in 5 mL of dichloromethane, and then the system was placed in an ice-water bath to cool down under stirring. After 10 min, diisopropylethylamine (194 mg, 1.50 mmol) was added, followed by addition of 4-((1r,4r)-4-aminocyclohexyl)oxy)-2-chlorobenzonitrile (150 mg, 0.50 mmol). After that, the ice bath was removed, and the reaction was stirred overnight at room temperature. TLC indicated the consumption of raw materials, to which were added dichloromethane and water for extraction. The organic layer was washed with saturated brine, dried over anhydrous sodium sulfate, rotatory evaporated to dry, and separated and purified by Pre-TLC, to provide compound 5-chloro-N-((1r,4r)-4-(3-chloro-4-cyanophenoxy) cyclohexyl)pyrimidine-2-carboxamide (185 mg), with a yield of 92%. LC/MS ($ESI^+$) calcd for $C_{18}H_{16}Cl_2N_4O_2$ ($[M+H]^+$) m/z 391.25; found 391.1.

Step 5: 5-Chloro-N-((1 r,4r)-4-(3-chloro-4-cyanophenoxy)cyclohexyl)pyrimidine-2-carboxamide (185 mg, 0.46 mmol), piperidin-4-ylmethanol (260 mg, 0.92 mmol) and diisopropylethylamine (297 mg, 2.30 mmol) were added to 8 mL of dioxane, and then the system was heated to 115° C., stirred and reacted overnight under reflux. The reaction solution was cooled to room temperature, to which were added ethyl acetate and water for extraction. The organic phase was washed with 0.05 N HCl, and then washed with saturated brine, dried over anhydrous sodium sulfate. The solvent was removed by rotary evaporation to obtain the crude product, which was separated and purified by Pre-TLC, to provide compound N-((1r,4r)-4-(3-chloro-4-cyanophenoxy)cyclohexyl)-5-(4-(hydroxymethyl)piperidin-1-yl) pyrimidine-2-carboxamide (109 mg), with a yield of 37%. LC/MS ($ESI^+$) calcd for $C_{24}H_{28}ClN_5O_3$ ($[M+H]^+$) m/z 469.97; found 470.1.

Step 6: N-((1r,4r)-4-(3-chloro-4-cyanophenoxy)cyclohexyl)-5-(4-(hydroxymethyl) piperidin-1-yl)pyrimidine-2-carboxamide (50 mg, 0.11 mmol) was placed in a 25 mL single-neck round bottom flask, to which was added dichloromethane (5 mL), and the mixture was stirred to dissolve and make the solution become clear at room temperature. Then, the system was placed in an ice-water bath to cool down under stirring. When the internal temperature of the system dropped to about 0° C., Dess-Martin periodinane (72 mg, 0.17 mmol) was added to the system. After that, the system was allowed to naturally warm to room temperature and react under stirring. After 2 h, TLC showed that the raw materials had almost disappeared, and the reaction was stopped. The system was subjected to suction filtration through celite, and the filter cake was rinsed with dichloromethane several times in a small amount. The filtrate was combined, and the solvent was removed by rotary evaporation to obtain the crude product, which was then separated and purified by Pre-TLC to obtain compound N-((1r,4r)-4-(3-chloro-4-cyanophenoxy)cyclohexyl)-5-(4-formylpiperidin-1-yl)pyrimidine-2-carboxamide (30 mg), with a yield of 58%. LC/MS ($ESI^+$) calcd for $C_{24}H_{26}ClN_5O_3$ ($[M+H]^+$) m/z 467.95; found 468.1.

Step 7: N-((1r,4r)-4-(3-chloro-4-cyanophenoxy)cyclohexyl)-5-(4-formylpiperidin-1-yl)pyrimidine-2-carboxamide (30 mg, 0.06 mmol) was weighed and added into a 25 mL single-neck round bottom flask, to which was added dichloromethane (3 mL), and the mixture was stirred at room temperature to dissolve and make the solution become clear. Then, 2-(2,6-dioxopiperidin-3-yl)-5-(2,7-diazaspiro[3.5]nonan-2-yl)isoindole-1,3-dione (24 mg, 0.06 mmol) was added to the system, and the reaction solution was stirred and reacted at room temperature for 15 min. Subsequently, sodium triacetylborohydride (38 mg, 0.18 mmol) was added to the system, and the system was allowed to react at room temperature under stirring. After 4 h, the sample was taken out and subjected to TLC, and the result indicated the complete consumption of raw materials. The stirring was stopped, and then dichloromethane (15 mL) and water (15 mL) were added to the system. The system was stirred vigorously, and then allowed to stand for separation of layers. The aqueous layer was extracted with dichloromethane (10 mL*3). The organic phase was combined, successively washed with water (10 mL*2) and saturated brine (15 mL), and dried over anhydrous sodium sulfate. The solvent was removed by rotary evaporation to obtain the crude product, which was then separated and purified by Pre-TLC to obtain compound N-((1r,4r)-4-(3-chloro-4-cyanophenoxy)cyclohexyl)-6-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl)pyridazine-3-formamide (21 mg), with a yield of 39%. $^1H$ NMR (400 MHz, DMSO-$d_6$) δ 8.51 (s, 2H), 8.33 (d, J=8.1 Hz, 1H), 7.86 (d, J=8.7 Hz, 1H), 7.63 (d, J=8.1 Hz, 1H), 7.38 (s, 1H), 7.13 (d, J=8.4 Hz, 1H), 6.78 (s, 1H), 6.65 (d, J=8.2 Hz, 1H), 5.05 (dd, J=12.8, 5.3 Hz, 1H), 4.53 (s, 1H), 3.97 (d, J=11.3 Hz, 3H), 2.87 (t, J=11.9 Hz, 3H), 2.60 (s, 2H), 2.32 (s, 4H), 2.12 (s, 4H), 1.99 (d, J=5.1 Hz, 1H), 1.88 (s, 2H), 1.79 (s, 2H), 1.67-1.42 (m, 6H), 1.23 (s, 4H), 1.16 (d, J=10.9 Hz, 3H), 0.84 (d, J=7.3 Hz, 2H). LC/MS ($ESI^+$) calcd for $C_{44}H_{18}ClN_9O_6$ ($[M+H]^+$) m/z 834.38; found 834.3.

136: N-((1r,4r)-4-((6-cyano-5-(trifluoromethyl)pyridin-3-yl)oxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridazine-3-formamide

136

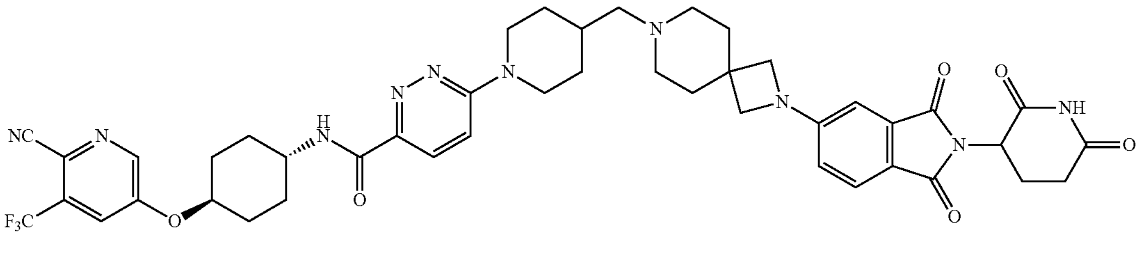

LC/MS (ESI$^+$) for $C_{44}H_{48}F_3N_{10}O_6$ ([M+H]$^+$) m/z 869.

137: N-((1r,4r)-4-(3-chloro-4-cyanophenoxy)cyclohexyl)-6-(3-((5-(2,6-dioxopiperidin-3-yl)-6-fluoro-1,3-dioxoisoindolin-5-yl)hexahydropyrrolo[3,4-c]pyrrol-2(1H)-yl)methyl)azitidin-1-yl)pyridazine-3-formamide

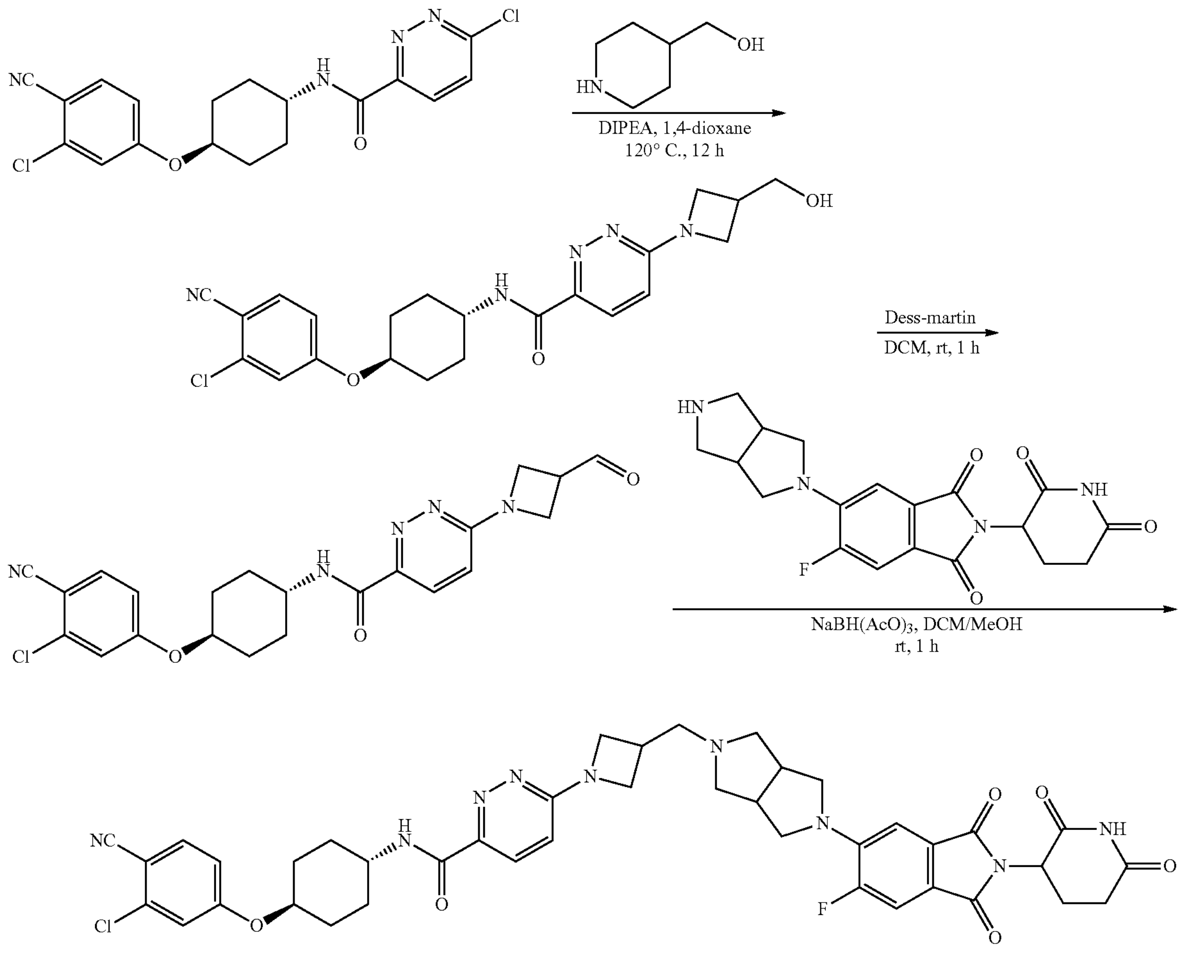

137

$^1$H NMR (400 MHz, DMSO-$d_6$) β 11.10 (s, 1H), 8.53 (d, J=8.1 Hz, 1H), 7.85 (d, J=8.8 Hz, 1H), 7.79 (d, J=9.2 Hz, H), 7.66-7.61 (m, 1H), 7.38 (d, J=2.4 Hz, DH7.17-7.11 (m, 2H), 6.83 (d, J=9.3 Hz, H), 5.08 (dd, J=12.9, 5.4 Hz, 1H), 4.53 (s, 1H), 4.20 (t, J=8.3 Hz, 2H), 4.10 (s, 3H), 3.85 (s, 1H), 3.78 (dd, J=8.4, 5.5 Hz, 2H), 3.70 (s, 2H), 2.87 (d, J=13.9 Hz, 3H), 2.70 (d, J=7.4 Hz, 2H), 2.67-2.59 (m, 2H), 2.09 (d, J=11.3 Hz, 2H), 2.05-1.99 (m, 1H), 1.89 (s, 3H), 1.70-1.56 (m, 2H), 1.52 (t, J=11.2 Hz, 2H), 1.23 (s, 2H). LC/MS (ESI$^+$) calcd for $C_{41}H_{41}ClFN_9O_6$ ([M+H]$^+$) m/z 810.28; found 810.3.

138: N-((1r,4r)-4-(3-chloro-4-cyanophenoxy)cyclohexyl)-5(3-((5-(2,6-dioxopiperidin-3-yl)-6-fluoro-1,3)-dioxoisoindolin-5-yl)hexahydropyrrolo[3,4-c]pyrrol-2(1H)-yl)methyl)azitidin-1-yl)pyrazine-2-carboxamide

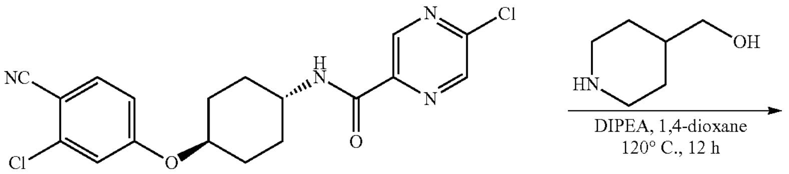

-continued
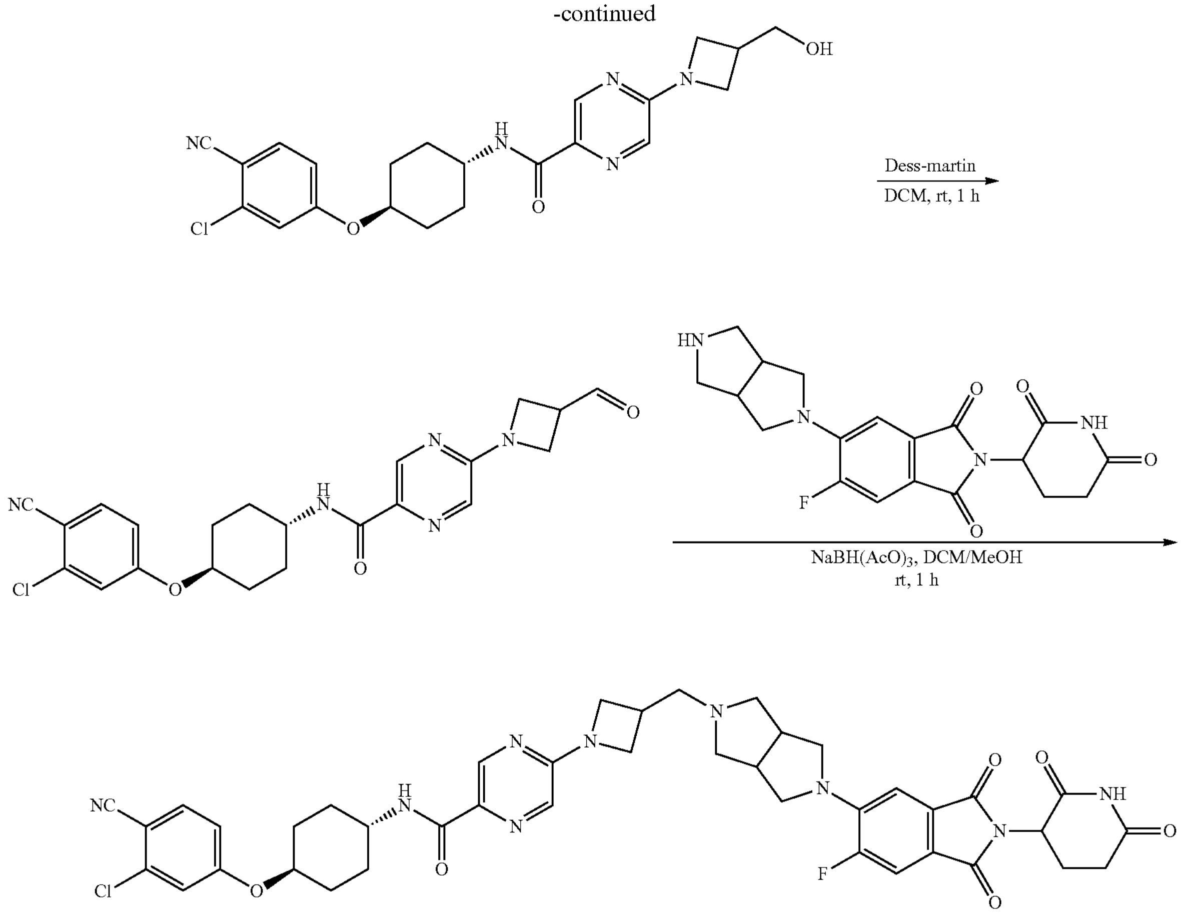
138
$^1$H NMR (400 MHz, DMSO-$d_6$) δ 11.10 (s, 1H), 8.55 (d, J=1.3 Hz, 1H), 8.10 (d, J=8.3 Hz, 1H), 7.86 (d, J=8.8 Hz, 1H), 7.77 (d, J=1.3 Hz, 1H), 7.64 (d, J=12.5 Hz, 1H), 7.37 (d, J=2.4 Hz, 1H), 7.17-7.09 (m, 2H), 5.76 (s, 2H), 5.08 (dd, J=12.9, 5.3 Hz, 1H), 4.50 (s, 1H), 4.20 (t, J=8.5 Hz, 2H), 3.80 (dd, J=8.8, 5.5 Hz, 3H), 3.70 (s, 2H), 2.87 (d, J=13.5 Hz, 3H), 2.70 (d, J=7.3 Hz, 2H), 2.67-2.58 (m, 3H), 2.55 (d, J=10.3 Hz, 2H), 2.08 (s, 3H), 1.85 (s, 2H), 1.56 (dt, J=27.5, 11.6 Hz, 4H), 1.23 (s, 2H), 1.05 (t, 0.1=7.0 Hz, 1H). LC/MS ($ESI^+$) calcd for $C_{41}H_{41}ClFN_9O_6$ ($[M+H]^+$) m/z 810.28; found 810.2.
139: N-((1r,4r)-4-(3-chloro-4-cyanophenoxy)cyclohexyl)-6-(4-((2-(2,6-dioxopiperidin-3-yl)-6-fluoro-1,3-dioxoisoindolin-5-yl)amino)piperidin-1-yl)methyl)piperidin-1-yl)pyridazine-3-formamide
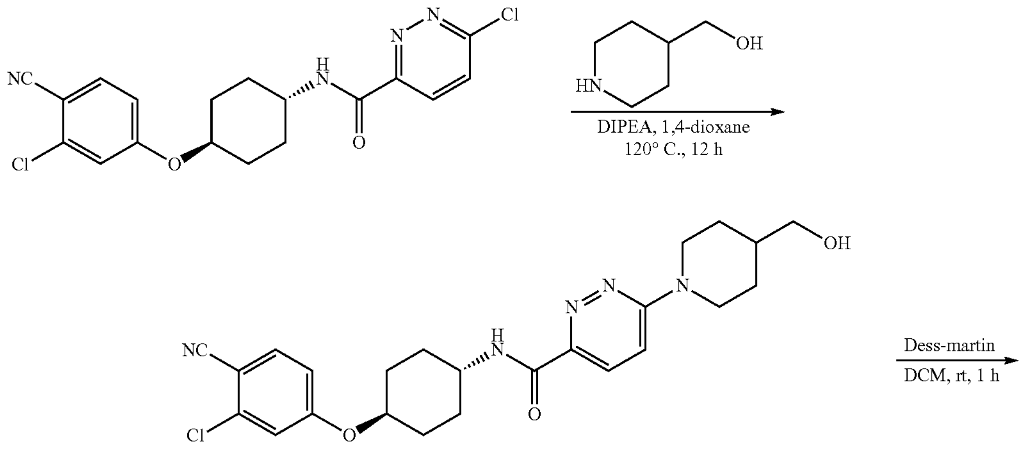

-continued

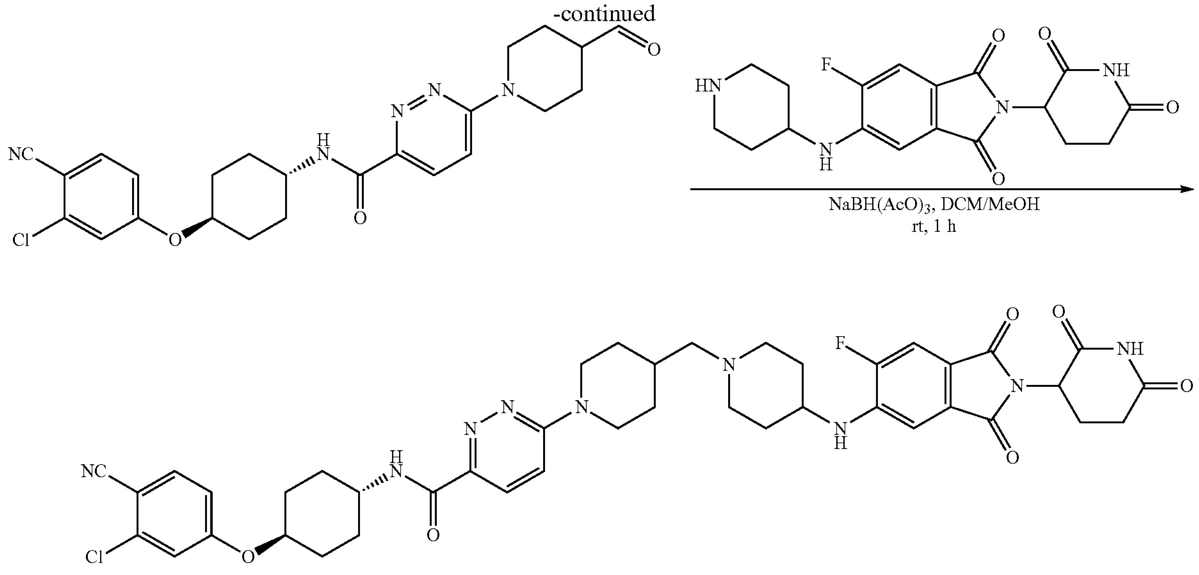

139

$^1$H NMR (400 MHz, DMSO-$d_6$) δ 11.06 (s, 1H), 8.56 (d, J=8.2 Hz, 1H), 7.85 (d, J=8.8 Hz, 1H), 7.80 (d, J=9.6 Hz, 1H), 7.57 (d, J=10.3 Hz, 1H), 7.38 (d, J=2.3 Hz, 1H), 7.32 (d, J=9.7 Hz, 1H), 7.18 (d, J=7.1 Hz, 1H), 7.13 (dd, J=8.7, 2.4 Hz, 1H), 6.58 (d, J=5.8 Hz, 1H), 5.05 (dd, J=12.8, 5.4 Hz, 1H), 4.54 (s, 1H), 4.47 (d, J=12.6 Hz, 2H), 3.87 (s, 1H), 3.54 (s, 1H), 3.40 (d, J=5.9 Hz, 1H), 3.01 (t. J=12.1 Hz, 2H), 2.85 (d, J=12.5 Hz, 3H), 2.60 (s, 1H), 2.55 (d, J=6.0 Hz, 2H), 2.17 (d, J=6.9 Hz, 2H), 2.08 (d, J=10.3 Hz, 2H), 1.94-1.77 (m, 7H), 1.67-1.58 (m, 3H), 1.58-1.48 (m, 3H), 1.24 (s, 1H), 1.11 (d, J=11.0 Hz, 2H). LC/MS ($ESI^+$) calcd for $C_{42}H_{45}ClFN_9O_6$ ($[M+H]^+$) m/z 826.33; found 826.2.

140: N-((1r,4r)-4-(3-chloro-4-cyanophenoxy)cyclohexyl)-2-(3-((5-(2,6-dioxopiperidin-3-yl)-6-fluoro-1,3-dioxoisoindolin-5-yl)hexahydropyrrolo[3,4-c]pyrrol-2(1H)-yl)methyl)azetidine-1-yl)pyrimidine-5-carboxamide

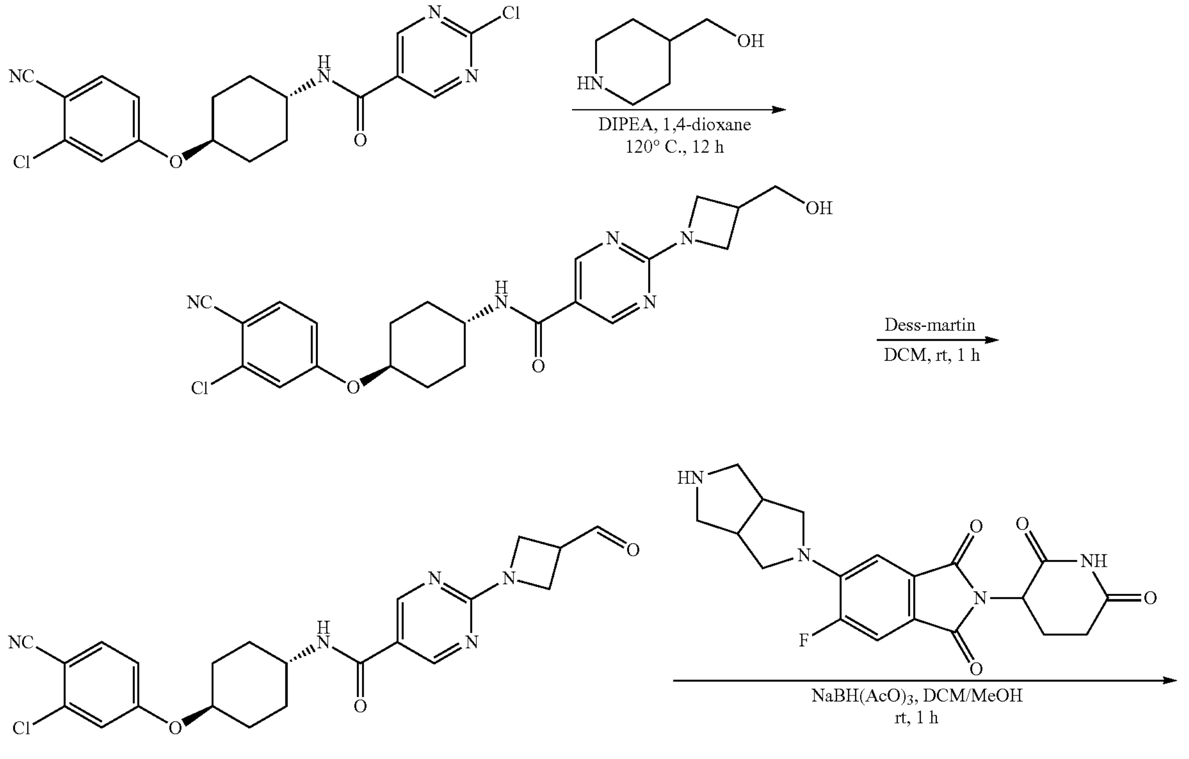

-continued
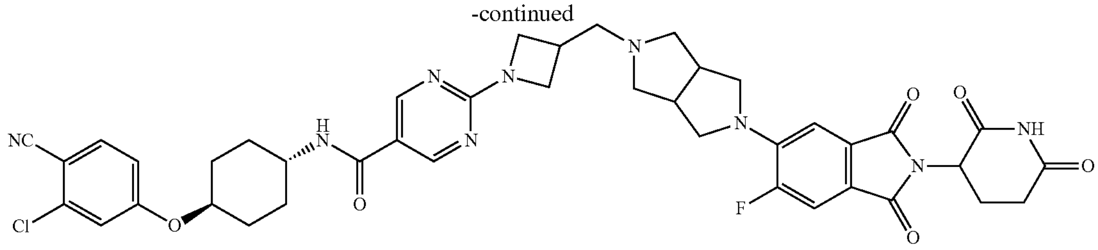
140
$^1$H NMR (400 MHz, DMSO-$d_6$) δ 11.06 (s, 1H), 8.71 (s, 2H), 8.14 (d, J=7.5 Hz, 1H), 7.86 (d, J=8.8 Hz, 1H), 7.63 (d, J=12.5 Hz, 1H), 7.38 (d, J=2.4 Hz, 1H), 7.17-7.10 (m, 2H), 5.76 (s, 1H), 5.08 (dd, J=12.9, 5.4 Hz, 1H), 4.54 (s, 1H), 4.16 (t, J=8.6 Hz, 2H), 3.75 (dd, J=9.2, 5.5 Hz, 3H), 3.69 (d, J=8.2 Hz, 2H), 2.87 (d, J=11.6 Hz, 4H), 2.67 (d, J=7.4 Hz, 2H), 2.62 (d, J=6.3 Hz, 2H), 2.09 (s, 2H), 2.06-1.96 (m, 1H), 1.88 (s, 3H), 1.49 (s, 4H), 1.23 (s, 1H). LC/MS ($ESI^+$) calcd for $C_{41}H_{41}ClFN_9O_6$ ($[M+H]^+$) m/z 810.28; found 809.8.
141: N-((1r,4r)-4-(3-chloro-4-cyanophenoxy)cyclohexyl)-5-(4-((7-(2,6-dioxopiperidin-3-yl)-6-fluoro-1,3-dioxoisoindolin-5-yl)-2,7-diazaspiro[4.4]nonan-2-yl)methyl)piperidin-1-yl)pyrazine-2-carboxamide
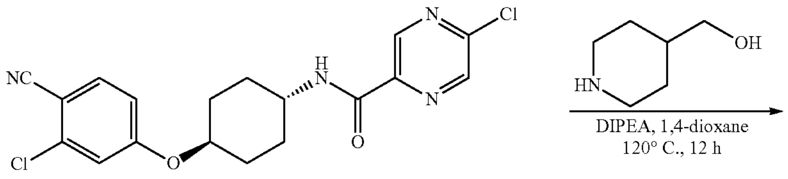
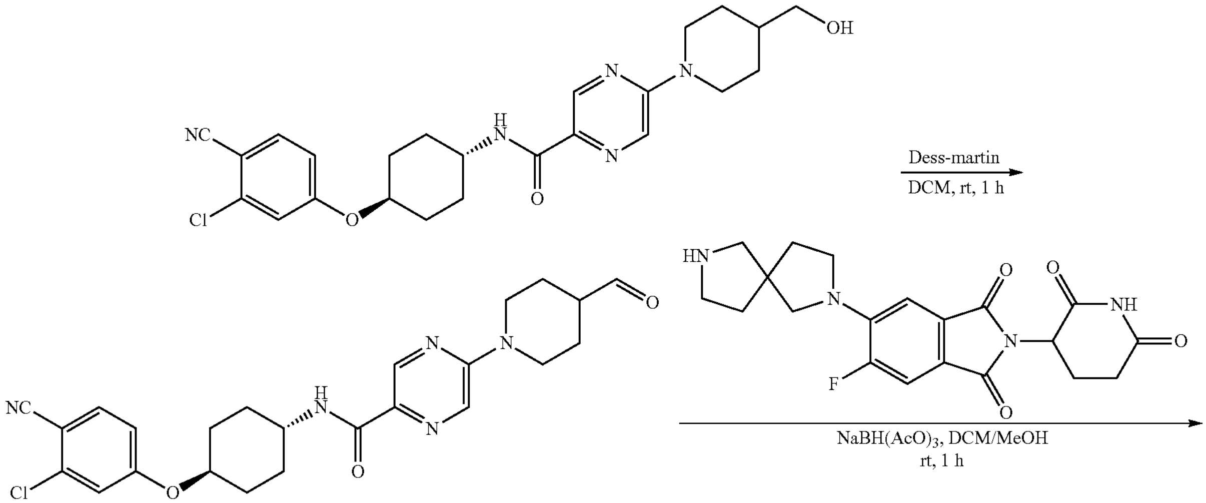
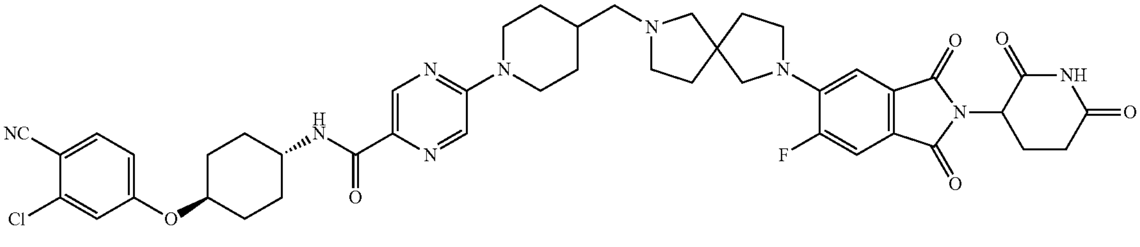
141

$^1H$ NMR (400 MHz, DMSO-$d_6$) δ 11.12 (s, 1H), 8.58 (s, 1H), 8.24 (s, 1H), 8.08 (d, J=8.3 Hz, 1H), 7.87 (d, J=8.8 Hz, 1H), 7.61 (d, J=12.6 Hz, 1H), 7.38 (d, J=2.3 Hz, 1H), 7.13 (dd, J=8.8, 2.2 Hz, 1H), 7.05 (d, J=7.5 Hz, 1H), 5.07 (dd, J=12.9, 5.3 Hz, 1H), 4.52 (s, 1H), 4.45 (d, J=12.2 Hz, 2H), 3.81 (s, 1H), 3.62 (s, 2H), 3.50 (dd, J=25.3, 8.1 Hz, 3H), 3.17 (s, 1H), 2.97 (t, J=12.5 Hz, 2H), 2.87 (d, J=12.0 Hz, 1H), 2.62 (s, 1H), 2.56 (d, J=5.6 Hz, 2H), 2.42 (d, J=9.2 Hz, 1H), 2.28 (d, J=6.8 Hz, 2H), 2.09 (d, J=10.7 Hz, 2H), 1.98 (ddd, J=19.7, 12.2, 6.3 Hz, 3H), 1.83-1.71 (m, 4H), 1.67-1.56 (m, 2H), 1.55-1.45 (m, 2H), 1.28 (d, J=16.1 Hz, 1H), 1.24 (s, 1H), 1.10 (d, J=12.2 Hz, 2H), 0.86 (s, 1H). LC/MS (ESI$^+$) calcd for $C_{44}H_{47}ClFN_9O_6$ ([M+H]$^+$) m/z 852.37; found 851.8.

142: N-((1r,4r)-4-(3-chloro-4-cyanophenoxy)cyclohexyl)-6-(4-((7-(2-(2,6-dioxopiperidin-3-yl)-6-fluoro-1,3-dioxoisoindol-5-yl)-2,7-diazaspiro[4.4]nonan-2-yl)methyl)piperidin-1-yl)pyridazine-3-formamide

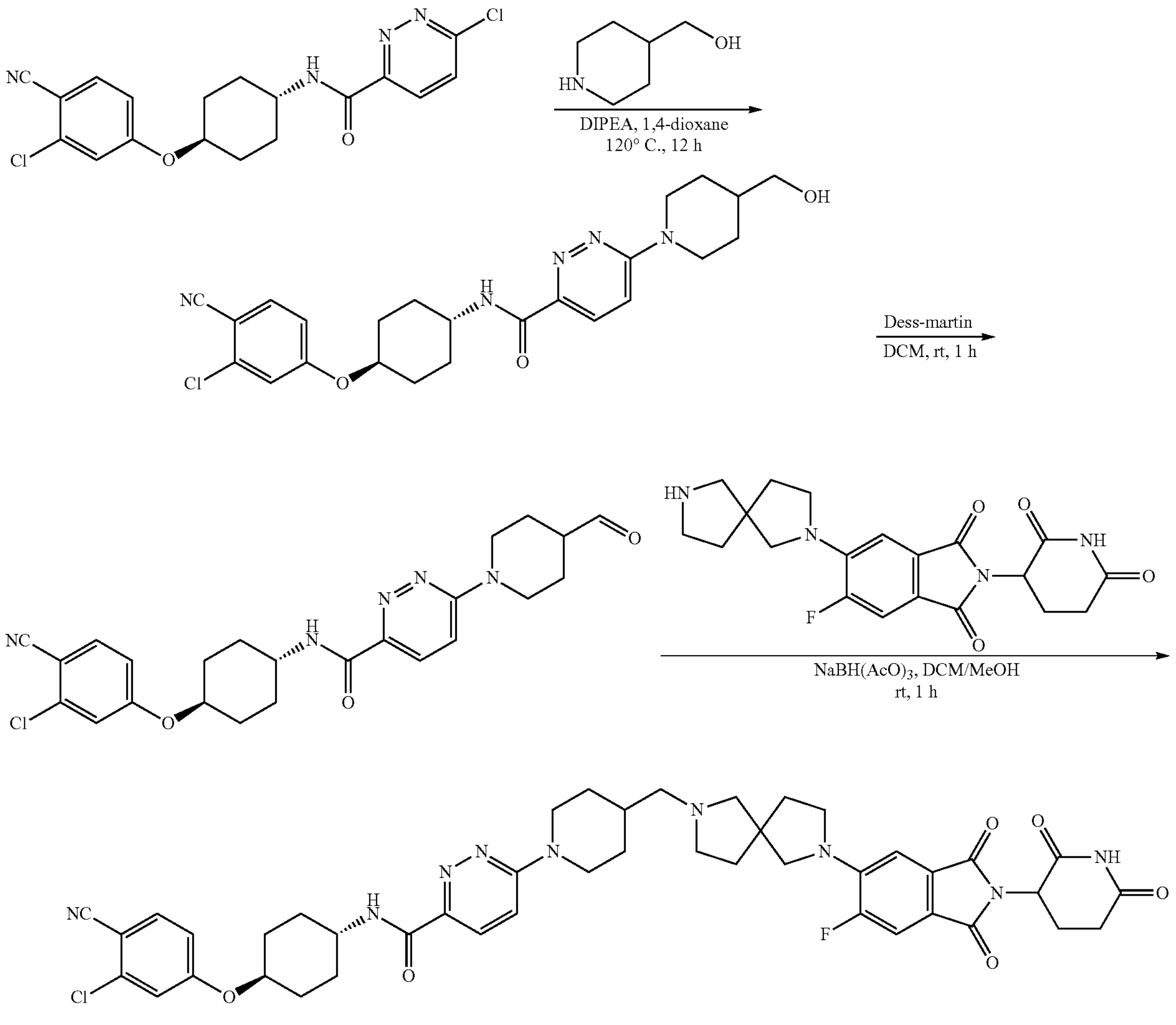

142

$^1H$ NMR (400 MHz, $CDCl_3$) δ 8.18 (s, 1H), 7.99 (d, J=9.5 Hz, 1H), 7.90 (d, J=8.4 Hz, 1H), 7.58 (d, J=8.7 Hz, 1H), 7.42 (d, J=12.2 Hz, 1H), 7.04 (d, J=7.6 Hz, 1H), 7.02 (d, J=2.2 Hz, 1H), 6.99 (d, J=9.6 Hz, 1H), 6.87 (dd, J=8.7, 2.2 Hz, 1H), 4.94 (dd, J=12.1, 5.4 Hz, 1H), 4.53 (d, J=13.3 Hz, 2H), 4.32 (d, J=15.1 Hz, 1H), 4.06 (s, 1H), 3.73-3.59 (m, 3H), 3.55 (d, J=8.8 Hz, 1H), 3.07 (t, J=12.4 Hz, 3H), 2.94 (s, 1H), 2.89 (s, 2H), 2.86-2.80 (m, 2H), 2.77 (d, J=16.8 Hz, 2H), 2.60 (d, J=5.5 Hz, 2H), 2.18 (d, J=10.2 Hz, 4H), 2.07 (d, J=7.3 Hz, 1H), 2.01 (d, J=11.3 Hz, 5H), 1.74-1.64 (m, 2H), 1.54-1.44 (m, 2H), 1.35 (s, 1H), 1.30 (s, 1H), 0.90 (s, 1H). LC/MS (ESI) calcd for $C_{44}H_{47}ClFN_9O_6$ ([M+H]$^+$) m/z 852.37; found 852.2.

143: N-((1r,4r)-4-(3-chloro-4-cyanophenoxy)cyclohexyl)-6-(4-((2-(2,6-dioxopiperidin-3-yl)-1,3-dioxoisoindolin-5-yl)amino)piperidin-1-yl)methyl)piperidin-1-yl)pyridazine-3-formamide

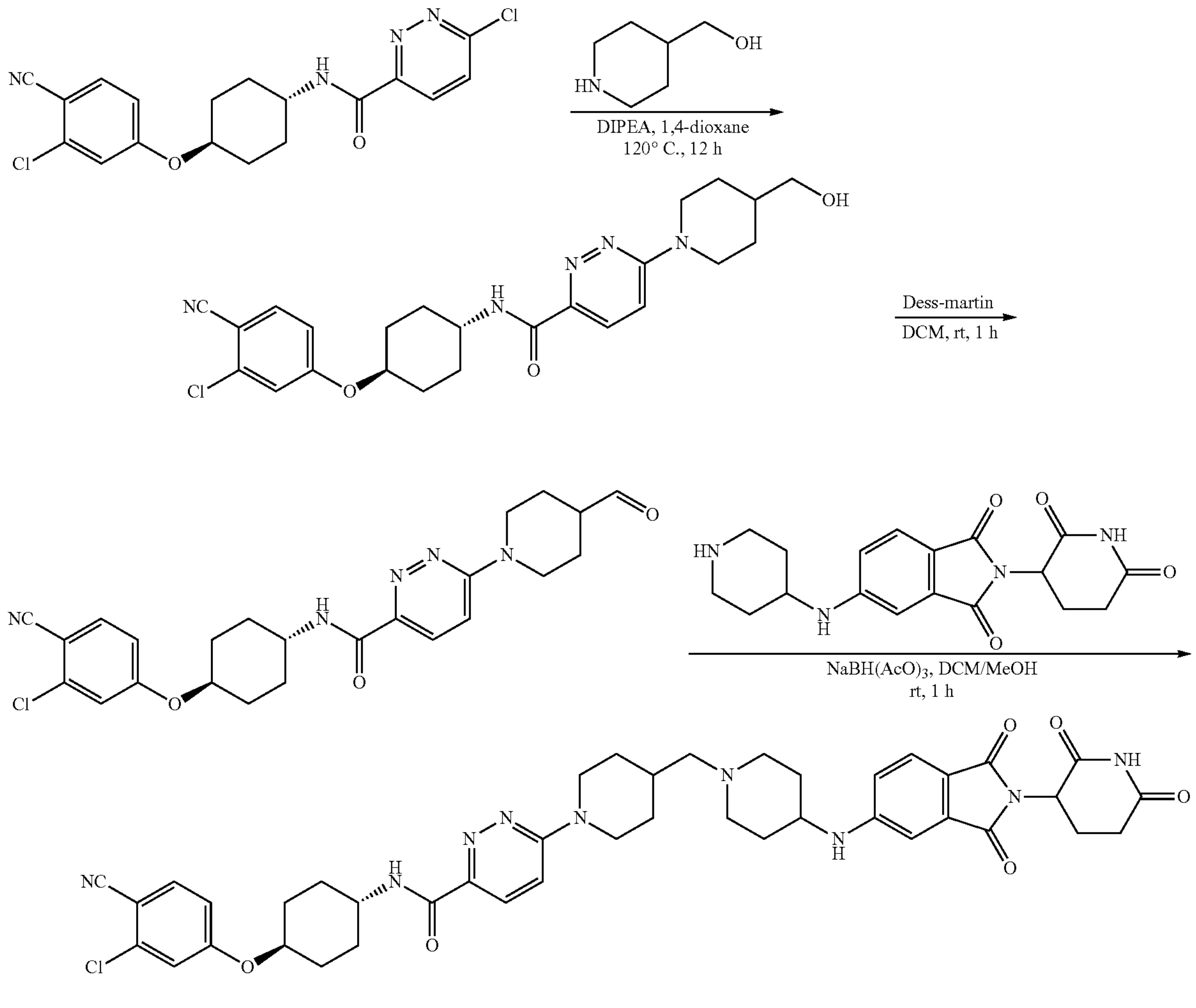

143

$^1H$ NMR (400 MHz, $CDCl_3$) δ 7.99 (d, J=9.5 Hz, 1H), 7.90 (d, J=8.2 Hz, 1H), 7.64 (d, J=8.3 Hz, 1H), 7.58 (d, J=8.8 Hz, 1H), 7.02 (d, J=2.4 Hz, 1H), 7.01 (s, 1H), 6.88 (dd, J=8.8, 2.3 Hz, 1H), 6.77 (d, J=6.5 Hz, 1H), 4.99-4.92 (m, 1H), 4.53 (d, J=12.7 Hz, 2H), 4.34 (s, 1H), 4.09 (s, 1H), 3.90 (s, 1H), 3.69 (s, 1H), 3.50-3.42 (m, 1H), 3.06 (t, J=12.6 Hz, 3H), 2.92 (d, J=13.2 Hz, 1H), 2.80 (dd, J=24.9, 12.5 Hz, 2H), 2.38 (s, 2H), 2.27 (d, J=14.7 Hz, 3H), 1.96 (s, 4H), 1.70 (s, 4H), 1.56-1.41 (m, 3H), 1.29 (d, J=11.8 Hz, 5H), 0.90 (s, 1H). LC/MS ($ESI^+$) calcd for $C_{42}H_{46}ClNO_6$ ($[M+H]^+$) m/z 808.34; found 808.3.

145: N-((1r,4r)-4-(3-chloro-4-cyanophenoxy)cyclohexyl)-5-(4-((2-(2,6-dioxopiperidin-3-yl)-6-fluoro-1,3-dioxoisoindolin-5-yl)amino)piperidin-1-yl)methyl)piperidin-1-yl)pyrazine-2-carboxamide

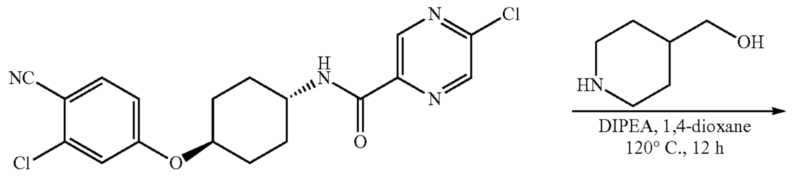

-continued
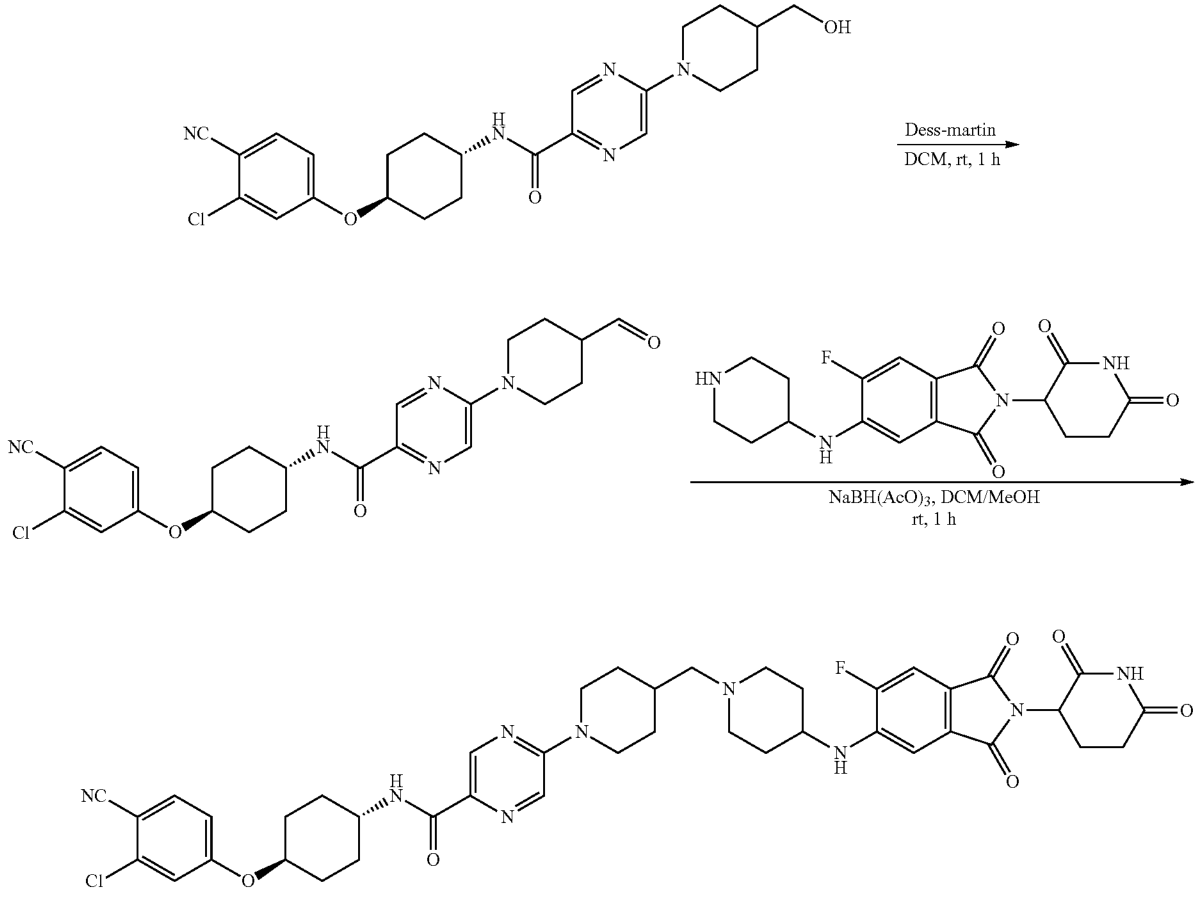
145
$^1$H NMR (400 MHz, $CDCl_3$) δ 8.85 (s, 1H), 8.19 (s, 1H), 7.98 (s, 1H), 7.58 (d, J=8.7 Hz, 1H), 7.43 (dd, J=15.2, 9.1 Hz, 2H), 7.11 (d, J=7.0 Hz, 1H), 7.01 (d, J=2.4 Hz, 1H), 6.87 (dd, J=8.7, 2.4 Hz, 1H), 4.95 (dd, J=12.2, 5.4 Hz, 1H), 4.62 (s, 1H), 4.48 (d, J=13.3 Hz, 2H), 4.34 (d, J=9.8 Hz, 1H), 4.05 (s, 1H), 3.48-3.40 (m, 1H), 3.02 (d, J=12.6 Hz, 1H), 2.99-2.88 (m, 3H), 2.87-2.73 (m, 3H), 2.31 (d, J=6.9 Hz, 2H), 2.21 (d, J=11.5 Hz, 5H), 1.94 (d, J=11.9 Hz, 3H), 1.68 (dd, J=23.4, 11.7 Hz, 4H), 1.54-1.41 (m, 3H), 1.27 (t, J=13.9 Hz, 4H), 0.90 (s, 1H). LC/MS ($ESI^+$) calcd for $C_{42}H_{45}ClFN_9O_6$ ($[M+H]^+$) m/z 826.33; found 826.2.
146: N-((1r,4r)-4-(3-chloro-4-cyanophenoxy)cyclohexyl)-5-(4-((2-(2,6-dioxopiperidin-3-yl)-1,3-dioxoisoindolin-5-yl)amino)piperidin-1-yl)methyl)piperidin-1-yl)pyrazine-2-carboxamide
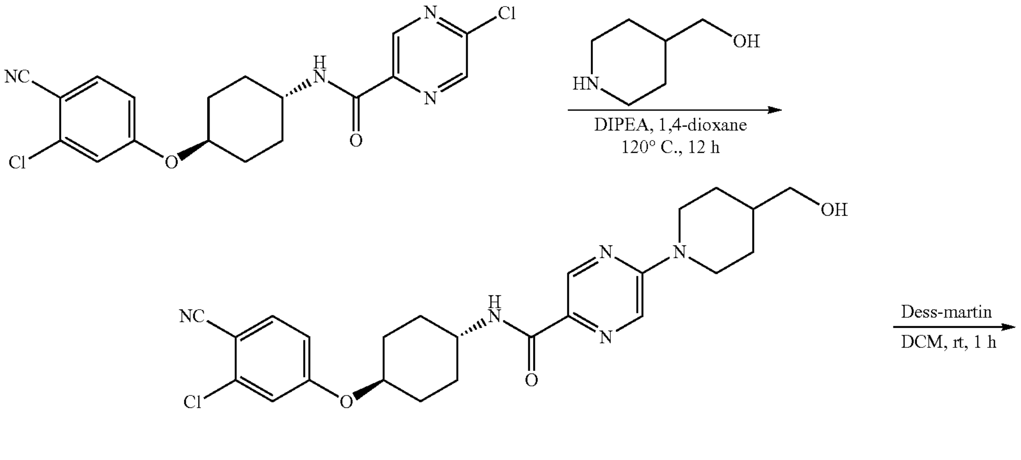

-continued
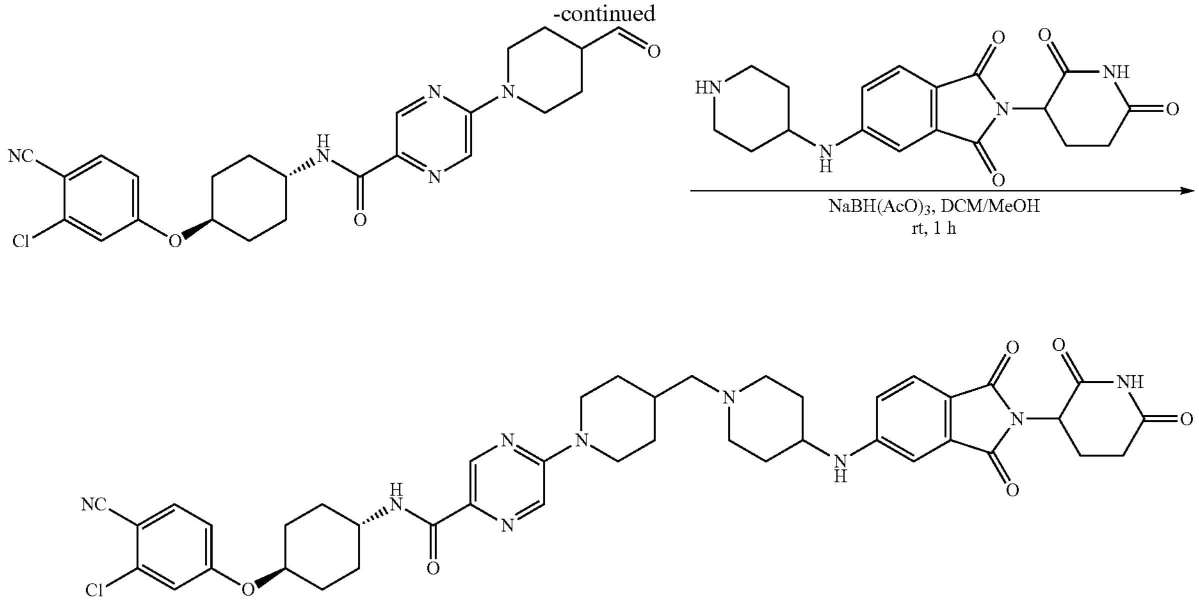
146
$^{1}H$ NMR (400 MHz, $CDCl_3$) δ8.84 (s, 1H), 7.97 (s, 1H), 7.63 (d, J=8.3 Hz, 1H), 7.58 (d, J=8.7 Hz, 1H), 7.41 (d, J=8.2 Hz, 1H), 7.01 (d, J=2.2 Hz, 2H), 6.87 (dd, J=8.8, 2.3 Hz, 1H), 6.77 (d, J=8.5 Hz, 1H), 4.96 (dd, J=12.1, 5.4 Hz, 1H), 4.81 (s, 1H), 4.49 (d, J=13.0 Hz, 2H), 4.31 (d, J=10.3 Hz, 1H), 4.06 (d, J=8.2 Hz, 2H), 3.68 (s, 1H), 3.16 (s, 2H), 3.01 (t, J=12.2 Hz, 2H), 2.91 (d, J=14.5 Hz, 1H), 2.84-2.77 (m, 2H), 2.49 (s, 3H), 2.02 (s, 6H), 1.78-1.63 (m, 4H), 1.49 (dd, J=22.3, 10.8 Hz, 4H), 1.33 (d, J=19.5 Hz, 3H), 0.90 (s, 1H).
LC/MS ($ESI^+$) calcd for $C_{42}H_{46}ClN_9O_6$ ($[M+H]^+$) m/z 808.34; found 808.3.
147: N-((1r,4r)-4-(3-chloro-4-cyanophenoxy)cyclohexyl)-6-(4-((2-(2,6-dioxopiperidin-3-yl)-1,3-dioxoisoindolin-5-yl)oxy)piperidin-1-yl)methyl) piperidin-1-yl)pyridazine-3-formamide
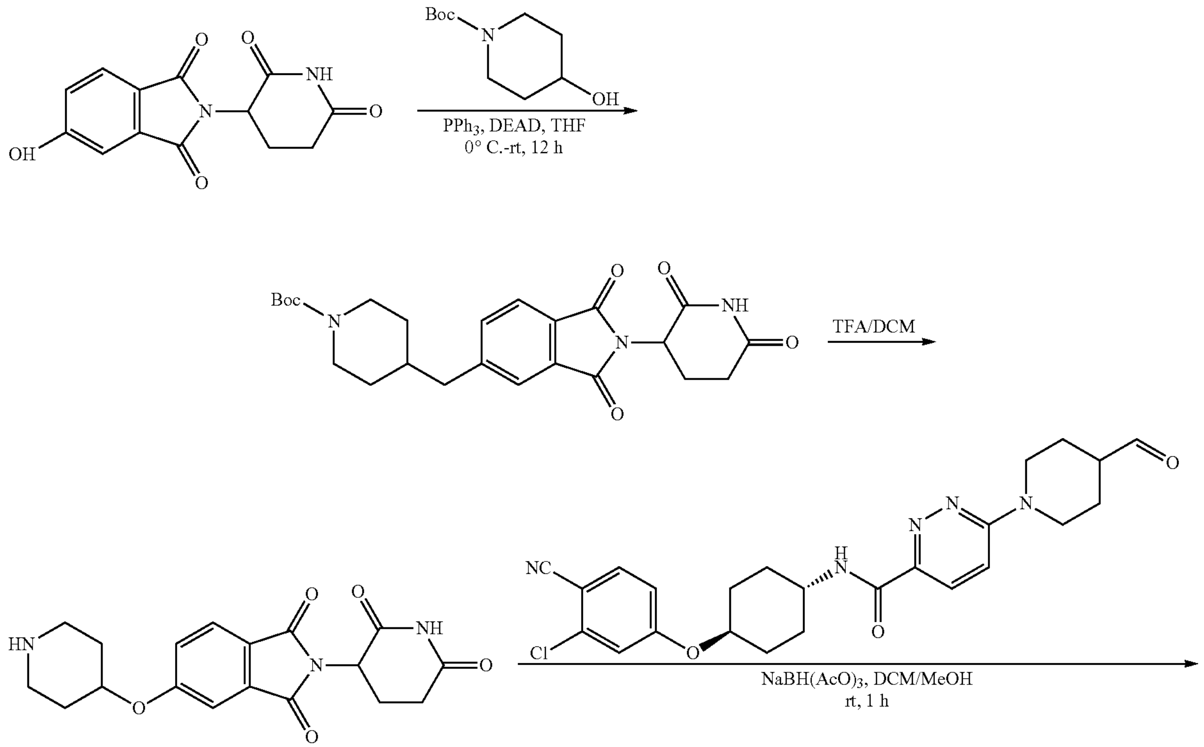

-continued

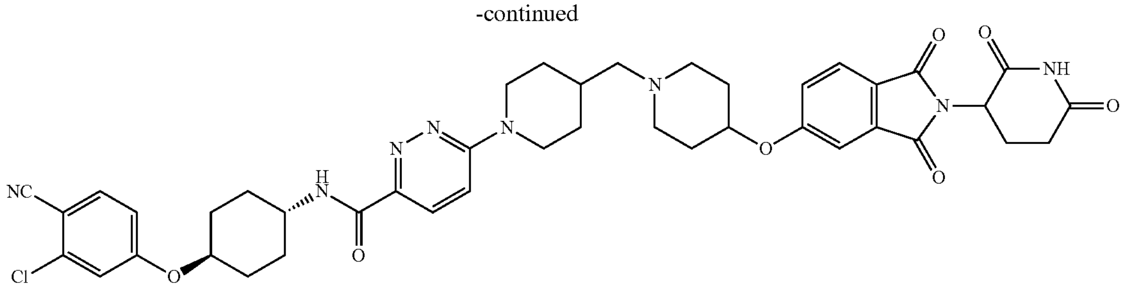

147

Step 1: t-Butyl 2-(2,6-dioxopiperidin-3-yl)-5-hydroxylisoindoline-1,3-dione (274 mg, 1.0 mmol), t-butyl 4-hydroxypiperidine-1-carboxylate (201 mg, 1.0 mmol). DEAD (209 mg, 1.2 mmol) and triphenylphosphine (314 mg, 1.2 mmol) were added in 10 mL of THF. Under the protection of nitrogen, the reaction was allowed to react overnight under stirring at room temperature, to which were added ethyl acetate and water for extraction. The organic phase was washed with saturated brine, and dried over anhydrous sodium sulfate. The solvent was removed by rotary evaporation to obtain a crude product, which was separated and purified by Pre-TLC, to provide compound t-butyl 4-((2-(2,6-dioxopiperidin-3-yl)-1,3-dioxoisoindol-5-yl)oxy)piperidine-1-carboxylate (326 mg), with a yield of 71%. LC/MS ($ESI^+$) calcd for $C_{23}H_{27}N_3O_7$ ($[M+H]^+$) m/z 457.18; found 458.1.

Step 2: Compound t-butyl 4-((2-(2,6-dioxopiperidin-3-yl)-1,3-dioxoisoindolin-5-yl) oxy)piperidine-1-carboxylate (326 mg, 0.71 mmol) was dissolved in 10 ml dichloromethane, to which was then added 4 ml trifluoroacetic acid, and the mixture was allowed to react 3 h under stirring at room temperature. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound 2-(2,6-dioxopiperidin-3-yl)-5-(piperidine-4-oxy)isoindole-1,3-dione (213 mg), with a yield of 84%. LC/MS ($ESI^+$) calcd for $C_{18}H_{19}N_3O_5$ ($[M+H]^+$) m/z 357.136; found 358.2.

Step 3: N-((1r,4r)-4-(3-chloro-4-cyanophenoxy)cyclohexyl)-6-(4-formylpiperidin-1-yl)pyridazine-3-formamide (57 mg, 0.12 mmol) was weighed and placed in a 25 mL single-neck round bottom flask, to which was added dichloromethane (5 mL), and the mixture was stirred at room temperature to dissolve and make the solution become clear. Subsequently, 2-(2,6-dioxopiperidin-3-yl)-5-(piperidine-4-oxy)isoindole-1,3-dione (44 mg, 0.12 mmol) was added to the system, and the reaction was stirred at room temperature for 15 min. After that, sodium triacetylborohydride (100 mg, 0.48 mmol) was added to the system, and the system was allowed to react under stirring at room temperature. After 4 h, the sample was taken out and subjected to TLC, and the result indicated the disappearance of the starting material. The stirring was stopped. Dichloromethane (15 mL) and water (15 mL) were added to the system. The system was stirred vigorously, and then allowed to stand for separation of layers. The water layer was extracted with dichloromethane (10 mL*3). The organic phases were combined, successively washed with water (10 mL*2) and saturated brine (15 mL), and dried over anhydrous sodium sulfate. The solvent was removed by rotary evaporation to obtain the crude product, which was then separated and purified by Pre-TLC to obtain compound N-((1r,4r)-4-(3-chloro-4-cyanophenoxy)cyclohexyl)-6-(4-((2-(2,6-dioxopiperidin-3-yl)-1,3-dioxoisoindolin-5-yl)oxy)piperidin-1-yl)methyl)piperidin-1-yl)pyridazine-3-formamide (23 mg), with a yield of 33%. $^1H$ NMR (400 MHz, DMSO-$d_6$) δ 8.60 (d, J=8.4 Hz, 1H), 7.88-7.83 (m, 2H), 7.80 (d, J=11.3 Hz, 1H), 7.46 (s, 1H), 7.40 (d, J=2.3 Hz, 1H), 7.37 (d, J=8.3 Hz, 1H), 7.33 (d, J=9.8 Hz, 1H), 7.14 (dd, J=8.8, 2.3 Hz, 1H), 5.12 (dd, J=13.0, 5.4 Hz, 1H), 4.72 (s, 1H), 4.48 (d, J=13.3 Hz, 3H), 3.86 (s, 2H), 3.05-2.96 (m, 3H), 2.67 (s, 2H), 2.25 (s, 2H), 2.17 (d, J=6.9 Hz, 2H), 2.09 (s, 3H), 1.97 (s, 2H), 1.88 (s, 3H), 1.82 (d, J=12.7 Hz, 2H), 1.70-1.61 (m, 4H), 1.51 (d, J=11.4 Hz, 3H), 1.10 (d, J=12.8 Hz, 2H). LC/MS ($ESI^+$) calcd for $C_{42}H_{42}ClN_8O_7$ ($[M+H]^+$) m/z: 809.32; found 809.2.

148: N-((1r,4r)-4-(3-chloro-4-cyanophenoxy)cyclohexyl)-5-(4-((2-(2,6-dioxopiperidin-3-yl)-6-fluoro-1,3-dioxoisoindolin-5-yl)-2,7-diazaspiro[3.5]nonan-7-yl)methyl)piperidin-1-yl)pyrimidine-2-carboxamide

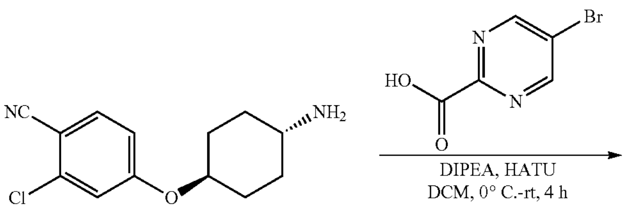

-continued

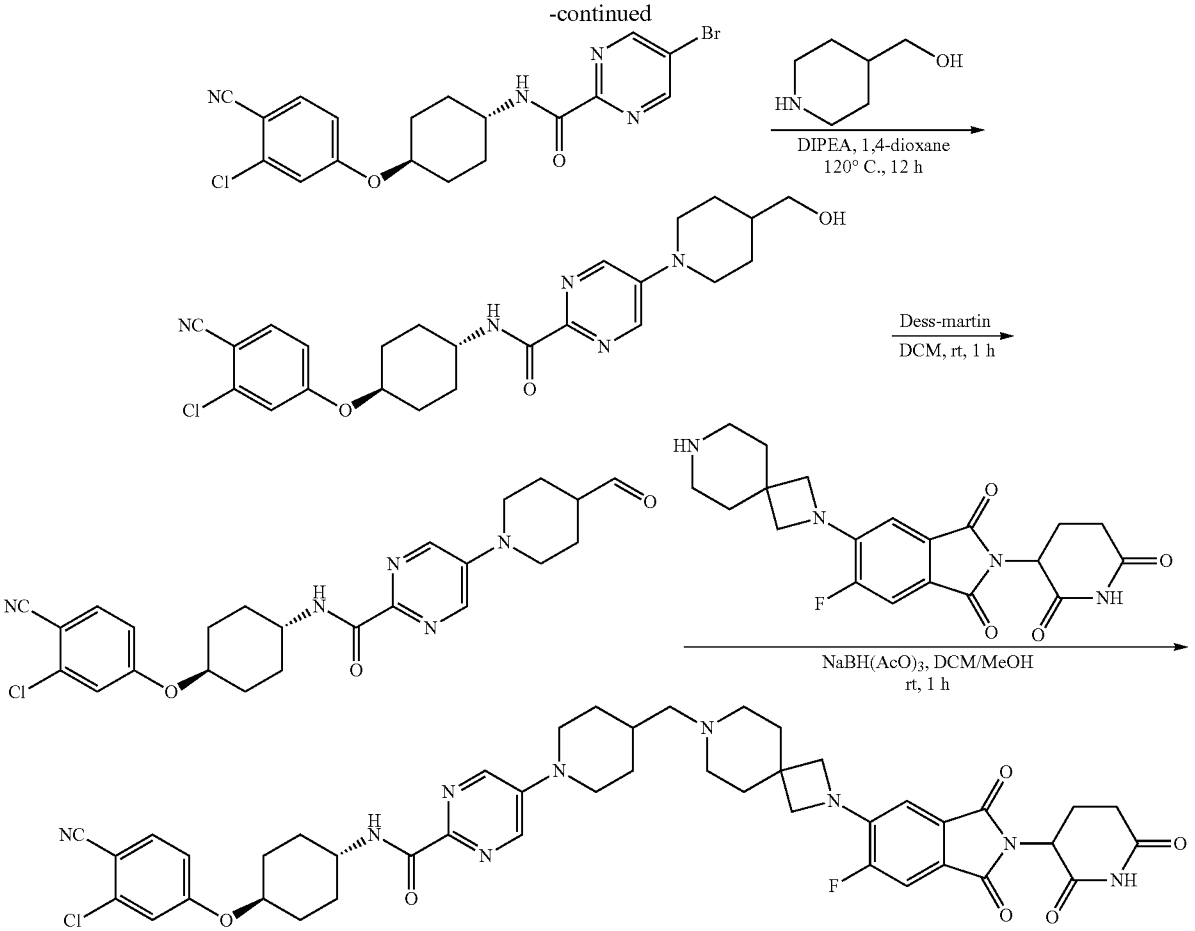

148

Step 1: Compound 5-bromopyrimidine-2-carboxylic acid (0.80 g, 3.94 mmol) and HATU (2.41 g, 6.22 mmol) were added in 30 mL of dichloromethane, and then the system was moved in an ice water bath to cool down under stirring. After 10 min, diisopropylethylamine (1.03 g, 7.97 mmol) was added, followed by addition of 4-((1r,4r)-4-aminocyclohexyl)oxy)-2-chlorobenzonitrile (1.01 g, 3.99 mmol). After that, the ice bath was removed, and the reaction was allowed to react overnight under stirring at room temperature. TLC indicated the disappearance of raw material. To the reaction solution, were added dichloromethane and water for extraction. The organic layer was washed with saturated brine, dried over anhydrous sodium sulfate, rotatory evaporated to dry, and separated and purified by Pre-TLC, to provide compound 5-bromo-N-((1r,4r)-4-(3-chloro-4-cyanophenoxy)cyclohexyl)pyrimidine-2-carboxamide (1.09 g), with a yield of 63.5%. LC/MS (ESI$^+$) calcd for $C_{18}H_{16}BrClN_4O_2$ ([M+H]$^+$) m/z 434.01; found 435.1.

Step 2: 5-Bromo-N-((1r,4r)-4-(3-chloro-4-cyanophenoxy)cyclohexyl)pyrimidine-2-carboxamide (435 mg, 1.0 mmol), piperidin-4-yl methanol (116 mg, 1.0 mmol), palladium acetate (15 mg, 0.05 mmol), diisopropylethylamine (35 mg, 0.05 mmol) and cesium carbonate (652 mg, 2.0 mmol) were added to 10 mL of dioxane. Under the protection of nitrogen, the reaction solution was heated to 110° C., stirred and reacted overnight under reflux. After cooling to room temperature, the reaction solution was added with ethyl acetate and water for extraction. The organic phase was successively washed with 0.05 N HCl and saturated brine, and dried over anhydrous sodium sulfate. The solvent was removed by rotary evaporation to obtain the crude product, which was separated and purified by Pre-TLC, to provide compound N-((1r,4r)-4-(3-chloro-4-cyanophenoxy)cyclohexyl)-5-(4-(hydroxymethyl)piperidin-1-yl)pyrimidine-2-carboxamide (191 mg), with a yield of 41%. LC/MS (ESI$^+$) calcd for $C_{24}H_{28}ClN_5O_3$ ([M+H]$^+$) m/z 469.97; found 470.1.

Step 3: N-((1r,4r)-4-(3-chloro-4-cyanophenoxy)cyclohexyl)-5-(4-(hydroxymethyl) piperidin-1-yl)pyrimidine-2-carboxamide (50 mg, 0.11 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (72 mg, 0.17 mmol) was added to the system. After that, the system was warmed to room temperature and reacted under stirring. After 2 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4r)-4-(3-chloro-4-cyanophenoxy)cyclohexyl)-5-(4-formylpiperidin-1-yl)pyrimidine-2-carboxamide (30 mg), with a yield of 58%. LC/MS (ESI$^+$) calcd for $C_{24}H_{26}ClN_5O_3$ ([M+H]$^+$) m/z 467.95; found 468.1.

Step 4: N-((1r,4r)-4-(3-chloro-4-cyanophenoxy)cyclohexyl)-5-(4-formylpiperidin-1-yl)pyrimidine-2-carboxamide (30 mg, 0.06 mmol) was weighed and placed in a 25 mL single-neck round bottom flask, to which was added dichloromethane (3 mL), and the mixture was stirred at room temperature to dissolve and make the solution become clear. Subsequently, 2-(2,6-dioxopiperidin-3-yl)-5-(2,7-diazaspiro[3.5]nonan-2-yl)isoindole-1,3-dione (24 mg, 0.06 mmol) was added to the system, and the reaction was stirred at room temperature for 15 min. After that, sodium triacetylborohydride (38 mg, 0.18 mmol) was added to the system, and the system was allowed to react under stirring at room temperature. After 4 h, the sample was taken out and subjected to TLC, and the result indicated the disappearance of the starting material. The stirring was stopped. Dichloromethane (15 mL) and water (15 mL) were added to the system. The system was stirred vigorously, and then allowed to stand for separation of layers. The water layer was extracted with dichloromethane (10 mL*3). The organic phases were combined, successively washed with water (10 mL*2) and saturated brine (15 mL), and dried over anhydrous sodium sulfate. The solvent was removed by rotary evaporation to obtain the crude product, which was then separated and purified by Pre-TLC to obtain compound N-((1r,4r)-4-(3-chloro-4-cyanophenoxy)cyclohexyl)-5-(4-((2-(2,6-dioxopiperidin-3-yl)-6-fluoro-1,3-dioxoisoindol-5-yl)-2,7-diazaspiro[3.5]nonan-7-yl)methyl)piperidin-1-yl)pyrimidine-2-carboxamide (21 mg), with a yield of 39%. $^1$H NMR (400 MHz, DMSO-$d_6$) δ 8.51 (s, 2H), 8.32 (d, J=8.1 Hz, 1H), 7.87 (d, J=8.6 Hz, 1H), 7.67 (d, J=8.0 Hz, 1H), 7.60 (d, J=10.7 Hz, 1H), 7.38 (s, 1H), 7.29 (d, J=7.9 Hz, 1H), 7.23 (d, J=7.4 Hz, 1H), 7.13 (d, J=9.5 Hz, 1H), 6.90 (d, J=7.7 Hz, 1H), 6.85 (s, 1H), 5.07 (s, 1H), 4.53 (s, 1H), 3.96 (s, 4H), 2.86 (d, J=12.7 Hz, 5H), 2.64 (d, J=28.8 Hz, 2H), 2.33 (s, 4H), 2.12 (s, 5H), 2.05-1.96 (m, 2H), 1.87 (s, 3H), 1.63-1.48 (m, 6H), 1.20-1.11 (m, 4H), 0.85 (s, 2H). LC/MS (ESI$^+$) calcd for $C_{44}H_{47}ClFN_9O_6$ ([M+H]$^+$) m/z 852.37; found 852.3.

149: N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl)methyl)piperidin-1-yl)pyrimidine-2-carboxamide

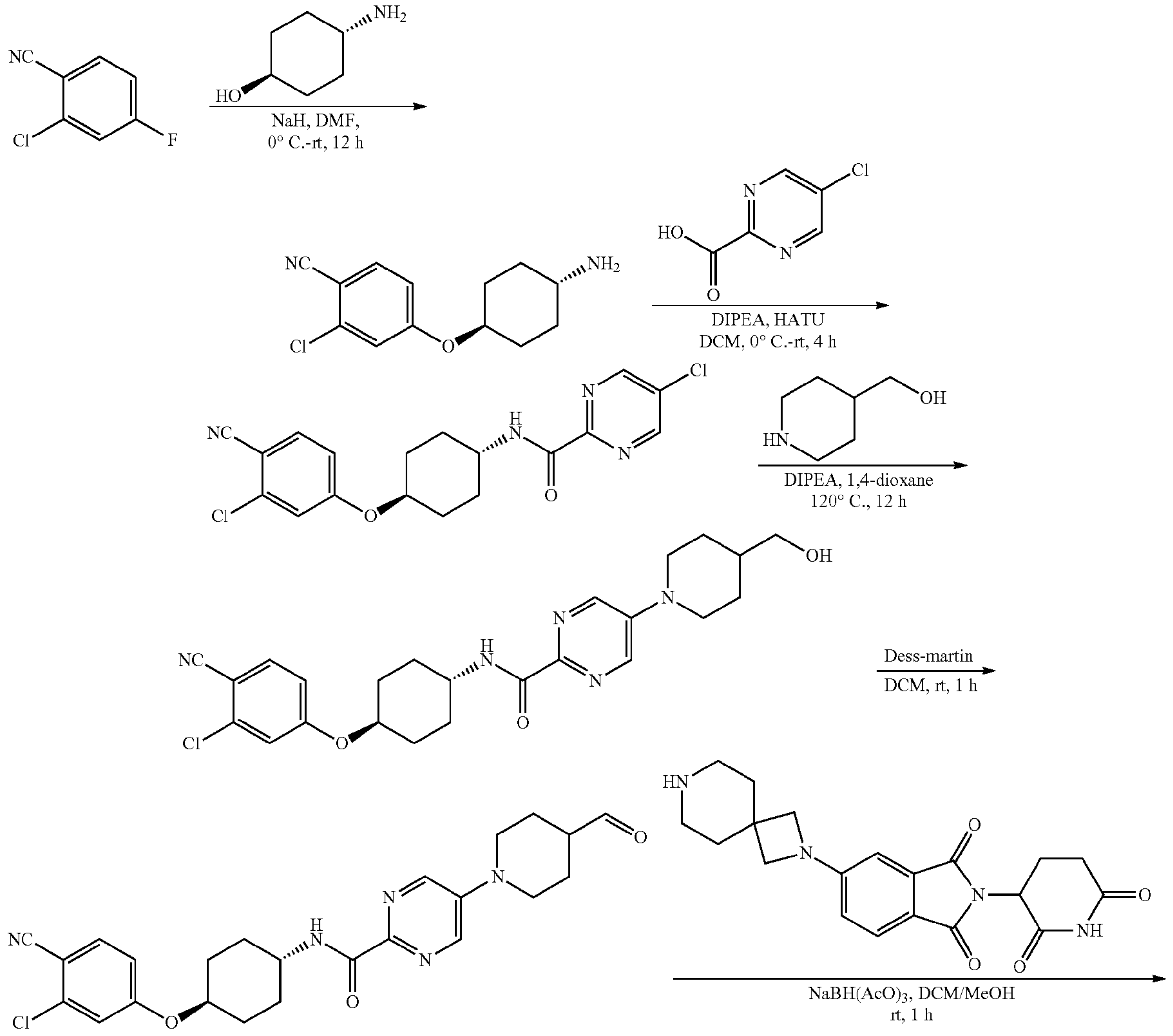

-continued
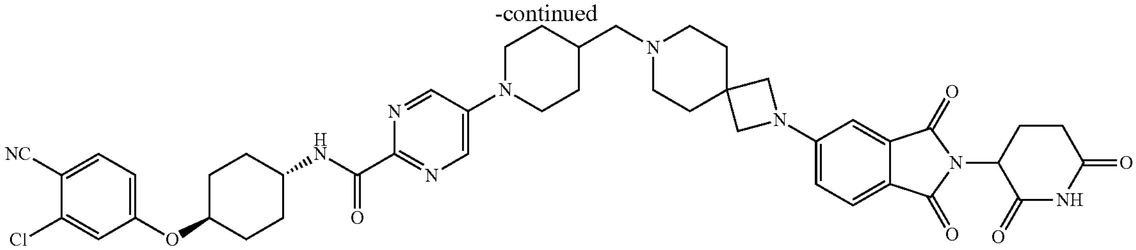
149
$^1$H NMR (400 MHz, DMSO-$d_6$) δ 8.51 (s, 2H), 8.33 (d, J=8.1 Hz, 1H), 7.86 (d, J=8.7 Hz, 1H), 7.63 (d, J=8.1 Hz, 1H), 7.38 (s, 1H), 7.13 (d, J=8.4 Hz, 1H), 6.78 (s, 1H), 6.65 (d, J=8.2 Hz, 1H), 5.05 (dd, J=12.8, 5.3 Hz, 1H), 4.53 (s, 1H), 3.97 (d, J=11.3 Hz, 3H), 2.87 (t, J=11.9 Hz, 3H), 2.60 (s, 2H), 2.32 (s, 4H), 2.12 (s, 4H), 1.99 (d, J=5.1 Hz, 1H), 1.88 (s, 2H), 1.79 (s, 2H), 1.67-1.42 (m, 6H), 1.23 (s, 4H), 1.16 (d, J=10.9 Hz, 3H), 0.84 (d, J=7.3 Hz, 2H). LC/MS (ESI$^+$) calcd for $C_{44}H_{48}ClN_9O_6$ ($[M+H]^+$) m/z 834.38; found 834.3.
150: N-((1r,4r)-4-(3-chloro-4-cyanophenoxy)cyclohexyl)-5-(7-((1-(2,6-dioxopiperidin-3-yl)-6-fluoro-1,3-dioxoisoindolin-5-yl)piperidine-4-yl)methyl)-2,7-diazaspiro[3.5]nonan-2-yl)pyrimidine-2-carboxamide
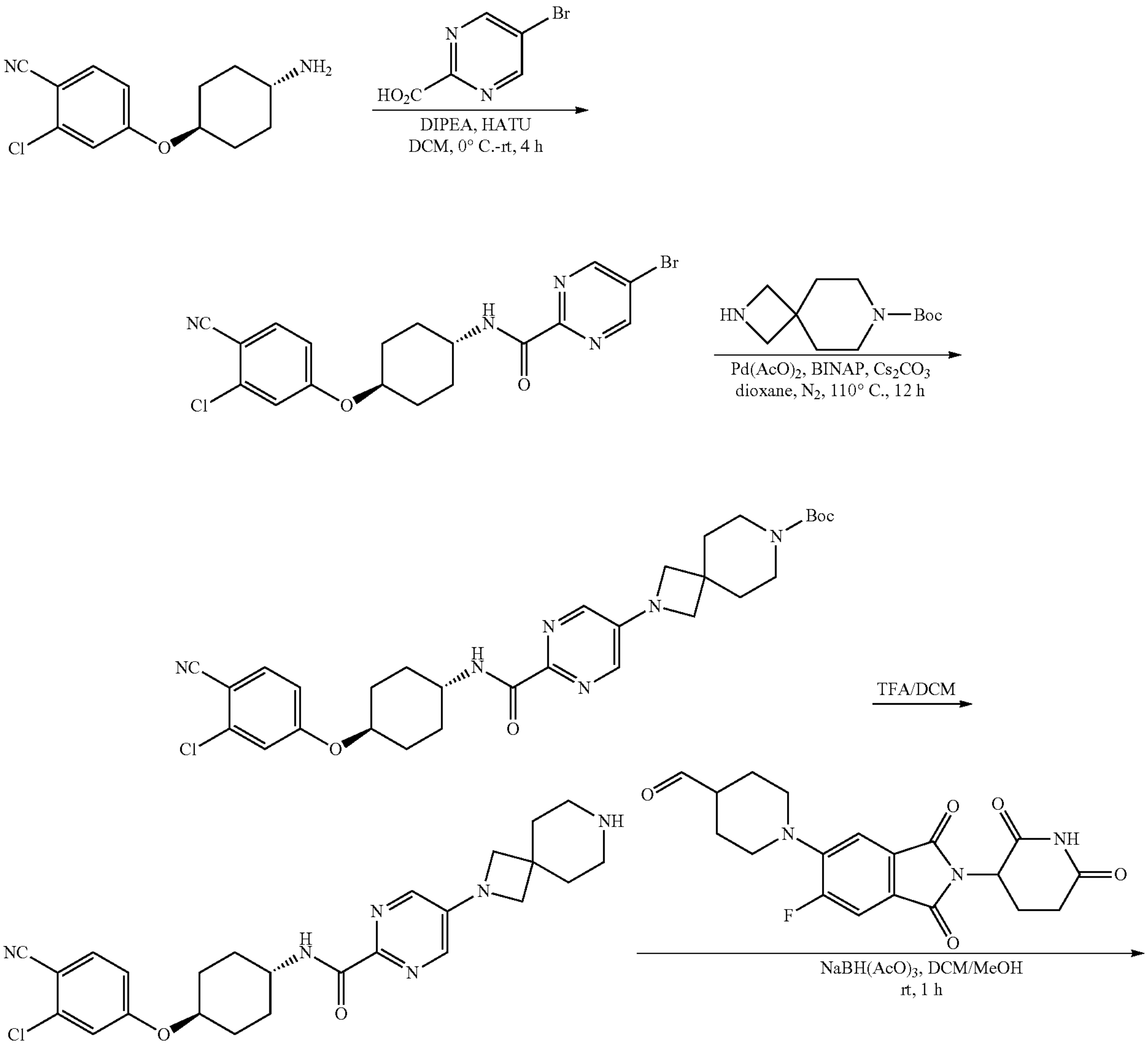

-continued
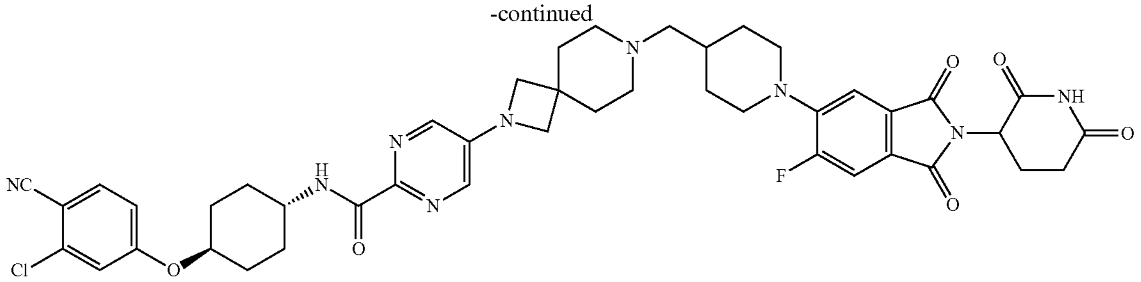
150
$^1$H NMR (400 MHz, DMSO-$d_6$) δ 11.12 (s, 1H), 8.31 (d, J=8.2 Hz, 1H), 8.05 (s, 2H), 7.86 (d, J=8.8 Hz, 1H), 7.71 (d, J=11.4 Hz, 1H), 7.43 (d, J=7.4 Hz, 1H), 7.38 (d, J=2.3 Hz, 1H), 7.13 (dd, J=8.8, 2.2 Hz, 1H), 5.10 (dd, J=12.7, 5.2 Hz, 1H), 4.52 (s, 1H), 3.60 (d, J=10.9 Hz, 5H), 2.88 (t, J=12.2 Hz, 3H), 2.32 (s, 3H), 2.15 (d, J=6.5 Hz, 2H), 2.06 (d, J=29.5 Hz, 4H), 1.87 (s, 2H), 1.78 (s, 5H), 1.65-1.46 (m, 5H), 1.23 (s, 6H), 0.84 (d, J=7.1 Hz, 1H). LC/MS (ESI$^+$) calcd for $C_{44}H_{47}ClFN_9O_6$ ([M+H]$^+$) m/z 852.37; found 852.3.
151: N-((1r,4r)-4-(4-cyano-3-(trifluoromethyl)phenoxy)cyclohexyl)-6-(4-((2-(2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide
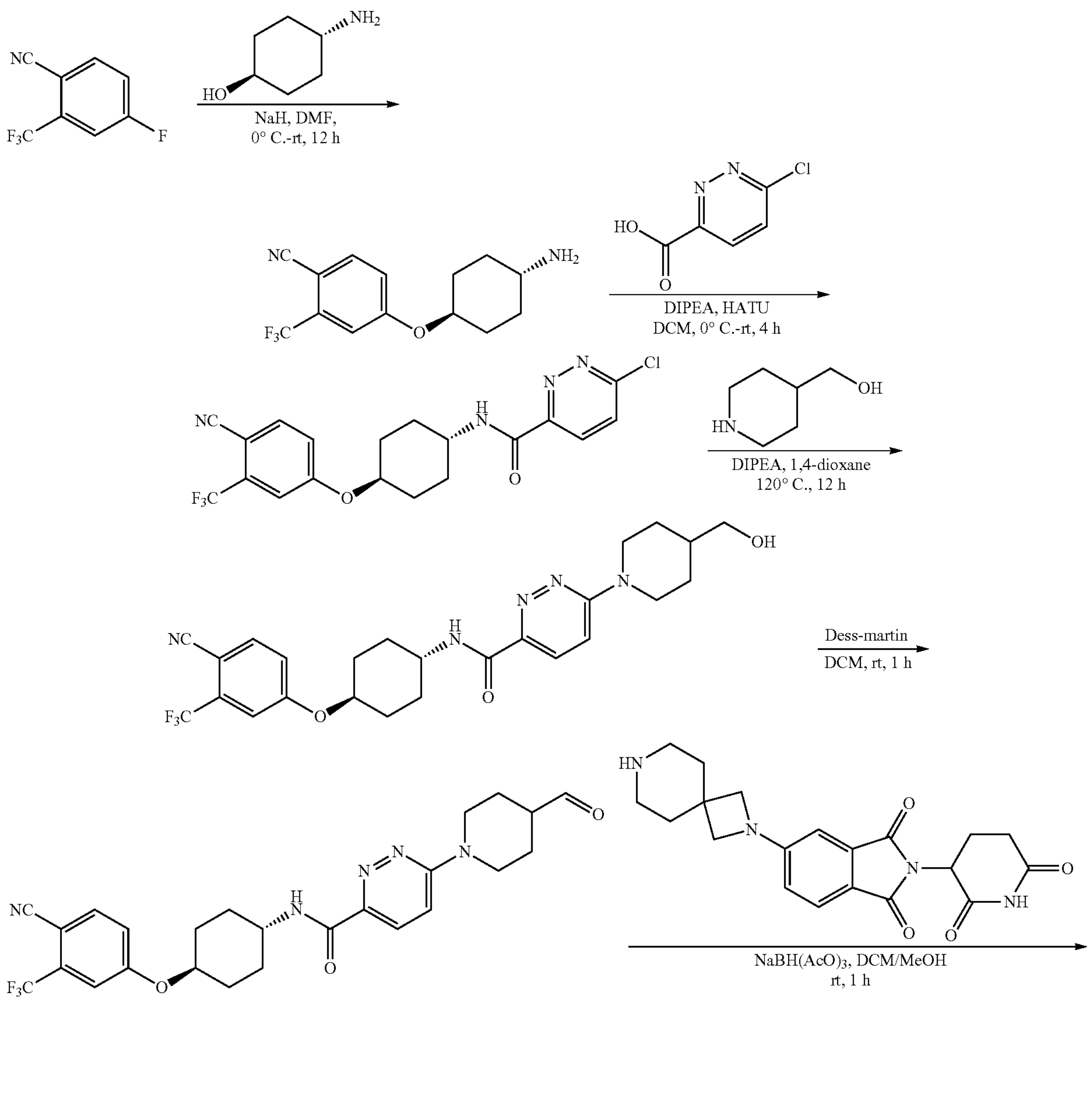

-continued

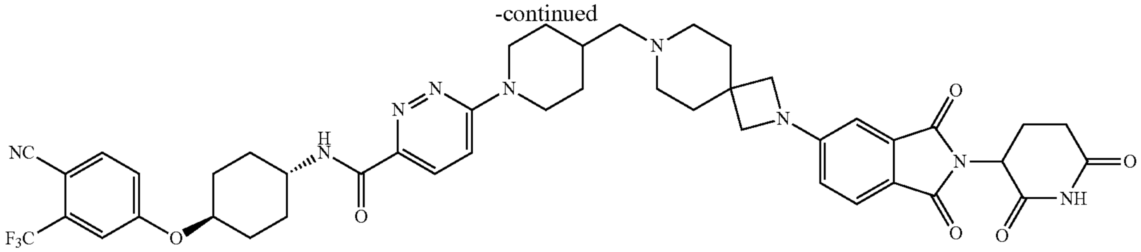

151

$^1$H NMR (400 MHz, DMSO-$d_6$) δ 11.09 (s, 1H), 8.61 (d, J=8.3 Hz, 1H), 8.07 (d, J=8.4 Hz, 1H), 7.80 (d, J=9.5 Hz, 1H), 7.63 (d, J=8.3 Hz, 1H), 7.49 (s, 1H), 7.33 (d, J=9.7 Hz, 1H), 6.78 (d, J=1.7 Hz, 1H), 6.70-6.60 (m, 1H), 5.05 (dd, J=12.8, 5.4 Hz, 1H), 4.63 (s, 2H), 4.47 (d, J=12.7 Hz, 3H), 3.87 (d, J=8.3 Hz, 2H), 3.75 (s, 4H), 3.00 (t, J=11.8 Hz, 2H), 2.88 (dd, J=15.4, 10.0 Hz, 1H), 2.32 (s, 3H), 2.12 (d, J=7.0 Hz, 4H), 2.05-1.95 (m, 1H), 1.89 (s, 3H), 1.82 (s, 3H), 1.65 (dd, J=24.3, 11.0 Hz, 3H), 1.60-1.46 (an, 3H), 1.29-1.17 (m, 2H), 0.86 (dd, J=18.3, 7.5 Hz, 1H). LC/MS (ESI$^+$) calcd for $C_{45}H_{48}F_3N_9O_6$ ([M+H]$^+$) m/z 867.93; found 868.4.

152: N-((1r,4r)-4-(4-cyano-3-(trifluoromethyl)phenoxy)cyclohexyl)-6-(4-(2-(2,6-dioxopiperidin-3-yl)-6-fluoro-1,3-dioxoisoindolin-5-yl)-2,7-diazaspiro[3.5]nonan-7-yl)methyl)piperidin-1-yl)pyridazine-3-formamide

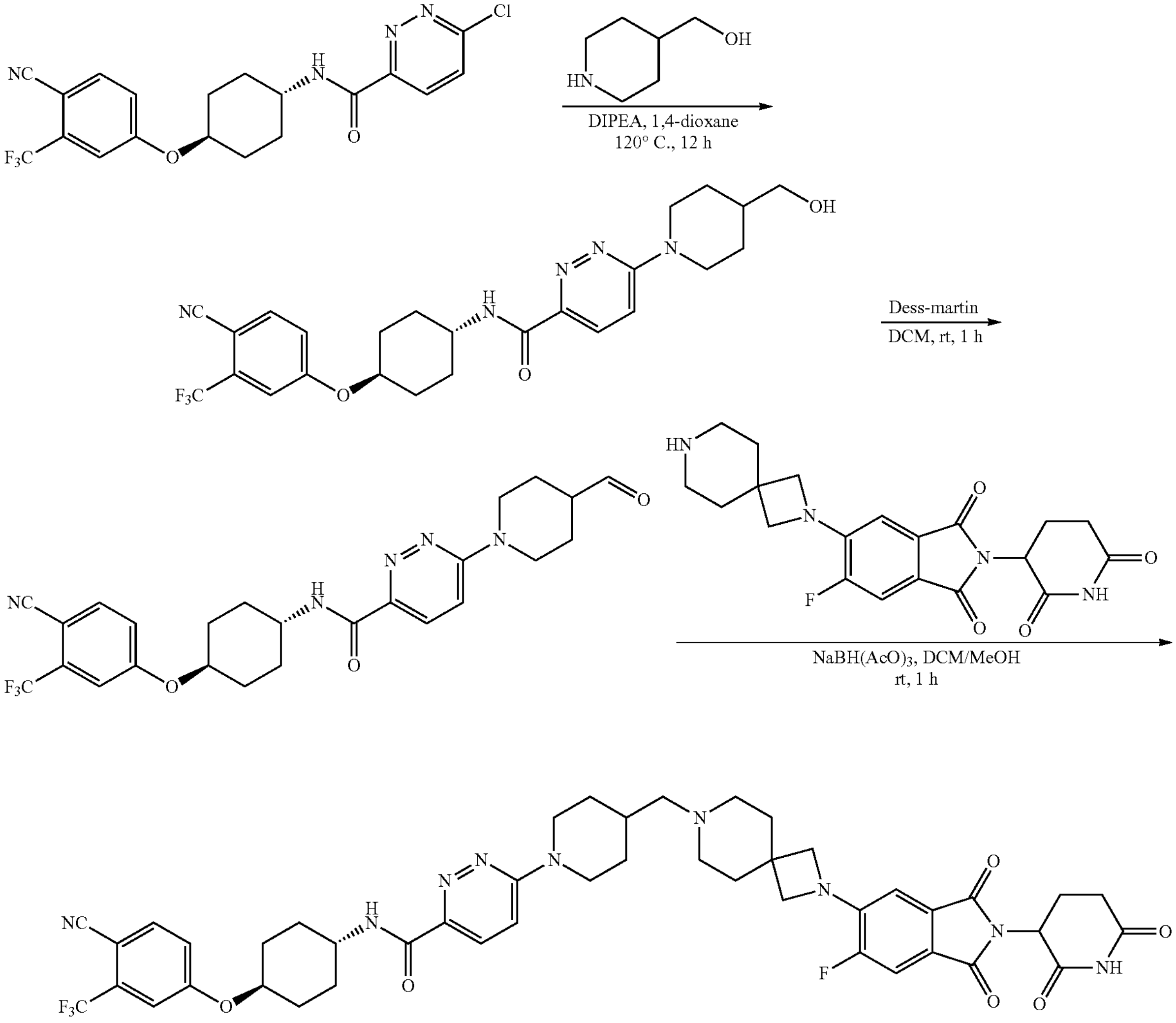

152

$^1$H NMR (400 MHz, DMSO-$d_6$) δ 8.61 (d, J=8.4 Hz, 1H), 8.07 (d, J=8.4 Hz, 1H), 7.80 (d, J=9.5 Hz, 1H), 7.59 (d, J=11.2 Hz, 1H), 7.51 (s, 1H), 7.33 (d, J=9.8 Hz, 1H), 6.90 (d, J=7.7 Hz, 1H), 5.06 (dd, J=12.9, 5.5 Hz, 1H), 4.63 (s, 1H), 4.47 (d, J=12.3 Hz, 2H), 3.00 (t, J=11.6 Hz, 2H), 2.87 (t, J=13.0 Hz, 1H), 2.58 (d, J=17.8 Hz, 1H), 2.30 (s, 3H), 2.12 (d, J=6.8 Hz, 4H), 2.06-1.96 (m, 1H), 1.90 (d, J=10.2 Hz, 3H), 1.77 (s, 5H), 1.68 (s, 5H), 1.59-1.46 (m, 3H), 1.23 (s, 2H), 1.06 (dd, J=17.3, 10.3 Hz, 3H), 0.84 (d, J=7.5 Hz, 1H). LCMS (ESI$^+$) calcd for $C_{45}H_{47}F4N_9O_6$ ($[M+H]^+$) m/z 885.92; found 886.4.
153: N-((1r,4r)-4-(4-cyano-3-(methoxy-ds)phenoxy) cyclohexyl)-6-(4-((2-(2,6-dioxopiperidin-3-yl)-1,3)-dioxoisoindolin-5-yl)-2,7-diazaspiro[3.5]nonan-7-yl) methyl)piperidin-1-yl)pyridazine-3-carboxamide
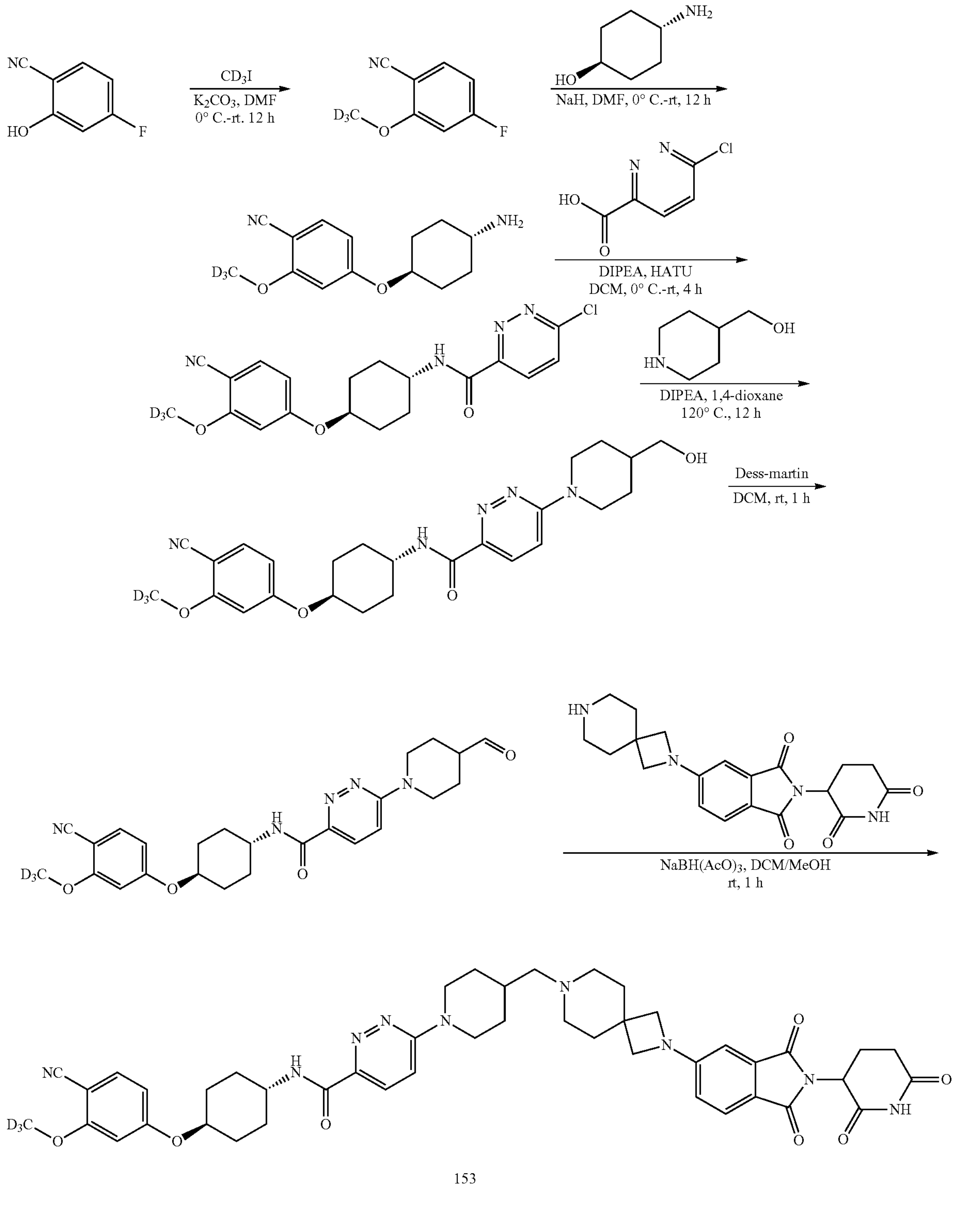

$^1H$ NMR (400 MHz, DMSO-$d_6$) δ 11.08 (s, 1H), 8.58 (d, J=8.3 Hz, 1H), 7.81 (t, J=8.5 Hz, 1H), 7.68-7.56 (m, 2H), 7.32 (d, J=9.7 Hz, 1H), 6.77 (s, 1H), 6.74-6.69 (m, 2H), 6.65 (d, J=8.3 Hz, 1H), 5.76 (s, 1H, 5.05 (dd, J=12.9, 5.4 Hz, 1H), 4.47 (d, J=11.7 Hz, 3H), 3.85 (s, 1H), 3.16 (s, 1H), 3.00 (t, J=11.8 Hz, 2H), 2.94-2.81 (m, 1H), 2.63-2.53 (m, 2H), 2.32 (s, 4H), 2.12 (d, J=6.9 Hz, 4H), 2.04-1.97 (m, 1H), 1.89 (s, 3H), 1.76 (s, 6H), 1.64 (dd, J=23.7, 11.0 Hz, 2H), 1.56-1.47 (m, 2H), 1.23 (s, 2H), 1.09 (dd, J=22.4, 9.9 Hz, 2H), 0.84 (d, J=6.8 Hz, 1H). LC/MS (ESI$^+$) calcd for $C_{45}H_{48}D_3N_9O_7$ ($[M+H]^+$) m/z 832.98; found 833.3.
154: N-((1r,4r)-4-(4-cyano-3-ethoxyphenoxy)cyclohexyl)-6-(4-((2-(2,6-dioxopiperidin-3-yl)-1,3-dioxoisoindolin-5-yl)-2,7-diazaspiro[3.5]nonan-7-yl)methyl)piperidin-1-yl)pyridazine-3-formamide
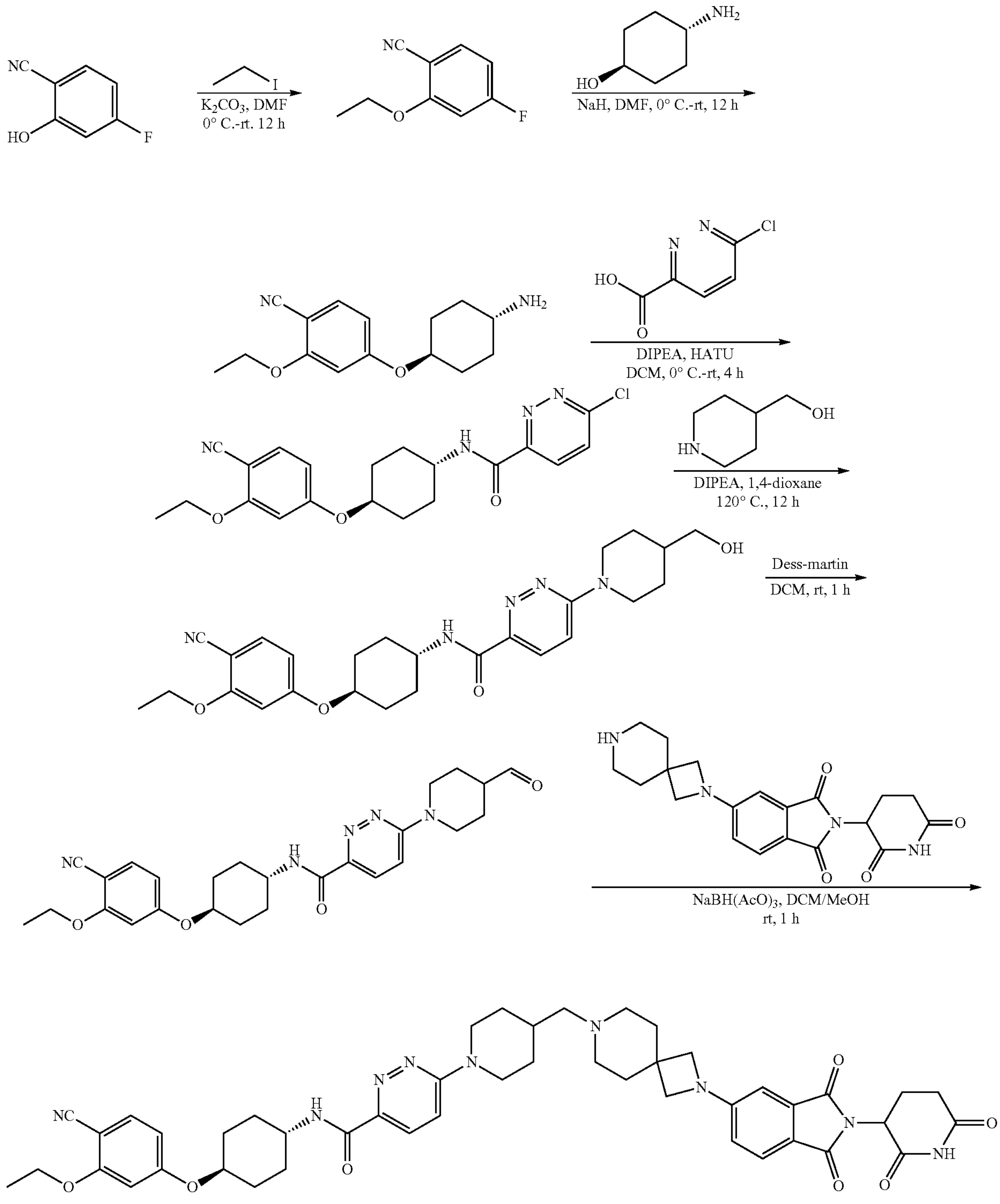
154

$^1$H NMR (400 MHz, DMSO-$d_6$) δ 11.08 (s, 1H), 8.58 (d, J=8.3 Hz, 1H), 7.80 (d, J=9.6 Hz, 1H), 7.66-7.56 (m, 2H), 7.32 (d, J=9.8 Hz, 1H), 6.78 (d, J=1.8 Hz, 1H), 6.70 (dd, J=4.5, 2.4 Hz, 2H), 6.65 (dd, J=8.4, 1.9 Hz, 1H), 5.76 (s, 1H), 5.05 (dd, J=12.8, 5.4 Hz, 1H), 4.53-4.42 (m, 3H) 4.17 (q, J=7.0 Hz, 2H), 3.85 (d, J=8.2 Hz, 1H), 3.75 (s, 4H), 3.16 (s, 1H), 3.00 (t, J=11.8 Hz, 2H), 2.94-2.81 (m, 1H), 2.57 (dd, J=18.9, 5.0 Hz, 2H), 2.32 (s, 3H), 2.12 (d, J=6.5 Hz, 4H), 2.04-1.96 (m, 1H), 1.89 (s, 3H), 1.76 (s, 4H), 1.63 (dd, J=24.3, 10.8 Hz, 2H), 1.50 (dd, J=23.3, 10.4 Hz, 2H), 1.35 (t, J=7.0 Hz, 3H), 1.23 (s, 1H), 1.17-1.01 (m, 2H-1, 0.84 (d, J=6.9 Hz, 1H). LC/MS ($ESI^+$) calcd for $C_{46}H_{53}N_9O_7$ ($[M+H]^+$) m/z 843.99; found 844.4.

155: N-((1r,4r)-4-(4-cyano-3-(2-methoxyethoxy)phenoxy)cyclohexyl)-6-(4-((2-(2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide

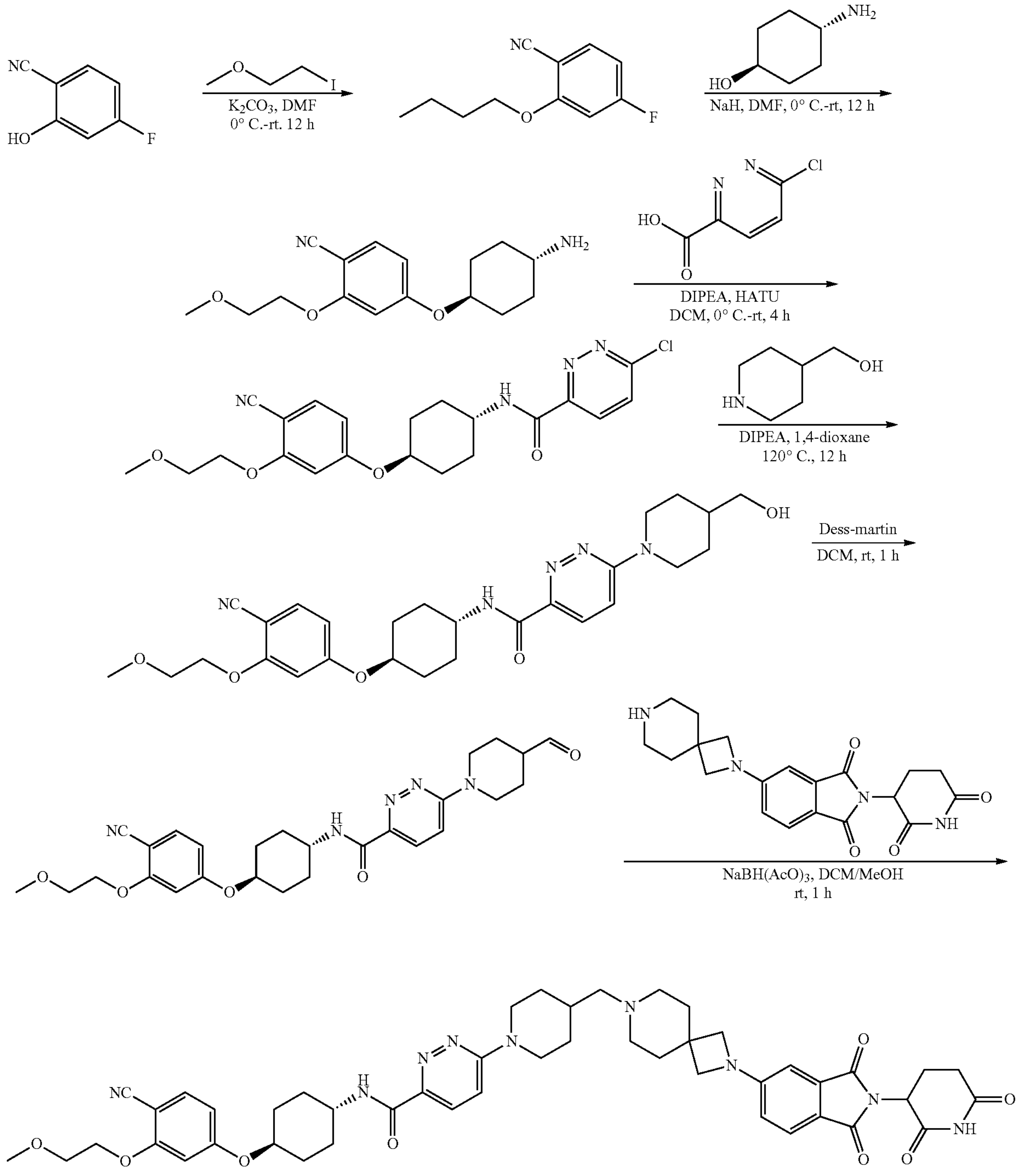

155

$^1$H NMR (400 MHz, DMSO-$d_6$) β 11.07 (s, 1H), 8.59 (d, J=8.1 Hz, 1H), 7.80 (d, J=9.5 Hz, 1H), 7.62 (dd, J=12.7, 8.5 Hz, 2H), 7.33 (d, J=9.5 Hz, 1H), 6.76 (d, J=9.6 Hz, 2H), 6.71 (d, J=8.6 Hz, 1H), 6.65 (d, J=8.5 Hz, 1H), 5.76 (s, 2H), 5.05 (dd, J=12.8, 5.4 Hz, 1H), 4.47 (d, J=10.1 Hz, 3H), 4.30-4.22 (m, 2H), 3.85 (s, 1H), 3.75 (s, 4H), 3.71-3.65 (m, 2H), 3.30 (s, 2H), 3.17 (d, J=5.3 Hz, 1H), 3.00 (t, J=11.7 Hz, 2H), 2.86 (d, J=10.9 Hz, 1H), 2.59 (s, 2H), 2.33 (s, 4H), 2.12 (s, 4H), 1.99 (s, 1H), 1.89 (d, J=9.7 Hz, 3H), 1.79 (d, J=21.6 Hz, 6H), 1.63 (d, J=12.9 Hz, 2H), 1.50 (d, J=12.8 Hz, 2H), 1.17-1.01 (m, 3H), 0.85 (s, 1H). LC/MS (ESI[+]) calcd for $C_{47}H_{55}N_9O_8$ ([M+H][+]) m/z 874.01; found 875.0.

156: N-((1r,4r)-4-(3-chloro-4-cyanophenoxy)cyclohexyl)-5-(5-((1-(2-(2,6-dioxopiperidin-3-yl)-1,3-dioxoisoindolin-5-yl)piperidine-4-yl)methyl) hexahydropyrrolo[3,4-c]pyrrol-2(1H)-yl)pyrazine-2-carboxamide

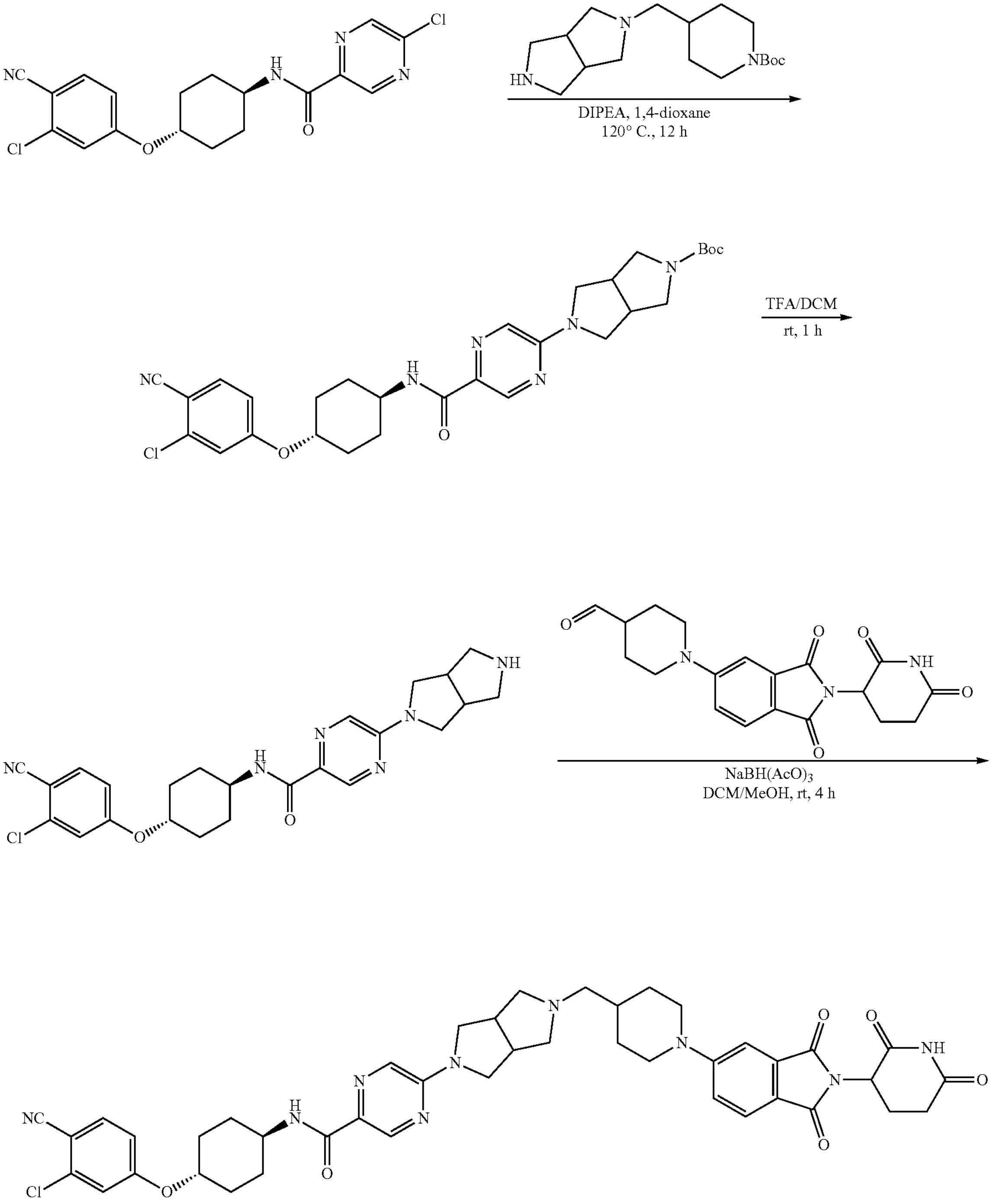

Step 1: 5-chloro-N-((1r,4r)-4-(3-chloro-4-cyanophenoxy)cyclohexyl)pyrazine-2-carboxamide (185 mg, 0.46 mmol), t-butyl 4-((hexahydropyrrolo[3,4-c]pyrrol-2(1H)-yl)methyl)piperidine-1-carboxylate (260 mg, 0.92 mmol) and diisopropylethylamine (297 mg, 2.30 mmol) were added in 8 mL of dioxane. The reaction solution was heated to 115° C., stirred and reacted overnight under reflux. After cooling to room temperature, the reaction solution was added with ethyl acetate and water for extraction. The organic phase was successively washed with 0.05 N HCl and saturated brine, and dried over anhydrous sodium sulfate. The solvent was removed by rotary evaporation to obtain the crude product, which was separated and purified by Pre-TLC, to provide compound t-butyl 5-(5-((1r,4r)-4-(3-chloro-4-cyanophenoxy)cyclohexyl)carbamoyl)pyrazine-2-yl)hexahydropyrrolo[3,4-c]pyrrol-2(1H)-carboxylate (109 mg), with a yield of 37%. LC/MS (ESI$^+$) calcd for $C_{29}H_{35}ClN_6O_4$ ([M+H]$^+$) m/z 567.09; found 567.1.

Step 2: Compound t-butyl 5-(5-((1r,4r)-4-(3-chloro-4-cyanophenoxy)cyclohexyl) carbamoyl)pyrazine-2-yl)hexahydropyrrolo[3,4-c]pyrrol-2(1H)-carboxylate (200 mg, 0.41 mmol) was dissolved in 5 ml dichloromethane, to which was then added 2 ml trifluoroacetic acid, and the mixture was allowed to react 3 h under stirring at room temperature. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound N-((1r,4r)-4-(3-chloro-4-cyanophenoxy) cyclohexyl)-5-(hexahydropyrrolo[3,4-c]pyrrol-2(1H)-yl)pyrazine-2-carboxamide (142 mg), with a yield of 90%. LC/MS (ESI$^+$) calcd for $C_{24}H_{27}ClN_6O_2$ ([M+H]$^+$) m/z 466.97; found 467.1.

Step 3: N-((1r,4r)-4-(3-chloro-4-cyanophenoxy)cyclohexyl)-5-(hexahydropyrrolo[3,4-c]pyrrol-2(1H)-yl)pyrazine-2-carboxamide (30 mg, 0.06 mmol) was weighed and placed in a 25 mL single-neck round bottom flask, to which was added dichloromethane (3 mL), and the mixture was stirred at room temperature to dissolve and make the solution become clear. Subsequently, 1-(2-(2,6-dioxopiperidin-3-yl)-1,3-dioxoisoindol-5-yl)piperidine-4-acetaldehyde (24 mg, 0.06 mmol) was added to the system, and the reaction was stirred and reacted at room temperature for 15 min. After that, sodium triacetylborohydride (38 mg, 0.18 mmol) was added to the system, and the system was allowed to react under stirring at room temperature. After 4 h, the sample was taken out and subjected to TLC, and the result indicated the disappearance of the starting material. The stirring was stopped. Dichloromethane (15 mL) and water (15 mL) were added to the system. The system was stirred vigorously, and then allowed to stand for separation of layers. The water layer was extracted with dichloromethane (10 mL*3). The organic phases were combined, successively washed with water (10 mL*2) and saturated brine (15 mL), and dried over anhydrous sodium sulfate. The solvent was removed by rotary evaporation to obtain the crude product, which was then separated and purified by Pre-TLC to obtain compound N-((1r,4r)-4-(3-chloro-4-cyanophenoxy)cyclohexyl)-5-(5-((1-(2-(2,6-dioxopiperidin-3-yl)-1,3-dioxoisoindolin-5-yl)piperidine-4-yl)methyl)hexahydropyrrolo[3,4-c]pyrrol-2(1H)-yl)pyrazine-2-carboxamide (21 mg), with a yield of 39%. $^1$H NMR (400 MHz, DMSO-$d_6$) δ 11.05 (s, 1H), 8.59 (d, J=1.0 Hz, 1H), 8.07 (d, J=8.2 Hz, 1H), 7.91 (s, 1H), 7.84 (d, J=8.7 Hz, 1H), 7.61 (d, J=8.5 Hz, 1H), 7.35 (d, J=2.3 Hz, 1H), 7.26 (s, 1H), 7.18 (d, J=8.7 Hz, 1H), 7.11 (dd, J=8.8, 2.3 Hz, 1H), 5.74 (s, 1H), 5.03 (dd, J=12.9, 5.2 Hz, 1H), 4.48 (d, J=5.6 Hz, 1H), 3.99 (d, J=12.6 Hz, 2H), 3.78 (d, J=8.7 Hz, 3H), 3.49 (s, 1H), 3.39 (d, J=11.1 Hz, 2H), 2.91 (s, 2H), 2.56 (d, J=9.0 Hz, 3H), 2.22 (d, J=6.3 Hz, 2H), 2.07 (d, J=11.1 Hz, 2H), 1.98 (d, J=8.8 Hz, 2H), 1.85 (s, 2H), 1.74 (d, J=11.0 Hz, 3H), 1.59 (d, J=12.9 Hz, 2H), 1.55-1.43 (m, 3H), 1.16-1.05 (m, 3H), 0.82 (d, J=7.0 Hz, 1H). LC/MS (ESI$^+$) calcd for $C_{43}H_{46}ClN_9O_6$ ([M+H]$^+$) m/z 820.35. found 820.3.

157: N-((1r,4r)-4-(3-chloro-4-cyanophenoxy)cyclohexyl)-5-(5-((1-(2-(2,6-dioxopiperidin-3-yl)-6-fluoro-1,3-dioxoisoindolin-5-yl)piperidine-4-yl)methyl)hexahydropyrrolo[3,4-c]pyrrol-2(1H)-yl)pyrazine-2-carboxamide

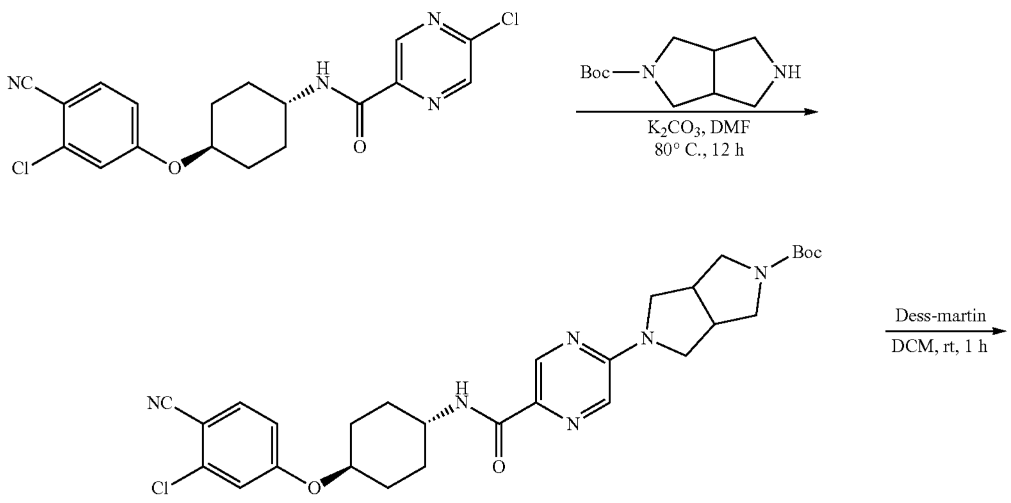

-continued

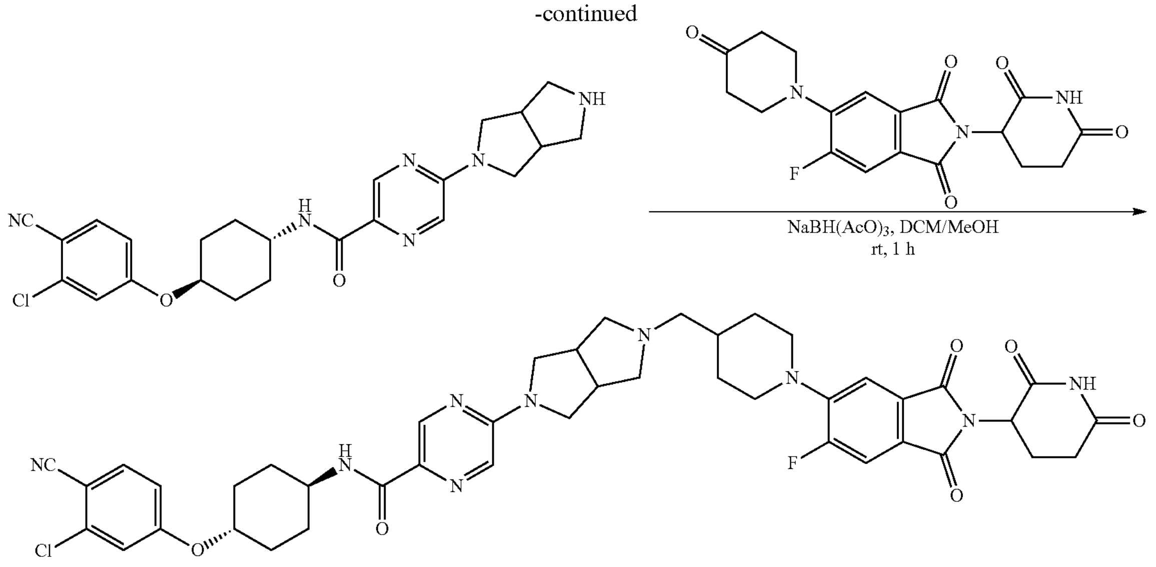

157

$^1$H NMR (400 MHz, DMSO-$d_6$) δ 11.10 (s, 1H), 8.60 (s, 1H), 8.08 (d, J=8.2 Hz, 1H), 7.93 (s, 1H), 7.86 (d, J=8.8 Hz, 1H), 7.69 (d, J=11.7 Hz, 1H), 7.41 (d, J=7.2 Hz, 1H), 7.37 (s, 1H), 7.12 (d, J=8.9 Hz, 1H), 5.09 (dd, J=12.7, 5.3 Hz, 1H), 4.51 (s, 1H), 4.10 (q, J=5.3 Hz, 2H), 3.79 (s, 3H), 3.57 (d, J=11.7 Hz, 2H), 3.41 (d, J=11.6 Hz, 2H), 3.17 (d, J=5.2 Hz, 5H), 2.94 (s, 2H), 2.90-2.79 (m, 3H), 2.59 (d, J=9.0 Hz, 2H), 2.28 (d, J=6.7 Hz, 2H), 2.07 (s, 2H), 1.90-1.75 (m, 4H), 1.60 (d, J=12.4 Hz, 2H), 1.56-1.47 (m, 2H), 1.23 (s, 1H). LC/MS ($ESI^+$) calcd for $C_{43}H_{45}ClFN_9O_6$ ($[M+H]^+$) m/z 838.34; found 838.3.

158: N-((1r,4r)-4-(3-chloro-4-cyanophenoxy)cyclohexyl)-3-(4-((2-(2,6-dioxopiperidin-3-yl)-6-fluoro-1,3-dioxoisoindolin-5-yl)-2,7-diazaspiro[3.5]nonan-7-yl)methyl)piperidin-1-yl)-1,2,4-triazine-6-formamide

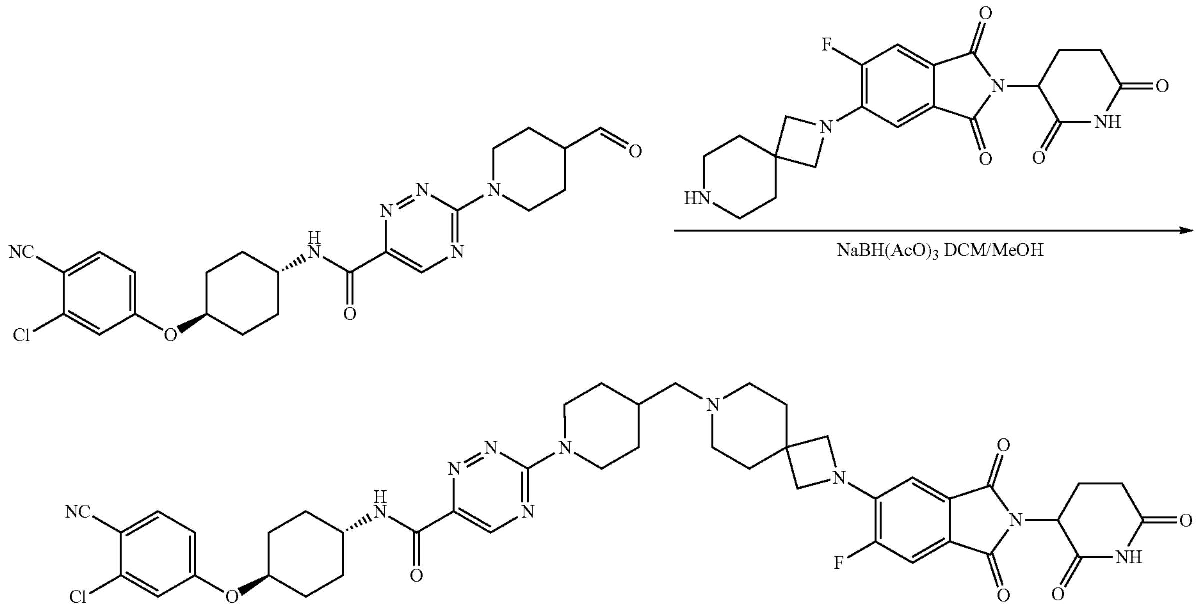

157

LC/MS ($ESI^+$) Calcd for $C_{43}H_{46}FClN_{10}O_6(M+H^+)$ m/z, 853.3; found 853.3. $^1$H NMR (400 MHz, $CDCl_3$) δ 8.81 (s, 1H), 8.05 (s, 1H), 7.57 (dd, J=8.4, 2.5 Hz, 2H), 7.36 (d, J=10.9 Hz, 1H), 7.00 (d, J=2.4 Hz, 1H), 6.87-6.79 (m, 2H), 4.91 (dd, J=12.3, 5.3 Hz, 2H), 4.31 (dd, J=12.2, 8.3 Hz, 1H), 4.10-4.01 (m, 1H), 3.89 (d, J=1.9 Hz, 4H), 3.05 (s, 2H), 2.94-2.65 (m, 4H), 2.40 (s, 3H), 2.23-2.15 (m, 5H), 1.90-1.85 (m, 7H), 1.69 (d, J=12.4 Hz, 3H), 1.46 (d, J=12.7 Hz, 3H), 1.25 (s, 3H).

159: N-((1r,4r)-4-(3-chloro-4-cyanophenoxy)cyclohexyl)-5-(5-((1-(2,6-dioxopiperidin-3-yl)-6-fluoro-1,3-dioxoisoindolin-5-yl(azetidine-3-yl)methyl) hexahydropyrrolo[3,4-c]pyrrol-2(1H)-yl)pyrazine-2-carboxamide

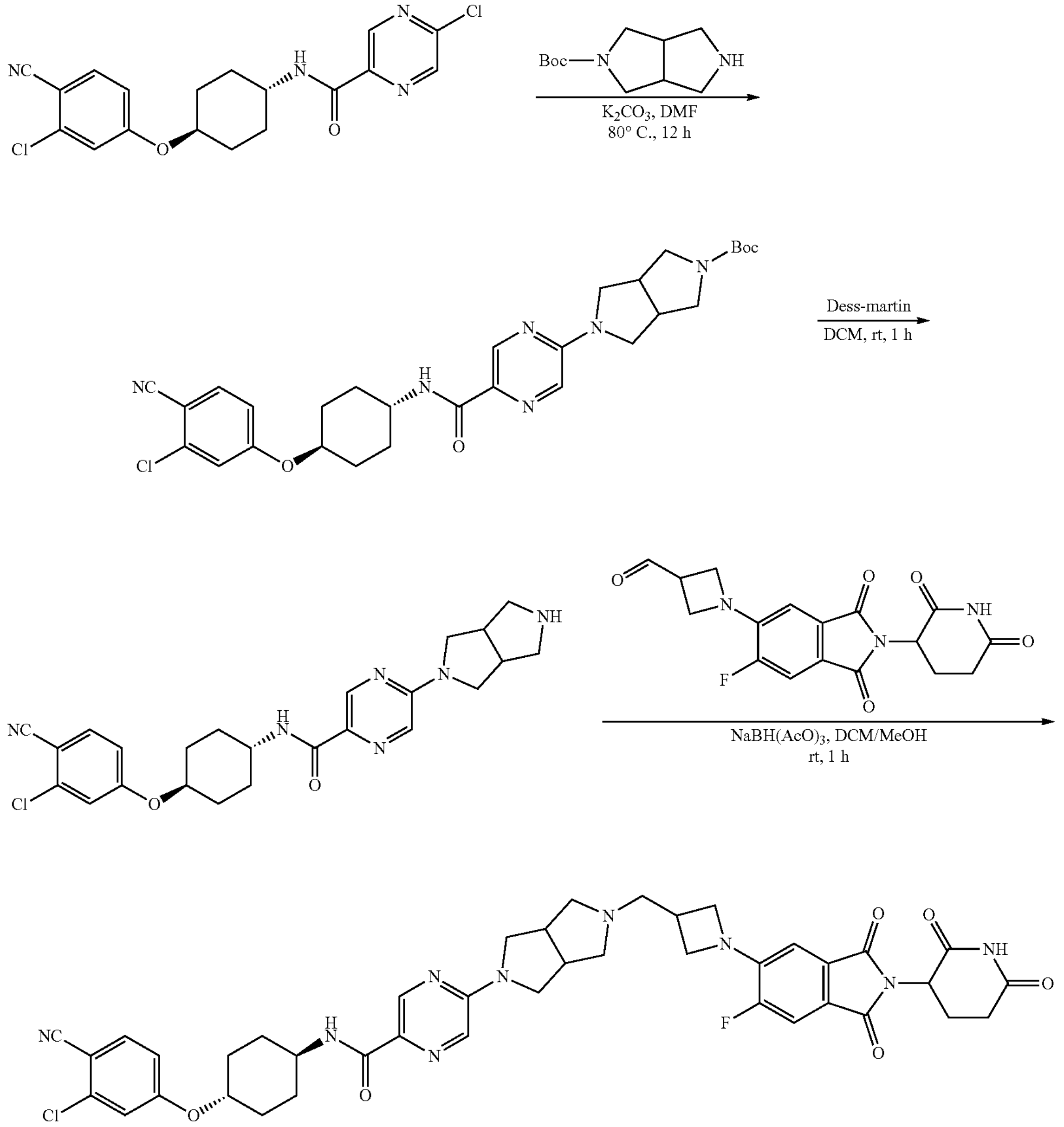

159

$^1$H NMR (400 MHz, DMSO-$d_6$) δ11.08 (s, 1H), 8.60 (d, J=1.3 Hz, 1H), 8.09 (d, J=8.3 Hz, 1H), 7.93 (d, J=1.2 Hz, 1H), 7.86 (d, J=8.8 Hz, 1H), 7.57 (d, J=11.2 Hz, 1H), 7.37 (d, J=2.4 Hz, 1H), 7.13 (dd, J=8.8, 2.4 Hz, 1H), 6.88 (d, J=7.6 Hz, 1H), 5.05 (dd, J=12.8, 5.4 Hz, 1H), 4.52 (s, 1H), 4.24 (t, J=8.4 Hz, 2H), 3.85-3.79 (m, 3H), 3.77 (d, J=3.1 Hz, 1H), 3.51 (s, 1H), 3.41 (d, J=9.9 Hz, 2H), 2.94 (s, 2H), 2.87 (dd, J=15.8, 10.1 Hz, 2H), 2.69 (s, 1H), 2.67 (s, 1H), 2.60 (s, 2H), 2.55 (s, 2H), 2.17 (t, J=8.0 Hz, 1H), 2.09 (d, J=11.6 Hz, 2H), 2.00 (d, J=5.5 Hz, 1H), 1.91-1.86 (m, 2H), 1.60 (d, J=13.0 Hz, 1H), 1.56-1.47 (m, 2H), 1.30 (s, 1H), 1.26 (s, 1H), 0.84 (d, J=7.1 Hz, 1H). LC/MS (ESI$^+$) calcd for $C_{41}H_{41}ClFN_9O_6$ ([M+H]$^+$) m/z 810.28, found 810.3.

160: N-((1r,4r)-4-(3-chloro-4-cyanophenoxy)cyclohexyl)-6-(5-((1-(2,6-dioxopiperidin-3-yl)-6-fluoro-1,3-dioxoisoindolin-5-yl)azetidine-3-yl)methyl) hexahydropyrrolo[3,4-c]pyrrol-2(1H)-yl)pyridazine-3-formamide

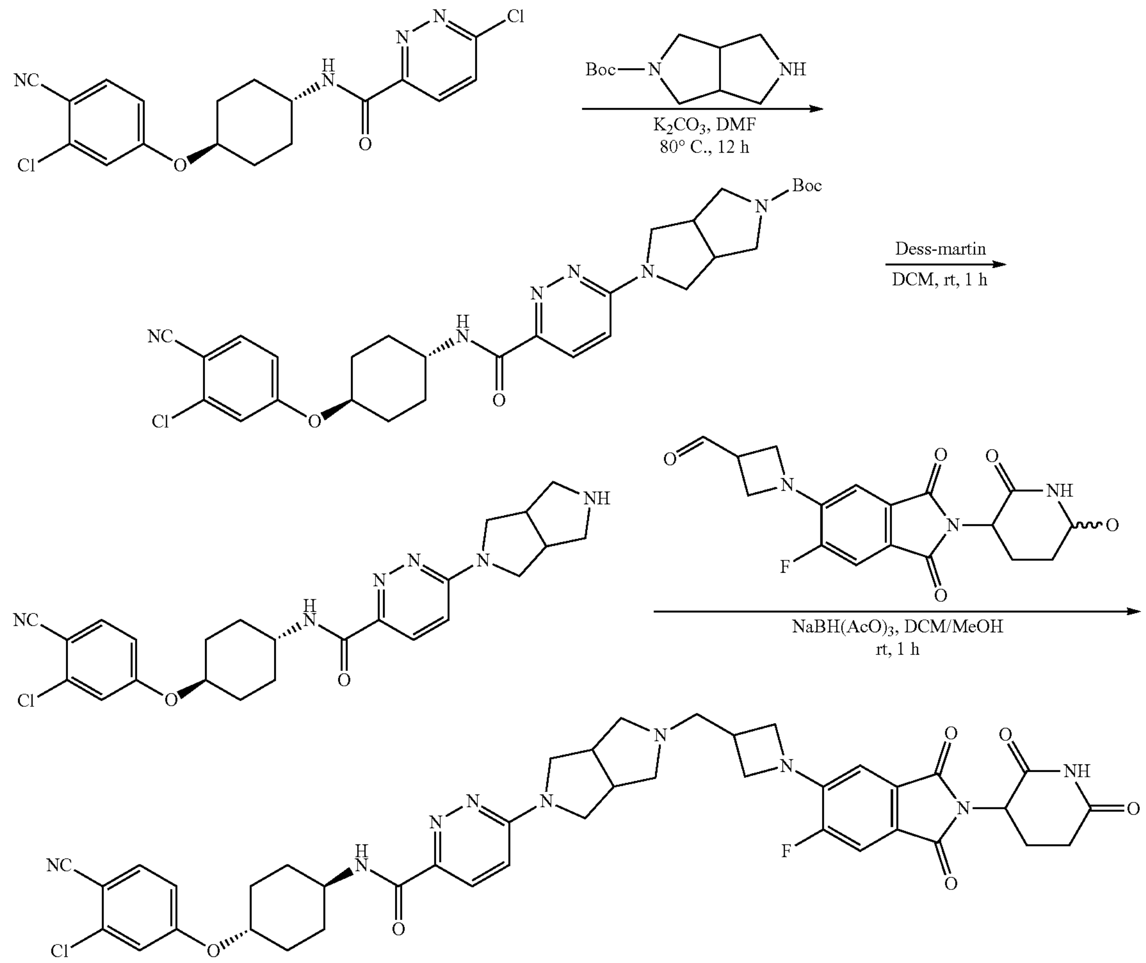

160

$^1$H NMR (400 MHz, DMSO-d$_6$) δ 11.08 (s, 1H), 8.57 (d, J=8.1 Hz, 1H), 7.84 (dd, J=12.4, 9.1 Hz, 2H), 7.57 (d, J=11.2 Hz, 1H), 7.39 (d, J=2.3 Hz, 1H), 7.14 (dd, J=8.8, 2.3 Hz, 1H), 7.00 (d, J=9.4 Hz, 1H), 6.88 (d, J=7.7 Hz, 1H), 5.76 (s, 1H), 5.05 (dd, J=12.8, 5.3 Hz, 1H), 4.54 (s, 1H), 4.25 (t, J=7.1 Hz, 2H), 3.83 (d, J=7.0 Hz, 3H), 3.77 (s, 2H), 3.41 (d, J=11.3 Hz, 3H), 2.96 (s, 2H), 2.92-2.81 (m, 2H), 2.62 (d, J=6.3 Hz, 2H), 2.10 (d, J=11.1 Hz, 2H), 2.00 (d, J=5.6 Hz, 1H), 1.91 (d, J=8.3 Hz, 2H), 1.78 (s, 1H), 1.64 (dd, J=23.8, 10.9 Hz, 2H), 1.57-1.46 (m, 2H), 1.28 (d, J=16.0 Hz, 1H), 1.23 (s, 1H), 0.88 (d, J=23.7 Hz, 1H). LC/MS (ESI$^+$) calcd for $C_{41}H_{41}ClFN_9O_6$ ([M+H]$^+$) m/z 810.28; found 810.3.

161: N-((1r,3r)-3-(3-chloro-4-cyanophenoxy)-2,2,4,4-tetramethylcyclobutyl)-6-(5-((1-(2-(2,6-dioxopiperidin-3-yl)-6-fluoro-1,3-dioxoisoindolin-5-yl)azelaic acid-3-yl)methyl)hexahydropyrrolo[3,4-c]pyrrol-2(1H)-pyrazole)formamide

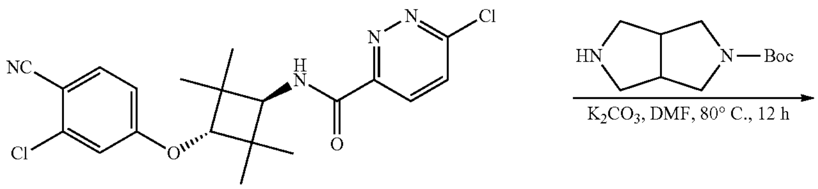

-continued
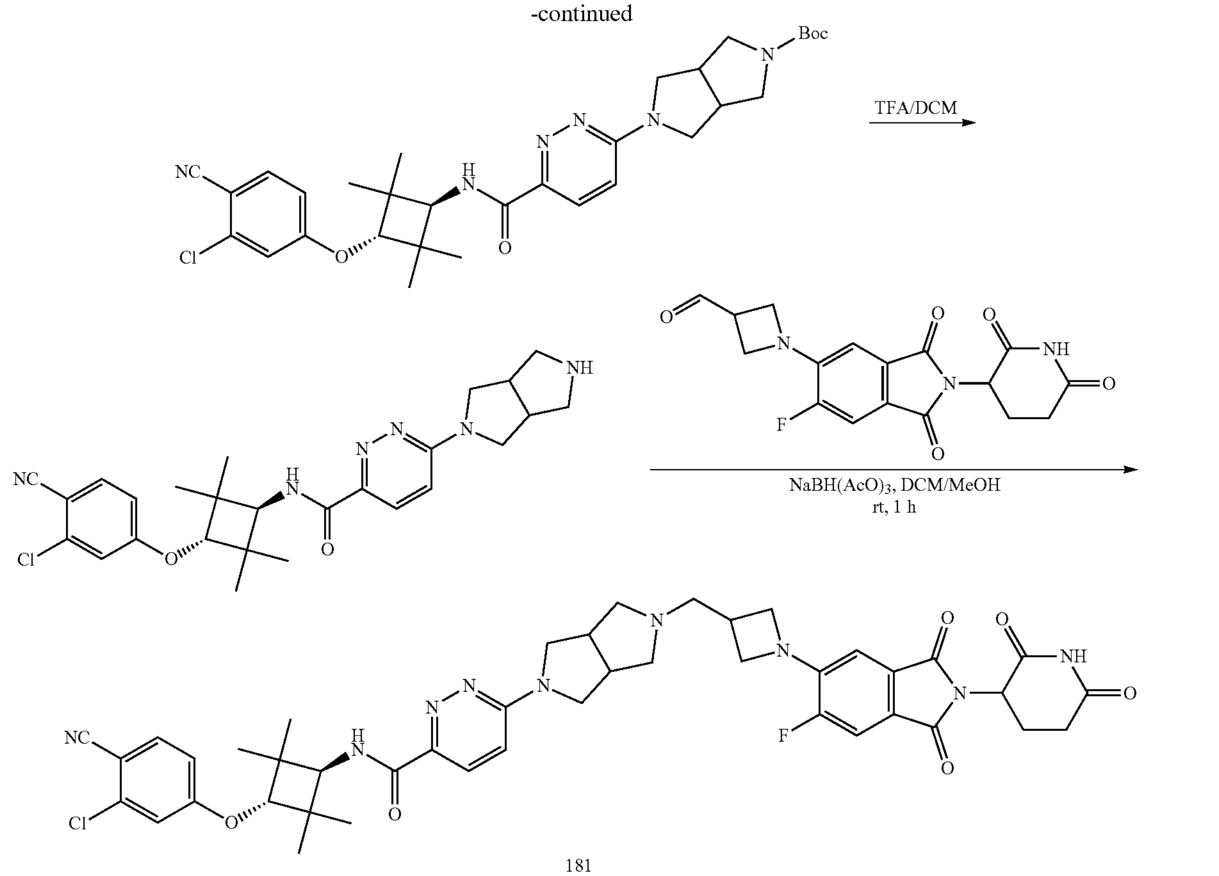
181
$^1$H NMR (400 MHz, DMSO-$d_6$) δ 11.08 (s, 1H), 8.25 (d, J=9.3 Hz, 1H), 7.91 (d, J=8.7 Hz, 1H), 7.85 (d, J=9.4 Hz, 1H), 7.57 (d, J=11.2 Hz, 1H), 7.25 (d, J=2.4 Hz, 1H), 7.03 (dd, J=9.3, 3.2 Hz, 2H), 6.88 (d, J=7.6 Hz, 1H), 5.76 (s, 2H), 5.05 (dd, J=12.9, 5.3 Hz, 1H), 4.46 (s, 1H), 4.25 (t, J=7.2 Hz, 2H), 4.01 (d, J=9.2 Hz, 1H), 3.85-3.74 (m, 4H), 3.51 (s, 1H), 3.44 (d, J=7.4 Hz, 3H), 2.97 (s, 2H), 2.92-2.82 (m, 2H), 2.67 (dd, J=13.8, 8.2 Hz, 4H), 1.30 (s, 1H), 1.26 (s, 1H), 1.22 (s, 6H), 1.14 (s, 6H). LC/MS (ESI$^+$) calcd for $C_{41}H_{41}ClFN_9O_6$ ([M+H]$^+$) m/z 838.34; found 838.2.
162: N-((1r,4r)-4-(3-chloro-4-cyanophenoxy)cyclohexyl)-6-(7-((1-(2-(2,6-dioxopiperidin-3-yl)-6-fluoro-1,3-dioxoisoindolin-5-yl)piperidine-4-yl)methyl)-2,7-diazaspiro[4.4]nonan-2-yl)pyridazine-3-formamide
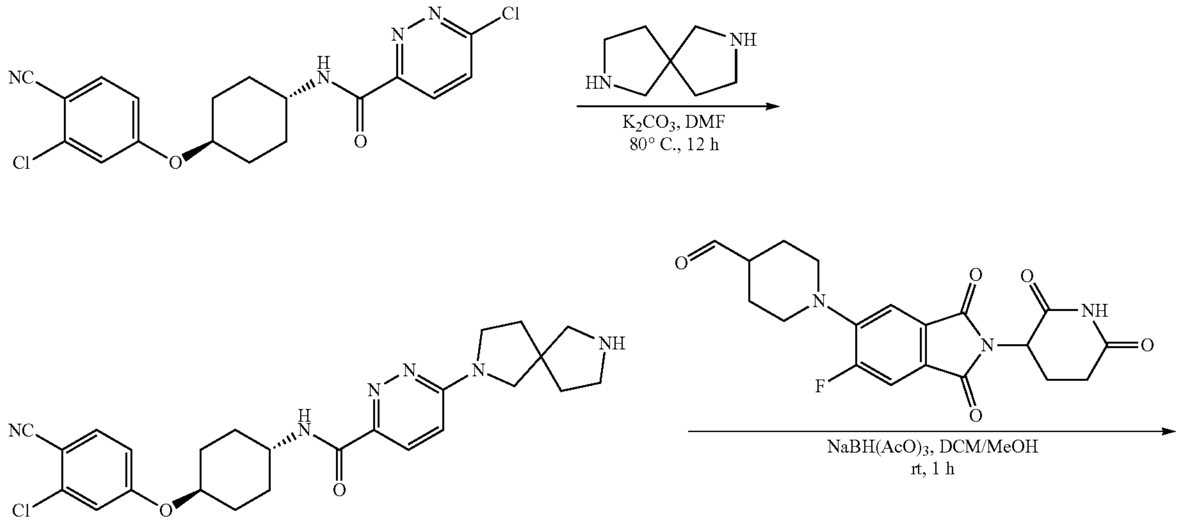

-continued

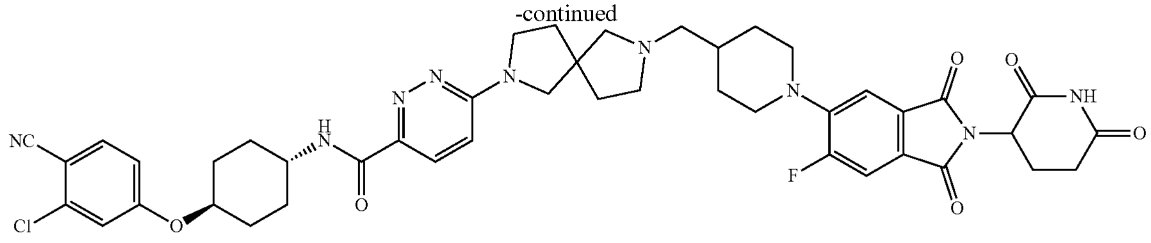

162

$^1$H NMR (400 MHz, DMSO-$d_6$) δ 11.12 (s, 1H), 8.55 (d, J=8.1 Hz, 1H), 7.84 (dd, J=17.9, 9.1 Hz, 2H), 7.71 (d, J=11.4 Hz, 1H), 7.44 (d, J=7.3 Hz, 1H), 7.40 (d, J=2.4 Hz, 1H), 7.14 (dd, J=8.8, 2.4 Hz, 1H), 6.95 (d, J=9.5 Hz, 1H), 5.10 (dd, J=13.0, 5.4 Hz, 1H), 4.54 (s, 1H), 3.85 (s, 1H), 3.60 (d, J=9.5 Hz, 3H), 3.44 (s, 1H), 3.17 (d, J=5.1 Hz, 1H), 2.94-2.82 (m, 3H), 2.69-2.61 (m, 1H), 2.55 (d, J=10.1 Hz, 2H), 2.43 (d, J=9.2 Hz, 2H), 2.32 (d, J=7.4 Hz, 2H), 2.10 (s, 2H), 2.02 (dd, J=13.1, 6.4 Hz, 3H), 1.90 (d, J=13.6 Hz, 2H), 1.82 (d, J=6.3 Hz, 3H), 1.71-1.58 (m, 3H), 1.57-1.46 (m, 2H), 1.29 (s, 1H), 1.25 (d, J=6.2 Hz, 3H), 0.86 (s, 1H). LC/MS (ESI$^+$) calcd for $C_{44}H_{47}ClFN_9O_6$ ([M+H]$^+$) m/z 852.37; found 851.8.

163: N-((1r,4r)-4-(3-chloro-4-cyanophenoxy)cyclohexyl)-S-(7-((1-(2,6-dioxopiperidin-3-yl)-6-fluoro-1,3-dioxoisoindolin-5-yl)piperidine-4-yl)methyl)-2,7-diazaspiro[4.4]nonan-2-yl)pyrazine-2-carboxamide

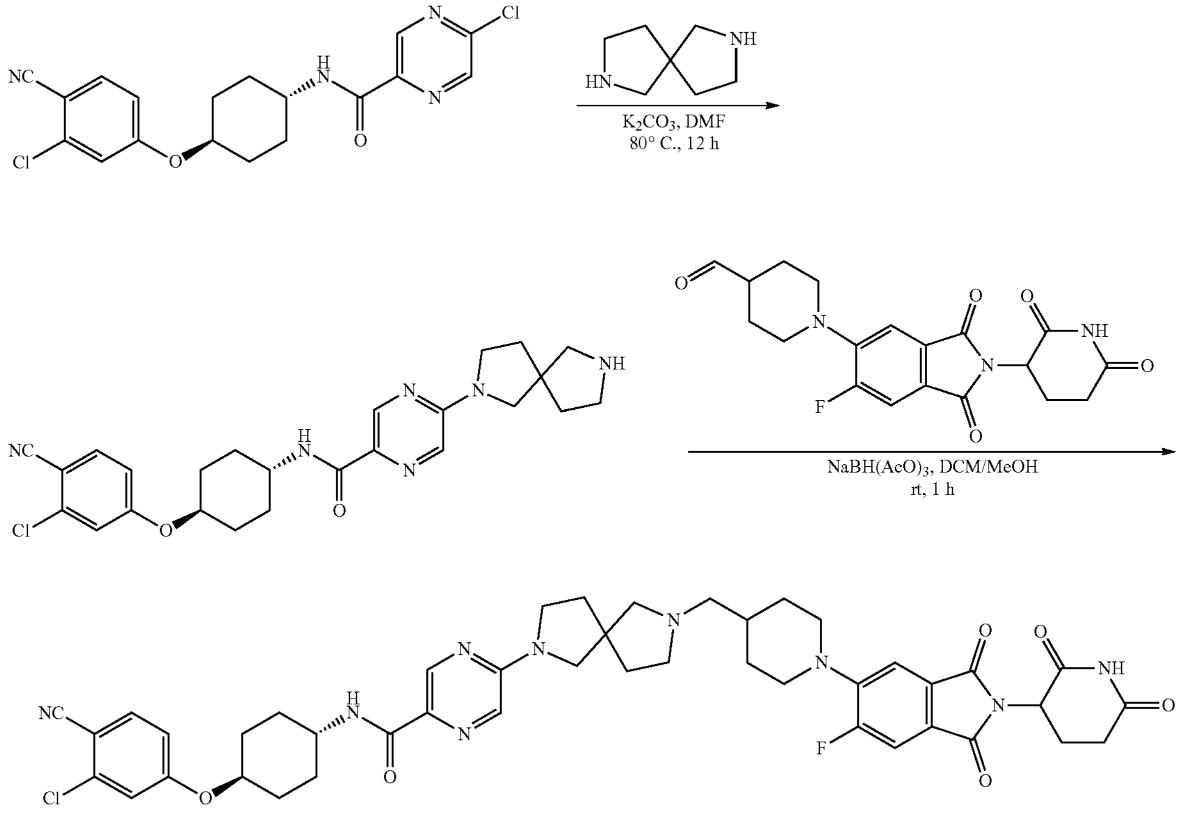

163

$^1$H NMR (400 MHz, $CDCl_3$) δ 8.87 (d, J=1.2 Hz, 1H), 7.73 (d, J=1.2 Hz, 1H), 7.61-7.55 (m, 1H), 7.47 (d, J=11.0 Hz, 1H), 7.43 (d, J=8.2 Hz, 1H), 7.39 (d, J=7.3 Hz, 1H), 7.01 (d, J=2.4 Hz, 1H), 6.87 (dd, J=8.7, 2.4 Hz, 1H), 4.95 (dd, J=12.3, 5.3 Hz, 1H), 4.40-4.26 (m, 1H), 4.05 (dd, J=11.7, 7.2 Hz, 1H), 3.72-3.58 (m, 6H), 2.96-2.71 (m, 8H), 2.54 (d, J=6.9 Hz, 2H), 2.24-2.13 (m, 5H), 2.00-1.86 (m, 4H), 1.71 (dd, J=22.4, 9.7 Hz, 3H), 1.56-1.38 (m, 4H), 1.33 (d, J=19.3 Hz, 1H), 1.27 (s, 1H), 0.90 (s, 1H). LC/MS (ESI$^+$) calcd for $C_{44}H_{47}ClFN_9O_6$ ([M+H]$^+$) m/z 852.37; found 852.3.

164: N-((1r,4r)-4-(3-chloro-4-cyanophenoxy)cyclohexyl)-6-(4-(7-(2-(2,6-dioxopiperidin-3-yl)-6-fluoro-1,3-dioxoisoindol-5-yl)-2,7-diazaspiro[4.4]nonan-2-yl)piperidin-1-yl)pyridazine-3-formamide

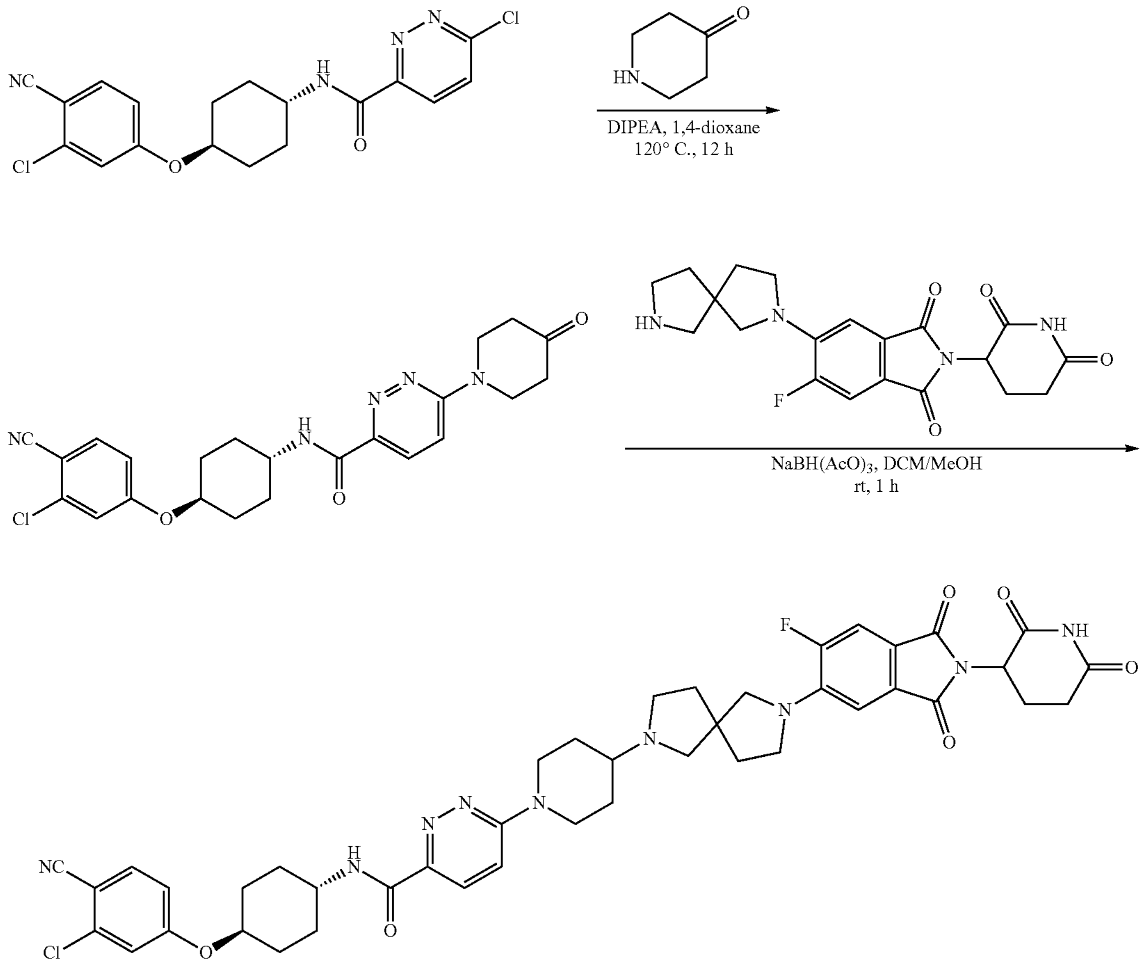

164

$^1$H NMR (400 MHz, DMSO-$d_6$) δ 11.09 (s, 1H), 8.59 (d, J=1.1 Hz, 1H), 8.26 (s, 1H), 8.09 (d, J=8.2 Hz, 1H), 7.87 (d, J=8.8 Hz, 1H), 7.59 (d, J=12.6 Hz, 1H), 7.38 (d, J=2.4 Hz, 1H), 7.13 (dd, J=8.8, 2.4 Hz, 1H), 7.04 (d, J=7.6 Hz, 1H), 5.76 (s, 1H), 5.06 (dd, J=12.9, 5.4 Hz, 1H), 4.53 (d, J=9.9 Hz, 1H), 4.27 (d, J=9.7 Hz, 2H), 3.83 (d, J=7.3 Hz, 1H), 3.62 (s, 2H), 3.51 (s, 1H), 3.46 (d, J=10.4 Hz, 2H), 3.21-3.13 (m, 5H), 2.89 (dd, J=22.4, 8.2 Hz, 1H), 2.72 (d, J=6.3 Hz, 1H), 2.66-2.58 (m, 2H), 2.55 (d, J=10.7 Hz, 1H), 2.35 (d, J=9.0 Hz, 1H), 2.09 (d, J=10.9 Hz, 2H), 2.04-1.96 (m, 1H), 1.90 (d, J=11.8 Hz, 2H), 1.87 (s, 2H), 1.79 (dd, J=14.7, 7.1 Hz, 2H), 1.67-1.56 (m, 2H), 1.56-1.47 (m, 2H), 1.47-1.38 (m, 2H), 0.95 (d, J=6.5 Hz, 1H). LC/MS (ESI$^+$) calcd for $C_{43}H_{45}ClFN_9O_6$ ([M+H]$^+$) m/z 838.34; found 837.8.

165: N-((1r,4r)-4-(3-chloro-4-cyanophenoxy)cyclohexyl)-5-(4-(7-(2-(2,6-dioxopiperidin-3-yl)-6-fluoro-1,3-dioxoisoindolin-5-yl)-2,7-diazaspiro[4.4]nonan-2-yl)piperidin-1-yl)pyrazine-2-carboxamide

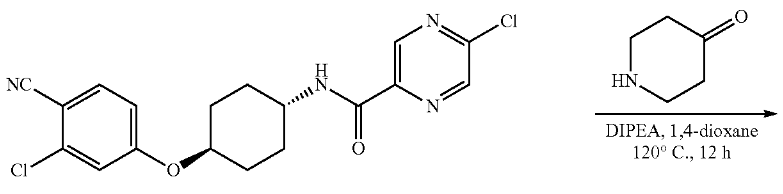

-continued

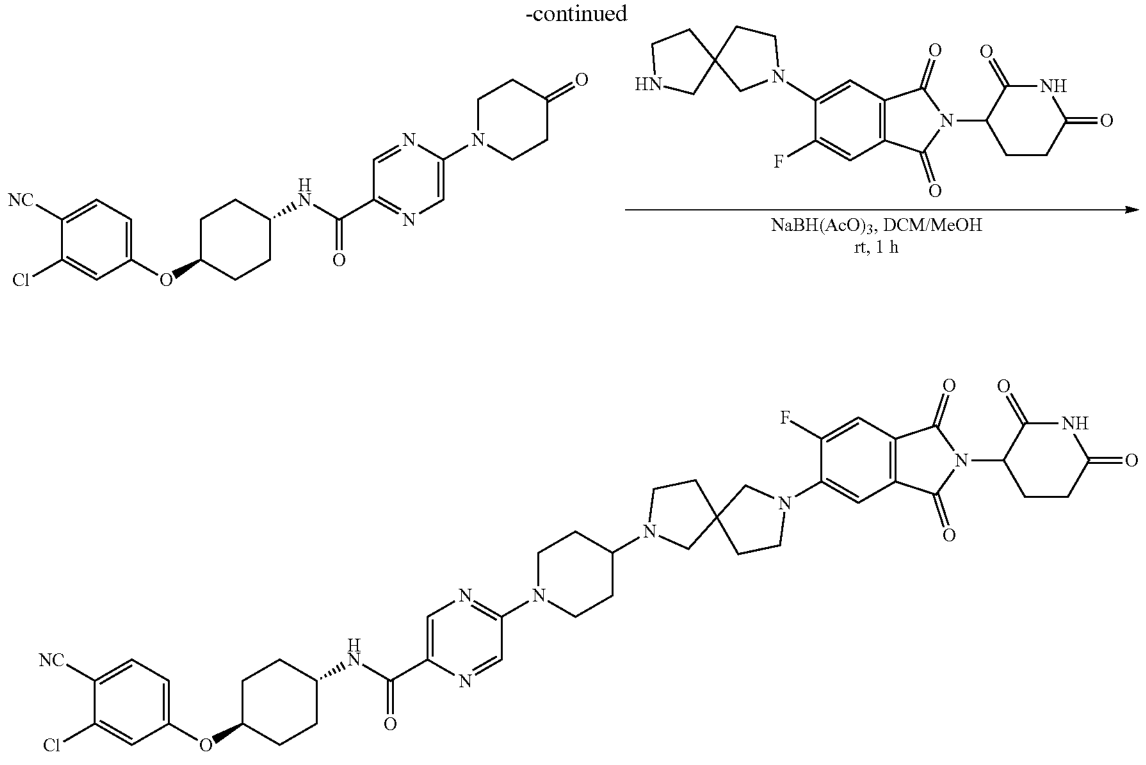

165

$^1$H NMR (400 MHz, DMSO-$d_6$) δ 11.09 (s, 1H), 8.60 (d, J=8.2 Hz, 1H), 7.86 (d, J=8.8 Hz, 1H), 7.81 (d, J=9.6 Hz, 1H), 7.59 (d, J=12.6 Hz, 1H), 7.40 (d, J=2.4 Hz, 1H), 7.35 (d, J=9.7 Hz, 1H), 7.14 (dd, J=8.8, 2.4 Hz, 1H), 7.05 (d, J=7.5 Hz, 1H), 5.06 (dd, J=12.9, 5.3 Hz, 1H), 4.53 (d, J=9.8 Hz, 1H), 4.30 (d, J=9.4 Hz, 2H), 3.85 (s, 1H), 3.62 (s, 2H), 3.53-3.43 (m, 4H), 3.22 (s, 1H), 2.94-2.83 (m, 1H), 2.72 (d, J=6.1 Hz, 1H), 2.63 (t, J=9.8 Hz, 2H), 2.55 (d, J=11.0 Hz, 1H), 2.35 (d, J=13.6 Hz, 2H), 2.11 (d, J=9.8 Hz, 2H), 2.01 (dd, J=12.0, 6.2 Hz, 1H), 1.90 (d, J=11.5 Hz, 3H), 1.83 (s, 1H), 1.78 (dd, J=14.4, 7.8 Hz, 2H), 1.64 (dd, J=23.9, 10.6 Hz, 2H), 1.56-1.49 (m, 2H), 1.42 (d, J=9.3 Hz, 2H), 1.24 (s, 1H), 0.95 (d, J=6.6 Hz, 1H). LC/MS ($ESI^+$) calcd for $C_{43}H_{45}ClFN_9O_6$ ($[M+H]^+$) m/z 838.34; found 837.7.

166: N-((1r,4r)-4-(3-chloro-4-cyanophenoxy)cyclohexyl)-6-(7-(1-(2-(2,6-dioxopiperidin-3-yl)-6-fluoro-1,3-dioxoisoindolin-5-yl)piperidine-4-yl)-2,7-diazaspiro[4.4]nonan-2-yl)pyridazine-3-formamide

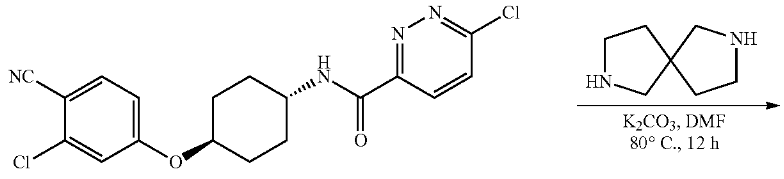

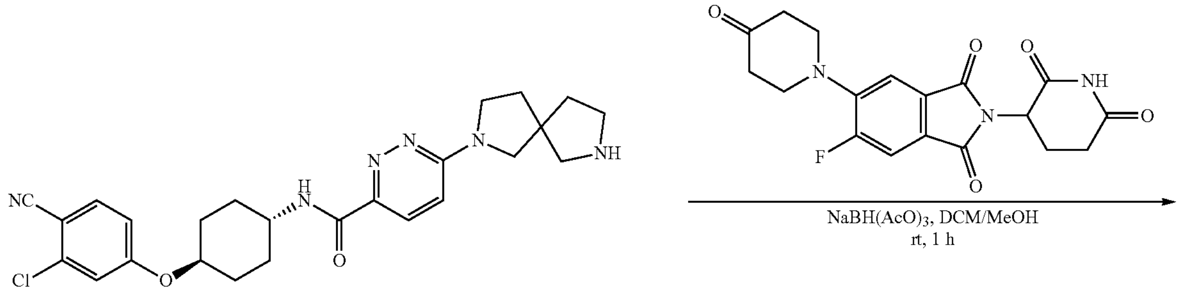

-continued

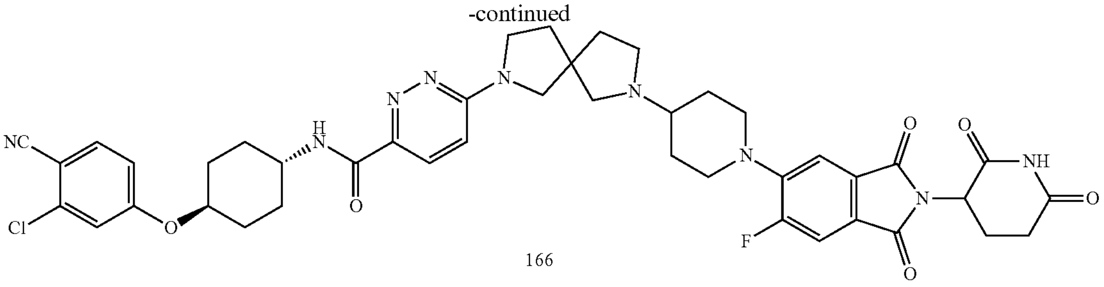

166

$^1$H NMR (400 MHz, DMSO-$d_6$) δ 11.12 (s, 1H), 8.55 (d, J=8.1 Hz, 1H), 7.87 (d, J=8.8 Hz, 1H), 7.82 (d, J=9.3 Hz, 1H), 7.72 (d, J=11.5 Hz, 1H), 7.45 (d, J=7.3 Hz, 1H), 7.40 (d, J=2.4 Hz, 1H), 7.14 (dd, J=8.8, 2.4 Hz, 1H), 6.95 (d, J=9.6 Hz, 1H), 5.11 (dd, J=12.9, 5.3 Hz, 1H), 4.54 (s, 1H), 3.85 (s, 2H), 3.57 (s, 4H), 3.17 (s, 1H), 2.99-2.91 (m, 2H), 2.90 (s, 1H), 2.86 (s, 1H), 2.75 (d, J=10.1 Hz, 1H), 2.70-2.59 (m, 3H), 2.33 (s, 1H), 2.26 (s, 1H), 2.10 (s, 2H), 2.01 (d, J=13.9 Hz, 2H), 1.91 (d, J=14.5 Hz, 3H), 1.81 (s, 2H), 1.65 (d, J=17.6 Hz, 2H), 1.56-1.49 (m, 3H), 1.25 (d, J=6.2 Hz, 2H), 0.86 (s, 1H). LC/MS (ESI$^+$) calcd for $C_{43}H_{45}ClFN_9O_6$ ($[M+H]^+$) m/z 838.34; found 837.8.

167: N-((1r,4r)-4-(3-chloro-4-cyanophenoxy)cyclohexyl)-5-(7-(1-(2-(2,6-dioxopiperidin-3-yl)-6-fluoro-1,3-dioxoisoindolin-5-yl)piperidine-4-yl)-2,7-diazaspiro[4.4]nonan-2-yl)pyrazine-2-carboxamide

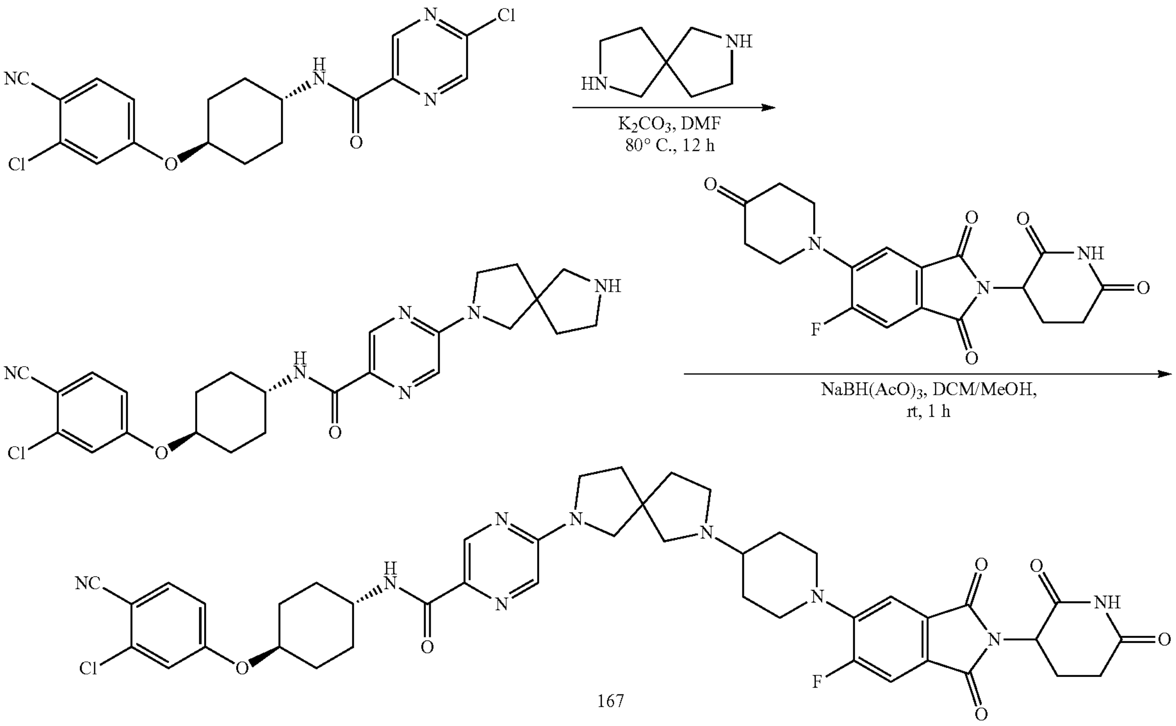

167

$^1$H NMR (400 MHz, DMSO-$d_6$) δ 11.12 (s, 1H), 8.60 (s, 1H), 8.08 (d, J=8.2 Hz, 1H), 7.96-7.82 (m, 2H), 7.72 (d, J=11.5 Hz, 1H), 7.45 (d, J=7.5 Hz, 1H), 7.38 (d, J=2.4 Hz, 1H), 7.13 (dd, J=8.8, 2.4 Hz, 1H), 5.77 (s, 1H), 5.11 (dd, J=12.7, 5.3 Hz, 1H), 4.52 (s, 1H), 3.84 (s, 1H), 3.59 (dd, J=25.2, 19.3 Hz, 4H), 3.53 (d, J=10.9 Hz, 1H), 3.44 (d, J=10.8 Hz, 1H), 3.00-2.91 (m, 2H), 2.88 (d, J=15.1 Hz, 1H), 2.74 (s, 1H), 2.69-2.61 (m, 2H), 2.56 (d, J=12.3 Hz, 2H), 2.25 (s, 1H), 2.09 (d, J=11.8 Hz, 2H), 1.97 (dd, J=46.8, 19.5 Hz, 5H), 1.85 (s, 1H), 1.81 (s, 1H), 1.67-1.45 (m, 5H), 1.32 (d, J=15.0 Hz, 1H), 1.27-1.22 (m, 1H), 0.86 (s, 1H). LC/MS (ESI$^+$) calcd for $C_{43}H_{45}ClFN_9O_6$ ($[M+H]^+$) m/z 838.34; found 837.8.

168: N-((1r,4S)-4-(3-chloro-4-cyanophenoxy)cyclohexyl)-6-((3S)-4-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-3-methylpiperazin-1-yl)pyridazine-3-formamide

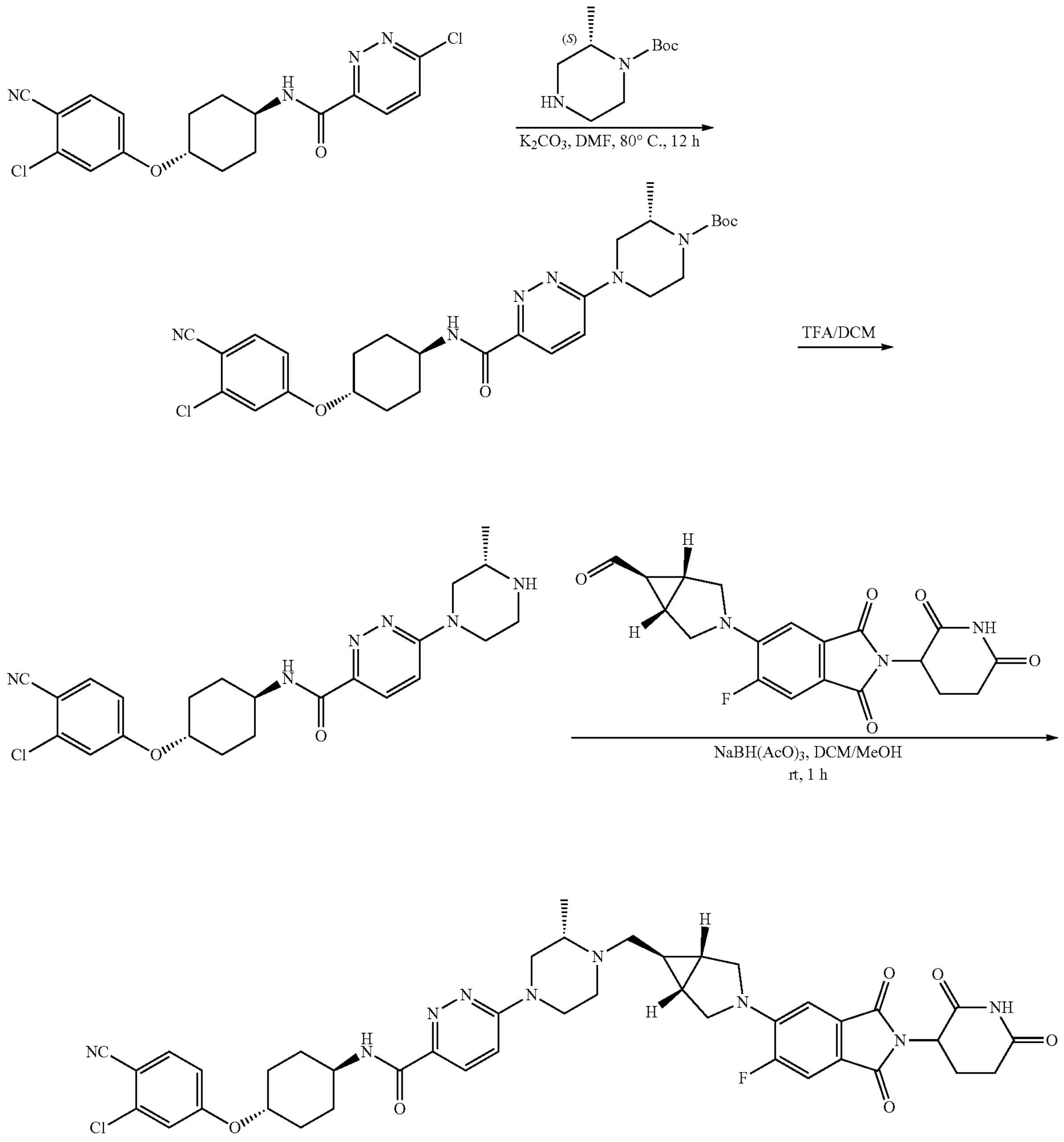

168

$^1$H NMR (400 MHz, $CDCl_3$) δ 8.06 (s, 1H), 8.00 (d, J=9.5 Hz, 1H), 7.87 (d, J=8.2 Hz, 1H), 7.56 (d, J=8.7 Hz, 1H), 7.39 (d, J=12.5 Hz, 1H), 7.03 (d, J=7.3 Hz, 1H), 6.99 (dd, J=11.2, 6.0 Hz, 2H), 6.85 (dd, J=8.7, 2.3 Hz, 1H), 4.91 (dd, J=12.3, 5.3 Hz, 1H), 4.32 (s, 1H), 4.18 (d, J=12.7 Hz, 2H), 4.05 (d, J=8.1 Hz, 1H), 3.87 (d, J=10.2 Hz, 2H), 3.59 (d, J=9.3 Hz, 3H), 3.41 (s, 1H), 3.09 (dd, J=25.2, 13.8 Hz, 2H), 2.90 (d, J=13.5 Hz, 1H), 2.84-2.78 (m, 1H), 2.74 (dd, J=12.2, 5.5 Hz, 2H), 2.60 (s, 1H), 2.51 (d, J=8.7 Hz, 1H), 2.45-2.37 (m, 1H), 2.24-2.10 (m, 6H), 1.60 (dd, J=8.2, 3.7 Hz, 3H), 1.52-1.37 (m, 4H), 0.91 (s, 1H). LC/MS ($ESI^+$) calcd for $C_{42}H_{43}ClFN_9O_6$ ($[M+H]^+$) m/z 824.31; found 824.2.

169: N-((1r,4S)-4-(3-chloro-4-cyanophenoxy)cyclohexyl)-5-((3S)-4-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-3-methylpiperazin-1-yl)pyrazine-2-carboxamide
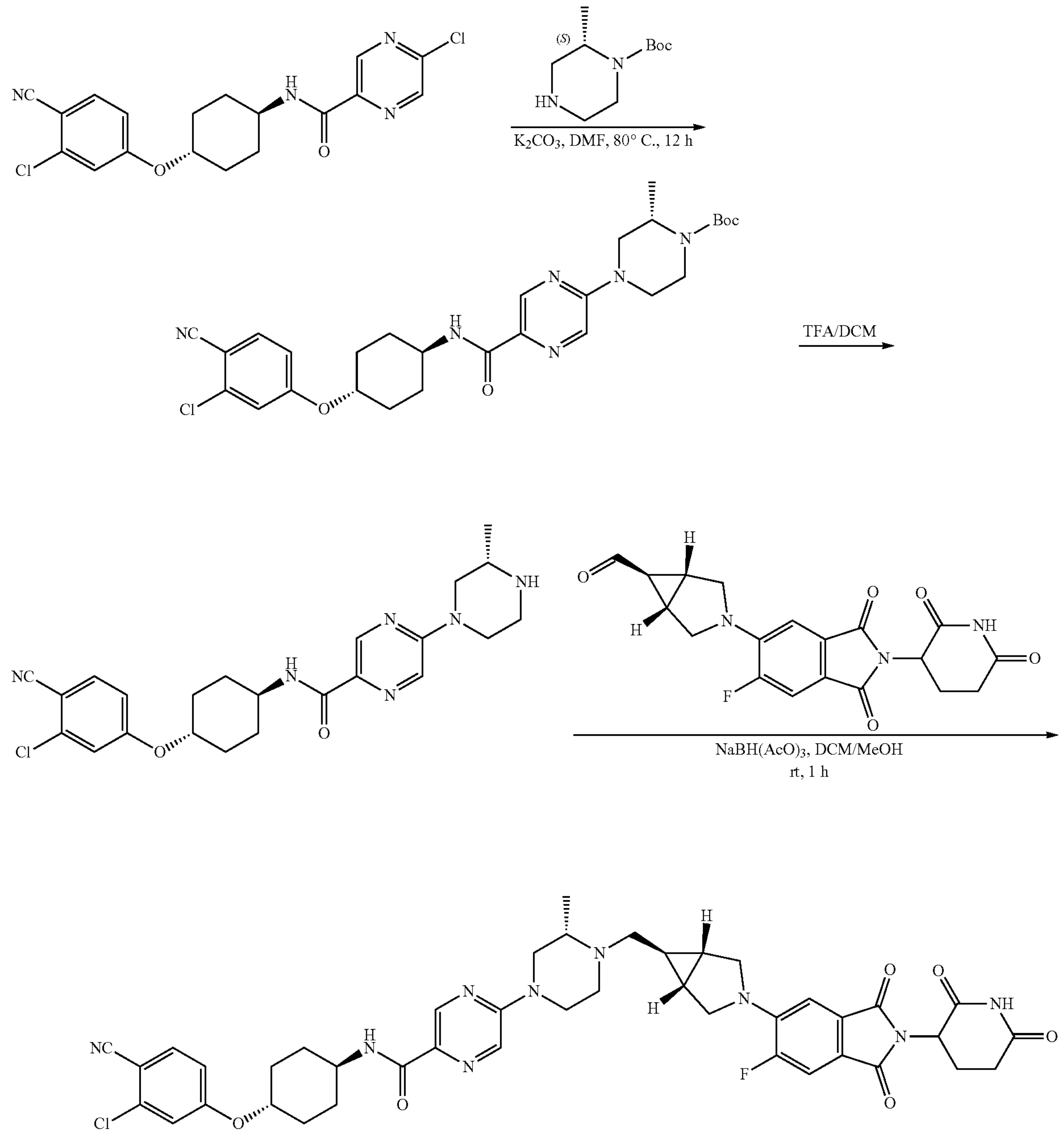
169
$^1$H NMR (400 MHz, $CDCl_3$) δ 8.85 (s, 1H), 8.05 (s, 1H), 7.97 (s, 1H), 7.56 (d, J=8.7 Hz, 1H), 7.41 (d, J=4.6 Hz, 1H), 7.38 (s, 1H), 7.03 (d, J=7.4 Hz, 1H), 6.99 (d, J=2.4 Hz, 1H), 6.84 (dd, J=8.8, 2.4 Hz, 1H), 4.91 (dd, J=12.1, 5.4 Hz, 1H), 4.30 (t, J=10.0 Hz, 1H), 4.04 (s, 1H), 3.89 (s, 2H), 3.64-3.54 (m, 2H), 2.94-2.69 (m, 4H), 2.26-2.10 (m, 5H), 1.65 (d, J=13.5 Hz, 10H), 1.53-1.39 (m, 4H), 1.25 (s, 3H), 0.88 (s, 1H). LC/MS ($ESI^+$) calcd for $C_{42}H_{43}ClFN_9O_6$ ($[M+H]^+$) m/z 824.31; found 824.3.

170: N-((1r,4S)-4-(3-chloro-4-cyanophenoxy)cyclohexyl)-6-((2S)-4-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2-methylpiperazin-1-yl)pyridazine-3-formamide

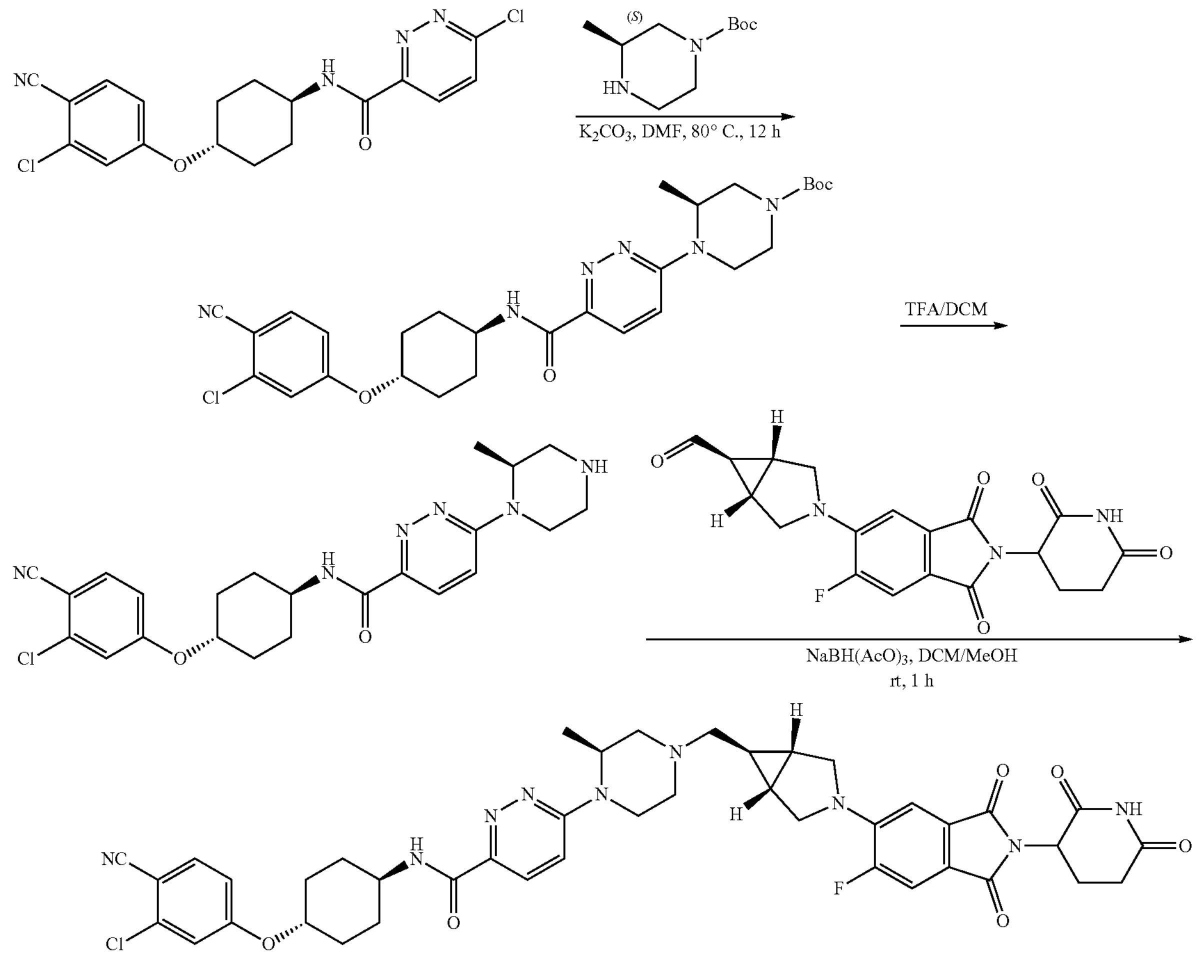

170

$^1$H NMR (400 MHz, DMSO-$d_6$) δ 11.10 (s, 1H), 8.65 (d, J=8.2 Hz, 1H), 7.85 (t, J=9.5 Hz, 2H), 7.62 (s, 1H), 7.40 (d, J=2.4 Hz, 1H), 7.30 (d, J=9.7 Hz, 1H), 7.14 (dd, J=8.8, 2.3 Hz, 1H), 7.09 (d, J=7.5 Hz, 1H), 5.05 (d, J=5.3 Hz, 1H), 4.66 (s, 1H), 4.53 (s, 1H), 4.22 (d, J=11.7 Hz, 1H), 3.92 (dd, J=10.7, 3.3 Hz, 1H), 3.89-3.83 (m, 3H), 3.70 (d, J=10.2 Hz, 1H), 3.61 (d, J=9.1 Hz, 2H), 3.21-3.12 (m, 2H), 3.08 (d, J=9.8 Hz, 1H), 2.97-2.81 (m, 3H), 2.60 (s, 1H), 2.38-2.31 (m, 2H), 2.26 (d, J=7.9 Hz, 1H), 2.10 (d, J=11.0 Hz, 3H), 2.05-1.96 (m, 2H), 1.95-1.83 (m, 3H), 1.51 (dd, J=23.1, 10.3 Hz, 3H), 1.18 (d, J=6.4 Hz, 1H), 0.82 (s, 1H). LC/MS ($ESI^+$) calcd for $C_{42}H_{43}ClFN_9O_6$ ($[M+H]^+$) m/z 824.31; found 824.3.

171: N-((1r,4S)-4-(3-chloro-4-cyanophenoxy)cyclohexyl)-S-((2S)-4-((1r,5S,6s)-3-(2-(2,6-dioxopiperidin-3-yl)-6-fluoro-1,3-dioxoisoindol-5-yl)-3-azabicyclo[3.1.0]n-hexane-6-yl)methyl)-2-methylpiperazin-1-yl)pyrazine-2-carboxamide

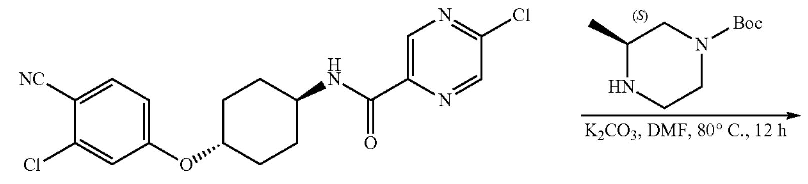

-continued

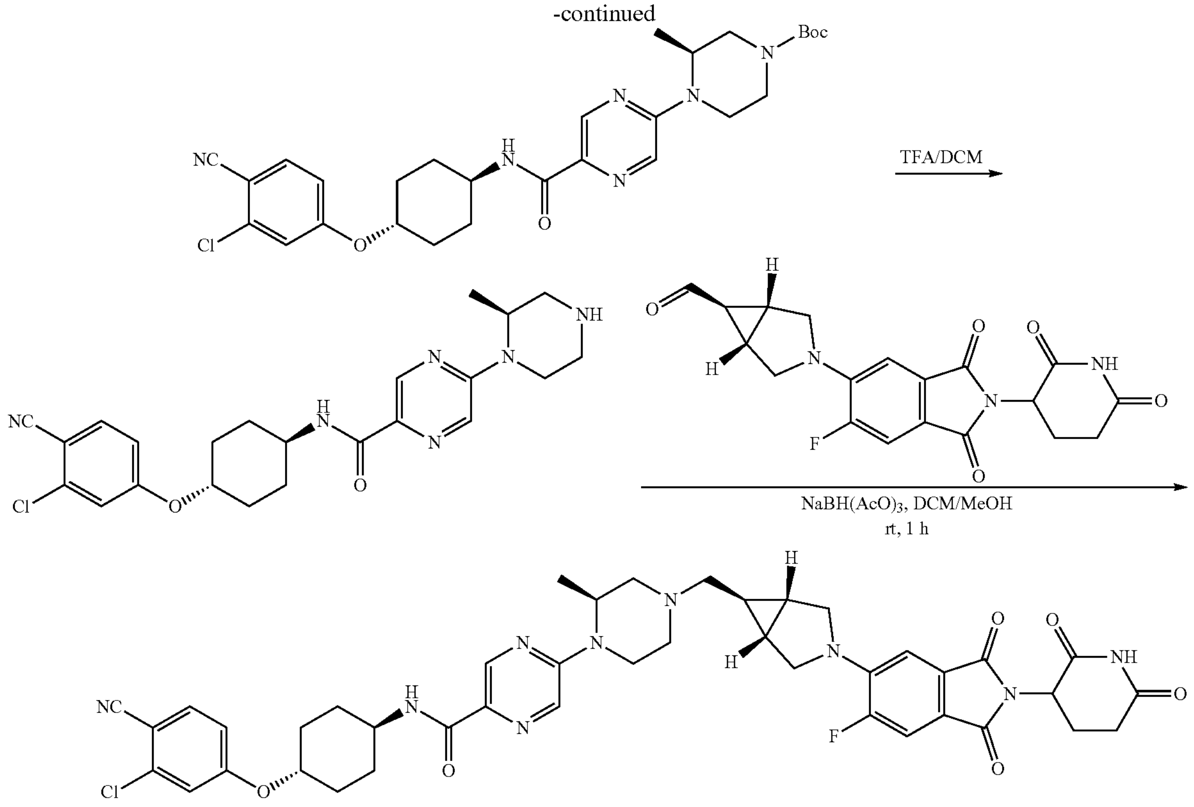

171

$^1$H NMR (400 MHz, DMSO-d6) δ 11.10 (s, 1H), 8.62 (d, J=0.9 Hz, 1H), 8.21 (s, 1H), 8.12 (d, J=8.3 Hz, 1H), 7.86 (d, J=8.8 Hz, 1H), 7.61 (d, J=12.8 Hz, 1H), 7.38 (d, J=2.4 Hz, 1H), 7.16-7.04 (m, 2H), 5.07 (dd, J=12.8, 5.4 Hz, 1H), 4.65 (s, 1H), 4.52 (s, 1H), 4.27-4.18 (m, 1H), 3.85 (d, J=10.3 Hz, 3H), 3.60 (d, J=8.4 Hz, 2H), 3.15 (t, J=10.9 Hz, 2H), 3.06 (d, J=10.2 Hz, 1H), 2.89 (t, J=15.1 Hz, 2H), 2.58 (d, J=18.2 Hz, 2H), 2.41-2.28 (m, 2H), 2.24 (d, J=7.6 Hz, 1H), 2.08 (d, J=7.5 Hz, 3H), 2.05-1.97 (m, 2H), 1.89 (d, J=18.4 Hz, 2H), 1.59 (s, 1H), 1.57-1.43 (m, 3H), 1.23 (d, J=6.5 Hz, 3H), 0.81 (s, 1H). LC/MS (ESI$^+$) calcd for $C_{42}H_{43}ClFN_9O_6$ ($[M+H]^+$) m/z: 824.31; found 824.3.

172: 2-chloro-4-((1r,4r)-4-(2-((1-((2-(2,6-dioxopiperidin-3-yl)-1,3-dioxoisoindolin-5-yl)piperidine-4-yl)methyl)piperidine-4-yl)amino)-5-oxo-5,7-dihydro-6H-pyrrolo[3,4-b]pyridin-6-yl)cyclohexyl)oxy)benzonitrile

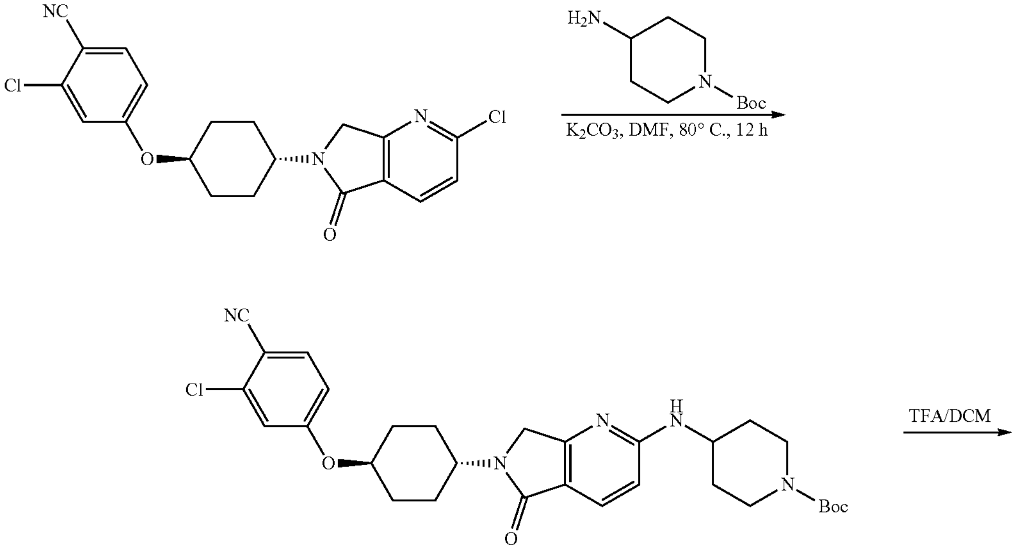

-continued
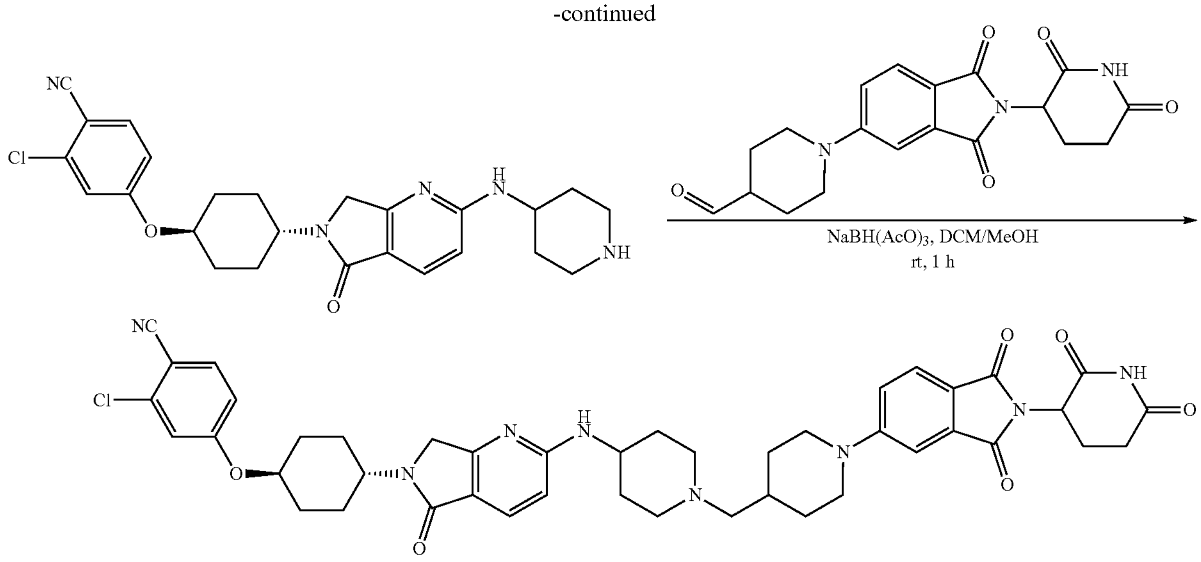
172
LC/MS (ESI+) calcd for $C_{44}H_{47}ClN_8O_6$ ($[M+H]^+$) m/z 819.36; found 819.3.
173: 2-chloro-4-((1r,4r)-4-(2-(4-((4-((2-(2,6-dioxopiperidin-3-yl)-1,3-dioxoisoindolin-5-yl)amino)piperidin-1-yl)methyl)piperidin-1-yl)-5-oxo-5,7-dihydro-6H-pyrrolo[3,4-b]pyridin-6-yl)cyclohexyl)oxy)benzonitrile
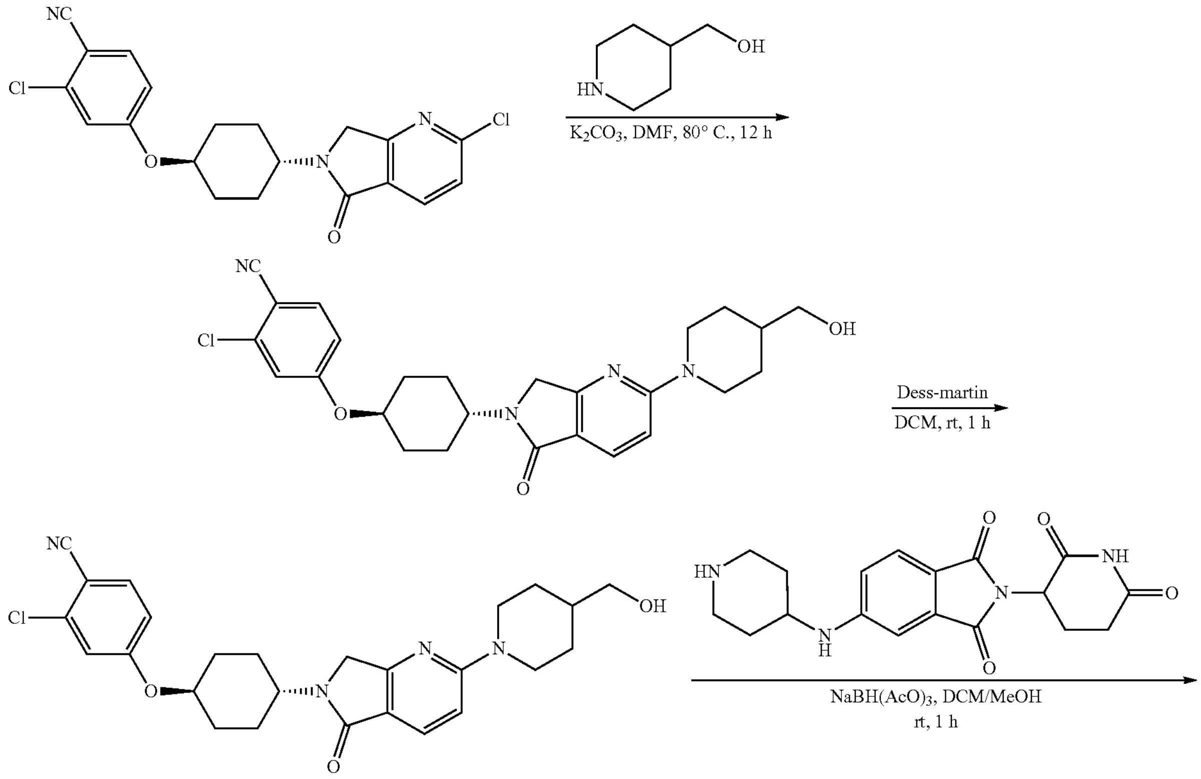

-continued

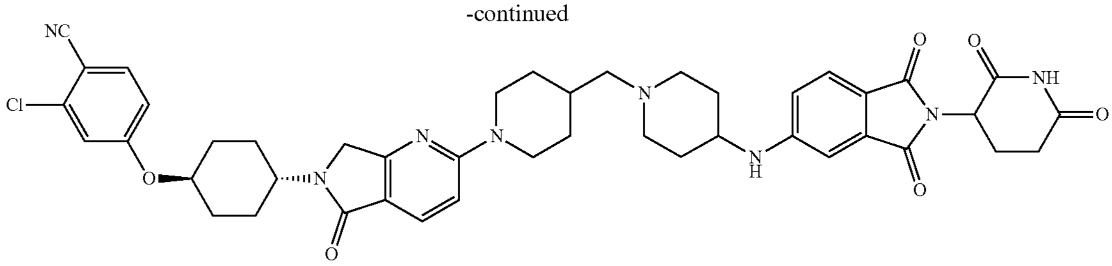

173

$^1$H NMR (400 MHz, DMSO-$d_6$) δ 11.08 (s, 1H), 7.88 (d, J=8.8 Hz, 1H), 7.71-7.68 (m, 1H), 7.56 (d, J=8.4 Hz, 1H), 7.40 (d, J=2.3 Hz, 1H), 7.17-7.11 (m, 1H), 7.04 (d, J=7.1 Hz, 1H), 6.98 (s, 1H), 6.88 (d, J=9.7 Hz, 1H), 5.03 (dd, J=12.7, 5.1 Hz, 1H), 4.57 (s, 1H), 4.43 (d, J=12.1 Hz, 2H), 4.25 (s, 2H), 4.07 (s, 1H), 3.17 (s, 1H), 2.93 (t, J=12.3 Hz, 3H), 2.82 (d, J=10.3 Hz, 2H), 2.58 (d, J=16.2 Hz, 1H), 2.16 (d, J=6.4 Hz, 3H), 2.12-2.03 (m, 2H), 2.00 (s, 1H), 1.92 (d, J=10.9 Hz, 2H), 1.85 (s, 2H), 1.79 (s, 6H), 1.56 (s, 2H), 1.44 (d, J=10.3 Hz, 2H), 1.25 (d, J=10.2 Hz, 1H), 1.07 (d, J=12.2 Hz, 2H). LC/MS (ESI$^+$) calcd for $C_{44}H_{47}ClN_8O_6$ ([M+H]$^+$) m/z 819.36; found 819.3.

174: 2-chloro-4-(((3aR,5r,6aS)-2-(5-(4-((4-(2-(2,6-dioxopiperidin-3-yl)-1,3-dioxoisoindolin-5-yl)piperazin-1-yl)methyl)piperidin-1-yl)pyrazine-2-carbonyl) octahydrocyclopenta[c]pyrrol-5-yl)oxy) benzonitrile

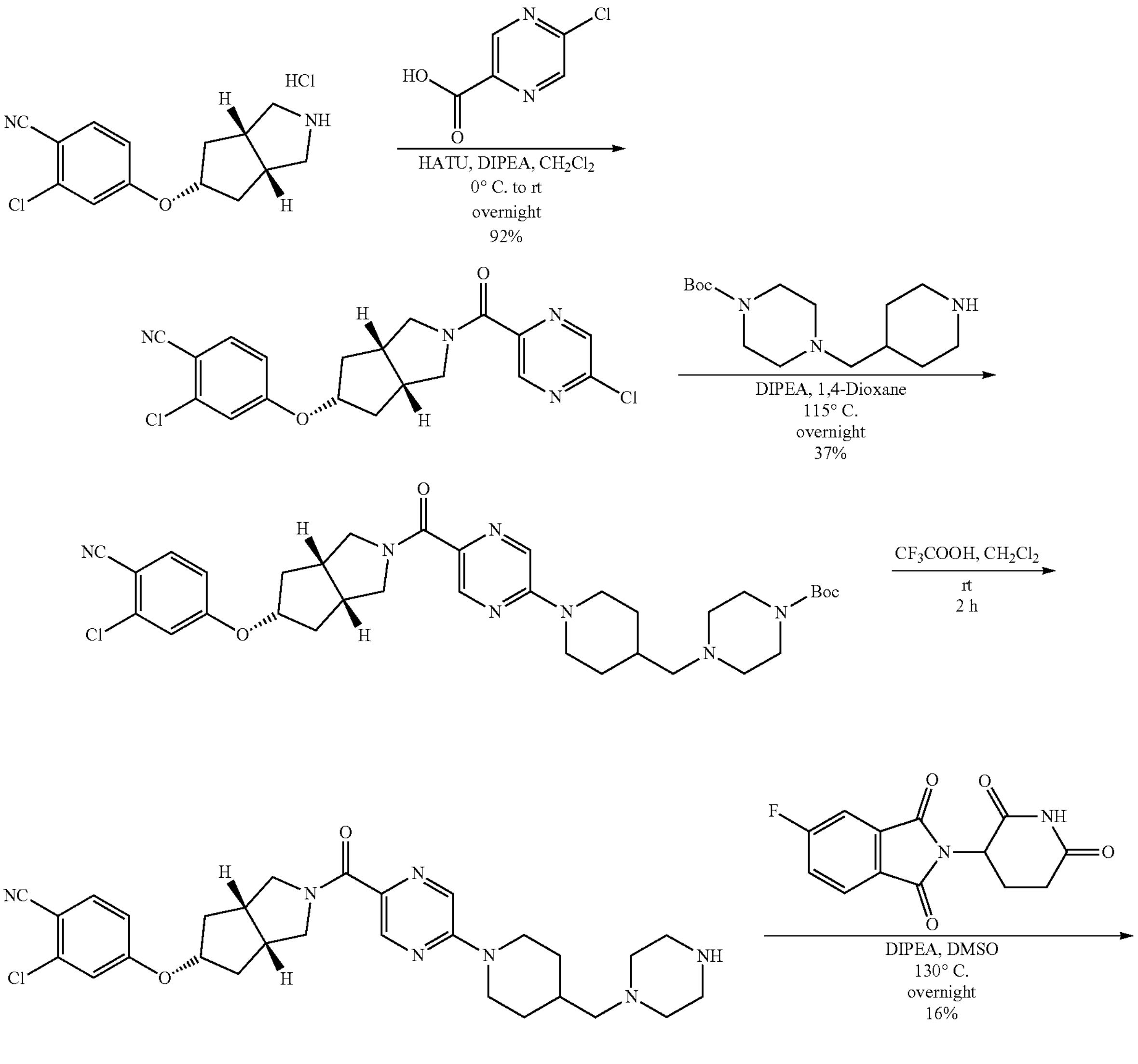

-continued

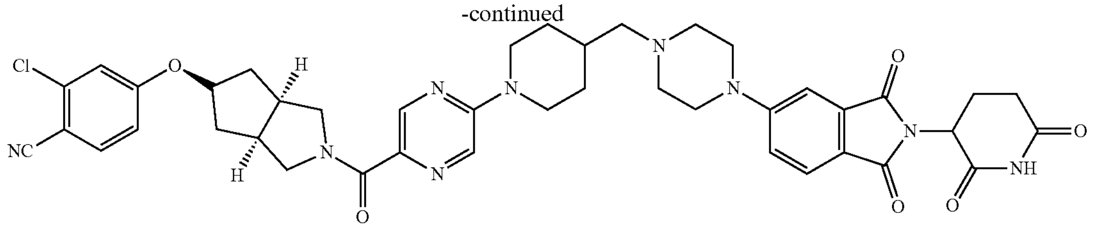

174

1. 2-Chloro-4-(((3aR,5r,6aS)-2-(5-chloropyrazine-22-carbonyl) octahydrocyclopenta[c]pyrrol-5-yl) oxy)benzonitrile Compound 5-chloropyrazine-22-carboxylic acid (79 mg, 0.50 mmol) and HATU (304 mg, 0.80 mmol) were added in 5 mL of dichloromethane, and then the system was moved in an ice water bath to cool down under stirring. After 10 min, diisopropylethylamine (194 mg, 1.50 mmol) was added, followed by addition of 2-chloro-4-(((3aR,5r,6aS)-octahydrocyclopenta[c]pyrrol-5-yl)oxy)benzonitrile hydrochloride (150 mg, 0.50 mmol). After that, the ice bath was removed, and the reaction was allowed to react overnight under stirring at room temperature. TLC indicated the disappearance of raw material. To the reaction solution, were added dichloromethane and water for extraction. The organic layer was washed with saturated brine, dried over anhydrous sodium sulfate, rotatory evaporated to dry, and separated and purified by Pre-TLC, to provide compound 2-chloro-4-(((3aR,5r,6aS)-2-(5-chloropyrazine-22-carbonyl)octahydrocyclopenta[c]pyrrol-5-yl)oxy)benzonitrile (185 mg), with a yield of 92%. LC/MS (ESI) calcd for $C_{19}H_{16}Cl_2N_4O_2$ $[M+H]^+$ m/z, 403.3; found, 403.0.

2. Synthesis of t-butyl-4-((1-(5-((3aR,5r,6aS)-5-(3-chloro-4-cyanophenoxy) octahydrocyclopenta[c] pyrrol-2-carbonyl)pyrazine-2-yl)piperidine-4-yl) methyl) piperazine-1-carboxylate 2-Chloro-4-(((3aR,5r,6aS)-2-(5-chloropyrazine-22-carbonyl)octahydrocyclopenta[c] pyrrol-5-yl)oxy)benzonitrile (185 mg, 0.46 mmol), t-butyl-4-(piperidin-4-ylmethyl) piperazine-1-carboxylate (260 mg, 0.92 mmol) and diisopropylethylamine (297 mg, 2.30 mmol) were added in 8 mL of dioxane. The reaction solution was heated to 115° C., stirred and reacted overnight under reflux. After cooling to room temperature, the reaction solution was added with ethyl acetate and water for extraction. The organic phase was successively washed with 0.05 N HCl and saturated brine, and dried over anhydrous sodium sulfate. The solvent was removed by rotary evaporation to obtain the crude product, which was separated and purified by Pre-TLC, to provide compound butyl-4-((1-(5-((3aR,5r,6aS)-5-(3-chloro-4-cyanophenoxy)octahydrocyclopenta[c]pyrrol-2-carbonyl)pyrazine-2-yl)piperidine-4-yl)methyl)piperazine-1-carboxylate (109 mg), with a yield of 37%. LC/MS ($ESI^+$) calcd for $C_{34}H_{44}ClN_7O_4$ $[M+H]^+$ m/z, 650.2; found, 650.2.

3. Synthesis of Compound 2-chloro-4-(((3aR,5r,6aS)-2-(5-(4-(piperazin-1-ylmethyl) piperidin-1-yl) pyrazine-2-carbonyl)octahydrocyclopenta[c]pyrrol-5-yl)oxy) benzonitriletrifluoroacetate Compound butyl-4-((1-(5-((3aR,5r,6aS)-5-(3-chloro-4-cyanophenoxy)octahydro cyclopenta[c]pyrrol-2-carbonyl) pyrazine-2-yl)piperidine-4-yl)methyl)piperazine-1-carboxylate (109 mg, 0.17 mmol) was dissolved in 6 mL of dichloromethane and 3 mL of trifluoroacetic acid, and the reaction solution was stirred and reacted at room temperature for 2 h. The solvent was removed by rotary evaporation, and the residual trifluoroacetic acid was removed by evaporation with dichloromethane, to provide the compound 2-chloro-4-(((3aR,5r,6aS)-2-(5-(4-(piperazin-1-ylmethyl)piperidin-1-yl) pyrazine-2-carbonyl)octahydrocyclopenta[c] pyrrol-5-yl)oxy) benzonitriletrifluoroacetate, which was directly used in the next reaction, without further purification.

LC/MS ($ESI^+$) calcd for $C_{31}H_{37}ClF_3N_7O_4[M+H]^+$ m/z, 550.1; found, 550.4.

4. 2-Chloro-4-(((3aR,5r,6aS)-2-(5-(4-((4-(2-(2,6-dioxopiperidin-3-yl)-1,3-dioxoisoindolin-5-yl)piperazin-1-yl)methyl)piperidin-1-yl)pyrazine-2-carbonyl) octahydrocyclopenta[c]pyrrol-5-yl)oxy) benzonitrile 2-Chloro-4-(((3aR,5r,6aS)-2-(5-(4-(piperazin-1-ylmethyl)piperidin-1-yl)pyrazine-2-carbonyl)octahydrocyclopenta[c]pyrrol-5-yl)oxy)benzonitriletrifluoroacetate, 2-(2,6-dioxopiperidin-3-yl)-5-fluoroisoindoline-1,3-dione (47 mg, 0.17 mmol) and diisopropylethylamine (181 mg, 1.40 mmol) were added to 5 mL of dimethylsulfoxide. After that, the system was placed in an oil bath at 130° C., and the reaction was stirred overnight. After cooling to room temperature, the reaction solution was added with ethyl acetate and water for extraction. The organic phase was successively washed with 0.05 N HCl and saturated brine, and dried over anhydrous sodium sulfate. The solvent was removed by rotary evaporation, and the residue was separated and purified by Pre-TLC, to provide compound 2-chloro-4-(((3aR,5r,6aS)-2-(5-(4-((4-(2-(2,6-dioxopiperidin-3-yl)-1,3-dioxoisoindolin-5-yl)piperazin-1-yl)methyl) piperidin-1-yl)pyrazine-2-carbonyl)octahydrocyclopenta[c] pyrrol-5-yl)oxy)benzonitrile (22 mg), with a yield of 16%.

LC/MS ($ESI^+$) calcd for $C_{31}H_{37}ClF_3N_7O_4$ $[M+H]^+$ m/z, 806.3; found, 806.3.

$^1$H NMR (400 MHz, DMSO-$d_6$) δ 11.06 (s, 1H), 8.46 (s, 1H), 8.23 (s, 1H), 7.85 (d, J=8.7 Hz, 1H), 7.68 (d, J=8.4 Hz, 1H), 7.34 (s, 1H), 7.26 (dd, J=8.2, 1.6 Hz, 1H), 7.20 (d, J=2.1 Hz, 1H), 7.02 (dd, J=8.6, 2.0 Hz, 1H), 5.05 (dt, J=13.2, 7.8 Hz, 2H), 4.43 (d, J=11.6 Hz, 2H), 3.91 (dd, J=13.9, 7.3 Hz, 1H), 3.79 (t, J=11.7 Hz, 1H), 3.67 (d, J=17.5 Hz, 2H), 3.45 (s, 4H), 3.01-2.92 (m, 2H), 2.87 (d, J=23.0 Hz, 1H), 2.76 (s, 2H), 2.59 (d, J=31.6 Hz, 2H), 2.33 (s, 3H), 2.21 (d, J=7.1 Hz, 2H), 2.05-1.96 (m, 3H), 1.83 (d, J=15.2 Hz, 21-), 1.76-1.58 (m, 4H), 1.32 (d, J=8.7 Hz, 1H), 1.11 (d, J=12.6 Hz, 1H).

175: 2-chloro-4-(((3aR,5s,6aS)-2-(6-(4-((4-(2-(2,6-dioxopiperidin-3-yl)-1,3-dioxoisoindolin-5-yl)piperazin-1-yl)methyl)piperidin-1-yl)pyridazine-3-carbonyl) octahydrocyclopenta[c]pyrrol-5-yl)oxy) benzonitrile

175

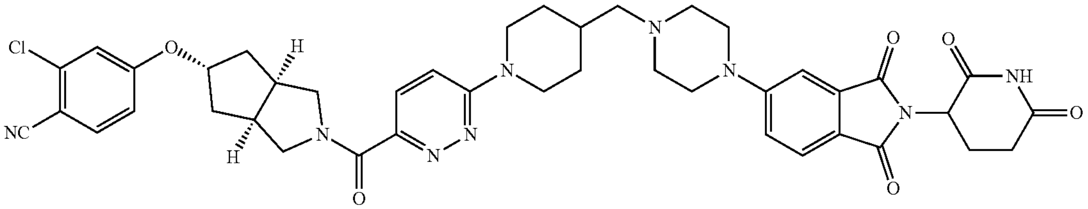

LC/MS ($ESI^+$) calcd for $C_{42}H_{44}ClN_9O_6$ $[M+H]^+$ m/z, 806.3; found, 806.2.

$^1H$ NMR (400 MHz, $CDCl_3$) δ 8.28 (s, 1H), 7.87 (d, J=9.4 Hz, 1H), 7.70 (d, J=8.4 Hz, 1H), 7.56 (d, J=8.9 Hz, 1H), 7.29 (s, 1H), 7.06 (dd, J=7.0, 1.1 Hz, 1H), 7.02-6.87 (m, 2H), 6.81 (dd, J=8.1, 1.9 Hz, 1H), 4.94 (s, 31-), 4.54 (d, J=12.6 Hz, 2H), 4.14 (dd, J=42.5, 8.5 Hz, 3H), 3.98-3.79 (m, 1H), 3.69 (d, J=11.0 Hz, 1H), 3.44 (br, 4H), 3.17-2.67 (m, 7H), 2.60 (s, 4H), 2.36-2.19 (m, 3H), 2.19-2.02 (m, 4H), 1.95 (d, J=11.0 Hz, 3H).

176: Synthesis of N-((1r,4R)-4-(3-chloro-4-cyano-phenoxy)cyclohexyl)-5-((1R,5S,6S)-6-((4-(2-(2,6-dioxopiperidin-3-yl)-6-fluoro-1,3-dioxoisoindolin-5-yl)piperazin-1-yl) methyl)-3-azabicyclo[3.1.0] hexan-3-yl)pyrazine-2-carboxamide

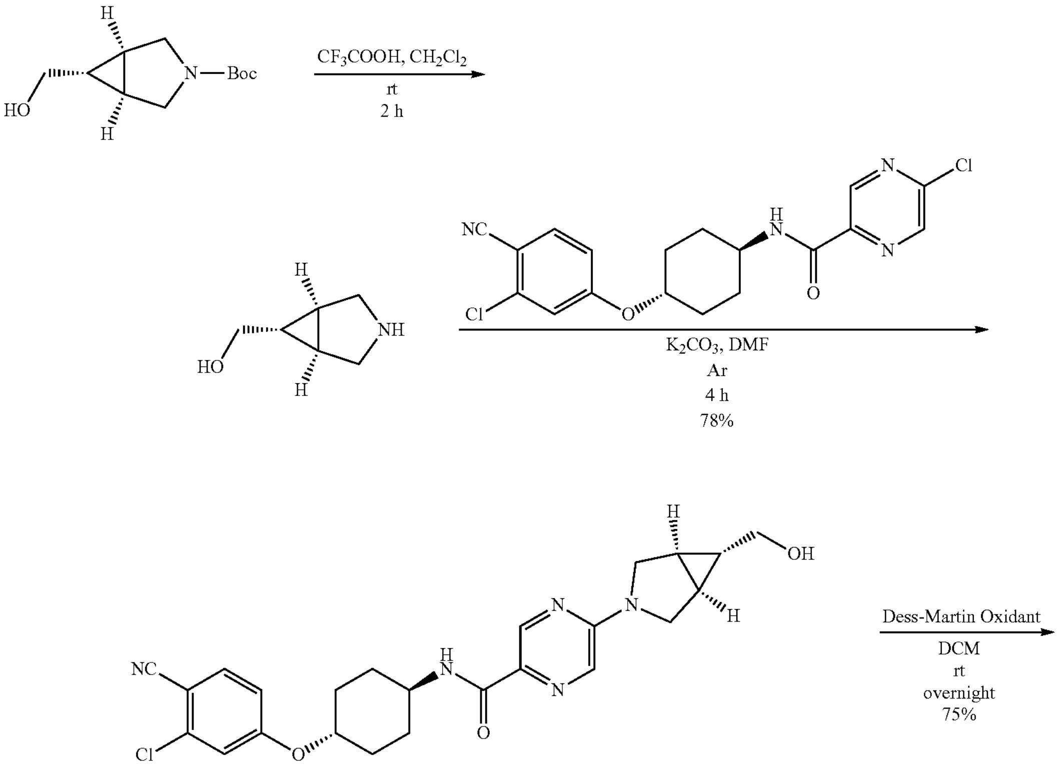

-continued

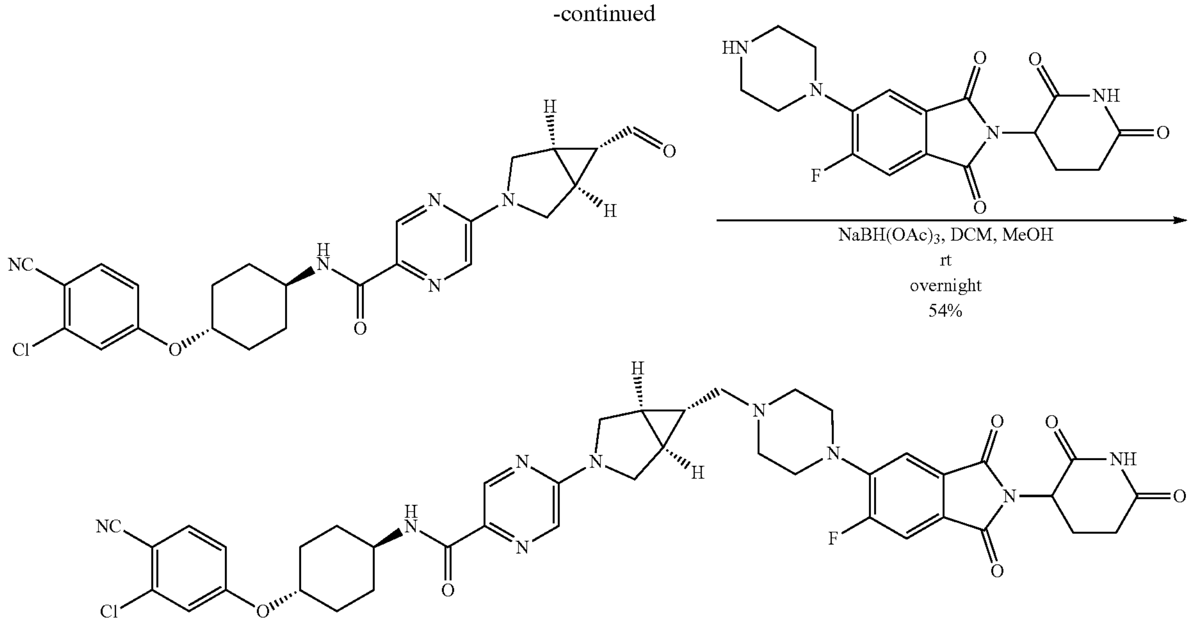

176

1. Synthesis of Compound (1R,5S,6r)-3-azabicyclo[3.1.0]hexan-6-ylmethanol

Compound (1R,5S,6r)-t-butyl 6-(hydroxymethyl)-3-azabicyclo[3.1.0]hexan-3-carboxylate (50 mg, 0.23 mmol) was dissolved in 3 mL of dichloromethane, to which was added 1.5 mL of trifluoroacetic acid. After the reaction solution was stirred at room temperature for 2 h, TLC indicated that the starting material had disappeared, and then excess trifluoroacetic acid and the solvent were removed by rotary evaporation, and residual trifluoroacetic acid was removed by rotatory evaporation with dichloromethane several times, to provide compound (1R,5S,6r)-3-azabicyclo[3.1.0]hexan-6-ylmethanoltrifluoroacetate, which was directly used in the next reaction, without further purification.

2. Synthesis of Compound N-((1r,4R)-4-(3-chloro-4-cyanophenoxy)cyclohexyl)-5-((1R,5S,6R)-6-(hydroxymethyl)-3-azabicyclo[3.1.0]hexan-3-yl)pyrazine-2-carboxamide To a round bottom flask containing (1R,5S,6r)-3-heterobicyclo[3.1.0]hexan-6-ylmethanoltrifluoroacetate, was added 5 mL of DMF, and the mixture was stirred at room temperature to dissolve and make the solution become clear, to which were then added 5-chloro-N-((1r,4r)-4-(3-chloro-4-cyanophenoxy)cyclohexyl)pyrazine-2-carboxamide (82 mg, 0.21 mmol) and potassium carbonate (95 mg, 0.69 mmol). After that, the system was evacuated and purged with argon gas, that was repeated 5 times, to ensure the inert gas atmosphere in the system. After that, the system was moved to an oil bath at 80° C. for heating and reacting under stirring. After 4 h, the sample was taken out and subjected to TLC, and the result indicated the completion of the reaction. Heating was stopped, and once the system was cooled to room temperature, ethyl acetate (10 mL) and water (15 mL) were added to the system. The system was stirred vigorously, and stood still 3 min for separation of the layers. The aqueous layer was extracted with ethyl acetate (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by Pre-TLC, to provide N-((1r,4R)-4-(3-chloro-4-cyanophenoxy)cyclohexyl)-5-((1R,5S,6R)-6-(hydroxymethyl)-3-azabicyclo[3.1.0]hexan-3-yl)pyrazine-2-carboxamide (82 mg, 0.17 mmol), with a yield of 76%.

LC/MS (ESI$^+$) calcd for $C_{24}H_{26}ClN_5O_3[M+H]^+$ m/z, 467.9; found, 468.1.

3. Synthesis of N-((1r,4R)-4-(3-chloro-4-cyanophenoxy)cyclohexyl)-5-((1R,5S,6R)-6-formyl-3-azabicyclo[3.1.0]hexan-3-yl)pyrazine-2-carboxamide N-((1r,4R)-4-(3-chloro-4-cyanophenoxy)cyclohexyl)-5-((1R,5S,6R)-6-(hydroxymethyl)-3-azabicyclo[3.1.0]hexan-3-yl)pyrazine-2-carboxamide (80 mg, 0.17 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (144 mg, 0.34 mmol) was added to the system. After that, the system was warmed to room temperature and reacted under stirring at room temperature. Next day, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4R)-4-(3-chloro-4-cyanophenoxy)cyclohexyl)-5-((1R,5S,6R)-6-formyl-3-azabicyclo[3.1.0]hexan-3-yl)pyrazine-2-carboxamide (60 mg), with a yield of 76%. LC/MS ($ESI^+$) calcd for $C_{24}H_{24}ClN_5O_3$ $[M+H]^+$ m/z, 465.9; found, 466.1.

4. N-((1r,4R)-4-(3-chloro-4-cyanophenoxy)cyclohexyl)-5-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyrazine-2-carboxamide (25 mg, 0.05 mmol) was placed in a 25 mL single-neck round bottom flask, to which were added dichloromethane (3 mL) and methanol (1 mL), and then the reaction solution was stirred at room temperature to dissolve and make the solution become clear. Subsequently, 2-(2,6-dioxopiperidin-3-yl)-5-fluoro-6-(piperazin-1-yl)isoindoline-1,3-dione (18 mg, 0.05 mmol) and one drop of glacial acetic acid were added to the system. After that, the mixture was stirred at room temperature for 15 min, to which was then added sodium triacetylborohydride (32 mg, 0.15 mmol). The system was allowed to react overnight under stirring at room temperature. Next day, the sample was taken out and subjected to TLC, and the result showed the completion of the reaction. Stirring was stopped, and the solvent was removed by rotatory evaporation. Dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by Pre-TLC, to provide compound N-((1r,4R)-4-(3-chloro-4-cyanophenoxy)cyclohexyl)-5-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyrazine-2-carboxamide (22 mg), with a yield of 54%. LC/MS ($ESI^+$) calcd for $C_{41}H_{41}ClFN_9O_6$ $[M+H]^+$ m/z, 810.3; found, 810.3.

$^1H$ NMR (400 MHz, $CDCl_3$) δ 8.84 (d, J=1.2 Hz, 1H), 8.56 (br, 1H), 7.68 (d, J=1.1 Hz, 1H), 7.56 (d, J=8.7 Hz, 1H), 7.49 (d, J=10.9 Hz, 1H), 7.42 (dd, J=13.6, 7.7 Hz, 2H), 6.99 (d, J=2.3 Hz, 1H), 6.85 (dd, J=8.7, 2.4 Hz, 1H), 4.94 (dd, J=12.2, 5.3 Hz, 1H), 4.47 (br, 1H), 4.31 (ddd, J=13.6, 9.9, 3.5 Hz, 1H), 4.09-3.96 (m, 1H), 3.87 (d, J=10.5 Hz, 2H), 3.61 (d, J=10.4 Hz, 2H), 3.36 (br, 4H), 2.97-2.64 (m, 7H), 2.53 (d, J=4.5 Hz, 2H), 2.23-2.10 (m, 5H), 1.66 (dd, J=12.7, 2.7 Hz, 3H), 1.54-1.37 (m, 3H).

177: N-((1r,4R)-4-(3-chloro-4-cyanophenoxy)cyclohexyl)-5-((1R,5S,6S)-6-((4-(2-(2,6-dioxopiperidin-3-yl)-1,3-dioxoisoindolin-5-yl)piperazin-1-yl)methyl)-3-azabicyclo[3.1.0]hexan-3-yl)pyrazine-2-carboxamide

177

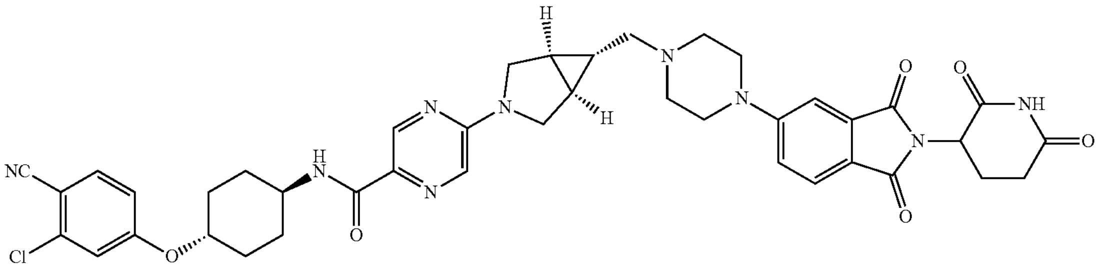

LC/MS ($ESI^+$) calcd for $C_{41}H_{42}ClN_9O$ $[M+H]^+$ m/z, 792.3; found 792.3.

$^1H$ NMR (400 MHz, $CDCl_3$) δ 8.84 (d, J=1.2 Hz, 1H), 8.47 (s, 1H), 7.70 (d, J=8.6 Hz, 2H), 7.56 (d, J=8.7 Hz, 1H), 7.41 (d, J=8.2 Hz, 1H), 7.29 (d, J=2.1 Hz, 1H), 7.07 (dd, J=8.6, 2.2 Hz, 1H), 6.99 (d, J=2.3 Hz, 1H), 6.85 (dd, J=8.8, 2.4 Hz, 1H), 4.95 (dd, J=12.3, 5.3 Hz, 1H), 4.60 (br, 2H), 4.30 (ddd, J=13.2, 9.7, 3.1 Hz, 1H), 4.09-3.97 (m, 1H), 3.87 (d, J=10.3 Hz, 2H), 3.61 (d, J=10.5 Hz, 2H), 3.47 (br, 4H), 2.94-2.73 (m, 3H), 2.71 (br, 4H), 2.47 (d, J=6.5 Hz, 2H), 2.24-2.08 (m, 5H), 1.71 (dd, J=13.6, 3.7 Hz, 3H), 1.54-1.39 (m, 2H).

178: Synthesis of N-((1r,4R)-4-(3-chloro-4-cyanophenoxy)cyclohexyl)-6-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyridazine-3-formamide

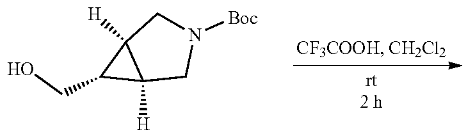

-continued

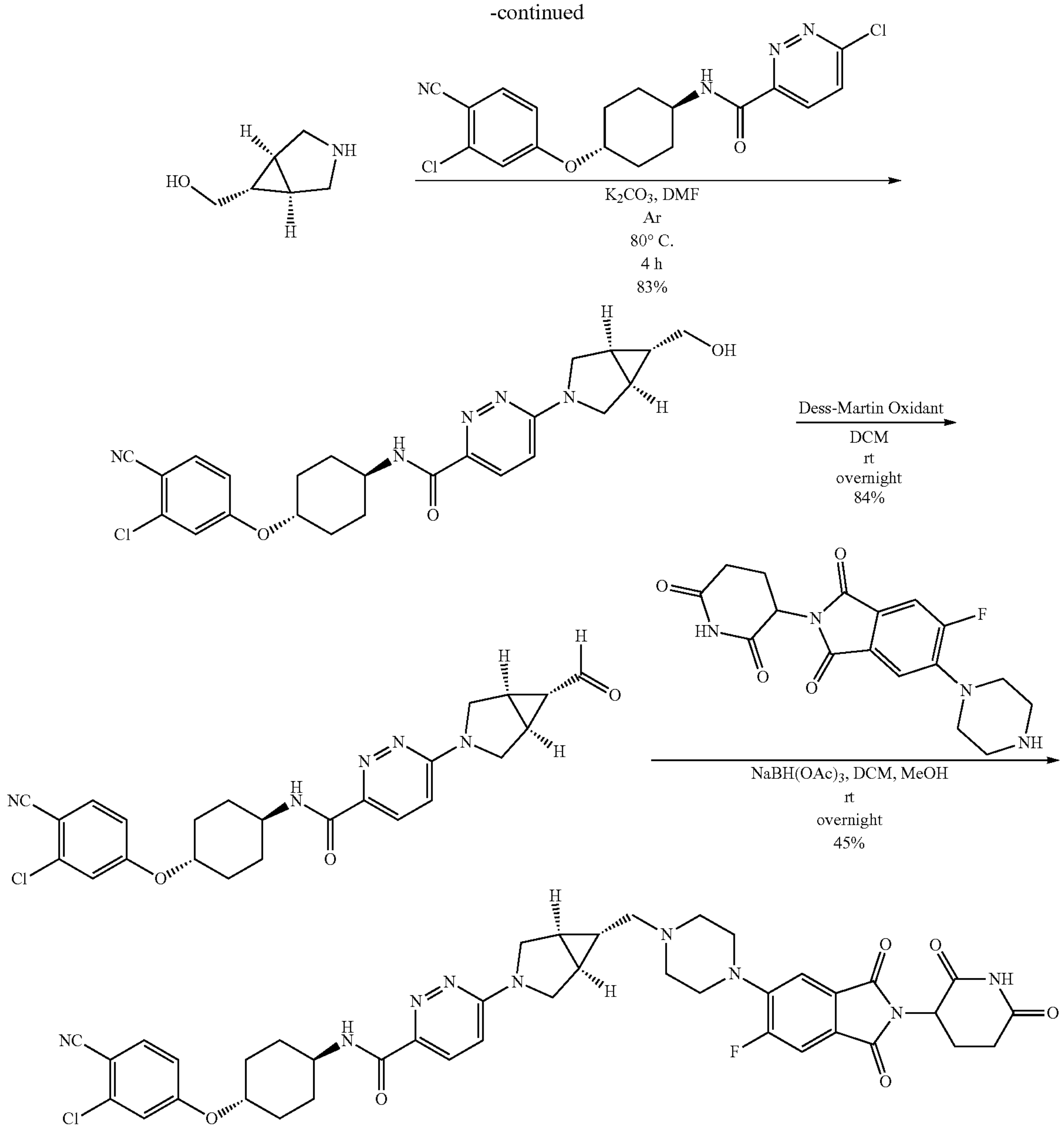

178

1. Synthesis of Compound (1R,5S,6r)-3-azabicyclo[3.1.0]hexan-6-ylmethanol

Compound (1R,5S,6r)-t-butyl 6-(hydroxymethyl)-3-azabicyclo[3.1.0]hexan-3-carboxylate (50 mg, 0.23 mmol) was dissolved in 3 mL of dichloromethane, to which was added 1.5 mL of trifluoroacetic acid. After the reaction solution was stirred at room temperature for 2 h, TLC indicated that the starting material had disappeared, and then excess trifluoroacetic acid and the solvent were removed by rotary evaporation, and residual trifluoroacetic acid was removed by rotatory evaporation with dichloromethane several times, to provide compound (1R,5S,6r)-3-azabicyclo[3.1.0]hexan-6-ylmethanoltrifluoroacetate, which was directly used in the next reaction, without further purification.

2. Synthesis of Compound N-((1r,4R)-4-(3-chloro-4-cyanophenoxy)cyclohexyl)-6-((1R,5S,6R)-6-(hydroxymethyl)-3-azabicyclo[3.1.0]hexan-3-yl)pyridazine-3-formamide To a round bottom flask containing (1R,5S,6r)-3-heterobicyclo[3.1.0]hexan-6-ylmethanoltrifluoroacetate, was added 5 mL of DMF, and the mixture was stirred at room temperature to dissolve and make the solution become clear, to which were then added 6-chloro-N-((1r,4r)-4-(3-chloro-4-cyanophenoxy)cyclohexyl)pyridazine-3-formamide (82 mg, 0.21 mmol) and potassium carbonate (95 mg, 0.69 mmol). After that, the system was evacuated and purged with argon gas, that was repeated 5 times, to ensure the inert gas atmosphere in the system. After that, the system was moved to an oil bath at 80° C. for heating and reacting under stirring. After 4 h, the sample was taken out and subjected to TLC, and the result indicated the completion of the reaction. Heating was stopped, and once the system was cooled to room temperature, ethyl acetate (10 mL) and water (15 mL) were added to the system. The system was stirred vigorously, and stood still for separation of the layers. The aqueous layer was extracted with ethyl acetate (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by Pre-TLC, to provide compound N-((1r,4R)-4-(3-chloro-4-cyanophenoxy)cyclohexyl)-6-((1R,5S,6R)-6-(hydroxymethyl)-3-azabicyclo[3.1.0]hexan-3-yl)pyridazine-3-formamide (91 mg, 0.19 mmol), with a yield of 83%. LC/MS (ESI$^+$) calcd for $C_{22}H_{33}N_2O_5$ [M+H]$^+$ m/z, 467.9; found, 468.1.

3. Synthesis of Compound N-((1r,4R)-4-(3-chloro-4-cyanophenoxy)cyclohexyl)-6-((1R,5S,6R)-6-formyl-3-azabicyclo[3.1.0]hexan-3-yl)pyridazine-3-formamide N-((1r,4R)-4-(3-chloro-4-cyanophenoxy)cyclohexyl)-6-((1R,5S,6R)-6-(hydroxymethyl)-3-azabicyclo[3.1.0]hexan-3-yl)pyridazine-3-formamide (91 mg, 0.19 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (161 mg, 0.38 mmol) was added to the system. After that, the system was warmed to room temperature and reacted under stirring at room temperature. Next day, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4R)-4-(3-chloro-4-cyanophenoxy) cyclohexyl)-6-((1R,5S,6R)-6-formyl-3-azabicyclo[3.1.0]hexan-3-yl)pyridazine-3-formamide (76 mg, 0.16 mmol), with a yield of 84%.

LC/MS (ESI$^+$) calcd for $C_{35}H_{46}ClN_4O_5$ [M+H]$^+$ m/z, 465.9; found, 466.1.

4. N-((1r,4R)-4-(3-chloro-4-cyanophenoxy)cyclohexyl)-6-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyridazine-3-formamide N-((1r,4R)-4-(3-chloro-4-cyanophenoxy)cyclohexyl)-6-((1R,5S,6R)-6-formyl-3-azabicyclo[3.1.0]hexan-3-yl) pyridazine-3-formamide (35 mg, 0.07 mmol) was weighed and placed in a 25 mL single-neck round bottom flask, to which were added dichloromethane (3 mL) and methanol (1 mL), and then the reaction solution was stirred at room temperature to dissolve and make the solution become clear. Subsequently, 2-(2,6-dioxopiperidin-3-yl)-5-fluoro-6-(piperazin-1-yl)isoindoline-1,3-dione (24 mg, 0.07 mmol) and one drop of glacial acetic acid were added to the system. After that, the mixture was stirred and reacted at room temperature for 15 min, to which was then added sodium triacetylborohydride (45 mg, 0.21 mmol). The system was allowed to react overnight under stirring at room temperature. Next day, the sample was taken out and subjected to TLC, and the result showed the completion of the reaction. Stirring was stopped, and the solvent was removed by rotatory evaporation. Dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by Pre-TLC, to provide compound N-((1r,4R)-4-(3-chloro-4-cyanophenoxy)cyclohexyl)-6-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyridazine-3-formamide (28 mg, 0.03 mmol), with a yield of 45%. LC/MS (ESI$^+$) calcd for $C_{43}H_{46}ClN_6O_7$ [M+H]$^+$ m/z, 810.3; found, 810.3.

$^1$H NMR (400 MHz, $CDCl_3$) δ 8.44 (s, 1H), 8.00 (d, J=9.4 Hz, 1H), 7.91 (d, J=8.2 Hz, 1H), 7.58 (d, J=8.7 Hz, 1H), 7.51 (d, J=10.9 Hz, 1H), 7.45 (d, J=7.2 Hz, 1H), 7.02 (d, J=2.4 Hz, 1H), 6.87 (dd, J=8.7, 2.4 Hz, 1H), 6.71 (d, J=9.4 Hz, 1H), 4.96 (dd, J=12.2, 5.3 Hz, 1H), 4.37-4.30 (m, 1H), 4.15-4.00 (m, 1H), 3.94 (br, 2H), 3.68 (d, J=9.4 Hz, 2H), 3.41 (s, 4H), 2.99-2.68 (m, 6H), 2.60 (br, 2H), 2.27-2.09 (m, 5H), 1.78-1.65 (m, 6H), 1.48 (dd, J=22.4, 10.3 Hz, 2H).

179: N-((1r,4R)-4-(3-chloro-4-cyanophenoxy)cyclohexyl)-6-((1R,5S,6S)-6-((4-(2-(2,6-dioxopiperidin-3-yl)-1,3-dioxoisoindolin-5-yl)piperazin-1-yl)methyl)-3-azabicyclo[3.1.0]hexan-3-yl)pyridazine-3-formamide

178

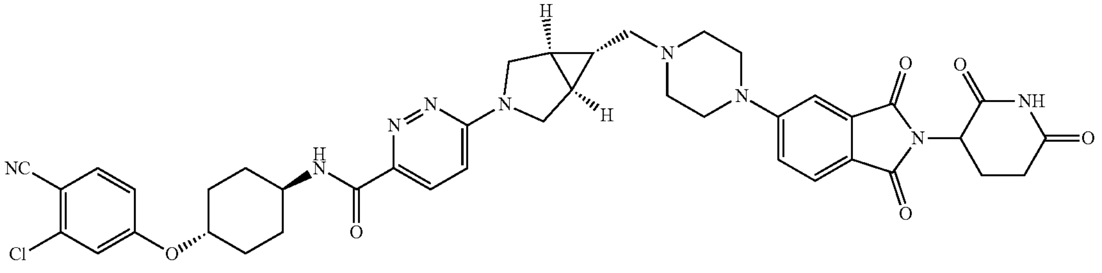

LC/MS ($ESI^+$) calcd for $C_{41}H_{42}ClN_9O_6[M+H]^+$ m/z, 792.3; found, 792.3.
$^1H$ NMR (400 MHz, $CDCl_3$) δ 8.35 (s, 1H), 7.98 (d, J=9.3 Hz, 1H), 7.90 (d, J=8.0 Hz, 1H), 7.71 (d, J=8.4 Hz, 1H), 7.56 (d, J=8.7 Hz, 1H), 7.30 (s, 1H), 7.08 (d, J=8.4 Hz, 1H), 7.00 (d, J=2.0 Hz, 1H), 6.86 (dd, J=8.7, 2.1 Hz, 1H), 6.69 (d, J=9.4 Hz, 1H), 4.95 (dd, J=11.9, 5.0 Hz, 1H), 4.40-4.24 (m, 1H), 4.15-3.99 (m, 1H), 3.91 (br, 2H), 3.66 (d, J=8.7 Hz, 2H), 3.51 (br, 4H), 2.82 (ddd, J=26.2, 22.5, 13.7 Hz, 7H), 2.52 (br, 2H), 2.18 (br, 5H), 1.69 (dd, J=22.6, 11.7 Hz, 5H), 1.46 (dd, J=22.4, 10.6 Hz, 2H).
180: Synthesis of N-((1r,4r)-4-(3-chloro-4-cyano-phenoxy)cyclohexyl)-6-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl) pyridazine-3-formamide
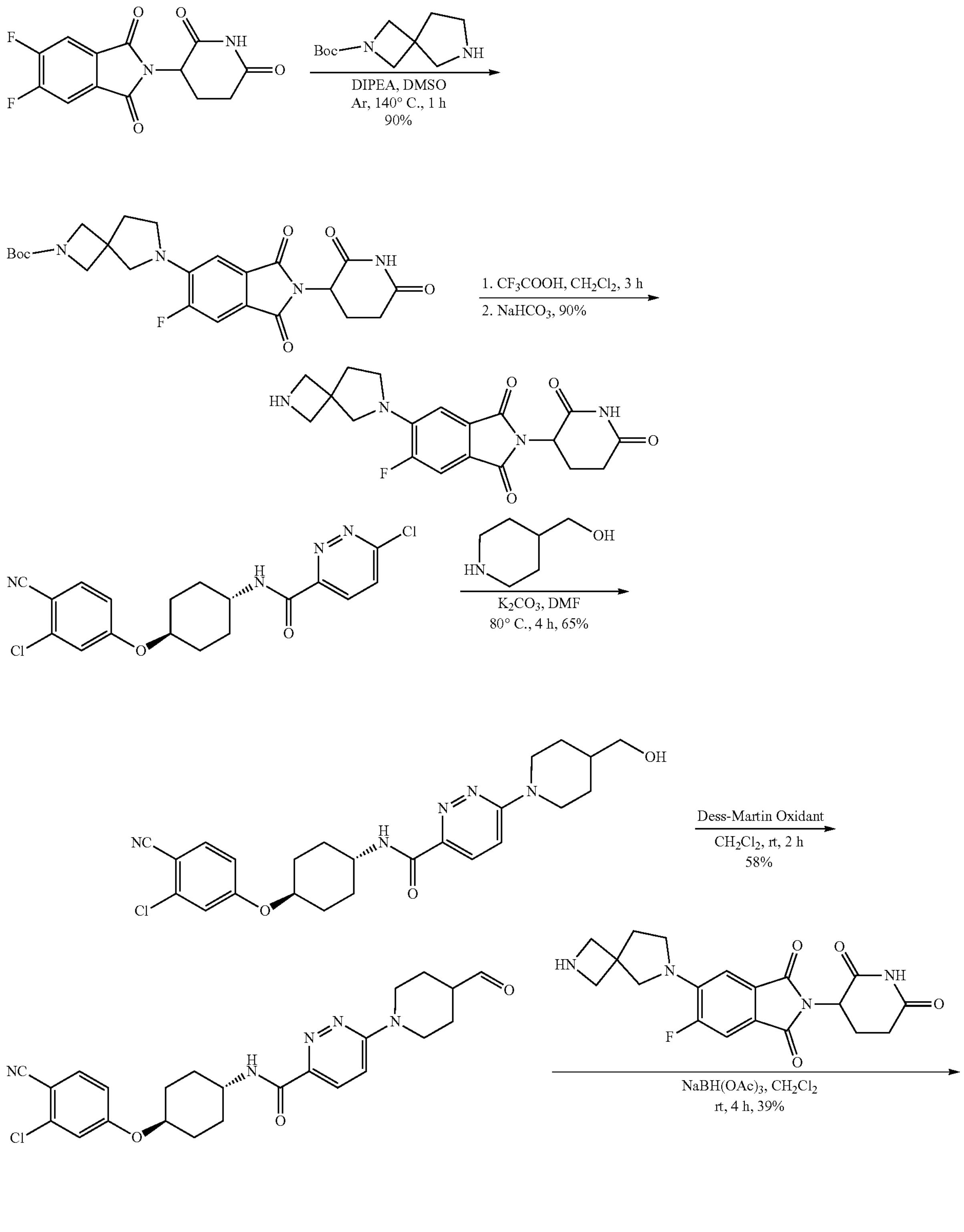

-continued

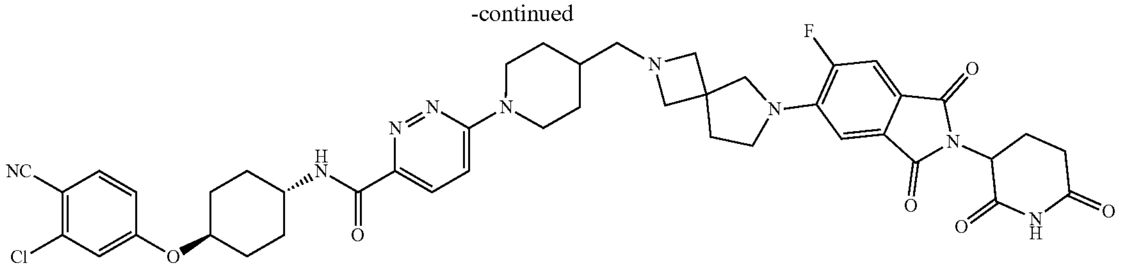

180

1. N-((1r,4r)-4-(3-chloro-4-cyanophenoxy)cyclohexyl)-6-(4-(hydroxymethyl) piperidin-1-ylpyridazine-3-formamide To a round bottom flask containing piperidin-4-ylmethanol (82 mg, 0.71 mmol), was added 5 mL of DMF, and then the reaction solution was stirred at room temperature to dissolve and make the solution become clear. Subsequently, 6-chloro-N-((1r,4r)-4-(3-chloro-4-cyanophenoxy)cyclohexyl)pyridazine-3-formamide (250 mg, 0.64 mmol) and potassium carbonate (294 mg, 2.13 mmol) were added to the system. After that, the system was evacuated and purged with argon gas, that was repeated 5 times, to ensure the inert gas atmosphere in the system. After that, the system was moved to an oil bath at 80° C. for heating and reacting under stirring. After 4 h, TLC indicated the completion of the reaction. Heating was stopped, and once the system was cooled to room temperature, ethyl acetate (10 mL) and water (15 mL) were added to the system. The system was stirred vigorously, and stood still for separation of the layers. The aqueous layer was extracted with ethyl acetate (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by column chromatography, to provide compound N-((1r,4r)-4-(3-chloro-4-cyanophenoxy)cyclohexyl)-6-(4-(hydroxymethyl)piperidin-1-ylpyridazine-3-formamide (218 mg), with a yield of 65%. LC/MS ($ESI^+$) calcd for $C_{24}H_{28}ClN_5O_3[M+H]^+$ m/z, 470.0; found, 469.9.

2. N-((1r,4r)-4-(3-chloro-4-cyanophenoxy)cyclohexyl)-6-(4-formylpiperidin-1-yl) pyridazine-3-formamide N-((1r,4r)-4-(3-chloro-4-cyanophenoxy)cyclohexyl)-6-(4-(hydroxymethyl)piperidin-1-ylpyridazine-3-formamide (50 mg, 0.11 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (72 mg, 0.17 mmol) was added to the system. After that, the system was warmed to room temperature and reacted under stirring at room temperature. After 2 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4r)-4-(3-chloro-4-cyanophenoxy)cyclohexyl)-6-(4-formylpiperidin-1-yl)pyridazine-3-formamide (30 mg), with a yield of 58%. LC/MS ($ESI^+$) calcd for $C_{24}H_{26}ClN_3O_3$ $[M+H]^+$ m/z, 468.0; found, 467.9.

3. Synthesis of Compound butyl-6-(2-(2,6-dioxopiperidin-3-yl)-6-fluoro-1,3-dioxoisoindolin-5-yl)-2,6-diazaspiro[3.4]octan-2-carboxylate 2-(2,6-Dioxopiperidin-3-yl)-5,6-difluoroisoindoline-1,3-dione (200 mg, 0.68 mmol) butyl-2,6-diazaspiro[3.4]octan-2-carboxylate (144 mg, 0.68 mmol) and DIPEA (264 mg, 2.04 mmol) were added in 5 mL DMSO. The reaction solution was heated to 140° C. and stirred for 1 h. The reaction solution was cooled to room temperature, to which were added water and ethyl acetate for extraction. The organic layer was successively washed with 0.1 N HCl and brine, dried over anhydrous sodium sulfate, rotatory evaporated to dry, and the crude product was separated and purified by column chromatography, to provide compound butyl-6-(2-(2,6-dioxopiperidin-3-yl)-6-fluoro-1,3-dioxoisoindolin-5-yl)-2,6-diazaspiro[3.4]octan-2-carboxylate (325 mg), with a yield of 98%.

LC/MS ($ESI^+$) calcd for $C_{24}H_{27}FN_4O_6$ $[M+H]^+$ m/z, 486.5; found, 486.9, 430.9.

4. 2-(2,6-dioxopiperidin-3-yl)-5-fluoro-6-(2,6-diazaspiro[3.4]octan-6-yl)isoindoline-1,3-dione Compound butyl-6-(2-(2,6-dioxopiperidin-3-yl)-6-fluoro-1,3-dioxoisoindolin-5-yl)-2,6-diazaspiro[3.4]octan-2-carboxylate (200 mg, 0.41 mmol) was dissolved in 5 mL of dichloromethane, to which was added 2 mL of trifluoroacetic acid, and the mixture was allowed to react under stirring at room temperature for 3 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound 2-(2,6-dioxopiperidin-3-yl)-5-fluoro-6-(2,6-diazaspiro[3.4]octan-6-yl)isoindoline-1,3-dione (142 mg), with a yield of 90%.

LC/MS ($ESI^+$) calcd for $C_{19}H_{19}FN_4O_4[M+H]^+$ m/z, 386.4; found, 387.0.

5. N-((1r,4r)-4-(3-chloro-4-cyanophenoxy)cyclohexyl)-6-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl)pyridazine-3-formamide N-((1r,4r)-4-(3-chloro-4-cyanophenoxy)cyclohexyl)-6-(4-formylpiperidin-1-yl) pyridazine-3-formamide (30 mg, 0.06 mmol) was weighed and placed in a 25 mL single-neck round bottom flask, to which were added dichloromethane (3 mL), and then the reaction solution was stirred at room temperature to dissolve and make the solution become clear. Subsequently, 2-(2,6-dioxopiperidin-3-yl)-5-fluoro-6-(2,6-diazaspiro[3.4]octan-6-yl)isoindoline-1,3-dione (24 mg, 0.06 mmol) and one drop of glacial acetic acid were added to the system. After that, the mixture was stirred and reacted at room temperature for 15 min, to which was then added sodium triacetylborohydride (38 mg, 0.18 mmol). The system was allowed to react under stirring at room temperature. After 4 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*3) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-6-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl)pyridazine-3-formamide (21 mg), with a yield of 39%.

LC/MS ($ESI^+$) calcd for $C_{43}H_{45}ClFN_9O_6$ $[M+H]^+$ m/z, 838.3; found, 837.8.

$^1H$ NMR (400 MHz, $CDCl_3$) δ 8.37 (s, 1H), 7.97 (d, J=9.5 Hz, 1H), 7.88 (d, J=8.0 Hz, 1H), 7.56 (d, J=8.7 Hz, 1H), 7.40 (d, J=12.2 Hz, 1H), 7.10-6.91 (m, 3H), 6.86 (dd, J=8.7, 2.2 Hz, 1H), 4.92 (dd, J=12.0, 5.0 Hz, 1H), 4.50 (d, J=13.2 Hz, 2H), 4.32 (t, J=9.6 Hz, 1H), 4.12-3.99 (m, 1H), 3.73 (s, 2H), 3.59 (br, 2H), 3.35 (br, 4H), 3.02 (t. J=11.9 Hz, 2H), 2.94-2.66 (m, 3H), 2.49 (br, 2H), 2.29-2.08 (m, 7H), 1.91 (d, J=11.9 Hz, 3H), 1.68 (dd, J=22.2, 10.1 Hz, 3H), 1.46 (dd, J=22.2, 10.3 Hz, 3H).

181: Synthesis of N-((1r,3R)-3-(3-chloro-4-cyanophenoxy)-2,2,4,4-tetramethylcyclobutyl)-6-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyridazine-3-formamide

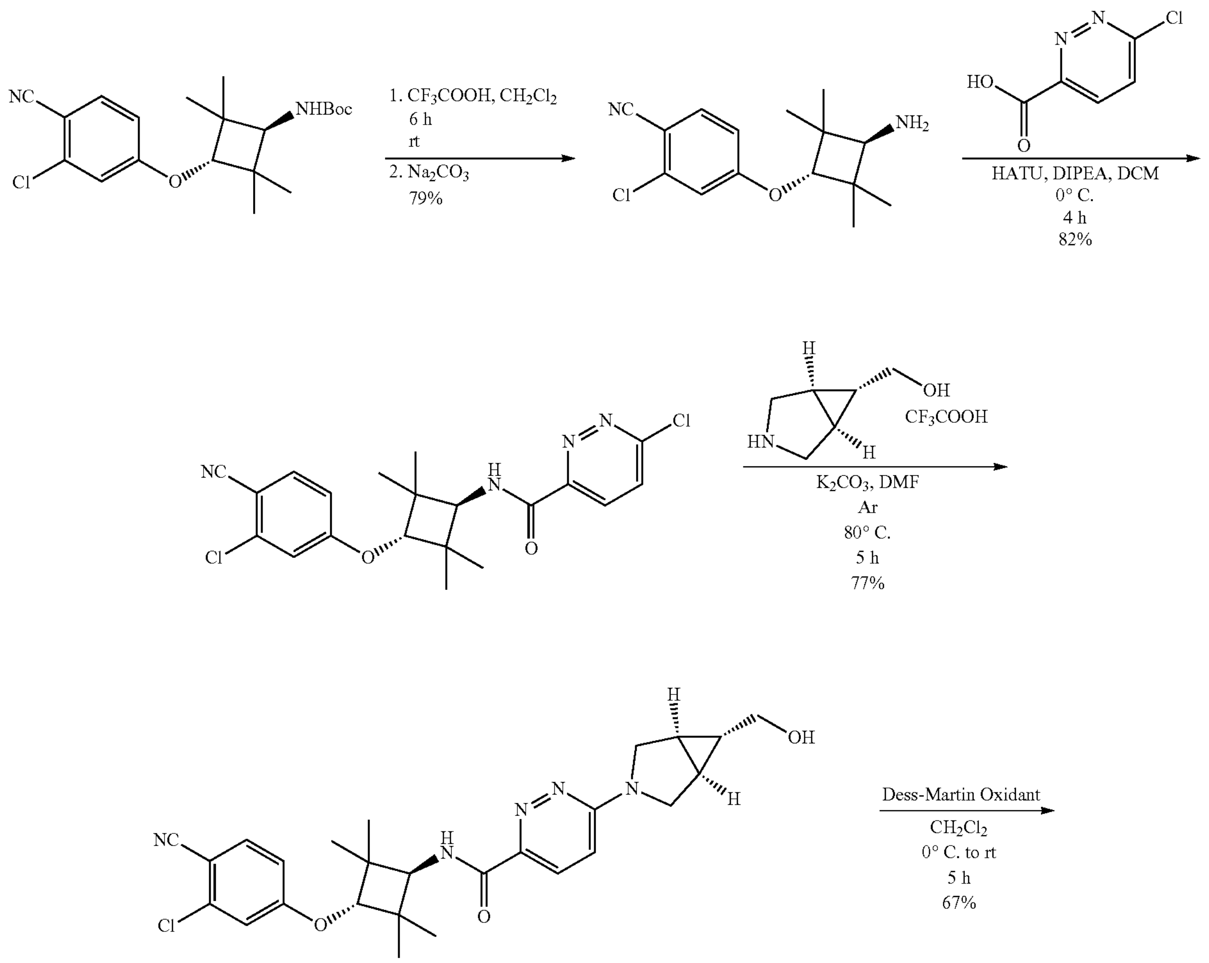

-continued

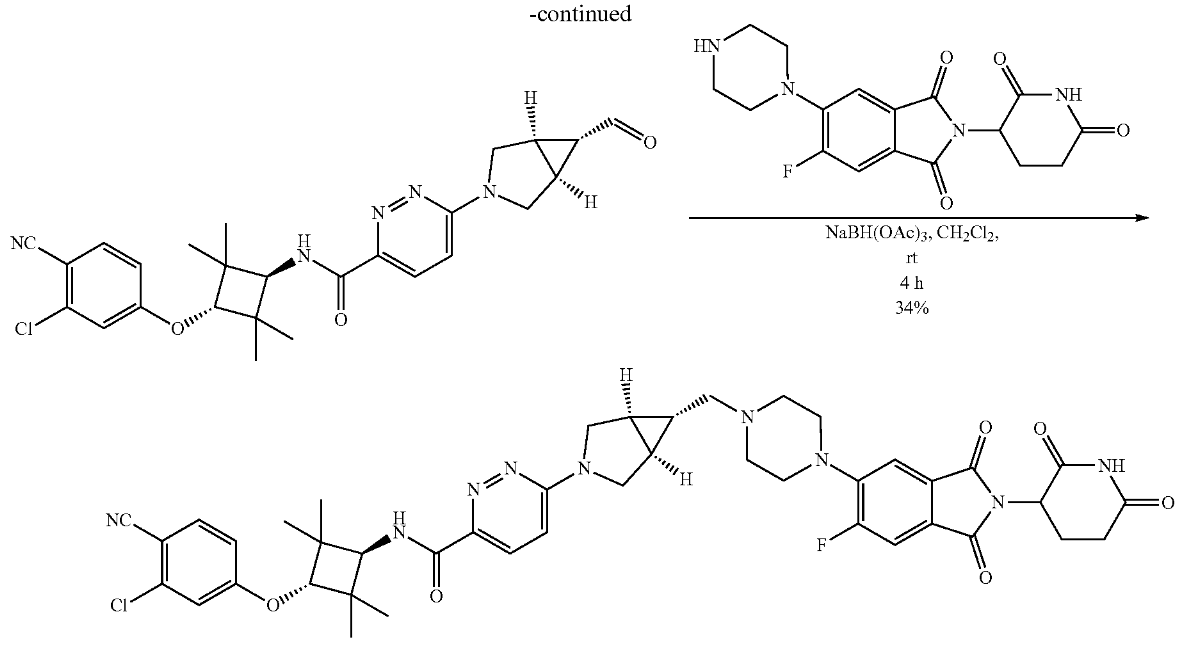

181

1. Synthesis of Compound 4-((1r,3r)-3-amino-2,2,4,4-tetramethylcyclobutoxy)-2-chlorobenzonitrile Compound t-butyl ((1r,3r)-3-(3-chloro-4-cyanophenoxy)-2,2,4,4-tetramethylcyclobutyl)carbamate (2400 mg, 6.33 mmol) was dissolved in 24 mL of dichloromethane, to which was added 6 mL of trifluoroacetic acid, and the mixture was allowed to react under stirring at room temperature for 6 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 30 mL of dichloromethane and 15 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane/methanol (10:1) (30 mL*3). The organic layers were combined, successively washed with water and saturated brine, and dried over anhydrous sodium sulfate. The crude product was separated and purified by column chromatography to obtain compound 4-((1r,3r)-3-amino-2,2,4,4-tetramethylcyclobutoxy)-2-chlorobenzonitrile (1400 mg), with a yield of 79%.

2. Synthesis of Compound 6-chloro-N-((1r,3r)-3-(3-chloro-4-cyanophenoxy)-2,2,4,4-tetramethylcyclobutyl)pyridazine-3-formamide 6-Chloropyridazine-3-carboxylic acid (143 mg, 0.90 mmol) was weighed and placed in a 50 mL single-necked round bottom flask, to which was added 10 mL of dichloromethane, and the mixture was stirred well at room temperature. Then, the system was moved to an ice-water bath to continue cooling under stirring, to which were added HATU (513 mg, 1.35 mmol) and DIPEA (233.0 mg, 1.80 mmol). After that, the system was stirred in the ice-water bath for 20 min, and 4-((1r,3r)-3-amino-2,2,4,4-tetramethylcyclobutoxy)-2-chlorobenzonitrile (250 mg, 0.90 mmol) was added to the system. The system was stirred and reacted in an ice-water bath. After 4 h. TLC showed the complete disappearance of the starting material. The reaction was stopped, and dichloromethane (10 mL) and water (10 mL) were added to the system. The system was stirred vigorously, and stood still for separation of the layers. The aqueous phase was extracted with dichloromethane (5 mL*3). The organic phase was combined, and successively washed with water and saturated brine, dried over anhydrous sodium sulfate. The solvent was removed by rotatory evaporation, to obtain a crude product, which was separated by column chromatography, to provide compound 6-chloro-N-((1r,3r)-3-(3-chloro-4-cyanophenoxy)-2,2,4,4-tetramethylcyclobutyl)pyridazine-3-formamide (312 mg), with a yield of 82%. LC/MS (ESI) calcd for $C_{20}H_{20}Cl_2N_4O_2$ $[M+H]^+$ m/z, 419.3; found, 418.9.

3. Synthesis of Compound N-((1r,3R)-3-(3-chloro-4-cyanophenoxy)-2,2,4,4-tetramethylcyclobutyl)-6-((1R,5S,6R)-6-(hydroxymethyl)-3-azabicyclo[3.1.0]hexan-3-yl)pyridazine-3-formamide To a round bottom flask containing ((1R,5S,6r)-3-azabicyclo[3.1.0]hexan-6-yl)methanol trifluoroacetate (80 mg, 0.35 mmol), was added 5 mL of DMF, and then the reaction solution was stirred at room temperature to dissolve and make the solution become clear. Subsequently, 6-chloro-N-((1r,3r)-3-(3-chloro-4-cyanophenoxy)-2,2,4,4-tetramethylcyclobutyl)pyridazine-3-formamide (130 mg, 0.31 mmol) and potassium carbonate (242 mg, 1.75 mmol) were added to the system. After that, the system was evacuated and purged with argon gas, that was repeated 5 times, to ensure the inert gas atmosphere in the system. After that, the system was moved to an oil bath at 80° C. for heating and reacting under stirring. After 5 h, TLC indicated the completion of the reaction. Heating was stopped, and once the system was cooled to room temperature, ethyl acetate (10 mL) and water (15 mL) were added to the system. The system was stirred vigorously, and stood still for separation of the layers. The aqueous layer was extracted with ethyl acetate (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by column chromatography, to provide compound N-((1r,3R)-3-(3-chloro-4-cyanophenoxy)-2,2,4,4-tetramethylcyclobutyl)-6-((1R,5S,6R)-6-(hydroxymethyl)-3-azabicyclo[3.1.0]hexan-3-yl)pyridazine-3-formamide (118 mg), with a yield of 77%.

LC/MS (ESI+) calcd for $C_{26}H_{30}ClN_5O_3[M+H]^+$ m/z, 496.0; found, 495.9.

4. Synthesis of Compound N-((1r,3R)-3-(3-chloro-4-cyanophenoxy)-2,2,4,4-tetramethylcyclobutyl)-6-((1R,5S,6R)-6-formyl-3-azabicyclo[3.1.0]hexan-3-yl) pyridazine-3-formamide N-((1r,3R)-3-(3-chloro-4-cyanophenoxy)-2,2,4,4-tetramethylcyclobutyl)-6-((1R,5S,6R)-6-(hydroxymethyl)-3-azabicyclo[3.1.0]hexan-3-yl)pyridazine-3-formamide (60 mg, 0.12 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (102 mg, 0.24 mmol) was added to the system. After that, the system was warmed to room temperature and reacted under stirring at room temperature. After 5 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,3R)-3-(3-chloro-4-cyanophenoxy)-2,2,4,4-tetramethylcyclobutyl)-6-((1R,5S,6R)-6-formyl-3-azabicyclo[3.1.0]hexan-3-yl)pyridazine-3-formamide (40 mg), with a yield of 67%.

LC/MS (ESI+) calcd for $C_{26}H_{28}ClN_5O_3$ $[M+H]^+$ m/z, 494.0; found, 493.9.

5. Synthesis of Compound N-((1r,3R)-3-(3-chloro-4-cyanophenoxy)-2,2,4,4-tetramethylcyclobutyl)-6-((1R,5S,6S)-6-((4-(2-(2,6-dioxopiperidin-3-yl)-6-fluoro-1,3-dioxoisoindolin-5-yl)piperazin-1-yl) methyl)-3-azabicyclo[3.1.0]hexan-3-yl) pyridazine-3-formamide N-((1r,3R)-3-(3-chloro-4-cyanophenoxy)-2,2,4,4-tetramethylcyclobutyl)-6-((1R,5S,6R)-6-formyl-3-azabicyclo[3.1.0]hexan-3-yl)pyridazine-3-formamide (40 mg, 0.08 mmol) was weighed and placed in a 25 mL single-neck round bottom flask, to which were added dichloromethane (5 mL), and then the reaction solution was stirred at room temperature to dissolve and make the solution become clear. Subsequently, 2-(2,6-dioxopiperidin-3-yl)-5-fluoro-6-(piperazin-1-yl)isoindoline-1,3-dione (29 mg, 0.08 mmol) and one drop of glacial acetic acid were added to the system. After that, the mixture was stirred and reacted at room temperature for 15 min, to which was then added sodium triacetylborohydride (51 mg, 0.24 mmol). The system was allowed to react under stirring at room temperature. After 4 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,3R)-3-(3-chloro-4-cyanophenoxy)-2,2,4,4-tetramethylcyclobutyl)-6-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyridazine-3-formamide (23 mg), with a yield of 34%.

LC/MS (ESI+) calcd for $C_{43}H_{45}ClFN_9O_6$ $[M+H]^+$ m/z, 838.3; found, 837.7.

$^1$H NMR (400 MHz, $CDCl_3$) δ 8.59 (br, 1H), 8.18 (d, J=9.1 Hz, 1H), 7.99 (d, J=9.4 Hz, 1H), 7.57 (d, J=8.7 Hz, 1H), 7.48 (d, J=10.9 Hz, 1H), 7.43 (d, J=7.2 Hz, 1H), 6.97 (d, J=2.3 Hz, 1H), 6.81 (dd, J=8.7, 2.3 Hz, 1H), 6.71 (d, J=9.4 Hz, 1H), 4.94 (dd, J=12.1, 5.3 Hz, 1H), 4.19 (d, J=9.1 Hz, 1H), 4.07 (s, 1H), 3.92 (br, 2H), 3.67 (d, J=9.1 Hz, 2H), 3.32 (br, 4H), 2.93-2.68 (m, 7H), 2.50 (d, J=6.5 Hz, 2H), 2.24-2.20 (m, 1H), 2.19-2.09 (m, 2H), 2.01 (dd, J=12.9, 7.4 Hz, 1H), 1.28 (s, 6H), 1.21 (s, 6H).

182: N-((1r,3R)-3-(3-chloro-4-cyanophenoxy)-2,2,4,4-tetramethylcyclobutyl)-5-((1R,5S,6S)-6-((4-(2-(2,6-dioxopiperidin-3-yl)-6-fluoro-1,3-dioxoisoindolin-5-yl)piperazin-1-yl)methyl)-3-azabicyclo[3.1.0]hexan-3-yl)pyrazine-2-carboxamide

182

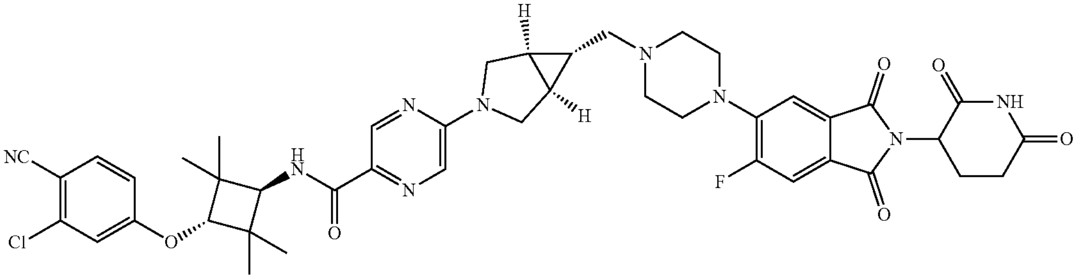

LC/MS ($ESI^+$) calcd for $C_{43}H_{45}ClFN_9O_6$ $[M+H]^+$ m/z, 838.3; found, 837.8.

$^1H$ NMR (400 MHz, $CDCl_3$) δ 8.83 (s, 1H), 8.47 (br, 1H), 7.77 (d, J=8.9 Hz, 1H), 7.72 (s, 1H), 7.57 (d, J=8.7 Hz, 1H), 7.48 (d, J=11.0 Hz, 1H), 7.43 (d, J=7.2 Hz, 1H), 6.97 (d, J=2.3 Hz, 1H), 6.81 (dd, J=8.7, 2.3 Hz, 1H), 4.94 (dd, J=12.2, 5.3 Hz, 1H), 4.14 (d, J=8.8 Hz, 1H), 4.07 (s, 1H), 3.87 (d, J=9.9 Hz, 2H), 3.62 (d, J=10.2 Hz, 2H), 3.32 (br, 4H), 2.95-2.64 (m, 7H), 2.48 (d, J=6.4 Hz, 2H), 2.21 (dd, J=17.9, 9.8 Hz, 1H), 2.19-2.09 (m, 2H), 2.01 (ddd, J=10.1, 8.4, 2.8 Hz, 1H), 1.26 (s, 6H), 1.21 (s, 6H).

183: Synthesis of N-((1r,4r)-4-(3-chloro-4-cyano-phenoxy)cyclohexyl)-6-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl) pyridazine-3-formamide 1. Synthesis of 2-(2,6-dioxopiperidin-3-yl)-5-fluoro-6-(4-(hydroxymethyl)piperidin-1-yl)isoindoline-1,3-dione 2-(2,6-dioxopiperidin-3-yl)-5,6-difluoroisoindoline-1,3-dione (294 mg, 1.00 mmol), piperidin-4-ylmethanol (115 mg, 1.00 mmol) and DIPEA (388 mg, 3.00 mmol) were added in 5 mL DMSO. The reaction solution was heated to 140° C. and stirred for 1 h. The reaction solution was cooled to room temperature, to which were added water and ethyl acetate for extraction. The organic layer was successively washed with 0.1 N HCl and brine, dried over anhydrous sodium sulfate, rotatory evaporated to dry, and the crude product was separated and purified by column chromatography, to provide compound 2-(2,6-dioxopiperidin-3-yl)-5-fluoro-6-(4-(hydroxymethyl)piperidin-1-yl)isoindoline-1,3-dione (311 mg), with a yield of 80%.

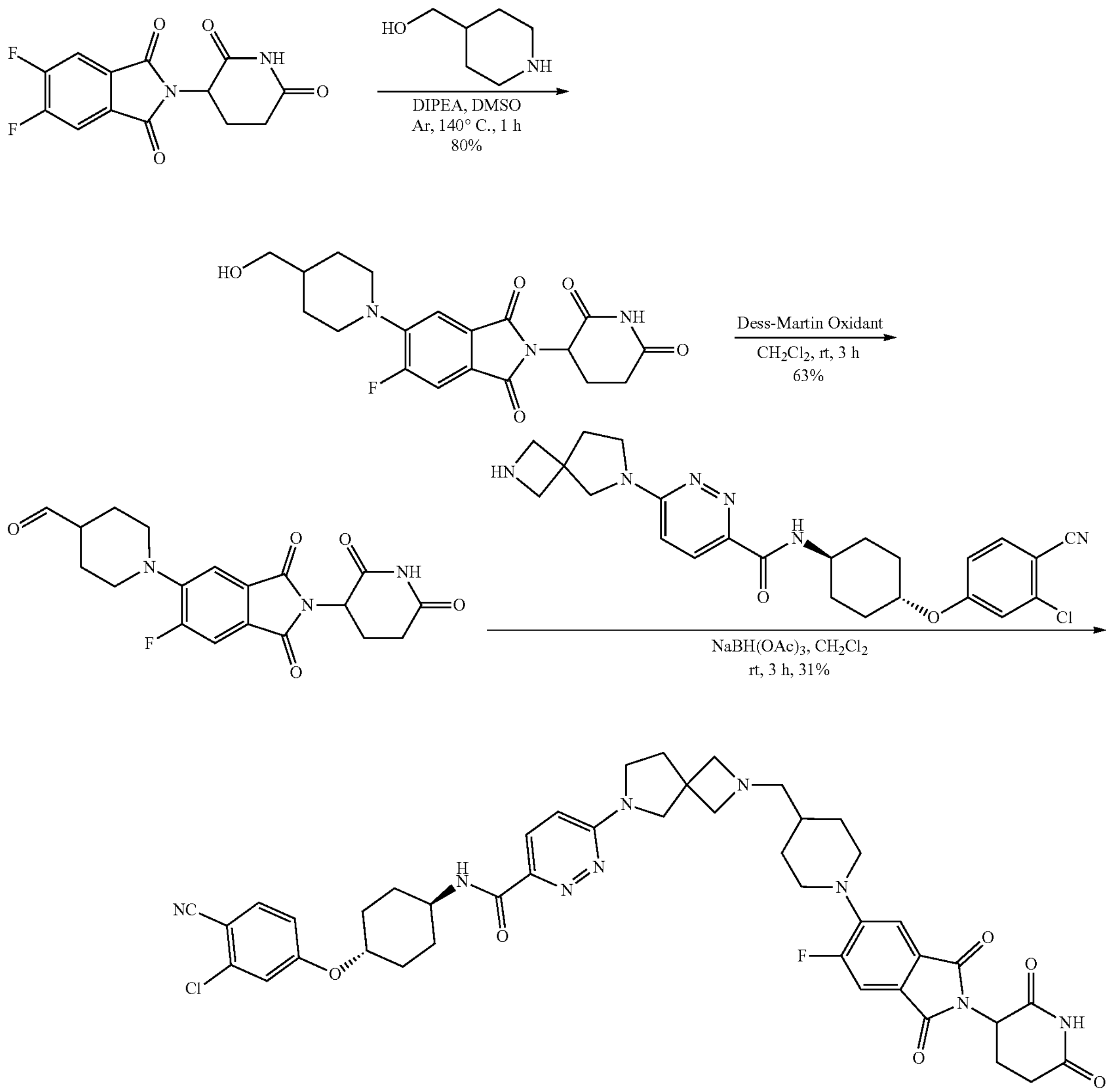

LC/MS ($ESI^+$) calcd for $C_{19}H_{20}FN_3O_5[M+H]^+$ m/z, 389.4; found, 389.7.

2. Synthesis of 1-(2-(2,6-dioxopiperidin-3-yl)-6-fluoro-1,3-dioxoisoindolin-5-yl)piperidine-4-formaldehyde 2-(2,6-Dioxopiperidin-3-yl)-5-fluoro-6-(4-(hydroxymethyl)piperidin-1-yl)isoindoline-1,3-dione (100 mg, 0.26 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (220 mg, 0.52 mmol) was added to the system. After that, the system was warmed to room temperature and reacted under stirring at room temperature. After 3 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound 1-(2-(2,6-dioxopiperidin-3-yl)-6-fluoro-1,3-dioxoisoindolin-5-yl)piperidine-4-formaldehyde (63 mg), with a yield of 63%. LC/MS ($ESI^+$) calcd for $C_{19}H_{18}FN_3O_5^+$ $[M+H]^+$ m/z, 387.4; found, 387.7.

3. Synthesis of Compound N-((1r,4r)-4-(3-chloro-4-cyanophenoxy)cyclohexyl)-6-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl)pyridazine-3-formamide 1-(2-(2,6-Dioxopiperidin-3-yl)-6-fluoro-1,3-dioxoisoindolin-5-yl)piperidine-4-formaldehyde (30 mg, 0.08 mmol) was weighed and placed in a 25 mL single-neck round bottom flask, to which were added dichloromethane (5 mL), and then the reaction solution was stirred at room temperature to dissolve and make the solution become clear. Subsequently, N-((1r,4r)-4-(3-chloro-4-cyanophenoxy)cyclohexyl)-6-(2,6-diazaspiro[3.4]octan-6-yl)pyridazine-3-formamide (37 mg, 0.08 mmol) and one drop of glacial acetic acid were added to the system. After that, the mixture was stirred and reacted at room temperature for 15 min, to which was then added sodium triacetylborohydride (51 mg, 0.24 mmol). The system was allowed to react under stirring at room temperature. After 3 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-6-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl)pyridazine-3-formamide (21 mg), with a yield of 31%.

LC/MS ($ESI^+$) calcd for $C_{43}H_{45}ClFN_9O_6$ $[M+H]^+$ m/z, 838.3; found, 837.7.

$^1H$ NMR (400 MHz, $CDCl_3$) δ 8.59 (br, 1H), 8.00 (d, J=9.3 Hz, 1H), 7.91 (d, J=8.1 Hz, 1H), 7.56 (d, J=8.7 Hz, 1H), 7.46 (d, J=11.0 Hz, 1H), 7.38 (d, J=7.2 Hz, 1H), 7.01 (d, J=2.1 Hz, 1H), 6.86 (dd, J=8.7, 2.2 Hz, 1H), 6.71 (d, J=9.4 Hz, 1H), 4.94 (dd, J=12.1, 5.2 Hz, 1H), 4.37-4.27 (m, 1H), 4.12-3.99 (m, 1H), 3.74 (br, 2H), 3.64 (d, J=11.2 Hz, 4H), 3.38 (dd, J=25.3, 6.9 Hz, 4H), 2.95-2.67 (m, 5H), 2.52 (d, J=6.6 Hz, 2H), 2.31-2.28 (m, 2H), 2.13 (dd, J=14.2, 6.3 Hz, 3H), 1.86 (d, J=11.9 Hz, 3H), 1.76-1.54 (m, 4H), 1.44 (dt, J=21.3, 11.1 Hz, 4H).

184: Synthesis of N-((1r,4r)-4-(3-chloro-4-cyanophenoxy)cyclohexyl)-6-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl)pyridazine-3-formamide

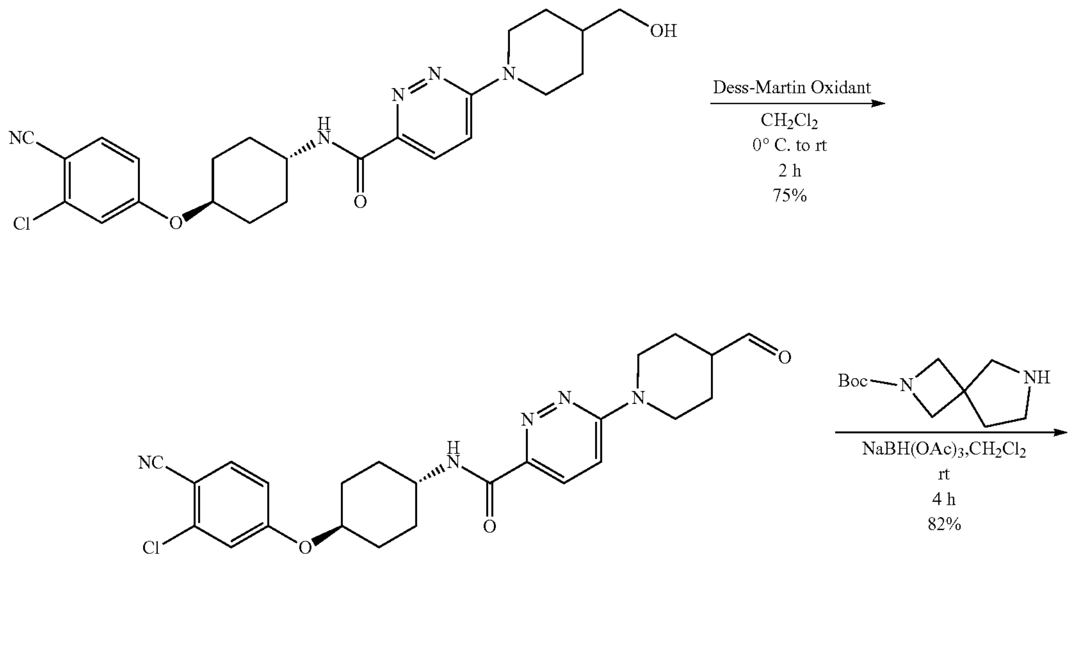

-continued

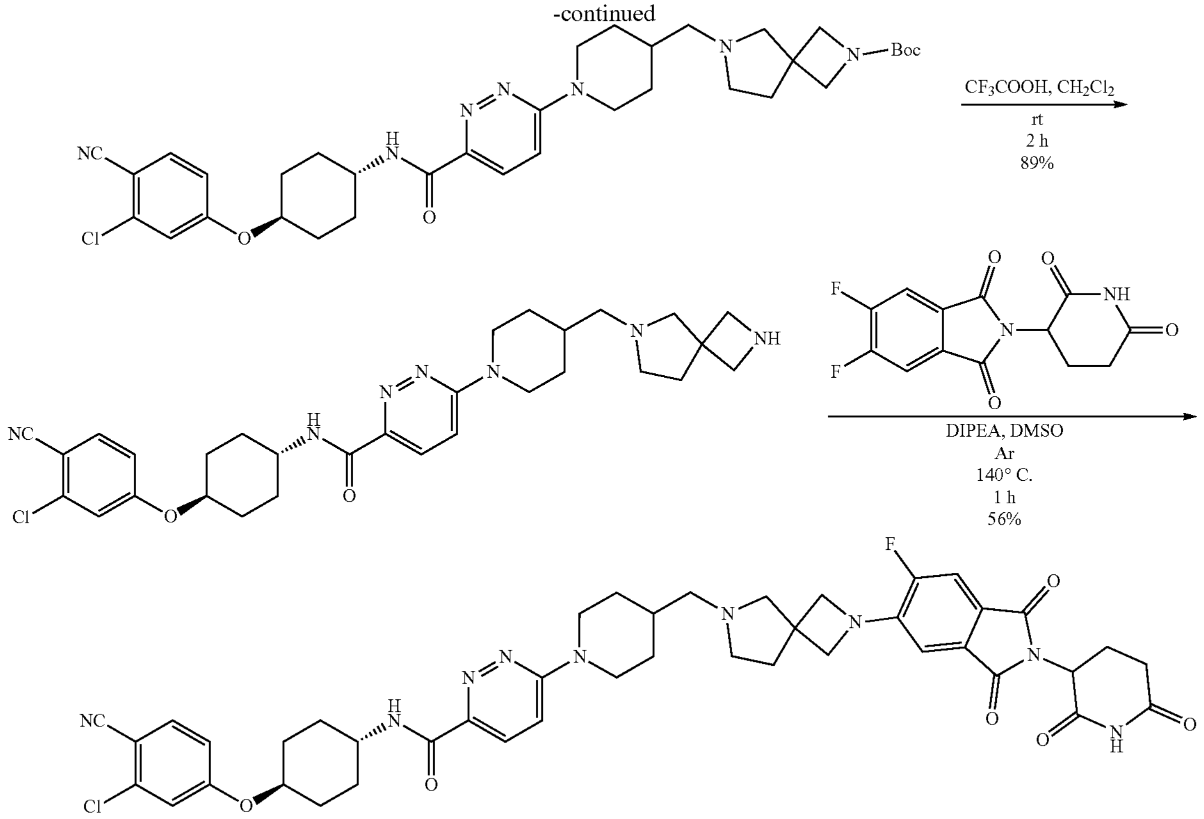

184

1. Compound N-((1r,4r)-4-(3-chloro-4-cyanophenoxy)cyclohexyl)-6-(4-formylpiperidin-1-yl) pyridazine-3-formamide N-((1r,4r)-4-(3-chloro-4-cyanophenoxy)cyclohexyl)-6-(4-(hydroxymethyl)piperidin-1-ylpyridazine-3-formamide (80 mg, 0.17 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (110 mg, 0.26 mmol) was added to the system. After that, the system was warmed to room temperature and reacted under stirring at room temperature. After 2 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4r)-4-(3-chloro-4-cyanophenoxy)cyclohexyl)-6-(4-formylpiperidin-1-yl)pyridazine-3-formamide (60 mg), with a yield of 75%.

LC/MS (ESI) calcd for $C_{24}H_{26}ClN_5O_3[M+H]^+$ m/z, 467.9; found, 468.0.

2. Synthesis of Compound t-butyl 6-((1-(6-(((1r,4r)-4-(3-chloro-4-cyanophenoxy)cyclohexyl)carbamoyl) pyridazine-3-yl)piperidine-4-yl)methyl)-2,6-diazaspiro[3.4]octan-2-carboxylic acid N-((1r,4r)-4-(3-chloro-4-cyanophenoxy)cyclohexyl)-6-(4-formylpiperidin-1-yl) pyridazine-3-formamide (60 mg, 0.13 mmol) was weighed and placed in a 25 mL single-neck round bottom flask, to which were added dichloromethane (3 mL), and then the reaction solution was stirred at room temperature to dissolve and make the solution become clear. Subsequently, t-butyl 2,6-diazaspiro[3.4]octan-2-carboxylate (28 mg, 0.13 mmol) and one drop of glacial acetic acid were added to the system. After that, the mixture was stirred and reacted at room temperature for 15 min, to which was then added sodium triacetylborohydride (83 mg, 0.39 mmol). The system was allowed to react under stirring at room temperature. After 4 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound t-butyl 6-((1-(6-(((1r,4r)-4-(3-chloro-4-cyanophenoxy)cyclohexyl) carbamoyl)pyridazine-3-yl)piperidine-4-yl)methyl)-2,6-diazaspiro[3.4]octan-2-carboxylate (70 mg), with a yield of 82%.

LC/MS ($ESI^+$) calcd for $C_{35}H_{46}ClN_7O_4$ $[M+H]^+$ m/z, 664.2; found, 664.7.

3. Synthesis of Compound 6-(4-((2,6-diazaspiro[3.4]octan-6-yl)methyl)piperidin-1-yl)-N-((1r,4r)-4-(3-chloro-4-cyanophenoxy)cyclohexyl)pyridazine-3-formamide t-Butyl 6-((1-(6-(((1r,4r)-4-(3-chloro-4-cyanophenoxy)cyclohexyl)carbamoyl) pyridazine-3-yl)piperidine-4-yl)methyl)-2,6-diazaspiro[3.4]octan-2-carboxylate (70 mg, 0.11 mmol) was dissolved in 6 mL of dichloromethane, to which was added 2 mL of trifluoroacetic acid, and the mixture was allowed to react under stirring at room temperature for 2 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound 6-(4-((2,6-diazaspiro[3.4]octan-6-yl)methyl)piperidin-1-yl)-N-((1r,4r)-4-(3-chloro-4-cyanophenoxy)cyclohexyl) pyridazine-3-formamide (53 mg), with a yield of 89%. LC/MS ($ESI^+$) calcd for $C_{30}H_{38}ClN_7O_2$ $[M+H]^+$ m/z, 564.1; found, 564.3.

4. Synthesis of compound N-((1r,4r)-4-(3-chloro-4-cyanophenoxy)cyclohexyl)-6-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl) pyridazine-3-formamide 6-(4-((2,6-diazaspiro[3.4]octan-6-yl)methyl)piperidin-1-yl)-N-((1r,4r)-4-(3-chloro-4-cyanophenoxy)cyclohexyl) pyridazine-3-formamide (28 mg, 0.05 mmol), 2-(2,6-dioxopiperidin-3-yl)-5,6-difluoroisoindoline-1,3-dione (15 mg, 0.05 mmol) and DIPEA (20 mg, 0.15 mmol) were added in 3 mL of DMSO. The reaction solution was heated to 140° C. and allowed to react for 1 h under stirring. The reaction solution was cooled to room temperature, to which were added water and ethyl acetate for extraction. The organic layer was successively washed with 0.1 N HCl and brine, dried over anhydrous sodium sulfate, rotatory evaporated to dry, and the crude product was separated and purified by Pre-TLC, to provide compound N-((1r,4r)-4-(3-chloro-4-cyanophenoxy)cyclohexyl)-6-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl)pyridazine-3-formamide (24 mg), with a yield of 56%.

LC/MS (ESI) calcd for $C_{43}H_{45}ClFN_9O_6[M+H]^+$ m/z, 838.3; found, 837.7.

$^1H$ NMR (400 MHz, $CDCl_3$) δ 8.84 (br, 1H), 7.97 (d, J=9.6 Hz, 1H), 7.88 (d, J=8.2 Hz, 1H), 7.56 (d, J=8.7 Hz, 1H), 7.37 (d, J=10.7 Hz, 1H), 7.00 (d, J=2.3 Hz, 1H), 6.98 (d, J=9.7 Hz, 1H), 6.92 (d, J=7.5 Hz, 1H), 6.86 (dd, J=8.8, 2.4 Hz, 1H), 4.92 (dd, J=12.3, 5.2 Hz, 1H), 4.51 (d, J=11.1 Hz, 2H), 4.32 (ddd, J=13.4, 9.9, 3.5 Hz, 1H), 4.25-3.94 (m, 5H), 3.04 (t, J=12.2 Hz, 2H), 2.96-2.63 (m, 6H), 2.44 (br, 2H), 2.29-2.05 (m, 7H), 2.03-1.92 (m, 2H), 1.77-1.60 (m, 6H), 1.52-1.40 (m, 2H).

185: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,6-diazaspiro[3.4]octan-6-yl)methyl)piperidin-1-yl)pyridazine-3-formamide

185

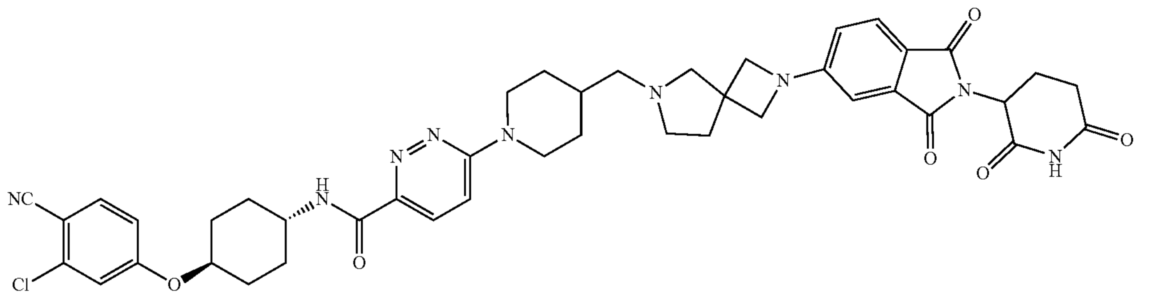

LC/MS ($ESI^+$) calcd for $C_{43}H_{46}ClN_9O_6$ $[M+H]^+$ m/z, 820.3; found, 819.8.

$^1H$ NMR (400 MHz, $CDCl_3$) θ 8.53 (br, 1H), 7.97 (d, J=9.6 Hz, 1H), 7.88 (d, J=8.2 Hz, 1H), 7.65 (d, J=8.3 Hz, 1H), 7.56 (d, J=8.7 Hz, 1H), 7.00 (d, J=2.3 Hz, 1H), 6.98 (d, J=9.7 Hz, 1H), 6.86 (dd, J=9.0, 2.2 Hz, 2H), 6.53 (dd, J=8.3, 1.6 Hz, 1H), 4.94 (dd, J=12.3, 5.3 Hz, 1H), 4.52 (d, J=11.4 Hz, 2H), 4.32 (ddd, J=8.4, 7.9, 3.1 Hz, 1H), 4.14-3.85 (m, 5H), 3.04 (t, J=11.8 Hz, 2H), 2.80 (dddd, J=32.8, 29.2, 14.3, 4.0 Hz, 6H), 2.44 (br, 2H), 2.27-2.09 (m, 7H), 2.03-1.93 (m, 2H), 1.73-1.63 (m, 6H), 1.51-1.41 (m, 2H).

186: Synthesis of N-((1r,4r)-4-(3-chloro-4-cyano-phenoxy)cyclohexyl)-5-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl)pyrazine-2-carboxamide
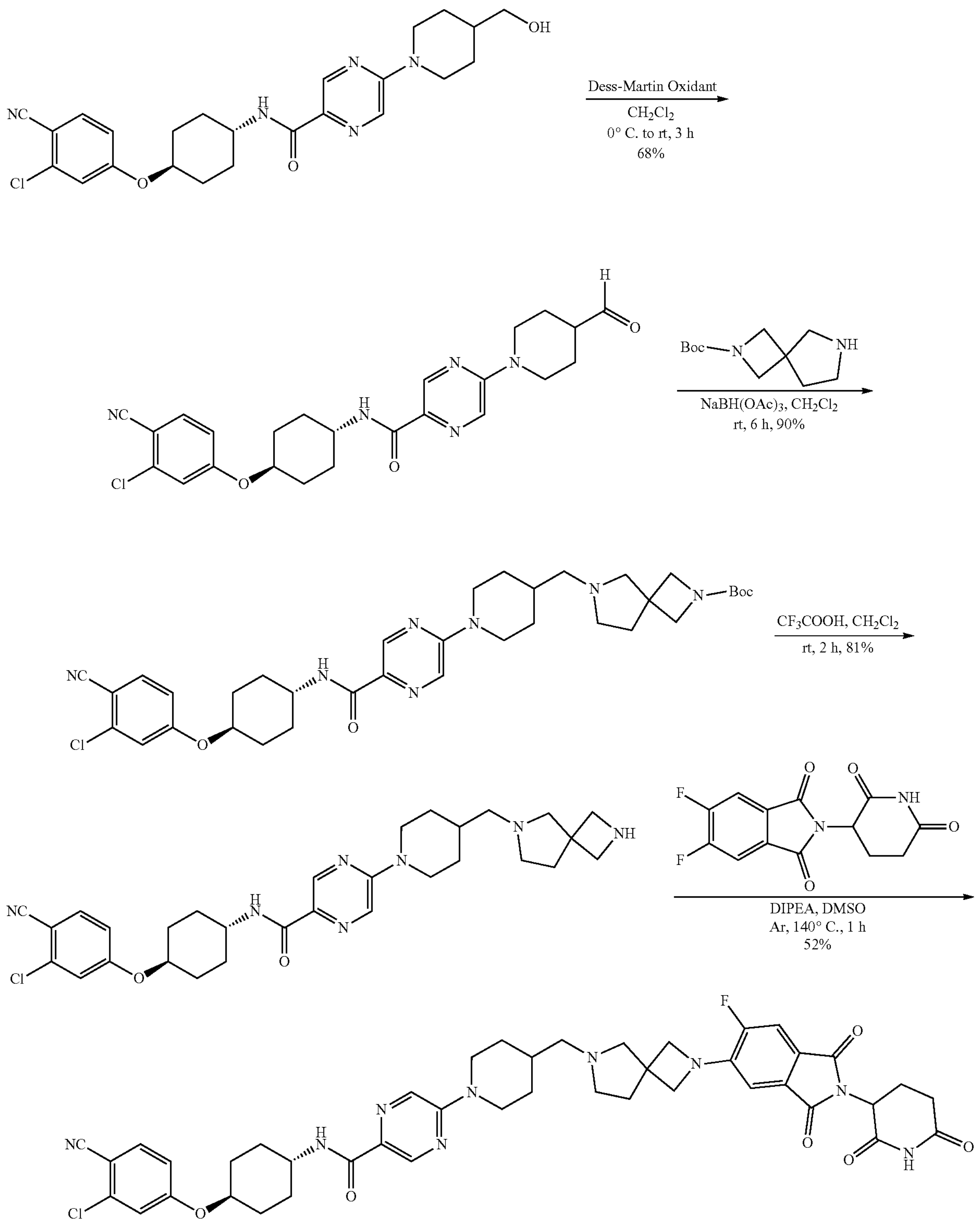

1. N-((1r,4r)-4-(3-chloro-4-cyanophenoxy)cyclohexyl)-5-(4-formylpiperidin-1-yl)pyrazine-2-carboxamide N-((1r,4r)-4-(3-chloro-4-cyanophenoxy)cyclohexyl)-5-(4-(hydroxymethyl)piperidin-1-yl)pyrazine-2-carboxamide (300 mg, 0.64 mmol) was placed in a 25 mL single-neck round bottom flask, to which was added dichloromethane (10 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (407 mg, 0.96 mmol) was added to the system. After that, the system was warmed to room temperature and reacted under stirring at room temperature. After 3 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4r)-4-(3-chloro-4-cyanophenoxy)cyclohexyl)-5-(4-formylpiperidin-1-yl)pyrazine-2-carboxamide (205 mg), with a yield of 68%.

LC/MS (ESI$^+$) calcd for $C_{24}H_{26}ClN_5O_3$ $[M+H]^+$ m/z, 467.9; found, 468.0.

2. Synthesis of Compound t-butyl 6-((1-(5-(((1r,4r)-4-(3-chloro-4-cyanophenoxy)cyclohexyl)carbamoyl)pyrazine-2-yl)piperidine-4-yl)methyl)-2,6-diazaspiro[3.4]octan-2-carboxylate N-((1r,4r)-4-(3-chloro-4-cyanophenoxy)cyclohexyl)-5-(4-formylpiperidin-1-yl) pyrazine-2-carboxamide (70 mg, 0.15 mmol) was weighed and placed in a 25 mL single-neck round bottom flask, to which were added dichloromethane (5 mL), and then the reaction solution was stirred at room temperature to dissolve and make the solution become clear. Subsequently, t-butyl 2,6-diazaspiro[3.4]octan-2-carboxylate (32 mg, 0.15 mmol) and one drop of glacial acetic acid were added to the system. After that, the mixture was stirred and reacted at room temperature for 15 min, to which was then added sodium triacetylborohydride (95 mg, 0.45 mmol). The system was allowed to react under stirring at room temperature. After 6 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound t-butyl 6-((1-(5-(((1r,4r)-4-(3-chloro-4-cyanophenoxy)cyclohexyl)carbamoyl)pyrazine-2-yl)piperidine-4-yl)methyl)-2,6-diazaspiro[3.4]octan-2-carboxylate (80 mg), with a yield of 80%.

LC/MS (ESI$^+$) calcd for $C_{35}H_{46}ClN_7O_4[M+H]^+$ m/z, 664.2; found, 664.7.

3. Synthesis of Compound 5-(4-((2,6-diazaspiro[3.4]octan-6-yl)methyl)piperidin-1-yl)-N-((1r,4r)-4-(3-chloro-4-cyanophenoxy)cyclohexyl)pyrazine-2-carboxamide Butyl-6-((1-(6-(((1r,4r)-4-(3-chloro-4-cyanophenoxy)cyclohexyl)carbamoyl) pyridazine-3-yl)piperidine-4-yl)methyl)-2,6-diazaspiro[3.4]octan-2-carboxylate (70 mg, 0.11 mmol) was dissolved in 5 mL of dichloromethane, to which was added 2 mL of trifluoroacetic acid, and the mixture was allowed to react under stirring at room temperature for 2 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound 5-(4-((2,6-diazaspiro[3.4]octan-6-yl)methyl)piperidin-1-yl)-N-((1r,4r)-4-(3-chloro-4-cyanophenoxy)cyclohexyl)pyrazine-2-carboxamide (57 mg), with a yield of 91%.

LC/MS (ESI$^+$) calcd for $C_{30}H_{38}ClN_7O_2[M+H]^+$ m/z, 564.1; found, 564.3.

4. Synthesis of Compound N-((1r,4r)-4-(3-chloro-4-cyanophenoxy)cyclohexyl)-5-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl)pyrazine-2-carboxamide 5-(4-((2,6-diazaspiro[3.4]octan-6-yl)methyl)piperidin-1-yl)-N-((1r,4r)-4-(3-chloro-4-cyanophenoxy)cyclohexyl)pyrazine-2-carboxamide (30 mg, 0.05 mmol), 2-(2,6-dioxopiperidin-3-yl)-5,6-difluoroisoindoline-1,3-dione (15 mg, 0.05 mmol) and DIPEA (19 mg, 0.15 mmol) were added in 3 mL of DMSO. The reaction solution was heated to 140° C. and allowed to react for 1 h under stirring. The reaction solution was cooled to room temperature, to which were added water and ethyl acetate for extraction. The organic layer was successively washed with 0.1 N HCl and brine, dried over anhydrous sodium sulfate, rotatory evaporated to dry, and the crude product was separated and purified by Pre-TLC, to provide compound N-((1r,4r)-4-(3-chloro-4-cyanophenoxy)cyclohexyl)-5-(4-((2-(2-(2,6-dioxopiperidin-3-yl)-6-fluoro-1,3-dioxoisoindolin-5-yl)-2,6-diazaspiro[3.4]octan-6-yl)methyl)piperidin-1-yl)pyrazine-2-carboxamide (22 mg), with a yield of 52%.

LC/MS (ESI$^+$) calcd for $C_{43}H_{45}ClFN_9O_6$ $[M+H]^+$ m/z, 838.3; found, 837.7.

$^1H$ NMR (400 MHz, $CDCl_3$) δ 9.05 (br, 1H), 8.83 (s, 1H), 7.96 (s, 1H), 7.56 (d, J=8.7 Hz, 1H), 7.38 (dd, J=9.2, 6.6 Hz, 2H), 6.99 (d, J=2.2 Hz, 1H), 6.94 (d, J=7.5 Hz, 1H), 6.85 (dd, J=8.7, 2.2 Hz, 1H), 4.92 (dd, J=12.3, 5.2 Hz, 1H), 4.46 (d, J=12.7 Hz, 2H), 4.36-4.26 (m, 1H), 4.08 (tdd, J=22.2, 13.9, 8.5 Hz, 5H), 2.97 (t, J=12.6 Hz, 2H), 2.92-2.62 (m, 6H), 2.49-2.30 (m, 2H), 2.25-2.07 (m, 7H), 1.83 (br, 5H), 1.75-1.60 (m, 3H), 1.46 (dt, J=14.7, 7.3 Hz, 2H).

187: N-((1r,4r)-4-(3-chloro-4-cyanophenoxy)cyclohexyl)-5-(4-((2-(2-(2,6-dioxopiperidin-3-yl)-1,3-dioxoisoindolin-5-yl)-2,6-diazaspiro[3.4]octan-6-yl)methyl)piperidin-1-yl)pyrazine-2-carboxamide

187

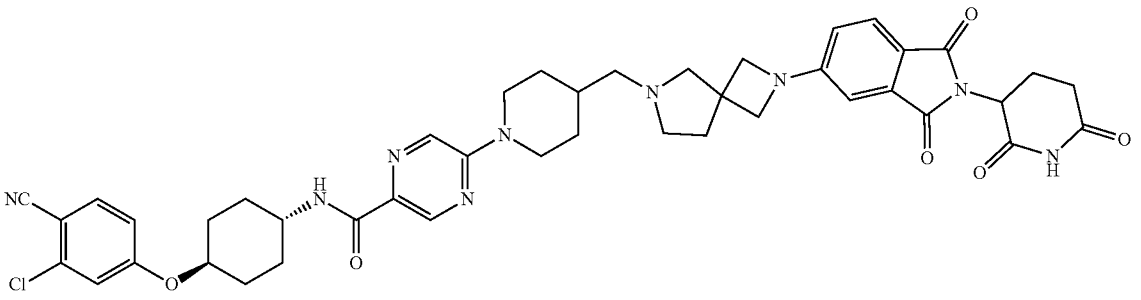

LC/MS (ESI+) calcd for $C_{43}H_{45}ClFN_9O_6$ $[M+H]^+$ m/z, 820.3; found, 819.8.

$^1H$ NMR (400 MHz, $CDCl_3$) δ 8.83 (s, 1H), 8.61 (br, 1H), 7.96 (s, 1H), 7.65 (d, J=7.9 Hz, 1H), 7.56 (d, J=8.9 Hz, 1H), 7.39 (d, J=9.0 Hz, 1H), 6.99 (s, 1H), 6.85 (d, J=6.6 Hz, 2H), 6.53 (d, J=8.5 Hz, 1H), 4.89 (dd, J=12.3, 5.2 Hz, 1H), 4.47 (d, J=12.7 Hz, 2H), 4.30 (br, 1H), 4.08-3.91 (m, 5H), 2.97 (t, J=12.6 Hz, 2H), 2.91-2.59 (m, 6H), 2.48-2.29 (m, 2H), 2.23-2.04 (m, 7H), 1.85 (br, 5H), 1.73-1.58 (m, 3H), 1.48 (dt, J=14.7, 7.3 Hz, 2H).

188: N-((1r,4r)-4-(3-chloro-4-cyanophenoxy)cyclohexyl)-5-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl)pyrazine-2-carboxamide

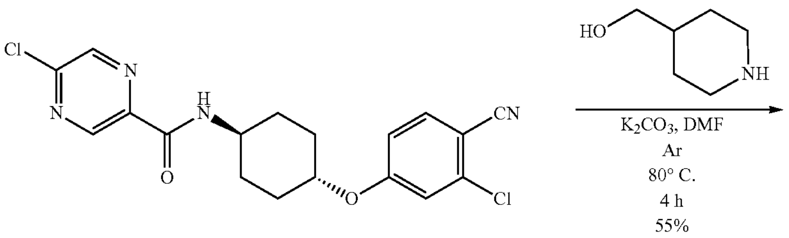

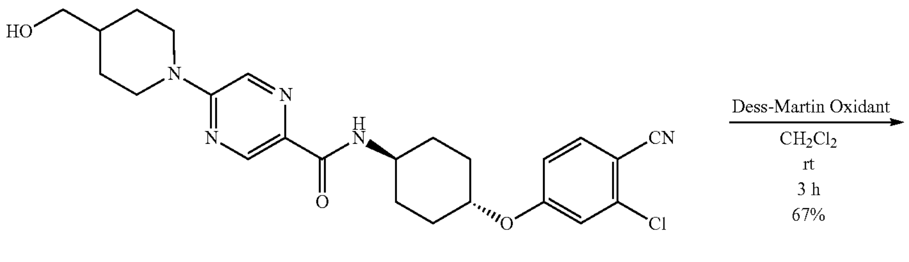

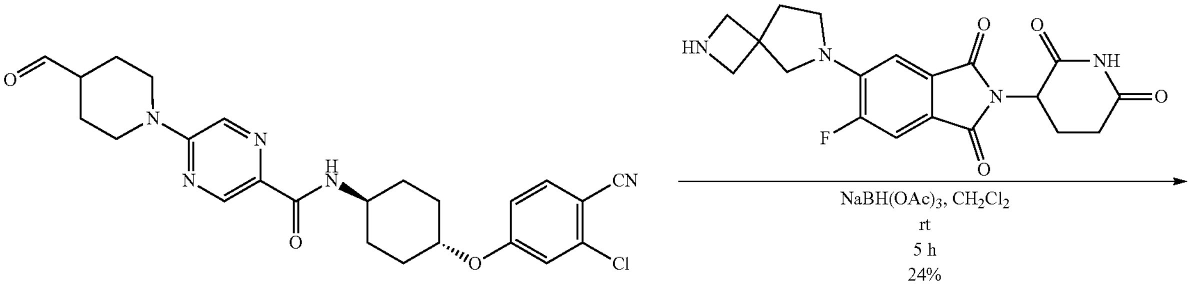

-continued

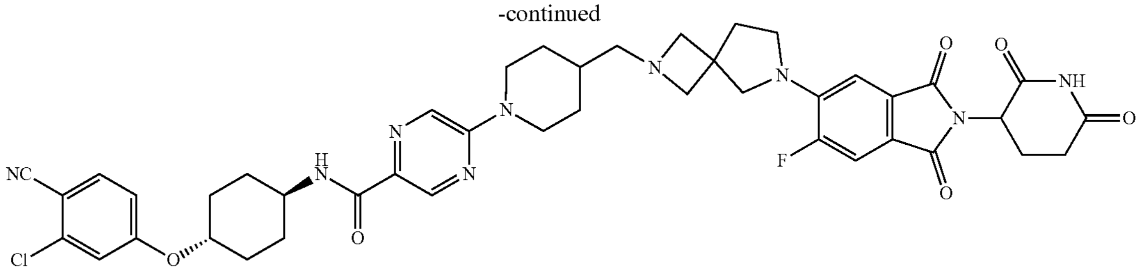

188

1. N-((1r,4r)-4-(3-chloro-4-cyanophenoxy)cyclohexyl)-5-(4-(hydroxymethyl) piperidin-1-yl)pyrazine-2-carboxamide To a round bottom flask containing piperidin-4-ylmethanol (66 mg, 0.57 mmol), was added 5 mL of DMF, and then the reaction solution was stirred at room temperature to dissolve and make the solution become clear. Subsequently, 5-chloro-N-((1r,4r)-4-(3-chloro-4-cyanophenoxy)cyclohexyl)pyrazine-2-carboxamide (200 mg, 0.51 mmol) and potassium carbonate (236 mg, 1.71 mmol) were added to the system. After that, the system was evacuated and purged with argon gas, that was repeated 5 times, to ensure the inert gas atmosphere in the system. After that, the system was moved to an oil bath at 80° C. for heating and reacting under stirring. After 4 h, TLC indicated the completion of the reaction. Heating was stopped, and once the system was cooled to room temperature, ethyl acetate (10 mL) and water (15 mL) were added to the system. The system was stirred vigorously, and stood still for separation of the layers. The aqueous layer was extracted with ethyl acetate (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by column chromatography, to provide compound N-((1r,4r)-4-(3-chloro-4-cyanophenoxy)cyclohexyl)-5-(4-(hydroxymethyl)piperidin-1-yl)pyrazine-2-carboxamide (132 mg), with a yield of 55%.

LC/MS (ESI$^+$) calcd for $C_{24}H_{28}ClN_5O_3$[M+H]$^+$ m/z, 470.0; found, 469.9.

2. N-((1r,4r)-4-(3-chloro-4-cyanophenoxy)cyclohexyl)-5-(4-formylpiperidin-1-yl) pyrazine-2-carboxamide N-((1r,4r)-4-(3-chloro-4-cyanophenoxy)cyclohexyl)-5-(4-(hydroxymethyl)piperidin-1-yl)pyrazine-2-carboxamide (60 mg, 0.13 mmol) was placed in a 25 mL single-neck round bottom flask, to which was added dichloromethane (5 mL), and then the reaction solution was stirred at room temperature to dissolve and make the solution become clear. Then, the system was placed in an ice water bath to cool down under stirring. When the internal temperature of the system dropped to about 0° C., Dess-Martin periodinane (85 mg, 0.20 mmol) was added to the system. After that, the system was warmed to room temperature and reacted under stirring at room temperature. After 3 h, TLC showed that the raw materials were almost completely disappeared, and the reaction was stopped. The system was subjected to suction filtration through celite, and the filter cake was rinsed with dichloromethane several times in a small amount. The filtrate was combined, and the solvent was removed by rotary evaporation to obtain a crude product, which was then separated and purified by Pre-TLC to obtain compound N-((1r,4r)-4-(3-chloro-4-cyanophenoxy)cyclohexyl)-5-(4-formylpiperidin-1-yl)pyrazine-2-carboxamide (41 mg), with a yield of 67%.

LC/MS (ESI$^+$) calcd for $C_{24}H_{26}ClN_3O_3$ [M+H]$^+$ m/z, 467.9; found, 468.0.

3. Synthesis of Compound N-((1r,4r)-4-(3-chloro-4-cyanophenoxy)cyclohexyl)-5-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl) pyrazine-2-carboxamide N-((1r,4r)-4-(3-chloro-4-cyanophenoxy)cyclohexyl)-5-(4-formylpiperidin-1-yl) pyrazine-2-carboxamide (22 mg, 0.05 mmol) was weighed and placed in a 25 mL single-neck round bottom flask, to which were added dichloromethane (4 mL), and then the reaction solution was stirred at room temperature to dissolve and make the solution become clear. Subsequently, 2-(2,6-dioxopiperidin-3-yl)-5-fluoro-6-(2,6-diazaspiro[3.4]octan-6-yl)isoindoline-1,3-dione (19 mg, 0.05 mmol) and one drop of glacial acetic acid were added to the system. After that, the mixture was stirred and reacted at room temperature for 15 min, to which was then added sodium triacetylborohydride (32 mg, 0.15 mmol). The system was allowed to react under stirring at room temperature. After 5 h, the sample was taken out and subjected to TLC, and the result showed the complete disappearance of the starting material. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-5-(4-((6-(2-(2,6-dioxopiperidin-3-yl)-6-fluoro-1,3-dioxoisoindolin-5-yl)-2,6-diazaspiro[3.4]octan-2-yl)methyl)piperidin-1-yl)pyrazine-2-carboxamide (10 mg), with a yield of 24%.

LC/MS (ESI$^+$) calcd for $C_{43}H_{45}ClFN_9O_6$, [M+H]$^+$ m/z, 838.3; found, 837.8.

$^1$H NMR (400 MHz, $CDCl_3$) δ 8.82 (s, 1H), 8.09 (br, 1H), 7.95 (s, 1H), 7.56 (d, J=8.8 Hz, 1H), 7.39 (t, J=10.3 Hz, 2H), 7.00 (dd, J=8.6, 4.9 Hz, 2H), 6.85 (dd, J=8.7, 2.2 Hz, 1H), 5.38-5.32 (m, 1H), 4.92 (dd, J=12.2, 5.1 Hz, 1H), 4.45 (d, J=13.7 Hz, 2H), 4.35-4.26 (m, 1H), 4.08-3.98 (m, 1H), 3.72 (br, 2H), 3.59 (dd, J=6.1, 4.2 Hz, 2H), 3.43-3.20 (m, 4H), 3.01-2.90 (m, 2H), 2.90-2.64 (m, 3H), 2.45 (d, J=6.2 Hz,

2H), 2.27-2.10 (m, 7H), 2.06-1.96 (m, 2H), 1.87 (d, J=13.3 Hz, 3H), 1.46 (dd, J=21.9, 12.2 Hz, 3H).

189: N-((1r,4r)-4-(3-chloro-4-cyanophenoxy)cyclohexyl)-5-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl)pyrazine-2-carboxamide

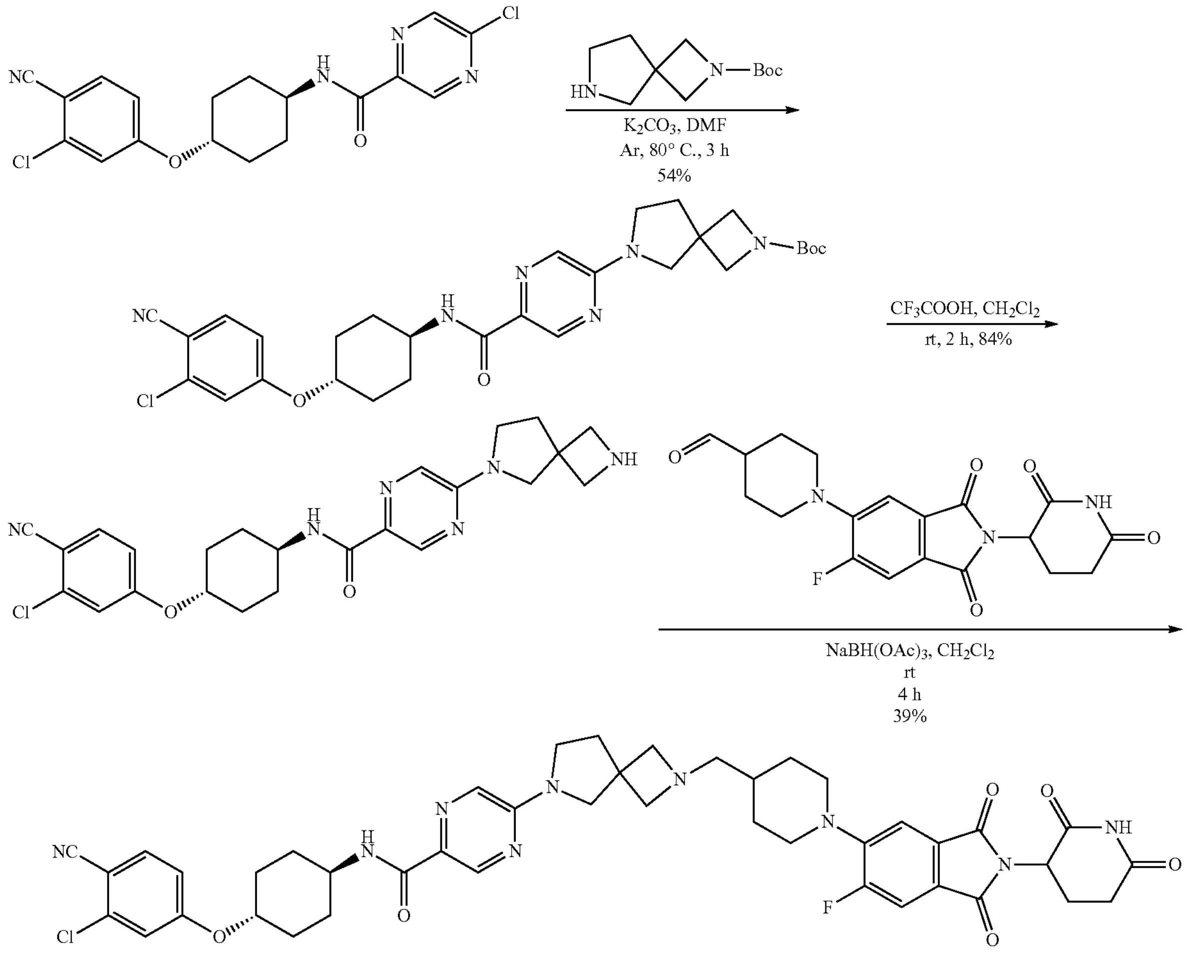

189

1. Synthesis of Compound butyl-6-(5-(((1r,4r)-4-(3-chloro-4-cyanophenoxy)cyclohexyl)carbamoyl)pyrazine-2-yl)-2,6-diazaspiro[3.4]octan-2-carboxylate To a round bottom flask containing butyl-2,6-diazaspiro[3.4]octan-2-carboxylate (55 mg, 0.26 mmol), was added 5 mL of DMF, and then the reaction solution was stirred at room temperature to dissolve and make the solution become clear. Subsequently, 5-chloro-N-((1r,4r)-4-(3-chloro-4-cyanophenoxy)cyclohexyl)pyrazine-2-carboxamide (100 mg, 0.26 mmol) and potassium carbonate (101 mg, 0.78 mmol) were added to the system. After that, the system was evacuated and purged with argon gas, that was repeated 5 times, to ensure the inert gas atmosphere in the system. After that, the system was moved to an oil bath at 80° C. for heating and reacting under stirring. After 3 h, TLC indicated the completion of the reaction. Heating was stopped, and once the system was cooled to room temperature, ethyl acetate (10 mL) and water (15 mL) were added to the system. The system was stirred vigorously, and stood still for separation of the layers. The aqueous layer was extracted with ethyl acetate (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound butyl-6-(5-(((1r,4r)-4-(3-chloro-4-cyanophenoxy) cyclohexyl)carbamoyl)pyrazine-2-yl)-2,6-diazaspiro[3.4]octan-2-carboxylate (80 mg), with a yield of 54%.

LC/MS ($ESI^+$) calcd for $C_{29}H_{35}ClN_6O_4[M+H]^+$ m/z, 567.1; found, 566.9.

2. Synthesis of Compound N-((1r,4r)-4-(3-chloro-4-cyanophenoxy)cyclohexyl)-5-(2,6-diazaspiro[3.4]octan-6-yl)pyrazine-2-carboxamide Butyl-6-(5-(((1r,4r)-4-(3-chloro-4-cyanophenoxy)cyclohexyl)carbamoyl)pyrazine-2-yl)-2,6-diazaspiro[3.4]octan-2-carboxylate (80 mg, 0.14 mmol) was dissolved in 5 mL of dichloromethane, to which was added 2 mL of trifluoroacetic acid, and the mixture was allowed to react under stirring at room temperature for 2 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 10 mL of dichloromethane and 3 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (3 mL*3). The organic layers were combined, washed with brine, and dried over anhydrous sodium sulfate. The crude product was separated and purified by column chromatography to obtain compound N-((1r,4r)-4-(3-chloro-4-cyanophenoxy)cyclohexyl)-5-(2,6-diazaspiro[3.4]octan-6-yl)pyrazine-2-carboxamide (44 mg), with a yield of 64%.

LC/MS (ESI$^+$) calcd for $C_{24}H_{27}ClNO_2$ [M+H]$^+$ m/z, 467.0; found, 467.7.

3. N-((1r,4r)-4-(3-chloro-4-cyanophenoxy)cyclohexyl)-5-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl)pyrazine-2-carboxamide N-((1r,4r)-4-(3-chloro-4-cyanophenoxy)cyclohexyl)-5-(2,6-diazaspiro[3.4]octan-6-yl)pyrazine-2-carboxamide (44 mg, 0.09 mmol) was weighed and placed in a 25 mL single-neck round bottom flask, to which were added dichloromethane (5 mL), and then the reaction solution was stirred at room temperature to dissolve and make the solution become clear. Subsequently, 1-(2-(2,6-dioxopiperidin-3-yl)-6-fluoro-1,3-dioxoisoindolin-5-yl)piperidine-4-formaldehyde (35 mg, 0.09 mmol) and one drop of glacial acetic acid were added to the system. After that, the mixture was stirred and reacted at room temperature for 15 min, to which was then added sodium triacetylborohydride (57 mg, 0.27 mmol). The system was allowed to react under stirring at room temperature. After 4 h, the sample was taken out and subjected to TLC, and the result showed the completion of the reaction. Stirring was stopped, and dichloromethane (15 mL) and water (15 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-5-(2-((1-(2-(2,6-dioxopiperidin-3-yl)-6-fluoro-1,3-dioxoisoindolin-5-yl)piperidine-4-yl)methyl)-2,6-diazaspiro[3.4]octan-6-yl)pyrazine-2-carboxamide (30 mg), with a yield of 39%.

LC/MS (ESI$^+$) calcd for $C_{43}H_{45}ClFN_9O_6$[M+H]$^+$ m/z, 838.3; found, 838.3.

$^1$H NMR (400 MHz, $CDCl_3$) δ 8.61 (br, 1H), 8.02 (d, J=9.3 Hz, 1H), 7.89 (d, J=8.1 Hz, 1H), 7.54 (d, J=8.7 Hz, 1H), 7.43 (d, J=11.0 Hz, 1H), 7.35 (d, J=7.2 Hz, 1H), 6.99 (d, J=2.1 Hz, 1H), 6.83 (dd, J=8.7, 2.2 Hz, 1H), 6.68 (d, J=9.4 Hz, 1H), 4.91 (dd, J=12.1, 5.2 Hz, 1H), 4.33-4.23 (m, 1H), 4.09-3.92 (m, 1H), 3.71 (br, 2H), 3.61 (d, J=11.2 Hz, 4H), 3.34 (dd, J=25.3, 6.9 Hz, 4H), 2.89-2.62 (m, 5H), 2.48 (d, J=6.6 Hz, 2H), 2.29-2.26 (m, 2H), 2.11 (dd, J=14.2, 6.3 Hz, 3H), 1.83 (d, J=11.9 Hz, 3H), 1.72-1.51 (m, 4H), 1.48-1.38 (m, 4H).

190: N-((1r,4r)-4-(3-chloro-4-cyanophenoxy)cyclohexyl)-6-(2-((1-(2-(2,6-dioxopiperidin-3-yl)-1,3-dioxoisoindolin-5-yl)piperidine-4-yl)methyl)-2,7-diazaspiro[3.5]nonan-7-yl)pyridazine-3-formamide

190

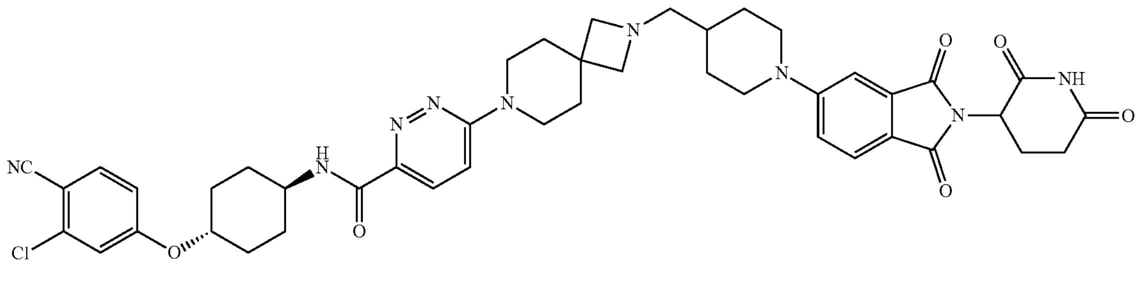

LC/MS (ESI$^+$) calcd for $C_{44}H_{48}ClN_9O_6$[M+H]$^+$ m/z, 834.4; found 833.9.

$^1$H NMR (400 MHz, $CDCl_3$) δ 8.60 (br, 1H), 7.98 (d, J=9.5 Hz, 1H), 7.88 (d, J=8.0 Hz, 1H), 7.67 (d, J=8.3 Hz, 1H), 7.56 (d, J=8.6 Hz, 1H), 7.14-6.89 (m, 4H), 6.85 (d, J=8.4 Hz, 1H), 4.94 (dd, J=11.3, 5.2 Hz, 1H), 4.31 (br, 1H), 4.00 (dd, J=42.4, 8.2 Hz, 4H), 3.71 (br, 5H), 3.22 (br, 5H), 3.07-2.63 (m, 7H), 2.50 (br, 3H), 1.73-1.63 (m, 4H), 1.53-1.39 (m, 3H), 1.29 (dt, J=24.2, 12.5 Hz, 5H).

191: N-((1r,4r)-4-(3-chloro-4-cyanophenoxy)cyclohexyl)-4-(4-((2-(2-(2,6-dioxopiperidin-3-yl)-6-fluoro-1,3-dioxoisoindolin-5-yl)-2,7-diazaspiro[3.5]nonan-7-yl)methyl)piperidin-1-yl)benzamide

191

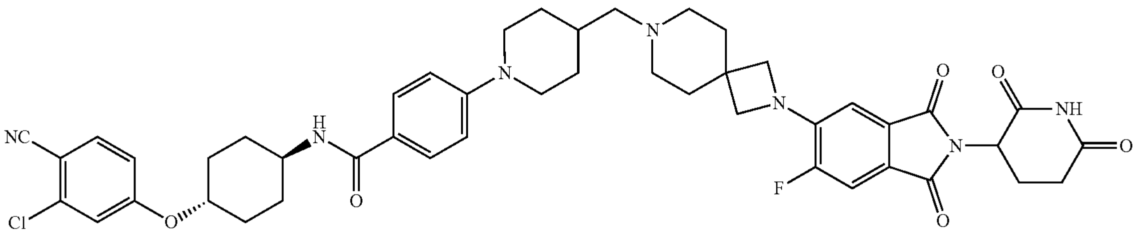

LC/MS (ESI+) calcd for $C_{46}H_{49}ClFN_7O_6$ $[M+H]^+$ m/z, 850.4; found, 850.3.

$^1H$ NMR (400 MHz, $CDCl_3$) δ 8.20 (br, 1H), 7.65 (d, J=8.9 Hz, 2H), 7.56 (d, J=8.7 Hz, 1H), 7.36 (d, J=10.9 Hz, 1H), 6.99 (d, J=2.3 Hz, 1H), 6.89 (d, J=9.0 Hz, 2H), 6.84 (dd, J=8.8, 2.4 Hz, 1H), 6.81 (d, J=7.6 Hz, 1H), 5.86 (d, J=7.7 Hz, 1H), 4.91 (dd, J=12.2, 5.3 Hz, 1H), 4.28 (ddd, J=13.8, 10.3, 3.7 Hz, 1H), 4.11-3.97 (m, 1H), 3.89 (s, 4H), 3.82 (d, J=12.7 Hz, 2H), 2.95-2.65 (m, 5H), 2.38 (br, 4H), 2.24-2.09 (m, 7H), 1.68 (dd, J=23.2, 10.2 Hz, 5H), 1.48-1.33 (m, 3H), 1.28 (dt, J=19.6, 7.3 Hz, 5H).

192: N-((1r,4r)-4-(3-chloro-4-cyanophenoxy)cyclohexyl)-4-(4-((2-(2-(2,6-dioxopiperidin-3-yl)-1,3-dioxoisoindolin-5-yl)-2,7-diazaspiro[3.5]nonan-7-piperidin-1-yl)benzamide

192

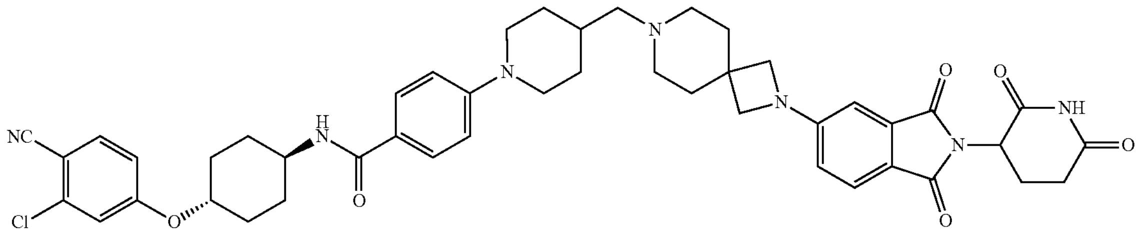

LC/MS (ESI+) calcd for $C_{46}H_{50}ClN_7O_6$ $[M+H]^+$ m/z, 832.4; found, 832.3.

$^1H$ NMR (400 MHz, $CDCl_3$) δ 8.17 (br, 1H), 7.65 (dd, J=8.0, 5.5 Hz, 3H), 7.56 (d, J=8.7 Hz, 1H), 6.99 (d, J=1.6 Hz, 1H), 6.95-6.82 (m, 2H), 6.77 (s, 1H), 6.51 (d, J=8.2 Hz, 1H), 5.87 (d, J=7.4 Hz, 1H), 4.93 (dd, J=11.6, 4.4 Hz, 1H), 4.33-4.24 (m, 1H), 4.04 (d, J=8.0 Hz, 1H), 3.83 (d, J=12.6 Hz, 2H), 3.74 (s, 4H), 3.03-2.60 (m, 5H), 2.40 (br, 4H), 2.29-2.03 (m, 8H), 1.68 (dd, J=22.7, 10.5 Hz, 5H), 1.35 (ddd, J=33.0, 21.7, 9.7 Hz, 7H).

193: N-((1r,4r)-4-(3-chloro-4-cyanophenoxy)cyclohexyl)-5-(7-(1-(2-(2,6-dioxopiperidin-3-yl)-1,3-dioxoisoindolin-5-yl)piperidine-4-yl)-2,7-diazaspiro[3.5]nonan-2-yl)-1,3,4-thiadiazole-2-carboxamide

193

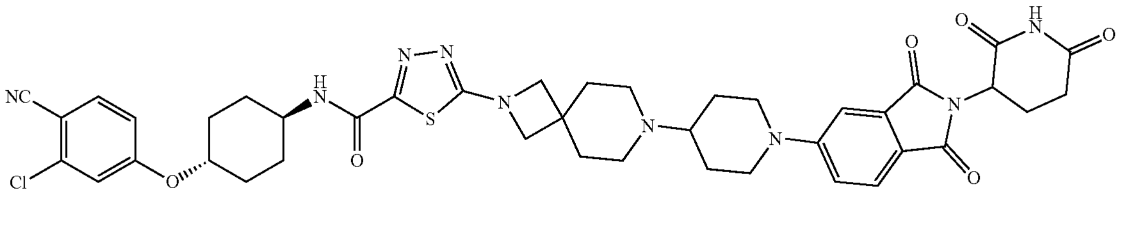

LC/MS (ESI+) calcd for $C_{41}H_{44}ClN_9O_6S$ $[M+H]^+$ m/z, 826.4; found, 826.2.

$^1H$ NMR (400 MHz, $CDCl_3$) δ 8.06 (br, 1H), 7.69 (d, J=8.5 Hz, 1H), 7.56 (d, J=8.7 Hz, 1H), 7.28 (d, J=2.4 Hz, 1H), 7.06 (dd, J=8.4, 1.7 Hz, 1H), 7.00 (t, J=5.2 Hz, 2H), 6.84 (dd, J=8.7, 2.3 Hz, 1H), 5.41-5.28 (m, 1H), 4.94 (dd, J=12.2, 5.2 Hz, 1H), 4.31 (t, J=10.0 Hz, 1H), 4.02 (d, J=12.4 Hz, 3H), 3.91 (s, 4H), 2.99 (t, J=12.4 Hz, 2H), 2.94-2.57 (m, 7H), 2.26-2.07 (m, 6H), 2.01 (dd, J=12.5, 6.5 Hz, 6H), 1.54-1.40 (m, 4H).

194: N-((1r,4r)-4-(3-chloro-4-cyanophenoxy)cyclohexyl)-4-(7-((1-(2-(2,6-dioxopiperidin-3-yl)-1,3-dioxoisoindolin-5-yl)piperidine-4-yl)methyl)-2,7-diazaspiro[3.5]nonan-2-yl)benzamide

194

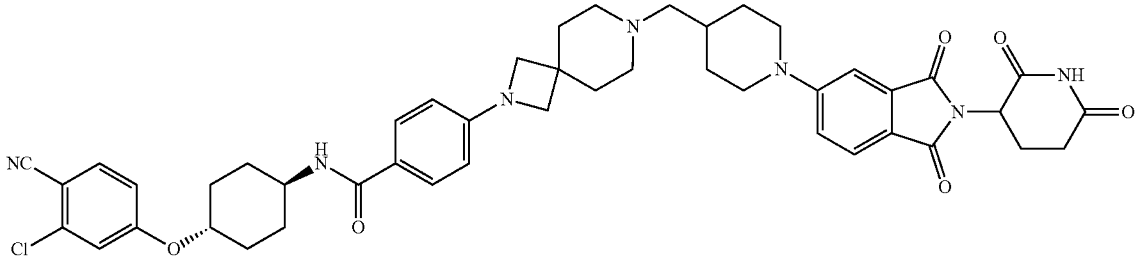

LC/MS (ESI+) calcd for $C_{46}H_{50}ClN_7O_6$ $[M+H]^+$ m/z, 832.4; found, 832.3.

$^1H$ NMR (400 MHz, $CDCl_3$) δ 8.26 (br, 1H), 7.67 (d, J=8.6 Hz, 1H), 7.63 (d, J=8.7 Hz, 2H), 7.56 (d, J=8.7 Hz, 1H), 7.28 (d, J=2.2 Hz, 1H), 7.04 (dd, J=8.7, 2.3 Hz, 1H), 6.99 (d, J=2.4 Hz, 1H), 6.84 (dd, J=8.7, 2.4 Hz, 1H), 6.39 (d, J=8.7 Hz, 2H), 5.82 (d, J=7.8 Hz, 1H), 4.94 (dd, J=12.3, 5.4 Hz, 1H), 4.28 (ddd, J=13.7, 10.3, 3.7 Hz, 1H), 4.10-3.99 (m, 1H), 3.95 (d, J=12.8 Hz, 2H), 3.65 (s, 4H), 3.07-2.63 (m, 6H), 2.42 (br, 4H), 2.28-2.09 (m, 8H), 1.89-1.80 (m, 6H), 1.67 (dd, J=23.3, 10.3 Hz, 3H), 1.39 (dd, J=23.7, 10.4 Hz, 2H).

195: N-((1r,4r)-4-(3-chloro-4-cyanophenoxy)cyclohexyl)-6-(4-((2-(2-(2,6-dioxopiperidin-3-yl)-6-fluoro-1-oxoisoindolin-5-yl)-2,7-diazaspiro[3.5]nonan-7-yl)methyl)piperidin-1-yl)pyridazine-3-formamide

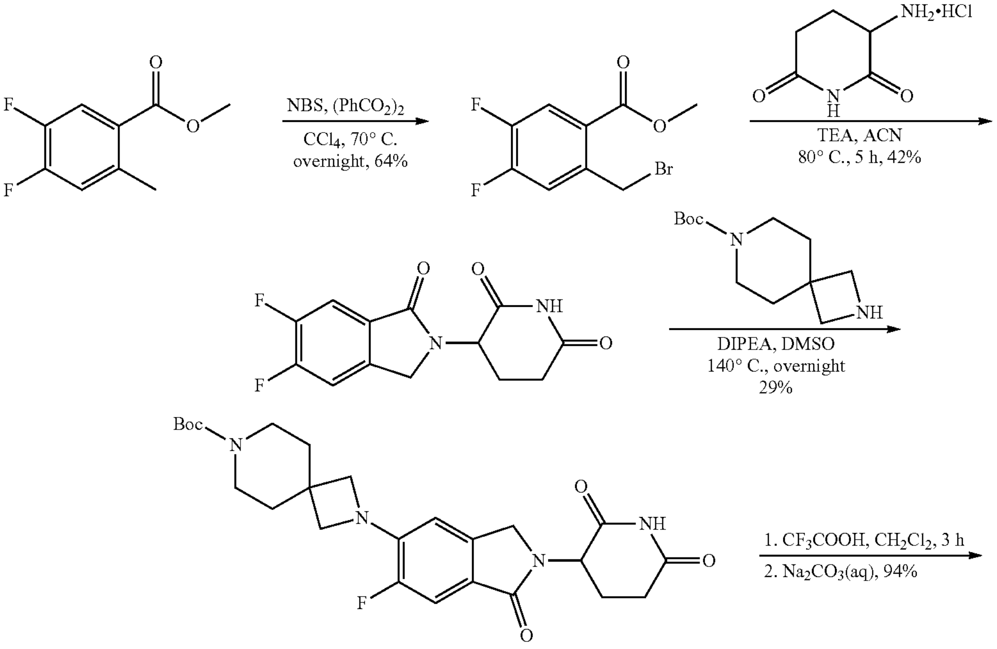

-continued

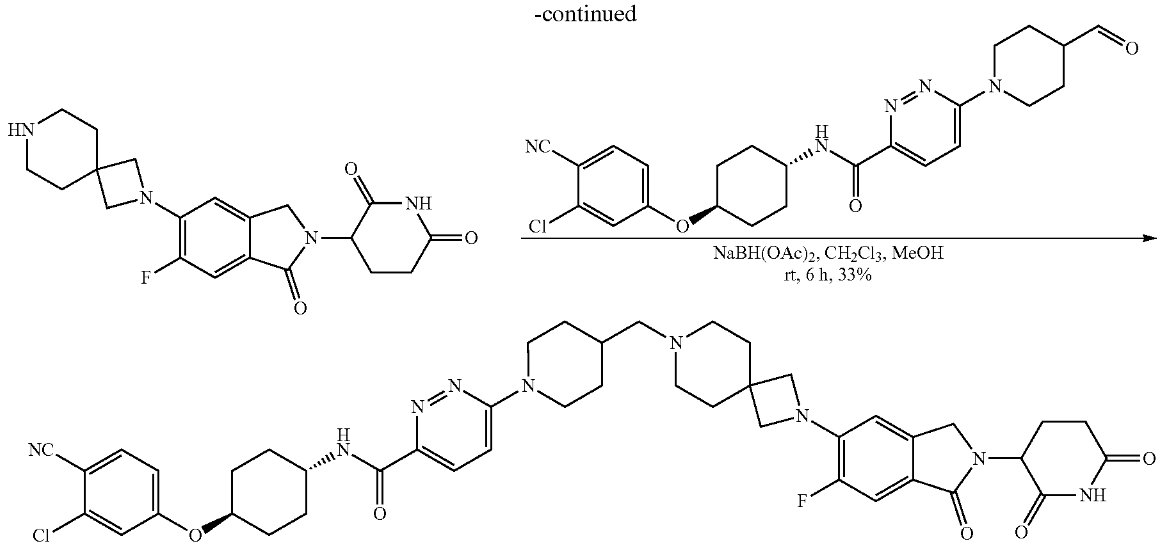

195

1. Synthesis of Compound methyl 2-(bromomethyl)-4,5-difluorobenzoate

Methyl 4,5-difluoro-2-methylbenzoate (3500 mg, 18.80 mmol) was weighed and placed in a 100 mL single-neck round bottom flask, to which was added 25 mL of $CCl_4$, and then the reaction solution was stirred at room temperature to dissolve and make the solution become clear. Subsequently, NBS (3680 mg, 20.68 mmol) and dibenzoyl peroxide (136 mg, 0.56 mmol) were successively added to the system. After that, the system was moved to an oil bath at 70° C. for heating and reacting under stirring. Next day, TLC indicated the starting material had almost disappeared. Heating was stopped, and once the system was cooled to room temperature, the solvent was removed by rotatory evaporation. Dichloromethane (30 mL) and water (15 mL) were then added to the system. The system was stirred vigorously, and stood still for separation of the layers. The aqueous phase was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound methyl 2-(bromomethyl)-4,5-difluorobenzoate (3180 mg), with a yield of 64%.

2. Synthesis of Compound 3-(5,6-difluoro-1-oxoisoindolin-2-yl))piperidine-2,6-dione Methyl 2-(bromomethyl)-4,5-difluorobenzoate (1500 mg, 5.66 mmol) was weighed and placed into a 100 mL single-neck round bottom flask, to which was added 25 mL of acetonitrile, and then the reaction solution was stirred at room temperature to dissolve and make the solution become clear. Subsequently, 3-aminopiperdine-2,6-dione hydrochloride (931 mg, 5.66 mmol) was slowly added to the system, and then the solution of triethylamine (1145 mg, 11.32 mmol) in acetonitrile (5 mL) was added dropwise. After that, the system was moved to an oil bath at 80° C. for heating and reacting under stirring. After 5 h, the reaction was completed by LCMS detection. Heating was stopped, and once the system was cooled to room temperature, the solvent was removed by rotatory evaporation. Dichloromethane (50 mL) and water (25 mL) were then added to the system. The system was stirred vigorously, and stood still for separation of the layers. The aqueous phase was extracted with dichloromethane (20 mL*3). The organic phase was combined, and successively washed with water (15 mL*2) and saturated brine (20 mL), dried over anhydrous sodium sulfate. The solvent was removed by rotatory evaporation, to obtain a crude product, which was separated and purified by column chromatography, to provide compound 3-(5,6-difluoro-1-oxoisoindolin-2-yl)piperidine-2,6-dione (664 mg), with a yield of 42%.

LC/MS (ESI+) calcd for $C_{13}H_{10}F_2N_2O_3$ $[M+H]^+$ m/z, 280.2; found, 281.1.

3. Synthesis of t-butyl 2-(2-(2,6-dioxopiperidin-3-yl)-6-fluoro-1-oxoisoindolin-5-yl)-2,7-diazaspiro[3.5]nonan-7-carboxylate t-Butyl 3-(5,6-difluoro-1-oxoisoindolin-2-yl))piperidine-2,6-dione (200 mg, 0.71 mmol), 2,7-diazaspiro[3.5]nonan-7-carboxylate (160 mg, 0.71 mmol) and DIPEA (275 mg, 2.13 mmol) were added into 5 mL of DMSO. The reaction solution was heated to 140° C. and allowed to react overnight. Next day, TLC indicated the complete disappearance of the starting material. Heating was stopped, and the system was allowed to naturally cool to room temperature, to which were added water and ethyl acetate for extraction. The organic layer was successively washed with 0.1 N HCl and brine, dried over anhydrous sodium sulfate, rotatory evaporated to dry, and the crude product was separated and purified by Pre-TLC, to provide compound t-butyl 2-(2-(2,6-dioxopiperidin-3-yl)-6-fluoro-1-oxoisoindolin-5-yl)-2,7-diazaspiro[3.5]nonan-7-carboxylate (102 mg), with a yield of 29%.

LC/MS (ESI+) calcd for $C_{25}H_{31}FN_4O_5$ $[M+H]^+$ m/z, 486.5; found, 487.1.

4. Compound 3-(6-fluoro-1-oxo-5-(2,7-diazaspiro[3.5]nonan-2-yl)isoindolin-2-yl)piperidine-2,6-dione Compound t-butyl 2-(2-(2,6-dioxopiperidin-3-yl)-6-fluoro-1-oxoisoindolin-5-yl)-2,7-diazaspiro[3.5]nonan-7-carboxylate (65 mg, 0.13 mmol) was dissolved in 5 mL of dichloromethane, to which was added 2 mL of trifluoroacetic acid, and the mixture was allowed to react under stirring at room temperature for 3 h. TLC indicated that the raw materials had disappeared, and then the excess trifluoroacetic acid and the solvent were removed by rotary evaporation, and the residual trifluoroacetic acid was removed by evaporation with dichloromethane for several times. To the residue, were added 15 mL of dichloromethane and 5 mL of water again, and then the system was moved to an ice-water bath to cool down under stirring. Subsequently, the saturated solution of sodium bicarbonate was added dropwise to the system to adjust pH to be about 9. After that, the solution was allowed to stand for separation of layers. The aqueous phase was washed with dichloromethane (5 mL*3). The organic layers were combined, washed with brine, and dried over anhydrous sodium sulfate. The crude product was separated and purified by Pre-TLC to obtain compound 3-(6-fluoro-1-oxo-5-(2,7-diazaspiro[3.5]nonan-2-yl)isoindolin-2-yl)piperidine-2,6-dione (49 mg), with a yield of 94%.

LC/MS (ESI+) calcd for $C_{20}H_{23}FN_4O_3[M+H]^+$ m/z, 386.4; found, 387.1.

5. Synthesis of Compound N-((1r,4r)-4-(3-chloro-4-cyanophenoxy)cyclohexyl)-6-(4-((2-(2-(2,6-dioxopiperidin-3-yl)-6-fluoro-1-oxoisoindolin-5-yl)-2,7-diazaspiro[3.5]nonan-7-yl)methyl)piperidin-1-yl) pyridazine-3-formamide N-((1r,4r)-4-(3-chloro-4-cyanophenoxy)cyclohexyl)-6-(4-formylpiperidin-1-yl) pyridazine-3-formamide (61 mg, 0.13 mmol) and 3-(6-fluoro-1-oxo-5-(2,7-diazaspiro[3.5]nonan-2-yl)isoindolin-2-yl)piperidine-2,6-dione (49 mg, 0.13 mmol) were weighed and placed in a 25 mL single-neck round bottom flask, to which were added dichloromethane (5 mL), and then the reaction solution was stirred at room temperature to dissolve and make the solution become clear. Subsequently, one drop of glacial acetic acid was added to the system. After that, the mixture was stirred and reacted at room temperature for 15 min, to which was then added sodium triacetylborohydride (83 mg, 0.39 mmol). The system was allowed to react under stirring at room temperature. After 6 h, the sample was taken out and subjected to TLC, and the result showed the completion of the reaction. Stirring was stopped, and dichloromethane (20 mL) and water (10 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-6-(4-((2-(2-(2,6-dioxopiperidin-3-yl)-6-fluoro-1-oxoisoindolin-5-yl)-2,7-diazaspiro[3.5]nonan-7-yl)methyl)piperidin-1-yl)pyridazine-3-formamide (35 mg), with a yield of 33%. LC/MS (ESI+) calcd for $C_{44}H_{49}ClFN_9O_5$ $[M+H]^+$ m/z, 838.4; found, 838.3.

$^1H$ NMR (400 MHz, $CDCl_3/CD_3OD$) δ 7.97 (dd, J=8.6, 4.8 Hz, 1H), 7.57 (d, J=8.7 Hz, 1H), 7.40 (d, J=11.3 Hz, 1H), 7.02 (dd, J=5.9, 3.5 Hz, 2H), 6.87 (dd, J=8.8, 2.4 Hz, 1H), 6.41 (d, J=7.6 Hz, 1H), 5.13 (dd, J=13.3, 5.1 Hz, 1H), 4.51 (d, J=12.9 Hz, 2H), 4.33 (dd, J=15.8, 9.5 Hz, 2H), 4.22 (d, J=15.8 Hz, 1H), 4.04 (ddd, J=10.4, 7.9, 4.0 Hz, 1H), 3.84 (br, 4H), 3.40 (dt, J=3.2, 1.6 Hz, 1H), 3.07 (t, J=12.3 Hz, 2H), 2.96-2.74 (m, 3H), 2.31 (ddd, J=25.5, 12.5, 5.6 Hz, 3H), 2.18 (d, J=10.6 Hz, 6H), 1.99 (br, 6H), 1.69 (dd, J=22.1, 10.1 Hz, 3H), 1.49 (dd, J=22.2, 10.9 Hz, 3H).

196: Synthesis of N-((1r,4r)-4-(3-chloro-4-cyanophenoxy)cyclohexyl)-6-(4-((2-(2-(2,6-dioxopiperidin-3-yl)-1-oxoisoindolin-5-yl)-2,7-diazaspiro[3.5]nonan-7-yl)methyl)piperidin-1-yl)pyridazine-3-formamide

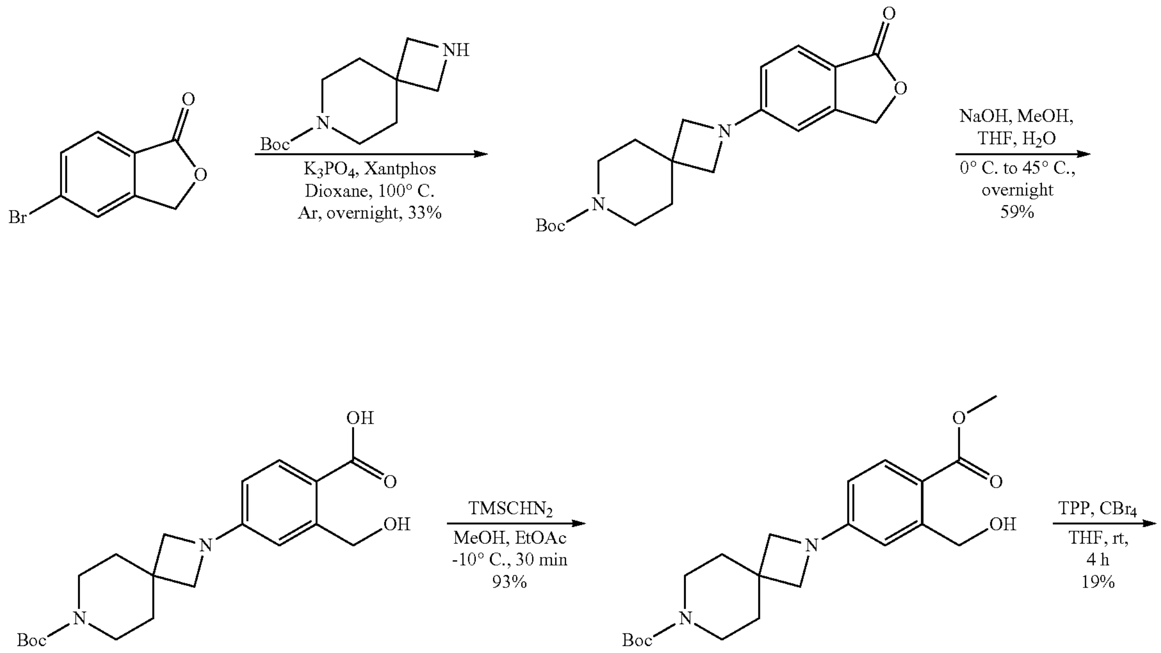

-continued

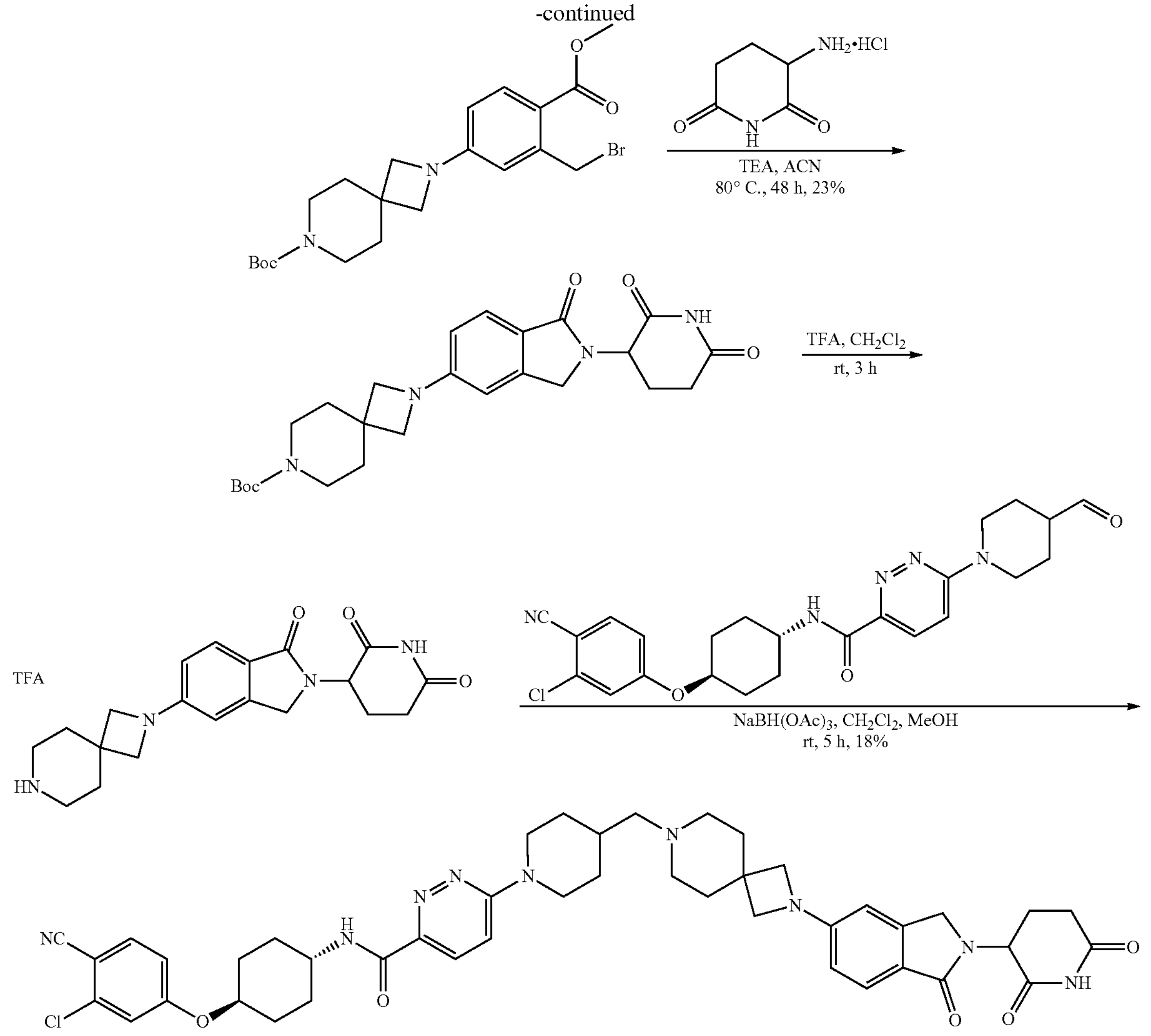

196

1. t-Butyl 2-(1-oxo-1,3-dihydroisobenzofuran-5-yl)-2,7-diazaspiro[3.5]nonan-7-carboxylate 5-Bromoisobenzofuran-1(3H)-one (2500 mg, 11.74 mmol), t-butyl 2,7-diazaspiro[3.5]nonan-7-carboxylate (2657 mg, 11.74 mmol), $Pd_2(dba)_3$ (540 mg, 0.59 mmol), Xantphos (341 mg, 0.59 mmol) and potassium phosphate (4984 mg, 23.48 mmol) were weighed and placed in a 150 single-neck round bottom flask, to which was added 1,4-dioxane (40 mL), and the mixture was stirred at room temperature. Then, the system was evacuated and purged with argon gas, that was repeated 7 times, to ensure the inert gas atmosphere in the system. After that, the system was moved to an oil bath at 100° C. for heating and reacting overnight under stirring. Next day, TLC indicated the disappearance of the starting material. Heating was stopped, and the system was cooled to room temperature. Then, the system was subjected to suction filtration (through celite), and the filter cake was rinsed with dioxane in a small amount for several times. The filtrate was combined, and the solvent was removed by rotatory evaporation to obtain a crude product, which was boated in (ethyl acetate/petroleum ether=1/2), to provide compound t-butyl 2-(1-oxo-1,3-dihydroisobenzofuran-5-yl)-2,7-diazaspiro[3.5]nonan-7-carboxylate (1400 mg), with a yield of 33%. LCMS ($ESI^+$) calcd for $C_{20}H_{26}N_2O_4$ $[M+H]^+$ m/z, 358.4; found, 359.2.

2. Synthesis of Compound 4-(7-(t-butoxycarbonyl)-2,7-diazaspiro[3.5]nonan-2-yl)-2-(hydroxymethyl) benzoic acid t-Butyl 2-(1-oxo-1,3-dihydroisobenzofuran-5-yl)-2,7-diazaspiro[3.5]nonan-7-carboxylate (1400 mg, 3.91 mmol) was weighed and placed in a 100 mL single-neck round bottom flask, to which were added 18 mL of MeOH and 18 mL of THF, and then the reaction solution was stirred at room temperature. Subsequently, 5 mL aqueous solution of sodium hydroxide (626 mg, 15.64 mmol) was added dropwise to the system. After that, the system was transferred to an oil bath at 45° C. for heating and reacting overnight under stirring. Next day. TLC indicated the completion of the reaction. Heating was stopped, and once the system was cooled to room temperature, most of the solvent was removed by rotatory evaporation, to which was added 10 mL of water. Then, the system was transferred to an ice-water bath to cool down under stirring. After 10 min, dilute hydrochloric acid solution (0.5 N) was added dropwise to the system to adjust the pH value to be about 4-5, and then ethyl acetate was added to the system. The system was stirred vigorously, and allowed to stand for separation of layers. The aqueous phase was extracted with ethyl acetate. The organic layers were combined, washed with brine, and dried over anhydrous sodium sulfate. The solvent was removed by rotatory evaporation to obtain a crude product, which was beated (ethyl acetate/petroleum ether=1/2), to provide compound 4-(7-(t-butoxycarbonyl)-2,7-diazaspiro [3.5]nonan-2-yl)-2-(hydroxymethyl)benzoic acid (874 mg), with a yield of 59%. LC/MS ($ESI^+$) calcd for $C_{20}H_{28}N_2O_5$ $[M+H]^+$ m/z, 376.4; found, 377.2, 321.1, 277.1.

3. Synthesis of t-butyl 2-(3-(hydroxymethyl)-4-(methoxycarbonyl)phenyl)-2,7-diazaspiro[3.5] nonan-7-carboxylate 4-(7-(t-Butoxycarbonyl)-2,7-diazaspiro[3.5]nonan-2-yl)-2-(hydroxymethyl)benzoic acid (700 mg, 1.86 mmol) was placed in 50 mL single-neck round bottom flask, to which were added 8 mL of MeOH and 8 mL of ethyl acetate, and then the reaction solution was stirred at room temperature. Then, the system was transferred to an ice-salt bath to cool down under stirring. When the internal temperature of the system lowered to −10° C., 3 mL of (trimethylsilyl)diazomethane (2.0 N) was added dropwise to the system. After that, the temperature was maintained, and the system was allowed to react under stirring. After 30 min, TLC indicated the disappearance of raw materials. 10 mL of water and 20 mL of ethyl acetate were added to the system, and then the system was stirred vigorously and stood still for separation of layers. The aqueous phase was extracted with ethyl acetate. The organic layer was combined, washed with brine, and dried over anhydrous sodium sulfate. The solvent was removed by rotary evaporation to obtain the crude product, which was separated and purified by column chromatography to provide compound t-butyl 2-(3-(hydroxymethyl)-4-(methoxycarbonyl)phenyl)-2,7-diazaspiro[3.5]nonan-7-carboxylate (676 mg), with a yield of 93%. LC/MS ($ESI^+$) calcd for $C_{21}H_{30}N_2O_5[M+H]^+$ m/z, 390.5; found, 391.2, 335.1, 291.2.

4. t-Butyl 2-(3-(bromomethyl)-4-(methoxycarbonyl) phenyl)-2,7-diazaspiro[3.5]nonan-7-carboxylate t-Butyl 2-(3-(hydroxymethyl)-4-(methoxycarbonyl)phenyl)-2,7-diazaspiro[3.5]nonan-7-carboxylate (676 mg, 1.73 mmol) was weighed and placed in a 50 mL single-neck round bottom flask, to which was added 10 mL of THF, and then the reaction solution was stirred at room temperature to dissolve and make the solution become clear. Subsequently, triphenylphosphine (682 mg, 2.60 mmol) and $CBr_4$ (862 mg, 2.60 mmol) were successively added to the system. After that, the system was allowed to react at room temperature under stirring. After 4 h, TLC indicated the completion of the reaction. Water (10 mL) and ethyl acetate (30 mL) were added to the system. The system was stirred vigorously, and stood still for separation of the layers. The aqueous phase was extracted with ethyl acetate. The organic phase was combined, washed with saturated brine, and dried over anhydrous sodium sulfate. The solvent was removed by rotatory evaporation, to obtain a crude product, which was separated and purified by column chromatography, to provide compound t-butyl 2-(3-(bromomethyl)-4-(methoxycarbonyl)phenyl)-2,7-diazaspiro[3.5]nonan-7-carboxylate (147 mg), with a yield of 19%.

LC/MS ($ESI^+$) calcd for $C_{21}H_{29}BrN_2O_4[M+H]^+$ m/z, 453.4; found, 353.1.

5. t-Butyl 2-(2-(2,6-dioxopiperidin-3-yl)-1-oxoisoindolin-5-yl)-2,7-diazaspiro[3.5]nonan-7-carboxylate 3-Aminopiperdine-2,6-dione hydrochloride (53 mg, 0.32 mmol) was weighed and placed in a 25 mL single-neck round bottom flask, to which was added 4 mL acetonitrile, and then the system was stirred well at room temperature. Then, the solution of triethylamine (65 mg, 0.64 mmol) in acetonitrile (1 mL) was slowly added dropwise to the system. After 5 min, the solution oft-butyl 2-(3-(bromomethyl)-4-(methoxycarbonyl)phenyl)-2,7-diazaspiro[3.5] nonan-7-carboxylate (147 mg, 0.32 mmol) in acetonitrile (1 mL) was add to the system. Then, the system was moved to an oil bath at 80° C. for heating and reacting under stirring. After 48 h, the reaction was completed by LCMS detection. Heating was stopped, and once the system was cooled to room temperature, the solvent was removed by rotatory evaporation. Dichloromethane (20 mL) and water (10 mL) were then added to the system. The system was stirred vigorously, and stood still for separation of the layers. The aqueous phase was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound 2-(2-(2,6-dioxopiperidin-3-yl)-1-oxoisoindolin-5-yl)-2,7-diazaspiro[3.5]nonan-7-carboxylate t-butyl(35 mg), with a yield of 23%.

LC/MS ($ESI^+$) calcd for $C_{25}H_{32}N_4O_5$ $[M+H]^+$ m/z, 468.5; found, 469.2.

6. Synthesis of Compound 3-(1-oxo-5-(2,7-diazaspiro[3.5]nonan-2-yl)isoindolin-2-yl)piperidine-2,6-dione Compound t-butyl 2-(2-(2,6-dioxopiperidin-3-yl)-1-oxoisoindolin-5-yl)-2,7-diazaspiro[3.5]nonan-7-carboxylate (35 mg, 0.07 mmol) was dissolved in 3 mL of dichloromethane, to which was added 1 mL of trifluoroacetic acid. After the reaction solution was stirred at room temperature for 3 h, TLC indicated that the completion of the reaction, and then excess trifluoroacetic acid and the solvent were removed by rotary evaporation, and residual trifluoroacetic acid was removed by rotatory evaporation with dichloromethane several times, to provide compound 3-(6-fluoro-1-oxo-5-(2,7-diazaspiro[3.5]nonan-2-yl)isoindolin-2-yl)piperidine-2,6-dionetrifluoroacetate (39 mg), which was directly used in the next reaction, without further purification.

7. Synthesis of Compound N-((1r,4r)-4-(3-chloro-4-cyanophenoxy)cyclohexyl)-6-(4-((2-(2-(2,6-dioxopiperidin-3-yl)-1-oxoisoindolin-5-yl)-2,7-diazaspiro [3.5]nonan-7-yl)methyl)piperidin-1-yl)pyridazine-3-formamide N-((1r,4r)-4-(3-chloro-4-cyanophenoxy)cyclohexyl)-6-(4-formylpiperidin-1-yl) pyridazine-3-formamide (37 mg, 0.08 mmol) and 3-(6-fluoro-1-oxo-5-(2,7-diazaspiro[3.5] nonan-2-yl)isoindolin-2-yl)piperidine-2,6-dionetrifluoroacetate (39 mg, 0.08 mmol) were weighed and placed in a 25 mL single-neck round bottom flask, to which were added dichloromethane (3 mL) and methanol (1 mL), and then the system was stirred and reacted at room temperature for 15 min, to which was then added sodium triacetylborohydride (51 mg, 0.24 mmol). The system was allowed to react under stirring at room temperature. After 5 h, TLC showed the completed disappearance of the starting materials. The solvent was removed by rotatory evaporation. Dichloromethane (20 mL) and water (10 mL) were added to the system. The system was stirred vigorously, and stood still for separation of the layers. The aqueous layer was extracted with dichloromethane (10 mL*3). The organic phase was combined, and successively washed with water (10 mL*2) and saturated brine (15 mL), dried over anhydrous sodium sulfate. The solvent was removed by rotatory evaporation, to obtain a crude product, which was separated and purified by Pre-TLC, to provide compound N-((1r,4r)-4-(3-chloro-4-cyanophenoxy)cyclohexyl)-6-(4-((2-(2-(2,6-dioxopiperidin-3-yl)-1-oxoisoindolin-5-yl)-2,7-diazaspiro[3.5]nonan-7-yl)methyl)piperidin-1-yl)pyridazine-3-formamide (12 mg), with a yield of 18%.

LC/MS ($ESI^+$) calcd for $C_{44}H_{50}ClN_9O_5$ $[M+H]^+$ m/z, 820.4; found, 820.3.

$^1H$ NMR (400 MHz, $CDCl_3$) δ 8.03 (s, 1H), 7.97 (d, J=9.6 Hz, 1H), 7.87 (d, J=8.2 Hz, 1H), 7.69 (d, J=8.3 Hz, 1H), 7.56 (d, J=8.7 Hz, 1H), 6.99 (dd, J=10.5, 6.0 Hz, 2H), 6.86 (dd, J=8.7, 2.3 Hz, 1H), 6.45 (dd, J=8.6, 1.3 Hz, 1H), 6.37 (s, 1H), 5.19 (dd, J=13.2, 5.1 Hz, 1H), 4.52 (d, J=12.4 Hz, 2H), 4.38 (d, J=15.7 Hz, 1H), 4.35-4.27 (m, 1H), 4.23 (d, J=15.7 Hz, 1H), 4.05 (ddd, J=11.0, 9.6, 5.1 Hz, 1H), 3.69 (br, 4H), 3.05 (t, J=12.3 Hz, 2H), 2.86 (dddd, J=17.0, 12.6, 7.1, 3.9 Hz, 2H), 2.32 (ddd, J=25.5, 12.7, 5.0 Hz, 3H), 2.24-2.10 (m, 6H), 2.10-1.82 (m, 7H), 1.68 (dd, J=21.7, 9.6 Hz, 6H), 1.46 (dd, J=22.2, 11.0 Hz, 3H).

197: N-((1r,4r)-4-(4-cyano-3-(methoxy-$d_3$)phenoxy)cyclohexyl)-3-(4-((2-(2-(2,6-dioxopiperidin-3-yl)-1,3-dioxoisoindolin-5-yl)-2,7-diazaspiro[3.5]nonan-7-yl)methyl)piperidin-1-yl)-1,2,4-triazine-6-carboxamide

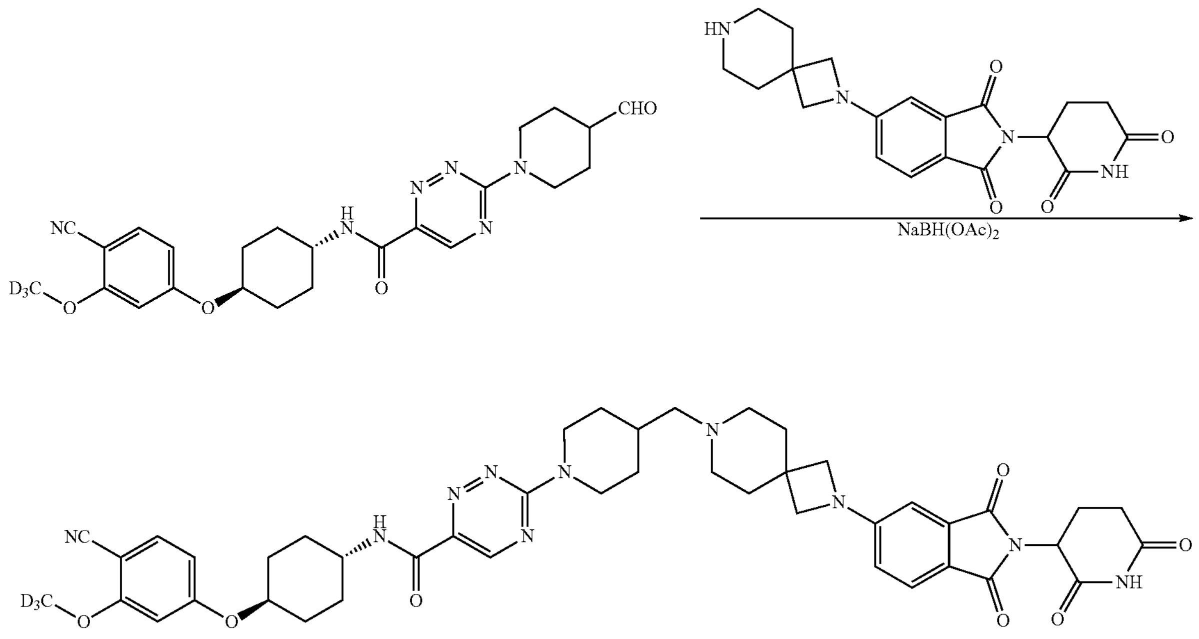

197

LC/MS ($ESI^+$) calcd for $C_{44}H_{48}D_3N_{10}O_7$ $[M+H]^+$ m/z, 834.4; found 835.

198: 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile

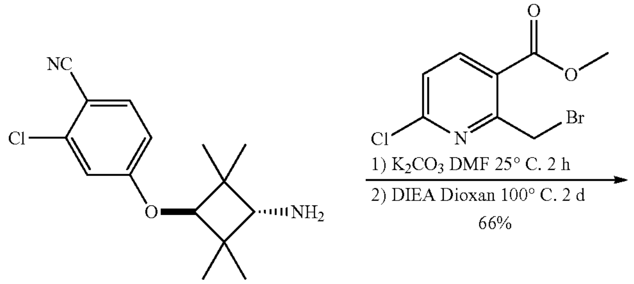

-continued

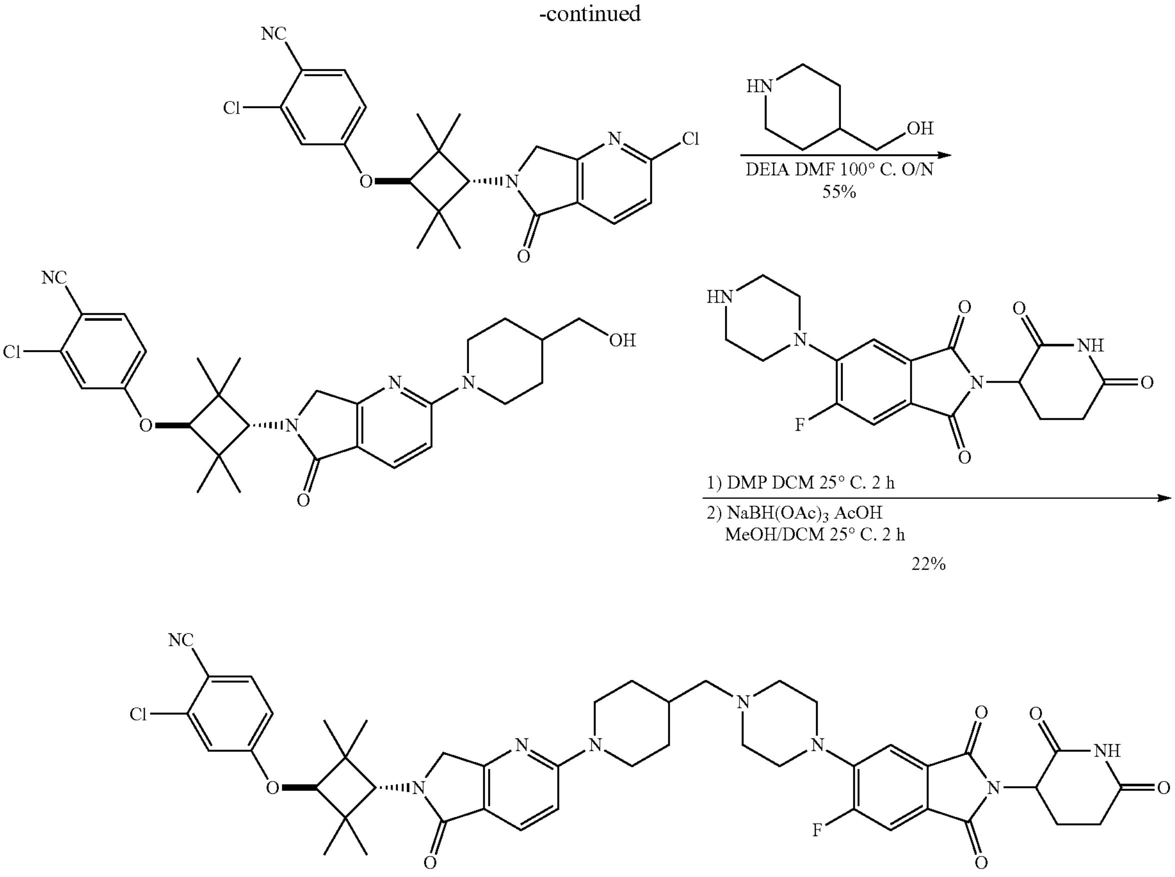

198

1. Synthesis of compound 2-chloro-4-((1r,3r)-3-(2-chloro-5-oxo-5,7-dihydro-6H-pyrrolo[3,4-b]pyridin-6-yl)-2,2,4,4-tetramethylcyclobutoxy)benzonitrile 4-((1r,3r)-3-Amino-2,2,4,4-tetramethylcyclobutoxy)-2-chlorobenzonitrile (527 mg, 1.89 mmol), potassium carbonate (392 mg, 2.84 mmol) and 10 mL of DMF were sequentially added. Under nitrogen protection, the mixture was stirred thoroughly, and then the solution of methyl 2-(bromomethyl)-6-chloronicotinate (500 mg, 1.89 mmol) in DMF was drop added. The resultant solution was stirred at room temperature for 2 h. The reaction was completed by TLC detection. The reaction solution was added with water, extracted three times with ethyl acetate, and dried over anhydrous sodium sulfate. The organic phase was washed three times with saturated brine, dried over anhydrous sodium sulfate, and rotatory evaporated to dry, to obtain the crude product, which was separated by silica gel column chromatography, to provide the intermediate. The intermediate was added with DIEA (734 mg, 1.48 mmol) and 5 mL of 1,4-dioxane, and reacted at 100° C. for two days. The end point of the reaction was confirmed by TLC, followed by separation over silica gel column chromatography, to obtain the intermediate 2-chloro-4-((1r,3r)-3-(2-chloro-5-oxo-5,7-dihydro-6H-pyrrolo[3,4-b] pyridin-6-yl)-2,2,4,4-tetramethylcyclobutoxy)benzonitrile (536 mg, 1.25 mmol), with a yield of 66%.

LC/MS (ESI$^+$) calcd for $C_{22}H_{21}ClN_3O_2$[M+H]$^+$ m/z, 430.1; found, 430.1.

2. Synthesis of 2-chloro-4-((1r,3r)-3-(2-(4-(hydroxymethyl)piperidin-1-yl)-5-oxo-5,7-dihydro-6H-pyrrolo[3,4-b]pyridin-6-yl)-2,2,4,4-tetramethylcyclobutoxy)benzonitrile Compound 2-chloro-4-((1r,3r)-3-(2-chloro-5-oxo-5,7-dihydro-6H-pyrrolo[3,4-b] pyridin-6-yl)-2,2,4,4-tetramethylcyclobutoxy)benzonitrile (150 mg, 0.35 mmol), 4-piperidinemethanol (120 mg, 1.05 mmol), DIEA (225 mg, 1.74 mmol) and 3 mL of DMF were successively added to the reactor, and under the nitrogen protection, the resultant solution was allowed to react overnight under stirring at 100° C. The end point of the reaction was determined by TLC. The reaction solution was added with water, extracted with ethyl acetate three times, and dried over anhydrous sodium sulfate. The organic phase was washed three times with saturated brine, dried over anhydrous sodium sulfate, and rotatory evaporated to dry to obtain the crude product, which was separated by Pre-TLC, to provide compound 3-((4-(2-((1r,3r)-3-(3-chloro-4-cyanophenoxy)-2,2,4,4-tetramethylcyclobutyl)-1-oxoisopropylpiperidin-5-yl)but-3-yn-1-yl)oxy)-N-(2-(2,6-dioxopiperidin-3-yl)-1-oxoisopropylpiperidin-4-yl)propionamide as an off-white solid (97 mg, 0.19 mmol), with a yield of 55%.

LC/MS (ESI$^+$) calcd for $C_{28}H_{33}ClN_4O_3$[M+H]$^+$ m/z, 509.2; found, 509.2.

3. 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile Compound 3-((4-(2-((1r,3r)-3-(3-chloro-4-cyanophenoxy)-2,2,4,4-tetramethylcyclobutyl)-1-oxoisopropylpiperidin-5-yl)but-3-yn-1-yl)oxy)-N-(2-(2,6-dioxopiperidin-3-yl)-1-oxoisopropylpiperidin-4-yl)propionamide (60 mg, 0.12 mmol) was dissolved in 2 mL of DCM, to which was added DMP (60 mg, 1.4 mmol), and the mixture was stirred 2 h at room temperature. TLC indicated the completion of the reaction. The reaction solution was filtered, and the filter cake was rinsed with DCM. The filtrate was rotatory evaporated to dry, to obtain a crude product, to which was added 2-(2,6-dioxopiperidin-3-yl)-5-fluoro-6-(piperazin-1-yl) isoindole-1,3-dione (41 mg, 1.2 mmol), followed by addition of 2 mL DCM/MeOH (1:1) to dissolve the reactions. Then, glacial acetic acid (14 mg, 0.24 mmol) was added, and the reaction solution was stirred and reacted at room temperature for 30 min, to which was then added sodium cyanoborohydride (30 mg, 0.47 mmol). The resultant solution was stirred at room temperature for 2 h. The end point of the reaction was determined by TLC, and then the saturated aqueous solution of sodium bicarbonate was added. The reaction solution was extracted three times with dichloromethane, dried, rotatory evaporated to dry, and separated by pre-TLC, to provide compound 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile as an off-white solid (22 mg, 0.19 mmol), with a yield of 22%.

LC/MS (ESI$^+$) calcd for $C_{45}H_{48}ClFN_8O_6$ $[M+H]^+$ m/z, 851.3; found, 851.2.

$^1H$ NMR (400 MHz, $CDCl_3$) δ 8.05 (s, 1H), 7.74 (d, J=8.8 Hz, 1H), 7.50 (d, J=8.7 Hz, 1H), 7.46-7.38 (m, 1H), 7.34 (s, 1H), 6.92 (t, J=3.9 Hz, 1H), 6.76 (dd, J=8.7, 2.4 Hz, 1H), 6.61 (d, J=8.9 Hz, 1H), 4.87 (dd, J=12.3, 5.3 Hz, 1H), 4.52-4.46 (m, 2H), 4.41 (d, J=12.6 Hz, 3H), 4.18 (s, 1H), 3.68 (s, 2H), 3.23 (s, 3H), 2.84 (ddd, J=21.4, 21.0, 7.8 Hz, 4H), 2.76-2.63 (m, 2H), 2.56 (s, 3H), 2.17 (dd, J=21.7, 14.1 Hz, 2H), 2.09 (dd, J=11.2, 4.6 Hz, 1H), 2.02-1.70 (m, 4H), 1.42-1.33 (m, 6H), 1.17 (s, 6H).

199: Synthesis of 2-chloro-4-((1r,3r)-3-(5-(4-(2,6-dioxopiperidin-3-yl)-6-fluoro-1,3-dioxoisoindolin-5-yl)piperazin-1-yl)but-1-yn-1-yl)-1-oxoisoindolin-2-yl)-2,4,4-tetramethylcyclobutoxy)benzonitrile

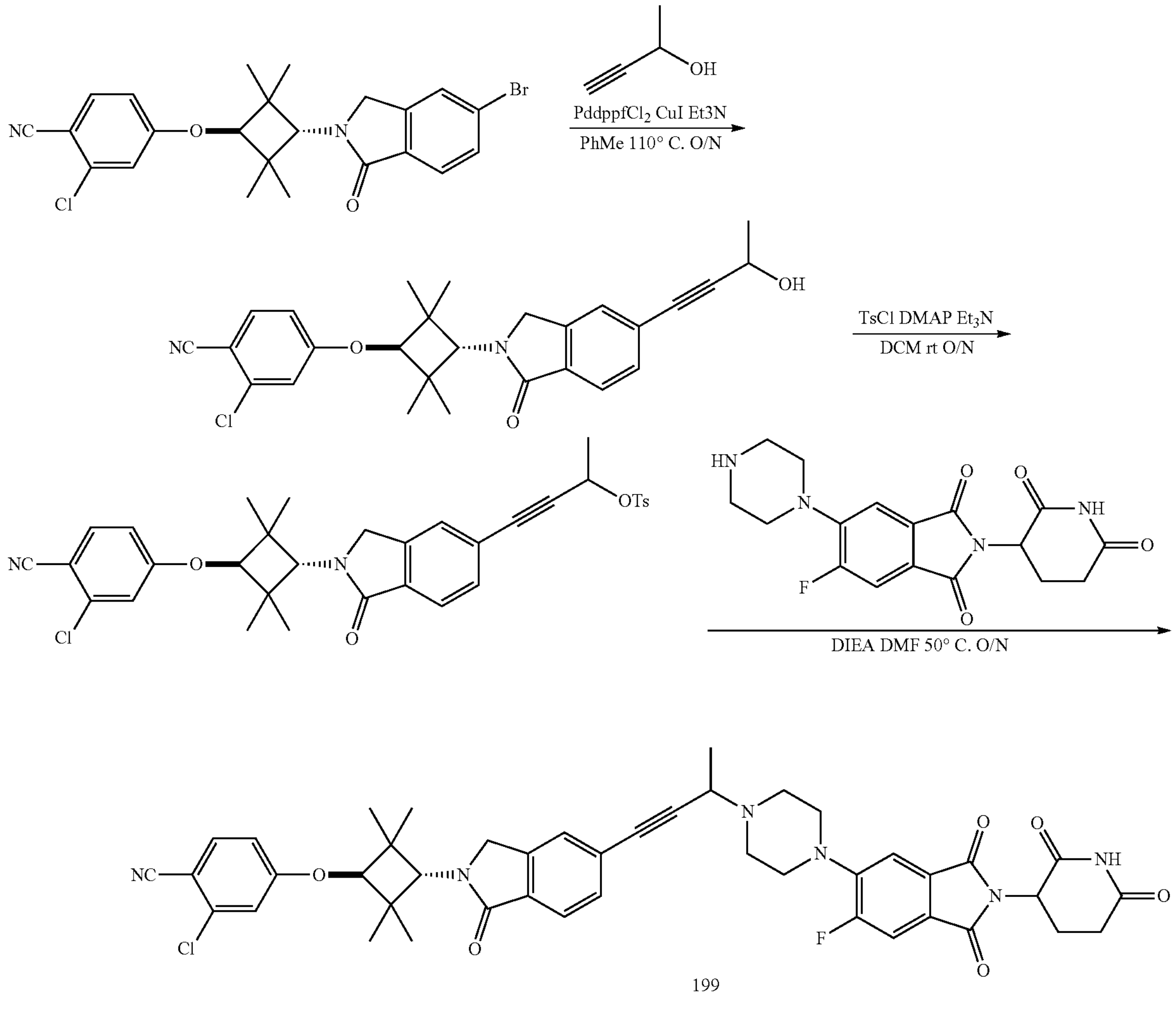

1. 2-chloro-4-((1r,3r)-3-(5-(3-hydroxybut-1-yn-1-yl)-1-oxoisoindolin-2-yl)-2,2,4,4-tetramethylcyclobutoxy)benzonitrile Compound but-3-yn-2-ol (178 mg, 2.53 mmol), 4-((1r,3r)-3-(5-bromo-1-oxoisoindol-2-yl)-2,2,4,4-tetramethylcyclobutoxy)-2-chlorobenzonitrile (400 mg, 0.84 mmol), [1,1'-bis(diphenylphosphino)ferrocene]dichloropalladium (62 mg, 0.084 mmol). CuI (48 mg, 0.25 mmol), 1 mL of triethylamine and 3 mL of toluene were sequentially added to the reactor, and under nitrogen protection, the mixture was allowed to react overnight at 110° C. TLC indicated the completion of the reaction, and the reaction solution was filtered. The filter cake was rinsed with dichloromethane, rotatory evaporated to dry, and purified by silica gel column chromatography, to obtain 2-chloro-4-((1r,3r)-3-(5-(3-hydroxy-but-1-yn-1-yl)-1-oxoisoindol-2-yl)-2,2,4,4-tetramethylcyclobutoxy) benzonitrile as a brown solid (300 mg, 0.65 mmol), with a yield of 77%.

LC/MS (ESI$^+$) calcd for $C_{27}H_{27}ClN_2O_3$[M+H]$^+$ m/z, 463.2; found, 463.1.

2. Synthesis of Compound 4-(2-((1r,3r)-3-(3-chloro-4-cyanophenoxy)-2,2,4,4-tetramethylcyclobutyl)-1-oxoisoindolin-5-yl)but-3-yn-2-yl-4-methyl benzenesulfonate Compound 2-chloro-4-((1r,3r)-3-(5-(3-hydroxybut-1-yn-1-yl)-1-oxoisoindol-2-yl)-2,2,4,4-tetramethylcyclobutoxy) benzonitrile (50 mg, 0.11 mmol), DMAP (1 mg, 0.11 mmol), triethylamine (33 mg, 0.32 mmol) and 2 mL of DCM were sequentially added to the reactor, and then under nitrogen protection, TsCl (25 mg, 0.13 mmol) was added at 0° C. The reaction solution was gradually warmed to room temperature and reacted overnight under stirring. TLC confirmed that the reaction was completed. The reaction solution was added with water, extracted three times with dichloromethane, dried over anhydrous sodium sulfate, filtered, rotatory evaporated to dry, and separated by pre-TLC, to provide 4-(2-((1r,3r)-3-(3-chloro-4-cyanophenoxy)-2,2,4,4-tetramethylcyclobutyl)-1-oxoisoindol-5-yl)but-3-yn-2-yl-4-methylbenzenesulfonate as an off-white solid (16 mg, 0.026 mmol), with a yield of 24%.

LC/MS (ESI$^+$) calcd for $C_{34}H_{33}ClN_2O_5S$ [M+H]$^+$ m/z, 617.2; found, 617.2.

3. Synthesis of Compound 2-chloro-4-((1r,3r)-3-(5-(4-(2,6-dioxopiperidin-3-yl)-6-fluoro-1,3-dioxoisoindolin-5-yl)piperazin-1-yl)but-1-yn-1-yl)-1-oxoisoindolin-2-yl)-2,4,4-tetramethylcyclobutoxy) benzonitrile Compound 4-(2-((1r,3r)-3-(3-chloro-4-cyanophenoxy)-2,2,4,4-tetramethylcyclobutyl)-1-oxoisoindol-5-yl)but-3-yn-2-yl-4-methyl benzenesulfonate (16 mg, 0.026 mmol), 2-(2,6-dioxopiperidin-3-yl)-5-fluoro-6-(piperazin-1-yl) isoindole-1,3-dione (9 mg, 0.026 mmol), DIEA (10 mg, 0.077 mmol) and 1 mL of DMF were sequentially added to the reactor, and under nitrogen protection, the mixture was allowed to react overnight at 50° C. TLC confirmed that the reaction was completed. The reaction solution was added with water, extracted three times with ethyl acetate, and dried over anhydrous sodium sulfate. The organic phase was washed three times with saturated brine, dried over anhydrous sodium sulfate, rotatory evaporated to dry to obtain the crude product, which was separated by pre-TLC, to provide 2-chloro-4-((1r,3r)-3-(5-(4-(2,6-dioxopiperidin-3-yl)-6-fluoro-1,3-dioxoisoindolin-5-yl) piperazin-1-yl)but-1-yn-1-yl)-1-oxoisoindolin-2-yl)-2,4,4-tetramethylcyclobutoxy) benzonitrile as pale yellow solid (5 mg, 0.006 mmol), with a yield of 24%. LC/MS (ESI$^+$) calcd for $C_{44}H_{42}ClFN_6O_6$ [M+H]$^+$ m/z, 805.3; found, 805.2.

$^1$H NMR (400 MHz, $CDCl_3$) δ 8.11 (d, J=8.8 Hz, 1H), 7.72 (d, J=7.8 Hz, 1H), 7.53-7.44 (m, 3H), 7.41 (d, J=11.1 Hz, 1H), 7.34 (d, J=7.3 Hz, 1H), 6.92 (d, J=2.4 Hz, 1H), 6.77 (dd, J=8.7, 2.4 Hz, 1H), 4.87 (dd, J=12.3, 5.2 Hz, 1H), 4.58 (s, 2H), 4.34 (s, 1H), 4.25 (s, 1H), 3.76 (d, J=7.1 Hz, 1H), 3.29 (s, 4H), 2.83 (dd, J=13.4, 9.9 Hz, 3H), 2.78-2.65 (m, 4H), 2.11-2.04 (m, 1H), 1.43 (d, J=7.0 Hz, 3H), 1.37 (d, J=7.5 Hz, 6H), 1.19-1.17 (m, 6H).

HC-2954-01

200: 2-chloro-4-((1r,4r)-4-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy) benzonitrile

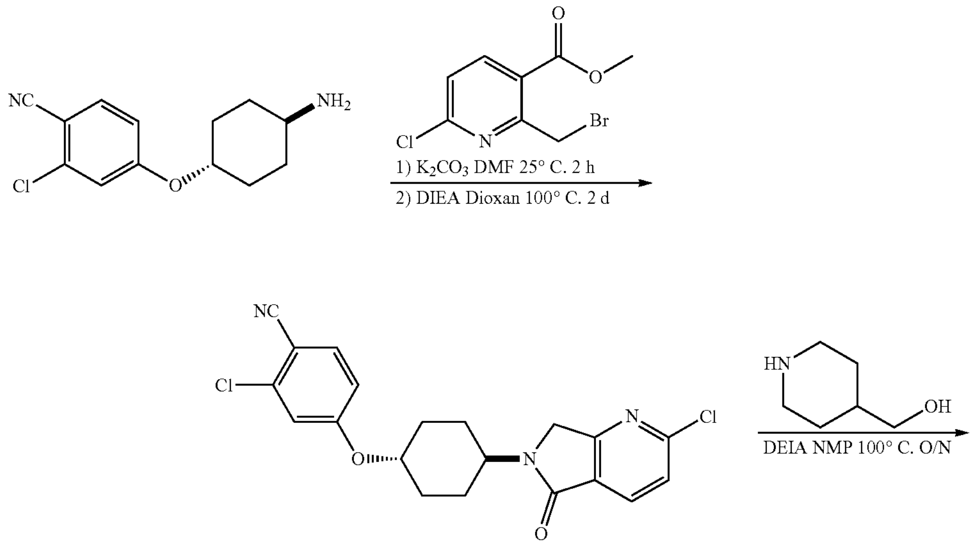

-continued

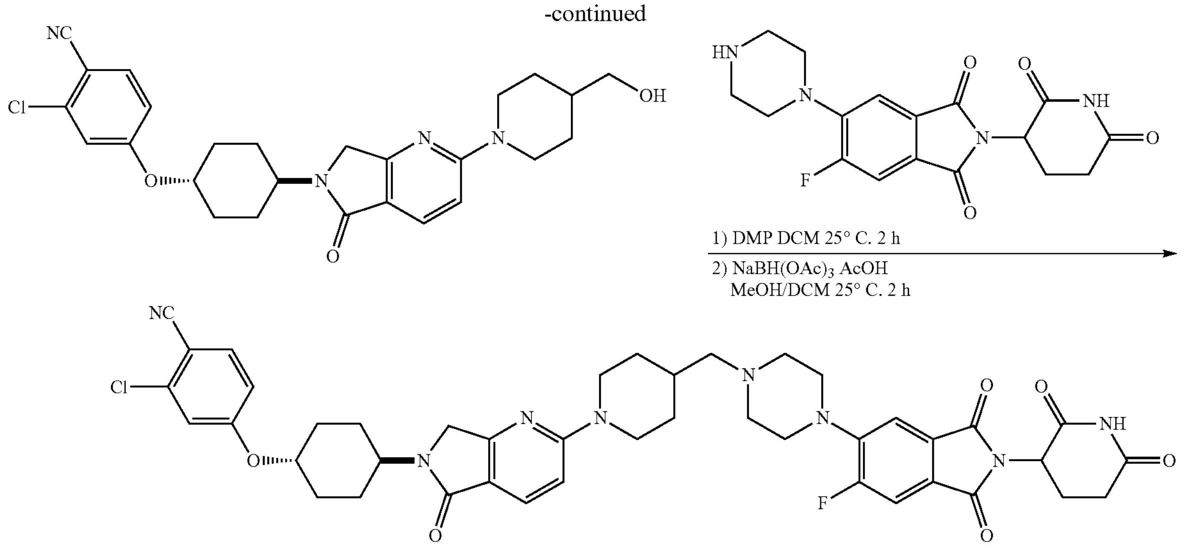

200

1. Synthesis of 2-chloro-4-((1r,4r)-4-(2-chloro-5-oxo-5,7-dihydro-6H-pyrrolo[3,4-b]pyridin-6-yl)cyclohexyl)oxy)benzonitrile Compound 4-((1r,4r)-4-aminocyclohexyl)oxy)-2-chlorobenzonitrile (2.37 g, 9.45 mmol), potassium carbonate (1.96 g, 14.18 mmol), and 40 ml DMF were successively added, and then under nitrogen protection, after stirring evenly, the solution of methyl 2-(bromomethyl)-6-chloronicotinate (2.5 g, 9.45 mmol) in DMF was added dropwise. The mixture was stirred at room temperature for 2 h. The end point of the reaction was determined by TLC. The reaction solution was added with water, extracted three times with ethyl acetate, washed three times with saturated brine, dried over anhydrous sodium sulfate, and rotatory evaporated to dry, to provide a crude product, which was separated by silica gel column chromatography, to provide the intermediate. To the intermediate, were added DIEA (4.73 mg, 36.61 mmol) and 20 mL of 1,4-dioxane, and the mixture was allowed to react at 100° C. for two days. The end point of the reaction was confirmed by TLC, followed by separation by silica gel column chromatography, to provide the intermediate 2-chloro-4-((1r,4r)-4-(2-chloro-5-oxo-5,7-dihydro-6H-pyrrolo[3,4-b]pyridin-6-yl)cyclohexyl)oxy)benzonitrile (1.85 g, 4.60 mmol), with a yield of 49%.

LC/MS ($ESI^+$) calcd for $C_{20}H_{17}Cl_2N_3O_2$ $[M+H]^+$ m/z, 402.1; found, 402.1.

$^1H$ NMR (400 MHz, $CDCl_3$) δ 8.00 (d, J=8.0 Hz, 1H), 7.50 (d, J=8.7 Hz, 1H), 7.39 (d, J=8.0 Hz, 1H), 6.94 (d, J=2.3 Hz, 1H), 6.80 (dd, J=8.7, 2.3 Hz, 1H), 4.32 (s, 2H), 4.27 (dd, J=9.6, 4.0 Hz, 2H), 2.23 (s, 2H), 1.98 (d, J=7.0 Hz, 2H), 1.67 (dd, J=17.0, 8.4 Hz, 4H).

2. 2-chloro-4-((1r,4r)-4-(2-(4-(hydroxymethyl)piperidin-1-yl)-5-oxo-5,7-dihydro-6H-pyrrolo[3,4-b]pyridin-6-yl)cyclohexyl)oxy)benzonitrile Compound 2-chloro-4-((1r,4r)-4-(2-chloro-5-oxo-5,7-dihydro-6H-pyrrolo[3,4-b]pyridin-6-yl)cyclohexyl)oxy)benzonitrile (900 mg, 2.24 mmol), 4-piperidinemethanol (773 mg, 6.71 mmol), DIEA (1.45 mg, 11.19 mmol) and 10 mL of NMP were sequentially added to a reactor, and under nitrogen protection, the mixture was allowed to react overnight at 100° C. TLC confirmed that the reaction was completed. The reaction solution was added with water, extracted three times with ethyl acetate, and dried over anhydrous sodium sulfate. The organic phase was washed three times with saturated brine, dried over anhydrous sodium sulfate, rotatory evaporated to dry to obtain the crude product, which was separated by silica gel column chromatography, to provide 2-chloro-4-((1r,4r)-4-(2-(4-(hydroxymethyl)piperidin-1-yl)-5-oxo-5,7-dihydro-6H-pyrrolo[3,4-b]pyridin-6-yl)cyclohexyl)oxy)benzonitrile as an off-white solid (1.05 mg, 2.18 mmol), with a yield of 98%. LC/MS ($ESI^+$) calcd for $C_{26}H_{29}ClN_4O_3[M+H]^+$ m/z, 481.2; found, 481.2.

3. Compound 2-chloro-4-((1r,4r)-4-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile Compound 2-chloro-4-((1r,4r)-4-(2-(4-(hydroxymethyl)piperidin-1-yl)-5-oxo-5,7-dihydro-6H-pyrrolo[3,4-b]pyridin-6-yl)cyclohexyl)oxy)benzonitrile (60 mg, 0.12 mmol) was dissolved in 2 mL of DCM, to which was added DMP (60 mg, 1.4 mmol), and the mixture was stirred and reacted 2 h at room temperature. TLC indicated the completion of the reaction. The reaction solution was filtered, and the filter cake was rinsed with DCM. The filtrate was rotatory evaporated to dry, to obtain a crude product, to which was added 2-(2,6-dioxopiperidin-3-yl)-5-fluoro-6-(piperazin-1-yl)isoindole-1,3-dione (43 mg, 0.092 mmol), followed by addition of 2 mL DCM/MeOH (1:1) to dissolve the reactions. Then, glacial acetic acid (10 mg, 0.17 mmol) was added, and the reaction solution was stirred and reacted at room temperature for 30 min, to which was then added sodium triacetylborohydride (71 mg, 0.33 mmol). The resultant solution was stirred and reacted at room temperature for 2 h. The end point of the reaction was determined by TLC, and then the saturated aqueous solution of sodium bicarbonate was added. The reaction solution was extracted three times with dichloromethane. The organic phase was combined, dried, rotatory evaporated to dry, and separated by pre-TLC, to provide compound 2-chloro-4-((1r,4r)-4-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile as an off-white solid (32 mg, 0.39 mmol), with a yield of 46%.

LC/MS (ESI$^+$) calcd for $C_{43}H_{44}ClFN_8O_6$ $[M+H]^+$ m/z, 822.3; found, 822.3.

$^1$H NMR (400 MHz, $CDCl_3$) δ 8 23 (s, 1H), 7.81 (d, J=8.8 Hz, 1H), 7.56 (d, J=8.7 Hz, 1H), 7.48 (d, J=10.9 Hz, 1H), 7.40 (d, J=6.8 Hz, 1H), 7.00 (d, J=2.4 Hz, 1H), 6.86 (dd, J=8.8, 2.4 Hz, 1H), 6.66 (d, J=8.9 Hz, 1H), 4.95 (d, J=5.5 Hz, 1H), 4.47 (d, J=13.0 Hz, 2H), 4.27 (dd, J=12.6, 8.7 Hz, 2H), 4.19 (s, 2H), 3.33 (s, 4H), 2.89 (ddd, J=21.7, 20.6, 8.4 Hz, 4H), 2.78 (dd, J=17.9, 8.4 Hz, 2H), 2.72-2.49 (m, 3H), 2.20 (d, J=22.8 Hz, 4H), 2.16-2.11 (m, 1H), 2.01 (t, J=11.6 Hz, 5H), 1.70 (s, 6H).

201: Synthesis of 2-chloro-4-((1r,4r)-4-(2-((4-(2-(2,6-dioxopiperidin-3-yl)-1,3-dioxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile

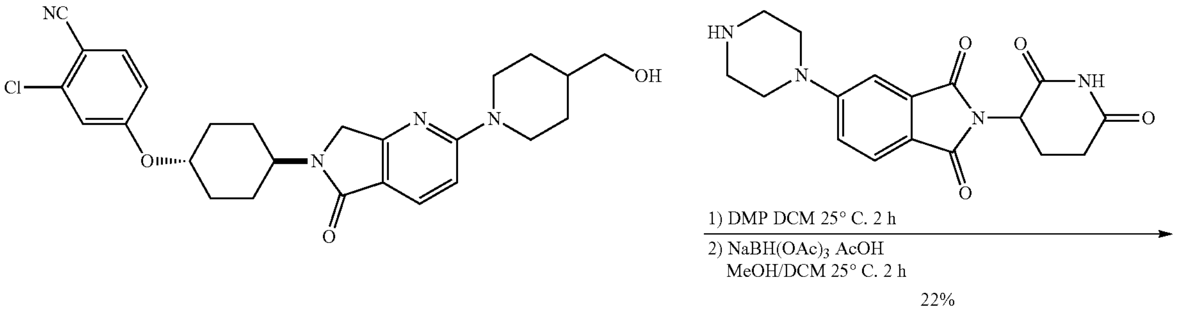

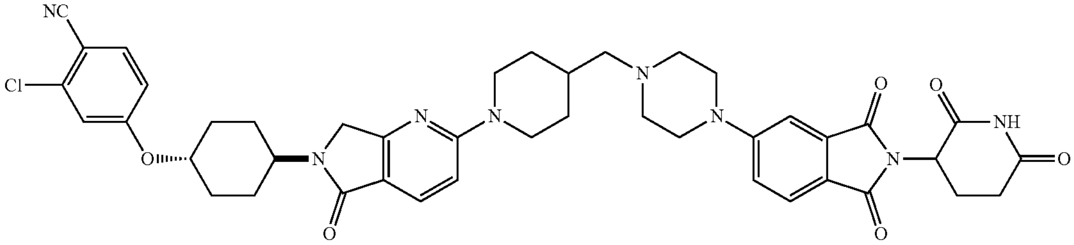

201

LC/MS (ESI$^+$) calcd for $C_{43}H_{45}ClNO_6$ $[M+H]^+$ m/z, 805.3; found, 805.3.

$^1$H NMR (400 MHz, $CDCl_3$) δ 8.11 (s, 1H), 7.74 (d, J=8.8 Hz, 1H), 7.64 (d, J=8.4 Hz, 1H), 7.49 (d, J=8.7 Hz, 1H), 7.23 (s, 1H), 7.00 (d, J=8.5 Hz, 1H), 6.94 (d, J=2.3 Hz, 1H), 6.79 (dd, J=8.8, 2.4 Hz, 1H), 6.59 (d, J=8.9 Hz, 1H), 4.88 (dd, J=12.1, 5.2 Hz, 1H), 4.40 (d, J=12.4 Hz, 2H), 4.23 (d, J=7.0 Hz, 2H), 4.13 (s, 2H), 3.38 (s, 3H), 2.95-2.68 (m, 5H), 2.53 (s, 3H), 2.17 (s, 4H), 2.11-2.03 (m, 1H), 1.94 (s, 5H), 1.62 (d, J=7.9 Hz, 8H).

202: Synthesis of 2-chloro-4-((1r,3r)-3-(2-(4-((4-(2,6-dioxopiperidin-3-yl-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile

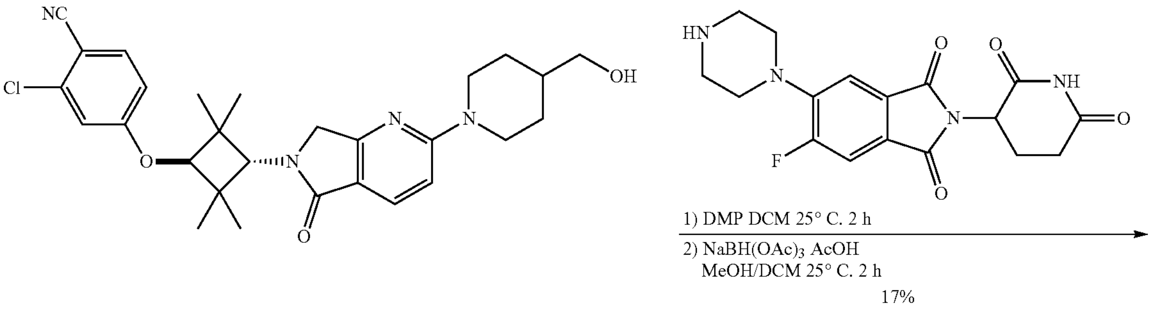

-continued

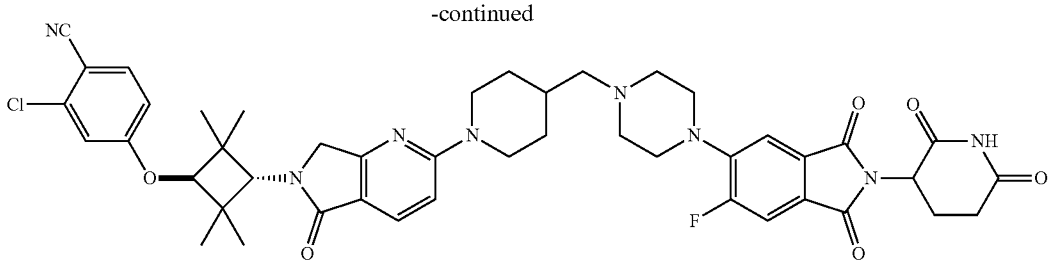

202

The target compound was obtained as an off-white solid (17 mg, 0.20 mmol), with a yield of 17%.

LC/MS (ESI+) calcd for $C_{45}H_{49}ClN_8O_6$ $[M+H]^+$ m/z, 833.4; found, 833.3.

$^1H$ NMR (400 MHz, $CDCl_3$) δ 8.11 (s, 1H), 7.74 (d, J=8.8 Hz, 1H), 7.64 (d, J=8.4 Hz, 1H), 7.49 (d, J=8.7 Hz, 1H), 7.23 (s, 1H), 7.00 (d, J=8.5 Hz, 1H), 6.94 (d, J=2.3 Hz, 1H), 6.79 (dd, J=8.8, 2.4 Hz, 1H), 6.59 (d, J=8.9 Hz, 1H), 4.88 (dd, J=12.1, 5.2 Hz, 1H), 4.40 (d, J=12.4 Hz, 2H), 4.23 (d, J=7.0 Hz, 2H), 4.13 (s, 2H), 3.38 (s, 3H), 2.95-2.68 (m, 5H), 2.53 (s, 3H), 2.17 (s, 4H), 2.11-2.03 (m, 1H), 1.94 (s, 5H), 1.62 (d, J=7.9 Hz, 8H).

203: Synthesis of 2-chloro-4-((1r,4r)-4-(2-(4-((4-(2,6-dioxopiperidin-3-yl)-6-fluoro-3-oxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile 204: Synthesis of 2-chloro-4-((1r,4r)-4-(2-(4-((4-(2,6-dioxopiperidin-3-yl)-6-fluoro-1-oxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile

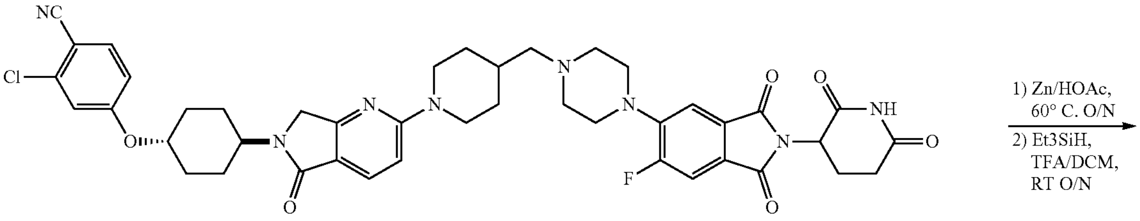

202

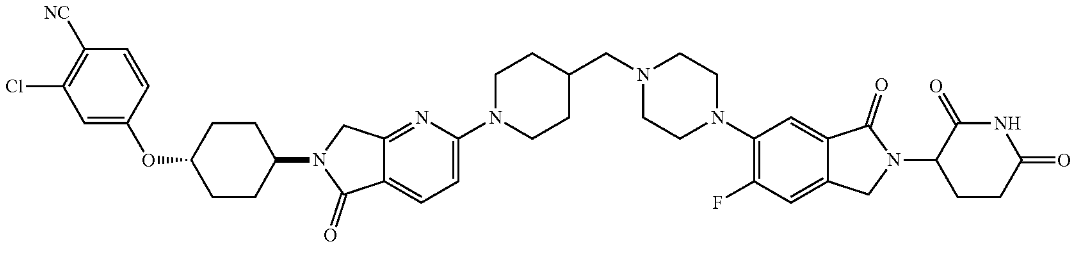

203

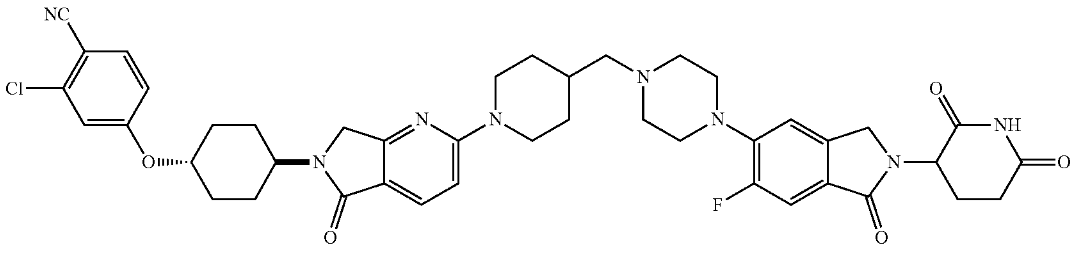

204

Compound 2-chloro-4-((1r,4r)-4-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile (57 mg, 0.070 mmol) was dissolved in 1 mL of HOAc, to which was added Zn powder (92 mg, 1.41 mmol), and the mixture was stirred and reacted overnight at 60° C. TLC indicated the completion of the reaction, and the reaction solution was filtered. The filter cake was rinsed with DCM. The filtrate was rotatory evaporated to dry to obtain the crude product, to which were added 2 mL DCM and triethylsilane (33 mg, 0.28 mmol, and then 1 mL of TFA was added. The reaction was stirred and reacted overnight at room temperature. The end point of the reaction was determined by TLC. The solvent was evaporated under reduced pressure. To the residue, was added the saturated aqueous solution of sodium bicarbonate. The resultant solution was extracted with dichloromethane three times. The organic phase was combined, dried, rotatory evaporated to dry, and separated by pre-TLC (EA:MeOH 10:1), to provide the off-white solid compound 2-chloro-4-((1r,4r)-4-(2-(4-((4-(2,6-dioxopiperidin-3-yl)-6-fluoro-3-oxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile 203 (6 mg, 0.007 mmol) as the upper spot, with a yield of 11%.

LC/MS (ESI+) calcd for $C_{43}H_{46}ClFN_8O_5$ $[M+H]^+$ m/z, 810.3; found, 810.3.

$^1H$ NMR (400 MHz, $CDCl_3$) δ 9.16 (s, OH), 7.73 (d, J=8.9 Hz, 1H), 7.49 (d, J=8.7 Hz, 1H), 7.40 (d, J=7.9 Hz, 1H), 7.07 (d, J=11.3 Hz, 1H), 6.95 (t, J=4.1 Hz, 1H), 6.80 (dd, J=8.7, 2.4 Hz, 1H), 6.60 (d, J=8.9 Hz, 1H), 5.09 (dd, J=13.3, 5.1 Hz, 1H), 4.43-4.29 (m, 3H), 4.21 (d, J=16.1 Hz, 3H), 4.13 (s, 2H), 3.09 (s, 4H), 2.88 (dd, J=21.9, 10.5 Hz, 2H), 2.78 (dt, J=18.1, 5.2 Hz, 2H), 2.59 (s, 4H), 2.38-2.24 (m, 6H), 2.21-2.08 (m, 4H), 1.94 (d, J=16.5 Hz, 2H), 1.85 (d, J=11.7 Hz, 3H), 1.69-1.56 (m, 4H).

And the off-white solid compound 2-chloro-4-((1r,4r)-4-(2-(4-((4-(2,6-dioxopiperidin-3-yl)-6-fluoro-1-oxoisoindolin-5-yl)piperazin-1-yl)methyl)piperidin-1-yl)-5-oxo-5,7-dihydro-6H-pyrrolo[3,4-b]pyridin-6-yl)cyclohexyl)oxy) benzonitrile 204 (11 mg, 0.014 mmol) as the lower spot, with a yield of 19%.

LC/MS (ESI+) calcd for $C_{43}H_{46}ClFN_8O_5$ $[M+H]^+$ m/z, 810.3; found, 810.3.

$^1H$ NMR (400 MHz, $CDCl_3$) δ 9.57 (s, OH), 7.73 (d, J=8.9 Hz, 1H), 7.50 (d, J=8.7 Hz, 1H), 7.41 (d, J=11.3 Hz, 1H), 6.95 (d, J=2.3 Hz, 1H), 6.92 (d, J=7.2 Hz, 1H), 6.80 (dd, J=8.8, 2.4 Hz, 1H), 6.61 (d, J=8.9 Hz, 1H), 5.06 (dd, J=13.3, 5.1 Hz, 1H), 5.06 (dd, J=13.3, 5.1 Hz, 1H), 4.43-4.30 (m, 3H), 4.21 (d, J=16.0 Hz, 3H), 4.14 (s, 2H), 3.15 (s, 4H), 2.98 (s, 2H), 2.90 (t, J=12.2 Hz, 2H), 2.77 (dd, J=11.2, 4.4 Hz, 2H), 2.60 (s, 4H), 2.33-2.22 (m, 3H), 2.13 (ddd, J=12.6, 11.1, 7.8 Hz, 3H), 1.85 (d, J=12.1 Hz, 3H), 1.70-1.55 (m, 4H).

205: Synthesis of 2-chloro-4-((1r,3r)-3-(2-(4-((4-(2,6-dioxopiperidin-3-yl)-6-fluoro-3-oxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile 206: Synthesis of 2-chloro-4-((1r,3r)-3-(2-(4-((4-(2,6-dioxopiperidin-3-yl)-6-fluoro-1-oxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile

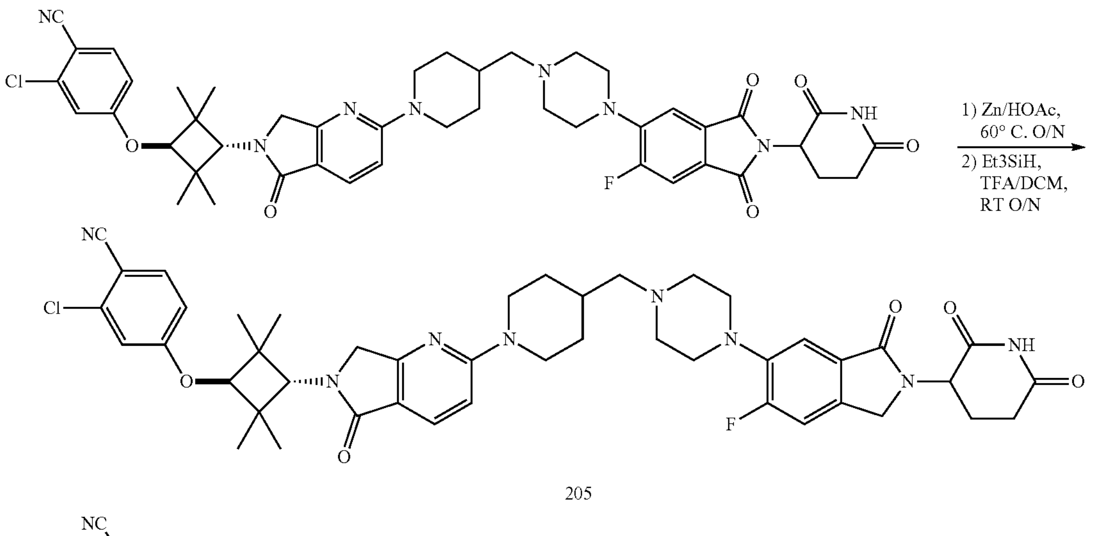

205

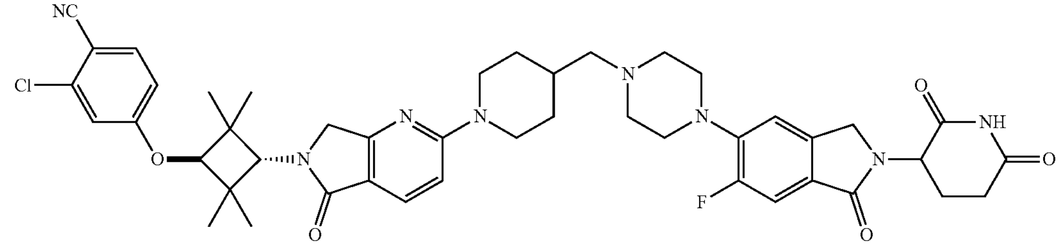

206

2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile (47 mg, 0.055 mmol) was dissolved in 1 mL of HOAc, to which was added Zn powder (92 mg, 1.41 mmol), and the mixture was stirred and reacted overnight at 60° C. TLC indicated the completion of the reaction, and the reaction solution was filtered. The filter cake was rinsed with DCM. The filtrate was rotatory evaporated to dry to obtain the crude product, to which were added 2 mL DCM and triethylsilane (33 mg, 0.28 mmol), and then 1 mL of TFA was added. The reaction was stirred and reacted overnight at room temperature. The end point of the reaction was determined by TLC. The solvent was evaporated under reduced pressure. To the residue, was added the saturated aqueous solution of sodium bicarbonate. The resultant solution was extracted with dichloromethane three times. The organic phase was combined, dried, rotatory evaporated to dry, and separated by pre-TLC (EA:MeOH 10:1), to provide the off-white solid compound 2-chloro-4-((1r,3r)-3-(2-(4-((4-(2,6-dioxopiperidin-3-yl)-6-fluoro-3-oxoisoindol-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile (18 mg, 0.022 mmol) as the upper spot, with a yield of 39%.

LC/MS ($ESI^+$) calcd for $C_{45}H_{50}ClFN_8O_5[M+H]^+$ m/z, 837.4; found, 837.4.

$^1H$ NMR (400 MHz, $CDCl_3$) δ 7.81 (d, J=8.8 Hz, 1H), 7.58 (d, J=8.7 Hz, 1H), 7.48 (d, J=7.9 Hz, 1H), 7.15 (d,

J=11.2 Hz, 1H), 6.99 (d, J=2.2 Hz, 1H), 6.84 (dd, J=8.7, 2.3 Hz, 1H), 6.69 (d, J=8.9 Hz, 1H), 5.17 (dd, J=13.3, 5.0 Hz, 1H), 4.55 (s, 2H), 4.45 (d, J=12.0 Hz, 3H), 4.35 (d, J=36.4 Hz, 2H), 4.25 (s, 1H), 3.17 (s, 3H), 3.05-2.92 (m, 3H), 2.91-2.87 (m, 1H), 2.68 (s, 4H), 2.33 (d, J=6.1 Hz, 3H), 1.93 (d, J=11.4 Hz, 3H), 1.44 (d, J=9.2 Hz, 6H), 1.36 (s, 2H), 1.29 (s, 2H), 1.23 (s, 6H).

And the off-white solid compound 2-chloro-4-((1r,3r)-3-(2-(4-((4-(2,6-dioxopiperidin-3-yl)-6-fluoro-1-oxoisoindol-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile (8 mg, 0.010 mmol) as the lower spot, with a yield of 17%.

LC/MS ($ESI^+$) calcd for $C_{45}H_{50}ClFN_8O_5[M+H]^+$ m/z, 837.4; found, 837.4.

$^1H$ NMR (400 MHz, $CDCl_3$) δ 7.81 (d, J=8.8 Hz, 1H), 7.58 (d, J=8.7 Hz, 1H), 7.48 (d, J=7.9 Hz, 1H), 7.14 (s, 1H), 6.88 (d, J=10.2 Hz, 1H), 6.84 (dd, J=8.7, 2.3 Hz, 1H), 6.69 (d, J=8.9 Hz, 1H), 5.17 (dd, J=13.3, 5.0 Hz, 1H), 4.55 (s, 2H), 4.45 (d, J=12.0 Hz, 3H), 4.35 (d, J=36.4 Hz, 2H), 4.25 (s, 1H), 3.17 (s, 3H), 3.05-2.92 (m, 3H), 2.91-2.87 (m, 1H), 2.68 (s, 4H), 2.33 (d, J=6.1 Hz, 3H), 1.93 (d, J=11.4 Hz, 3H), 1.44 (d, J=9.2 Hz, 6H), 1.36 (s, 2H), 1.29 (s, 2H), 1.23 (s, 6H).

207: (3-(5-(4-((1-(6-((1r,4r)-4-(3-chloro-4-cyanophenoxy)cyclohexyl)-5-oxo-6,7-dihydro-5H-pyrrolo[3,4-b]pyridin-2-yl)piperidine-4-yl)methyl)piperazin-1-yl)-6-fluoro-1-oxoisoindigo-2-yl)-2,6-dioxopiperidin-1-yl)methyl isopropyl carbonate

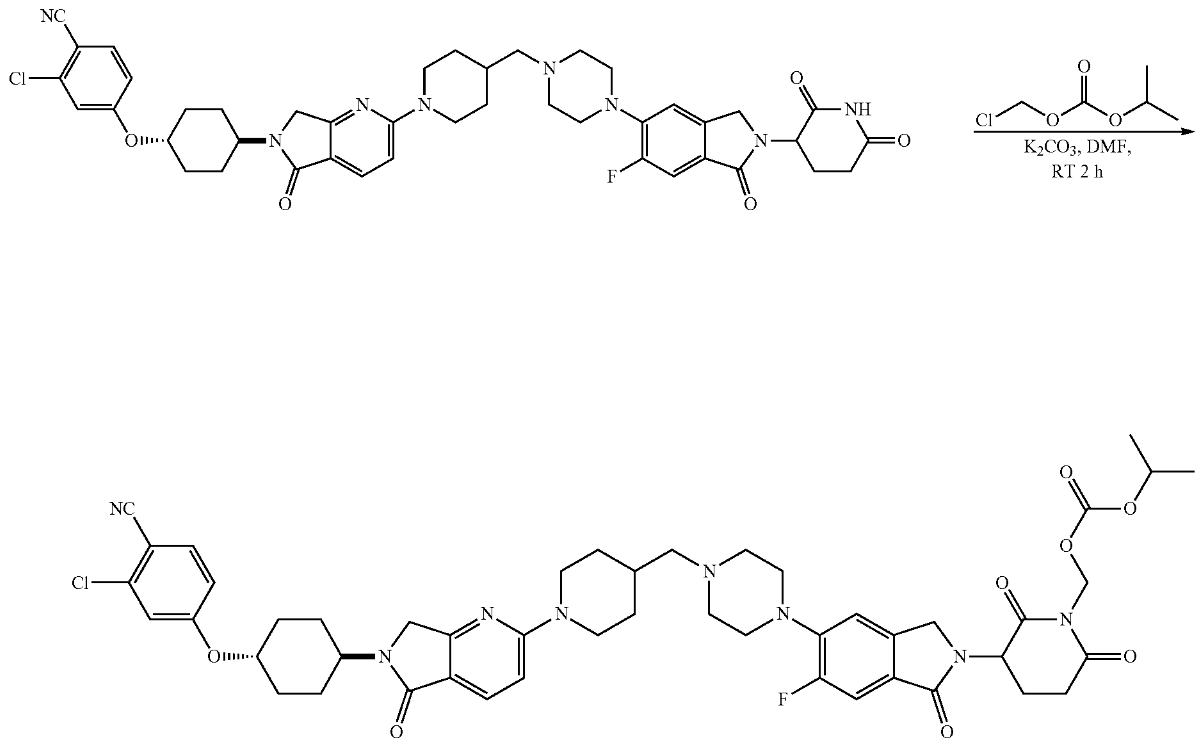

207

1. Synthesis of the compound chloromethyl isopropyl carbonate diester

Compound chloromethyl chloroformate (2 g, 15.51 mmol) was dissolved in 100 mL of DCM, to which were added triethylamine (1.57 g, 15.51 mmol) and isopropanol (932 mg, 15.51 mmol) at 0° C. The reaction was stirred and reacted at room temperature for 1 h. The reaction was completed by TLC detection. The reaction solution was filtered, and the filter cake was rinsed with DCM. The filtrate was rotatory evaporated to dry, to obtain the crude product, which was purified by silica gel column chromatography, to provide chloromethyl isopropyl carbonate diester as a colorless oil (523 mg, 3.43 mmol), with a yield of 22%.

LC/MS (ESI$^+$) calcd for $C_5H_9ClO_3$ $[M+H]^+$ m/z, 153.0; found, 153.0.

2. (3-(5-(4-((1-(6-((1r,4r)-4-(3-chloro-4-cyanophenoxy)cyclohexyl)-5-oxo-6,7-dihydro-5H-pyrrolo[3,4-b]pyridin-2-yl)piperidine-4-yl)methyl)piperazin-1-yl)-6-fluoro-1-oxoisoindigo-2-yl)-2,6-dioxopiperidin-1-yl)methyl isopropyl carbonate Compound 2-chloro-4-((1r,4r)-4-(2-(4-((4-(2,6-dioxopiperidin-3-yl)-6-fluoro-1-oxoisoindol-5-yl)piperazin-1-yl)methyl)piperidin-1-yl)-5-oxo-5,7-dihydro-6H-pyrrolo[3,4-b]pyridin-6-yl)cyclohexyl)oxy)benzonitrile (10 mg, 0.012 mmol) was added to a reactor, to which were then added 1 mL of DMF and potassium carbonate (3 mg, 0.018 mmol). The solution of chloromethyl isopropyl carbonate diester (4 mg, 0.024 mmol) in DMF was drop added to the reaction solution, and the solution was stirred at room temperature for 2 h. The reaction was completed by TLC detection. The reaction solution was added with water, and extracted with ethyl acetate three times. The organic layer was washed three times with saturated brine, dried over anhydrous sodium sulfate, rotatory evaporated to dry, and separated by pre-TLC to obtain an off-white compound (3-(5-(4-((1-(6-((1r,4r)-4-(3-chloro-4-cyanophenoxy)cyclohexyl)-5-oxo-6,7-dihydro-5H-pyrrolo[3,4-b]pyridin-2-yl) piperidine-4-yl)methyl)piperazin-1-yl)-6-fluoro-1-oxoisoindigo-2-yl)-2,6-dioxopiperidin-1-yl)methyl isopropyl carbonate (2 mg, 0.002 mmol), with a yield of 17%.

LC/MS (ESI$^+$) calcd for $C_{48}H_{54}ClFN_8O_8$ $[M+H]^+$ m/z, 925.4; found, 925.3.

208: Synthesis of 2-chloro-4-((1S,4r)-4-(2-((3S)-3-((4-(2-(2,6-dioxopiperidin-3-yl)-6-fluoro-3-oxoisoindolin-5-yl)piperazin-1-yl)methyl)pyrrolidin-1-yl)-5-oxo-5,7-dihydro-6H-pyrrolo[3,4-b]pyridin-6-yl)cyclohexyl)oxy)benzonitrile

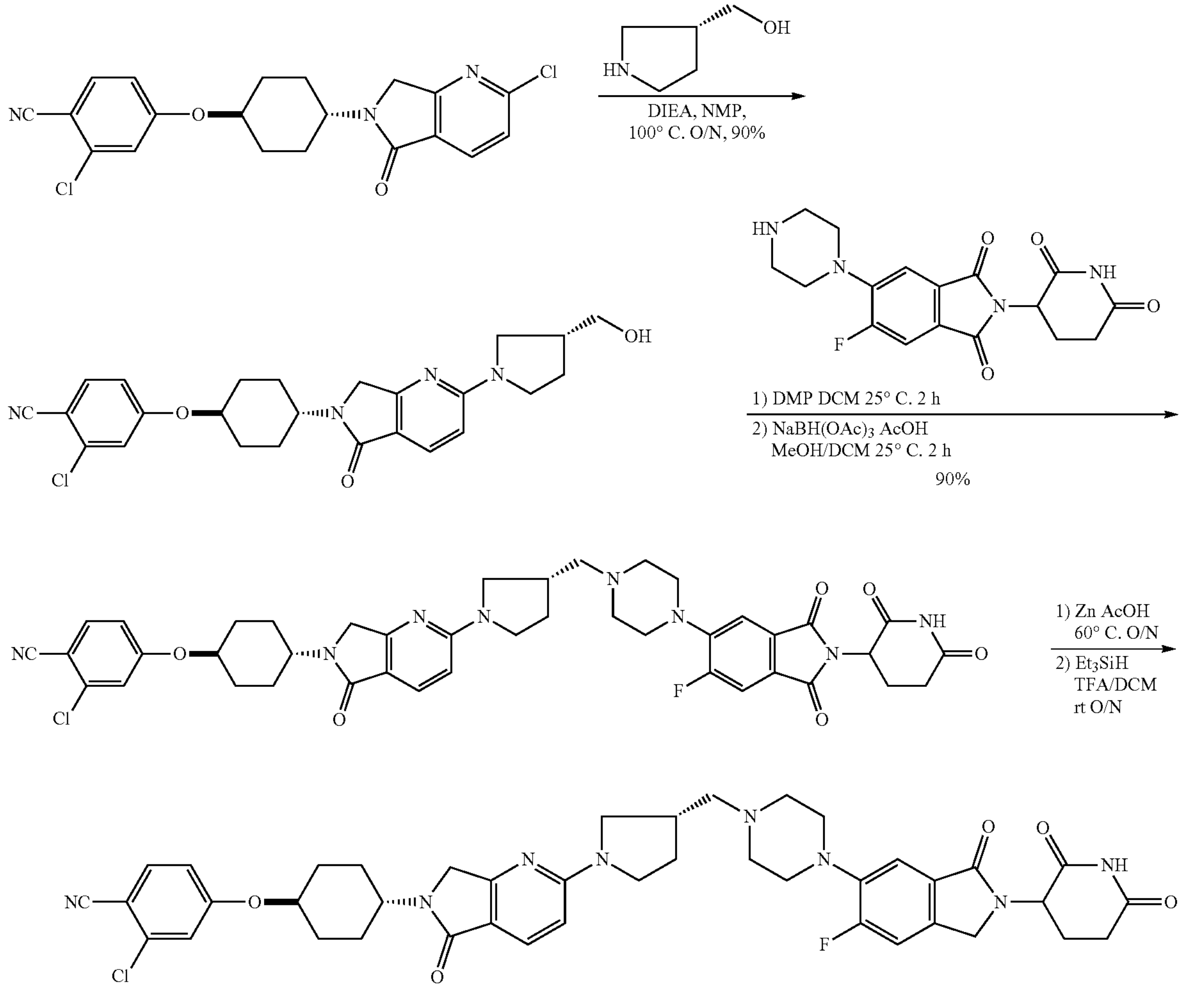

20% 208

-continued

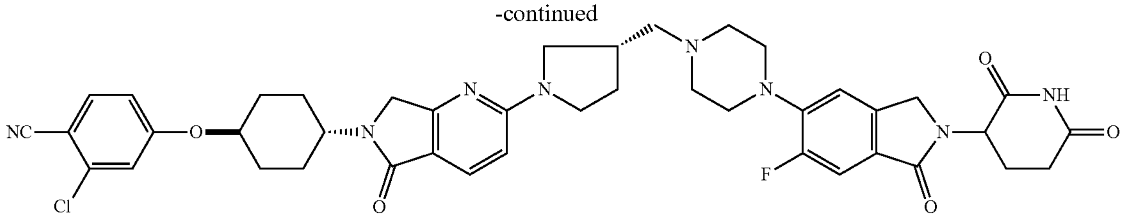

10% 209

LC/MS (ESI$^+$) calcd for $C_{42}H_{44}ClFN_8O_5$ $[M+H]^+$ m/z, 795.3; found, 795.3.

$^1$H NMR (400 MHz, $CDCl_3$) δ 9.45 (s, OH), 7.81 (d, J=8.7 Hz, 1H), 7.57 (d, J=8.7 Hz, 1H), 7.48 (d, J=7.9 Hz, 1H), 7.16 (d, J=11.2 Hz, 1H), 7.01 (t, J=7.5 Hz, 1H), 6.88 (dd, J=8.8, 2.4 Hz, 1H), 6.42 (d, J=8.8 Hz, 1H), 5.16 (dd, J=13.3, 5.1 Hz, 1H), 4.22 (d, J=17.5 Hz, 2H), 3.77 (s, 1H), 3.67 (d, J=16.9 Hz, 1H), 3.49 (t, J=16.0 Hz, 1H), 3.35-3.24 (m, 1H), 3.17 (s, 4H), 2.90-2.81 (m, 2H), 2.71 (s, 1H), 2.52 (dd, J=16.4, 8.4 Hz, 2H), 2.29-2.16 (m, 4H), 2.00 (s, 2H), 1.69 (dd, J=20.3, 11.0 Hz, 4H).

209: Synthesis of 2-chloro-4-((1S,4r)-4-(2-((3S)-3-((4-(2-(2,6-dioxopiperidin-3-yl)-6-fluoro-1-oxoisoindolin-5-yl)piperazin-1-yl)methyl)pyrrolidin-1-yl)-5-oxo-5,7-dihydro-6H-pyrrolo[3,4-b]pyridin-6-yl)cyclohexyl)oxy)benzonitrile LC/MS (ESI$^+$) calcd for $C_{42}H_{44}ClFN_8O_5$ $[M+H]^+$ m/z, 795.3; found, 795.3.

$^1$H NMR (400 MHz, $CDCl_3$) δ 7.82 (d, J=8.7 Hz, 1H), 7.57 (d, J=8.7 Hz, 1H), 7.51 (d, J=11.2 Hz, 1H), 7.01 (dd, J=8.6, 4.8 Hz, 2H), 6.87 (dd, J=8.7, 2.4 Hz, 1H), 6.41 (d, J=8.7 Hz, 1H), 5.17 (dd, J=13.3, 5.1 Hz, 1H), 4.42 (d, J=16.0 Hz, 1H), 4.34-4.26 (m, 3H), 4.23 (s, 2H), 3.79 (s, 1H), 3.66 (d, J=3.9 Hz, 1H), 3.52 (d, J=9.1 Hz, 1H), 3.27 (s, 5H), 2.90-2.49 (m, 9H), 2.34 (dd, J=13.0, 5.5 Hz, 1H), 2.30-2.14 (m, 5H), 1.93-1.80 (m, 2H), 1.70 (s, 4H).

210: Synthesis of 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile 211: Synthesis of 2-chloro-4-((1r,3r)-3-(2-(4-((4-(2,6-dioxopiperidin-3-yl)-6-fluoro-3-oxoisoindolin-5-yl)piperazin-1-yl)methyl)piperidin-1-yl)-S-oxo-5,7-dihydro-6H-pyrrolo[3,4-b]pyridin-6-yl)-2,2,4,4-tetramethylcyclobutoxy)benzonitrile 212: Synthesis of 2-chloro-4-((1r,3r)-3-(2-(4-((4-(2,6-dioxopiperidin-3-yl)-6-fluoro-1-oxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile

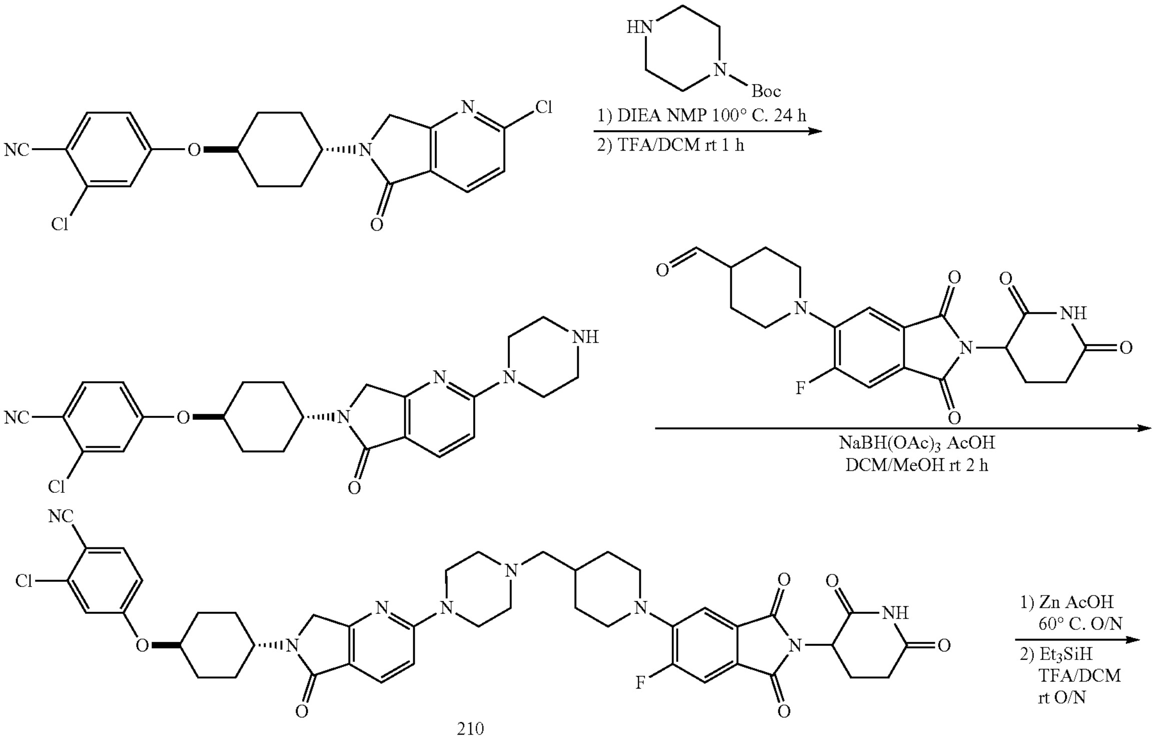

210

-continued

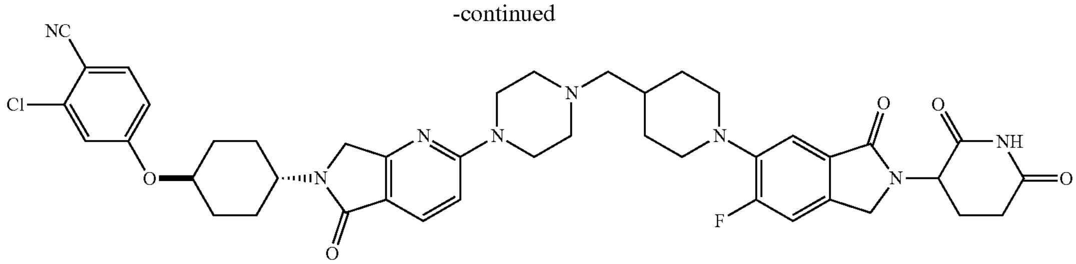

211

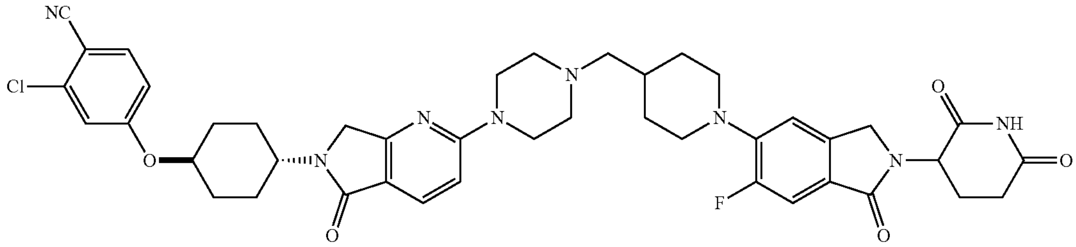

212

1. 2-chloro-4-((1r,4r)-4-(5-oxo-2-(piperazin-1-yl)-5,7-dihydro-6H-pyrrolo[3,4-b]pyridin-6-yl)cyclohexyl)oxy)benzonitrile Compound 2-chloro-4-((1r,4r)-4-(2-chloro-5-oxo-5,7-dihydro-6H-pyrrolo[3,4-b]pyridin-6-yl)cyclohexyl)oxy)benzonitrile (350 mg, 0.81 mmol), 1-t-butoxycarbonylpiperazine (454 mg, 2.44 mmol), DIEA (525 mg, 4.07 mmol) and 40 mL of NMP were sequentially added to a reactor, and under nitrogen protection, the mixture was allowed to react overnight at 100° C. TLC confirmed that the reaction was completed. The reaction solution was added with water, and extracted three times with ethyl acetate. The organic phase was washed three times with saturated brine, dried over anhydrous sodium sulfate, and rotatory evaporated to dry to obtain the crude product, which was separated by silica gel column chromatography, to provide the intermediate, which was dissolved in DCM/TFA. The reaction was stirred at room temperature for 1 h. The reaction was completed by TLC detection. The solvent was evaporated under reduced pressure, to which was added saturated sodium bicarbonate solution. The resultant solution was extracted three times with DCM, dried over anhydrous sodium sulfate, and rotatory evaporated to dry, to obtain compound 2-chloro-4-((1r,4r)-4-(5-oxo-2-(piperazin-1-yl)-5,7-dihydro-6H-pyrrolo[3,4-b]pyridin-6-yl)cyclohexyl)oxy) benzonitrile as an off-white solid (280 mg, 0.58 mmol), with a yield of 72%.

LC/MS (ESI$^+$) calcd for $C_{24}H_{26}ClN_5O_2$ $[M+H]^+$ m/z, 412.2; found, 412.2.

2. 2-Chloro-4-((1r,4r)-4-(2-(4-((1-(2,6-dioxopiperidin-3-yl)-6-fluoro-1,3-dioxoisoindol-5-yl)piperidine-4-yl)methyl)piperazin-1-yl)-5-oxo-5,7-dihydro-6H-pyrrolo[3,4-b]pyridin-6-yl)cyclohexyl)oxy) benzonitrile (210)

2-Chloro-4-((1r,4r)-4-(5-oxo-2-(piperazin-1-yl)-5,7-dihydro-6H-pyrrolo[3,4-b]pyridin-6-yl)cyclohexyl)oxy)benzonitrile (100 mg, 0.26 mmol) was added in 1-(2-(2,6-dioxopiperidin-3-yl)-6-fluoro-1,3-dioxopiperidin-5-yl) piperidine-4-acetaldehyde (117 mg, 0.26 mmol) and 2 mL DCM/MeOH (1:1) and dissolved, to which was added glacial acetic acid (31 mg, 0.52 mmol). The reaction solution was stirred and reacted at room temperature for 30 min, to which was then added sodium triacetylborohydride (219 mg, 1.03 mmol). The resultant solution was stirred at room temperature for 2 h. The end point of the reaction was determined by TLC, and then the saturated aqueous solution of sodium bicarbonate was added. The reaction solution was extracted three times with dichloromethane, dried, rotatory evaporated to dry, and separated by pre-TLC, to provide compound 2-chloro-4-((1r,4r)-4-(2-(4-((4-(2,6-dioxopiperidin-3-yl)-6-fluoro-1,3-dioxoisoindol-5-yl)piperazin-1-yl) methyl)piperidin-1-yl)-5-oxo-5,7-dihydro-6H-pyrrolo[3,4-b]pyridin-6-yl)cyclohexyl)oxy)benzonitrile as an off-white solid (45 mg, 0.055 mmol), with a yield of 21%.

LC/MS (ESI$^+$) calcd for $C_{43}H_{44}ClFN_8O_6$ $[M+H]^+$ m/z, 823.3; found, 823.2.

$^1$H NMR (400 MHz, $CDCl_3$) δ 8.28 (s, 1H), 7.84 (d, J=8.8 Hz, 1H), 7.56 (d, J=8.7 Hz, 1H), 7.46 (d, J=11.0 Hz, 1H), 7.40 (d, J=7.3 Hz, 1H), 7.01 (d, J=2.3 Hz, 1H), 6.86 (dd, J=8.7, 2.3 Hz, 1H), 6.66 (d, J=8.8 Hz, 1H), 4.94 (dd, J=12.2, 5.3 Hz, 1H), 4.30 (d, J=4.4 Hz, 2H), 4.21 (s, 2H), 3.74 (s, 3H), 3.67 (d, J=12.2 Hz, 2H), 2.94-2.75 (m, 5H), 2.61 (s, 4H), 2.36 (s, 2H), 2.24 (s, 2H), 2.18-2.10 (m, 1H), 2.05-1.94 (m, 4H), 1.70 (dd, J=16.5, 8.1 Hz, 5H), 1.54-1.36 (m, 3H).

3. 2-chloro-4-((1r,3r)-3-(2-(4-((4-(2,6-dioxopiperidin-3-yl)-6-fluoro-3-oxoisoindolin-5-yl)piperazin-1-yl)methyl)piperidin-1-yl)-5-oxo-5,7-dihydro-6H-pyrrolo[3,4-b]pyridin-6-yl)-2,2,4,4-tetramethylcyclobutoxy)benzonitrile (211)

2-Chloro-4-((1r,4r)-4-(2-(4-((4-(2,6-dioxopiperidin-3-yl)-6-fluoro-1,3-dioxoisoindolin-5-yl)piperazin-1-yl) methyl)piperidin-1-yl)-5-oxo-5,7-dihydro-6H-pyrrolo[3,4-b]pyridin-6-yl)cyclohexyl)oxy)benzonitrile (57 mg, 0.070 mmol) was dissolved in 1 mL of HOAc, to which was added Zn powder (92 mg, 1.41 mmol), and the mixture was stirred and reacted overnight at 60° C. TLC indicated the completion of the reaction, and the reaction solution was filtered. The filter cake was rinsed with DCM. The filtrate was rotatory evaporated to dry to obtain the crude product, to which were added 2 mL DCM and triethylsilane (33 mg, 0.28 mmol), and then 1 mL of TFA was added. The reaction was stirred and reacted overnight at room temperature. The end point of the reaction was determined by TLC. The solvent was evaporated under reduced pressure. To the residue, was added the saturated aqueous solution of sodium bicarbonate. The resultant solution was extracted with dichloromethane three times. The organic phase was combined, dried, rotatory evaporated to dry, and separated by pre-TLC (EA:MeOH 20:1), to provide the off-white solid compound 2-chloro-4-((1r,3r)-3-(2-(4-((4-(2,6-dioxopiperidin-3-yl)-6-fluoro-3-oxoisoindolin-5-yl) piperazin-1-yl) methyl)piperidin-1-yl)-5-oxo-5,7-dihydro-6H-pyrrolo[3,4-b]pyridin-6-yl)-2,2,4,4-tetramethylcyclobutoxy) benzonitrile (17 mg, 0.021 mmol) as the upper spot, with a yield of 47%.

LC/MS ($ESI^+$) calcd for $C_{43}H_{46}ClFN_8O_5$ $[M+H]^+$ m/z, 809.3; found, 809.2.

$^1H$ NMR (400 MHz, $CDCl_3$) δ 8.01 (s, 1H), 7.86 (d, J=8.5 Hz, 1H), 7.56 (d, J=8.7 Hz, 1H), 7.48 (d, J=7.7 Hz, 1H), 7.12 (t, J=9.9 Hz, 1H), 7.00 (t, J=4.4 Hz, 1H), 6.86 (dd, J=8.7, 2.3 Hz, 1H), 6.67 (d, J=8.5 Hz, 1H), 5.19 (dd, J=13.2, 5.1 Hz, 1H), 4.34 (dd, J=54.6, 15.8 Hz, 4H), 4.21 (s, 2H), 3.73 (s, 3H), 3.49 (s, 2H), 2.99-2.83 (m, 2H), 2.80-2.70 (m, 2H), 2.59 (s, 3H), 2.35 (dt, J=13.0, 8.2 Hz, 2H), 2.30-2.19 (m, 3H), 2.02 (s, 4H), 1.77-1.57 (m, 7H).

212: The Off-White Solid Compound 2-chloro-4-((1r,3r)-3-(2-(4-((4-(2,6-dioxopiperidin-3-yl)-6-fluoro-1-oxoisoindolin-5-yl)piperazin-1-yl)methyl) piperidin-1-yl)-5-oxo-5,7-dihydro-6H-pyrrolo[3,4-b] pyridin-6-yl)-2,2,4,4-tetramethylcyclobutoxy) benzonitrile (5 mg, 0.006 mmol) as the lower spot, with a yield of 14%

LC/MS ($ESI^+$) calcd for $C_{43}H_{46}ClFN_8O_5$ $[M+H]^+$ m/z, 809.3; found, 809.2.

213: Synthesis of N-((1r,3r)-3-(3-chloro-4-cyano-phenoxy)-2,2,4,4-tetramethylcyclobutyl)-6-(4-(2-(2,6-dioxopiperidin-3-yl)-6-fluoro-1-oxoisoindolin-5-yl)piperazin-1-yl)methyl)piperidin-1-yl)nicotinamide 214: Synthesis of N-((1r,3r)-3-(3-chloro-4-cyano-phenoxy)-2,2,4,4-tetramethylcyclobutyl)-6-(4-(2-(2,6-dioxopiperidin-3-yl)-6-fluoro-3-oxoisoindolin-5-yl)piperazin-1-yl)methyl)piperidin-1-yl)nicotinamide

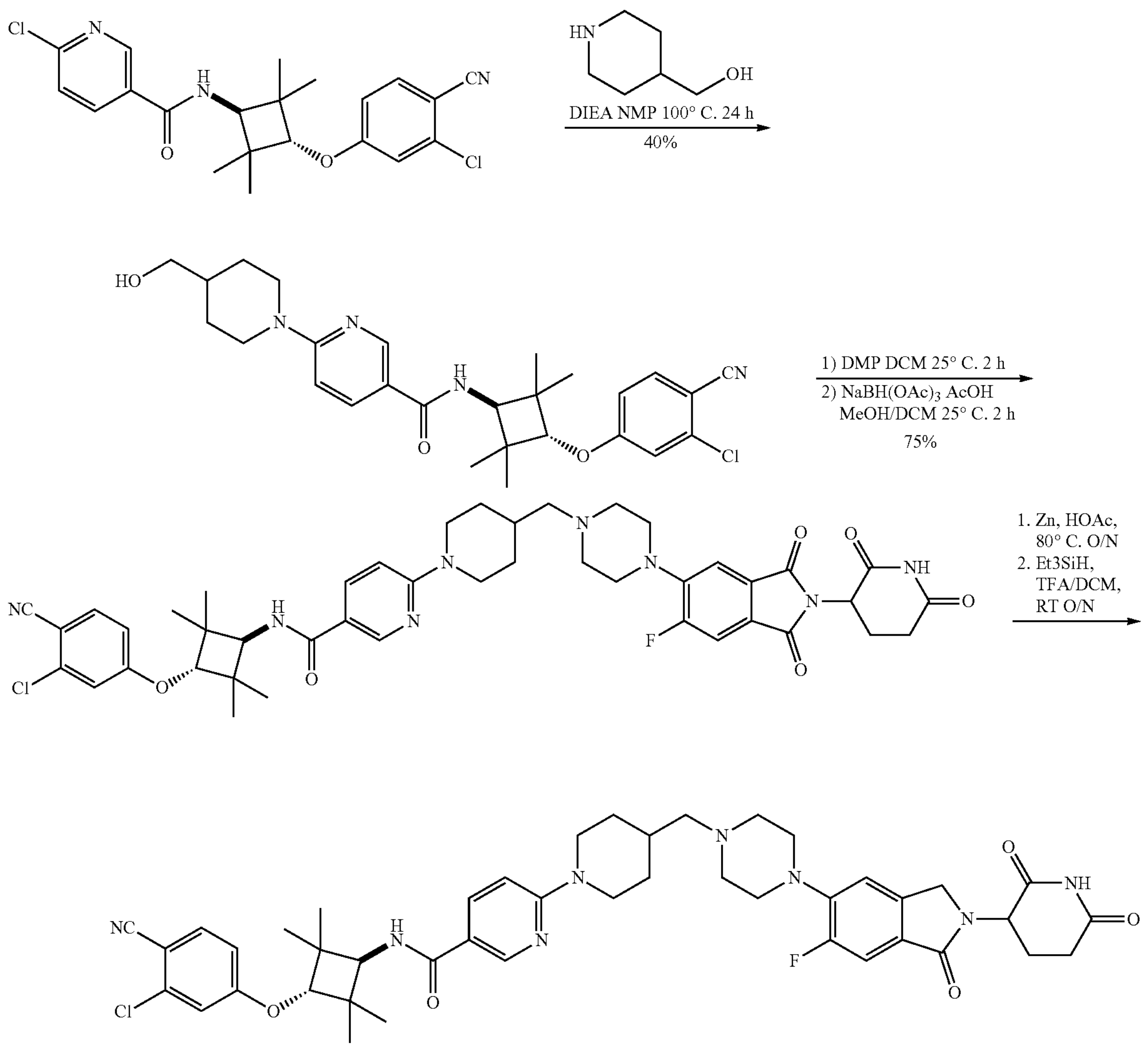

213

-continued

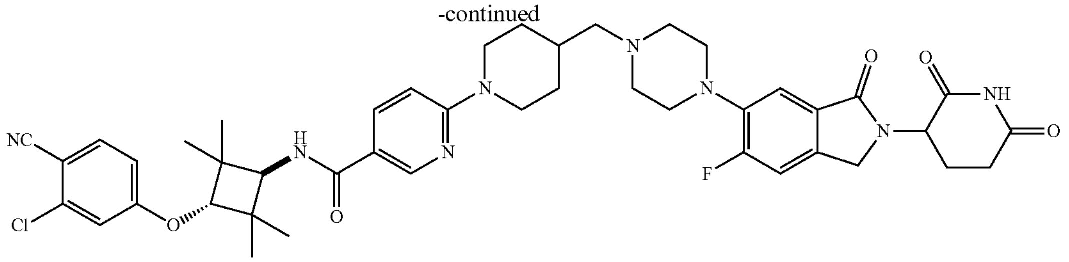

55% 214

213: LC/MS (ESI+) calcd for $C_{44}H_{50}ClFN_8O_5[M+H]^+$ m/z, 825.4; found, 825.3.

$^1H$ NMR (400 MHz, $CDCl_3$) δ 9.30 (s, 1H), 8.55 (d, J=2.2 Hz, 1H), 7.90 (dd, J=9.0, 2.4 Hz, 1H), 7.58 (d, J=8.7 Hz, 1H), 7.49 (d, J=7.9 Hz, 1H), 7.16 (d, J=11.2 Hz, 1H), 6.98 (d, J=2.3 Hz, 1H), 6.82 (dd, J=8.7, 2.3 Hz, 1H), 6.69 (d, J=9.1 Hz, 1H), 6.23 (d, J=8.3 Hz, 1H), 5.16 (dd, J=13.3, 5.2 Hz, 1H), 4.42 (d, J=16.0 Hz, 3H), 4.29 (d, J=16.1 Hz, 1H), 4.14 (d, J=8.2 Hz, 1H), 4.06 (s, 1H), 3.19 (s, 3H), 2.96 (t, J=12.2 Hz, 3H), 2.86 (dd, J=12.7, 5.2 Hz, 2H), 2.71 (s, 4H), 2.35 (s, 4H), 2.22-2.15 (m, 1H), 1.93 (d, J=11.9 Hz, 3H), 1.26 (s, 6H), 1.22 (s, 6H).

214: LC/MS (ESI+) calcd for $C_{44}H_{50}ClFN_8O_5$ $[M+H]^+$ m/z, 825.4; found, 825.3

$^1H$ NMR (400 MHz, $CDCl_3$) δ 8.55 (d, J=2.2 Hz, 1H), 7.90 (dd, J=9.0, 2.4 Hz, 1H), 7.58 (d, J=8.7 Hz, 1H), 7.50 (d, J=11.3 Hz, 1H), 7.01-6.94 (m, 2H), 6.81 (dd, J=8.7, 2.4 Hz, 1H), 6.69 (d, J=9.1 Hz, 1H), 6.19 (d, J=8.2 Hz, 1H), 5.16 (dd, J=13.3, 5.1 Hz, 1H), 4.47-4.37 (m, 3H), 4.28 (d, J=16.0 Hz, 1H), 4.14 (d, J=8.2 Hz, 1H), 4.06 (s, 1H), 3.21 (s, 4H), 3.04-2.80 (m, 5H), 2.66 (s, 4H), 2.33 (d, J=2.3 Hz, 4H), 1.92 (d, J=11.7 Hz, 4H), 1.26 (s, 6H), 1.21-1.20 (m, 6H).

215: Synthesis of N-((1r,3r)-3-(3-chloro-4-cyanophenoxy)-2,2,4,4-tetramethylcyclobutyl)-6-(4-((4-(2-(2,6-dioxopiperidin-3-yl)-6-fluoro-3-oxoisoindolin-5-yl)piperazin-1-yl)methyl)piperidin-1-yl)-N-(methyl-d3)nicotinamide 216: Synthesis of N-((1r,3r)-3-(3-chloro-4-cyanophenoxy)-2,2,4,4-tetramethylcyclobutyl)-6-(4-((4-(2-(2,6-dioxopiperidin-3-yl)-6-fluoro-1-oxoisoindolin-5-yl)piperazin-1-yl)methyl)piperidin-1-yl)-N-(methyl-d3)nicotinamide

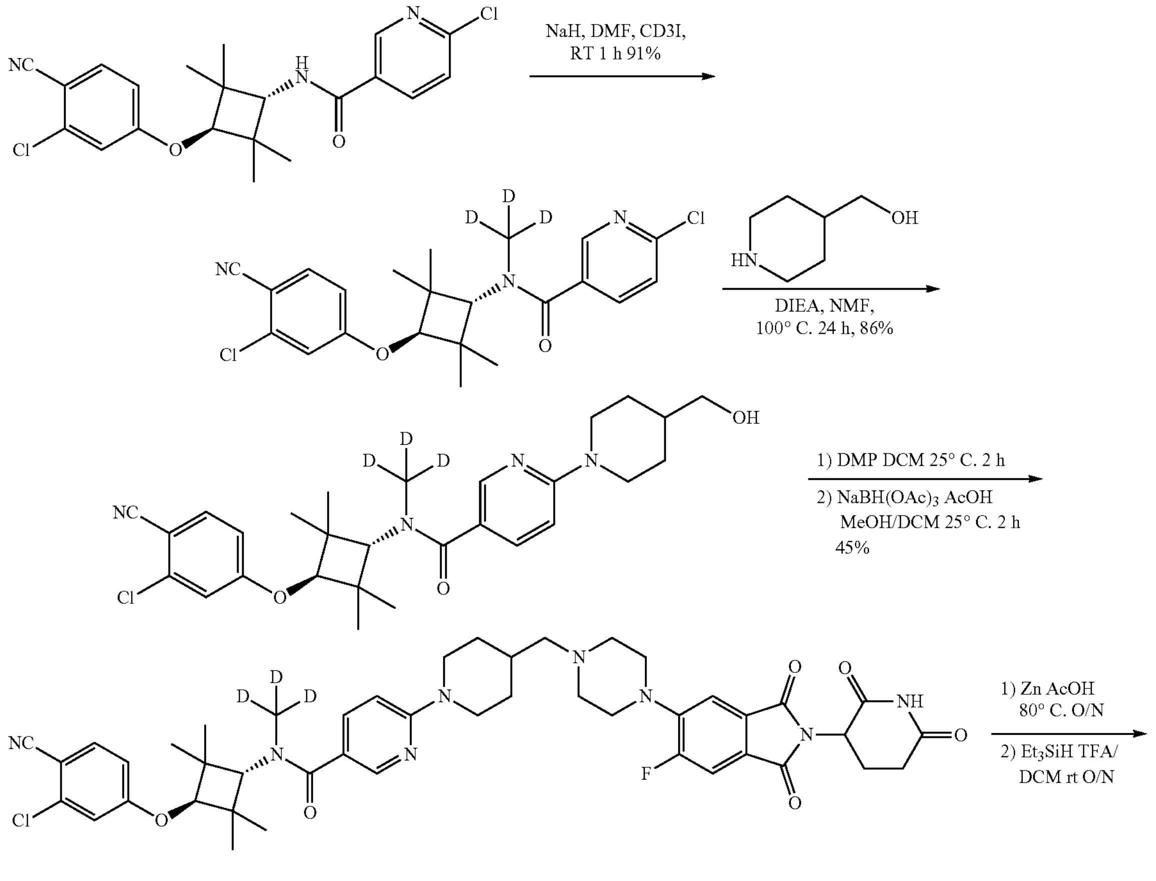

-continued

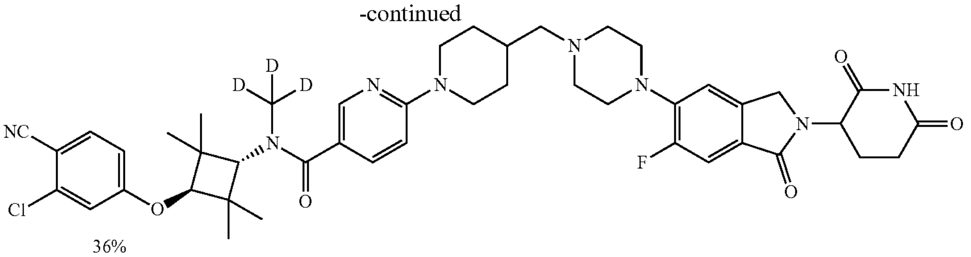

36%

216

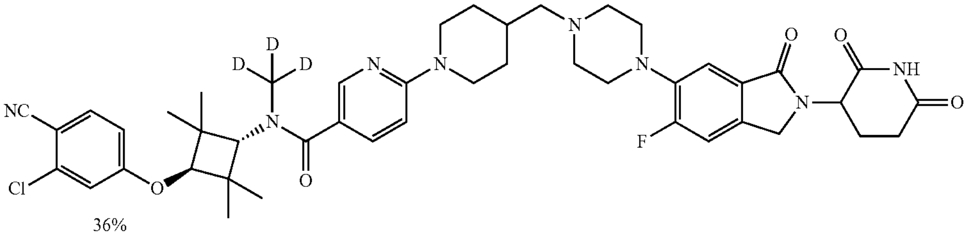

36%

215

215: LC/MS ($ESI^+$) calcd for $C_{45}H_{49}D_3ClFN_8O_5[M+H]^+$ m/z, 842.4; found, 842.3.

$^1H$ NMR (400 MHz, $CDCl_3$) δ 8.28 (s, 1H), 8.06 (s, 1H), 7.57 (d, J=8.6 Hz, 1H), 7.49 (d, J=8.7 Hz, 1H), 7.41 (d, J=7.8 Hz, 1H), 7.07 (d, J=11.1 Hz, 1H), 6.90 (d, J=2.3 Hz, 1H), 6.73 (dd, J=8.7, 2.3 Hz, 1H), 6.58 (d, J=9.0 Hz, 1H), 5.12 (dd, J=13.3, 5.1 Hz, 1H), 4.35 (d, J=15.8 Hz, 3H), 4.21 (d, J=15.9 Hz, 1H), 4.06 (s, 1H), 3.84 (s, 1H), 3.12 (s, 4H), 2.81 (ddd, J=25.5, 20.8, 12.0 Hz, 4H), 2.70-2.46 (m, 3H), 2.28 (ddd, J=25.8, 12.7, 4.9 Hz, 2H), 2.15 (dd, J=10.2, 5.2 Hz, 1H), 1.91 (d, J=37.5 Hz, 3H), 1.66 (d, J=6.5 Hz, 3H), 1.34 (s, 6H), 1.19 (s, 6H).

216: LC/MS ($ESI^+$) calcd for $C_{45}H_{49}D_3ClFN_8O_5$ $[M+H]^+$ m/z, 842.4; found, 842.3

$^1H$ NMR (400 MHz, $CDCl_3$) δ 8.28 (s, 1H), 8.12 (s, 1H), 7.57 (d, J=7.4 Hz, 1H), 7.49 (d, J=8.7 Hz, 1H), 7.43 (d, J=11.3 Hz, 1H), 6.90 (d, J=6.9 Hz, 2H), 6.73 (dd, J=8.7, 2.1 Hz, 1H), 6.58 (d, J=8.9 Hz, 1H), 5.11 (dd, J=13.2, 5.0 Hz, 1H), 4.34 (d, J=15.3 Hz, 3H), 4.19 (d, J=15.9 Hz, 1H), 4.06 (s, 1H), 3.84 (s, 1H), 3.18 (s, 4H), 2.92-2.74 (m, 4H), 2.63 (s, 3H), 2.27 (dd, J=13.0, 4.9 Hz, 3H), 2.19-2.09 (m, 1H), 1.86 (d, J=11.5 Hz, 3H), 1.67 (s, 6H), 1.34 (s, 6H), 1.18 (s, 6H).

217: Synthesis of 2-chloro-4-((1r,4r)-4-(2-(4-((4-(2,6-dioxopiperidin-3-yl)-1,3-dioxoisoindolin-4-yl)piperazin-1-yl)methyl)piperidin-1-yl)-5-oxo-5,7-dihydro-6H-pyrrolo[3,4-b]pyridin-6-yl)cyclohexyl)oxy)benzonitrile

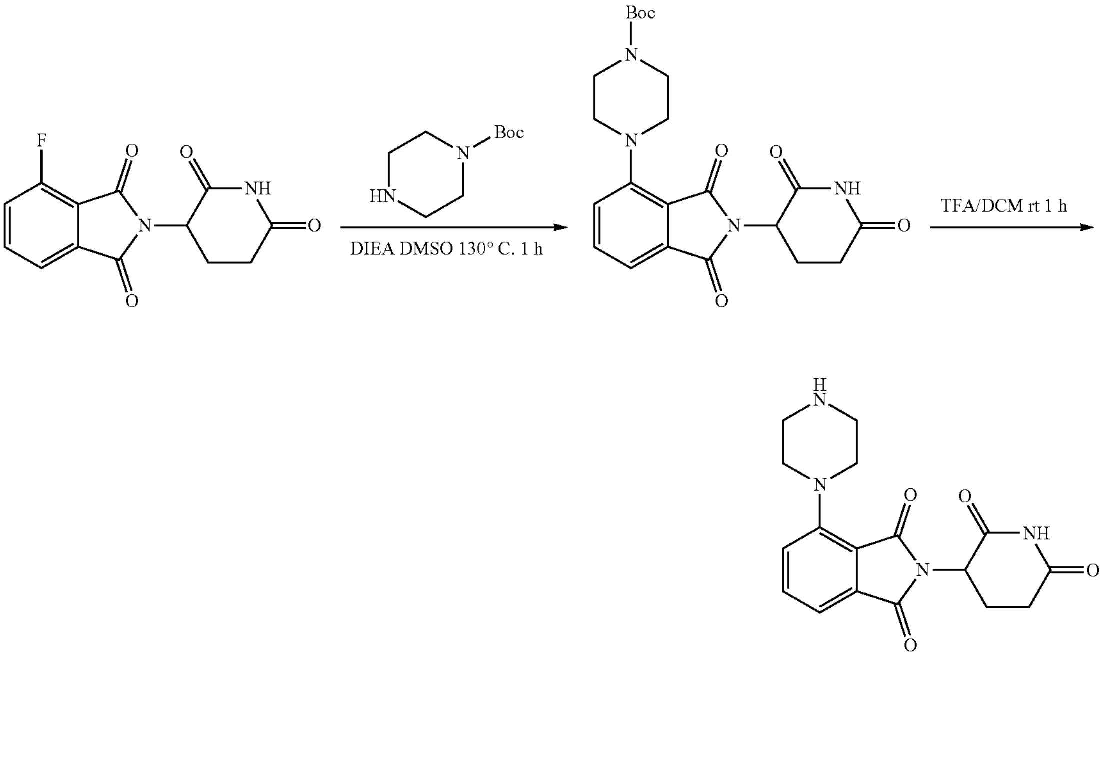

-continued

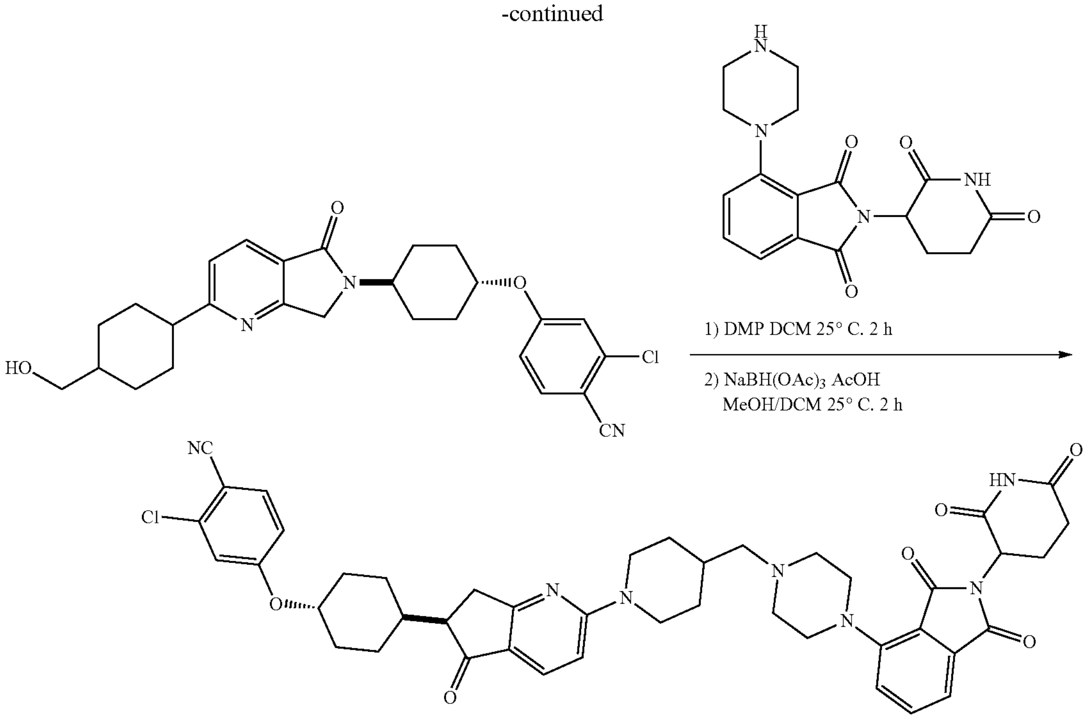

217

1. Synthesis of Compound t-butyl 4-(2,6-dioxopiperidin-3-yl)-1,3-dioxoisoindol-4-yl)piperazine-1-carboxylate Compound 2-(2,6-dioxo-piperidin-3-yl)-4-fluoro-isoindole-1,3-dione (500 mg, 1.81 mmol), 1-t-butoxycarbonylpiperazine (404 mg, 2.17 mmol), DIEA (702 mg, 5.43 mmol) and 10 mL of DMSO were sequentially added to a reactor, and under nitrogen protection, the mixture was allowed to react 1 h under stirring at 130° C. TLC confirmed that the reaction was completed. The reaction solution was added with water, and extracted three times with ethyl acetate. The organic phase was washed three times with saturated brine, dried over anhydrous sodium sulfate, and rotatory evaporated to dry to obtain the crude product, which was separated by silica gel column chromatography, to provide compound t-butyl 4-(2,6-dioxopiperidin-3-yl)-1,3-dioxoisoindol-4-yl) piperazine-1-carboxylate as a yellow solid (780 mg, 1.76 mmol), with a yield of 97%.

LC/MS (ESI$^+$) calcd for $C_{22}H_{26}N_4O_6$ [M+H]$^+$ m/z, 443.2; found, 443.2.

2. Synthesis of Compound 2-(2,6-dioxopiperidin-3-yl)-4-(piperazin-1-yl)isoindole-1,3-dione Compound t-butyl 4-(2,6-dioxopiperidin-3-yl)-1,3-dioxoisoindol-4-yl)piperazine-1-carboxylate (110 mg, 0.25 mmol) was dissolved in 1 mL DCM, to which was added 1 mL of TFA, and the reaction solution was stirred and reacted 1 h at room temperature. The reaction was completed by TLC detection, and the reaction solution was evaporated to remove the solvent, to which was added the saturated aqueous solution of sodium bicarbonate. The resultant solution was extracted three times with DCM, dried over anhydrous sodium sulfate, and rotatory evaporated to dry, to provide compound 2-(2,6-dioxopiperidin-3-yl)-4-(piperazin-1-yl)isoindole-1,3-dione as a yellow solid (76 mg, 0.22 mmol), with a yield of 89%. LC/MS (ESI$^+$) calcd for $C_{17}H_{18}N_4O_4$[M+H]$^+$ m/z, 343.1; found, 343.1.

3. Synthesis of Compound 2-chloro-4-((1r,4r)-4-(2-(4-((4-(2,6-dioxopiperidin-3-yl)-1,3-dioxoisoindol-4-yl)piperazin-1-yl)methyl)piperidin-1-yl)-5-oxo-5,7-dihydro-6H-pyrrolo[3,4-b]pyridin-6-yl)cyclohexyl)oxy)benzonitrile Compound 2-chloro-4-((1r,4r)-4-(2-(4-(hydroxymethyl)piperidin-1-yl)-5-oxo-5,7-dihydro-6H-pyrrolo[3,4-b]pyridin-6-yl)cyclohexyl)oxy)benzonitrile (70 mg, 0.14 mmol) was dissolved in 2 mL of DCM, to which was added DMP (74 mg, 0.17 mmol), and the reaction was stirred and reacted 2 h at room temperature. TLC indicated the completion of the reaction. The reaction solution was filtered, and the filter cake was rinsed with DCM. The filtrate was rotatory evaporated to dry to obtain the crude product, to which was added 2-(2.6-dioxopiperidin-3-yl)-4-(piperazin-1-yl)isoindole-1,3-dione (50 mg, 0.14 mmol) and 2 mL DCM/MeOH (1:1) and dissolved, and then glacial acetic acid (17 mg, 0.29 mmol) was added. The reaction solution was stirred and reacted at room temperature for 30 min, to which was then added sodium triacetylborohydride (123 mg, 0.58 mmol). The resultant solution was stirred at room temperature for 2 h. The end point of the reaction was determined by TLC, and then the saturated aqueous solution of sodium bicarbonate was added. The reaction solution was extracted three times with dichloromethane, dried, rotatory evaporated to dry, and separated by pre-TLC, to provide compound 2-chloro-4-((1r,4r)-4-(2-(4-((4-(2,6-dioxopiperidin-3-yl)-1,3-dioxoisoindol-4-yl)piperazin-1-yl)methyl)piperidin-1-yl)-5-oxo-5,7-dihydro-6H-pyrrolo[3,4-b]pyridin-6-yl)cyclohexyl)oxy)

benzonitrile as an off-white solid (55 mg, 0.068 mmol), with a yield of 47%. LC/MS (ESI+) calcd for $C_{43}H_{45}ClN_8O_6$ $[M+H]^+$ m/z, 805.3; found, 805.3.

$^1$H NMR (400 MHz, $CDCl_3$) δ 7.74 (dd, J=8.8, 5.0 Hz, 1H), 7.63-7.49 (m, 2H), 7.37 (s, 1H), 7.28-7.21 (m, 1H), 7.17 (d, J=5.4 Hz, 1H), 7.02-6.93 (m, 1H), 6.83 (dd, J=7.4, 4.8 Hz, 1H), 6.64 (dd, J=8.8, 5.6 Hz, 1H), 4.91 (s, 1H), 4.73 (s, 1H), 4.45-4.03 (m, 5H), 3.67 (s, 6H), 3.33 (d, J=25.4 Hz, 4H), 2.92 (t, J=12.7 Hz, 2H), 2.74 (dd, J=38.7, 12.5 Hz, 6H), 2.31 (s, 1H), 2.20 (s, 2H), 2.05 (s, 1H), 1.99-1.74 (m, 5H), 1.64 (s, 2H), 1.19 (s, 2H).

218: 2-chloro-4-((3aR,5r,6aR)-2-(6-(4-((4-(2,6-dioxopiperidin-3-yl)-1,3-dioxoisoindolin-5-yl)piperazin-1-yl)methyl)piperidin-1-yl)pyridazine-3-carbonyl) octylcyclopenta[c]pyrrol-5-yl)oxy)benzonitrile

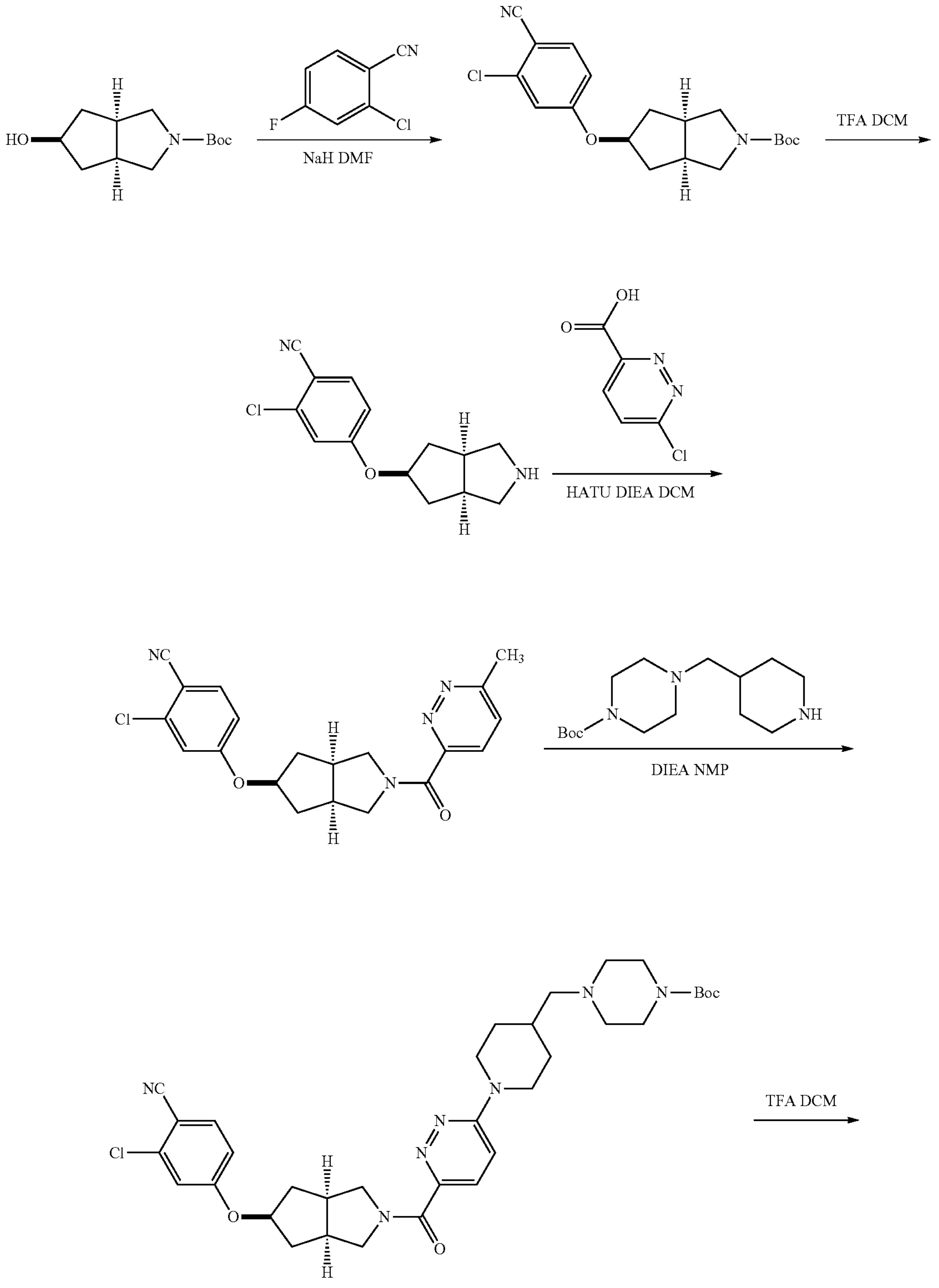

-continued

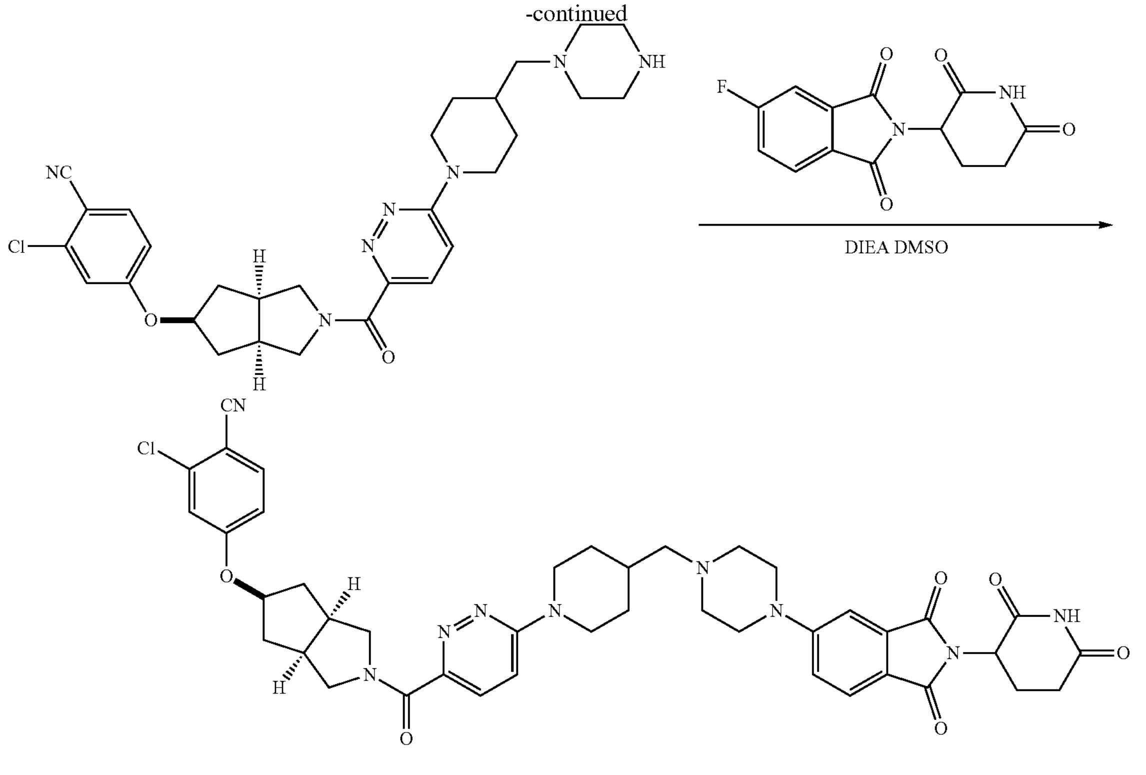

218

1. Compound t-butyl (3aR,5r,6aS)-5-(3-chloro-4-cyanophenoxy) hexahydrocyclopenta[c]pyrrole-2(1H)-carboxylate Compound t-butyl (3aR,5r,6aS)-5-hydroxylhexahydrocyclopenta[c]pyrrole-2(1H)-carboxylate (500.0 mg, 2.20 mmol) was dissolved in 2 mL of DMF, to which was added NaH (106.0 mg, 2.6 mmol) in an ice bath, and then the temperature was maintained, and the mixture was allowed to react 30 min. 2-Chloro-4-fluorobenzonitrile (342.0 mg, 2.2 mmol) was dissolved in 2 mL DMF, which was slowly added dropwise to the reaction solution, and then the mixture was reacted at room temperature for 2 h. The reaction solution was added with water and ethyl acetate for extraction. The organic layer was further washed twice with saturated brine, and then dried over anhydrous sodium sulfate, rotatory evaporated to dry, and purified by silica gel column chromatography to obtain compound t-butyl (3aR,5r,6aS)-5-(3-chloro-4-cyanophenoxy)hexahydrocyclopenta[c]pyrrole-2(1H)-carboxylate as a white solid (550.0 mg, 1.52 mmol), with a yield of 69%.

LC/MS ($ESI^+$) calcd for $C_{19}H_{22}ClN_2O_3$ ($M-56+H^+$) m/z, 307.1; found, 307.1.

2. Synthesis of Compound 2-chloro-4-((3aR,5r,6aS)-octahydrocyclopenta[c]pyrrol-5-yl)oxy)benzonitrile trifluoroacetate Compound t-butyl (3aR,5r,6aS)-5-(3-chloro-4-cyanophenoxy)hexahydrocyclopenta [c]pyrrole-2(1H)-carboxylate (520 mg, 1.40 mmol) was dissolved in 2 mL DCM and 2 mL TFA, and the solution was stirred and reacted at room temperature for 1 h. The reaction was completed by TLC detection, and the solvent was evaporated under reduced pressure, to provide the crude compound 2-chloro-4-((3aR,5r,6aS)-octahydrocyclopenta[c]pyrrol-5-yl)oxy)benzonitrile trifluoroacetate (538 mg, 1.40 mmol) (which was directly used in the next reaction), with a yield of 100%.

LC/MS ($ESI^+$) calcd for $C_{14}H_{14}ClN_2O$ $[M+H]^+$ m/z, 263.1; found, 263.1.

3. Compound 2-chloro-4-((((3Ar,5R,6aS)-2-(6-chloropyridazine-3-carbonyl) hexahydrocyclopenta[c]pyrrole-5-yl)oxy)benzonitrile Compound 6-chloropyridazine-3-carboxylic acid (159 mg, 1.0 mmol) and HATU (400 mg, 1.10 mmol) were added in 5 mL of DCM, to which was then added DIEA (388.8 mg, 3.10 mmol) in an ice-water bath, followed by addition of 2-chloro-4-((3aR,5r,6aS)-octahydrocyclopenta[c]pyrrol-5-yl)oxy)benzonitrile trifluoroacetate (300.0 mg, 1.0 mmol). The mixture was stirred 2 h at room temperature. The reaction solution was added with DCM and water for extraction, dried over anhydrous sodium sulfate, rotatory evaporated to dry, and purified by silica gel column chromatography to obtain compound 2-chloro-4-((((3Ar,5R,6aS)-2-(6-chloropyridazine-3-carbonyl) hexahydrocyclopenta[c]pyrrole-5-yl)oxy)benzonitrile as a pale yellow oil (226 mg, 0.60 mmol), with a yield of 56%.

LC/MS ($ESI^+$) calcd for $C_{19}H_{16}C_{12}N_4O_2^+$ $[M+H]^+$ m/z, 402.1; found, 402.1.

4. Synthesis of Compound t-butyl 4-((1-(6-((3aR,5r,6aS)-5-(3-chloro-4-cyanophenoxy)hexahydrocyclopenta[c]pyrrole-2-carbonyl)pyridazine-3-yl)piperidine-4-yl)methyl)piperazine-1-carboxylate Compounds 2-chloro-4-((((3Ar,5R,6aS)-2-(6-chloropyridazine-3-carbonyl)hexahydrocyclopenta[c]pyrrole-5-yl)oxy)benzonitrile (220 mg, 0.50 mmol) and t-butyl 4-(piperidin-4-ylmethyl)piperazine-1-carboxylate (186 mg, 0.60 mmol) were sequentially added, followed by addition of 3 mL NMP and DIEA (211.5 mg, 1.6 mmol). Under nitrogen protection, the mixture was allowed to react overnight under stirring at 110° C. The reaction solution was added with water and ethyl acetate for extraction. The organic layer was further washed with saturated brine, dried over anhydrous sodium sulfate, rotatory evaporated to dry, and purified by silica gel column chromatography, to provide compound t-butyl 4-((1-(6-((3aR,5r,6aS)-5-(3-chloro-4-cyanophenoxy) hexahydrocyclopenta[c]pyrrole-2-carbonyl)pyridazine-3-yl)piperidine-4-yl)methyl)piperazine-1-carboxylate as pale yellow oil (207.0 mg, 0.3 mmol), with a yield of 58.3%.

LC/MS (ESI$^+$) calcd for $C_{34}H_{44}ClN_7O_4$(M-56+H$^+$) m/z, 594.3; found, 594.3.

5. Synthesis of Compound 2-chloro-4-((3aR,5r,6aS)-2-(6-(4-(piperazin-1-ylmethyl)piperidin-1-yl) pyridazine-3-carbonyl)hexahydrocyclopenta[c]pyrrole-5-yl)oxy)benzonitrile Compound t-butyl 4-((1-(6-((3aR,5r,6aS)-5-(3-chloro-4-cyanophenoxy) hexahydrocyclopenta[c]pyrrole-2-carbonyl) pyridazine-3-yl)piperidine-4-yl)methyl) piperazine-1-carboxylate (100.0 mg, 0.15 mmol) was dissolved in 2 mL DCM and 2 mL TFA, and the mixture was stirred 2 h at room temperature. The solvent was evaporated to dry, to provide compound 2-chloro-4-((3aR,5r,6aS)-2-(6-(4-(piperazin-1-ylmethyl)piperidin-1-yl)pyridazine-3-carbonyl)hexahydrocyclopenta[c]pyrrole-5-yl)oxy)benzonitrile (102.0 mg, 0.15 mmol), with a yield of 100.0%.

LC/MS (ESI$^+$) calcd for $C_{29}H_{35}ClN_7O_2$[M+H]$^+$ m/z, 550.3; found, 550.3.

6. Synthesis of Compound 2-chloro-4-((3aR,5r,6aR)-2-(6-(4-((4-(2,6-dioxopiperidin-3-yl)-1,3-dioxoisoindolin-5-yl)piperazin-1-yl)methyl)piperidin-1-yl)pyridazine-3-carbonyl)octylcyclopenta[c]pyrrol-5-yl)oxy)benzonitrile 2-Chloro-4-((3aR,5r,6aS)-2-(6-(4-(piperazin-1-ylmethyl) piperidin-1-yl)pyridazine-3-carbonyl)hexahydrocyclopenta [c]pyrrole-5-yl)oxy)benzonitrile (102 mg, 0.15 mmol), 2-(2,6-dioxopiperidin-3-yl)-5-fluoroisoindole-1,3-dione (47 mg, 0.17 mmol) and DIEA (60 mg, 0.46 mmol) were added in 3 mL of DMSO. The reaction solution was heated to 130° C. and stirred overnight. The reaction solution was cooled to room temperature, to which were added water and ethyl acetate for extraction. The organic layer was successively washed with 0.5 N HCl and brine, dried over anhydrous sodium sulfate, rotatory evaporated to dry, and purified by silica gel column chromatography, to provide compound 2-chloro-4-((3aR,5r,6aR)-2-(6-(4-((4-(2,6-dioxopiperidin-3-yl)-1,3-dioxoisoindolin-5-yl)piperazin-1-yl)methyl)piperidin-1-yl)pyridazine-3-carbonyl) octylcyclopenta[c]pyrrol-5-yl)oxy)benzonitrile (56 mg, 0.07 mmol), with a yield of 69.4%.

LC/MS (ESI$^+$) calcd for $C_{42}H_{44}ClN_9O_6$ [M+H]$^+$ m/z, 806.3; found, 806.2.

$^1$H NMR (400 MHz, $CDCl_3$) δ 8.26 (s, 1H), 7.87 (d, J=9.5 Hz, 1H), 7.70 (d, J=8.4 Hz, 1H), 7.52 (d, J=8.7 Hz, 1H), 7.28 (d, J=5.1 Hz, 1H), 7.06 (d, J=8.2 Hz, 1H), 6.96 (d, J=9.6 Hz, 1H), 6.89 (s, 1H), 6.77 (d, J=8.2 Hz, 1H), 4.95 (dd, J=11.8, 4.9 Hz, 1H), 4.86 (s, 1H), 4.52 (d, J=12.2 Hz, 2H), 4.28 (dd, J=12.2, 8.0 Hz, 1H), 4.15 (dd, J=12.3, 3.6 Hz, 1H), 3.91 (dt, J=12.8, 10.8 Hz, 2H), 3.45 (s, 4H), 3.03 (t, J=12.2 Hz, 2H), 2.95-2.70 (m, 5H), 2.61 (s, 3H), 2.43-2.21 (m, 4H), 2.19-2.09 (m, 1H), 1.91 (dd, J=32.7, 13.2 Hz, 5H), 1.73 (s, 3H).

219: N-((1r,4r)-4-(3-chloro-4-cyanophenoxy)cyclohexyl)-4-(4-((1-(2-(2,6-dioxopiperidin-3-yl)-6-fluoro-1,3-dioxoisoindolin-5-yl)piperidine-4-yl) amino) piperidin-1-yl)benzamide

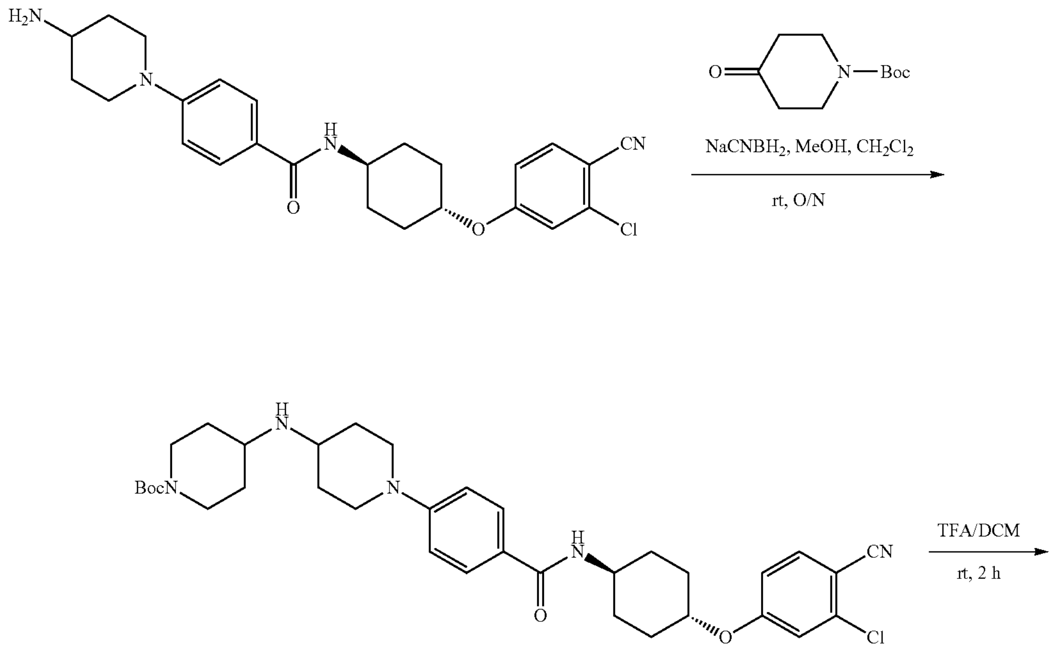

-continued

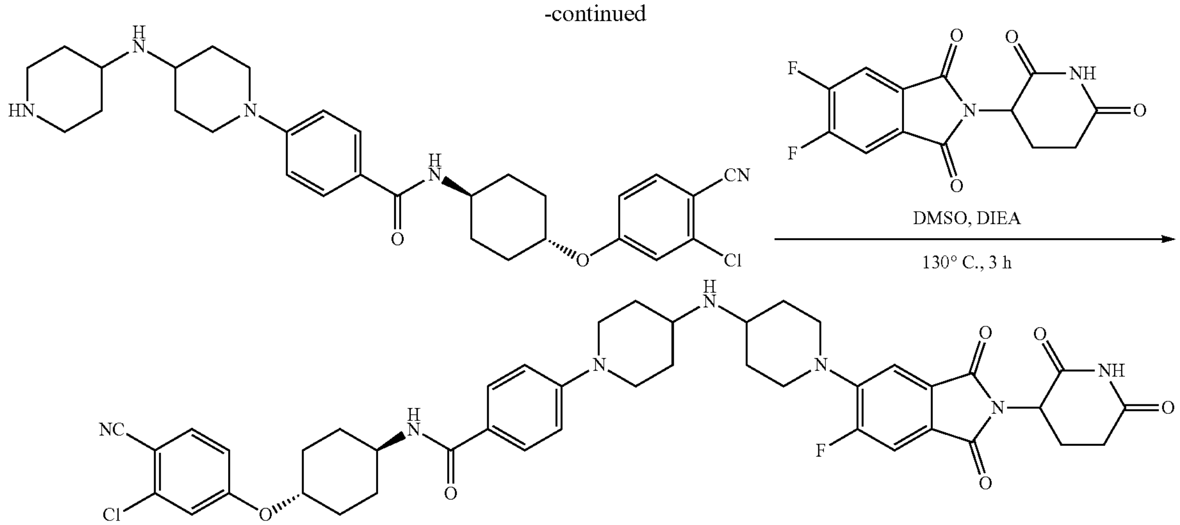

219

LC/MS (ESI+) calcd for $C_{43}H_{45}ClFN_7O_6$ ($[M+H]^+$) m/z: 810.3; found 810.2.

220: Synthesis of N-((1s,4S)-4-(3-chloro-4-cyano-phenoxy)cyclohexyl)-2-((3aR,6aS)-5-(1-(2-(2,6-dioxopiperidin-3-yl)-6-fluoro-1,3-dioxoisoindolin-5-yl)piperidine-4-yl)hexahydropyrrolo[3,4-c]pyrrol-2(1H)-yl)pyrimidine-5-carboxamide

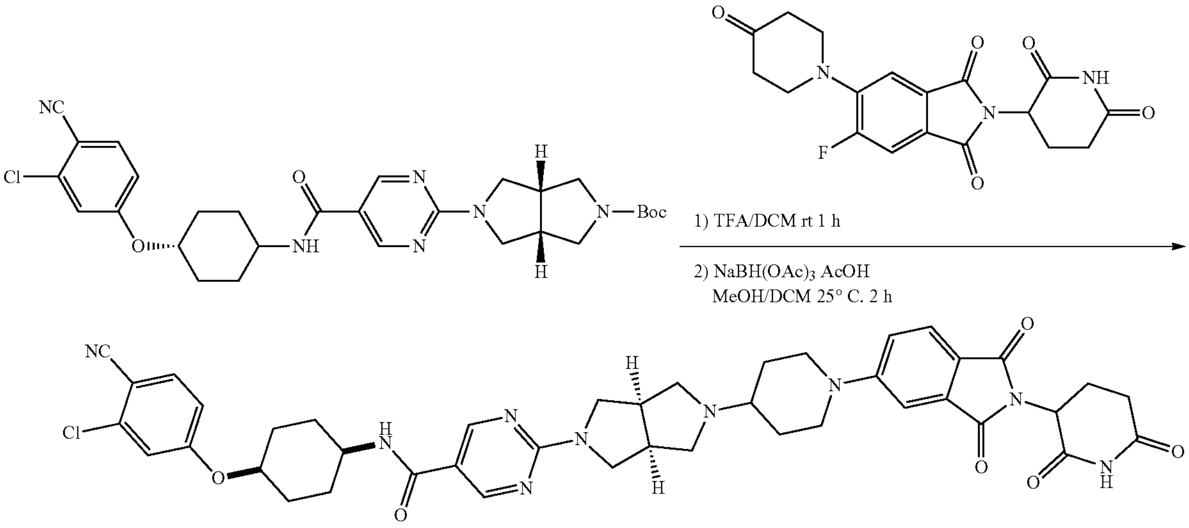

220

Compound t-butyl (3aR,6aS)-5-(5-((s,4S)-4-(3-chloro-4-cyanophenoxy)cyclohexyl) carbamoyl)pyrimidine-2-yl) hexahydropyrrolo[3,4-c]pyrrol-2(1H)-carboxylate (100 mg, 0.18 mmol) was dissolved in 1 mL of DCM, to which was then added 1 mL of TFA, and the mixture was stirred and reacted 1 h at room temperature. TLC indicated the completion of the reaction. The reaction solution was evaporated to remove the solvent, to which was added the saturated aqueous solution of sodium bicarbonate. The resultant solution was extracted three times with DCM, dried over anhydrous sodium sulfate, rotatory evaporated to dry, to obtain the intermediate. The intermediate 2-(2,6-dioxopiperidin-3-yl)-5-fluoro-6-(4-oxopiperidin-1-yl)isoindole-1,3-dione (66 mg, 0.18 mmol) was dissolved in 2 mL DCM/MeOH (1H), to which was added glacial acetic acid (21 mg, 0.35 mmol), and the reaction was stirred at room temperature for 30 min, followed by addition of sodium triacetylborohydride (149 mg, 0.70 mmol). The reaction was stirred and reacted at room temperature for 2 h. The reaction was completed by TLC detection, to which was added the saturated aqueous solution of sodium bicarbonate, and then extracted with dichloromethane three times, dried, and rotatory evaporated to dry, and separated by pre-TLC to obtain compound N-((1s,4S)-4-(3-chloro-4-cyanophenoxy)cyclohexyl)-2-((3aR,6aS)-5-(1-(2-(2,6-dioxopiperidin-3-yl)-6-fluoro-3-dioxoisoindol-5-yl)piperidine-4-yl)hexahydropyrrolo[3,4-c]pyrrol-2(1H)-yl)pyrimidine-5-carboxamide as a yellow solid (19 mg, 0.023 mmol), with a yield of 13%.

LC/MS ($ESI^+$) calcd for $C_{42}H_{43}ClFN_9O_6$ $[M+H]^+$ m/z, 824.3; found, 824.2.

$^1H$ NMR (400 MHz, $CDCl_3$) δ 8.71 (s, 1H), 7.57 (d, J=8.7 Hz, 1H), 7.46 (d, J=10.9 Hz, 1H), 7.38 (d, J=7.3 Hz, 1H), 7.01 (d, J=2.3 Hz, 1H), 6.87 (dd, J=8.8, 2.3 Hz, 1H), 4.93 (dd, J=12.0, 5.4 Hz, 1H), 4.30 (t, J=10.5 Hz, 1H), 3.99 (t, J=11.1 Hz, 1H), 3.83 (s, 1H), 3.66 (d, J=5.2 Hz, 2H), 3.10 (s, 2H), 2.89 (dd, J=19.6, 8.7 Hz, 2H), 2.82-2.72 (m, 1H), 2.67 (s, 1H), 2.14 (dd, J=13.6, 6.2 Hz, 3H), 2.04 (s, 1H), 1.82 (s, 1H), 1.66 (dd, J=22.9, 10.1 Hz, 1H), 1.46 (dd, J=20.5, 9.6 Hz, 1H), 1.29 (s, 1H).

221: Synthesis of N-((1r,3R)-3-(3-chloro-4-cyanophenoxy)-2,2,4,4-tetramethylcyclobutyl)-6-(4-((3aR,6aS)-5-(2-(2,6-dioxopiperidin-3-yl)-6-fluoro-1,3-dioxoisoindolin-5-yl)hexahydropyrrolo[3,4-c]pyrrol-2(1H)-yl)piperidin-1-yl)pyridazine-3-carboxamide hexahydropyrrolo[3,4-c]pyrrol-2(1H)-yl)isoindoline-1,3-dione (24 mg, 0.062 mmol) were sequentially added in a reactor, to which was added 2 mL DCM/MeOH (1:1) to dissolve the reactions, followed by addition of glacial acetic acid (8 mg, 0.12 mmol), and the mixture was stirred and reacted at room temperature for 30 min, followed by addition of sodium triacetylborohydride (53 mg, 0.25 mmol). The reaction was stirred and reacted at room temperature for 2 h. The reaction was completed by TLC detection, to which was added the saturated aqueous solution of sodium bicarbonate, and then extracted with dichloromethane three times, dried, and rotatory evaporated to dry, and separated by pre-TLC to obtain compound N-((1r,3r)-3-(3-chloro-4-cyanophenoxy)-2,2,4,4-tetramethylcyclobutyl)-6-(4-((3aR,6aS)-5-(2-(2,6-dioxopiperidin-3-yl)-6-fluoro-1,3-dioxoisoindolin-5-yl)hexahydropyrrolo[3,4-c]pyrrol-2(1H)-yl)piperidin-1-yl)pyridazine-3-carboxamide as a yellow solid (44 mg, 0.052 mmol), with a yield of 83%.

LC/MS ($ESI^+$) calcd for $C_{44}H_{47}ClFN_9O_6[M+H]^+$ m/z, 852.3; found, 852.3.

$^1H$ NMR (400 MHz, $CDCl_3$) δ 8.30 (s, 1H), 8.15 (d, J=9.1 Hz, 1H), 7.98 (d, J=9.6 Hz, 1H), 7.55 (t, J=10.0 Hz, 1H), 7.40 (t, J=13.2 Hz, 1H), 7.13 (d, J=7.3 Hz, 1H), 7.00 (d, J=9.6 Hz, 1H), 6.97 (d, J=2.4 Hz, 1H), 6.81 (dd, J=8.7, 2.4 Hz, 1H), 4.91 (dd, J=12.2, 5.3 Hz, 1H), 4.91 (dd, J=12.2, 5.3 Hz, 1H), 4.41 (d, J=13.1 Hz, 2H), 4.18 (d, J=9.0 Hz, 1H),

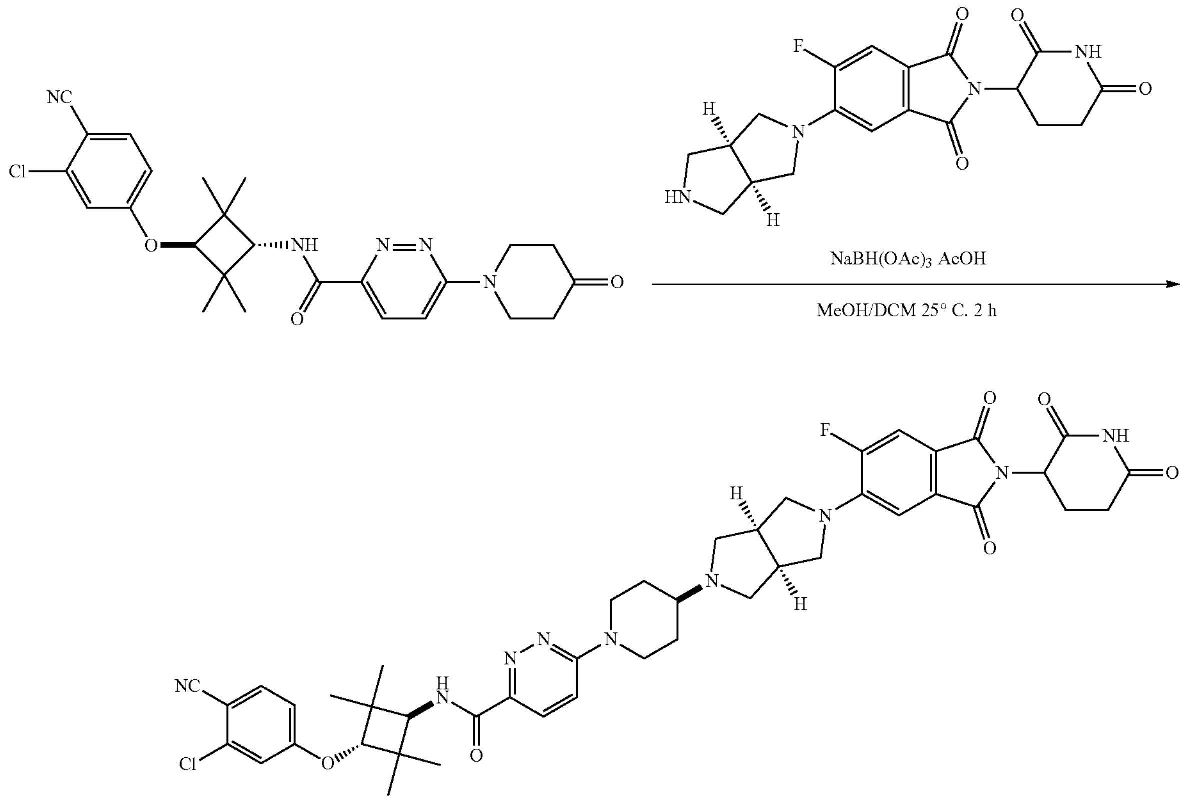

221

Compounds N-((1r,3r)-3-(3-chloro-4-cyanophenoxy)-2,2,4,4-tetramethylcyclobutyl)-6-(4-oxopiperidin-1-yl)pyridazine-3-formamide (30 mg, 0.062 mmol) and 2-(2,6-dioxopiperidin-3-yl)-5-fluoro-6-((3aR,6aS)-

4.07 (s, 1H), 3.65 (d, J=9.8 Hz, 2H), 3.45 (d, J=10.3 Hz, 2H), 3.20 (dd, J=12.6, 9.9 Hz, 2H), 3.03 (s, 4H), 2.93-2.67 (m, 4H), 2.61 (d, J=4.7 Hz, 2H), 2.52 (s, 1H), 1.68 (d, J=10.4 Hz, 2H), 1.31-1.23 (m, 8H), 1.21 (s, 6H).

222: Synthesis of N-((1r,4r)-4-(3-chloro-4-cyanophenoxy)cyclohexyl)-6-((3aR,5R, 6aS)-5-((5-(2-(2,6-dioxopiperidin-3-yl)-6-fluoro-1,3-dioxoisoindolin-5-yl) hexahydropyrrolo[3,4-c]pyrrol-2(1H)-yl) methyl)hexahydrocyclopenta[c]pyrrole-2(1H)-yl) pyridazine-3-formamide 的合成

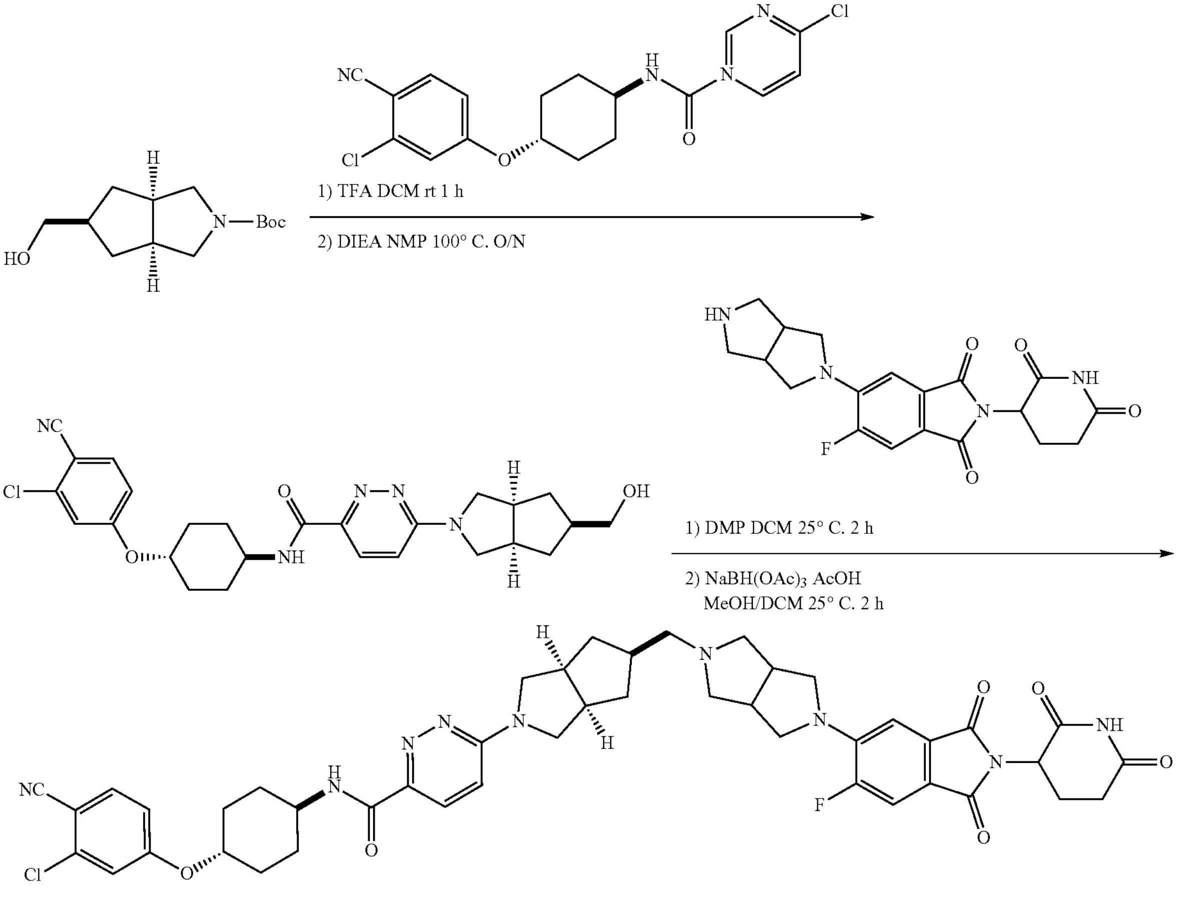

222

1. Synthesis of Compound N-((1r,4r)-4-(3-chloro-4-cyanophenoxy)cyclohexyl)-6-((3aR,5R,6aS)-5-(hydroxymethyl)hexahydrocyclopenta[c]pyrrole-2(1H)-yl) pyridazine-3-formamide Compound t-butyl (3aR,5r,6aS)-5-(hydroxymethyl)hexahydrocyclopenta[c]pyrrole-2(1H)-carboxylate (161 mg, 0.67 mmol) was dissolved in 2 mL of DCM, to which was added 2 mL of TFA, and the mixture was allowed to react under stirring at room temperature for 1 h. TLC indicated the completion of the reaction, and then the reaction solution was evaporated under reduced pressure to remove the solvent. To the residue, was added the saturated aqueous solution of sodium bicarbonate, and then extracted with DCM three times, dried over anhydrous sodium sulfate, and rotatory evaporated to dry, to obtain the crude product, to which were added 6-chloro-N-((1r,4r)-4-(3-chloro-4-cyanophenoxy)cyclohexyl)pyridazine-3-formamide (218 mg, 0.56 mmol), 3 mL DMF and DIPEA (216 mg, 1.67 mmol). Under the nitrogen protection, the solution was stirred and reacted overnight at 110° C. The reaction was completed by TLC detection, to which was added water, and then extracted three times with ethyl acetate, followed by drying over anhydrous sodium sulfate. The organic layer was washed three times with saturated brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-((3aR,5R,6aS)-5-(hydroxymethyl)hexahydrocyclopenta[c]pyrrole-2(1H)-yl)pyridazine-3-formamide as off-white solid (151 mg, 0.30 mmol), with a yield of 55%. LC/MS (ESI$^+$) calcd for $C_{26}H_{30}ClN_5O_3$ $[M+H]^+$ m/z, 496.2; found, 496.2.

2. Synthesis of Compound N-((1r,4r)-4-(3-chloro-4-cyanophenoxy)cyclohexyl)-6-((3aR,5R,6aS)-5-((5-(2-(2,6-dioxopiperidin-3-yl)-6-fluoro-1,3-dioxoisoindolin-5-yl)hexahydropyrrolo[3,4-c]pyrrol-2(1H)-yl) methyl)hexahydrocyclopenta[c]pyrrole-2(1H)-yl) pyridazine-3-formamide Compound N-((1r,4r)-4-(3-chloro-4-cyanophenoxy)cyclohexyl)-6-((3aR,5R,6aS)-5-(hydroxymethyl)hexahydrocyclopenta[c]pyrrole-2(1H)-yl)pyridazine-3-formamide (60 mg, 0.12 mmol) was dissolved in 2 mL of DCM, to which was added DMP (61 mg, 1.4 mmol), and the reaction was stirred and reacted 2 h at room temperature. TLC indicated the completion of the reaction. The reaction solution was filtered, and the filter cake was rinsed with DCM. The filtrate was rotatory evaporated to dry to obtain the crude product, to which was added 2-(2,6-dioxopiperidin-3-yl)-5-fluoro-6-(hexahydropyrrolo[3,4-c]pyrrol-2(1H)-yl)isoindole-1,3-dione (47 mg, 0.12 mmol) and 2 mL DCM/MeOH (1:1) and dissolved, and then glacial acetic acid (14 mg, 0.24 mmol) was added. The reaction solution was stirred and reacted at room temperature for 30 min, to which was then added sodium triacetylborohydride (102 mg, 0.48 mmol). The resultant solution was stirred at room temperature for 2 h. The end point of the reaction was determined by TLC, and then the saturated aqueous solution of sodium bicarbonate was added. The reaction solution was extracted three times with dichloromethane. The organic phase was combined, dried, rotatory evaporated to dry, and separated by pre-TLC, to provide compound N-((1r,4r)-4-(3-chloro-4-cyanophenoxy)cyclohexyl)-6-((3aR,5R, 6aS)-5-((5-(2-(2,6-dioxopiperidin-3-yl)-6-fluoro-1,3-dioxoisoindol-5-yl)hexahydropyrrolo[3,4-c]pyrrol-2(1H)-yl)methyl)hexahydrocyclopenta[c]pyrrole-2(1H)-yl)pyridazine-3-formamide as an off-white solid (41 mg, 0.047 mmol), with a yield of 39%.

LC/MS (ESI$^+$) calcd for $C_45H4_7ClFN_9O_6$ [M+H]$^+$ m/z, 864.3; found, 864.1.

$^1$H NMR (400 MHz, $CDCl_3$) δ 8.32 (s, OH), 7.90 (dd, J=9.4, 2.5 Hz, 1H), 7.84 (d, J=8.2 Hz, OH), 7.49 (d, J=8.7 Hz, 1H), 7.36 (dd, J=12.0, 1.9 Hz, 1H), 7.07 (dd, J=7.3, 3.3 Hz, 1H), 6.93 (d, J=2.3 Hz, OH), 6.79 (dd, J=8.7, 2.4 Hz, OH), 6.63 (dd, J=9.4, 4.0 Hz, OH), 4.85 (dd, J=12.2, 5.4 Hz, OH), 4.25 (t, J=9.8 Hz, OH), 3.98 (d, J=8.1 Hz, OH), 3.69 (d, J=34.5 Hz, 1H), 3.48 (s, 1H), 3.41 (t, J=10.4 Hz, 2H), 3.00 (s, 2H), 2.85-2.64 (m, 2H), 2.47 (s, 1H), 2.30-2.14 (m, 3H), 1.75 (d, J=6.0 Hz, OH), 1.63-1.57 (m, 1H), 1.39 (dd, J=21.6, 9.8 Hz, 1H).

223: Synthesis of N-((1r,4r)-4-(3-chloro-4-cyanophenoxy)cyclohexyl)-6-(3-(5-(2-(2,6-dioxopiperidin-3-yl)-6-fluoro-1,3-dioxoisoindolin-5-yl)hexahydropyrrolo[3,4-c]pyrrol-2(1H)-yl)azitidin-1-yl) pyridazine-3-carboxamide

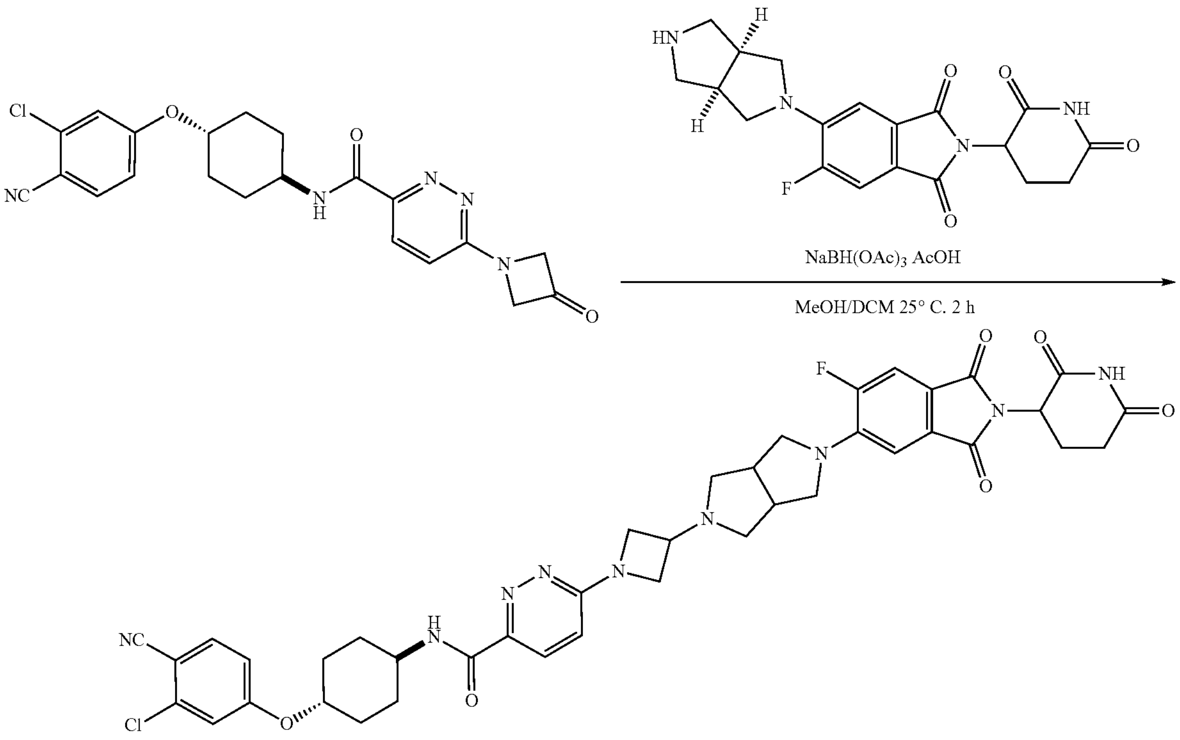

223

Compounds N-((1r,4r)-4-(3-chloro-4-cyanophenoxy)cyclohexyl)-6-(3-oxoazetidin-1-yl)pyridazine-3-formamide (100 mg, 0.23 mmol) and 2-(2,6-dioxopiperidin-3-yl)-5-fluoro-6-((3aR,6aS)-hexahydropyrrolo[3,4-c]pyrrol-2(1H)-yl)isoindoline-1,3-dione (91 mg, 0.23 mmol) were sequentially added in a reactor, to which was added 2 mL of DCM/MeOH (1:1) to dissolve the reactions, followed by addition of glacial acetic acid (28 mg, 0.47 mmol), and the mixture was stirred and reacted at room temperature for 30 min, followed by addition of sodium triacetylborohydride (199 mg, 0.94 mmol). The reaction was stirred and reacted at room temperature for 2 h. The reaction was completed by TLC detection, to which was added the saturated aqueous solution of sodium bicarbonate, and then extracted with dichloromethane three times, dried, rotatory evaporated to dry, and separated by pre-TLC to obtain compound N-((1r, 4r)-4-(3-chloro-4-cyanophenoxy)cyclohexyl)-6-(3-(5-(2-(2, 6-dioxopiperidin-3-yl)-6-fluoro-1,3-dioxoisoindol-5-yl) hexahydropyrrolo[3,4-c]pyrrol-2(1H)-yl)azitidin-1-yl) pyridazine-3-carboxamide as a yellow solid (72 mg, 0.090 mmol), with a yield of 38%. LC/MS (ESI$^+$) calcd for $C_{40}H_{39}ClFN_9O_6$ [M+H]$^+$ m/z, 796.3; found 796.2.

$^1$H NMR (400 MHz, $CDCl_3$) δ 8.54 (s, 1H), 7.90 (d, J=9.2 Hz, 1H), 7.83 (d, J=8.1 Hz, 1H), 7.49 (d, J=8.7 Hz, 1H), 7.34

(d, J=12.1 Hz, 1H), 7.05 (d, J=7.3 Hz, 1H), 6.93 (d, J=2.1 Hz, 1H), 6.78 (dd, J=8.7, 2.1 Hz, 1H), 6.53 (d, J=9.2 Hz, 1H), 4.83 (dd, J=12.0, 5.2 Hz, 1H), 4.31-4.14 (m, 3H), 4.12-4.01 (m, 2H), 3.97 (d, J=8.1 Hz, 1H), 3.69-3.47 (m, 3H), 3.38 (d, J=10.1 Hz, 2H), 2.97 (s, 2H), 2.80 (d, J=15.4 Hz, 3H), 2.74-2.60 (m, 2H), 2.51 (d, J=7.1 Hz, 21-1), 2.21-1.99 (m, 51-H), 1.68-1.53 (m, 21-H), 1.39 (dd, J=22.0, 10.3 Hz, 2H).

224: N-((1r,4r)-4-(3-chloro-4-cyanophenoxy)cyclohexyl)-6-((3aR,5R,6aS)-5-((4-(2-(2,6-dioxopiperidin-3-yl)-6-fluoro-1,3-dioxoisoindolin-5-yl)piperazin-1-yl)methyl)hexahydrocyclopenta[c]pyrrole-2(1H)-yl)pyridazine-3-formamide

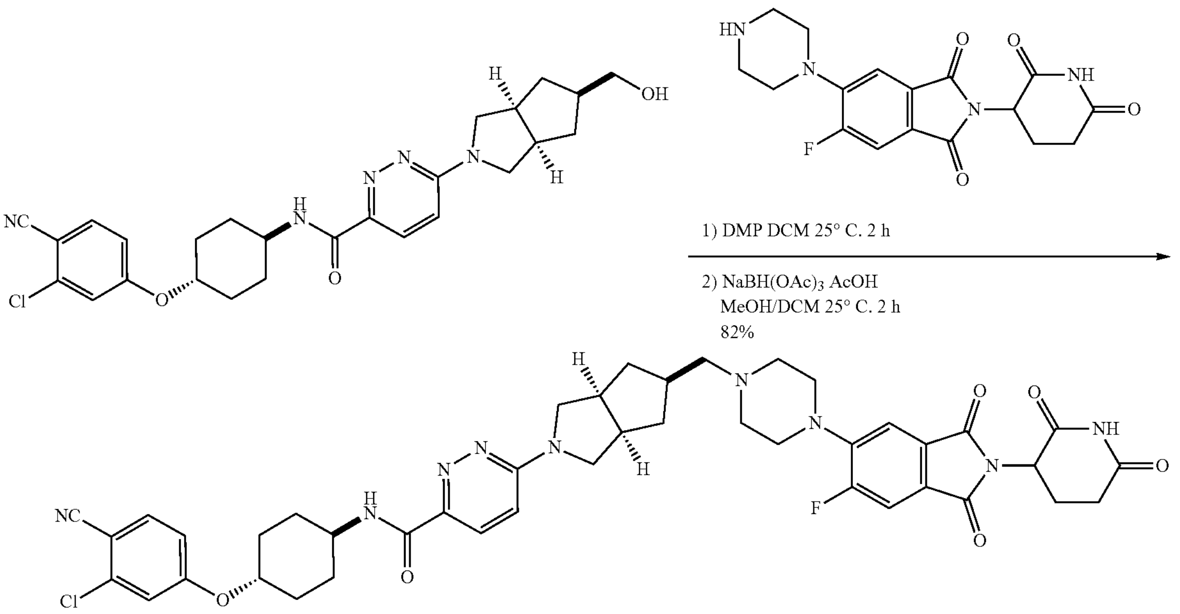

224

LC/MS (ESI$^+$) calcd for $C_{43}H_{45}ClFN_9O_6$ $[M+H]^+$ m/z, 838.3; found 837.7.

$^1$H NMR (400 MHz, $CDCl_3$) δ 8.73 (s, 1H), 7.98 (d, J=9.4 Hz, 1H), 7.93 (d, J=8.2 Hz, 1H), 7.57 (d, J=8.7 Hz, 1H), 7.52-7.44 (m, 1H), 7.41 (dd, J=7.2, 2.5 Hz, 1-H), 7.01 (d, J=2.3 Hz, 1H), 6.86 (dd, J=8.7, 2.3 Hz, 1H), 6.72 (d, J=9.4 Hz, 1H), 4.95 (dd, J=11.8, 5.3 Hz, 1H), 4.33 (t, J=9.9 Hz, 1H), 4.13-4.00 (m, 1H), 3.83 (s, 1H), 3.75 (s, 1H), 3.52 (d, J=9.0 Hz, 1H), 3.43 (d, J=10.0 Hz, 1H), 3.31 (s, 4H), 2.98 (s, 1H), 2.94-2.84 (m, 2H), 2.83-2.58 (m, 6H), 2.48 (d, J=26.8 Hz, 31-H), 2.17 (dd, J=16.7, 8.9 Hz, 6H), 1.84 (d, J=10.5 Hz, 2H), 1.74-1.64 (m, 3H), 1.47 (dd, J=22.6, 10.4 Hz, 21-).

225: Synthesis of N-((1r,4r)-4-(3-chloro-4-cyanophenoxy)cyclohexyl)-5-(3-(5-(2-(2,6-dioxopiperidin-3-yl)-6-fluoro-1,3-dioxoisoindolin-5-yl)hexahydropyrrolo[3,4-c]pyrrol-2(1H)-yl)azitidin-1-yl)pyrazine-2-carboxamide

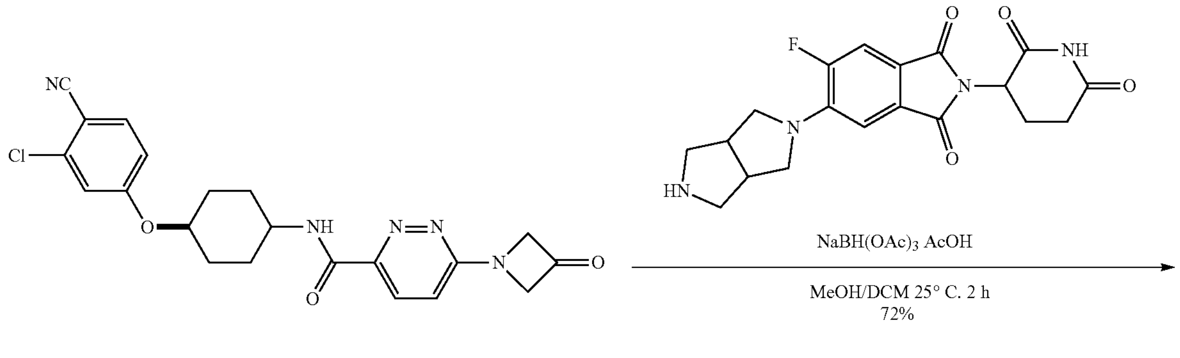

-continued

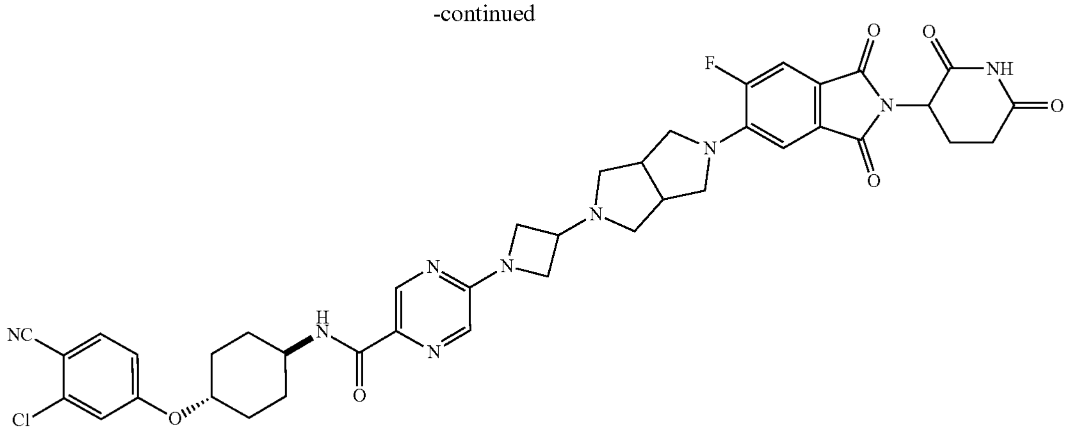

225

LC/MS (ESI$^+$) calcd for $C_{40}H_{39}ClFN_9O_6[M+H]^+$ m/z, 796.3; found, 796.7.

$^1$H NMR (400 MHz, $CDCl_3$) δ 8.83 (s, OH), 8.42 (s, 0H), 7.67-7.52 (m, 1H), 7.42 (t, J=9.2 Hz, 1H), 7.14 (d, J=7.3 Hz, OH), 7.00 (d, J=2.2 Hz, OH), 6.86 (dd, J=8.7, 2.2 Hz, OH), 4.92 (dd, J=12.1, 5.2 Hz, OH), 4.37-4.22 (m, 1H), 4.14 (d, J=4.3 Hz, 1H), 4.03 (d, J=8.0 Hz, OH), 3.77-3.58 (m, 1H), 3.48 (d, J=10.1 Hz, 1H), 3.07 (s, 1H), 2.90 (d, J=12.6 Hz, 1H), 2.77 (dd, J=17.1, 7.5 Hz, 1H), 2.60 (d, J=7.4 Hz, 1H), 2.17 (dd, J=16.2, 11.2 Hz, 2H), 1.72-1.63 (m, 1H), 1.47 (dd, J=22.6, 10.5 Hz, 1H).

226: Synthesis of N-((1r,4r)-4-(3-chloro-4-cyano-phenoxy)cyclohexyl)-6-(4-((3aR,5r,6aS)-2-(2-(2,6-dioxopiperidin-3-yl)-6-fluoro-1,3-dioxoisoindolin-5-yl) octahydrocyclopenta[c]pyrrol-5-yl)methyl) piperazin-1-yl)pyridazine-3-formamide

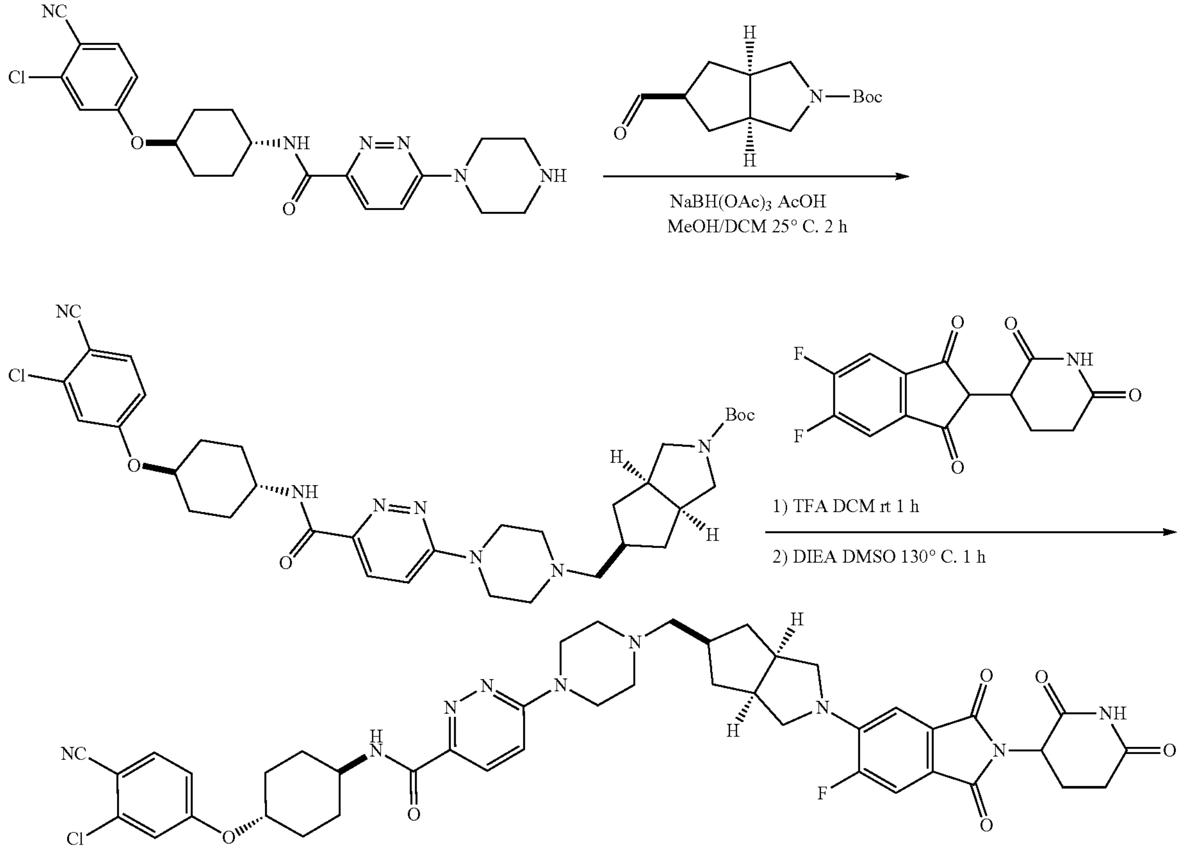

226

1. Synthesis of Compound t-butyl (3aR,5r,6aS)-5-((4-(6-((1r,4r)-4-(3-chloro-4-cyanophenoxy)cyclohexyl)carbamoyl)pyridazine-3-yl)piperazin-1-yl) methyl) hexahydrocyclopenta[c]pyrrole-2(1H)-carboxylate Compounds 2-chloro-4-((1r,4r)-4-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-6H-pyrrolo [3,4-b]pyridin-6-yl)cyclohexyl)oxy)benzonitrile (130 mg, 0.29 mmol), t-butyl N-((1r,4r)-4-(3-chloro-4-cyanophenoxy)cyclohexyl)-6-(piperazin-1-yl)pyridazine-3-formamide,5-formylhexahydrocyclopenta[c]pyrrole-2(1H)2-carboxylate (78 mg, 0.32 mmol) were dissolved in 2 mL of DCM/MeOH (1:1), to which was added glacial acetic acid (35 mg, 0.59 mmol), and the mixture was stirred and reacted at room temperature for 30 min, followed by addition of sodium triacetylborohydride (250 mg, 1.18 mmol). The reaction was stirred and reacted at room temperature for 2 h. The reaction was completed by TLC detection, to which was added the saturated aqueous solution of sodium bicarbonate, and then extracted with dichloromethane three times, dried, rotatory evaporated to dry, and separated by pre-TLC to obtain compound t-butyl (3aR,5r,6aS)-5-((4-(6-((1r,4r)-4-(3-chloro-4-cyanophenoxy)cyclohexyl)carbamoyl) pyridazine-3-yl)piperazin-1-yl)methyl)hexahydrocyclopenta[c]pyrrole-2(1H)-carboxylate as an off-white solid (183 mg, 0.28 mmol), with a yield of 93%. LC/MS (ESI$^+$) calcd for $C_{35}H_{46}ClN_7O_4$[M+H]$^+$ m/z, 664.3; found, 664.3.

2. Synthesis of Compound N-((1r,4r)-4-(3-chloro-4-cyanophenoxy)cyclohexyl)-6-(4-((3aR,5r,6aS)-2-(2-(2,6-dioxopiperidin-3-yl)-6-fluoro-1,3-dioxoisoindolin-5-yl)octahydrocyclopenta[c]pyrrol-5-yl)methyl) piperazin-1-yl)pyridazine-3-formamide Compound t-butyl (3aR,5r,6aS)-5-((4-(6-((1 r,4r)-4-(3-chloro-4-cyanophenoxy) cyclohexyl)carbamoyl)pyridazine-3-yl)piperazin-1-yl)methyl)hexahydrocyclopenta[c] pyrrole-2(1H)-carboxylate (80 mg, 0.12 mmol) was dissolved in 1 mL of DCM, to which was added 1 mL of TFA, and the mixture was allowed to react under stirring at room temperature for 1 h. TLC indicated the completion of the reaction, and then the reaction solution was evaporated under reduced pressure to remove the solvent. To the residue, was added the saturated aqueous solution of sodium bicarbonate, and then extracted with DCM three times, dried over anhydrous sodium sulfate, and rotatory evaporated to dry, to obtain the intermediate as an off-white solid. The intermediate, 2-(2,6-dioxo-piperidin-3-yl)-5,6-difluoroisoindoline-1,3-dione (42 mg, 0.14 mmol), DIEA (78 mg, 0.60 mmol), and 1 mL of DMSO were sequentially added to a reactor. Under the nitrogen protection, the solution was stirred and reacted 1 h at 130° C. The reaction was completed by TLC detection, to which was added water, and then extracted three times with ethyl acetate. The organic layer was washed three times with saturated brine, dried over anhydrous sodium sulfate, rotatory evaporated to dry to obtain the crude product, which was purified by prep-TLC, to provide compound N-((1r,4r)-4-(3-chloro-4-cyanophenoxy)cyclohexyl)-6-(4-((3aR,5r,6aS)-2-(2-(2,6-dioxopiperidin-3-yl)-6-fluoro-1,3-dioxoisoindolin-5-yl)octahydrocyclopenta[c]pyrrol-5-yl)methyl) piperazin-1-yl)pyridazine-3-formamide as a yellow solid (780 mg, 1.76 mmol), with a yield of 97%.

LC/MS (ESI$^+$) calcd for $C_{43}H_{45}ClFN_9O_6$[M+H]$^+$ m/z, 838.3; found, 837.7.

$^1$H NMR (400 MHz, $CDCl_3$) δ 8.22 (s, OH), 8.01 (d, J=9.3 Hz, OH), 7.89 (d, J=8.2 Hz, OH), 7.56 (d, J=8.7 Hz, OH), 7.41 (d, J=12.2 Hz, OH), 7.08 (d, J=7.3 Hz, OH), 6.98 (dd, J=15.1, 2.5 Hz, 1H), 6.85 (dd, J=8.7, 2.1 Hz, OH), 4.92 (dd, J=12.2, 5.3 Hz, OH), 4.32 (t, J=10.0 Hz, OH), 4.06 (d, J=8.3 Hz, OH), 3.81 (s, 1H), 3.72 (s, OH), 3.51 (dd, J=22.5, 7.9 Hz, 1H), 3.34 (d, J=10.7 Hz, OH), 2.90 (d, J=13.6 Hz, 1H), 2.85-2.72 (m, 1H), 2.62 (s, 1H), 2.43 (s, 1H), 2.26-2.10 (m, 2H), 1.79 (s, OH), 1.68 (d, J=11.2 Hz, 2H), 1.47 (dd, J=22.3, 10.4 Hz, 1H).

227: Synthesis of N-(4-(3-chloro-4-cyanophenoxy) phenyl)-6-(4-((4-(2-(2,6-dioxopiperidin-3-yl)-6-fluoro-1,3-dioxoisoindolin-5-yl)piperazin-1-yl) methyl) piperidin-1-yl)pyridazine-3-formamide

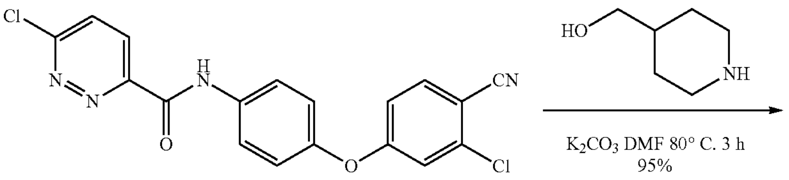

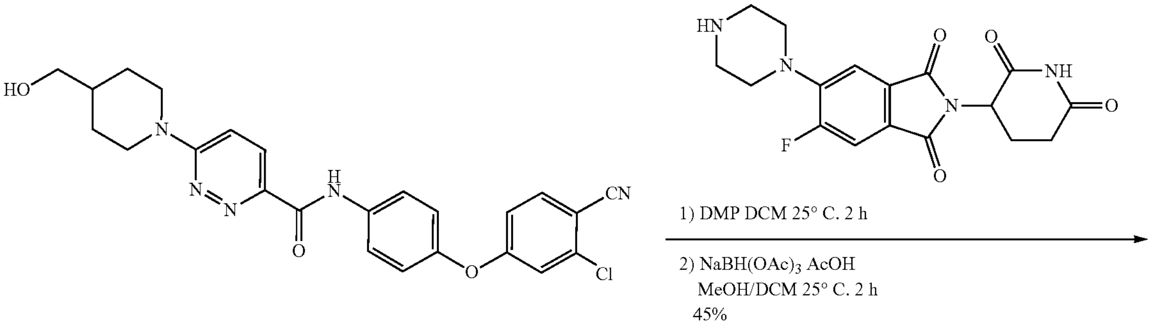

-continued

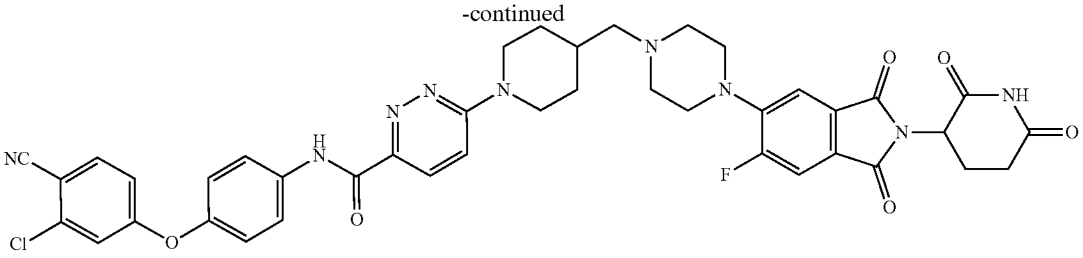

227

LC/MS (ESI+) calcd for $C_{41}H_{37}ClFN_9O_6$ $[M+H]^+$ m/z, 806.2; found, 805.7.

$^1$H NMR (400 MH, DMSO-$d_6$) δ 11.12 (s, 1H), 10.87 (s, 1H), 8.08-7.98 (m, 2H), 7.97-7.88 (m, 2H), 7.73 (d, J=11.4 Hz, 1H), 7.46 (d, J=7.4 Hz, 1H), 7.40 (d, J=9.8 Hz, 1H), 7.29 (d, J=2.4 Hz, 1H), 7.20 (d, J=9.0 Hz, 2H), 7.04 (dd, J=8.7, 2.4 Hz, 1H), 5.76 (s, 1H), 5.11 (dd, J=12.8, 5.4 Hz, 1H), 4.54 (d, J=12.1 Hz, 2H), 3.26 (s, 4H), 3.07 (t, J=11.9 Hz, 2H), 2.95-2.82 (m, 1H), 2.56 (dd, J=25.7, 14.6 Hz, 5H), 2.24 (d, J=6.6 Hz, 2H), 2.08-2.00 (m, 1H), 1.94 (s, 1H), 1.86 (d, J=12.7 Hz, 2H), 1.16 (dd, J=21.3, 10.8 Hz, 2H).

228: Synthesis of N-((1r,4r)-4-(3-chloro-4-cyano-phenoxy)cyclohexyl)-5-(4-(7-(2-(2,6-dioxopiperidin-3-yl)-6-fluoro-1,3-dioxoisoindolin-5-yl)-2,7-diazaspiro[3.5] nonan-2-yl)piperidin-1-yl)pyrazine-2-carboxamide

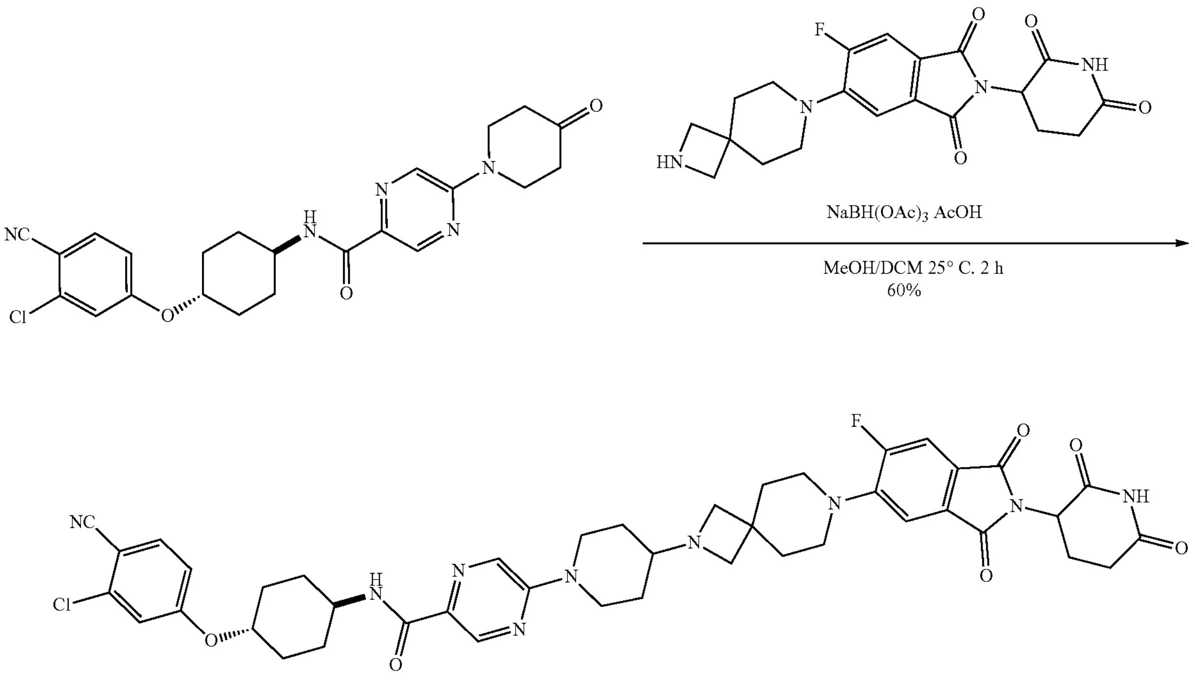

228

LC/MS (ESI+) calcd for $C_{43}H_{45}ClFN_9O_6$$[M+H]^+$ m/z, 838.3; found, 837.7.

$^1$H NMR (400 MHz, $CDCl_3$) δ 8.98 (s, 1H), 8.76 (s, 1H), 7.89 (s, 1H), 7.49 (d, J=8.7 Hz, 1H), 7.40 (d, J=10.9 Hz, 1H), 7.35-7.29 (m, 2H), 6.92 (d, J=2.3 Hz, 1H), 6.78 (dd, J=8.7, 2.3 Hz, 1H), 4.85 (dd, J=12.2, 5.4 Hz, 1H), 4.32-4.13 (m, 2H), 4.02-3.89 (m, 1H), 3.09 (dd, J=18.1, 7.0 Hz, 8H), 2.86-2.77 (m, 1H), 2.69 (td, J=15.4, 4.1 Hz, 2H), 2.43 (s, 1H), 2.17-2.01 (m, 4H), 1.89 (s, 3H), 1.79 (d, J=10.5 Hz, 2H), 1.62 (dd, J=22.4, 9.8 Hz, 3H), 1.46-1.32 (m, 4H).

229: Synthesis of N-((1r,4r)-4-(3-chloro-4-cyano-phenoxy)cyclohexyl)-5-(4-(7-(2-(2,6-dioxopiperidin-3-yl)-1,3-dioxoisoindolin-5-yl)-2,7-diazaspiro[3.5] nonan-2-yl) piperidin-1-yl)pyrazine-2-carboxamide

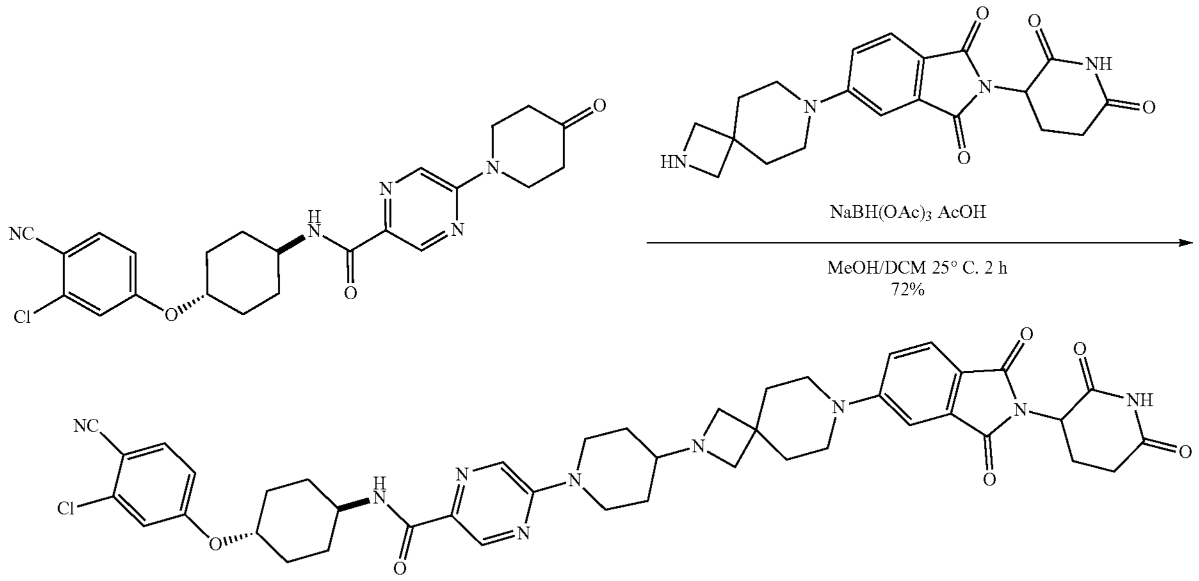

229

LC/MS (ESI$^+$) calcd for $C_{43}H_{43}ClN_9O_6$ [M+H]$^+$ m/z, 820.3; found, 819.8.

$^1$H NMR (400 MHz, CDCl$_3$) δ 8.84 (d, J=1.2 Hz, 1H), 8.61 (s, 1H), 7.98 (d, J=1.1 Hz, 1H), 7.69 (d, J=8.5 Hz, 1H), 7.57 (d, J=8.7 Hz, 1H), 7.40 (d, J=8.2 Hz, 1H), 7.30 (d, J=2.2 Hz, 1H), 7.07 (dd, J=8.6, 2.3 Hz, 1H), 7.01 (d, J=2.4 Hz, 1H), 6.86 (dd, J=8.7, 2.4 Hz, 1H), 4.95 (dd, J=12.3, 5.3 Hz, 1H), 4.40-4.23 (m, 3H), 4.12-3.99 (m, 1H), 3.49-3.32 (m, 4H), 3.18 (d, J=14.9 Hz, 6H), 2.96-2.70 (m, 3H), 2.50 (s, 1H), 2.27-2.10 (m, 5H), 1.89 (d, J=14.4 Hz, 4H), 1.84 (s, 2H), 1.77-1.63 (m, 3H), 1.48 (dd, J=22.6, 10.2 Hz, 4H).

230: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonan-7-yl) methyl)piperidin-1-yl)pyridazine-3-carboxamide

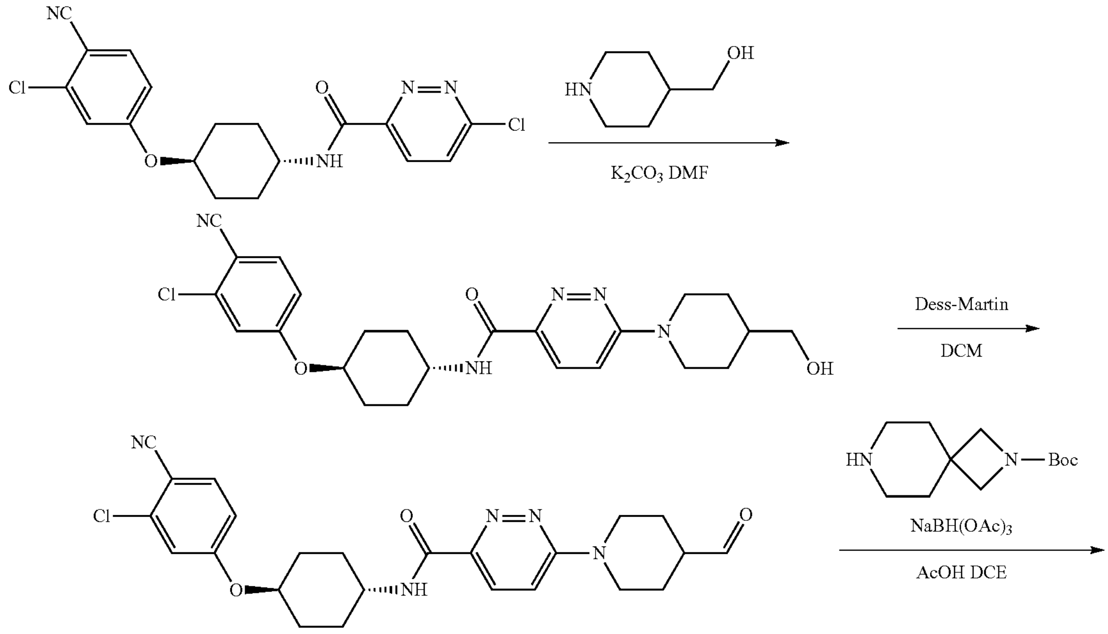

-continued

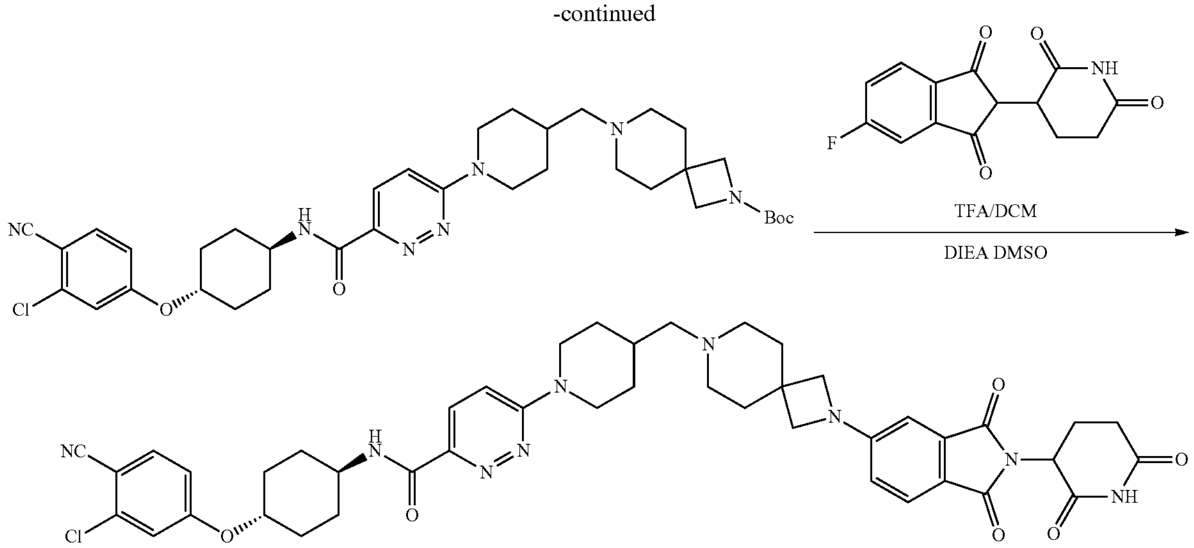

230

1. Compound N-((1r,4r)-4-(3-chloro-4-cyanophenoxy)cyclohexyl)-6-(4-(hydroxymethyl)piperidin-1-yl)pyridazine-3-formamide Compounds 6-chloro-N-((1r,4r)-4-(3-chloro-4-cyanophenoxy)cyclohexyl)pyridazine-3-formamide (1.00 g, 2.56 mmol), 4-hydroxymethylpiperidine (883 mg, 7.67 mmol), potassium carbonate (1.77 g, 12.78 mmol) and DMF 12 mL were sequentially added to a reactor. Under the nitrogen protection, the solution was allowed to react 3 h at 80° C. The reaction was completed by TLC detection, to which was added water, and then extracted three times with ethyl acetate. The organic layer was combined, washed three times with saturated brine, dried, rotatory evaporated to dry, and separated by column chromatography, to provide compound N-((1r,4r)-4-(3-chloro-4-cyanophenoxy) cyclohexyl)-6-(4-(hydroxymethyl)piperidin-1-yl)pyridazine-3-formamide as a white solid (1.09 g, 2.32 mmol), with a yield of 91%.

LC/MS (ESI$^+$) calcd for $C_{24}H_{27}ClN_5O_3$[M+H]$^+$ m/z, 470.2; found, 470.2.

2. Compound N-((1r,4r)-4-(3-chloro-4-cyanophenoxy)cyclohexyl)-6-(4-formylpiperidin-1-yl) pyridazine-3-carboxamide Compound N-((1r,4r)-4-(3-chloro-4-cyanophenoxy)cyclohexyl)-6-(4-(hydroxymethyl) piperidin-1-yl)pyridazine-3-formamide (95 mg, 0.20 mmol) was dissolved in 2 mL DCM, to which was added Dess-Martin periodinane (128 mg, 0.30 mmol), and the solution was stirred and reacted 3 h at room temperature. The reaction was completed by TLC detection. The reaction solution was filtered, and the filter cake was rinsed with dichloromethane. The filtrate was washed with sodium sulfite solution, dried, and rotatory evaporated to dry, to provide the crude product as a pale yellow solid, which was directly used for the next reaction.

LC/MS (ESI$^+$) calcd for $C_{24}H_{25}ClN_5O_3$ [M+H]$^+$ m/z, 467.2; found, 467.9.

3. Synthesis of compound t-butyl 7-((1-(6-(((1r,4r)-4-(3-chloro-4-cyanophenoxy) cyclohexyl)carbamoyl)pyridazine-3-yl)piperidine-4-yl)methyl)-2,7-diazaspiro[3.5] nonane-2-carboxylate Compound crude N-((1r,4r)-4-(3-chloro-4-cyanophenoxy)cyclohexyl)-6-(4-formylpiperidin-1-yl)pyridazine-3-carboxamide was dissolved in 1,2-dichloroethane (2 mL), to which were successively added t-butyl 2,7-diazaspiro[3.5] nonane-2-carboxylate (55 mg, 0.24 mmol), glacial acetic acid (24 mg, 0.40 mmol), and then the mixture was stirred for 30 min at room temperature, followed by addition of sodium triacetylborohydride (128 mg, 0.61 mmol). The reaction solution was stirred 2 h at room temperature, to which was then added with DCM and water for extraction. The organic layer was washed with brine, dried over anhydrous sodium sulfate, rotatory evaporated to dry, and purified by silica gel column chromatography, to provide compound t-butyl 7-((1-(6-(((1r,4r)-4-(3-chloro-4-cyanophenoxy)cyclohexyl)carbamoyl)pyridazine-3-yl) piperidine-4-yl)methyl)-2,7-diazaspiro[3.5]nonane-2-carboxylate (113.0 mg, 0.17 mmol), with a yield of 85.0%.

LC/MS (ESI$^+$) calcd for $C_{36}H_{47}ClN_7O_4$ [M+H]$^+$ m/z, 678.4; found, 678.0.

4. Synthesis of Compound N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)piperidin-1-yl) pyridazine-3-carboxamide Compound t-butyl 7-((1-(6-(((1r,4r)-4-(3-chloro-4-cyanophenoxy)cyclohexyl) carbamoyl)pyridazine-3-yl)piperidine-4-yl)methyl)-2,7-diazaspiro[3.5]nonane-2-carboxylate (50 mg, 0.074 mmol) was dissolved in 2 mL $CH_2Cl_2$ and 2 mL TFA. The solution was stirred for 2 h at room temperature, and then rotatory evaporated to remove the solvent, to which were added 2-(2,6-dioxopiperidin-3-yl)-5-fluoroisoindole-1,3-dione (24 mg, 0.088 mmol), 1 mL of DMSO and DIEA (95 mg, 0.737 mmol). Under the nitrogen protection, the solution was stirred and reacted overnight at 120° C. The reaction was completed by TLC detection. To the reaction solution, was added water, and then the solution was extracted three times with ethyl acetate. The organic layer was combined, washed three times with saturated brine, dried, rotatory evaporated to dry, and separated by column chromatography, to provide compound N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)piperidin-1-yl) pyridazine-3-carboxamide as a yellow solid (17 mg, 0.020 mmol), with a yield of 27%.

LC/MS (ESI$^+$) calcd for $C_{45}H_{48}ClN_8O_6$ [M+H]$^+$ m/z, 834.3; found, 834.3.

$^1$H NMR (400 MHz, DMSO-d$_6$) δ 11.08 (s, 1H), 8.60 (d, J=8.2 Hz, 1H), 7.86 (d, J=8.8 Hz, 1H), 7.80 (d, J=9.6 Hz, 1H), 7.63 (d, J=8.3 Hz, 1H), 7.39 (d, J=2.3 Hz, 1H), 7.33 (d, J=9.7 Hz, 1H), 7.13 (dd, J=8.8, 2.4 Hz, 1H), 6.77 (s, 1H), 6.65 (dd, J=8.5, 1.7 Hz, 1H), 5.05 (dd, J=12.8, 5.3 Hz, 1H), 4.53 (t, J=7.4 Hz, 1H), 4.47 (d, J=13.3 Hz, 2H), 3.85 (d, J=8.0 Hz, 1H), 3.74 (s, 4H), 2.99 (t, J=11.8 Hz, 2H), 2.93-2.79 (m, 1H), 2.63-2.51 (m, 2H), 2.31 (s, 4H), 2.11 (s, 4H), 2.06-1.95 (m, 1H), 1.84 (dd, J=40.7, 16.8 Hz, 9H), 1.63 (dd, J=23.7, 10.8 Hz, 2H), 1.50 (dd, J=22.8, 10.0 Hz, 2H), 1.16-1.01 (m, 2H).

231: Synthesis of N-((1r,4r)-4-(3-chloro-4-cyanophenoxy)cyclohexyl)-6-(4-((2-(2-(2-,2,6-dioxopiperidin-3-yl)-6-fluoro-1,3-dioxoisoindolin-5-yl)-2,7-diazaspiro[3.5]nonan-7-yl)methyl)piperidin-1-yl) pyridazine-3-carboxamide

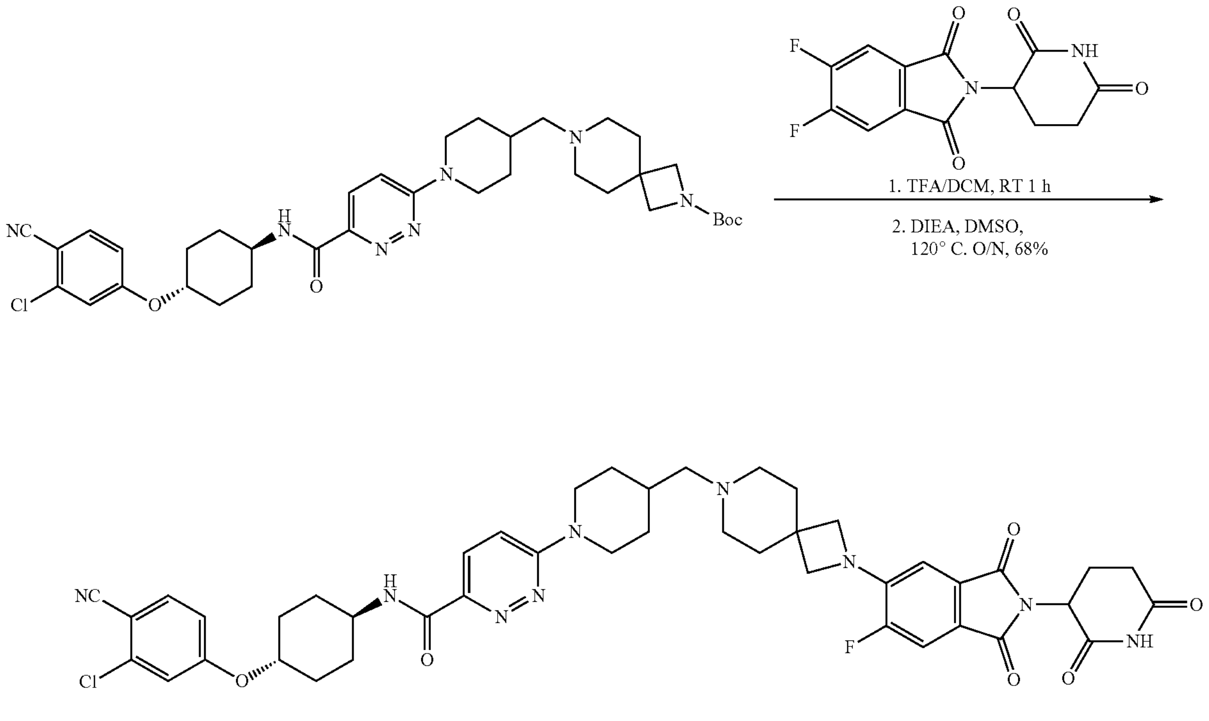

231

LC/MS (ESI$^+$) calcd for $C_{44}H_{47}ClFN_9O_6$ [M+H]$^+$ m/z, 852.3; found, 852.3.

$^1$H NMR (400 MHz, $CDCl_3$) δ 8.10 (s, 1H), 7.97 (d, J=9.3 Hz, 1H), 7.88 (d, J=8.1 Hz, 1H), 7.56 (d, J=8.7 Hz, 1H), 7.36 (d, J=10.8 Hz, 1H), 7.00 (d, J=2.4 Hz, 1H), 6.98 (d, J=9.8 Hz, 1H), 6.86 (dd, J=8.8, 2.4 Hz, 1H), 6.81 (d, J=7.5 Hz, 1H), 4.91 (dd, J=12.2, 5.3 Hz, 1H), 4.51 (d, J=11.8 Hz, 2H), 4.35-4.27 (m, 1H), 4.05 (dd, J=11.5, 7.4 Hz, 1H), 3.89 (s, 4H), 3.04 (s, 2H), 2.92-2.74 (m, 4H), 2.37 (s, 3H), 2.22-2.09 (m, 8H), 1.86 (s, 4H), 1.64 (d, J=21.2 Hz, 4H), 1.46 (dd, J=20.7, 8.5 Hz, 3H).

232: Synthesis of N-((1r,4r)-4-(3-chloro-4-cyano-phenoxy)cyclohexyl)-6-(7-((1-(2,6-dioxopiperidin-3-yl)-6-fluoro-1,3-dioxoisoindolin-5-yl)piperidine-4-yl)methyl)-2,7-diazaspiro[3.5]nonan-2-yl) pyridazine-3-formamide

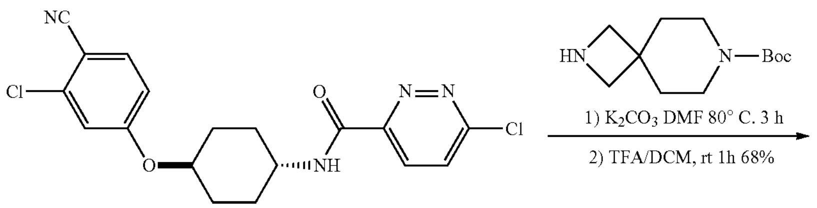

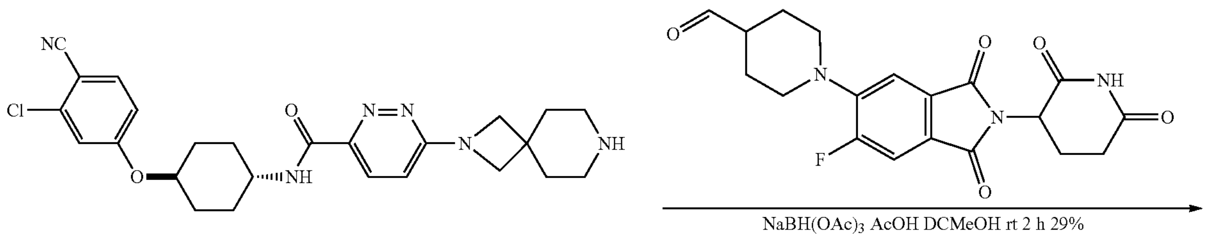

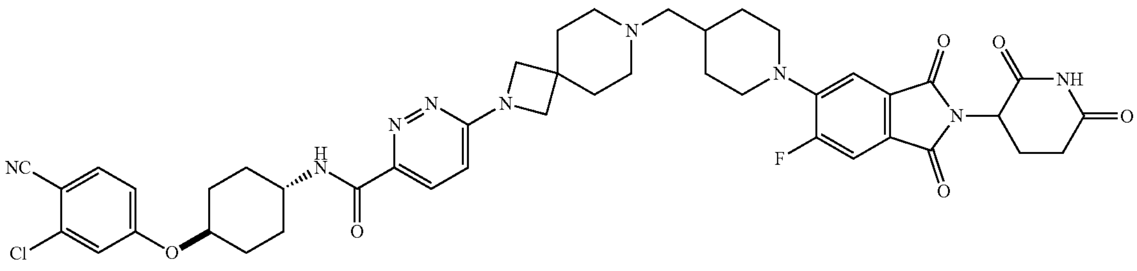

232

LC/MS ($ESI^+$) calcd for $C_{44}H_{47}ClFN_9O_6$ $[M+H]^+$ m/z, 852.3; found 851.8.

$^1H$ NMR (400 MHz, $CDCl_3$) δ 8.11 (s, 1H), 7.98 (d, J=9.2 Hz, 1H), 7.87 (d, J=8.0 Hz, 1H), 7.56 (d, J=8.7 Hz, 1H), 7.46 (d, J=11.0 Hz, 1H), 7.38 (d, J=7.3 Hz, 1H), 7.00 (d, J=2.4 Hz, 1H), 6.85 (dd, J=8.8, 2.4 Hz, 1H), 6.59 (d, J=9.3 Hz, 1H), 4.93 (dd, J=12.2, 5.3 Hz, 1H), 4.32 (t, J=9.8 Hz, 1H), 4.05 (d, J=8.1 Hz, 1H), 3.93 (s, 3H), 3.66 (d, J=12.1 Hz, 2H), 2.81 (dtd, J=24.4, 13.3, 5.9 Hz, 5H), 2.24-2.09 (m, 5H), 1.96 (s, 5H), 1.69 (d, J=12.2 Hz, 10H), 1.47 (dd, J=22.5, 10.3 Hz, 6H).

233: Synthesis of N-((1r,4r)-4-(3-chloro-4-cyano-phenoxy)cyclohexyl)-5-(4-((2-(2,6-dioxopiperidin-3-yl)-6-fluoro-1,3-dioxoisoindolin-5-yl)-2,7-diazaspiro [3.5]nonan-7-yl)methyl)piperidin-1-yl)pyrazine-2-carboxamide

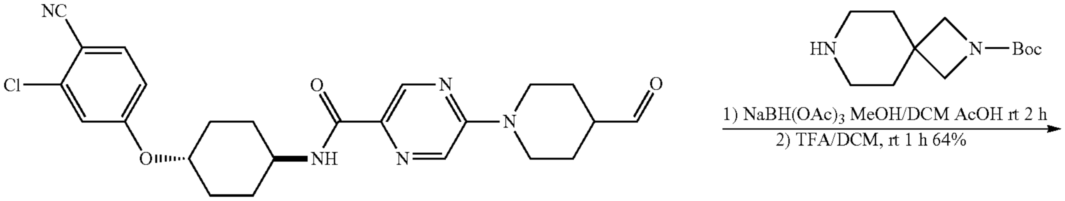

-continued

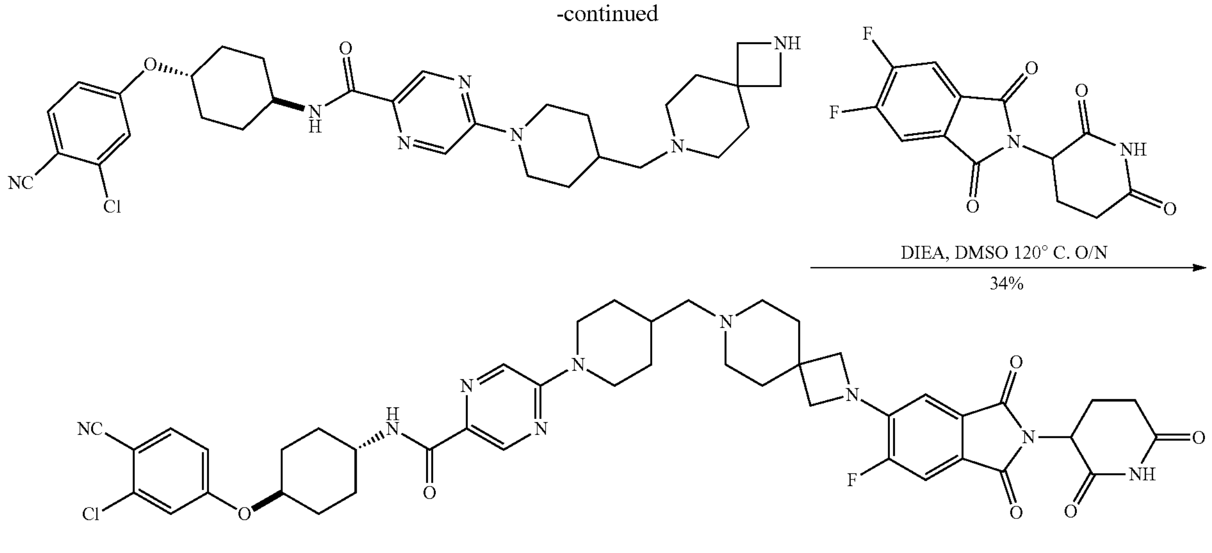

233

LC/MS ($ESI^+$) calcd for $C_{44}H_{47}ClFN_9O_6[M+H]^+$ m/z, 852.3; found 851.8.

$^1H$ NMR (400 MHz, $CDCl_3$) δ8.82 (s, 14), 8.78-8.49 (m, 1H), 7.95 (s, 1H), 7.56 (d, J=8.7 Hz, 1H), 7.47 (d, J=10.8 Hz, 1H) 7.38 (d, J=6.6 Hz, 2H), 6.99 (dd, 2.0 Hz, 1H), 6.85 (dd, J=8.7, 2.1 Hz, 1H), 4.93 (dd, J=12.1, 5.3 Hz, 1H), 4.45 (d, J=13.2 Hz, 2H), 4.32 (d, J=10.0 Hz, 1H), 4.03 (d, J=7.6 Hz, 1H), 3.24 (s, 2H), 3.17 (s, 5H), 3.03-2.92 (m, 2H), 2.87 (d, J=11.0 Hz, 1H), 2.78 (dd, J=23.8, 12.5 Hz, 2H), 2.53 (s, 2H), 2.18 (s, 5H), 2.05-1.84 (m, 8H), 1.66 (d, J=10.1 Hz, 2H), 1.52-1.40 (m, 2H), 1.26 (t, J=10.7 Hz, 3H).

234: Synthesis of N-((1r,4r)-4-(3-chloro-4-cyano-phenoxy)cyclohexyl)-5-(4-((7-(2,6-dioxopiperidin-3-yl)-6-fluoro-1,3-dioxoisoindolin-5-yl)-2,7-diazaspiro[3.5]nonan-2-yl)methyl)piperidin-1-yl)pyrazine-2-carboxamide

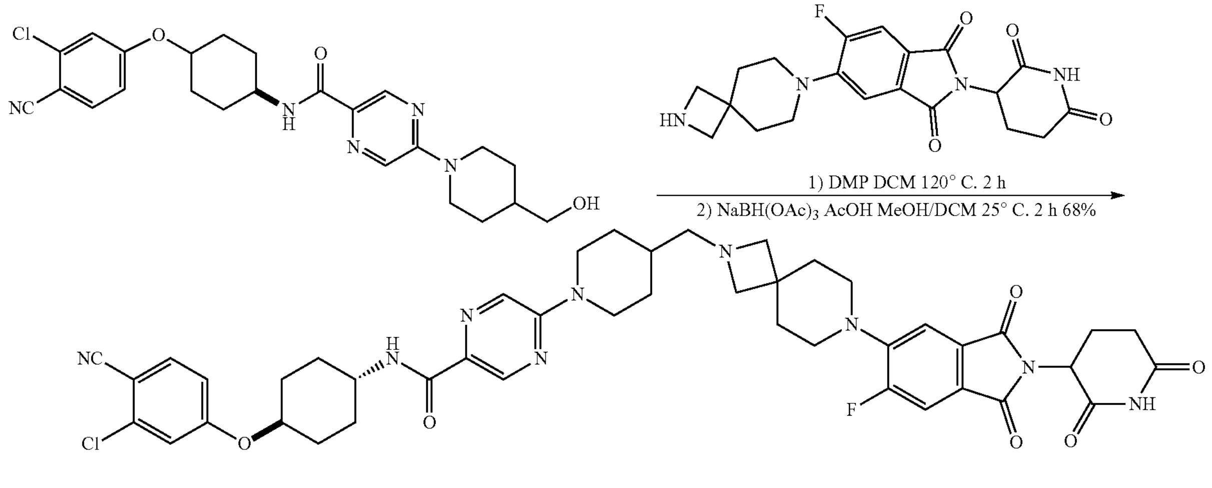

234

LC/MS ($ESI^+$) calcd for $C_{44}H_{47}ClFN_9O_6[M+H]^+$ m/z, 852.3; found, 852.3.

$^1H$ NMR (400 MHz, $CDCl_3$) δ 8.82 (d, J=1.1 Hz, 1H), 8.43 (s, 1H), 7.95 (d, J=0.9 Hz, 1H), 7.56 (d, J=8.7 Hz, 1H), 7.47 (d, J=10.9 Hz, 1H), 7.42-7.33 (m, 2H), 6.99 (d, J=2.3 Hz, 1H), 6.85 (dd, J=8.8, 2.4 Hz, 1H), 4.93 (dd, J=12.3, 5.3 Hz, 1H), 4.46 (d, J=13.2 Hz, 21-1), 4.35-4.24 (m, 1H), 4.09-3.98 (m, 1H), 3.16 (d, J=5.2 Hz, 6H), 3.03-2.87 (m,

3H), 2.84-2.71 (m, 2H), 2.55 (s, 2H), 2.15 (dd, J=14.9, 4.7 Hz, 5H), 2.06-1.85 (m, 6H), 1.70 (s, 4H), 1.53-1.38 (m, 3H), 1.29 (s, 2H).

235: Synthesis of N-((1r,4r)-4-(3-chloro-4-cyanophenoxy)cyclohexyl)-5-(7-((1-(2-(2,6-dioxopiperidin-3-yl)-6-fluoro-1,3-dioxoisoindolin-5-yl)piperidine-4-yl)methyl)-2,7-diazaspiro[3.5]nonan-2-yl)pyrazine-2-carboxamide

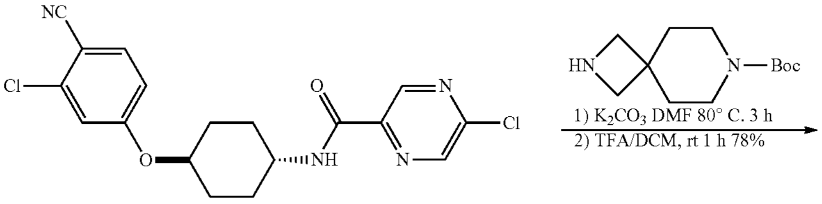

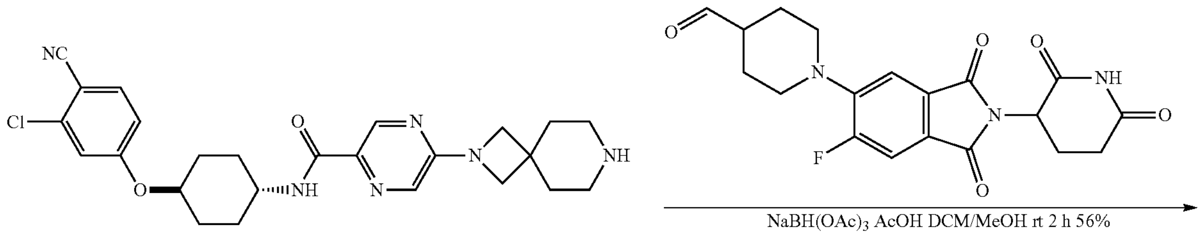

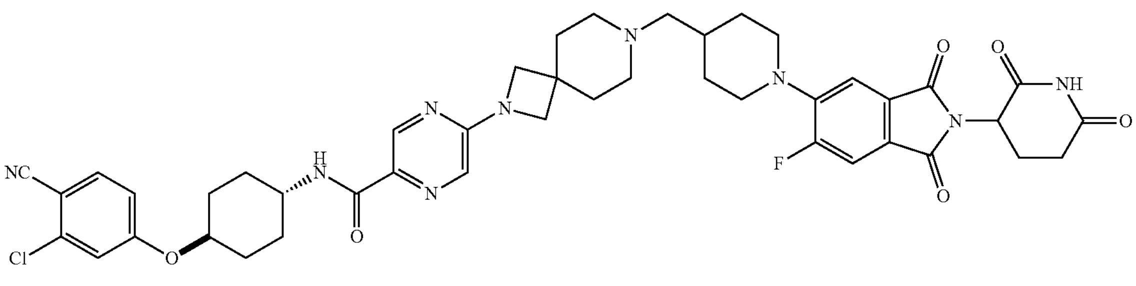

235

LC/MS (ESI+) calcd for $C_{44}H_{47}ClFN_9O_6$ $[M+H]^+$ m/z, 852.3; found, 852.3.

$^1H$ NMR (400 MHz, DMSO-$d_6$) δ 11.12 (s, 1H), 8.57 (d, J=1.1 Hz, 1H), 8.12 (d, J=8.2 Hz, 1H), 7.86 (d, J=8.8 Hz, 1H), 7.79 (d, J=1.0 Hz, 1H), 7.70 (d, J=11.4 Hz, 1H), 7.43 (d, J=7.4 Hz, 1H), 7.37 (d, J=2.4 Hz, 11H), 7.12 (dd, J=8.8, 2.4 Hz, 1H), 5.10 (dd, J=12.8, 5.4 Hz, 1H), 4.50 (d, J=9.8 Hz, 1H), 3.84 (s, 4H), 3.60 (d, J=11.8 Hz, 2H), 3.31 (s, 1H), 2.88 (t, J=11.4 Hz, 3H), 2.59 (d, J=18.3 Hz, 1H), 2.32 (s, 3H), 2.20-2.00 (m, 5H), 1.92-1.81 (m, 3H), 1.77 (s, 6H), 1.55 (ddd, J=32.5, 23.2, 10.3 Hz, 5H), 1.26 (s, 2H).

236: Synthesis of N-((1r,4r)-4-(4-cyano-3-(trifluoromethyl)phenoxy)cyclohexyl)-5-(4-(7-(2-(2,6-dioxopiperidin-3-yl)-6-fluoro-1,3-dioxoisoindolin-5-yl)-2,7-diazaspiro[3.5]nonan-2-yl)piperidin-1-yl)pyrazine-2-carboxamide

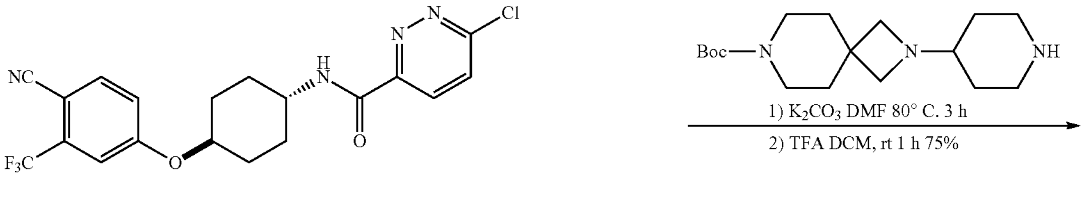

-continued
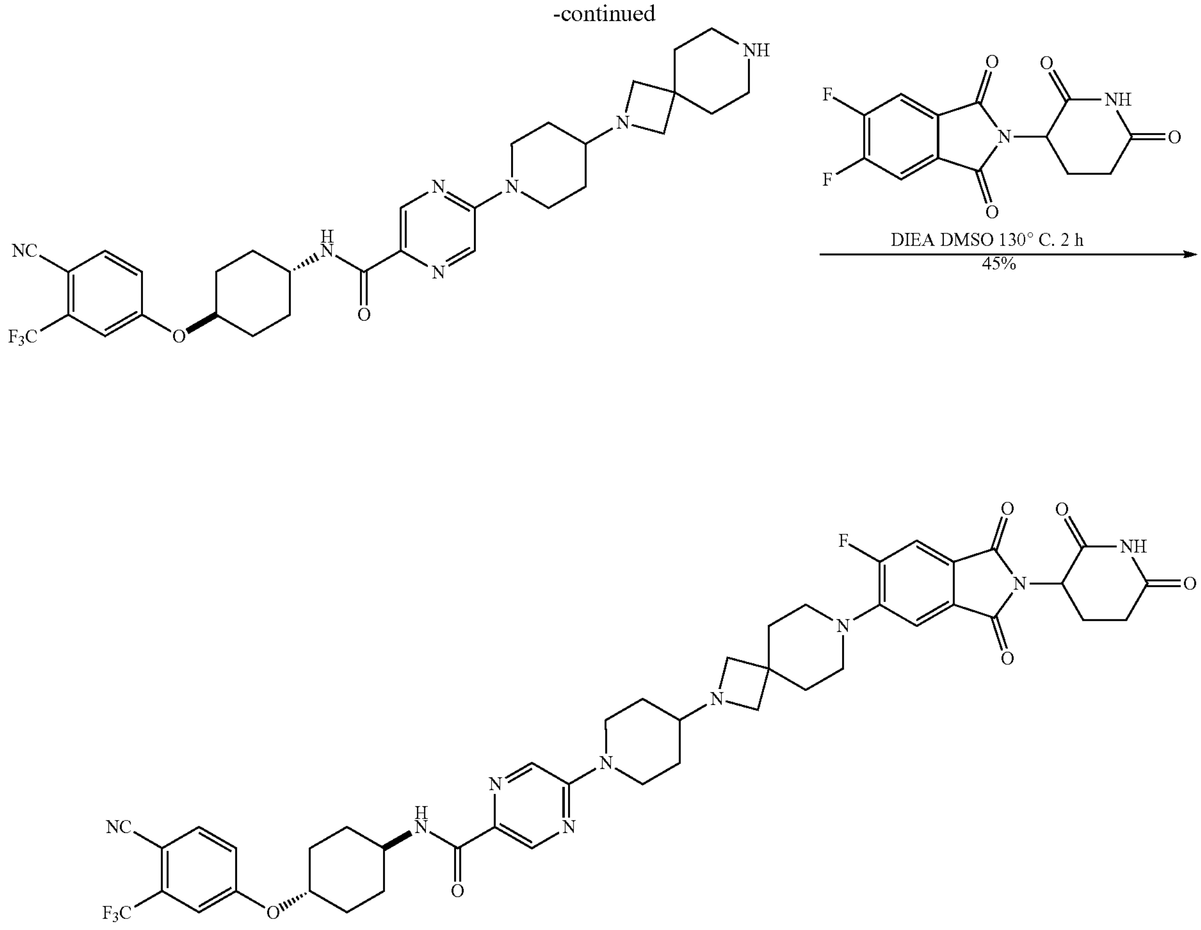
236
LC/MS (ESI+) calcd for $C_{44}H_{45}F_4N_9O_6$ $[M+H]^+$ m/z, 872.3 found, 872.2.
$^1H$ NMR (400 MHz, $CDCl_3$) δ 8.83 (d, J=1.1 Hz, 1H), 8.54 (s, 1H), 7.96 (d, J=1.0 Hz, 1H), 7.74 (d, J=8.6 Hz, 1H), 7.47 (d, J=10.9 Hz, 1H), 7.39 (dd, J=7.7, 3.2 Hz, 2H), 7.25 (d, J=2.4 Hz, 1H), 7.10 (dd, J=8.6, 2.4 Hz, 1H), 4.93 (dd, J=12.3, 5.4 Hz, 1H), 4.37 (dd, J=22.3, 11.9 Hz, 3H), 4.04 (dd, J=11.5, 7.5 Hz, 1H), 3.24 (d, J=26.5 Hz, 3H), 3.20-3.06 (m, 4H), 2.94-2.67 (m, 3H), 2.26-2.10 (m, 5H), 1.99 (s, 4H), 1.93-1.79 (m, 3H), 1.55-0.40 (m, 4H).
237: Synthesis of N-((1r,4r)-4-(3-chloro-4-cyano-phenoxy)cyclohexyl)-6-(5-((1r,5S,6s)-3-(2-(2,6-di-oxopiperidin-3-yl)-6-fluoro-1,3-dioxoisoindolin-5-yl)-3-azabicyclo[3.1.0]n-hexane-6-yl)methyl)-2,5-diazabicyclo[2.2.1]heptan-2-yl) pyridazine-3-formamide
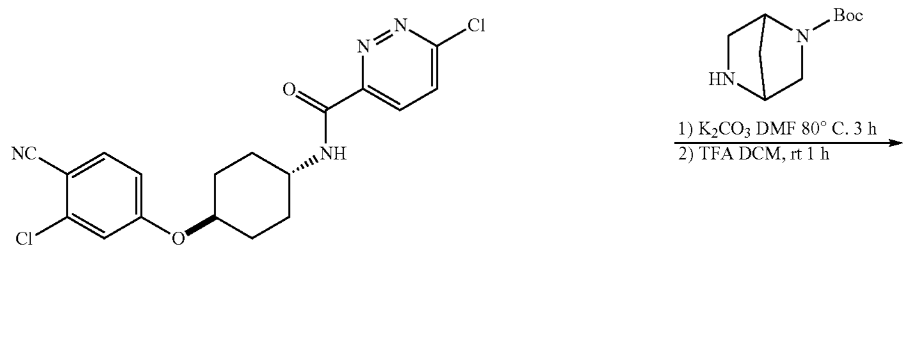

-continued

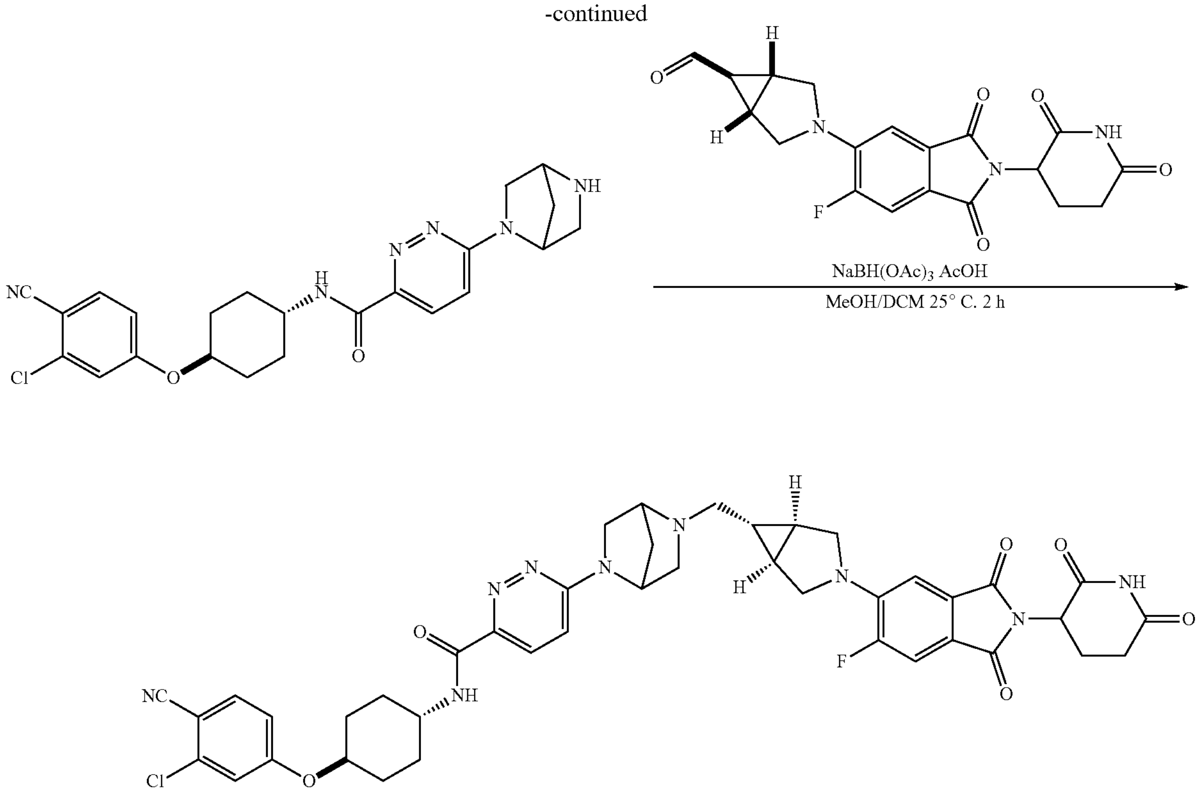

237

1. Synthesis of Compound 6-(2,5-diazabicyclo[2.2.1]heptan-2-yl)-N-(((r,4r)-4-(3-chloro-4-cyanophenoxy)cyclohexyl)pyridazine-3-formamide Compounds 6-chloro-N-((1r,4r)-4-(3-chloro-4-cyanophenoxy)cyclohexyl)pyridazine-3-formamide (150 mg, 0.38 mmol), t-butyl 2,5-diazabicyclo[2.2.1]heptane-2-carboxylate (114 mg, 0.58 mmol), potassium carbonate (265 mg, 1.92 mmol) and 2 mL of DMF were sequentially added to a reactor. Under the nitrogen protection, the solution was allowed to react 3 h at 80° C. The action was completed by TLC detection, to which was added water, and then extracted three times with ethyl acetate. The organic layer was washed three times with saturated brine, dried over anhydrous sodium sulfate, and rotatory evaporated to dry to obtain the crude product, which was separated by silica gel column chromatography to provide the intermediate as an off-white solid. The intermediate was dissolved in 1 mL of DCM, to which was then added 1 mL of TFA, and the resultant solution was stirred and reacted at room temperature for 1 h. The end of the reaction was confirmed by TLC. The reaction solution was added with the saturated aqueous solution of sodium bicarbonate, extracted with DCM for three times, dried over anhydrous sodium sulfate, and rotatory evaporated to dry, to provide compound 6-(2,5-diazabicyclo[2.2.1]heptan-2-yl)-N-(((1r,4r)-4-(3-chloro-4-cyanophenoxy)cyclohexyl)pyridazine-3-formamide as an off-white solid (130 mg, 0.29 mmol), with a yield of 75%.

LC/MS (ESI$^+$) calcd for $C_{23}H_{25}ClN_6O_2$[M+H]$^+$ m/z, 453.2; found, 453.2.

2. Synthesis of Compound N-((1r,4r)-4-(3-chloro-4-cyanophenoxy)cyclohexyl)-6-(5-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2,5-diazabicyclo[2.2.1]heptan-2-yl) pyridazine-3-formamide 6-(2,5-Diazabicyclo[2.2.1]heptan-2-yl)-N-(((1r,4r)-4-(3-chloro-4-cyanophenoxy) cyclohexyl)pyridazine-3-formamide (50 mg, 0.11 mmol) was added in (1R,5S,6r)-3-(2-(2,6-dioxopiperidin-3-yl)-6-fluoro-1,3-dioxoisoindol-5-yl)-3-azabicyclo[3.1.0]hexan-6-formaldehyde (36 mg, 0.092 mmol) and 2 mL of DCM/MeOH (1:1), and then the mixture was dissolve to obtain a clear solution, to which was added glacial acetic acid (II mg, 0.18 mmol), and the mixture was stirred and reacted at room temperature for 30 min, followed by addition of sodium triacetylborohydride (78 mg, 0.37 mmol). The reaction was stirred and reacted at room temperature for 2 h. The reaction was completed by TLC detection, to which was added the saturated aqueous solution of sodium bicarbonate, and then extracted with dichloromethane three times. The organic phase was combined, dried, rotatory evaporated to dry, and separated by pre-TLC to obtain compound N-((1r,4r)-4-(3-chloro-4-cyanophenoxy)cyclohexyl)-645-((1r,5S,6s)-3-(2-(2,6-dioxopiperidin-3-yl)-6-fluoro-1,3-dioxoisoindol-5-yl)-3-azabicyclo[3.1.0]n-hexane-6-yl)methyl)-2,5-diazabicyclo[2.2.1]heptan-2-yl) pyridazine-3-formamide as an off-white solid (68 mg, 0.083 mmol), with a yield of 90%. LC/MS (ESI$^+$) calcd for $C_{42}H_{41}ClFN_9O_6$ [M+H]$^+$ m/z, 822.3; found, 822.0.

$^1$H NMR (400 MHz, $CDCl_3$) δ 8.74 (d, J=32.3 Hz, 1H), 8.02 (d, J=9.3 Hz, 1H), 7.89 (t, J=11.6 Hz, 1H), 7.55 (t, J=9.3

Hz, 1H), 7.38 (d, J=12.5 Hz, 1H), 7.06-6.96 (m, 2H), 6.86 (dd, J=8.8, 2.4 Hz, 1H), 6.73 (d, J=9.4 Hz, 1H), 4.94-4.86 (m, 1H), 4.37-4.26 (m, 1H), 4.12-3.94 (m, 2H), 3.84 (dd, J=8.2, 4.7 Hz, 3H), 3.53 (d, J=6.2 Hz, 3H), 3.28 (s, 1H), 2.95-2.72 (m, 4H), 2.67 (s, 2H), 2.33 (s, 5H), 2.14 (dd, J=18.6, 7.2 Hz, 6H), 2.09-1.97 (m, 3H), 1.47 (dd, J=22.6, 10.5 Hz, 2H).

238: Synthesis of N-((1r,4r)-4-(3-chloro-4-cyano-phenoxy)cyclohexyl)-6-(5-((1r,5S,6s)-3-(2-(2,6-di-oxopiperidin-3-yl)-6-fluoro-1,3-dioxoisoindolin-5-yl)-3-azabicyclo[3.1.0]n-hexane-6-yl)methyl)-2,5-diazabicyclo[2.2.1]heptan-2-yl)pyrazine-3-formamide

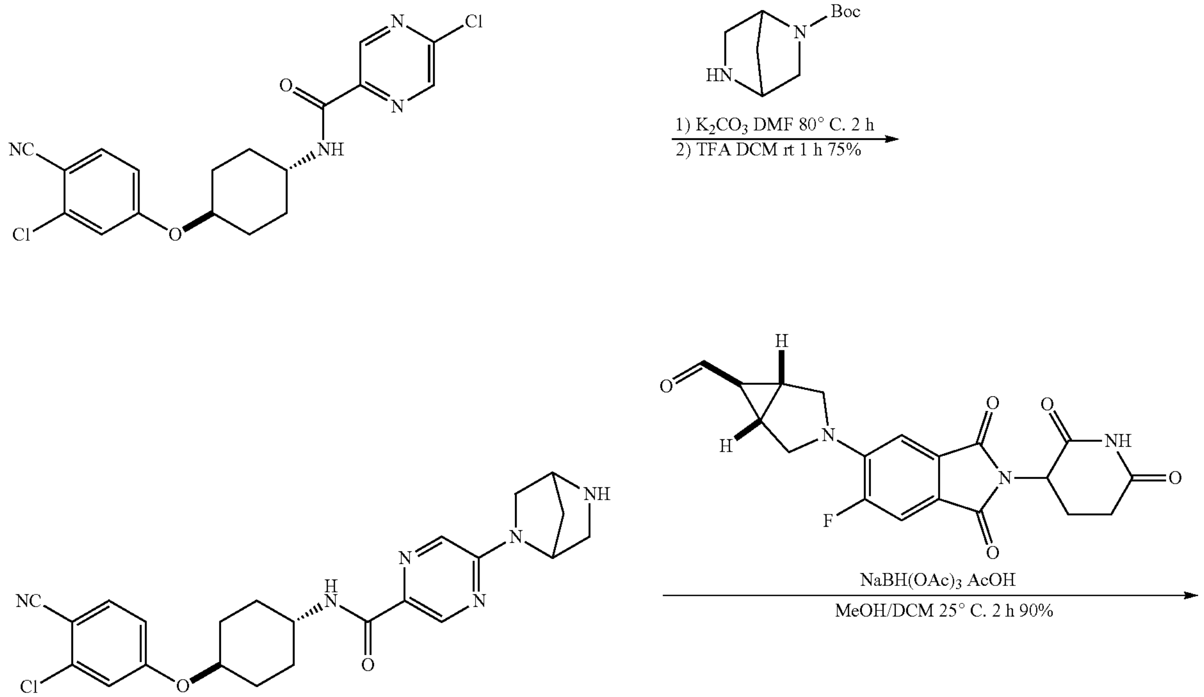

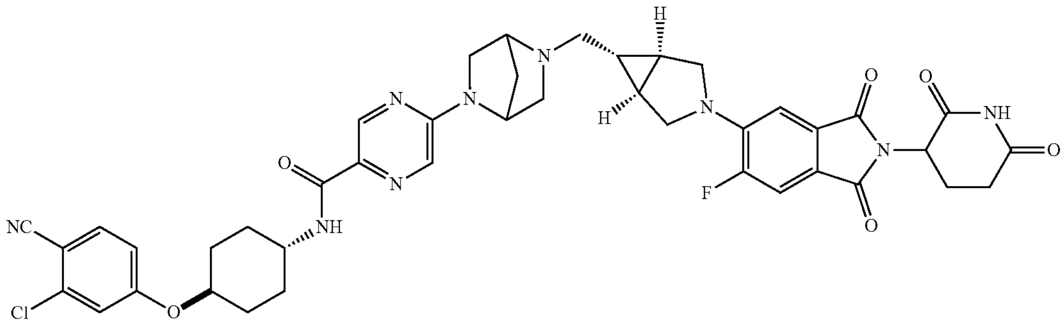

238

LC/MS (ESI$^+$) calcd for $C_{42}H_{41}ClFN_9O_6$[M+H]$^+$ m/z, 822.3; found, 822.0.

$^1$H NMR (400 MHz, $CDCl_3$) δ 8.95 (d, J=56.0 Hz, 1H), 8.83 (d, J=0.9 Hz, 1H), 7.70 (s, 1H), 7.56 (d, J=8.7 Hz, 1H), 7.39 (dd, J=10.3, 4.7 Hz, 2H), 7.39 (dd, J=10.3, 4.7 Hz, 2H), 7.05 (dd, J=7.3, 4.6 Hz, 1H), 6.99 (d, J=2.3 Hz, 1H), 6.85 (dd, J=8.7, 2.4 Hz, 1H), 4.95-4.88 (m, 1H), 4.36-4.24 (m, 1H), 4.02 (dd, J=11.4, 7.5 Hz, 1H), 3.85 (dd, J=13.9, 6.6 Hz, 3H), 3.72 (dd, J=14.0, 7.0 Hz, 1H), 3.57 (t, J=9.4 Hz, 2H), 3.48 (d, J=9.4 Hz, 1H), 3.19 (s, 1H), 2.94-2.66 (m, 4H), 2.59 (s, 2H), 2.24-2.03 (m, 6H), 1.93 (d, J=8.5 Hz, 1H), 1.71 (d, J=9.7 Hz, 6H), 1.47 (dd, J=22.5, 10.5 Hz, 2H).

239: Synthesis of N-((1r,4r)-4-(3-chloro-4-cyano-phenoxy)cyclohexyl)-6-((1r,5S)-8-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-3,8-diazabicyclo[3.2.1]octan-3-yl) pyridazine-3-formamide
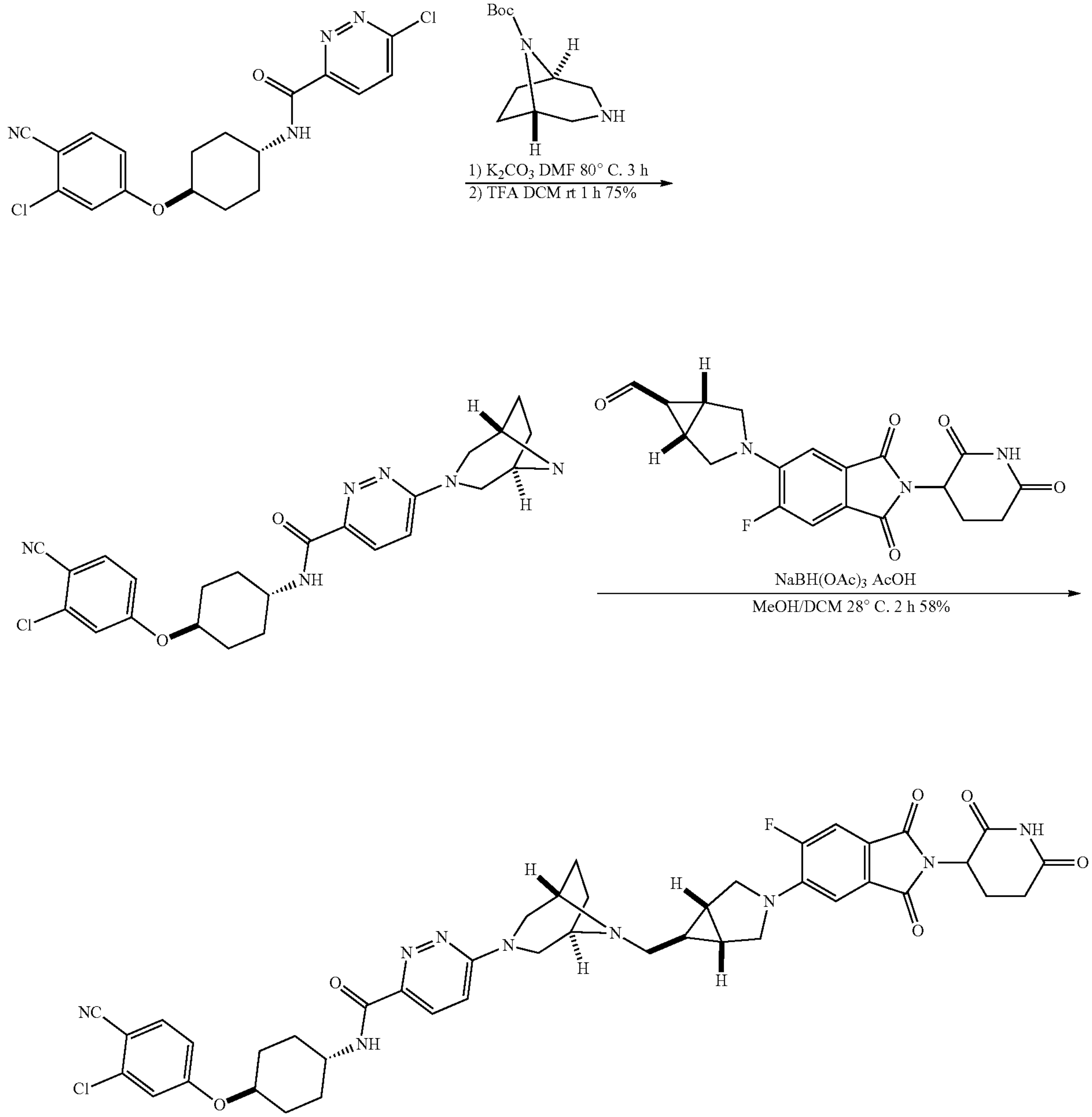
235
LC/MS ($ESI^+$) calcd for $C_{43}H_{43}ClFN_9O_6$ $[M+H]^+$ m/z, 836.3; found, 836.2.
$^1H$ NMR (400 MHz, $CDCl_3$) δ 8.42 (s, 1H), 8.01 (d, J=9.5 Hz, 1H), 7.89 (d, J=8.2 Hz, 1H), 7.56 (d, J=8.7 Hz, 1H), 7.40 (d, J=12.5 Hz, 1H), 7.05 (d, J=7.4 Hz, 1H), 7.00 (d, J=2.4 Hz, 1H), 6.93-6.81 (m, 2H), 4.92 (dd, J=12.3, 5.3 Hz, 1H), 4.37-4.26 (m, 1H), 4.13-3.95 (m, 3H), 3.91 (d, J=10.0 Hz, 2H), 3.61 (d, J=8.8 Hz, 4H), 3.45 (d, J=31.8 Hz, 2H), 2.94-2.71 (m, 3H), 2.53 (s, 2H), 2.23-2.10 (m, 5H), 2.04 (s, 2H), 1.86-1.69 (m, 6H), 1.53-1.39 (m, 3H), 1.02 (s, 1H).

240: Synthesis of N-((1r,4r)-4-(3-chloro-4-cyano-phenoxy)cyclohexyl)-6-((1r,5S)-8-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-3,8-diazabicyclo[3.2.1]octan-3-yl)pyrazine-3-formamide

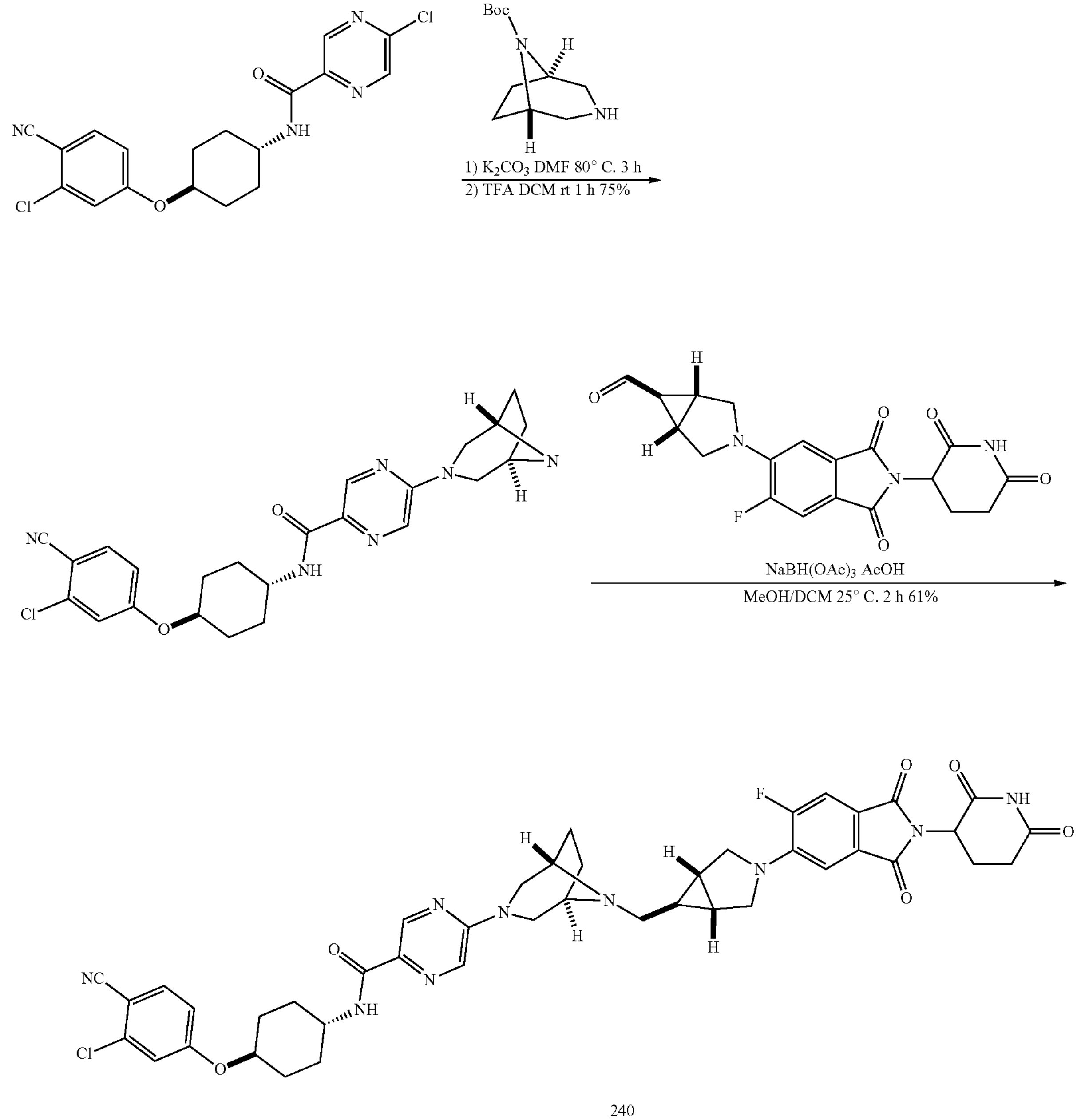

240

LC/MS ($ESI^+$) calcd for $C_{43}H_{43}ClFN_9O_6$ $[M+H]^+$ m/z, 836.3; found, 836.2.

$^1H$ NMR (400 MHz, $CDCl_3$) δ 8.85 (d, J=1.1 Hz, 1H), 8.50 (s, 1H), 7.87 (d, J=0.9 Hz, 1H), 7.56 (d, J=8.7 Hz, 1H), 7.42-7.36 (m, 2H), 7.05 (d, J=7.4 Hz, 1H), 6.99 (d, J=2.4 Hz, 1H), 6.85 (dd, J=8.7, 2.4 Hz, 1H), 4.92 (dd, J=12.3, 5.3 Hz, 1H), 4.34-4.26 (m, 1H), 4.09-4.01 (m, 1H), 4.01-3.93 (m, 2H), 3.93-3.86 (m, 2H), 3.60 (d, J=9.6 Hz, 2H), 3.58-3.50 (m, 2H), 3.36 (s, 2H), 2.94-2.84 (m, 1H), 2.83-2.71 (m, 2H), 2.50 (s, 2H), 2.16 (ddd, J=19.5, 8.5, 5.2 Hz, 5H), 2.00 (s, 2H), 1.70 (s, 6H), 1.47 (dd, J=22.6, 10.5 Hz, 2H), 1.00 (s, 1H).

241: Synthesis of N-((1r,4r)-4-(3-chloro-4-cyanophenoxy)cyclohexyl)-6-(4-((2-(2-(2-,2,6-dioxopiperidin-3-yl)-1,3-dioxoisoindolin-5-yl)-2,7-diazaspiro [3.5]nonan-7-yl)methyl)piperidin-1-yl)pyrazine-3-carboxamide

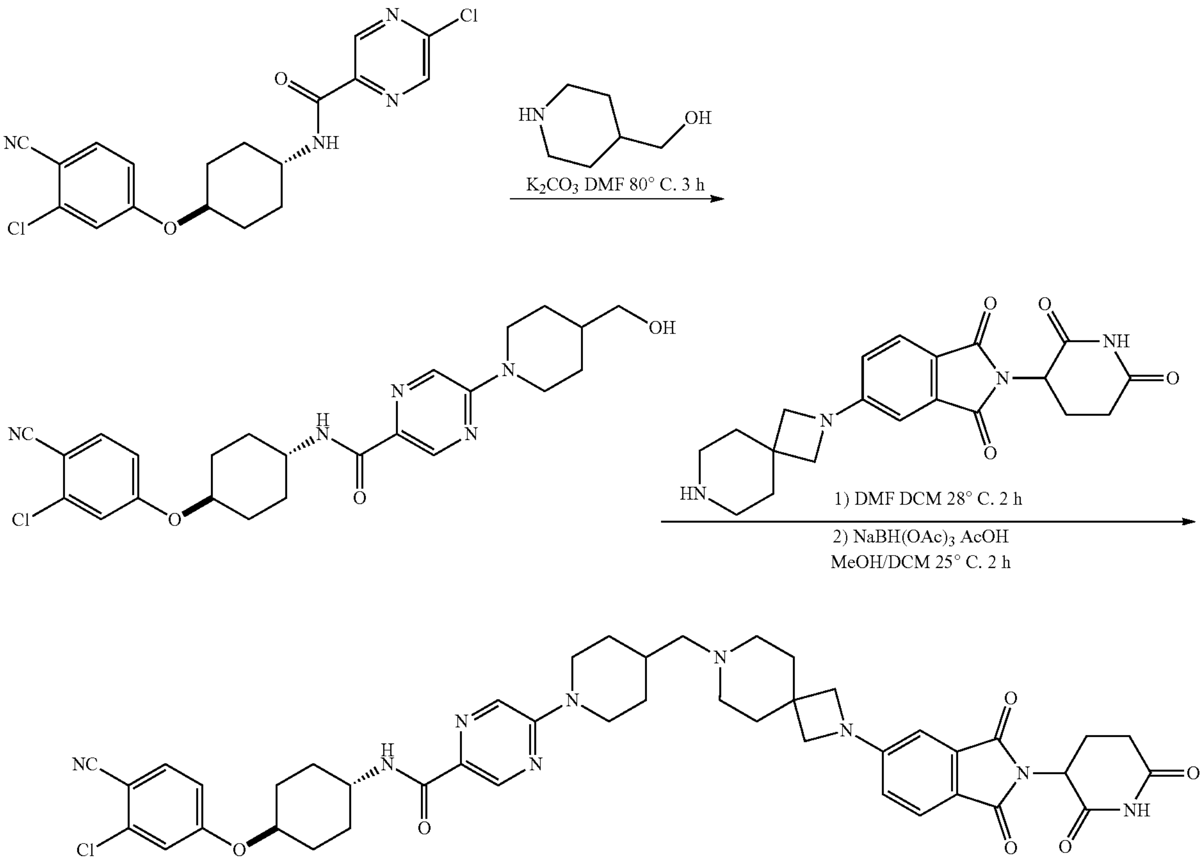

341

1. Compound N-((1r,4r)-4-(3-chloro-4-cyanophenoxy)cyclohexyl)-6-(4-(hydroxymethyl)piperidin-1-yl)pyrazine-3-formamide Compounds 6-chloro-N-((1r,4r)-4-(3-chloro-4-cyanophenoxy)cyclohexyl)pyrazine-3-formamide (300 mg, 0.77 mmol), 4-hydroxymethylpiperidine (265 mg, 2.30 mmol), potassium carbonate (530 mg, 3.83 mmol) and DMF (5 mL) were sequentially added to a reactor. Under the nitrogen protection, the solution was allowed to react 3 h at 80° C. The reaction was completed by TLC detection, to which was added water, and then extracted three times with ethyl acetate. The organic layer was combined and washed three times with saturated brine, dried over anhydrous sodium sulfate, rotatory evaporated to dry, and separated by column chromatography, to provide compound N-((1r,4r)-4-(3-chloro-4-cyanophenoxy)cyclohexyl)-6-(4-(hydroxymethyl) piperidin-1-yl)pyrazine-3-formamide as a white solid (355 mg, 0.76 mmol), with a yield of 98%.

LC/MS (ESI$^+$) calcd for $C_{24}H_{27}ClN_5O_3$ $[M+H]^+$ m/z, 470.2; found, 470.2.

2. Synthesis of Compound N-((1r,4r)-4-(3-chloro-4-cyanophenoxy)cyclohexyl)-6-((3aR,5R,6aS)-5-((5-(2-(2,6-dioxopiperidin-3-yl)-6-fluoro-1,3-dioxoisoindolin-5-yl) hexahydropyrrolo[3,4-c]pyrrol-2(1H)-yl) methyl)hexahydrocyclopenta[c]pyrrole-2(1H)-yl) pyrazine-3-formamide Compound N-((1r,4r)-4-(3-chloro-4-cyanophenoxy)cyclohexyl)-6-(4-(hydroxymethyl) piperidin-1-yl)pyrazine-3-formamide (70 mg, 0.15 mmol) was dissolved in 2 mL of DCM, to which was added DMP (76 mg, 0.18 mmol), and the mixture was stirred and reacted at room temperature for 2 h. The completion of the reaction was detected by TLC. The reaction solution was filtered, and the filter cake was rinsed with DCM. The filtrate was rotatory evaporated to dry to obtain a crude product, to which was added 2-(2,6-dioxopiperidin-3-yl)-5-fluoro-6-(hexahydropyrrolo[3,4-c] pyrrol-2(1H)-yl) isoindole-1,3-dione (68 mg, 0.18 mmol) and 2 mL of DCM/MeOH (1:1). The reaction was dissolved, and then glacial acetic acid (18 mg, 0.30 mmol) was added. The mixture was stirred and reacted at room temperature for 30 min, to which was then added sodium triacetylborohydride (126 mg, 0.60 mmol). The reaction was stirred and reacted at room temperature for 2 h. The reaction was completed by TLC detection, to which was added the saturated aqueous solution of sodium bicarbonate, and then extracted with dichloromethane three times. The organic phase was combined, dried, rotatory evaporated to dry, and separated by pre-TLC to obtain compound N-((1r,4r)-4-(3-chloro-4-cyanophenoxy)cyclohexyl)-6-((3aR,5R, 6aS)-5-((5-(2-(2,6-dioxopiperidin-3-yl)-6-fluoro-1,3-dioxoisoindolin-5-yl)hexahydropyrrolo[3,4-c]pyrrol-2(1H)-yl)methyl) hexahydrocyclopenta[c]pyrrole-2(1H)-yl)pyrazine-3-formamide as an off-white solid (86 mg, 0.10 mmol), with a yield of 69%.

LC/MS (ESI$^+$) calcd for $C_{45}H_{48}ClN_8O_6$ $[M+H]^+$ m/z, 834.3; found, 834.3.

$^1$H NMR (400 MHz, $CDCl_3$) δ 8.79 (s, 1H), 7.98 (s, 1H), 7.64 (d, J=8.2 Hz, 1H), 7.57 (d, J=8.7 Hz, 1H), 7.48 (d, J=8.1 Hz, 1H), 7.01 (d, J=2.0 Hz, 1H), 6.86 (dd, J=8.7, 2.0 Hz, 1H), 6.78 (s, 1H), 6.52 (d, J=8.3 Hz, 1H), 4.93 (dd, J=12.0, 5.2 Hz, 1H), 4.93 (dd, J=12.0, 5.2 Hz, 1H), 4.46 (d, J=12.8 Hz, 2H), 4.32 (t, J=9.9 Hz, 1H), 4.01 (d, J=7.6 Hz, 1H), 3.75 (s, 4H), 3.08-2.96 (m, 3H), 2.82-2.75 (m, 3H), 2.40 (s, 4H), 2.15 (dd, J=25.3, 8.7 Hz, 7H), 1.91 (d, J=22.6 Hz, 6H), 1.69 (dd, J=22.2, 10.6 Hz, 2H), 1.48 (dd, J=22.2, 10.9 Hz, 2H), 1.23 (d, J=18.1 Hz, 2H).

242: Synthesis of N-((1r,4r)-4-(3-chloro-4-cyanophenoxy)cyclohexyl)-5-(7-(1-(2-(2,6-dioxopiperidin-3-yl)-6-fluoro-1,3-dioxoisoindolin-5-yl)piperidine-4-yl)-2,7-diazaspiro[3.5]nonan-2-yl)pyrazine-2-carboxamide

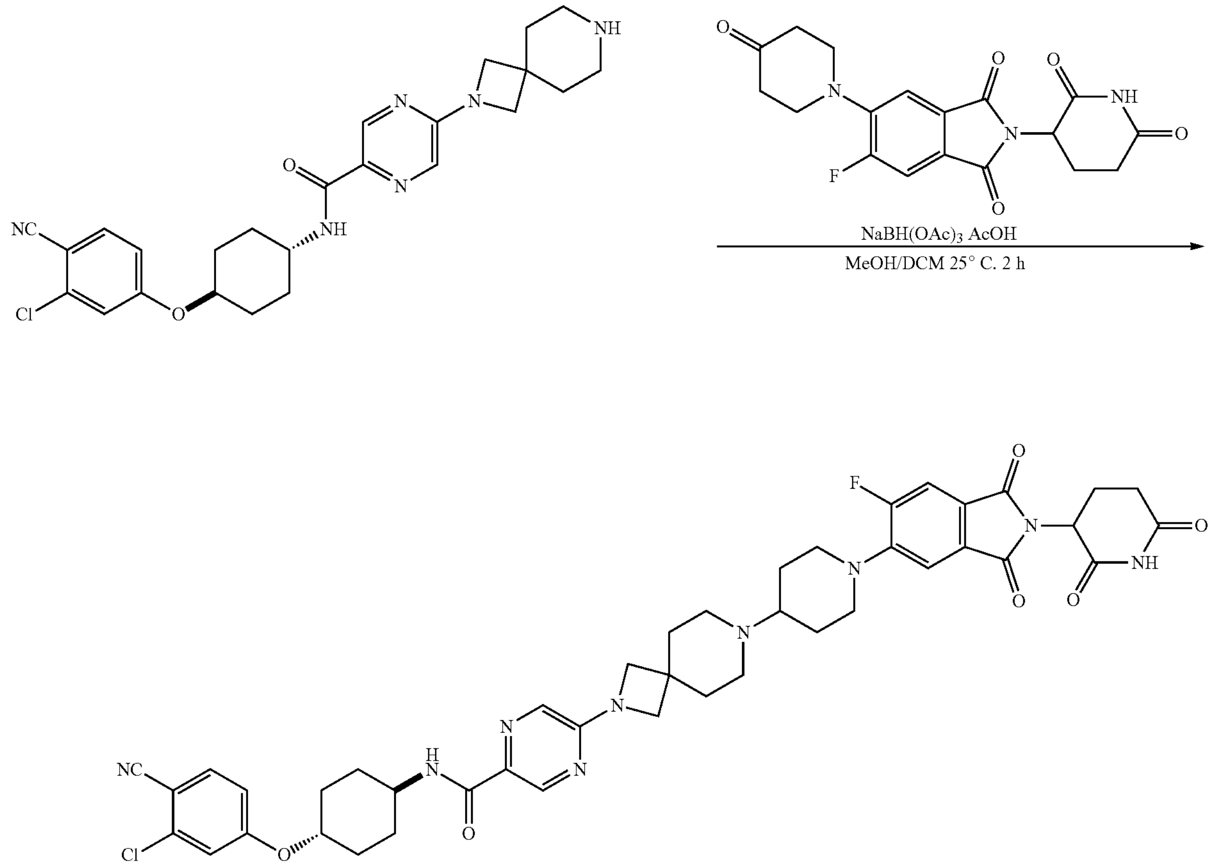

242

LC/MS (ESI$^+$) calcd for $C_{43}H_{45}ClFN_9O_6$ $[M+H]^+$ m/z, 838.3; found 838.3.

$^1$H NMR (400 MHz, $CDCl_3$) δ 8.83 (d, J=1.2 Hz, 1H), 8.24 (s, 1H), 7.59 (d, J=1.1 Hz, 1H), 7.56 (d, J=8.7 Hz, 1H), 7.47 (d, J=10.9 Hz, 1H), 7.39 (d, J=7.2 Hz, 2H), 6.99 (d, J=2.4 Hz, 1H), 6.85 (dd, J=8.7, 2.4 Hz, 1H), 4.94 (dd, J=12.3, 5.3 Hz, 1H), 4.35-4.25 (m, 1H), 4.08-3.98 (m, 1H), 3.90 (s, 4H), 3.73 (d, J=11.9 Hz, 2H), 2.95-2.83 (m, 4H), 2.82-2.71 (m, 2H), 2.66 (d, J=30.0 Hz, 4H), 2.23-2.10 (m, 5H), 1.94 (s, 6H), 1.84-1.61 (m, 6H), 1.46 (dd, J=22.8, 10.5 Hz, 2H).

243: Synthesis of N-((1r,4r)-4-(3-chloro-4-cyano-phenoxy)cyclohexyl)-5-(4-((2-(2,6-dioxopiperidin-3-yl)-1,3-dioxoisoindolin-5-yl)-2,7-diazaspiro[3.5] nonan-7-yl) methyl)piperidin-1-yl)-1,3,4-thiadiazole-2-carboxamide

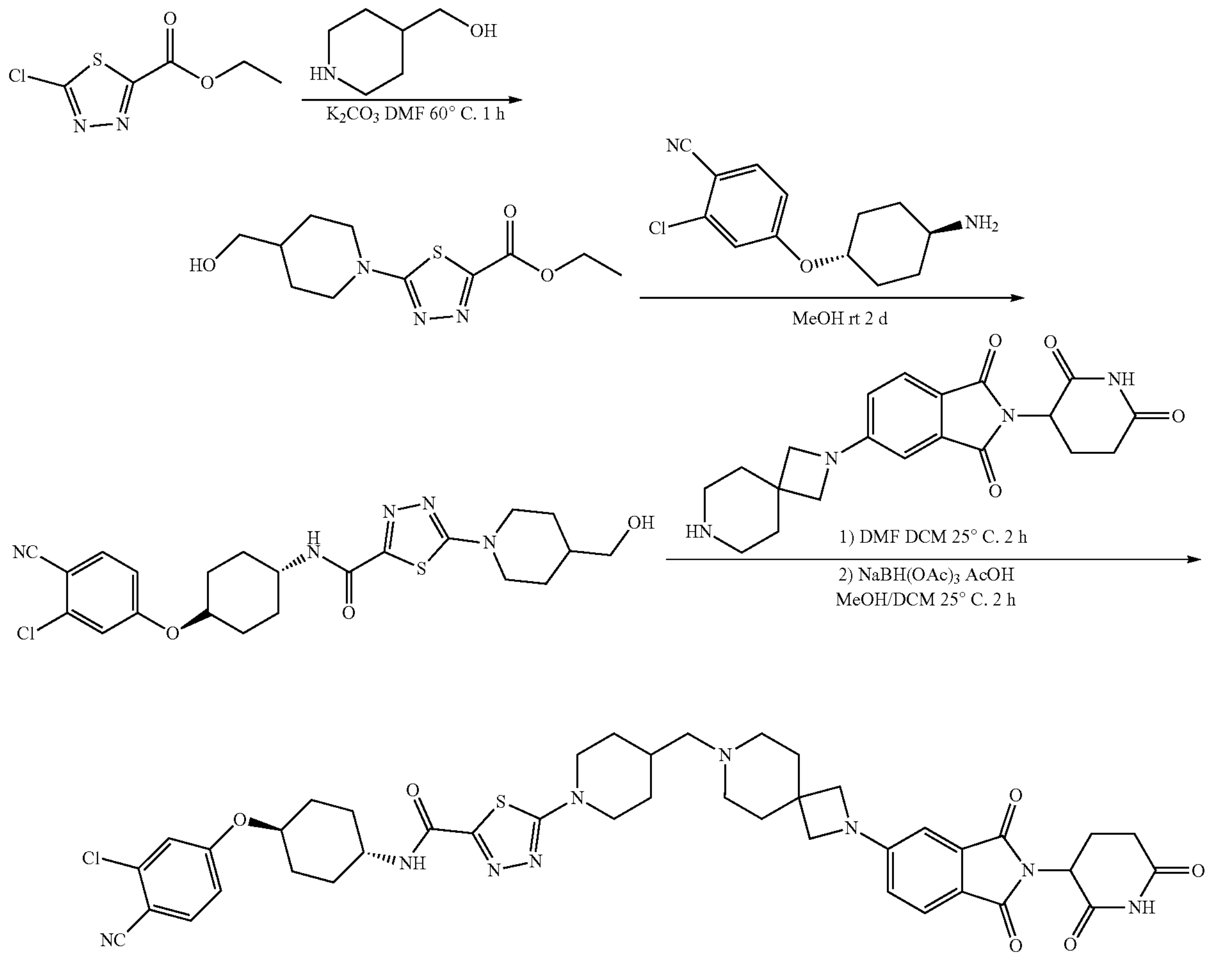

243

1. Synthesis of compound ethyl 5-(4-(hydroxymethyl)piperidin-1-yl)-1,3,4-thiadiazole-2-carboxylate Compound ethyl 5-chloro-1,3,4-thiadiazole-2-carboxylate (200 mg, 1.04 mmol), 4-hydroxymethylpiperidine (179 mg, 1.56 mmol), potassium carbonate (287 mg, 2.08 mmol) and DMF (5 mL) were sequentially added to a reactor. Under the nitrogen protection, the solution was allowed to react 1 h at 60° C. The reaction was completed by TLC detection, to which was added water, and then extracted three times with ethyl acetate. The organic phase was washed two times with saturated brine, dried, rotatory evaporated to dry, and separated by pre-TLC, to provide compound ethyl 5-(4-(hydroxymethyl)piperidin-1-yl)-1,3,4-thiadiazole-2-carboxylate as a white solid (167 mg, 0.61 mmol), with a yield of 59%. LC/MS ($ESI^+$) calcd for $C_{13}H_{17}N_3O_3S$ $[M+H]^+$ m/z, 272.1; found, 272.1.

2. N-(1r,4r)-4-(3-chloro-4-cyanophenoxy)cyclohexyl)-5-(4-(hydroxymethyl) piperidin-1-yl)-1,3,4-thiadiazole-2-carboxamide Compound ethyl 5-(4-(hydroxymethyl)piperidin-1-yl)-1,3,4-thiadiazole-2-carboxylate (80 mg, 0.29 mmol), 4-((1r,4r)-4-aminocyclohexyl)oxy)-2-chlorobenzonitrile (110 mg, 0.44 mmol) and absolute methanol (1 mL) were sequentially added to the reactor, and the reaction solution was allowed to react under reflux for two days. TLC confirmed the end of the reaction. After the reaction was completed, the solvent was removed by rotatory evaporation, and the residue was purified by pre-TLC to obtain N-(1r,4r)-4-(3-chloro-4-cyanophenoxy)cyclohexyl)-5-(4-(hydroxymethyl)piperidin-1-yl)-1,3,4-thiadiazole-2-carboxamide as a pale yellow solid (88 mg, 0.18 mmol), with a yield of 63%; LC/MS ($ESI^+$) calcd for $C_{22}H_{26}ClN_5O_3S$ $[M+H]^+$ m/z, 476.1; found, 476.1.

3. Synthesis of Compound N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl)methyl)piperidin-1-yl)-1,3,4-thiadiazole-2-carboxamide Compound N-(1r,4r)-4-(3-chloro-4-cyanophenoxy)cyclohexyl)-5-(4-(hydroxymethyl) piperidin-1-yl)-1,3,4-thiadiazole-2-carboxamide (44 mg, 0.92 mmol) was dissolved in 2 mL of DCM, to which was added DMP (47 mg, 0.11 mmol), and the mixture was stirred and reacted at room temperature for 2 h. The completion of the reaction was detected by TLC. The reaction solution was filtered, and the filter cake was rinsed with DCM. The filtrate was rotatory evaporated to dry to obtain a crude product, to which was added 2-(2,6-dioxopiperidin-3-yl)-4-(piperazin-1-yl)isoindole-1,3-dione (41 mg, 0.10 mmol) and 2 mL of DCM/MeOH (1:1). The reaction was dissolved, and then glacial acetic acid (11 mg, 0.60 mmol) was added. The mixture was stirred and reacted at room temperature for 30 min, to which was then added sodium triacetylborohydride (78 mg, 0.60 mmol). The reaction was stirred and reacted at room temperature for 2 h. The reaction was completed by TLC detection, to which was added the saturated aqueous solution of sodium bicarbonate, and then extracted with dichloromethane three times. The organic phase was combined, dried, rotatory evaporated to dry, and separated by pre-TLC to obtain compound N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5] nonan-7-yl)methyl)piperidin-1-yl)-1,3,4-thiadiazole-2-carboxamide as an off-white solid (50 mg, 0.058 mmol), with a yield of 63%.

LC/MS (ESI+) calcd for $C_{42}H_{46}ClN_9O_6S$ $[M+H]^+$ m/z, 840.3; found, 840.3.

$^1$H NMR (400 MHz, $CDCl_3$) δ 8.08 (s, 1H), 7.64 (d, J=8.2 Hz, 1H), 7.56 (d, J=8.7 Hz, 1H), 7.00 (t, J=5.0 Hz, 2H), 6.84 (dd, J=8.7, 2.4 Hz, 1H), 6.78 (d, J=1.9 Hz, 1H), 6.51 (d, J=8.4 Hz, 1H), 4.94 (dd, J=12.3, 5.3 Hz, 1H), 4.36-4.26 (m, 1H), 4.00 (dd, J=23.9, 12.2 Hz, 3H), 3.74 (s, 4H), 3.19 (t, J=11.9 Hz, 2H), 2.94-2.73 (m, 3H), 2.38 (s, 3H), 2.15 (ddd, J=17.9, 11.1, 5.1 Hz, 7H), 1.85 (s, 6H), 1.70-1.57 (m, 4H), 1.53-1.40 (m, 2H), 1.32 (d, J=13.0 Hz, 2H).

244: Synthesis of N-((1r,4r)-4-(3-chloro-4-cyanophenoxy)cyclohexyl)-5-(4-((2-(2,6-dioxopiperidin-3-yl)-6-fluoro-1,3-dioxoisoindolin-5-yl)-2,7-diazaspiro[3.5]nonan-7-yl)methyl)piperidin-1-yl)-1,3,4-thiadiazole-2-carboxamide

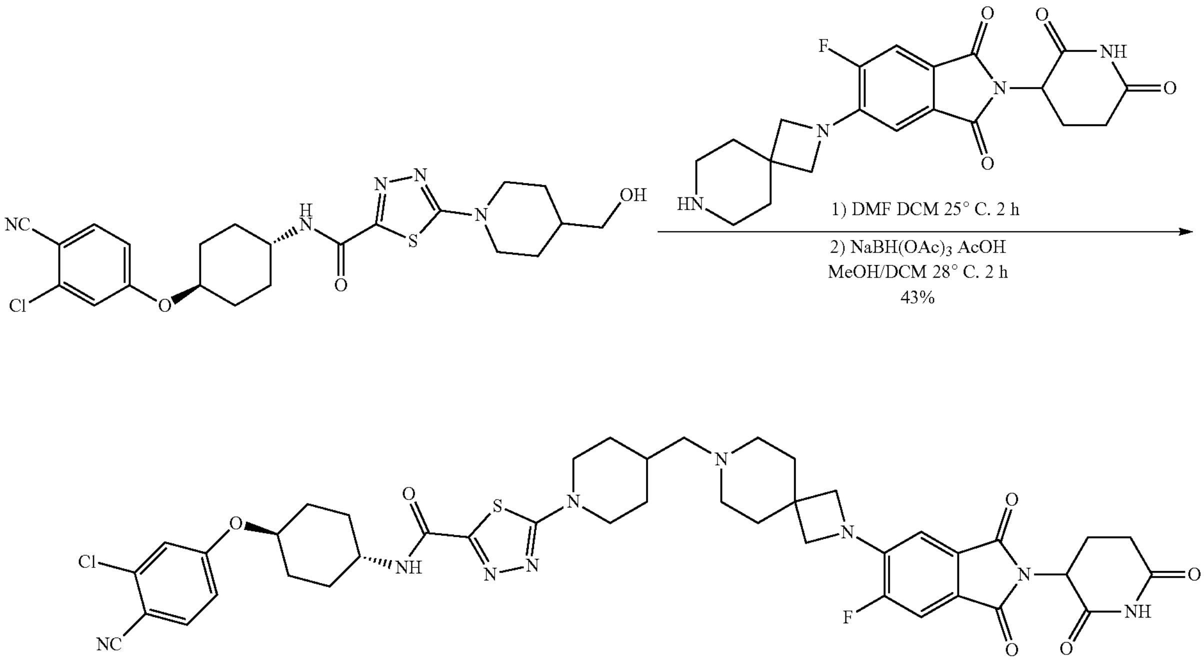

244

LC/MS (ESI+) calcd for $C_{42}H_{46}ClFN_9O_6S$ $[M+H]^+$ m/z, 858.3; found 858.3.

$^1$H NMR (400 MHz, $CDCl_3$) δ 7.61-7.52 (m, 1H), 7.36 (d, J=10.9 Hz, 1H), 7.01 (d, J=2.4 Hz, 1H), 6.86 (dd, J=8.8, 2.4 Hz, 1H), 6.81 (d, J=7.5 Hz, 1H), 4.91 (dd, J=12.1, 5.6 Hz, 1H), 4.33 (t, J=9.9 Hz, 1H), 3.99 (dd, J=19.1, 11.8 Hz, 3H), 3.90 (d, J=1.9 Hz, 4H), 3.20 (dd, J=12.6, 10.3 Hz, 2H), 2.44 (s, 4H), 2.26 (d, J=6.9 Hz, 2H), 2.23-2.10 (m, 5H), 2.05 (s, 1H), 1.98-1.79 (m, 7H), 1.66 (dt, J=20.0, 10.1 Hz, 2H), 1.50 (dd, J=22.0, 11.4 Hz, 2H), 1.39-1.29 (m, 2H

245: N-((1r,4R)-4-(3-chloro-4-cyanophenoxy)cyclohexyl)-1-((1r,4R)-4-((2-(2,6-dioxopiperidin-3-yl)-1,3-dioxoisoindolin-5-yl)-2,7-diazaspiro[3.5]nonan-7-yl)methyl)cyclohexyl)-1H-pyrazole-4-carboxamide

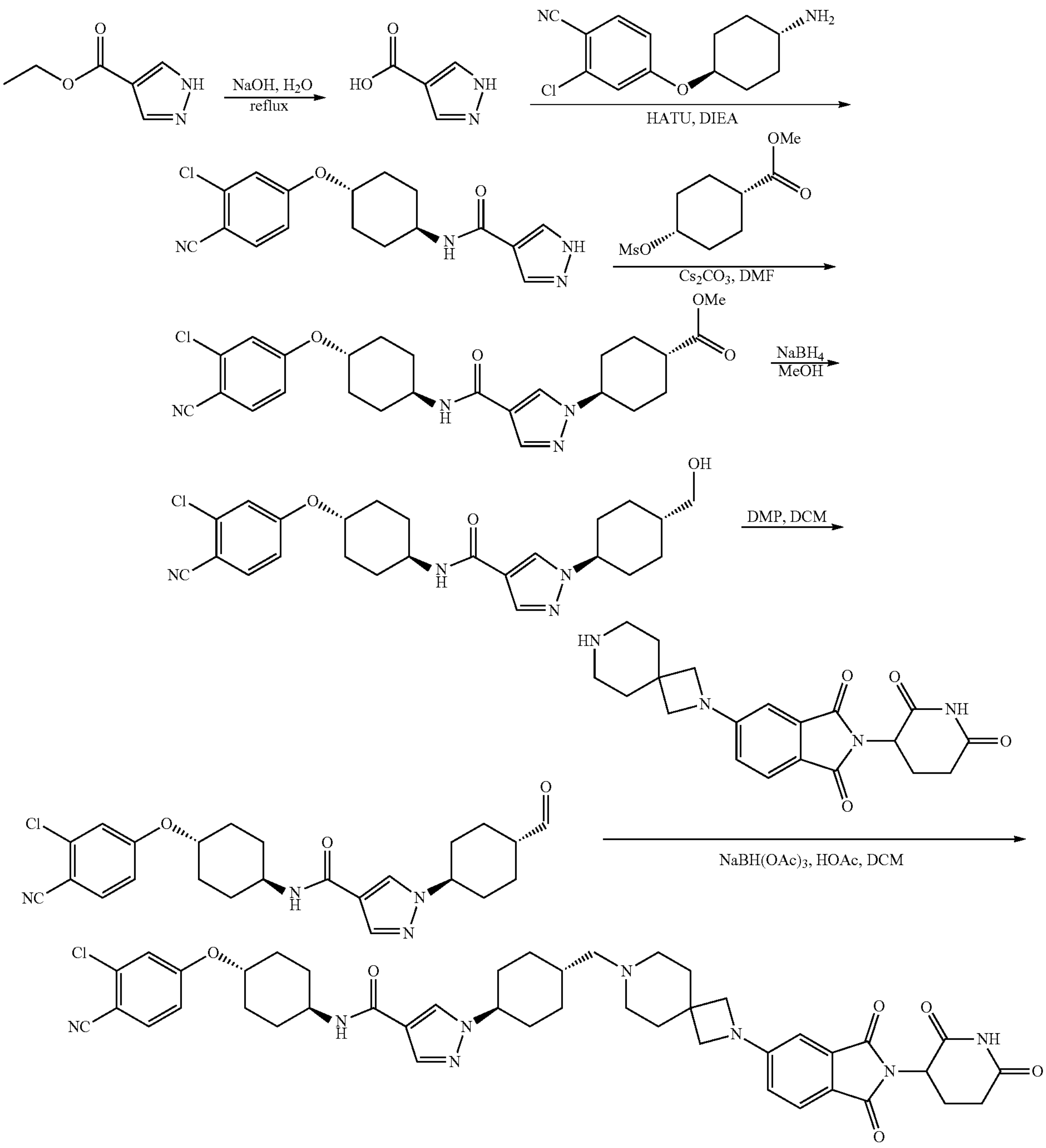

248

Step 1: Ethyl 1H-pyrazole-4-carboxylate (1.4 g, 10 mmol) and NaOH (0.8 g, 20 mmol) were successively added to 10 mL of water, and the mixture was heated and reacted under reflux for 2 h. TLC indicated the completion of the reaction, and the reaction solution was naturally cooled to room temperature, whose pH was adjusted to about 4-5 with 6 N hydrochloric acid solution. The solution was filtered to obtain compound 1H-pyrazole-4-carboxylic acid (1.05 g).

Step 2: 1H-pyrazole-4-carboxylic acid (336 mg, 3 mmol) was dissolved in 10 mL of DMF, to which were successively added DIEA (774 mg, 6 mmol) and HATU (1.36 g, 3.6 mmol). The mixture was stirred at room temperature for 30 min, to which was added 4-(((1r,4r)-4-aminocyclohexyl)oxy)-2-chlorobenzonitrile (750 mg, 3 mmol). The solution was allowed to react 6 h. After the reaction was completed by TLC detection, the reaction was quenched with the saturated solution of ammonium chloride (5 mL). The reaction solution was extracted with ethyl acetate (10 mL), and the water layer was further back-extracted once. The organic layers were combined, washed with saturated brine, dried over anhydrous sodium sulfate, concentrated, and purified by column chromatography, to provide compound N-((1r,4r)-4-(3-chloro-4-cyanophenoxy) cyclohexyl)-1H-pyrazole-4-formamide (490 mg), with a yield of 48%.

Step 3: N-((1r,4r)-4-(3-chloro-4-cyanophenoxy)cyclohexyl)-1H-pyrazole-4-formamide (344 mg, 1 mmol) and methyl (1s,4s)-4-((methylsulfonyl)oxy)cyclohexane-1-carboxylate (708 mg, 3 mmol) were dissolved in 4 mL of DMF, to which was added potassium carbonate (414 mg, 3 mmol). The solution was allowed to react overnight at 80° C. The reaction was quenched with 5 mL of saturated sodium bicarbonate solution, extracted with 10 mL of ethyl acetate, and the aqueous layer was back-extracted once. The organic layer was combined, washed with saturated brine, dried over anhydrous sodium sulfate, concentrated, and purified by column chromatography to obtain 144 mg of compound methyl (1R,4r)-4-(4-((1r,4R)-4-(3-chloro-4-cyanophenoxy) cyclohexyl)carbamoyl)-1H-pyrazol-1-yl)cyclohexane-1-carboxylate, with a yield of 30%.

Step 4: Methyl (1R,4r)-4-(4-((1r,4R)-4-(3-chloro-4-cyanophenoxy)cyclohexyl) carbamoyl)-1H-pyrazol-1-yl)cyclohexane-1-carboxylate (144 mg, 0.3 mmol) was dissolved in 10 mL of methanol, to which was then added sodium borohydride (58 mg, 1.5 mmol) in an ice bath. After that, the reaction solution was slowly warmed to room temperature, and the solution was stirred overnight at 60° C. The reaction was quenched with the saturated solution of ammonium chloride (5 mL). The reaction solution was extracted with ethyl acetate (10 mL). The organic layer was concentrated under reduced pressure, and the residue was separated and purified by TLC, to provide 106 mg of compound N-((1r, 4R)-4-(3-chloro-4-cyanophenoxy)cyclohexyl)-1-((1r,4R)-4-(hydroxymethyl)cyclohexyl)-1H-pyrazole-4-formamide, with a yield of 77%.

Step 5: N-((1r,4R)-4-(3-chloro-4-cyanophenoxy)cyclohexyl)-1-((1r,4R)-4-(hydroxymethyl)cyclohexyl)-1H-pyrazole-4-formamide (106 mg, 0.23 mmol) was dissolved in 4 mL of dichloromethane, to which was added DMP (127 mg, 0.3 mmol), and the mixture was allowed to react overnight. The reaction solution was filtered, concentrated, and purified by column chromatography, to provide 88 mg of N-((1r, 4R)-4-(3-chloro-4-cyanophenoxy)cyclohexyl)-1-((1r,4R)-4-formylcyclohexyl)-1H-pyrazole-4-formamide, with a yield of 85%.

Step 6: N-((1r,4R)-4-(3-chloro-4-cyanophenoxy)cyclohexyl)-1-((1r,4R)-4-formylcyclohexyl)-1H-pyrazole-4-formamide (45 mg, 0.1 mmol) was dissolved in 3 mL of dichloromethane, to which were successively added 2-(2,6-dioxopiperidin-3-yl)-5-(2,7-diazaspiro[3.5]nonan-2-yl) isoindole-1,3-dione (76 mg, 0.2 mmol) and glacial acetic acid (12 mg, 0.02 mmol). The mixture was stirred at room temperature for 30 min, to which was then added sodium triacetylborohydride (78 mg, 0.60 mmol). The solution was allowed to react 2 h at room temperature. The reaction was quenched with 5 mL of saturated sodium bicarbonate solution, and extracted with 10 mL of ethyl acetate. The organic layer was concentrated under reduced pressure, and then separated purified by TLC to obtain 30 mg of compound N-((1r,4R)-4-(3-chloro-4-cyanophenoxy)cyclohexyl)-1-((1r,4R)-4-((2-(2,6-dioxopiperidin-3-yl)-1,3-dioxoisoindol-5-yl)-2,7-diazaspiro[3.5]nonan-7-yl)methyl)cyclohexyl)-1H-pyrazole-4-carboxamide, with a yield of 37%. $^1$H NMR (400 MHz, $CDCl_3$) δ 7.91 (s, 1H), 7.70 (d, J=5.6 Hz, 1H), 7.64 (d, J=8.0 Hz, 1H), 7.55 (d, J=8.8 Hz, 1H), 6.98 (d, J=2.4 Hz, 1H), 6.84 (dd, J=8.8, 2.4 Hz, 1H), 6.77 (d, J=2.0 Hz, 1H), 6.50 (dd, J=8.8, 2.0 Hz, 1H), 5.60 (d, J=8.0 Hz, 1H), 4.93 (dd, J=12.0, 5.2 Hz, 1H), 4.16 (m, 4H), 3.73 (s, 4H), 3.02 (s, 1H), 2.81 (m, 4H), 2.37 (s, 4H), 2.17 (m, 8H), 2.01 (m, 2H), 1.86 (m, 4H), 1.40 (m, 3H), 1.09 (m, 3H). LC/MS ($ESI^+$) calcd for $C_{44}H_{49}ClN_8O_6$ ($[M+H]^+$) m/z: 821.4; found 821.4.

246: N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5] nonan-7-yl)methyl)cyclohexyl)-1H-pyrazole-4-carboxamide

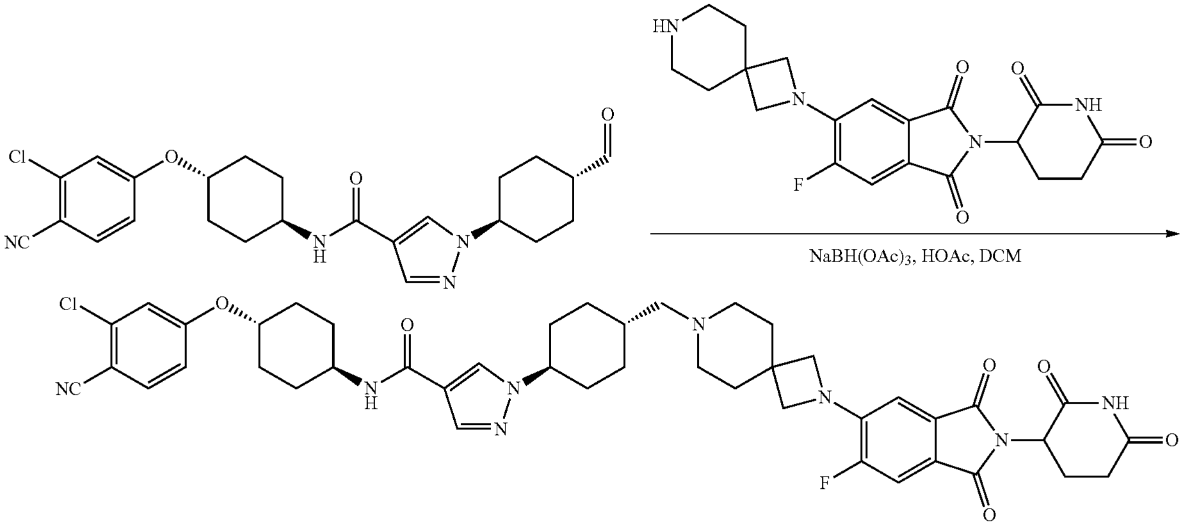

246

N-((1r,4R)-4-(3-chloro-4-cyanophenoxy)cyclohexyl)-1-((1r,4R)-4-formylcyclohexyl)-1H-pyrazole-4-formamide (38 mg, 0.08 mmol) was dissolved in 3 mL of dichloromethane, to which were successively added 2-(2,6-dioxopiperidin-3-yl)-5-fluoro-6-(2,7-diazaspiro[3.5]nonan-2-yl)isoindole-1,3-dione (40 mg, 0.1 mmol) and glacial acetic acid (6 mg, 0.01 mmol). The mixture was stirred at room temperature for 30 min, to which was then added sodium triacetylborohydride (53 mg, 0.25 mmol). The solution was allowed to react 2 h at room temperature. The reaction was quenched with 5 mL of saturated sodium bicarbonate solution, and extracted with 10 mL of ethyl acetate. The organic layer was concentrated under reduced pressure, and then separated purified by TLC to obtain 24 mg of compound N-((1r,4R)-4-(3-chloro-4-cyanophenoxy)cyclohexyl)-1-((1r,4R)-4-((2-(2,6-dioxopiperidin-3-yl)-6-fluoro-1,3-dioxoisoindolin-5-yl)-2,7-diazaspiro[3.5]nonan-7-yl)methyl)cyclohexyl)-1H-pyrazole-4-carboxamide, with a yield of 36%. $^1H$ NMR (400 MHz, $CDCl_3$) δ 8.24 (s, 1H), 7.94 (s, 1H), 7.72 (d, J=5.6 Hz, 1H), 7.55 (d, J=8.8 Hz, 1H), 7.35 (d, J=7.6 Hz, 1H), 6.98 (d, J=2.4 Hz, 1H), 6.84 (dd, J=8.8, 2.4 Hz, 1H), 6.80 (d, J=7.6 Hz, 1H), 5.67 (d, J=8.0 Hz, 1H), 4.91 (dd, J=12.0, 5.6 Hz, 1H), 4.27 (m, 1H), 4.04 (m, 2H), 3.89 (s, 4H), 2.80 (m, 8H), 1.67 (m, 8H), 1.31 (m, 15H). LC/MS ($ESI^+$) calcd for $C_{44}H_{48}ClFN_8O_6$ ($[M+H]^+$) m/z: 839.4; found 839.4.

247: N-((1r,4r)-4-(3-chloro-4-cyanophenoxy)cyclohexyl)-6-(4-((2-(2,6-dioxopiperidin-3-yl)-4-oxo-3,4-dihydroquinazoline-7-yl)-2,7-diazaspiro[3.5] nonan-7-yl)methyl)piperidin-1-yl)pyridazine-3-carboxamide

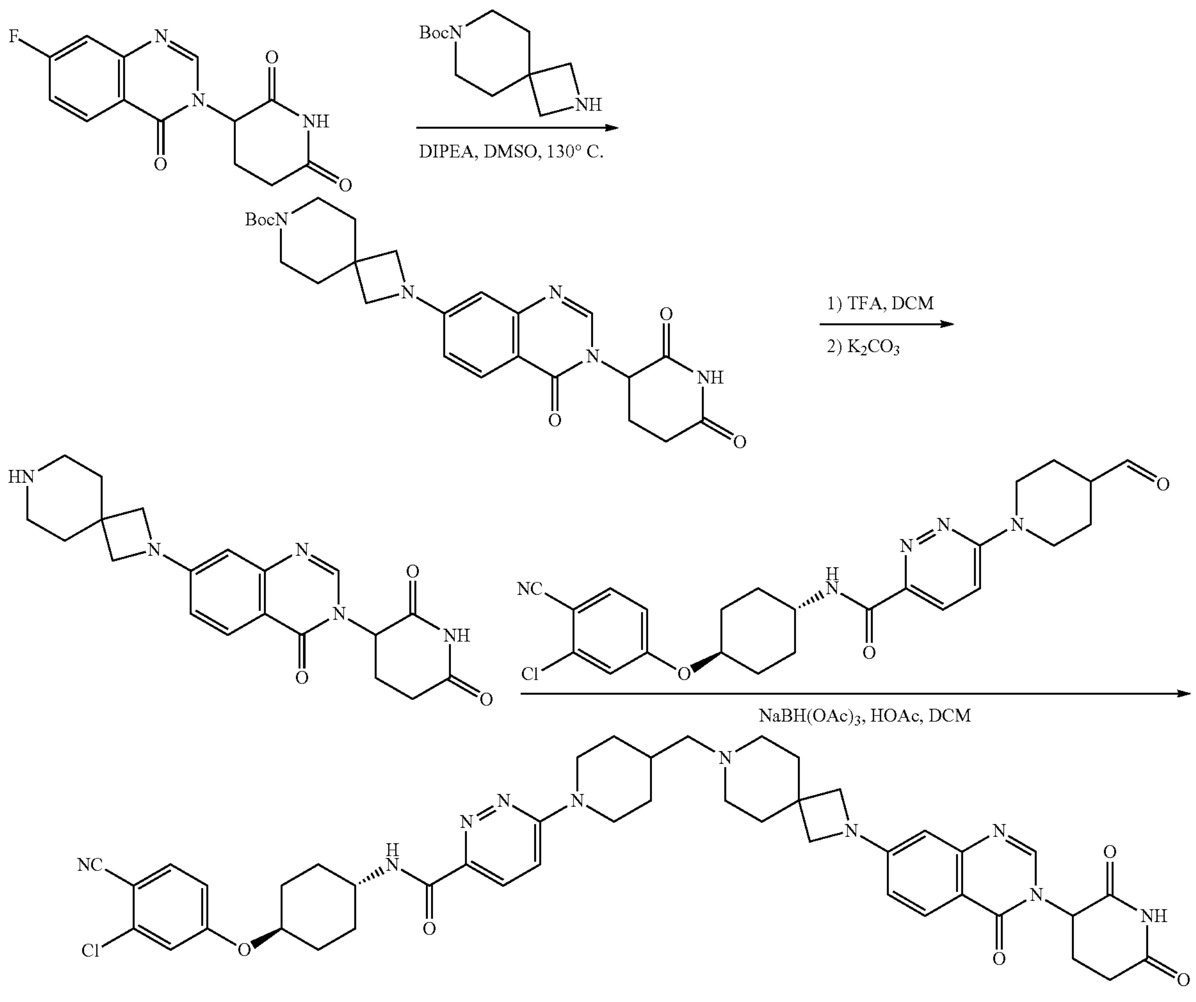

247

Step 1: 3-(7-fluoro-4-oxoquinazolin-3(4H)-yl)piperidine-2,6-dione (275 mg, 1 mmol) and t-butyl 2,7-diazaspiro[3.5] nonane-7-carboxylate (226 mg, 1 mmol) were dissolved in 4 mL of DMSO, to which was added DIPEA (258 mg, 2 mmol). Under $N_2$ protection, the solution was allowed to react 2 h at 130° C. The reaction was quenched with the saturated solution of ammonium chloride (5 mL). The reaction solution was extracted with ethyl acetate (10 mL), and the water layer was further back-extracted once. The organic layers were combined, washed with saturated brine, dried over anhydrous sodium sulfate, concentrated, and purified by column chromatography, to provide 112 mg of compound t-butyl 2-(3-(2,6-dioxopiperidin-3-yl)-4-oxo-3,4-dihydroquinazoline-7-yl)-2,7-diazaspiro[3.5]nonane-7-carboxylate, with a yield of 23%.

Step 2: t-butyl 2-(3-(2,6-dioxopiperidin-3-yl)-4-oxo-3,4-dihydroquinazoline-7-yl)-2,7-diazaspiro[3.5]nonane-7-carboxylate (112 mg, 0.23 mmol) was dissolved in 5 mL of dichloromethane, to which was added 5 mL of trifluoroacetic acid, and the mixture was allowed to react at room temperature for 2 h. The solution was concentrated under reduced pressure to remove the solvent and trifluoroacetic acid, to which were successively added 5 mL of dichloromethane and 0.5 mL of saturated sodium bicarbonate solution. The resultant solution was extracted with 5 mL of dichloromethane several times. The organic layers were combined, dried over anhydrous sodium sulfate, concentrated, and purified by column chromatography, to provide 46 mg of compound 3-(4-oxo-7-(2,7-diazaspiro[3.5]nonan-2-yl)quinazolin-3(4H)-yl)piperidine-2,6-dione, with a yield of 53%.

Step 3: 3-(4-oxo-7-(2,7-diazaspiro[3.5]nonan-2-yl)quinazolin-3(4H)-yl)piperidine-2,6-dione (46 mg, 0.12 mmol) was dissolved in 3 mL of dichloromethane, to which were successively added N-((1r,4r)-4-(3-chloro-4-cyanophenoxy) cyclohexyl)-6-(4-formylpiperidin-1-yl)pyridazine-3-formamide (93 mg, 0.2 mmol) and glacial acetic acid (12 mg, 0.02 mmol). The mixture was stirred at room temperature for 30 min, to which was then added sodium triacetylborohydride (51 mg, 0.24 mmol). The solution was allowed to react 2 h at room temperature. The reaction was quenched with 5 mL of saturated sodium bicarbonate solution, and extracted with 10 mL of ethyl acetate. The organic layer was concentrated under reduced pressure, and then separated purified by TLC to obtain 21 mg of compound N-((1r,4r)-4-(3-chloro-4-cyanophenoxy) cyclohexyl)-6-(4-((2-(2,6-dioxopiperidin-3-yl)-4-oxo-3,4-dihydroquinazoline-7-yl)-2,7-diazaspiro[3.5] nonan-7-yl)methyl)piperidin-1-yl)pyridazine-3-carboxamide, with a yield of 21%. $^1$H NMR (400 MHz, $CDCl_3$) δ 8.59 (s, 1H), 8.05 (d, J=8.8 Hz, 1H), 7.96 (d, J=9.2 Hz, 1H), 7.89 (d, J=8.0 Hz, 1H), 7.55 (d, J=8.8 Hz, 1H), 6.98 (m, 2H), 6.84 (dd, J=8.4, 2.4 Hz, 1H), 6.55 (dd, J=7.6, 2.4 Hz, 1H), 6.50 (d, J=2.4 Hz, 1H), 5.14 (d, J=2.8 Hz, 1H), 4.53 (m, 5H), 4.31 (m, 1H), 4.05 (m, 1H), 3.73 (s, 4H), 3.48 (s, 2H), 3.03 (t, J=12.4 Hz, 2H), 2.92 (m, 1H), 2.77 (m, 2H), 2.21 (m, 7H), 1.69 (m, 4H), 1.44 (m, 4H), 0.85 (m, 4H). LC/MS ($ESI^+$) calcd for $C_{44}H_{49}ClN_{10}O_5$ ($[M+H]^+$) m/z: 834.4; found 834.4.

248: 2-chloro-4-((1r,3r)-3-(5-(4-((4-(2-(2, 6-dioxopiperidin-3-yl)-1-oxoisoindolin-5-yl)piperazin-1-yl) methyl)piperidin-1-yl)-1-oxoisoindolin-2-yl))-2,2,4, 4-tetramethylcyclobutoxy)benzonitrile

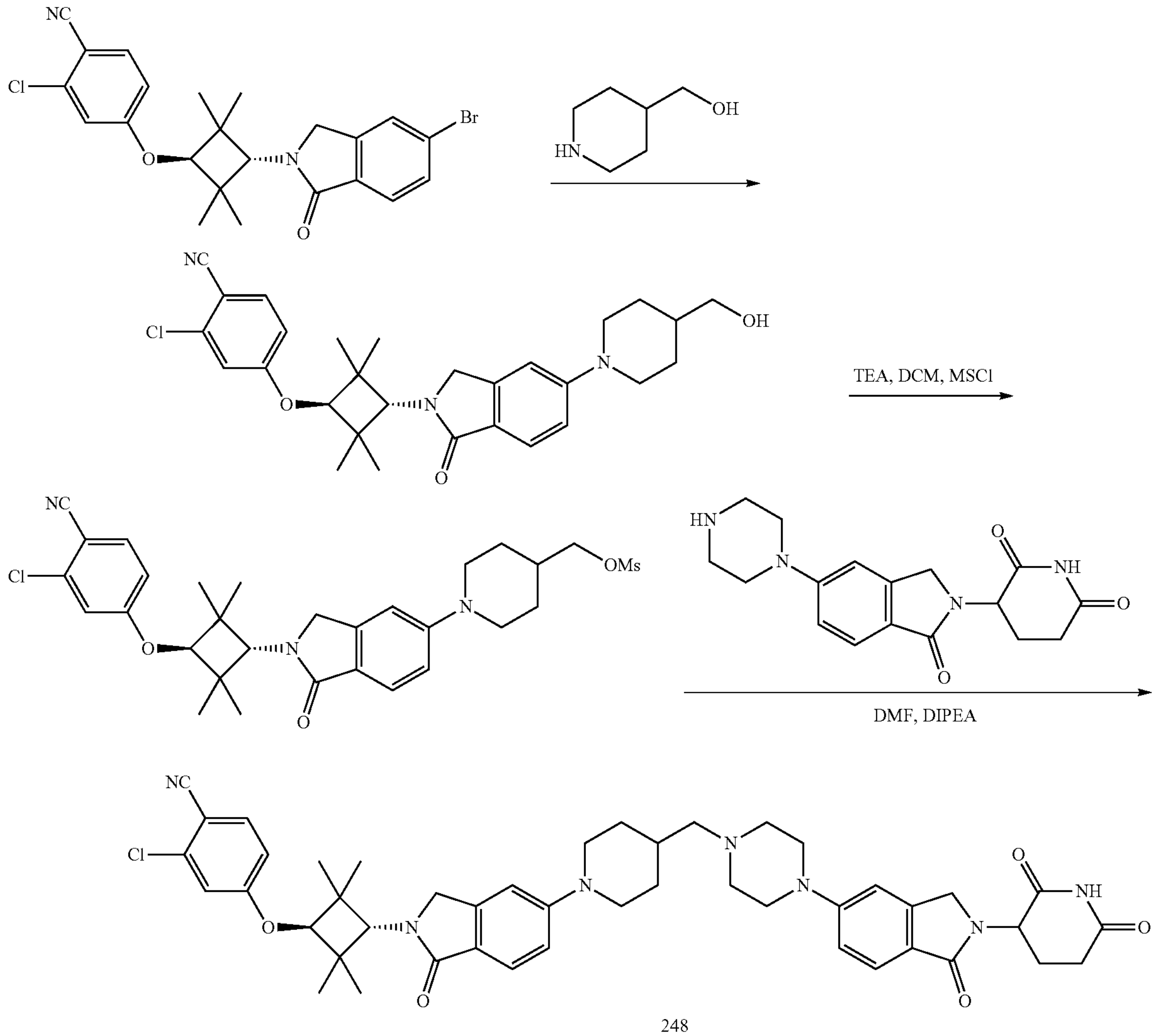

248

1. Synthesis of Intermediate 24-1: 2-chloro-4-((1r, 3r)-3-(5-(4-(hydroxymethyl) piperidin-1-yl)-1-oxoisoindolin-2-yl))-2,2,4,4-tetramethylcyclobutoxy) benzonitrile Compounds 4-((1R,3R)-3-(5-bromo-1-oxoisoindolin-2-yl))-2,2,4,4-tetramethyl cyclobutoxy)-2-chlorobenzonitrile (1-1) (189 mg, 0.4 mmol) and piperidin-4-ylmethanol (69 mg, 0.6 mmol) were dissolved in 3 mL of toluene, to which were added 1 mL of triethylamine, $Pd(dppf)_2Cl_2$ (30 mg) and CuI (150 mg). Under $N_2$ protection, the reaction solution was heated to 90-100° C., and further stirred and reacted for 12 h. After completion of the reaction, the solvent was removed by evaporation under reduced pressure. The crude product was purified by TLC (PE:EA=1:1), to provide 163 mg of intermediate 24-1, with a yield of 80%. MS (ES): m/z=508 $[M+H]^+$.

2. (1-(2-((1r,3r)-3-(3-chloro-4-cyanophenoxy)-2,2,4, 4-tetramethylcyclobutyl)-1-oxoisoindolin-5-yl)piperidine-4-yl)methyl methanesulfonate The intermediate (508 mg, 1 mmol) obtained in the previous step was dissolved in 10 mL of DCM, to which was added TEA (152 mg, 1.5 mmol), and then methylsulfonyl chloride (137 mg, 1.2 mmol) was added dropwise in an ice bath. The mixture was stirred and reacted for 3 h. After the reaction was completed, 5 mL of water and 20 mL of dichloromethane were added for extraction. The organic phase obtained was evaporated under reduced pressure to remove the solvent. The crude product was not purified and directly used in the next reaction.

3. 2-Chloro-4-((1r,3r)-3-(5-(4-((4-(2-(2, 6-dioxopiperidin-3-yl)-1-oxoisoindolin-5-yl) piperazin-1-yl) methyl)piperidin-1-yl)-1-oxoisoindolin-2-yl))-2,2,4, 4-tetramethyl cyclobutoxy)benzonitrile Compound (1-(2-((1r,3r)-3-(3-chloro-4-cyanophenoxy)-2,2,4,4-tetramethyl cyclobutyl)-1-oxoisooctanol-5-yl)piperidine-4-yl)methyl methanesulfonate (intermediate 24-2) (76 mg, 0.13 mmol) was dissolved in 2 mL of DMSO, to which was added 3-(1-oxo-5-(piperazin-1-yl)isoindolin-2-yl)piperidine-2,6-dione (43 mg, 0.13 mmol). The reaction solution was heated to 80° C., and further stirred for 2 h to complete the reaction. After completion of the reaction, the reaction solution was cooled to room temperature, to which were added 10 mL of water and 15 mL of ethyl acetate for extraction. The organic phase obtained was evaporated under reduced pressure to remove the solvent. The crude product was purified by TLC (DCM:MeOH=10:1) to obtain 62 mg of the final product, with a yield of 58%. MS (ES): m/z=818 $[M+H]^+$.

$^1$H NMR (400 MHz, DMSO-$d_6$) δ 10.95 (s, 1H), 7.91 (d, J=8.7 Hz, 1H), 7.53 (d, J=8.4 Hz, 1H), 7.47 (d, J=9.1 Hz, 1H), 7.29 (d, J=2.2 Hz, 1H), 7.15-6.99 (m, 5H), 5.11-5.01 (m, 1H), 4.67 (s, 2H), 4.53 (s, 1H), 4.28 (t, J=16.7 Hz, 3H), 3.87 (d, J=11.9 Hz, 2H), 3.44 (s, 3H), 2.85 (d, J=11.5 Hz, 3H), 2.72-2.55 (m, 1H), 2.45-2.29 (m, 2H), 2.22 (d, J=6.5 Hz, 2H), 2.04-1.74 (m, 6H), 1.39 (s, 6H), 1.22 (d, J=17.3 Hz, 4H), 1.14 (s, 6H).

249: 2-chloro-4-((1r,3r)-3-(5-(4-((4-(2, 6-dioxopiperidin-3-yl)-1, 3-dioxoisoindolin-5-yl)piperazin-1-yl)methyl)piperidin-1-yl)-1-oxoisoindolin-2-yl)-2,2, 4,4-tetramethylcyclobutoxy)benzonitrile

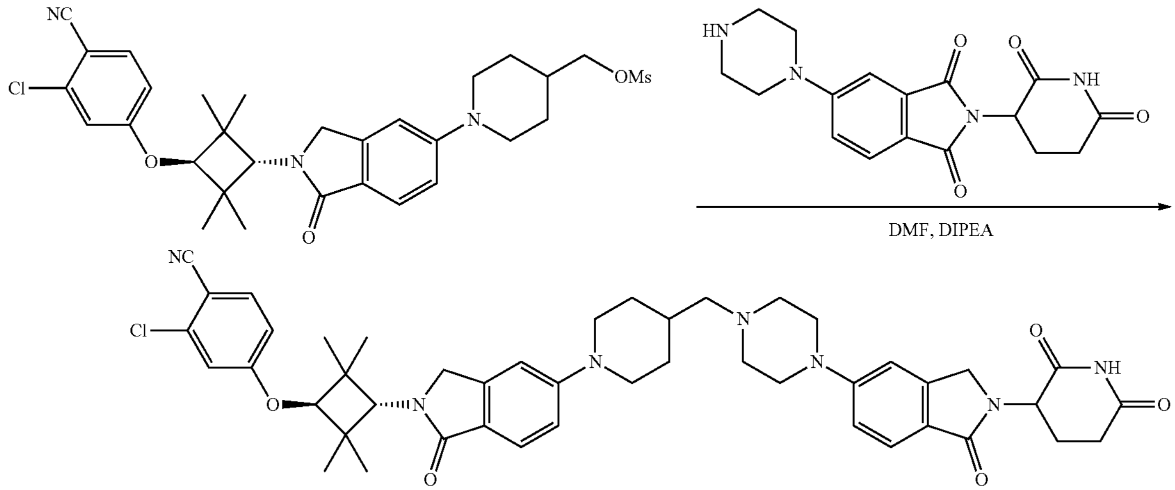

249

Compound (1-(2-((1r,3r)-3-(3-chloro-4-cyanophenoxy)-2,2,4,4-tetramethylcyclobutyl)-1-oxoisoindolin-5-yl)piperidine-4-yl)methyl methanesulfonate (intermediate 24-2) (76 mg, 0.13 mmol) was dissolved in 2 mL of DMSO, to which was added 2-(2,6-dioxopiperidin-3-yl)-5-(piperazin-1-yl) isoindoline-1,3-dione (45 mg, 0.13 mmol). The reaction solution was heated to 80° C., and further stirred for 2 h to complete the reaction. After completion of the reaction, the reaction solution was cooled to room temperature, to which were added 10 mL of water and 15 mL of ethyl acetate for extraction. The organic phase obtained was evaporated under reduced pressure to remove the solvent. The crude product was purified by TLC (DCM:MeOH=10:1) to obtain 61 mg of the final product, with a yield of 56%. MS (ES): m/z=832 $[M+H]^+$.

$^1$H NMR (400 MHz, DMSO-$d_6$) δ 11.09 (s, 1H), 7.91 (d, J=8.7 Hz, 1H), 7.69 (d, J=8.4 Hz, 1H), 7.47 (d, J=9.0 Hz, 1H), 7.30 (t, J=19.4 Hz, 3H), 7.11-7.00 (m, 3H), 5.14-5.04 (m, 1H), 4.67 (s, 2H), 4.53 (s, 1H), 4.29 (s, 1H), 3.87 (d,

J=12.0 Hz, 2H), 3.45 (s, 3H), 2.84 (t, J=11.7 Hz, 3H), 2.58 (d, J=25.3 Hz, 4H), 2.22 (d, J=5.9 Hz, 2H), 2.00 (s, 2H), 1.82 (d, J=9.9 Hz, 3H), 1.39 (s, 6H), 1.30-1.17 (m, 4H), 1.16 (d, J=15.4 Hz, 6H).

250: 2-chloro-4-((1r,3r)-3-(5-(4-((4-(2,6-dioxopiperidin-3-yl)-6-fluoro-3-oxoisoindolin-5-yl)piperazin-1-yl)methyl)piperidin-1-yl)-1-oxoisoindolin-2-yl))-2,2,4,4-tetramethylcyclobutoxy)benzonitrile

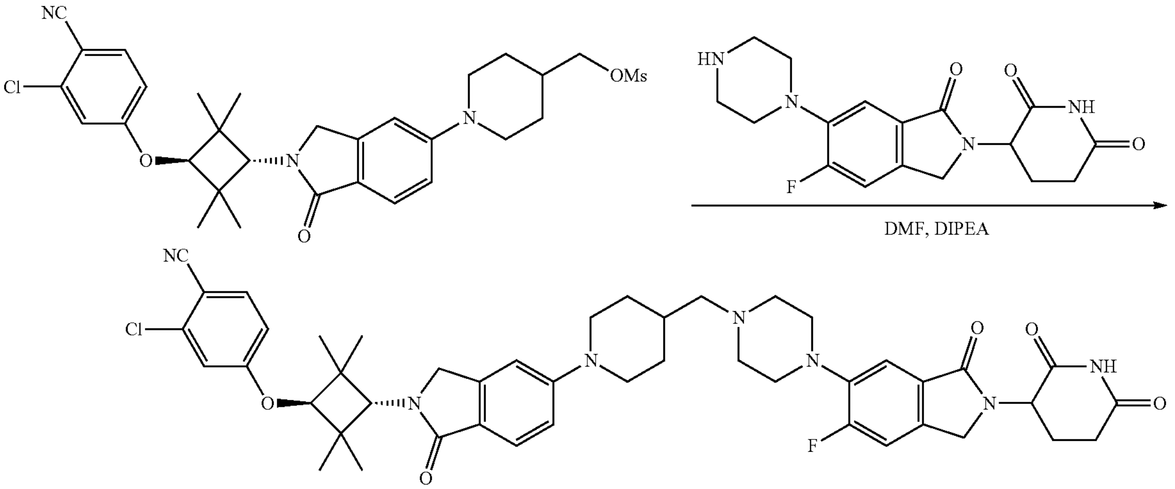

250

Compound (1-(2-((1r,3r)-3-(3-chloro-4-cyanophenoxy)-2,2,4,4-tetramethylcyclobutyl)-1-oxoisooctanol-5-yl)piperidine-4-yl)methyl methanesulfonate (76 mg, 0.13 mmol) was dissolved in 2 mL of DMSO, to which was added 3-(5-fluoro-1-oxo-6-(piperazin-1-yl)isopropanol-2-yl)piperidine-2,6-dione (45 mg, 0.13 mmol). The reaction solution was heated to 80° C., and further stirred for 2 h to complete the reaction. After completion of the reaction, the reaction solution was cooled to room temperature, to which were added 10 mL of water and 15 mL of ethyl acetate for extraction. The organic phase obtained was evaporated under reduced pressure to remove the solvent. The crude product was purified by TLC (DCM:MeOH=10:1) to obtain 63 mg of the final product, with a yield of 56%. MS (ES): m/z=836 $[M+H]^+$.

$^1$H NMR (400 MHz, DMSO-$d_6$) δ 11.03 (s, 1H), 7.93-7.89 (m, 1H), 7.46 (s, 3H), 7.29 (s, 2H), 7.05 (s, 3H), 5.16-5.03 (m, 2H), 4.68 (s, 2H), 4.53 (s, 2H), 4.42-4.34 (m, 2H), 4.29 (s, 2H), 3.93-3.86 (m, 2H), 2.94-2.78 (m, 4H), 2.25-2.21 (m, 2H), 2.03-1.96 (m, 3H), 1.88-1.76 (m, 4H), 1.39 (s, 6H), 1.24 (s, 4H), 1.14 (s, 6H).

251: 2-chloro-4-((1r,3r)-3-(5-(4-((4-(2-(2,6-dioxopiperidin-3-yl)-6-fluoro-1-oxoisoindolin-5-yl)piperazin-1-yl)methyl)piperidin-1-yl)-1-oxoisoindolin-2-yl))-2,2,4,4-tetramethylcyclobutoxy)benzonitrile

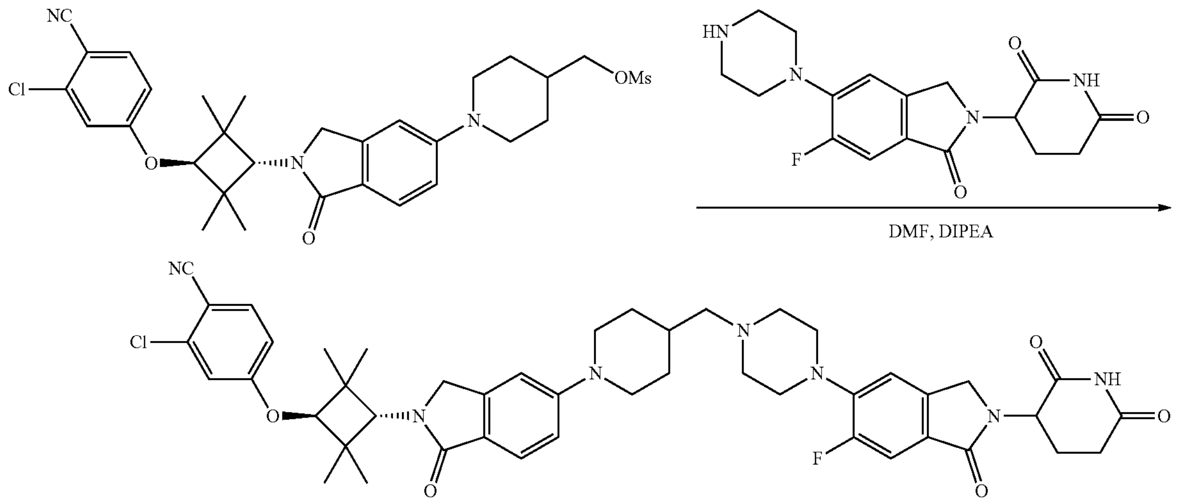

251

Compound (1-(2-((1r,3r)-3-(3-chloro-4-cyanophenoxy)-2,2,4,4-tetramethylcyclobutyl)-1-oxoisooctanol-5-yl)piperidine-4-yl)methyl methanesulfonate (76 mg, 0.13 mmol) was dissolved in 2 mL of DMSO, to which was added 3-(6-fluoro-1-oxo-5-(piperazin-1-yl)isolactam-2-yl)piperidine-2,6-dione (45 mg, 0.13 mmol). The reaction solution was heated to 80° C., and further stirred for 2 h to complete the reaction. After completion of the reaction, the reaction solution was cooled to room temperature, to which were added 10 mL of water and 15 mL of ethyl acetate for extraction. The organic phase obtained was evaporated under reduced pressure to remove the solvent. The crude product was purified by TLC (DCM:MeOH=10:1) to obtain 65 mg of the final product, with a yield of 58%. MS (ES): m/z=836 $[M+H]^+$.

$^1H$ NMR (400 MHz, DMSO-$d_6$) δ 10.99 (s, 1H), 7.91 (d, J=8.8 Hz, 1H), 7.45 (dd, J=16.3, 10.3 Hz, 2H), 7.26 (dd, J=16.5, 4.8 Hz, 2H), 7.07 (d, J=11.7 Hz, 3H), 5.12-5.02 (m, 1H), 4.67 (s, 2H), 4.53 (s, 1H), 4.35 (s, 1H), 4.28 (d, J=4.7 Hz, 2H), 3.87 (d, J=11.9 Hz, 2H), 3.13 (s, 3H), 2.85 (d, J=13.3 Hz, 3H), 2.55 (s, 3H), 2.42-2.31 (m, 111), 2.24 (d, J=6.2 Hz, 2H), 1.99 (s, 2H), 1.82 (d, J=10.9 Hz, 3H), 1.37 (d, J=11.8 Hz, 6H), 1.25 (d, J=9.9 Hz, 4H), 1.14 (s, 6H).

252: N-((1r,4r)-4-(3-chloro-4-cyanophenoxy)cyclohexyl)-6-(4-((5-(2-(2,6-dioxopiperidin-3-yl)-1,3-dioxoisoindolin-5-yl)Hexahydropyrrolo[3,4-c]pyrrol-2(11H)-yl)methyl)piperidin-1-yl)pyridazine-3-formamide 253: N-((1r,4r)-4-(3-chloro-4-cyanophenoxy)cyclohexyl)-6-(4-((5-(2-(2,6-dioxopiperidin-3-yl)-6-fluoro-1,3-dioxoisoindolin-5-yl)Hexahydropyrrolo[3,4-c]pyrrol-2(1H)-yl)methyl)piperidin-1-yl)pyridazine-3-formamide

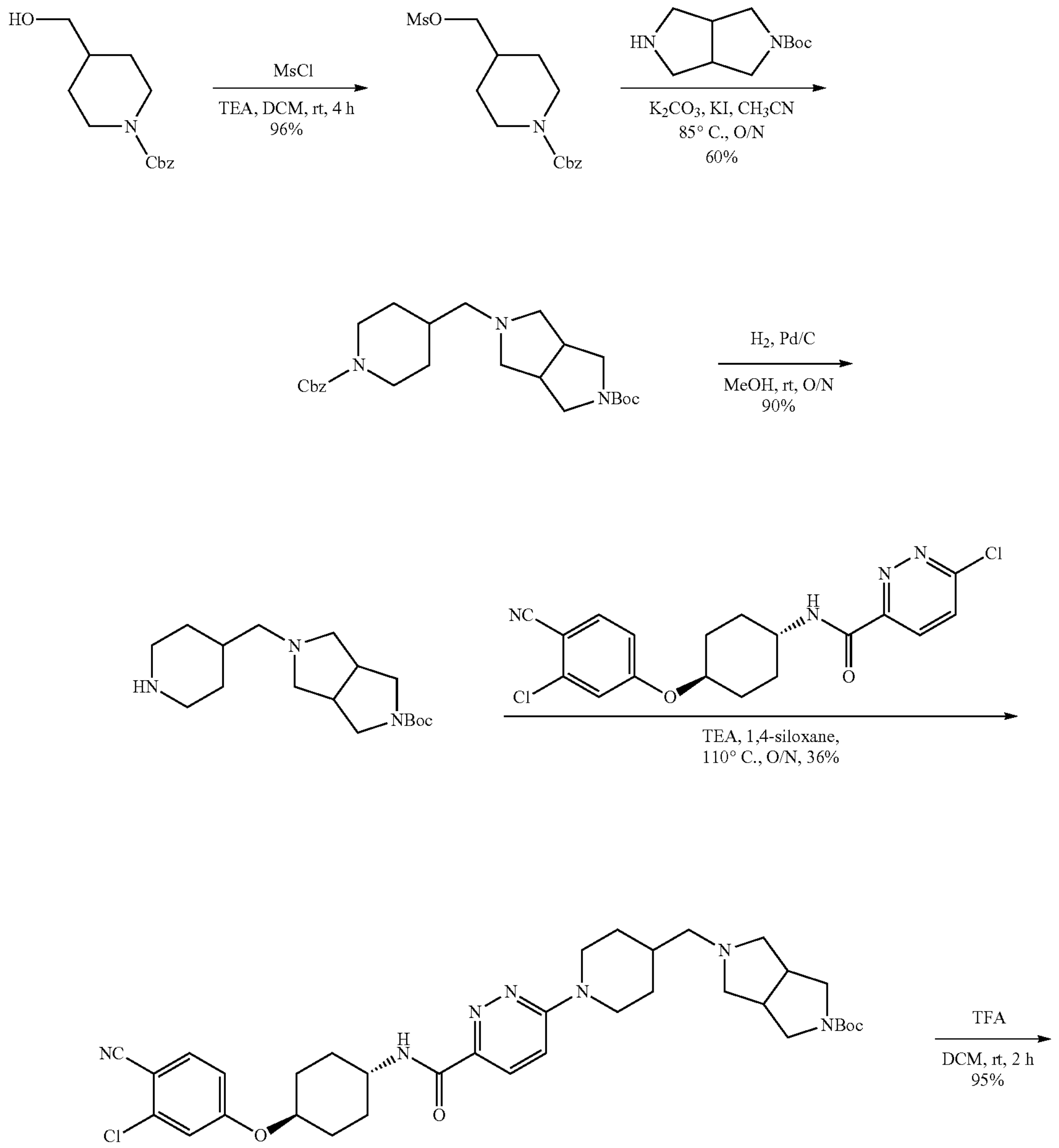

-continued

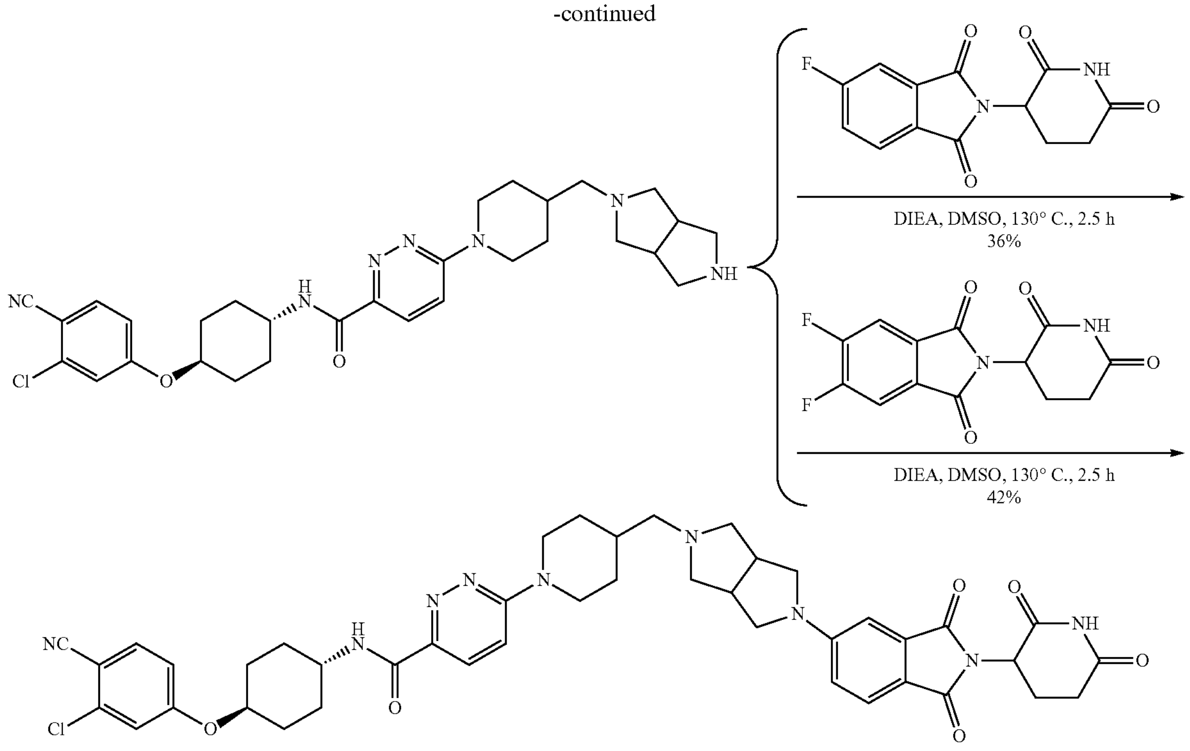

252

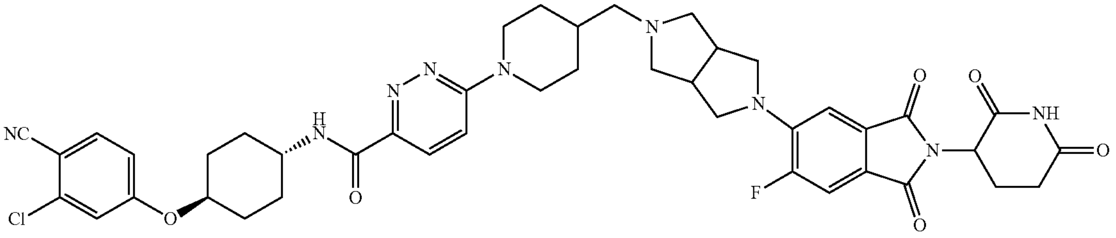

253

1. Synthesis of benzyl 4-(((methylsulfonyl)oxy) methyl)piperidine-1-carboxylate

Compound benzyl 4-(hydroxymethyl)piperidine-1-carboxylate (2.00 g, 8.00 mmol) was added in 20 ml of $CH_2Cl_2$, and the reaction solution was stirred in an ice bath, to which were also added TEA (2.5 mL, 16.00 mmol) and MsCl (1.10 g, 7.30 mmol). After that, the ice bath was removed, and the mixture was allowed to react at room temperature for 4 h. The reaction solution was diluted with DCM, washed successively with 1 N hydrochloric acid solution, saturated $NaHCO_3$ solution and saturated NaCl solution, dried over anhydrous sodium sulfate, and rotatory evaporated to dry to obtain a colorless oily compound benzyl 4-(((methylsulfonyl)oxy)methyl)piperidine-1-carboxylate (2.50 g, 7.60 mmol), with a yield of 96%.

LC/MS ($ESI^+$) calcd for $C_{15}H_{20}NO_5S$ $[M+H]^+$ m/z, 328.2; found, 328.2.

2. Compound t-butyl 5-((1-((benzoxy)carbonyl) piperidine-4-yl)methyl) hexahydropyrrolo[3,4-c] pyrrol-2(1H)-carboxylate Compound benzyl 4-(((methylsulfonyl)oxy)methyl)piperidine-1-carboxylate (2.00 g, 6.10 mmol), 2-BOC-octahydropyrrolo[3,4-c]pyrrole (1.30 g, 6.10 mmol), $K_2CO_3$ (2.10 g, 15.00 mmol) and KI (199 mg, 1.20 mmol) were added in $CH_3CN$, and then the reaction solution was heated to 85° C. and reacted overnight. The reaction solution was cooled to room temperature, to which were added water and ethyl acetate for extraction. The organic layer was further washed with saturated brine, dried over anhydrous sodium sulfate, rotatory evaporated to dry, and purified by silica gel column chromatography, to provide the colorless oily compound t-butyl 5-((1-((benzoxy)carbonyl)piperidine-4-yl)methyl) hexahydropyrrolo[3,4-c]pyrrol-2(1H)-carboxylate (1.60 g, 3.60 mmol), with a yield of 60%. LC/MS ($ESI^+$) calcd for: $C_{25}H_{36}N_3O_4[M+H]^+$ m/z, 444.2; found, 444.2.

3. Synthesis of Compound t-butyl 5-(piperidin-4-ylmethyl)hexahydropyrrolo[3,4-c]pyrrol-2(1H)-carboxylate Compound t-butyl 5-((1-((benzoxy)carbonyl)piperidine-4-yl)methyl) hexahydropyrrolo[3,4-c]pyrrol-2(1H)-carboxylate (1.60 g, 3.60 mmol) was dissolved in MeOH, and the system was evacuated three times under Ar protection, to which was then added Pd/C. The mixture was allowed to react at room temperature overnight. The reaction solution was filtered through celite, and the filtrate was concentrated to obtain a gray oily compound t-butyl 5-(piperidin-4-ylmethyl)hexahydropyrrolo[3,4-c]pyrrol-2(1H)-carboxylate (1.00 g, 3.20 mmol), with a yield of 90%. LC/MS (ESI+) calcd for: $C_{17}H_{30}N_3O_2$ $[M+H]^+$ m/z, 400.2; found, 400.2.

4. Synthesis of Compound t-butyl 5-((1-(6-(((1r,4r)-4-(3-chloro-4-cyanophenoxy) cyclohexyl)carbamoyl)pyridazine-3-yl)piperidine-4-yl)methyl)hexahydropyrrolidono [3,4-c]pyrrole-2(1H)-carboxylate Compounds t-butyl 5-(piperidin-4-ylmethyl)hexahydropyrrolo[3,4-c]pyrrol-2(1H)-carboxylate (98 mg, 0.30 mmol), 6-chloro-N-((1r,4r)-4-(3-chloro-4-cyanophenoxy) cyclohexyl)pyridazine-3-formamide (117 mg, 0.30 mmol) and TEA (60 mg, 0.60 mmol) were added in 3 mL of 1,4-dioxane, and then the reaction solution was heated to 110° C. and reacted overnight. The reaction solution was cooled to room temperature, to which were added water and ethyl acetate for extraction. The organic layer was further washed with saturated brine, dried over anhydrous sodium sulfate, rotatory evaporated to dry, and purified by silica gel column chromatography, to provide compound t-butyl 5-((1-(6-(((1r,4r)-4-(3-chloro-4-cyanophenoxy)cyclohexyl) carbamoyl)pyridazine-3-yl)piperidine-4-yl)methyl)hexahydropyrrolidono[3,4-c]pyrrole-2(1H)-carboxylate (70 mg, 0.10 mmol), with a yield of 35%.

LC/MS (ESI+) calcd for: $C_{35}H_{45}ClN_7O_4$ $[M+H]^+$ m/z, 664.3; found, 664.3.

5. Compound N-((1r,4r)-4-(3-chloro-4-cyanophenoxy)cyclohexyl)-6-(4-((hexahydropyrrolo[3,4-c] pyrrol-2(1H)-yl)methyl)piperidin-1-yl)pyridazine-3-formamide Compound N-((1r,4r)-4-(3-chloro-4-cyanophenoxy)cyclohexyl)-6-(4-((hexahydropyrrolo[3,4-c]pyrrol-2(1H)-yl) methyl)piperidin-1-yl)pyridazine-3-formamide (70 mg, 0.10 mmol) was dissolved in 1 mL of $CH_2Cl_2$, and the solution was stirred in an ice bath, to which was then slowly added 2 mL of TFA dropwise. After that, the ice bath was removed, and the mixture was allowed to react at room temperature for 2 h. The solvent was removed by rotatory evaporation, to obtain compound N-((1R,4R)-4-(3-chloro-4-cyanophenoxy) cyclohexyl)-6-(4-((hexahydropyrrolo[3,4-c] pyrrol-2(1H)-yl)methyl)piperidin-1-yl)pyridazine-3-formamide (53 mg, 0.09 mmol), with a yield of 95%.

LC/MS (ESI+) calcd for: $C_{30}H_{37}ClN_7O_2[M+H]^+$ m/z, 564.2; found, 564.2.

6. Synthesis of Compound N-((1r,4r)-4-(3-chloro-4-cyanophenoxy)cyclohexyl)-6-(4-((5-(2-(2,6-dioxopiperidin-3-yl)-1,3-dioxoisoindolin-5-yl)Hexahydropyrrolo[3,4-c] pyrrol-2(1H)-yl)methyl)piperidin-1-yl)pyridazine-3-formamide Compounds N-((1r,4r)-4-(3-chloro-4-cyanophenoxy)cyclohexyl)-6-(4-((hexahydropyrrolo[3,4-c]pyrrol-2(1H)-yl) methyl)piperidin-1-yl)pyridazine-3-formamide (53 mg, 0.09 mmol), 2-(2,6-dioxopiperidin-3-yl)-5-fluoroisoindole-1,3-dione (24 mg, 0.09 mmol) and DIEA (34 mg, 0.27 mmol) were added in DMSO, and then the reaction solution was heated to 130° C. and stirred 2.5 h. The reaction solution was cooled to room temperature, to which were added water and ethyl acetate for extraction. The organic layer was washed with brine, dried over anhydrous sodium sulfate, rotatory evaporated to dry, and purified by silica gel column chromatography, to provide compound N-((1r,4r)-4-(3-chloro-4-cyanophenoxy)cyclohexyl)-6-(4-((5-(2-(2,6-dioxopiperidin-3-yl)-1,3-dioxoisoindolin-5-yl)hexahydropyrrolo[3,4-c] pyrrol-2(1H)-yl)methyl)piperidin-1-yl)pyridazine-3-formamide (252) (26 mg, 0.03 mg), with a yield of 36%. LC/MS (ESI+) calcd for: $C_{45}H_{45}ClN_9O_6[M+H]^+$ m/z, 820.3; found, 820.3. $^1H$ NMR (400 MHz, $CDCl_3$) δ 8.18 (s, 1H), 7.98 (d, J=9.4 Hz, 1H), 7.88 (d, J=8.2 Hz, 1H), 7.70 (d, J=8.4 Hz, 1H), 7.58 (d, J=8.7 Hz, 1H), 7.07-6.94 (m, 3H), 6.87 (dd, J=8.8, 2.4 Hz, 1H), 4.96 (m, 1H), 4.44 (m, 6H), 4.07 (d, J=10.8 Hz, 1H), 3.69 (d, J=26.3 Hz, 3H), 3.39 (s, 2H), 3.12-2.60 (m, 9H), 2.28-2.11 (m, 6H), 1.54-1.42 (m, 4H), 1.37 (d, J=15.3 Hz, 2H), 0.90 (t, J=6.5 Hz, 2H).

7. Compound N-((1r,4r)-4-(3-chloro-4-cyanophenoxy)cyclohexyl)-6-(4-((5-(2-(2,6-dioxopiperidin-3-yl)-6-fluoro-1,3-dioxoisoindolin-5-yl)Hexahydropyrrolo[3,4-c]pyrrol-2(1H)-yl)methyl)piperidin-1-yl) pyridazine-3-formamide The target compound 253 was obtained, with a yield of 42%. LC/MS (ESI+) calcd for: $C_{43}H_{45}ClFN_9O_6$ $[M+H]^+$ m/z 838.2; found, 838.2. $^1H$ NMR (400 MHz, DMSO-$d_6$) δ 11.11 (s, 1H), 8.59 (d, J=8.2 Hz, 1H), 7.85 (d, J=8.8 Hz, 1H), 7.78 (d, J=9.5 Hz, 1H), 7.64 (d, J=12.5 Hz, 1H), 7.38 (d, J=2.4 Hz, 1H), 7.30 (d, J=9.7 Hz, 1H), 7.20-7.01 (m, 2H), 5.08 (dd, J=12.8, 5.4 Hz, 1H), 4.49 (dd, J=28.6, 8.6 Hz, 3H), 3.91-3.65 (m, 3H), 3.04-2.78 (m, 5H), 2.64-2.56 (m, 1H), 2.50 (m, J=1.8 Hz, 5H), 2.25 (d, J=6.6 Hz, 2H), 2.15-1.97 (m, 4H), 1.84 (dd, J=31.4, 11.7 Hz, 5H), 1.69-1.43 (m, 4H), 1.14 (dd, J=47.4, 16.7 Hz, 3H).

254: N-((1r,4r)-4-(3-chloro-4-cyanophenoxy)cyclohexyl)-5-(4-((5-(2-(2,6-dioxopiperidin-3-yl)-1,3-dioxoisoindolin-5-yl)Hexahydropyrrolo[3,4-c]pyrrol-2(11H)-yl)methyl)piperidin-1-yl)pyrazine-2-carboxamide

254

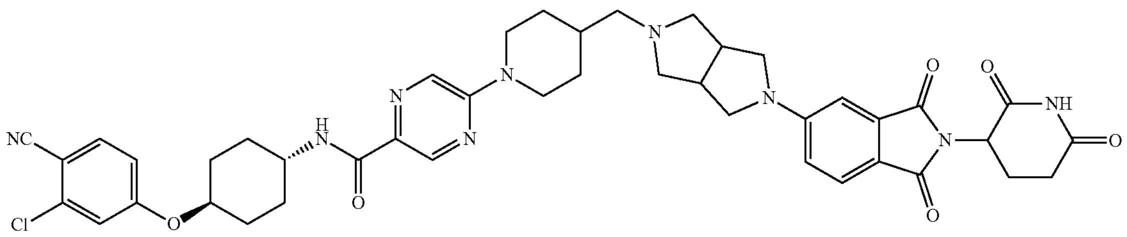

LC/MS (ESI$^+$) calcd for: $C_{43}H_{46}ClN_9O_6$[M+H]$^+$ m/z, 820.3; found 820.3.

$^1$H NMR (400 MHz, DMSO-$d_6$) δ 11.09 (s, 1H), 8.56 (d, J=1.2 Hz, 1H), 8.20 (s, 1H), 8.07 (d, J=8.2 Hz, 1H), 7.85 (d, J=8.8 Hz, 1H), 7.65 (d, J=8.4 Hz, 1H), 7.36 (d, J=2.4 Hz, 1H), 7.11 (dd, J=8.8, 2.4 Hz, 1H), 6.95 (d, J=2.1 Hz, 1H), 6.86 (dd, J=8.6, 2.1 Hz, 1H), 5.06 (dd, J=12.8, 5.4 Hz, 1H), 4.50 (td, J=9.9, 4.4 Hz, 1H), 4.42 (d, J=13.0 Hz, 2H), 3.80 (dd, J=7.8, 3.8 Hz, 1H), 3.73-3.59 (m, 2H), 3.01-2.79 (m, 6H), 2.25 (d, J=6.6 Hz, 2H), 2.04-1.94 (m, 2H), 1.91-1.68 (m, 6H), 1.66-1.42 (m, 6H), 1.34 (d, J=5.8 Hz, 1H), 1.27-1.17 (m, 5H), 1.06 (q, J=12.9 Hz, 2H), 0.84 (t, J=6.6 Hz, 1H).

255: N-((1r,4r)-4-(3-chloro-4-cyanophenoxy)cyclohexyl)-5-(4-((5-(2-(2,6-dioxopiperidin-3-yl)-6-fluoro-1,3-dioxoisoindolin-5-yl)Hexahydropyrrolo [3,4-c] pyrrol-2(1H)-yl)methyl)piperidin-1-yl) pyrazine-2-carboxamide

255

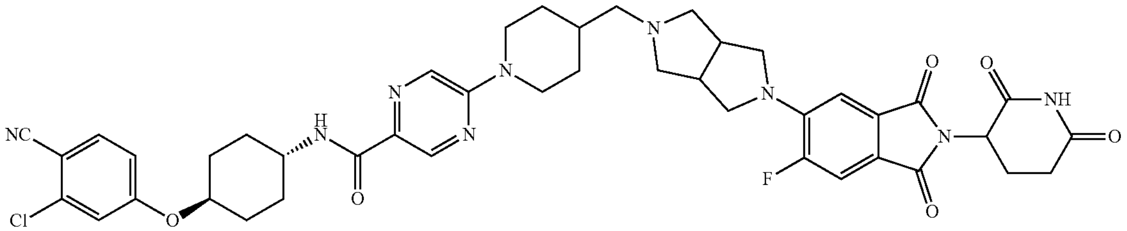

LC/MS (ESI$^+$) calcd for: $C_{43}H_{45}ClFN_9O_6$[M+H]$^+$ m/z, 838.2; found 838.2.

$^1$H NMR (400 MHz, DMSO-$d_6$) δ 11.11 (s, 1H), 8.56 (d, J=1.2 Hz, 1H), 8.21 (d, J=1.4 Hz, 1H), 8.07 (d, J=8.3 Hz, 1H), 7.85 (d, J=8.8 Hz, 1H), 7.63 (d, J=12.5 Hz, 1H), 7.36 (d, J=2.4 Hz, 1H), 7.17-7.06 (m, 2H), 5.08 (dd, J=12.9, 5.4 Hz, 1H), 4.55-4.38 (m, 3H), 3.76 (dt, J=34.4, 9.7 Hz, 3H), 3.01-2.80 (m, 5H), 2.57 (s, 1H), 2.54 (s, 1H), 2.50 (p, J=1.8 Hz, 5H), 2.25 (d, J=6.7 Hz, 2H), 2.13-1.97 (m, 3H), 1.91-1.72 (m, 51H), 1.67-1.40 (m, 4H), 1.23 (d, J=8.4 Hz, 1H), 1.14-0.97 (m, 2H).

256: N-((1r,4r)-4-(3-chloro-4-cyanophenoxy)cyclohexyl)-2-(4-((5-(2-(2,6-dioxopiperidin-3-yl)-1,3-dioxoisoindolin-5-yl)Hexahydropyrrolo[3,4-c]pyrrol-2(11H)-yl)methyl)piperidin-1-yl)pyrimidine-5-carboxamide

256

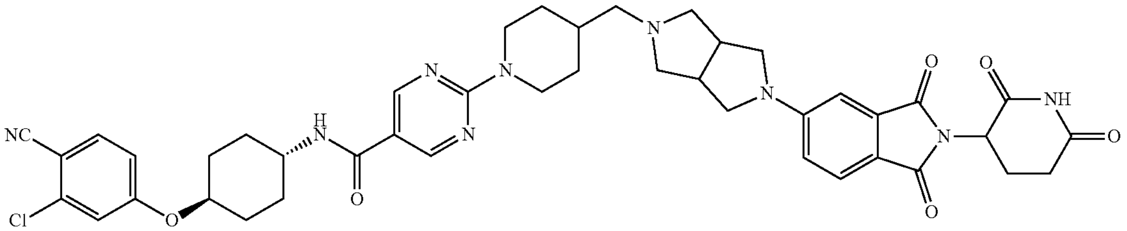

LC/MS (ESI$^+$) calcd for: $C_{34}H_{46}ClN_9O_6$ [M+H]$^+$ m/z, 820.3; found 820.3.

$^1$H NMR (400 MHz, DMSO-$d_6$) δ 11.07 (s, 1H), 8.71 (s, 2H), 8.10 (d, J=7.5 Hz, 1H), 7.85 (d, J=8.7 Hz, 1H), 7.65 (d, J=8.4 Hz, 1H), 7.37 (d, J=2.4 Hz, 1H), 7.12 (dd, J=8.8, 2.5 Hz, 1H), 6.95 (d, J=2.1 Hz, 1H), 6.85 (dd, J=8.6, 2.1 Hz, 1H), 5.06 (dd, J=12.9, 5.4 Hz, 1H), 4.68 (d, J=12.9 Hz, 2H), 4.59-4.44 (m, 1H), 3.84-3.59 (m, 3H), 3.01-2.78 (m, 5H), 2.23 (d, J=6.7 Hz, 2H), 2.14-1.95 (m, 4H), 1.90 (t, J=9.3 Hz, 2H), 1.77 (d, J=12.6 Hz, 3H), 1.48 (p, J=5.4, 4.7 Hz, 5H), 1.33 (d, J=5.8 Hz, 1H), 1.27-1.17 (m, 4H), 0.98 (d, J=12.6 Hz, 2H), 0.83 (d, J=7.1 Hz, 1H).

257: N-((1r,4r)-4-(3-chloro-4-cyanophenoxy)cyclohexyl)-2-(4-((5-(2-(2,6-dioxopiperidin-3-yl)-6-fluoro-1,3-dioxoisoindolin-5-yl)Hexahydropyrrolo [3,4-c] pyrrol-2(1H)-yl)methyl)piperidin-1-yl) pyrimidine-5-carboxamide

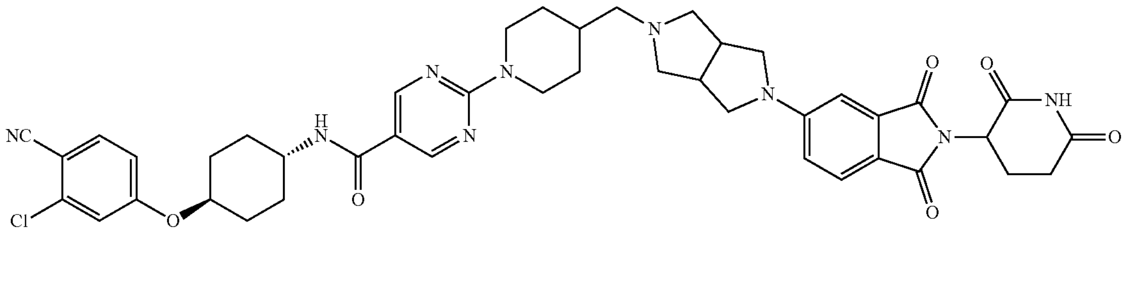

257

LC/MS (ESI+) calcd for: $C_{43}H_{45}ClFN_9O_6[M+H]^+$ m/z, 838.2; found 838.2.

$^1H$ NMR (400 MHz, DMSO-$d_6$) δ 11.11 (s, 1H), 8.72 (s, 2H), 8.10 (d, J=7.5 Hz, 1H), 7.85 (d, J=8.8 Hz, 1H), 7.63 (d, J=12.5 Hz, 1H), 7.38 (d, J=2.4 Hz, 1H), 7.32-6.97 (m, 2H), 5.08 (dd, J=12.8, 5.4 Hz, 1H), 4.69 (d, J=12.7 Hz, 2H), 4.53 (d, J=4.6 Hz, 1H), 3.74 (d, J=29.2 Hz, 3H), 3.00-2.80 (m, 6H), 2.60 (d, J=3.3 Hz, 1H), 2.50 (m, 6H), 2.25 (d, J=6.6 Hz, 2H), 2.09 (s, 2H), 1.95-1.85 (m, 2H), 1.78 (d, J=12.5 Hz, 3H), 1.57-1.42 (m, 4H), 1.23 (d, J=7.9 Hz, 1H), 1.00 (d, J=12.6 Hz, 2H).

258: N-((1r,4r)-4-(3-chloro-4-cyanophenoxy)cyclohexyl)-4-(4-((5-(2-(2,6-dioxopiperidin-3-yl)-1,3-dioxoisoindolin-5-yl)Hexahydropyrrolo[3,4-c]pyrrol-2(11H)-yl)methyl)piperidin-1-yl)benzamide

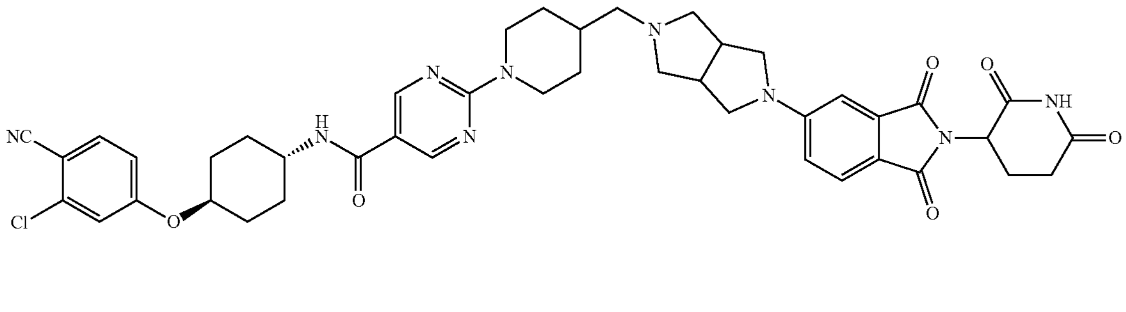

258

LC/MS (ESI+) calcd for: $C_{45}H_{48}ClN_7O_6[M+H]^+$ m/z, 818.3; found, 818.3.

$^1H$ NMR (400 MHz, DMSO-$d_6$) δ 11.09 (s, 1H), 7.95 (d, J=7.6 Hz, 1H), 7.85 (d, J=8.7 Hz, 1H), 7.68 (dd, J=19.6, 8.4 Hz, 2H), 7.65 (d, J=8.4 Hz, 1H), 7.38 (d, J=2.4 Hz, 1H), 7.13 (dd, J=8.8, 2.5 Hz, 1H), 7.01-6.76 (m, 4H), 5.06 (dd, J=12.9, 5.4 Hz, 1H), 4.57-4.43 (m, 1H), 3.86-3.58 (m, 5H), 3.30-3.19 (m, 2H), 3.02-2.81 (m, 2H), 2.71 (t, J=12.1 Hz, 2H), 2.57 (dd, J=19.0, 7.2 Hz, 4H), 2.25 (d, J=17.2 Hz, 21H), 2.13-2.06 (m, 2H), 2.04-1.96 (m, 2H), 1.93-1.84 (m, 2H), 1.75 (d, J=12.6 Hz, 2H), 1.69-1.58 (m, 1H), 1.49 (q, J=12.8 Hz, 4H), 1.23 (d, J=7.4 Hz, 2H), 1.14 (m, 6.8 Hz, 2H).

259: N-((1r,4r)-4-(3-chloro-4-cyanophenoxy)cyclohexyl)-6-(5-((1-(2-(2,6-dioxopiperidin-3-yl)-6-fluoro-1,3-dioxoisoindolin-5-yl)piperidine-4-yl) methyl) hexahydropyrrolo[3,4-c]pyrrol-2(11H)-yl) pyridazine-3-carboxamide

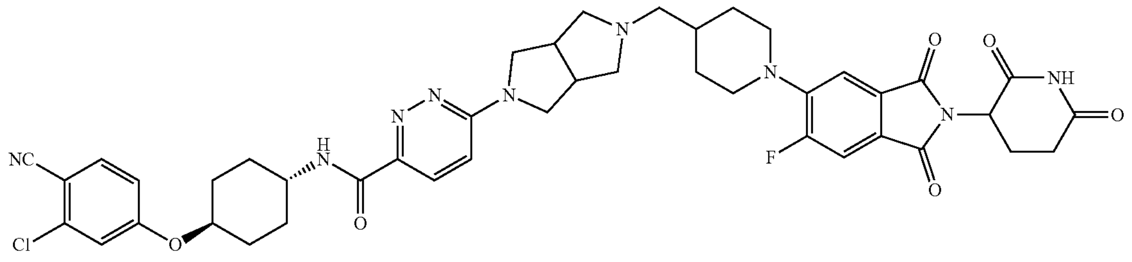

259

LC/MS (ESI+) calcd for. $C_{43}H_{46}ClN_9O_6$[M+H]+ m/z, 820.3; found 820.3.

$^1$H NMR (400 MHz, DMSO-$d_6$) δ 11.08 (s, 1H), 8.58 (d, J=8.2 Hz, 1H), 7.84 (dd, J=10.5, 9.1 Hz, 2H), 7.63 (d, J=8.6 Hz, 1H), 7.39 (d, J=2.4 Hz, 1H), 7.28 (d, J=2.3 Hz, 1H), 7.19 (dd, J=8.7, 2.3 Hz, 1H), 7.13 (dd, J=8.8, 2.4 Hz, 1H), 7.00 (d, J=9.4 Hz, 1H), 5.05 (dd, J=12.9, 5.4 Hz, 1H), 4.53 (dt, J=10.3, 5.8 Hz, 1H), 4.01 (dd, J=10.2, 6.8 Hz, 2H), 3.90-3.71 (m, 3H), 3.40 (d, J=10.3 Hz, 2H), 3.01-2.80 (m, 5H), 2.62-2.52 (m, 4H), 2.24 (d, J=6.6 Hz, 2H), 2.15-2.05 (m, 2H), 2.00 (m, 1H), 1.94-1.85 (m, 2H), 1.81-1.42 (m, 8H), 1.22 (s, 1H), 1.11 (d, J=11.7 Hz, 2H).

260: N-((1r,4r)-4-(3-chloro-4-cyanophenoxy)cyclohexyl)-6-(5-((1-(2-(2,6-dioxopiperidin-3-yl)-1,3-dioxoisoindolin-5-yl)piperidine-4-yl)methyl) hexahydropyrrolo[3,4-c]pyrrol-2(1H)-yl)pyridazine-3-carboxamide

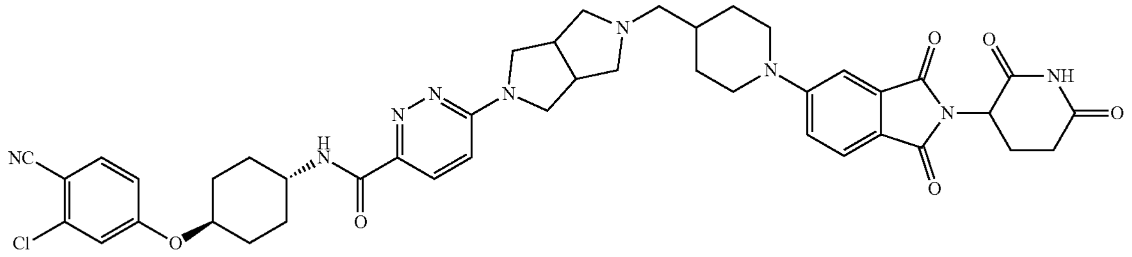

260

LC/MS (ESI+) calcd for: $C_{43}H_{45}ClfN_9O_6$[M+H]+ m/z, 838.3; found 838.3.

$^1$H NMR (400 MHz, DMSO-$d_6$) δ 11.11 (s, 1H), 8.57 (d, J=8.2 Hz, 1H), 7.85 (dd, J=11.7, 9.0 Hz, 2H), 7.69 (d, J=11.5 Hz, 1H), 7.45-7.36 (m, 2H), 7.14 (dd, J=8.8, 2.4 Hz, 1H), 7.01 (d, J=9.5 Hz, 1H), 5.10 (dd, J=12.8, 5.4 Hz, 1H), 4.54 (td, J=10.3, 5.1 Hz, 1H), 3.82 (m, 3H), 3.57 (d, J=12.1 Hz, 2H), 3.46-3.39 (m, 2H), 3.04-2.78 (m, 5H), 2.63-2.55 (m, 3H), 2.29 (d, J=7.1 Hz, 2H), 2.21-1.96 (m, 4H), 1.95-1.86 (m, 2H), 1.85-1.74 (m, 2H), 1.72-1.58 (m, 3H), 1.51 (q, J=11.5 Hz, 2H), 1.23 (t, J=6.2 Hz, 4H).

261: N-((1r,4r)-4-(3-chloro-4-cyanophenoxy)cyclohexyl)-6-(9-((1-(2,6-dioxopiperidin-3-yl)-6-fluoro-1,3-dioxoisoindolin-5-yl)piperidine-4-yl)methyl)-3,9-diazaspiro[5.5]undecan-3-yl)pyridazine-3-formamide

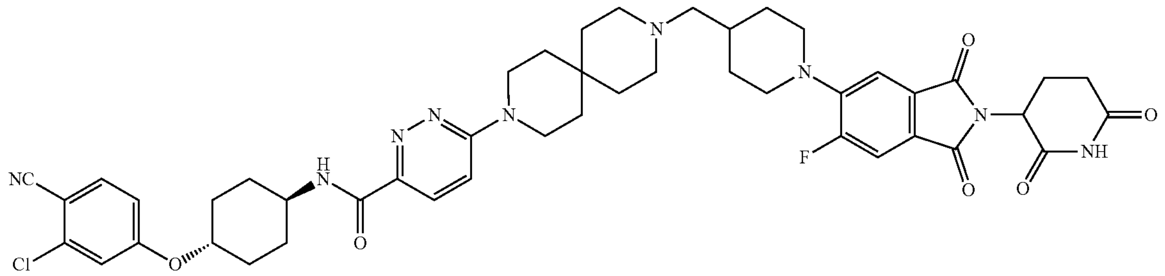

261

LC/MS ($ESI^+$) calcd for: $C_{46}H_{52}ClFN_9O_6$ $[M+H]^+$ m/z, 880.3; found 880.3.

$^1H$ NMR (400 MHz, DMSO-$d_6$) δ 11.12 (s, 1H), 8.61 (d, J=8.2 Hz, 1H), 7.83 (dd, J=22.8, 9.0 Hz, 2H), 7.70 (d, J=11.3 Hz, 1H), 7.46-7.36 (m, 2H), 7.32 (d, J=9.7 Hz, 1H), 7.13 (dd, J=8.8, 2.5 Hz, 1H), 5.10 (dd, J=12.8, 5.4 Hz, 1H), 4.51 (d, J=11.4 Hz, 1H), 3.85 (d, J=10.4 Hz, 1H), 3.76-3.52 (m, 4H), 3.58 (t, J=9.2 Hz, 2H), 2.87 (t, J=11.9 Hz, 3H), 2.34 (s, 4H), 2.24-1.96 (m, 6H), 1.94-1.76 (m, 5H), 1.50 (d, J=8.2 Hz, 10H), 1.31-1.11 (m, 5H).

262: N-((1r,4r)-4-(3-chloro-4-cyanophenoxy)cyclohexyl)-6-(9-((1-(2-(2,6-dioxopiperidin-3-yl)-1,3-dioxoisoindolin-5-yl)piperidine-4-yl)methyl)-3,9-diazaspiro[5.5]undecan-3-yl)pyridazine-3-formamide

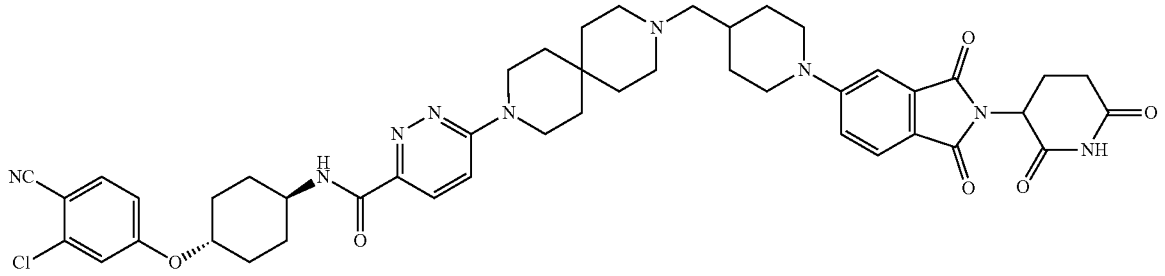

262

LC/MS ($ESI^+$) calcd for: $C_{46}H_{52}ClN_9O_6[M+H]^+$ m/z, 862.3; found 862.3.

$^1H$ NMR (400 MHz, DMSO-$d_6$) δ 11.09 (s, 1H), 8.61 (d, J=8.2 Hz, 1H), 7.83 (dd, J=23.3, 9.1 Hz, 2H), 7.65 (d, J=8.5 Hz, 1H), 7.39 (d, J=2.4 Hz, 1H), 7.31 (d, J=10.3 Hz, 2H), 7.22 (d, J=8.7 Hz, 1H), 7.13 (dd, J=8.8, 2.4 Hz, 1H), 5.06 (dd, J=12.9, 5.4 Hz, 1H), 4.53 (s, 1H), 4.03 (d, J=13.1 Hz, 2H), 3.91-3.80 (m, 1H), 3.68 (d, J=6.3 Hz, 4H), 2.90 (dq, J=31.6, 9.1, 5.8 Hz, 3H), 2.34 (s, 4H), 2.12 (dd, J=19.3, 9.1 Hz, 4H), 2.00 (d, J=13.5 Hz, 2H), 1.93-1.73 (m, 5H), 1.50 (d, J=6.8 Hz, 10-H), 1.29-1.06 (m, 5H).

263: N-((1r,4R)-4-(3-chloro-4-cyanophenoxy)cyclohexyl)-6-((2R)-4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2-methylpiperazin-1-yl)pyridazine-3-formamide
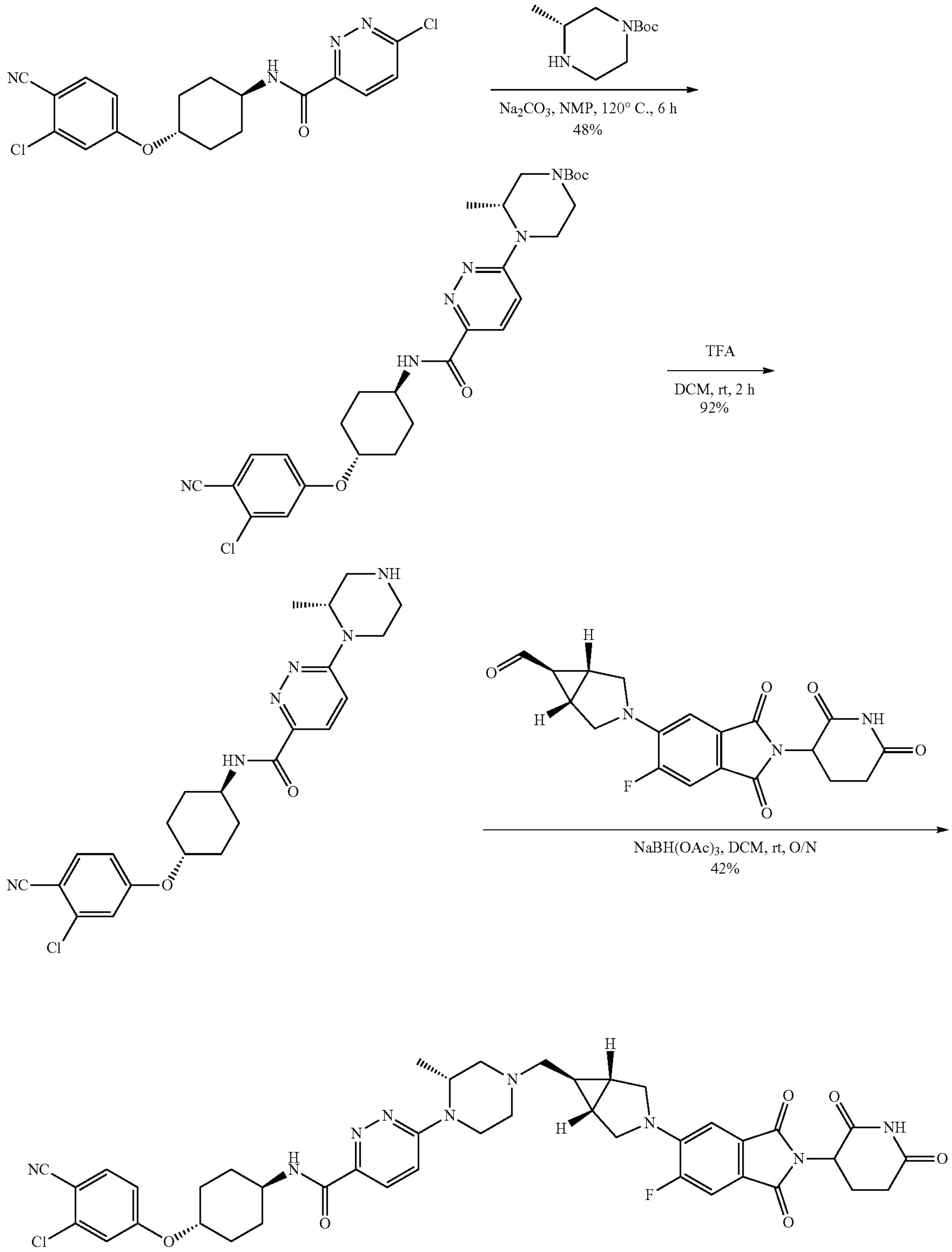
263

1. Synthesis of t-butyl (R)-4-(6-((1r,4R)-4-(3-chloro-4-cyanophenoxy)cyclohexyl) carbamoyl) pyridazine-3-yl)-3-methylpiperazine-1-carboxylate Compounds 6-chloro-N-((1r,4r)-4-(3-chloro-4-cyanophenoxy)cyclohexyl)pyridazine-3-formamide (200 mg, 0.51 mmol), t-butyl (R)-3-methylpiperazine-1-carboxylate (200 mg, 1.00 mmol) and $K_2CO_3$ (207 mg, 1.50 mmol) were added in 5 mL of NMP, and the mixture was allowed to react 6 h at 120° C. The reaction solution was diluted with a large amount of EA, and then the organic phase was washed with water and saturated NaCl solution respectively. The organic phase was dried over anhydrous sodium sulfate, rotatory evaporated to dry, and purified by column chromatography to obtain compound t-butyl (R)-4-(6-((1r,4R)-4-(3-chloro-4-cyanophenoxy)cyclohexyl)carbamoyl) pyridazine-3-yl)-3-methylpiperazine-1-carboxylate (135 mg, 0.24 mmol), with a yield of 48%.

LC/MS ($ESI^+$) calcd for $C_{28}H_{35}ClN_6O_4[M+H]^+$ m/z, 555.2; found, 555.2.

2. Synthesis of N-((1r,4R)-4-(3-chloro-4-cyanophenoxy)cyclohexyl)-6-((R)-2-methylpiperazin-1-yl) pyridazine-3-formamide The target compound was obtained, with a yield of 92%. LC/MS ($ESI^+$) calcd for $C_{23}H_{27}ClN_6O_2$ $[M+H]^+$ m/z 455.1; found 455.1.

3. Synthesis of N-((1r,4R)-4-(3-chloro-4-cyanophenoxy)cyclohexyl)-6-((2R)-4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)-2-methylpiperazin-1-yl)pyridazine-3-formamide The target compound was obtained, with a yield of 42%. LC/MS ($ESI^+$) calcd for: $C_{46}H_{50}ClFN_9O_6[M+H]^+$ m/z, 824.3; found 824.3. $^1H$ NMR (400 MHz, DMSO-$d_6$) δ 11.10 (s, 1H), 8.64 (d, J=8.2 Hz, 1H), 7.84 (dd, J=9.2, 7.3 Hz, 2H), 7.59 (d, J=12.9 Hz, 1H), 7.38 (d, J=2.4 Hz, 1H), 7.30 (d, J=9.7 Hz, 1H), 7.19-6.99 (m, 2H), 5.07 (dd, J=12.8, 5.4 Hz, 1H), 4.71-4.46 (m, 2H), 4.28-4.16 (m, 1H), 3.85 (dt, J=9.6, 4.2 Hz, 3H), 3.60 (d, J=9.5 Hz, 2H), 3.22-3.04 (m, 2H), 2.97-2.81 (m, 2H), 2.42-2.23 (m, 3H), 2.17-1.97 (m, 51H), 1.89 (d, J=12.3 Hz, 2H), 1.63 (q, J=5.5, 3.2 Hz, 4H), 1.56-1.44 (m, 2H), 1.26-1.13 (m, 5H).

264: N-((1r,4R)-4-(3-chloro-4-cyanophenoxy)cyclohexyl)-5-((2R)-4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl-2-methylpiperazin-1-yl)pyrazine-2-carboxamide

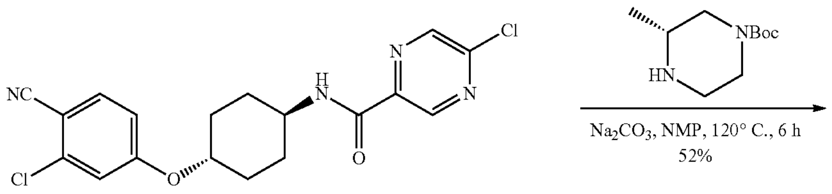

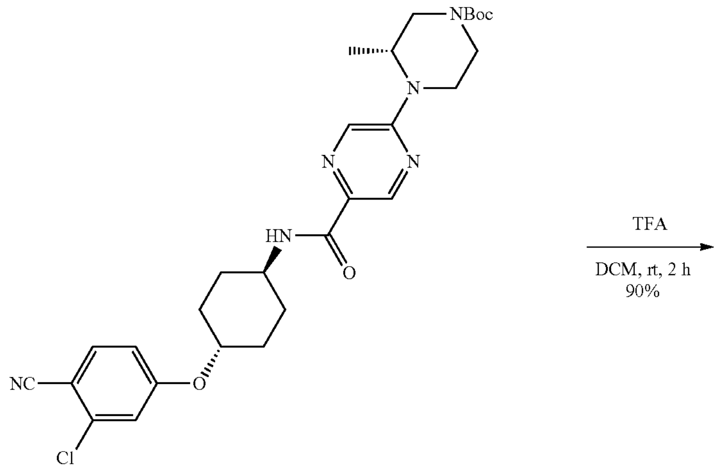

-continued

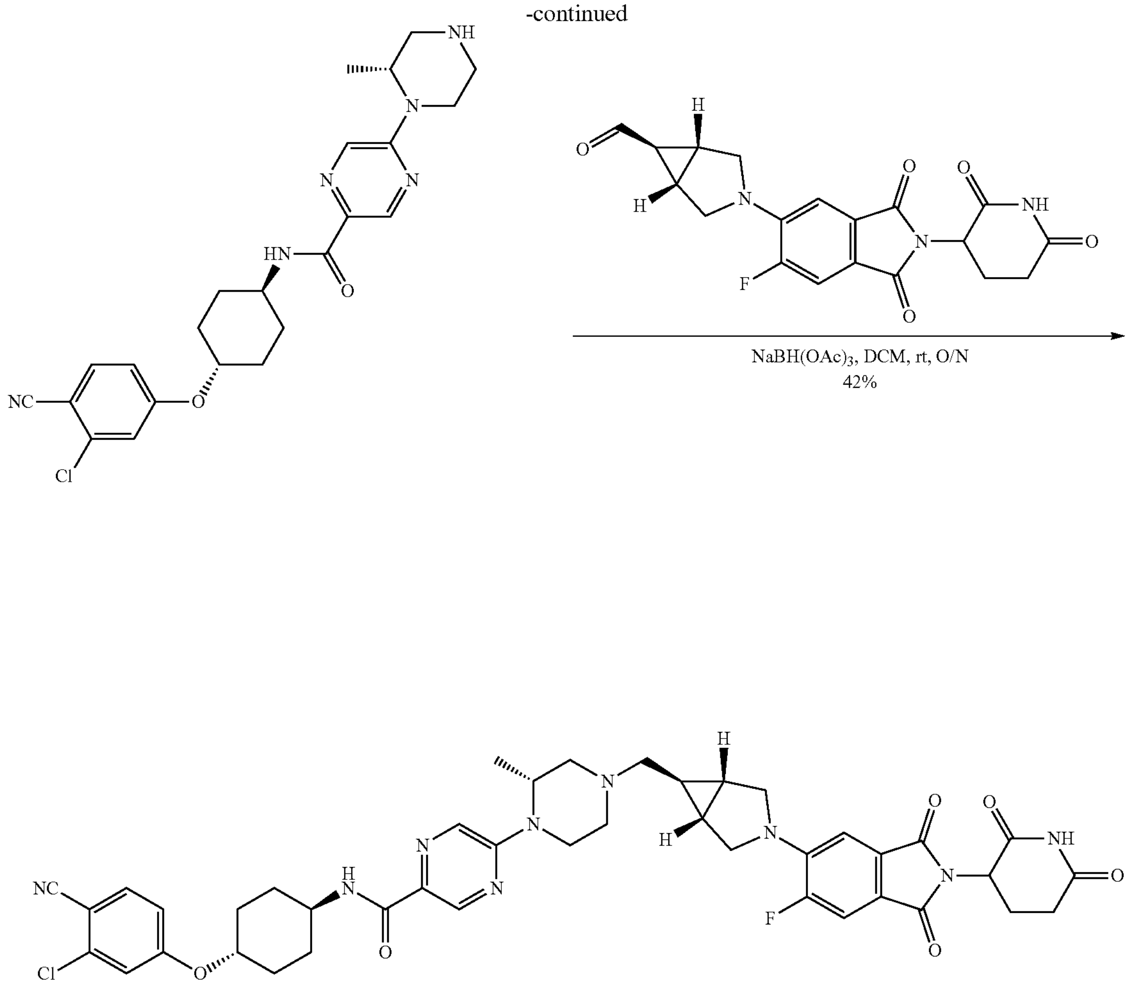

264

1. Synthesis of t-butyl (R)-4-(5-((1r,4R)-4-(3-chloro-4-cyanophenoxy)cyclohexyl) carbamoyl) pyrazine-2-yl)-3-methylpiperazine-1-carboxylate The target compound was obtained, with a yield of 52%. LC/MS (ESI) calcd for $C_{28}H_{35}ClN_6O_4[M+H]^+$ m/z 555.2; found 555.2.

2. Synthesis of N-((1r,4R)-4-(3-chloro-4-cyanophenoxy)cyclohexyl)-5-((R)-2-methylpiperazin-1-yl) pyrazine-2-carboxamide The target compound was obtained, with a yield of 92%. LC/MS ($ESI^+$) calcd for: $C_{23}H_{27}ClN_6O_2[M+H]^+$ m/z, 455.1; found 455.1.

3. Synthesis of N-((1r,4R)-4-(3-chloro-4-cyanophenoxy)cyclohexyl)-5-((2R)-4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl-2-methylpiperazin-1-yl)pyrazine-2-carboxamide The target compound was obtained, with a yield of 42%. LC/MS ($ESI^+$) calcd for: $C_{46}H_{50}ClFN_9O_6[M+H]+$ m/z, 824.3; found, 824.3. $^1H$ NMR (400 MHz, DMSO-$d_6$) δ 11.10 (s, 1H), 8.61 (d, J=1.2 Hz, 1H), 8.20 (s, 1H), 8.11 (d, J=8.2 Hz, 1H), 7.85 (d, J=8.8 Hz, 1H), 7.59 (d, J=12.8 Hz, 1H), 7.36 (d, J=2.4 Hz, 1H), 7.16-6.94 (m, 2H), 5.07 (dd, J=12.8, 5.4 Hz, 1H), 4.72-4.45 (m, 2H), 4.21 (d, J=12.7 Hz, 1H), 3.84 (dq, J=12.7, 4.9, 4.4 Hz, 3H), 3.59 (d, J=9.5 Hz, 2H), 3.24-3.01 (m, 2H), 2.94-2.79 (m, 2H), 2.33 (dd, J=11.1, 6.9 Hz, 3H), 2.13-1.96 (m, 5H), 1.91-1.80 (m, 2H), 1.70-1.43 (m, 6H), 1.20 (dd, J=17.2, 6.6 Hz, 5H).

265: N-((1r,4R)-4-(3-chloro-4-cyanophenoxy)cyclohexyl)-6-((3R)-4-((1R,5S,6s)-3-(2-(2,6-dioxopiperidin-3-yl)-6-fluoro-1,3-dioxoisoindolin-5-yl)-3-azabicyclo[3.1.0] n-hexane-6-yl)methyl)-3-methylpiperazin-1-yl)pyridazine-3-formamide
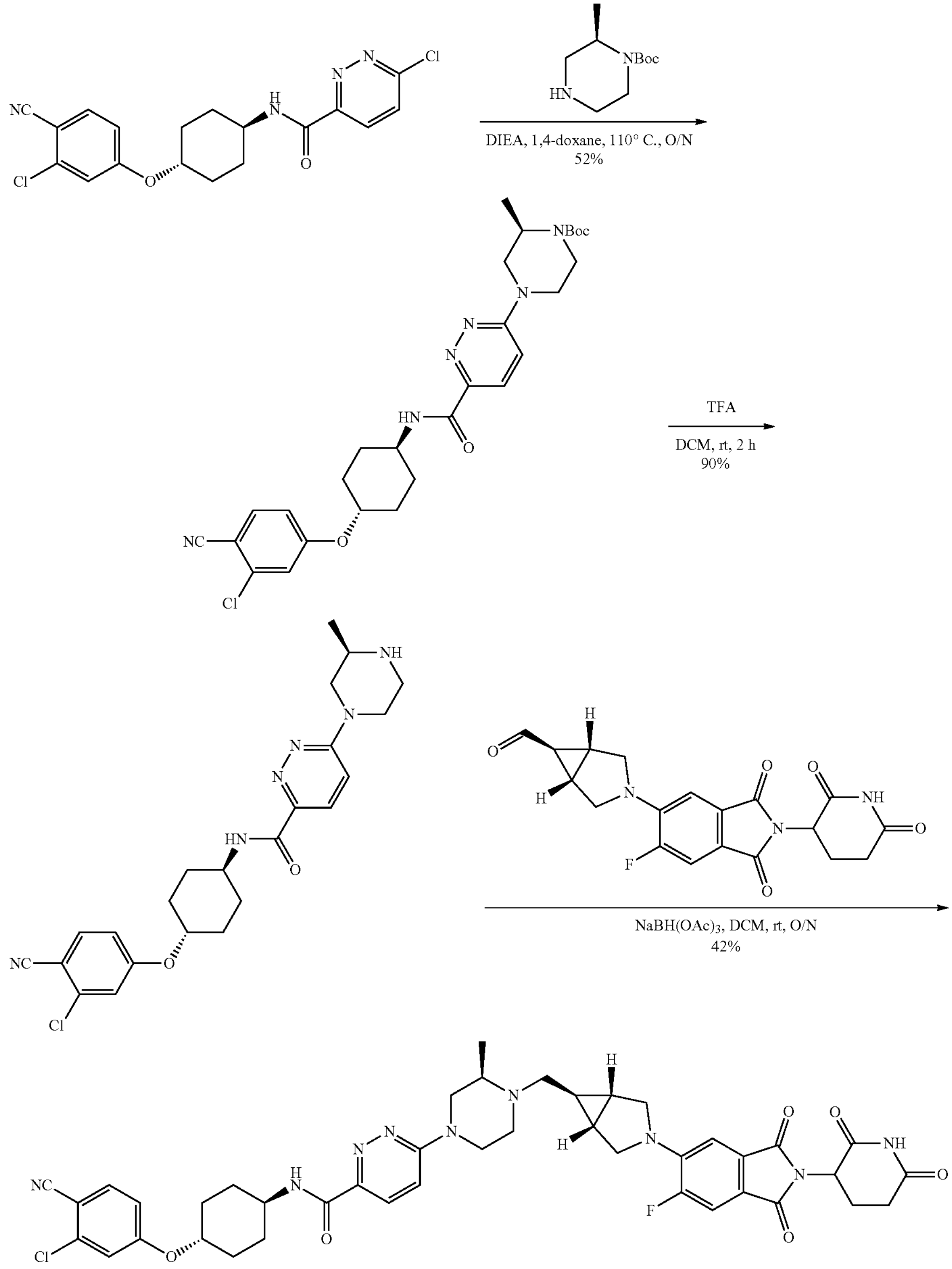
265

LC/MS (ESI+) calcd for: $C_{46}H_{50}ClFN_9O_6[M+H]^+$ m/z, 824.3; found 824.3, found 824.3.
$^1$H NMR (400 MHz, DMSO-$d_6$) δ 11.10 (s, 1H), 8.62 (d, J=8.2 Hz, 1H), 7.84 (dd, J=14.6; 9.1 Hz, 7.60 (d, J=12.8 Hz, 1H), 7.44-7.33 (m, 2R), 7.19-7.05 (m, 2H), 5.07 (dd, 12.8, 5.4 Hz, 1H), 4.54 (dd, J=12.9, 8.3 Hz, 1H), 4.15 (dd, J=39.2, 12.6 Hz, 2H), 3.84 (dt, J=9.6, 4.6 Hz, 3H), 3.59 (d, J=9.7 Hz, 2H), 3.09-2.79 (m, 3H), 2.43-2.27 (m, 2H), 2.15-1.80 (m, 7H), 1.70-1.57 (m, 4H), 1·57-1.45 (m, 3H), 1.23 (s, 2H), 1.05 (d, J=6.1 Hz, 3H), 0.88-0.71 (m, 1H).
266: N-((1r,4R)-4-(3-chloro-4-cyanophenoxy)cyclohexyl)-5-((3R)-4-((1R,5S,6s)-3-(2-(2,6-dioxopiperidin-3-yl)-6-fluoro-1,3-dioxoisoindolin-5-yl)-3-azabicyclo[3.1.0]n-hexane-6-yl)methyl-3-methylpiperazin-1-yl)pyrazine-2-carboxamide
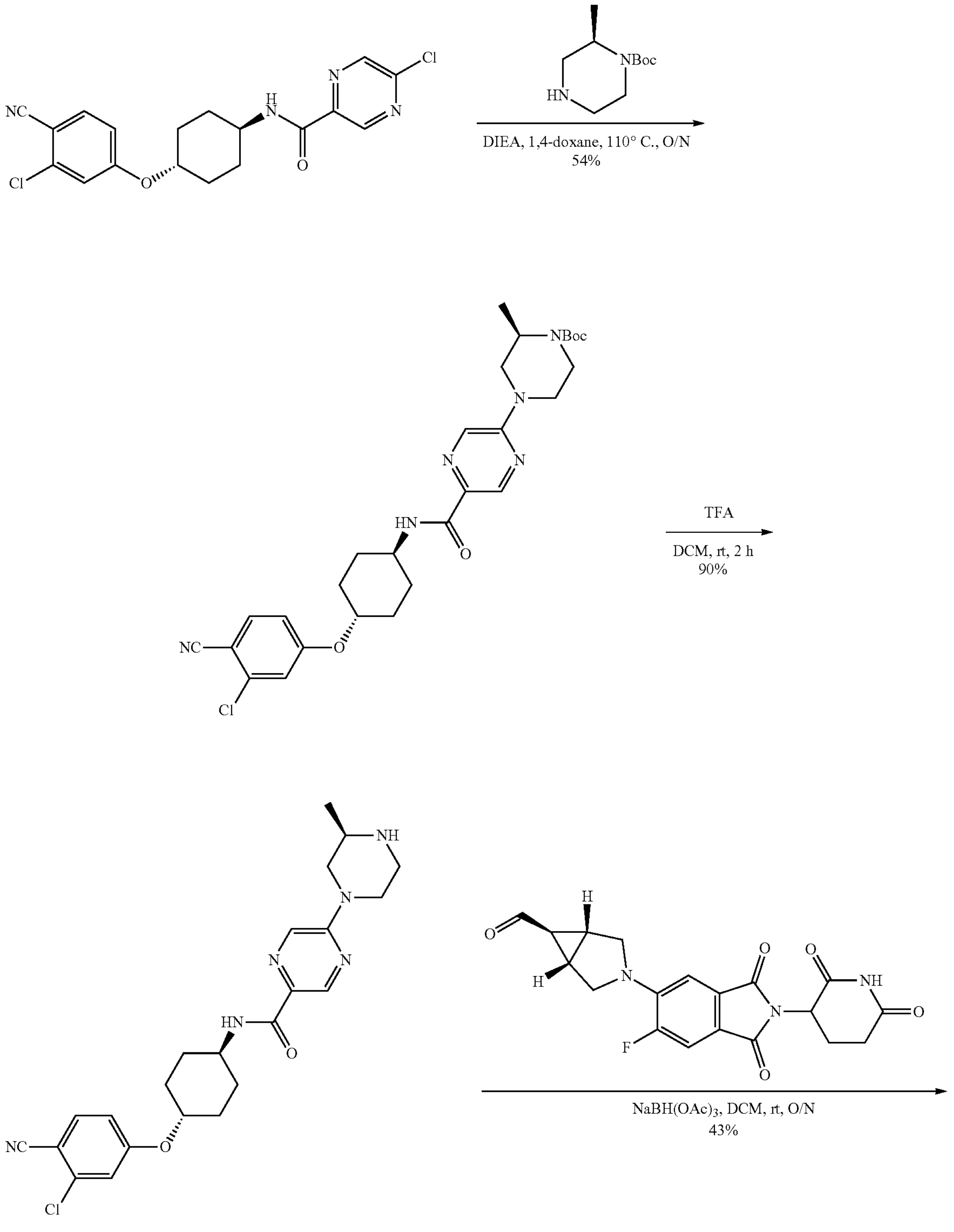

-continued

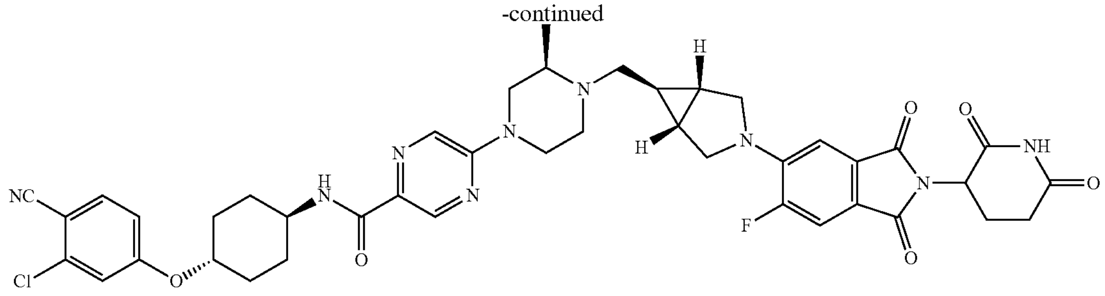

266

LC/MS (ESI$^+$) calcd for: $C_{46}H_{49}ClFN_9O_6$[M+H]$^+$ m/z, 824.3; found 824.3.

$^1$H NMR (400 MHz, DMSO-$d_6$) δ 11.10 (s, 1H), 8.59 (s, 1H), 8.26 (s, 1H), 8.10 (d, J=8.2 Hz, 1H), 7.85 (d, J=8.8 Hz, 1H), 7.58 (d, J=12.8 Hz, 1H), 7.37 (d, J=2.4 Hz, 1H), 7.18-6.92 (m, 2H), 5.06 (dd, J=12.8, 5.4 Hz, 1H), 4.51 (tt, J=9.9, 4.3 Hz, 1H), 4.13 (t, J=12.5 Hz, 2H), 3.83 (dd, J=10.3, 5.3 Hz, 31H), 3.58 (d, J=9.6 Hz, 2H), 3.27 (d, J=3.4 Hz, 1H), 3.08-2.99 (m, 1H), 2.97-2.80 (m, 2H), 2.34 (td, J=12.7, 7.7 Hz, 2H), 2.15-1.77 (m, 6H), 1.71-1.41 (m, 7H), 1.22 (s, 2H), 1.05 (d, J=6.1 Hz, 3H), 0.91-0.70 (m, 1H).

267: N-((1r,4r)-4-(3-chloro-4-cyanophenoxy)cyclohexyl)-2-(4-((2-(2,6-dioxopiperidin-3-yl)-1,3-dioxoisoindolin-5-yl)-2,7-diazaspiro[3.5]nonan-7-yl)methyl)piperidin-1-yl)pyrimidine-5-formamide

267

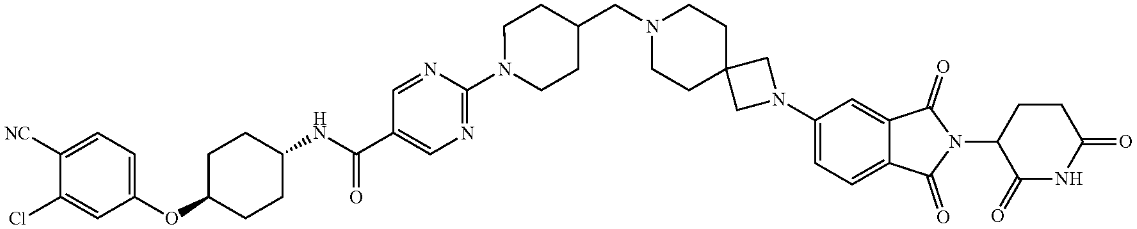

LC/MS (ESI$^+$) calcd for: $C_{41}H_{48}ClN_9O_6$ [M+H]$^+$ m/z, 834.3; found, 834.3.

1H NMR (400 MHz, DMSO-$d_6$) δ 11.08 (s, 1H), 8.74 (s, 2H), 8.11 (d, J=7.4 Hz, 1H), 7.86 (d, J=8.7 Hz, 1H), 7.63 (d, J=8.2 Hz, 1H), 7.38 (d, J=2.4 Hz, 1H), 7.14 (dd, J=8.8, 2.4 Hz, 1H), 6.77 (d, J=2.0 Hz, 1H), 6.64 (dd, J=8.4, 2.1 Hz, 1H), 5.05 (dd, J=12.9, 5.4 Hz, 1H), 4.72 (d, J=12.8 Hz, 2H), 4.59-4.48 (m, 1H), 3.74 (s, 5H), 3.01-2.81 (m, 3H), 2.55 (d, J=6.5 Hz, 1H), 2.31 (s, 3H), 2.11 (t, J=6.6 Hz, 4H), 2.03-1.95 (m, 2H), 1.91 (t, J=6.3 Hz, 2H), 1.77 (q, J=8.3, 5.7 Hz, 6H), 1.56-1.42 (m, 4H), 1.24-1.13 (m, 2H), 1.07-0.93 (m, 2H).

268: N-((1r,4r)-4-(3-chloro-4-cyanophenoxy)cyclohexyl)-2-(4-((2-(2,6-dioxopiperidin-3-yl)-6-fluoro-1,3-dioxoisoindolin-5-yl)-2,7-diazaspiro[3.5]nonan-7-yl)methyl)piperidin-1-yl)pyrimidine-5-formamide

268

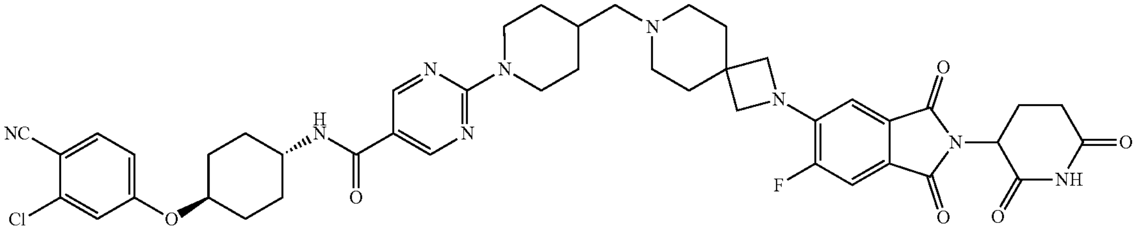

LC/MS ($ESI^+$) calcd for: $C_{44}H_{47}ClFN_9O_6[M+H]^+$ m/z, 852.3; found 852.3.
$^1H$ NMR (400 MHz, DMSO-$d_6$) δ 11.10 (s, 1H), 8.73 (s, 2H), 8.11 (d, J=7.5 Hz, 1H), 7.88-7.84 (m, 1H), 7.59 (d, J=11.2 Hz, 1H), 7.39 (d, J=2.4 Hz, 1H), 7.14 (dd, J=8.8, 2.5 Hz, 1H), 6.89 (d, J=7.6 Hz, 1H), 5.06 (dd, J=12.8, 5.4 Hz, 1H), 4.71 (d, J=12.8 Hz, 2H), 4.54 (dd, J=9.6, 4.6 Hz, 1H), 3.94-3.72 (m, 5H), 2.99-2.79 (m, 3H), 2.30 (s, 3H), 2.10 (q, J=7.2 Hz, 4H), 2.04-1.97 (m, 1H), 1.95-1.87 (m, 2H), 1.77 (q, J=5.5, 4.9 Hz, 6H), 1.57-1.41 (m, 4H), 1.20 (d, J=21.9 Hz, 3H), 1.01 (q, J=11.4, 10.6 Hz, 2H), 0.84 (d, J=7.2 Hz, 1H).
269: N-((1r,4r)-4-(3-chloro-4-cyanophenoxy)cyclohexyl)-6-(2-(2,6-dioxopiperidin-3-yl)-6-fluoro-1,3-dioxoisoindolin-5-yl)piperazin-1-yl)-7-azaspiro[3.5]nonan-7-yl)pyridazine-3-formamide
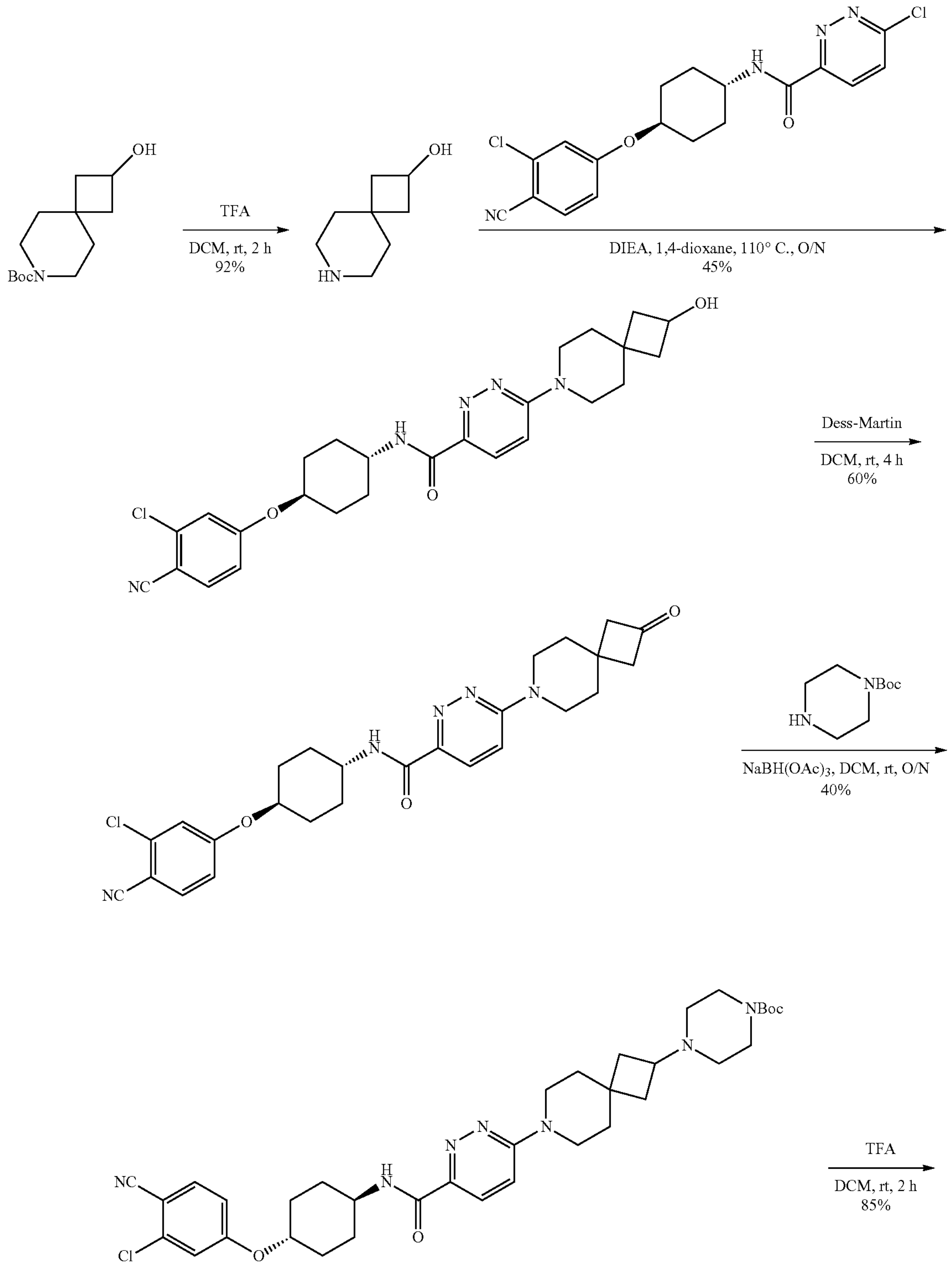

-continued

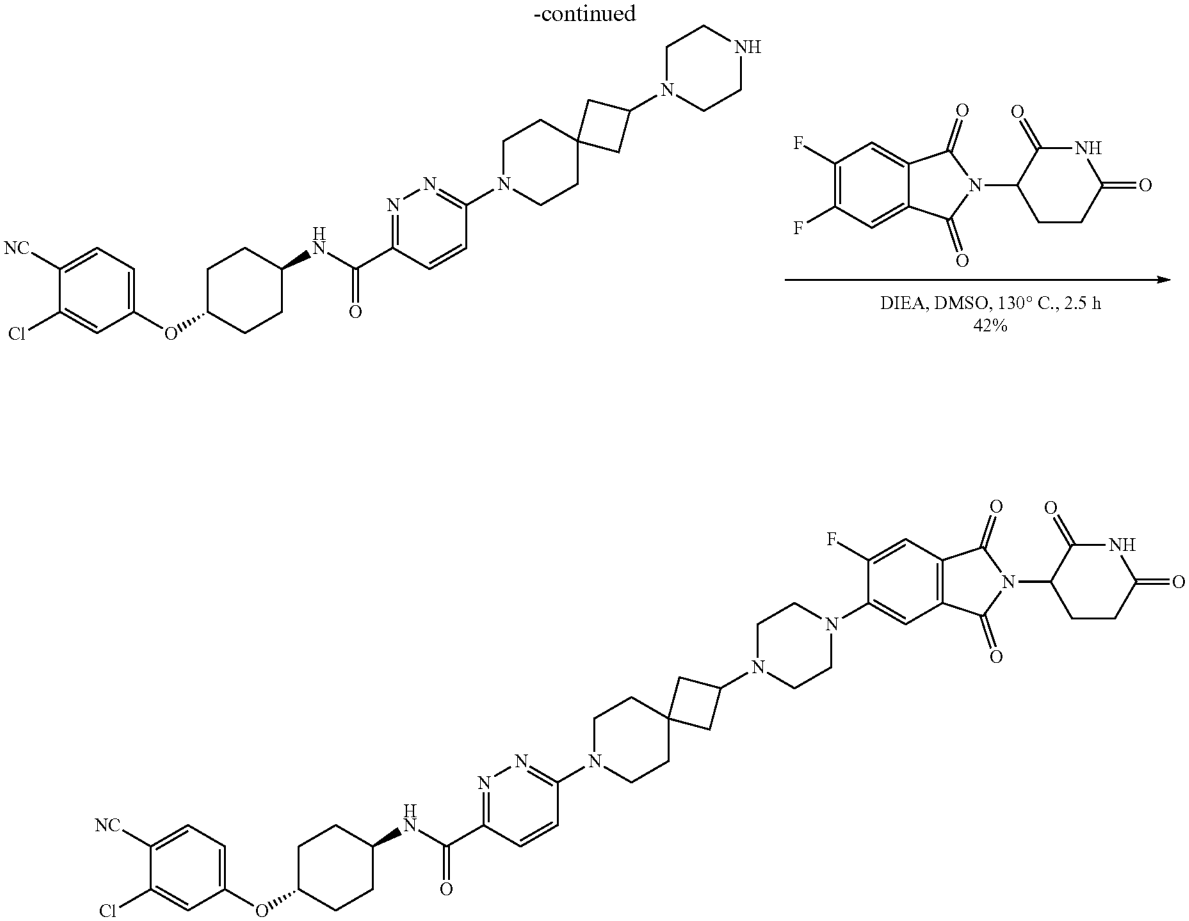

269

LC/MS (ESI$^+$) calcd for: $C_{43}H_{45}ClFN_9O_6[M+H]^+$ m/z, 838.3: found. 838.3.

$^1$H NMR (400 MHz, DMSO-$d_6$) δ11.12 (s, 1H), 8.60 (d, J=8.2 Hz, 1H), 7.86 (d, J=8.8 $H_z$, 1H), 7.79 (d, J=9.5 $H_z$, 1H), 7.74 (d, J=11.5 $H_z$, 1H), 7.46 (d, J=7.3 $H_z$, 1H), 7.39(d, J=2.5 $H_z$, 1H), 7.35 (d, J=9.6 $H_z$, 1H), 7.13 (dd, J=8.8, 2.4 $H_z$, 1H), 5.11 (dd, J=12.8, 5.4 $H_z$, 1H), 4.52 (d, J=10.4 $H_z$, 2H), 4.03 (d, J=7.1 $H_z$, 1H), 3.85 (s, 2H), 3.67 (d, J=30.6 $H_z$, 5H), 3.06 (s, 2H),2.88 (m, 4H), 1.99 (s, 2H), 1.89 (d, J=12.4$H_z$, 3H), 1.63 (d, J=9.6 $H_z$, 7H), 1.58-1.45 (m, 7H).

270: N-((1r,4r)-4-(3-chloro-4-cyanophenoxy)cyclohexyl)-6-(4-(7-(2-(2,6-dioxopiperidin-3-yl)-6-fluoro-13-dioxoisoindolin-5-yl) -7-azaspiro[3.5]nonan-2-yl) piperazin-1-yl)pyridazine-3-formamide

270

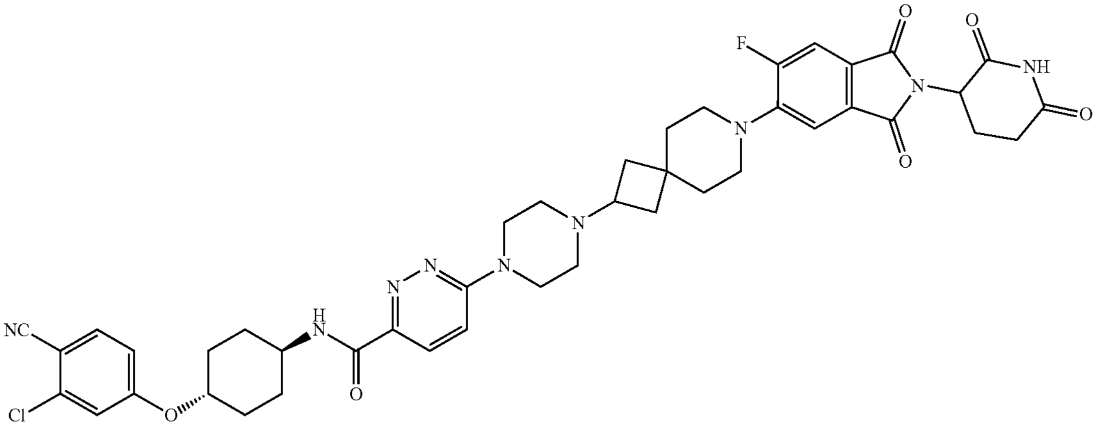

LC/MS ($ESI^+$) calcd for $C_{43}H_{45}ClFN_9O_6$[M+H]$^+$ m/z, 838.3; found 838.3.

$^1$H NMR (400 MHz, DMSO-$d_6$) δ 11.12 (s, 1H), 8.63 (d, J=8.2 Hz, 1H), 7.84 (t, J=8.6 Hz, 2H), 7.70 (d, J=11.4 Hz, 1H), 7.43 (d, J=7.4 Hz, 1H), 7.38 (d, J=2.4 Hz, 1H), 7.35 (d, J=9.7 Hz, 1H), 7.13 (dd, J=8.8, 2.5 Hz, 1H), 5.10 (dd, J=12.8, 5.4 Hz, 1H), 4.53 (dt, J=10.7, 6.1 Hz, 1H), 3.85 (dd, J=7.8, 3.8 Hz, 1H), 3.70 (d, J=5.2 Hz, 4H), 2.96-2.83 (m, 1H), 2.78-2.69 (m, 1H), 2.65-2.55 (m, 1H), 2.37 (t, J=4.9 Hz, 4H), 2.06 (dt, J=32.9, 6.7 Hz, 6H), 1.94-1.83 (m, 2H), 1.67 (dt, J=27.9, 5.5 Hz, 9H), 1.52 (t, J=11.0 Hz, 3H), 1.22 (s, 2H).

271: N-((1r,4r)-4-(3-chloro-4-cyanophenoxy)cyclohexyl)-6-(4-(7-(2-(2,6-dioxopiperidin-3-yl)-1,3-dioxoisoindolin-5-yl)-7-azaspiro[3.5]nonan-2-yl) piperazin-1-yl)pyridazine-3-formamide

271

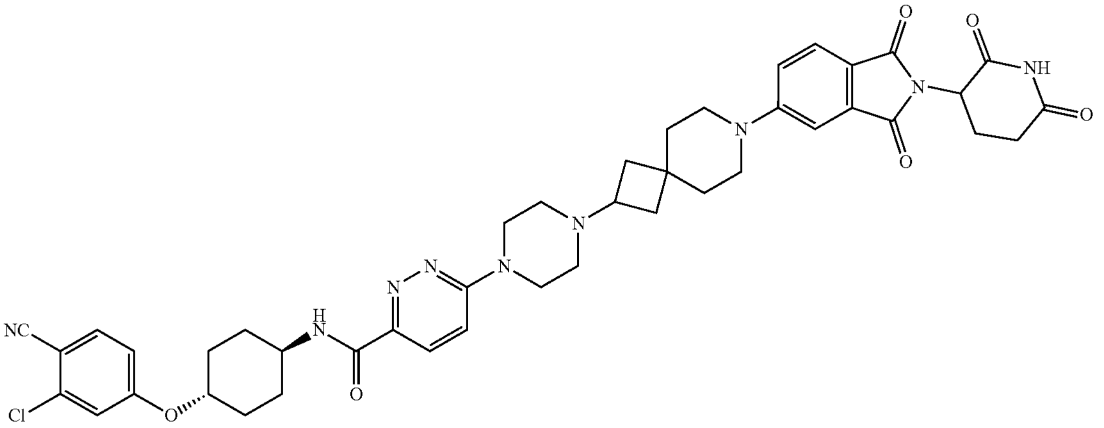

LC/MS ($ESI^+$) calcd for $C_{43}H_{46}ClN_9O_6$ [M+H]$^+$ m/z 820.3; found 820.3.

$^1$H NMR (400 MHz, DMSO-$d_6$) δ 11.05 (s, 1H), 8.61 (d, J=8.2 Hz, 1H), 7.84 (dd, J=9.2, 7.8 Hz, 2H), 7.64 (d, J=8.5 Hz, 1H), 7.40-7.29 (m, 3H), 7.23 (dd, J=8.8, 2.3 Hz, 1H), 7.13 (dd, J=8.8, 2.4 Hz, 1H), 5.06 (dd, J=12.9, 5.4 Hz, 1H), 4.52 (dd, J=9.5, 5.0 Hz, 1H), 3.92-3.79 (m, 1H), 3.70 (s, 4H), 2.95-2.81 (m, 1H), 2.73 (dd, J=13.7, 6.2 Hz, 1H), 2.50 (p, J=1.8 Hz, 6H), 2.37 (d, J=6.4 Hz, 4H), 2.16-1.97 (m, 5H), 1.89 (d, J=11.4 Hz, 2H), 1.64 (d, J=9.7 Hz, 5H), 1.56 (s, 4H), 1.22 (s, 1H).

272: N-((1r,4r)-4-(3-chloro-4-cyanophenoxy)cyclohexyl)-2-(5-((1-(2,6-dioxopiperidin-3-yl)-6-fluoro-1,3-dioxoisoindol-5-yl)piperidine-4-yl)methyl) hexahydropyrrolo[3,4-c]pyrrol-2(1H)-yl)pyrimidine-5-formamide

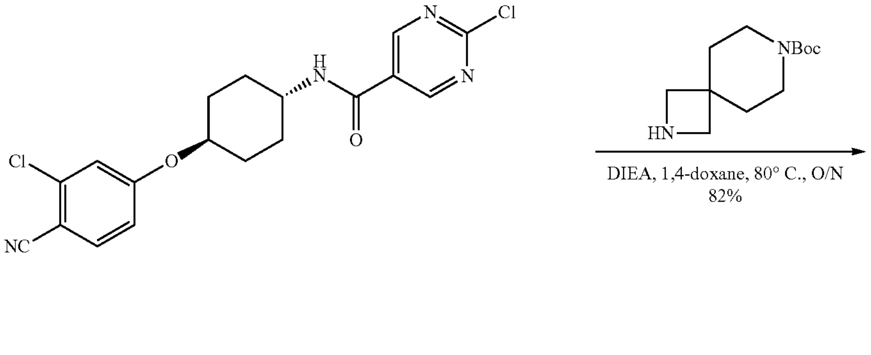

-continued
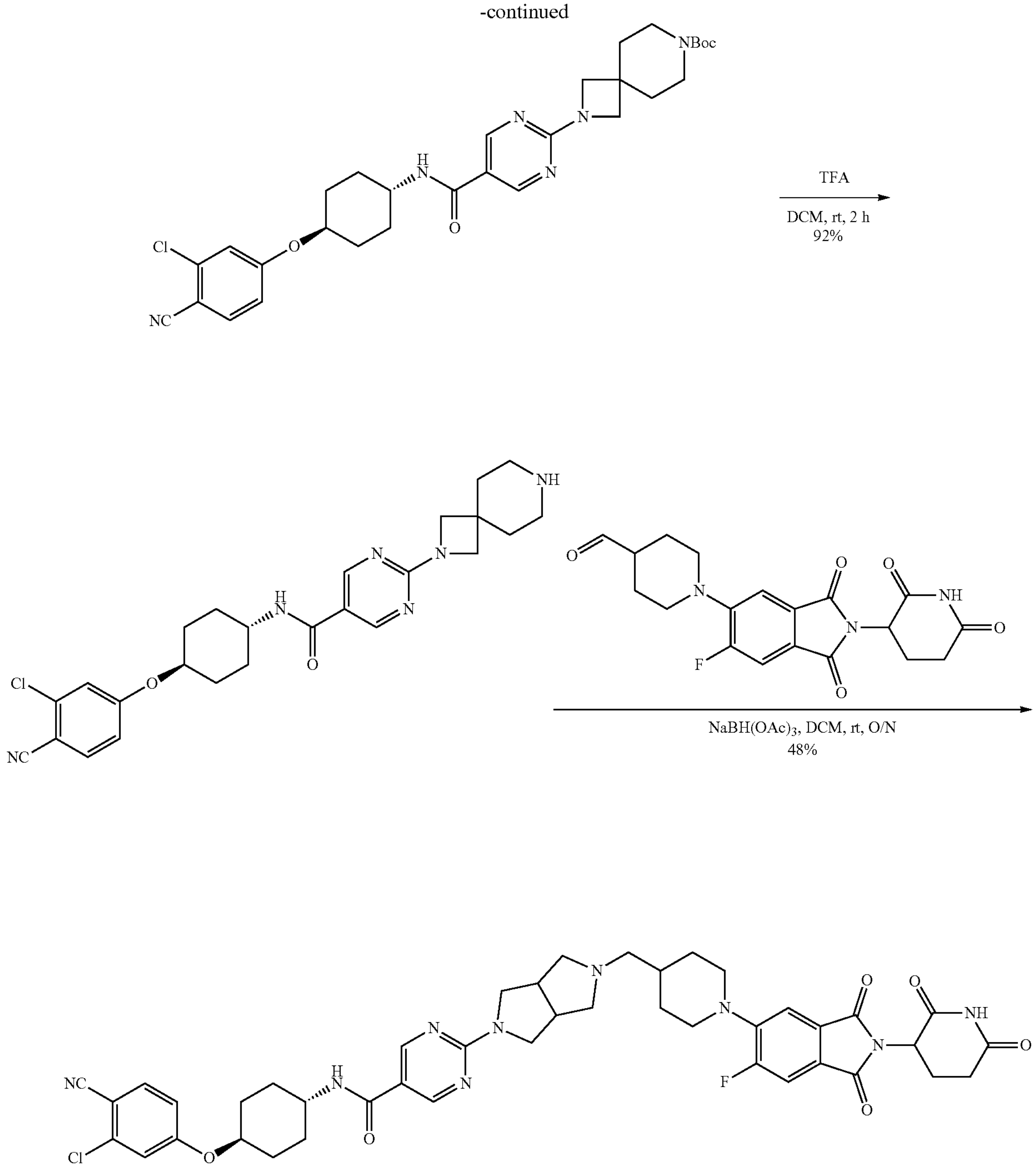
272
LC/MS (ESI+) calcd for: $C_{43}H_{45}ClFN_9O_6$ $[M+H]^+$ m/z, 838.3; found, 838.3. $^1H$ NMR (400 MHz, DMSO-$d_6$) δ 11.12 (s, 1H), 8.73 (s, 2H), 8.15 (d, J=7.4 Hz, 1H), 7.86 (d, J=8.8 Hz, 1H), 7.70 (d, J=11.4 Hz, 1H), 7.47-7.30 (m, 2H), 7.14 (dd, J=8.8, 2.5 Hz, 1H), 5.10 (dd, J=12.8, 5.4 Hz, 1H), 4.60-4.47 (m, 1H), 3.79 (s, 5H), 3.64-3.54 (m, 3H), 2.87 (td, J=12.9, 11.4, 5.5 Hz, 3H), 2.40-2.25 (m, 3H), 2.22-2.06 (m, 4H), 1.90 (d, J=7.9 Hz, 2H), 1.74 (d, J=5.9 Hz, 5H), 1.49 (p, J=5.9, 5.5 Hz, 5H), 1.32-1.13 (m, 4H).

273: N-((1r,4r)-4-(3-chloro-4-cyanophenoxy)cyclohexyl)-2-(7-(1-(2-(2,6-dioxopiperidin-3-yl)-6-fluoro-1,3-dioxoisoindolin-5-yl)piperidine-4-yl)-2,7-diazaspiro[3.5]nonan-2-yl)pyrimidine-5-carboxamide
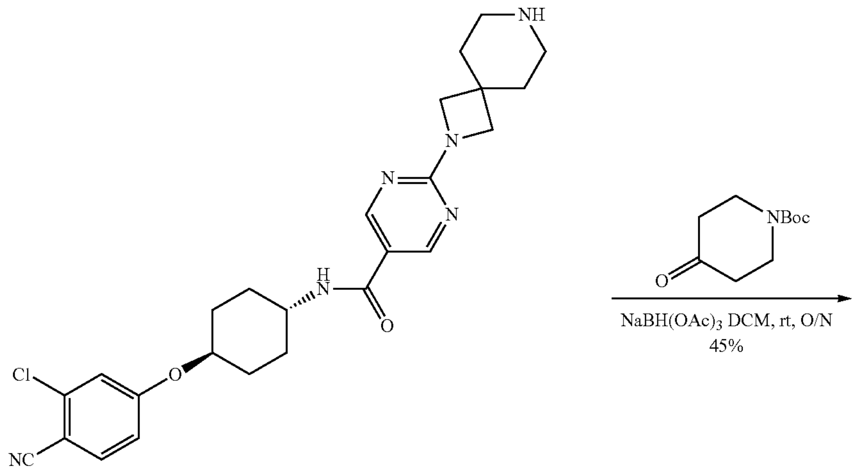
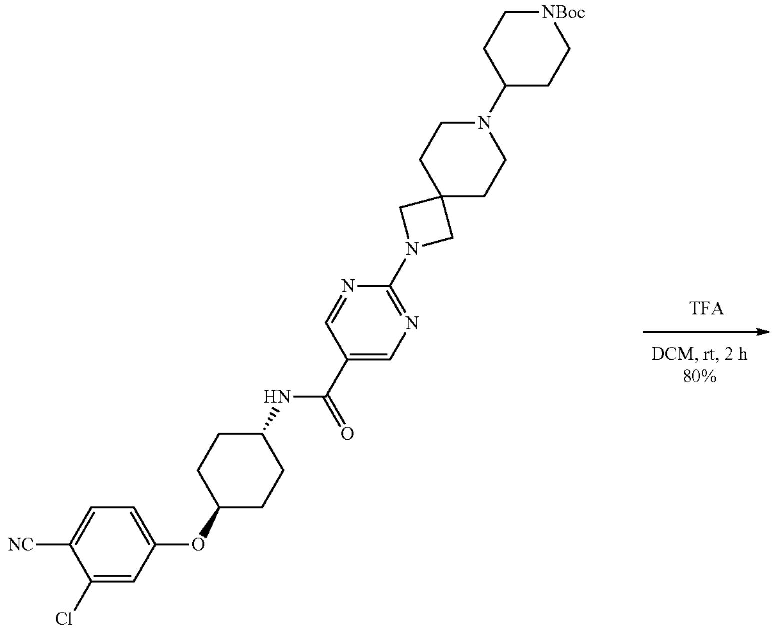

-continued
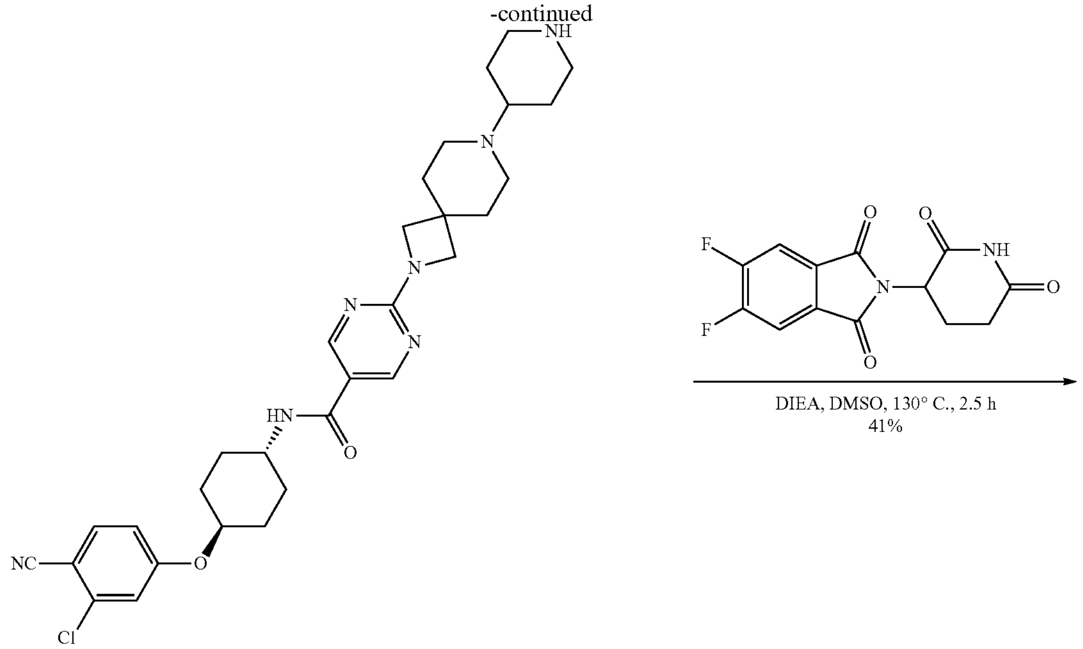
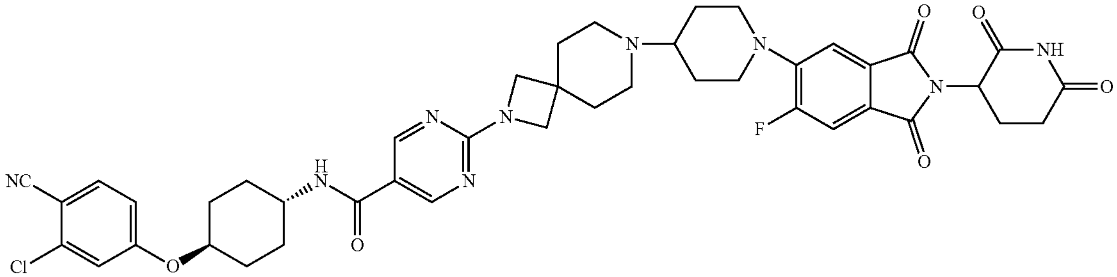
273
LC/MS (ESI+) calcd for: $C_{43}H_{45}ClFN_9O_6$ $[M+H]^+$ m/z, 838.3; found, 838.3. $^1H$ NMR (400 MHz, DMSO-$d_6$) δ 11.12 (s, 1H), 8.74 (s, 2H), 8.17 (d, J=7.5 Hz, 1H), 7.86 (d, J=8.8 Hz, 1H), 7.73 (d, J=11.4 Hz, 1H), 7.47 (d, J=7.4 Hz, 1H), 7.38 (d, J=2.4 Hz, 1H), 7.14 (dd, J=8.8, 2.5 Hz, 1H), 5.11 (dd, J=12.7, 5.4 Hz, 1H), 4.54 (d, J=8.5 Hz, 1H), 3.82 (d, J=21.0 Hz, 511), 3.69 (s, 4H), 3.10 (dd, J=15.7, 7.7 Hz, 3H), 2.98-2.80 (m, 5H), 2.14-2.05 (m, 3H), 1.90 (s, 6H), 1.70 (s, 2H), 1.56-1.40 (m, 5H), 1.18-1.12 (m, 1H).
274: N-((1r,4r)-4-(3-bromo-4-cyanophenoxy)cyclohexyl)-6-(4-((2-(2-(2-,2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide
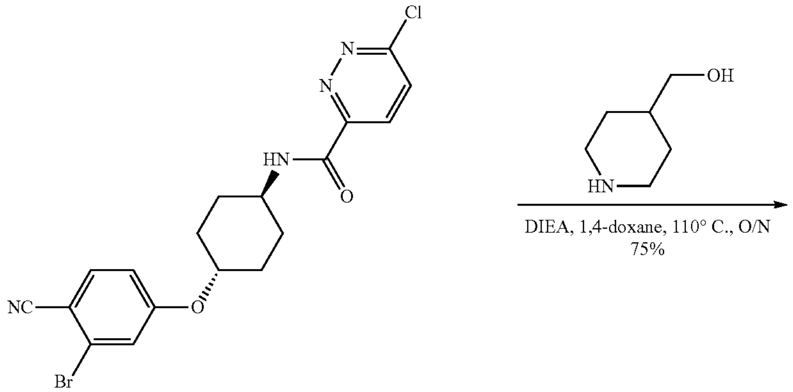

-continued
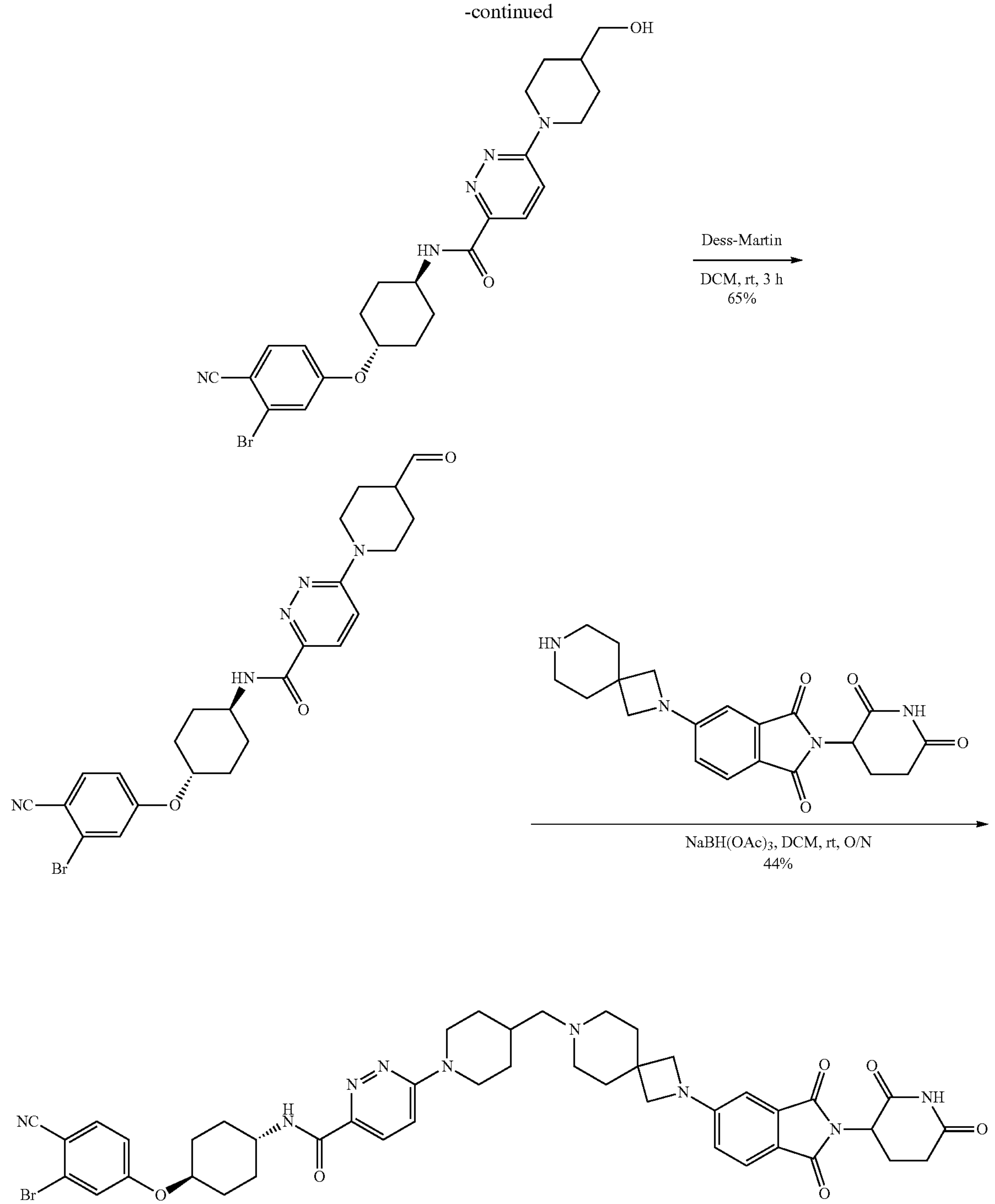
274
LC/MS ($ESI^+$) calcd for $C_{44}H_{47}BrFN_9O_6[M+H]^+$ m/z 880.3; found 880.3. $^1H$ NMR (400 MHz, DMSO-$d_6$) δ 11.08 (s, 1H), 8.58 (d, J=8.2 Hz, 1H), 7.81 (t, J=9.4 Hz, 2H), 7.63 (d, J=8.3 Hz, 1H), 7.49 (d, J=2.4 Hz, 1H), 7.33 (d, J=9.7 Hz, 1H), 7.16 (dd, J=8.8, 2.5 Hz, 1H), 6.77 (d, J=2.1 Hz, 1H), 6.64 (dd, J=8.4, 2.1 Hz, 1H), 5.05 (dd, J=12.9, 5.4 Hz, 1H), 4.58-4.41 (m, 3H), 3.90-3.82 (m, 1H), 3.75 (s, 4H), 3.08-2.80 (m, 4H), 2.64-2.53 (m, 2H), 2.21 (s, 2H), 2.14-2.06 (m, 2H), 2.00 (ddd, J=13.0, 5.5, 3.4 Hz, 1H), 1.89 (d, J=11.7 Hz, 4H), 1.81 (d, J=11.4 Hz, 6H), 1.71-1.43 (m, 5H), 1.22 (s, 1H), 1.10 (dd, J=18.1, 6.7 Hz, 2H).

275: N-((1r,4r)-4-(4-cyano-3-methylphenoxy)cyclohexyl)-6-(4-((2-(2-(2-(2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide
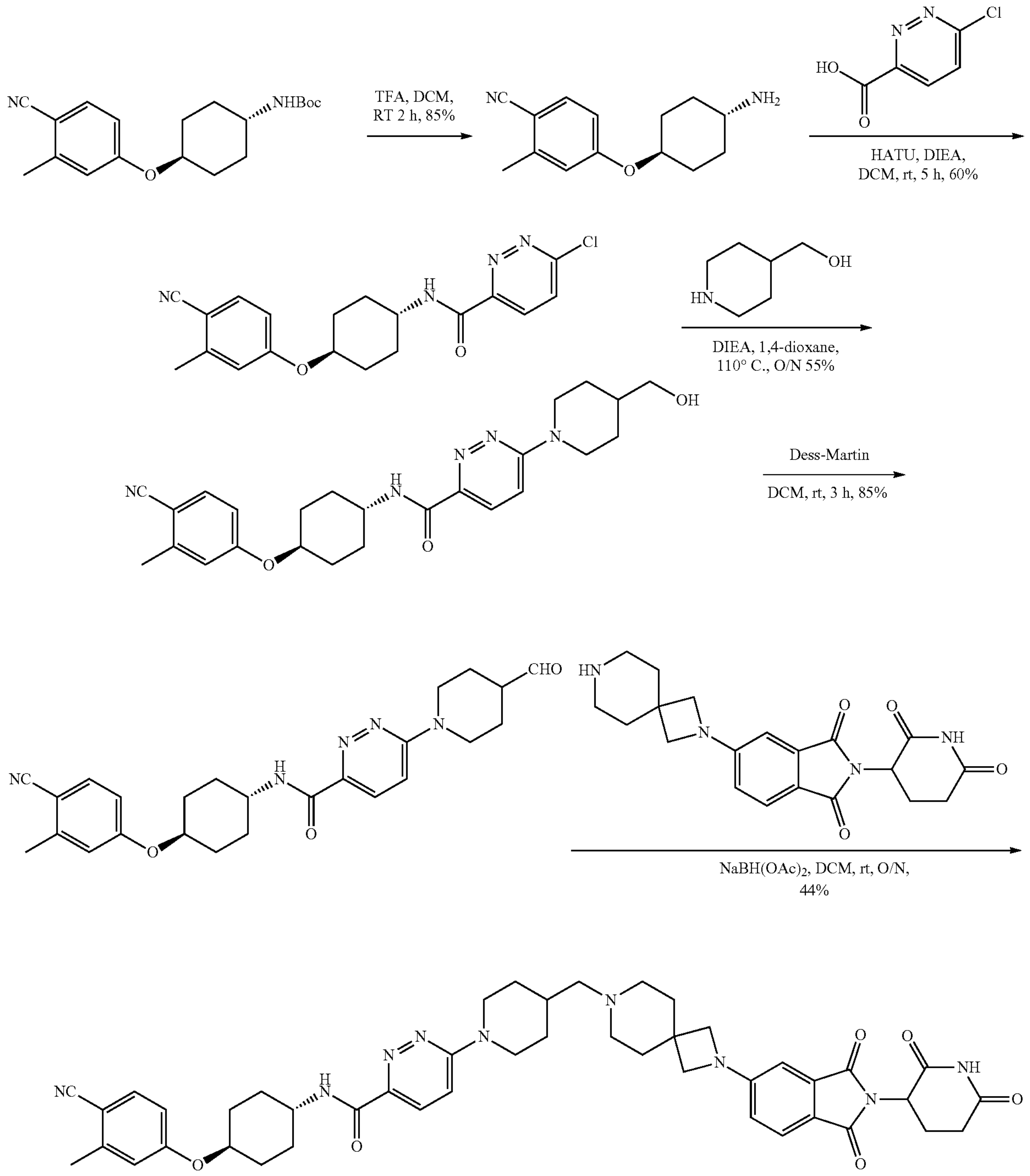
275
LC/MS (ESI$^+$) calcd for $C_{45}H_{51}N_9O_6$ $[M+H]^+$ m/z 814.4; found 814.4.
$^1$H NMR (400 MHz, DMSO-d$_6$) δ 11.08 (s, 1H), 8.58 (d, J=8.3 Hz, 1H), 7.80 (d, J=9.5 Hz, 1H), 7.64 (dd, J=8.5, 6.7 Hz, 2H), 7.32 (d, J=9.7 Hz, 1H), 7.04 (d, J=2.4 Hz, 1H), 6.93 (dd, J=8.6, 2.5 Hz, 1H), 6.77 (d, J=2.1 Hz, 1H), 6.64 (dd, J=8.5, 2.1 Hz, 1H), 5.05 (dd, J=12.9, 5.4 Hz, 1H), 4.45 (t, J=10.9 Hz, 3H), 3.86 (d, J=9.0 Hz, 1H), 3.74 (s, 4H), 2.99 (t, J=12.4 Hz, 2H), 2.89-2.81 (m, 1H), 2.43 (s, 3H), 2.32 (s, 3H), 2.11 (t, J=9.2 Hz, 3H), 2.00 (dd, J=8.9, 4.3 Hz, 1H), 1.91 (s, 6H), 1.76 (q, J=5.4 Hz, 5H), 1.67-1.44 (m, 5H), 1.22 (s, 1H), 1.10 (t, J=11.9 Hz, 2H).

276: N-((1r,4r)-4-(4-cyano-3-methoxyphenoxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridazine-3-carboxamide

276

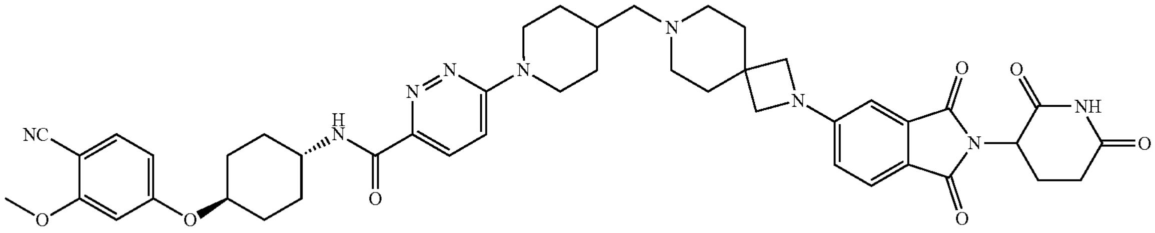

LC/MS (ESI$^+$) calcd for $C_{45}H_{51}N_9O_7$ $[M+H]^+$ m/z 830.3; found 830.3.

$^1H$ NMR (400 MHz, DMSO-$d_6$) δ 11.08 (s, 1H), 8.58 (d, J=8.2 Hz, 1H), 7.80 (d, J=9.5 Hz, 1H), 7.62 (dd, J=10.5, 8.7 Hz, 2H), 7.33 (d, J=9.7 Hz, 1H), 6.78 (d, J=2.1 Hz, 1H), 6.72 (dd, J=6.3, 2.4 Hz, 2H), 6.65 (dd, J=8.4, 2.1 Hz, 1H), 5.05 (dd, J=12.8, 5.4 Hz, 1H), 4.49 (dd, J=13.3, 8.9 Hz, 3H), 3.89 (s, 4H), 3.75 (s, 4H), 3.08-2.80 (m, 4H), 2.12 (d, J=12.9 Hz, 5H), 2.06-1.96 (m, 2H), 1.90 (d, J=7.6 Hz, 4H), 1.78 (s, 5H), 1.67-1.42 (m, 51-1), 1.23 (s, 2H), 1.18-1.02 (m, 2H).

277: N-((1r,4r)-4-(3-chloro-4-cyanophenoxy)cyclohexyl)-5-(4-(7-(2-(2,6-dioxopiperidin-3-yl)-6-fluoro-1,3-dioxoisoindolin-5-yl)-7-azaspiro[3.5]nonan-2-yl)piperazin-1-yl)pyrazine-2-carboxamide

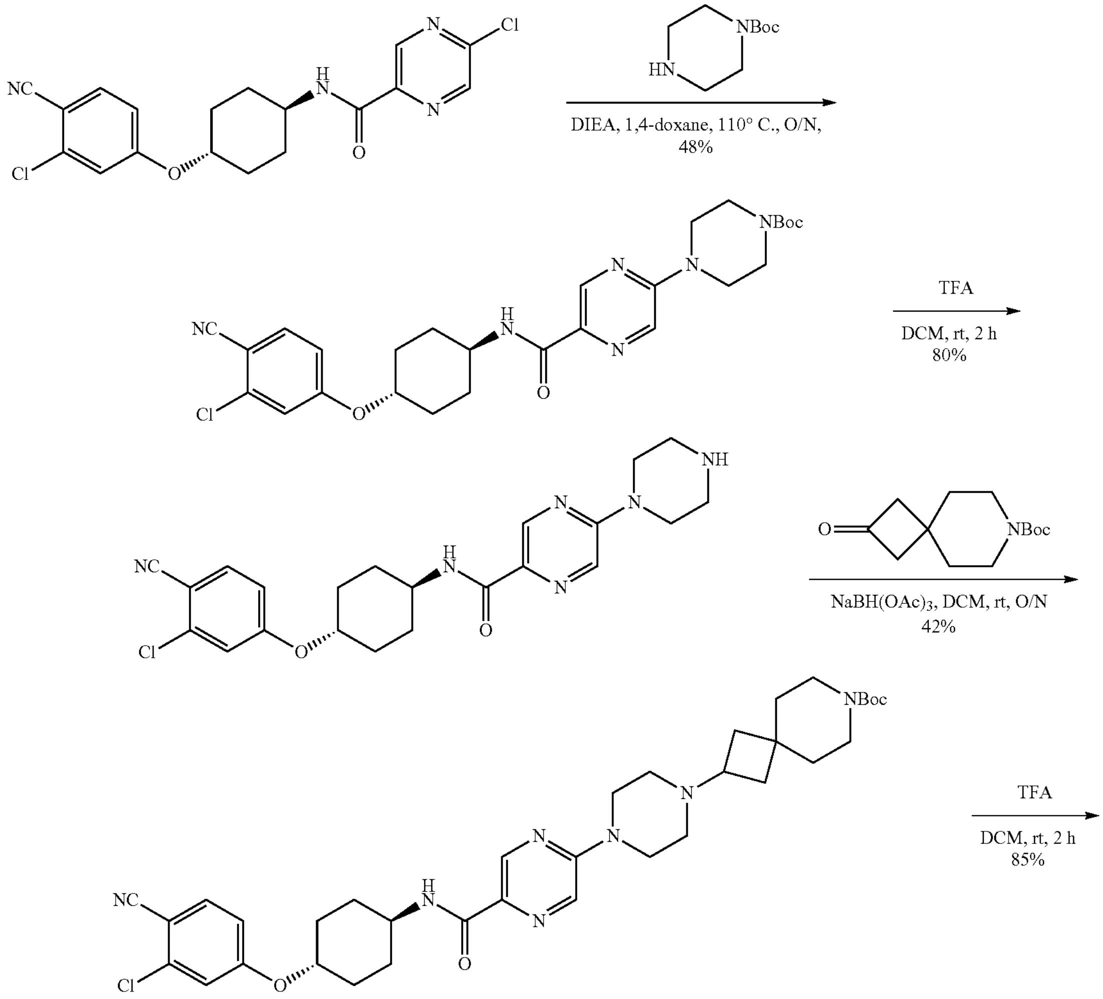

-continued

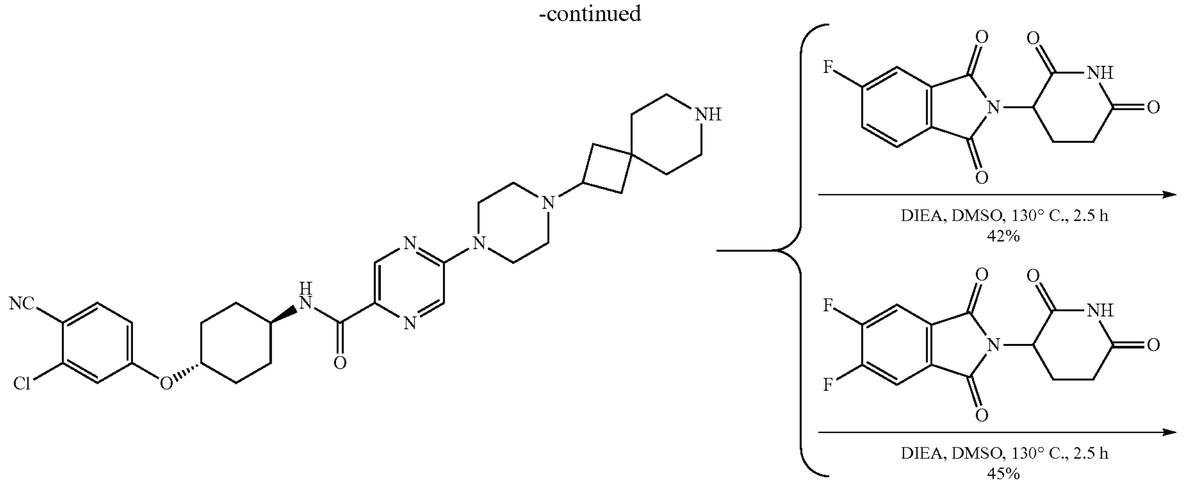

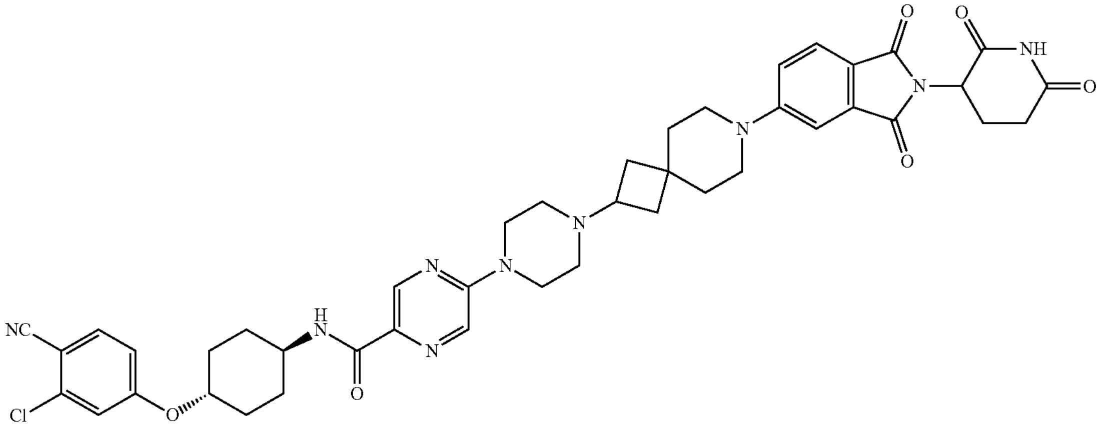

276

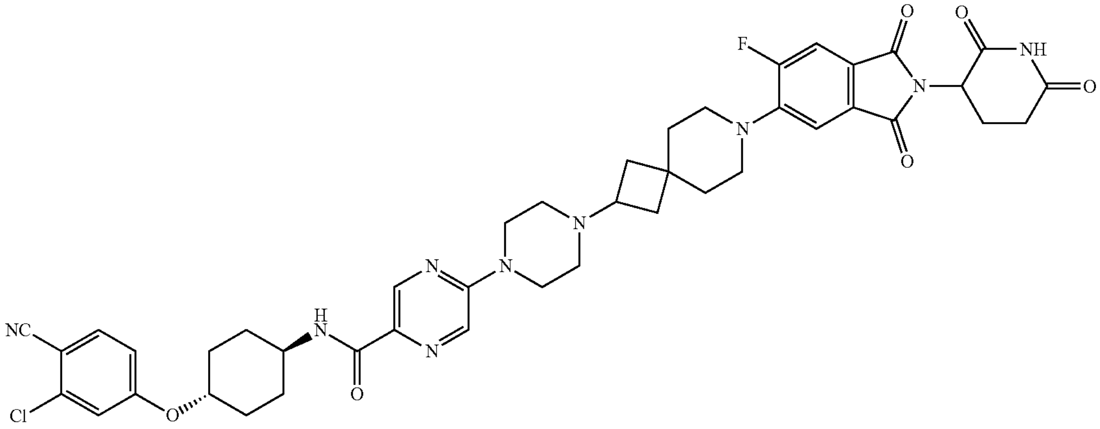

277

LC/MS (ESI+) calcd for: $C_{43}H_{45}ClFN_9O_6$ $[M+H]^+$ m/z, 838.3. found, 838.3. $^1H$ NMR (400 MHz, DMSO-$d_6$) δ 11.11 (s, 1H), 8.60 (d, J=1.2 Hz, 1H), 8.25 (s, 1H), 8.12 (d, J=8.2 Hz, 1H), 7.86 (d, J=8.8 Hz, 1H), 7.70 (d, J=11.4 Hz, 1H), 7.43 (d, J=7.3 Hz, 1H), 7.37 (d, J=2.5 Hz, 1H), 7.12 (dd, J=8.8, 2.5 Hz, 1H), 5.10 (dd, J=12.8, 5.4 Hz, 1H), 4.51 (s, 1H), 3.82 (d, J=10.1 Hz, 1H), 3.69 (s, 4H), 2.88 (td, J=16.4, 15.3, 5.5 Hz, 1H), 2.73 (dd, J=13.2, 5.6 Hz, 1H), 2.36 (d, J=5.9 Hz, 4H), 2.15-1.98 (m, 5H), 1.86 (s, 2H), 1.75-1.44 (m, 11H), 1.23 (s, 4H), 0.84 (d, J=7.0 Hz, 1H).

278: N-((1r,4r)-4-(3-chloro-4-cyanophenoxy)cyclohexyl)-5-(4-(7-(2-(2,6-dioxopiperidin-3-yl)-1,3-dioxoisoindolin-5-yl)-7-azaspiro[3.5]nonan-2-yl)piperazin-1-yl)pyrazine-2-carboxamide LC/MS (ESI+) calcd for: $C_{43}H_{46}ClN_9O_6$ $[M+H]^+$ m/z, 820.3; found, 820.3.

$^1H$ NMR (400 MHz, DMSO-$d_6$) δ 11.08 (s, 1H), 8.60 (s, 1H), 8.25 (s, 1H), 8.11 (d, J=8.1 Hz, 1H), 7.85 (d, J=8.7 Hz, 1H), 7.64 (d, J=8.4 Hz, 1H), 7.33 (dd, J=21.0, 2.3 Hz, 2H), 7.25-7.19 (m, 1H), 7.11 (dd, J=8.8, 2.4 Hz, 1H), 5.06 (dd, J=12.8, 5.4 Hz, 1H), 4.50 (s, 1H), 3.92-3.78 (m, 1H), 3.68

(t, J=4.9 Hz, 5H), 2.94-2.68 (m, 3H), 2.34 (t, J=5.0 Hz, 4H), 2.04 (dt, J=30.8, 9.6 Hz, 6H), 1.87 (d, J=12.1 Hz, 3H), 1.60 (dd, J=23.8, 11.0 Hz, 11H), 1.22 (s, 1H).

279: N-((1r,4r)-4-(3-chloro-4-cyanophenoxy)cyclohexyl)-3-(4-((2-(2-(2,6-dioxopiperidin-3-yl)-1,3-dioxoisoindolin-5-yl)-2,7-diazaspiro[3.5]nonane-7-yl) methyl)piperidin-1-yl)-1,2,4-triazine-6-formamide

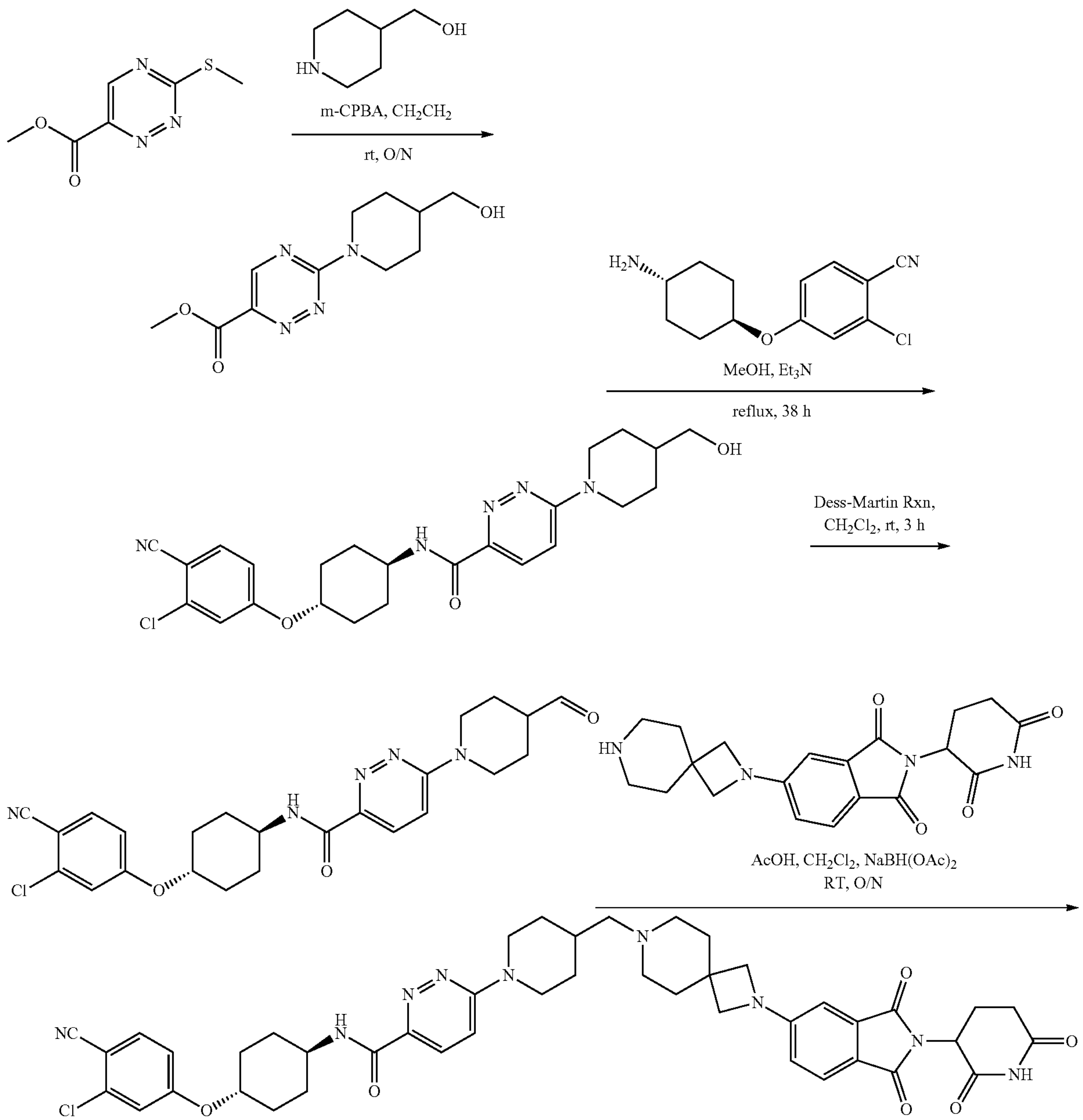

278

1. Methyl 3-(methylthio)-1,2,4-triazine-6-carboxylate

Using 3-amino-6-bromo-1,2,4-triazine as raw material, methyl 3-amino-1,2,4-triazine-6-carboxylate was prepared by a method in literature (PCT Int. Appl., 2015182712). Then, using methyl 3-amino-1,2,4-triazine-6-carboxylate as a raw material, methyl 3-(methylthio)-1,2,4-triazine-6-carboxylate was prepared as a pale yellow solid using a method in literature (PCT Int. Appl., 2015181539). MS: calcd. for $C_6H_7N_3O_2S$ $[M+H]^+$: 186.0; found: 186.3. $^1H$ NMR (400 MHz, $CDCl_3$) δ 8.95 (s, 1H), 4.08 (s, 3H), 2.73 (s, 3H).

2. Methyl 3-(4-(hydroxymethyl)piperidin-1-yl)-1,2,4-triazine-6-carboxylate

Methyl 3-(methylthio)-1,2,4-triazine-6-carboxylate (5.0 g, 27.00 mmol) was dissolved in 200 mL of dichloromethane, to which was added m-chloroperoxybenzoic acid (10.7 g, 62.09 mmol) in batches. The solution was stirred at room temperature for 4 h, to which was added triethylamine (10.9 g, 107.99 mmol), followed by addition of 4-piperidinemethanol (9.3 g, 80.99 mmol). The mixture was stirred overnight at room temperature. The reaction solution was added with water and dichloromethane, whose pH was adjusted to 8-9 with sodium carbonate. Then, the reaction solution was extracted. The organic layer was washed with the solution of sodium thiosulfate, dried, rotatory evaporated to dry, and purified by a silica gel column, to provide compound methyl 3-(4-(hydroxymethyl)piperidin-1-yl)-1,2,4-triazine-6-carboxylate (2.0 g, 7.93 mmol), with a yield of 29.9%. LC/MS (ESI$^+$) calcd for $C_{11}H_{17}N_4O_3^+$ ([M+H]$^+$) m/z: 253.1; found 253.1.

3. Synthesis of compound N-((1r,4r)-4-(3-chloro-4-cyanophenoxy)cyclohexyl)-3-(4-hydroxymethyl)piperidin-1-yl)-1,2,4-triazine-6-formamide Methyl 3-(4-(hydroxymethyl)piperidin-1-yl)-1,2,4-triazine-6-carboxylate (100.0 mg, 0.39 mmol) and 4-(((1r,4r)-4-aminocyclohexyl)oxy)-2-chlorobenzonitrile (149.1 mg, 0.59 mmol) were dissolved in 2 mL of methanol and 0.3 mL of triethylamine, and the reaction solution was heated 36 h under reflux. Then, the solution was cooled to room temperature, rotatory evaporated to dry, and purified by silica gel column chromatography, to provide compound N-((1r,4r)-4-(3-chloro-4-cyanophenoxy) cyclohexyl)-3-(4-hydroxymethyl)piperidin-1-yl)-1,2,4-triazine-6-formamide (72.0 mg, 0.15 mmol), with a yield of 38.5%. LC/MS (ESI$^+$) calcd for $C_{23}H_{28}ClN_6O_3^+$ ([M+H]$^+$) m/z: 471.2; found 471.1.

4. Synthesis of compound N-((1r,4r)-4-(3-chloro-4-cyanophenoxy)cyclohexyl)-3-(4-formylpiperidin-1-yl)-1,2,4-triazine-6-formamide N-((1r,4r)-4-(3-chloro-4-cyanophenoxy)cyclohexyl)-3-(4-hydroxymethyl)piperidin-1-yl)-1,2,4-triazine-6-formamide (72.0 mg, 0.15 mmol) was dissolved in 5 mL of dichloromethane, to which was added Dess-Martin periodinane (86 mg, 0.21 mmol), and the solution was stirred 4 h at room temperature. The reaction solution was added with dichloromethane and water for extraction, and the organic layer was washed with saturated brine, dried, and rotatory evaporated to dry, to provide compound N-((1r,4r)-4-(3-chloro-4-cyanophenoxy)cyclohexyl)-3-(4-formylpiperidin-1-yl)-1,2,4-triazine-6-formamide (80 mg, 0.15 mmol), with a yield of 100.0%.

LC/MS (ESI$^+$) calcd for $C_{23}H_{26}ClN_6O_3^+$ ([M+H]$^+$) m/z: 469.2; found 469.3.

5. Synthesis of Compound N-((1r,4r)-4-(3-chloro-4-cyanophenoxy)cyclohexyl)-3-(4-((2-(2,6-dioxopiperidin-3-yl)-1,3-dioxoisoindolin-5-yl)-2,7-diazaspiro[3.5]nonan-7-yl)methyl)piperidin-1-yl)-1,2,4-triazine-6-formamide N-((1r,4r)-4-(3-chloro-4-cyanophenoxy)cyclohexyl)-3-(4-formylpiperidin-1-yl)-1,2,4-triazine-6-formamide (80 mg, 0.15 mmol) and 2-(2,6-dioxopiperidin-3-yl)-5-(2,7-diazaspiro[3.5]nonan-2-yl)isoindoline-1,3-dione (57.0 mg, 0.15 mmol) were dissolved in 2 mL of dichloromethane, and then one drop of acetic acid was added, followed by addition of sodium triethoxyborohydride (126.0 mg, 0.60 mmol). The solution was stirred overnight at room temperature. Then, the reaction solution was added with dichloromethane and water for extraction, and the organic layer was washed with saturated brine, dried, rotatory evaporated to dry, and purified by prep.-TLC, to provide the target compound (56 mg, 0.06 mmol), with a yield of 44.9%.

LC/MS (ESI$^+$) calcd for $C_{43}H_{48}ClN_{10}O_6$ ([M+H]$^+$) m/z: 835.3; found 835.3.

$^1$H NMR (400 MHz, $CDCl_3$) δ 8.82 (s, 1H), 8.15 (s, 1H), 7.65 (d, J=8.3 Hz, 1H), 7.57 (t, J=8.6 Hz, 2H), 7.00 (d, J=2.3 Hz, 1H), 6.85 (dd, J=8.7, 2.4 Hz, 1H), 6.78 (d, J=1.9 Hz, 1H), 6.51 (dd, J=8.3, 1.9 Hz, 1H), 4.94 (dd, J=12.2, 5.3 Hz, 3H), 4.31 (t, J=9.9 Hz, 1H), 4.13-4.00 (m, 1H), 3.75 (s, 4H), 3.06 (s, 2H), 2.93-2.66 (m, 4H), 2.45 (s, 3H), 2.35-2.07 (m, 8H), 1.96 (s, 8H), 1.72-1.63 (m, 2H), 1.44 (dd, J=17.2, 8.6 Hz, 2H).

280: N-((1r,4r)-4-(3-chloro-4-cyanophenoxy)cyclohexyl)-5-(4-(2-(2-(2,6-dioxopiperidin-3-yl)-1,3-dioxoisoindolin-5-yl)-2,7-diazaspiro[3.5]nonan-7-yl)piperidin-1-yl)pyrazine-2-carboxamide

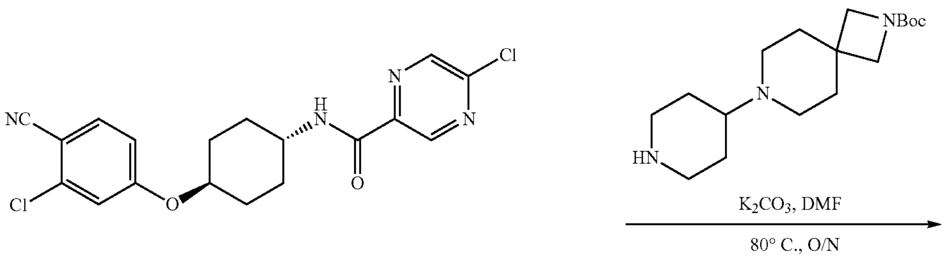

-continued
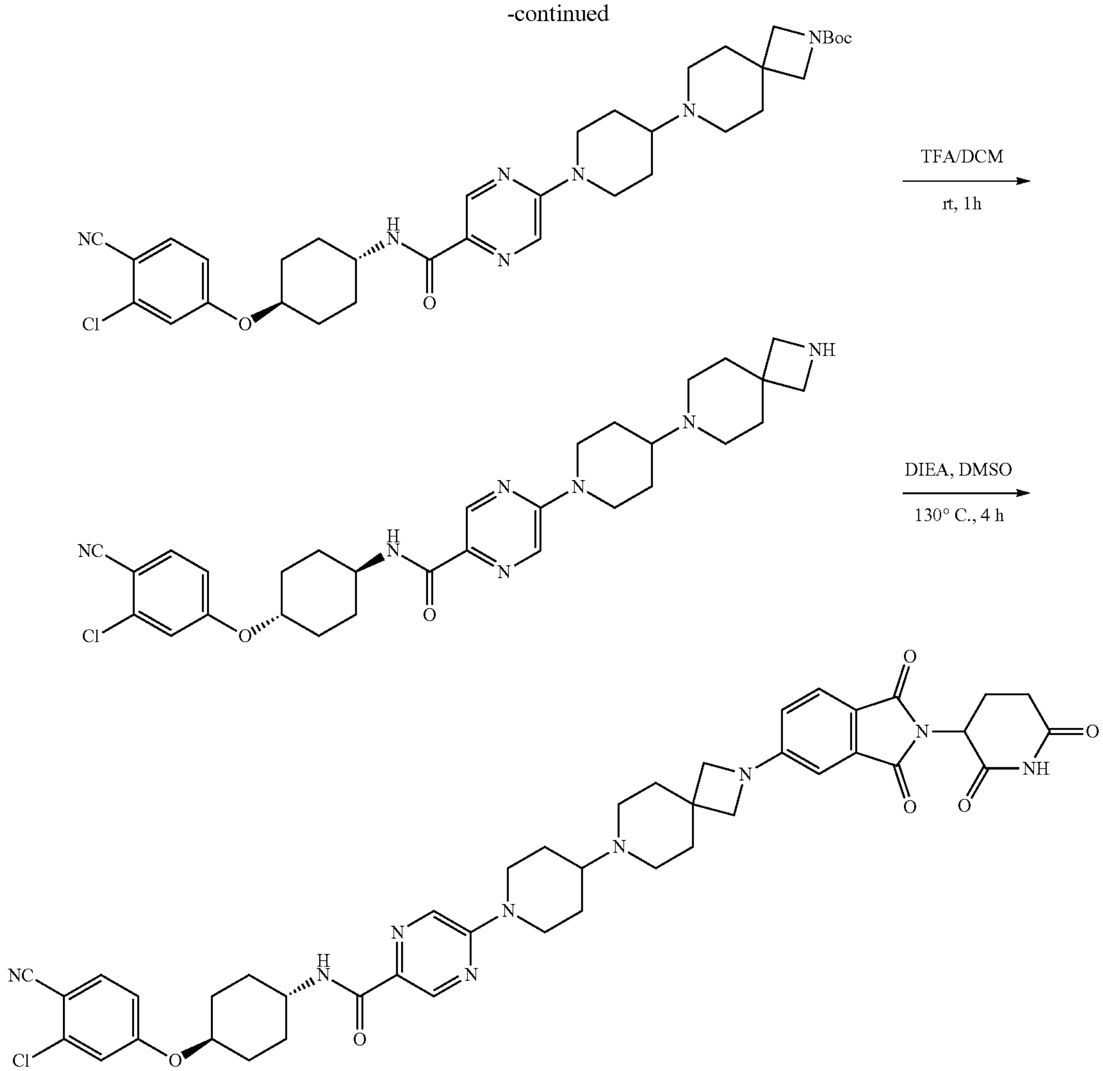
280
LC/MS (ESI+) calcd for $C_{43}H_{47}ClN_9O_6^+$ ([M+H]+) m/z: 820.3; found 820.3.
1H NMR (400 MHz, CDCl3) δ 8.84 (d, J=0.9 Hz, 1H), 8.20 (s, 1H), 7.99 (s, 1H), 7.65 (d, J=8.3 Hz, 1H), 7.56 (d, J=8.7 Hz, 1H), 7.40 (d, J=8.3 Hz, 1H), 6.99 (d, J=2.3 Hz, 1H), 6.85 (dd, J=8.7, 2.3 Hz, 1H), 6.78 (d, J=1.9 Hz, 1H), 6.51 (dd, J=8.3, 1.9 Hz, 1H), 4.93 (dd, J=12.2, 5.3 Hz, 1H), 4.54 (d, J=12.5 Hz, 2H), 4.30 (t, J=10.0 Hz, 1H), 4.10-3.96 (m, 1H), 3.75 (s, 4H), 3.00 (t, J=11.9 Hz, 2H), 2.91-2.67 (m, 5H), 2.17 (dd, J=9.1, 5.0 Hz, 5H), 2.01 (d, J=31.7 Hz, 5H), 1.75-1.64 (m, 8H), 1.52-1.44 (m, 2H).
281: N-((1r,4r)-4-(3-chloro-4-cyanophenoxy)cyclohexyl)-6-(4-(2-(2-(2,6-dioxopiperidin-3-yl)-1,3-dioxoisoindolin-5-yl)-2,7-diazaspiro[3.5]nonan-7-yl)piperidin-1-yl)pyridazine-3-formamide
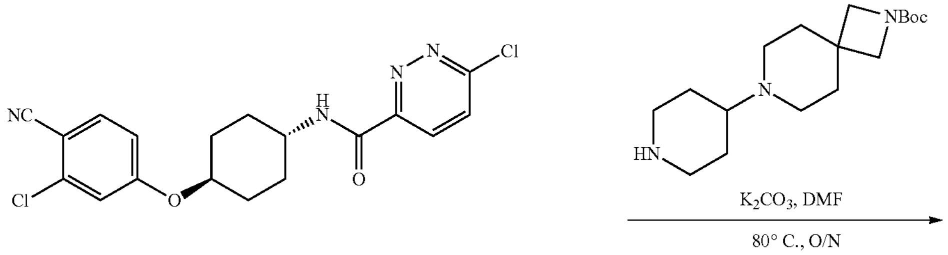

-continued
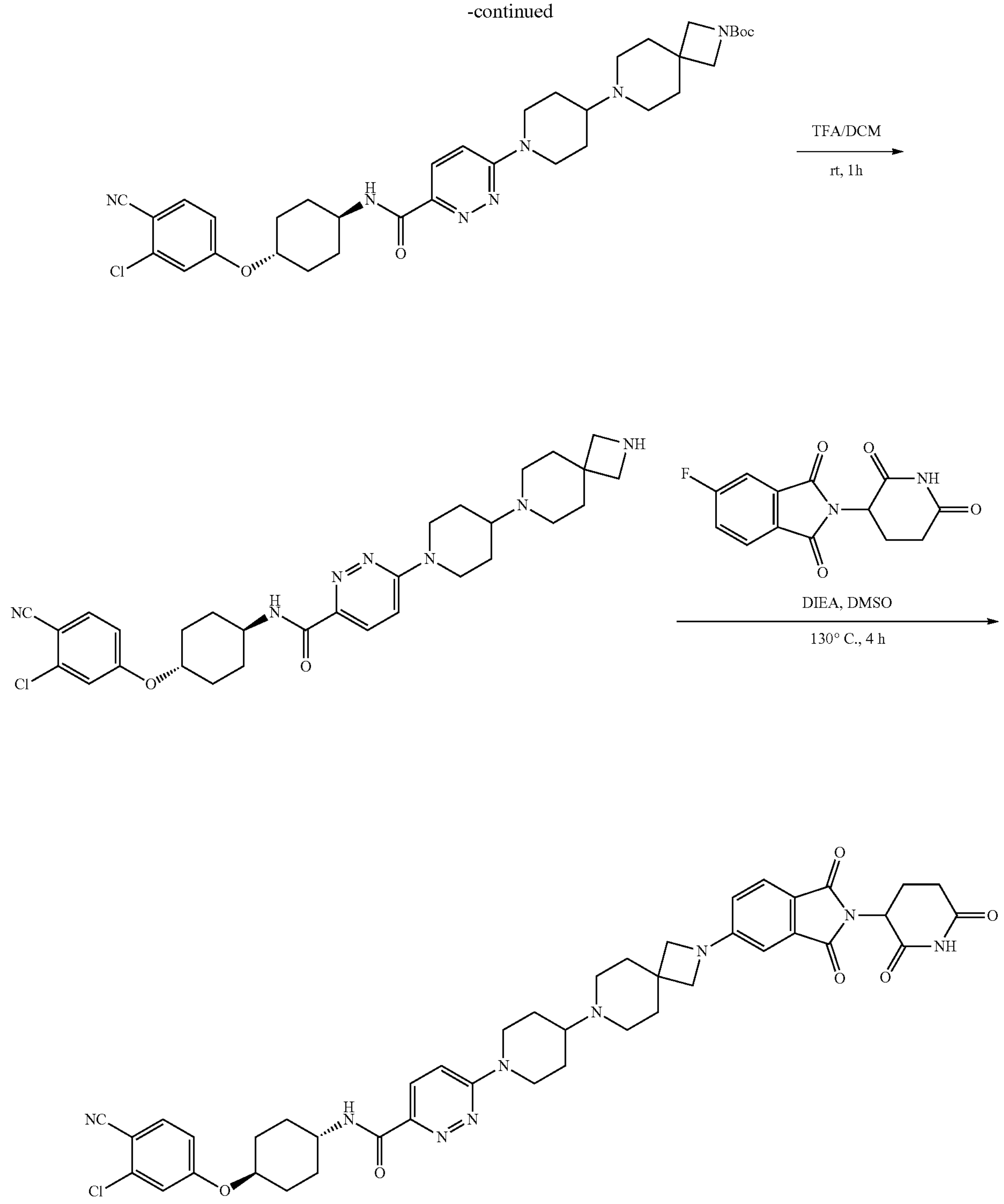
281
LC/MS ($ESI^+$) calcd for $C_{43}H_{47}ClN_2O_6^+$ ($[M+H]^+$) m/z 820.3; found 820.3.
$^1H$ NMR (400 MHz, $CDCl_3$) δ 8.14 (s, 1H), 8.01 (d, J=9.4 Hz, 1H), 7.88 (d, J=8.2 Hz, 1H), 7.65 (d, J=8.3 Hz, 1H), 7.56 (d, J=8.7 Hz, 1H), 7.01 (t, J=6.0 Hz, 2H), 6.86 (dd, J=8.7, 2.3 Hz, 1H), 6.78 (d, J=1.7 Hz, 1H), 6.52 (d, J=8.4 Hz, 1H), 4.93 (dd, J=12.2, 5.3 Hz, 1H), 4.61 (s, 2H), 4.32 (s, 1H), 4.06 (d, J=8.0 Hz, 1H), 3.76 (s, 4H), 3.07 (t, J=12.5 Hz, 2H), 2.94-2.83 (m, 2H), 2.82-2.67 (m, 3H), 2.28-2.67 (m, 101H), 1.64 (s, 8H), 1.50-1.42 (m, 2H).

282: N-((1r,4r)-4-(3-chloro-4-cyanophenoxy)cyclohexyl)-6-(7-((1-(2-(2,6-dioxopiperidin-3-yl)-1,3-dioxoisoindolin-5-yl)piperidine-4-yl)methyl)-2,7-diazaspiro[3.5]nonan-2-yl)pyridazine-3-formamide

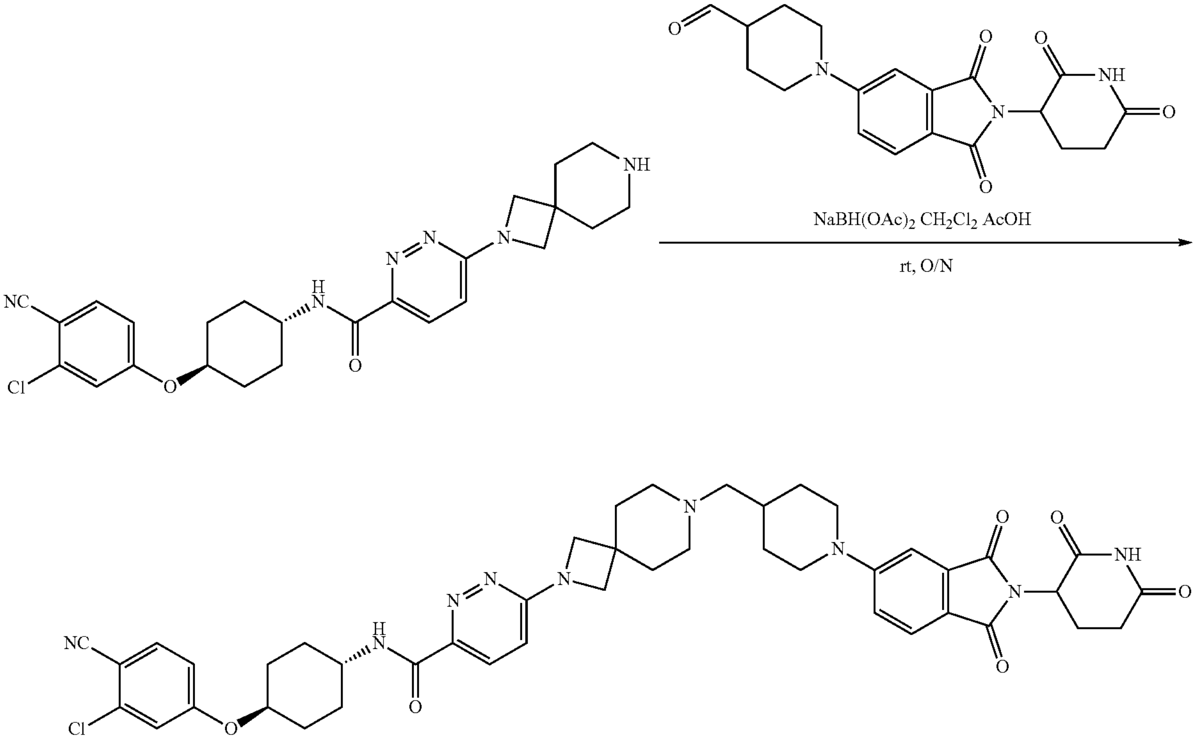

282

LC/MS ($ESI^+$) calcd for $C_{44}H_{49}ClN_9O_6^+$ ($[M+H]^+$) m/z: 834.3; found 834.3.

$^1$H NMR (400 MHz, $CDCl_3$) δ 8.23 (s, 1H), 7.98 (d, J=9.2 Hz, 1H), 7.88 (d, J=8.2 Hz, 1H), 7.68 (d, J=8.5 Hz, 1H), 7.56 (d, J=8.7 Hz, 1H), 7.28 (d, J=2.2 Hz, 1H), 7.05 (dd, J=8.6, 2.3 Hz, 1H), 7.00 (d, J=2.4 Hz, 1H), 6.85 (dd, J=8.8, 2.4 Hz, H), 6.59 (d, J=9.3 Hz, 1H), 4.94 (dd, J=12.3, 5.3 Hz, 1H), 4.38-4.26 (m, 1H), 4.15-3.79 (m, 7H), 2.98 (t, J=12.1 Hz, 2H), 2.92-2.71 (m, 3H), 2.42 (s, 4H), 2.15 (dt, J=12.8, 7.9 Hz, 6H), 1.92 (s, 5H), 1.71 (dd, J=19.8, 10.2 Hz, 8H), 1.46 (dt, J=14.3, 7.3 Hz, 2H).

283: N-((1r,4r)-4-(3-chloro-4-cyanophenoxy)cyclohexyl)-6-(7-((1-(2-(2,6-dioxopiperidin-3-yl)-1,3-dioxoisoindolin-5-yl)piperidine-4-yl)methyl)-2,7-diazaspiro[3.5]nonan-2-yl)pyrazine-3-formamide

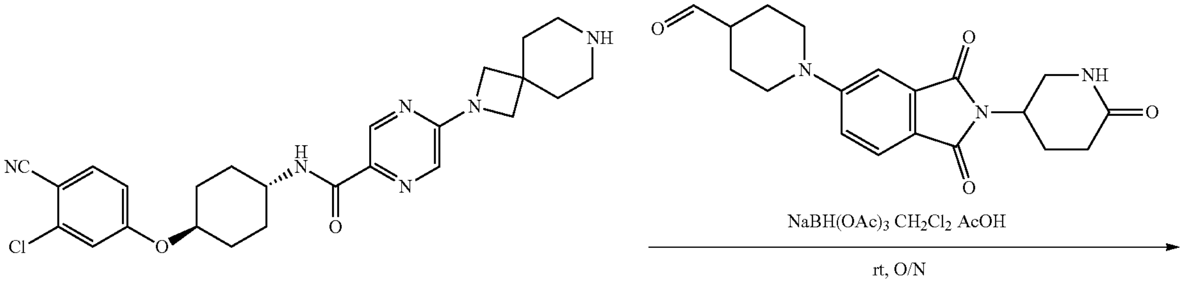

-continued

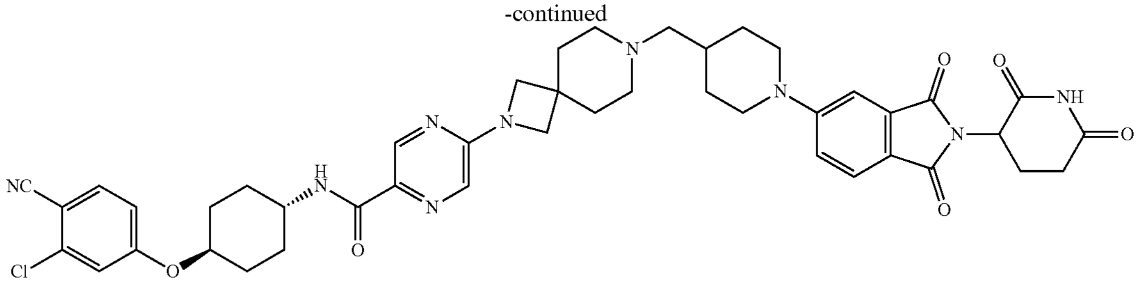

283

LC/MS (ESI+) calcd for $C_{44}H_{49}ClN_9O_6^+$ ([M+H]+) m/z: 834.3; found 834.3.

$^1$H NMR (400 MHz, $CDCl_3$) δ 8.84 (s, 1H), 8.01 (d, J=8.8 Hz, 1H), 7.70 (d, J=8.2 Hz, 1H), 7.62 (d, J=8.5 Hz, 1H), 7.55 (d, J=8.7 Hz, 1H), 7.39 (d, J=2.2 Hz, 1H), 7.30 (dd, J=8.6, 2.3 Hz, 1H), 7.06 (d, J=2.4 Hz, 1H), 6.99 (dd, J=8.8, 2.4 Hz, 1H), 6.86 (d, J=9.3 Hz, 1H), 4.99-4.92 (m, 1H), 4.35-4.28 (m, 1H), 3.98 (m, 6H), 3.69-3.61 (m, 1H), 2.95 (d, J=55.1 Hz, 9H), 2.18 (m, 6H), 2.00 (m, 5H), 1.55-1.43 (m, 10H).

284: N-((1r,4r)-4-(3-chloro-4-cyanophenoxy)cyclohexyl)-5-(7-((1-(2-(2,6-dioxopiperidin-3-yl)-1,3-dioxoisoindolin-5-yl)piperidine-4-yl)methyl)-2,7-diazaspiro[3.5]nonan-2-yl)pyrazine-2-carboxamide

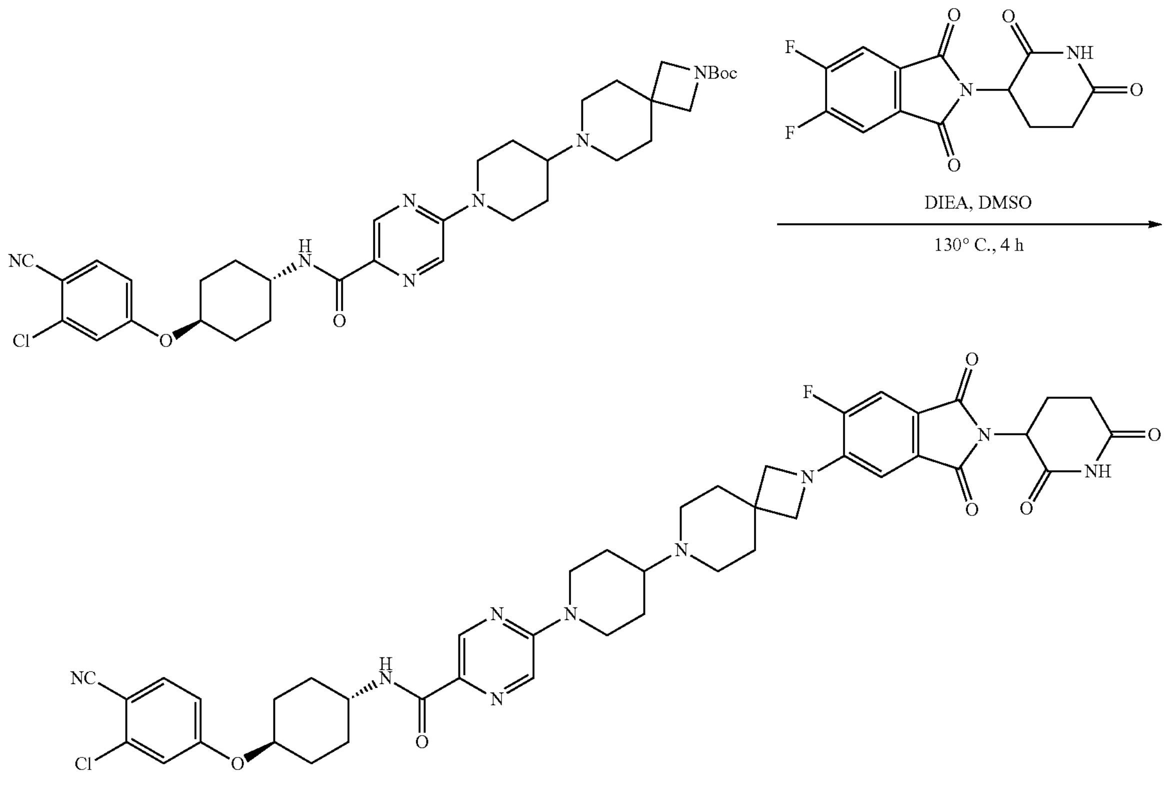

284

LC/MS(ESI+) calcd for $C_{43}H_{46}ClFN_9O_6^+$ ([M+H]+) m/z: 838.3, found 838.2.

$^1$H NMR (400 MHz, $CDCl_3$) δ 8.12 (s, 1H), 7.99 (d, J=9.6 Hz, 1H), 7.87 (d, J=8.0 Hz, 1H), 7.56 (d, J=8.7 Hz, 1H), 7.36 (d, J=10.9 Hz, 1H), 7.04-6.96 (m, 2H), 6.86 (dd, J=8.8, 2.1 Hz, 1H), 6.80 (d, J=7.5 Hz, 1H), 4.91 (dd, J=12.2, 5.0 Hz, 1H), 4.57 (d, J=13.0 Hz, 2H), 4.32 (s, 1H), 4.05 (s, 1H), 3.89 (s, 4H), 3.79 (s, 1H), 3.46 (d, J=6.7 Hz, 1H), 3.20 (s, 1H), 3.05 (t, J=12.3 Hz, 2H), 2.89 (d, J=14.4 Hz, 1H), 2.82-2.68

(m, 3H), 2.17 (d, J=10.9 Hz, 5H), 2.00 (s, 4H), 1.66 (dd, J=24.2, 11.3 Hz, 8H), 1.49 (d, J=12.1 Hz, 2H).

285: N-((1r,4r) 4-(4-cyano-3-(trifluoromethyl)phenoxy)cyclohexyl)-6-(2-((1-(2,6-dioxopiperidin-3-yl)-6-fluoro-1,3-dioxoisoindolin-5-yl)piperidine-4-yl) methyl)-2,7-diazaspiro [3.5] nonan-7-yl)pyridazine-3-formamide

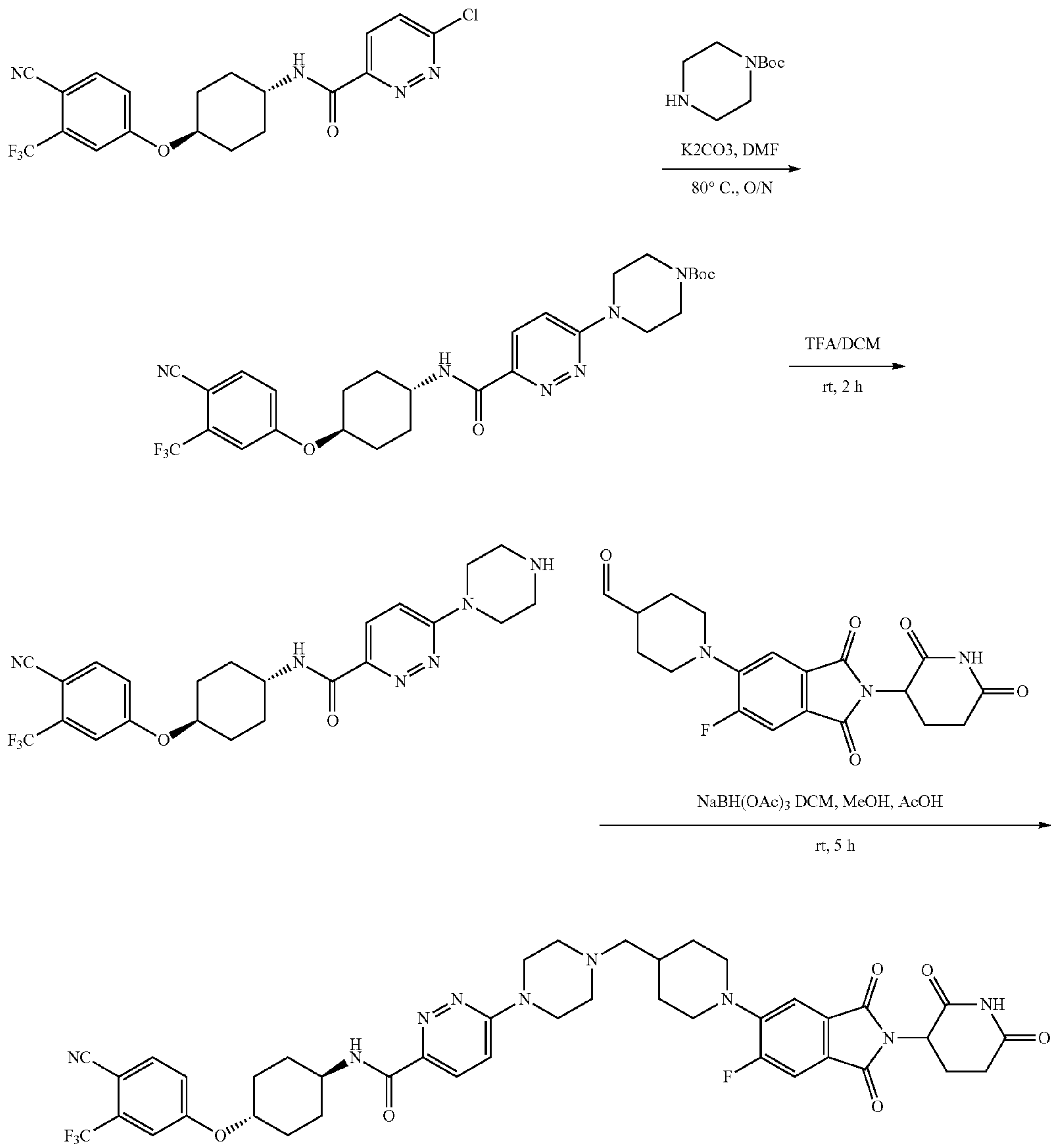

285

LC/MS ($ESI^+$) calcd for $C_{44}H_{49}ClN_9O_6^+$ ($[M+H]^+$) m/z: 886.4; found 886.3.

$^1H$ NMR (400 MHz, $CDCl_3$) (δ 8.39 (s, 1H), 7.99 (d, J=9.5 Hz, 1H), 7.88 (d, J=8.1 Hz, 1H), 7.75 (d, J=8.7 Hz, 1H), 7.46 (d, J=11.0 Hz, 1H), 7.38 (d, J=7.3 Hz, 1H), 7.25 (s, 1H), 7.10 (dd, J=8.7, 2.3 Hz, 1H), 7.00 (d, J=9.6 Hz, 1H), 4.93 (dd, J=12.3, 5.3 Hz, 1H), 4.39 (t, J=10.1 Hz, 1H), 4.07 (d, J=8.2 Hz, 1H), 3.72 (s, 4H), 3.64 (d, J=12.3 Hz, 2H), 3.28 (s, 2H), 2.96-2.72 (m, 5H), 2.58 (s, 2H), 2.27-2.09 (m, 5H), 1.90 (d, J=14.8 Hz, 5H), 1.79-1.59 (m, 8H), 1.46 (s, 2H).

286: N-((1r,4r)-4-(3-chloro-4-cyanophenoxy)cyclohexyl)-5-(4-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl)piperazin-1-yl) pyridineamide

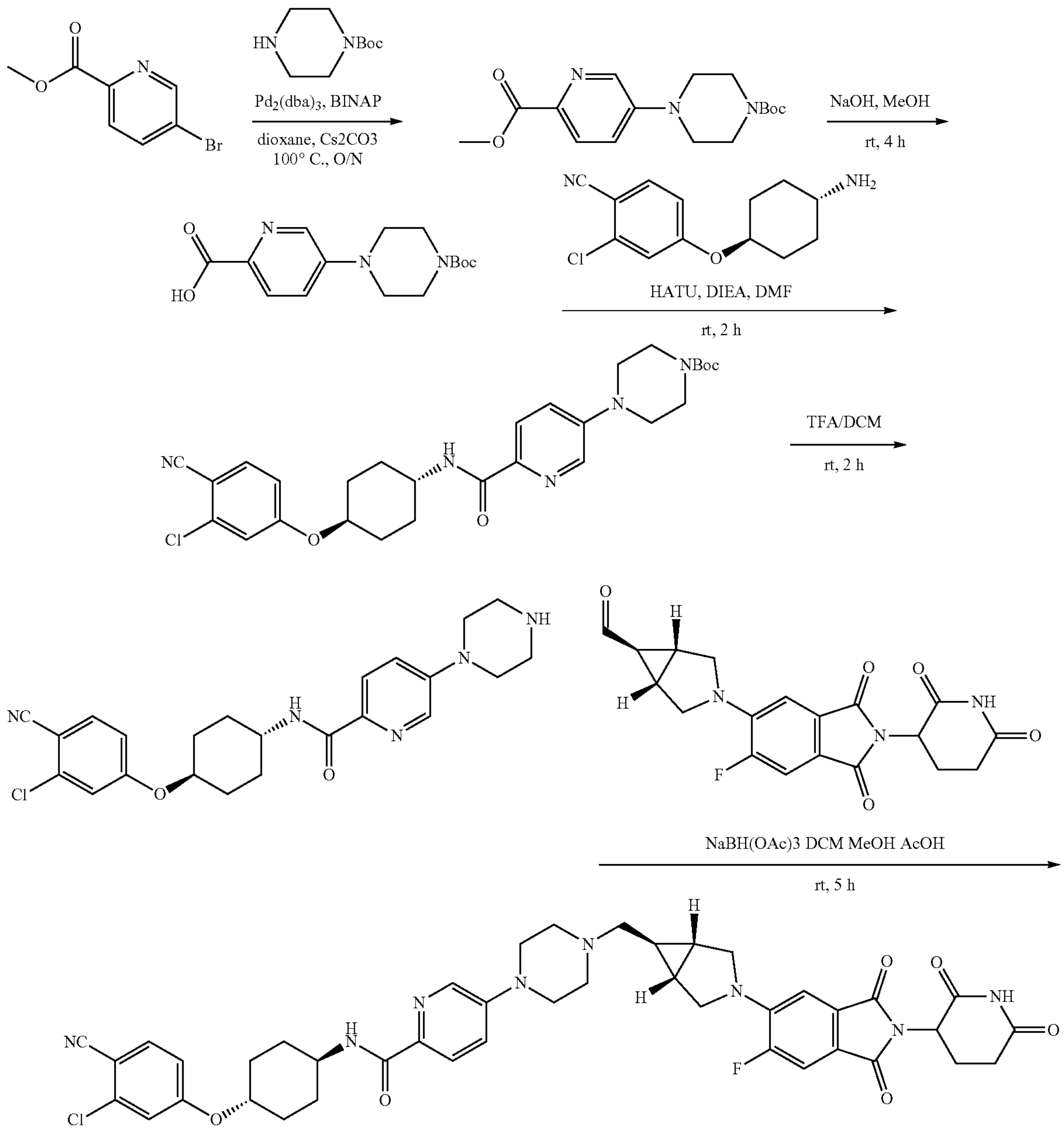

286

1. Synthesis of t-butyl 4-(6-(methoxycarbonyl)pyridin-3-yl)piperazine-1-carboxylate Under the nitrogen protection, methyl 5-bromopimarate (500.0 mg, 2.31 mmol), Boc-piperazine (646.0 mg, 3.47 mmol), $Pd_2(dba)_3$ (100.0 mg, 0.23 mmol), BINAP (100.0 mg, 0.23 mmol), and $Cs_2CO_3$ (1.51 g, 4.62 mmol) were added in 20 mL of toluene. The reaction solution was heated to 100° C. and stirred overnight, and then the solution was cooled to room temperature. The reaction solution was filtered, and the filter cake was washed with ethyl acetate. The filtrate was dried, rotatory evaporated to dry, and purified by silica gel column chromatography, to provide compound t-butyl 4-(6-(methoxycarbonyl)pyridin-3-yl)piperazine-1-carboxylate (450.0 mg, 1.40 mmol), with a yield of 60.5%. LC/MS ($ESI^+$) calcd for $C_{16}H_{24}N_3O_4^+$ ($[M+H]^+$) m/z: 322.2; found 322.0.

2. Synthesis of Compound 5-(4-(t-butoxycarbonyl) piperazin-1-yl)pyridinecarboxylic acid t-Butyl 4-(6-(methoxycarbonyl)pyridin-3-yl)piperazine-1-carboxylate (450.0 mg, 1.40 mmol) was dissolved in 5 mL of methanol, to which was added 5 mL of 2N NaOH. The reaction solution was stirred for 4 h at room temperature, whose pH was then adjusted to 4-5 with 0.5 N HCl. The resultant solution was extracted with ethyl acetate. The organic layer was washed with saturated brine, dried, and rotatory evaporated to dry, to provide compound 5-(4-(t-butoxycarbonyl)piperazin-1-yl)pyridinecarboxylic acid (450.0 mg, 1.40 mmol), with a yield of 100.0%.

3. Synthesis of Compound t-butyl 4-(6-((1r,4r)-4-(3-chloro-4-cyanophenoxy) cyclohexyl)carbamoyl) pyridin-3-yl)piperazine-1-carboxylate 5-(4-(t-Butoxycarbonyl)piperazin-1-yl)pyridinecarboxylic acid (200.0 mg, 0.65 mmol), HATU (260.0 mg, 0.71 mmol), and DIEA (252.0 mg, 1.95 mmol) were dissolved in 5 mL of dichloromethane, to which was added 4-((1r,4r)-4-aminocyclohexyl)oxy)-2-chlorobenzonitrile (163.0 mg, 0.65 mmol). The reaction solution was stirred for 2 h, to which were added water and ethyl acetate for extraction. The organic layer was washed with saturated brine, dried, rotatory evaporated to dry, and purified by silica gel column chromatography, to provide compound t-buty 4-(6-((1r,4r)-4-(3-chloro-4-cyanophenoxy)cyclohexyl)carbamoyl)pyridin-3-yl)piperazine-1-carboxylate (300.0 mg, 0.55 mmol), with a yield of 85.5%.

4. Synthesis of N-((1r,4r)-4-(3-chloro-4-cyanophenoxy)cyclohexyl)-5-(piperazin-1-yl)pyridineamide t-Butyl 4-(6-((1r,4r)-4-(3-chloro-4-cyanophenoxy)cyclohexyl)carbamoyl)pyridin-3-yl)piperazine-1-carboxylate (300 mg, 0.55 mmol) was dissolved in 5 mL of dichloromethane and 5 mL of trifluoroacetic acid. The reaction solution was stirred for 2 h at room temperature, concentrated, and rotatory evaporated to dry, to provide compound N-((1r,4r)-4-(3-chloro-4-cyanophenoxy)cyclohexyl)-5-(piperazin-1-yl)pyridineamide (250 mg, 0.55 mmol), with a yield of 100.0%.

5. Synthesis of compound N-((1r,4r)-4-(3-chloro-4-cyanophenoxy)cyclohexyl)-5-(4-((1r,5S,6s)-3-(2-(2,6-dioxopiperidin-3-yl)-6-fluoro-1,3-dioxoisoindolin-5-yl)-3-azabicyclo[3.1.0]n-hexane-6-yl)methyl) piperazin-1-yl)pyridineamide N-((1r,4r)-4-(3-chloro-4-cyanophenoxy)cyclohexyl)-5-(piperazin-1-yl)pyridineamide (50.0 mg, 0.11 mmol) and (1R,5S)-3-(2-(2,6-dioxopiperidin-3-yl)-6-fluoro-1,3-dioxoisoindolin-5-yl)-3-azabicyclo[3.1.0]n-hexane-6-formaldehyde (43.8 mg, 0.11 mmol) were dissolved in 2 mL of dichloromethane, and then one drop of acetic acid was added, followed by addition of sodium triethoxyborohydride (72.0 mg, 0.33 mmol). The solution was stirred overnight at room temperature. Then, the reaction solution was added with dichloromethane and water for extraction, and the organic layer was washed with saturated brine, dried, rotatory evaporated to dry, and purified by prep.-TLC, to provide the target compound (50 mg, 0.06 mmol), with a yield of 54.3%. LC/MS (ESI$^+$) calcd for $C_{42}H_{43}ClFN_8O_6^+$ ([M+H]+) m/z: 809.3; found 809.2.

$^1$H NMR (400 MHz, $CDCl_3$) δ 8.51 (s, 1H), 8.18 (d, J=2.7 Hz, 1H), 8.06 (d, J=8.7 Hz, 1H), 7.74 (d, J=8.3 Hz, 1H), 7.56 (d, J=8.7 Hz, 1H), 7.39 (d, J=12.5 Hz, 1H), 7.25-7.19 (m, 1H), 7.05 (d, J=7.4 Hz, 1H), 7.00 (d, J=2.3 Hz, 1H), 6.85 (dd, J=8.7, 2.4 Hz, 1H), 4.92 (dd, J=12.2, 5.3 Hz, 1H), 4.31 (dd, J=12.0, 8.3 Hz, 1H), 4.02 (dd, J=11.3, 7.3 Hz, 1H), 3.90 (d, J=10.1 Hz, 2H), 3.60 (d, J=9.3 Hz, 2H), 3.43 (s, 4H), 2.96-2.68 (m, 6H), 2.52 (s, 2H), 2.15 (dd, J=18.8, 7.6 Hz, 5H), 1.69 (d, J=12.0 Hz, 8H), 1.53-1.41 (m, 2H).

287: N-((1r,4r)-4-(3-chloro-4-cyanophenoxy)cyclohexyl)-5-(4-(2-(2-(2,6-dioxopiperidin-3-yl)-6-fluoro-1,3-dioxoisoindolin-5-yl)-2,7-diazaspiro[3.5]nonan-7-yl)piperidin-1-yl)pyrazine-2-carboxamide

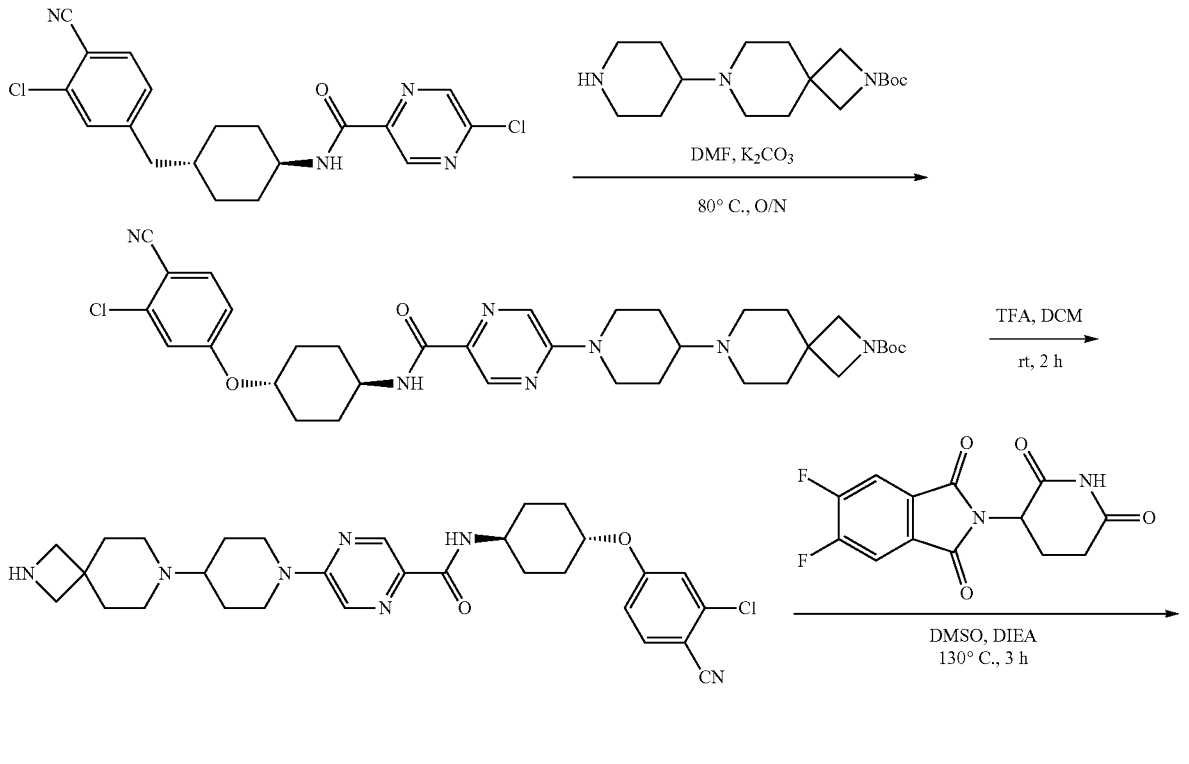

-continued

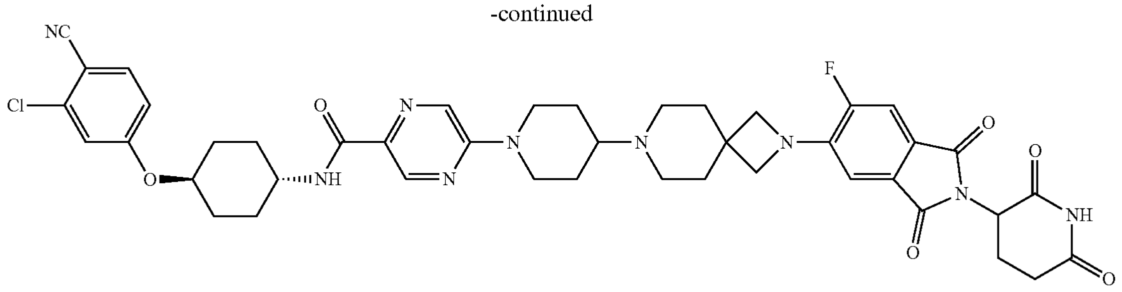

287

LC/MS (ESI+) calcd for $C_{43}H_{46}ClFN_9O_6^+$ ([M+H]+) m/z: 838.3; found 838.3.

$^1$H NMR (400 MHz, $CDCl_3$) δ 8.83 (s, 1H), 8.22 (s, 1H), 7.97 (s, 1H), 7.56 (d, J=8.7 Hz, 1H), 7.48 (d, J=10.8 Hz, 1H), 7.43-7.35 (m, 2H), 7.01 (t, J=6.6 Hz, 1H), 6.85 (dd, J=8.7, 2.3 Hz, 1H), 4.93 (dd, J=12.3, 5.2 Hz, 1H), 4.43 (s, 2H), 4.31 (t, J=10.1 Hz, 1H), 4.03 (d, J=8.1 Hz, 1H), 3.50 (s, 2H), 3.14 (d, J=31.2 Hz, 6H), 2.94-2.71 (m, 4H), 2.17 (d, J=8.4 Hz, 5H), 1.95 (s, 4H), 1.66 (d, J=9.9 Hz, 8H), 1.47 (d, J=11.8 Hz, 2H).

288: N-((1r,4r)-4-(3-chloro-4-cyanophenoxy)cyclohexyl)-5-(2-(2,6-dioxopiperidin-3-yl)-1,3-dioxoisoindolin-5-yl)piperidine-4-yl)-2,7-diazaspiro[3.5]nonan-7-yl)pyrazine-2-carboxamide

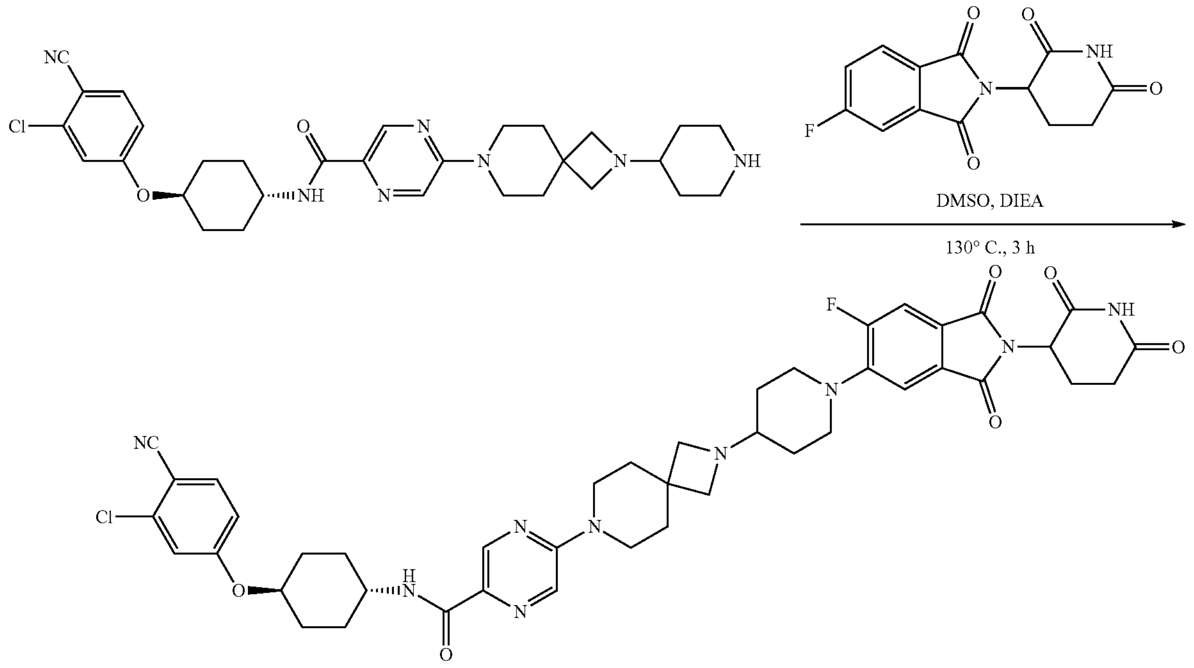

288

LC/MS (ESI+) calcd for $C_{43}H_{74}ClN_9O_6^+$ ([M+H]+) m/z: 820.3; found 820.3.

$^1$H NMR (400 MHz, CDCl3) δ 8.83 (d, J=1.2 Hz, 1H), 8.17 (s, 1H), 7.97 (d, J=1.2 Hz, 1H), 7.67 (d, J=8.5 Hz, 1H), 7.56 (d, J=8.7 Hz, 1H), 7.39 (d, J=8.2 Hz, 1H), 7.28 (s, 1H), 7.05 (dd, J=8.6, 2.3 Hz, 1H), 6.99 (d, J=2.4 Hz, 1H), 6.85 (dd, J=8.8, 2.4 Hz, 1H), 4.94 (dd, J=12.3, 5.3 Hz, 1H), 4.30 (d, J=3.7 Hz, 1H), 4.03 (d, J=8.1 Hz, 1H), 3.87 (d, J=13.1 Hz, 2H), 3.76-3.53 (m, 4H), 3.22 (s, 4H), 3.08 (t, J=10.5 Hz, 2H), 2.94-2.70 (m, 3H), 2.54-2.42 (m, 1H), 2.22-2.13 (m, 5H), 1.89 (s, 6H), 1.69 (dd, J=22.2, 9.7 Hz, 8H), 1.49-1.41 (m, 2H).

289: N-((1r,4r)-4-(3-chloro-4-cyanophenoxy)cyclohexyl)-5-(2-(2,6-dioxopiperidin-3-yl)-6-fluoro-1,3-dioxoisoindolin-5-yl)piperidine-4-yl)-2,7-diazaspiro[3.5]nonan-7-yl)pyrazine-2-carboxamide

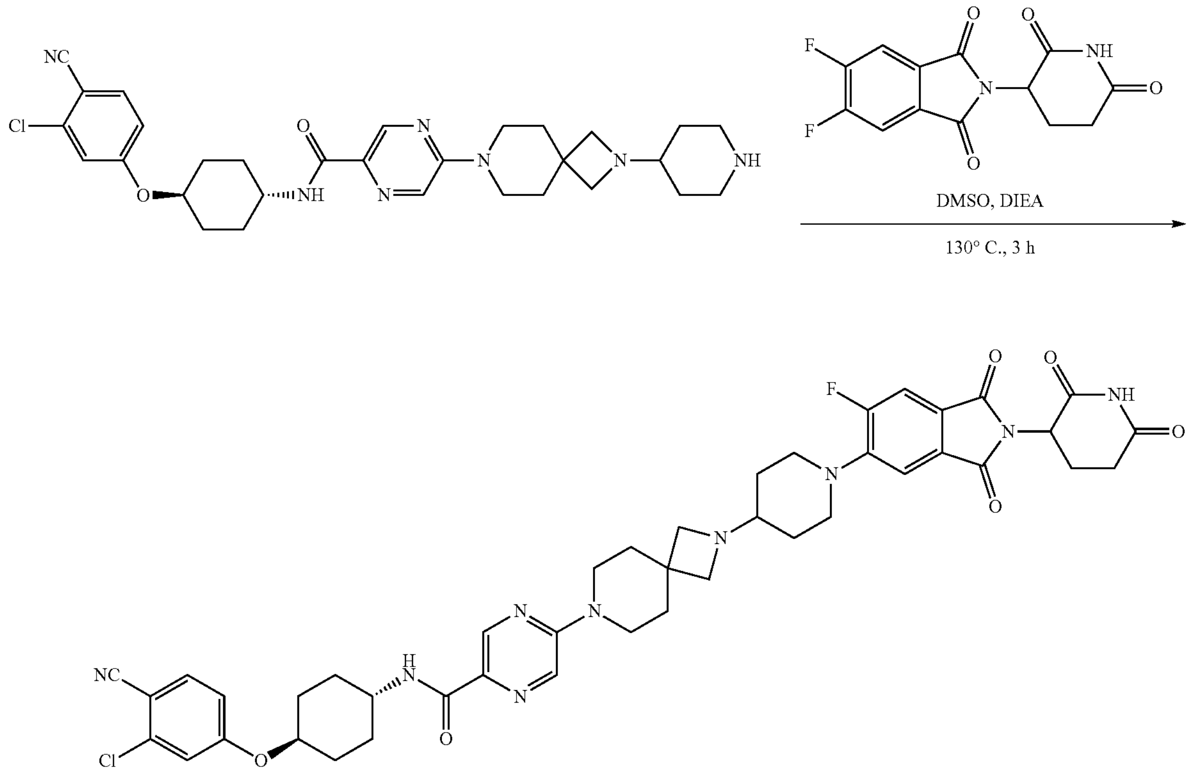

289

LC/MS ($ESI^+$) calcd for $C_{43}H_{46}ClFN_9O_6^+$ ($[M+H]^+$) m/z: 838.3; found 838.3.

$^1H$ NMR (400 MHz, $CDCl_3$) δ 8.83 (d, J=1.2 Hz, 1H), 8.33 (s, 1H), 7.98 (d, J=1.1 Hz, 1H), 7.56 (d, J=8.7 Hz, 1H), 7.46 (d, J=11.0 Hz, 1H), 7.39 (dd, J=7.7, 4.1 Hz, 2H), 6.99 (d, J=2.4 Hz, 1H), 6.85 (dd, J=8.8, 2.4 Hz, 1H), 4.93 (dd, J=12.3, 5.3 Hz, 1H), 4.30 (dd, J=11.9, 8.2 Hz, 1H), 4.02 (dd, J=11.6, 7.4 Hz, 1H), 3.73-3.57 (m, 6H), 3.24 (s, 4H), 2.93 (t, J=10.5 Hz, 2H), 2.84-2.72 (m, 2H), 2.44 (s, 1H), 2.20-2.13 (m, 4H), 1.88 (d, J=12.6 Hz, 10H), 1.74-1.55 (m, 6H), 1.47 (dd, J=22.6, 10.3 Hz, 2H).

290: (3aR,5s,6aS)-2-(2,6-dioxopiperidin-3-yl)-6-fluoro-1,3-dioxoisoindolin-5-yl)octahydrocyclopenta[c]pyrrol-5-yl 4-(6-((1r,4r)-4-(3-chloro-4-cyanophenoxy)cyclohexyl)carbamoyl)pyridazine-3-yl)piperazine-1-carboxylate

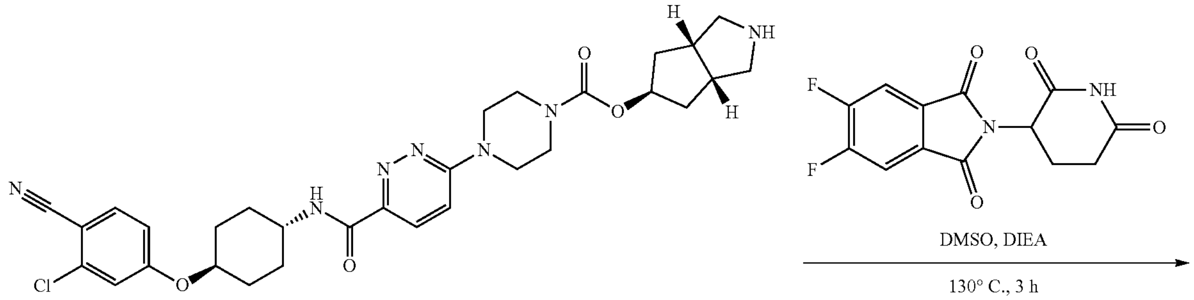

-continued

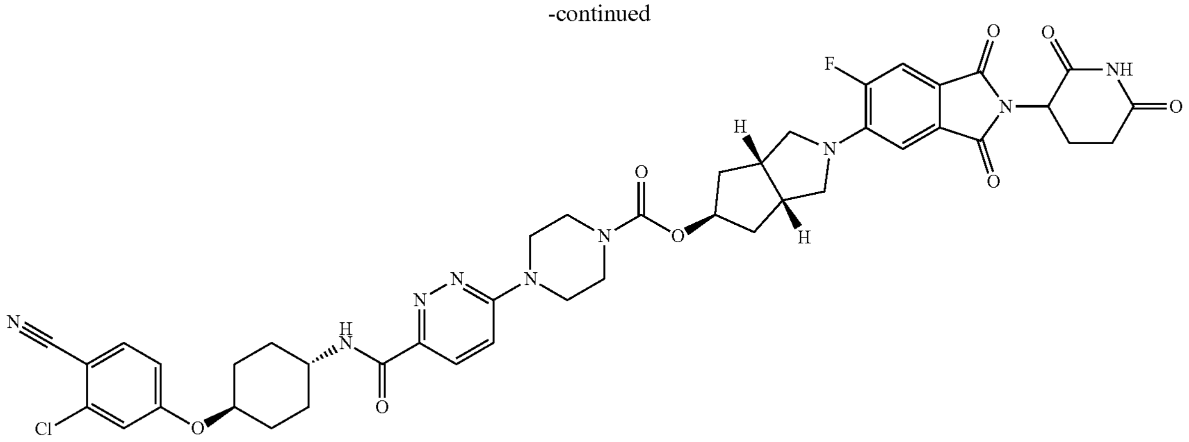

290

LC/MS ($ESI^+$) calcd for $C_{43}H_{46}ClFN_9O_6^+$ ($[M+H]^+$) m/z: 868.3; found 867.7.

$^1H$ NMR (400 MHz, $CDCl_3$) δ 8.24 (s, 1H), 8.07 (d, J=9.4 Hz, 1H), 7.91 (d, J=8.2 Hz, 1H), 7.56 (d, J=8.7 Hz, 1H), 7.41 (d, J=12.1 Hz, 1H), 7.09 (d, J=7.4 Hz, 1H), 7.04 (d, J=9.5 Hz, 1H), 7.00 (d, J=2.3 Hz, 1H), 6.86 (dd, J=8.7, 2.4 Hz, 1H), 5.33 (d, J=2.6 Hz, 1H), 4.93 (dd, J=12.2, 5.3 Hz, 1H), 4.31 (dd, J=11.8, 8.2 Hz, 1H), 4.06 (d, J=8.0 Hz, 1H), 3.81 (s, 4H), 3.60 (d, J=7.5 Hz, 2H), 3.45 (d, J=10.5 Hz, 2H), 2.98 (s, 2H), 2.93-2.72 (m, 3H), 2.39-2.02 (m, 8H), 1.99-1.81 (m, 5H), 1.69 (dd, J=22.2, 9.9 Hz, 2H), 1.55-1.43 (m, 2H).

291: N-((1r,3r)-3-(3-chloro-4-cyanophenoxy)-2,2,4,4-tetramethylcyclobutyl)-6-(4-((1-(2-(2,6-dioxopiperidin-3-yl)-6-fluoro-1,3-dioxoisoindoline)piperidine-4-yl)amino)piperidin-1-yl)pyridazine-3-formamide

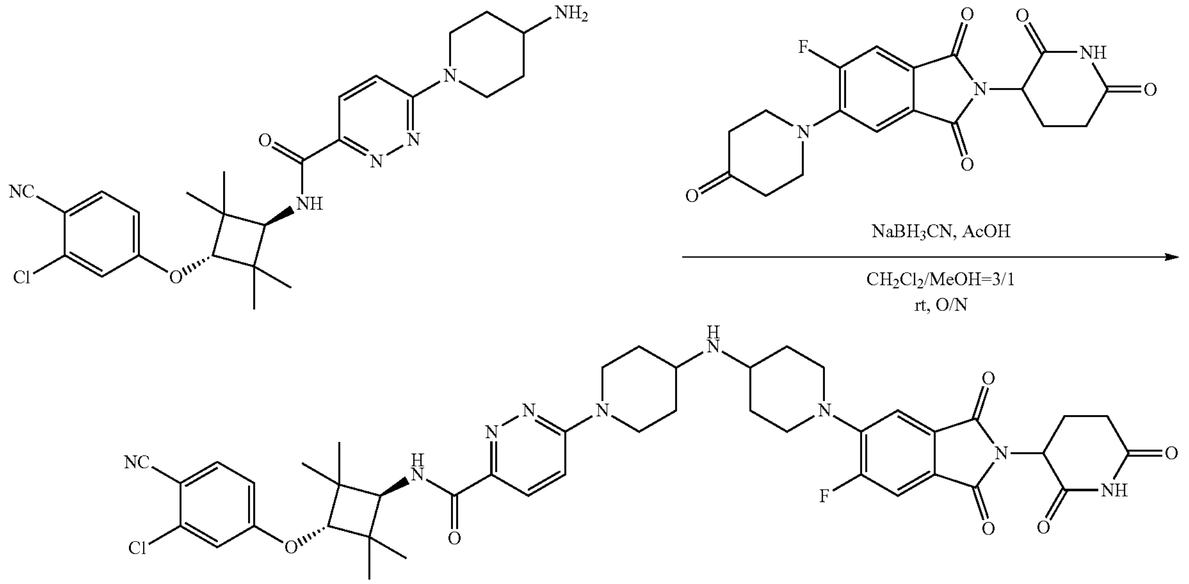

291

LC/MS ($ESI^+$) calcd for $C_{43}H_{48}ClFN_9O_6^+$ ($[M+H]^+$) m/z: 840.3; found 840.3.

$^1H$ NMR (400 MHz, CDCl3) δ 8.15 (d, J=9.2 Hz, 1H), 8.00 (d, J=9.5 Hz, 1H), 7.57 (d, J=8.7 Hz, 1H), 7.47 (d, J=10.9 Hz, 1H), 7.39 (d, J=7.2 Hz, 1H), 7.03 (d, J=9.6 Hz, 1H), 6.97 (d, J=2.3 Hz, 1H), 6.81 (dd, J=8.7, 2.3 Hz, 1H), 4.94 (dd, J=12.3, 5.3 Hz, 1H), 4.51 (d, J=12.2 Hz, 2H), 4.19 (d, J=9.1 Hz, 1H), 4.07 (s, 1H), 3.79-3.62 (m, 2H), 3.17 (t, J=11.7 Hz, 3H), 3.00-2.88 (m, 3H), 2.85-2.62 (m, 3H), 2.12 (s, 5H), 1.74 (d, J=21.4 Hz, 5H), 1.28 (s, 6H), 1.21 (s, 6H).

292: N-((1s,4S)-4-(3-chloro-4-cyanophenoxy)cyclohexyl)-6-((3aR,5R,6aS)-5-(4-(2-(2,6-dioxopiperidin-3-yl)-6-fluoro-1,3-dioxoisoindolin-5-yl)piperazin-1-yl) hexahydrocyclopenta[c]pyrrole-2(1H)-yl) pyridazine-3-formamide

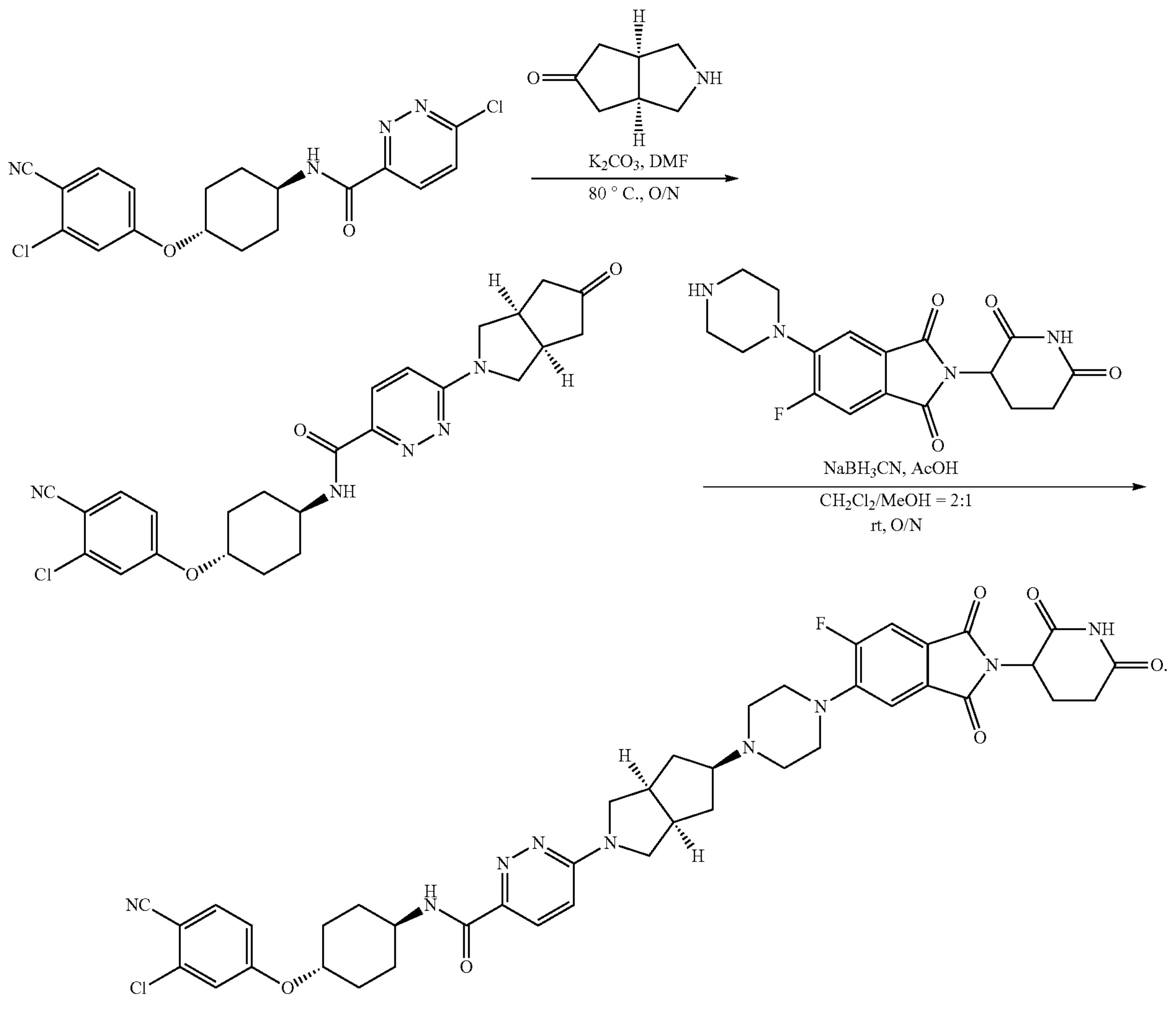

292

1. Synthesis of Compound N-((1s,4s)-4-(3-chloro-4-cyanophenoxy)cyclohexyl)-6-((3aR,6aS)-5-oxohexahydrocyclopenta[c]pyrrole-2(1H)-yl)pyridazine-3-formamide Compounds 6-chloro-N-((1s,4s)-4-(3-chloro-4-cyanophenoxy)cyclohexyl)pyridazine-3-formamide (200.0 mg, 0.5 mmol) and (3aR,6aS)-hexahydrocyclopenta[c]pyrrole-5(1H)-one (128.0 mg, 1.0 mmol) were dissolved in 5 mL of DMF, to which was added potassium carbonate (141.0 mg, 1.0 mmol). The reaction solution was heated to 80° C. and stirred overnight. Then, the reaction solution was added with dichloromethane and water for extraction, and the organic layer was washed with saturated brine, dried, rotatory evaporated to dry, and purified by silica gel column chromatography, to provide compound N-((1s,4s)-4-(3-chloro-4-cyanophenoxy)cyclohexyl)-6-((3aR,6aS)-5-oxohexahydrocyclopenta[c]pyrrole-2(1H)-yl)pyridazine-3-formamide (70.0 mg, 0.14 mmol), with a yield of 28.5%.

2. Synthesis of N-((1s,4s)-4-(3-chloro-4-cyanophenoxy)cyclohexyl)-6-((3aR,5R6aS)-5-(4-(2-(2,6-dioxopiperidin-3-yl)-6-fluoro-1,3-dioxoisoindolin-5-yl)piperazin-1-yl)hexahydrocyclopenta[c]pyrrole-2(1H)-yl)pyridazine-3-formamide Compounds N-((1s,4s)-4-(3-chloro-4-cyanophenoxy)cyclohexyl)-6-((3aR,6aS)-5-oxohexahydrocyclopenta[c]pyrrole-2(1H)-yl)pyridazine-3-formamide (60.0 mg, 0.12 mmol) and 2-(2,6-dioxopiperidin-3-yl)-5-fluoro-6-(piperazin-1-yl)isobenzyl-1,3-dione (45.0 mg, 0.12 mmol) were dissolved in 2 mL of dichloromethane and 5 mL of methanol, and then one drop of acetic acid was added, followed by addition of sodium cyanoborohydride (31.0 mg, 0.50 mmol). The solution was stirred overnight at room temperature. Then, the reaction solution was added with dichloromethane and water for extraction, and the organic layer was washed with saturated brine, dried, rotatory evaporated to dry, and purified by prep.-TLC, to provide compound N-((1s,4s)-4-(3-chloro-4-cyanophenoxy)cyclohexyl)-6-((3aR,5R,6aS)-5-(4-(2-(2,6-dioxopiperidin-3-yl)-6-fluoro-1,3-dioxoisoindolin-5-yl)piperazin-1-yl)hexahydrocyclopenta[c]pyrrole-2(1H)-yl)pyridazine-3-formamide (30.0 mg, 0.04 mmol), with a yield of 29.1%.

LC/MS (ESI+) calcd for $C_{42}H_{46}ClFN_9O_6^+$ ([M+H]+) m/z: 824.3; found 824.2.

$^1$H NMR (400 MHz, CDCl3) δ 8.41 (s, 1H), 7.98 (d, J=9.4 Hz, 1H), 7.90 (d, J=8.2 Hz, 1H), 7.56 (d, J=8.7 Hz, 1H), 7.48 (d, J=10.9 Hz, 1H), 7.41 (d, J=7.2 Hz, 1H), 7.01 (d, J=2.4 Hz, 1H), 6.86 (dd, J=8.8, 2.4 Hz, 1H), 6.72 (d, J=9.4 Hz, 1H), 4.93 (dd, J=12.2, 5.3 Hz, 1H), 4.38-4.28 (m, 1H), 4.05 (dd, J=11.4, 7.3 Hz, 1H), 3.76 (d, J=6.5 Hz, 2H), 3.66 (s, 2H), 3.49-3.18 (m, 4H), 2.90 (d, J=10.2 Hz, 2H), 2.76 (dq, J=13.4, 8.9 Hz, 4H), 2.42-2.26 (m, 2H), 2.16 (ddd, J=12.0, 10.1, 3.1 Hz, 5H), 1.85-1.61 (m, 8H), 1.46 (dd, J=12.4, 9.8 Hz, 2H).

293: N-((1r,4r)-4-(3-chloro-4-cyanophenoxy)cyclohexyl)-5-((3aR,5R,6aS)-5-(4-(2-(2,6-dioxopiperidin-3-yl)-6-fluoro-1,3-dioxoisoindolin-5-yl)piperazin-1-yl) hexahydrocyclopenta[c]pyrrole-2(1H)-yl) pyrazine-2-carboxamide

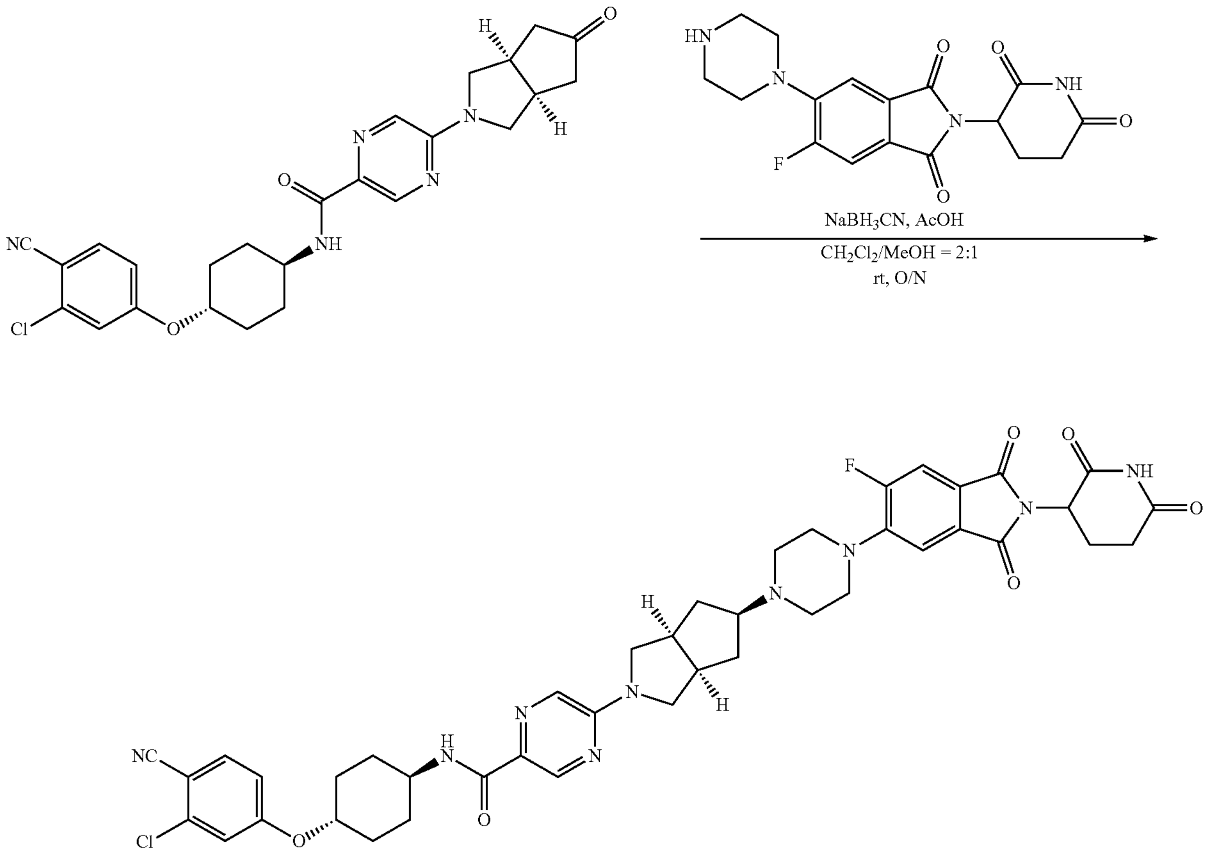

293

LC/MS (ESI+) calcd for $C_{42}H_{44}ClFN_9O_6^+$ ([M+H]+) m/z: 824.3; found 824.3.

$^1$H NMR (400 MHz, $CDCl_3$) δ 8.84 (d, J=1.3 Hz, 1H), 8.38 (s, 1H), 7.72 (d, J=1.2 Hz, 1H), 7.56 (d, J=8.7 Hz, 1H), 7.48 (d, J=10.9 Hz, 1H), 7.40 (d, J=7.5 Hz, 2H), 7.00 (d, J=2.4 Hz, 1H), 6.85 (dd, J=8.8, 2.4 Hz, 1H), 4.93 (dd, J=12.3, 5.3 Hz, 1H), 4.38-4.24 (m, 1H), 4.03 (dd, J=7.4, 3.4 Hz, 1H), 3.74 (dd, J=11.0, 7.5 Hz, 2H), 3.61 (d, J=10.3 Hz, 2H), 3.33 (s, 4H), 2.88-2.73 (m, 6H), 2.43-2.25 (m, 2H), 2.15 (dt, J=7.5, 6.4 Hz, 5H), 1.81-1.58 (m, 8H), 1.48 (dd, J=16.8, 6.3 Hz, 2H).

294: N-((1r,4r)-4-(3-chloro-4-cyanophenoxy)cyclohexyl)-5-((3aR,5R,6aS)-5-(4-(2-(2,6-dioxopiperidin-3-yl)-6-fluoro-1,3-dioxoisoindolin-5-yl)piperazin-1-yl) hexahydrocyclopenta[c]pyrrole-2(1H)-yl) pyrimidine-2-carboxamide

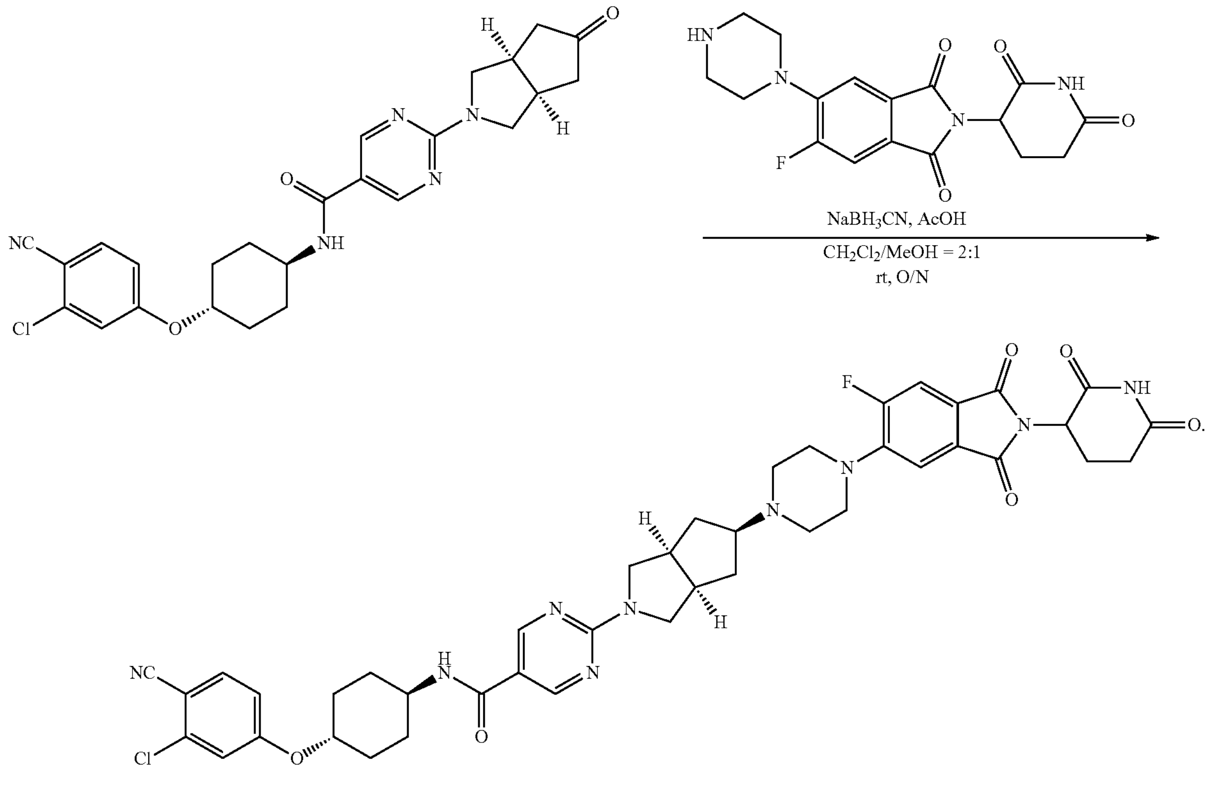

294

LC/MS (ESI$^+$) calcd for $C_{42}H_{44}ClFN_9O_6^+$ ([M+H]$^+$) m/z 824.3; found 824.2.

295: N-((1s,4s)-4-(3-chloro-4-cyanophenoxy)cyclohexyl)-5-(4-((3aR,5R,6aS)-2-(2-(2,6-dioxopiperidin-3-yl)-6-fluoro-1,3-dioxoisoindolin-5-yl)octahydrocyclopenta[c] pyrrol-5-yl)piperazin-1-yl)pyrazine-2-carboxamide

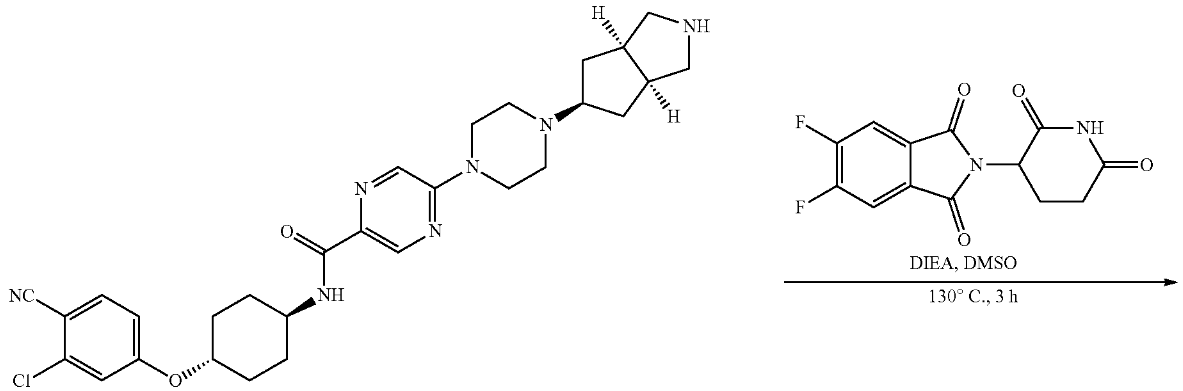

-continued

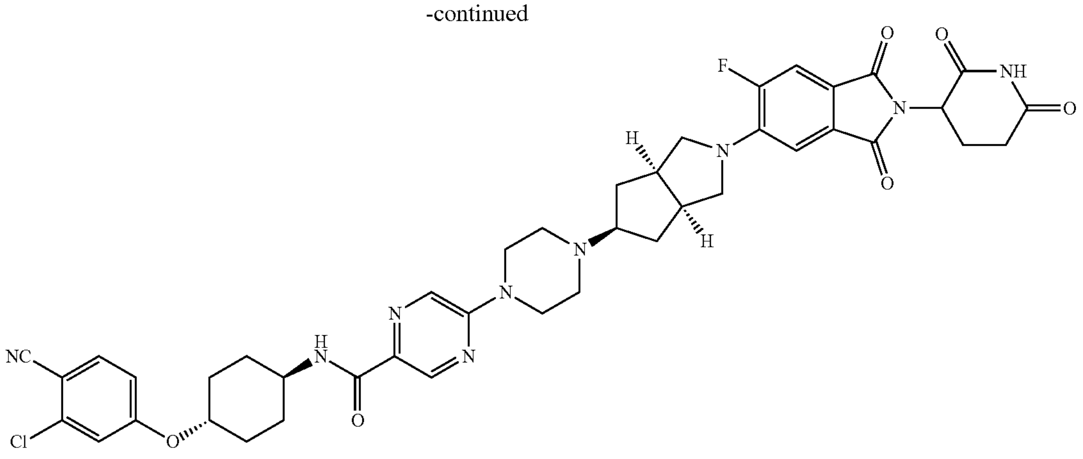

295

LC/MS ($ESI^+$) calcd for $C_{42}H_{44}ClFN_9O_6^+$ ($[M+H]^+$) m/z: 824.3; found 824.2.

295 Synthesis of the Intermediate

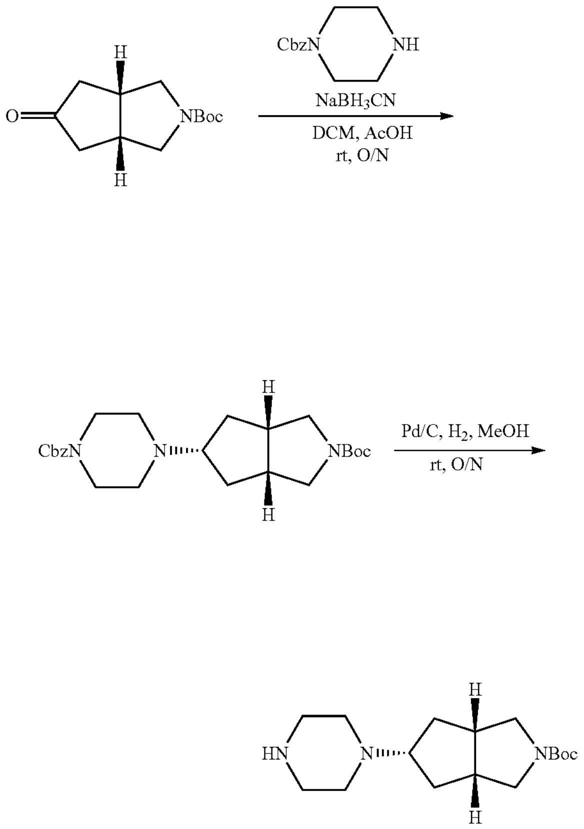

1. Synthesis of Compound (3aR,5R,6aS)-t-butyl5-(4-((benzoxy)carbonyl)piperazin-1-yl)hexahydrocyclopenta[c]pyrrole-2(1H)-carboxylate Compounds (3aR,6aS)-t-butyl5-oxohydrocyclopenta[c]pyrrole-2(1H)-carboxylate (1.0 g, 4.4 mmol) and benzyl piperazine-1-carboxylate (1.0 g, 4.4 mmol) were dissolved in 20 mL of dichloromethane, to which was added 0.2 mL of acetic acid, followed by addition of sodium cyanoborohydride (836.0 mg, 13.2 mmol). The solution was stirred overnight at room temperature. Then, the reaction solution was added with water and dichloromethane for extraction, and the organic layer was washed with saturated brine, dried, rotatory evaporated to dry, and purified by silica gel column chromatography, to provide compound (3aR,5R,6aS)-t-butyl 5-(4-((benzoxy)carbonyl)piperazin-1-yl) hexahydrocyclopenta[c]pyrrole-2(1H)-carboxylic acid (780.0 mg, 1.8 mmol), with a yield of 40.9%.

2. Compound (3aR,5R,6aS)-t-butyl 5-(piperazin-1-yl)hexahydrocyclopenta[c]pyrrole-2(1H)-carboxylate Compound (3aR,5R,6aS)-t-butyl5-(4-((benzoxy)carbonyl)piperazin-1-yl) hexahydrocyclopenta[c]pyrrole-2(1H)-carboxylic acid (780.0 mg, 1.8 mmol) was dissolved in 20 mL of methanol, to which was added wet Pd/C (300.0 mg). The system was purged with hydrogen three times using a hydrogen balloon. The reaction solution was stirred overnight at room temperature, and then subjected to suction filter through a pad of celite. The filter cake was washed twice with methanol. The filtrate was rotatory evaporated to dry, to obtain the crude compound (3aR,5R,6aS)-t-butyl 5-(piperazin-1-yl)hexahydrocyclopenta[c]pyrrole-2(1H)-carboxylate (530.0 mg, 1.8 mmol), with a yield of 98.8%.

296: N-((1r,4r)-4-(3-chloro-4-cyanophenoxy)cyclohexyl)-5-(4-((3aR,5R,6aS)-2-(2-(2,6-dioxopiperidin-3-yl)-1,3-dioxoisoindol-5-yl)octahydrocyclopenta[c]pyrrol-5-yl)piperazin-1-yl)pyrazine-2-carboxamide

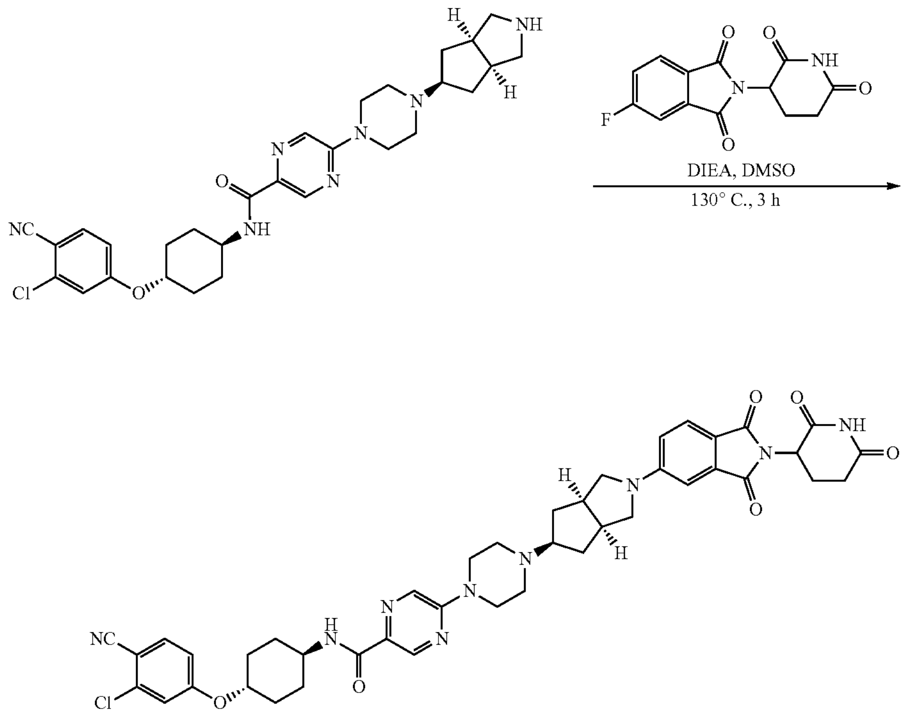

296

LC/MS (ESI+) calcd for $C_{42}H_{45}ClN_9O_6^+$ ([M+H]+) m/z: 806.3; found 806.2.

$^1$H NMR (400 MHz, $CDCl_3$) δ 8.86 (d, J=1.1 Hz, 1H), 8.23 (s, 1H), 7.97 (s, 1H), 7.66 (d, J=8.4 Hz, 1H), 7.56 (d, J=8.7 Hz, 1H), 7.41 (d, J=8.3 Hz, 1H), 6.98 (dd, J=10.2, 2.2 Hz, 2H), 6.84 (dd, J=8.8, 2.4 Hz, 1H), 6.71 (dd, J=8.5, 2.1 Hz, 1H), 4.94 (dd, J=12.3, 5.3 Hz, 1H), 4.30 (t, J=10.2 Hz, 1H), 4.04 (d, J=4.0 Hz, 1H), 3.93 (d, J=51.6 Hz, 4H), 3.68-3.58 (m, 2H), 3.48 (s, 2H), 2.91-2.72 (m, 7H), 2.33 (d, J=5.9 Hz, 2H), 2.23-2.06 (m, 5H), 1.69 (d, J=12.1 Hz, 8H), 1.52-1.43 (m, 2H).

297: N-((1r,4r)-4-(3-chloro-4-cyanophenoxy)cyclohexyl)-6-(4-((3aR,5R,6aS)-2-(2-(2,6-dioxopiperidin-3-yl)-6-fluoro-1,3-dioxoisoindolin-5-yl) octahydrocyclopenta[c]pyrrol-5-yl)piperazin-1-yl)pyridazine-3-formamide

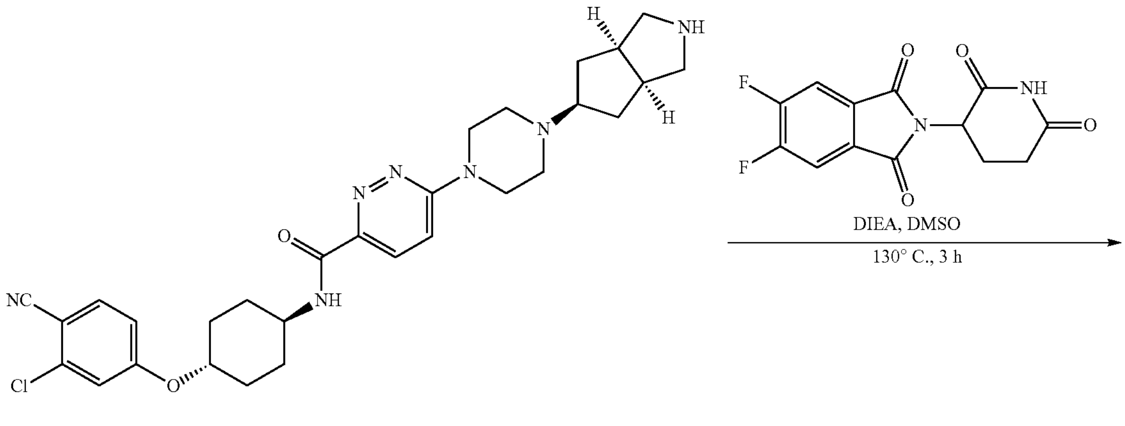

-continued
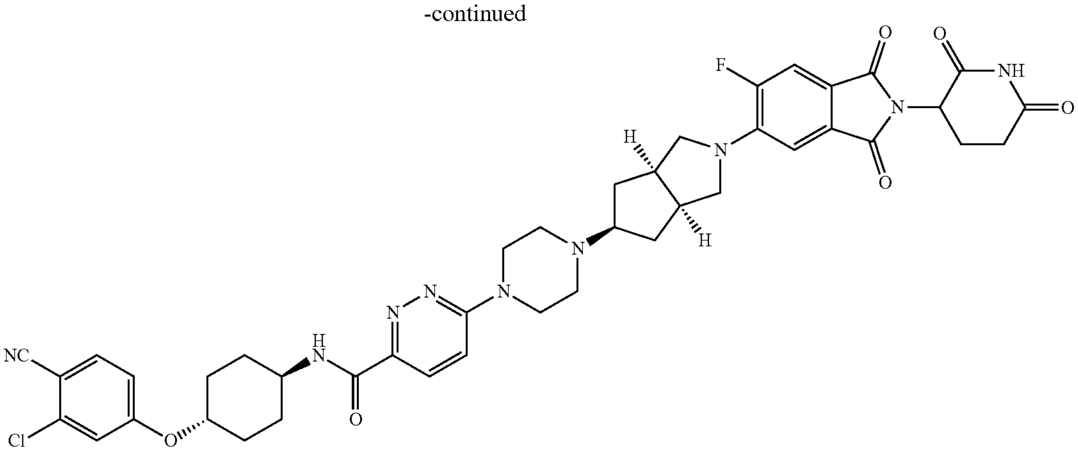
297
LC/MS (ESI+) calcd for $C_{42}H_{44}ClFN_9O_6^+$ ([M+H]+) m/z: 824.3; found 824.2.
$^1$H NMR (400 MHz, $CDCl_3$) δ 8.28 (s, 1H), 8.02 (d, J=9.5 Hz, 1H), 7.89 (d, J=8.3 Hz, 1H), 7.56 (d, J=8.7 Hz, 1H), 7.41 (d, J=12.2 Hz, 1H), 7.10 (d, J=7.4 Hz, 1H), 6.99 (t, J=6.3 Hz, 2H), 6.85 (dd, J=8.8, 2.4 Hz, 1H), 4.92 (dd, J=12.2, 5.3 Hz, 1H), 4.36-4.25 (m, 1H), 4.05 (dd, J=11.5, 7.3 Hz, 1H), 3.84 (s, 4H), 3.59 (s, 4H), 2.95-2.75 (m, 6H), 2.39-2.26 (m, 2H), 2.25-2.09 (m, 5H), 1.68 (dd, J=22.1, 9.7 Hz, 8H), 1.50-1.42 (m, 2H).
298: N-((1r,4r)-4-(3-chloro-4-cyanophenoxy)cyclohexyl)-6-(4-((3aR,5R,6aS)-2-(2-(2,6-dioxopiperidin-3-yl)-1,3-dioxoisoindolin-5-yl)octahydrocyclopenta[c]pyrrol-5-yl)piperazin-1-yl)pyridazine-3-formamide
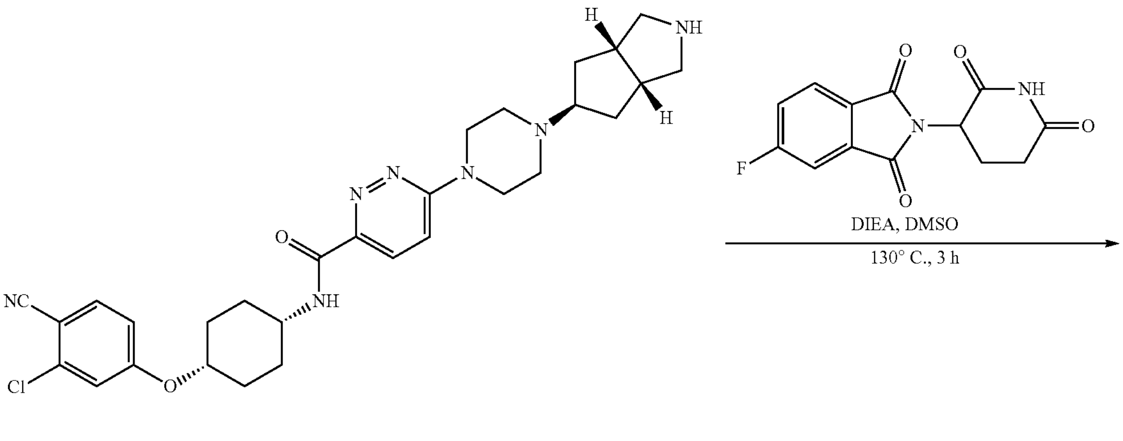

-continued
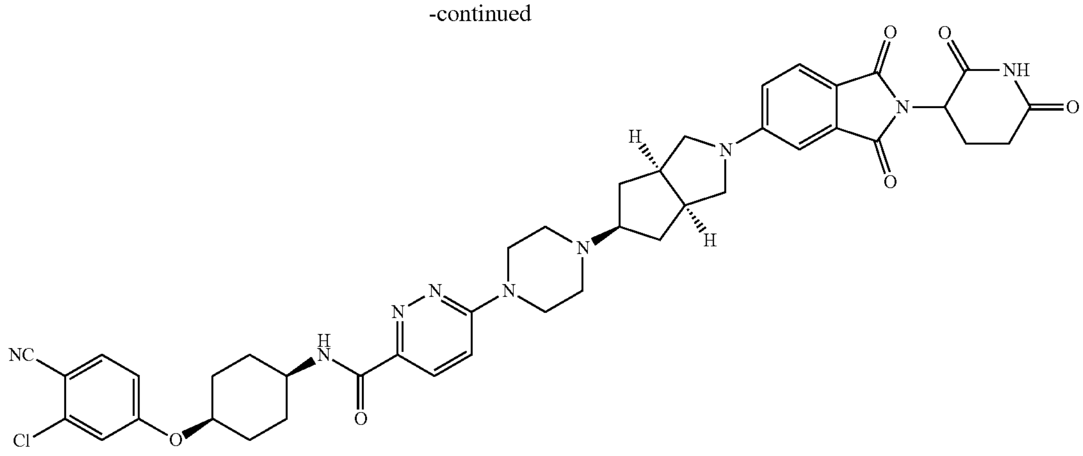
298
LC/MS ($ESI^+$) calcd for $C_{42}H_{45}ClN_9O_6^+$ ($[M+H]^+$) m/z: 806.3; found 806.2.
$^1H$ NMR (400 MHz, $CDCl_3$) δ 8.30 (s, 1H), 8.02 (d, J=9.5 Hz, 1H), 7.89 (d, J=8.2 Hz, 1H), 7.66 (d, J=8.4 Hz, 1H), 7.56 (d, J=8.7 Hz, 1H), 6.99 (dd, J=10.2, 2.2 Hz, 3H), 6.85 (dd, J=8.7, 2.4 Hz, 1H), 6.70 (dd, J=8.5, 2.1 Hz, 1H), 4.94 (dd, J=12.3, 5.3 Hz, 1H), 4.31 (t, J=3.7 Hz, 1H), 4.13-4.00 (m, 1H), 3.83 (s, 4H), 3.65-3.55 (m, 2H), 3.43 (d, J=9.1 Hz, 2H), 2.89-2.73 (m, 6H), 2.38-2.26 (m, 2H), 2.15 (dt, J=12.7, 7.3 Hz, 5H), 1.68 (dd, J=22.2, 9.8 Hz, 8H), 1.50-1.42 (m, 2H).
299: N-((1r,4r)-4-(3-chloro-4-cyanophenoxy)cyclohexyl)-2-(4-((3aR,5R,6aS)-2-(2-(2,6-dioxopiperidin-3-yl)-6-fluoro-1,3-dioxoisoindolin-5-yl) octahydrocyclopenta[c]pyrrol-5-yl)piperazin-1-yl)pyrimidine-5-formamide
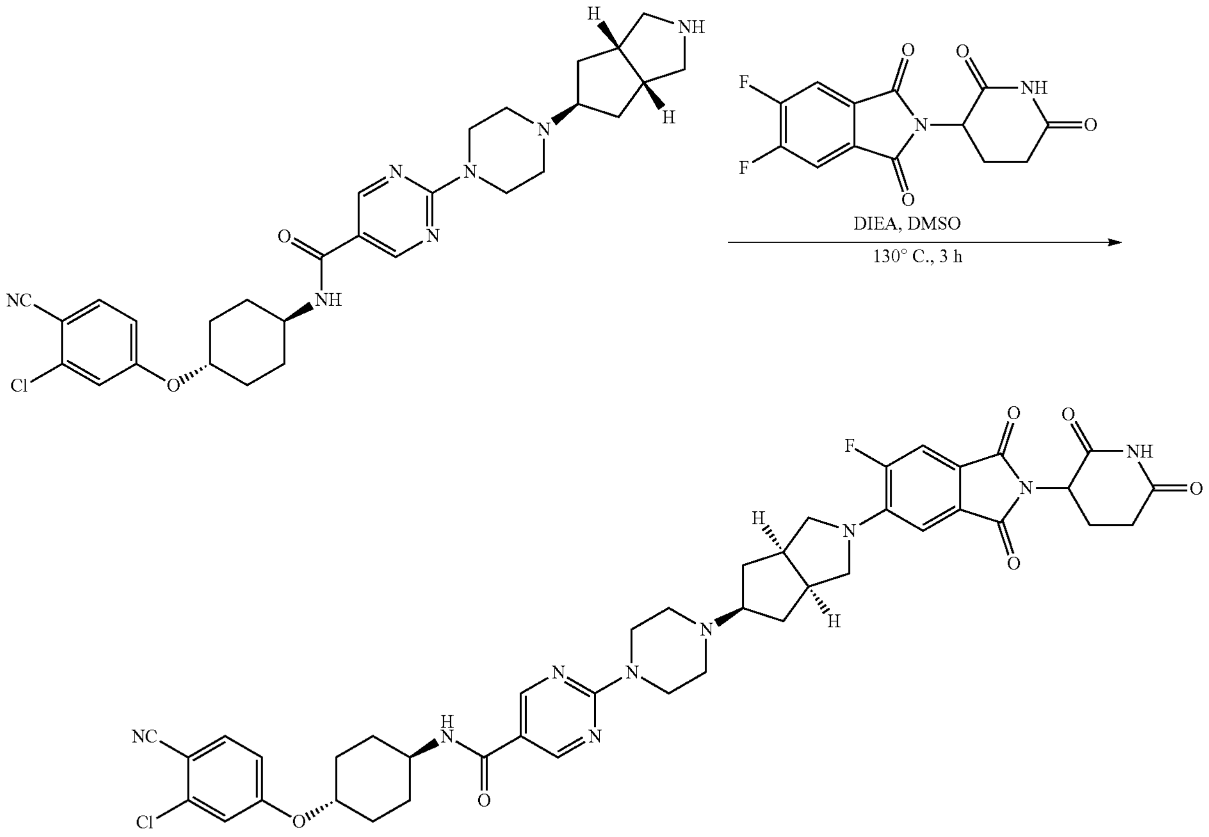
299

LC/MS ($ESI^+$) calcd for $C_{42}H_{44}ClFN_9O_6^+$ ($[M+H]^+$) m/z: 824.3; found 824.2.

$^1H$ NMR (400 MHz, $CDCl_3$) 8.69 (s, 2H), 8.36 (s, 1H), 7.56 (d, J=8.6 Hz, 1H), 7.40 (d, J=12.1 Hz, 1H), 7.09 (d, J=7.1 Hz, 1H), 6.99 (s, 1H), 6.85 (d, J=8.4 Hz, 1H), 5.89 (s, 1H), 4.92 (d, J=6.6 Hz, 1H), 4.29 (s, 1H), 3.97 (s, 4H), 3.58 (s, 4H), 2.82 (dd, J=58.5, 14.3 Hz, 6H), 2.30 (s, 2H), 2.17 (d, J=11.6 Hz, 5H), 1.84-1.50 (m, 8H), 1.43 (d, J=10.9 Hz, 2H).

300: N-((1r,4r)-4-(3-chloro-4-cyanophenoxy)cyclohexyl)-2-(4-((3aR,5R,6aS)-2-(2-(2,6-dioxopiperidin-3-yl)-1,3-dioxoisoindolin-5-yl)octahydrocyclopenta[c]pyrrol-5-yl)piperazin-1-yl)pyrimidine-5-carboxamide

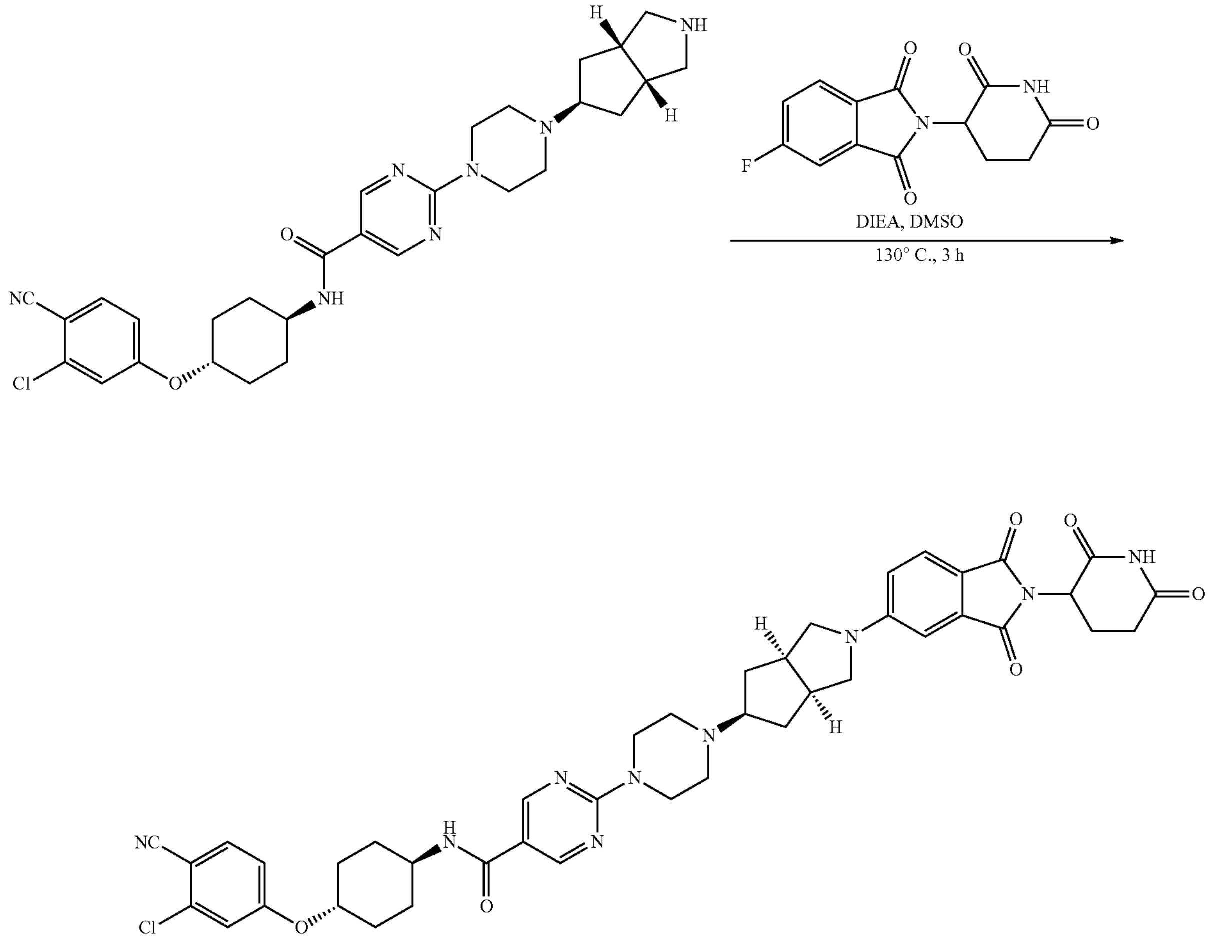

300

LC/MS ($ESI^+$) calcd for $C_{42}H_{45}ClN_9O_6^+$ ($[M+H]^+$) m: 806.3; found 806.3.

$^1H$ NMR (400 MHz, $CDCl_3$) δ 8.68 (s, 2H), 8.36 (s, 1H), 7.65 (d, J=8.4 Hz, 1H), 7.56 (d, J=8.7 Hz, 1H), 6.98 (dd, J=7.8, 2.2 Hz, 2H), 6.84 (dd, J=8.8, 2.4 Hz, 1H), 6.69 (dd, J=8.6, 2.1 Hz, 1H), 5.85 (d, J=7.7 Hz, 1H), 4.94 (dd, J=12.3, 5.4 Hz, 1H), 4.35-4.22 (m, 1H), 4.12-3.80 (m, 5H), 3.67-3.51 (m, 2H), 3.47-3.35 (m, 2H), 2.93-2.70 (m, 6H), 2.35-2.24 (m, 2H), 2.24-2.09 (m, 5H), 1.79-1.56 (m, 8H), 1.42 (dd, J=14.9, 8.8 Hz, 2H).

301: (3aR,5s,6aS)-2-(2,6-dioxopiperidin-3-yl)-1,3-dioxoisoindolin-5-yl) octahydrocyclopenta[c]pyrrol-5-yl 4-(5-(((1r,4r)-4-(3-chloro-4-cyanophenoxy)cyclohexyl)carbamoyl)pyrazine-2-yl)piperazine-1-carboxylate

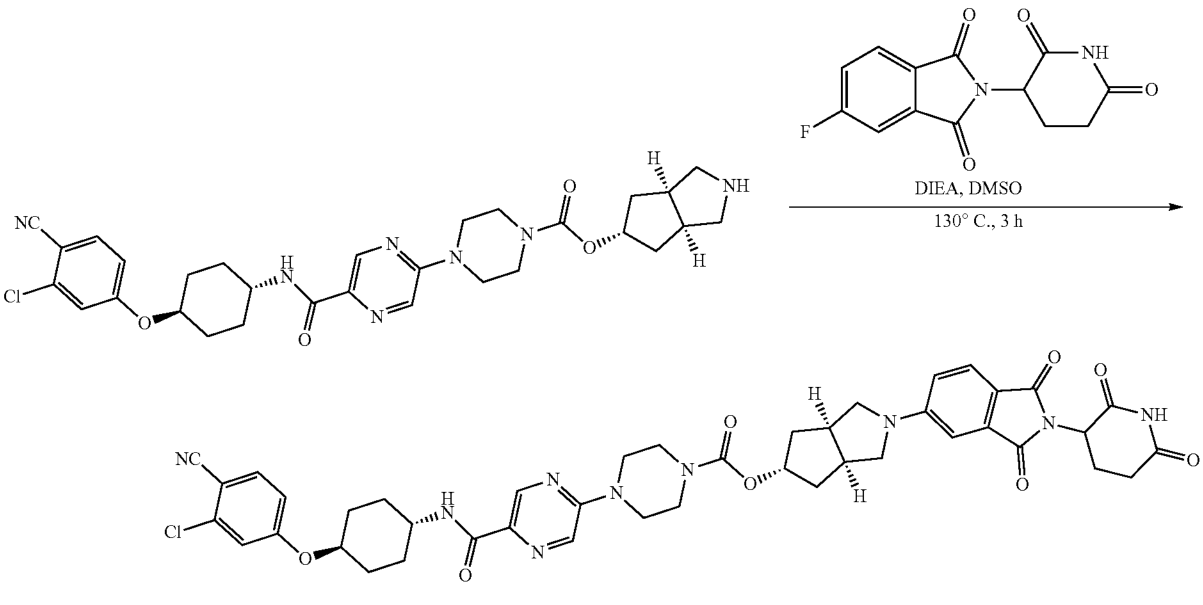

301

LC/MS (ESI+) calcd for $C_{43}H_{45}ClN_9O_8^+$ ($[M+H]^+$) m/z: 850.3; found 850.2.

$^1$H NMR (400 MHz, DMSO-$d_6$) δ 11.07 (s, 1H), 8.63 (d, J=1.2 Hz, 1H), 8.27 (s, 1H), 8.15 (d, J=8.4 Hz, 1H), 7.86 (d, J=8.8 Hz, 1H), 7.65 (d, J=8.4 Hz, 1H), 7.37 (d, J=2.4 Hz, 1H), 7.12 (dd, J=8.8, 2.4 Hz, 1H), 6.94 (s, 1H), 6.90-6.80 (m, 1H), 5.16 (s, 1H), 5.06 (dd, J=12.8, 5.4 Hz, 1H), 4.51 (t, J=9.8 Hz, 1H), 3.83 (d, J=8.0 Hz, 1H), 3.76-3.68 (m, 4H), 3.59 (dd, J=10.2, 7.4 Hz, 2H), 3.51 (s, 4H), 3.30 (s, 2H), 2.98 (s, 2H), 2.93-2.83 (m, 1H), 2.63-2.52 (m, 2H), 2.09 (d, J=10.5 Hz, 2H), 2.00 (dd, J=9.1, 3.9 Hz, 3H), 1.89 (dd, J=14.7, 8.0 Hz, 4H), 1.66-1.46 (m, 4H).

302: N-((1r,4r)-4-(3-chloro-4-cyanophenoxy)cyclohexyl)-4-(4-((1-(2-(2,6-dioxopiperidin-3-yl)-1,3-dioxoisoindolin-5-yl)piperidine-4-yl)amino)piperidin-1-yl)benzamide

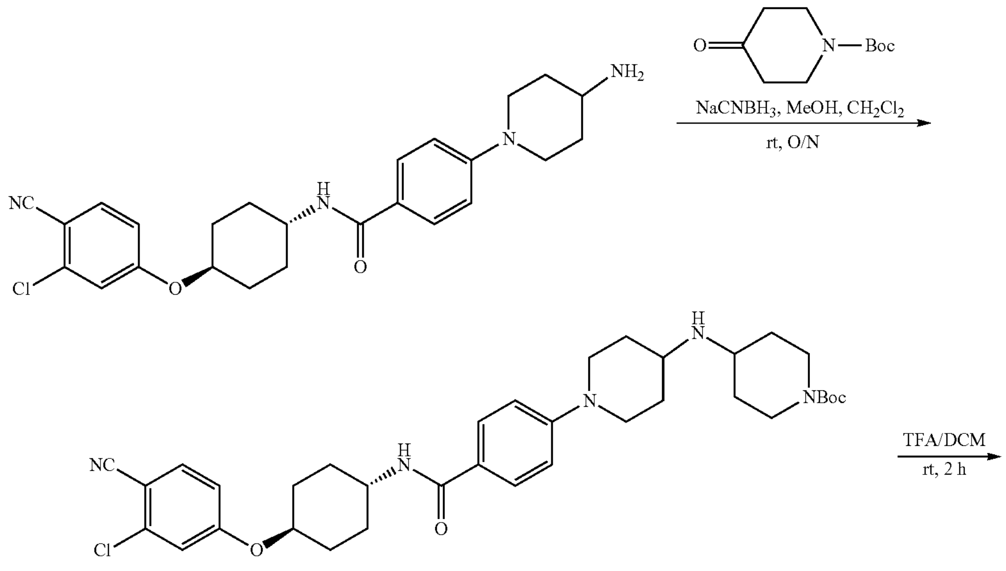

-continued
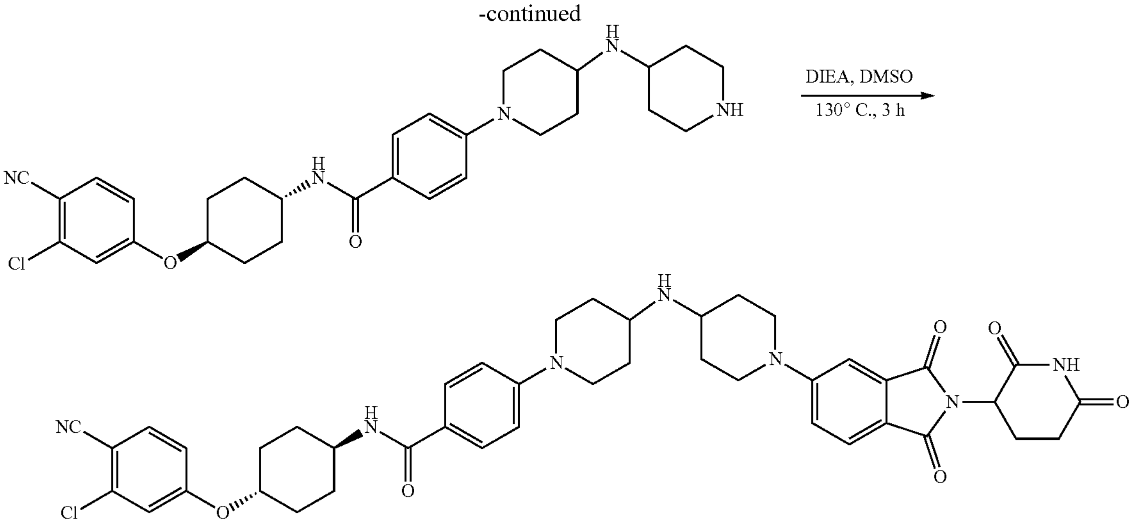
302
LC/MS (ESI+) calcd for $C_{43}H_{47}ClN_7O_6^+$ ([M+H]+) m/z: 792.3; found 792.2.
$^1$H NMR (400 MHz, $CDCl_3$) δ 7.67 (dd, J=13.0, 8.7 Hz, 3H), 7.56 (d, J=8.8 Hz, 1H), 7.35 (s, 1H), 7.18-7.11 (m, 1H), 7.08 (s, 1H), 6.99 (s, 1H), 6.90 (d, J=9.2 Hz, 2H), 6.85 (d, J=8.6 Hz, 1H), 4.98-4.91 (m, 1H), 4.33-4.27 (m, 1H), 4.10-3.90 (m, 4H), 3.87-3.76 (m, 2H), 3.09-3.00 (m, 2H), 2.89 (s, 3H), 2.78-2.73 (m, 1H), 2.17 (m, 6H), 2.04 (m, 6H), 1.60-1.49 (m, 7H).
303: N-((2s,3aR,5R,6aS)-5-(3-chloro-4-cyanophenoxy)octahydropenten-2-yl)-5-(4-((4-(2-(2,6-dioxopiperidin-3-yl)-1,3-dioxoisoindolin-5-yl)piperazin-1-yl)methyl)piperidin-1-yl)piperazine-2-carboxamide
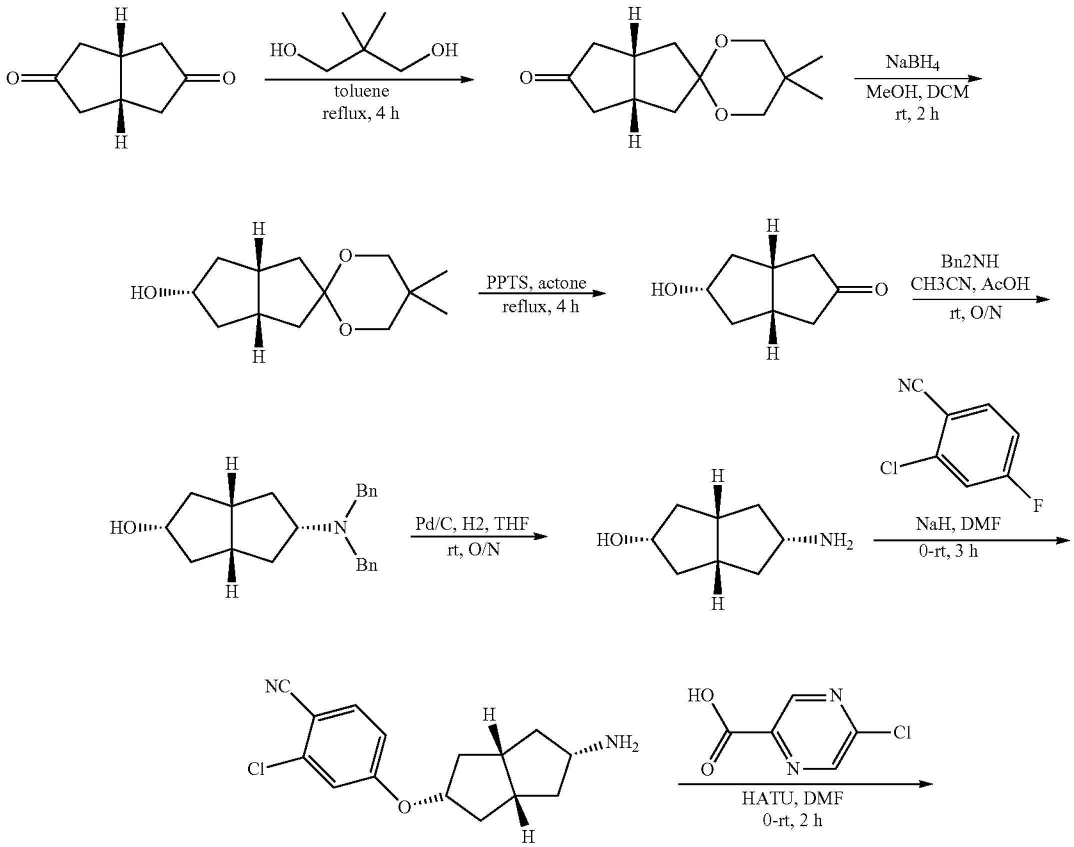

-continued

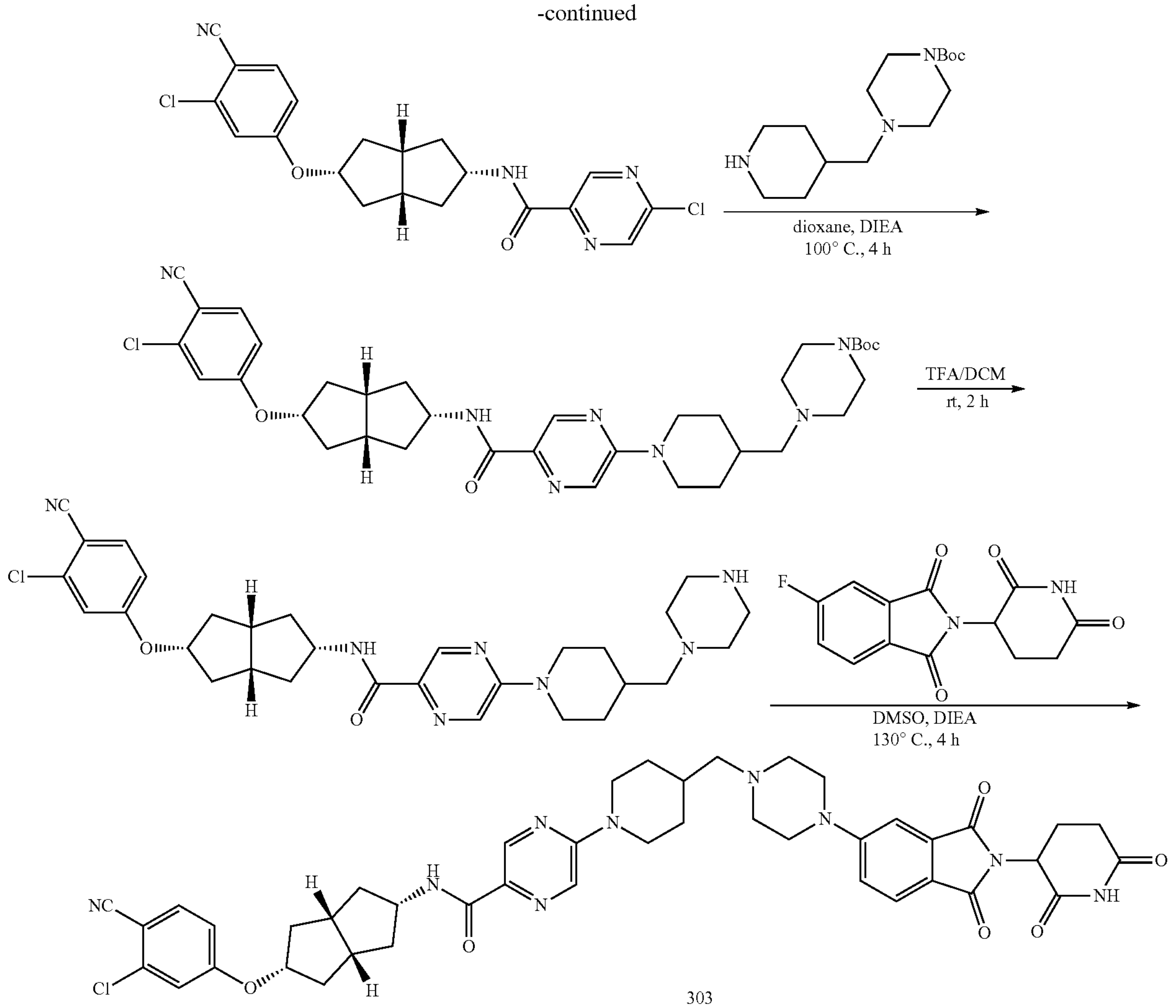

303

1. Compound (3a'R,6a'S)-5,5-dimethyltetrahydro-1'H-spiro[[1,3]dioxane-2,2'-pentene]-5'(3'H)-1

(3as,6as)-Tetrahydropentene-2,5(1H,3H)-dione (6.0 g, 43.4 mmol) and 2,2-dimethylpropane-1,3-diol (4.5 g, 43.4 mmol) were added to 200 mL, and then p-toluenesulfonic acid (150.0 mg, 43.4 mmol) was added. The mixture was heated 4 h under reflux. The reaction solution was cooled to room temperature, concentrated, rotatory evaporated to dry, and purified by silica gel column chromatography, to provide compound (3a'R,6a'S)-5,5-dimethyltetrahydro-$1^1$H-spiro[[1,3]dioxane-2,2'-pentene]-5'(3'H)-1 (4.5 g, 20.0 mmol), with a yield of 46%.

2. Compound (3a'R,5's,6a's)-5,5-dimethylhexahydro-1'H-spiro[[1,3]dioxane-2,2'-pentene]-5'-ol (3a'R,6a'S)-5,5-dimethyltetrahydro-1'H-spiro[[1,3]dioxane-2,2'-pentene]-5'(3'H)-1 (4.5 g, 20.0 mmol) was dissolved in 30 mL of methanol and 30 mL of dichloromethane, to which was added sodium borohydride (1.5 g, 40.0 mmol) in batches. The reaction solution was stirred at room temperature for 2 h, and then water and dichloromethane were added for extraction. The organic layer was washed with saturated brine, dried, and rotatory evaporated to dry, to provide crude compound (3a'R,5's,6a's)-5,5-dimethylhexahydro-1'H-spiro[[1,3]dioxane-2,2'-pentene]-5'-ol (3.5 g, 15.5 mmol), with a yield of 77.1%.

3. Compound (3aR,5s,6aS)-5-hydroxylhexahydropentene-2(1H)-one (3a'R,5's,6a's)-5,5-Dimethylhexahydro-1'H-spiro[[1.3]dioxane-2,2'-pentene]-5'-alcohol (2.5 g, 11.5 mmol) was dissolved in acetone (50 mL), to which was added 4-methylbenzenesulfonic acid pyridine (1.1 g, 4.6 mmol). The mixture was heated 4 h under reflux. The reaction solution was cooled to room temperature, and then ethyl acetate and water were added for extraction. The organic layer was washed with saturated brine, dried, rotatory evaporated to dry, and purified by silica gel column chromatography, to provide compound (3aR,5s,6aS)-5-hydroxylhexahydropentene-2(1H)-one (0.9 g, 6.2 mmol), with a yield of 58.1%.

4. Compound (2r,3aR,5s,6aS)-5-(dibenzylamino)octahydropenten-2-ol

Compound (3aR,5s,6aS)-5-hydroxylhexahydropentene-2(1H)-one (0.6 g, 4.3 mmol) and dibenzylamine (0.8 g, 4.3 mmol) were dissolved in 20 mL of acetonitrile, to which was added acetic acid (0.2 g, 4.3 mmol), followed by addition of sodium cyanoborohydride (0.8 g, 12.8 mmol). The solution was stirred overnight at room temperature. Then, the reaction solution was added with ethyl acetate and water for extraction. The organic layer was washed with saturated brine, dried, rotatory evaporated to dry, and purified by silica gel column chromatography, to provide compound (2r,3aR,5s,6aS)-5-(dibenzylamino)octahydropenten-2-ol (250.0 mg, 6.2 mmol), with a yield of 18.1%.

5. Compound (2r,3aR,5s,6aS)-5-aminooctahydropenten-2-ol

Compound (2r,3aR,5s,6aS)-5-(dibenzylamino)octahydropenten-2-ol (250.0 mg, 0.7 mmol) was dissolved in 5 mL of THF, to which was added wet Pd/C (100.0 mg). The system was purged with hydrogen three times using a hydrogen balloon. The reaction solution was stirred overnight at room temperature, and then subjected to suction filter through a pad of celite. The filter cake was washed twice with methanol. The filtrate was rotatory evaporated to dry, to obtain the crude compound (2r, 3aR,5s,6aS)-5-aminooctahydropenten-2-ol (35.0 mg, 0.2 mmol), with a yield of 32.8%.

6. Compound 4-((2r,3aR,5s,6aS)-5-aminooctahydropenten-2-yl)oxy)-2-chlorobenzonitrile Compound (2r,3aR,5s,6aS)-5-aminooctahydropenten-2-ol (35.0 mg, 0.2 mmol) was dissolved in DMF (3 mL), to which was added NaH (30.0 mg, 0.6 mmol) in an ice bath. Then, the reaction solution was stirred for 1 h in an ice bath, to which was added 2-chloro-4-fluorobenzonitrile (30.0 mg, 0.2 mmol). The solution was stirred 1 h at room temperature. Then, the reaction solution was added with ethyl acetate and water for extraction. The organic layer was washed with saturated brine, dried, rotatory evaporated to dry, and purified by silica gel column chromatography, to provide compound 4-((2r,3aR,5s,6aS)-5-aminooctahydropenten-2-yl)oxy)-2-chlorobenzonitrile (25 mg, 0.09 mmol), with a yield of 36.4%.

7. Compound 5-chloro-N-((2s,3aR,5R,6aS)-5-(3-chloro-4-cyanophenoxy) octahydropenten-2-yl)pyrazine-2-carboxamide 5-Chloropyrazine-22-carboxylic acid (14.0 mg, 0.09 mmol), compound 4-((2r, 3aR,5s,6aS)-5-aminooctahydropenten-2-yl)oxy)-2-chlorobenzonitrile (25.0 mg, 0.09 mmol), and HATU (32.0 mg, 0.09 mmol) were added in DMF (1 mL), and then DIEA (23.0 mg, 0.18 mmol) was added. The solution was stirred 1 h at room temperature. Then, the reaction solution was added with dichloromethane and water for extraction. The organic layer was washed with saturated brine, dried, rotatory evaporated to dry, and purified by silica gel column chromatography, to provide compound 5-chloro-N-((2s,3aR,5R,6aS)-5-(3-chloro-4-cyanophenoxy)octahydropenten2-yl)pyrazine-2-carboxamide (30.0 mg, 0.07 mmol), with a yield of 80.0%.

8. Compound t-butyl 4-((1-(5-((2s,3aR,5R,6aS)-5-(3-chloro-4-cyanophenoxy) octahydropenten-2-carbamoyl)pyrazine-2-yl)piperidine-4-yl)methyl)piperazine-1-carboxylate 5-Chloro-N-((2s,3aR,5R,6aS)-5-(3-chloro-4-cyanophenoxy)octahydropenten-2-yl) pyrazine-2-carboxamide (30.0 mg, 0.07 mmol), t-butyl 4-(piperidin-4-ylmethyl)piperazine-1-carboxylate (40.1 mg, 0.14 mmol), and DIEA (27.8 mg, 0.21 mmol) were added in dioxane (2 mL). The reaction solution was heated to 100° C. and stirred for 6 h, and then cooled to room temperature. The reaction solution was added with ethyl acetate and water for extraction. The organic layer was washed with saturated brine, dried, rotatory evaporated to dry, and purified by silica gel column chromatography, to provide compound t-butyl 4-((1-(5-((2s,3aR,5R,6aS)-5-(3-chloro-4-cyanophenoxy)octahydropenten-2-carbamoyl)pyrazine-2-yl)piperidine-4-yl)methyl) piperazine-1-carboxylate (30.0 mg, 0.45 mmol), with a yield of 62.8%.

9. Compound N-((2s,3aR,5R,6aS)-5-(3-chloro-4-cyanophenoxy)octahydropenten-2-yl)-5-(4-(piperazin-1-ylmethyl)piperidin-1-yl)pyrazine-2-carboxamide Compound t-butyl 4-((1-(5-((2s,3aR,5R,6aS)-5-(3-chloro-4-cyanophenoxy) octahydropenten-2-carbamoyl) pyrazine-2-yl)piperidine-4-yl)methyl)piperazine-1-carboxylate (30.0 mg, 0.45 mmol) was dissolved in trifluoroacetic acid (1 mL) and dichloromethane (1 mL), and the reaction solution was stirred at room temperature 1 h, and rotatory evaporated to dry, to provide crude compound N-((2s,3aR,5R,6aS)-5-(3-chloro-4-cyanophenoxy)octahydropenten-2-yl)-5-(4-(piperazin-1-ylmethyl)piperidin-1-yl) pyrazine-2-carboxamide (25.0 mg, 0.45 mmol), with a yield of 100.0%.

10. Compound N-((2s,3aR,5R,6aS)-5-(3-chloro-4-cyanophenoxy)octahydropenten-2-yl)-5-(4-((4-(2-(2,6-dioxopiperidin-3-yl)-1,3-dioxoisoindolin-5-yl) piperazin-1-yl) methyl)piperidine-1

Compound N-((2s, 3aR,5R,6aS)-5-(3-chloro-4-cyanophenoxy)octahydropenten-2-yl)-5-(4-(piperazin-1-ylmethyl)piperidin-1-yl)pyrazine-2-carboxamide (25.0 mg, 0.45 mmol), 2-(2,6-dioxopiperidin-3-yl)-5-fluoroisoindole-1,3-dione (12.0 mg, 0.45 mmol), and DIEA (57.0 mg, 4.5 mmol) were added in 1 mL of DMSO. The reaction solution was heated to 130° C. and stirred for 2 h, and then cooled to room temperature. The reaction solution was added with ethyl acetate and water for extraction. The organic layer was washed with saturated brine, dried, rotatory evaporated to dry, and purified by prep.-TLC, to provide the target compound (14 mg, 0.17 mmol), with a yield of 38.8%.

LC/MS ($ESI^+$) calcd for $C_{43}H_{47}ClN_9O_6^+$ ($[M+H]^+$) m/z: 820.3; found 820.3.

$^1H$ NMR (400 MHz, $CDCl_3$) δ 8.82 (d, J=1.2 Hz, 1H), 8.09 (s, 1H), 7.97 (s, 1H), 7.72 (d, J=8.5 Hz, 1H), 7.57 (d, J=8.7 Hz, 1H), 7.47 (d, J=8.3 Hz, 1H), 7.30 (d, J=1.9 Hz, 1H), 7.08 (d, J=8.4 Hz, 1H), 7.03 (d, J=2.4 Hz, 1H), 6.86 (dd, J=8.7, 2.4 Hz, 1H), 4.95 (dd, J=12.3, 5.2 Hz, 1H), 4.86 (s, 1H), 4.48 (d, J=13.1 Hz, 2H), 4.33 (d, J=8.0 Hz, 1H), 3.49 (s, 2H), 3.00 (t, J=12.3 Hz, 2H), 2.90 (d, J=16.9 Hz, 1H), 2.85 (s, 1H), 2.83-2.72 (m, 2H), 2.67 (d, J=24.9 Hz, 4H), 2.47-2.33 (m, 3H), 2.17 (td, J=14.9, 7.3 Hz, 3H), 2.01 (dd, J=14.9, 8.1 Hz, 2H), 1.89 (d, J=13.9 Hz, 2H), 1.63 (s, 7H), 1.48 (dd, J=17.5, 8.9 Hz, 2H).-

304: N-((1r,4r)-4-(3-chloro-4-cyanophenoxy)cyclohexyl)-4-(4-((1-(2-(2,6-dioxopiperidin-3-yl)-1,3-dioxoisoindolin-5-yl)piperidine-4-yl)oxy)piperidin-1-yl)benzamide

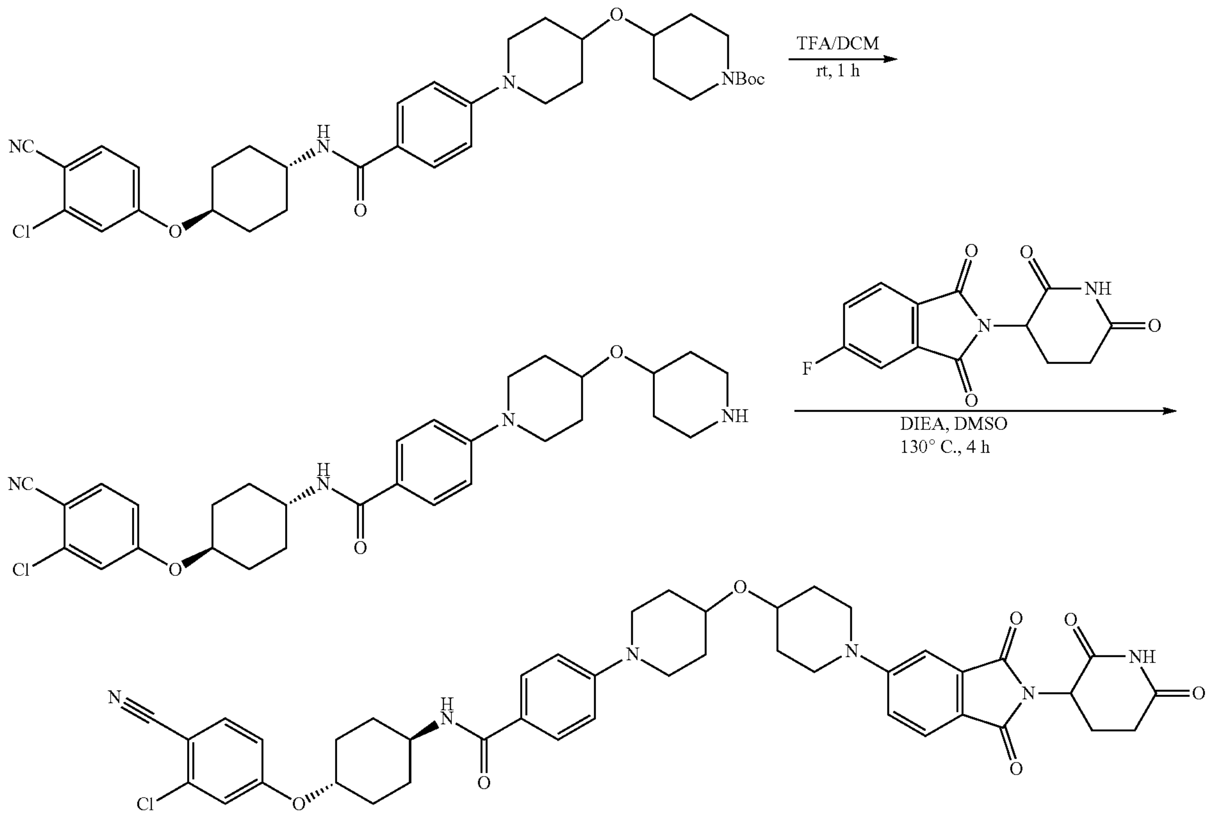

304

LC/MS (ESI+) calcd for $C_{43}H_{46}ClN_9O_6^+$ ([M+H]+) m/z: 793.3; found 793.2.

$^1$H NMR (400 MHz, DMSO-d$_6$) δ 11.09 (s, 1H), 7.97 (d, J=7.6 Hz, 1H), 7.86 (d, J=8.8 Hz, 1H), 7.74 (d, J=8.8 Hz, 2H), 7.66 (d, J=8.5 Hz, 1H), 7.39 (d, J=2.3 Hz, 1H), 7.34 (s, 1H), 7.26 (d, J=8.6 Hz, 1H), 7.15 (dd, J=8.8, 2.3 Hz, 1H), 6.96 (t, J=10.5 Hz, 2H), 5.08 (dd, J=12.9, 5.4 Hz, 1H), 4.53 (s, 1H), 3.90-3.74 (m, 4H), 3.74-3.57 (m, 3H), 3.26 (t, J=10.0 Hz, 2H), 3.03 (t. J=9.9 Hz, 2H), 2.94-2.81 (m, 1H), 2.64-2.55 (m, 2H), 2.11 (d, J=9.0 Hz, 2H), 2.06-1.99 (m, 1H), 1.90 (d, J=9.5 Hz, 6H), 1.54 (dd, J=21.9, 11.9 Hz, 8H).

305: N-((1r,4r)-4-(3-chloro-4-cyanophenoxy)cyclohexyl)-6-(4-((4-(2-(2,6-dioxopiperidin-3-yl)-6-fluoro-1-oxoisoindol-5-yl)piperazin-1-yl)methyl) piperidin-1-yl)-N-deuteromethylnicotinamide

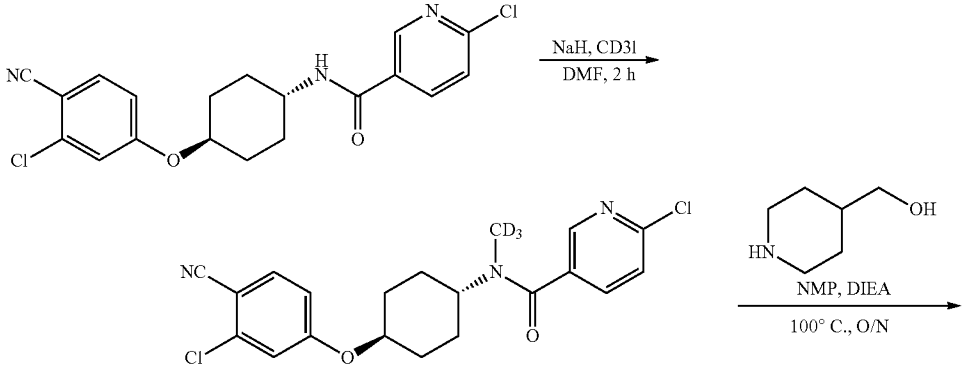

-continued
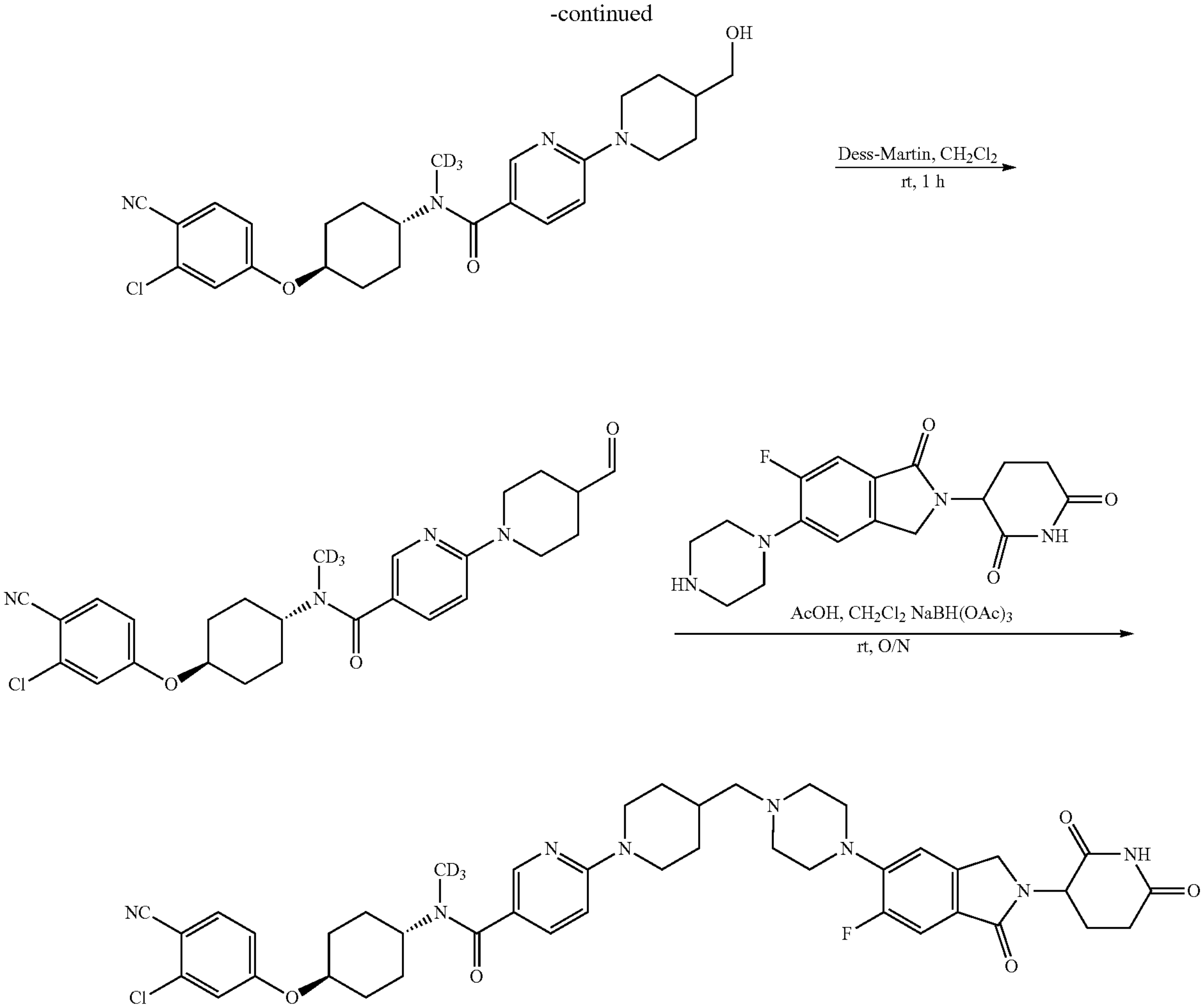
305
LC/MS (ESI$^+$) calcd for $C_{43}H_{46}D_3ClFN_8O_5^+ \times$ m/z 814.4; found 814.3.
306: N-((1r,4r)-4-(3-chloro-4-cyanophenoxy)cyclohexyl)-6-(4-((4-(2-(2,6-dioxopiperidin-3-yl)-6-fluoro-3-oxoisoindol-5-yl)piperazin-1-yl)methyl)piperidin-1-yl)-N-deuteromethylnicotinamide
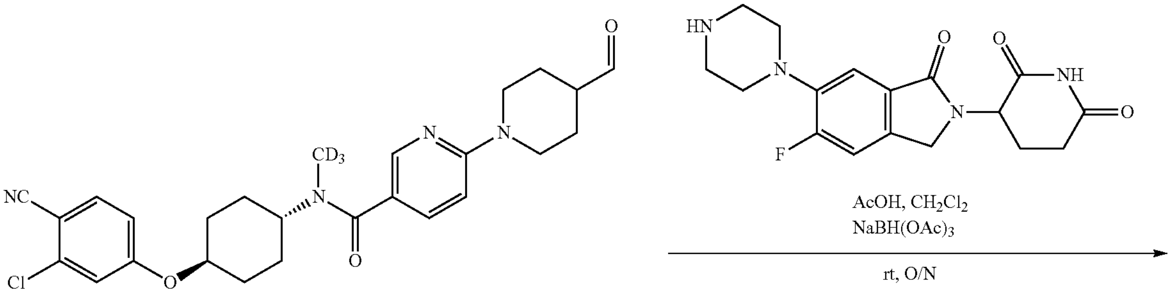

-continued
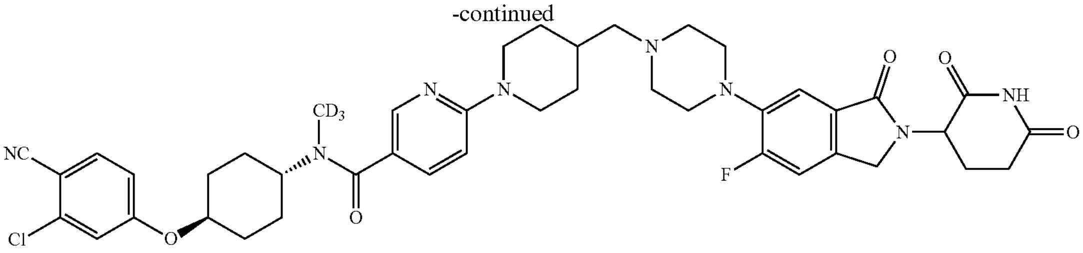
306
LC/MS ($ESI^+$) calcd for $C_{43}H_{46}D_3ClFN_8O_5^+$ m/z 814.4; found 814.3.
307: 2-chloro-4-((1r,4r)-4-(2-(4-((4-(6-fluoro-2-(1-methyl-2,6-dioxopiperidin-3-yl)-3-oxoisoindolin-5-yl)piperazin-1-yl)methyl)piperidin-1-yl)-5-oxo-5H-pyrrolo[3,4-b]pyridin-6(7H)-yl)cyclohexyl)oxy) benzonitrile
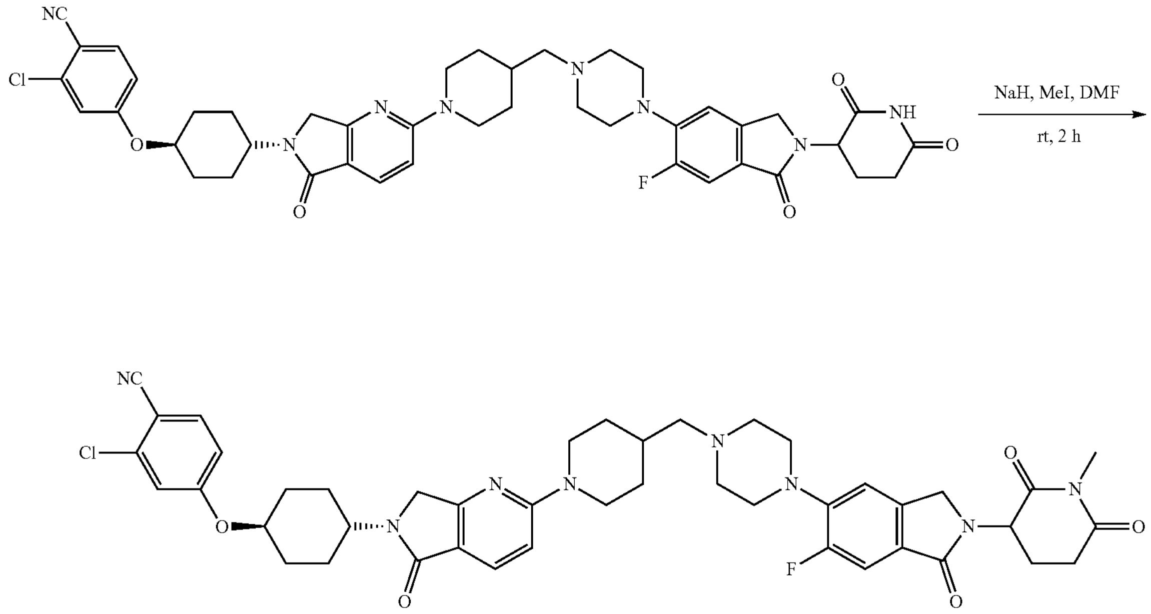
307
LC/MS ($ESI^+$) calcd for $C_{44}H_{49}ClFN_8O_5^+$ m/z 823.3, found 823.3.

308: (3-(5-(4-((1-(6-((1r,4r)-4-(3-chloro-4-cyanophenoxy)cyclohexyl)-5-oxo-6,7-dihydro-5H-pyrrolo[3,4-b]pyridin-2-yl)piperidine-4-yl)methyl)piperazin-1-yl)-6-fluoro-1-oxoisoindol-2-yl)-2,6-dioxopiperidin-1-yl)methyl 2,5,8,11-tetraoxopiperidine-13-ylamide

308

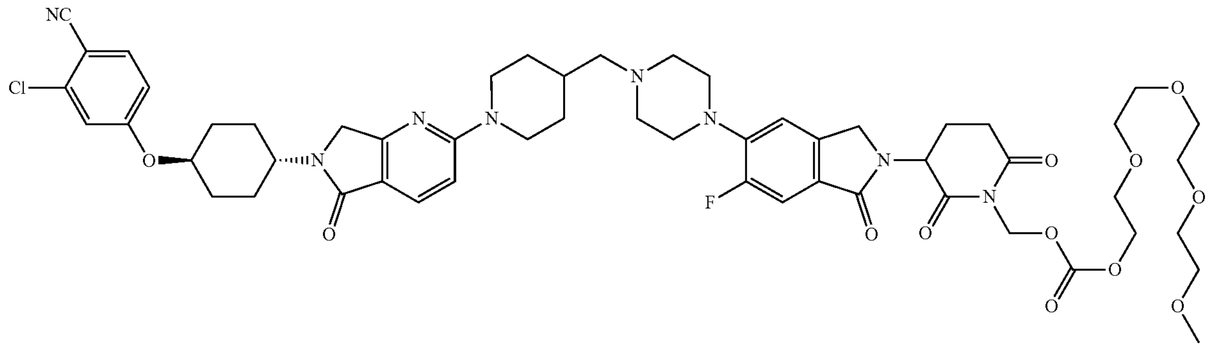

LC/MS ($ESI^+$) calcd for $C_{54}H_{67}ClFN_8O_{12}^+$ m/z 1073.5; found 1073.4.

309: 2-chloro-4-((1r,4r)-4-(2-(4-((4-(3-(2,6-dioxopiperidin-3-yl)-2-methyl-4-oxo-3,4-dihydroquinazoline-7-yl)piperazin-1-yl)methyl)piperidin-1-yl)-5-oxo-5H-pyrrolo[3,4-b]pyridin-6(7H)-yl)cyclohexyl)oxy)benzonitrile

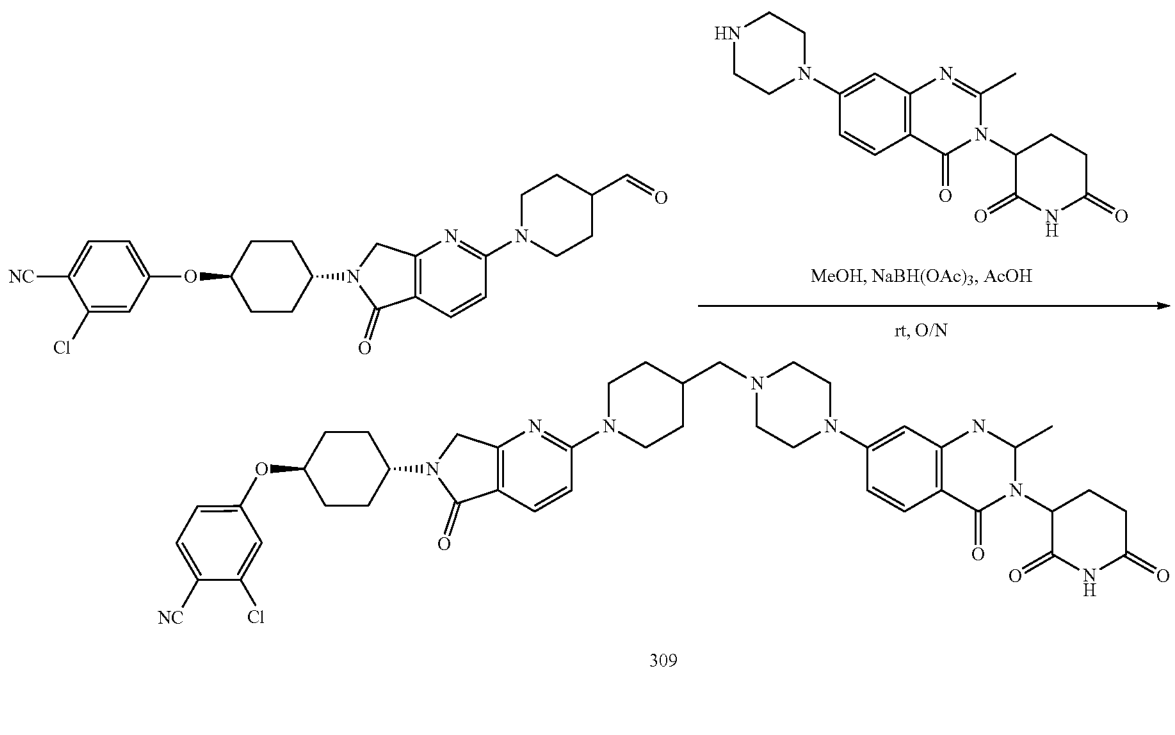

309

LC/MS ($ESI^+$) calcd for $C_{44}H_{49}ClN_9O_5^+$ m/z 818.4; found 818.4.

$^1$H NMR (400 MHz, $CDCl_3$) δ 8.20 (s, 1H), 8.03 (d, J=8.9 Hz, 1H), 7.83 (d, J=8.8 Hz, 1H), 7.58 (d, J=8.7 Hz, 1H), 7.03 (t, J=4.4 Hz, 2H), 6.95 (s, 1H), 6.88 (dd, J=8.7, 2.3 Hz, 1H), 6.68 (d, J=8.9 Hz, 1H), 4.74 (dd, J=11.2, 5.9 Hz, 1H), 4.50 (d, J=12.4 Hz, 2H), 4.31 (s, 2H), 4.21 (s, 2H), 3.55 (d, J=31.2 Hz, 4H), 2.97 (dd, J=26.9, 15.2 Hz, 4H), 2.84-2.71 (m, 2H), 2.68 (s, 3H), 2.26 (s, 2H), 2.19 (d, J=5.5 Hz, 1H), 2.03 (s, 4H), 1.84-1.64 (m, 10H).
310: 2-chloro-4-((1r,3r)-3-(5-((1-(1-(2-(2,6-dioxopiperidin-3-yl)-6-fluoro-1,3-dioxoisoindolin-5-yl)azetidine-3-yl)-1H-pyrazol-4-yl)ethynyl)-1-oxoisoindolin-2-yl)-2,2,4,4-tetramethylcyclobutoxy) benzonitrile
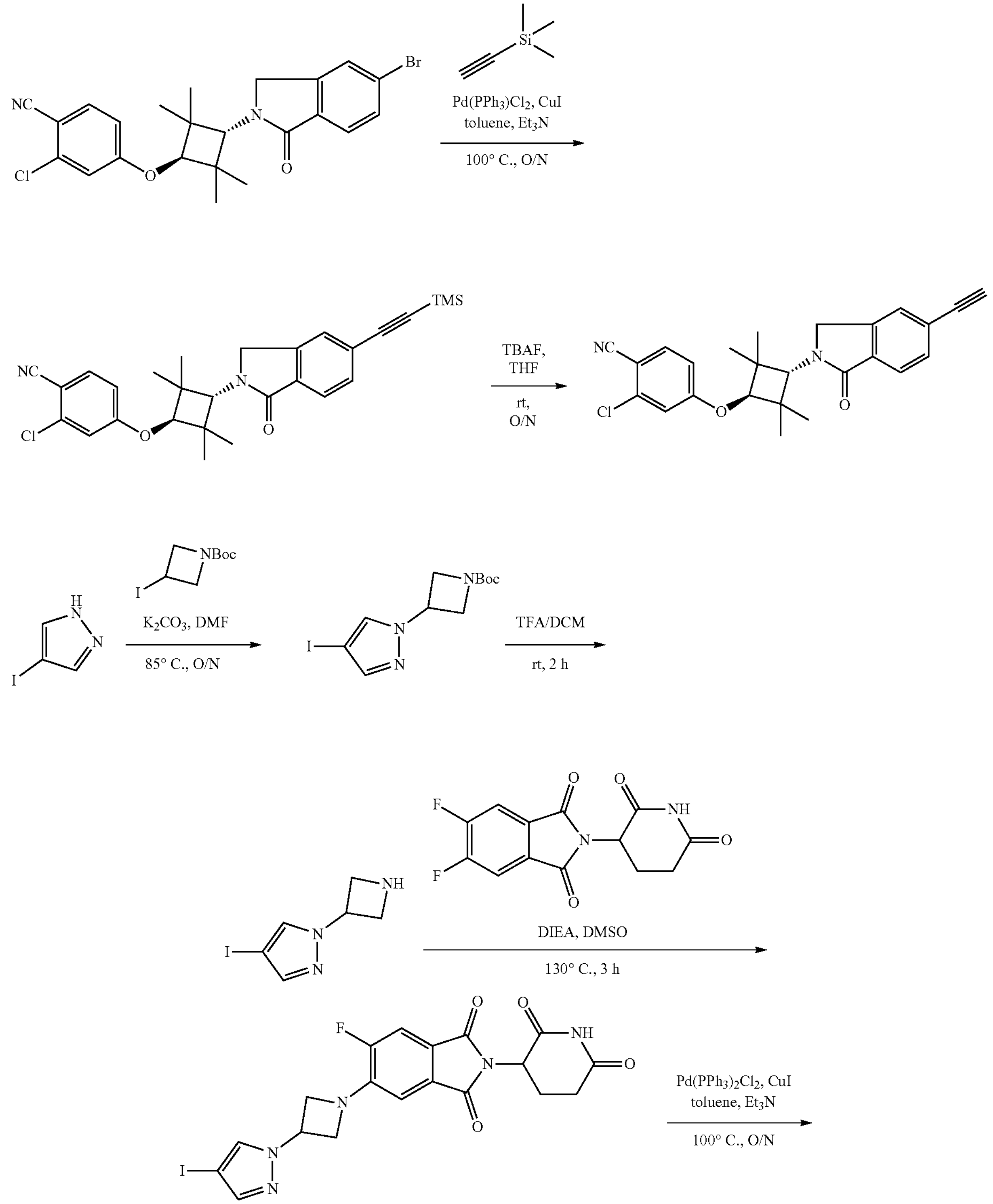

-continued

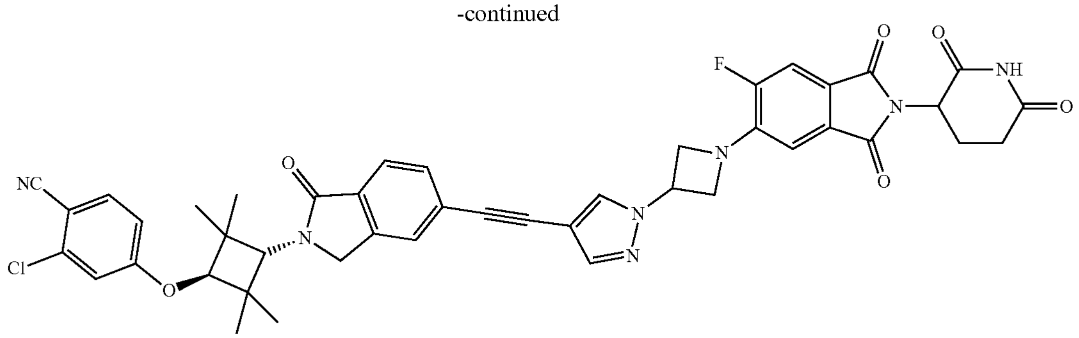

310

1. Synthesis of Compound (2-chloro-4-((1r,3r)-2,2,4,4-tetramethyl-3-(1-oxo-5-((trimethylsilyl)ethynyl)isoindol-2-yl)cyclobutyloxy)benzonitrile Under the nitrogen protection, 4-((1r,3r)-3-(5-bromo-1-oxoisoindol-2-yl)-2,2,4,4-tetramethylcyclobutoxy)-2-chlorobenzonitrile (500.0 mg, 1.06 mmol), ethynyltrimethylsilane (518.0 mg, 5.28 mmol), $Pd(PPh_3)_2Cl_2$ (100.0 mg, 0.1 mmol), CuI (60.0 mg, 0.2 mmol), and 2 mL of triethylamine were added to 6 mL of toluene. The reaction solution was heated to 100° C. and stirred overnight, and then cooled to room temperature. The reaction solution was subjected to suction filter, and the filter cake was washed with ethyl acetate. The filtrate was dried, rotatory evaporated to dry, and purified by silica gel column chromatography, to obtain compound (2-chloro-4-((1r,3r)-2,2,4,4-tetramethyl-3-(1-oxo-5-((trimethylsilyl)ethynyl)isoindol-2-yl) cyclobutyloxy)benzonitrile (400 mg, 0.80 mmol), with a yield of 77.2%.

LC/MS ($ESI^+$) calcd for $C_{25}H_{24}ClN_2O_2Si^+$ ($[M+H]^+$) m/z: 491.2; found 491.1.

2. Synthesis of Compound 2-chloro-4-((1r,3r)-3-(5-ethynyl-1-oxoisoindol-2-yl)-2,2,4,4-tetramethylcyclobutoxy)benzonitrile 2-chloro-4-((1r,3r)-2,2,4,4-tetramethyl-3-(1-oxo-5-((trimethylsilyl)ethynyl) isoindolin-2-yl)cyclobutyloxy) benzonitrile (400 mg, 0.80 mmol) and TBAF (1 g, 1.60 mmol) were dissolved in 10 mL of THF. The solution was stirred overnight at room temperature. Then, the reaction solution was added with water and ethyl acetate for extraction. The organic layer was washed with saturated brine, dried, rotatory evaporated to dry, and purified by silica gel column chromatography, to provide compound 2-chloro-4-((1r,3r)-3-(5-ethynyl-1-oxoisoindolin-2-yl)-2,2,4,4-tetramethyl cyclobutoxy)benzonitrile (150 mg, 0.35 mmol), with a yield of 43.9%.

LC/MS ($ESI^+$) calcd for $C_{25}H_{24}ClN_2O_2^+$ ($[M+H]^+$) m/z: 419.2; found 419.1.

3. Synthesis of Compound t-butyl 3-(4-iodo-1H-pyrazol-1-yl)azetidine-1-carboxylate 4-Iodo-1H-pyrazole (400 mg, 1.40 mmol), N-Boc-3-iodoazetidine (274 mg, 1.41 mmol), and $K_2CO_3$ (292 mg, 2.12 mmol) were dissolved in 5 mL DMF. The reaction solution was heated to 85° C. and stirred overnight, and then cooled to room temperature. The reaction solution was added with water and ethyl acetate for extraction. The organic layer was washed with saturated brine, dried, rotatory evaporated to dry, and purified by silica gel column chromatography, to provide compound t-butyl 3-(4-iodo-1H-pyrazol-1-yl)azetidine-1-carboxylate (380 mg, 1.08 mmol), with a yield of 77.0%.

4. Synthesis of Compound 1-(azetidine-3-yl)-4-iodo-1H-pyrazole t-Butyl 3-(4-iodo-1H-pyrazol-1-yl)azetidine-1-carboxylate (380 mg, 1.08 mmol) was dissolved in 2 mL of dichloromethane and 2 mL of trifluoroacetic acid. The reaction solution was stirred 2 h at room temperature, and rotatory evaporated to dry, to obtain the target compound (180 mg, 1.08 mmol), with a yield of 100.0%.

5. Synthesis of Compound 2-(2,6-dioxopiperidin-3-yl)-5-fluoro-6-(3-(4-iodo-1H-pyrazol-1-yl)azetidine-1-yl)isoindoline-1,3-dione 1-(Azetidine-3-yl)-4-iodo-1H-pyrazole (180.0 mg, 1.08 mmol), 2-(2,6-dioxopiperidin-3-yl)-5,6-difluoroisoindoline-1,3-dione (100 mg, 0.339 mmol), and DIEA (219 mg, 1.70 mmol) were dissolved in 3 mL of DMSO. The reaction solution was heated to 130° C. and stirred for 3 h. and then cooled to room temperature. The reaction solution was added with water and ethyl acetate for extraction. The organic layer was washed with saturated brine, dried, rotatory evaporated to dry, and purified by silica gel column chromatography, to provide compound 2-(2,6-dioxopiperidin-3-yl)-5-fluoro-6-(3-(4-iodo-1H-pyrazol-1-yl)azetidine-1-yl)isoindoline-1,3-dione (150 mg, 0.26 mmol), with a yield of 84.0%.

LC/MS ($ESI^+$) calcd for $C_{19}H_{16}FIN_5O_4^+$ ($[M+H]^+$) m/z: 524.0; found 524.0.

6. Synthesis of Compound 2-chloro-4-((1r,3r)-3-(5-((1-(1-(2-(2,6-dioxopiperidin-3-yl)-6-fluoro-1,3-dioxoisoindolin-5-yl)azetidine-3-yl)-1H-pyrazol-4-yl)ethynyl)-1-oxoisoindolin-2-yl)-2,2,4,4-tetramethylcyclobutoxy)benzonitrile Under the nitrogen protection, 2-(2,6-dioxopiperidin-3-yl)-5-fluoro-6-(3-(4-iodo-1H-pyrazol-1-yl)azetidine-1-yl) isoindoline-1,3-dione (50 mg, 0.10 mmol), 2-chloro-4-((1r,3r)-3-(5-ethynyl-1-oxoisoindol-2-yl)-2,2,4,4-tetramethylcyclobutoxy)benzonitrile (40 mg, 0.10 mmol), $Pd(PPh_3)_2Cl_2$ (8 mg, 0.01 mmol), CuI (10 mg, 0.02 mmol)

and 0.3 mL of triethylamine were added to 1 mL of toluene. The reaction solution was heated to 100° C. and stirred overnight, and then cooled to room temperature. The reaction solution was subjected to suction filter, and the filter cake was washed with ethyl acetate. The filtrate was dried, rotatory evaporated to dry, and purified by silica gel column chromatography, to obtain compound (2-chloro-4-((1r,3r)-3-(5-((1-(1-(2-(2,6-dioxopiperidin-3-yl)-6-fluoro-1,3-dioxoisoindolin-5-yl)azetidine-3-yl)-1H-pyrazol-4-yl)ethynyl)-1-oxoisoindolin-2-yl)-2,2,4,4-tetramethylcyclobutoxy) benzonitrile (15 mg, 0.80 mmol), with a yield of 19.2%.

LC/MS (ESI$^+$) calcd for $C_{44}H_{38}ClFN_7O_6^+$ ([M+H]$^+$) m/z: 814.3; found 814.2. $^1$H NMR (400 MHz, $CDCl_3$) δ 8.05-7.98 (m, 1H), 7.81 (d, J=7.9 Hz, 1H), 7.74 (s, 1H), 7.64 (s, 1H), 7.60-7.49 (m, 3H), 7.41 (d, J=12.2 Hz, 1H), 7.09 (d, J=7.2 Hz, 1H), 7.00 (d, J=2.4 Hz, 1H), 6.85 (dd, J=8.7, 2.4 Hz, 1H), 5.11-4.98 (m, 1H), 4.97-4.88 (m, 1H), 4.66 (s, 2H), 3.81-3.69 (m, 3H), 3.23 (td, J=9.8, 5.1 Hz, 1H), 2.99-2.85 (m, 5H), 2.85-2.70 (m, 2H), 2.16-2.08 (m, 1H), 1.46 (s, 6H), 1.27 (s, 6H).

311: 2-chloro-4-((1r,4r)-4-(6-((4-(2-(2,6-dioxopiperidin-3-yl)-6-fluoro-1,3-dioxoisoindolin-5-yl)piperazin-1-yl)methyl)piperidin-1-yl)-3-oxo-1,3-dihydro-2H-pyrrolo[3,4-c](pyridin-2-yl)cyclohexyl)oxy) benzonitrile

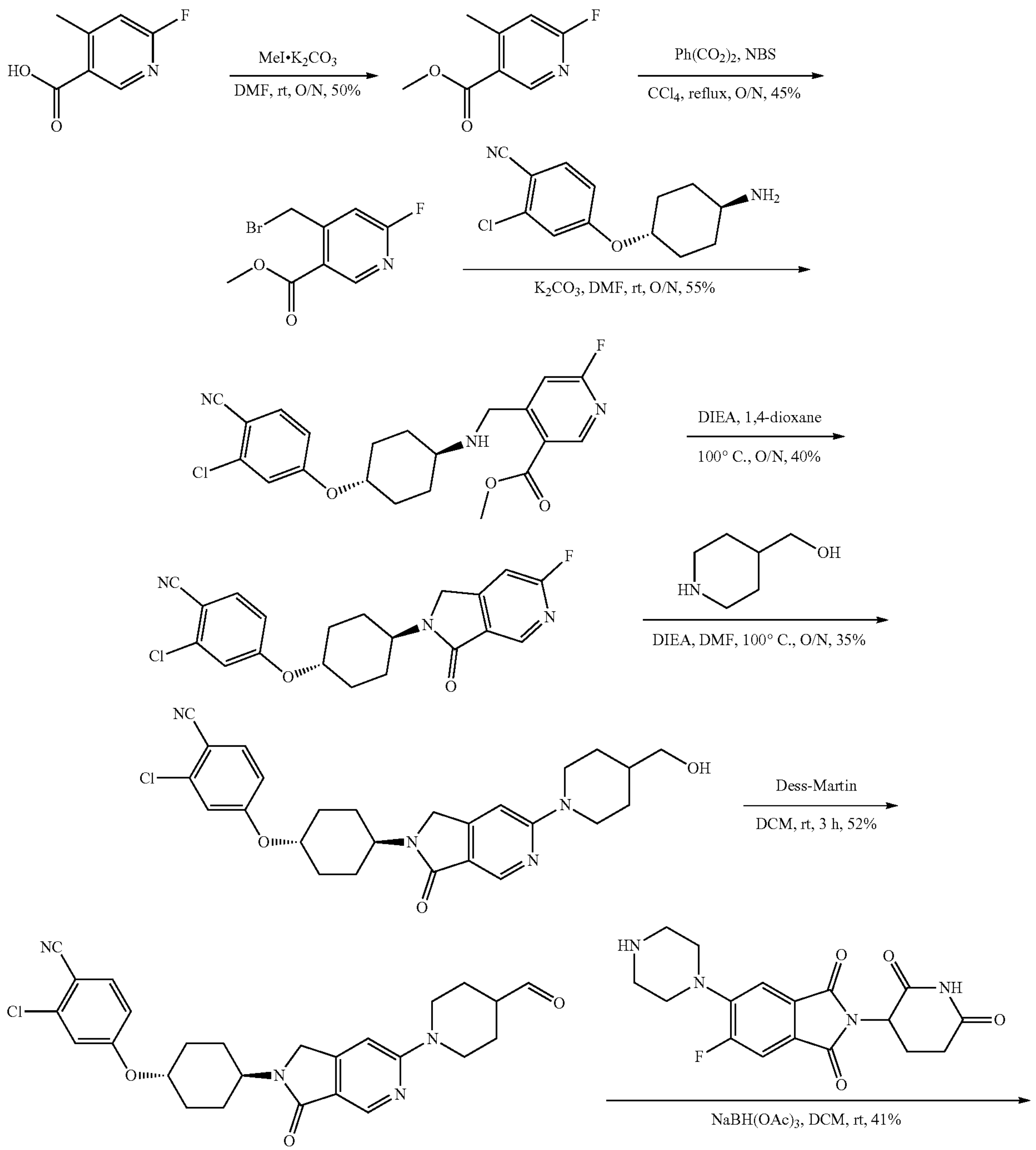

-continued

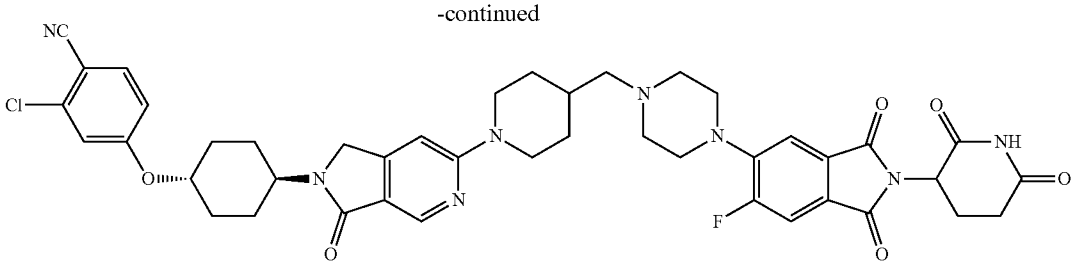

311

1. Synthesis of methyl 6-fluoro-4-methylnicotinate

Yield 50%. LC/MS (ESI+) calcd for: $C_8H_8FNO_2$ $[M+H]^+$ m/z, 170.1; found, 170.1.

2. Synthesis of methyl 4-(bromomethyl)-6-fluoronicotinate

Yield 45%. LC/MS (ESI+) calcd for: $C_8H_7BrFNO_2$ $[M+H]^+$ m/z, 170.1; found, 170.1.

3. Synthesis of methyl 4-(((1r,4r)-4-(3-chloro-4-cyanophenoxy)cyclohexyl)amino) methyl)-6-fluoronicotinate Yield 55%. LC/MS (ESI+) calcd for: $C_{21}H_{21}ClFN_3O_3$ $[M+H]^+$ m/z, 170.1; found, 170.1.

4. 2-Chloro-4-((1r,4r)-4-(6-fluoro-3-oxo-1,3-dihydro-2H-pyrrolo[3,4-c](pyridin-2-yl)cyclohexyl) oxy)benzonitrile Yield 40%. LC/MS (ESI+) calcd for: $C_{20}H_{17}ClFN_3O_2$ $[M+H]^+$ m/z, 386.1; found, 386.1.

5. Synthesis of 2-chloro-4-((1r,4r)-4-(6-(4-(hydroxymethyl)piperidin-1-yl)-3-oxo-1,3-dihydro-2H-pyrrolo[3,4-c](pyridin-2-yl)cyclohexyl)oxy)benzonitrile Yield 35%. LC/MS (ESI+) calcd for: $C_{26}H_{29}ClN_4O_3$[M+H]+ m/z, 481.2; found, 481.2.

6. Synthesis of 2-chloro-4-((1r,4r)-4-(6-(4-formylpiperidin-1-yl)-3-oxo-1,3-dihydro-2H-pyrrolo[3,4-c](pyridin-2-yl)cyclohexyl)oxy)benzonitrile Yield 52%. LC/MS (ESI+) calcd for: $C_{26}H_{27}ClN_4O_3$[M+H]+ m/z, 479.1; found, 479.1.

7. Synthesis of 2-chloro-4-((1r,4r)-4-(6-((4-(2-(2,6-dioxopiperidin-3-yl)-6-fluoro-1,3-dioxoisoindol-5-yl)piperazin-1-yl)methyl)piperidin-1-yl)-3-oxo-1,3-dihydro-2H-pyrrolo[3,4-c](pyridin-2-yl)cyclohexyl) oxy)benzonitrile Synthesized according to the previous example, with a yield of 41%. LC/MS (ESI+) calcd for: $C_{43}H_{44}ClFN_8O_6$ $[M+H]^+$ m/z, 479.1; found, 479.1.

312: 2-chloro-4-((1r,4r)-4-(6-((4-(2-(2,6-dioxopiperidin-3-yl)-1-oxoisoindolin-5-yl) piperazin-1-yl) methyl)piperidin-1-yl)-3-oxo-1,3-dihydro-2H-pyrrolo[3,4-c] (pyridin-2-yl)cyclohexyl)oxy) benzonitrile

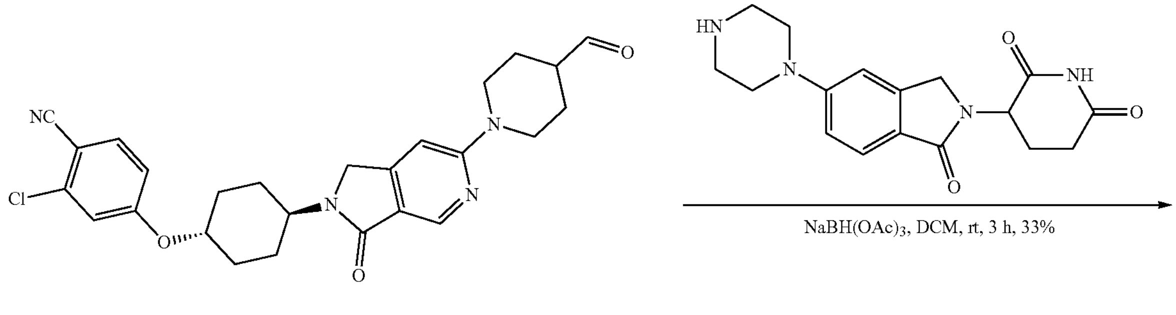

-continued

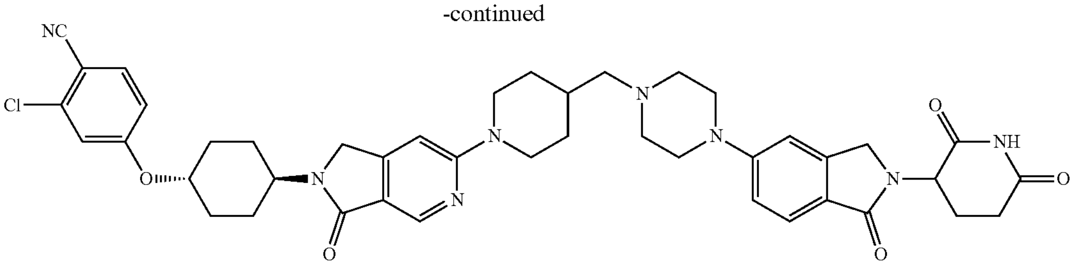

312

Synthesized according to the previous example, with a yield of 33%. LC/MS ($ESI^+$) calcd for: $C_{43}H_{47}ClN_8O_5$ $[M+H]^+$ m/z, 791.3; found, 791.3.

$^1H$ NMR (400 MHz, $CDCl_3$) δ 8.64 (d, J=0.9 Hz, 1H), 8.06 (s, 1H), 7.77 (d, J=8.5 Hz, 1H), 7.58 (d, J=8.8 Hz, 1H), 7.07-6.99 (m, 2H), 6.92 (s, 1H), 6.88 (dd, J=8.8, 2.4 Hz, 1H), 6.67-6.63 (m, 1H), 5.22 (dd, J=13.3, 5.2 Hz, 1H), 4.46 (t, J=14.4 Hz, 3H), 4.34-4.23 (m, 5H), 3.49 (s, 4H), 3.04-2.73 (m, 8H), 2.47 (s, 2H), 2.35 (dd, J=13.0, 5.1 Hz, 1H), 2.24 (d, J=12.6 Hz, 3H), 2.00 (d, J=12.4 Hz, 5H), 1.30 (d, J=20.2 Hz, 6H).

313: 2-Chloro-4-((1r,4r)-4-(6-((4-(2-(2,6-dioxopiperidin-3-yl)-6-fluoro-1-oxoisoindolin-5-yl)piperazin-1-yl)methyl)piperidin-1-yl)-3-oxo-1,3-dihydro-2H-pyrrolo[3,4-c](pyridin-2-yl)cyclohexyl)oxy) benzonitrile

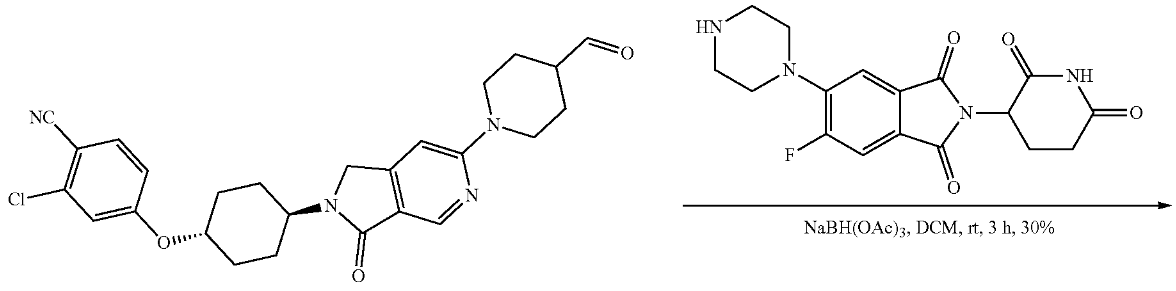

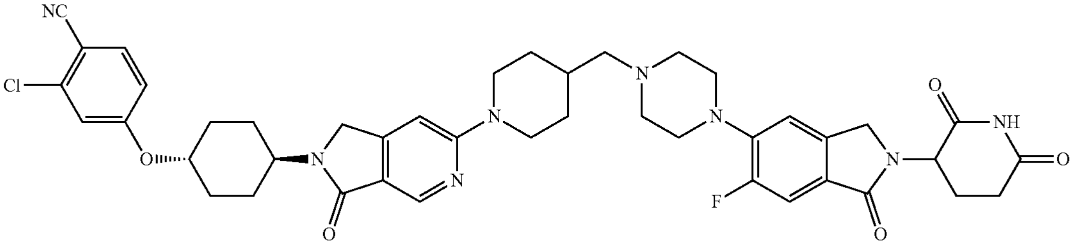

313

Synthesized according to the previous example, with a yield of 30%. LC/MS ($ESI^+$) calcd for: $C_{43}H_{46}ClFN_8O_5$ $[M+H]^+$ m/z, 809.3; found, 809.3.

314: 2-chloro-4-((1r,4r)-4-(6-((4-(2-(2,6-dioxopiperidin-3-yl)-1,3-dioxoisoindolin-5-yl)piperazin-1-yl)methyl)piperidin-1-yl)-3-oxo-1,3-dihydro-2H-pyrrolo[3,4-c](pyridin-2-yl)cyclohexyl)oxy)benzonitrile

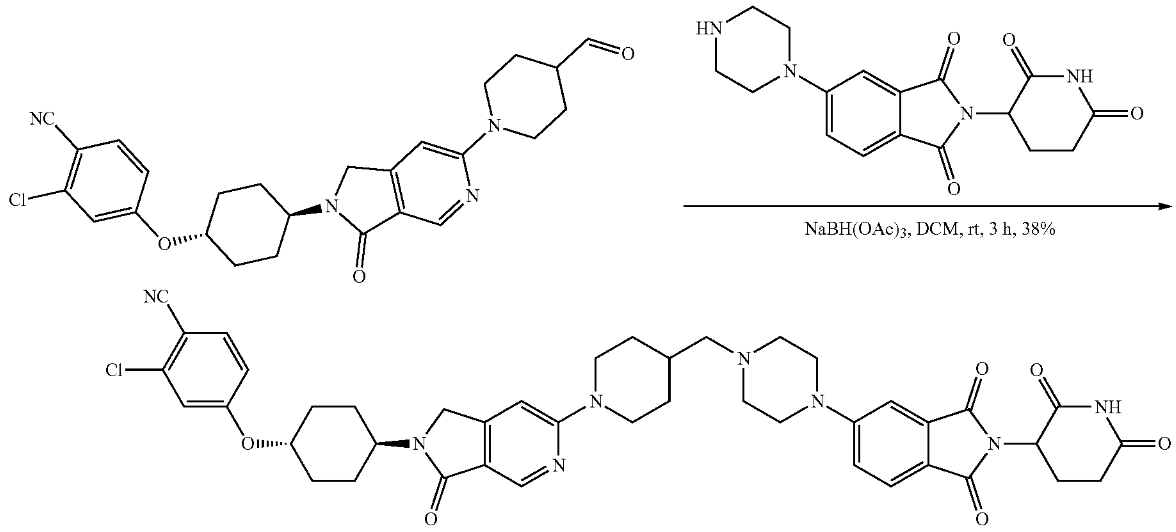

314

Synthesized according to the previous example, with a yield of 38%. LC/MS (ESI+) calcd for: $C_{43}H_{45}ClN_8O_6$ $[M+H]^+$ m/z, 805.3; found, 805.3.

315:2-chloro-4-((1r,3r)-3-(2-((1'-(2-(2,6-dioxopiperidin-3-yl)-1,3-dioxoisoindolin-5-yl)-[1,4'-dipiperidine]4-yl)ethynyl)-5-oxo-5,7-dihydro-6H-pyrrolo[3,4-b] pyridin-6-yl)-2,2,4,4-tetramethylcyclobutoxy) benzonitrile

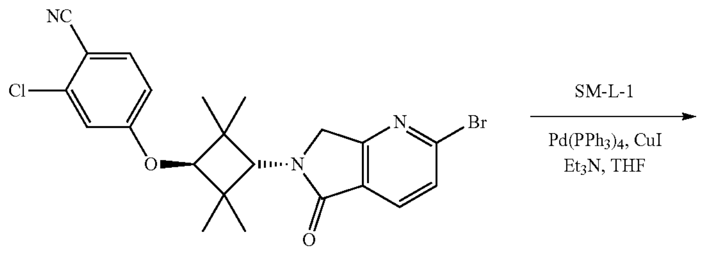

SM-A-1

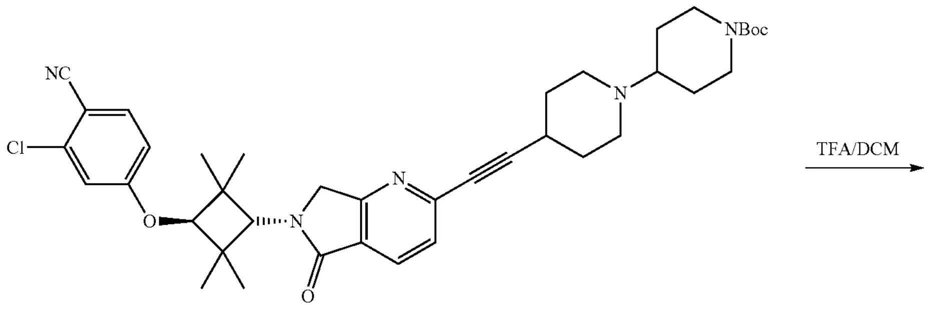

-continued

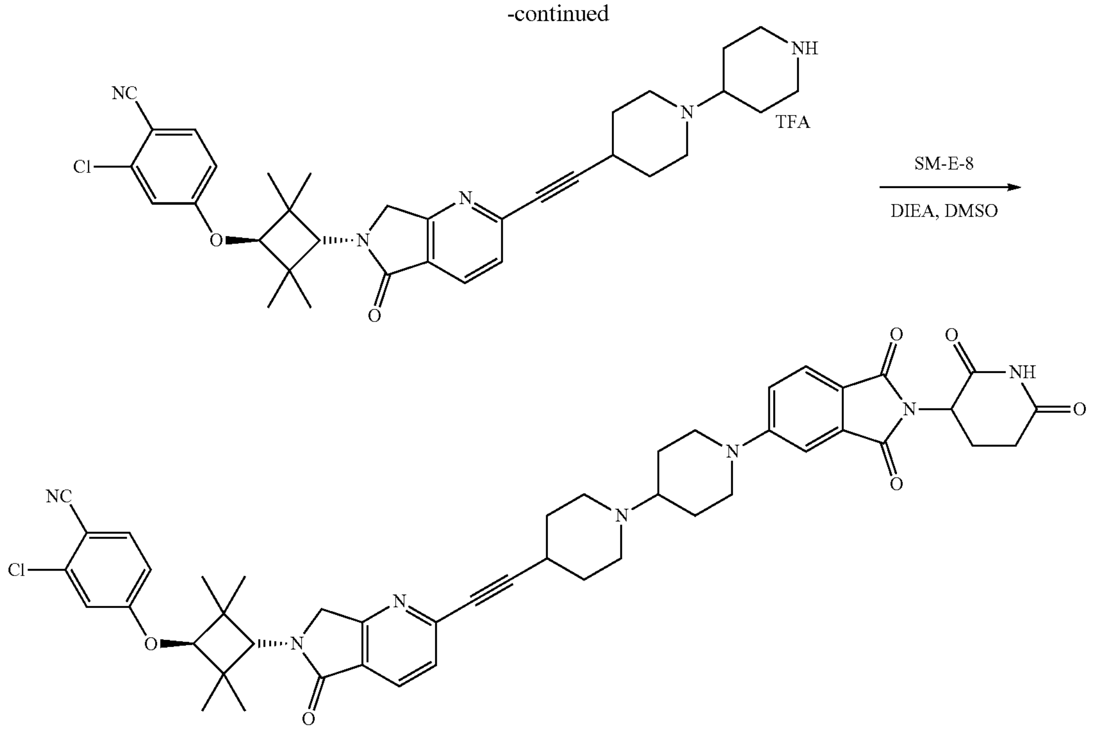

315

1. Compound t-butyl 4-((6-((1r,3r)-3-(3-chloro-4-cyanophenoxy)-2,2,4,4-tetramethylcyclobutyl)-5-oxo-6,7-dihydro-5H-pyrrolo[3,4-b]pyridin-2-yl)ethynyl)-1,4'-bipyridin-1'-carboxylate 4-((1r,3r)-3-(2-bromo-5-oxo-5H-pyrrolo[3,4-b]pyridin-6(7H)-yl)-2,2,4,4-tetramethylcyclobutoxy)-2-chlorobenzonitrile (500 mg, 1.06 mmol), t-butyl 4-ethynyl-1,4'-dipiperidine-1'-carboxylate (619 mg, 2.12 mmol) and triethylamine (0.5 mL) were dissolved in tetrahydrofuran (20 mL), to which were added tetrakis(triphenylphosphine)palladium (127 mg, 0.11 mmol) and CuI (42 mg, 0.22 mmol) under nitrogen protection. The reaction solution was stirred overnight at room temperature, and then rotatory evaporated to dry. The residue was purified by silica gel column chromatography (dichloromethane:methanol=100:1 to 25:1) to obtain a yellow solid t-butyl 4-((6-((1r,3r)-3-(3-chloro-4-cyanophenoxy)-2,2,4,4-tetramethylcyclobutyl)-5-oxo-6,7-dihydro-5H-pyrrolo[3,4-b]pyridin-2-yl)ethynyl)-1,4'-bipyridin-1'-carboxylate (280 mg, 0.41 mmol), with a yield of 39%. MS: calcd. for $C_{39}H_{49}ClO_5N_4$ $[M+H]^+$: 686.3; found: 686.4.

2. Compound 4-((1r,3r)-3-(2-(1,4'-dipiperidine-4-phenylene)-5-oxo-5H-pyrrolo[3,4-b] pyridin-6(7H)-yl)-2,2,4,4-tetramethylcyclobutoxy)-2-chlorobenzonitrile t-Butyl 4-((6-((1r,3r)-3-(3-chloro-4-cyanophenoxy)-2,2,4,4-tetramethylcyclobutyl)-5-oxo-6,7-dihydro-5H-pyrrolo[3,4-b]pyridin-2-yl)ethynyl)-1,4'-bipyridin-1'-carboxylate (140 mg, 0.12 mmol) was dissolved in dichloromethane (4 mL), and then trifluoroacetic acid (2 mL) was added in an ice bath. The reaction solution was stirred 1 h at room temperature, and rotatory evaporated to dry, to obtain the crude product 4-((1r,3r)-3-(2-(1,4'-dipiperidine-4-phenylene)-5-oxo-5H-pyrrolo[3,4-b]pyridin-6(7H)-yl)-2,2,4,4-tetramethylcyclobutoxy)-2-chlorobenzonitrile, which was directly used in next reaction. MS: calcd. for $C_{34}H_{41}ClO_5N_2$ $[M+H]^+$: 586.3; found: 586.2.

3. Compound 2-chloro-4-((1r,3r)-3-(2-((1'-(2,6-dioxopiperidin-3-yl)-1,3-dioxoisoindol-5-yl)-1,4'-dipiperidine-4-yl)ethynyl)-5-oxo-5H-pyrrolo[3,4-b]pyridin-6(7H)-yl)-2,2,4,4-tetramethylcyclobutoxy)benzonitrile 4-((1r,3r)-3-(2-(1,4'-Dipiperidine-4-phenylene)-5-oxo-5H-pyrrolo[3,4-b]pyridin-6(7H)-yl)-2,2,4,4-tetramethylcyclobutoxy)-2-chlorobenzonitrile (0.12 mmol, the crude product from the previous step) and N,N-diisopropylethylamine (105 mg, 1.2 mmol) were dissolved in dimethylsulfoxide (3 mL), to which was then added 2-(2,6-dioxopiperidin-3-yl)-5-fluoroisoindole-1,3-dione (36 mg, 0.13 mmol). The reaction solution was heated to 110° C. and allowed to react for 5 h. The reaction solution was diluted with water (10 mL) and then extracted with ethyl acetate (10 mL×3). The organic phases were combined and washed with saturated brine (10 mL×3), dried over sodium sulfate, and purified by prep.-TLC (silica gel) (dichloromethane:methanol=25:1) to obtain a yellow solid 2-chloro-4-((1r,3r)-3-(2-((1'-(2,6-dioxopiperidin-3-yl)-1,3-dioxoisoindol-5-yl)-1,4'-dipiperidine-4-yl)ethynyl)-5-oxo-5H-pyrrolo[3,4-b]pyridin-6(7H)-yl)-2,2,4,4-tetramethylcyclobutoxy)benzonitrile (15 mg, 0.018 mmol), with a yield of 9%.

MS: calcd. for $C_{47}H_{49}ClO_7N_6$ $[M+H]^+$: 842.3; found: 842.2. $^1H$ NMR (400 MHz, DMSO-$d_6$) δ 11.06 (s, 1H), 8.03 (d, J=7.9 Hz, 1H), 7.88 (d, J=8.6 Hz, 1H), 7.61 (t, J=15.8 Hz, 1H), 7.48 (t, J=30.7 Hz, 1H), 7.37-7.05 (m, 3H), 7.07 (t, J=13.8 Hz, 1H), 5.04 (dd, J=12.7, 5.2 Hz, 1H), 4.78 (s, 2H), 4.52 (s, 1H), 4.28 (d, J=31.9 Hz, 1H), 4.07 (d, J=11.9 Hz, 2H), 3.01-2.89 (m, 2H), 2.89-2.63 (m, 4H), 2.89-2.63 (m, 2H), 2.37-2.31 (m, 2H), 2.00-1.97 (m, 2H), 1.89-1.80 (m, 4H), 1.63-1.61 (m, 2H), 1.49-1.43 (m, 2H), 1.38 (s, 6H), 1.14 (s, 6H). MS: calcd. for $C_{47}H_{49}ClO_7N_6[M+H]^+$: 842.3; found: 842.2.
The following compounds 316-402 were synthesized by a method similar to that of compound 315.
316: 2-Chloro-4-((1r,3r)-3-(2-((1'-(2,6-dioxopiperidin-3-yl)-6-fluoro-1,3-dioxoisoindolin-5-yl)-1,4'-dipiperidine-4-yl)ethynyl)-5-oxo-5H-pyrrolo[3,4-b]pyridin-6(7H)-yl)-2,2,4,4-tetramethylcyclobutoxy) benzonitrile
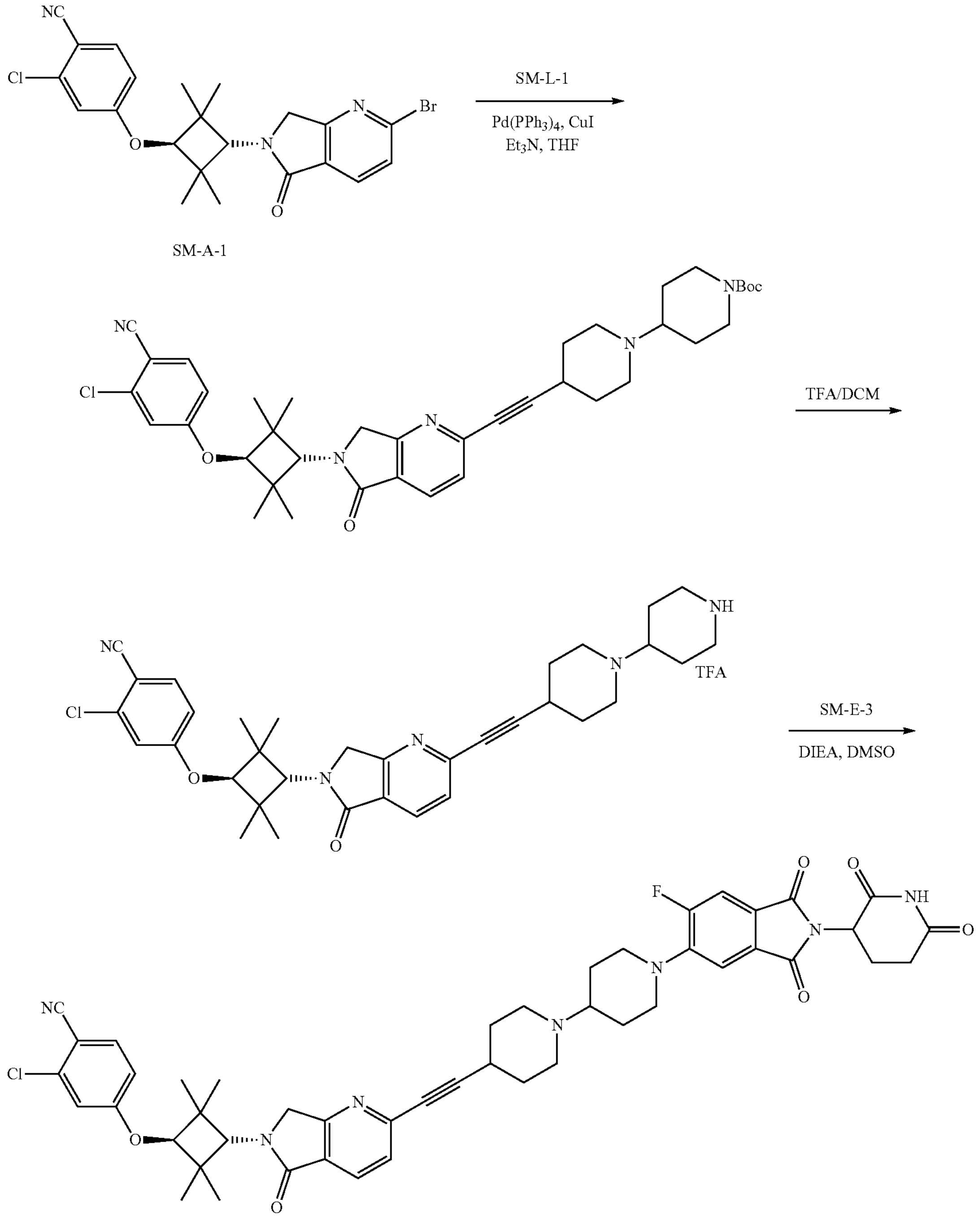
316

$^1$H NMR (400 MHz, DMSO-$d_6$) δ 11.09 (s, 1H), 8.03 (d, J=7.9 Hz, 1H), 7.89 (d, J=8.6 Hz, 1H), 7.69 (d, J=11.3 Hz, 1H), 7.54 (d, J=7.9 Hz, 1H), 7.43 (d, J=7.3 Hz, 1H), 7.22 (t, J=32.1 Hz, 1H), 7.05 (d, J=8.7 Hz, 1H), 5.08 (dd, J=12.5, 5.2 Hz, 1H), 4.79 (s, 2H), 4.52 (s, 1H), 4.32 (s, 1H), 3.65 (d, J=10.5 Hz, 2H), 2.90-2.72 (m, 6H), 2.63-2.55 (m, 2H), 2.45-2.32 (m, 2H), 2.03-1.97 (m, 2H), 1.89-1.83 (m, 414), 1.63-1.58 (m, 4H), 1.38 (s, 6H), 1.14 (s, 6H). MS: calcd. for $C_{13}H_{11}FO_3N_3[M+H]^+$: 860.3; found: 860.3.
317: 2-Chloro-4-((1r,3r)-3-(2-((1-(1-(2-(2,6-dioxopiperidin-3-yl)-6-fluoro-1,3-dioxoisoindolin-5-yl)azitidin-3-yl)piperidine-4-yl)ethynyl)-5-oxo-5H-pyrrolino [3,4-b]pyridin-6(7H)-yl)-2,2,4,4-tetramethylcyclobutoxy)benzonitrile
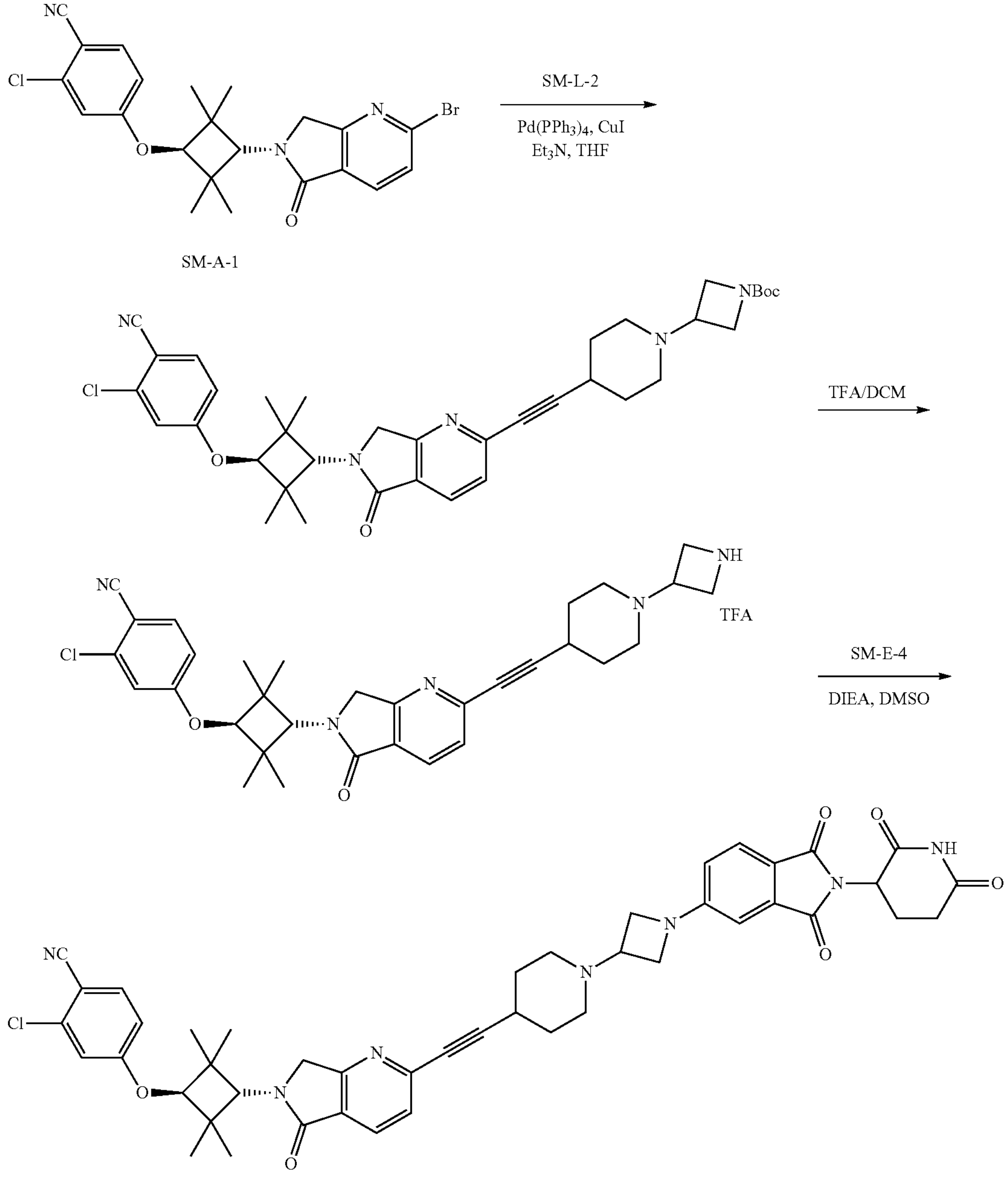
317

$^1H$ NMR (400 MHz, DMSO-$d_6$) δ 11.06 (s, 1H), 8.03 (d, J=7.9 Hz, 1H), 7.88 (d, J=8.8 Hz, 1H), 7.63 (d, J=8.2 Hz, 1H), 7.54 (d, J=7.9 Hz, 1H), 7.27 (d, J=2.4 Hz, 1H), 7.04 (dd, J=8.8, 2.4 Hz, 1H), 6.78 (d, J=1.7 Hz, 1H), 6.64 (dd, J=8.3, 1.9 Hz, 1H), 5.04 (dd, J=12.8, 5.3 Hz, 1H), 4.78 (s, 2H), 4.52 (s, 1H), 4.32 (s, 1H), 4.09 (t, J=7.6 Hz, 2H), 3.92-3.66 (m, 2H), 2.95-2.72 (m, 2H), 2.72-2.57 (m, 2H), 2.56-2.49 (m, 21H), 2.40-2.24 (m, 1H), 2.24-2.06 (m, 2H), 2.04-1.81 (m, 3H), 1.73-1.57 (m, 2H), 1.38 (s, 6H), 1.14 (s, 6H). MS: calcd. for $C_{45}H_{44}ClN_7O_6$ $[M+H]^+$: 814.3; found: 813.8.

318: 2-Chloro-4-((1r,3r)-3-(2-((1-(1-(2-(2,6-dioxopiperidin-3-yl)-6-fluoro-1,3-dioxoisoindolin-5-yl)azetidin-3-yl)piperidine-4-yl)ethynyl)-5-oxo-5H-pyrrolino [3,4-b]pyridin-6(7H)-yl)-2,2,4,4-tetramethylcyclobutoxy)benzonitrile

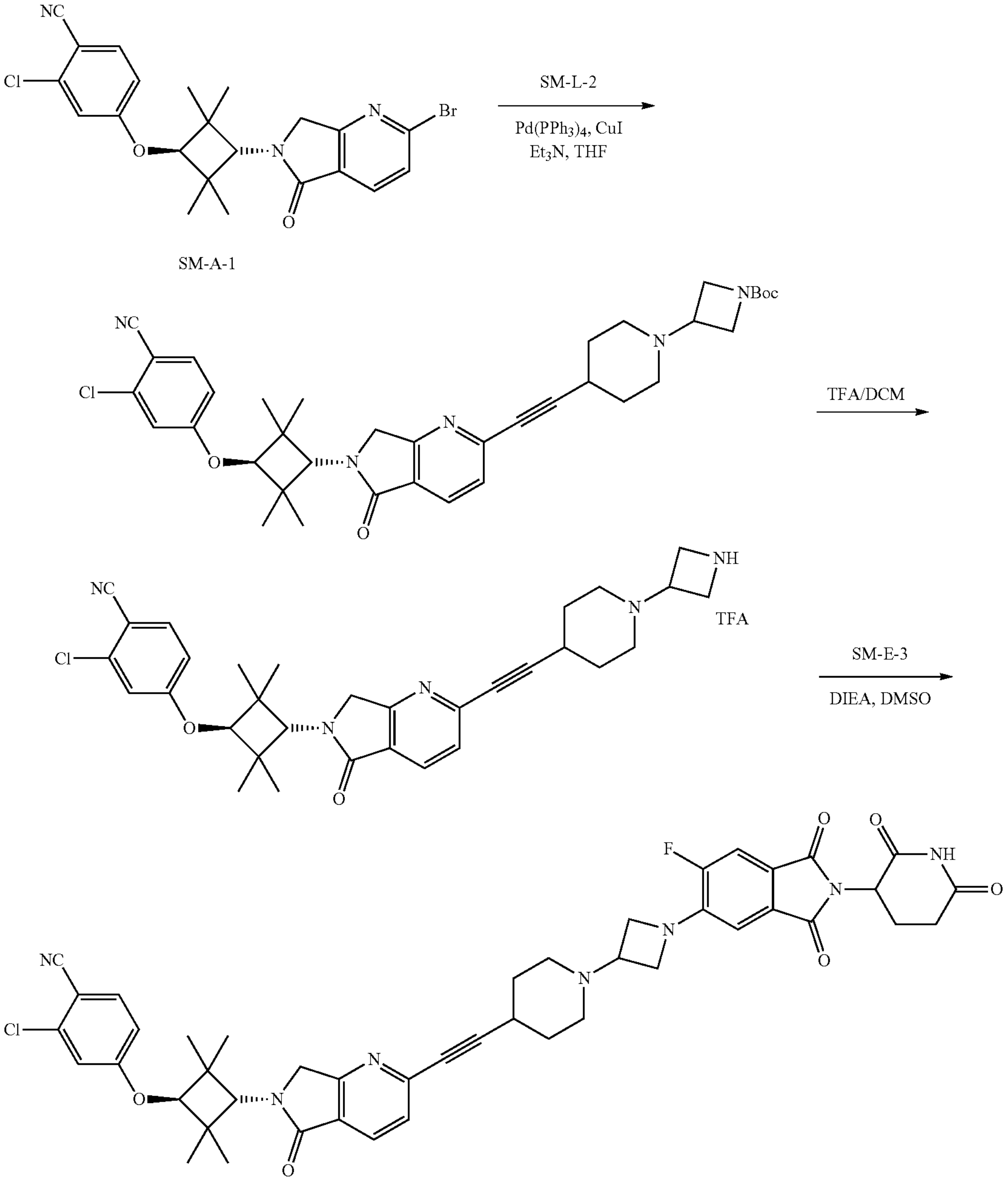

318

$^1H$ NMR (400 MHz, DMSO-$d_6$) δ 11.07 (s, 1H), 8.03 (d, J=7.9 Hz, 1H), 7.88 (d, J=8.8 Hz, 1H), 7.56 (dd, J=17.6, 9.5 Hz, 2H), 7.27 (d, J=2.4 Hz, 1H), 7.04 (dd, J=8.8, 2.4 Hz, 1H), 6.90 (d, J=7.7 Hz, 1H), 5.05 (dd, J=12.8, 5.3 Hz, 1H), 4.78 (s, 2H) 4.52 (s, 1H), 4.32 (s, 1H), 4.26-4.09 (m, 2H), 4.04-3.84 (m, 2H) 2.91-2.72 (m, 2H), 2.68-2.58 (m, 2H), 2.58-2.49 (m, 2H), 2.42-2.22 (m, 1H), 2.22-2.05 (m, 2H), 2.04-1.87 (m, 3H), 1.74-1.56 (m, 2H), 1.38 (s, 6H), 1.14 (s, 6H). MS: calcd. for $C_{45}H_{43}ClFN_7O_6[M+H]^+$: 832.3; found: 831.7.
319: 2-Chloro-4-((1r,3r)-3-(2-((1-(1-(2-(2,6-dioxopiperidin-3-yl)-1,3-dioxoisoindolin-5-yl)piperidine-4-yl)azelaic acid-3-yl)ethynyl)-5-oxo-5H-pyrrolo[3,4-b]pyridin-6(7H)-yl)-2,2,4,4-tetramethylcyclobutoxy) benzonitrile
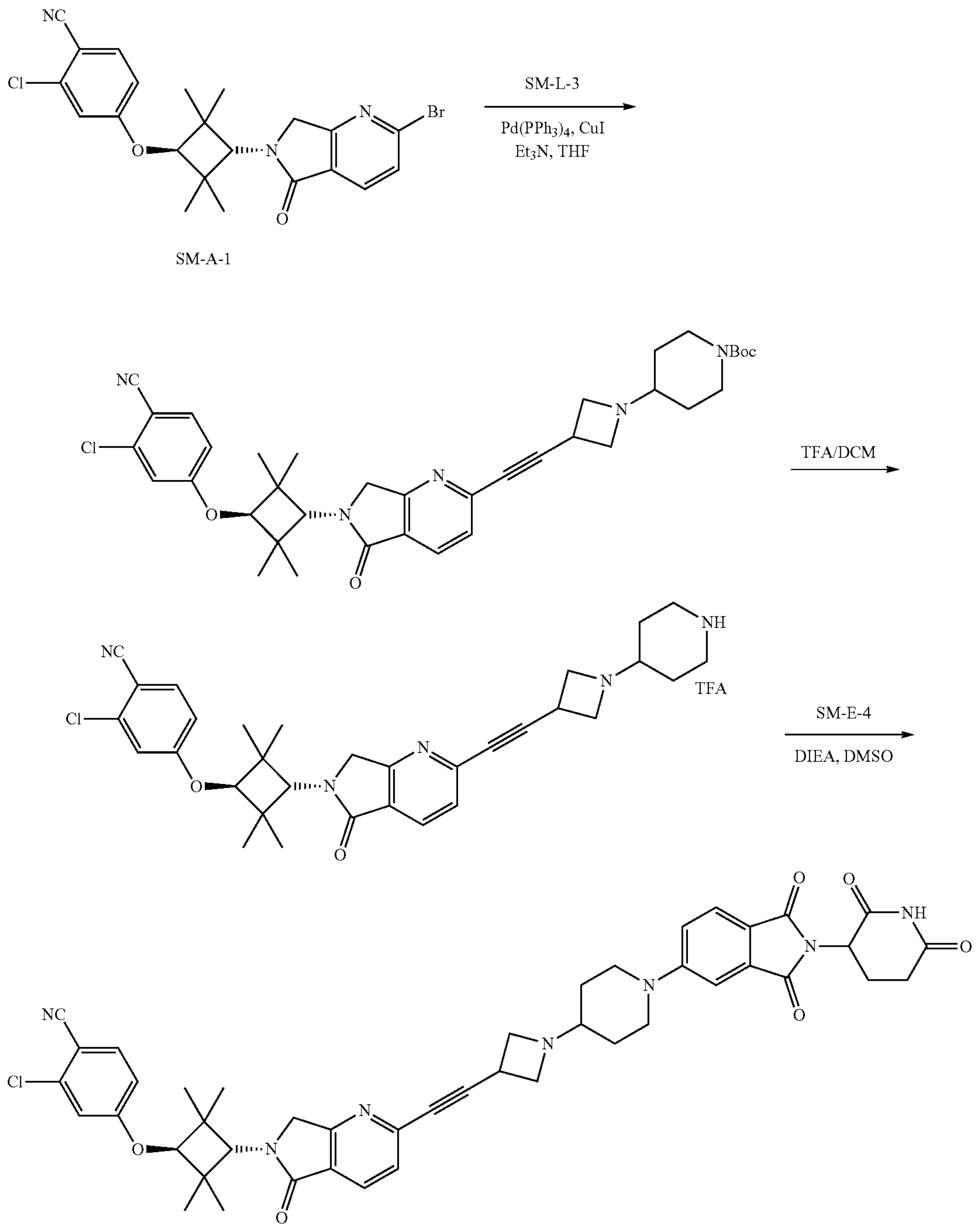
319

$^1$H NMR (400 MHz, DMSO-$d_6$) δ 11.06 (s, 1H), 8.04 (d, J=7.9 Hz, 1H), 7.88 (d, J=8.8 Hz, 1H), 7.64 (d, J=8.5 Hz, 1H), 7.57 (d, J=7.9 Hz, 1H), 7.39-7.15 (m, 3H), 7.05 (dd, J=8.8, 2.4 Hz, 1H), 5.04 (dd, J=12.8, 5.4 Hz, 1H), 4.78 (s, 2H), 4.52 (s, 1H), 4.31 (s, 1H), 3.83 (d, J=12.9 Hz, 2H), 3.60 (s, 2H), 3.51-3.45 (m, 1H), 3.18-2.99 (m, 4H), 2.91-2.79 (m, 1H), 2.61-2.50 (m, 2H), 2.40-2.32 (m, 1H), 2.01-1.96 (m, 1H), 1.77-1.63 (m, 2H), 1.36 (s, 6H), 1.29-1.22 (m, 2H), 1.14 (s, 6H). MS: calcd. for $C_{45}H_{44}ClN_7O_6$ $[M+H]^+$: 814.3; found: 814.3.
320: 2-Chloro-4-((1r,3r)-3-(2-((1-(1-(2-(2,6-dioxopiperidin-3-yl)-6-fluoro-1,3-dioxoisoindolin-5-yl)piperidine-4-yl)azelaic acid-3-yl)ethynyl)-5-oxo-5H-pyrrolino[3,4-b]pyridin-6(7H)-yl)-2,2,4,4-tetramethylcyclobutoxy)benzonitrile
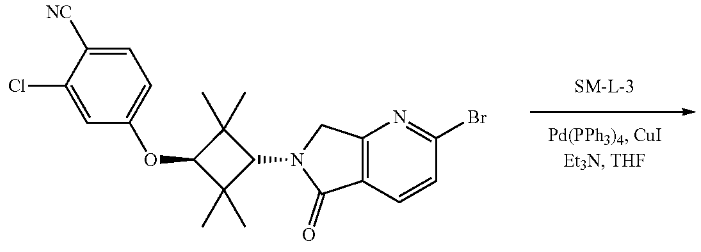
SM-A-1
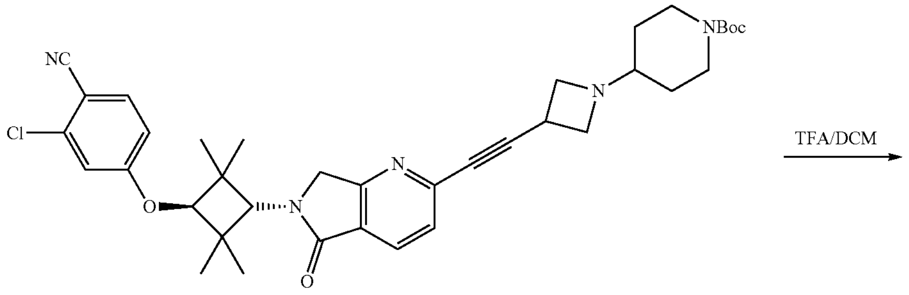
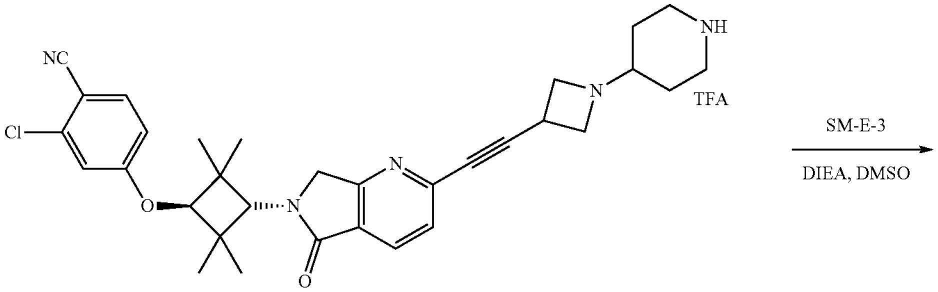

-continued
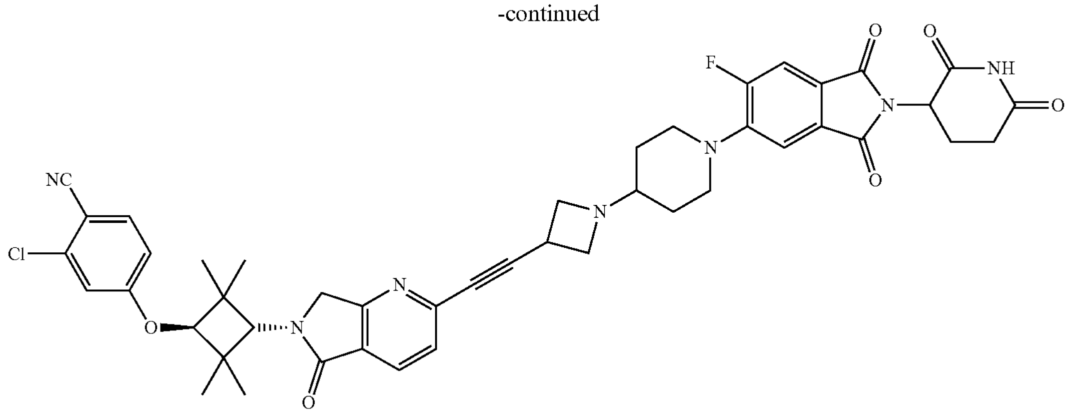
320
$^{1}H$ NMR (400 MHz, DMSO-$d_6$) δ 11.09 (s, 1H), 8.05 (d, J=7.1 Hz, 1H), 7.89 (d, J=8.8 Hz, 1H), 7.69 (d, J=11.6 Hz, 1H), 7.58 (d, J=7.6 Hz, 1H), 7.43 (d, J=7.7 Hz, 1H), 7.27 (d, J=2.2 Hz, 1H), 7.05 (dd, J=8.8, 2.2 Hz, 1H), 5.08 (dd, J=12.4, 5.3 Hz, 1H), 4.79 (s, 2H), 4.53 (s, 1H), 4.32 (s, 1H), 3.66-3.44 (m, 4H), 3.14-3.07 (m, 1H), 2.99-2.78 (m, 3H), 2.63-2.52 (m, 2H), 2.32-2.20 (m, 2H), 2.06-1.90 (m, 2H), 1.83-1.68 (m, 2H), 1.49-1.22 (m, 8H), 1.14 (s, 6H). MS: calcd. for $C_{45}H_{43}ClFN_7O_6$ $[M+H]^+$: 832.3; found: 832.3.
321: 2-Chloro-4-((1r,3r)-3-(2-((1'-(2,6-dioxopiperidin-3-yl)-1,3-dioxoisoindolin-5-yl)-1,3'-diazolidin-3-yl)ethynyl)-5-oxo-5H-pyrrolo[3,4-b]pyridin-6(7H)-yl)-2,2,4,4-tetramethylcyclobutoxy)benzonitrile
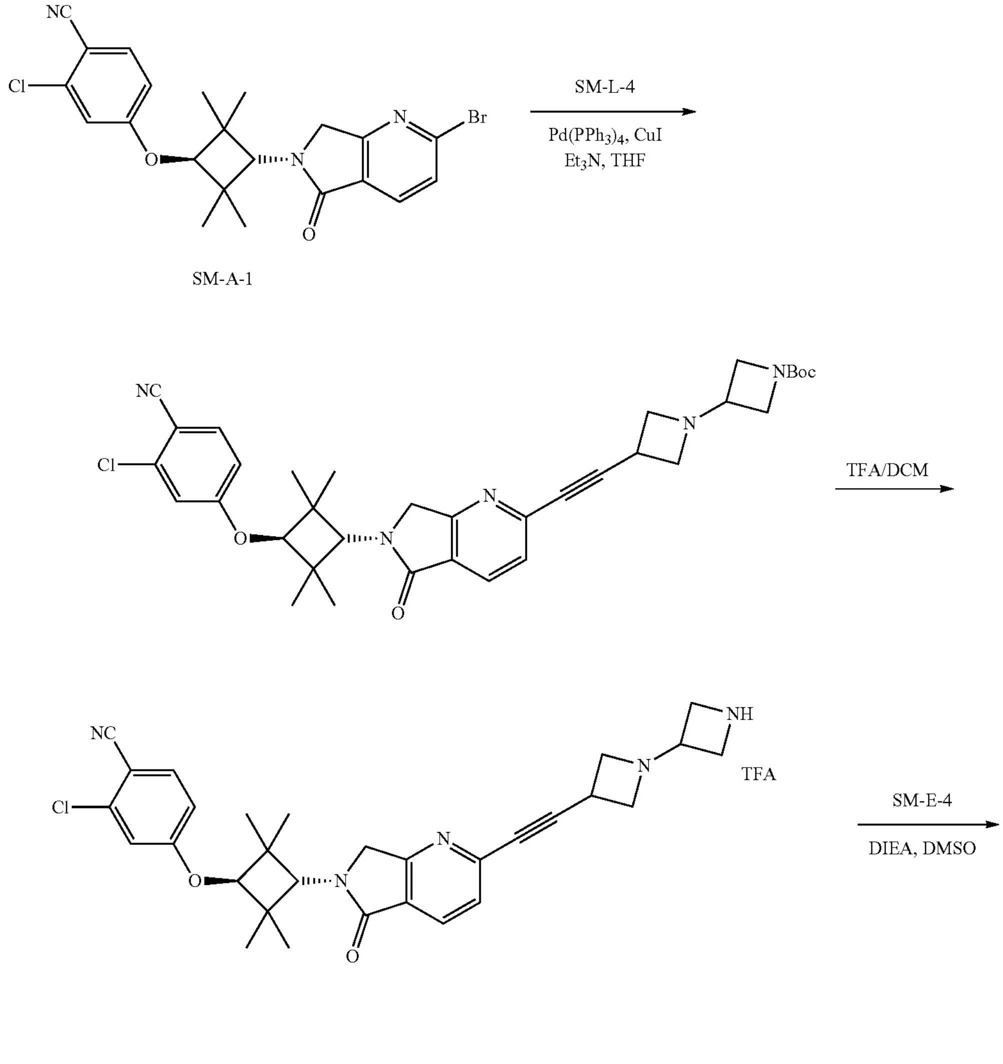

-continued
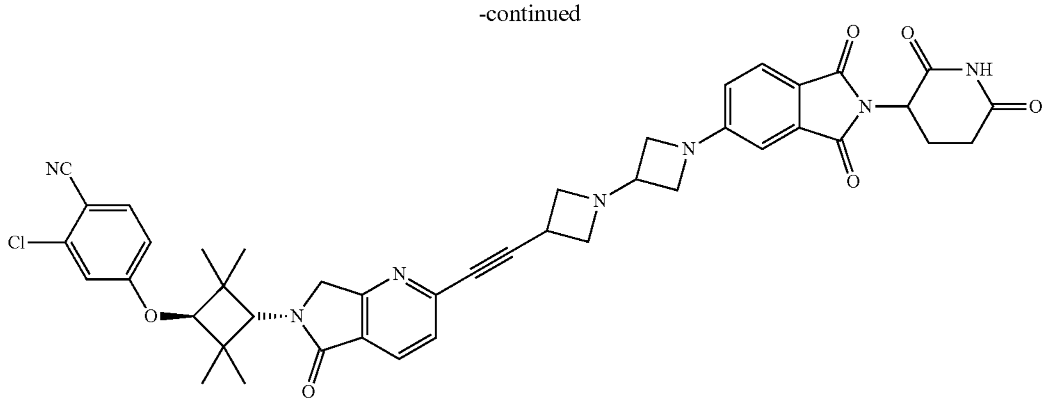
321
$^{1}$H NMR (400 MHz, DMSO-$d_6$) δ 11.05 (s, 1H), 8.05 (d, J=7.9 Hz, 1H), 7.88 (d, J=8.8 Hz, 1H), 7.60 (d, J=18.3, 8.1 Hz, 2H), 7.27 (d, J=2.4 Hz, 1H), 7.05 (d, J=8.8, 2.4 Hz, 1H), 6.77 (d, J=1.9 Hz, 1H), 6.64 (d, J=8.4, 2.0 Hz, 1H), 5.03 (dd, J=12.9, 5.4 Hz, 1H), 4.78 (s, 2H), 4.52 (s, 1H), 4.31 (s, 1H), 4.03 (t, J=7.9 Hz, 2H), 3.81 (dd, J=8.8, 4.1 Hz, 2H), 3.64-3.52 (m, 4H), 3.25 (d, J=15.6, 9.3 Hz, 2H), 2.95-2.75 (m, 1H), 2.56-2.50 (m, 2H), 2.08-1.90 (m, 1H), 1.38 (s, 6H), 1.14 (s, 6H). MS: calcd. for $C_{43}H_{40}ClN_7O_6$ $[M+H]^+$: 786.3; found:785.8.
322: 2-Chloro-4-((1r,3r)-3-(2-((1'-(2,6-dioxopiperidin-3-yl)-6-fluoro-1,3-dioxoisoindolin-5-yl)-1,3'-diazolidin-3-yl)ethynyl)-5-oxo-5H-pyrrolo[3,4-b]pyridin-6(7H)-yl)-2,2,4,4-tetramethylcyclobutoxy)benzonitrile
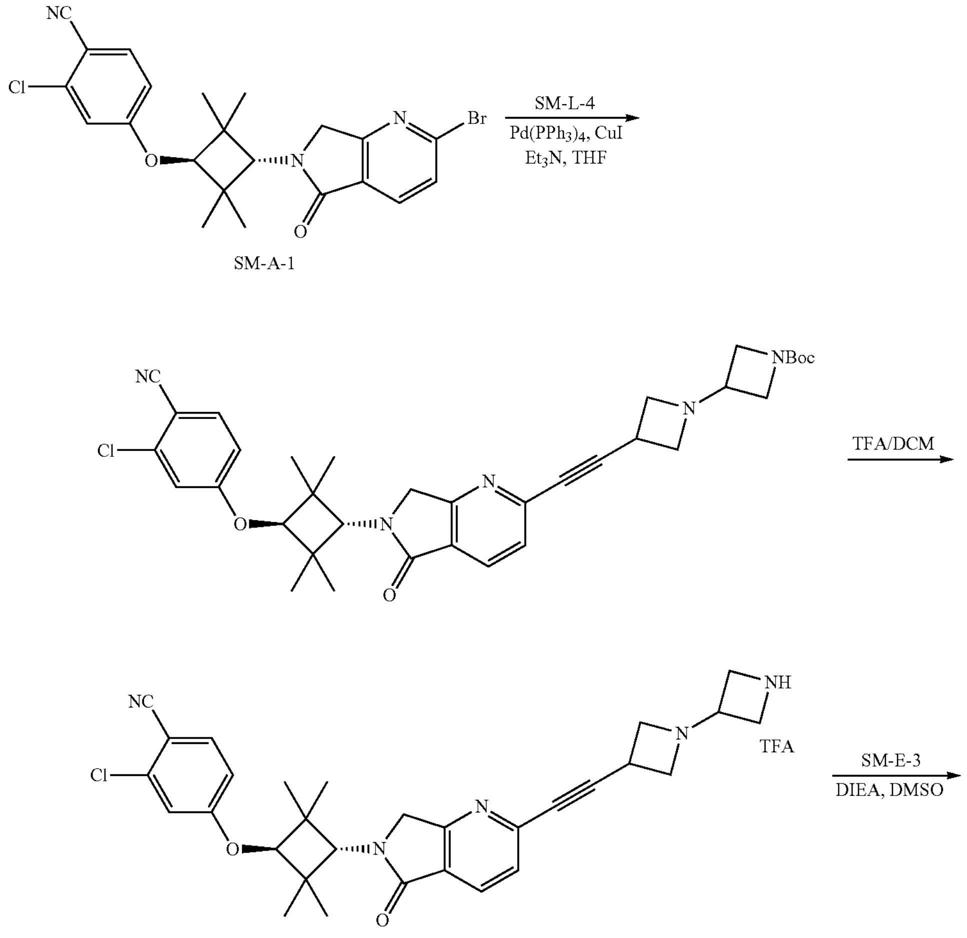

-continued
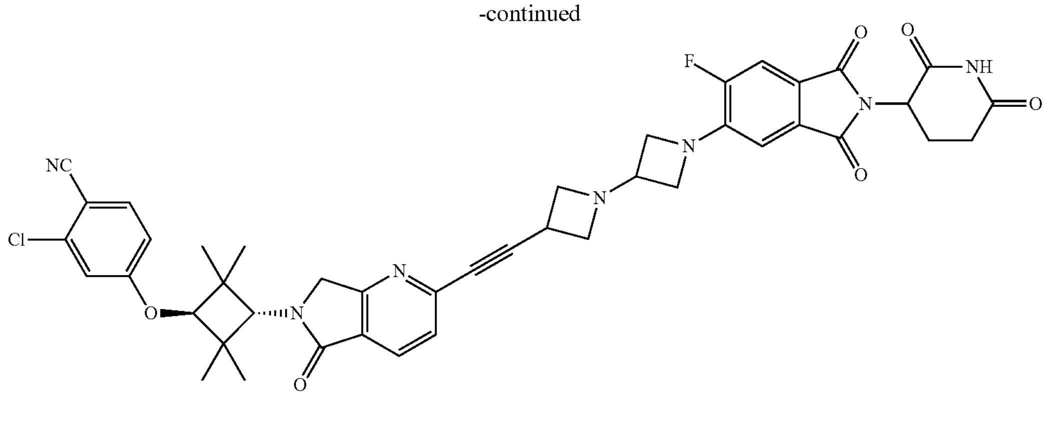
322
$^1$H NMR (400 MHz, DMSO-$d_6$) δ 11.07 (s, 1H), 8.05 (d, J=7.8 Hz, 1H), 7.89 (d, J=8.8 Hz, 1H), 7.64-7.53 (m, 2H), 7.27 (d, J=1.9 Hz, 1H), 7.05 (d, J=8.6 Hz, 1H), 6.90 (d, J=7.7 Hz, 1H), 5.04 (d, J=12.8, 5.5 Hz, 1H), 4.78 (s, 2H), 4.53 (s, 1H), 4.31 (s, 1H), 4.18 (s, 2H), 3.94 (s, 2H), 3.72-3.48 (m, 4H), 3.25 (d, J=6.5 Hz, 2H), 2.85 (t, J=12.8 Hz, 1H), 2.69-2.53 (m, 2H), 2.09-1.89 (m, 1H), 1.38 (s, 6H), 1.14 (s, 6H). MS: calcd. for $C_{43}H_{39}ClFN_7O_6$ $[M+H]^+$: 804.3; found: 804.2.
323: 2-Chloro-4-((1r,4r)-4-(2-((1'-(2,6-dioxopiperidin-3-yl)-1,3-dioxoisoindolin-5-yl)-1,4'-dipiperidine-4-yl)ethynyl)-5-oxo-5H-pyrrolo[3,4-b]pyridin-6(7H)-yl) cyclohexaneoxy)benzonitrile
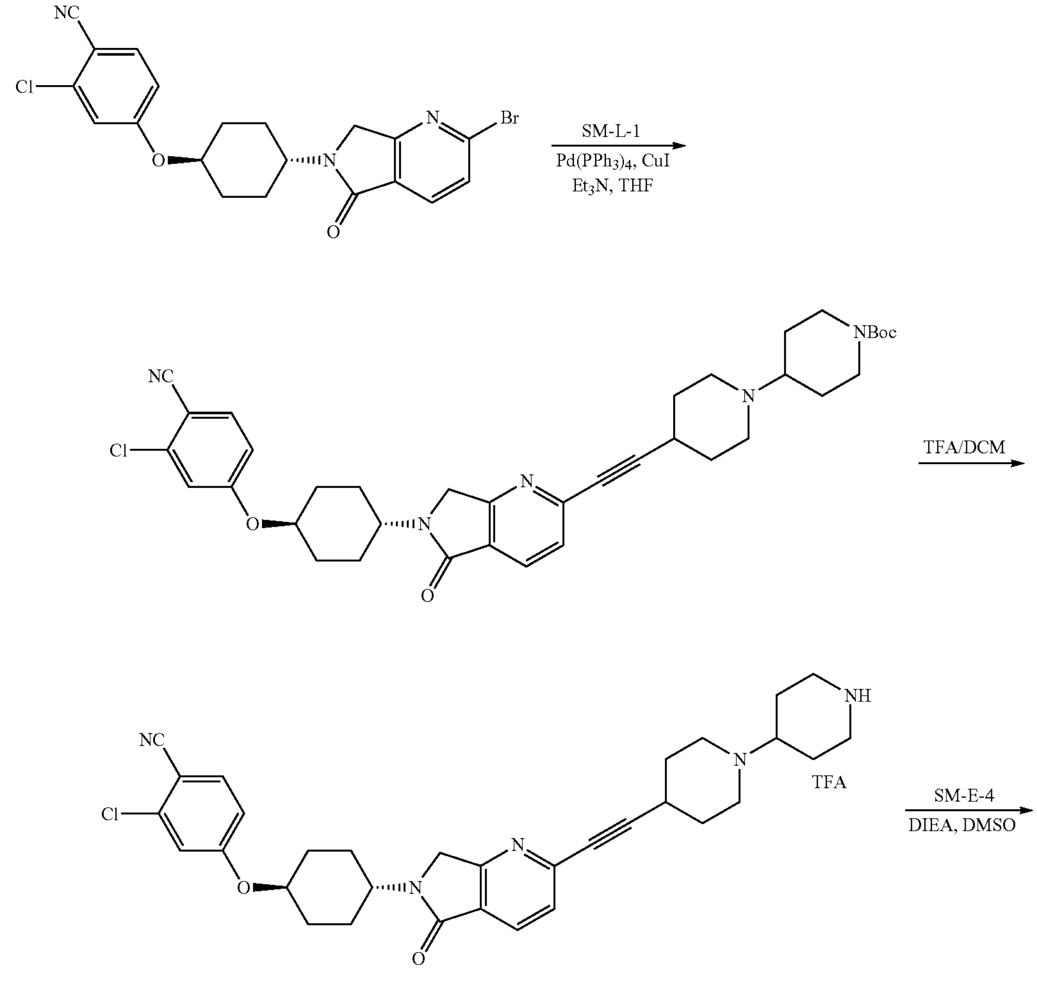

-continued
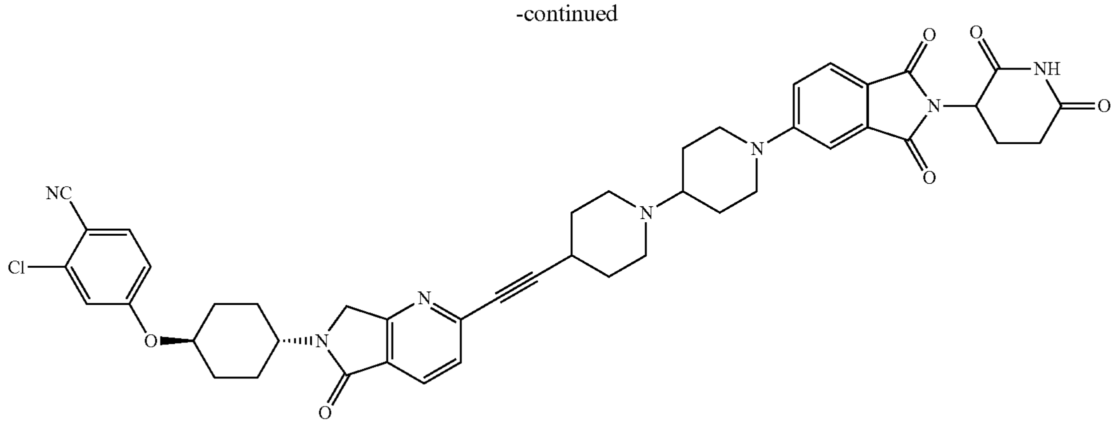
323
$^1$H NMR (400 MHz, DMSO-$d_6$) δ 11.06 (s, 1H), 8.01 (d, J=7.9 Hz, 1H), 7.85 (d, J=8.8 Hz, 1H), 7.63 (d, J=8.5 Hz, 1H), 7.51 (d, J=7.9 Hz, 1H), 7.39 (d, J=2.3 Hz, 1H), 7.30 (s, 1H), 7.23 (d, J=8.5 Hz, 1H), 7.11 (dd, J=8.8, 2.3 Hz, 1H), 5.04 (dd, J=12.9, 5.3 Hz, 1H), 4.56 (d, J=10.7 Hz, 1H), 4.45 (s, 2H), 4.14-4.01 (m, 3H), 3.01-2.64 (m, 6H), 2.56-2.50 (m, 3H), 2.310-2.32 (m, 2H), 2.13 (d, J=10.3 Hz, 2H), 2.03-1.93 (m, 1H), 1.90-1.80 (m, 8H), 1.71-1.40 (m, 6H). MS: calcd. for $C_{45}H_{44}ClN_7O_6$ $[M+H]^+$: 814.3; found:814.3.
324: 2-Chloro-4-((1r,4r)-4-(2-((1'-(2,6-dioxopiperidin-3-yl)-6-fluoro-1,3-dioxoisoindolin-5-yl)-1,4'-dipiperidine-4-yl)ethynyl)-5-oxo-5H-pyrrolo[3,4-b]pyridin-6(7H)-cyclohexaneoxy)benzonitrile
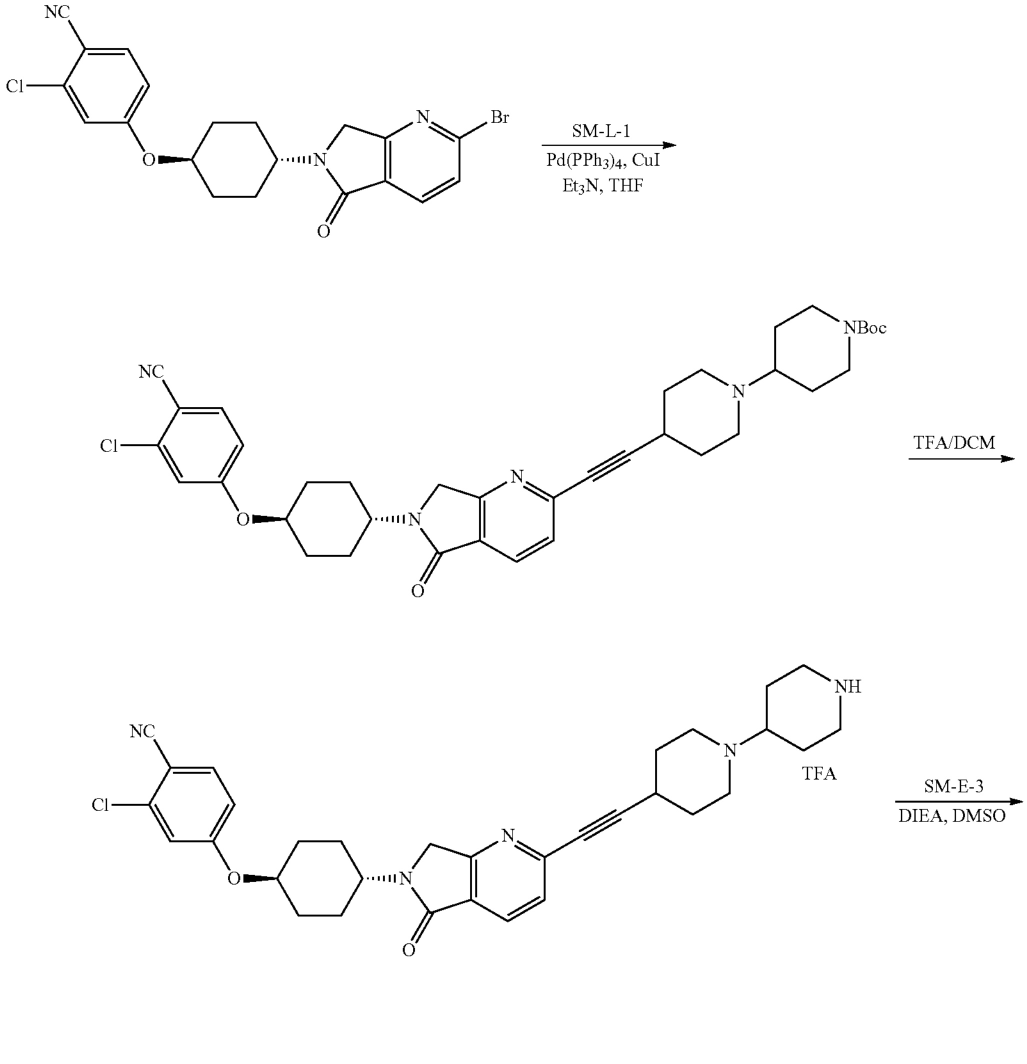

-continued
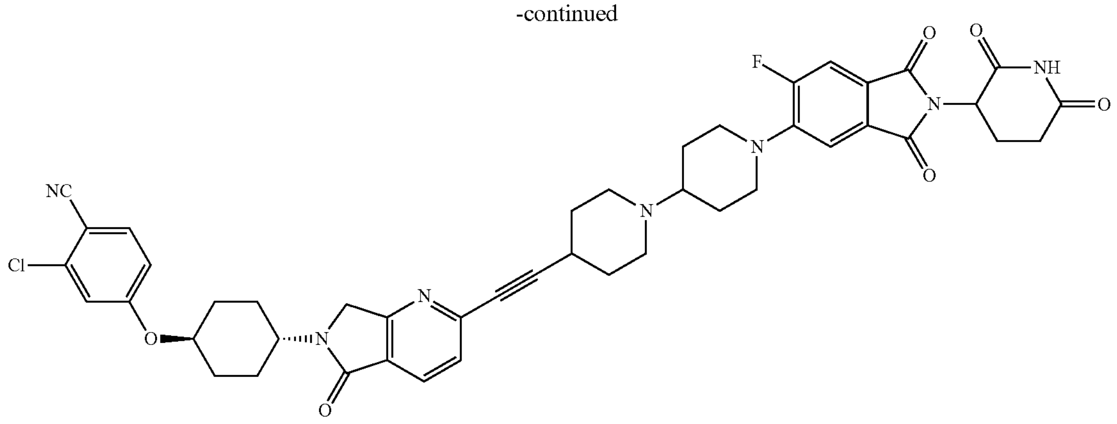
324
$^1$H NMR (400 MHz, DMSO-$d_6$) δ 11.11 (s, 1H), 8.04 (d, J=7.9 Hz, 1H), 7.87 (d, J=8.8 Hz, 1H), 7.71 (d, J=11.4 Hz, 1H), 7.55 (d, J=7.9 Hz, 1H), 7.45 (d, J=7.4 Hz, 1H), 7.41 (d, J=2.4 Hz, 1H), 7.13 (dd, J=8.8, 2.4 Hz, 1H), 5.10 (dd, J=12.8, 5.3 Hz, 1H), 4.59 (t, J=10.8 Hz, 1H), 4.47 (s, 2H), 4.22-4.08 (m, 1H), 3.67 (d, J=11.6 Hz, 2H), 2.98-2.68 (m, 6H), 2.63-2.52 (m, 2H), 2.35-2.32 (m, 2H), 2.16 (d, J=10.7 Hz, 2H), 2.08-1.76 (m, 10H), 1.65-1.56 (m, 6H). MS: calcd. for $C_{45}H_{43}ClFN_7O_6$ $[M+H]^+$: 832.3; found: 832.2.
325: 2-Chloro-4-((1r,3r)-3-(2-((1r,4r)-4-(4-(2-(2,6-dioxopiperidin-3-yl)-1,3-dioxoisoindolin-5-yl)piperazin-1-yl)cyclohexyl)ethynyl)-5-oxo-5H-pyrrolo[3,4-b]pyridin-6(7H)-yl)-2,2,4,4-tetramethylcyclobutoxy)benzonitrile
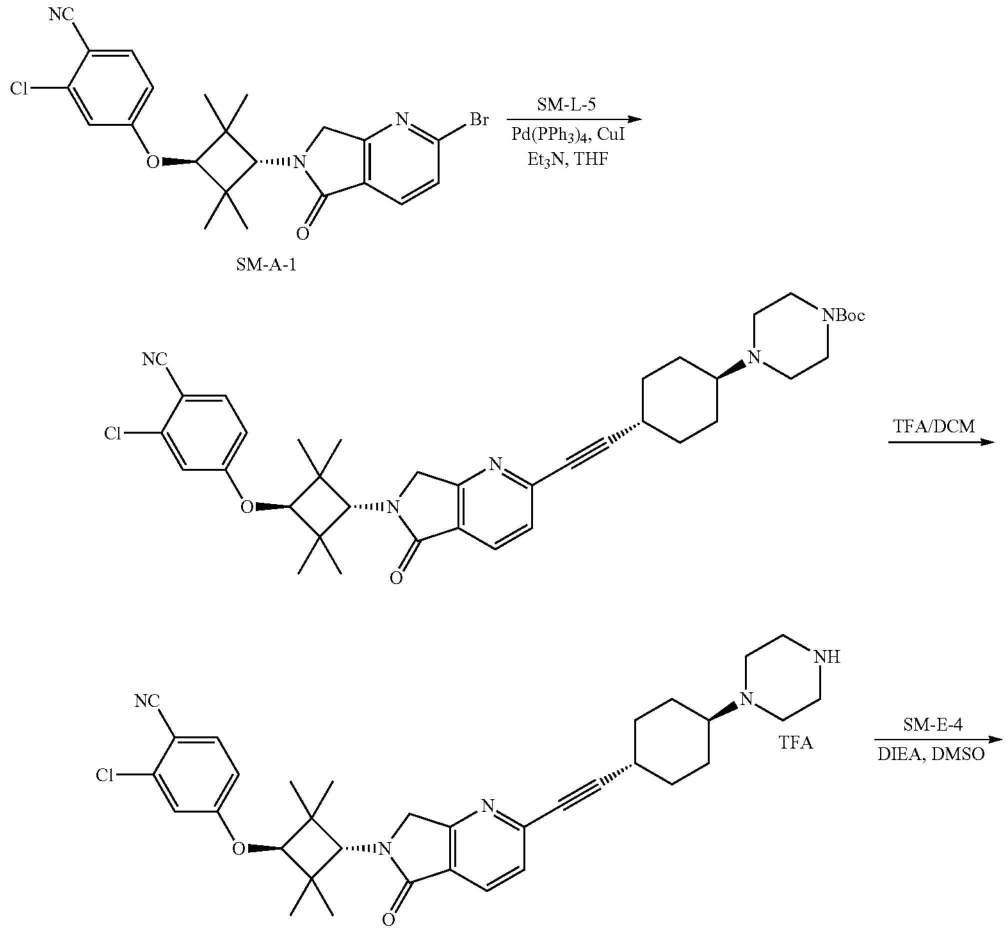

-continued
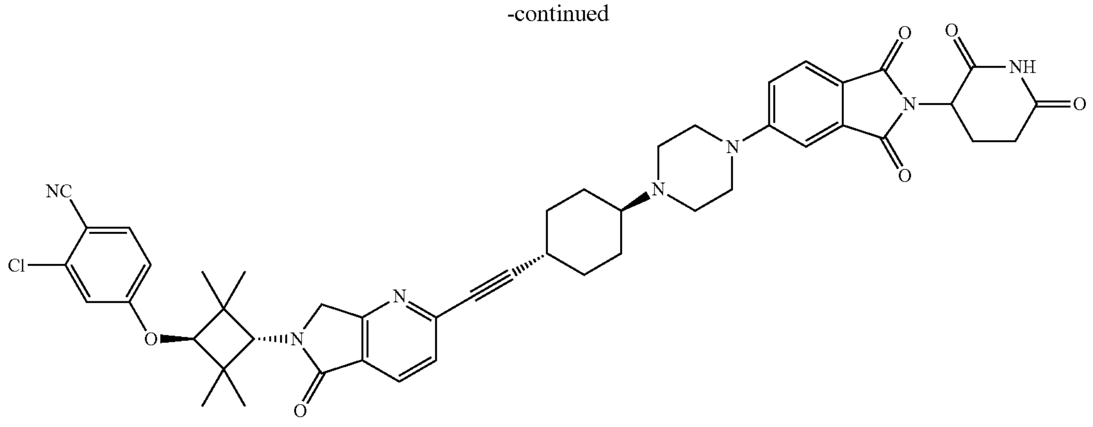
325
$^1$H NMR (400 MHz, DMSO-$d_6$) δ 11.09 (s, 1H), 8.04 (d, J=7.9 Hz, 1H), 7.90 (d, J=8.7 Hz, 1H), 7.68 (d, J=8.5 Hz, 1H), 7.54 (d, J=7.9 Hz, 1H), 7.33 (s, 1H), 7.27 (dd, J=12.2, 5.5 Hz, 2H), 7.06 (dd, J=8.8, 2.3 Hz, 1H), 5.07 (dd, J=12.9, 5.3 Hz, 1H), 4.79 (s, 2H), 4.54 (s, 1H), 4.33 (s, 1H), 3.42 (s, 4H), 2.96-2.81 (m, 1H), 2.71-2.56 (m, 6H), 2.36 (d, J=24.4 Hz, 2H), 2.17-1.95 (m, 3H), 1.86 (d, J=10.3 Hz, 2H), 1.55-1.29 (m, 10H), 1.16 (s, 6H). MS: calcd. for $C_{47}H_{48}ClN_7O_6$ $[M+H]^+$: 842.3; found: 842.2.
326: 2-Chloro-4-((1r,3r)-3-(2-((1r,4r)-4-(4-(2-(2,6-dioxopiperidin-3-yl)-6-fluoro-1,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)benzonitrile
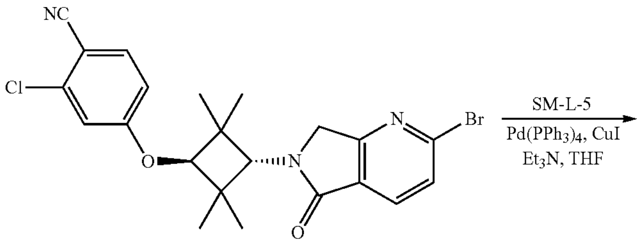
SM-A-1
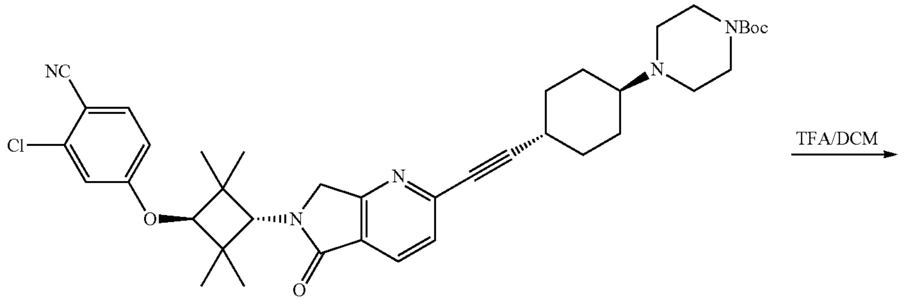
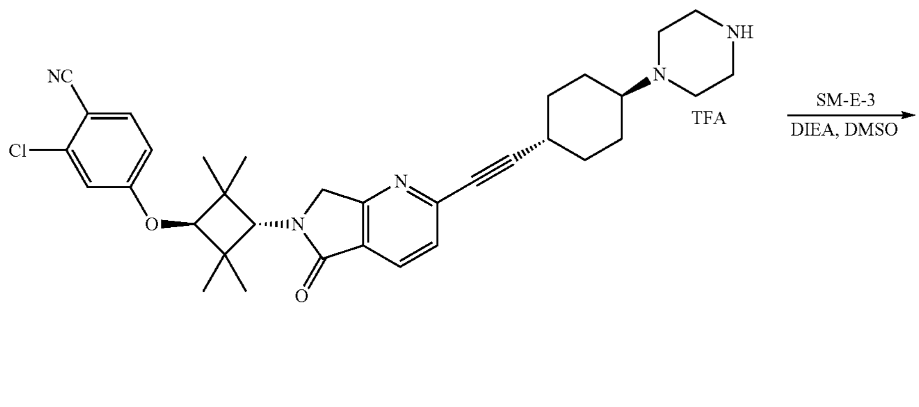

-continued
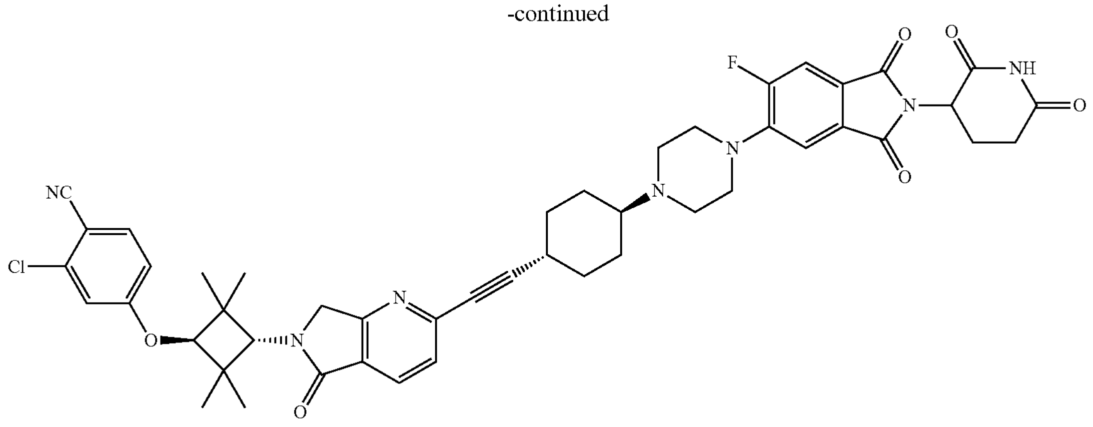
325
$^1$H NMR (400 MHz, DMSO-$d_6$) δ 11.09 (s, 1H), 8.02 (d, J=7.9 Hz, 1H), 7.89 (d, J=8.7 Hz, 1H), 7.71 (d, J=11.5 Hz, 1H), 7.52 (d, J=7.9 Hz, 1H), 7.42 (d, J=7.4 Hz, 1H), 7.27 (d, J=2.4 Hz, 1H), 7.05 (dd, J=8.8, 2.4 Hz, 1H), 5.08 (dd, J=12.8, 5.4 Hz, 1H), 4.78 (s, 2H), 4.52 (s, 1H), 4.31 (s, 1H), 3.21 (s, 4H), 2.85 (dd, J=21.2, 9.5 Hz, 1H), 2.65 (s, 4H), 2.60-2.55 (m, 2H), 2.32-2.21 (m, 2H), 2.11-1.96 (m, 3H), 1.85 (d, J=10.6 Hz, 2H), 1.51-1.28 (m, 10H), 1.14 (s, 6H). MS: calcd. for $C_{47}H_{47}ClFN_7O_6$ $[M+H]^+$: 860.3; found: 860.3.
327: 2-Chloro-4-((1r,3r)-3-(2-((3-(1-(2-(2,6-dioxopiperidin-3-yl)-1,3-dioxoisoindolin-5-yl)piperidine-4-ylamino)cyclobutyl)ethynyl)-5-oxo-5,7-dihydro-pyrrolo[3,4-b]pyridin-6-yl)-2,2,4,4-tetramethylcyclobutoxy)benzonitrile
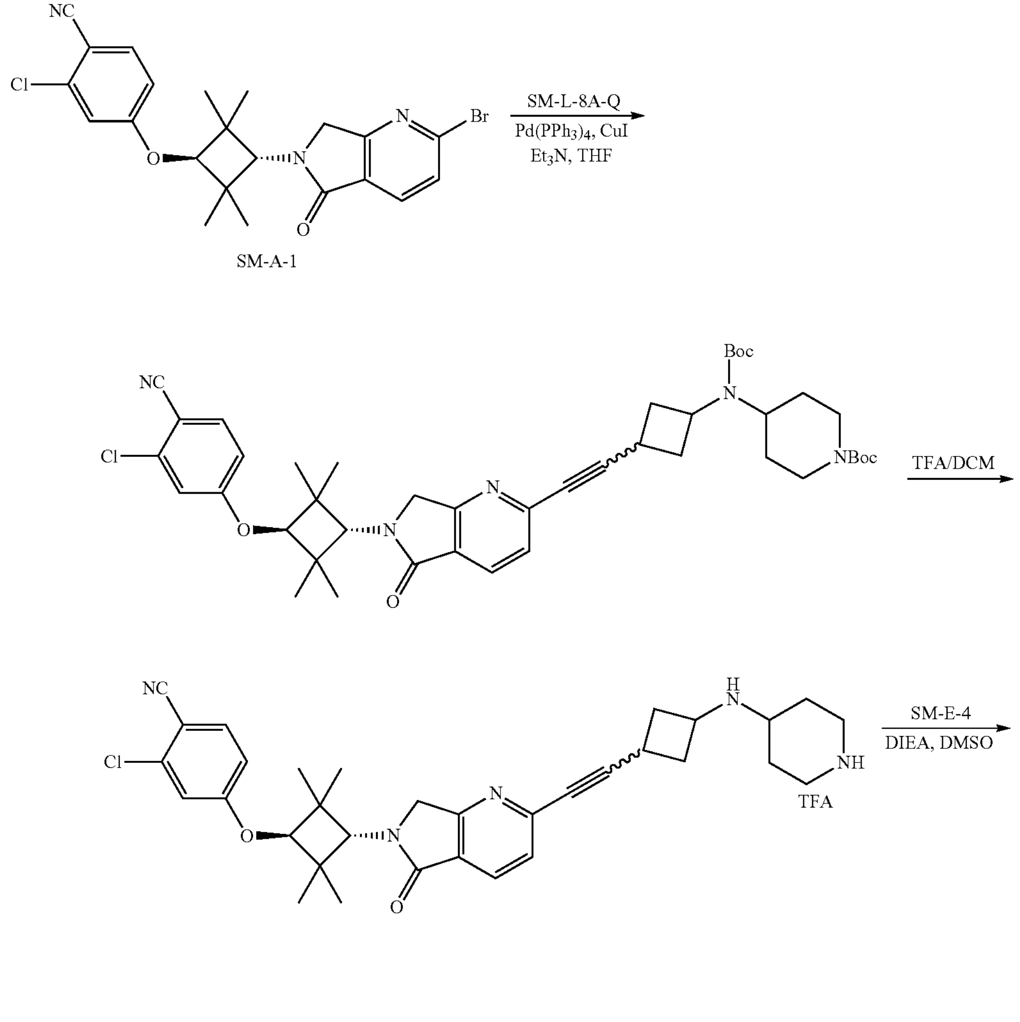

-continued
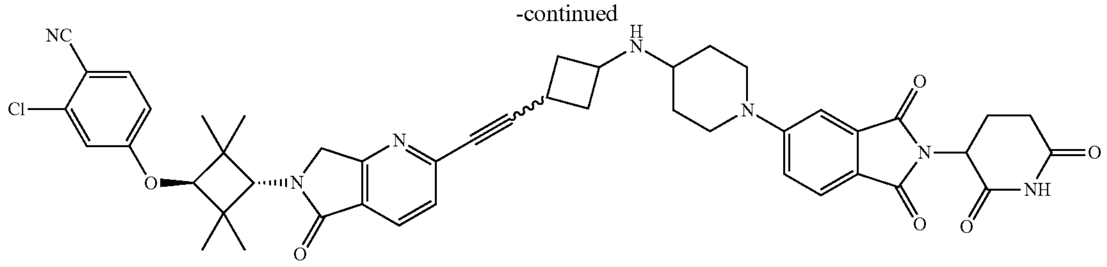
327
$^1$H NMR (400 MHz, DMSO-$d_6$) δ 11.08 (s, 1H), 8.05 (d, J=7.9 Hz, 1H), 7.91 (d, J=8.8 Hz, 1H), 7.66 (d, J=8.6 Hz, 1H), 7.58 (d, J=7.9 Hz, 1H), 7.35-7.28 (m, 2H), 7.24 (dd, J=8.7, 2.0 Hz, 1H), 7.07 (dd, J=8.8, 2.4 Hz, 1H), 5.07 (dd, J=12.9, 5.4 Hz, 1H), 4.81 (s, 2H), 4.55 (s, 1H), 4.34 (s, 1H), 3.96 (d, J=13.6 Hz, 2H), 3.67 (s, 1H), 3.27-3.17 (m, 1H), 3.05 (t, J=11.3 Hz, 2H), 2.94-2.83 (m, 1H), 2.72-2.74 (m, 1H), 2.63-2.55 (m, 1H), 2.34 (d, J=7.9 Hz, 4H), 2.19-2.21 (m, 2H), 2.05-1.94 (m, 1H), 1.84 (d, J=10.8 Hz, 2H), 1.39 (d, J=12.4 Hz, 6H), 1.32-1.23 (m, 2H), 1.16 (s, 6H). MS: calcd. for $C_{46}H_{46}ClN_7O_6$ $[M+H]^+$: 828.3; found: 828.3.
328: 2-Chloro-4-((1r,3r)-3-(2-((3-(1-(2-(2,6-dioxopiperidin-3-yl)-1,3-dioxoisoindolin-5-yl)piperidine-4-ylamino)cyclobutyl)ethynyl)-5-oxo-5,7-dihydro-6H-pyrrolo[3,4-b]pyridin-6-yl)-2,2,4,4-tetramethylcyclobutoxy) benzonitrile
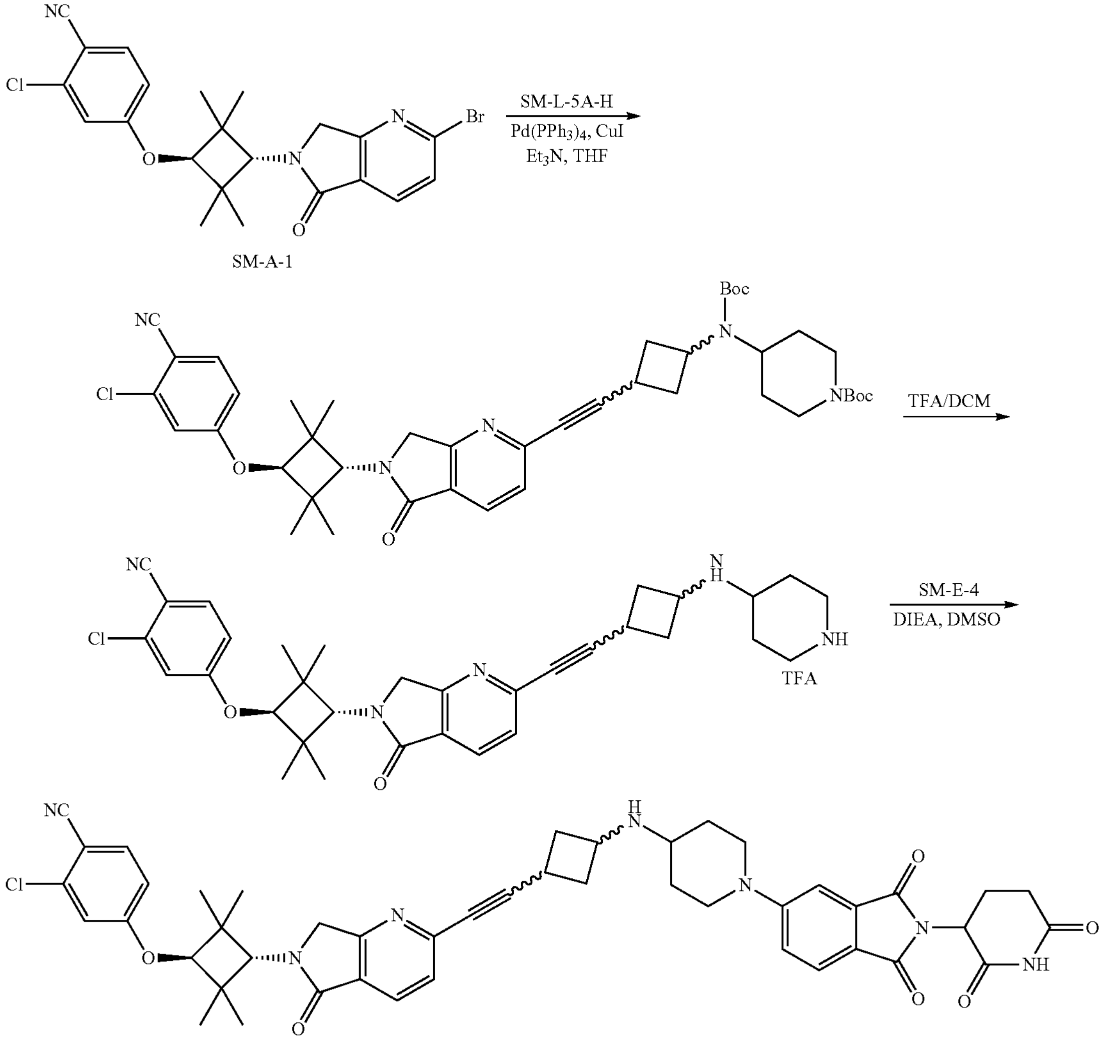
325

$^1H$ NMR (400 MHz, DMSO-$d_6$) δ 11.06 (s, 1H), 8.02 (d, J=7.9 Hz, 1H), 7.89 (d, J=8.8 Hz, 1H), 7.63 (d, J=8.5 Hz, 1H), 7.51 (d, J=7.9 Hz, 1H), 7.35-7.23 (m, 2H), 7.21 (d, J=6.6 Hz, 1H), 7.05 (dd, J=8.8, 2.4 Hz, 1H), 5.04 (dd, J=12.9, 5.4 Hz, 1H), 4.76 (s, 2H), 4.52 (s, 1H), 4.31 (s, 1H), 3.93 (d, J=13.4 Hz, 2H), 3.28-3.15 (m, 2H), 3.03 (t, J=11.2 Hz, 2H), 2.96-2.79 (m, 2H), 2.75-2.51 (m, 4H), 2.04-1.84 (m, 3H), 1.80 (d, J=9.6 Hz, 2H), 1.38 (s, 6H), 1.33-1.22 (m, 2H), 1.14 (s, 6H). MS: calcd. for $C_{46}H_{46}ClN_7O_6$ ($[M+H]^+$: 828.3; found: 828.3.

329: 2-Chloro-4-((1r,3r)-3-(2-((3-(1-(2,6-dioxopiperidin-3-yl)-6-fluoro-1,3-dioxoisoindolin-5-yl)piperidine-4-ylamino)cyclobutyl)ethynyl)-5-oxo-5,7-dihydro-6H-pyrrolo[3,4-b]pyridin-6-yl)-2,2,4,4-tetramethylcyclobutoxy) benzonitrile

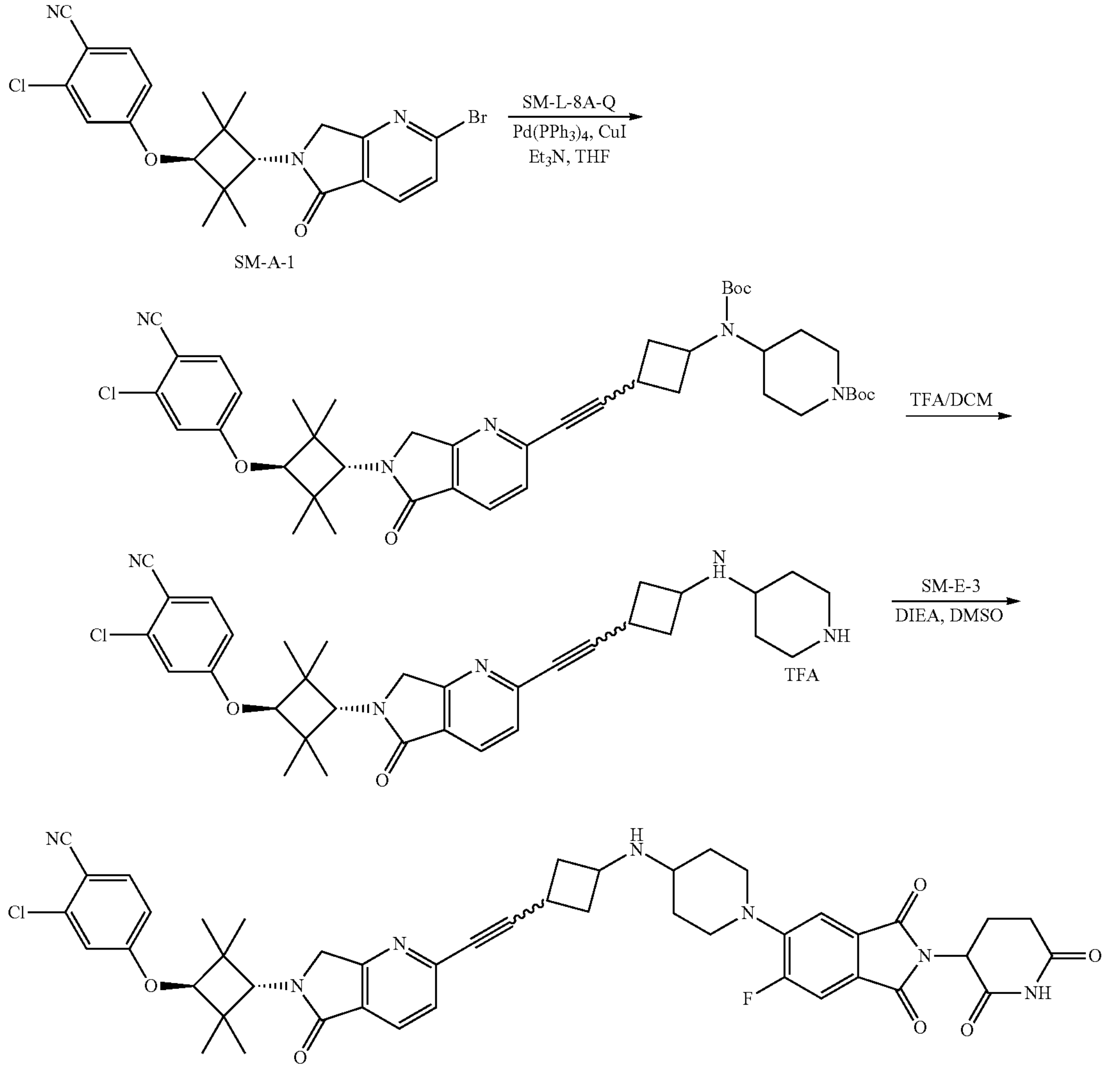

SM-A-1

329

$^1H$ NMR (400 MHz, DMSO-$d_6$) δ 11.09 (s, 1H), 8.03 (d, J=7.9 Hz, 1H), 7.89 (d, J=8.8 Hz, 1H), 7.68 (d, J=11.5 Hz, 1H), 7.55 (d, J=7.9 Hz, 1H), 7.42 (d, J=7.5 Hz, 1H), 7.27 (d, J=2.4 Hz, 1H), 7.05 (dd, J=8.8, 2.4 Hz, 1H), 5.08 (dd, J=12.8, 5.4 Hz, 1H), 4.78 (s, 2H), 4.53 (s, 1H), 4.32 (s, 1H), 3.69-3.58 (m, 1H), 3.54 (d, J=12.1 Hz, 2H), 3.25 (d, J=4.8 Hz, 1H), 2.90-2.75 (m, 3H), 2.61-2.53 (m, 1H), 2.43-2.25 (m, 4H), 2.16 (d, J=9.4 Hz, 2H), 2.03-1.96 (m, 1H), 1.85 (d, J=11.3 Hz, 2H), 1.41-1.38 (m, 8H), 1.14 (s, 6H). MS: calcd. for $C_{46}H_{45}ClFN_7O_6$ $[M+H]^+$: 846.3; found:846.3.

330: 2-Chloro-4-((1r,3r)-3-(2-((3-(1-(2,6-dioxopiperidin-3-yl)-6-fluoro-1,3-dioxoisoindolin-5-yl)piperidine-4-ylamino)cyclobutyl)ethynyl)-5-oxo-5,7-dihydro-6H-pyrrolo[3,4-b]pyridin-6-yl)-2,2,4,4-tetramethylcyclobutoxy) benzonitrile
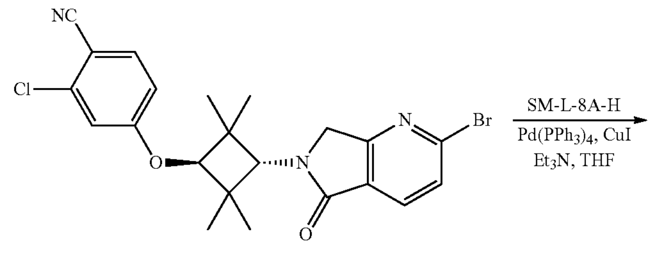
SM-A-1
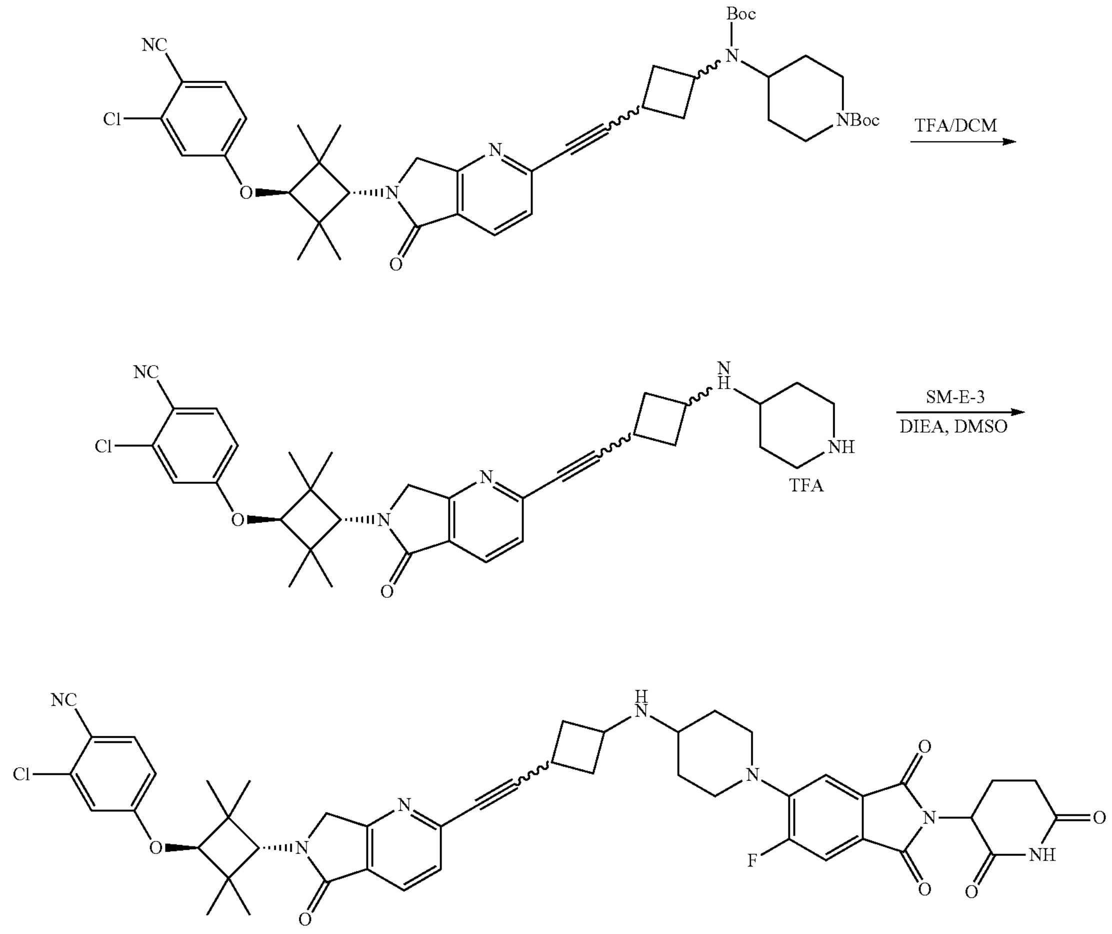
330
$^1$H NMR (400 MHz, DMSO-$d_6$) δ 11.09 (s, 1H), 8.02 (d, J=7.9 Hz, 1H), 7.89 (d, J=8.8 Hz, 1H), 7.69 (d, J=11.4 Hz, 1H), 7.52 (d, J=7.9 Hz, 1H), 7.42 (d, J=7.5 Hz, 1H), 7.27 (d, J=2.4 Hz, 1H), 7.05 (dd, J=8.8, 2.4 Hz, 1H), 5.08 (dd, J=12.8, 5.4 Hz, 1H), 4.77 (s, 2H), 4.53 (s, 1H), 4.31 (s, 1H), 3.54 (d, J=12.2 Hz, 2H), 3.28 (s, 2H), 3.01-2.77 (m, 4H), 2.72-2.50 (m, 4H), 2.03-1.80 (m, 5H), 1.47-1.23 (m, 8H), 1.15 (s, 6H). MS: calcd. for $C_{46}H_{45}ClFN_7O_6$ $[M+H]^+$: 846.3; found:846.2.

331: 2-Chloro-4-((1r,3r)-3-(2-((3-((1-(2,6-dioxopiperidin-3-yl)-1,3-dioxoisoindolin-5-yl)piperidine-4-yl)(methyl)amino)cyclobutyl)ethynyl)-5-oxo-5,7-dihydro-6H-pyrrolo[3,4-b]pyridin-6-yl)-2,2,4,4-tetramethylcyclobutoxy)benzonitrile
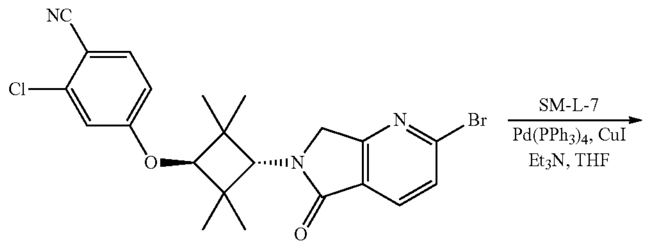
SM-A-1
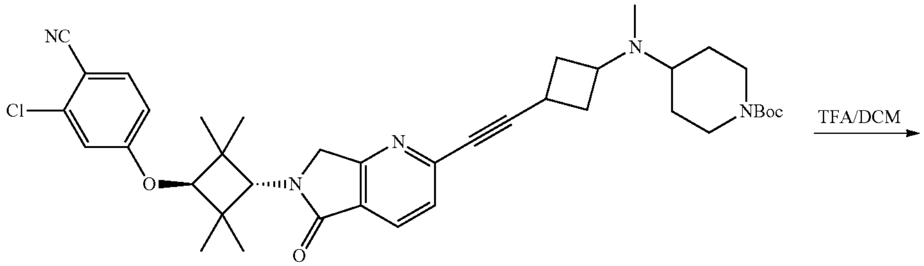
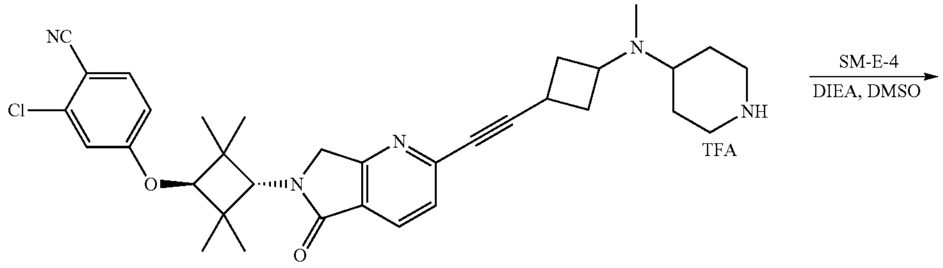
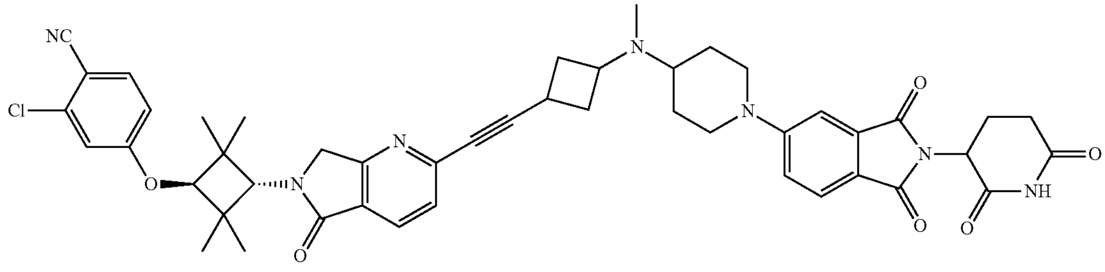
331
$^1$H NMR (400 MHz, DMSO-$d_6$) δ 11.06 (s, 1H), 8.02 (d, J=7.9 Hz, 1H), 7.88 (d, J=8.8 Hz, 1H), 7.63 (d, J=8.6 Hz, 1H), 7.54 (d, J=7.9 Hz, 1H), 7.33-7.17 (m, 3H), 7.05 (dd, J=8.8, 2.4 Hz, 1H), 5.04 (dd, J=12.9, 5.4 Hz, 1H), 4.77 (s, 2H), 4.53 (s, 1H), 4.31 (s, 1H), 4.10 (d, J=13.2 Hz, 2H), 3.16-3.06 (m, 1H), 2.95-2.78 (m, 4H), 2.68-2.55 (m, 1H), 2.55-2.50 (m, 4H), 2.05-1.91 (m, 6H), 1.63 (d, J=11.8 Hz, 2H), 1.48-1.44 (m, 2H), 1.38 (s, 6H), 1.14 (s, 6H). MS: calcd. for $C_{47}H_{47}ClN_7O_6$ $[M+H]^+$: 842.3; found: 842.3.

332: 2-Chloro-4-((1r,3r)-3-(2-((3-((1-(2,6-dioxopiperidin-3-yl)-6-fluoro-1,3-dioxoisoindolin-5-yl)piperidine-4-yl)(methyl)amino)cyclobutyl)ethynyl)-5-oxo-5,7-dihydro-6H-pyrrolo[3,4-b]pyridin-6-yl)-2,2,4,4-tetramethylcyclobutoxy) benzonitrile
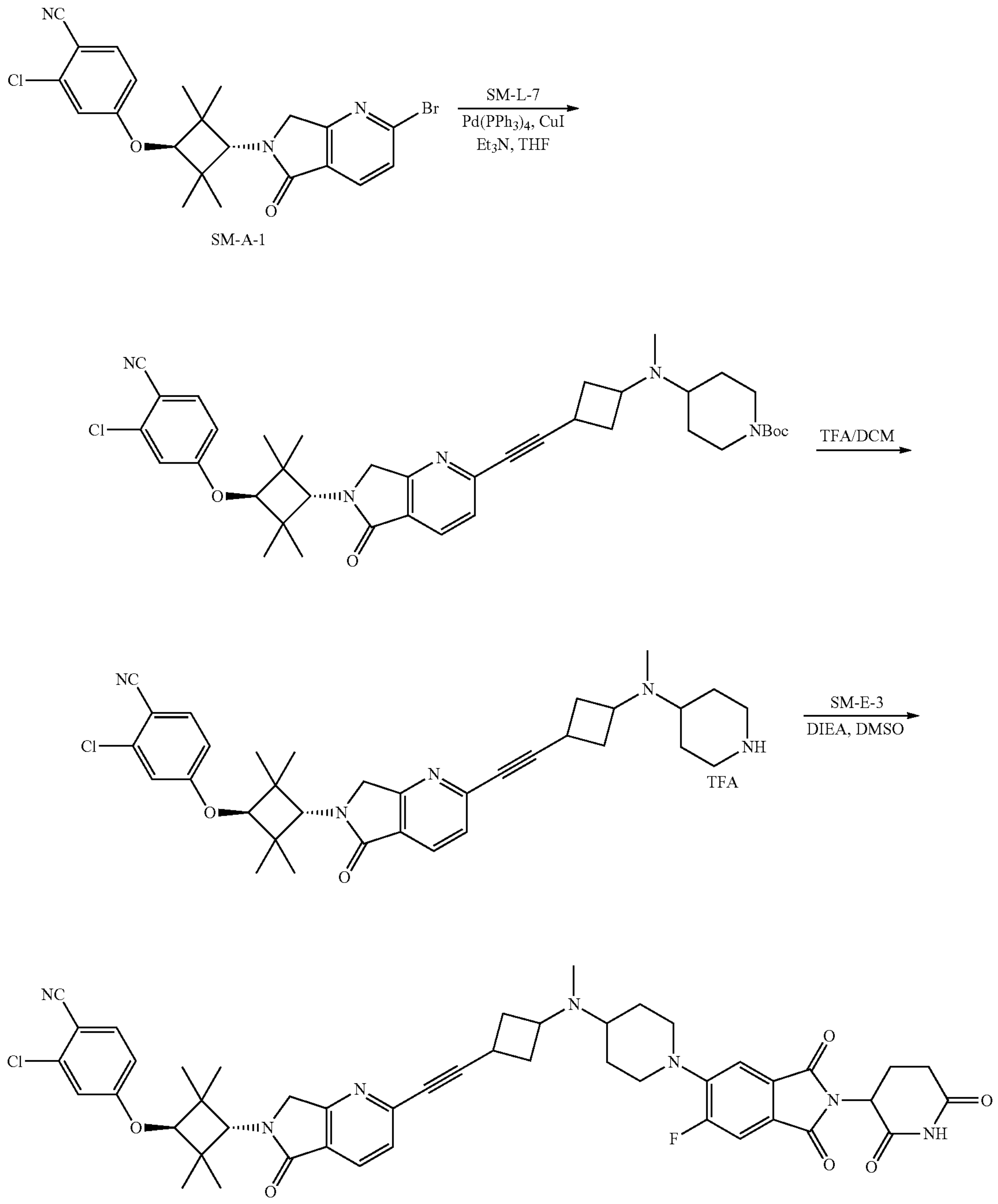
332
$^1$H NMR (400 MHz, DMSO-$d_6$) δ 11.09 (s, 1H), 8.02 (d, J=7.9 Hz, 1H), 7.88 (d, J=8.8 Hz, 1H), 7.68 (d, J=11.4 Hz, 1H), 7.54 (d, J=7.9 Hz, 1H), 7.42 (d, J=7.5 Hz, 1H), 7.26 (d, J=2.4 Hz, 1H), 7.04 (dd, J=8.8, 2.4 Hz, 1H), 5.08 (dd, J=12.8, 5.4 Hz, 1H), 4.77 (s, 2H), 4.52 (s, 1H), 4.31 (s, 1H), 3.64 (d, J=11.4 Hz, 2H), 3.18-3.06 (m, 1H), 3.05-2.91 (m, 1H), 2.86 (t, J=12.4 Hz, 3H), 2.62-2.49 (m, 5H), 2.13-2.03 (m, 3H), 2.03-1.90 (m, 3H), 1.76-1.53 (m, 4H), 1.38 (s, 6H), 1.124 (s, 6H). MS: calcd. for $C_{47}H_{47}ClFN_7O_6$ $[M+H]^+$: 860.3; found: 860.3.

333: 2-Chloro-4-((1r,3r)-3-(2-((1-((2-(2,6-dioxopiperidin-3-yl)-6-fluoro-1,3-dioxoisoindolin-5-yl)piperidine-4-yl)methyl)piperidine-4-yl)ethynyl)-5-oxo-5,7-dihydro-6H-pyrrolo[3,4-b]pyridin-6-yl)-2,2,4,4-tetramethylcyclobutoxy) benzonitrile
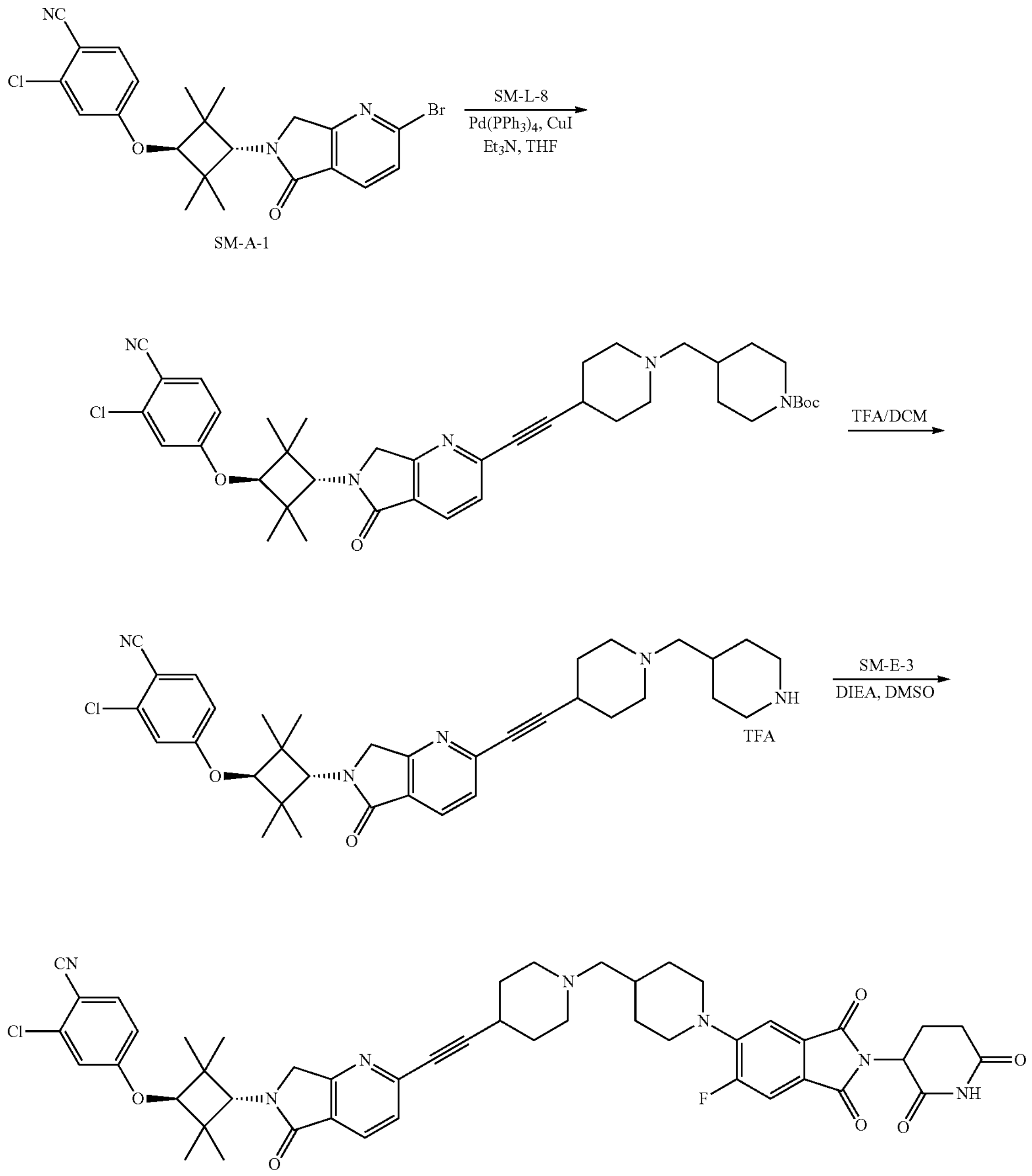
SM-A-1
TFA
333
$^1$H NMR (400 MHz, DMSO-$d_6$) δ 11.09 (s, 1H), 8.04 (d, J=7.9 Hz, 1H), 7.89 (d, J=8.8 Hz, 1H), 7.69 (d, J=11.5 Hz, 1H), 7.54 (d, J=7.9 Hz, 1H), 7.42 (d, J=7.5 Hz, 1H), 7.28 (d, J=2.4 Hz, 1H), 7.05 (dd, J=8.8, 2.4 Hz, 1H), 5.09 (dd, J=12.7, 5.4 Hz, 1H), 4.79 (s, 2H), 4.53 (s, 1H), 4.33 (s, 1H), 3.59 (d, J=12.3 Hz, 2H), 3.29 (s, 1H), 2.84 (t, J=12.0 Hz, 3H), 2.79-2.55 (m, 4H), 2.18-2.16 (m, 4H), 2.04-2.00 (m, 1H), 1.90-1.88 (m, 2H), 1.82-1.79 (m, 2H), 1.74-1.61 (m, 3H), 1.39 (s, 6H), 1.28-1.20 (m, 2H), 1.15 (s, 6H). MS: calcd. for $C_{48}H_{49}ClFN_7O_6$ $[M+H]^+$: 874.3; found: 874.0.

334: 2-Chloro-4-((1r,3r)-3-(2-((1-((2-(2,6-dioxopiperidin-3-yl)-6-fluoro-1,3-dioxoisoindolin-5-yl)azitidin-3-yl)methyl)piperidine-4-yl)ethynyl)-5-oxo-5,7-dihydro-6H-pyrrolo[3,4-b]pyridin-6-yl)-2,2,4,4-tetramethylcyclobutoxy) benzonitrile
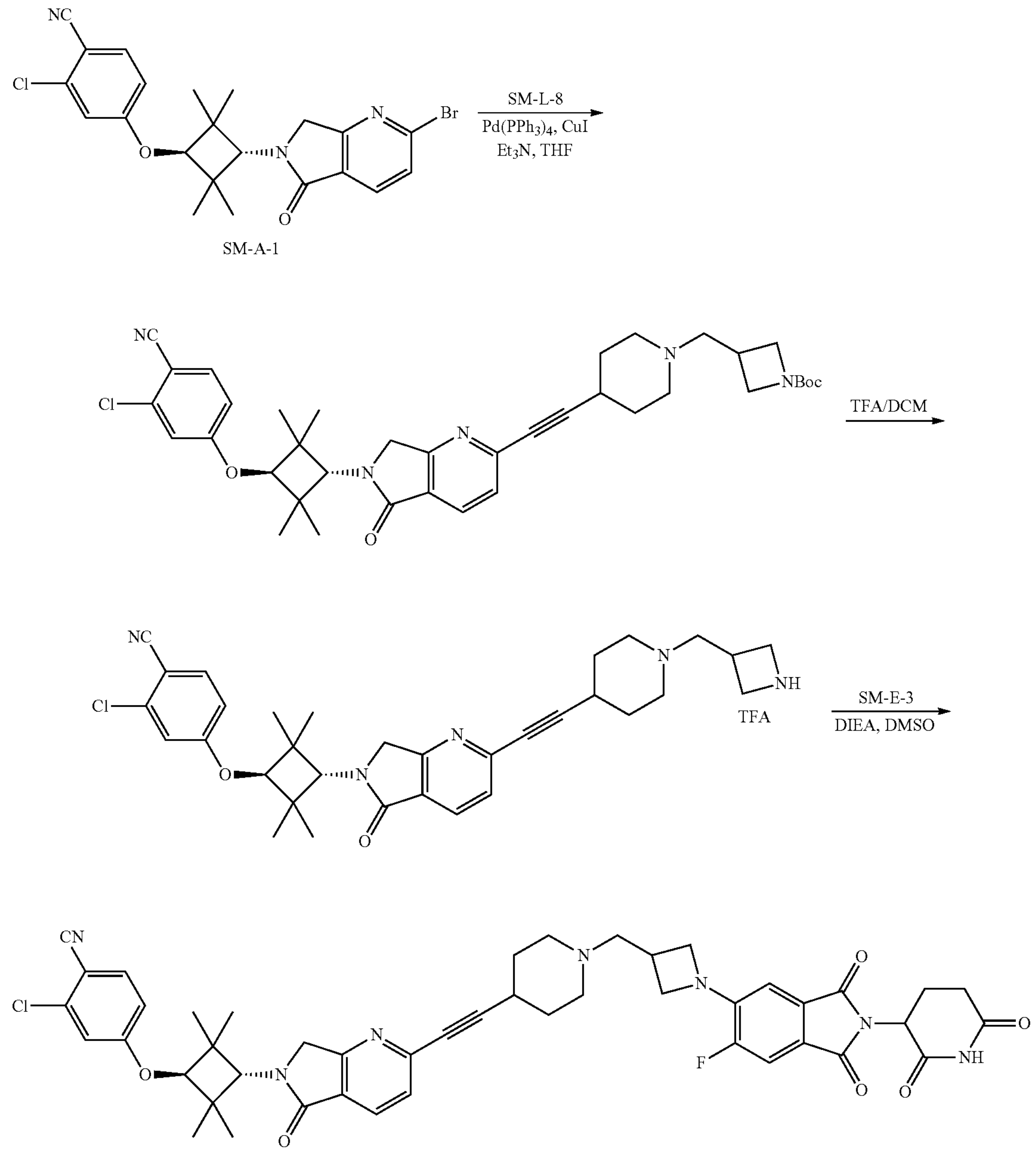
SM-A-1
334
$^1$H NMR (400 MHz, DMSO-$d_6$) δ 11.09 (s, 1H), 8.05 (d, J=7.9 Hz, 1H), 7.91 (d, J=8.7 Hz, 1H), 7.58 (dd, J=11.4, 9.7 Hz, 2H), 7.29 (d, J=2.4 Hz, 1H), 7.07 (dd, J=8.8, 2.4 Hz, 1H), 6.90 (d, J=7.6 Hz, 1H), 5.06 (dd, J=12.8, 5.4 Hz, 1H), 4.81 (s, 2H), 4.54 (s, 1H), 4.34 (s, 1H), 4.30-4.16 (m, 2H), 3.91-3.79 (m, 2H), 3.08-2.82 (m, 2H), 2.74-2.65 (m, 3H), 2.68-2.52 (m, 4H), 2.38-2.12 (m, 2H), 2.11-1.98 (m, 1H), 1.96-1.82 (m, 2H), 1.74-1.58 (m, 2H), 1.41 (s, 6H), 1.16 (s, 6H). MS: calcd. for $C_{46}H_{45}ClFN_7O_6$ $[M+H]^+$: 846.3; found: 845.8.

335: 2-Chloro-4-((1r,3r)-3-(2-((1-((2-(2,6-dioxopiperidin-3-yl)-6-fluoro-1,3-dioxoisoindolin-5-yl)piperidine-4-yl)methyl)azelaic acid-3-yl)ethynyl)-5-oxo-5,7-dihydro-6H-pyrrolo[3,4-b]pyridin-6-yl)-2,2,4,4-tetramethylcyclobutoxy) benzonitrile
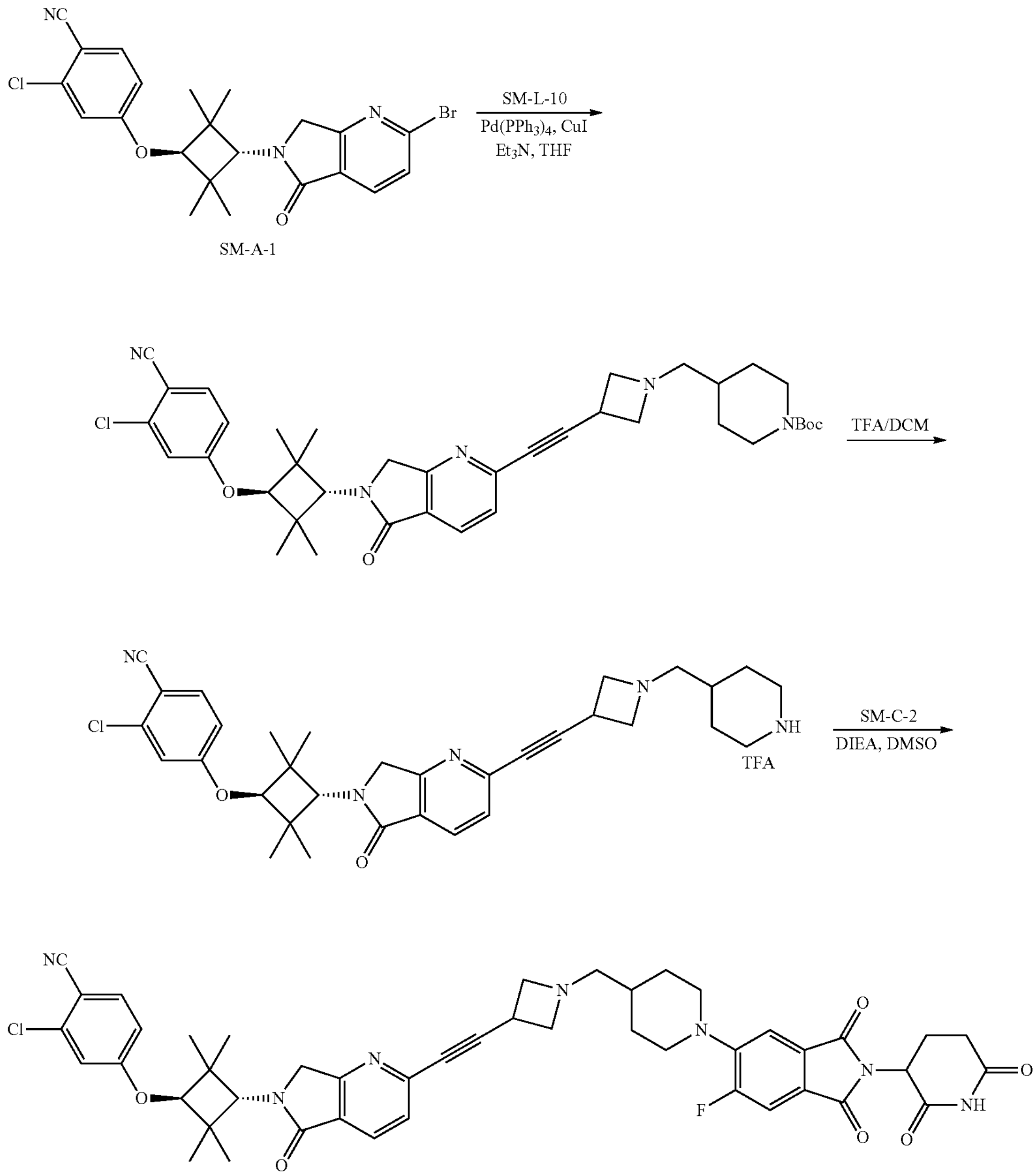
SM-A-1
335
$^1$H NMR (400 MHz, DMSO-$d_6$) δ 11.09 (s, 1H), 8.04 (d, J=7.9 Hz, 1H), 7.89 (d, J=8.8 Hz, 1H), 7.68 (d, J=11.5 Hz, 1H), 7.57 (d, J=7.9 Hz, 1H), 7.41 (d, J=7.5 Hz, 1H), 7.27 (d, J=2.4 Hz, 1H), 7.05 (d, J=8.8, 2.4 Hz, 1H), 5.08 (dd, J=12.8, 5.4 Hz, 1H), 4.78 (s, 2H), 4.53 (s, 1H), 4.32 (s, 1H), 3.64-3.42 (m, 5H), 3.07 (t, J=6.5 Hz, 2H), 2.85 (dd, J=22.0, 10.1 Hz, 3H), 2.67-2.51 (m, 2H), 2.32 (d, J=6.7 Hz, 2H), 2.08-1.94 (m, 1H), 1.77 (d, J=11.2 Hz, 2H), 1.47 (s, 1H) 1.38 (s, 6H), 1.30-1.25 (m, 2H), 1.12 (s, 6H). MS: calcd. for $C_{46}H_{45}ClFN_7O_6$ $[M+H]^+$: 846.3. found: 845.8.

336: 2-Chloro-4-((1r,3r)-3-(2-(3-(4-(2,6-dioxopiperidin-3-yl)-6-fluoro-1,3-dioxoisoindolin-5-yl)piperazin-1-yl)-3-methylbut-1-ynyl)-5-oxo-5,7-dihydro-6H-pyrrolo[3,4-b]pyridin-6-yl)-2,2,4,4-tetramethylcyclobutoxy)benzonitrile
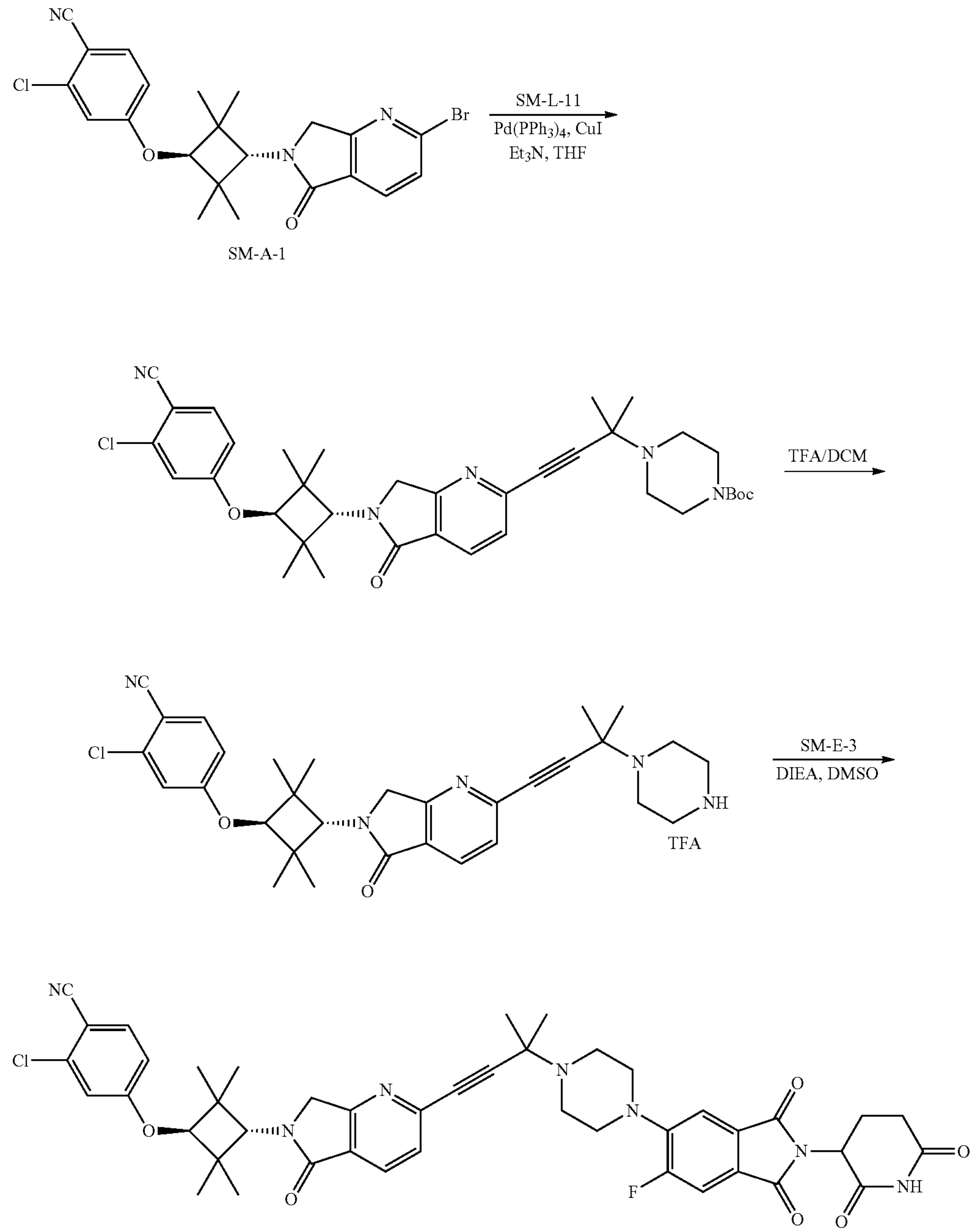
336
$^1$H NMR (400 MHz, DMSO-$d_6$) δ 11.09 (s, 1H), 8.04 (d, J=7.9 Hz, 1H), 7.88 (d, J=8.8 Hz, 1H), 7.73 (d, J=11.4 Hz, 1H), 7.58 (d, J=7.9 Hz, 1H), 7.45 (d, J=7.4 Hz, 1H), 7.27 (d, J=2.4 Hz, 1H), 7.04 (d, J=8.8, 2.4 Hz, 1H), 5.09 (dd, J=12.8, 5.3 Hz, 1H), 4.81 (s, 2H), 4.51 (s, 1H), 4.32 (s, 1H), 2.93-2.76 (m, 5H), 2.68-2.50 (m, 6H), 2.07-1.95 (m, 1H), 1.48 (s, 6H), 1.38 (s, 6H), 1.13 (s, 6H). MS: calcd. for $C_{44}H_{43}ClFN_7O_6$ $[M+H]^+$: 820.3; found: 819.7.

337: 2-Chloro-4-((1r,3r)-3-(2-(1-(2,6-dioxopiperidin-3-yl)-6-fluoro-1,3-dioxoisoindolin-5-yl)piperidine-4-ylamino)-3-methylbut-1-ynyl)-5-oxo-5,7-dihydro-6H-pyrrolo[3,4-b]pyridin-6-yl)-2,2,4,4-tetramethylcyclobutoxy) benzonitrile
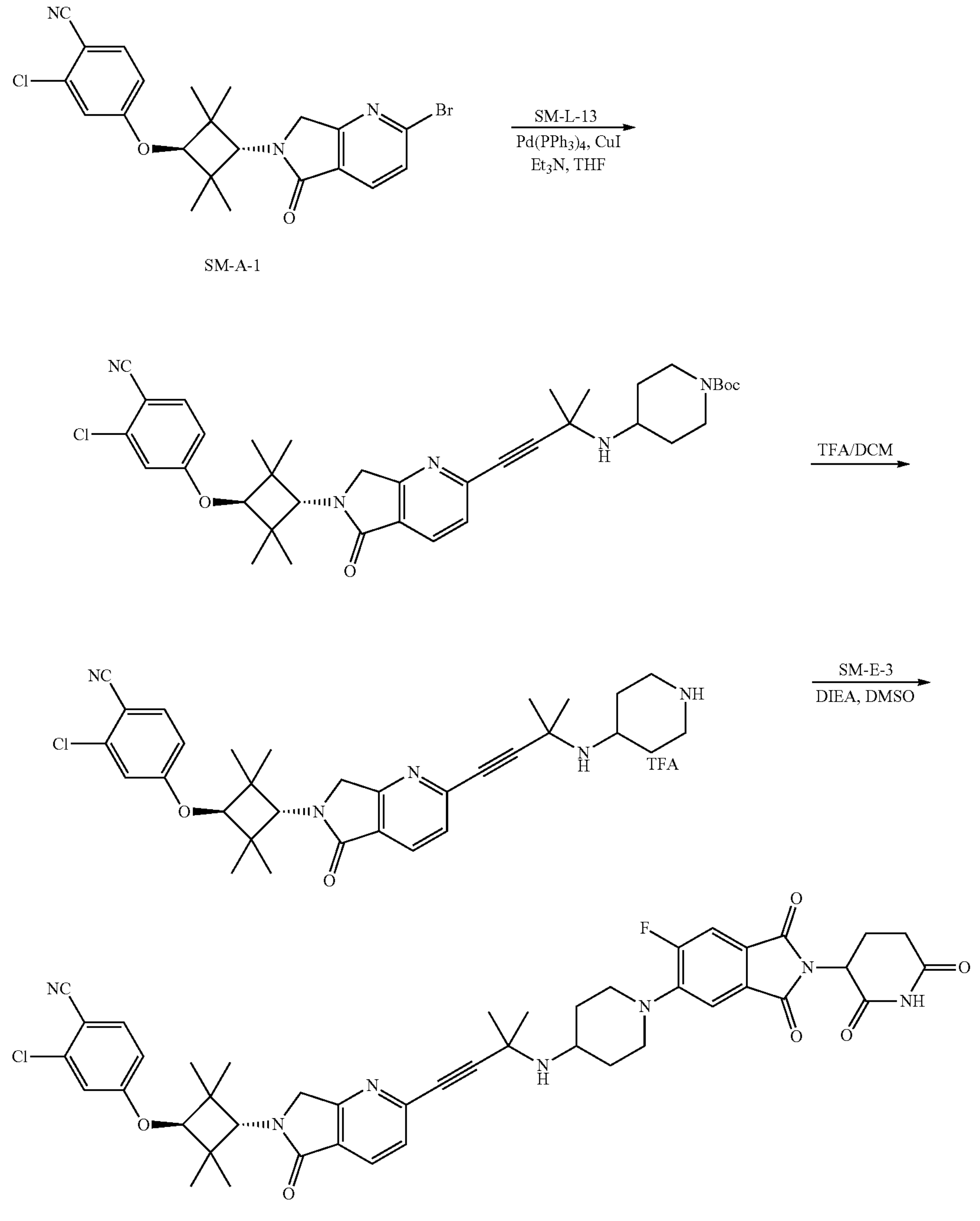
337
$^1$H NMR (400 MHz, DMSO-$d_6$) δ 11.09 (s, 1H), 8.04 (d, J=7.8 Hz, 1H), 7.89 (d, J=8.8 Hz, 1H), 7.69 (d, J=11.5 Hz, 1H), 7.53 (d, J=7.8 Hz, 1H), 7.42 (d, J=7.4 Hz, 1H), 7.27 (d, J=2.4 Hz, 1H), 7.05 (dd, J=8.8, 2.4 Hz, 1H), 5.08 (dd, J=12.8, 5.4 Hz, 1H), 4.79 (s, 2H), 4.52 (s, 1H), 4.32 (s, 1H), 3.55 (d, J=13.3 Hz, 2H), 3.09-2.76 (m, 4H), 2.62-2.49 (m, 2H), 2.07-1.89 (m, 3H), 1.59-1.45 (m, 2H), 1.42-1.35 (m, 12H), 1.14 (s, 6H). MS: calcd. for $C_{45}H_{45}ClFN_7O_6$ $[M+H]^+$: 834.3; found: 834.0.

338: 2-Chloro-4-((1r,3r)-3-(2-((4-(4-(2-(2,6-dioxopiperidin-3-yl)-6-fluoro-1,3-dioxoisoindolin-5-yl)piperazin-1-yl)phenyl)ethynyl)-5-oxo-5,7-dihydro-6H-pyrrolo[3,4-b]pyridin-6-yl)-2,2,4,4-tetramethylcyclobutoxy)benzonitrile
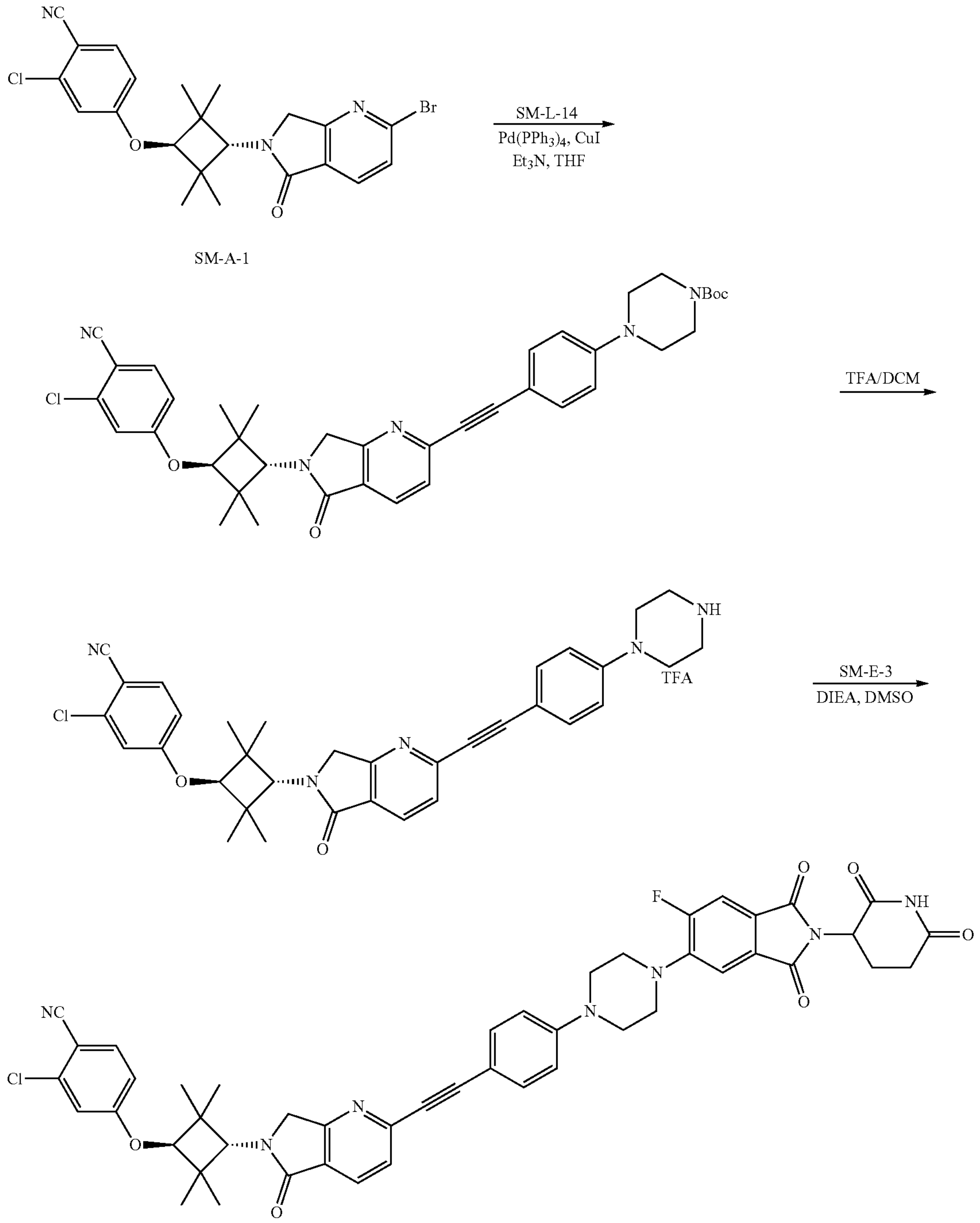
338
$^1$H NMR (400 MHz, DMSO-d$_6$) δ 11.10 (s, 1H), 8.07 (d, J=8.0 Hz, 1H), 7.89 (d, J=8.8 Hz, 1H), 7.76 (d, J=11.3 Hz, 1H), 7.66 (d, J=7.9 Hz, 1H), 7.58-7.45 (m, 3H), 7.28 (d, J=2.4 Hz, 1H), 7.05 (d, J=9.0 Hz, 3H), 5.10 (dd, J=12.9, 5.4 Hz, 1H), 4.81 (s, 2H), 4.54 (s, 1H), 4.33 (s, 1H), 3.45 (s, 41H), 3.41 (s, 4H), 2.87-2.65 (m, 1H), 2.59-2.55 (m, 2H), 2.08-2.00 (m, 1H), 1.40 (s, 6H), 1.15 (s, 6H). MS: calcd. for $C_{47}H_{41}ClFN_7O_6$ [M+H]$^+$: 854.3; found: 853.7.

339: 2-Chloro-4-((1r,3r)-3-(2-((4-(5-(2,6-dioxopiperidin-3-yl)-6-fluoro-1,3-dioxoisoindolin-5-yl)hexahydropyrrolo[3,4-c]pyrrol-2(1H)-yl)cyclohexyl)ethynyl)-5-oxo-5,7-dihydro-6H-pyrrolo[3,4-b]pyridin-6-yl)-2,2,4,4-tetramethylcyclobutoxy)benzonitrile
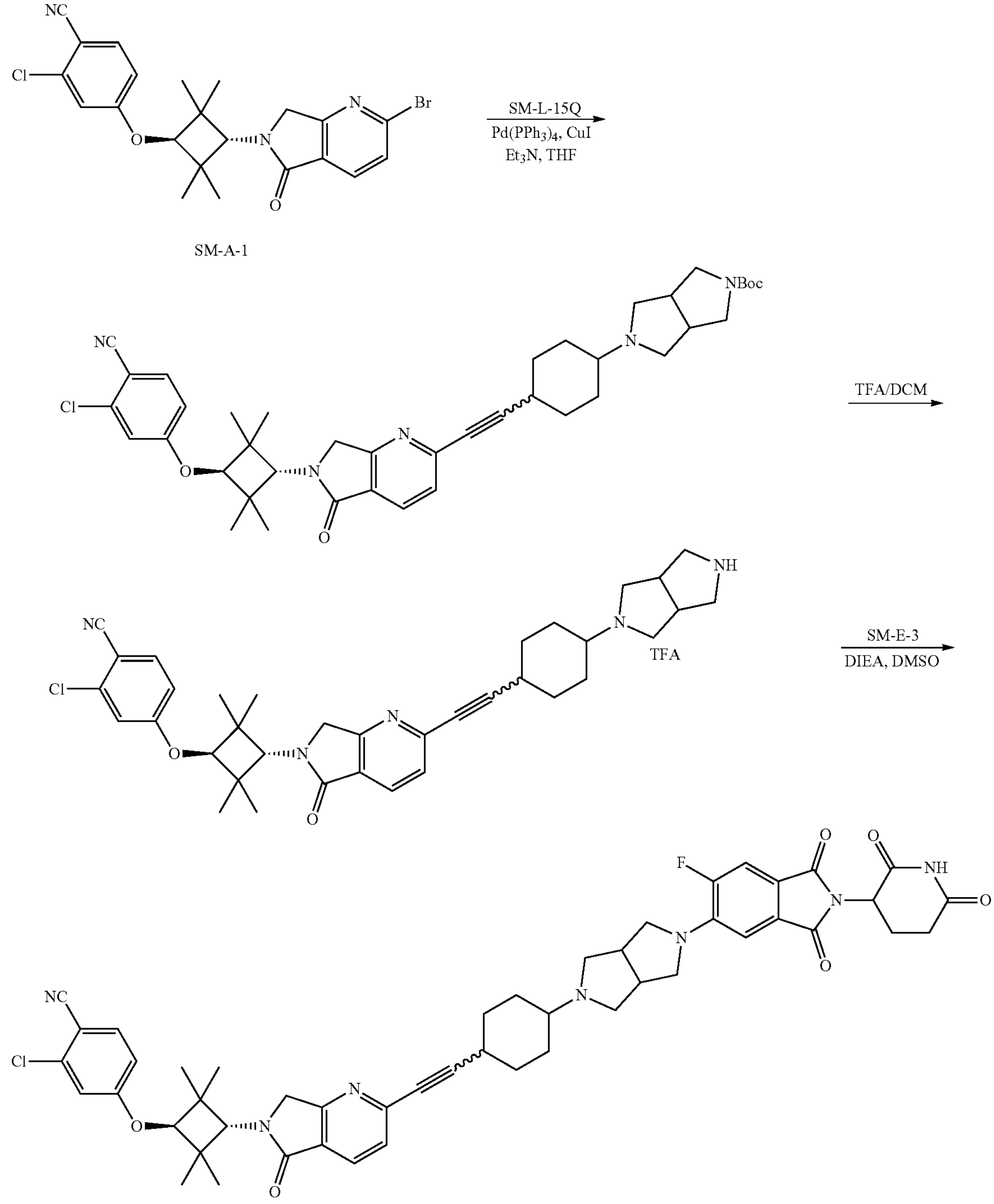
339
$^1$H NMR (400 MHz, DMSO-$d_6$) δ 11.07 (s, 1H), 8.01 (d, J=7.7 Hz, 1H), 7.88 (d, J=8.7 Hz, 1H), 7.61 (d, J=12.3 Hz, 1H), 7.51 (d, J=7.6 Hz, 1H), 7.26 (d, J=2.2 Hz, 1H), 7.13 (d, J=7.2 Hz, 1H), 7.04 (d, J=8.8 Hz, 1H), 5.04 (d, J=12.7, 5.3 Hz, 1H), 4.77 (s, 2H), 4.50 (s, 1H), 4.31 (s, 1H), 3.68 (s, 2H), 3.19-3.08 (m, 2H), 2.88 (s, 5H), 2.70-2.53 (m, 5H), 1.97 (d, J=5.4 Hz, 2H), 1.77-1.72 (m, 8H), 1.36 (s, 6H), 1.13 (s, 6H). MS: calcd. for $C_{49}H_{49}ClFN_7O_6$ $[M+H]^+$: 886.3; found: 885.7.
340: 2-Chloro-4-((1r,3r)-3-(2-((4-(5-(2,6-dioxopiperidin-3-yl)-6-fluoro-1,3-dioxoisoindolin-5-yl)hexahydropyrrolo[3,4-c]pyrrol-2(1H)-yl)cyclohexyl) ethynyl)-5-oxo-5,7-dihydro-6H-pyrrolo[3,4-b]pyridin-6-yl)-2,2,4,4-tetramethylcyclobutoxy)benzonitrile
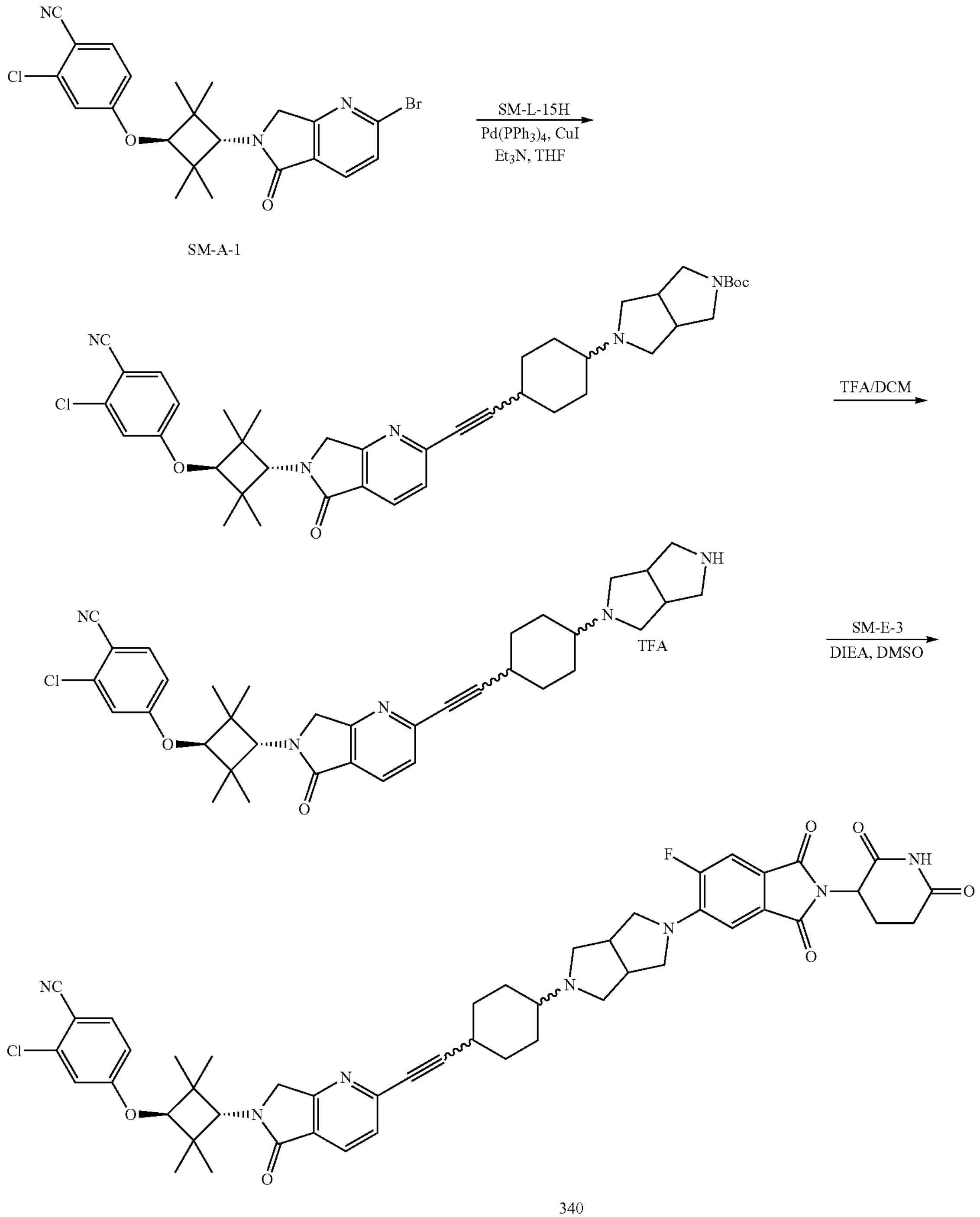
340

$^1$H NMR (400 MHz, DMSO-$d_6$) δ 11.08 (s, 1H), 8.02 (d, J=7.9 Hz, 1H), 7.88 (d, J=8.7 Hz, 1H), 7.63 (d, J=12.0 Hz, 1H), 7.51 (d, J=7.8 Hz, 1H), 7.27 (d, J=2.2 Hz, 1H), 7.13 (d, J=7.6 Hz, 1H), 7.08-7.00 (m, 1H), 5.06 (d, J=12.8, 5.2 Hz, 1H), 4.77 (s, 2H), 4.52 (s, 1H), 4.31 (s, 1H), 3.69 (s, 2H), 2.85 (d, J=12.8 Hz, 5H), 2.74-2.53 (m, 5H), 2.07-2.00 (s, 8H), 1.43 (d, J=11.2 Hz, 2H), 1.38 (s, 6H), 1.26-1.21 (m, 2H), 1.13 (s, 6H). MS: calcd. for $C_{49}H_{49}ClFN_7O_6$ $[M+H]^+$: 886.3; found: 886.2.
341: 2-Chloro-4-((1r,3r)-3-(2-((4-(6-(2,6-dioxopiperidin-3-yl)-6-fluoro-1,3-dioxoisoindolin-5-yl)-2,6-diazaspiro[3.3]heptane-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
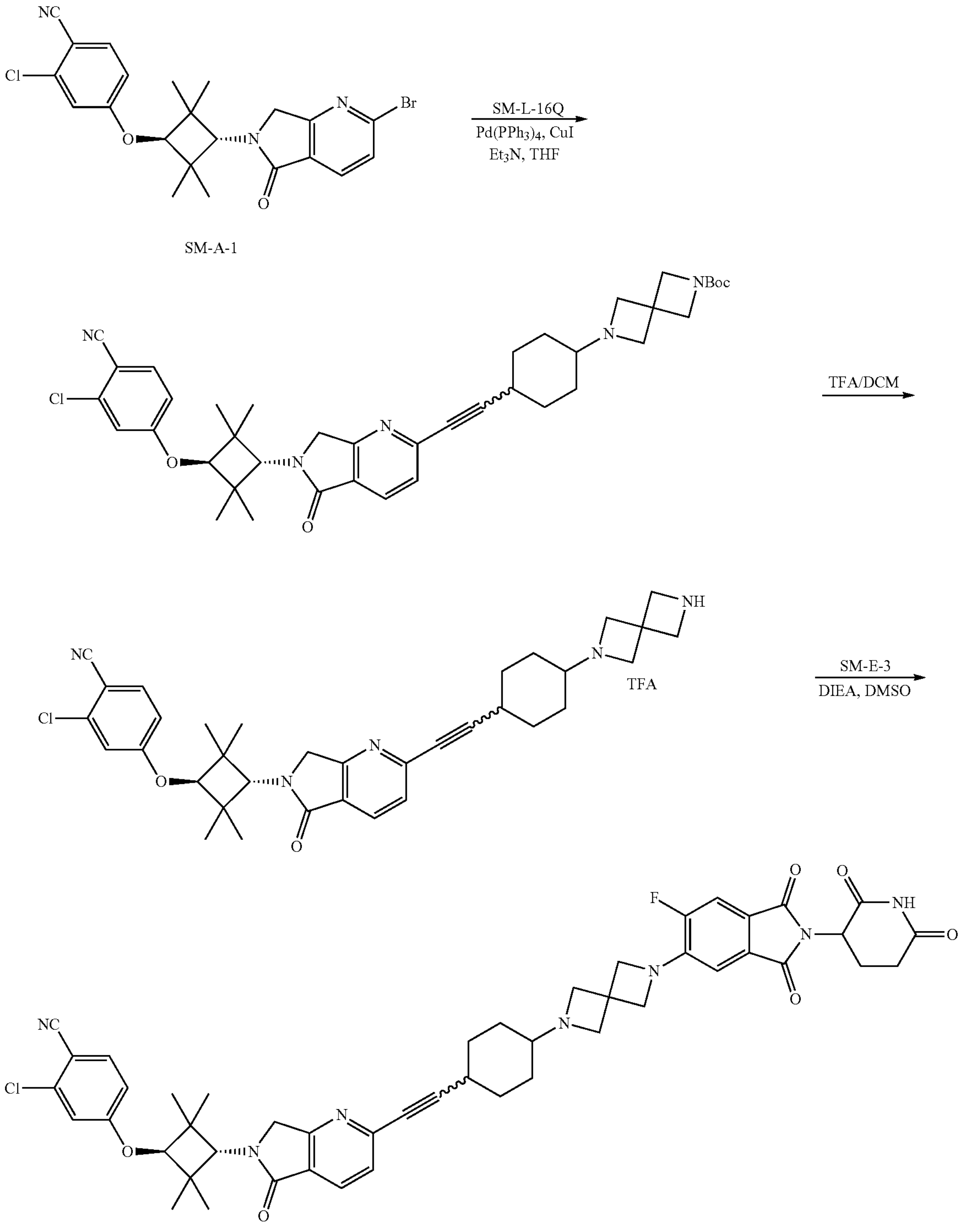
341

$^1$H NMR (400 MHz, DMSO-$d_6$) δ 11.07 (s, 1H), 8.03 (d, J=7.9 Hz, 1H), 7.89 (d, J=8.8 Hz, 1H), 7.56 (dd, J=19.2, 9.5 Hz, 2H), 7.27 (d, J=2.4 Hz, 1H), 7.05 (dd, J=8.8, 2.4 Hz, 1H), 6.90 (d, J=7.4 Hz, 1H), 5.04 (dd, J=12.8, 5.3 Hz, 1H), 4.80 (s, 2H), 4.52 (s, 1H), 4.33 (s, 1H), 4.22 (s, 4H), 3.30-3.01 (m, 4H), 2.99-2.75 (m, 2H), 2.72-2.49 (m, 1H), 2.45-2.18 (m, 2H), 2.12-1.90 (m, 2H), 1.88-1.71 (m, 2H), 1.70-1.41 (m, 4H), 1.39 (s, 6H), 1.14 (s, 6H). MS: calcd. for $C_{48}H_{47}ClFN_7O$ [M+H]$^+$: 872.3; found: 871.8.
342: 2-Chloro-4-((1r,3r)-3-(2-((4-(6-(2,6-dioxopiperidin-3-yl)-6-fluoro-1,3-dioxoisoindolin-5-yl)-2,6-diazaspiro[3.3]heptane-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
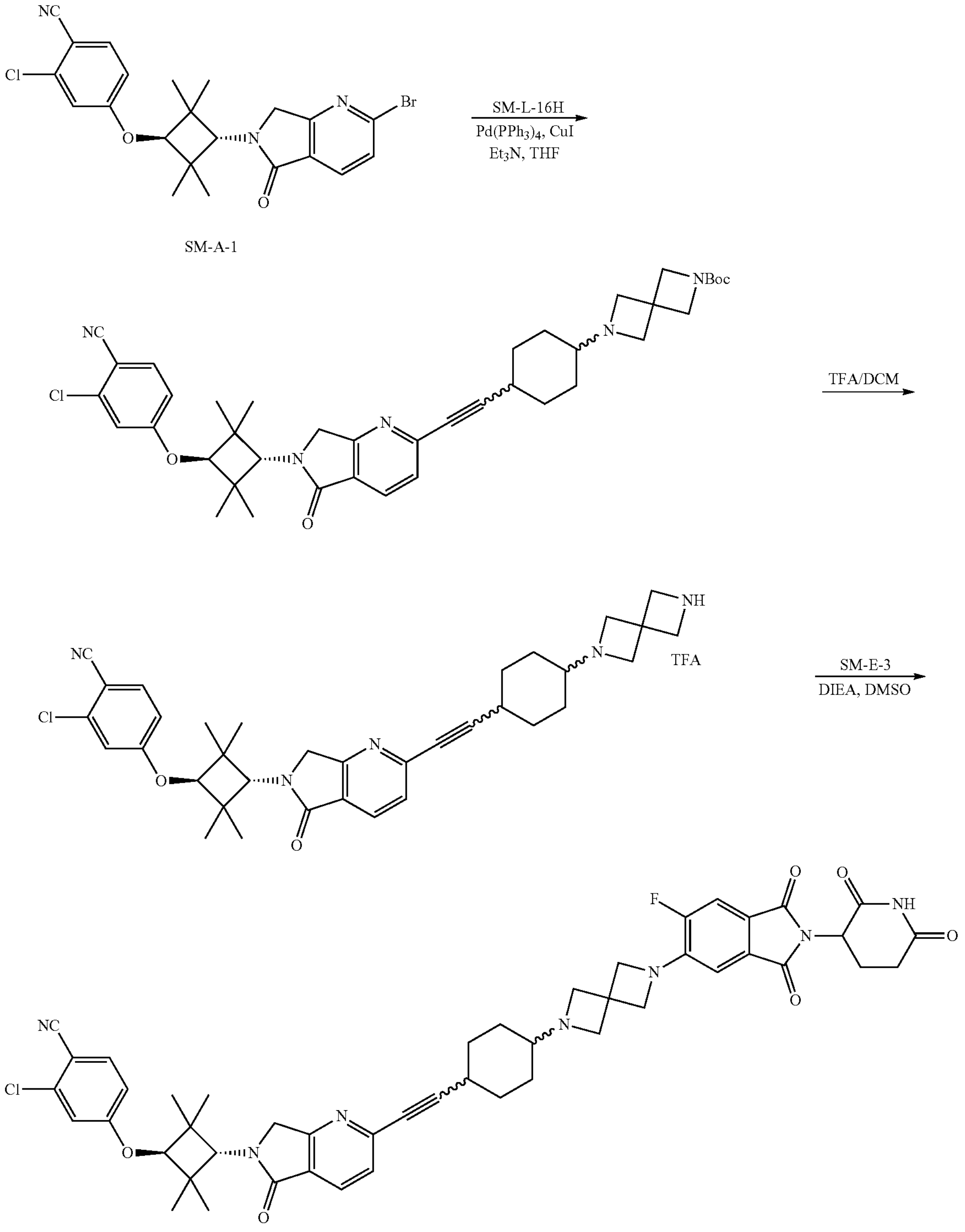

$^1$H NMR (400 MHz, DMSO-$d_6$) δ 11.07 (s, 1H), 8.02 (d, J=7.9 Hz, 1H), 7.88 (d, J=8.8 Hz, 1H), 7.55 (dd, J=27.6, 9.5 Hz, 2H), 7.27 (d, J=2.3 Hz, 1H), 7.04 (dd, J=8.8, 2.3 Hz, 1H), 6.90 (d, J=7.7 Hz, 1H), 5.04 (dd, J=12.9, 5.3 Hz, 1H), 4.77 (s, 2H), 4.52 (s, 1H), 4.31 (s, 1H), 4.21 (s, 4H), 3.29-3.03 (m, 4H), 2.95-2.76 (m, 1H), 2.67-2.51 (m, 2H), 2.45-2.35 (m, 1H), 2.09-1.85 (m, 4H), 1.80-1.63 (m, 2H), 1.52-1.38 (m, 2H), 1.38 (s, 6H), 1.14 (s, 6H), 1.04-0.91 (m, 2H). MS: calcd. for $C_{48}H_{47}ClFN\ O_6$ $[M+H]^+$: 872.3; found: 871.8.
343: 2-Chloro-4-((1r,3r)-3-(2-((4-(5-(2,6-dioxopiperidin-3-yl)-6-fluoro-1,3-dioxoisoindolin-5-yl)-2,5-diazabicyclo[2.2.1]heptan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
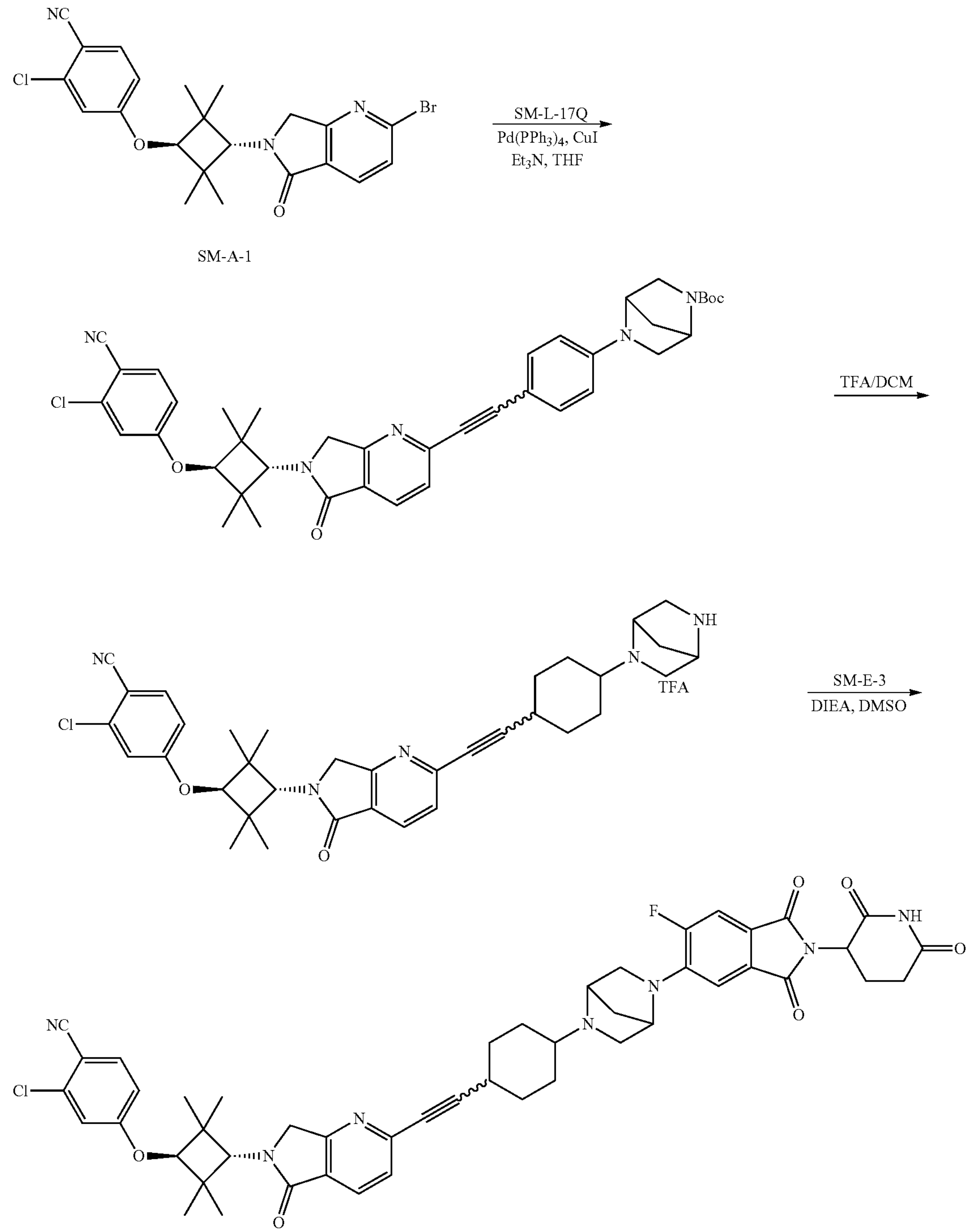
343

$^1$H NMR (400 MHz, DMSO-$d_6$) δ 11.10 (s, 1H), 8.05 (d, J=7.9 Hz, 1H), 7.91 (d, J=8.7 Hz, 1H), 7.63 (d, J=12.3 Hz, 1H), 7.55 (d, J=7.9 Hz, 1H), 7.30 (d, J=2.2 Hz, 1H), 7.16 (d, J=7.3 Hz, 1H), 7.12-7.03 (m, 1H), 5.07 (dd, J=12.7, 5.2 Hz, 1H), 4.82 (s, 2H), 4.61 (s, 1H), 4.54 (s, 1H), 4.35 (s, 1H), 3.79 (s, 1H), 3.61 (s, 1H), 3.51 (s, 1H), 3.16-3.08 (m, 1H), 2.91-2.85 (m, 2H), 2.62-2.53 (m, 1H), 2.32-2.30 (m, 2H), 2.04-2.00 (m, 2H), 1.80-1.76 (m, 3H), 1.72-1.48 (m, 7H), 1.41 (s, 6H), 1.16 (s, 6H). MS: calcd. for $C_{48}H_{47}ClFN_7O_6$ $[M+H]^+$: 872.3; found:873.3.
344: 2-Chloro-4-((1r,3r)-3-(2-((4-(5-(2,6-dioxopiperidin-3-yl)-6-fluoro-1,3-dioxoisoindolin-5-yl)-2,5-diazabicyclo[2.2.1]heptan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
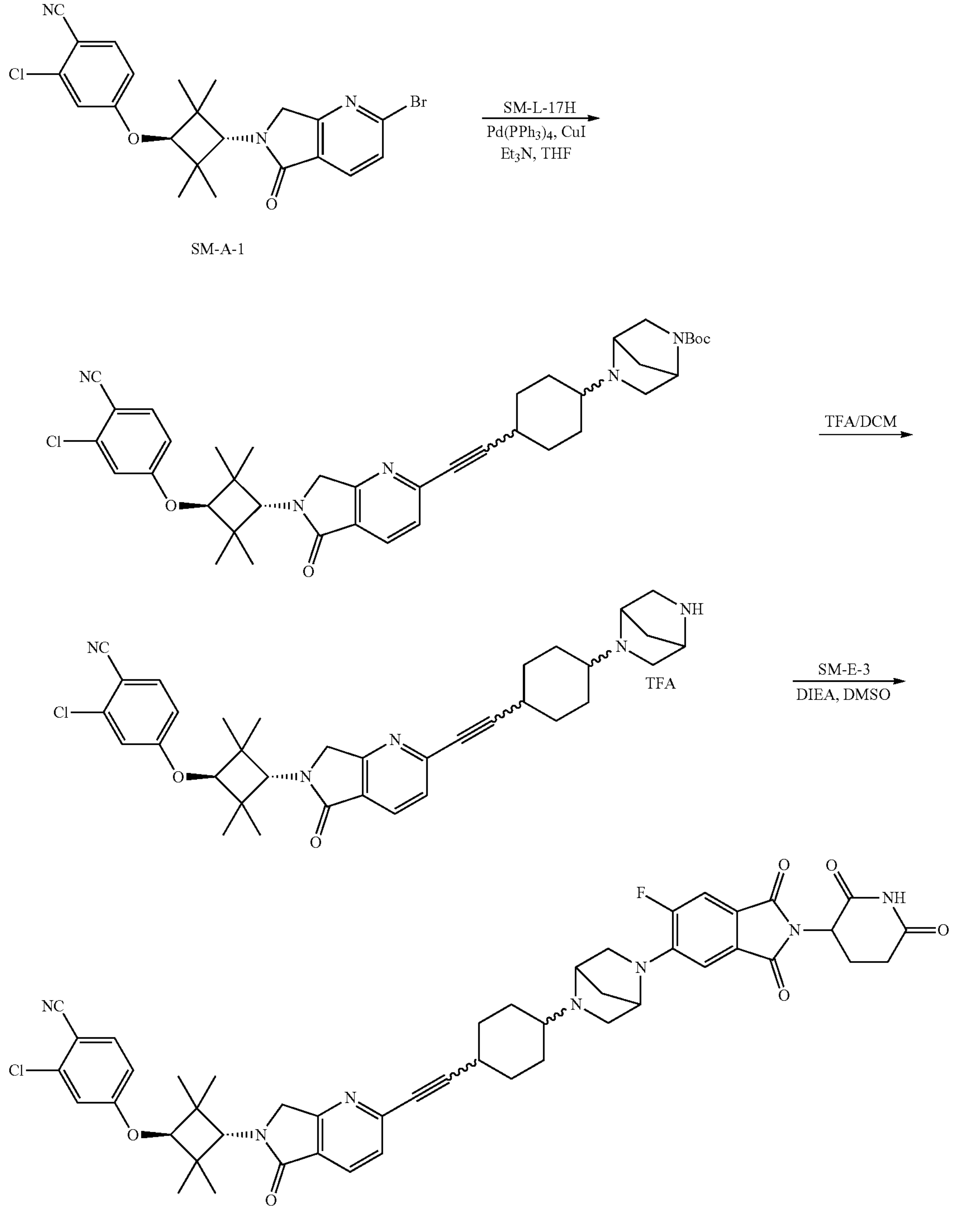
344

$^1$H NMR (400 MHz, DMSO-$d_6$) δ 11.08 (s, 1H), 8.00 (d, J=7.9 Hz, 1H), 7.88 (d, J=8.8 Hz, 1H), 7.61 (d, J=12.4 Hz, 1H), 7.49 (d, J=7.9 Hz, 1H), 7.26 (d, J=2.3 Hz, 1H), 7.13 (d, J=7.7 Hz, 1H), 7.04 (dd, J=8.8, 2.4 Hz, 1H), 5.05 (dd, J=12.9, 5.3 Hz, 1H), 4.76 (s, 2H), 4.58 (s, 1H), 4.51 (s, 1H), 4.31 (s, 1H), 3.76 (s, 1H), 3.61-3.58 (m, 1H), 3.50-3.46 (m, 1H), 3.10 (d, J=7.7 Hz, 1H), 2.87-2.64 (m, 1H), 2.59-2.48 (m, 4H), 2.27-2.24 (m, 1H), 2.03-1.84 (m, 7H), 1.49-1.32 (m, 8H), 1.15-1.19 (m, 8H). MS: calcd. for $C_{45}H_{47}ClFN_7O_6$ $[M+H]^+$: 872.3; found: 872.0.

345: 2-Chloro-4-((1r,3r)-3-(2-((1-((2-(2,6-dioxopiperidin-3-yl)-1,3-dioxoisoindolin-5-yl)piperidine-4-yl)methyl)piperidine-4-yl)ethynyl)-5-oxo-5,7-dihydro-6H-pyrrolo[3,4-b]pyridin-6-yl)-2,2,4,4-tetramethylcyclobutoxy) benzonitrile

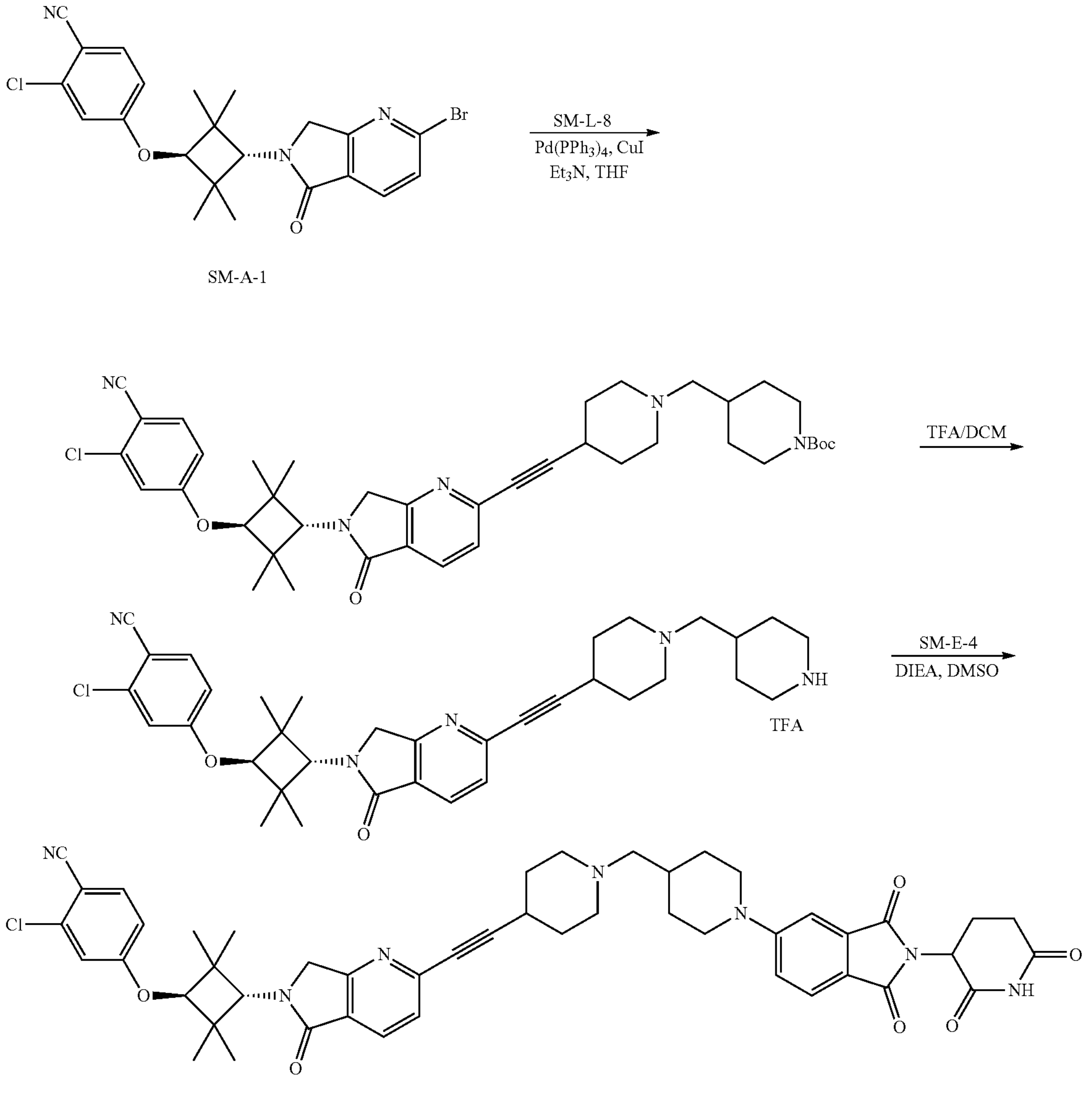

345

$^1$H NMR (400 MHz, DMSO-$d_6$) δ 11.06 (s, 1H), 8.03 (d, J=7.9 Hz, 1H), 7.89 (d, J=8.7 Hz, 1H), 7.63 (d, J=8.5 Hz, 1H), 7.54 (d, J=7.9 Hz, 1H), 7.36-7.21 (m, 2H), 7.21 (d, J=8.7 Hz, 1H), 7.05 (dd, J=8.8, 2.4 Hz, 1H), 5.04 (dd, J=13.0, 5.4 Hz, 1H), 4.79 (s, 2H), 4.52 (s, 1H), 4.32 (s, 1H), 4.02 (d, J=12.6 Hz, 2H), 3.28 (s, 1H), 2.97-2.82 (m, 3H), 2.78-2.50 (m, 4H), 2.13-2.08 (m, 4H), 2.00-1.98 (m, 1H), 1.87-1.83 (m, 2H), 1.78-1.75 (m, 3H), 1.65-1.62 (m, 2H), 1.38 (s, 6H), 1.14-1.07 (m, 8H). MS: calcd. for $C_{48}H_{50}ClN_7O_6$ $[M+H]^+$: 856.4; found: 856.0.

346: 2-Chloro-4-((1r,3r)-3-(2-((1-((2-(2,6-dioxopiperidin-3-yl)-1,3-dioxoisoindolin-5-yl)azitidin-3-yl)methyl)piperidine-4-yl)ethynyl)-5-oxo-5,7-dihydro-6H-pyrrolino[3,4-b]pyridin-6-yl)-2,2,4,4-tetramethylcyclobutoxy) benzonitrile
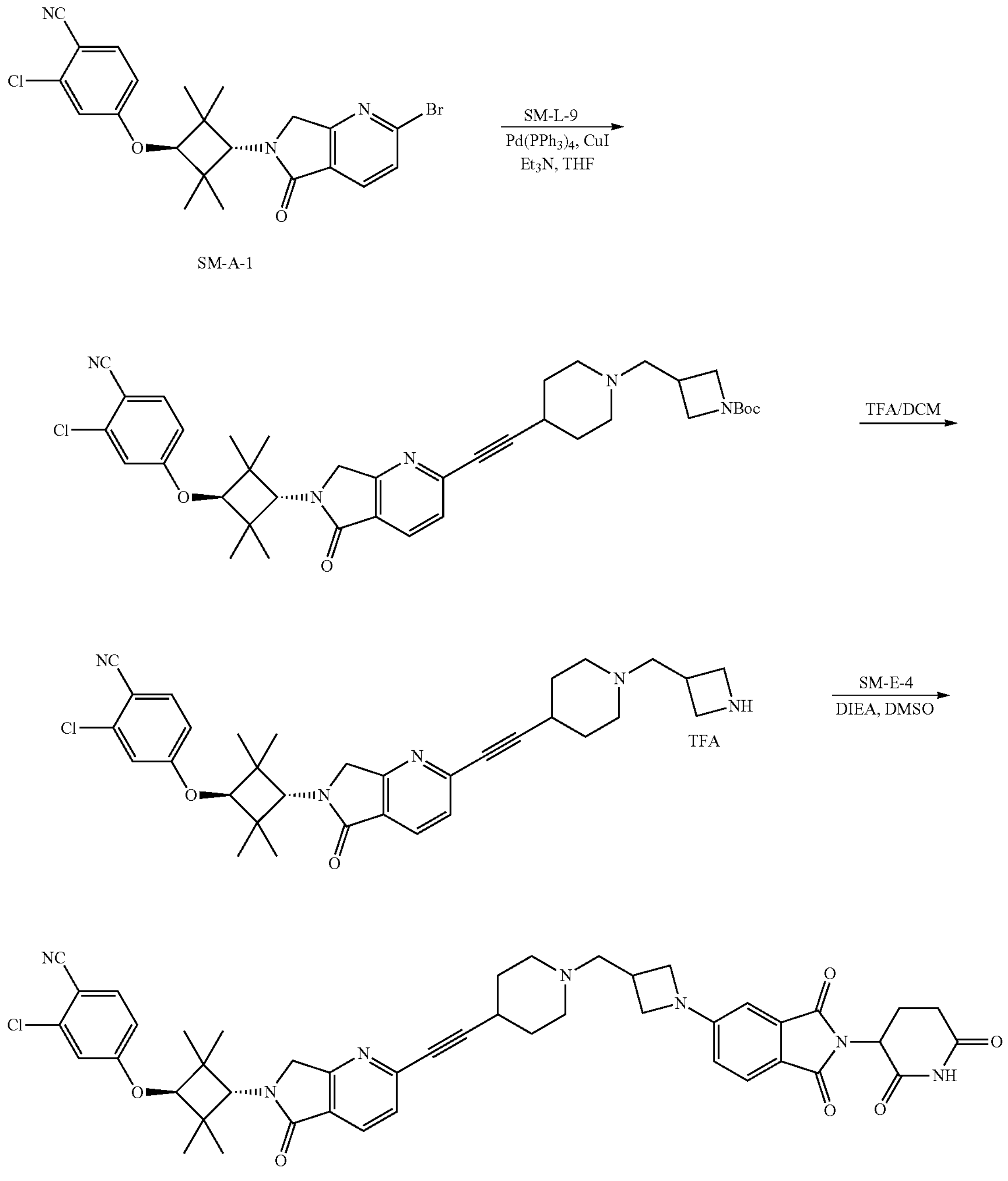
346
$^1$H NMR (400 MHz, DMSO-$d_6$) δ 11.05 (s, 1H), 8.03 (d, J=7.9 Hz, 1H), 7.89 (d, J=8.8 Hz, 1H), 7.61 (d, J=8.3 Hz, 1H), 7.54 (d, J=7.8 Hz, 1H), 7.27 (d, J=2.4 Hz, 1H), 7.05 (dd, J=8.8, 2.4 Hz, 1H), 6.76 (d, J=2.0 Hz, 1H), 6.69-6.49 (m, 1H), 5.03 (dd, J=13.0, 5.4 Hz, 1H), 4.79 (s, 2H), 4.52 (s, 1H), 4.32 (s, 1H), 4.11 (t, J=8.1 Hz, 2H), 3.76-3.41 (m, 2H), 3.22-2.84 (m, 2H), 2.83-2.59 (m, 3H), 2.59-2.49 (m, 4H), 2.44-2.15 (m, 2H), 2.13-1.95 (m, 1H), 1.95-1.66 (m, 2H), 1.76-1.46 (m, 2H), 1.38 (s, 6H), 1.14 (s, 6H). MS: calcd. for $C_{46}H_{46}ClN_7O_6$ $[M+H]^+$: 828.3; found: 827.8.

347: 2-Chloro-4-((1r,3r)-3-(2-((1-((2-(2,6-dioxopiperidin-3-yl)-1,3-dioxoisoindolin-5-yl)piperidine-4-yl)methyl)azelaic acid-3-yl)ethynyl)-5-oxo-5,7-dihydro-6H-pyrrolino[3,4-b]pyridin-6-yl)-2,2,4,4-tetramethylcyclobutoxy)benzonitrile
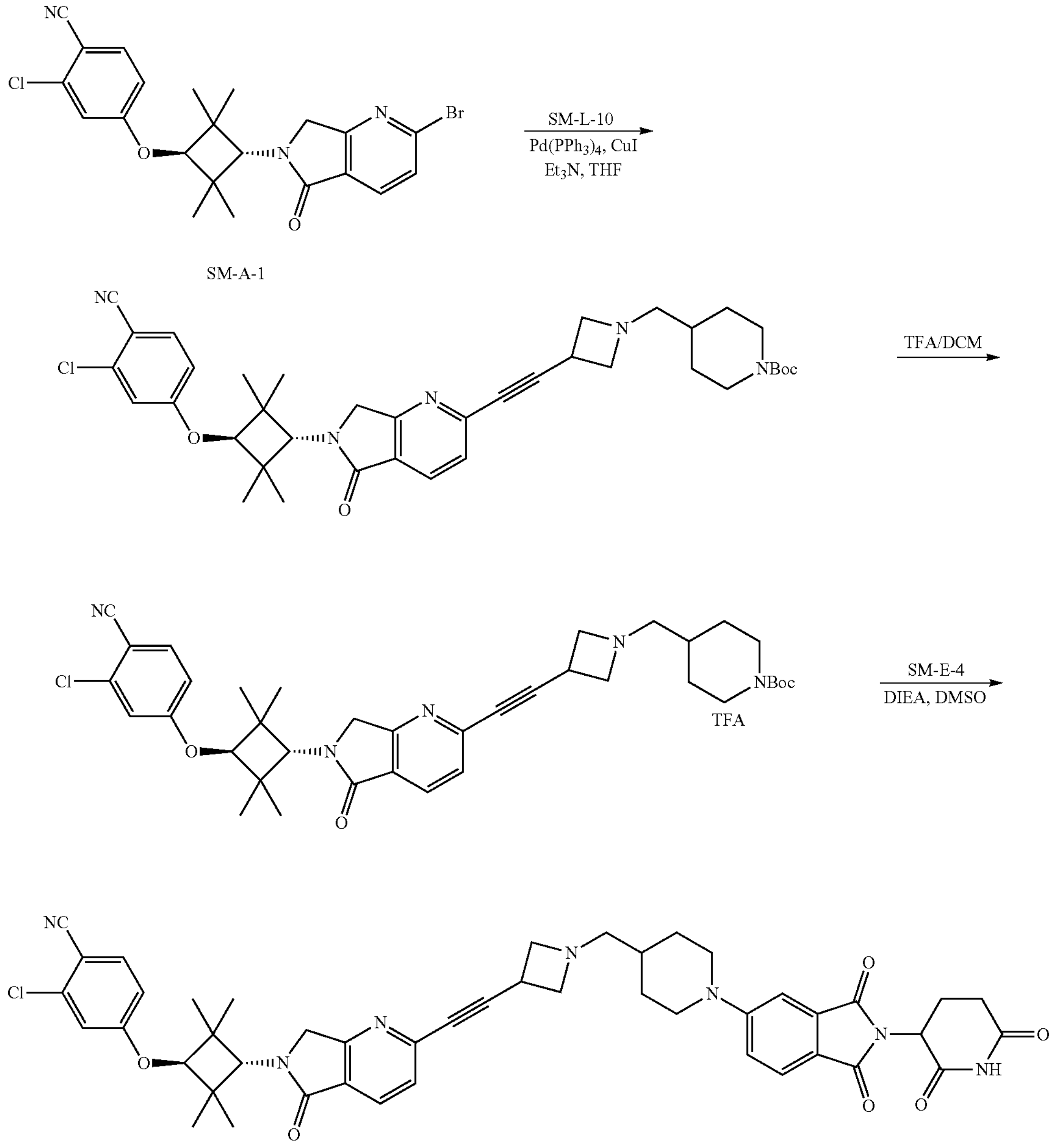
347
$^1$H NMR (400 MHz, DMSO-$d_6$) δ 11.06 (s, 1H), 8.05 (d, J=7.9 Hz, 1H), 7.89 (d, J=8.7 Hz, 1H), 7.63 (d, J=8.5 Hz, 1H), 7.57 (d, J=7.9 Hz, 1H), 7.28 (d, J=2.5 Hz, 2H), 7.21 (d, J=8.7, 2.1 Hz, 1H), 7.05 (d, J=8.8, 2.4 Hz, 1H), 5.05 (d, J=12.9, 5.3 Hz, 1H), 4.79 (s, 2H), 4.53 (s, 1H), 4.32 (s, 1H), 4.01 (d, J=13.3 Hz, 2H), 3.61-3.47 (m, 3H), 3.07 (t, J=6.3 Hz, 2H), 3.00-2.80 (m, 3H), 2.63-2.53 (m, 2H), 2.29 (d, J=6.6 Hz, 2H), 2.06-1.93 (m, 1H), 1.74 (d, J=11.5 Hz, 2H), 1.57 (s, 1H), 1.39 (s, 6H), 1.20-1.03 (m, 8H). MS: calcd. for $C_{46}H_{46}ClN_7O_6$ $[M+H]^+$: 828.3; found: 827.8.

348: 2-chloro-4-((1r,3r)-3-(2-((4-(5-(2-(2,6-dioxopiperidin-3-yl)-1,3-dioxoisoindolin-5-yl)hexahydropyrrolo[3,4-c]pyrrol-2(1H)-yl)cyclohexyl) ethynyl)-5-oxo-5,7-dihydro-6H-pyrrolo[3,4-b]pyridin-6-yl)-2,2,4,4-tetramethylcyclobutoxy)benzonitrile
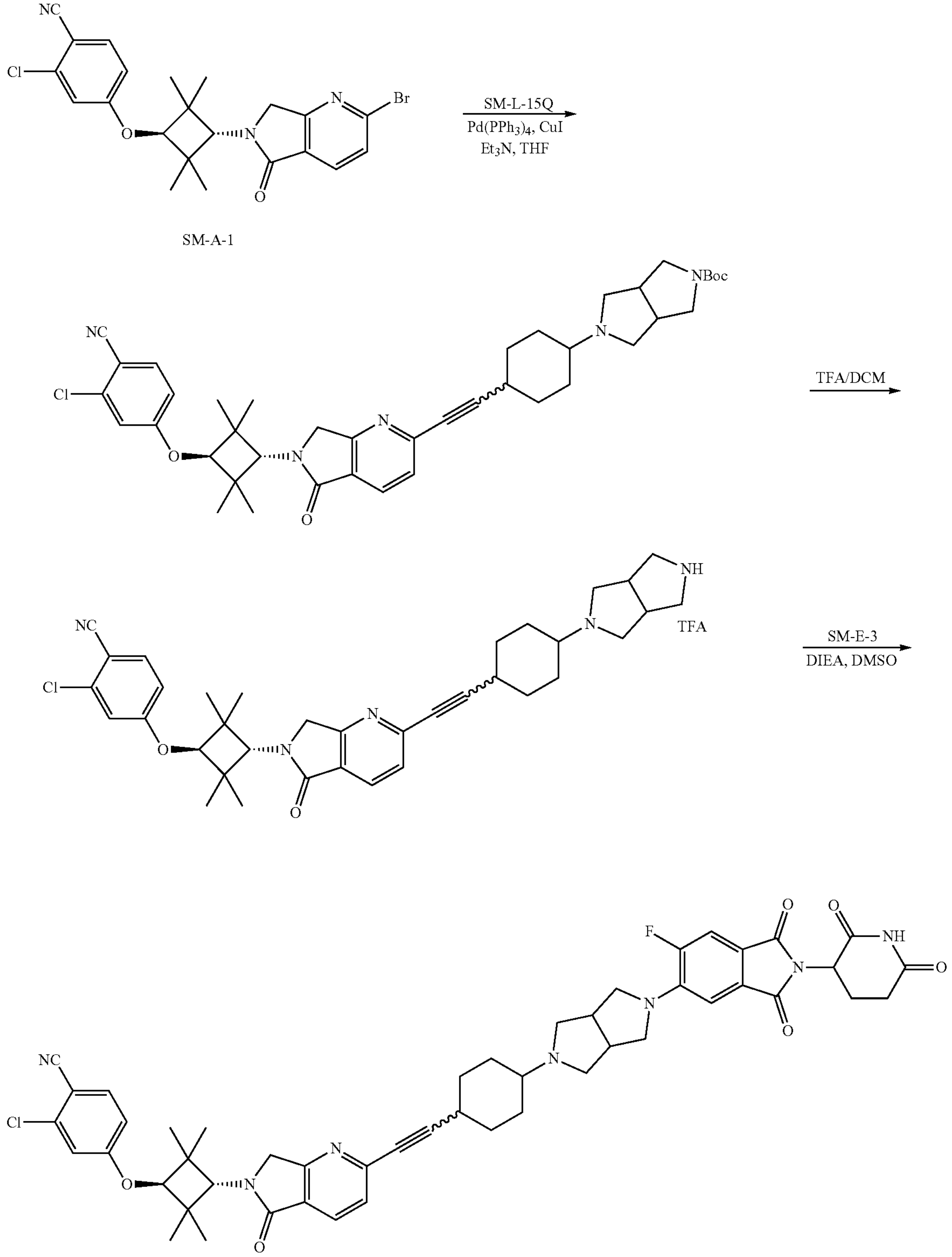

$^1$H NMR (400 MHz, DMSO-$d_6$) δ 11.05 (s, 1H), 7.99 (d, J=7.9 Hz, 1H), 7.88 (d, J=8.8 Hz, 1H), 7.62 (d, J=8.4 Hz, 1H), 7.48 (d, J=7.9 Hz, 1H), 7.26 (d, J=2.2 Hz, 1H), 7.04 (d, J=8.8, 2.2 Hz, 1H), 6.93 (s, 1H), 6.84 (d, J=8.6 Hz, 1H), 5.02 (d, J=12.9, 5.3 Hz, 1H), 4.76 (s, 2H), 4.50 (s, 1H), 4.30 (s, 1H), 3.66 (s, 2H), 3.28 (d, J=7.0 Hz, 2H), 2.90-2.85 (m, 5H), 2.64-2.59 (m, 5H), 2.08-1.92 (m, 2H), 1.88-1.54 (m, 8H), 1.36 (s, 6H), 1.12 (s, 6H). MS: calcd. for $C_{49}H_{50}ClN_7O_6$ $[M+H]^+$: 868.4; found: 867.8.
349: 2-Chloro-4-((1r,3r)-3-(2-((4-(5-(2-(2,6-dioxopiperidin-3-yl)-1,3-dioxoisoindolin-5-yl)hexahydropyrrolo[3,4-c]pyrrol-2(1H)-yl)cyclohexyl) ethynyl)-5-oxo-5,7-dihydro-6H-pyrrolo[3,4-b]pyridin-6-yl)-2,2,4,4-tetramethylcyclobutoxy)benzonitrile
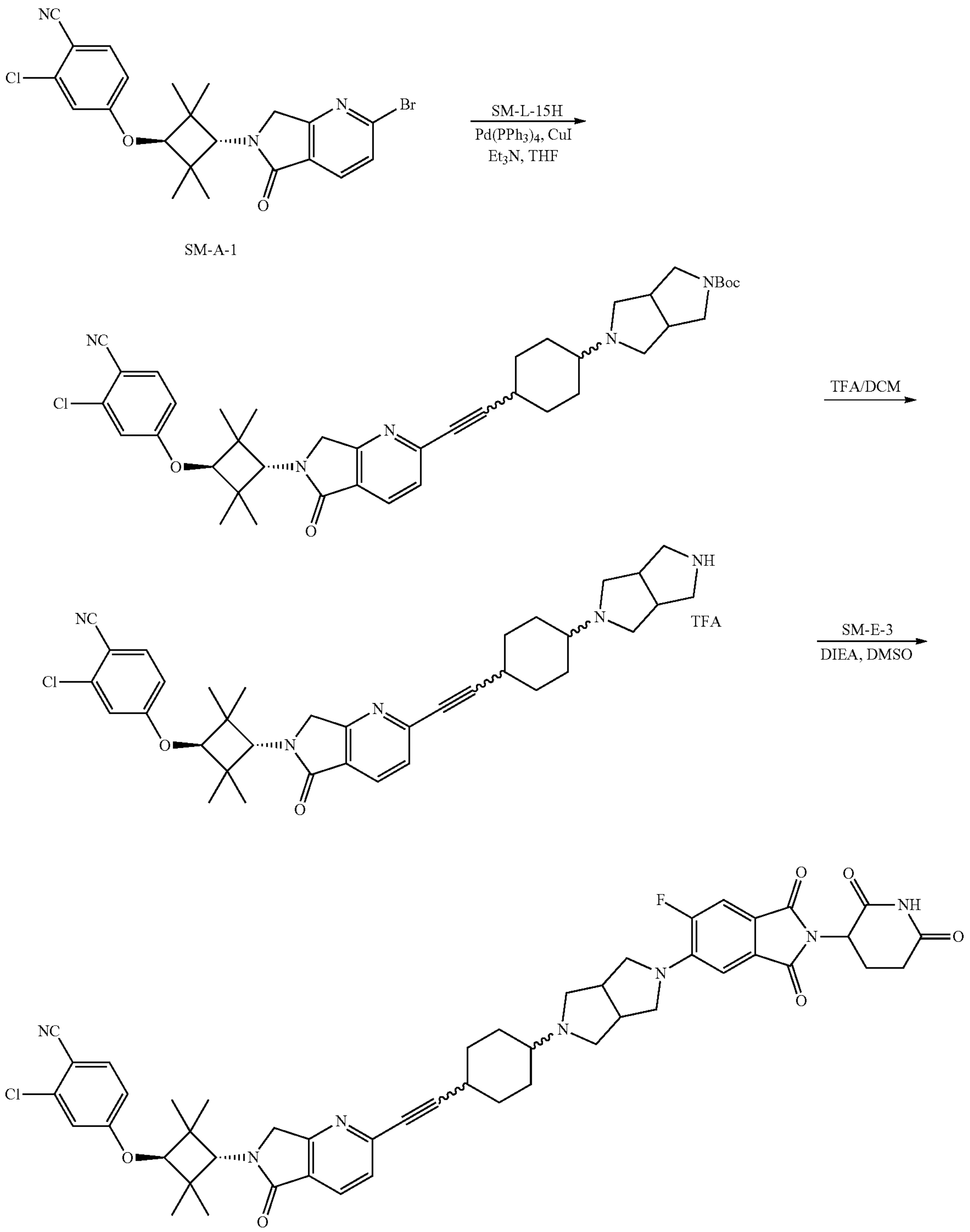
349

$^1$H NMR (400 MHz, DMSO-$d_6$) δ 11.09 (s, 1H), 8.04 (d, J=7.6 Hz, 1H), 7.91 (d, J=8.8 Hz, 1H), 7.67 (d, J=9.0 Hz, 1H), 7.53 (d, J=7.8 Hz, 1H), 7.29 (d, J=2.2 Hz, 1H), 7.07 (d, J=8.8 Hz, 1H), 6.96 (s, 1H), 6.86 (d, J=7.8 Hz, 1H), 5.10-5.02 (m, 1H), 4.79 (s, 2H), 4.54 (s, 1H), 4.33 (s, 1H), 3.67 (s, 2H), 3.49-3.38 (m, 3H), 3.38 (s, 2H), 2.93-2.73 (m, 4H), 2.07-2.01 (m, 8H), 1.50-1.45 (m, 2H), 1.39 (s, 6H), 1.28-1.24 (m, 3H), 1.15 (s, 6H). MS: calcd. for $C_{49}H_{50}ClN_7O_6$ $[M+H]^+$: 868.4; found: 868.3.
350: 2-Chloro-4-((1r,3r)-3-(2-((4-(6-(2-(2,6-dioxopiperidin-3-yl)-1,3-dioxoisoindolin-5-yl)-2,6-diazaspiro[3.3]heptane-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
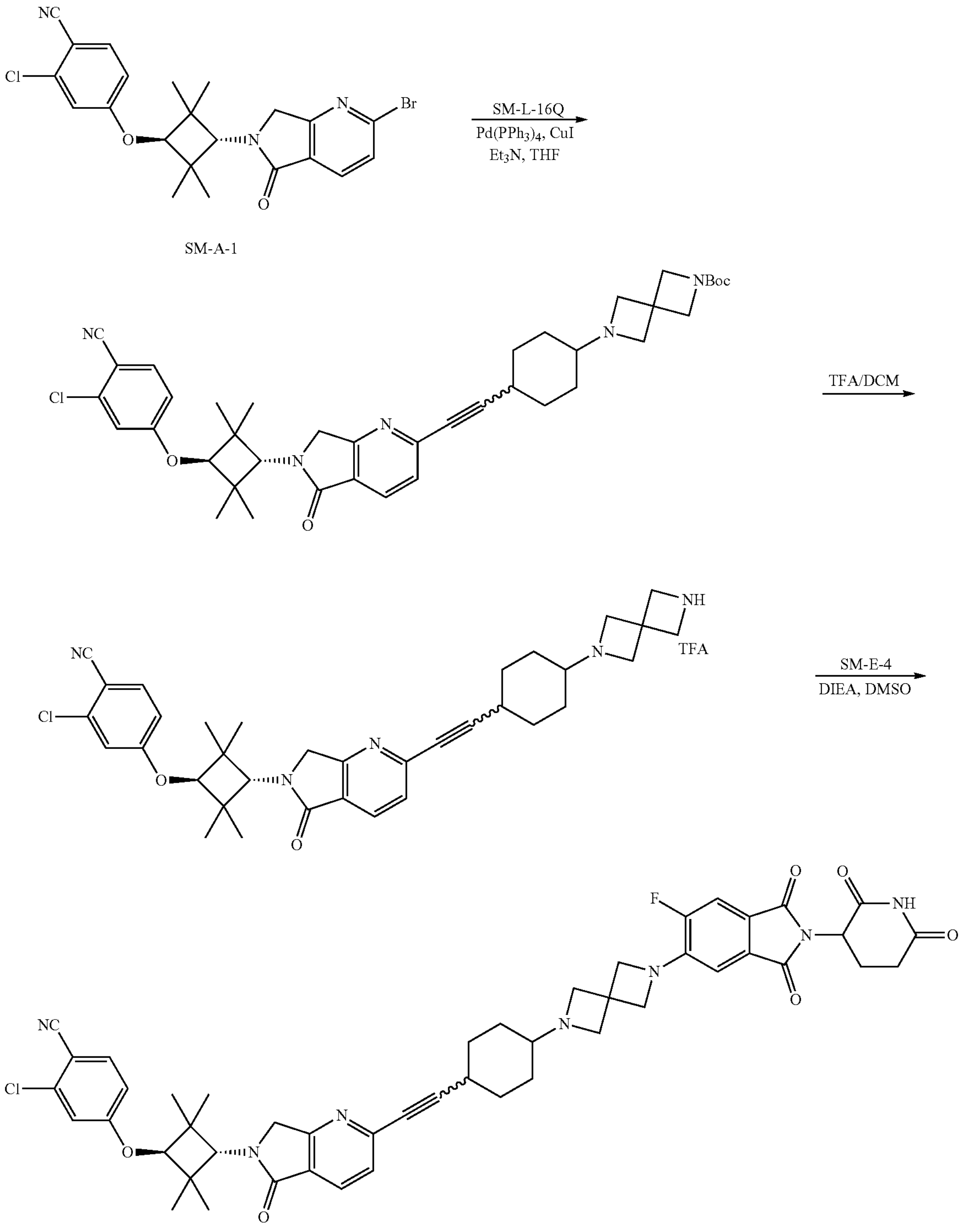
350

$^1$H NMR (400 MHz, DMSO-$d_6$) δ 11.05 (s, 1H), 8.03 (d, J=7.9 Hz, 1H), 7.89 (d, J=8.8 Hz, 1H), 7.62 (d, J=8.3 Hz, 1H), 7.54 (d, J=7.9 Hz, 1H), 7.27 (d, J=2.4 Hz, 1H), 7.05 (dd, J=8.8, 2.4 Hz, 1H), 6.77 (d, J=1.8 Hz, 1H), 6.62 (dd, J=8.4, 1.9 Hz, 1H), 5.03 (dd, J=12.9, 5.5 Hz, 1H), 4.80 (s, 2H), 4.52 (s, 1H), 4.33 (s, 1H), 4.08 (s, 4H), 3.25 (s, 4H), 3.01-2.75 (m, 2H), 2.68-2.52 (m, 2H), 2.41-2.17 (m, 2H), 2.09-1.91 (m, 2H), 1.87-1.71 (m, 2H), 1.69-1.41 (m, 4H), 1.39 (s, 6H), 1.14 (s, 6H). MS: calcd. for $C_{48}H_{48}ClN_7O_6$ $[M+H]^+$: 854.3; found: 853.8.
351: 2-Chloro-4-((1r,3r)-3-(2-((4-(6-(2-(2,6-dioxopiperidin-3-yl)-1,3-dioxoisoindolin-5-yl)-2,6-diazaspiro[3.3]heptane-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
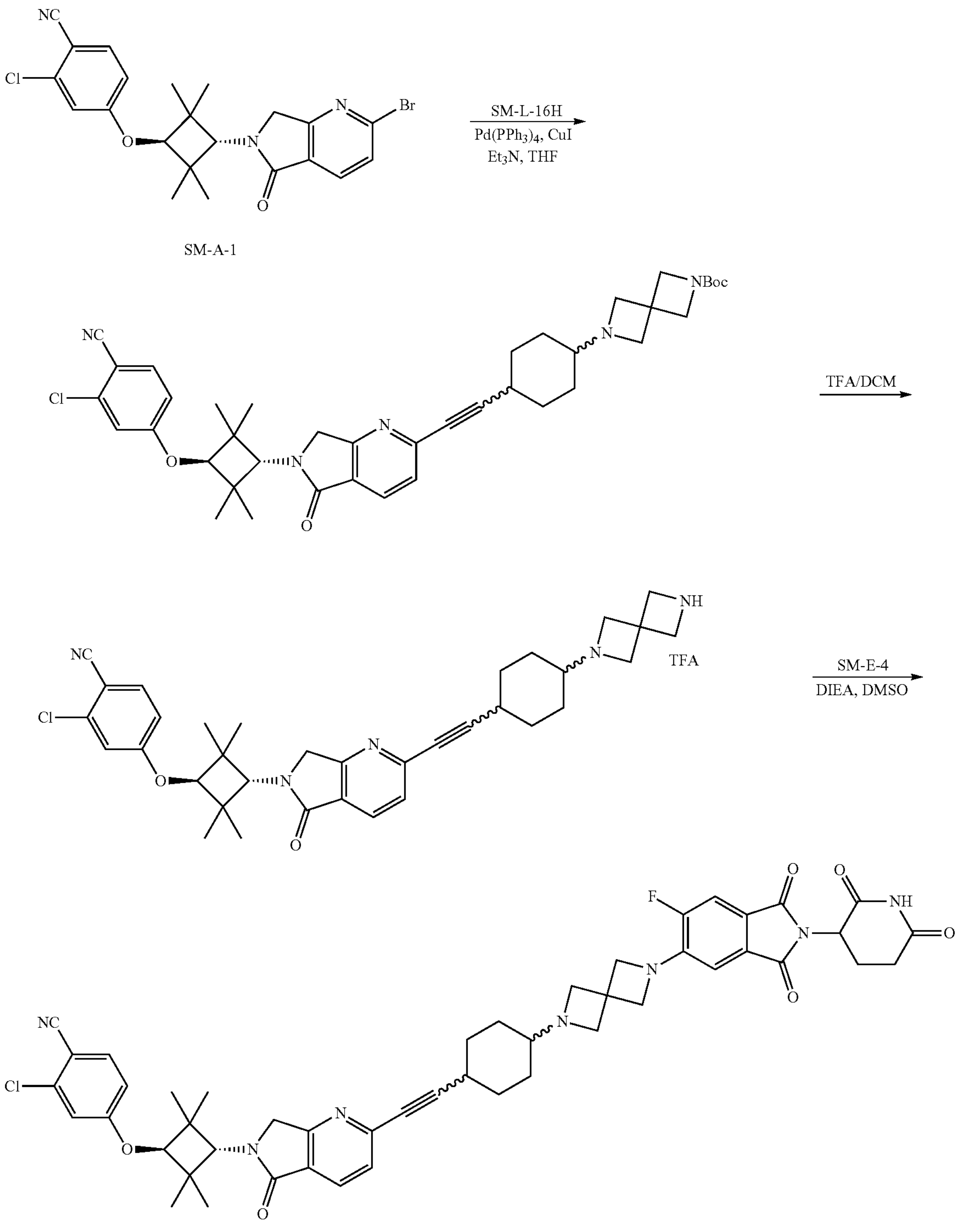
351

$^1$H NMR (400 MHz, DMSO-$d_6$) δ 11.06 (s, 1H), 8.02 (d, J=7.9 Hz, 1H), 7.88 (d, J=8.8 Hz, 1H), 7.62 (d, J=8.3 Hz, 1H), 7.52 (d, J=7.9 Hz, 1H), 7.27 (d, J=2.4 Hz, 1H), 7.05 (dd, J=8.8, 2.4 Hz, 1H), 6.77 (s, 1H), 6.63 (d, J=8.3 Hz, 1H), 5.03 (dd, J=12.9, 5.3 Hz, 1H), 4.77 (s, 2H), 4.52 (s, 1H), 4.31 (s, 1H), 4.08 (s, 4H), 3.30-3.23 (m, 4H), 2.98-2.75 (m, 1H), 2.67-2.50 (m, 2H), 2.46-2.40 (m, 1H), 2.21-1.85 (m, 4H), 1.78-1.62 (m, 2H), 1.56-1.39 (m, 2H), 1.38 (s, 6H), 1.14 (s, 6H), 1.03-0.83 (m, 2H). MS: calcd. for $C_{48}H_{48}ClN_7O_6$ $[M+H]^+$: 854.3; found: 853.8.

352: 2-Chloro-4-((1r,3r)-3-(2-((4-(5-(2-(2,6-dioxopiperidin-3-yl)-1,3-dioxoisoindolin-5-yl)-2,5-diazabicyclo[2.2.1]heptan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile

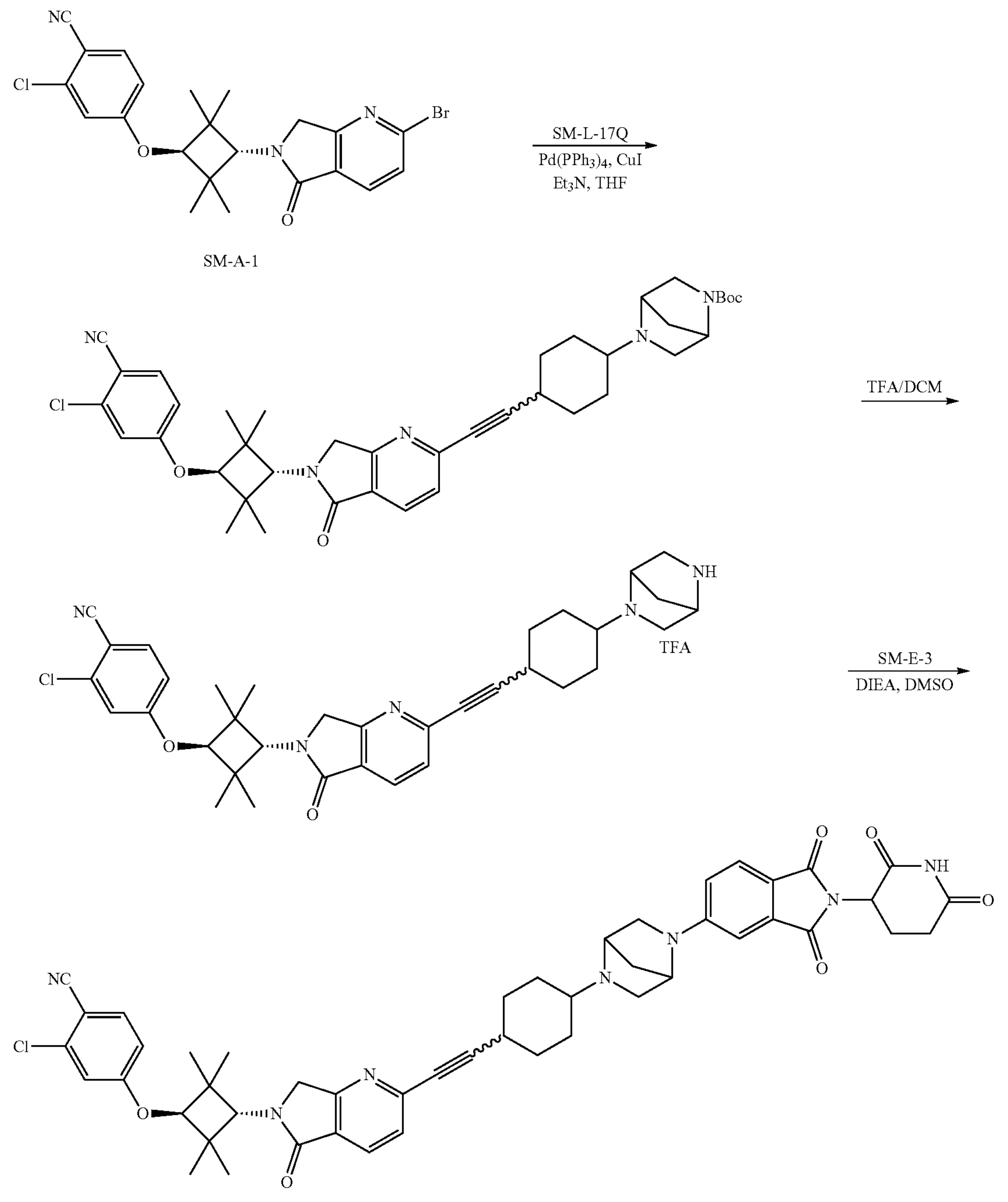

352

$^1$H NMR (400 MHz, DMSO-$d_6$) δ 11.08 (s, 1H), 8.05 (d, J=7.9 Hz, 1H), 7.91 (d, J=8.8 Hz, 1H), 7.63 (d, J=8.5 Hz, 1H), 7.55 (d, J=7.9 Hz, 1H), 7.30 (d, J=2.3 Hz, 1H), 7.07 (dd, J=8.8, 2.4 Hz, 2H), 6.89 (s, 1H), 5.06 (dd, J=12.9, 5.3

Hz, 1H), 4.82 (s, 2H), 4.63 (s, 1H), 4.54 (s, 1H), 4.35 (s, 1H), 3.85 (s, 1H), 3.42 (s, 2H), 3.11 (d, J=12.1 Hz, 1H), 2.89-2.67 (m, 2H), 2.60-2.53 (m, 1H), 2.34-2.32 (m, 1H), 2.25-2.23 (m, 1H), 2.18-2.02 (m, 2H), 1.86-1.75 (m, 4H), 1.74-1.50 (m, 6H), 1.41 (s, 6H), 1.16 (s, 6H). MS: calcd. for $C_{48}H_{48}ClN_7O_6$ $[M+H]^+$: 854.3; found: 854.3.
353: 2-Chloro-4-((1r,3r)-3-(2-((4-(5-(2-(2,6-dioxopiperidin-3-yl)-1,3-dioxoisoindolin-5-yl)-2,5-diazabicyclo[2.2.1]heptan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
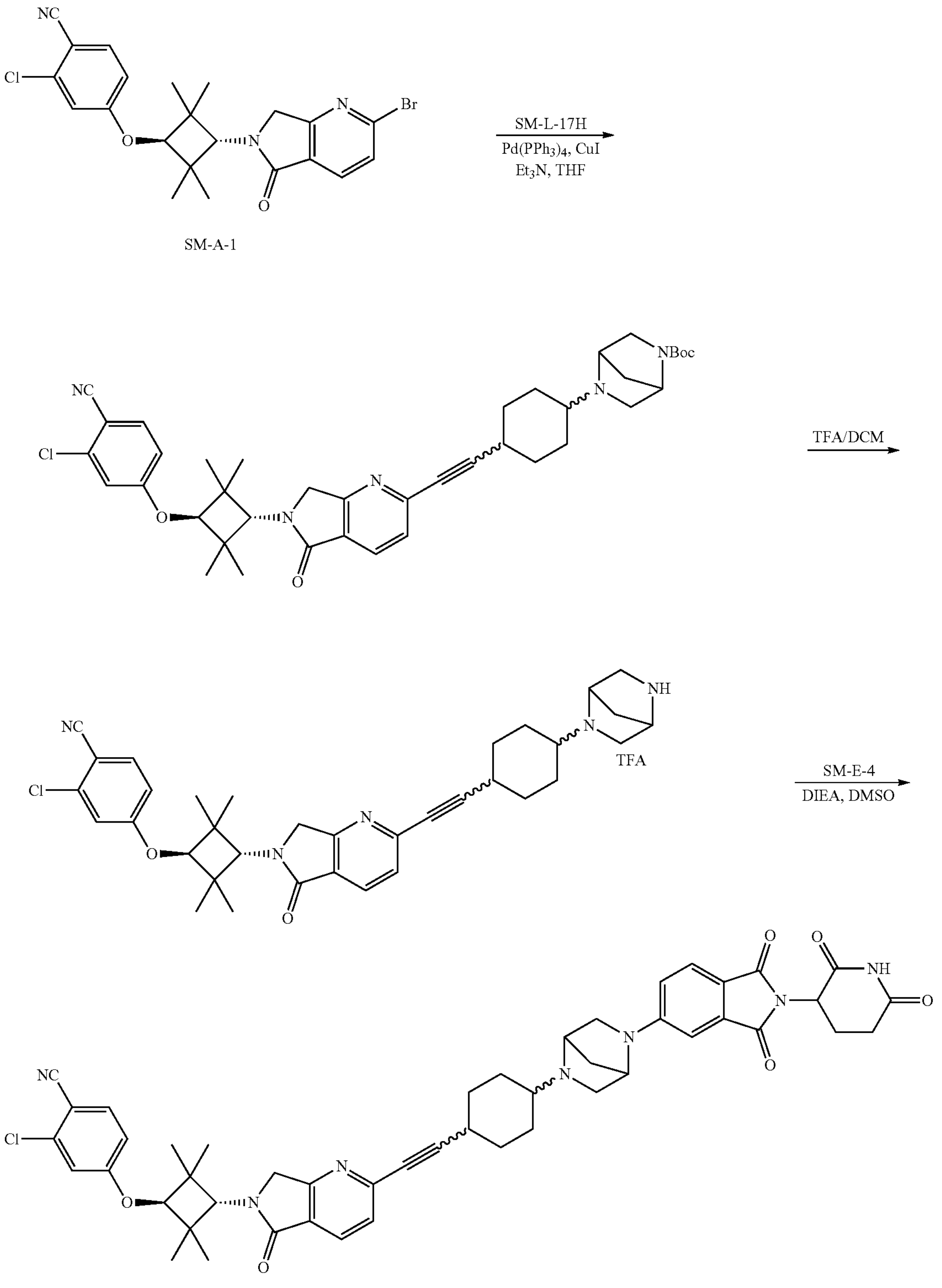

$^1$H NMR (400 MHz, DMSO-$d_6$) δ 11.06 (s, 1H), 8.01 (d, J=7.9 Hz, 1H), 7.88 (d, J=8.8 Hz, 1H), 7.62 (d, J=8.4 Hz, 1H), 7.49 (d, J=7.9 Hz, 1H), 7.27 (d, J=2.3 Hz, 1H), 7.04 (dd, J=8.8, 2.3 Hz, 2H), 6.87 (s, 1H), 5.04 (dd, J=13.0, 5.3 Hz, 1H), 4.76 (s, 2H), 4.62 (s, 1H), 4.51 (s, 1H), 4.31 (s, 1H), 3.81 (s, 1H), 3.39 (s, 2H), 3.07 (s, 1H), 2.85-2.66 (m, 1H), 2.59-2.51 (m, 2H), 2.33-2.30 (m, 2H), 2.21-2.19 (m, 1H), 2.03-1.73 (m, 7H), 1.45-1.34 (m, 8H), 1.25-1.13 (m, 8H). MS: calcd. for $C_{48}H_{48}ClN_7O_6$ [M+H]$^+$: 854.3; found: 854.0.

354: 2-Chloro-4-((1r,3r)-3-(2-((1s, 3S)-3-(4-(2-(2,6-dioxopiperidin-3-yl)-1,3-dioxoisoindolin-5-yl)piperazin-1-yl)cyclobutyl)ethynyl)-5-oxo-5,7-dihydro-6H-pyrrolo[3,4-b]pyridin-6-yl)-2,2,4,4-tetramethylcyclobutoxy)benzonitrile

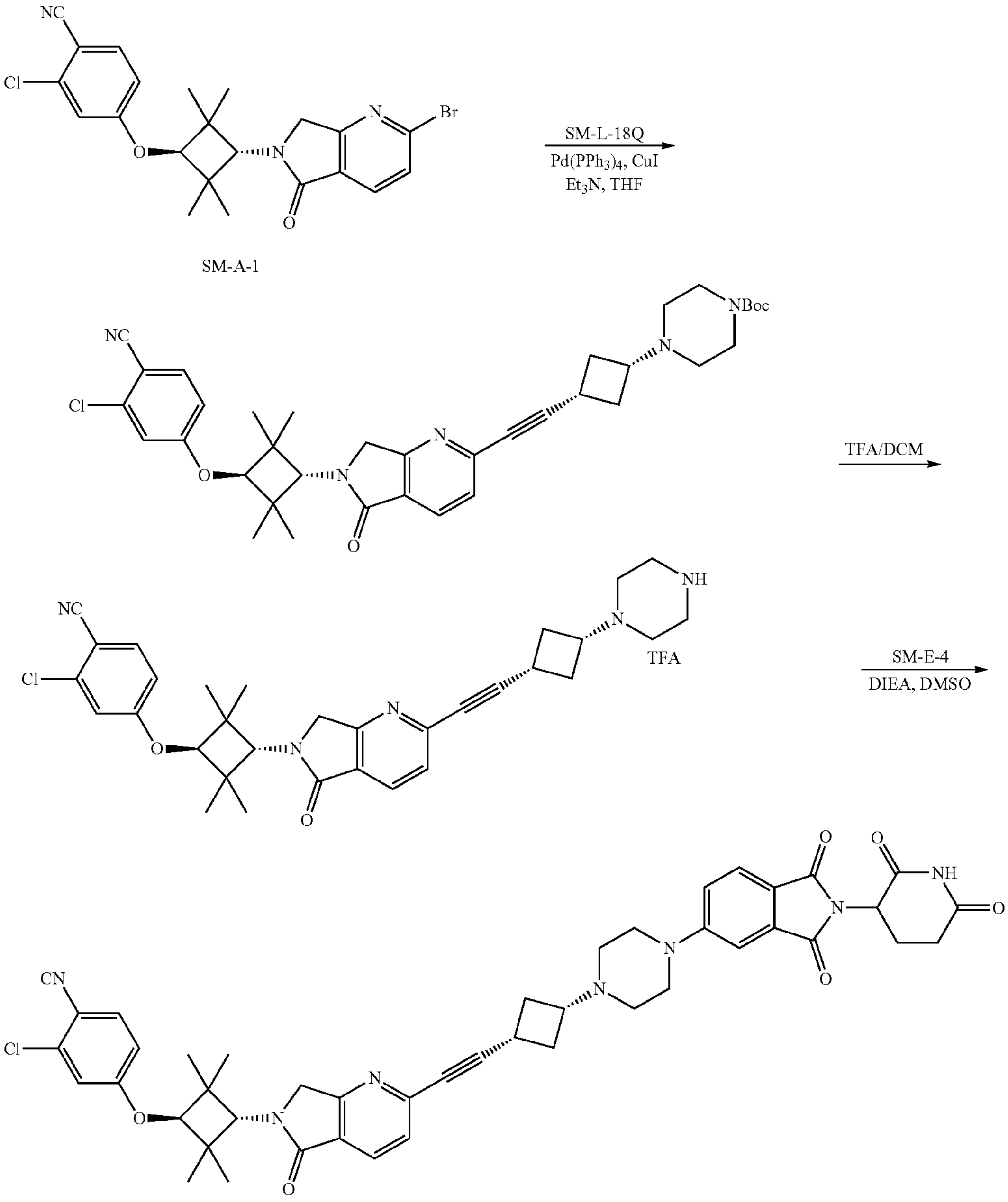

354

$^1$H NMR (400 MN-z, DMSO-$d_6$) δ 11.07 (s, 1H), 8.03 (d, J=7.9 Hz, 1H), 7.88 (d, J=8.8 Hz, 1H), 7.66 (d, J=8.5 Hz, 1H), 7.54 (s, 1H), 7.33 (s, 1H), 7.29-7.24 (m, 2H), 7.04 (dd, J=8.8, 2.4 Hz, 1H), 5.05 (dd, J=12.8, 5.3 Hz, 1H), 4.77 (s, 2H), 4.52 (s, 1H), 4.31 (s, 1H), 3.40 (d, J=20.9 Hz, 4H), 3.08-2.97 (m, 1H), 2.93-2.79 (m, 1H), 2.79-2.67 (m, 1H), 2.66-2.49 (m, 4H), 2.39 (s, 4H), 2.05-1.96 (m, 3H), 1.38 (s, 6H), 1.14 (s, 6H). MS: calcd. for $C_{45}H_{44}ClN_7O_6$ $[M+H]^+$: 814.3; found: 814.0.
355: 2-Chloro-4-((1r,3r)-3-(2-((1r,3r)-3-(4-(2-(2,6-dioxopiperidin-3-yl)-1,3-dioxoisoindolin-5-yl)piperazin-1-yl)cyclobutyl)ethynyl)-5-oxo-5,7-dihydro-6H-pyrrolo[3,4-b]pyridin-6-yl)-2,2,4,4-tetramethylcyclobutoxy)benzonitrile
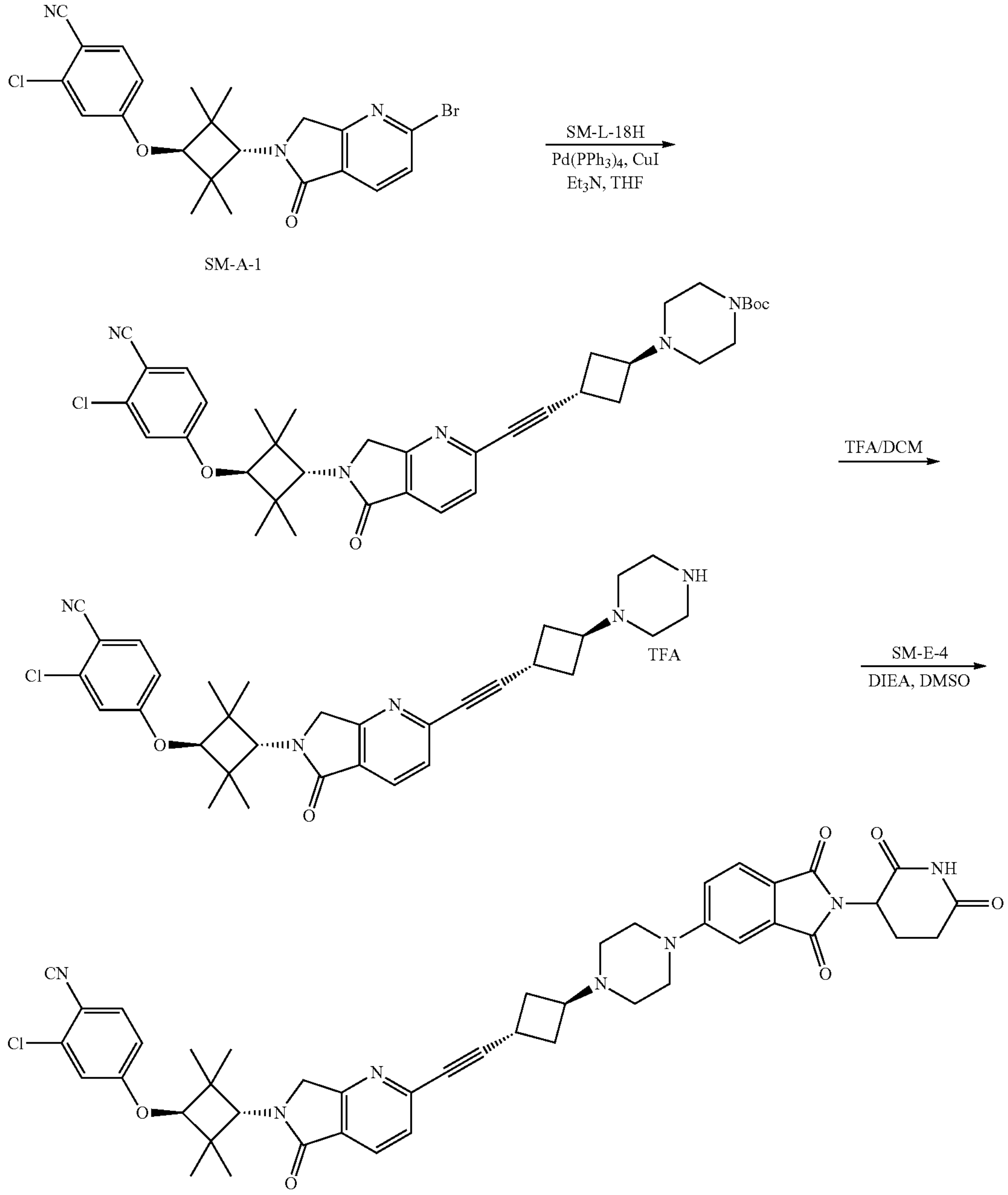
355
$^1H$ NMR (400 MHz, DMSO-$d_6$) δ 11.06 (s, 1H), 8.04 (d, J=7.8 Hz, 1H), 7.89 (d, J=8.7 Hz, 1H), 7.67 (d, J=8.4 Hz, 1H), 7.56 (d, J=7.9 Hz, 1H), 7.34 (s, 1H), 7.29-7.24 (m, 2H), 7.05 (dd, J=8.8, 2.5 Hz, 1H), 5.05 (dd, J=12.6, 5.3 Hz, 1H), 4.78 (s, 2H), 4.53 (s, 1H), 4.32 (s, 1H), 3.43 (s, 4H), 3.13-3.02 (m, 1H), 2.91-2.78 (m, 1H), 2.60-2.50 (m, 2H), 2.41 (s, 4H), 2.38-2.25 (m, 3H), 2.27-2.13 (m, 2H), 2.03-1.96 (m, 1H), 1.38 (s, 6H), 1.14 (s, 6H). MS: calcd. for $C_{45}H_{44}ClN_7O_6$ $[M+H]^+$: 814.3; found: 813.8.
356: 2-Chloro-4-((1r,3r)-3-(2-((3-(4-(2,6-dioxopiperidin-3-yl)-6-fluoro-1,3-dioxoisoindolin-5-yl)piperazin-1-yl)cyclobutyl)ethynyl)-5-oxo-5,7-dihydro-6H-pyrrolo[3,4-b]pyridin-6-yl)-2,2,4,4-tetramethylcyclobutoxy)benzonitrile
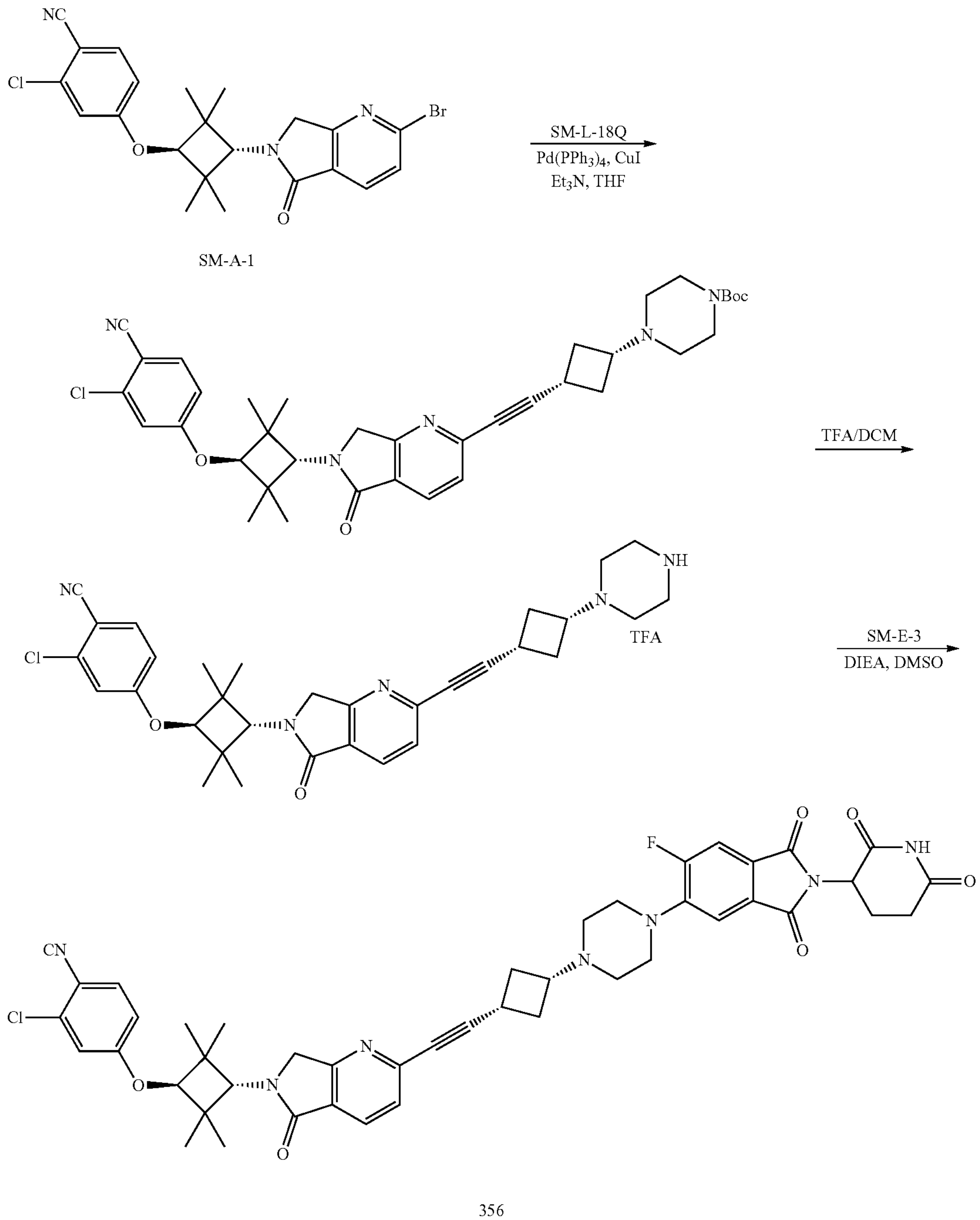
$^1$H NMR (400 MHz, DMSO-$d_6$) δ 11.10 (s, 1H), 8.03 (d, J=7.9 Hz, 1H), 7.88 (d, J=8.8 Hz, 1H), 7.71 (d, J=11.4 Hz, 1H), 7.55 (d, J=7.9 Hz, 1H), 7.44 (d, J=7.4 Hz, 1H), 7.27 (d, J=2.3 Hz, 1H), 7.04 (dd, J=8.8, 2.4 Hz, 1H), 5.09 (dd, J=12.8, 5.4 Hz, 1H), 4.78 (s, 2H), 4.52 (s, 1H), 4.31 (s, 1H), 3.23 (s, 4H), 3.09-2.98 (m, 1H), 2.92-2.71 (m, 2H), 2.61-

2.49 (m, 4H), 2.43 (s, 4H), 2.07-1.92 (m, 3H), 1.38 (s, 6H), 1.14 (s, 6H). MS: calcd. for $C_{45}H_{43}ClFN_7O_6$ $[M+H]^+$: 832.3; found: 832.0.
357: 2-Chloro-4-((1r,3r)-3-(2-((3-(4-(2,6-dioxopiperidin-3-yl)-6-fluoro-1,3-dioxoisoindolin-5-yl)piperazin-1-yl)cyclobutyl)ethynyl)-5-oxo-5,7-dihydro-6H-pyrrolo[3,4-b]pyridin-6-yl)-2,2,4,4-tetramethylcyclobutoxy)benzonitrile
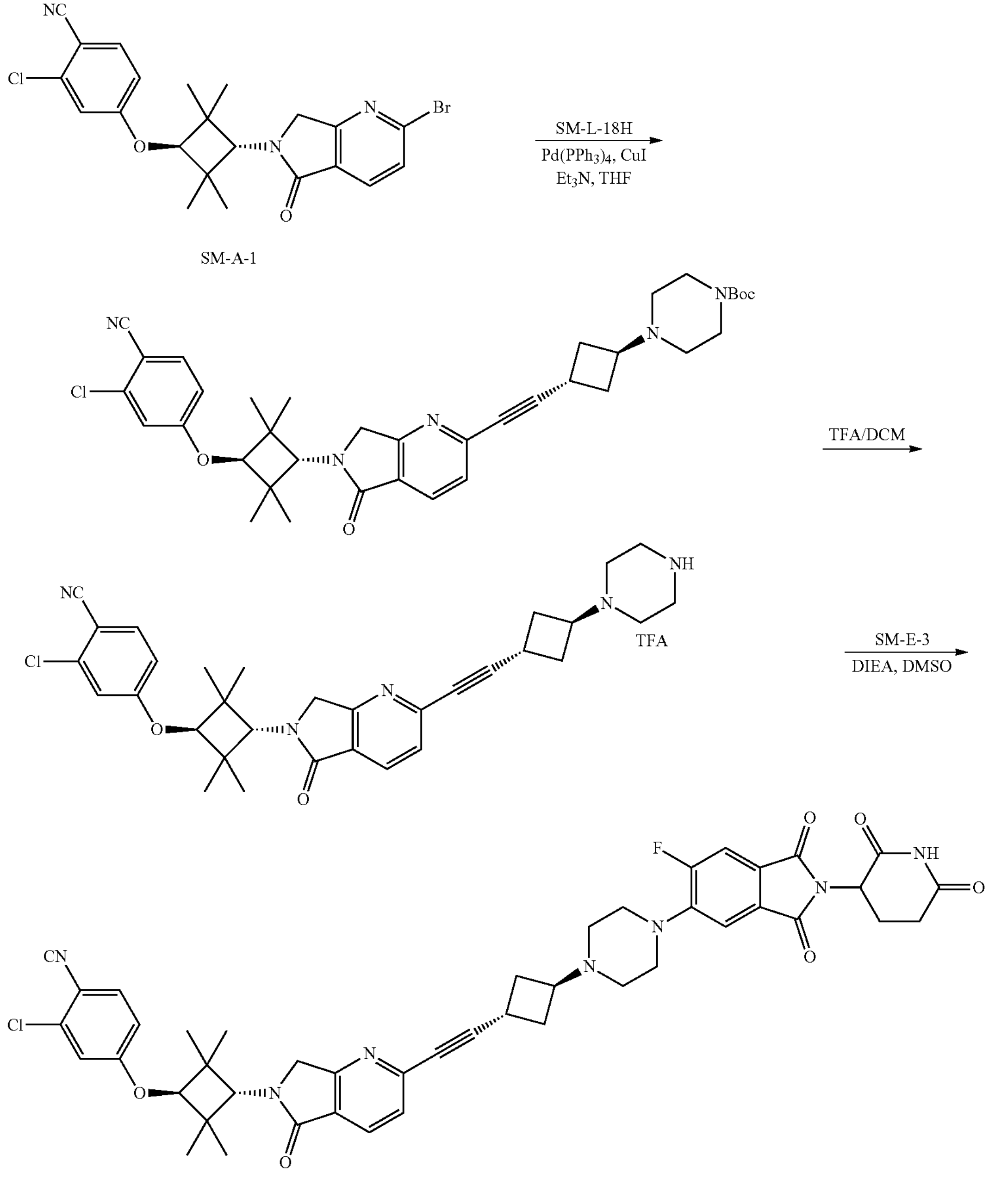
357
$^1H$ NMR (400 MHz, DMSO-$d_6$) δ 11.09 (s, 1H), 8.04 (d, J=7.9 Hz, 1H), 7.89 (d, J=8.7 Hz, 1H), 7.72 (d, J=11.4 Hz, 1H), 7.57 (d, J=7.9 Hz, 1H), 7.44 (d, J=7.7 Hz, 1H), 7.27 (d, J=2.4 Hz, 1H), 7.05 (dd, J=8.8, 2.4 Hz, 1H), 5.09 (dd, J=12.8, 5.4 Hz, 1H), 4.79 (s, 2H), 4.53 (s, 1H), 4.32 (s, 1H), 3.24 (s, 4H), 3.17-3.07 (m, 1H), 2.92-2.79 (m, 1H), 2.62-

2.49 (m, 2H), 2.45-2.37 (m, 4H), 2.36-2.26 (m, 3H), 2.26-2.15 (m, 2H), 2.05-1.97 (m, 1H), 1.31 (s, 6H), 1.18 (s, 6H). MS: calcd. for $C_{45}H_{43}ClFN_7O_6$ $[M+H]^+$: 832.3; found: 831.7.
358: 2-chloro-4-((1r,3r)-3-(2-((3-(5-(2-(2,6-dioxopiperidin-3-yl)-1,3-dioxoisoindolin-5-yl)hexahydropyrrolo[3,4-c]pyrrol-2(1H)-yl)cyclobutyl) ethynyl)-5-oxo-5,7-dihydro-6H-pyrrolo[3,4-b]pyridin-6-yl)-2,2,4,4-tetramethylcyclobutoxy)benzonitrile
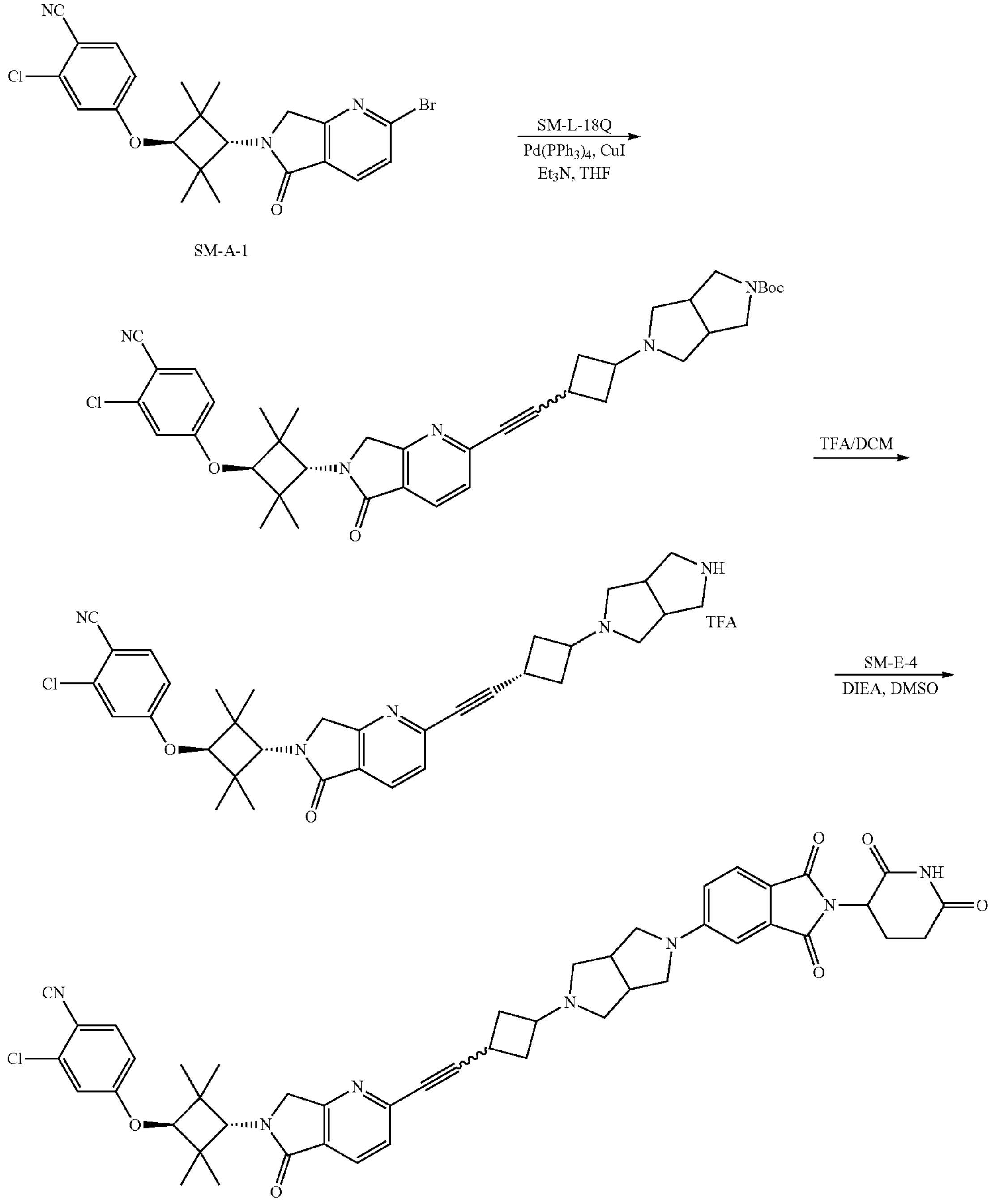
358

$^1$H NMR (400 MHz, DMSO-$d_6$) δ 11.08 (s, 1H), 8.02 (d, J=7.9 Hz, 1H), 7.91 (d, J=8.8 Hz, 1H), 7.66 (d, J=8.3 Hz, 1H), 7.54 (d, J=7.9 Hz, 1H), 7.29 (d, J=2.3 Hz, 1H), 7.06 (dd, J=8.8, 2.3 Hz, 1H), 6.96 (s, 1H), 6.86 (d, J=8.4 Hz, 1H), 5.06 (dd, J=12.9, 5.3 Hz, 1H), 4.78 (s, 2H), 4.54 (s, 1H), 4.32 (s, 1H), 3.67 (s, 2H), 3.31 (s, 3H), 3.30-3.25 (m, 1H), 3.11-2.82 (m, 5H), 2.66-2.53 (m, 4H), 2.46-2.39 (m, 2H), 2.14-1.94 (m, 3H), 1.39 (s, 6H), 1.15 (s, 6H). MS: calcd. for $C_{47}H_{46}ClN_7O_6$ $[M+H]^+$: 840.3; found: 840.3.
359: 2-Chloro-4-((1r,3r)-3-(2-((3-(5-(2-(2,6-dioxopiperidin-3-yl)-1,3-dioxoisoindolin-5-yl)hexahydropyrrolo[3,4-c]pyrrol-2(1H)-yl)cyclobutyl) ethynyl)-5-oxo-5,7-dihydro-6H-pyrrolo[3,4-b]pyridin-6-yl)-2,2,4,4-tetramethylcyclobutoxy)benzonitrile
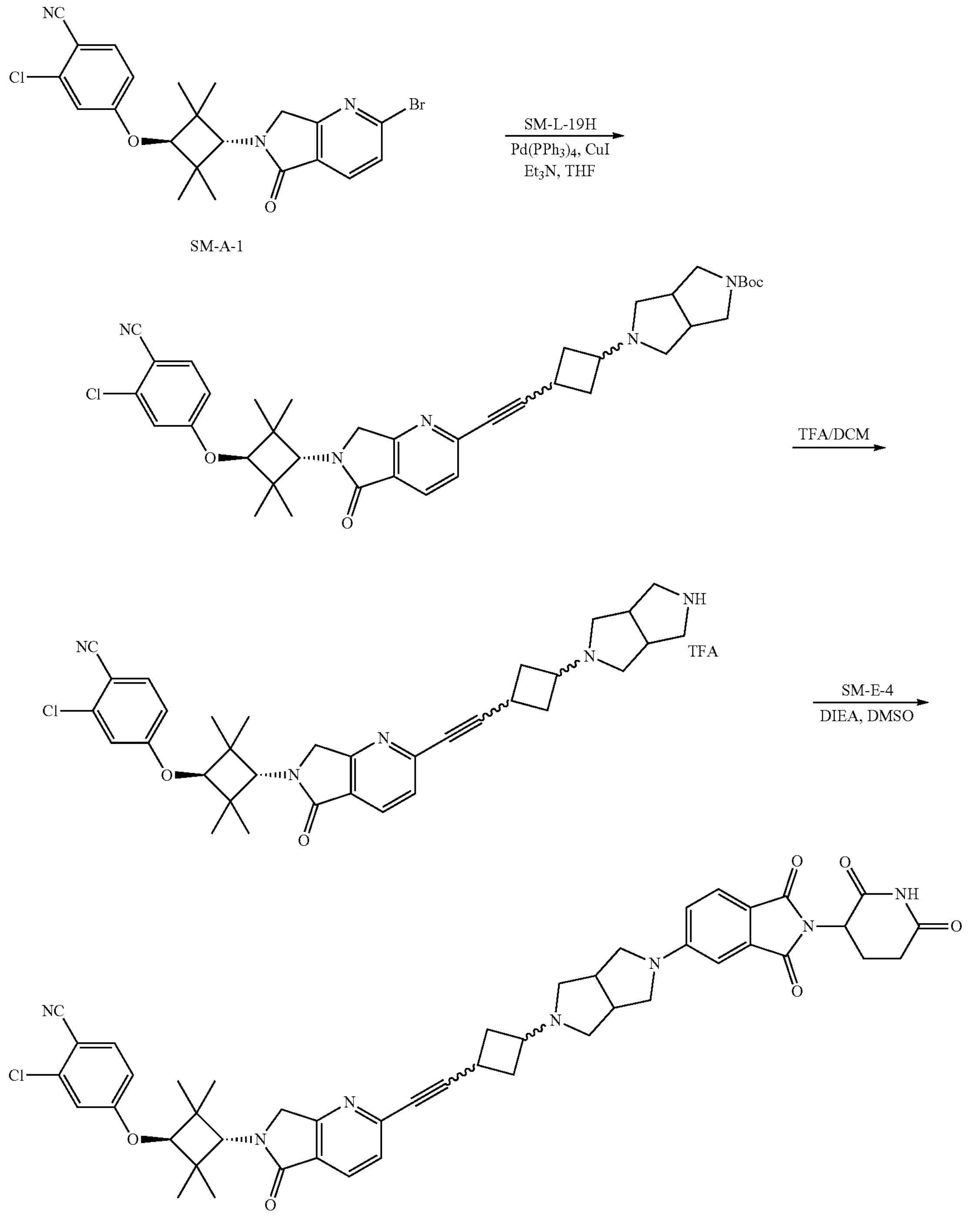
359

$^1$H NMR (400 MHz, DMSO-$d_6$) δ 11.09 (s, 1H), 8.05 (d, J=7.9 Hz, 1H), 7.91 (d, J=8.8 Hz, 1H), 7.67 (d, J=8.4 Hz, 1H), 7.56 (d, J=7.9 Hz, 1H), 7.29 (d, J=2.3 Hz, 1H), 7.07 (d, J=8.8, 2.3 Hz, 1H), 6.96 (s, 1H), 6.87 (d, J=8.8 Hz, 1H), 5.07 (d, J=12.9, 5.4 Hz, 1H), 4.80 (s, 2H), 4.54 (s, 1H), 4.34 (s, 1H), 3.67 (s, 2H), 3.31 (d, J=8.8 Hz, 2H), 3.20 (s, 1H), 2.99-2.78 (m, 3H), 2.63-2.58 (m, 5H), 2.48-2.42 (m, 2H), 2.33 (s, 2H), 2.20 (s, 2H), 2.07-2.02 (m, 1H), 1.40 (s, 6H), 1.16 (s, 6H). MS: calcd. for $C_{47}H_{46}ClN_7O$; $[M+H]^+$: 840.3; found: 840.3.
360: 2-Chloro-4-((1r,3r)-3-(2-((3-(5-(2,6-dioxopiperidin-3-yl)-6-fluoro-1,3-dioxoisoindolin-5-yl)hexahydropyrrolo[3,4-c]pyrrol-2(1H)-cyclobutyl)ethynyl)-5-oxo-5,7-dihydro-6H-pyrrolo[3,4-b]pyridin-6-yl)-2,2,4,4-tetramethylcyclobutoxy benzonitrile
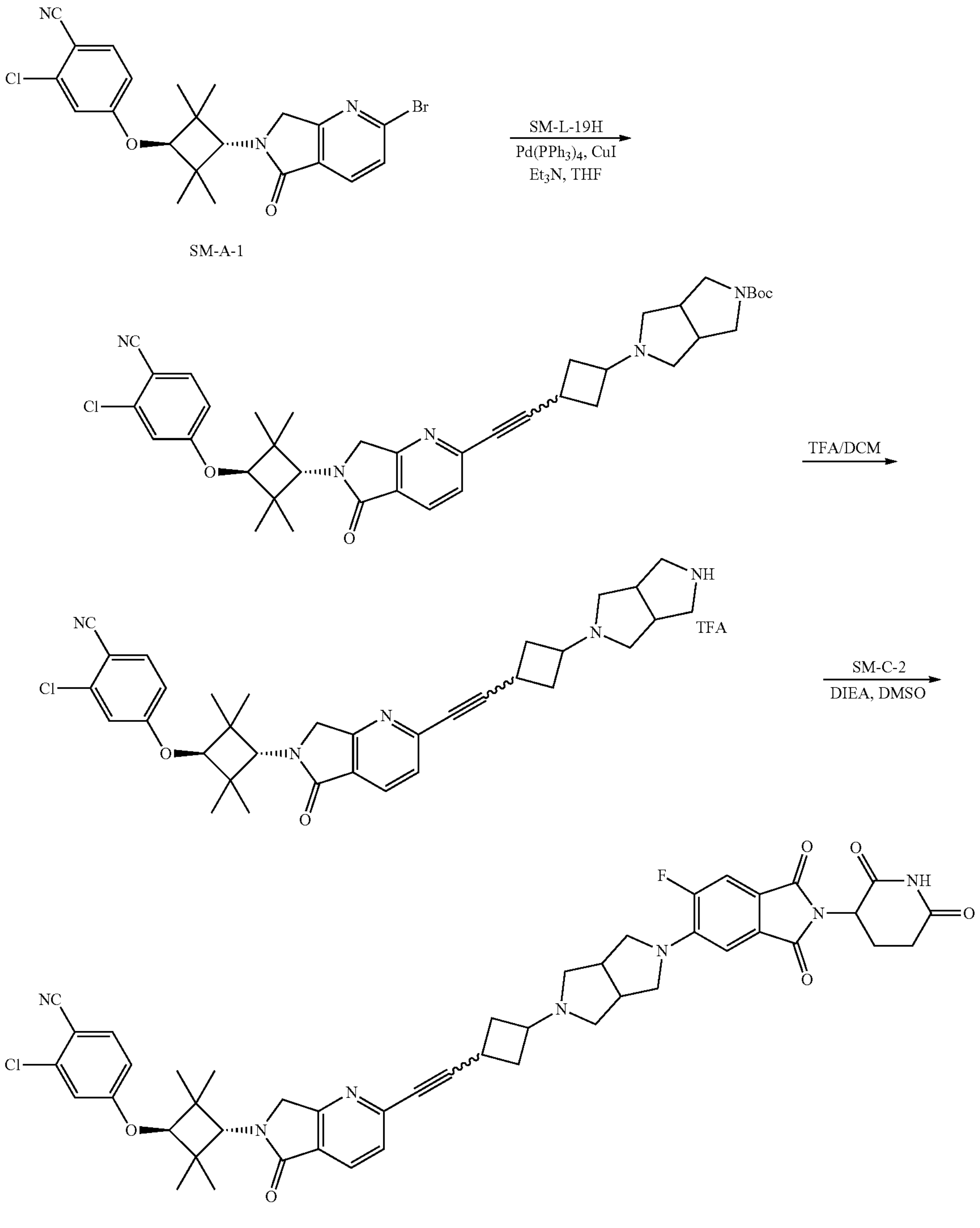
360

$^1$H NMR (400 MHz, DMSO-$d_6$) δ 11.10 (s, 1H), 8.03 (d, J=7.9 Hz, 1H), 7.91 (d, J=8.8 Hz, 1H), 7.64 (d, J=12.7 Hz, 1H), 7.54 (d, J=7.9 Hz, 1H), 7.29 (d, J=2.2 Hz, 1H), 7.15 (d, J=7.6 Hz, 1H), 7.07 (d, J=8.6 Hz, 1H), 5.08 (dd, J=12.5, 5.1 Hz, 1H), 4.78 (s, 2H), 4.54 (s, 1H), 4.33 (s, 1H), 3.72 (s, 2H), 3.32 (s, 4H), 3.11-3.02 (m, 1H), 2.89 (s, 4H), 2.60 (s, 1H), 2.48-2.40 (m, 5H), 2.10-2.05 (m, 3H), 1.40 (s, 6H), 1.15 (s, 6H). MS: calcd. for $C_{47}H_{45}ClFN_7O_6$ $[M+H]^+$: 858.3; found: 857.8.
361: 2-Chloro-4-((1r,3r)-3-(2-((3-(5-(2,6-dioxopiperidin-3-yl)-6-fluoro-1,3-dioxoisoindolin-5-yl)hexahydropyrrolo[3,4-c]pyrrol-2(1H)-cyclobutyl)ethynyl)-5-oxo-5,7-dihydro-6H-pyrrolo[3,4-b]pyridin-6-yl)-2,2,4,4-tetramethylcyclobutoxy) benzonitrile
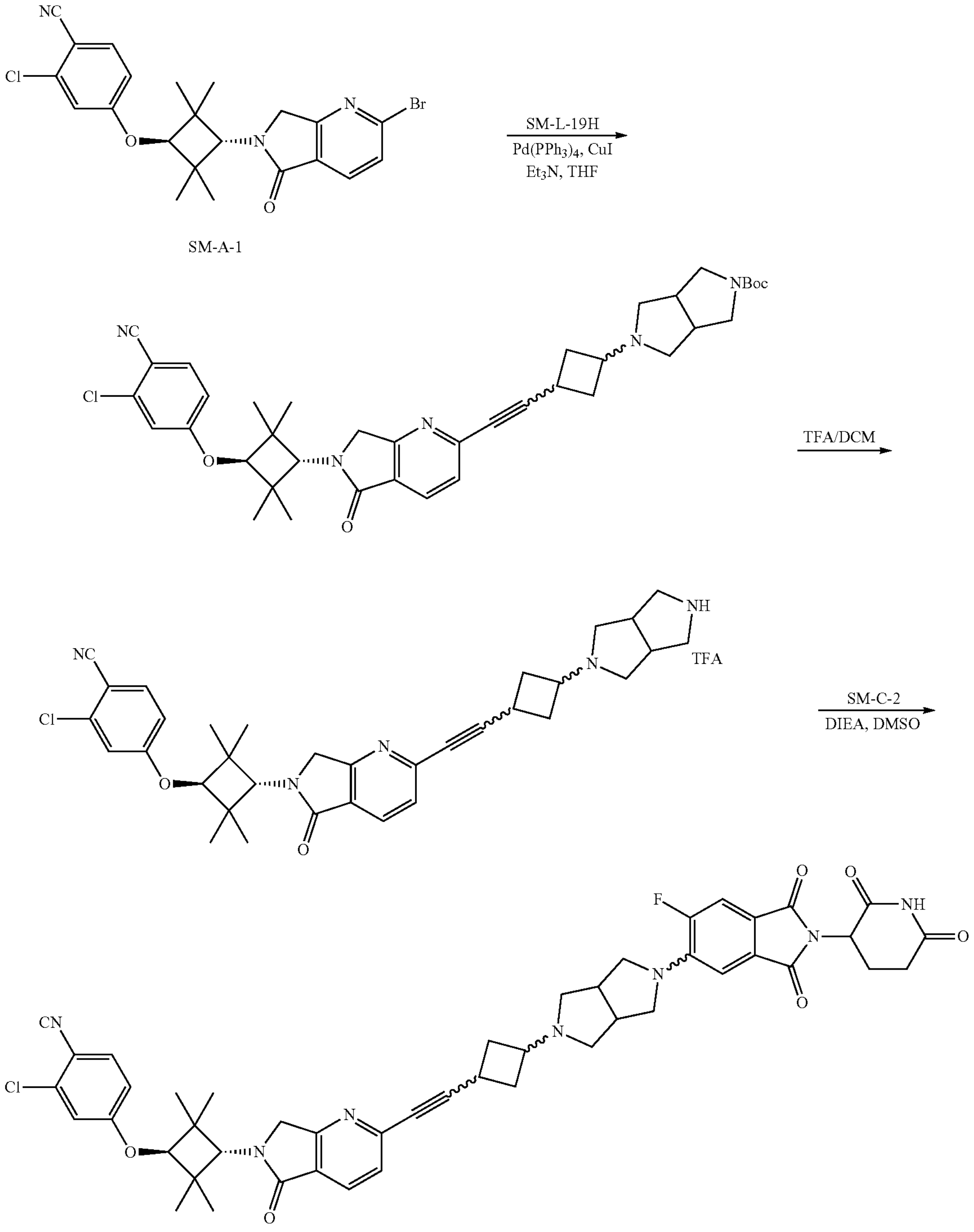
361

$^1H$ NMR (400 MHz, DMSO-$d_6$) δ 11.11 (s, 1H), 8.05 (d, J=7.9 Hz, 1H), 7.91 (d, J=8.7 Hz, 1H), 7.65 (d, J=12.5 Hz, 1H), 7.57 (d, J=7.9 Hz, 1H), 7.29 (d, J=2.2 Hz, 1H), 7.16 (d, J=7.4 Hz, 1H), 7.07 (d, J=8.8, 2.2 Hz, 1H), 5.08 (dd, J=12.8, 5.3 Hz, 1H), 4.80 (s, 2H), 4.54 (s, 1H), 4.34 (s, 1H), 3.71 (s, 2H), 3.32 (s, 2H), 3.20 (s, 1H), 2.88-2.80 (m, 3H), 2.56-2.50 (m, 5H), 2.49-2.41 (m, 2H), 2.34 (s, 2H), 2.21 (s, 2H), 2.09-2.04 (m, 1H), 1.40 (s, 6H), 1.16 (s, 6H). MS: calcd. for $C_{47}H_{45}ClFN_7O_6$ $[M+H]^+$: 858.3; found: 858.3.
362: 2-Chloro-4-((1r,3r)-3-(2-((4-(2-(2,6-dioxopiperidin-3-yl)-1,3-dioxoisoindolin-5-yl)-2,7-diazaspiro[3.5]nonan-7-yl)cyclohexyl)ethynyl)-5-oxo-5,7-dihydro-6H-pyrrolo[3,4-b]pyridin-6-yl)-2,2,4,4-tetramethylcyclobutoxy)benzonitrile
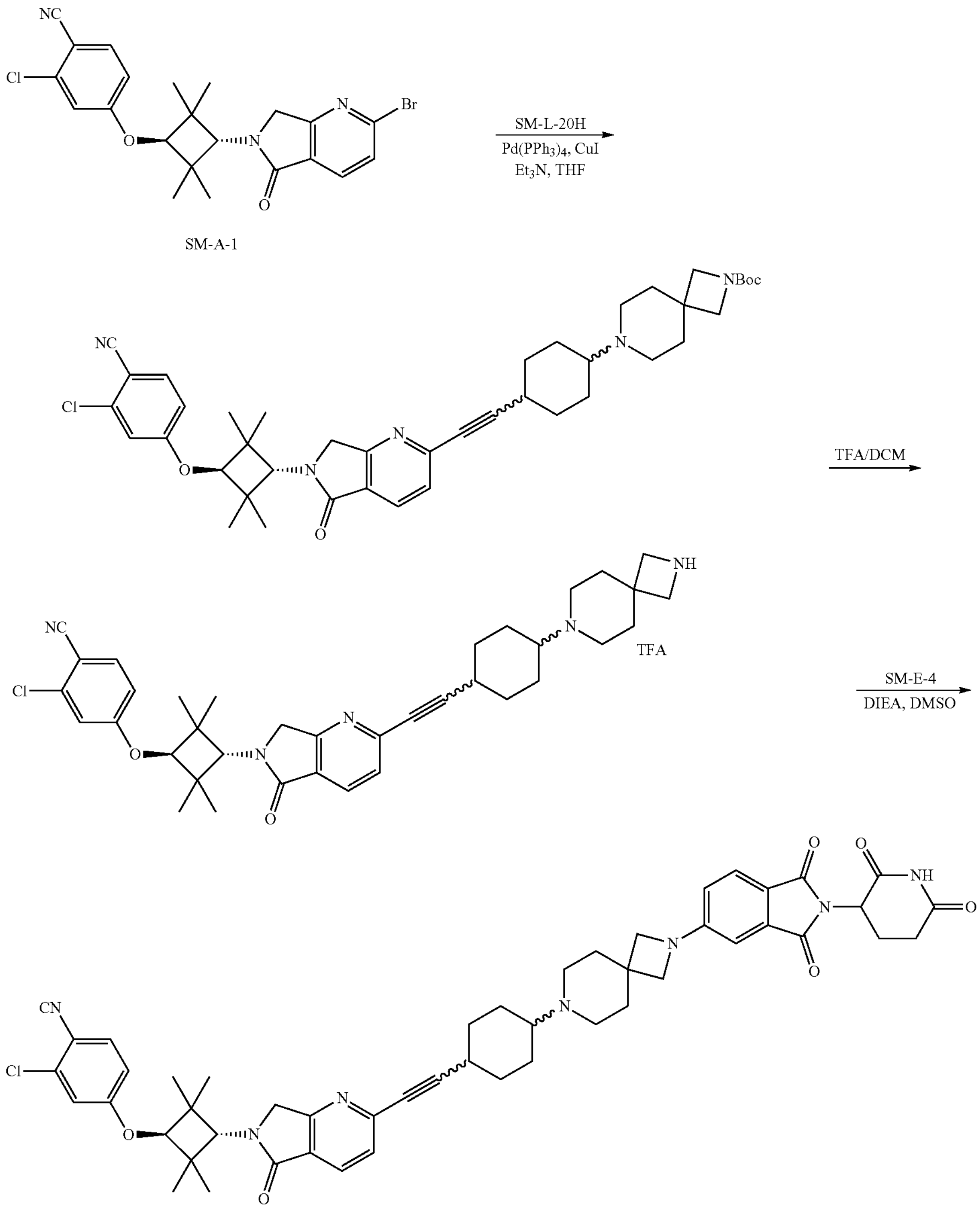

$^1$H NMR (400 MHz, DMSO-$d_6$) δ 11.09 (s, 1H), 8.04 (d, J=7.9 Hz, 1H), 7.91 (d, J=8.7 Hz, 1H), 7.64 (d, J=8.3 Hz, 1H), 7.53 (d, J=7.9 Hz, 1H), 7.29 (d, J=2.3 Hz, 1H), 7.07 (dd, J=8.8, 2.4 Hz, 1H), 6.77 (s, 1H), 6.65 (dd, J=8.3, 1.7 Hz, 1H), 5.05 (dd, J=12.8, 5.4 Hz, 1H), 4.80 (s, 2H), 4.54 (s, 1H), 4.34 (s, 1H), 3.74 (s, 4H), 3.25-3.16 (m, 2H), 2.91-2.83 (m, 1H), 2.68-2.57 (m, 2H), 2.33 (s, 2H), 2.09-1.98 (m, 4H), 1.75 (s, 6H), 1.45-1.35 (m, 111H), 1.16 (s, 6H). MS: calcd. for $C_{50}H_{52}ClN_7O_6$ $[M+H]^+$: 882.4; found: 882.2.
363: 2-Chloro-4-((1r,3r)-3-(2-((4-(2-(2,6-dioxopiperidin-3-yl)-6-fluoro-1,3-dioxoisoindolin-5-yl)-2,7-diazaspiro[3.5]nonan-7-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
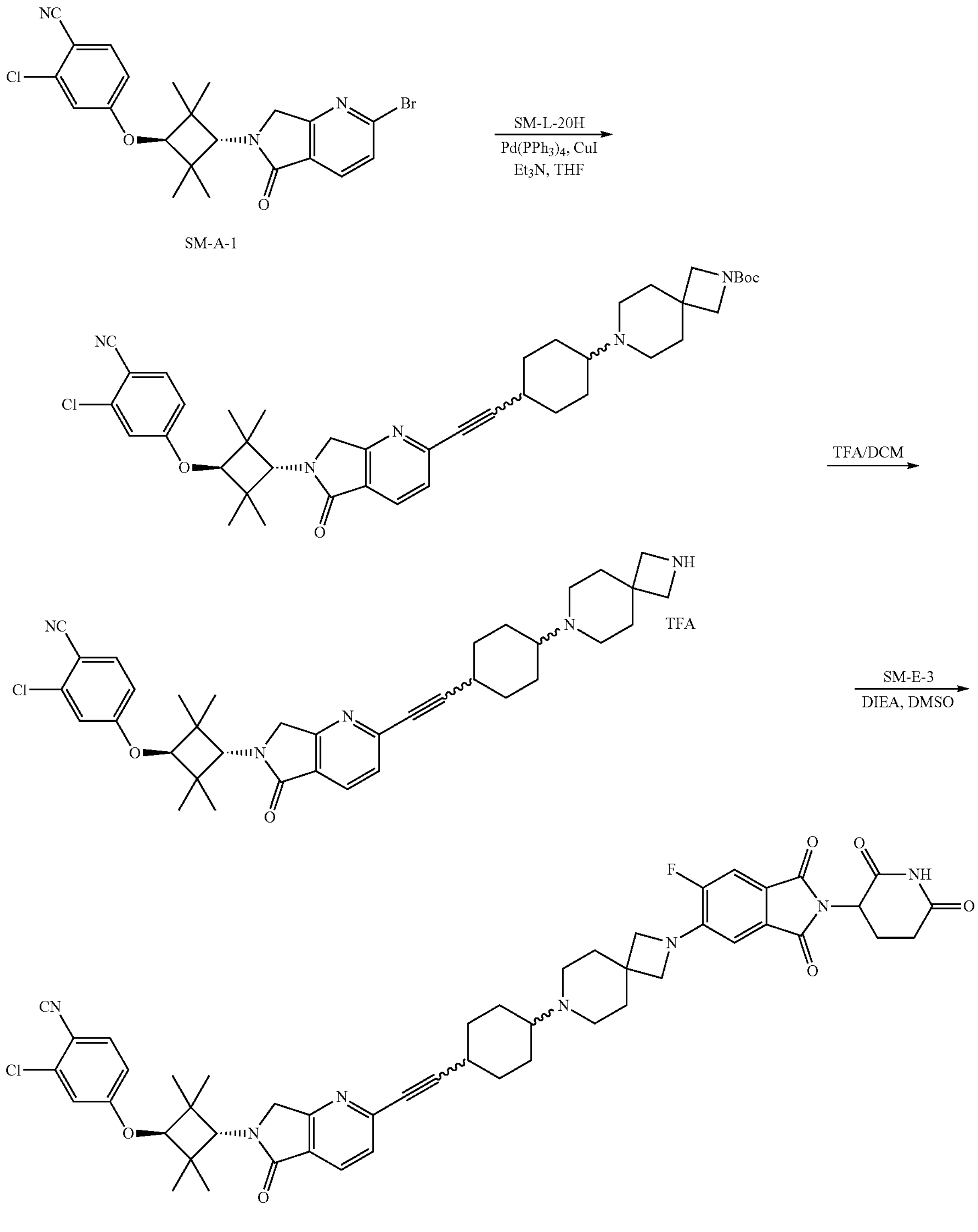

$^1$H NMR (400 MHz, DMSO-$d_6$) δ 11.10 (s, 1H), 8.04 (d, J=8.0 Hz, 1H), 7.91 (d, J=8.8 Hz, 1H), 7.59 (t, J=12.2 Hz, 1H), 7.53 (d, J=7.9 Hz, 1H), 7.29 (d, J=2.2 Hz, 1H), 7.07 (dd, J=8.8, 2.3 Hz, 1H), 6.90 (d, J=7.7 Hz, 1H), 5.06 (dd, J=12.8, 5.3 Hz, 1H), 4.80 (s, 2H), 4.55 (s, 1H), 4.34 (s, 1H), 3.89 (s, 4H), 3.32 (s, 2H), 2.91-2.84 (m, 1H), 2.67-2.56 (m, 2H), 2.50-2.33 (m, 2H), 2.09-2.00 (m, 4H), 1.76-1.68 (m, 6H), 1.50-1.22 (m, 11H), 1.16 (s, 6H). MS: calcd. for $C_{50}H_{51}ClFN_7O_6$ $[M+H]^+$: 900.4; found: 900.3.
364: 2-Chloro-4-((1r,3r)-3-(2-((4-(7-(2-(2,6-dioxopiperidin-3-yl)-1,3-dioxoisoindolin-5-yl)-2,7-Diazaspiro[4.4]nonan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
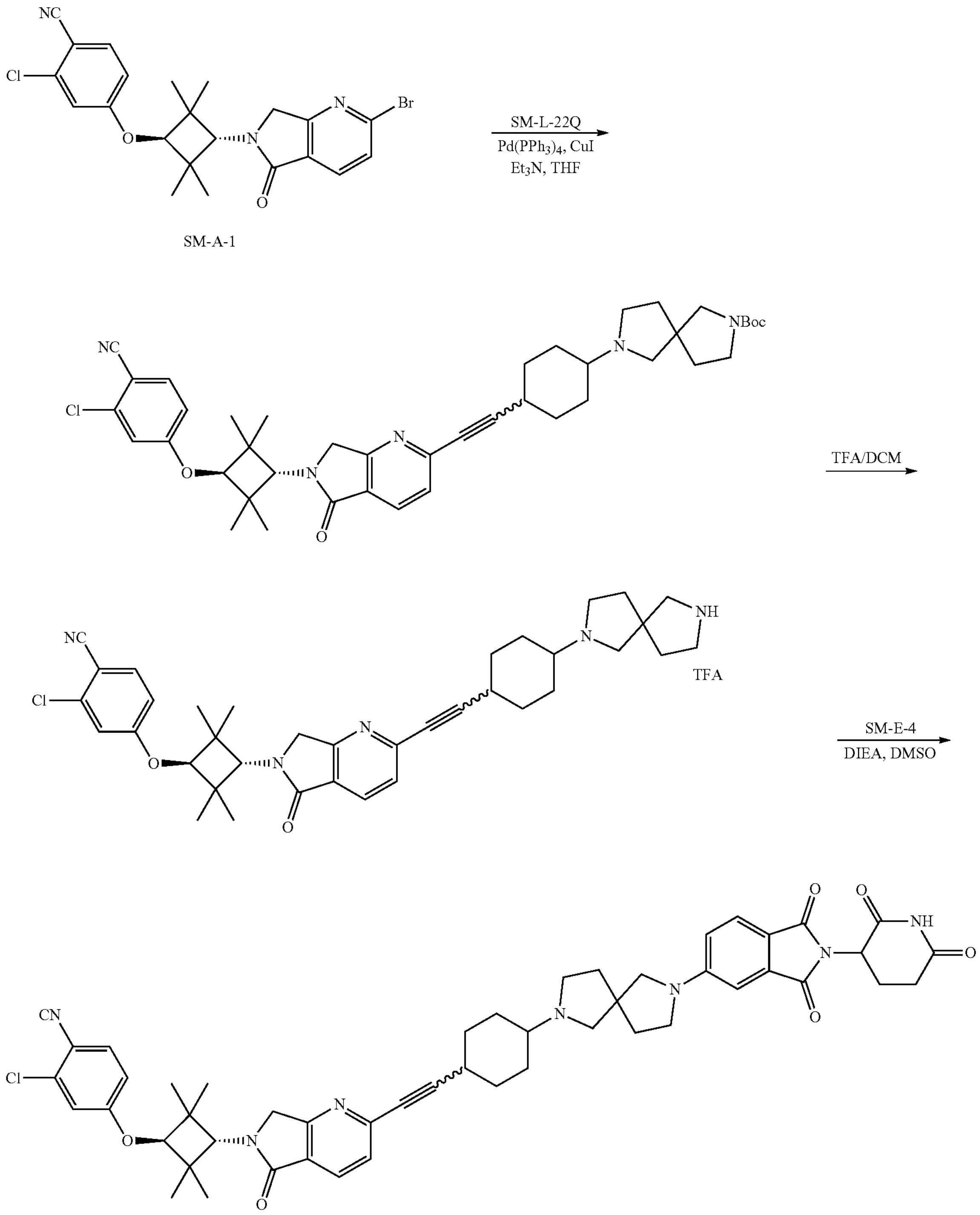
364

$^1$H NMR (400 MHz, DMSO-$d_6$) δ 11.08 (s, 1H), 8.04 (d, J=7.9 Hz, 1H), 7.91 (d, J=8.7 Hz, 1H), 7.64 (d, J=8.5 Hz, 1H), 7.54 (d, J=7.9 Hz, 1H), 7.29 (d, J=2.2 Hz, 1H), 7.07 (dd, J=8.8, 2.3 Hz, 1H), 6.90 (s, 1H), 6.81 (d, J=8.3 Hz, 1H), 5.06 (dd, J=13.0, 5.3 Hz, 1H), 4.80 (s, 2H), 4.54 (s, 1H), 4.34 (s, 1H), 3.46 (s, 2H), 2.41-3.38 (m, 1H), 3.32 (s, 2H), 2.93-2.84 (m, 1H), 2.60-2.54 (m, 6H), 2.12-1.89 (m, 8H), 1.77-1.75 (m, 2H), 1.50-1.44 (m, 2H), 1.40 (s, 6H), 1.31-1.24 (m, 2H), 1.16 (s, 6H). MS: calcd. for $C_{50}H_{52}ClN_7O_6$ $[M+H]^+$: 882.4; found: 882.3.

365: 2-Chloro-4-((1r,3r)-3-(2-((4-(7-(2-(2,6-dioxopiperidin-3-yl)-1,3-dioxoisoindolin-5-yl)-2,7-Diazaspiro[4.4]nonan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile

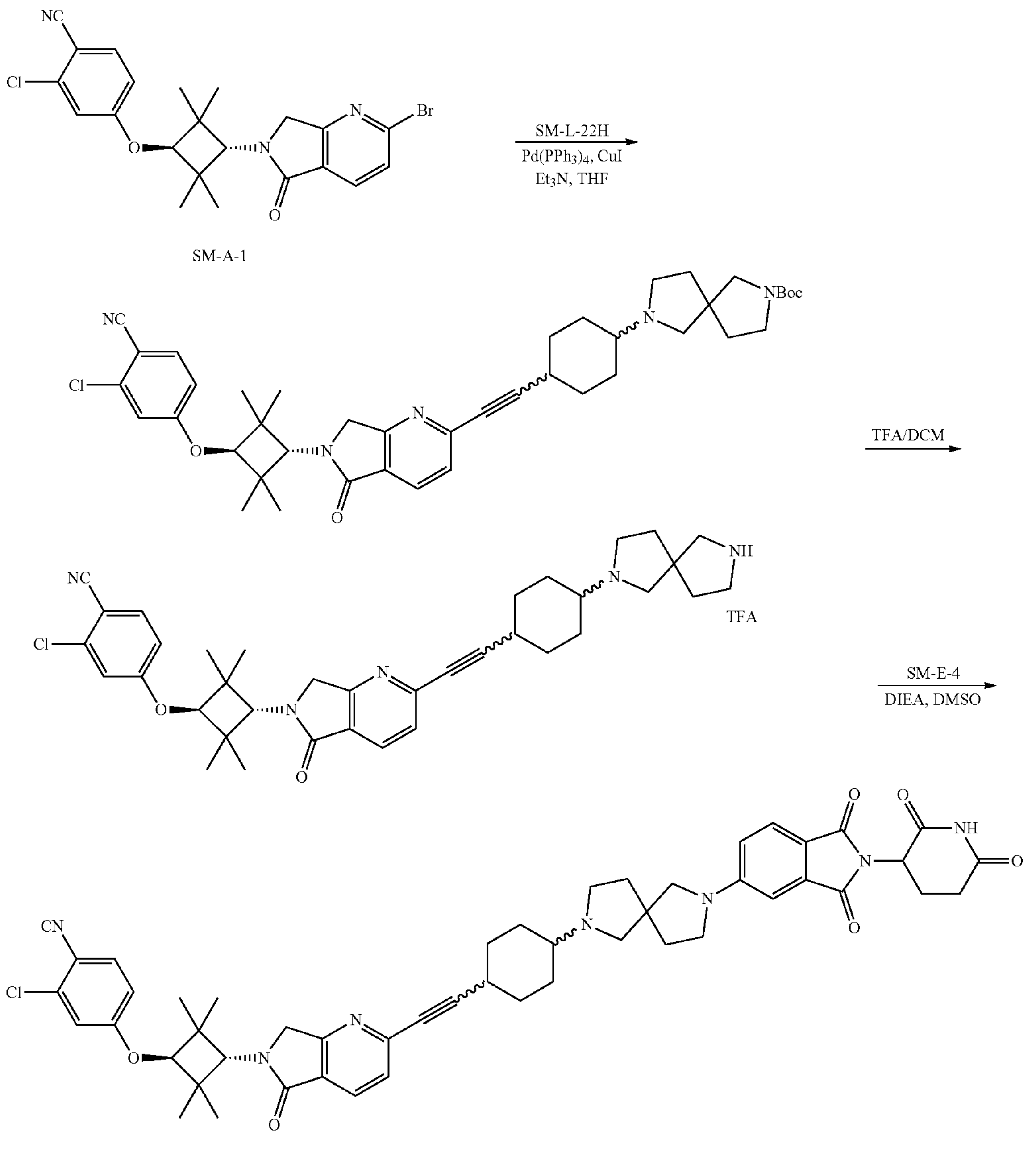

365

$^1$H NMR (400 MHz, DMSO-$d_6$) δ 11.08 (s, 1H), 8.07 (d, J=7.9 Hz, 1H), 7.91 (d, J=8.7 Hz, 1H), 7.71-7.50 (m, 2H), 7.30 (d, J=2.4 Hz, 1H), 7.07 (dd, J=8.8, 2.4 Hz, 1H), 6.90 (s, 1H), 6.81 (d, J=6.8 Hz, 1H), 5.05 (dd, J=12.6, 5.4 Hz, 1H), 4.82 (s, 2H), 4.55 (s, 1H), 4.35 (s, 1H), 3.48 (s, 2H), 3.42-3.35 (m, 1H), 3.28-3.17 (m, 2H), 2.92-2.84 (m, 1H), 2.67-2.54 (m, 6H), 2.02-1.91 (m, 2H), 1.85-1.64 (m, 8H), 1.41 (s, 6H), 1.35-1.29 (m, 2H), 1.23-1.20 (m, 2H), 1.16 (s, 6H). MS: calcd. for $C_{50}H_{52}ClN_7O_6$ $[M+H]^+$: 882.4; found: 882.3.

366: 2-Chloro-4-((1r,3r)-3-(2-((4-(7-(2-(2,6-dioxopiperidin-3-yl)-6-fluoro-1,3-dioxoisoindolin-5-yl)-2,7-diazaspiro[4.4]nonan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile

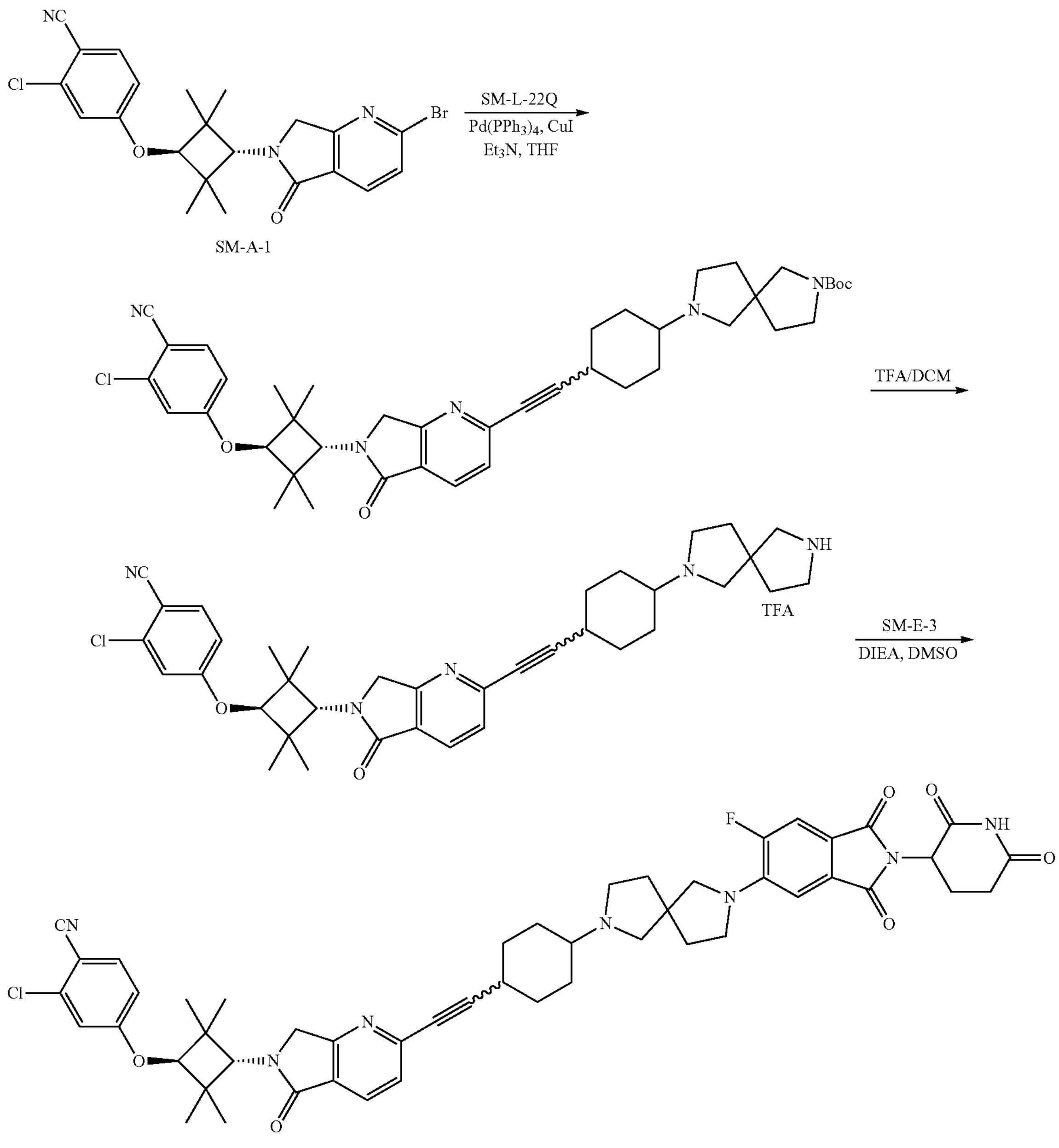

366

$^1$H NMR (400 MHz, DMSO-$d_6$) δ 11.06 (s, 1H), 8.02 (d, J=7.8 Hz, 1H), 7.88 (d, J=8.7 Hz, 1H), 7.58 (d, J=12.5 Hz, 1H), 7.51 (d, J=7.9 Hz, 1H), 7.27 (d, J=2.1 Hz, 1H), 7.03 (t, J=9.1 Hz, 2H), 5.04 (dd, J=12.7, 5.1 Hz, 1H), 4.77 (s, 2H), 4.52 (s, 1H), 4.31 (s, 1H), 3.60 (s, 2H), 3.55-3.42 (m, 2H), 3.28 (s, 1H), 2.91-2.82 (m, 1H), 2.62-2.54 (m, 6H), 2.11-1.91 (m, 8H), 1.78-1.70 (m, 2H), 1.48-1.40 (m, 2H), 1.38 (s, 6H), 1.31-1.19 (m, 2H), 1.14 (s, 6H). MS: calcd. for $C_{50}H_{51}ClFN_7O_6$ $[M+H]^+$: 900.4, found: 900.3.

367: 2-Chloro-4-((1r,3r)-3-(2-((4-(7-(2-(2,6-dioxopiperidin-3-yl)-6-fluoro-1,3-dioxoisoindolin-5-yl)-2,7-diazaspiro[4.4]nonan-2-yl)cyclohexyl)ethynyl)-5-oxo-5,7-dihydro-6H-pyrrolo[3,4-b]pyridin-6-yl)-2,2,4,4-tetramethylcyclobutoxy) benzonitrile
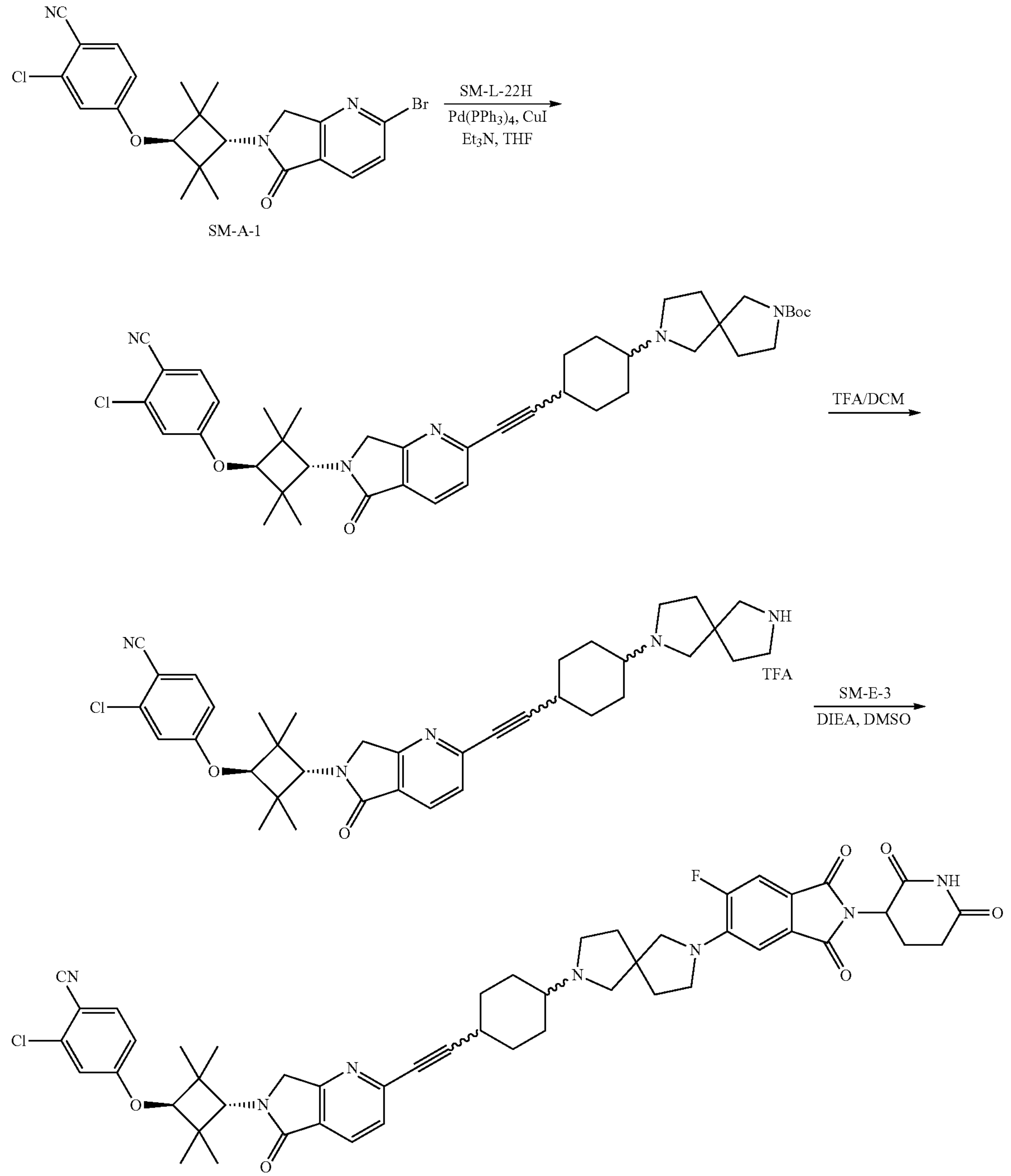
367
$^1$H NMR (400 MHz, DMSO-$d_6$) δ 11.09 (s, 1H), 8.06 (d, J=7.7 Hz, 1H), 7.91 (d, J=8.8 Hz, 1H), 7.59 (t, J=10.2 Hz, 2H), 7.30 (d, J=2.4 Hz, 1H), 7.07 (dd, J=13.5, 4.8 Hz, 2H), 5.06 (dd, J=13.6, 5.5 Hz, 1H), 4.81 (s, 2H), 4.54 (s, 1H), 4.35 (s, 1H), 3.64-3.60 (m, 2H), 3.55-3.49 (m, 2H), 3.31 (s, 1H), 2.87-2.85 (m, 1H), 2.67-2.54 (m, 6H), 2.03-1.75 (m, 8H), 1.68-1.63 (m, 2H), 1.44 (s, 6H), 1.34-1.28 (m, 2H), 1.20-1.17 (m, 2H), 1.16 (s, 6H). MS: calcd. for $C_{49}H_{50}ClFN_7O_6$ $[M+H]^+$: 900.4; found: 900.3.

368: 2-Chloro-4-((1r,3r)-3-(2-((4-(6-(2-(2,6-dioxopiperidin-3-yl)-1,3-dioxoisoindolin-5-yl)-2,6-diazaspiro[3.4]octane-2-yl)cyclohexyl)ethynyl)-5-oxo-5,7-dihydro-pyrrolo[3,4-b]pyridin-6-yl)-2,2,4,4-tetramethylcyclobutoxy) benzonitrile
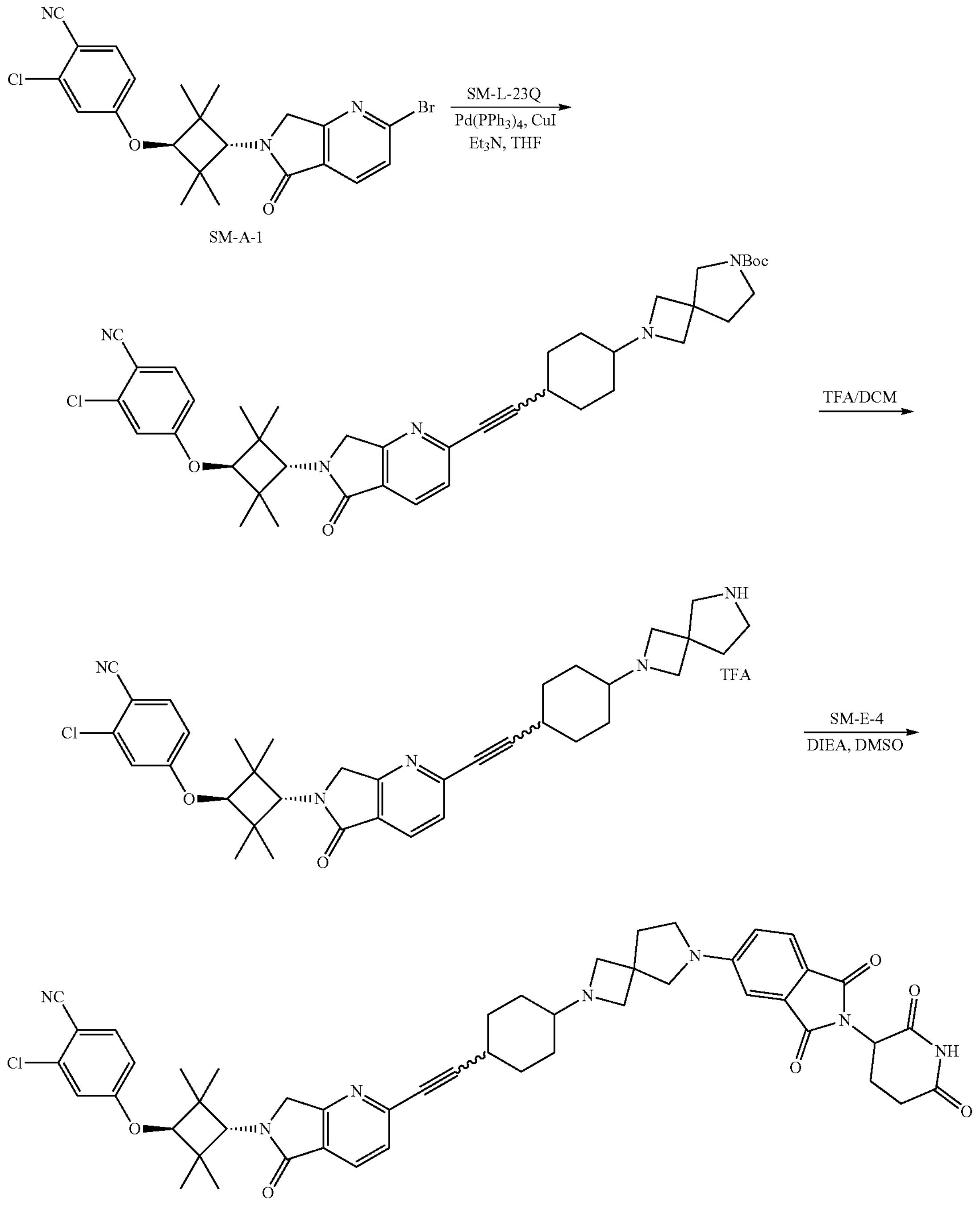
368
$^1$H NMR (400 MHz, $CDCl_3$) δ 8.04 (d, J=7.9 Hz, 1H), 7.99 (s, 1H), 7.66 (d, J=8.4 Hz, 1H), 7.58 (d, J=8.7 Hz, 1H), 7.53-7.44 (m, 1H), 7.00 (d, J=2.3 Hz, 1H), 6.93 (s, 1H), 6.84 (dd, J=8.7, 2.4 Hz, 1H), 6.67 (d, J=9.3 Hz, 1H), 4.93 (dd, J=12.3, 5.3 Hz, 1H), 4.69 (s, 2H), 4.46 (s, 1H), 4.34-4.27 (m, 1H), 3.56 (s, 2H), 3.45 (s, 2H), 3.23 (s, 3H), 3.01-2.65 (m, 4H), 2.27-2.23 (m, 2H), 2.14-2.10 (m, 2H), 2.02-1.97 (m, 2H), 1.64-1.50 (m, 7H), 1.46 (s, 6H), 1.27 (s, 6H). MS: calcd. for $C_{49}H_{50}ClN_7O_6$ $[M+H]^+$:868.4; found: 868.3.

369: 2-Chloro-4-((1r,3r)-3-(2-((4-(6-(2-(2,6-dioxopiperidin-3-yl)-1,3-dioxoisoindolin-5-yl)-2,6-diazaspiro[3.4]octane-2-yl)cyclohexyl)ethynyl)-5-oxo-5,7-dihydro-pyrrolo[3,4-b]pyridin-6-yl)-2,2,4,4-tetramethylcyclobutoxy) benzonitrile
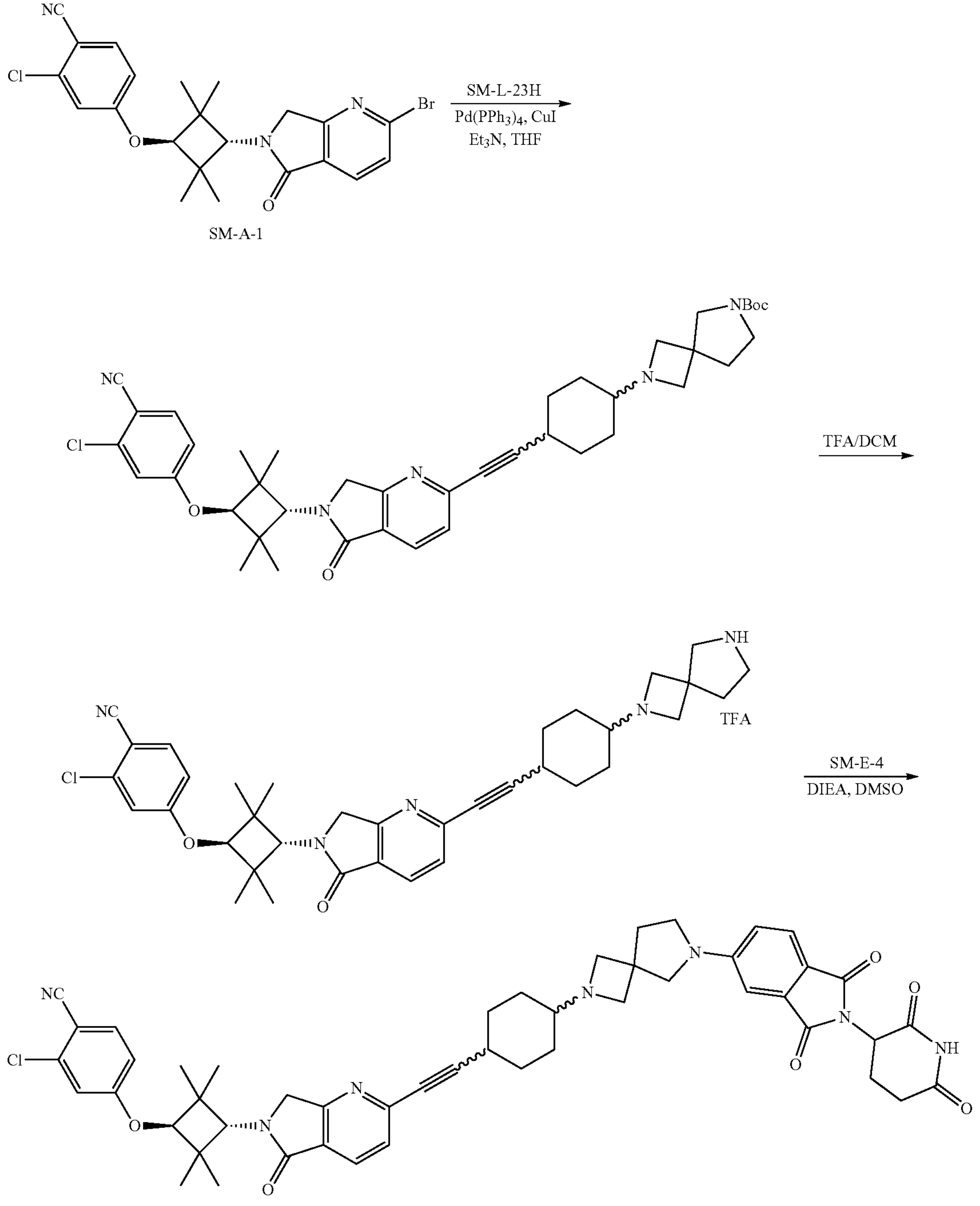
SM-A-1
369
$^1$H NMR (400 MHz, DMSO-$d_6$) δ 11.08 (s, 1H), 8.04 (d, J=7.9 Hz, 1H), 7.91 (d, J=8.7 Hz, 1H), 7.65 (d, J=8.4 Hz, 1H), 7.54 (d, J=7.9 Hz, 1H), 7.29 (d, J=2.4 Hz, 1H), 7.07 (dd, 0.1=8.8, 2.4 Hz, 1H), 6.90 (s, 1H), 6.82 (d, J=8.7 Hz, 1H), 5.06 (dd, J=13.0, 5.4 Hz, 1H), 4.80 (s, 2H), 4.54 (s, 1H), 4.34 (s, 1H), 3.53 (s, 2H), 3.44 (t, J=6.6 Hz, 2H), 3.12 (d, J=23.5 Hz, 3H), 2.88-2.65 (m, 1H), 2.56 (dd, J=16.7, 11.9 Hz, 4H), 2.18-2.15 (m, 2H), 2.18-2.02 (m, 4H), 1.78-1.74 (m, 2H), 1.47-1.33 (m, 8H), 1.16 (s, 6H), 1.10-1.00 (m, 2H). MS: calcd. for $C_{49}H_{50}ClN_7O_6$ [M+H]$^+$; 868.4; found: 868.3.

370: 2-Chloro-4-((1r,3r)-3-(2-((4-(6-(2,6-dioxopiperidin-3-yl)-6-fluoro-1,3-dioxoisoindolin-5-yl)-2,6-diazaspiro[3.4]octan-2-yl)cyclohexyl)ethynyl)-5-oxo-5,7-dihydro-pyrrolo[3,4-b]pyridin-6-yl)-2,2,4,4-tetramethylcyclobutoxy)benzonitrile
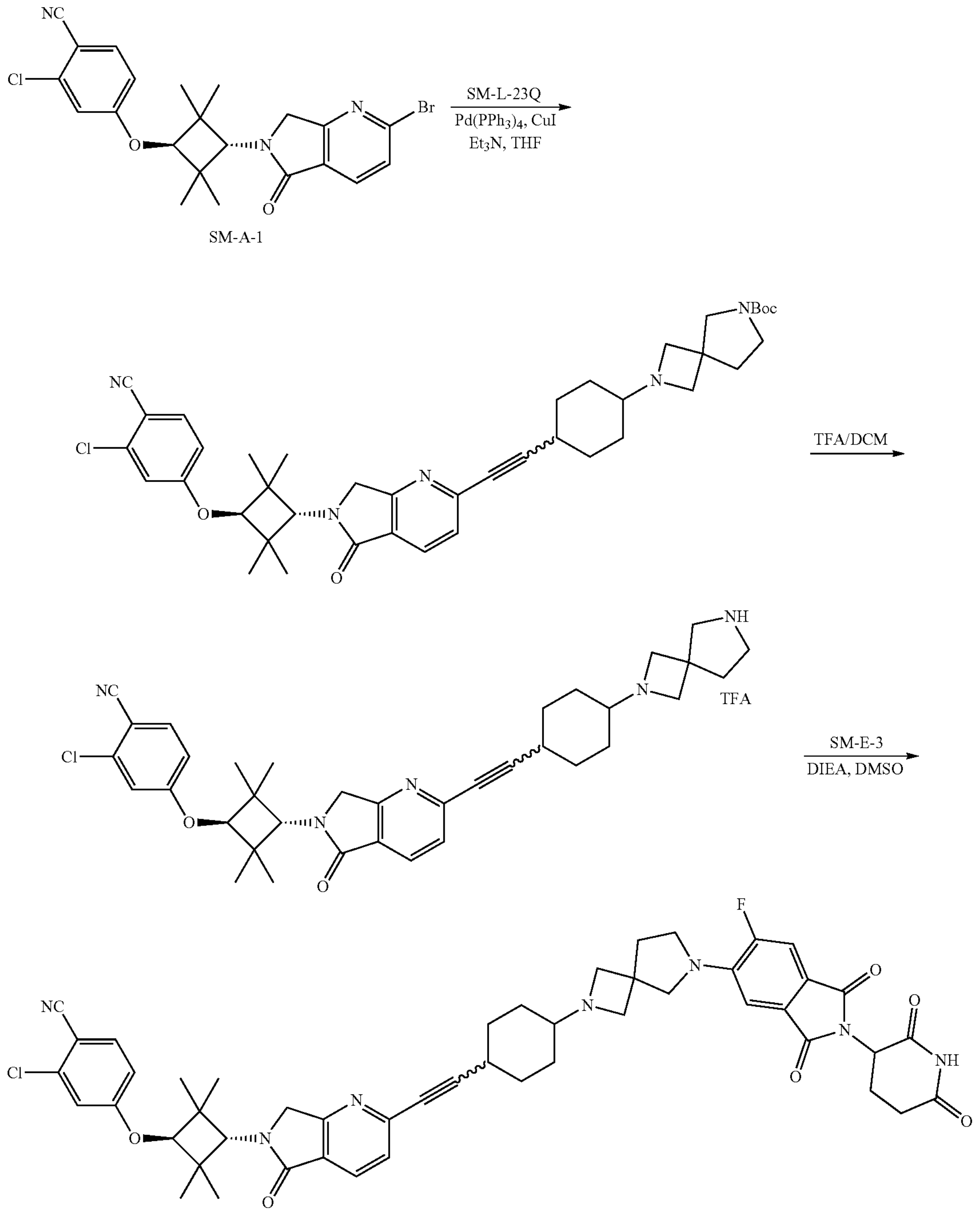
370
$^1$H NMR (400 MHz, DMSO-$d_6$) δ 11.10 (s, 1H), 8.06 (d, J=7.9 Hz, 1H), 7.91 (d, J=8.8 Hz, 1H), 7.59 (dd, J=18.4, 10.2 Hz, 2H), 7.30 (d, J=2.4 Hz, 1H), 7.12-7.00 (m, 2H), 5.06 (dd, J=12.9, 5.5 Hz, 1H), 4.82 (s, 2H), 4.54 (s, 1H), 4.35 (s, 1H), 3.67 (s, 2H), 3.57 (s, 2H), 3.15-3.05 (m, 4H), 3.01-2.82 (m, 2H), 2.63-2.51 (m, 2H), 2.12-2.10 (m, 2H), 2.05-1.97 (m, 2H), 1.85-1.81 (m, 2H), 1.60-1.50 (m, 4H), 1.45-1.30 (m, 8H), 1.16 (s, 6H). MS: calcd. for $C_{49}H_{49}ClFN_7O_6$ $[M+H]^+$:886.3; found: 886.3.

371: 2-Chloro-4-((1r,3r)-3-(2-((4-(6-(2,6-dioxopiperidin-3-yl)-6-fluoro-1,3-dioxoisoindolin-5-yl)-2,6-diazaspiro[3.4]octan-2-yl)cyclohexyl)ethynyl)-5-oxo-5,7-dihydro-pyrrolo[3,4-b]pyridin-6-yl)-2,2,4,4-tetramethylcyclobutoxy)benzonitrile
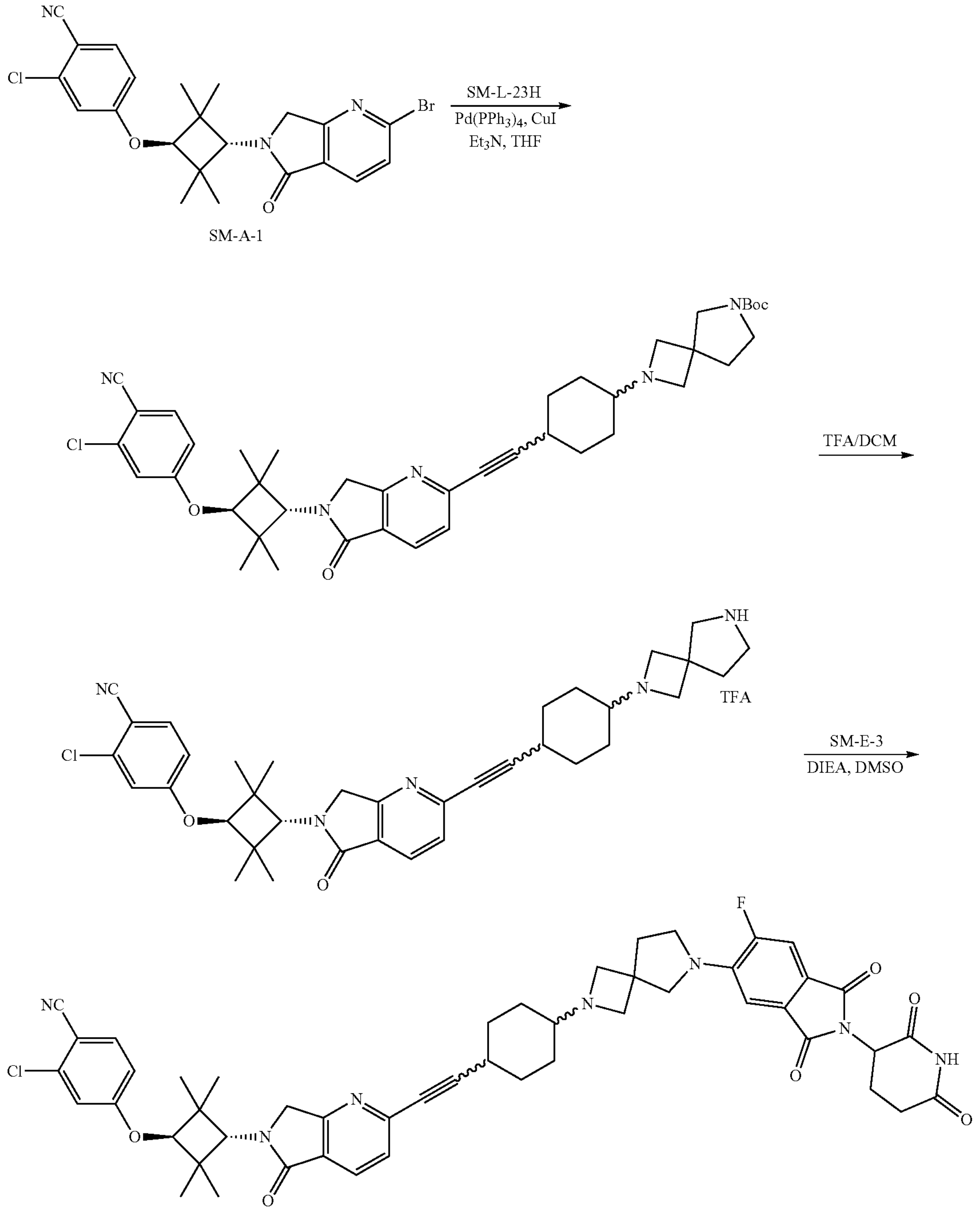
371
$^1$H NMR (400 MHz, DMSO-$d_6$) δ 11.10 (s, 1H), 8.04 (d, J=8.0 Hz, 1H), 7.91 (d, J=8.8 Hz, 1H), 7.61 (d, J=12.6 Hz, 1H), 7.54 (d, J=7.9 Hz, 1H), 7.30 (s, 1H), 7.06 (t, J=8.6 Hz, 2H), 5.07 (dd, J=12.7, 5.0 Hz, 1H), 4.80 (s, 2H), 4.54 (s, 1H), 4.34 (s, 1H), 3.66 (s, 2H), 3.57 (s, 2H), 3.11-3.07 (m, 3H), 2.88-2.88 (m, 1H), 2.66-2.54 (m, 4H), 211-2.01 (m, 6H), 1.78-1.74 (m, 2H), 1.50-1.39 (m, 8H), 1.16 (s, 6H), 1.10-1.00 (m, 2H). MS: calcd. for $C_{49}H_{49}ClFN_7O_6$ $[M+H]^+$: 886.3; found: 886.3.

372: 2-Chloro-4-((1r,3r)-3-(2-((4-(2-(2,6-dioxopiperidin-3-yl)-1,3-dioxoisoindolin-5-yl)-2,6-diazaspiro[3.4]octan-6-yl)cyclohexyl)ethynyl)-5-oxo-5,7-dihydro-pyrrolo[3,4-b]pyridin-6-yl)-2,2,4,4-tetramethylcyclobutoxy)benzonitrile
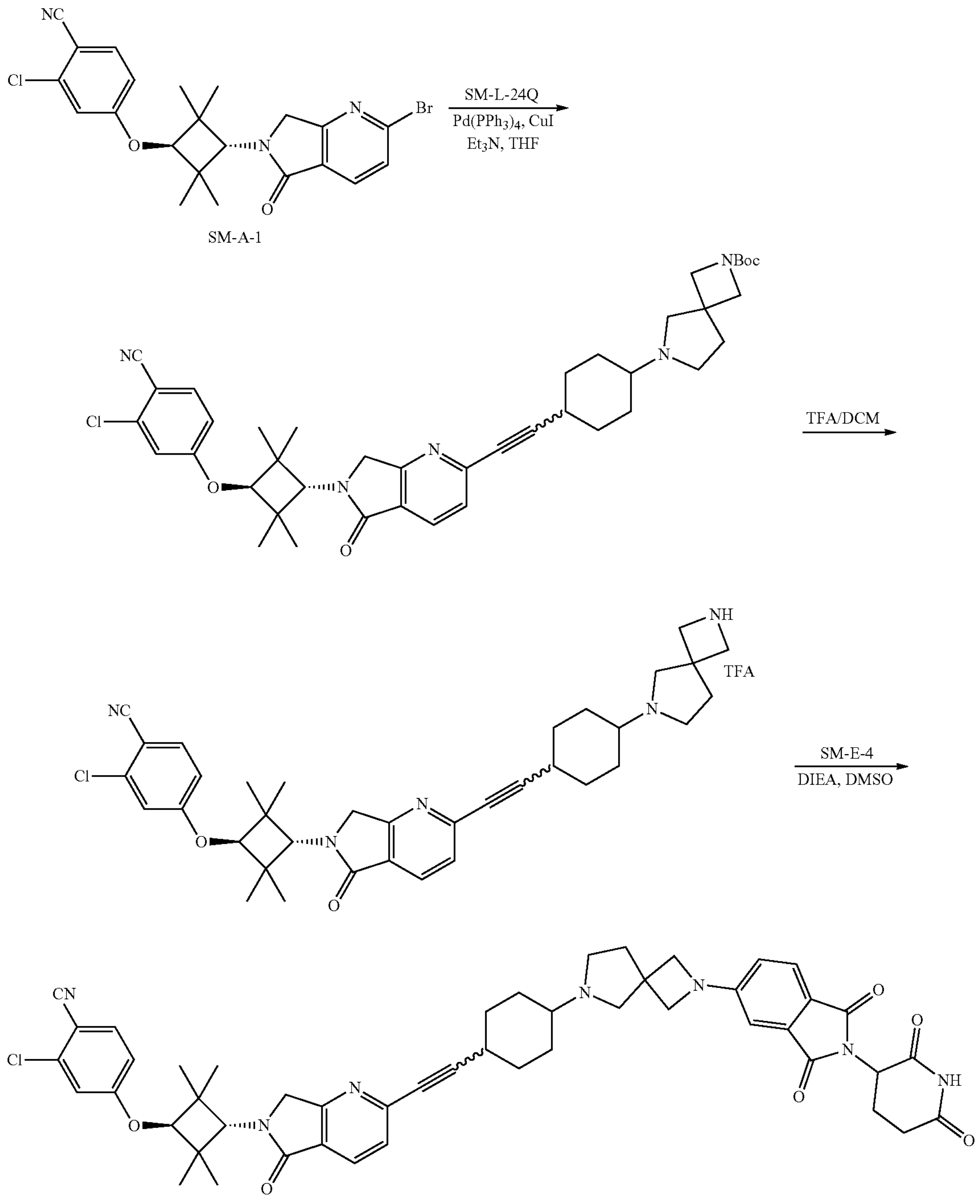
372
$^1$H NMR (400 MHz, DMSO-$d_6$) δ 11.05 (s, 1H), 8.04 (d, J=8.1 Hz, 1H), 7.89 (d, J=8.7 Hz, 1H), 7.63 (d, J=8.9 Hz, 1H), 7.55 (d, J=8.2 Hz, 1H), 7.27 (d, J=2.4 Hz, 1H), 7.05 (dd, J=8.8, 2.5 Hz, 1H), 6.78 (s, 1H), 6.63 (s, 1H), 5.03 (dd, J=12.7, 5.4 Hz, 1H), 4.80 (s, 2H), 4.52 (s, 1H), 4.33 (s, 1H), 4.06-3.78 (m, 4H), 2.99-2.69 (m, 4H), 2.66-2.51 (m, 4H), 2.15-1.94 (m, 3H), 1.93-1.71 (m, 3H), 1.65 (m, 6H), 1.30 (s, 6H), 1.18 (s, 6H). MS: calcd. for $C_{49}H_{50}ClN_7O_6$ $[M+H]^+$: 868.4; found: 868.3.

373: 2-Chloro-4-((1r,3r)-3-(2-((4-(2-(2,6-dioxopiperidin-3-yl)-1,3-dioxoisoindolin-5-yl)-2,6-diazaspiro[3.4]octan-6-yl)cyclohexyl)ethynyl)-5-oxo-5,7-dihydro-pyrrolo[3,4-b]pyridin-6-yl)-2,2,4,4-tetramethylcyclobutoxy)benzonitrile
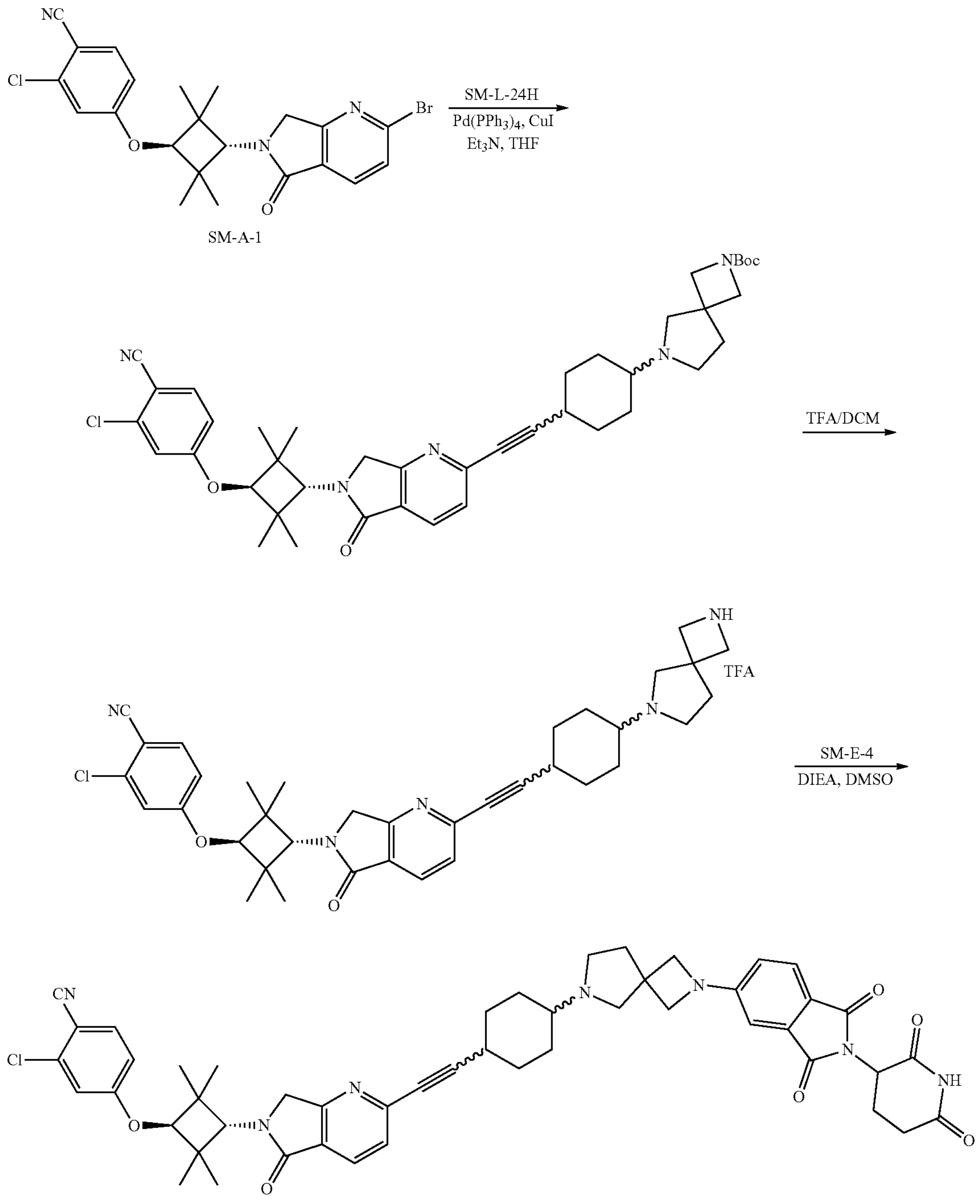
373
$^1$H NMR (400 MHz, DMSO-$d_6$) δ 11.07 (s, 1H), 8.02 (d, J=7.9 Hz, 1H), 7.89 (d, J=8.8 Hz, 1H), 7.63 (d, J=8.3 Hz, 1H), 7.52 (d, J=7.9 Hz, 1H), 7.27 (d, J=2.4 Hz, 1H), 7.04 (dd, J=8.8, 2.4 Hz, 1H), 6.77 (s, 1H), 6.64 (d, J=8.4 Hz, 1H), 5.04 (dd, J=12.9, 5.5 Hz, 1H), 4.78 (s, 2H), 4.52 (s, 1H), 4.31 (s, 1H), 4.13-3.68 (m, 4H), 2.92-2.69 (m, 3H), 2.67-2.50 (m, 4H), 2.46-2.39 (m, 1H), 2.16-1.81 (m, 8H), 1.50-1.30 (m, 8H), 1.32-1.22 (m, 2H), 1.13 (s, 6H). MS: calcd. for $C_{49}H_{50}ClN_7O_6$ $[M+H]^+$: 868.4; found: 868.3.

374: 2-Chloro-4-((1r,3r)-3-(2-((4-(2-(2,6-dioxopiperidin-3-yl)-6-fluoro-1,3-dioxoisoindolin-5-yl)-2,6-diazaspiro [3.4]octan-6-yl)cyclohexyl)ethynyl)-5-oxo-5,7-dihydro-pyrrolo [3,4-b]pyridin-6-yl)-2,2,4,4-tetramethylcyclobutoxy)benzonitrile
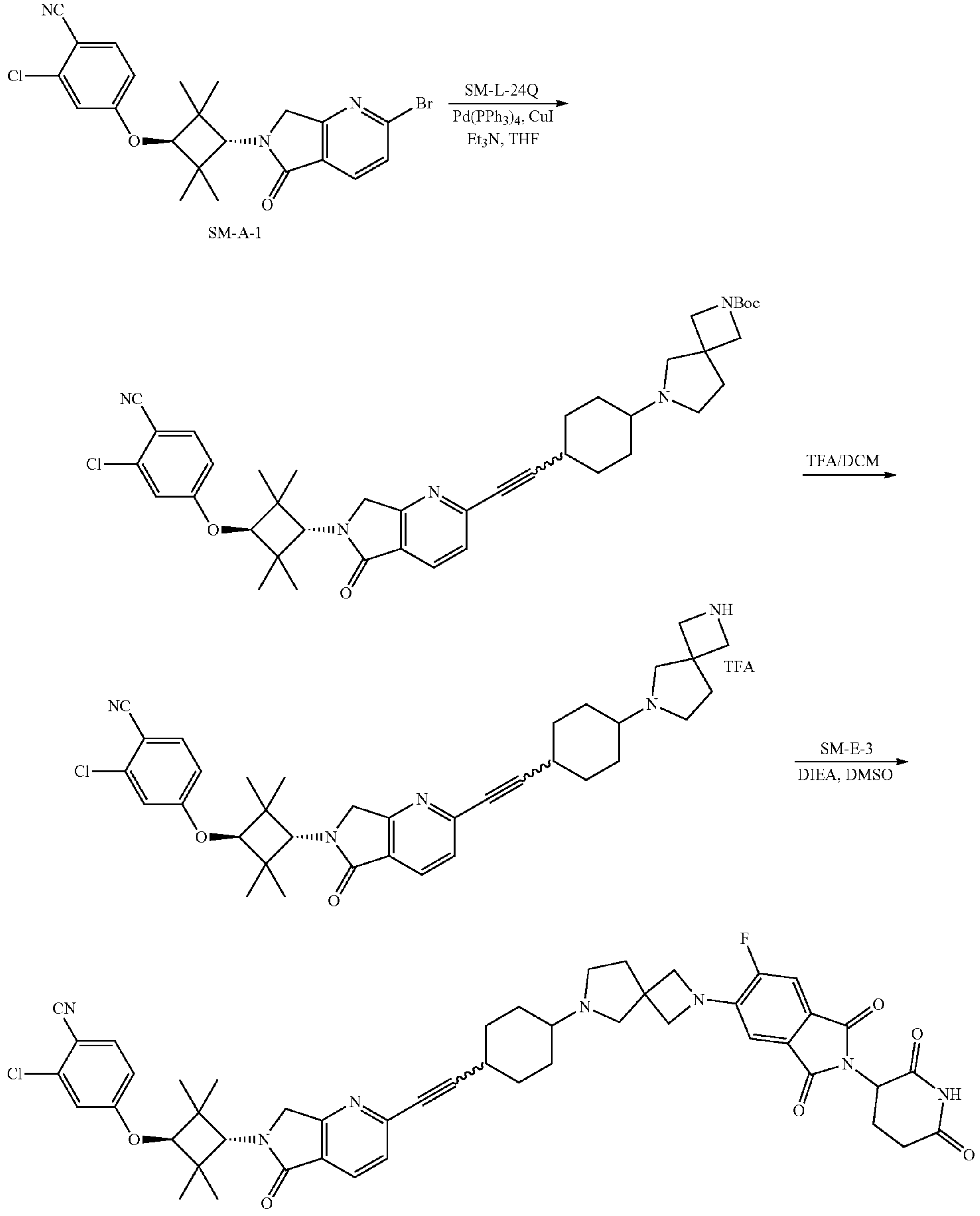
374
$^1$H NMR (400 MHz, DMSO-$d_6$) δ 11.07 (s, 1H), 8.04 (d, J=7.6 Hz, 1H), 7.89 (d, J=8.8 Hz, 1H), 7.57 (dd, J=15.4, 9.5 Hz, 2H), 7.27 (d, J=2.4 Hz, 1H), 7.05 (dd, J=8.8, 2.4 Hz, 1H), 6.90 (d, J=6.7 Hz, 1H), 5.04 (dd, J=12.9, 5.4 Hz, 1H), 4.80 (s, 2H), 4.52 (s, 1H), 4.33 (s, 1H), 4.08 (s, 4H), 2.98-2.74 (m, 3H), 2.61-2.50 (m, 2H), 2.44-2.31 (m, 3H), 2.12-1.92 (m, 4H), 1.89-1.77 (m, 2H), 1.76-1.47 (m, 6H), 1.39 (s, 6H), 1.14 (s, 6H). MS: calcd. for $C_{49}H_{49}ClFN_7O_6$ $[M+H]^+$: 886.3; found: 886.3.

375: 2-Chloro-4-((1r,3r)-3-(2-((4-(2-(2,6-dioxopiperidin-3-yl)-6-fluoro-1,3-dioxoisoindolin-5-yl)-2,6-diazaspiro[3.4]octan-6-yl)cyclohexyl)ethynyl)-5-oxo-5,7-dihydro-pyrrolo[3,4-b]pyridin-6-yl)-2,2,4,4-tetramethylcyclobutoxy)benzonitrile
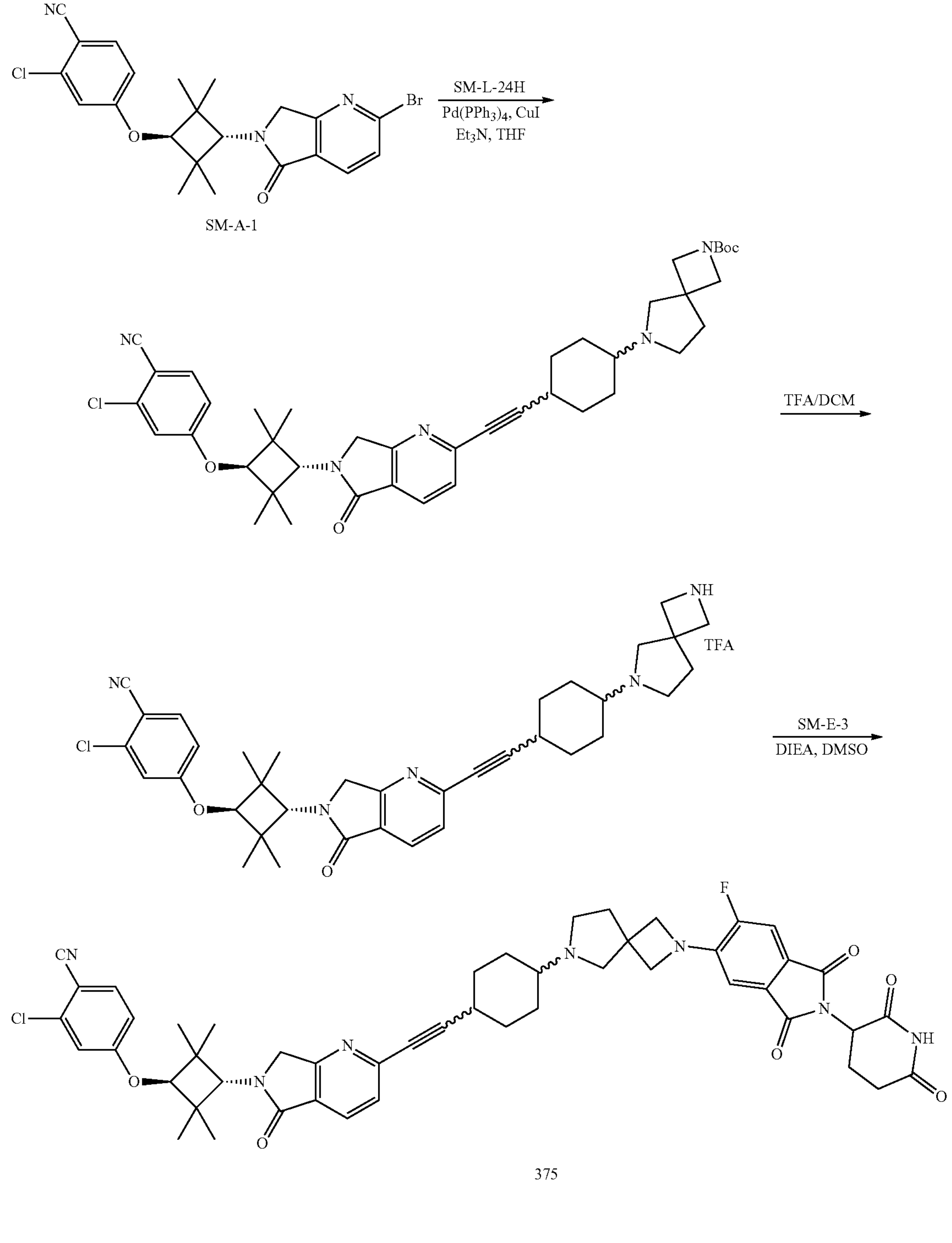
375
$^1$H NMR (400 MHz, DMSO-$d_6$) δ 11.10 (s, 1H), 8.04 (d, J=7.9 Hz, 1H), 7.91 (d, J=8.7 Hz, 1H), 7.61 (d, J=11.1 Hz, 1H), 7.54 (d, J=7.8 Hz, 1H), 7.29 (d, J=2.2 Hz, 1H), 7.07 (dd, J=8.8, 2.2 Hz, 1H), 6.93 (d, J=7.7 Hz, 1H), 5.07 (dd, J=12.8, 5.3 Hz, 1H), 4.80 (s, 2H), 4.54 (s, 1H), 4.34 (s, 1H), 4.09 (s, 4H), 2.94-2.70 (m, 3H), 2.69-2.53 (m, 4H), 2.46-2.39 (m, 1H), 2.24-1.75 (m, 8H), 1.56-1.29 (m, 8H), 1.35-1.21 (m, 2H), 1.16 (s, 6H). MS: calcd. for $C_{49}H_{49}ClFN_7O_6$ $[M+H]^+$: 886.3; found: 886.3.

376: 2-Chloro-4-((1r,3r)-3-(2-((4-(7-(2-(2,6-dioxopiperidin-3-yl)-1,3-dioxoisoindolin-5-yl)-2,7-diazaspiro[3.5]nonan-2-yl)cyclohexyl)ethynyl)-S-oxo-5,7-dihydro-pyrrolo[3,4-b]pyridin-6-yl)-2,2,4,4-tetramethylcyclobutoxy) benzonitrile
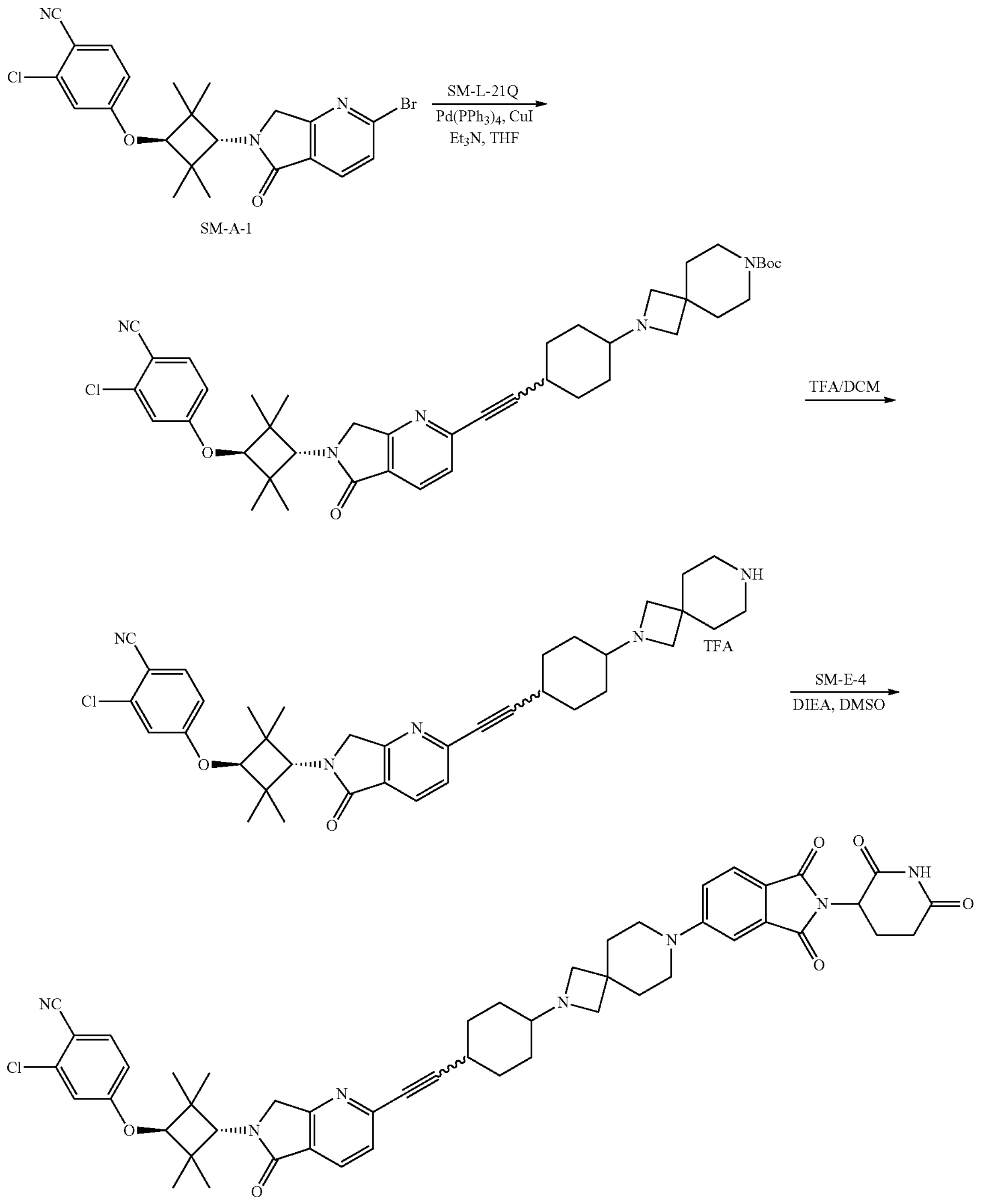
SM-A-1
376
$^1$H NMR (400 MHz, DMSO-$d_6$) δ 11.08 (s, 1H), 8.06 (d, J=7.7 Hz, 1H), 7.91 (d, J=8.8 Hz, 1H), 7.63 (d, J=8.4 Hz, 1H), 7.57 (d, J=7.9 Hz, 1H), 7.30 (d, J=2.3 Hz, 1H), 7.07 (dd, J=8.7, 2.3 Hz, 1H), 6.90 (s, 1H), 6.81 (d, J=8.4 Hz, 1H), 5.05 (dd, J=12.8, 5.4 Hz, 1H), 4.82 (s, 2H), 4.55 (s, 1H), 4.35 (s, 1H), 3.70-3.37 (m, 4H), 3.05-2.82 (m, 2H), 2.81-2.55 (m, 4H), 2.37-1.92 (m, 6H), 1.98-1.48 (m, 10H), 1.41 (s, 6H), 1.16 (s, 6H). MS: calcd. for $C_{50}H_{52}ClN_7O_6$ $[M+H]^+$: 882.4; found: 882.3.
377: 2-Chloro-4-((1r,3r)-3-(2-((4-(7-(2-(2,6-dioxopiperidin-3-yl)-1,3-dioxoisoindolin-5-yl)-2,7-diazaspiro[3.5]nonan-2-yl)cyclohexyl)ethynyl)-5-oxo-5,7-dihydro-pyrrolo[3,4-b]pyridin-6-yl)-2,2,4,4-tetramethylcyclobutoxy) benzonitrile
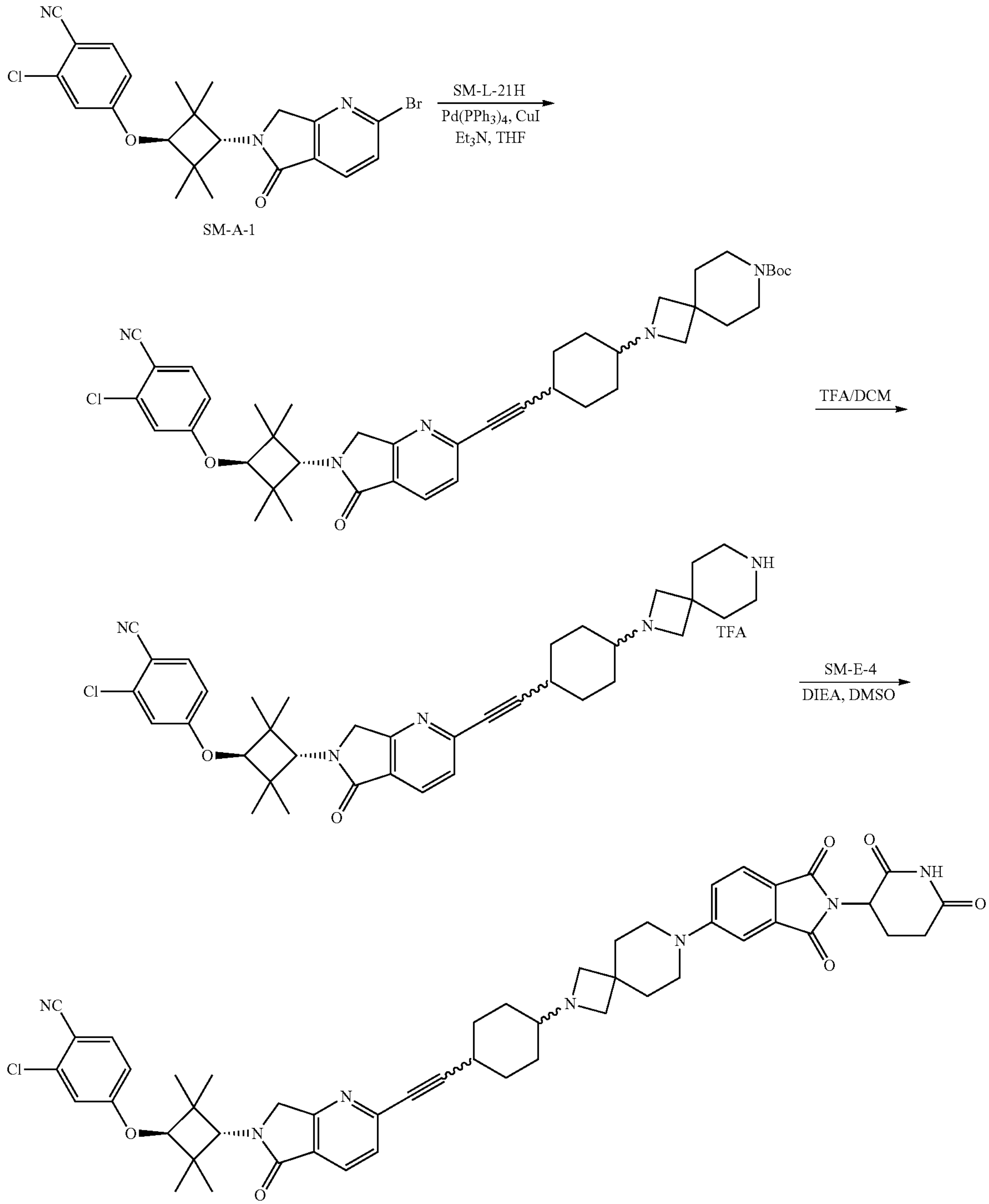
377

$^1$H NMR (400 MHz, DMSO-$d_6$) δ 11.08 (s, 1H), 8.04 (d, J=7.9 Hz, 1H), 7.91 (d, J=8.7 Hz, 1H), 7.64 (d, J=84 Hz, 1H), 7.54 (d, J=7.9 Hz, 1H), 7.29 (d, J=2.2 Hz, 1H), 7.07 (dd, J=8.8, 2.2 Hz, 1H), 6.90 (s, 1H), 6.81 (d, J=8.4 Hz, 1H), 5.06 (dd, J=12.9, 5.3 Hz, 1H), 4.80 (s, 2H), 4.54 (s, 1H), 4.33 (s, 1H), 3.53-3.37 (m, 4H), 2.89-2.76 (m, 1H), 2.63-2.52 (m, 6H), 2.10-2.02 (m, 9H), 1.78 (s, 2H), 1.51-1.45 (m, 2H), 1.40 (s, 6H), 1.31-1.27 (m, 2H), 1.16 (s, 6H). MS: calcd. for $C_{50}H_{52}ClN_7O_6$ $[M+H]^+$: 882.4; found: 882.3.
378: 2-Chloro-4-((1 r,3r)-3-(2-((4-(7-(2-(2,6-dioxopiperidin-3-yl)-6-fluoro-1,3-dioxoisoindolin-5-yl)-2,7-diazaspiro[3.5]nonan-2-yl)cyclohexyl)ethynyl)-5-oxo-5,7-dihydro-pyrrolo[3,4-b]pyridin-6-yl)-2,2,4,4-tetramethylcyclobutoxy) benzonitrile
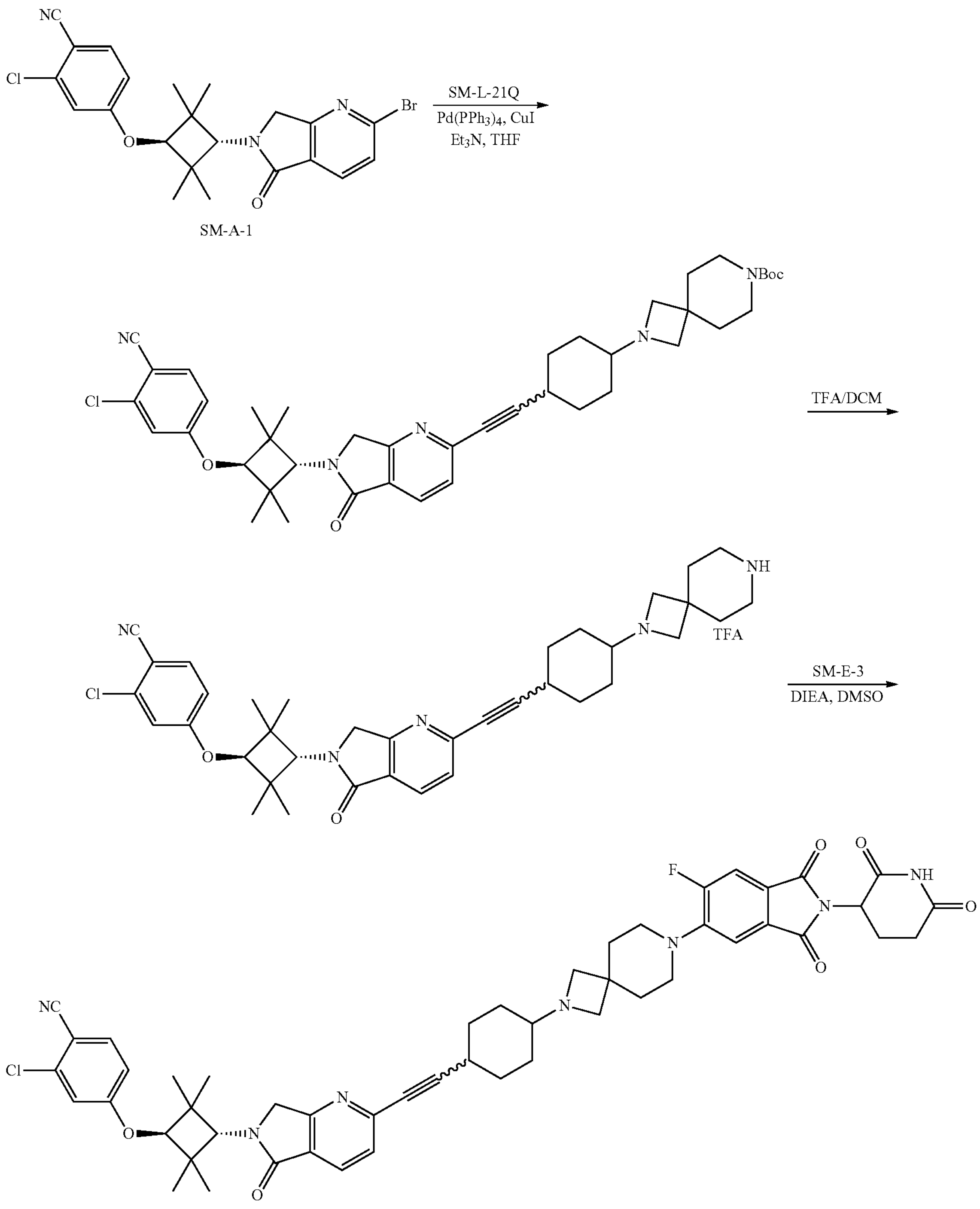
378

$^1$H NMR (400 MHz, DMSO-$d_6$) δ 11.09 (s, 1H), 8.06 (d, J=7.9 Hz, 1H), 7.91 (d, J=8.7 Hz, 1H), 7.58 (t, J 10.5 Hz, 2H), 7.30 (d, J=2.3 Hz, 1H), 7.07 (dd, J=14.2, 5.1 Hz, 2H), 5.06 (dd, J=12.8, 5.2 Hz, 1H), 4.82 (s, 2H), 4.55 (s, 1H), 4.35 (s, 1H), 3.70-3.48 (m, 4H), 2.95-2.84 (m, 2H), 2.70-2.55 (m, 4H), 2.39-1.94 (m, 6H), 1.90-1.60 (m, 10H), 1.41 (s, 6H), 1.16 (s, 6H). MS: calcd. for $C_{50}H_{51}ClFN_7O_6[M+H]^+$: 900.4. found: 900.3.
379: 2-Chloro-4-((1r,3r)-3-(2-((4-(7-(2-(2,6-dioxopiperidin-3-yl)-6-fluoro-1,3-dioxoisoindolin-5-yl)-2,7-diazaspiro[3.5]nonan-2-yl)cyclohexyl)ethynyl)-5-oxo-5,7-dihydro-pyrrolo[3,4-b]pyridin-6-yl)-2,2,4,4-tetramethylcyclobutoxy) benzonitrile
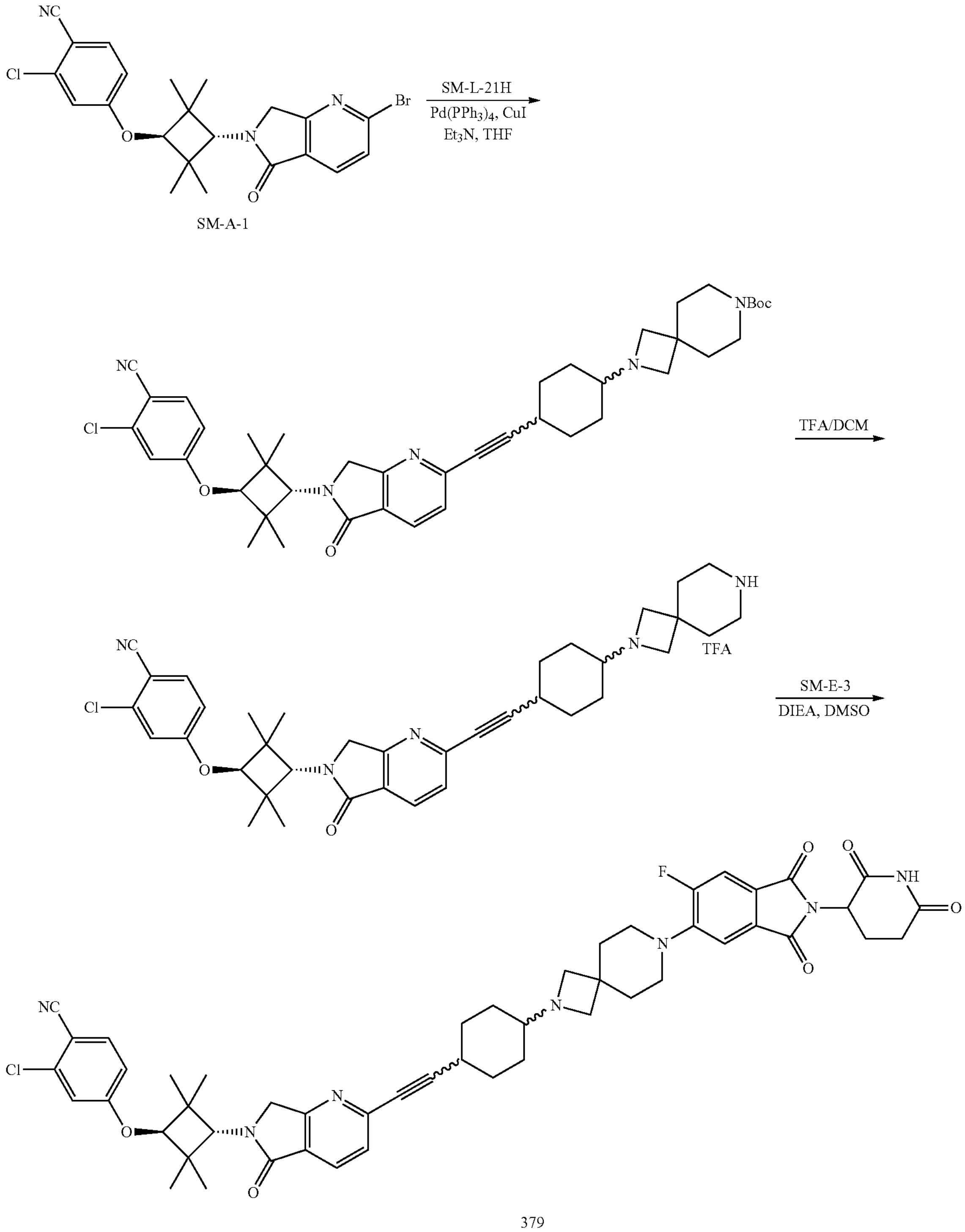

$^1$H NMR (400 MHz, DMSO-$d_6$) δ 11.10 (s, 1H), 8.04 (d, J=7.9 Hz, 1H), 7.91 (d, J=8.8 Hz, 1H), 7.57 (dd, J=27.6, 10.2 Hz, 2H), 7.29 (d, J=2.2 Hz, 1H), 7.06 (dd, J=13.2, 4.8 Hz, 2H), 5.07 (dd, J=12.9, 5.4 Hz, 1H), 4.80 (s, 2H), 4.54 (s, 1H), 4.34 (s, 1H), 3.68-3.44 (m, 4H), 2.94-2.83 (m, 1H), 2.67-2.59 (m, 6H), 2.17-1.69 (m, 11H), 1.51-1.46 (m, 2H),
1.40 (s, 6H), 1.33-1.27 (m, 2H), 1.16 (s, 6H). MS: calcd. for $C_{50}H_{51}ClFN_7O_6$ $[M+H]^+$: 900.4; found: 900.4.
380: 2-Chloro-4-((1r,3r)-3-(2-((1r,4r)-4-(4-(2-(2,6-dioxopiperidin-3-yl)-6-fluoro-1,3-dioxoisoindolin-5-yl)piperazin-1-yl)cyclohexyl)ethynyl)-5-oxo-5,7-dihydro-pyrrolo[3,4-b]pyrazine-26-yl)-2,2,4,4-tetramethylcyclobutoxy)benzonitrile
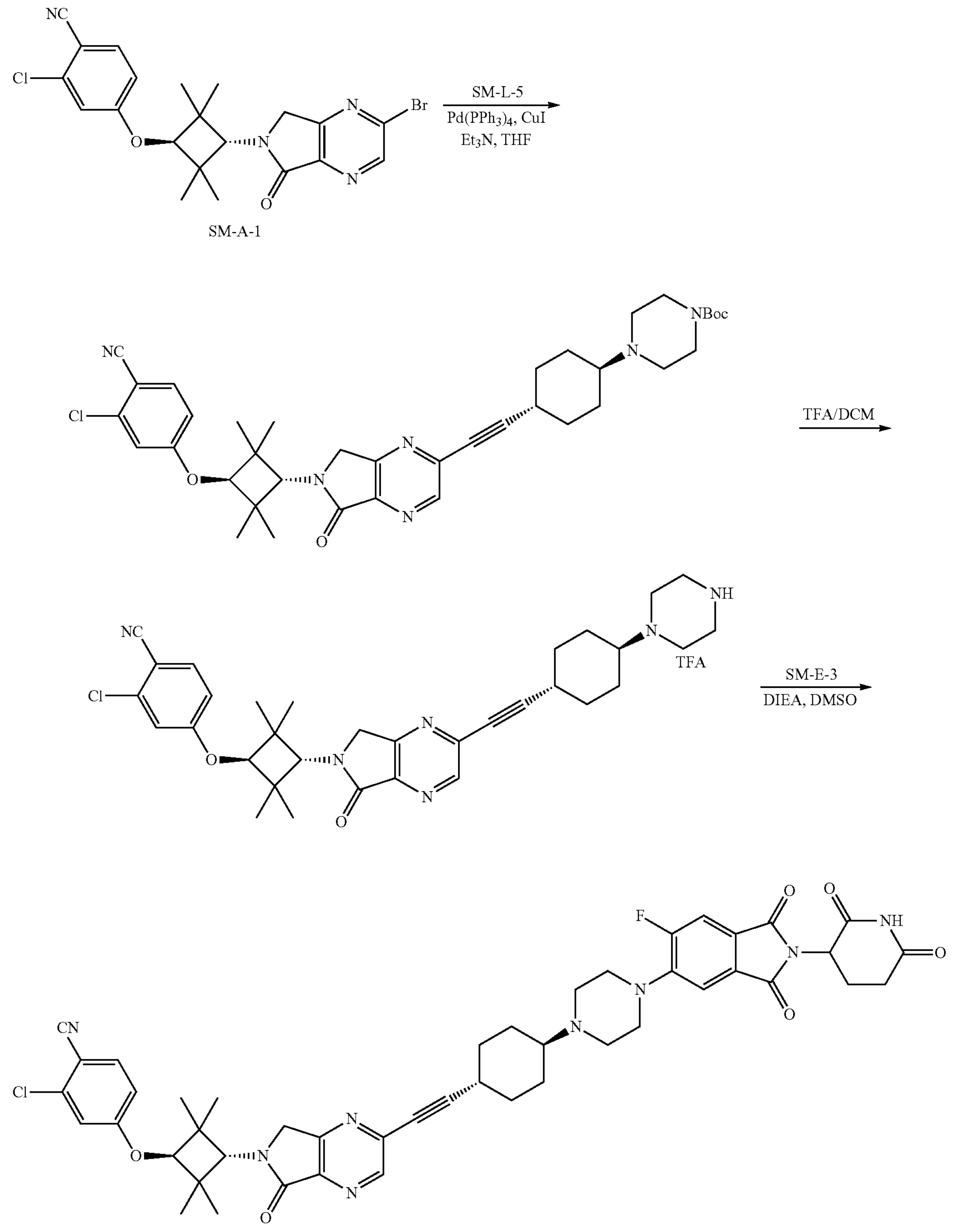

$^1$H NMR (400 MHz, DMSO-$d_6$) δ 8.82 (s, 1H), 7.92 (d, J=8.7 Hz, 1H), 7.74 (d, J=11.5 Hz, 1H), 7.45 (d, J=7.3 Hz, 1H), 7.28 (t, J=12.3 Hz, 1H), 7.08 (dd, J=8.8, 2.3 Hz, 1H), 5.11 (dd, J=12.8, 5.4 Hz, 1H), 4.82 (d, J=19.3 Hz, 2H), 4.63-4.49 (m, 1H), 4.37 (s, 1H), 3.24 (s, 4H), 2.93-2.82 (m, 1H), 2.77-2.54 (m, 6H), 2.39-2.34 (m, 2H), 2.12-1.97 (m, 3H), 1.90-1.87 (m, 2H), 1.59-1.32 (m, 10H), 1.17 (s, 6H).
MS: calcd. for $C_{46}H_{46}ClFN_8O_6$ $[M+H]^+$: 861.3; found: 861.3.
381: 2-Chloro-4-((1r,3r)-3-(2-((1r,4r)-4-(4-(2-(2,6-dioxopiperidin-3-yl)-1,3-dioxoisoindolin-5-yl)piperazin-1-yl)cyclohexyl)ethynyl)-5-oxo-5,7-dihydropyrrolo[3,4-b]pyrazine-26-yl)-2,2,4,4-tetramethylcyclobutoxy)benzonitrile
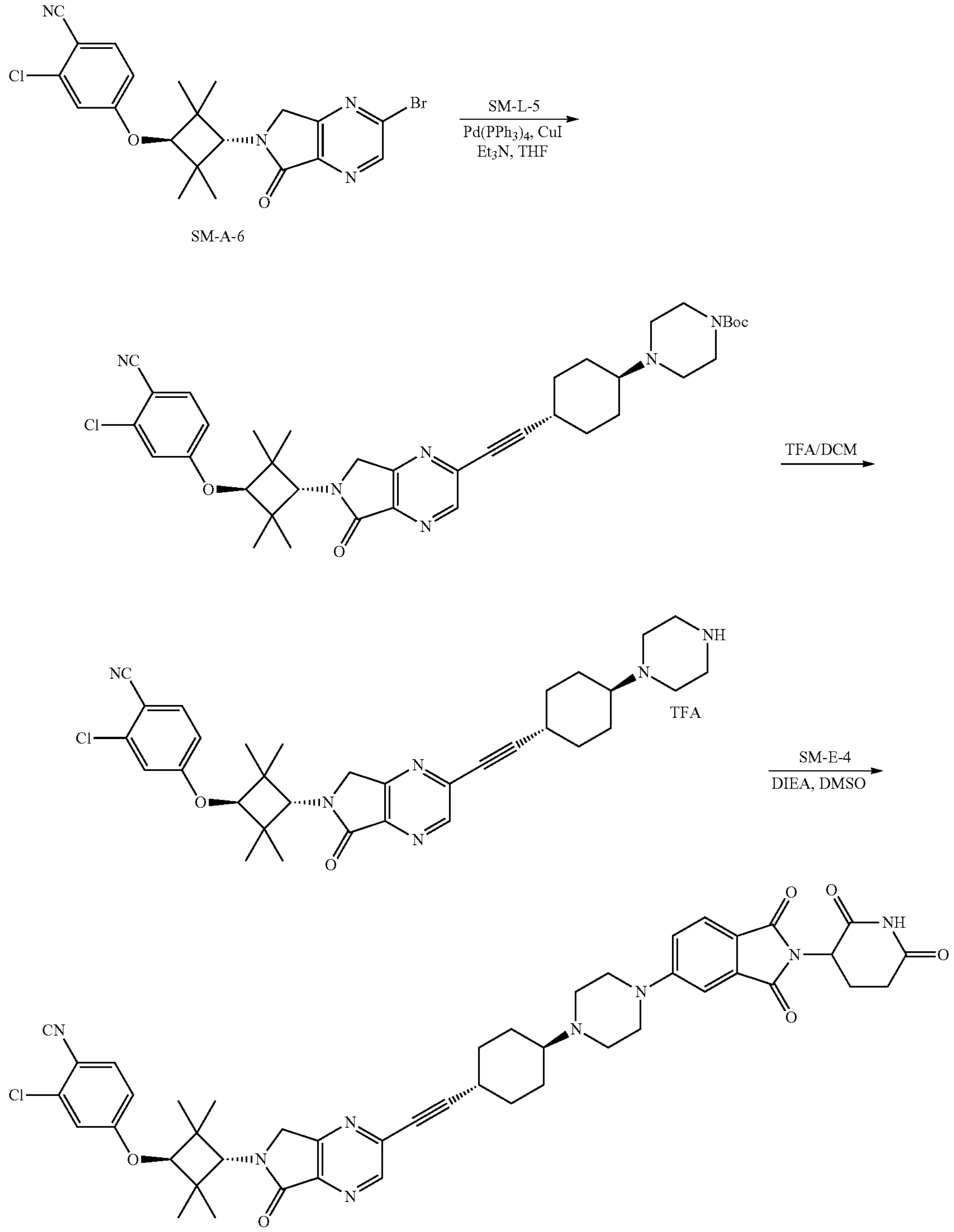

$^1H$ NMR (400 MHz, DMSO-$d_6$) δ 11.10 (s, 1H), 8.82 (s, 1H), 7.91 (d, J=8.7 Hz, 1H), 7.68 (d, J=8.5 Hz, 1H), 7.55-7.06 (m, 3H), 7.08 (dd, J=8.8, 2.4 Hz, 1H), 5.08 (dd, J=12.8, 5.3 Hz, 1H), 4.84 (s, 2H), 4.56 (s, 1H), 4.37 (s, 1H), 3.43 (s, 4H), 2.92-2.84 (m, 1H), 2.71-2.55 (m, 6H), 2.49-2.33 (m, 2H), 2.13-2.10 (m, 2H), 2.03-1.99 (m, 1H), 1.89-1.87 (m, 2H), 1.55-1.46 (m, 2H), 1.43 (s, 6H), 1.38-1.23 (m, 2H), 1.17 (s, 6H). MS: calcd. for $C_{46}H_{47}ClNO_6$ $[M+H]^+$: 843.3; found: 843.0.
382: 2-Chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-pyrrolo[3,4-d]pyrimidin-6-yl)-2,2,4,4-tetramethylcyclobutoxy)benzonitrile
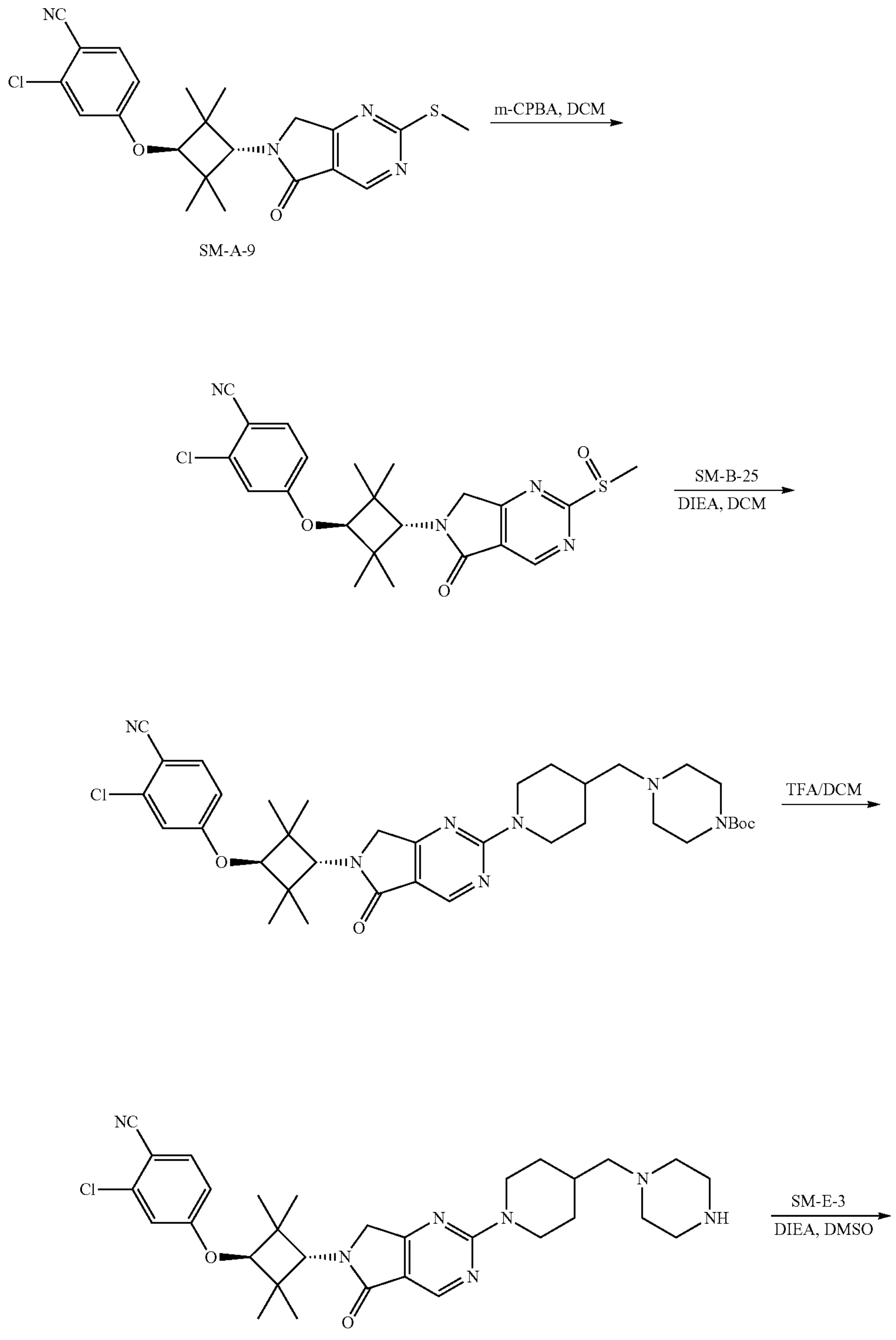

-continued

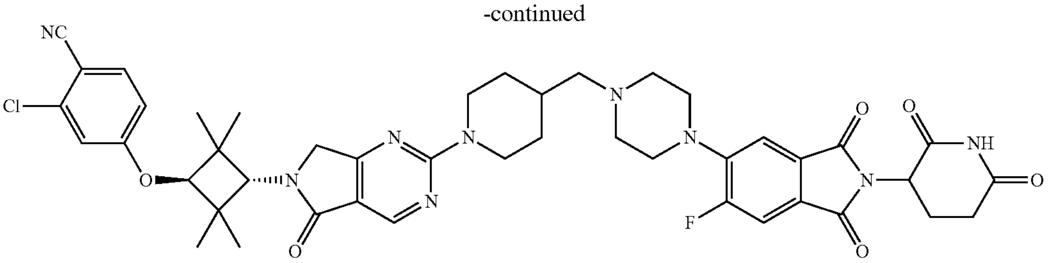

382

1. Synthesis of compound 2-Chloro-4-((1r,3r)-2,2,4,4-tetramethyl-3-(2-(methylsulfinyl)-5-oxo-5H-pyrrolo[3,4-d]pyrimidin-6(7H)-yl) cyclobutyloxy)benzonitrile (1054-1)

The compound 2-chloro-4-((1r,3r)-2,2,4,4-tetramethyl-3-(2-(methylthio)-5-oxo-5H-pyrrolo[3,4-d]pyrimidin-6(7H)-yl)cyclobutyloxy)benzonitrile (300 mg, 0.68 mmol) was dissolved in dichloromethane (20 mL), and then m-chloroperoxybenzoic acid (300 mg, 1.70 mmol) was added in batches. The reaction solution was stirred at room temperature overnight. The reaction solution was diluted with water (20 mL) and then extracted with dichloromethane (10 mL×3). The organic phase was combined and then successively washed with saturated sodium sulfite solution (10 mL×3) and saturated brine (10 mL×3), dried over anhydrous sodium sulfate, and rotatory evaporated to dry, to obtain a crude compound 2-chloro-4-((1r,3r)-2,2,4,4-tetramethyl-3-(2-(methylsulfinyl)-5-oxo-5H-pyrrolo[3,4d]pyrimidin-6(7H)-yl)cyclobutyloxy) benzonitrile as a white solid (1054-1), which was directly used in next reaction. MS: calcd. for $C_{22}H_{24}ClO_4N_3S$ $[M+H]^+$: 459.1; found: 459.1.

2. Synthesis of Compound t-butyl 4-((1-(6-((1r,3r)-3-(3-chloro-4-cyanophenoxy)-2,2,4,4-tetramethylcyclobutyl)-5-oxo-6,7-dihydro-5H-pyrrolo[3,4-d]pyrimidin-2-yl)piperidine-4-yl)methyl)piperazine-1-carboxylate (1054-2)

2-Chloro-4-((1r,3r)-2,2,4,4-tetramethyl-3-(2-(methylsulfinyl)-5-oxo-5H-pyrrolo[3,4-d]pyrimidin-6(7H)-yl) cyclobutyloxy)benzonitrile (0.68 mmol, the crude product from the previous reaction) and t-butyl 4-(piperidin-4-ylmethyl)piperazine-1-carboxylate (193 mg, 0.68 mmol) were dissolved in dichloromethane (20 mL), to which was then added N,N-diisopropylethylamine (310 mg, 2.38 mmol). The reaction solution was stirred at room temperature overnight. The reaction solution was diluted with dichloromethane (30 mL), washed with saturated brine (20 mL×3), dried over anhydrous sodium sulfate, and purified by silica gel column chromatography (dichloromethane:methanol=100:1 to 20:1), to provide t-butyl 4-((1-(6-((1r,3r)-3-(3-chloro-4-cyanophenoxy)-2,2,4,4-tetramethylcyclobutyl)-5-oxo-6,7-dihydro-5H-pyrrolo[3,4-d]pyrimidin-2-yl)piperidine-4-yl) methyl)piperazine-1-carboxylate as a yellow solid (1054-2) (365 mg, 0.54 mmol), with a two-step yield of 80%. MS: calcd. for $C_{36}H_{49}ClO_7N_4$ $[M+H]^+$: 678.4; found: 678.3.

3. Synthesis of 2-chloro-4-((1r,3r)-2,2,4,4-tetramethyl-3-(5-oxo-2-(4-(piperazin-1-ylmethyl)piperidin-1-yl)-5Hpyrrolo[3,4-d]pyrimidin-6(7H)-yl)cyclobutyloxy) benzonitrile (1054-3)

t-Butyl 4-((1-(6-((1r,3r)-3-(3-chloro-4-cyanophenoxy)-2,2,4,4-tetramethylcyclobutyl)-5-oxo-6,7-dihydro-5H-pyrrolo[3,4-d]pyrimidin-2-yl)piperidine-4-yl)methyl) piperazine-1-carboxylate (1054-2) (200 mg, 0.30 mmol) was dissolved in dichloromethane (4 mL), and then trifluoroacetic acid (2 mL) was added in an ice bath. The reaction solution was stirred at room temperature for 1 h, and rotatory evaporated to dry. Then, the residue was dissolved in dichloromethane (20 mL), successively washed with saturated sodium carbonate solution (10 mL×3) and saturated brine (10 mL×2), dried over anhydrous sodium sulfate, and rotatory evaporated to dry, to provide the crude product 2-chloro-4-((1r,3r)-2,2,4,4-tetramethyl-3-(5-oxo-2-(4-(piperazin-1-ylmethyl)piperidin-1-yl)-5Hpyrrolo[3,4-d]pyrimidin-6(7H)-yl) cyclobutyloxy) benzonitrile (1054-3), which was directly used in next reaction. MS: calcd. for $C_{31}H_{41}ClO_7N_2$[M+H]$^+$: 578.3; found: 578.3.

4. Compound 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydro-pyrrolo[3,4-d]pyrimidin-6-yl)-2,2,4,4-tetramethylcyclobutoxy)benzonitrile 2-chloro-4-((1r,3r)-2,2,4,4-tetramethyl-3-(5-oxo-2-(4-(piperazin-1-ylmethyl) piperidin-1-yl)-5Hpyrrolo[3,4-d]pyrimidin-6(7H)-yl)cyclobutyloxy)benzonitrile (0.14 mmol, the crude product from the previous reaction) and N,N-diisopropylethylamine (90 mg, 0.7 mmol) were dissolved in dimethylsulfoxide (3 mL), to which was then added 2-(2,6-dioxopiperidin-3-yl)-5,6-difluoroisoindol-1,3-dione (60 mg, 0.20 mmol). The reaction solution was heated to 110° C. and allowed to react for 5 h. The reaction solution was diluted with water (10 mL) and then extracted with ethyl acetate (10 mL×3). The organic phase was combined and washed with saturated brine (10 mL×3), dried over anhydrous sodium sulfate, and purified by prep.-TLC (silica gel) (dichloromethane:methanol=25:1) to obtain a yellow solid 2-chloro-4-((1r,3r)-3-(2-(4-((4-(2,6-dioxopiperidin-3-yl)-6-fluoro-1,3-dioxoisoindolin-5-yl)piperazin-1-yl) methyl)piperidin-1-yl)-5-oxo-5,7-dihydro-pyrrolo[3,4-d]pyrimidin-6-yl)-2,2,4,4-tetramethylcyclobutoxy)benzonitrile (25 mg, 0.029 mmol), with a yield of 21%. MS: calcd. for $C_{44}H_{48}ClFO_9N_6$ $[M+H]^+$: 852.3; found: 852.3.

$^1$H NMR (400 MHz, DMSO-$d_6$) δ 11.13 (s, 1H), 8.63 (s, 1H), 7.90 (d, J=8.8 Hz, 1H), 7.74 (d, J=11.5 Hz, 1H), 7.46 (d, J=7.3 Hz, 1H), 7.28 (d, J=2.3 Hz, 1H), 7.05 (d, J=8.8, 2.4 Hz, 1H), 5.11 (d, J=12.8, 5.3 Hz, 1H), 4.78 (d, J=11.6 Hz, 2H), 4.67 (s, 2H), 4.49 (s, 1H), 4.28 (s, 1H), 3.26 (s, 4H), 3.15-3.01 (m, 3H), 2.95-2.82 (m, 1H), 2.59-2.53 (m, 3H), 2.23 (d, J=6.6 Hz, 3H), 2.10-1.78 (m, 5H), 1.38 (s, 6H), 1.19-1.00 (m, 8H).

383: 2-Chloro-4-((1r,3r)-3-(2-(4-((4-(2,6-dioxopiperidin-3-yl)-1,3-dioxoisoindolin-5-yl)piperazin-1-yl)methyl)piperidin-1-yl)-5-oxo-5,7-dihydro-pyrrolo[3,4-d]pyrimidin-6-yl)-2,2,4,4-tetramethylcyclobutoxy)benzonitrile
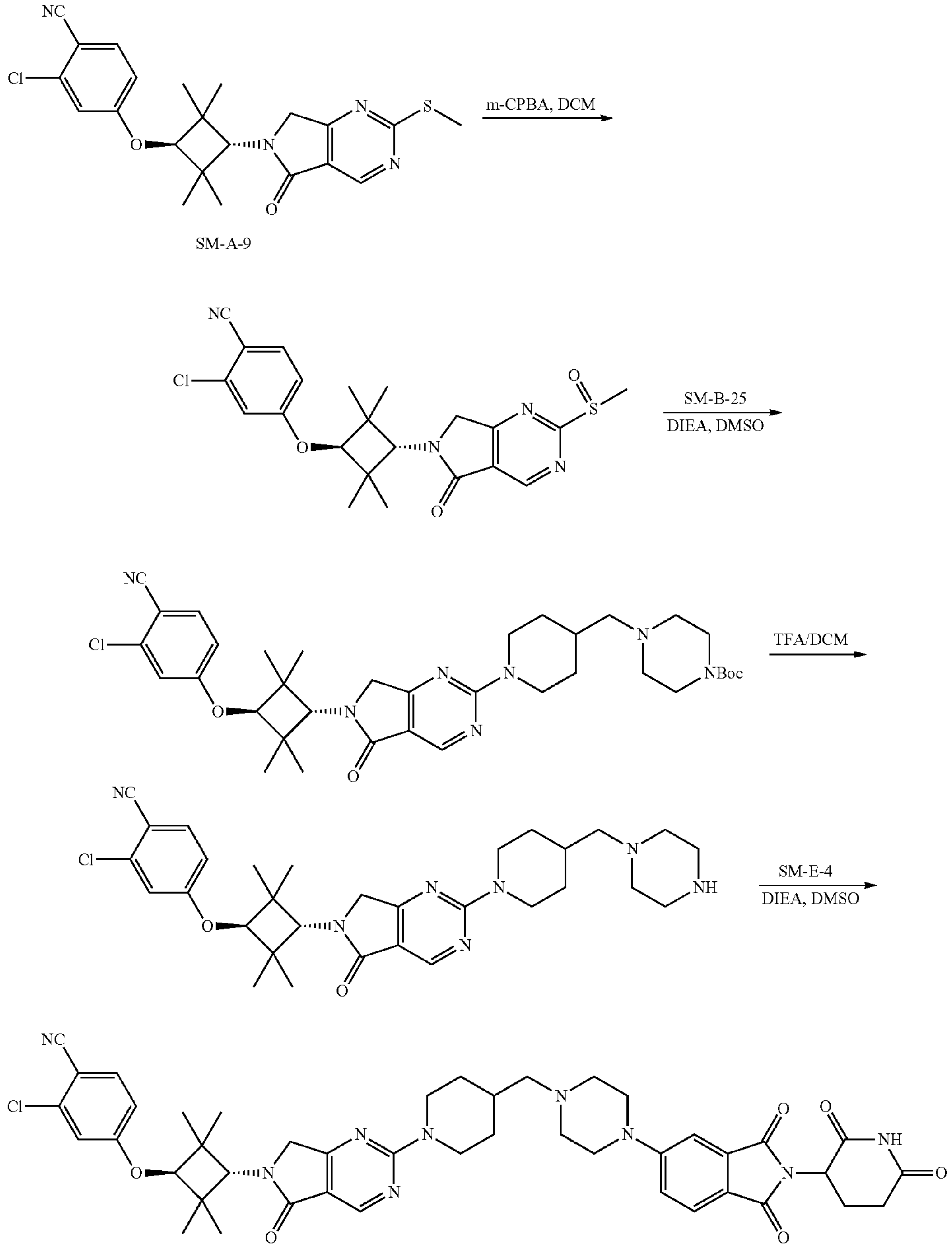
SM-A-9
383
$^1$H NMR (400 MHz, DMSO-$d_6$) δ 11.10 (s, 1H), 8.63 (s, 1H), 7.90 (d, J=8.7 Hz, 1H), 7.69 (d, J=8.5 Hz, 1H), 7.35 (s, 1H), 7.27 (d, J=8.5 Hz, 2H), 7.05 (dd, J=8.8, 2.0 Hz, 1H), 5.08 (d, J=12.8, 5.3 Hz, 1H), 4.78 (d, J=11.9 Hz, 2H), 4.66 (s, 2H), 4.49 (s, 1H), 4.28 (s, 1H), 3.45 (s, 4H), 3.09-2.82 (m, 4H), 2.59-2.53 (m, 3H), 2.21 (d, J=6.9 Hz, 3H), 2.10-1.76 (m, 5H), 1.38 (s, 6H), 1.14-1.06 (m, 8H). MS: calcd. for $C_{44}H_{48}ClN_9O_6$ $[M+H]^+$: 834.3; found: 832.9.

384: 2-Chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5,7-dihydropyrrolo[3,4-b]pyrazine-26-yl)-2,2,4,4-tetramethylcyclobutoxy) benzonitrile

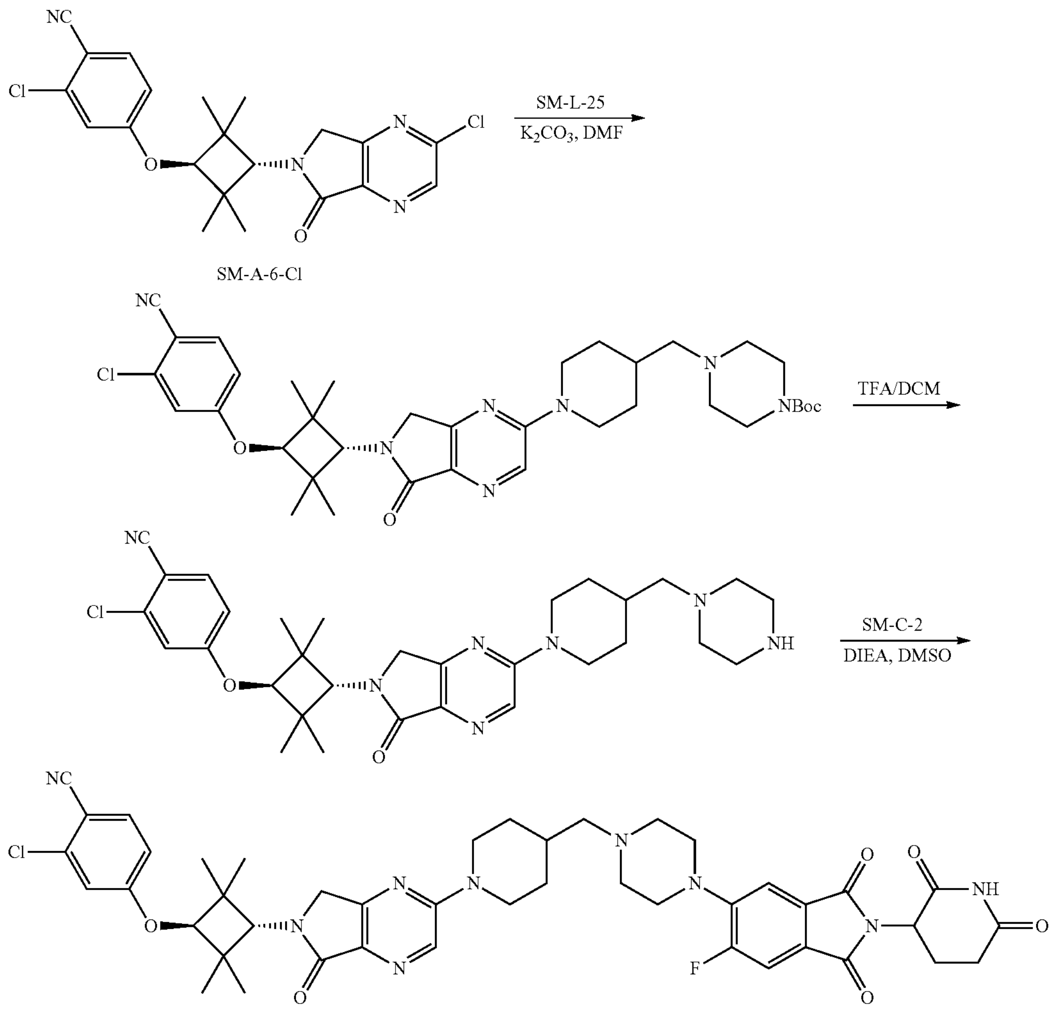

384

1. Compound t-butyl 4-((1-(6-((1r,3r)-3-(3-chloro-4-cyanophenoxy)-2,2,4,4-tetramethylcyclobutyl)-5-oxo-6,7-dihydro-5H-pyrrolo[3,4-b]pyrazine-22-yl) piperidine-4-yl)methyl)piperazine-1-carboxylic acid 2-Chloro-4-((1r,3r)-3-(2-chloro-5-oxo-5H-pyrrolo[3,4-b] pyrazine-26(7H)-yl)-2,2,4,4-tetramethylcyclobutoxy)benzonitrile (200 mg, 0.46 mmol) and t-butyl 4-(piperidin-4-ylmethyl)piperazine-1-carboxylate (328 mg, 1.16 mmol) were dissolved in N,N-dimethylformamide (5 mL), to which was then added potassium carbonate (190 mg, 1.38 mmol). The reaction solution was heated to 80° C. and allowed to react overnight under stirring. The reaction solution was diluted with water (10 mL) and then extracted with ethyl acetate (10 mL×3). The organic phase was combined and washed with saturated brine (10 mL×3), dried over anhydrous sodium sulfate, and purified by silica gel column chromatography (dichloromethane:methanol=100:1 to 20:1) to obtain a yellow solid t-butyl 4-((1-(6-((1r,3r)-3-(3-chloro-4-cyanophenoxy)-2,2,4,4-tetramethylcyclobutyl)-5-oxo-6,7-dihydro-5H-pyrrolo[3,4-b]pyrazine-22-yl) piperidine-4-yl)methyl)piperazine-1-carboxylate (1056-1) (190 mg, 0.28 mmol), with a yield of 61%. MS: calcd. for $C_{36}H_{49}ClO_7N_4$ $[M+H]^+$: 678.4; found: 678.3.

2. Compound 2-chloro-4-((1r,3r)-2,2,4,4-tetramethyl-3-(5-oxo-2-(4-(piperazin-1-ylmethyl)piperidin-1-yl)-5Hpyrrolo[3,4-b]pyrazine-26(7H)-yl)cyclobutyloxy) benzonitrile t-Butyl 4-((1-(6-((1r,3r)-3-(3-chloro-4-cyanophenoxy)-2,2,4,4-tetramethylcyclobutyl)-5-oxo-6,7-dihydro-5H-pyrrolo [3,4-b]pyrazine-22-yl)piperidine-4-yl)methyl) piperazine-1-carboxylate (190 mg, 0.28 mmol) was dissolved in dichloromethane (4 mL), to which was added trifluoroacetic acid (2 mL) in an ice bath. The reaction solution was stirred at room temperature for 1 h, and rotatory evaporated to dry. Then, the residue was dissolved in dichloromethane (20 mL), washed with saturated sodium carbonate solution (10 mL×3) and saturated brine (10 mL×2), dried over anhydrous sodium sulfate, and rotatory evaporated to dry, to provide the crude product 2-chloro-4-((1r,3r)-2,2,4,4-tetramethyl-3-(5-oxo-2-(4-(piperazin-1-ylmethyl)piperidin-1-yl)-5Hpyrrolo [3,4-b]pyrazine-26(7H)-yl)cyclobutyloxy)benzonitrile, which was directly used in next reaction.

MS: calcd. for $C_{31}H_{41}ClO_7N_2[M+H]^+$: 578.3; found: 578.3.

3. Compound 2-chloro-4-((1r,3r)-3-(2-(4-((4-(2,6-dioxopiperidin-3-yl)-6-fluoro-1,3-dioxoisoindolin-5-yl)piperazin-1-yl)methyl)piperidin-1-yl)-5-oxo-5H-pyrrolo[3,4-b]pyrazine-26(7H)-yl)-2,2,4,4-tetramethylcyclobutoxy)benzonitrile 2-chloro-4-((1r,3r)-2,2,4,4-tetramethyl-3-(5-oxo-2-(4-(piperazin-1-ylmethyl) piperidin-1-yl)-5H-pyrrolo[3,4-b] pyrazine-26(7H)-yl)cyclobutyloxy)benzonitrile (1056-2) (0.11 mmol, the crude product from the previous reaction) and N,N-diisopropylethylamine (71 mg, 0.55 mmol) were dissolved in dimethylsulfoxide (3 mL), to which was then added 2-(2,6-dioxopiperidin-3-yl)-5,6-difluoroisoindol-1,3-dione (SM-C-2) (42 mg, 0.15 mmol). The reaction solution was heated to 110° C. and allowed to react for 5 h. The reaction solution was diluted with water (10 mL) and then extracted with ethyl acetate (10 mL×3). The organic phase was combined and washed with saturated brine (10 mL×3), dried over anhydrous sodium sulfate, and purified by prep.-TLC (silica gel) (dichloromethane:methanol=25:1) to obtain a yellow solid 2-chloro-4-((1r,3r)-3-(2-(4-((4-(2,6-dioxopiperidin-3-yl)-6-fluoro-1,3-dioxoisoindol-5-yl) piperazin-1-yl)methyl)piperidin-1-yl)-5-oxo-5H-pyrrolo[3,4-b]pyrazine-26(7H)-yl)-2,2,4,4-tetramethylcyclobutoxy) benzonitrile (19 mg, 0.022 mmol), with a yield of 20%. MS: calcd. for $C_{44}H_{48}ClFO_9N_F[M+H]^+$: 852.3; found: 852.3. $^1H$ NMR (400 MHz, DMSO-$d_6$) δ 11.13 (s, 1H), 8.53 (s, 1H), 7.91 (d, J=8.8 Hz, 1H), 7.74 (d, J=11.3 Hz, 1H), 7.46 (d, J=7.4 Hz, 1H), 7.29 (d, J=2.4 Hz, 1H), 7.07 (dd, J=8.8, 2.4 Hz, 1H), 5.11 (dd, J=12.6, 4.9 Hz, 1H), 4.68 (s, 2H), 4.55 (s, 1H), 4.43 (d, J=12.7 Hz, 2H), 4.32 (s, 1H), 3.29-3.10 (m, 4H), 3.04-2.78 (m, 3H), 2.68-2.53 (m, 4H), 2.44-2.18 (m, 4H), 2.09-1.95 (m, 2H), 1.92-1.62 (m, 4H), 1.40 (s, 6H), 1.17 (s, 6H).

385: 2-Chloro-4-((1r,3r)-3-(2-(4-((4-(2,6-dioxopiperidin-3-yl)-1,3-dioxoisoindolin-5-yl)piperazin-1-yl) methyl)piperidin-1-yl)-5-oxo-5,7-dihydro-pyrrolo[3,4-b]pyrazine-26-yl)-2,2,4,4-tetramethylcyclobutoxy) benzonitrile

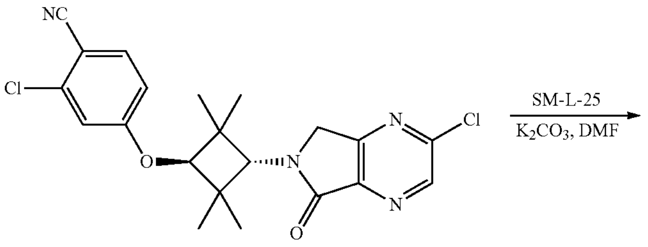

SM-A-6-Cl

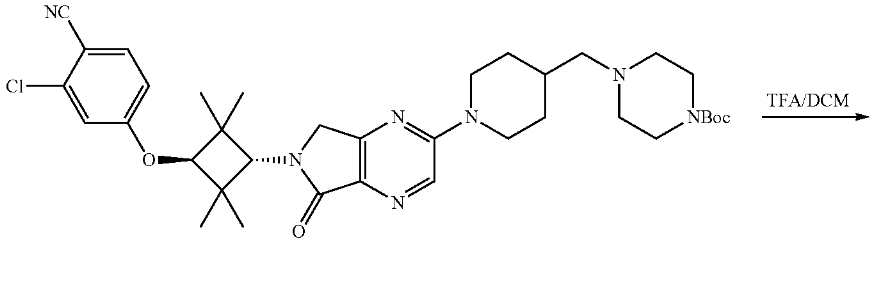

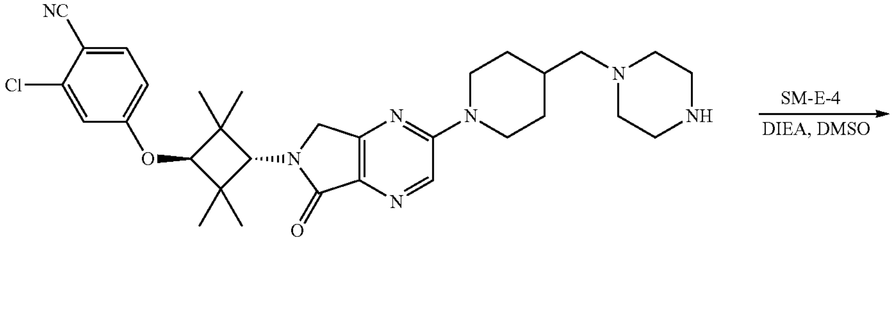

-continued
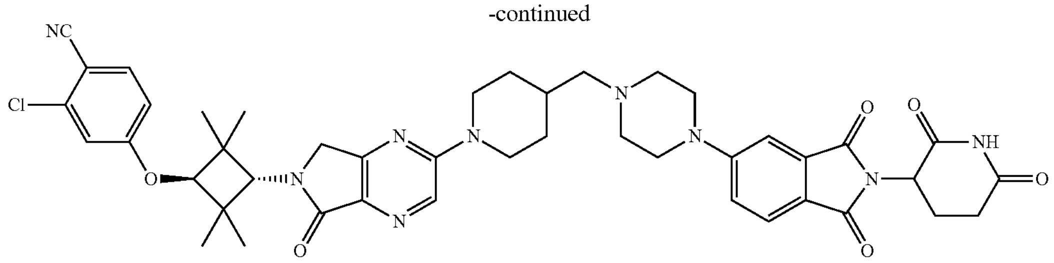
385
$^1$H NMR (400 MHz, DMSO-$d_6$) δ 11.10 (s, 1H), 8.52 (s, 1H), 7.91 (d, J=8.7 Hz, 1H), 7.69 (d, J=8.5 Hz, 1H), 7.35 (s, 1H), 7.28 (dd, J=10.1, 5.8 Hz, 2H), 7.07 (dd, J=8.8, 2.3 Hz, 1H), 5.08 (dd, J=12.7, 5.4 Hz, 1H), 4.68 (s, 2H), 4.55 (s, 1H), 4.43 (d, J=12.4 Hz, 2H), 4.32 (s, 1H), 3.58-3.37 (m, 4H), 3.04-2.80 (m, 3H), 2.71-2.51 (m, 4H), 2.40-2.15 (m, 4H), 2.10-1.96 (m, 2H), 1.94-1.71 (m, 4H), 1.40 (s, 6H), 1.17 (s, 6H). MS: calcd. for $C_{44}H_{46}ClN_9O_6$ $[M+H]^+$:834.3; found:834.3.
386: 2-Chloro-4-((1r,3r)-3-(2-((4-(5-(2,6-dioxopiperidin-3-yl)-6-fluoro-1,3-dioxoisoindolin-5-yl)-2,5-diazabicyclo[2.2.1]heptan-2-yl)cyclohexyl)ethynyl)-5-oxo-5,7-dihydro-pyrrolo[3,4-b]pyrazine-26-yl)-2,2,4,4-tetramethylcyclobutoxy) benzonitrile
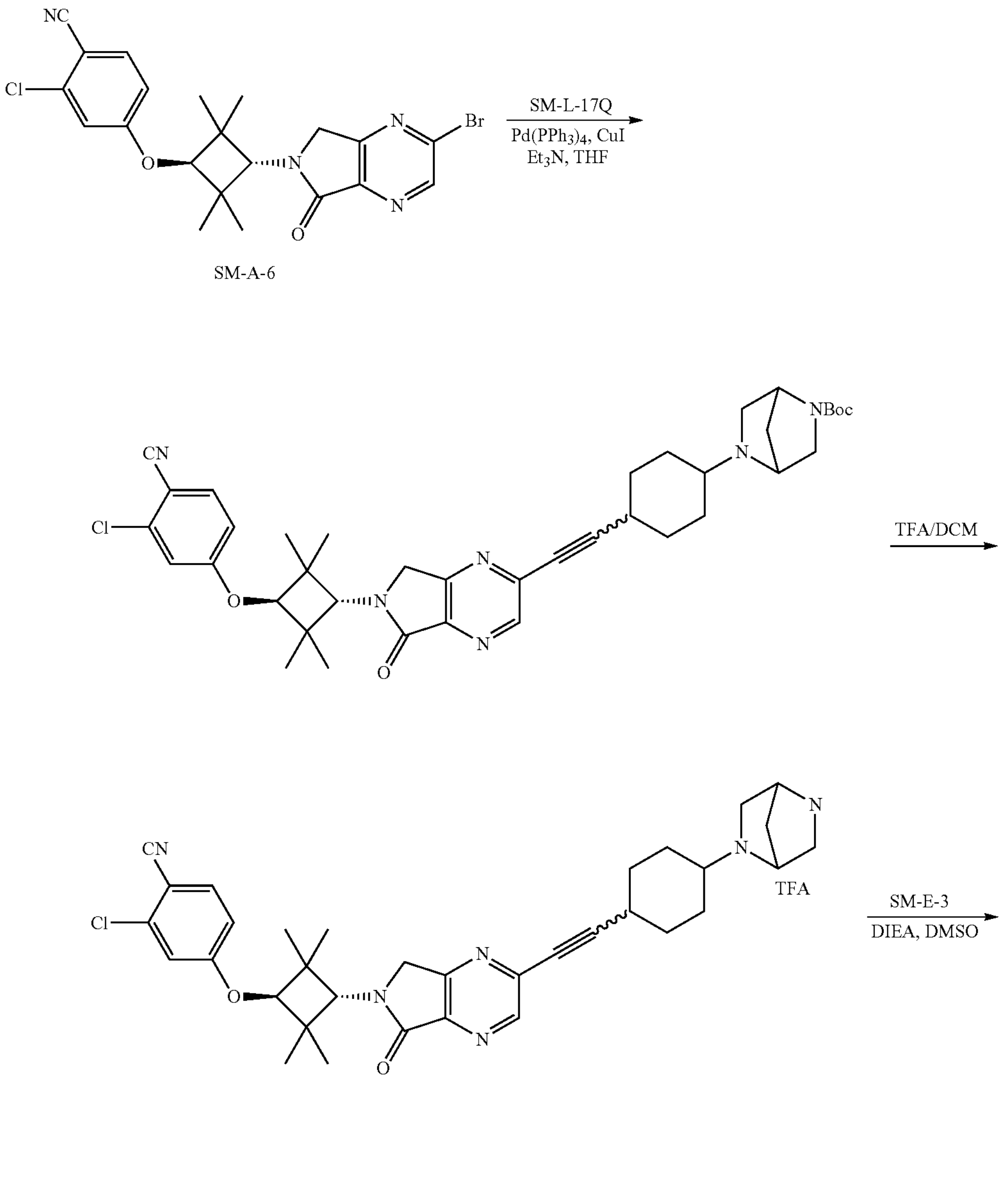
SM-A-6

-continued
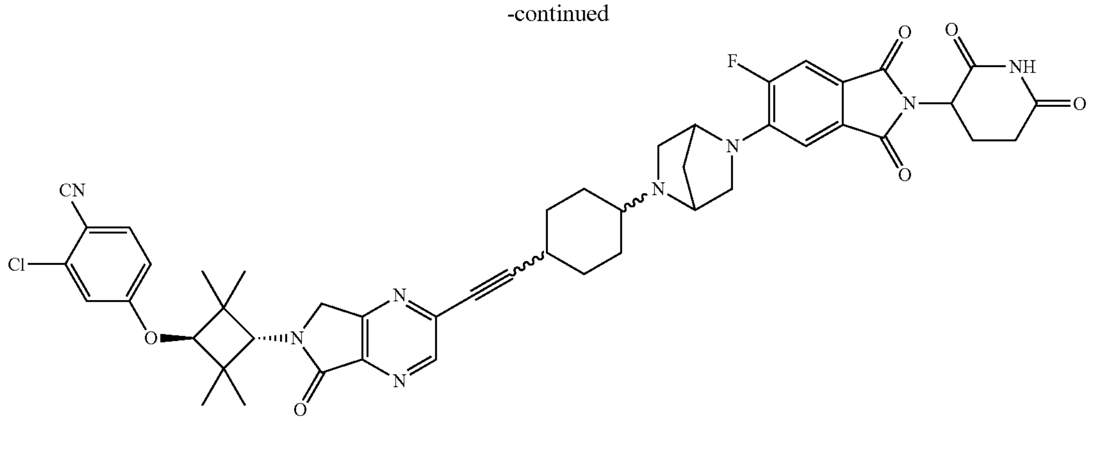
386
$^1$H NMR (400 MHz, DMSO-$d_6$) δ 11.10 (s, 1H), 8.83 (s, 1H), 7.92 (d, J=8.8 Hz, 1H), 7.63 (d, J=12.4 Hz, 1H), 7.30 (d, J=2.4 Hz, 1H), 7.16 (d, J=7.5 Hz, 1H), 7.08 (dd, J=8.8, 2.4 Hz, 1H), 5.07 (dd, J=12.8, 5.4 Hz, 1H), 4.86 (s, 2H), 4.61 (s, 1H), 4.55 (s, 1H), 4.38 (s, 1H), 3.79 (s, 1H), 3.62 (d, J=8.9 Hz, 1H), 3.52 (d, J=8.7 Hz, 1H), 3.13 (d, J=8.7 Hz, 1H), 2.95-2.63 (m, 2H), 2.57-2.63 (m, 1H), 2.46-2.38 (m, 2H), 2.35-2.32 (m, 1H), 2.04-1.94 (m, 1H), 1.85-1.75 (m, 4H), 1.74-1.49 (m, 6H), 1.40 (s, 6H), 1.17 (s, 6H). MS: calcd. for $C_{47}H_{46}ClFN_8O_6$ $[M+H]^+$: 873.3; found: 873.3.
387: 2-Chloro-4-((1r,3r)-3-(2-((4-(5-(2,6-dioxopiperidin-3-yl)-6-fluoro-1,3-dioxoisoindolin-5-yl)-2,5-diazabicyclo[2.2.1]heptan-2-yl)cyclohexyl)ethynyl)-5-oxo-5,7-dihydro-pyrrolo[3,4-b]pyrazine-26-yl)-2,2,4,4-tetramethylcyclobutoxy) benzonitrile
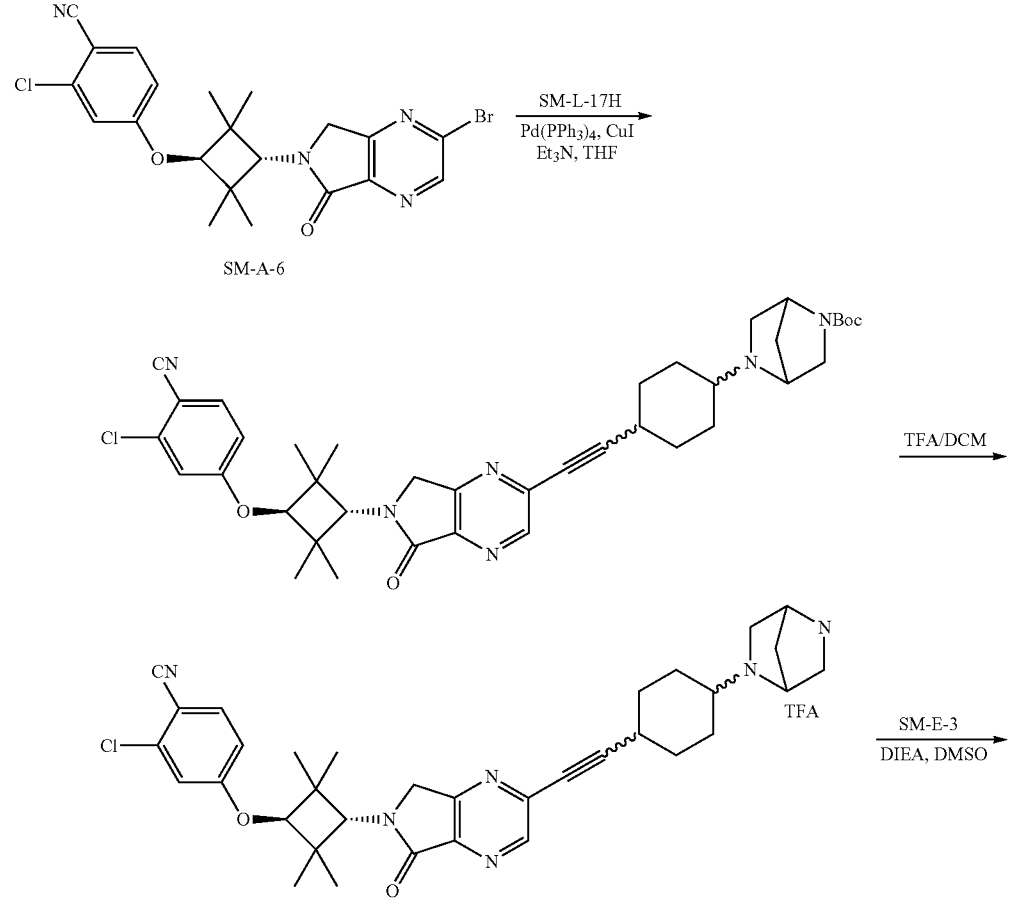

-continued
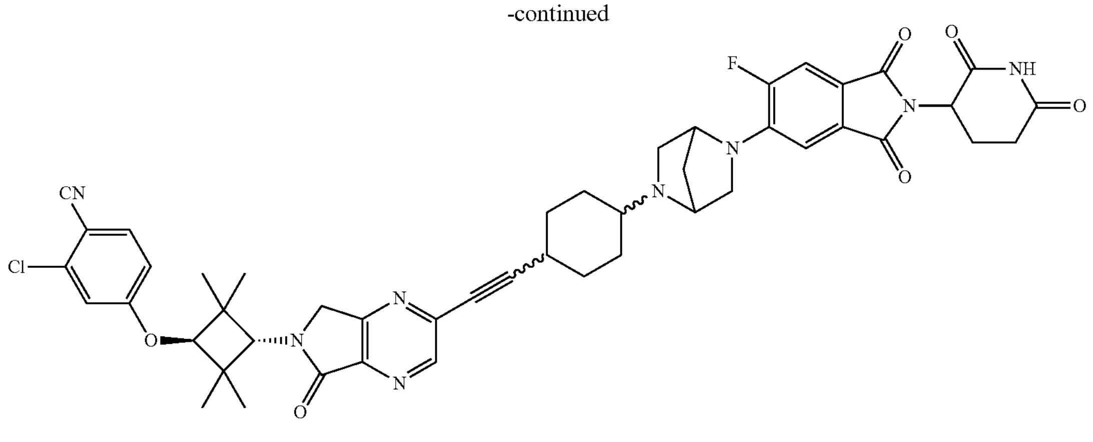
387
$^{1}$H NMR (400 MHz, DMSO-$d_6$) δ 11.11 (s, 1H), 8.81 (d, J=8.5 Hz, 1H), 7.91 (d, J=8.8 Hz, 1H), 7.64 (d, J=12.4 Hz, 1H), 7.30 (d, J=2.3 Hz, 1H), 7.16 (d, J=6.7 Hz, 1H), 7.07 (dd, J=8.8, 2.3 Hz, 1H), 5.08 (dd, J=12.9, 5.2 Hz, 1H), 4.88-4.83 (m, 2H), 4.61-4.55 (m, 2H), 4.36 (s, 1H), 3.79 (s, 1H), 3.63 (s, 1H), 3.52 (s, 1H), 3.14-3.11 (m, 1H), 2.98-2.76 (m, 1H), 2.67-2.54 (m, 4H), 2.33-2.25 (m, 1H), 2.03-1.85 (m, 7H), 1.58-1.37 (m, 8H), 1.23-1.16 (m, 8H). MS: calcd. for $C_{47}H_{46}ClFN_8O_6$ [M+H]$^+$: 873.3; found: 872.8.
388: 2-Chloro-4-((1r,3r)-3-(2-((4-(5-(2-(2,6-dioxopiperidin-3-yl)-1,3-dioxoisoindolin-5-yl)-2,5-diazabicyclo[2.2.1]heptan-2-yl)cyclohexyl)ethynyl)-5-oxo-5,7-dihydro-pyrrolo[3,4-b]pyrazine-26-yl)-2,2,4,4-tetramethylcyclobutoxy) benzonitrile
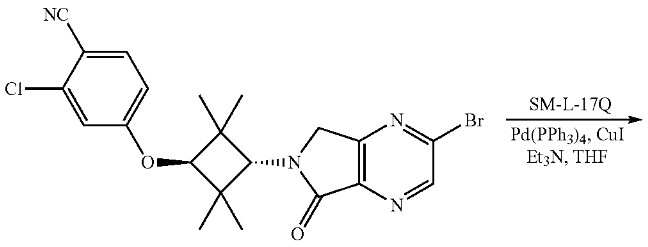
SM-A-6
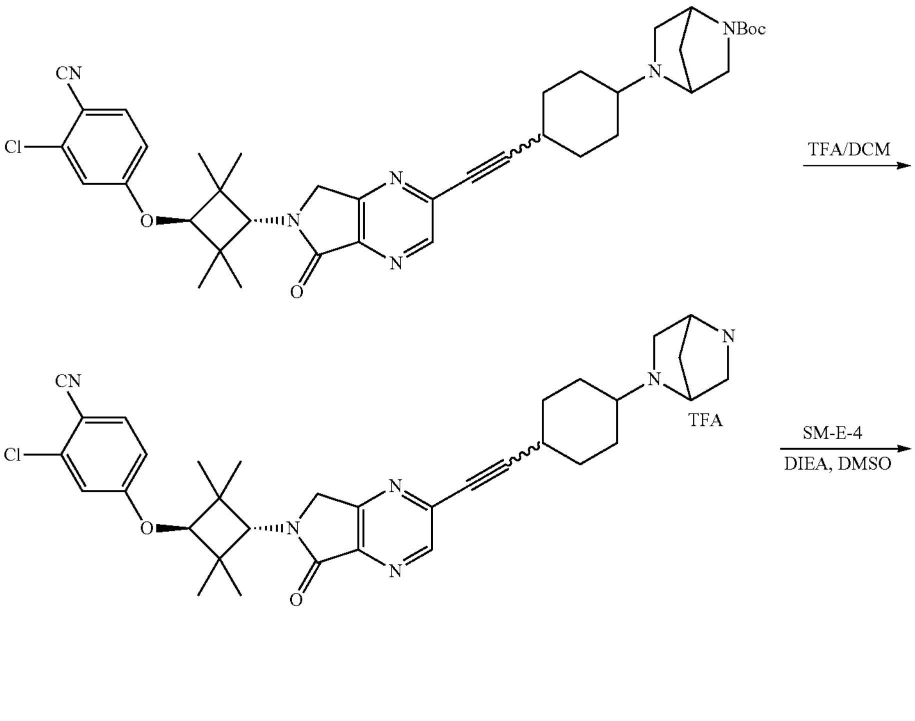

-continued
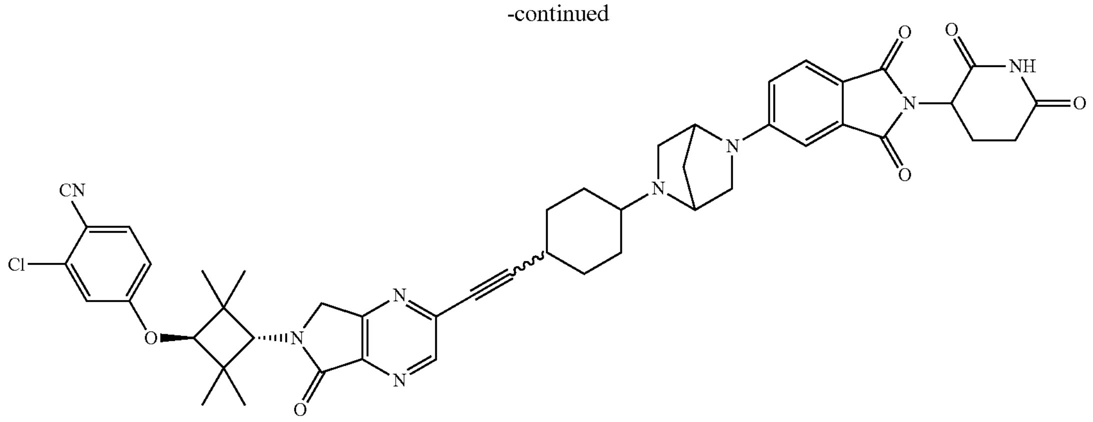
388
$^1$H NMR (400 MHz, DMSO-$d_6$) δ 11.09 (s, 1H), 8.83 (s, 1H), 7.92 (d, J=8.7 Hz, 1H), 7.64 (d, J=8.4 Hz, 1H), 7.30 (d, J=2.3 Hz, 1H), 7.07 (dt, J=12.0, 6.0 Hz, 2H), 6.88 (s, 1H), 5.06 (dd, J=12.9, 5.4 Hz, 1H), 4.86 (s, 2H), 4.64 (s, 1H), 4.55 (s, 1H), 4.38 (s, 1H), 3.86 (s, 1H), 3.42 (s, 2H), 3.12 (d, J=8.4 Hz, 1H), 3.03-2.81 (m, 2H), 2.65-2.54 (m, 2H), 2.35-2.25 (m, 2H), 2.04-1.94 (m, 1H), 1.93-1.78 (m, 4H), 1.75-1.52 (m, 6H), 1.43 (s, 6H), 1.17 (s, 6H). MS: calcd. for $C_{47}H_{47}ClN_8O_6$ $[M+H]^+$: 855.3; found: 855.3.
389: 2-Chloro-4-((1r,3r)-3-(2-((4-(5-(2-(2,6-dioxopiperidin-3-yl)-1,3-dioxoisoindolin-5-yl)-2,5-diazabicyclo[2.2.1]heptan-2-yl)cyclohexyl)ethynyl)-5-oxo-5,7-dihydro-pyrrolo[3,4-b]pyrazine-26-yl)-2,2,4,4-tetramethylcyclobutoxy) benzonitrile
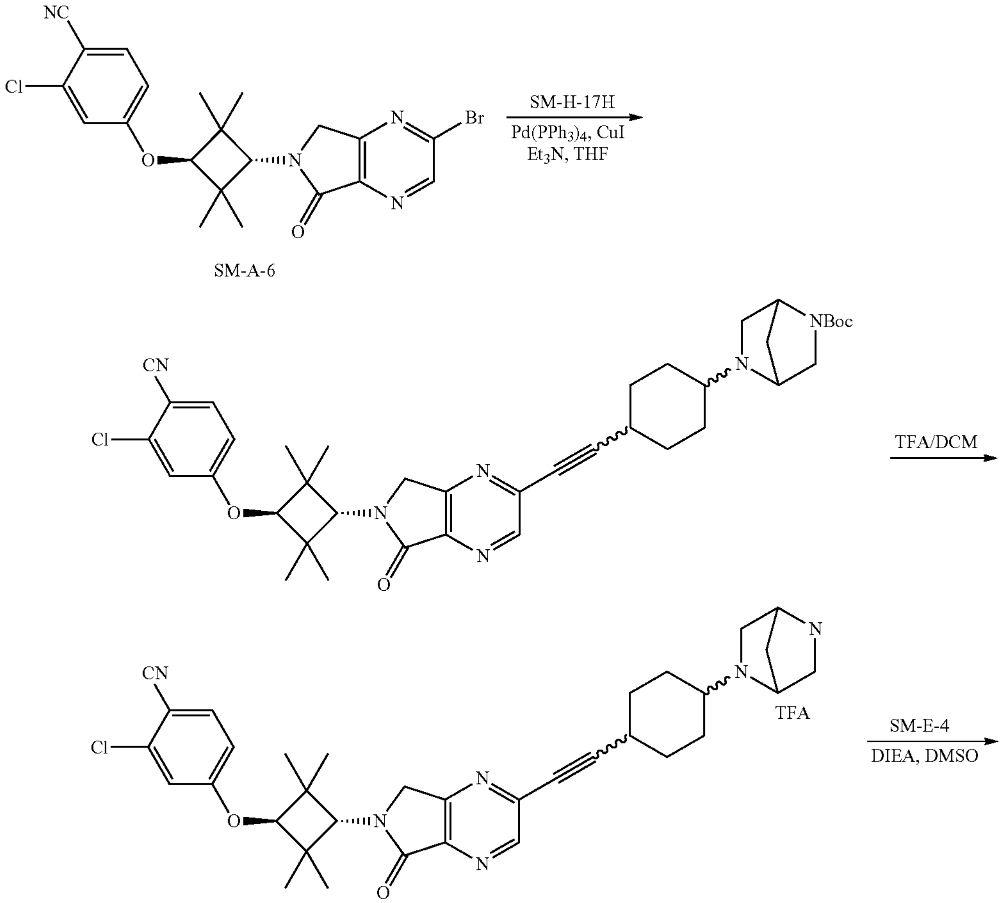
SM-A-6

-continued
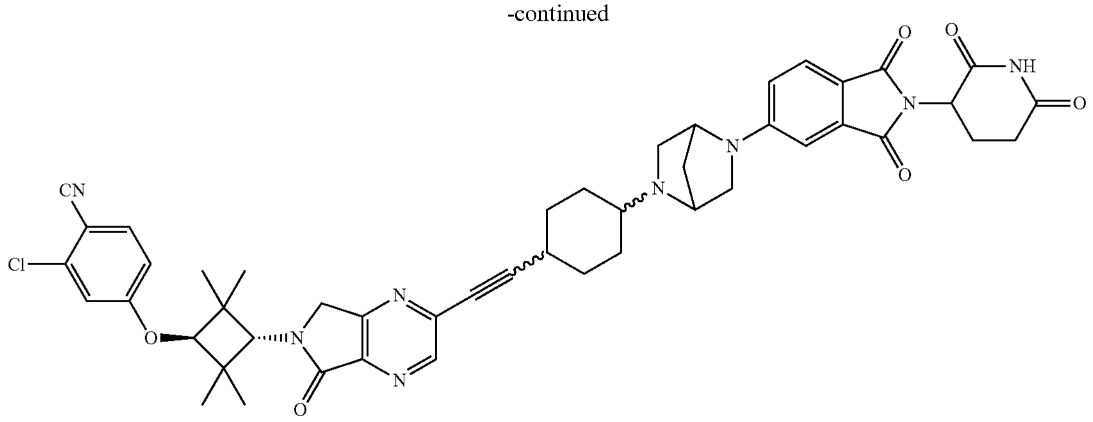
389
$^1$H NMR (400 MHz, DMSO-$d_6$) δ 11.08 (s, 1H), 8.81 (d, J=8.6 Hz, 1H), 7.91 (d, J=8.8 Hz, 1H), 7.64 (d, J=8.4 Hz, 1H), 7.30 (d, J=2.3 Hz, 1H), 7.08-6.87 (m, 3H), 5.06 (dd, J=12.9, 5.2 Hz, 1H), 4.88-4.83 (m, 2H), 4.60 (d, J=34.6 Hz, 1H), 4.55 (s, 1H), 4.36 (s, 1H), 3.84 (s, 1H), 3.42 (s, 2H), 3.11-3.09 (m, 1H), 2.92-2.84 (m, 1H), 2.67-2.55 (m, 4H), 2.25-2.19 (m, 1H), 2.02-1.81 (m, 7H), 1.51-1.38 (m, 8H), 1.27-1.16 (m, 8H). MS: calcd. for $C_{47}H_{47}ClN_8O_6$ $[M+H]^+$: 855.3; found: 854.9.
390: 2-chloro-4-((1r,3r)-3-(2-((1r,3r)-3-(4-(2-(2,6-dioxopiperidin-3-yl)-1,3-dioxoisoindolin-5-yl)piperazin-1-yl)cyclobutyl)ethynyl)-5-oxo-5,7-dihydro-pyrrolo[3,4-b]pyrazine-26-yl)-2,2,4,4-tetramethylcyclobutoxy)benzonitrile
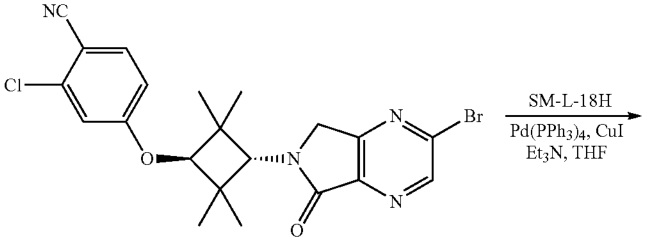
SM-A-6
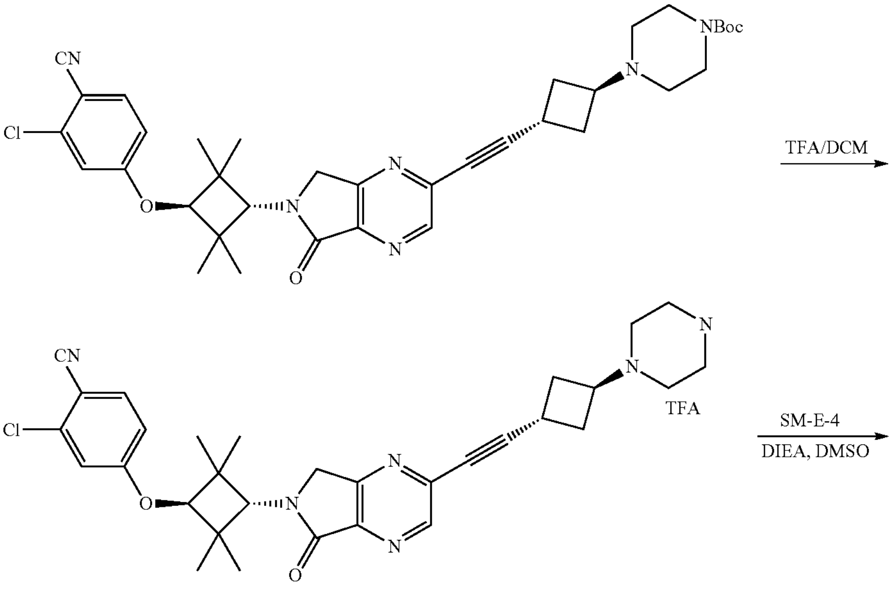

-continued
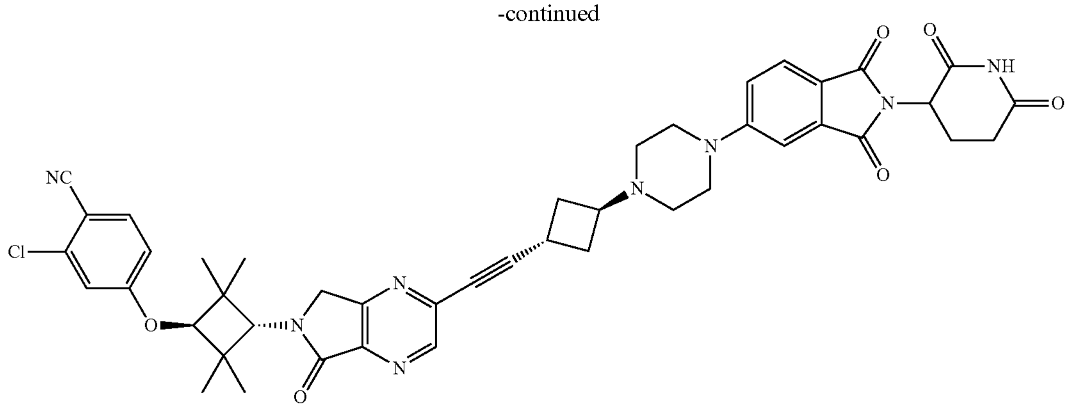
390
$^1$H NMR (400 MHz, DMSO-$d_6$) δ 11.10 (s, 1H), 8.88 (d, J=7.6 Hz, 1H), 7.91 (d, J=8.7 Hz, 1H), 7.69 (d, J=8.4 Hz, 1H), 7.34 (d, J=20.1 Hz, 1H), 7.29 (dd, J=9.7, 5.6 Hz, 2H), 7.08 (dd, J=8.8, 2.2 Hz, 1H), 5.08 (dd, J=12.9, 5.3 Hz, 1H), 4.90-4.85 (m, 2H), 4.55 (d, J=2.7 Hz, 1H), 4.38 (d, J=2.0 Hz, 1H), 3.46 (s, 4H), 3.15-3.12 (m, 1H), 2.93-2.84 (m, 1H), 2.68-2.55 (m, 2H), 2.46-2.40 (m, 4H), 2.39-2.33 (m, 3H), 2.30-2.28 (m, 2H), 2.04-2.01 (m, 1H), 1.43 (s, 6H), 1.17 (s, 6H). MS: calcd. for $C_{44}H_{43}ClN_8O_6$ $[M+H]^+$: 815.3; found: 815.3.
391: 2-Chloro-4-((1r,3r)-3-(2-((1r,3r)-3-(4-(2-(2,6-dioxopiperidin-3-yl)-6-fluoro-1,3-dioxoisoindolin-5-yl)piperazin-1-yl)cyclobutyl)ethynyl)-5-oxo-5,7-dihydro-pyrrolo[3,4-b]pyrazine-26-yl)-2,2,4,4-tetramethylcyclobutoxy)benzonitrile
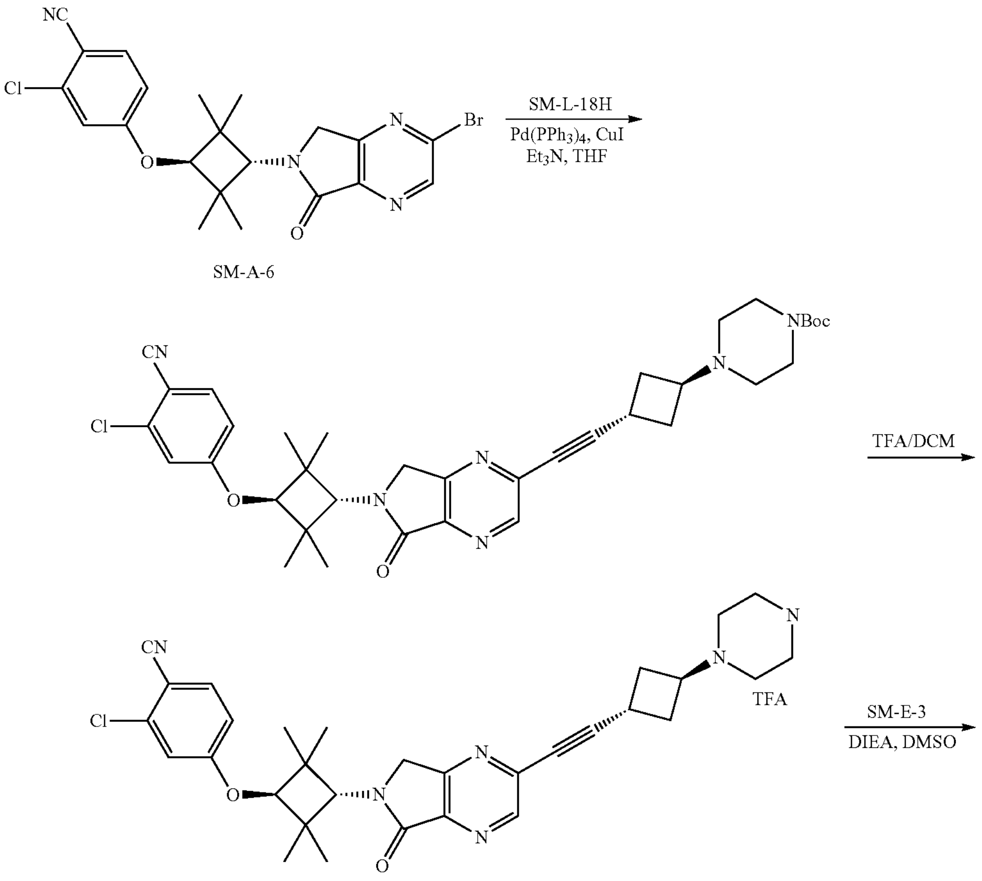

-continued
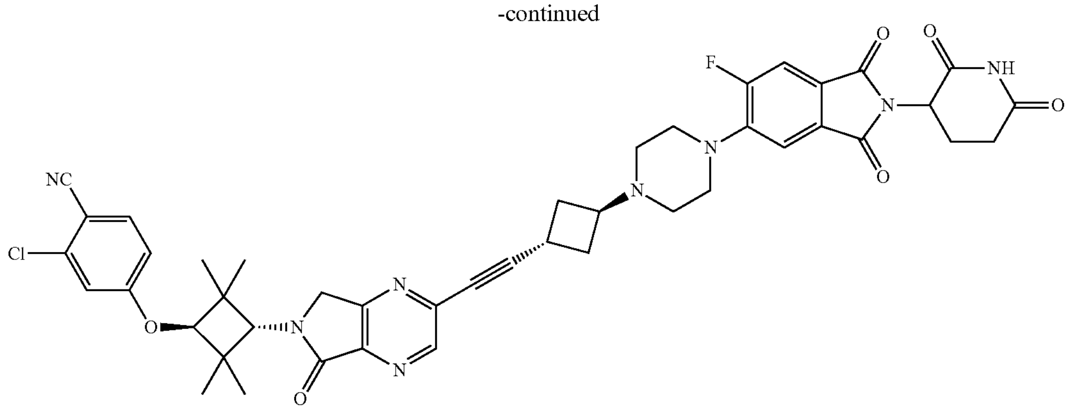
391
$^1$H NMR (400 MHz, DMSO-$d_6$) δ 11.13 (s, 1H), 8.88 (d, J=7.7 Hz, 1H), 7.91 (d, J=8.7 Hz, 1H), 7.75 (d, J=11.4 Hz, 1H), 7.47 (d, J=7.3 Hz, 1H), 7.30 (d, J=2.3 Hz, 1H), 7.08 (dd, J=8.8, 2.3 Hz, 1H), 5.11 (dd, J=12.8, 5.4 Hz, 1H), 4.90-4.85 (m, 2H), 4.56 (d, J=2.7 Hz, 1H), 4.38 (s, 1H), 3.27 (s, 4H), 3.20-3.15 (m, 1H), 2.92-2.84 (m, 1H), 2.68-2.52 (m, 2H), 2.47-2.29 (m, 9H), 2.08-2.02 (m, 1H), 1.43 (s, 6H), 1.18 (s, 6H). MS: calcd. for $C_{44}H_{42}ClFN_8O_6$ $[M+H]^+$: 833.3; found: 833.3.
392: 4-((1r,3r)-3-(2-((1r,3r)-3-(4-(2,6-Dioxopiperidin-3-yl)-1,3-dioxoisoindolin-5-yl)piperazin-1-yl) cyclobutyl)ethynyl)-5-oxo-5,7-dihydro-pyrrolo[3,4-b]pyridin-6-yl)-2,2,4,4-tetramethylcyclobutoxy)-2-methoxybenzonitrile
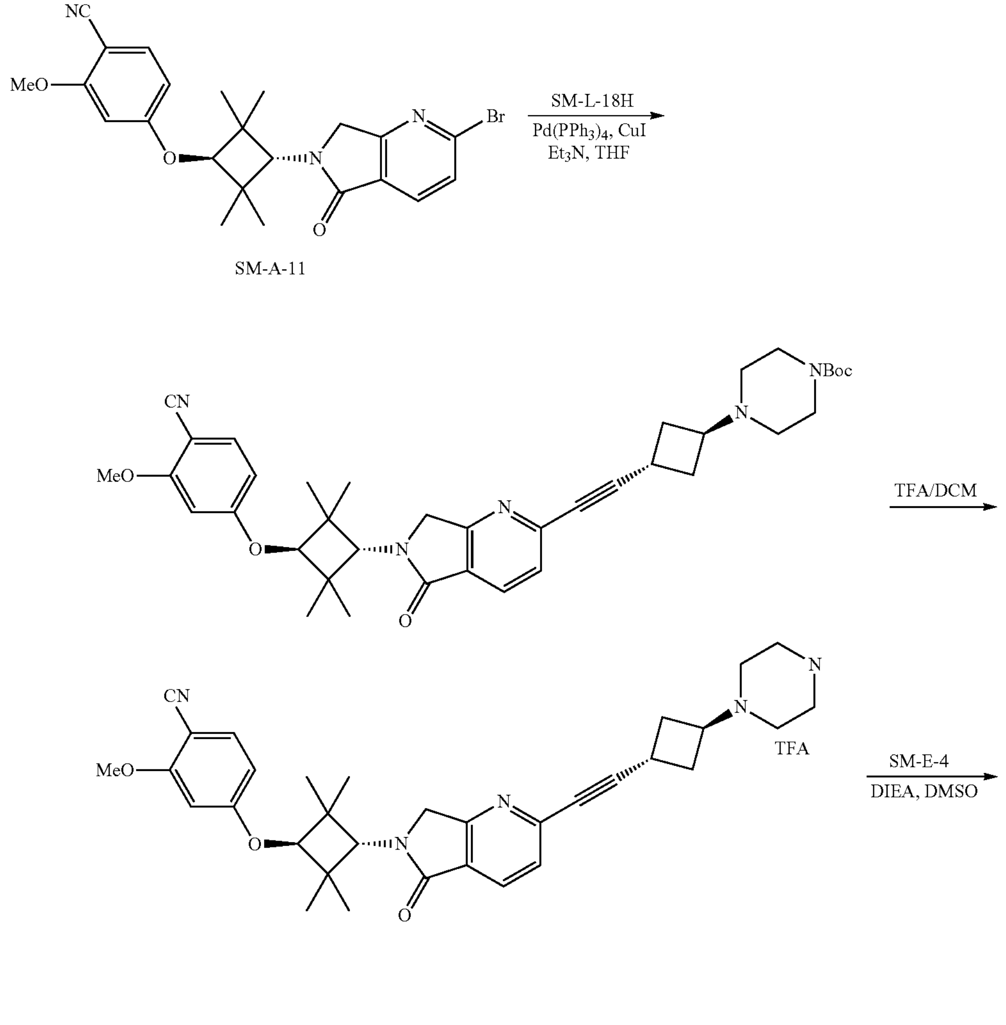

-continued
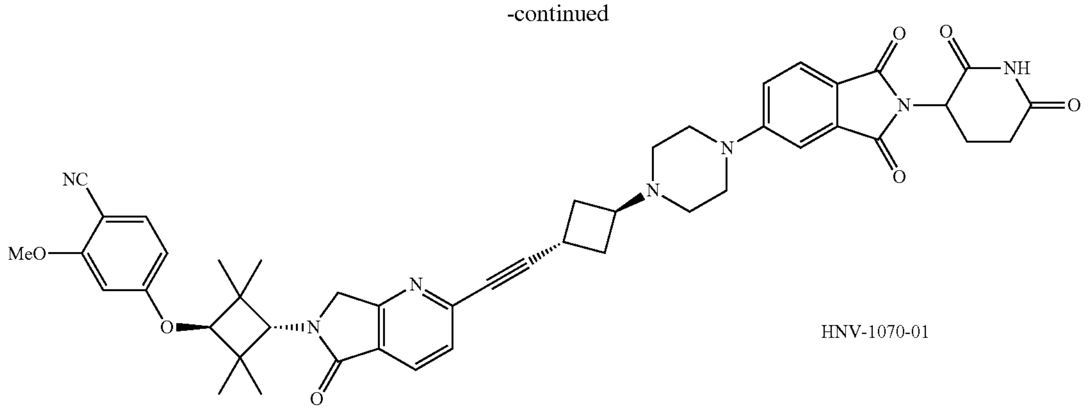
HNV-1070-01
392
$^1$H NMR (400 MHz, DMSO-$d_6$) δ 11.09 (s, 1H), 8.06 (d, J=7.9 Hz, 1H), 7.69 (d, J=8.5 Hz, 1H), 7.65 (d, J=8.6 Hz, 1H), 7.59 (d, J=7.8 Hz, 1H), 7.36 (s, 1H), 7.28 (d, J=8.0 Hz, 1H), 6.69 (d, J=2.0 Hz, 1H), 6.60 (dd, J=8.7, 2.1 Hz, 1H), 5.08 (dd, J=12.9, 5.5 Hz, 1H), 4.82 (s, 2H), 4.49 (s, 1H), 4.34 (s, 1H), 3.92 (s, 3H), 3.64-3.34 (m, 4H), 3.32-3.18 (m, 2H), 3.17-3.03 (m, 1H), 2.93-2.79 (m, 1H), 2.71-2.54 (m, 2H), 2.48-2.37 (m, 4H), 2.38-2.31 (m, 1H), 2.30-2.19 (m, 2H), 2.08-1.95 (m, 1H), 1.41 (s, 6H), 1.18 (s, 6H). MS: calcd. for $C_{46}H_{47}N_7O_7$ [M+H]$^+$:810.4; found:810.3.
393: 4-((1r,3r)-3-(2-((1r,3r)-3-(4-(2,6-Dioxopiperidin-3-yl)-6-fluoro-1,3-dioxoisoindolin-5-yl)piperazin-1-yl)cyclobutyl)ethynyl)-5-oxo-5,7-dihydro-pyrrolo[3,4-b]pyridin-6-yl)-2,2,4,4-tetramethylcyclobutoxy)-2-methoxybenzonitrile
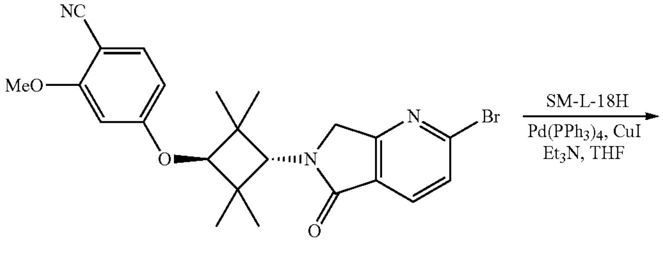
SM-A-11
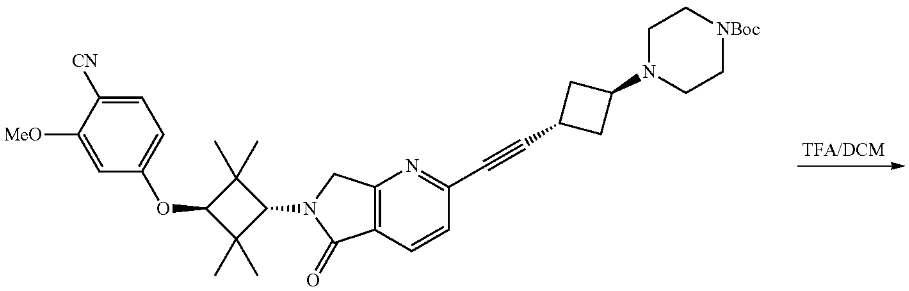
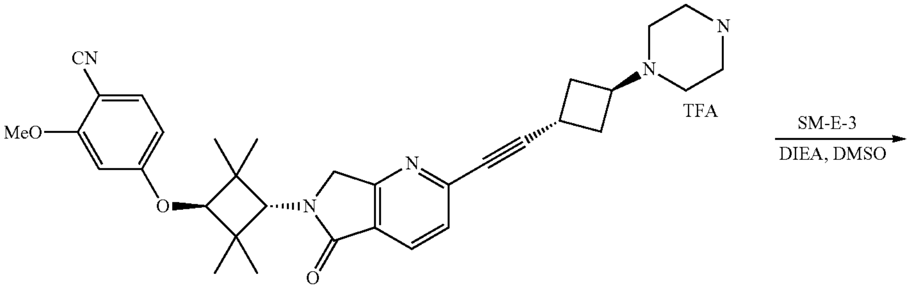

-continued
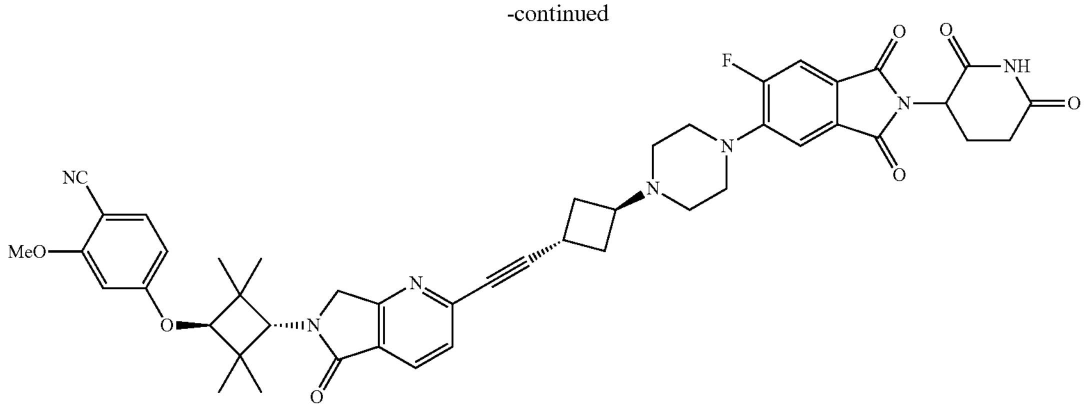
393
$^1$H NMR (400 MHz, DMSO-$d_6$) δ 11.12 (s, 1H), 8.06 (d, J=7.9 Hz, 1H), 7.74 (d, J=11.1 Hz, 1H), 7.65 (d, J=8.6 Hz, 1H), 7.59 (d, J=7.9 Hz, 1H), 7.47 (d, J=7.6 Hz, 1H), 6.70 (d, J=2.1 Hz, 1H), 6.60 (dd, J=8.7, 2.2 Hz, 1H), 5.11 (dd, J=12.7, 5.4 Hz, 1H), 4.82 (s, 2H), 4.49 (s, 1H), 4.34 (s, 1H), 3.92 (s, 3H), 3.33-3.17 (m, 6H), 3.17-3.10 (m, 1H), 2.96-2.83 (m, 1H), 2.74-2.54 (m, 2H), 2.47-2.37 (m, 4H), 2.36-2.33 (m, 1H), 2.28-2.19 (m, 2H), 2.07-1.99 (m, 1H), 1.42 (s, 6H), 1.18 (s, 6H). MS: calcd. for $C_{41}H_{46}FN_7O_7$ $[M+H]^+$: 828.3; found: 828.3.
394: 2-Chloro-4-((1r,3r)-3-(2-((1r,3r)-3-(4-(1-(2,6-dioxopiperidin-3-yl)-6-oxo-1,6-dihydropyridazine-4-yl)piperazin-1-yl)cyclobutyl)ethynyl)-5-oxo-5,7-dihydro-pyrrolino[3,4-b]pyridin-6-yl)-2,2,4,4-tetramethylcyclobutoxy)benzonitrile
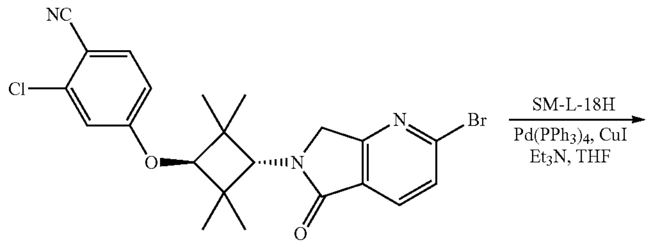
SM-A-1
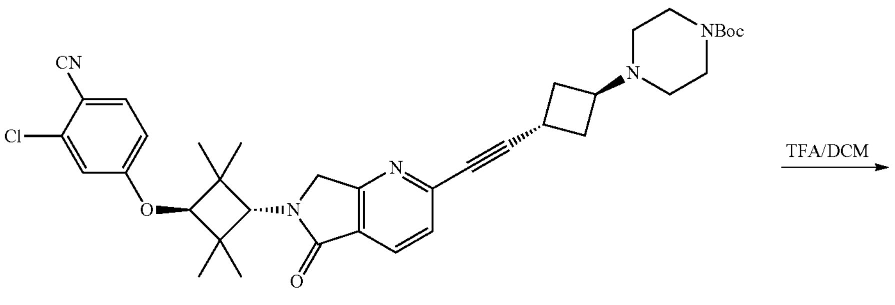

-continued
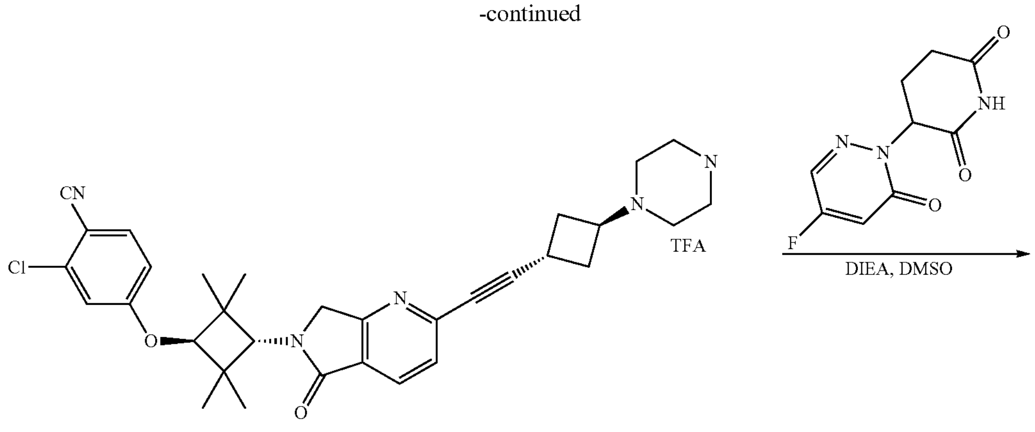
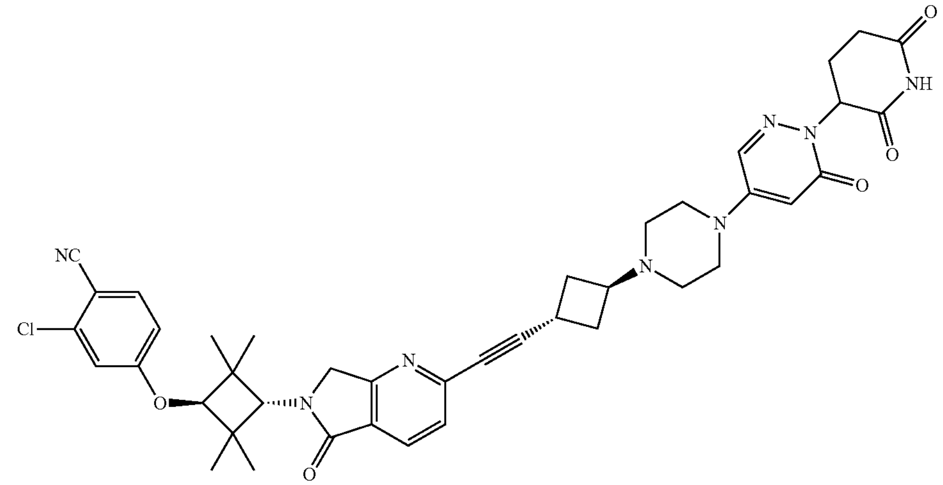
394
$^1$H NMR (400 MHz, DMSO-$d_6$) δ 10.99 (s, 1H), 8.06 (d, J=7.9 Hz, 2H), 7.91 (d, J=8.8 Hz, 1H), 7.58 (d, J=7.9 Hz, 1H), 7.30 (d, J=2.4 Hz, 1H), 7.07 (d, J=8.8, 2.4 Hz, 1H), 5.87 (d, J=2.7 Hz, 1H), 5.59 (d, J=12.1, 5.2 Hz, 1H), 4.81 (s, 2H), 4.55 (s, 1H), 4.34 (s, 1H), 3.28 (d, J=9.0 Hz, 4H), 3.14-3.07 (m, 1H), 2.92-2.80 (m, 1H), 2.37 (s, 5H), 2.23 (s, 2H), 2.04-1.93 (m, 1H), 1.69 (s, 6H), 1.41 (s, 4H), 1.16 (s, 6H). MS: calcd. for $C_{41}H_{43}ClN_8O_5$ $[M+H]^+$: 763.3; found: 763.3.
395: 2-Chloro-4-((1r,3r)-3-(2-((1r,3r)-3-(4-(1-(2,6-dioxopiperidin-3-yl)-6-oxo-1,6-dihydropyrimidin-4-yl)piperazin-1-yl)cyclobutyl)ethynyl)-5-oxo-5H-pyrrolo[3,4-b]pyridin-6(7H)-yl)-2,2,4,4-tetramethylcyclobutoxy)benzonitrile
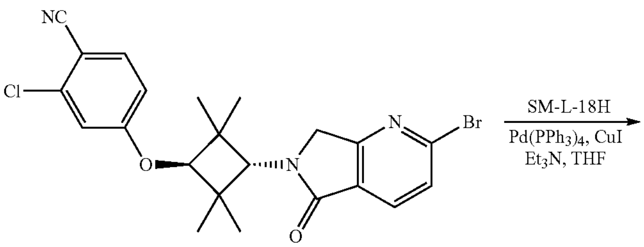
SM-A-1

-continued
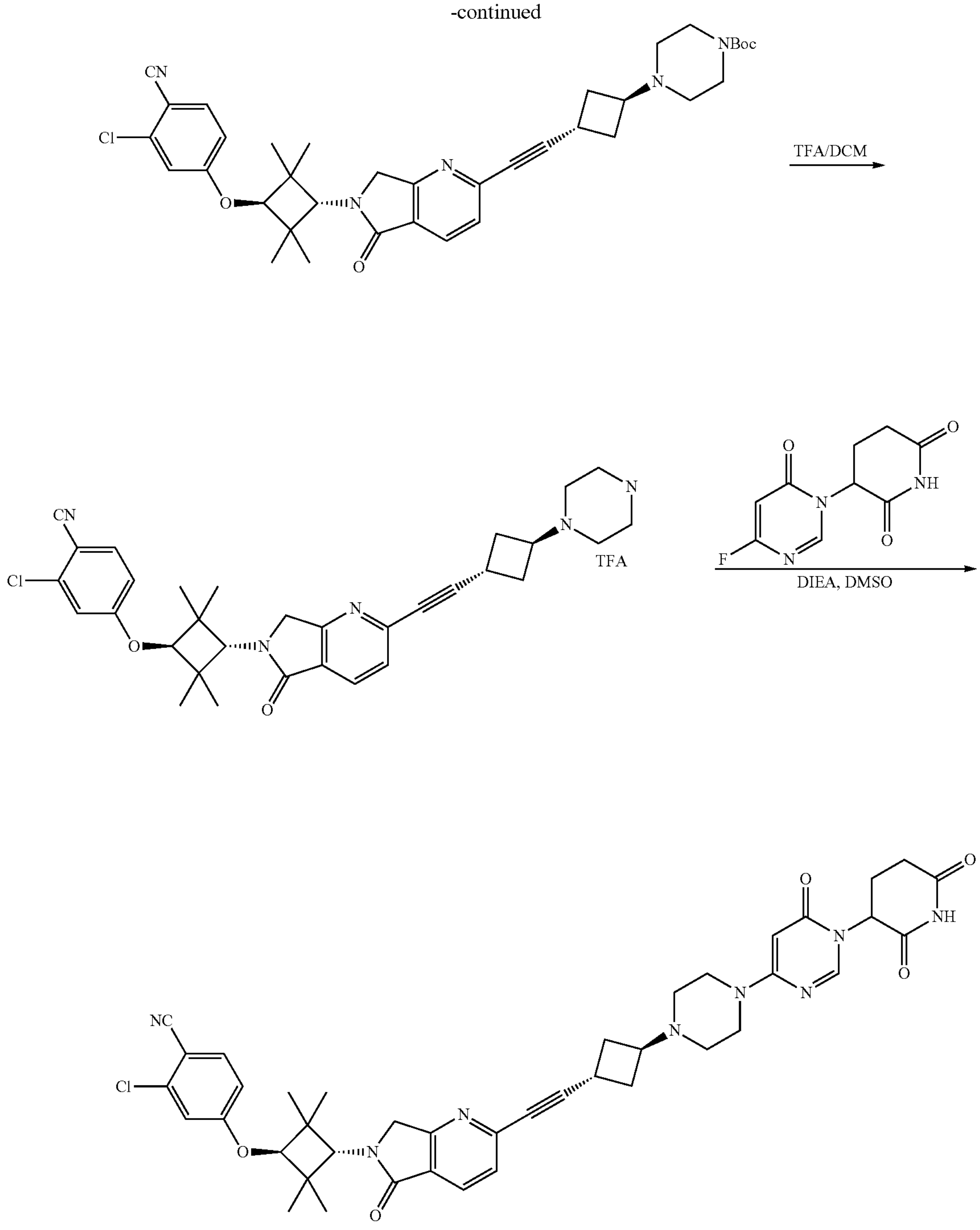
395
$^{1}$H NMR (400 MHz, DMSO-$d_6$) $\delta$ 11.04 (s, 1H), 8.17 (s, 1H), 8.05 (d, J=7.9 Hz, 1H), 7.91 (d, J=8.8 Hz, 1H), 7.58 (d, J=7.9 Hz, 1H), 7.29 (d, J=2.4 Hz, 1H), 7.07 (dd, J=8.8, 2.4 Hz, 1H), 5.39 (s, 1H), 5.32-5.07 (m, 1H), 4.81 (s, 2H), 4.55 (s, 1H), 4.34 (s, 1H), 3.51 (s, 4H), 3.29-3.25 (m, 1H), 3.14-3.05 (m, 1H), 2.80-2.75 (m, 1H), 2.60-2.53 (m, 2H), 2.35-2.30 (m, 6H), 2.24-2.20 (m, 2H), 2.02-1.89 (m, 1H), 1.41 (s, 6H), 1.16 (s, 6H). MS: calcd. for $C_{41}H_{43}ClN_8O_5$ $[M+H]^+$: 763.3; found: 763.3.

396: 2-Chloro-4-((1r,3r)-3-(2-((1r,3r)-3-(4-(3-(2,6-dioxopiperidin-3-yl)-4-oxo-3,4-dihydroquinazoline-7-yl)piperazin-1-yl)cyclobutyl)ethynyl)-5-oxo-5H-pyrrolino[3,4-b]pyridin-6(7H)-yl)-2,2,4,4-tetramethylcyclobutoxy)benzonitrile
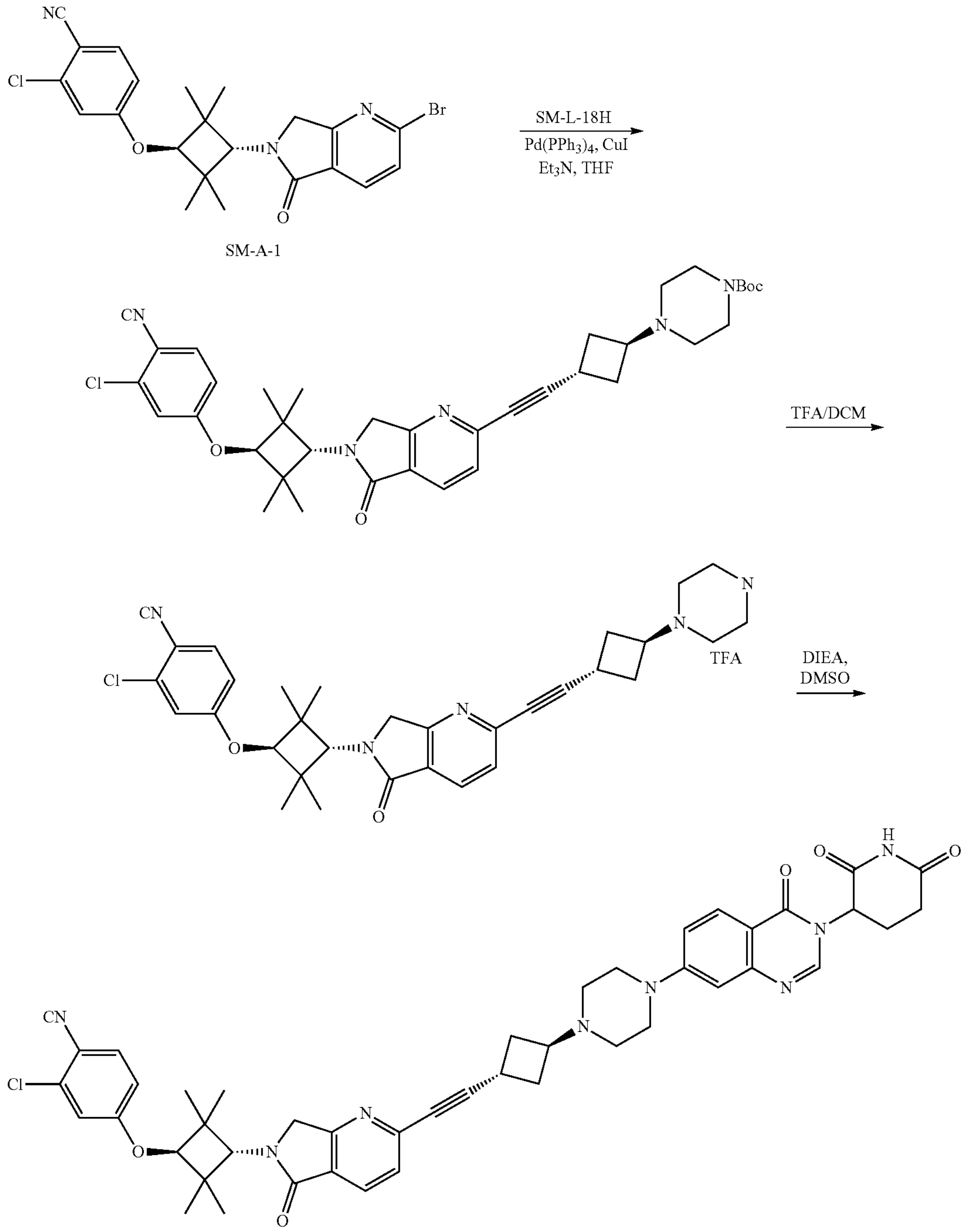
396
$^1$H NMR (400 MHz, DMSO-$d_6$) δ 11.12 (s, 1H), 8.22 (s, 1H), 8.06 (d, J=7.9 Hz, 1H), 7.91 (d, J=8.8 Hz, 2H), 7.59 (d, J=7.9 Hz, 1H), 7.27 (dd, J=24.2, 5.8 Hz, 2H), 7.07 (dd, J=8.8, 2.4 Hz, 1H), 6.97 (s, 1H), 4.81 (s, 2H), 4.55 (s, 1H), 4.34 (s, 1H), 3.40 (s, 4H), 3.14-3.05 (m, 1H), 2.88-2.81 (m, 1H), 2.67-2.57 (m, 2H), 2.47-2.37 (m, 3H), 2.36-2.27 (m, 1H), 2.28-2.15 (m, 2H), 2.14-2.05 (m, 1H), 1.76 (s, 4H), 1.36 (s, 6H), 1.16 (s, 6H). MS: calcd. for $C_{45}H_{45}ClN_8O_5$ $[M+H]^+$: 813.3; found: 813.3.

397: 2-Bromo-4-((1r,3r)-3-(2-((1r,4r)-4-(4-(2-(2,6-dioxopiperidin-3-yl)-6-fluoro-1,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)benzonitrile
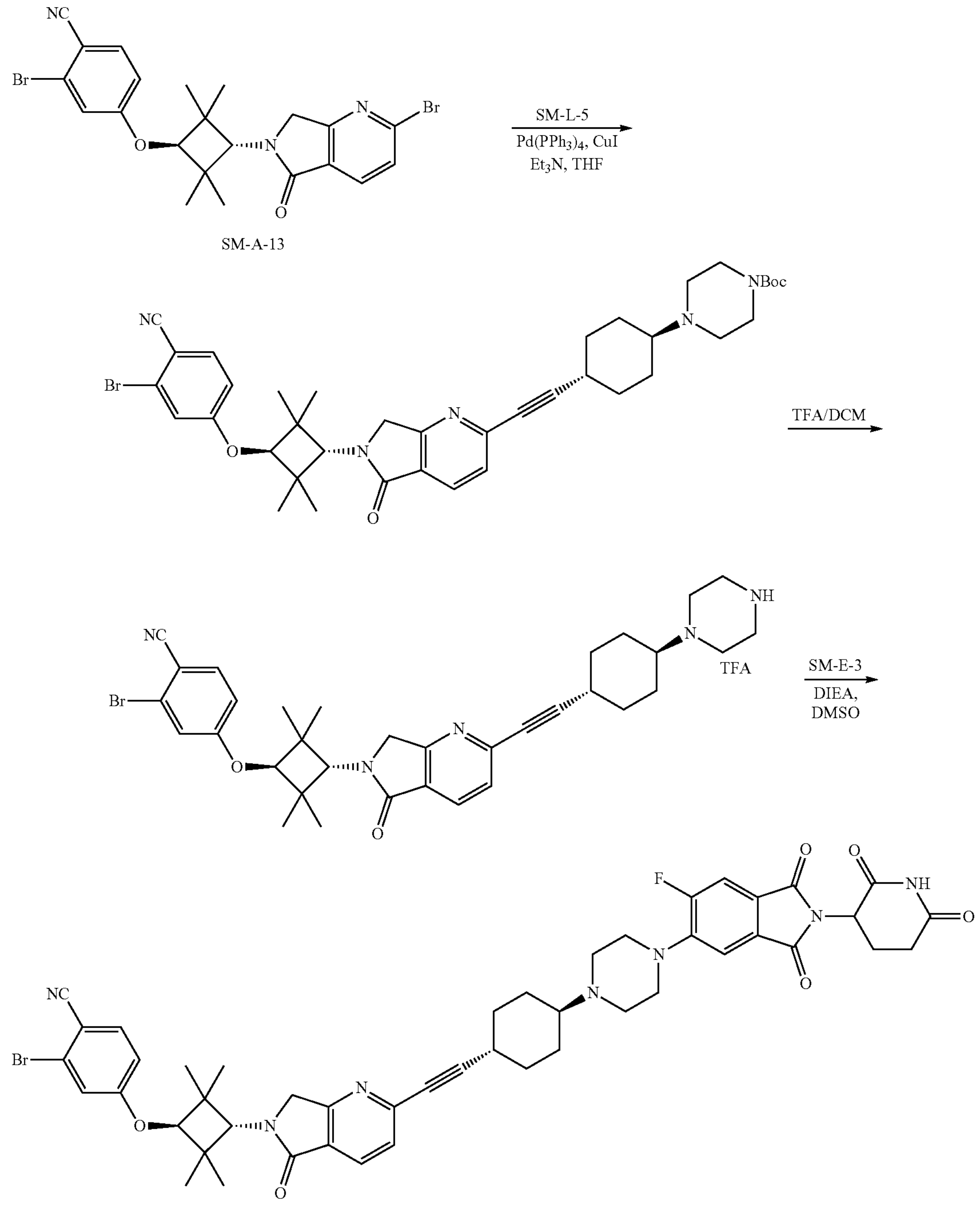
397
$^1$H NMR (400 MHz, DMSO-D6) δ 11.12 (s, 1H), 8.05 (d, J=7.9 Hz, 1H), 7.88 (d, J=8.7 Hz, 1H), 7.73 (d, J=11.4 Hz, 1H), 7.55 (d, J=7.9 Hz, 1H), 7.43 (dd, J=13.7, 4.8 Hz, 2H), 7.10 (dd, J=8.8, 2.3 Hz, 1H), 5.11 (dd, J=12.7, 5.4 Hz, 1H), 4.80 (s, 2H), 4.54 (s, 1H), 4.34 (s, 1H), 3.24 (s, 4H), 2.92-2.84 (m, 1H), 2.73-2.57 (m, 6H), 2.46-2.31 (m, 2H), 2.12-1.99 (m, 3H), 1.88 (d, J=10.0 Hz, 2H), 1.49-1.35 (m, 10H), 1.16 (s, 6H). MS: calcd. for $C_{47}H_{47}BrFIN_7O_6$ $[M+H]^+$: 904.3; found: 904.2.

398: 2-Bromo-4-((1r,3r)-3-(2-((1r,4r)-4-(4-(2-(2,6-dioxopiperidin-3-yl)-1,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)benzonitrile
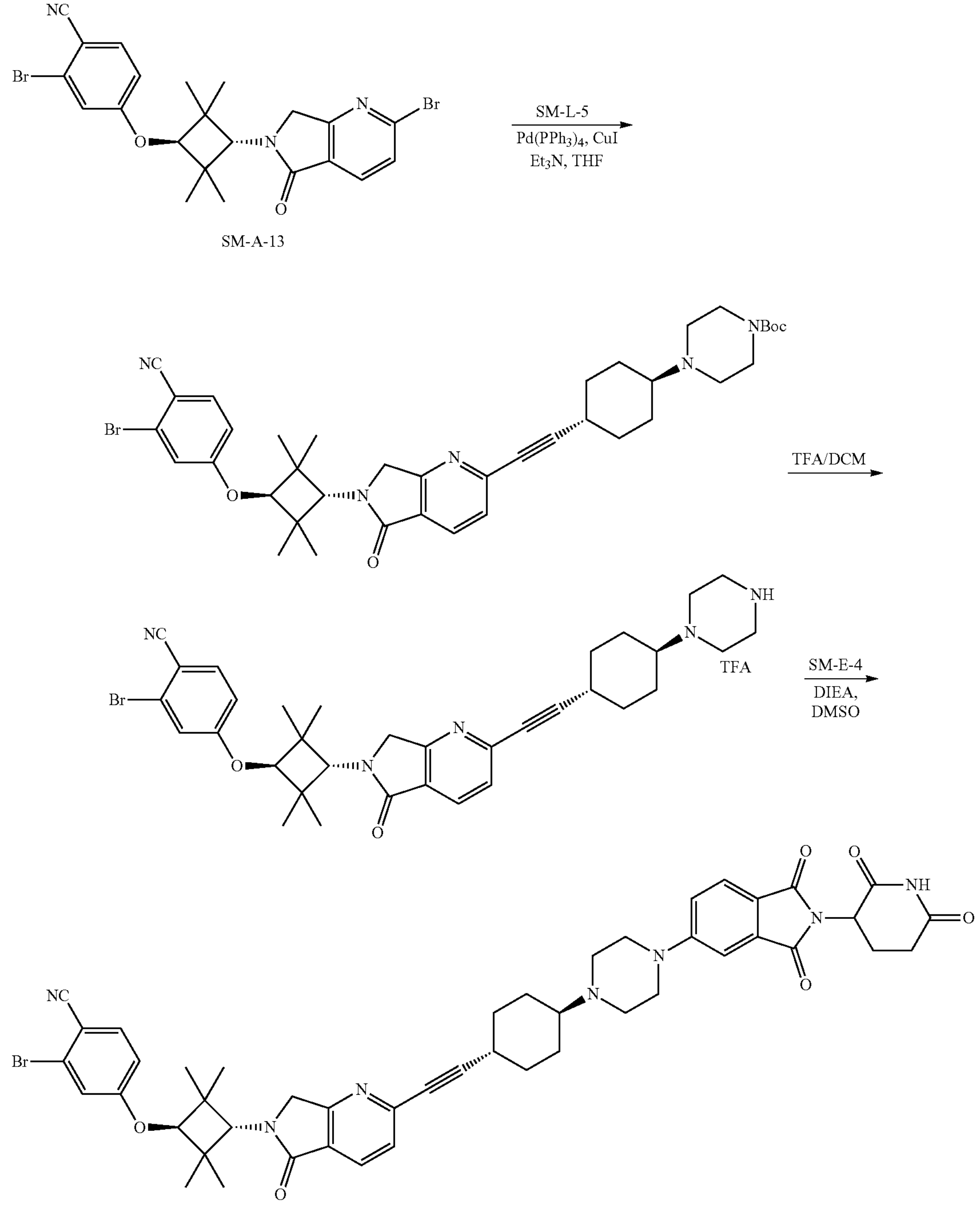
398
$^1$H NMR (400 MHz, DMSO-D6-$d_6$) δ 11.09 (s, 1H), 8.04 (d, J=7.9 Hz, 1H), 7.88 (d, J=8.7 Hz, 1H), 7.68 (d, J=8.5 Hz, 1H), 7.54 (d, J=7.9 Hz, 1H), 7.42 (d, J=2.4 Hz, 1H), 7.34 (s, 1H), 7.26 (d, J=8.6 Hz, 1H), 7.10 (dd, J=8.8, 2.4 Hz, 1H), 5.07 (dd, J=12.9, 5.3 Hz, 1H), 4.80 (s, 2H), 4.54 (s, 1H), 4.33 (s, 1H), 3.42 (s, 4H), 2.94-2.82 (m, 1H), 2.72-2.52 (m, 6H), 2.44-2.30 (m, 2H), 2.12-1.98 (m, 3H), 1.86 (d, J=11.0 Hz, 2H), 1.57-1.26 (m, 10H), 1.16 (s, 6H). MS: calcd. for $C_{47}H_{48}BrIN_7O_6$ $[M+H]^+$:886.3; found:886.2.

399: 4-((1r,3r)-3-(2-((1r,4r)-4-(4-(2-(2,6-dioxopiperidin-3-yl)-6-fluoro-1,3-dioxoisoindolin-5-yl)piperazin-1-yl)cyclohexyl)ethynyl)-5-oxo-5,7-dihydropyrrolo[3,4-b]pyridin-6-yl)-2,2,4,4-tetramethylcyclobutoxy)-2-methoxybenzonitrile
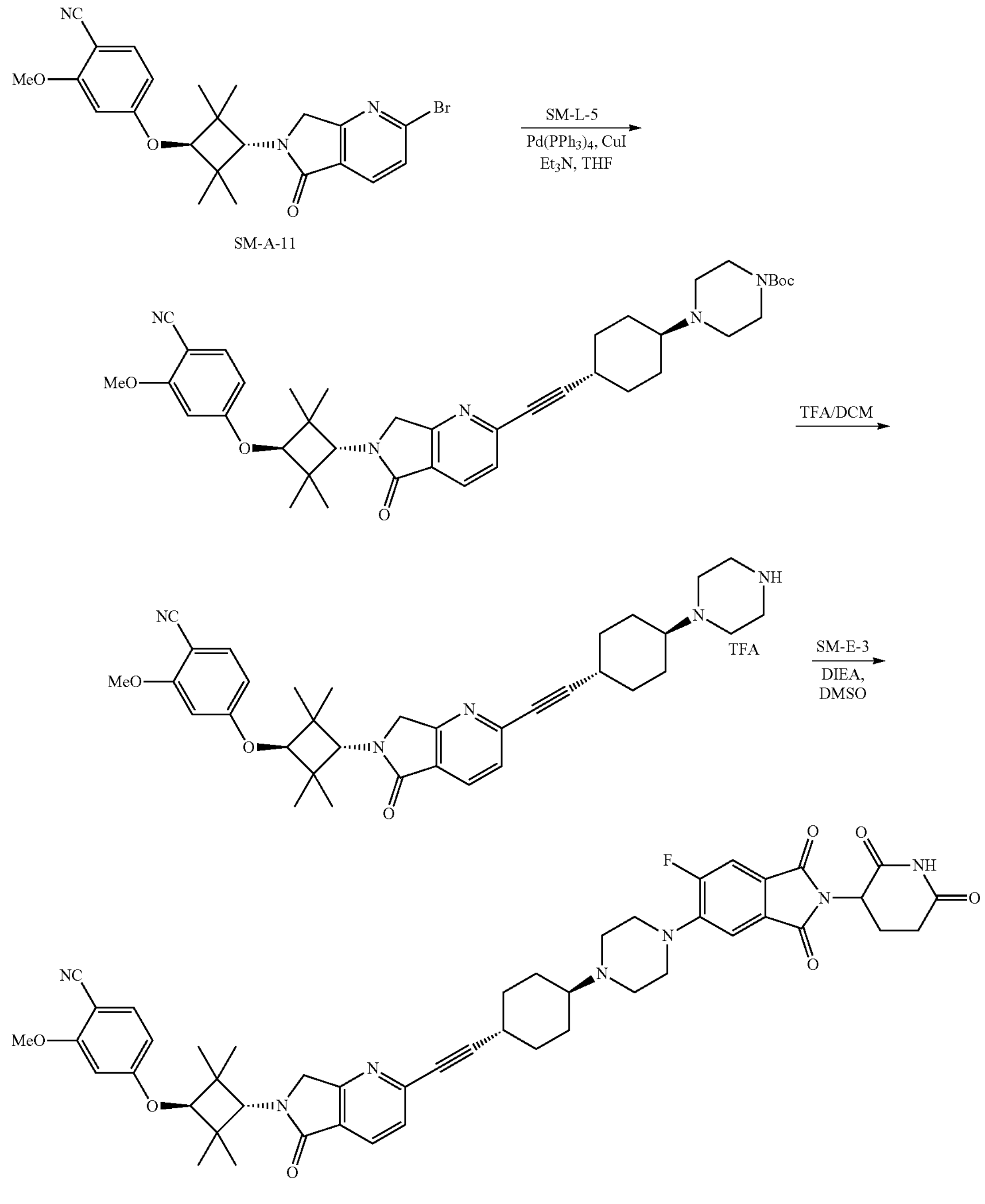
399
$^1$H NMR (400 MHz, DMSO-$d_6$) δ 11.12 (s, 1H), 8.04 (d, J=7.9 Hz, 1H), 7.73 (d, J=11.4 Hz, 1H), 7.65 (d, J=8.6 Hz, 1H), 7.54 (d, J=7.9 Hz, 1H), 7.45 (d, J=7.3 Hz, 1H), 6.69 (d, J=1.9 Hz, 1H), 6.60 (dd, J=8.7, 2.0 Hz, 1H), 5.11 (dd, J=12.7, 5.4 Hz, 1H), 4.81 (s, 2H), 4.49 (s, 1H), 4.34 (s, 1H), 3.92 (s, 3H), 3.24 (s, 4H), 2.96-2.81 (m, 1H), 2.72-2.53 (m, 6H), 2.44-2.30 (m, 2H), 2.15-1.97 (m, 3H), 1.87 (d, J=9.3 Hz, 2H), 1.57-1.28 (m, 10H), 1.18 (s, 6H). MS: calcd. for $C_{48}H_{50}FN_7O_7$[M+H]$^+$: 856.4; found: 856.3.

400: 4-((1r,3r)-3-(2-((1r,4r)-4-(4-(2,6-dioxopiperidin-3-yl)-1,3-dioxoisoindolin-5-yl)piperazin-1-2-methoxybenzonitrile
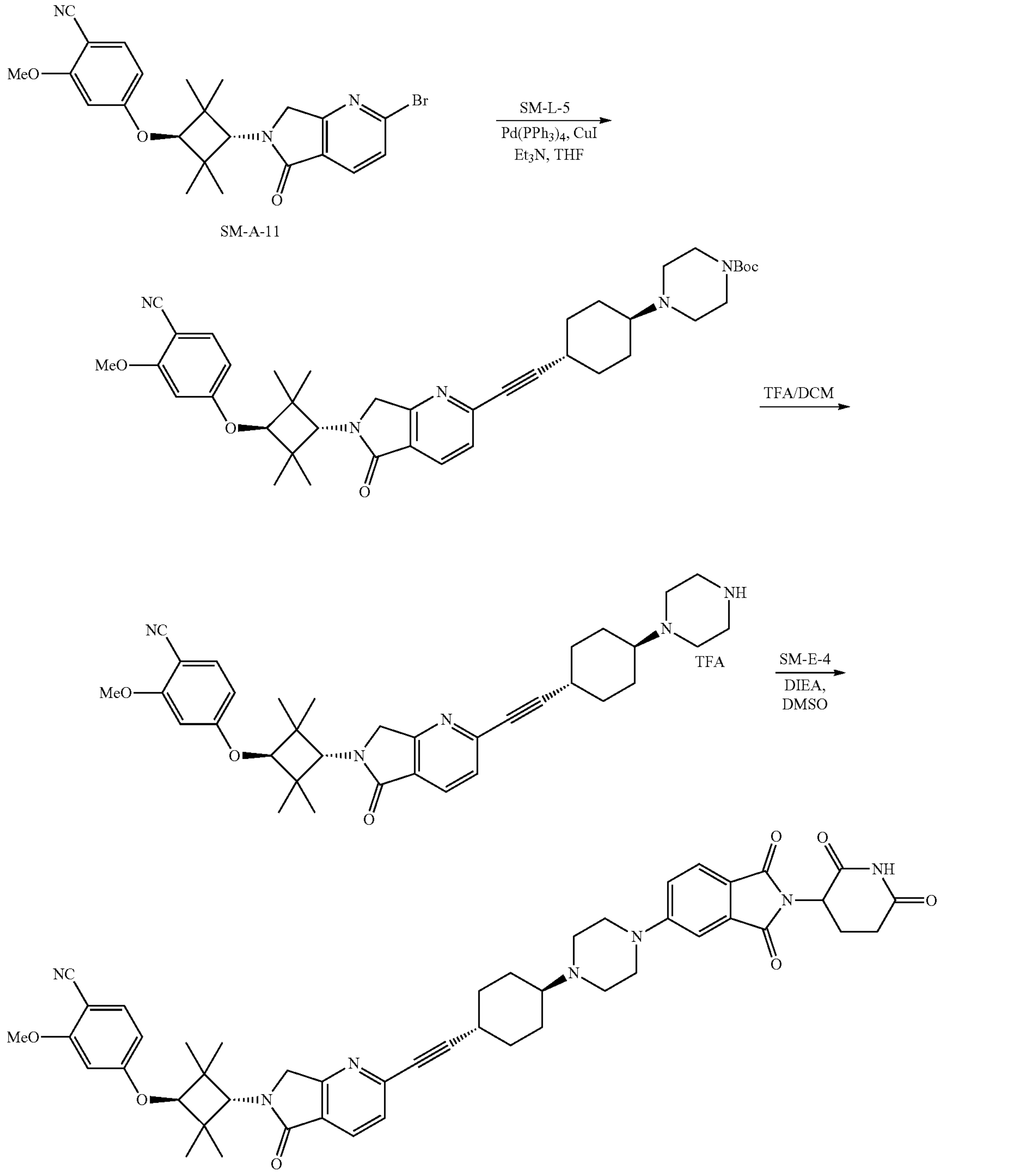
400
$^1$H NMR (400 MHz, DMSO-$d_6$) δ 0.1.09 (s, 1H), 8.04 (d, J=7.9 Hz, 1H), 7.66 (dd, J=12.1, 8.6 Hz, 2H), 7.54 (d, J=7.9 Hz, 1H), 7.34 (s, 1H), 7.26 (d, J=8.8 Hz, 1H), 6.69 (d, J=2.1 Hz, 1H), 6.60 (dd, J=8.7, 2.1 Hz, 1H), 5.08 (dd, J=12.9, 5.4 Hz, 1H), 4.81 (s, 2H), 4.49 (s, 1H), 4.34 (s, 1H), 3.92 (s, 3H), 3.42 (s, 4H), 2.97-2.80 (m, 1H), 2.70-2.52 (m, 6H), 2.45-2.22 (m, 2H), 2.12-1.91 (m, 3H), 1.86 (d, J=10.5 Hz, 2H), 1.66-1.21 (m, 10H), 1.10 (d, J=63.9 Hz, 6H). MS: calcd. for $C_{48}H_{51}N_7O_7$ $[M+H]^+$: 838.4; found: 838.3.

401: 4-((1r,3r)-3-(2-((1r,4r)-4-(4-(2,6-dioxopiperdin-3-yl)-6-fluoro-,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)-2-methylbenzonitrile
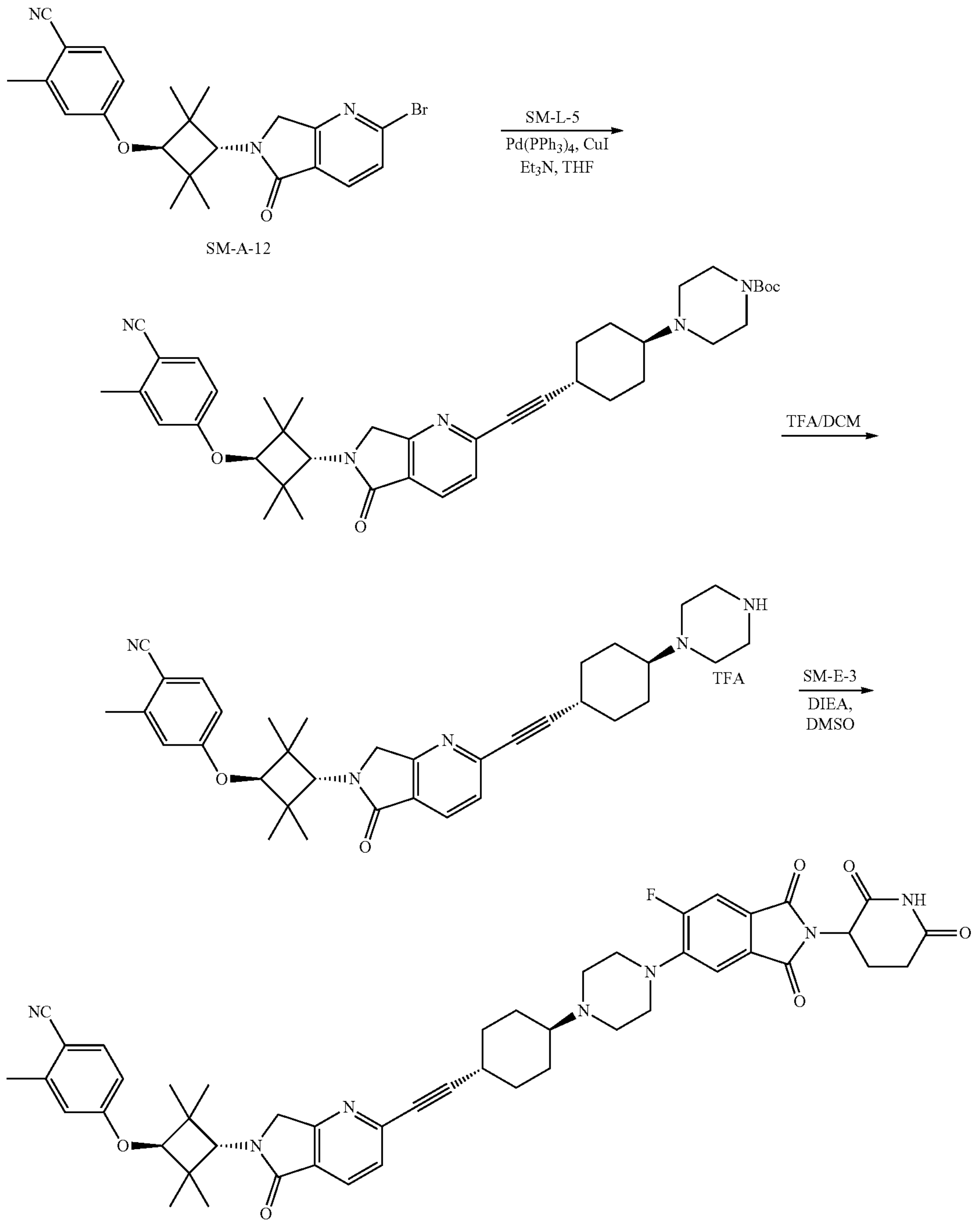
401
$^1$H NMR (400 MHz, DMSO-$d_6$) δ 11.10 (s, 1H), 8.02 (d, J=7.9 Hz, 1H), 7.77-7.63 (m, 2H), 7.52 (d, J=7.8 Hz, 1H), 7.42 (d, J=7.3 Hz, 1H), 6.96 (s, 1H), 6.85 (d, J=8.6 Hz, 1H), 5.09 (dd, J=12.8, 5.5 Hz, 1H), 4.78 (s, 2H), 4.40 (s, 1H), 4.30 (s, 1H), 3.21 (s, 4H), 2.92-2.80 (m, 1H), 2.70-2.52 (m, 5H), 2.40-2.24 (m, 2H), 2.10-1.95 (m, 3H), 1.85 (d, J=9.8 Hz, 2H), 1.59-1.23 (m, 9H), 1.13 (s, 5H). MS: calcd. for $C_{48}H_{50}FN_7O_6$ $[M+H]^+$: 840.4; found: 840.3.

402: 4-((1r,3r)-3-(2-((1r,4r)-4-(4-(2-(2,6-Dioxopiperidin-3-yl)-1,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)-2-methylbenzonitrile
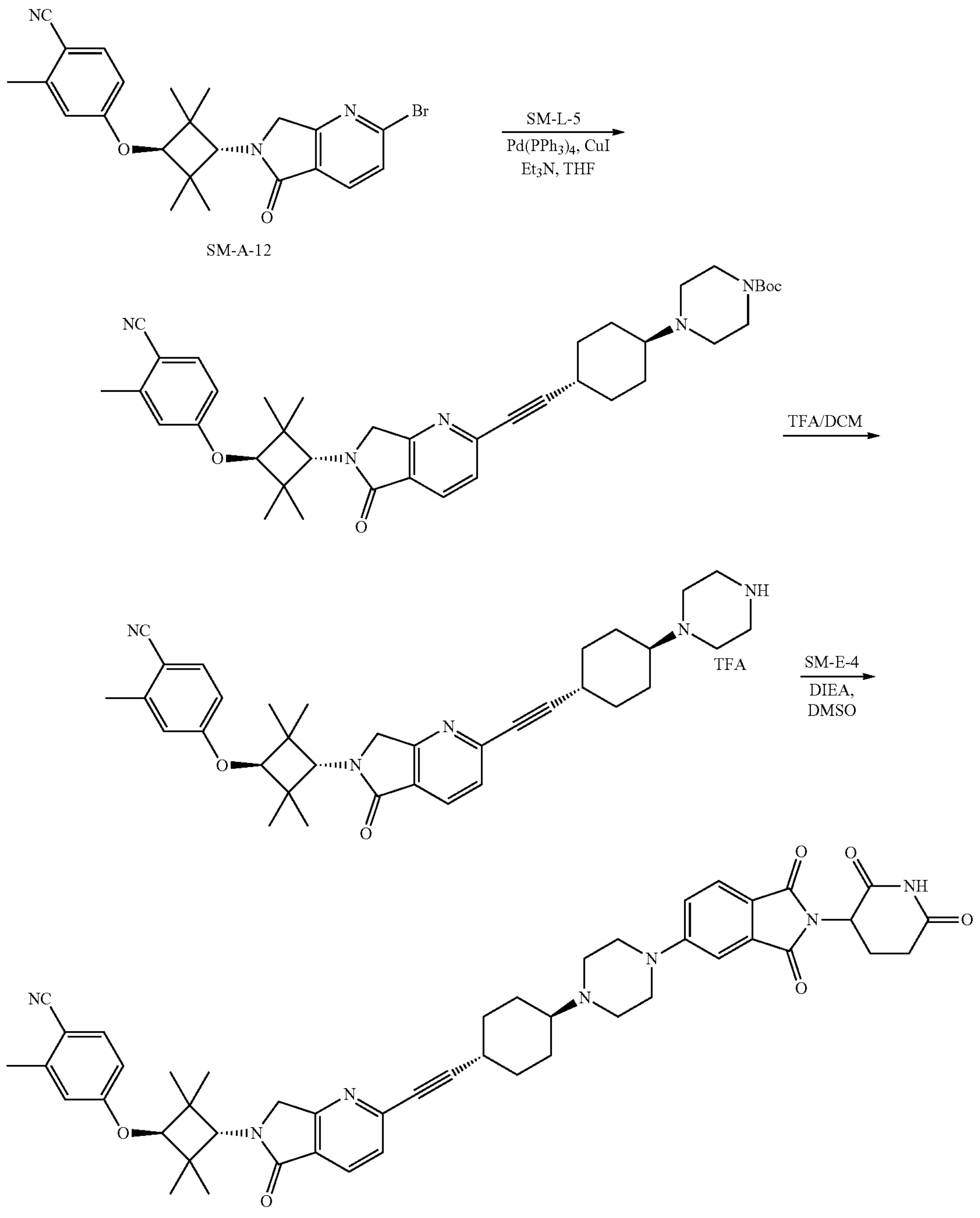
402
$^1$H NMR (400 MHz, DMSO-$d_6$) δ 11.09 (s, 1H), 8.04 (d, J=7.9 Hz, 1H), 7.69 (t, J=8.8 Hz, 2H), 7.54 (d, J=7.9 Hz, 1H), 7.34 (s, 1H), 7.26 (d, J=9.0 Hz, 1H), 6.99 (d, J=2.2 Hz, 1H), 6.87 (dd, J=8.7, 2.4 Hz, 1H), 5.07 (dd, J=12.9, 5.4 Hz, 1H), 4.80 (s, 2H), 4.42 (s, 1H), 4.32 (s, 1H), 3.42 (s, 4H), 2.94-2.82 (m, 1H), 2.78-2.51 (m, 6H), 2.47-2.28 (m, 5H), 2.14-1.95 (m, 3H), 1.86 (d, J=10.7 Hz, 2H), 1.55-1.27 (m, 10H), 1.08 (d, J=63.5 Hz, 6H). MS: calcd. for $C_{45}H_{51}N_7O_6$ $[M+H]^+$: 822.4; found: 822.3.

403: (2S,4R)-1-((S)-2-(2-((5-(2-((1r,3r)-3-(3-chloro-4-cyanophenoxy)-2,2,4,4-tetramethylcyclobutyl)-1-oxoisoindolin-5-yl-3,3-$d_2$)pent-4-yn-1-yl)oxy) acetamido)-3,3-dimethylbutanol)-4-hydroxy-N-((S)-1-(4-methylthiazol-5-yl) phenyl)ethyl)pyrrolidine-2-carboxamide
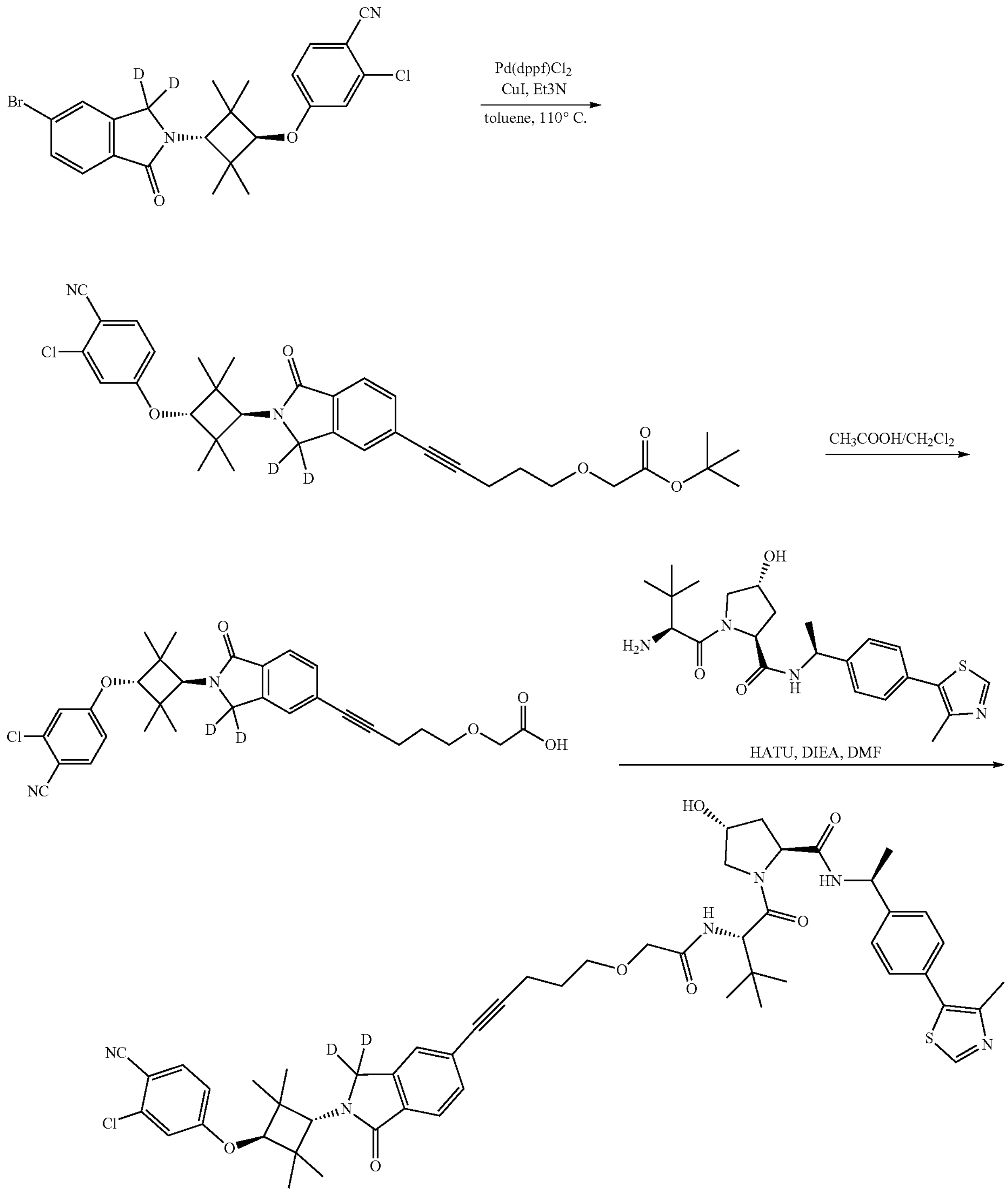
403
LC/MS ($ESI^+$) calcd for $C_{53}H_{60}D_2ClN_6O_7S^+$ ($[M+H]^+$) m/z: 963.4; found 963.4.

404: (2S,4R)-1-((S)-2-(2-((6-(4-((1r,3r)-3-(3-bromo-4-cyanophenoxy)-2,2,4,4-tetramethylcyclobutyl) carbamoyl)phenyl)hex-5-yn-1-yl)oxy)acetamide)-3, 3-dimethylbutyryl)-4-hydroxy-N-((S)-1-(4-(4-methylthiazol-5-yl)phenyl)ethyl) pyrrolidine-2-carboxamide
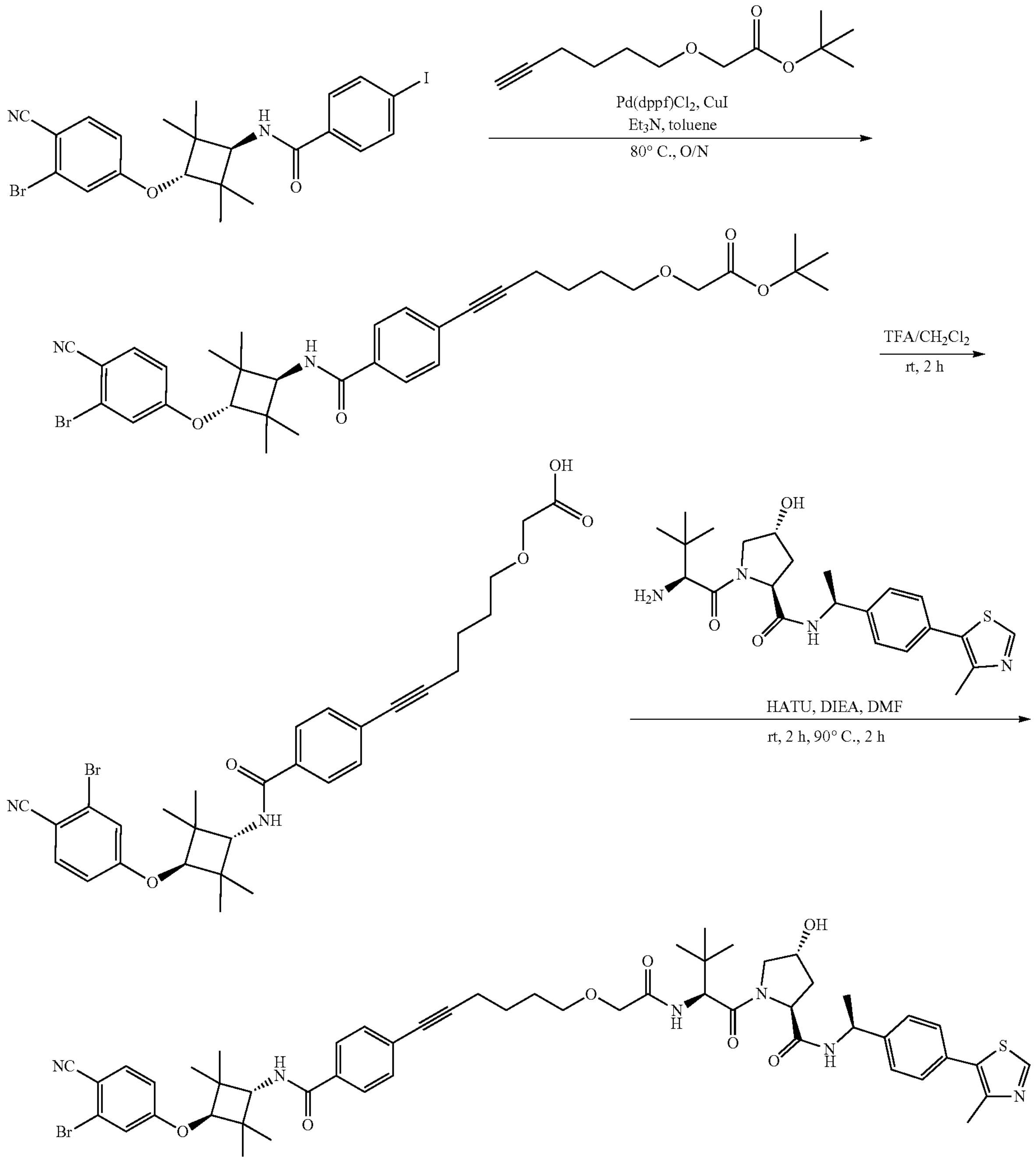
404
LC/MS (ESI+) calcd for $C_{53}H_{64}BrN_6O_7S^+$ ([M+H]+) m/z: 1007.4; found 1007.4.
$^1$H NMR (400 MHz, $CDCl_3$) δ 8.89 (s, 1H), 7.70 (d, J=8.1 Hz, 2H), 7.56 (d, J=8.7 Hz, 1H), 7.46 (t, J=9.5 Hz, 3H), 7.38 (d, J=17.8 Hz, 4H), 7.22 (d, J=8.6 Hz, 1H), 7.15 (d, J=2.2 Hz, 1H), 6.85 (dd, J=8.7, 2.2 Hz, 1H), 6.26 (d, J=7.9 Hz, 1H), 5.13-5.03 (m, 1H), 4.76 (t, J=7.8 Hz, 1H), 4.54 (d, J=8.5 Hz, 2H), 4.19-4.10 (m, 2H), 4.06 (s, 1H), 3.97 (q, J=15.4 Hz, 2H), 3.59 (t, J=6.4 Hz, 3H), 2.60-2.47 (m, 6H), 2.10-2.02 (m, 2H), 1.82 (dd, J=13.7, 6.5 Hz, 2H), 1.77-1.69 (m, 2H), 1.47 (d, J=6.9 Hz, 3H), 1.27 (s, 6H), 1.23 (s, 6H), 1.07 (s, 9H).
405: (2R,4R)-1-((S)-2-(2-((5-((4-((1r,3r)-3-(4-(4H-1,2,4-triazol-1-yl)phenoxy)-2,2,4,4-tetramethylcyclobutyl)carbamoyl)phenyl)amino)pentyl)oxy)acetamide)-3,3-dimethylbutyryl)-4-hydroxy-N-((S)-1-(4-(4-methylthiazol-5-yl)phenyl)ethyl) pyrrolidine-2-carboxamide
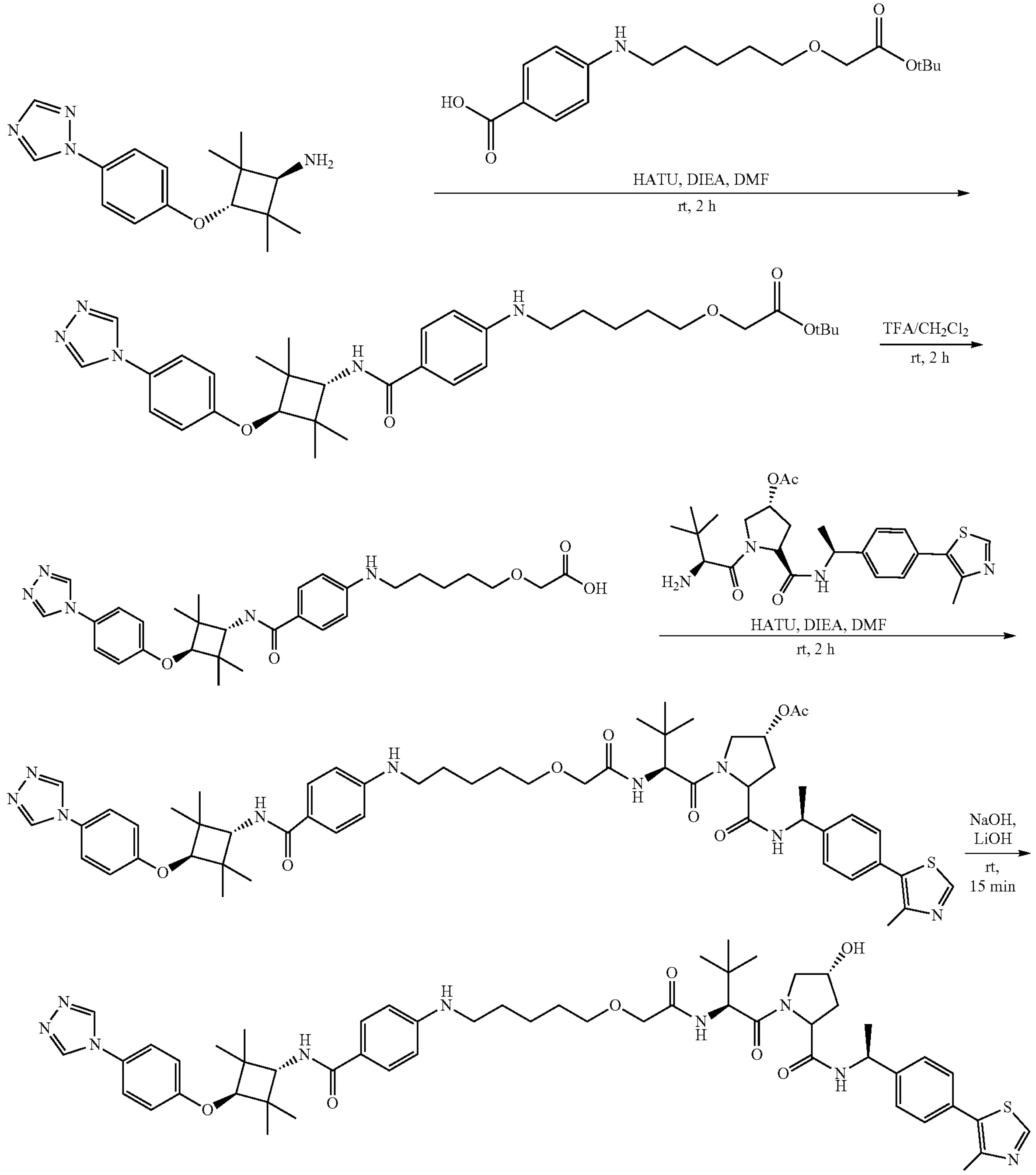

LC/MS (ESI+) calcd for $C_{53}H_{70}N_9O_7S^+$ ($[M+H]^+$) m/z: 976.5, found 976.4.

$^1H$ NMR (400) MHz, $CDCl_3$) δ 8.67 (s, 1H), 8.46 (s, 1H), 8.08 (s, 1H), 7.64 (d, J=8.6 Hz, 2H), 7.55 (d, J=8.9 Hz, 2H), 7.36 (dd, J=18.2, 8.3 Hz, 5H), 7.24 (d, J=9.0 Hz, 1H), 6.97 (t, J=12.3 Hz, 2H), 6.63 (d, J=8.2 Hz, 2H), 6.12 (d, J=8.1 Hz, 1H), 5.12-4.98 (m, 1H), 4.74 (t, J=7.9 Hz, 1H), 4.58 (d, J=9.0 Hz, 1H), 4.53 (s, 1H), 4.13 (t, J=10.5 Hz, 2H), 4.06 (d, J=8.2 Hz, 1H), 3.71-3.41 (m, 4H), 3.20 (t, J=6.4 Hz, 2H), 2.50 (d, J=19.3 Hz, 4H), 2.16-2.02 (m, 2H), 1.72-1.65 (m, 4H), 1.53 (dd, J=15.1, 9.7 Hz, 2H), 1.45 (s, 3H), 1.30-1.24 (m, 12H), 1.05 (d, J=18.9 Hz, 9H).

406: (2S,4R)-1-((S)-2-(2-((2-((5-(1r,3r)-3-(3-chloro-4-cyanophenoxy)-2,2,4,4-tetramethylcyclobutyl)-1-oxoisoindolin-5-yl)oxy)pentyl)oxy)acetamide)-3,3-dimethylbutyryl)-4-hydroxy-N-((S)-1-(4-(4-methylthiazol-5-yl)phenyl)ethyl) pyrrolidine-2-carboxamide

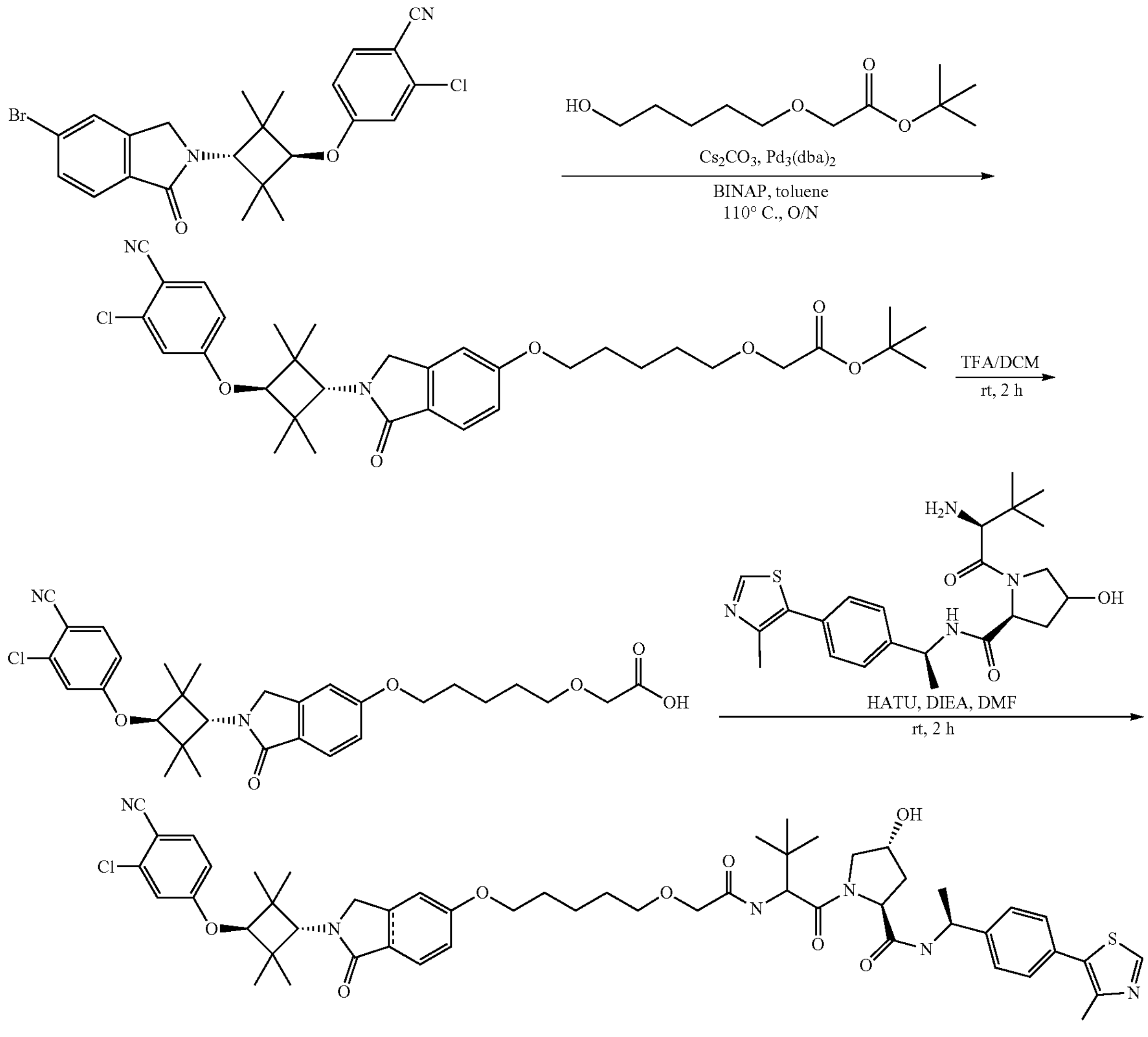

406

LC/MS (ESI+) calcd for $C_{53}H_{70}N_9O_7S^+$ ($[M+H]^+$) m/z: 981.4; found 981.2.

$^1H$ NMR (400 MHz, $CDCl_3$) δ 8.80 (s, 1H), 7.75 (d, J=8.4 Hz, 1H), 7.62-7.56 (m, 1H), 7.47-7.33 (m, 6H), 7.21 (d, J=8.4 Hz, 1H), 7.01-6.96 (m, 1H), 6.91 (s, 1H), 5.12-5.04 (m, 1H), 4.75 (t, J=7.8 Hz, 1H), 4.61 (d, J=4.4 Hz, 2H), 4.54 (d, J=8.6 Hz, 2H), 4.30 (d, J=7.2 Hz, 1H), 4.14 (d, J=11.4 Hz, 1H), 4.04 (t, J=6.3 Hz, 2H), 3.95 (q, J=15.4 Hz, 2H), 3.67 (s, 1H), 3.61 (dd, J=11.3, 3.5 Hz, 1H), 3.56 (t, J=6.5 Hz, 2H), 2.54 (d, J=10.1 Hz, 4H), 2.08 (d, J=13.5 Hz, 2H), 1.91-1.82 (m, 2H), 1.75-1.67 (m, 2H), 1.63-1.57 (m, 2H), 1.47 (d, J=6.9 Hz, 3H), 1.43 (d, J=5.4 Hz, 6H), 1.25 (s, 6H), 1.08-1.04 (m, 9H).

407: (2S,4R)-1-((S)-2-(2-((6-(2-((1r,3r)-3-(3-chloro-4-cyanophenoxy)-2,2,4,4-tetramethylcyclobutyl)-1-oxoisoindolin-5-yl)-hex-5-yn-1-yl)oxy)acetamido)-3,3-dimethylbutyryl)-4-hydroxy-N-((S)-1-(4-(4-methylthiazol-5-yl)-phenyl)ethyl) pyrrolidine-2-carboxamide

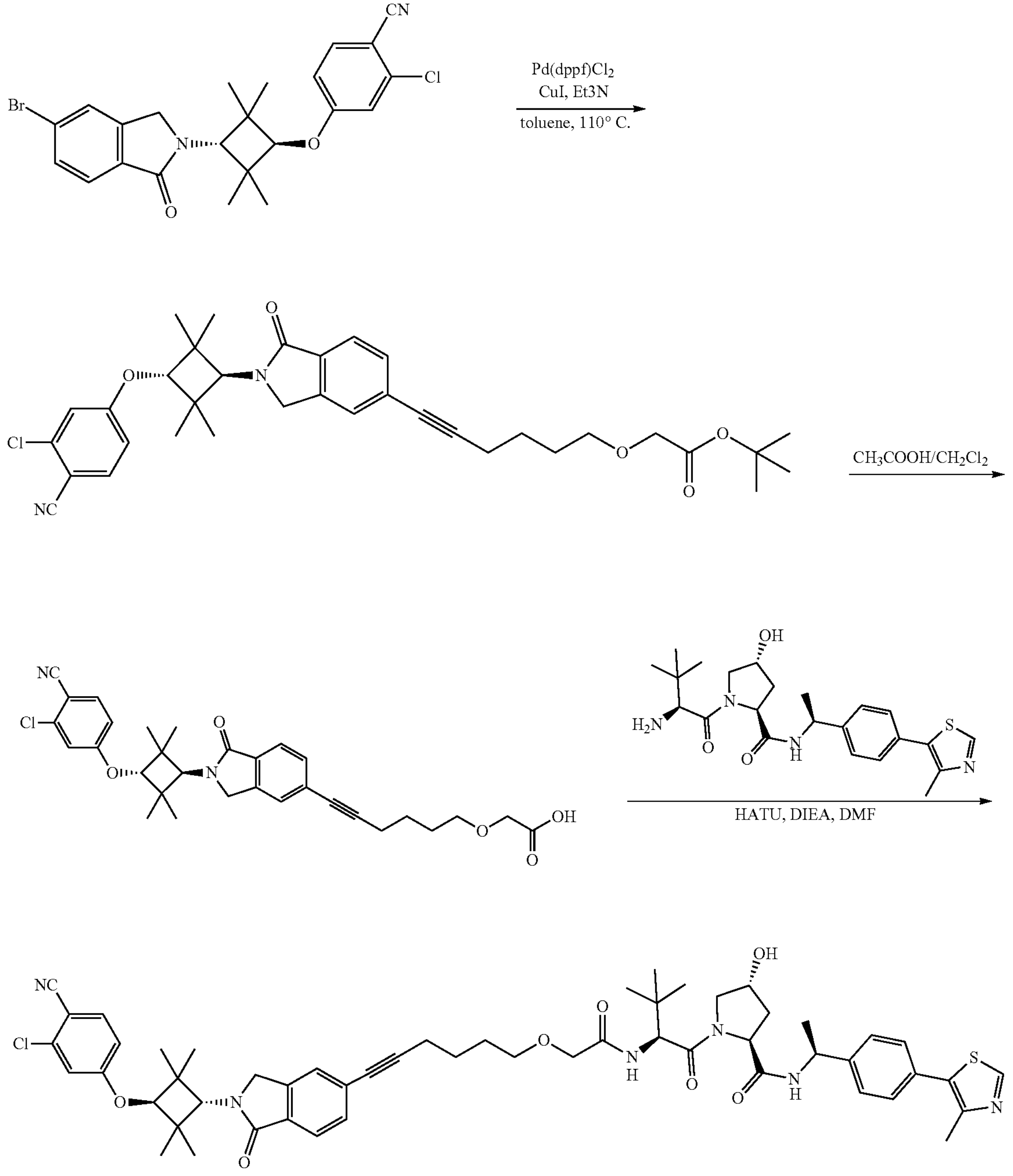

407

LC/MS ($ESI^+$) calcd for $C_{54}H_{64}ClN_6O_7S^+$ ($[M+H]^+$) m/z: 975.4; found 975.3.

$^1H$ NMR (400 MHz, $CDCl_3$) δ 8.68 (s, 1H), 7.76 (d, J=7.9 Hz, 1H), 7.57 (d, J=8.7 Hz, 1H), 7.48 (d, J=8.1 Hz, 1H), 7.46-7.33 (m, 5H), 7.22 (d, J=8.2 Hz, 1H), 6.99 (d, J=2.2 Hz, 1H), 6.84 (dd, J=8.8, 2.2 Hz, 1H), 5.14-5.01 (m, 1H), 4.75 (t, J=7.8 Hz, 1H), 4.63 (s, 2H), 4.54 (d, J=8.6 Hz, 2H), 4.39 (s, 1H), 4.32 (s, 1H), 4.15 (d, J=11.8 Hz, 1H), 3.97 (q, J=15.4 Hz, 2H), 3.61 (d, J=6.9 Hz, 3H), 2.89 (s, 1H), 2.62-2.48 (m, 5H), 2.14-1.94 (m, 2H), 1.88-1.79 (m, 2H), 1.77-1.70 (m, 2H), 1.47 (d, J=6.9 Hz, 3H), 1.44 (s, 6H), 1.25 (s, 6H), 1.07 (s, 9H).

408: (2S,4R)-1-((S)-2-(2-((6-(2-((1r,3r)-3-(3-chloro-4-cyanophenoxy)-2,2,4,4-tetramethylcyclobutyl)-1-oxoisoindolin-5-yl)hexyl)oxy)acetamide)-3,3-dimethylbutyryl)-4-hydroxy-N-((S)-1-(4-(4-methylthiazol-5-yl)phenyl)ethyl) pyrrolidine-2-carboxamide

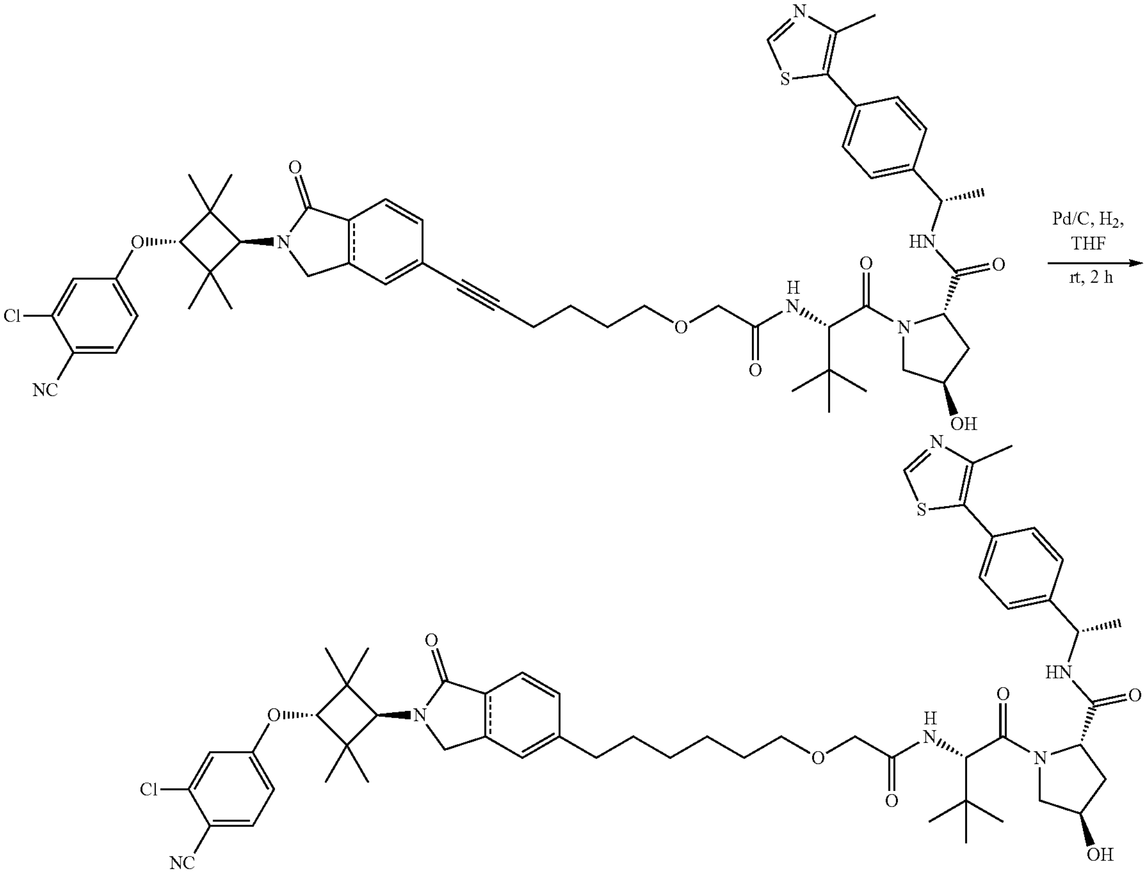

408

LC/MS ($ESI^+$) calcd for $C54H68ClN6O7S^+$ m/z: 979.5; found 979.4.

409: Synthesis of Compound (2S,4R)-1-((S)-2-(2-((1-(2-((1r,3r)-3-(3-chloro-4-cyanophenoxy)-2,2,4,4-tetramethylcyclobutyl)-1-oxoisoindolin-5-piperidin-4-methoxy)acetamide)-3,3-dimethylbutyryl)-4-hydroxy-N-((S)-1-(4-(4-methylthiazol-5-phenyl) ethyl)pyrrolidine-2-carboxamide

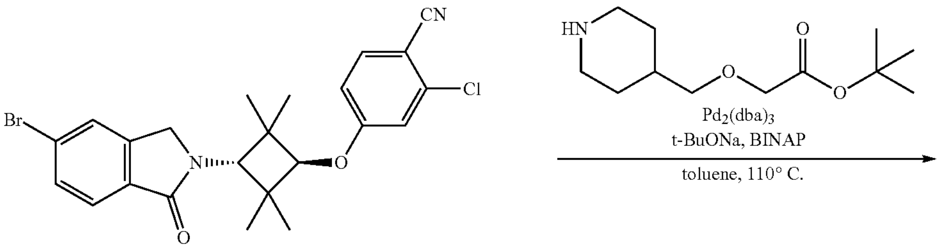

-continued

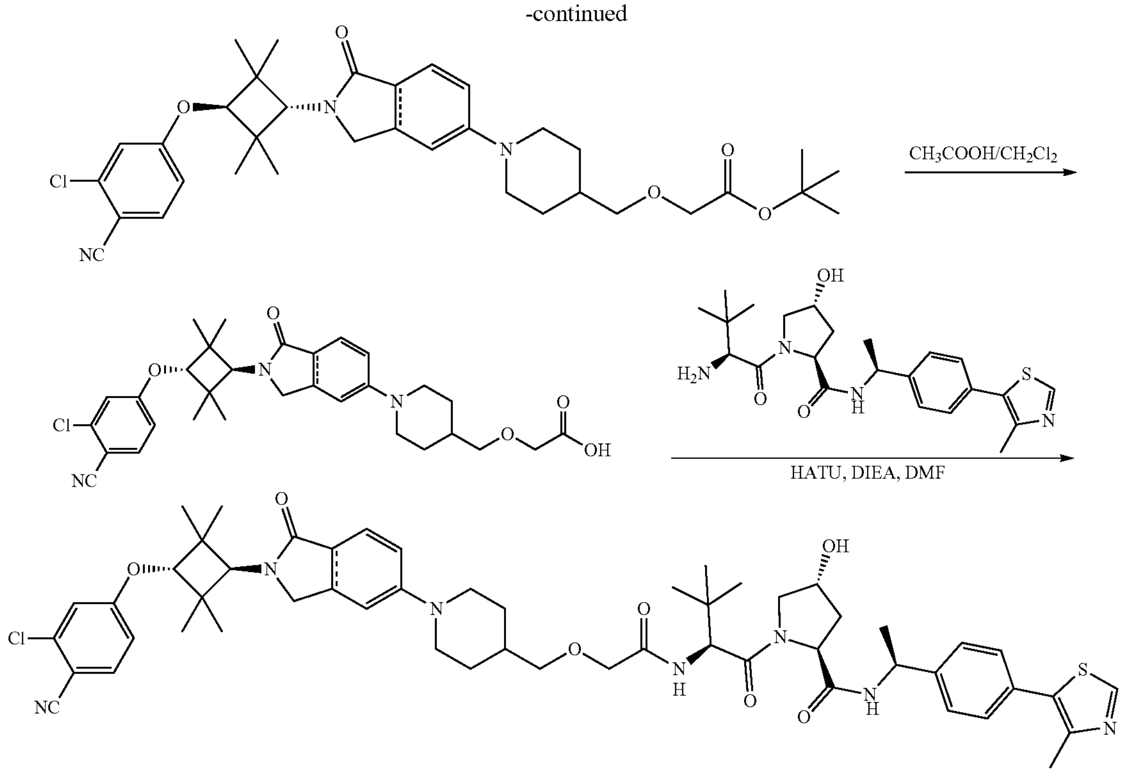

409

1. Synthesis of Compound t-butyl 2-((1-(2-((1r,3r)-3-(3-chloro-4-cyanophenoxy)-2,2,4,4-tetramethylcyclobutyl)-1-isoindoline-5-piperidin-4-methoxy)acetate Under the protection of nitrogen, compounds 4-((1r,3r)-3-(5-bromo-1-isoindolin-2-yl)-2,2,4,4-tetramethylcyclobutyloxy)-2-chlorobenzonitrile (200.0 mg, 0.42 mmol), $Pd_2(dba)_3$ (80.0 mg, 0.04 mmol), BINAP (100.0 mg, 0.08 mmol), t-butyl 2-(piperidine-4-methoxy)acetate (193.0 mg, 0.84 mmol) and sodium t-butoxide (81.0 mg, 0.84 mmol) were added to 4 mL of toluene, and the system was purged with nitrogen three times. The reaction solution was heated to 110° C. and stirred for 12 h. The solution was cooled to room temperature, to which were added ethyl acetate and water for extraction. The organic layer was washed twice with saturated brine, dried over anhydrous sodium sulfate, rotatory evaporated to dry, and purified by silica gel column chromatography to obtain t-butyl 2-((1-(2-((1r,3r)-3-(3-chloro-4-cyanophenoxy)-2,2,4,4-tetramethylcyclobutyl)-1-isoindoline-5-piperidin-4-methoxy)acetate as a colorless oily liquid (90.0 mg, 0.14 mmol), with a yield of 34.3%.

2. Synthesis of Compound 2-((1-(2-((1r,3r)-3-(3-chloro-4-cyanophenoxy)-2,2,4,4-tetramethylcyclobutyl)-1-isoindoline-5-piperidin-4-methoxy)acetic acid Compound t-butyl 2-((1-(2-((1r,3r)-3-(3-chloro-4-cyanophenoxy)-2,2,4,4-tetramethylcyclobutyl)-1-isoindoline-5-piperidin-4-methoxy)acetate (90.0 mg, 0.14 mmol) was dissolved in 2 mL of trifluoroacetic acid and 1 mL of dichloromethane, and then the solution was stirred at room temperature for 1 h. The solvent was removed by rotatory evaporation in vacuo, to obtain crude compound 2-((1-(2-((1r,3r)-3-(3-chloro-4-cyanophenoxy)-2,2,4,4-tetramethylcyclobutyl)-1-isoindoline-5-piperidin-4-methoxy)acetic acid (90.0 mg, 0.14 mmol), which was directly used in next reaction, with a yield of 100.0%. MS (ESI) m/z 513.0, 515.0 $[M+H]^+$.

3. Synthesis of Compound (2S,4R)-1-((S)-2-(2-((1-(2-((1r,3r)-3-(3-chloro-4-cyanophenoxy)-2,2,4,4-tetramethylcyclobutyl)-1-isoindoline-5-piperidin-4-methoxy) acetamide)-3,3-dimethylbutyryl)-4-hydroxy-N-((S)-1-(4-(4-methylthiazol-5-phenyl) ethyl)pyrrolidine-2-carboxamide Compound 2-((1-(2-((1r,3r)-3-(3-chloro-4-cyanophenoxy)-2,2,4,4-tetramethyl cyclobutyl)-1-isoindoline-5-piperidin-4-methoxy)acetic acid (25.0 mg, 0.04 mmol), HATU (18.8 mg, 0.05 mmol) and triethylamine (29.0 mg, 0.20 mmol) were dissolved in 2 mL of DMF, to which was added compound (2S,4R)-1-((S)-2-amino-3,3-dimethylbutyryl)-4-hydroxy-N-((S)-1-(4-(4-methylthiazol-5-yl)phenyl)ethyl) amido) pyrrolidine-2-carboxamide (24.0 mg, 0.05 mmol), and the reaction solution was stirred 1 h at room temperature, to which were added ethyl acetate and 1N hydrochloric acid solution for extraction. The organic layer was washed twice with brine, dried, rotatory evaporated to dry, and purified by silica gel column chromatography, to provide compound (2S,4R)-1-((S)-2-(2-((1-(2-((1r,3r)-3-(3-chloro-4-cyanophenoxy)-2,2,4,4-tetramethylcyclobutyl)-1-isoindoline-5-piperidin-4-methoxy)acetamide)-3,3-dimethylbutyryl)-4-hydroxy-N-((S)-1-(4-(4-methylthiazol-5-phenyl) ethyl)pyrrolidine-2-carboxamide (22.0 mg, 0.02 mmol), with a yield of 50.2%.

LC/MS ($ESI^+$) calcd for $C_{54}H_{67}ClN_7O_7S^+$ ($[M+H]^+$) m/z: 992.5; found 992.5.

$^1H$ NMR (400 MHz, $CDCl_3$) δ 8.71 (s, 1H), 7.79 (s, 1H), 7.57 (d, J=8.7 Hz, 1H), 7.51-7.30 (m, 6H), 7.12 (d, J=8.3 Hz, 1H), 6.99 (d, J=2.3 Hz, 1H), 6.84 (dd, J=8.7, 2.3 Hz, 1H), 5.13-5.05 (m, 1H), 4.78 (t, J=7.9 Hz, 1H), 4.67 (d, J=20.7 Hz, 2H), 4.60-4.49 (m, 2H), 4.39 (s, 1H), 4.31 (s, 1H), 4.10 (d, J=11.0 Hz, 1H), 3.98 (dd, J=33.0, 15.2 Hz, 2H), 3.82 (d, J=11.1 Hz, 2H), 3.62 (dd, J=11.3, 3.4 Hz, 1H), 3.46 (s, 2H), 3.07 (s, 2H), 2.53 (s, 4H), 2.12 (s, 1H), 1.95 (s, 6H), 1.49 (d, J=6.9 Hz, 3H), 1.44 (s, 6H), 1.25 (s, 6H), 1.07 (s, 9H).

410: (3R,5S)-1-((S)-2-(2-((1-(2-((1r,3r)-3-(3-chloro-4-cyanophenoxy)-2,2,4,4-tetramethylcyclobutyl)-1-oxoisoindolin-5-piperidine-4-methoxy)acetamido)-3,3-dimethylbutyryl)-5-(((S)-1-(4-(4-methylthiazol-5-phenyl)ethyl)amido) pyrrolidine-3-acetate

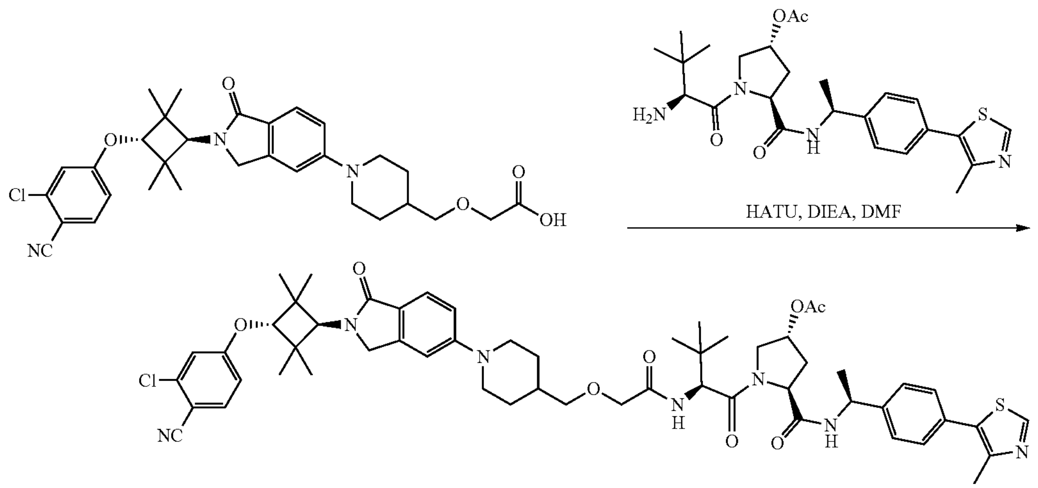

410

Compound 2-((1-(2-((1r,3r)-3-(3-chloro-4-cyanophenoxy)-2,2,4,4-tetramethyl cyclobutyl)-1-isoindoline-5-piperidin-4-methoxy)acetic acid (25.0 mg, 0.04 mmol), HATU (18.8 mg, 0.05 mmol) and triethylamine (29.0 mg, 0.20 mmol) were dissolved in 2 mL of DMF, to which was added compound (2S,4R)-1-((S)-2-amino-3,3-dimethylbutyryl)-4-hydroxy-N-((S)-1-(4-(4-methylthiazol-5-yl)phenyl)ethyl) amido) pyrrolidine-2-carboxamide (24.0 mg, 0.05 mmol), and the reaction solution was stirred at room temperature for 1 h, to which were added ethyl acetate and 1N hydrochloric acid solution for extraction. The organic layer was washed twice with brine, dried, rotatory evaporated to dry, and purified by silica gel column chromatography, to obtain compound (3R,5S)-1-((S)-2-(2-((1-(2-((1r,3r)-3-(3-chloro-4-cyanophenoxy)-2,2,4,4-tetramethylcyclobutyl)-1-oxoisoindolin-5-piperidine-4-methoxy)acetamido)-3,3-dimethylbutyryl)-5-(((S)-1-(4-(4-methylthiazol-5-phenyl)ethyl) amido)pyrrolidine-3-acetate (20 mg, 0.02 mmol), with a yield of 50.1%. MS (ESI) m/z 513.0, 515.0 $[M+H]^+$.

411: Synthesis of (2S,4R)-1-((S)-2-(2-((5-((2-((1r, 3r)-3-(3-chloro-4-cyanophenoxy)-2,2,4,4-methylcyclobutyl)-1-oxoisoindolin-5-amino)pentane)oxy) acetamido)-3,3-dimethylbutyryl)-4-hydroxy-N-((S)-1-(4-(4-methylthiazol-5-phenyl)ethyl) pyrrolidine-2-amide

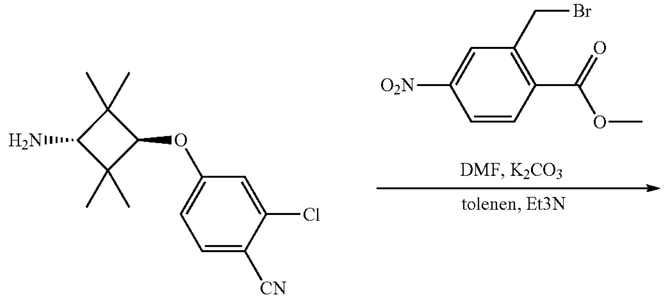

-continued

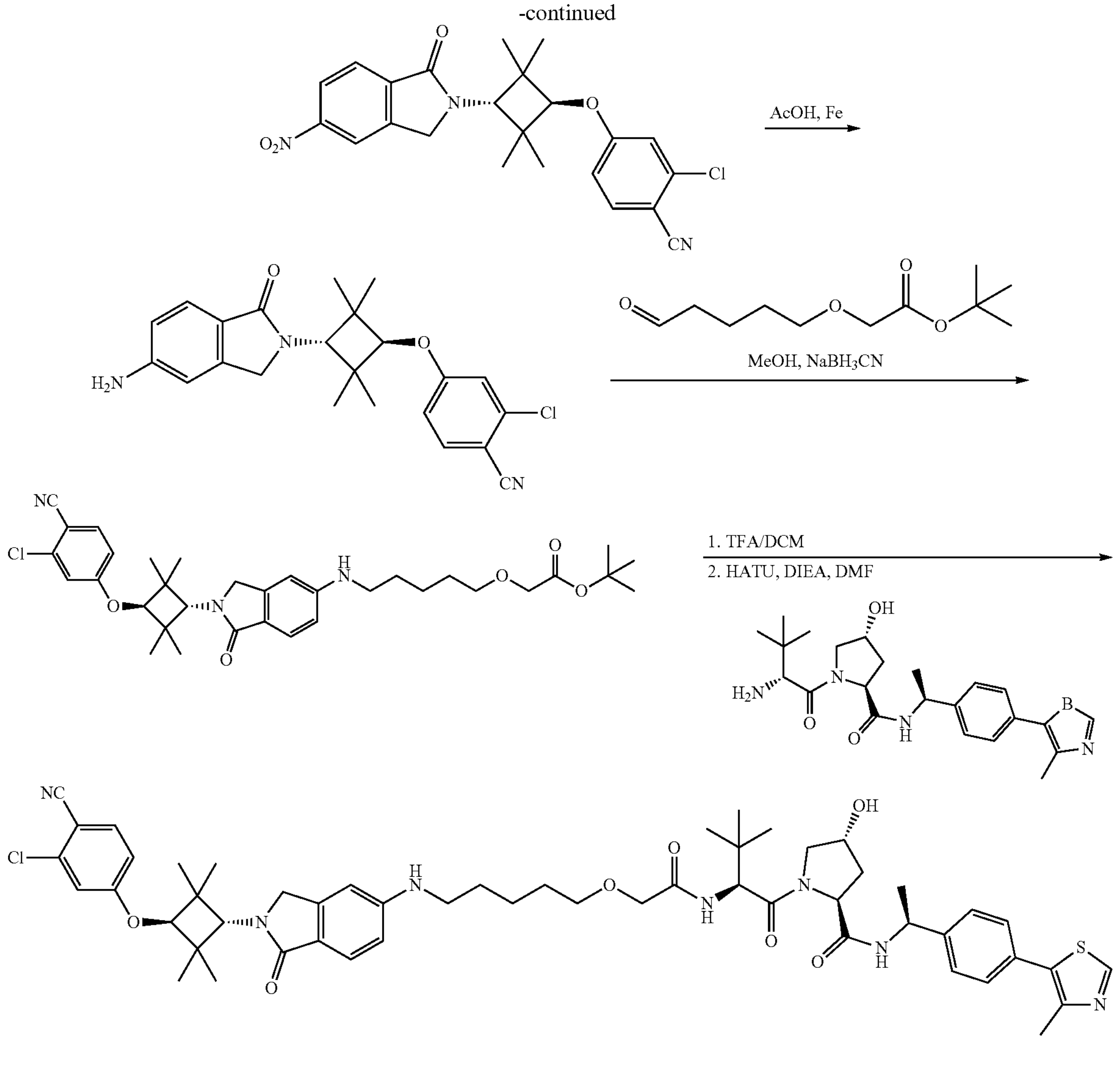

411

1. Synthesis of 2-chloro-4-((1r,3r)-2,2,4,4-tetramethyl-3-5-nitro-1-isoindoline-2-cyclobutyloxy)benzonitrile Compound 4-((1r,3r)-3-amino-2,2,4,4-tetramethylcyclobutyloxy)-2-chlorobenzonitrile (300.0 mg, 1.08 mmol) and $K_2CO_3$ (446.2 mg, 3.23 mmol) were added in 5 mL of DMF, and then methyl 2-bromomethyl-4-nitrobenzoate (324.4 mg, 1.18 mmol) was added the reaction solution in batches. After stirred at room temperature for 1 h, TLC indicated that the reaction was completed and a new spot appeared. To the reaction solution, were added 30 mL ethyl acetate and saturated brine for extraction. The organic layer was washed twice with saturated brine, dried over anhydrous sodium sulfate, rotatory evaporated to dry, and purified by silica gel column chromatography, to obtain 300 mg of oily liquid, to which were added 10 mL of toluene and 1 mL of triethylamine. The reaction solution was heated and stirred for 16 h under reflux. The solvent was rotatory evaporated to dry, and then a small amount of petroleum ether and ethyl acetate (10:1) were added to the residue. The solid was filtered and dried, to obtain a white solid 2-chloro-4-((1r,3r)-2,2,4,4-tetramethyl-3-5-nitro-1-isoindoline-2-cyclobutyloxy) benzonitrile (250.0 mg, 0.56 mmol), with a yield of 49.9%.

2. Synthesis of Compound 4-((1r,3r)-3-(5-amino)-1-isoindolin-2-yl-2,2,4,4-tetramethylcyclobutyloxy-2-chlorobenzonitrile Compound 2-chloro-4-((1r,3r)-2,2,4,4-tetramethyl-3-5-nitro-1-isoindoline-2-cyclobutyloxy)benzonitrile (250.0 mg, 0.56 mmol) was dissolved in 5 mL of acetic acid, to which was added iron powder (317.4 mg, 5.68 mmol). The reaction solution was heated to 50° C. and stirred for 1 h. The reaction was completed by TLC detection. The reaction solution was concentrated to remove the solvent, and then ethyl acetate was added. The resultant solution was filtered through a pad of celite, and the filter cake was washed with ethyl acetate and water. The filtrate was adjusted to be pH 8-9 with the saturated solution of potassium carbonate, and then extracted. The organic layer was washed twice with brine, dry over anhydrous sodium sulfate, and rotatory evaporated to dry, to provide compound 4-((1r,3r)-3-(5-amino)-1-isoindolin-2-yl-2,2,4,4-tetramethylcyclobutyloxy-2-chlorobenzonitrile (249.0 mg, 1.7 mmol), with a yield of 100%.

3. Synthesis of Compound t-butyl 2-((5-((2-((1r,3r)-3-(3-chloro-4-cyanophenoxy)-2,2,4,4-tetramethylcyclobutyl)-1-isoindoline-5-amino)pentane)oxy)acetate Compound 4-((1r,3r)-3-(5-amino)-1-isoindolin-2-yl-2,2,4,4-tetramethylcyclobutyloxy-2-chlorobenzonitrile (110.0 mg, 0.26 mmol) and compound t-butyl 2-((5-formylpentane)oxy)acetate (65.0 mg, 0.29 mmol) were added in 2 ml of methanol, to which were added acetic acid (32.0 mg, 0.53 mmol) and sodium cyanoborohydride (67.0 mg, 1.07 mmol), and then the mixture was stirred at room temperature for 16 h. Ethyl acetate and the saturated solution of sodium bicarbonate were added for extraction. The organic layer was washed twice with brine, dried, rotatory evaporated to dry, and purified by silica gel column chromatography, to provide compound t-butyl 2-((5-((2-((1r,3r)-3-(3-chloro-4-cyanophenyloxy)-2,2,4,4-tetramethylcyclobutyl)-1-isoindoline-5-amino)pentane)oxy)acetate (60.0 mg, 0.09 mmol), with a yield of 36.6%. MS (ESI) m/z 513.0, 515.0 $[M+H]^+$.

4. Synthesis of Compound 2-((5-((2-((1r,3r)-3-(3-chloro-4-cyanophenyloxy)-2,2,4,4-tetramethylcyclobutyl)-1-isoindoline-5-amino)pentane)oxy)acetic acid Compound t-butyl 2-((5-((2-((1r,3r)-3-(3-chloro-4-cyanophenyloxy)-2,2,4,4-tetramethylcyclobutyl)-1-isoindoline-5-amino)pentane)oxy)acetate (60.0 mg, 0.09 mmol) was dissolved in 2 mL of trifluoroacetic acid and 1 mL of dichloromethane, and the mixture was stirred at room temperature for 1 h. The solvent was rotatory evaporated in vacuo to obtain the crude compound 2-((5-((2-((1r,3r)-3-(3-chloro-4-cyanophenyloxy)-2,2,4,4-tetramethylcyclobutyl)-1-isoindoline-5-amino)pentane)oxy) acetic acid (70.0 mg, 0.09 mmol), with a yield of 100.0%, which was directly used in next reaction. MS (ESI) m/z 513.0, 515.0 $[M+H]^+$.

5. Synthesis of Compound (2S,4R)-1-((S)-2-(2-((5-((2-((1r,3r)-3-(3-chloro-4-cyanophenoxy)-2,2,4,4-methylcyclobutyl)-1-oxoisoindolin-5-amino)pentane)oxy) acetamido)-3,3-dimethylbutyryl)-4-hydroxy-N-((S)-1-(4-(4-methylthiazol-5-phenyl)ethyl)pyrrolidine-2-carboxamide Compound 2-((5-((2-((1r,3r)-3-(3-chloro-4-cyanophenyloxy)-2,2,4,4-tetramethylcyclobutyl)-1-isoindoline-5-amino)pentane)oxy)acetic acid (25.0 mg, 0.04 mmol), HATU (18.8 mg, 0.05 mmol) and triethylamine (29.0 mg, 0.20 mmol) were dissolved in 2 mL of DMF, to which was then added compound (2S,4R)-1-((S)-2-amino-3,3-dimethylbutyryl)-4-hydroxy-N-((S)-1-(4-(4-methylthiazol-5-yl) phenyl) ethyl)amido)pyrrolidine-2-carboxamide (24.0 mg, 0.05 mmol). The mixture was stirred at room temperature for 1 h, and then ethyl acetate and 1 N hydrochloric acid solution were added for extraction. The organic layer was washed twice with brine, dried, rotatory evaporated to dry, and purified by silica gel column chromatography, to obtain compound (2S,4R)-1-((S)-2-(2-((5-((2-((1r,3r)-3-(3-chloro-4-cyanophenoxy)-2,2,4,4-methylcyclobutyloxy-1-isoindoline-5-amino)pentane)oxy)acetamido)-3,3-dimethylbutyryl)-4-hydroxylacetyloxy-N-((S)-1-(4-(4-methylthiazol-5-phenyl)ethyl) pyrrolidine-2-carboxamide (25 mg, 0.02 mmol), with a yield of 54.2%.

LC/MS ($ESI^+$) calcd for $C_{53}H_{67}ClN_7O_7S^+$ ($[M+H]^+/2$) m/z: 980.5/2 found 490.3.

$^1H$ NMR (400 MHz, $CDCl_3$) δ 8.69 (s, 1H), 7.73 (d, J=8.0 Hz, 1H), 7.70-7.60 (m, 1H), 7.57 (d, J=8.7 Hz, 1H), 7.34 (dd, J=20.7, 8.0 Hz, 4H), 7.23 (d, J=9.4 Hz, 1H), 6.99 (d, J=1.9 Hz, 1H), 6.97-6.87 (m, 1H), 6.83 (dd, J=8.7, 2.0 Hz, 1H), 5.00-4.89 (m, 1H), 4.82 (s, 1H), 4.67-4.58 (m, 2H), 4.53 (s, 1H), 4.38 (s, 1H), 4.30 (s, 1H), 4.09 (d, J=11.4 Hz, 1H), 3.95 (dd, J=50.0, 15.2 Hz, 2H), 3.71-3.57 (m, 2H), 3.52 (s, 1H), 3.39-3.28 (m, 1H), 3.26-3.15 (m, 1H), 2.52 (s, 3H), 2.36 (s, 1H), 2.21 (d, J=7.6 Hz, 1H), 2.09-1.98 (m, 2H), 1.81 (s, 2H), 1.70 (d, J=6.3 Hz, 2H), 1.57-1.50 (m, 2H), 1.43 (t, J=3.9 Hz, 9H), 1.29 (d, J=2.4 Hz, 6H), 1.09 (s, 9H).

412: (3R,5S)-1-((S)-2-(2-((5-((2-((1r,3r)-3-(3-chloro-4-cyanophenoxy)-2,2,4,4-tetramethylcyclobutyl)-1-oxoisoindolin-5-amino)pentane)oxy) acetamido)-3,3-dimethylbutyryl)-5-(((S)-1-(4-(4-methylthiazol-5-phenyl)ethyl)formamide) pyrrolidine-3-acetate

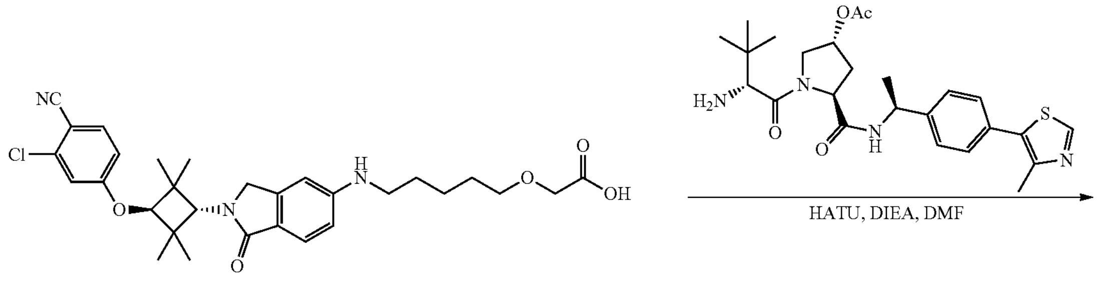

-continued

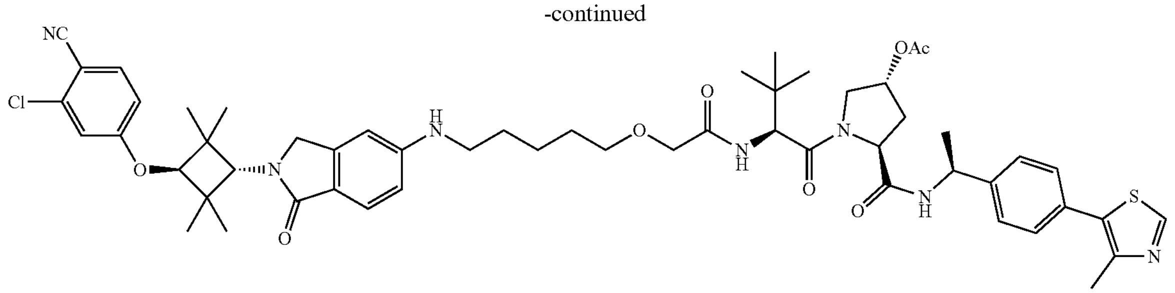

412

Compound 2-((5-((2-((1r,3r)-3-(3-chloro-4-cyanophenyloxy)-2,2,4,4-tetramethylcyclobutyl)-1-isoindoline-5-amino)pentane)oxy)acetic acid (25.0 mg, 0.04 mmol), HATU (18.8 mg, 0.05 mmol) and triethylamine (29.0 mg, 0.20 mmol) were dissolved in 2 mL of DMF, to which was then added compound (3R,5S)-1-((S)-2-amino-3,3-dimethylbutyryl)-5-(((S)-1-(4-(4-methylthiazol-5-yl)phenyl)ethyl) amido) pyrrolidine-3-acetate (24.0 mg, 0.05 mmol). The mixture was stirred at room temperature for 1 h, and then ethyl acetate and 1 N hydrochloric acid solution were added for extraction. The organic layer was washed twice with brine, dried, rotatory evaporated to dry, and purified by silica gel column chromatography, to obtain compound (3R,5S)-1-((S)-2-(2-((5-((2-((1r,3r)-3-(3-chlorocyanophenoxy)-2,2,4,4-methylcyclobutyl)-1-oxoisoindolin-5-amino)pentane) oxy)acetamido)-3,3-dimethylbutyryl)-5-(((S)-1-(4-(4-methylthiazol-5-phenyl)ethyl)pyrrolidine-2-carboxamide (25 mg, 0.02 mmol), with a yield of 54.2%. MS (ESI) m/z 1022 [M+H]+.

413: N-((1r,4r)-4-(3-chloro-4-cyanophenoxy)cyclohexyl)-3-(4-((2-(2,6-dioxopiperidin-3-yl)-1,3-dioxoisoindolin-5-yl)-2,7-diazaspiro[3.5]nonan-7-yl) methyl)piperidin-1-yl)-1,2,4-oxadiazole-5-formamide

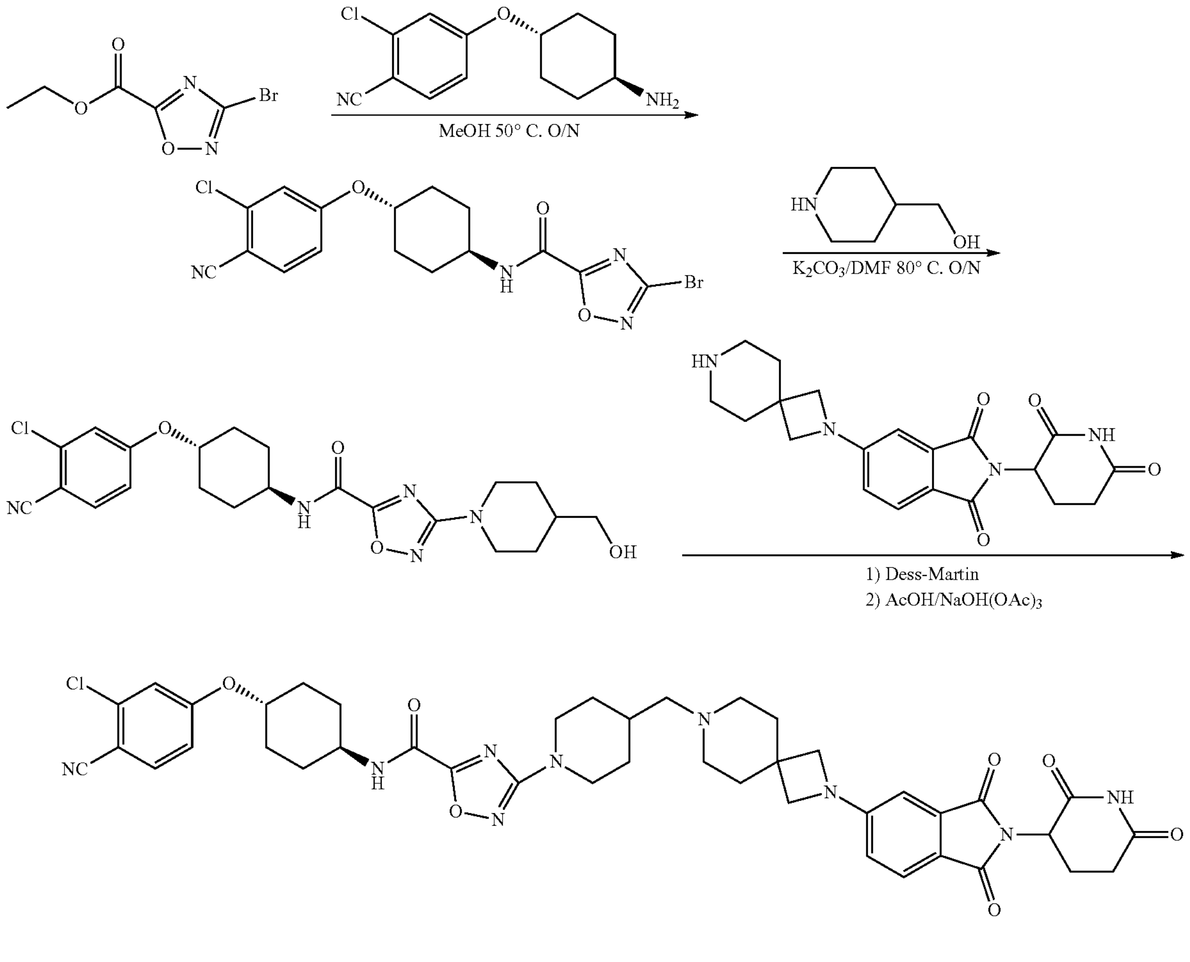

Ethyl 3-bromo-1,2,4-oxadiazole-5-carboxylate (221 mg, 1.0 mmol) and 4-((1r,4r)-4-aminocyclohexyl)oxy)-2-chlorobenzonitrile (251 mg, 1.0 mmol) were dissolved in 5 mL of absolute methanol, and the solution was heated overnight at 50° C. Then, the solution was cooled to room temperature, and separated and purified by thin layer chromatography to obtain the product 3-bromo-N-((1r,4r)-4-(3-chloro-4-cyanophenoxy) cyclohexyl)-1,2,4-oxadiazole-5-formamide (35 mg), with a yield of 8.2%, LC/MS ($ESI^+$) calcd for $C_{16}H_{14}BrClN_4O_3$ ($[M+H]^+$) m/z 425.0.

4-Piperidinemethanol (30 mg, 0.26 mmol) was dissolved in 5 mL of DMF, to which was added potassium carbonate (69 mg, 0.5 mmol), followed by addition of 3-bromo-N-((1r,4r)-4-(3-chloro-4-cyanophenoxy)cyclohexyl)-1,2,4-oxadiazole-5-formamide (35 mg, 0.082 mmol), and then the mixture was allowed to react overnight at 80° C. The reaction solution was cooled to room temperature, and then 10 mL of water and 15 mL of ethyl acetate were added for extraction. The organic layer was successively washed with water and saturated brine, dried over anhydrous sodium sulfate, concentrated under reduced pressure to dryness, and separated and purified by thin layer chromatography, to provide N-((1r,4r)-4-(3-chloro-4-cyanophenoxy)cyclohexyl)-3-(4-hydroxymethyl)piperidin-1-yl)-1,2,4-oxadiazole-5-formamide (30 mg), with a yield of 79.5%. LC/MS ($ESI^+$) calcd for $C_{22}H_{26}ClN_5O_4$ ($[M+H]^+$) m/z 460.1. N-((1r,4r)-4-(3-chloro-4-cyanophenoxy)cyclohexyl)-3-(4-hydroxymethyl)piperidin-1-yl)-1,2,4-oxadiazole-5-formamide (30 mg, 0.067 mmol) was dissolved in 5 mL of dichloromethane, to which was added Dess-Martin periodinane (64 mg, 0.15 mmol). The reaction solution was stirred for 1 h at room temperature, and filtered. The filtrate was concentrated under reduced pressure, to which were successively added 5 mL of dichloromethane, 2-(2,6-dioxopiperidin-3-yl)-5-fluoro-6-(2,7-diazaspiro[3.5]nonan-2-yl)isoindoline-1,3-dione (26 mg, 0.066 mmol), and 0.3 drops of acetic acid. The mixture was stirred at room temperature for 10 min, and then sodium triacetylborohydride (106 mg, 0.5 mmol) was added. The reaction solution was stirred at room temperature for 3 h, successively washed with water and saturated brine, dried over anhydrous magnesium sulfate, concentrated to dryness under reduced pressure, and separated and purified by thin layer chromatography, to provide the product N-((1r,4r)-4-(3-chloro-4-cyanophenoxy)cyclohexyl)-3-(4-((2-(2,6-dioxopiperidin-3-yl)-1,3-dioxoisoindolin-5-yl)-2,7-diazaspiro[3.5]nonan-7-yl)methyl)piperidin-1-yl)-1,2,4-oxadiazole-5-formamide (12 mg), with a yield of 21.7%, LC/MS ($ESI^+$) calcd for $C_{42}H_{46}ClN_9O_7$ ($[M+H]^+$) m/z 824.2, $^1H$ NMR (400 MHz, $CDCl_3$) δ 8.06 (s, 1H), 7.65 (d, J=8.3 Hz, 1H), 7.57 (d, J=8.7 Hz, 1H), 6.99 (d, J=2.4 Hz, 1H), 6.88-6.80 (m, 2H), 6.79 (d, J=2.0 Hz, 1H), 6.52 (dd, J=8.3, 2.1 Hz, 1H), 4.93 (dd, J=12.2, 5.3 Hz, 1H), 4.31 (d, J=10.1 Hz, 1H), 4.06 (d, J=11.8 Hz, 2H), 4.00 (dd, J=7.2, 3.6 Hz, 1H), 3.78 (s, 4H), 3.01-2.72 (m, 6H), 2.45 (s, 2H), 2.20 (dd, J=8.9, 5.1 Hz, 4H), 2.07 (s, 3H), 1.93 (d, J=11.2 Hz, 4H), 1.83 (s, 6H), 1.66 (s, 2H), 1.53-1.45 (m, 2H).

414: N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl)methyl)piperidin-1-yl)-1,3,4-oxadiazole-2-carboxamide

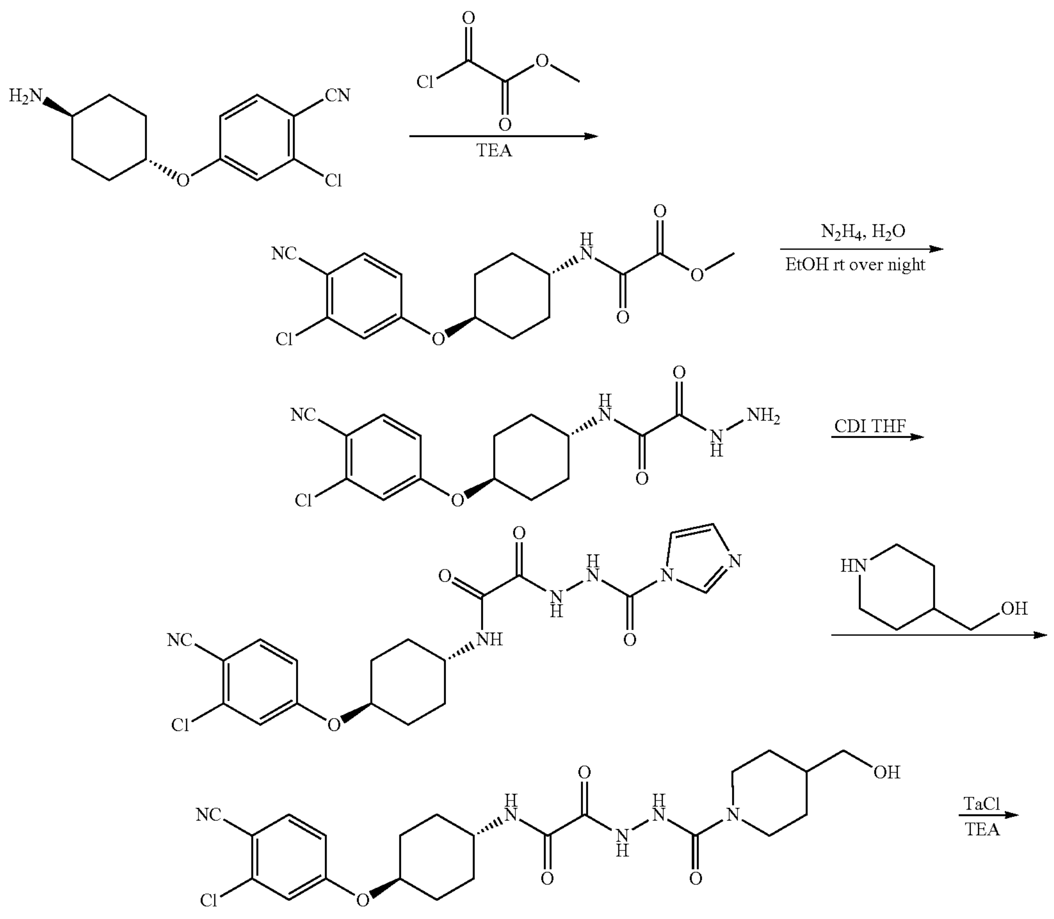

-continued

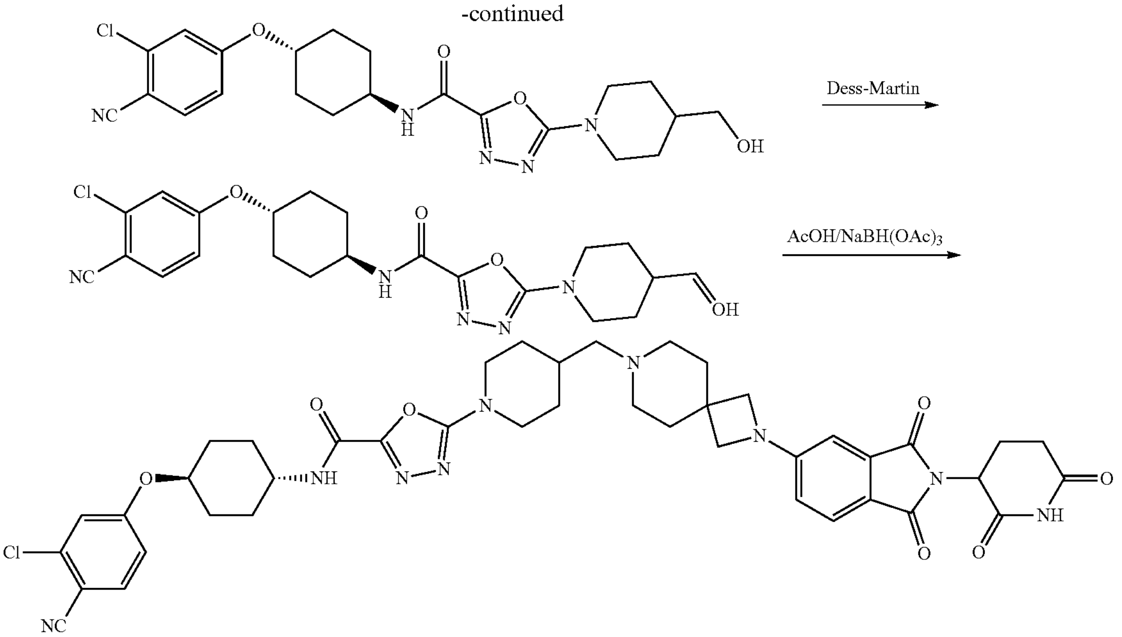

414

4-((1r,4r)-4-Aminocyclohexyl)oxy)-2-chlorobenzonitrile (1.0 g, 4.0 mmol) was dissolved in 25 mL of dichloromethane, to which was added triethylamine (1.21 g, 120 mmol) in an ice-water bath. Methyl 2-chloro-2-oxoacetate (635 mg, 5.2 mmol) was dissolved in 10 mL of dichloromethane and then added dropwise to the reaction system. After that, the solution was slowly warmed to room temperature and reacted overnight. Then, the reaction solution was washed twice with the saturated aqueous solution of ammonium chloride and once with saturated brine, dried over anhydrous magnesium sulfate, filtered, and concentrated to dryness under reduced pressure, to provide methyl 2-((1r,4r)-4-(3-chloro-4-cyanophenoxy)cyclohexyl)amino)-2-oxoacetate (1.30 g), with a yield of 96.5%, LC/MS (ESI+) calcd for $C_{16}H_{17}ClN_2O_4$ ([M+H]+) m/z 337.1.

Methyl 2-((1r,4r)-4-(3-chloro-4-cyanophenoxy)cyclohexyl)amino)-2-oxoacetate (1.30 g, 3.86 mmol) was dissolved in 30 mL of absolute ethanol, to which was added hydrazine hydrate (706 mg, 14.1 mmol), and then the mixture was stirred overnight at room temperature. TLC analysis indicated that the reaction was completed. The reaction solution was filtered, and the filter cake was beaten once with 10 mL of absolute ethanol, and filtered. The filter cake was dried, to provide N-((1r,4r)-4-(3-chloro-4-cyanophenoxy)cyclohexyl)-2-hydrazino-2-oxoacetamide (1.25 g), with a yield of 96.2%, LC/MS (ESI+) calcd for $C_{15}H_{17}ClN_4O_3$ ([M+H]+) m/z 337.1. N-((1r,4r)-4-(3-Chloro-4-cyanophenoxy)cyclohexyl)-2-hydrazino-2-oxoacetamide (400 mg, 1.19 mmol) was dissolved in 5 mL of tetrahydrofuran, to which was added CDI (211 mg, 1.5 mmol). Under the protection of argon, the mixture was allowed to react at room temperature for 3 h, and the reaction was completed, to which was then added 4-piperidinemethanol (164 mg, 1.43 mmol). The reaction solution was dissolved and became clear, and then reacted overnight at room temperature. The solution was concentrated to dry under reduced pressure, and separated and purified by thin layer chromatography, to provide N-((1r,4r)-4-(3-chloro-4-cyanophenoxy)cyclohexyl)-2-(2-(4-(hydroxymethyl)piperidine-1-carbonyl)hydrazino)-2-oxoacetamide (511 mg), with a yield of 89.8%, LC/MS (ESI+) calcd for $C_{22}H_{28}ClN_5O_5$ ([M+H]+) m/z 478.2.

N-((1r,4r)-4-(3-chloro-4-cyanophenoxy)cyclohexyl)-2-(2-(4-(hydroxymethyl) piperidine-1-carbonyl)hydrazino)-2-oxoacetamide (120 mg, 0.25 mmol) was dissolved in 5 mL of dichloromethane, to which were successively added triethylamine (125 mg, 1.25 mmol) and p-toluenesulfonyl chloride (95 mg, 0.5 mmol). The mixture was allowed to react overnight at room temperature. Then, the reaction solution was washed twice with the saturated aqueous solution of ammonium chloride and once with saturated brine, dried over anhydrous magnesium sulfate, concentrated to dryness under reduced pressure, and separated and purified by TLC, to provide N-((1r,4r)-4-(3-chloro-4-cyanophenoxy)cyclohexyl)-5-(4-(hydroxymethyl)piperidin-1-yl)-1,3,4-oxadiazole-2-carboxamide (75 mg), with a yield of 65.2%, LC/MS (ESI+) calcd for $C_{22}H_{26}ClN_5O_4$ ([M+H]+) m/z 460.2. N-((1r,4r)-4-(3-chloro-4-cyanophenoxy)cyclohexyl)-5-(4-(hydroxymethyl)piperidin-1-yl)-1,3,4-oxadiazole-2-carboxamide (40 mg, 0.087 mmol) was dissolved in 5 mL of dichloromethane, to which was added Dess-Martin periodinane (72 mg, 0.17 mmol). The reaction solution was stirred for 1 h at room temperature, and filtered. The filtrate was concentrated to dry under reduced pressure, to which were successively added 5 mL of dichloromethane, 2-(2,6-dioxopiperidin-3-yl)-5-fluoro-6-(2,7-diazaspiro[3.5]nonan-2-yl)isoindoline-1,3-dione (33 mg, 0.087 mmol), and 0.3 drops of acetic acid. The mixture was stirred at room temperature for 10 min, and then sodium triacetylborohydride (106 mg, 0.5 mmol) was added. The reaction solution was stirred at room temperature for 3 h, successively washed with water and saturated brine, dried over anhydrous magnesium sulfate, concentrated to dryness under reduced pressure, and separated and purified by thin layer chromatography to obtain the product N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl)methyl)piperidin-1-yl)-1,3,4-oxadiazole-2-carboxamide (30 mg), with a yield of 41.8%, LC/MS (ESI) calcd for $C_{42}H_{46}ClN_9O_7$ ($[M+H]^+$) m/z 824.3, $^1H$ NMR (400 MHz, $CDCl_3$) δ 8.15-8.00 (m, 1H), 7.72-7.61 (m, 1H), 7.56 (d, J=8.7 Hz, 1H), 6.99 (d, J=2.4 Hz, 1H), 6.84 (dd, J=8.7, 2.4 Hz, 2H), 6.78 (s, 1H), 6.59-6.47 (m, 1H), 5.00-4.86 (m, 1H), 4.34-4.25 (m, 1H), 4.23-4.10 (m, 2H), 4.05-3.94 (m, 1H), 3.93-3.68 (m, 4H), 3.69-3.48 (m, 1H), 3.23-3.03 (m, 2H), 2.97-2.65 (m, 5H), 2.45-2.28 (m, 2H), 2.17 (d, J=10.7 Hz, 7H), 1.97-1.79 (m, 3H), 1.72-1.63 (m, 2H), 1.61 (s, 5H), 1.52-1.43 (m, 2H).

415: N-((1r,4r)-4-(3-chloro-4-cyanophenoxy)cyclohexyl)-5-(4-((2-(2,6-dioxopiperidin-3-yl)-1,3-dioxoisoindolin-5-yl)-2,7-diazaspiro[3.5]nonan-7-yl)methyl)piperidin-1-yl)-1,2,4-oxadiazole-3-formamide

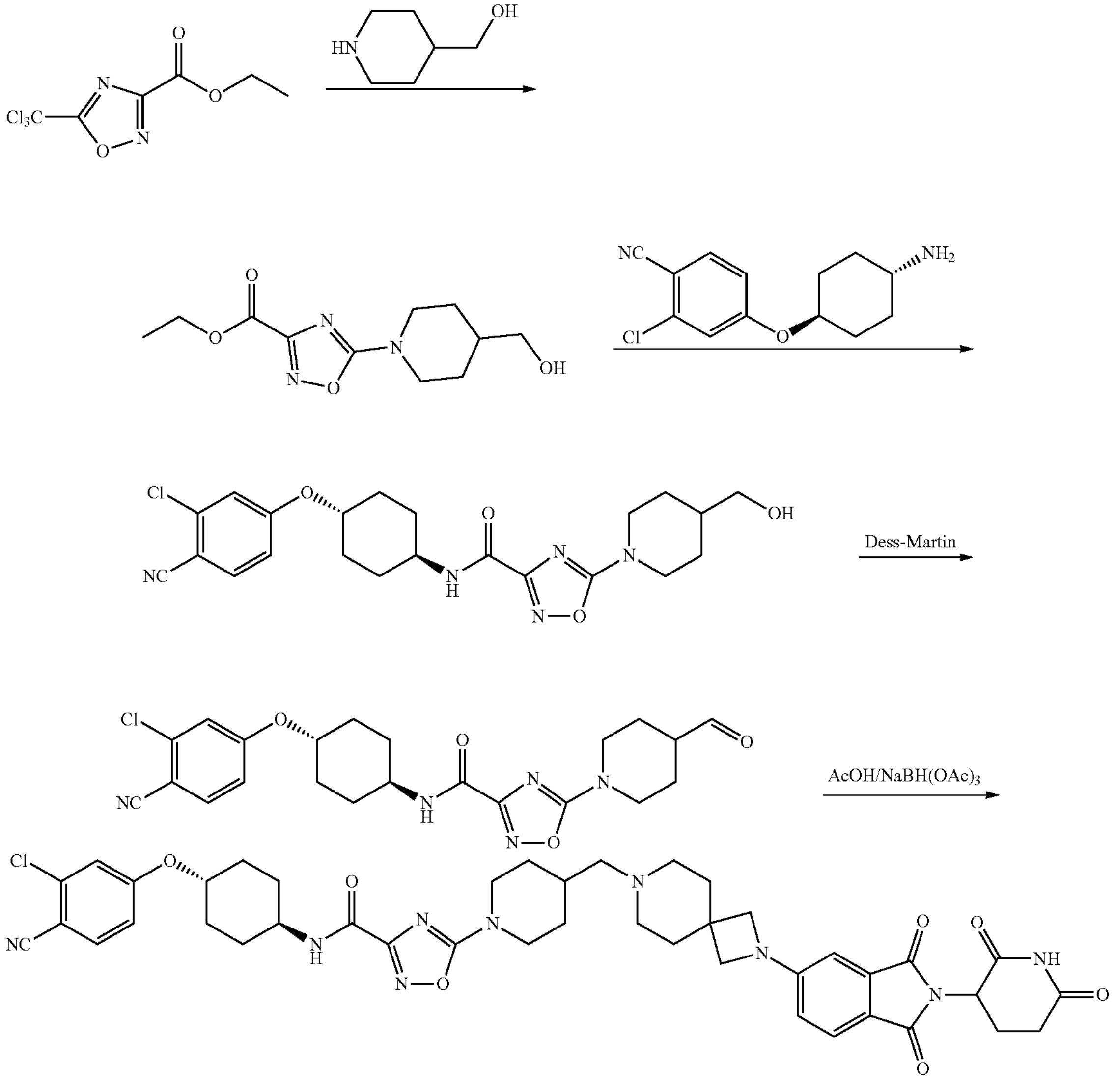

415

LC/MS ($ESI^+$) calcd for $C_{42}H_{46}ClN_9O_7$ ($[M+H]^+$) m/z 824.3, $^1H$ NMR (400 MHz, $CDCl_3$) δ 8.06 (s, 1H), 7.65 (d, J=8.2 Hz, 1H), 7.59-7.52 (m, 1H), 6.99 (d, J=2.4 Hz, 1H), 6.84 (dd, J=8.7, 2.4 Hz, 1H), 6.78 (d, J=1.9 Hz, 1H), 6.72 (d, J=8.1 Hz, 1H), 6.52 (d, J=8.7 Hz, 1H), 4.93 (dd, J=12.2, 5.3 Hz, 1H), 4.29 (d, J=10.1 Hz, 1H), 4.23 (d, J=14.0 Hz, 2H), 4.03 (dd, J=11.3, 7.7 Hz, 1H), 3.78 (d, J=21.3 Hz, 4H), 3.12 (t, J=12.7 Hz, 2H), 2.94-2.68 (m, 4H), 2.38 (s, 3H), 2.26-2.09 (m, 7H), 1.87 (s, 4H), 1.72-1.54 (m, 7H), 1.49-1.40 (m, 2H).

416: N-((1r,4R)-4-(3-chloro-4-cyanophenoxy)cyclohexyl)-1-((1r,4R)-4-((2-(2-(2,6-dioxopiperidin-3-yl)-1,3-dioxoisoindolin-5-yl)-2,7-diazaspiro[3.5]nonan-7-yl)methyl)cyclohexyl)-1H-pyrazole-3-formamide
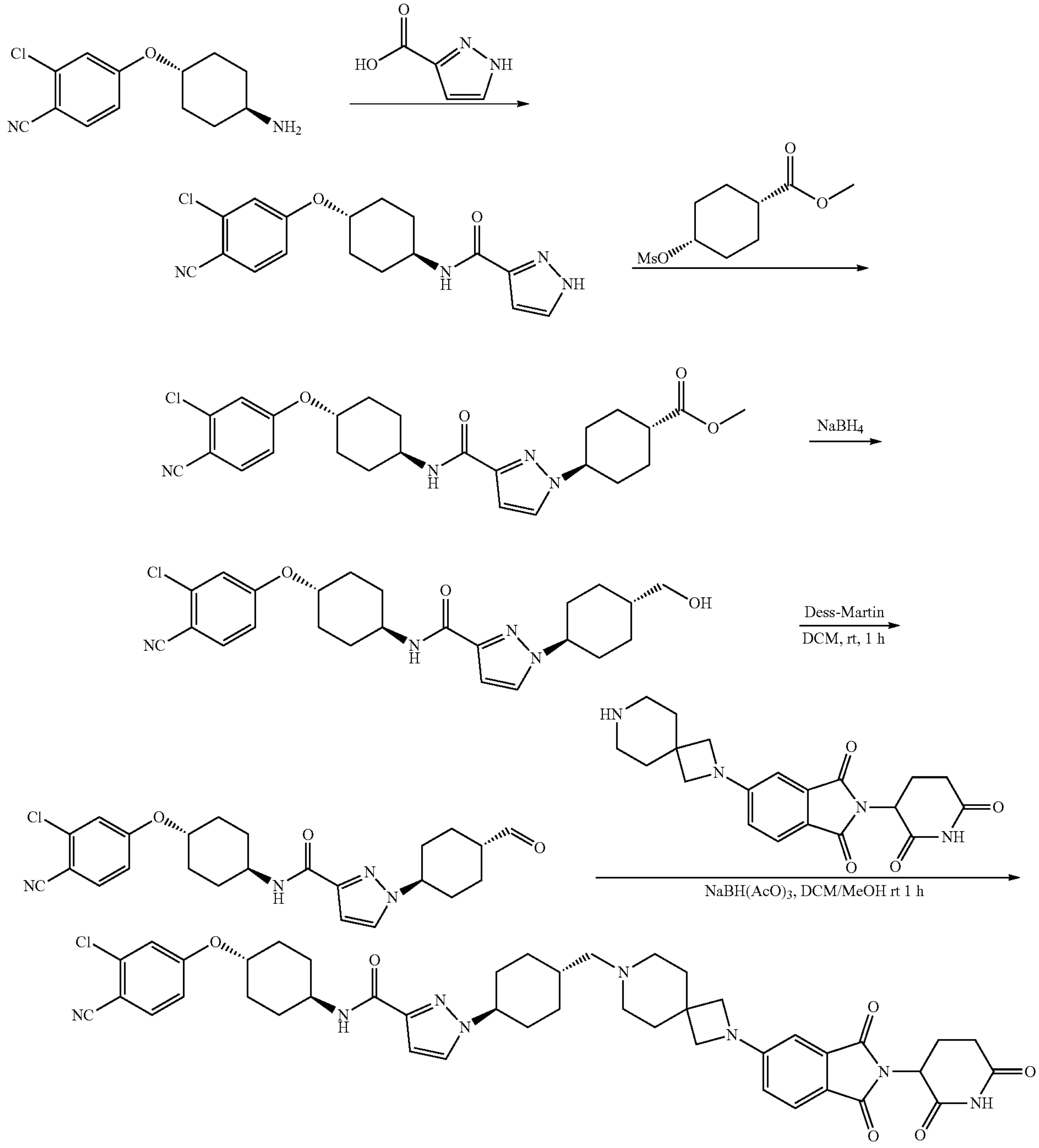
416
$^1$H NMR (400 MHz, DMSO-D6-$d_6$) β 11.08 (s, 1H), 7.86 (d, J=8.8 Hz, 1H), 7.82 (d, J=2.3 Hz, 1H), 7.77 (d, J=8.1 Hz, 1H), 7.64 (d, J=8.3 Hz, 1H), 7.37 (d, J=2.4 Hz, 1H), 7.13 (dd, J=8.8, 2.4 Hz, 1H), 6.78 (s, 1H), 6.65 (d, J=8.3 Hz, 1H), 6.62 (d, J=2.3 Hz, 1H), 5.05 (dd, J=12.8, 5.2 Hz, 1H), 4.50 (s, 1H), 4.17 (s, 1H), 2.86 (dd, J=21.5, 9.9 Hz, 1H), 2.61-2.52 (m, 1H), 2.33 (s, 4H), 2.14-1.98 (m, 7H), 1.76 (s, 6H), 1.63-1.43 (m, 6H), 1.23 (s, 6H), 1.05 (dd, J=12.2, 5.2 Hz, 3H), 0.84 (d, J=7.0 Hz, 2H). LC/MS ($ESI^+$) calcd for $C_{44}H_{49}ClN_8O_6$ ($[M+H]^+$) m/z 821.38; found 821.3.-

417: N-((1r,4r)-4-(3-chloro-4-cyanophenoxy)cyclohexyl)-3-(4-((2-(2,6-dioxopiperidin-3-yl)-6-fluoro-1-oxoisoindolin-5-yl)-2,7-diazaspiro[3.5]nonan-7-yl)methyl)piperidin-1-yl)-1,2,4-triazine-6-formamide

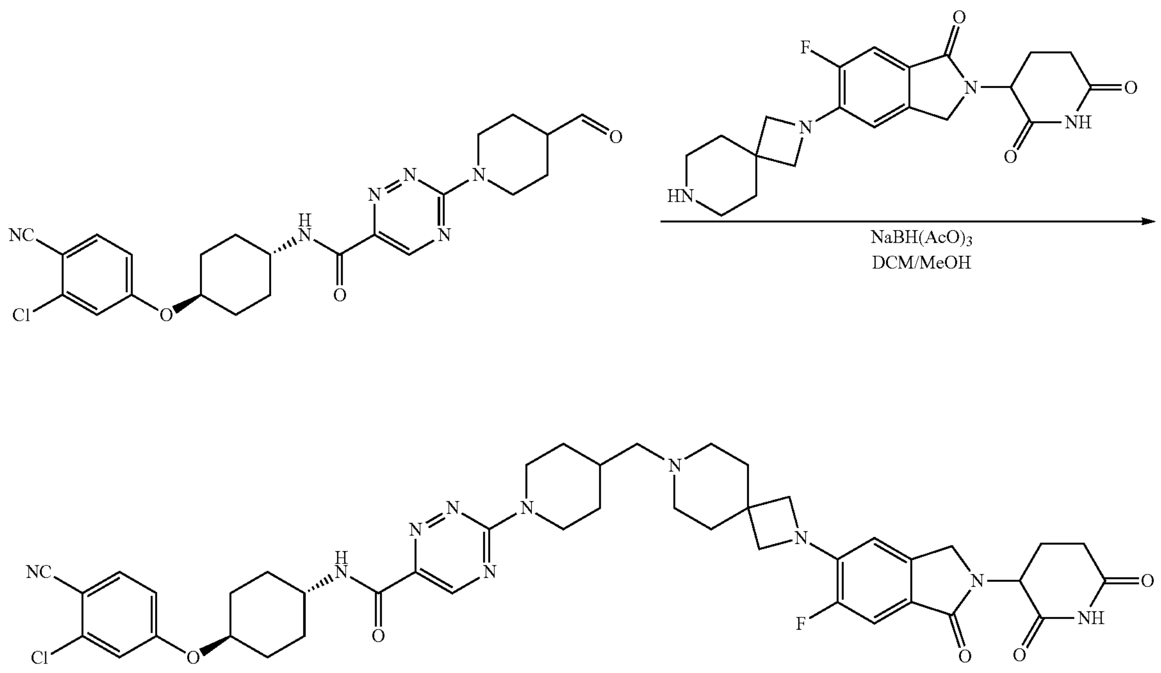

417

LC/MS (ESI$^+$) Calcd for $C_{43}H_{48}FClN_{10}O_5$(M+H$^+$) m/z, 839.3; found 839.3. H NMR (400 MHz, $CDCl_3$) δ 8.82 (s, 1H), 8.09 (s, 1H), 7.57 (dd, J=8.5, 5.4 Hz, 2H), 7.40 (d, J=11.3 Hz, 1H), 7.00 (d, J=2.4 Hz, 1H), 6.85 (dd, J=8.8, 2.4 Hz, 1H), 6.39 (d, J=7.6 Hz, 1H), 5.18 (dd, J=13.2, 5.2 Hz, 1H), 4.33 (dd, J=18.8, 12.9 Hz, 2H), 4.10-4.00 (m, 1H), 3.83 (s, 3H), 3.06 (s, 2H), 2.92-2.75 (m, 2H), 2.58 (s, 3H), 2.45-2.27 (m, 4H), 2.25-2.12 (m, 5H), 2.09 (s, 2H), 1.99 (s, 5H), 1.72-1.62 (m, 2H), 1.52-1.41 (m, 2H), 1.32-1.20 (m, 3H).

418: N-((1r,4r)-4-(3-chloro-4-cyanophenoxy)cyclohexyl)-6-(4-((7-(2-(2,6-dioxopiperidin-3-yl)-1,3-dioxoisoindolin-5-yl)-2,7-diazaspiro[3.5]nonane-2-yl) methyl)-4-methylpiperidin-1-yl)pyridazine-3-formamide

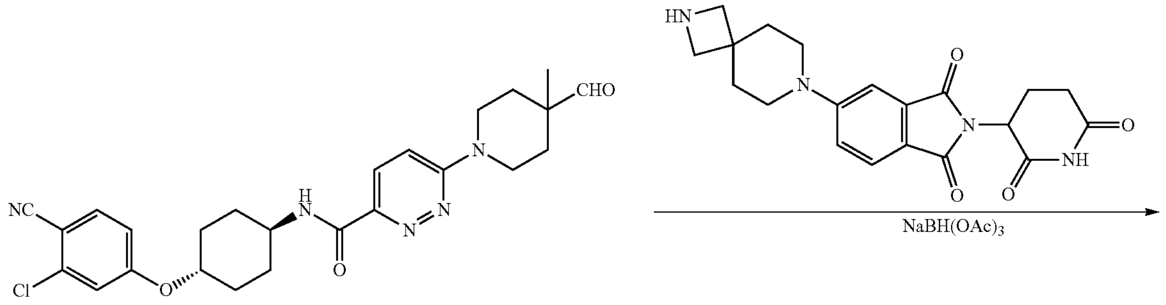

-continued
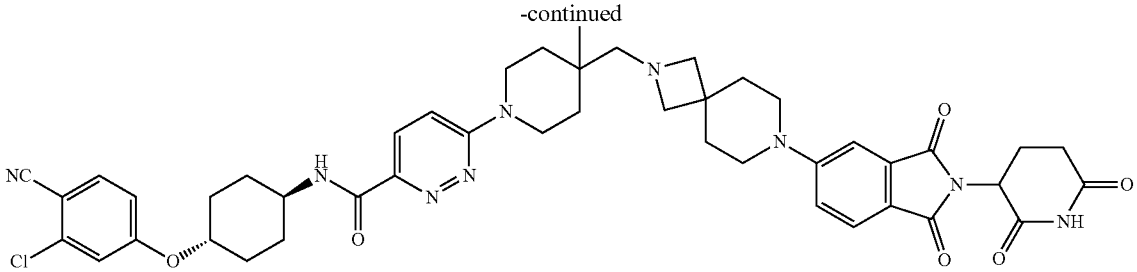
418
HC-4521
LC/MS ($ESI^+$) for $C_{45}H_{51}ClN_9O_6[M+H]^+$ m/z 848.
419: N-((1r,4r)-4-(3-bromo-4-cyanophenoxy)cyclohexyl)-3-(4-((2-(2-(2,6-dioxopiperidin-3-yl)-1,3-dioxoisoindolin-5-yl)-2,7-diazaspiro[3.5]nonane-7-yl) methyl)piperidin-1-yl)-1,2,4-triazole-6-formamide
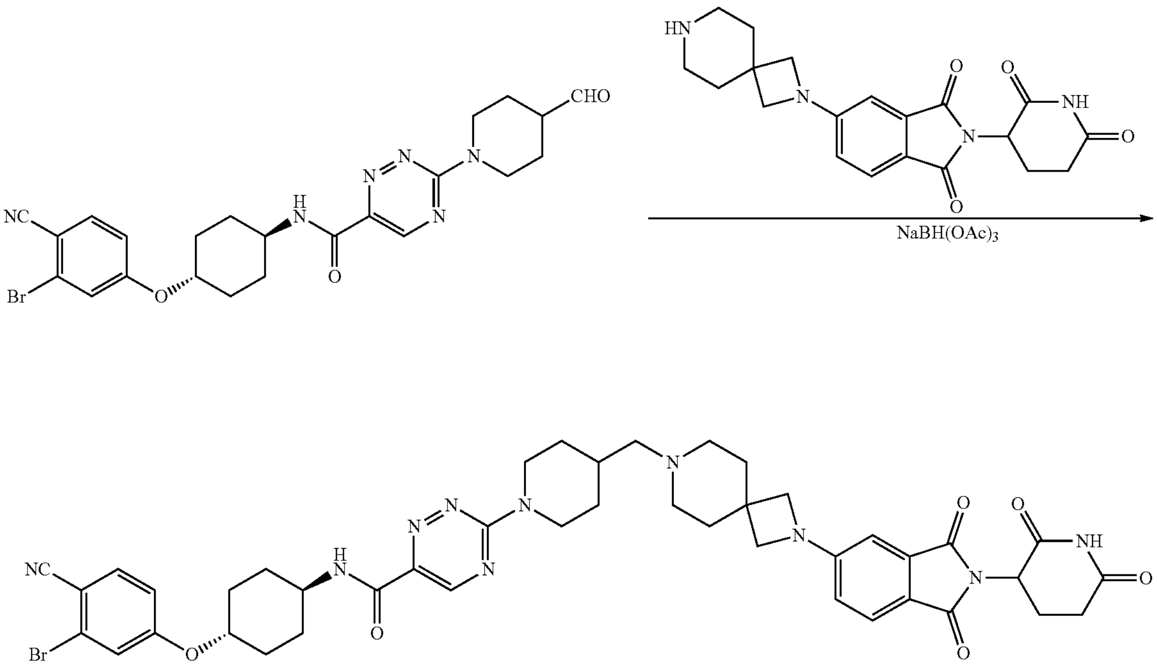
419
LC/MS ($ESI^+$) for $C_{43}H_{48}BrN_{10}O_6$ $[M+H]^+$ m/z 879.

420: N-((1r,4r)-4-(4-cyano-3-trifluoromethyl-phenoxy) cyclohexyl)-3-(4-((2-(2-(2,6-dioxopiperidin-3-yl)-1,3-dioxoisoindolin-5-yl)-2,7-diazaspiro[3.5] nonane-7-yl)methyl)piperidin-1-yl)-1,2,4-triazine-6-formamide

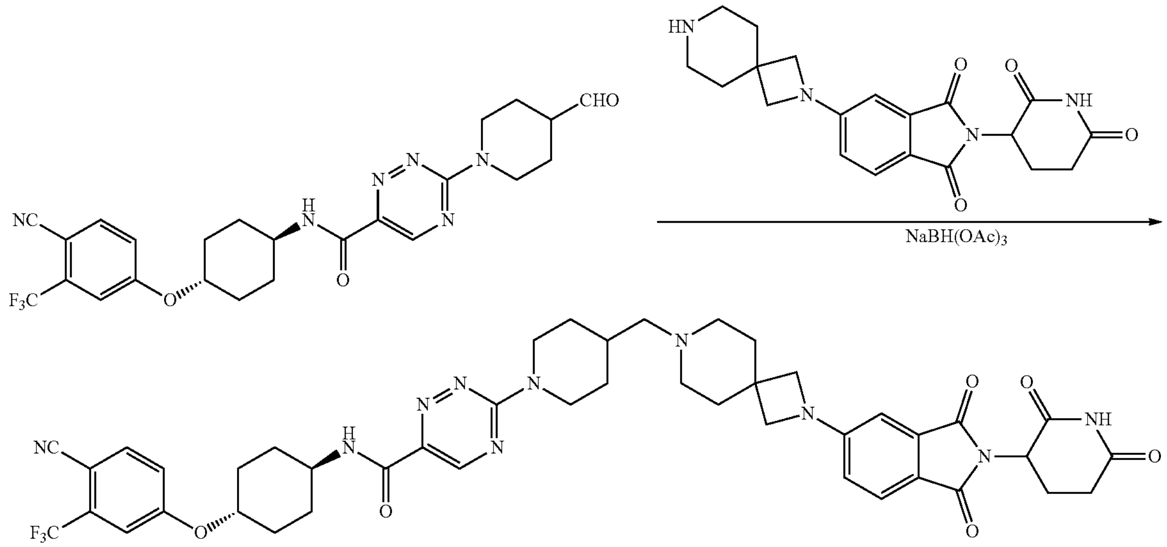

420

LC/MS ($ESI^+$) for $C_{44}H_{48}F_3N_{10}O_6$ $[M+H]^+$ m/z 869.

421: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonane-7-yl)methyl)piperidin-1-yl)-1,2,4-triazine-3-formamide

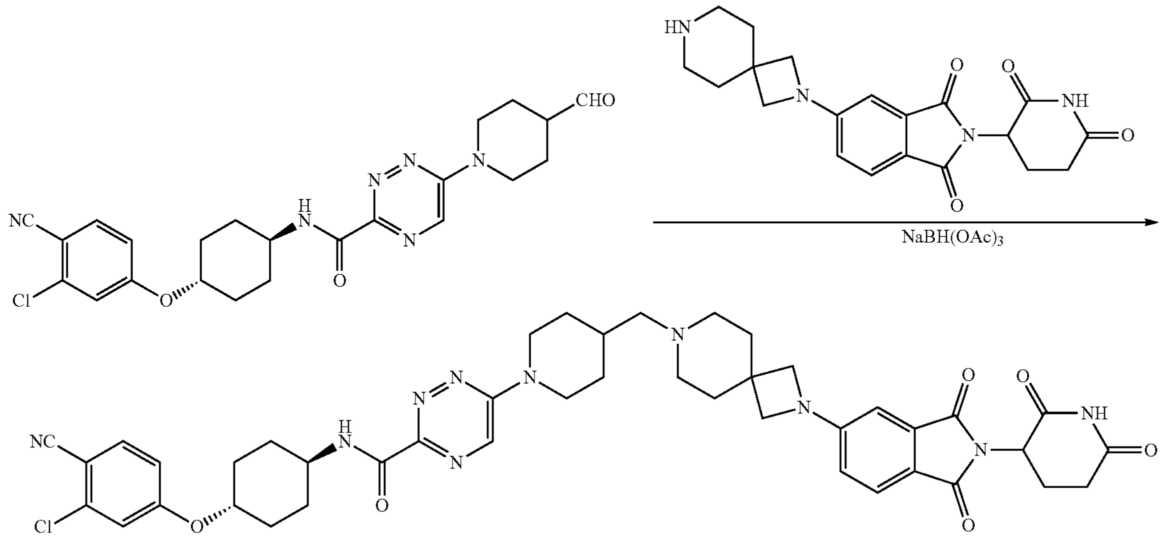

421

LC/MS ($ESI^+$) for $C_{43}H_{48}ClN_{10}O_6$ $[M+H]^+$ m/z 835.

422: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonan-7-yl)methyl)-4-methylpiperidin-1-yl)pyridazine-3-formamide

422

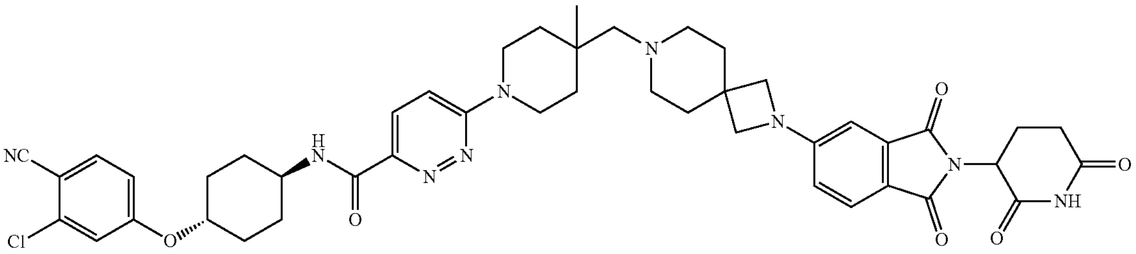

LC/MS (ESI$^+$) for $C_{45}H_{51}ClNO_6$ $[M+H]^+$ m/z 848.

423: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonane-7-yl) methyl)-4-hydroxypiperidin-1-yl)pyridazine-3-formamide

423

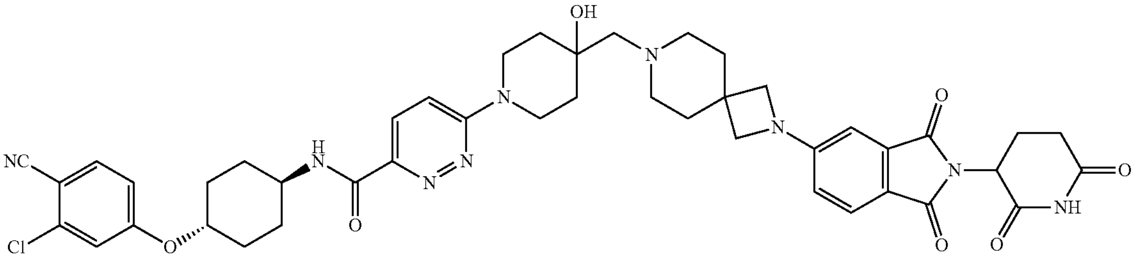

LC/MS (ESI$^+$) for $C_{44}H_{49}ClN_9O_7$ $[M+H]^+$ m/z 850.

424: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonane-7-yl) methyl)-4-fluoropiperidin-1-yl)pyridazine-3-formamide

424

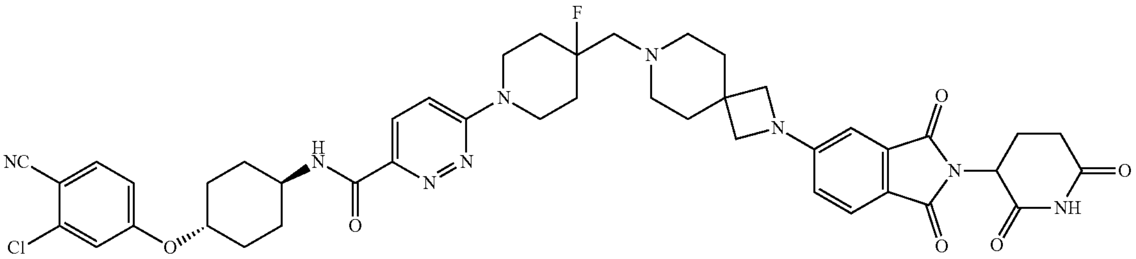

LC/MS (ESI$^+$) for $C_{44}H_{48}ClFN_9O_6$ $[M+H]^+$ m/z 852.

425: 2-Chloro-4-(((1r,4r)-4-(((6-(4-((2-(2-(2,6-dioxopiperidin-3-yl)-1,3-dioxoisoindolin-5-yl)-2,7-diazaspiro[3.5]nonan-7-yl)methyl)piperidin-1-yl)pyridazine-3-yl)methyl)amino)cyclohexyl)oxy)benzonitrile

425

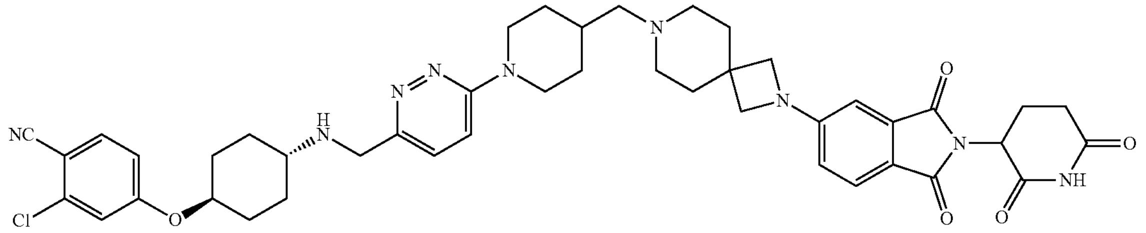

LC/MS (ESI$^+$) for $C_{44}H_{50}ClN_9O_5$[M+H]$^+$ m/z 820.

426: N-((1r,4r)-4-(3-chloro-4-cyanophenoxy)cyclohexyl)-6-(4-((2-(2-(2,6-dioxopiperidin-3-yl)-1,3-dioxoisoindolin-5-yl)-2,7-diazaspiro[3.5]nonane-7-yl)methyl)-4-fluoropiperidin-1-yl)-1,2,4-triazine-6-formamide

426

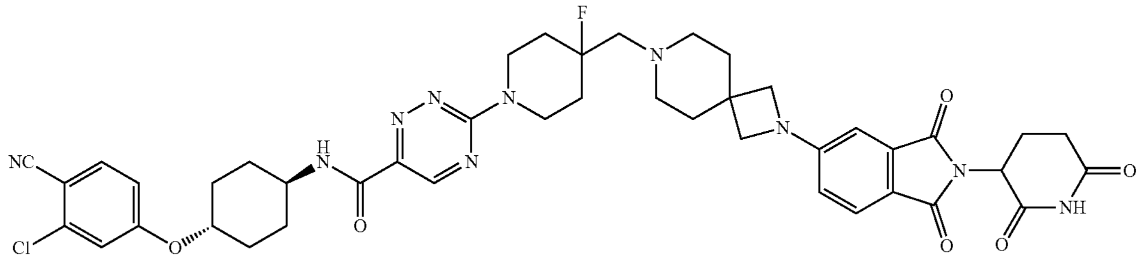

LC/MS (ESI$^+$) for $C_{43}H_{47}ClFN_{10}O_6$ [M+H]$^+$ m/z 853.

427: N-((1r,4r)-4-((5-chloro-6-cyanopyridin-3-yl)oxy)cyclohexyl)-6-(4-((2-(2-(2,6-dioxopiperidin-3-yl)-1,3-dioxoisoindolin-5-yl)-2,7-diazaspiro[3.5]nonane-7-yl) piperidin-1-yl)pyridazine-3-formamide

427

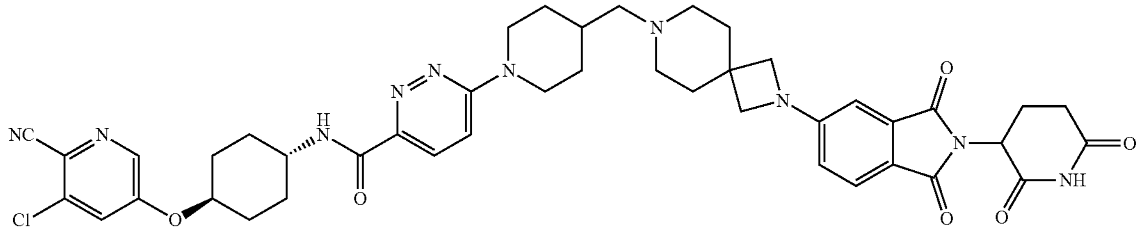

LC/MS (ESI$^+$) for $C_{43}H_{48}ClN_{10}O_6$[M+H]$^+$ m/z 835.

428: N-((1r,4r)-4-(3-chloro-4-cyanophenoxy)cyclohexyl)-6-(4-((2-(6-(2,6-dioxopiperidin-3-yl)-5-oxo-6,7-dihydro-5H-pyrrolo[3,4-b]pyridin-2-yl)-2,7-diazaspiro[3.5]nonane-7-yl)methyl)piperidin-1-yl) pyridazine-3-formamide
428
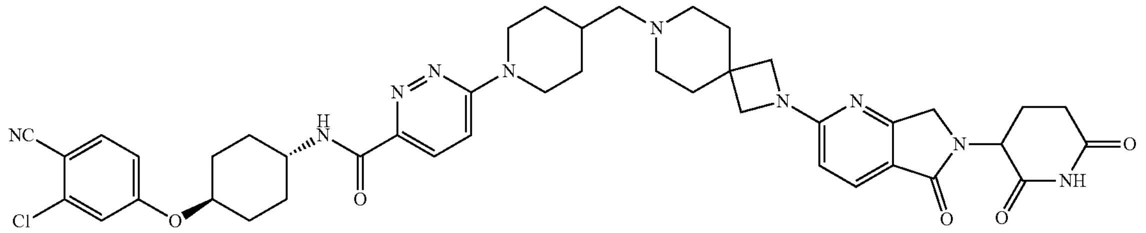
LC/MS (ESI+) for $C_{43}H_{50}ClN_{10}O_5$ $[M+H]^+$ m/z 821.
429: 4-((1r,3r)-3-(2-((1r,4r)-4-(4-(2,6-dioxopiperidin-3-yl)-1,3-dioxoisoindolin-5-yl)piperazin-1-yl) cyclohexyl)ethynyl)-5-oxo-5,7-dihydro-pyrrolo[3,4-b]pyridin-6-yl)-2,2,4,4-tetramethylcyclobutoxy)-2-deuteromethoxybenzonitrile
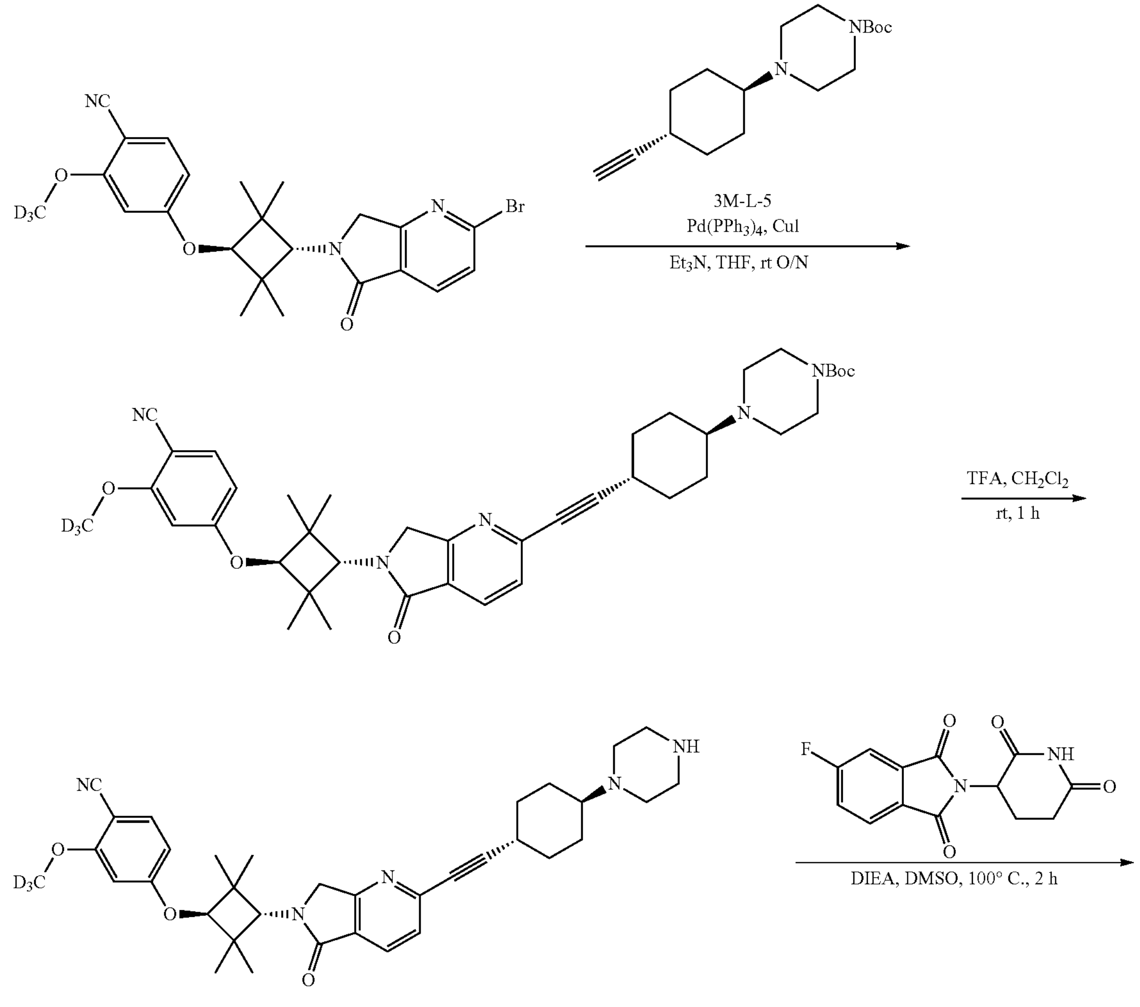

-continued
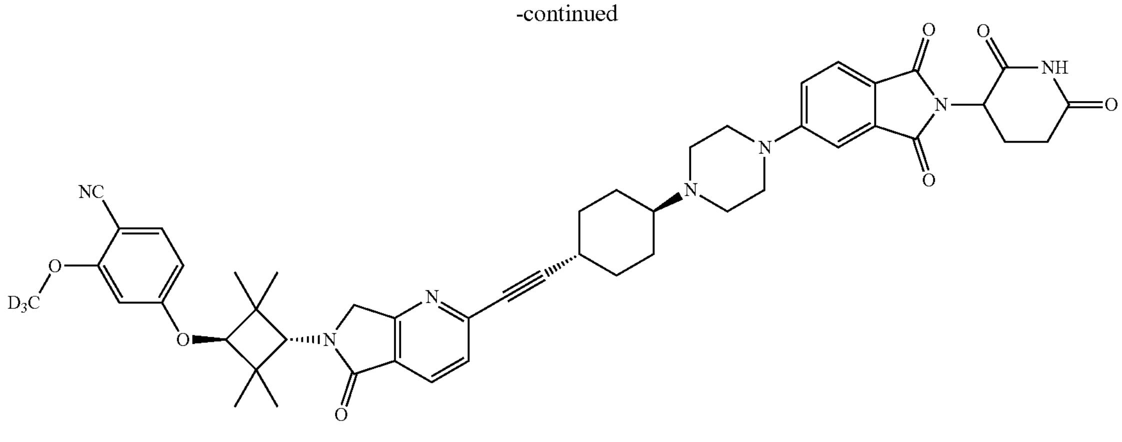
429
$^1$H NMR (400 MHz, DMSO-d$_6$) δ 11.09 (s, 1H), 8.04 (d, J=7.9 Hz, 1H), 7.66 (dd, J=13.5, 8.6 Hz, 2H), 7.54 (d, J=7.9 Hz, 1H), 7.34 (s, 1H), 7.26 (d, J=8.6 Hz, 1H), 6.69 (d, J=2.1 Hz, 1H), 6.60 (dd, J=8.7, 2.2 Hz, 1H), 5.07 (dd, J=12.9, 5.3 Hz, 1H), 4.81 (s, 2H), 4.49 (s, 1H), 4.33 (s, 1H), 3.42 (s, 4H), 2.97-2.78 (m, 1H), 2.74-2.52 (m, 6H), 2.46-2.33 (m, 2H), 2.18-1.94 (m, 3H), 1.87 (d, J=10.1 Hz, 2H), 1.55-1.28 (m, 101-), 1.18 (s, 6H). MS: calcd. for $C_{48}H_{48}D_3N_7O_7$ [M+H]$^+$: 841.40; found: 841.3.
430: 4-((1r,3r)-3-(2-((1r,4r)-4-(4-(2-(2,6-Dioxopiperidin-3-yl)-1,3-dioxoisoindolin-5-yl)piperazin-1-yl)cyclohexyl)ethynyl)-5-oxo-5,7-dihydro-pyrrolo[3,4-b]pyridin-6-yl)-2,2,4,4-tetramethylcyclobutoxy)-2-ethoxybenzonitrile
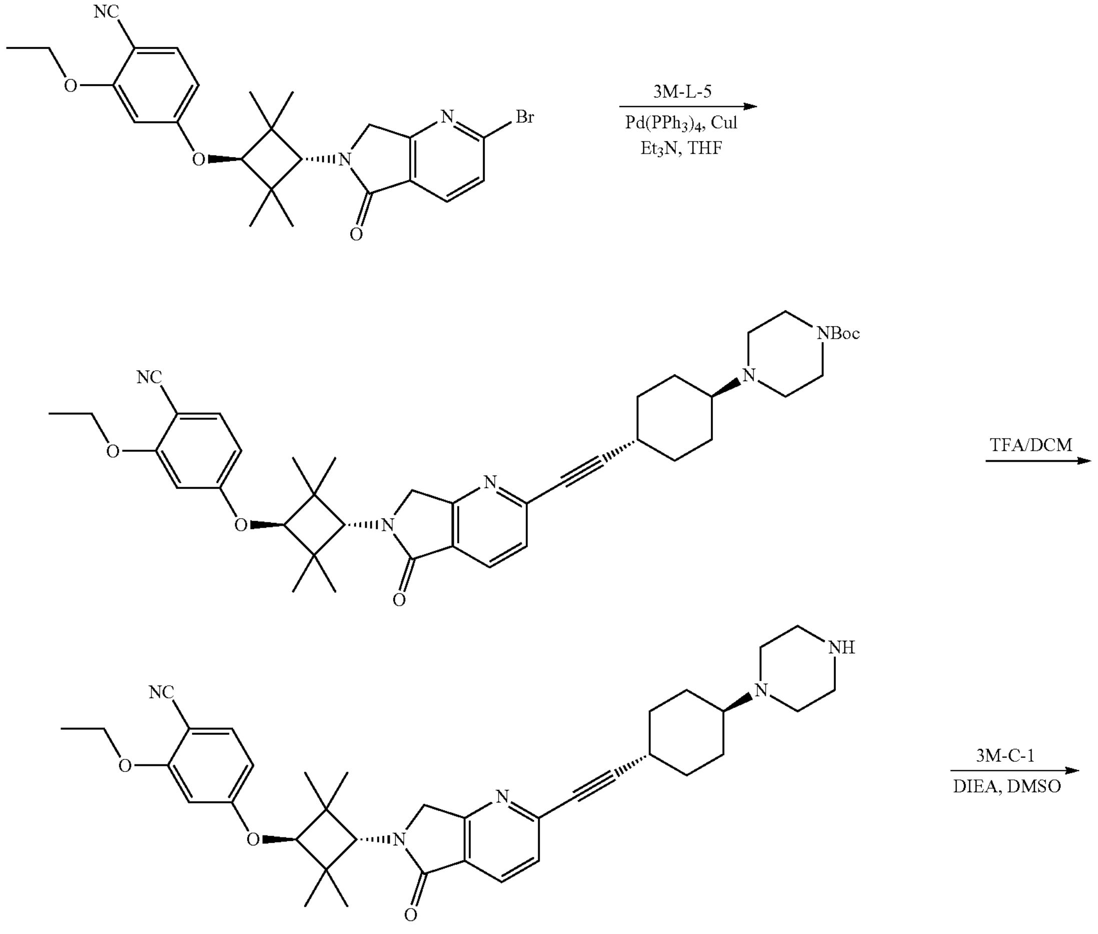

-continued
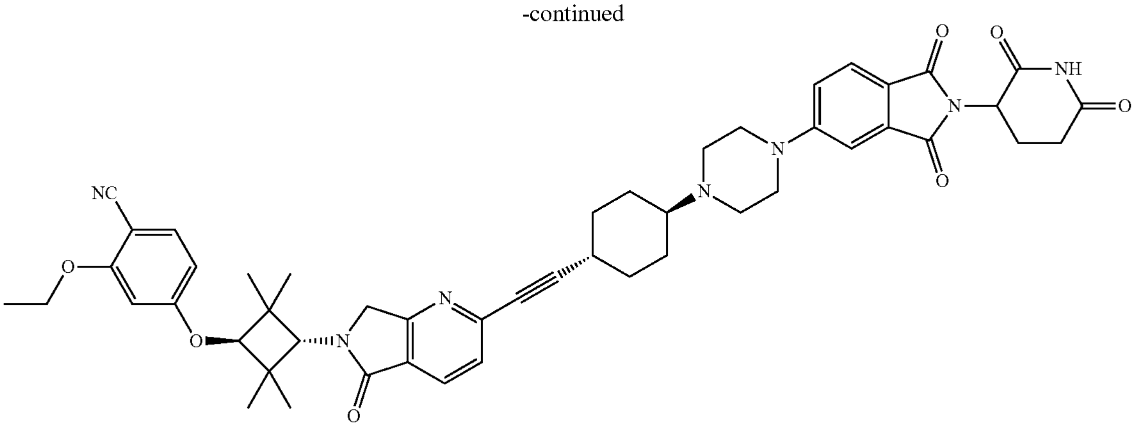
430
$^1$H NMR (400 MHz, DMSO-$d_6$) δ 11.09 (s, 1H), 8.04 (d, J=7.9 Hz, 1H), 7.68 (d, J=8.5 Hz, 1H), 7.64 (d, J=8.6 Hz, 1H), 7.54 (d, J=7.9 Hz, 1H), 7.34 (s, 1H), 7.26 (d, J=8.7 Hz, 1H), 6.67 (d, J=2.0 Hz, 1H), 6.59 (d, J=8.8 Hz, 1H), 5.07 (dd, J=12.8, 5.4 Hz, 1H), 4.80 (s, 2H), 4.48 (s, 1H), 4.33 (s, 1H), 4.19 (q, 0.1=7.0 Hz, 2H), 3.42 (s, 4H), 2.87-2.65 (m, 1H), 2.63-2.53 (m, 6H), 2.41-2.35 (m, 1H), 2.15-1.98 (m, 4H), 1.86 (d, J=10.3 Hz, 2H), 1.47-1.36 (m, 13H), 1.17 (s, 6H). MS: calcd. for $C_{49}H_{53}N_7O_7[M+H]^+$: 852.4; found: 852.2.
431: 2-bromo-4-((1r,3r)-3-(2-((1r,3r)-3-(4-(2-(2,6-dioxopiperidin-3-yl)-1,3-dioxoisoindolin-5-yl)piperazin-1-yl)cyclobutyl)ethynyl)-5-oxo-5,7-dihydro-6H-pyrrolo[3,4-b]pyridin-6-yl)-2,2,4,4-tetramethylcyclobutoxy)benzonitrile
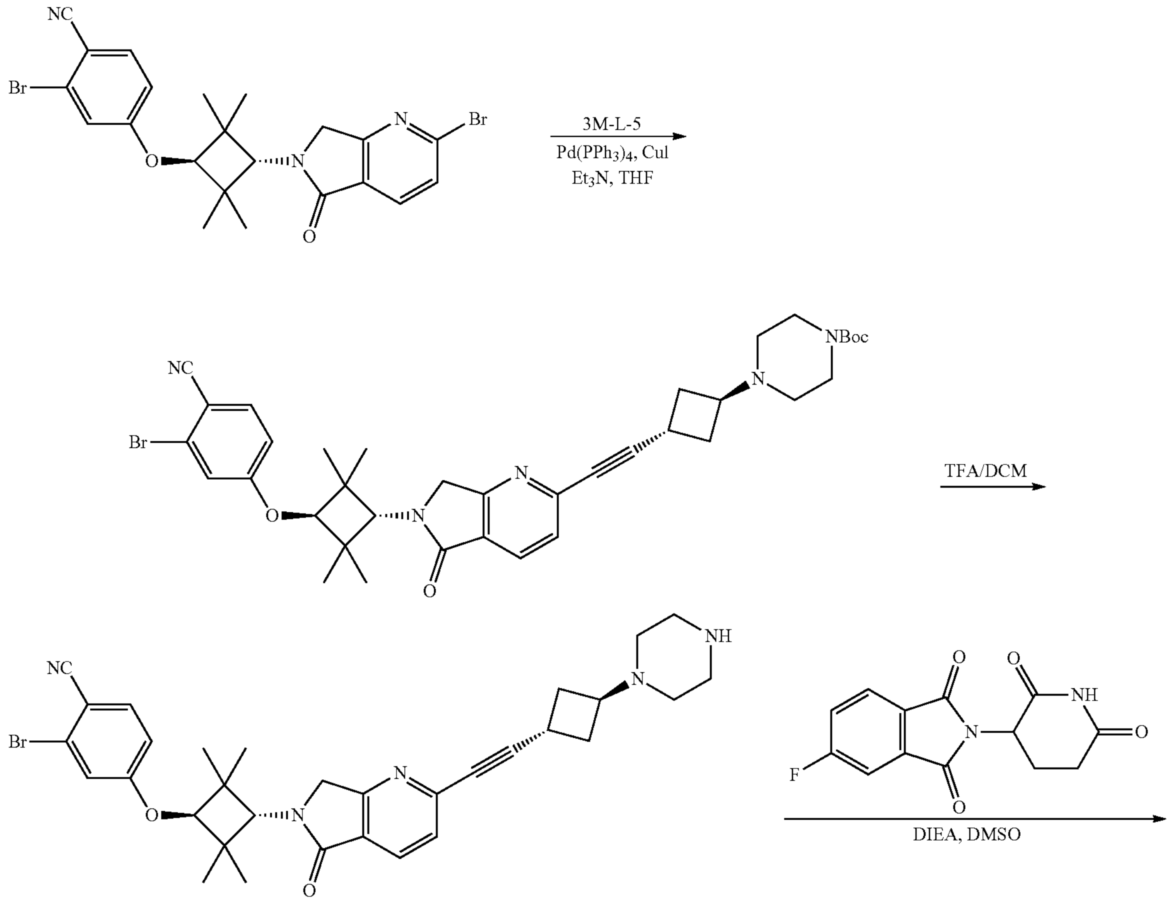

-continued
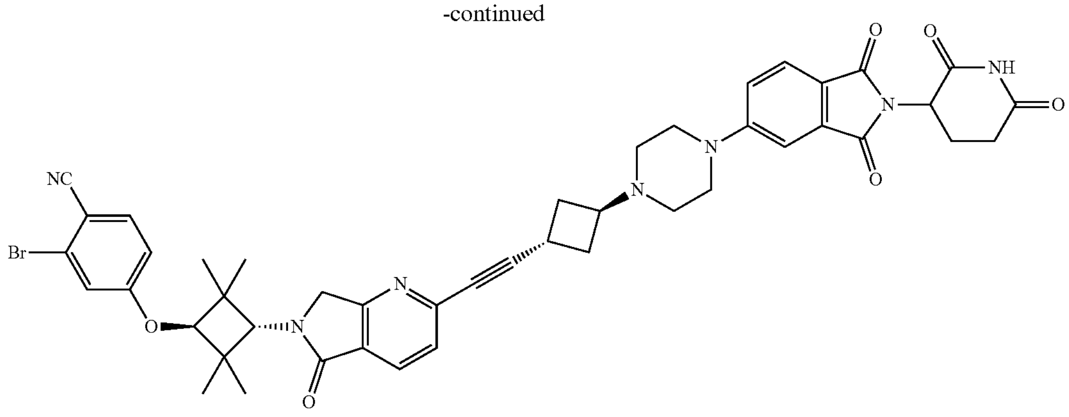
431
$^1H$ NMR (400 MHz, DMSO-$d_6$) δ 8.06 (d, J=7.9 Hz, 1H), 7.88 (d, J=8.7 Hz, 1H), 7.69 (d, J=8.5 Hz, 1H), 7.59 (d, J=7.9 Hz, 1H), 7.42 (d, J=2.4 Hz, 1H), 7.36 (s, 1H), 7.28 (d, J=8.8 Hz, 1H), 7.10 (dd, J=8.8, 2.4 Hz, 1H), 5.08 (dd, J=12.9, 5.3 Hz, 1H), 4.81 (s, 2H), 4.54 (s, 1H), 4.34 (s, 1H), 3.46 (s, 4H), 3.28-3.20 (m, 1H), 3.18-3.05 (m, 1H), 2.96-2.81 (m, 1H), 2.66-2.53 (m, 2H), 2.43-2.35 (m, 6H), 2.28-2.24 (m, 2H), 2.08-1.94 (m, 1H), 1.40 (s, 6H), 1.16 (s, 6H). MS: calcd. for $C_{45}H_{44}BrN_7O_6$ $[M+H]^+$: 858.3; found: 858.2.
432: 2-chloro-4-((1R,3r)-3-(2-(((1r,4R)-4-(4-(2-(2,6-dioxopiperidin-3-yl)-1-oxoisoindolin-5-yl)piperazin-1-yl)cyclohexyl)ethynyl)-5-oxo-5,7-dihydro-6H-pyrrolo[3,4-b]pyridin-6-yl)-2,2,4,4-tetramethylcyclobutoxy)benzonitrile
432
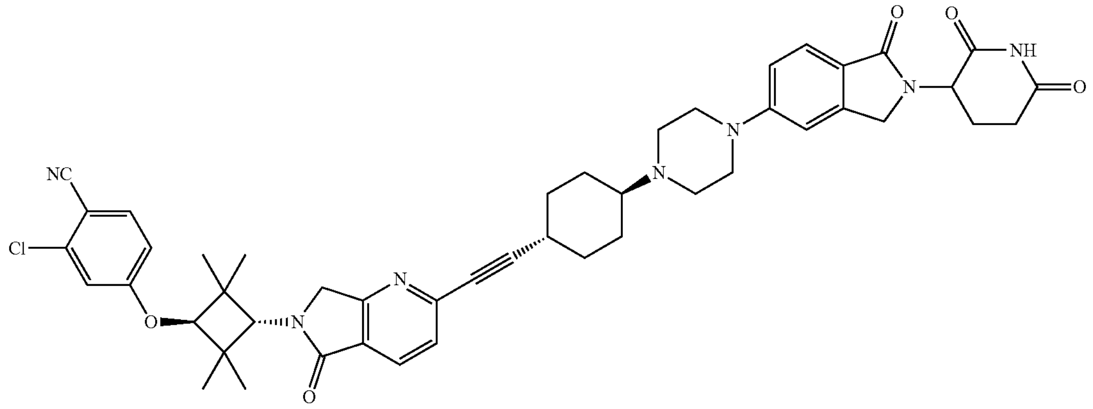
LCMS for $C_{47}H_{51}ClN_7O_5$ $[M+H]^+$ m/z 828.

433: (2S,4R)-1-((S)-2-(2-((5-((2-((1r,3r)-3-(3-bromo-4-cyanophenoxy)-2,2,4,4-tetramethylcyclobutyl)-1-oxoisoindolin-5-yl)amino)pentyl)oxy) acetylamino)-3,3-dimethylbutyryl)-4-hydroxy-N-((S)-1-(4-(4-methylthiazole5-yl)phenyl)ethyl) pyrrolidinyl-2-carboxamide

433

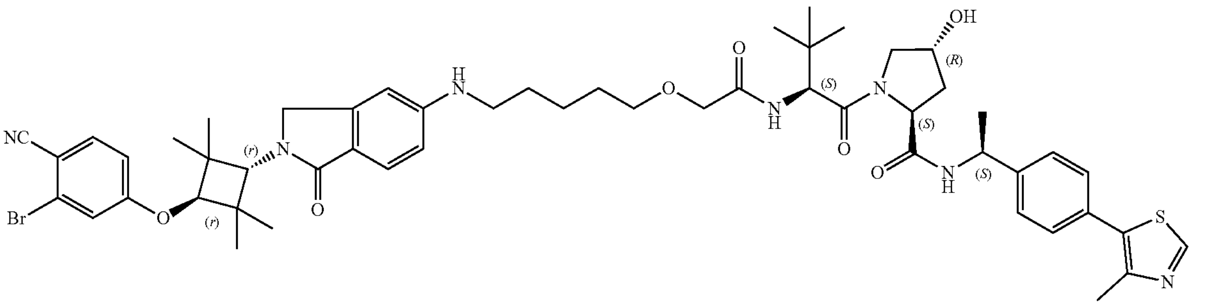

LCMS for $C_{53}H_{67}BrN_7O_5S$ $[M+H]^+$ m/z 1024.

434: (3R,5S)-1-((S)-2-(2-((5-((2-((1r,3r)-3-(3-bromo-4-cyanophenoxy)-2,2,4,4-tetramethylcyclobutyl)-1-isoindoline-5-amino)pentanyl)oxy)acetamido)-3,3-dimethylbutyryl)-5-(((S)-1-(4-(4-methylthiazol-5-phenyl)ethyl)carbamoyl) pyrrolidinyl-3-acetate

434

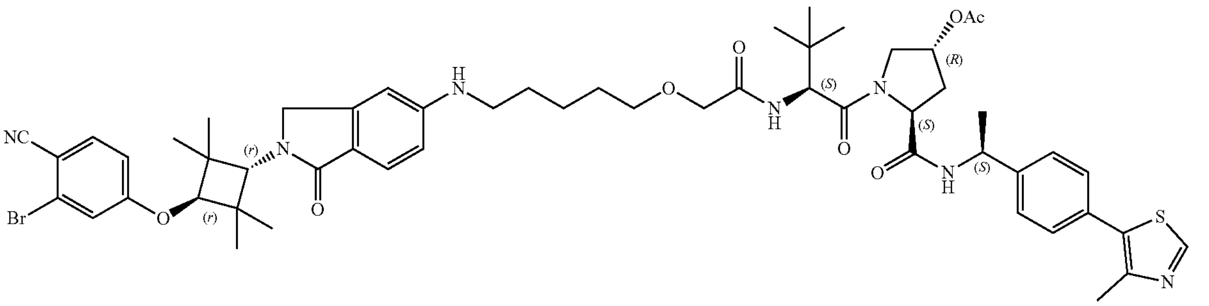

$^1H$ NMR (400 MHz, DMSO-$d_6$) δ 8.98 (s, 1H), 8.46 (d, J=7.7 Hz, 1H), 7.86 (d, J=8.7 Hz, 1H), 7.39 (m, 6H), 7.08 (dd, J=8.8, 2.4 Hz, 1H), 6.62 (m, 2H), 6.33 (t, J=5.2 Hz, 1H), 5.20 (s, 1H), 4.89 (m, 1H), 4.61 (s, 2H), 4.49 (s, 1H), 4.45 (m, 2H), 4.25 (s, 1H), 3.91 (m, 3H), 3.77 (dd, J=11.8, 3.9 Hz, 1H), 3.50 (dd, J=15.0, 8.6 Hz, 2H), 3.30 (s, 1H), 3.08 (m, 2H), 2.45 (s, 3H), 2.27 (m, 1H), 2.00 (s, 3H), 1.96 (m, 1H), 1.59 (dd, J=13.8, 7.0 Hz, 4H), 1.45 (m, 2H), 1.36 (s, 6H), 1.34 (s, 3H), 1.12 (s, 6H), 0.95 (s, 9H). LC/MS ($ESI^+$) calcd for $C_{55}H_{68}BrN_7O_8S$ ($[M+H]^+$) m/z 1066.4; found 1066.4.

435: (2R,4R)-1-((S)-2-(2-((6-(4-(((1r,3r)-3-(3-chloro-4-cyanophenoxy)-2,2,4,4-tetramethylcyclobutyl)(methoxy)benzamido)hex-5-yn-1-)oxy) acetamido)-3,3-dimethylbutyryl)-4-hydroxy-N-((S)-1-(4-(4-methylthiazol-5-)phenyl)ethyl) tetrahydropyrrole-2-amide

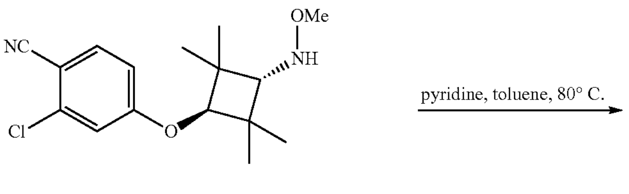

-continued

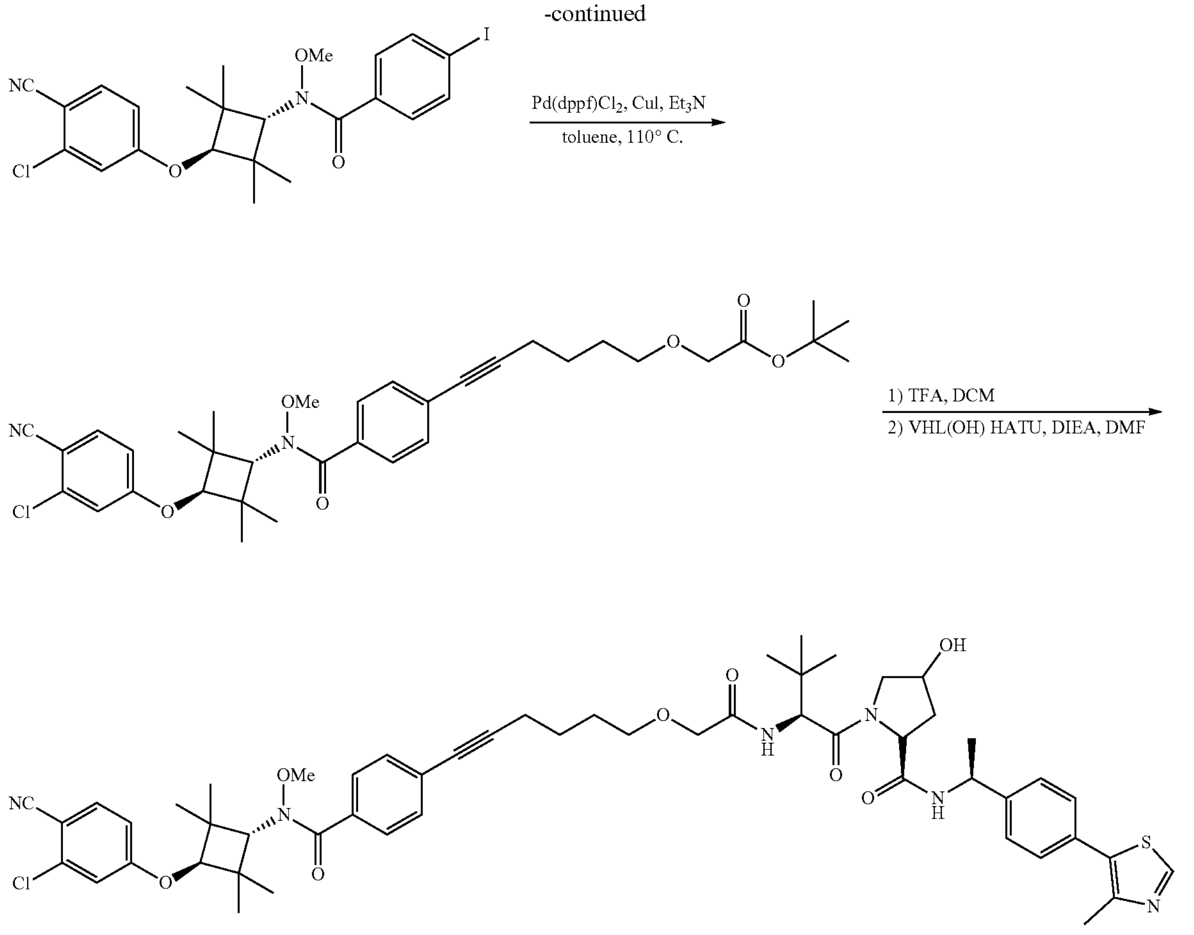

434

Step 1: 2-Chloro-4-((1r,3r)-3-(methoxyamino)-2,2,4,4-tetramethylcyclobutyl) benzonitrile was dissolved in toluene, to which were added methyl p-iodobenzoate and pyridine, and then the mixture was stirred overnight at 60° C. After the reaction was completed, the reaction was quenched with 0.5 N hydrochloric acid, and the resultant solution was extracted with ethyl acetate. The organic layer was successively washed with the saturated solution of sodium bicarbonate, water, and the saturated NaCl solution, dried, concentrated, and purified by column chromatography, to provide the product (100 mg, yield 12%). LC/MS (ESI$^+$) calcd for $C_{23}H_{25}ClIN_2O_3$ ([M+H]$^+$) m/z 539.1; found 539.1.

Step 2: Synthesis of intermediate t-butyl 2-((6-(4-(((1r,3r)-3-(3-chloro-4-cyanophenoxy)-2,2,4,4-tetramethylcyclobutyl)(methoxy)benzamido)hex-5-yn-1-yl) oxy)acetate The above-obtained product N-((1r,3r)-3-(3-chloro-4-cyanophenoxy)-2,2,4,4-tetramethylcyclobutyl)-4-iodo-N-methoxybenzamide, t-butyl 2-(hex-5-yn-1-oxy)acetate. PbdppfCl$_2$, CuI, and Et$_3$N were dissolved in toluene, and then the mixture was stirred 24 h at 110° C. Once the system was cooled, the reaction solution was filtered through a pad of celite. The filter cake was rinsed with ethyl acetate. The filtrate was successively washed with the dilute HCl solution, the saturated solution of sodium bicarbonate, water, and the saturated NaCl solution, dried, concentrated, and purified by column chromatography, to provide the product (56 mg, yield 49%). LC/MS (ESI$^+$) calcd for $C_{35}H_{44}ClN_2O_6$ ([M+H]$^+$) m/z 623.3; found 623.3.

Step 3: Synthesis of final product: (2R,4R)-1-((S)-2-(2-((6-(4-(((1r,3r)-3-(3-chloro-4-cyanophenoxy)-2,2,4,4-tetramethylcyclobutyl)(methoxy)benzamido)hex-5-yn-1-yl) oxy)acetamido)-3,3-dimethylbutyryl)-4-hydroxy-N-((S)-1-(4-(4-methylthiazol-5-)phenyl)ethyl)tetrahydropyrrole-2-amide The product obtained above t-butyl 2-((6-(4-(((1r,3r)-3-(3-chloro-4-cyanophenoxy)-2,2,4,4-tetramethylcyclobutyl) (methoxy)benzamido)hex-5-yn-1-yl)oxy)acetate was dissolved in dichloromethane, to which was added trifluoroacetic acid, and the mixture was stirred at room temperature overnight. TLC analysis indicated the disappearance of the raw material, and then the reaction solution was concentrated, which was dissolved in DMF. Then, excess DIEA was added, followed by addition of VHL(OH) and HATU, and the mixture was stirred at room temperature for 4 h. After completion of the reaction, the reaction was quenched with 0.5 N dilute hydrochloric acid solution, and then extracted with ethyl acetate. The organic layer was successively washed with the saturated solution of sodium bicarbonate, water, and the saturated NaCl solution, dried, concentrated, and purified by column chromatography, to provide the product (9 mg, yield 47%). $^1$H NMR (400 MHz, DMSO-$d_6$) δ 8.96 (s, 1H), 8.44 (d, J=7.7 Hz, 1H), 7.84 (d, J=8.7 Hz, 1H), 7.41 (m, 7H), 7.08 (dd, J=8.8, 2.4 Hz, 1H), 6.64 (m, 2H), 6.33 (t, J=5.2 Hz, 1H), 5.19 (s, 1H), 4.88 (m, 1H), 4.52 (s, 1H), 4.25 (s, 1H), 3.88 (m, 3H), 3.78 (dd, J=11.8, 3.9 Hz, 1H), 3.67 (s, 3H), 3.58 (m, 1H), 3.52 (dd, J=15.0, 8.6 Hz, 2H), 3.07 (m, 2H), 2.26 (m, 1H), 2.00 (s, 3H), 1.95 (m, 1H), 1.58 (dd, J=13.8, 7.0 Hz, 4H), 1.44 (m, 2H), 1.35 (s, 6H), 1.33 (s, 3H), 1.11 (s, 6H), 0.94 (s, 9H). LC/MS ($ESI^+$) calcd for $C_{54}H_{66}ClNO_8S$ ($[M+H]^+$) m/z 993.4; found 993.4.

In the following, the beneficial effect of the present invention was demonstrated by experimental examples.

Experimental Example 1 the Inhibitory Activity of the Compound According to the Present Invention on the Proliferation of Prostate Cancer Cells (1) Experimental Materials and Instruments:

LNCaP/AR cell line (provided by Sichuan Kangcheng Biotechnology Co., Ltd.)
Fetal bovine serum FBS (Gibco, Cat. No. 10099-141)
0.01M PBS (Biosharp, Cat. No. 162262)
RIPM1640 media (Hyclone, Cat. No. 308090.01)
Penicillin-Streptomycin (Hyclone, Cat. No. SV30010)
Cell counting kit-8 (Signalway Antibody, Cat. No. CP002)
DMSO (Sigma, Cat. No. D5879)
Centrifuge Tube, 15 ml (Excell Bio, Cat. No. CSU15-0001)
Cell Culture Dish, (Excell Bio, Cat. No. CS016-0128)
96-well cell culture cluster (Corning, Cat. No. 3599)
Microplate reader (Thermo Multiskan MK3 type)

(2) Experimental Methods:

a. Preparation of Buffer

Cell culture medium: RIPM1640 media, 10% FBS, 1% Pen Strep;

PBS buffer: PBS powder was dissolved in 2 L of ultrapure water and sterilized.

b. Experimental Procedures

1) LNCaP/AR cells were subcultured in cell culture media, and then the cells in good growth condition were seeded in a 96-well plate at 80 μL/well (1000 cells/well), and cultured overnight in a 37° C., 5% $CO_2$ cell incubator.

2) The test compound was prepared into a 10 mM stock solution with dimethyl sulfoxide (DMSO). Prior to use, the solution was diluted 3 times with DMSO, and then diluted at a 3-fold gradient to obtain 9 serial concentrations. Then, each concentration of compound was diluted 200 times with the culture medium (to ensure that the DMSO concentration in the culture system was 0.1%), and two holes was set for each concentration. 20 μL of the diluted compound solution was added to the cell culture well (with a final concentration of 10 μM, 3.3 μM, 1.1 μM . . . ), and then the plate was gently shaken to mix. In addition, the experiment included 3 negative control wells only containing cells and 3 blank control wells only containing culture medium (6 wells were each added with DMSO diluted 200 times with 20 μL of culture medium).

c. Result detection:

1) After culturing for 6 days, 10 μL of CCK-8 was added to each well, and the plate was further incubated for 1 h in a 37° C., 5% $CO_2$ cell incubator.

2) The absorbance (OD value) was measured at 450 nm with a multifunctional microplate reader.

3) The data was analyzed by the Dose-response-inhibition equation in the software GraphPad Prism5, and the $IC_{50}$ value was obtained.

(3) Experimental results:

The inhibitory results of the compounds, obtained in the examples of the present invention, on the proliferation of LNCap/AR cells were listed in Table 1. It could be seen that the compounds of the present invention could effectively inhibit the proliferation of LNCap/AR cells, and most of the compounds had $IC_{50}$ values of even <0.1 μM against LNCap/AR cells.

TABLE 1

The inhibitory activities of the compounds according to the present invention on the proliferation of LNCap/AR cells.

| Compound | $IC_{50}$ (μM) |
|---|---|
| 1 | D |
| 3 | B |
| 4 | A |
| 5 | A |
| 6 | A |
| 7 | A |
| 9 | A |
| 10 | B |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | B |
| 31 | A |
| 32 | A |
| 33 | B |
| 34 | A |
| 35 | A |
| 37 | A |
| 38 | A |
| 39 | A |
| 40 | B |
| 41 | A |
| 42 | A |
| 43 | A |
| 44 | B |
| 45 | D |
| 46 | A |
| 47 | A |
| 48 | A |
| 49 | A |
| 51 | B |
| 52 | B |
| 53 | B |
| 54 | D |
| 55 | B |
| 57 | D |
| 59 | D |
| 60 | D |
| 198 | B |
| 199 | D |
| 200 | D |
| 201 | D |
| 202 | B |
| 203 | D |
| 204 | A |
| 205 | A |
| 210 | D |
| 211 | B |

TABLE 1-continued

The inhibitory activities of the compounds according to the present invention on the proliferation of LNCap/AR cells.

| Compound | $IC_{50}$ (μM) |
|---|---|
| 213 | D |
| 214 | A |
| 215 | D |
| 216 | B |
| 217 | D |
| 218 | D |
| 219 | C |
| 248 | B |
| 249 | B |
| 250 | B |
| 251 | B |
| 305 | C |
| 306 | D |
| 307 | C |
| 309 | B |
| 310 | D |
| 311 | D |
| 312 | B |
| 313 | A |
| 403 | A |
| 404 | A |
| 405 | D |
| 406 | B |
| 407 | A |
| 408 | B |
| 409 | A |
| 410 | A |
| 411 | A |
| 412 | A |
| 433 | D |
| 435 | C |

A: <0.1 μM,
B: 0.1-0.5 μM,
C: 0.5-1 μM,
D: >1 μM.

Experimental Example 2 Analysis of the Degradation Activity of the Compound According to the Present Invention on Androgen Receptor (AR) Protein by Enzyme-Linked Immunosorbent Assay (ELISA)

Experimental Materials:
Prostate cancer VCaP cells (ATCC. CRL-2876)
Charcoal stripped FBS (Gibco. Cat. No. 12676-029)
Metribolone(R1881) (Macklin Biochemical. CAS. No. 965-93-5)

0.01M PBS (Biosbarp. Cat. No. 162262)
DMEM/HIGH GLUCOSE (Hyclone. Cat. No. SH30243.01)
Penicillin-Streptomycin (Hyclone. Cat. No. SV30010)
DMSO (Sigma. Cat. No. D5879)
Centrifuge Tube. 15 ml (Excell Bio. Cat. No. CS015-0001)
Cell Culture Dish (Excell Bio. Cat. No. CS016-0128)
PathScan® Total Androgen Receptor Sandwich ELISA Kit (CST. Cat. No. 12850C)
Experimental Methods:
1. Preparation of Buffer

| | | | | | |
|---|---|---|---|---|---|
| Cell culture medium: DMEM/HIGH GLUCOSE meida, 10% CSS-FBS, 1% Pen Strep, 0.1 nM R1881 | PBS buffer: PBS powder was dissolved in 2 L of ultrapure water and sterilized. | Cell lysis buffer: cell lysis buffer was diluted with purified water in a ratio of 1:10. | 1× washing buffer: Washing buffer was diluted with purified water in a ratio of 1:20. | Detection of antibodies: the detection antibody was dissolved in the diluent of detection antibody (green solution) and mixed well | HRP-labeled secondary antibody: the antibody was dissolved in HRP diluent (red solution) and mixed well |

2. Experimental Procedures

1) After VCaP cells were subcultured in cell culture medium, the cells in good growth condition were inoculated in a 96 well plate at 80 al/well ($3\times10^4$ cells/well). The plate was cultured in a 5% $CO_2$ cell incubator at 37° C. for 3 days until the cells adhered to the wall.

2) The test compound was prepared into 10 mM stock solution with dimethylsulfoxide (DMSO). Prior to use, the stock solution was diluted with cell culture medium, and 20 μl of the diluted compound solution was transferred to a cell culture well, to obtain 8 serial concentrations (300, 100, 10, 3, 1, 0.3, 0.1, 0.03 nM), one well for each concentration. The plate was gently shaken and mixed. In addition, negative control wells (only containing culture medium) and positive control wells (only containing cells and DMSO) were set.

3) After the cells were cultured in an incubator for 16 h. the medium was removed and the cells were rinsed once with ice cold 1×PBS.

4) PBS was removed, and then 50 μl of ice-cold 1× cell lysis buffer was added to each well of the cell culture plate. After the plate was incubated on ice for 15 min. the plate was tapped to mix.

5) 115 μl of sample diluent was added to a new 96 well plate, and then 5 μl supernatant of the cell lysate was transferred from the cell culture plate to the sample diluent and shaken to mix.

6) 100 μl of diluted sample was added into the plate for ELISA, and the ELISA plate was sealed with plastic film. The plate was incubated in a 37° C. incubator for 2 h.

7) The plastic film was gently removed, and 200 μl of 1× washing buffer was added to each well. The plate was shaken for 5 min. and the medium was poured out. The plate was blotted against clean paper towel, followed by washing 4 times.

8) 100 μl of fresh detection antibody (green) was added to each well of an ELISA plate, and after sealing with plastic film, the plate was cultured in an incubator at 37° C. for 1 h.

9) The adhesive film was gently removed, and the detection antibody was poured out followed by blotting with paper towel. 200 μl of 1× washing buffer was added to each well. The plate was shaken for 5 min. The washing buffer was poured out, and the plate was blotted with paper towel and washed four times.

10) 100 μl of fresh HRP-labeled secondary antibody (red) was added to each well of an ELISA plate, and after scaling with plastic film, the plate was cultured in an incubator at 37° C. for 30 min.

11) The adhesive film was gently removed, and the secondary antibody was poured out followed by blotting with paper towel. 200 μl of 1× washing buffer was added to each well. The plate was shaken for 5 min. The washing buffer was poured out, and the plate was blotted with paper towel and washed four times.

12) 100 μl of TMB substrate was added to each well of an ELISA plate, and the plate was cultured in 37° C. incubator for 5 min.

13) 100 μl of stop solution was added to each well of an ELISA plate, and the plate was gently tapped for several seconds.

3. Result Reading

The bottom of each well was wiped with a lint-free thin cloth. The absorbance was read at 450 nm within 30 min after adding the stop solution. Using the formula: residual AR %=100*(OD value of test well−OD value of blank control well)/(OD value of positive control well−OD value of blank control well), the data were analyzed by the dose-response equation in the software GraphPad Prism5, to obtain $DC_{50}$ and $D_{max}$ values. $DC_{50}$ is the compound concentration corresponding to degradating 50% of the target protein. $D_{max}$ is the percentage of the target protein that can be degraded to the greatest extent.

Experimental Results:

The degradation activity of the compound according to the present invention on androgen receptor (AR) at the concentration of 100 nm was shown in Table 2, in which % degradation was the percentage of degraded AR. The degradation activity of the compound according to the present invention on androgen receptor (AR) at concentration gradients was shown in Tables 3-1 and 3-2. In Tables 3-1 and 3-2, $DC_{50}$ was the compound concentration when androgen receptor was degraded by 50%. $D_{max}$ was the percentage of androgen receptor (AR) that can be degraded to the greatest extent.

As shown, the compound of the present invention could effectively degrade androgen receptor, and $DC_{50}$ values of most compounds against androgen receptor were less than 0.3 μM. and some were even <10 nM, $D_{max}$ values of most compounds against androgen receptor were more than 40%, and some were even >80%

TABLE 2

Degradation activity of compound on androgen receptor (AR) at the concentration of 100 nM.

| Compound | % degradation |
|---|---|
| 1 | D |
| 2 | D |
| 3 | B |
| 4 | C |
| 5 | C |
| 6 | B |
| 7 | B |
| 8 | C |
| 9 | A |
| 10 | C |
| 11 | B |
| 12 | B |
| 13 | B |
| 14 | B |
| 15 | C |
| 16 | C |
| 17 | B |
| 18 | A |
| 19 | D |
| 20 | C |
| 22 | C |
| 23 | C |
| 24 | B |
| 25 | C |
| 26 | D |
| 27 | B |
| 28 | C |
| 31 | B |
| 32 | B |
| 33 | 0 |
| 35 | B |
| 36 | C |
| 37 | B |
| 38 | B |
| 39 | C |
| 40 | C |
| 42 | B |
| 43 | B |
| 44 | B |
| 46 | C |
| 47 | B |
| 48 | A |
| 49 | C |
| 51 | B |
| 54 | C |
| 55 | C |
| 57 | D |
| 59 | D |
| 60 | D |
| 197 | A |
| 198 | B |
| 199 | D |
| 200 | B |
| 201 | B |
| 203 | D |
| 204 | B |
| 206 | C |
| 210 | D |
| 212 | C |
| 213 | C |
| 215 | D |
| 216 | A |
| 217 | D |
| 250 | D |

A: >80%,
B: 79%-50%,
C: 49%-25%,
D: <25%

TABLE 3-1

$DC_{50}$ and $D_{max}$ for the degradation of compounds on androgen receptor (AR).

| Compound | $DC_{50}$ (nM) | $D_{max}$ (%) |
|---|---|---|
| 75 | A | ++++ |
| 76 | A | ++++ |
| 77 | A | ++++ |
| 78 | A | ++++ |
| 79 | B | ++++ |
| 80 | B | +++ |
| 81 | A | ++++ |
| 82 | A | ++++ |
| 83 | D | + |
| 84 | A | ++++ |
| 85 | B | ++++ |
| 86 | C | +++ |

TABLE 3-1-continued

DC50 and $D_{max}$ for the degradation of compounds on androgen receptor (AR).

| Compound | $DC_{50}$ (nM) | $D_{max}$ (%) |
|---|---|---|
| 87 | C | ++ |
| 88 | A | ++++ |
| 89 | A | ++++ |
| 90 | B | +++ |
| 91 | D | + |
| 92 | A | ++++ |
| 93 | B | +++ |
| 94 | B | +++ |
| 95 | B | +++ |
| 96 | A | ++++ |
| 97 | A | ++++ |
| 112 | D | + |
| 113 | A | ++++ |
| 114 | A | ++++ |
| 115 | A | ++++ |
| 116 | A | ++++ |
| 117 | C | ++++ |
| 119 | A | ++++ |
| 121 | A | ++++ |
| 122 | A | ++++ |
| 123 | A | ++++ |
| 124 | A | ++++ |
| 125 | A | ++++ |
| 126 | A | ++++ |
| 127 | A | ++++ |
| 128 | B | +++ |
| 129 | A | ++++ |
| 130 | A | ++++ |
| 131 | B | +++ |
| 132 | B | +++ |
| 133 | D | + |
| 135 | D | + |
| 147 | B | +++ |
| 148 | D | ++ |
| 149 | D | + |
| 150 | D | + |
| 151 | A | ++++ |
| 152 | B | ++++ |
| 153 | A | ++++ |
| 154 | A | ++++ |
| 155 | A | ++++ |
| 166 | A | ++++ |
| 168 | A | ++++ |
| 169 | B | +++ |
| 170 | A | ++++ |
| 171 | B | ++++ |
| 186 | A | ++++ |
| 187 | A | ++++ |
| 188 | A | ++++ |
| 189 | A | ++++ |
| 190 | A | ++++ |
| 191 | A | ++++ |
| 192 | A | ++++ |
| 193 | A | ++++ |
| 194 | A | ++++ |
| 196 | A | ++++ |
| 233 | A | ++++ |
| 234 | A | ++++ |
| 235 | A | ++++ |
| 236 | A | ++++ |
| 237 | C | ++ |
| 238 | B | ++ |
| 239 | B | +++ |
| 240 | B | +++ |
| 241 | A | ++++ |
| 242 | A | ++++ |
| 243 | A | ++++ |
| 244 | A | ++++ |
| 245 | B | +++ |
| 246 | B | +++ |
| 247 | A | ++++ |
| 261 | A | ++++ |
| 262 | A | ++++ |
| 263 | A | +++ |
| 264 | B | +++ |

TABLE 3-1-continued $DC_{50}$ and $D_{max}$ for the degradation of compounds on androgen receptor (AR).

| Compound | $DC_{50}$ (nM) | $D_{max}$ (%) |
|---|---|---|
| 265 | B | +++ |
| 266 | B | ++++ |
| 267 | A | ++++ |
| 268 | A | ++++ |
| 269 | A | ++++ |
| 270 | A | ++++ |
| 271 | A | ++++ |
| 272 | A | ++++ |
| 273 | B | +++ |
| 274 | A | ++++ |
| 275 | A | ++++ |
| 276 | A | ++++ |
| 277 | B | ++++ |
| 278 | A | ++++ |
| 279 | A | ++++ |
| 280 | B | ++++ |
| 281 | A | ++++ |
| 282 | A | ++++ |
| 283 | A | ++++ |
| 284 | A | ++++ |
| 285 | A | ++++ |
| 286 | B | +++ |
| 287 | A | ++++ |
| 288 | A | ++++ |
| 322 | A | +++ |
| 325 | A | ++++ |
| 340 | A | ++++ |
| 341 | B | +++ |
| 343 | D | ++ |
| 349 | B | ++++ |
| 350 | C | ++ |
| 351 | A | ++++ |
| 352 | D | ++ |
| 353 | D | ++ |
| 355 | A | ++++ |
| 357 | A | ++++ |
| 358 | B | +++ |
| 359 | B | +++ |
| 360 | B | +++ |
| 361 | B | +++ |
| 362 | A | ++++ |
| 363 | B | +++ |
| 364 | A | ++++ |
| 365 | B | ++++ |
| 366 | A | ++++ |
| 367 | C | ++ |
| 368 | C | ++ |
| 369 | B | +++ |
| 370 | C | ++ |
| 371 | B | ++++ |
| 372 | D | + |
| 373 | D | + |
| 374 | A | ++++ |
| 375 | A | ++++ |
| 376 | D | ++ |
| 377 | A | ++++ |
| 378 | D | + |
| 379 | B | ++++ |
| 380 | B | +++ |
| 381 | B | ++++ |
| 382 | B | ++++ |
| 383 | B | ++++ |
| 384 | A | +++ |

$DC_{50}$: A: <10 nM, B: 10-100 nM, C: 0.1-0.3 μM, D: >0.3 μM $D_{max}$: ++++: >80%, +++: 80%-60%, ++: 60%-40%, +: <40%

TABLE 3-2

DC$_{50}$ and D$_{max}$ for the degradation of compounds on androgen receptor (AR).

| Compound | DC$_{50}$ (nM) | D$_{max}$ (%) |
|---|---|---|
| 385 | C | +++ |
| 386 | D | ++ |
| 387 | D | + |
| 388 | C | ++ |
| 389 | D | + |
| 390 | A | +++ |
| 391 | C | ++++ |
| 392 | B | ++++ |
| 393 | B | ++++ |
| 394 | B | +++ |
| 395 | C | ++ |
| 396 | B | ++++ |
| 397 | B | ++++ |
| 398 | B | ++++ |
| 399 | A | ++++ |
| 400 | A | ++++ |
| 401 | B | ++++ |
| 402 | A | ++++ |
| 106 | D | + |
| 107 | A | ++++ |
| 158 | A | ++++ |
| 413 | A | ++++ |
| 414 | A | ++++ |
| 415 | A | ++++ |
| 416 | A | ++++ |
| 417 | A | ++++ |
| 419 | A | ++++ |
| 420 | A | ++++ |
| 429 | A | ++++ |
| 430 | C | +++ |

DC$_{50}$: A: <10 nM, B: 10-100 nM, C: 0.1-0.3 μM, D: >0.3 μM
D$_{max}$: ++++: >80%, +++: 80%-60%, ++: 60%-40%, +: <40%

Experimental Example 3. Determination of the Degradation Activity of the Compound on Androgen Receptor (AR) Protein by Western Blot Experimental Materials:

Prostate cancer VCaP cells (ATCC, CRL-2876)

FBS (Gibco, Cat. No. 10099-141)

0.01M PBS (Biosharp, Cat. No. 162262)

Metribolone (R1881) (Macklin Biochemical. CAS. No. 965-93-5)

DMEM/HIGH GLUCOSE (Hyclone. Cat. No. SH30243.01)

Penicillin-Streptomycin (Hyclone, Cat. No. SV30010)

DMSO (Sigma, Cat. No. D5879)

Centrifuge tube. 15 ml (Excell Bio, Cat. No. CS015-0001)

Cell culture disk, (Excell Bio, Cat. No. CS016-0128)

6-well cell culture cluster (Corning, Cat. No. 3516)

RIPA lysate buffer (Beyotime, Cat. No. P0013B)

Protein loading buffer (Beyotime, Cat. No. P0015L)

BCA protein assay kit (Beyotime. Cat. No. P0012)

SDS-PAGE gel preparation kit (Chengdu Baihe Technology Co. Ltd. Cat. No. PG112)

Anti-β-Actin rabbit mAb (CST. Cat. No. 4970)

Androgen Receptor (D6F11) XP Rabbit mAb (CST, Cat. No. 5153)

Peroxidase Affinipure (HRP) Goat Anti-Rabbit IgG (Zen Bioscience, Cat. No. 511203)

TBST (Biosharp. Cat. No. BL601A)

ECL chemiluminescence kit (Beyotime, Cat. No. P0018)

Experimental Methods:

1. Preparation of Suffer

| | | |
|---|---|---|
| Cell culture medium: DMEM/HIGH GLUCOSE medium, 10% FBS, 1% Pen Strep, 0.1 nM R1881 | PBS buffer: PBS powder was dissolved in 2 L of ultrapure water and sterilized. | Cell lysate: Protease inhibitor was added in RIPA lysate buffer in a ratio of 1:1000 prior to use. |

2. Experimental Procedures:

1) VCaP cells were subcultured in cell culture media, and then the cells in good growth condition were seeded in a 12-well plate at 1 ml/well ($5\times10^5$ cells/well), and cultured overnight in a 37° C., 5% $CO_2$ cell incubator.

2) The test compound was prepared into a 10 mM stock solution with dimethyl sulfoxide (DMSO). Prior to use, the solution was diluted 3 times with DMSO. 2 μL of the diluted compound solution was added to the cell culture well (ensuring that the DMSO concentration in the culture system was 0.1%), and two wells were set for each concentration. The plate was gently shaken to mix. In addition, the experiment included negative control wells (containing equal amount of DMSO) and positive control wells.

3) After culturing 16 h. the cells were lysed with RIPA cell lysate, and the protein was extracted. The protein concentration was measured with BCA kit. 5-fold concentrated protein loading buffer was added, and after heated at 100° C. for 5 min. the sample was stored at −20° C.

4) for each well, 30 μg of protein was loaded on polyacrylamide gel for electrophoresis.

5) The protein was transferred from polyacrylamide gel to PVDF membrane, and then 5% skim milk was added to close for 1 h at room temperature. The first antibody (Androgen Receptor (D6F11) XP Rabbit mAb and Anti-β-Actin Rabbit mAb) was added and incubated overnight at 4° C. The membrane was washed with TBST solution three times. 10 min for each time. The secondary antibody (horseradish peroxidase labeled goat anti mouse IgG) was added and incubated at room temperature for 2 h, and then the membrane was washed with TBST solution three times. 10 min for each time.

3. Detection of Results:

Finally, ECL chemiluminescence solution was added, and then photos were taken with automatic chemiluminescence instrument to collect pictures for analysis.

Experimental Results:

The degradation activity of the compound according to the present invention on androgen receptor (AR) at the concentration of 100 nM was measured by Western blot. As shown in Table 4, % degradation was the percentage of degraded AR. As shown, the compound of the present invention could effectively degrade androgen receptors.

TABLE 4

Degradation activity of compounds according to the present invention on AR.

| Compound | % degradation |
|---|---|
| 58 | C |
| 59 | D |
| 61 | A |
| 62 | B |
| 63 | B |
| 64 | B |
| 67 | D |

TABLE 4-continued

Degradation activity of compounds according to the present invention on AR.

| Compound | % degradation |
|---|---|
| 69 | D |
| 71 | A |
| 72 | C |
| 73 | A |
| 74 | A |
| 100 | B |
| 101 | C |
| 102 | B |
| 103 | A |
| 105 | B |
| 109 | D |
| 111 | D |
| 118 | C |
| 120 | D |
| 137 | B |
| 138 | C |
| 139 | A |
| 140 | C |
| 141 | A |
| 142 | A |
| 143 | A |
| 145 | A |
| 146 | A |
| 157 | A |
| 158 | A |
| 159 | B |
| 160 | D |
| 161 | B |
| 162 | A |
| 163 | A |
| 164 | A |
| 165 | A |
| 167 | B |
| 172 | D |
| 173 | D |
| 174 | D |
| 175 | D |
| 176 | B |
| 177 | B |
| 178 | B |
| 179 | C |
| 180 | A |
| 181 | B |
| 182 | B |
| 183 | A |
| 184 | A |
| 185 | A |
| 205 | D |
| 211 | D |
| 214 | B |
| 218 | D |
| 219 | C |
| 220 | D |
| 221 | C |
| 222 | A |
| 223 | A |
| 224 | B |
| 225 | B |
| 226 | B |
| 227 | C |
| 228 | A |
| 229 | A |
| 230 | A |
| 231 | A |
| 232 | A |
| 248 | D |
| 249 | D |
| 250 | D |
| 251 | C |
| 252 | C |
| 253 | B |
| 254 | B |
| 255 | B |
| 256 | C |
| 257 | C |
| 258 | C |
| 259 | A |
| 260 | A |
| 289 | A |
| 290 | B |
| 291 | B |
| 292 | D |
| 293 | B |
| 294 | C |
| 295 | C |
| 296 | D |
| 297 | C |
| 298 | D |
| 299 | D |
| 300 | D |
| 301 | B |
| 302 | D |
| 303 | D |
| 309 | C |
| 315 | D |
| 316 | C |
| 317 | B |
| 318 | B |
| 319 | D |
| 320 | B |
| 323 | D |
| 324 | C |
| 326 | B |
| 327 | B |
| 328 | B |
| 329 | B |
| 330 | B |
| 331 | C |
| 332 | B |
| 333 | B |
| 334 | A |

A: >80%,
B: 79%-50%,
C: 49%-25%,
D: <25%

FIG. 1 shows the Western blot results of compound 99 at different concentrations. It could be seen from the photos that the degradation activity of the compound according to the present invention on AR was in concentration-dependent manner, and the degradation activity increased with the increase of compound concentration.

Experiment Example 4 Experiment on Metabolic Stability of the Compound of the Present Invention 1. Materials and Instruments HPLC (Shimadzu). MS (API 4000 instrument from AB Inc (Canada) with an ESI interface), chromatographic column (ACE Excel 3 AQ 30×2.1 mm Column), human hepatic drug enzyme (Corning, Cat. #452117), phosphate buffer, ultrapure water, $MgCl_2$ solution, NADPH.

2. Methods and Results

10 μl of 20 mg/ml liver microsomes and 40 μl of 10 mM NADPH were added to the incubation tube. The final concentrations of liver microsomes and NADPH were 0.5 mg/mL and 1 mM, respectively. At the same time, a group without NADPH and only containing the same amount of ultrapure water was used as the control group. Then, 4 μl solution of control compound (verapamil) or test compound at the concentration of 200 μM was added. The final concentration of the compound was 2 μM. 50 μl of reaction solution was collected when incubating for 0 min, 15 min, 30 min, 45 min and 60 min. respectively, and 4-fold volume of ice acetonitrile was added to the solution to stop the reaction. After the sample was centrifuged for 40 min (3220 g), 100 μl of supernatant was taken out, to which was added 100 μl of ultrapure water, followed by mixing well for LC-MS/MS detection. Finally, the experimental parameters for metabolic stability of liver microsomes were calculated.

The experimental results showed that the compound of the present invention had good metabolic stability.

Experimental Example 5 Pharmacokinetics of the Compound of the Present Invention 1. Experimental Materials and Instruments:
   - LC-20AD high performance liquid chromatography (SHIMADZU, Japan)
   - API4000 triple quadrupole mass spectrometer (Applied Biosystem, USA)
   - PhenixWinnolin Pharmacokinetic software (Version 6.3, Certara, USA)
   - High speed freezing centrifuge (Thermo Fisher Scientific)
   - Analytical balance (Sartorius, SECURA225D-1CN)
   - Experimental animals: ICR mice (Chengdu Dossy Experimental Animals CO., LTD.)
   - DMSO (Sigma)
   - CMC-Na (Chengdu Kelong Chemical Co., Ltd)
   - Heparin (Chengdu Kelong Chemical Co., Ltd)
2. Experimental Methods and Results The test compound was accurately weighed according to the dosage, and then the solvent was added to the final volume of 10 ml. The solution was thoroughly mixed by ultrasonic vortex. A solution at the concentration of 0.5 mg/ml was prepared, and 0.2 ml of the prepared final solution was stored at −20° C. for concentration determination. Nine healthy adult ICR mice (20-30 g) were administered at a dosage of 0.2 ml/10 g by gavage after fasting overnight (free drinking water); before administration and 0.5 h, 1 h, 2 h, 4 h, 6 h, 8 h, 12 h and 24 h after administration, 0.1 ml of blood was collected from the posterior orbital venous plexus, centrifuged at 4° C. for 5 min to separate the plasma, and stored at −20° C. for detection. Then, the concentration of test compounds in plasma was determined by LC/MS/MS.

The experimental results showed that the compound of the present invention had good pharmacokinetics.

In summary, the present invention provided a class of compounds of formula (I), which could perform targeted degradation on androgen receptors in prostate cancer cells, and suppress proliferation of the prostate cancer cells, and show good metabolic stability and pharmacokinetic properties. The compound had good application prospect in preparation of targeted chimeras for protein degradation of androgen receptors and in the preparation of drugs for treating related diseases (including prostate cancer, breast cancer, Kennedy's disease) regulated by the androgen receptors.

The invention claimed is:

1. Compound of formula (I), or an isotopic compound thereof, or an optical isomer thereof, or a tautomer thereof, or a pharmaceutically acceptable salt thereof:

(I)

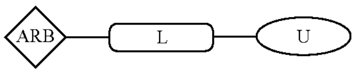

wherein, ARB is an androgen receptor recognition/binding part, L is the linking part, and U is a ubiquitin protease recognition/binding part; and the three parts are connected by chemical bonds;

wherein, said ARB is selected from the structure of the following formulas:

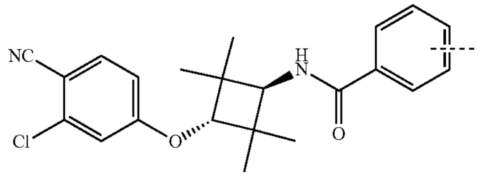

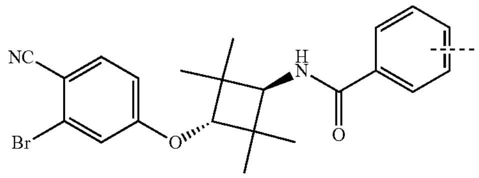

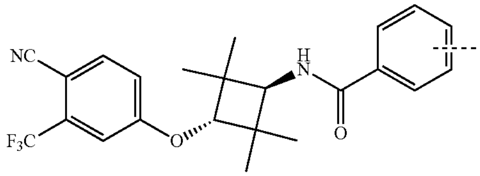

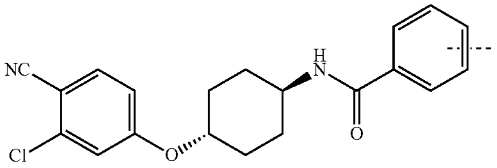

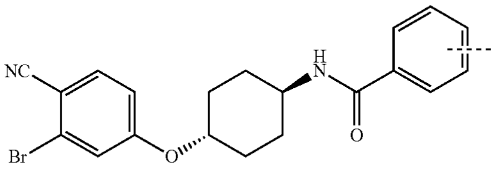

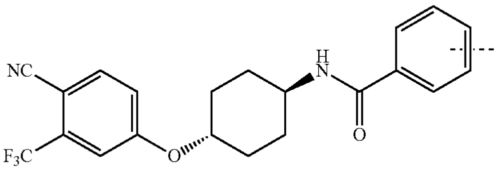

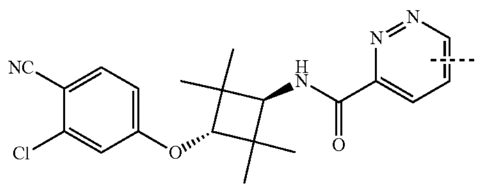

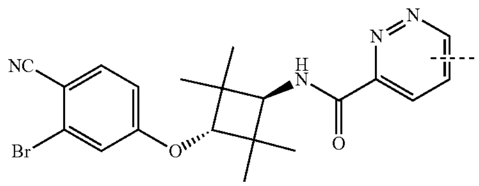

-continued
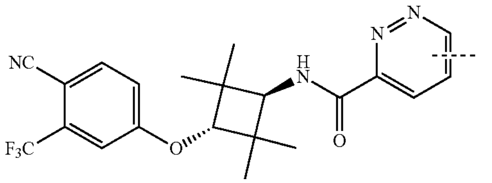
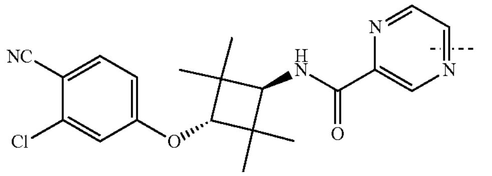
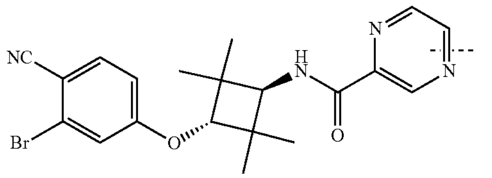
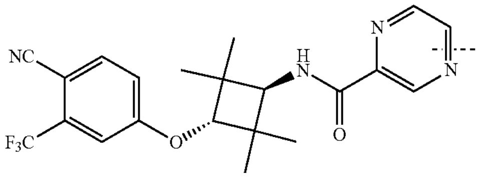
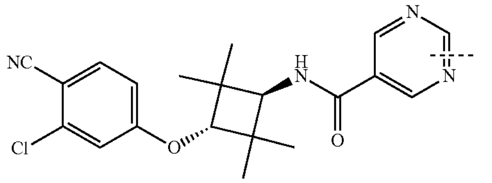
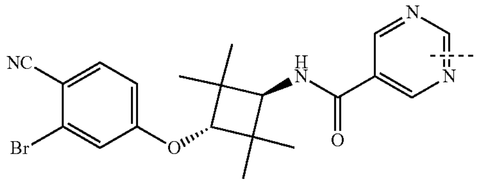
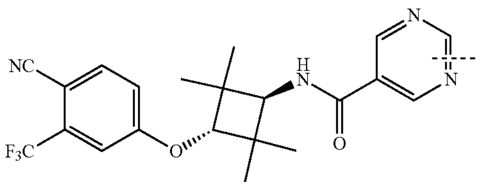
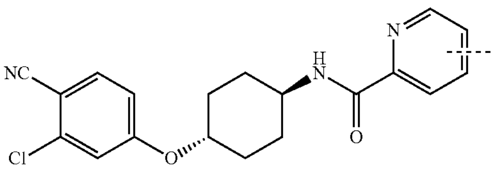
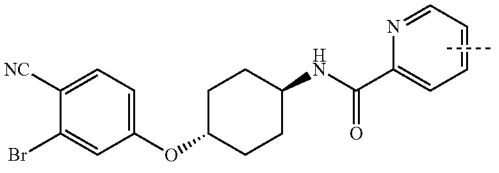
-continued
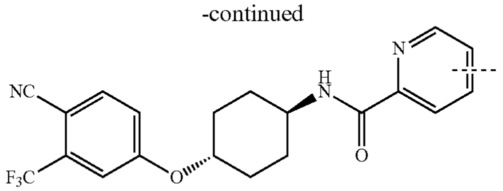
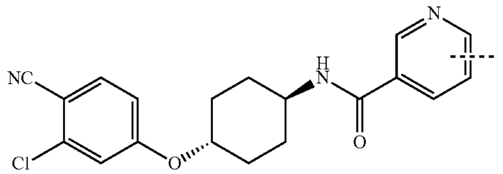
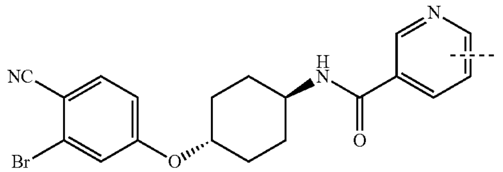
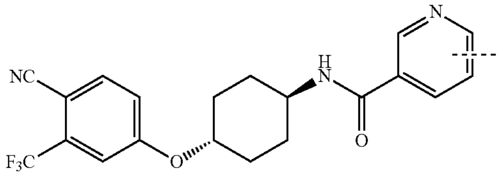
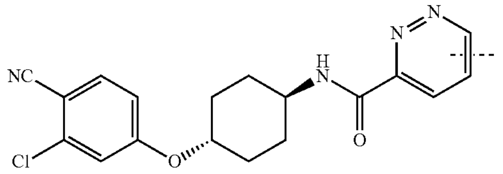
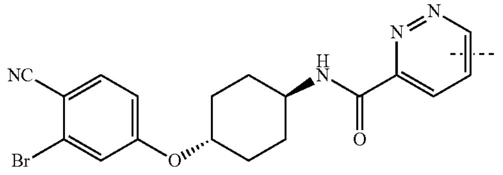
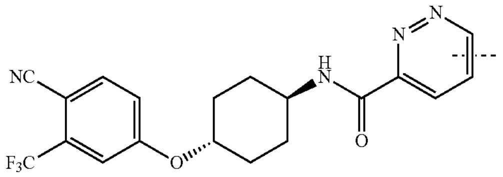
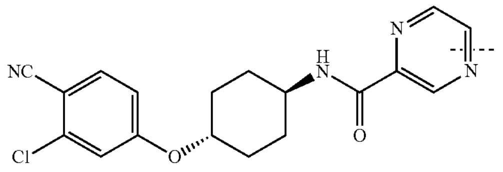
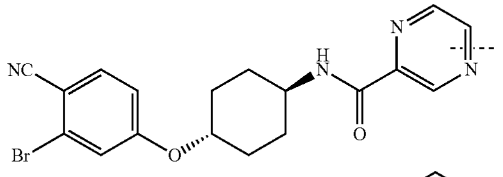
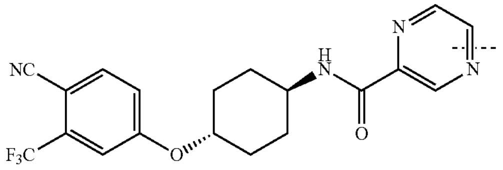

-continued
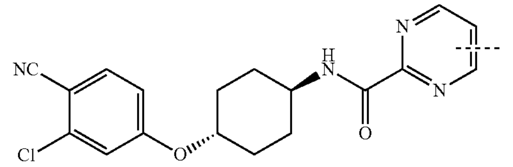
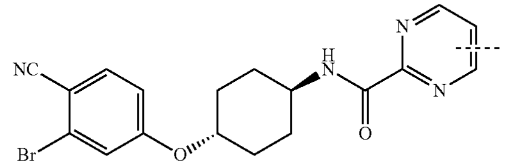
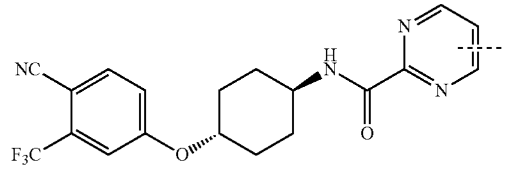
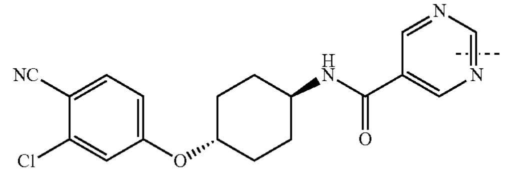
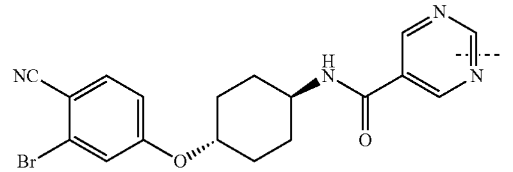
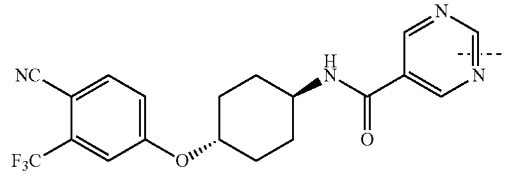
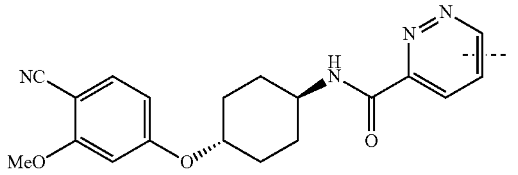
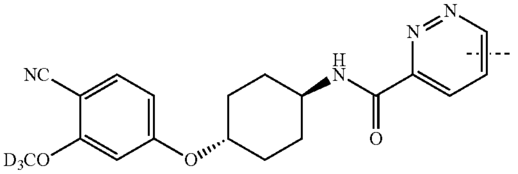
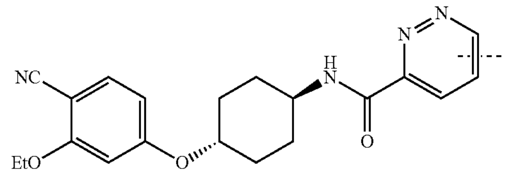
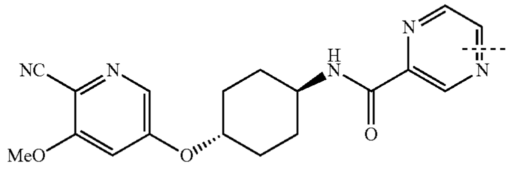
-continued
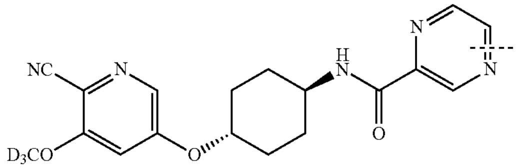
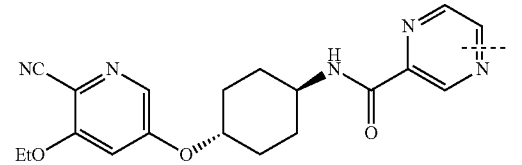
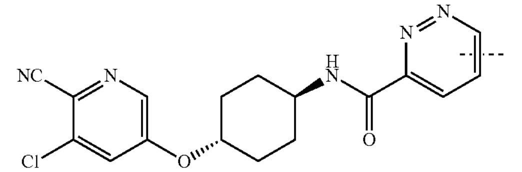
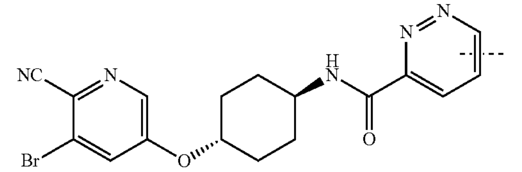
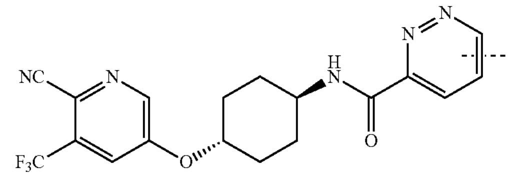
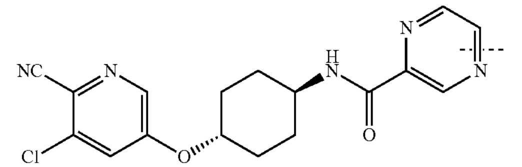
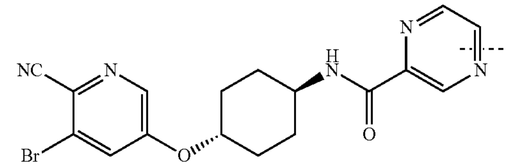
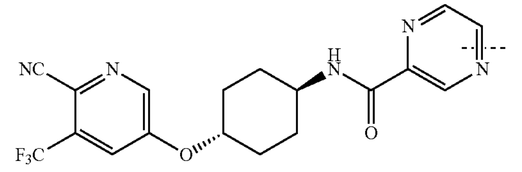
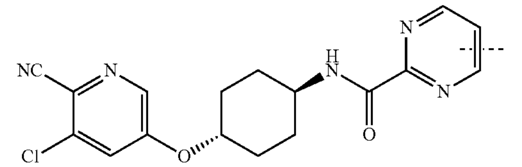
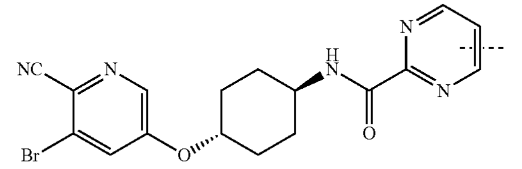

-continued
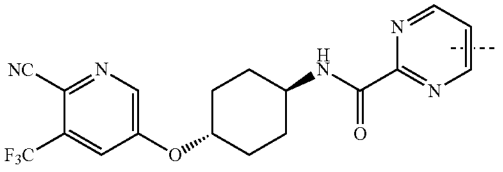
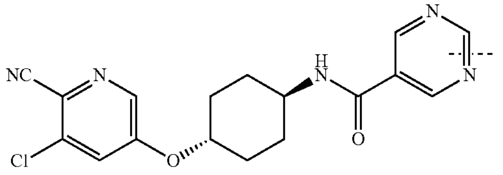
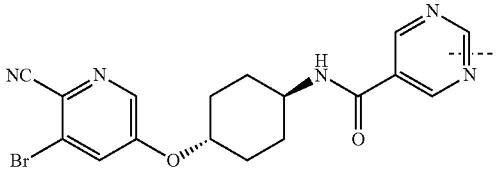
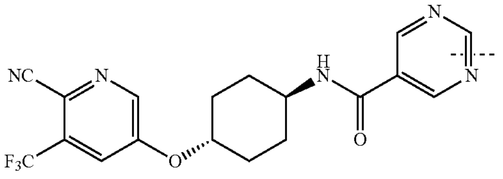
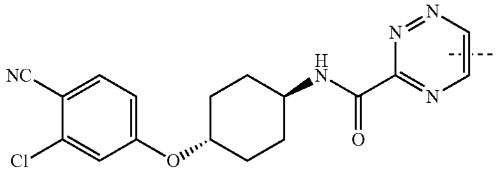
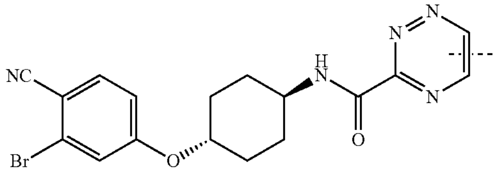
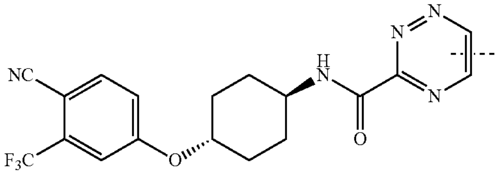
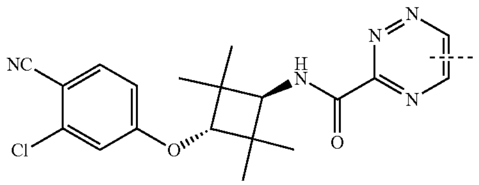
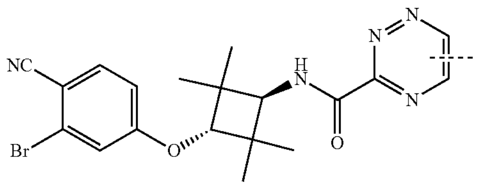
-continued
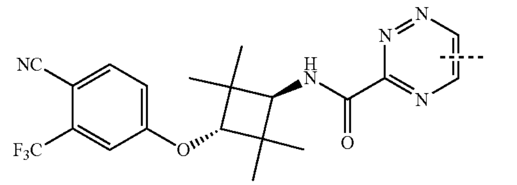
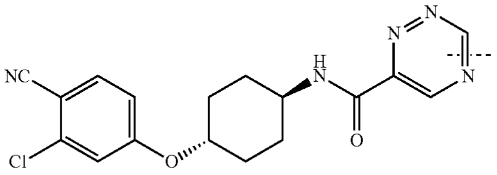
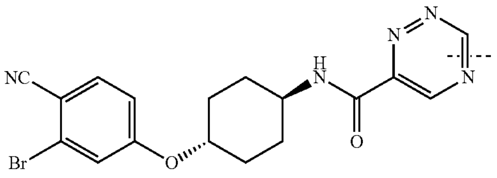
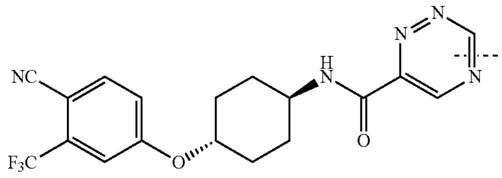
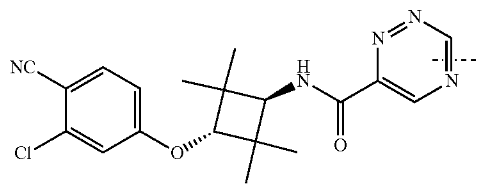
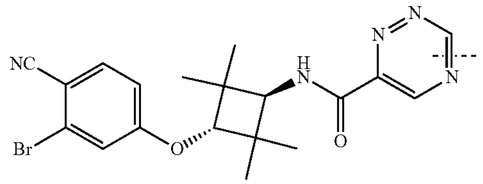
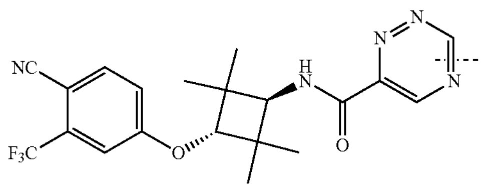
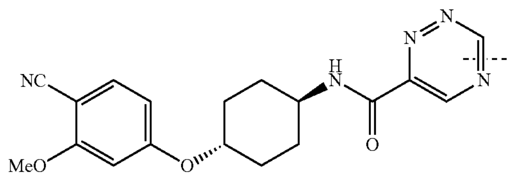
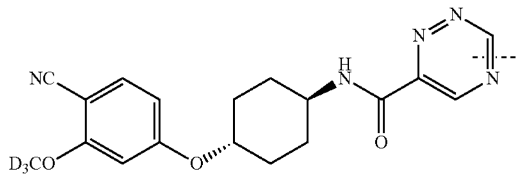

-continued
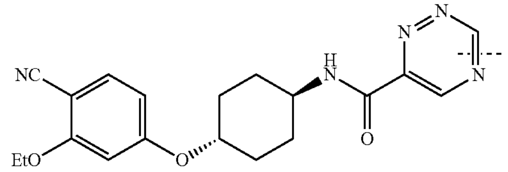
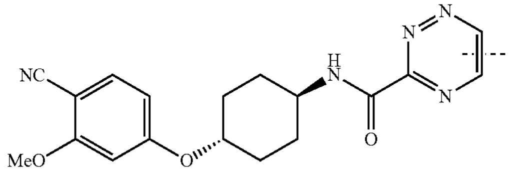
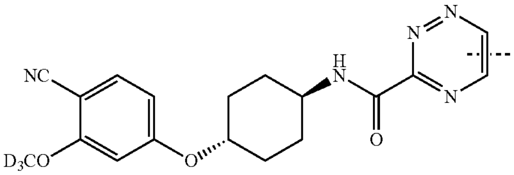
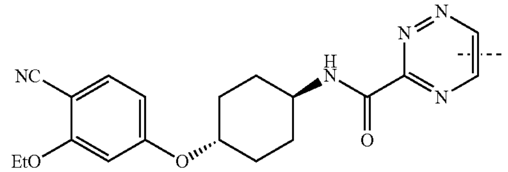
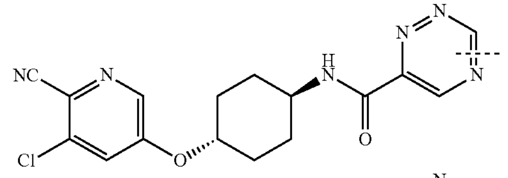
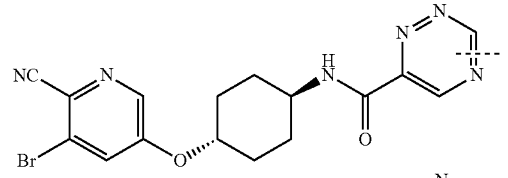
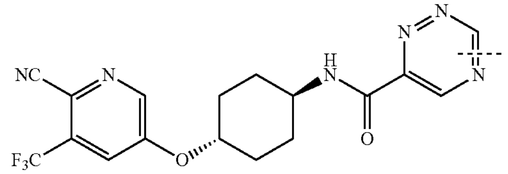
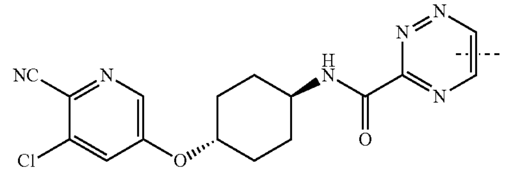
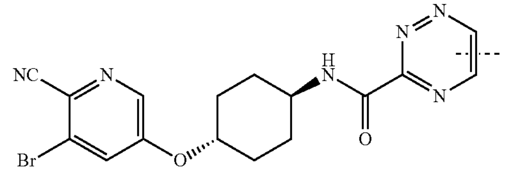
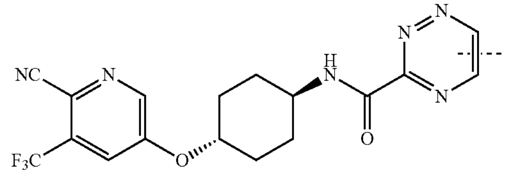
-continued
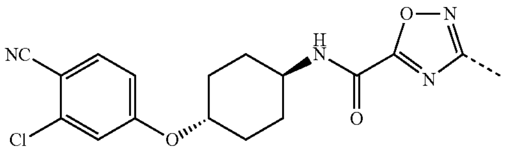
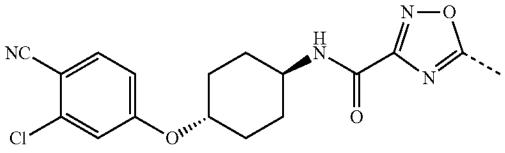
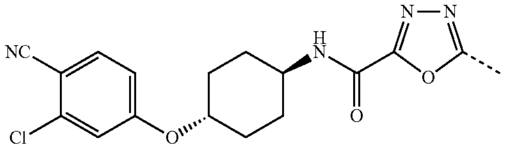
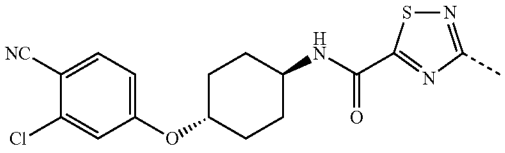
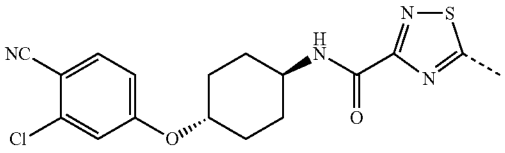
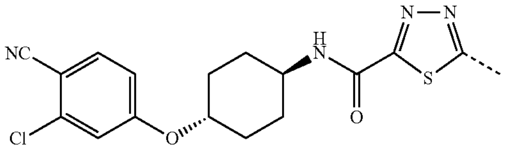
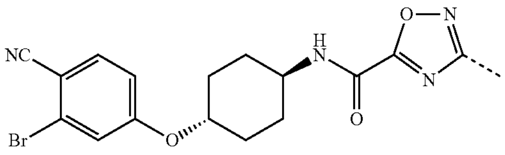
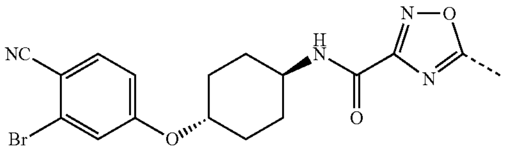
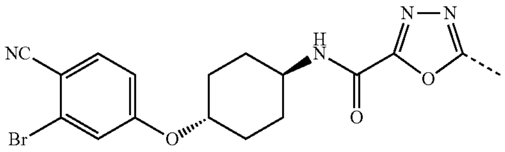
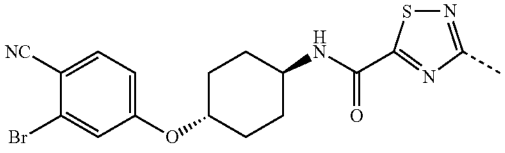
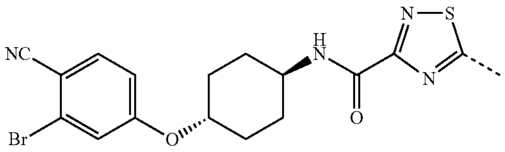

-continued
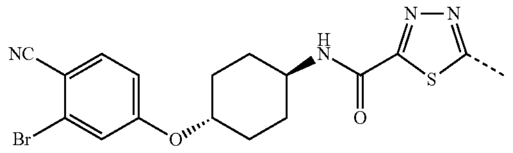
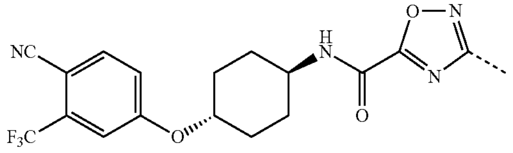
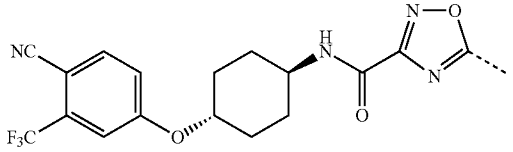
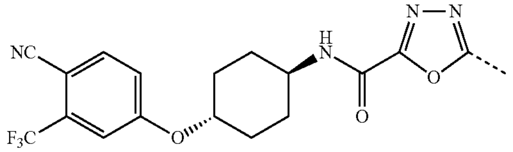
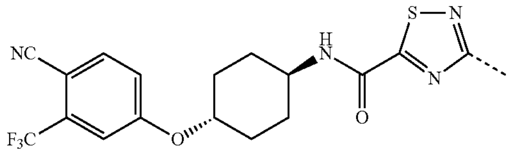
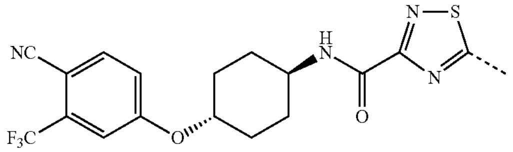
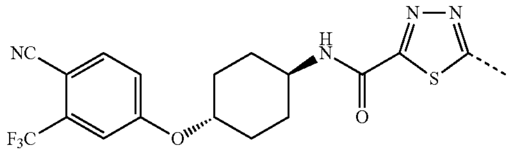
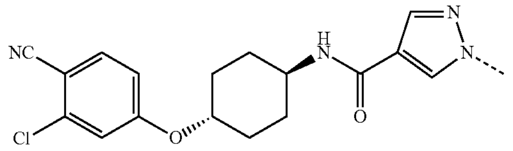
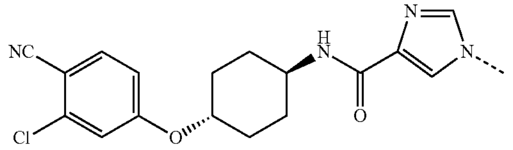
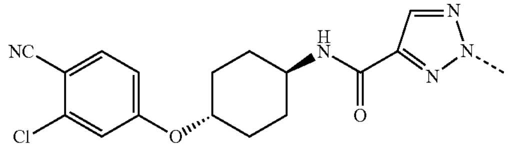
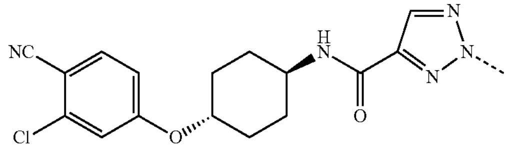
-continued
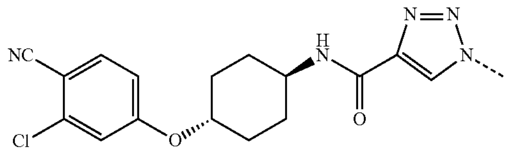
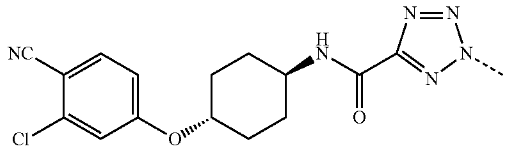
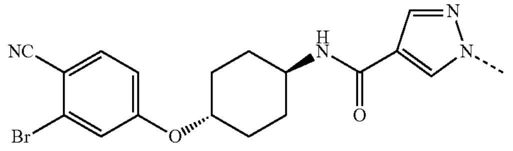
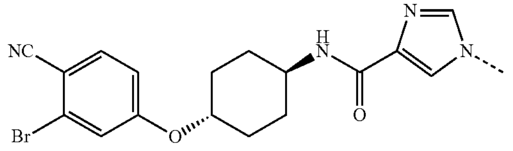
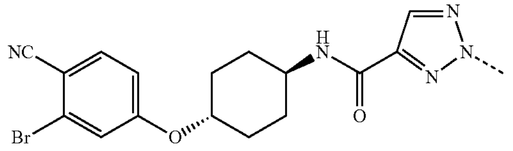
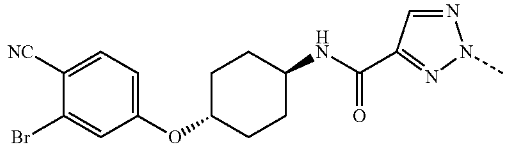
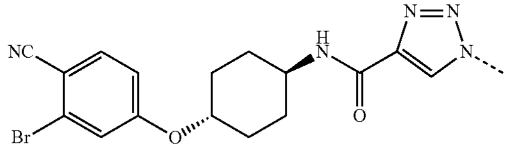
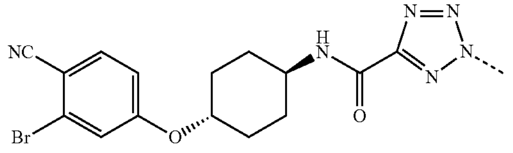
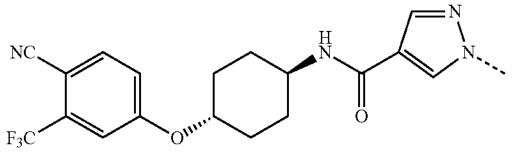
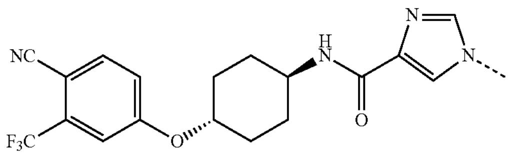
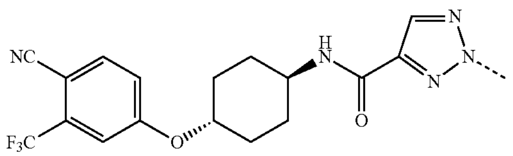

-continued
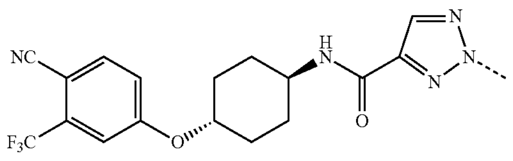
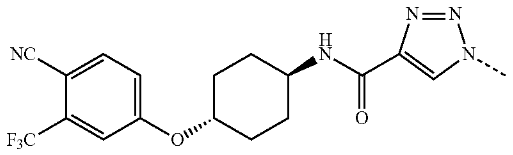
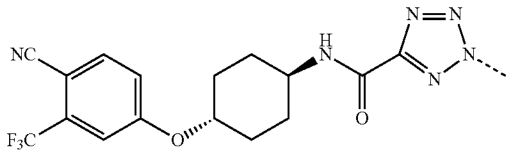
and
said L is selected from the following structures:
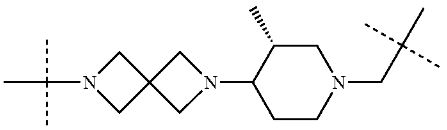
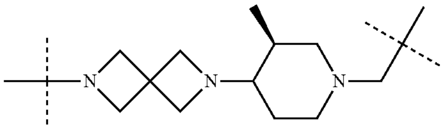
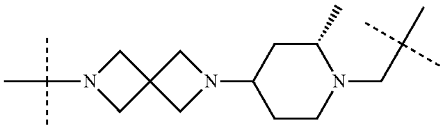
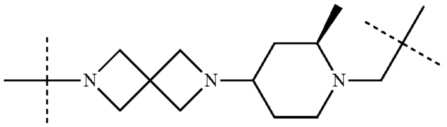
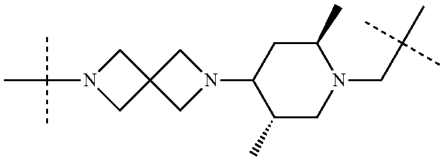
or formula (VIII-B):
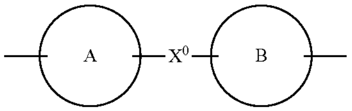
(VIII-B)
wherein ring A is selected from the following structures which are halogenated or non-halogenated:
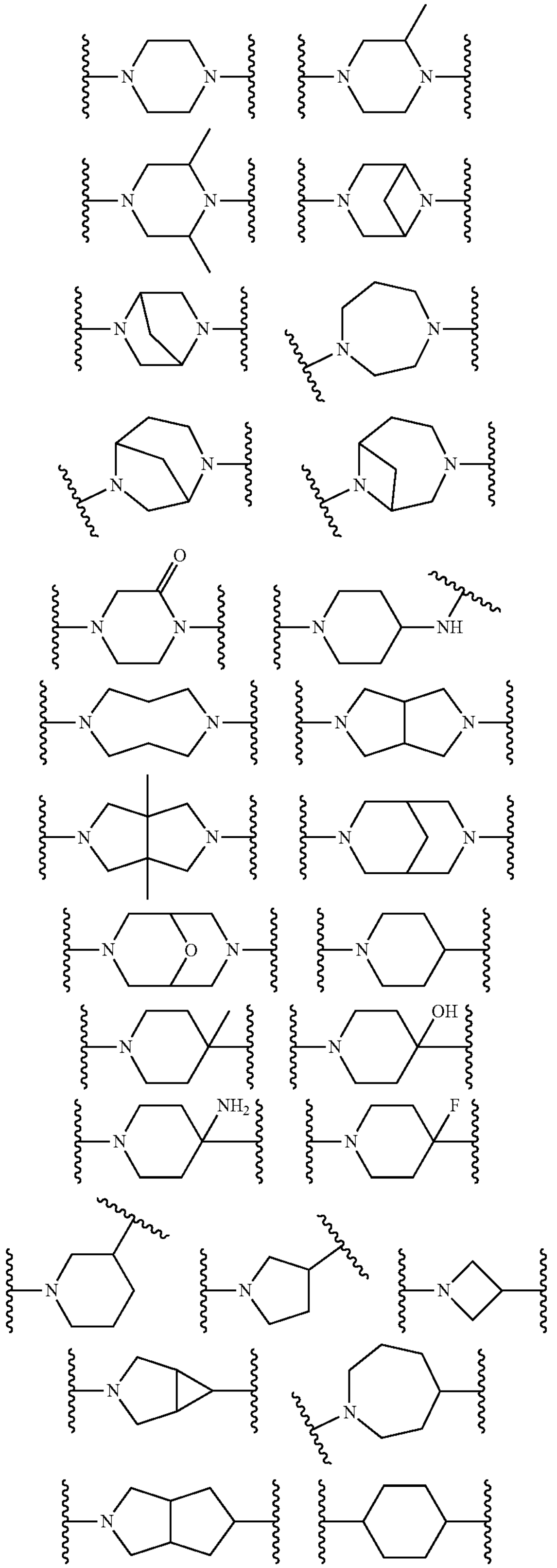

-continued
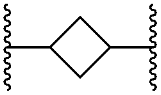
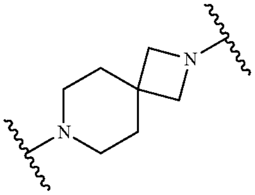
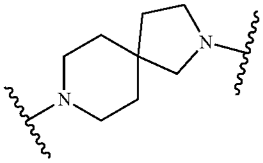
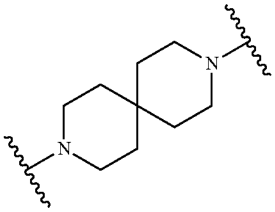
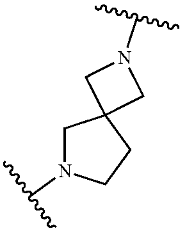
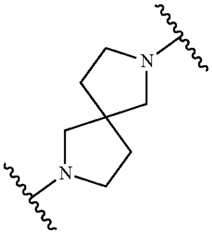
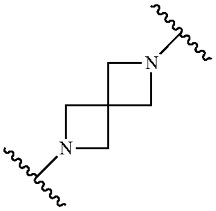
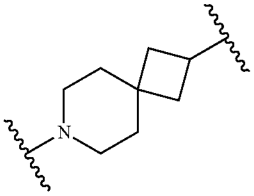
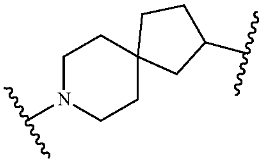
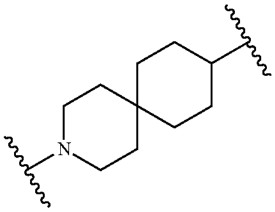
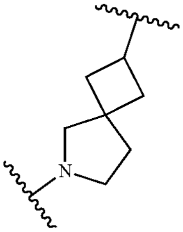
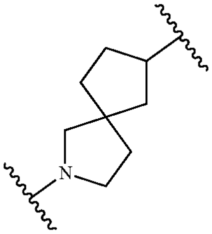
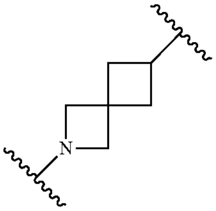
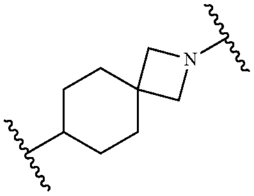
-continued
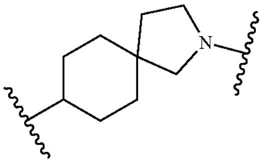
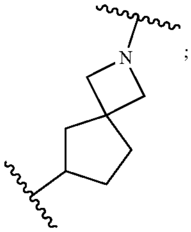
;
ring B is selected from the following structures which are halogenated or non-halogenated:
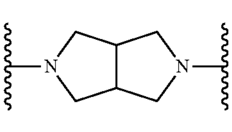
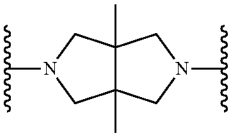
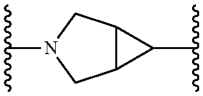
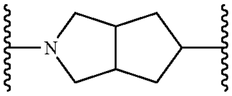
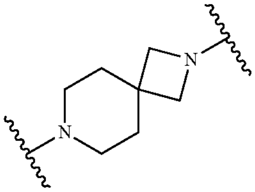
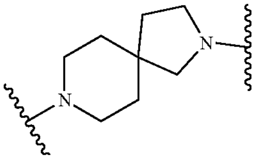
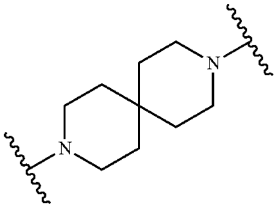
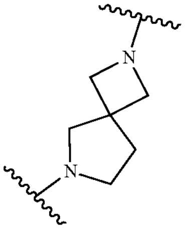
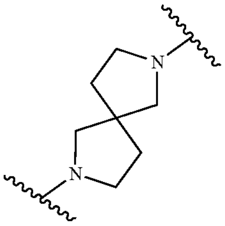
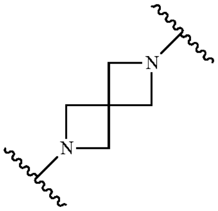
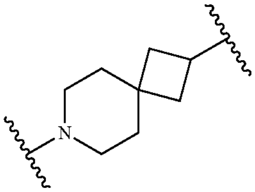
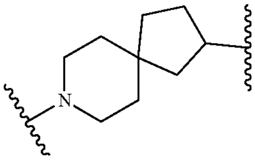
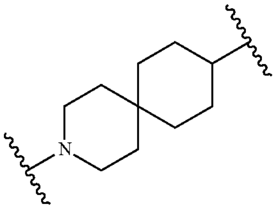
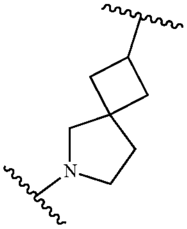

-continued

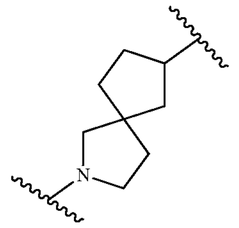
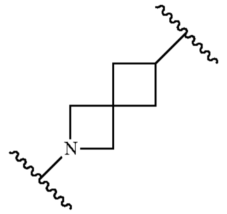
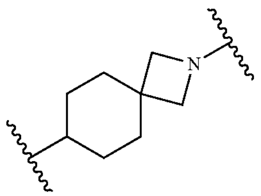
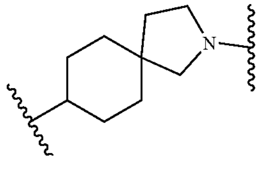
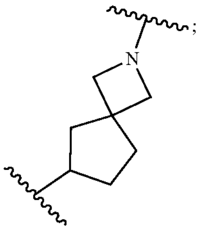

$X^0$ is selected from the group consisting of none, O, S, SO, $SO_2$, NH, $NCH_3$, —$CH_2$;

ring A and ring B can freely link to ARB or U respectively;

said U is selected from the structures of the following structures:

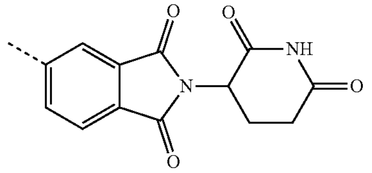
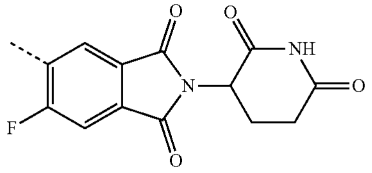
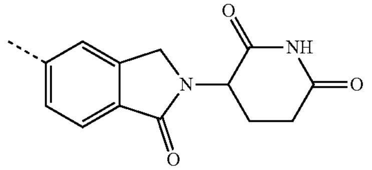
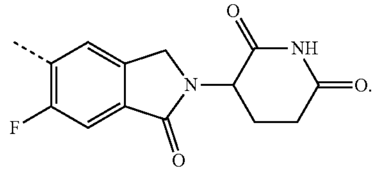

2. The compound according to claim 1, or an isotopic compound thereof, or an optical isomer thereof, or a tautomer thereof, or a pharmaceutically acceptable salt thereof, wherein said L is selected from the structures of the following structures:

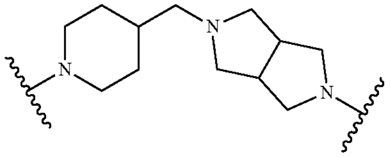
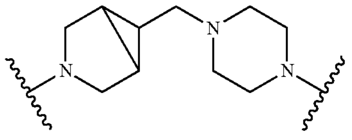
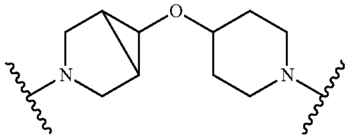
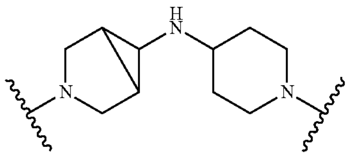
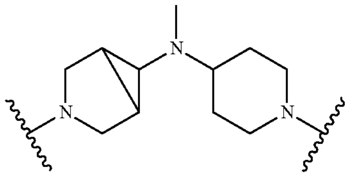
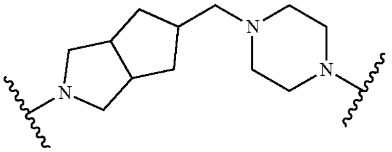
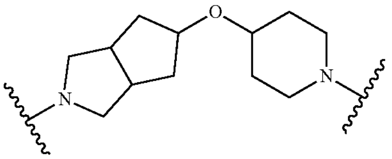
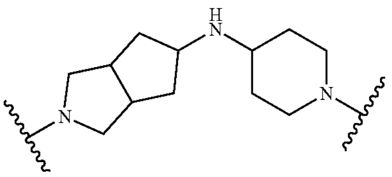
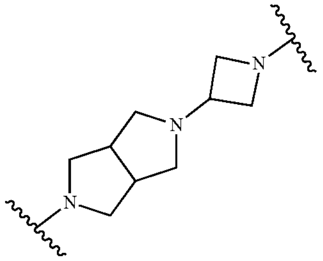

-continued
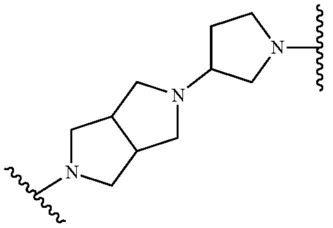
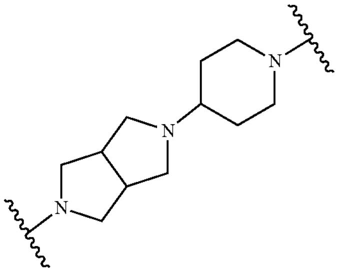
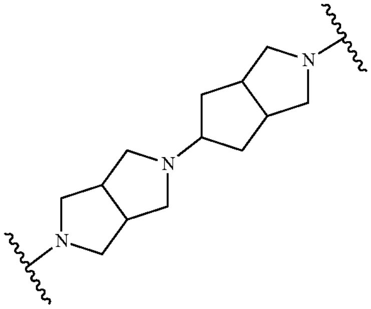
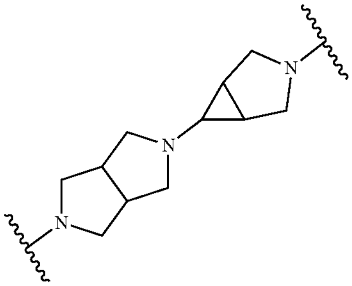
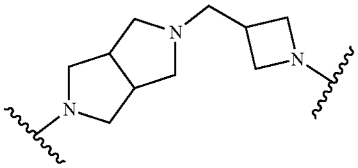
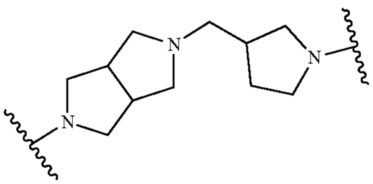
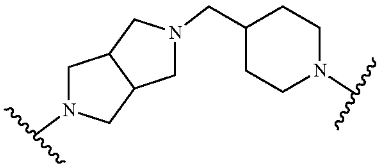
-continued
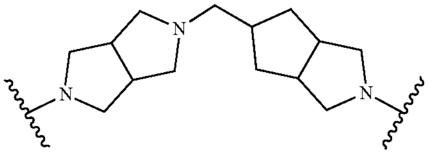
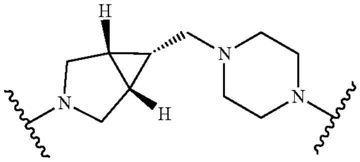
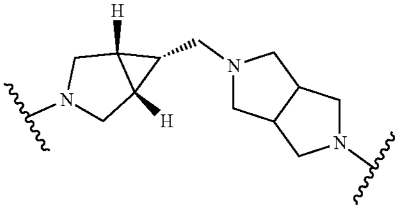
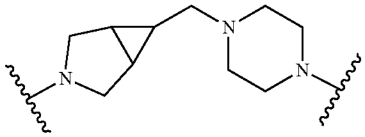
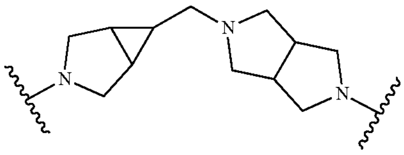
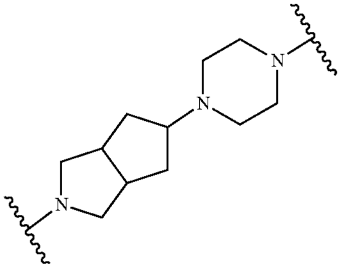
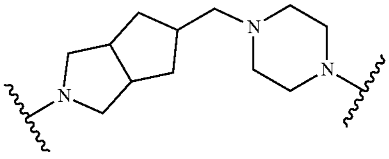
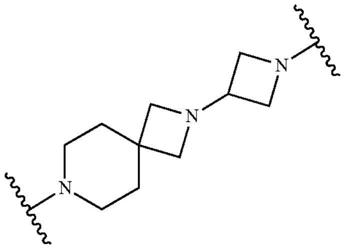
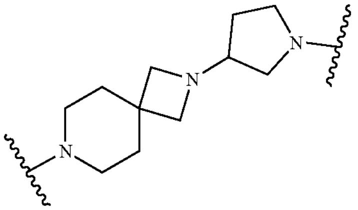

-continued
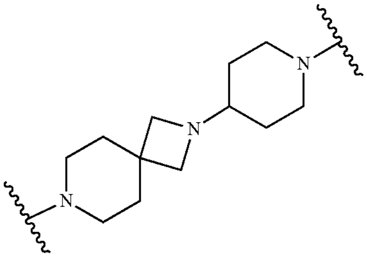
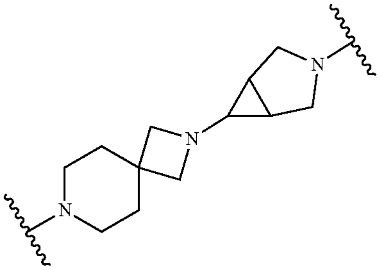
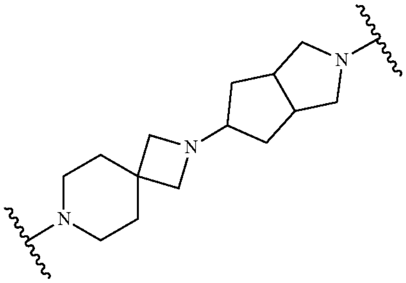
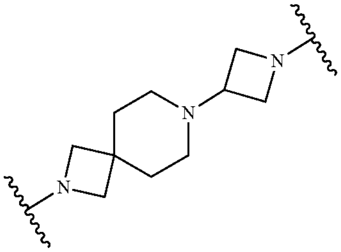
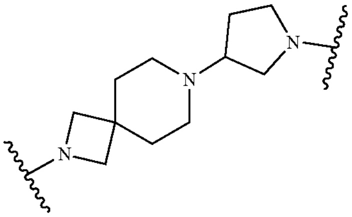
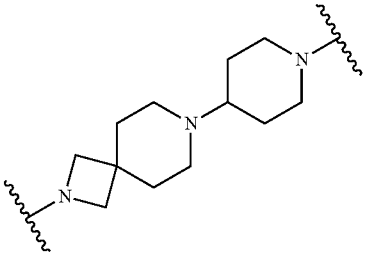
-continued
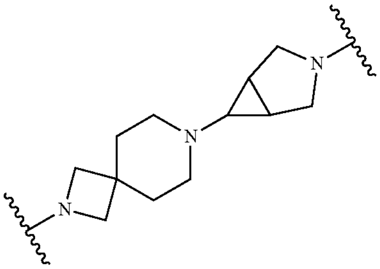
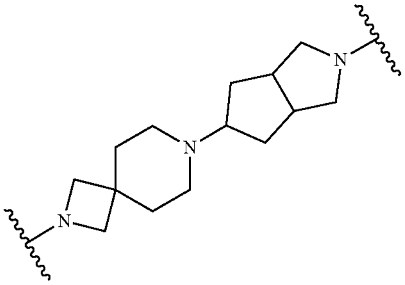
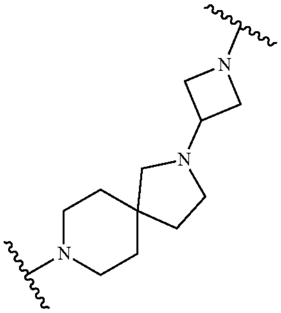
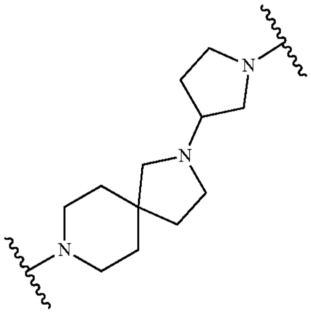
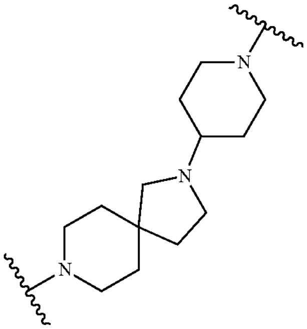

-continued
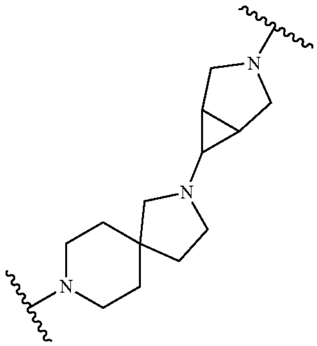
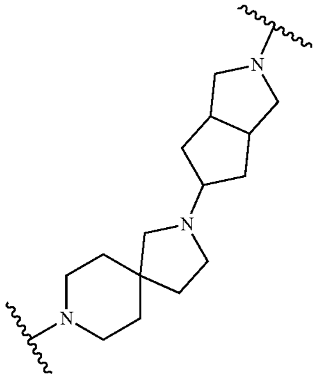
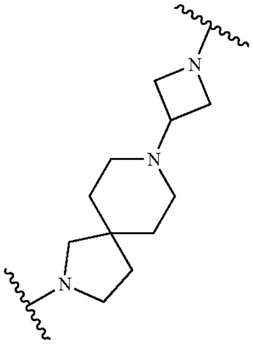
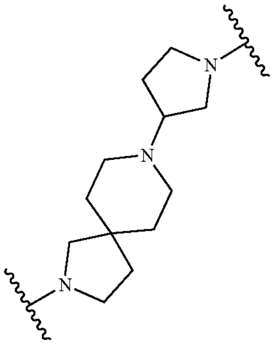
-continued
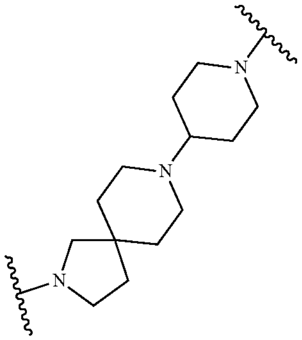
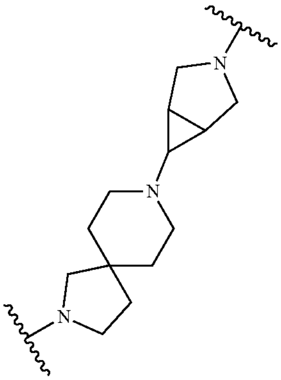
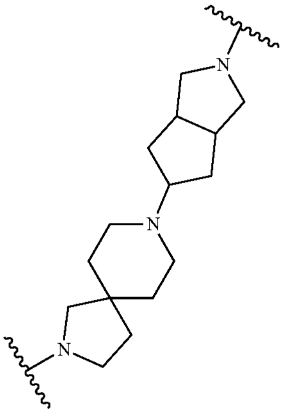
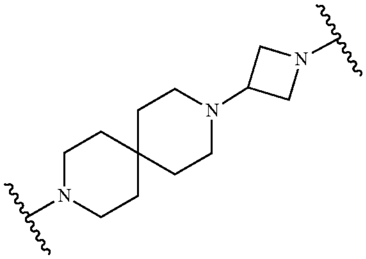
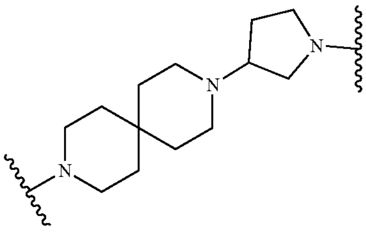

-continued
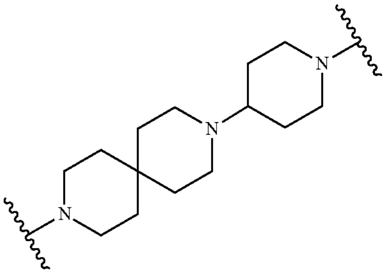
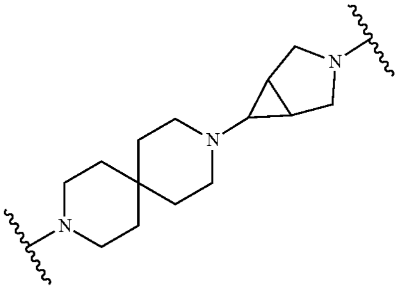
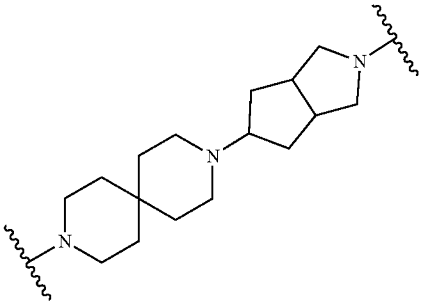
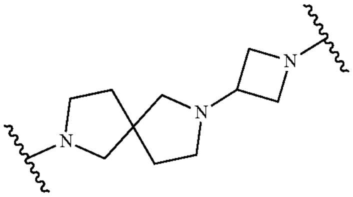
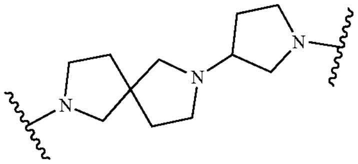
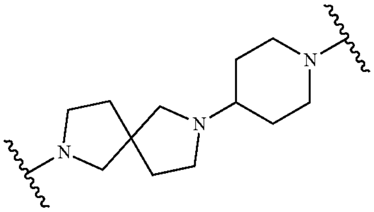
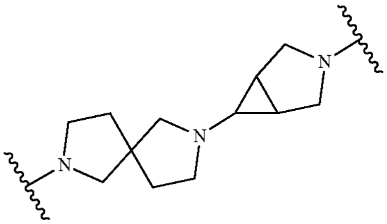
-continued
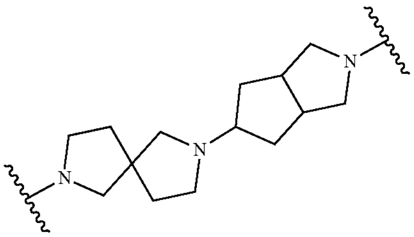
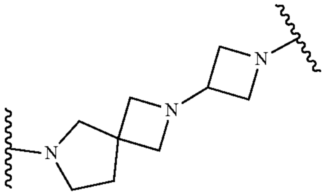
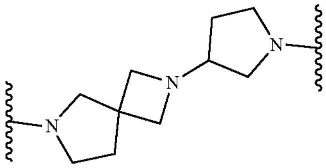
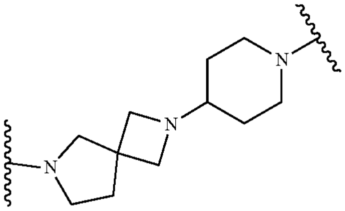
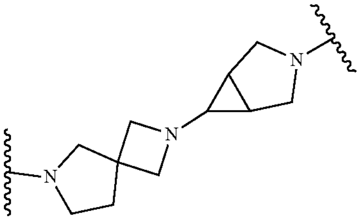
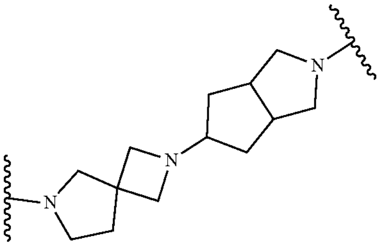
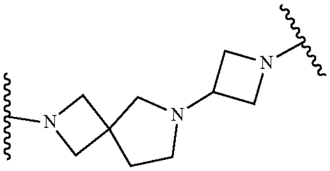
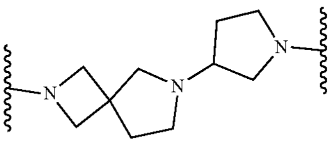

-continued
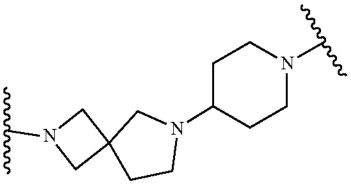
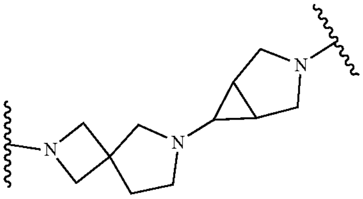
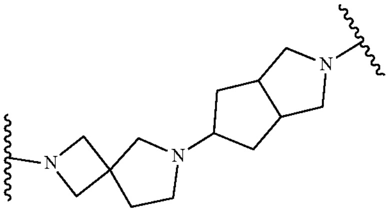
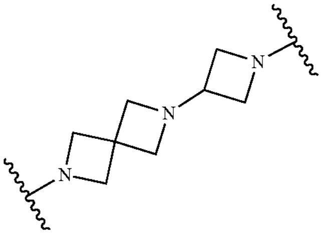
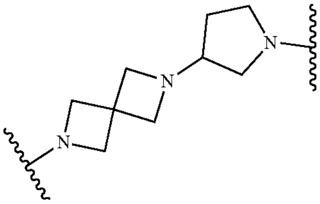
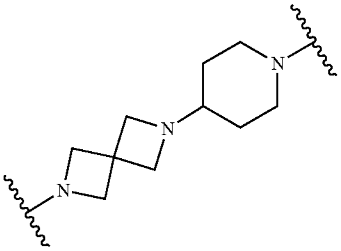
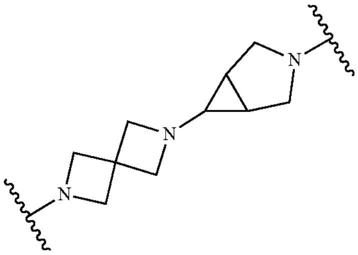
-continued
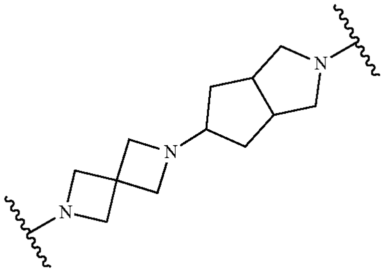
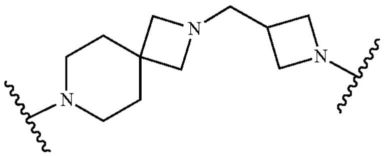
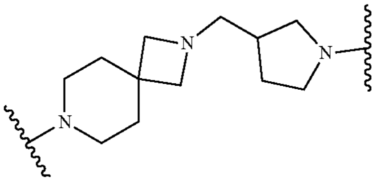
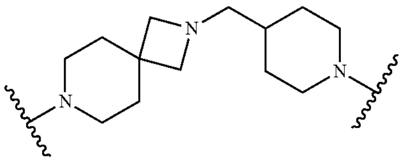
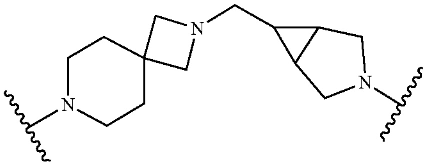
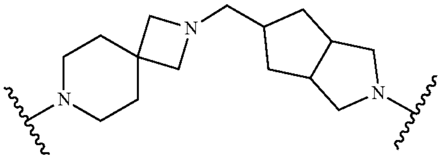
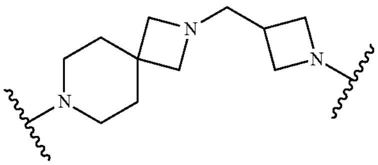
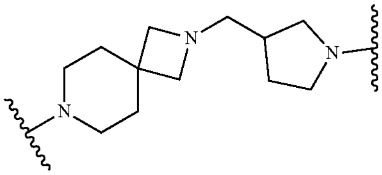
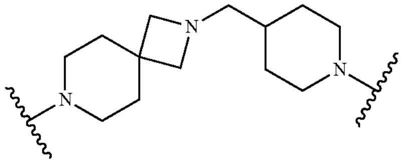

-continued
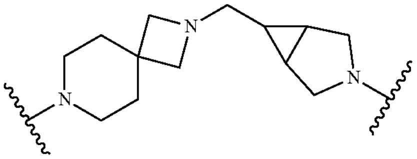
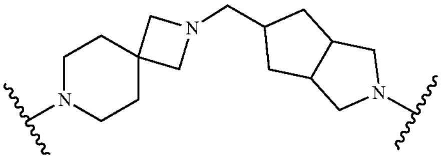
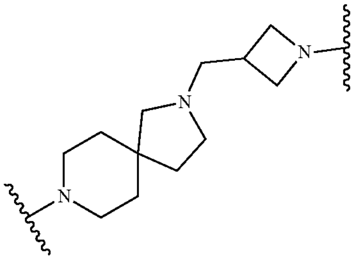
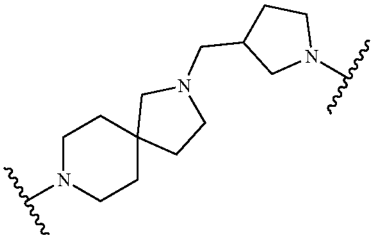
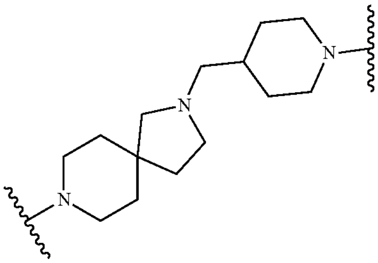
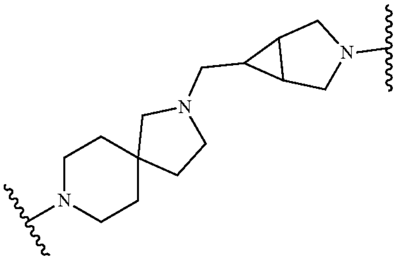
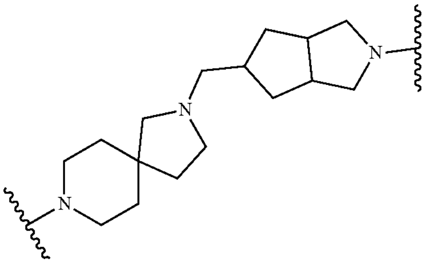
-continued
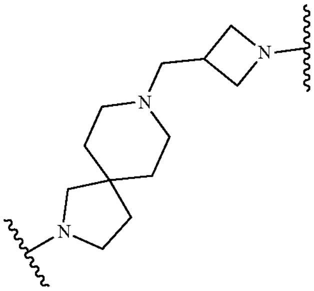
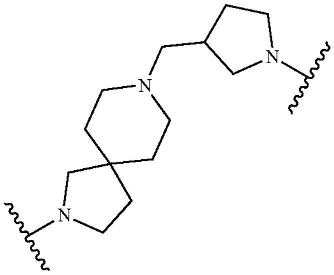
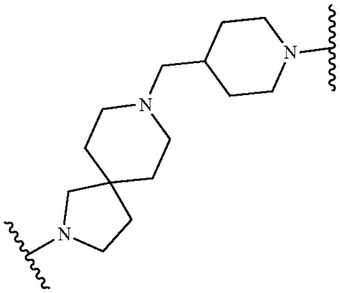
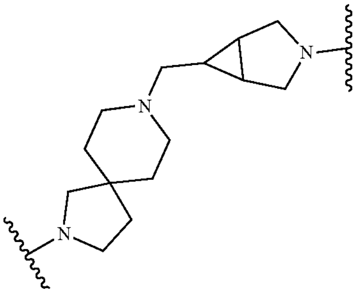
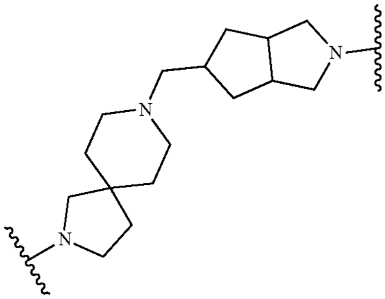
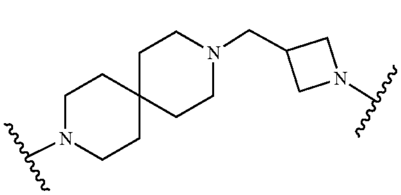

-continued
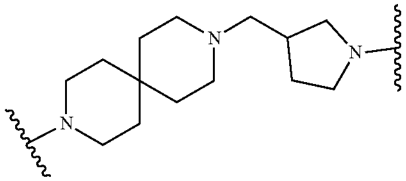
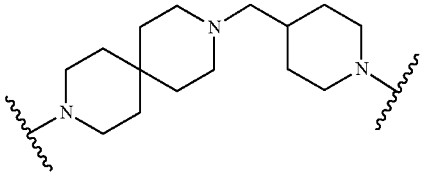
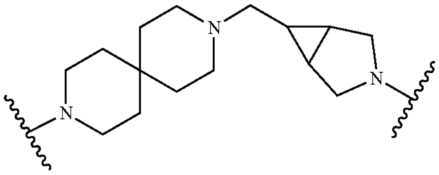
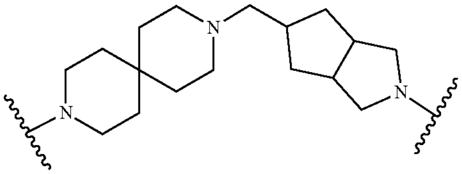
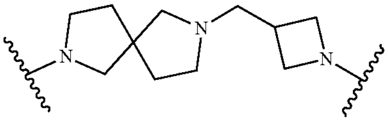
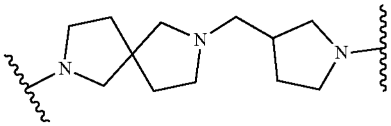
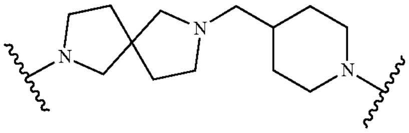
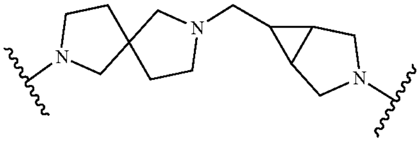
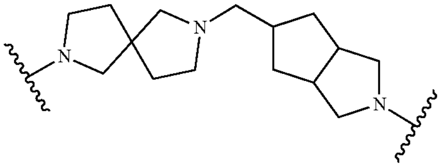
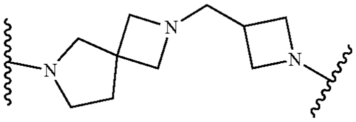
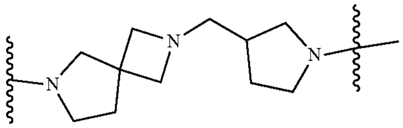
-continued
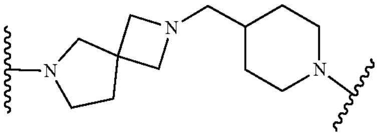
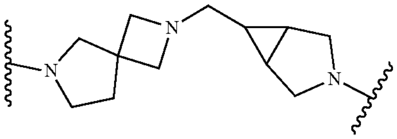
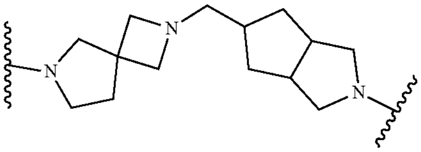
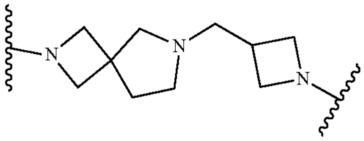
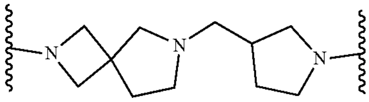
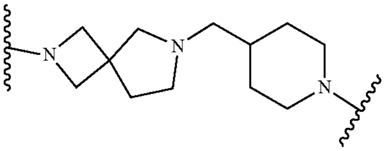
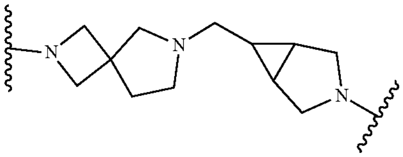
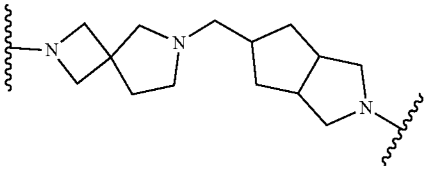
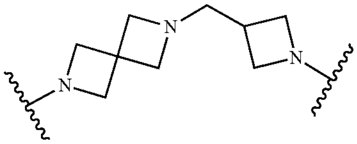
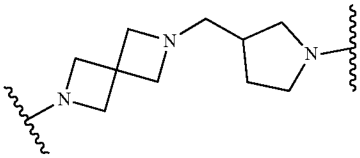
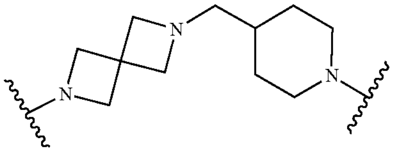

-continued
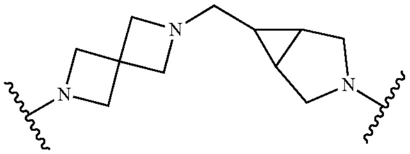
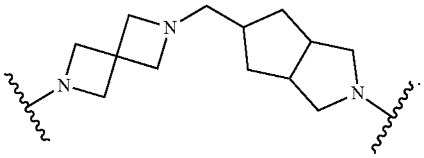
3. The compound according to claim 1, or an isotopic compound thereof, or an optical isomer thereof, or a tautomer thereof, or a pharmaceutically acceptable salt thereof, wherein said L is selected from the structures of the following structures:
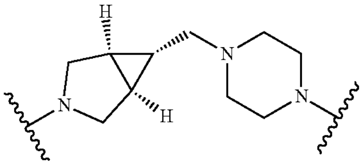
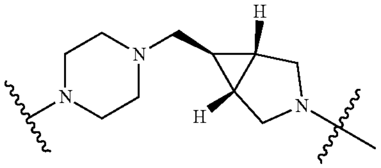
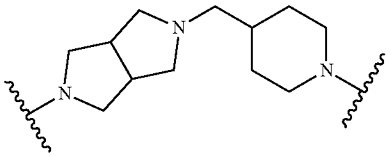
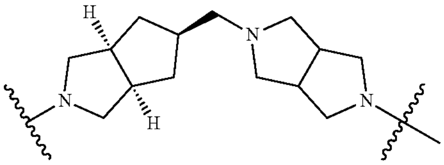
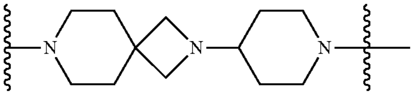
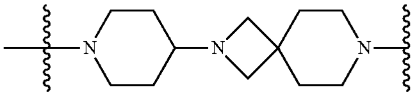
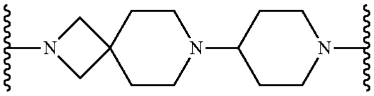
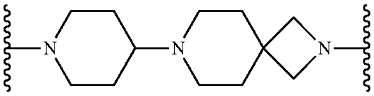
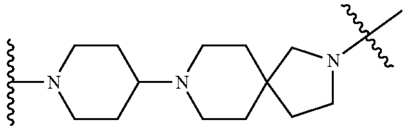
-continued
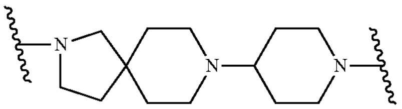
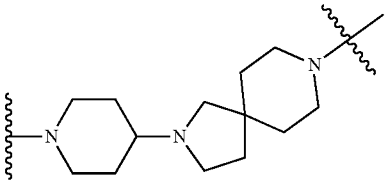
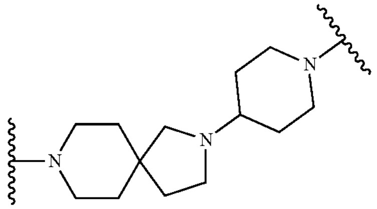
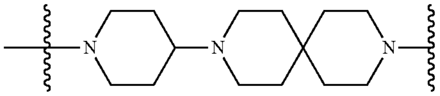
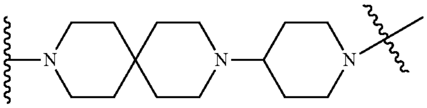
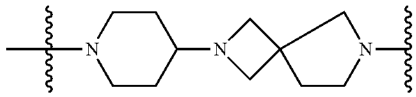
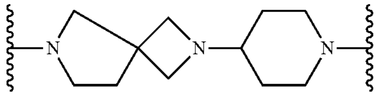
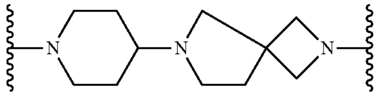
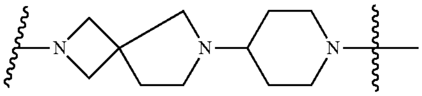
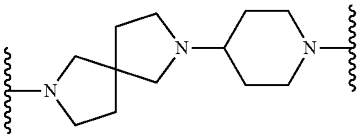
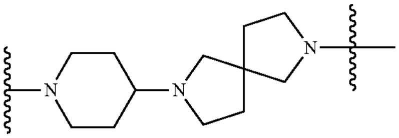
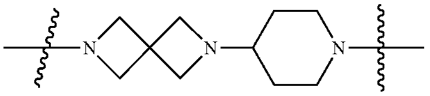
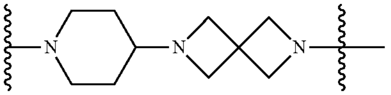
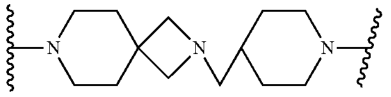

-continued
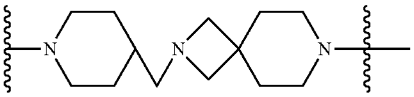
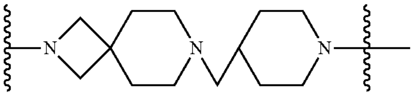
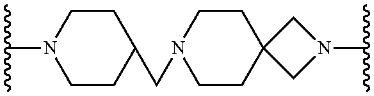
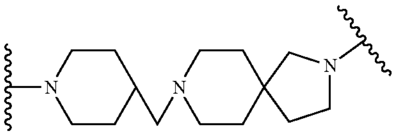
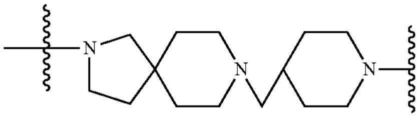
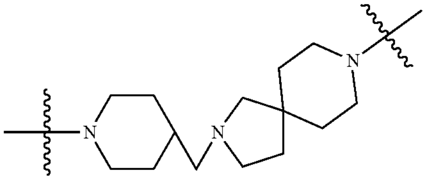
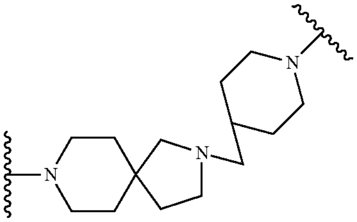
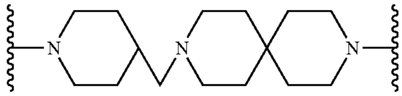
-continued
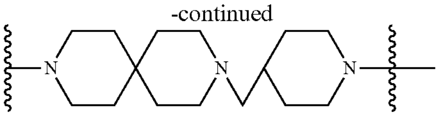
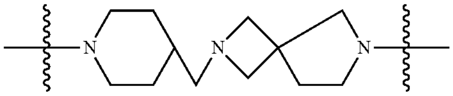
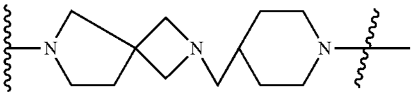
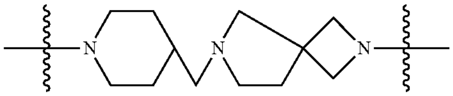
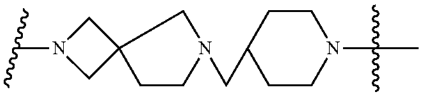
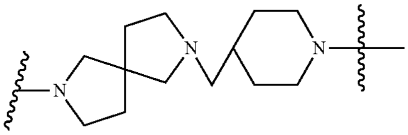
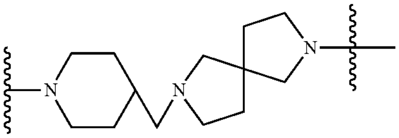
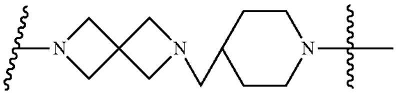
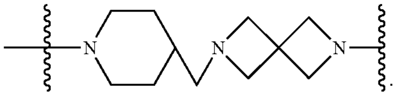
.
4. The compound according to claim 1, or an isotopic compound thereof, or an optical isomer thereof, or a tautomer thereof, or a pharmaceutically acceptable salt thereof, wherein said compound is selected from one of the following compounds:
61
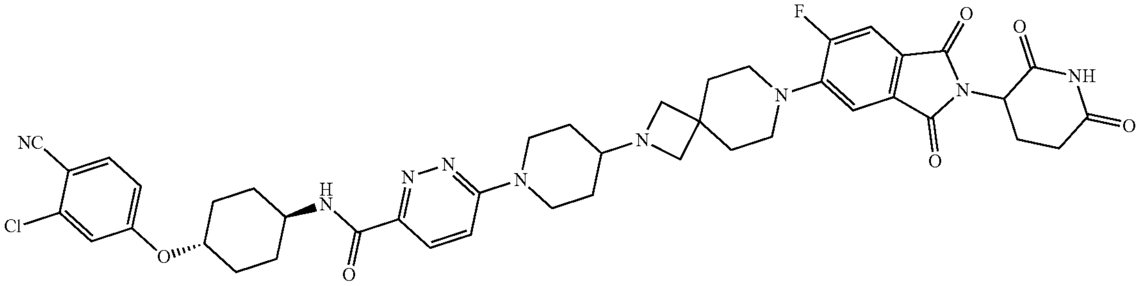

-continued
62
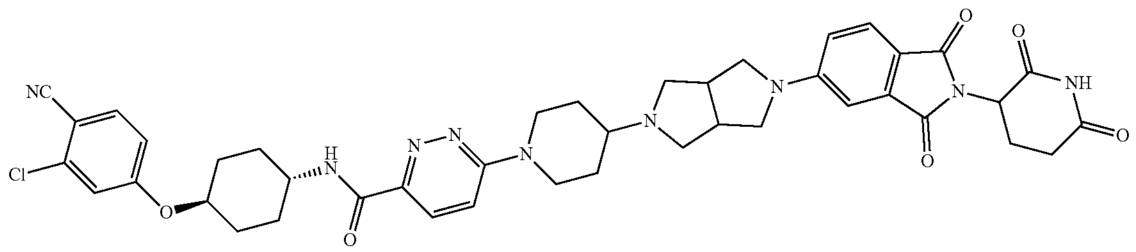
63
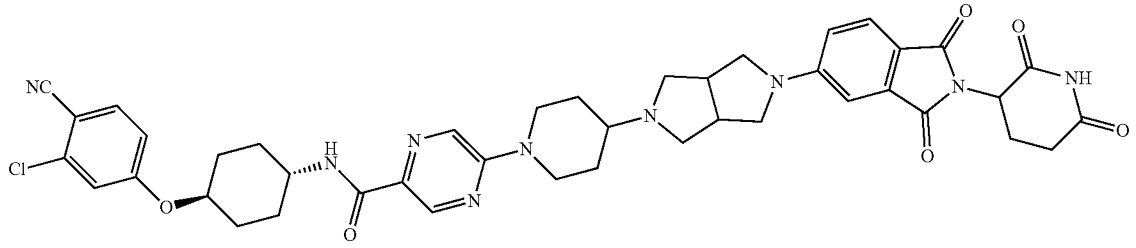
64
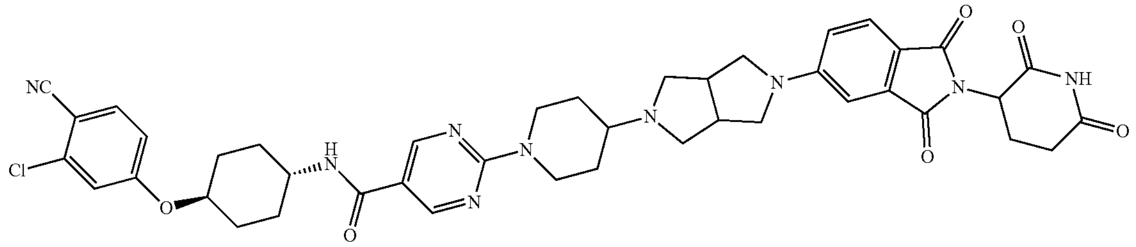
65
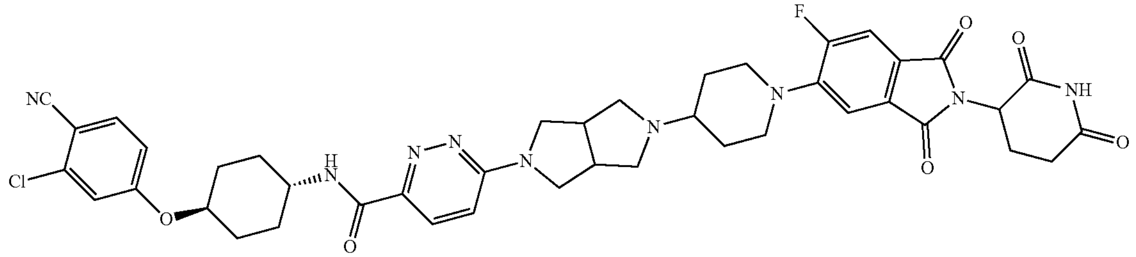
66
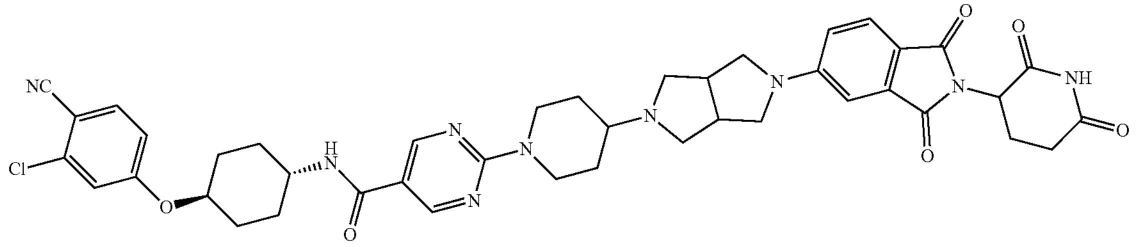
67
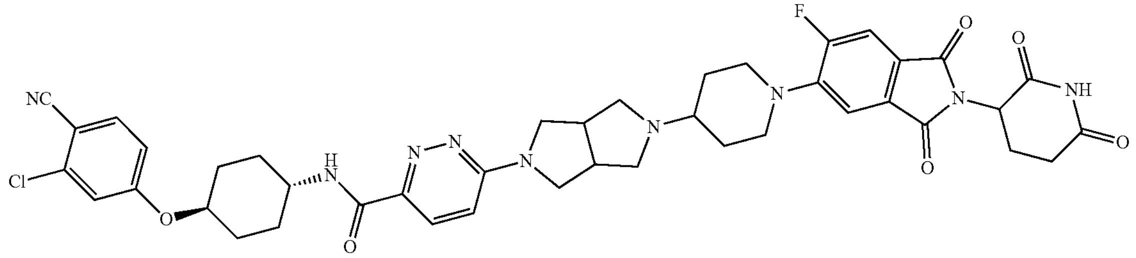

-continued
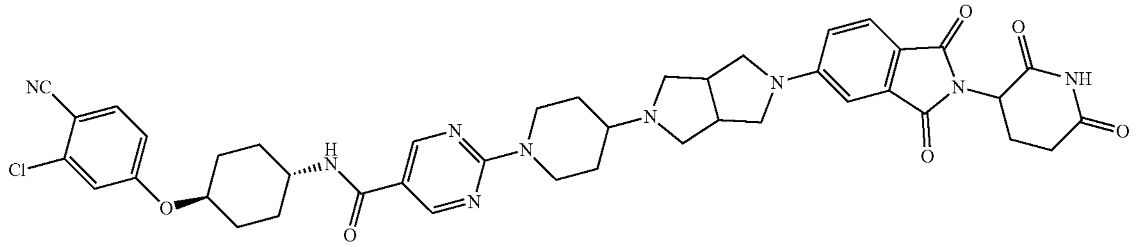
68
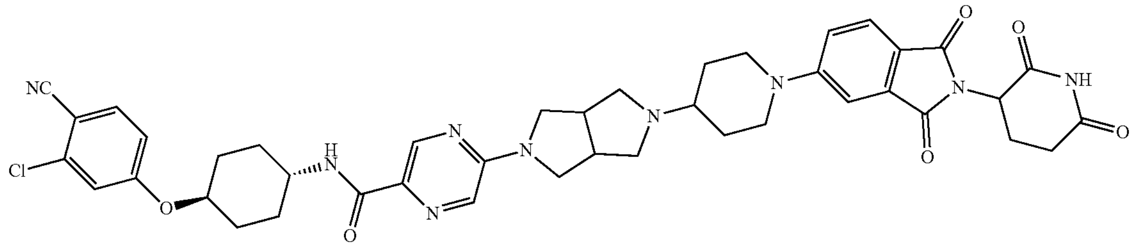
69
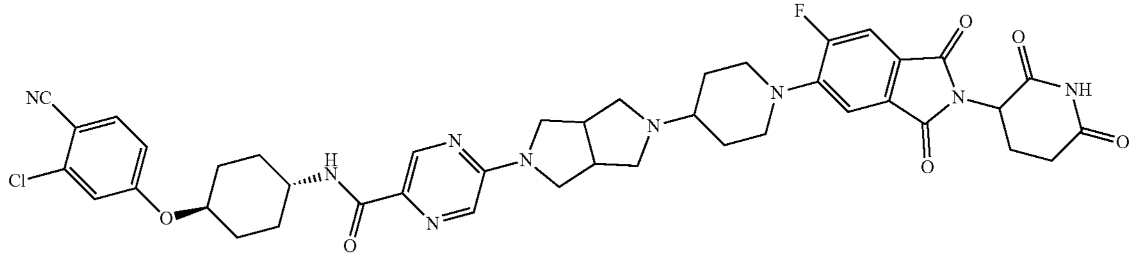
70
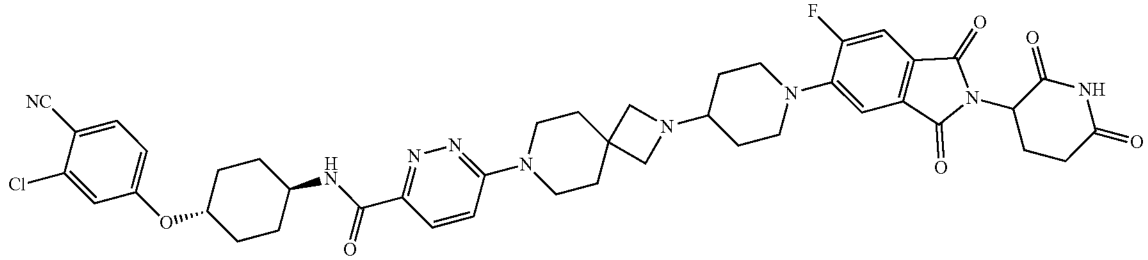
71
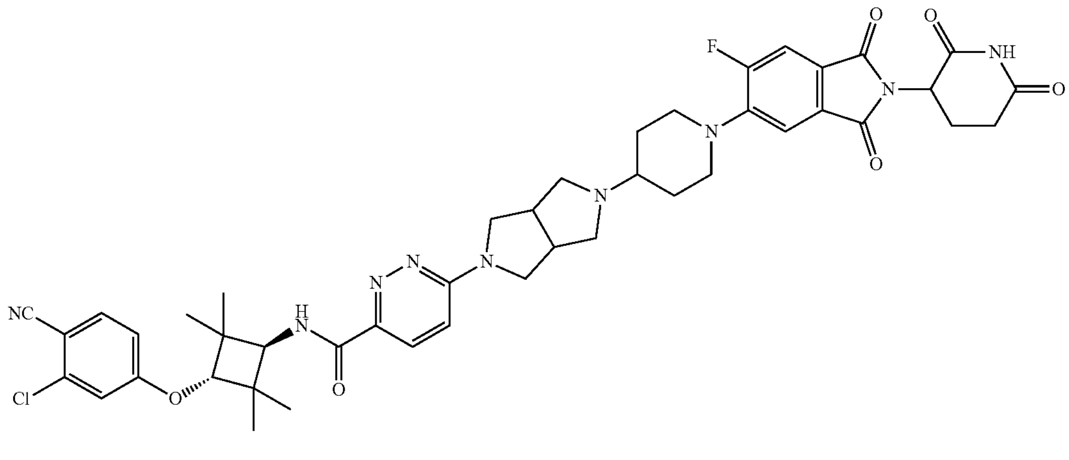
72

-continued
74
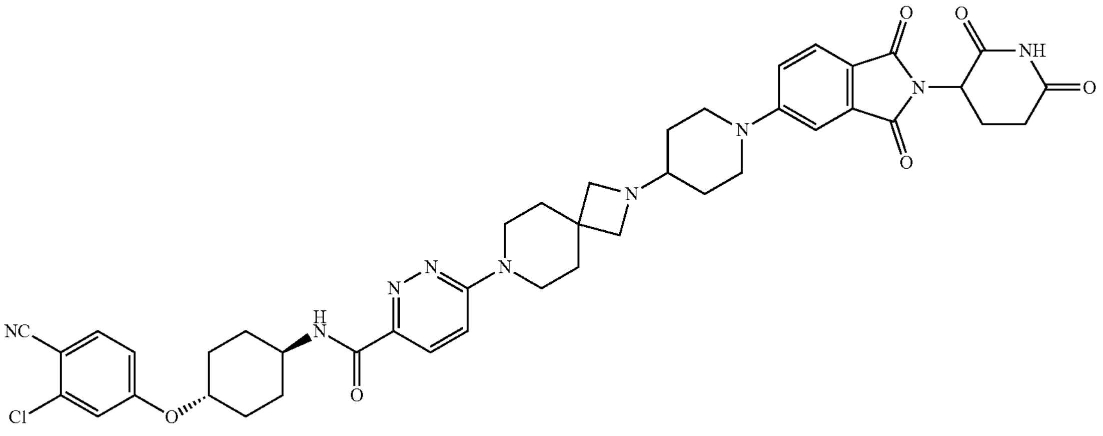
75
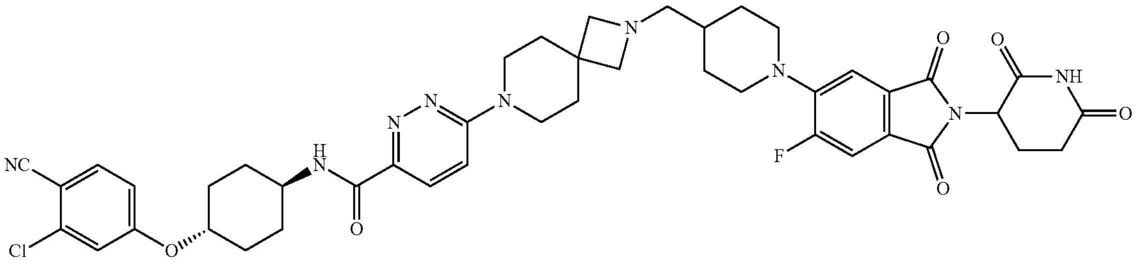
76
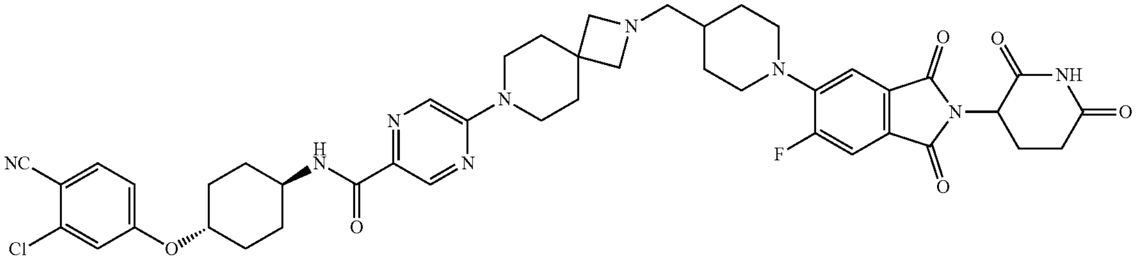
77
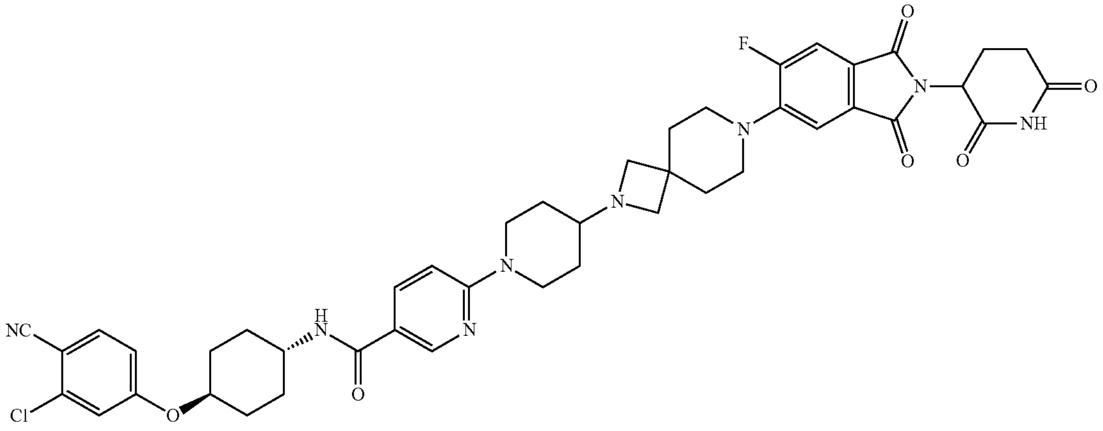

-continued
78
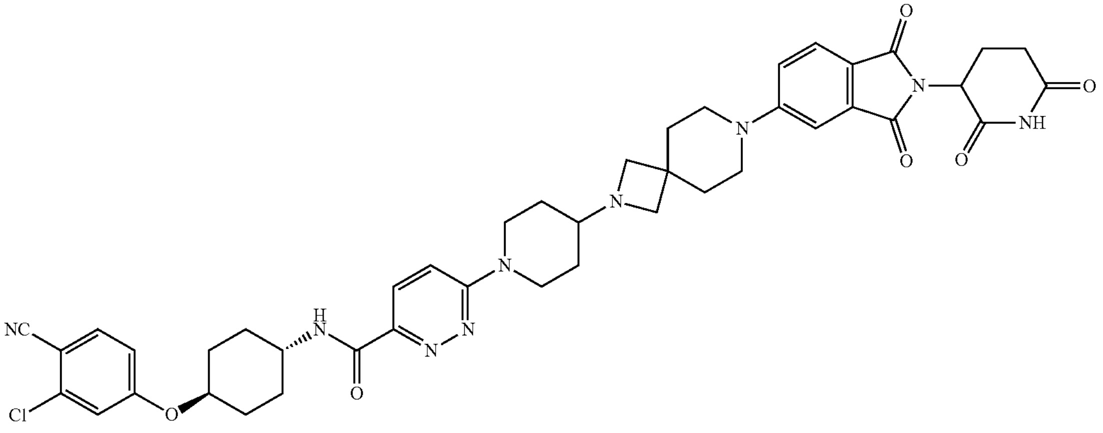
79
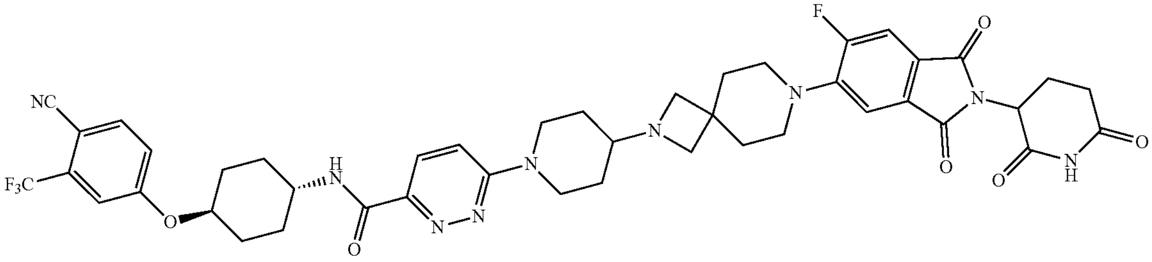
80
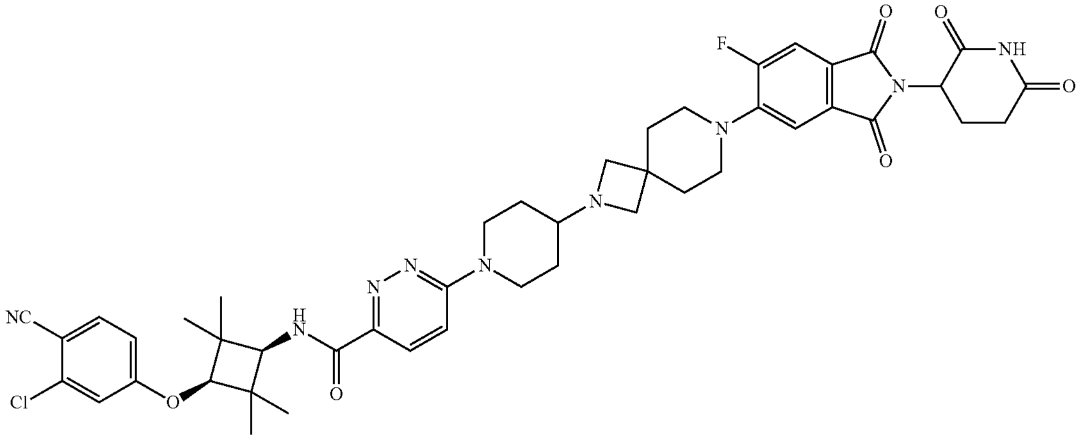
81
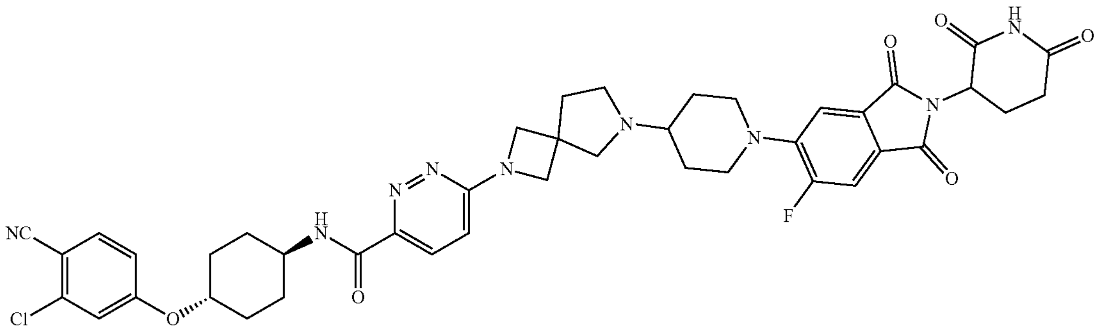

-continued
82
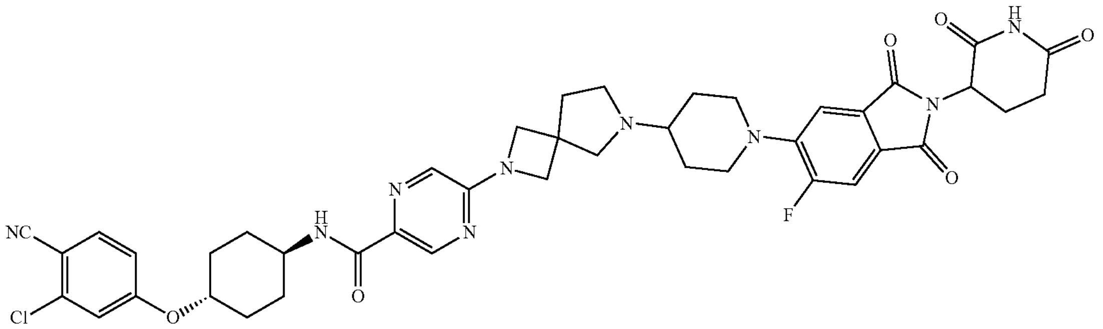
83
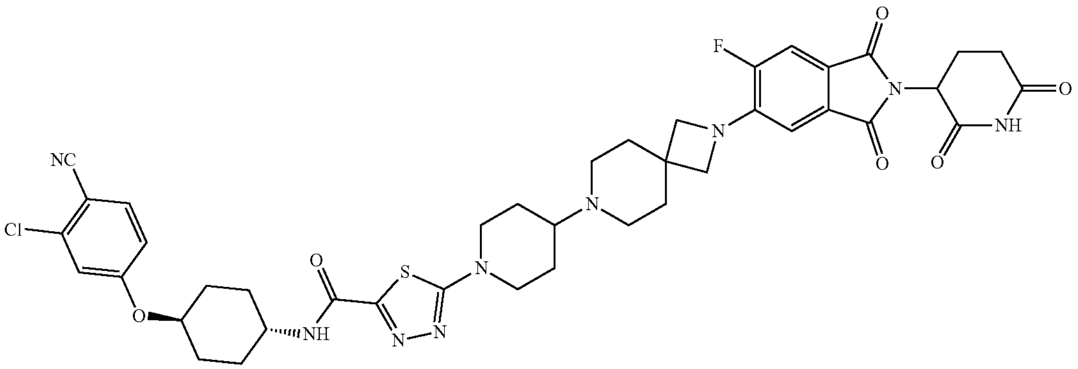
88
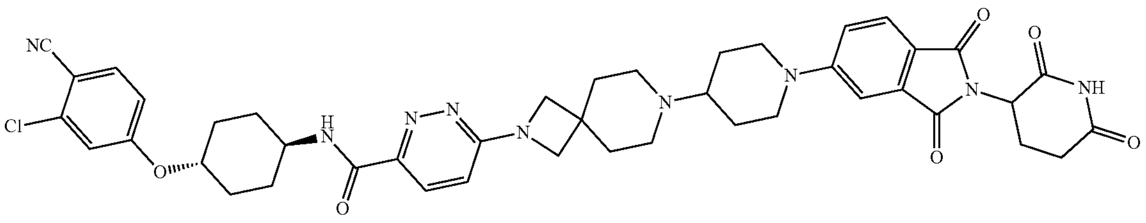
89
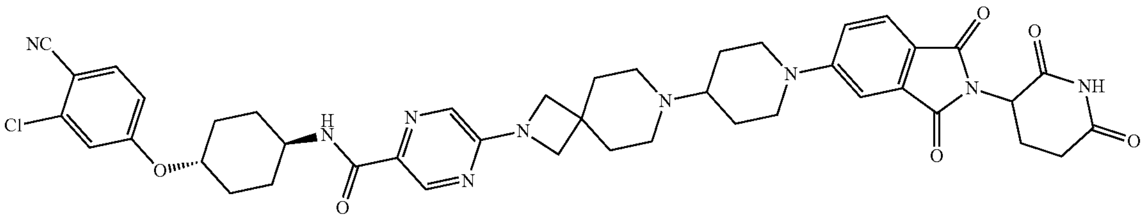
92
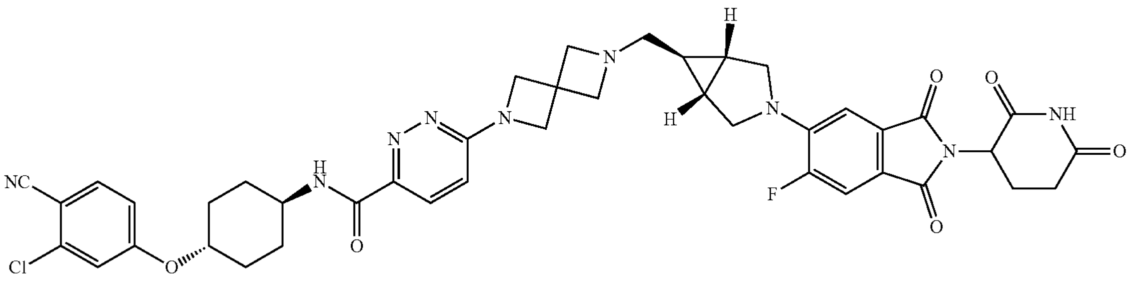

-continued
93
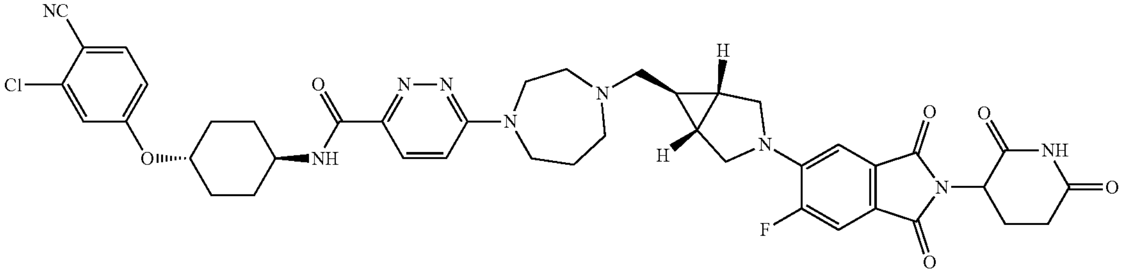
94
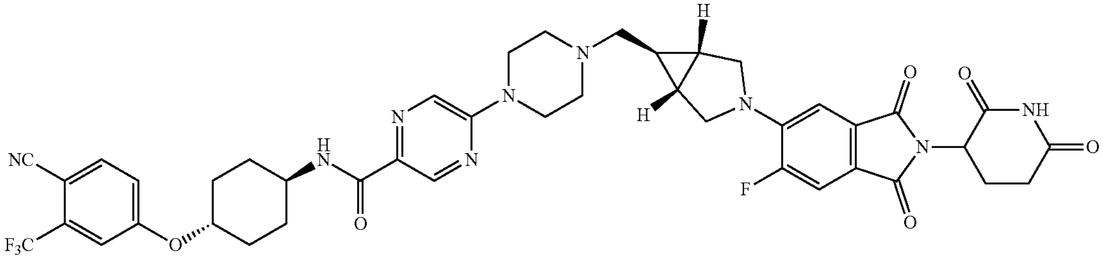
95
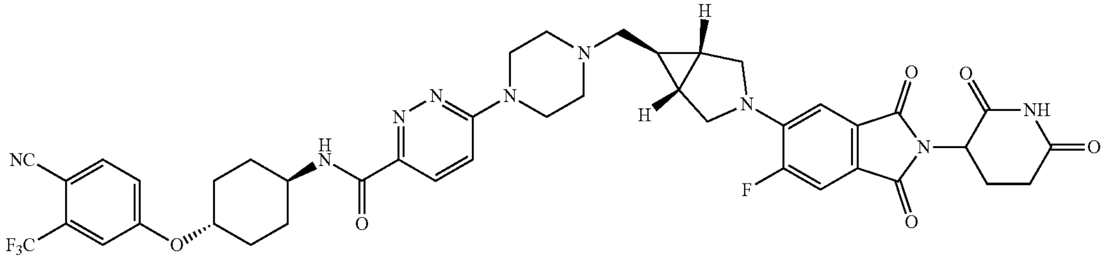
96
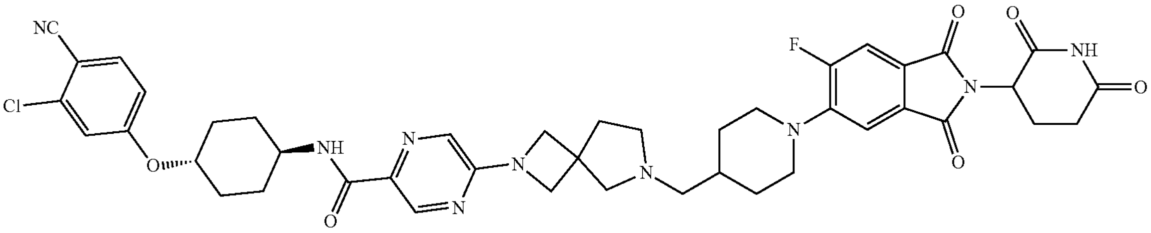
97
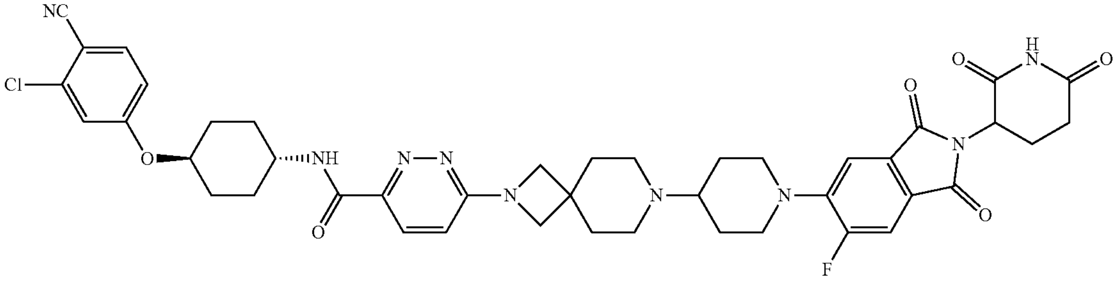
98
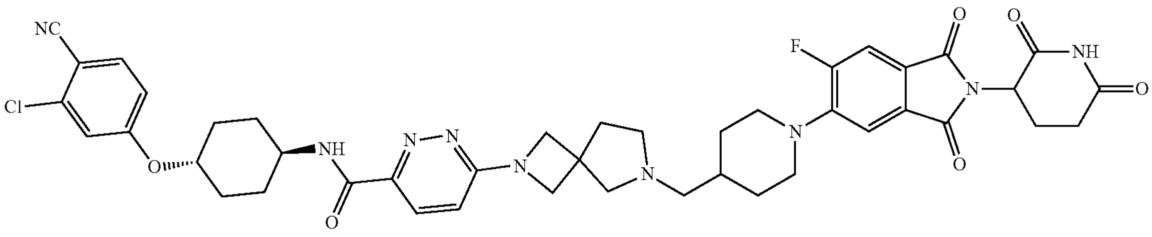

-continued
99
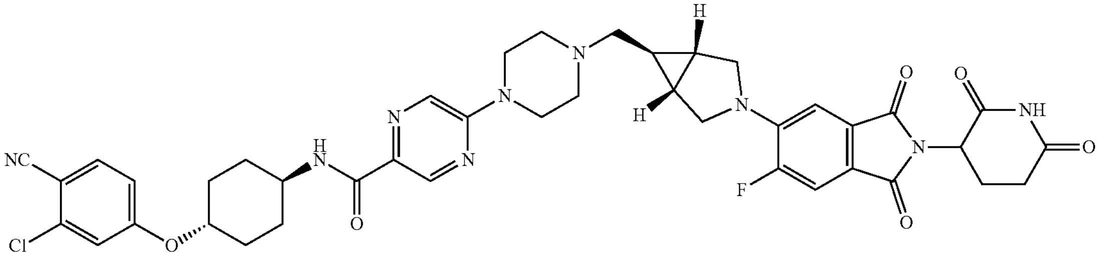
100
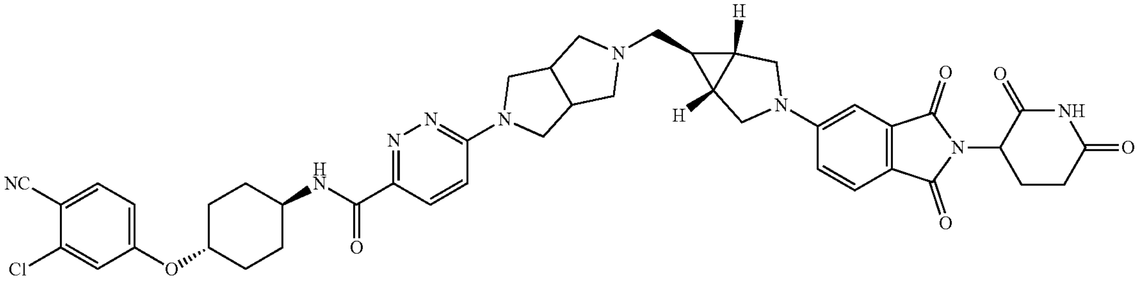
101
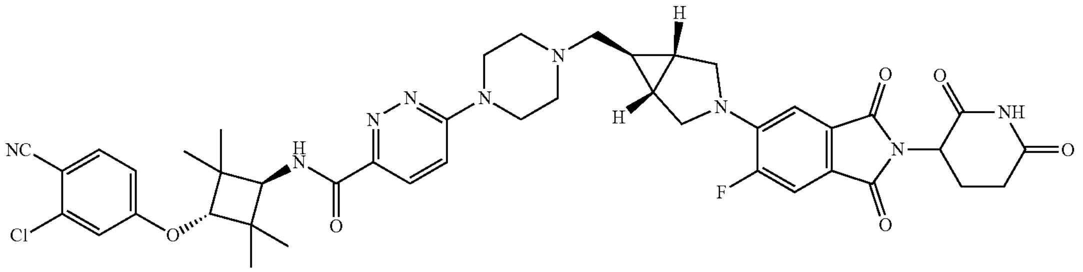
102
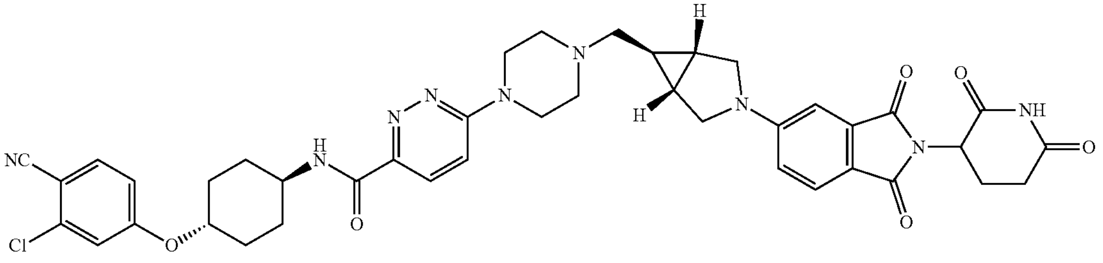
103
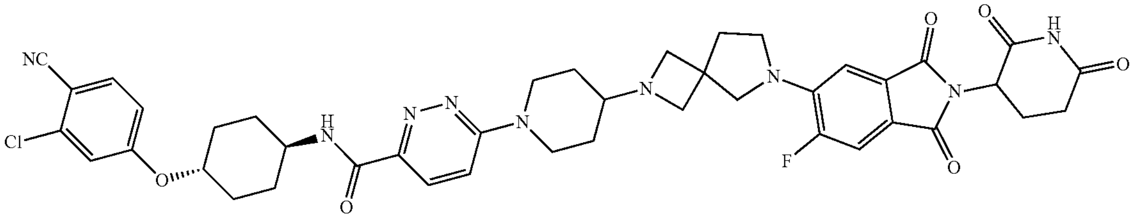
104
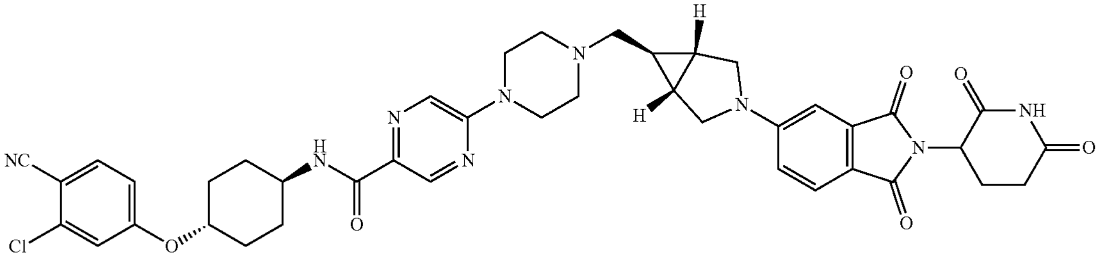

-continued
105
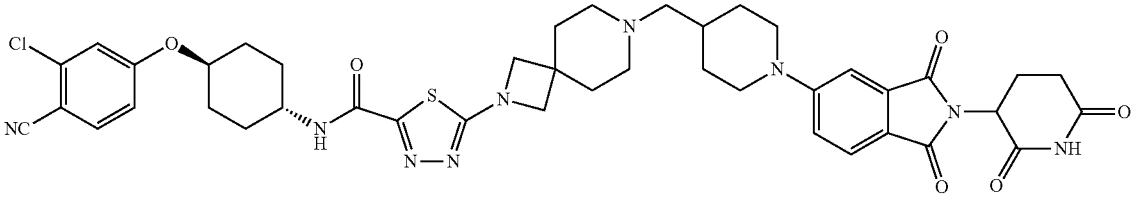
106
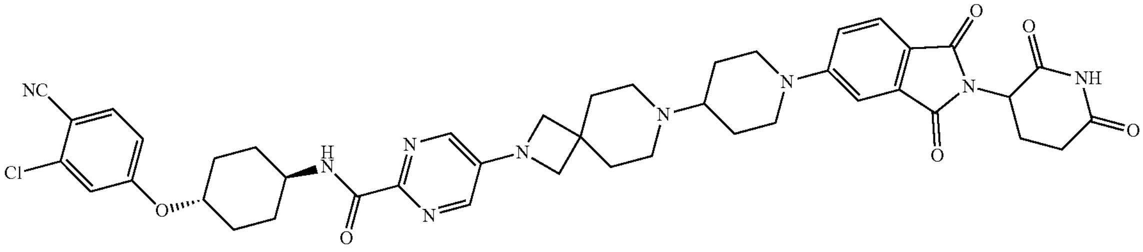
107
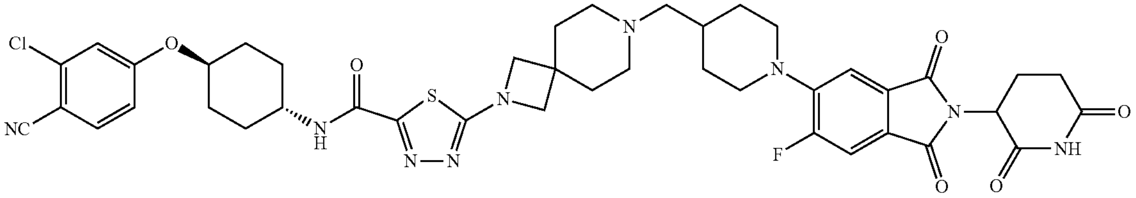
114
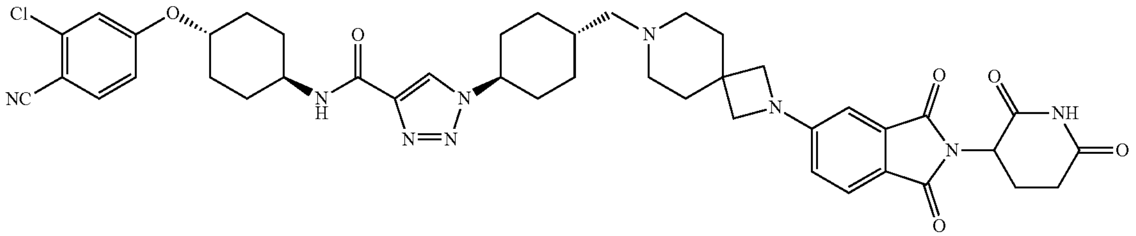
115
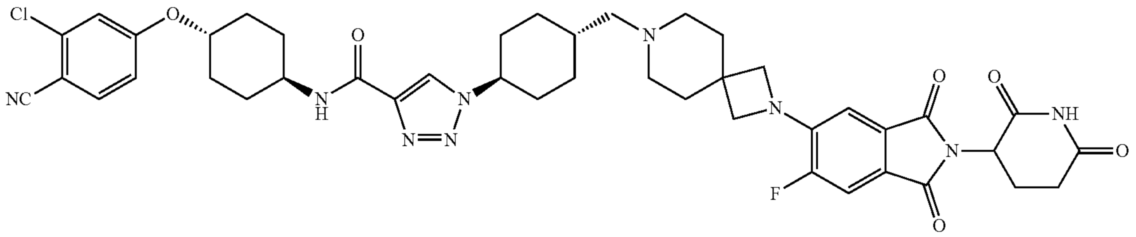
116
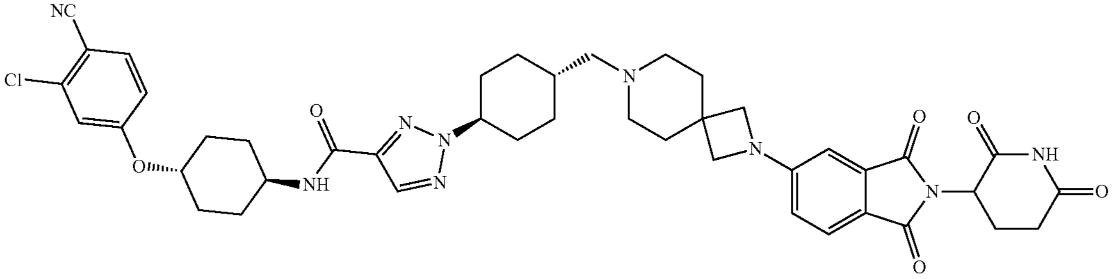

-continued
117
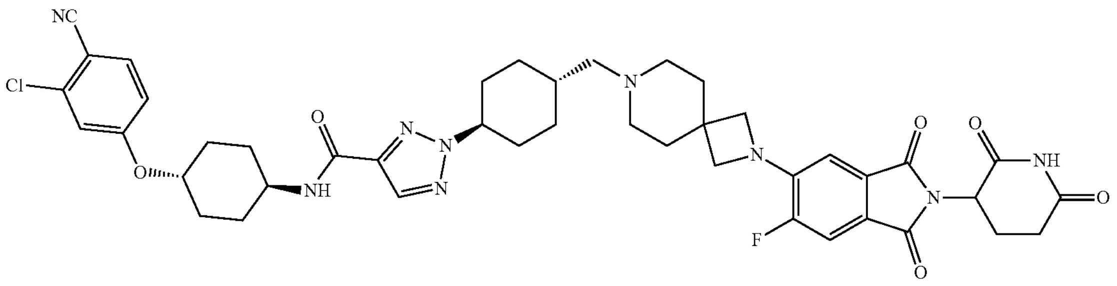
121
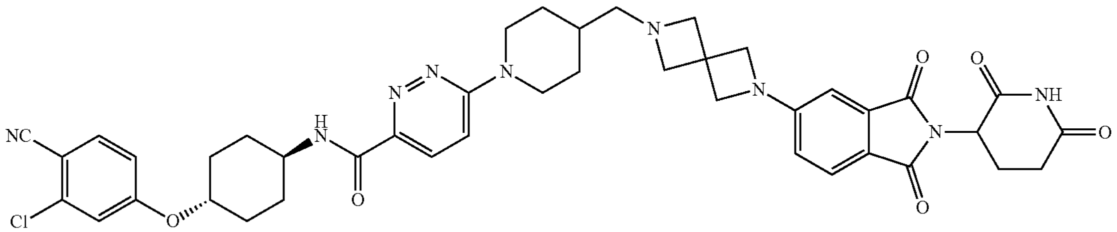
122
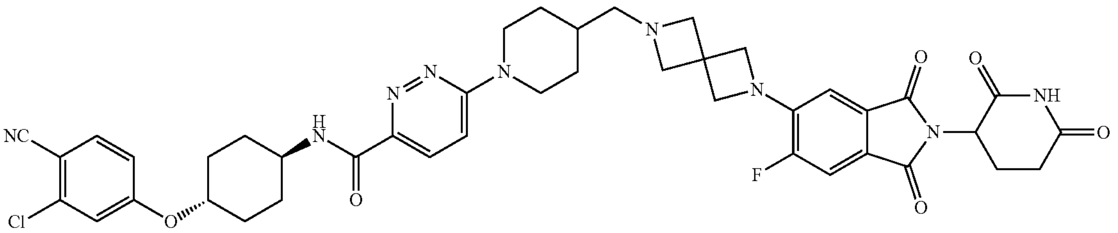
123
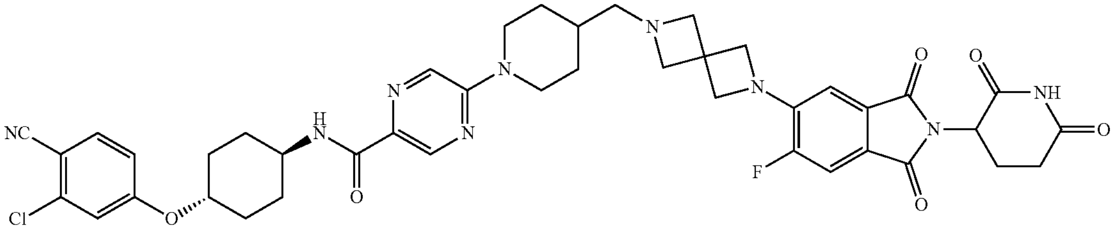
124
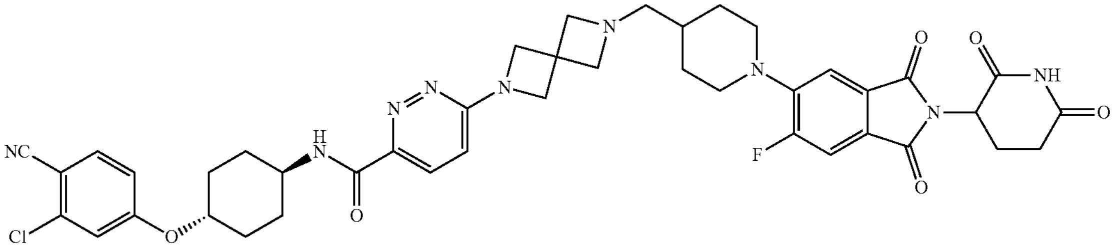
125
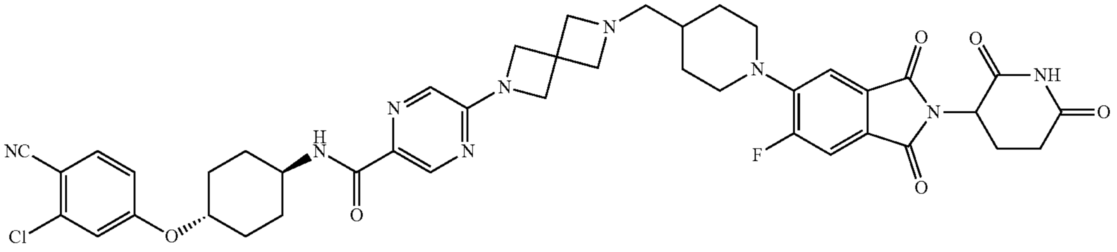

-continued
126
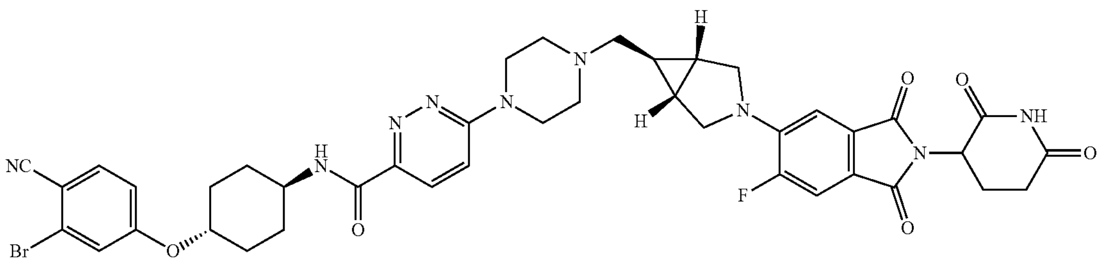
127
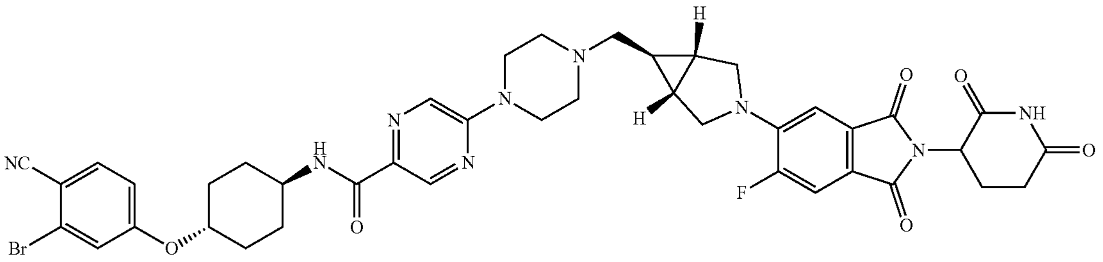
128
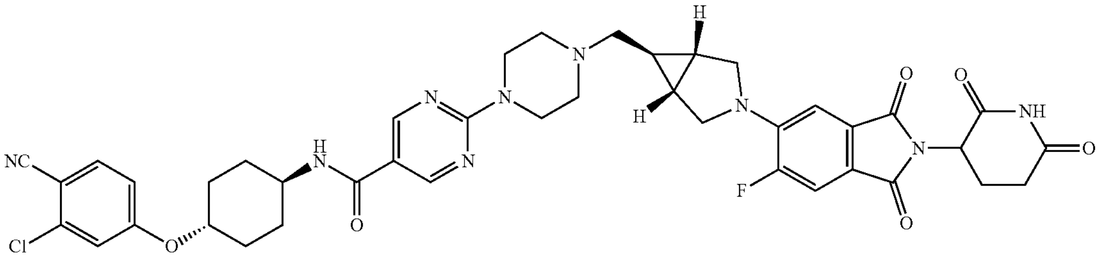
129
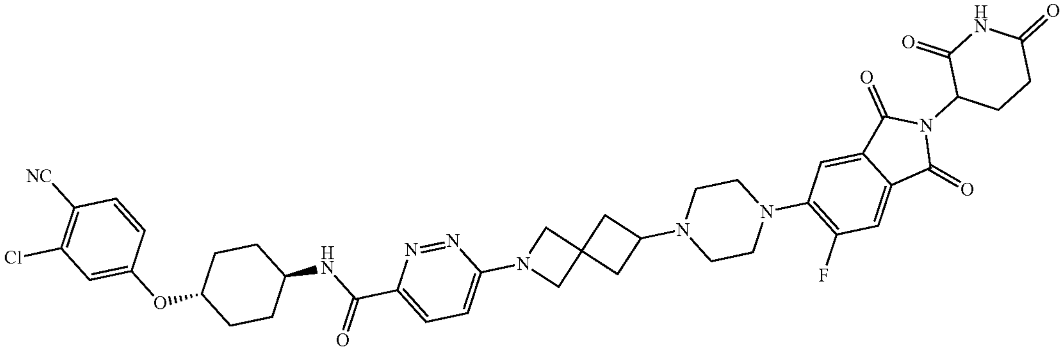
130
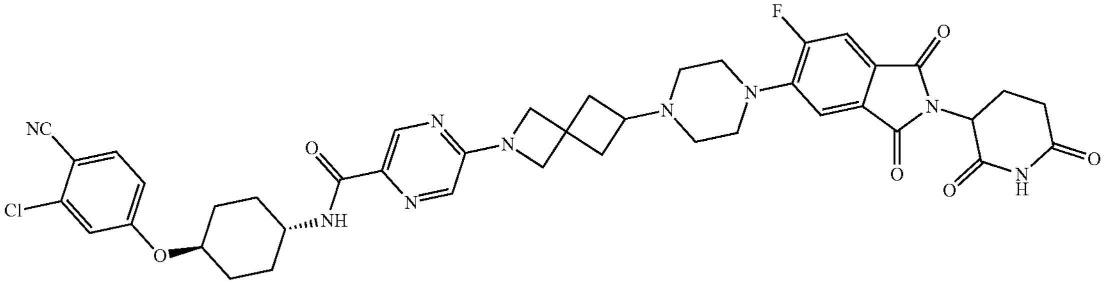

-continued
134
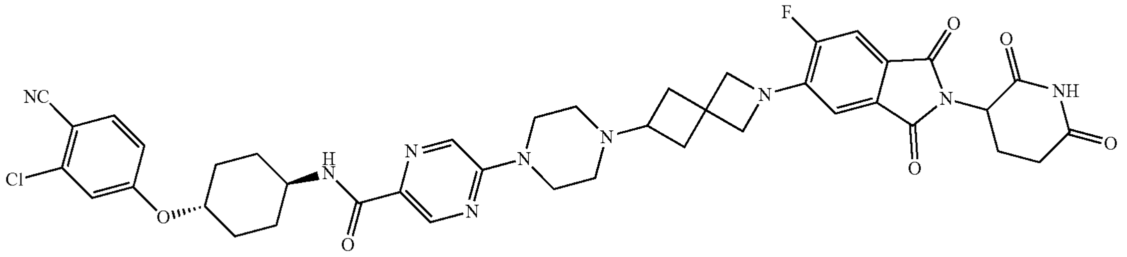
135
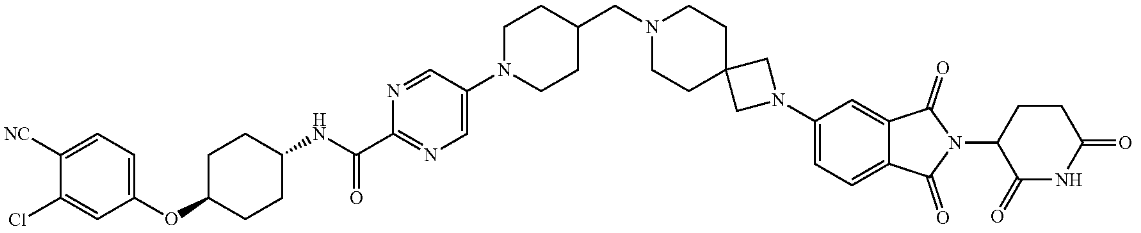
136
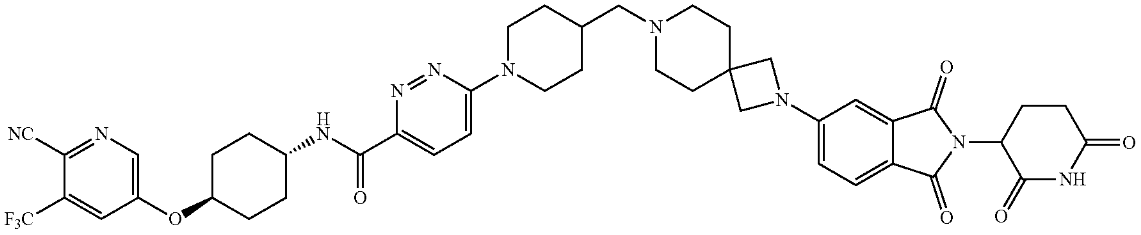
137
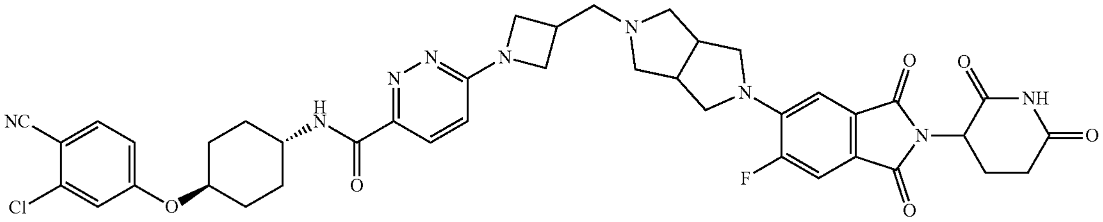
138
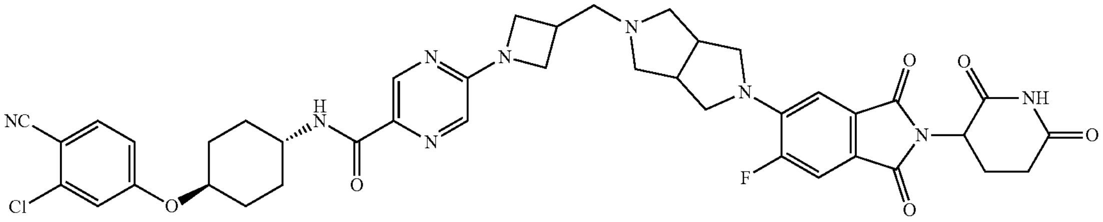
140
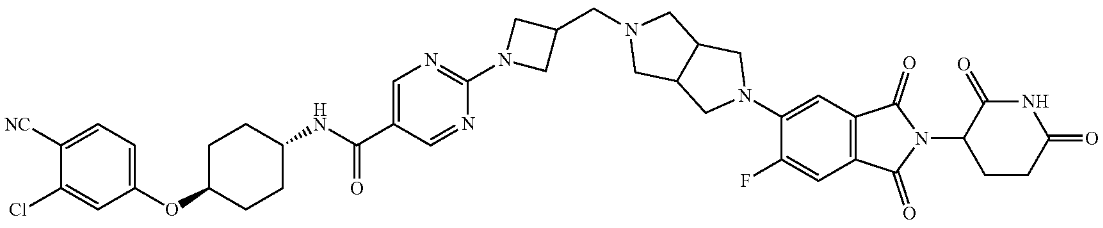

-continued
141
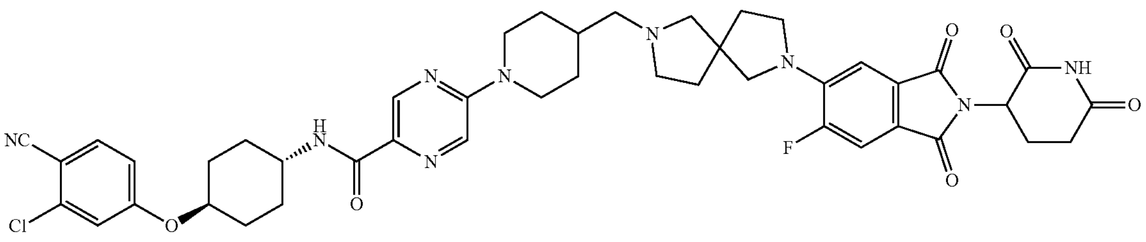
142
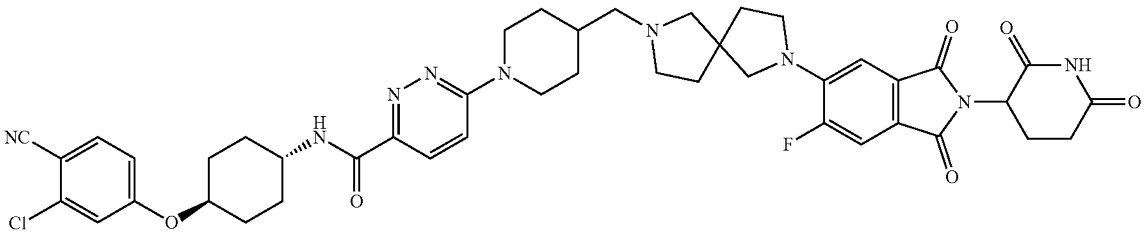
148
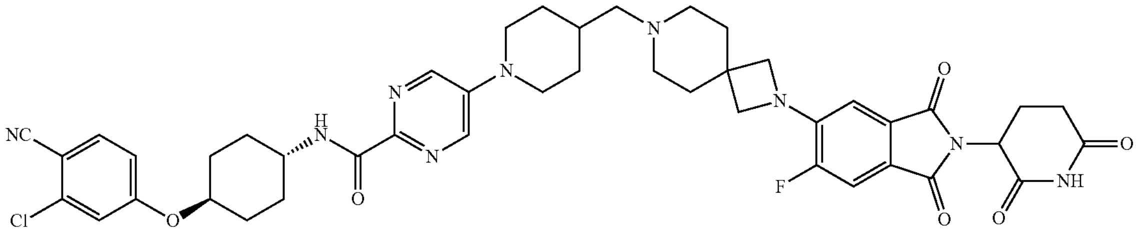
149
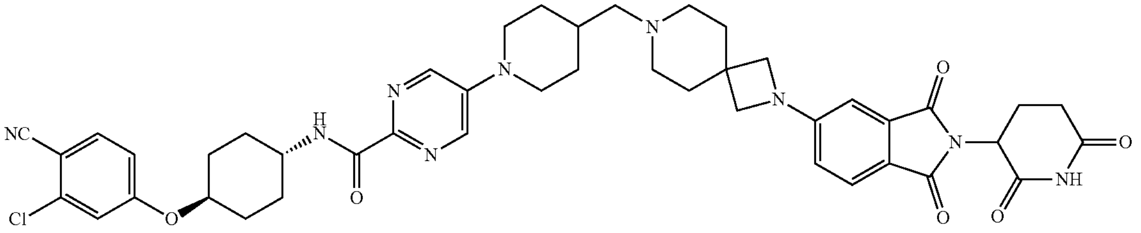
150
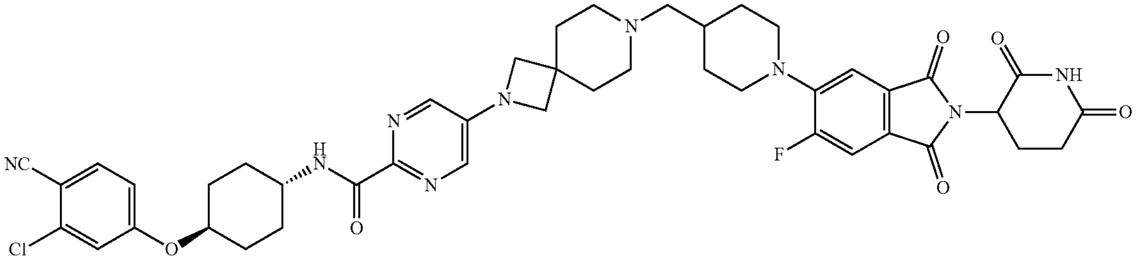
151
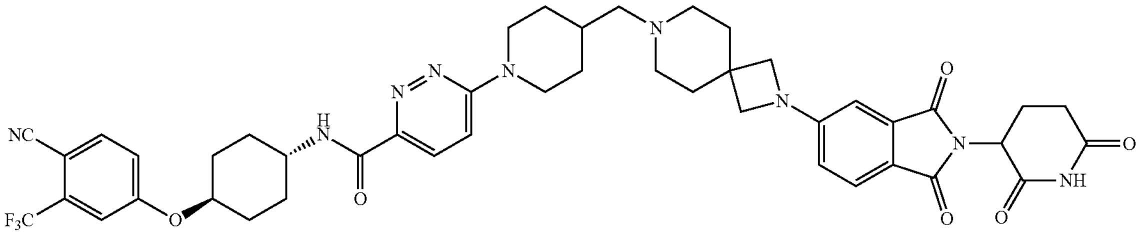

-continued
152
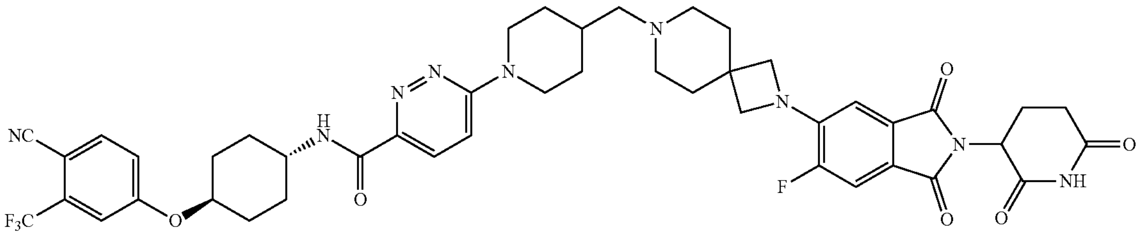
153
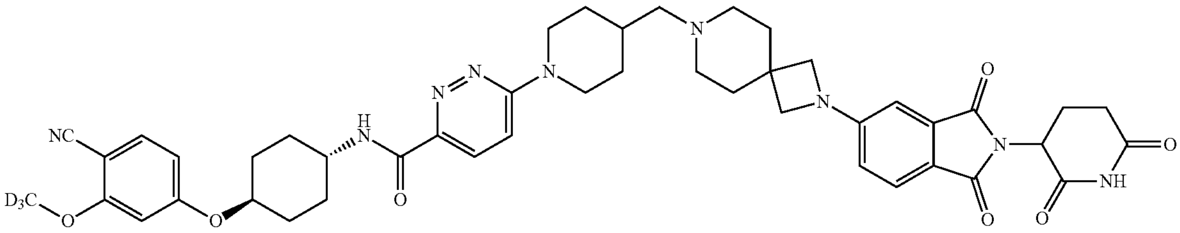
154
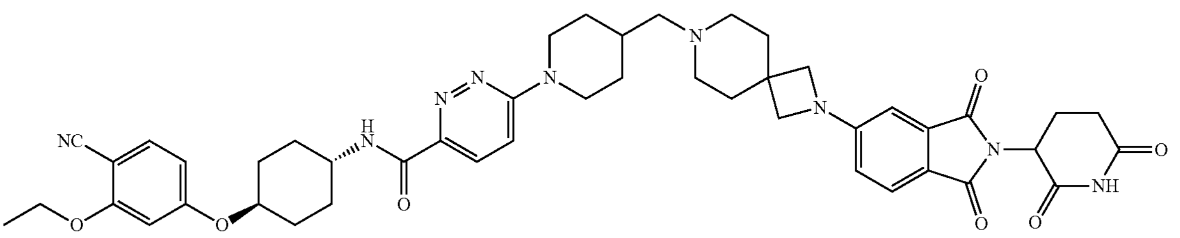
156
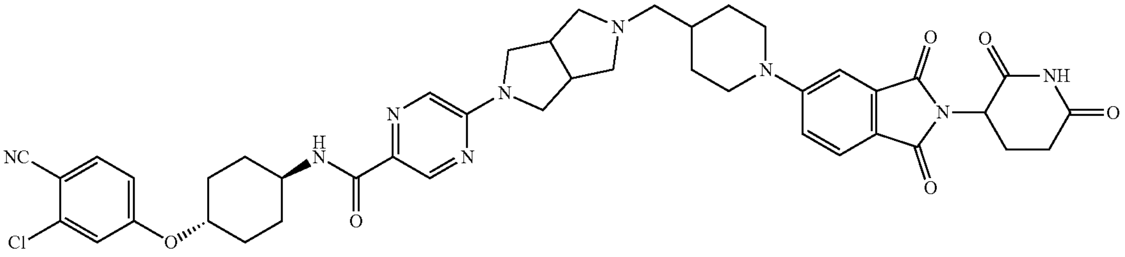
157
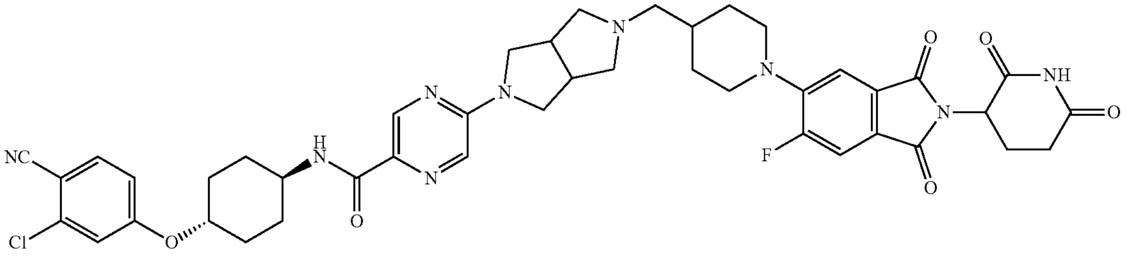
158
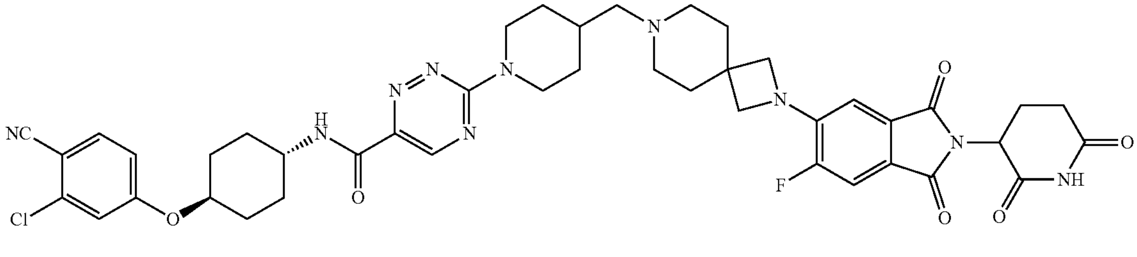

-continued
159
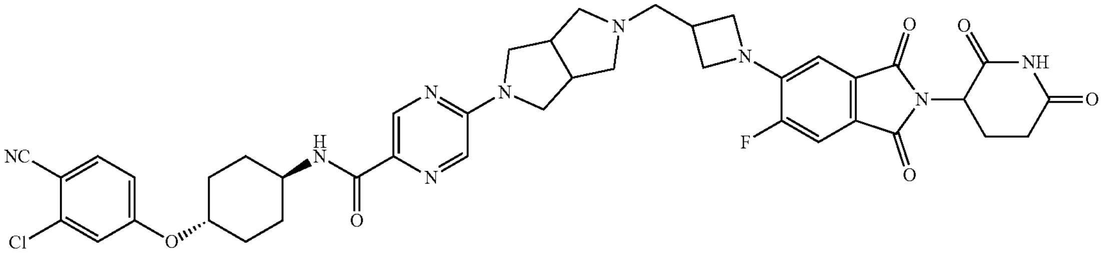
160
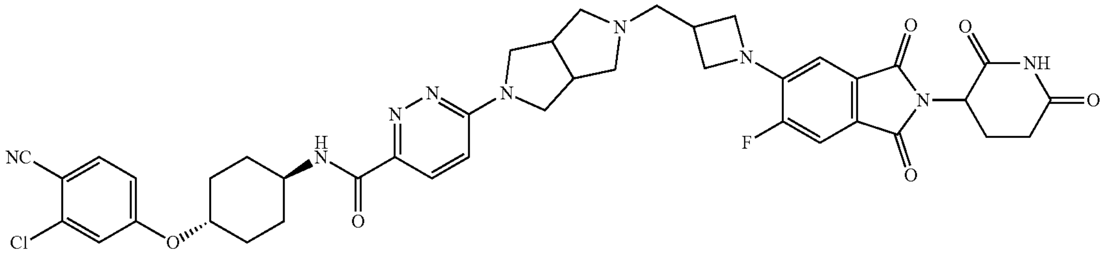
161
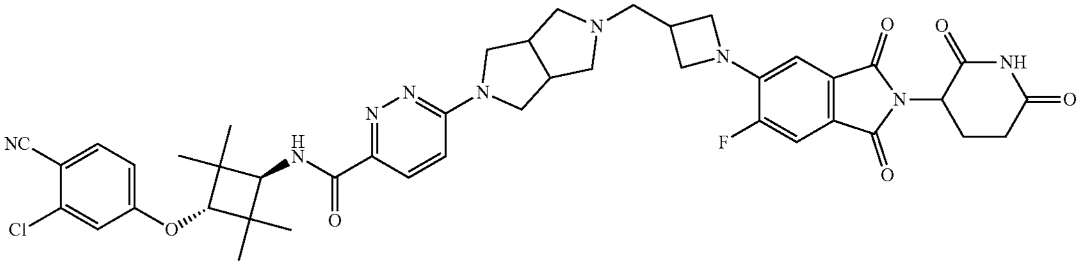
162
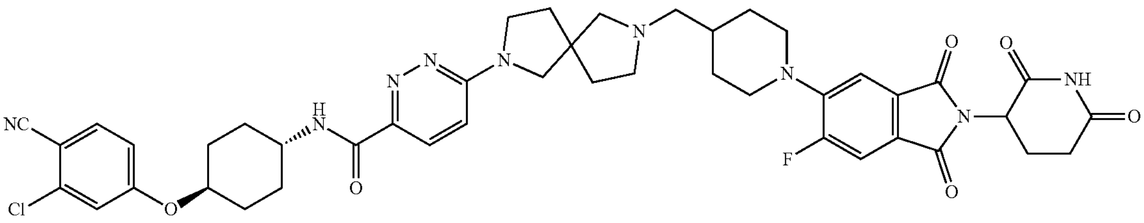
163
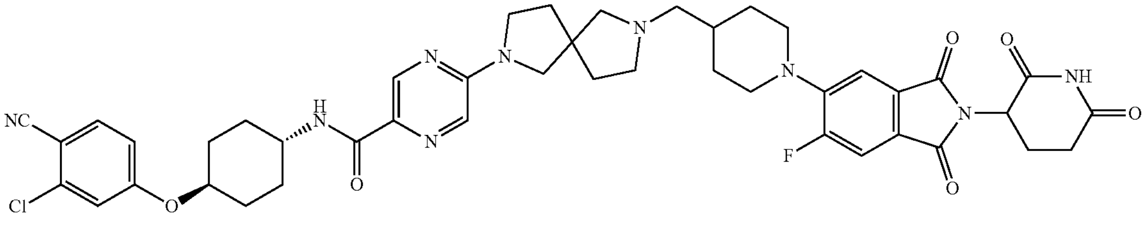
164
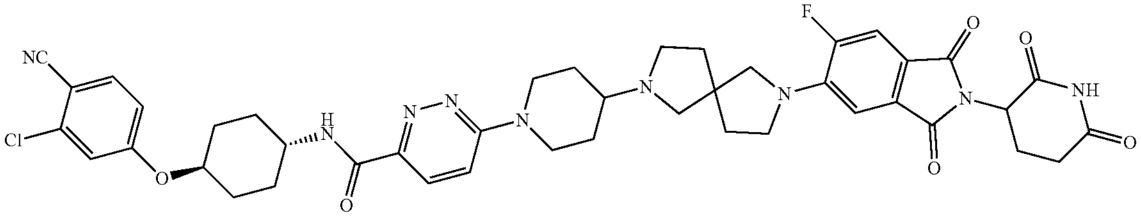

-continued
165
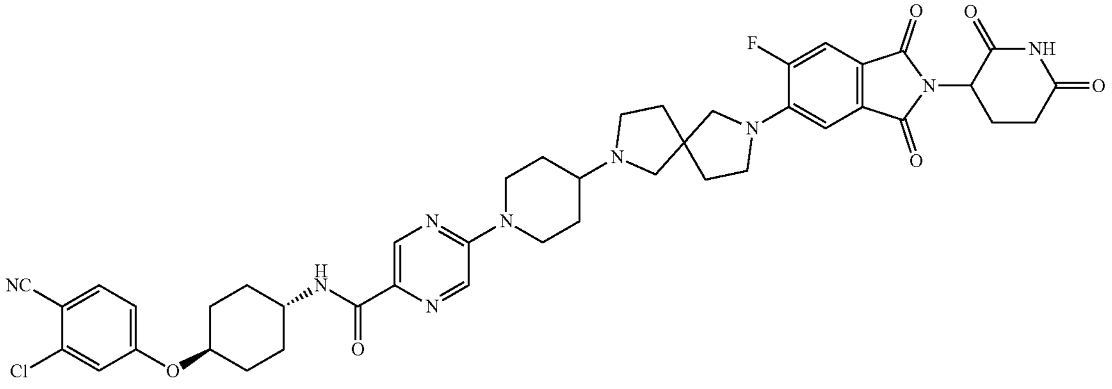
166
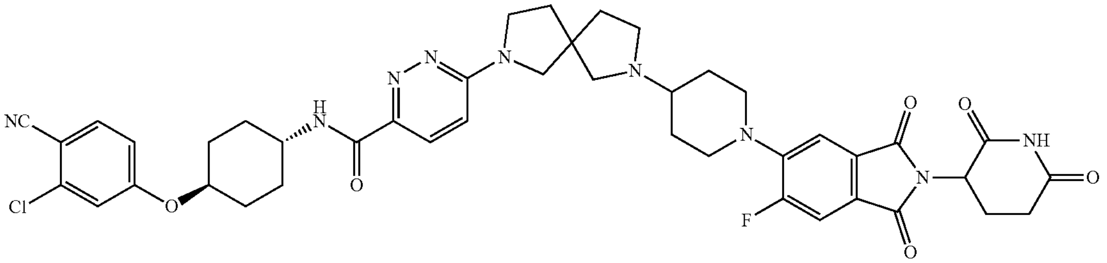
167
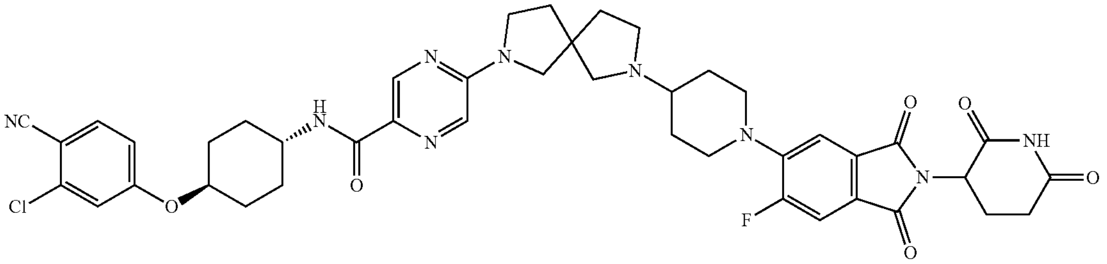
168
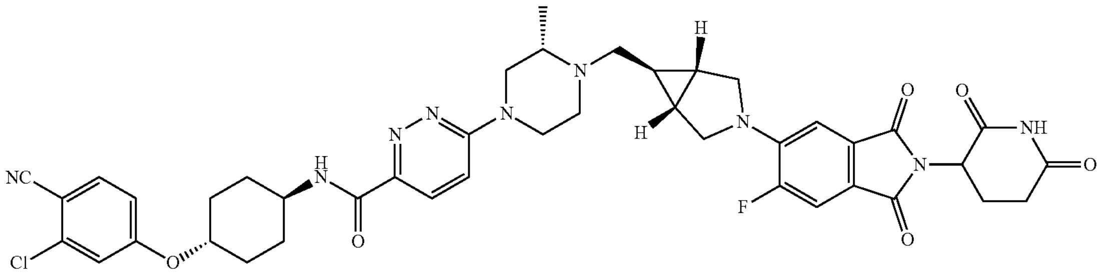
169
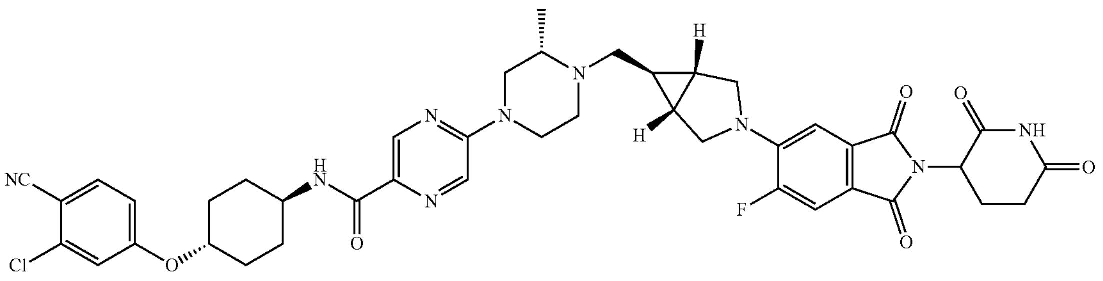

-continued
170
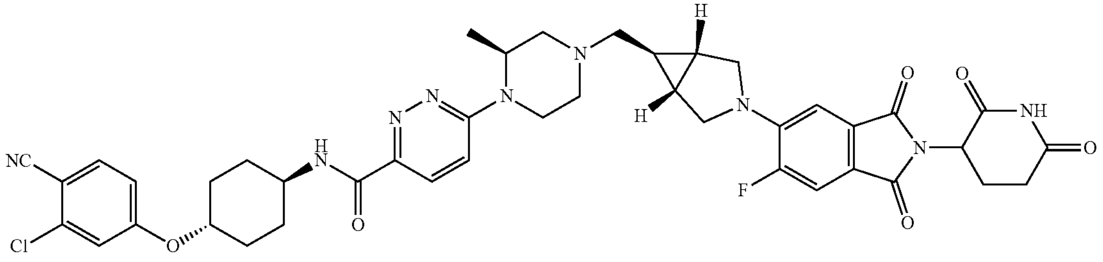
171
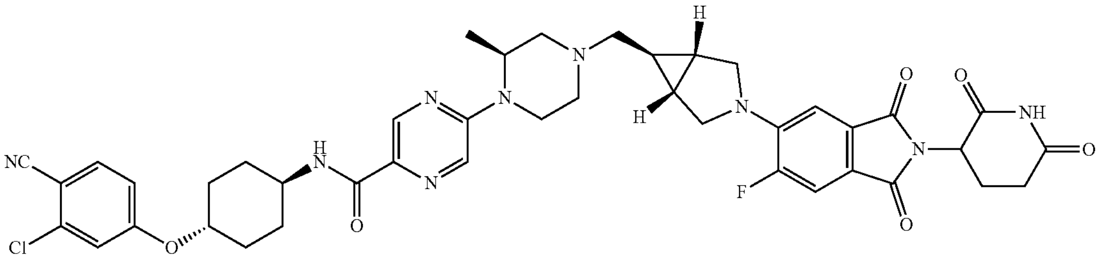
176
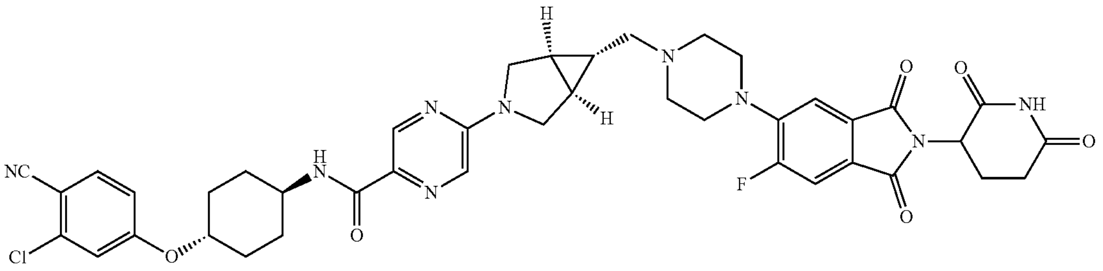
177
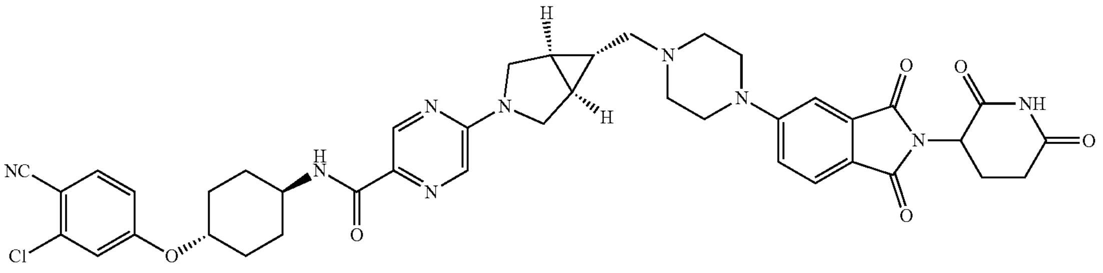
178
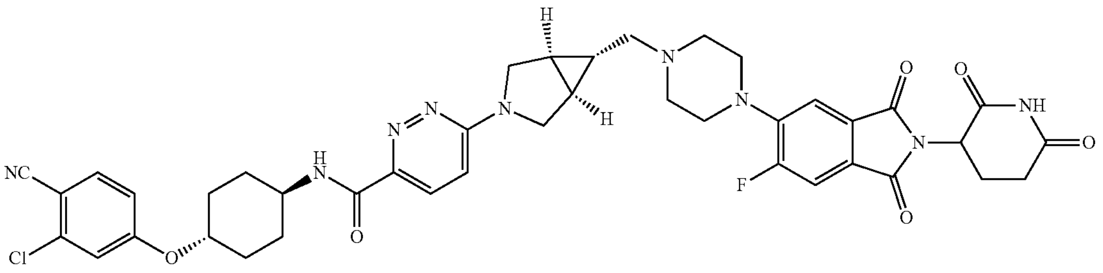
179
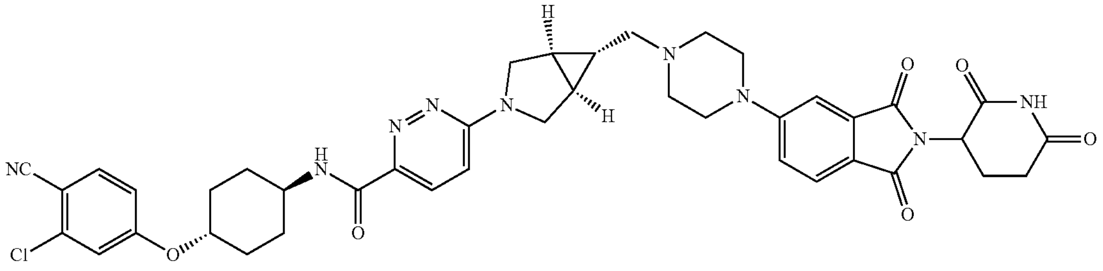

-continued
180
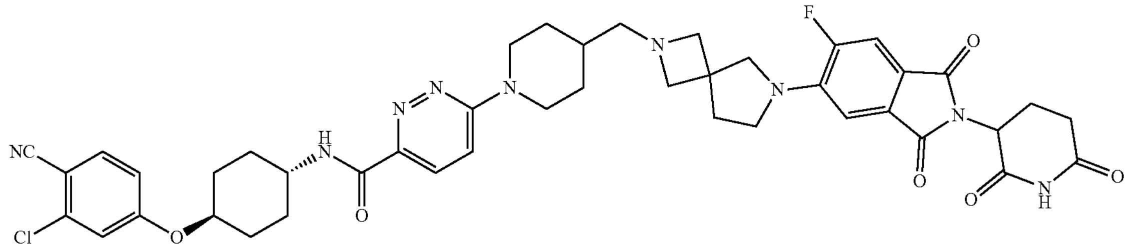
181
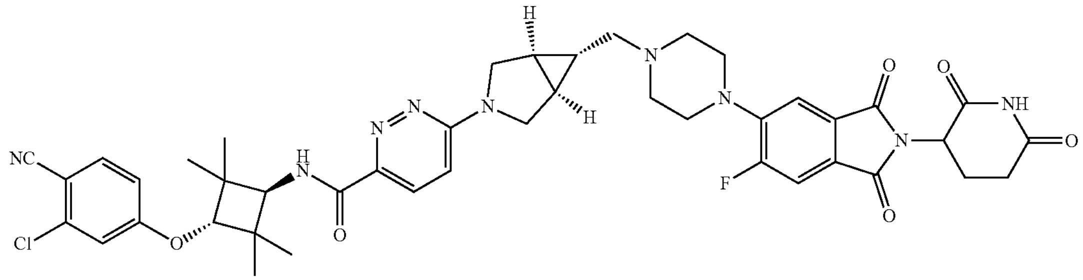
182
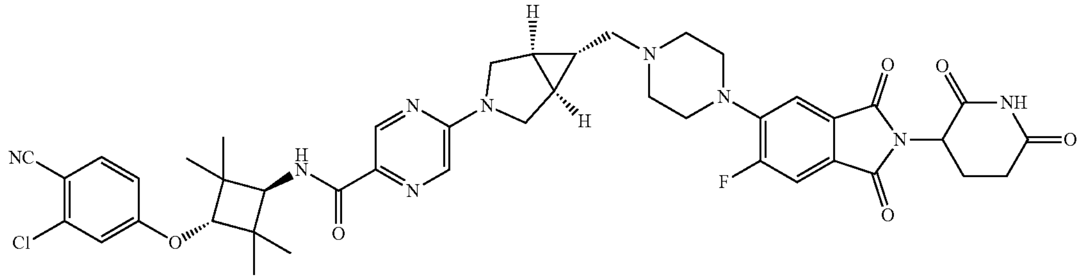
183
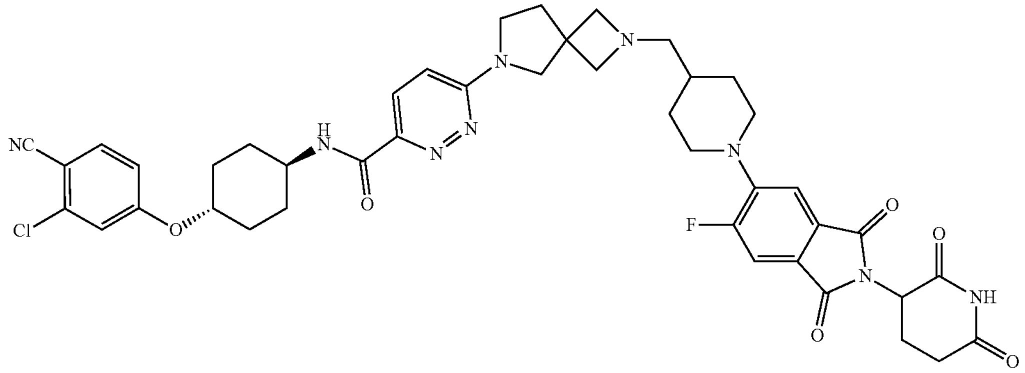
184
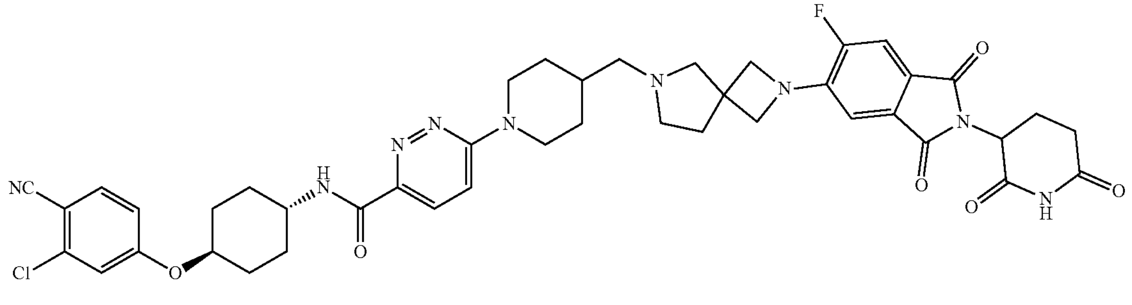

-continued
185
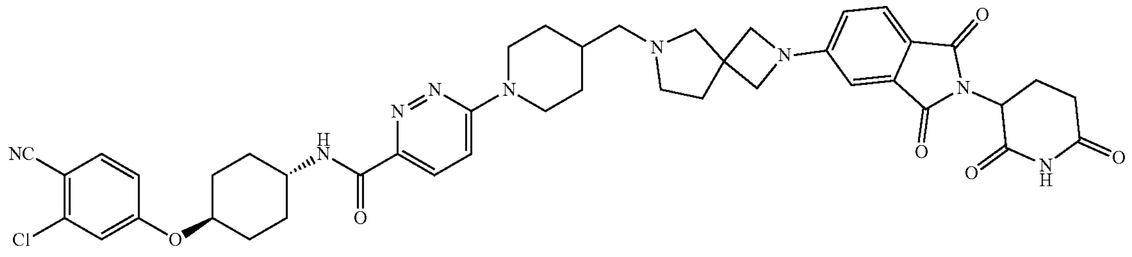
186
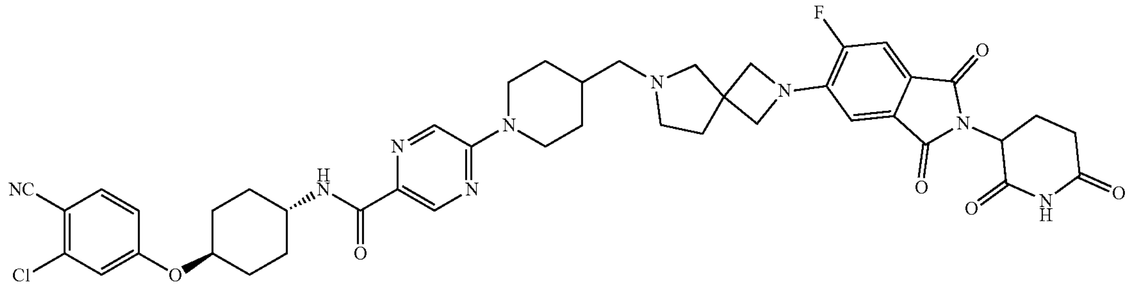
187
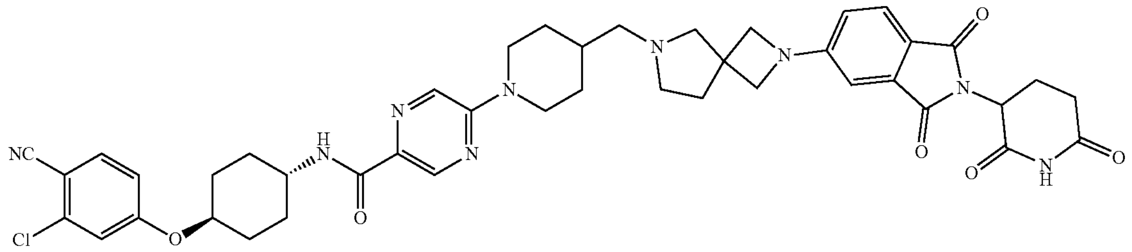
188
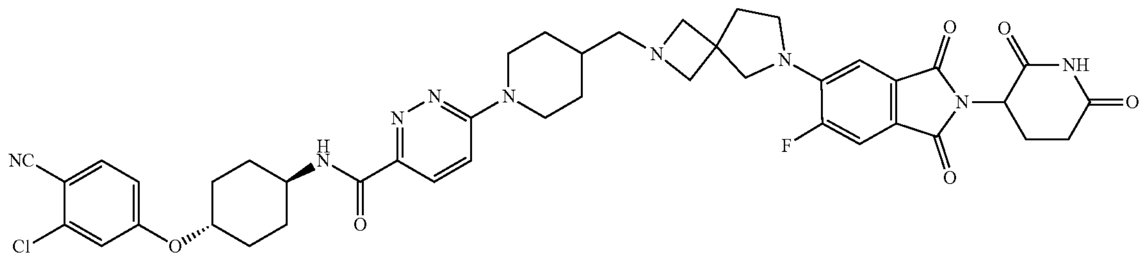
189
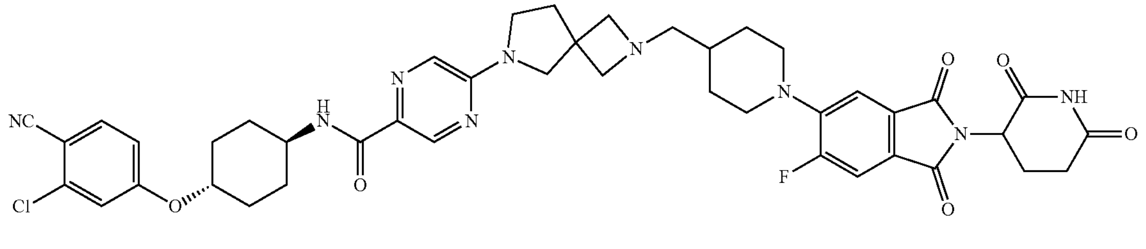
190
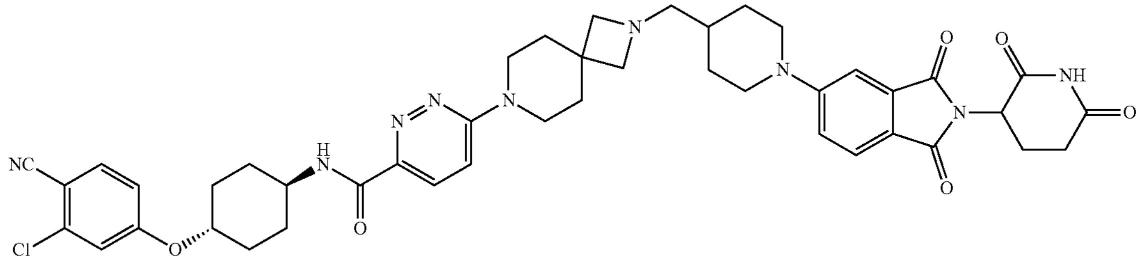

-continued
191
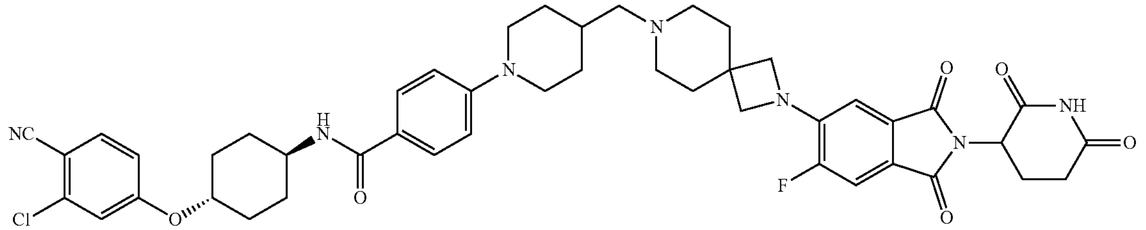
192
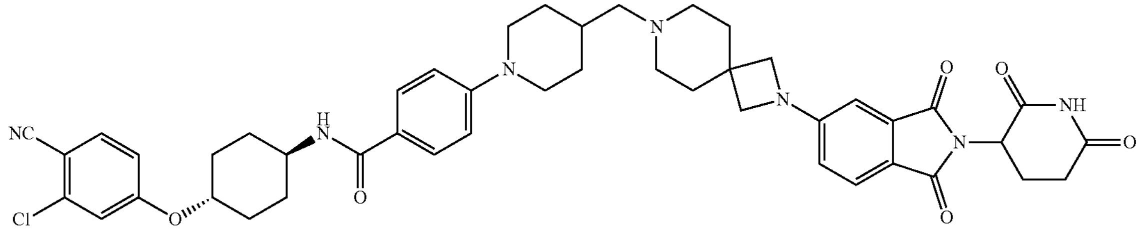
193
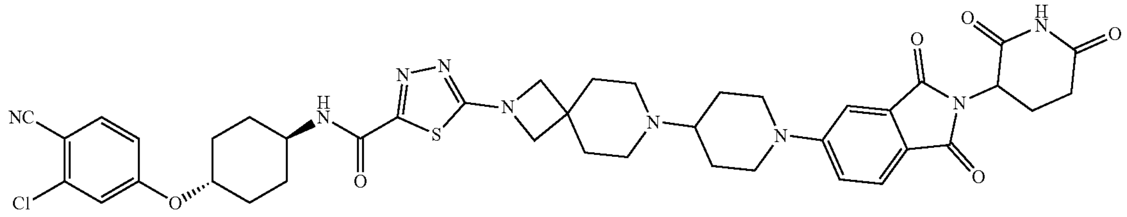
194
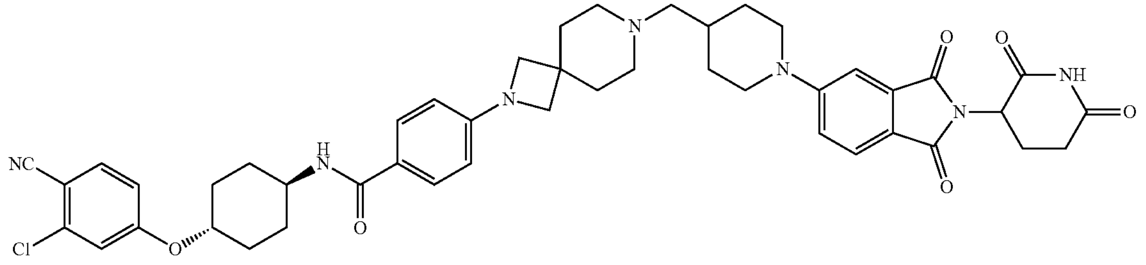
195
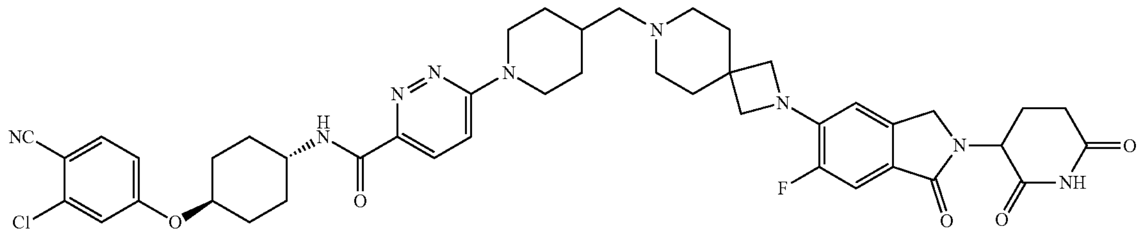
196
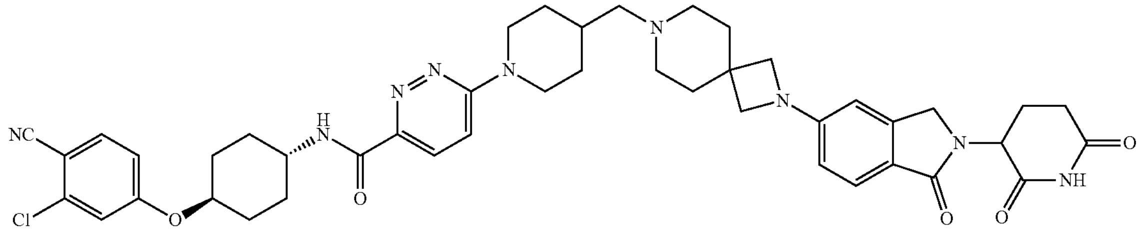

-continued
197
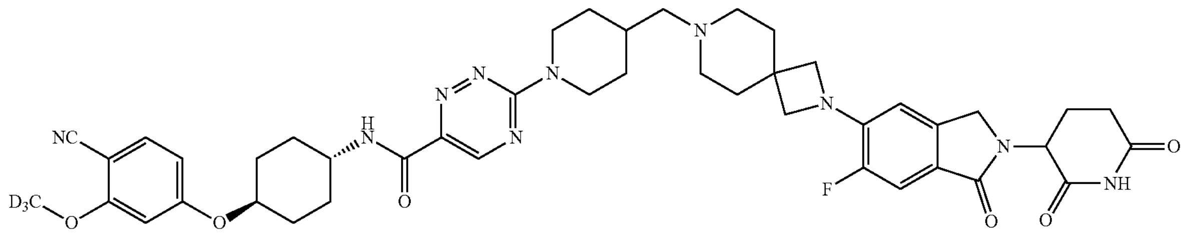
220
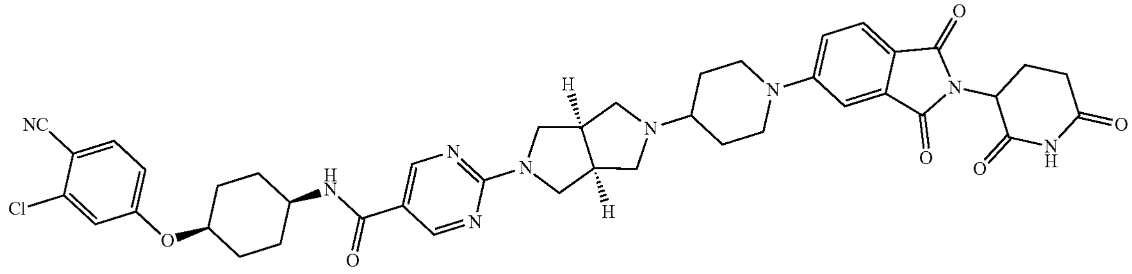
221
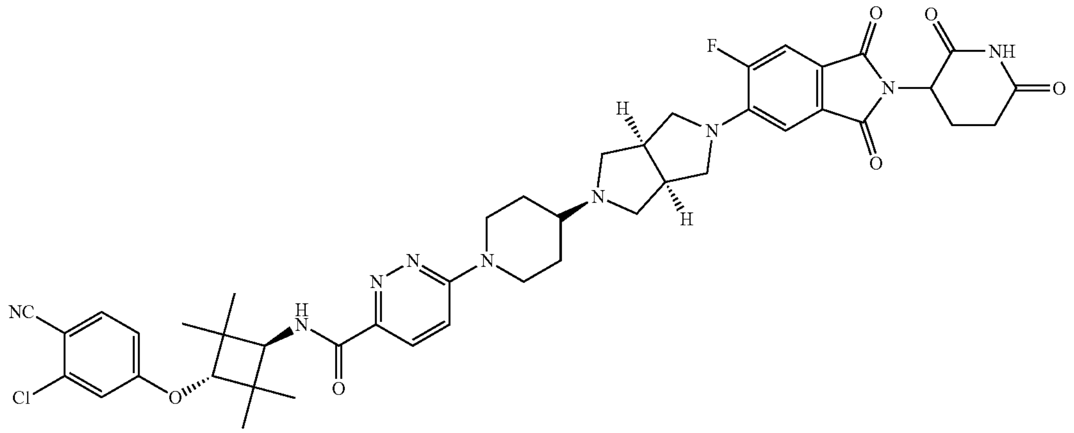
222
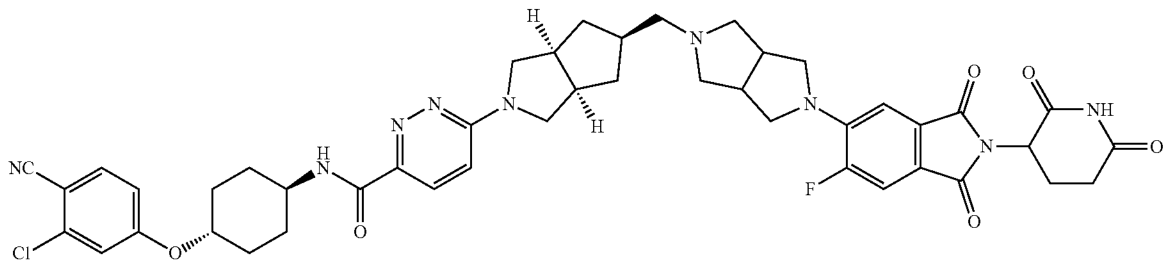

-continued
223
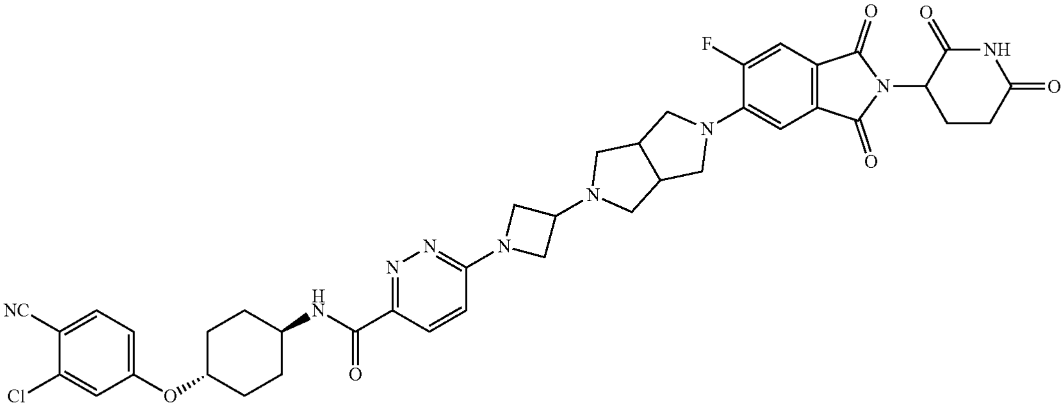
224
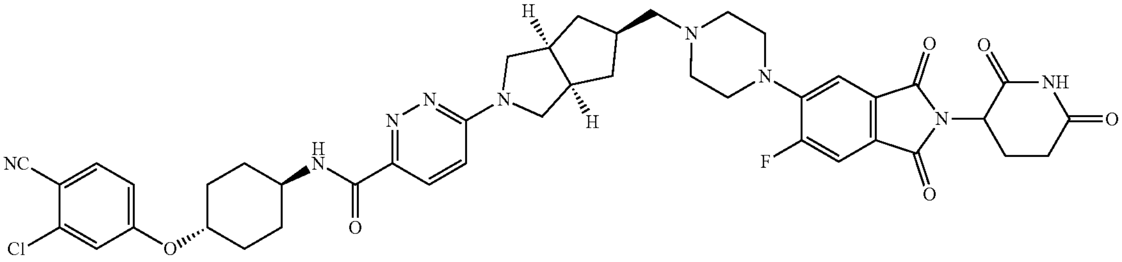
225
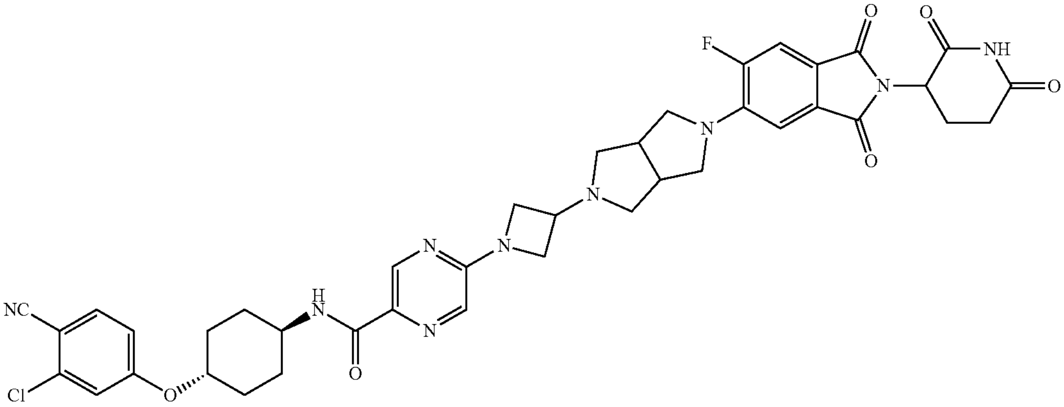
226
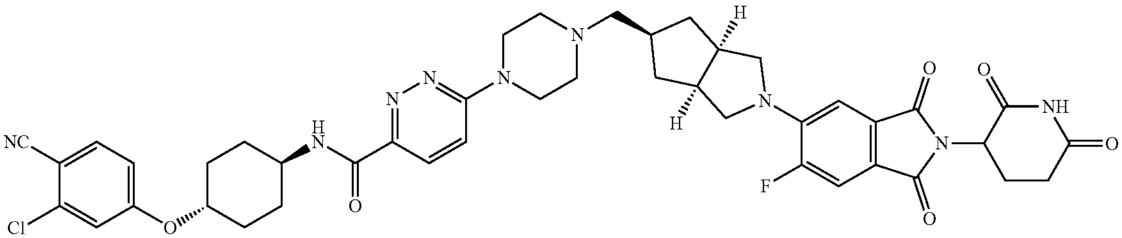
228
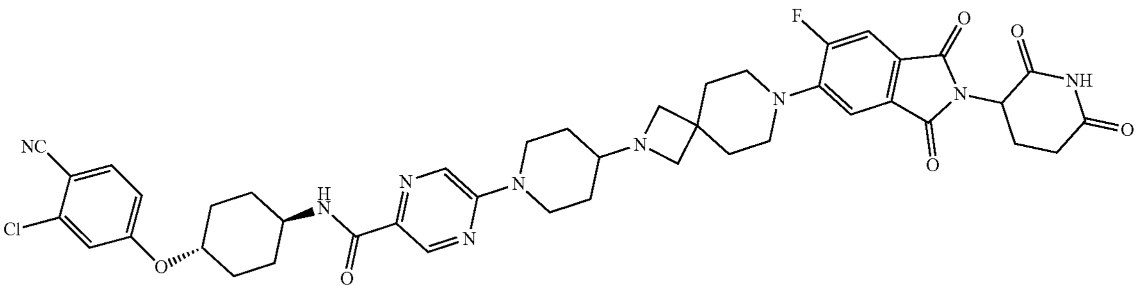

-continued
229
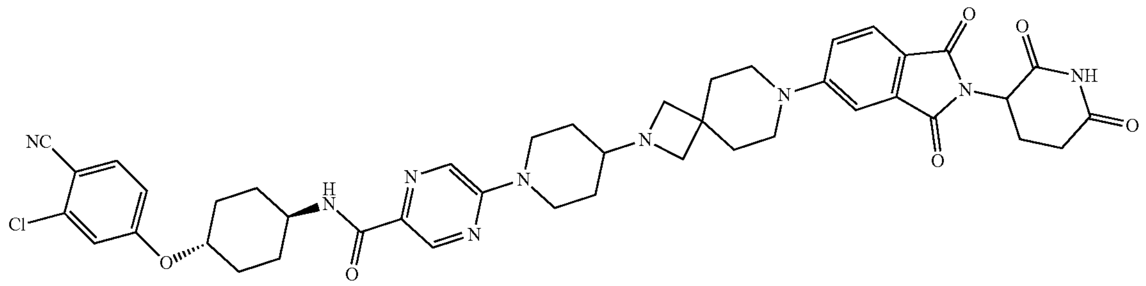
230
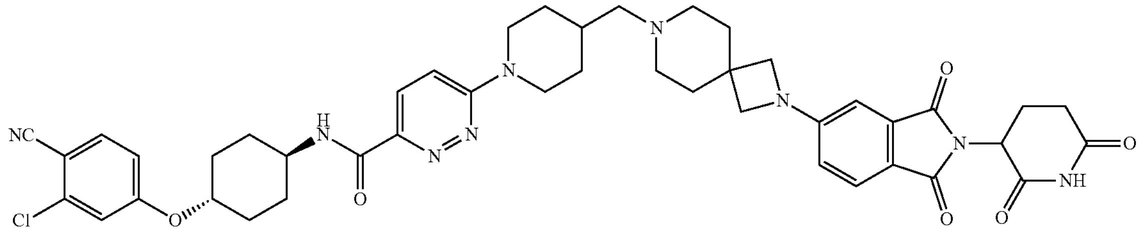
231
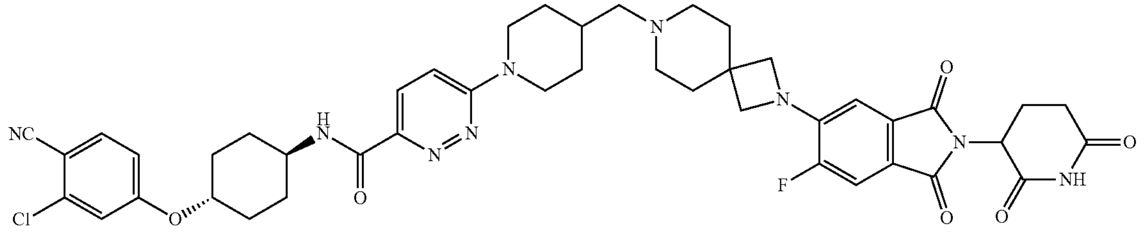
232
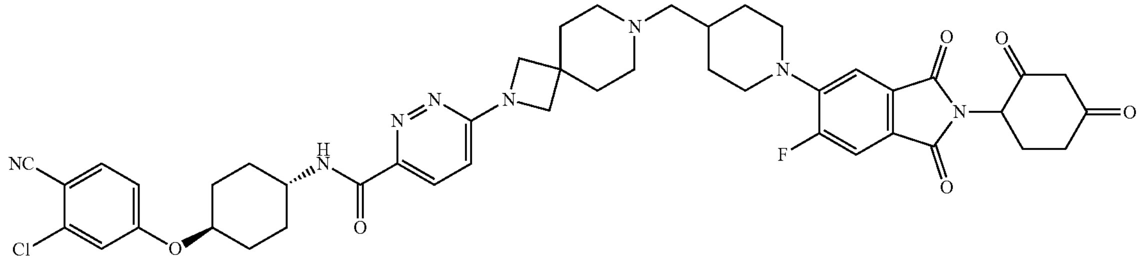
233
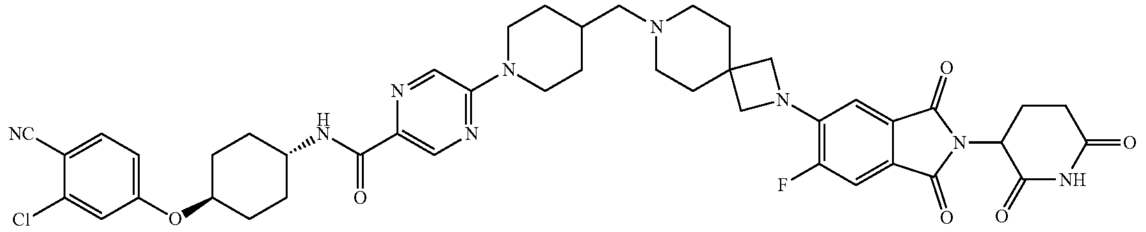
234
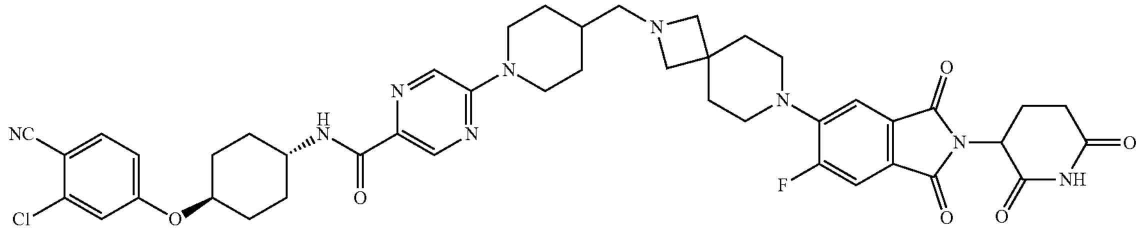

-continued
235
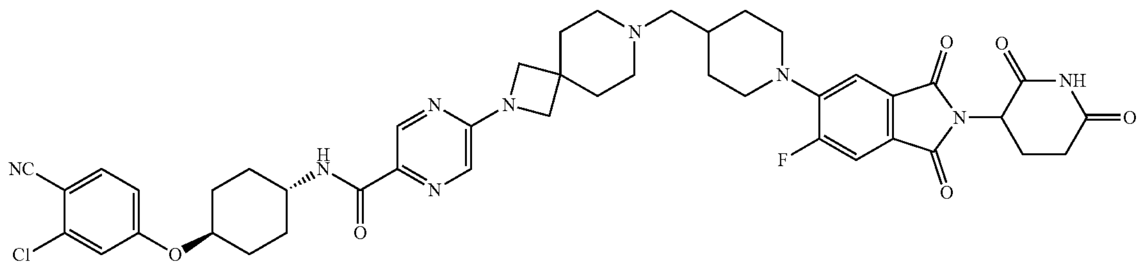
236
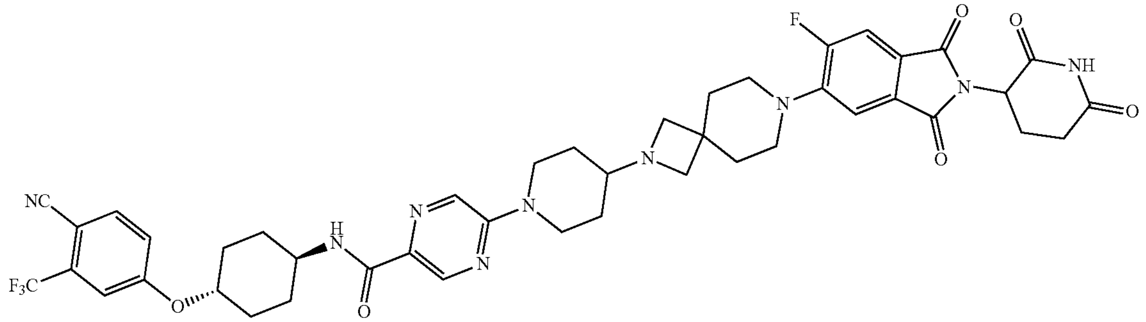
237
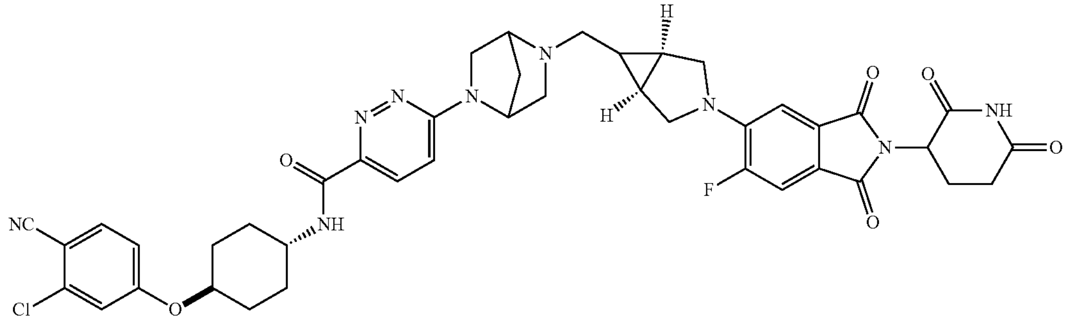
238
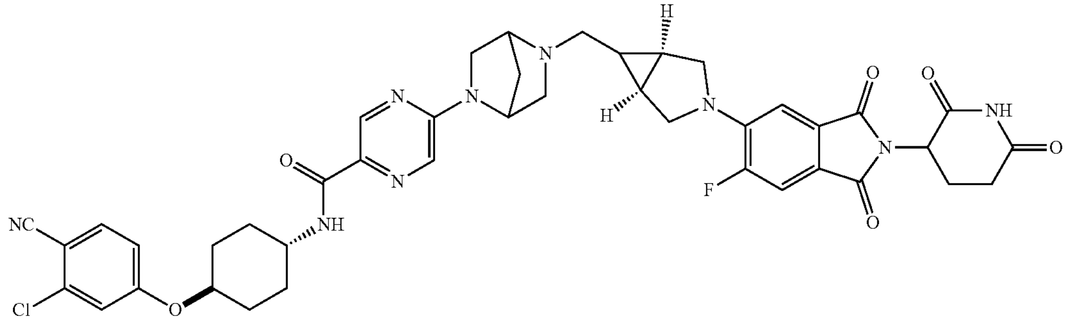
241
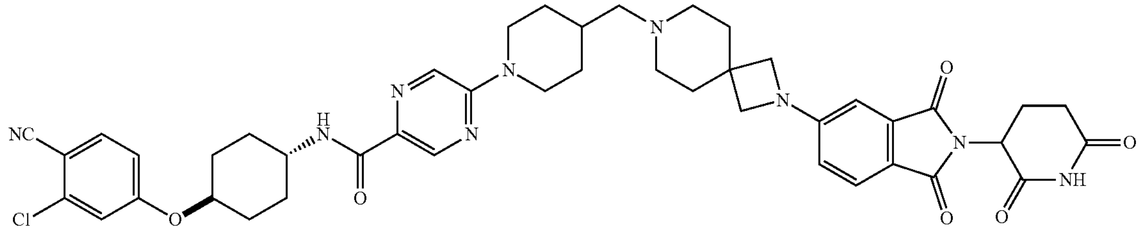

-continued
242
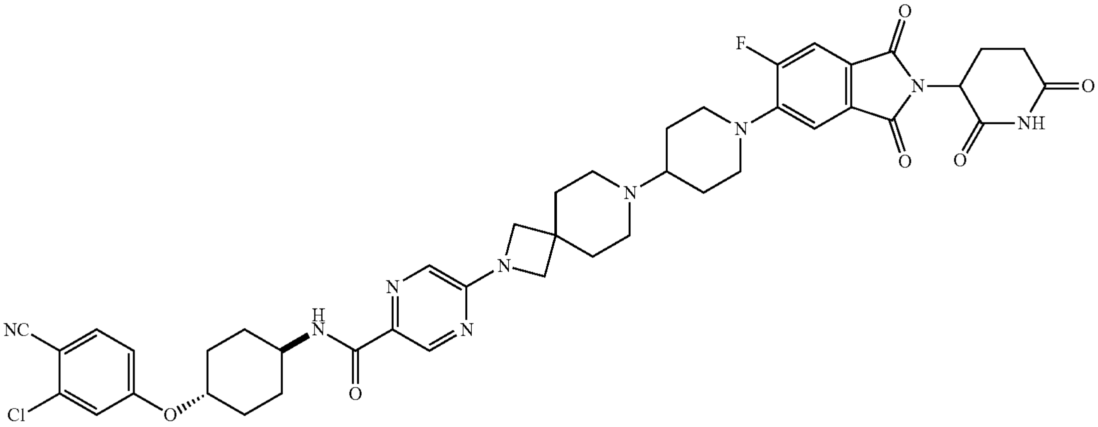
243
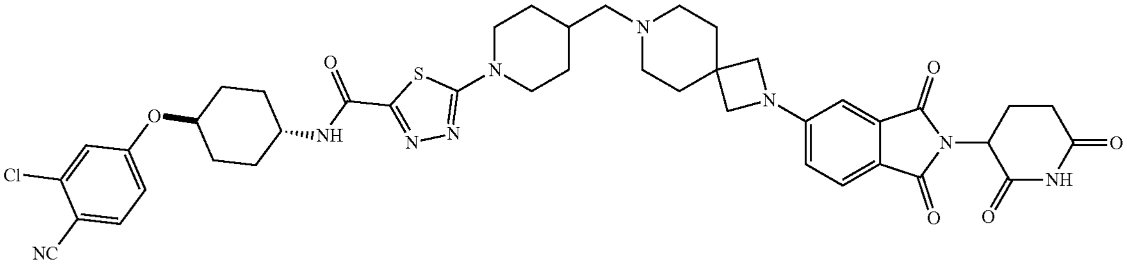
244
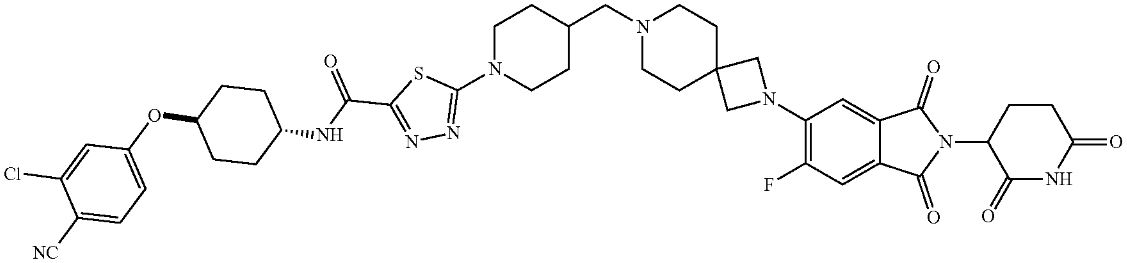
245
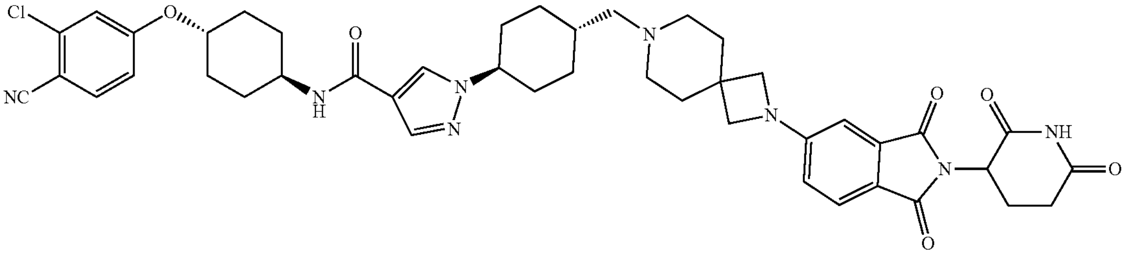
246
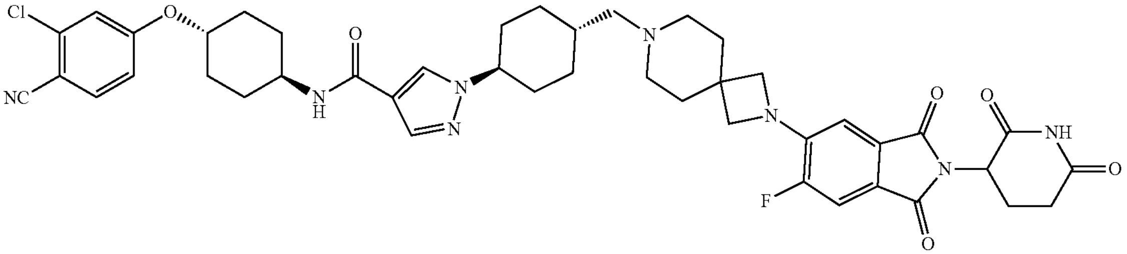

-continued
252
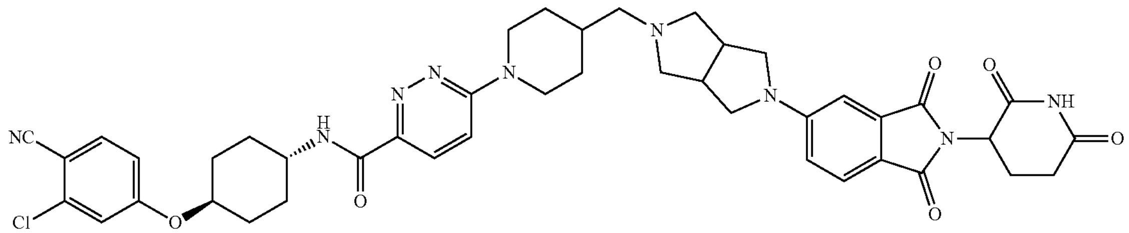
253
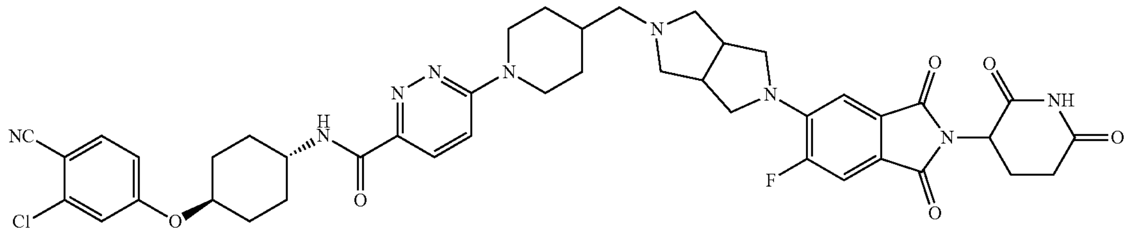
254
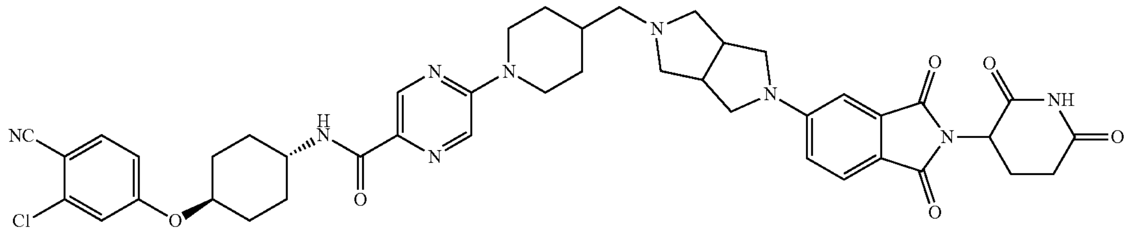
255
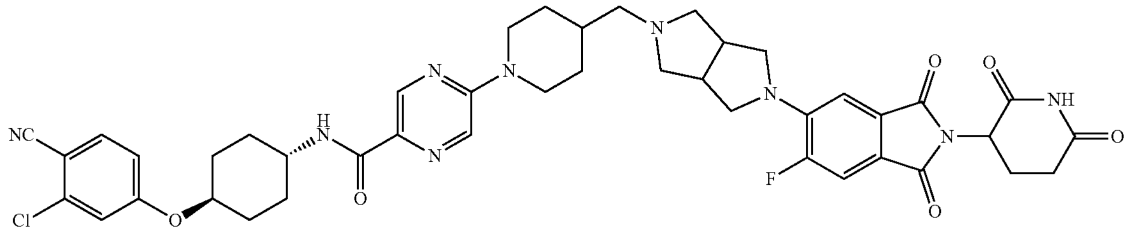
256
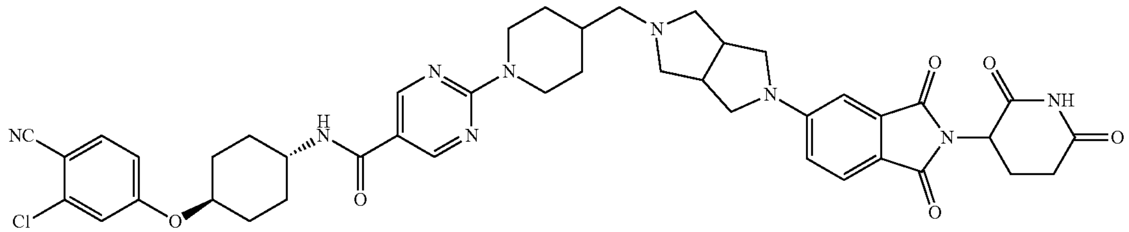
257
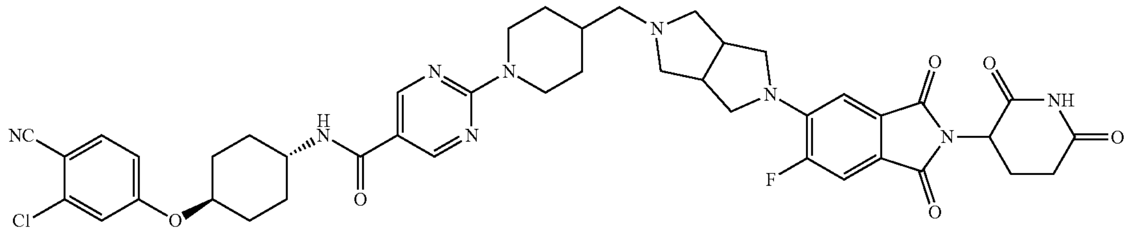

-continued
258
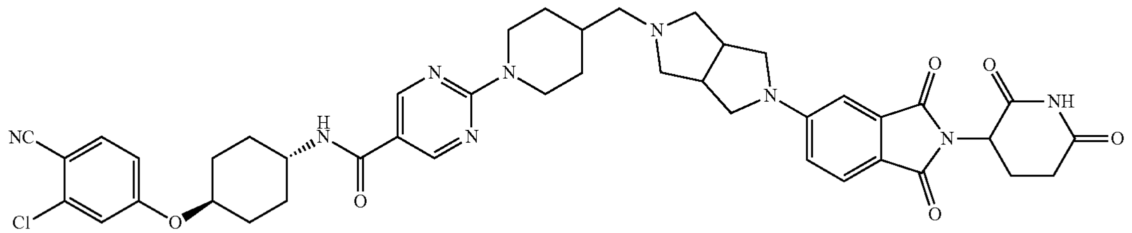
259
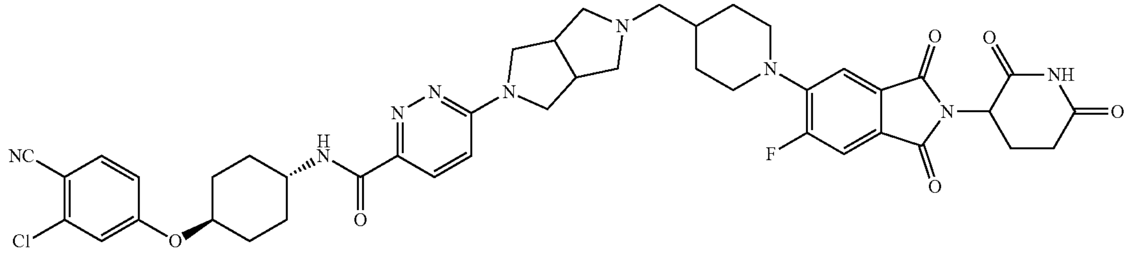
260
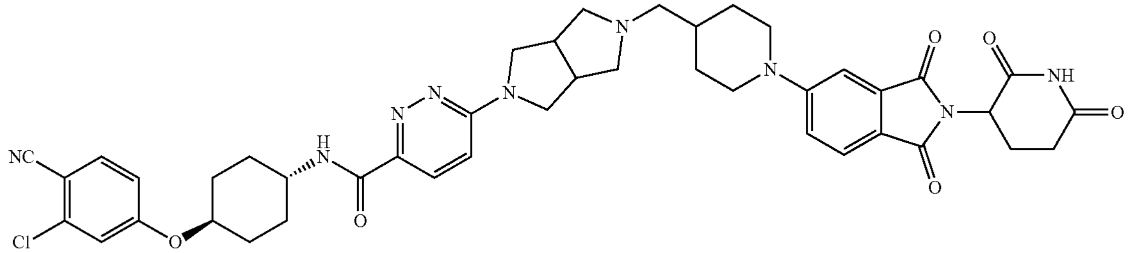
261
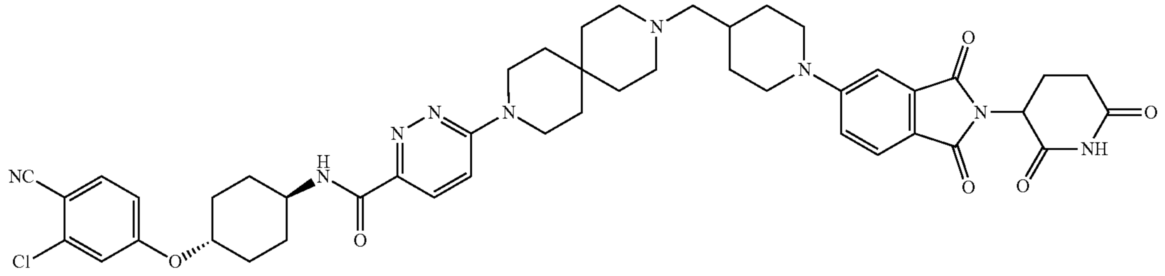
262
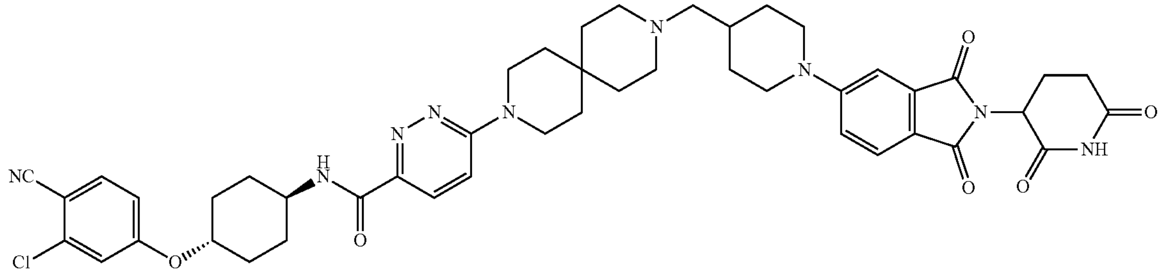
263
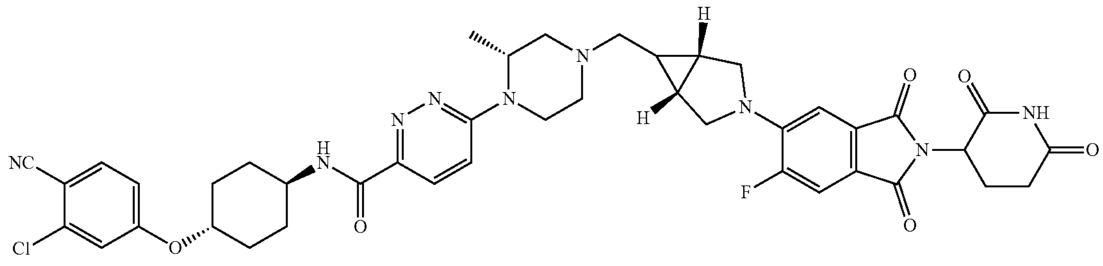

-continued
264
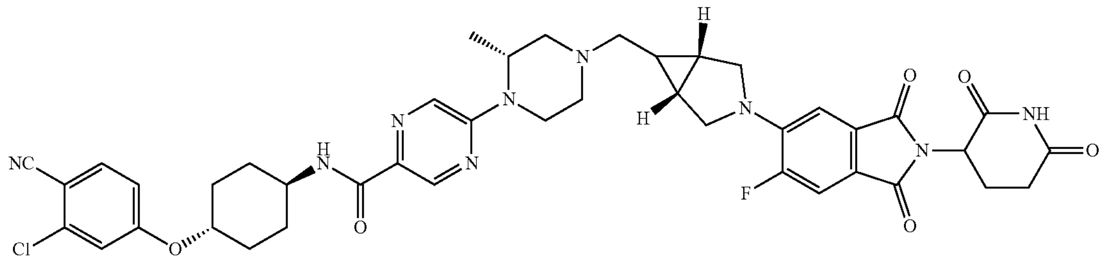
265
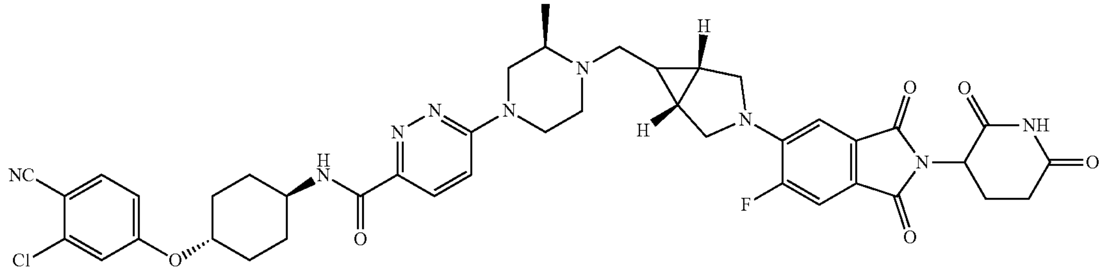
266
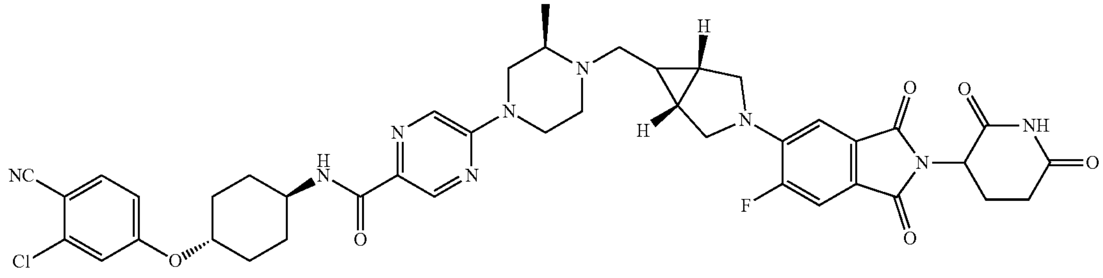
267
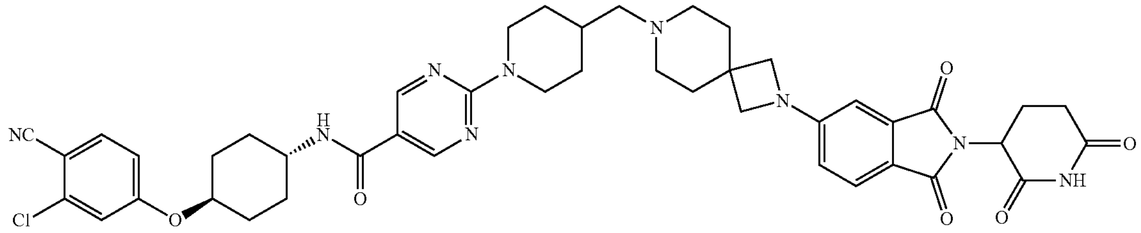
268
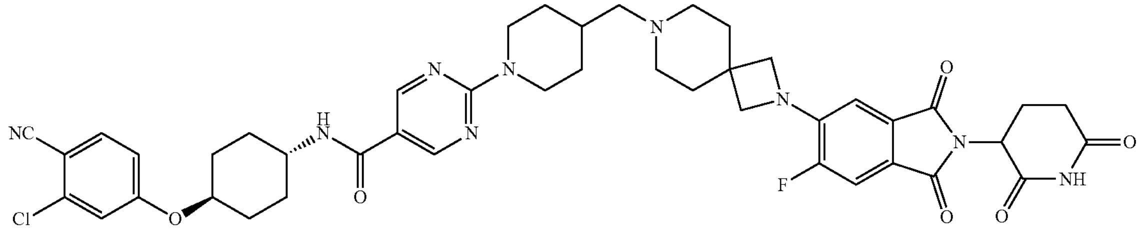
269
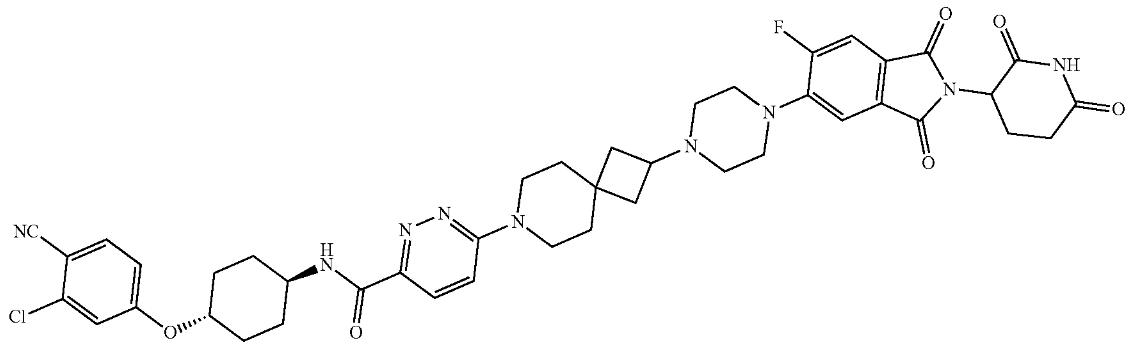

-continued
270
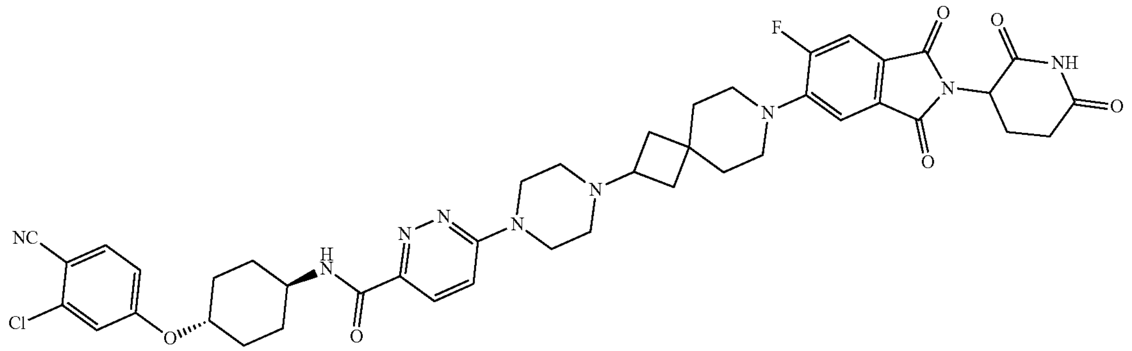
271
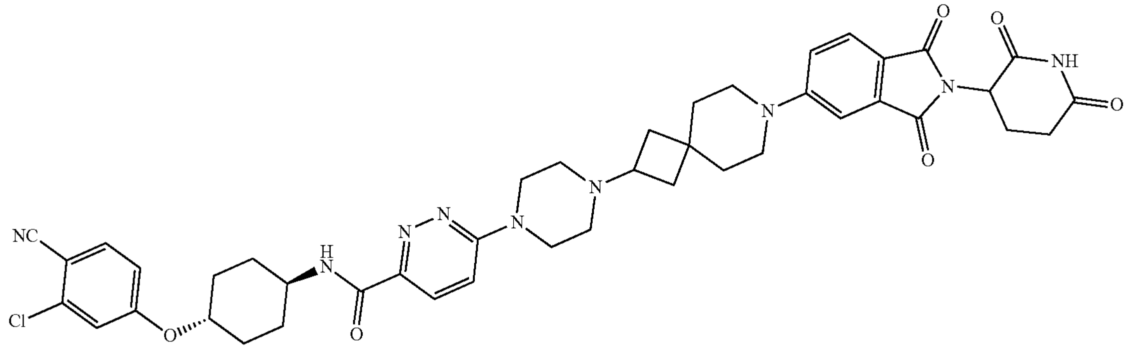
272
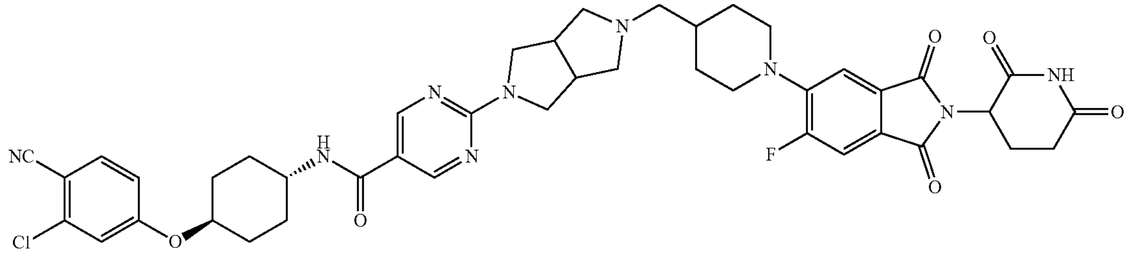
273
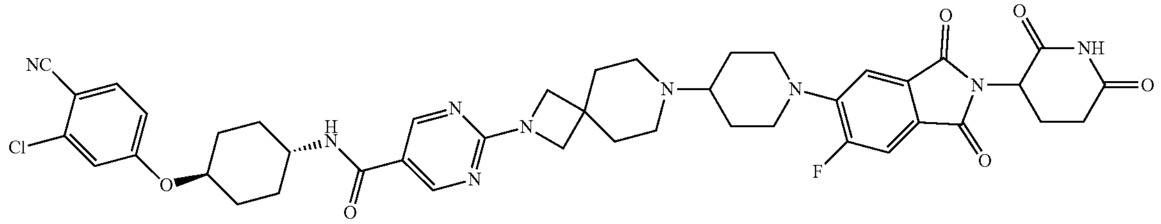
274
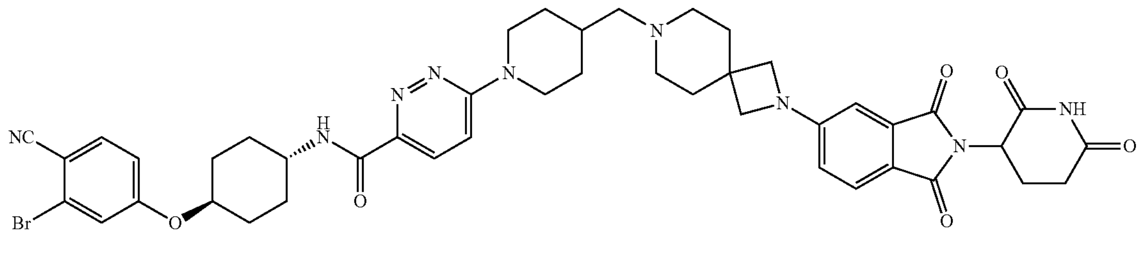

-continued
276
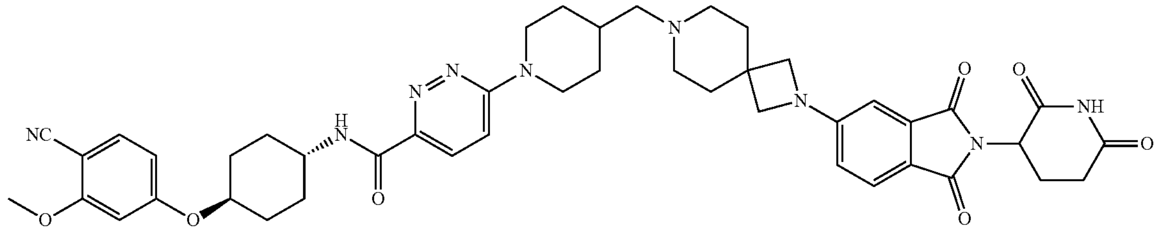
277
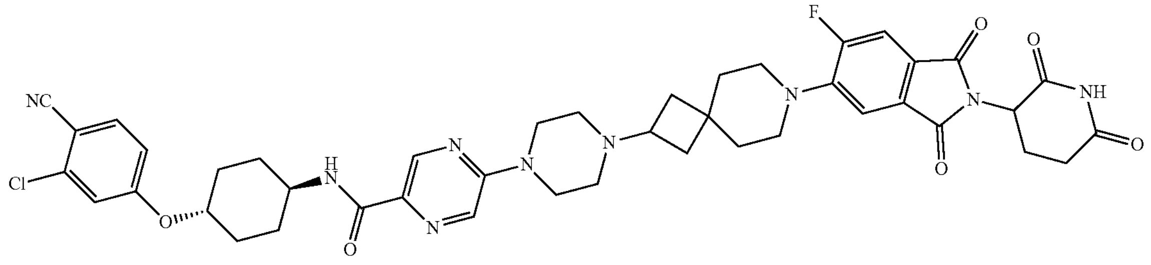
278
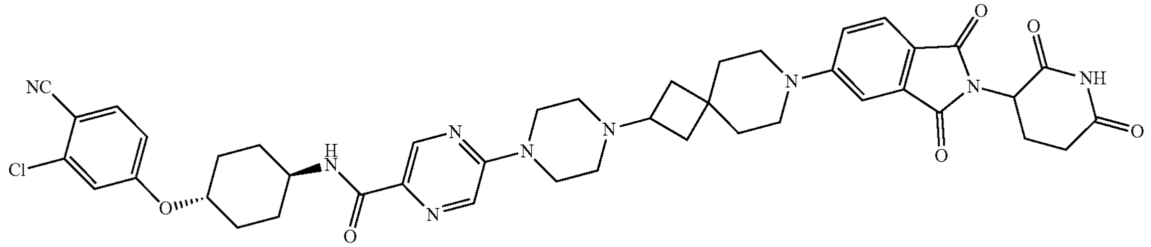
279
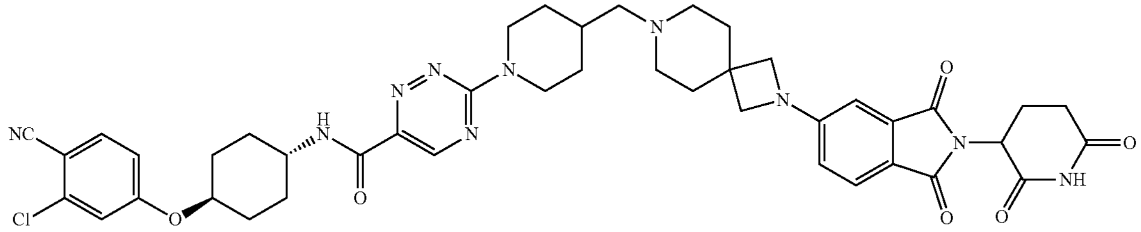
280
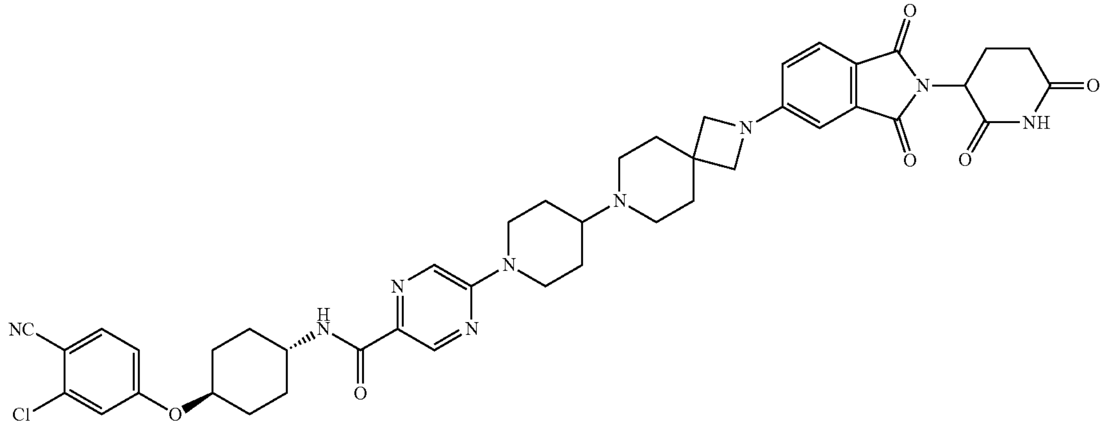

-continued
281
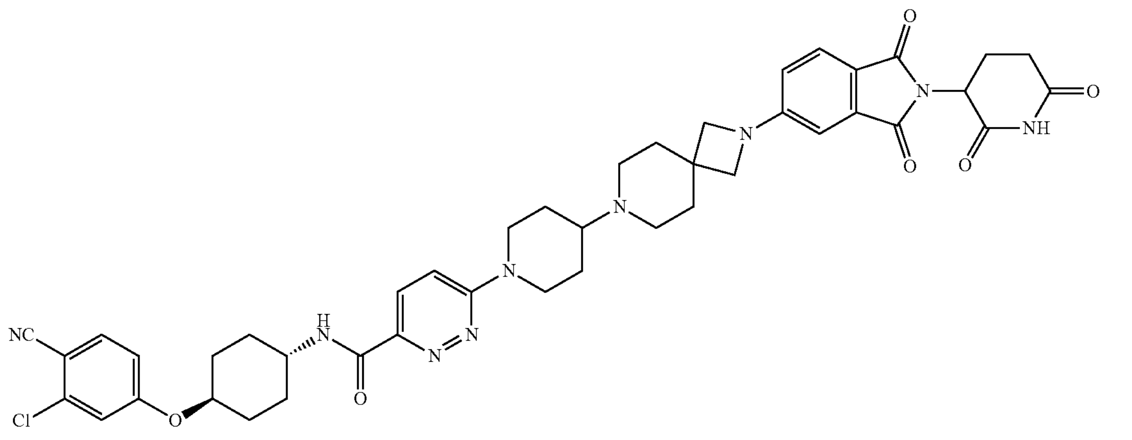
282
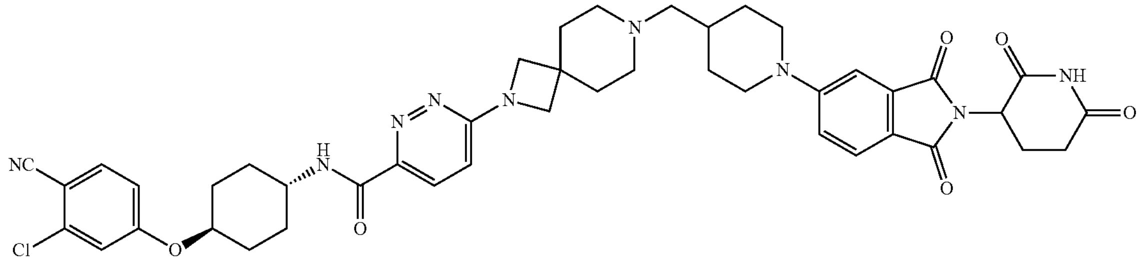
283
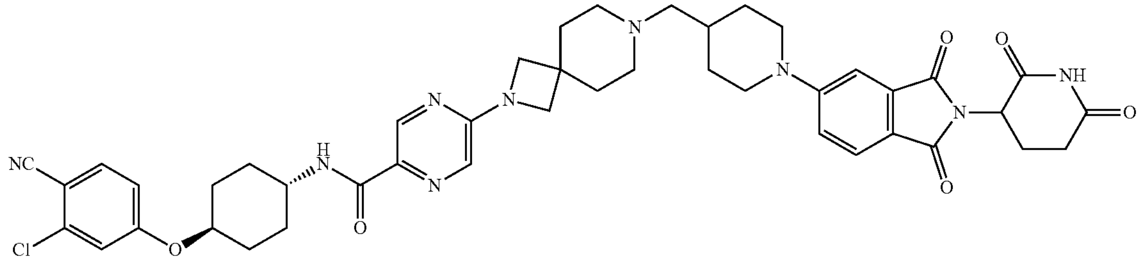
284
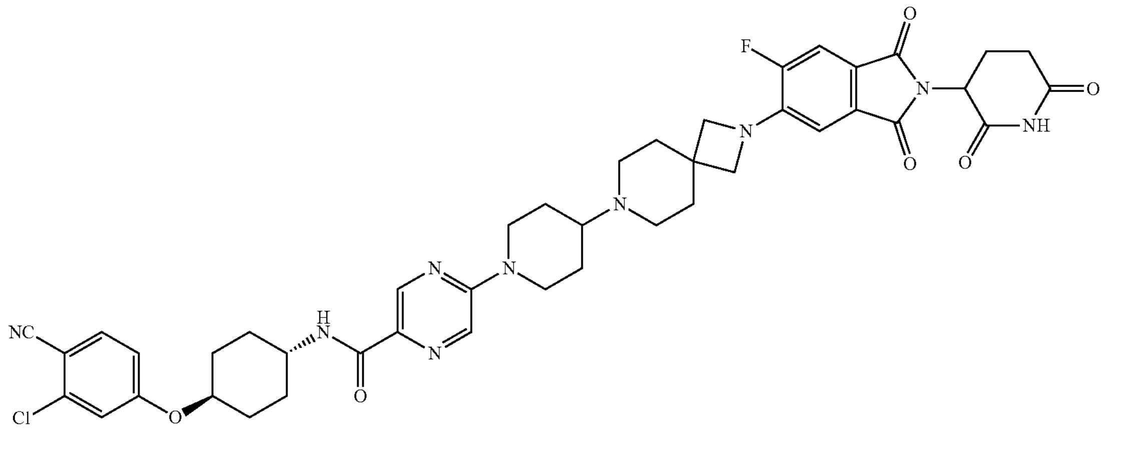

-continued
286
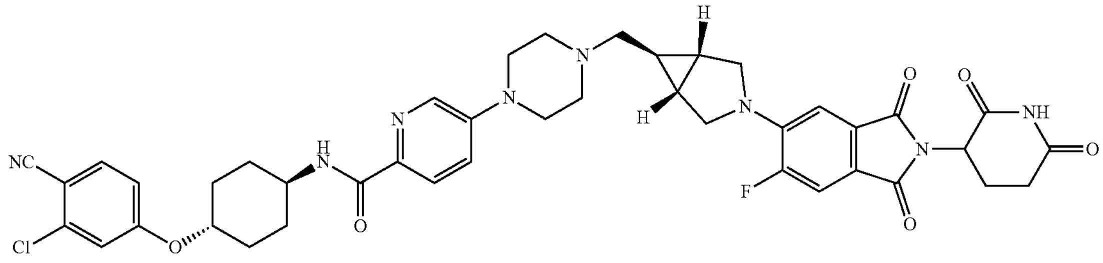
287
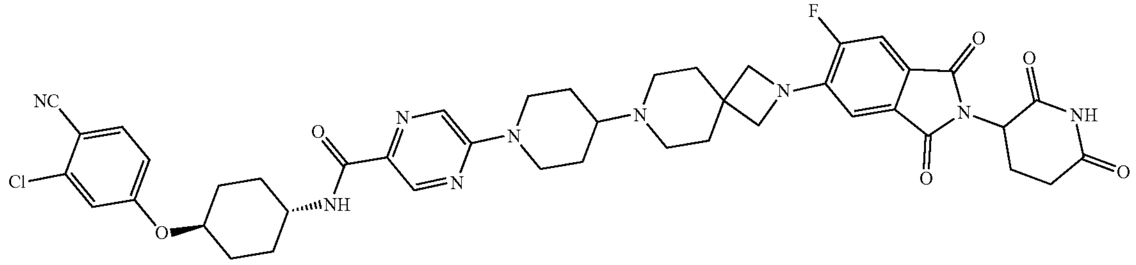
288
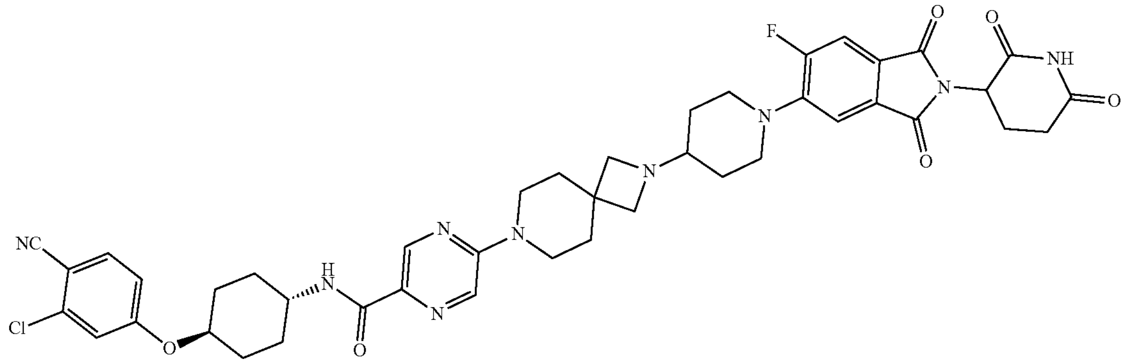
289
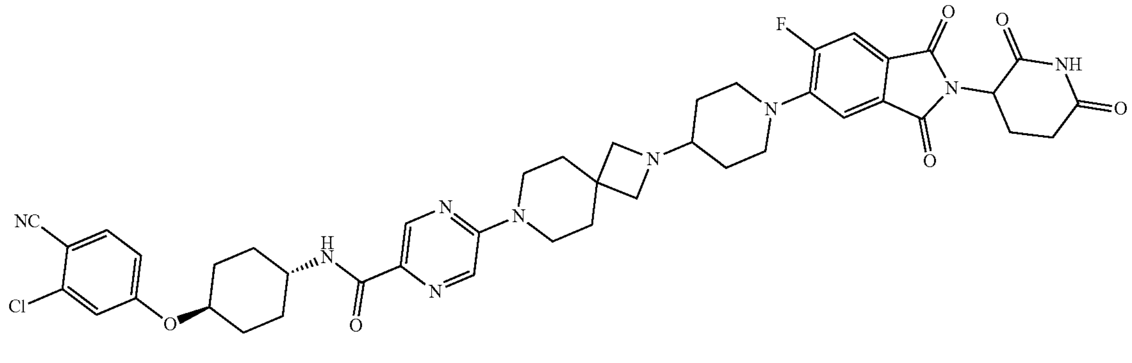

-continued
292
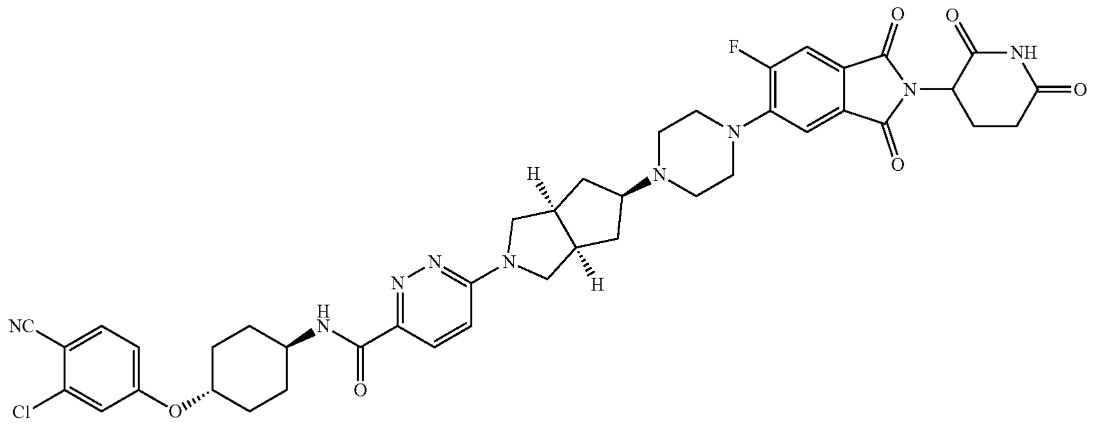
293
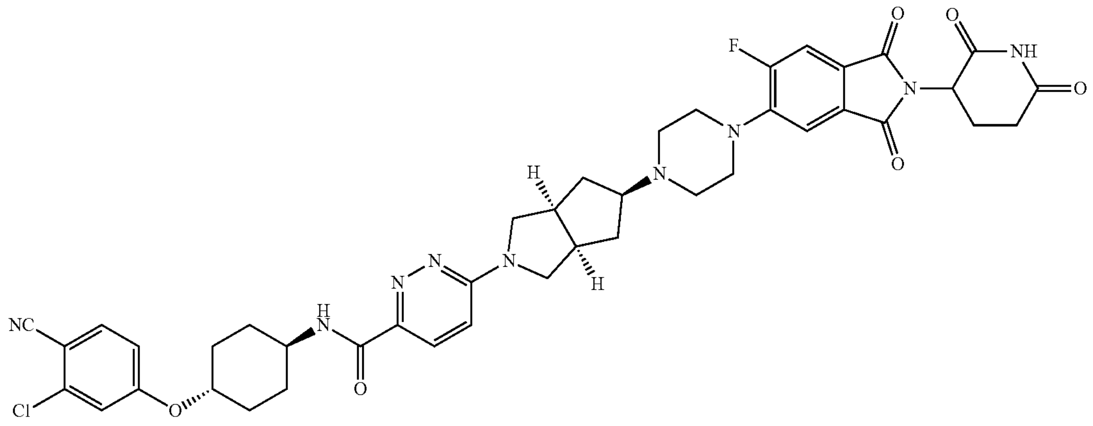
294
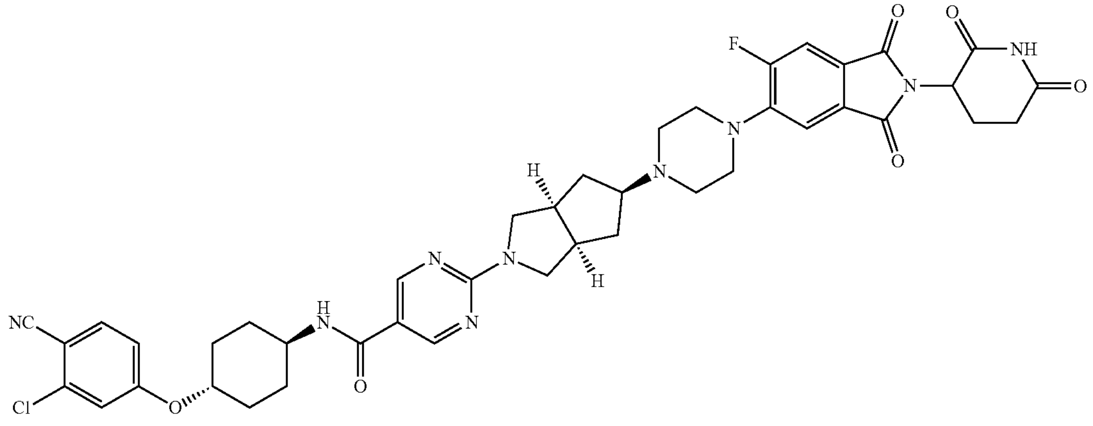

-continued
295
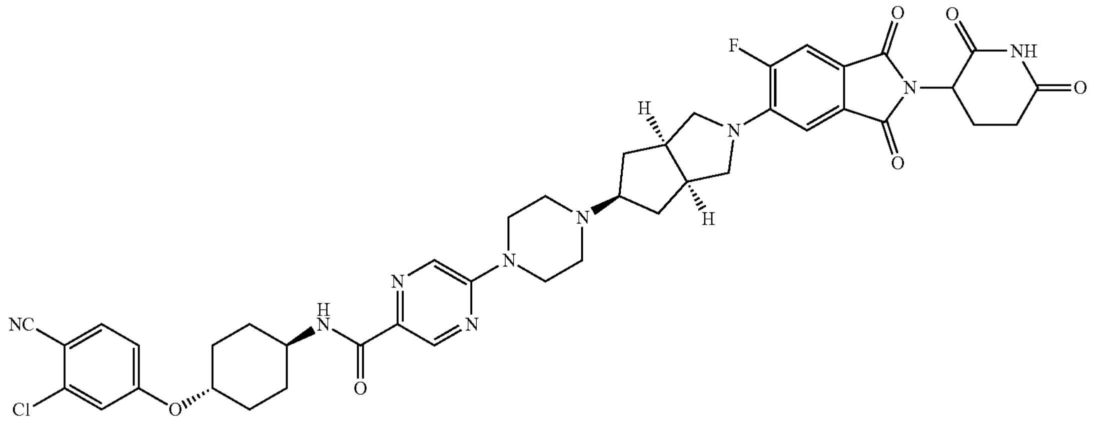
296
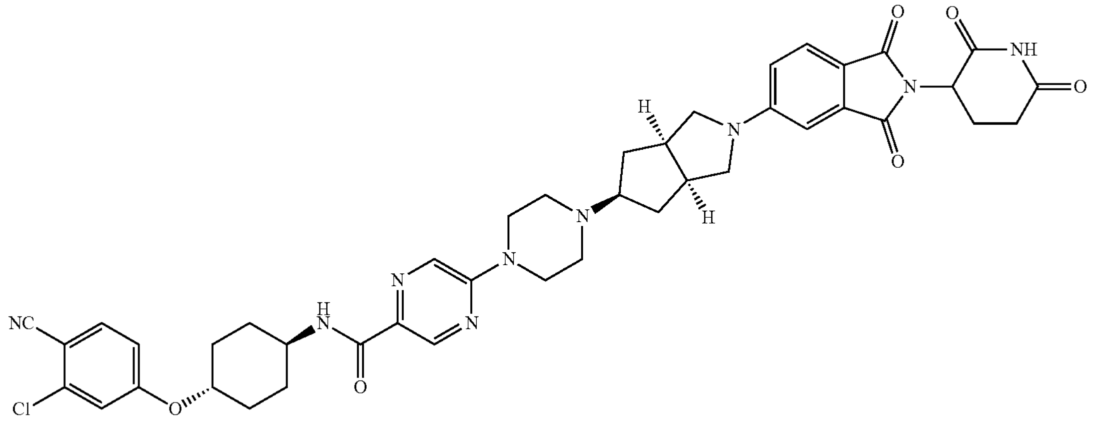
297
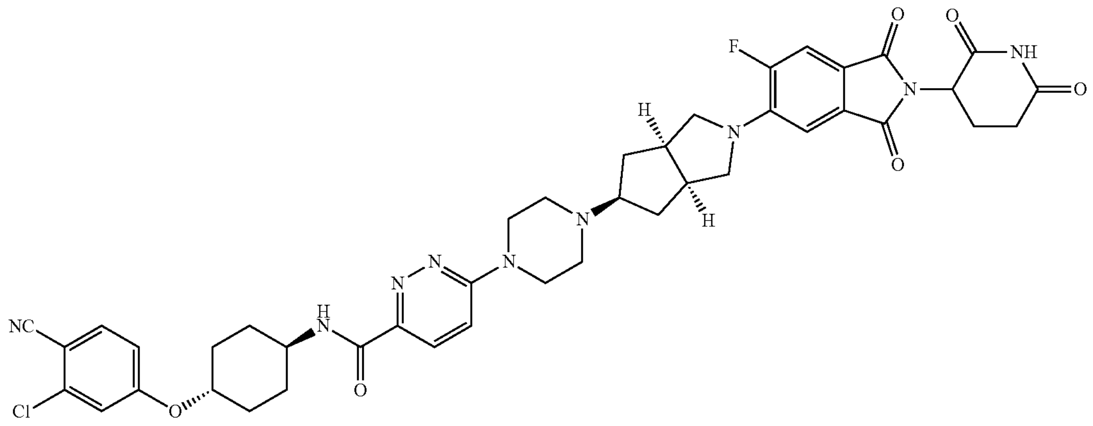

-continued
298
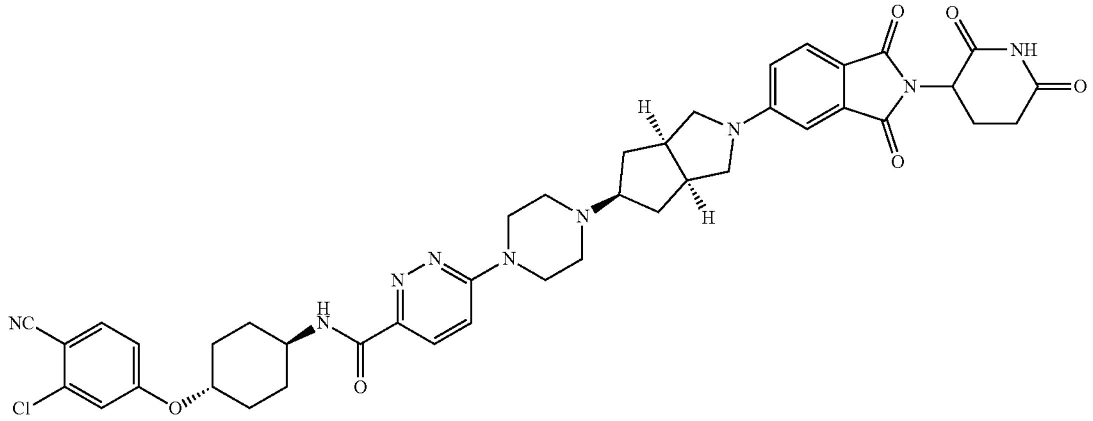
299
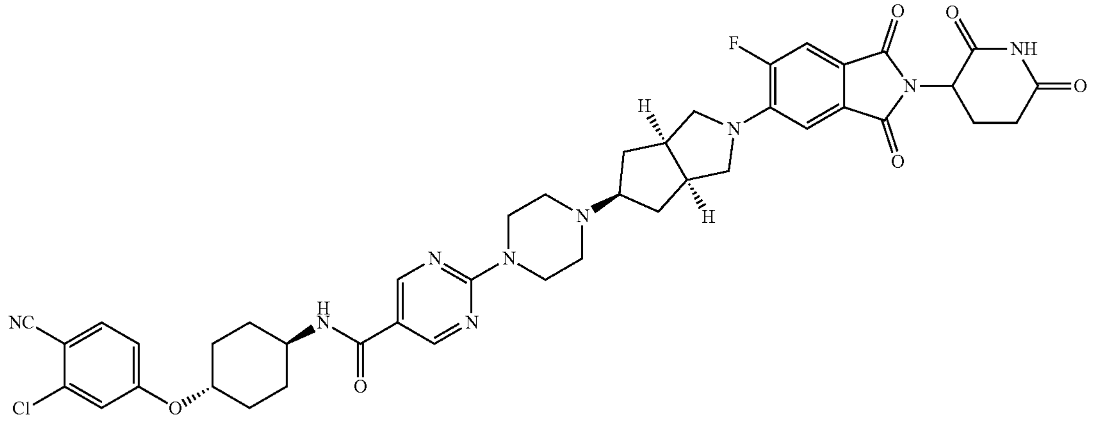
300
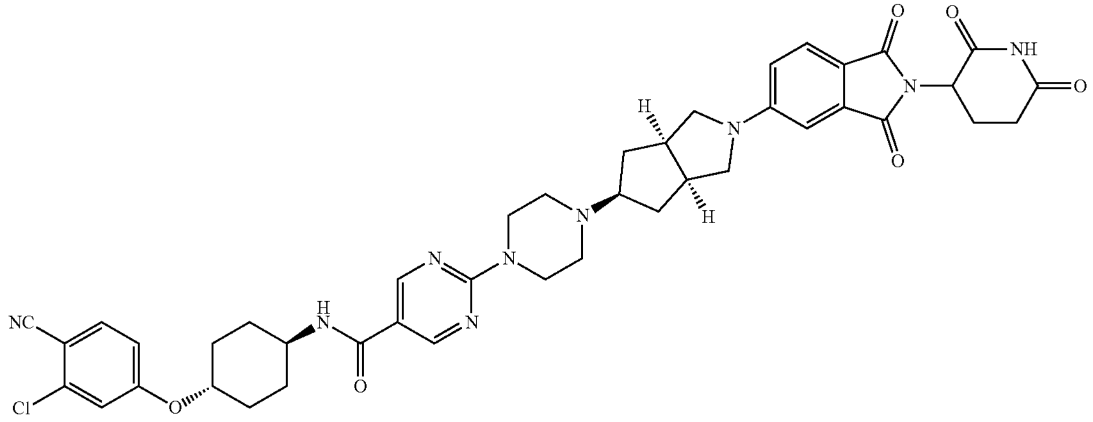
413
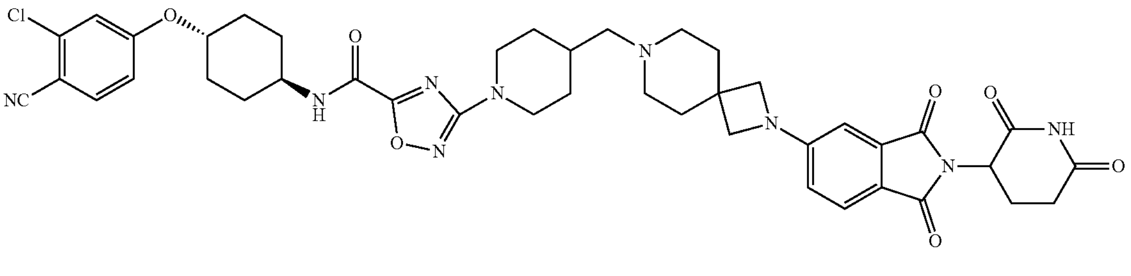

-continued
414
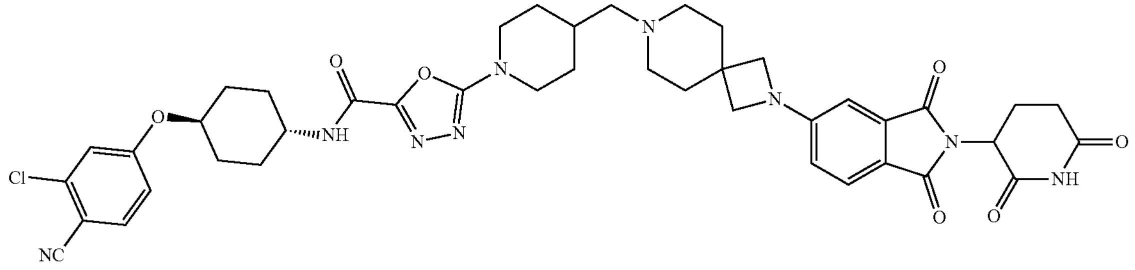
415
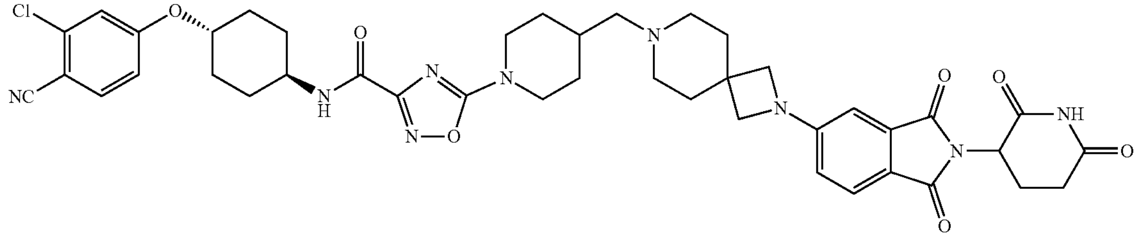
418
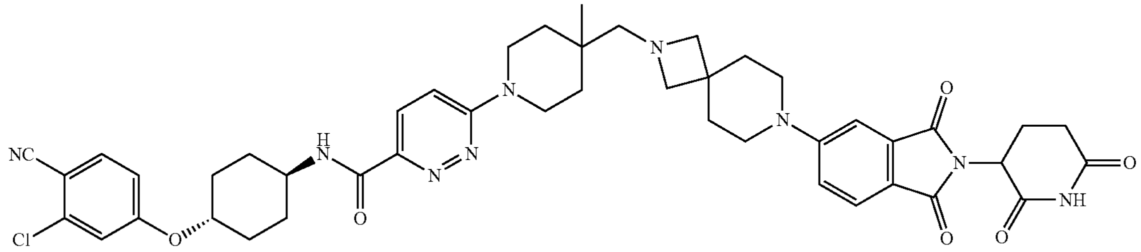
419
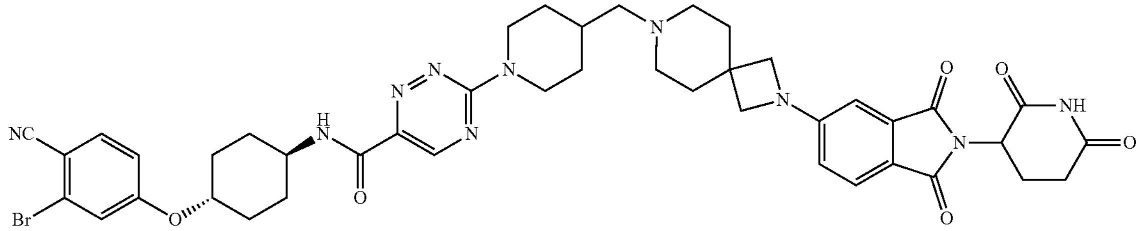
420
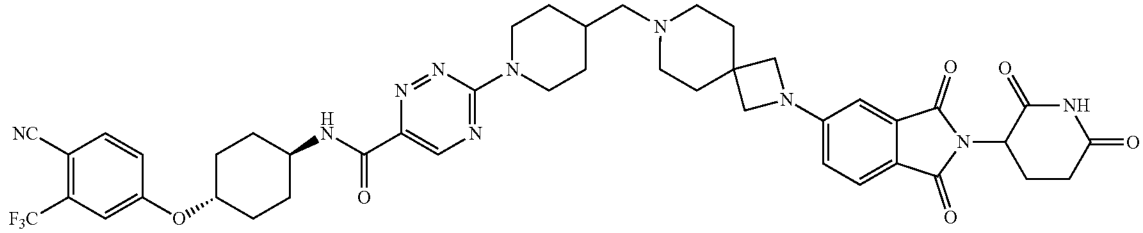
421
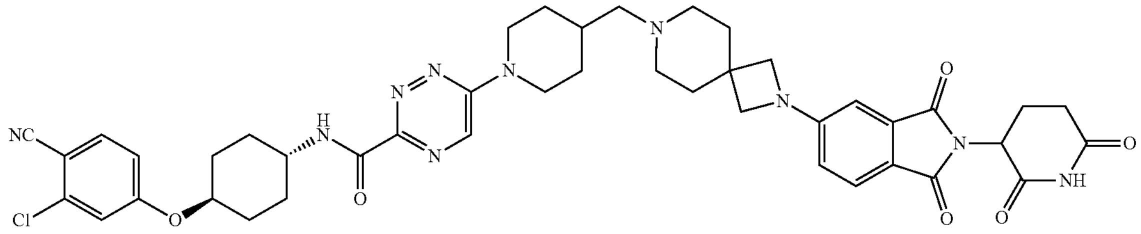

-continued

422

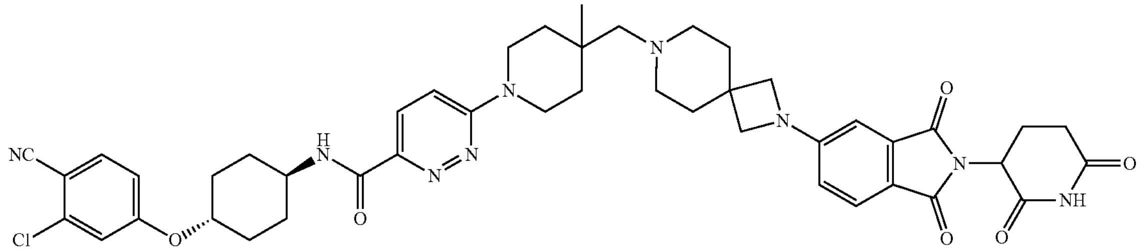

423

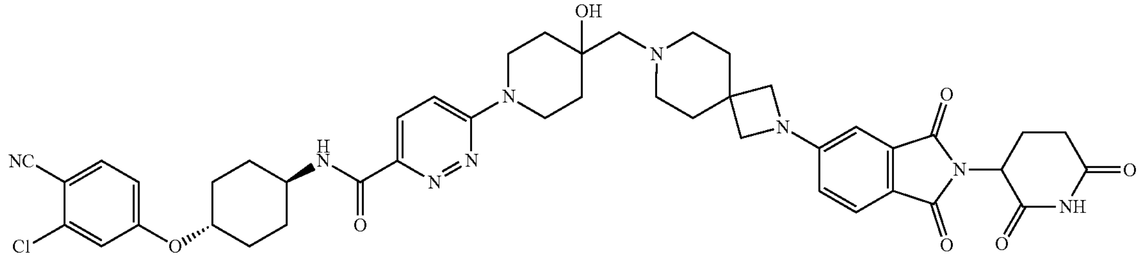

424

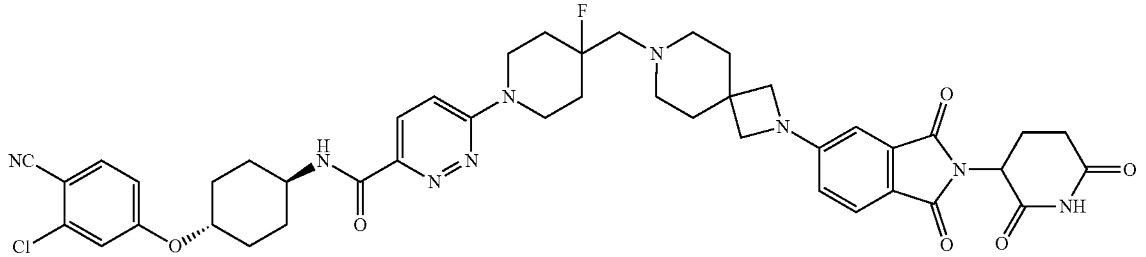

426

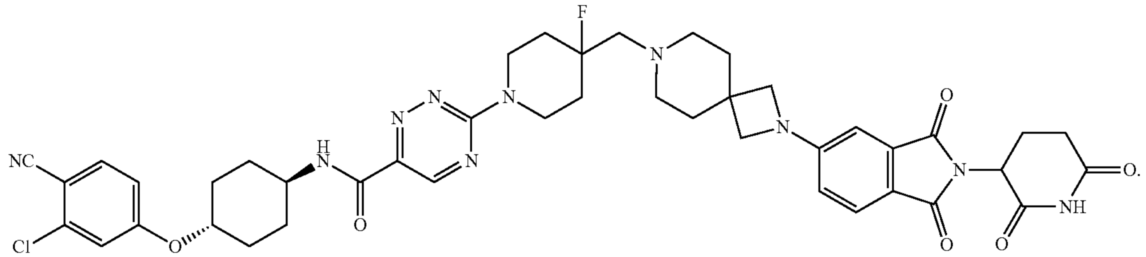

5. A method of targeting chimeras for protein degradation of androgen receptors, comprising administering an effective amount of a composition to a subject in need thereof, wherein the composition comprises the compound according to claim 4, or an isotopic compound thereof, or an optical isomer thereof, or a tautomer thereof, or a pharmaceutically acceptable salt thereof; said targeting chimeras is an active ingredient of drugs for the treatment of related diseases regulated by androgen receptors; and said disease is selected from the group consisting of prostate cancer, breast cancer, and Kennedy's disease.

6. The method according to claim 5, wherein said targeting chimeras can specifically recognize and/or bind to androgen receptors.

7. The method according to claim 5, wherein said targeting chimeras can degrade and/or down-regulate androgen receptors.

* * * * *